US008471005B2

(12) United States Patent
Breslin et al.

(10) Patent No.: US 8,471,005 B2
(45) Date of Patent: Jun. 25, 2013

(54) PYRROLOTRIAZINES AS ALK AND JAK2 INHIBITORS

(75) Inventors: Henry J. Breslin, Lansdale, PA (US); Sankar Chatterjee, Wynnewood, PA (US); James L. Diebold, Eagleville, PA (US); Bruce D. Dorsey, Ambler, PA (US); Derek D. Dunn, Coatesville, PA (US); Diane E. Gingrich, Downingtown, PA (US); Greg A. Hostetler, Newark, DE (US); Robert L. Hudkins, Chester Springs, PA (US); Rachael Hunter, Media, PA (US); Kurt A. Josef, Radnor, PA (US); Joseph Lisko, Alpharetta, GA (US); Eugen F. Mesaros, Wallingford, PA (US); Karen L. Milkiewicz, Exton, PA (US); Gregory R. Ott, Media, PA (US); Babu G. Sundar, West Chester, PA (US); Jay P. Theroff, West Chester, PA (US); Tho Thieu, Ambler, PA (US); Rabindranath Tripathy, Churchville, PA (US); Theodore L. Underiner, Malvern, PA (US); Linda Weinberg, King of Prussia, PA (US); Gregory J. Wells, West Chester, PA (US); Craig A. Zificsak, Downingtown, PA (US)

(73) Assignee: Cephalon, Inc., Frazer, PA (US)

( * ) Notice: Subject to any disclaimer, the term of this patent is extended or adjusted under 35 U.S.C. 154(b) by 0 days.

(21) Appl. No.: 13/160,890

(22) Filed: Jun. 15, 2011

(65) Prior Publication Data
US 2012/0028919 A1    Feb. 2, 2012

Related U.S. Application Data

(63) Continuation of application No. PCT/US2009/069006, filed on Dec. 21, 2009.

(60) Provisional application No. 61/139,545, filed on Dec. 19, 2008.

(51) Int. Cl.
C07D 487/04 (2006.01)
C07D 403/12 (2006.01)
A61K 31/53 (2006.01)
A61K 31/5377 (2006.01)
A61P 35/00 (2006.01)

(52) U.S. Cl.
USPC .......................................... 544/183; 514/243

(58) Field of Classification Search
USPC .......................................... 544/183; 514/243
See application file for complete search history.

(56) References Cited

U.S. PATENT DOCUMENTS

| 4,838,925 | A | 6/1989 | Tseng |
| 2003/0186982 | A1 | 10/2003 | Godfrey et al. |
| 2004/0157846 | A1 | 8/2004 | Chen et al. |
| 2005/0043306 | A1 | 2/2005 | Leftheris et al. |
| 2005/0288289 | A1 | 12/2005 | Crispino et al. |
| 2005/0288290 | A1 | 12/2005 | Borzilleri et al. |
| 2006/0003967 | A1 | 1/2006 | Shi et al. |
| 2006/0004006 | A1 | 1/2006 | Borzilleri et al. |
| 2006/0009454 | A1 | 1/2006 | Cai et al. |
| 2006/0014741 | A1 | 1/2006 | DiMarco et al. |
| 2006/0019928 | A1 | 1/2006 | Lin et al. |
| 2006/0035886 | A1 | 2/2006 | Cann et al. |
| 2006/0084650 | A1 | 4/2006 | Dong et al. |
| 2006/0089358 | A1 | 4/2006 | Gavai et al. |
| 2006/0148801 | A1 | 7/2006 | Hsieh et al. |
| 2006/0211695 | A1 | 9/2006 | Borzilleri et al. |
| 2006/0229449 | A1 | 10/2006 | Bhattacharya et al. |
| 2006/0235020 | A1 | 10/2006 | Kim et al. |
| 2006/0257400 | A1 | 11/2006 | Fargnoli |
| 2007/0004732 | A1 | 1/2007 | Gavai et al. |
| 2007/0123534 | A1 | 5/2007 | Cai et al. |
| 2007/0191375 | A1 | 8/2007 | Wei et al. |
| 2007/0249610 | A1 | 10/2007 | Crispino et al. |

FOREIGN PATENT DOCUMENTS

| EP | 0 301 919 A2 | 2/1989 |
| EP | 0 662 477 A1 | 7/1995 |
| WO | WO 96/21662 | 7/1996 |
| WO | WO 00/71129 A1 | 11/2000 |
| WO | WO 01/14378 A1 | 1/2001 |
| WO | WO 02/40486 A2 | 5/2002 |
| WO | WO 03/042172 A2 | 5/2003 |
| WO | WO 03/090912 A1 | 11/2003 |
| WO | WO 03/091229 A1 | 11/2003 |

(Continued)

OTHER PUBLICATIONS

Nishimura et al. Carbohydrate Research 331, 77-82, 2001.*
Ewald et al. Justus Liebigs Annalen der Chemie (1977), (10), 1718-24. CA 88:121117, 1978. CAPLUS Abstract provided.*
Cecil Textbook of Medicine, edited by Bennet, J.C., and Plum F., 20th edition, vol. 1, 1004-1010, 1996.*

(Continued)

Primary Examiner — Venkataraman Balasubramanian

(57) ABSTRACT

The present invention provides a compound of formula I

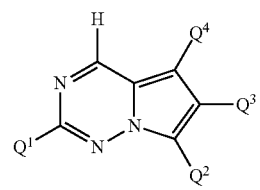

or a salt form thereof, wherein $Q^1$, $Q^2$, $Q^3$, and $Q^4$ are as defined herein. The compound of formula I has ALK and/or JAK2 inhibitory activity, and may be used to treat proliferative disorders.

10 Claims, No Drawings

FOREIGN PATENT DOCUMENTS

| | | |
|---|---|---|
| WO | WO 03/099286 A1 | 12/2003 |
| WO | WO 2004/009542 A2 | 1/2004 |
| WO | WO 2004/009601 A1 | 1/2004 |
| WO | WO 2004/009784 A2 | 1/2004 |
| WO | WO 2004/013145 A1 | 2/2004 |
| WO | WO 2004/046331 A2 | 6/2004 |
| WO | WO 2004/054514 A2 | 7/2004 |
| WO | WO 2004/071460 A2 | 8/2004 |
| WO | WO 2004/087056 A2 | 10/2004 |
| WO | WO 2005/020899 A2 | 3/2005 |
| WO | WO 2005/021500 A1 | 3/2005 |
| WO | WO 2005/058245 A2 | 6/2005 |
| WO | WO 2005/065266 A2 | 7/2005 |
| WO | WO 2005/066176 A1 | 7/2005 |
| WO | WO 2005/097052 A1 | 10/2005 |
| WO | WO 2005/121147 A1 | 12/2005 |
| WO | WO 2006/007468 A1 | 1/2006 |
| WO | WO 2006/030941 A1 | 3/2006 |
| WO | WO 2006/035061 A1 | 4/2006 |
| WO | WO 2006/069395 A2 | 6/2006 |
| WO | WO 2006/116016 A2 | 11/2006 |
| WO | WO 2006/116713 A1 | 11/2006 |
| WO | WO 2006/130657 A2 | 12/2006 |
| WO | WO 2007/004731 A1 | 1/2007 |
| WO | WO 2007/004732 A1 | 1/2007 |
| WO | WO 2007/005631 A1 | 1/2007 |
| WO | WO 2007/005707 A2 | 1/2007 |
| WO | WO 2007/005709 A1 | 1/2007 |
| WO | WO 2007/015569 A1 | 2/2007 |
| WO | WO 2007/015578 A1 | 2/2007 |
| WO | WO 2007/038648 A1 | 4/2007 |
| WO | WO 2007/056170 A2 | 5/2007 |
| WO | WO 2007/061882 A2 | 5/2007 |
| WO | WO 2007/064883 A2 | 6/2007 |
| WO | WO 2007/064931 A2 | 6/2007 |
| WO | WO 2007/064932 A2 | 6/2007 |
| WO | WO 2007/068895 A1 | 6/2007 |
| WO | WO 2007/103839 A2 | 9/2007 |
| WO | WO 2007/104557 A2 | 9/2007 |
| WO | WO 2008/005956 A2 | 1/2008 |
| WO | WO 2008/012635 A2 | 1/2008 |
| WO | WO 2008/021859 A1 | 2/2008 |
| WO | WO 2008/021924 A1 | 2/2008 |
| WO | WO 2008/027013 A2 | 3/2008 |
| WO | WO 2008/053221 A2 | 5/2008 |
| WO | WO 2008/057775 A2 | 5/2008 |
| WO | WO 2008/057863 A1 | 5/2008 |
| WO | WO 2008/057994 A2 | 5/2008 |
| WO | WO 2008/070616 A2 | 6/2008 |

OTHER PUBLICATIONS

Freshney et al.,Culture of Animal Cells, A Manual of Basic Technique, Alan R. Liss, Inc., 1983, New York, p. 4.*
Dermer et al., Bio/Technology, 1994, 12:320.*
Cohen et al., Current Opinion in Chemical Biology, 3,459-465, 1999.*
Golub et al., Science, 286, 531-537, 1999.*
Mass, R. D., Int. J. Radiation Oncology Bio. Phys.vol. 58(3): 932-940, 2004.*
Fabbro et al. Pharmacology & Therapeutics 93, 79-98, 2002.*
Ewald et al., "Cycloadditionen mit Azabenzolen, XII: Reaktionen von 1,2,4-Triazinen mit Acetylendicarbonsauredimethylester", *Liebigs Ann. Chem.* (1977), pp. 1718-1724.
Hayashi et al., "C-Nucleosides. 17.: A Synthesis of 2-substituted 7-(B-D-Ribofuranosyl)-pyrrolo[2,1=t]-1,2,4-triazines. A New Type of"Purine Like" C-Nucleoside", *Heterocycles* (1992), vol. 34(3), pp. 569-574.
Nishimura et al., "Synthesis of pyrrolo[2,1-f][1,2,4]triazine C-nucleosides. Isosteres of sangivamycin, tubercidin, and toyocamycin", *Carbohydrate Res.* (2001), 331, pp. 77-82.
Patil et al., "Synthesis of Pyrrolo[2,1-f][1,2,4]triazine Congeners of Nucleic Acid Purines via the N-Amination of 2-Substituted Pyrroles[1]", *J. Heterocyclic Chem.* (1994), 31, pp. 781-786.
Ostrowska et al., N-Alkyl-, N-Aryl-, and N-Hetaryl-Substituted Amidines (Imidamides), *Science of Synthesis* (2005), vol. 22, pp. 379-488.
Database Registry (Online) Chemical Abstracts Service, Columbus, Ohio, US; Registry No. 444284-33-7.

\* cited by examiner

PYRROLOTRIAZINES AS ALK AND JAK2 INHIBITORS

CROSS REFERENCE TO RELATED APPLICATIONS

This application is a continuation of International Application PCT/US2009/069006, filed Dec. 21, 2009, which claims the benefit of U.S. Provisional Application No. 61/139,545, filed Dec. 19, 2008, the disclosures of which are incorporated herein by reference in their entireties.

BACKGROUND OF THE INVENTION

Anaplastic Lymphoma Kinase (ALK) is a cell membrane-spanning receptor tyrosine kinase, which belongs to the insulin receptor subfamily. The most abundant expression of ALK occurs in the neonatal brain, suggesting a possible role for ALK in brain development (Duyster, J. et al., *Oncogene*, 2001, 20, 5623-5637).

ALK is also implicated in the progression of certain tumors. For example, approximately sixty percent of anaplastic large cell lymphomas (ALCL) are associated with a chromosome mutation that generates a fusion protein consisting of nucleophosmin (NPM) and the intracellular domain of ALK. (Armitage, J. O. et al., *Cancer: Principle and Practice of Oncology*, 6$^{th}$ edition, 2001, 2256-2316; Kutok J. L. & Aster J. C., *J. Clin. Oncol.*, 2002, 20, 3691-3702). This mutant protein, NPM-ALK, possesses a constitutively active tyrosine kinase domain that is responsible for its oncogenic property through activation of downstream effectors. (Falini, B. et al., *Blood*, 1999, 94, 3509-3515; Morris, S. W. et al., *Brit. J. Haematol.*, 2001, 113, 275-295; Duyster et al.; Kutok & Aster). In addition, the transforming EML4-ALK fusion gene has been identified in non-small-cell lung cancer (NSCLC) patients (Soda, M., et al., *Nature*, 2007, 448, 561-566) and represents another in a list of ALK fusion proteins that are promising targets for ALK inhibitor therapy. Experimental data have demonstrated that the aberrant expression of constitutively active ALK is directly implicated in the pathogenesis of ALCL and that inhibition of ALK can markedly impair the growth of ALK+ lymphoma cells (Kuefer, Mu et al. *Blood*, 1997, 90, 2901-2910; Bai, R. Y. et al., *Mol. Cell. Biol.*, 1998, 18, 6951-6961; Bai, R. Y. et al., *Blood*, 2000, 96, 4319-4327; Ergin, M. et al., *Exp. Hematol.*, 2001, 29, 1082-1090; Slupianek, A. et al., *Cancer Res.*, 2001, 61, 2194-2199; Turturro, F. et al., *Clin. Cancer Res.*, 2002, 8, 240-245). The constitutively activated chimeric ALK has also been demonstrated in about 60% of inflammatory myofibroblastic tumors (IMTs), a slow-growing sarcoma that mainly affects children and young adults. (Lawrence, B. et al., *Am. J. Pathol.*, 2000, 157, 377-384; Duyster et al.).

In addition, ALK and its putative ligand, pleiotrophin, are overexpressed in human glioblastomas (Stoica, G. et al., *J. Biol. Chem.*, 2001, 276, 16772-16779). In mouse studies, depletion of ALK reduced glioblastoma tumor growth and prolonged animal survival (Powers, C. et al., *J. Biol. Chem.*, 2002, 277, 14153-14158; Mentlein, R. et al, *J. Neurochem.*, 2002, 83, 747-753).

An ALK inhibitor would be expected to either permit durable cures when combined with current chemotherapy for ALCL, IMT, proliferative disorders, glioblastoma and possible other solid tumors, or, as a single therapeutic agent, could be used in a maintenance role to prevent cancer recurrence in those patients. Various ALK inhibitors have been reported, such as indazoloisoquinolines (WO 2005/009389), thiazole amides and oxazole amides (WO 2005/097765), pyrrolopyrimidines (WO 2005080393), and pyrimidinediamines (WO 2005/016894).

The Janus kinases (JAKs) are a family of kinases of which there are four in mammals (JAK1, JAK2, JAK3 and TYK2) integral in signaling from extracellular cytokines, including the interleukins, interferons, as well as numerous hormones (Aringer, M., et al., *Life Sci*, 1999. 64(24): p. 2173-86; Briscoe, J., et al., *Philos Trans R Soc Lond B Biol Sci*, 1996. 351(1336): p. 167-71; Ihle, J. N., *Semin Immunol*, 1995. 7(4): p. 247-54; Ihle, J. N., *Philos Trans R Soc Lond B Biol Sci*, 1996. 351(1336): p. 159-66; Firmbach-Kraft, I., et al., *Oncogene*, 1990. 5(9): p. 1329-36; Harpur, A. G., et al., *Oncogene*, 1992. 7(7): p. 1347-53; Rane, S. G. and E. P. Reddy, *Oncogene*, 1994. 9(8): p. 2415-23; Wilks, A. F., *Methods Enzymol*, 1991. 200: p. 533-46). These non-receptor tyrosine kinases associate with various cytokine receptors and act to transduce the signal from extracellular ligand-receptor binding into the cytoplasm, by phosphorylating STAT (signal transducer and activator of transcription) molecules, which then enter the nucleus and direct transcription of various target genes involved in growth and proliferation (Briscoe, J., et al.; Ihle, J. N. (1995); Ihle, J. N. (1996); Rawlings, J. S., K. M. Rosier and D. A. Harrison, *J Cell Sci*, 2004. 117(Pt 8): p. 1281-3.). The importance of these kinases in cellular survival is made evident by the fact that the loss of JAKs is often accompanied by immunodeficiency and non-viability in animal models (Aringer, M., et al.). The JAK family of enzymes is characterized by a number of JAK homology (JH) domains, including a carboxy-terminal protein tyrosine kinase domain (JH1) and an adjacent kinase-like domain (JH2), which is thought to regulate the activity of the JH1 domain (Harpur, A. G., et al.). The four JAK isoforms transduce different signals by being associated specifically with certain cytokine receptors, and activating a subset of downstream genes. For example, JAK2 associates with cytokine receptors specific for interleukin-3 (Silvennoinen, O., et al., *Proc Natl Acad Sci USA*, 1993. 90(18): p. 8429-33), erythropoietin (Witthuhn, B. A., et al., *Cell*, 1993. 74(2): p. 227-36), granulocyte colony stimulating factor (Nicholson, S. E., et al., *Proc Natl Acad Sci USA*, 1994. 91(8): p. 2985-8), and growth hormone (Argetsinger, L. S., et al., *Cell*, 1993. 74(2): p. 237-44).

The JAK family of enzymes has become an interesting set of targets for various hematological and immunological disorders; JAK2 specifically is currently under study as a viable target for neoplastic disease, especially leukemias and lymphomas (Benekli, M., et al., *Blood*, 2003. 101(8): p. 2940-54; Peeters, P., et al., *Blood*, 1997. 90(7): p. 2535-40; Reiter, A., et al., *Cancer Res*, 2005. 65(7): p. 2662-7; Takemoto, S., et al., *Proc Natl Acad Sci USA*, 1997. 94(25): p. 13897-902) as well as solid tumors (Walz, C., et al., *J Biol Chem*, 2006. 281(26): p. 18177-83), and other myeloproliferative disorders such as polycythemia vera (Baxter, E. J., et al., *Lancet*, 2005. 365 (9464): p. 1054-61; James, C., et al., *Nature*, 2005. 434(7037): p. 1144-8; Levine, R. L., et al., *Cancer Cell*, 2005. 7(4): p. 387-97; Shannon, K. and R. A. Van Etten, *Cancer Cell*, 2005. 7(4): p. 291-3), due to its activation of downstream effector genes involved in proliferation. JAK2 is also known to be mutated in hematologic malignancies, such that it no longer requires ligand binding to the cytokine receptor and is instead in a state of constitutive activation. This can occur through translocation between the JAK2 gene with genes encoding the ETV6, BCR or PCM1 proteins (Peeters, P., et al.; Reiter, A., et al.; Griesinger, F., et al., *Genes Chromosomes Cancer*, 2005. 44(3): p. 329-33; Lacronique, V., et al., *Science*, 1997. 278(5341): p. 1309-12) to create an oncogenic fusion protein, analogous to the BCR-ABL protein seen in chronic myelogenous leukemia. Overactivation of JAK2 can also occur through mutation of the JAK2 sequence itself; for example, the myeloproliferative disease polycythemia vera is associated with a point mutation that causes a valine-to-phenylalanine substitution at amino acid 617 (JAK2 V617F) (Walz, C., et al.). Because of its association with, and deregulation in, neoplastic and myeloproliferative disorders, small molecule JAK2 inhibitors for the treatment of human malignancies are of significant interest.

A need exists for ALK and JAK2 inhibitors for use as pharmaceutical agents.

SUMMARY OF THE INVENTION

The present invention provides a compound of formula I

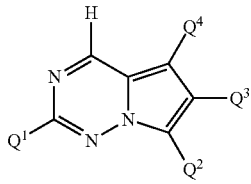

I or a pharmaceutically acceptable salt form thereof, wherein $Q^1$, $Q^2$, $Q^3$, and $Q^4$ are as defined herein.

The compound of formula I has ALK and/or JAK2 inhibitory activity, and may be used to treat ALK- or JAK2-mediated disorders or conditions.

The present invention further provides a pharmaceutical composition comprising at least one compound of the present invention together with at least one pharmaceutically acceptable carrier, diluent, or excipient therefor.

In another aspect, the present invention provides a method of treating a subject suffering from an ALK- or JAK2-mediated disorder or condition comprising: administering to the subject the pharmaceutical composition of the present invention.

The present invention further provides a method of treating a proliferative disorder in a subject, comprising administering to the subject a therapeutically effective amount of a compound of the present invention.

DETAILED DESCRIPTION OF THE INVENTION

I. Definitions

As used herein, the following terms have the meanings ascribed to them unless specified otherwise.

"Alkyl" or "alkyl group" refers to a monoradical of a branched or unbranched saturated hydrocarbon chain. Examples include, but are not limited to, methyl, ethyl, n-propyl, n-butyl, n-pentyl, n-hexyl, n-heptyl, n-octyl, n-nonyl, n-decyl, isopropyl, tert-butyl, isobutyl, etc. Alkyl groups typically contain 1-10 carbon atoms, such as 1-6 carbon atoms, and can be substituted or unsubstituted.

The term "$C_{x-y}$" indicates the number of carbon atoms in a group. For example, a "$C_{1-6}$-alkyl" is an alkyl group having from one (1) to six (6) carbon atoms. In some instances, x=0, i.e., "$C_{0-y}$". The term "$C_{0-y}$" indicates that the group may be absent or present, and if present, defines the number of carbon atoms in the group. For example, "$C_{0-6}$-alkyl" indicates that an alkyl group may be absent (x=0) or present (x=1-6), and if present contains from one (1) to six (6) carbon atoms. For example, "—$C_{0-6}$-alkyl-C(=O)—$C_{0-6}$-alkyl-" includes —C(=O)—, —$C_{1-6}$-alkyl-C(=O)—, and —$C_{1-6}$-alkyl-C(=O)—$C_{1-6}$-alkyl-. Examples of —$C_{0-6}$-alkyl-C(=O)—$C_{0-6}$-alkyl- include, but are not limited to, —C(=O)—, —CH$_2$CH$_2$—C(=O)—, and —CH(CH$_3$)CH$_2$CH$_2$—C(=O)—CH$_2$—.

The term "alkyl-(R)$_x$," wherein "x is chosen from 0, 1, 2, 3, 4, 5, and 6" refers to an alkyl group that is substituted at any position(s) by 0, 1, 2, 3, 4, 5, or 6 identical or different "R" substituents. For example, in the group —CH$_2$CF$_2$CH$_3$, R=F and x=2. In the group —CH$_2$CH(OH)CF$_3$, R=F, —OH and x=4. In the group —CH$_2$CH$_2$CH$_3$, x=0.

"Alkylene" or "alkylene group" refers to a diradical of a branched or unbranched saturated hydrocarbon chain. Examples include, but are not limited to, methylene (—CH$_2$—), the ethylene isomers (—CH(CH$_3$)— and —CH$_2$CH$_2$—), the propylene isomers (—CH(CH$_3$)CH$_2$—, —CH(CH$_2$CH$_3$)—, —C(CH$_3$)$_2$—, and —CH$_2$CH$_2$CH$_2$—), etc. Alkylene groups typically contain 1-10 carbon atoms, such as 1-6 carbon atoms, and can be substituted or unsubstituted.

"Alkenyl" or "alkenyl group" refers to a monoradical of a branched or unbranched hydrocarbon chain containing at least one double bond. Examples include, but are not limited to, ethenyl, 3-buten-1-yl, 2-ethenylbutyl, and 3-hexen-1-yl. Alkenyl groups typically contain 2-10 carbon atoms, such as 2-6 carbon atoms, and can be substituted or unsubstituted.

"Alkenylene" or "alkenylene group" refers to a diradical of a branched or unbranched hydrocarbon chain containing at least one double bond. Examples include, but are not limited to, the ethenylene isomers (—C(=CH$_2$)— and —CH=CH—), the propenylene isomers (—C(=CH$_2$)CH$_2$—, —C(CH$_3$)=CH—, —C(=CHCH$_3$)—, —C(CH=CH$_2$)—, and —CH=CHCH$_2$—), etc. Alkenylene groups typically contain 2-10 carbon atoms, such as 2-6 carbon atoms, and can be substituted or unsubstituted.

"Alkynyl" or "alkynyl group" refers to a monoradical of a branched or unbranched hydrocarbon chain containing at least one triple bond. Examples include, but are not limited to, ethynyl, 3-butyn-1-yl, propynyl, 2-butyn-1-yl, and 3-pentyn-1-yl. Alkynyl groups typically contain 2-10 carbon atoms, such as 2-6 carbon atoms, and can be substituted or unsubstituted.

"Alkynylene" or "alkynylene group" refers to a diradical of a branched or unbranched hydrocarbon chain containing at least one triple bond. Examples include, but are not limited to, ethynylene (—C≡CH—), propynylene (—C≡CHCH$_2$—), etc. Alkynylene groups typically contain 2-10 carbon atoms, such as 2-6 carbon atoms, and can be substituted or unsubstituted.

"Haloalkyl" or "haloalkyl group" refers to alkyl groups in which one or more hydrogen atoms are replaced by halogen atoms. Haloalkyl includes both saturated alkyl groups and unsaturated alkenyl and alkynyl groups, such as for example —CF$_3$, —CHF$_2$, —CH$_2$F, —CF$_2$CF$_3$, —CHFCF$_3$, —CH$_2$CF$_3$, —CF$_2$CH$_3$, —CHFCH$_3$, —CF$_2$CF$_2$CF$_3$, —CF$_2$CH$_2$CH$_3$, —CF=CF$_2$, —CCl=CH$_2$, —CBr=CH$_2$, —CI=CH$_2$, —C≡C—CF$_3$, —CHFCH$_2$CH$_3$ and —CHFCH$_2$CF$_3$.

"Halogen" includes fluorine, chlorine, bromine and iodine atoms.

"Pseudohalogen" refers to —OCN, —SCN, —CF$_3$, and —CN.

"Cycloalkyl" or "cycloalkyl group" refers to a monoradical non-aromatic carbocyclic ring system, which may be saturated or unsaturated, substituted or unsubstituted, and may be monocyclic, bicyclic, or tricyclic, and may be bridged, spiro, and/or fused. Examples include, but are not limited to, cyclopropyl, cyclopropenyl, cyclobutyl, cyclobutenyl, cyclopentyl, cyclopentenyl, cyclohexyl, cyclohexenyl, norbornyl, norbornenyl, bicyclo[2.2.1]hexane, bicyclo[2.2.1]heptane, bicyclo[2.2.1]heptene, bicyclo[3.1.1]heptane, bicyclo[3.2.1]octane, bicyclo[2.2.2]octane, bicyclo[3.2.2]nonane, bicyclo[3.3.1]nonane, and bicyclo[3.3.2]decane. Preferably, the cycloalkyl group contains from 3 to 10 ring atoms. More preferably, the cycloalkyl group contains from 3 to 7 ring atoms, such as 3 ring atoms, 5 ring atoms, 6 ring atoms, or 7 ring atoms. A cycloalkyl group can also include ring systems substituted on ring carbons with one or more —OH functional groups (which may further tautomerize to give a ring C=O group).

"Cycloalkylene" or "cycloalkylene group" refers to a diradical non-aromatic carbocyclic ring system, which may be saturated or unsaturated, substituted or unsubstituted, and may be monocyclic, bicyclic, or tricyclic, and may be bridged, spiro, and/or fused. Examples include, but are not limited to, the cyclopropylene isomers

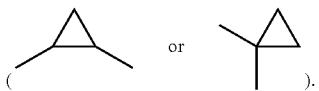

Preferably, the cycloalkylene group contains from 3 to 10 ring atoms. More preferably, the cycloalkylene group contains from 3 to 7 ring atoms, such as 3 ring atoms, 5 ring atoms, 6 ring atoms, or 7 ring atoms. A cycloalkylene group can also include ring systems substituted on ring carbons with one or more —OH functional groups (which may further tautomerize to give a ring C=O group).

"Cycloalkylalkyl" or "cycloalkylalkyl group" refers to an alkyl group in which a hydrogen atom is replaced by a cycloalkyl group, wherein alkyl group and cycloalkyl group are as previously defined (i.e., cycloalkylalkyl-). Cycloalkylalkyl groups can be substituted or unsubstituted. Examples include, but are not limited to, cyclohexylmethyl ($C_6H_{11}CH_2$—).

"Cycloalkylalkylene" or "cycloalkylalkylene group" refers to an alkyl group in which a hydrogen atom is replaced by a cycloalkylene group, wherein alkyl group and cycloalkylene group are as previously defined (i.e., -cycloalkylalkyl-). Cylcloalkylalkylene groups can be substituted or unsubstituted. Examples include, but are not limited to, the cyclopropylmethylene isomers

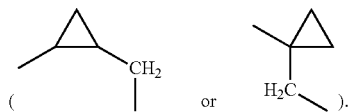

"Aryl" or "aryl group" refers to phenyl and 7-15 membered monoradical bicyclic or tricyclic hydrocarbon ring systems, including bridged, spiro, and/or fused ring systems, in which at least one of the rings is aromatic. Aryl groups can be substituted or unsubstituted. Examples include, but are not limited to, naphthyl, indanyl, 1,2,3,4-tetrahydronaphthalenyl, 6,7,8,9-tetrahydro-5H-benzocycloheptenyl, and 6,7,8,9-tetrahydro-5H-benzocycloheptenyl. Preferably, the aryl group contains 6 (i.e., phenyl) or 9 to 15 ring atoms. More preferably, the aryl group contains 6 (i.e., phenyl), 9 or 10 ring atoms. More preferably, the aryl group contains 6 (i.e., phenyl), or 9-11 ring atoms. An aryl group can also include ring systems substituted on ring carbons with one or more —OH functional groups (which may further tautomerize to give a ring C=O group).

"Arylene" or "arylene group" refers to a phenylene (—$C_6H_4$—) or a 7-15 membered diradical bicyclic or tricyclic hydrocarbon ring systems, including bridged, spiro, and/or fused ring systems, in which at least one of the rings is aromatic. Arylene groups can be substituted or unsubstituted. Preferably, the arylene group contains 6 (i.e., phenylene) or 9 to 15 ring atoms. More preferably, the arylene group contains 6 (i.e., phenylene) or 9-11 ring atoms. More preferably, the arylene group contains 6 (i.e., phenylene), 9 or 10 ring atoms. An arylene group can also include ring systems substituted on ring carbons with one or more —OH functional groups (which may further tautomerize to give a ring C=O group).

"Arylalkyl" or "arylalkyl group" refers to an alkyl group in which a hydrogen atom is replaced by an aryl group, wherein alkyl group and aryl group are as previously defined (i.e., arylalkyl-). Arylalkyl groups can be substituted or unsubstituted. Examples include, but are not limited to, benzyl ($C_6H_5CH_2$—).

"Arylalkylene" or "arylalkylene group" refers to an alkyl group in which a hydrogen atom is replaced by an arylene group, wherein alkyl group and arylene group are as previously defined (i.e., -arylalkyl-). Arylalkylene groups can be substituted or unsubstituted. Examples include, but are not limited to, the benzylene isomers (—$C_6H_4CH_2$—).

"Heterocycloalkyl" or "heterocycloalkyl group" refers to 3-15 membered monocyclic, bicyclic, and tricyclic non-aromatic rings, which may be saturated or unsaturated, can be substituted or unsubstituted, may be bridged, spiro, and/or fused, and which contain, in addition to carbon atom(s), at least one heteroatom, such as nitrogen, oxygen, sulfur or phosphorus. Examples include, but are not limited to, tetrahydrofuranyl, pyrrolidinyl, pyrrolinyl, imidazolidinyl, imidazolinyl, pyrazolidinyl, pyrazolinyl, piperidyl, piperazinyl, indolinyl, isoindolinyl, morpholinyl, thiomorpholinyl, homomorpholinyl, homopiperidyl, homopiperazinyl, thiomorpholinyl-5-oxide, thiomorpholinyl-S,S-dioxide, pyrrolidinyl, tetrahydropyranyl, piperidinyl, tetrahydrothienyl, homopiperidinyl, homothiomorpholinyl-S,S-dioxide, oxazolidinonyl, dihydropyrazolyl, dihydropyrrolyl, dihydropyrazinyl, dihydropyridinyl, dihydropyrimidinyl, dihydrofuryl, dihydropyranyl, tetrahydrothienyl-5-oxide, tetrahydrothienyl-S,S-dioxide, homothiomorpholinyl-5-oxide, quinuclidinyl, 2-oxa-5-azabicyclo[2.2.1]heptane, 8-oxa-3-aza-bicyclo[3.2.1]octane, 3,8-diaza-bicyclo[3.2.1]octane, 2,5-diazabicyclo[2.2.1]heptane, 3,8-diaza-bicyclo[3.2.1]octane, 3,9-diaza-bicyclo[4.2.1]nonane, 2,6-diaza-bicyclo[3.2.2]nonane, [1,4]oxaphosphinane 4-oxide, [1,4]azaphosphinane 4-oxide, [1,2]oxaphospholane 2-oxide, phosphinane 1-oxide, [1,3]azaphospholidine 3-oxide, and [1,3]oxaphospholane 3-oxide. Preferably, the heterocycloalkyl group contains, in addition to carbon atom(s), at least one nitrogen, oxygen, or sulfur. More preferably, the heterocycloalkyl group contains, in addition to carbon atom(s), at least one nitrogen or oxygen. More preferably, the heterocycloalkyl group contains, in addition to carbon atom(s), at least one nitrogen. Preferably, the heterocycloalkyl group contains from 3 to 10 ring atoms. More preferably, the heterocycloalkyl group contains from 3 to 7 ring atoms. More preferably, the heterocycloalkyl group contains from 5 to 7 ring atoms, such as 5 ring atoms, 6 ring atoms, or 7 ring atoms. Unless otherwise indicated, the foregoing heterocycloalkyl groups can be C-attached or N-attached where such is possible and results in the creation of a stable structure. For example, piperidinyl can be piperidin-1-yl (N-attached) or piperidin-4-yl (C-attached). A heterocycloalkyl group can also include ring systems substituted on ring carbons with one or more —OH functional groups (which may further tautomerize to give a ring C=O group) and/or substituted on a ring sulfur atom by one (1) or two (2) oxygen atoms to give S=O or $SO_2$ groups, respectively, and/or substituted on a ring phosphorus by an oxygen atom to give P=O.

"Heterocycloalkylene" or "heterocycloalkylene group" refers to diradical, 3-15 membered monocyclic, bicyclic, or tricyclic non-aromatic ring systems, which may be saturated or unsaturated, can be substituted or unsubstituted, may be bridged, spiro, and/or fused, and which contain, in addition to carbon atom(s), at least one heteroatom, such as nitrogen, oxygen, sulfur or phosphorus. Examples include, but are not limited to, the azridinylene isomers

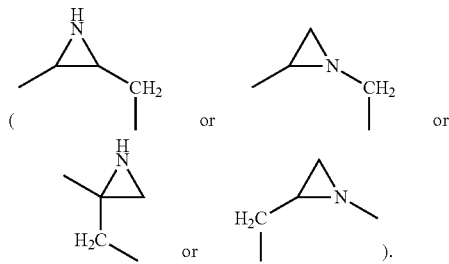

Preferably, the heterocycloalkylene group contains, in addition to carbon atom(s), at least one nitrogen, oxygen, or sulfur. More preferably, the heterocycloalkylene group contains, in addition to carbon atom(s), at least one nitrogen or oxygen. More preferably, the heterocycloalkylene group contains, in addition to carbon atom(s), at least one nitrogen. Preferably, the heterocycloalkylene group contains from 3 to 10 ring atoms. More preferably, the heterocycloalkylene group contains from 3 to 7 ring atoms. More preferably, the heterocycloalkylene group contains from 5 to 7 ring atoms, such as 5 ring atoms, 6 ring atoms, or 7 ring atoms. Unless otherwise indicated, the foregoing heterocycloalkylene groups can be C-attached and/or N-attached where such is possible and results in the creation of a stable structure. A heterocycloalkylene group can also include ring systems substituted on ring carbons with one or more —OH functional groups (which may further tautomerize to give a ring C=O group) and/or substituted on a ring sulfur atom by one (1) or two (2) oxygen atoms to give S=O or $SO_2$ groups, respectively, and/or substituted on a ring phosphorus by an oxygen atom to give P=O.

"Heterocycloalkylalkyl" or "heterocycloalkylalkyl group" refers to an alkyl group in which a hydrogen atom is replaced by a heterocycloalkyl group, wherein alkyl group and heterocycloalkyl group are as previously defined (i.e., heterocycloalkylalkyl-). Heteroycloalkylalkyl groups can be substituted or unsubstituted. Examples include, but are not limited to, pyrrolidinylmethyl ($C_4H_8CH_2$—).

"Heterocycloalkylalkylene" or "heterocycloalkylalkylene group" refers to an alkyl group in which a hydrogen atom is replaced by a heterocycloalkylene group, wherein alkyl group and heterocycloalkylene group are as previously defined (i.e., -heterocycloalkylalkyl-). Heterocylcloalkylalkylene groups can be substituted or unsubstituted. Examples include, but are not limited to, the azrizidinylmethylene isomers

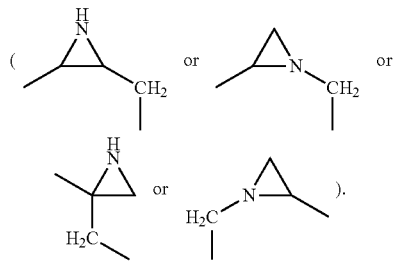

"Heteroaryl" or "heteroaryl group" refers to (a) 5 and 6 membered monocyclic aromatic rings, which contain, in addition to carbon atom(s), at least one heteroatom, such as nitrogen, oxygen or sulfur, and (b) 7-15 membered bicyclic and tricyclic rings, which contain, in addition to carbon atom(s), at least one heteroatom, such as nitrogen, oxygen or sulfur, and in which at least one of the rings is aromatic. Heteroaryl groups can be substituted or unsubstituted, and may be bridged, spiro, and/or fused. Examples include, but are not limited to, 2,3-dihydrobenzofuranyl, 1,2-dihydroquinolinyl, 3,4-dihydroisoquinolinyl, 1,2,3,4-tetrahydroisoquinolinyl, 1,2,3,4-tetrahydroquinolinyl, benzoxazinyl, benzthiazinyl, chromanyl, furanyl, 2-furanyl, 3-furanyl, imidazolyl, isoxazolyl, isothiazolyl, oxadiazolyl, oxazolyl, pyridinyl, 2-, 3-, or 4-pyridinyl, pyrimidinyl, 2-, 4-, or 5-pyrimidinyl, pyrazolyl, pyrrolyl, 2- or 3-pyrrolyl, pyrazinyl, pyridazinyl, 3- or 4-pyridazinyl, 2-pyrazinyl, thienyl, 2-thienyl, 3-thienyl, tetrazolyl, thiazolyl, thiadiazolyl, triazinyl, triazolyl, pyridin-2-yl, pyridin-4-yl, pyrimidin-2-yl, pyridazin-4-yl, pyrazin-2-yl, naphthyridinyl, pteridinyl, phthalazinyl, purinyl, alloxazinyl, benzimidazolyl, benzofuranyl, benzofurazanyl, 2H-1-benzopyranyl, benzothiadiazine, benzothiazinyl, benzothiazolyl, benzothiophenyl, benzoxazolyl, cinnolinyl, furopyridinyl, indolinyl, indolizinyl, indolyl, or 2-, 3-, 4-, 5-, 6-, or 7-indolyl, 3H-indolyl, quinazolinyl, quinoxalinyl, isoindolyl, isoquinolinyl, 10-aza-tricyclo[6.3.1.0*2,7*]dodeca-2(7), 3,5-trienyl, 12-oxa-10-aza-tricyclo[6.3.1.0*2,7*]dodeca-2(7), 3,5-trienyl, 12-aza-tricyclo[7.2.1.0*2,7*]dodeca-2(7), 3,5-trienyl, 10-aza-tricyclo[6.3.2.0*2,7*]trideca-2(7), 3,5-trienyl, 2,3,4,5-tetrahydro-1H-benzo[d]azepinyl, 1,3,4,5-tetrahydro-benzo[d]azepin-2-onyl, 1,3,4,5-tetrahydro-benzo[b]azepin-2-onyl, 2,3,4,5-tetrahydro-benzo[c]azepin-1-onyl, 1,2,3,4-tetrahydro-benzo[e][1,4]diazepin-5-onyl, 2,3,4,5-tetrahydro-1H-benzo[e][1,4]diazepinyl, 5,6,8,9-tetrahydro-7-oxa-benzocycloheptenyl, 2,3,4,5-tetrahydro-1H-benzo[b]azepinyl, 1,2,4,5-tetrahydro-benzo[e][1,3]diazepin-3-onyl, 3,4-dihydro-2H-benzo[b][1,4]dioxepinyl, 3,4-dihydro-2H-benzo[f][1,4]oxazepin-5-onyl, 6,7,8,9-tetrahydro-5-thia-8-aza-benzocycloheptenyl, 5,5-dioxo-6,7,8,9-tetrahydro-5-thia-8-aza-benzocycloheptenyl, and 2,3,4,5-tetrahydro-benzo[f][1,4]oxazepinyl. Preferably, the heteroaryl group contains 5, 6, or 8-15 ring atoms. More preferably, the heteroaryl group contains 5 to 10 ring atoms, such as 5, 6, 9, or 10 ring atoms. A heteroaryl group can also include ring systems substituted on ring carbons with one or more —OH or C=O functional groups and/or substituted on a ring sulfur atom by one (1) or two (2) oxygen atoms to give S=O or $SO_2$ groups, respectively.

"Heteroarylene" or "heteroarylene group" refers to (a) diradical 5 and 6 membered monocyclic aromatic rings, which contain, in addition to carbon atom(s), at least one heteroatom, such as nitrogen, oxygen or sulfur, and (b) diradical 7-15 membered bicyclic and tricyclic rings, which contain, in addition to carbon atom(s), at least one heteroatom, such as nitrogen, oxygen or sulfur, and in which at least one of the rings is aromatic. Heteroarylene groups can be substituted or unsubstituted, and may be bridged, spiro, and/or fused. Preferably, the heteroarylene group contains 5, 6, or 8-15 ring atoms. More preferably, the heteroarylene group contains 5 to 10 ring atoms, such as 5, 6, 9, or 10 ring atoms. A heteroarylene group can also include ring systems substituted on ring carbons with one or more —OH or C=O functional groups and/or substituted on a ring sulfur atom by one (1) or two (2) oxygen atoms to give S=O or $SO_2$ groups, respectively.

"Heteroarylalkyl" or "heteroarylalkyl group" refers to an alkyl group in which a hydrogen atom is replaced by a heteroaryl group, wherein alkyl group and heteroaryl group are as previously defined (i.e., heteroarylalkyl-). Heteroarylalkyl groups can be substituted or unsubstituted. Examples include, but are not limited to, the pyridinylmethyl isomers

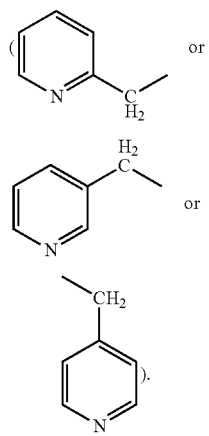

"Heteroarylalkylene" or "heteroarylalkylene group" refers to an alkyl group in which a hydrogen atom is replaced by a heteroarylene group, wherein alkyl group and heteroarylene group are as previously defined (i.e., -heteroarylalkyl-). Heteroarylalkylene groups can be substituted or unsubstituted. Examples include, but are not limited to, the pyridinylmethylene isomers

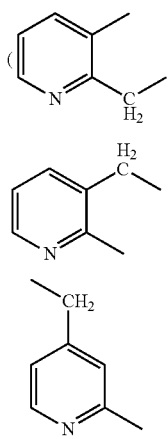

-continued

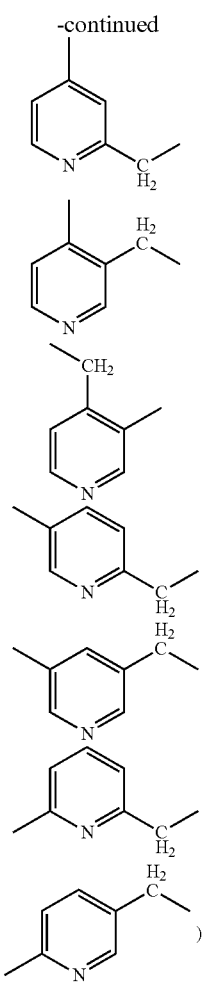

"Chemically stable" or "stable" refers to a compound that is sufficiently robust to be isolated to a useful degree of purity from a reaction mixture. The present invention is directed only to stable compounds.

"Pharmaceutical composition" refers to a composition suitable for administration in medical or veterinary use.

When lists of alternative substituents include members which, owing to valency requirements, chemical stability, or other reasons, cannot be used to substitute a particular group, the list is intended to be read in context to include those members of the list that are suitable for substituting the particular group. For example, when $L^1$ is $C_{1-6}$alkylene optionally substituted by 1-12 $R^9$, and the $C_{1-6}$-alkylene group is methylene, the methylene group is optionally substituted by 1 or 2 $R^9$.

"Functionalized derivative" refers to a compound that contains at least one additional functional group as compared to a reference compound. An example of a functionalized derivative of benzene is bromobenzene. An example of a functionalized derivative of bromobenzene is 2-bromophenol. Functional groups include, but are not limited to, halogen, nitro, hydroxy, alkoxy, aryloxy, ketone, ester, amide, amino, alkylamino, alkyl, double bond, triple bond, alkoxyalkyl, aminoalkyl, haloalkyl, alkenyl, alkynyl, aryl, heteroaryl, cycloalkyl, heterocycloalkyl, pseudohalogen, alkylthio, sulfonyl, alkylsulfonyl, alkylaminosulfonyl, alkylcarbonyloxy, aminocarbonyloxy, alkylaminocarbonyloxy, alkylcarbonylamino, alkoxycarbonylamino, alkylsulfonylamino, aminocarbonylamino, and alkylaminocarbonylamino functional group, and derivatives of these and other functional groups in which a heteroatom is derivatized with a removable protecting group.

"Pharmaceutically acceptable" refers to physiologically tolerable materials, which do not typically produce an allergic or other untoward reaction, such as gastric upset, dizziness and the like, when administered to a mammal.

"Therapeutically effective amount" refers to an amount of a compound, or a pharmaceutically acceptable salt thereof, sufficient to inhibit, halt, or cause an improvement in a disorder or condition being treated in a particular subject or subject population. For example in a human or other mammal, a therapeutically effective amount can be determined experimentally in a laboratory or clinical setting, or may be the amount required by the guidelines of the United States Food and Drug Administration, or equivalent foreign agency, for the particular disease and subject being treated.

It should be appreciated that determination of proper dosage forms, dosage amounts, and routes of administration is within the level of ordinary skill in the pharmaceutical and medical arts, and is described below.

"Subject" refers to a member of the class Mammalia. Examples of mammals include, without limitation, humans, primates, chimpanzees, rodents, mice, rats, rabbits, horses, livestock, dogs, cats, sheep, and cows.

"Treatment" refers to the acute or prophylactic diminishment or alleviation of at least one symptom or characteristic associated or caused by a disorder being treated. For example, treatment can include diminishment of several symptoms of a disorder or complete eradication of a disorder.

"Administering" refers to the method of contacting a compound with a subject. Modes of "administering" include, but are not limited to, methods that involve contacting the compound intravenously, intraperitoneally, intranasally, transdermally, topically, via implantation, subcutaneously, parentally, intramuscularly, orally, systemically, and via adsorption.

II. Compounds

The present invention provides a compound of formula (I)

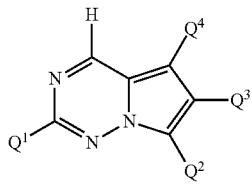

(I)

or a pharmaceutically acceptable salt form thereof,
wherein
$Q^1$ is -$L^1$-$A^1$-$G^1$-$X^1$—$Z^1$;
$Q^2$ is -$L^2$-$A^2$-$G^2$-$X^2$—$Z^2$;
$Q^3$ is -$L^3$-$A^3$-$G^3$-$X^3$—$Z^3$;
$Q^4$ is -$L^4$-$A^4$-$G^4$-$X^4$—$Z^4$;
$L^1$ is $C_{1-6}$alkylene optionally substituted by 1-12 $R^9$, $C_{2-6}$alkenylene optionally substituted by 1-10 $R^9$, $C_{2-6}$alkynylene optionally substituted by 1-8 $R^9$, $C_{6-11}$arylene optionally substituted by 1-10 $R^9$, $C_{7-16}$arylalkylene optionally substituted by 1-18 $R^9$, $C_{3-11}$cycloalkylene optionally substituted by 1-20 $R^9$, $C_{4-17}$cycloalkylalkylene optionally substituted by 1-31 $R^9$, 3-15 membered heterocycloalkylene optionally substituted by 1-27 $R^9$, 4-21 membered heterocycloalkylalkylene optionally substituted by 1-39 $R^9$, 5-15 membered heteroarylene optionally substituted by 1-14 $R^9$, 6-21 membered heteroarylalkylene optionally substituted by 1-26 $R^9$, —$C_{0-3}$alkylC(=O)$C_{0-3}$alkyl-, —$C_{0-3}$alkylC(=O)OC$_{0-3}$alkyl-, —$C_{0-3}$alkylC(=O)NR$^4$C$_{0-3}$alkyl-, —$C_{0-3}$alkylC(=O)C(=O)C$_{0-3}$alkyl-, —$C_{0-3}$alkylC(=NR$^5$)C$_{0-3}$alkyl-, —$C_{0-3}$alkylC(=NR$^5$)NR$^4$C$_{0-3}$alkyl-, —$C_{0-3}$alkylC(=NOH)NR$^4$C$_{0-3}$alkyl-, —$C_{0-3}$alkylC(=NOR$^6$)C$_{0-3}$alkyl-, —$C_{0-3}$alkylC(=NNR$^2$R$^3$)C$_{0-3}$alkyl-, —$C_{0-3}$alkylC(=NNR$^4$C(=O)R$^1$)C$_{0-3}$alkyl-, —$C_{0-3}$alkylC(=NNR$^4$C(=O)OR$^1$)C$_{0-3}$alkyl-, —$C_{0-3}$alkylC(=S)NR$^4$C$_{0-3}$alkyl-, —$C_{0-3}$alkylNR$^4$C$_{0-3}$alkyl-, —$C_{0-3}$alkylNR$^4$NR$^4$C$_{0-3}$alkyl-, —$C_{0-3}$alkylN=NC$_{0-3}$alkyl-, —$C_{0-3}$alkylNR$^4$C(=O)C$_{0-3}$alkyl-, —$C_{0-3}$alkylNR$^4$C(=O)C(=O)C$_{0-3}$alkyl-, —$C_{0-3}$alkylNR$^4$C(=O)OC$_{0-3}$alkyl-, —$C_{0-3}$alkylNR$^4$C(=O)C(=O)OC$_{0-3}$alkyl-, —$C_{0-3}$alkylNR$^4$C(=O)NR$^4$C$_{0-3}$alkyl-, —$C_{0-3}$alkylNR$^4$C(=O)NR$^4$C(=O)C$_{0-3}$ alkyl-, —$C_{0-3}$alkylNR$^4$C(=O)NR$^4$C(=O)OC$_{0-3}$ alkyl-, —$C_{0-3}$alkylNR$^4$C(=NR$^5$)NR$^4$C$_{0-3}$alkyl-, —$C_{0-3}$ alkylNR$^4$C(=O)C(=O)NR$^4$C$_{0-3}$alkyl-, —$C_{0-3}$alkylNR$^4$C(=S)C$_{0-3}$alkyl-, —$C_{0-3}$alkylNR$^4$C(=S) OC$_{0-3}$alkyl-, —$C_{0-3}$alkylNR$^4$C(=S)NR$^4$C$_{0-3}$alkyl-, —$C_{0-3}$alkylNR$^4$S(=O)$_2$C$_{0-3}$alkyl-, —$C_{0-3}$alkylNR$^4$S(=O)$_2$NR$^4$C$_{0-3}$alkyl-, —$C_{0-3}$alkylOC$_{0-3}$alkyl-, —$C_{0-3}$alkylOC(=O)C$_{0-3}$alkyl-, —$C_{0-3}$alkylOC(=O) NR$^4$C$_{0-3}$ alkyl-, —$C_{0-3}$alkylOC(=O)OC$_{0-3}$alkyl-, —$C_{0-3}$alkylOC(=NR$^5$)NR$^4$C$_{0-3}$alkyl-, —$C_{0-3}$alkylOS(=O)C$_{0-3}$ alkyl-, —$C_{0-3}$alkylOS(=O)$_2$C$_{0-3}$alkyl-, —$C_{0-3}$ alkylOS(=O)$_2$OC$_{0-3}$alkyl-, —$C_{0-3}$alkylOS(=O)$_2$ NR$^4$C$_{0-3}$alkyl-, —$C_{0-3}$alkylS(=O)$_n$C$_{0-3}$alkyl-, —$C_{0-3}$alkylS(=O)$_2$OC$_{0-3}$alkyl-, —$C_{0-3}$alkylSO$_3$C$_{0-3}$ alkyl-, —$C_{0-3}$alkylS(=O)$_2$NR$^4$C$_{0-3}$alkyl-, —$C_{0-3}$alkylS(=O)NR$^4$C$_{0-3}$alkyl-, or absent;

$A^1$ is $C_{1-6}$alkylene optionally substituted by 1-12 $R^a$, $C_{2-6}$alkenylene optionally substituted by 1-10 $R^a$, $C_{2-6}$alkynylene optionally substituted by 1-8 $R^a$, $C_{6-11}$arylene optionally substituted by 1-10 $R^a$, $C_{7-16}$arylalkylene optionally substituted by 1-18 $R^a$, $C_{3-11}$cycloalkylene optionally substituted by 1-20 $R^a$, $C_{4-17}$cycloalkylalkylene optionally substituted by 1-31 $R^a$, 3-15 membered heterocycloalkylene optionally substituted by 1-27 $R^a$, 4-21 membered heterocycloalkylalkylene optionally substituted by 1-39 $R^a$, 5-15 membered heteroarylene optionally substituted by 1-14 $R^a$, 6-21 membered heteroarylalkylene optionally substituted by 1-26 $R^a$, wherein each $R^a$ is independently chosen from $C_{1-6}$alkyl optionally substituted by 1-13 $R^{19}$, $C_{2-6}$alkenyl optionally substituted by 1-11 $R^{19}$, $C_{2-6}$alkynyl optionally substituted by 1-9 $R^{19}$, $C_{6-11}$ aryl optionally substituted by 1-11 $R^{19}$, $C_{7-16}$arylalkyl optionally substituted by 1-19 $R^{19}$, $C_{3-11}$cycloalkyl optionally substituted by 1-21 $R^{19}$, $C_{4-17}$cycloalkylalkyl optionally substituted by 1-32 $R^{19}$, 3-15 membered heterocycloalkyl optionally substituted by 1-28 $R^{19}$, 4-21 membered heterocycloalkylalkyl optionally substituted by 1-40 $R^{19}$, 5-15 membered heteroaryl optionally substituted by 1-15 $R^{19}$, 6-21 membered heteroarylalkyl optionally substituted by 1-27 $R^{19}$, halogen, —CN, —C(=O)R$^{10}$, —C(=O)OR$^{10}$, —C(=O)NR$^{12}$R$^{13}$, —C(=O)C(=O)R$^{10}$, —C(=NR$^{15}$)R$^{10}$, —C(=NR$^{15}$)NR$^{12}$R$^{13}$, —C(=NOH)NR$^{12}$R$^{13}$, —C(=NOR$^{16}$)R$^{10}$, —C(=NNR$^{12}$R$^{13}$)R$^{10}$, —C(=NNR$^{14}$C(=O)R$^{11}$) R$^{10}$, —C(=NNR$^{14}$C(=O)OR$^{11}$)R$^{10}$, —C(=S) NR$^{12}$R$^{13}$, —NC, —NO$_2$, —NR$^{12}$R$^{13}$, —NR$^{14}$NR$^{12}$R$^{13}$, —N=NR$^{14}$, =NR$^{10}$, =NOR$^{10}$, —NR$^{14}$OR$^{16}$, —NR$^{14}$C(=O)R$^{10}$, —NR$^{14}$C(=O)C(=O)R$^{10}$, —NR$^{14}$C(=O)OR$^{11}$, —NR$^{14}$C(=O)C(=O)OR$^{11}$, —NR$^{14}$C(=O)NR$^{12}$R$^{13}$, —NR$^{14}$C(=NR$^{14}$C(=O)R$^{10}$, —NR$^{14}$C(=O)NR$^{14}$C(=O)OR$^{10}$, —NR$^{14}$C(=NR$^{15}$)NR$^{12}$R$^{13}$, —NR$^{14}$C(=O)C(=O)NR$^{12}$R$^{13}$, —NR$^{14}$C(=S)R$^{10}$, —NR$^{14}$S(=S)OR$^{10}$, —NR$^{14}$C(=S)NR$^{12}$R$^{13}$, —NR$^{14}$S(=O)$_2$R$^{11}$, —NR$^{14}$S(=O)$_2$NR$^{12}$R$^{13}$, —NR$^{14}$P(=O)R$^{18}$R$^{18}$, —NR$^{14}$P(=O)(NR$^{12}$R$^{13}$)(NR$^{12}$R$^{13}$), —NR$^{14}$P(=O)(OR$^{10}$)(OR$^{10}$), —NR$^{14}$P(=O)(SR$^{10}$)(SR$^{10}$), —OR$^{10}$, =O, —OCN, —OC(=O)R$^{10}$, —OC(=O)NR$^{12}$R$^{13}$, —OC(=O)OR$^{10}$, —OC(=NR$^{15}$)NR$^{12}$R$^{13}$, —OS(=O)R$^{10}$, —OS(=O)$_2$R$^{10}$, —OS(=O)$_2$OR$^{10}$, —OS(=O)$_2$NR$^{12}$R$^{13}$, —OP(=O)R$^{18}$R$^{18}$, —OP(=O)(NR$^{12}$R$^{13}$)(NR$^{12}$R$^{13}$), —OP(=O)(OR$^{10}$)(OR$^{10}$), —OP(=O)(SR$^{10}$(SR$^{10}$), —SCN, =S, —S(=O)$_n$R$^{10}$, —S(=O)$_2$OR$^{10}$, —SO$_3$R$^{17}$, —S(=O)$_2$NR$^{12}$R$^{13}$, —S(=O)NR$^{12}$R$^{13}$, —SP(=O)R$^{18}$R$^{18}$, —SP(=O)(NR$^{12}$R$^{13}$)(NR$^{12}$R$^{13}$), —SP(=O)(OR$^{10}$)(OR$^{10}$), —SP(=O)(SR$^{10}$)(SR$^{10}$), —P(=O)R$^{18}$R$^{18}$, —P(=O)(NR$^{12}$R$^{13}$)(NR$^{12}$R$^{13}$), —P(=O)(OR$^{10}$)(OR$^{10}$), and —P(=O)(SR$^{10}$)(SR$^{10}$);

G$^1$ is C$_{1-6}$alkylene optionally substituted by 1-12 R$^{29}$, C$_{2-6}$alkenylene optionally substituted by 1-10 R$^{29}$, C$_{2-6}$alkynylene optionally substituted by 1-8 R$^{29}$, C$_{6-11}$arylene optionally substituted by 1-10 R$^{29}$, C$_{7-16}$arylalkylene optionally substituted by 1-18 R$^{29}$, C$_{3-11}$cycloalkylene optionally substituted by 1-20 R$^{29}$, C$_{4-17}$cycloalkylalkylene optionally substituted by 1-31 R$^{29}$, 3-15 membered heterocycloalkylene optionally substituted by 1-27 R$^{29}$, 4-21 membered heterocycloalkylalkylene optionally substituted by 1-39 R$^{29}$, 5-15 membered heteroarylene optionally substituted by 1-14 R$^{29}$, 6-21 membered heteroarylalkylene optionally substituted by 1-26 R$^{29}$, —C$_{0-3}$alkylC(=O)C$_{0-3}$alkyl-, —C$_{0-3}$alkylC(=O)OC$_{0-3}$alkyl-, —C$_{0-3}$alkylC(=O)NR$^{24}$C$_{0-3}$alkyl-, —C$_{0-3}$alkylC(=O)C(=O)C$_{0-3}$alkyl-, —C$_{0-3}$alkylC(=NR$^{25}$)C$_{0-3}$alkyl-, —C$_{0-3}$alkylC(=NR$^{25}$)NR$^{24}$C$_{0-3}$alkyl-, —C$_{0-3}$alkylC(=NOH)NR$^{24}$C$_{0-3}$alkyl-, —C$_{0-3}$alkylC(=NOR$^{26}$)C$_{0-3}$alkyl-, —C$_{0-3}$alkylC(=NNR$^{22}$R$^{23}$)C$_{0-3}$alkyl-, —C$_{0-3}$alkylC(=NNR$^{24}$C(=O)R$^{21}$)C$_{0-3}$alkyl-, —C$_{0-3}$alkylC(=NNR$^{24}$C(=O)OR$^{21}$)C$_{0-3}$alkyl-, —C$_{0-3}$alkylC(=S)NR$^{24}$C$_{0-3}$alkyl-, —C$_{0-3}$alkylNR$^{24}$C$_{0-3}$alkyl-, —C$_{0-3}$alkylNR$^{24}$NR$^{24}$C$_{0-3}$alkyl-, —C$_{0-3}$alkylN=NC$_{0-3}$alkyl-, —C$_{0-3}$alkylNR$^{24}$C(=O)C$_{0-3}$alkyl-, —C$_{0-3}$alkylNR$^{24}$C(=O)C(=O)C$_{0-3}$alkyl-, —C$_{0-3}$alkylNR$^{24}$C(=O)OC$_{0-3}$alkyl-, —C$_{0-3}$alkylNR$^{24}$C(=O)C(=O)OC$_{0-3}$alkyl-, —C$_{0-3}$alkylNR$^{24}$C(=O)NR$^{24}$C$_{0-3}$alkyl-, —C$_{0-3}$alkylNR$^{24}$C(=O)NR$^{24}$C(=O)C$_{0-3}$alkyl-, —C$_{0-3}$alkylNR$^{24}$C(=O)NR$^{24}$C(=O)OC$_{0-3}$alkyl-, —C$_{0-3}$alkylNR$^{24}$C(=NR$^{25}$)NR$^{24}$C$_{0-3}$alkyl-, —C$_{0-3}$alkylNR$^{24}$C(=O)C(=O)NR$^{24}$C$_{0-3}$alkyl-, —C$_{0-3}$alkylNR$^{24}$C(=S)C$_{0-3}$alkyl-, —C$_{0-3}$alkylNR$^{24}$C(=S)OC$_{0-3}$alkyl-, —C$_{0-3}$alkylNR$^{24}$C(=S)NR$^{24}$C$_{0-3}$alkyl-, —C$_{0-3}$alkylNR$^{24}$S(=O)$_2$C$_{0-3}$alkyl-, —C$_{0-3}$alkylNR$^{24}$S(=O)$_2$NR$^{24}$C$_{0-3}$alkyl-, —C$_{0-3}$alkylOC$_{0-3}$alkyl-, —C$_{0-3}$alkylOC(=O)C$_{0-3}$alkyl-, —C$_{0-3}$alkylOC(=O)NR$^{24}$C$_{0-3}$alkyl-, —C$_{0-3}$alkylOC(=O)OC$_{0-3}$alkyl-, —C$_{0-3}$alkylOC(=NR$^{25}$)NR$^{24}$C$_{0-3}$alkyl-, —C$_{0-3}$alkylOS(=O)C$_{0-3}$alkyl-, —C$_{0-3}$alkylOS(=O)$_2$C$_{0-3}$alkyl-, —C$_{0-3}$alkylOS(=O)$_2$OC$_{0-3}$alkyl-, —C$_{0-3}$alkylOS(=O)$_2$NR$^{24}$C$_{0-3}$alkyl-, —C$_{0-3}$alkylS(=O)$_n$C$_{0-3}$alkyl-, —C$_{0-3}$alkylS(=O)$_2$OC$_{0-3}$alkyl-, —C$_{0-3}$alkylSO$_3$C$_{0-3}$alkyl-, —C$_{0-3}$alkylS(=O)$_2$NR$^{24}$C$_{0-3}$alkyl-, —C$_{0-3}$alkylS(=O)NR$^{24}$C$_{0-3}$alkyl-, or absent;

X$^1$ is C$_{1-6}$alkylene optionally substituted by 1-12 R$^{39}$, C$_{2-6}$alkenylene optionally substituted by 1-10 R$^{39}$, C$_{2-6}$alkynylene optionally substituted by 1-8 R$^{39}$, C$_{6-11}$arylene optionally substituted by 1-10 R$^{39}$, C$_{7-16}$arylalkylene optionally substituted by 1-18 R$^{39}$, C$_{3-11}$cycloalkylene optionally substituted by 1-20 R$^{39}$, C$_{4-17}$cycloalkylalkylene optionally substituted by 1-31 R$^{39}$, 3-15 membered heterocycloalkylene optionally substituted by 1-27 R$^{39}$, 4-21 membered heterocycloalkylalkylene optionally substituted by 1-39 R$^{39}$, 5-15 membered heteroarylene optionally substituted by 1-14 R$^{39}$, 6-21 membered heteroarylalkylene optionally substituted by 1-26 R$^{39}$, —C$_{0-3}$alkylC(=O)C$_{0-3}$alkyl-, —C$_{0-3}$alkylC(=O)OC$_{0-3}$alkyl-, —C$_{0-3}$alkylC(=O)NR$^{34}$C$_{0-3}$alkyl-, —C$_{0-3}$alkylC(=O)C(=O)C$_{0-3}$alkyl-, —C$_{0-3}$alkylC(=NR$^{35}$)C$_{0-3}$alkyl-, —C$_{0-3}$alkylC(=NR$^{35}$)NR$^{34}$C$_{0-3}$alkyl-, —C$_{0-3}$alkylC(=NOH)NR$^{34}$C$_{0-3}$alkyl-, —C$_{0-3}$alkylC(=NOR$^{36}$)C$_{0-3}$alkyl-, —C$_{0-3}$alkylC(=NNR$^{32}$R$^{33}$)C$_{0-3}$alkyl-, —C$_{0-3}$alkylC(=NNR$^{34}$C(=O)R$^{31}$)C$_{0-3}$alkyl-, —C$_{0-3}$alkylC(=NNR$^{34}$C(=O)OR$^{31}$)C$_{0-3}$alkyl-, —C$_{0-3}$alkylC(=S)NR$^{34}$C$_{0-3}$alkyl-, —C$_{0-3}$alkylNR$^{34}$C$_{0-3}$alkyl-, —C$_{0-3}$alkylNR$^{34}$NR$^{34}$C$_{0-3}$alkyl-, —C$_{0-3}$alkylN=NC$_{0-3}$alkyl-, —C$_{0-3}$alkylNR$^{34}$C(=O)C$_{0-3}$alkyl-, —C$_{0-3}$alkylNR$^{34}$C(=O)C(=O)C$_{0-3}$alkyl-, —C$_{0-3}$alkylNR$^{34}$C(=O)OC$_{0-3}$alkyl-, —C$_{0-3}$alkylNR$^{34}$C(=O)C(=O)OC$_{0-3}$alkyl-, —C$_{0-3}$alkylNR$^{34}$C(=O)NR$^{34}$C$_{0-3}$alkyl-, —C$_{0-3}$alkylNR$^{34}$C(=O)NR$^{34}$C(=O)C$_{0-3}$alkyl-, —C$_{0-3}$alkylNR$^{34}$C(=O)NR$^{34}$C(=O)OC$_{0-3}$alkyl-, —C$_{0-3}$alkylNR$^{34}$C(=NR$^{35}$)NR$^{34}$C$_{0-3}$alkyl-, —C$_{0-3}$alkylNR$^{34}$C(=O)C(=O)NR$^{34}$C$_{0-3}$alkyl-, —C$_{0-3}$alkylNR$^{34}$C(=S)C$_{0-3}$alkyl-, —C$_{0-3}$alkylNR$^{34}$C(=S)OC$_{0-3}$alkyl-, —C$_{0-3}$alkylNR$^{34}$C(=S)NR$^{34}$C$_{0-3}$alkyl-, —C$_{0-3}$alkylNR$^{34}$S(=O)$_2$C$_{0-3}$alkyl-, —C$_{0-3}$alkylNR$^{34}$S(=O)$_2$NR$^{34}$C$_{0-3}$alkyl-, —C$_{0-3}$alkylOC$_{0-3}$alkyl-, —C$_{0-3}$alkylOC(=O)C$_{0-3}$alkyl-, —C$_{0-3}$alkylOC(=O)NR$^{34}$C$_{0-3}$alkyl-, —C$_{0-3}$alkylOC(=O)OC$_{0-3}$alkyl-, —C$_{0-3}$alkylOC(=NR$^{35}$)NR$^{34}$C$_{0-3}$alkyl-, —C$_{0-3}$alkylOS(=O)C$_{0-3}$alkyl-, —C$_{0-3}$alkylOS(=O)$_2$C$_{0-3}$alkyl-, —C$_{0-3}$alkylOS(=O)$_2$OC$_{0-3}$alkyl-, —C$_{0-3}$alkylOS(=O)$_2$NR$^{34}$C$_{0-3}$alkyl-, —C$_{0-3}$alkylS(=O)$_n$C$_{0-3}$alkyl-, —C$_{0-3}$alkylS(=O)$_2$OC$_{0-3}$alkyl-, —C$_{0-3}$alkylSO$_3$C$_{0-3}$alkyl-, —C$_{0-3}$alkylS(=O)$_2$NR$^{34}$C$_{0-3}$alkyl-, —C$_{0-3}$alkylS(=O)NR$^{34}$C$_{0-3}$alkyl-, or absent;

Z$^1$ is H, C$_{1-6}$alkyl optionally substituted by 1-13 R$^{49}$, C$_{2-6}$alkenyl optionally substituted by 1-11 R$^{49}$, C$_{2-6}$alkynyl optionally substituted by 1-9 R$^{49}$, C$_{6-11}$aryl optionally substituted by 1-11 R$^{49}$, C$_{7-16}$arylalkyl optionally substituted by 1-19 R$^{49}$, C$_{3-11}$cycloalkyl optionally substituted by 1-21 R$^{49}$, C$_{4-17}$cycloalkylalkyl optionally substituted by 1-32 R$^{49}$, 3-15 membered heterocycloalkyl optionally substituted by 1-28 R$^{49}$, 4-21 membered heterocycloalkylalkyl optionally substituted by 1-40 R$^{49}$, 5-15 membered heteroaryl optionally substituted by 1-15 R$^{49}$, 6-21 membered heteroarylalkyl optionally substituted by 1-27 R$^{49}$, halogen, —CN, —C(=O)R$^{100}$, —C(=O)OR$^{100}$, —C(=O)NR$^{102}$R$^{103}$, —C(=O)C(=O)R$^{100}$, —C(=NR$^{105}$)R$^{100}$, —C(NR$^{105}$)NR$^{102}$R$^{103}$, —C(=NOH)NR$^{102}$R$^{103}$, —C(=NOR$^{106}$)R$^{100}$, —C(=NNR$^{102}$R$^{103}$)R$^{100}$, —C(=NNR$^{104}$C(=O)R$^{101}$)R$^{100}$, —C(=NNR$^{104}$C(=O)OR$^{101}$)R$^{100}$, —C(=S)NR$^{102}$R$^{103}$, —NC, —NO$_2$, —NR$^{102}$R$^{103}$, —NR$^{104}$NR$^{102}$R$^{103}$, —N=NR$^{104}$, =NR$^{100}$, =NOR$^{100}$, —NR$^{104}$OR$^{106}$, —NR$^{104}$C(=O)R$^{100}$, —NR$^{104}$C(=O)C(=O)R$^{100}$, —NR$^{104}$C(=O)OR$^{101}$, —NR$^{104}$C(=O)C(=O) OR$^{101}$, —NR$^{104}$C(=O)NR$^{102}$R$^{103}$, —NR$^{104}$C(=O) NR$^{104}$C(=O)R$^{100}$, —NR$^{104}$C(=O)NR$^{104}$C(=O) OR$^{100}$, —NR$^{104}$C(=NR$^{105}$)NR$^{102}$R$^{103}$, —NR$^{104}$C (=O)C(=O)NR$^{102}$R$^{103}$, —NR$^{104}$C(=S)R$^{100}$, —NR$^{104}$C(=S)OR$^{100}$, —NR$^{104}$C(=S)NR$^{102}$R$^{103}$, —NR$^{104}$S(=O)$_2$R$^{101}$, —NR$^{104}$S(=O)$_2$NR$^{102}$R$^{103}$, —NR$^{104}$P(=O)R$^{108}$R$^{108}$, —NR$^{104}$P(=O) (NR$^{102}$R$^{103}$)(R$^{102}$R$^{103}$), —NR$^{104}$P(=O)(OR$^{100}$) (OR$^{100}$), —NR$^{104}$P(=O)(SR$^{100}$)(SR$^{100}$), —OR$^{100}$, =O, —OCN, —OC(=O)R$^{100}$, —OC(=O) NR$^{102}$R$^{103}$, —OC(=O)OR$^{100}$, —OC(=NR$^{105}$) NR$^{102}$R$^{103}$, —OS(=O)R$^{100}$, —OS(=O)$_2$R$^{100}$, —OS (=O)$_2$OR$^{100}$, —OS(=O)$_2$NR$^{102}$R$^{103}$, —OP(=O) R$^{108}$R$^{108}$, —OP(=O)(NR$^{102}$R$^{103}$)(NR$^{102}$R$^{103}$), —OP (=O)(OR$^{100}$)(OR$^{100}$), —OP(=O)(SR$^{100}$)(SR$^{100}$), —SCN, =S, —S(=O)$_n$R$^{100}$, —S(=O)$_2$OR$^{100}$, —SO$_3$R$^{107}$, —S(=O)$_2$NR$^{102}$R$^{103}$, —S(=O) NR$^{102}$R$^{103}$, —SP(=O)R$^{108}$R$^{108}$, —SP(=O) (NR$^{102}$R$^{103}$)(NR$^{102}$R$^{103}$), —SP(=O)(OR$^{100}$)(OR$^{100}$), —SP(=O)(SR$^{100}$)(SR$^{100}$), —P(=O)R$^{108}$R$^{108}$, —P(=O)(NR$^{102}$R$^{103}$)(NR$^{102}$R$^{103}$), —P(=O)(OR$^{100}$) (OR$^{100}$), or —P(=O)(SR$^{100}$)(SR$^{100}$);

L$^2$, L$^3$, and L$^4$ are independently present or absent, and if present each is independently chosen from —C$_{0-3}$alkylC(=O)C$_{0-3}$alkyl-, —C$_{0-3}$alkylC(=O)OC$_{0-3}$alkyl-, —C$_{0-3}$alkylC(=O)NR$^{44}$C$_{0-3}$alkyl-, —C$_{0-3}$alkylC(=O)C(=O)C$_{0-3}$alkyl-, —C$_{0-3}$alkylC(=NR$^{45}$)C$_{0-3}$alkyl-, —C$_{0-3}$alkylC(=NR$^{45}$)NR$^{44}$C$_{0-3}$ alkyl-, —C$_{0-3}$alkylC(=NOH)NR$^{44}$C$_{0-3}$alkyl-, —C$_{0-3}$ alkylC(=NOR$^{46}$)C$_{0-3}$alkyl-, —C$_{0-3}$alkylC(=NNR$^{42}$R$^{43}$)C$_{0-3}$ alkyl-, —C$_{0-3}$alkylC(=NNR$^{44}$C(=O)R$^{41}$)C$_{0-3}$ lkyl-, —C$_{0-3}$alkylC(=NNR$^{44}$C(=O)OR$^{41}$)C$_{0-3}$ lkyl-, —C$_{0-3}$ alkylC(=S)NR$^{44}$C$_{0-3}$alkyl-, —C$_{0-3}$alkylNR$^{44}$C$_{0-3}$ alkyl-, —C$_{0-3}$alkylNR$^{44}$NR$^{44}$C$_{0-3}$ alkyl-, —C$_{0-3}$ alkylN=NC$_{0-3}$alkyl-, —C$_{0-3}$alkylNR$^{44}$C(=O)C$_{0-3}$ alkyl-, —C$_{0-3}$alkylNR$^{44}$C(=O)C(=O)C$_{0-3}$alkyl-, —C$_{0-3}$alkylNR$^{44}$C(=O)OC$_{0-3}$ lkyl-, —C$_{0-3}$ alkylNR$^{44}$C(=O)C(=O)OC$_{0-3}$alkyl-, —C$_{0-3}$ alkylNR$^{44}$C(=O)NR$^{44}$C$_{0-3}$alkyl-, —C$_{0-3}$ alkylNR$^{44}$C(=O)NR$^{44}$C(=O)C$_{0-3}$alkyl-, —C$_{0-3}$ alkylNR$^{44}$C(=O)NR$^{44}$C(=O)OC$_{0-3}$alkyl-, —C$_{0-3}$ alkylNR$^{44}$C(=NR$^{45}$)NR$^{44}$C$_{0-3}$alkyl-, —C$_{0-3}$ alkylNR$^{44}$C(=O)C(=O)NR$^{44}$C$_{0-3}$alkyl-, —C$_{0-3}$ alkylNR$^{44}$C(=S)C$_{0-3}$alkyl-, —C$_{0-3}$alkylNR$^{44}$C(=S) OC$_{0-3}$alkyl-, —C$_{0-3}$alkylNR$^{44}$C(=S)NR$^{44}$C$_{0-3}$alkyl-, —C$_{0-3}$alkylNR$^{44}$S(=O)$_2$C$_{0-3}$alkyl-, —C$_{0-3}$ alkylNR$^{44}$S(=O)$_2$NR$^{44}$C$_{0-3}$alkyl-, —C$_{0-3}$alkylOC$_{0-3}$ alkyl-, —C$_{0-3}$alkylOC(=O)C$_{0-3}$alkyl-, —C$_{0-3}$alkylOC (=O)NR$^{44}$C$_{0-3}$alkyl-, —C$_{0-3}$alkylOC(=O)OC$_{0-3}$ alkyl-, —C$_{0-3}$alkylOC(=NR$^{45}$)NR$^{44}$C$_{0-3}$alkyl-, —C$_{0-3}$ alkylOS(=O)C$_{0-3}$alkyl-, —C$_{0-3}$alkylOS(=O)$_2$C$_{0-3}$ alkyl-, —C$_{0-3}$alkylOS(=O)$_2$OC$_{0-3}$alkyl-, —C$_{0-3}$ alkylOS(=O)$_2$NR$^{44}$C$_{0-3}$alkyl-, —C$_{0-3}$alkylS(=O)—C$_{0-3}$ alkyl-, —C$_{0-3}$alkylS(=O)$_2$OC$_{0-3}$alkyl-, —C$_{0-3}$ alkylSO$_3$C$_{0-3}$alkyl-, —C$_{0-3}$alkylS(=O)$_2$NR$^{44}$C$_{0-3}$ alkyl-, and —C$_{0-3}$alkylS(=O)NR$^{44}$C$_{0-3}$alkyl-;

A$^2$, A$^3$, and A$^4$ are independently present or absent, and if present each is independently chosen from C$_{1-6}$alkylene optionally substituted by 1-12 R$^b$, C$_{2-6}$alkenylene optionally substituted by 1-10 R$^b$, C$_{2-6}$alkynylene optionally substituted by 1-8 R$^b$, C$_{6-11}$arylene optionally substituted by 1-10 R$^b$, C$_{7-16}$arylalkylene optionally substituted by 1-18 R$^b$, C$_{3-11}$cycloalkylene optionally substituted by 1-20 R$^b$, C$_{4-17}$cycloalkylalkylene optionally substituted by 1-31 R$^b$, 3-15 membered heterocycloalkylene optionally substituted by 1-27 R$^b$, 4-21 membered heterocycloalkylalkylene optionally substituted by 1-39 R$^b$, 5-15 membered heteroarylene optionally substituted by 1-14 R$^b$, or 6-21 membered heteroarylalkylene optionally substituted by 1-26 R$^b$;

wherein each R$^b$ is independently chosen from C$_{1-6}$alkyl optionally substituted by 1-13 R$^{59}$, C$_{2-6}$alkenyl optionally substituted by 1-11 R$^{59}$, C$_{2-6}$alkynyl optionally substituted by 1-9 R$^{59}$, C$_{6-11}$aryl optionally substituted by 1-11 R$^{59}$, C$_{7-16}$arylalkyl optionally substituted by 1-19 R$^{59}$, C$_{3-11}$cycloalkyl optionally substituted by 1-21 R$^{59}$, C$_{4-17}$cycloalkylalkyl optionally substituted by 1-32 R$^{59}$, 3-15 membered heterocycloalkyl optionally substituted by 1-28 R$^{59}$, 4-21 membered heterocycloalkylalkyl optionally substituted by 1-40 R$^{59}$, 5-15 membered heteroaryl optionally substituted by 1-15 R$^{59}$, 6-21 membered heteroarylalkyl optionally substituted by 1-27 R$^{59}$, halogen, —CN, —C(=O)R$^{50}$, —C(=O)OR$^{50}$, —C(=O)NR$^{52}$R$^{53}$, —C(=O)C(=O)R$^{50}$, —C(=NR$^{55}$)R$^{50}$, —C(=NR$^{55}$)NR$^{52}$R$^{53}$, —C(=NOH)NR$^{52}$R$^{53}$, —C(=NOR$^{56}$)R$^{50}$, —C(=NNR$^{52}$R$^{53}$)R$^{50}$, —C(=NNR$^{54}$C(=O)R$^{51}$)R$^{59}$, —C(=NNR$^{54}$C(=O)OR$^{51}$)R$^{59}$, —C(=S)NR$^{52}$R$^{53}$, —NC, —NO$_2$, —NR$^{52}$R$^{53}$, —NR$^{54}$NR$^{52}$R$^{53}$, —N=NR$^{54}$, =NR$^{50}$, =NOR$^{50}$, —NR$^{54}$OR$^{56}$, —NR$^{54}$C(=O)R$^{50}$, —NR$^{54}$C(=O)C (=O)R$^{50}$, —NR$^{54}$C(=O)OR$^{51}$, —NR$^{54}$C(=O)C (=O)OR$^{51}$, —NR$^{54}$C(=O)NR$^{52}$R$^{53}$, —NR$^{54}$C (=O)NR$^{54}$C(=O)R$^{50}$, —NR$^{54}$C(=O)NR$^{54}$C(=O) OR$^{50}$, —NR$^{54}$C(=NR$^{55}$)NR$^{52}$R$^{53}$, —NR$^{54}$C(=O) C(=O)NR$^{52}$R$^{53}$, —NR$^{54}$C(=S)R$^{50}$, —NR$^{54}$C (=S)OR$^{50}$, —NR$^{54}$C(=S)NR$^{52}$R$^{53}$, —NR$^{54}$S (=O)$_2$ R$^{51}$, —NR$^{54}$S(=O)$_2$NR$^{52}$R$^{53}$, —NR$^{54}$P (=O)R$^{58}$R$^{58}$, —NR$^{54}$P(=O)(NR$^{52}$R$^{53}$)(NR$^{52}$R$^{53}$), —NR$^{54}$P(=O)(OR$^{50}$)(OR$^{50}$), —NR$^{54}$P(=O)(SR$^{50}$) (SR$^{50}$), —OR$^{50}$, =O, —OCN, —OC(=O)R$^{50}$, —OC(=O)NR$^{52}$R$^{53}$, —OC(=O)OR$^{50}$, —OC (=NR$^{55}$)NR$^{52}$R$^{53}$, —OS(=O)R$^{50}$, —OS(=O)$_2$ R$^{50}$, —OS(=O)$_2$OR$^{50}$, —OS(=O)$_2$NR$^{52}$R$^{53}$, —OP (=O)R$^{58}$R$^{58}$, —OP(=O)(NR$^{52}$R$^{53}$)(NR$^{52}$R$^{53}$), —OP(=O)(OR$^{50}$)(OR$^{50}$), —OP(=O)(SR$^{50}$)(SR$^{50}$), —SCN, =S, —S(=O)$_n$R$^{50}$, —S(=O)$_2$OR$^{50}$, —SO$_3$R$^{57}$, —S(=O)$_2$NR$^{52}$R$^{53}$, —S(=O)NR$^{52}$R$^{53}$, —SP(=O)R$^{58}$R$^{58}$, —SP(=O)(NR$^{52}$R$^{53}$) (NR$^{52}$R$^{53}$), —SP(=O)(OR$^{50}$)(OR$^{50}$), —SP(=O) (SR$^{50}$)(SR$^{50}$), —P(=O)R$^{58}$R$^{58}$, —P(=O) (NR$^{52}$R$^{53}$)(NR$^{52}$R$^{53}$), —P(=O)(OR$^{50}$)(OR$^{50}$), and —P(=O)(SR$^{50}$)(SR$^{50}$);

G$^2$, G$^3$, and G$^4$ are independently present or absent, and if present each is independently chosen from C$_{1-6}$alkylene optionally substituted by 1-12 R$^{69}$, C$_{2-6}$alkenylene optionally substituted by 1-10 R$^{69}$, C$_{2-6}$alkynylene optionally substituted by 1-8 R$^{69}$, C$_{6-11}$arylene optionally substituted by 1-10 R$^{69}$, C$_{7-16}$arylalkylene optionally substituted by 1-18 R$^{69}$, C$_{3-11}$cycloalkylene optionally substituted by 1-20 R$^{69}$, C$_{4-17}$cycloalkylalkylene optionally substituted by 1-31 R$^{69}$, 3-15 membered heterocycloalkylene optionally substituted by 1-27 R$^{69}$, 4-21 membered heterocycloalkylalkylene optionally substituted by 1-39 R$^{69}$, 5-15 membered heteroarylene optionally substituted by 1-14 R$^{69}$, 6-21 membered heteroarylalkylene optionally substituted by 1-26 R$^{69}$, —C$_{0-3}$alkylC(=O)C$_{0-3}$alkyl-, —C$_{0-3}$alkylC(=O) OC$_{0-3}$ alkyl-, —C$_{0-3}$alkylC(=O)NR$^{64}$C$_{0-3}$alkyl-, —C$_{0-3}$ alkylC(=O)C(=O)C$_{0-3}$alkyl-, —C$_{0-3}$alkylC (=NR$^{65}$)C$_{0-3}$alkyl-, —C$_{0-3}$alkylC(=NR$^{65}$)NR$^{64}$C$_{0-3}$ alkyl-, —C$_{0-3}$alkylC(=NOH)NR$^{64}$C$_{0-3}$alkyl-, —C$_{0-3}$ alkylC(=NOR$^{66}$)C$_{0-3}$alkyl-, —C$_{0-3}$alkylC(=NNR$^{62}$R$^{63}$)C$_{0-3}$alkyl-, —C$_{0-3}$alkylC(=NNR$^{64}$C(=O)R$^{61}$)C$_{0-3}$alkyl-, —C$_{0-3}$alkylC(=NNR$^{64}$C(=O)OR$^{61}$)C$_{0-3}$alkyl-, —C$_{0-3}$alkylC(=S)NR$^{64}$C$_{0-3}$alkyl-, —C$_{0-3}$alkylNR$^{64}$NR$^{64}$C$_{0-3}$ alkyl-, —C$_{0-3}$alkylN=NC$_{0-3}$ alkyl-, —C$_{0-3}$ alkylNR$^{64}$C(=O)C$_{0-3}$alkyl-, —C$_{0-3}$alkylNR$^{64}$C(=O)C(=O)C$_{0-3}$alkyl-, —C$_{0-3}$alkylNR$^{64}$C(=O)OC$_{0-3}$ alkyl-, —C$_{0-3}$alkylNR$^{64}$C(=O)C(=O)OC$_{0-3}$alkyl-, —C$_{0-3}$alkylNR$^{64}$C(=O)NR$^{64}$C$_{0-3}$alkyl-, —C$_{0-3}$ alkylNR$^{64}$C(=O)NR$^{64}$C(=O)C$_{0-3}$alkyl-, —C$_{0-3}$ alkylNR$^{64}$C(=O)NR$^{64}$C(=O)OC$_{0-3}$ alkyl-, —C$_{0-3}$ alkylNR$^{64}$C(=NR$^{65}$)NR$^{64}$C$_{0-3}$ alkyl-, —C$_{0-3}$ alkylNR$^{64}$C(=O)C(=O)NR$^{64}$C$_{0-3}$ alkyl-, —C$_{0-3}$ alkylNR$^{64}$C(=S)C$_{0-3}$alkyl-, —C$_{0-3}$ alkylNR$^{64}$C(=S)OC$_{0-3}$alkyl-, —C$_{0-3}$alkylNR$^{64}$C(=S)NR$^{64}$C$_{0-3}$alkyl-, —C$_{0-3}$alkylNR$^{64}$S(=O)$_2$C$_{0-3}$ alkyl-, —C$_{0-3}$alkylNR$^{64}$S(=O)$_2$NR$^{64}$C$_{0-3}$alkyl-, —C$_{0-3}$alkylOC$_{0-3}$alkyl-, —C$_{0-3}$alkylOC(=O)C$_{0-3}$ alkyl-, —C$_{0-3}$alkylOC(=O)NR$^{64}$C$_{0-3}$alkyl-, —C$_{0-3}$ alkylOC(=O)OC$_{0-3}$alkyl-, —C$_{0-3}$alkylOC(=NR$^{65}$)NR$^{64}$C$_{0-3}$alkyl-, —C$_{0-3}$alkylOS(=O)C$_{0-3}$alkyl-, —C$_{0-3}$ alkylOS(=O)$_2$C$_{0-3}$alkyl-, —C$_{0-3}$alkylOS(=O)$_2$OC$_{0-3}$ alkyl-, —C$_{0-3}$alkylOS(=O)$_2$NR$^{64}$C$_{0-3}$alkyl-, —C$_{0-3}$ alkylS(=O)—C$_{0-3}$alkyl-, —C$_{0-3}$alkylS(=O)$_2$OC$_{0-3}$ alkyl-, —C$_{0-3}$alkylSO$_3$C$_{0-3}$alkyl-, —C$_{0-3}$alkylS(=O)$_2$ NR$^{64}$C$_{0-3}$ alkyl-, and —C$_{0-3}$alkylS(=O)NR$^{64}$C$_{0-3}$ alkyl-;

X$^2$, X$^3$, and X$^4$ are independently present or absent, and if present each is independently chosen from C$_{1-6}$alkylene optionally substituted by 1-12 R$^{79}$, C$_{2-6}$alkenylene optionally substituted by 1-10 R$^{79}$, C$_{2-6}$alkynylene optionally substituted by 1-8 R$^{79}$, C$_{6-11}$arylene optionally substituted by 1-10 R$^{79}$, C$_{7-16}$arylalkylene optionally substituted by 1-18 R$^{79}$, C$_{3-11}$ cycloalkylene optionally substituted by 1-20 R$^{79}$, C$_{4-17}$cycloalkylalkylene optionally substituted by 1-31 R$^{79}$, 3-15 membered heterocycloalkylene optionally substituted by 1-27 R$^{79}$, 4-21 membered heterocycloalkylalkylene optionally substituted by 1-39 R$^{79}$, 5-15 membered heteroarylene optionally substituted by 1-14 R$^{79}$, 6-21 membered heteroarylalkylene optionally substituted by 1-26 R$^{79}$, —C$_{0-3}$ alkylC(=O)C$_{0-3}$ alkyl-, —C$_{0-3}$ alkylC(=O)OC$_{0-3}$ alkyl-, —C$_{0-3}$ alkylC(=O)NR$^{74}$C$_{0-3}$ alkyl-, —C$_{0-3}$ alkylC(=O)C(=O)C$_{0-3}$ alkyl-, —C$_{0-3}$ alkylC(=NR$^{75}$)C$_{0-3}$ alkyl-, —C$_{0-3}$ alkylC(=NR$^{75}$)NR$^{74}$C$_{0-3}$ alkyl-, —C$_{0-3}$ alkylC(=NOH)NR$^{74}$C$_{0-3}$ alkyl-, —C$_{0-3}$ alkylC(=NOR$^{76}$)C$_{0-3}$ alkyl-, —C$_{0-3}$ alkylC(=NNR$^{72}$R$^{73}$)C$_{0-3}$ alkyl-, —C$_{0-3}$ alkylC(=NNR$^{74}$C(=O)R$^{71}$)C$_{0-3}$ alkyl-, —C$_{0-3}$ alkylC(=NNR$^{74}$C(=O)OR$^{71}$)C$_{0-3}$ alkyl-, —C$_{0-3}$ alkylC(=S)NR$^{74}$C$_{0-3}$ alkyl-, —C$_{0-3}$ alkylNR$^{74}$C$_{0-3}$ alkyl-, —C$_{0-3}$ alkylNR$^{74}$NR$^{74}$C$_{0-3}$ alkyl-, —C$_{0-3}$ alkylN=NC$_{0-3}$ alkyl-, —C$_{0-3}$ alkylNR$^{74}$C(=O)C$_{0-3}$ alkyl-, —C$_{0-3}$ alkylNR$^{74}$C(=O)C(=O)C$_{0-3}$ alkyl-, —C$_{0-3}$ alkylNR$^{74}$C(=O)OC$_{0-3}$ alkyl-, —C$_{0-3}$ alkylNR$^{74}$C(=O)C(=O)OC$_{0-3}$ alkyl-, —C$_{0-3}$ alkylNR$^{74}$C(=O)NR$^{74}$C$_{0-3}$ alkyl-, —C$_{0-3}$ alkylNR$^{74}$C(=O)NR$^{74}$C(=O)C$_{0-3}$ alkyl-, —C$_{0-3}$ alkylNR$^{74}$C(=O)NR$^{74}$C(=O)OC$_{0-3}$ alkyl-, —C$_{0-3}$ alkylNR$^{74}$C(=NR$^{75}$)NR$^{74}$C$_{0-3}$ alkyl-, —C$_{0-3}$ alkylNR$^{74}$C(=O)C(=O)NR$^{74}$C$_{0-3}$ alkyl-, —C$_{0-3}$ alkylNR$^{74}$C(=S)C$_{0-3}$ alkyl-, —C$_{0-3}$ alkylNR$^{74}$C(=S)OC$_{0-3}$ alkyl-, —C$_{0-3}$ alkylNR$^{74}$C(=S)NR$^{74}$C$_{0-3}$ alkyl-, —C$_{0-3}$ alkylNR$^{74}$S(=O)$_2$C$_{0-3}$ alkyl-, —C$_{0-3}$ alkylNR$^{74}$S(=O)$_2$NR$^{74}$C$_{0-3}$ alkyl-, —C$_{0-3}$ alkylOC$_{0-3}$ alkyl-, —C$_{0-3}$ alkylOC(=O)C$_{0-3}$ alkyl-, —C$_{0-3}$ alkylOC(=O)NR$^{74}$C$_{0-3}$ alkyl-, —C$_{0-3}$ alkylOC(=O)OC$_{0-3}$ alkyl-, —C$_{0-3}$ alkylOC(=NR$^{75}$)NR$^{74}$C$_{0-3}$ alkyl-, —C$_{0-3}$ alkylOS(=O)C$_{0-3}$ alkyl-, —C$_{0-3}$ alkylOS(=O)$_2$C$_{0-3}$ alkyl-, —C$_{0-3}$ alkylOS(=O)$_2$OC$_{0-3}$ alkyl-, —C$_{0-3}$ alkylOS(=O)$_2$NR$^{74}$C$_{0-3}$ alkyl-, —C$_{0-3}$ alkylS(=O)—C$_{0-3}$ alkyl-, —C$_{0-3}$ alkylS(=O)$_2$OC$_{0-3}$ alkyl-, —C$_{0-3}$ alkylSO$_3$C$_{0-3}$ alkyl-, —C$_{0-3}$ alkylS(=O)$_2$NR$^{74}$C$_{0-3}$ alkyl-, and —C$_{0-3}$ alkylS(=O)NR$^{74}$C$_{0-3}$ alkyl-;

Z$^2$, Z$^3$, and Z$^4$ are independently chosen from H, C$_{1-6}$alkyl optionally substituted by 1-13 R$^{89}$, C$_{2-6}$alkenyl optionally substituted by 1-11 R$^{89}$, C$_{2-6}$alkynyl optionally substituted by 1-9 R$^{89}$, C$_{6-11}$ aryl optionally substituted by 1-11 R$^{89}$, C$_{7-16}$arylalkyl optionally substituted by 1-19 R$^{89}$, C$_{3-11}$ cycloalkyl optionally substituted by 1-21 R$^{89}$, C$_{4-17}$cycloalkylalkyl optionally substituted by 1-32 R$^{89}$, 3-15 membered heterocycloalkyl optionally substituted by 1-28 R$^{89}$, 4-21 membered heterocycloalkylalkyl optionally substituted by 1-40 R$^{89}$, 5-15 membered heteroaryl optionally substituted by 1-15 R$^{89}$, 6-21 membered heteroarylalkyl optionally substituted by 1-27 R$^{89}$, halogen, —CN, —C(=O)R$^{80}$, —C(=O)OR$^{80}$, —C(=O)NR$^{82}$R$^{83}$, —C(=O)C(=O)R$^{80}$, —C(=NR$^{85}$)R$^{80}$, —C(=NR$^{85}$)NR$^{82}$R$^{83}$, —C(=NOH)NR$^{82}$R$^{83}$, —C(=NOR$^{86}$)R$^{80}$, —C(=NNR$^{82}$R$^{83}$)R$^{80}$, —C(=NNR$^{84}$C(=O)R$^{81}$)R$^{80}$, —C(=NNR$^{84}$C(=O)OR$^{81}$)R$^{80}$, —C(=S)NR$^{82}$R$^{83}$, —NC, —NO$_2$, —NR$^{82}$R$^{83}$, —NR$^{84}$NR$^{82}$R$^{83}$, —N=NR$^{84}$, =NR$^{80}$, =NOR$^{80}$, —NR$^{84}$OR$^{86}$, —NR$^{84}$C(=O)R$^{80}$, —NR$^{84}$C(=O)C(=O)R$^{80}$, —NR$^{84}$C(=O)OR$^{81}$, —NR$^{84}$C(=O)C(=O)OR$^{81}$, —NR$^{84}$C(=O)NR$^{82}$R$^{83}$, —NR$^{84}$C(=O)R$^{80}$, —NR$^{84}$C(=O)NR$^{84}$C(=O)OR$^{80}$, —NR$^{84}$C(=NR$^{85}$)NR$^{82}$R$^{83}$, —NR$^{84}$C(=O)C(=O)NR$^{82}$R$^{83}$, —NR$^{84}$C(=S)R$^{80}$, —NR$^{84}$C(=S)OR$^{80}$, —NR$^{84}$C(=S)NR$^{82}$R$^{83}$, —NR$^{84}$S(=O)$_2$R$^{81}$, —NR$^{84}$S(=O)$_2$NR$^{82}$R$^{83}$, —NR$^{84}$P(=O)R$^{88}$R$^{88}$, —NR$^{84}$P(=O)(NR$^{82}$R$^{83}$)(NR$^{82}$R$^{83}$), —NR$^{84}$P(=O)(OR$^{80}$)(OR$^{80}$), —NR$^{84}$P(=O)(SR$^{80}$)(SR$^{80}$), —OR$^{80}$, =O, —OCN, —OC(=O)R$^{80}$, —OC(=O)NR$^{82}$R$^{83}$, —OC(=O)OR$^{80}$, —OC(=NR$^{85}$)NR$^{82}$R$^{83}$, —OS(=O)R$^{80}$, —OS(=O)$_2$R$^{80}$, —OS(=O)$_2$OR$^{80}$, —OS(=O)$_2$NR$^{82}$R$^{83}$, —OP(=O)R$^{88}$R$^{88}$, —OP(=O)(NR$^{82}$R$^{83}$)(NR$^{82}$R$^{83}$), —OP(=O)(OR$^{80}$)(OR$^{80}$), —OP(=O)(SR$^{80}$)(SR$^{80}$), —SCN, =S, —S(=O)$_n$R$^{80}$, —S(=O)$_2$OR$^{80}$, —SO$_3$R$^{87}$, —S(=O)$_2$NR$^{82}$R$^{83}$, —S(=O)NR$^{82}$R$^{83}$, —SP(=O)R$^{88}$R$^{88}$, —SP(=O)(NR$^{82}$R$^{83}$)(NR$^{82}$R$^{83}$), —SP(=O)(OR$^{80}$)(OR$^{80}$), —SP(=O)(SR$^{80}$)(SR$^{80}$), —P(=O)R$^{88}$R$^{88}$, —P(=O)(NR$^{82}$R$^{83}$)(NR$^{82}$R$^{83}$), —P(=O)(OR$^{80}$)(OR$^{80}$), and —P(=O)(SR$^{80}$)(SR$^{80}$);

alternatively, when L$^2$, A$^2$, G$^2$, X$^2$, L$^3$, A$^3$, G$^3$ and X$^3$ are absent, Z$^2$ and Z$^3$ can together form a group of formula -A$^{21}$-A$^{22}$-A$^{23}$-, or when L$^3$, A$^3$, G$^3$, X$^3$, L$^4$, A$^4$, G$^4$ and X$^4$ are absent, Z$^3$ and Z$^4$ can together form a group of formula -A$^{21}$-A$^{22}$-A$^{23}$-;

wherein A$^{21}$, A$^{22}$, and A$^{23}$ are independently chosen from —CZ$^{21}$Z$^{22}$—, —CZ$^{23}$Z$^{24}$CZ$^{25}$Z$^{26}$—, —C(=O)—, —NZ$^{27}$—, —S—, —S(=O)—, —S(=O)$_2$—, or —O—;

wherein:

(a) when any two of Z$^{21}$, Z$^{22}$, Z$^{23}$, Z$^{24}$, Z$^{25}$, Z$^{26}$ and Z$^{27}$ are located on adjacent atoms, they may together form a bond between the atoms, and (b) any of Z$^{21}$, Z$^{22}$, Z$^{23}$, Z$^{24}$, Z$^{25}$, Z$^{26}$ and Z$^{27}$ may be independently chosen from H, C$_{1-6}$alkyl optionally substituted by 1-13 R$^{99}$, C$_{2-6}$alkenyl optionally substituted by 1-11 R$^{99}$, C$_{2-6}$alkynyl optionally substituted by 1-9 R$^{99}$, C$_{6-11}$aryl optionally substituted by 1-11 $R^{99}$, $C_{7-16}$arylalkyl optionally substituted by 1-19 $R^{99}$, $C_{3-11}$cycloalkyl optionally substituted by 1-21 $R^{99}$, $C_{4-17}$cycloalkylalkyl optionally substituted by 1-32 $R^{99}$, 3-15 membered heterocycloalkyl optionally substituted by 1-28 $R^{99}$, 4-21 membered heterocycloalkylalkyl optionally substituted by 1-40 $R^{99}$, 5-15 membered heteroaryl optionally substituted by 1-15 $R^{99}$, 6-21 membered heteroarylalkyl optionally substituted by 1-27 $R^{99}$, halogen, —CN, —C(=O)$R^{90}$, —C(=O)O$R^{90}$, —C(=O)N$R^{92}R^{93}$, —C(=O)C(=O)$R^{90}$, —C(=N$R^{95}$)$R^{90}$, —C(=N$R^{95}$)N$R^{92}R^{93}$, —C(=NOH)N$R^{92}R^{93}$, —C(=NO$R^{96}$)$R^{90}$, —C(=NN$R^{92}R^{93}$)$R^{90}$, —C(=NN$R^{94}$C(=O)$R^{91}$)$R^{90}$, —C(=NN$R^{94}$C(=O)O$R^{91}$)$R^{90}$, —C(=S)N$R^{92}R^{93}$, —NC, —NO$_2$, —N$R^{92}R^{93}$, —N$R^{94}$N$R^{92}R^{93}$, —N=N$R^{94}$, =N$R^{90}$, =NO$R^{90}$, —N$R^{94}$O$R^{96}$, —N$R^{94}$C(=O)$R^{90}$, —N$R^{94}$C(=O)C(=O)$R^{90}$, —N$R^{94}$C(=O)O$R^{91}$, —N$R^{94}$C(=O)C(=O)O$R^{91}$, —N$R^{94}$C(=O)N$R^{92}R^{93}$, —N$R^{94}$C(=O)N$R^{94}$C(=O)$R^{90}$, —N$R^{94}$C(=O)N$R^{94}$C(=O)O$R^{90}$, —N$R^{94}$C(=N$R^{95}$)N$R^{92}R^{93}$, —N$R^{94}$C(=O)C(=O)N$R^{92}R^{93}$, —N$R^{94}$C(=S)$R^{90}$, —N$R^{94}$C(=S)O$R^{90}$, —N$R^{94}$C(=S)N$R^{92}R^{93}$, —N$R^{94}$S(=O)$_2R^{91}$, —N$R^{94}$S(=O)$_2$N$R^{92}R^{93}$, —N$R^{94}$P(=O)$R^{98}R^{98}$, —N$R^{94}$P(=O)(N$R^{92}R^{93}$)(N$R^{92}R^{93}$), —N$R^{94}$P(=O)(O$R^{90}$)(O$R^{90}$), N$R^{94}$P(=O)(S$R^{90}$)(S$R^{90}$), —O$R^{90}$, =O, —OCN, —OC(=O)$R^{90}$, —OC(=O)N$R^{92}R^{93}$, —OC(=O)O$R^{90}$, —OC(=N$R^{95}$)N$R^{92}R^{93}$, —OS(=O)$R^{90}$, —OS(=O)$_2R^{90}$, —OS(=O)$_2$O$R^{90}$, —OS(=O)$_2$N$R^{92}R^{93}$, —OP(=O)$R^{98}R^{98}$, —OP(=O)(N$R^{92}R^{93}$)(N$R^{92}R^{93}$), —OP(=O)(O$R^{90}$(O$R^{90}$, —OP(=O)(S$R^{90}$)(S$R^{90}$), —SCN, =S, —S(=O)$_nR^{90}$, —S(=O)$_2$O$R^{90}$, —SO$_3R^{97}$, —S(=O)$_2$N$R^{92}R^{93}$, —S(=O)N$R^{92}R^{93}$, —SP(=O)$R^{98}R^{98}$, —SP(=O)(N$R^{92}R^{93}$)(N$R^{92}R^{93}$), —SP(=O)(O$R^{90}$)(O$R^{90}$), —SP(=O)(S$R^{90}$)(S$R^{90}$), —P(=O)$R^{98}R^{98}$, —P(=O)(N$R^{92}R^{93}$)(N$R^{92}R^{93}$), —P(=O)(O$R^{90}$)(O$R^{90}$), and P(=O)(S$R^{90}$)(S$R^{90}$); and (c) any two of $Z^{21}$, $Z^{22}$, $Z^{23}$, $Z^{24}$, $Z^{25}$, $Z^{26}$ and $Z^{27}$ may together form a group of formula -$A^{31}$-$A^{32}$-$A^{33}$-, wherein $A^{31}$, $A^{32}$, and $A^{33}$ are independently chosen from —C$Z^{31}Z^{32}$—, —C$Z^{33}Z^{34}$C$Z^{35}Z^{36}$—, —C(=O)—, —N$Z^{37}$—, —S—, —S(=O)—, —S(=O)$_2$—, or —O— wherein:

(i) when any two of $Z^{31}$, $Z^{32}$, $Z^{33}$, $Z^{34}$, $Z^{35}$, $Z^{36}$ and $Z^{37}$ are located on adjacent atoms, they may together form a bond between the atoms, and (ii) any of any of $Z^{21}$, $Z^{22}$, $Z^{23}$, $Z^{24}$, $Z^{25}$, $Z^{26}$ and $Z^{27}$ may be independently chosen from H, $C_{1-6}$alkyl optionally substituted by 1-13 $R^{139}$, $C_{2-6}$alkenyl optionally substituted by 1-11 $R^{139}$, $C_{2-6}$alkynyl optionally substituted by 1-9 $R^{139}$, $C_{6-11}$aryl optionally substituted by 1-11 $R^{139}$, $C_{7-16}$arylalkyl optionally substituted by 1-19 $R^{139}$, $C_{3-11}$cycloalkyl optionally substituted by 1-21 $R^{139}$, $C_{4-17}$cycloalkylalkyl optionally substituted by 1-32 $R^{139}$, 3-15 membered heterocycloalkyl optionally substituted by 1-28 $R^{139}$, 4-21 membered heterocycloalkylalkyl optionally substituted by 1-40 $R^{139}$, 5-15 membered heteroaryl optionally substituted by 1-15 $R^{139}$, 6-21 membered heteroarylalkyl optionally substituted by 1-27 $R^{139}$, halogen, —CN, —C(=O)$R^{130}$, —C(=O)O$R^{130}$, —C(=O)N$R^{132}R^{133}$, —C(=O) $R^{130}$, —C(=N$R^{135}$)$R^{130}$, —C(=N$R^{135}$)N$R^{132}R^{133}$, —C(=NOH)N$R^{132}R^{133}$, —C(=NO$R^{136}$)$R^{130}$, —C(=NN$R^{132}R^{133}$)$R^{130}$, —C(=NN$R^{134}$C(=O)$R^{131}$)$R^{130}$, —C(=NN$R^{134}$C(=O)O$R^{131}$)$R^{130}$, —C(=S)N$R^{132}R^{133}$, —NC, —NO$_2$, —N$R^{132}R^{133}$, —N$R^{134}$N$R^{132}R^{133}$, —N=N$R^{134}$, =N$R^{130}$, =NO$R^{130}$, —N$R^{134}$O$R^{136}$, —N$R^{134}$C(=O)$R^{130}$, —N$R^{134}$C(=O)C(=O)$R^{130}$, —N$R^{134}$C(=O)O$R^{131}$, —N$R^{134}$C(=O)C(=O)O$R^{131}$, —N$R^{134}$C(=O)N$R^{132}R^{133}$, —N$R^{134}$C(=O)N$R^{134}$C(=O)$R^{130}$, —N$R^{134}$C(=O)N$R^{134}$C(=O)O$R^{130}$, —N$R^{134}$C(=N$R^{135}$)N$R^{132}R^{133}$, —N$R^{134}$C(=O)C(=O)N$R^{132}R^{133}$, —N$R^{134}$C(=S)$R^{130}$, —N$R^{134}$C(=S)O$R^{130}$, N$R^{134}$C(=S)N$R^{132}R^{133}$, —N$R^{134}$S(=O)$_2R^{131}$, —N$R^{134}$S(=O)$_2$N$R^{132}R^{133}$, —N$R^{134}$P(=O)$R^{138}R^{138}$, N$R^{134}$P(=O)(N$R^{132}R^{133}$)(N$R^{132}R^{133}$), —N$R^{134}$P(=O)(O$R^{130}$)(O$R^{130}$), —N$R^{134}$P(=O)(S$R^{130}$)(S$R^{130}$), —O$R^{130}$, =O, —OCN, —OC(=O)$R^{130}$, —OC(=O)N$R^{132}R^{133}$, —OC(=O)O$R^{130}$, —OC(=N$R^{135}$)N$R^{132}R^{133}$, —OS(=O)$R^{130}$, —OS(=O)$_2R^{130}$, —OS(=O)$_2$O$R^{130}$, —OS(=O)$_2$N$R^{132}R^{133}$, —OP(=O)$R^{138}R^{138}$, —OP(=O)(N$R^{132}R^{133}$)(N$R^{132}R^{133}$), —OP(=O)(O$R^{130}$)(O$R^{130}$), —OP(=O)(S$R^{130}$)(S$R^{130}$), —SCN, =S, —S(=O)$_nR^{130}$, —S(=O)$_2$O$R^{130}$, —SO$_3R^{137}$, —S(=O)$_2$N$R^{132}R^{133}$, —S(=O)N$R^{132}R^{133}$, —SP(=O)$R^{138}R^{138}$, —SP(=O)(N$R^{132}R^{133}$)(N$R^{132}R^{133}$), —SP(=O)(O$R^{130}$)(O$R^{13}$), —SP(=O)(S$R^{130}$)(S$R^{130}$), —P(=O)$R^{138}R^{138}$, —P(=O)(N$R^{132}R^{133}$)(N$R^{132}R^{133}$), —P(=O)(O$R^{130}$)(O$R^{130}$), and —P(=O)(S$R^{130}$)(S$R^{130}$);

$R^9$, $R^{19}$, $R^{29}$, $R^{39}$, $R^{49}$, $R^{59}$, $R^{69}$, $R^{79}$, $R^{89}$, $R^{99}$, and $R^{139}$ at each occurrence is independently chosen from $C_{1-6}$alkyl optionally substituted by 1-13 $R^{179}$, $C_{2-6}$alkenyl optionally substituted by 1-11 $R^{179}$, $C_{2-6}$alkynyl optionally substituted by 1-9 $R^{179}$, $C_{6-11}$aryl optionally substituted by 1-11 $R^{179}$, $C_{7-16}$arylalkyl optionally substituted by 1-19 $R^{179}$, $C_{3-11}$cycloalkyl optionally substituted by 1-21 $R^{179}$, $C_{4-17}$cycloalkylalkyl optionally substituted by 1-32 $R^{179}$, 3-15 membered heterocycloalkyl optionally substituted by 1-28 $R^{179}$, 4-21 membered heterocycloalkylalkyl optionally substituted by 1-40 $R^{179}$, 5-15 membered heteroaryl optionally substituted by 1-15 $R^{179}$, 6-21 membered heteroarylalkyl optionally substituted by 1-27 $R^{179}$, halogen, —CN, —C(=O)$R^{170}$, —C(=O)O$R^{170}$, —C(=O)N$R^{172}R^{173}$, —C(=O)C(=O)$R^{170}$, —C(=N$R^{175}$)$R^{170}$, —C(=N$R^{175}$)N$R^{172}R^{173}$, —C(=NOH)N$R^{172}R^{173}$, —C(NO$R^{176}$)$R^{170}$, —C(NN$R^{172}R^{173}$)$R^{170}$, —C(NN$R^{174}$C(=O)$R^{171}$)$R^{170}$, —C(=NN$R^{174}$C(=O)O$R^{171}$)$R^{170}$, —C(=S)N$R^{172}R^{173}$, —NC, —NO$_2$, —N$R^{172}R^{173}$, —N$R^{174}$N$R^{172}R^{173}$, N=N$R^{174}$, —N$R^{170}$, —NO$R^{170}$, N$R^{174}$O$R^{176}$, —N$R^{174}$C(=O)$R^{170}$, —N$R^{174}$C(=O)C(=O)$R^{170}$, —N$R^{174}$C(=O)O$R^{171}$, —N$R^{174}$C(=O)C(=O)O$R^{171}$, —N$R^{174}$C(=O)N$R^{172}R^{173}$, —N$R^{174}$C(=O)N$R^{174}$C(=O)$R^{170}$, —N$R^{174}$C(=O)N$R^{174}$C(=O)O$R^{170}$, —N$R^{174}$C(=N$R^{175}$)N$R^{172}R^{173}$, —N$R^{174}$C(=O)C(=O)N$R^{172}R^{173}$, —N$R^{174}$C(=S)$R^{170}$, —N$R^{174}$C(=S)O$R^{170}$, —N$R^{174}$C(=S)N$R^{172}R^{173}$, —N$R^{174}$S(=O)$_2R^{171}$, —N$R^{174}$S(=O)$_2$N$R^{172}R^{173}$, —N$R^{174}$P(=O)$R^{178}R^{178}$, —N$R^{174}$P $(=O)(NR^{172}R^{173})(NR^{172}R^{173})$, $-NR^{174}P(=O)$ $(OR^{170})(OR^{170})$, $-NR^{174}P(=O)(SR^{170})(SR^{170})$, $-OR^{170}$, $=O$, $-OCN$, $-OC(=O)R^{170}$, $-OC(=O)$ $NR^{172}R^{173}$, $-OC(=O)OR^{170}$, $-OC(=NR^{175})$ $NR^{172}R^{173}$, $-OS(=O)R^{170}$, $-OS(=O)_2R^{170}$, $-OS$ $(=O)_2OR^{170}$, $-OS(=O)_2NR^{172}R^{173}$, $-OP(=O)$ $R^{178}R^{178}$, $-OP(=O)(NR^{172}R^{173})(NR^{172}R^{173})$, $-OP$ $(=O)(OR^{170})(OR^{170})$, $-OP(=O)(SR^{170})(SR^{170})$, $-SCN$, $=S$, $-S(=O)_nR^{170}$, $-S(=O)_2OR^{170}$, $-SO_3R^{177}$, $-S(=O)_2NR^{172}R^{173}$, $-S(=O)$ $NR^{172}R^{173}$, $-SP(=O)R^{178}R^{178}$, $SP(=O)(NR^{172}R^{173})$ $(NR^{172}R^{173})$, $-SP(=O)(OR^{170})(OR^{17})$, $-SP(=O)$ $(SR^{170})(SR^{170})$, $-P(=O)R^{178}R^{178}$, $-P(=O)$ $(NR^{172}R^{173})(NR^{172}R^{173})$, $-P(=O)(OR^{170})(OR^{170})$, and $-P(=O)(SR^{170})(SR^{170})$;

$R^1$, $R^4$, $R^5$, $R^6$, $R^{10}$, $R^{11}$, $R^{14}$, $R^{15}$, $R^{16}$, $R^{17}$, $R^{21}$, $R^{24}$, $R^{25}$, $R^{26}$, $R^{31}$, $R^{34}$, $R^{35}$, $R^{36}$, $R^{41}$, $R^{44}$, $R^{45}$, $R^{46}$, $R^{50}$, $R^{51}$, $R^{54}$, $R^{55}$, $R^{56}$, $R^{57}$, $R^{61}$, $R^{64}$, $R^{65}$, $R^{66}$, $R^{71}$, $R^{74}$, $R^{75}$, $R^{76}$, $R^{80}$, $R^{81}$, $R^{84}$, $R^{85}$, $R^{86}$, $R^{87}$, $R^{90}$, $R^{91}$, $R^{94}$, $R^{95}$, $R^{96}$, $R^{97}$, $R^{100}$, $R^{101}$, $R^{104}$, $R^{105}$, $R^{106}$, $R^{107}$, $R^{130}$, $R^{131}$, $R^{134}$, $R^{135}$, $R^{136}$, $R^{137}$, $R^{170}$, $R^{171}$, $R^{174}$, $R^{175}$, $R^{176}$ and $R^{177}$ at each occurrence is independently chosen from H, $C_{1-6}$alkyl optionally substituted by 1-13 $R^{189}$, $C_{2-6}$alkenyl optionally substituted by 1-11 $R^{189}$, $C_{2-6}$alkynyl optionally substituted by 1-9 $R^{189}$, $C_{6-11}$aryl optionally substituted by 1-11 $R^{189}$, $C_{7-16}$arylalkyl optionally substituted by 1-19 $R^{189}$, $C_{3-11}$cycloalkyl optionally substituted by 1-21 $R^{189}$, $C_{4-17}$cycloalkylalkyl optionally substituted by 1-32 $R^{189}$, 3-15 membered heterocycloalkyl optionally substituted by 1-28 $R^{189}$, 4-21 membered heterocycloalkylalkyl optionally substituted by 1-40 $R^{189}$, 5-15 membered heteroaryl optionally substituted by 1-15 $R^{189}$, and 6-21 membered heteroarylalkyl optionally substituted by 1-27 $R^{189}$;

$R^{18}$, $R^{58}$, $R^{88}$, $R^{98}$, $R^{108}$, $R^{138}$, and $R^{178}$ at each occurrence is independently chosen from $C_{1-6}$alkyl optionally substituted by 1-13 $R^{189}$, $C_{2-6}$alkenyl optionally substituted by 1-11 $R^{189}$, $C_{2-6}$alkynyl optionally substituted by 1-9 $R^{189}$, $C_{6-11}$aryl optionally substituted by 1-11 $R^{189}$, $C_{7-16}$arylalkyl optionally substituted by 1-19 $R^{189}$, $C_{3-11}$cycloalkyl optionally substituted by 1-21 $R^{189}$, $C_{4-17}$cycloalkylalkyl optionally substituted by 1-32 $R^{189}$, 3-15 membered heterocycloalkyl optionally substituted by 1-28 $R^{189}$, 4-21 membered heterocycloalkylalkyl optionally substituted by 1-40 $R^{189}$, 5-15 membered heteroaryl optionally substituted by 1-15 $R^{189}$, and 6-21 membered heteroarylalkyl optionally substituted by 1-27 $R^{189}$;

$R^2$, $R^3$, $R^{12}$, $R^{13}$, $R^{22}$, $R^{23}$, $R^{32}$, $R^{33}$, $R^{42}$, $R^{43}$, $R^{52}$, $R^{53}$, $R^{62}$, $R^{63}$, $R^{72}$, $R^{73}$, $R^{82}$, $R^{83}$, $R^{92}$, $R^{93}$, $R^{102}$, $R^{103}$, $R^{132}$, $R^{133}$, $R^{172}$ and $R^{173}$ at each occurrence is independently chosen from H, $C_{1-6}$alkyl optionally substituted by 1-13 $R^{199}$, $C_{2-6}$alkenyl optionally substituted by 1-11 $R^{199}$, $C_{2-6}$alkynyl optionally substituted by 1-9 $R^{199}$, $C_{6-11}$aryl optionally substituted by 1-11 $R^{199}$, $C_{7-16}$arylalkyl optionally substituted by 1-19 $R^{199}$, $C_{3-11}$cycloalkyl optionally substituted by 1-21 $R^{199}$, $C_{4-17}$cycloalkylalkyl optionally substituted by 1-32 $R^{199}$, 3-15 membered heterocycloalkyl optionally substituted by 1-28 $R^{199}$, 4-21 membered heterocycloalkylalkyl optionally substituted by 1-40 $R^{199}$, 5-15 membered heteroaryl optionally substituted by 1-15 $R^{199}$, and 6-21 membered heteroarylalkyl optionally substituted by 1-27 $R^{199}$;

or any $R^2$ and $R^3$, $R^{12}$ and $R^{13}$, $R^{22}$ and $R^{23}$, $R^{32}$ and $R^{33}$, $R^{42}$ and $R^{43}$, $R^{52}$ and $R^{53}$, $R^{62}$ and $R^{63}$, $R^{72}$ and $R^{73}$, $R^{82}$ and $R^{83}$, $R^{92}$ and $R^{93}$, $R^{102}$ and $R^{103}$, $R^{132}$ and $R^{133}$, or $R^{172}$ and $R^{173}$ may form, together with the nitrogen atom to which they are attached, a 3-15 membered heterocycloalkyl optionally substituted by 1-28 $R^{209}$ or a 5-15 membered heteroaryl optionally substituted by 1-15 $R^{209}$;

$R^{179}$, $R^{189}$, $R^{199}$ and $R^{209}$ at each occurrence is independently chosen from $C_{1-6}$alkyl optionally substituted by 1-13 $R^{219}$, $C_{2-6}$alkenyl optionally substituted by 1-11 $R^{219}$, $C_{2-6}$alkynyl optionally substituted by 1-9 $R^{219}$, $C_{6-11}$aryl optionally substituted by 1-11 $R^{219}$, $C_{7-16}$arylalkyl optionally substituted by 1-19 $R^{219}$, $C_{3-11}$cycloalkyl optionally substituted by 1-21 $R^{219}$, $C_{4-17}$cycloalkylalkyl optionally substituted by 1-32 $R^{219}$, 3-15 membered heterocycloalkyl optionally substituted by 1-28 $R^{219}$, 4-21 membered heterocycloalkylalkyl optionally substituted by 1-40 $R^{219}$, 5-15 membered heteroaryl optionally substituted by 1-15 $R^{219}$, 6-21 membered heteroarylalkyl optionally substituted by 1-27 $R^{219}$, halogen, $-CN$, $-C(=O)R^{210}$, $-C(=O)OR^{210}$, $-C(=O)NR^{212}R^{213}$, $-C(=O)C(=O)R^{210}$, $-C(=NR^{215})R^{210}$, $-C(=NR^{215})NR^{212}R^{213}$, $-C(=NOH)NR^{212}R^{213}$, $-C(=NOR^{216})R^{210}$, $-C(=NR^{215})NR^{212}R^{213}$, $-C(=NNR^{214}C(=O)$ $R^{211})R^{210}$, $-C(=NNR^{214}C(=O)OR^{211})R^{210}$, $-C(=S)NR^{212}R^{213}$, $-NC$, $-NO_2$, $-NR^{212}R^{213}$, $NR^{214}NR^{212}R^{213}$, $-N=NR^{214}$, $=NR^{210}$, $=NOR^{210}$, $-NR^{214}OR^{216}$, $-NR^{214}C(=O)R^{210}$, $-NR^{214}C(=O)$ $C(=O)R^{210}$, $-NR^{214}C(=O)OR^{211}$, $-NR^{214}C(=O)$ $C(=O)OR^{211}$, $-NR^{214}C(=O)NR^{212}R^{213}$, $-NR^{214}C(=O)NR^{214}C(=O)R^{210}$, $-NR^{214}C(=O)NR^{214}C(=O)OR^{210}$, $-NR^{214}C(=NR^{215})NR^{212}R^{213}$, $-NR^{214}C(=O)C(=O)NR^{212}R^{213}(=S)R^{210}$, $-NR^{214}C(=S)OR^{210}$, $-NR^{214}C(=S)NR^{212}R^{213}$, $-NR^{214}S(=O)_2R^{211}$, $-NR^{214}S(=O)_2NR^{212}R^{213}$, $-NR^{214}P(=O)NR^{218}R^{218}$, $-NR^{214}P(=O)$ $(NR^{212}R^{213})(NR^{212}R^{213})$, $-NR^{214}P(=O)(OR^{210})$ $(OR^{210})(OR^{210})$, $-NR^{214}P(=O)(SR^{210})(SR^{210})$, $-OR^{210}$, $=O$, $-OCN$, $-OC(=O)R^{210}$, $-OC(=O)$ $NR^{212}R^{213}$, $-OC(=O)OR^{210}$, $-OC(=NR^{215})$ $NR^{212}R^{213}$, $-OS(=O)R^{210}$, $-OS(=O)_2R^{210}$, $-OS$ $(=O)_2OR^{210}$, $-OS(=O)_2NR^{212}R^{213}$, $-OP(=O)$ $R^{218}R^{218}$, $-OP(=O)(NR^{212}R^{213})(NR^{212}R^{213})$, $-OP$ $(=O)(OR^{210})(OR^{210})$, $-OP(=O)(SR^{210})(SR^{210})$, $-SCN$, $=S$, $-S(=O)_nR^{210}$, $-S(=O)_2OR^{210}$, $-SO_3R^{217}$, $-S(=O)_2NR^{212}R^{213}$, $-S(=O)$ $NR^{212}R^{213}$, $-SP(=O)R^{218}R^{218}$, $-S(=O)_2NR^{212}R^{213}$, $-S(=O)NR^{212}R^{213}$, $-SP(=O)R^{218}R^{218}$, $-SP(=O)(NR^{212}R^{213})(NR^{212}R^{213})$, $-SP(=O)$ $(OR^{210})(OR^{210})$, $-SP(=O)(SR^{210})(SR^{210})$, $-P(=O)$ $R^{218}R^{218}$, $-P(=O)(NR^{212}R^{213})(NR^{212}R^{213})$, $-P(=O)(OR^{210})(OR^{210})$, and $-P(=O)(SR^{210})$ $(SR^{210})$;

$R^{210}$, $R^{210}$, $R^{211}$, $R^{214}$, $R^{215}$, $R^{216}$ and $R^{217}$ at each occurrence is independently chosen from H, $C_{1-6}$alkyl optionally substituted by 1-13 $R^{229}$, $C_{2-6}$alkenyl optionally substituted by 1-11 $R^{229}$, $C_{2-6}$alkynyl optionally substituted by 1-9 $R^{229}$, $C_{6-11}$aryl optionally substituted by 1-11 $R^{229}$, $C_{7-16}$arylalkyl optionally substituted by 1-19 $R^{229}$, $C_{3-11}$cycloalkyl optionally substituted by 1-21 $R^{229}$, $C_{4-17}$cycloalkylalkyl optionally substituted by 1-32 $R^{229}$, 3-15 membered heterocycloalkyl optionally substituted by 1-28 $R^{229}$, 4-21 membered heterocycloalkylalkyl optionally substituted by 1-40 $R^{229}$, 5-15 membered heteroaryl optionally substituted by 1-15 $R^{229}$, and 6-21 membered heteroarylalkyl optionally substituted by 1-27 $R^{229}$;

$R^{218}$ at each occurrence is independently chosen from $C_{1-6}$alkyl optionally substituted by 1-13 $R^{229}$, $C_{2-6}$alkenyl optionally substituted by 1-11 $R^{229}$, $C_{2-6}$alkynyl optionally substituted by 1-9 $R^{229}$, $C_{6-11}$ aryl optionally substituted by 1-11 $R^{229}$, $C_{7-16}$arylalkyl optionally substituted by 1-19 $R^{229}$, $C_{3-11}$cycloalkyl optionally substituted by 1-21 $R^{229}$, $C_{4-17}$cycloalkylalkyl optionally substituted by 1-32 $R^{229}$, 3-15 membered heterocycloalkyl optionally substituted by 1-28 $R^{229}$, 4-21 membered heterocycloalkylalkyl optionally substituted by 1-40 $R^{229}$, 5-15 membered heteroaryl optionally substituted by 1-15 $R^{229}$, and 6-21 membered heteroarylalkyl optionally substituted by 1-27 $R^{229}$;

$R^{212}$ and $R^{213}$ at each occurrence is independently chosen from H, $C_{1-6}$alkyl optionally substituted by 1-13 $R^{239}$, $C_{2-6}$alkenyl optionally substituted by 1-11 $R^{239}$, $C_{2-6}$alkynyl optionally substituted by 1-9 $R^{239}$, $C_{6-11}$aryl optionally substituted by 1-11 $R^{239}$, $C_{7-16}$arylalkyl optionally substituted by 1-19 $R^{239}$, $C_{3-11}$cycloalkyl optionally substituted by 1-21 $R^{239}$, $C_{4-17}$cycloalkylalkyl optionally substituted by 1-32 $R^{239}$, 3-15 membered heterocycloalkyl optionally substituted by 1-28 $R^{239}$, 4-21 membered heterocycloalkylalkyl optionally substituted by 1-40 $R^{239}$, 5-15 membered heteroaryl optionally substituted by 1-15 $R^{239}$, and 6-21 membered heteroarylalkyl optionally substituted by 1-27 $R^{239}$;

or any $R^{212}$ and $R^{213}$ may form, together with the nitrogen atom to which they are attached, a 3-15 membered heterocycloalkyl optionally substituted by 1-28 $R^{249}$ or a 5-15 membered heteroaryl optionally substituted by 1-15 $R^{249}$;

$R^{219}$, $R^{229}$, $R^{239}$ and $R^{249}$ at each occurrence is independently chosen from $C_{1-6}$alkyl optionally substituted by 1-13 halogen, $C_{2-6}$alkenyl, $C_{2-6}$alkynyl, $C_{6-11}$aryl, $C_{7-16}$arylalkyl, $C_{3-11}$ cycloalkyl, $C_{4-17}$cycloalkylalkyl, 3-15 membered heterocycloalkyl, 4-21 membered heterocycloalkylalkyl, 5-15 membered heteroaryl, 6-21 membered heteroarylalkyl, halogen, —CN, —C(=O)$R^{250}$, —C(=O)O$R^{250}$, —C(=O)N$R^{250}R^{250}$, —C(=O)C(=O)$R^{250}$, —C(=N$R^{250}$)$R^{250}$, —C(=N$R^{250}$)N$R^{250}R^{250}$, —C(=NOH)N$R^{250}R^{250}$, —C(=NO$R^{250}$)$R^{250}$, —C(=NN$R^{250}R^{250}$)$R^{250}$, —C(=NN$R^{250}$C(=O)$R^{250}$)$R^{250}$, —C(=NN$R^{250}$C(=O)O$R^{250}$)$R^{250}$, —C(=S)N$R^{250}R^{250}$, —NC, —NO$_2$, —N$R^{250}R^{250}$, —N$R^{250}$N$R^{250}R^{250}$, —N=N$R^{250}$, =N$R^{250}$, =NO$R^{250}$, —N$R^{250}$O$R^{250}$, —N$R^{250}$C(=O)$R^{250}$, —N$R^{250}$C(=O)C(=O)$R^{250}$, —N$R^{250}$C(=O)O$R^{250}$, —N$R^{250}$C(=O)C(=O)O$R^{250}$, —N$R^{250}$C(=O)N$R^{250}R^{250}$, —N$R^{250}$C(=O)N$R^{250}$C(=O)$R^{250}$, —N$R^{250}$C(=O)N$R^{250}$C(=O)O$R^{250}$, —N$R^{250}$C(=N$R^{250}$)N$R^{250}R^{250}$, —N$R^{250}$C(=O)C(=O)N$R^{250}R^{250}$, —N$R^{250}$C(=S)$R^{250}$, —N$R^{250}$C(=S)O$R^{250}$, —N$R^{250}$C(=S)N$R^{250}R^{250}$, —N$R^{250}$S(=O)$_2R^{250}$, —N$R^{250}$S(=O)$_2$N$R^{250}R^{250}$, —N$R^{250}$P(=O)$R^{251}R^{251}$, —N$R^{250}$P(=O)(N$R^{250}R^{250}$)(N$R^{250}R^{250}$), —N$R^{250}$P(=O)(O$R^{250}$)(O$R^{250}$), —N$R^{250}$P(=O)(S$R^{250}$)(S$R^{250}$), —O$R^{250}$, =O, —OCN, —OC(=O)$R^{250}$, —OC(=O)N$R^{250}R^{250}$, —OC(=O)O$R^{250}$, —OC(=N$R^{250}$)N$R^{250}R^{250}$, —OS(=O)$R^{250}$, —OS(=O)$_2R^{250}$, —OS(=O)$_2$O$R^{250}$, —OS(=O)$_2$N$R^{250}R^{250}$, —OP(=O)$R^{251}R^{251}$, —OP(=O)(N$R^{250}R^{250}$)(N$R^{250}R^{250}$), —OP(=O)(O$R^{250}$)(O$R^{250}$), —OP(=O)(S$R^{250}$)(S$R^{250}$), —SCN, =S, —S(=O)$_nR^{250}$, —S(=O)$_2$O$R^{250}$, —SO$_3R^{250}$, —S(=O)$_2$N$R^{250}R^{250}$, —S(=O)N$R^{250}R^{250}$, —SP(=O)$R^{251}R^{251}$, —SP(=O)(N$R^{250}R^{250}$)(N$R^{250}R^{250}$), —SP(=O)(O$R^{250}$)(O$R^{250}$), —SP(=O)(S$R^{250}$)(S$R^{250}$), —P(=O)$R^{251}R^{251}$, —P(=O)(N$R^{250}R^{250}$)(N$R^{250}R^{250}$), —P(=O)(O$R^{250}$)(O$R^{250}$), and —P(=O)(S$R^{250}$)(S$R^{250}$);

$R^{250}$ at each occurrence is independently chosen from H, $C_{1-6}$alkyl and $C_{1-6}$-haloalkyl;

$R^{251}$ at each occurrence is independently chosen from $C_{1-6}$alkyl and $C_{1-6}$-haloalkyl; and n at each occurrence is independently chosen from 0, 1, and 2;

with the proviso that the compound is not:

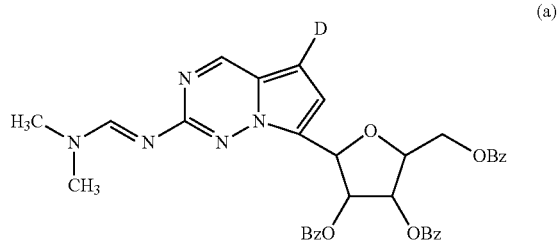

(a)

wherein
Bz is benzoyl, and
D is —C(=O)H or H,

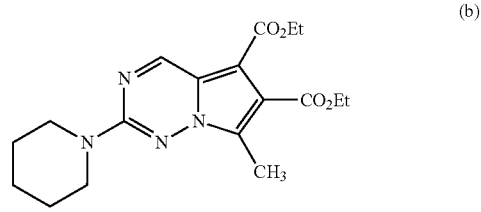

(b)

wherein Et is ethyl, or

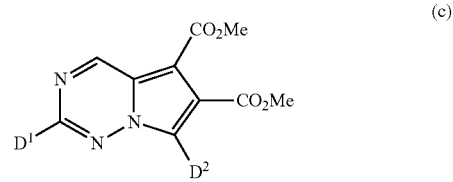

(c)

wherein
$D^1$ is methoxy, phenyl, or 4-methylphenyl,
$D^2$ is —CH$_2$C(=O)OMe or —C(=O)OMe, and
Me is methyl.

In one embodiment, at least one of $Q^2$, $Q^3$, and $Q^4$ is not H. In another embodiment, one of $Q^2$, $Q^3$, and $Q^4$ is not H. In another embodiment, two of $Q^2$, $Q^3$, and $Q^4$ are not H. In another embodiment, neither $Q^2$, $Q^3$, nor $Q^4$ is H. In another embodiment, neither $Q^1$, $Q^2$, $Q^3$, nor $Q^4$ is —C(C(=O)-A-$X^1$)=C($X^4$)—(B)$_{16}$—$X^2$, —C(C(=O)-A-$X^1$)=N—(B)$_{16}$—$X^2$, —C(=O)C(=O)-A-$X^1$, or

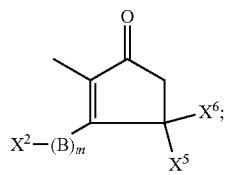

wherein: (a) A and B at each occurrence are independently chosen from —O—, —S—, and —NX$^3$—, (b) X$^1$, X$^2$, X$^3$, X$^4$, X$^5$, and X$^6$ at each occurrence are independently chosen from H, C$_{1-4}$alkyl, and C$_{1-4}$haloalkyl, and (c) m is 0 or 1. In another embodiment, neither group of formula (A), (B), (C), (D), (E) or (F):

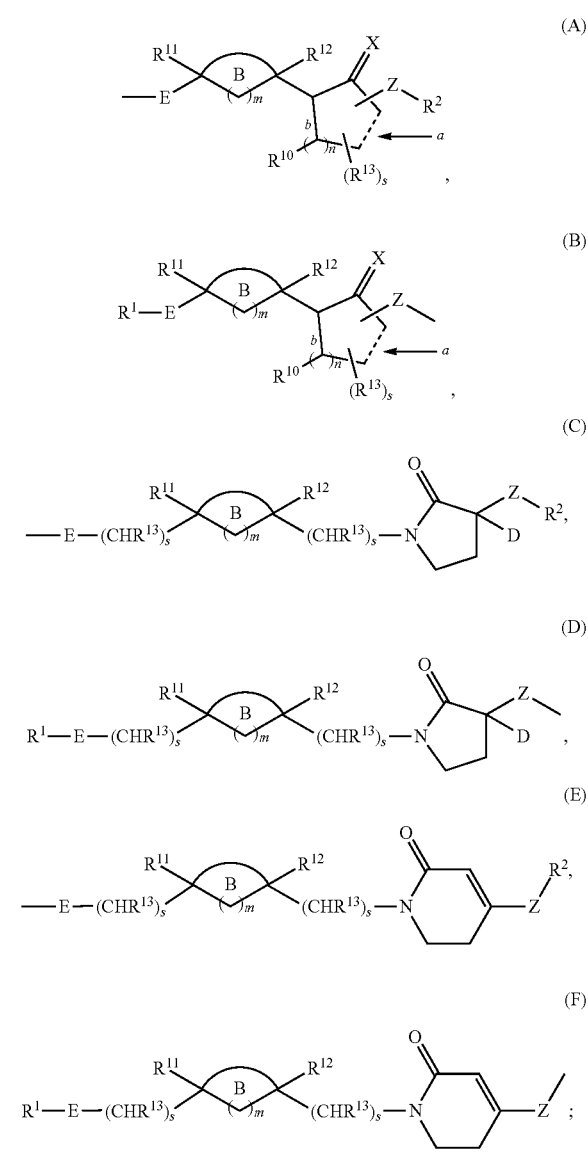

wherein D is H or methyl, and R$^1$, R$^2$, R$^{10}$, R$^{11}$, R$^{12}$, R$^{13}$, a, b, B, E, m, n, s, X and Z are as defined in WO 2004/071460. In another embodiment, neither Q$^1$, Q$^2$, Q$^3$ nor Q$^4$ is a group of formula (A), (B), (C) or (D):

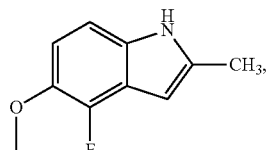

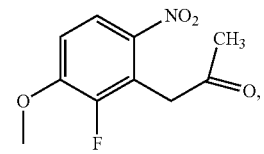

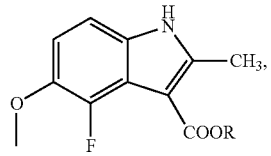

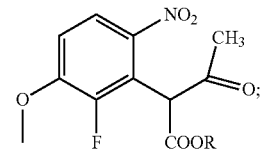

wherein R is an esterifying group such as C$_{1-6}$alkyl or benzyl.

In each embodiment of the present invention that is described in the paragraphs that precede or follow this paragraph, the definition of Q$^1$ may be chosen from any of the embodiments that are described in this paragraph. In one embodiment, Q$^1$ is -L$^1$-A$^1$-G$^1$-X$^1$—Z$^1$. In another embodiment, Q$^1$ is -A$^1$-G$^1$-X$^1$—Z$^1$. In another embodiment, Q$^1$ is -L$^1$-A$^1$-X$^1$—Z$^1$. In another embodiment, Q$^1$ is -L$^1$-A$^1$-G$^1$-Z$^1$. In another embodiment, Q$^1$ is -L$^1$-A$^1$-Z$^1$. In another embodiment, Q$^1$ is -A$^1$-Z$^1$. In another embodiment, Q$^1$ is not C$_{1-3}$alkyl, C$_{1-3}$alkoxy, C$_{1-2}$haloalkoxy, or C$_{1-2}$alkyl substituted with —OCH$_3$, —SCH$_3$ or —CN. In another embodiment, Q$^1$ is not C$_{1-3}$alkyl. In another embodiment, Q$^1$ is not an alkylsulfonyloxy or arylsulfonyloxy leaving group such as triflyloxy or p-tosyloxy.

In each embodiment of the present invention that is described in the paragraphs that precede or follow this paragraph, the definition of Q$^2$ may be chosen from any of the embodiments that are described in this paragraph. In one embodiment, Q$^2$ is -L$^2$-A$^2$-G$^2$-X$^2$—Z$^2$. In another embodiment, Q$^2$ is -A$^2$-G$^2$-X$^2$—Z$^2$. In another embodiment, Q$^2$ is -G$^2$-X$^2$—Z$^2$. In another embodiment, Q$^2$ is —X$^2$—Z$^2$. In another embodiment, Q$^2$, is Z$^2$. In another embodiment, Q$^2$ is -L$^2$-Z$^2$. In another embodiment, Q$^2$ is -L$^2$-A$^2$-Z$^2$. In another embodiment, Q$^2$ is -L$^2$-A$^2$-G$^2$-Z$^2$. In another embodiment, Q$^2$ is -A$^2$-Z$^2$. In another embodiment, Q$^2$ is not H. In another embodiment, Q$^2$ is H. In another embodiment, Q$^2$ is not

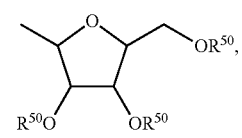

wherein R$^{50}$ is as defined herein. In another embodiment, Q$^2$ is not —S(=O)$_2$NH$_2$, —S(=O)$_2$NHC(=O)O-phenyl, —S(=O)$_2$NHC(=S)O-phenyl, —S(=O)$_2$Cl, —NO$_2$, Cl, Br, I, H, —S(=O)$_2$NHC(=O)NX$^1$X$^2$, or —S(=O)$_2$NHC(=S)NX$^1$X$^2$, wherein X$^1$ is H or CH$_3$ and X$^2$ is substituted or unsubstituted heteroaryl. In another embodiment, Q$^2$ is not —S(=O)$_2$NH$_2$, —S(=O)$_2$NHC(=O)O-phenyl, —S(=O)$_2$NHC(=S)O-phenyl, —S(=O)$_2$Cl, —NO$_2$, Cl, Br, I, —S(=O)$_2$NHC(=O)NX$^1$X$^2$, or —S(=O)$_2$NHC(=S)NX$^1$X$^2$, wherein X$^1$ is H or CH$_3$ and X$^2$ is substituted or unsubstituted heteroaryl. In another embodiment, Q$^2$ is not —C(=W)NRS(=O)$_2$L or —C(G)=NS(=O)$_2$L, wherein: (a) R is H; C$_{1-3}$alkyl optionally substituted by one or more halogens; C$_{1-3}$thioalkyl optionally substituted by one or more halogens; benzyl optionally substituted by one or more groups chosen from F, Cl, —OCH$_3$, —SCH$_3$, and —NO$_2$; allyl; propargyl; —C(=O)C$_{1-3}$alkyl; —C(=O)OCH$_3$; or —C(=O)OCH$_2$CH$_3$; (b) G is Cl, OR' or SR'; (c) R' is C$_{1-3}$alkyl optionally substituted by one or more halogens; (d) W is O, S, NR" or NOR"; (e) R" is H or C$_{1-3}$alkyl optionally substituted with one or more halogens; and (f) L is optionally substituted aryl or optionally substituted heteroaryl. In another embodiment, Q$^2$ is not H, Br, or —C(=O)OM, wherein M is H, Li, K, Na, Cl, imidazolyl, C$_{1-5}$alkyl, benzyl, or

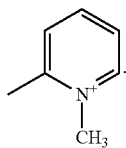

In another embodiment, Q$^2$ is not a group of formula (A), (B), or (C):

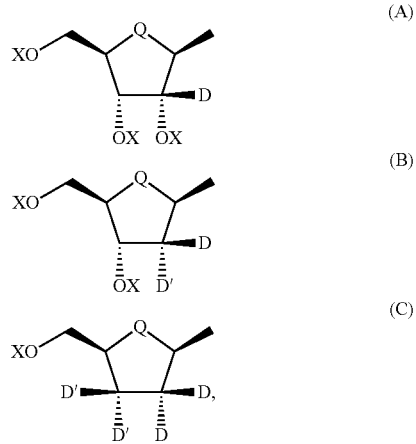

wherein Q is O, S, SO$_2$ or CH$_2$; X is R$^{50}$, —CN, —C(=O)R$^{50}$, —C(=O)NR$^{52}$R$^{53}$, —C(=O)OR$^{50}$, —C(=NR$^{55}$)NR$^{52}$R$^{53}$, —S(=O)R$^{50}$, —S(=O)$_2$R$^{50}$, —S(=O)$_2$OR$^{50}$, or —S(=O)$_2$NR$^{52}$R$^{53}$; each D is independently chosen from R$^b$; and each D' is independently chosen from H and R$^b$; wherein R$^{50}$, R$^{52}$, R$^{53}$, R$^{55}$, and R$^b$ are as defined herein.

In each embodiment of the present invention that is described in the paragraphs that precede or follow this paragraph, the definition of Q$^3$ may be chosen from any of the embodiments that are described in this paragraph. In one embodiment, Q$^3$ is -L$^3$-A$^3$-G$^3$-X$^3$—Z$^3$. In another embodiment, Q$^3$ is -A$^3$-G$^3$-X$^3$—Z$^3$. In another embodiment, Q$^3$ is -G$^3$-X$^3$—Z$^3$. In another embodiment, Q$^3$ is —X$^3$—Z$^3$. In another embodiment, Q$^3$ is Z$^3$. In another embodiment, Q$^3$ is -L$^3$-Z$^3$. In another embodiment, Q$^3$ is -L$^3$-A$^3$-Z$^3$. In another embodiment, Q$^3$ is -L$^3$-A$^3$-G$^3$-Z$^3$. In another embodiment, Q$^3$ is -A$^3$-Z$^3$. In another embodiment, Q$^3$ is not H. In another embodiment, Q$^3$ is H.

In each embodiment of the present invention that is described in the paragraphs that precede or follow this paragraph, the definition of Q$^4$ may be chosen from any of the embodiments that are described in this paragraph. In one embodiment, Q$^4$ is -L$^4$-A$^4$-G$^4$-X$^4$—Z$^4$. In another embodiment, Q$^4$ is -A$^4$-G$^4$-X$^4$—Z$^4$. In another embodiment, Q$^4$ is -G$^4$X$^4$—Z$^4$. In another embodiment, Q$^4$ is —X$^4$—Z$^4$. In another embodiment, Q$^4$ is Z$^4$. In another embodiment, Q$^4$ is -L$^4$-Z$^4$. In another embodiment, Q$^4$ is -L$^4$-A$^4$-Z$^4$. In another embodiment, Q$^4$ is -L$^4$-A$^4$-G$^4$-Z$^4$. In another embodiment, Q$^4$ is -A$^4$-Z$^4$. In another embodiment, Q$^4$ is not H. In another embodiment, Q$^4$ is H. In another embodiment, when Q$^1$ is C$_{1-6}$alkyl, C$_{6-11}$aryl, —OC$_{1-6}$alkyl, —NHC$_{1-6}$alkyl, or —N(C$_{1-6}$alkyl)$_2$, then Q$^4$ is not -A-D; wherein: (a) A is —C(=O)—, —CRR'—, —O—, —NR—, —S—, —SO—, or —SO$_2$—; (b) D is C$_{6-11}$aryl or 5-15 membered heteroaryl; (c) R and R' are independently chosen from H, C$_{1-6}$alkyl, C$_{2-6}$alkenyl, C$_{2-6}$alkynyl, C$_{6-11}$aryl, 5-15 membered heteroaryl, C$_{3-11}$cycloalkyl, 3-15 membered heterocycloalkyl, —SO$_3$R$_a$, —SO$_2$R$_a$, —SO$_2$NR$_a$R$_b$, —C(=O)R$_a$, —C(=O)OR$_a$, and —C(=O)NR$_a$R$_b$; (d) each R$_a$ and R$_b$ is independently chosen from H, C$_{1-6}$alkyl, C$_{2-6}$alkenyl, C$_{2-6}$alkynyl, C$_{6-11}$aryl, 5-15 membered heteroaryl, C$_{3-11}$cycloalkyl, and 3-15 membered heterocycloalkyl; and (e) each C$_{1-6}$alkyl, C$_{2-6}$alkenyl, C$_{2-6}$alkynyl, C$_{6-11}$aryl, 5-15 membered heteroaryl, C$_{3-11}$cycloalkyl, 3-15 membered heterocycloalkyl is optionally substituted.

In each embodiment of the present invention that is described in the paragraphs that precede or follow this paragraph, the definition of L$^1$ may be chosen from any of the embodiments that are described in this paragraph. In one embodiment, L$^1$ is C$_{1-6}$alkylene optionally substituted by 1-12 R$^9$, C$_{2-6}$alkenylene optionally substituted by 1-10 R$^9$, C$_{2-6}$alkynylene optionally substituted by 1-8 R$^9$, C$_{6-11}$arylene optionally substituted by 1-10 R$^9$, C$_{7-16}$aryla- lkylene optionally substituted by 1-18 R$^9$, C$_{3-11}$cycloalkylene optionally substituted by 1-20 R$^9$, C$_{4-17}$cycloalkylalkylene optionally substituted by 1-31 R$^9$, 3-15 membered heterocycloalkylene optionally substituted by 1-27 R$^9$, 4-21 membered heterocycloalkylalkylene optionally substituted by 1-39 R$^9$, 5-15 membered heteroarylene optionally substituted by 1-14 R$^9$, 6-21 membered heteroarylalkylene optionally substituted by 1-26 R$^9$, —C$_{0-3}$alkylC(=O)C$_{0-3}$alkyl-, —C$_{0-3}$alkylC(=O)OC$_{0-3}$alkyl-, —C$_{0-3}$alkylC(=O)NR$^4$C$_{0-3}$alkyl-, —C$_{0-3}$alkylC(=O)C(=O)C$_{0-3}$alkyl-, —C$_{0-3}$alkylC(=NR$^5$)C$_{0-3}$alkyl-, —C$_{0-3}$alkylC(=NR$^5$)NR$^4$C$_{0-3}$alkyl-, —C$_{0-3}$alkylC(=NOH)NR$^4$C$_{0-3}$alkyl-, —C$_{0-3}$alkylC(=NOR$^6$)C$_{0-3}$alkyl-, —C$_{0-3}$alkylC(=NNR$^2$R$^3$)C$_{0-3}$alkyl-, —C$_{0-3}$alkylC(=NNR$^4$C(=O)R$^1$)C$_{0-3}$alkyl-, —C$_{0-3}$alkylC(=NNR$^4$C(=O)OR$^1$)C$_{0-3}$alkyl-, —C$_{0-3}$alkylC(=S)NR$^4$C$_{0-3}$alkyl-, —C$_{0-3}$alkylNR$^4$C$_{0-3}$alkyl-, —C$_{0-3}$alkylNR$^4$NR$^4$C$_{0-3}$alkyl-, —C$_{0-3}$alkylN=NC$_{0-3}$alkyl-, —C$_{0-3}$ alkylNR$^4$C(=O)C$_{0-3}$alkyl-, —C$_{0-3}$alkylNR$^4$C(=O)C(=O)C$_{0-3}$alkyl-, —C$_{0-3}$alkylNR$^4$C(=O)OC$_{0-3}$alkyl-, —C$_{0-3}$alkylNR$^4$C(=O)C(=O)OC$_{0-3}$alkyl-, —C$_{0-3}$alkylNR$^4$C(=O)NR$^4$C$_{0-3}$alkyl-, —C$_{0-3}$alkylNR$^4$C(=O)NR$^4$C(=O)C$_{0-3}$alkyl-, —C$_{0-3}$alkylNR$^4$C(=O)NR$^4$C(=O)OC$_{0-3}$alkyl-, —C$_{0-3}$alkylNR$^4$C(=NR$^5$)NR$^4$C$_{0-3}$alkyl-, —C$_{0-3}$alkylNR$^4$C(=O)C(=O)NR$^4$C$_{0-3}$alkyl-, —C$_{0-3}$alkylNR$^4$C(=S)C$_{0-3}$alkyl-, —C$_{0-3}$alkylNR$^4$C(=S)OC$_{0-3}$alkyl-, —C$_{0-3}$ alkylNR$^4$C(=S)NR$^4$C$_{0-3}$alkyl-, —C$_{0-3}$alkylNR$^4$S(=O)$_2$C$_{0-3}$alkyl-, —C$_{0-3}$alkylNR$^4$S(=O)$_2$ $NR^4C_{0-3}$alkyl-, —$C_{0-3}$alkyl$OC_{0-3}$alkyl-, —$C_{0-3}$alkylOC(=O)$C_{0-3}$alkyl-, —$C_{0-3}$alkylOC(=O)$NR^4C_{0-3}$alkyl-, —$C_{0-3}$alkylOC(=O)$OC_{0-3}$alkyl-, —$C_{0-3}$alkylOC(=$NR^5$)$NR^4C_{0-3}$alkyl-, —$C_{0-3}$alkylOS(=O)$C_{0-3}$alkyl-, —$C_{0-3}$alkylOS(=O)$_2C_{0-3}$alkyl-, —$C_{0-3}$alkylOS(=O)$_2OC_{0-3}$alkyl-, —$C_{0-3}$alkylOS(=O)$_2NR^4C_{0-3}$alkyl-, —$C_{0-3}$alkylS(=O)—$C_{0-3}$alkyl-, —$C_{0-3}$alkylS(=O)$_2OC_{0-3}$alkyl-, —$C_{0-3}$alkylSO$_3C_{0-3}$alkyl-, —$C_{0-3}$alkylS(=O)$_2NR^4C_{0-3}$alkyl-, —$C_{0-3}$alkylS(=O)$NR^4C_{0-3}$alkyl-, or absent. In another embodiment, $L^1$ is $C_{1-6}$alkylene optionally substituted by 1-12 $R^9$, $C_{7-16}$arylalkylene optionally substituted by 1-18 $R^9$, $C_{3-11}$cycloalkylene optionally substituted by 1-20 $R^9$, $C_{4-17}$cycloalkylalkylene optionally substituted by 1-31 $R^9$, 3-15 membered heterocycloalkylene optionally substituted by 1-27 $R^9$, 4-21 membered heterocycloalkylalkylene optionally substituted by 1-39 $R^9$, 5-15 membered heteroarylene optionally substituted by 1-14 $R^9$, 6-21 membered heteroarylalkylene optionally substituted by 1-26 $R^9$, —$C_{0-3}$alkylC(=O)$C_{0-3}$alkyl-, —$C_{0-3}$alkylC(=O)$OC_{0-3}$alkyl-, —$C_{0-3}$alkylC(=O)$NR^4C_{0-3}$alkyl-, —$C_{0-3}$alkylC(=O)$C(=O)C_{0-3}$alkyl-, —$C_{0-3}$alkylC(=S)$NR^4C_{0-3}$alkyl-, —$C_{0-3}$alkylNR$^4C_{0-3}$alkyl-, —$C_{0-3}$alkylNR$^4NR^4C_{0-3}$alkyl-, —$C_{0-3}$alkylNR$^4C$(=O)$C_{0-3}$alkyl-, —$C_{0-3}$alkylNR$^4C$(=O)$C$(=O)$C_{0-3}$alkyl-, —$C_{0-3}$alkylNR$^4C$(=O)$OC_{0-3}$alkyl-, —$C_{0-3}$alkylNR$^4C$(=O)$C$(=O)$OC_{0-3}$alkyl-, —$C_{0-3}$alkylNR$^4C$(=O)$NR^4C_{0-3}$alkyl-, —$C_{0-3}$alkylNR$^4C$(=O)$NR^4C$(=O)$C_{0-3}$alkyl-, —$C_{0-3}$alkylNR$^4C$(=O)$NR^4C$(=O)$OC_{0-3}$alkyl-, —$C_{0-3}$alkylNR$^4C$(=O)$C$(=O)$NR^4C_{0-3}$alkyl-, —$C_{0-3}$alkylNR$^4C$(=S)$C_{0-3}$alkyl-, —$C_{0-3}$alkylNR$^4C$(=S)$OC_{0-3}$alkyl-, —$C_{0-3}$alkylNR$^4C$(=S)$NR^4C_{0-3}$alkyl-, —$C_{0-3}$alkylNR$^4S$(=O)$_2 C_{0-3}$alkyl-, —$C_{0-3}$alkylNR$^4S$(=O)$_2 NR^4C_{0-3}$alkyl-, —$C_{0-3}$alkylOC$_{0-3}$alkyl-, —$C_{0-3}$alkylOC(=O)$C_{0-3}$alkyl-, —$C_{0-3}$alkylOC(=O)$NR^4C_{0-3}$alkyl-, —$C_{0-3}$alkylOC(=O)$OC_{0-3}$alkyl-, —$C_{0-3}$alkylOS(=O)$C_{0-3}$alkyl-, —$C_{0-3}$alkylOS(=O)$_2C_{0-3}$alkyl-, —$C_{0-3}$alkylOS(=O)$_2OC_{0-3}$alkyl-, —$C_{0-3}$alkylOS(=O)$_2NR^4C_{0-3}$alkyl-, —$C_{0-3}$alkylS(=O)—$C_{0-3}$alkyl-, —$C_{0-3}$alkylS(=O)$_2OC_{0-3}$alkyl-, —$C_{0-3}$alkylSO$_3C_{0-3}$alkyl-, —$C_{0-3}$alkylS(=O)$_2NR^4C_{0-3}$alkyl-, —$C_{0-3}$alkylS(=O)$NR^4C_{0-3}$alkyl-, or absent. In another embodiment, $L^1$ is $C_{1-6}$alkylene optionally substituted by 1-12 $R^9$, 3-15 membered heterocycloalkylene optionally substituted by 1-27 $R^9$, 4-21 membered heterocycloalkylalkylene optionally substituted by 1-39 $R^9$, 5-15 membered heteroarylene optionally substituted by 1-14 $R^9$, 6-21 membered heteroarylalkylene optionally substituted by 1-26 $R^9$, —$C_{0-3}$alkylNR$^4C_{0-3}$alkyl-, —$C_{0-3}$alkylNR$^4NR^4C_{0-3}$alkyl-, —$C_{0-3}$alkylNR$^4C$(=O)$C_{0-3}$alkyl-, —$C_{0-3}$alkylNR$^4C$(=O)$OC_{0-3}$alkyl-, —$C_{0-3}$lkylNR$^4C$(=O)$NR^4C_{0-3}$alkyl-, —$C_{0-3}$alkylNR$^4C$(=O)$NR^4C$(=O)$C_{0-3}$alkyl-, —$C_{0-3}$alkylNR$^4C$(=S)$C_{0-3}$alkyl-, —$C_{0-3}$alkylNR$^4C$(=S)$NR^4C_{0-3}$alkyl-, —$C_{0-3}$alkylNR$^4S$(=O)$_2C_{0-3}$alkyl-, —$C_{0-3}$alkylOC$_{0-3}$alkyl-, —$C_{0-3}$alkylS(=O)$_nC_{0-3}$alkyl-, or absent. In another embodiment, $L^1$ is $C_{1-6}$alkylene optionally substituted by 1-6 $R^9$, $C_{7-16}$arylalkylene optionally substituted by 1-6 $R^9$, $C_{3-11}$cycloalkylene optionally substituted by 1-6 $R^9$, $C_{4-17}$cycloalkylalkylene optionally substituted by 1-6 $R^9$, 3-15 membered heterocycloalkylene optionally substituted by 1-6 $R^9$, 4-21 membered heterocycloalkylalkylene optionally substituted by 1-6 $R^9$, 5-15 membered heteroarylene optionally substituted by 1-6 $R^9$, 6-21 membered heteroarylalkylene optionally substituted by 1-6 $R^9$, —C(=O)—, —C(=O)O—, —C(=O)NR$^4$—, —C(=O)C(=S)—, —C(=S)NR$^4$—, —NR$^4$—, —NR$^4$NR$^4$—, —NR$^4$C(=O)—, —NR$^4$C(=O)C(=O)—, —NR$^4$C(=O)O—, —NR$^4$C(=O)C(=O)O—, —NR$^4$C(=O)NR$^4$—, —NR$^4$C(=O)NR$^4$C(=O)—, —NR$^4$C(=O)NR$^4$C(=O)O—, —NR$^4$C(=O)C(=O)NR$^4$—, —NR$^4$C(=S)—, —NR$^4$C(=S)O—, —NR$^4$C(=S)NR$^4$—, —NR$^4$S(=O)$_2$—, —NR$^4$S(=O)$_2$NR$^4$—, —O—, —OC(=O)—, —OC(=O)NR$^4$—, —OC(=O)O—, —OS(=O)—, —OS(=O)$_2$—, —OS(=O)$_2$O—, —OS(=O)$_2$NR$^4$—, —S(=O)$_n$—, —S(=O)$_2$O—, —SO$_3$—, —S(=O)$_2$NR$^4$—, —S(=O)NR$^4$—, or absent. In another embodiment, $L^1$ is $C_{1-6}$alkylene optionally substituted by 1-6 $R^9$, $C_{7-16}$arylalkylene optionally substituted by 1-6 $R^9$, $C_{3-11}$cycloalkylene optionally substituted by 1-6 $R^9$, $C_{4-17}$cycloalkylalkylene optionally substituted by 1-6 $R^9$, 3-15 membered heterocycloalkylene optionally substituted by 1-6 $R^9$, 4-21 membered heterocycloalkylalkylene optionally substituted by 1-6 $R^9$, 5-15 membered heteroarylene optionally substituted by 1-6 $R^9$, 6-21 membered heteroarylalkylene optionally substituted by 1-6 $R^9$, —C(=O)—, —C(=O)O—, —C(=O)NR$^4$—, —C(=S)NR$^4$—, —NR$^4$—, —NR$^4$NR$^4$—, —NR$^4$C(=O)—, —NR$^4$C(=O)O—, —NR$^4$C(=O)NR$^4$—, —NR$^4$C(=O)NR$^4$C(=O)—, —NR$^4$C(=S)—, —NR$^4$C(=S)O—, —NR$^4$C(=S)NR$^4$—, —NR$^4$S(=O)$_2$—, —O—, —OC(=O)—, —OC(=O)NR$^4$—, —S(=O)$_n$—, —S(=O)$_2$NR$^4$—, —S(=O)NR$^4$—, or absent. In another embodiment, $L^1$ is $C_{1-6}$alkylene optionally substituted by 1-6 $R^9$, 3-15 membered heterocycloalkylene optionally substituted by 1-6 $R^9$, 4-21 membered heterocycloalkylalkylene optionally substituted by 1-6 $R^9$, 5-15 membered heteroarylene optionally substituted by 1-6 $R^9$, 6-21 membered heteroarylalkylene optionally substituted by 1-6 $R^9$, —NR$^4$—, —NR$^4$NR$^4$—, —NR$^4$C(=O)—, —NR$^4$C(=O)O—, —NR$^4$C(=O)NR$^4$—, —NR$^4$C(=O)NR$^4$C(=O)—, —NR$^4$C(=S)—, —NR$^4$C(=S)NR$^4$—, —NR$^4$S(=O)$_2$—, —O—, —S(=O)$_n$—, or absent. In another embodiment, $L^1$ is $C_{1-6}$alkylene optionally substituted by 1-6 $R^9$, 3-15 membered heterocycloalkylene optionally substituted by 1-6 $R^9$, 4-21 membered heterocycloalkylalkylene optionally substituted by 1-6 $R^9$, 5-15 membered heteroarylene optionally substituted by 1-6 $R^9$, 6-21 membered heteroarylalkylene optionally substituted by 1-6 $R^9$, —NR$^4$—, —NR$^4$NR$^4$—, —NR$^4$C(=O)—, —NR$^4$C(=O)

O—, —NR$^4$C(=O)NR$^4$—, —NR$^4$C(=O)NR$^4$C(=O)—, —NR$^4$C(=S)—, —NR$^4$C(=S)NR$^4$—, —NR$^4$S(=O)$_2$—, —C$_{0-3}$alkylOC$_{0-3}$alkyl-, —S(=O)$_n$—, or absent. In another embodiment, L$^1$ is C$_{1-6}$alkylene optionally substituted by 1-6 R$^9$, —NR$^4$—, —NR$^4$NR$^4$—, —NR$^4$C(=O)—, —NR$^4$C(=O)O—, —NR$^4$C(=O)NR$^4$—, —NR$^4$C(=O)NR$^4$C(=O)—, —NR$^4$C(=S)—, —NR$^4$C(=S)NR$^4$—, —NR$^4$S(=O)$_2$—, —O—, —S(=O)$_n$—, or absent. In another embodiment, L$^1$ is 5-15 membered heteroarylene optionally substituted by 1-6 R$^9$, —C$_{0-3}$alkylNR$^4$C$_{0-3}$alkyl-, —NR$^4$NR$^4$—, —NR$^4$C(=O)—, —NR$^4$C(=O)O—, —NR$^4$C(=O)NR$^4$—, —NR$^4$C(=O)NR$^4$C(=O)—, —NR$^4$C(=S)—, —NR$^4$C(=S)NR$^4$—, —NR$^4$S(=O)$_2$—, —C$_{0-3}$alkylOC$_{0-3}$alkyl-, —S(=O)$_n$—, or absent. In another embodiment, L$^1$ is 5-15 membered heteroarylene optionally substituted by 1-6 R$^9$, —C$_{0-3}$alkylNR$^4$—, —NR$^4$NR$^4$—, —NR$^4$C(=O)—, —NR$^4$C(=O)O—, —NR$^4$C(=O)NR$^4$—, —NR$^4$C(=O)NR$^4$C(=O)—, —NR$^4$C(=S)—, —NR$^4$C(=S)NR$^4$—, —NR$^4$S(=O)$_2$—, —OC$_{0-3}$alkyl-, —S(=O)$_n$—, or absent. In another embodiment, L$^1$ is 5-6 membered heteroarylene optionally substituted by 1-6 R$^9$, —C$_{0-3}$alkylNR$^4$C$_{0-3}$alkyl-, —NR$^4$C(=O)NR$^4$—, —C$_{0-3}$alkylOC$_{0-3}$alkyl-, or absent. In another embodiment, L$^1$ is 5 membered heteroarylene optionally substituted by 1-6 R$^9$, —C$_{0-3}$alkylNR$^4$C$_{0-3}$alkyl-, —NR$^4$C(=O)NR$^4$—, —C$_{0-3}$alkylOC$_{0-3}$alkyl-, or absent. In another embodiment, L$^1$ is —C$_{0-3}$alkylNR$^4$C$_{0-3}$alkyl-, —NR$^4$NR$^4$—, —NR$^4$C(=O)—, —NR$^4$C(=O)O—, —NR$^4$C(=O)NR$^4$—, —NR$^4$C(=O)NR$^4$C(=O)—, —NR$^4$C(=S)—, —NR$^4$C(=S)NR$^4$—, —NR$^4$S(=O)$_2$—, —C$_{0-3}$alkylOC$_{0-3}$alkyl-, —S(=O)$_n$—, or absent. In another embodiment, L$^1$ is —C$_{0-3}$alkylNR$^4$—, —NR$^4$NR$^4$—, —NR$^4$C(=O)—, —NR$^4$C(=O)O—, —NR$^4$C(=O)NR$^4$—, —NR$^4$C(=O)NR$^4$C(=O)—, —NR$^4$C(=S)—, —NR$^4$C(=S)NR$^4$—, —NR$^4$S(=O)$_2$—, —OC$_{0-3}$alkyl-, —S(=O)$_n$—, or absent. In another embodiment, L$^1$ is —C$_{0-3}$alkylNR$^4$C$_{0-3}$alkyl-, —NR$^4$C(=O)NR$^4$—, —C$_{0-3}$alkylOC$_{0-3}$alkyl-, or absent. In another embodiment, L$^1$ is —C$_{0-3}$alkylNR$^4$C$_{0-3}$alkyl-, —NR$^4$C(=O)NR$^4$—, —C$_{0-3}$alkylOC$_{0-3}$alkyl-, or absent. In another embodiment, L$^1$ is —NR$^4$—, —NR$^4$C(=O)NR$^4$—, —O—, or absent. In another embodiment, L$^1$ is —NR$^4$—, —NR$^4$C(=O)NR$^4$—, or —O—. In another embodiment, L$^1$ is —NH—, —NHC(=O)NH—, or —O—. In another embodiment, L$^1$ is —NR$^4$—, —O—, or absent. In another embodiment, L$^1$ is —NR$^4$— or —O—. In another embodiment, L$^1$ is —NH—, —CH$_2$—, —S—, —O—, or absent. In another embodiment, L$^1$ is —NH—, —CH$_2$—, —S—, or —O—. In another embodiment, L$^1$ is —NH—, —O—, or absent. In another embodiment, L$^1$ is —NH— or —O—. In another embodiment, L$^1$ is —NH—.

In each embodiment of the present invention that is described in the paragraphs that precede or follow this paragraph, the definition of A$^1$ may be chosen from any of the embodiments that are described in this paragraph. In one embodiment, A$^1$ is C$_{1-6}$alkylene optionally substituted by 1-12 R$^a$, C$_{2-6}$alkenylene optionally substituted by 1-10 R$^a$, C$_{2-6}$alkynylene optionally substituted by 1-8 R$^a$, C$_{6-11}$arylene optionally substituted by 1-10 R$^a$, C$_{7-16}$arylalkylene optionally substituted by 1-18 R$^a$, C$_{3-11}$cycloalkylene optionally substituted by 1-20 R$^a$, C$_{4-17}$cycloalkylalkylene optionally substituted by 1-31 R$^a$, 3-15 membered heterocycloalkylene optionally substituted by 1-27 R$^a$, 4-21 membered heterocycloalkylalkylene optionally substituted by 1-39 R$^a$, 5-15 membered heteroarylene optionally substituted by 1-14 R$^a$, or 6-21 membered heteroarylalkylene optionally substituted by 1-26 R$^a$. In another embodiment, A$^1$ is C$_{1-6}$alkylene optionally substituted by 1-12 R$^a$, C$_{6-11}$arylene optionally substituted by 1-6 R$^a$, C$_{7-16}$arylalkylene optionally substituted by 1-18 R$^a$, C$_{3-11}$cycloalkylene optionally substituted by 1-20 R$^a$, C$_{4-6}$cycloalkylalkylene optionally substituted by 1-31 R$^a$, 3-15 membered heterocycloalkylene optionally substituted by 1-27 R$^a$, 4-21 membered heterocycloalkylalkylene optionally substituted by 1-39 R$^a$, 5-15 membered heteroarylene optionally substituted by 1-14 R$^a$, or 6-21 membered heteroarylalkylene optionally substituted by 1-26 R$^a$. In another embodiment, A$^1$ is C$_{1-6}$alkylene optionally substituted by 1-12 R$^a$, C$_{6-11}$arylene optionally substituted by 1-6 R$^a$, C$_{7-16}$arylalkylene optionally substituted by 1-18 R$^a$, C$_{3-11}$cycloalkylene optionally substituted by 1-20 R$^a$, C$_{4-17}$cycloalkylalkylene optionally substituted by 1-31 R$^a$, 3-15 membered heterocycloalkylene optionally substituted by 1-27 R$^a$, 4-21 membered heterocycloalkylalkylene optionally substituted by 1-39 R$^a$, 5-15 membered heteroarylene optionally substituted by 1-14 R$^a$, or 6-21 membered heteroarylalkylene optionally substituted by 1-26 R$^a$. In another embodiment, A$^1$ is C$_{1-6}$alkylene optionally substituted by 1-12 R$^a$, C$_{6-11}$arylene optionally substituted by 1-6 R$^a$, C$_{7-16}$arylalkylene optionally substituted by 1-18 R$^a$, 5-15 membered heteroarylene optionally substituted by 1-14 R$^a$, or 6-21 membered heteroarylalkylene optionally substituted by 1-26 R$^a$. In another embodiment, A$^1$ is C$_{1-6}$alkylene optionally substituted by 1-12 R$^a$, C$_{6-11}$arylene optionally substituted by 1-6 R$^a$, C$_{7-16}$arylalkylene optionally substituted by 1-18 R$^a$, 5-15 membered heteroarylene optionally substituted by 1-14 R$^a$, or 6-21 membered heteroarylalkylene optionally substituted by 1-26 R$^a$. In another embodiment, A$^1$ is C$_{1-6}$alkylene optionally substituted by 1-6 R$^a$, C$_{6-11}$arylene optionally substituted by 1-6 R$^a$, C$_{7-16}$arylalkylene optionally substituted by 1-6 R$^a$, C$_{3-11}$cycloalkylene optionally substituted by 1-6 R$^a$, C$_{4-17}$cycloalkylalkylene optionally substituted by 1-6 R$^a$, 3-15 membered heterocycloalkylene optionally substituted by 1-6 R$^a$, 4-21 membered heterocycloalkylalkylene optionally substituted by 1-6 R$^a$, 5-15 membered heteroarylene optionally substituted by 1-6 R$^a$, or 6-21 membered heteroarylalkylene optionally substituted by 1-6 R$^a$. In another embodiment, A$^1$ is C$_{1-6}$alkylene optionally substituted by 1-6 R$^a$, C$_{6-11}$arylene optionally substituted by 1-6 R$^a$, C$_{7-16}$arylalkylene optionally substituted by 1-6 R$^a$, C$_{3-11}$cycloalkylene optionally substituted by 1-6 R$^a$, C$_{4-17}$cycloalkylalkylene optionally substituted by 1-6 R$^a$, 3-15 membered heterocycloalkylene optionally substituted by 1-6 R$^a$, 4-21 membered heterocycloalkylalkylene optionally substituted by 1-6 R$^a$, 5-15 membered heteroarylene optionally substituted by 1-6 R$^a$, or 6-21 membered heteroarylalkylene optionally substituted by 1-6 R$^a$. In another embodiment, A$^1$ is C$_{1-6}$alkylene optionally substituted by 1-6 R$^a$, C$_{6-11}$arylene optionally substituted by 1-6 R$^a$, —C$_{7-16}$arylalkylene optionally substituted by 1-6 R$^a$, 5-15 membered heteroarylene optionally substituted by 1-6 R$^a$, or 6-21 membered heteroarylalkylene optionally substituted by 1-6 R$^a$. In another embodiment, A$^1$ is C$_{1-6}$alkylene optionally substituted by 1-6 R$^a$, C$_{6-11}$arylene optionally substituted by 1-6 R$^a$, C$_{7-16}$arylalkylene optionally substituted by 1-6 R$^a$, 5-15 membered heteroarylene optionally substituted by 1-6 R$^a$, or 6-21 membered heteroarylalkylene optionally substituted by 1-6 R$^a$. In another embodiment, A$^1$ is C$_{1-6}$alkylene optionally substituted by 1-12 R$^a$, C$_{6-11}$arylene optionally substituted by 1-10 R$^a$, 3-15 membered heterocycloalkylene optionally substituted by 1-27 R$^a$, or 5-15 membered heteroarylene optionally substituted by 1-14 R$^a$. In another embodiment, A$^1$ is C$_{1-6}$alkylene optionally substituted by 1-6 R$^a$, C$_{6-11}$arylene optionally substituted by 1-6 R$^a$, 3-15 membered heterocycloalkylene optionally substituted by 1-6 R$^a$, or 5-15 membered heteroarylene optionally substituted by 1-6 $R^a$. In another embodiment, $A^1$ is $C_{1-6}$alkylene optionally substituted by 1-12 $R^a$, or 5-15 membered heteroarylene optionally substituted by 1-14 $R^a$. In another embodiment, $A^1$ is $C_{1-6}$alkylene optionally substituted by 1-6 $R^a$, or 5-15 membered heteroarylene optionally substituted by 1-6 $R^a$. In another embodiment, $A^1$ is $C_{1-6}$alkylene optionally substituted by 1-3 $R^a$, or 5-15 membered heteroarylene optionally substituted by 1-3 $R^a$. In another embodiment, $A^1$ is 5-15 membered heteroarylene optionally substituted by 1-14 $R^a$. In another embodiment, $A^1$ is 5-15 membered heteroarylene optionally substituted by 1-6 $R^a$. In another embodiment, $A^1$ is 5-15 membered heteroarylene optionally substituted by 1-3 $R^a$. In another embodiment, $A^1$ is $C_{1-6}$alkylene optionally substituted by 1-12 $R^a$, $C_{6-11}$arylene optionally substituted by 1-10 $R^a$, or 5-15 membered heteroarylene optionally substituted by 1-14 $R^a$. In another embodiment, $A^1$ is $C_{1-6}$alkylene optionally substituted by 1-6 $R^a$, $C_{6-11}$arylene optionally substituted by 1-6 $R^a$, or 5-15 membered heteroarylene optionally substituted by 1-6 $R^a$. In another embodiment, $A^1$ is $C_{1-6}$alkylene optionally substituted by 1-6 $R^a$, phenylene optionally substituted by 1-4 $R^a$, $C_{9-11}$ arylene optionally substituted by 1-6 $R^a$, or 5-15 membered heteroarylene optionally substituted by 1-6 $R^a$. In another embodiment, $A^1$ is $C_{1-6}$alkylene optionally substituted by 1-6 $R^a$, phenylene optionally substituted by 1-4 $R^a$, $C_{10-11}$arylene optionally substituted by 1-6 $R^a$, or 5-15 membered heteroarylene optionally substituted by 1-6 $R^a$. In another embodiment, $A^1$ is $C_{1-6}$alkylene optionally substituted by 1-6 $R^a$, phenylene optionally substituted by 1-4 $R^a$, $C_{11}$arylene optionally substituted by 1-6 $R^a$, or 5-15 membered heteroarylene optionally substituted by 1-6 $R^a$. In another embodiment, $A^1$ is $C_{1-6}$alkylene optionally substituted by 1-2 $R^a$, $C_{6-11}$ arylene optionally substituted by 1-2 $R^a$, or 5-15 membered heteroarylene optionally substituted by 1-2 $R^a$. In another embodiment, $A^1$ is $C_{1-6}$alkylene optionally substituted by 1-12 $R^a$, phenylene optionally substituted by 1-4 $R^a$, or 5-11 membered heteroarylene optionally substituted by 1-14 $R^a$. In another embodiment, $A^1$ is $C_{1-6}$alkylene optionally substituted by 1-12 $R^a$, phenylene optionally substituted by 1-4 $R^a$, $C_{11}$aryl or $C_{11}$arylene optionally substituted by 1-6 $R^a$, or 5, 6, 9-12, or 15 membered heteroarylene optionally substituted by 1-14 $R^a$. In another embodiment, $A^1$ is $C_{1-6}$alkylene optionally substituted by 1-12 $R^a$, phenylene optionally substituted by 1-4 $R^a$, or 5, 6, 9-12, or 15 membered heteroarylene optionally substituted by 1-14 $R^a$. In another embodiment, $A^1$ is $C_{1-6}$alkylene optionally substituted by 1-6 $R^a$, phenylene optionally substituted by 1-4 $R^a$, or 5, 6, 9-12, or 15 membered heteroarylene optionally substituted by 1-6 $R^a$. In another embodiment, $A^1$ is $C_{1-6}$alkylene optionally substituted by 1-3 $R^a$, phenylene optionally substituted by 1-3 $R^a$, or 5, 6, 9-12, or 15 membered heteroarylene optionally substituted by 1-3 $R^a$. In another embodiment, $A^1$ is $C_{1-6}$alkylene optionally substituted by 1-12 $R^a$, phenylene optionally substituted by 1-4 $R^a$, or 5, 6 or 9-11 membered heteroarylene optionally substituted by 1-14 $R^a$. In another embodiment, $A^1$ is $C_{1-6}$alkylene optionally substituted by 1-12 $R^a$, phenylene optionally substituted by 1-4 $R^a$, or 5 or 9-11 membered heteroarylene optionally substituted by 1-14 $R^a$. In another embodiment, $A^1$ is $C_{1-6}$alkylene optionally substituted by 1-3 $R^a$, phenylene optionally substituted by 1-3 $R^a$, or 5 or 9-11 membered heteroarylene optionally substituted by 1-3 $R^a$. In another embodiment, $A^1$ is $C_{1-6}$alkylene optionally substituted by 1-3 $R^a$, phenylene optionally substituted by 1-3 $R^a$, or 5-11 membered heteroarylene optionally substituted by 1-3 $R^a$. In another embodiment, $A^1$ is $C_{1-6}$alkylene optionally substituted by 1-3 $R^a$, phenylene optionally substituted by 1-3 $R^a$, or 5-11 membered heteroarylene optionally substituted by 1-3 $R^a$. In another embodiment, $A^1$ is $C_{1-6}$alkylene, phenylene optionally substituted by 1-2 $R^a$, or 5-11 membered heteroarylene optionally substituted by 1-2 $R^a$. In another embodiment, $A^1$ is $C_{1-6}$alkylene optionally substituted by 1-6 $R^a$, phenylene optionally substituted by 1-4 $R^a$, $C_{9-11}$ arylene optionally substituted by 1-6 $R^a$, or 5, 6, 9-12, or 15 membered heteroarylene optionally substituted by 1-6 $R^a$, wherein the heteroarylene group contains, in addition to carbon atoms, 1-4 heteroatoms chosen from nitrogen, oxygen, and sulfur. In another embodiment, $A^1$ is $C_{1-6}$alkylene optionally substituted by 1-6 $R^a$, phenylene optionally substituted by 1-4 $R^a$, $C_{11}$arylene optionally substituted by 1-6 $R^a$, or 5, 6, 9-12, or 15 membered heteroarylene optionally substituted by 1-6 $R^a$, wherein the heteroarylene group contains, in addition to carbon atoms, 1-3 heteroatoms chosen from nitrogen, oxygen, and sulfur. In another embodiment, $A^1$ is $C_{1-6}$alkylene optionally substituted by 1-6 $R^a$, phenylene optionally substituted by 1-4 $R^a$, $C_{9-11}$arylene optionally substituted by 1-6 $R^a$, or 5, 6, 9-12, or 15 membered heteroarylene optionally substituted by 1-6 $R^a$, wherein the heteroarylene group contains, in addition to carbon atoms, 1-4 heteroatoms chosen from nitrogen and oxygen. In another embodiment, $A^1$ is $C_{1-6}$alkylene optionally substituted by 1-6 $R^a$, phenylene optionally substituted by 1-4 $R^a$, $C_{11}$arylene optionally substituted by 1-6 $R^a$, or 5, 6, 9-12, or 15 membered heteroarylene optionally substituted by 1-6 $R^a$, wherein the heteroarylene group contains, in addition to carbon atoms, 1-3 heteroatoms chosen from nitrogen and oxygen. In another embodiment, $A^1$ is $C_{1-6}$alkylene optionally substituted by 1-6 $R^a$, phenylene optionally substituted by 1-4 $R^a$, or 5, 6, 9-12, or 15 membered heteroarylene optionally substituted by 1-6 $R^a$, wherein the heteroarylene group contains, in addition to carbon atoms, 1-4 heteroatoms chosen from nitrogen, oxygen, and sulfur. In another embodiment, $A^1$ is $C_{1-6}$alkylene optionally substituted by 1-6 $R^a$, phenylene optionally substituted by 1-4 $R^a$, or 5, 6, 9-12, or 15 membered heteroarylene optionally substituted by 1-6 $R^a$, wherein the heteroarylene group contains, in addition to carbon atoms, 1-3 heteroatoms chosen from nitrogen, oxygen, and sulfur. In another embodiment, $A^1$ is $C_{1-6}$alkylene optionally substituted by 1-6 $R^a$, phenylene optionally substituted by 1-4 $R^a$, or 5, 6, 9-12, or 15 membered heteroarylene optionally substituted by 1-6 $R^a$, wherein the heteroarylene group contains, in addition to carbon atoms, 1-4 heteroatoms chosen from nitrogen and oxygen. In another embodiment, $A^1$ is $C_{1-6}$alkylene optionally substituted by 1-6 $R^a$, phenylene optionally substituted by 1-4 $R^a$, or 5, 6, 9-12, or 15 membered heteroarylene optionally substituted by 1-6 $R^a$, wherein the heteroarylene group contains, in addition to carbon atoms, 1-3 heteroatoms chosen from nitrogen and oxygen. In another embodiment, $A^1$ is $C_{1-6}$alkylene, phenylene optionally substituted by 1-2 $R^a$, or 5 or 9-11 membered heteroarylene optionally substituted by 1-2 $R^a$, wherein the heteroarylene group contains, in addition to carbon atoms, one or two heteroatoms chosen from nitrogen and oxygen. In another embodiment, $A^1$ is $C_{1-6}$alkylene, phenylene optionally substituted by 1-2 $R^a$, or 5 or 9-11 membered heteroarylene optionally substituted by 1-2 $R^a$, wherein the heteroarylene group contains, in addition to carbon atoms, one nitrogen atom or two oxygen atoms. In another embodiment, $A^1$ is chosen from phenylene, 2,3,4,5-tetrahydro-1H-benzo[d]azepin-7-ylene, methylene, ethylene, propylene, pyridinylene, 1,3,4,5-tetrahydro-benzo[b]azepin-2-one-8-ylene, isopropylene, pyrazolylene, 1,3-benzodioxolylene, indolylene, quinolinylene, imidazolylene, imidazopyridinylene, 1,3-dihydro-indolylene, 2,3,4,5-tetrahydro-1H-1-benzazepinylene, 6,7,8,9-tetrahydro-5H-benzocycloheptenylene, 2,3,4,5-tetrahydro-1H-benzo[d]azepinylene, spiro (2H-1-benzopyran-2,4'-piperdinylene, spiro(2H-1-benzopyran-2,4'-piperidin-4-(3H)-one-ylene, 2,3-dihydrobenzofuranylene, 2,3-dihydrobenzodioxinylene, benzaoxazolylene, benzthiazolylene, 1,6-dihydropyridinylene, 2,3-dihydrobenzo-benzoxazolylene, 2,3,4,5-tetrahydrobenzo[b]azepinylene, 2,3-dihydro-1H-indolylene, 3,5-dihydro[1,4]oxazinylene, 2,2-dioxo-2,3-dihydro-1H-2lambda*6*-benzo[c]thiophenylene, pyridinylene, 2,3-dihydro-1H-isoindolylene, 2,3-dihydro-1H-indolylene, 3,4-dihydro-1H-isoquinolinylene, 3,4-dihydrospiro[chromene-2,4'-piperidin]ylene, 3H-benzoimidazolylene, piperazinylene, pyrazolylene, 2,3-dihydro-1H-benzimidazolylene, 1H-indazolylene, 2H-indazolylene, thiazolylene, 4H-[1,2,4]triazolylene, 1H-tetrazolylene, 1H-benzimidazolylene, 3,4-dihydro-2H-1,4-ethano-quinolinylene, and 6,7,8,9-tetrahydro-5H-benzo[7]annulenylene, wherein each $A^1$ is optionally substituted by 1-6 $R^a$. In another embodiment, $A^1$ is chosen from phenylene, 2,3,4,5-tetrahydro-1H-benzo[d]azepin-7-ylene, methylene, ethylene, propylene, pyridin-3-ylene, 1,3,4,5-tetrahydro-benzo[b]azepin-2-one-8-ylene, isopropylene, 1H-pyrazol-3-yl, 1H-pyrazol-3-ylene, 1,3-benzodioxol-5-ylene, 1H-indol-5-yl, 1H-indol-5-ylene, quinolin-6-ylene, imidazolylene, 1H-imidazo[4,5-c]pyridinylene, 1,3-dihydro-indolylene, 2,3,4,5-tetrahydro-1H-1-benzazepin-8-ylene, 6,7,8,9-tetrahydro-5H-benzocyclohepten-2-ylene, 2,3,4,5-tetrahydro-1H-benzo[d]azepin-7-ylene, spiro(2H-1-benzopyran-2,4'-piperdinylene, spiro(2H-1-benzopyran-2,4'-piperidin-4-(3H)-one-ylene, 7-quinolin-8-ylene, 2,3-dihydrobenzofuran-7-ylene, 2,3-dihydrobenzodioxin-5-ylene, 5-benzaoxazolylene, 5-benzthiazolylene, 1,6-dihydropyridinylene, 2,3-dihydrobenzo-6-oxobenzoxazolylene, 2,3,4,5-tetrahydrobenzo[b]azepinylene, 2,3-dihydro-1H-indolylene, 3,5-dihydro[1,4]oxazinylene, 3,5-dihydro[1,4]oxazinylene, 2,3-dihydro-1H-2lambda*6*-benzo[c]thiophen-5-ylene, pyridin-3-ylene, 2,3-dihydro-1H-isoindol-5-ylene, 2,3-dihydro-1H-indol-6-ylene, 3,4-dihydro-1H-isoquinolin-2-ylene, 3,4-dihydro-1H-quinolinylene, 3,4-dihydrospiro[chromene-2,4'-piperidin]-6-ylene, 3H-benzoimidazol-5-ylene, pyrazolylene, piperazinylene, 2,3-dihydro-1H-benzimidazol-5-ylene, 1H-indazol-5-ylene, 1H-indazol-6-ylene, 2H-indazol-6-ylene, 2H-indazol-5-ylene, thiazol-2-ylene, pyridin-4-ylene, 4H-[1,2,4]triazol-3-ylene, 1H-tetrazol-5-ylene, 1H-benzimidazol-2-ylene, 3,4-dihydro-2H-1,4-ethano-quinolin-7-ylene, and 6,7,8,9-tetrahydro-5H-benzo[7]annulen-2-ylene, wherein each $A^1$ is optionally substituted by 1-6 $R^a$. In another embodiment, $A^1$ is phenylene, 2,3,4,5-tetrahydro-1H-benzo[d]azepin-7-ylene, methylene, ethylene, propylene, pyridinylene, 1,3,4,5-tetrahydro-benzo[b]azepin-2-one-8-ylene, isopropylene, pyrazolylene, 1,3-benzodioxolylene, indolylene, quinolinylene. In another embodiment, $A^1$ is 2,3,4,5-tetrahydro-1H-benzo[d]azepin-7-ylene, methylene, ethylene, propylene, pyridinylene, 1,3,4,5-tetrahydro-benzo[b]azepin-2-one-8-ylene, or isopropylene. In another embodiment, $A^1$ is phenylene, 2,3,4,5-tetrahydro-1H-benzo[d]azepin-7-ylene, methylene, ethylene, propylene, pyridin-3-ylene, 1,3,4,5-tetrahydro-benzo[b]azepin-2-one-8-ylene, isopropylene, 1H-pyrazol-3-ylene, 1,3-benzodioxol-5-ylene, 1H-indol-5-ylene, or quinolin-6-ylene. In another embodiment, $A^1$ is phenylene, 2,3,4,5-tetrahydro-1H-benzo[d]azepin-7-ylene, methylene, ethylene, propylene, pyridin-3-ylene, 1,3,4,5-tetrahydro-benzo[b]azepin-2-one-8-ylene, isopropylene, 1H-pyrazol-3-ylene, 1,3-benzodioxol-5-ylene, 1H-indol-5-ylene, or quinolin-6-ylene.

In each embodiment of the present invention that is described in the paragraphs that precede or follow this paragraph, the definition of $R^a$ may be chosen from any of the embodiments that are described in this paragraph. In one embodiment, each $R^a$ is independently chosen from $C_{1-6}$alkyl optionally substituted by 1-13 $R^{19}$, $C_{2-6}$alkenyl optionally substituted by 1-11 $R^{19}$, $C_{2-6}$alkynyl optionally substituted by 1-9 $R^{19}$, $C_{6-11}$aryl optionally substituted by 1-11 $R^{19}$, $C_{7-16}$arylalkyl optionally substituted by 1-19 $R^{19}$, $C_{3-11}$cycloalkyl optionally substituted by 1-21 $R^{19}$, $C_{4-17}$cycloalkylalkyl optionally substituted by 1-32 $R^{19}$, 3-15 membered heterocycloalkyl optionally substituted by 1-28 $R^{19}$, 4-21 membered heterocycloalkylalkyl optionally substituted by 1-40 $R^{19}$, 5-15 membered heteroaryl optionally substituted by 1-15 $R^{19}$, 6-21 membered heteroarylalkyl optionally substituted by 1-27 $R^{19}$, halogen, —CN, —C(=O)$R^{10}$, —C(=O)O$R^{10}$, —C(=O)N$R^{12}R^{13}$, —C(=O)C(=O)$R^{10}$, —C(=N$R^{15}$)$R^{10}$, —C(=N$R^{15}$)N$R^{12}R^{13}$, —C(=NOH)N$R^{12}R^{13}$, —C(=NO$R^{16}$)$R^{10}$, —C(=NN$R^{12}R^{13}$)$R^{10}$, —C(=NN$R^{14}$C(=O)$R^1$)$R^{10}$, —C(=NN$R^{14}$C(=O)O$R^{11}$)$R^{10}$, —C(=S)N$R^{12}R^{13}$, —NC, —NO$_2$, —N$R^{12}R^{13}$, —N$R^{12}R^{13}$, —N=N$R^{14}$, =N$R^{10}$, =NO$R^{10}$, —N$R^{14}$O$R^{16}$, —N$R^{14}$C(=O)$R^{10}$, —N$R^{14}$C(=O)C(=O)$R^{10}$, —N$R^{14}$C(=O)O$R^{11}$, —N$R^{14}$C(=O)C(=O)O$R^{11}$, —N$R^{14}$C(=O)N$R^{12}R^{13}$, —N$R^{14}$C(=O)N$R^{14}$C(=O)$R^{10}$, —N$R^{14}$C(=O)N$R^{14}$C(=O)O$R^{10}$, —N$R^{14}$C(=N$R^{15}$)N$R^{12}R^{13}$, —N$R^{14}$C(=O)C(=O)N$R^{12}R^{13}$, —N$R^{14}$C(=S)$R^{10}$, —N$R^{14}$C(=S)O$R^{10}$, —N$R^{14}$C(=S)N$R^{12}R^{13}$, —N$R^{14}$S(=O)$_2R^{11}$, —N$R^{14}$S(=O)$_2$N$R^{12}R^{13}$, —N$R^{14}$P(=O)$R^{18}R^{18}$, —N$R^{14}$P(=O)(N$R^{12}R^{13}$)(N$R^{12}R^{13}$), —N$R^{14}$P(=O)(O$R^{10}$)(O$R^{10}$), —N$R^{14}$P(=O)(S$R^{10}$)(S$R^{10}$), —O$R^{10}$, =O, —OCN, —OC(=O)$R^{10}$, —OC(=O)N$R^{12}R^{13}$, —OC(=O)O$R^{10}$, —OC(=N$R^{15}$)N$R^{12}R^{13}$, —OS(=O)$R^{10}$, —OS(=O)$_2R^{10}$, —OS(=O)$_2$O$R^{10}$, —OS(=O)$_2$N$R^{12}R^{13}$, —OP(=O)$R^{18}R^{18}$, —OP(=O)(N$R^{12}R^{13}$)(N$R^{12}R^{13}$), —OP(=O)(O$R^{10}$)(O$R^{10}$), —OP(=O)(S$R^{10}$)(S$R^{10}$), —SCN, =S, —S(=O)$_nR^{10}$, —S(=O)$_2$O$R^{10}$, —SO$_3R^{17}$, —S(=O)$_2$N$R^{12}R^{13}$, —S(=O)N$R^{12}R^{13}$, —SP(=O)$R^{18}R^{18}$, —SP(=O)(N$R^{12}R^{13}$)(N$R^{12}R^{13}$), —SP(=O)(O$R^{10}$)(O$R^{10}$), —SP(=O)(S$R^{10}$)(S$R^{10}$), —P(=O)$R^{18}R^{18}$, —SP(=O)(N$R^{12}R^{13}$)(N$R^{12}R^{13}$), —SP(=O)(O$R^{10}$)(O$R^{10}$), —SP(=O)(S$R^{10}$)(S$R^{10}$), —P(=O)$R^{18}R^{18}$, —P(=O)(N$R^{12}R^{13}$)(N$R^{12}R^{13}$), —P(=O)(O$R^{10}$)(O$R^{10}$), and —P(=O)(S$R^{10}$)(S$R^{10}$). In another embodiment, each $R^a$ is independently chosen from $C_{1-6}$alkyl optionally substituted by 1-13 $R^{19}$, $C_{2-6}$alkenyl optionally substituted by 1-11 $R^{19}$, $C_{2-6}$alkynyl optionally substituted by 1-9 $R^{19}$, $C_{6-11}$aryl optionally substituted by 1-11 $R^{19}$, $C_{7-16}$arylalkyl optionally substituted by 1-19 $R^{19}$, $C_{3-11}$cycloalkyl optionally substituted by 1-21 $R^{19}$, $C_{4-17}$cycloalkylalkyl optionally substituted by 1-32 $R^{19}$, 3-15 membered heterocycloalkyl optionally substituted by 1-28 $R^{19}$, 4-21 membered heterocycloalkylalkyl optionally substituted by 1-40 $R^{19}$, 5-15 membered heteroaryl optionally substituted by 1-15 $R^{19}$, 6-21 membered heteroarylalkyl optionally substituted by 1-27 $R^{19}$, halogen, —CN, —C(=O)$R^{10}$, —C(=O)O$R^{10}$, —C(=O)N$R^{12}R^{13}$, —C(=O)C(=O)$R^{10}$, —C(=N$R^{15}$)$R^{10}$, —C(=N$R^{15}$)N$R^{12}R^{13}$, —C(=NOH)N$R^{12}R^{13}$, —C(=NO$R^{16}$)$R^{10}$, —C(=NN$R^{12}R^{13}$)$R^{10}$, —C(=NN$R^{14}$C(=O)$R^{11}$)$R^{10}$, —C(=NN$R^{14}$C(=O)O$R^{11}$)$R^{10}$, —C(=S)N$R^{12}R^{13}$, —NC, —NO$_2$, —N$R^{12}R^{13}$, —N$R^{14}$N$R^{12}R^{13}$, —N=N$R^{14}$, =N$R^{10}$, =NO$R^{10}$, —N$R^{14}$O$R^{16}$, —N$R^{14}$C(=O)$R^{10}$, —N$R^{14}$C(=O)C(=O)$R^{10}$, —N$R^{14}$C(=O)O$R^{11}$, —N$R^{14}$C(=O)C(=O)O$R^{11}$, —N$R^{14}$C(=O)N$R^{12}R^{13}$, —N$R^{14}$C(=O)N$R^{14}$C(=O)$R^{10}$, —N$R^{14}$C(=O)N$R^{14}$C(=O)O$R^{10}$, —N$R^{14}$C(=N$R^{15}$)N$R^{12}R^{13}$, —N$R^{14}$C(=O)C(=O)N$R^{12}R^{13}$, —N$R^{14}$C(=S)$R^{10}$, —N$R^{14}$C(=S)O$R^{10}$, —N$R^{14}$C(=S)N$R^{12}R^{13}$, —N$R^{14}$S(=O)$_2R^{11}$, —N$R^{14}$S(=O)$_2$N$R^{12}R^{13}$, —N$R^{14}$P(=O)$R^{18}R^{18}$, —O$R^{10}$, =O, —OCN, —OC(=O)$R^{10}$, —OC(=O)N$R^{12}R^{13}$, —OC(=O)O$R^{10}$, —OC(=N$R^{15}$)N$R^{12}R^{13}$, —OS(=O)R$^{10}$, —OS(=O)$_2$R$^{10}$, —OS(=O)$_2$OR$^{10}$, —OS(=O)$_2$NR$^{12}$R$^{13}$, —SCN, =S, —S(=O)$_n$R$^{10}$, —S(=O)$_2$OR$^{10}$, —SO$_3$R$^{17}$, —S(=O)$_2$NR$^{12}$R$^{13}$, —S(=O)NR$^{12}$R$^{13}$, and —P(=O)R$^{18}$R$^{18}$. In another embodiment, each R$^a$ is independently chosen from C$_{1-6}$alkyl optionally substituted by 1-13 R$^{19}$, C$_{2-6}$alkenyl optionally substituted by 1-11 R$^{19}$, C$_{2-6}$alkynyl optionally substituted by 1-9 R$^{19}$, C$_{6-11}$ aryl optionally substituted by 1-11 R$^{19}$, C$_{7-16}$arylalkyl optionally substituted by 1-19 R$^{19}$, C$_{3-11}$cycloalkyl optionally substituted by 1-21 R$^{19}$, C$_{4-17}$cycloalkylalkyl optionally substituted by 1-32 R$^{19}$, 3-15 membered heterocycloalkyl optionally substituted by 1-28 R$^{19}$, 4-21 membered heterocycloalkylalkyl optionally substituted by 1-40 R$^{19}$, 5-15 membered heteroaryl optionally substituted by 1-15 R$^{19}$, 6-21 membered heteroarylalkyl optionally substituted by 1-27 R$^{19}$, halogen, —CN, —C(=O)R$^{10}$, —C(=O)OR$^{10}$, —C(=O)NR$^{12}$R$^{13}$, —C(=O)C(=O)R$^{10}$, —C(=NR$^{15}$)R$^{10}$, —C(=NR$^{15}$)NR$^{12}$R$^{13}$, —C(=NOH)NR$^{12}$R$^{13}$, —C(=NOR$^{16}$)R$^{10}$, —C(=NNR$^{12}$R$^{13}$)R$^{10}$, —C(=NNR$^{14}$C(=O)R$^{11}$)R$^{10}$, —C(=NNR$^{14}$C(=O)OR$^{11}$)R$^{10}$, —C(=S)NR$^{12}$R$^{13}$, —NC, —NO$_2$, —NR$^{12}$R$^{13}$, —NR$^{14}$NR$^{12}$R$^{13}$, —N=NR$^{14}$, =NR$^{10}$, =NOR$^{10}$, —NR$^{14}$OR$^{16}$, —NR$^{14}$C(=O)R$^{10}$, —NR$^{14}$C(=O)C(=O)R$^{10}$, —NR$^{14}$C(=O)OR$^{11}$, —NR$^{14}$C(=O)C(=O)OR$^{11}$, —NR$^{14}$C(=O)NR$^{12}$R$^{13}$, —NR$^{14}$C(=O)NR$^{14}$C(=O)R$^{10}$, —NR$^{14}$C(=O)NR$^{14}$C(=O)OR$^{10}$, —NR$^{14}$C(=NR$^{15}$)NR$^{12}$R$^{13}$, —NR$^{14}$C(=O)C(=O)NR$^{12}$R$^{13}$, —NR$^{14}$C(=S)R$^{10}$, —NR$^{14}$C(=S)OR$^{10}$, —NR$^{14}$C(=S)NR$^{12}$R$^{13}$, —NR$^{14}$S(=O)$_2$R$^{11}$, —NR$^{14}$S(=O)$_2$NR$^{12}$R$^{13}$, —OR$^{10}$, =O, —OCN, —OC(=O)R$^{10}$, —OC(=O)NR$^{12}$R$^{13}$, —OC(=O)OR$^{10}$, —OC(=NR$^{15}$)NR$^{12}$R$^{13}$, —OS(=O)R$^{10}$, —OS(=O)$_2$R$^{10}$, —OS(=O)$_2$OR$^{10}$, —OS(=O)$_2$NR$^{12}$R$^{13}$, —SCN, =S, —S(=O)$_n$R$^{10}$, —S(=O)$_2$OR$^{10}$, —SO$_3$R$^{17}$, —S(=O)$_2$NR$^{12}$R$^{13}$, and —S(=O)NR$^{12}$R$^{13}$. In another embodiment, each R$^a$ is independently chosen from C$_{1-6}$alkyl optionally substituted by 1-13 R$^{19}$, C$_{2-6}$alkenyl optionally substituted by 1-11 R$^{19}$, C$_{2-6}$alkynyl optionally substituted by 1-9 R$^{19}$, C$_{6-11}$ aryl optionally substituted by 1-7 R$^{19}$, C$_{7-16}$arylalkyl optionally substituted by 1-19 R$^{19}$, C$_{3-11}$cycloalkyl optionally substituted by 1-21 R$^{19}$, C$_{4-17}$cycloalkylalkyl optionally substituted by 1-32 R$^{19}$, 3-15 membered heterocycloalkyl optionally substituted by 1-28 R$^{19}$, 4-21 membered heterocycloalkylalkyl optionally substituted by 1-40 R$^{19}$, 5-15 membered heteroaryl optionally substituted by 1-15 R$^{19}$, 6-21 membered heteroarylalkyl optionally substituted by 1-27 R$^{19}$, halogen, —CN, —C(=O)R$^{10}$, —C(=O)OR$^{10}$, —C(=O)NR$^{12}$R$^{13}$, —C(=O)C(=O)R$^{10}$, —C(=S)NR$^{12}$R$^{13}$, —NC, —NO$_2$, —NR$^{12}$R$^{13}$, —NR$^{14}$NR$^{12}$R$^{13}$, —NR$^{14}$OR$^{16}$, —NR$^{14}$C(=O)R$^{10}$, —NR$^{14}$C(=O)C(=O)R$^{10}$, —NR$^{14}$C(=O)OR$^{11}$, —NR$^{14}$C(=O)C(=O)OR$^{11}$, —NR$^{12}$R$^{13}$, —NR$^{14}$C(=O)NR$^{14}$C(=O)R$^{10}$, —NR$^{14}$C(=O)NR$^{14}$C(=O)OR$^{10}$, —NR$^{14}$C(=NR$^{15}$)NR$^{12}$R$^{13}$, —NR$^{14}$C(=O)C(=O)NR$^{12}$R$^{13}$, —NR$^{14}$C(=S)R$^{10}$, —NR$^{14}$C(=S)OR$^{10}$, —NR$^{14}$C(=S)NR$^{12}$R$^{13}$, —NR$^{14}$S(=O)$_2$R$^{11}$, —NR$^{14}$S(=O)$_2$NR$^{12}$R$^{13}$, —OR$^{10}$, =O, —OCN, —OC(=O)R$^{10}$, —OC(=O)NR$^{12}$R$^{13}$, —OC(=O)OR$^{10}$, —OS(=O)R$^{10}$, —OS(=O)$_2$R$^{10}$, —OS(=O)$_2$OR$^{10}$, —OS(=O)$_2$NR$^{12}$R$^{13}$, —SCN, =S, —S(=O)$_n$R$^{10}$, —S(=O)$_2$OR$^{10}$, —SO$_3$R$^{17}$, —S(=O)$_2$NR$^{12}$R$^{13}$, and —S(=O)NR$^{12}$R$^{13}$. In another embodiment, each R$^a$ is independently chosen from C$_{1-6}$alkyl optionally substituted by 1-13 R$^{19}$, C$_{6-11}$ aryl optionally substituted by 1-7 R$^{19}$, C$_{7-16}$arylalkyl optionally substituted by 1-19 R$^{19}$, C$_{3-11}$cycloalkyl optionally substituted by 1-21 R$^{19}$, C$_{4-17}$cycloalkylalkyl optionally substituted by 1-32 R$^{19}$, 3-15 membered heterocycloalkyl optionally substituted by 1-28 R$^{19}$, 4-21 membered heterocycloalkylalkyl optionally substituted by 1-40 R$^{19}$, 5-15 membered heteroaryl optionally substituted by 1-15 R$^{19}$, 6-21 membered heteroarylalkyl optionally substituted by 1-27 R$^{19}$, halogen, —CN, —C(=O)R$^{10}$, —C(=O)OR$^{10}$, —C(=O)NR$^{12}$R$^{13}$, —C(=S)NR$^{12}$R$^{13}$, —NC, —NO$_2$, —NR$^{12}$R$^{13}$, —NR$^{14}$NR$^{12}$R$^{13}$, —NR$^{14}$OR$^{16}$, —NR$^{14}$C(=O)R$^{10}$, —NR$^{14}$C(=O)OR$^{11}$, —NR$^{14}$C(=O)NR$^{12}$R$^{13}$, —NR$^{14}$C(=O)NR$^{14}$C(=O)R$^{10}$, —NR$^{14}$C(=O)NR$^{14}$C(=O)OR$^{10}$, —NR$^{14}$C(=NR$^{15}$)NR$^{12}$R$^{13}$, —NR$^{14}$C(=S)R$^{10}$, —NR$^{14}$C(=S)NR$^{12}$R$^{13}$, —NR$^{14}$S(=O)$_2$R$^{11}$, —OR$^{10}$, =O, —OCN, —OC(=O)R$^{10}$, —OC(=O)NR$^{12}$R$^{13}$, —SCN, =S, —S(=O)$_n$R$^{10}$, and —S(=O)$_2$NR$^{12}$R$^{13}$. In another embodiment, each R$^a$ is independently chosen from C$_{1-6}$alkyl optionally substituted by 1-13 R$^{19}$, C$_{6-11}$aryl optionally substituted by 1-7 R$^{19}$, C$_{7-16}$arylalkyl optionally substituted by 1-19 R$^{19}$, C$_{3-11}$cycloalkyl optionally substituted by 1-21 R$^{19}$, C$_{4-17}$cycloalkylalkyl optionally substituted by 1-32 R$^{19}$, 3-15 membered heterocycloalkyl optionally substituted by 1-28 R$^{19}$, 4-21 membered heterocycloalkylalkyl optionally substituted by 1-40 R$^{19}$, 5-15 membered heteroaryl optionally substituted by 1-15 R$^{19}$, 6-21 membered heteroarylalkyl optionally substituted by 1-27 R$^{19}$, halogen, —CN, —C(=O)R$^{10}$, —C(=O)OR$^{10}$, —C(=O)NR$^{12}$R$^{13}$, —C(=S)NR$^{12}$R$^{13}$, —NO$_2$, —NR$^{12}$R$^{13}$, —NR$^{14}$C(=)R$^{10}$, —NR$^{14}$C(=O)OR$^{11}$, —NR$^{14}$C(=O)NR$^{12}$R$^{13}$, —NR$^{14}$C(=O)NR$^{14}$C(=O)R$^{10}$, —NR$^{14}$C(=O)NR$^{14}$C(=O)OR$^{10}$, —NR$^{14}$C(=S)R$^{10}$, —NR$^{14}$S(=O)$_2$R$^{11}$, —NR$^{14}$P(=O)R$^{18}$R$^{18}$, —OR$^{10}$, =O, —OC(=O)R$^{10}$, —OC(=O)NR$^{12}$R$^{13}$, =S, —S(=O)$_n$R$^{10}$, —S(=O)$_2$NR$^{12}$R$^{13}$, and —P(=O)R$^{18}$R$^{18}$. In another embodiment, each R$^a$ is independently chosen from C$_{1-6}$alkyl optionally substituted by 1-13 R$^{19}$, C$_{6-11}$aryl optionally substituted by 1-7 R$^{19}$, C$_{7-16}$arylalkyl optionally substituted by 1-19 R$^{19}$, C$_{3-11}$cycloalkyl optionally substituted by 1-21 R$^{19}$, C$_{4-17}$cycloalkylalkyl optionally substituted by 1-32 R$^{19}$, 3-15 membered heterocycloalkyl optionally substituted by 1-28 R$^{19}$, 4-21 membered heterocycloalkylalkyl optionally substituted by 1-40 R$^{19}$, 5-15 membered heteroaryl optionally substituted by 1-15 R$^{19}$, 6-21 membered heteroarylalkyl optionally substituted by 1-27 R$^{19}$, halogen, —CN, —C(=O)R$^{10}$, —C(=O)OR$^{10}$, —C(=O)NR$^{12}$R$^{13}$, —C(=S)NR$^{12}$R$^{13}$, —NO$_2$, —NR$^{12}$R$^{13}$, —NR$^{14}$C(=O)R$^{10}$, —NR$^{14}$C(=O)OR$^{11}$, —NR$^{14}$C(=O)NR$^{12}$R$^{13}$, —NR$^{14}$C(=)NR$^{14}$C(=O)R$^{10}$, —NR$^{14}$C(=O)NR$^{14}$C(=O)OR$^{10}$, —NR$^{14}$C(=S)R$^{10}$, —NR$^{14}$S(=O)$_2$R$^{11}$, —OR$^{10}$, =O, —OC(=O)R$^{10}$, —OC(=O)NR$^{12}$R$^{13}$, =S, —S(=O)$_n$R$^{10}$, and —S(=O)$_2$NR$^{12}$R$^{13}$. In another embodiment, each R$^a$ is independently chosen from C$_{1-6}$alkyl optionally substituted by 1-13 R$^{19}$, C$_{6-11}$aryl optionally substituted by 1-7 R$^{19}$, C$_{7-16}$arylalkyl optionally substituted by 1-19 $R^{19}$, $C_{3-11}$cycloalkyl optionally substituted by 1-21 $R^{19}$, $C_{4-17}$cycloalkylalkyl optionally substituted by 1-32 $R^{19}$, 3-15 membered heterocycloalkyl optionally substituted by 1-28 $R^{19}$, 4-21 membered heterocycloalkylalkyl optionally substituted by 1-40 $R^{19}$, 5-15 membered heteroaryl optionally substituted by 1-15 $R^{19}$, 6-21 membered heteroarylalkyl optionally substituted by 1-27 $R^{19}$, halogen, —CN, —C(=O)$R^{10}$, —C(=O)O$R^{10}$, —C(=O)N$R^{12}R^{13}$, —N$R^{12}R^{13}$, —N$R^{14}$C(=O)$R^{10}$, —N$R^{14}$C(=O)O$R^{11}$, —N$R^{14}$C(=O)N$R^{12}R^{13}$, —N$R^{14}$S(=O)$_2R^{11}$, —N$R^{14}$P(=O)$R^{18}R^{18}$, —O$R^{10}$, =O, —OC(=O)$R^{10}$, —OC(=O)N$R^{12}R^{13}$, =S, —S(=O)$_nR^{10}$, —S(=O)$_2$N$R^{12}R^{13}$, and —P(=O)$R^{18}R^{18}$. In another embodiment, each $R^a$ is independently chosen from $C_{1-6}$alkyl optionally substituted by 1-13 $R^{19}$, $C_{6-11}$aryl optionally substituted by 1-7 $R^{19}$, $C_{7-16}$arylalkyl optionally substituted by 1-19 $R^{19}$, $C_{3-11}$cycloalkyl optionally substituted by 1-21 $R^{19}$, $C_{4-17}$cycloalkylalkyl optionally substituted by 1-32 $R^{19}$, 3-15 membered heterocycloalkyl optionally substituted by 1-28 $R^{19}$, 4-21 membered heterocycloalkylalkyl optionally substituted by 1-40 $R^{19}$, 5-15 membered heteroaryl optionally substituted by 1-15 $R^{19}$, 6-21 membered heteroarylalkyl optionally substituted by 1-27 $R^{19}$, halogen, —CN, —C(=O)$R^{10}$, —C(=O)O$R^{10}$, —C(=O)N$R^{12}R^{13}$, —N$R^{12}R^{13}$, —N$R^{14}$C(=O)$R^{10}$, —N$R^{14}$C(=O)O$R^{11}$, —N$R^{14}$C(=O)N$R^{12}R^{13}$, —N$R^{14}$S(=O)$_2R^{11}$, —O$R^{10}$, =O, —OC(=O)$R^{10}$, —OC(=O)N$R^{12}R^{13}$, =S, —S(=O)$_nR^{10}$, and —S(=O)$_2$N$R^{12}R^{13}$. In another embodiment, each $R^a$ is independently chosen from $C_{1-6}$alkyl optionally substituted by 1-6 $R^{19}$, $C_{2-6}$alkenyl optionally substituted by 1-6 $R^{19}$, $C_{2-6}$alkynyl optionally substituted by 1-6 $R^{19}$, $C_{6-11}$aryl optionally substituted by 1-6 $R^{19}$, $C_{7-16}$arylalkyl optionally substituted by 1-6 $R^{19}$, $C_{3-11}$cycloalkyl optionally substituted by 1-6 $R^{19}$, $C_{4-17}$cycloalkylalkyl optionally substituted by 1-6 $R^{19}$, 3-15 membered heterocycloalkyl optionally substituted by 1-6 $R^{19}$, 4-21 membered heterocycloalkylalkyl optionally substituted by 1-6 $R^{19}$, 5-15 membered heteroaryl optionally substituted by 1-6 $R^{19}$, 6-21 membered heteroarylalkyl optionally substituted by 1-6 $R^{19}$, halogen, —CN, —C(=O)$R^{10}$, —C(=O)O$R^{10}$, —C(=O)N$R^{12}R^{13}$, —C(=O)C(=O)$R^{10}$, —C(=S)N$R^{12}R^{13}$, —NC, —NO$_2$, —N$R^{12}R^{13}$, —N$R^{14}$N$R^{12}R^{13}$, —N$R^{14}$O$R^{16}$, —N$R^{14}$C(=O)$R^{10}$, —N$R^{14}$C(=O)C(=O)$R^{10}$, —N$R^{14}$C(=O)O$R^{11}$, —N$R^{14}$C(=O)C(=O)O$R^{11}$, —N$R^{14}$C(=O)N$R^{12}R^{13}$, —N$R^{14}$C(=O)N$R^{14}$C(=O)$R^{10}$, —N$R^{14}$C(=O)N$R^{14}$C(=O)O$R^{10}$, —N$R^{14}$C(=N$R^{15}$)N$R^{12}R^{13}$, —N$R^{14}$C(=O)C(=O)N$R^{12}R^{13}$, —N$R^{14}$C(=S)$R^{10}$, —N$R^{14}$C(=S)O$R^{10}$, —N$R^{14}$C(=S)N$R^{12}R^{13}$, —N$R^{14}$S(=O)$_2R^{11}$, —N$R^{14}$S(=O)$_2$N$R^{12}R^{13}$, —O$R^{10}$, =O, —OCN, —OC(=O)$R^{10}$, —OC(=O)N$R^{12}R^{13}$, —OC(=O)O$R^{10}$, —OS(=O)$R^{10}$, —OS(=O)$_2R^{10}$, —OS(=O)$_2$O$R^{10}$, —OS(=O)$_2$N$R^{12}R^{13}$, —SCN, =S, —S(=O)$_nR^{10}$, —S(=O)$_2$O$R^{10}$, —SO$_3R^{17}$, —S(=O)$_2$N$R^{12}R^{13}$, and —S(=O)N$R^{12}R^{13}$. In another embodiment, each $R^a$ is independently chosen from $C_{1-6}$alkyl optionally substituted by 1-6 $R^{19}$, $C_{6-11}$aryl optionally substituted by 1-6 $R^{19}$, $C_{7-16}$arylalkyl optionally substituted by 1-6 $R^{19}$, $C_{3-11}$cycloalkyl optionally substituted by 1-6 $R^{19}$, $C_{4-17}$cycloalkylalkyl optionally substituted by 1-6 $R^{19}$, 3-15 membered heterocycloalkyl optionally substituted by 1-6 $R^{19}$, 4-21 membered heterocycloalkylalkyl optionally substituted by 1-6 $R^{19}$, 5-15 membered heteroaryl optionally substituted by 1-6 $R^{19}$, 6-21 membered heteroarylalkyl optionally substituted by 1-6 $R^{19}$, halogen, —CN, —C(=O)$R^{10}$, —C(=O)O$R^{10}$, —C(=O)N$R^{12}R^{13}$, —C(=S)N$R^{12}R^{13}$, —NC, —NO$_2$, —N$R^{12}R^{13}$, —N$R^{14}$N$R^{12}R^{13}$, —N$R^{14}$O$R^{16}$, —N$R^{14}$C(=O)$R^{10}$, —N$R^{14}$C(=O)O$R^{11}$, —N$R^{14}$C(=O)N$R^{12}R^{13}$, —N$R^{14}$C(=O)N$R^{14}$C(=O)$R^{10}$, —N$R^{14}$C(=O)N$R^{14}$C(=O)O$R^{10}$, —N$R^{14}$C(=N$R^{15}$)N$R^{12}R^{13}$, —N$R^{14}$C(=S)$R^{10}$, —N$R^{14}$C(=S)N$R^{12}R^{13}$, —N$R^{14}$S(=O)$_2R^{11}$, —N$R^{14}$P(=O)$R^{18}R^{18}$, —O$R^{10}$, =O, —OCN, —OC(=O)$R^{10}$, —OC(=O)N$R^{12}R^{13}$, —SCN, =S, —S(=O)$_nR^{10}$, —S(=O)$_2$N$R^{12}R^{13}$, and —P(=O)$R^{18}R^{18}$. In another embodiment, each $R^a$ is independently chosen from $C_{1-6}$alkyl optionally substituted by 1-6 $R^{19}$, $C_{6-11}$aryl optionally substituted by 1-6 $R^{19}$, $C_{7-16}$arylalkyl optionally substituted by 1-6 $R^{19}$, $C_{3-11}$cycloalkyl optionally substituted by 1-6 $R^{19}$, $C_{4-17}$cycloalkylalkyl optionally substituted by 1-6 $R^{19}$, 3-15 membered heterocycloalkyl optionally substituted by 1-6 $R^{19}$, 4-21 membered heterocycloalkylalkyl optionally substituted by 1-6 $R^{19}$, 5-15 membered heteroaryl optionally substituted by 1-6 $R^{19}$, 6-21 membered heteroarylalkyl optionally substituted by 1-6 $R^{19}$, halogen, —CN, —C(=O)$R^{10}$, —C(=O)O$R^{10}$, —C(=O)N$R^{12}R^{13}$, —C(=S)N$R^{12}R^{13}$, —NO$_2$, —N$R^{14}$C(=O)$R^{10}$, —N$R^{14}$C(=O)O$R^{11}$, —N$R^{14}$C(=O)N$R^{12}R^{13}$, —N$R^{14}$C(=O)N$R^{14}$C(=O)$R^{10}$, —N$R^{14}$C(=O)N$R^{14}$C(=O)O$R^{10}$, —N$R^{14}$C(=S)$R^{10}$, —N$R^{14}$S(=O)$_2R^{11}$, —N$R^{14}$P(=O)$R^{18}R^{18}$, —O$R^{10}$, =O, —OC(=O)$R^{10}$, —OC(=O)N$R^{12}R^{13}$, =S, —S(=O)$_nR^{10}$, —S(=O)$_2$N$R^{12}R^{13}$, and —P(=O)$R^{18}R^{18}$. In another embodiment, each $R^a$ is independently chosen from $C_{1-6}$alkyl optionally substituted by 1-6 $R^{19}$, $C_{6-11}$aryl optionally substituted by 1-6 $R^{19}$, $C_{7-16}$arylalkyl optionally substituted by 1-6 $R^{19}$, $C_{3-11}$cycloalkyl optionally substituted by 1-6 $R^{19}$, $C_{4-17}$cycloalkylalkyl optionally substituted by 1-6 $R^{19}$, 3-15 membered heterocycloalkyl optionally substituted by 1-6 $R^{19}$, 4-21 membered heterocycloalkylalkyl optionally substituted by 1-6 $R^{19}$, 5-15 membered heteroaryl optionally substituted by 1-6 $R^{19}$, 6-21 membered heteroarylalkyl optionally substituted by 1-6 $R^{19}$, halogen, —CN, —C(=O)$R^{10}$, —C(=O)O$R^{10}$, —C(=O)N$R^{12}R^{13}$, —C(=S)N$R^{12}R^{13}$, —NO$_2$, —N$R^{12}R^{13}$, —N$R^{14}$C(=O)$R^{10}$, —N$R^{14}$C(=O)O$R^{11}$, —N$R^{14}$C(=O)N$R^{12}R^{13}$, —N$R^{14}$C(=O)N$R^{14}$C(=O)$R^{10}$, —N$R^{14}$C(=O)N$R^{14}$C(=O)O$R^{10}$, —N$R^{14}$C(=S)$R^{10}$, —N$R^{14}$S(=O)$_2R^{11}$, —O$R^{10}$, =O, —OC(=O)$R^{10}$, —OC(=O)N$R^{12}R^{13}$, =S, —S(=O)$_nR^{10}$, and —S(=O)$_2$N$R^{12}R^{13}$. In another embodiment, each $R^a$ is independently chosen from $C_{1-6}$alkyl optionally substituted by 1-6 $R^{19}$, $C_{6-11}$aryl optionally substituted by 1-6 $R^{19}$, $C_{7-16}$arylalkyl optionally substituted by 1-6 $R^{19}$, $C_{3-11}$cycloalkyl optionally substituted by 1-6 $R^{19}$, $C_{4-17}$cycloalkylalkyl optionally substituted by 1-6 $R^{19}$, 3-15 membered heterocycloalkyl optionally substituted by 1-6 $R^{19}$, 4-21 membered heterocycloalkylalkyl optionally substituted by 1-6 $R^{19}$, 5-15 membered heteroaryl optionally substituted by 1-6 $R^{19}$, 6-21 membered heteroarylalkyl optionally substituted by 1-6 $R^{19}$, halogen, —CN, —C(=O)$R^{10}$, —C(=O)

$-OR^{10}$, $-C(=O)NR^{12}R^{13}$, $-NR^{12}R^{13}$, $-NR^{14}C(=O)R^{10}$, $-NR^{14}C(=O)OR^{11}$, $-NR^{14}C(=O)NR^{12}R^{13}$, $-NR^{14}S(=O)_2R^{11}$, $-OR^{10}$, $=O$, $-OC(=O)R^{10}$, $-OC(=O)NR^{12}R^{13}$, $=S$, $-S(=O)_nR^{10}$, and $-S(=O)_2NR^{12}R^{13}$. In another embodiment, each $R^a$ is independently chosen from $C_{1-6}$alkyl optionally substituted by 1-13 $R^{19}$, halogen, $-OR^{10}$, and $=O$. In another embodiment, each $R^a$ is independently chosen from $C_{1-6}$alkyl optionally substituted by 1-3 $R^{19}$, halogen, $-OR^{10}$, and $=O$. In another embodiment, each $R^a$ is independently chosen from $C_{1-6}$alkyl optionally substituted by 1-3 $R^{19}$, halogen, $-OC_{1-6}$alkyl, and $=O$. In another embodiment, each $R^a$ is independently chosen from $C_{1-6}$alkyl, halogen, $-OC_{1-6}$alkyl, and $=O$. In another embodiment, each $R^a$ is independently chosen from methyl, halogen, $-OCH_3$, and $=O$. In another embodiment, each $R^a$ is independently chosen from methyl, chloro, fluoro, $-OCH_3$, and $=O$.

In each embodiment of the present invention that is described in the paragraphs that precede or follow this paragraph, the definition of $G^1$ may be chosen from any of the embodiments that are described in this paragraph. In one embodiment, $G^1$ is $C_{1-6}$alkylene optionally substituted by 1-12 $R^{29}$, $C_{2-6}$alkenylene optionally substituted by 1-10 $R^{29}$, $C_{2-6}$alkynylene optionally substituted by 1-8 $R^{29}$, $C_{6-11}$arylene optionally substituted by 1-10 $R^{29}$, $C_{7-6}$arylalkylene optionally substituted by 1-18 $R^{29}$, $C_{3-11}$cycloalkylene optionally substituted by 1-20 $R^{29}$, $C_{4-17}$cycloalkylalkylene optionally substituted by 1-31 $R^{29}$, 3-15 membered heterocycloalkylene optionally substituted by 1-27 $R^{29}$, 4-21 membered heterocycloalkylalkylene optionally substituted by 1-39 $R^{29}$, 5-15 membered heteroarylene optionally substituted by 1-14 $R^{29}$, 6-21 membered heteroarylalkylene optionally substituted by 1-26 $R^{29}$, $-C_{0-3}$alkylC$(=O)C_{0-3}$alkyl-, $-C_{0-3}$alkylC$(=O)OC_{0-3}$alkyl-, $-C_{0-3}$alkylC$(=O)NR^{24}C_{0-3}$alkyl-, $-C_{0-3}$alkylC$(=O)C(=O)C_{0-3}$alkyl-, $-C_{0-3}$alkylC$(=NR^{25})C_{0-3}$alkyl-, $-C_{0-3}$alkylC$(=NR^{25})NR^{24}C_{0-3}$alkyl-, $-C_{0-3}$alkylC$(=NOH)NR^{24}C_{0-3}$alkyl-, $-C_{0-3}$alkylC$(=NOR^{26})C_{0-3}$alkyl-, $-C_{0-3}$alkylC$(=NNR^{22}R^{23})C_{0-3}$alkyl-, $-C_{0-3}$alkylC$(=NNR^{24}C(=O)R^{21})C_{0-3}$alkyl-, $-C_{0-3}$alkylC$(=NNR^{24}C(=O)OR^{21})C_{0-3}$alkyl-, $-C_{0-3}$alkylC$(=S)NR^{24}C_{0-3}$alkyl-, $-C_{0-3}$alkylNR$^{24}C_{0-3}$alkyl-, $-C_{0-3}$alkylNR$^{24}NR^{24}C_{0-3}$alkyl-, $-C_{0-3}$alkylN$=NC_{0-3}$alkyl-, $-C_{0-3}$alkylNR$^{24}C(=O)C_{0-3}$alkyl-, $-C_{0-3}$alkylNR$^{24}C(=O)C(=O)C_{0-3}$alkyl-, $-C_{0-3}$alkylNR$^{24}C(=O)OC_{0-3}$alkyl-, $-C_{0-3}$alkylNR$^{24}C(=O)NR^{24}C_{0-3}$alkyl-, $-C_{0-3}$alkylNR$^{24}C(=O)NR^{24}C(=O)C_{0-3}$alkyl-, $-C_{0-3}$alkylNR$^{24}C(=O)NR^{24}C(=O)OC_{0-3}$alkyl-, $-C_{0-3}$alkylNR$^{24}C(=NR^{25})NR^{24}C_{0-3}$alkyl-, $-C_{0-3}$alkylNR$^{24}C(=O)C(=O)NR^{24}C_{0-3}$alkyl-, $-C_{0-3}$alkylNR$^{24}C(=S)C_{0-3}$alkyl-, $-C_{0-3}$alkylNR$^{24}C(=S)OC_{0-3}$alkyl-, $-C_{0-3}$alkylNR$^{24}C(=S)NR^{24}C_{0-3}$alkyl-, $-C_{0-3}$alkylNR$^{24}S(=O)_2C_{0-3}$alkyl-, $-C_{0-3}$alkylNR$^{24}S(=O)_2NR^{24}C_{0-3}$alkyl-, $-C_{0-3}$alkylOC$_{0-3}$alkyl-, $-C_{0-3}$alkylOC$(=O)C_{0-3}$alkyl-, $-C_{0-3}$alkylOC$(=O)NR^{24}C_{0-3}$alkyl-, $-C_{0-3}$alkylOC$(=O)OC_{0-3}$alkyl-, $-C_{0-3}$alkylOC$(=NR^{25})NR^{24}C_{0-3}$alkyl-, $-C_{0-3}$alkylOS$(=O)C_{0-3}$alkyl-, $-C_{0-3}$alkylOS$(=O)_2C_{0-3}$alkyl-, $-C_{0-3}$alkylOS$(=O)_2OC_{0-3}$alkyl-, $-C_{0-3}$alkylOS$(=O)_2NR^{24}C_{0-3}$alkyl-, $-C_{0-3}$alkylS$(=O)-C_{0-3}$alkyl-, $-C_{0-3}$alkylS$(=O)_2OC_{0-3}$alkyl-, $-C_{0-3}$alkylSO$_3C_{0-3}$alkyl-, $-C_{0-3}$alkylS$(=O)_2NR^{24}C_{0-3}$alkyl-, $-C_{0-3}$alkylS$(=O)NR^{24}C_{0-3}$alkyl-, or absent. In another embodiment, $G^1$ is $C_{1-6}$alkylene optionally substituted by 1-12 $R^{29}$, $C_{6-11}$arylene optionally substituted by 1-6 $R^{29}$, $C_{7-16}$arylalkylene optionally substituted by 1-18 $R^{29}$, $C_{3-11}$cycloalkylene optionally substituted by 1-20 $R^{29}$, $C_{4-17}$cycloalkylalkylene optionally substituted by 1-31 $R^{29}$, 3-15 membered heterocycloalkylene optionally substituted by 1-27 $R^{29}$, 4-21 membered heterocycloalkylalkylene optionally substituted by 1-39 $R^{29}$, 5-15 membered heteroarylene optionally substituted by 1-14 $R^{29}$, 6-21 membered heteroarylalkylene optionally substituted by 1-26 $R^{29}$, $-C_{0-3}$alkylC$(=O)C_{0-3}$alkyl-, $-C_{0-3}$alkylC$(=O)OC_{0-3}$alkyl-, $-C_{0-3}$alkylC$(=O)NR^{24}C_{0-3}$alkyl-, $-C_{0-3}$alkylC$(=S)NR^{24}C_{0-3}$alkyl-, $-C_{0-3}$alkylNR$^{24}C_{0-3}$alkyl-, $-C_{0-3}$alkylNR$^{24}NR^{24}C_{0-3}$alkyl-, $-C_{0-3}$alkylNR$^{24}C(=O)C_{0-3}$alkyl-, $-C_{0-3}$alkylNR$^{24}C(=O)OC_{0-3}$alkyl-, $-C_{0-3}$alkylNR$^{24}C(=O)NR^{24}C_{0-3}$alkyl-, $-C_{0-3}$alkylNR$^{24}C(=O)NR^{24}C(=O)C_{0-3}$alkyl-, $-C_{0-3}$alkylNR$^{24}C(=O)NR^{24}C(=O)OC_{0-3}$alkyl-, $-C_{0-3}$alkylNR$^{24}C(=S)C_{0-3}$alkyl-, $-C_{0-3}$alkylNR$^{24}S(=O)_2C_{0-3}$alkyl-, $-C_{0-3}$alkylOC$_{0-3}$alkyl-, $-C_{0-3}$alkylOC$(=O)C_{0-3}$ alkyl-, —$C_{0-3}$alkylOC(=O)NR$^{24}$C$_{0-3}$alkyl-, —$C_{0-3}$alkylS(=O)—$C_{0-3}$alkyl-, —$C_{0-3}$alkylS(=O)$_2$NR$^{24}$C$_{0-3}$alkyl-, —$C_{0-3}$alkylS(=O)NR$^{24}$C$_{0-3}$alkyl-, or absent. In another embodiment, G$^1$ is C$_{1-6}$alkylene optionally substituted by 1-12 R$^{29}$, C$_{6-11}$ arylene optionally substituted by 1-6 R$^{29}$, C$_{3-11}$cycloalkylene optionally substituted by 1-20 R$^{29}$, 3-15 membered heterocycloalkylene optionally substituted by 1-27 R$^{29}$, 5-15 membered heteroarylene optionally substituted by 1-14 R$^{29}$, —$C_{0-3}$alkylC(=O)C$_{0-3}$alkyl-, —$C_{0-3}$alkylC(=O)OC$_{0-3}$alkyl-, —$C_{0-3}$alkylC(=O)NR$^{24}$C$_{0-3}$alkyl-, —$C_{0-3}$alkylNR$^{24}$C$_{0-3}$alkyl-, —$C_{0-3}$alkylNR$^{24}$C(=O)C$_{0-3}$alkyl-, —$C_{0-3}$alkylNR$^{24}$C(=O)OC$_{0-3}$alkyl-, —$C_{0-3}$alkylNR$^{24}$C(=O)NR$^{24}$C$_{0-3}$alkyl-, —$C_{0-3}$alkylNR$^{24}$S(=O)$_{2\ 0-3}$ alkyl-, —$C_{0-3}$alkylOC$_{0-3}$alkyl-, —$C_{0-3}$alkylOC(=O)C$_{0-3}$alkyl-, —$C_{0-3}$alkylOC(=O)NR$^{24}$C$_{0-3}$alkyl-, —$C_{0-3}$alkylS(=O)—$C_{0-3}$alkyl-, —$C_{0-3}$alkylS(=O)$_2$ NR$^{24}$C$_{0-3}$alkyl-, or absent. In another embodiment, G$^1$ is C$_{1-6}$alkylene optionally substituted by 1-12 R$^{29}$, C$_{6-11}$arylene optionally substituted by 1-10 R$^{29}$, C$_{3-11}$cycloalkylene optionally substituted by 1-20 R$^{29}$, 3-15 membered heterocycloalkylene optionally substituted by 1-27 R$^{29}$, 5-15 membered heteroarylene optionally substituted by 1-14 R$^{29}$, —$C_{0-3}$ alkylC(=O)C$_{0-3}$alkyl-, —$C_{0-3}$alkylC(=O)OC$_{0-3}$alkyl-, —$C_{0-3}$alkylC(=O)NR$^{24}$C$_{0-3}$alkyl-, —$C_{0-3}$alkylNR$^{24}$C$_{0-3}$alkyl-, —$C_{0-3}$alkylNR$^{24}$C(=O)NR$^{24}$C$_{0-3}$alkyl-, —$C_{0-3}$ alkylNR$^{24}$C(=O)NR$^{24}$C$_{0-3}$alkyl-, —$C_{0-3}$alkylNR$^{24}$S(=O)$_2$ C$_{0-3}$alkyl-, —$C_{0-3}$alkylOC$_{0-3}$alkyl-, —$C_{0-3}$alkylOC(=O)C$_{0-3}$alkyl-, —$C_{0-3}$alkylS(=O)—$C_{0-3}$alkyl-, —$C_{0-3}$alkylS(=O)$_2$NR$^{24}$C$_{0-3}$alkyl-, or absent. In another embodiment, G$^1$ is C$_{1-6}$alkylene optionally substituted by 1-6 R$^{29}$, C$_{6-11}$arylene optionally substituted by 1-6 R$^{29}$, C$_{3-11}$cycloalkylene optionally substituted by 1-6 R$^{29}$, 3-15 membered heterocycloalkylene optionally substituted by 1-6 R$^{29}$, 5-15 membered heteroarylene optionally substituted by 1-6 R$^{29}$, —$C_{0-3}$alkylC(=O)C$_{0-3}$alkyl-, —$C_{0-3}$alkylC(=O)OC$_{0-3}$ alkyl-, —$C_{0-3}$alkylC(=O)NR$^{24}$C$_{0-3}$alkyl-, —$C_{0-3}$ alkylNR$^{24}$C$_{0-3}$alkyl-, —$C_{0-3}$alkylNR$^{24}$C(=O)C$_{0-3}$alkyl-, —$C_{0-3}$alkylNR$^{24}$C(=O)NR$^{24}$C$_{0-3}$alkyl-, —$C_{0-3}$alkylNR$^{24}$S(=O)$_2$C$_{0-3}$alkyl-, —$C_{0-3}$alkylOC$_{0-3}$alkyl-, —$C_{0-3}$alkylOC(=O)C$_{0-3}$alkyl-, —$C_{0-3}$alkylS(=O)$_2$C$_{0-3}$alkyl-, —$C_{0-3}$ alkylS(=O)$_2$ NR$^{24}$C$_{0-3}$alkyl-, or absent. In another embodiment, G$^1$ is C$_{1-6}$alkylene optionally substituted by 1-3 R$^{29}$, C$_{6-11}$arylene optionally substituted by 1-3 R$^{29}$, C$_{3-11}$cycloalkylene optionally substituted by 1-3 R$^{29}$, 3-15 membered heterocycloalkylene optionally substituted by 1-3 R$^{29}$, 5-15 membered heteroarylene optionally substituted by 1-3 R$^{29}$, —$C_{0-3}$alkylC(=O)C$_{0-3}$alkyl-, —$C_{0-3}$alkylC(=O)OC$_{0-3}$ alkyl-, —$C_{0-3}$ alkylC(=O)NR$^{24}$C$_{0-3}$alkyl-, —$C_{0-3}$ alkylNR$^{24}$C$_{0-3}$alkyl-, —$C_{0-3}$alkylNR$^{24}$C(=O)C$_{0-3}$alkyl-, —$C_{0-3}$alkylNR$^{24}$C(=O)NR$^{24}$C$_{0-3}$alkyl-, —$C_{0-3}$alkylNR$^{24}$S(=O)$_2$C$_{0-3}$alkyl-, —$C_{0-3}$alkylOC$_{0-3}$alkyl-, —$C_{0-3}$alkylOC(=O)C$_{0-3}$alkyl-, —$C_{0-3}$alkylS(=O)$_2$C$_{0-3}$alkyl-, —$C_{0-3}$ alkylS(=O)$_2$ NR$^{24}$C$_{0-3}$alkyl-, or absent. In another embodiment, G$^1$ is C$_{1-6}$alkylene optionally substituted by 1-3 R$^{29}$, C$_{6-11}$arylene optionally substituted by 1-3 R$^{29}$, C$_{3-11}$cycloalkylene optionally substituted by 1-3 R$^{29}$, 3-15 membered heterocycloalkylene optionally substituted by 1-3 R$^{29}$, 5-15 membered heteroarylene optionally substituted by 1-3 R$^{29}$, —C(=O)—, —C(=O)O—, —C(=O)NR$^{24}$—, —NR$^{24}$—, —NR$^{24}$C(=O)—, —NR$^{24}$C(=O)NR$^{24}$—, —NR$^{24}$S(=O)$_2$—, —O—, —OC(=O)—, —S(=O)$_2$—, —S(=O)$_2$NR$^{24}$—, or absent. In another embodiment, G$^1$ is C$_{1-6}$alkylene optionally substituted by 1-6 R$^{29}$, C$_{6-11}$arylene optionally substituted by 1-6 R$^{29}$, C$_{7-16}$arylalkylene optionally substituted by 1-6 R$^{29}$, C$_{3-11}$cycloalkylene optionally substituted by 1-6 R$^{29}$, C$_{4-17}$cycloalkylalkylene optionally substituted by 1-6 R$^{29}$, 3-15 membered heterocycloalkylene optionally substituted by 1-6 R$^{29}$, 4-21 membered heterocycloalkylalkylene optionally substituted by 1-6 R$^{29}$, 5-15 membered heteroarylene optionally substituted by 1-6 R$^{29}$, 6-21 membered heteroarylalkylene optionally substituted by 1-6 R$^{29}$, —C(=O)—, —C(=O)O—, —C(=O)NR$^{24}$—, —C(=O)C(=O)—, —C(=S)NR$^{24}$—, —NR$^{24}$—, —NR$^{24}$NR$^{24}$—, —NR$^{24}$C(=O)—, —NR$^{24}$C(=O)C(=O)—, —NR$^{24}$C(=O)O—, —NR$^{24}$C(=O)C(=O)O—, —NR$^{24}$C(=O)NR$^{24}$—, —NR$^{24}$C(=O)NR$^{24}$C(=O)—, —NR$^{24}$C(=O)NR$^{24}$C(=O)O—, —NR$^{24}$C(=O)C(=O)NR$^{24}$—, —NR$^{24}$C(=S)—, —NR$^{24}$C(=S)O—, —NR$^{24}$C(=S)NR$^{24}$—, —NR$^{24}$S(=O)$_2$—, —NR$^{24}$S(=O)$_2$NR$^{27}$—, —O—, —OC(=O)—, —OC(=O)NR$^{24}$—, —OC(=O)O—, —OS(=O)—, —OS(=O)$_2$—, —OS(=O)$_2$O—, —OS(=O)$_2$NR$^{24}$—, —S(=O)$_n$—, —S(=O)$_2$O—, —SO$_3$—, —S(=O)$_2$NR$^{24}$—, —S(=O)NR$^{24}$—, or absent. In another embodiment, G$^1$ is C$_{1-6}$alkylene optionally substituted by 1-6 R$^{29}$, C$_{6-11}$arylene optionally substituted by 1-6 R$^{29}$, C$_{7-16}$arylalkylene optionally substituted by 1-6 R$^{29}$, C$_{3-11}$cycloalkylene optionally substituted by 1-6 R$^{29}$, C$_{4-17}$cycloalkylalkylene optionally substituted by 1-6 R$^{29}$, 3-15 membered heterocycloalkylene optionally substituted by 1-6 R$^{29}$, 4-21 membered heterocycloalkylalkylene optionally substituted by 1-6 R$^{29}$, 5-15 membered heteroarylene optionally substituted by 1-6 R$^{29}$, 6-21 membered heteroarylalkylene optionally substituted by 1-6 R$^{29}$, —C(=O)—, —C(=O)O—, —C(=O)NR$^{24}$—, —C(=S)NR$^{24}$—, —NR$^{24}$—, —NR$^{24}$NR$^{24}$—, —NR$^{24}$C(=O)—, —NR$^{24}$C(=O)O—, —NR$^{24}$C(=O)NR$^{24}$—, —NR$^{24}$C(=O)NR$^{24}$C(=O)—, —NR$^{24}$C(=O)NR$^{24}$C(=O)O—, —NR$^{24}$C(=S)—, —NR$^{24}$C(=S)NR$^{24}$—, —NR$^{24}$S(=O)$_2$—, —O—, —OC(=O)—, —OC(=O)NR$^{24}$—, —S(=O)$_n$—, —S(=O)$_2$NR$^{24}$—, or absent. In another embodiment, G$^1$ is C$_{1-6}$alkylene optionally substituted by 1-6 R$^{29}$, C$_{6-11}$arylene optionally substituted by 1-6 R$^{29}$, C$_{7-16}$arylalkylene optionally substituted by 1-6 R$^{29}$, C$_{3-11}$cycloalkylene optionally substituted by 1-6 R$^{29}$, C$_{4-17}$cycloalkylalkylene optionally substituted by 1-6 R$^{29}$, 3-15 membered heterocycloalkylene optionally substituted by 1-6 R$^{29}$, 4-21 membered heterocycloalkylalkylene optionally substituted by 1-6 R$^{29}$, 5-15 membered heteroarylene optionally substituted by 1-6 R$^{29}$, 6-21 membered heteroarylalkylene optionally substituted by 1-6 R$^{29}$, —C(=O)—, —C(=O)O—, —C(=O)NR$^{24}$—, —C(=S)NR$^{24}$—, —NR$^{24}$—, —NR$^{24}$C(=O)—, —NR$^{24}$C(=O)O—, —NR$^{24}$C(=O)NR$^{24}$—, —NR$^{24}$C(=O)NR$^{24}$C(=O)—, —NR$^{24}$C(=O)NR$^{24}$C(=O)O—, —NR$^{24}$C(=S)—, —NR$^{24}$S(=O)$_2$—, —O—, —OC(=O)—, —OC(=O)NR$^{24}$—, —S(=O)$_n$—, —S(=O)$_2$NR$^{24}$—, —S(=O)NR$^{24}$—, or absent. In another embodiment, G$^1$ is C$_{1-6}$alkylene optionally substituted by 1-6 R$^{29}$, C$_{6-11}$arylene optionally substituted by 1-6 R$^{29}$, C$_{3-11}$cycloalkylene optionally substituted by 1-6 R$^{29}$, 3-15 membered heterocycloalkylene optionally substituted by 1-6 R$^{29}$, 5-15 membered heteroarylene optionally substituted by 1-6 R$^{29}$, —C(=O)—, —C(=O)O—, —C(=O)NR$^{24}$—, —NR$^{24}$—, —NR$^{24}$C(=O)—, —NR$^{24}$C(=O)O—, —NR$^{24}$C(=O)NR$^{24}$—, —NR$^{24}$S(=O)$_2$—, —O—, —OC(=O)—, —OC(=O)NR$^{24}$—, —S(=O)$_n$—, —S(=O)$_2$NR$^{24}$—, or absent. In another embodiment, G$^1$ is C$_{1-6}$alkylene optionally substituted by 1-12 R$^{29}$, 3-15 membered heterocycloalkylene optionally substituted by 1-27 R$^{29}$, 5-15 membered heteroarylene optionally substituted by 1-14 R$^{29}$, —$C_{0-3}$alkylC(=O)NR$^{24}$C$_{0-3}$alkyl-, —$C_{0-3}$alkylNR$^{24}$C$_{0-3}$alkyl-, —$C_{0-3}$alkylOC$_{0-3}$alkyl-, —$C_{0-3}$alkylS(=O)$_2$NR$^{24}$C$_{0-3}$alkyl-, or absent. In another embodiment, G$^1$ is C$_{1-6}$alkylene optionally substituted by 1-3 R$^{29}$, 3-15 membered heterocycloalkylene optionally substituted by 1-3 R$^{29}$, 5-15 membered heteroarylene optionally substituted by 1-3 $R^{29}$, —C(=O)$NR^{24}$—, —$NR^{24}$—, —$OC_{0-3}$alkyl-, —S(=O)$_2NR^{24}$—, or absent. In another embodiment, $G^1$ is $C_{1-6}$alkylene optionally substituted by 1-3 $R^{29}$, phenylene optionally substituted by 1-3 $R^{29}$, $C_{3-7}$cycloalkylene optionally substituted by 1-3 $R^{29}$, 3-11 membered heterocycloalkylene optionally substituted by 1-3 $R^{29}$, 5-10 membered heteroarylene optionally substituted by 1-3 $R^{29}$, —C(=O)—, —C(=O)O—, —C(=O)$NR^{24}$—, —$NR^{24}$—, —$NR^{24}$C(=O)—, —$NR^{24}$C(=O)$NR^{24}$—, —$NR^{24}$S(=O)$_2$—, —O—, —OC(=O)—, —S(=O)$_2$—, —S(=O)$_2NR^{24}$—, or absent. In another embodiment, $G^1$ is $C_{1-6}$alkylene optionally substituted by 1-3 $R^{29}$, phenylene optionally substituted by 1-3 $R^{29}$, $C_{3-7}$cycloalkylene optionally substituted by 1-3 $R^{29}$, 3-11 membered heterocycloalkylene optionally substituted by 1-3 $R^{29}$, 5-6 membered heteroarylene optionally substituted by 1-3 $R^{29}$, —C(=O)—, —C(=O)O—, —C(=O)$NR^{24}$—, —$NR^{24}$—, —$NR^{24}$C(=O)—, —$NR^{24}$C(=O)$NR^{24}$—, —$NR^{24}$S(=O)$_2$—, —O—, —OC(=O)—, —S(=O)$_2$—, —S(=O)$_2NR^{24}$—, or absent. In another embodiment, $G^1$ is $C_{1-6}$alkylene optionally substituted by 1-3 $R^{29}$, phenylene optionally substituted by 1-3 $R^{29}$, $C_{4-7}$cycloalkylene optionally substituted by 1-3 $R^{29}$, 4-8 or 11 membered heterocycloalkylene optionally substituted by 1-3 $R^{29}$, 5-6 membered heteroarylene optionally substituted by 1-3 $R^{29}$, —C(=O)—, —C(=O)O—, —C(=O)$NR^{24}$—, —$NR^{24}$—, —$NR^{24}$C(=O)—, —$NR^{24}$C(=O)$NR^{24}$—, —$NR^{24}$S(=O)$_2$—, —O—, —OC(=O)—, —S(=O)$_2$—, —S(=O)$_2NR^{24}$—, or absent. In another embodiment, $G^1$ is $C_{1-6}$alkylene optionally substituted by 1-3 $R^{29}$, 5-6 membered heterocycloalkylene optionally substituted by 1-3 $R^{29}$, 5-6 membered heteroarylene optionally substituted by 1-3 $R^{29}$, —C(=O)$NR^{24}$—, —$NR^{24}$—, —$OC_{0-3}$alkyl-, —S(=O)$_2NR^{24}$—, or absent. In another embodiment, $G^1$ is $C_{1-6}$alkylene optionally substituted by 1-3 $R^{29}$, 5-6 membered heterocycloalkylene optionally substituted by 1-3 $R^{29}$, pyridinylene optionally substituted by 1-3 $R^{29}$, —C(=O)$NR^{24}$—, —$NR^{24}$—, —$OC_{0-3}$alkyl-, —S(=O)$_2NR^{24}$—, or absent. In another embodiment, $G^1$ is $C_{1-6}$alkylene optionally substituted by 1-3 $R^{29}$, 5-6 membered heterocycloalkylene optionally substituted by 1-3 $R^{29}$, wherein the heterocycloalkylene group contains, in addition to carbon atoms, one or two heteroatoms chosen from nitrogen and oxygen, pyridinylene optionally substituted by 1-3 $R^{29}$, —C(=O)$NR^{24}$—, —$NR^{24}$—, —$OC_{0-3}$alkyl-, —S(=O)$_2NR^{24}$—, or absent. In another embodiment, $G^1$ is $C_{1-6}$alkylene, 5-6 membered heterocycloalkylene, wherein the heterocycloalkylene group contains, in addition to carbon atoms, one or two heteroatoms chosen from nitrogen and oxygen, pyridinylene, —C(=O)NH—, —N($C_{1-6}$alkyl)-, —$OC_{0-3}$alkyl-, —S(=O)$_2$N($C_{1-6}$alkyl)-, or absent. In another embodiment, $G^1$ is $C_{1-6}$alkylene, morpholinylene, piperazinylene, piperidinylene, pyrrolidinylene, pyridinylene, —C(=O)NH—, —N($C_{1-6}$alkyl)-, —$OC_{0-3}$alkyl-, —S(=O)$_2$N($C_{1-6}$alkyl)-, or absent. In another embodiment, $G^1$ is methylene, ethylene, morpholinylene, piperazinylene, piperidinylene, pyrrolidinylene, pyridinylene, —C(=O)NH—, —N(CH$_3$)—, —O—, —OCH$_2$CH$_2$—, —OCH$_2$CH$_2$CH$_2$—, —S(=O)$_2$N(CH$_3$)—, or absent. In another embodiment, $G^1$ is methylene, ethylene, morpholin-4-ylene, morpholin-2-ylene, piperazin-1-ylene, piperidin-1-ylene, pyrrolidin-1-ylene, 3-pyridinylene, —C(=O)NH—, —N(CH$_3$)—, —O—, —OCH$_2$CH$_2$—, —OCH$_2$CH$_2$CH$_2$—, —S(=O)$_2$N(CH$_3$)—, or absent.

In each embodiment of the present invention that is described in the paragraphs that precede or follow this paragraph, the definition of $X^1$ may be chosen from any of the embodiments that are described in this paragraph. In one embodiment, $X^1$ is $C_{1-6}$alkylene optionally substituted by 1-12 $R^{39}$, $C_{2-6}$alkenylene optionally substituted by 1-10 $R^{39}$, $C_{2-6}$alkynylene optionally substituted by 1-8 $R^{39}$, $C_{6-11}$arylene optionally substituted by 1-10 $R^{39}$, $C_{7-16}$arylalkylene optionally substituted by 1-18 $R^{39}$, $C_{3-11}$cycloalkylene optionally substituted by 1-20 $R^{39}$, $C_{4-17}$cycloalkylalkylene optionally substituted by 1-31 $R^{39}$, 3-15 membered heterocycloalkylene optionally substituted by 1-27 $R^{39}$, 4-21 membered heterocycloalkylalkylene optionally substituted by 1-39 $R^{39}$, 5-15 membered heteroarylene optionally substituted by 1-14 $R^{39}$, 6-21 membered heteroarylalkylene optionally substituted by 1-26 $R^{39}$, —$C_{0-3}$alkylC(=O)$C_{0-3}$alkyl-, —$C_{0-3}$alkylC(=O)O$C_{0-3}$alkyl-, —$C_{0-3}$alkylC(=O)$NR^{34}C_{0-3}$alkyl-, —$C_{0-3}$alkylC(=O)C(=O)$C_{0-3}$alkyl-, —$C_{0-3}$alkylC(=$NR^{35}$)$C_{0-3}$alkyl-, —$C_{0-3}$alkylC(=$NR^{35}$)$NR^{34}C_{0-3}$alkyl-, —$C_{0-3}$alkylC(=NOH)$NR^{34}C_{0-3}$alkyl-, —$C_{0-3}$alkylC(=NO$R^{36}$)$C_{0-3}$alkyl-, —$C_{0-3}$alkylC(=NN$R^{32}R^{33}$)$C_{0-3}$alkyl-, —$C_{0-3}$alkylC(=NN$R^{34}$C(=O)$R^{31}$)$C_{0-3}$alkyl-, —$C_{0-3}$alkylC(=NN$R^{34}$C(=O)O$R^{31}$)$C_{0-3}$alkyl-, —$C_{0-3}$alkylC(=S)$NR^{34}C_{0-3}$alkyl-, —$C_{0-3}$alkylN$R^{34}C_{0-3}$alkyl-, —$C_{0-3}$alkylN$R^{34}$N$R^{34}C_{0-3}$alkyl-, —$C_{0-3}$alkylN=N$C_{0-3}$alkyl-, —$C_{0-3}$alkylN$R^{34}$C(=O)$C_{0-3}$alkyl-, —$C_{0-3}$alkylN$R^{34}$C(=O)C(=O)$C_{0-3}$alkyl-, —$C_{0-3}$alkylN$R^{34}$C(=O)O$C_{0-3}$alkyl-, —$C_{0-3}$alkylN$R^{34}$C(=O)C(=O)O$C_{0-3}$alkyl-, —$C_{0-3}$alkylN$R^{34}$C(=O)N$R^{34}C_{0-3}$alkyl-, —$C_{0-3}$alkylN$R^{34}$C(=O)N$R^{34}$C(=O)$C_{0-3}$alkyl-, —$C_{0-3}$alkylN$R^{34}$C(=O)N$R^{34}$C(=O)O$C_{0-3}$alkyl-, —$C_{0-3}$alkylN$R^{34}$C(=N$R^{35}$)N$R^{34}C_{0-3}$alkyl-, —$C_{0-3}$alkylN$R^{34}$C(=O)C(=O)N$R^{34}C_{0-3}$alkyl-, —$C_{0-3}$alkylN$R^{34}$C(=S)$C_{0-3}$alkyl-, —$C_{0-3}$alkylN$R^{34}$C(=S)O$C_{0-3}$alkyl-, —$C_{0-3}$alkylN$R^{34}$C(=S)N$R^{34}C_{0-3}$alkyl-, —$C_{0-3}$alkylN$R^{34}$S(=O)$_2C_{0-3}$alkyl-, —$C_{0-3}$alkylN$R^{34}$S(=O)$_2$N$R^{34}C_{0-3}$alkyl-, —$C_{0-3}$alkylO$C_{0-3}$alkyl-, —$C_{0-3}$alkylOC(=O)$C_{0-3}$alkyl-, —$C_{0-3}$alkylOC(=O)N$R^{34}C_{0-3}$alkyl-, —$C_{0-3}$alkylOC(=O)O$C_{0-3}$alkyl-, —$C_{0-3}$alkylOC(=N$R^{35}$)N$R^{34}C_{0-3}$alkyl-, —$C_{0-3}$alkylOS(=O)$C_{0-3}$alkyl-, —$C_{0-3}$alkylOS(=O)$_2C_{0-3}$alkyl-, —$C_{0-3}$alkylOS(=O)$_2$O$C_{0-3}$alkyl-, —$C_{0-3}$alkylOS(=O)$_2$N$R^{34}C_{0-3}$alkyl-, —$C_{0-3}$alkylS(=O)—$C_{0-3}$alkyl-, —$C_{0-3}$alkylS(=O)$_2$O$C_{0-3}$alkyl-, —$C_{0-3}$alkylSO$_3C_{0-3}$alkyl-, —$C_{0-3}$alkylS(=O)$_2$N$R^{34}C_{0-3}$alkyl-, —$C_{0-3}$alkylS(=O)N$R^{34}C_{0-3}$alkyl-, or absent. In another embodiment, $X^1$ is $C_{1-6}$alkylene optionally substituted by 1-12 $R^{39}$, $C_{6-11}$ arylene optionally substituted by 1-6 $R^{39}$, $C_{7-16}$arylalkylene optionally substituted by 1-18 $R^{39}$, $C_{3-11}$cycloalkylene optionally substituted by 1-20 $R^{39}$, $C_{4-17}$cycloalkylalkylene optionally substituted by 1-31 $R^{39}$, 3-15 membered heterocycloalkylene optionally substituted by 1-27 $R^{39}$, 4-21 membered heterocycloalkylalkylene optionally substituted by 1-39 $R^{39}$, 5-15 membered heteroarylene optionally substituted by 1-14 $R^{39}$, 6-21 membered heteroarylalkylene optionally substituted by 1-26 $R^{39}$, —$C_{0-3}$alkylC(=O)$C_{0-3}$alkyl-, —$C_{0-3}$alkylC(=O)O$C_{0-3}$alkyl-, —$C_{0-3}$alkylC(=O)N$R^{34}C_{0-3}$alkyl-, —$C_{0-3}$alkylC(=O)C(=O)$C_{0-3}$alkyl-, —$C_{0-3}$alkylC(=S)N$R^{34}C_{0-3}$alkyl-, —$C_{0-3}$alkylN$R^{34}C_{0-3}$alkyl-, —$C_{0-3}$alkylN$R^{34}$N$R^{34}C_{0-3}$alkyl-, —$C_{0-3}$alkylN$R^{34}$C(=O)$C_{0-3}$alkyl-, —$C_{0-3}$alkylN$R^{34}$C(=O)C(=O)$C_{0-3}$alkyl-, —$C_{0-3}$alkylN$R^{34}$C(=O)O$C_{0-3}$alkyl-, —$C_{0-3}$alkylN$R^{34}$C(=O)C(=O)O$C_{0-3}$alkyl-, —$C_{0-3}$alkylN$R^{34}$C(=O)N$R^{34}C_{0-3}$alkyl-, —$C_{0-3}$alkylN$R^{34}$C(=O)N$R^{34}C_{0-3}$alkyl-, —$C_{0-3}$alkylN$R^{34}$C(=O)N$R^{34}$C(=O)O$C_{0-3}$alkyl-, —$C_{0-3}$alkylN$R^{34}$C(=N$R^{35}$)N$R^{34}C_{0-3}$alkyl-, —$C_{0-3}$alkylN$R^{34}$C(=O)C(=O)N$R^{34}C_{0-3}$alkyl-, —$C_{0-3}$alkylN$R^{34}$C(=S)$C_{0-3}$alkyl-, —$C_{0-3}$alkylN$R^{34}$C(=S)O$C_{0-3}$alkyl-, —$C_{0-3}$alkylN$R^{34}$C(=S)N$R^{34}C_{0-3}$alkyl-, —$C_{0-3}$alkylN$R^{34}$S(=O)$_2C_{0-3}$alkyl-, —$C_{0-3}$alkylN$R^{34}$S(=O)$_2$N$R^{34}C_{0-3}$alkyl-, —$C_{0-3}$alkylO$C_{0-3}$alkyl-, —$C_{0-3}$alkylOC(=O)$C_{0-3}$alkyl-, —$C_{0-3}$alkylOC(=O)N$R^{34}C_{0-3}$alkyl-, —$C_{0-3}$alkylOC(=O)O$C_{0-3}$ alkyl-, —C$_{0-3}$alkylOS(=O)C$_{0-3}$alkyl-, —C$_{0-3}$alkylOS(=O)$_2$C$_{0-3}$alkyl-, —C$_{0-3}$alkylOS(=O)$_2$OC$_{0-3}$alkyl-, —C$_{0-3}$alkylOS(=O)$_2$NR$^{34}$C$_{0-3}$alkyl-, —C$_{0-3}$alkylS(=O)—C$_{0-3}$alkyl-, —C$_{0-3}$alkylS(=O)$_2$OC$_{0-3}$alkyl-, —C$_{0-3}$alkylSO$_3$C$_{0-3}$alkyl-, —C$_{0-3}$alkylS(=O)$_2$NR$^{34}$C$_{0-3}$alkyl-, —C$_{0-3}$alkylS(=O)NR$^{34}$C$_{0-3}$alkyl-, or absent. In another embodiment, X$^1$ is C$_{1-6}$alkylene optionally substituted by 1-12 R$^{39}$, C$_{6-11}$arylene optionally substituted by 1-6 R$^{39}$, C$_{7-16}$arylalkylene optionally substituted by 1-18 R$^{39}$, C$_{3-11}$cycloalkylene optionally substituted by 1-20 R$^{39}$, C$_{4-17}$cycloalkylalkylene optionally substituted by 1-31 R$^{39}$, 3-15 membered heterocycloalkylene optionally substituted by 1-27 R$^{39}$, 4-21 membered heterocycloalkylalkylene optionally substituted by 1-39 R$^{39}$, 5-15 membered heteroarylene optionally substituted by 1-14 R$^{39}$, 6-21 membered heteroarylalkylene optionally substituted by 1-26 R$^{39}$, —C$_{0-3}$alkylC(=O)C$_{0-3}$alkyl-, —C$_{0-3}$alkylC(=O)OC$_{0-3}$alkyl-, —C$_{0-3}$alkylC(=O)NR$^{34}$C$_{0-3}$alkyl-, —C$_{0-3}$alkylC(=S)NR$^{34}$C$_{0-3}$alkyl-, —C$_{0-3}$alkylNR$^{34}$C$_{0-3}$alkyl-, —C$_{0-3}$alkylNR$^{34}$NR$^{34}$C$_{0-3}$alkyl-, —C$_{0-3}$alkylNR$^{34}$C(=O)C$_{0-3}$alkyl-, —C$_{0-3}$alkylNR$^{34}$C(=O)OC$_{0-3}$alkyl-, —C$_{0-3}$alkylNR$^{34}$C(=O)NR$^{34}$C$_{0-3}$alkyl-, —C$_{0-3}$alkylNR$^{34}$C(=O)NR$^{34}$C(=O)C$_{0-3}$alkyl-, —C$_{0-3}$alkylNR$^{34}$C(=O)NR$^{34}$C(=O)OC$_{0-3}$alkyl-, —C$_{0-3}$alkylNR$^{34}$C(=NR$^{35}$)NR$^{34}$C$_{0-3}$alkyl-, —C$_{0-3}$alkylNR$^{34}$C(=S)NR$^{34}$C$_{0-3}$alkyl-, —C$_{0-3}$alkylNR$^{34}$S(=O)$_2$C$_{0-3}$alkyl-, —C$_{0-3}$alkylOC$_{0-3}$alkyl-, —C$_{0-3}$alkylOC(=O)C$_{0-3}$alkyl-, —C$_{0-3}$alkylOC(=O)NR$^{34}$C$_{0-3}$alkyl-, —C$_{0-3}$alkylS(=O)—C$_{0-3}$alkyl-, —C$_{0-3}$alkylS(=O)$_2$NR$^{34}$C$_{0-3}$alkyl-, or absent. In another embodiment, X$^1$ is C$_{1-6}$alkylene optionally substituted by 1-12 R$^{39}$, C$_{6-11}$ arylene optionally substituted by 1-6 R$^{39}$, C$_{7-16}$arylalkylene optionally substituted by 1-18 R$^{39}$, C$_{3-11}$ cycloalkylene optionally substituted by 1-20 R$^{39}$, C$_{4-17}$cycloalkylalkylene optionally substituted by 1-31 R$^{39}$, 3-15 membered heterocycloalkylene optionally substituted by 1-27 R$^{39}$, 4-21 membered heterocycloalkylalkylene optionally substituted by 1-39 R$^{39}$, 5-15 membered heteroarylene optionally substituted by 1-14 R$^{39}$, 6-21 membered heteroarylalkylene optionally substituted by 1-26 R$^{39}$, —C$_{0-3}$ alkylC(=O)C$_{0-3}$alkyl-, —C$_{0-3}$alkylC(=O)OC$_{0-3}$alkyl-, —C$_{0-3}$alkylC(=O)NR$^{34}$C$_{0-3}$alkyl-, —C$_{0-3}$alkylC(=S)NR$^{34}$C$_{0-3}$alkyl-, —C$_{0-3}$alkylNR$^{34}$C$_{0-3}$alkyl-, —C$_{0-3}$alkylNR$^{34}$C(=O)C$_{0-3}$alkyl-, —C$_{0-3}$alkylNR$^{34}$C(=O)OC$_{0-3}$alkyl-, —C$_{0-3}$alkylNR$^{34}$C(=O)NR$^{34}$C$_{0-3}$alkyl-, —C$_{0-3}$alkylNR$^{34}$C(=O)NR$^{34}$C(=O)C$_{0-3}$alkyl-, —C$_{0-3}$alkylNR$^{34}$C(=O)NR$^{34}$C(=O)OC$_{0-3}$alkyl-, —C$_{0-3}$alkylNR$^{34}$S(=O)$_2$C$_{0-3}$alkyl-, —C$_{0-3}$alkylOC$_{0-3}$alkyl-, —C$_{0-3}$alkylOC(=O)C$_{0-3}$alkyl-, —C$_{0-3}$alkylOC(=O)NR$^{34}$C$_{0-3}$alkyl-, —C$_{0-3}$alkylS(=O)—C$_{0-3}$alkyl-, —C$_{0-3}$alkylS(=O)$_2$NR$^{34}$C$_{0-3}$alkyl-, or absent. In another embodiment, X$^1$ is C$_{1-6}$alkylene optionally substituted by 1-12 R$^{39}$, C$_{6-11}$arylene optionally substituted by 1-6 R$^{39}$, C$_{3-11}$ cycloalkylene optionally substituted by 1-20 R$^{39}$, 3-15 membered heterocycloalkylene optionally substituted by 1-27 R$^{39}$, 5-15 membered heteroarylene optionally substituted by 1-14 R$^{39}$, —C$_{0-3}$alkylC(=O)C$_{0-3}$alkyl-, —C$_{0-3}$alkylC(=O)OC$_{0-3}$alkyl-, —C$_{0-3}$alkylC(=O)NR$^{34}$C$_{0-3}$alkyl-, —C$_{0-3}$alkylNR$^{34}$C$_{0-3}$alkyl-, —C$_{0-3}$alkylNR$^{34}$C(=O)C$_{0-3}$alkyl-, —C$_{0-3}$alkylNR$^{34}$C(=O)OC$_{0-3}$alkyl-, —C$_{0-3}$alkylNR$^{34}$C(=O)NR$^{34}$C$_{0-3}$alkyl-, —C$_{0-3}$alkylNR$^{34}$S(=O)$_2$C$_{0-3}$alkyl-, —C$_{0-3}$alkylOC$_{0-3}$alkyl-, —C$_{0-3}$alkylOC(=O)C$_{0-3}$alkyl-, —C$_{0-3}$alkylOC(=O)NR$^{34}$C$_{0-3}$alkyl-, —C$_{0-3}$alkylS(=O)—C$_{0-3}$alkyl-, —C$_{0-3}$alkylS(=O)$_2$NR$^{34}$C$_{0-3}$alkyl-, or absent. In another embodiment, X$^1$ is C$_{1-6}$alkylene optionally substituted by 1-12 R$^{39}$, 3-15 membered heterocycloalkylene optionally substituted by 1-27 R$^{39}$, 5-15 membered heteroarylene optionally substituted by 1-14 R$^{39}$, —C$_{0-3}$alkylC(=O)C$_{0-3}$alkyl-, —C$_{0-3}$alkylC(=O)OC$_{0-3}$alkyl-, —C$_{0-3}$alkylNR$^{34}$C$_{0-3}$alkyl-, —C$_{0-3}$alkylOC$_{0-3}$alkyl-, —C$_{0-3}$alkyloC(=O)C$_{0-3}$alkyl-, —C$_{0-3}$alkylS(=O)—C$_{0-3}$alkyl-, or absent. In another embodiment, X$^1$ is C$_{1-6}$alkylene optionally substituted by 1-6 R$^{39}$, 3-15 membered heterocycloalkylene optionally substituted by 1-6 R$^{39}$, 5-15 membered heteroarylene optionally substituted by 1-6 R$^{39}$, —C$_{0-3}$alkylC(=O)C$_{0-3}$alkyl-, —C$_{0-3}$alkylC(=O)OC$_{0-3}$alkyl-, —C$_{0-3}$alkylNR$^{34}$C$_{0-3}$alkyl-, —C$_{0-3}$alkylOC$_{0-3}$alkyl-, —C$_{0-3}$alkylOC(=O)C$_{0-3}$alkyl-, —C$_{0-3}$alkylS(=O)$_2$C$_{0-3}$alkyl-, or absent. In another embodiment, X$^1$ is C$_{1-6}$alkylene optionally substituted by 1-6 R$^{39}$, 3-7 membered heterocycloalkylene optionally substituted by 1-6 R$^{39}$, 5-6 membered heteroarylene optionally substituted by 1-6 R$^{39}$, —C$_{0-3}$alkylC(=O)C$_{0-3}$alkyl-, —C$_{0-3}$alkylC(=O)OC$_{0-3}$alkyl-, —C$_{0-3}$alkylNR$^{34}$C$_{0-3}$alkyl-, —C$_{0-3}$alkylOC$_{0-3}$alkyl-, —C$_{0-3}$alkyloC(=O)C$_{0-3}$alkyl-, —C$_{0-3}$alkylS(=O)$_2$C$_{0-3}$alkyl-, or absent. In another embodiment, X$^1$ is C$_{1-6}$alkylene optionally substituted by 1-6 R$^{39}$, 3-7 membered heterocycloalkylene optionally substituted by 1-6 R$^{39}$, 5-6 membered heteroarylene optionally substituted by 1-6 R$^{39}$, —C(=O)—, —C(=O)O—, —NR$^{34}$—, —O—, —OC(=O)—, —S(=O)$_2$—, or absent. In another embodiment, X$^1$ is C$_{1-6}$alkylene optionally substituted by 1-6 R$^{39}$, C$_{6-11}$arylene optionally substituted by 1-6 R$^{39}$, C$_{7-16}$arylalkylene optionally substituted by 1-6 R$^{39}$, C$_{3-11}$cycloalkylene optionally substituted by 1-6 R$^{39}$, C$_{4-17}$cycloalkylalkylene optionally substituted by 1-6 R$^{39}$, 3-15 membered heterocycloalkylene optionally substituted by 1-6 R$^{39}$, 4-21 membered heterocycloalkylalkylene optionally substituted by 1-6 R$^{39}$, 5-15 membered heteroarylene optionally substituted by 1-6 R$^{39}$, 6-21 membered heteroarylalkylene optionally substituted by 1-6 R$^{39}$, —C(=O)—, —C(=O)O—, —C(=O)NR$^{34}$—, —C(=O)C(=O)—, —C(=S)NR$^{34}$—, —NR$^{34}$—, —NR$^{34}$NR$^{34}$—, —NR$^{34}$C(=O)—, —NR$^{34}$C(=O)C(=O)—, —NR$^{34}$C(=O)O—, —NR$^{34}$C(=O)C(=O)O—, —NR$^{34}$C(=O)NR$^{34}$—, —NR$^{34}$C(=O)NR$^{34}$C(=O)—, —NR$^{34}$C(=O)NR$^{34}$C(=O)O—, —NR$^{34}$C(=NR$^{35}$)NR$^{34}$—, —NR$^{34}$C(=O)C(=O)NR$^{34}$—, —NR$^{34}$C(=S)—, —NR$^{34}$C(=S)O—, —NR$^{34}$C(=S)NR$^{34}$—, —NR$^{34}$S(=O)$_2$—, —NR—, —O—, —OC(=O)—, —OC(=O)NR$^{34}$—, —OC(=O)O—, —OS(=O)—, —OS(=O)$_2$—, —OS(=O)$_2$O—, —OS(=O)$_2$NR$^{34}$—, —S(=O)$_n$—, —S(=O)$_2$O—, —SO$_3$—, —S(=O)$_2$NR$^{34}$—, —S(=O)NR$^{34}$—, or absent. In another embodiment, X$^1$ is C$_{1-6}$alkylene optionally substituted by 1-6 R$^{39}$, C$_{6-11}$arylene optionally substituted by 1-6 R$^{39}$, C$_{7-16}$arylalkylene optionally substituted by 1-6 R$^{39}$, C$_{3-11}$cycloalkylene optionally substituted by 1-6 R$^{39}$, C$_{4-17}$cycloalkylalkylene optionally substituted by 1-6 R$^{39}$, 3-15 membered heterocycloalkylene optionally substituted by 1-6 R$^{39}$, 4-21 membered heterocycloalkylalkylene optionally substituted by 1-6 R$^{39}$, 5-15 membered heteroarylene optionally substituted by 1-6 R$^{39}$, 6-21 membered heteroarylalkylene optionally substituted by 1-6 R$^{39}$, —C(=O)—, —C(=O)O—, —C(=O)NR$^{34}$—, —C(=S)NR$^{34}$—, —NR$^{34}$—, —NR$^{34}$NR$^{34}$—, —NR$^{34}$C(=O)—, —NR$^{34}$C(=O)O—, —NR$^{34}$C(=O)NR$^{34}$—, —NR$^{34}$C(=O)NR$^{34}$C(=O)—, —NR$^{34}$C(=O)NR$^{34}$C(=O)O—, —NR$^{34}$C(=NR$^{35}$)NR$^{34}$—, —NR$^{34}$C(=S)NR$^{34}$—, —NR$^{34}$S(=O)$_2$—, —O—, —OC(=O)—, —OC(=O)NR$^{34}$—, —S(=O)$_n$—, —S(=O)$_2$NR$^{34}$—, or absent. In another embodiment, X$^1$ is C$_{1-6}$alkylene optionally substituted by 1-6 R$^{39}$, C$_{6-11}$arylene optionally substituted by 1-6 R$^{39}$, C$_{7-16}$arylalkylene optionally substituted by 1-6 R$^{39}$, C$_{3-11}$cycloalkylene optionally substituted by 1-6 R$^{39}$, C$_{4-17}$cycloalkylalkylene optionally substituted by 1-6 R$^{39}$, 3-15 membered heterocycloalkylene optionally substituted by 1-6 R$^{39}$, 4-21 membered heterocycloalkylalkylene optionally substituted by 1-6 $R^{39}$, 5-15 membered heteroarylene optionally substituted by 1-6 $R^{39}$, 6-21 membered heteroarylalkylene optionally substituted by 1-6 $R^{39}$, —C(=O)—, —C(=O)O—, —C(=O)NR$^{34}$—, —C(=S)NR$^{34}$—, —NR$^{34}$—, —NR$^{34}$C(=O)—, —NR$^{34}$C(=O)O—, —NR$^{34}$C(=O)NR$^{34}$—, —NR$^{34}$C(=O)NR$^{34}$C(=O)—, —NR$^{34}$C(=O)NR$^{34}$C(=O)O—, —NR$^{34}$S(=O)$_2$—, —O—, —OC(=O)—, —OC(=O)NR$^{34}$—, —S(=O)$_n$—, —S(=O)$_2$NR$^{34}$—, or absent. In another embodiment, $X^1$ is $C_{1-6}$alkylene optionally substituted by 1-6 $R^{39}$, $C_{6-11}$arylene optionally substituted by 1-6 $R^{39}$, $C_{3-11}$cycloalkylene optionally substituted by 1-6 $R^{39}$, 3-15 membered heterocycloalkylene optionally substituted by 1-6 $R^{39}$, 5-15 membered heteroarylene optionally substituted by 1-6 $R^{39}$, —C(=O)—, —C(=O)O—, —C(=O)NR$^{34}$—, —NR$^{34}$—, —NR$^{34}$C(=O)—, —NR$^{34}$C(=O)O—, —NR$^{34}$C(=)NR$^{34}$—, —NR$^{34}$S(=O)$_2$—, —O—, —OC(=O)—, —OC(=O)NR$^{34}$—, —S(=O)$_n$—, —S(=O)$_2$NR$^{34}$—, or absent. In another embodiment, $X^1$ is $C_{1-6}$alkylene optionally substituted by 1-12 $R^{39}$, 3-15 membered heterocycloalkylene optionally substituted by 1-27 $R^{39}$, —C$_{0-3}$alkylOC$_{0-3}$alkyl-, or absent. In another embodiment, $X^1$ is $C_{1-6}$alkylene optionally substituted by 1-3 $R^{39}$, 3-15 membered heterocycloalkylene optionally substituted by 1-3 $R^{39}$, —C$_{0-3}$alkylOC$_{0-3}$alkyl-, or absent. In another embodiment, $X^1$ is $C_{1-6}$alkylene optionally substituted by 1-3 $R^{39}$, 3-15 membered heterocycloalkylene optionally substituted by 1-3 $R^{39}$, —O—, or absent. In another embodiment, $X^1$ is $C_{1-6}$alkylene optionally substituted by 1-3 $R^{39}$, 5-6 membered heterocycloalkylene optionally substituted by 1-3 $R^{39}$, —O—, or absent. In another embodiment, $X^1$ is $C_{1-6}$alkylene, 5-6 membered heterocycloalkylene, —O—, or absent. In another embodiment, $X^1$ is $C_{1-6}$alkylene optionally substituted by 1-3 $R^{39}$, 6 membered heterocycloalkylene optionally substituted by 1-3 $R^{39}$, —O—, or absent. In another embodiment, $X^1$ is $C_{1-6}$alkylene, 6 membered heterocycloalkylene, —O—, or absent. In another embodiment, $X^1$ is $C_{1-6}$alkylene, 6 membered heterocycloalkylene, wherein the heterocycloalkylene group contains, in addition to carbon atoms, one or two heteroatoms chosen from nitrogen and oxygen, —O—, or absent. In another embodiment, $X^1$ is $C_{1-6}$alkylene, 6 membered heterocycloalkylene, wherein the heterocycloalkylene group contains, in addition to carbon atoms, one or two nitrogen atoms or one nitrogen atom and one oxygen atom, —O—, or absent. In another embodiment, $X^1$ is $C_{1-6}$alkylene, piperazinylene, morpholinylene, piperidinylene, —O—, or absent. In another embodiment, $X^1$ is $C_{1-6}$alkylene, piperazinylene, morpholinylene, piperidinylene, —O—, or absent. In another embodiment, $X^1$ is methylene, ethylene, propylene, butylene, piperazinylene, morpholinylene, piperidinylene, —O—, or absent. In another embodiment, $X^1$ is methylene, ethylene, propylene, butylene, piperazin-1-ylene, morpholin-4-ylene, piperidin-4-ylene, —O—, or absent.

In each embodiment of the present invention that is described in the paragraphs that precede or follow this paragraph, the definition of $Z^1$ may be chosen from any of the embodiments that are described in this paragraph. In one embodiment, $Z^1$ is H, $C_{1-6}$alkyl optionally substituted by 1-13 $R^{49}$, $C_{2-6}$alkenyl optionally substituted by 1-11 $R^{49}$, $C_{2-6}$alkynyl optionally substituted by 1-9 $R^{49}$, $C_{6-11}$ aryl optionally substituted by 1-11 $R^{49}$, $C_{7-16}$arylalkyl optionally substituted by 1-19 $R^{49}$, $C_{3-11}$cycloalkyl optionally substituted by 1-21 $R^{49}$, $C_{4-17}$cycloalkylalkyl optionally substituted by 1-32 $R^{49}$, 3-15 membered heterocycloalkyl optionally substituted by 1-28 $R^{49}$, 4-21 membered heterocycloalkylalkyl optionally substituted by 1-40 $R^{49}$, 5-15 membered heteroaryl optionally substituted by 1-15 $R^{49}$, 6-21 membered heteroarylalkyl optionally substituted by 1-27 $R^{49}$, halogen, —CN, —C(=O)R$^{100}$, —C(=O)OR$^{100}$, —C(=O)NR$^{102}$R$^{103}$, —C(=O)C(=O)R$^{100}$, —C(=NR$^{105}$)R$^{100}$, —C(=NR$^{105}$)NR$^{102}$R$^{103}$, —C(=NOH)NR$^{102}$R$^{103}$, —C(=NOR$^{106}$)R$^{100}$, —C(=NNR$^{102}$R$^{103}$)R$^{100}$, —C(=NNR$^{104}$C(=O)R$^{101}$)R$^{100}$, —C(=NNR$^{104}$C(=O)OR$^{101}$)R$^{100}$, —C(=S)NR$^{102}$R$^{103}$, —NC, —NO$_2$, —NR$^{102}$R$^{103}$, —NR$^{104}$NR$^{102}$R$^{103}$, —N=NR$^{104}$, =NR$^{100}$, =NOR$^{100}$, —NR$^{104}$OR$^{106}$, —NR$^{104}$C(=O)R$^{100}$, —NR$^{104}$C(=O)C(=O)R$^{100}$, —NR$^{104}$C(=O)OR$^{101}$, —NR$^{104}$C(=O)C(=O)OR$^{101}$, —NR$^{104}$C(=O)NR$^{102}$R$^{103}$, NR$^{104}$C(=O)NR$^{104}$C(=O)R$^{100}$, —NR$^{104}$C(=O)NR$^{104}$C(=O)OR$^{100}$, —NR$^{104}$C(=NR$^{105}$)NR$^{102}$R$^{103}$, —NR$^{104}$C(=O)C(=O)NR$^{102}$R$^{103}$, —NR$^{104}$C(=S)R$^{100}$, —NR$^{104}$C(=S)OR$^{100}$, —NR$^{104}$C(=S)NR$^{102}$R$^{103}$, —NR$^{104}$S(=O)$_2$R$^{101}$, —NR$^{104}$S(=O)$_2$NR$^{102}$R$^{103}$, —NR$^{104}$P(=O)R$^{108}$R$^{108}$, —NR$^{104}$P(=O)(NR$^{102}$R$^{103}$)(NR$^{102}$R$^{103}$), NR$^{104}$P(=O)(OR$^{100}$)(OR$^{100}$), —NR$^{104}$P(=O)(SR$^{100}$)(SR$^{100}$), —OR$^{100}$, =O, —OCN, —OC(=O)R$^{100}$, —OC(=O)NR$^{102}$R$^{103}$, —OC(=O)OR$^{100}$, —OC(=NR$^{105}$)NR$^{102}$R$^{103}$, —OS(=O)R$^{100}$, —OS(=O)$_2$R$^{100}$, —OS(=O)$_2$OR$^{100}$, —OS(=O)$_2$NR$^{102}$R$^{103}$, —OP(=O)R$^{108}$R$^{108}$, —OP(=O)(NR$^{102}$R$^{103}$)(NR$^{102}$R$^{103}$), —OP(=O)(OR$^{100}$)(OR$^{100}$), —OP(=O)(SR$^{100}$)(SR$^{100}$), —SCN, =S, —S(=O)$_n$R$^{100}$, —S(=O)$_n$R$^{100}$, —S(=O)$_2$OR$^{100}$, —SO$_3$R$^{107}$, —S(=O)$_2$NR$^{102}$R$^{103}$, —S(=O)NR$^{102}$R$^{103}$, —SP(=O)R$^{108}$R$^{108}$, —SP(=O)(NR$^{102}$R$^{103}$)(NR$^{102}$R$^{103}$), —SP(=O)(OR$^{100}$)(OR$^{100}$), —SP(=O)(SR$^{100}$)(SR$^{100}$), —P(=O)R$^{108}$R$^{108}$, —P(=O)(NR$^{102}$R$^{103}$)(NR$^{102}$R$^{103}$), —P(=O)(OR$^{100}$)(OR$^{100}$), or —P(=O)(SR$^{100}$)(SR$^{100}$). In another embodiment, $Z^1$ is H, $C_{1-6}$alkyl optionally substituted by 1-13 $R^{49}$, $C_{2-6}$alkenyl optionally substituted by 1-11 $R^{49}$, $C_{2-6}$alkynyl optionally substituted by 1-9 $R^{49}$, $C_{6-11}$ aryl optionally substituted by 1-11 $R^{49}$, $C_{7-16}$arylalkyl optionally substituted by 1-19 $R^{49}$, $C_{3-11}$cycloalkyl optionally substituted by 1-21 $R^{49}$, $C_{4-17}$cycloalkylalkyl optionally substituted by 1-32 $R^{49}$, 3-15 membered heterocycloalkyl optionally substituted by 1-28 $R^{49}$, 4-21 membered heterocycloalkylalkyl optionally substituted by 1-40 $R^{49}$, 5-15 membered heteroaryl optionally substituted by 1-15 $R^{49}$, 6-21 membered heteroarylalkyl optionally substituted by 1-27 $R^{49}$, halogen, —CN, —C(=O)R$^{100}$, —C(=O)OR$^{100}$, —C(=O)NR$^{102}$R$^{103}$, —C(=O)C(=O)R$^{100}$, —C(=NR$^{105}$)R$^{100}$, —C(=NR$^{105}$)NR$^{102}$R$^{103}$, —C(=NOH)NR$^{102}$R$^{103}$, —C(=NOR$^{106}$)R$^{100}$, —C(=NNR$^{102}$R$^{103}$)R$^{100}$, —C(=NNR$^{104}$C(=O)R$^{101}$)R$^{100}$, C(=NNR$^{104}$C(O)OR$^{101}$)R$^{100}$, —C(=S)NR$^{102}$R$^{103}$, —NC, —NO$_2$, —NR$^{102}$R$^{103}$, —NR$^{104}$NR$^{102}$R$^{103}$, —N=NR$^{104}$, =NOR$^{100}$, —NR$^{104}$OR$^{106}$, —NR$^{104}$C(=O)R$^{100}$, —NR$^{104}$C(=O)C(=O)R$^{100}$, —NR$^{104}$C(=O)OR$^{101}$, —NR$^{104}$C(=O)C(=O)OR$^{101}$, —NR$^{104}$C(=O)NR$^{102}$R$^{103}$, —NR$^{104}$C(=O)NR$^{104}$C(=O)R$^{100}$, —NR$^{104}$C(=O)NR$^{104}$C(=O)OR$^{100}$, —NR$^{104}$(=NR$^{105}$)NR$^{102}$R$^{103}$, —NR$^{104}$C(=O)C(=O)NR$^{102}$R$^{103}$, —NR$^{104}$C(=S)R$^{100}$, —NR$^{104}$C(=S)OR$^{100}$, —NR$^{104}$C(=S)NR$^{102}$R$^{103}$, —NR$^{104}$S(=O)$_2$R$^{101}$, —NR$^{104}$S(=O)$_2$NR$^{102}$R$^{103}$, —NR$^{104}$P(=O)R$^{108}$R$^{108}$, —OR$^{100}$, =O, —OCN, —OC(=O)R$^{100}$, —OC(=O)NR$^{102}$R$^{103}$, —OC(=O)OR$^{100}$, —OC(=NR$^{105}$)NR$^{102}$R$^{103}$, —OS(=O)R$^{100}$, —OS(=O)$_2$R$^{100}$, —OS(=O)$_2$OR$^{100}$, —OS(=O)$_2$NR$^{102}$R$^{103}$, —SCN, =S, —S(=O)$_n$R$^{100}$, —S(=O)$_2$OR$^{100}$, —SO$_3$R$^{107}$, —S(=O)$_2$NR$^{102}$R$^{103}$, —S(=O)NR$^{102}$R$^{103}$, or —P(=O)R$^{108}$R$^{108}$. In another embodiment, $Z^1$ is H, $C_{1-6}$alkyl optionally substituted by 1-13 $R^{49}$, $C_{2-6}$alkenyl optionally substituted by 1-11 $R^{49}$, $C_{2-6}$alkynyl optionally substituted by 1-9 $R^{49}$, $C_{6-11}$ aryl optionally substituted by 1-11 $R^{49}$, $C_{7-16}$arylalkyl optionally substituted by 1-19 $R^{49}$, $C_{3-11}$cycloalkyl optionally substituted by 1-21 $R^{49}$, $C_{4-17}$cycloalkylalkyl optionally substituted by 1-32 $R^{49}$, 3-15 membered heterocycloalkyl optionally substituted by 1-28 $R^{49}$, 4-21 membered heterocycloalkylalkyl optionally substituted by 1-40 $R^{49}$, 5-15 membered heteroaryl optionally substituted by 1-15 $R^{49}$, 6-21 membered heteroarylalkyl optionally substituted by 1-27 $R^{49}$, halogen, —CN, —C(=O)$R^{100}$, —C(=O)OR$^{100}$, —C(=O)NR$^{102}$R$^{103}$, —C(=O)C(=O)R$^{100}$, —C(=NR$^{105}$)R$^{100}$, —C(=NR$^{105}$)NR$^{102}$R$^{103}$, —C(=NOH)NR$^{102}$R$^{103}$, —C(=NOH)NR$^{102}$R$^{103}$, —C(=NOR$^{106}$)R$^{100}$, —C(=NNR$^{102}$R$^{103}$)R$^{100}$, —C(=NNR$^{104}$C(=O)R$^{101}$)R$^{100}$, —C(NNR$^{104}$C(O)OR$^{101}$)R$^{100}$, —C(=S)NR$^{102}$R$^{103}$, —NC, —NO$_2$, —NR$^{102}$R$^{103}$, —NR$^{104}$R$^{102}$R$^{103}$, —N=NR$^{104}$, =NR$^{100}$, =NOR$^{100}$, —NR$^{104}$OR$^{106}$, —NR$^{104}$C(=O)R$^{100}$, —NR$^{104}$C(=O)C(=O)R$^{100}$, —NR$^{104}$C(=O)OR$^{101}$, —NR$^{104}$C(=O)C(=O)OR$^{101}$, —NR$^{104}$C(=O)R$^{100}$, —NR$^{104}$NR$^{104}$C(=O)R$^{100}$, —NR$^{104}$C(=O)NR$^{104}$C(=O)OR$^{100}$, —NR$^{104}$C(=NR$^{105}$)NR$^{102}$R$^{103}$, —NR$^{104}$C(=O)C(=O)NR$^{102}$R$^{103}$, —NR$^{104}$C(=S)R$^{100}$, —NR$^{104}$C(=S)OR$^{100}$, —NR$^{104}$C(=S)NR$^{102}$R$^{103}$, —NR$^{104}$S(=O)$_2$R$^{101}$, —NR$^{104}$S(=O)$_2$NR$^{102}$R$^{103}$, —OR$^{100}$, =O, —OCN, —OC(=O)R$^{100}$, —OC(=O)NR$^{102}$R$^{103}$, —OC(=O)OR$^{100}$, —OC(=NR$^{105}$)NR$^{102}$R$^{103}$, —OS(=O)R$^{100}$, —OS(=O)$_2$R$^{100}$, —OS(=O)$_2$ OR$^{100}$, —OS(=O)$_2$NR$^{102}$R$^{103}$, —SCN, =S, —S(=O)$_n$R$^{100}$, —S(=O)$_2$OR$^{100}$, —SO$_3$R$^{107}$, —S(=O)$_2$NR$^{102}$R$^{103}$, or —S(=O)NR$^{102}$R$^{103}$. In another embodiment, $Z^1$ is H, $C_{1-6}$alkyl optionally substituted by 1-13 $R^{49}$, $C_{7-16}$arylalkyl optionally substituted by 1-19 $R^{49}$, $C_{3-11}$cycloalkyl optionally substituted by 1-21 $R^{49}$, $C_{4-17}$cycloalkylalkyl optionally substituted by 1-32 $R^{49}$, 3-15 membered heterocycloalkyl optionally substituted by 1-28 $R^{49}$, 4-21 membered heterocycloalkylalkyl optionally substituted by 1-40 $R^{49}$, 5-15 membered heteroaryl optionally substituted by 1-15 $R^{49}$, 6-21 membered heteroarylalkyl optionally substituted by 1-27 $R^{49}$, halogen, —CN, —C(=O)R$^{100}$, —C(=O)OR$^{100}$, —C(=O)NR$^{102}$R$^{103}$, —C(=O)C(=O)R$^{100}$, —C(=S)NR$^{102}$R$^{103}$, —NC, —NO$_2$, —NR$^{102}$R$^{103}$, —NR$^{104}$NR$^{102}$R$^{103}$, —NR$^{104}$C(=O)R$^{100}$, —NR$^{104}$C(=O)C(=O)R$^{100}$, —NR$^{104}$C(=O)OR$^{101}$, —NR$^{104}$C(=O)C(=O)OR$^{101}$, —NR$^{104}$C(=O)NR$^{102}$R$^{103}$, —NR$^{104}$C(=O)NR$^{104}$C(=O)R$^{100}$, —NR$^{104}$C(=O)NR$^{104}$C(=O)OR$^{100}$, —NR$^{104}$C(=NR$^{105}$)NR$^{102}$R$^{103}$, —NR$^{104}$C(=O)C(=O)NR$^{102}$R$^{103}$, —NR$^{104}$C(=S)R$^{100}$, —NR$^{104}$C(=S)OR$^{100}$, —NR$^{104}$C(=S)NR$^{102}$R$^{103}$, —NR$^{104}$S(=O)$_2$R$^{101}$, —NR$^{104}$S(=O)$_2$NR$^{102}$R$^{103}$, —OR$^{100}$, =O, —OCN, —OC(=O)R$^{100}$, —OC(=O)NR$^{102}$R$^{103}$, —OC(=O)OR$^{100}$, —OS(=O)R$^{100}$, —OS(=O)$_2$R$^{100}$, —OS(=O)$_2$OR$^{100}$, —OS(=O)$_2$NR$^{102}$R$^{103}$, —SCN, =S, —S(=O)$_n$R$^{100}$, —S(=O)$_2$OR$^{100}$, —SO$_3$R$^{107}$, —S(=O)$_2$NR$^{102}$R$^{103}$, or —S(=O)NR$^{102}$R$^{103}$. In another embodiment, $Z^1$ is H, $C_{1-6}$alkyl optionally substituted by 1-13 $R^{49}$, $C_{7-16}$arylalkyl optionally substituted by 1-19 $R^{49}$, $C_{3-11}$cycloalkyl optionally substituted by 1-21 $R^{49}$, $C_{4-17}$cycloalkylalkyl optionally substituted by 1-32 $R^{49}$, 3-15 membered heterocycloalkyl optionally substituted by 1-28 $R^{49}$, 4-21 membered heterocycloalkylalkyl optionally substituted by 1-40 $R^{49}$, 5-15 membered heteroaryl optionally substituted by 1-15 $R^{49}$, 6-21 membered heteroarylalkyl optionally substituted by 1-27 $R^{49}$, halogen, —CN, —C(=O)R$^{100}$, —C(=O)OR$^{100}$, —C(=O)NR$^{102}$R$^{103}$, —C(=S)NR$^{102}$R$^{103}$, —NC, —NO$_2$, —NR$^{102}$R$^{103}$, —NR$^{104}$NR$^{102}$R$^{103}$, —NR$^{104}$C(=O)R$^{100}$, —NR$^{104}$C(=O)OR$^{101}$, —NR$^{104}$C(=O)NR$^{102}$R$^{103}$, —NR$^{104}$C(=NR$^{105}$)NR$^{102}$R$^{103}$, —NR$^{104}$C(=S)R$^{100}$, —NR$^{104}$C(=S)NR$^{102}$R$^{103}$, —NR$^{104}$S(=O)$_2$R$^{101}$, —NR$^{104}$P(=O)R$^{108}$R$^{108}$, —OR$^{100}$, =O, —OCN, —OC(=O)R$^{100}$, —OC(=O)NR$^{102}$R$^{103}$, —SCN, =S, —S(=O)$_n$R$^{100}$, —S(=O)$_2$NR$^{102}$R$^{103}$, or —P(=O)R$^{108}$R$^{108}$. In another embodiment, $Z^1$ is H, $C_{1-6}$alkyl optionally substituted by 1-13 $R^{49}$, $C_{7-16}$arylalkyl optionally substituted by 1-19 $R^{49}$, $C_{3-11}$cycloalkyl optionally substituted by 1-21 $R^{49}$, $C_{4-17}$cycloalkylalkyl optionally substituted by 1-32 $R^{49}$, 3-15 membered heterocycloalkyl optionally substituted by 1-28 $R^{49}$, 4-21 membered heterocycloalkylalkyl optionally substituted by 1-40 $R^{49}$, 5-15 membered heteroaryl optionally substituted by 1-15 $R^{49}$, 6-21 membered heteroarylalkyl optionally substituted by 1-27 $R^{49}$, halogen, —CN, —C(=O)R$^{100}$, —C(=O)OR$^{100}$, —C(=O)NR$^{102}$R$^{103}$, —C(=S)NR$^{102}$R$^{103}$, —NC, —NO$_2$, —NR$^{102}$R$^{103}$, —NR$^{104}$NR$^{102}$R$^{103}$, —NR$^{104}$C(=O)R$^{100}$, —NR$^{104}$C(=O)OR$^{101}$, —NR$^{104}$C(=O)NR$^{102}$R$^{103}$, —NR$^{104}$C(=O)NR$^{104}$C(=O)R$^{100}$, —NR$^{104}$C(=NR$^{105}$)NR$^{102}$R$^{103}$, —NR$^{104}$C(=S)R$^{100}$, —NR$^{104}$C(=S)NR$^{102}$R$^{103}$, —NR$^{104}$S(=O)$_2$R$^{101}$, —OR$^{100}$, =O, —OCN, —OC(=O)R$^{100}$, —OC(=O)NR$^{102}$R$^{103}$, —SCN, =S, —S(=O)$_n$R$^{100}$, or —S(=O)$_2$NR$^{102}$R$^{103}$. In another embodiment, $Z^1$ is H, $C_{1-6}$alkyl optionally substituted by 1-13 $R^{49}$, $C_{6-11}$aryl optionally substituted by 1-11 $R^{49}$, 3-15 membered heterocycloalkyl optionally substituted by 1-28 $R^{49}$, 5-15 membered heteroaryl optionally substituted by 1-15 $R^{49}$, halogen, —CN, —C(=O)R$^{100}$, —C(=O)OR$^{100}$, —C(=O)NR$^{102}$R$^{103}$, —NR$^{102}$R$^{103}$, —NR$^{104}$OR$^{106}$, —OR$^{100}$, =O, or —S(=O)$_n$R$^{100}$. In another embodiment, $Z^1$ is H, $C_{1-6}$alkyl optionally substituted by 1-6 $R^{49}$, $C_{6-11}$ aryl optionally substituted by 1-6 $R^{49}$, 3-15 membered heterocycloalkyl optionally substituted by 1-6 $R^{49}$, 5-15 membered heteroaryl optionally substituted by 1-6 $R^{49}$, halogen, —CN, —C(=O)R$^{100}$, —C(=O)OR$^{100}$, —C(=O)NR$^{102}$R$^{103}$, —NR$^{102}$R$^{103}$, —NR$^{104}$OR$^{106}$, —OR$^{100}$, =O, or —S(=O)$_n$R$^{100}$. In another embodiment, $Z^1$ is H, $C_{1-6}$alkyl optionally substituted by 1-6 $R^{49}$, phenyl optionally substituted by 1-6 $R^{49}$, 3-7 membered heterocycloalkyl optionally substituted by 1-6 $R^{49}$, 5-6 membered heteroaryl optionally substituted by 1-6 $R^{49}$, halogen, —CN, —C(=O)R$^{100}$, —C(=O)OR$^{100}$, —C(=O)NR$^{102}$R$^{103}$, —NR$^{102}$R$^{103}$, —NR$^{104}$OR$^{06}$, —OR$^{100}$, =O, or —S(=O)$_n$R$^{100}$. In another embodiment, $Z^1$ is H, $C_{1-6}$alkyl optionally substituted by 1-6 $R^{49}$, phenyl optionally substituted by 1-6 $R^{49}$, 4-6 membered heterocycloalkyl optionally substituted by 1-6 $R^{49}$, 5 membered heteroaryl optionally substituted by 1-6 $R^{49}$, halogen, —CN, —C(=O)R$^{100}$, —C(=O)OR$^{100}$, —C(=O)NR$^{102}$R$^{103}$, —NR$^{102}$R$^{103}$, —NR$^{104}$OR$^{106}$, —OR$^{100}$, =O, or —S(=O)$_n$R$^{100}$. In another embodiment, $Z^1$ is H, $C_{1-6}$alkyl optionally substituted by 1-13 $R^{49}$, $C_{7-16}$arylalkyl optionally substituted by 1-19 $R^{49}$, $C_{3-11}$cycloalkyl optionally substituted by 1-21 $R^{49}$, $C_{4-17}$cycloalkylalkyl optionally substituted by 1-32 $R^{49}$, 3-15 membered heterocycloalkyl optionally substituted by 1-28 $R^{49}$, 4-21 membered heterocycloalkylalkyl optionally substituted by 1-40 $R^{49}$, 5-15 membered heteroaryl optionally substituted by 1-15 $R^{49}$, 6-21 membered heteroarylalkyl optionally substituted by 1-27 $R^{49}$, halogen, —CN, —C(=O)R$^{100}$, —C(=O)(OR$^{100}$, —C(=O)NR$^{102}$R$^{103}$, —C(=S)NR$^{102}$R$^{103}$, —NR$^{102}$R$^{103}$, —NR$^{104}$C(=O)R$^{100}$, —NR$^{104}$C(=O)OR$^{101}$, —NR$^{104}$C(=S)NR$^{102}$R$^{103}$, —NR$^{102}$R$^{103}$, —NR$^{104}$C(=O)NR$^{104}$C(=O)R$^{100}$, —NR$^{104}$C(=S)R$^{100}$, —NR$^{104}$S(=O)$_2$R$^{101}$, —OR$^{100}$, =O, —OC(=O)R$^{100}$, —OC(=O)NR$^{102}$R$^{103}$, =S, —S(=O)$_n$R$^{100}$, or —S(=O)$_2$NR$^{102}$R$^{103}$. In another embodiment, $Z^1$ is H, $C_{1-6}$alkyl optionally substituted by 1-13 $R^{49}$, $C_{6-11}$ aryl optionally substituted by 1-6 $R^{49}$, $C_{3-11}$cycloalkyl optionally substituted by 1-21 $R^{49}$, 3-15 membered heterocycloalkyl optionally substituted by 1-28 $R^{49}$, 5-15 membered heteroaryl optionally substituted by 1-15 $R^{49}$, halogen, —CN, —C(=O)R$^{100}$, —C(=O)OR$^{100}$, —C(=O)NR$^{102}$R$^{103}$, —NR$^{102}$R$^{103}$, —NR$^{104}$C(=O)R$^{100}$, —NR$^{104}$C(=O)OR$^{101}$, —NR$^{104}$C(=O)NR$^{102}$R$^{103}$, —NR$^{104}$C(=O)NR$^{104}$C(=O)R$^{100}$, —NR$^{104}$S(=O)$_2$R$^{101}$, —NR$^{104}$P(=O)R$^{108}$R$^{108}$, —OR$^{100}$, =O, —C(=O)R$^{100}$, —OC(=O)NR$^{102}$R$^{103}$, =S, —S(=O)$_n$R$^{100}$, —S(=O)$_2$NR$^{102}$R$^{103}$, or —P(=O)R$^{108}$R$^{108}$. In another embodiment, Z$^1$ is H, C$_{1-6}$alkyl optionally substituted by 1-13 R$^{49}$, C$_{6-11}$ aryl optionally substituted by 1-6 R$^{49}$, C$_{3-11}$cycloalkyl optionally substituted by 1-21 R$^{49}$, 3-15 membered heterocycloalkyl optionally substituted by 1-28 R$^{49}$, 5-15 membered heteroaryl optionally substituted by 1-15 R$^{49}$, halogen, —CN, —C(=O)R$^{100}$, —C(=O)OR$^{100}$, —C(=O)NR$^{102}$R$^{103}$, —NR$^{102}$R$^{103}$, —NR$^{104}$C(=O)R$^{100}$, —NR$^{104}$C(=O)OR$^{101}$, —NR$^{104}$C(=O)NR$^{102}$R$^{103}$, —NR$^{104}$C(=O)NR$^{104}$C(=O)R$^{100}$, —NR$^{104}$S(=O)$_2$R$^{101}$, —OR$^{100}$, =O, —OC(=O)R$^{100}$, —OC(=O)NR$^{102}$R$^{103}$, =S, —S(=O)$_n$R$^{100}$, or —S(=O)$_2$NR$^{102}$R$^{103}$. In another embodiment, Z$^1$ is H, C$_{1-6}$alkyl optionally substituted by 1-6 R$^{49}$, C$_{7-16}$arylalkyl optionally substituted by 1-6 R$^{49}$, C$_{3-11}$cycloalkyl optionally substituted by 1-6 R$^{49}$, C$_{4-17}$cycloalkylalkyl optionally substituted by 1-6 R$^{49}$, 3-15 membered heterocycloalkyl optionally substituted by 1-6 R$^{49}$, 4-21 membered heterocycloalkylalkyl optionally substituted by 1-6 R$^{49}$, 5-15 membered heteroaryl optionally substituted by 1-6 R$^{49}$, 6-21 membered heteroarylalkyl optionally substituted by 1-6 R$^{49}$, halogen, —CN, —C(=O)R$^{100}$, —C(=O)OR$^{100}$, —C(=O)NR$^{102}$R$^{103}$, —C(=O)C(=O)R$^{100}$, —C(=S)NR$^{102}$R$^{103}$, —NC, —NO$_2$, —NR$^{102}$R$^{103}$, —NR$^{104}$NR$^{102}$R$^{103}$, —NR$^{104}$C(=O)R$^{100}$, —NR$^{104}$C(=O)C(=O)R$^{100}$, —NR$^{104}$C(=O)OR$^{101}$, —NR$^{104}$C(=O)C(=O)OR$^{101}$, —NR$^{104}$C(=O)NR$^{102}$R$^{103}$, —NR$^{104}$C(=O)NR$^{104}$C(=O)R$^{100}$, —NR$^{104}$C(=O)NR$^{104}$C(=O)OR$^{100}$, —NR$^{104}$C(=NR$^{105}$)NR$^{102}$R$^{103}$, —NR$^{104}$C(=O)C(=O)NR$^{102}$R$^{103}$, —NR$^{104}$C(=S)R$^{100}$, —NR$^{104}$C(=S)OR$^{100}$, —NR$^{104}$C(=S)NR$^{102}$R$^{103}$, —NR$^{104}$S(=O)$_2$R$^{101}$, —NR$^{104}$S(=O)$_2$NR$^{102}$R$^{103}$, —NR$^{104}$P(=O)R$^{108}$R$^{108}$, —OR$^{100}$, =O, —OCN, —OC(=O)R$^{100}$, —OC(=O)NR$^{102}$R$^{103}$, —OC(=O)OR$^{100}$, —OS(=O)R$^{100}$, —OS(=O)$_2$R$^{100}$, —OS(=O)$_2$OR$^{100}$, —OS(=O)$_2$NR$^{102}$R$^{103}$, —SCN, =S, —S(=O)$_n$R$^{100}$, —S(=O)$_2$OR$^{100}$, —SO$_3$R$^{107}$, —S(=O)$_2$NR$^{102}$R$^{103}$, —S(=O)NR$^{102}$R$^{103}$, or —P(=O)R$^{108}$R$^{108}$. In another embodiment, Z$^1$ is H, C$_{1-6}$alkyl optionally substituted by 1-6 R$^{49}$, C$_{7-16}$arylalkyl optionally substituted by 1-6 R$^{49}$, C$_{3-11}$cycloalkyl optionally substituted by 1-6 R$^{49}$, C$_{4-17}$cycloalkylalkyl optionally substituted by 1-6 R$^{49}$, 3-15 membered heterocycloalkyl optionally substituted by 1-6 R$^{49}$, 4-21 membered heterocycloalkylalkyl optionally substituted by 1-6 R$^{49}$, 5-15 membered heteroaryl optionally substituted by 1-6 R$^{49}$, 6-21 membered heteroarylalkyl optionally substituted by 1-6 R$^{49}$, halogen, —CN, —C(=O)R$^{100}$, —C(=O)OR$^{100}$, —C(=O)NR$^{102}$R$^{103}$, —C(=O)C(=O)R$^{100}$, —C(=S)NR$^{102}$R$^{103}$, —NC, —NO$_2$, —NR$^{102}$R$^{103}$, —NR$^{104}$NR$^{102}$R$^{103}$, —NR$^{104}$C(=O)R$^{100}$, NR$^{104}$C(=O)R$^{100}$, —NR$^{104}$C(=O)OR$^{101}$, —NR$^{104}$C(=O)C(=O)OR$^{101}$, —NR$^{104}$C(=O)NR$^{102}$R$^{103}$, —NR$^{104}$C(=O)NR$^{104}$C(=O)R$^{100}$, —NR$^{104}$C(=NR$^{105}$)NR$^{102}$R$^{103}$, —NR$^{104}$C(=O)C(=O)NR$^{102}$R$^{103}$, —NR$^{104}$C(=S)R$^{100}$, —NR$^{104}$C(=S)OR$^{100}$, —NR$^{104}$C(=S)NR$^{102}$R$^{103}$, —NR$^{104}$S(=O)$_2$R$^{101}$, —NR$^{104}$S(=O)$_2$NR$^{102}$R$^{103}$, —OR$^{100}$, =O, —OCN, —OC(=O)R$^{100}$, —OC(=O)NR$^{102}$R$^{103}$, —OC(=O)OR$^{100}$, —OS(=O)R$^{100}$, —OS(=O)$_2$R$^{100}$, —OS(=O)$_2$OR$^{100}$, —OS(=O)$_2$NR$^{102}$R$^{103}$, —SCN, =S, —S(=O)$_n$R$^{100}$, —S(=O)$_2$OR$^{100}$, —SO$_3$R$^{107}$, —S(=O)$_2$NR$^{102}$R$^{103}$, or —S(=O)NR$^{102}$R$^{103}$. In another embodiment, Z$^1$ is H, C$_{1-6}$alkyl optionally substituted by 1-6 R$^{49}$, C$_{7-16}$arylalkyl optionally substituted by 1-6 R$^{49}$, C$_{3-11}$cycloalkyl optionally substituted by 1-6 R$^{49}$, C$_{4-17}$cycloalkylalkyl optionally substituted by 1-6 R$^{49}$, 3-15 membered heterocycloalkyl optionally substituted by 1-6 R$^{49}$, 4-21 membered heterocycloalkylalkyl optionally substituted by 1-6 R$^{49}$, 5-15 membered heteroaryl optionally substituted by 1-6 R$^{49}$, 6-21 membered heteroarylalkyl optionally substituted by 1-6 R$^{49}$, halogen, —CN, —C(=O)R$^{100}$, —C(=O)OR$^{100}$, —C(=O)NR$^{102}$R$^{103}$, —C(=S)NR$^{102}$R$^{103}$, —NC, —NO$_2$, —NR$^{102}$R$^{103}$, —NR$^{104}$NR$^{102}$R$^{103}$, —NR$^{104}$C(=O)R$^{100}$, —NR$^{104}$C(=O)OR$^{101}$, —NR$^{104}$C(=O)NR$^{102}$R$^{103}$, —NR$^{104}$C(=O)NR$^{104}$C(=O)R$^{100}$, —NR$^{104}$C(=NR$^{105}$) NR$^{102}$R$^{103}$, —NR$^{104}$C(=S)R$^{100}$, —NR$^{104}$C(=S) NR$^{102}$R$^{103}$, —NR$^{104}$S(=O)$_2$R$^{101}$, —OR$^{100}$, =O, —OCN, —OC(=O)R$^{100}$, —OC(=O)NR$^{102}$R$^{103}$, —SCN, =S, —S(=O)$_n$R$^{100}$, or —S(=O)$_2$NR$^{102}$R$^{103}$. In another embodiment, Z$^1$ is H, C$_{1-6}$alkyl optionally substituted by 1-6 R$^{49}$, C$_{7-16}$arylalkyl optionally substituted by 1-6 R$^{49}$, C$_{3-11}$cycloalkyl optionally substituted by 1-6 R$^{49}$, C$_{4-17}$cycloalkylalkyl optionally substituted by 1-6 R$^{49}$, 3-15 membered heterocycloalkyl optionally substituted by 1-6 R$^{49}$, 4-21 membered heterocycloalkylalkyl optionally substituted by 1-6 R$^{49}$, 5-15 membered heteroaryl optionally substituted by 1-6 R$^{49}$, 6-21 membered heteroarylalkyl optionally substituted by 1-6 R$^{49}$, halogen, —CN, —C(=O)R$^{100}$, —C(=O)OR$^{100}$, —C(=O)NR$^{102}$R$^{103}$, —C(=S) NR$^{102}$R$^{103}$, —NR$^{102}$R$^{103}$, —NR$^{104}$C(=O)R$^{100}$, —NR$^{104}$C(=O)OR$^{101}$, —NR$^{104}$C(=O)NR$^{102}$R$^{103}$, —NR$^{104}$C(=O) NR$^{104}$C(=O)R$^{100}$, —NR$^{104}$C(=S)R$^{100}$, —NR$^{104}$S(=O)$_2$ R$^{101}$, —NR$^{104}$P(=O)R$^{108}$R$^{108}$, —OR$^{100}$, =O, —OC(=O) R$^{100}$, —OC(=O)NR$^{102}$R$^{103}$, =S, —S(=O)$_n$R$^{100}$, —S(=O)$_2$NR$^{102}$R$^{103}$, or —P(=O)R$^{108}$R$^{108}$. In another embodiment, Z$^1$ is H, C$_{1-6}$alkyl optionally substituted by 1-6 R$^{49}$, C$_{7-16}$arylalkyl optionally substituted by 1-6 R$^{49}$, C$_{3-11}$cycloalkyl optionally substituted by 1-6 R$^{49}$, C$_{4-17}$cycloalkylalkyl optionally substituted by 1-6 R$^{49}$, 3-15 membered heterocycloalkyl optionally substituted by 1-6 R$^{49}$, 4-21 membered heterocycloalkylalkyl optionally substituted by 1-6 R$^{49}$, 5-15 membered heteroaryl optionally substituted by 1-6 R$^{49}$, 6-21 membered heteroarylalkyl optionally substituted by 1-6 R$^{49}$, halogen, —CN, —C(=O)R$^{100}$, —C(=O)OR$^{100}$, —C(=O)NR$^{102}$R$^{103}$, —C(=S) NR$^{102}$R$^{103}$, —NR$^{102}$R$^{103}$, —NR$^{104}$C(=O)R$^{100}$, —NR$^{104}$C(=O)OR$^{101}$, —NR$^{104}$C(=O)NR$^{102}$R$^{103}$, —NR$^{104}$C(=O) NR$^{104}$C(=O)R$^{100}$, —NR$^{104}$C(=S)R$^{100}$, —NR$^{104}$S(=O)$_2$ R$^{101}$, —OR$^{100}$, =O, —OC(=O)R$^{100}$, —OC(=O) NR$^{102}$R$^{103}$, =S, —S(=O)$_n$R$^{100}$, or —S(=O)$_2$NR$^{102}$R$^{103}$. In another embodiment, Z$^1$ is H, C$_{1-6}$alkyl optionally substituted by 1-6 R$^{49}$, C$_{6-11}$ aryl optionally substituted by 1-6 R$^{49}$, C$_{3-11}$cycloalkyl optionally substituted by 1-6 R$^{49}$, 3-15 membered heterocycloalkyl optionally substituted by 1-6 R$^{49}$, 5-15 membered heteroaryl optionally substituted by 1-6 R$^{49}$, halogen, —CN, —C(=O)R$^{100}$, —C(=O)OR$^{100}$, —C(=O) NR$^{102}$R$^{103}$, —NR$^{102}$R$^{103}$, —NR$^{104}$C(=O)R$^{100}$, —NR$^{104}$C(=O)OR$^{101}$, —NR$^{104}$C(=O)NR$^{102}$R$^{103}$, —NR$^{104}$C(=O) NR$^{104}$C(=O)R$^{100}$, —NR$^{104}$S(=O)$_2$R$^{101}$, —OR$^{100}$, =O, —OC(=O)R$^{100}$, —OC(=O)NR$^{102}$R$^{103}$, =S, —S(=O)$_n$R$^{100}$, or —S(=O)$_2$NR$^{102}$R$^{103}$. In another embodiment, Z$^1$ is H, C$_{1-6}$alkyl optionally substituted by 1-13 R$^{49}$, 3-15 membered heterocycloalkyl optionally substituted by 1-28 R$^{49}$, halogen, —C(=O)R$^{100}$, —C(=O)OR$^{100}$, —C(=O) NR$^{102}$R$^{103}$, —OR$^{100}$, or —S(=O)$_n$R$^{100}$. In another embodiment, Z$^1$ is H, C$_{1-6}$alkyl optionally substituted by 1-3 R$^{49}$, 3-15 membered heterocycloalkyl optionally substituted by 1-3 R$^{49}$, halogen, —C(=O)R$^{100}$, —C(=O)OR$^{100}$, —C(=O)NR$^{102}$R$^{103}$, —OR$^{100}$, or —S(=O)$_n$R$^{100}$. In another embodiment, Z$^1$ is H, C$_{1-6}$alkyl optionally substituted by 1-3 $R^{49}$, 5-6 membered heterocycloalkyl optionally substituted by 1-3 $R^{49}$, halogen, —C(=O)$R^{100}$, —C(=O)O$R^{100}$, —C(=O)N$R^{102}R^{103}$, —O$R^{100}$, or —S(=O)$_n R^{100}$. In another embodiment, $Z^1$ is H, $C_{1-6}$alkyl optionally substituted by 1-3 $R^{49}$, 5-6 membered heterocycloalkyl optionally substituted by 1-3 $R^{49}$, halogen, —C(=O)$C_{1-6}$alkyl, —C(=O)OH, —C(=O)O$C_{1-6}$alkyl, —C(=O)O$C_{7-12}$arylalkyl, —C(=O)NH$_2$, —C(=O)NH$C_{1-6}$alkyl, —C(=O)N($C_{1-6}$alkyl)$_2$, —OH, —O$C_{1-6}$alkyl, or —S(=O)$_2 C_{1-6}$alkyl. In another embodiment, $Z^1$ is H, $C_{1-6}$alkyl, 5-6 membered heterocycloalkyl, halogen, —C(=O)$C_{1-6}$alkyl, —C(=O)OH, —C(=O)O$C_{1-6}$alkyl, —C(=O)O$C_{7-12}$arylalkyl, —C(=O)NH$_2$, —C(=O)NH$C_{1-6}$alkyl, —C(=O)N($C_{1-6}$alkyl)$_2$, —OH, —O$C_{1-6}$alkyl, or —S(=O)$_2 C_{1-6}$alkyl. In another embodiment, $Z^1$ is H, $C_{1-6}$alkyl, 5-6 membered heterocycloalkyl, wherein the heterocycloalkyl or heterocycloalkylene group contains, in addition to carbon atoms, one or two heteroatoms chosen from nitrogen and oxygen, halogen, —C(=O)$C_{1-6}$alkyl, —C(=O)OH, —C(=O)O$C_{1-6}$alkyl, —C(=O)O$C_{7-12}$arylalkyl, —C(=O)NH$_2$, —C(=O)NH$C_{1-6}$alkyl, —C(=O)N($C_{1-6}$alkyl)$_2$, —OH, —O$C_{1-6}$alkyl, or —S(=O)$_2 C_{1-6}$alkyl. In another embodiment, $Z^1$ is H, $C_{1-6}$alkyl, pyrrolidinyl, morpholinyl, halogen, —C(=O)$C_{1-6}$alkyl, —C(=O)O$C_{7-12}$arylalkyl, —C(=O)NH$_2$, —OH, or —S(=O)$_2 C_{1-6}$alkyl. In another embodiment, $Z^1$ is H, methyl, pyrrolidin-1-yl, morpholin-4-yl, chloro, —C(=O)CH$_3$, —C(=O)OCH$_2$phenyl, —C(=O)NH$_2$, —OH, or —S(=O)$_2$CH$_3$. In another embodiment, $Z^1$ is H.

In each embodiment of the present invention that is described in the paragraphs that precede or follow this paragraph, the definition of $L^2$ may be chosen from any of the embodiments that are described in this paragraph. In one embodiment, $L^2$ is —$C_{0-3}$alkylC(=O)$C_{0-3}$alkyl-, —$C_{0-3}$alkylC(=O)O$C_{0-3}$alkyl-, —$C_{0-3}$alkylC(=O)N$R^{44}C_{0-3}$alkyl-, —$C_{0-3}$alkylC(=O)C(=O)$C_{0-3}$alkyl-, —$C_{0-3}$alkylC(=N$R^{45}$)$C_{0-3}$alkyl-, —$C_{0-3}$alkylC(=N$R^{45}$)N$R^{44}C_{0-3}$alkyl-, —$C_{0-3}$alkylC(=NOH)N$R^{44}C_{0-3}$alkyl-, —$C_{0-3}$alkylC(=NO$R^{46}$)$C_{0-3}$alkyl-, —$C_{0-3}$alkylC(=NN$R^{42}R^{43}$)$C_{0-3}$alkyl-, —$C_{0-3}$alkylC(=NNR$^{44}$C(=O)$R^{41}$)$C_{0-3}$alkyl-, —$C_{0-3}$ alkylC(=NN$R^{44}$C(=O)O$R^{41}$)$C_{0-3}$alkyl-, —$C_{0-3}$alkylC(=S)N$R^{44}C_{0-3}$alkyl-, —$C_{0-3}$alkylN$R^{44}C_{0-3}$alkyl-, —$C_{0-3}$ alkylN$R^{44}$N$R^{44}C_{0-3}$alkyl-, —$C_{0-3}$alkylN=N$C_{0-3}$alkyl-, —$C_{0-3}$alkylN$R^{44}$C(=O)$C_{0-3}$alkyl-, —$C_{0-3}$alkylN$R^{44}$C(=O)C(=O)$C_{0-3}$alkyl-, —$C_{0-3}$alkylN$R^{44}$C(=O)O$C_{0-3}$ alkyl-, —$C_{0-3}$alkylN$R^{44}$C(=O)C(=O)O$C_{0-3}$alkyl-, —$C_{0-3}$alkylN$R^{44}$C(=O)N$R^{44}C_{0-3}$alkyl-, —$C_{0-3}$alkylN$R^{44}$C(=O)N$R^{44}$C(=O)$C_{0-3}$alkyl-, —$C_{0-3}$alkylN$R^{44}$C(=O)N$R^{44}$C(=O)O$C_{0-3}$alkyl-, —$C_{0-3}$alkylN$R^{44}$C(=N$R^{45}$)N$R^{44}C_{0-3}$alkyl-, —$C_{0-3}$alkylN$R^{44}$C(=O)C(=O)N$R^{44}C_{0-3}$ alkyl-, —$C_{0-3}$alkylN$R^{44}$C(=S)$C_{0-3}$ alkyl-, —$C_{0-3}$ alkylN$R^{44}$C(=S)O$C_{0-3}$alkyl-, —$C_{0-3}$alkylN$R^{44}$C(=S)N$R^{44}C_{0-3}$alkyl-, —$C_{0-3}$alkylN$R^{44}$S(=O)$_2 C_{0-3}$alkyl-, —$C_{0-3}$ alkylN$R^{44}$S(=O)$_2$N$R^{44}C_{0-3}$alkyl-, —$C_{0-3}$ alkylO$C_{0-3}$ alkyl-, —$C_{0-3}$alkylOC(=O)$C_{0-3}$alkyl-, —$C_{0-3}$ alkylOC(=O)N$R^{44}C_{0-3}$alkyl-, —$C_{0-3}$alkylOC(=O) O$C_{0-3}$ alkyl-, —$C_{0-3}$alkylOC(=N$R^{45}$)N$R^{44}C_{0-3}$alkyl-, —$C_{0-3}$ alkylOS(=O)$C_{0-3}$alkyl-, —$C_{0-3}$alkylOS(=O)$_2 C_{0-3}$ alkyl-, —$C_{0-3}$ alkylOS(=O)$_2$O$C_{0-3}$alkyl-, —$C_{0-3}$alkylOS(=O)$_2$ N$R^{44}C_{0-3}$ alkyl-, —$C_{0-3}$alkylS(=O)—$C_{0-3}$alkyl-, —$C_{0-3}$ alkylS(=O)$_2$ O$C_{0-3}$alkyl-, —$C_{0-3}$alkylSO$_3 C_{0-3}$alkyl-, —$C_{0-3}$ alkylS(=O)$_2$N$R^{44}C_{0-3}$alkyl-, —$C_{0-3}$alkylS(=O)N$R^{44}C_{0-3}$ alkyl-, or absent. In another embodiment, $L^2$ is —$C_{0-3}$alkylC(=O)$C_{0-3}$alkyl-, —$C_{0-3}$alkylC(=O)O$C_{0-3}$ alkyl-, —$C_{0-3}$ alkylC(=O)N$R^{44}C_{0-3}$alkyl-, —$C_{0-3}$alkylC(=O)C(=O)$C_{0-3}$ alkyl-, —$C_{0-3}$alkylC(=S)N$R^{44}C_{0-3}$ alkyl-, —$C_{0-3}$ alkylN$R^{44}C_{0-3}$alkyl-, —$C_{0-3}$ alkylN$R^{44}$N$R^{44}C_{0-3}$alkyl-, —$C_{0-3}$alkylN$R^{44}$C(=O)$C_{0-3}$alkyl-, —$C_{0-3}$alkylN$R^{44}$C(=O)C(=O)$C_{0-3}$alkyl-, —$C_{0-3}$alkylN$R^{44}$C(=O)O$C_{0-3}$alkyl-, —$C_{0-3}$alkylN$R^{44}$C(=O)N$R^{44}C_{0-3}$alkyl-, —$C_{0-3}$alkylN$R^{44}$C(=O)N$R^{44}$C(=O)$C_{0-3}$alkyl-, —$C_{0-3}$alkylN$R^{44}$C(=O)N$R^{44}$C(=O)$C_{0-3}$alkyl-, —$C_{0-3}$alkylN$R^{44}$C(=O)N$R^{44}$C(=O)O$C_{0-3}$alkyl-, —$C_{0-3}$alkylN$R^{44}$C(=N$R^{45}$)N$R^{44}C_{0-3}$alkyl-, —$C_{0-3}$alkylN$R^{44}$C(=S)$C_{0-3}$alkyl-, —$C_{0-3}$alkylN$R^{44}$S(=O)$_2 C_{0-3}$ alkyl-, —$C_{0-3}$alkylO$C_{0-3}$alkyl-, —$C_{0-3}$alkylOC(=O)$C_{0-3}$ alkyl-, —$C_{0-3}$alkylOC(=O)N$R^{44}C_{0-3}$alkyl-, —$C_{0-3}$alkylS(=O)—$C_{0-3}$alkyl-, —$C_{0-3}$alkylS(=O)$_2$N$R^{44}C_{0-3}$alkyl-, or absent. In another embodiment, $L^2$ is —$C_{0-3}$alkylC(=O)$C_{0-3}$ alkyl-, —$C_{0-3}$alkylC(=O)O$C_{0-3}$alkyl-, —$C_{0-3}$alkylC(=O) N$R^{44}C_{0-3}$alkyl-, —$C_{0-3}$alkylC(=S)N$R^{44}C_{0-3}$alkyl-, —$C_{0-3}$alkylN$R^{44}C_{0-3}$alkyl-, —$C_{0-3}$alkylN$R^{44}$N$R^{44}C_{0-3}$alkyl-, —$C_{0-3}$alkylN$R^{44}$C(=O)$C_{0-3}$alkyl-, —$C_{0-3}$alkylN$R^{44}$C(=O)O$C_{0-3}$alkyl-, —$C_{0-3}$alkylN$R^{44}$C(=O)N$R^{44}C_{0-3}$alkyl-, —$C_{0-3}$alkylN$R^{44}$C(=O)N$R^{44}$C(=O)$C_{0-3}$alkyl-, —$C_{0-3}$alkylN$R^{44}$C(=O)N$R^{44}$C(=O)O$C_{0-3}$alkyl-, —$C_{0-3}$alkylN$R^{44}$C(=S)$C_{0-3}$alkyl-, —$C_{0-3}$alkylN$R^{44}$S(=O)$_2 C_{0-3}$ alkyl-, —$C_{0-3}$alkylO$C_{0-3}$alkyl-, —$C_{0-3}$alkylOC(=O)$C_{0-3}$ alkyl-, —$C_{0-3}$alkylOC(=O)N$R^{44}C_{0-3}$alkyl-, —$C_{0-3}$alkylS(=O)—$C_{0-3}$alkyl-, —$C_{0-3}$alkylS(=O)$_2$N$R^{44}C_{0-3}$alkyl-, or absent. In another embodiment, $L^2$ is —$C_{0-3}$alkylC(=O)$C_{0-3}$alkyl-, —$C_{0-3}$alkylS(=O)—$C_{0-3}$alkyl-, or absent. In another embodiment, $L^2$ is —$C_{0-3}$alkylC(=O)—, —C(=O)$C_{0-3}$ lkyl-, —N$R^{44}C_{0-3}$alkyl-, —$C_{0-3}$alkylN$R^{44}$—, —$C_{0-3}$ alkylS(=O)$_n$—, —S(=O)$_n C_{0-3}$alkyl-, or absent. In another embodiment, $L^2$ is —C(=O)—, —N$R^{44}C_{0-3}$alkyl-, —$C_{0-3}$alkylN$R^{44}$—, —S(=O)$_n$—, or absent. In another embodiment, $L^2$ is —C(=O)—, —N$R^{44}C_{0-3}$alkyl-, —$C_{0-3}$alkylN$R^{44}$—, —S—, —S(=O)$_2$—, or absent. In another embodiment, $L^2$ is —C(=O)—, —C(=O)O—, —C(=O)N$R^{44}$—, —C(=O)C(=O)—, —C(=S)N$R^{44}$—, —N$R^{44}$—, —N$R^{44}$N$R^{44}$—, —N$R^{44}$C(=O)—, —N$R^{44}$C(=O)C(=O)—, —N$R^{44}$C(=O)O—, —N$R^{44}$C(=O)N$R^{44}$—, —N$R^{44}$C(=O)N$R^{44}$C(=O)—, —N$R^{44}$C(=O)N$R^{44}$C(=O)O—, —N$R^{44}$C(=N$R^{45}$)

NR$^{44}$—, —NR$^{44}$C(=O)C(=O)NR$^{44}$—, —NR$^{44}$C(=S)—, —NR$^{44}$C(=S)O—, —NR$^{44}$C(=S)NR$^{44}$—, —NR$^{44}$S(=O)$_2$—, —NR—, —O—, —OC(=O)—, —OC(=O)NR$^{44}$—, —OC(=O)O—, —OS(=O)—, —OS(=O)$_2$—, —OS(=O)$_2$O—, —OS(=O)$_2$NR$^{44}$—, —S(=O)$_n$—, —S(=O)$_2$O—, —SO$_3$—, —S(=O)$_2$NR$^{44}$—, —S(=O)NR$^{44}$—, or absent. In another embodiment, L$^2$ is —C(=O)—, —C(=O)O—, —C(=O)NR$^{44}$—, —C(=S)NR$^{44}$—, —NR$^{44}$—, —NR$^{44}$NR$^{44}$—, —NR$^{44}$C(=O)—, —NR$^{44}$C(=O)O—, —NR—, —NR$^{44}$C(=O)NR$^{44}$C(=O)—, —NR$^{44}$C(=O)NR$^{44}$C(=O)O—, —NR$^{44}$C(=NR$^{45}$)NR$^{44}$—, —NR$^{44}$C(=S)NR$^{44}$—, —NR$^{44}$S(=O)$_2$—, —O—, —OC(=O)—, —OC(=O)NR$^{44}$—, —S(=O)$_n$—, —S(=O)$_2$NR$^{44}$—, or absent. In another embodiment, L$^2$ is —C(=O)—, —C(=O)O—, —C(=O)NR$^{44}$—, —C(=S)NR$^{44}$—, —NR$^{44}$—, —NR—, —NR$^{44}$C(=O)—, —NR$^{44}$C(=O)O—, —NR$^{44}$C(=O)NR$^{44}$—, —NR$^{44}$C(=O)NR$^{44}$C(=O)—, —NR$^{44}$C(=O)NR$^{44}$C(=O)O—, —NR—, —NR$^{44}$S(=O)$_2$—, —O—, —OC(=O)—, —OC(=O)NR$^{44}$—, —S(=O)$_n$—, —S(=O)$_2$NR$^{44}$—, or absent. In another embodiment, L$^2$ is —C(=O)—, —C(=O)O—, —C(=O)NR$^{44}$—, —NR$^{44}$—, —NR$^{44}$C(=O)—, —NR$^{44}$C(=O)O—, —NR$^{44}$C(=O)NR$^{44}$—, —NR$^{44}$S(=O)$_2$—, —O—, —OC(=O)—, —OC(=O)NR$^{44}$—, —S(=O)$_n$—, —S(=O)$_2$NR$^{44}$—, or absent. In another embodiment, L$^2$ is —C$_{0-3}$alkylC(=O)C$_{0-3}$alkyl-, —C$_{0-3}$alkylNR$^{44}$C$_{0-3}$alkyl-, —C$_{0-3}$alkylOC$_{0-3}$alkyl-, —C$_{0-3}$alkylS(=O)—C$_{0-3}$alkyl-, or absent. In another embodiment, L$^2$ is —C(=O)—, —NR$^{44}$—, —O—, —S(=O)$_n$—, or absent. In another embodiment, L$^2$ is —C(=O)—, —NR$^{44}$, —O—, —S—, —S(=O)$_2$—, or absent. In another embodiment, L$^2$ is —C(=O)—, —NH—, —NC$_{1-6}$alkyl-, —O—, —S—, S(=O)$_2$—, or absent. In another embodiment, L$^2$ is —C(=O)—, —NH—, —O—, —S—, —S(=O)$_2$—, or absent. In another embodiment, L$^2$ is —C(=O)—, —NH—, —NC$_{1-6}$alkyl-, —S—, —S(=O)$_2$—, or absent. In another embodiment, L$^2$ is —C(=O)—, —NH—, —S—, —S(=O)$_2$—, or absent.

In each embodiment of the present invention that is described in the paragraphs that precede or follow this paragraph, the definition of A$^2$ may be chosen from any of the embodiments that are described in this paragraph. In one embodiment, A$^2$ is C$_{1-6}$alkylene optionally substituted by 1-12 R$^b$, C$_{2-6}$alkenylene optionally substituted by 1-10 R$^b$, C$_{2-6}$alkynylene optionally substituted by 1-8 R$^b$, C$_{6-11}$arylene optionally substituted by 1-10 R$^b$, C$_{7-16}$arylalkylene optionally substituted by 1-18 R$^b$, C$_{3-11}$cycloalkylene optionally substituted by 1-20 R$^b$, C$_{4-17}$cycloalkylalkylene optionally substituted by 1-31 R$^b$, 3-15 membered heterocycloalkylene optionally substituted by 1-27 R$^b$, 4-21 membered heterocycloalkylalkylene optionally substituted by 1-39 R$^b$, 5-15 membered heteroarylene optionally substituted by 1-14 R$^b$, 6-21 membered heteroarylalkylene optionally substituted by 1-26 R$^b$, or absent. In another embodiment, A$^2$ is C$_{1-6}$alkylene optionally substituted by 1-12 R$^b$, C$_{6-11}$arylene optionally substituted by 1-6 R$^b$, C$_{7-16}$arylalkylene optionally substituted by 1-18 R$^b$, C$_{3-11}$cycloalkylene optionally substituted by 1-20 R$^b$, C$_{4-6}$cycloalkylalkylene optionally substituted by 1-31 R$^b$, 3-15 membered heterocycloalkylene optionally substituted by 1-27 R$^b$, 4-21 membered heterocycloalkylalkylene optionally substituted by 1-39 R$^b$, 5-15 membered heteroarylene optionally substituted by 1-14 R$^b$, 6-21 membered heteroarylalkylene optionally substituted by 1-26 R$^b$, or absent. In another embodiment, A$^2$ is C$_{1-6}$alkylene optionally substituted by 1-12 R$^b$, C$_{6-11}$ arylene optionally substituted by 1-6 R$^b$, C$_{3-11}$cycloalkylene optionally substituted by 1-20 R$^b$, 3-15 membered heterocycloalkylene optionally substituted by 1-27 R$^b$, 5-15 membered heteroarylene optionally substituted by 1-14 R$^b$, or absent. In another embodiment, A$^2$ is C$_{1-6}$alkylene optionally substituted by 1-12 R$^b$, C$_{6-11}$arylene optionally substituted by 1-6 R$^b$, C$_{3-40}$cycloalkylene optionally substituted by 1-20 R$^b$, 3-10 membered heterocycloalkylene optionally substituted by 1-27 R$^b$, 5-10 membered heteroarylene optionally substituted by 1-14 R$^b$, or absent. In another embodiment, A$^2$ is C$_{1-6}$alkylene optionally substituted by 1-6 R$^b$, C$_{6-11}$arylene optionally substituted by 1-6 R$^b$, C$_{7-16}$arylalkylene optionally substituted by 1-6 R$^b$, C$_{3-11}$cycloalkylene optionally substituted by 1-6 R$^b$, C$_{4-17}$cycloalkylalkylene optionally substituted by 1-6 R$^b$, 3-15 membered heterocycloalkylene optionally substituted by 1-6 R$^b$, 4-21 membered heterocycloalkylalkylene optionally substituted by 1-6 R$^b$, 5-15 membered heteroarylene optionally substituted by 1-6 R$^b$, 6-21 membered heteroarylalkylene optionally substituted by 1-6 R$^b$, or absent. In another embodiment, A$^2$ is C$_{1-6}$alkylene optionally substituted by 1-6 R$^b$, C$_{6-11}$ arylene optionally substituted by 1-6 R$^b$, C$_{3-11}$cycloalkylene optionally substituted by 1-6 R$^b$, 3-15 membered heterocycloalkylene optionally substituted by 1-6 R$^b$, 5-15 membered heteroarylene optionally substituted by 1-6 R$^b$, or absent. In another embodiment, A$^2$ is C$_{1-6}$alkylene optionally substituted by 1-6 R$^b$, C$_{6-10}$aryl or C$_{6-10}$arylene optionally substituted by 1-6 R$^b$, C$_{3-40}$cycloalkylene optionally substituted by 1-6 R$^b$, 3-10 membered heterocycloalkylene optionally substituted by 1-6 R$^b$, 5-10 membered heteroarylene optionally substituted by 1-6 R$^b$, or absent. In another embodiment, A$^2$ is C$_{6-11}$arylene optionally substituted by 1-10 R$^b$, C$_{3-11}$cycloalkylene optionally substituted by 1-20 R$^b$, 3-15 membered heterocycloalkylene optionally substituted by 1-27 R$^b$, 5-15 membered heteroarylene optionally substituted by 1-14 R$^b$, or absent. In another embodiment, A$^2$ is C$_{6-11}$ arylene optionally substituted by 1-6 R$^b$, C$_{3-11}$cycloalkylene optionally substituted by 1-6 R$^b$, 3-15 membered heterocycloalkylene optionally substituted by 1-6 R$^b$, 5-15 membered heteroarylene optionally substituted by 1-6 R$^b$, or absent. In another embodiment, A$^2$ is C$_{6-10}$arylene optionally substituted by 1-6 R$^b$, C$_{5-6}$cycloalkylene optionally substituted by 1-6 R$^b$, 5-10 membered heterocycloalkylene optionally substituted by 1-6 R$^b$, 5-15 membered heteroarylene optionally substituted by 1-6 R$^b$, or absent. In another embodiment, A$^2$ is C$_{6-10}$arylene optionally substituted by 1-6 R$^b$, C$_6$cycloalkylene optionally substituted by 1-6 R$^b$, 5-6 membered heterocycloalkylene optionally substituted by 1-6 R$^b$, 5-15 membered heteroarylene optionally substituted by 1-6 R$^b$, or absent. In another embodiment, A$^2$ is C$_{6-10}$arylene optionally substituted by 1-6 R$^b$, C$_6$cycloalkylene optionally substituted by 1-6 R$^b$, 5-6 membered heterocycloalkylene optionally substituted by 1-6 R$^b$, 5-15 membered heteroarylene optionally substituted by 1-6 R$^b$, or absent; wherein the heterocycloalkylene group and the heteroarylene group each contain, in addition to carbon atoms, 1-3 heteroatoms chosen from nitrogen and oxygen. In another embodiment, A$^2$ is C$_{6-10}$arylene optionally substituted by 1-6 R$^b$, C$_{5-6}$cycloalkylene optionally substituted by 1-6 R$^b$, 5-6 membered heterocycloalkylene optionally substituted by 1-6 R$^b$, 5-11 membered heteroarylene optionally substituted by 1-6 R$^b$, or absent. In another embodiment, A$^2$ is C$_{6-10}$arylene optionally substituted by 1-6 R$^b$, C$_{5-6}$cycloalkylene optionally substituted by 1-6 R$^b$, 5-6 membered heterocycloalkylene optionally substituted by 1-6 R$^b$, 5-11 membered heteroarylene optionally substituted by 1-6 R$^b$, or absent; wherein the heterocycloalkylene group and the heteroarylene group each contain, in addition to carbon atoms, 1-3 heteroatoms chosen from nitrogen and oxygen. In another embodiment, A$^2$ is phenylene optionally substituted by 1-4 R$^b$, C$_6$cycloalkylene optionally substituted by 1-6 R$^b$, 5-6 membered heterocycloalkylene optionally substituted by 1-6 $R^b$, 5-11 membered heteroarylene optionally substituted by 1-6 $R^b$, or absent. In another embodiment, $A^2$ is phenylene optionally substituted by 1-4 $R^b$, $C_6$cycloalkylene optionally substituted by 1-6 $R^b$, 5-6 membered heterocycloalkylene optionally substituted by 1-6 $R^b$, 5-11 membered heteroarylene optionally substituted by 1-6 $R^b$, or absent; wherein the heterocycloalkylene group and the heteroarylene group each contain, in addition to carbon atoms, 1-3 heteroatoms chosen from nitrogen and oxygen. In another embodiment, $A^2$ is phenylene optionally substituted by 1-3 $R^b$, $C_6$cycloalkylene optionally substituted by 1-3 $R^b$, 5-6 membered heterocycloalkylene optionally substituted by 1-3 $R^b$, 5-11 membered heteroarylene optionally substituted by 1-3 $R^b$, or absent. In another embodiment, $A^2$ is phenylene optionally substituted by 1-3 $R^b$, $C_6$cycloalkylene optionally substituted by 1-3 $R^b$, 5-6 membered heterocycloalkylene optionally substituted by 1-3 $R^b$, 5-11 membered heteroarylene optionally substituted by 1-3 $R^b$, or absent; wherein the heterocycloalkylene group and the heteroarylene group each contain, in addition to carbon atoms, 1-3 heteroatoms chosen from nitrogen and oxygen. In another embodiment, $A^2$ is $C_{6-11}$ arylene optionally substituted by 1-10 $R^b$, $C_{3-11}$cycloalkylene optionally substituted by 1-20 $R^b$, 5-15 membered heteroarylene optionally substituted by 1-14 $R^b$, or absent. In another embodiment, $A^2$ is $C_{6-11}$arylene optionally substituted by 1-3 $R^b$, $C_{3-11}$cycloalkylene optionally substituted by 1-3 $R^b$, 5-15 membered heteroarylene optionally substituted by 1-3 $R^b$, or absent. In another embodiment, $A^2$ is phenylene optionally substituted by 1-3 $R^b$, $C_{5-6}$cycloalkylene optionally substituted by 1-3 $R^b$, 5-10 membered heteroarylene optionally substituted by 1-3 $R^b$, or absent. In another embodiment, $A^2$ is phenylene optionally substituted by 1-3 $R^b$, or 5-11 membered heteroarylene optionally substituted by 1-3 $R^b$, or absent. In another embodiment, $A^2$ is phenylene optionally substituted by 1-3 $R^b$, cyclohexylene, 5-10 membered heteroarylene, or absent. In another embodiment, $A^2$ is phenylene optionally substituted by 1-3 $R^b$, cyclohexylene, 5, 6 or 10 membered heteroarylene, or absent. In another embodiment, $A^2$ is phenylene optionally substituted by halogen or $C_{1-6}$alkyl, cyclohexylene, 5, 6 or 10 membered heteroarylene, or absent. In another embodiment, $A^2$ is phenylene optionally substituted by halogen or $C_{1-6}$alkyl, cyclohexylene, 5, 6 or 10 membered heteroarylene, wherein the heteroarylene group contains, in addition to carbon atoms, one or two heteroatoms chosen from nitrogen and oxygen, or absent. In another embodiment, $A^2$ is phenylene optionally substituted by halogen or $C_{1-6}$alkyl, cyclohexylene, pyridinylene, pyrazolylene, 2,3-dihydrobenzo[1,4]dioxinylene, or absent. In another embodiment, $A^2$ is phenylene optionally substituted by halogen or $C_{1-6}$alkyl, cyclohexylene, pyridinylene, pyrazolylene, 2,3-dihydrobenzo[1,4]dioxinylene, or absent. In another embodiment, $A^2$ is phenylene, chlorophenylene, fluorophenylene, methylphenylene, cyclohexylene, pyridinylene, pyrazolylene, 2,3-dihydrobenzo[1,4]dioxinylene, or absent. In another embodiment, $A^2$ is phenylene, chlorophenylene, fluorophenylene, methylphenylene, cyclohexylene, pyridine-3-ylene, pyridine-4-ylene, pyrazol-4-ylene, 2,3-dihydrobenzo[1,4]dioxin-6-ylene, or absent.

In each embodiment of the present invention that is described in the paragraphs that precede or follow this paragraph, the definition of $R^b$ may be chosen from any of the embodiments that are described in this paragraph. In one embodiment, each $R^b$ is independently chosen from $C_{1-6}$alkyl optionally substituted by 1-13 $R^{59}$, $C_{2-6}$alkenyl optionally substituted by 1-11 $R^{59}$, $C_{2-6}$alkynyl optionally substituted by 1-9 $R^{59}$, $C_{6-11}$aryl optionally substituted by 1-11 $R^{59}$, $C_{7-16}$arylalkyl optionally substituted by 1-19 $R^{59}$, $C_{3-11}$cycloalkyl optionally substituted by 1-21 $R^{59}$, $C_{4-17}$cycloalkylalkyl optionally substituted by 1-32 $R^{59}$, 3-15 membered heterocycloalkyl optionally substituted by 1-28 $R^{59}$, 4-21 membered heterocycloalkylalkyl optionally substituted by 1-40 $R^{59}$, 5-15 membered heteroaryl optionally substituted by 1-15 $R^{59}$, 6-21 membered heteroarylalkyl optionally substituted by 1-27 $R^{59}$, halogen, —CN, —C(=O)$R^{50}$, —C(=O)O$R^{50}$, —C(=O)N$R^{52}R^{53}$, —C(=O)C(=O)$R^{50}$, —C(=N$R^{55}$)$R^{50}$, —C(=N$R^{55}$)N$R^{52}R^{53}$, —C(=NOH)N$R^{52}R^{53}$, —C(=NO$R^{56}$)$R^{50}$, —C(=NN$R^{52}R^{53}$)$R^{50}$, —C(=NN$R^{54}$C(=O)$R^{51}$)$R^{50}$, —C(=NN$R^{54}$C(=O)O$R^{51}$)$R^{50}$, —C(=S)N$R^{52}R^{53}$, —NC, —NO$_2$, —N$R^{52}R^{53}$, —N$R^{54}$N$R^{52}R^{53}$, —N=N$R^{54}$, =N$R^{50}$, =NO$R^{50}$, —N$R^{54}$O$R^{56}$, —N$R^{54}$C(=O)$R^{50}$, —N$R^{54}$C(=O)C(=O)$R^{50}$, —N$R^{54}$C(=O)O$R^{51}$, —N$R^{54}$C(=O)C(=O)O$R^{51}$, —N$R^{54}$C(=O)N$R^{52}R^{53}$, —N$R^{54}$C(=O)N$R^{54}$C(=O)$R^{50}$, —N$R^{54}$C(=O)N$R^{54}$C(=O)O$R^{50}$, —N$R^{54}$C(=N$R^{55}$)N$R^{52}R^{53}$, —N$R^{54}$C(=O)C(=O)N$R^{52}R^{53}$, —N$R^{54}$C(=S)$R^{50}$, —N$R^{54}$C(=S)O$R^{50}$, —N$R^{54}$C(=S)N$R^{52}R^{53}$, —N$R^{54}$S(=O)$_2R^{51}$, —N$R^{54}$S(=O)$_2$N$R^{52}R^{53}$, —N$R^{54}$P(=O)$R^{58}R^{58}$, —N$R^{54}$P(=O)(N$R^{52}R^{53}$)(N$R^{52}R^{53}$), —N$R^{54}$P(=O)(O$R^{50}$)(O$R^{50}$), —N$R^{54}$P(=O)(S$R^{50}$)(S$R^{50}$), —O$R^{50}$, =O, —OCN, —OC(=O)$R^{50}$, —OC(=O)N$R^{52}R^{53}$, —OC(=O)O$R^{50}$, —OC(=N$R^{55}$)N$R^{52}R^{53}$, —OS(=O)$R^{50}$, —OS(=O)$_2R^{50}$, —OS(=O)$_2$O$R^{50}$, —OS(=O)$_2$N$R^{52}R^{53}$, —OP(=O)$R^{58}R^{58}$, —OP(=O)(N$R^{52}R^{53}$)(N$R^{52}R^{53}$), —OP(=O)(O$R^{50}$)(O$R^{50}$), —OP(=O)(S$R^{50}$)(S$R^{50}$), —SCN, =S, —S(=O)$_nR^{50}$, —S(=O)$_2$O$R^{50}$, —SO$_3R^{57}$, —S(=O)$_2$N$R^{52}R^{53}$, —S(=O)N$R^{52}R^{53}$, —SP(=O)$R^{58}R^{58}$, —SP(=O)(N$R^{52}R^{53}$)(N$R^{52}R^{53}$), —SP(=O)(O$R^{50}$)(O$R^{50}$), —SP(=O)(S$R^{50}$)(S$R^{50}$), —P(=O)$R^{58}R^{58}$, —P(=O)(N$R^{52}R^{53}$)(N$R^{52}R^{53}$), —P(=O)(O$R^{50}$)(O$R^{50}$), and —P(=O)(S$R^{50}$)(S$R^{50}$). In another embodiment, each $R^b$ is independently chosen from $C_{1-6}$alkyl optionally substituted by 1-13 $R^{59}$, $C_{2-6}$alkenyl optionally substituted by 1-11 $R^{59}$, $C_{2-6}$alkynyl optionally substituted by 1-9 $R^{59}$, $C_{6-11}$aryl optionally substituted by 1-11 $R^{59}$, $C_{7-16}$arylalkyl optionally substituted by 1-19 $R^{59}$, $C_{3-11}$cycloalkyl optionally substituted by 1-21 $R^{59}$, $C_{4-17}$cycloalkylalkyl optionally substituted by 1-32 $R^{59}$, 3-15 membered heterocycloalkyl optionally substituted by 1-28 $R^{59}$, 4-21 membered heterocycloalkylalkyl optionally substituted by 1-40 $R^{59}$, 5-15 membered heteroaryl optionally substituted by 1-15 $R^{59}$, 6-21 membered heteroarylalkyl optionally substituted by 1-27 $R^{59}$, halogen, —CN, —C(=O)$R^{50}$, —C(=O)O$R^{50}$, —C(=O)N$R^{52}R^{53}$, —C(=O)C(=O)$R^{50}$, —C(=N$R^{55}$)$R^{50}$, —C(=N$R^{55}$)N$R^{52}R^{53}$, —C(=NOH)N$R^{52}R^{53}$, —C(=NO$R^{56}$)$R^{50}$, —C(=NN$R^{52}R^{53}$)$R^{50}$, —C(=NN$R^{54}$C(=O)$R^{51}$)$R^{50}$, —C(=NN$R^{54}$C(=O)O$R^{51}$)$R^{50}$, —C(=S)N$R^{52}R^{53}$, —NC, —NO$_2$, —N$R^{52}R^{53}$, —N$R^{54}$N$R^{52}R^{53}$, —N=N$R^{54}$, =N$R^{50}$, =NO$R^{50}$, —N$R^{54}$O$R^{56}$, —N$R^{54}$C(=O)$R^{50}$, —N$R^{54}$C(=O)C(=O)$R^{50}$, —N$R^{54}$C(=O)O$R^{51}$, —N$R^{54}$C(=O)C(=O)O$R^{51}$, —N$R^{54}$C(=O)N$R^{52}R^{53}$, —N$R^{54}$C(=O)N$R^{54}$C(=O)$R^{50}$, —N$R^{54}$C(=O)N$R^{54}$C(=O)O$R^{50}$, —N$R^{54}$C(=N$R^{55}$)N$R^{52}R^{53}$, —N$R^{54}$C(=O)C(=O)N$R^{52}R^{53}$, —N$R^{54}$C(=S)$R^{50}$, —N$R^{54}$C(=S)O$R^{50}$, —N$R^{54}$C(=S)N$R^{52}R^{53}$, —N$R^{54}$S(=O)$_2R^{51}$, —N$R^{54}$S(=O)$_2$N$R^{52}R^{53}$, —N$R^{54}$P(=O)$R^{58}R^{58}$, —O$R^{50}$, =O, —OCN, —OC(=O)$R^{50}$, —OC(=O)N$R^{52}R^{53}$, —OC(=O)O$R^{50}$, —OC(=N$R^{55}$)N$R^{52}R^{53}$, —OS(=O)$R^{50}$, —OS(=O)$_2R^{50}$, —OS(=O)$_2$O$R^{50}$, —OS(=O)$_2$N$R^{52}R^{53}$, —SCN, =S, —S(=O)$_nR^{50}$, —S(=O)$_2$O$R^{50}$, —SO$_3R^{57}$, —S(=O)$_2$N$R^{52}R^{53}$, —S(=O)N$R^{52}R^{53}$, and —P(=O)$R^{58}R^{58}$. In another embodiment, each $R^b$ is independently chosen from $C_{1-6}$alkyl optionally substituted by 1-13 $R^{59}$, $C_{2-6}$alkenyl optionally substituted by 1-11 $R^{59}$, $C_{2-6}$alkynyl optionally substituted by 1-9 $R^{59}$, $C_{6-11}$ aryl optionally substituted by 1-11 $R^{59}$, $C_{7-16}$arylalkyl optionally substituted by 1-19 $R^{59}$, $C_{3-11}$cycloalkyl optionally substituted by 1-21 $R^{59}$, $C_{4-17}$cycloalkylalkyl optionally substituted by 1-32 $R^{59}$, 3-15 membered heterocycloalkyl optionally substituted by 1-28 $R^{59}$, 4-21 membered heterocycloalkylalkyl optionally substituted by 1-40 $R^{59}$, 5-15 membered heteroaryl optionally substituted by 1-15 $R^{59}$, 6-21 membered heteroarylalkyl optionally substituted by 1-27 $R^{59}$, halogen, —CN, —C(=O)$R^{50}$, —C(=O)O$R^{50}$, —C(=O)N$R^{52}R^{53}$, —C(=O)C(=O)$R^{50}$, —C(=N$R^{55}$)$R^{50}$, —C(=N$R^{55}$)N$R^{52}R^{53}$, —C(=NOH)N$R^{52}R^{53}$, —C(=NO$R^{56}$)$R^{50}$, —C(=NN$R^{52}R^{53}$)$R^{50}$, —C(=NN$R^{54}$C(=O)$R^{51}$)$R^{50}$, —C(=NN$R^{54}$C(=O)O$R^{51}$)$R^{50}$, —C(=S)N$R^{52}R^{53}$, —NC, —NO$_2$, —N$R^{52}R^{53}$, —N$R^{54}$N$R^{52}R^{53}$, —N=N$R^{54}$, =N$R^{50}$, =NO$R^{50}$, —N$R^{54}$O$R^{56}$, —N$R^{54}$C(=O)$R^{50}$, —N$R^{54}$C(=O)C(=O)$R^{50}$, —N$R^{54}$C(=O)O$R^{51}$, —N$R^{54}$C(=O)C(=O)O$R^{51}$, —N$R^{54}$C(=O)N$R^{52}R^{53}$, —N$R^{54}$C(=O)N$R^{54}$C(=O)$R^{50}$, —N$R^{54}$C(=O)N$R^{54}$C(=O)O$R^{50}$, —N$R^{54}$C(=N$R^{55}$)N$R^{52}R^{53}$, —N$R^{54}$C(=O)C(=O)N$R^{52}R^{53}$, —N$R^{54}$C(=S)$R^{50}$, —N$R^{54}$C(=S)O$R^{50}$, —N$R^{54}$C(=S)N$R^{52}R^{53}$, —N$R^{54}$S(=O)$_2R^{51}$, —N$R^{54}$S(=O)$_2$N$R^{52}R^{53}$, —O$R^{50}$, =O, —OCN, —OC(=O)$R^{50}$, —OC(=O)N$R^{52}R^{53}$, —OC(=O)O$R^{50}$, —OC(=N$R^{55}$)N$R^{52}R^{53}$, —OS(=O)$R^{50}$, —OS(=O)$_2R^{50}$, —OS(=O)$_2$O$R^{50}$, —OS(=O)$_2$N$R^{52}R^{53}$, —SCN, =S, —S(=O)$_nR^{50}$, —S(=O)$_2$O$R^{50}$, —SO$_3R^{57}$, —S(=O)$_2$N$R^{52}R^{53}$, and —S(=O)N$R^{52}R^{53}$. In another embodiment, each $R^b$ is independently chosen from $C_{1-6}$alkyl optionally substituted by 1-13 $R^{59}$, $C_{2-6}$alkenyl optionally substituted by 1-11 $R^{59}$, $C_{2-6}$alkynyl optionally substituted by 1-9 $R^{59}$, $C_{6-11}$ aryl optionally substituted by 1-7 $R^{59}$, $C_{7-16}$arylalkyl optionally substituted by 1-19 $R^{59}$, $C_{3-11}$cycloalkyl optionally substituted by 1-21 $R^{59}$, $C_{4-17}$cycloalkylalkyl optionally substituted by 1-32 $R^{59}$, 3-15 membered heterocycloalkyl optionally substituted by 1-28 $R^{59}$, 4-21 membered heterocycloalkylalkyl optionally substituted by 1-40 $R^{59}$, 5-15 membered heteroaryl optionally substituted by 1-15 $R^{59}$, 6-21 membered heteroarylalkyl optionally substituted by 1-27 $R^{59}$, halogen, —CN, —C(=O)$R^{50}$, —C(=O)O$R^{50}$, —C(=O)N$R^{52}R^{53}$, —C(=O)C(=O)$R^{50}$, —C(=S)N$R^{52}R^{53}$, —NC, —NO$_2$, —N$R^{52}R^{53}$, —N$R^{54}$N$R^{52}R^{53}$, —N$R^{54}$C(=O)$R^{50}$, —N$R^{54}$C(=O)C(=O)$R^{50}$, —N$R^{54}$C(=O)O$R^{51}$, —N$R^{54}$C(=O)C(=O)O$R^{51}$, —N$R^{52}R^{53}$, —N$R^{54}$C(=O)N$R^{54}$C(=O)$R^{50}$, —N$R^{54}$C(=O)N$R^{54}$C(=O)O$R^{50}$, —N$R^{54}$C(=N$R^{55}$)N$R^{52}R^{53}$, —N$R^{54}$C(=O)C(=O)N$R^{52}R^{53}$, —N$R^{54}$C(=S)$R^{50}$, —N$R^{54}$C(=S)O$R^{50}$, —N$R^{54}$C(=S)N$R^{52}R^{53}$, —N$R^{54}$S(=O)$_2R^{51}$, —N$R^{54}$S(=O)$_2$N$R^{52}R^{53}$, —O$R^{50}$, =O, —OCN, —OC(=O)$R^{50}$, —OC(=O)N$R^{52}R^{53}$, —OC(=O)O$R^{50}$, —OS(=O)$R^{50}$, —OS(=O)$_2R^{50}$, —OS(=O)$_2$O$R^{50}$, —OS(=O)$_2$N$R^{52}R^{53}$, —SCN, =S, —S(=O)$_nR^{50}$, —S(=O)$_2$O$R^{50}$, —SO$_3R^{57}$, —S(=O)$_2$N$R^{52}R^{53}$, and —S(=O)N$R^{52}R^{53}$. In another embodiment, each $R^b$ is independently chosen from $C_{1-6}$alkyl optionally substituted by 1-13 $R^{59}$, $C_{2-6}$alkenyl optionally substituted by 1-11 $R^{59}$, $C_{2-6}$alkynyl optionally substituted by 1-9 $R^{59}$, $C_{6-11}$aryl optionally substituted by 1-7 $R^{59}$, $C_{7-16}$arylalkyl optionally substituted by 1-19 $R^{59}$, $C_{3-11}$cycloalkyl optionally substituted by 1-21 $R^{59}$, $C_{4-17}$cycloalkylalkyl optionally substituted by 1-32 $R^{59}$, 3-15 membered heterocycloalkyl optionally substituted by 1-28 $R^{59}$, 4-21 membered heterocycloalkylalkyl optionally substituted by 1-40 $R^{59}$, 5-15 membered heteroaryl optionally substituted by 1-15 $R^{59}$, 6-21 membered heteroarylalkyl optionally substituted by 1-27 $R^{59}$, halogen, —CN, —C(=O)$R^{50}$, —C(=O)O$R^{50}$, —C(=O)N$R^{52}R^{53}$, —NC, —NO$_2$, —N$R^{52}R^{53}$, —N$R^{54}$N$R^{52}R^{53}$, —N$R^{54}$C(=O)$R^{50}$, —N$R^{54}$C(=O)O$R^{51}$, —N$R^{54}$C(=O)N$R^{52}R^{53}$, —N$R^{54}$C(=N$R^{55}$)N$R^{52}R^{53}$, —N$R^{54}$C(=S)N$R^{52}R^{53}$, —N$R^{54}$S(=O)$_2R^{51}$, —N$R^{54}$P(=O)$R^{58}R^{58}$, —O$R^{50}$, =O, —OCN, —OC(=O)$R^{50}$, —OC(=O)N$R^{52}R^{53}$, —SCN, =S, —S(=O)$_nR^{50}$, —S(=O)$_2$N$R^{52}R^{53}$, and —P(=O)$R^{58}R^{58}$. In another embodiment, each $R^b$ is independently chosen from $C_{1-6}$alkyl optionally substituted by 1-13 $R^{59}$, $C_{2-6}$alkenyl optionally substituted by 1-11 $R^{59}$, $C_{2-6}$alkynyl optionally substituted by 1-9 $R^{59}$, $C_{6-11}$aryl optionally substituted by 1-7 $R^{59}$, $C_{7-16}$arylalkyl optionally substituted by 1-19 $R^{59}$, $C_{3-11}$cycloalkyl optionally substituted by 1-21 $R^{59}$, $C_{4-17}$cycloalkylalkyl optionally substituted by 1-32 $R^{59}$, 3-15 membered heterocycloalkyl optionally substituted by 1-28 $R^{59}$, 4-21 membered heterocycloalkylalkyl optionally substituted by 1-40 $R^{59}$, 5-15 membered heteroaryl optionally substituted by 1-15 $R^{59}$, 6-21 membered heteroarylalkyl optionally substituted by 1-27 $R^{59}$, halogen, —CN, —C(=O)$R^{50}$, —C(=O)O$R^{50}$, —C(=O)N$R^{52}R^{53}$, —C(=S)N$R^{52}R^{53}$, —NC, —NO$_2$, —N$R^{52}R^{53}$, —N$R^{54}$N$R^{52}R^{53}$, —N$R^{54}$C(=O)$R^{50}$, —N$R^{54}$C(=O)O$R^{51}$, —N$R^{54}$C(=O)N$R^{52}R^{53}$, —N$R^{54}$C(=O)N$R^{54}$C(=O)$R^{50}$, —N$R^{54}$C(=N$R^{55}$)N$R^{52}R^{53}$, —N$R^{54}$C(=S)N$R^{52}R^{53}$, —N$R^{54}$S(=O)$_2R^{51}$, —O$R^{50}$, =O, —OCN, —OC(=O)$R^{50}$, —OC(=O)N$R^{52}R^{53}$, —SCN, =S, —S(=O)$_nR^{50}$, —S(=O)$_2$N$R^{52}R^{53}$. In another embodiment, each $R^b$ is independently chosen from $C_{1-6}$alkyl optionally substituted by 1-13 $R^{59}$, $C_{6-11}$aryl optionally substituted by 1-7 $R^{59}$, $C_{7-16}$arylalkyl optionally substituted by 1-19 $R^{59}$, $C_{3-11}$cycloalkyl optionally substituted by 1-21 $R^{59}$, $C_{4-17}$cycloalkylalkyl optionally substituted by 1-32 $R^{59}$, 3-15 membered heterocycloalkyl optionally substituted by 1-28 $R^{59}$, 4-21 membered heterocycloalkylalkyl optionally substituted by 1-40 $R^{59}$, 5-15 membered heteroaryl optionally substituted by 1-15 $R^{59}$, 6-21 membered heteroarylalkyl optionally substituted by 1-27 $R^{59}$, halogen, —CN, —C(=O)$R^{50}$, —C(=O)O$R^{50}$, —C(=O)N$R^{52}R^{53}$, —C(=S)N$R^{52}R^{53}$, —N$R^{52}R^{53}$, —N$R^{54}$C(=O)$R^{50}$, —N$R^{54}$C(=O)O$R^{51}$, —N$R^{54}$C(=O)N$R^{52}R^{53}$, —N$R^{54}$C(=O)N$R^{52}R^{53}$, —N$R^{54}$C(=O)N$R^{54}$C(=O)$R^{50}$, —N$R^{54}$C(=O)N$R^{54}$C(=O)O$R^{50}$, —N$R^{54}$C(=S)$R^{50}$, —N$R^{54}$S(=O)$_2R^{51}$, —O$R^{50}$, =O, —OCN, —OC(=O)$R^{50}$, —OC(=O)N$R^{52}R^{53}$, =S, —S(=O)$_nR^{50}$, and —S(=O)$_2$N$R^{52}R^{53}$. In another embodiment, each $R^b$ is independently chosen from $C_{1-6}$alkyl optionally substituted by 1-13 $R^{59}$, $C_{6-11}$aryl optionally substituted by 1-7 $R^{59}$, $C_{7-16}$arylalkyl optionally substituted by 1-19 $R^{59}$, $C_{3-11}$cycloalkyl optionally substituted by 1-21 $R^{59}$, $C_{4-17}$cycloalkylalkyl optionally substituted by 1-32 $R^{59}$, 3-15 membered heterocycloalkyl optionally substituted by 1-28 $R^{59}$, 4-21 membered heterocycloalkylalkyl optionally substituted by 1-40 $R^{59}$, 5-15 membered heteroaryl optionally substituted by 1-15 $R^{59}$, 6-21 membered heteroarylalkyl optionally substituted by 1-27 $R^{59}$, halogen, —CN, —C(=O)$R^{50}$, —C(=O)O$R^{50}$, —C(=O)N$R^{52}R^{53}$, —N$R^{52}R^{53}$, —N$R^{54}$C(=O)$R^{50}$, —N$R^{54}$C(=O)O$R^{51}$, —N$R^{54}$C(=O)N$R^{52}R^{53}$, —N$R^{54}$S(=O)$_2R^{51}$, —O$R^{50}$, =O, —OCN, —OC(=O)$R^{50}$, —OC(=O)N$R^{52}R^{53}$, =S, —S(=O)$_nR^{50}$, and —S(=O)$_2$N$R^{52}R^{53}$. In another embodiment, each $R^b$ is independently chosen from $C_{1-6}$alkyl optionally substituted by 1-6 $R^{59}$, $C_{2-6}$alkenyl optionally substituted by 1-6 $R^{59}$, $C_{2-6}$alkynyl optionally substituted by 1-6 $R^{59}$, $C_{6-11}$aryl optionally substituted by 1-6 $R^{59}$, $C_{7-16}$arylalkyl optionally substituted by 1-6 $R^{59}$, $C_{3-11}$cycloalkyl optionally substituted by 1-6 $R^{59}$, $C_{4-17}$cycloalkylalkyl optionally substituted by 1-6 $R^{59}$, 3-15 membered heterocycloalkyl optionally substituted by 1-6 $R^{59}$, 4-21 membered heterocycloalkylalkyl optionally substituted by 1-6 $R^{59}$, 5-15 membered heteroaryl optionally substituted by 1-6 $R^{59}$, 6-21 membered heteroarylalkyl optionally substituted by 1-6 $R^{59}$, halogen, —CN, —C(=O)$R^{50}$, —C(=O)O$R^{50}$, —C(=O)N$R^{52}R^{53}$, —C(=O)C(=O)$R^{50}$, —C(=S)N$R^{52}R^{53}$, —NC, —NO$_2$, —N$R^{52}R^{53}$, —N$R^{54}$N$R^{52}R^{53}$, —N$R^{54}$C(=O)$R^{50}$, —N$R^{54}$C(=O)C(=O)$R^{50}$, —N$R^{54}$C(=O)O$R^{51}$, —N$R^{54}$C(=O)C(=O)O$R^{51}$, —N$R^{54}$C(=O)N$R^{52}R^{53}$, —N$R^{54}$C(=O)N$R^{54}$C(=O)$R^{50}$, —N$R^{54}$C(=O)N$R^{54}$C(=O)O$R^{50}$, —N$R^{54}$C(=N$R^{55}$)N$R^{52}R^{53}$, —N$R^{54}$C(=O)C(=O)N$R^{52}R^{53}$, —N$R^{54}$C(=S)$R^{50}$, —N$R^{54}$C(=S)O$R^{50}$, —N$R^{54}$C(=S)N$R^{52}R^{53}$, —N$R^{54}$S(=O)$_2R^{51}$, —N$R^{54}$S(=O)$_2$N$R^{52}R^{53}$, —N$R^{54}$P(=O)$R^{58}R^{58}$, —O$R^{50}$, =O, —OCN, —OC(=O)$R^{50}$, —OC(=O)N$R^{52}R^{53}$, —OC(=O)O$R^{50}$, —OS(=O)$R^{50}$, —OS(=O)$_2R^{50}$, —OS(=O)$_2$O$R^{50}$, —OS(=O)$_2$N$R^{52}R^{53}$, —SCN, =S, —S(=O)$_nR^{50}$, —S(=O)$_2$O$R^{50}$, —SO$_3R^{57}$, —S(=O)$_2$N$R^{52}R^{53}$, —S(=O)N$R^{52}R^{53}$, and —P(=O)$R^{58}R^{58}$. In another embodiment, each $R^b$ is independently chosen from $C_{1-6}$alkyl optionally substituted by 1-6 $R^{59}$, $C_{2-6}$alkenyl optionally substituted by 1-6 $R^{59}$, $C_{2-6}$alkynyl optionally substituted by 1-6 $R^{59}$, $C_{6-11}$ aryl optionally substituted by 1-6 $R^{59}$, $C_{7-16}$arylalkyl optionally substituted by 1-6 $R^{59}$, $C_{3-11}$cycloalkyl optionally substituted by 1-6 $R^{59}$, $C_{4-17}$cycloalkylalkyl optionally substituted by 1-6 $R^{59}$, 3-15 membered heterocycloalkyl optionally substituted by 1-6 $R^{59}$, 4-21 membered heterocycloalkylalkyl optionally substituted by 1-6 $R^{59}$, 5-15 membered heteroaryl optionally substituted by 1-6 $R^{59}$, 6-21 membered heteroarylalkyl optionally substituted by 1-6 $R^{59}$, halogen, —CN, —C(=O)$R^{50}$, —C(=O)O$R^{50}$, —C(=O)N$R^{52}R^{53}$, —C(=O)C(=O)$R^{50}$, —C(=S)N$R^{52}R^{53}$, —NC, —NO$_2$, —N$R^{52}R^{53}$, —N$R^{54}$N$R^{52}R^{53}$, —N$R^{54}$C(=O)$R^{50}$, —N$R^{54}$C(=O)C(=O)$R^{50}$, —N$R^{54}$C(=O)O$R^{51}$, —N$R^{54}$C(=O)O$R^{51}$, —N$R^{54}$C(=O)N$R^{52}R^{53}$, —N$R^{54}$C(=O)N$R^{54}$C(=O)$R^{50}$, —N$R^{54}$C(=O)N$R^{54}$C(=O)O$R^{50}$, —N$R^{54}$C(=N$R^{55}$)N$R^{52}R^{53}$, —N$R^{54}$C(=O)C(=O)N$R^{52}R^{53}$, —N$R^{54}$C(=S)$R^{50}$, —N$R^{54}$C(=S)O$R^{50}$, —N$R^{54}$C(=S)N$R^{52}R^{53}$, —N$R^{54}$S(=O)$_2R^{51}$, —NR—O$R^{50}$, =O, —OCN, —OC(=O)$R^{50}$, —OC(=O)N$R^{52}R^{53}$, —OC(=O)O$R^{50}$, —OS(=O)$R^{50}$, —OS(=O)$_2R^{50}$, —OS(=O)$_2$O$R^{50}$, —OS(=O)$_2$N$R^{52}R^{53}$, —SCN, =S, —S(=O)$_n$ $R^{50}$, —S(=O)$_2$O$R^{50}$, —SO$_3R^{57}$, —S(=O)$_2$N$R^{52}R^{53}$, and —S(=O)N$R^{52}R^{53}$. In another embodiment, each $R^b$ is independently chosen from $C_{1-6}$alkyl optionally substituted by 1-6 $R^{59}$, $C_{2-6}$alkenyl optionally substituted by 1-6 $R^{59}$, $C_{2-6}$alkynyl optionally substituted by 1-9 $R^{59}$, $C_{6-11}$aryl optionally substituted by 1-7 $R^{59}$, $C_{7-16}$arylalkyl optionally substituted by 1-6 $R^{59}$, $C_{3-11}$cycloalkyl optionally substituted by 1-6 $R^{59}$, $C_{4-17}$cycloalkylalkyl optionally substituted by 1-6 $R^{59}$, 3-15 membered heterocycloalkyl optionally substituted by 1-6 $R^{59}$, 4-21 membered heterocycloalkylalkyl optionally substituted by 1-6 $R^{59}$, 5-15 membered heteroaryl optionally substituted by 1-6 $R^{59}$, 6-21 membered heteroarylalkyl optionally substituted by 1-6 $R^{59}$, halogen, —CN, —C(=O)$R^{50}$, —C(=O)O$R^{50}$, —C(=O)N$R^{52}R^{53}$, —C(=S)N$R^{52}R^{53}$, —NC, —NO$_2$, —N$R^{52}R^{53}$, —N$R^{54}$N$R^{52}R^{53}$, —N$R^{54}$C(=O)$R^{50}$, —N$R^{54}$C(=O)O$R^{51}$, —N$R^{54}$C(=O)N$R^{52}R^{53}$, —N$R^{54}$C(=O)N$R^{54}$C(=O)$R^{50}$, —N$R^{54}$C(=O)N$R^{54}$C(=O)O$R^{50}$, —N$R^{54}$C(=N$R^{55}$)N$R^{52}R^{53}$, —N$R^{54}$C(=S)N$R^{52}R^{53}$, —N$R^{54}$S(=O)$_2R^{51}$, —N$R^{54}$P(=O)$R^{58}R^{58}$, —O$R^{50}$, =O, —OCN, —OC(=O)$R^{50}$, —OC(=O)N$R^{52}R^{53}$, —SCN, =S, —S(=O)$_nR^{50}$, —S(=O)$_2$N$R^{52}R^{53}$, and —P(=O)$R^{58}R^{58}$. In another embodiment, each $R^b$ is independently chosen from $C_{1-6}$alkyl optionally substituted by 1-6 $R^{59}$, $C_{2-6}$alkenyl optionally substituted by 1-6 $R^{59}$, $C_{2-6}$alkynyl optionally substituted by 1-9 $R^{59}$, $C_{6-11}$aryl optionally substituted by 1-7 $R^{59}$, $C_{7-16}$arylalkyl optionally substituted by 1-6 $R^{59}$, $C_{3-11}$cycloalkyl optionally substituted by 1-6 $R^{59}$, $C_{4-17}$cycloalkylalkyl optionally substituted by 1-6 $R^{59}$, 3-15 membered heterocycloalkyl optionally substituted by 1-6 $R^{59}$, 4-21 membered heterocycloalkylalkyl optionally substituted by 1-6 $R^{59}$, 5-15 membered heteroaryl optionally substituted by 1-6 $R^{59}$, 6-21 membered heteroarylalkyl optionally substituted by 1-6 $R^{59}$, halogen, —CN, —C(=O)$R^{50}$, —C(=O)O$R^{50}$, —C(=O)N$R^{52}R^{53}$, —C(=S)N$R^{52}R^{53}$, —NC, —NO$_2$, —N$R^{52}R^{53}$, —N$R^{54}$N$R^{52}R^{53}$, —N$R^{54}$C(=O)$R^{50}$, —N$R^{54}$C(=O)O$R^{51}$, —N$R^{54}$C(=O)N$R^{52}R^{53}$, —N$R^{54}$C(=O)N$R^{54}$C(=O)$R^{50}$, —N$R^{54}$C(=O)N$R^{54}$C(=O)O$R^{50}$, —N$R^{54}$C(=N$R^{55}$)N$R^{52}R^{53}$, —N$R^{54}$C(=S)N$R^{52}R^{53}$, —N$R^{54}$S(=O)$_2R^{51}$, —O$R^{50}$, =O, —OCN, —OC(=O)$R^{50}$, —OC(=O)N$R^{52}R^{53}$, —SCN, =S, —S(=O)$_nR^{50}$, and —S(=O)$_2$N$R^{52}R^{53}$. In another embodiment, each $R^b$ is independently chosen from $C_{1-6}$alkyl optionally substituted by 1-6 $R^{59}$, $C_{6-11}$aryl optionally substituted by 1-7 $R^{59}$, $C_{7-16}$arylalkyl optionally substituted by 1-6 $R^{59}$, $C_{3-11}$cycloalkyl optionally substituted by 1-6 $R^{59}$, $C_{4-17}$cycloalkylalkyl optionally substituted by 1-6 $R^{59}$, 3-15 membered heterocycloalkyl optionally substituted by 1-6 $R^{59}$, 4-21 membered heterocycloalkylalkyl optionally substituted by 1-6 $R^{59}$, 5-15 membered heteroaryl optionally substituted by 1-6 $R^{59}$, 6-21 membered heteroarylalkyl optionally substituted by 1-6 $R^{59}$, halogen, —CN, —C(=O)$R^{50}$, —C(=O)O$R^{50}$, —C(=O)N$R^{52}R^{53}$, —C(=S)N$R^{52}R^{53}$, —N$R^{52}R^{53}$, —N$R^{54}$C(=O)$R^{50}$, —N$R^{54}$C(=O)O$R^{51}$, —N$R^{54}$C(=O)N$R^{52}R^{53}$, —N$R^{54}$C(=O)N$R^{54}$C(=O)$R^{50}$, —N$R^{54}$C(=O)N$R^{54}$C(=O)O$R^{50}$, —N$R^{54}$C(=S)$R^{50}$, —N$R^{54}$S(=O)$_2R^{51}$, —O$R^{50}$, =O, —OCN, —OC(=O)$R^{50}$, —OC(=O)N$R^{52}R^{53}$, =S, —S(=O)$_nR^{50}$, and —S(=O)$_2$N$R^{52}R^{53}$. In another embodiment, each $R^b$ is independently chosen from $C_{1-6}$alkyl optionally substituted by 1-6 $R^{59}$, $C_{6-11}$aryl optionally substituted by 1-7 $R^{59}$, $C_{7-16}$arylalkyl optionally substituted by 1-6 $R^{59}$, $C_{3-11}$cycloalkyl optionally substituted by 1-6 $R^{59}$, $C_{4-17}$cycloalkylalkyl optionally substituted by 1-6 $R^{59}$, 3-15 membered heterocycloalkyl optionally substituted by 1-6 $R^{59}$, 4-21 membered heterocycloalkylalkyl optionally substituted by 1-6 $R^{59}$, 5-15 membered heteroaryl optionally substituted by 1-6 $R^{59}$, 6-21 membered heteroarylalkyl optionally substituted by 1-6 $R^{59}$, halogen, —CN, —C(=O)$R^{50}$, —C(=O)O$R^{50}$, —C(=O)N$R^{52}R^{53}$, —N$R^{52}R^{53}$, —N$R^{54}$C(=O)$R^{50}$, —N$R^{54}$C(=O)O$R^{51}$, —N$R^{54}$C(=O)N$R^{52}R^{53}$, —N$R^{54}$S(=O)$_2R^{51}$, —O$R^{50}$, =O, —OCN, —OC(=O)$R^{50}$, —OC(=O)N$R^{52}R^{53}$, =S, —S(=O)$_nR^{50}$, and —S(=O)$_2$N$R^{52}R^{53}$. In another embodiment, each $R^b$ is independently chosen from $C_{1-6}$alkyl optionally substituted by 1-13 $R^{59}$, and halogen. In another embodiment, each $R^b$ is independently chosen from $C_{1-6}$alkyl optionally substituted by 1-3 $R^{59}$, and halogen. In another embodiment, each $R^b$ is independently chosen from $C_{1-6}$alkyl, and halogen. In another embodiment, each $R^b$ is independently chosen from $CH_3$, chloro, and fluoro.

In each embodiment of the present invention that is described in the paragraphs that precede or follow this paragraph, the definition of $G^2$ may be chosen from any of the embodiments that are described in this paragraph. In one embodiment, $G^2$ is $C_{1-6}$alkylene optionally substituted by 1-12 $R^{69}$, $C_{2-6}$alkenylene optionally substituted by 1-10 $R^{69}$, $C_{2-6}$alkynylene optionally substituted by 1-8 $R^{69}$, $C_{6-11}$arylene optionally substituted by 1-10 $R^{69}$, $C_{7-16}$aralkylene optionally substituted by 1-18 $R^{69}$, $C_{3-11}$cycloalkylene optionally substituted by 1-20 $R^{69}$, $C_{4-17}$cycloalkylalkylene optionally substituted by 1-31 $R^{69}$, 3-15 membered heterocycloalkylene optionally substituted by 1-27 $R^{69}$, 4-21 membered heterocycloalkylalkylene optionally substituted by 1-39 $R^{69}$, 5-15 membered heteroarylene optionally substituted by 1-14 $R^{69}$, 6-21 membered heteroarylalkylene optionally substituted by 1-26 $R^{69}$, —$C_{0-3}$alkylC(=O)$C_{0-3}$alkyl-, —$C_{0-3}$alkylC(=O)O$C_{0-3}$alkyl-, —$C_{0-3}$alkylC(=O)N$R^{64}C_{0-3}$alkyl-, —$C_{0-3}$alkylC(=O)C(=O)$C_{0-3}$alkyl-, —$C_{0-3}$alkylC(=N$R^{65}$)$C_{0-3}$alkyl-, —$C_{0-3}$alkylC(=N$R^{65}$)N$R^{64}C_{0-3}$alkyl-, —$C_{0-3}$alkylC(=NOH)N$R^{64}C_{0-3}$alkyl-, —$C_{0-3}$alkylC(=NO$R^{66}$)$C_{0-3}$alkyl-, —$C_{0-3}$alkylC(=NN$R^{62}R^{63}$)$C_{0-3}$alkyl-, —$C_{0-3}$alkylC(=NN$R^{64}$C(=O)$R^{61}$)$C_{0-3}$alkyl-, —$C_{0-3}$alkylC(=NN$R^{64}$C(=O)O$R^{61}$)$C_{0-3}$alkyl-, —$C_{0-3}$alkylC(=S)N$R^{64}C_{0-3}$alkyl-, —$C_{0-3}$alkylN$R^{64}C_{0-3}$alkyl-, —$C_{0-3}$alkylN$R^{64}$N$R^{64}C_{0-3}$alkyl-, —$C_{0-3}$alkylN=N$C_{0-3}$alkyl-, —$C_{0-3}$alkylN$R^{64}$C(=O)$C_{0-3}$alkyl-, —$C_{0-3}$alkylN$R^{64}$C(=O)C(=O)$C_{0-3}$alkyl-, —$C_{0-3}$alkylN$R^{64}$C(=O)O$C_{0-3}$alkyl-, —$C_{0-3}$alkylN$R^{64}$C(=O)C(=O)O$C_{0-3}$alkyl-, —$C_{0-3}$alkylN$R^{64}$C(=O)N$R^{64}C_{0-3}$alkyl-, —$C_{0-3}$alkylN$R^{64}$C(=O)N$R^{64}$C(=O)$C_{0-3}$alkyl-, —$C_{0-3}$alkylN$R^{64}$C(=O)N$R^{64}$C(=O)O$C_{0-3}$alkyl-, —$C_{0-3}$alkylN$R^{64}$C(=N$R^{65}$)N$R^{64}C_{0-3}$alkyl-, —$C_{0-3}$alkylN$R^{64}$C(=O)C(=O)N$R^{64}C_{0-3}$alkyl-, —$C_{0-3}$alkylN$R^{64}$C(=S)$C_{0-3}$alkyl-, —$C_{0-3}$alkylN$R^{64}$C(=S)O$C_{0-3}$alkyl-, —$C_{0-3}$alkylN$R^{64}$C(=S)N$R^{64}C_{0-3}$alkyl-, —$C_{0-3}$alkylN$R^{64}$S(=O)$_2C_{0-3}$alkyl-, —$C_{0-3}$alkylN$R^{64}$S(=O)$_2$N$R^{64}C_{0-3}$alkyl-, —$C_{0-3}$alkylO$C_{0-3}$alkyl-, —$C_{0-3}$alkylOC(=O)$C_{0-3}$alkyl-, —$C_{0-3}$alkylOC(=O)N$R^{64}C_{0-3}$alkyl-, —$C_{0-3}$alkylOC(=O)O$C_{0-3}$alkyl-, —$C_{0-3}$alkylOC(=N$R^{65}$)N$R^{64}C_{0-3}$alkyl-, —$C_{0-3}$alkylOS(=O)$C_{0-3}$alkyl-, —$C_{0-3}$alkylOS(=O)$_2C_{0-3}$alkyl-, —$C_{0-3}$alkylOS(=O)$_2$O$C_{0-3}$alkyl-, —$C_{0-3}$alkylOS(=O)$_2$N$R^{64}C_{0-3}$alkyl-, —$C_{0-3}$alkylS(=O)—$C_{0-3}$alkyl-, —$C_{0-3}$alkylS(=O)$_2$O$C_{0-3}$alkyl-, —$C_{0-3}$alkylSO$_3C_{0-3}$alkyl-, —$C_{0-3}$alkylS(=O)$_2$N$R^{64}C_{0-3}$alkyl-, —$C_{0-3}$alkylS(=O)N$R^{64}C_{0-3}$alkyl-, or absent. In another embodiment, $G^2$ is $C_{1-6}$alkylene optionally substituted by 1-12 $R^{69}$, $C_{6-11}$arylene optionally substituted by 1-6 $R^{69}$, $C_{7-16}$arylalkylene optionally substituted by 1-18 $R^{69}$, $C_{3-11}$cycloalkylene optionally substituted by 1-20 $R^{69}$, $C_{4-17}$cycloalkylalkylene optionally substituted by 1-6 $R^{69}$, 3-15 membered heterocycloalkylene optionally substituted by 1-27 $R^{69}$, 4-21 membered heterocycloalkylalkylene optionally substituted by 1-39 $R^{69}$, 5-15 membered heteroarylene optionally substituted by 1-14 $R^{69}$, 6-21 membered heteroarylalkylene optionally substituted by 1-26 $R^{69}$, —$C_{0-3}$alkylC(=O)$C_{0-3}$alkyl-, —$C_{0-3}$alkylC(=O)O$C_{0-3}$alkyl-, —$C_{0-3}$alkylC(=O)N$R^{64}C_{0-3}$alkyl-, —$C_{0-3}$alkylC(=O)C(=O)$C_{0-3}$alkyl-, —$C_{0-3}$alkylC(=S)N$R^{64}C_{0-3}$alkyl-, —$C_{0-3}$alkylN$R^{64}C_{0-3}$alkyl-, —$C_{0-3}$alkylN$R^{64}$N$R^{64}C_{0-3}$alkyl-, —$C_{0-3}$alkylN$R^{64}$C(=O)$C_{0-3}$alkyl-, —$C_{0-3}$alkylN$R^{64}$C(=O)O$C_{0-3}$alkyl-, —$C_{0-3}$alkylN$R^{64}$C(=O)N$R^{64}C_{0-3}$alkyl-, —$C_{0-3}$alkylN$R^{64}$C(=O)N$R^{64}$C(=O)$C_{0-3}$alkyl-, —$C_{0-3}$alkylN$R^{64}$C(=N$R^{65}$)N$R^{64}C_{0-3}$alkyl-, —$C_{0-3}$alkylN$R^{64}$C(=S)$C_{0-3}$alkyl-, —$C_{0-3}$alkylN$R^{64}$C(=S)N$R^{64}C_{0-3}$alkyl-, —$C_{0-3}$alkylN$R^{64}$S(=O)$_2C_{0-3}$alkyl-, —$C_{0-3}$alkylO$C_{0-3}$alkyl-, —$C_{0-3}$alkylOC(=O)$C_{0-3}$alkyl-, —$C_{0-3}$alkylOC(=O)N$R^{64}C_{0-3}$alkyl-, —$C_{0-3}$alkylS(=O)—$C_{0-3}$alkyl-, —$C_{0-3}$alkylS(=O)$_2$N$R^{64}C_{0-3}$alkyl-, or absent. In another embodiment, $G^2$ is $C_{1-6}$alkylene optionally substituted by 1-12 $R^{69}$, $C_{6-11}$ arylene optionally substituted by 1-6 $R^{69}$, $C_{7-16}$arylalkylene optionally substituted by 1-18 $R^{69}$, $C_{3-11}$cycloalkylene optionally substituted by 1-20 $R^{69}$, $C_{4-17}$cycloalkylalkylene optionally substituted by 1-6 $R^{69}$, 3-15 membered heterocycloalkylene optionally substituted by 1-27 $R^{69}$, 4-21 membered heterocycloalkylalkylene optionally substituted by 1-39 $R^{69}$, 5-15 membered heteroarylene optionally substituted by 1-14 $R^{69}$, 6-21 membered heteroarylalkylene optionally substituted by 1-26 $R^{69}$, —$C_{0-3}$alkylC(=O)$C_{0-3}$alkyl-, —$C_{0-3}$alkylC(=O)O$C_{0-3}$alkyl-, —$C_{0-3}$alkylC(=O)N$R^{64}C_{0-3}$alkyl-, —$C_{0-3}$alkylC(=S)N$R^{64}C_{0-3}$alkyl-, —$C_{0-3}$alkylN$R^{64}C_{0-3}$alkyl-, —$C_{0-3}$alkylN$R^{64}$N$R^{64}C_{0-3}$alkyl-, —$C_{0-3}$alkylN$R^{64}$C(=O)$C_{0-3}$alkyl-, —$C_{0-3}$alkylN$R^{64}$C(=O)O$C_{0-3}$alkyl-, —$C_{0-3}$alkylN$R^{64}$C(=O)N$R^{64}C_{0-3}$alkyl-, —$C_{0-3}$alkylN$R^{64}$C(=O)N$R^{64}$C(=O)$C_{0-3}$alkyl-, —$C_{0-3}$alkylN$R^{64}$C(=O)$C_{0-3}$alkyl-, alkylNR$^{64}$C(=S)C$_{0-3}$alkyl-, —C$_{0-3}$alkylNR$^{64}$S(=O)$_2$C$_{0-3}$ alkyl-, —C$_{0-3}$alkylOC$_{0-3}$alkyl-, —C$_{0-3}$alkylOC(=O)C$_{0-3}$ alkyl-, —C$_{0-3}$alkylOC(=O)NR$^{64}$C$_{0-3}$alkyl-, —C$_{0-3}$alkylS (=O)—C$_{0-3}$alkyl-, —C$_{0-3}$alkylS(=O)$_2$NR$^{64}$C$_{0-3}$alkyl-, or absent. In another embodiment, G$^2$ is C$_{1-6}$alkylene optionally substituted by 1-12 R$^{69}$, C$_{6-11}$arylene optionally substituted by 1-6 R$^{69}$, C$_{3-11}$cycloalkylene optionally substituted by 1-20 R$^{69}$, 3-15 membered heterocycloalkylene optionally substituted by 1-27 R$^{69}$, 5-15 membered heteroarylene optionally substituted by 1-14 R$^{69}$, —C$_{0-3}$alkylC(=O)C$_{0-3}$alkyl-, —C$_{0-3}$ alkylC(=O)OC$_{0-3}$alkyl-, —C$_{0-3}$alkylC(=O) NR$^{64}$C$_{0-3}$ alkyl-, —C$_{0-3}$alkylNR$^{64}$C$_{0-3}$alkyl-, —C$_{0-3}$alkylNR$^{64}$C(=O)C$_{0-3}$alkyl-, —C$_{0-3}$alkylNR$^{64}$C(=O)OC$_{0-3}$ alkyl-, —C$_{0-3}$alkylNR$^{64}$C(=O)NR$^{64}$C$_{0-3}$alkyl-, —C$_{0-3}$ alkylNR$^{64}$S(=O)$_2$C$_{0-3}$alkyl-, —C$_{0-3}$alkylOC$_{0-3}$alkyl-, —C$_{0-3}$alkylOC(=O)C$_{0-3}$alkyl-, —C$_{0-3}$alkylOC(=O) NR$^{64}$C$_{0-3}$alkyl-, —C$_{0-3}$alkylS(=O)—C$_{0-3}$alkyl-, —C$_{0-3}$ alkylS(=O)$_2$ NR$^{64}$C$_{0-3}$alkyl-, or absent. In another embodiment, G$^2$ is C$_{1-6}$alkylene optionally substituted by 1-12 R$^{69}$, C$_{6-11}$arylene optionally substituted by 1-6 R$^{69}$, 3-15 membered heterocycloalkylene optionally substituted by 1-27 R$^{69}$, 5-15 membered heteroarylene optionally substituted by 1-14 R$^{69}$, —C$_{0-3}$ alkylC(=O)C$_{0-3}$alkyl-, —C$_{0-3}$alkylC(=O) OC$_{0-3}$alkyl-, —C$_{0-3}$alkylC(=O)NR$^{64}$C$_{0-3}$alkyl-, —C$_{0-3}$ alkylNR$^{64}$C$_{0-3}$ alkyl-, —C$_{0-3}$alkylNR$^{64}$C(=O)C$_{0-3}$alkyl-, —C$_{0-3}$ alkylNR$^{64}$C(=O)NR$^{64}$C$_{0-3}$alkyl-, —C$_{0-3}$ alkylNR$^{64}$S(=O)$_2$ C$_{0-3}$alkyl-, —C$_{0-3}$alkylOC$_{0-3}$alkyl-, —C$_{0-3}$alkylOC(=O)C$_{0-3}$alkyl-, —C$_{0-3}$alkylS(=O)—C$_{0-3}$ alkyl-, —C$_{0-3}$alkylS(=O)$_2$NR$^{64}$C$_{0-3}$alkyl-, or absent. In another embodiment, G$^2$ is C$_{1-6}$alkylene optionally substituted by 1-12 R$^{69}$, C$_{6-11}$arylene optionally substituted by 1-6 R$^{69}$, 3-15 membered heterocycloalkylene optionally substituted by 1-27 R$^{69}$, —C$_{0-3}$alkylC(=O)C$_{0-3}$alkyl-, —C$_{0-3}$ alkylC(=O)OC$_{0-3}$ alkyl-, —C$_{0-3}$alkylC(=O)NR$^{64}$C$_{0-3}$ alkyl-, —C$_{0-3}$ alkylNR$^{64}$C$_{0-3}$alkyl-, —C$_{0-3}$alkylNR$^{64}$C (=O)C$_{0-3}$alkyl-, —C$_{0-3}$alkylNR$^{64}$C(=O)NR$^{64}$C$_{0-3}$alkyl-, —C$_{0-3}$alkylNR$^{64}$S(=O)$_2$C$_{0-3}$alkyl-, —C$_{0-3}$alkylOC$_{0-3}$ alkyl-, —C$_{0-3}$alkylOC(=O)C$_{0-3}$alkyl-, —C$_{0-3}$alkylS (=O)—C$_{0-3}$alkyl-, —C$_{0-3}$ alkylS(=O)$_2$NR$^{64}$C$_{0-3}$alkyl-, or absent. In another embodiment, G$^2$ is C$_{1-6}$alkylene optionally substituted by 1-12 R$^{69}$, C$_{6-11}$arylene optionally substituted by 1-6 R$^{69}$, 3-15 membered heterocycloalkylene optionally substituted by 1-27 R$^{69}$, —C$_{0-3}$alkylC(=O)C$_{0-3}$alkyl-, —C$_{0-3}$ alkylC(=O)OC$_{0-3}$alkyl-, —C$_{0-3}$alkylC(=O) NR$^{64}$C$_{0-3}$ alkyl-, —C$_{0-3}$alkylNR$^{64}$C$_{0-3}$alkyl-, —C$_{0-3}$ alkylNR$^{64}$C(=O)C$_{0-3}$ alkyl-, —C$_{0-3}$alkylNR$^{64}$S(=O)$_2$C$_{0-3}$ alkyl-, —C$_{0-3}$ alkylOC$_{0-3}$alkyl-, —C$_{0-3}$alkylOC(=O)C$_{0-3}$ alkyl-, —C$_{0-3}$ alkylS(=O)—C$_{0-3}$alkyl-, —C$_{0-3}$alkylS(=O)$_2$ NR$^{64}$C$_{0-3}$ alkyl-, or absent. In another embodiment, G$^2$ is C$_{1-6}$alkylene optionally substituted by 1-6 R$^{69}$, C$_{6-11}$arylene optionally substituted by 1-6 R$^{69}$, 3-15 membered heterocycloalkylene optionally substituted by 1-6 R$^{69}$, —C$_{0-3}$alkylC (=O)C$_{0-3}$ alkyl-, —C$_{0-3}$ alkylC(=O)OC$_{0-3}$alkyl-, —C$_{0-3}$ alkylC(=O)NR$^{64}$C$_{0-3}$ alkyl-, —C$_{0-3}$alkylNR$^{64}$C$_{0-3}$alkyl-, —C$_{0-3}$ alkylNR$^{64}$C(=O)C$_{0-3}$alkyl-, —C$_{0-3}$alkylNR$^{64}$S (=O)$_2$C$_{0-3}$alkyl-, —C$_{0-3}$ alkylOC$_{0-3}$alkyl-, —C$_{0-3}$alkylOC (=O)C$_{0-3}$alkyl-, —C$_{0-3}$ alkylS(=O)—C$_{0-3}$alkyl-, —C$_{0-3}$ alkylS(=O)$_2$NR$^{64}$C$_{0-3}$ alkyl-, or another embodiment, G$^2$ is C$_{1-6}$alkylene optionally substituted by 1-6 R$^{69}$, phenylene optionally substituted by 1-4 R$^{69}$, 5-6 membered heterocycloalkylene optionally substituted by 1-6 R$^{69}$, —C$_{0-3}$ alkylC(=O)C$_{0-3}$ alkyl-, —C$_{0-3}$alkylC(=O)OC$_{0-3}$ alkyl-, —C$_{0-3}$alkylC(=O)NR$^{64}$C$_{0-3}$alkyl-, —C$_{0-3}$ alkylNR$^{64}$C$_{0-3}$ alkyl-, —C$_{0-3}$ alkylNR$^{64}$C(=O)C$_{0-3}$alkyl-, —C$_{0-3}$ alkylNR$^{64}$S(=O)$_2$C$_{0-3}$ alkyl-, —C$_{0-3}$alkylOC$_{0-3}$ alkyl-, —C$_{0-3}$alkylOC(=O)C$_{0-3}$ alkyl-, —C$_{0-3}$alkylS (=O)—C$_{0-3}$ lkyl-, —C$_{0-3}$alkylS(=O)$_2$ NR$^{64}$C$_{0-3}$alkyl-, or absent. In another embodiment, G$^2$ is C$_{1-6}$alkylene optionally substituted by 1-6 R$^{69}$, phenylene optionally substituted by 1-4 R$^{69}$, 5 membered heterocycloalkylene optionally substituted by 1-6 R$^{69}$, —C$_{0-3}$alkylC(=O)C$_{0-3}$alkyl-, —C$_{0-3}$ alkylC(=O)OC$_{0-3}$alkyl-, —C$_{0-3}$alkylC(=O)NR$^{64}$C$_{0-3}$ alkyl-, —C$_{0-3}$alkylNR$^{64}$C$_{0-3}$alkyl-, —C$_{0-3}$alkylNR$^{64}$C(=O) C$_{0-3}$alkyl-, —C$_{0-3}$alkylNR$^{64}$S(=O)$_2$C$_{0-3}$alkyl-, —C$_{0-3}$ alkyl OC$_{0-3}$alkyl-, —C$_{0-3}$alkylOC(=O)C$_{0-3}$alkyl-, —C$_{0-3}$ alkylS (=O)—C$_{0-3}$alkyl-, —C$_{0-3}$alkylS(=O)$_2$NR$^{64}$C$_{0-3}$ alkyl-, or absent. In another embodiment, G$^2$ is C$_{1-6}$alkylene optionally substituted by 1-6 R$^{69}$, phenylene optionally substituted by 1-4 R$^{69}$, 5 membered heterocycloalkylene optionally substituted by 1-6 R$^{69}$, —C$_{0-3}$alkylC(=O)C$_{0-3}$alkyl-, —C$_{0-3}$ alkylC(=O)OC$_{0-3}$alkyl-, —C$_{0-3}$alkylC(=O)NR$^{64}$C$_{0-3}$ alkyl-, —C$_{0-3}$alkylNR$^{64}$C$_{0-3}$alkyl-, —C$_{0-3}$ alkylNR$^{64}$C (=O)C$_{0-3}$alkyl-, —C$_{0-3}$alkylNR$^{64}$S(=O)$_2$C$_{0-3}$ alkyl-, —C$_{0-3}$ alkylOC$_{0-3}$alkyl-, —C$_{0-3}$alkylOC(=O)C$_{0-3}$ alkyl-, —C$_{0-3}$ alkylS(=O)$_n$C$_{0-3}$alkyl-, —C$_{0-3}$alkylS(=O)$_2$ NR$^{64}$C$_{0-3}$ alkyl-, or absent; wherein the heterocycloalkylene group contains, in addition to carbon atoms, 1-3 heteroatoms chosen from nitrogen and oxygen. In another embodiment, G$^2$ is C$_{1-6}$alkylene optionally substituted by 1-6 R$^{69}$, C$_{6-11}$arylene optionally substituted by 1-6 R$^{69}$, C$_{7-16}$arylalkylene optionally substituted by 1-6 R$^{69}$, C$_{3-11}$cycloalkylene optionally substituted by 1-6 R$^{69}$, C$_{4-17}$cycloalkylalkylene optionally substituted by 1-6 R$^{69}$, 3-15 membered heterocycloalkylene optionally substituted by 1-6 R$^{69}$, 4-21 membered heterocycloalkylalkylene optionally substituted by 1-6 R$^{69}$, 5-15 membered heteroarylene optionally substituted by 1-6 R$^{69}$, 6-21 membered heteroarylalkylene optionally substituted by 1-6 R$^{69}$, —C(=O)—, —C(=O)O—, —C(=O) NR$^{64}$—, —C(=O)C(=O)—, —C(=S)NR$^{64}$—, —NR$^{64}$—, —NR$^{64}$NR$^{64}$—, —NR$^{64}$C(=O)—, —NR$^{64}$C(=O)C (=O)—, —NR$^{64}$C(=O)O—, —NR$^{64}$C(=O)C(=O)O—, —NR$^{64}$C(=O)NR$^{64}$—, —NR$^{64}$C(=O)NR$^{64}$C(=O)—, —NR$^{64}$C(=O)NR$^{64}$C(=O)O—, —NR$^{64}$C(=NR$^{65}$) NR$^{64}$—, —NR$^{64}$C(=O)C(=O)NR$^{64}$—, —NR$^{64}$C(=S)—, —NR$^{64}$C(=S)O—, —NR$^{64}$C(=S)NR$^{64}$—, —NR$^{64}$S(= O)$_2$—, —NR—, —O—, —OC(=O)—, —OC(=O) NR$^{64}$—, —OC(=O)O—, —OS(=O)—, —OS(=O)$_2$—, —OS(=O)$_2$O—, —OS(=O)$_2$NR$^{64}$—, —S(=O)$_n$—, —S(=O)$_2$O—, —SO$_3$—, —S(=O)$_2$NR$^{64}$—, —S(=O) NR$^{64}$—, or absent. In another embodiment, G$^2$ is C$_{1-6}$alkylene optionally substituted by 1-6 R$^{69}$, C$_{6-11}$arylene optionally substituted by 1-6 R$^{69}$, C$_{7-16}$arylalkylene optionally substituted by 1-6 R$^{69}$, C$_{3-11}$cycloalkylene optionally substituted by 1-6 R$^{69}$, C$_{4-17}$cycloalkylalkylene optionally substituted by 1-6 R$^{69}$, 3-15 membered heterocycloalkylene optionally substituted by 1-6 R$^{69}$, 4-21 membered heterocycloalkylalkylene optionally substituted by 1-6 R$^{69}$, 5-15 membered heteroarylene optionally substituted by 1-6 R$^{69}$, 6-21 membered heteroarylalkylene optionally substituted by 1-6 R$^{69}$, —C(=O)—, —C(=O)O—, —C(=O)NR$^{64}$—, —C(=S)NR$^{64}$—, —NR$^{64}$—, —NR$^{64}$NR$^{64}$—, —NR$^{64}$C (=O)—, —NR$^{64}$C(=O)O—, —NR$^{64}$C(=O)NR$^{64}$—, —NR$^{64}$C(=O)NR$^{64}$C(=O)—, —NR$^{64}$C(=NR$^{65}$)NR$^{64}$—, —NR$^{64}$C(=S)—, —NR$^{64}$C(=O)NR$^{64}$—, —NR$^{64}$S(= O)$_2$—, —O—, —OC(=O)—, —OC(=O)NR$^{64}$—, —S(=O)$_n$—, —S(=O)$_2$NR$^{64}$—, or absent. In another embodiment, G$^2$ is C$_{1-6}$alkylene optionally substituted by 1-6 R$^{69}$, C$_{6-11}$arylene optionally substituted by 1-6 R$^{69}$, 3-15 membered heterocycloalkylene optionally substituted by 1-6 R$^{69}$, —C$_{0-3}$alkylC(=O)—, —C(=O)C$_{0-3}$alkyl-, —C(=O) O—, —C(=O)NR$^{64}$—, —NR$^{64}$C$_{0-3}$alkyl-, —C$_{0-3}$alky-lNR$^{64}$—, —NR$^{64}$C(=O)—, NR$^{64}$S(=O)$_2$—, —OC$_{0-3}$ alkyl-, —C$_{0-3}$alkylO—, —OC(=O)—, —S(=O)$_n$—, —S(=O)$_2$NR$^{64}$—, or absent. In another embodiment, G$^2$ is $C_{1-6}$alkylene optionally substituted by 1-6 $R^{69}$, $C_{6-11}$arylene optionally substituted by 1-6 $R^{69}$, 3-15 membered heterocycloalkylene optionally substituted by 1-6 $R^{69}$, —$C_{0-3}$alkylC(=O)—, —C(=O)$C_{0-3}$alkyl-, —C(=O)O—, —C(=O)NR$^{64}$—, —NR$^{64}C_{0-3}$alkyl-, —$C_{0-3}$alkylNR$^{64}$—, —NR$^{64}$C(=O)—, NR$^{64}$S(=O)$_2$—, —O$C_{0-3}$alkyl-, —$C_{0-3}$alkylO—, —OC(=O)—, —S(=O)—, —S(=O)$_2$—, —S(=O)$_2$NR$^{64}$—, or absent. In another embodiment, G$^2$ is $C_{1-6}$alkylene optionally substituted by 1-6 $R^{69}$, phenylene optionally substituted by 1-4 $R^{69}$, 5-6 membered heterocycloalkylene optionally substituted by 1-6 $R^{69}$, —$C_{0-3}$alkylC(=O)—, —C(=O)$C_{0-3}$alkyl-, —C(=O)O—, —C(=O)NR$^{64}$—, —NR$^{64}C_{0-3}$alkyl-, —$C_{0-3}$alkylNR$^{64}$—, —NR$^{64}$C(=O)—, NR$^{64}$S(=O)$_2$—, —O$C_{0-3}$alkyl-, —$C_{0-3}$alkylO—, —OC(=O)—, —S(=O)$_n$—, —S(=O)$_2$NR$^{64}$—, or absent. In another embodiment, G$^2$ is $C_{1-6}$alkylene optionally substituted by 1-6 $R^{69}$, phenylene optionally substituted by 1-4 $R^{69}$, 5-6 membered heterocycloalkylene optionally substituted by 1-6 $R^{69}$, —$C_{0-3}$alkylC(=O)—, —C(=O)$C_{0-3}$alkyl-, —C(=O)O—, —C(=O)NR$^{64}$—, —NR$^{64}C_{0-3}$alkyl-, —$C_{0-3}$alkylNR$^{64}$—, —NR$^{64}$C(=O)—, —NR$^{64}$S(=O)$_2$—, —O$C_{0-3}$alkyl-, —$C_{0-3}$alkylO—, —OC(=O)—, —S(=O)—, —S(=O)$_2$—, —S(=O)$_2$NR$^{64}$—, or absent. In another embodiment, G$^2$ is $C_{1-6}$alkylene optionally substituted by 1-6 $R^{69}$, phenylene optionally substituted by 1-4 $R^{69}$, 5 membered heterocycloalkylene optionally substituted by 1-6 $R^{69}$, —$C_{0-3}$alkylC(=O)—, —C(=O)$C_{0-3}$alkyl-, —C(=O)O—, —C(=O)NR$^{64}$—, —NR$^{64}C_{0-3}$alkyl-, —$C_{0-3}$alkylNR$^{64}$—, —NR$^{64}$C(=O)—, NR$^{64}$S(=O)$_2$—, —O$C_{0-3}$alkyl-, —$C_{0-3}$alkylO—, —OC(=O)—, —S(=O)$_n$—, —S(=O)$_2$NR$^{64}$—, or absent. In another embodiment, G$^2$ is $C_{1-6}$alkylene optionally substituted by 1-6 $R^{69}$, phenylene optionally substituted by 1-4 $R^{69}$, 5 membered heterocycloalkylene optionally substituted by 1-6 $R^{69}$, —$C_{0-3}$alkylC(=O)—, —C(=O)$C_{0-3}$alkyl-, —C(=O)O—, —C(=O)NR$^{64}$—, —NR$^{64}C_{0-3}$alkyl-, —$C_{0-3}$alkylNR$^{64}$—, —NR$^{64}$C(=O)—, NR$^{64}$S(=O)$_2$—, —O$C_{0-3}$alkyl-, —$C_{0-3}$alkylO—, —OC(=O)—, —S(=O)—, —S(=O)$_2$—, —S(=O)$_2$NR$^{64}$—, or absent; wherein the heterocycloalkylene group contains, in addition to carbon atoms, 1-3 heteroatoms chosen from nitrogen and oxygen. In another embodiment, G$^2$ is $C_{1-6}$alkylene optionally substituted by 1-6 $R^{69}$, $C_{6-11}$arylene optionally substituted by 1-6 $R^{69}$, $C_{7-16}$arylalkylene optionally substituted by 1-6 $R^{69}$, $C_{3-11}$cycloalkylene optionally substituted by 1-6 $R^{69}$, $C_{4-17}$cycloalkylalkylene optionally substituted by 1-6 $R^{69}$, 3-15 membered heterocycloalkylene optionally substituted by 1-6 $R^{69}$, 4-21 membered heterocycloalkylalkylene optionally substituted by 1-6 $R^{69}$, 5-15 membered heteroarylene optionally substituted by 1-6 $R^{69}$, 6-21 membered heteroarylalkylene optionally substituted by 1-6 $R^{69}$, —C(=O)—, —C(=O)O—, —C(=O)NR$^{64}$—, —C(=S)NR$^{64}$—, —NR$^{64}$—, —NR$^{64}$C(=O)—, —NR$^{64}$C(=O)O—, —NR$^{64}$C(=O)NR$^{64}$—, —NR$^{64}$C(=O)NR$^{64}$C(=O)—, —NR$^{64}$C(=S)—, —NR$^{64}$S(=O)$_2$—, —O—, —OC(=O)—, —OC(=O)NR$^{64}$—, —S(=O)$_n$—, —S(=O)$_2$ NR$^{64}$—, or absent. In another embodiment, G$^2$ is $C_{1-6}$alkylene optionally substituted by 1-6 $R^{69}$, $C_{6-11}$arylene optionally substituted by 1-6 $R^{69}$, $C_{3-11}$cycloalkylene optionally substituted by 1-6 $R^{69}$, 3-15 membered heterocycloalkylene optionally substituted by 1-6 $R^{69}$, 5-15 membered heteroarylene optionally substituted by 1-6 $R^{69}$, —C(=O)—, —C(=O)O—, —C(=O)NR$^{64}$—, —NR$^{64}$—, —NR$^{64}$C(=O)—, —NR$^{64}$C(=O)O—, —NR$^{64}$S(=O)$_2$—, —O—, —OC(=O)—, —OC(=O)NR$^{64}$—, —S(=O)$_n$—, —S(=O)$_2$NR$^{64}$—, or absent. In another embodiment, G$^2$ is —$C_{0-3}$alkylC(=O)$C_{0-3}$alkyl-, —$C_{0-3}$alkylC(=O)O$C_{0-3}$alkyl-, —$C_{0-3}$alkylC(=O)NR$^{64}C_{0-3}$alkyl-, —$C_{0-3}$alkylNR$^{64}$S(=O)$_2C_{0-3}$alkyl-, —$C_{0-3}$alkylO$C_{0-3}$alkyl-, —$C_{0-3}$alkylS(=O)—$C_{0-3}$alkyl-, —$C_{0-3}$alkylS(=O)$_2$NR$^{64}C_{0-3}$alkyl-, or absent. In another embodiment, G$^2$ is —C(=O)—, —C(=O)O—, —C(=O)NR$^{64}$—, —NR$^{64}$S(=O)$_2$—, —O—, —S(=O)$_n$—, —S(=O)$_2$NR$^{64}$—, or absent. In another embodiment, G$^2$ is —C(=O)—, —C(=O)O—, —C(=O)NR$^{64}$—, —NR$^{64}$S(=O)$_2$—, —O—, —S(=O)$_2$—, —S(=O)$_2$NR$^{64}$—, or absent. In another embodiment, G$^2$ is —C(=O)—, —C(=O)O—, —C(=O)NH—, —NHS(=O)$_2$—, —C(=O)N($C_{1-6}$alkyl)-, —N($C_{1-6}$alkyl)S(=O)$_2$—, —O—, —S(=O)$_2$—, —S(=O)$_2$NH—, —S(=O)$_2$N($C_{1-6}$alkyl)-, or absent. In another embodiment, G$^2$ is —C(=O)—, —C(=O)O—, —C(=O)NH—, —NHS(=O)$_2$—, —O—, —S(=O)$_2$—, —S(=O)$_2$NH—, —S(=O)$_2$N($C_{1-6}$alkyl)-, or absent. In another embodiment, G$^2$ is —C(=O)—, —C(=O)O—, —C(=O)NH—, —NHS(=O)$_2$—, —O—, —S(=O)$_2$—, —S(=O)$_2$NH—, —S(=O)$_2$N(CH$_3$)—, or absent.

In each embodiment of the present invention that is described in the paragraphs that precede or follow this paragraph, the definition of X$^2$ may be chosen from any of the embodiments that are described in this paragraph. In one embodiment, X$^2$ is $C_{1-6}$alkylene optionally substituted by 1-12 $R^{79}$, $C_{2-6}$alkenylene optionally substituted by 1-10 $R^{79}$, $C_{2-6}$alkynylene optionally substituted by 1-8 $R^{79}$, $C_{6-11}$arylene optionally substituted by 1-10 $R^{79}$, $C_{7-16}$arylalkylene optionally substituted by 1-18 $R^{79}$, $C_{3-11}$cycloalkylene optionally substituted by 1-20 $R^{79}$, $C_{4-17}$cycloalkylalkylene optionally substituted by 1-31 $R^{79}$, 3-15 membered heterocycloalkylene optionally substituted by 1-27 $R^{79}$, 4-21 membered heterocycloalkylalkylene optionally substituted by 1-39 $R^{79}$, 5-15 membered heteroarylene optionally substituted by 1-14 $R^{79}$, 6-21 membered heteroarylalkylene optionally substituted by 1-26 $R^{79}$, —$C_{0-3}$alkylC(=O)$C_{0-3}$alkyl-, —$C_{0-3}$alkylC(=O)O$C_{0-3}$alkyl-, —$C_{0-3}$alkylC(=O)NR$^{74}C_{0-3}$alkyl-, —$C_{0-3}$alkylC(=O)C(=O)$C_{0-3}$alkyl-, —$C_{0-3}$alkylC(=NR$^{75}$)$C_{0-3}$alkyl-, —$C_{0-3}$alkylC(=NR$^{75}$)NR$^{74}C_{0-3}$alkyl-, —$C_{0-3}$alkylC(=NOH)NR$^{74}C_{0-3}$alkyl-, —$C_{0-3}$alkylC(=NOR$^{76}$)$C_{0-3}$alkyl-, —$C_{0-3}$alkylC(=NNR$^{72}$R$^{73}$)$C_{0-3}$alkyl-, —$C_{0-3}$alkylC(=NNR$^{74}$C(=O)R$^{71}$)$C_{0-3}$alkyl-, —$C_{0-3}$alkylC(=NNR$^{74}$C(=O)OR$^{71}$)$C_{0-3}$alkyl-, —$C_{0-3}$alkylC(=S)NR$^{74}C_{0-3}$alkyl-, —$C_{0-3}$alkylNR$^{74}C_{0-3}$alkyl-, —$C_{0-3}$alkylNR$^{74}$NR$^{74}C_{0-3}$alkyl-, —$C_{0-3}$alkylN=NC$_{0-3}$alkyl-, —$C_{0-3}$alkylNR$^{74}$C(=O)$C_{0-3}$alkyl-, —$C_{0-3}$alkylNR$^{74}$C(=O)C(=O)$C_{0-3}$alkyl-, —$C_{0-3}$alkylNR$^{74}$C(=O)O$C_{0-3}$alkyl-, —$C_{0-3}$alkylNR$^{74}$C(=O)C(=O)O$C_{0-3}$alkyl-, —$C_{0-3}$alkylNR$^{74}$C(=O)NR$^{74}C_{0-3}$alkyl-, —$C_{0-3}$alkylNR$^{74}$C(=O)NR$^{74}$C(=O)$C_{0-3}$alkyl-, —$C_{0-3}$alkylNR$^{74}$C(=O)NR$^{74}$C(=O)O$C_{0-3}$alkyl-, —$C_{0-3}$alkylNR$^{74}$C(=NR$^{75}$)NR$^{74}C_{0-3}$alkyl-, —$C_{0-3}$alkylNR$^{74}$C(=O)C(=O)NR$^{74}C_{0-3}$alkyl-, —$C_{0-3}$alkylNR$^{74}$C(=S)$C_{0-3}$alkyl-, —$C_{0-3}$alkylNR$^{74}$C(=S)O$C_{0-3}$alkyl-, —$C_{0-3}$alkylNR$^{74}$C(=S)NR$^{74}C_{0-3}$alkyl-, —$C_{0-3}$alkylNR$^{74}$S(=O)$_2C_{0-3}$alkyl-, —$C_{0-3}$alkylNR$^{74}$S(=O)$_2$NR$^{74}C_{0-3}$alkyl-, —$C_{0-3}$alkylO$C_{0-3}$alkyl-, —$C_{0-3}$alkylOC(=O)$C_{0-3}$alkyl-, —$C_{0-3}$alkylOC(=O)NR$^{74}C_{0-3}$alkyl-, —$C_{0-3}$alkylOC(=O)O$C_{0-3}$alkyl-, —$C_{0-3}$alkylOC(=NR$^{75}$)NR$^{74}C_{0-3}$alkyl-, —$C_{0-3}$alkylOS(=O)$C_{0-3}$alkyl-, —$C_{0-3}$alkylOS(=O)$_2C_{0-3}$alkyl-, —$C_{0-3}$alkylOS(=O)$_2$O$C_{0-3}$alkyl-, —$C_{0-3}$alkylOS(=O)$_2$N$R^{74}C_{0-3}$alkyl-, —$C_{0-3}$alkylS(=O)—$C_{0-3}$alkyl-, —$C_{0-3}$alkylS(=O)$_2$O$C_{0-3}$alkyl-, —$C_{0-3}$alkylSO$_3C_{0-3}$alkyl-, —$C_{0-3}$alkylS(=O)$_2$N$R^{74}C_{0-3}$alkyl-, —$C_{0-3}$alkylS(=O)N$R^{74}C_{0-3}$alkyl-, or absent. In another embodiment, $X^2$ is $C_{1-6}$alkylene optionally substituted by 1-12 $R^{79}$, $C_{6-11}$arylene optionally substituted by 1-6 $R^{79}$, $C_{7-16}$arylalkylene optionally substituted by 1-18 $R^{79}$, $C_{3-11}$cycloalkylene optionally substituted by 1-20 $R^{79}$, $C_{4-17}$cycloalkylalkylene optionally substituted by 1-31 $R^{79}$, 3-15 membered heterocycloalkylene optionally substituted by 1-27 $R^{79}$, 4-21 membered heterocycloalkylalkylene optionally substituted by 1-39 $R^{79}$, 5-15 membered heteroarylene optionally substituted by 1-14 $R^{79}$, 6-21 membered heteroarylalkylene optionally substituted by 1-26 $R^{79}$, —$C_{0-3}$alkylC(=O)$C_{0-3}$alkyl-, —$C_{0-3}$alkylC(=O)O$C_{0-3}$alkyl-, —$C_{0-3}$alkylC(=O)N$R^{74}C_{0-3}$alkyl-, —$C_{0-3}$alkylC(=O)C(=O)$C_{0-3}$alkyl-, —$C_{0-3}$alkylC(=S)N$R^{74}C_{0-3}$alkyl-, —$C_{0-3}$alkylN$R^{74}C_{0-3}$alkyl-, —$C_{0-3}$alkylN$R^{74}$N$R^{74}C_{0-3}$alkyl-, —$C_{0-3}$alkylN$R^{74}$C(=O)$C_{0-3}$alkyl-, —$C_{0-3}$alkylN$R^{74}$C(=O)C(=O)$C_{0-3}$alkyl-, —$C_{0-3}$alkylN$R^{74}$C(=O)O$C_{0-3}$alkyl-, —$C_{0-3}$alkylN$R^{74}$C(=O)C(=O)O$C_{0-3}$alkyl-, —$C_{0-3}$alkylN$R^{74}$C(=O)N$R^{74}C_{0-3}$alkyl-, —$C_{0-3}$alkylN$R^{74}$C(=O)N$R^{74}$C(=O)$C_{0-3}$alkyl-, —$C_{0-3}$alkylN$R^{74}$C(=O)N$R^{74}$C(=O)O$C_{0-3}$alkyl-, —$C_{0-3}$alkylN$R^{74}$C(=N$R^{75}$)N$R^{74}C_{0-3}$alkyl-, —$C_{0-3}$alkylN$R^{74}$C(=O)C(=O)N$R^{74}C_{0-3}$alkyl-, —$C_{0-3}$alkylN$R^{74}$C(=S)$C_{0-3}$alkyl-, —$C_{0-3}$alkylN$R^{74}$C(=S)O$C_{0-3}$alkyl-, —$C_{0-3}$alkylN$R^{74}$C(=S)N$R^{74}C_{0-3}$alkyl-, —$C_{0-3}$alkylN$R^{74}$S(=O)$_2C_{0-3}$alkyl-, —$C_{0-3}$alkylN$R^{74}$S(=O)$_2$N$R^{74}C_{0-3}$alkyl-, —$C_{0-3}$alkylO$C_{0-3}$alkyl-, —$C_{0-3}$alkylOC(=O)$C_{0-3}$alkyl-, —$C_{0-3}$alkylOC(=O)N$R^{74}C_{0-3}$alkyl-, —$C_{0-3}$alkylOC(=O)O$C_{0-3}$alkyl-, —$C_{0-3}$alkylOS(=O)$C_{0-3}$alkyl-, —$C_{0-3}$alkylOS(=O)$_2C_{0-3}$alkyl-, —$C_{0-3}$alkylOS(=O)$_2$O$C_{0-3}$alkyl-, —$C_{0-3}$alkylOS(=O)$_2$N$R^{74}C_{0-3}$alkyl-, —$C_{0-3}$alkylS(=O)—$C_{0-3}$alkyl-, —$C_{0-3}$alkylS(=O)$_2$O$C_{0-3}$alkyl-, —$C_{0-3}$alkylSO$_3C_{0-3}$alkyl-, —$C_{0-3}$alkylS(=O)$_2$N$R^{74}C_{0-3}$alkyl-, —$C_{0-3}$alkylS(=O)N$R^{74}C_{0-3}$alkyl-, or absent. In another embodiment, $X^2$ is $C_{1-6}$alkylene optionally substituted by 1-12 $R^{79}$, $C_{6-11}$arylene optionally substituted by 1-6 $R^{79}$, $C_{7-16}$arylalkylene optionally substituted by 1-18 $R^{79}$, $C_{3-11}$cycloalkylene optionally substituted by 1-20 $R^{79}$, $C_{4-17}$cycloalkylalkylene optionally substituted by 1-31 $R^{79}$, 3-15 membered heterocycloalkylene optionally substituted by 1-27 $R^{79}$, 4-21 membered heterocycloalkylalkylene optionally substituted by 1-39 $R^{79}$, 5-15 membered heteroarylene optionally substituted by 1-14 $R^{79}$, 6-21 membered heteroarylalkylene optionally substituted by 1-26 $R^{79}$, —$C_{0-3}$alkylC(=O)$C_{0-3}$alkyl-, —$C_{0-3}$alkylC(=O)O$C_{0-3}$alkyl-, —$C_{0-3}$alkylC(=O)N$R^{74}C_{0-3}$alkyl-, —$C_{0-3}$alkylC(=S)N$R^{74}C_{0-3}$alkyl-, —$C_{0-3}$alkylN$R^{74}C_{0-3}$alkyl-, —$C_{0-3}$alkylN$R^{74}$C(=O)$C_{0-3}$alkyl-, —$C_{0-3}$alkylN$R^{74}$C(=O)O$C_{0-3}$alkyl-, —$C_{0-3}$alkylN$R^{74}$C(=O)N$R^{74}C_{0-3}$alkyl-, —$C_{0-3}$alkylN$R^{74}$C(=O)N$R^{74}$C(=O)$C_{0-3}$alkyl-, —$C_{0-3}$alkylN$R^{74}$C(=O)N$R^{74}$C(=O)O$C_{0-3}$alkyl-, —$C_{0-3}$alkylN$R^{74}$C(=S)$C_{0-3}$alkyl-, —$C_{0-3}$alkylN$R^{74}$S(=O)$_2C_{0-3}$alkyl-, —$C_{0-3}$alkylO$C_{0-3}$alkyl-, —$C_{0-3}$alkylOC(=O)$C_{0-3}$alkyl-, —$C_{0-3}$alkylOC(=O)N$R^{74}C_{0-3}$alkyl-, —$C_{0-3}$alkylS(=O)—$C_{0-3}$alkyl-, —$C_{0-3}$alkylS(=O)$_2$N$R^{74}C_{0-3}$alkyl-, or absent. In another embodiment, $X^2$ is $C_{1-6}$alkylene optionally substituted by 1-12 $R^{79}$, $C_{6-11}$arylene optionally substituted by 1-6 $R^{79}$, $C_{3-11}$cycloalkylene optionally substituted by 1-20 $R^{79}$, 3-15 membered heterocycloalkylene optionally substituted by 1-27 $R^{79}$, 5-15 membered heteroarylene optionally substituted by 1-14 $R^{79}$, —$C_{0-3}$alkylC(=O)$C_{0-3}$alkyl-, —$C_{0-3}$alkylC(=O)O$C_{0-3}$alkyl-, —$C_{0-3}$alkylC(=O)N$R^{74}C_{0-3}$alkyl-, —$C_{0-3}$alkylN$R^{74}C_{0-3}$alkyl-, —$C_{0-3}$alkylN$R^{74}$C(=O)$C_{0-3}$alkyl-, —$C_{0-3}$alkylN$R^{74}$C(=O)O$C_{0-3}$alkyl-, —$C_{0-3}$alkylN$R^{74}$C(=O)N$R^{74}C_{0-3}$alkyl-, —$C_{0-3}$alkylS(=O)$_2C_{0-3}$alkyl-, —$C_{0-3}$alkylO$C_{0-3}$alkyl-, —$C_{0-3}$alkylOC(=O)$C_{0-3}$alkyl-, —$C_{0-3}$alkylOC(=O)N$R^{74}C_{0-3}$alkyl-, —$C_{0-3}$alkylS(=O)—$C_{0-3}$alkyl-, —$C_{0-3}$alkylS(=O)$_2$N$R^{74}C_{0-3}$alkyl-, or absent. In another embodiment, $X^2$ is $C_{1-6}$alkylene optionally substituted by 1-12 $R^{79}$, $C_{3-11}$cycloalkylene optionally substituted by 1-20 $R^{79}$, 3-15 membered heterocycloalkylene optionally substituted by 1-27 $R^{79}$, —$C_{0-3}$alkylC(=O)O$C_{0-3}$alkyl-, —$C_{0-3}$alkylN$R^{74}C_{0-3}$alkyl-, —$C_{0-3}$alkylS(=O)$_2C_{0-3}$alkyl-, or absent. In another embodiment, $X^2$ is $C_{1-6}$alkylene optionally substituted by 1-6 $R^{79}$, $C_{3-11}$cycloalkylene optionally substituted by 1-6 $R^{79}$, 3-15 membered heterocycloalkylene optionally substituted by 1-6 $R^{79}$, —$C_{0-3}$alkylC(=O)O$C_{0-3}$alkyl-, —$C_{0-3}$alkylN$R^{74}C_{0-3}$alkyl-, —$C_{0-3}$alkylS(=O)$_2C_{0-3}$alkyl-, or absent. In another embodiment, $X^2$ is $C_{1-6}$alkylene optionally substituted by 1-6 $R^{79}$, $C_{3-6}$cycloalkylene optionally substituted by 1-6 $R^{79}$, 3-6 membered heterocycloalkylene optionally substituted by 1-6 $R^{79}$, —$C_{0-3}$alkylC(=O)O$C_{0-3}$alkyl-, —$C_{0-3}$alkylN$R^{74}C_{0-3}$alkyl-, —$C_{0-3}$alkylS(=O)$_2C_{0-3}$alkyl-, or absent. In another embodiment, $X^2$ is $C_{1-6}$alkylene optionally substituted by 1-6 $R^{79}$, $C_3$cycloalkylene optionally substituted by 1-6 $R^{79}$, 5-6 membered heterocycloalkylene optionally substituted by 1-6 $R^{79}$, —$C_{0-3}$alkylC(=O)O$C_{0-3}$alkyl-, —$C_{0-3}$alkylN$R^{74}C_{0-3}$alkyl-, —$C_{0-3}$alkylS(=O)$_2C_{0-3}$alkyl-, or absent. In another embodiment, $X^2$ is $C_{1-6}$alkylene optionally substituted by 1-6 $R^{79}$, $C_3$cycloalkylene optionally substituted by 1-6 $R^{79}$, 5-6 membered heterocycloalkylene optionally substituted by 1-6 $R^{79}$, —$C_{0-3}$alkylC(=O)O$C_{0-3}$alkyl-, —$C_{0-3}$alkylN$R^{74}C_{0-3}$alkyl-, —$C_{0-3}$alkylS(=O)$_2C_{0-3}$alkyl-, or absent; wherein the heterocycloalkylene group contains, in addition to carbon atoms, 1-3 heteroatoms chosen from N, O, and S. In another embodiment, $X^2$ is $C_{1-6}$alkylene optionally substituted by 1-6 $R^{79}$, $C_{3-6}$cycloalkylene optionally substituted by 1-6 $R^{79}$, 3-6 membered heterocycloalkylene optionally substituted by 1-6 $R^{79}$, —C(=O)O—, —N$R^{74}C_{0-3}$alkyl-, —$C_{0-3}$alkylN$R^{74}$—, —$C_{0-3}$alkylS(=O)$_2$—, or absent. In another embodiment, $X^2$ is $C_{1-6}$alkylene optionally substituted by 1-6 $R^{79}$, $C_{3-6}$cycloalkylene optionally substituted by 1-6 $R^{79}$, 3-6 membered heterocycloalkylene optionally substituted by 1-6 $R^{79}$, —C(=O)O—, —N$R^{74}C_{0-3}$alkyl-, —$C_{0-3}$alkylN$R^{74}$—, —$C_{0-3}$alkylS(=O)$_2$—, or absent; wherein the heterocycloalkylene group contains, in addition to carbon atoms, 1-3 heteroatoms chosen from N, O, and S. In another embodiment, $X^2$ is $C_{1-6}$alkylene optionally substituted by 1-6 $R^{79}$, $C_3$cycloalkylene optionally substituted by 1-6 $R^{79}$, 5-6 membered heterocycloalkylene optionally substituted by 1-6 $R^{79}$, —C(=O)O—, —NR$^{74}$C$_{0-3}$ alkyl-, —C$_{0-3}$alkylNR$^{74}$—, —C$_{0-3}$alkylS(=O)$_2$—, or absent. In another embodiment, $X^2$ is $C_{1-6}$alkylene optionally substituted by 1-6 $R^{79}$, $C_3$cycloalkylene optionally substituted by 1-6 $R^{79}$, 5-6 membered heterocycloalkylene optionally substituted by 1-6 $R^{79}$, —C(=O)O—, —NR$^{74}$C$_{0-3}$ alkyl-, —C$_{0-3}$alkylNR$^{74}$—, —C$_{0-3}$alkylS(=O)$_2$—, or absent; wherein the heterocycloalkylene group contains, in addition to carbon atoms, 1-3 heteroatoms chosen from N, O, and S. In another embodiment, $X^2$ is $C_{1-6}$alkylene optionally substituted by 1-6 $R^{79}$, $C_{6-11}$arylene optionally substituted by 1-6 $R^{79}$, $C_{7-16}$arylalkylene optionally substituted by 1-6 $R^{79}$, $C_{3-11}$cycloalkylene optionally substituted by 1-6 $R^{79}$, $C_{4-17}$cycloalkylalkylene optionally substituted by 1-6 $R^{79}$, 3-15 membered heterocycloalkylene optionally substituted by 1-6 $R^{79}$, 4-21 membered heterocycloalkylalkylene optionally substituted by 1-6 $R^{79}$, 5-15 membered heteroarylene optionally substituted by 1-6 $R^{79}$, 6-21 membered heteroarylalkylene optionally substituted by 1-6 $R^{79}$, —C(=O)—, —C(=O)O—, —C(=O)NR$^{74}$—, —C(=O)C(=O)—, —C(=S)NR$^{74}$—, —NR$^{74}$—, —NR$^{74}$NR$^{74}$—, —NR$^{74}$C(=O)—, —NR$^{74}$C(=O)C(=O)—, —NR$^{74}$C(=O)O—, —NR$^{74}$C(=O)C(=O)O—, —NR$^{74}$C(=O)NR$^{74}$—, —NR$^{74}$C(=O)NR$^{74}$C(=O)—, —NR$^{74}$C(=O)NR$^{74}$C(=O)O—, —NR$^{74}$C(=NR$^{75}$)NR$^{74}$—, —NR$^{74}$C(=O)C(=O)NR$^{74}$—, —NR$^{74}$C(=S)—, —NR$^{74}$C(=S)O—, —NR$^{74}$C(=S)NR$^{74}$—, —NR$^{74}$S(=O)$_2$—, —NR$^{74}$S(=O)$_2$NR$^{74}$—, —O—, —OC(=O)—, —OC(=O)NR$^{74}$—, —OC(=O)O—, —OS(=O)—, —OS(=O)$_2$—, —OS(=O)$_2$O—, —OS(=O)$_2$NR$^{74}$—, —S(=O)$_n$—, —S(=O)$_2$O—, —SO$_3$—, —S(=O)$_2$NR$^{74}$—, —S(=O)NR$^{74}$—, or absent. In another embodiment, $X^2$ is $C_{1-6}$alkylene optionally substituted by 1-6 $R^{79}$, $C_{6-11}$ arylene optionally substituted by 1-6 $R^{79}$, $C_{7-16}$arylalkylene optionally substituted by 1-6 $R^{79}$, $C_{3-11}$cycloalkylene optionally substituted by 1-6 $R^{79}$, $C_{4-17}$cycloalkylalkylene optionally substituted by 1-6 $R^{79}$, 3-15 membered heterocycloalkylene optionally substituted by 1-6 $R^{79}$, 4-21 membered heterocycloalkylalkylene optionally substituted by 1-6 $R^{79}$, 5-15 membered heteroarylene optionally substituted by 1-6 $R^{79}$, 6-21 membered heteroarylalkylene optionally substituted by 1-6 $R^{79}$, —C(=O)—, —C(=O)O—, —C(=O)NR$^{74}$—, —C(=S)NR$^{74}$—, —NR$^{74}$—, —NR$^{74}$C(=O)—, —NR$^{74}$C(=O)O—, —NR$^{74}$C(=O)NR$^{74}$—, —NR$^{74}$C(=O)NR$^{74}$C(=O)—, —NR$^{74}$C(=O)NR$^{74}$C(=O)O—, —NR$^{74}$C(=S)—, —NR$^{74}$S(=O)$_2$—, —O—, —OC(=O)—, —OC(=O)NR$^{74}$—, —S(=O)$_n$—, —S(=O)$_2$NR$^{74}$—, or absent. In another embodiment, $X^2$ is $C_{1-6}$alkylene optionally substituted by 1-6 $R^{79}$, $C_{6-11}$arylene optionally substituted by 1-6 $R^{79}$, $C_{3-11}$cycloalkylene optionally substituted by 1-6 $R^{79}$, 3-15 membered heterocycloalkylene optionally substituted by 1-6 $R^{79}$, 5-15 membered heteroarylene optionally substituted by 1-6 $R^{79}$, —C(=O)—, —C(=O)O—, —C(=O)NR$^{74}$—, —NR$^{74}$—, —NR$^{74}$C(=O)—, —NR$^{74}$C(=O)O—, —NR$^{74}$C(=O)NR$^{74}$—, —NR$^{74}$S(=O)$_2$—, —O—, —OC(=O)—, —OC(=O)NR$^{74}$—, —S(=O)$_n$—, —S(=O)$_2$NR$^{74}$—, or absent. In another embodiment, $X^2$ is $C_{1-6}$alkylene optionally substituted by 1-12 $R^{79}$, or absent. In another embodiment, $X^2$ is $C_{1-6}$alkylene optionally substituted by 1-3 $R^{79}$, or absent. In another embodiment, $X^2$ is $C_{1-6}$alkylene, or absent. In another embodiment, $X^2$ is $C_{1-6}$alkylene, or absent. In another embodiment, $X^2$ is ethylene, propylene, or absent.

In each embodiment of the present invention that is described in the paragraphs that precede or follow this paragraph, the definition of $Z^2$ may be chosen from any of the embodiments that are described in this paragraph. In one embodiment, $Z^2$ is H, $C_{1-6}$alkyl optionally substituted by 1-13 $R^{89}$, $C_{2-6}$alkenyl optionally substituted by 1-11 $R^{89}$, $C_{2-6}$alkynyl optionally substituted by 1-9 $R^{89}$, $C_{6-11}$ aryl optionally substituted by 1-11 $R^{89}$, $C_{7-16}$arylalkyl optionally substituted by 1-19 $R^{89}$, $C_{3-11}$cycloalkyl optionally substituted by 1-21 $R^{89}$, $C_{4-17}$cycloalkylalkyl optionally substituted by 1-32 $R^{89}$, 3-15 membered heterocycloalkyl optionally substituted by 1-28 $R^{89}$, 4-21 membered heterocycloalkylalkyl optionally substituted by 1-40 $R^{89}$, 5-15 membered heteroaryl optionally substituted by 1-15 $R^{89}$, 6-21 membered heteroarylalkyl optionally substituted by 1-27 $R^{89}$, halogen, —CN, —C(=O)R$^{80}$, —C(=O)OR$^{80}$, —C(=O)NR$^{82}$R$^{83}$, —C(=O)C(=O)R$^{80}$, —C(=NR$^{85}$)R$^{80}$, —C(=NR$^{85}$)NR$^{82}$R$^{83}$, —C(=NOH)NR$^{82}$R$^{83}$, —C(=NOR$^{86}$)R$^{80}$, —C(=NNR$^{82}$R$^{83}$)R$^{80}$, —C(=NNR$^{84}$C(=O)R$^{81}$)R$^{80}$, —C(=NNR$^{84}$C(=O)OR$^{81}$)R$^{80}$, —C(=S)NR$^{82}$R$^{83}$, —NC, —NO$_2$, —NR$^{82}$R$^{83}$, —NR$^{84}$NR$^{82}$R$^{83}$, —N=NR$^{84}$, =NR$^{80}$, =NOR$^{80}$, —NR$^{84}$OR$^{86}$, —NR$^{84}$C(=O)R$^{80}$, —NR$^{84}$C(=O)C(=O)R$^{80}$, —NR$^{84}$C(=O)OR$^{81}$—NR$^{84}$C(=O)C(=O)OR$^{81}$, —NR$^{84}$C(=O)NR$^{82}$R$^{83}$, —NR$^{84}$C(=O)NR$^{84}$C(=O)R$^{80}$, —NR$^{84}$C(=O)NR$^{84}$C(=O)OR$^{80}$, —NR$^{84}$C(=NR$^{85}$)NR$^{82}$R$^{83}$, —NR$^{84}$C(=O)C(=O)NR$^{82}$R$^{83}$, —NR$^{84}$C(=S)R$^{80}$, —NR$^{84}$C(=S)OR$^{80}$, —NR$^{84}$C(=NR$^{82}$R$^{83}$, —NR$^{84}$S(=O)$_2$R$^{81}$, —NR$^{84}$S(=O)$_2$NR$^{82}$R$^{83}$, —NR$^{84}$P(=O)R$^{88}$R$^{88}$, —NR$^{84}$P(=O)(NR$^{82}$R$^{83}$)(NR$^{82}$R$^{83}$), —NR$^{84}$P(=O)(OR$^{80}$)(OR$^{80}$), —NR$^{84}$P(=O)(SR$^{80}$)(SR$^{80}$), —OR$^{80}$, =O, —OCN, —OC(=O)R$^{80}$, —OC(=O)NR$^{82}$R$^{83}$, —OC(=O)OR$^{80}$, —OC(=NR$^{85}$)NR$^{82}$R$^{83}$, —OS(=O)R$^{80}$, —OS(=O)$_2$R$^{80}$, —OS(=O)$_2$OR$^{80}$, —OS(=O)$_2$NR$^{82}$R$^{83}$, —OP(=O)R$^{88}$R$^{88}$, —OP(=O)(NR$^{82}$R$^{83}$)(NR$^{82}$R$^{83}$), —OP(=O)(OR$^{80}$)(OR$^{80}$), —OP(=O)(SR$^{80}$)(SR$^{80}$), —SCN, =S, —S(=O)$_n$R$^{80}$, —S(=O)$_2$OR$^{80}$, —SO$_3$R$^{87}$, —S(=O)$_2$NR$^{82}$R$^{83}$, —S(=O)NR$^{82}$R$^{83}$, —SP(=O)R$^{88}$R$^{88}$, —SP(=O)(NR$^{82}$R$^{83}$)(NR$^{82}$R$^{83}$), —SP(=O)(OR$^{80}$)(OR$^{80}$), —SP(=O)(SR$^{80}$)(SR$^{80}$), —P(=O)R$^{88}$R$^{88}$, —P(=O)(NR$^{82}$R$^{83}$)(NR$^{82}$R$^{83}$), —P(=O)(OR$^{80}$)(OR$^{80}$), or —P(=O)(SR$^{80}$)(SR$^{80}$); alternatively, when $L^2$, $A^2$, $G^2$, $X^2$, $L^3$, $A^3$, $G^3$ and $X^3$ are absent, $Z^2$ and $Z^3$ can together form a group of formula -$A^{21}$-$A^{22}$-$A^{23}$-; wherein $A^{21}$, $A^{22}$, and $A^{23}$ are independently chosen from —C$Z^{21}Z^{22}$—, —C$Z^{23}Z^{24}$C$Z^{25}Z^{26}$—, —C(=O)—, —N$Z^{27}$—, —S—, —S(=O)—, —S(=O)$_2$—, or —O—; wherein:

(a) when any two of $Z^{21}$, $Z^{22}$, $Z^{23}$, $Z^{24}$, $Z^{25}$, $Z^{26}$ and $Z^{27}$ are located on adjacent atoms, they may together form a bond between the atoms, and (b) any of $Z^{21}$, $Z^{22}$, $Z^{23}$, $Z^{24}$, $Z^{25}$, $Z^{26}$ and $Z^{27}$ may be independently chosen from H, $C_{1-6}$alkyl optionally substituted by 1-13 $R^{99}$, $C_{2-6}$alkenyl optionally substituted by 1-11 $R^{99}$, $C_{2-6}$alkynyl optionally substituted by 1-9 $R^{99}$, $C_{6-11}$ aryl optionally substituted by 1-11 $R^{99}$, $C_{7-16}$arylalkyl optionally substituted by 1-19 $R^{99}$, $C_{3-11}$cycloalkyl optionally substituted by 1-21 $R^{99}$, $C_{4-17}$cycloalkylalkyl optionally substituted by 1-32 $R^{99}$, 3-15 membered heterocycloalkyl optionally substituted by 1-28 $R^{99}$, 4-21 membered heterocycloalkylalkyl optionally substituted by 1-40 $R^{99}$, 5-15 membered heteroaryl optionally substituted by 1-15 $R^{99}$, 6-21 membered heteroarylalkyl optionally substituted by 1-27 $R^{99}$, halogen, —CN, —C(=O)$R^{90}$, —C(=O)O$R^{90}$, —C(=O)N$R^{92}R^{93}$, —C(=O)C(=O)$R^{90}$, —C(=N$R^{95}$)$R^{90}$, —C(=N$R^{95}$)N$R^{92}R^{93}$, —C(=NOH)N$R^{92}R^{93}$, —C(=NO$R^{96}$)$R^{90}$, —C(=NN$R^{92}R^{93}$)$R^{90}$, —C(=NN$R^{94}$C(=O)$R^{91}$)$R^{90}$, —C(=NN$R^{94}$C(=O)O$R^{91}$)$R^{90}$, —C(=S)N$R^{92}R^{93}$, —NC, —NO$_2$, —N$R^{92}R^{93}$, —N$R^{94}$N$R^{92}R^{93}$, —N=N$R^{94}$, =N$R^{90}$, =NO$R^{90}$, —N$R^{94}$O$R^{96}$, —N$R^{94}$C(=O)$R^{90}$, —N$R^{94}$C(=O)C(=O)$R^{90}$, —N$R^{94}$C(=O)O$R^{91}$, —N$R^{94}$C(=O)C(=O)O$R^{91}$, —N$R^{94}$C(=O)N$R^{92}R^{93}$, —N$R^{94}$C(=O)N$R^{94}$C(=O)$R^{90}$, —N$R^{94}$C(=O)N$R^{94}$C(=O)O$R^{90}$, —N$R^{94}$C(=N$R^{95}$)N$R^{92}R^{93}$, —N$R^{94}$C(=O)C(=O)N$R^{92}R^{93}$, —N$R^{94}$C(=S)$R^{90}$, —N$R^{94}$C(=S)O$R^{90}$, —N$R^{94}$C(=S)N$R^{92}R^{93}$, —N$R^{94}$S(=O)$_2R^{91}$, —N$R^{94}$S(=O)$_2$N$R^{92}R^{93}$, —N$R^{94}$P(=O)$R^{98}R^{98}$, —N$R^{94}$P(=O)(N$R^{92}R^{93}$)(N$R^{92}R^{93}$), —N$R^{94}$P(=O)(O$R^{90}$)(O$R^{90}$), —N$R^{94}$P(=O)(S$R^{90}$)(S$R^{90}$), —O$R^{90}$, =O, —OCN, —OC(=O)$R^{90}$, —OC(=O)N$R^{92}R^{93}$, —OC(=O)O$R^{90}$, —OC(=N$R^{95}$)N$R^{92}R^{93}$, —OS(=O)$R^{90}$, —OS(=O)$_2R^{90}$, —OS(=O)$_2$O$R^{90}$, —OS(=O)$_2$N$R^{92}R^{93}$, —OP(=O)$R^{98}R^{98}$, —OP(=O)(N$R^{92}R^{93}$)(N$R^{92}R^{93}$), —OP(=O)(O$R^{90}$)(O$R^{90}$), —OP(=O)(S$R^{90}$)(S$R^{90}$), —SCN, =S, —S(=O)$_nR^{90}$, —S(=O)$_2$O$R^{90}$, —SO$_3R^{97}$, —S(=O)$_2$N$R^{92}R^{93}$, —S(=O)N$R^{92}R^{93}$, —SP(=O)$R^{98}R^{98}$, —SP(=O)(N$R^{92}R^{93}$)(N$R^{92}R^{93}$), —SP(=O)(O$R^{90}$)(O$R^{90}$), —SP(=O)(S$R^{90}$)(S$R^{90}$), —P(=O)$R^{98}R^{98}$, —P(=O)(N$R^{92}R^{93}$)(N$R^{92}R^{93}$), —P(=O)(O$R^{90}$)(O$R^{90}$), and —P(=O)(S$R^{90}$)(S$R^{90}$); and (c) any two of $Z^{21}$, $Z^{22}$, $Z^{23}$, $Z^{24}$, $Z^{25}$, $Z^{26}$ and $Z^{27}$ may together form a group of formula -$A^{31}$-$A^{32}$-$A^{33}$-, wherein $A^{31}$, $A^{32}$, and $A^{33}$ are independently chosen from —C$Z^{31}Z^{32}$—, —C$Z^{33}Z^{34}$C$Z^{35}Z^{36}$—, —C(=O)—, —N$Z^{37}$—, —S—, —S(=O)—, —S(=O)$_2$—, or —O— wherein:

(i) when any two of $Z^{31}$, $Z^{32}$, $Z^{33}$, $Z^{34}$, $Z^{35}$, $Z^{36}$ and $Z^{37}$ are located on adjacent atoms, they may together form a bond between the atoms, and (ii) any of any of $Z^{21}$, $Z^{22}$, $Z^{23}$, $Z^{24}$, $Z^{25}$, $Z^{26}$ and $Z^{27}$ may be independently chosen from H, $C_{1-6}$alkyl optionally substituted by 1-13 $R^{139}$, $C_{2-6}$alkenyl optionally substituted by 1-11 $R^{139}$, $C_{2-6}$alkynyl optionally substituted by 1-9 $R^{139}$, $C_{6-11}$aryl optionally substituted by 1-11 $R^{139}$, $C_{7-16}$arylalkyl optionally substituted by 1-19 $R^{139}$, $C_{3-11}$cycloalkyl optionally substituted by 1-21 $R^{139}$, $C_{4-17}$cycloalkylalkyl optionally substituted by 1-32 $R^{139}$, 3-15 membered heterocycloalkyl optionally substituted by 1-28 $R^{139}$, 4-21 membered heterocycloalkylalkyl optionally substituted by 1-40 $R^{139}$, 5-15 membered heteroaryl optionally substituted by 1-15 $R^{139}$, 6-21 membered heteroarylalkyl optionally substituted by 1-27 $R^{139}$, halogen, —CN, —C(=O)$R^{130}$, —C(=O)O$R^{130}$, —C(=O)N$R^{132}R^{133}$, —C(=O)C(=O)$R^{130}$, —C(=N$R^{135}$)$R^{130}$, —C(=N$R^{135}$)N$R^{132}R^{133}$, —C(=NOH)N$R^{132}R^{133}$, —C(=NO$R^{136}$)$R^{130}$, —C(=NN$R^{132}R^{133}$)$R^{130}$, —C(=NN$R^{134}$C(=O)$R^{131}$)$R^{130}$, —C(=NN$R^{134}$C(=O)O$R^{131}$)$R^{130}$, —C(=S)N$R^{132}R^{133}$, —NC, —NO$_2$, —N$R^{132}R^{133}$, —N$R^{134}$N$R^{132}R^{133}$, —N=N$R^{134}$, =N$R^{130}$, =NO$R^{130}$, —N$R^{134}$O$R^{136}$, —N$R^{134}$C(=O)$R^{130}$, —N$R^{134}$C(=O)C(=O)$R^{130}$, —N$R^{134}$C(=O)O$R^{131}$, —N$R^{134}$C(=O)N$R^{132}R^{133}$, —N$R^{134}$C(=O)NR$^{134}$C(=O)$R^{130}$, —N$R^{134}$C(=O)N$R^{134}$C(=O)O$R^{130}$, —N$R^{134}$C(=N$R^{135}$)N$R^{132}R^{133}$, —N$R^{134}$C(=O)C(=O)N$R^{132}R^{133}$, —N$R^{134}$C(=S)$R^{130}$, —N$R^{134}$C(=S)O$R^{130}$, —N$R^{134}$C(=S)N$R^{132}R^{133}$, —N$R^{134}$S(=O)$_2R^{131}$, —N$R^{134}$S(=O)$_2$N$R^{132}R^{133}$, —N$R^{134}$P(=O)$R^{138}R^{138}$, —N$R^{134}$P(=O)(N$R^{132}R^{133}$)(N$R^{132}R^{133}$), —N$R^{134}$P(=O)(O$R^{130}$)(O$R^{130}$), —N$R^{134}$P(=O)(S$R^{130}$)(S$R^{130}$), —O$R^{130}$, =O, —OCN, —OC(=O)$R^{130}$, —OC(=O)N$R^{132}R^{133}$, —OC(=O)O$R^{130}$, —OC(=N$R^{135}$)N$R^{132}R^{133}$, —OS(=O)$R^{130}$, —OS(=O)$_2R^{130}$, —OS(=O)$_2$O$R^{130}$, —OS(=O)$_2$N$R^{132}R^{133}$, —OP(=O)$R^{138}R^{138}$, —OP(=O)(N$R^{132}R^{133}$)(N$R^{132}R^{133}$), —OP(=O)(O$R^{130}$)(O$R^{130}$), —OP(=O)(S$R^{130}$)(S$R^{130}$), —SCN, =S, —S(=O)$_nR^{130}$, —S(=O)$_2$O$R^{130}$, —SO$_3R^{137}$, —S(=O)$_2$N$R^{132}R^{133}$, —S(=O)N$R^{132}R^{133}$, —SP(=O)$R^{138}R^{138}$, —SP(=O)(N$R^{132}R^{133}$)(N$R^{132}R^{133}$), —SP(=O)(O$R^{130}$)(O$R^{130}$), —SP(=O)(S$R^{130}$)(S$R^{130}$), —P(=O)$R^{138}R^{138}$, —P(=O)(N$R^{132}R^{133}$)(N$R^{132}R^{133}$), —P(=O)(O$R^{130}$)(O$R^{130}$), and —P(=O)(S$R^{130}$)(S$R^{130}$). In another embodiment, $Z^2$ is H, $C_{1-6}$alkyl optionally substituted by 1-13 $R^{89}$, $C_{2-6}$alkenyl optionally substituted by 1-11 $R^{89}$, $C_{2-6}$alkynyl optionally substituted by 1-9 $R^{89}$, $C_{6-11}$ aryl optionally substituted by 1-11 $R^{89}$, $C_{7-16}$arylalkyl optionally substituted by 1-19 $R^{89}$, $C_{3-11}$cycloalkyl optionally substituted by 1-21 $R^{89}$, $C_{4-17}$cycloalkylalkyl optionally substituted by 1-32 $R^{89}$, 3-15 membered heterocycloalkyl optionally substituted by 1-28 $R^{89}$, 4-21 membered heterocycloalkylalkyl optionally substituted by 1-40 $R^{89}$, 5-15 membered heteroaryl optionally substituted by 1-15 $R^{89}$, 6-21 membered heteroarylalkyl optionally substituted by 1-27 $R^{89}$, halogen, —CN, —C(=O)$R^{80}$, —C(=O)O$R^{80}$, —C(=O)N$R^{82}R^{83}$, —C(=O)C(=O)$R^{80}$, —C(=N$R^{85}$)$R^{80}$, —C(=N$R^{85}$)N$R^{82}R^{83}$, —C(=NOH)N$R^{82}R^{83}$, —C(=NO$R^{86}$)$R^{80}$, —C(=NN$R^{82}R^{83}$)$R^{80}$, —C(=NN$R^{84}$C(=O)$R^{81}$)$R^{80}$, —C(=NN$R^{84}$C(=O)O$R^{81}$)$R^{80}$, —C(=S)N$R^{82}R^{83}$, —NC, —NO$_2$, —N$R^{82}R^{83}$, —N$R^{84}$N$R^{82}R^{83}$, —N=N$R^{84}$, =N$R^{80}$, =NO$R^{80}$, —N$R^{84}$O$R^{86}$, —N$R^{84}$C(=O)$R^{80}$, —N$R^{84}$C(=O)C(=O)$R^{80}$, —N$R^{84}$C(=O)O$R^{81}$, —N$R^{84}$C(=O)C(=O)O$R^{81}$, —N$R^{84}$C(=O)N$R^{82}R^{83}$, —N$R^{84}$C(=O)N$R^{84}$C(=O)$R^{80}$, —N$R^{84}$C(=O)N$R^{84}$C(=O)O$R^{80}$, —N$R^{84}$C(=N$R^{85}$)N$R^{82}R^{83}$, —N$R^{84}$C(=O)C(=O)N$R^{82}R^{83}$, —N$R^{84}$C(=S)$R^{80}$, —N$R^{84}$C(=S)O$R^{80}$, —N$R^{84}$C(=S)N$R^{82}R^{83}$, —N$R^{84}$S(=O)$_2R^{81}$, —N$R^{84}$S(=O)$_2$N$R^{82}R^{83}$, —N$R^{84}$P(=O)$R^{88}R^{88}$, —O$R^{80}$, =O, —OCN, —OC(=O)$R^{80}$, —OC(=O)N$R^{82}R^{83}$, —OC(=O)O$R^{80}$, —OC(=N$R^{85}$)N$R^{82}R^{83}$, —OS(=O)$R^{80}$, —OS(=O)$_2R^{80}$, —OS(=O)$_2$O$R^{80}$, —OS(=O)$_2$N$R^{82}R^{83}$, —SCN, =S, —S(=O)$_nR^{80}$, —S(=O)$_2$O$R^{80}$, —SO$_3R^{87}$, —S(=O)$_2$N$R^{82}R^{83}$, —S(=O)N$R^{82}R^{83}$, or —P(=O)$R^{88}R^{88}$;

alternatively, when $L^2$, $A^2$, $G^2$, $X^2$, $L^3$, $A^3$, $G^3$ and $X^3$ are absent, $Z^2$ and $Z^3$ can together form a group of formula -$A^{21}$-$A^{22}$-$A^{23}$-; wherein $A^{21}$, $A^{22}$, and $A^{23}$ are independently chosen from —C$Z^{21}Z^{22}$—, —C$Z^{23}Z^{24}$C$Z^{25}Z^{26}$—, —C(=O)—, —N$Z^{27}$—, —S—, —S(=O)—, —S(=O)$_2$—, or —O—; wherein:

(a) when any two of $Z^{21}$, $Z^{22}$, $Z^{23}$, $Z^{24}$, $Z^{25}$, $Z^{26}$ and $Z^{27}$ are located on adjacent atoms, they may together form a bond between the atoms, and (b) any of $Z^{21}$, $Z^{22}$, $Z^{23}$, $Z^{24}$, $Z^{25}$, $Z^{26}$ and $Z^{27}$ may be independently chosen from H, $C_{1-6}$alkyl optionally substituted by 1-13 $R^{99}$, $C_{2-6}$alkenyl optionally substituted by 1-11 $R^{99}$, $C_{2-6}$alkynyl optionally substituted by 1-9 $R^{99}$, $C_{6-11}$ aryl optionally substituted by 1-11 $R^{99}$, $C_{7-16}$arylalkyl optionally substituted by 1-19 $R^{99}$, $C_{3-11}$cycloalkyl optionally substituted by 1-21 $R^{99}$, $C_{4-17}$cycloalkylalkyl optionally substituted by 1-32 $R^{99}$, 3-15 membered heterocycloalkyl optionally substituted by 1-28 $R^{99}$, 4-21 membered heterocycloalkylalkyl optionally substituted by 1-40 $R^{99}$, 5-15 membered heteroaryl optionally substituted by 1-15 $R^{99}$, 6-21 membered heteroarylalkyl optionally substituted by 1-27 $R^{99}$, halogen, —CN, —C(=O)$R^{90}$, —C(=O)O$R^{90}$, —C(=O)N$R^{92}R^{93}$, —C(=O)C(=O)$R^{90}$, —C(=N$R^{95}$)$R^{90}$, —C(=N$R^{95}$)N$R^{92}R^{93}$, —C(=NOH)N$R^{92}R^{93}$, —C(=NO$R^{96}$)$R^{90}$, —C(=NN$R^{92}R^{93}$)$R^{90}$, —C(=NN$R^{94}$C(=O)$R^{91}$)$R^{90}$, —C(=NN$R^{94}$C(=O)O$R^{91}$)$R^{90}$, —C(=S)N$R^{92}R^{93}$, —NC, —NO$_2$, —N$R^{92}R^{93}$, —N$R^{94}$N$R^{92}R^{93}$, —N=N$R^{94}$, =N$R^{90}$, =NO$R^{90}$, —N$R^{94}$O$R^{96}$, —N$R^{94}$C(=O)$R^{90}$, —N$R^{94}$C(=O)C(=O)$R^{90}$, —N$R^{94}$C(=O)O$R^{91}$, —N$R^{94}$C(=O)C(=O)O$R^{91}$, —N$R^{94}$C(=O)N$R^{92}R^{93}$, —N$R^{94}$C(=O)N$R^{94}$C(=O)$R^{90}$, —N$R^{94}$C(=O)N$R^{94}$C(=O)O$R^{90}$, —N$R^{94}$C(=N$R^{95}$)N$R^{92}R^{93}$, —N$R^{94}$C(=O)C(=O)N$R^{92}R^{93}$, —N$R^{94}$C(=S)$R^{90}$, —N$R^{94}$C(=S)O$R^{90}$, —N$R^{94}$C(=S)N$R^{92}R^{93}$, —N$R^{94}$S(=O)$_2R^{91}$, —N$R^{94}$S(=O)$_2$N$R^{92}R^{93}$, —N$R^{94}$P(=O)$R^{98}R^{98}$, —O$R^{90}$, =O, —OCN, —OC(=O)$R^{90}$, —OC(=O)N$R^{92}R^{93}$, —OC(=O)O$R^{90}$, —OC(=N$R^{95}$)N$R^{92}R^{93}$, —OS(=O)$R^{90}$, —OS(=O)$_2R^{90}$, —OS(=O)$_2$O$R^{90}$, —OS(=O)$_2$N$R^{92}R^{93}$, —SCN, =S, —S(=O)$_nR^{90}$, —S(=O)$_2$O$R^{90}$, —SO$_3R^{97}$, —S(=O)$_2$N$R^{92}R^{93}$, —S(=O)N$R^{92}R^{93}$, and —P(=O)$R^{98}R^{98}$; and (c) any two of $Z^{21}$, $Z^{22}$, $Z^{23}$, $Z^{24}$, $Z^{25}$, $Z^{26}$ and $Z^{27}$ may together form a group of formula -$A^{31}$-$A^{32}$-$A^{33}$-, wherein $A^{31}$, $A^{32}$, and $A^{33}$ are independently chosen from —C$Z^{31}Z^{32}$—, —C$Z^{33}Z^{34}$C$Z^{35}Z^{36}$—, —C(=O)—, —N$Z^{37}$—, —S—, —S(=O)—, —S(=O)$_2$—, or —O— wherein:

(i) when any two of $Z^{31}$, $Z^{32}$, $Z^{33}$, $Z^{34}$, $Z^{35}$, $Z^{36}$ and $Z^{37}$ are located on adjacent atoms, they may together form a bond between the atoms, and (ii) any of any of $Z^{21}$, $Z^{22}$, $Z^{23}$, $Z^{24}$, $Z^{25}$, $Z^{26}$ and $Z^{27}$ may be independently chosen from H, $C_{1-6}$alkyl optionally substituted by 1-13 $R^{139}$, $C_{2-6}$alkenyl optionally substituted by 1-11 $R^{139}$, $C_{2-6}$alkynyl optionally substituted by 1-9 $R^{139}$, $C_{6-11}$ aryl optionally substituted by 1-11 $R^{139}$, $C_{7-16}$arylalkyl optionally substituted by 1-19 $R^{139}$, $C_{3-11}$cycloalkyl optionally substituted by 1-21 $R^{139}$, $C_{4-17}$cycloalkylalkyl optionally substituted by 1-32 $R^{139}$, 3-15 membered heterocycloalkyl optionally substituted by 1-28 $R^{139}$, 4-21 membered heterocycloalkylalkyl optionally substituted by 1-40 $R^{139}$, 5-15 membered heteroaryl optionally substituted by 1-15 $R^{139}$, 6-21 membered heteroarylalkyl optionally substituted by 1-27 $R^{139}$, halogen, —CN, —C(=O)$R^{130}$, —C(=O)O$R^{130}$, —C(=O)N$R^{132}R^{133}$, —C(=O)C(=O)$R^{130}$, —C(=N$R^{135}$)$R^{130}$, —C(=N$R^{135}$)N$R^{132}R^{133}$, —C(=NOH)N$R^{132}R^{133}$, —C(=NO$R^{136}$)$R^{130}$, —C(=NN$R^{132}R^{133}$)$R^{130}$, —C(=NN$R^{134}$C(=O)$R^{131}$)$R^{130}$, —C(=NN$R^{134}$C(=O)O$R^{131}$)$R^{130}$, —C(=S)N$R^{132}R^{133}$, —NC, —NO$_2$, —N$R^{132}R^{133}$, —N$R^{134}$N$R^{132}R^{133}$, —N=N$R^{134}$, =N$R^{130}$, =NO$R^{130}$, —N$R^{134}$O$R^{136}$, —N$R^{134}$C(=O)$R^{130}$, —N$R^{134}$C(=O)C(=O)$R^{130}$, —N$R^{134}$C(=O)O$R^{131}$, —N$R^{134}$C(=O)C(=O)O$R^{131}$, —N$R^{134}$C(=O)N$R^{132}R^{133}$, —N$R^{134}$C(=O)N$R^{134}$C(=O)$R^{130}$, —N$R^{134}$C(=O)N$R^{134}$C(=O)O$R^{130}$, —N$R^{134}$C(=N$R^{135}$)N$R^{132}R^{133}$, —N$R^{134}$C(=O)C(=O)N$R^{132}R^{133}$, —N$R^{134}$C(=S)$R^{130}$, —N$R^{134}$C(=S)O$R^{130}$, —N$R^{134}$C(=S)N$R^{132}R^{133}$, —N$R^{134}$S(=O)$_2R^{131}$, —N$R^{134}$S(=O)$_2$N$R^{132}R^{133}$, —N$R^{134}$P(=O)$R^{138}R^{138}$, —O$R^{130}$, =O, —OCN, —OC(=O)$R^{130}$, —OC(=O)N$R^{132}R^{133}$, —OC(=O)O$R^{130}$, —OC(=N$R^{135}$)N$R^{132}R^{133}$, —OS(=O)$R^{130}$, —OS(=O)$_2R^{130}$, —OS(=O)$_2$O$R^{130}$, —OS(=O)$_2$N$R^{132}R^{133}$, —SCN, =S, —S(=O)$_nR^{130}$, —S(=O)$_2$O$R^{130}$, —SO$_3R^{137}$, —S(=O)$_2$N$R^{132}R^{133}$, —S(=O)N$R^{132}R^{133}$, and —P(=O)$R^{138}R^{138}$. In another embodiment, $Z^2$ is H, $C_{1-6}$alkyl optionally substituted by 1-13 $R^{89}$, $C_{2-6}$alkenyl optionally substituted by 1-11 $R^{89}$, $C_{2-6}$alkynyl optionally substituted by 1-9 $R^{89}$, $C_{6-11}$ aryl optionally substituted by 1-11 $R^{89}$, $C_{7-16}$arylalkyl optionally substituted by 1-19 $R^{89}$, $C_{3-11}$cycloalkyl optionally substituted by 1-21 $R^{89}$, $C_{4-17}$cycloalkylalkyl optionally substituted by 1-32 $R^{89}$, 3-15 membered heterocycloalkyl optionally substituted by 1-28 $R^{89}$, 4-21 membered heterocycloalkylalkyl optionally substituted by 1-40 $R^{89}$, 5-15 membered heteroaryl optionally substituted by 1-15 $R^{89}$, 6-21 membered heteroarylalkyl optionally substituted by 1-27 $R^{89}$, halogen, —CN, —C(=O)$R^{80}$, —C(=O)O$R^{80}$, —C(=O)N$R^{82}R^{83}$, —C(=O)C(=O)$R^{80}$, —C(=N$R^{85}$)$R^{80}$, —C(=N$R^{85}$)N$R^{82}R^{83}$, —C(=NOH)N$R^{82}R^{83}$, —C(=NO$R^{86}$)$R^{80}$, —C(=NN$R^{82}R^{83}$)$R^{80}$, —C(=NN$R^{84}$C(=O)$R^{81}$)$R^{80}$, —C(=NN$R^{84}$C(=O)O$R^{81}$)$R^{80}$, —C(=S)N$R^{82}R^{83}$, —NC, —NO$_2$, —N$R^{82}R^{83}$, —N$R^{84}$N$R^{82}R^{83}$, —N=N$R^{84}$, =N$R^{80}$, =NO$R^{80}$, —N$R^{84}$O$R^{86}$, —N$R^{84}$C(=O)$R^{80}$, —N$R^{84}$C(=O)C(=O)$R^{80}$, —N$R^{84}$C(=O)O$R^{81}$, —N$R^{84}$C(=O)C(=O)O$R^{81}$, —N$R^{84}$C(=O)N$R^{82}R^{83}$, —N$R^{84}$C(=O)N$R^{84}$C(=O)$R^{80}$, —N$R^{84}$C(=O)C(=O)$R^{80}$, —N$R^{84}$C(=N$R^{85}$)N$R^{82}R^{83}$, —N$R^{84}$C(=O)C(=O)N$R^{82}R^{83}$, —N$R^{84}$C(=S)$R^{80}$, —N$R^{84}$C(=S)O$R^{80}$, —N$R^{84}$C(=S)N$R^{82}R^{83}$, —N$R^{84}$S(=O)$_2R^{81}$, —N$R^{84}$S(=O)$_2$N$R^{82}R^{83}$, —O$R^{80}$, =O, —OCN, —OC(=O)$R^{80}$, —OC(=O)N$R^{82}R^{83}$, —OC(=O)O$R^{80}$, —OC(=N$R^{85}$)N$R^{82}R^{83}$, —OS(=O)$R^{80}$, —OS(=O)$_2R^{80}$, —OS(=O)$_2$O$R^{80}$, —OS(=O)$_2$N$R^{82}R^{83}$, —SCN, =S, —S(=O)$_nR^{80}$, —S(=O)$_2$O$R^{80}$, —SO$_3R^{87}$, —S(=O)$_2$N$R^{82}R^{83}$, or —S(=O)N$R^{82}R^{83}$; alternatively, when $L^2$, $A^2$, $G^2$, $X^2$, $L^3$, $A^3$, $G^3$ and $X^3$ are absent, $Z^2$ and $Z^3$ can together form a group of formula -$A^{21}$-$A^{22}$-$A^{23}$-, wherein $A^{21}$, $A^{22}$, and $A^{23}$ are independently chosen from —C$Z^{21}Z^{22}$—, —C$Z^{23}Z^{24}$C$Z^{25}Z^{26}$—, —C(=O)—, —N$Z^{27}$—, —S—, —S(=O)—, —S(=O)$_2$—, or —O—; wherein:

(a) when any two of $Z^{21}$, $Z^{22}$, $Z^{23}$, $Z^{24}$, $Z^{25}$, $Z^{26}$ and $Z^{27}$ are located on adjacent atoms, they may together form a bond between the atoms, and (b) any a $Z^{21}$, $Z^{22}$, $Z^{23}$, $Z^{24}$, $Z^{25}$, $Z^{26}$ and $Z^{27}$ may be independently chosen from H, $C_{1-6}$alkyl optionally substituted by 1-13 $R^{99}$, $C_{2-6}$alkenyl optionally substituted by 1-11 $R^{99}$, $C_{2-6}$alkynyl optionally substituted by 1-9 $R^{99}$, $C_{6-11}$ aryl optionally substituted by 1-11 $R^{99}$, $C_{7-16}$arylalkyl optionally substituted by 1-19 $R^{99}$, $C_{3-11}$cycloalkyl optionally substituted by 1-21 $R^{99}$, $C_{4-17}$cycloalkylalkyl optionally substituted by 1-32 $R^{99}$, 3-15 membered heterocycloalkyl optionally substituted by 1-28 $R^{99}$, 4-21 membered heterocycloalkylalkyl optionally substituted by 1-40 $R^{99}$, 5-15 membered heteroaryl optionally substituted by 1-15 $R^{99}$, 6-21 membered heteroarylalkyl optionally substituted by 1-27 $R^{99}$, halogen, —CN, —C(=O)$R^{90}$, —C(=O)O$R^{90}$, —C(=O)N$R^{92}R^{93}$, —C(=O)C(=O)$R^{90}$, —C(=N$R^{95}$)$R^{90}$, —C(=N$R^{95}$)N$R^{92}R^{93}$, —C(=NOH)N$R^{92}R^{93}$, —C(=NO$R^{96}$)$R^{90}$, —C(=NN$R^{92}R^{93}$)$R^{90}$, —C(=NN$R^{94}$C(=O)$R^{91}$)$R^{90}$, —C(=NN$R^{94}$C(=O)O$R^{91}$)$R^{90}$, —C(=S)N$R^{92}R^{93}$, —NC, —NO$_2$, —N$R^{92}R^{93}$, —N$R^{94}$N$R^{92}R^{93}$, —N=N$R^{94}$, =N$R^{90}$, =NO$R^{90}$, —N$R^{94}$O$R^{96}$, —N$R^{94}$C(=O)$R^{90}$, —N$R^{94}$C(=O)C(=O)$R^{90}$, —N$R^{94}$C(=O)O$R^{91}$, —N$R^{94}$C(=O)C(=O)O$R^{91}$, —N$R^{94}$C(=O)N$R^{92}R^{93}$, —N$R^{94}$C(=O)N$R^{94}$C(=O)$R^{90}$, —N$R^{94}$C(=O)N$R^{94}$C(=O)O$R^{90}$, —N$R^{94}$C(=N$R^{95}$)N$R^{92}R^{93}$, —N$R^{94}$C(=O)C(=O)N$R^{92}R^{93}$, —N$R^{94}$C(=S)$R^{90}$, —N$R^{94}$C(=S)O$R^{90}$, —N$R^{94}$C(=S)N$R^{92}R^{93}$, —N$R^{94}$S(=O)$_2R^{91}$, —N$R^{94}$S(=O)$_2$N$R^{92}R^{93}$, —O$R^{90}$, =O, —OCN, —OC(=O)$R^{90}$, —OC(=O)N$R^{92}R^{93}$, —OC (=O)OR$^{90}$, —OC(=NR$^{95}$)NR$^{92}$R$^{93}$, —OS(=O)R$^{90}$, —OS(=O)$_2$R$^{90}$, —OS(=O)$_2$OR$^{90}$, —OS(=O)$_2$NR$^{92}$R$^{93}$, —SCN, =S, —S(=O)$_n$R$^{90}$, —S(=O)$_2$OR$^{90}$, —SO$_3$R$^{97}$, —S(=O)$_2$NR$^{92}$R$^{93}$, and —S(=O)NR$^{92}$R$^{93}$; and (c) any two of $Z^{21}$, $Z^{22}$, $Z^{23}$, $Z^{24}$, $Z^{25}$, $Z^{26}$ and $Z^{27}$ may together form a group of formula -A$^{31}$-A$^{32}$-A$^{33}$-, wherein A$^{31}$, A$^{32}$, and A$^{33}$ are independently chosen from —CZ$^{31}$Z$^{32}$—, —CZ$^{33}$Z$^{34}$CZ$^{35}$Z$^{36}$—, —C(=O)—, —NZ$^{37}$—, —S—, —S(=O)—, —S(=O)$_2$—, or —O— wherein:

(i) when any two of $Z^{31}$, $Z^{32}$, $Z^{33}$, $Z^{34}$, $Z^{35}$, $Z^{36}$ and $Z^{37}$ are located on adjacent atoms, they may together form a bond between the atoms, and (ii) any of any of $Z^{21}$, $Z^{22}$, $Z^{23}$, $Z^{24}$, $Z^{25}$, $Z^{26}$ and $Z^{27}$ may be independently chosen from H, C$_{1-6}$alkyl optionally substituted by 1-13 R$^{139}$, C$_{2-6}$alkenyl optionally substituted by 1-11 R$^{139}$, C$_{2-6}$alkynyl optionally substituted by 1-9 R$^{139}$, C$_{6-11}$ aryl optionally substituted by 1-11 R$^{139}$, C$_{7-16}$arylalkyl optionally substituted by 1-19 R$^{139}$, C$_{3-11}$cycloalkyl optionally substituted by 1-21 R$^{139}$, C$_{4-17}$cycloalkylalkyl optionally substituted by 1-32 R$^{139}$, 3-15 membered heterocycloalkyl optionally substituted by 1-28 R$^{139}$, 4-21 membered heterocycloalkylalkyl optionally substituted by 1-40 R$^{139}$, 5-15 membered heteroaryl optionally substituted by 1-15 R$^{139}$, 6-21 membered heteroarylalkyl optionally substituted by 1-27 R$^{139}$, halogen, —CN, —C(=O)R$^{130}$, —C(=O)OR$^{130}$, —C(=O)NR$^{132}$R$^{133}$, —C(=O)C(=O)R$^{130}$, —C(=NR$^{135}$)R$^{130}$, —C(=NR$^{135}$)NR$^{132}$R$^{133}$, —C(=NOH)NR$^{132}$R$^{133}$, —C(=NOR$^{136}$)R$^{130}$, —C(=NNR$^{132}$R$^{133}$)R$^{130}$, —C(=NNR$^{134}$C(=O)R$^{131}$)R$^{130}$, —C(=NNR$^{134}$C(=O)OR$^{131}$)R$^{130}$, —C(=S)NR$^{132}$R$^{133}$, —NC, —NO$_2$, —NR$^{132}$R$^{133}$, —NR$^{134}$NR$^{132}$R$^{133}$, —N=NR$^{134}$, =NR$^{130}$, =NOR$^{130}$, —NR$^{134}$OR$^{136}$, —NR$^{134}$C(=O)R$^{130}$, —NR$^{134}$C(=O)C(=O)R$^{130}$, —NR$^{134}$C(=O)OR$^{131}$, —NR$^{134}$C(=O)C(=O)OR$^{131}$, —NR$^{134}$C(=O)NR$^{132}$R$^{133}$, —NR$^{134}$C(=O)NR$^{134}$C(=O)R$^{130}$, —NR$^{134}$C(=O)NR$^{134}$C(=O)OR$^{130}$, —NR$^{134}$C(=NR$^{135}$)NR$^{132}$R$^{133}$, —NR$^{134}$C(=O)C(=O)NR$^{132}$R$^{133}$, —NR$^{134}$C(=S)R$^{130}$, —NR$^{134}$C(=S)OR$^{130}$, —NR$^{134}$C(=S)NR$^{132}$R$^{133}$, —NR$^{134}$S(=O)$_2$R$^{131}$, —NR$^{134}$S(=O)$_2$NR$^{132}$R$^{133}$, —OR$^{130}$, =O, —OCN, —OC(=O)R$^{130}$, —OC(=O)NR$^{132}$R$^{133}$, —OC(=O)OR$^{130}$, —OC(=NR$^{135}$)NR$^{132}$R$^{133}$, —OS(=O)R$^{130}$, —OS(=O)$_2$R$^{130}$, —OS(=O)$_2$OR$^{130}$, —OS(=O)$_2$NR$^{132}$R$^{133}$, —SCN, =S, —S(=O)$_n$R$^{130}$, —S(=O)$_2$OR$^{130}$, —SO$_3$R$^{137}$, —S(=O)$_2$NR$^{132}$R$^{133}$, and —S(=O)NR$^{132}$R$^{133}$. In another embodiment, Z$^2$ is H, C$_{1-6}$alkyl optionally substituted by 1-13 R$^{89}$, C$_{6-11}$aryl optionally substituted by 1-7 R$^{89}$, C$_{7-16}$arylalkyl optionally substituted by 1-19 R$^{89}$, C$_{3-11}$cycloalkyl optionally substituted by 1-21 R$^{89}$, C$_{4-17}$cycloalkylalkyl optionally substituted by 1-32 R$^{89}$, 3-15 membered heterocycloalkyl optionally substituted by 1-28 R$^{89}$, 4-21 membered heterocycloalkylalkyl optionally substituted by 1-40 R$^{89}$, 5-15 membered heteroaryl optionally substituted by 1-15 R$^{89}$, 6-21 membered heteroarylalkyl optionally substituted by 1-27 R$^{89}$, halogen, —CN, —C(=O)R$^{80}$, —C(=O)OR$^{80}$, —C(=O)NR$^{82}$R$^{83}$, —C(=O)C(=O)R$^{80}$, —C(=S)NR$^{82}$R$^{83}$, —NC, —NO$_2$, —NR$^{82}$R$^{83}$, —NR$^{84}$NR$^{82}$R$^{83}$, —NR$^{84}$C(=O)R$^{80}$, —NR$^{84}$C(=O)C(=O)R$^{80}$, —NR$^{84}$C(=O)OR$^{81}$, —NR$^{84}$C(=O)C(=O)OR$^{81}$, —NR$^{84}$C(=O)NR$^{82}$R$^{83}$, —NR$^{84}$C(=O)NR$^{84}$C(=O)R$^{80}$, —NR$^{84}$C(=O)NR$^{84}$C(=O)OR$^{80}$, —NR$^{84}$C(=NR$^{85}$)NR$^{82}$R$^{83}$, —NR$^{84}$C(=O)C(=O)NR$^{82}$R$^{83}$, —NR$^{84}$C(=S)R$^{80}$, —NR$^{84}$C(=S)OR$^{80}$, —NR$^{84}$C(=S)NR$^{82}$R$^{83}$, —NR$^{84}$S(=O)$_2$R$^{81}$, —NR$^{84}$S(=O)$_2$NR$^{82}$R$^{83}$, —OR$^{80}$, =O, —OCN, —OC(=O)R$^{80}$, —OC(=O)NR$^{82}$R$^{83}$, —OC(=O)OR$^{80}$, —OS(=O)R$^{80}$, —OS(=O)$_2$R$^{80}$, —OS(=O)$_2$OR$^{80}$, —OS(=O)$_2$NR$^{82}$R$^{83}$, —SCN, =S, —S(=O)$_n$R$^{80}$, —S(=O)$_2$OR$^{80}$, —SO$_3$R$^{87}$, —S(=O)$_2$NR$^{82}$R$^{83}$, or —S(=O)NR$^{82}$R$^{83}$; alternatively, when L$^2$, A$^2$, G$^2$, X$^2$, L$^3$, A$^3$, G$^3$ and X$^3$ are absent, Z$^2$ and Z$^3$ can together form a group of formula -A$^{21}$-A$^{22}$-A$^{23}$-, wherein A$^{21}$, A$^{22}$, and A$^{23}$ are independently chosen from —CZ$^{21}$Z$^{22}$—, —CZ$^{23}$Z$^{24}$CZ$^{25}$Z$^{26}$—, —C(=O)—, —NZ$^{27}$—, —S—, —S(=O)—, —S(=O)$_2$—, or —O—; wherein:

(a) when any two of $Z^{21}$, $Z^{22}$, $Z^{23}$, $Z^{24}$, $Z^{25}$, $Z^{26}$ and $Z^{27}$ are located on adjacent atoms, they may together form a bond between the atoms, and (b) any of $Z^{21}$, $Z^{22}$, $Z^{23}$, $Z^{24}$, $Z^{25}$, $Z^{26}$ and $Z^{27}$ may be independently chosen from H, C$_{1-6}$alkyl optionally substituted by 1-13 R$^{99}$, C$_{6-11}$ aryl optionally substituted by 1-7 R$^{99}$, C$_{7-16}$arylalkyl optionally substituted by 1-19 R$^{99}$, C$_{3-11}$cycloalkyl optionally substituted by 1-21 R$^{99}$, C$_{4-17}$cycloalkylalkyl optionally substituted by 1-32 R$^{99}$, 3-15 membered heterocycloalkyl optionally substituted by 1-28 R$^{99}$, 4-21 membered heterocycloalkylalkyl optionally substituted by 1-40 R$^{99}$, 5-15 membered heteroaryl optionally substituted by 1-15 R$^{99}$, 6-21 membered heteroarylalkyl optionally substituted by 1-27 R$^{99}$, halogen, —CN, —C(=O)R$^{90}$, —C(=O)OR$^{90}$, —C(=O)NR$^{92}$R$^{93}$, —C(=O)C(=O)R$^{90}$, —C(=S)NR$^{92}$R$^{93}$, —NC, —NO$_2$, —NR$^{92}$R$^{93}$, —NR$^{94}$NR$^{92}$R$^{93}$, —NR$^{94}$C(=O)R$^{90}$, —NR$^{94}$C(=O)C(=O)R$^{90}$, —NR$^{94}$C(=O)OR$^{91}$, —NR$^{94}$C(=O)C(=O)OR$^{91}$, —NR$^{94}$C(=O)NR$^{92}$R$^{93}$, —NR$^{94}$C(=O)NR$^{94}$C(=O)R$^{90}$, —NR$^{94}$C(=O)NR$^{94}$C(=O)OR$^{90}$, —NR$^{94}$C(=NR$^{9}$)NR$^{92}$R$^{93}$, —NR$^{94}$C(=O)C(=O)NR$^{92}$R$^{93}$, —NR$^{94}$C(=S)R$^{90}$, —NR$^{94}$C(=S)OR$^{90}$, —NR$^{94}$C(=S)NR$^{92}$R$^{93}$, —NR$^{94}$S(=O)$_2$R$^{91}$, —NR$^{94}$S(=O)$_2$NR$^{92}$R$^{93}$, —OR$^{90}$, =O, —OCN, —OC(=O)R$^{90}$, —OC(=O)NR$^{92}$R$^{93}$, —OC(=O)OR$^{90}$, —OS(=O)R$^{90}$, —OS(=O)$_2$R$^{90}$, —OS(=O)$_2$OR$^{90}$, —OS(=O)$_2$NR$^{92}$R$^{93}$, —SCN, =S, —S(=O)$_n$R$^{90}$, —S(=O)$_2$OR$^{90}$, —SO$_3$R$^{97}$, —S(=O)$_2$NR$^{92}$R$^{93}$, and —S(=O)NR$^{92}$R$^{93}$; and (c) any two of $Z^{21}$, $Z^{22}$, $Z^{23}$, $Z^{24}$, $Z^{25}$, $Z^{26}$ and $Z^{27}$ may together form a group of formula -A$^{31}$-A$^{32}$-A$^{33}$-, wherein A$^{31}$, A$^{32}$, and A$^{33}$ are independently chosen from —CZ$^{31}$Z$^{32}$—, —CZ$^{33}$Z$^{34}$CZ$^{35}$Z$^{36}$—, —C(=O)—, —NZ$^{37}$—, —S—, —S(=O)—, —S(=O)$_2$—, or —O— wherein:

(i) when any two of $Z^{31}$, $Z^{32}$, $Z^{33}$, $Z^{34}$, $Z^{35}$, $Z^{36}$ and $Z^{37}$ are located on adjacent atoms, they may together form a bond between the atoms, and (ii) any of any of $Z^{21}$, $Z^{22}$, $Z^{23}$, $Z^{24}$, $Z^{25}$, $Z^{26}$ and $Z^{27}$ may be independently chosen from H, C$_{1-6}$alkyl optionally substituted by 1-13 R$^{139}$, C$_{6-11}$ aryl optionally substituted by 1-7 R$^{139}$, C$_{7-16}$arylalkyl optionally substituted by 1-19 R$^{139}$, C$_{3-11}$cycloalkyl optionally substituted by 1-21 R$^{139}$, C$_{4-17}$cycloalkylalkyl optionally substituted by 1-32 R$^{139}$, 3-15 membered heterocycloalkyl optionally substituted by 1-28 R$^{139}$, 4-21 membered heterocycloalkylalkyl optionally substituted by 1-40 R$^{139}$, 5-15 membered heteroaryl optionally substituted by 1-15 R$^{139}$, 6-21 membered heteroarylalkyl optionally substituted by 1-27 R$^{139}$, halogen, —CN, —C(=O)R$^{130}$, —C(=O)OR$^{130}$, —C(=O)NR$^{132}$R$^{133}$, —C(=O)C(=O)R$^{130}$, —C(=S)NR$^{132}$R$^{133}$, —NC, —NO$_2$, —NR$^{132}$R$^{133}$, —NR$^{134}$NR$^{132}$R$^{133}$, —NR$^{134}$C(=O)R$^{130}$, —NR$^{134}$C(=O)C(=O)R$^{130}$, —NR$^{134}$C(=O)OR$^{131}$, —NR$^{134}$C(=O)C(=O)OR$^{131}$, —NR$^{134}$C(=O)NR$^{132}$R$^{133}$, —NR$^{134}$C(=O)NR$^{134}$C(=O)R$^{130}$, —NR$^{134}$C(=O)NR$^{134}$C(=O)OR$^{130}$, —NR$^{134}$C(=NR$^{135}$)NR$^{132}$R$^{133}$, —NR$^{134}$C(=O)C(=O)NR$^{132}$R$^{133}$, —NR$^{134}$C(=S)R$^{130}$, —NR$^{134}$C(=S)OR$^{130}$, —NR$^{134}$C(=S)NR$^{132}$R$^{133}$, —NR$^{134}$S(=O)$_2$R$^{131}$, —NR$^{134}$S(=O)$_2$NR$^{132}$R$^{133}$, —OR$^{130}$, =O, —OCN, —OC(=O)R$^{130}$, —OC(=O)NR$^{132}$R$^{133}$, —OC(=O)OR$^{130}$, —OS(=O)R$^{130}$, —OS(=O)$_2$R$^{130}$, —OS(=O)$_2$OR$^{130}$, —OS(=O)$_2$NR$^{132}$R$^{133}$, —SCN, =S, —S(=O)$_n$R$^{130}$, —S(=O)$_2$OR$^{130}$, —SO$_3$R$^{137}$, —S(=O)$_2$NR$^{132}$R$^{133}$, and —S(=O)NR$^{132}$R$^{133}$. In another embodiment, Z$^2$ is H, C$_{1-6}$alkyl optionally substituted by 1-13 R$^{89}$, C$_{6-11}$aryl optionally substituted by 1-7 R$^{89}$, C$_{7-16}$arylalkyl optionally substituted by 1-19 R$^{89}$, C$_{3-11}$cycloalkyl optionally substituted by 1-21 R$^{89}$, C$_{4-17}$cycloalkylalkyl optionally substituted by 1-32 R$^{89}$, 3-15 membered heterocycloalkyl optionally substituted by 1-28 R$^{89}$, 4-21 membered heterocycloalkylalkyl optionally substituted by 1-40 R$^{89}$, 5-15 membered heteroaryl optionally substituted by 1-15 R$^{89}$, 6-21 membered heteroarylalkyl optionally substituted by 1-27 R$^{89}$, halogen, —CN, —C(=O)R$^{80}$, —C(=O)OR$^{80}$, —C(=O)NR$^{82}$R$^{83}$, —C(=S)NR$^{82}$R$^{83}$, —NC, —NO$_2$, —NR$^{82}$R$^{83}$, —NR$^{84}$NR$^{82}$R$^{83}$, —NR$^{84}$C(=O)R$^{80}$, —NR$^{84}$C(=O)OR$^{81}$, —NR$^{84}$C(=O)NR$^{82}$R$^{83}$, —NR$^{84}$C(=O)NR$^{84}$C(=)R$^{80}$, —NR$^{84}$C(=O)NR$^{84}$C(=O)R$^{80}$, —NR$^{84}$C(=NR$^{85}$)NR$^{82}$R$^{83}$, —NR$^{84}$C(=O)NR$^{84}$C(=O) R$^{80}$, —NR$^{84}$C(=O)NR$^{84}$C(=O)OR$^{80}$, —NR$^{84}$C(=NR$^{85}$) NR$^{82}$R$^{83}$, —NR$^{84}$C(=S)R$^{80}$, —NR$^{84}$C(=S)NR$^{82}$R$^{83}$, —NR$^{84}$S(O)$_2$R$^{81}$, —NR$^{84}$P(=O)R$^{88}$R$^{88}$, —OR$^{80}$, =O, —OCN, —OC(=O)R$^{80}$, —OC(=O)NR$^{82}$R$^{83}$, —SCN, =S, —S(=O)$_n$R$^{80}$, —S(=O)$_2$OR$^{80}$, —S(=O)$_2$NR$^{82}$R$^{83}$, or —P(=O)R$^{88}$R$^{88}$; alternatively, when L$^2$, A$^2$, G$^2$, X$^2$, L$^3$, A$^3$, G$^3$ and X$^3$ are absent, Z$^2$ and Z$^3$ can together form a group of formula -A$^{21}$-A$^{22}$-A$^{23}$-, wherein A$^{21}$, A$^{22}$, and A$^{23}$ are independently chosen from —CZ$^{21}$Z$^{22}$—, —CZ$^{23}$Z$^{24}$CZ$^{25}$Z$^{26}$—, —C(=O)—, —NZ$^{27}$—, —S—, —S(=O)—, —S(=O)$_2$—, or —O—; wherein:

(a) when any two of Z$^{21}$, Z$^{22}$, Z$^{23}$, Z$^{24}$, Z$^{25}$, Z$^{26}$ and Z$^{27}$ are located on adjacent atoms, they may together form a bond between the atoms, and (b) any of Z$^{21}$, Z$^{22}$, Z$^{23}$, Z$^{24}$, Z$^{25}$, Z$^{26}$ and Z$^{27}$ may be independently chosen from H, C$_{1-6}$alkyl optionally substituted by 1-13 R$^{99}$, C$_{6-11}$ aryl optionally substituted by 1-7 R$^{99}$, C$_{7-16}$arylalkyl optionally substituted by 1-19 R$^{99}$, C$_{3-11}$cycloalkyl optionally substituted by 1-21 R$^{99}$, C$_{4-17}$cycloalkylalkyl optionally substituted by 1-32 R$^{99}$, 3-15 membered heterocycloalkyl optionally substituted by 1-28 R$^{99}$, 4-21 membered heterocycloalkylalkyl optionally substituted by 1-40 R$^{99}$, 5-15 membered heteroaryl optionally substituted by 1-15 R$^{99}$, 6-21 membered heteroarylalkyl optionally substituted by 1-27 R$^{99}$, halogen, —CN, —C(=O)R$^{90}$, —C(=O)OR$^{90}$, —C(=O)NR$^{92}$R$^{93}$, —C(=S)NR$^{92}$R$^{93}$, —NC, —NO$_2$, —NR$^{92}$R$^{93}$, —NR$^{94}$NR$^{92}$R$^{93}$, —NR$^{94}$C (=O)R$^{90}$, —NR$^{94}$C(=O)OR$^{91}$, —NR$^{94}$C(=O)NR$^{92}$R$^{93}$, —NR$^{94}$C(=O)NR$^{94}$C(=O)R$^{90}$, —NR$^{94}$C(=O)NR$^{94}$ (=O)OR$^{90}$, —NR$^{94}$C(=NR$^{95}$)NR$^{92}$R$^{93}$, —NR$^{94}$C(=S) R$^{90}$,—NR$^{94}$C(=S)NR$^{92}$R$^{93}$, —NR$^{94}$S(=O)$_2$R$^{91}$, —NR$^{94}$P (=O)R$^{98}$R$^{98}$, —OR$^{90}$, =O, —OCN, —OC(=O)NR$^{92}$R$^{93}$, —SCN, =S, —S(=O)$_n$R$^{90}$, —S(=O)$_2$NR$^{92}$R$^{93}$, and —P(=O)R$^{98}$R$^{98}$; and (c) any two of Z$^{21}$, Z$^{22}$, Z$^{23}$, Z$^{24}$, Z$^{25}$, Z$^{26}$ and Z$^{27}$ may together form a group of formula -A$^{31}$-A$^{32}$-A$^{33}$-, wherein A$^{31}$, A$^{32}$, and A$^{33}$ are independently chosen from —CZ$^{31}$Z$^{32}$—, —CZ$^{33}$Z$^{34}$CZ$^{35}$Z$^{36}$—, —C(=O)—, —NZ$^{37}$—, —S—, —S(=O)—, —S(=O)$_2$—, or —O— wherein:

(i) when any two of Z$^{31}$, Z$^{32}$, Z$^{33}$, Z$^{34}$, Z$^{35}$, Z$^{36}$ and Z$^{37}$ are located on adjacent atoms, they may together form a bond between the atoms, and (ii) any of any of Z$^{21}$, Z$^{22}$, Z$^{23}$, Z$^{24}$, Z$^{25}$, Z$^{26}$ and Z$^{27}$ may be independently chosen from H, C$_{1-6}$alkyl optionally substituted by 1-13 R$^{139}$, C$_{6-11}$ aryl optionally substituted by 1-7 R$^{139}$, C$_{7-16}$ arylalkyl optionally substituted by 1-19 R$^{139}$, C$_{3-11}$cycloalkyl optionally substituted by 1-21 R$^{139}$, C$_{4-17}$cycloalkylalkyl optionally substituted by 1-32 R$^{139}$, 3-15 membered heterocycloalkyl optionally substituted by 1-28 R$^{139}$, 4-21 membered heterocycloalkylalkyl optionally substituted by 1-40 R$^{139}$, 5-15 membered heteroaryl optionally substituted by 1-15 R$^{139}$, 6-21 membered heteroarylalkyl optionally substituted by 1-27 R$^{139}$, halogen, —CN, —C(=O)R$^{130}$, —C(=O)OR$^{130}$, —C(=O)NR$^{132}$R$^{133}$, —C(=S) NR$^{132}$R$^{133}$, —NC, —NO$_2$, —NR$^{132}$R$^{133}$, —NR$^{134}$NR$^{132}$R$^{133}$, —NR$^{134}$C(=O)R$^{130}$, —NR$^{134}$C(=O) OR$^{131}$, —NR$^{134}$C(=O)NR$^{132}$R$^{133}$, —NR$^{134}$C(=O) NR$^{134}$C(=O)R$^{130}$, —NR$^{134}$C(=NR$^{135}$)NR$^{132}$R$^{133}$, —NR$^{134}$C(=S)R$^{130}$, —NR$^{134}$C(=S)NR$^{132}$R$^{133}$, —NR$^{134}$S(=O)$_2$R$^{131}$, —NR$^{134}$P(=O)R$^{138}$R$^{138}$, —OR$^{130}$, =O, —OCN, —OC(=O)R$^{130}$, —OC(=O)NR$^{132}$R$^{133}$, —SCN, =S, —S(=O)$_n$R$^{130}$, —S(=O)$_2$NR$^{132}$R$^{133}$, and —P(=O)R$^{138}$R$^{138}$. In another embodiment, Z$^2$ is H, C$_{1-6}$alkyl optionally substituted by 1-13 R$^{89}$, C$_{6-11}$ aryl optionally substituted by 1-7 R$^{89}$, C$_{7-16}$arylalkyl optionally substituted by 1-19 R$^{89}$, C$_{3-11}$cycloalkyl optionally substituted by 1-21 R$^{89}$, C$_{4-17}$cycloalkylalkyl optionally substituted by 1-32 R$^{89}$, 3-15 membered heterocycloalkyl optionally substituted by 1-28 R$^{89}$, 4-21 membered heterocycloalkylalkyl optionally substituted by 1-40 R$^{89}$, 5-15 membered heteroaryl optionally substituted by 1-15 R$^{89}$, 6-21 membered heteroarylalkyl optionally substituted by 1-27 R$^{89}$, halogen, —CN, —C(=O)R$^{80}$, —C(=O)OR$^{80}$, —C(=O)NR$^{82}$R$^{83}$, —C(=S)NR$^{82}$R$^{83}$, —NC, —NO$_2$, —NR$^{82}$R$^{83}$, —NR$^{84}$NR$^{82}$R$^{83}$, —NR$^{84}$C(=O)R$^{80}$, —NR$^{84}$C(=O)OR$^{81}$, —NR$^{84}$C(=O)NR$^{82}$R$^{83}$, —NR$^{84}$C (=O)NR$^{84}$C(=O)R$^{80}$, —NR$^{84}$C(=O)NR$^{84}$C(=O)OR$^{80}$, —NR$^{84}$C(=NR$^{85}$)NR$^{82}$R$^{83}$, —NR$^{84}$C(=S)R$^{80}$, —NR$^{84}$C (=S)NR$^{82}$R$^{83}$, —NR$^{84}$S(=O)$_2$R$^{81}$, —OR$^{80}$, =O, —OCN, —OC(=O)R$^{80}$, —OC(=O)NR$^{82}$R$^{83}$, —SCN, =S, —S(=O)$_n$R$^{80}$, —S(=O)$_2$OR$^{80}$, or —S(=O)$_2$NR$^{82}$R$^{83}$; alternatively, when L$^2$, A$^2$, G$^2$, X$^2$, L$^3$, A$^3$, G$^3$ and X$^3$ are absent, Z$^2$ and Z$^3$ can together form a group of formula -A$^{21}$-A$^{22}$-A$^{23}$-, wherein A$^{21}$, A$^{22}$, and A$^{23}$ are independently chosen from —CZ$^{21}$Z$^{22}$—, —CZ$^{23}$Z$^{24}$CZ$^{25}$Z$^{26}$—, —C(=O)—, —NZ$^{27}$—, —S—, —S(=O)—, —S(=)$_2$—, or —O—; wherein:

(a) when any two of Z$^{21}$, Z$^{22}$, Z$^{23}$, Z$^{24}$, Z$^{25}$, Z$^{26}$ and Z$^{27}$ are located on adjacent atoms, they may together form a bond between the atoms, and (b) any of Z$^{21}$, Z$^{22}$, Z$^{23}$, Z$^{24}$, Z$^{25}$, Z$^{26}$ and Z$^{27}$ may be independently chosen from H, C$_{1-6}$alkyl optionally substituted by 1-13 R$^{99}$, C$_{6-11}$ aryl optionally substituted by 1-7 R$^{99}$, C$_{7-16}$arylalkyl optionally substituted by 1-19 R$^{99}$, C$_{3-11}$cycloalkyl optionally substituted by 1-21 R$^{99}$, C$_{4-17}$cycloalkylalkyl optionally substituted by 1-32 R$^{99}$, 3-15 membered heterocycloalkyl optionally substituted by 1-28 R$^{99}$, 4-21 membered heterocycloalkylalkyl optionally substituted by 1-40 R$^{99}$, 5-15 membered heteroaryl optionally substituted by 1-15 R$^{99}$, 6-21 membered heteroarylalkyl optionally substituted by 1-27 R$^{99}$, halogen, —CN, —C(=O)R$^{90}$, —C(=O)OR$^{90}$, —C(=O)NR$^{92}$R$^{93}$, —C(=S)NR$^{92}$R$^{93}$, —NC, —NO$_2$, —NR$^{92}$R$^{93}$, —NR$^{94}$NR$^{92}$R$^{93}$, —NR$^{94}$C (=O)R$^{90}$, —NR$^{94}$C(=O)OR$^{91}$, —NR$^{94}$C(=O)NR$^{92}$R$^{93}$, —NR$^{94}$C(=O)NR$^{94}$C(=O)R$^{90}$, —NR$^{94}$C(=O)NR$^{94}$ (=O)OR$^{90}$, —NR$^{94}$C(=NR$^{95}$)NR$^{92}$R$^{93}$, —NR$^{94}$C(=S) R$^{90}$, —NR$^{94}$C(=S)NR$^{92}$R$^{93}$, —NR$^{94}$S(=O)$_2$R$^{91}$, —OR$^{90}$, =O, —OCN, —OC(=O)NR$^{92}$R$^{93}$, —SCN, =S, —S(=O)$_n$ R$^{90}$, and —S(=O)$_2$NR$^{92}$R$^{93}$; and (c) any two of Z$^{21}$, Z$^{22}$, Z$^{23}$, Z$^{24}$, Z$^{25}$, Z$^{26}$ and Z$^{27}$ may together form a group of formula -A$^{31}$-A$^{32}$-A$^{33}$-, wherein A$^{31}$, A$^{32}$, and A$^{33}$ are independently chosen from —$CZ^{31}Z^{32}$—, —$CZ^{33}Z^{34}CZ^{35}Z^{36}$—, —$C(=O)$—, —$NZ^{37}$—, —S—, —$S(=O)$—, —$S(=O)_2$—, or —O— wherein:

(i) when any two of $Z^{31}$, $Z^{32}$, $Z^{33}$, $Z^{34}$, $Z^{35}$, $Z^{36}$ and $Z^{37}$ are located on adjacent atoms, they may together form a bond between the atoms, and (ii) any of any of $Z^{21}$, $Z^{22}$, $Z^{23}$, $Z^{24}$, $Z^{25}$, $Z^{26}$ and $Z^{27}$ may be independently chosen from H, $C_{1-6}$alkyl optionally substituted by 1-13 $R^{139}$, $C_{6-11}$ aryl optionally substituted by 1-7 $R^{139}$, $C_{7-16}$arylalkyl optionally substituted by 1-19 $R^{139}$, $C_{3-11}$cycloalkyl optionally substituted by 1-21 $R^{139}$, $C_{4-17}$cycloalkylalkyl optionally substituted by 1-32 $R^{139}$, 3-15 membered heterocycloalkyl optionally substituted by 1-28 $R^{139}$, 4-21 membered heterocycloalkylalkyl optionally substituted by 1-40 $R^{139}$, 5-15 membered heteroaryl optionally substituted by 1-15 $R^{139}$, 6-21 membered heteroarylalkyl optionally substituted by 1-27 $R^{139}$, halogen, —CN, —$C(=O)R^{130}$, —$C(=O)OR^{130}$, —$C(=O)NR^{132}R^{133}$, —$C(=S)NR^{132}R^{133}$, —NC, —$NO_2$, —$NR^{132}R^{133}$, —$NR^{134}NR^{132}R^{133}$, —$NR^{134}C(=O)R^{130}$, —$NR^{134}C(=O)OR^{131}$, —$NR^{134}C(=O)NR^{132}R^{133}$, —$NR^{134}C(=O)NR^{134}C(=O)R^{130}$, —$NR^{134}C(=NR^{135})NR^{132}R^{133}$, —$NR^{134}C(=S)R^{130}$, —$NR^{134}C(=S)NR^{132}R^{133}$, —$NR^{134}S(=O)_2R^{131}$, —$OR^{130}$, =O, —OCN, —$OC(=O)R^{130}$, —$OC(=O)NR^{132}R^{133}$, —SCN, =S, —$S(=O)_nR^{130}$, and —$S(=O)_2NR^{132}R^{133}$. In another embodiment, $Z^2$ is H, $C_{1-6}$alkyl optionally substituted by 1-13 $R^{89}$, $C_{6-11}$aryl optionally substituted by 1-7 $R^{89}$, $C_{7-16}$arylalkyl optionally substituted by 1-19 $R^{89}$, $C_{3-11}$cycloalkyl optionally substituted by 1-21 $R^{89}$, $C_{4-17}$cycloalkylalkyl optionally substituted by 1-32 $R^{89}$, 3-15 membered heterocycloalkyl optionally substituted by 1-28 $R^{89}$, 4-21 membered heterocycloalkylalkyl optionally substituted by 1-40 $R^{89}$, 5-15 membered heteroaryl optionally substituted by 1-15 $R^{89}$, 6-21 membered heteroarylalkyl optionally substituted by 1-27 $R^{89}$, halogen, —CN, —$C(=O)R^{80}$, —$C(=O)OR^{80}$, —$C(=O)NR^{82}R^{83}$, —$C(=S)NR^{82}R^{83}$, —$NR^{82}R^{83}$, —$NR^{84}C(=O)R^{80}$, —$NR^{84}C(=O)OR^{81}$, —$NR^{84}C(=O)NR^{82}R^{83}$, —$NR^{84}C(=O)NR^{84}C(=O)R^{80}$, —$NR^{84}C(=O)NR^{84}C(=O)OR^{80}$, —$NR^{84}C(=S)R^{80}$, —$NR^{84}S(=O)_2R^{81}$, —$OR^{80}$, =O, —$OC(=O)R^{80}$, —$OC(=O)NR^{82}R^{83}$, =S, —$S(=O)_nR^{80}$, or —$S(=O)_2NR^{82}R^{83}$; alternatively, when $L^2$, $A^2$, $G^2$, $X^2$, $L^3$, $A^3$, $G^3$ and $X^3$ are absent, $Z^2$ and $Z^3$ can together form a group of formula -$A^{21}$-$A^{22}$-$A^{23}$-, wherein $A^{21}$, $A^{22}$, and $A^{23}$ are independently chosen from —$CZ^{21}Z^{22}$—, —$CZ^{23}Z^{24}CZ^{25}Z^{26}$—, —$C(=O)$—, —$NZ^{27}$—, —S—, —$S(=O)$—, —$S(=O)_2$—, or —O—; wherein:

(a) when any two of $Z^{21}$, $Z^{22}$, $Z^{23}$, $Z^{24}$, $Z^{25}$, $Z^{26}$ and $Z^{27}$ are located on adjacent atoms, they may together form a bond between the atoms, and (b) any of $Z^{21}$, $Z^{22}$, $Z^{23}$, $Z^{24}$, $Z^{25}$, $Z^{26}$ and $Z^{27}$ may be independently chosen from H, $C_{1-6}$alkyl optionally substituted by 1-13 $R^{99}$, $C_{6-11}$aryl optionally substituted by 1-7 $R^{99}$, $C_{7-16}$arylalkyl optionally substituted by 1-19 $R^{99}$, $C_{3-11}$cycloalkyl optionally substituted by 1-21 $R^{99}$, $C_{4-17}$cycloalkylalkyl optionally substituted by 1-32 $R^{99}$, 3-15 membered heterocycloalkyl optionally substituted by 1-28 $R^{99}$, 4-21 membered heterocycloalkylalkyl optionally substituted by 1-40 $R^{99}$, 5-15 membered heteroaryl optionally substituted by 1-15 $R^{99}$, 6-21 membered heteroarylalkyl optionally substituted by 1-27 $R^{99}$, halogen, —CN, —$C(=O)R^{90}$, —$C(=O)OR^{90}$, —$C(=O)NR^{92}R^{93}$, —$C(=S)NR^{92}R^{93}$, —$NR^{92}R^{93}$, —$NR^{94}C(=O)R^{90}$, —$NR^{94}C(=O)OR^{91}$, —$NR^{94}C(=O)NR^{92}R^{93}$, —$NR^{94}C(=O)NR^{94}C(=O)R^{90}$, —$NR^{94}C(=O)NR^{94}C(=O)OR^{90}$, —$NR^{94}C(=S)R^{90}$, —$NR^{94}S(=O)_2R^{91}$, —$OR^{90}$, =O, —$OC(=O)R^{90}$, —$OC(=O)NR^{92}R^{93}$, =S, —$S(=O)_nR^{90}$, and —$S(=O)_2NR^{92}R^{93}$; and (c) any two of $Z^{21}$, $Z^{22}$, $Z^{23}$, $Z^{24}$, $Z^{25}$, $Z^{26}$ and $Z^{27}$ may together form a group of formula -$A^{31}$-$A^{32}$-$A^{33}$-, wherein $A^{31}$, $A^{32}$, and $A^{33}$ are independently chosen from —$CZ^{31}Z^{32}$—, —$CZ^{33}Z^{34}CZ^{35}Z^{36}$—, —$C(=O)$—, —$NZ^{37}$—, —S—, —$S(=O)$—, —$S(=O)_2$—, or —O— wherein:

(i) when any two of $Z^{31}$, $Z^{32}$, $Z^{33}$, $Z^{34}$, $Z^{35}$, $Z^{36}$ and $Z^{37}$ are located on adjacent atoms, they may together form a bond between the atoms, and (ii) any of any of $Z^{21}$, $Z^{22}$, $Z^{23}$, $Z^{24}$, $Z^{25}$, $Z^{26}$ and $Z^{27}$ may be independently chosen from H, $C_{1-6}$alkyl optionally substituted by 1-13 $R^{139}$, $C_{6-11}$ aryl optionally substituted by 1-7 $R^{139}$, $C_{7-16}$arylalkyl optionally substituted by 1-19 $R^{139}$, $C_{3-11}$cycloalkyl optionally substituted by 1-21 $R^{139}$, $C_{4-17}$cycloalkylalkyl optionally substituted by 1-32 $R^{139}$, 3-15 membered heterocycloalkyl optionally substituted by 1-28 $R^{139}$, 4-21 membered heterocycloalkylalkyl optionally substituted by 1-40 $R^{139}$, 5-15 membered heteroaryl optionally substituted by 1-15 $R^{139}$, 6-21 membered heteroarylalkyl optionally substituted by 1-27 $R^{139}$, halogen, —CN, —$C(=O)R^{130}$, —$C(=O)OR^{130}$, —$C(=O)NR^{132}R^{133}$, —$C(=S)NR^{132}R^{133}$, —$NR^{132}R^{133}$, —$NR^{134}C(=O)R^{130}$, —$NR^{134}C(=O)OR^{131}$, —$NR^{134}C(=O)NR^{132}R^{133}$, —$NR^{134}C(=O)NR^{134}C(=O)R^{130}$, —$NR^{134}C(=S)R^{130}$, —$NR^{134}S(=O)_2R^{131}$, —$OR^{130}$, =O, —OCN, —$OC(=O)R^{130}$, —$OC(=O)NR^{132}R^{133}$, =S, —$S(=O)_nR^{130}$, and —$S(=O)_2NR^{132}R^{133}$. In another embodiment, $Z^2$ is H, $C_{1-6}$alkyl optionally substituted by 1-13 $R^{89}$, $C_{6-11}$ aryl optionally substituted by 1-7 $R^{89}$, $C_{7-16}$arylalkyl optionally substituted by 1-19 $R^{89}$, $C_{3-11}$cycloalkyl optionally substituted by 1-21 $R^{89}$, $C_{4-17}$cycloalkylalkyl optionally substituted by 1-32 $R^{89}$, 3-15 membered heterocycloalkyl optionally substituted by 1-28 $R^{89}$, 4-21 membered heterocycloalkylalkyl optionally substituted by 1-40 $R^{89}$, 5-15 membered heteroaryl optionally substituted by 1-15 $R^{89}$, 6-21 membered heteroarylalkyl optionally substituted by 1-27 $R^{89}$, halogen, —CN, —$C(=O)R^{80}$, —$C(=O)OR^{80}$, —$C(=O)NR^{82}R^{83}$, —$NR^{82}R^{83}$, —$NR^{84}C(=)R^{80}$, —$NR^{84}C(=O)OR^{81}$, —$NR^{84}C(=O)NR^{82}R^{83}$, —$NR^{84}S(=O)_2R^{81}$, —$NR^{84}P(=O)R^{88}R^{88}$, —$OR^{80}$, =O, —$OC(=O)R^{80}$, —$OC(=O)NR^{82}R^{83}$, =S, —$S(=O)_nR^{80}$, —$S(=O)_2NR^{82}R^{83}$, or —$P(=O)R^{88}R^{88}$; alternatively, when $L^2$, $A^2$, $G^2$, $X^2$, $L^3$, $A^3$, $G^3$ and $X^3$ are absent, $Z^2$ and $Z^3$ can together form a group of formula -$A^{21}$-$A^{22}$-$A^{23}$-, wherein $A^{21}$, $A^{22}$, and $A^{23}$ are independently chosen from —$CZ^{21}Z^{22}$—, —$CZ^{23}Z^{24}CZ^{25}Z^{26}$—, or —$NZ^{27}$—; wherein:

(a) when any two of $Z^{21}$, $Z^{22}$, $Z^{23}$, $Z^{24}$, $Z^{25}$, $Z^{26}$ and $Z^{27}$ are located on adjacent atoms, they may together form a bond between the atoms, and (b) any of $Z^{21}$, $Z^{22}$, $Z^{23}$, $Z^{24}$, $Z^{25}$, $Z^{26}$ and $Z^{27}$ may be independently chosen from H, $C_{1-6}$alkyl optionally substituted by 1-13 $R^{99}$, $C_{6-11}$ aryl optionally substituted by 1-7 $R^{99}$, $C_{7-16}$arylalkyl optionally substituted by 1-19 $R^{99}$, $C_{3-11}$cycloalkyl optionally substituted by 1-21 $R^{99}$, $C_{4-17}$cycloalkylalkyl optionally substituted by 1-32 $R^{99}$, 3-15 membered heterocycloalkyl optionally substituted by 1-28 $R^{99}$, 4-21 membered heterocycloalkylalkyl optionally substituted by 1-40 $R^{99}$, 5-15 membered heteroaryl optionally substituted by 1-15 $R^{99}$, 6-21 membered heteroarylalkyl optionally substituted by 1-27 $R^{99}$, halogen, —CN, —$C(=O)R^{90}$, —$C(=O)OR^{90}$, —$C(=O)NR^{92}R^{93}$, —$NR^{92}R^{93}$, —$NR^{94}C(=O)R^{90}$, —$NR^{94}C(=O)OR^{91}$, —$NR^{94}C(=O)NR^{92}R^{93}$, —$NR^{94}S(=O)_2R^{91}$, —$NR^{94}P(=O)R^{98}R^{98}$, —$OR^{90}$, =O, —OC(=O)R$^{90}$, —OC(=O)NR$^{92}$R$^{93}$, =S, —S(=O)$_n$R$^{90}$, —S(=O)$_2$NR$^{92}$R$^{93}$, and —P(=O)R$^{98}$R$^{98}$; and (c) any two of Z$^{21}$, Z$^{22}$, Z$^{23}$, Z$^{24}$, Z$^{25}$, Z$^{26}$ and Z$^{27}$ may together form a group of formula -A$^{31}$-A$^{32}$-A$^{33}$-, wherein A$^{31}$, A$^{32}$, and A$^{33}$ are independently chosen from —CZ$^{31}$Z$^{32}$—, —CZ$^{33}$Z$^{34}$CZ$^{35}$Z$^{36}$—, or —NZ$^{37}$— wherein:

(i) when any two of Z$^{31}$, Z$^{32}$, Z$^{33}$, Z$^{34}$, Z$^{35}$, Z$^{36}$ and Z$^{37}$ are located on adjacent atoms, they may together form a bond between the atoms, and (ii) any of any of Z$^{21}$, Z$^{22}$, Z$^{23}$, Z$^{24}$, Z$^{25}$, Z$^{26}$ and Z$^{27}$ may be independently chosen from H, C$_{1-6}$alkyl optionally substituted by 1-13 R$^{139}$, C$_{6-11}$aryl optionally substituted by 1-7 R$^{139}$, C$_{7-16}$arylalkyl optionally substituted by 1-19 R$^{139}$, C$_{3-11}$cycloalkyl optionally substituted by 1-21 R$^{139}$, C$_{4-17}$cycloalkylalkyl optionally substituted by 1-32 R$^{139}$, 3-15 membered heterocycloalkyl optionally substituted by 1-28 R$^{139}$, 4-21 membered heterocycloalkylalkyl optionally substituted by 1-40 R$^{139}$, 5-15 membered heteroaryl optionally substituted by 1-15 R$^{139}$, 6-21 membered heteroarylalkyl optionally substituted by 1-27 R$^{139}$, halogen, —CN, —C(=O)R$^{130}$, —C(=O)OR$^{130}$, —C(=O)NR$^{132}$R$^{133}$, —NR$^{132}$R$^{133}$, —NR$^{134}$C(=O)R$^{130}$, —NR$^{134}$C(=O)OR$^{131}$, —NR$^{134}$C(=O)NR$^{132}$R$^{133}$, —NR$^{134}$S(=O)$_2$R$^{131}$, —OR$^{130}$, =O, —OCN, —OC(=O)R$^{130}$, —OC(=O)NR$^{132}$R$^{133}$, =S, —S(=O)$_n$R$^{130}$, and —S(=O)$_2$NR$^{132}$R$^{133}$. In another embodiment, Z$^2$ is H, C$_{1-6}$alkyl optionally substituted by 1-13 R$^{89}$, C$_{6-11}$aryl optionally substituted by 1-7 R$^{89}$, C$_{7-16}$arylalkyl optionally substituted by 1-19 R$^{89}$, C$_{3-11}$cycloalkyl optionally substituted by 1-21 R$^{89}$, C$_{4-17}$cycloalkylalkyl optionally substituted by 1-32 R$^{89}$, 3-15 membered heterocycloalkyl optionally substituted by 1-28 R$^{89}$, 4-21 membered heterocycloalkylalkyl optionally substituted by 1-40 R$^{89}$, 5-15 membered heteroaryl optionally substituted by 1-15 R$^{89}$, 6-21 membered heteroarylalkyl optionally substituted by 1-27 R$^{89}$, halogen, —CN, —C(=O)R$^{80}$, —C(=O)OR$^{80}$, —C(=O)NR$^{82}$R$^{83}$, —C(=S)NR$^{82}$R$^{83}$, —NR$^{82}$R$^{83}$, —NR$^{84}$C(=O)R$^{80}$, —NR$^{84}$C(=O)OR$^{81}$, —NR$^{84}$C(=O)NR$^{82}$R$^{83}$, —NR$^{84}$C(=O)NR$^{84}$C(=O)R$^{80}$, —NR$^{84}$C(=O)NR$^{84}$C(=O)OR$^{80}$, —NR$^{84}$C(=S)R$^{80}$, —NR$^{84}$S(=O)$_2$R$^{81}$, —OR$^{80}$, =O, —OC(=O)R$^{80}$, —OC(=O)NR$^{82}$R$^{83}$, =S, —S(=O)$_n$R$^{80}$, or —S(=O)$_2$NR$^{82}$R$^{83}$; alternatively, when L$^2$, A$^2$, G$^2$, X$^2$, L$^3$, A$^3$, G$^3$ and X$^3$ are absent, Z$^2$ and Z$^3$ can together form a group of formula -A$^{21}$-A$^{22}$-A$^{23}$-, wherein A$^{21}$, A$^{22}$, and A$^{23}$ are independently chosen from —CZ$^{21}$Z$^{22}$—, —CZ$^{23}$Z$^{24}$CZ$^{25}$Z$^{26}$—, —C(=O)—, —NZ$^{27}$—, —S—, —S(=O)—, —S(=O)$_2$—, or —O—; wherein:

(a) when any two of Z$^{21}$, Z$^{22}$, Z$^{23}$, Z$^{24}$, Z$^{25}$, Z$^{26}$ and Z$^{27}$ are located on adjacent atoms, they may together form a bond between the atoms, and (b) any of Z$^{21}$, Z$^{22}$, Z$^{23}$, Z$^{24}$, Z$^{25}$, Z$^{26}$ and Z$^{27}$ may be independently chosen from H, C$_{1-6}$alkyl optionally substituted by 1-13 R$^{99}$, C$_{6-11}$ aryl optionally substituted by 1-7 R$^{99}$, C$_{7-16}$arylalkyl optionally substituted by 1-19 R$^{99}$, C$_{3-11}$cycloalkyl optionally substituted by 1-21 R$^{99}$, C$_{4-17}$cycloalkylalkyl optionally substituted by 1-32 R$^{99}$, 3-15 membered heterocycloalkyl optionally substituted by 1-28 R$^{99}$, 4-21 membered heterocycloalkylalkyl optionally substituted by 1-40 R$^{99}$, 5-15 membered heteroaryl optionally substituted by 1-15 R$^{99}$, 6-21 membered heteroarylalkyl optionally substituted by 1-27 R$^{99}$, halogen, —CN, —C(=O)R$^{90}$, —C(=O)OR$^{90}$, —C(=O)NR$^{92}$R$^{93}$, —C(=S)NR$^{92}$R$^{93}$, —NR$^{92}$R$^{93}$, —NR$^{94}$C(=O)R$^{90}$, —NR$^{94}$C(=O)OR$^{91}$, —NR$^{94}$C(=O)NR$^{92}$R$^{93}$, —NR$^{94}$C(=O)NR$^{94}$C(=)R$^{90}$, —NR$^{94}$C(=O)NR$^{94}$C(=O)OR$^{90}$, —NR$^{94}$C(=S)R$^{90}$, —NR$^{94}$S(=O)$_2$R$^{91}$, —OR$^{90}$, =O, —OC(=O)R$^{90}$, —OC(=O)NR$^{92}$R$^{93}$, =S, —S(=O)$_n$R$^{90}$, and —S(=O)$_2$NR$^{92}$R$^{93}$; and (c) any two of Z$^{21}$, Z$^{22}$, Z$^{23}$, Z$^{24}$, Z$^{25}$, Z$^{26}$ and Z$^{27}$ may together form a group of formula -A$^{31}$-A$^{32}$-A$^{33}$-, wherein A$^{31}$, A$^{32}$, and A$^{33}$ are independently chosen from —CZ$^{31}$Z$^{32}$—, —CZ$^{33}$Z$^{34}$CZ$^{35}$Z$^{36}$—, —C(=O)—, —NZ$^{37}$—, —S—, —S(=O)—, —S(=O)$_2$—, or —O— wherein:

(i) when any two of Z$^{31}$, Z$^{32}$, Z$^{33}$, Z$^{34}$, Z$^{35}$, Z$^{36}$ and Z$^{37}$ are located on adjacent atoms, they may together form a bond between the atoms, and (ii) any of any of Z$^{21}$, Z$^{22}$, Z$^{23}$, Z$^{24}$, Z$^{25}$, Z$^{26}$ and Z$^{27}$ may be independently chosen from H, C$_{1-6}$alkyl optionally substituted by 1-13 R$^{139}$, C$_{6-11}$ aryl optionally substituted by 1-7 R$^{139}$, C$_{7-16}$arylalkyl optionally substituted by 1-19 R$^{139}$, C$_{3-11}$cycloalkyl optionally substituted by 1-21 R$^{139}$, C$_{4-17}$cycloalkylalkyl optionally substituted by 1-32 R$^{139}$, 3-15 membered heterocycloalkyl optionally substituted by 1-28 R$^{139}$, 4-21 membered heterocycloalkylalkyl optionally substituted by 1-40 R$^{139}$, 5-15 membered heteroaryl optionally substituted by 1-15 R$^{139}$, 6-21 membered heteroarylalkyl optionally substituted by 1-27 R$^{139}$, halogen, —CN, —C(=O)R$^{130}$, —C(=O)OR$^{130}$, —C(=O)NR$^{132}$R$^{133}$, —C(=S)NR$^{132}$R$^{133}$, —NR$^{132}$R$^{133}$, —NR$^{134}$C(=O)R$^{130}$, —NR$^{134}$C(=O)OR$^{131}$, —NR$^{134}$C(=O)NR$^{132}$R$^{133}$, —NR$^{134}$C(=O)NR$^{134}$C(=O)R$^{130}$, —NR$^{134}$C(=S)R$^{130}$, —NR$^{134}$S(=O)$_2$R$^{131}$, —OR$^{130}$, =O, —OCN, —OC(=O)R$^{130}$, —OC(=O)NR$^{132}$R$^{133}$, =S, —S(=O)$_n$R$^{130}$, and —S(=O)$_2$NR$^{132}$R$^{133}$. In another embodiment, Z$^2$ is H, C$_{1-6}$alkyl optionally substituted by 1-13 R$^{89}$, C$_{6-11}$aryl optionally substituted by 1-7 R$^{89}$, C$_{7-16}$arylalkyl optionally substituted by 1-19 R$^{89}$, C$_{3-11}$cycloalkyl optionally substituted by 1-21 R$^{89}$, 3-15 membered heterocycloalkyl optionally substituted by 1-28 R$^{89}$, 5-15 membered heteroaryl optionally substituted by 1-15 R$^{89}$, halogen, —CN, —C(=O)R$^{80}$, —C(=O)OR$^{80}$, —C(=O)NR$^{82}$R$^{83}$, —NR$^{82}$R$^{83}$, —NR$^{84}$C(=O)R$^{80}$, —NR$^{84}$C(=O)OR$^{81}$, —NR$^{84}$C(=O)NR$^{82}$R$^{83}$, —NR$^{84}$S(=O)$_2$R$^{81}$, —NR$^{84}$P(=O)R$^{88}$R$^{88}$, —OR$^{80}$, =O, —OC(=O)R$^{80}$, —OC(=O)NR$^{82}$R$^{83}$, =S, —S(=O)$_n$R$^{80}$, —S(=O)$_2$NR$^{82}$R$^{83}$, or —P(=O)R$^{88}$R$^{88}$; alternatively, when L$^2$, A$^2$, G$^2$, X$^2$, L$^3$, A$^3$, G$^3$ and X$^3$ are absent, Z$^2$ and Z$^3$ can together form a group of formula -A$^{21}$-A$^{22}$-A$^{23}$-, wherein A$^{21}$, A$^{22}$, and A$^{23}$ are independently chosen from —CZ$^{21}$Z$^{22}$—, —CZ$^{23}$Z$^{24}$CZ$^{25}$Z$^{26}$—, or —NZ$^{27}$—; wherein:

(a) when any two of Z$^{21}$, Z$^{22}$, Z$^{23}$, Z$^{24}$, Z$^{25}$, Z$^{26}$ and Z$^{27}$ are located on adjacent atoms, they may together form a bond between the atoms, and (b) any of Z$^{21}$, Z$^{22}$, Z$^{23}$, Z$^{24}$, Z$^{25}$, Z$^{26}$ and Z$^{27}$ may be independently chosen from H, C$_{1-6}$alkyl optionally substituted by 1-13 R$^{99}$, C$_{6-11}$ aryl optionally substituted by 1-7 R$^{99}$, C$_{3-11}$cycloalkyl optionally substituted by 1-21 R$^{99}$, 3-15 membered heterocycloalkyl optionally substituted by 1-28 R$^{99}$, 5-15 membered heteroaryl optionally substituted by 1-15 R$^{99}$, halogen, —CN, —C(=O)R$^{90}$, —C(=O)OR$^{90}$, —C(=O)NR$^{92}$R$^{93}$, —NR$^{92}$R$^{93}$, —NR$^{94}$C(=O)R$^{90}$, —NR$^{94}$C(=O)OR$^{91}$, —NR$^{94}$C(=O)NR$^{92}$R$^{93}$, —NR$^{94}$S(=O)$_2$R$^{91}$, —NR$^{94}$P(=O)R$^{98}$R$^{98}$, —OR$^{90}$, =O, —OC(=O)R$^{90}$, —OC(=O)NR$^{92}$R$^{93}$, =S, —S(=O)$_n$R$^{90}$, —S(=O)$_2$NR$^{92}$R$^{93}$, and —P(=O)R$^{98}$R$^{98}$. In another embodiment, Z$^2$ is H, C$_{1-6}$alkyl optionally substituted by 1-13 R$^{89}$, C$_{6-11}$aryl optionally substituted by 1-7 R$^{89}$, C$_{7-16}$arylalkyl optionally substituted by 1-19 R$^{89}$, C$_{3-11}$cycloalkyl optionally substituted by 1-21 R$^{89}$, 3-15 membered heterocycloalkyl optionally substituted by 1-28 R$^{89}$, 5-15 membered heteroaryl optionally substituted by 1-15 R$^{89}$, halogen, —CN, —C(=O)R$^{80}$, —C(=O)OR$^{80}$, —C(=O)NR$^{82}$R$^{83}$, —NR$^{82}$R$^{83}$, —NR$^{84}$C(=O)R$^{80}$, —NR$^{84}$C(=O)OR$^{81}$, —NR$^{84}$C(=O)NR$^{82}$R$^{83}$, —NR$^{84}$S(=O)$_2$R$^{81}$, —OR$^{80}$, =O, —OC(=O)R$^{80}$, —OC(=O)NR$^{82}$R$^{83}$, =S, —S(=O)$_n$R$^{80}$, or —S(=O)$_2$NR$^{82}$R$^{83}$; alternatively, when L$^2$, A$^2$, G$^2$, X$^2$, L$^3$, A$^3$, G$^3$ and X$^3$ are absent, Z$^2$ and Z$^3$ can together form a group of formula -A$^{21}$-A$^{22}$-A$^{23}$-, wherein A$^{21}$, A$^{22}$, and A$^{23}$ are independently chosen from —CZ$^{21}$Z$^{22}$—, —CZ$^{23}$Z$^{24}$CZ$^{25}$Z$^{26}$—, or —NZ$^{27}$—; wherein:

(a) when any two of Z$^{21}$, Z$^{22}$, Z$^{23}$, Z$^{24}$, Z$^{25}$, Z$^{26}$ and Z$^{27}$ are located on adjacent atoms, they may together form a bond between the atoms, and (b) any of Z$^{21}$, Z$^{22}$, Z$^{23}$, Z$^{24}$, Z$^{25}$, Z$^{26}$ and Z$^{27}$ may be independently chosen from H, C$_{1-6}$alkyl optionally substituted by 1-13 R$^{99}$, C$_{6-11}$aryl optionally substituted by 1-7 R$^{99}$, C$_{3-11}$cycloalkyl optionally substituted by 1-21 R$^{99}$, 3-15 membered heterocycloalkyl optionally substituted by 1-28 R$^{99}$, 5-15 membered heteroaryl optionally substituted by 1-15 R$^{99}$, halogen, —CN, —C(=O)R$^{90}$, —C(=O)OR$^{90}$, —C(=O)NR$^{92}$R$^{93}$, —C(=O)C(=O)R$^{90}$, —C(=S)NR$^{92}$R$^{93}$, —NC, —NO$_2$, —NR$^{92}$R$^{93}$, —NR$^{94}$NR$^{92}$R$^{93}$, —NR$^{94}$C(=O)R$^{90}$, —NR$^{94}$C(=O)C(=O)R$^{90}$, —NR$^{94}$C(=O)OR$^{91}$, —NR$^{94}$C(=O)C(=O)OR$^{91}$, —NR$^{94}$C(=O)NR$^{92}$R$^{93}$, —NR$^{94}$C(=O)NR$^{94}$C(=O)R$^{90}$, —NR$^{94}$C(=O)OR$^{90}$, —NR$^{94}$C(=S)NR$^{92}$R$^{93}$, —NR$^{94}$C(=O)C(=O)NR$^{92}$R$^{93}$, —NR$^{94}$C(=S)R$^{90}$, —NR$^{94}$C(=S)OR$^{90}$, —NR$^{94}$C(=S)NR$^{92}$R$^{93}$, —NR$^{94}$S(=O)$_2$R$^{91}$, are independently chosen from —CZ$^{21}$Z$^{22}$—, —CZ$^{23}$Z$^{24}$CZ$^{25}$Z$^{26}$—, or —NZ$^{27}$—; wherein:

(a) when any two of Z$^{21}$, Z$^{22}$, Z$^{23}$, Z$^{24}$, Z$^{25}$, Z$^{26}$ and Z$^{27}$ are located on adjacent atoms, they may together form a bond between the atoms, and (b) any of Z$^{21}$, Z$^{22}$, Z$^{23}$, Z$^{24}$, Z$^{25}$, Z$^{26}$ and Z$^{27}$ may be independently chosen from H, C$_{1-6}$alkyl optionally substituted by 1-13 R$^{99}$, C$_{6-11}$aryl optionally substituted by 1-7 R$^{99}$, C$_{3-11}$cycloalkyl optionally substituted by 1-21 R$^{99}$, 3-15 membered heterocycloalkyl optionally substituted by 1-28 R$^{99}$, 5-15 membered heteroaryl optionally substituted by 1-15 R$^{99}$, halogen, —CN, —C(=O)R$^{90}$, —C(=O)OR$^{90}$, —C(=O)NR$^{92}$R$^{93}$, —NR$^{92}$R$^{93}$, —NR$^{94}$C(=O)R$^{90}$, —NR$^{94}$C(=O)OR$^{91}$, —NR$^{94}$C(=O)NR$^{92}$R$^{93}$, —NR$^{94}$S(=O)$_2$R$^{91}$, —OR$^{90}$, =O, —OC(=O)R$^{90}$, —OC(=O)NR$^{92}$R$^{93}$, =S, —S(=O)$_n$R$^{90}$, and —S(=O)$_2$NR$^{92}$R$^{93}$. In another embodiment, Z$^2$ is H, C$_{1-6}$alkyl optionally substituted by 1-6 R$^{89}$, C$_{6-11}$aryl optionally substituted by 1-6 R$^{89}$, C$_{7-16}$arylalkyl optionally substituted by 1-6 R$^{89}$, C$_{3-11}$cycloalkyl optionally substituted by 1-6 R$^{89}$, C$_{4-17}$cycloalkylalkyl optionally substituted by 1-6 R$^{89}$, 3-15 membered heterocycloalkyl optionally substituted by 1-6 R$^{89}$, 4-21 membered heterocycloalkylalkyl optionally substituted by 1-6 R$^{89}$, 5-15 membered heteroaryl optionally substituted by 1-6 R$^{89}$, 6-21 membered heteroarylalkyl optionally substituted by 1-6 R$^{89}$, halogen, —CN, —C(=O)R$^{80}$, —C(=O)OR$^{80}$, —C(=O)NR$^{82}$R$^{83}$, —C(=O)C(=O)R$^{80}$, —C(=S)NR$^{82}$R$^{83}$, —NC, —NO$_2$, —NR$^{82}$R$^{83}$, —NR$^{84}$NR$^{82}$R$^{83}$, —NR$^{84}$C(=O)R$^{80}$, —NR$^{84}$C(=O)C(=O)R$^{80}$, —NR$^{84}$C(=O)OR$^{81}$, —NR$^{84}$C(=O)C(=O)OR$^{81}$, —NR$^{84}$C(=O)NR$^{82}$R$^{83}$, —NR$^{84}$C(=O)NR$^{84}$C(=O)R$^{80}$, —NR$^{84}$C(=O)NR$^{84}$C(=O)OR$^{80}$, —NR$^{84}$C(=NR$^{85}$)NR$^{82}$R$^{83}$, —NR$^{84}$C(=O)C(=O)NR$^{82}$R$^{83}$, —NR$^{84}$C(=S)R$^{80}$, —NR$^{84}$C(=S)OR$^{80}$, —NR$^{84}$C(=S)NR$^{82}$R$^{83}$, —NR$^{84}$S(=O)$_2$R$^{81}$, —NR$^{84}$S(=O)$_2$NR$^{82}$R$^{83}$, —NR$^{84}$P(=O)R$^{88}$R$^{88}$, —OR$^{80}$, =O, —OCN, —OC(=O)R$^{80}$, —OC(=O)NR$^{82}$R$^{83}$, —OC(=O)OR$^{80}$, —OS(=O)R$^{80}$, —OS(=O)$_2$R$^{80}$, —OS(=O)$_2$OR$^{80}$, —OS(=O)$_2$NR$^{82}$R$^{83}$, —SCN, =S, —S(=O)$_n$R$^{80}$, —S(=O)$_2$OR$^{80}$, —SO$_3$R$^{87}$, —S(=O)$_2$NR$^{82}$R$^{83}$, —S(=O)NR$^{82}$R$^{83}$, or —P(=O)R$^{88}$R$^{88}$; alternatively, when L$^2$, A$^2$, G$^2$, X$^2$, L$^3$, A$^3$, G$^3$ and X$^3$ are absent, Z$^2$ and Z$^3$ can together form a group of formula -A$^{21}$-A$^{22}$-A$^{23}$-; wherein A$^{21}$, A$^{22}$, and A$^{23}$ are independently chosen from —CZ$^{21}$Z$^{22}$—, —CZ$^{23}$Z$^{24}$CZ$^{25}$Z$^{26}$—, —C(=O)—, —NZ$^{27}$—, —S—, —S(=O)—, —S(=O)$_2$—, or —O—; wherein:

(a) when any two of Z$^{21}$, Z$^{22}$, Z$^{23}$, Z$^{24}$, Z$^{25}$, Z$^{26}$ and Z$^{27}$ are located on adjacent atoms, they may together form a bond between the atoms, and (b) any of Z$^{21}$, Z$^{22}$, Z$^{23}$, Z$^{24}$, Z$^{25}$, Z$^{26}$ and Z$^{27}$ may be independently chosen from H, C$_{1-6}$alkyl optionally substituted by 1-6 R$^{99}$, C$_{6-11}$ aryl optionally substituted by 1-7 R$^{99}$, C$_{7-16}$arylalkyl optionally substituted by 1-6 R$^{99}$, C$_{3-11}$cycloalkyl optionally substituted by 1-6 R$^{99}$, C$_{4-17}$cycloalkylalkyl optionally substituted by 1-6 R$^{99}$, 3-15 membered heterocycloalkyl optionally substituted by 1-6 R$^{99}$, 4-21 membered heterocycloalkylalkyl optionally substituted by 1-6 R$^{99}$, 5-15 membered heteroaryl optionally substituted by 1-6 R$^{99}$, 6-21 membered heteroarylalkyl optionally substituted by 1-6 R$^{99}$, halogen, —CN, —C(=O)R$^{90}$, —C(=O)OR$^{90}$, —C(=O)NR$^{92}$R$^{93}$, —C(=O)C(=O)R$^{90}$, —C(=S)NR$^{92}$R$^{93}$, —NC, —NO$_2$, —NR$^{92}$R$^{93}$, —NR$^{94}$NR$^{92}$R$^{93}$, —NR$^{94}$C(=O)R$^{90}$, —NR$^{94}$C(=O)C(=O)R$^{90}$, —NR$^{94}$C(=O)OR$^{91}$, —NR$^{94}$C(=O)C(=O)OR$^{91}$, —NR$^{94}$C(=O)NR$^{92}$R$^{93}$, —NR$^{94}$C(=O)NR$^{94}$C(=O)R$^{90}$, —NR$^{94}$C(=O)OR$^{90}$, —NR$^{94}$C(=S)NR$^{92}$R$^{93}$, —NR$^{94}$C(=O)C(=O)NR$^{92}$R$^{93}$, —NR$^{94}$C(=S)R$^{90}$, —NR$^{94}$C(=S)OR$^{90}$, —NR$^{94}$C(=S)NR$^{92}$R$^{93}$, —NR$^{94}$S(=O)$_2$R$^{91}$, —NR$^{94}$S(=O)$_2$NR$^{92}$R$^{93}$, —NR$^{94}$P(=O)R$^{98}$R$^{98}$, —OR$^{90}$, =O, —OCN, —OC(=O)R$^{90}$, —OC(=O)NR$^{92}$R$^{93}$, —OC(=O)OR$^{90}$, —OS(=O)R$^{90}$, —OS(=O)$_2$R$^{90}$, —OS(=O)$_2$OR$^{90}$, —OS(=O)$_2$NR$^{92}$R$^{93}$, —SCN, =S, —S(=O)$_n$R$^{90}$, —S(=O)$_2$OR$^{90}$, —SO$_3$R$^{97}$, —S(=O)$_2$NR$^{92}$R$^{93}$, —S(=O)NR$^{92}$R$^{93}$, and —P(=O)R$^{98}$R$^{98}$; and (c) any two of Z$^{21}$, Z$^{22}$, Z$^{23}$, Z$^{24}$, Z$^{25}$, Z$^{26}$ and Z$^{27}$ may together form a group of formula -A$^{31}$-A$^{32}$-A$^{33}$-, wherein A$^{31}$, A$^{32}$, and A$^{33}$ are independently chosen from —CZ$^{31}$Z$^{32}$—, —CZ$^{33}$Z$^{34}$CZ$^{35}$Z$^{36}$—, —C(=O)—, —NZ$^{37}$—, —S—, —S(=O)—, —S(=O)$_2$—, or —O—
wherein:

(i) when any two of Z$^{31}$, Z$^{32}$, Z$^{33}$, Z$^{34}$, Z$^{35}$, Z$^{36}$ and Z$^{37}$ are located on adjacent atoms, they may together form a bond between the atoms, and (ii) any of any of Z$^{21}$, Z$^{22}$, Z$^{23}$, Z$^{24}$, Z$^{25}$, Z$^{26}$ and Z$^{27}$ may be independently chosen from H, C$_{1-6}$alkyl optionally substituted by 1-6 R$^{139}$, C$_{6-11}$aryl optionally substituted by 1-7 R$^{139}$, C$_{7-16}$arylalkyl optionally substituted by 1-6 R$^{139}$, C$_{3-11}$cycloalkyl optionally substituted by 1-6 R$^{139}$, C$_{4-17}$cycloalkylalkyl optionally substituted by 1-6 R$^{139}$, 3-15 membered heterocycloalkyl optionally substituted by 1-6 R$^{139}$, 4-21 membered heterocycloalkylalkyl optionally substituted by 1-6 R$^{139}$, 5-15 membered heteroaryl optionally substituted by 1-6 R$^{139}$, 6-21 membered heteroarylalkyl optionally substituted by 1-6 R$^{139}$, halogen, —CN, —C(=O)R$^{130}$, —C(=O)OR$^{130}$, —C(=O)NR$^{132}$R$^{133}$, —C(=O)C(=O)R$^{130}$, —C(=S)NR$^{132}$R$^{133}$, —NC, —NO$_2$, —NR$^{132}$R$^{133}$, —NR$^{134}$NR$^{132}$R$^{133}$, —NR$^{134}$C(=O)R$^{130}$, —NR$^{134}$C(=O)C(=O)R$^{130}$, —NR$^{134}$C(=O)OR$^{131}$, —NR$^{134}$C(=O)C(=O)OR$^{131}$, —NR$^{134}$C(=O)NR$^{132}$R$^{133}$, —NR$^{134}$C(=O)NR$^{134}$C(=O)R$^{130}$, —NR$^{134}$C(=O)NR$^{134}$C(=O)OR$^{130}$, —NR$^{134}$C(=NR$^{135}$)NR$^{132}$R$^{133}$, —NR$^{134}$C(=O)C(=O)NR$^{132}$R$^{133}$, —NR$^{134}$C(=S)R$^{130}$, —NR$^{134}$C(=S)OR$^{130}$, —NR$^{134}$C(=S)NR$^{132}$R$^{133}$, —NR$^{134}$S(=O)$_2$R$^{131}$, —NR$^{134}$S(=O)$_2$NR$^{132}$R$^{133}$, —NR$^{134}$P(=O)R$^{138}$R$^{138}$, —OR$^{130}$, =O, —OCN, —OC(=O)R$^{130}$, —OC(=O)NR$^{132}$R$^{133}$, —OC(=O)OR$^{130}$, —OS(=O)R$^{130}$, —OS(=O)$_2$R$^{130}$, —OS(=O)$_2$OR$^{130}$, —OS(=O)$_2$NR$^{132}$R$^{133}$, —SCN, =S, —S(=O)$_n$R$^{130}$, —S(=O)$_2$OR$^{130}$, —SO$_3$R$^{137}$, —S(=O)$_2$NR$^{132}$R$^{133}$, —S(=O)NR$^{132}$R$^{133}$, and —P(=O)R$^{138}$R$^{138}$. In another embodiment, Z$^2$ is H, C$_{1-6}$alkyl optionally substituted by 1-6 R$^{89}$, C$_{6-11}$ aryl optionally substituted by 1-6 R$^{89}$, C$_{7-16}$arylalkyl optionally substituted by 1-6 R$^{89}$, C$_{3-11}$cycloalkyl optionally substituted by 1-6 R$^{89}$, C$_{4-17}$cycloalkylalkyl optionally substituted by 1-6 R$^{89}$, 3-15 membered heterocycloalkyl optionally substituted by 1-6 R$^{89}$, 4-21 membered heterocycloalkylalkyl optionally substituted by 1-6 R$^{89}$, 5-15 membered heteroaryl optionally substituted by 1-6 R$^{89}$, 6-21 membered heteroarylalkyl optionally substituted by 1-6 R$^{89}$, halogen, —CN, —C(=O)R$^{80}$, —C(=O)OR$^{80}$, —C(=O)NR$^{82}$R$^{83}$, —C(=O)C(=O)R$^{80}$, —C(=S)NR$^{82}$R$^{83}$, —NC, —NO$_2$, —NR$^{82}$R$^{83}$, —NR$^{84}$NR$^{82}$R$^{83}$, —NR$^{84}$C(=O)R$^{80}$, —NR$^{84}$C(=O)C(=O)R$^{80}$, —NR$^{84}$C(=O)OR$^{81}$, —NR$^{84}$C(=O)C(=O)OR$^{81}$, —NR$^{84}$C(=O)NR$^{82}$R$^{83}$, —NR$^{84}$C(=O)NR$^{84}$C(=O)R$^{80}$, —NR$^{84}$C(=O)NR$^{84}$C(=O)OR$^{80}$, —NR$^{84}$C(=NR$^{85}$)NR$^{82}$R$^{83}$, —NR$^{84}$C(=O)C(=O)NR$^{82}$R$^{83}$, —NR$^{84}$C(=S)R$^{80}$, —NR$^{84}$C(=S)OR$^{80}$, —NR$^{84}$C(=S)NR$^{82}$R$^{83}$, —NR$^{84}$S(=O)$_2$R$^{81}$, —NR$^{84}$S(=O)$_2$NR$^{82}$R$^{83}$, —OR$^{80}$, =O, —OCN, —OC(=O)R$^{80}$, —OC(=O)NR$^{82}$R$^{83}$, —OC(=O)OR$^{80}$, —OS(=O)R$^{80}$, —OS(=O)$_2$R$^{80}$, —OS(=O)$_2$OR$^{80}$, —OS(=O)$_2$NR$^{82}$R$^{83}$, —SCN, =S, —S(=O)$_n$R$^{80}$, —S(=O)$_2$OR$^{80}$, —SO$_3$R$^{87}$, —S(=O)$_2$NR$^{82}$R$^{83}$, or —S(=O)NR$^{82}$R$^{83}$; alternatively, when L$^2$, A$^2$, G$^2$, X$^2$, L$^3$, A$^3$, G$^3$ and X$^3$ are absent, Z$^2$ and Z$^3$ can together form a group of formula -A$^{21}$-A$^{22}$-A$^{23}$-; wherein A$^{21}$, A$^{22}$, and A$^{23}$ are independently chosen from —CZ$^{21}$Z$^{22}$—, —CZ$^{23}$Z$^{24}$CZ$^{25}$Z$^{26}$—, —C(=O)—, —NZ$^{27}$—, —S—, —S(=O)—, —S(=O)$_2$—, or —O—;
wherein:

(a) when any two of Z$^{21}$, Z$^{22}$, Z$^{23}$, Z$^{24}$, Z$^{25}$, Z$^{26}$ and Z$^{27}$ are located on adjacent atoms, they may together form a bond between the atoms, and (b) any of Z$^{21}$, Z$^{22}$, Z$^{23}$, Z$^{24}$, Z$^{25}$, Z$^{26}$ and Z$^{27}$ may be independently chosen from H, C$_{1-6}$alkyl optionally substituted by 1-6 R$^{99}$, C$_{6-11}$aryl optionally substituted by 1-7 R$^{99}$, C$_{7-16}$arylalkyl optionally substituted by 1-6 R$^{99}$, C$_{3-11}$cycloalkyl optionally substituted by 1-6 R$^{99}$, C$_{4-17}$cycloalkylalkyl optionally substituted by 1-6 R$^{99}$, 3-15 membered heterocycloalkyl optionally substituted by 1-6 R$^{99}$, 4-21 membered heterocycloalkylalkyl optionally substituted by 1-6 R$^{99}$, 5-15 membered heteroaryl optionally substituted by 1-6 R$^{99}$, 6-21 membered heteroarylalkyl optionally substituted by 1-6 R$^{99}$, halogen, —CN, —C(=O)R$^{90}$, —C(=O)OR$^{90}$, —C(=O)NR$^{92}$R$^{93}$, —C(=O)C(=O)R$^{90}$, —C(=S)NR$^{92}$R$^{93}$, —NC, —NO$_2$, —NR$^{92}$R$^{93}$, —NR$^{94}$NR$^{92}$R$^{93}$, —NR$^{94}$C(=O)R$^{90}$, —NR$^{94}$C(=O)C(=O)R$^{90}$, —NR$^{94}$C(=O)OR$^{91}$, —NR$^{94}$C(=O)C(=O)OR$^{91}$, —NR$^{94}$C(=O)NR$^{92}$R$^{93}$, —NR$^{94}$C(=O)NR$^{94}$C(=O)R$^{90}$, —NR$^{94}$C(=O)NR$^{94}$C(=O)OR$^{90}$, —NR$^{94}$C(=NR$^{95}$)NR$^{92}$R$^{93}$, —NR$^{94}$C(=O)C(=O)NR$^{92}$R$^{93}$, —NR$^{94}$C(=S)R$^{90}$, —NR$^{94}$C(=S)OR$^{90}$, —NR$^{94}$C(=S)NR$^{92}$R$^{93}$, —NR$^{94}$S(=O)$_2$R$^{91}$, —NR$^{94}$S(=O)$_2$NR$^{92}$R$^{93}$, —OR$^{90}$, =O, —OCN, —OC(=O)R$^{90}$, —OC(=O)NR$^{92}$R$^{93}$, —OC(=O)OR$^{90}$, —OS(=O)R$^{90}$, —OS(=O)$_2$R$^{90}$, —OS(=O)$_2$OR$^{90}$, —OS(=O)$_2$NR$^{92}$R$^{93}$, —SCN, =S, —S(=O)$_n$R$^{90}$, —S(=O)$_2$OR$^{90}$, —SO$_3$R$^{97}$, —S(=O)$_2$NR$^{92}$R$^{93}$, and —S(=O)NR$^{92}$R$^{93}$; and (c) any two of Z$^{21}$, Z$^{22}$, Z$^{23}$, Z$^{24}$, Z$^{25}$, Z$^{26}$ and Z$^{27}$ may together form a group of formula -A$^{31}$-A$^{32}$-A$^{33}$-, wherein A$^{31}$, A$^{32}$, and A$^{33}$ are independently chosen from —CZ$^{31}$Z$^{32}$—, —CZ$^{33}$Z$^{34}$CZ$^{35}$Z$^{36}$—, —C(=O)—, —NZ$^{37}$—, —S—, —S(=O)—, —S(=O)$_2$—, or —O—
wherein:

(i) when any two of Z$^{31}$, Z$^{32}$, Z$^{33}$, Z$^{34}$, Z$^{35}$, Z$^{36}$ and Z$^{37}$ are located on adjacent atoms, they may together form a bond between the atoms, and (ii) any of any of Z$^{21}$, Z$^{22}$, Z$^{23}$, Z$^{24}$, Z$^{25}$, Z$^{26}$ and Z$^{27}$ may be independently chosen from H, C$_{1-6}$alkyl optionally substituted by 1-6 R$^{139}$, C$_{6-11}$aryl optionally substituted by 1-7 R$^{139}$, C$_{7-16}$arylalkyl optionally substituted by 1-6 R$^{139}$, C$_{3-11}$cycloalkyl optionally substituted by 1-6 R$^{139}$, C$_{4-17}$cycloalkylalkyl optionally substituted by 1-6 R$^{139}$, 3-15 membered heterocycloalkyl optionally substituted by 1-6 R$^{139}$, 4-21 membered heterocycloalkylalkyl optionally substituted by 1-6 R$^{139}$, 5-15 membered heteroaryl optionally substituted by 1-6 R$^{139}$, 6-21 membered heteroarylalkyl optionally substituted by 1-6 R$^{139}$, halogen, —CN, —C(=O)R$^{130}$, —C(=O)OR$^{130}$, —C(=O)NR$^{132}$R$^{133}$, —C(=O)C(=O)R$^{130}$, —C(=S)NR$^{132}$R$^{133}$, —NC, —NO$_2$, —NR$^{132}$R$^{133}$, —NR$^{134}$NR$^{132}$R$^{133}$, —NR$^{134}$C(=O)R$^{130}$, —NR$^{134}$C(=O)C(=O)R$^{130}$, —NR$^{134}$C(=O)OR$^{131}$, —NR$^{134}$C(=O)C(=O)OR$^{131}$, —NR$^{134}$C(=O)NR$^{132}$R$^{133}$, —NR$^{134}$C(=O)NR$^{134}$C(=O)R$^{130}$, —NR$^{134}$C(=O)NR$^{134}$C(=O)OR$^{130}$, —NR$^{134}$C(=NR$^{135}$)NR$^{132}$R$^{133}$, —NR$^{134}$C(=O)C(=O)NR$^{132}$R$^{133}$, —NR$^{134}$C(=S)R$^{130}$, —NR$^{134}$C(=S)OR$^{130}$, —NR$^{134}$C(=S)NR$^{132}$R$^{133}$, —NR$^{134}$S(=O)$_2$R$^{131}$, —NR$^{134}$S(=O)$_2$NR$^{132}$R$^{133}$, —OR$^{130}$, =O, —OCN, —OC(=O)R$^{130}$, —OC(=O)NR$^{132}$R$^{133}$, —OC(=O)OR$^{130}$, —OS(=O)R$^{130}$, —OS(=O)$_2$R$^{130}$, —OS(=O)$_2$OR$^{130}$, —OS(=O)$_2$NR$^{132}$R$^{133}$, —SCN, =S, —S(=O)$_n$R$^{130}$, —S(=O)$_2$OR$^{130}$, —SO$_3$R$^{137}$, —S(=O)$_2$NR$^{132}$R$^{133}$, and —S(=O)NR$^{132}$R$^{133}$. In another embodiment, Z$^2$ is H, C$_{1-6}$alkyl optionally substituted by 1-6 R$^{89}$, C$_{6-11}$aryl optionally substituted by 1-7 R$^{89}$, C$_{7-16}$arylalkyl optionally substituted by 1-6 $R^{89}$, $C_{3-11}$cycloalkyl optionally substituted by 1-6 $R^{89}$, $C_{4-17}$cycloalkylalkyl optionally substituted by 1-6 $R^{89}$, 3-15 membered heterocycloalkyl optionally substituted by 1-6 $R^{89}$, 4-21 membered heterocycloalkylalkyl optionally substituted by 1-6 $R^{89}$, 5-15 membered heteroaryl optionally substituted by 1-6 $R^{89}$, 6-21 membered heteroarylalkyl optionally substituted by 1-6 $R^{89}$, halogen, —CN, —C(=O)$R^{80}$, —C(=O)O$R^{80}$, —C(=O)N$R^{82}R^{83}$, —C(=S)N$R^{82}R^{83}$, —NC, —NO$_2$, —N$R^{82}R^{83}$, —N$R^{84}$N$R^{82}R^{83}$, —N$R^{84}$C(=O)$R^{80}$, —N$R^{84}$C(=O)O$R^{81}$, —N$R^{84}$C(=O)N$R^{82}R^{83}$, —N$R^{84}$C(=O)N$R^{84}$C(=O)$R^{80}$, —N$R^{84}$C(=O)N$R^{84}$C(=O)O$R^{80}$, —N$R^{84}$C(=N$R^{85}$)N$R^{82}R^{83}$, —N$R^{84}$C(=S)$R^{80}$, —N$R^{84}$C(=S)N$R^{82}R^{83}$, —N$R^{84}$S(=O)$_2R^{81}$, —O$R^{80}$, =O, —OCN, —OC(=O)$R^{80}$, —OC(=O)N$R^{82}R^{83}$, —SCN, =S, —S(=O)$_nR^{80}$, —S(=O)$_2$O$R^{80}$, or —S(=O)$_2$N$R^{82}R^{83}$; alternatively, when $L^2$, $A^2$, $G^2$, $X^2$, $L^3$, $A^3$, $G^3$ and $X^3$ are absent, $Z^2$ and $Z^3$ can together form a group of formula -$A^{21}$-$A^{22}$-$A^{23}$-; wherein $A^{21}$, $A^{22}$, and $A^{23}$ are independently chosen from —C$Z^{21}Z^{22}$—, —C$Z^{23}Z^{24}$C$Z^{25}Z^{26}$—, —C(=O)—, —N$Z^{27}$—, —S—, —S(=O)—, —S(=O)$_2$—, or —O—; wherein:

(a) when any two of $Z^{21}$, $Z^{22}$, $Z^{23}$, $Z^{24}$, $Z^{25}$, $Z^{26}$ and $Z^{27}$ are located on adjacent atoms, they may together form a bond between the atoms, and (b) any of $Z^{21}$, $Z^{22}$, $Z^{23}$, $Z^{24}$, $Z^{25}$, $Z^{26}$ and $Z^{27}$ may be independently chosen from H, $C_{1-6}$alkyl optionally substituted by 1-6 $R^{99}$, $C_{6-11}$ aryl optionally substituted by 1-7 $R^{99}$, $C_{7-16}$arylalkyl optionally substituted by 1-6 $R^{99}$, $C_{3-11}$cycloalkyl optionally substituted by 1-6 $R^{99}$, $C_{4-17}$cycloalkylalkyl optionally substituted by 1-6 $R^{99}$, 3-15 membered heterocycloalkyl optionally substituted by 1-6 $R^{99}$, 4-21 membered heterocycloalkylalkyl optionally substituted by 1-6 $R^{99}$, 5-15 membered heteroaryl optionally substituted by 1-6 $R^{99}$, 6-21 membered heteroarylalkyl optionally substituted by 1-6 $R^{99}$, halogen, —CN, —C(=O)$R^{90}$, —C(=O)O$R^{90}$, —C(=O)N$R^{92}R^{93}$, —C(=S)N$R^{92}R^{93}$, —NC, —NO$_2$, —N$R^{92}R^{93}$, —N$R^{94}$N$R^{92}R^{93}$, —N$R^{94}$C(=O)$R^{90}$, —N$R^{94}$C(=O)O$R^{91}$, —N$R^{94}$C(=O)N$R^{92}R^{93}$, —N$R^{94}$C(=O)N$R^{94}$C(=O)$R^{90}$, —N$R^{94}$C(=O)N$R^{94}$C(=O)O$R^{90}$, —N$R^{94}$C(=N$R^{95}$)N$R^{92}R^{93}$, —N$R^{94}$C(=S)$R^{90}$, —N$R^{94}$C(=S)N$R^{92}R^{93}$, —N$R^{94}$S(=O)$_2R^{91}$, —O$R^{90}$, =O, —OCN, —OC(=O)N$R^{92}R^{93}$, —SCN, =S, —S(=O)$_nR^{90}$, and —S(=O)$_2$N$R^{92}R^{93}$; and (c) any two of $Z^{21}$, $Z^{22}$, $Z^{23}$, $Z^{24}$, $Z^{25}$, $Z^{26}$ and $Z^{27}$ may together form a group of formula -$A^{31}$-$A^{32}$-$A^{33}$-, wherein $A^{31}$, $A^{32}$, and $A^{33}$ are independently chosen from —C$Z^{31}Z^{32}$—, —C$Z^{33}Z^{34}$C$Z^{35}Z^{36}$—, —C(=O)—, —N$Z^{37}$—, —S—, —S(=O)—, —S(=O)$_2$—, or —O— wherein:

(i) when any two of $Z^{31}$, $Z^{32}$, $Z^{33}$, $Z^{34}$, $Z^{35}$, $Z^{36}$ and $Z^{37}$ are located on adjacent atoms, they may together form a bond between the atoms, and (ii) any of any of $Z^{21}$, $Z^{22}$, $Z^{23}$, $Z^{24}$, $Z^{25}$, $Z^{26}$ and $Z^{27}$ may be independently chosen from H, $C_{1-6}$alkyl optionally substituted by 1-6 $R^{139}$, $C_{6-11}$aryl optionally substituted by 1-7 $R^{139}$, $C_{7-16}$arylalkyl optionally substituted by 1-6 $R^{139}$, $C_{3-11}$cycloalkyl optionally substituted by 1-6 $R^{139}$, $C_{4-17}$cycloalkylalkyl optionally substituted by 1-6 $R^{139}$, 3-15 membered heterocycloalkyl optionally substituted by 1-6 $R^{139}$, 4-21 membered heterocycloalkylalkyl optionally substituted by 1-6 $R^{139}$, 5-15 membered heteroaryl optionally substituted by 1-6 $R^{139}$, 6-21 membered heteroarylalkyl optionally substituted by 1-6 $R^{139}$, halogen, —CN, —C(=O)$R^{130}$, —C(=O)O$R^{130}$, —C(=O)N$R^{132}R^{133}$, —C(=S)N$R^{132}R^{133}$, —NC, —NO$_2$, —N$R^{132}R^{133}$, —N$R^{134}$N$R^{132}R^{133}$, —N$R^{134}$C(=O)$R^{130}$, —N$R^{134}$C(=O)O$R^{131}$, —N$R^{134}$C(=O)N$R^{132}R^{133}$, —N$R^{134}$C(=O)

N$R^{134}$C(=O)$R^{130}$, —N$R^{134}$C(=N$R^{135}$)N$R^{132}R^{133}$, —N$R^{134}$C(=S)$R^{130}$, —N$R^{134}$C(=S)N$R^{132}R^{133}$, —N$R^{134}$S(=O)$_2R^{131}$, —O$R^{130}$, =O, —OCN, —OC(=O)$R^{130}$, —OC(=O)N$R^{132}R^{133}$, —SCN, =S, —S(=O)$_nR^{130}$, and —S(=O)$_2$N$R^{132}R^{133}$. In another embodiment, $Z^2$ is H, $C_{1-6}$alkyl optionally substituted by 1-6 $R^{89}$, $C_{6-11}$aryl optionally substituted by 1-7 $R^{89}$, $C_{7-16}$arylalkyl optionally substituted by 1-6 $R^{89}$, $C_{3-11}$cycloalkyl optionally substituted by 1-6 $R^{89}$, $C_{4-17}$cycloalkylalkyl optionally substituted by 1-6 $R^{89}$, 3-15 membered heterocycloalkyl optionally substituted by 1-6 $R^{89}$, 4-21 membered heterocycloalkylalkyl optionally substituted by 1-6 $R^{89}$, 5-15 membered heteroaryl optionally substituted by 1-6 $R^{89}$, 6-21 membered heteroarylalkyl optionally substituted by 1-6 $R^{89}$, halogen, —CN, —C(=O)$R^{80}$, —C(=O)O$R^{80}$, —C(=O)N$R^{82}R^{83}$, —C(=S)N$R^{82}R^{83}$, —N$R^{82}R^{83}$, —N$R^{84}$C(=O)$R^{80}$, —N$R^{84}$C(=O)O$R^{81}$, —N$R^{84}$C(=O)N$R^{82}R^{83}$, —N$R^{84}$C(=O)N$R^{84}$C(=O)$R^{80}$, —N$R^{84}$C(=O)N$R^{84}$C(=O)O$R^{80}$, —N$R^{84}$C(=S)$R^{80}$, —N$R^{84}$S(=O)$_2R^{81}$, —N$R^{84}$P(=O)$R^{88}R^{88}$, —O$R^{80}$, =O, —OC(=O)$R^{80}$, —OC(=O)N$R^{82}R^{83}$, =S, —S(=O)$_nR^{80}$, —S(=O)$_2$N$R^{82}R^{83}$, or —P(=O)$R^{88}R^{88}$; alternatively, when $L^2$, $A^2$, $G^2$, $X^2$, $L^3$, $A^3$, $G^3$ and $X^3$ are absent, $Z^2$ and $Z^3$ can together form a group of formula -$A^{21}$-$A^{22}$-$A^{23}$-; wherein $A^{21}$, $A^{22}$, and $A^{23}$ are independently chosen from —C$Z^{21}Z^{22}$—, —C$Z^{23}Z^{24}$C$Z^{25}Z^{26}$—, —C(=O)—, —N$Z^{27}$—, —S—, —S(=O)—, —S(=O)$_2$—, or —O—; wherein:

(a) when any two of $Z^{21}$, $Z^{22}$, $Z^{23}$, $Z^{24}$, $Z^{25}$, $Z^{26}$ and $Z^{27}$ are located on adjacent atoms, they may together form a bond between the atoms, and (b) any of $Z^{21}$, $Z^{22}$, $Z^{23}$, $Z^{24}$, $Z^{25}$, $Z^{26}$ and $Z^{27}$ may be independently chosen from H, $C_{1-6}$alkyl optionally substituted by 1-6 $R^{99}$, $C_{6-11}$aryl optionally substituted by 1-7 $R^{99}$, $C_{7-16}$arylalkyl optionally substituted by 1-6 $R^{99}$, $C_{3-11}$cycloalkyl optionally substituted by 1-6 $R^{99}$, $C_{4-17}$cycloalkylalkyl optionally substituted by 1-6 $R^{99}$, 3-15 membered heterocycloalkyl optionally substituted by 1-6 $R^{99}$, 4-21 membered heterocycloalkylalkyl optionally substituted by 1-6 $R^{99}$, 5-15 membered heteroaryl optionally substituted by 1-6 $R^{99}$, 6-21 membered heteroarylalkyl optionally substituted by 1-6 $R^{99}$, halogen, —CN, —C(=O)$R^{90}$, —C(=O)O$R^{90}$, —C(=O)N$R^{92}R^{93}$, —C(=S)N$R^{92}R^{93}$, —N$R^{92}R^{93}$, —N$R^{94}$C(=O)$R^{90}$, —N$R^{94}$C(=O)O$R^{91}$, —N$R^{94}$C(=O)N$R^{92}R^{93}$, —N$R^{94}$C(=O)N$R^{94}$C(=O)$R^{90}$, —N$R^{94}$C(=O)N$R^{94}$C(=O)O$R^{90}$, —N$R^{94}$C(=S)$R^{90}$, —N$R^{94}$S(=O)$_2R^{91}$, —N$R^{94}$P(=O)$R^{98}R^{98}$, —O$R^{90}$, =O, —OC(=O)$R^{90}$, —OC(=O)N$R^{92}R^{93}$, =S, —S(=O)$_nR^{90}$, —S(=O)$_2$N$R^{92}R^{93}$, and —P(=O)$R^{98}R^{98}$; and (c) any two of $Z^{21}$, $Z^{22}$, $Z^{23}$, $Z^{24}$, $Z^{25}$, $Z^{26}$ and $Z^{27}$ may together form a group of formula -$A^{31}$-$A^{32}$-$A^{33}$-, wherein $A^{31}$, $A^{32}$, and $A^{33}$ are independently chosen from —C$Z^{31}Z^{32}$—, —C$Z^{33}Z^{34}$C$Z^{35}Z^{36}$—, —C(=O)—, —N$Z^{37}$—, —S—, —S(=O)—, —S(=O)$_2$—, or —O— wherein:

(i) when any two of $Z^{31}$, $Z^{32}$, $Z^{33}$, $Z^{34}$, $Z^{35}$, $Z^{36}$ and $Z^{37}$ are located on adjacent atoms, they may together form a bond between the atoms, and (ii) any of any of $Z^{21}$, $Z^{22}$, $Z^{23}$, $Z^{24}$, $Z^{25}$, $Z^{26}$ and $Z^{27}$ may be independently chosen from H, $C_{1-6}$alkyl optionally substituted by 1-6 $R^{139}$, $C_{6-11}$ aryl optionally substituted by 1-7 $R^{139}$, $C_{7-16}$arylalkyl optionally substituted by 1-6 $R^{139}$, $C_{3-11}$cycloalkyl optionally substituted by 1-6 $R^{139}$, $C_{4-17}$cycloalkylalkyl optionally substituted by 1-6 $R^{139}$, 3-15 membered heterocycloalkyl optionally substituted by 1-6 $R^{139}$, 4-21 membered heterocycloalkylalkyl optionally substituted by 1-6 $R^{139}$, 5-15 membered heteroaryl optionally substituted by 1-6 $R^{139}$, 6-21 membered heteroarylalkyl optionally substituted by 1-6 $R^{139}$, halogen, —CN, —C(=O)$R^{130}$, —C(=O)O$R^{130}$, —C(=O)N$R^{132}R^{133}$, —C(=S)N$R^{132}R^{133}$, —N$R^{132}R^{133}$, —N$R^{134}$C(=O)$R^{130}$, —N$R^{134}$C(=O)O$R^{131}$, —N$R^{134}$C(=O)N$R^{132}R^{133}$, —N$R^{134}$C(=O)N$R^{134}$C(=O)$R^{130}$, —N$R^{134}$C(=S)$R^{130}$, —N$R^{134}$S(=O)$_2$$R^{131}$, —N$R^{134}$P(=O)$R^{138}R^{138}$, —O$R^{130}$, =O, —OCN, —OC(=O)$R^{130}$, —OC(=O)N$R^{132}R^{133}$, =S, —S(=O)$_n$$R^{130}$, —S(=O)$_2$N$R^{132}R^{133}$, and —P(=O)$R^{138}R^{138}$. In another embodiment, $Z^2$ is H, $C_{1-6}$alkyl optionally substituted by 1-6 $R^{89}$, $C_{6-11}$aryl optionally substituted by 1-7 $R^{89}$, $C_{7-16}$arylalkyl optionally substituted by 1-6 $R^{89}$, $C_{3-11}$cycloalkyl optionally substituted by 1-6 $R^{89}$, $C_{4-17}$cycloalkylalkyl optionally substituted by 1-6 $R^{89}$, 3-15 membered heterocycloalkyl optionally substituted by 1-6 $R^{89}$, 4-21 membered heterocycloalkylalkyl optionally substituted by 1-6 $R^{89}$, 5-15 membered heteroaryl optionally substituted by 1-6 $R^{89}$, 6-21 membered heteroarylalkyl optionally substituted by 1-6 $R^{89}$, halogen, —CN, —C(=O)$R^{80}$, —C(=O)O$R^{80}$, —C(=O)N$R^{82}R^{83}$, —C(=S)N$R^{82}R^{83}$, —N$R^{84}$C(=O)$R^{80}$, —N$R^{84}$C(=O)O$R^{81}$, —N$R^{84}$C(=O)N$R^{82}R^{83}$, —N$R^{84}$C(=O)N$R^{84}$C(=O)$R^{80}$, —N$R^{84}$C(=O)N$R^{84}$C(=O)O$R^{80}$, —N$R^{84}$C(=S)$R^{80}$, —N$R^{84}$S(=O)$_2$$R^{81}$, —O$R^{80}$, =O, —OC(=O)$R^{80}$, —OC(=O)N$R^{82}R^{83}$, =S, —S(=O)$_n$$R^{80}$, or —S(=O)$_2$N$R^{82}R^{83}$; alternatively, when $L^2$, $A^2$, $G^2$, $X^2$, $L^3$, $A^3$, $G^3$ and $X^3$ are absent, $Z^2$ and $Z^3$ can together form a group of formula -$A^{21}$-$A^{22}$-$A^{23}$-; wherein $A^{21}$, $A^{22}$, and $A^{23}$ are independently chosen from —C$Z^{21}Z^{22}$—, —C$Z^{23}Z^{24}$C$Z^{25}Z^{26}$—, —C(=O)—, —N$Z^{27}$—, —S—, —S(=O)—, —S(=O)$_2$—, or —O—; wherein:

(a) when any two of $Z^{21}$, $Z^{22}$, $Z^{23}$, $Z^{24}$, $Z^{25}$, $Z^{26}$ and $Z^{27}$ are located on adjacent atoms, they may together form a bond between the atoms, and (b) any of $Z^{21}$, $Z^{22}$, $Z^{23}$, $Z^{24}$, $Z^{25}$, $Z^{26}$ and $Z^{27}$ may be independently chosen from H, $C_{1-6}$alkyl optionally substituted by 1-6 $R^{99}$, $C_{6-11}$aryl optionally substituted by 1-7 $R^{99}$, $C_{7-16}$arylalkyl optionally substituted by 1-6 $R^{99}$, $C_{3-11}$cycloalkyl optionally substituted by 1-6 $R^{99}$, $C_{4-17}$cycloalkylalkyl optionally substituted by 1-6 $R^{99}$, 3-15 membered heterocycloalkyl optionally substituted by 1-6 $R^{99}$, 4-21 membered heterocycloalkylalkyl optionally substituted by 1-6 $R^{99}$, 5-15 membered heteroaryl optionally substituted by 1-6 $R^{99}$, 6-21 membered heteroarylalkyl optionally substituted by 1-6 $R^{99}$, halogen, —CN, —C(=O)$R^{90}$, —C(=O)O$R^{90}$, —C(=O)N$R^{92}R^{93}$, —C(=S)N$R^{92}R^{93}$, —N$R^{92}R^{93}$, —N$R^{94}$C(=O)$R^{90}$, —N$R^{94}$C(=O)O$R^{91}$, —N$R^{94}$C(=O)N$R^{92}R^{93}$, —N$R^{94}$C(=O)N$R^{94}$C(=O)$R^{90}$, —N$R^{94}$C(=O)N$R^{94}$C(=O)O$R^{90}$, —N$R^{94}$C(=S)$R^{90}$, —N$R^{94}$S(=O)$_2$$R^{91}$, —O$R^{90}$, =O, —OC(=O)$R^{90}$, —OC(=O)N$R^{92}R^{93}$, =S, —S(=O)$_n$$R^{90}$, and —S(=O)$_2$N$R^{92}R^{93}$; and (c) any two of $Z^{21}$, $Z^{22}$, $Z^{23}$, $Z^{24}$, $Z^{25}$, $Z^{26}$ and $Z^{27}$ may together form a group of formula -$A^{31}$-$A^{32}$-$A^{33}$-, wherein $A^{31}$, $A^{32}$, and $A^{33}$ are independently chosen from —C$Z^{31}Z^{32}$—, —C$Z^{33}Z^{34}$C$Z^{35}Z^{36}$—, or —N$Z^{37}$— wherein:

(i) when any two of $Z^{31}$, $Z^{32}$, $Z^{33}$, $Z^{34}$, $Z^{35}$, $Z^{36}$ and $Z^{37}$ are located on adjacent atoms, they may together form a bond between the atoms, and (ii) any of any of $Z^{21}$, $Z^{22}$, $Z^{23}$, $Z^{24}$, $Z^{25}$, $Z^{26}$ and $Z^{27}$ may be independently chosen from H, $C_{1-6}$alkyl optionally substituted by 1-6 $R^{139}$, $C_{6-11}$aryl optionally substituted by 1-7 $R^{139}$, $C_{7-16}$arylalkyl optionally substituted by 1-6 $R^{139}$, $C_{3-11}$cycloalkyl optionally substituted by 1-6 $R^{139}$, $C_{4-17}$cycloalkylalkyl optionally substituted by 1-6 $R^{139}$, 3-15 membered heterocycloalkyl optionally substituted by 1-6 $R^{139}$, 4-21 membered heterocycloalkylalkyl optionally substituted by 1-6 $R^{139}$, 5-15 membered heteroaryl optionally substituted by 1-6 $R^{139}$, 6-21 membered heteroarylalkyl optionally substituted by 1-6 $R^{139}$, halogen, —CN, —C(=O)$R^{130}$, —C(=O)O$R^{130}$, —C(=O)N$R^{132}R^{133}$, —N$R^{132}R^{133}$, —N$R^{134}$C(=O)$R^{130}$, —N$R^{134}$C(=O)N$R^{132}R^{133}$, —N$R^{134}$C(=O)N$R^{134}$C(=O)$R^{130}$, —N$R^{134}$C(=S)$R^{130}$, —N$R^{134}$S(=O)$_2$$R^{131}$, —O$R^{130}$, =O, —OCN, —OC(=O)$R^{130}$, —OC(=O)N$R^{132}R^{133}$, =S, —S(=O)$_n$$R^{130}$, and —S(=O)$_2$N$R^{132}R^{133}$.

In another embodiment, $Z^2$ is H, $C_{1-6}$alkyl optionally substituted by 1-6 $R^{89}$, $C_{6-11}$aryl optionally substituted by 1-7 $R^{89}$, $C_{7-16}$arylalkyl optionally substituted by 1-6 $R^{89}$, $C_{3-11}$cycloalkyl optionally substituted by 1-6 $R^{89}$, $C_{4-17}$cycloalkylalkyl optionally substituted by 1-6 $R^{89}$, 3-15 membered heterocycloalkyl optionally substituted by 1-6 $R^{89}$, 4-21 membered heterocycloalkylalkyl optionally substituted by 1-6 $R^{89}$, 5-15 membered heteroaryl optionally substituted by 1-6 $R^{89}$, 6-21 membered heteroarylalkyl optionally substituted by 1-6 $R^{89}$, halogen, —CN, —C(=O)$R^{80}$, —C(=O)O$R^{80}$, —C(=O)N$R^{82}R^{83}$, —N$R^{82}R^{83}$, —N$R^{84}$C(=O)$R^{80}$, —N$R^{84}$C(=O)O$R^{81}$, —N$R^{84}$C(=O)N$R^{82}R^{83}$, —N$R^{84}$S(=O)$_2$$R^{81}$, —O$R^{80}$, =O, —OC(=O)$R^{80}$, —OC(=O)N$R^{82}R^{83}$, =S, —S(=O)$_n$$R^{80}$, or —S(=O)$_2$N$R^{82}R^{83}$; alternatively, when $L^2$, $A^2$, $G^2$, $X^2$, $L^3$, $A^3$, $G^3$ and $X^3$ are absent, $Z^2$ and $Z^3$ can together form a group of formula -$A^{21}$-$A^{22}$-$A^{23}$-, wherein $A^{21}$, $A^{22}$, and $A^{23}$ are independently chosen from —C$Z^{21}Z^{22}$—, —C$Z^{23}Z^{24}$C$Z^{25}Z^{26}$—, or —N$Z^{27}$—; wherein:

(a) when any two of $Z^{21}$, $Z^{22}$, $Z^{23}$, $Z^{24}$, $Z^{25}$, $Z^{26}$ and $Z^{27}$ are located on adjacent atoms, they may together form a bond between the atoms, and (b) any of $Z^{21}$, $Z^{22}$, $Z^{23}$, $Z^{24}$, $Z^{25}$, $Z^{26}$ and $Z^{27}$ may be independently chosen from H, $C_{1-6}$alkyl optionally substituted by 1-6 $R^{99}$, $C_{6-11}$ aryl optionally substituted by 1-7 $R^{99}$, $C_{7-16}$arylalkyl optionally substituted by 1-6 $R^{99}$, $C_{3-11}$cycloalkyl optionally substituted by 1-6 $R^{99}$, $C_{4-17}$cycloalkylalkyl optionally substituted by 1-6 $R^{99}$, 3-15 membered heterocycloalkyl optionally substituted by 1-6 $R^{99}$, 4-21 membered heterocycloalkylalkyl optionally substituted by 1-6 $R^{99}$, 5-15 membered heteroaryl optionally substituted by 1-6 $R^{99}$, 6-21 membered heteroarylalkyl optionally substituted by 1-6 $R^{99}$, halogen, —CN, —C(=O)$R^{90}$, —C(=O)O$R^{90}$, —C(=O)N$R^{92}R^{93}$, —N$R^{92}R^{93}$, —N$R^{94}$C(=O)$R^{90}$, —N$R^{94}$C(=O)O$R^{91}$, —N$R^{94}$C(=O)N$R^{92}R^{93}$, —N$R^{94}$S(=O)$_2$$R^{91}$, —O$R^{90}$, =O, —OC(=O)$R^{90}$, —OC(=O)N$R^{92}R^{93}$, =S, —S(=O)$_n$$R^{90}$, and —S(=O)$_2$N$R^{92}R^{93}$; and (c) any two of $Z^{21}$, $Z^{22}$, $Z^{23}$, $Z^{24}$, $Z^{25}$, $Z^{26}$ and $Z^{27}$ may together form a group of formula -$A^{31}$-$A^{32}$-$A^{33}$-, wherein $A^{31}$, $A^{32}$, and $A^{33}$ are independently chosen from —C$Z^{31}Z^{32}$—, —C$Z^{33}Z^{34}$C$Z^{35}Z^{36}$—, or —N$Z^{37}$— wherein:

(i) when any two of $Z^{31}$, $Z^{32}$, $Z^{33}$, $Z^{34}$, $Z^{35}$, $Z^{36}$ and $Z^{37}$ are located on adjacent atoms, they may together form a bond between the atoms, and (ii) any of any of $Z^{21}$, $Z^{22}$, $Z^{23}$, $Z^{24}$, $Z^{25}$, $Z^{26}$ and $Z^{27}$ may be independently chosen from H, $C_{1-6}$alkyl optionally substituted by 1-6 $R^{139}$, $C_{6-11}$ aryl optionally substituted by 1-7 $R^{139}$, $C_{7-16}$arylalkyl optionally substituted by 1-6 $R^{139}$, $C_{3-11}$cycloalkyl optionally substituted by 1-6 $R^{139}$, $C_{4-17}$cycloalkylalkyl optionally substituted by 1-6 $R^{139}$, 3-15 membered heterocycloalkyl optionally substituted by 1-6 $R^{139}$, 4-21 membered heterocycloalkylalkyl optionally substituted by 1-6 $R^{139}$, 5-15 membered heteroaryl optionally substituted by 1-6 $R^{139}$, 6-21 membered heteroarylalkyl optionally substituted by 1-6 $R^{139}$, halogen, —CN, —C(=O)$R^{130}$, —C(=O)O$R^{130}$, —C(=O)N$R^{132}R^{133}$, —N$R^{132}R^{133}$, —N$R^{134}$C(=O)$R^{130}$, —N$R^{134}$C(=O)O$R^{131}$, —N$R^{134}$C(=O)N$R^{132}R^{133}$, —N$R^{134}$S(=O)$_2$$R^{131}$, —O$R^{130}$, =O, —OCN, —OC(=O)R$^{130}$, —OC(=O)NR$^{132}$R$^{133}$, =S, —S(=O)$_n$R$^{130}$, and —S(=O)$_2$NR$^{132}$R$^{133}$. In another embodiment, Z$^2$ is H, C$_{1-6}$alkyl optionally substituted by 1-6 R$^{89}$, C$_{6-11}$aryl optionally substituted by 1-7 R$^{89}$, C$_{7-16}$arylalkyl optionally substituted by 1-6 R$^{89}$, C$_{3-11}$cycloalkyl optionally substituted by 1-6 R$^{89}$, C$_{4-17}$cycloalkylalkyl optionally substituted by 1-6 R$^{89}$, 3-15 membered heterocycloalkyl optionally substituted by 1-6 R$^{89}$, 4-21 membered heterocycloalkylalkyl optionally substituted by 1-6 R$^{89}$, 5-15 membered heteroaryl optionally substituted by 1-6 R$^{89}$, 6-21 membered heteroarylalkyl optionally substituted by 1-6 R$^{89}$, halogen, —CN, —C(=O)R$^{80}$, —C(=O)OR$^{80}$, —C(=O)NR$^{82}$R$^{83}$, —C(=S)NR$^{82}$R$^{83}$, —NR$^{82}$R$^{83}$, —NR$^{84}$C(=O)R$^{80}$, —NR$^{84}$C(=O)OR$^{81}$, —NR$^{84}$C(=O)NR$^{82}$R$^{83}$, —NR$^{84}$C(=O)NR$^{84}$C(=O)R$^{80}$, —NR$^{84}$C(=O)NR$^{84}$C(=O)OR$^{80}$, —NR$^{84}$C(=S)R$^{80}$, —NR$^{84}$S(=O)$_2$R$^{81}$, —NR$^{84}$P(=O)R$^{88}$R$^{88}$, —OR$^{80}$, =O, —OC(=O)R$^{80}$, —OC(=O)NR$^{82}$R$^{83}$, =S, —S(=O)$_n$R$^{80}$, —S(=O)$_2$NR$^{82}$R$^{83}$, or —P(=O)R$^{88}$R$^{88}$; alternatively, when L$^2$, A$^2$, G$^2$, X$^2$, L$^3$, A$^3$, G$^3$ and X$^3$ are absent, Z$^2$ and Z$^3$ can together form a group of formula -A$^{21}$-A$^{22}$-A$^{23}$, wherein A$^{21}$, A$^{22}$, and A$^{23}$ are independently chosen from —CZ$^{21}$Z$^{22}$—, —CZ$^{23}$Z$^{24}$CZ$^{25}$Z$^{26}$—, —C(=O)—, —NZ$^{27}$—, —S—, —S(=O)—, —S(=O)$_2$—, or —O—; wherein:

(a) when any two of Z$^{21}$, Z$^{22}$, Z$^{23}$, Z$^{24}$, Z$^{25}$, Z$^{26}$ and Z$^{27}$ are located on adjacent atoms, they may together form a bond between the atoms, and (b) any a Z$^{21}$, Z$^{22}$, Z$^{23}$, Z$^{24}$, Z$^{25}$, Z$^{26}$ and Z$^{27}$ may be independently chosen from H, C$_{1-6}$alkyl optionally substituted by 1-6 R$^{99}$, C$_{6-11}$aryl optionally substituted by 1-7 R$^{99}$, C$_{7-16}$arylalkyl optionally substituted by 1-6 R$^{99}$, C$_{3-11}$cycloalkyl optionally substituted by 1-6 R$^{99}$, C$_{4-17}$cycloalkylalkyl optionally substituted by 1-6 R$^{99}$, 3-15 membered heterocycloalkyl optionally substituted by 1-6 R$^{99}$, 4-21 membered heterocycloalkylalkyl optionally substituted by 1-6 R$^{99}$, 5-15 membered heteroaryl optionally substituted by 1-6 R$^{99}$, 6-21 membered heteroarylalkyl optionally substituted by 1-6 R$^{99}$, halogen, —CN, —C(=O)R$^{90}$, —C(=O)OR$^{90}$, —C(=O)NR$^{92}$R$^{93}$, —C(=S)NR$^{92}$R$^{93}$, —NR$^{92}$R$^{93}$, —NR$^{94}$C(=O)R$^{90}$, —NR$^{94}$C(=O)OR$^{91}$, —NR$^{94}$C(=O)NR$^{92}$R$^{93}$, —NR$^{94}$C(=O)NR$^{94}$C(=O)R$^{90}$, —NR$^{94}$C(=O)NR$^{94}$C(=O)OR$^{90}$, —NR$^{94}$C(=S)R$^{90}$, —NR$^{94}$S(=O)$_2$R$^{91}$, —NR$^{94}$P(=O)R$^{98}$R$^{98}$, —OR$^{90}$, =O, —OC(=O)R$^{90}$, —OC(=O)NR$^{92}$R$^{93}$, =S, —S(=O)$_n$R$^{90}$, —S(=O)$_2$NR$^{92}$R$^{93}$, and —P(=O)R$^{98}$R$^{98}$; and (c) any two of Z$^{21}$, Z$^{22}$, Z$^{23}$, Z$^{24}$, Z$^{25}$, Z$^{26}$ and Z$^{27}$ may together form a group of formula -A$^{31}$-A$^{32}$-A$^{33}$-, wherein A$^{31}$, A$^{32}$, and A$^{33}$ are independently chosen from —CZ$^{31}$Z$^{32}$—, —CZ$^{33}$Z$^{34}$CZ$^{35}$Z$^{36}$—, —C(=O)—, —NZ$^{37}$—, —S—, —S(=O)—, —S(=O)$_2$—, or —O— wherein:

(i) when any two of Z$^{31}$, Z$^{32}$, Z$^{33}$, Z$^{34}$, Z$^{35}$, Z$^{36}$ and Z$^{37}$ are located on adjacent atoms, they may together form a bond between the atoms, and (ii) any of any of Z$^{21}$, Z$^{22}$, Z$^{23}$, Z$^{24}$, Z$^{25}$, Z$^{26}$ and Z$^{27}$ may be independently chosen from H, C$_{1-6}$alkyl optionally substituted by 1-6 R$^{139}$, C$_{6-11}$aryl optionally substituted by 1-7 R$^{139}$, C$_{7-16}$arylalkyl optionally substituted by 1-6 R$^{139}$, C$_{3-11}$cycloalkyl optionally substituted by 1-6 R$^{139}$, C$_{4-17}$cycloalkylalkyl optionally substituted by 1-6 R$^{139}$, 3-15 membered heterocycloalkyl optionally substituted by 1-6 R$^{139}$, 4-21 membered heterocycloalkylalkyl optionally substituted by 1-6 R$^{139}$, 5-15 membered heteroaryl optionally substituted by 1-6 R$^{139}$, 6-21 membered heteroarylalkyl optionally substituted by 1-6 R$^{139}$, halogen, —CN, —C(=O)R$^{130}$, —C(=O)OR$^{130}$, —C(=O)NR$^{132}$R$^{133}$, —C(=S)NR$^{132}$R$^{133}$, —NR$^{132}$R$^{133}$, —NR$^{134}$C(=O)R$^{130}$, —NR$^{134}$C(=O)OR$^{131}$, —NR$^{134}$C(=O)NR$^{132}$R$^{133}$, —NR$^{134}$C(=O)NR$^{134}$C(=O)R$^{130}$, —NR$^{134}$C(=S)R$^{130}$, —NR$^{134}$S(=O)$_2$R$^{131}$, —NR$^{134}$P(=O)R$^{138}$R$^{138}$, —OR$^{130}$, =O, —OCN, —OC(=O)R$^{130}$, —OC(=O)NR$^{132}$R$^{133}$, =S, —S(=O)$_n$R$^{130}$, —S(=O)$_2$NR$^{132}$R$^{133}$, and —P(=O)R$^{138}$R$^{138}$. In another embodiment, Z$^2$ is H, C$_{1-6}$alkyl optionally substituted by 1-6 R$^{89}$, C$_{6-11}$aryl optionally substituted by 1-7 R$^{89}$, C$_{7-16}$arylalkyl optionally substituted by 1-6 R$^{89}$, C$_{3-11}$cycloalkyl optionally substituted by 1-6 R$^{89}$, C$_{4-17}$cycloalkylalkyl optionally substituted by 1-6 R$^{89}$, 3-15 membered heterocycloalkyl optionally substituted by 1-6 R$^{89}$, 4-21 membered heterocycloalkylalkyl optionally substituted by 1-6 R$^{89}$, 5-15 membered heteroaryl optionally substituted by 1-6 R$^{89}$, 6-21 membered heteroarylalkyl optionally substituted by 1-6 R$^{89}$, halogen, —CN, —C(=O)R$^{80}$, —C(=O)OR$^{80}$, —C(=O)NR$^{82}$R$^{83}$, —C(=S)NR$^{82}$R$^{83}$, —NR$^{84}$C(=O)R$^{80}$, —NR$^{84}$C(=O)OR$^{81}$, —NR$^{84}$C(=O)NR$^{82}$R$^{83}$, —NR$^{84}$C(=O)NR$^{84}$C(=O)R$^{80}$, —NR$^{84}$C(=O)NR$^{84}$C(=O)OR$^{80}$, —NR$^{84}$C(=S)R$^{80}$, —NR$^{84}$S(=O)$_2$R$^{81}$, —OR$^{80}$, =O, —OC(=O)R$^{80}$, —OC(=O)NR$^{82}$R$^{83}$, =S, —S(=O)$_n$R$^{80}$, or —S(=O)$_2$NR$^{82}$R$^{83}$; alternatively, when L$^2$, A$^2$, G$^2$, X$^2$, L$^3$, A$^3$, G$^3$ and X$^3$ are absent, Z$^2$ and Z$^3$ can together form a group of formula -A$^{21}$-A$^{22}$-A$^{23}$-, wherein A$^{21}$, A$^{22}$, and A$^{23}$ are independently chosen from —CZ$^{21}$Z$^{22}$—, —CZ$^{23}$Z$^{24}$CZ$^{25}$Z$^{26}$—, —C(=O)—, —NZ$^{27}$—, —S—, —S(=O)—, —S(=O)$_2$—, or —O—; wherein:

(a) when any two of Z$^{21}$, Z$^{22}$, Z$^{23}$, Z$^{24}$, Z$^{25}$, Z$^{26}$ and Z$^{27}$ are located on adjacent atoms, they may together form a bond between the atoms, and (b) any of Z$^{21}$, Z$^{22}$, Z$^{23}$, Z$^{24}$, Z$^{25}$, Z$^{26}$ and Z$^{27}$ may be independently chosen from H, C$_{1-6}$alkyl optionally substituted by 1-6 R$^{99}$, C$_{6-11}$aryl optionally substituted by 1-7 R$^{99}$, C$_{7-16}$arylalkyl optionally substituted by 1-6 R$^{99}$, C$_{3-11}$cycloalkyl optionally substituted by 1-6 R$^{99}$, C$_{4-17}$cycloalkylalkyl optionally substituted by 1-6 R$^{99}$, 3-15 membered heterocycloalkyl optionally substituted by 1-6 R$^{99}$, 4-21 membered heterocycloalkylalkyl optionally substituted by 1-6 R$^{99}$, 5-15 membered heteroaryl optionally substituted by 1-6 R$^{99}$, 6-21 membered heteroarylalkyl optionally substituted by 1-6 R$^{99}$, halogen, —CN, —C(=O)R$^{90}$, —C(=O)OR$^{90}$, —C(=O)NR$^{92}$R$^{93}$, —C(=S)NR$^{92}$R$^{93}$, —NR$^{92}$R$^{93}$, —NR$^{94}$C(=O)R$^{90}$, —NR$^{94}$C(=O)OR$^{91}$, —NR$^{94}$C(=O)NR$^{92}$R$^{93}$, —NR$^{92}$R$^{93}$, —NR$^{94}$C(=O)R$^{90}$, —NR$^{94}$C(=O)NR$^{94}$C(=O)OR$^{90}$, —NR$^{94}$C(=S)R$^{90}$, —NR$^{94}$S(=O)$_2$R$^{91}$, —OR$^{90}$, =O, —OC(=O)R$^{90}$, —OC(=O)NR$^{92}$R$^{93}$, =S, —S(=O)$_n$R$^{90}$, and —S(=O)$_2$NR$^{92}$R$^{93}$; and (c) any two of Z$^{21}$, Z$^{22}$, Z$^{23}$, Z$^{24}$, Z$^{25}$, Z$^{26}$ and Z$^{27}$ may together form a group of formula -A$^{31}$-A$^{32}$-A$^{33}$-, wherein A$^{31}$, A$^{32}$, and A$^{33}$ are independently chosen from —CZ$^{31}$Z$^{32}$—, —CZ$^{33}$Z$^{34}$CZ$^{35}$Z$^{36}$—, —C(=O)—, —NZ$^{37}$—, —S—, —S(=O)—, —S(=O)$_2$—, or —O— wherein:

(i) when any two of Z$^{31}$, Z$^{32}$, Z$^{33}$, Z$^{34}$, Z$^{35}$, Z$^{36}$ and Z$^{37}$ are located on adjacent atoms, they may together form a bond between the atoms, and (ii) any of any of Z$^{21}$, Z$^{22}$, Z$^{23}$, Z$^{24}$, Z$^{25}$, Z$^{26}$ and Z$^{27}$ may be independently chosen from H, C$_{1-6}$alkyl optionally substituted by 1-6 R$^{139}$, C$_{6-11}$aryl optionally substituted by 1-7 R$^{139}$, C$_{7-16}$arylalkyl optionally substituted by 1-6 R$^{139}$, C$_{3-11}$cycloalkyl optionally substituted by 1-6 R$^{139}$, C$_{4-17}$cycloalkylalkyl optionally substituted by 1-6 R$^{139}$, 3-15 membered heterocycloalkyl optionally substituted by 1-6 R$^{139}$, 4-21 membered heterocycloalkylalkyl optionally substituted by 1-6 R$^{139}$, 5-15 membered heteroaryl optionally substituted by 1-6 R$^{139}$, 6-21 membered heteroarylalkyl optionally substituted by 1-6 R$^{139}$, halogen, —CN, —C(=O)R$^{130}$, —C(=O)OR$^{130}$, —C(=O)NR$^{132}$R$^{133}$, —C(=S)

$NR^{132}R^{133}$, $NR^{132}R^{133}$, —$NR^{134}C(=O)R^{130}$, —$NR^{134}(=O)OR^{131}$, —$NR^{134}C(=O)NR^{132}R^{133}$, —$NR^{134}C(=O)NR^{134}C(=O)R^{130}$, —$NR^{134}C(=S)R^{130}$, —$NR^{134}S(=O)_2R^{131}$, —$OR^{130}$, =O, —OCN, —OC(=O)R^{130}, —OC(=O)NR^{132}R^{133}$, =S, —$S(=O)_nR^{130}$, and —$S(=O)_2NR^{132}R^{133}$. In another embodiment, $Z^2$ is H, $C_{1-6}$alkyl optionally substituted by 1-6 $R^{89}$, $C_{6-11}$aryl optionally substituted by 1-7 $R^{89}$, $C_{3-11}$cycloalkyl optionally substituted by 1-6 $R^{89}$, halogen, —CN, —C(=O)R^{80}, —C(=O)OR^{80}, —C(=O)NR^{82}R^{83}, —NR^{84}C(=O)R^{80}, —NR^{84}C(=O)OR^{81}, —NR^{84}C(=O)NR^{82}R^{83}, —NR^{84}S(=O)_2R^{81}, —OR^{80}, =O, —OC(O)R^{80}, —OC(=O)NR^{82}R^{83}, =S, —S(=O)_nR^{80}$, or —$S(=O)_2NR^{82}R^{83}$; alternatively, when $L^2$, $A^2$, $G^2$, $X^2$, $L^3$, $A^3$, $G^3$ and $X^3$ are absent, $Z^2$ and $Z^3$ can together form a group of formula -$A^{21}$-$A^{22}$-$A^{23}$-, wherein $A^{21}$, $A^{22}$, and $A^{23}$ are independently chosen from —$CZ^{21}Z^{22}$—, —$CZ^{23}Z^{24}CZ^{25}Z^{26}$—, —$NZ^{27}$—; wherein:

(a) when any two of $Z^{21}$, $Z^{22}$, $Z^{23}$, $Z^{24}$, $Z^{25}$, $Z^{26}$ and $Z^{27}$ are located on adjacent atoms, they may together form a bond between the atoms, and (b) any of $Z^{21}$, $Z^{22}$, $Z^{23}$, $Z^{24}$, $Z^{25}$, $Z^{26}$ and $Z^{27}$ may be independently chosen from H, $C_{1-6}$alkyl optionally substituted by 1-6 $R^{99}$, $C_{6-11}$aryl optionally substituted by 1-7 $R^{99}$, $C_{3-11}$cycloalkyl optionally substituted by 1-6 $R^{99}$, 3-15 membered heterocycloalkyl optionally substituted by 1-6 $R^{99}$, 5-15 membered heteroaryl optionally substituted by 1-6 $R^{99}$, halogen, —CN, —C(=O)R^{90}, —C(=O)OR^{90}, —C(=O)NR^{92}R^{93}, —NR^{92}R^{93}, —NR^{94}C(=O)R^{90}, —NR^{94}C(=O)OR^{91}, —NR^{94}C(=O)NR^{92}R^{93}, —NR^{94}S(=O)_2R^{91}, —OR^{90}, =O, —OC(=O)R^{90}, —OC(=O)NR^{92}R^{93}, =S, —S(=O)_nR^{90}$, and —$S(=O)_2NR^{92}R^{93}$. In another embodiment, $Z^2$ is H, $C_{1-6}$alkyl optionally substituted by 1-6 $R^{89}$, phenyl optionally substituted by 1-4 $R^{89}$, $C_{3-6}$cycloalkyl optionally substituted by 1-6 $R^{89}$, halogen, —CN, —C(=O)R^{80}, —C(=O)OR^{80}, —C(=O)NR^{82}R^{83}, —NR^{82}R^{83}, —NR^{84}C(=O)R^{80}, —NR^{84}C(=O)OR^{81}, —NR^{84}C(=O)NR^{82}R^{83}, —NR^{84}S(=O)_2R^{81}, —OR^{80}, =O, —OC(=O)R^{80}, —OC(=O)NR^{82}R^{83}, =S, —S(=O)_nR^{80}$, or —$S(=O)_2 NR^{82}R^{83}$; alternatively, when $L^2$, $A^2$, $G^2$, $X^2$, $L^3$, $A^3$, $G^3$ and $X^3$ are absent, $Z^2$ and $Z^3$ can together form a group of formula -$A^{21}$-$A^{22}$-$A^{23}$-, wherein $A^{21}$, $A^{22}$, and $A^{23}$ are independently chosen from —$CZ^{21}Z^{22}$—, —$CZ^{23}Z^{24}CZ^{25}Z^{26}$—, or —$NZ^{27}$—; wherein:

(a) when any two of $Z^{21}$, $Z^{22}$, $Z^{23}$, $Z^{24}$, $Z^{25}$, $Z^{26}$ and $Z^{27}$ are located on adjacent atoms, they may together form a bond between the atoms, and (b) any of $Z^{21}$, $Z^{22}$, $Z^{23}$, $Z^{24}$, $Z^{25}$, $Z^{26}$ and $Z^{27}$ may be independently chosen from H, $C_{1-6}$alkyl optionally substituted by 1-6 $R^{99}$, $C_{6-11}$aryl optionally substituted by 1-7 $R^{99}$, $C_{3-11}$cycloalkyl optionally substituted by 1-6 $R^{99}$, 3-15 membered heterocycloalkyl optionally substituted by 1-6 $R^{99}$, 5-15 membered heteroaryl optionally substituted by 1-6 $R^{99}$, halogen, —CN, —C(=O)R^{90}, —C(=O)OR^{90}, —C(=O)NR^{92}R^{93}, —NR^{92}R^{93}, —NR^{94}C(=O)R^{90}, —NR^{94}C(=O)OR^{91}, —NR^{94}C(=O)NR^{92}R^{93}, —NR^{94}S(=O)_2R^{91}, —OR^{90}, =O, —OC(=O)R^{90}, —OC(=O)NR^{92}R^{93}, =S, —S(=O)_nR^{90}$, and —$S(=O)_2NR^{92}R^{93}$. In another embodiment, $Z^2$ is H, $C_{1-6}$alkyl optionally substituted by 1-6 $R^{89}$, phenyl optionally substituted by 1-4 $R^{89}$, $C_3$cycloalkyl optionally substituted by 1-6 $R^{89}$, halogen, —CN, —C(=O)R^{80}, —C(=O)OR^{80}, —C(=O)NR^{82}R^{83}, —NR^{82}R^{83}, —NR^{84}C(=O)R^{80}, —NR^{84}C(=O)OR^{81}, —NR^{84}C(=O)NR^{82}R^{83}, —NR^{84}S(=O)_2R^{81}, —OR^{80}, =O, —OC(=O)R^{80}, —OC(=O)NR^{82}R^{83}, =S, —S(=O)_nR^{80}$, or —$S(=O)_2 NR^{82}R^{83}$; alternatively, when $L^2$, $A^2$, $G^2$, $X^2$, $L^3$, $A^3$, $G^3$ and $X^3$ are absent, $Z^2$ and $Z^3$ can together form a group of formula -$A^{21}$-$A^{22}$-$A^{23}$-, wherein $A^{21}$, $A^{22}$, and $A^{23}$ are independently chosen from —$CZ^{21}Z^{22}$—, —$CZ^{23}Z^{24}CZ^{25}Z^{26}$—, or —$NZ^{27}$—; wherein:

(a) when any two of $Z^{21}$, $Z^{22}$, $Z^{23}$, $Z^{24}$, $Z^{25}$, $Z^{26}$ and $Z^{27}$ are located on adjacent atoms, they may together form a bond between the atoms, and (b) any of $Z^{21}$, $Z^{22}$, $Z^{23}$, $Z^{24}$, $Z^{25}$, $Z^{26}$ and $Z^{27}$ may be independently chosen from H, $C_{1-6}$alkyl optionally substituted by 1-6 $R^{99}$, $C_{6-11}$aryl optionally substituted by 1-7 $R^{99}$, $C_{3-11}$cycloalkyl optionally substituted by 1-6 $R^{99}$, 3-15 membered heterocycloalkyl optionally substituted by 1-6 $R^{99}$, 5-15 membered heteroaryl optionally substituted by 1-6 $R^{99}$, halogen, —CN, —C(=O)R^{90}, —C(=O)OR^{90}, —C(=O)NR^{92}R^{93}, —NR^{94}C(=O)R^{90}, —NR^{94}C(=O)OR^{91}, —NR^{94}C(=O)NR^{92}R^{93}, —NR^{94}S(=O)_2R^{91}, —OR^{90}, =O, —OC(=O)R^{90}, —OC(=O)NR^{92}R^{93}, =S, —S(=O)_nR^{90}$, and —$S(=O)_2NR^{92}R^{93}$. In another embodiment, $Z^2$ is H, $C_{1-6}$alkyl optionally substituted by 1-6 $R^{89}$, $C_{6-11}$ aryl optionally substituted by 1-7 $R^{89}$, $C_{7-16}$arylalkyl optionally substituted by 1-6 $R^{89}$, $C_{3-11}$cycloalkyl optionally substituted by 1-6 $R^{89}$, 3-15 membered heterocycloalkyl optionally substituted by 1-6 $R^{89}$, 5-15 membered heteroaryl optionally substituted by 1-6 $R^{89}$, halogen, —CN, —C(=O)R^{80}, —C(=O)OR^{80}, —C(=O)NR^{82}R^{83}, —NR^{82}R^{83}, —NR^{84}C(=O)R^{80}, —NR^{84}C(=O)OR^{81}, —NR^{84}C(=O)NR^{82}R^{83}, —NR^{84}S(=O)_2R^{81}, —OR^{80}, =O, —OC(=O)R^{80}, —OC(=O)NR^{82}R^{83}, =S, —S(=O)_nR^{80}$, or —$S(=O)_2NR^{82}R^{83}$; alternatively, when $L^2$, $A^2$, $G^2$, $X^2$, $L^3$, $A^3$, $G^3$ and $X^3$ are absent, $Z^2$ and $Z^3$ can together form a group of formula -$A^{21}$-$A^{22}$-$A^{23}$-, wherein $A^{21}$, $A^{22}$, and $A^{23}$ are independently chosen from —$CZ^{21}Z^{22}$—, —$CZ^{23}Z^{24}CZ^{25}Z^{26}$—, or —$NZ^{27}$—; wherein:

(a) when any two of $Z^{21}$, $Z^{22}$, $Z^{23}$, $Z^{24}$, $Z^{25}$, $Z^{26}$ and $Z^{27}$ are located on adjacent atoms, they may together form a bond between the atoms, and (b) any of $Z^{21}$, $Z^{22}$, $Z^{23}$, $Z^{24}$, $Z^{25}$, $Z^{26}$ and $Z^{27}$ may be independently chosen from H, $C_{1-6}$alkyl optionally substituted by 1-6 $R^{99}$, $C_{6-11}$aryl optionally substituted by 1-7 $R^{99}$, $C_{3-11}$cycloalkyl optionally substituted by 1-6 $R^{99}$, 3-15 membered heterocycloalkyl optionally substituted by 1-6 $R^{99}$, 5-15 membered heteroaryl optionally substituted by 1-6 $R^{99}$, halogen, —CN, —C(=O)R^{90}, —C(=O)OR^{90}, —C(=O)NR^{92}R^{93}, —NR^{94}C(=O)R^{90}, —NR^{94}C(=O)OR^{91}, —NR^{94}C(=O)NR^{92}R^{93}, —NR^{94}S(=O)_2R^{91}, —OR^{90}, =O, —OC(=O)R^{90}, —OC(=O)NR^{92}R^{93}, =S, —S(=O)_nR^{90}$, and —$S(=O)_2NR^{92}R^{93}$. In another embodiment, $Z^2$ is H, $C_{1-6}$alkyl optionally substituted by 1-6 $R^{89}$, $C_{6-11}$ aryl optionally substituted by 1-7 $R^{89}$, $C_{3-11}$cycloalkyl optionally substituted by 1-6 $R^{89}$, halogen, —CN, —C(=O)OR^{80}, —NR^{82}R^{83}$, or —$S(=O)_nR^{16}$; alternatively, when $L^2$, $A^2$, $G^2$, $X^2$, $L^3$, $A^3$, $G^3$ and $X^3$ are absent, $Z^2$ and $Z^3$ can together form a group of formula -$A^{21}$-$A^{22}$-$A^{23}$-, wherein $A^{21}$, $A^{22}$, and $A^{23}$ are independently chosen from —$CZ^{21}Z^{22}$—, —$CZ^{23}Z^{24}CZ^{25}Z^{26}$—, —C(=O)—, —$NZ^{27}$—, —S—, —S(=O)—, —$S(=O)_2$—, or —O—; wherein when any two of $Z^{21}$, $Z^{22}$, $Z^{23}$, $Z^{24}$, $Z^{25}$, $Z^{26}$ and $Z^{27}$ are located on adjacent atoms, they may together form a bond between the atoms, and wherein any of $Z^{21}$, $Z^{22}$, $Z^{23}$, $Z^{24}$, $Z^{25}$, $Z^{26}$ and $Z^{27}$ may be independently chosen from H and —$OR^{90}$. In another embodiment, $Z^2$ is H, $C_{1-6}$alkyl optionally substituted by 1-6 $R^{89}$, phenyl optionally substituted by 1-4 $R^{89}$, $C_{3-6}$cycloalkyl optionally substituted by 1-6 $R^{89}$, halogen, —CN, —C(=O)OR^{80}, —NR^{82}R^{83}$, or —$S(=O)_nR^{80}$; alternatively, when $L^2$, $A^2$, $G^2$, $X^2$, $L^3$, $A^3$, $G^3$ and $X^3$ are absent, $Z^2$ and $Z^3$ can together form a group of formula -$A^{21}$-$A^{22}$-$A^{23}$-, wherein $A^{21}$, $A^{22}$, and $A^{23}$ are independently chosen from —$CZ^{21}Z^{22}$—, —$CZ^{23}Z^{24}CZ^{25}Z^{26}$—, —C(=O)—, —$NZ^{27}$—, —S—, —S(=O)—, —S(=O)$_2$—, or —O—; wherein when any two of $Z^{21}$, $Z^{22}$, $Z^{23}$, $Z^{24}$, $Z^{25}$, $Z^{26}$ and $Z^{27}$ are located on adjacent atoms, they may together form a bond between the atoms, and wherein any of $Z^{21}$, $Z^{22}$, $Z^{23}$, $Z^{24}$, $Z^{25}$, $Z^{26}$ and $Z^{27}$ may be independently chosen from H and —$OR^{90}$. In another embodiment, $Z^2$ is H, $C_{1-6}$alkyl optionally substituted by 1-6 $R^{89}$, phenyl optionally substituted by 1-4 $R^{89}$, $C_3$cycloalkyl optionally substituted by 1-6 $R^{89}$, halogen, —CN, —C(=O)$OR^{80}$, —$NR^{82}R^{83}$, or —S(=O)$_n R^{80}$; alternatively, when $L^2$, $A^2$, $G^2$, $X^2$, $L^3$, $A^3$, $G^3$ and $X^3$ are absent, $Z^2$ and $Z^3$ can together form a group of formula -$A^{21}$-$A^{22}$-$A^{23}$, wherein $A^{21}$, $A^{22}$, and $A^{23}$ are independently chosen from —$CZ^{21}Z^{22}$—, —$CZ^{23}Z^{24}CZ^{25}Z^{26}$—, —C(=O)—, —$NZ^{27}$—, —S—, —S(=O)—, —S(=O)$_2$—, or —O—; wherein when any two of $Z^{21}$, $Z^{22}$, $Z^{23}$, $Z^{24}$, $Z^{25}$, $Z^{26}$ and $Z^{27}$ are located on adjacent atoms, they may together form a bond between the atoms, and wherein any of $Z^{21}$, $Z^{22}$, $Z^{23}$, $Z^{24}$, $Z^{25}$, $Z^{26}$ and $Z^{27}$ may be independently chosen from H and —$OR^{90}$. In another embodiment, $Z^2$ is H, $C_{1-6}$alkyl optionally substituted by 1-13 $R^{89}$, 3-15 membered heterocycloalkyl optionally substituted by 1-28 $R^{89}$, halogen, —CN, —C(=O)$OR^{80}$, —$NR^{82}R^{83}$, or —S(=O)$_n R^{80}$; alternatively, when $L^2$, $A^2$, $G^2$, $X^2$, $L^3$, $A^3$, $G^3$ and $X^3$ are absent, $Z^2$ and $Z^3$ can together form a group of formula -$A^{21}$-$A^{22}$-$A^{23}$, wherein $A^{21}$, $A^{22}$, and $A^{23}$ are independently chosen from —$CZ^{21}Z^{22}$—, —$CZ^{23}Z^{24}CZ^{25}Z^{26}$—, —C(=O)—, —$NZ^{27}$—, —S—, —S(=O)—, —S(=O)$_2$—, or —O—; wherein when any two of $Z^{21}$, $Z^{22}$, $Z^{23}$, $Z^{24}$, $Z^{25}$, $Z^{26}$ and $Z^{27}$ are located on adjacent atoms, they may together form a bond between the atoms, and wherein any of $Z^{21}$, $Z^{22}$, $Z^{23}$, $Z^{24}$, $Z^{25}$, $Z^{26}$ and $Z^{27}$ may be independently chosen from H and —$OR^{90}$. In another embodiment, $Z^2$ is H, $C_{1-6}$alkyl optionally substituted by 1-13 $R^{89}$, 3-15 membered heterocycloalkyl optionally substituted by 1-28 $R^{89}$, halogen, —CN, —C(=O)$OR^{80}$, —$NR^{82}R^{83}$, or —S(=O)$_n R^{80}$; alternatively, when $L^2$, $A^2$, $G^2$, $X^2$, $L^3$, $A^3$, $G^3$ and $X^3$ are absent, $Z^2$ and $Z^3$ can together form a group of formula -$A^{21}$-$A^{22}$-$A^{23}$, wherein $A^{21}$, $A^{22}$, and $A^{23}$ are independently chosen from —$CZ^{21}Z^{22}$— and —$CZ^{23}Z^{24}CZ^{25}Z^{26}$—; wherein when any two of $Z^{21}$, $Z^{22}$, $Z^{23}$, $Z^{24}$, $Z^{25}$, $Z^{26}$ and $Z^{27}$ are located on adjacent atoms, they may together form a bond between the atoms, and wherein any of $Z^{21}$, $Z^{22}$, $Z^{23}$, $Z^{24}$, $Z^{25}$, $Z^{26}$ and $Z^{27}$ may be independently chosen from H and —$OR^{90}$. In another embodiment, $Z^2$ is H, $C_{1-6}$alkyl optionally substituted by 1-3 $R^{89}$, 3-15 membered heterocycloalkyl optionally substituted by 1-3 $R^{89}$, halogen, —CN, —C(=O)$OR^{80}$, —$NR^{82}R^{83}$, or —S(=O)$_n R^{80}$; alternatively, when $L^2$, $A^2$, $G^2$, $X^2$, $L^3$, $A^3$, $G^3$ and $X^3$ are absent, $Z^2$ and $Z^3$ can together form a group of formula -$A^{21}$-$A^{22}$-$A^{23}$, wherein $A^{21}$, $A^{22}$, and $A^{23}$ are independently chosen from —$CZ^{21}Z^{22}$— and —$CZ^{23}Z^{24}CZ^{25}Z^{26}$—; wherein when any two of $Z^{21}$, $Z^{22}$, $Z^{23}$, $Z^{24}$, $Z^{25}$, $Z^{26}$ and $Z^{27}$ are located on adjacent atoms, they may together form a bond between the atoms, and wherein any of $Z^{21}$, $Z^{22}$, $Z^{23}$, $Z^{24}$, $Z^{25}$, $Z^{26}$ and $Z^{27}$ may be independently chosen from H and —$OR^{90}$. In another embodiment, $Z^2$ is H, $C_{1-6}$alkyl optionally substituted by 1-3 $R^{89}$, 5-6 membered heterocycloalkyl optionally substituted by 1-3 $R^{89}$, halogen, —CN, —C(=O)$OR^{80}$, —$NR^{82}R^{83}$, or —S(=O)$_2 R^{80}$; alternatively, when $L^2$, $A^2$, $G^2$, $X^2$, $L^3$, $A^3$, $G^3$ and $X^3$ are absent, $Z^2$ and $Z^3$ can together form a phenyl group optionally substituted by —$OR^{90}$. In another embodiment, $Z^2$ is H, $C_{1-6}$alkyl, 5-6 membered heterocycloalkyl, halogen, —CN, —C(=O)OH, —$NH_2$, —$NHC_{1-6}$alkyl, —$N(C_{1-6}$alkyl)$_2$, or —S(=O)$_2 C_{1-6}$alkyl; alternatively, when $L^2$, $A^2$, $G^2$, $X^2$, $L^3$, $A^3$, $G^3$ and $X^3$ are absent, $Z^2$ and $Z^3$ can together form a phenyl group optionally substituted by —OH or —$OC_{1-6}$alkyl. In another embodiment, $Z^2$ is H, $C_{1-6}$alkyl, 5-6 membered heterocycloalkyl, wherein the heterocycloalkyl group contains, in addition to carbon atoms, one or two heteroatoms chosen from nitrogen and oxygen, halogen, —CN, —C(=O)OH, —$NH_2$, —$NHC_{1-6}$alkyl, —$N(C_{1-6}$alkyl)$_2$, or —S(=O)$_2 C_{1-6}$alkyl; alternatively, when $L^2$, $A^2$, $G^2$, $X^2$, $L^3$, $A^3$, $G^3$ and $X^3$ are absent, $Z^2$ and $Z^3$ can together form a phenyl group optionally substituted by —OH or —$OC_{1-6}$alkyl. In another embodiment, $Z^2$ is H, $C_{1-6}$alkyl, morpholinyl, pyrrolidinyl, halogen, —CN, —C(=O)OH, —$NH_2$, —$NHC_{1-6}$alkyl, —$N(C_{1-6}$alkyl)$_2$, or —S(=O)$_2 C_{1-6}$alkyl; alternatively, when $L^2$, $A^2$, $G^2$, $X^2$, $L^3$, $A^3$, $G^3$ and $X^3$ are absent, $Z^2$ and $Z^3$ can together form a phenyl group optionally substituted by —OH or —$OC_{1-6}$alkyl. In another embodiment, $Z^2$ is H, $C_{1-6}$alkyl, morpholinyl, pyrrolidinyl, halogen, —CN, —C(=O)OH, —$NH_2$, —$N(C_{1-6}$alkyl)$_2$, or —S(=O)$_2 C_{1-6}$alkyl; alternatively, when $L^2$, $A^2$, $G^2$, $X^2$, $L^3$, $A^3$, $G^3$ and $X^3$ are absent, $Z^2$ and $Z^3$ can together form a phenyl group optionally substituted by —$OC_{1-6}$alkyl. In another embodiment, $Z^2$ is H, $C_{1-6}$alkyl, morpholin-4-yl, pyrrolidin-1-yl, halogen, —CN, —C(=O)OH, —$NH_2$, —$N(C_{1-6}$alkyl)$_2$, or —S(=O)$_2 C_{1-6}$alkyl; alternatively, when $L^2$, $A^2$, $G^2$, $X^2$, $L^3$, $A^3$, $G^3$ and $X^3$ are absent, $Z^2$ and $Z^3$ can together form a phenyl group optionally substituted by —$OC_{1-6}$alkyl. In another embodiment, $Z^2$ is H, methyl, ethyl, isopropyl, t-butyl, morpholin-4-yl, pyrrolidin-1-yl, halogen, —CN, —C(=O)OH, —$NH_2$, —$N(CH_3)_2$, or —S(=O)$_2 CH_3$; alternatively, when $L^2$, $A^2$, $G^2$, $X^2$, $L^3$, $A^3$, $G^3$ and $X^3$ are absent, $Z^2$ and $Z^3$ can together form a phenyl group optionally substituted by —$OCH_3$. In another embodiment, $Z^2$ is H.

In each embodiment of the present invention that is described in the paragraphs that precede or follow this paragraph, the definition of $L^3$ may be chosen from any of the embodiments that are described in this paragraph. In one embodiment, $L^3$ is —$C_{0-3}$alkylC(=O)$C_{0-3}$alkyl-, —$C_{0-3}$alkylC(=O)$OC_{0-3}$alkyl-, —$C_{0-3}$alkylC(=O)$NR^{44}C_{0-3}$alkyl-, —$C_{0-3}$alkylC(=O)C(=O)$C_{0-3}$alkyl-, —$C_{0-3}$alkylC(=$NR^{45}$)$C_{0-3}$alkyl-, —$C_{0-3}$alkylC(=$NR^{45}$)$NR^{44}C_{0-3}$alkyl-, —$C_{0-3}$alkylC(=NOH)$NR^{44}C_{0-3}$alkyl-, —$C_{0-3}$alkylC(=$NOR^{46}$)$C_{0-3}$alkyl-, —$C_{0-3}$alkylC(=$NNR^{42}R^{43}$)$C_{0-3}$alkyl-, —$C_{0-3}$alkylC(=$NNR^{44}C$(=O)$R^{41}$)$C_{0-3}$alkyl-, —$C_{0-3}$alkylC(=$NNR^{44}C$(=O)$OR^{41}$)$C_{0-3}$alkyl-, —$C_{0-3}$alkylC(=S)$NR^{44}C_{0-3}$alkyl-, —$C_{0-3}$alkyl$NR^{44}C_{0-3}$alkyl-, —$C_{0-3}$alkyl$NR^{44}NR^{44}C_{0-3}$alkyl-, —$C_{0-3}$alkylN=$NC_{0-3}$alkyl-, —$C_{0-3}$alkyl$NR^{44}C$(=O)$C_{0-3}$alkyl-, —$C_{0-3}$alkyl$NR^{44}C$(=O)C(=O)$C_{0-3}$alkyl-, —$C_{0-3}$alkyl$NR^{44}C$(=O)$OC_{0-3}$alkyl-, —$C_{0-3}$alkyl$NR^{44}C$(=O)C(=O)$OC_{0-3}$alkyl-, —$C_{0-3}$alkyl$NR^{44}C$(=O)$NR^{44}C_{0-3}$alkyl-, —$C_{0-3}$alkyl$NR^{44}C$(=O)$NR^{44}C$(=O)$C_{0-3}$alkyl-, —$C_{0-3}$alkyl$NR^{44}C$(=O)$NR^{44}C$(=O)$OC_{0-3}$alkyl-, —$C_{0-3}$alkyl$NR^{44}C$(=$NR^{45}$)$NR^{44}C_{0-3}$alkyl-, —$C_{0-3}$alkyl$NR^{44}C$(=O)C(=O)$NR^{44}C_{0-3}$alkyl-, —$C_{0-3}$alkyl$NR^{44}C$(=S)$C_{0-3}$alkyl-, —$C_{0-3}$alkyl$NR^{44}C$(=S)$OC_{0-3}$alkyl-, —$C_{0-3}$alkyl$NR^{44}C$(=S)$NR^{44}C_{0-3}$alkyl-, —$C_{0-3}$alkyl$NR^{44}S$(=O)$_2 C_{0-3}$alkyl-, —$C_{0-3}$alkyl$NR^{44}S$(=O)$_2 NR^{44}C_{0-3}$alkyl-, —$C_{0-3}$alkyl$OC_{0-3}$alkyl-, —$C_{0-3}$alkylOC(=O)$C_{0-3}$alkyl-, —$C_{0-3}$alkylOC(=O)$NR^{44}C_{0-3}$alkyl-, —$C_{0-3}$alkylOC(=O)$OC_{0-3}$alkyl-, —$C_{0-3}$alkylOC(=$NR^{45}$)$NR^{44}C_{0-3}$alkyl-, —$C_{0-3}$alkylOS(=O)$C_{0-3}$alkyl-, —$C_{0-3}$alkylOS(=O)$_2 C_{0-3}$alkyl-, —$C_{0-3}$alkylOS(=O)$_2 OC_{0-3}$alkyl-, —$C_{0-3}$alkylOS(=O)$_2 NR^{44}C_{0-3}$alkyl-, —$C_{0-3}$alkylS(=O)—$C_{0-3}$alkyl-, —$C_{0-3}$alkylS(=O)$_2 OC_{0-3}$alkyl-, —$C_{0-3}$alkylSO$_3 C_{0-3}$alkyl-, —$C_{0-3}$alkylS(=O)$_2 NR^{44}C_{0-3}$alkyl-, —$C_{0-3}$alkylS(=O)$NR^{44}C_{0-3}$alkyl-, or absent. In another embodiment, $L^3$ is —$C_{0-3}$alkylC(=O)$C_{0-3}$alkyl-, —$C_{0-3}$alkylC(=O)$OC_{0-3}$alkyl-, —$C_{0-3}$alkylC(=O)$NR^{44}C_{0-3}$alkyl-, —$C_{0-3}$alkylC(=O)C(=O)$C_{0-3}$alkyl-, —$C_{0-3}$alkylC(=S)$NR^{44}C_{0-3}$alkyl-, —$C_{0-3}$alkyl$NR^{44}C_{0-3}$alkyl-, —$C_{0-3}$alkyl$NR^{44}NR^{44}C_{0-3}$alkyl-, —C$_{0-3}$alkylNR$^{44}$C(=O)C$_{0-3}$alkyl-, —C$_{0-3}$alkylNR$^{44}$C(=O)C(=O)C$_{0-3}$alkyl-, —C$_{0-3}$alkylNR$^{44}$C(=O)OC$_{0-3}$alkyl-, —C$_{0-3}$alkylNR$^{44}$C(=O)C(=O)OC$_{0-3}$alkyl-, —C$_{0-3}$alkylNR$^{44}$C(=O)NR$^{44}$C$_{0-3}$alkyl-, —C$_{0-3}$alkylNR$^{44}$C(=O)NR$^{44}$C(=O)C$_{0-3}$alkyl-, —C$_{0-3}$alkylNR$^{44}$C(=O)NR$^{44}$C(=O)OC$_{0-3}$alkyl-, —C$_{0-3}$alkylNR$^{44}$C(=NR$^{45}$)NR$^{44}$C$_{0-3}$alkyl-, —C$_{0-3}$alkylNR$^{44}$C(=O)C(=O)NR$^{44}$C$_{0-3}$ alkyl-, —C$_{0-3}$alkylNR$^{44}$C(=S)C$_{0-3}$alkyl-, —C$_{0-3}$alkylNR$^{44}$C(=S)OC$_{0-3}$alkyl-, —C$_{0-3}$alkylNR$^{44}$C(=S)NR$^{44}$C$_{0-3}$alkyl-, —C$_{0-3}$ alkylNR$^{44}$S(=O)$_2$C$_{0-3}$alkyl-, —C$_{0-3}$ alkylNR$^{44}$S(=O)$_2$ NR$^{44}$C$_{0-3}$alkyl-, —C$_{0-3}$alkylOC$_{0-3}$ alkyl-, —C$_{0-3}$ alkylOC(=O)C$_{0-3}$alkyl-, —C$_{0-3}$alkylOC(=O)NR$^{44}$C$_{0-3}$alkyl-, —C$_{0-3}$alkylOC(=O)OC$_{0-3}$alkyl-, —C$_{0-3}$alkylOS(=O)C$_{0-3}$alkyl-, —C$_{0-3}$alkylOS(=O)$_2$C$_{0-3}$ alkyl-, —C$_{0-3}$alkylOS(=O)$_2$OC$_{0-3}$alkyl-, —C$_{0-3}$alkylOS(=O)$_2$NR$^{44}$C$_{0-3}$alkyl-, —C$_{0-3}$alkylS(=O)$_n$C$_{0-3}$alkyl-, —C$_{0-3}$alkylS(=O)$_2$OC$_{0-3}$alkyl-, —C$_{0-3}$alkylSO$_3$C$_{0-3}$alkyl-, —C$_{0-3}$alkylS(=O)$_2$NR$^{44}$C$_{0-3}$alkyl-, —C$_{0-3}$alkylS(=O)NR$^{44}$C$_{0-3}$alkyl-, or absent. In another embodiment, L$^3$ is —C$_{0-3}$alkylC(=O)C$_{0-3}$alkyl-, —C$_{0-3}$alkylC(=O)OC$_{0-3}$ alkyl-, —C$_{0-3}$alkylC(=O)NR$^{44}$C$_{0-3}$alkyl-, —C$_{0-3}$alkylC(=S)NR$^{44}$C$_{0-3}$alkyl-, —C$_{0-3}$alkylNR$^{44}$C$_{0-3}$alkyl-, —C$_{0-3}$alkylNR$^{44}$NR$^{44}$C$_{0-3}$alkyl-, —C$_{0-3}$alkylNR$^{44}$C(=O)C$_{0-3}$alkyl-, —C$_{0-3}$alkylNR$^{44}$C(=O)OC$_{0-3}$alkyl-, —C$_{0-3}$alkylNR$^{44}$C(=O)NR$^{44}$C$_{0-3}$alkyl-, —C$_{0-3}$alkylNR$^{44}$C(=O)NR$^{44}$C(=O)C$_{0-3}$alkyl-, —C$_{0-3}$ alkylNR$^{44}$C(=O)NR$^{44}$C(=O)OC$_{0-3}$alkyl-, —C$_{0-3}$ alkylNR$^{44}$C(=NR$^{45}$)NR$^{44}$C$_{0-3}$alkyl-, —C$_{0-3}$alkylNR$^{44}$C(=S)NR$^{44}$C$_{0-3}$alkyl-, —C$_{0-3}$alkylNR$^{44}$S(=O)$_2$C$_{0-3}$alkyl-, —C$_{0-3}$alkylOC$_{0-3}$alkyl-, —C$_{0-3}$alkylOC(=O)C$_{0-3}$alkyl-, —C$_{0-3}$alkylOC(=O)NR$^{44}$C$_{0-3}$alkyl-, —C$_{0-3}$alkylS(=O)—C$_{0-3}$alkyl-, —C$_{0-3}$alkylS(=O)$_2$NR$^{44}$C$_{0-3}$alkyl-, or absent. In another embodiment, L$^3$ is —C$_{0-3}$alkylC(=O)C$_{0-3}$alkyl-, —C$_{0-3}$alkylC(=O)OC$_{0-3}$alkyl-, —C$_{0-3}$alkylC(=O)NR$^{44}$C$_{0-3}$alkyl-, —C$_{0-3}$alkylNR$^{44}$C$_{0-3}$alkyl-, —C$_{0-3}$alkylNR$^{44}$C(=O)C$_{0-3}$alkyl-, —C$_{0-3}$alkylNR$^{44}$C(=O)OC$_{0-3}$alkyl-, —C$_{0-3}$alkylNR$^{44}$C(=O)NR$^{44}$C$_{0-3}$alkyl-, —C$_{0-3}$alkylNR$^{44}$S(=O)$_2$C$_{0-3}$alkyl-, —C$_{0-3}$alkylOC$_{0-3}$alkyl-, —C$_{0-3}$alkylOC(=O)C$_{0-3}$alkyl-, —C$_{0-3}$alkylOC(=O)NR$^{44}$C$_{0-3}$alkyl-, —C$_{0-3}$alkylS(=O)—C$_{0-3}$alkyl-, —C$_{0-3}$alkylS(=O)$_2$NR$^{44}$C$_{0-3}$alkyl-, or absent. In another embodiment, L$^3$ is —C(=O)—, —C(=O)O—, —C(=O)NR$^{44}$—, —C(=O)C(=O)—, —C(=S)NR$^{44}$—, —NR$^{44}$—, —NR$^{44}$NR$^{44}$—, —NR$^{44}$C(=O)—, —NR$^{44}$C(=O)C(=O)—, —NR$^{44}$C(=O)O—, —NR$^{44}$C(=O)C(=O)O—, —NR$^{44}$C(=O)NR$^{44}$—, —NR$^{44}$C(=O)NR$^{44}$C(=O)—, —NR$^{44}$C(=O)NR$^{44}$C(=O)O—, —NR$^{44}$C(=NR$^{45}$)NR$^{44}$—, —NR$^{44}$C(=O)C(=O)NR$^{44}$—, —NR$^{44}$C(=S)—, —NR—, —NR$^{44}$C(=S)NR$^{44}$—, —NR$^{44}$S(=O)$_2$—, —NR—, —O—, —OC(=O)—, —OC(=O)NR$^{44}$—, —OC(=O)O—, —OS(=O)—, —OS(=O)$_2$—, —OS(=O)$_2$O—, —OS(=O)$_2$NR$^{44}$—, —S(=O)$_n$—, —S(=O)$_2$O—, —SO$_3$—, —S(=O)$_2$NR$^{44}$—, —S(=O)NR$^{44}$—, or absent. In another embodiment, L$^3$ is —C(=O)—, —C(=O)O—, —C(=O)NR$^{44}$—, —C(=S)NR$^{44}$—, —NR$^{44}$—, —NR$^{44}$NR$^{44}$—, —NR$^{44}$C(=O)—, —NR$^{44}$C(=O)O—, —NR$^{44}$C(=O)NR$^{44}$—, —NR$^{44}$C(=O)NR$^{44}$—, —NR$^{44}$C(=O)NR$^{44}$C(=O)—, —NR$^{44}$C(=O)NR$^{44}$C(=O)O—, —NR$^{44}$C(=NR$^{45}$)NR$^{44}$—, —NR$^{44}$C(=S)NR$^{44}$—, —NR$^{44}$S(=O)$_2$—, —O—, —OC(=O)—, —OC(=O)NR$^{44}$—, —S(=O)$_n$—, —S(=O)$_2$NR$^{44}$—, or absent. In another embodiment, L$^3$ is —C(=O)—, —C(=O)O—, —C(=O)NR$^{44}$—, —C(=S)NR$^{44}$—, —NR$^{44}$—, —NR$^{44}$NR$^{44}$—, —NR$^{44}$C(=O)—, —NR$^{44}$C(=O)O—, —NR$^{44}$C(=O)NR$^{44}$—, —NR$^{44}$C(=O)NR$^{44}$C(=O)—, —NR$^{44}$C(=O)NR$^{44}$C(=O)O—, —NR$^{44}$C(=S)—, —NR$^{44}$S(=O)$_2$—, —O—, —OC(=O)—, —OC(=O)NR$^{44}$—, —S(=O)$_n$—, —S(=O)$_2$NR$^{44}$—, or absent. In another embodiment, L$^3$ is —C(=O)—, —C(=O)O—, —C(=O)NR$^{44}$—, —NR$^{44}$—, —NR$^{44}$C(O)—, —NR$^{44}$C(=O)O—, —NR$^{44}$C(=O)NR$^{44}$—, —NR$^{44}$S(=O)$_2$—, —O—, —OC(=O)—, —OC(=O)NR$^{44}$—, —S(=O)$_n$—, —S(=O)$_2$NR$^{44}$—, or absent. In another embodiment, L$^3$ is absent.

In each embodiment of the present invention that is described in the paragraphs that precede or follow this paragraph, the definition of A$^3$ may be chosen from any of the embodiments that are described in this paragraph. In one embodiment, A$^3$ is C$_{1-6}$alkylene optionally substituted by 1-12 R$^b$, C$_{2-6}$alkenylene optionally substituted by 1-10 R$^b$, C$_{2-6}$alkynylene optionally substituted by 1-8 R$^b$, C$_{6-11}$arylene optionally substituted by 1-10 R$^b$, C$_{7-16}$arylalkylene optionally substituted by 1-18 R$^b$, C$_{3-11}$cycloalkylene optionally substituted by 1-20 R$^b$, C$_{4-17}$cycloalkylalkylene optionally substituted by 1-31 R$^b$, 3-15 membered heterocycloalkylene optionally substituted by 1-27 R$^b$, 4-21 membered heterocycloalkylalkylene optionally substituted by 1-39 R$^b$, 5-15 membered heteroarylene optionally substituted by 1-14 R$^b$, 6-21 membered heteroarylalkylene optionally substituted by 1-26 R$^b$, or absent. In another embodiment, A$^3$ is C$_{1-6}$alkylene optionally substituted by 1-12 R$^b$, C$_{6-11}$arylene optionally substituted by 1-6 R$^b$, C$_{7-16}$arylalkylene optionally substituted by 1-18 R$^b$, C$_{3-11}$cycloalkylene optionally substituted by 1-20 R$^b$, C$_{4-6}$cycloalkylalkylene optionally substituted by 1-31 R$^b$, 3-15 membered heterocycloalkylene optionally substituted by 1-27 R$^b$, 4-21 membered heterocycloalkylalkylene optionally substituted by 1-39 R$^b$, 5-15 membered heteroarylene optionally substituted by 1-14 R$^b$, 6-21 membered heteroarylalkylene optionally substituted by 1-26 R$^b$, or absent. In another embodiment, A$^3$ is C$_{1-6}$alkylene optionally substituted by 1-12 R$^b$, C$_{6-11}$arylene optionally substituted by 1-6 R$^b$, C$_{3-11}$cycloalkylene optionally substituted by 1-20 R$^b$, 3-15 membered heterocycloalkylene optionally substituted by 1-27 R$^b$, 5-15 membered heteroarylene optionally substituted by 1-14 R$^b$, or absent. In another embodiment, A$^3$ is C$_{1-6}$alkylene optionally substituted by 1-12 R$^b$, C$_{6-11}$arylene optionally substituted by 1-6 R$^b$, C$_{3-10}$cycloalkylene optionally substituted by 1-20 R$^b$, 3-10 membered heterocycloalkylene optionally substituted by 1-27 R$^b$, 5-10 membered heteroarylene optionally substituted by 1-14 R$^b$, or absent. In another embodiment, A$^3$ is C$_{1-6}$alkylene optionally substituted by 1-6 R$^b$, C$_{6-11}$arylene optionally substituted by 1-6 R$^b$, C$_{7-16}$arylalkylene optionally substituted by 1-6 R$^b$, C$_{3-11}$cycloalkylene optionally substituted by 1-6 R$^b$, C$_{4-17}$cycloalkylalkylene optionally substituted by 1-6 R$^b$, 3-15 membered heterocycloalkylene optionally substituted by 1-6 R$^b$, 4-21 membered heterocycloalkylalkylene optionally substituted by 1-6 R$^b$, 5-15 membered heteroarylene optionally substituted by 1-6 R$^b$, 6-21 membered heteroarylalkylene optionally substituted by 1-6 R$^b$, or absent. In another embodiment, A$^3$ is C$_{1-6}$alkylene optionally substituted by 1-6 R$^b$, C$_{6-11}$ arylene optionally substituted by 1-6 R$^b$, C$_{3-11}$cycloalkylene optionally substituted by 1-6 $R^b$, 3-15 membered heterocycloalkylene optionally substituted by 1-6 $R^b$, 5-15 membered heteroarylene optionally substituted by 1-6 $R^b$, or absent. In another embodiment, $A^3$ is $C_{1-6}$alkylene optionally substituted by 1-6 $R^b$, $C_{6-11}$arylene optionally substituted by 1-6 $R^b$, $C_{3-10}$cycloalkylene optionally substituted by 1-6 $R^b$, 3-10 membered heterocycloalkylene optionally substituted by 1-6 $R^b$, 5-10 membered heteroarylene optionally substituted by 1-6 $R^b$, or absent. In another embodiment, $A^3$ is $C_{1-6}$alkylene optionally substituted by 1-6 $R^b$, phenylene optionally substituted by 1-4 $R^b$, $C_{3-6}$cycloalkylene optionally substituted by 1-6 $R^b$, 3-7 membered heterocycloalkylene optionally substituted by 1-3 $R^b$, 5-6 membered heteroarylene optionally substituted by 1-3 $R^b$, or absent. In another embodiment, $A^3$ is phenylene optionally substituted by 1-4 $R^b$, 5-6 membered heteroarylene optionally substituted by 1-3 $R^b$, or absent. In another embodiment, $A^3$ is phenylene optionally substituted by 1-4 $R^b$, 6 membered heteroarylene optionally substituted by 1-6 $R^b$, or absent. In another embodiment, $A^3$ is 5-6 membered heteroarylene optionally substituted by 1-3 $R^b$, or absent. In another embodiment, $A^3$ is 6 membered heteroarylene optionally substituted by 1-3 $R^b$, or absent. In another embodiment, $A^3$ is 6 membered heteroarylene optionally substituted by 1-3 $R^b$, or absent; wherein the heteroarylene group contains, in addition to carbon atoms, 1-3 nitrogen atoms. In another embodiment, $A^3$ is pyridinylene optionally substituted by 1-3 $R^b$, or absent. In another embodiment, $A^3$ is absent.

In each embodiment of the present invention that is described in the paragraphs that precede or follow this paragraph, the definition of $G^3$ may be chosen from any of the embodiments that are described in this paragraph. In one embodiment, $G^3$ is $C_{1-6}$alkylene optionally substituted by 1-12 $R^{69}$, $C_{2-6}$alkenylene optionally substituted by 1-10 $R^{69}$, $C_{2-6}$alkynylene optionally substituted by 1-8 $R^{69}$, $C_{6-11}$arylene optionally substituted by 1-10 $R^{69}$, $C_{7-16}$arylalkylene optionally substituted by 1-18 $R^{69}$, $C_{3-11}$cycloalkylene optionally substituted by 1-20 $R^{69}$, $C_{4-17}$cycloalkylalkylene optionally substituted by 1-31 $R^{69}$, 3-15 membered heterocycloalkylene optionally substituted by 1-27 $R^{69}$, 4-21 membered heterocycloalkylalkylene optionally substituted by 1-39 $R^{69}$, 5-15 membered heteroarylene optionally substituted by 1-14 $R^{69}$, 6-21 membered heteroarylalkylene optionally substituted by 1-26 $R^{69}$, —$C_{0-3}$alkylC(=O)$C_{0-3}$alkyl-, —$C_{0-3}$alkylC(=O)O$C_{0-3}$alkyl-, —$C_{0-3}$alkylC(=O)NR$^{64}C_{0-3}$alkyl-, —$C_{0-3}$alkylC(=O)C(=O)$C_{0-3}$alkyl-, —$C_{0-3}$alkylC(=NR$^{65}$)$C_{0-3}$alkyl-, —$C_{0-3}$alkylC(=NR$^{65}$)NR$^{64}C_{0-3}$alkyl-, —$C_{0-3}$alkylC(=NOH)NR$^{64}C_{0-3}$alkyl-, —$C_{0-3}$alkylC(=NOR$^{66}$)$C_{0-3}$alkyl-, —$C_{0-3}$alkylC(=NNR$^{62}R^{63}$)$C_{0-3}$alkyl-, —$C_{0-3}$alkylC(=NNR$^{64}$C(=O)R$^{61}$)$C_{0-3}$alkyl-, —$C_{0-3}$alkylC(=NNR$^{64}$C(=O)OR$^{61}$)$C_{0-3}$alkyl-, —$C_{0-3}$alkylC(=S)NR$^{64}C_{0-3}$alkyl-, —$C_{0-3}$alkylNR$^{64}C_{0-3}$alkyl-, —$C_{0-3}$alkylNR$^{64}$NR$^{64}C_{0-3}$alkyl-, —$C_{0-3}$alkylN=NC$_{0-3}$alkyl-, —$C_{0-3}$alkylNR$^{64}$C(=O)$C_{0-3}$alkyl-, —$C_{0-3}$alkylNR$^{64}$C(=O)C(=O)$C_{0-3}$alkyl-, —$C_{0-3}$alkylNR$^{64}$C(=O)O$C_{0-3}$alkyl-, —$C_{0-3}$alkylNR$^{64}$C(=O)C(=O)O$C_{0-3}$alkyl-, —$C_{0-3}$alkylNR$^{64}$C(=O)NR$^{64}C_{0-3}$alkyl-, —$C_{0-3}$alkylNR$^{64}$C(=O)NR$^{64}$C(=O)$C_{0-3}$alkyl-, —$C_{0-3}$alkylNR$^{64}$C(=O)NR$^{64}$C(=O)O$C_{0-3}$alkyl-, —$C_{0-3}$alkylNR$^{64}$C(=NR$^{65}$)NR$^{64}C_{0-3}$alkyl-, —$C_{0-3}$alkylNR$^{64}$C(=O)C(=O)NR$^{64}C_{0-3}$alkyl-, —$C_{0-3}$alkylNR$^{64}$C(=S)$C_{0-3}$alkyl-, —$C_{0-3}$alkylNR$^{64}$C(=S)O$C_{0-3}$alkyl-, —$C_{0-3}$alkylNR$^{64}$C(=S)NR$^{64}C_{0-3}$alkyl-, —$C_{0-3}$alkylNR$^{64}$S(=O)$_2$$C_{0-3}$alkyl-, —$C_{0-3}$alkylNR$^{64}$S(=O)$_2$NR$^{64}C_{0-3}$alkyl-, —$C_{0-3}$alkylOC$_{0-3}$alkyl-, —$C_{0-3}$alkylOC(=O)$C_{0-3}$alkyl-, —$C_{0-3}$alkylOC(=O)NR$^{64}C_{0-3}$alkyl-, —$C_{0-3}$alkylOC(=O)O$C_{0-3}$alkyl-, —$C_{0-3}$alkylOC(=NR$^{65}$)NR$^{64}C_{0-3}$alkyl-, —$C_{0-3}$alkylOS(=O)$C_{0-3}$alkyl-, —$C_{0-3}$alkylOS(=O)$_2C_{0-3}$alkyl-, —$C_{0-3}$alkylOS(=O)$_2$O$C_{0-3}$alkyl-, —$C_{0-3}$alkylOS(=O)$_2$NR$^{64}C_{0-3}$akyl-, —$C_{0-3}$alkylS(=O)—$C_{0-3}$alkyl-, —$C_{0-3}$alkylS(=O)$_2$O$C_{0-3}$alkyl-, —$C_{0-3}$alkylSO$_3C_{0-3}$alkyl-, —$C_{0-3}$alkylS(=O)$_2$ NR$^{64}C_{0-3}$alkyl-, —$C_{0-3}$alkylS(=O)NR$^{64}C_{0-3}$alkyl-, or absent. In another embodiment, $G^3$ is $C_{1-6}$alkylene optionally substituted by 1-12 $R^{69}$, $C_{6-11}$arylene optionally substituted by 1-6 $R^{69}$, $C_{7-16}$arylalkylene optionally substituted by 1-18 $R^{69}$, $C_{3-11}$cycloalkylene optionally substituted by 1-20 $R^{69}$, $C_{4-17}$cycloalkylalkylene optionally substituted by 1-6 $R^{69}$, 3-15 membered heterocycloalkylene optionally substituted by 1-27 $R^{69}$, 4-21 membered heterocycloalkylalkylene optionally substituted by 1-39 $R^{69}$, 5-15 membered heteroarylene optionally substituted by 1-14 $R^{69}$, 6-21 membered heteroarylalkylene optionally substituted by 1-26 $R^{69}$, —$C_{0-3}$alkylC(=O)$C_{0-3}$alkyl-, —$C_{0-3}$alkylC(=O)O$C_{0-3}$alkyl-, —$C_{0-3}$alkylC(=O)NR$^{64}C_{0-3}$alkyl-, —$C_{0-3}$alkylC(=S)NR$^{64}C_{0-3}$alkyl-, —$C_{0-3}$lkylNR$^{64}C_{0-3}$alkyl-, —$C_{0-3}$alkylNR$^{64}$NR$^{64}C_{0-3}$alkyl-, —$C_{0-3}$alkylNR$^{64}$C(=O)$C_{0-3}$alkyl-, —$C_{0-3}$alkylNR$^{64}$C(=O)O$C_{0-3}$alkyl-, —$C_{0-3}$alkylNR$^{64}$C(=O)NR$^{64}C_{0-3}$alkyl-, —$C_{0-3}$alkylNR$^{64}$C(=O)NR$^{64}$C(=O)$C_{0-3}$alkyl-, —$C_{0-3}$alkylNR$^{64}$C(=NR$^{65}$)NR$^{64}C_{0-3}$alkyl-, —$C_{0-3}$alkylNR$^{64}$C(=S)$C_{0-3}$alkyl-, —$C_{0-3}$alkylNR$^{64}$C(=S)NR$^{64}C_{0-3}$alkyl-, —$C_{0-3}$alkylNR$^{64}$S(=O)$_2$$C_{0-3}$alkyl-, —$C_{0-3}$alkylOC$_{0-3}$alkyl-, —$C_{0-3}$alkylOC(=O)$C_{0-3}$alkyl-, —$C_{0-3}$alkylOC(=O)NR$^{64}C_{0-3}$alkyl-, —$C_{0-3}$alkylS(=O)—$C_{0-3}$alkyl-, —$C_{0-3}$alkylS(=O)$_2$NR$^{64}C_{0-3}$ alkyl-, or absent. In another embodiment, $G^3$ is $C_{1-6}$alkylene optionally substituted by 1-12 $R^{69}$, $C_{6-11}$arylene optionally substituted by 1-6 $R^{69}$, $C_{7-16}$arylalkylene optionally substituted by 1-18 $R^{69}$, $C_{3-11}$cycloalkylene optionally substituted by 1-20 $R^{69}$, $C_{4-17}$cycloalkylalkylene optionally substituted by 1-6 $R^{69}$ 3-15 membered heterocycloalkylene optionally substituted by 1-27 $R^{69}$, 4-21 membered heterocycloalkylalkylene optionally substituted by 1-39 $R^{69}$, 5-15 membered heteroarylene optionally substituted by 1-14 $R^{69}$, 6-21 membered heteroarylalkylene optionally substituted by 1-26 $R^{69}$, —$C_{0-3}$alkylC(=O)$C_{0-3}$alkyl-, —$C_{0-3}$alkylC(=O)O$C_{0-3}$alkyl-, —$C_{0-3}$alkylC(=O)N$R^{64}C_{0-3}$alkyl-, —$C_{0-3}$alkylC(=S)N$R^{64}C_{0-3}$alkyl-, —$C_{0-3}$alkylN$R^{64}C_{0-3}$alkyl-, —$C_{0-3}$alkylN$R^{64}$C(=O)$C_{0-3}$alkyl-, —$C_{0-3}$alkylN$R^{64}$C(=O)O$C_{0-3}$alkyl-, —$C_{0-3}$alkylN$R^{64}$C(=O)N$R^{64}C_{0-3}$alkyl-, —$C_{0-3}$alkylN$R^{64}$C(=O)N$R^{64}$C(=O)$C_{0-3}$alkyl-, —$C_{0-3}$alkylN$R^{64}$C(=S)$C_{0-3}$alkyl-, —$C_{0-3}$alkylN$R^{64}$S(=O)$_2C_{0-3}$alkyl-, —$C_{0-3}$alkylO$C_{0-3}$alkyl-, —$C_{0-3}$alkylOC(=O)$C_{0-3}$alkyl-, —$C_{0-3}$alkylOC(=O)N$R^{64}C_{0-3}$alkyl-, —$C_{0-3}$alkylS(=O)—$C_{0-3}$alkyl-, —$C_{0-3}$alkylS(=O)$_2N R^{64}C_{0-3}$alkyl-, or absent. In another embodiment, $G^3$ is $C_{1-6}$alkylene optionally substituted by 1-12 $R^{69}$, $C_{6-11}$arylene optionally substituted by 1-6 $R^{69}$, $C_{3-11}$cycloalkylene optionally substituted by 1-20 $R^{69}$, 3-15 membered heterocycloalkylene optionally substituted by 1-27 $R^{69}$, 5-15 membered heteroarylene optionally substituted by 1-14 $R^{69}$, —$C_{0-3}$alkylC(=O)$C_{0-3}$alkyl-, —$C_{0-3}$alkylC(=O)O$C_{0-3}$alkyl-, —$C_{0-3}$alkylC(=O)N$R^{64}C_{0-3}$alkyl-, —$C_{0-3}$alkylN$R^{64}C_{0-3}$alkyl-, —$C_{0-3}$alkylN$R^{64}$C(=O)$C_{0-3}$alkyl-, —$C_{0-3}$alkylN$R^{64}$C(=O)O$C_{0-3}$alkyl-, —$C_{0-3}$alkylN$R^{64}$C(=O)N$R^{64}C_{0-3}$alkyl-, —$C_{0-3}$alkylN$R^{64}$S(=O)$_2C_{0-3}$alkyl-, —$C_{0-3}$alkylO$C_{0-3}$alkyl-, —$C_{0-3}$alkylOC(=O)$C_{0-3}$alkyl-, —$C_{0-3}$alkylOC(=O)N$R^{64}C_{0-3}$alkyl-, —$C_{0-3}$alkylS(=O)—$C_{0-3}$alkyl-, —$C_{0-3}$alkylS(=O)$_2 NR^{64}C_{0-3}$alkyl-, or absent. In another embodiment, $G^3$ is $C_{1-6}$alkylene optionally substituted by 1-6 $R^{69}$, $C_{6-11}$ arylene optionally substituted by 1-6 $R^{69}$, $C_{7-16}$arylalkylene optionally substituted by 1-6 $R^{69}$, $C_{3-11}$cycloalkylene optionally substituted by 1-6 $R^{69}$, $C_{4-6}$cycloalkylalkylene optionally substituted by 1-6 $R^{69}$, 3-15 membered heterocycloalkylene optionally substituted by 1-6 $R^{69}$, 4-21 membered heterocycloalkylalkylene optionally substituted by 1-6 $R^{69}$, 5-15 membered heteroarylene optionally substituted by 1-6 $R^{69}$, 6-21 membered heteroarylalkylene optionally substituted by 1-6 $R^{69}$, —C(=O)—, —C(=O)O—, —C(=O)N$R^{64}$—, —C(=O)C(=O)—, —C(=S)N$R^{64}$—, —N$R^{64}$—, —N$R^{64}$N$R^{64}$—, —N$R^{64}$C(=O)—, —N$R^{64}$C(=O)C(=O)—, —N$R^{64}$C(=O)O—, —N$R^{64}$C(=O)C(=O)O—, —N$R^{64}$C(=O)N$R^{64}$—, —N$R^{64}$C(=O)N$R^{64}$C(=O)—, —N$R^{64}$C(=O)N$R^{64}$C(=O)O—, —N$R^{64}$C(=N$R^{65}$)N$R^{64}$—, —N$R^{64}$C(=O)C(=O)N$R^{64}$—, —N$R^{64}$C(=S)—, —N$R^{64}$C(=S)O—, —N$R^{64}$C(=S)N$R^{64}$—, —N$R^{64}$S(=O)$_2$—, —NR—, —O—, —OC(=O)—, —OC(=O)N$R^{64}$—, —OC(=O)O—, —OS(=O)—, —OS(=O)$_2$—, —OS(=O)$_2$O—, —OS(=O)$_2$N$R^{64}$—, —S(=O)$_n$—, —S(=O)$_2$O—, —SO$_3$—, —S(=O)$_2$N$R^{64}$—, —S(=O)N$R^{64}$—, or absent.

In another embodiment, $G^3$ is $C_{1-6}$alkylene optionally substituted by 1-6 $R^{69}$, $C_{6-11}$ arylene optionally substituted by 1-6 $R^{69}$, $C_{7-16}$arylalkylene optionally substituted by 1-6 $R^{69}$, $C_{3-11}$cycloalkylene optionally substituted by 1-6 $R^{69}$, $C_{4-17}$cycloalkylalkylene optionally substituted by 1-6 $R^{69}$, 3-15 membered heterocycloalkylene optionally substituted by 1-6 $R^{69}$, 4-21 membered heterocycloalkylalkylene optionally substituted by 1-6 $R^{69}$, 5-15 membered heteroarylene optionally substituted by 1-6 $R^{69}$, 6-21 membered heteroarylalkylene optionally substituted by 1-6 $R^{69}$, —C(=O)—, —C(=O)O—, —C(=O)N$R^{64}$—, —C(=S)N$R^{64}$—, —N$R^{64}$—, —N$R^{64}$C(=O)—, —N$R^{64}$C(=O)O—, —NR—, —N$R^{64}$C(=O)N$R^{64}$C(=O)—, —N$R^{64}$C(=S)—, —N$R^{64}$S(=O)$_2$—, —O—, —OC(=O)—, —OC(=O)N$R^{64}$—, —S(=O)$_n$—, —S(=O)$_2$N$R^{64}$—, or absent. In another embodiment, $G^3$ is $C_{1-6}$alkylene optionally substituted by 1-6 $R^{69}$, $C_{6-11}$arylene optionally substituted by 1-6 $R^{69}$, $C_{3-11}$cycloalkylene optionally substituted by 1-6 $R^{69}$, 3-15 membered heterocycloalkylene optionally substituted by 1-6 $R^{69}$, 5-15 membered heteroarylene optionally substituted by 1-6 $R^{69}$, —C(=O)—, —C(=O)O—, —C(=O)N$R^{64}$—, —N$R^{64}$—, —N$R^{64}$C(=O)—, —N$R^{64}$C(=O)O—, —N$R^{64}$C(=O)N$R^{64}$—, —N$R^{64}$S(=O)$_2$—, —$C_{0-3}$alkylO$C_{0-3}$alkyl-, —OC(=O)—, —OC(=O)N$R^{64}$—, —S(=O)$_n$—, —S(=O)$_2$N$R^{64}$—, or absent. In another embodiment, $G^3$ is —$C_{0-3}$alkylO$C_{0-3}$alkyl- or absent. In another embodiment, $G^3$ is $C_{1-6}$alkylene optionally substituted by 1-6 $R^{69}$, $C_{6-11}$arylene optionally substituted by 1-6 $R^{69}$, $C_{3-11}$cycloalkylene optionally substituted by 1-6 $R^{69}$, 3-15 membered heterocycloalkylene optionally substituted by 1-6 $R^{69}$, 5-15 membered heteroarylene optionally substituted by 1-6 $R^{69}$, —C(=O)—, —C(=O)O—, —C(=O)N$R^{64}$—, —N$R^{64}$—, —N$R^{64}$C(=O)—, —N$R^{64}$C(=O)O—, —NR—, —N$R^{64}$S(=O)$_2$—, —O—, —OC(=O)—, —OC(=O)N$R^{64}$—, —S(=O)$_n$—, —S(=O)$_2$N$R^{64}$—, or absent. In another embodiment, $G^3$ is —O— or absent. In another embodiment, $G^3$ is absent.

In each embodiment of the present invention that is described in the paragraphs that precede or follow this paragraph, the definition of $X^3$ may be chosen from any of the embodiments that are described in this paragraph. In one embodiment, $X^3$ is $C_{1-6}$alkylene optionally substituted by 1-12 $R^{79}$, $C_{2-6}$alkenylene optionally substituted by 1-10 $R^{79}$, $C_{2-6}$alkynylene optionally substituted by 1-8 $R^{79}$, $C_{6-11}$arylene optionally substituted by 1-10 $R^{79}$, $C_{7-16}$arylalkylene optionally substituted by 1-18 $R^{79}$, $C_{3-11}$cycloalkylene optionally substituted by 1-20 $R^{79}$, $C_{4-17}$cycloalkylalkylene optionally substituted by 1-31 $R^{79}$, 3-15 membered heterocycloalkylene optionally substituted by 1-27 $R^{79}$, 4-21 membered heterocycloalkylalkylene optionally substituted by 1-39 $R^{79}$, 5-15 membered heteroarylene optionally substituted by 1-14 $R^{79}$, 6-21 membered heteroarylalkylene optionally substituted by 1-26 $R^{79}$, —$C_{0-3}$alkylC(=O)$C_{0-3}$alkyl-, —$C_{0-3}$alkylC(=O)O$C_{0-3}$alkyl-, —$C_{0-3}$alkylC(=O)N$R^{74}C_{0-3}$alkyl-, —$C_{0-3}$alkylC(=O)C(=O)$C_{0-3}$alkyl-, —$C_{0-3}$alkylC(=N$R^{75}$)$C_{0-3}$alkyl-, —$C_{0-3}$alkylC(=N$R^{75}$)N$R^{74}C_{0-3}$alkyl-, —$C_{0-3}$alkylC(=NOH)N$R^{74}C_{0-3}$alkyl-, —$C_{0-3}$alkylC(=NO$R^{76}$)$C_{0-3}$alkyl-, —$C_{0-3}$alkylC(=NN$R^{72}R^{73}$)$C_{0-3}$alkyl-, —$C_{0-3}$alkylC(=NN$R^{74}$C(=O)$R^{71}$)$C_{0-3}$alkyl-, —$C_{0-3}$alkylC(=NN$R^{74}$C(=O)O$R^{71}$)$C_{0-3}$alkyl-, —$C_{0-3}$alkylC(=S)N$R^{74}C_{0-3}$alkyl-, —$C_{0-3}$alkylN$R^{74}C_{0-3}$alkyl-, —$C_{0-3}$alkylN$R^{74}$N$R^{74}C_{0-3}$alkyl-, —$C_{0-3}$alkylN=N$C_{0-3}$alkyl-, —$C_{0-3}$alkylN$R^{74}$C(=O)$C_{0-3}$alkyl-, —$C_{0-3}$alkylN$R^{74}$C(=O)C(=O)$C_{0-3}$alkyl-, —$C_{0-3}$alkylN$R^{74}$C(=O)O$C_{0-3}$alkyl-, —$C_{0-3}$alkylN$R^{74}$C(=O)C(=O)O$C_{0-3}$alkyl-, —$C_{0-3}$alkylN$R^{74}$C(=O)N$R^{74}C_{0-3}$alkyl-, —$C_{0-3}$alkylN$R^{74}$C(=O)N$R^{74}$C(=O)$C_{0-3}$alkyl-, —$C_{0-3}$alkylN$R^{74}$C(=O)N$R^{74}$C(=O)O$C_{0-3}$alkyl-, —$C_{0-3}$alkylN$R^{74}$C(=N$R^{75}$)N$R^{74}C_{0-3}$alkyl-, —$C_{0-3}$alkylN$R^{74}$C(=O)C(=O)N$R^{74}C_{0-3}$alkyl-, —$C_{0-3}$alkylN$R^{74}$C(=S)$C_{0-3}$ alkyl-, —$C_{0-3}$alkylNR$^{74}$C(=S)OC$_{0-3}$alkyl-, —$C_{0-3}$alkylNR$^{74}$C(=S)NR$^{74}$C$_{0-3}$alkyl-, —$C_{0-3}$alkylNR$^{74}$S(=O)$_2$C$_{0-3}$alkyl-, —$C_{0-3}$alkylNR$^{74}$S(=O)$_2$NR$^{74}$C$_{0-3}$alkyl-, —$C_{0-3}$alkylOC$_{0-3}$alkyl-, —$C_{0-3}$alkylOC(=O)C$_{0-3}$alkyl-, —$C_{0-3}$alkylOC(=O)NR$^{74}$C$_{0-3}$alkyl-, —$C_{0-3}$alkylOC(=O)OC$_{0-3}$alkyl-, —$C_{0-3}$alkylOC(=NR$^{75}$)NR$^{74}$C$_{0-3}$alkyl-, —$C_{0-3}$alkylOS(=O)C$_{0-3}$alkyl-, —$C_{0-3}$alkylOS(=O)$_2$C$_{0-3}$ alkyl-, —$C_{0-3}$alkylOS(=O)$_2$OC$_{0-3}$alkyl-, —$C_{0-3}$alkylOS(=O)$_2$NR$^{74}$C$_{0-3}$alkyl-, —$C_{0-3}$alkylS(=O)—C$_{0-3}$alkyl-, —$C_{0-3}$alkylS(=O)$_2$OC$_{0-3}$alkyl-, —$C_{0-3}$alkylSO$_3$C$_{0-3}$alkyl-, —$C_{0-3}$alkylS(=O)$_2$NR$^{74}$C$_{0-3}$alkyl-, —$C_{0-3}$alkylS(=O)NR$^{74}$C$_{0-3}$alkyl-, or absent. In another embodiment, $X^3$ is $C_{1-6}$alkylene optionally substituted by 1-12 R$^{79}$, $C_{6-11}$arylene optionally substituted by 1-6 R$^{79}$, $C_{7-16}$arylalkylene optionally substituted by 1-18 R$^{79}$, $C_{3-11}$cycloalkylene optionally substituted by 1-20 R$^{79}$, $C_{4-17}$cycloalkylalkylene optionally substituted by 1-31 R$^{79}$, 3-15 membered heterocycloalkylene optionally substituted by 1-27 R$^{79}$, 4-21 membered heterocycloalkylalkylene optionally substituted by 1-39 R$^{79}$, 5-15 membered heteroarylene optionally substituted by 1-14 R$^{79}$, 6-21 membered heteroarylalkylene optionally substituted by 1-26 R$^{79}$, —$C_{0-3}$alkylC(=O)C$_{0-3}$alkyl-, —$C_{0-3}$alkylC(=O)OC$_{0-3}$alkyl-, —$C_{0-3}$alkylC(=O)NR$^{74}$C$_{0-3}$alkyl-, —$C_{0-3}$ alkylC(=O)C(=O)C$_{0-3}$alkyl-, —$C_{0-3}$alkylC(=S)NR$^{74}$C$_{0-3}$alkyl-, —$C_{0-3}$alkylNR$^{74}$C$_{0-3}$alkyl-, —$C_{0-3}$alkylNR$^{74}$NR$^{74}$C$_{0-3}$ alkyl-, —$C_{0-3}$alkylNR$^{74}$C(=O)C$_{0-3}$alkyl-, —$C_{0-3}$ alkylNR$^{74}$C(=O)C(=O)C$_{0-3}$alkyl-, —$C_{0-3}$alkylNR$^{74}$C(=O)OC$_{0-3}$alkyl-, —$C_{0-3}$alkylNR$^{74}$C(=O)C(=O)OC$_{0-3}$ alkyl-, —$C_{0-3}$alkylNR$^{74}$C(=O)NR$^{74}$C$_{0-3}$alkyl-, —$C_{0-3}$ alkylNR$^{74}$C(=O)NR$^{74}$C(=O)C$_{0-3}$alkyl-, —$C_{0-3}$ alkylNR$^{74}$C(=O)NR$^{74}$C(=O)OC$_{0-3}$alkyl-, —$C_{0-3}$alkylNR$^{74}$C(=NR$^{75}$)NR$^{74}$C$_{0-3}$alkyl-, —$C_{0-3}$alkylNR$^{74}$C(=O)C(=O)NR$^{74}$C$_{0-3}$alkyl-, —$C_{0-3}$alkylNR$^{74}$C(=S)C$_{0-3}$alkyl-, —$C_{0-3}$alkylNR$^{74}$C(=S)OC$_{0-3}$alkyl-, —$C_{0-3}$alkylNR$^{74}$C(=S)NR$^{74}$C$_{0-3}$alkyl-, —$C_{0-3}$alkylNR$^{74}$S(=O)$_2$C$_{0-3}$alkyl-, —$C_{0-3}$alkylNR$^{74}$S(=O)$_2$NR$^{74}$C$_{0-3}$alkyl-, —$C_{0-3}$alkylOC$_{0-3}$alkyl-, —$C_{0-3}$alkylOC(=O)C$_{0-3}$alkyl-, —$C_{0-3}$alkylOC(=O)NR$^{74}$C$_{0-3}$alkyl-, —$C_{0-3}$alkylOC(=O)OC$_{0-3}$alkyl-, —$C_{0-3}$alkylOS(=O)C$_{0-3}$alkyl-, —$C_{0-3}$alkylOS(=O)$_2$ C$_{0-3}$alkyl-, —$C_{0-3}$alkylOS(=O)$_2$OC$_{0-3}$alkyl-, —$C_{0-3}$alkylOS(=O)$_2$NR$^{74}$C$_{0-3}$alkyl-, —$C_{0-3}$alkylS(=O)$_n$C$_{0-3}$alkyl-, —$C_{0-3}$alkylS(=O)$_2$OC$_{0-3}$alkyl-, —$C_{0-3}$alkylSO$_3$C$_{0-3}$alkyl-, —$C_{0-3}$alkylS(=O)$_2$NR$^{74}$C$_{0-3}$alkyl-, —$C_{0-3}$alkylS(=O)NR$^{74}$C$_{0-3}$alkyl-, or absent. In another embodiment, $X^3$ is $C_{1-6}$alkylene optionally substituted by 1-12 R$^{79}$, $C_{6-11}$arylene optionally substituted by 1-6 R$^{79}$, $C_{7-16}$arylalkylene optionally substituted by 1-18 R$^{79}$, $C_{3-11}$cycloalkylene optionally substituted by 1-20 R$^{79}$, $C_{4-17}$cycloalkylalkylene optionally substituted by 1-31 R$^{79}$, 3-15 membered heterocycloalkylene optionally substituted by 1-27 R$^{79}$, 4-21 membered heterocycloalkylalkylene optionally substituted by 1-39 R$^{79}$, 5-15 membered heteroarylene optionally substituted by 1-14 R$^{79}$, 6-21 membered heteroarylalkylene optionally substituted by 1-26 R$^{79}$, —$C_{0-3}$alkylC(=O)C$_{0-3}$lkyl-, —$C_{0-3}$alkylC(=O)OC$_{0-3}$alkyl-, —$C_{0-3}$alkylC(=O)NR$^{74}$C$_{0-3}$alkyl-, —$C_{0-3}$ alkylC(=S)NR$^{74}$C$_{0-3}$alkyl-, —$C_{0-3}$lkylNR$^{74}$C$_{0-3}$alkyl-, —$C_{0-3}$alkylNR$^{74}$NR$^{74}$C$_{0-3}$alkyl-, —$C_{0-3}$ alkylNR$^{74}$C(=O)C$_{0-3}$alkyl-, —$C_{0-3}$alkylNR$^{74}$C(=O)OC$_{0-3}$ alkyl-, —$C_{0-3}$ alkylNR$^{74}$C(=O)NR$^{74}$C$_{0-3}$alkyl-, —$C_{0-3}$ alkylNR$^{74}$C(=O)NR$^{74}$C(=O)C$_{0-3}$alkyl-, —$C_{0-3}$ alkylNR$^{74}$C(=O)NR$^{74}$C(=O)OC$_{0-3}$alkyl-, —$C_{0-3}$alkylNR$^{74}$C(=NR$^{75}$)NR$^{74}$C$_{0-3}$alkyl-, —$C_{0-3}$alkylNR$^{74}$C(=S)C$_{0-3}$alkyl-, —$C_{0-3}$ alkylNR$^{74}$C(=S)NR$^{74}$C$_{0-3}$alkyl-, —$C_{0-3}$alkylNR$^{74}$S(=O)$_2$C$_{0-3}$alkyl-, —$C_{0-3}$alkylOC$_{0-3}$ alkyl-, —$C_{0-3}$alkylOC(=O)C$_{0-3}$alkyl-, —$C_{0-3}$alkylOC(=O)NR$^{74}$C$_{0-3}$alkyl-, —$C_{0-3}$ alkylS(=O)—C$_{0-3}$alkyl-, —$C_{0-3}$alkylS(=O)$_2$NR$^{74}$C$_{0-3}$ alkyl-, or absent. In another embodiment, $X^3$ is $C_{1-6}$alkylene optionally substituted by 1-12 R$^{79}$, $C_{6-11}$arylene optionally substituted by 1-6 R$^{79}$, $C_{7-16}$arylalkylene optionally substituted by 1-18 R$^{79}$, $C_{3-11}$cycloalkylene optionally substituted by 1-20 R$^{79}$, $C_{4-6}$cycloalkylalkylene optionally substituted by 1-31 R$^{79}$, 3-15 membered heterocycloalkylene optionally substituted by 1-27 R$^{79}$, 4-21 membered heterocycloalkylalkylene optionally substituted by 1-39 R$^{79}$, 5-15 membered heteroarylene optionally substituted by 1-14 R$^{79}$, 6-21 membered heteroarylalkylene optionally substituted by 1-26 R$^{79}$, —$C_{0-3}$alkylC(=O)C$_{0-3}$alkyl-, —$C_{0-3}$alkylC(=O)OC$_{0-3}$ alkyl-, —$C_{0-3}$alkylC(=O)NR$^{74}$C$_{0-3}$alkyl-, —$C_{0-3}$alkylC(=S)NR$^{74}$C$_{0-3}$alkyl-, —$C_{0-3}$alkylNR$^{74}$C$_{0-3}$alkyl-, —$C_{0-3}$ alkylNR$^{74}$C(=O)C$_{0-3}$alkyl-, —$C_{0-3}$alkylNR$^{74}$C(=O)OC$_{0-3}$ alkyl-, —$C_{0-3}$alkylNR$^{74}$C(=O)NR$^{74}$C$_{0-3}$alkyl-, —$C_{0-3}$ alkylNR$^{74}$C(=O)NR$^{74}$C(=O)C$_{0-3}$alkyl-, —$C_{0-3}$ alkylNR$^{74}$C(=O)NR$^{74}$C(=O)OC$_{0-3}$alkyl-, —$C_{0-3}$ alkylNR$^{74}$C(=S)C$_{0-3}$alkyl-, —$C_{0-3}$alkylNR$^{74}$S(=O)$_2$C$_{0-3}$ alkyl-, —$C_{0-3}$alkylOC$_{0-3}$alkyl-, —$C_{0-3}$alkylOC(=O)C$_{0-3}$ alkyl-, —$C_{0-3}$alkylOC(=O)NR$^{74}$C$_{0-3}$alkyl-, —$C_{0-3}$alkylS(=O)—C$_{0-3}$alkyl-, —$C_{0-3}$alkylS(=O)$_2$NR$^{74}$C$_{0-3}$alkyl-, or absent. In another embodiment, $X^3$ is $C_{1-6}$alkylene optionally substituted by 1-12 R$^{79}$, $C_{6-11}$arylene optionally substituted by 1-6 R$^{79}$, $C_{3-11}$cycloalkylene optionally substituted by 1-20 R$^{79}$, 3-15 membered heterocycloalkylene optionally substituted by 1-27 R$^{79}$, 5-15 membered heteroarylene optionally substituted by 1-14 R$^{79}$, —$C_{0-3}$alkylC(=O)C$_{0-3}$alkyl-, —$C_{0-3}$ alkylC(=O)OC$_{0-3}$alkyl-, —$C_{0-3}$alkylC(=O)NR$^{74}$C$_{0-3}$ alkyl-, —$C_{0-3}$alkylNR$^{74}$C$_{0-3}$alkyl-, —$C_{0-3}$alkylNR$^{74}$C(=O)C$_{0-3}$alkyl-, —$C_{0-3}$alkylNR$^{74}$C(=O)OC$_{0-3}$ alkyl-, —$C_{0-3}$alkylNR$^{74}$C(=O)NR$^{74}$C$_{0-3}$alkyl-, —$C_{0-3}$ alkylNR$^{74}$S(=O)$_2$C$_{0-3}$alkyl-, —$C_{0-3}$alkylOC$_{0-3}$alkyl-, —$C_{0-3}$alkylOC(=O)C$_{0-3}$alkyl-, —$C_{0-3}$alkylOC(=O)NR$^{74}$C$_{0-3}$alkyl-, —$C_{0-3}$alkylS(=O)—C$_{0-3}$alkyl-, —$C_{0-3}$alkylS(=O)$_2$ NR$^{74}$C$_{0-3}$alkyl-, or absent. In another embodiment, $X^3$ is $C_{1-6}$alkylene optionally substituted by 1-6 R$^{79}$, $C_{6-11}$ arylene optionally substituted by 1-6 R$^{79}$, $C_{7-16}$arylalkylene optionally substituted by 1-6 R$^{79}$, $C_{3-11}$cycloalkylene optionally substituted by 1-6 R$^{79}$, $C_{4-17}$cycloalkylalkylene optionally substituted by 1-6 R$^{79}$, 3-15 membered heterocycloalkylene optionally substituted by 1-6 R$^{79}$, 4-21 membered heterocycloalkylalkylene optionally substituted by 1-6 R$^{79}$, 5-15 membered heteroarylene optionally substituted by 1-6 R$^{79}$, 6-21 membered heteroarylalkylene optionally substituted by 1-6 R$^{79}$, —C(=O)—, —C(=O)O—, —C(=O)NR$^{74}$—, —C(=O)C(=O)—, —C(=S)NR$^{74}$—, —NR$^{74}$—, —NR$^{74}$NR$^{74}$—, —NR$^{74}$C(=O)—, —NR$^{74}$C(=O)C(=O)—, —NR$^{74}$C(=O)O—, —NR$^{74}$C(=O)C(=O)O—, —NR$^{74}$C(=O)NR$^{74}$—, —NR$^{74}$C(=O)NR$^{74}$C(=O)—, —NR$^{74}$C(=O)NR$^{74}$C(=O)O—, —NR$^{74}$C(=NR$^{75}$)NR$^{74}$—, —NR$^{74}$C(=O)C(=O)NR$^{74}$—, —NR$^{74}$C(=S)—, —NR$^{74}$C(=S)O—, —NR$^{74}$C(=S)NR$^{74}$—, —NR$^{74}$S(=O)$_2$—, —NR—, —O—, —OC(=O)—, —OC(=O)NR$^{74}$—, —OC(=O)O—, —OS(=O)—, —OS(=O)$_2$—, —OS(=O)$_2$O—, —OS(=O)$_2$NR$^{74}$—, —S(=O)$_n$—, —S(=O)$_2$O—, —SO$_3$—, —S(=O)$_2$NR$^{74}$—, —S(=O)NR$^{74}$—, or absent.

In another embodiment, $X^3$ is $C_{1-6}$alkylene optionally substituted by 1-6 R$^{79}$, $C_{6-11}$arylene optionally substituted by 1-6 R$^{79}$, $C_{7-16}$arylalkylene optionally substituted by 1-6 R$^{79}$, $C_{3-11}$cycloalkylene optionally substituted by 1-6 R$^{79}$, $C_{4-17}$cycloalkylalkylene optionally substituted by 1-6 R$^{79}$, 3-15 membered heterocycloalkylene optionally substituted by 1-6 R$^{79}$, 4-21 membered heterocycloalkylalkylene optionally substituted by 1-6 R$^{79}$, 5-15 membered heteroarylene optionally substituted by 1-6 R$^{79}$, 6-21 membered heteroarylalkylene optionally substituted by 1-6 R$^{79}$, —C(=O)—, —C(=O)O—, —C(=O)NR$^{74}$—, —C(=S)NR$^{74}$—, —NR$^{74}$—, —NR$^{74}$NR$^{74}$—, —NR$^{74}$C(=O)—, —NR$^{74}$C(=O)O—, —NR—, —NR$^{74}$C(=O)NR$^{74}$C(=O)—, —NR$^{74}$C(=O)NR$^{74}$C(=O)O—, —NR$^{74}$C(=NR$^{75}$)NR$^{74}$—, —NR$^{74}$C(=S)—, —NR$^{74}$C(=S)NR$^{74}$—, —NR$^{74}$S(=O)$_2$—, —O—, —OC(=O)—, —OC(=O)NR$^{74}$—, —S(=O)$_n$—, —S(=O)$_2$NR$^{74}$—, or absent. In another embodiment, X$^3$ is C$_{1-6}$alkylene optionally substituted by 1-6 R$^{79}$, C$_{6-11}$ arylene optionally substituted by 1-6 R$^{79}$, C$_{7-16}$arylalkylene optionally substituted by 1-6 R$^{79}$, C$_{3-11}$cycloalkylene optionally substituted by 1-6 R$^{79}$, C$_{4-6}$cycloalkylalkylene optionally substituted by 1-6 R$^{79}$, 3-15 membered heterocycloalkylene optionally substituted by 1-6 R$^{79}$, 4-21 membered heterocycloalkylalkylene optionally substituted by 1-6 R$^{79}$, 5-15 membered heteroarylene optionally substituted by 1-6 R$^{79}$, 6-21 membered heteroarylalkylene optionally substituted by 1-6 R$^{79}$, —C(=O)—, —C(=O)O—, —C(=O)NR$^{74}$—, —C(=S)NR$^{74}$—, —NR$^{74}$—, —NR$^{74}$C(=O)—, —NR$^{74}$C(=O)O—, —NR$^{74}$C(=O)NR$^{74}$—, —NR$^{74}$C(=O)NR$^{74}$C(=O)—, —NR$^{74}$C(=O)NR$^{74}$C(=O)O—, —NR$^{74}$C(=S)—, —NR$^{74}$S(=O)$_2$—, —O—, —OC(=O)—, —OC(=O)NR$^{74}$—, —S(=O)$_n$—, —S(=O)$_2$NR$^{74}$—, or absent. In another embodiment, X$^3$ is C$_{1-6}$alkylene optionally substituted by 1-6 R$^{79}$, C$_{6-11}$arylene optionally substituted by 1-6 R$^{79}$, C$_{3-11}$cycloalkylene optionally substituted by 1-6 R$^{79}$, 3-15 membered heterocycloalkylene optionally substituted by 1-6 R$^{79}$, 5-15 membered heteroarylene optionally substituted by 1-6 R$^{79}$, —C(=O)—, —C(=O)O—, —C(=O)NR$^{74}$—, —NR$^{74}$—, —NR$^{74}$C(=O)—, —NR$^{74}$C(=O)O—, —NR$^{74}$C(=O)NR$^{74}$—, —NR$^{74}$S(=O)$_2$—, —O—, —OC(=O)—, —OC(=O)NR$^{74}$—, —S(=O)$_n$—, —S(=O)$_2$NR$^{74}$—, or absent. In another embodiment, X$^3$ is C$_{1-6}$alkylene optionally substituted by 1-3 R$^{79}$, phenylene optionally substituted by 1-3 R$^{79}$, C$_{3-6}$cycloalkylene optionally substituted by 1-3 R$^{79}$, 3-6 membered heterocycloalkylene optionally substituted by 1-3 R$^{79}$, 5-6 membered heteroarylene optionally substituted by 1-3 R$^{79}$, —C(=O)—, —C(=O)O—, —C(=O)NR$^{74}$—, —NR$^{74}$—, —NR$^{74}$C(=O)—, —NR—, —NR$^{74}$S(=O)$_2$—, —O—, —OC(=O)—, —S(=O)$_2$—, —S(=O)$_2$NR$^{74}$—, or absent. In another embodiment, X$^3$ is C$_{1-6}$alkylene optionally substituted by 1-3 R$^{79}$ or absent. In another embodiment, X$^3$ is absent.

In each embodiment of the present invention that is described in the paragraphs that precede or follow this paragraph, the definition of Z$^3$ may be chosen from any of the embodiments that are described in this paragraph. In one embodiment, Z$^3$ is H, C$_{1-6}$alkyl optionally substituted by 1-13 R$^{89}$, C$_{2-6}$alkenyl optionally substituted by 1-11 R$^{89}$, C$_{2-6}$alkynyl optionally substituted by 1-9 R$^{89}$, C$_{6-11}$ aryl optionally substituted by 1-11 R$^{89}$, C$_{7-16}$arylalkyl optionally substituted by 1-19 R$^{89}$, C$_{3-11}$cycloalkyl optionally substituted by 1-21 R$^{89}$, C$_{4-17}$cycloalkylalkyl optionally substituted by 1-32 R$^{89}$, 3-15 membered heterocycloalkyl optionally substituted by 1-28 R$^{89}$, 4-21 membered heterocycloalkylalkyl optionally substituted by 1-40 R$^{89}$, 5-15 membered heteroaryl optionally substituted by 1-15 R$^{89}$, 6-21 membered heteroarylalkyl optionally substituted by 1-27 R$^{89}$, halogen, —CN, —C(=O)R$^{80}$, —C(=O)OR$^{80}$, —C(=O)NR$^{82}$R$^{83}$, —C(=O)C(=O)R$^{80}$, —C(=NR$^{85}$)R$^{80}$, —C(=NR$^{85}$)NR$^{82}$R$^{83}$, —C(=NOH)NR$^{82}$R$^{83}$, —C(=NOR$^{86}$)R$^{80}$, —C(=NNR$^{82}$R$^{83}$)R$^{80}$, —C(NNR$^{84}$C(=O)R$^{81}$)R$^{80}$, —C(=NNR$^{84}$C(=O)OR$^{81}$)R$^{80}$, —C(=S)NR$^{82}$R$^{83}$, —NC, —NO$_2$, —NR$^{82}$R$^{83}$, —NR$^{84}$NR$^{82}$R$^{83}$, —N=NR$^{84}$, =NR$^{80}$, =NOR$^{80}$, —NR$^{84}$OR$^{86}$, —NR$^{84}$C(=O)R$^{80}$, —NR$^{84}$C(=O)OR$^{81}$—NR$^{84}$C(=O)C(=O)OR$^{81}$, —NR$^{84}$C(=O) NR$^{82}$R$^{83}$, —NR$^{84}$C(=O)NR$^{84}$C(=O)R$^{80}$, —NR$^{84}$C(=O) NR$^{84}$C(=O)OR$^{80}$, —NR$^{84}$C(=NR$^{85}$)NR$^{82}$R$^{83}$, —NR$^{84}$C (=O)C(=O)NR$^{82}$R$^{83}$, —NR$^{84}$C(=S)NR$^{82}$R$^{83}$, —NR$^{84}$S (=O)$_2$R$^{81}$, —NR$^{84}$S(=O)$_2$NR$^{82}$R$^{83}$, —NR$^{84}$P(=O) R$^{88}$R$^{88}$, —NR$^{84}$P(=O)(NR$^{82}$R$^{83}$)(NR$^{82}$R$^{83}$), —NR$^{84}$P (=O)(OR$^{80}$)(OR$^{80}$), —NR$^{84}$P(=O)(SR$^{80}$)(SR$^{80}$), —OR$^{80}$, =O, —OCN, —OC(=O)R$^{80}$, —OC(=O)NR$^{82}$R$^{83}$, —OC (=O)OR$^{80}$, —OC(=NR$^{85}$)NR$^{82}$R$^{83}$, —OS(=O)R$^{80}$, —OS (=O)$_2$R$^{80}$, —OS(=O)$_2$OR$^{80}$, —OS(=O)$_2$NR$^{82}$R$^{83}$, —OP (=O)R$^{88}$R$^{88}$, —OP(=O)(NR$^{82}$R$^{83}$)(NR$^{82}$R$^{83}$), —OP(=O) (OR$^{80}$)(OR$^{80}$), —OP(=O)(SR$^{80}$)(SR$^{80}$), —SCN, =S, —S(=O)$_n$R$^{80}$, —S(=O)$_2$OR$^{80}$, —SO$_3$R$^{87}$, —S(=O)$_2$ NR$^{82}$R$^{83}$, —S(=O)NR$^{82}$R$^{83}$, —SP(=O)R$^{88}$R$^{88}$, —SP (=O)(NR$^{82}$R$^{83}$)(NR$^{82}$R$^{83}$), —SP(=O)(OR$^{80}$)(OR$^{80}$), —SP(=O)(SR$^{80}$)(SR$^{80}$), —P(=O)R$^{88}$R$^{88}$, —P(=O) (NR$^{82}$R$^{83}$)(NR$^{82}$R$^{83}$), —P(=O)(OR$^{80}$)(OR$^{80}$), or —P(=O) (SR$^{80}$)(SR$^{80}$); alternatively, when L$^2$, A$^2$, G$^2$, X$^2$, L$^3$, A$^3$, G$^3$ and X$^3$ are absent, Z$^2$ and Z$^3$ can together form a group of formula -A$^{21}$-A$^{22}$-A$^{23}$-, or when L$^3$, A$^3$, G$^3$, X$^3$, L$^4$, A$^4$, G$^4$ and X$^4$ are absent, Z$^3$ and Z$^4$ can together form a group of formula -A$^{21}$-A$^{22}$-A$^{23}$-; wherein A$^{21}$, A$^{22}$, and A$^{23}$ are independently chosen from —CZ$^{21}$Z$^{22}$—, —CZ$^{23}$Z$^{24}$CZ$^{25}$Z$^{26}$—, —C(=O)—, —NZ$^{27}$—, —S—, —S(=O)—, —S(=O)$_2$—, or —O—; wherein:

(a) when any two of Z$^{21}$, Z$^{22}$, Z$^{23}$, Z$^{24}$, Z$^{25}$, Z$^{26}$ and Z$^{27}$ are located on adjacent atoms, they may together form a bond between the atoms, and (b) any of Z$^{21}$, Z$^{22}$, Z$^{23}$, Z$^{24}$, Z$^{25}$, Z$^{26}$ and Z$^{27}$ may be independently chosen from H, C$_{1-6}$alkyl optionally substituted by 1-13 R$^{99}$, C$_{2-6}$alkenyl optionally substituted by 1-11 R$^{99}$, C$_{2-6}$alkynyl optionally substituted by 1-9 R$^{99}$, C$_{6-11}$ aryl optionally substituted by 1-11 R$^{99}$, C$_{7-16}$arylalkyl optionally substituted by 1-19 R$^{99}$, C$_{3-11}$cycloalkyl optionally substituted by 1-21 R$^{99}$, C$_{4-17}$cycloalkylalkyl optionally substituted by 1-32 R$^{99}$, 3-15 membered heterocycloalkyl optionally substituted by 1-28 R$^{99}$, 4-21 membered heterocycloalkylalkyl optionally substituted by 1-40 R$^{99}$, 5-15 membered heteroaryl optionally substituted by 1-15 R$^{99}$, 6-21 membered heteroarylalkyl optionally substituted by 1-27 R$^{99}$, halogen, —CN, —C(=O)R$^{90}$, —C(=O)OR$^{90}$, —C(=O)NR$^{92}$R$^{93}$, —C(=O)C(=O)R$^{90}$, —C(=NR$^{95}$) R$^{90}$, —C(=NR$^{95}$)NR$^{92}$R$^{93}$, —C(=NOH)NR$^{92}$R$^{93}$, —C(=NOR$^{96}$)R$^{90}$, —C(=NNR$^{92}$R$^{93}$)R$^{90}$, —C(=NNR$^{94}$C(=O)R$^{91}$)R$^{90}$, —C(=NNR$^{94}$C(=O) OR$^{91}$)R$^{90}$, —C(=S)NR$^{92}$R$^{93}$, —NC, —NO$_2$, —NR$^{92}$R$^{93}$, —NR$^{94}$NR$^{92}$R$^{93}$, —N=NR$^{94}$, =NR$^{90}$, =NOR$^{90}$, —NR$^{94}$OR$^{96}$, —NR$^{94}$C(=O)R$^{90}$, —NR$^{94}$C(=O)C(=O) R$^{90}$, —NR$^{94}$C(=O)OR$^{91}$, —NR$^{94}$C(=O)C(=O)OR$^{91}$, —NR$^{94}$C(=O)NR$^{92}$R$^{93}$, —NR$^{94}$C(=O)NR$^{94}$C(=O)R$^{90}$, —NR$^{94}$C(=O)NR$^{94}$C(=O)OR$^{90}$, —NR$^{94}$C(=NR$^{95}$) NR$^{92}$R$^{93}$, —NR$^{94}$C(=O)C(=O)NR$^{92}$R$^{93}$, —NR$^{94}$C(=S) R$^{90}$, —NR$^{94}$C(=S)OR$^{90}$, —NR$^{94}$C(=S)NR$^{92}$R$^{93}$, —NR$^{94}$S(=O)$_2$R$^{91}$, —NR$^{94}$S(=O)$_2$NR$^{92}$R$^{93}$, —NR$^{94}$P (=O)R$^{98}$R$^{98}$, —NR$^{94}$P(=O)(NR$^{92}$R$^{93}$)(NR$^{92}$R$^{93}$), —NR$^{94}$P(=O)(OR$^{90}$)(OR$^{90}$), —NR$^{94}$P(=O)(SR$^{90}$)(SR$^{90}$), —OR$^{90}$, =O, —OCN, —OC(=O)R$^{90}$, —OC(=O) NR$^{92}$R$^{93}$, —OC(=O)OR$^{90}$, —OC(=NR$^{95}$)NR$^{92}$R$^{93}$, —OS (=O)R$^{90}$, —OS(=O)$_2$R$^{90}$, —OS(=O)$_2$OR$^{90}$, —OS(=O)$_2$ NR$^{92}$R$^{93}$, —OP(=O)R$^{98}$R$^{98}$, —OP(=O)(NR$^{92}$R$^{93}$) (NR$^{92}$R$^{93}$), —OP(=O)(OR$^{90}$)(OR$^{90}$), —OP(=O)(SR$^{90}$) (SR$^{90}$), —SCN, =S, —S(=O)$_n$R$^{90}$, —S(=O)$_2$OR$^{90}$, —SO$_3$R$^{97}$, —S(=O)$_2$NR$^{92}$R$^{93}$, —S(=O)NR$^{92}$R$^{93}$, —SP (=O)R$^{98}$R$^{98}$, —SP(=O)(NR$^{92}$R$^{93}$)(NR$^{92}$R$^{93}$), —SP(=O) (OR$^{90}$)(OR$^{90}$), —SP(=O)(SR$^{90}$)(SR$^{90}$), —P(=O)R$^{98}$R$^{98}$, —P(=O)(NR$^{92}$R$^{93}$)(NR$^{92}$R$^{93}$), —P(=O)(OR$^{90}$)(OR$^{90}$), and —P(=O)(SR$^{90}$)(SR$^{90}$); and (c) any two of $Z^{21}$, $Z^{22}$, $Z^{23}$, $Z^{24}$, $Z^{25}$, $Z^{26}$ and $Z^{27}$ may together form a group of formula -$A^{31}$-$A^{32}$-$A^{33}$-, wherein $A^{31}$, $A^{32}$, and $A^{33}$ are independently chosen from —$CZ^{31}Z^{32}$—, —$CZ^{33}Z^{34}CZ^{35}Z^{36}$—, —C(=O)—, —$NZ^{37}$—, —S—, —S(=O)—, —S(=O)$_2$—, or —O— wherein:

(i) when any two of $Z^{31}$, $Z^{32}$, $Z^{33}$, $Z^{34}$, $Z^{35}$, $Z^{36}$ and $Z^{37}$ are located on adjacent atoms, they may together form a bond between the atoms, and (ii) any of any of $Z^{21}$, $Z^{22}$, $Z^{23}$, $Z^{24}$, $Z^{25}$, $Z^{26}$ and $Z^{27}$ may be independently chosen from H, $C_{1-6}$alkyl optionally substituted by 1-13 $R^{139}$, $C_{2-6}$alkenyl optionally substituted by 1-11 $R^{139}$, $C_{2-6}$alkynyl optionally substituted by 1-9 $R^{139}$, $C_{6-11}$aryl optionally substituted by 1-11 $R^{139}$, $C_{7-16}$arylalkyl optionally substituted by 1-19 $R^{139}$, $C_{3-11}$cycloalkyl optionally substituted by 1-21 $R^{139}$, $C_{4-17}$cycloalkylalkyl optionally substituted by 1-32 $R^{139}$, 3-15 membered heterocycloalkyl optionally substituted by 1-28 $R^{139}$, 4-21 membered heterocycloalkylalkyl optionally substituted by 1-40 $R^{139}$, 5-15 membered heteroaryl optionally substituted by 1-15 $R^{139}$, 6-21 membered heteroarylalkyl optionally substituted by 1-27 $R^{139}$, halogen, —CN, —C(=O)$R^{130}$, —C(=O)O$R^{130}$, —C(=O)N$R^{132}R^{133}$, —C(=O)C(=O)$R^{130}$, —C(=N$R^{135}$)$R^{130}$, —C(=N$R^{135}$)N$R^{132}R^{133}$, —C(=NOH)N$R^{132}R^{133}$, —C(=NO$R^{136}$)$R^{130}$, —C(=NN$R^{132}R^{133}$)$R^{130}$, —C(=NN$R^{134}$C(=O)$R^{131}$)$R^{130}$, —C(=NN$R^{134}$C(=O)O$R^{131}$)$R^{130}$, —C(=S)N$R^{132}R^{133}$, —NC, —NO$_2$, —N$R^{132}R^{133}$, —N$R^{134}$N$R^{132}R^{133}$, —N=N$R^{134}$, =N$R^{130}$, =NO$R^{130}$, —N$R^{134}$O$R^{136}$, —N$R^{134}$C(=O)$R^{130}$, —N$R^{134}$C(=O)C(=O)$R^{130}$, —N$R^{134}$C(=O)O$R^{131}$, —N$R^{134}$C(=O)C(=O)O$R^{131}$, —N$R^{134}$C(=O)N$R^{132}R^{133}$, —N$R^{134}$C(=O)N$R^{134}$C(=O)$R^{130}$, —N$R^{134}$C(=O)N$R^{134}$C(=O)O$R^{130}$, —N$R^{134}$C(=N$R^{135}$)N$R^{132}R^{133}$, —N$R^{134}$C(=O)C(=O)N$R^{132}R^{133}$, —N$R^{134}$C(=S)$R^{130}$, —N$R^{134}$C(=S)O$R^{130}$, —N$R^{134}$C(=S)N$R^{132}R^{133}$, —N$R^{134}$S(=O)$_2R^{131}$, —N$R^{134}$S(=O)$_2$N$R^{132}R^{133}$, —N$R^{134}$P(=O)$R^{138}R^{138}$, —N$R^{134}$P(=O)(N$R^{132}R^{133}$)(N$R^{132}R^{133}$), —N$R^{134}$P(=O)(O$R^{130}$)(O$R^{130}$), —N$R^{134}$P(=O)(S$R^{130}$)(S$R^{130}$), —O$R^{130}$, =O, —OCN, —OC(=O)$R^{130}$, —OC(=O)N$R^{132}R^{133}$, —OC(=O)O$R^{130}$, —OC(=N$R^{135}$)N$R^{132}R^{133}$, —OS(=O)$R^{130}$, —OS(=O)$_2R^{130}$, —OS(=O)$_2$O$R^{130}$, —OS(=O)$_2$N$R^{132}R^{133}$, —OP(=O)$R^{138}R^{138}$, —OP(=O)(N$R^{132}R^{133}$)(N$R^{132}R^{133}$), —OP(=O)(O$R^{130}$)(O$R^{130}$), —OP(=O)(S$R^{130}$)(S$R^{130}$), —SCN, =S, —S(=O)$_nR^{130}$, —S(=O)$_2$O$R^{130}$, —SO$_3R^{137}$, —S(=O)$_2$N$R^{132}R^{133}$, —S(=O)N$R^{132}R^{133}$, —SP(=O)$R^{138}R^{138}$, —SP(=O)(N$R^{132}R^{133}$)(N$R^{132}R^{133}$), —SP(=O)(O$R^{130}$)(O$R^{130}$), —SP(=O)(S$R^{130}$)(S$R^{130}$), —P(=O)$R^{138}R^{138}$, —P(=O)(N$R^{132}R^{133}$)(N$R^{132}R^{133}$), —P(=O)(O$R^{130}$)(O$R^{130}$), and P(=O)(S$R^{130}$)(S$R^{130}$). In another embodiment, $Z^3$ is H, $C_{1-6}$alkyl optionally substituted by 1-13 $R^{89}$, $C_{2-6}$alkenyl optionally substituted by 1-11 $R^{89}$, $C_{2-6}$alkynyl optionally substituted by 1-9 $R^{89}$, $C_{6-11}$aryl optionally substituted by 1-11 $R^{89}$, $C_{7-16}$arylalkyl optionally substituted by 1-19 $R^{89}$, $C_{3-11}$cycloalkyl optionally substituted by 1-21 $R^{89}$, $C_{4-17}$cycloalkylalkyl optionally substituted by 1-32 $R^{89}$, 3-15 membered heterocycloalkyl optionally substituted by 1-28 $R^{89}$, 4-21 membered heterocycloalkylalkyl optionally substituted by 1-40 $R^{89}$, 5-15 membered heteroaryl optionally substituted by 1-15 $R^{89}$, 6-21 membered heteroarylalkyl optionally substituted by 1-27 $R^{89}$, halogen, —CN, —C(=O)$R^{80}$, —C(=O)O$R^{80}$, —C(=O)N$R^{82}R^{83}$, —C(=O)C(=O)$R^{80}$, —C(=N$R^{85}$)$R^{80}$, —C(=N$R^{85}$)N$R^{82}R^{83}$, —C(=NOH)N$R^{82}R^{83}$, —C(=NO$R^{86}$)$R^{80}$, —C(=NN$R^{82}R^{83}$)$R^{80}$, —C(=NN$R^{84}$C(=O)$R^{81}$)$R^{80}$, —C(=NN$R^{84}$C(=O)O$R^{81}$)$R^{80}$, —C(=S)N$R^{82}R^{83}$, —NC, —NO$_2$, —N$R^{82}R^{83}$, —N$R^{84}$N$R^{82}R^{83}$, —N=N$R^{84}$, =N$R^{80}$, =NO$R^{80}$, —N$R^{84}$O$R^{86}$, —N$R^{84}$C(=O)$R^{80}$, —N$R^{84}$C(=O)C(=O)$R^{80}$, —N$R^{84}$C(=O)O$R^{81}$, —N$R^{84}$C(=O)C(=O)O$R^{81}$, —N$R^{84}$C(=O)$R^{82}R^{83}$, —N$R^{84}$C(=O)N$R^{84}$C(=O)$R^{80}$, —N$R^{84}$C(=O)N$R^{84}$C(=O)O$R^{80}$, —N$R^{84}$C(=N$R^{85}$)N$R^{82}R^{83}$, —N$R^{84}$C(=O)C(=O)N$R^{82}R^{83}$, —N$R^{84}$C(=S)$R^{80}$, —N$R^{84}$C(=S)O$R^{80}$, —N$R^{84}$C(=S)N$R^{82}R^{83}$, —N$R^{84}$S(=O)$_2R^{81}$, —N$R^{84}$S(=O)$_2$N$R^{82}R^{83}$, —N$R^{84}$P(=O)$R^{88}R^{88}$, —O$R^{80}$, =O, —OCN, —OC(=O)$R^{80}$, —OC(=O)N$R^{82}R^{83}$, —OC(=O)O$R^{80}$, —OC(=N$R^{85}$)N$R^{82}R^{83}$, —OS(=O)$R^{80}$, —OS(=O)$_2R^{80}$, —OS(=O)$_2$O$R^{80}$, —OS(=O)$_2$N$R^{82}R^{83}$, —SCN, =S, —S(=O)$_nR^{80}$, —S(=O)$_2$O$R^{80}$, —SO$_3R^{87}$, —S(=O)$_2$N$R^{82}R^{83}$, —S(=O)N$R^{82}R^{83}$, or —P(=O)$R^{88}R^{88}$; alternatively, when $L^2$, $A^2$, $G^2$, $X^2$, $L^3$, $A^3$, $G^3$ and $X^3$ are absent, $Z^2$ and $Z^3$ can together form a group of formula -$A^{21}$-$A^{22}$-$A^{23}$-, or when $L^3$, $A^3$, $G^3$, $X^3$, $L^4$, $A^4$, $G^4$ and $X^4$ are absent, $Z^3$ and $Z^4$ can together form a group of formula -$A^{21}$-$A^{22}$-$A^{23}$-; wherein $A^{21}$, $A^{22}$, and $A^{23}$ are independently chosen from —$CZ^{21}Z^{22}$—, —$CZ^{23}Z^{24}CZ^{25}Z^{26}$—, —C(=O)—, —$NZ^{27}$—, —S—, —S(=O)—, —S(=O)$_2$—, or —O—; wherein:

(a) when any two of $Z^{21}$, $Z^{22}$, $Z^{23}$, $Z^{24}$, $Z^{25}$, $Z^{26}$ and $Z^{27}$ are located on adjacent atoms, they may together form a bond between the atoms, and (b) any of $Z^{21}$, $Z^{22}$, $Z^{23}$, $Z^{24}$, $Z^{25}$, $Z^{26}$ and $Z^{27}$ may be independently chosen from H, $C_{1-6}$alkyl optionally substituted by 1-13 $R^{99}$, $C_{2-6}$alkenyl optionally substituted by 1-11 $R^{99}$, $C_{2-6}$alkynyl optionally substituted by 1-9 $R^{99}$, $C_{6-11}$aryl optionally substituted by 1-11 $R^{99}$, $C_{7-16}$arylalkyl optionally substituted by 1-19 $R^{99}$, $C_{3-11}$cycloalkyl optionally substituted by 1-21 $R^{99}$, $C_{4-17}$cycloalkylalkyl optionally substituted by 1-32 $R^{99}$, 3-15 membered heterocycloalkyl optionally substituted by 1-28 $R^{99}$, 4-21 membered heterocycloalkylalkyl optionally substituted by 1-40 $R^{99}$, 5-15 membered heteroaryl optionally substituted by 1-15 $R^{99}$, 6-21 membered heteroarylalkyl optionally substituted by 1-27 $R^{99}$, halogen, —CN, —C(=O)$R^{90}$, —C(=O)O$R^{90}$, —C(=O)N$R^{92}R^{93}$, —C(=O)C(=O)$R^{90}$, —C(=N$R^{95}$)$R^{90}$, —C(=N$R^{95}$)N$R^{92}R^{93}$, —C(=NOH)N$R^{92}R^{93}$, —C(=NO$R^{96}$)$R^{90}$, —C(=NN$R^{92}R^{93}$)$R^{90}$, —C(=NN$R^{94}$C(=O)$R^{91}$)$R^{90}$, —C(=NN$R^{94}$C(=O)O$R^{91}$)$R^{90}$, —C(=S)N$R^{92}R^{93}$, —NC, —NO$_2$, —N$R^{92}R^{93}$, —N$R^{94}$N$R^{92}R^{93}$, —N=N$R^{94}$, =N$R^{90}$, =NO$R^{90}$, —N$R^{94}$O$R^{96}$, —N$R^{94}$C(=O)$R^{90}$, —N$R^{94}$C(=O)C(=O)$R^{90}$, —N$R^{94}$C(=O)O$R^{91}$, —N$R^{94}$C(=O)C(=O)O$R^{91}$, —N$R^{94}$C(=O)N$R^{92}R^{93}$, —N$R^{94}$C(=O)N$R^{94}$C(=O)$R^{90}$, —N$R^{94}$C(=O)N$R^{94}$C(=O)O$R^{90}$, —N$R^{94}$C(=N$R^{95}$)N$R^{92}R^{93}$, —N$R^{94}$C(=O)C(=O)N$R^{92}R^{93}$, —N$R^{94}$C(=S)$R^{90}$, —N$R^{94}$C(=S)O$R^{90}$, —N$R^{94}$C(=S)N$R^{92}R^{93}$, —N$R^{94}$S(=O)$_2R^{91}$, —N$R^{94}$S(=O)$_2$N$R^{92}R^{93}$, —N$R^{94}$P(=O)$R^{98}R^{98}$, —O$R^{90}$, =O, —OCN, —OC(=O)$R^{90}$, —OC(=O)N$R^{92}R^{93}$, —OC(=O)O$R^{90}$, —OC(=N$R^{95}$)N$R^{92}R^{93}$, —OS(=O)$R^{90}$, —OS(=O)$_2R^{90}$, —OS(=O)$_2$O$R^{90}$, —OS(=O)$_2$N$R^{92}R^{93}$, —SCN, =S, —S(=O)$_nR^{90}$, —S(=O)$_2$O$R^{90}$, —SO$_3R^{97}$, —S(=O)$_2$N$R^{92}R^{93}$, —S(=O)N$R^{92}R^{93}$, and —P(=O)$R^{98}R^{98}$; and (c) any two of $Z^{21}$, $Z^{22}$, $Z^{23}$, $Z^{24}$, $Z^{25}$, $Z^{26}$ and $Z^{27}$ may together form a group of formula -$A^{31}$-$A^{32}$-$A^{33}$-, wherein $A^{31}$, $A^{32}$, and $A^{33}$ are independently chosen from —$CZ^{31}Z^{32}$—, —$CZ^{33}Z^{34}CZ^{35}Z^{36}$—, —C(=O)—, —$NZ^{37}$—, —S—, —S(=O)—, —S(=O)$_2$—, or —O— wherein:

(i) when any two of $Z^{31}$, $Z^{32}$, $Z^{33}$, $Z^{34}$, $Z^{35}$, $Z^{36}$ and $Z^{37}$ are located on adjacent atoms, they may together form a bond between the atoms, and (ii) any of any of $Z^{21}$, $Z^{22}$, $Z^{23}$, $Z^{24}$, $Z^{25}$, $Z^{26}$ and $Z^{27}$ may be independently chosen from H, $C_{1-6}$alkyl optionally substituted by 1-13 $R^{139}$, $C_{2-6}$alkenyl optionally substituted by 1-11 $R^{139}$, $C_{2-6}$alkynyl optionally substituted by 1-9 $R^{139}$, $C_{6-11}$ aryl optionally substituted by 1-11 $R^{139}$, $C_{7-16}$arylalkyl optionally substituted by 1-19 $R^{139}$, $C_{3-11}$cycloalkyl optionally substituted by 1-21 $R^{139}$, $C_{4-17}$cycloalkylalkyl optionally substituted by 1-32 $R^{139}$, 3-15 membered heterocycloalkyl optionally substituted by 1-28 $R^{139}$, 4-21 membered heterocycloalkylalkyl optionally substituted by 1-40 $R^{139}$, 5-15 membered heteroaryl optionally substituted by 1-15 $R^{139}$, 6-21 membered heteroarylalkyl optionally substituted by 1-27 $R^{139}$, halogen, —CN, —C(=O)$R^{130}$, —C(=O)O$R^{130}$, —C(=O)N$R^{132}R^{133}$, —C(=O)C(=O)$R^{130}$, —C(=N$R^{135}$)$R^{130}$, —C(=N$R^{135}$)N$R^{132}R^{133}$, —C(=NOH)N$R^{132}R^{133}$, —C(=NO$R^{136}$)$R^{130}$, —C(=NN$R^{132}R^{133}$)$R^{130}$, —C(=NN$R^{134}$C(=O)$R^{131}$)$R^{130}$, —C(=NN$R^{134}$C(=O)O$R^{131}$)$R^{130}$, —C(=S)N$R^{132}R^{133}$, —NC, —NO$_2$, —N$R^{132}R^{133}$, —N$R^{134}$N$R^{132}R^{133}$, —N=N$R^{134}$, =N$R^{130}$, =NO$R^{130}$, —N$R^{134}$O$R^{136}$, —N$R^{134}$C(=O)$R^{130}$, —N$R^{134}$C(=O)C(=O)$R^{130}$, —N$R^{134}$C(=O)O$R^{131}$, —N$R^{134}$C(=O)C(=O)O$R^{131}$, —N$R^{134}$C(=O)N$R^{132}R^{133}$, —N$R^{134}$C(=O)N$R^{134}$C(=O)$R^{130}$, —N$R^{134}$C(=O)N$R^{134}$C(=O)O$R^{130}$, —N$R^{134}$C(=N$R^{13}$)N$R^{132}R^{133}$, —N$R^{134}$C(=O)C(=O)N$R^{132}R^{133}$, —N$R^{134}$C(=S)$R^{130}$, —N$R^{134}$C(=S)O$R^{130}$, —N$R^{134}$C(=S)N$R^{132}R^{133}$, —N$R^{134}$S(=O)$_2R^{131}$, —N$R^{134}$S(=O)$_2$N$R^{132}R^{133}$, —N$R^{134}$P(=O)$R^{138}R^{138}$, —O$R^{130}$, =O, —OCN, —OC(=O)$R^{130}$, —OC(=O)N$R^{132}R^{133}$, —OC(=O)O$R^{130}$, —OC(=N$R^{135}$)N$R^{132}R^{133}$, —OS(=O)$R^{130}$, —OS(=O)$_2R^{130}$, —OS(=O)$_2$O$R^{130}$, —OS(=O)$_2$N$R^{132}R^{133}$, —SCN, =S, —S(=O)$_nR^{130}$, —S(=O)$_2$O$R^{130}$, —SO$_3R^{137}$, —S(=O)$_2$N$R^{132}R^{133}$, —S(=O)N$R^{132}R^{133}$, and —P(=O)$R^{138}R^{138}$. In another embodiment, $Z^3$ is H, $C_{1-6}$alkyl optionally substituted by 1-13 $R^{89}$, $C_{2-6}$alkenyl optionally substituted by 1-11 $R^{89}$, $C_{2-6}$alkynyl optionally substituted by 1-9 $R^{89}$, $C_{6-11}$ aryl optionally substituted by 1-11 $R^{89}$, $C_{7-16}$arylalkyl optionally substituted by 1-19 $R^{89}$, $C_{3-11}$cycloalkyl optionally substituted by 1-21 $R^{89}$, $C_{4-17}$cycloalkylalkyl optionally substituted by 1-32 $R^{89}$, 3-15 membered heterocycloalkyl optionally substituted by 1-28 $R^{89}$, 4-21 membered heterocycloalkylalkyl optionally substituted by 1-40 $R^{89}$, 5-15 membered heteroaryl optionally substituted by 1-15 $R^{89}$, 6-21 membered heteroarylalkyl optionally substituted by 1-27 $R^{89}$, halogen, —CN, —C(=O)$R^{80}$, —C(=O)O$R^{80}$, —C(=O)N$R^{82}R^{83}$, —C(=O)C(=O)$R^{80}$, —C(=N$R^{85}$)$R^{80}$, —C(=N$R^{85}$)N$R^{82}R^{83}$, —C(=NOH)N$R^{82}R^{83}$, —C(=NO$R^{86}$)$R^{80}$, —C(=NN$R^{82}R^{83}$)$R^{80}$, —C(=NN$R^{84}$C(=O)$R^{81}$)$R^{80}$, —C(=NN$R^{84}$C(=O)O$R^{81}$)$R^{80}$, —C(=S)N$R^{82}R^{83}$, —NC, —NO$_2$, —N$R^{82}R^{83}$, —N$R^{84}$N$R^{82}R^{83}$, —N=N$R^{84}$, =N$R^{80}$, =NO$R^{80}$, —N$R^{84}$O$R^{86}$, —N$R^{84}$C(=O)$R^{80}$, —N$R^{84}$C(=O)C(=O)$R^{80}$, —N$R^{84}$C(=O)O$R^{81}$, —N$R^{84}$C(=O)C(=O)O$R^{81}$, —N$R^{84}$C(=O)N$R^{82}R^{83}$, —N$R^{84}$C(=O)N$R^{84}$C(=O)$R^{80}$, —N$R^{84}$C(=O)N$R^{84}$C(=O)O$R^{80}$, —N$R^{84}$C(=N$R^{85}$)N$R^{82}R^{83}$, —N$R^{84}$C(=O)C(=O)N$R^{82}R^{83}$, —N$R^{84}$C(=S)$R^{80}$, —N$R^{84}$C(=S)O$R^{80}$, —N$R^{84}$C(=N$R^{85}$)N$R^{82}R^{83}$, —N$R^{84}$S(=O)$_2R^{81}$, —N$R^{84}$S(=O)$_2$N$R^{82}R^{83}$, —O$R^{80}$, =O, —OCN, —OC(=O)$R^{80}$, —OC(=O)N$R^{82}R^{83}$, —OC(=O)O$R^{80}$, —OC(=N$R^{85}$)N$R^{82}R^{83}$, —OS(=O)$R^{80}$, —OS(=O)$_2R^{80}$, —OS(=O)$_2$O$R^{80}$, —OS(=O)$_2$N$R^{82}R^{83}$, —SCN, =S, —S(=O)$_nR^{80}$, —S(=O)$_2$O$R^{80}$, —SO$_3R^{87}$, —S(=O)$_2$N$R^{82}R^{83}$, or —S(=O)N$R^{82}R^{83}$; alternatively, when $L^2$, $A^2$, $G^2$, $X^2$, $L^3$, $A^3$, $G^3$ and $X^3$ are absent, $Z^2$ and $Z^3$ can together form a group of formula -$A^{21}$-$A^{22}$-$A^{23}$-, or when $L^3$, $A^3$, $G^3$, $X^3$, $L^4$, $A^4$, $G^4$ and $X^4$ are absent, $Z^3$ and $Z^4$ can together form a group of formula -$A^{21}$-$A^{22}$-$A^{23}$-; wherein $A^{21}$, $A^{22}$, and $A^{23}$ are independently chosen from —C$Z^{21}Z^{22}$—, —C$Z^{23}Z^{24}$C$Z^{25}Z^{26}$—, —C(=O)—, —N$Z^{27}$—, —S—, —S(=O)—, —S(=O)$_2$—, or —O—; wherein:

(a) when any two of $Z^{21}$, $Z^{22}$, $Z^{23}$, $Z^{24}$, $Z^{25}$, $Z^{26}$ and $Z^{27}$ are located on adjacent atoms, they may together form a bond between the atoms, and (b) any of $Z^{21}$, $Z^{22}$, $Z^{23}$, $Z^{24}$, $Z^{25}$, $Z^{26}$ and $Z^{27}$ may be independently chosen from H, $C_{1-6}$alkyl optionally substituted by 1-13 $R^{99}$, $C_{2-6}$alkenyl optionally substituted by 1-11 $R^{99}$, $C_{2-6}$alkynyl optionally substituted by 1-9 $R^{99}$, $C_{6-11}$ aryl optionally substituted by 1-11 $R^{99}$, $C_{7-16}$arylalkyl optionally substituted by 1-19 $R^{99}$, $C_{3-11}$cycloalkyl optionally substituted by 1-21 $R^{99}$, $C_{4-17}$cycloalkylalkyl optionally substituted by 1-32 $R^{99}$, 3-15 membered heterocycloalkyl optionally substituted by 1-28 $R^{99}$, 4-21 membered heterocycloalkylalkyl optionally substituted by 1-40 $R^{99}$, 5-15 membered heteroaryl optionally substituted by 1-15 $R^{99}$, 6-21 membered heteroarylalkyl optionally substituted by 1-27 $R^{99}$, halogen, —CN, —C(=O)$R^{90}$, —C(=O)O$R^{90}$, —C(=O)N$R^{92}R^{93}$, —C(=O)C(=O)$R^{90}$, —C(=N$R^{95}$)$R^{90}$, —C(=N$R^{95}$)N$R^{92}R^{93}$, —C(=NOH)N$R^{92}R^{93}$, —C(=NO$R^{96}$)$R^{90}$, —C(=NN$R^{92}R^{93}$)$R^{90}$, —C(=NN$R^{94}$C(=O)$R^{91}$)$R^{90}$, —C(=NN$R^{94}$C(=O)O$R^{91}$)$R^{90}$, —C(=S)N$R^{92}R^{93}$, —NC, —NO$_2$, —N$R^{92}R^{93}$, —N$R^{94}$N$R^{92}R^{93}$, —N=N$R^{94}$, =N$R^{90}$, =NO$R^{90}$, —N$R^{94}$O$R^{96}$, —N$R^{94}$C(=O)$R^{90}$, —N$R^{94}$C(=O)C(=O)$R^{90}$, —N$R^{94}$C(=O)O$R^{91}$, —N$R^{94}$C(=O)C(=O)O$R^{91}$, —N$R^{94}$C(=O)N$R^{92}R^{93}$, —N$R^{94}$C(=O)N$R^{94}$C(=O)$R^{90}$, —N$R^{94}$C(=O)N$R^{94}$C(=O)O$R^{90}$, —N$R^{94}$C(=N$R^{95}$)N$R^{92}R^{93}$, —N$R^{94}$C(=O)C(=O)N$R^{92}R^{93}$, —N$R^{94}$C(=S)$R^{90}$, —N$R^{94}$C(=S)O$R^{90}$, —N$R^{94}$C(=S)N$R^{92}R^{93}$, —N$R^{94}$S(=O)$_2R^{91}$, —N$R^{94}$S(=O)$_2$N$R^{92}R^{93}$, —O$R^{90}$, =O, —OCN, —OC(=O)$R^{90}$, —OC(=O)N$R^{92}R^{93}$, —OC(=O)O$R^{90}$, —OC(=N$R^{95}$)N$R^{92}R^{93}$, —OS(=O)$R^{90}$, —OS(=O)$_2R^{90}$, —OS(=O)$_2$O$R^{90}$, —OS(=O)$_2$N$R^{92}R^{93}$, —SCN, =S, —S(=O)$_nR^{90}$, —S(=O)$_2$O$R^{90}$, —SO$_3R^{97}$, —S(=O)$_2$N$R^{92}R^{93}$, and —S(=O)N$R^{92}R^{93}$; and (c) any two of $Z^{21}$, $Z^{22}$, $Z^{23}$, $Z^{24}$, $Z^{25}$, $Z^{26}$ and $Z^{27}$ may together form a group of formula -$A^{31}$-$A^{32}$-$A^{33}$-, wherein $A^{31}$, $A^{32}$, and $A^{33}$ are independently chosen from —C$Z^{31}Z^{32}$—, —C$Z^{33}Z^{34}$C$Z^{35}Z^{36}$—, —C(=O)—, —N$Z^{37}$—, —S—, —S(=O)—, —S(=O)$_2$—, or —O— wherein:

(i) when any two of $Z^{31}$, $Z^{32}$, $Z^{33}$, $Z^{34}$, $Z^{35}$, $Z^{36}$ and $Z^{37}$ are located on adjacent atoms, they may together form a bond between the atoms, and (ii) any of any of $Z^{21}$, $Z^{22}$, $Z^{23}$, $Z^{24}$, $Z^{25}$, $Z^{26}$ and $Z^{27}$ may be independently chosen from H, $C_{1-6}$alkyl optionally substituted by 1-13 $R^{139}$, $C_{2-6}$alkenyl optionally substituted by 1-11 $R^{139}$, $C_{2-6}$alkynyl optionally substituted by 1-9 $R^{139}$, $C_{6-11}$ aryl optionally substituted by 1-11 $R^{139}$, $C_{7-16}$arylalkyl optionally substituted by 1-19 $R^{139}$, $C_{3-11}$cycloalkyl optionally substituted by 1-21 $R^{139}$, $C_{4-17}$cycloalkylalkyl optionally substituted by 1-32 $R^{139}$, 3-15 membered heterocycloalkyl optionally substituted by 1-28 $R^{139}$, 4-21 membered heterocycloalkylalkyl optionally substituted by 1-40 $R^{139}$, 5-15 membered heteroaryl optionally substituted by 1-15 $R^{139}$, 6-21 membered heteroarylalkyl optionally substituted by 1-27 $R^{139}$, halogen, —CN, —C(=O)$R^{130}$, —C(=O)O$R^{130}$, —C(=O)N$R^{132}R^{133}$, —C(=O)C(=O)$R^{130}$, —C(=N$R^{135}$)$R^{130}$, —C(=N$R^{135}$)N$R^{132}R^{133}$, —C(=NOH)N$R^{132}R^{133}$, —C(=NO$R^{136}$)$R^{130}$, —C(=NN$R^{132}R^{133}$)$R^{130}$, —C(=NN$R^{134}$C(=O)$R^{131}$)$R^{130}$, —C(=NN$R^{134}$C(=O)O$R^{131}$)$R^{130}$, —C(=S)N$R^{132}R^{133}$, —NC, —NO$_2$, —N$R^{132}R^{133}$, —N$R^{134}$N$R^{132}R^{133}$, —N=N$R^{134}$, =N$R^{130}$, =NO$R^{130}$, —N$R^{134}$O$R^{136}$, —N$R^{134}$C(=O)$R^{130}$, —N$R^{134}$C(=O)C (=O)R$^{130}$, —NR$^{134}$C(=O)OR$^{131}$, —NR$^{134}$C(=O)C(=O) OR$^{131}$, —NR$^{134}$C(=O)NR$^{132}$R$^{133}$, —NR$^{134}$C(=O) NR$^{134}$C(=O)R$^{130}$, —NR$^{134}$C(=O)NR$^{134}$C(=O)OR$^{130}$, —NR$^{134}$C(=NR$^{13}$)NR$^{132}$R$^{133}$, —NR$^{134}$C(=O)C(=O) NR$^{132}$R$^{133}$, —NR$^{134}$C(=S)R$^{130}$, —NR$^{134}$C(=S)OR$^{130}$, —NR$^{134}$C(=S)NR$^{132}$R$^{133}$, —NR$^{134}$S(=O)$_2$R$^{131}$, —NR$^{134}$S(=O)$_2$NR$^{132}$R$^{133}$, —OR$^{130}$, =O, —OCN, —OC (=O)R$^{130}$, —OC(=O)NR$^{132}$R$^{133}$, —OC(=O)OR$^{130}$, —OC(=NR$^{135}$)NR$^{132}$R$^{133}$, —OS(=O)R$^{130}$, —OS(=O)$_2$ R$^{130}$, —OS(=O)$_2$OR$^{130}$, —OS(=O)$_2$NR$^{132}$R$^{133}$, —SCN, =S, —S(=O)$_n$R$^{130}$, —S(=O)$_2$OR$^{130}$, —SO$_3$R$^{137}$, —S(=O)$_2$NR$^{132}$R$^{133}$, and —S(=O)NR$^{132}$R$^{133}$. In another embodiment, Z$^3$ is H, C$_{1-6}$alkyl optionally substituted by 1-13 R$^{89}$, C$_{6-11}$aryl optionally substituted by 1-7 R$^{89}$, C$_{7-16}$arylalkyl optionally substituted by 1-19 R$^{89}$, C$_{3-11}$cycloalkyl optionally substituted by 1-21 R$^{89}$, C$_{4-17}$cycloalkylalkyl optionally substituted by 1-32 R$^{89}$, 3-15 membered heterocycloalkyl optionally substituted by 1-28 R$^{89}$, 4-21 membered heterocycloalkylalkyl optionally substituted by 1-40 R$^{89}$, 5-15 membered heteroaryl optionally substituted by 1-15 R$^{89}$, 6-21 membered heteroarylalkyl optionally substituted by 1-27 R$^{89}$, halogen, —CN, —C(=O)R$^{80}$, —C(=O) OR$^{80}$, —C(=O)NR$^{82}$R$^{83}$, —C(=O)C(=O)R$^{80}$, —C(=S) NR$^{82}$R$^{83}$, —NC, —NO$_2$, —NR$^{82}$R$^{83}$, —NR$^{84}$NR$^{82}$R$^{83}$, —NR$^{84}$C(=O)R$^{80}$, —NR$^{84}$C(=O)C(=O)R$^{80}$, —NR$^{84}$C (=O)OR$^{81}$, —NR$^{84}$C(=O)C(=O)OR$^{81}$, —NR$^{84}$C(=O) NR$^{82}$R$^{83}$, —NR$^{84}$C(=O)NR$^{84}$C(=O)R$^{80}$, —NR$^{84}$C(=O) NR$^{84}$C(=O)OR$^{80}$, —NR$^{84}$C(=NR$^{85}$)NR$^{82}$R$^{83}$, —NR$^{84}$C (=O)C(=O)NR$^{82}$R$^{83}$, —NR$^{84}$C(=S)R$^{80}$, —NR$^{84}$C(=S) OR$^{80}$, —NR$^{84}$C(=S)NR$^{82}$R$^{83}$, —NR$^{84}$S(=O)$_2$R$^{81}$, —NR$^{84}$S(=O)$_2$NR$^{82}$R$^{83}$, —OR$^{80}$, =O, —OCN, —OC (=O)R$^{80}$, —OC(=O)NR$^{82}$R$^{83}$, —OC(=O)OR$^{80}$, —OS (=O)R$^{80}$, —OS(=O)$_2$R$^{80}$, —OS(=O)$_2$OR$^{80}$, —OS(=O)$_2$ NR$^{82}$R$^{83}$, —SCN, =S, —S(=O)$_n$R$^{80}$, —S(=O)$_2$OR$^{80}$, —SO$_3$R$^{87}$, —S(=O)$_2$NR$^{82}$R$^{83}$, or —S(=O)NR$^{82}$R$^{83}$; alternatively, when L$^2$, A$^2$, G$^2$, X$^2$, L$^3$, A$^3$, G$^3$ and X$^3$ are absent, Z$^2$ and Z$^3$ can together form a group of formula -A$^{21}$-A$^{22}$-A$^{23}$-, or when L$^3$, A$^3$, G$^3$, X$^3$, L$^4$, A$^4$, G$^4$ and X$^4$ are absent, Z$^3$ and Z$^4$ can together form a group of formula -A$^{21}$-A$^{22}$-A$^{23}$-; wherein A$^{21}$, A$^{22}$, and A$^{23}$ are independently chosen from —CZ$^{21}$Z$^{22}$—, —CZ$^{23}$Z$^{24}$CZ$^{25}$Z$^{26}$—, —C(=O)—, —NZ$^{27}$—, —S—, —S(=O)—, —S(=O)$_2$—, or —O—; wherein:
(a) when any two of Z$^{21}$, Z$^{22}$, Z$^{23}$, Z$^{24}$, Z$^{25}$, Z$^{26}$ and Z$^{27}$ are located on adjacent atoms, they may together form a bond between the atoms, and
(b) any of Z$^{21}$, Z$^{22}$, Z$^{23}$, Z$^{24}$, Z$^{25}$, Z$^{26}$ and Z$^{27}$ may be independently chosen from H, C$_{1-6}$alkyl optionally substituted by 1-13 R$^{99}$, C$_{6-11}$ aryl optionally substituted by 1-7 R$^{99}$, C$_{7-16}$arylalkyl optionally substituted by 1-19 R$^{99}$, C$_{3-11}$cycloalkyl optionally substituted by 1-21 R$^{99}$, C$_{4-17}$cycloalkylalkyl optionally substituted by 1-32 R$^{99}$, 3-15 membered heterocycloalkyl optionally substituted by 1-28 R$^{99}$, 4-21 membered heterocycloalkylalkyl optionally substituted by 1-40 R$^{99}$, 5-15 membered heteroaryl optionally substituted by 1-15 R$^{99}$, 6-21 membered heteroarylalkyl optionally substituted by 1-27 R$^{99}$, halogen, —CN, —C(=O)R$^{90}$, —C(=O)OR$^{90}$, —C(=O)NR$^{92}$R$^{93}$, —C(=O)C(=O)R$^{90}$, —C(=S)NR$^{92}$R$^{93}$, —NC, —NO$_2$, —NR$^{92}$R$^{93}$, —NR$^{94}$NR$^{92}$R$^{93}$, —NR$^{94}$C(=O)R$^{90}$, —NR$^{94}$C(=O)C (=O)R$^{90}$, —NR$^{94}$C(=O)OR$^{91}$, —NR$^{94}$C(=O)C(=O) OR$^{91}$, —NR$^{94}$C(=O)NR$^{92}$R$^{93}$, —NR$^{94}$C(=O)NR$^{94}$C (=O)R$^{90}$, —NR$^{94}$C(=O)NR$^{94}$C(=O)OR$^{90}$, —NR$^{94}$C (=NR$^{95}$)NR$^{92}$R$^{93}$, —NR$^{94}$C(=O)C(=O)NR$^{92}$R$^{93}$, —NR$^{94}$C(=S)R$^{90}$, —NR$^{94}$C(=S)OR$^{90}$, —NR$^{94}$C(=S) NR$^{92}$R$^{93}$, —NR$^{94}$S(=O)$_2$R$^{91}$, —NR$^{94}$S(=O)$_2$NR$^{92}$R$^{93}$, —OR$^{90}$, =O, —OCN, —OC(=O)R$^{90}$, —OC(=O) NR$^{92}$R$^{93}$, —OC(=O)OR$^{90}$, —OS(=O)R$^{90}$, —OS(=O)$_2$ R$^{90}$, —OS(=O)$_2$OR$^{90}$, —OS(=O)$_2$NR$^{92}$R$^{93}$, —SCN, =S, —S(=O)$_n$R$^{90}$, —S(=O)$_2$OR$^{90}$, —SO$_3$R$^{97}$, —S(=O)$_2$ NR$^{92}$R$^{93}$, and —S(=O)NR$^{92}$R$^{93}$; and
(c) any two of Z$^{21}$, Z$^{22}$, Z$^{23}$, Z$^{24}$, Z$^{25}$, Z$^{26}$ and Z$^{27}$ may together form a group of formula -A$^{31}$-A$^{32}$-A$^{33}$-, wherein A$^{31}$, A$^{32}$, and A$^{33}$ are independently chosen from —CZ$^{31}$Z$^{32}$—, —CZ$^{33}$Z$^{34}$CZ$^{35}$Z$^{36}$—, —C(=O)—, —NZ$^{37}$—, —S—, —S(=O)—, —S(=O)$_2$—, or —O— wherein:
(i) when any two of Z$^{31}$, Z$^{32}$, Z$^{33}$, Z$^{34}$, Z$^{35}$, Z$^{36}$ and Z$^{37}$ are located on adjacent atoms, they may together form a bond between the atoms, and
(ii) any of any of Z$^{21}$, Z$^{22}$, Z$^{23}$, Z$^{24}$, Z$^{25}$, Z$^{26}$ and Z$^{27}$ may be independently chosen from H, C$_{1-6}$alkyl optionally substituted by 1-13 R$^{139}$, C$_{6-11}$aryl optionally substituted by 1-7 R$^{139}$, C$_{7-16}$arylalkyl optionally substituted by 1-19 R$^{139}$, C$_{3-11}$cycloalkyl optionally substituted by 1-21 R$^{139}$, C$_{4-17}$cycloalkylalkyl optionally substituted by 1-32 R$^{139}$, 3-15 membered heterocycloalkyl optionally substituted by 1-28 R$^{139}$, 4-21 membered heterocycloalkylalkyl optionally substituted by 1-40 R$^{139}$, 5-15 membered heteroaryl optionally substituted by 1-15 R$^{139}$, 6-21 membered heteroarylalkyl optionally substituted by 1-27 R$^{139}$, halogen, —CN, —C(=O)R$^{130}$, —C(=O)OR$^{130}$, —C(=O)NR$^{132}$R$^{133}$, —C(=O)C(=O) R$^{130}$, —C(=S)NR$^{132}$R$^{133}$, —NC, —NO$_2$, —NR$^{132}$R$^{133}$, —NR$^{134}$NR$^{132}$R$^{133}$, —NR$^{134}$C(=O)R$^{130}$, —NR$^{134}$C(=O) C(=O)R$^{130}$, —NR$^{134}$C(=O)OR$^{131}$, —NR$^{134}$C(=O)C (=O)OR$^{131}$, —NR$^{134}$C(=O)NR$^{132}$R$^{133}$, —NR$^{134}$C(=O) NR$^{134}$C(=O)R$^{130}$, —NR$^{134}$C(=O)NR$^{134}$C(=O)OR$^{130}$, —NR$^{134}$C(=NR$^{135}$)NR$^{132}$R$^{133}$, —NR$^{134}$C(=O)C(=O) NR$^{132}$R$^{133}$, —NR$^{134}$C(=S)R$^{130}$, —NR$^{134}$C(=S)OR$^{130}$, —NR$^{134}$C(=S)NR$^{132}$R$^{133}$, —NR$^{134}$S(=O)$_2$R$^{131}$, —NR$^{134}$S(=O)$_2$NR$^{132}$R$^{133}$, —OR$^{130}$, =O, —OCN, —OC (=O)R$^{130}$, —OC(=O)NR$^{132}$R$^{133}$, —OC(=O)OR$^{130}$, —OS(=O)R$^{130}$, —OS(=O)$_2$R$^{130}$, —OS(=O)$_2$OR$^{130}$, —OS(=O)$_2$NR$^{132}$R$^{133}$, —SCN, =S, —S(=O)$_n$R$^{130}$, —S(=O)$_2$OR$^{130}$, —SO$_3$R$^{137}$, —S(=O)$_2$NR$^{132}$R$^{133}$, and —S(=O)NR$^{132}$R$^{133}$. In another embodiment, Z$^3$ is H, C$_{1-6}$alkyl optionally substituted by 1-13 R$^{89}$, C$_{6-11}$aryl optionally substituted by 1-7 R$^{89}$, C$_{7-16}$arylalkyl optionally substituted by 1-19 R$^{89}$, C$_{3-11}$cycloalkyl optionally substituted by 1-21 R$^{89}$, C$_{4-17}$cycloalkylalkyl optionally substituted by 1-32 R$^{89}$, 3-15 membered heterocycloalkyl optionally substituted by 1-28 R$^{89}$, 4-21 membered heterocycloalkylalkyl optionally substituted by 1-40 R$^{89}$, 5-15 membered heteroaryl optionally substituted by 1-15 R$^{89}$, 6-21 membered heteroarylalkyl optionally substituted by 1-27 R$^{89}$, halogen, —CN, —C(=O)R$^{80}$, —C(=O)OR$^{80}$, —C(=O)NR$^{82}$R$^{83}$, —C(=S)NR$^{82}$R$^{83}$, —NC, —NO$_2$, —NR$^{82}$R$^{83}$, —NR$^{84}$NR$^{82}$R$^{83}$, —NR$^{84}$C(=O)R$^{80}$, —NR$^{84}$C(=O)OR$^{81}$, —NR$^{84}$C(=O)NR$^{82}$R$^{83}$, —NR$^{84}$C (=O)NR$^{84}$C(=O)R$^{80}$, —NR$^{84}$C(=O)NR$^{84}$C(=O)OR$^{80}$, —NR$^{84}$C(=NR$^{85}$)NR$^{82}$R$^{83}$, —NR$^{84}$C(=S)R$^{80}$, —NR$^{84}$C (=S)NR$^{82}$R$^{83}$, —NR$^{84}$S(=O)$_2$R$^{81}$, —NR—OR$^{80}$, =O, —OCN, —OC(=O)R$^{80}$, —OC(=O)NR$^{82}$R$^{83}$, —SCN, =S, —S(=O)$_n$R$^{80}$, —S(=O)$_2$OR$^{80}$, —S(=O)$_2$NR$^{82}$R$^{83}$, or —P(=O)R$^{88}$R$^{88}$; alternatively, when L$^2$, A$^2$, G$^2$, X$^2$, L$^3$, A$^3$, G$^3$ and X$^3$ are absent, Z$^2$ and Z$^3$ can together form a group of formula -A$^{21}$-A$^{22}$-A$^{23}$-, or when L$^3$, A$^3$, G$^3$, X$^3$, L$^4$, A$^4$, G$^4$ and X$^4$ are absent, Z$^3$ and Z$^4$ can together form a group of formula -A$^{21}$-A$^{22}$-A$^{23}$-; wherein A$^{21}$, A$^{22}$, and A$^{23}$ are independently chosen from —CZ$^{21}$Z$^{22}$—, —CZ$^{23}$Z$^{24}$CZ$^{25}$Z$^{26}$—, —C(=O)—, —NZ$^{27}$—, —S—, —S(=O)—, —S(=O)$_2$—, or —O—; wherein:

(a) when any two of $Z^{21}$, $Z^{22}$, $Z^{23}$, $Z^{24}$, $Z^{25}$, $Z^{26}$ and $Z^{27}$ are located on adjacent atoms, they may together form a bond between the atoms, and (b) any of $Z^{21}$, $Z^{22}$, $Z^{23}$, $Z^{24}$, $Z^{25}$, $Z^{26}$ and $Z^{27}$ may be independently chosen from H, $C_{1-6}$alkyl optionally substituted by 1-13 $R^{99}$, $C_{6-11}$ aryl optionally substituted by 1-7 $R^{99}$, $C_{7-16}$arylalkyl optionally substituted by 1-19 $R^{99}$, $C_{3-11}$cycloalkyl optionally substituted by 1-21 $R^{99}$, $C_{4-17}$cycloalkylalkyl optionally substituted by 1-32 $R^{99}$, 3-15 membered heterocycloalkyl optionally substituted by 1-28 $R^{99}$, 4-21 membered heterocycloalkylalkyl optionally substituted by 1-40 $R^{99}$, 5-15 membered heteroaryl optionally substituted by 1-15 $R^{99}$, 6-21 membered heteroarylalkyl optionally substituted by 1-27 $R^{99}$, halogen, —CN, —C(=O)$R^{90}$, —C(=O)O$R^{90}$, —C(=O)N$R^{92}R^{93}$, —C(=S)N$R^{92}R^{93}$, —NC, —NO$_2$, —N$R^{92}R^{93}$, —N$R^{94}$N$R^{92}R^{93}$, —N$R^{94}$C(=O)$R^{90}$, —N$R^{94}$C(=O)O$R^{91}$, —N$R^{94}$C(=O)N$R^{92}R^{93}$, —N$R^{94}$C(=O)N$R^{94}$C(=O)$R^{90}$, —N$R^{94}$C(=O)N$R^{94}$C(=O)O$R^{90}$, —N$R^{94}$C(=N$R^{95}$)N$R^{92}R^{93}$, —N$R^{94}$C(=S)$R^{90}$, —N$R^{94}$C(=S)N$R^{92}R^{93}$, —N$R^{94}$S(=O)$_2R^{91}$, —N$R^{94}$P(=O)$R^{98}R^{98}$, —O$R^{90}$, =O, —OCN, —OC(=O)N$R^{92}R^{93}$, —SCN, =S, —S(=O)$_n R^{90}$, —S(=O)$_2$N$R^{92}R^{93}$, and —P(=O)$R^{98}R^{98}$; and (c) any two of $Z^{21}$, $Z^{22}$, $Z^{23}$, $Z^{24}$, $Z^{25}$, $Z^{26}$ and $Z^{27}$ may together form a group of formula -$A^{31}$-$A^{32}$-$A^{33}$-, wherein $A^{31}$, $A^{32}$, and $A^{33}$ are independently chosen from —C$Z^{31}Z^{32}$—, —C$Z^{33}Z^{34}$C$Z^{35}Z^{36}$—, —C(=O)—, —N$Z^{37}$—, —S—, —S(=O)—, —S(=O)$_2$—, or —O— wherein:

(i) when any two of $Z^{31}$, $Z^{32}$, $Z^{33}$, $Z^{34}$, $Z^{35}$, $Z^{36}$ and $Z^{37}$ are located on adjacent atoms, they may together form a bond between the atoms, and (ii) any of any of $Z^{21}$, $Z^{22}$, $Z^{23}$, $Z^{24}$, $Z^{25}$, $Z^{26}$ and $Z^{27}$ may be independently chosen from H, $C_{1-6}$alkyl optionally substituted by 1-13 $R^{139}$, $C_{6-11}$ aryl optionally substituted by 1-7 $R^{139}$, $C_{7-16}$arylalkyl optionally substituted by 1-19 $R^{139}$, $C_{3-11}$cycloalkyl optionally substituted by 1-21 $R^{139}$, $C_{4-17}$cycloalkylalkyl optionally substituted by 1-32 $R^{139}$, 3-15 membered heterocycloalkyl optionally substituted by 1-28 $R^{139}$, 4-21 membered heterocycloalkylalkyl optionally substituted by 1-40 $R^{139}$, 5-15 membered heteroaryl optionally substituted by 1-15 $R^{139}$, 6-21 membered heteroarylalkyl optionally substituted by 1-27 $R^{139}$, halogen, —CN, —C(=O)$R^{130}$, —C(=O)O$R^{130}$, —C(=O)N$R^{132}R^{133}$, —C(=S)N$R^{132}R^{133}$, —NC, —NO$_2$, —N$R^{132}R^{133}$, —N$R^{134}$N$R^{132}R^{133}$, —N$R^{134}$C(=O)$R^{130}$, —N$R^{134}$C(=O)O$R^{131}$, —N$R^{134}$C(=O)N$R^{132}R^{133}$, —N$R^{134}$C(=O)N$R^{134}$C(=O)$R^{130}$, —N$R^{134}$C(=N$R^{135}$)N$R^{132}R^{133}$, —N$R^{134}$C(=S)$R^{130}$, —N$R^{134}$C(=S)N$R^{132}R^{133}$, —N$R^{134}$S(=O)$_2R^{131}$, —N$R^{134}$P(=O)$R^{138}R^{138}$, —O$R^{130}$, =O, —OCN, —OC(=O)$R^{130}$, —OC(=O)N$R^{132}R^{133}$, —SCN, =S, —S(=O)$_n R^{130}$, —S(=O)$_2$N$R^{132}R^{133}$, and —P(=O)$R^{138}R^{138}$. In another embodiment, $Z^3$ is H, $C_{1-6}$alkyl optionally substituted by 1-13 $R^{89}$, $C_{6-11}$ aryl optionally substituted by 1-7 $R^{89}$, $C_{7-16}$arylalkyl optionally substituted by 1-19 $R^{89}$, $C_{3-11}$cycloalkyl optionally substituted by 1-21 $R^{89}$, $C_{4-17}$cycloalkylalkyl optionally substituted by 1-32 $R^{89}$, 3-15 membered heterocycloalkyl optionally substituted by 1-28 $R^{89}$, 4-21 membered heterocycloalkylalkyl optionally substituted by 1-40 $R^{89}$, 5-15 membered heteroaryl optionally substituted by 1-15 $R^{89}$, 6-21 membered heteroarylalkyl optionally substituted by 1-27 $R^{89}$, halogen, —CN, —C(=O)$R^{80}$, —C(=O)O$R^{80}$, —C(=O)N$R^{82}R^{83}$, —C(=S)N$R^{82}R^{83}$, —NC, —NO$_2$, —N$R^{82}R^{83}$, —N$R^{84}$N$R^{82}R^{83}$, —N$R^{84}$C(=O)$R^{80}$, —N$R^{84}$C(=O)O$R^{81}$, —N$R^{84}$C(=O)N$R^{82}R^{83}$, —N$R^{84}$C(=O)N$R^{84}$C(=O)$R^{80}$, —N$R^{84}$C(=O)N$R^{84}$C(=O)O$R^{80}$, —N$R^{84}$C(=N$R^{85}$)N$R^{82}R^{83}$, —N$R^{84}$C(=S)$R^{80}$, —N$R^{84}$C(=S)N$R^{82}R^{83}$, —N$R^{84}$S(=O)$_2R^{81}$, —O$R^{80}$, =O, —OCN, —OC(=O)$R^{80}$, —OC(=O)N$R^{82}R^{83}$, —SCN, =S, —S(=O)$_n R^{80}$, —S(=O)$_2$O$R^{80}$, or —S(=O)$_2$N$R^{82}R^{83}$; alternatively, when $L^2$, $A^2$, $G^2$, $X^2$, $L^3$, $A^3$, $G^3$ and $X^3$ are absent, $Z^2$ and $Z^3$ can together form a group of formula -$A^{21}$-$A^{22}$-$A^{23}$-, or when $L^3$, $A^3$, $G^3$, $X^3$, $L^4$, $A^4$, $G^4$ and $X^4$ are absent, $Z^3$ and $Z^4$ can together form a group of formula -$A^{21}$-$A^{22}$-$A^{23}$-; wherein $A^{21}$, $A^{22}$, and $A^{23}$ are independently chosen from —C$Z^{21}Z^{22}$—, —C$Z^{23}Z^{24}$C$Z^{25}Z^{26}$—, —C(=O)—, —N$Z^{27}$—, —S—, —S(=O)—, —S(=O)$_2$—, or —O—; wherein:

(a) when any two of $Z^{21}$, $Z^{22}$, $Z^{23}$, $Z^{24}$, $Z^{25}$, $Z^{26}$ and $Z^{27}$ are located on adjacent atoms, they may together form a bond between the atoms, and (b) any of $Z^{21}$, $Z^{22}$, $Z^{23}$, $Z^{24}$, $Z^{25}$, $Z^{26}$ and $Z^{27}$ may be independently chosen from H, $C_{1-6}$alkyl optionally substituted by 1-13 $R^{99}$, $C_{6-11}$ aryl optionally substituted by 1-7 $R^{99}$, $C_{7-16}$arylalkyl optionally substituted by 1-19 $R^{99}$, $C_{3-11}$cycloalkyl optionally substituted by 1-21 $R^{99}$, $C_{4-17}$cycloalkylalkyl optionally substituted by 1-32 $R^{99}$, 3-15 membered heterocycloalkyl optionally substituted by 1-28 $R^{99}$, 4-21 membered heterocycloalkylalkyl optionally substituted by 1-40 $R^{99}$, 5-15 membered heteroaryl optionally substituted by 1-15 $R^{99}$, 6-21 membered heteroarylalkyl optionally substituted by 1-27 $R^{99}$, halogen, —CN, —C(=O)$R^{90}$, —C(=O)O$R^{90}$, —C(=O)N$R^{92}R^{93}$, —C(=S)N$R^{92}R^{93}$, —NC, —NO$_2$, —N$R^{92}R^{93}$, —N$R^{94}$N$R^{92}R^{93}$, —N$R^{94}$C(=O)$R^{90}$, —N$R^{94}$C(=O)O$R^{91}$, —N$R^{94}$C(=O)N$R^{92}R^{93}$, —N$R^{94}$C(=O)N$R^{94}$C(=O)$R^{90}$, —N$R^{94}$C(=O)N$R^{94}$C(=O)O$R^{90}$, —N$R^{94}$C(=N$R^{95}$)N$R^{92}R^{93}$, —N$R^{94}$C(=S)$R^{90}$, —N$R^{94}$C(=S)N$R^{92}R^{93}$, —N$R^{94}$S(=O)$_2R^{91}$, —O$R^{90}$, =O, —OCN, —OC(=O)N$R^{92}R^{93}$, —SCN, =S, —S(=O)$_n R^{90}$, and —S(=O)$_2$N$R^{92}R^{93}$; and (c) any two of $Z^{21}$, $Z^{22}$, $Z^{23}$, $Z^{24}$, $Z^{25}$, $Z^{26}$ and $Z^{27}$ may together form a group of formula -$A^{31}$-$A^{32}$-$A^{33}$-, wherein $A^{31}$, $A^{32}$, and $A^{33}$ are independently chosen from —C$Z^{31}Z^{32}$—, —C$Z^{33}Z^{34}$C$Z^{35}Z^{36}$—, —C(=O)—, —N$Z^{37}$—, —S—, —S(=O)—, —S(=O)$_2$—, or —O— wherein:

(i) when any two of $Z^{31}$, $Z^{32}$, $Z^{33}$, $Z^{34}$, $Z^{35}$, $Z^{36}$ and $Z^{37}$ are located on adjacent atoms, they may together form a bond between the atoms, and (ii) any of any of $Z^{21}$, $Z^{22}$, $Z^{23}$, $Z^{24}$, $Z^{25}$, $Z^{26}$ and $Z^{27}$ may be independently chosen from H, $C_{1-6}$alkyl optionally substituted by 1-13 $R^{139}$, $C_{6-11}$ aryl optionally substituted by 1-7 $R^{139}$, $C_{7-16}$arylalkyl optionally substituted by 1-19 $R^{139}$, $C_{3-11}$cycloalkyl optionally substituted by 1-21 $R^{139}$, $C_{4-17}$cycloalkylalkyl optionally substituted by 1-32 $R^{139}$, 3-15 membered heterocycloalkyl optionally substituted by 1-28 $R^{139}$, 4-21 membered heterocycloalkylalkyl optionally substituted by 1-40 $R^{139}$, 5-15 membered heteroaryl optionally substituted by 1-15 $R^{139}$, 6-21 membered heteroarylalkyl optionally substituted by 1-27 $R^{139}$, halogen, —CN, —C(=O)$R^{130}$, —C(=O)O$R^{130}$, —C(=O)N$R^{132}R^{133}$, —C(=S)N$R^{132}R^{133}$, —NC, —NO$_2$, —N$R^{132}R^{133}$, —N$R^{134}$N$R^{132}R^{133}$, —N$R^{134}$C(=O)$R^{130}$, —N$R^{134}$C(=O)O$R^{131}$, —N$R^{134}$C(=O)N$R^{132}R^{133}$, —N$R^{134}$C(=O)N$R^{134}$C(=O)$R^{130}$, —N$R^{134}$C(=N$R^{135}$)N$R^{132}R^{133}$, —N$R^{134}$C(=S)$R^{130}$, —N$R^{134}$C(=S)N$R^{132}R^{133}$, —N$R^{134}$S(=O)$_2R^{131}$, —O$R^{130}$, =O, —OCN, —OC(=O)$R^{130}$, —OC(=O)N$R^{132}R^{133}$, —SCN, =S, —S(=O)$_n R^{130}$, and —S(=O)$_2$N$R^{132}R^{133}$. In another embodiment, $Z^3$ is H, $C_{1-6}$alkyl optionally substituted by 1-13 $R^{89}$, $C_{6-11}$aryl optionally substituted by 1-7 $R^{89}$, $C_{7-16}$arylalkyl optionally substituted by 1-19 $R^{89}$, $C_{3-11}$cycloalkyl optionally substituted by 1-21 $R^{89}$, $C_{4-17}$cycloalkylalkyl optionally substituted by 1-32 $R^{89}$, 3-15 membered heterocycloalkyl optionally substituted by 1-28 $R^{89}$, 4-21 membered heterocycloalkylalkyl optionally substituted by 1-40 $R^{89}$, 5-15 membered heteroaryl optionally substituted by 1-15 $R^{89}$, 6-21 membered heteroarylalkyl optionally substituted by 1-27 $R^{89}$, halogen, —CN, —C(=O)$R^{80}$, —C(=O)O$R^{80}$, —C(=O)N$R^{82}R^{83}$, —C(=S)N$R^{82}R^{83}$, —N$R^{82}R^{83}$, —N$R^{84}$C(=O)$R^{80}$, —N$R^{84}$C(=O)O$R^{81}$, —N$R^{84}$C(=O)N$R^{82}R^{83}$, —N$R^{84}$C(=O)N$R^{84}$C(=O)$R^{80}$, —N$R^{84}$C(=O)N$R^{84}$C(=O)O$R^{80}$, —N$R^{84}$C(=S)$R^{80}$, —N$R^{84}$S(=O)$_2R^{81}$, —O$R^{80}$, =O, —OC(=O)$R^{80}$, —OC(=O)N$R^{82}R^{83}$, =S, —S(=O)$_nR^{80}$, or —S(=O)$_2$N$R^{82}R^{83}$; alternatively, when $L^2$, $A^2$, $G^2$, $X^2$, $L^3$, $A^3$, $G^3$ and $X^3$ are absent, $Z^2$ and $Z^3$ can together form a group of formula -$A^{21}$-$A^{22}$-$A^{23}$-, or when $L^3$, $A^3$, $G^3$, $X^3$, $L^4$, $A^4$, $G^4$ and $X^4$ are absent, $Z^3$ and $Z^4$ can together form a group of formula -$A^{21}$-$A^{22}$-$A^{23}$-; wherein $A^{21}$, $A^{22}$, and $A^{23}$ are independently chosen from —C$Z^{21}Z^{22}$—, —C$Z^{23}Z^{24}$C$Z^{25}Z^{26}$—, —C(=O)—, —N$Z^{27}$—, —S—, —S(=O)—, —S(=O)$_2$—, or —O—; wherein:

(a) when any two of $Z^{21}$, $Z^{22}$, $Z^{23}$, $Z^{24}$, $Z^{25}$, $Z^{26}$ and $Z^{27}$ are located on adjacent atoms, they may together form a bond between the atoms, and (b) any of $Z^{21}$, $Z^{22}$, $Z^{23}$, $Z^{24}$, $Z^{25}$, $Z^{26}$ and $Z^{27}$ may be independently chosen from H, $C_{1-6}$alkyl optionally substituted by 1-13 $R^{99}$, $C_{6-11}$ aryl optionally substituted by 1-7 $R^{99}$, $C_{7-16}$arylalkyl optionally substituted by 1-19 $R^{99}$, $C_{3-11}$cycloalkyl optionally substituted by 1-21 $R^{99}$, $C_{4-17}$cycloalkylalkyl optionally substituted by 1-32 $R^{99}$, 3-15 membered heterocycloalkyl optionally substituted by 1-28 $R^{99}$, 4-21 membered heterocycloalkylalkyl optionally substituted by 1-40 $R^{99}$, 5-15 membered heteroaryl optionally substituted by 1-15 $R^{99}$, 6-21 membered heteroarylalkyl optionally substituted by 1-27 $R^{99}$, halogen, —CN, —C(=O)$R^{90}$, —C(=O)O$R^{90}$, —C(=O)N$R^{92}R^{93}$, —C(=S)N$R^{92}R^{93}$, —N$R^{92}R^{93}$, —N$R^{94}$C(=O)$R^{90}$, —N$R^{94}$C(=O)O$R^{91}$, —N$R^{94}$C(=O)N$R^{92}R^{93}$, —N$R^{94}$C(=O)N$R^{94}$C(=O)$R^{90}$, —N$R^{94}$C(=O)N$R^{94}$C(=O)O$R^{90}$, —N$R^{94}$C(=S)$R^{90}$, —N$R^{94}$S(=O)$_2R^{91}$, —O$R^{90}$, =O, —OC(=O)$R^{90}$, —OC(=O)N$R^{92}R^{93}$, =S, —S(=O)$_nR^{90}$, and —S(=O)$_2$N$R^{92}R^{93}$; and (c) any two of $Z^{21}$, $Z^{22}$, $Z^{23}$, $Z^{24}$, $Z^{25}$, $Z^{26}$ and $Z^{27}$ may together form a group of formula -$A^{31}$-$A^{32}$-$A^{33}$-, wherein $A^{31}$, $A^{32}$, and $A^{33}$ are independently chosen from —C$Z^{31}Z^{32}$—, —C$Z^{33}Z^{34}$C$Z^{35}Z^{36}$—, —C(=O)—, —N$Z^{37}$—, —S—, —S(=O)—, —S(=O)$_2$—, or —O— wherein:

(i) when any two of $Z^{31}$, $Z^{32}$, $Z^{33}$, $Z^{34}$, $Z^{35}$, $Z^{36}$ and $Z^{37}$ are located on adjacent atoms, they may together form a bond between the atoms, and (ii) any of any of $Z^{21}$, $Z^{22}$, $Z^{23}$, $Z^{24}$, $Z^{25}$, $Z^{26}$ and $Z^{27}$ may be independently chosen from H, $C_{1-6}$alkyl optionally substituted by 1-13 $R^{139}$, $C_{6-11}$ aryl optionally substituted by 1-7 $R^{139}$, $C_{7-16}$arylalkyl optionally substituted by 1-19 $R^{139}$, $C_{3-11}$cycloalkyl optionally substituted by 1-21 $R^{139}$, $C_{4-17}$cycloalkylalkyl optionally substituted by 1-32 $R^{139}$, 3-15 membered heterocycloalkyl optionally substituted by 1-28 $R^{139}$, 4-21 membered heterocycloalkylalkyl optionally substituted by 1-40 $R^{139}$, 5-15 membered heteroaryl optionally substituted by 1-15 $R^{139}$, 6-21 membered heteroarylalkyl optionally substituted by 1-27 $R^{139}$, halogen, —CN, —C(=O)$R^{130}$, —C(=O)O$R^{130}$, —C(=O)N$R^{132}R^{133}$, —C(=S)N$R^{132}R^{133}$, —N$R^{132}R^{133}$, —N$R^{134}$C(=O)$R^{130}$, —N$R^{134}$C(=O)O$R^{131}$, —N$R^{134}$C(=O)N$R^{132}R^{133}$, —N$R^{134}$C(=O)N$R^{134}$C(=O)$R^{130}$, —N$R^{134}$C(=S)$R^{130}$, —N$R^{134}$S(=O)$R^{131}$, —O$R^{130}$, =O, —OCN, —OC(=O)$R^{130}$, —OC(=O)N$R^{132}R^{133}$, =S, —S(=O)$_nR^{130}$, and —S(=O)$_2$N$R^{132}R^{133}$.

In another embodiment, $Z^3$ is H, $C_{1-6}$alkyl optionally substituted by 1-13 $R^{89}$, $C_{6-11}$aryl optionally substituted by 1-7 $R^{89}$, $C_{7-16}$arylalkyl optionally substituted by 1-19 $R^{89}$, $C_{3-11}$cycloalkyl optionally substituted by 1-21 $R^{89}$, $C_{4-6}$cycloalkylalkyl optionally substituted by 1-32 $R^{89}$, 3-15 membered heterocycloalkyl optionally substituted by 1-28 $R^{89}$, 4-21 membered heterocycloalkylalkyl optionally substituted by 1-40 $R^{89}$, 5-15 membered heteroaryl optionally substituted by 1-15 $R^{89}$, 6-21 membered heteroarylalkyl optionally substituted by 1-27 $R^{89}$, halogen, —CN, —C(=O)$R^{80}$, —C(=O)O$R^{80}$, —C(=O)N$R^{82}R^{83}$, —N$R^{82}R^{83}$, —N$R^{84}$C(=O)$R^{80}$, —N$R^{84}$C(=O)O$R^{81}$, —N$R^{84}$C(=O)N$R^{82}R^{83}$, —N$R^{84}$S(=O)$_2R^{81}$, —N$R^{84}$P(=O)$R^{88}R^{88}$, —O$R^{80}$, =O, —OC(=O)$R^{80}$, —OC(=O)N$R^{82}R^{83}$, =S, —S(=O)$_nR^{80}$, —S(=O)$_2$N$R^{82}R^{83}$, or —P(=O)$R^{88}R^{88}$; alternatively, when $L^2$, $A^2$, $G^2$, $X^2$, $L^3$, $A^3$, $G^3$ and $X^3$ are absent, $Z^2$ and $Z^3$ can together form a group of formula -$A^{21}$-$A^{22}$-$A^{23}$-, or when $L^3$, $A^3$, $G^3$, $X^3$, $L^4$, $A^4$, $G^4$ and $X^4$ are absent, $Z^3$ and $Z^4$ can together form a group of formula -$A^{21}$-$A^{22}$-$A^{23}$-; wherein $A^{21}$, $A^{22}$, and $A^{23}$ are independently chosen from —C$Z^{21}Z^{22}$—, —C$Z^{23}Z^{24}$C$Z^{25}Z^{26}$—, or —N$Z^{27}$—; wherein:

(a) when any two of $Z^{21}$, $Z^{22}$, $Z^{23}$, $Z^{24}$, $Z^{25}$, $Z^{26}$ and $Z^{27}$ are located on adjacent atoms, they may together form a bond between the atoms, and (b) any of $Z^{21}$, $Z^{22}$, $Z^{23}$, $Z^{24}$, $Z^{25}$, $Z^{26}$ and $Z^{27}$ may be independently chosen from H, $C_{1-6}$alkyl optionally substituted by 1-13 $R^{99}$, $C_{6-11}$ aryl optionally substituted by 1-7 $R^{99}$, $C_{7-16}$arylalkyl optionally substituted by 1-19 $R^{99}$, $C_{3-11}$cycloalkyl optionally substituted by 1-21 $R^{99}$, $C_{4-17}$cycloalkylalkyl optionally substituted by 1-32 $R^{99}$, 3-15 membered heterocycloalkyl optionally substituted by 1-28 $R^{99}$, 4-21 membered heterocycloalkylalkyl optionally substituted by 1-40 $R^{99}$, 5-15 membered heteroaryl optionally substituted by 1-15 $R^{99}$, 6-21 membered heteroarylalkyl optionally substituted by 1-27 $R^{99}$, halogen, —CN, —C(=O)$R^{90}$, —C(=O)O$R^{90}$, —C(=O)N$R^{92}R^{93}$, —N$R^{92}R^{93}$, —N$R^{94}$C(=O)$R^{90}$, —N$R^{94}$C(=O)O$R^{91}$, —N$R^{94}$C(=O)N$R^{92}R^{93}$, —N$R^{94}$S(=O)$_2R^{91}$, —N$R^{94}$P(=O)$R^{98}R^{98}$, —O$R^{90}$, =O, —OC(=O)$R^{90}$, —OC(=O)N$R^{92}R^{93}$, =S, —S(=O)$_nR^{90}$, —S(=O)$_2$N$R^{92}R^{93}$, and —P(=O)$R^{98}R^{98}$; and (c) any two of $Z^{21}$, $Z^{22}$, $Z^{23}$, $Z^{24}$, $Z^{25}$, $Z^{26}$ and $Z^{27}$ may together form a group of formula -$A^{31}$-$A^{32}$-$A^{33}$-, wherein $A^{31}$, $A^{32}$, and $A^{33}$ are independently chosen from —C$Z^{31}Z^{32}$—,—C$Z^{33}Z^{34}$C$Z^{35}Z^{36}$—, or —N$Z^{37}$— wherein:

(i) when any two of $Z^{31}$, $Z^{32}$, $Z^{33}$, $Z^{34}$, $Z^{35}$, $Z^{36}$ and $Z^{37}$ are located on adjacent atoms, they may together form a bond between the atoms, and (ii) any of any of $Z^{21}$, $Z^{22}$, $Z^{23}$, $Z^{24}$, $Z^{25}$, $Z^{26}$ and $Z^{27}$ may be independently chosen from H, $C_{1-6}$alkyl optionally substituted by 1-13 $R^{139}$, $C_{6-11}$ aryl optionally substituted by 1-7 $R^{139}$, $C_{7-16}$arylalkyl optionally substituted by 1-19 $R^{139}$, $C_{3-11}$cycloalkyl optionally substituted by 1-21 $R^{139}$, $C_{4-17}$cycloalkylalkyl optionally substituted by 1-32 $R^{139}$, 3-15 membered heterocycloalkyl optionally substituted by 1-28 $R^{139}$, 4-21 membered heterocycloalkylalkyl optionally substituted by 1-40 $R^{139}$, 5-15 membered heteroaryl optionally substituted by 1-15 $R^{139}$, 6-21 membered heteroarylalkyl optionally substituted by 1-27 $R^{139}$, halogen, —CN, —C(=O)$R^{130}$, —C(=O)O$R^{130}$, —C(=O)N$R^{132}R^{133}$, —N$R^{132}R^{133}$, —N$R^{134}$C(=O)$R^{130}$, —N$R^{134}$C(=O)O$R^{131}$, —N$R^{134}$C(=O)N$R^{132}R^{133}$, —N$R^{134}$S(=O)$_2R^{131}$, —N$R^{134}$P(=O)$R^{138}R^{138}$, —O$R^{130}$, =O, —OCN, —OC(=O)$R^{130}$, —OC(=O)N$R^{132}R^{133}$, =S, —S(=O)$_nR^{130}$, —S(=O)$_2$N$R^{132}R^{133}$, and —P(=O)$R^{138}R^{138}$. In another embodiment, $Z^3$ is H, $C_{1-6}$alkyl optionally substituted by 1-13 $R^{89}$, $C_{6-11}$ aryl optionally substituted by 1-7 $R^{89}$, $C_{7-16}$arylalkyl optionally substituted by 1-19 $R^{89}$, $C_{3-11}$cycloalkyl optionally substituted by 1-21 $R^{89}$, $C_{4-17}$cycloalkylalkyl optionally substituted by 1-32 $R^{89}$, 3-15 membered heterocycloalkyl optionally substituted by 1-28 $R^{89}$, 4-21 membered heterocycloalkylalkyl optionally substituted by 1-40 $R^{89}$, 5-15 membered heteroaryl optionally substituted by 1-15 $R^{89}$, 6-21 membered heteroarylalkyl optionally substituted by 1-27 $R^{89}$, halogen, —CN, —C(=O)$R^{80}$, —C(=O)OR$^{80}$, —C(=O)NR$^{82}$R$^{83}$, —NR$^{82}$R$^{83}$, —NR$^{84}$C(=O)R$^{80}$, —NR$^{84}$C(=O)OR$^{81}$, —NR$^{84}$C(=O)NR$^{82}$R$^{83}$, —NR$^{84}$S(=O)$_2$R$^{81}$, —OR$^{80}$, =O, —OC(=O)R$^{80}$, —OC(=O)NR$^{82}$R$^{83}$, =S, —S(=O)$_n$R$^{80}$, or —S(=O)$_2$NR$^{82}$R$^{83}$; alternatively, when $L^2$, $A^2$, $G^2$, $X^2$, $L^3$, $A^3$, $G^3$ and $X^3$ are absent, $Z^2$ and $Z^3$ can together form a group of formula -A$^{21}$-A$^{22}$-A$^{23}$-, or when $L^3$, $A^3$, $G^3$, $X^3$, $L^4$, $A^4$, $G^4$ and $X^4$ are absent, $Z^3$ and $Z^4$ can together form a group of formula -A$^{21}$-A$^{22}$-A$^{23}$-; wherein $A^{21}$, $A^{22}$, and $A^{23}$ are independently chosen from —CZ$^{21}$Z$^{22}$—, —CZ$^{23}$Z$^{24}$CZ$^{25}$Z$^{26}$—, —C(=O)—, —NZ$^{27}$—, —S—, —S(=O)—, —S(=O)$_2$—, or —O—; wherein:

(a) when any two of $Z^{21}$, $Z^{22}$, $Z^{23}$, $Z^{24}$, $Z^{25}$, $Z^{26}$ and $Z^{27}$ are located on adjacent atoms, they may together form a bond between the atoms, and (b) any of $Z^{21}$, $Z^{22}$, $Z^{23}$, $Z^{24}$, $Z^{25}$, $Z^{26}$ and $Z^{27}$ may be independently chosen from H, $C_{1-6}$alkyl optionally substituted by 1-13 $R^{99}$, $C_{6-11}$ aryl optionally substituted by 1-7 $R^{99}$, $C_{7-16}$arylalkyl optionally substituted by 1-19 $R^{99}$, $C_{3-11}$cycloalkyl optionally substituted by 1-21 $R^{99}$, $C_{4-17}$cycloalkylalkyl optionally substituted by 1-32 $R^{99}$, 3-15 membered heterocycloalkyl optionally substituted by 1-28 $R^{99}$, 4-21 membered heterocycloalkylalkyl optionally substituted by 1-40 $R^{99}$, 5-15 membered heteroaryl optionally substituted by 1-15 $R^{99}$, 6-21 membered heteroarylalkyl optionally substituted by 1-27 $R^{99}$, halogen, —CN, —C(=O)R$^{90}$, —C(=O)OR$^{90}$, —C(=O)NR$^{92}$R$^{93}$, —C(=S)NR$^{92}$R$^{93}$, —NR$^{92}$R$^{93}$, —NR$^{94}$C(=O)R$^{90}$, —NR$^{94}$C(=O)OR$^{91}$, —NR$^{94}$C(=O)NR$^{92}$R$^{93}$, —NR$^{94}$C(=O)NR$^{94}$C(=O)R$^{90}$, —NR$^{94}$C(=O)NR$^{94}$C(=O)OR$^{90}$, —NR—NR$^{94}$S(=O)$_2$R$^{91}$, —OR$^{90}$, =O, —OC(=O)R$^{90}$, —OC(=O)NR$^{92}$R$^{93}$, =S, —S(=O)$_n$R$^{90}$, and —S(=O)$_2$NR$^{92}$R$^{93}$; and (c) any two of $Z^{21}$, $Z^{22}$, $Z^{23}$, $Z^{24}$, $Z^{25}$, $Z^{26}$ and $Z^{27}$ may together form a group of formula -A$^{31}$-A$^{32}$-A$^{33}$-, wherein $A^{31}$, $A^{32}$, and $A^{33}$ are independently chosen from —CZ$^{31}$Z$^{32}$—, —CZ$^{33}$Z$^{34}$CZ$^{35}$Z$^{36}$—, —C(=O)—, —NZ$^{37}$—, —S—, —S(=O)—, —S(=O)$_2$—, or —O— wherein:

(i) when any two of $Z^{31}$, $Z^{32}$, $Z^{33}$, $Z^{34}$, $Z^{35}$, $Z^{36}$ and $Z^{37}$ are located on adjacent atoms, they may together form a bond between the atoms, and (ii) any of any of $Z^{21}$, $Z^{22}$, $Z^{23}$, $Z^{24}$, $Z^{25}$, $Z^{26}$ and $Z^{27}$ may be independently chosen from H, $C_{1-6}$alkyl optionally substituted by 1-13 $R^{139}$, $C_{6-11}$ aryl optionally substituted by 1-7 $R^{139}$, $C_{7-16}$arylalkyl optionally substituted by 1-19 $R^{139}$, $C_{3-11}$cycloalkyl optionally substituted by 1-21 $R^{139}$, $C_{4-17}$cycloalkylalkyl optionally substituted by 1-32 $R^{139}$, 3-15 membered heterocycloalkyl optionally substituted by 1-28 $R^{139}$, 4-21 membered heterocycloalkylalkyl optionally substituted by 1-40 $R^{139}$, 5-15 membered heteroaryl optionally substituted by 1-15 $R^{139}$, 6-21 membered heteroarylalkyl optionally substituted by 1-27 $R^{139}$, halogen, —CN, —C(=O)R$^{130}$, —C(=O)OR$^{130}$, —C(=O)NR$^{132}$R$^{133}$, —C(=S)NR$^{132}$R$^{133}$, —NR$^{132}$R$^{133}$, —NR$^{134}$C(=O)R$^{130}$, —NR$^{134}$C(=O)OR$^{131}$, —NR$^{134}$C(=O)NR$^{132}$R$^{133}$, —NR$^{134}$C(=O)NR$^{134}$C(=O)R$^{130}$, —NR$^{134}$C(=S)R$^{130}$, —NR$^{134}$S(=O)$_2$R$^{131}$, —OR$^{130}$, =O, —OCN, —OC(=O)R$^{130}$, —OC(=O)NR$^{132}$R$^{133}$, =S, —S(=O)$_n$R$^{130}$, and —S(=O)$_2$NR$^{132}$R$^{133}$. In another embodiment, $Z^3$ is H, $C_{1-6}$alkyl optionally substituted by 1-13 $R^{89}$, $C_{6-11}$aryl optionally substituted by 1-7 $R^{89}$, $C_{7-16}$arylalkyl optionally substituted by 1-19 $R^{89}$, $C_{3-11}$cycloalkyl optionally substituted by 1-21 $R^{89}$, $C_{4-17}$cycloalkylalkyl optionally substituted by 1-32 $R^{89}$, 3-15 membered heterocycloalkyl optionally substituted by 1-28 $R^{89}$, 4-21 memcloalkyl optionally substituted by 1-21 $R^{89}$, 3-15 membered heterocycloalkyl optionally substituted by 1-28 $R^{89}$, 5-15 membered heteroaryl optionally substituted by 1-15 $R^{89}$, halogen, —CN, —C(=O)$R^{80}$, —C(=O)O$R^{80}$, —C(=O)N$R^{82}R^{83}$, —N$R^{82}R^{83}$, —N$R^{84}$C(=O)$R^{80}$, —N$R^{84}$C(=O)$R^{80}$, —N$R^{84}$C(=O)O$R^{81}$, —N$R^{84}$C(=O)N$R^{82}R^{83}$, —N$R^{84}$S(O)$_2R^{81}$, —N$R^{84}$P(=O)$R^{88}R^{88}$, —O$R^{80}$, =O, —OC(=O)$R^{80}$, —OC(=O)N$R^{82}R^{83}$, =S, —S(=O)$_nR^{80}$, —S(=O)$_2$N$R^{82}R^{83}$, or —P(=O)$R^{88}R^{88}$; alternatively, when $L^2$, $A^2$, $G^2$, $X^2$, $L^3$, $A^3$, $G^3$ and $X^3$ are absent, $Z^2$ and $Z^3$ can together form a group of formula -$A^{21}$-$A^{22}$-$A^{23}$-, or when $L^3$, $A^3$, $A^3$, $G^3$, $X^3$, $L^4$, $A^4$, $G^4$ and $X^4$ are absent, $Z^3$ and $Z^4$ can together form a group of formula -$A^{21}$-$A^{22}$-$A^{23}$-; wherein $A^{21}$, $A^{22}$, and $A^{23}$ are independently chosen from —C$Z^{21}Z^{22}$—, —C$Z^{23}Z^{24}$C$Z^{25}Z^{26}$—, or —N$Z^{27}$—; wherein:

(a) when any two of $Z^{21}$, $Z^{22}$, $Z^{23}$, $Z^{24}$, $Z^{25}$, $Z^{26}$ and $Z^{27}$ are located on adjacent atoms, they may together form a bond between the atoms, and (b) any of $Z^{21}$, $Z^{22}$, $Z^{23}$, $Z^{24}$, $Z^{25}$, $Z^{26}$ and $Z^{27}$ may be independently chosen from H, $C_{1-6}$alkyl optionally substituted by 1-13 $R^{99}$, $C_{6-11}$ aryl optionally substituted by 1-7 $R^{99}$, $C_{3-11}$cycloalkyl optionally substituted by 1-21 $R^{99}$, 3-15 membered heterocycloalkyl optionally substituted by 1-28 $R^{99}$, 5-15 membered heteroaryl optionally substituted by 1-15 $R^{99}$, halogen, —CN, —C(=O)$R^{90}$, —C(=O)O$R^{90}$, —C(=O)N$R^{92}R^{93}$, —N$R^{92}R^{93}$, —N$R^{94}$C(=O)$R^{90}$, —N$R^{94}$C(=O)O$R^{91}$, —N$R^{94}$C(=O)N$R^{92}R^{93}$, —N$R^{94}$S(=O)$_2R^{91}$, —N$R^{94}$P(=O)$R^{98}R^{98}$, —O$R^{90}$, =O, —OC(=O)$R^{90}$, —OC(=O)N$R^{92}R^{93}$, =S, —S(=O)$_nR^{90}$, —S(=O)$_2$N$R^{92}R^{93}$, and —P(=O)$R^{98}R^{98}$. In another embodiment, $Z^3$ is H, $C_{1-6}$alkyl optionally substituted by 1-13 $R^{89}$, $C_{6-11}$aryl optionally substituted by 1-7 $R^{89}$, $C_{7-16}$aralkyl optionally substituted by 1-19 $R^{89}$, $C_{3-11}$ cycloalkyl optionally substituted by 1-21 $R^{89}$, 3-15 membered heterocycloalkyl optionally substituted by 1-28 $R^{89}$, 5-15 membered heteroaryl optionally substituted by 1-15 $R^{89}$, halogen, —CN, —C(=O)$R^{80}$, —C(=O)O$R^{80}$, —C(=O)N$R^{82}R^{83}$, —N$R^{82}R^{83}$, —N$R^{84}$C(=O)$R^{80}$, —N$R^{84}$C(=O)O$R^{81}$, —N$R^{84}$C(=O)N$R^{82}R^{83}$, —N$R^{84}$S(=O)$_2R^{81}$, —O$R^{80}$, =O, —OC(=O)$R^{80}$, —OC(=O)N$R^{82}R^{83}$, =S, —S(=O)$_nR^{80}$, or —S(=O)$_2$N$R^{82}R^{83}$; alternatively, when $L^2$, $A^2$, $G^2$, $X^2$, $L^3$, $A^3$, $G^3$ and $X^3$ are absent, $Z^2$ and $Z^3$ can together form a group of formula -$A^{21}$-$A^{22}$-$A^{23}$-, or when $L^3$, $A^3$, $G^3$, $X^3$, $L^4$, $A^4$, $G^4$ and $X^4$ are absent, $Z^3$ and $Z^4$ can together form a group of formula -$A^{21}$-$A^{22}$-$A^{23}$-; wherein $A^{21}$, $A^{22}$, and $A^{23}$ are independently chosen from —C$Z^{21}Z^{22}$—, —C$Z^{23}Z^{24}$C$Z^{25}Z^{26}$—, or —N$Z^{27}$—; wherein:

(a) when any two of $Z^{21}$, $Z^{22}$, $Z^{23}$, $Z^{24}$, $Z^{24}$, $Z^{26}$ and $Z^{27}$ are located on adjacent atoms, they may together form a bond between the atoms, and (b) any of $Z^{21}$, $Z^{22}$, $Z^{23}$, $Z^{24}$, $Z^{24}$, $Z^{26}$ and $Z^{27}$ may be independently chosen from H, $C_{1-6}$alkyl optionally substituted by 1-13 $R^{99}$, $C_{6-11}$ aryl optionally substituted by 1-7 $R^{99}$, $C_{3-11}$cycloalkyl optionally substituted by 1-21 $R^{99}$, 3-15 membered heterocycloalkyl optionally substituted by 1-28 $R^{99}$, 5-15 membered heteroaryl optionally substituted by 1-15 $R^{99}$, halogen, —CN, —C(=O)$R^{90}$, —C(=O)O$R^{90}$, —C(=O)N$R^{92}R^{93}$, —N$R^{92}R^{93}$, —N$R^{94}$C(=O)$R^{90}$, —N$R^{94}$C(=O)O$R^{91}$, —N$R^{94}$C(=O)N$R^{92}R^{93}$, —N$R^{94}$S(=O)$_2R^{91}$, —O$R^{90}$, =O, —OC(=O)$R^{90}$, —OC(=O)N$R^{92}R^{93}$, =S, —S(=O)$_nR^{90}$, and —S(=O)$_2$N$R^{92}R^{93}$. In another embodiment, $Z^3$ is H, $C_{1-6}$alkyl optionally substituted by 1-6 $R^{89}$, $C_{6-11}$aryl optionally substituted by 1-6 $R^{89}$, $C_{7-16}$arylalkyl optionally substituted by 1-6 $R^{89}$, $C_{3-11}$cycloalkyl optionally substituted by 1-6 $R^{89}$, $C_{4-17}$cycloalkylalkyl optionally substituted by 1-6 $R^{89}$, 3-15 membered heterocycloalkyl optionally substituted by 1-6 $R^{89}$, 4-21 membered heterocycloalkylalkyl optionally substituted by 1-6 $R^{89}$, 5-15 membered heteroaryl optionally substituted by 1-6 $R^{89}$, 6-21 membered heteroarylalkyl optionally substituted by 1-6 $R^{89}$, halogen, —CN, —C(=O)$R^{80}$, —C(=O)O$R^{80}$, —C(=O)N$R^{82}R^{83}$, —C(=O)C(=O)$R^{80}$, —C(=S)N$R^{82}R^{83}$, —NC, —NO$_2$, —N$R^{82}R^{83}$, —N$R^{84}$N$R^{82}R^{83}$, —N$R^{84}$C(=O)$R^{80}$, —N$R^{84}$C(=O)C(=O)$R^{80}$, —N$R^{84}$C(=O)O$R^{81}$, —N$R^{84}$C(=O)C(=O)O$R^{81}$, —N$R^{84}$C(=O)N$R^{82}R^{83}$, —N$R^{84}$C(=O)N$R^{84}$C(=O)$R^{80}$, —N$R^{84}$C(=O)N$R^{84}$C(=O)O$R^{80}$, —N$R^{84}$C(=O)C(=O)N$R^{82}R^{83}$, —N$R^{84}$C(=S)$R^{80}$, —N$R^{84}$C(=S)O$R^{80}$, —N$R^{84}$C(=S)N$R^{82}R^{83}$, —N$R^{84}$S(=O)$_2R^{81}$, —N$R^{84}$S(=O)$_2$N$R^{82}R^{83}$, —N$R^{84}$P(=O)$R^{88}R^{88}$, —O$R^{80}$, =O, —OCN, —OCN, —OC(=O)$R^{80}$, —OC(=O)N$R^{82}R^{83}$, —OC(=O)O$R^{80}$, —OS(=O)$R^{80}$, —OS(=O)$_2R^{80}$, —OS(=O)$_2$O$R^{80}$, —OS(=O)$_2$N$R^{82}R^{83}$, —SCN, =S, —S(=O)$_nR^{80}$, —S(=O)$_2R^{80}$, —SO$_3R^{87}$, —S(=O)$_2$N$R^{82}R^{83}$, —S(=O)N$R^{82}R^{83}$, or —P(=O)$R^{88}R^{88}$; alternatively, when $L^2$, $A^2$, $G^2$, $X^2$, $L^3$, $A^3$, $G^3$ and $X^3$ are absent, $Z^2$ and $Z^3$ can together form a group of formula -$A^{21}$-$A^{22}$-$A^{23}$-, or when $L^3$, $A^3$, $G^3$, $X^3$, $L^4$, $A^4$, $G^4$ and $X^4$ are absent, $Z^3$ and $Z^4$ can together form a group of formula -$A^{21}$-$A^{22}$-$A^{23}$-; wherein $A^{21}$, $A^{22}$, and $A^{23}$ are independently chosen from —C$Z^{21}Z^{22}$—, —C$Z^{23}Z^{24}$C$Z^{25}Z^{26}$—, —C(=O)—, —N$Z^{27}$—, —S—, —S(=O)—, —S(=O)$_2$—, or —O—; wherein:

(a) when any two of $Z^{21}$, $Z^{22}$, $Z^{23}$, $Z^{24}$, $Z^{25}$, $Z^{26}$ and $Z^{27}$ are located on adjacent atoms, they may together form a bond between the atoms, and (b) any of $Z^{21}$, $Z^{22}$, $Z^{23}$, $Z^{24}$, $Z^{25}$, $Z^{26}$ and $Z^{27}$ may be independently chosen from H, $C_{1-6}$alkyl optionally substituted by 1-6 $R^{99}$, $C_{6-11}$aryl optionally substituted by 1-7 $R^{99}$, $C_{7-16}$arylalkyl optionally substituted by 1-6 $R^{99}$, $C_{3-11}$cycloalkyl optionally substituted by 1-6 $R^{99}$, $C_{4-17}$cycloalkylalkyl optionally substituted by 1-6 $R^{99}$, 3-15 membered heterocycloalkyl optionally substituted by 1-6 $R^{99}$, 4-21 membered heterocycloalkylalkyl optionally substituted by 1-6 $R^{99}$, 5-15 membered heteroaryl optionally substituted by 1-6 $R^{99}$, 6-21 membered heteroarylalkyl optionally substituted by 1-6 $R^{99}$, halogen, —CN, —C(=O)$R^{90}$, —C(=O)O$R^{90}$, —C(=O)N$R^{92}R^{93}$, —C(=O)C(=O)$R^{90}$, —C(=S)N$R^{92}R^{93}$, —NC, —NO$_2$, —N$R^{92}R^{93}$, —N$R^{94}$N$R^{92}R^{93}$, —N$R^{94}$C(=O)$R^{90}$, —N$R^{94}$C(=O)C(=O)$R^{90}$, —N$R^{94}$C(=O)O$R^{91}$, —N$R^{94}$C(=O)C(=O)O$R^{91}$, —N$R^{94}$C(=O)N$R^{92}R^{93}$, —N$R^{94}$C(=O)N$R^{94}$C(=O)$R^{90}$, —N$R^{94}$C(=O)N$R^{94}$C(=O)O$R^{90}$, —N$R^{94}$C(=N$R^{95}$)N$R^{92}R^{93}$, —N$R^{94}$C(=O)C(=O)N$R^{92}R^{93}$, —N$R^{94}$C(=S)$R^{90}$, —N$R^{94}$C(=S)O$R^{90}$, —N$R^{94}$C(=S)N$R^{92}R^{93}$, —N$R^{94}$S(=O)$_2R^{91}$, —N$R^{94}$S(=O)$_2$N$R^{92}R^{93}$, —N$R^{94}$P(=O)$R^{98}R^{98}$, —O$R^{90}$, =O, —OCN, —OC(=O)$R^{90}$, —OC(=O)N$R^{92}R^{93}$, —OC(=O)O$R^{90}$, —OS(=O)$R^{90}$, —OS(=O)$_2R^{90}$, —OS(=O)$_2$O$R^{90}$, —OS(=O)$_2$N$R^{92}R^{93}$, —SCN, =S, —S(=O)$_nR^{90}$, —S(=O)$_2$O$R^{90}$, —SO$_3R^{97}$, —S(=O)$_2$N$R^{92}R^{93}$, —S(=O)N$R^{92}R^{93}$, and —P(=O)$R^{98}R^{98}$; and (c) any two of $Z^{21}$, $Z^{22}$, $Z^{23}$, $Z^{24}$, $Z^{25}$, $Z^{26}$ and $Z^{27}$ may together form a group of formula -$A^{31}$-$A^{32}$-$A^{33}$-, wherein $A^{31}$, $A^{32}$, and $A^{33}$ are independently chosen from —C$Z^{31}Z^{32}$—, —C$Z^{33}Z^{34}$C$Z^{35}Z^{36}$—, —C(=O)—, —N$Z^{37}$—, —S—, —S(=O)—, —S(=O)$_2$—, or —O— wherein:

(i) when any two of $Z^{31}$, $Z^{32}$, $Z^{33}$, $Z^{34}$, $Z^{35}$, $Z^{36}$ and $Z^{37}$ are located on adjacent atoms, they may together form a bond between the atoms, and (ii) any of any of $Z^{21}$, $Z^{22}$, $Z^{23}$, $Z^{24}$, $Z^{25}$, $Z^{26}$ and $Z^{27}$ may be independently chosen from H, $C_{1-6}$alkyl optionally substituted by 1-6 $R^{139}$, $C_{6-11}$aryl optionally substituted by 1-7

$R^{139}$, $C_{7-16}$arylalkyl optionally substituted by 1-6 $R^{139}$, $C_{3-11}$cycloalkyl optionally substituted by 1-6 $R^{139}$, $C_{4-17}$cycloalkylalkyl optionally substituted by 1-6 $R^{139}$, 3-15 membered heterocycloalkyl optionally substituted by 1-6 $R^{139}$, 4-21 membered heterocycloalkylalkyl optionally substituted by 1-6 $R^{139}$, 5-15 membered heteroaryl optionally substituted by 1-6 $R^{139}$, 6-21 membered heteroarylalkyl optionally substituted by 1-6 $R^{139}$, halogen, —CN, —C(=O)$R^{130}$, —C(=O)O$R^{130}$, —C(=O)N$R^{132}R^{133}$, —C(=O)C(=O)$R^{130}$, —C(=S)N$R^{132}R^{133}$, —NC, —NO$_2$, —N$R^{132}R^{133}$, —N$R^{134}$N$R^{132}R^{133}$, —N$R^{134}$C(=O)$R^{130}$, —N$R^{134}$C(=O)C(=O)$R^{130}$, —N$R^{134}$C(=O)O$R^{131}$, —N$R^{134}$C(=O)C(=O)O$R^{131}$, —N$R^{134}$C(=O)N$R^{132}R^{133}$, —N$R^{134}$C(=O)N$R^{134}$C(=O)$R^{130}$, —N$R^{134}$C(=O)N$R^{134}$C(=O)O$R^{130}$, —N$R^{134}$C(=N$R^{135}$)N$R^{132}R^{133}$, —N$R^{134}$C(=O)C(=O)N$R^{132}R^{133}$, —N$R^{134}$C(=S)$R^{130}$, —N$R^{134}$C(=S)O$R^{130}$, —N$R^{134}$C(=S)N$R^{132}R^{133}$, —N$R^{134}$S(=O)$_2R^{131}$, —N$R^{134}$S(=O)$_2$N$R^{132}R^{133}$, —N$R^{134}$P(=O)$R^{138}R^{138}$, —O$R^{130}$, =O, —OCN, —OC(=O)$R^{130}$, —OC(=O)N$R^{132}R^{133}$, —OC(=O)O$R^{130}$, —OS(=O)$R^{130}$, —OS(=O)$_2R^{130}$, —OS(=O)$_2$O$R^{130}$, —OS(=O)$_2$N$R^{132}R^{133}$, —SCN, =S, —S(=O)$_nR^{130}$, —S(=O)$_2$O$R^{130}$, —SO$_3R^{137}$, —S(=O)$_2$N$R^{132}R^{133}$, —S(=O)N$R^{132}R^{133}$, and —P(=O)$R^{138}R^{138}$. In another embodiment, $Z^3$ is H, $C_{1-6}$alkyl optionally substituted by 1-6 $R^{89}$, $C_{6-11}$aryl optionally substituted by 1-6 $R^{89}$, $C_{7-16}$arylalkyl optionally substituted by 1-6 $R^{89}$, $C_{3-11}$cycloalkyl optionally substituted by 1-6 $R^{89}$, $C_{4-17}$cycloalkylalkyl optionally substituted by 1-6 $R^{89}$, 3-15 membered heterocycloalkyl optionally substituted by 1-6 $R^{89}$, 4-21 membered heterocycloalkylalkyl optionally substituted by 1-6 $R^{89}$, 5-15 membered heteroaryl optionally substituted by 1-6 $R^{89}$, 6-21 membered heteroarylalkyl optionally substituted by 1-6 $R^{89}$, halogen, —CN, —C(=O)$R^{80}$, —C(=O)O$R^{80}$, —C(=O)N$R^{82}R^{83}$, —C(=O)C(=O)$R^{80}$, —C(=S)N$R^{82}R^{83}$, —NC, —NO$_2$, —N$R^{82}R^{83}$, —N$R^{84}$N$R^{82}R^{83}$, —N$R^{84}$C(=O)$R^{80}$, —N$R^{84}$C(=O)C(=O)$R^{80}$, —N$R^{84}$C(=O)O$R^{81}$, —N$R^{84}$C(=O)C(=O)O$R^{81}$, —N$R^{84}$C(=O)N$R^{82}R^{83}$, —N$R^{84}$C(=O)N$R^{84}$C(=O)$R^{80}$, —N$R^{84}$C(=O)N$R^{84}$C(=O)O$R^{80}$, —N$R^{84}$C(=N$R^{85}$)N$R^{82}R^{83}$, —N$R^{84}$C(=O)C(=O)N$R^{82}R^{83}$, —N$R^{84}$C(=S)$R^{80}$, —N$R^{84}$C(=S)O$R^{80}$, —N$R^{84}$C(=S)N$R^{82}R^{83}$, —N$R^{84}$S(=O)$_2R^{81}$, —N$R^{84}$S(=O)$_2$N$R^{82}R^{83}$, —O$R^{80}$, =O, —OCN, —OC(=O)$R^{80}$, —OC(=O)N$R^{82}R^{83}$, —OC(=O)O$R^{80}$, —OS(=O)$R^{80}$, —OS(=O)$_2R^{80}$, —OS(=O)$_2$O$R^{80}$, —OS(=O)$_2$N$R^{82}R^{83}$, —SCN, =S, —S(=O)$_nR^{80}$, —S(=O)$_2$O$R^{80}$, —SO$_3R^{87}$, —S(=O)$_2$N$R^{82}R^{83}$, or —S(=O)N$R^{82}R^{83}$; alternatively, when $L^2$, $A^2$, $G^2$, $X^2$, $L^3$, $A^3$, $G^3$ and $X^3$ are absent, $Z^2$ and $Z^3$ can together form a group of formula -$A^{21}$-$A^{22}$-$A^{23}$-, or when $L^3$, $A^3$, $G^3$, $X^3$, $L^4$, $A^4$, $G^4$ and $X^4$ are absent, $Z^3$ and $Z^4$ can together form a group of formula -$A^{21}$-$A^{22}$-$A^{23}$-; wherein $A^{21}$, $A^{22}$, and $A^{23}$ are independently chosen from —C$Z^{21}Z^{22}$—, —C$Z^{23}Z^{24}$C$Z^{25}Z^{26}$—, —C(=O)—, —N$Z^{27}$—, —S—, —S(=O)—, —S(=O)$_2$—, or —O—; wherein:

(a) when any two of $Z^{21}$, $Z^{22}$, $Z^{23}$, $Z^{24}$, $Z^{25}$, $Z^{26}$ and $Z^{27}$ are located on adjacent atoms, they may together form a bond between the atoms, and (b) any of $Z^{21}$, $Z^{22}$, $Z^{23}$, $Z^{24}$, $Z^{25}$, $Z^{26}$ and $Z^{27}$ may be independently chosen from H, $C_{1-6}$alkyl optionally substituted by 1-6 $R^{99}$, $C_{6-11}$aryl optionally substituted by 1-7 $R^{99}$, $C_{7-16}$arylalkyl optionally substituted by 1-6 $R^{99}$, $C_{3-11}$cycloalkyl optionally substituted by 1-6 $R^{99}$, $C_{4-17}$cycloalkylalkyl optionally substituted by 1-6 $R^{99}$, 3-15 membered heterocycloalkyl optionally substituted by 1-6 $R^{99}$, 4-21 membered heterocycloalkylalkyl optionally substituted by 1-6 $R^{99}$, 5-15 membered heteroaryl optionally substituted by 1-6 $R^{99}$, 6-21 membered heteroarylalkyl optionally substituted by 1-6 $R^{99}$, halogen, —CN, —C(=O)$R^{90}$, —C(=O)O$R^{90}$, —C(=O)N$R^{92}R^{93}$, —C(=O)C(=O)$R^{90}$, —C(=S)N$R^{92}R^{93}$, —NC, —NO$_2$, —N$R^{92}R^{93}$, —N$R^{94}$N$R^{92}R^{93}$, —N$R^{94}$C(=O)$R^{90}$, —N$R^{94}$C(=O)C(=O)$R^{90}$, —N$R^{94}$C(=O)O$R^{91}$, —N$R^{94}$C(=O)C(=O)O$R^{91}$, —N$R^{94}$C(=O)N$R^{92}R^{93}$, —N$R^{94}$C(=O)N$R^{94}$C(=O)$R^{90}$, —N$R^{94}$C(=O)N$R^{94}$C(=O)O$R^{90}$, —N$R^{94}$C(=N$R^{95}$)N$R^{92}R^{93}$, —N$R^{94}$C(=O)C(=O)N$R^{92}R^{93}$, —N$R^{94}$C(=S)$R^{90}$, —N$R^{94}$C(=S)O$R^{90}$, —N$R^{94}$C(=S)N$R^{92}R^{93}$, —N$R^{94}$S(=O)$_2R^{91}$, —N$R^{94}$S(=O)$_2$N$R^{92}R^{93}$, —O$R^{90}$, =O, —OCN, —OC(=O)$R^{90}$, —OC(=O)N$R^{92}R^{93}$, —OC(=O)O$R^{90}$, —OS(=O)$R^{90}$, —OS(=O)$_2R^{90}$, —OS(=O)$_2$O$R^{90}$, —OS(=O)$_2$N$R^{92}R^{93}$, —SCN, =S, —S(=O)$_nR^{90}$, —S(=O)$_2$O$R^{90}$, —SO$_3R^{97}$, —S(=O)$_2$N$R^{92}R^{93}$, and —S(=O)N$R^{92}R^{93}$; and (c) any two of $Z^{21}$, $Z^{22}$, $Z^{23}$, $Z^{24}$, $Z^{25}$, $Z^{26}$ and $Z^{27}$ may together form a group of formula -$A^{31}$-$A^{32}$-$A^{33}$-, wherein $A^{31}$, $A^{32}$, and $A^{33}$ are independently chosen from —C$Z^{31}Z^{32}$—, —C$Z^{33}Z^{34}$C$Z^{35}Z^{36}$—, —C(=O)—, —N$Z^{37}$—, —S—, —S(=O)—, —S(=O)$_2$—, or —O— wherein:

(i) when any two of $Z^{31}$, $Z^{32}$, $Z^{33}$, $Z^{34}$, $Z^{35}$, $Z^{36}$ and $Z^{37}$ are located on adjacent atoms, they may together form a bond between the atoms, and (ii) any of any of $Z^{21}$, $Z^{22}$, $Z^{23}$, $Z^{24}$, $Z^{25}$, $Z^{26}$ and $Z^{27}$ may be independently chosen from H, $C_{1-6}$alkyl optionally substituted by 1-6 $R^{139}$, $C_{6-11}$aryl optionally substituted by 1-7 $R^{139}$, $C_{7-16}$arylalkyl optionally substituted by 1-6 $R^{139}$, $C_{3-11}$cycloalkyl optionally substituted by 1-6 $R^{139}$, $C_{4-17}$cycloalkylalkyl optionally substituted by 1-6 $R^{139}$, 3-15 membered heterocycloalkyl optionally substituted by 1-6 $R^{139}$, 4-21 membered heterocycloalkylalkyl optionally substituted by 1-6 $R^{139}$, 5-15 membered heteroaryl optionally substituted by 1-6 $R^{139}$, 6-21 membered heteroarylalkyl optionally substituted by 1-6 $R^{139}$, halogen, —CN, —C(=O)$R^{130}$, —C(=O)O$R^{130}$, —C(=O)N$R^{132}R^{133}$, —C(=O)C(=O)$R^{130}$, —C(=S)N$R^{132}R^{133}$, —NC, —NO$_2$, —N$R^{132}R^{133}$, —N$R^{134}$N$R^{132}R^{133}$, —N$R^{134}$C(=O)$R^{130}$, —N$R^{134}$C(=O)C(=O)$R^{130}$, —N$R^{134}$C(=O)O$R^{131}$, —N$R^{134}$C(=O)C(=O)O$R^{131}$, —N$R^{134}$C(=O)N$R^{132}R^{133}$, —N$R^{134}$C(=O)N$R^{134}$C(=O)$R^{130}$, —N$R^{134}$C(=O)N$R^{134}$C(=O)O$R^{130}$, —N$R^{134}$C(=N$R^{135}$)N$R^{132}R^{133}$, —N$R^{134}$C(=O)C(=O)N$R^{132}R^{133}$, —N$R^{134}$C(=S)$R^{130}$, —N$R^{134}$C(=S)O$R^{130}$, —N$R^{134}$C(=S)N$R^{132}R^{133}$, —N$R^{134}$S(=O)$_2R^{131}$, —N$R^{134}$S(=O)$_2$N$R^{132}R^{133}$, —O$R^{130}$, =O, —OCN, —OC(=O)$R^{130}$, —OC(=O)N$R^{132}R^{133}$, —OC(=O)O$R^{130}$, —OS(=O)$R^{130}$, —OS(=O)$_2R^{130}$, —OS(=O)$_2$O$R^{130}$, —OS(=O)$_2$N$R^{132}R^{133}$, —SCN, =S, —S(=O)$_nR^{130}$, —S(=O)$_2$O$R^{130}$, —SO$_3R^{137}$, —S(=O)$_2$N$R^{132}R^{133}$, and —S(=O)N$R^{132}R^{133}$. In another embodiment, $Z^3$ is H, $C_{1-6}$alkyl optionally substituted by 1-6 $R^{89}$, $C_{6-11}$aryl optionally substituted by 1-7 $R^{89}$, $C_{7-16}$arylalkyl optionally substituted by 1-6 $R^{89}$, $C_{3-11}$cycloalkyl optionally substituted by 1-6 $R^{89}$, $C_{4-17}$cycloalkylalkyl optionally substituted by 1-6 $R^{89}$, 3-15 membered heterocycloalkyl optionally substituted by 1-6 $R^{89}$, 4-21 membered heterocycloalkylalkyl optionally substituted by 1-6 $R^{89}$, 5-15 membered heteroaryl optionally substituted by 1-6 $R^{89}$, 6-21 membered heteroarylalkyl optionally substituted by 1-6 $R^{89}$, halogen, —CN, —C(=O)$R^{80}$, —C(=O)O$R^{80}$, —C(=O)N$R^{82}R^{83}$, —C(=S)N$R^{82}R^{83}$, —NC, —NO$_2$, —N$R^{82}R^{83}$, —N$R^{84}$N$R^{82}R^{83}$, —N$R^{84}$C(=O)$R^{80}$, —N$R^{84}$C(=O)O$R^{81}$, —N$R^{84}$C(=O)N$R^{82}R^{83}$, —N$R^{84}$C(=O)N$R^{84}$C(=O)$R^{80}$, —N$R^{84}$C(=O)O$R^{80}$, —N$R^{84}$C(=N$R^{85}$)N$R^{82}R^{83}$, —N$R^{84}$C(=S)$R^{80}$, —N$R^{84}$C(=S)N$R^{82}R^{83}$, —N$R^{84}$S(=O)$_2R^{81}$, —O$R^{80}$, =O, —OCN, —OC(=O)$R^{80}$, —OC(=O)N$R^{82}R^{83}$, —SCN, =S, —S(=O)$_nR^{80}$, —S(=O)$_2$O$R^{80}$, or —S(=O)$_2$N$R^{82}R^{83}$; alternatively, when $L^2$, $A^2$, $G^2$, $X^2$, $L^3$, $A^3$, $G^3$ and $X^3$ are absent, $Z^2$ and $Z^3$ can together form a group of formula $-A^{21}-A^{22}-A^{23}-$, or when $L^3$, $A^3$, $G^3$, $X^3$, $L^4$, $A^4$, $G^4$ and $X^4$ are absent, $Z^3$ and $Z^4$ can together form a group of formula $-A^{21}-A^{22}-A^{23}-$; wherein $A^{21}$, $A^{22}$, and $A^{23}$ are independently chosen from $-CZ^{21}Z^{22}-$, $-CZ^{23}Z^{24}CZ^{25}Z^{26}-$, $-C(=O)-$, $-NZ^{27}-$, $-S-$, $-S(=O)-$, $-S(=O)_2-$, or $-O-$; wherein:

(a) when any two of $Z^{21}$, $Z^{22}$, $Z^{23}$, $Z^{24}$, $Z^{25}$, $Z^{26}$ and $Z^{27}$ are located on adjacent atoms, they may together form a bond between the atoms, and (b) any of $Z^{21}$, $Z^{22}$, $Z^{23}$, $Z^{24}$, $Z^{25}$, $Z^{26}$ and $Z^{27}$ may be independently chosen from H, $C_{1-6}$alkyl optionally substituted by 1-6 $R^{99}$, $C_{6-11}$aryl optionally substituted by 1-7 $R^{99}$, $C_{7-16}$arylalkyl optionally substituted by 1-6 $R^{99}$, $C_{3-11}$cycloalkyl optionally substituted by 1-6 $R^{99}$, $C_{4-17}$cycloalkylalkyl optionally substituted by 1-6 $R^{99}$, 3-15 membered heterocycloalkyl optionally substituted by 1-6 $R^{99}$, 4-21 membered heterocycloalkylalkyl optionally substituted by 1-6 $R^{99}$, 5-15 membered heteroaryl optionally substituted by 1-6 $R^{99}$, 6-21 membered heteroarylalkyl optionally substituted by 1-6 $R^{99}$, halogen, $-CN$, $-C(=O)R^{90}$, $-C(=O)OR^{90}$, $-C(=O)NR^{92}R^{93}$, $-C(=S)NR^{92}R^{93}$, $-NC$, $-NO_2$, $-NR^{92}R^{93}$, $-NR^{94}NR^{92}R^{93}$, $-NR^{94}C(=O)R^{90}$, $-NR^{94}C(=O)OR^{91}$, $-NR^{94}C(=O)NR^{92}R^{93}$, $-NR^{94}C(=O)NR^{94}C(=O)R^{90}$, $-NR^{94}C(=O)NR^{94}C(=O)OR^{90}$, $-NR^{94}C(=NR^{95})NR^{92}R^{93}$, $-NR^{94}C(=S)R^{90}$, $-NR^{94}C(=S)NR^{92}R^{93}$, $-NR^{94}S(=O)_2R^{91}$, $-OR^{90}$, $=O$, $-OCN$, $-OC(=O)NR^{92}R^{93}$, $-SCN$, $=S$, $-S(=O)_nR^{90}$, and $-S(=O)_2NR^{92}R^{93}$; and (c) any two of $Z^{21}$, $Z^{22}$, $Z^{23}$, $Z^{24}$, $Z^{25}$, $Z^{26}$ and $Z^{27}$ may together form a group of formula $-A^{31}-A^{32}-A^{33}-$, wherein $A^{31}$, $A^{32}$, and $A^{33}$ are independently chosen from $-CZ^{31}Z^{32}-$, $-CZ^{33}Z^{34}CZ^{35}Z^{36}-$, $-C(=O)-$, $-NZ^{37}-$, $-S-$, $-S(=O)-$, $-S(=O)_2-$, or $-O-$ wherein:

(i) when any two of $Z^{31}$, $Z^{32}$, $Z^{33}$, $Z^{34}$, $Z^{35}$, $Z^{36}$ and $Z^{37}$ are located on adjacent atoms, they may together form a bond between the atoms, and (ii) any of any of $Z^{21}$, $Z^{22}$, $Z^{23}$, $Z^{24}$, $Z^{25}$, $Z^{26}$ and $Z^{27}$ may be independently chosen from H, $C_{1-6}$alkyl optionally substituted by 1-6 $R^{139}$, $C_{6-11}$aryl optionally substituted by 1-7 $R^{139}$, $C_{7-16}$arylalkyl optionally substituted by 1-6 $R^{139}$, $C_{3-11}$cycloalkyl optionally substituted by 1-6 $R^{139}$, $C_{4-17}$cycloalkylalkyl optionally substituted by 1-6 $R^{139}$, 3-15 membered heterocycloalkyl optionally substituted by 1-6 $R^{139}$, 4-21 membered heterocycloalkylalkyl optionally substituted by 1-6 $R^{139}$, 5-15 membered heteroaryl optionally substituted by 1-6 $R^{139}$, 6-21 membered heteroarylalkyl optionally substituted by 1-6 $R^{139}$, halogen, $-CN$, $-C(=O)R^{130}$, $-C(=O)OR^{130}$, $-C(=O)NR^{132}R^{133}$, $-C(=S)NR^{132}R^{133}$, $-NC$, $-NO_2$, $-NR^{132}R^{133}$, $-NR^{134}NR^{132}R^{133}$, $-NR^{134}C(=O)R^{130}$, $-NR^{134}C(=O)OR^{131}$, $-NR^{134}C(=O)NR^{132}R^{133}$, $-NR^{134}C(=O)NR^{134}C(=O)R^{130}$, $-NR^{134}C(=NR^{135})NR^{132}R^{133}$, $-NR^{134}C(=S)R^{130}$, $-NR^{134}C(=S)NR^{132}R^{133}$, $-NR^{134}S(=O)_2R^{131}$, $-OR^{130}$, $=O$, $-OCN$, $-OC(=O)R^{130}$, $-OC(=O)NR^{132}R^{133}$, $-SCN$, $=S$, $-S(=O)_nR^{130}$, and $-S(=O)_2NR^{132}R^{133}$. In another embodiment, $Z^3$ is H, $C_{1-6}$alkyl optionally substituted by 1-6 $R^{89}$, $C_{6-11}$aryl optionally substituted by 1-7 $R^{89}$, $C_{7-16}$arylalkyl optionally substituted by 1-6 $R^{89}$, $C_{3-11}$cycloalkyl optionally substituted by 1-6 $R^{89}$, $C_{4-17}$cycloalkylalkyl optionally substituted by 1-6 $R^{89}$, 3-15 membered heterocycloalkyl optionally substituted by 1-6 $R^{89}$, 4-21 membered heterocycloalkylalkyl optionally substituted by 1-6 $R^{89}$, 5-15 membered heteroaryl optionally substituted by 1-6 $R^{89}$, 6-21 membered heteroarylalkyl optionally substituted by 1-6 $R^{89}$, halogen, $-CN$, $-C(=O)R^{80}$, $-C(=O)OR^{80}$, $-C(=O)NR^{82}R^{83}$, $-C(=S)NR^{82}R^{83}$, $-NR^{82}R^{83}$, $-NR^{84}C(=O)R^{80}$, $-NR^{84}C(=O)OR^{81}$, $-NR^{84}C(=O)NR^{82}R^{83}$, $-NR^{84}C(=O)NR^{84}C(=O)OR^{80}$, $-NR^{84}C(=O)NR^{84}C(=O)OR^{80}$, $-NR^{82}R^{83}$, $=S$, $-NR^{84}S(=O)_2R^{81}$, $-NR^{84}P(=O)R^{88}R^{88}$, $-OR^{80}$, $=O$, $-OC(=O)R^{80}$, $-OC(=O)NR^{82}R^{83}$, $=S$, $-S(=O)_nR^{80}$, $-S(=O)_2NR^{82}R^{83}$, or $-P(=O)R^{88}R^{88}$; alternatively, when $L^2$, $A^2$, $G^2$, $X^2$, $L^3$, $A^3$, $G^3$ and $X^3$ are absent, $Z^2$ and $Z^3$ can together form a group of formula $-A^{21}-A^{22}-A^{23}-$, or when $L^3$, $A^3$, $G^3$, $X^3$, $L^4$, $A^4$, $G^4$ and $X^4$ are absent, $Z^3$ and $Z^4$ can together form a group of formula $-A^{21}-A^{22}-A^{23}-$; wherein $A^{21}$, $A^{22}$, and $A^{23}$ are independently chosen from $-CZ^{21}Z^{22}-$, $-CZ^{23}Z^{24}CZ^{25}Z^{26}-$, $-C(=O)-$, $-NZ^{27}-$, $-S-$, $-S(=O)-$, $-S(=O)_2-$, or $-O-$; wherein:

(a) when any two of $Z^{21}$, $Z^{22}$, $Z^{23}$, $Z^{24}$, $Z^{25}$, $Z^{26}$ and $Z^{27}$ are located on adjacent atoms, they may together form a bond between the atoms, and (b) any of $Z^{21}$, $Z^{22}$, $Z^{23}$, $Z^{24}$, $Z^{25}$, $Z^{26}$ and $Z^{27}$ may be independently chosen from H, $C_{1-6}$alkyl optionally substituted by 1-6 $R^{99}$, $C_{6-11}$aryl optionally substituted by 1-7 $R^{99}$, $C_{7-16}$arylalkyl optionally substituted by 1-6 $R^{99}$, $C_{3-11}$cycloalkyl optionally substituted by 1-6 $R^{99}$, $C_{4-17}$cycloalkylalkyl optionally substituted by 1-6 $R^{99}$, 3-15 membered heterocycloalkyl optionally substituted by 1-6 $R^{99}$, 4-21 membered heterocycloalkylalkyl optionally substituted by 1-6 $R^{99}$, 5-15 membered heteroaryl optionally substituted by 1-6 $R^{99}$, 6-21 membered heteroarylalkyl optionally substituted by 1-6 $R^{99}$, halogen, $-CN$, $-C(=O)R^{90}$, $-C(=O)OR^{90}$, $-C(=O)NR^{92}R^{93}$, $-C(=S)NR^{92}R^{93}$, $-NR^{92}R^{93}$, $-NR^{94}C(=O)R^{90}$, $-NR^{94}C(=O)OR^{91}$, $-NR^{94}C(=O)NR^{92}R^{93}$, $-NR^{94}C(=O)NR^{94}C(=O)R^{90}$, $-NR^{94}C(=O)NR^{94}C(=O)OR^{90}$, $-NR^{94}C(=S)R^{90}$, $-NR^{94}S(=O)_2R^{91}$, $-NR^{94}P(=O)R^{98}R^{98}$, $-OR^{90}$, $=O$, $-OC(=O)R^{90}$, $-OC(=O)NR^{92}R^{93}$, $=S$, $-S(=O)_nR^{90}$, $-S(=O)_2NR^{92}R^{93}$, and $-P(=O)R^{98}R^{98}$; and (c) any two of $Z^{21}$, $Z^{22}$, $Z^{23}$, $Z^{24}$, $Z^{25}$, $Z^{26}$ and $Z^{27}$ may together form a group of formula $-A^{31}-A^{32}-A^{33}-$, wherein $A^{31}$, $A^{32}$, and $A^{33}$ are independently chosen from $-CZ^{31}Z^{32}-$, $-CZ^{33}Z^{34}CZ^{35}Z^{36}-$, $-C(=O)-$, $-NZ^{37}-$, $-S-$, $-S(=O)-$, $-S(=O)_2-$, or $-O-$ wherein:

(i) when any two of $Z^{31}$, $Z^{32}$, $Z^{33}$, $Z^{34}$, $Z^{35}$, $Z^{36}$ and $Z^{37}$ are located on adjacent atoms, they may together form a bond between the atoms, and (ii) any of any of $Z^{21}$, $Z^{22}$, $Z^{23}$, $Z^{24}$, $Z^{25}$, $Z^{26}$ and $Z^{27}$ may be independently chosen from H, $C_{1-6}$alkyl optionally substituted by 1-6 $R^{139}$, $C_{6-11}$aryl optionally substituted by 1-7 $R^{139}$, $C_{7-16}$arylalkyl optionally substituted by 1-6 $R^{139}$, $C_{3-11}$cycloalkyl optionally substituted by 1-6 $R^{139}$, $C_{4-17}$cycloalkylalkyl optionally substituted by 1-6 $R^{139}$, 3-15 membered heterocycloalkyl optionally substituted by 1-6 $R^{139}$, 4-21 membered heterocycloalkylalkyl optionally substituted by 1-6 $R^{139}$, 5-15 membered heteroaryl optionally substituted by 1-6 $R^{139}$, 6-21 membered heteroarylalkyl optionally substituted by 1-6 $R^{139}$, halogen, $-CN$, $-C(=O)OR^{130}$, $-C(=O)OR^{130}$, $-C(=O)NR^{132}R^{133}$, $-C(=S)NR^{132}R^{133}$, $-NR^{132}R^{133}$, $-NR^{134}C(=O)R^{130}$, $NR^{134}(=O)OR^{131}$, $-NR^{134}C(=O)NR^{132}R^{133}$, $-NR^{134}C(=O)NR^{134}C(=O)R^{130}$, $-NR^{134}C(=S)R^{130}$, $-NR^{134}S(=O)_2R^{131}$, $NR^{134}P(=O)R^{138}R^{138}$, $-OR^{130}$, $=O$, $-OCN$, $-OC(=O)R^{130}$, $-OC(=O)NR^{132}R^{133}$, $=S$, $-S(=O)_n R^{130}$, $-S(=O)_2NR^{132}R^{133}$, and $-P(=O)R^{138}R^{138}$. In another embodiment, $Z^3$ is H, $C_{1-6}$alkyl optionally substituted by 1-6 $R^{89}$, $C_{6-11}$aryl optionally substituted by 1-7 $R^{89}$, $C_{7-16}$arylalkyl optionally substituted by 1-6 $R^{89}$, $C_{3-11}$cycloalkyl optionally substituted by 1-6 $R^{89}$, $C_{4-17}$cycloalkylalkyl optionally substituted by 1-6 $R^{89}$, 3-15 membered heterocycloalkyl optionally substituted by 1-6 $R^{89}$, 4-21 membered heterocycloalkylalkyl optionally substituted by 1-6 $R^{89}$, 5-15 membered heteroaryl optionally substituted by 1-6 $R^{89}$, 6-21 membered heteroarylalkyl optionally substituted by 1-6 $R^{89}$, halogen, —CN, —C(=O)$R^{80}$, —C(=O)O$R^{80}$, —C(=O)N$R^{82}R^{83}$, —C(=S)N$R^{82}R^{83}$, —N$R^{82}R^{83}$, —N$R^{84}$C(=O)$R^{80}$, —N$R^{84}$C(=O)O$R^{81}$, —N$R^{84}$C(=O)N$R^{82}R^{83}$, —N$R^{84}$C(=O)N$R^{84}$C(=O)$R^{80}$, —N$R^{84}$C(=O)N$R^{84}$C(=O)O$R^{80}$, —N$R^{84}$C(=S)$R^{80}$, —N$R^{84}$S(=O)$_2R^{81}$, —O$R^{80}$, =O, —OC(=O)$R^{80}$, —OC(=O)N$R^{82}R^{83}$, =S, —S(=O)$_n R^{80}$, or —S(=O)$_2$N$R^{82}R^{83}$; alternatively, when $L^2$, $A^2$, $G^2$, $X^2$, $L^3$, $A^3$, $G^3$ and $X^3$ are absent, $Z^2$ and $Z^3$ can together form a group of formula -$A^{21}$-$A^{22}$-$A^{23}$-, or when $L^3$, $A^3$, $G^3$, $X^3$, $L^4$, $A^4$, $G^4$ and $X^4$ are absent, $Z^3$ and $Z^4$ can together form a group of formula -$A^{21}$-$A^{22}$-$A^{23}$-; wherein $A^{21}$, $A^{22}$, and $A^{23}$ are independently chosen from —C$Z^{21}Z^{22}$—, —C$Z^{23}Z^{24}$C$Z^{25}Z^{26}$—, —C(=O)—, —N$Z^{27}$—, —S—, —S(=O)—, —S(=O)$_2$—, or —O—; wherein:

(a) when any two of $Z^{21}$, $Z^{22}$, $Z^{23}$, $Z^{24}$, $Z^{25}$, $Z^{26}$ and $Z^{27}$ are located on adjacent atoms, they may together form a bond between the atoms, and (b) any of $Z^{21}$, $Z^{22}$, $Z^{23}$, $Z^{24}$, $Z^{25}$, $Z^{26}$ and $Z^{27}$ may be independently chosen from H, $C_{1-6}$alkyl optionally substituted by 1-6 $R^{99}$, $C_{6-11}$aryl optionally substituted by 1-7 $R^{99}$, $C_{7-16}$arylalkyl optionally substituted by 1-6 $R^{99}$, $C_{3-11}$cycloalkyl optionally substituted by 1-6 $R^{99}$, $C_{4-17}$cycloalkylalkyl optionally substituted by 1-6 $R^{99}$, 3-15 membered heterocycloalkyl optionally substituted by 1-6 $R^{99}$, 4-21 membered heterocycloalkylalkyl optionally substituted by 1-6 $R^{99}$, 5-15 membered heteroaryl optionally substituted by 1-6 $R^{99}$, 6-21 membered heteroarylalkyl optionally substituted by 1-6 $R^{99}$, halogen, —CN, —C(=O)$R^{90}$, —C(=O)O$R^{90}$, —C(=O)N$R^{92}R^{93}$, —C(=S)N$R^{92}R^{93}$, —N$R^{94}$C(=O)$R^{90}$, —N$R^{94}$C(=O)O$R^{91}$, —N$R^{94}$C(=O)N$R^{92}R^{93}$, —N$R^{94}$C(=O)N$R^{94}$C(=O)$R^{90}$, —N$R^{94}$C(=O)N$R^{94}$C(=O)O$R^{90}$, —N$R^{94}$C(=S)$R^{90}$, —N$R^{94}$S(=O)$_2R^{91}$, —O$R^{90}$, =O, —OC(=O)$R^{90}$, —OC(=O)N$R^{92}R^{93}$, =S, —S(=O)$_n R^{90}$, and —S(=O)$_2$N$R^{92}R^{93}$; and (c) any two of $Z^{21}$, $Z^{22}$, $Z^{23}$, $Z^{24}$, $Z^{25}$, $Z^{26}$ and $Z^{27}$ may together form a group of formula -$A^{31}$-$A^{32}$-$A^{33}$-, wherein $A^{31}$, $A^{32}$, and $A^{33}$ are independently chosen from —C$Z^{31}Z^{32}$—, —C$Z^{33}Z^{34}$C$Z^{35}Z^{36}$—, —C(=O)—, —N$Z^{37}$—, —S—, —S(=O)—, —S(=O)$_2$—, or —O— wherein:

(i) when any two of $Z^{31}$, $Z^{32}$, $Z^{33}$, $Z^{34}$, $Z^{35}$, $Z^{36}$ and $Z^{37}$ are located on adjacent atoms, they may together form a bond between the atoms, and (ii) any of any of $Z^{21}$, $Z^{22}$, $Z^{23}$, $Z^{24}$, $Z^{25}$, $Z^{26}$ and $Z^{27}$ may be independently chosen from H, $C_{1-6}$alkyl optionally substituted by 1-6 $R^{139}$, $C_{6-11}$ aryl optionally substituted by 1-7 $R^{139}$, $C_{7-16}$arylalkyl optionally substituted by 1-6 $R^{139}$, $C_{3-11}$cycloalkyl optionally substituted by 1-6 $R^{139}$, $C_{4-17}$cycloalkylalkyl optionally substituted by 1-6 $R^{139}$, 3-15 membered heterocycloalkyl optionally substituted by 1-6 $R^{139}$, 4-21 membered heterocycloalkylalkyl optionally substituted by 1-6 $R^{139}$, 5-15 membered heteroaryl optionally substituted by 1-6 $R^{139}$, 6-21 membered heteroarylalkyl optionally substituted by 1-6 $R^{139}$, halogen, —CN, —C(=O)$R^{130}$, —C(=O)O$R^{130}$, —C(=O)N$R^{132}R^{133}$, —C(=S)N$R^{132}R^{133}$, —N$R^{132}R^{133}$, —N$R^{134}$C(=O)$R^{130}$, —N$R^{134}$C(=O)O$R^{131}$, —N$R^{134}$C(=O)N$R^{132}R^{133}$, —N$R^{134}$C(=O)N$R^{134}$C(=O)$R^{130}$, —N$R^{134}$C(=S)$R^{130}$, —N$R^{134}$S(=O)$_2R^{131}$, —O$R^{130}$, =O, —OCN, —OC(=O)$R^{130}$, —OC(=O)N$R^{132}R^{133}$, =S, —S(=O)$_n R^{130}$, and —S(=O)$_2$N$R^{132}R^{133}$. In another embodiment, $Z^3$ is H, $C_{1-6}$alkyl optionally substituted by 1-6 $R^{89}$, $C_{6-11}$aryl optionally substituted by 1-7 $R^{89}$, $C_{7-16}$arylalkyl optionally substituted by 1-6 $R^{89}$, $C_{3-11}$cycloalkyl optionally substituted by 1-6 $R^{89}$, $C_{4-17}$cycloalkylalkyl optionally substituted by 1-6 $R^{89}$, 3-15 membered heterocycloalkyl optionally substituted by 1-6 $R^{89}$, 4-21 membered heterocycloalkylalkyl optionally substituted by 1-6 $R^{89}$, 5-15 membered heteroaryl optionally substituted by 1-6 $R^{89}$, 6-21 membered heteroarylalkyl optionally substituted by 1-6 $R^{89}$, halogen, —CN, —C(=O)$R^{80}$, —C(=O)O$R^{80}$, —C(=O)N$R^{82}R^{83}$, —C(=S)N$R^{82}R^{83}$, —N$R^{82}R^{83}$, —N$R^{84}$C(=O)$R^{80}$, —N$R^{84}$C(=O)O$R^{81}$, —N$R^{84}$C(=O)N$R^{82}R^{83}$, —N$R^{84}$C(=O)N$R^{84}$C(=O)$R^{80}$, —N$R^{84}$C(=O)N$R^{84}$C(=O)O$R^{80}$, —N$R^{84}$C(=S)$R^{80}$, —N$R^{84}$S(=O)$_2R^{81}$, —N$R^{84}$P(=O)$R^{88}R^{88}$, —O$R^{80}$, =O, —OC(=O)$R^{80}$, —OC(=O)N$R^{82}R^{83}$, =S, —S(=O)$_nR^{80}$, —S(=O)$_2$N$R^{82}R^{83}$, or —P(=O)$R^{88}R^{88}$; alternatively, when $L^2$, $A^2$, $G^2$, $X^2$, $L^3$, $A^3$, $G^3$ and $X^3$ are absent, $Z^2$ and $Z^3$ can together form a group of formula -$A^{21}$-$A^{22}$-$A^{23}$-, or when $L^3$, $A^3$, $G^3$, $X^3$, $L^4$, $A^4$, $G^4$ and $X^4$ are absent, $Z^3$ and $Z^4$ can together form a group of formula -$A^{21}$-$A^{22}$-$A^{23}$-; wherein $A^{21}$, $A^{22}$, and $A^{23}$ are independently chosen from —C$Z^{21}Z^{22}$—, —C$Z^{23}Z^{24}$C$Z^{25}Z^{26}$—, —C(=O)—, —N$Z^{27}$—, —S—, —S(=O)—, —S(=O)$_2$—, or —O—; wherein:

(a) when any two of $Z^{21}$, $Z^{22}$, $Z^{23}$, $Z^{24}$, $Z^{25}$, $Z^{26}$ and $Z^{27}$ are located on adjacent atoms, they may together form a bond between the atoms, and (b) any of $Z^{21}$, $Z^{22}$, $Z^{23}$, $Z^{24}$, $Z^{25}$, $Z^{26}$ and $Z^{27}$ may be independently chosen from H, $C_{1-6}$alkyl optionally substituted by 1-6 $R^{99}$, $C_{6-11}$aryl optionally substituted by 1-7 $R^{99}$, $C_{7-16}$arylalkyl optionally substituted by 1-6 $R^{99}$, $C_{3-11}$cycloalkyl optionally substituted by 1-6 $R^{99}$, $C_{4-17}$cycloalkylalkyl optionally substituted by 1-6 $R^{99}$, 3-15 membered heterocycloalkyl optionally substituted by 1-6 $R^{99}$, 4-21 membered heterocycloalkylalkyl optionally substituted by 1-6 $R^{99}$, 5-15 membered heteroaryl optionally substituted by 1-6 $R^{99}$, 6-21 membered heteroarylalkyl optionally substituted by 1-6 $R^{99}$, halogen, —CN, —C(=O)$R^{90}$, —C(=O)O$R^{90}$, —C(=O)N$R^{92}R^{93}$, —C(=S)N$R^{92}R^{93}$, —N$R^{92}R^{93}$, —N$R^{94}$C(=O)$R^{90}$, —N$R^{94}$C(=O)O$R^{91}$, —N$R^{94}$C(=O)N$R^{92}R^{93}$, —N$R^{94}$C(=O)N$R^{94}$C(=O)$R^{90}$, —N$R^{94}$C(=O)N$R^{94}$C(=O)O$R^{90}$, —N$R^{94}$C(=S)$R^{90}$, —N$R^{94}$S(=O)$_2R^{91}$, —N$R^{94}$P(=O)$R^{98}R^{98}$, —O$R^{90}$, =O, —OC(=O)$R^{90}$, —OC(=O)N$R^{92}R^{93}$, =S, —S(=O)$_nR^{90}$, —S(=O)$_2$N$R^{92}R^{93}$, and —P(=O)$R^{98}R^{98}$; and (c) any two of $Z^{21}$, $Z^{22}$, $Z^{23}$, $Z^{24}$, $Z^{25}$, $Z^{26}$ and $Z^{27}$ may together form a group of formula -$A^{31}$-$A^{32}$-$A^{33}$-, wherein $A^{31}$, $A^{32}$, and $A^{33}$ are independently chosen from —C$Z^{31}Z^{32}$—, —C$Z^{33}Z^{34}$C$Z^{35}Z^{36}$—, —C(=O)—, —N$Z^{37}$—, —S—, —S(=O)—, —S(=O)$_2$—, or —O— wherein:

(i) when any two of $Z^{31}$, $Z^{32}$, $Z^{33}$, $Z^{34}$, $Z^{35}$, $Z^{36}$ and $Z^{37}$ are located on adjacent atoms, they may together form a bond between the atoms, and (ii) any of any of $Z^{21}$, $Z^{22}$, $Z^{23}$, $Z^{24}$, $Z^{25}$, $Z^{26}$ and $Z^{27}$ may be independently chosen from H, $C_{1-6}$alkyl optionally substituted by 1-6 $R^{139}$, $C_{6-11}$aryl optionally substituted by 1-7 $R^{139}$, $C_{7-16}$arylalkyl optionally substituted by 1-6 $R^{139}$, $C_{3-11}$cycloalkyl optionally substituted by 1-6 $R^{139}$, $C_{4-17}$cycloalkylalkyl optionally substituted by 1-6 $R^{139}$, 3-15 membered heterocycloalkyl optionally substituted by 1-6 $R^{139}$, 4-21 membered heterocycloalkylalkyl optionally substituted by 1-6 $R^{139}$, 5-15 membered heteroaryl optionally substituted by 1-6 $R^{139}$, 6-21 membered heteroarylalkyl optionally substituted by 1-6 $R^{139}$, halogen, —CN, —C(=O)$R^{130}$, —C(=O)O$R^{130}$, —C(=O)N$R^{132}R^{133}$, —C(=S)N$R^{132}R^{133}$, —N$R^{132}R^{133}$, —N$R^{134}$C(=O)$R^{130}$, —N$R^{134}$C(=O)O$R^{131}$, —N$R^{134}$C(=O)N$R^{132}R^{133}$, —N$R^{134}$C(=O)N$R^{134}$C(=O)$R^{130}$, N$R^{134}$C(=S)$R^{130}$, N$R^{134}$S(=O)N$R^{132}R^{133}$, —N$R^{134}$P(=O)$R^{138}R^{138}$, —O$R^{130}$, =O, —OCN, —OC(=O)$R^{130}$, —OC(=O)N$R^{132}R^{133}$, =S, —S(=O)$_nR^{130}$, —S(=O)$_2$N$R^{132}R^{133}$, and —P(=O)$R^{138}R^{138}$. In another embodiment, $Z^3$ is H, $C_{1-6}$alkyl optionally substituted by 1-6 $R^{89}$, $C_{6-11}$aryl optionally substituted by 1-7 $R^{89}$, $C_{7-16}$arylalkyl optionally substituted by 1-6 $R^{89}$, $C_{3-11}$cycloalkyl optionally substituted by 1-6 $R^{89}$, $C_{4-17}$cycloalkylalkyl optionally substituted by 1-6 $R^{89}$, 3-15 membered heterocycloalkyl optionally substituted by 1-6 $R^{89}$, 4-21 membered heterocycloalkylalkyl optionally substituted by 1-6 $R^{89}$, 5-15 membered heteroaryl optionally substituted by 1-6 $R^{89}$, 6-21 membered heteroarylalkyl optionally substituted by 1-6 $R^{89}$, halogen, —CN, —C(=O)$R^{80}$, —C(=O)O$R^{80}$, —C(=O)N$R^{82}R^{83}$, —C(=S)N$R^{82}R^{83}$, —N$R^{84}$C(=O)$R^{80}$, —N$R^{84}$C(=O)O$R^{81}$, —N$R^{84}$C(=O)N$R^{82}R^{83}$, —N$R^{84}$C(=O)N$R^{84}$C(=O)$R^{80}$, —N$R^{84}$C(=O)N$R^{84}$C(=O)O$R^{80}$, —N$R^{84}$C(=S)$R^{80}$, —N$R^{84}$S(=O)$_2R^{81}$, —O$R^{80}$, =O, —OC(=O)$R^{80}$, —OC(=O)N$R^{82}R^{83}$, =S, —S(=O)$_nR^{80}$, or —S(=O)$_2$N$R^{82}R^{83}$; alternatively, when $L^2$, $A^2$, $G^2$, $X^2$, $L^3$, $A^3$, $G^3$ and $X^3$ are absent, $Z^2$ and $Z^3$ can together form a group of formula -$A^{21}$-$A^{22}$-$A^{23}$-, or when $L^3$, $A^3$, $G^3$, $X^3$, $L^4$, $A^4$, $G^4$ and $X^4$ are absent, $Z^3$ and $Z^4$ can together form a group of formula -$A^{21}$-$A^{22}$-$A^{23}$-; wherein $A^{21}$, $A^{22}$, and $A^{23}$ are independently chosen from —C$Z^{21}Z^{22}$—, —C$Z^{23}Z^{24}$C$Z^{25}Z^{26}$—, —C(=O)—, —N$Z^{27}$—, —S—, —S(=O)—, —S(=O)$_2$—, or —O—; wherein:

(a) when any two of $Z^{21}$, $Z^{22}$, $Z^{23}$, $Z^{24}$, $Z^{25}$, $Z^{26}$ and $Z^{27}$ are located on adjacent atoms, they may together form a bond between the atoms, and (b) any of $Z^{21}$, $Z^{22}$, $Z^{23}$, $Z^{24}$, $Z^{25}$, $Z^{26}$ and $Z^{27}$ may be independently chosen from H, $C_{1-6}$alkyl optionally substituted by 1-6 $R^{99}$, $C_{6-11}$aryl optionally substituted by 1-7 $R^{99}$, $C_{7-16}$arylalkyl optionally substituted by 1-6 $R^{99}$, $C_{3-11}$cycloalkyl optionally substituted by 1-6 $R^{99}$, $C_{4-17}$cycloalkylalkyl optionally substituted by 1-6 $R^{99}$, 3-15 membered heterocycloalkyl optionally substituted by 1-6 $R^{99}$, 4-21 membered heterocycloalkylalkyl optionally substituted by 1-6 $R^{99}$, 5-15 membered heteroaryl optionally substituted by 1-6 $R^{99}$, 6-21 membered heteroarylalkyl optionally substituted by 1-6 $R^{99}$, halogen, —CN, —C(=O)$R^{90}$, —C(=O)O$R^{90}$, —C(=O)N$R^{92}R^{93}$, —C(=S)N$R^{92}R^{93}$, —N$R^{92}R^{93}$, —N$R^{94}$C(=O)$R^{90}$, —N$R^{94}$C(=O)O$R^{91}$, —N$R^{94}$C(=O)N$R^{92}R^{93}$, —N$R^{94}$C(=O)N$R^{94}$C(=O)$R^{90}$, —N$R^{94}$C(=O)N$R^{94}$C(=O)O$R^{90}$, —N$R^{94}$C(=S)$R^{90}$, —N$R^{94}$S(=O)$_2R^{91}$, —O$R^{90}$, =O, —OC(=O)$R^{90}$, —OC(=O)N$R^{92}R^{93}$, =S, —S(=O)$_nR^{90}$, and —S(=O)$_2$N$R^{92}R^{93}$; and (c) any two of $Z^{21}$, $Z^{22}$, $Z^{23}$, $Z^{24}$, $Z^{25}$, $Z^{26}$ and $Z^{27}$ may together form a group of formula -$A^{31}$-$A^{32}$-$A^{33}$-, wherein $A^{31}$, $A^{32}$, and $A^{33}$ are independently chosen from —C$Z^{31}Z^{32}$—, —C$Z^{33}Z^{34}$C$Z^{35}Z^{36}$—, —C(=O)—, —N$Z^{37}$—, —S—, —S(=O)—, —S(=O)$_2$—, or —O— wherein:

(i) when any two of $Z^{31}$, $Z^{32}$, $Z^{33}$, $Z^{34}$, $Z^{35}$, $Z^{36}$ and $Z^{37}$ are located on adjacent atoms, they may together form a bond between the atoms, and (ii) any of any of $Z^{21}$, $Z^{22}$, $Z^{23}$, $Z^{24}$, $Z^{25}$, $Z^{26}$ and $Z^{27}$ may be independently chosen from H, $C_{1-6}$alkyl optionally substituted by 1-6 $R^{139}$, $C_{6-11}$aryl optionally substituted by 1-7 $R^{139}$, $C_{7-16}$arylalkyl optionally substituted by 1-6 $R^{139}$, $C_{3-11}$cycloalkyl optionally substituted by 1-6 $R^{139}$, $C_{4-17}$cycloalkylalkyl optionally substituted by 1-6 $R^{139}$, 3-15 membered heterocycloalkyl optionally substituted by 1-6 $R^{139}$, 4-21 membered heterocycloalkylalkyl optionally substituted by 1-6 $R^{139}$, 5-15 membered heteroaryl optionally substituted by 1-6 $R^{139}$, 6-21 membered heteroarylalkyl optionally substituted by 1-6 $R^{139}$, halogen, —CN, —C(=O)$R^{130}$, —C(=O)O$R^{130}$, —C(=O)N$R^{132}R^{133}$, —C(=S)N$R^{132}R^{133}$, —N$R^{132}R^{133}$, —N$R^{134}$C(=O)$R^{130}$, —N$R^{134}$C(=O)O$R^{131}$, —N$R^{134}$C(=O)N$R^{132}R^{133}$, —N$R^{134}$C(=O)$R^{130}$, —N$R^{134}$C(=S)$R^{130}$, —N$R^{134}$S(=O)$_2R^{131}$, —O$R^{130}$, =O, —OCN, —OC(=O)$R^{130}$, —OC(=O)N$R^{132}R^{133}$, =S, —S(=O)$_nR^{130}$, and —S(=O)$_2$N$R^{132}R^{133}$.

In another embodiment, $Z^3$ is H, $C_{1-6}$alkyl optionally substituted by 1-6 $R^{89}$, $C_{6-11}$aryl optionally substituted by 1-7 $R^{89}$, $C_{7-16}$arylalkyl optionally substituted by 1-6 $R^{89}$, $C_{3-11}$cycloalkyl optionally substituted by 1-6 $R^{89}$, 3-15 membered heterocycloalkyl optionally substituted by 1-6 $R^{89}$, 5-15 membered heteroaryl optionally substituted by 1-6 $R^{89}$, halogen, —CN, —C(=O)$R^{80}$, —C(=O)O$R^{80}$, —C(=O)N$R^{82}R^{83}$, —N$R^{84}$C(=O)$R^{80}$, —N$R^{84}$C(=O)O$R^{81}$, —N$R^{84}$C(=O)N$R^{82}R^{83}$, —N$R^{84}$S(=O)$_2R^{81}$, —O$R^{80}$, =O, —OC(=O)$R^{80}$, —OC(=O)N$R^{82}R^{83}$, =S, —S(=O)$_n$$R^{80}$, or —S(=O)$_2$N$R^{82}R^{83}$; alternatively, when $L^2$, $A^2$, $G^2$, $X^2$, $L^3$, $A^3$, $G^3$ and $X^3$ are absent, $Z^2$ and $Z^3$ can together form a group of formula -$A^{21}$-$A^{22}$-$A^{23}$-, or when $L^3$, $A^3$, $G^3$, $X^3$, $L^4$, $A^4$, $G^4$ and $X^4$ are absent, $Z^3$ and $Z^4$ can together form a group of formula -$A^{21}$-$A^{22}$-$A^{23}$; wherein $A^{21}$, $A^{22}$, and $A^{23}$ are independently chosen from —C$Z^{21}Z^{22}$—, —C$Z^{23}Z^{24}$C$Z^{25}Z^{26}$, or —N$Z^{27}$—; wherein:

(a) when any two of $Z^{21}$, $Z^{22}$, $Z^{23}$, $Z^{24}$, $Z^{25}$, $Z^{26}$ and $Z^{27}$ are located on adjacent atoms, they may together form a bond between the atoms, and (b) any of $Z^{21}$, $Z^{22}$, $Z^{23}$, $Z^{24}$, $Z^{25}$, $Z^{26}$ and $Z^{27}$ may be independently chosen from H, $C_{1-6}$alkyl optionally substituted by 1-6 $R^{99}$, $C_{6-11}$aryl optionally substituted by 1-7 $R^{99}$, $C_{3-11}$cycloalkyl optionally substituted by 1-6 $R^{99}$, 3-15 membered heterocycloalkyl optionally substituted by 1-6 $R^{99}$, 5-15 membered heteroaryl optionally substituted by 1-6 $R^{99}$, halogen, —CN, —C(=O)$R^{90}$, —C(=O)O$R^{90}$, —C(=O)N$R^{92}R^{93}$, —N$R^{92}R^{93}$, —N$R^{94}$C(=O)$R^{90}$, —N$R^{94}$C(=O)O$R^{91}$, —N$R^{94}$C(=O)N$R^{92}R^{93}$, —N$R^{94}$S(=O)$_2R^{91}$, —O$R^{90}$, =O, —OC(=O)$R^{90}$, —OC(=O)N$R^{92}R^{93}$, =S, —S(=O)$_nR^{90}$, and —S(=O)$_2$N$R^{92}R^{93}$. In another embodiment, $Z^3$ is H, $C_{1-6}$alkyl optionally substituted by 1-13 $R^{89}$, or halogen; alternatively, when $L^2$, $A^2$, $G^2$, $X^2$, $L^3$, $A^3$, $G^3$ and $X^3$ are absent, $Z^2$ and $Z^3$ can together form a group of formula -$A^{21}$-$A^{22}$-$A^{23}$-, wherein $A^{21}$, $A^{22}$, and $A^{23}$ are independently chosen from —C$Z^{21}Z^{22}$—, —C$Z^{23}Z^{24}$C$Z^{25}Z^{26}$—, wherein when any two of $Z^{21}$, $Z^{22}$, $Z^{23}$, $Z^{24}$, $Z^{25}$, $Z^{26}$ and $Z^{27}$ are located on adjacent atoms, they may together form a bond between the atoms, and wherein any of $Z^{21}$, $Z^{22}$, $Z^{23}$, $Z^{24}$, $Z^{25}$, $Z^{26}$ and $Z^{27}$ may be independently chosen from H and —O$R^{90}$. In another embodiment, $Z^3$ is H, $C_{1-6}$alkyl optionally substituted by 1-3 $R^{89}$, or halogen; alternatively, when $L^2$, $A^2$, $G^2$, $X^2$, $L^3$, $A^3$, $G^3$ and $X^3$ are absent, $Z^2$ and $Z^3$ can together form a group of formula -$A^{21}$-$A^{22}$-$A^{23}$-, wherein $A^{21}$, $A^{22}$, and $A^{23}$ are independently chosen from —C$Z^{21}Z^{22}$—, —C$Z^{23}Z^{24}$C$Z^{25}Z^{26}$—, wherein when any two of $Z^{21}$, $Z^{22}$, $Z^{23}$, $Z^{24}$, $Z^{25}$, $Z^{26}$ and $Z^{27}$ are located on adjacent atoms, they may together form a bond between the atoms, and wherein any of $Z^{21}$, $Z^{22}$, $Z^{23}$, $Z^{24}$, $Z^{25}$, $Z^{26}$ and $Z^{27}$ may be independently chosen from H and —O$R^{90}$. In another embodiment, $Z^3$ is H, $C_{1-6}$alkyl optionally substituted by 1-3 $R^{89}$, or halogen; alternatively, when $L^2$, $A^2$, $G^2$, $X^2$, $L^3$, $A^3$, $G^3$ and $X^3$ are absent, $Z^2$ and $Z^3$ can together form a phenyl group optionally substituted by —O$R^{90}$. In another embodiment, $Z^3$ is H, $C_{1-6}$alkyl, or halogen; alternatively, when $L^2$, $A^2$, $G^2$, $X^2$, $L^3$, $A^3$, $G^3$ and $X^3$ are absent, $Z^2$ and $Z^3$ can together form a phenyl group optionally substituted by —OH or —O$C_{1-6}$alkyl. In another embodiment, $Z^3$ is H, $C_{1-6}$alkyl, or halogen; alternatively, when $L^2$, $A^2$, $G^2$, $X^2$, $L^3$, $A^3$, $G^3$ and $X^3$ are absent, $Z^2$ and $Z^3$ can together form a phenyl group optionally substituted by —O$C_{1-6}$alkyl. In another embodiment, $Z^3$ is H, methyl, or bromo; alternatively, when $L^2$, $A^2$, $G^2$, $X^2$, $L^3$, $A^3$, $G^3$ and $X^3$ are absent, $Z^2$ and $Z^3$ can together form a phenyl group optionally substituted by —OCH$_3$. In another embodiment, $Z^3$ is H.

In each embodiment of the present invention that is described in the paragraphs that precede or follow this paragraph, the definition of $L^4$ may be chosen from any of the embodiments that are described in this paragraph. In one embodiment, $L^4$ is —$C_{0-3}$alkylC(=O)$C_{0-3}$alkyl-, —$C_{0-3}$alkylC(=O)O$C_{0-3}$alkyl-, —$C_{0-3}$alkylC(=O)N$R^{44}C_{0-3}$alkyl-, —$C_{0-3}$alkylC(=O)C(=O)$C_{0-3}$alkyl-, —$C_{0-3}$alkylC(=N$R^{45}$)$C_{0-3}$alkyl-, —$C_{0-3}$alkylC(=N$R^{45}$)N$R^{44}C_{0-3}$alkyl-, —$C_{0-3}$alkylC(=NOH)N$R^{44}C_{0-3}$alkyl-, —$C_{0-3}$alkylC(=NO$R^{46}$)$C_{0-3}$alkyl-, —$C_{0-3}$alkylC(=NN$R^{42}R^{43}$)$C_{0-3}$alkyl-, —$C_{0-3}$alkylC(=NN$R^{44}$C(=O)$R^{41}$)$C_{0-3}$alkyl-, —$C_{0-3}$alkylC(=NN$R^{44}$C(=O)O$R^{41}$)$C_{0-3}$alkyl-, —$C_{0-3}$alkylC(=S)N$R^{44}C_{0-3}$alkyl-, —$C_{0-3}$alkylN$R^{44}C_{0-3}$alkyl-, —$C_{0-3}$alkylN$R^{44}$N$R^{44}C_{0-3}$alkyl-, —$C_{0-3}$alkylN=N$C_{0-3}$alkyl-, —$C_{0-3}$alkylN$R^{44}$C(=O)$C_{0-3}$alkyl-, —$C_{0-3}$alkylN$R^{44}$C(=O)C(=O)$C_{0-3}$alkyl-, —$C_{0-3}$alkylN$R^{44}$C(=O)O$C_{0-3}$alkyl-, —$C_{0-3}$alkylN$R^{44}$C(=O)C(=O)O$C_{0-3}$alkyl-, —$C_{0-3}$alkylN$R^{44}$C(=O)N$R^{44}C_{0-3}$alkyl-, —$C_{0-3}$alkylN$R^{44}$C(=O)N$R^{44}$C(=O)$C_{0-3}$alkyl-, —$C_{0-3}$alkylN$R^{44}$C(=O)N$R^{44}$C(=O)O$C_{0-3}$alkyl-, —$C_{0-3}$alkylN$R^{44}$C(=N$R^{45}$)N$R^{44}C_{0-3}$alkyl-, —$C_{0-3}$alkylN$R^{44}$C(=O)C(=O)N$R^{44}C_{0-3}$alkyl-, —$C_{0-3}$alkylN$R^{44}$C(=S)$C_{0-3}$alkyl-, —$C_{0-3}$alkylN$R^{44}$C(=S)O$C_{0-3}$alkyl-, —$C_{0-3}$alkylN$R^{44}$C(=S)N$R^{44}C_{0-3}$alkyl-, —$C_{0-3}$alkylN$R^{44}$S(=O)$_2C_{0-3}$alkyl-, —$C_{0-3}$alkylN$R^{44}$S(=O)$_2$N$R^{44}C_{0-3}$alkyl-, —$C_{0-3}$alkylO$C_{0-3}$alkyl-, —$C_{0-3}$alkylOC(=O)$C_{0-3}$alkyl-, —$C_{0-3}$alkylOC(=O)N$R^{44}C_{0-3}$alkyl-, —$C_{0-3}$alkylOC(=O)O$C_{0-3}$alkyl-, —$C_{0-3}$alkylOC(=N$R^{45}$)N$R^{44}C_{0-3}$alkyl-, —$C_{0-3}$alkylOS(=O)$C_{0-3}$alkyl-, —$C_{0-3}$alkylOS(=O)$_2C_{0-3}$alkyl-, —$C_{0-3}$alkylOS(=O)$_2$O$C_{0-3}$alkyl-, —$C_{0-3}$alkylOS(=O)$_2$N$R^{44}C_{0-3}$alkyl-, —$C_{0-3}$alkylS(=O)$_nC_{0-3}$alkyl-, —$C_{0-3}$alkylS(=O)$_2$O$C_{0-3}$alkyl-, —$C_{0-3}$alkylSO$_3C_{0-3}$alkyl-, —$C_{0-3}$alkylS(=O)$_2$N$R^{44}C_{0-3}$alkyl-, —$C_{0-3}$alkylS(=O)N$R^{44}C_{0-3}$alkyl-, or absent. In another embodiment, $L^4$ is —$C_{0-3}$alkylC(=O)$C_{0-3}$alkyl-, —$C_{0-3}$alkylC(=O)O$C_{0-3}$alkyl-, —$C_{0-3}$alkylC(=O)N$R^{44}C_{0-3}$alkyl-, —$C_{0-3}$alkylC(=O)C(=O)$C_{0-3}$alkyl-, —$C_{0-3}$alkylC(=S)N$R^{44}C_{0-3}$alkyl-, —$C_{0-3}$alkylN$R^{44}C_{0-3}$alkyl-, —$C_{0-3}$alkylN$R^{44}$N$R^{44}C_{0-3}$alkyl-, —$C_{0-3}$alkylN$R^{44}$C(=O)$C_{0-3}$alkyl-, —$C_{0-3}$alkylN$R^{44}$C(=O)C(=O)$C_{0-3}$alkyl-, —$C_{0-3}$alkylN$R^{44}$C(=O)O$C_{0-3}$alkyl-, —$C_{0-3}$alkylN$R^{44}$C(=O)C(=O)O$C_{0-3}$alkyl-, —$C_{0-3}$alkylN$R^{44}$C(=O)N$R^{44}C_{0-3}$alkyl-, —$C_{0-3}$alkylN$R^{44}$C(=O)N$R^{44}$C(=O)$C_{0-3}$alkyl-, —$C_{0-3}$alkylN$R^{44}$C(=O)N$R^{44}$C(=O)O$C_{0-3}$alkyl-, —$C_{0-3}$alkylN$R^{44}$C(=N$R^{45}$)N$R^{44}C_{0-3}$alkyl-, —$C_{0-3}$alkylN$R^{44}$C(=O)C(=O)N$R^{44}C_{0-3}$alkyl-, —$C_{0-3}$alkylN$R^{44}$C(=S)$C_{0-3}$alkyl-, —$C_{0-3}$alkylN$R^{44}$C(=S)O$C_{0-3}$alkyl-, —$C_{0-3}$alkylN$R^{44}$C(=S)N$R^{44}C_{0-3}$alkyl-, —$C_{0-3}$alkylN$R^{44}$S(=O)$_2C_{0-3}$alkyl-, —$C_{0-3}$alkylN$R^{44}$S(=O)$_2$N$R^{44}C_{0-3}$alkyl-, —$C_{0-3}$alkylO$C_{0-3}$alkyl-, —$C_{0-3}$alkylOC(=O)$C_{0-3}$alkyl-, —$C_{0-3}$alkylOC(=O)N$R^{44}C_{0-3}$alkyl-, —$C_{0-3}$alkylOC(=O)O$C_{0-3}$alkyl-, —$C_{0-3}$alkylOS(=O)$C_{0-3}$alkyl-, —$C_{0-3}$alkylOS(=O)$_2C_{0-3}$alkyl-, —$C_{0-3}$alkylOS(=O)$_2$O$C_{0-3}$alkyl-, —$C_{0-3}$alkylOS(=O)$_2$N$R^{44}C_{0-3}$alkyl-, —$C_{0-3}$alkylS(=O)$_nC_{0-3}$alkyl-, —$C_{0-3}$alkylS(=O)$_2$O$C_{0-3}$alkyl-, —$C_{0-3}$alkylSO$_3C_{0-3}$alkyl-, —$C_{0-3}$alkylS(=O)$_2$N$R^{44}C_{0-3}$alkyl-, —$C_{0-3}$alkylS(=O)N$R^{44}C_{0-3}$alkyl-, or absent. In another embodiment, $L^4$ is —$C_{0-3}$alkylC(=O)$C_{0-3}$alkyl-, —$C_{0-3}$alkylC(=O)O$C_{0-3}$alkyl-, —$C_{0-3}$alkylC(=O)N$R^{44}C_{0-3}$alkyl-, —$C_{0-3}$alkylC(=S)N$R^{44}C_{0-3}$alkyl-, —$C_{0-3}$alkylN$R^{44}C_{0-3}$alkyl-, —$C_{0-3}$alkylN$R^{44}$N$R^{44}C_{0-3}$alkyl-, —$C_{0-3}$alkylN$R^{44}$C(=O)$C_{0-3}$alkyl-, —$C_{0-3}$alkylN$R^{44}$C(=O)O$C_{0-3}$alkyl-, —$C_{0-3}$alkylN$R^{44}$C(=O)N$R^{44}C_{0-3}$alkyl-, —$C_{0-3}$alkylN$R^{44}$C(=O)N$R^{44}$C(=O)$C_{0-3}$alkyl-, —$C_{0-3}$alkylN$R^{44}$C(=O)N$R^{44}$C(=O)O$C_{0-3}$alkyl-, —$C_{0-3}$alkylN$R^{44}$C(=N$R^{45}$)N$R^{44}C_{0-3}$alkyl-, —$C_{0-3}$alkylN$R^{44}$C(=S)N$R^{44}C_{0-3}$alkyl-, —$C_{0-3}$alkylN$R^{44}$S(=O)$_2C_{0-3}$alkyl-, —$C_{0-3}$alkylO$C_{0-3}$alkyl-, —$C_{0-3}$alkylOC(=O)$C_{0-3}$alkyl-, —$C_{0-3}$alkylOC(=O)N$R^{44}C_{0-3}$alkyl-, —$C_{0-3}$alkylS(=O)—

$C_{0-3}$alkyl-, —$C_{0-3}$alkylS(=O)$_2$NR$^{44}$C$_{0-3}$alkyl-, or absent. In another embodiment, L$^4$ is —C$_{0-3}$alkylC(=O)C$_{0-3}$alkyl-, —C$_{0-3}$alkylC(=O)OC$_{0-3}$alkyl-, —C$_{0-3}$alkylC(=O)NR$^{44}$C$_{0-3}$alkyl-, —C$_{0-3}$alkylC(=S)NR$^{44}$C$_{0-3}$alkyl-, —C$_{0-3}$alkylNR$^{44}$C$_{0-3}$alkyl-, —C$_{0-3}$alkylNR$^{44}$NR$^{44}$C$_{0-3}$alkyl-, —C$_{0-3}$alkylNR$^{44}$C(=O)C$_{0-3}$alkyl-, —C$_{0-3}$alkylNR$^{44}$C(=O)OC$_{0-3}$alkyl-, —C$_{0-3}$alkylNR$^{44}$C(=O)NR$^{44}$C$_{0-3}$alkyl-, —C$_{0-3}$alkylNR$^{44}$C(=O)NR$^{44}$C(=O)C$_{0-3}$alkyl-, —C$_{0-3}$alkylNR$^{44}$C(=O)NR$^{44}$C(=O)OC$_{0-3}$alkyl-, —C$_{0-3}$alkylNR$^{44}$C(=S)C$_{0-3}$alkyl-, —C$_{0-3}$alkylNR$^{44}$S(=O)$_2$C$_{0-3}$alkyl-, —C$_{0-3}$alkylOC$_{0-3}$alkyl-, —C$_{0-3}$alkylOC(=O)C$_{0-3}$alkyl-, —C$_{0-3}$alkylOC(=O)NR$^{44}$C$_{0-3}$alkyl-, —C$_{0-3}$alkylS(=O)—C$_{0-3}$alkyl-, —C$_{0-3}$alkylS(=O)$_2$NR$^{44}$C$_{0-3}$alkyl-, or absent. In another embodiment, L$^4$ is —C$_{0-3}$alkylC(=O)C$_{0-3}$alkyl-, —C$_{0-3}$alkylC(=O)OC$_{0-3}$alkyl-, —C$_{0-3}$alkylC(=O)NR$^{44}$C$_{0-3}$alkyl-, —C$_{0-3}$alkylNR$^{44}$C$_{0-3}$alkyl-, —C$_{0-3}$alkylNR$^{44}$C(=O)C$_{0-3}$alkyl-, —C$_{0-3}$alkylNR$^{44}$C(=O)OC$_{0-3}$alkyl-, —C$_{0-3}$alkylNR$^{44}$C(=O)NR$^{44}$C$_{0-3}$alkyl-, —C$_{0-3}$alkylNR$^{44}$S(=O)$_2$C$_{0-3}$alkyl-, —C$_{0-3}$alkylOC$_{0-3}$alkyl-, —C$_{0-3}$alkylOC(=O)C$_{0-3}$alkyl-, —C$_{0-3}$alkylOC(=O)NR$^{44}$C$_{0-3}$alkyl-, —C$_{0-3}$alkylS(=O)—C$_{0-3}$alkyl-, —C$_{0-3}$alkylS(=O)$_2$NR$^{44}$C$_{0-3}$alkyl-, or absent. In another embodiment, L$^4$ is —C(=O)—, —C(=O)O—, —C(=O)NR$^{44}$—, —C(=O)C(=O)—, —C(=S)NR$^{44}$—, —NR$^{44}$—, —NR$^{44}$NR$^{44}$—, —NR$^{44}$C(=O)—, —NR$^{44}$C(=O)C(=O)—, —NR$^{44}$C(=O)O—, —NR$^{44}$C(=O)C(=O)O—, —NR$^{44}$C(=O)NR$^{44}$—, —NR$^{44}$C(=O)NR$^{44}$C(=O)—, —NR$^{44}$C(=O)NR$^{44}$C(=O)O—, —NR$^{44}$C(=NR$^{45}$)NR$^{44}$—, —NR$^{44}$C(=O)C(=O)NR$^{44}$—, —NR$^{44}$C(=S)—, —NR—, —NR$^{44}$C(=S)NR$^{44}$—, —NR$^{44}$S(=O)$_2$—, —NR$^{44}$S(=O)$_2$NR$^{44}$—, —O—, —OC(=O)—, —OC(=O)NR$^{44}$—, —OC(=O)O—, —OS(=O)—, —OS(=O)$_2$—, —OS(=O)$_2$O—, —OS(=O)$_2$NR$^{44}$—, —S(=O)$_n$—, —S(=O)$_2$O—, —SO$_3$—, —S(=O)$_2$NR$^{44}$—, —S(=O)NR$^{44}$—, or absent. In another embodiment, L$^4$ is —C(=O)—, —C(=O)O—, —C(=O)NR$^{44}$—, —C(=S)NR$^{44}$—, —NR$^{44}$—, —NR$^{44}$C(=O)—, —NR$^{44}$C(=O)O—, —NR$^{44}$C(=O)NR$^{44}$—, —NR$^{44}$C(=O)NR$^{44}$C(=O)—, —NR$^{44}$C(=O)NR$^{44}$C(=O)O—, —NR$^{44}$C(=NR$^{45}$)NR$^{44}$—, —NR$^{44}$C(=S)NR$^{44}$—, —NR$^{44}$S(=O)$_2$—, —O—, —OC(=O)—, —OC(=O)NR$^{44}$—, —S(=O)$_n$—, —S(=O)$_2$NR$^{44}$—, or absent. In another embodiment, L$^4$ is —C(=O)—, —C(=O)O—, —C(=O)NR$^{44}$—, —C(=S)NR$^{44}$—, —NR$^{44}$—, —NR$^{44}$NR$^{44}$—, —NR$^{44}$C(=O)—, —NR$^{44}$C(=O)O—, —NR$^{44}$C(=O)NR$^{44}$—, —NR$^{44}$C(=O)NR$^{44}$C(=O)—, —NR$^{44}$C(=O)NR$^{44}$C(=O)O—, —NR$^{44}$C(=S)—, —NR$^{44}$S(=O)$_2$—, —O—, —OC(=O)—, —OC(=O)NR$^{44}$—, —S(=O)$_n$—, —S(=O)$_2$NR$^{44}$—, or absent. In another embodiment, L$^4$ is —C(=O)—, —C(=O)O—, —C(=O)NR$^{44}$—, —NR$^{44}$—, —NR$^{44}$C(=O)—, —NR$^{44}$C(=O)O—, —NR$^{44}$C(=O)NR$^{44}$—, —NR$^{44}$S(=O)$_2$—, —O—, —OC(=O)—, —OC(=O)NR$^{44}$—, —S(=O)$_n$—, —S(=O)$_2$NR$^{44}$—, or absent. In another embodiment, L$^4$ is absent. In another embodiment, when Q$^2$ and Q$^3$ are each phenyl, then each of the following is true: (a) L$^4$ is not —O—, —S—, —S(=O), —S(=O)$_2$—, —OC(=O)—, —OC(=O)O—, or —OC(=O)NR$^{44}$—; (b) G$^4$ is not —O—, —S—, —S(=O), —S(=O)$_2$—, —OC(=O)—, —OC(=O)O—, or —OC(=O)NR$^{64}$—; and (c) X$^4$ is not —O—, —S—, —S(=O)—, —S(=O)$_2$—, —OC(=O)—, —OC(=O)O—, or —OC(=O)NR$^{74}$—. In another embodiment, when Q$^2$ and Q$^3$ are each phenyl, then each of the following is true:

(a) L$^4$ is not —O—, —S—, —S(=O)—, —S(=O)$_2$—, —OC(=O)—, —OC(=O)O—, or —OC(=O)NR$^{44}$—;
(b) when L$^4$ is absent, G$^4$ is not —O—, —S—, —S(=O), —S(=O)$_2$—, —OC(=O)—, —OC(=O)O—, or —OC(=O)NR$^{64}$—; and (c) when L$^4$ and G$^4$ are each absent, X$^4$ is not —O—, —S—, —S(=O), —S(=O)$_2$—, —OC(=O)—, —OC(=O)O—, or —OC(=O)NR$^{74}$—.

In each embodiment of the present invention that is described in the paragraphs that precede or follow this paragraph, the definition of A$^4$ may be chosen from any of the embodiments that are described in this paragraph. In one embodiment, A$^4$ is $C_{1-6}$alkylene optionally substituted by 1-12 R$^b$, $C_{2-6}$alkenylene optionally substituted by 1-10 R$^b$, $C_{2-6}$alkynylene optionally substituted by 1-8 R$^b$, $C_{6-11}$arylene optionally substituted by 1-10 R$^b$, $C_{7-16}$arylalkylene optionally substituted by 1-18 R$^b$, $C_{3-11}$cycloalkylene optionally substituted by 1-20 R$^b$, $C_{4-17}$cycloalkylalkylene optionally substituted by 1-31 R$^b$, 3-15 membered heterocycloalkylene optionally substituted by 1-27 R$^b$, 4-21 membered heterocycloalkylalkylene optionally substituted by 1-39 R$^b$, 5-15 membered heteroarylene optionally substituted by 1-14 R$^b$, 6-21 membered heteroarylalkylene optionally substituted by 1-26 R$^b$, or absent. In another embodiment, A$^4$ is $C_{1-6}$alkylene optionally substituted by 1-12 R$^b$, $C_{6-11}$arylene optionally substituted by 1-6 R$^b$, $C_{7-16}$arylalkylene optionally substituted by 1-18 R$^b$, $C_{3-11}$cycloalkylene optionally substituted by 1-20 R$^b$, $C_{4-6}$cycloalkylalkylene optionally substituted by 1-31 R$^b$, 3-15 membered heterocycloalkylene optionally substituted by 1-27 R$^b$, 4-21 membered heterocycloalkylalkylene optionally substituted by 1-39 R$^b$, 5-15 membered heteroarylene optionally substituted by 1-14 R$^b$, 6-21 membered heteroarylalkylene optionally substituted by 1-26 R$^b$, or absent. In another embodiment, A$^4$ is $C_{1-6}$alkylene optionally substituted by 1-12 R$^b$, $C_{6-11}$arylene optionally substituted by 1-6 R$^b$, $C_{3-11}$cycloalkylene optionally substituted by 1-20 R$^b$, 3-15 membered heterocycloalkylene optionally substituted by 1-27 R$^b$, 5-15 membered heteroarylene optionally substituted by 1-14 R$^b$, or absent. In another embodiment, A$^4$ is $C_{1-6}$alkylene optionally substituted by 1-12 R$^b$, $C_{6-11}$arylene optionally substituted by 1-6 R$^b$, $C_{3-16}$cycloalkylene optionally substituted by 1-20 R$^b$, 3-10 membered heterocycloalkylene optionally substituted by 1-27 R$^b$, 5-10 membered heteroarylene optionally substituted by 1-14 R$^b$, or absent. In another embodiment, A$^4$ is $C_{1-6}$alkylene optionally substituted by 1-6 R$^b$, $C_{6-11}$arylene optionally substituted by 1-6 R$^b$, $C_{7-16}$arylalkylene optionally substituted by 1-6 R$^b$, $C_{3-11}$cycloalkylene optionally substituted by 1-6 R$^b$, $C_{4-17}$cycloalkylalkylene optionally substituted by 1-6 R$^b$, 3-15 membered heterocycloalkylene optionally substituted by 1-6 R$^b$, 4-21 membered heterocycloalkylalkylene optionally substituted by 1-6 R$^b$, 5-15 membered heteroarylene optionally substituted by 1-6 R$^b$, 6-21 membered heteroarylalkylene optionally substituted by 1-6 R$^b$, or absent. In another embodiment, A$^4$ is $C_{1-6}$alkylene optionally substituted by 1-6 R$^b$, $C_{6-11}$ arylene optionally substituted by 1-6 R$^b$, $C_{3-11}$cycloalkylene optionally substituted by 1-6 R$^b$, 3-15 membered heterocycloalkylene optionally substituted by 1-6 R$^b$, 5-15 membered heteroarylene optionally substituted by 1-6 R$^b$, or absent. In another embodiment, A$^4$ is $C_{1-6}$alkylene optionally substituted by 1-3 R$^b$, $C_{6-11}$arylene optionally substituted by 1-3 R$^b$, $C_{3-6}$cycloalkylene optionally substituted by 1-3 R$^b$, 3-6 membered heterocycloalkylene optionally substituted by 1-3 R$^b$, 5-6 membered heteroarylene optionally substituted by 1-3 R$^b$, or absent. In another embodiment, A$^4$ is $C_{1-6}$alkylene optionally substituted by 1-6 R$^b$, $C_{6-11}$arylene optionally substituted by 1-6 R$^b$, $C_{3-40}$cycloalkylene optionally substituted by 1-6 R$^b$, 3-10 membered heterocycloalkylene optionally substituted by 1-6 R$^b$, 5-10 membered heteroarylene optionally substituted by 1-6 R$^b$, or absent. In another embodiment, A$^4$ is $C_{6-11}$arylene optionally substituted by 1-10 $R^b$, or absent. In another embodiment, $A^4$ is $C_{6-10}$aryl or $C_{6-10}$arylene optionally substituted by 1-3 $R^b$, or absent. In another embodiment, $A^4$ is phenylene optionally substituted by 1-3 $R^b$, or absent. In another embodiment, $A^4$ is phenyl, phenylene, or absent.

In each embodiment of the present invention that is described in the paragraphs that precede or follow this paragraph, the definition of $G^4$ may be chosen from any of the embodiments that are described in this paragraph. In one embodiment, $G^4$ is $C_{1-6}$alkylene optionally substituted by 1-12 $R^{69}$, $C_{2-6}$alkenylene optionally substituted by 1-10 $R^{69}$, $C_{2-6}$alkynylene optionally substituted by 1-8 $R^{69}$, $C_{6-11}$arylene optionally substituted by 1-10 $R^{69}$, $C_{7-16}$arylalkylene optionally substituted by 1-18 $R^{69}$, $C_{3-11}$cycloalkylene optionally substituted by 1-20 $R^{69}$, $C_{4-17}$cycloalkylalkylene optionally substituted by 1-31 $R^{69}$, 3-15 membered heterocycloalkylene optionally substituted by 1-27 $R^{69}$, 4-21 membered heterocycloalkylalkylene optionally substituted by 1-39 $R^{69}$, 5-15 membered heteroarylene optionally substituted by 1-14 $R^{69}$, 6-21 membered heteroarylalkylene optionally substituted by 1-26 $R^{69}$, —$C_{0-3}$alkylC(=O)$C_{0-3}$alkyl-, —$C_{0-3}$alkylC(=O)O$C_{0-3}$alkyl-, —$C_{0-3}$alkylC(=O)NR$^{64}C_{0-3}$alkyl-, —$C_{0-3}$alkylC(=O)C(=O)$C_{0-3}$alkyl-, —$C_{0-3}$alkylC(=NR$^{65}$)$C_{0-3}$alkyl-, —$C_{0-3}$alkylC(=NR$^{65}$)NR$^{64}C_{0-3}$alkyl-, —$C_{0-3}$alkylC(=NOH)NR$^{64}C_{0-3}$alkyl-, —$C_{0-3}$alkylC(=NOR$^{66}$)$C_{0-3}$alkyl-, —$C_{0-3}$alkylC(=NNR$^{62}$R$^{63}$)$C_{0-3}$alkyl-, —$C_{0-3}$alkylC(=NNR$^{64}$C(=O)R$^{61}$)$C_{0-3}$alkyl-, —$C_{0-3}$alkylC(=NNR$^{64}$C(=O)OR$^{61}$)$C_{0-3}$alkyl-, —$C_{0-3}$alkylC(=S)NR$^{64}C_{0-3}$alkyl-, —$C_{0-3}$alkylNR$^{64}C_{0-3}$alkyl-, —$C_{0-3}$alkylNR$^{64}$NR$^{64}C_{0-3}$alkyl-, —$C_{0-3}$alkylN=N$C_{0-3}$alkyl-, —$C_{0-3}$alkylNR$^{64}$C(=O)$C_{0-3}$alkyl-, —$C_{0-3}$alkylNR$^{64}$C(=O)C(=O)$C_{0-3}$alkyl-, —$C_{0-3}$alkylNR$^{64}$C(=O)O$C_{0-3}$alkyl-, —$C_{0-3}$alkylNR$^{64}$C(=O)C(=O)O$C_{0-3}$alkyl-, —$C_{0-3}$alkylNR$^{64}$C(=O)NR$^{64}C_{0-3}$alkyl-, —$C_{0-3}$alkylNR$^{64}$C(=O)NR$^{64}$C(=O)$C_{0-3}$alkyl-, —$C_{0-3}$alkylNR$^{64}$C(=O)NR$^{64}$C(=O)O$C_{0-3}$alkyl-, —$C_{0-3}$alkylNR$^{64}$C(=NR$^{65}$)NR$^{64}C_{0-3}$alkyl-, —$C_{0-3}$alkylNR$^{64}$C(=O)C(=O)NR$^{64}C_{0-3}$alkyl-, —$C_{0-3}$alkylNR$^{64}$C(=S)$C_{0-3}$alkyl-, —$C_{0-3}$alkylNR$^{64}$C(=S)O$C_{0-3}$alkyl-, —$C_{0-3}$alkylNR$^{64}$C(=S)NR$^{64}C_{0-3}$alkyl-, —$C_{0-3}$alkylNR$^{64}$S(=O)$_2C_{0-3}$alkyl-, —$C_{0-3}$alkylNR$^{64}$S(=O)$_2$NR$^{64}C_{0-3}$alkyl-, —$C_{0-3}$alkylO$C_{0-3}$alkyl-, —$C_{0-3}$alkylOC(=O)$C_{0-3}$alkyl-, —$C_{0-3}$alkylOC(=O)NR$^{64}C_{0-3}$alkyl-, —$C_{0-3}$alkylOC(=O)O$C_{0-3}$alkyl-, —$C_{0-3}$alkylOC(=NR$^{65}$)NR$^{64}C_{0-3}$alkyl-, —$C_{0-3}$alkylOS(=O)$C_{0-3}$alkyl-, —$C_{0-3}$alkylOS(=O)$_2C_{0-3}$alkyl-, —$C_{0-3}$alkylOS(=O)$_2$O$C_{0-3}$alkyl-, —$C_{0-3}$alkylOS(=O)$_2$NR$^{64}C_{0-3}$alkyl-, —$C_{0-3}$alkylS(=O)—$C_{0-3}$alkyl-, —$C_{0-3}$alkylS(=O)$_2$O$C_{0-3}$alkyl-, —$C_{0-3}$alkylSO$_3C_{0-3}$alkyl-, —$C_{0-3}$alkylS(=O)$_2$NR$^{64}C_{0-3}$alkyl-, —$C_{0-3}$alkylS(=O)NR$^{64}C_{0-3}$alkyl-, or absent. In another embodiment, $G^4$ is $C_{1-6}$alkylene optionally substituted by 1-12 $R^{69}$, $C_{6-11}$arylene optionally substituted by 1-6 $R^{69}$, $C_{7-16}$arylalkylene optionally substituted by 1-18 $R^{69}$, $C_{3-11}$cycloalkylene optionally substituted by 1-20 $R^{69}$, $C_{4-17}$cycloalkylalkylene optionally substituted by 1-6 $R^{69}$, 3-15 membered heterocycloalkylene optionally substituted by 1-27 $R^{69}$, 4-21 membered heterocycloalkylalkylene optionally substituted by 1-39 $R^{69}$, 5-15 membered heteroarylene optionally substituted by 1-14 $R^{69}$, 6-21 membered heteroarylalkylene optionally substituted by 1-26 $R^{69}$, —$C_{0-3}$alkylC(=O)$C_{0-3}$alkyl-, —$C_{0-3}$alkylC(=O)O$C_{0-3}$alkyl-, —$C_{0-3}$alkylC(=O)NR$^{64}C_{0-3}$alkyl-, —$C_{0-3}$alkylC(=S)NR$^{64}C_{0-3}$alkyl-, —$C_{0-3}$alkylNR$^{64}C_{0-3}$alkyl-, —$C_{0-3}$alkylNR$^{64}$NR$^{64}C_{0-3}$alkyl-, —$C_{0-3}$alkylNR$^{64}$C(=O)$C_{0-3}$alkyl-, —$C_{0-3}$alkylNR$^{64}$C(=O)O$C_{0-3}$alkyl-, —$C_{0-3}$alkylNR$^{64}$C(=O)NR$^{64}C_{0-3}$alkyl-, —$C_{0-3}$alkylNR$^{64}$C(=O)NR$^{64}$C(=O)$C_{0-3}$alkyl-, —$C_{0-3}$alkylNR$^{64}$C(=NR$^{65}$)NR$^{64}C_{0-3}$alkyl-, —$C_{0-3}$alkylNR$^{64}$C(=S)$C_{0-3}$alkyl-, —$C_{0-3}$alkylNR$^{64}$C(=S)NR$^{64}C_{0-3}$alkyl-, —$C_{0-3}$alkylNR$^{64}$S(=O)$_2C_{0-3}$alkyl-, —$C_{0-3}$alkylO$C_{0-3}$alkyl-, —$C_{0-3}$alkylOC(=O)$C_{0-3}$alkyl-, —$C_{0-3}$alkylOC(=O)NR$^{64}C_{0-3}$alkyl-, —$C_{0-3}$alkylS(=O)—$C_{0-3}$alkyl-, —$C_{0-3}$alkylS(=O)$_2$NR$^{64}C_{0-3}$alkyl-, or absent. In another embodiment, $G^4$ is $C_{1-6}$alkylene optionally substituted by 1-12 $R^{69}$, $C_{6-11}$arylene optionally substituted by 1-6 $R^{69}$, $C_{3-11}$cycloalkylene optionally substituted by 1-20 $R^{69}$, 3-15 membered heterocycloalkylene optionally substituted by 1-27 $R^{69}$, 5-15 membered heteroarylene optionally substituted by 1-14 $R^{69}$, —$C_{0-3}$alkylC(=O)$C_{0-3}$alkyl-, —$C_{0-3}$alkylC(=O)O$C_{0-3}$alkyl-, —$C_{0-3}$alkylC(=O)NR$^{64}C_{0-3}$alkyl-, —$C_{0-3}$alkylNR$^{64}C_{0-3}$alkyl-, —$C_{0-3}$alkylNR$^{64}$C(=O)$C_{0-3}$alkyl-, —$C_{0-3}$alkylNR$^{64}$C(=O)O$C_{0-3}$alkyl-, —$C_{0-3}$alkylNR$^{64}$C(=O)NR$^{64}C_{0-3}$alkyl-, —$C_{0-3}$ alkylNR$^{64}$S(=O)$_2$C$_{0-3}$alkyl-, —C$_{0-3}$alkylOC$_{0-3}$alkyl-, —C$_{0-3}$alkylOC(=O)C$_{0-3}$alkyl-, —C$_{0-3}$alkylOC(=O)NR$^{64}$C$_{0-3}$alkyl-, —C$_{0-3}$alkylS(=O)—C$_{0-3}$alkyl-, —C$_{0-3}$alkylS(=O)$_2$NR$^{64}$C$_{0-3}$alkyl-, or absent. In another embodiment, G$^4$ is C$_{1-6}$alkylene optionally substituted by 1-6 R$^{69}$, C$_{6-11}$arylene optionally substituted by 1-6 R$^{69}$, C$_{7-16}$arylalkylene optionally substituted by 1-6 R$^{69}$, C$_{3-11}$cycloalkylene optionally substituted by 1-6 R$^{69}$, C$_{4-6}$cycloalkylalkylene optionally substituted by 1-6 R$^{69}$, 3-15 membered heterocycloalkylene optionally substituted by 1-6 R$^{69}$, 4-21 membered heterocycloalkylalkylene optionally substituted by 1-6 R$^{69}$, 5-15 membered heteroarylene optionally substituted by 1-6 R$^{69}$, 6-21 membered heteroarylalkylene optionally substituted by 1-6 R$^{69}$, —C(=O)—, —C(=O)O—, —C(=O)NR$^{64}$—, —C(=O)C(=O)—, —C(=S)NR$^{64}$—, —NR$^{64}$—, —NR$^{64}$NR$^{64}$—, —NR$^{64}$C(=O)—, —NR$^{64}$C(=O)C(=O)—, —NR$^{64}$C(=O)O—, —NR$^{64}$C(=O)C(=O)O—, —NR$^{64}$C(=O)NR$^{64}$—, —NR$^{64}$C(=O)NR$^{64}$C(=O)—, —NR$^{64}$C(=O)NR$^{64}$C(=O)O—, —NR$^{64}$C(=NR$^{65}$)NR$^{64}$—, —NR$^{64}$C(=O)C(=O)NR$^{64}$—, —NR$^{64}$C(=S)—, —NR$^{64}$C(=S)O—, —NR$^{64}$C(=S)NR$^{64}$—, —NR$^{64}$S(=O)$_2$—, —NR—, —O—, —OC(=O)—, —OC(=O)NR$^{64}$—, —OC(=O)O—, —OS(=O)—, —OS(=O)$_2$—, —OS(=O)$_2$O—, —OS(=O)$_2$NR$^{64}$—, —S(=O)$_n$—, —S(=O)$_2$O—, —SO$_3$—, —S(=O)$_2$NR$^{64}$—, —S(=O)NR$^{64}$—, or absent.

In another embodiment, G$^4$ is C$_{1-6}$alkylene optionally substituted by 1-6 R$^{69}$, C$_{6-11}$arylene optionally substituted by 1-6 R$^{69}$, C$_{7-16}$arylalkylene optionally substituted by 1-6 R$^{69}$, C$_{3-11}$cycloalkylene optionally substituted by 1-6 R$^{69}$, C$_{4-17}$cycloalkylalkylene optionally substituted by 1-6 R$^{69}$, 3-15 membered heterocycloalkylene optionally substituted by 1-6 R$^{69}$, 4-21 membered heterocycloalkylalkylene optionally substituted by 1-6 R$^{69}$, 5-15 membered heteroarylene optionally substituted by 1-6 R$^{69}$, 6-21 membered heteroarylalkylene optionally substituted by 1-6 R$^{69}$, —C(=O)—, —C(=O)O—, —C(=O)NR$^{64}$—, —C(=S)NR$^{64}$—, —NR$^{64}$—, —NR$^{64}$NR$^{64}$—, —NR$^{64}$C(=O)—, —NR$^{64}$C(=O)O—, —NR$^{64}$C(=O)NR$^{64}$—, —NR$^{64}$C(=O)NR$^{64}$C(=O)—, —NR$^{64}$C(=NR$^{65}$)NR$^{64}$—, —NR—, —NR—, —NR$^{64}$S(=O)$_2$—, —O—, —OC(=O)—, —OC(=O)NR$^{64}$—, —S(=O)$_n$—, —S(=O)$_2$NR$^{64}$—, or absent. In another embodiment, G$^4$ is C$_{1-6}$alkylene optionally substituted by 1-6 R$^{69}$, C$_{6-11}$arylene optionally substituted by 1-6 R$^{69}$, C$_{7-16}$arylalkylene optionally substituted by 1-6 R$^{69}$, C$_{3-11}$cycloalkylene optionally substituted by 1-6 R$^{69}$, C$_{4-17}$cycloalkylalkylene optionally substituted by 1-6 R$^{69}$, 3-15 membered heterocycloalkylene optionally substituted by 1-6 R$^{69}$, 4-21 membered heterocycloalkylalkylene optionally substituted by 1-6 R$^{69}$, 5-15 membered heteroarylene optionally substituted by 1-6 R$^{69}$, 6-21 membered heteroarylalkylene optionally substituted by 1-6 R$^{69}$, —C(=O)—, —C(=O)O—, —C(=O)NR$^{64}$—, —C(=S)NR$^{64}$—, —NR$^{64}$—, —NR$^{64}$C(=O)—, —NR$^{64}$C(=O)O—, —NR—, —NR$^{64}$C(=O)NR$^{64}$—, —NR$^{64}$C(=S)—, —NR$^{64}$S(=O)$_2$—, —O—, —OC(=O)—, —OC(=O)NR$^{64}$—, —S(=O)$_n$—, —S(=O)$_2$NR$^{64}$—, or absent. In another embodiment, G$^4$ is C$_{1-6}$alkylene optionally substituted by 1-6 R$^{69}$, C$_{6-11}$arylene optionally substituted by 1-6 R$^{69}$, C$_{3-11}$cycloalkylene optionally substituted by 1-6 R$^{69}$, 3-15 membered heterocycloalkylene optionally substituted by 1-6 R$^{69}$, 5-15 membered heteroarylene optionally substituted by 1-6 R$^{69}$, —C(=O)—, —C(=O)O—, —C(=O)NR$^{64}$—, —NR$^{64}$—, —NR$^{64}$C(=O)—, —NR$^{64}$C(=O)O—, —NR$^{64}$C(=O)NR$^{64}$—, —NR$^{64}$S(=O)$_2$—, —O—, —OC(=O)—, —OC(=O)NR$^{64}$—, —S(=O)$_n$—, —S(=O)$_2$NR$^{64}$—, or absent. In another embodiment, G$^4$ is C$_{1-6}$alkylene optionally substituted by 1-3 R$^{69}$, C$_{6-11}$arylene optionally substituted by 1-3 R$^{69}$, C$_{3-6}$cycloalkylene optionally substituted by 1-3 R$^{69}$, 3-6 membered heterocycloalkylene optionally substituted by 1-3 R$^{69}$, 5-6 membered heteroarylene optionally substituted by 1-3 R$^{69}$, —C(=O)—, —C(=O)O—, —C(=O)NR$^{64}$—, —NR$^{64}$—, —NR$^{64}$C(=O)—, —NR$^{64}$C(=O)O—, —NR$^{64}$C(=O)NR$^{64}$—, —NR$^{64}$S(=O)$_2$—, —O—, —OC(=O)—, —OC(=O)NR$^{64}$—, —S(=O)$_n$—, —S(=O)$_2$NR$^{64}$—, or absent. In another embodiment, G$^4$ is C$_{1-6}$alkylene optionally substituted by 1-3 R$^{69}$, phenylene optionally substituted by 1-3 R$^{69}$, C$_{3-6}$cycloalkylene optionally substituted by 1-3 R$^{69}$, 3-6 membered heterocycloalkylene optionally substituted by 1-3 R$^{69}$, 5-6 membered heteroarylene optionally substituted by 1-3 R$^{69}$, —C(=O)—, —C(=O)O—, —C(=O)NR$^{64}$—, —NR$^{64}$—, —NR$^{64}$C(=O)—, —NR$^{64}$C(=O)O—, —NR$^{64}$C(=O)NR$^{64}$—, —NR$^{64}$S(=O)$_2$—, —O—, —OC(=O)—, —OC(=O)NR$^{64}$—, —S(=O)$_n$—, —S(=O)$_2$NR$^{64}$—, or absent. In another embodiment, G$^4$ is phenylene optionally substituted by 1-3 R$^{69}$, 5-6 membered heteroarylene optionally substituted by 1-3 R$^{69}$, —C(=O)—, —C(=O)O—, —C(=O)NR$^{64}$—, —NR$^{64}$—, —NR$^{64}$C(=O)—, —NR$^{64}$C(=O)O—, —NR$^{64}$C(=O)NR$^{64}$—, —NR$^{64}$S(=O)$_2$—, —O—, —OC(=O)—, —OC(=O)NR$^{64}$—, —S(=O)$_n$—, —S(=O)$_2$NR$^{64}$—, or absent. In another embodiment, G$^4$ is 5-6 membered heteroarylene optionally substituted by 1-3 R$^{69}$, —C(=O)—, —C(=O)O—, —C(=O)NR$^{64}$—, —NR$^{64}$—, —NR$^{64}$C(=O)—, —NR$^{64}$C(=O)O—, —NR$^{64}$C(=O)NR$^{64}$—, —NR$^{64}$S(=O)$_2$—, —O—, —OC(=O)—, —OC(=O)NR$^{64}$—, —S(=O)$_n$—, —S(=O)$_2$NR$^{64}$—, or absent. In another embodiment, G$^4$ is —C$_{0-3}$alkylOC$_{0-3}$alkyl- or absent. In another embodiment, G$^4$ is —O— or absent. In another embodiment, when Q$^2$ and Q$^3$ are each phenyl, then each of the following is true:

(a) L$^4$ is not —O—, —S—, —S(=O), —S(=O)$_2$—, —OC(=O)—, —OC(=O)O—, or —OC(=O)NR$^{44}$—;
(b) G$^4$ is not —O—, —S—, S(=O)—, —S(=O)$_2$—, —OC(=O)—, —OC(=O)O—, or —OC(=O)NR$^{64}$—; and (c) X$^4$ is not —O—, —S—, S(=O)—, —S(=O)$_2$—, —OC(=O)—, —OC(=O)O—, or —OC(=O)NR$^{74}$—. In another embodiment, when Q$^2$ and Q$^3$ are each phenyl, then each of the following is true: (a) L$^4$ is not —O—, —S—, S(=O)—, —S(=O)$_2$—, —OC(=O)—, —OC(=O)O—, or —OC(=O)NR$^{44}$—; (b) when L$^4$ is absent, G$^4$ is not —O—, —S—, —S(=O)—, —S(=O)$_2$—, —OC(=O)—, —OC(=O)O—, or —OC(=O)NR$^{64}$—; and (c) when L$^4$ and G$^4$ are each absent, X$^4$ is not —O—, —S—, —S(=O)—, —S(=O)$_2$—, —OC(=O)—, —OC(=O)O—, or —OC(=O)NR$^{74}$—.

In each embodiment of the present invention that is described in the paragraphs that precede or follow this paragraph, the definition of X$^4$ may be chosen from any of the embodiments that are described in this paragraph. In one embodiment, X$^4$ is C$_{1-6}$alkylene optionally substituted by 1-12 R$^{79}$, C$_{2-6}$alkenylene optionally substituted by 1-10 R$^{79}$, C$_{2-6}$alkynylene optionally substituted by 1-8 R$^{79}$, C$_{6-11}$arylene optionally substituted by 1-10 R$^{79}$, C$_{7-16}$arylalkylene optionally substituted by 1-18 R$^{79}$, C$_{3-11}$ cycloalkylene optionally substituted by 1-20 R$^{79}$, C$_{4-17}$cycloalkylalkylene optionally substituted by 1-31 R$^{79}$, 3-15 membered heterocycloalkylene optionally substituted by 1-27 R$^{79}$, 4-21 membered heterocycloalkylalkylene optionally substituted by 1-39 R$^{79}$, 5-15 membered heteroarylene optionally substituted by 1-14 R$^{79}$, 6-21 membered heteroarylalkylene optionally substituted by 1-26 R$^{79}$, —C$_{0-3}$alkylC(=O)C$_{0-3}$alkyl-, —C$_{0-3}$alkylC(=O)OC$_{0-3}$alkyl-, —C$_{0-3}$alkylC(=O)NR$^{74}$C$_{0-3}$alkyl-, —C$_{0-3}$alkylC(=O)C(=O)C$_{0-3}$alkyl-, —$C_{0-3}$alkylC(=N$R^{75}$)$C_{0-3}$alkyl-, —$C_{0-3}$alkylC(=N$R^{75}$)N$R^{74}$$C_{0-3}$alkyl-, —$C_{0-3}$alkylC(=NOH)N$R^{74}$$C_{0-3}$alkyl-, —$C_{0-3}$alkylC(=NO$R^{76}$)$C_{0-3}$alkyl-, —$C_{0-3}$alkylC(=NN$R^{72}$$R^{73}$)$C_{0-3}$alkyl-, —$C_{0-3}$alkylC(=NN$R^{74}$C(=O)$R^{71}$)$C_{0-3}$alkyl-, —$C_{0-3}$alkylC(=NN$R^{74}$C(=O)O$R^{71}$)$C_{0-3}$alkyl-, —$C_{0-3}$alkylC(=S)N$R^{74}$$C_{0-3}$alkyl-, —$C_{0-3}$alkylN$R^{74}$$C_{0-3}$alkyl-, —$C_{0-3}$alkylN$R^{74}$N$R^{74}$$C_{0-3}$alkyl-, —$C_{0-3}$alkylN=N$C_{0-3}$alkyl-, —$C_{0-3}$alkylN$R^{74}$C(=O)$C_{0-3}$alkyl-, —$C_{0-3}$alkylN$R^{74}$C(=O)C(=O)$C_{0-3}$alkyl-, —$C_{0-3}$alkylN$R^{74}$C(=O)O$C_{0-3}$alkyl-, —$C_{0-3}$alkylN$R^{74}$C(=O)C(=O)O$C_{0-3}$alkyl-, —$C_{0-3}$alkylN$R^{74}$C(=O)N$R^{74}$$C_{0-3}$alkyl-, —$C_{0-3}$alkylN$R^{74}$C(=O)N$R^{74}$C(=O)$C_{0-3}$alkyl-, —$C_{0-3}$alkylN$R^{74}$C(=O)N$R^{74}$C(=O)O$C_{0-3}$alkyl-, —$C_{0-3}$alkylN$R^{74}$C(=N$R^{75}$)N$R^{74}$$C_{0-3}$alkyl-, —$C_{0-3}$alkylN$R^{74}$C(=O)C(=O)N$R^{74}$$C_{0-3}$alkyl-, —$C_{0-3}$alkylN$R^{74}$C(=S)$C_{0-3}$alkyl-, —$C_{0-3}$alkylN$R^{74}$C(=S)O$C_{0-3}$alkyl-, —$C_{0-3}$alkylN$R^{74}$C(=S)N$R^{74}$$C_{0-3}$alkyl-, —$C_{0-3}$alkylN$R^{74}$S(=O)$_2$$C_{0-3}$alkyl-, —$C_{0-3}$alkylN$R^{74}$S(=O)$_2$N$R^{74}$$C_{0-3}$alkyl-, —$C_{0-3}$alkylO$C_{0-3}$alkyl-, —$C_{0-3}$alkylOC(=O)$C_{0-3}$alkyl-, —$C_{0-3}$alkylOC(=O)N$R^{74}$$C_{0-3}$alkyl-, —$C_{0-3}$alkylOC(=O)O$C_{0-3}$alkyl-, —$C_{0-3}$alkylOC(=N$R^{75}$)N$R^{74}$$C_{0-3}$alkyl-, —$C_{0-3}$alkylOS(=O)$C_{0-3}$alkyl-, —$C_{0-3}$alkylOS(=O)$_2$$C_{0-3}$alkyl-, —$C_{0-3}$alkylOS(=O)$_2$O$C_{0-3}$alkyl-, —$C_{0-3}$alkylOS(=O)$_2$N$R^{74}$$C_{0-3}$alkyl-, —$C_{0-3}$alkylS(=O)—$C_{0-3}$alkyl-, —$C_{0-3}$alkylS(=O)$_2$O$C_{0-3}$alkyl-, —$C_{0-3}$alkylSO$_3$$C_{0-3}$alkyl-, —$C_{0-3}$alkylS(=O)$_2$N$R^{74}$$C_{0-3}$alkyl-, —$C_{0-3}$alkylS(=O)N$R^{74}$$C_{0-3}$alkyl-, or absent. In another embodiment, $X^4$ is $C_{1-6}$alkylene optionally substituted by 1-12 $R^{79}$, $C_{6-11}$arylene optionally substituted by 1-6 $R^{79}$, $C_{7-16}$arylalkylene optionally substituted by 1-18 $R^{79}$, $C_{3-11}$cycloalkylene optionally substituted by 1-20 $R^{79}$, $C_{4-17}$cycloalkylalkylene optionally substituted by 1-31 $R^{79}$, 3-15 membered heterocycloalkylene optionally substituted by 1-27 $R^{79}$, 4-21 membered heterocycloalkylalkylene optionally substituted by 1-39 $R^{79}$, 5-15 membered heteroarylene optionally substituted by 1-14 $R^{79}$, 6-21 membered heteroarylalkylene optionally substituted by 1-26 $R^{79}$, —$C_{0-3}$alkylC(=O)$C_{0-3}$alkyl-, —$C_{0-3}$alkylC(=O)O$C_{0-3}$alkyl-, —$C_{0-3}$alkylC(=O)N$R^{74}$$C_{0-3}$alkyl-, —$C_{0-3}$alkylC(=O)C(=O)$C_{0-3}$alkyl-, —$C_{0-3}$alkylC(=S)N$R^{74}$$C_{0-3}$alkyl-, —$C_{0-3}$alkylN$R^{74}$$C_{0-3}$alkyl-, —$C_{0-3}$alkylN$R^{74}$N$R^{74}$$C_{0-3}$alkyl-, —$C_{0-3}$alkylN$R^{74}$C(=O)$C_{0-3}$alkyl-, —$C_{0-3}$alkylN$R^{74}$C(=O)C(=O)$C_{0-3}$alkyl-, —$C_{0-3}$alkylN$R^{74}$C(=O)O$C_{0-3}$alkyl-, —$C_{0-3}$alkylN$R^{74}$C(=O)C(=O)O$C_{0-3}$alkyl-, —$C_{0-3}$alkylN$R^{74}$C(=O)N$R^{74}$$C_{0-3}$alkyl-, —$C_{0-3}$alkylN$R^{74}$C(=O)N$R^{74}$C(=O)$C_{0-3}$alkyl-, —$C_{0-3}$alkylN$R^{74}$C(=O)N$R^{74}$C(=O)O$C_{0-3}$alkyl-, —$C_{0-3}$alkylN$R^{74}$C(=N$R^{75}$)N$R^{74}$$C_{0-3}$alkyl-, —$C_{0-3}$alkylN$R^{74}$C(=O)C(=O)N$R^{74}$$C_{0-3}$alkyl-, —$C_{0-3}$alkylN$R^{74}$C(=S)$C_{0-3}$alkyl-, —$C_{0-3}$alkylN$R^{74}$C(=S)O$C_{0-3}$alkyl-, —$C_{0-3}$alkylN$R^{74}$C(=S)N$R^{74}$$C_{0-3}$alkyl-, —$C_{0-3}$alkylN$R^{74}$S(=O)$_2$$C_{0-3}$alkyl-, —$C_{0-3}$alkylN$R^{74}$S(=O)$_2$N$R^{74}$$C_{0-3}$alkyl-, —$C_{0-3}$alkylO$C_{0-3}$alkyl-, —$C_{0-3}$alkylOC(=O)$C_{0-3}$alkyl-, —$C_{0-3}$alkylOC(=O)N$R^{74}$$C_{0-3}$alkyl-, —$C_{0-3}$alkylOC(=O)O$C_{0-3}$alkyl-, —$C_{0-3}$alkylOS(=O)$C_{0-3}$alkyl-, —$C_{0-3}$alkylOS(=O)$_2$$C_{0-3}$alkyl-, —$C_{0-3}$alkylOS(=O)$_2$O$C_{0-3}$alkyl-, —$C_{0-3}$alkylOS(=O)$_2$N$R^{74}$$C_{0-3}$alkyl-, —$C_{0-3}$alkylS(=O)—$C_{0-3}$alkyl-, —$C_{0-3}$alkylS(=O)$_2$O$C_{0-3}$alkyl-, —$C_{0-3}$alkylSO$_3$$C_{0-3}$alkyl-, —$C_{0-3}$alkylS(=O)$_2$N$R^{74}$$C_{0-3}$alkyl-, —$C_{0-3}$alkylS(=O)N$R^{74}$$C_{0-3}$alkyl-, or absent. In another embodiment, $X^4$ is $C_{1-6}$alkylene optionally substituted by 1-12 $R^{79}$, $C_{6-11}$arylene optionally substituted by 1-6 $R^{79}$, $C_{7-16}$arylalkylene optionally substituted by 1-18 $R^{79}$, $C_{3-11}$cycloalkylene optionally substituted by 1-20 $R^{79}$, $C_{4-17}$cycloalkylalkylene optionally substituted by 1-31 $R^{79}$, 3-15 membered heterocycloalkylene optionally substituted by 1-27 $R^{79}$, 4-21 membered heterocycloalkylalkylene optionally substituted by 1-39 $R^{79}$, 5-15 membered heteroarylene optionally substituted by 1-14 $R^{79}$, 6-21 membered heteroarylalkylene optionally substituted by 1-26 $R^{79}$, —$C_{0-3}$alkylC(=O)$C_{0-3}$alkyl-, —$C_{0-3}$alkylC(=O)O$C_{0-3}$alkyl-, —$C_{0-3}$alkylC(=O)N$R^{74}$$C_{0-3}$alkyl-, —$C_{0-3}$alkylC(=S)N$R^{74}$$C_{0-3}$alkyl-, —$C_{0-3}$alkylN$R^{74}$$C_{0-3}$alkyl-, —$C_{0-3}$alkylN$R^{74}$C(=O)$C_{0-3}$alkyl-, —$C_{0-3}$alkylN$R^{74}$C(=O)O$C_{0-3}$alkyl-, —$C_{0-3}$alkylN$R^{74}$C(=O)N$R^{74}$$C_{0-3}$alkyl-, —$C_{0-3}$alkylN$R^{74}$C(=O)N$R^{74}$C(=O)$C_{0-3}$alkyl-, —$C_{0-3}$alkylN$R^{74}$C(=O)N$R^{74}$C(=O)O$C_{0-3}$alkyl-, —$C_{0-3}$alkylN$R^{74}$C(=N$R^{75}$)N$R^{74}$$C_{0-3}$alkyl-, —$C_{0-3}$alkylN$R^{74}$C(=S)$C_{0-3}$alkyl-, —$C_{0-3}$alkylN$R^{74}$C(=S)N$R^{74}$$C_{0-3}$alkyl-, —$C_{0-3}$alkylN$R^{74}$S(=O)$_2$$C_{0-3}$alkyl-, —$C_{0-3}$alkylO$C_{0-3}$alkyl-, —$C_{0-3}$alkylOC(=O)$C_{0-3}$alkyl-, —$C_{0-3}$alkylOC(=O)N$R^{74}$$C_{0-3}$alkyl-, —$C_{0-3}$alkylS(=O)—$C_{0-3}$alkyl-, —$C_{0-3}$alkylS(=O)$_2$N$R^{74}$$C_{0-3}$alkyl-, or absent. In another embodiment, $X^4$ is $C_{1-6}$alkylene optionally substituted by 1-12 $R^{79}$, $C_{6-11}$arylene optionally substituted by 1-6 $R^{79}$, $C_{3-11}$cycloalkylene optionally substituted by 1-20 $R^{79}$, 3-15 membered heterocycloalkylene optionally substituted by 1-27 $R^{79}$, 5-15 membered heteroarylene optionally substituted by 1-14 $R^{79}$, —$C_{0-3}$alkylC(=O)$C_{0-3}$alkyl-, —$C_{0-3}$alkylC(=O)O$C_{0-3}$alkyl-, —$C_{0-3}$alkylC(=O)N$R^{74}$$C_{0-3}$alkyl-, —$C_{0-3}$alkylN$R^{74}$$C_{0-3}$alkyl-, —$C_{0-3}$alkylN$R^{74}$C(=O)$C_{0-3}$alkyl-, —$C_{0-3}$alkylN$R^{74}$C(=O)O$C_{0-3}$alkyl-, —$C_{0-3}$alkylN$R^{74}$C(=O)N$R^{74}$$C_{0-3}$alkyl-, —$C_{0-3}$alkylS(=O)$_2$$C_{0-3}$alkyl-, —$C_{0-3}$alkylO$C_{0-3}$alkyl-, —$C_{0-3}$alkylOC(=O)$C_{0-3}$alkyl-, —$C_{0-3}$alkylOC(=O)N$R^{74}$$C_{0-3}$alkyl-, —$C_{0-3}$alkylS(=O)$_n$$C_{0-3}$alkyl-, —$C_{0-3}$alkylS(=O)$_2$N$R^{74}$$C_{0-3}$alkyl-, or absent. In another embodiment, $X^4$ is $C_{1-6}$alkylene optionally substituted by 1-6 $R^{79}$, $C_{6-11}$arylene optionally substituted by 1-6 $R^{79}$, $C_{7-16}$arylalkylene optionally substituted by 1-6 $R^{79}$, $C_{3-11}$cycloalkylene optionally substituted by 1-6 $R^{79}$, $C_{4-17}$cycloalkylalkylene optionally substituted by 1-6 $R^{79}$, 3-15 membered heterocycloalkylene optionally substituted by 1-6 $R^{79}$, 4-21 membered heterocycloalkylalkylene optionally substituted by 1-6 $R^{79}$, 5-15 membered heteroarylene optionally substituted by 1-6 $R^{79}$, 6-21 membered heteroarylalkylene optionally substituted by 1-6 $R^{79}$, —C(=O)—, —C(=O)O—, —C(=O)N$R^{74}$—, —C(=O)C(=O)—, —C(=S)N$R^{74}$—, —N$R^{74}$—, —N$R^{74}$N$R^{74}$—, —N$R^{74}$C(=O)—, —N$R^{74}$C(=O)C(=O)—, —N$R^{74}$C(=O)O—, —N$R^{74}$C(=O)C(=O)O—, —N$R^{74}$C(=O)N$R^{74}$—, —N$R^{74}$C(=O)N$R^{74}$C(=O)—, —N$R^{74}$C(=O)N$R^{74}$C(=O)O—, —N$R^{74}$C(=N$R^{75}$)N$R^{74}$—, —N=—, —N$R^{74}$C(=S)—, —N$R^{74}$C(=S)O—, —N$R^{74}$C(=S)N$R^{74}$—, —N$R^{74}$S(=O)$_2$—, —N$R^{74}$S (=O)₂NR⁷⁴—, —O—, —OC(=O)—, —OC(=O)NR⁷⁴—, —OC(=O)O—, —OS(=O)—, —OS(=O)₂—, —OS(=O)₂O—, —OS(=O)₂NR⁷⁴—, —S(=O)ₙ—, —S(=O)₂O—, —SO₃—, —S(=O)₂NR⁷⁴—, —S(=O)NR⁷⁴—, or absent. In another embodiment, X⁴ is C₁₋₆alkylene optionally substituted by 1-6 R⁷⁹, C₆₋₁₁ arylene optionally substituted by 1-6 R⁷⁹, C₇₋₁₆arylalkylene optionally substituted by 1-6 R⁷⁹, C₃₋₁₁cycloalkylene optionally substituted by 1-6 R⁷⁹, C₄₋₁₇cycloalkylalkylene optionally substituted by 1-6 R⁷⁹, 3-15 membered heterocycloalkylene optionally substituted by 1-6 R⁷⁹, 4-21 membered heterocycloalkylalkylene optionally substituted by 1-6 R⁷⁹, 5-15 membered heteroarylene optionally substituted by 1-6 R⁷⁹, 6-21 membered heteroarylalkylene optionally substituted by 1-6 R⁷⁹, —C(=O)—, —C(=O)O—, —C(=O)NR⁷⁴—, —C(=S)NR⁷⁴—, —NR—, —NR⁷⁴NR⁷⁴—, —NR⁷⁴C(=O)—, —NR⁷⁴C(=O)O—, —NR—, —NR⁷⁴C(=O)NR⁷⁴C(=O)—, —NR⁷⁴C(=O)NR⁷⁴C(=O)O—, —NR⁷⁴C(=NR⁷⁵)NR⁷⁴—, —NR⁷⁴C(=S)—, —NR⁷⁴C(=S)NR⁷⁴—, —NR⁷⁴S(=O)₂—, —O—, —OC(=O)—, —OC(=O)NR⁷⁴—, —S(=O)ₙ—, —S(=O)₂NR⁷⁴—, or absent. In another embodiment, X⁴ is C₁₋₆alkylene optionally substituted by 1-6 R⁷⁹, C₆₋₁₁ arylene optionally substituted by 1-6 R⁷⁹, C₇₋₁₆arylalkylene optionally substituted by 1-6 R⁷⁹, C₃₋₁₁cycloalkylene optionally substituted by 1-6 R⁷⁹, C₄₋₆cycloalkylalkylene optionally substituted by 1-6 R⁷⁹, 3-15 membered heterocycloalkylene optionally substituted by 1-6 R⁷⁹, 4-21 membered heterocycloalkylalkylene optionally substituted by 1-6 R⁷⁹, 5-15 membered heteroarylene optionally substituted by 1-6 R⁷⁹, 6-21 membered heteroarylalkylene optionally substituted by 1-6 R⁷⁹, —C(=O)—, —C(=O)O—, —C(=O)NR⁷⁴—, —C(=S)NR⁷⁴—, —NR⁷⁴—, —NR⁷⁴C(=O)—, —NR⁷⁴C(=O)O—, —NR⁷⁴C(=O)NR⁷⁴—, —NR⁷⁴C(=O)NR⁷⁴C(=O)—, —NR⁷⁴C(=O)NR⁷⁴C(=O)O—, —NR⁷⁴C(=S)—, —NR⁷⁴S(=O)₂—, —O—, —OC(=O)—, —OC(=O)NR⁷⁴—, —S(=O)ₙ—, —S(=O)₂NR⁷⁴—, or absent. In another embodiment, X⁴ is C₁₋₆alkylene optionally substituted by 1-6 R⁷⁹, C₆₋₁₁ arylene optionally substituted by 1-6 R⁷⁹, C₃₋₁₁cycloalkylene optionally substituted by 1-6 R⁷⁹, 3-15 membered heterocycloalkylene optionally substituted by 1-6 R⁷⁹, 5-15 membered heteroarylene optionally substituted by 1-6 R⁷⁹, —C(=O)—, —C(=O)O—, —C(=O)NR⁷⁴—, —NR⁷⁴—, —NR⁷⁴C(=O)—, —NR⁷⁴C(=O)O—, —NR⁷⁴C(=O)NR⁷⁴—, —NR⁷⁴S(=O)₂—, —O—, —OC(=O)—, —OC(=O)NR⁷⁴—, —S(=O)ₙ—, —S(=O)₂NR⁷⁴—, or absent. In another embodiment, X⁴ is C₁₋₆alkylene optionally substituted by 1-3 R⁷⁹, C₆₋₁₁arylene optionally substituted by 1-3 R⁷⁹, C₃₋₆cycloalkylene optionally substituted by 1-3 R⁷⁹, 3-6 membered heterocycloalkylene optionally substituted by 1-3 R⁷⁹, 5-6 membered heteroarylene optionally substituted by 1-3 R⁷⁹, —C(=O)—, —C(=O)O—, —C(=O)NR⁷⁴—, —NR⁷⁴—, —NR⁷⁴C(=O)—, —NR⁷⁴C(=O)O—, —NR⁷⁴C(=O)NR⁷⁴—, —NR⁷⁴S(=O)₂—, —O—, —OC(=O)—, —OC(=O)NR⁷⁴—, —S(=O)ₙ—, —S(=O)₂NR⁷⁴—, or absent. In another embodiment, X⁴ is C₁₋₆alkylene optionally substituted by 1-3 R⁷⁹, phenylene optionally substituted by 1-3 R⁷⁹, C₃₋₆cycloalkylene optionally substituted by 1-3 R⁷⁹, 3-6 membered heterocycloalkylene optionally substituted by 1-3 R⁷⁹, 5-6 membered heteroarylene optionally substituted by 1-3 R⁷⁹, —C(=O)—, —C(=O)O—, —C(=O)NR⁷⁴—, —NR⁷⁴—, —NR⁷⁴C(=O)—, —NR⁷⁴C(=O)O—, —NR⁷⁴C(=O)NR⁷⁴—, —NR⁷⁴S(=O)₂—, —O—, —OC(=O)—, —OC(=O)NR⁷⁴—, —S(=O)ₙ—, —S(=O)₂NR⁷⁴—, or absent. In another embodiment, X⁴ is phenylene optionally substituted by 1-3 R⁷⁹, 5-6 membered heteroarylene optionally substituted by 1-3 R⁷⁹, —C(=O)—, —C(=O)O—, —C(=O)NR⁷⁴—, —NR⁷⁴—, —NR⁷⁴C(=O)—, —NR⁷⁴C(=O)O—, —NR⁷⁴C(=O)NR⁷⁴—, —NR⁷⁴S(=O)₂—, —O—, —OC(=O)—, —OC(=O)NR⁷⁴—, —S(=O)ₙ—, —S(=O)₂NR⁷⁴—, or absent. In another embodiment, X⁴ is absent. In another embodiment, when Q² and Q³ are each phenyl, then each of the following is true: (a) L⁴ is not —O—, —S—, —S(=O)—, —S(=O)₂—, —OC(=O)—, —OC(=O)O—, or —OC(=O)NR⁴⁴—; (b) G⁴ is not —O—, —S—, —S(=O)—, —S(=O)₂—, —OC(=O)—, —OC(=O)O—, or —OC(=O)NR⁶⁴—; and (c) X⁴ is not —O—, —S—, S(=O)—, —S(=O)₂—, —OC(=O)—, —OC(=O)O—, or —OC(=O)NR⁷⁴—. In another embodiment, when Q² and Q³ are each phenyl, then each of the following is true:

(a) L⁴ is not —O—, —S—, —S(=O)—, —S(=O)₂, —OC(=O)—, —OC(=O)O—, or —OC(=O)NR⁴⁴—;

(b) when L⁴ is absent, G⁴ is not —O—, —S—, S(=O)—, —S(=O)₂—, —OC(=O)—, —OC(=O)O—, or —OC(=O)NR⁶⁴—; and (c) when L⁴ and G⁴ are each absent, X⁴ is not —O—, —S—, —S(=O)—, —S(=O)₂—, —OC(=O)—, —OC(=O)O—, or —OC(=O)NR⁷⁴—.

In each embodiment of the present invention that is described in the paragraphs that precede or follow this paragraph, the definition of Z⁴ may be chosen from any of the embodiments that are described in this paragraph. In one embodiment, Z⁴ is H, C₁₋₆alkyl optionally substituted by 1-13 R⁸⁹, C₂₋₆alkenyl optionally substituted by 1-11 R⁸⁹, C₂₋₆alkynyl optionally substituted by 1-9 R⁸⁹, C₆₋₁₁aryl optionally substituted by 1-11 R⁸⁹, C₇₋₁₆arylalkyl optionally substituted by 1-19 R⁸⁹, C₃₋₁₁cycloalkyl optionally substituted by 1-21 R⁸⁹, C₄₋₁₇cycloalkylalkyl optionally substituted by 1-32 R⁸⁹, 3-15 membered heterocycloalkyl optionally substituted by 1-28 R⁸⁹, 4-21 membered heterocycloalkylalkyl optionally substituted by 1-40 R⁸⁹, 5-15 membered heteroaryl optionally substituted by 1-15 R⁸⁹, 6-21 membered heteroarylalkyl optionally substituted by 1-27 R⁸⁹, halogen, —CN, —C(=O)R⁸⁰, —C(=O)OR⁸⁰, —C(=O)NR⁸²R⁸³, —C(=O)C(=O)R⁸⁰, —C(=NR⁸⁵)R⁸⁰, —C(=NR⁸⁵)NR⁸²R⁸³, —C(=NOH)NR⁸²R⁸³, —C(=NOR⁸⁶)R⁸⁰, —C(=NNR⁸²R⁸³)R⁸⁰, —C(=NNR⁸⁴C(=O)R⁸¹)R⁸⁰, —C(=NNR⁸⁴C(=O)OR⁸¹)R⁸⁰, —C(=S)NR⁸²R⁸³, —NC, —NO₂, —NR⁸²R⁸³, —NR⁸⁴NR⁸²R⁸³, —N=NR⁸⁴, =NR⁸⁰, =NOR⁸⁰, —NR⁸⁴OR⁸⁶, —NR⁸⁴C(=O)R⁸⁰, —NR⁸⁴C(=O)C(=O)R⁸⁰, —NR⁸⁴C(=O)OR⁸¹, —NR⁸⁴C(=O)C(=O)OR⁸¹, —NR⁸⁴C(=O)NR⁸²R⁸³, —NR⁸⁴C(=O)NR⁸⁴C(=O)R⁸⁰, —NR⁸⁴C(=O)NR⁸⁴C(=O)OR⁸⁰, —NR⁸⁴C(=NR⁸⁵)NR⁸²R⁸³, —NR⁸⁴C(=O)C(=O)NR⁸²R⁸³, —NR⁸⁴C(=S)R⁸⁰, —NR⁸⁴C(=S)OR⁸⁰, —NR⁸⁴C(=S)NR⁸²R⁸³, —NR⁸⁴S(=O)₂R⁸¹, —NR⁸⁴S(=O)₂NR⁸²R⁸³, —NR⁸⁴P(=O)R⁸⁸R⁸⁸, —NR⁸⁴P(=O)(NR⁸²R⁸³)(NR⁸²R⁸³), —NR⁸⁴P(=O)(OR⁸⁰)(OR⁸⁰), —NR⁸⁴P(=O)(SR⁸⁰)(SR⁸⁰), —OR⁸⁰, =O, —OCN, —OC(=O)R⁸⁰, —OC(=O)NR⁸²R⁸³, —OC(=O)OR⁸⁰, —OC(=NR⁸⁵)NR⁸²R⁸³, —OS(=O)R⁸⁰, —OS(=O)₂R⁸⁰, —OS(=O)₂OR⁸⁰, —OS(=O)₂NR⁸²R⁸³, —OP(=O)R⁸⁸R⁸⁸, —OP(=O)(NR⁸²R⁸³)(NR⁸²R⁸³), —OP(=O)(OR⁸⁰)(OR⁸⁰), —OP(=O)(SR⁸⁰)(SR⁸⁰), —SCN, =S, —S(=O)ₙR⁸⁰, —S(=O)₂OR⁸⁰, —SO₃R⁸⁷, —S(=O)₂NR⁸²R⁸³, —S(=O)NR⁸²R⁸³, —SP(=O)R⁸⁸R⁸⁸, —SP(=O)(NR⁸²R⁸³)(NR⁸²R⁸³), —SP(=O)(OR⁸⁰)(OR⁸⁰), —SP(=O)(SR⁸⁰)(SR⁸⁰), —P(=O)R⁸⁸R⁸⁸, —P(=O)(NR⁸²R⁸³)(NR⁸²R⁸³), —P(=O)(OR⁸⁰)(OR⁸⁰), or —P(=O)(SR⁸⁰)(SR⁸⁰); alternatively, when L³, A³, G³, X³, L⁴, A⁴, G⁴ and X⁴ are absent, Z³ and Z⁴ can together form a group of formula -A²¹-A²²-A²³-; wherein A²¹, A²², and A²³ are independently chosen from —CZ²¹Z²²—, —CZ$^{23}$Z$^{24}$CZ$^{25}$Z$^{26}$—, —C(=O)—, —NZ$^{27}$-, —S—, —S(=O)—, —S(=O)$_2$—, or —O—; wherein:

(a) when any two of Z$^{21}$, Z$^{22}$, Z$^{23}$, Z$^{24}$, Z$^{25}$, Z$^{26}$ and Z$^{27}$ are located on adjacent atoms, they may together form a bond between the atoms, and (b) any of Z$^{21}$, Z$^{22}$, Z$^{23}$, Z$^{24}$, Z$^{25}$, Z$^{26}$ and Z$^{27}$ may be independently chosen from H, C$_{1-6}$alkyl optionally substituted by 1-13 R$^{99}$, C$_{2-6}$alkenyl optionally substituted by 1-11 R$^{99}$, C$_{2-6}$alkynyl optionally substituted by 1-9 R$^{99}$, C$_{6-11}$ aryl optionally substituted by 1-11 R$^{99}$, C$_{7-16}$arylalkyl optionally substituted by 1-19 R$^{99}$, C$_{3-11}$cycloalkyl optionally substituted by 1-21 R$^{99}$, C$_{4-17}$cycloalkylalkyl optionally substituted by 1-32 R$^{99}$, 3-15 membered heterocycloalkyl optionally substituted by 1-28 R$^{99}$, 4-21 membered heterocycloalkylalkyl optionally substituted by 1-40 R$^{99}$, 5-15 membered heteroaryl optionally substituted by 1-15 R$^{99}$, 6-21 membered heteroarylalkyl optionally substituted by 1-27 R$^{99}$, halogen, —CN, —C(=O)R$^{90}$, —C(=O)OR$^{90}$, —C(=O)NR$^{92}$R$^{93}$, —C(=O)C(=O)R$^{90}$, —C(=NR$^{95}$)R$^{90}$, —C(=NR$^{95}$)NR$^{92}$R$^{93}$, —C(=NOH)NR$^{92}$R$^{93}$, —C(=NOR$^{96}$)R$^{90}$, —C(=NNR$^{92}$R$^{93}$)R$^{90}$, —C(=NNR$^{94}$C(=O)R$^{91}$)R$^{90}$, —C(=NNR$^{94}$C(=O)OR$^{91}$)R$^{90}$, —C(=S)NR$^{92}$R$^{93}$, —NC, —NO$_2$, —NR$^{92}$R$^{93}$, —NR$^{94}$NR$^{92}$R$^{93}$, —N=NR$^{94}$, —NR$^{90}$, =NOR$^{90}$, —NR$^{94}$OR$^{96}$, —NR$^{94}$C(=O)R$^{90}$, —NR$^{94}$C(=O)C(=O)R$^{90}$, —NR$^{94}$C(=O)OR$^{91}$, —NR$^{94}$C(=O)C(=O)OR$^{91}$, —NR$^{94}$C(=O)NR$^{92}$R$^{93}$, —NR$^{94}$C(=O)NR$^{94}$C(=O)R$^{90}$, —NR$^{94}$C(=O)NR$^{94}$C(=O)OR$^{90}$, —NR$^{94}$C(=NR$^{95}$)NR$^{92}$R$^{93}$, —NR$^{94}$C(=O)C(=O)NR$^{92}$R$^{93}$, —NR$^{94}$C(=S)R$^{90}$, —NR$^{94}$C(=NR$^{95}$)NR$^{92}$R$^{93}$, —NR$^{94}$S(=O)$_2$R$^{91}$, —NR$^{94}$S(=O)$_2$NR$^{92}$R$^{93}$, —NR$^{94}$P(=O)R$^{98}$R$^{98}$, —NR$^{94}$P(=O)(NR$^{92}$R$^{93}$)(NR$^{92}$R$^{93}$), —NR$^{94}$P(=O)(OR$^{90}$)(OR$^{90}$), —NR$^{94}$P(=O)(SR$^{90}$)(SR$^{90}$), —OR$^{90}$, =O, —OCN, —OC(=O)R$^{90}$, —OC(=O)NR$^{92}$R$^{93}$, —OC(=O)OR$^{90}$, —OC(=NR$^{95}$)NR$^{92}$R$^{93}$, —OS(=O)R$^{90}$, —OS(=O)$_2$R$^{90}$, —OS(=O)$_2$OR$^{90}$, —OS(=O)$_2$NR$^{92}$R$^{93}$, —OP(=O)R$^{98}$R$^{98}$, —OP(=O)(NR$^{92}$R$^{93}$)(NR$^{92}$R$^{93}$), —OP(=O)(OR$^{90}$)(OR$^{90}$), —OP(=O)(SR$^{90}$)(SR$^{90}$), —SCN, =S, —S(=O)$_n$R$^{90}$, —S(=O)$_2$OR$^{90}$, —SO$_3$R$^{97}$, —S(=O)$_2$NR$^{92}$R$^{93}$, —S(=O)NR$^{92}$R$^{93}$, —SP(=O)R$^{98}$R$^{98}$, —SP(=O)(NR$^{92}$R$^{93}$)(NR$^{92}$R$^{93}$), —SP(=O)(OR$^{90}$)(OR$^{90}$), —SP(=O)(SR$^{90}$)(SR$^{90}$), —P(=O)R$^{98}$R$^{98}$, —P(=O)(NR$^{92}$R$^{93}$)(NR$^{92}$R$^{93}$), —P(=O)(OR$^{90}$)(OR$^{90}$), and —P(=O)(SR$^{90}$)(SR$^{90}$); and (c) any two of Z$^{21}$, Z$^{22}$, Z$^{23}$, Z$^{24}$, Z$^{25}$, Z$^{26}$ and Z$^{27}$ may together form a group of formula -A$^{31}$-A$^{32}$-A$^{33}$-, wherein A$^{31}$, A$^{32}$, and A$^{33}$ are independently chosen from —CZ$^{31}$Z$^{32}$—, —CZ$^{33}$Z$^{34}$CZ$^{35}$Z$^{36}$—, —C(=O)—, —NZ$^{37}$—, —S—, —S(=O)—, —S(=O)$_2$—, or —O— wherein:

(i) when any two of Z$^{31}$, Z$^{32}$, Z$^{33}$, Z$^{34}$, Z$^{35}$, Z$^{36}$ and Z$^{37}$ are located on adjacent atoms, they may together form a bond between the atoms, and (ii) any of any of Z$^{21}$, Z$^{22}$, Z$^{23}$, Z$^{24}$, Z$^{25}$, Z$^{26}$ and Z$^{27}$ may be independently chosen from H, C$_{1-6}$alkyl optionally substituted by 1-13 R$^{139}$, C$_{2-6}$alkenyl optionally substituted by 1-11 R$^{139}$, C$_{2-6}$alkynyl optionally substituted by 1-9 R$^{139}$, C$_{6-11}$ aryl optionally substituted by 1-11 R$^{139}$, C$_{7-16}$arylalkyl optionally substituted by 1-19 R$^{139}$, C$_{3-11}$cycloalkyl optionally substituted by 1-21 R$^{139}$, C$_{4-17}$cycloalkylalkyl optionally substituted by 1-32 R$^{139}$, 3-15 membered heterocycloalkyl optionally substituted by 1-28 R$^{139}$, 4-21 membered heterocycloalkylalkyl optionally substituted by 1-40 R$^{139}$, 5-15 membered heteroaryl optionally substituted by 1-15 R$^{139}$, 6-21 membered heteroarylalkyl optionally substituted by 1-27 R$^{139}$, halogen, —CN, —C(=O)R$^{130}$, —C(=O)OR$^{130}$, —C(=O)NR$^{132}$R$^{133}$, —C(=O)C(=O)R$^{130}$, —C(=NR$^{135}$)R$^{130}$, —C(=NR$^{135}$)NR$^{132}$R$^{133}$, —C(=NOH)NR$^{132}$R$^{133}$, —C(=NOR$^{136}$)R$^{130}$, —C(=NNR$^{132}$R$^{133}$)R$^{130}$, —C(=NNR$^{134}$C(=O)R$^{131}$)R$^{130}$, —C(=NNR$^{134}$C(=O)OR$^{131}$)R$^{130}$, —C(=S)NR$^{132}$R$^{133}$, —NC, —NO$_2$, —NR$^{132}$R$^{133}$, —NR$^{134}$NR$^{132}$R$^{133}$, —N=NR$^{134}$, =NR$^{130}$, =NOR$^{130}$, —NR$^{134}$OR$^{136}$, —NR$^{134}$C(=O)R$^{130}$, —NR$^{134}$C(=O)C(=O)R$^{130}$, —NR$^{134}$C(=O)OR$^{131}$, —NR$^{134}$C(=O)C(=O)OR$^{131}$, —NR$^{134}$C(=O)NR$^{132}$R$^{133}$, —NR$^{134}$C(=O)NR$^{134}$C(=O)R$^{130}$, —NR$^{134}$C(=O)NR$^{134}$C(=O)OR$^{130}$, —NR$^{134}$C(=NR$^{135}$)NR$^{132}$R$^{133}$, —NR$^{134}$C(=O)C(=O)NR$^{132}$R$^{133}$, —NR$^{134}$C(=S)R$^{130}$, —NR$^{134}$C(=S)OR$^{130}$, —NR$^{134}$C(=S)NR$^{132}$R$^{133}$, —NR$^{134}$S(=O)$_2$R$^{131}$, —NR$^{134}$S(=O)$_2$NR$^{132}$R$^{133}$, —NR$^{134}$P(=O)R$^{138}$R$^{138}$, —NR$^{134}$P(=O)(NR$^{132}$R$^{133}$)(NR$^{132}$R$^{133}$), —NR$^{134}$P(=O)(OR$^{130}$)(OR$^{130}$), —NR$^{134}$P(=O)(SR$^{130}$(SR$^{130}$, —OR$^{130}$, =O, —OCN, —OC(=O)R$^{130}$, —OC(=O)NR$^{132}$R$^{133}$, —OC(=O)OR$^{130}$, —OC(=NR$^{135}$)NR$^{132}$R$^{133}$, —OS(=O)R$^{130}$, —OS(=O)$_2$R$^{130}$, —OS(=O)$_2$OR$^{130}$, —OS(=O)$_2$NR$^{132}$R$^{133}$, —OP(=O)R$^{138}$R$^{138}$, —OP(=O)(NR$^{132}$R$^{133}$)(NR$^{132}$R$^{133}$), —OP(=O)(OR$^{130}$)(OR$^{130}$), —OP(=O)(SR$^{130}$)(SR$^{130}$), —SCN, =S, —S(=O)$_n$R$^{130}$, —S(=O)$_2$OR$^{130}$, —SO$_3$R$^{137}$, —S(=O)$_2$NR$^{132}$R$^{133}$, —S(=O)NR$^{132}$R$^{133}$, —SP(=O)R$^{138}$R$^{138}$, —SP(=O)(NR$^{132}$R$^{133}$)(NR$^{132}$R$^{133}$), —SP(=O)(OR$^{130}$)(OR$^{130}$), —SP(=O)(SR$^{130}$)(SR$^{130}$), —P(=O)R$^{138}$R$^{138}$, —P(=O)(NR$^{132}$R$^{133}$)(NR$^{132}$R$^{133}$), —P(=O)(OR$^{130}$)(OR$^{130}$), and —P(=O)(SR$^{130}$)(SR$^{130}$). In another embodiment, Z$^4$ is H, C$_{1-6}$alkyl optionally substituted by 1-13 R$^{89}$, C$_{2-6}$alkenyl optionally substituted by 1-11 R$^{89}$, C$_{2-6}$alkynyl optionally substituted by 1-9 R$^{89}$, C$_{6-11}$aryl optionally substituted by 1-11 R$^{89}$, C$_{7-16}$arylalkyl optionally substituted by 1-19 R$^{89}$, C$_{3-11}$cycloalkyl optionally substituted by 1-21 R$^{89}$, C$_{4-17}$cycloalkylalkyl optionally substituted by 1-32 R$^{89}$, 3-15 membered heterocycloalkyl optionally substituted by 1-28 R$^{89}$, 4-21 membered heterocycloalkylalkyl optionally substituted by 1-40 R$^{89}$, 5-15 membered heteroaryl optionally substituted by 1-15 R$^{89}$, 6-21 membered heteroarylalkyl optionally substituted by 1-27 R$^{89}$, halogen, —CN, —C(=O)R$^{80}$, —C(=O)OR$^{80}$, —C(=O)NR$^{82}$R$^{83}$, —C(=O)C(=O)R$^{80}$, —C(=NR$^{85}$)R$^{80}$, —C(=NR$^{85}$)NR$^{82}$R$^{83}$, —C(=NOH)NR$^{82}$R$^{83}$, —C(=NOR$^{86}$)R$^{80}$, —C(=NNR$^{82}$R$^{83}$)R$^{80}$, —C(=NNR$^{84}$C(=O)R$^{81}$)R$^{80}$, —C(=NNR$^{84}$C(=O)OR$^{81}$)R$^{80}$, —C(=S)NR$^{82}$R$^{83}$, —NC, —NO$_2$, —NR$^{82}$R$^{83}$, —NR$^{84}$NR$^{82}$R$^{83}$, —N=NR$^{84}$, =NR$^{80}$, =NOR$^{80}$, —NR$^{84}$OR$^{86}$, —NR$^{84}$C(=O)R$^{80}$, —NR$^{84}$C(=O)C(=O)R$^{80}$, —NR$^{84}$C(=O)OR$^{81}$, —NR$^{84}$C(=O)C(=O)OR$^{81}$, —NR$^{84}$C(=O)NR$^{82}$R$^{83}$, —NR$^{84}$C(=O)NR$^{84}$C(=O)R$^{80}$, —NR$^{84}$C(=O)NR$^{84}$C(=O)OR$^{80}$, —NR$^{84}$C(=NR$^{85}$)NR$^{82}$R$^{83}$, —NR$^{84}$C(=O)C(=O)NR$^{82}$R$^{83}$, —NR$^{84}$C(=S)R$^{80}$, —NR$^{84}$C(=S)OR$^{80}$, —NR$^{84}$C(=S)NR$^{82}$R$^{83}$, —NR$^{84}$S(=O)$_2$R$^{81}$, —NR$^{84}$S(=O)$_2$NR$^{82}$R$^{83}$, —NR$^{84}$P(=O)R$^{88}$R$^{88}$, —OR$^{80}$, =O, —OCN, —OC(=O)R$^{80}$, —OC(=O)NR$^{82}$R$^{83}$, —OC(=O)OR$^{80}$, —OC(=NR$^{85}$)NR$^{82}$R$^{83}$, —OS(=O)R$^{80}$, —OS(=O)$_2$R$^{80}$, —OS(=O)$_2$OR$^{80}$, —OS(=O)$_2$NR$^{82}$R$^{83}$, —SCN, =S, —S(=O)$_n$R$^{80}$, —S(=O)$_2$OR$^{80}$, —SO$_3$R$^{87}$, —S(=O)$_2$NR$^{82}$R$^{83}$, —S(=O)NR$^{82}$R$^{83}$, or —P(=O)R$^{88}$R$^{88}$;

alternatively, when L$^3$, A$^3$, G$^3$, X$^3$, L$^4$, A$^4$, G$^4$ and X$^4$ are absent, Z$^3$ and Z$^4$ can together form a group of formula -A$^{21}$-A$^{22}$-A$^{23}$-; wherein A$^{21}$, A$^{22}$, and A$^{23}$ are independently chosen from —CZ$^{21}$Z$^{22}$—, —CZ$^{23}$Z$^{24}$CZ$^{25}$Z$^{26}$—, —C(=O)—, —NZ$^{27}$—, —S—, —S(=O)—, —S(=O)$_2$—, or —O—; wherein:

(a) when any two of Z$^{21}$, Z$^{22}$, Z$^{23}$, Z$^{24}$, Z$^{25}$, Z$^{26}$ and Z$^{27}$ are located on adjacent atoms, they may together form a bond between the atoms, and (b) any of $Z^{21}$, $Z^{22}$, $Z^{23}$, $Z^{24}$, $Z^{25}$, $Z^{26}$ and $Z^{27}$ may be independently chosen from H, $C_{1-6}$alkyl optionally substituted by 1-13 $R^{99}$, $C_{2-6}$alkenyl optionally substituted by 1-11 $R^{99}$, $C_{2-6}$alkynyl optionally substituted by 1-9 $R^{99}$, $C_{6-11}$ aryl optionally substituted by 1-11 $R^{99}$, $C_{7-16}$arylalkyl optionally substituted by 1-19 $R^{99}$, $C_{3-11}$cycloalkyl optionally substituted by 1-21 $R^{99}$, $C_{4-17}$cycloalkylalkyl optionally substituted by 1-32 $R^{99}$, 3-15 membered heterocycloalkyl optionally substituted by 1-28 $R^{99}$, 4-21 membered heterocycloalkylalkyl optionally substituted by 1-40 $R^{99}$, 5-15 membered heteroaryl optionally substituted by 1-15 $R^{99}$, 6-21 membered heteroarylalkyl optionally substituted by 1-27 $R^{99}$, halogen, —CN, —C(=O)$R^{90}$, —C(=O)O$R^{90}$, —C(=O)N$R^{92}R^{93}$, —C(=O)C(=O)$R^{90}$, —C(=N$R^{95}$)$R^{90}$, —C(=N$R^{95}$)N$R^{92}R^{93}$, —C(=NOH)N$R^{92}R^{93}$, —C(=NO$R^{96}$)$R^{90}$, —C(=NN$R^{92}R^{93}$)$R^{90}$, —C(=NN$R^{94}$C(=O)$R^{91}$)$R^{90}$, —C(=NN$R^{94}$C(=O)O$R^{91}$)$R^{90}$, —C(=S)N$R^{92}R^{93}$, —NC, —NO$_2$, —N$R^{92}R^{93}$, —N$R^{94}$N$R^{92}R^{93}$, —N=N$R^{94}$, =N$R^{90}$, =NO$R^{90}$, —N$R^{94}$O$R^{96}$, —N$R^{94}$C(=O)$R^{90}$, —N$R^{94}$C(=O)C(=O)$R^{90}$, —N$R^{94}$C(=O)O$R^{91}$, —N$R^{94}$C(=O)C(=O)O$R^{91}$, —N$R^{94}$C(=O)N$R^{92}R^{93}$, —N$R^{94}$C(=O)N$R^{94}$C(=O)$R^{90}$, —N$R^{94}$C(=O)N$R^{94}$C(=O)O$R^{90}$, —N$R^{94}$C(=N$R^{95}$)N$R^{92}R^{93}$, —N$R^{94}$C(=O)C(=O)N$R^{92}R^{93}$, —N$R^{94}$C(=S)$R^{90}$, —N$R^{94}$C(=S)O$R^{90}$, —N$R^{94}$C(=S)N$R^{92}R^{93}$, —N$R^{94}$S(=O)$_2R^{91}$, —N$R^{94}$S(=O)$_2$N$R^{92}R^{93}$, —N$R^{94}$P(=O)$R^{98}R^{98}$, —O$R^{90}$, =O, —OCN, —OC(=O)$R^{90}$, —OC(=O)N$R^{92}R^{93}$, —OC(=O)O$R^{90}$, —OC(=N$R^{95}$)N$R^{92}R^{93}$, —OS(=O)$R^{90}$, —OS(=O)$_2R^{90}$, —OS(=O)$_2$O$R^{90}$, —OS(=O)$_2$N$R^{92}R^{93}$, —SCN, =S, —S(=O)$_nR^{90}$, —S(=O)$_2$O$R^{90}$, —SO$_3R^{97}$, —S(=O)$_2$N$R^{92}R^{93}$, —S(=O)N$R^{92}R^{93}$, and —P(=O)$R^{98}R^{98}$; and (c) any two of $Z^{21}$, $Z^{22}$, $Z^{23}$, $Z^{24}$, $Z^{25}$, $Z^{26}$ and $Z^{27}$ may together form a group of formula -$A^{31}$-$A^{32}$-$A^{33}$-, wherein $A^{31}$, $A^{32}$, and $A^{33}$ are independently chosen from —C$Z^{31}Z^{32}$—, —C$Z^{33}Z^{34}$C$Z^{35}Z^{36}$—, —C(=O)—, —N$Z^{37}$—, —S—, —S(=O)—, —S(=O)$_2$—, or —O— wherein:

(i) when any two of $Z^{31}$, $Z^{32}$, $Z^{33}$, $Z^{34}$, $Z^{35}$, $Z^{36}$ and $Z^{37}$ are located on adjacent atoms, they may together form a bond between the atoms, and (ii) any of any of $Z^{21}$, $Z^{22}$, $Z^{23}$, $Z^{24}$, $Z^{25}$, $Z^{26}$ and $Z^{27}$ may be independently chosen from H, $C_{1-6}$alkyl optionally substituted by 1-13 $R^{139}$, $C_{2-6}$alkenyl optionally substituted by 1-11 $R^{139}$, $C_{2-6}$alkynyl optionally substituted by 1-9 $R^{139}$, $C_{6-11}$ aryl optionally substituted by 1-11 $R^{139}$, $C_{7-16}$arylalkyl optionally substituted by 1-19 $R^{139}$, $C_{3-11}$cycloalkyl optionally substituted by 1-21 $R^{139}$, $C_{4-17}$cycloalkylalkyl optionally substituted by 1-32 $R^{139}$, 3-15 membered heterocycloalkyl optionally substituted by 1-28 $R^{139}$, 4-21 membered heterocycloalkylalkyl optionally substituted by 1-40 $R^{139}$, 5-15 membered heteroaryl optionally substituted by 1-15 $R^{139}$, 6-21 membered heteroarylalkyl optionally substituted by 1-27 $R^{139}$, halogen, —CN, —C(=O)$R^{130}$, —C(=O)O$R^{130}$, —C(=O)N$R^{132}R^{133}$, —C(=O)C(=O)$R^{130}$, —C(=N$R^{135}$)$R^{130}$, —C(=N$R^{135}$)N$R^{132}R^{133}$, —C(=NOH)N$R^{132}R^{133}$, —C(=NO$R^{136}$)$R^{130}$, —C(=NN$R^{132}R^{133}$)$R^{130}$, —C(=NN$R^{134}$C(=O)$R^{131}$)$R^{130}$, —C(=NN$R^{134}$C(=O)O$R^{131}$)$R^{130}$, —C(=S)N$R^{132}R^{133}$, —NC, —NO$_2$, —N$R^{132}R^{133}$, —N$R^{134}$N$R^{132}R^{133}$, —N=N$R^{134}$, =N$R^{130}$, =NO$R^{130}$, —N$R^{134}$O$R^{136}$, —N$R^{134}$C(=O)$R^{130}$, —N$R^{134}$C(=O)C(=O)$R^{130}$, —N$R^{134}$C(=O)O$R^{131}$, —N$R^{134}$C(=O)C(=O)O$R^{131}$, —N$R^{134}$C(=O)N$R^{132}R^{133}$, —N$R^{134}$C(=O)N$R^{134}$C(=O)$R^{130}$, —N$R^{134}$C(=O)N$R^{134}$C(=O)O$R^{130}$, —N$R^{134}$C(=N$R^{135}$)N$R^{132}R^{133}$, —N$R^{134}$C(=O)C(=O)N$R^{132}R^{133}$, —N$R^{134}$C(=S)$R^{130}$, —N$R^{134}$C(=S)O$R^{130}$, —N$R^{134}$C(=S)N$R^{132}R^{133}$, —N$R^{134}$S(=O)$_2R^{131}$, —N$R^{134}$S(=O)$_2$N$R^{132}R^{133}$, —N$R^{134}$P(=O)$R^{138}R^{138}$, —O$R^{130}$, =O, —OCN, —OC(=O)$R^{130}$, —OC(=O)N$R^{132}R^{133}$, —OC(=O)O$R^{130}$, —OC(=N$R^{135}$)N$R^{132}R^{133}$, —OS(=O)$R^{130}$, —OS(=O)$_2R^{130}$, —OS(=O)$_2$O$R^{130}$, —OS(=O)$_2$N$R^{132}R^{133}$, —SCN, =S, —S(=O)$_nR^{130}$, —S(=O)$_2$O$R^{130}$, —SO$_3R^{137}$, —S(=O)$_2$N$R^{132}R^{133}$, —S(=O)N$R^{132}R^{133}$, and —P(=O)$R^{138}R^{138}$. In another embodiment, $Z^4$ is H, $C_{1-6}$alkyl optionally substituted by 1-13 $R^{89}$, $C_{2-6}$alkenyl optionally substituted by 1-11 $R^{89}$, $C_{2-6}$alkynyl optionally substituted by 1-9 $R^{89}$, $C_{6-11}$ aryl optionally substituted by 1-11 $R^{89}$, $C_{7-16}$arylalkyl optionally substituted by 1-19 $R^{89}$, $C_{3-11}$cycloalkyl optionally substituted by 1-21 $R^{89}$, $C_{4-17}$cycloalkylalkyl optionally substituted by 1-32 $R^{89}$, 3-15 membered heterocycloalkyl optionally substituted by 1-28 $R^{89}$, 4-21 membered heterocycloalkylalkyl optionally substituted by 1-40 $R^{89}$, 5-15 membered heteroaryl optionally substituted by 1-15 $R^{89}$, 6-21 membered heteroarylalkyl optionally substituted by 1-27 $R^{89}$, halogen, —CN, —C(=O)$R^{80}$, —C(=O)O$R^{80}$, —C(=O)N$R^{82}R^{83}$, —C(=O)C(=O)$R^{80}$, —C(=N$R^{85}$)$R^{80}$, —C(=N$R^{85}$)N$R^{82}R^{83}$, —C(=NOH)N$R^{82}R^{83}$, —C(=NO$R^{86}$)$R^{80}$, —C(=NN$R^{82}R^{83}$)$R^{80}$, —C(=NN$R^{84}$C(=O)$R^{81}$)$R^{80}$, —C(=NN$R^{84}$C(=O)O$R^{81}$)$R^{80}$, —C(=S)N$R^{82}R^{83}$, —NC, —NO$_2$, —N$R^{82}R^{83}$, —N$R^{84}$N$R^{82}R^{83}$, —N=N$R^{84}$, =N$R^{80}$, =NO$R^{80}$, —N$R^{84}$O$R^{86}$, —N$R^{84}$C(=O)$R^{80}$, —N$R^{84}$C(=O)C(=O)$R^{80}$, —N$R^{84}$C(=O)O$R^{81}$, —N$R^{84}$C(=O)C(=O)O$R^{81}$, —N$R^{84}$C(=O)N$R^{82}R^{83}$, —N$R^{84}$C(=O)N$R^{84}$C(=O)$R^{80}$, —N$R^{84}$C(=O)N$R^{84}$C(=O)O$R^{80}$, —N$R^{84}$C(=N$R^{85}$)N$R^{82}R^{83}$, —N$R^{84}$C(=O)C(=O)N$R^{82}R^{83}$, —N$R^{84}$C(=S)$R^{80}$, —N$R^{84}$C(=S)N$R^{82}R^{83}$, —N$R^{84}$S(=O)$_2R^{81}$, —N$R^{84}$S(=O)$_2$N$R^{82}R^{83}$, —O$R^{80}$, =O, —OCN, —OC(=O)$R^{80}$, —OC(=O)N$R^{82}R^{83}$, —OC(=O)O$R^{80}$, —OC(=N$R^{85}$)N$R^{82}R^{83}$, —OS(=O)$R^{80}$, —OS(=O)$_2R^{80}$, —OS(=O)$_2$O$R^{80}$, —OS(=O)$_2$N$R^{82}R^{83}$, —SCN, =S, —S(=O)$_nR^{80}$, —S(=O)$_2$O$R^{80}$, —SO$_3R^{87}$, —S(=O)$_2$N$R^{82}R^{83}$, or —S(=O)N$R^{82}R^{83}$; alternatively, when $L^3$, $A^3$, $G^3$, $X^3$, $L^4$, $A^4$, $G^4$ and $X^4$ are absent, $Z^3$ and $Z^4$ can together form a group of formula -$A^{21}$-$A^{22}$-$A^{23}$-; wherein $A^{21}$, $A^{22}$, and $A^{23}$ are independently chosen from —C$Z^{21}Z^{22}$—, —C$Z^{23}Z^{24}$C$Z^{25}Z^{26}$—, —C(=O)—, —N$Z^{27}$—, —S—, —S(=O)—, —S(=O)$_2$—, or —O—; wherein:

(a) when any two of $Z^{21}$, $Z^{22}$, $Z^{23}$, $Z^{24}$, $Z^{25}$, $Z^{26}$ and $Z^{27}$ are located on adjacent atoms, they may together form a bond between the atoms, and (b) any of $Z^{21}$, $Z^{22}$, $Z^{23}$, $Z^{24}$, $Z^{25}$, $Z^{26}$ and $Z^{27}$ may be independently chosen from H, $C_{1-6}$alkyl optionally substituted by 1-13 $R^{99}$, $C_{2-6}$alkenyl optionally substituted by 1-11 $R^{99}$, $C_{2-6}$alkynyl optionally substituted by 1-9 $R^{99}$, $C_{6-11}$ aryl optionally substituted by 1-11 $R^{99}$, $C_{7-16}$arylalkyl optionally substituted by 1-19 $R^{99}$, $C_{3-11}$cycloalkyl optionally substituted by 1-21 $R^{99}$, $C_{4-17}$cycloalkylalkyl optionally substituted by 1-32 $R^{99}$, 3-15 membered heterocycloalkyl optionally substituted by 1-28 $R^{99}$, 4-21 membered heterocycloalkylalkyl optionally substituted by 1-40 $R^{99}$, 5-15 membered heteroaryl optionally substituted by 1-15 $R^{99}$, 6-21 membered heteroarylalkyl optionally substituted by 1-27 $R^{99}$, halogen, —CN, —C(=O)$R^{90}$, —C(=O)O$R^{90}$, —C(=O)N$R^{92}R^{93}$, —C(=O)C(=O)$R^{90}$, —C(=N$R^{95}$)$R^{90}$, —C(=N$R^{95}$)N$R^{92}R^{93}$, —C(=NOH)N$R^{92}R^{93}$, —C(=NO$R^{96}$)$R^{90}$, —C(=NN$R^{92}R^{93}$)$R^{90}$, —C(=NN$R^{94}$C(=O)$R^{91}$)$R^{90}$, —C(=NN$R^{94}$C(=O)O$R^{91}$)$R^{90}$, —C(=S)N$R^{92}R^{93}$, —NC, —NO$_2$, —N$R^{92}R^{93}$, —N$R^{94}$N$R^{92}R^{93}$, —N=N$R^{94}$, =N$R^{90}$, =NO$R^{90}$, —N$R^{94}$O$R^{96}$, —N$R^{94}$C(=O)$R^{90}$, —N$R^{94}$C(=O)C(=O)$R^{90}$, —N$R^{94}$C(=O)O$R^{91}$, —N$R^{94}$C(=O)C(=O)O$R^{91}$, —NR$^{94}$C(=O)NR$^{92}$R$^{93}$, —NR$^{94}$C(=O)NR$^{94}$C(=O)R$^{90}$, —NR$^{94}$C(=O)NR$^{94}$C(=O)OR$^{90}$, —NR$^{94}$C(=NR$^{95}$)NR$^{92}$R$^{93}$, —NR$^{94}$C(=O)C(=O)NR$^{92}$R$^{93}$, —NR$^{94}$C(=S)R$^{90}$, —NR$^{94}$C(=S)OR$^{90}$, —NR$^{94}$C(=S)NR$^{92}$R$^{93}$, —NR$^{94}$S(=O)$_2$R$^{91}$, —NR$^{94}$S(=O)$_2$NR$^{92}$R$^{93}$, —OR$^{90}$, =O, —OCN, —OC(=O)R$^{90}$, —OC(=O)NR$^{92}$R$^{93}$, —OC(=O)OR$^{90}$, —OC(=NR$^{95}$)NR$^{92}$R$^{93}$, —OS(=O)R$^{90}$, —OS(=O)$_2$R$^{90}$, —OS(=O)$_2$OR$^{90}$, —OS(=O)$_2$NR$^{92}$R$^{93}$, —SCN, =S, —S(=O)$_n$R$^{90}$, —S(=O)$_2$OR$^{90}$, —SO$_3$R$^{97}$, —S(=O)$_2$NR$^{92}$R$^{93}$, and —S(=O)NR$^{92}$R$^{93}$; and (c) any two of Z$^{21}$, Z$^{22}$, Z$^{23}$, Z$^{24}$, Z$^{25}$, Z$^{26}$ and Z$^{27}$ may together form a group of formula -A$^{31}$-A$^{32}$-A$^{33}$-, wherein A$^{31}$, A$^{32}$, and A$^{33}$ are independently chosen from —CZ$^{31}$Z$^{32}$—, —CZ$^{33}$Z$^{34}$CZ$^{35}$Z$^{36}$—, —C(=O)—, —NZ$^{37}$—, —S—, —S(=O)—, —S(=O)$_2$—, or —O— wherein:

(i) when any two of Z$^{31}$, Z$^{32}$, Z$^{33}$, Z$^{34}$, Z$^{35}$, Z$^{36}$ and Z$^{37}$ are located on adjacent atoms, they may together form a bond between the atoms, and (ii) any of any of Z$^{21}$, Z$^{22}$, Z$^{23}$, Z$^{24}$, Z$^{25}$, Z$^{26}$ and Z$^{27}$ may be independently chosen from H, C$_{1-6}$alkyl optionally substituted by 1-13 R$^{139}$, C$_{2-6}$alkenyl optionally substituted by 1-11 R$^{139}$, C$_{2-6}$alkynyl optionally substituted by 1-9 R$^{139}$, C$_{6-11}$ aryl optionally substituted by 1-11 R$^{139}$, C$_{7-16}$arylalkyl optionally substituted by 1-19 R$^{139}$, C$_{3-11}$cycloalkyl optionally substituted by 1-21 R$^{139}$, C$_{4-17}$cycloalkylalkyl optionally substituted by 1-32 R$^{139}$, 3-15 membered heterocycloalkyl optionally substituted by 1-28 R$^{139}$, 4-21 membered heterocycloalkylalkyl optionally substituted by 1-40 R$^{139}$, 5-15 membered heteroaryl optionally substituted by 1-15 R$^{139}$, 6-21 membered heteroarylalkyl optionally substituted by 1-27 R$^{139}$, halogen, —CN, —C(=O)R$^{130}$, —C(=O)OR$^{130}$, —C(=O)NR$^{132}$R$^{133}$, —C(=O)C(=O)R$^{130}$, —C(=NR$^{135}$)R$^{130}$, —C(=NR$^{135}$)NR$^{132}$R$^{133}$, —C(=NOH)NR$^{132}$R$^{133}$, —C(=NOR$^{136}$)R$^{130}$, —C(=NNR$^{132}$R$^{133}$)R$^{130}$, —C(=NNR$^{134}$C(=O)R$^{131}$)R$^{130}$, —C(=NNR$^{134}$C(=O)OR$^{131}$)R$^{130}$, —C(=S)NR$^{132}$R$^{133}$, —NC, —NO$_2$, —NR$^{132}$R$^{133}$, —NR$^{134}$NR$^{132}$R$^{133}$, —N=NR$^{134}$, =NR$^{130}$, =NOR$^{130}$, —NR$^{134}$OR$^{136}$, —NR$^{134}$C(=O)R$^{130}$, —NR$^{134}$C(=O)C(=O)R$^{130}$, —NR$^{134}$C(=O)OR$^{131}$, —NR$^{134}$C(=O)C(=O)OR$^{131}$, —NR$^{134}$C(=O)NR$^{132}$R$^{133}$, —NR$^{134}$C(=O)NR$^{134}$C(=O)R$^{130}$, —NR$^{134}$C(=O)NR$^{134}$C(=O)OR$^{130}$, —NR$^{134}$C(=NR$^{135}$)NR$^{132}$R$^{133}$, —NR$^{134}$C(=O)C(=O)NR$^{132}$R$^{133}$, —NR$^{134}$C(=S)R$^{130}$, —NR$^{134}$C(=S)OR$^{130}$, —NR$^{134}$C(=S)NR$^{132}$R$^{133}$, —NR$^{134}$S(=O)$_2$R$^{131}$, —NR$^{134}$S(=O)$_2$NR$^{132}$R$^{133}$, —OR$^{130}$, =O, —OCN, —OC(=O)R$^{130}$, —OC(=O)NR$^{132}$R$^{133}$, —OC(=O)OR$^{130}$, —OC(=NR$^{135}$)NR$^{132}$R$^{133}$, —OS(=O)R$^{130}$, —OS(=O)$_2$R$^{130}$, —OS(=O)$_2$OR$^{130}$, —OS(=O)$_2$NR$^{132}$R$^{133}$, —SCN, =S, —S(=O)$_n$R$^{130}$, —S(=O)$_2$OR$^{130}$, —SO$_3$R$^{137}$, —S(=O)$_2$NR$^{132}$R$^{133}$, and —S(=O)NR$^{132}$R$^{133}$. In another embodiment, Z$^4$ is H, C$_{1-6}$alkyl optionally substituted by 1-13 R$^{89}$, C$_{6-11}$aryl optionally substituted by 1-7 R$^{89}$, C$_{7-16}$arylalkyl optionally substituted by 1-19 R$^{89}$, C$_{3-11}$cycloalkyl optionally substituted by 1-21 R$^{89}$, C$_{4-17}$cycloalkylalkyl optionally substituted by 1-32 R$^{89}$, 3-15 membered heterocycloalkyl optionally substituted by 1-28 R$^{89}$, 4-21 membered heterocycloalkylalkyl optionally substituted by 1-40 R$^{89}$, 5-15 membered heteroaryl optionally substituted by 1-15 R$^{89}$, 6-21 membered heteroarylalkyl optionally substituted by 1-27 R$^{89}$, halogen, —CN, —C(=O)R$^{80}$, —C(=O)OR$^{80}$, —C(=O)NR$^{82}$R$^{83}$, —C(=O)C(=O)R$^{80}$, —C(=S)NR$^{82}$R$^{83}$, —NC, —NO$_2$, —NR$^{82}$R$^{83}$, —NR$^{84}$NR$^{82}$R$^{83}$, —NR$^{84}$C(=O)R$^{80}$, —NR$^{84}$C(=O)C(=O)R$^{80}$, —NR$^{84}$C(=O)OR$^{81}$, —NR$^{84}$C(=O)C(=O)OR$^{81}$, —NR$^{84}$C(=O)NR$^{82}$R$^{83}$, —NR$^{84}$C(=O)NR$^{84}$C(=O)R$^{80}$, —NR$^{84}$C(=O)NR$^{84}$C(=O)OR$^{80}$, —NR$^{84}$C(=NR$^{85}$)NR$^{82}$R$^{83}$, —NR$^{84}$C(=O)C(=O)NR$^{82}$R$^{83}$, —NR$^{84}$C(=S)R$^{80}$, —NR$^{84}$C(=S)OR$^{80}$, —NR$^{84}$C(=S)NR$^{82}$R$^{83}$, —NR$^{84}$S(=O)$_2$R$^{81}$, —NR$^{84}$S(=O)$_2$NR$^{82}$R$^{83}$, —OR$^{80}$, =O, —OCN, —OC(=O)R$^{80}$, —OC(=O)NR$^{82}$R$^{83}$, —OC(=O)OR$^{80}$, —OS(=O)R$^{80}$, —OS(=O)$_2$R$^{80}$, —OS(=O)$_2$OR$^{80}$, —OS(=O)$_2$NR$^{82}$R$^{83}$, —SCN, =S, —S(=O)$_n$R$^{80}$, —S(=O)$_2$OR$^{80}$, —SO$_3$R$^{87}$, —S(=O)$_2$NR$^{82}$R$^{83}$, or —S(=O)NR$^{82}$R$^{83}$; alternatively, when L$^3$, A$^3$, G$^3$, X$^3$, L$^4$, A$^4$, G$^4$ and X$^4$ are absent, Z$^3$ and Z$^4$ can together form a group of formula -A$^{21}$-A$^{22}$A$^{23}$-; wherein A$^{21}$, A$^{22}$, and A$^{23}$ are independently chosen from —CZ$^{21}$Z$^{22}$—, —CZ$^{23}$Z$^{24}$CZ$^{25}$Z$^{26}$—, —C(=O)—, —NZ$^{27}$—, —S—, —S(=O)—, —S(=O)$_2$—, or —O—; wherein:

(a) when any two of Z$^{21}$, Z$^{22}$, Z$^{23}$, Z$^{24}$, Z$^{25}$, Z$^{26}$ and Z$^{27}$ are located on adjacent atoms, they may together form a bond between the atoms, and (b) any of Z$^{21}$, Z$^{22}$, Z$^{23}$, Z$^{24}$, Z$^{25}$, Z$^{26}$ and Z$^{27}$ may be independently chosen from H, C$_{1-6}$alkyl optionally substituted by 1-13 R$^{99}$, C$_{6-11}$ aryl optionally substituted by 1-7 R$^{99}$, C$_{7-16}$arylalkyl optionally substituted by 1-19 R$^{99}$, C$_{3-11}$cycloalkyl optionally substituted by 1-21 R$^{99}$, C$_{4-17}$cycloalkylalkyl optionally substituted by 1-32 R$^{99}$, 3-15 membered heterocycloalkyl optionally substituted by 1-28 R$^{99}$, 4-21 membered heterocycloalkylalkyl optionally substituted by 1-40 R$^{99}$, 5-15 membered heteroaryl optionally substituted by 1-15 R$^{99}$, 6-21 membered heteroarylalkyl optionally substituted by 1-27 R$^{99}$, halogen, —CN, —C(=O)R$^{90}$, —C(=O)OR$^{90}$, —C(=O)NR$^{92}$R$^{93}$, —C(=O)C(=O)R$^{90}$, —C(=S)NR$^{92}$R$^{93}$, —NC, —NO$_2$, —NR$^{92}$R$^{93}$, —NR$^{94}$NR$^{92}$R$^{93}$, —NR$^{94}$C(=O)R$^{90}$, —NR$^{94}$C(=O)C(=O)R$^{90}$, —NR$^{94}$C(=O)OR$^{91}$, —NR$^{94}$C(=O)C(=O)OR$^{91}$, —NR$^{94}$C(=O)NR$^{92}$R$^{93}$, —NR$^{94}$C(=O)NR$^{94}$C(=O)R$^{90}$, —NR$^{94}$C(=O)NR$^{94}$C(=O)OR$^{90}$, —NR$^{94}$C(=NR$^{9}$)NR$^{92}$R$^{93}$, —NR$^{94}$C(=O)C(=O)NR$^{92}$R$^{93}$, —NR$^{94}$C(=S)R$^{90}$, —NR$^{94}$C(=S)OR$^{90}$, —NR$^{94}$C(=S)NR$^{92}$R$^{93}$, —NR$^{94}$S(=O)$_2$R$^{91}$, —NR$^{94}$S(=O)$_2$NR$^{92}$R$^{93}$, —OR$^{90}$, =O, —OCN, —OC(=O)R$^{90}$, —OC(=O)NR$^{92}$R$^{93}$, —OC(=O)OR$^{90}$, —OS(=O)R$^{90}$, —OS(=O)$_2$R$^{90}$, —OS(=O)$_2$OR$^{90}$, —OS(=O)$_2$NR$^{92}$R$^{93}$, —SCN, =S, —S(=O)$_n$R$^{90}$, —S(=O)$_2$OR$^{90}$, —SO$_3$R$^{97}$, —S(=O)$_2$NR$^{92}$R$^{93}$, and —S(=O)NR$^{92}$R$^{93}$; and (c) any two of Z$^{21}$, Z$^{22}$, Z$^{23}$, Z$^{24}$, Z$^{25}$, Z$^{26}$ and Z$^{27}$ may together form a group of formula -A$^{31}$-A$^{32}$-A$^{33}$-, wherein A$^{31}$, A$^{32}$, and A$^{33}$ are independently chosen from —CZ$^{31}$Z$^{32}$—, —CZ$^{33}$Z$^{34}$CZ$^{35}$Z$^{36}$—, —C(=O)—, —NZ$^{37}$—, —S—, —S(=O)—, —S(=O)$_2$—, or —O— wherein:

(i) when any two of Z$^{31}$, Z$^{32}$, Z$^{33}$, Z$^{34}$, Z$^{35}$, Z$^{36}$ and Z$^{37}$ are located on adjacent atoms, they may together form a bond between the atoms, and (ii) any of any of Z$^{21}$, Z$^{22}$, Z$^{23}$, Z$^{24}$, Z$^{25}$, Z$^{26}$ and Z$^{27}$ may be independently chosen from H, C$_{1-6}$alkyl optionally substituted by 1-13 R$^{139}$, C$_{6-11}$ aryl optionally substituted by 1-7 R$^{139}$, C$_{7-16}$arylalkyl optionally substituted by 1-19 R$^{139}$, C$_{3-11}$cycloalkyl optionally substituted by 1-21 R$^{139}$, C$_{4-17}$cycloalkylalkyl optionally substituted by 1-32 R$^{139}$, 3-15 membered heterocycloalkyl optionally substituted by 1-28 R$^{139}$, 4-21 membered heterocycloalkylalkyl optionally substituted by 1-40 R$^{139}$, 5-15 membered heteroaryl optionally substituted by 1-15 R$^{139}$, 6-21 membered heteroarylalkyl optionally substituted by 1-27 R$^{139}$, halogen, —CN, —C(=O)R$^{130}$, —C(=O)OR$^{130}$, —C(=O)NR$^{132}$R$^{133}$, —C(=O)C(=O)R$^{130}$, —C(=S)NR$^{132}$R$^{133}$, —NC, —NO$_2$, —NR$^{132}$R$^{133}$, —NR$^{134}$NR$^{132}$R$^{133}$, —NR$^{134}$C(=O)R$^{130}$, —NR$^{134}$C(=O)C(=O)R$^{130}$, —NR$^{134}$C(=O)OR$^{131}$, —NR$^{134}$C(=O)C(=O)OR$^{131}$, —NR$^{134}$C(=O)NR$^{132}$R$^{133}$, —NR$^{134}$C(=O)

—NR¹³⁴C(=O)R¹³⁰, —NR¹³⁴C(=O)NR¹³⁴C(=O)OR¹³⁰, —NR¹³⁴C(=NR¹³⁵)NR¹³²R¹³³, —NR¹³⁴C(=O)C(=O)NR¹³²R¹³³, —NR¹³⁴C(=S)R¹³⁰, —NR¹³⁴C(=S)NR¹³²R¹³³, —NR¹³⁴S(=O)₂R¹³¹, —NR¹³⁴S(=O)₂NR¹³²R¹³³, —OR¹³⁰, =O, —OCN, —OC(=O)R¹³⁰, —OC(=O)NR¹³²R¹³³, —OC(=O)OR¹³⁰, —OS(=O)R¹³⁰, —OS(=O)₂R¹³⁰, —OS(=O)₂OR¹³⁰, —OS(=O)₂NR¹³²R¹³³, —SCN, =S, —S(=O)ₙR¹³⁰, —S(=O)₂OR¹³⁰, —SO₃R¹³⁷, —S(=O)₂NR¹³²R¹³³, and —S(=O)NR¹³²R¹³³. In another embodiment, Z⁴ is H, C₁₋₆alkyl optionally substituted by 1-13 R⁸⁹, C₆₋₁₁aryl optionally substituted by 1-7 R⁸⁹, C₇₋₁₆arylalkyl optionally substituted by 1-19 R⁸⁹, C₃₋₁₁cycloalkyl optionally substituted by 1-21 R⁸⁹, C₄₋₁₇cycloalkylalkyl optionally substituted by 1-32 R⁸⁹, 3-15 membered heterocycloalkyl optionally substituted by 1-28 R⁸⁹, 4-21 membered heterocycloalkylalkyl optionally substituted by 1-40 R⁸⁹, 5-15 membered heteroaryl optionally substituted by 1-15 R⁸⁹, 6-21 membered heteroarylalkyl optionally substituted by 1-27 R⁸⁹, halogen, —CN, —C(=O)R⁸⁰, —C(=O)OR⁸⁰, —C(=O)NR⁸²R⁸³, —C(=S)NR⁸²R⁸³, —NC, —NO₂, —NR⁸²R⁸³, —NR⁸⁴NR⁸²R⁸³, —NR⁸⁴C(=O)R⁸⁰, —NR⁸⁴C(=O)OR⁸¹, —NR⁸⁴C(=O)NR⁸²R⁸³, —NR⁸⁴C(=O)NR⁸⁴C(=O)R⁸⁰, —NR⁸⁴C(=O)NR⁸⁴C(=O)OR⁸⁰, —NR⁸⁴C(=NR⁸⁵)NR⁸²R⁸³, —NR⁸⁴C(=S)R⁸⁰, —NR⁸⁴C(=S)NR⁸²R⁸³, —NR⁸⁴S(O)₂R⁸¹, NR⁸⁴P(=O)R⁸⁸R⁸⁸, —OR⁸⁰, =O, —OCN, —OC(=O)R⁸⁰, —OC(=O)NR⁸²R⁸³, —SCN, =S, —S(=O)ₙR⁸⁰, —S(=O)₂OR⁸⁰, —S(=O)₂NR⁸²R⁸³, or —P(=O)R⁸⁸R⁸⁸; alternatively, when L³, A³, G³, X³, L⁴, A⁴, G⁴ and X⁴ are absent, Z³ and Z⁴ can together form a group of formula -A²¹-A²²-A²³-; wherein A²¹, A²², and A²³ are independently chosen from —CZ²¹Z²²—, —CZ²³Z²⁴CZ²⁵Z²⁶—, —C(=O)—, —NZ²⁷—, —S—, —S(=O)—, —S(=O)₂—, or —O—; wherein:
(a) when any two of Z²¹, Z²², Z²³, Z²⁴, Z²⁵, Z²⁶ and Z²⁷ are located on adjacent atoms, they may together form a bond between the atoms, and
(b) any of Z²¹, Z²², Z²³, Z²⁴, Z²⁵, Z²⁶ and Z²⁷ may be independently chosen from H, C₁₋₆alkyl optionally substituted by 1-13 R⁹⁹, C₆₋₁₁ aryl optionally substituted by 1-7 R⁹⁹, C₇₋₁₆arylalkyl optionally substituted by 1-19 R⁹⁹, C₃₋₁₁cycloalkyl optionally substituted by 1-21 R⁹⁹, C₄₋₁₇cycloalkylalkyl optionally substituted by 1-32 R⁹⁹, 3-15 membered heterocycloalkyl optionally substituted by 1-28 R⁹⁹, 4-21 membered heterocycloalkylalkyl optionally substituted by 1-40 R⁹⁹, 5-15 membered heteroaryl optionally substituted by 1-15 R⁹⁹, 6-21 membered heteroarylalkyl optionally substituted by 1-27 R⁹⁹, halogen, —CN, —C(=O)R⁹⁰, —C(=O)OR⁹⁰, —C(=O)NR⁹²R⁹³, —C(=S)NR⁹²R⁹³, —NC, —NO₂, —NR⁹²R⁹³, —NR⁹⁴NR⁹²R⁹³, —NR⁹⁴C(=O)R⁹⁰, —NR⁹⁴C(=O)OR⁹¹, —NR⁹⁴C(=O)NR⁹²R⁹³, —NR⁹⁴C(=O)NR⁹⁴C(=O)R⁹⁰, —NR⁹⁴C(=O)NR⁹⁴C(=O)OR⁹⁰, —NR⁹⁴C(=NR⁹⁵)NR⁹²R⁹³, —NR⁹⁴C(=S)R⁹⁰, —NR⁹⁴C(=S)NR⁹²R⁹³, —NR⁹⁴S(=O)₂R⁹¹, —NR⁹⁴P(=O)R⁹⁸R⁹⁸, —OR⁹⁰, =O, —OCN, —OC(=O)NR⁹²R⁹³, —SCN, =S, —S(=O)ₙR⁹⁰, —S(=O)₂NR⁹²R⁹³, and —P(=O)R⁹⁸R⁹⁸; and
(c) any two of Z²¹, Z²², Z²³, Z²⁴, Z²⁵, Z²⁶ and Z²⁷ may together form a group of formula -A³¹-A³²-A³³-, wherein A³¹, A³², and A³³ are independently chosen from —CZ³¹Z³²—, —CZ³³Z³⁴CZ³⁵Z³⁶—, —C(=O)—, —NZ³⁷—, —S—, —S(=O)—, —S(=O)₂—, or —O— wherein:
(i) when any two of Z³¹, Z³², Z³³, Z³⁴, Z³⁵, Z³⁶ and Z³⁷ are located on adjacent atoms, they may together form a bond between the atoms, and (ii) any of any of Z²¹, Z²², Z²³, Z²⁴, Z²⁵, Z²⁶ and Z²⁷ may be independently chosen from H, C₁₋₆alkyl optionally substituted by 1-13 R¹³⁹, C₆₋₁₁ aryl optionally substituted by 1-7 R¹³⁹, C₇₋₁₆ arylalkyl optionally substituted by 1-19 R¹³⁹, C₃₋₁₁ cycloalkyl optionally substituted by 1-21 R¹³⁹, C₄₋₁₇cycloalkylalkyl optionally substituted by 1-32 R¹³⁹, 3-15 membered heterocycloalkyl optionally substituted by 1-28 R¹³⁹, 4-21 membered heterocycloalkylalkyl optionally substituted by 1-40 R¹³⁹, 5-15 membered heteroaryl optionally substituted by 1-15 R¹³⁹, 6-21 membered heteroarylalkyl optionally substituted by 1-27 R¹³⁹, halogen, —CN, —C(=O)R¹³⁰, —C(=O)OR¹³⁰, —C(=O)NR¹³²R¹³³, —C(=S)NR¹³²R¹³³, —NC, —NO₂, —NR¹³²R¹³³, —NR¹³⁴NR¹³²R¹³³, —NR¹³⁴C(=O)R¹³⁰, —NR¹³⁴C(=O)OR¹³¹, —NR¹³⁴C(=O)NR¹³²R¹³³, —NR¹³⁴C(=O)NR¹³⁴C(=O)R¹³⁰, —NR¹³⁴C(=NR¹³⁵)NR¹³²R¹³³, —NR¹³⁴C(=S)R¹³⁰, —NR¹³⁴C(=S)NR¹³²R¹³³, —NR¹³⁴S(=O)₂R¹³¹, —NR¹³⁴P(=O)R¹³⁸R¹³⁸, —OR¹³⁰, =O, —OCN, —OC(=O)R¹³⁰, —OC(=O)NR¹³²R¹³³, —SCN, =S, —S(=O)ₙR¹³⁰, —S(=O)₂NR¹³²R¹³³, and —P(=O)R¹³⁸R¹³⁸. In another embodiment, Z⁴ is H, C₁₋₆alkyl optionally substituted by 1-13 R⁸⁹, C₆₋₁₁ aryl optionally substituted by 1-7 R⁸⁹, C₇₋₁₆arylalkyl optionally substituted by 1-19 R⁸⁹, C₃₋₁₁cycloalkyl optionally substituted by 1-21 R⁸⁹, C₄₋₁₇cycloalkylalkyl optionally substituted by 1-32 R⁸⁹, 3-15 membered heterocycloalkyl optionally substituted by 1-28 R⁸⁹, 4-21 membered heterocycloalkylalkyl optionally substituted by 1-40 R⁸⁹, 5-15 membered heteroaryl optionally substituted by 1-15 R⁸⁹, 6-21 membered heteroarylalkyl optionally substituted by 1-27 R⁸⁹, halogen, —CN, —C(=O)R⁸⁰, —C(=O)OR⁸⁰, —C(=O)NR⁸²R⁸³, —C(=S)NR⁸²R⁸³, —NC, —NO₂, —NR⁸²R⁸³, —NR⁸⁴NR⁸²R⁸³, —NR⁸⁴C(=O)R⁸⁰, —NR⁸⁴C(=O)OR⁸¹, —NR⁸⁴C(=O)NR⁸²R⁸³, —NR⁸⁴C(=O)NR⁸⁴C(=O)R⁸⁰, —NR⁸⁴C(=O)NR⁸⁴C(=O)OR⁸⁰, —NR⁸⁴C(=NR⁸⁵)NR⁸²R⁸³, —NR⁸⁴C(=S)R⁸⁰, —NR⁸⁴C(=S)NR⁸²R⁸³, —NR⁸⁴S(=O)₂R⁸¹, —OR⁸⁰, =O, —OCN, —OC(=O)R⁸⁰, —OC(=O)NR⁸²R⁸³, —SCN, =S, —S(=O)ₙR⁸⁰, —S(=O)₂OR⁸⁰, or —S(=O)₂NR⁸²R⁸³; alternatively, when L³, A³, G³, X³, L⁴, A⁴, G⁴ and X⁴ are absent, Z³ and Z⁴ can together form a group of formula -A²¹-A²²-A²³-; wherein A²¹, A²², and A²³ are independently chosen from —CZ²¹Z²²—, —CZ²³Z²⁴CZ²⁵Z²⁶—, —C(=O)—, —NZ²⁷-, —S—, —S(=O)—, —S(=O)₂—, or —O—; wherein:
(a) when any two of Z²¹, Z²², Z²³, Z²⁴, Z²⁵, Z²⁶ and Z²⁷ are located on adjacent atoms, they may together form a bond between the atoms, and
(b) any of Z²¹, Z²², Z²³, Z²⁴, Z²⁵, Z²⁶ and Z²⁷ may be independently chosen from H, C₁₋₆alkyl optionally substituted by 1-13 R⁹⁹, C₆₋₁₁ aryl optionally substituted by 1-7 R⁹⁹, C₇₋₁₆arylalkyl optionally substituted by 1-19 R⁹⁹, C₃₋₁₁cycloalkyl optionally substituted by 1-21 R⁹⁹, C₄₋₁₇cycloalkylalkyl optionally substituted by 1-32 R⁹⁹, 3-15 membered heterocycloalkyl optionally substituted by 1-28 R⁹⁹, 4-21 membered heterocycloalkylalkyl optionally substituted by 1-40 R⁹⁹, 5-15 membered heteroaryl optionally substituted by 1-15 R⁹⁹, 6-21 membered heteroarylalkyl optionally substituted by 1-27 R⁹⁹, halogen, —CN, —C(=O)R⁹⁰, —C(=O)OR⁹⁰, —C(=O)NR⁹²R⁹³, —C(=S)NR⁹²R⁹³, —NC, —NO₂, —NR⁹²R⁹³, —NR⁹⁴NR⁹²R⁹³, —NR⁹⁴C(=O)R⁹⁰, —NR⁹⁴C(=O)OR⁹¹, —NR⁹⁴C(=O)NR⁹²R⁹³, —NR⁹⁴C(=O)NR⁹⁴C(=O)R⁹⁰, —NR⁹⁴C(=O)NR⁹⁴C(=O)OR⁹⁰, —NR⁹⁴C(=NR⁹⁵)NR⁹²R⁹³, —NR⁹⁴C(=S)R⁹⁰, —NR⁹⁴C(=S)NR⁹²R⁹³, —NR⁹⁴S(=O)₂R⁹¹, —OR⁹⁰, =O, —OCN, —OC(=O)NR⁹²R⁹³, —SCN, =S, —S(=O)ₙR⁹⁰, and —S(=O)₂NR⁹²R⁹³; and (c) any two of $Z^{21}$, $Z^{22}$, $Z^{23}$, $Z^{24}$, $Z^{25}$, $Z^{26}$ and $Z^{27}$ may together form a group of formula -$A^{31}$-$A^{32}$-$A^{33}$-, wherein $A^{31}$, $A^{32}$, and $A^{33}$ are independently chosen from —$CZ^{31}Z^{32}$—, —$CZ^{33}Z^{34}CZ^{35}Z^{36}$—, —C(=O)—, —$NZ^{37}$—, —S—, —S(=O)—, —S(=O)$_2$—, or —O— wherein:

(i) when any two of $Z^{31}$, $Z^{32}$, $Z^{33}$, $Z^{34}$, $Z^{35}$, $Z^{36}$ and $Z^{37}$ are located on adjacent atoms, they may together form a bond between the atoms, and (ii) any of any of $Z^{21}$, $Z^{22}$, $Z^{23}$, $Z^{24}$, $Z^{25}$, $Z^{26}$ and $Z^{27}$ may be independently chosen from H, $C_{1-6}$alkyl optionally substituted by 1-13 $R^{139}$, $C_{6-11}$ aryl optionally substituted by 1-7 $R^{139}$, $C_{7-16}$arylalkyl optionally substituted by 1-19 $R^{139}$, $C_{3-11}$cycloalkyl optionally substituted by 1-21 $R^{139}$, $C_{4-17}$cycloalkylalkyl optionally substituted by 1-32 $R^{139}$, 3-15 membered heterocycloalkyl optionally substituted by 1-28 $R^{139}$, 4-21 membered heterocycloalkylalkyl optionally substituted by 1-40 $R^{139}$, 5-15 membered heteroaryl optionally substituted by 1-15 $R^{139}$, 6-21 membered heteroarylalkyl optionally substituted by 1-27 $R^{139}$, halogen, —CN, —C(=O)$R^{130}$, —C(=O)O$R^{130}$, —C(=O)N$R^{132}R^{133}$, —C(=S)N$R^{132}R^{133}$, —NC, —NO$_2$, —N$R^{132}R^{133}$, —N$R^{134}$N$R^{132}R^{133}$, —N$R^{134}$C(=O)$R^{130}$, —N$R^{134}$C(=O)O$R^{131}$, —N$R^{134}$C(=O)N$R^{132}R^{133}$, —N$R^{134}$C(=O)N$R^{134}$C(=O)$R^{130}$, —N$R^{134}$C(=N$R^{135}$)N$R^{132}R^{133}$, —N$R^{134}$C(=S)$R^{130}$, —N$R^{134}$C(=S)N$R^{132}R^{133}$, —N$R^{134}$S(=O)$_2R^{131}$, —O$R^{130}$, =O, —OCN, —OC(=O)$R^{130}$, —OC(=O)N$R^{132}R^{133}$, —SCN, =S, —S(=O)$_nR^{130}$, and —S(=O)$_2$N$R^{132}R^{133}$. In another embodiment, $Z^4$ is H, $C_{1-6}$alkyl optionally substituted by 1-13 $R^{89}$, $C_{6-11}$aryl optionally substituted by 1-7 $R^{89}$, $C_{7-16}$arylalkyl optionally substituted by 1-19 $R^{89}$, $C_{3-11}$cycloalkyl optionally substituted by 1-21 $R^{89}$, $C_{4-17}$cycloalkylalkyl optionally substituted by 1-32 $R^{89}$, 3-15 membered heterocycloalkyl optionally substituted by 1-28 $R^{89}$, 4-21 membered heterocycloalkylalkyl optionally substituted by 1-40 $R^{89}$, 5-15 membered heteroaryl optionally substituted by 1-15 $R^{89}$, 6-21 membered heteroarylalkyl optionally substituted by 1-27 $R^{89}$, halogen, —CN, —C(=O)$R^{80}$, —C(=O)O$R^{80}$, —C(=O)N$R^{82}R^{83}$, —C(=S)N$R^{82}R^{83}$, —N$R^{82}R^{83}$, —N$R^{84}$C(=O)$R^{80}$, —N$R^{84}$C(=O)O$R^{81}$, —N$R^{84}$C(=O)N$R^{82}R^{83}$, —N$R^{84}$C(=O)N$R^{84}$C(=O)$R^{80}$, —N$R^{84}$C(=O)N$R^{84}$C(=O)O$R^{80}$, —N$R^{84}$C(=S)$R^{80}$, —N$R^{84}$S(=O)$_2R^{81}$, —O$R^{80}$, =O, —OC(=O)$R^{80}$, —OC(=O)N$R^{82}R^{83}$, =S, —S(=O)$_nR^{80}$, or —S(=O)$_2$N$R^{82}R^{83}$; alternatively, when $L^3$, $A^3$, $G^3$, $X^3$, $L^4$, $A^4$, $G^4$ and $X^4$ are absent, $Z^3$ and $Z^4$ can together form a group of formula -$A^{21}$-$A^{22}$-$A^{23}$-; wherein $A^{21}$, $A^{22}$, and $A^{23}$ are independently chosen from —$CZ^{21}Z^{22}$—, —$CZ^{23}Z^{24}CZ^{25}Z^{26}$—, —C(=O)—, —$NZ^{27}$—, —S—, —S(=O)—, —S(=O)$_2$—, or —O—; wherein:

(a) when any two of $Z^{21}$, $Z^{22}$, $Z^{23}$, $Z^{24}$, $Z^{25}$, $Z^{26}$ and $Z^{27}$ are located on adjacent atoms, they may together form a bond between the atoms, and (b) any of $Z^{21}$, $Z^{22}$, $Z^{23}$, $Z^{24}$, $Z^{25}$, $Z^{26}$ and $Z^{27}$ may be independently chosen from H, $C_{1-6}$alkyl optionally substituted by 1-13 $R^{99}$, $C_{6-11}$ aryl optionally substituted by 1-7 $R^{99}$, $C_{7-16}$arylalkyl optionally substituted by 1-19 $R^{99}$, $C_{3-11}$cycloalkyl optionally substituted by 1-21 $R^{99}$, $C_{4-17}$cycloalkylalkyl optionally substituted by 1-32 $R^{99}$, 3-15 membered heterocycloalkyl optionally substituted by 1-28 $R^{99}$, 4-21 membered heterocycloalkylalkyl optionally substituted by 1-40 $R^{99}$, 5-15 membered heteroaryl optionally substituted by 1-15 $R^{99}$, 6-21 membered heteroarylalkyl optionally substituted by 1-27 $R^{99}$, halogen, —CN, —C(=O)$R^{90}$, —C(=O)O$R^{90}$, —C(=O)N$R^{92}R^{93}$, —C(=S)N$R^{92}R^{93}$, —N$R^{92}R^{93}$, —N$R^{94}$C(=O)$R^{90}$, —N$R^{94}$C(=O)O$R^{91}$, —N$R^{94}$C(=O)N$R^{92}R^{93}$, —N$R^{94}$C(=O)N$R^{94}$C(=O)$R^{90}$, —N$R^{94}$C(=O)N$R^{94}$C(=O)O$R^{90}$, —N$R^{94}$C(=S)$R^{90}$, —N$R^{94}$S(=O)$_2R^{91}$, —O$R^{90}$, =O, —OC(=O)$R^{90}$, —OC(=O)N$R^{92}R^{93}$, =S, —S(=O)$_nR^{90}$, and —S(=O)$_2$N$R^{92}R^{93}$; and (c) any two of $Z^{21}$, $Z^{22}$, $Z^{23}$, $Z^{24}$, $Z^{25}$, $Z^{26}$ and $Z^{27}$ may together form a group of formula -$A^{31}$-$A^{32}$-$A^{33}$-, wherein $A^{31}$, $A^{32}$, and $A^{33}$ are independently chosen from —$CZ^{31}Z^{32}$—, —$CZ^{33}Z^{34}CZ^{35}Z^{36}$—, —C(=O)—, —$NZ^{37}$—, —S—, —S(=O)—, —S(=O)$_2$—, or —O— wherein:

(i) when any two of $Z^{31}$, $Z^{32}$, $Z^{33}$, $Z^{34}$, $Z^{35}$, $Z^{36}$ and $Z^{37}$ are located on adjacent atoms, they may together form a bond between the atoms, and (ii) any of any of $Z^{21}$, $Z^{22}$, $Z^{23}$, $Z^{24}$, $Z^{25}$, $Z^{26}$ and $Z^{27}$ may be independently chosen from H, $C_{1-6}$alkyl optionally substituted by 1-13 $R^{139}$, $C_{6-11}$ aryl optionally substituted by 1-7 $R^{139}$, $C_{7-16}$arylalkyl optionally substituted by 1-19 $R^{139}$, $C_{3-11}$cycloalkyl optionally substituted by 1-21 $R^{139}$, $C_{4-17}$cycloalkylalkyl optionally substituted by 1-32 $R^{139}$, 3-15 membered heterocycloalkyl optionally substituted by 1-28 $R^{139}$, 4-21 membered heterocycloalkylalkyl optionally substituted by 1-40 $R^{139}$, 5-15 membered heteroaryl optionally substituted by 1-15 $R^{139}$, 6-21 membered heteroarylalkyl optionally substituted by 1-27 $R^{139}$, halogen, —CN, —C(=O)$R^{130}$, —C(=O)O$R^{130}$, —C(=O)N$R^{132}R^{133}$, —C(=S)N$R^{132}R^{133}$, —N$R^{132}R^{133}$, —N$R^{134}$C(=O)$R^{130}$, —N$R^{134}$C(=O)O$R^{131}$, —N$R^{134}$C(=O)N$R^{132}R^{133}$, —N$R^{134}$C(=O)N$R^{134}$C(=O)$R^{130}$, —N$R^{134}$C(=S)$R^{130}$, —N$R^{134}$S(=O)$_2R^{131}$, —O$R^{130}$, =O, —OCN, —OC(=O)$R^{130}$, —OC(=O)N$R^{132}R^{133}$, =S, —S(=O)$_nR^{130}$, and —S(=O)$_2$N$R^{132}R^{133}$. In another embodiment, $Z^4$ is H, $C_{1-6}$alkyl optionally substituted by 1-13 $R^{89}$, $C_{6-11}$aryl optionally substituted by 1-7 $R^{89}$, $C_{7-16}$arylalkyl optionally substituted by 1-19 $R^{89}$, $C_{3-11}$cycloalkyl optionally substituted by 1-21 $R^{89}$, $C_{4-17}$cycloalkylalkyl optionally substituted by 1-32 $R^{89}$, 3-15 membered heterocycloalkyl optionally substituted by 1-28 $R^{89}$, 4-21 membered heterocycloalkylalkyl optionally substituted by 1-40 $R^{89}$, 5-15 membered heteroaryl optionally substituted by 1-15 $R^{89}$, 6-21 membered heteroarylalkyl optionally substituted by 1-27 $R^{89}$, halogen, —CN, —C(=O)$R^{80}$, —C(=O)O$R^{80}$, —C(=O)N$R^{82}R^{83}$, —N$R^{82}R^{83}$, —N$R^{84}$C(=O)$R^{80}$, —N$R^{84}$C(=O)O$R^{81}$, —N$R^{84}$C(=O)N$R^{82}R^{83}$, —N$R^{84}$S(=O)$_2R^{81}$, —N$R^{84}$P(=O)$R^{88}R^{88}$, —O$R^{80}$, =O, —OC(=O)$R^{80}$, —OC(=O)N$R^{82}R^{83}$, =S, —S(=O)$_nR^{80}$, —S(=O)$_2$N$R^{82}R^{83}$, or —P(=O)$R^{88}R^{88}$; alternatively, when $L^3$, $A^3$, $G^3$, $X^3$, $L^4$, $A^4$, $G^4$ and $X^4$ are absent, $Z^3$ and $Z^4$ can together form a group of formula -$A^{21}$-$A^{22}$-$A^{23}$-; wherein $A^{21}$, $A^{22}$, and $A^{23}$ are independently chosen from —$CZ^{21}Z^{22}$—, —$CZ^{23}Z^{24}CZ^{25}Z^{26}$—, or —$NZ^{27}$—; wherein:

(a) when any two of $Z^{21}$, $Z^{22}$, $Z^{23}$, $Z^{24}$, $Z^{25}$, $Z^{26}$ and $Z^{27}$ are located on adjacent atoms, they may together form a bond between the atoms, and (b) any of $Z^{21}$, $Z^{22}$, $Z^{23}$, $Z^{24}$, $Z^{25}$, $Z^{26}$ and $Z^{27}$ may be independently chosen from H, $C_{1-6}$alkyl optionally substituted by 1-13 $R^{99}$, $C_{6-11}$ aryl optionally substituted by 1-7 $R^{99}$, $C_{7-16}$arylalkyl optionally substituted by 1-19 $R^{99}$, $C_{3-11}$cycloalkyl optionally substituted by 1-21 $R^{99}$, $C_{4-17}$cycloalkylalkyl optionally substituted by 1-32 $R^{99}$, 3-15 membered heterocycloalkyl optionally substituted by 1-28 $R^{99}$, 4-21 membered heterocycloalkylalkyl optionally substituted by 1-40 $R^{99}$, 5-15 membered heteroaryl optionally substituted by 1-15 $R^{99}$, 6-21 membered heteroarylalkyl optionally substituted by 1-27 $R^{99}$, halogen, —CN, —C(=O)$R^{90}$, —C(=O)O$R^{90}$, —C(=O)N$R^{92}R^{93}$, —N$R^{94}$C(=O)$R^{90}$, —N$R^{94}$C(=O)O$R^{91}$, —N$R^{94}$C(=O)N$R^{92}R^{93}$, —N$R^{94}$S $(=O)_2R^{91}$, $-NR^{94}P(=O)R^{98}R^{98}$, $-OR^{90}$, $=O$, $-OC(=O)R^{90}$, $-OC(=O)NR^{92}R^{93}$, $=S$, $-S(=O)_nR^{90}$, $-S(=O)_2NR^{92}R^{93}$, and $-P(=O)R^{98}R^{98}$; and (c) any two of $Z^{21}$, $Z^{22}$, $Z^{23}$, $Z^{24}$, $Z^{25}$, $Z^{26}$ and $Z^{27}$ may together form a group of formula $-A^{31}-A^{32}-A^{33}-$, wherein $A^{31}$, $A^{32}$, and $A^{33}$ are independently chosen from $-CZ^{31}Z^{32}-$, $-CZ^{33}Z^{34}CZ^{35}Z^{36}-$, or $-NZ^{37}-$ wherein:

(i) when any two of $Z^{31}$, $Z^{32}$, $Z^{33}$, $Z^{34}$, $Z^{35}$, $Z^{36}$ and $Z^{37}$ are located on adjacent atoms, they may together form a bond between the atoms, and (ii) any of any of $Z^{21}$, $Z^{22}$, $Z^{23}$, $Z^{24}$, $Z^{25}$, $Z^{26}$ and $Z^{27}$ may be independently chosen from H, $C_{1-6}$alkyl optionally substituted by 1-13 $R^{139}$, $C_{6-11}$ aryl optionally substituted by 1-7 $R^{139}$, $C_{7-16}$arylalkyl optionally substituted by 1-19 $R^{139}$, $C_{3-11}$cycloalkyl optionally substituted by 1-21 $R^{139}$, $C_{4-17}$cycloalkylalkyl optionally substituted by 1-32 $R^{139}$, 3-15 membered heterocycloalkyl optionally substituted by 1-28 $R^{139}$, 4-21 membered heterocycloalkylalkyl optionally substituted by 1-40 $R^{139}$, 5-15 membered heteroaryl optionally substituted by 1-15 $R^{139}$, 6-21 membered heteroarylalkyl optionally substituted by 1-27 $R^{139}$, halogen, $-CN$, $-C(=O)R^{130}$, $-C(=O)OR^{130}$, $-C(=O)NR^{132}R^{133}$, $-NR^{132}R^{133}$, $-NR^{134}C(=O)R^{130}$, $-NR^{134}C(=O)OR^{131}$, $-NR^{134}C(=O)NR^{132}R^{133}$, $-NR^{134}P(=O)R^{138}R^{138}$, $-OR^{130}$, $=O$, $-OCN$, $-OS(=O)R^{130}$, $-OC(=O)NR^{132}R^{133}$, $=S$, $-S(=O)_nR^{130}$, $-S(=O)_2NR^{132}R^{133}$, and $-P(=O)R^{138}R^{138}$. In another embodiment, $Z^4$ is H, $C_{1-6}$alkyl optionally substituted by 1-13 $R^{89}$, $C_{6-11}$ aryl optionally substituted by 1-7 $R^{89}$, $C_{7-16}$arylalkyl optionally substituted by 1-19 $R^{89}$, $C_{3-11}$cycloalkyl optionally substituted by 1-21 $R^{89}$, $C_{4-17}$cycloalkylalkyl optionally substituted by 1-32 $R^{89}$, 3-15 membered heterocycloalkyl optionally substituted by 1-28 $R^{89}$, 4-21 membered heterocycloalkylalkyl optionally substituted by 1-40 $R^{89}$, 5-15 membered heteroaryl optionally substituted by 1-15 $R^{89}$, 6-21 membered heteroarylalkyl optionally substituted by 1-27 $R^{89}$, halogen, $-CN$, $-C(=O)R^{80}$, $-C(=O)OR^{80}$, $-C(=O)NR^{82}R^{83}$, $-NR^{82}R^{83}$, $-NR^{84}C(=O)R^{80}$, $-NR^{84}C(=O)OR^{81}$, $-NR^{84}C(=O)NR^{82}R^{83}$, $-NR^{84}S(=O)_2R^{81}$, $-OR^{80}$, $=O$, $-OC(=O)R^{80}$, $-OC(=O)NR^{82}R^{83}$, $=S$, $-S(=O)_nR^{80}$, or $-S(=O)_2NR^{82}R^{83}$; alternatively, when $L^3$, $A^3$, $G^3$, $X^3$, $L^4$, $A^4$, $G^4$ and $X^4$ are absent, $Z^3$ and $Z^4$ can together form a group of formula $-A^{21}-A^{22}-A^{23}-$; wherein $A^{21}$, $A^{22}$, and $A^{23}$ are independently chosen from $-CZ^{21}Z^{22}-$, $-CZ^{23}Z^{24}CZ^{25}Z^{26}-$, or $-NZ^{27}-$; wherein:

(a) when any two of $Z^{21}$, $Z^{22}$, $Z^{23}$, $Z^{24}$, $Z^{25}$, $Z^{26}$ and $Z^{27}$ are located on adjacent atoms, they may together form a bond between the atoms, and (b) any of $Z^{21}$, $Z^{22}$, $Z^{23}$, $Z^{24}$, $Z^{25}$, $Z^{26}$ and a $Z^{27}$ may be independently chosen from H, $C_{1-6}$alkyl optionally substituted by 1-13 $R^{99}$, $C_{6-11}$ aryl optionally substituted by 1-7 $R^{99}$, $C_{7-16}$arylalkyl optionally substituted by 1-19 $R^{99}$, $C_{3-11}$cycloalkyl optionally substituted by 1-21 $R^{99}$, $C_{4-17}$cycloalkylalkyl optionally substituted by 1-32 $R^{99}$, 3-15 membered heterocycloalkyl optionally substituted by 1-28 $R^{99}$, 4-21 membered heterocycloalkylalkyl optionally substituted by 1-40 $R^{99}$, 5-15 membered heteroaryl optionally substituted by 1-15 $R^{99}$, 6-21 membered heteroarylalkyl optionally substituted by 1-27 $R^{99}$, halogen, $-CN$, $-C(=O)R^{90}$, $-C(=O)OR^{90}$, $-C(=O)NR^{92}R^{93}$, $-NR^{92}R^{93}$, $-NR^{94}C(=O)R^{90}$, $-NR^{94}C(=O)OR^{91}$, $-NR^{94}C(=O)NR^{92}R^{93}$, $-NR^{94}S(=O)_2R^{91}$, $-OR^{90}$, $=O$, $-OC(=O)R^{90}$, $-OC(=O)NR^{92}R^{93}$, $=S$, $-S(=O)_nR^{90}$, and $-S(=O)_2NR^{92}R^{93}$; and (c) any two of $Z^{21}$, $Z^{22}$, $Z^{23}$, $Z^{24}$, $Z^{25}$, $Z^{26}$ and $Z^{27}$ may together form a group of formula $-A^{31}-A^{32}-A^{33}-$, wherein $A^{31}$, $A^{32}$, and $A^{33}$ are independently chosen from $-CZ^{31}Z^{32}-$, $-CZ^{33}Z^{34}CZ^{35}Z^{36}-$, or $-NZ^{37}-$ wherein:

(i) when any two of $Z^{31}$, $Z^{32}$, $Z^{33}$, $Z^{34}$, $Z^{35}$, $Z^{36}$ and $Z^{37}$ are located on adjacent atoms, they may together form a bond between the atoms, and (ii) any of any of $Z^{21}$, $Z^{22}$, $Z^{23}$, $Z^{24}$, $Z^{25}$, $Z^{26}$ and $Z^{27}$ may be independently chosen from H, $C_{1-6}$alkyl optionally substituted by 1-13 $R^{139}$, $C_{6-11}$ aryl optionally substituted by 1-7 $R^{139}$, $C_{7-16}$arylalkyl optionally substituted by 1-19 $R^{139}$, $C_{3-11}$cycloalkyl optionally substituted by 1-21 $R^{139}$, $C_{4-17}$cycloalkylalkyl optionally substituted by 1-32 $R^{139}$, 3-15 membered heterocycloalkyl optionally substituted by 1-28 $R^{139}$, 4-21 membered heterocycloalkylalkyl optionally substituted by 1-40 $R^{139}$, 5-15 membered heteroaryl optionally substituted by 1-15 $R^{139}$, 6-21 membered heteroarylalkyl optionally substituted by 1-27 $R^{139}$, halogen, $-CN$, $-C(=O)R^{130}$, $-C(=O)OR^{130}$, $-C(=O)NR^{132}R^{133}$, $-NR^{132}R^{133}$, $-NR^{134}C(=O)R^{130}$, $-NR^{134}C(=O)OR^{131}$, $-NR^{134}C(=O)NR^{132}R^{133}$, $-NR^{134}S(=O)_2R^{131}$, $-OR^{130}$, $=O$, $-OCN$, $-OC(=O)R^{130}$, $-OC(=O)NR^{132}R^{133}$, $=S$, $-S(=O)_nR^{130}$, and $-S(=O)_2NR^{132}R^{133}$. In another embodiment, $Z^4$ is H, $C_{1-6}$alkyl optionally substituted by 1-13 $R^{89}$, $C_{6-11}$aryl optionally substituted by 1-7 $R^{89}$, $C_{7-16}$arylalkyl optionally substituted by 1-19 $R^{89}$, $C_{3-11}$cycloalkyl optionally substituted by 1-21 $R^{89}$, $C_{4-17}$cycloalkylalkyl optionally substituted by 1-32 $R^{89}$, 3-15 membered heterocycloalkyl optionally substituted by 1-28 $R^{89}$, 4-21 membered heterocycloalkylalkyl optionally substituted by 1-40 $R^{89}$, 5-15 membered heteroaryl optionally substituted by 1-15 $R^{89}$, 6-21 membered heteroarylalkyl optionally substituted by 1-27 $R^{89}$, halogen, $-CN$, $-C(=O)R^{80}$, $-C(=O)OR^{80}$, $-C(=O)NR^{82}R^{83}$, $-C(=S)NR^{82}R^{83}$, $-NR^{82}R^{83}$, $-NR^{84}C(=O)R^{80}$, $-NR^{84}C(=O)OR^{81}$, $-NR^{84}C(=O)NR^{82}R^{83}$, $-NR^{84}C(=O)NR^{84}C(=O)R^{80}$, $-NR^{84}C(=O)NR^{84}C(=O)OR^{80}$, $-NR^{84}C(=S)R^{80}$, $-NR^{84}S(=O)_2R^{81}$, $-OR^{80}$, $=O$, $-OC(=O)R^{80}$, $-OC(=O)NR^{82}R^{83}$, $=S$, $-S(=O)_nR^{80}$, or $-S(=O)_2NR^{82}R^{83}$; alternatively, when $L^3$, $A^3$, $G^3$, $X^3$, $L^4$, $A^4$, $G^4$ and $X^4$ are absent, $Z^3$ and $Z^4$ can together form a group of formula $-A^{21}-A^{22}-A^{23}-$; wherein $A^{21}$, $A^{22}$, and $A^{23}$ are independently chosen from $-CZ^{21}Z^{22}-$, $-CZ^{23}Z^{24}CZ^{25}Z^{26}-$, $-C(=O)-$, $-NZ^{27}-$, $-S-$, $-S(=O)-$, $-S(=O)_2-$, or $-O-$; wherein:

(a) when any two of $Z^{21}$, $Z^{22}$, $Z^{23}$, $Z^{24}$, $Z^{25}$, $Z^{26}$ and $Z^{27}$ are located on adjacent atoms, they may together form a bond between the atoms, and (b) any of $Z^{21}$, $Z^{22}$, $Z^{23}$, $Z^{24}$, $Z^{25}$, $Z^{26}$ and $Z^{27}$ may be independently chosen from H, $C_{1-6}$alkyl optionally substituted by 1-13 $R^{99}$, $C_{6-11}$ aryl optionally substituted by 1-7 $R^{99}$, $C_{7-16}$arylalkyl optionally substituted by 1-19 $R^{99}$, $C_{3-11}$cycloalkyl optionally substituted by 1-21 $R^{99}$, $C_{4-17}$cycloalkylalkyl optionally substituted by 1-32 $R^{99}$, 3-15 membered heterocycloalkyl optionally substituted by 1-28 $R^{99}$, 4-21 membered heterocycloalkylalkyl optionally substituted by 1-40 $R^{99}$, 5-15 membered heteroaryl optionally substituted by 1-15 $R^{99}$, 6-21 membered heteroarylalkyl optionally substituted by 1-27 $R^{99}$, halogen, $-CN$, $-C(=O)R^{90}$, $-C(=O)OR^{90}$, $-C(=O)NR^{92}R^{93}$, $-C(=S)NR^{92}R^{93}$, $-NR^{92}R^{93}$, $-NR^{94}C(=O)R^{90}$, $-NR^{94}C(=O)OR^{91}$, $-NR^{94}C(=O)NR^{92}R^{93}$, $-NR^{94}C(=O)NR^{94}C(=O)R^{90}$, $-NR^{94}C(=O)NR^{94}C(=O)OR^{90}$, $-NR^{94}C(=S)R^{90}$, $-NR^{94}S(=O)_2R^{91}$, $-OR^{90}$, $=O$, $-OC(=O)R^{90}$, $-OC(=O)NR^{92}R^{93}$, $=S$, $-S(=O)_nR^{90}$, and $-S(=O)_2NR^{92}R^{93}$; and (c) any two of $Z^{21}$, $Z^{22}$, $Z^{23}$, $Z^{24}$, $Z^{25}$, $Z^{26}$ and $Z^{27}$ may together form a group of formula $-A^{31}-A^{32}-A^{33}-$, wherein $A^{31}$, $A^{32}$, and $A^{33}$ are independently chosen from —$CZ^{31}Z^{32}$—, —$CZ^{33}Z^{34}CZ^{35}Z^{36}$—, —C(=O)—, —$NZ^{37}$—, —S—, —S(=O)—, —$S(=O)_2$—, or —O— wherein:

(i) when any two of $Z^{31}$, $Z^{32}$, $Z^{33}$, $Z^{34}$, $Z^{35}$, $Z^{36}$ and $Z^{37}$ are located on adjacent atoms, they may together form a bond between the atoms, and (ii) any of any of $Z^{21}$, $Z^{22}$, $Z^{23}$, $Z^{24}$, $Z^{25}$, $Z^{26}$ and $Z^{27}$ may be independently chosen from H, $C_{1-6}$ alkyl optionally substituted by 1-13 $R^{139}$, $C_{6-11}$ aryl optionally substituted by 1-7 $R^{139}$, $C_{7-16}$ arylalkyl optionally substituted by 1-19 $R^{139}$, $C_{3-11}$ cycloalkyl optionally substituted by 1-21 $R^{139}$, $C_{4-17}$ cycloalkylalkyl optionally substituted by 1-32 $R^{139}$, 3-15 membered heterocycloalkyl optionally substituted by 1-28 $R^{139}$, 4-21 membered heterocycloalkylalkyl optionally substituted by 1-40 $R^{139}$, 5-15 membered heteroaryl optionally substituted by 1-15 $R^{139}$, 6-21 membered heteroarylalkyl optionally substituted by 1-27 $R^{139}$, halogen, —CN, —C(=O)$R^{130}$, —C(=O)O$R^{130}$, —C(=O)N$R^{132}R^{133}$, —C(=S)N$R^{132}R^{133}$, —N$R^{132}R^{133}$, —N$R^{134}$C(=O)$R^{130}$, —N$R^{134}$C(=O)O$R^{131}$, —N$R^{134}$C(=O)N$R^{132}R^{133}$, —N$R^{134}$C(=O)N$R^{134}$C(=O)$R^{130}$, —N$R^{134}$C(=S)$R^{130}$, —N$R^{134}$S(=O)$_2R^{131}$, —O$R^{130}$, =O, —OCN, —OC(=O)$R^{130}$, —OC(=O)N$R^{132}R^{133}$, =S, —S(=O)$_nR^{130}$, and —S(=O)$_2$N$R^{132}R^{133}$. In another embodiment, $Z^4$ is H, $C_{1-6}$ alkyl optionally substituted by 1-13 $R^{89}$, $C_{6-11}$ aryl optionally substituted by 1-7 $R^{89}$, $C_{7-16}$ arylalkyl optionally substituted by 1-19 $R^{89}$, $C_{3-11}$ cycloalkyl optionally substituted by 1-21 $R^{89}$, 3-15 membered heterocycloalkyl optionally substituted by 1-28 $R^{89}$, 5-15 membered heteroaryl optionally substituted by 1-15 $R^{89}$, halogen, —CN, —C(=O)$R^{80}$, —C(=O)O$R^{80}$, —C(=O)N$R^{82}R^{83}$, —N$R^{82}R^{83}$, —N$R^{84}$C(=O)$R^{80}$, —N$R^{84}$C(=O)O$R^{81}$, —N$R^{84}$C(=O)N$R^{82}R^{83}$, —N$R^{84}$S(=O)$_2R^{81}$, —N$R^{84}$P(=O)$R^{88}R^{88}$, —O$R^{80}$, =O, —OC(=O)$R^{80}$, —OC(=O)N$R^{82}R^{83}$, =S, —S(=O)$_nR^{80}$, —S(=O)$_2$N$R^{82}R^{83}$, or —P(=O)$R^{88}R^{88}$; alternatively, when $L^3$, $A^3$, $G^3$, $X^3$, $L^4$, $A^4$, $G^4$ and $X^4$ are absent, $Z^3$ and $Z^4$ can together form a group of formula -$A^{21}$-$A^{22}$-$A^{23}$-; wherein $A^{21}$, $A^{22}$, and $A^{23}$ are independently chosen from —$CZ^{21}Z^{22}$—, —$CZ^{23}Z^{24}CZ^{25}Z^{26}$—, or —$NZ^{27}$—; wherein:

(a) when any two of $Z^{21}$, $Z^{22}$, $Z^{23}$, $Z^{24}$, $Z^{25}$, $Z^{26}$ and $Z^{27}$ are located on adjacent atoms, they may together form a bond between the atoms, and (b) any of $Z^{21}$, $Z^{22}$, $Z^{23}$, $Z^{24}$, $Z^{25}$, $Z^{26}$ and $Z^{27}$ may be independently chosen from H, $C_{1-6}$ alkyl optionally substituted by 1-13 $R^{99}$, $C_{6-11}$ aryl optionally substituted by 1-7 $R^{99}$, $C_{3-11}$ cycloalkyl optionally substituted by 1-21 $R^{99}$, 3-15 membered heterocycloalkyl optionally substituted by 1-28 $R^{99}$, 5-15 membered heteroaryl optionally substituted by 1-15 $R^{99}$, halogen, —CN, —C(=O)$R^{90}$, —C(=O)O$R^{90}$, —C(=O)N$R^{92}R^{93}$, —N$R^{92}R^{93}$, —N$R^{94}$C(=O)$R^{90}$, —N$R^{94}$C(=O)O$R^{91}$, —N$R^{94}$C(=O)N$R^{92}R^{93}$, —N$R^{94}$S(=O)$_2R^{91}$, —N$R^{94}$P(=O)$R^{98}R^{98}$, —O$R^{90}$, =O, —OC(=O)$R^{90}$, —OC(=O)N$R^{92}R^{93}$, =S, —S(=O)$_nR^{90}$, —S(=O)$_2$N$R^{92}R^{93}$, and —P(=O)$R^{98}R^{98}$. In another embodiment, $Z^4$ is H, $C_{1-6}$ alkyl optionally substituted by 1-13 $R^{89}$, $C_{6-11}$ aryl optionally substituted by 1-7 $R^{89}$, $C_{7-16}$ arylalkyl optionally substituted by 1-19 $R^{89}$, $C_{3-11}$ cycloalkyl optionally substituted by 1-21 $R^{89}$, 3-15 membered heterocycloalkyl optionally substituted by 1-28 $R^{89}$, 5-15 membered heteroaryl optionally substituted by 1-15 $R^{89}$, halogen, —CN, —C(=O)$R^{80}$, —C(=O)O$R^{80}$, —C(=O)N$R^{82}R^{83}$, —N$R^{82}R^{83}$, —N$R^{84}$C(=O)$R^{80}$, —N$R^{84}$C(=O)O$R^{81}$, —N$R^{84}$C(=O)N$R^{82}R^{83}$, —N$R^{84}$S(=O)$_2R^{81}$, —O$R^{80}$, =O, —OC(=O)$R^{80}$, —OC(=O)N$R^{82}R^{83}$, =S, —S(=O)$_nR^{80}$, or —S(=O)$_2$N$R^{82}R^{83}$; alternatively, when $L^3$, $A^3$, $G^3$, $X^3$, $L^4$, $A^4$, $G^4$ and $X^4$ are absent, $Z^3$ and $Z^4$ can together form a group of formula -$A^{21}$-$A^{22}$-$A^{23}$-; wherein $A^{21}$, $A^{22}$, and $A^{23}$ are independently chosen from —$CZ^{21}Z^{22}$—, —$CZ^{23}Z^{24}CZ^{25}Z^{26}$—, or —$NZ^{27}$—; wherein:

(a) when any two of $Z^{21}$, $Z^{22}$, $Z^{23}$, $Z^{24}$, $Z^{25}$, $Z^{26}$ and $Z^{27}$ are located on adjacent atoms, they may together form a bond between the atoms, and (b) any of $Z^{21}$, $Z^{22}$, $Z^{23}$, $Z^{24}$, $Z^{25}$, $Z^{26}$ and $Z^{27}$ may be independently chosen from H, $C_{1-6}$ alkyl optionally substituted by 1-13 $R^{99}$, $C_{6-11}$ aryl optionally substituted by 1-7 $R^{99}$, $C_{3-11}$ cycloalkyl optionally substituted by 1-21 $R^{99}$, 3-15 membered heterocycloalkyl optionally substituted by 1-28 $R^{99}$, 5-15 membered heteroaryl optionally substituted by 1-15 $R^{99}$, halogen, —CN, —C(=O)$R^{90}$, —C(=O)O$R^{90}$, —C(=O)N$R^{92}R^{93}$, —N$R^{92}R^{93}$, —N$R^{94}$C(=O)$R^{90}$, —N$R^{94}$C(=O)O$R^{91}$, —N$R^{94}$C(=O)N$R^{92}R^{93}$, —N$R^{94}$S(=O)$_2R^{91}$, —O$R^{90}$, =O, —OC(=O)$R^{90}$, —OC(=O) N$R^{92}R^{93}$, =S, —S(=O)$_nR^{90}$, and —S(=O)$_2$N$R^{92}R^{93}$. In another embodiment, $Z^4$ is H, $C_{1-6}$ alkyl optionally substituted by 1-6 $R^{89}$, $C_{6-11}$ aryl optionally substituted by 1-6 $R^{89}$, $C_{7-16}$ arylalkyl optionally substituted by 1-6 $R^{89}$, $C_{3-11}$ cycloalkyl optionally substituted by 1-6 $R^{89}$, $C_{4-17}$ cycloalkylalkyl optionally substituted by 1-6 $R^{89}$, 3-15 membered heterocycloalkyl optionally substituted by 1-6 $R^{89}$, 4-21 membered heterocycloalkylalkyl optionally substituted by 1-6 $R^{89}$, 5-15 membered heteroaryl optionally substituted by 1-6 $R^{89}$, 6-21 membered heteroarylalkyl optionally substituted by 1-6 $R^{89}$, halogen, —CN, —C(=O)$R^{80}$, —C(=O)O$R^{80}$, —C(=O)N$R^{82}R^{83}$, —C(=O)C(=O)$R^{80}$, —C(=S)N$R^{82}R^{83}$, —NC, —$NO_2$, —N$R^{82}R^{83}$, —N$R^{84}$N$R^{82}R^{83}$, —N$R^{84}$C(=O)$R^{80}$, —N$R^{84}$C(=O)C(=O)$R^{80}$, —N$R^{84}$C(=O)O$R^{81}$, —N$R^{84}$C(=O)C(=O)O$R^{81}$, —N$R^{84}$C(=O)N$R^{82}R^{83}$, —N$R^{84}$C(=O)N$R^{84}$C(=O)O$R^{80}$, —N$R^{84}$C(=O)N$R^{84}$C(=O)O$R^{80}$, —N$R^{84}$C(=N$R^{85}$)N$R^{82}R^{83}$, —N$R^{84}$C(=O)C(=O)N$R^{82}R^{83}$, —N$R^{84}$C(=S)$R^{80}$, —N$R^{84}$C(=S)O$R^{80}$, —N$R^{84}$C(=S)N$R^{82}R^{83}$, —N$R^{84}$S(=O)$_2R^{81}$, —N$R^{84}$S(=O)$_2$N$R^{82}R^{83}$, —N$R^{84}$P(=O)$R^{88}R^{88}$, —O$R^{80}$, =O, —OCN, —OC(=O)$R^{80}$, —OC(=O)N$R^{82}R^{83}$, —OC(=O)O$R^{80}$, —OS(=O)$R^{80}$, —OS(=O)$_2R^{80}$, —OS(=O)$_2$O$R^{80}$, —OS(=O)$_2$N$R^{82}R^{83}$, —SCN, =S, —S(=O)$_nR^{80}$, —S(=O)$_2$O$R^{80}$, —$SO_3R^{87}$, —S(=O)$_2$N$R^{82}R^{83}$, —S(=O)N$R^{82}R^{83}$, or —P(=O)$R^{88}R^{88}$; alternatively, when $L^3$, $A^3$, $G^3$, $X^3$, $L^4$, $A^4$, $G^4$ and $X^4$ are absent, $Z^3$ and $Z^4$ can together form a group of formula -$A^{21}$-$A^{22}$-$A^{23}$-; wherein $A^{21}$, $A^{22}$, and $A^{23}$ are independently chosen from —$CZ^{21}Z^{22}$—, —$CZ^{23}Z^{24}CZ^{25}Z^{26}$—, —C(=O)—, —$NZ^{27}$—, —S—, —S(=O)—, —S(=O)$_2$—, or —O—; wherein:

(a) when any two of $Z^{21}$, $Z^{22}$, $Z^{23}$, $Z^{24}$, $Z^{25}$, $Z^{26}$ and $Z^{27}$ are located on adjacent atoms, they may together form a bond between the atoms, and (b) any of $Z^{21}$, $Z^{22}$, $Z^{23}$, $Z^{24}$, $Z^{25}$, $Z^{26}$ and $Z^{27}$ may be independently chosen from H, $C_{1-6}$ alkyl optionally substituted by 1-6 $R^{99}$, $C_{6-11}$ aryl optionally substituted by 1-7 $R^{99}$, $C_{7-16}$ arylalkyl optionally substituted by 1-6 $R^{99}$, $C_{3-11}$ cycloalkyl optionally substituted by 1-6 $R^{99}$, $C_{4-17}$ cycloalkylalkyl optionally substituted by 1-6 $R^{99}$, 3-15 membered heterocycloalkyl optionally substituted by 1-6 $R^{99}$, 4-21 membered heterocycloalkylalkyl optionally substituted by 1-6 $R^{99}$, 5-15 membered heteroaryl optionally substituted by 1-6 $R^{99}$, 6-21 membered heteroarylalkyl optionally substituted by 1-6 $R^{99}$, halogen, —CN, —C(=O)$R^{90}$, —C(=O)O$R^{90}$, —C(=O)N$R^{92}R^{93}$, —C(=O)C(=O)$R^{90}$, —C(=S)N$R^{92}R^{93}$, —NC, —$NO_2$, —N$R^{92}R^{93}$, —N$R^{94}$N$R^{92}R^{93}$, —N$R^{94}$C(=O)$R^{90}$, —N$R^{94}$C(=O)C(=O)$R^{90}$, —N$R^{94}$C(=O)O$R^{91}$, —N$R^{94}$C(=O)C(=O)O$R^{91}$, —N$R^{94}$C(=O)N$R^{92}R^{93}$, —N$R^{94}$C(=O)N$R^{94}$C(=O)$R^{90}$, —N$R^{94}$C(=O)N$R^{94}$C(=O)O$R^{90}$, —N$R^{94}$C(=N$R^{95}$)N$R^{92}R^{93}$, —N$R^{94}$C(=O)C(=O)

$NR^{92}R^{93}$, $-NR^{94}C(=S)R^{90}$, $-NR^{94}C(=S)OR^{90}$, $-NR^{94}C(=S)NR^{92}R^{93}$, $-NR^{94}S(=O)_2R^{91}$, $-NR^{94}S(=O)_2NR^{92}R^{93}$, $-NR^{94}P(=O)R^{98}R^{98}$, $-OR^{90}$, $=O$, $-OCN$, $-OC$, $-OC(=O)R^{90}$, $-OC(=O)NR^{92}R^{93}$, $-OC(=O)OR^{90}$, $-OS(=O)R^{90}$, $-OS(=O)_2R^{90}$, $-OS(=O)_2OR^{90}$, $-OS(=O)_2NR^{92}R^{93}$, $-SCN$, $=S$, $-S(=O)_nR^{90}$, $-S(=O)_2OR^{90}$, $-SO_3R^{97}$, $-S(=O)_2NR^{92}R^{93}$, $-S(=O)NR^{92}R^{93}$, and $-P(=O)R^{98}R^{98}$; and (c) any two of $Z^{21}$, $Z^{22}$, $Z^{23}$, $Z^{24}$, $Z^{25}$, $Z^{26}$ and $Z^{27}$ may together form a group of formula $-A^{31}-A^{32}-A^{33}-$, wherein $A^{31}$, $A^{32}$, and $A^{33}$ are independently chosen from $-CZ^{31}Z^{32}-$, $-CZ^{33}Z^{34}CZ^{35}Z^{36}-$, $-C(=O)-$, $-NZ^{37}-$, $-S-$, $-S(=O)-$, $-S(=O)_2-$, or $-O-$ wherein:

(i) when any two of $Z^{31}$, $Z^{32}$, $Z^{33}$, $Z^{34}$, $Z^{35}$, $Z^{36}$ and $Z^{37}$ are located on adjacent atoms, they may together form a bond between the atoms, and (ii) any of any of $Z^{21}$, $Z^{22}$, $Z^{23}$, $Z^{24}$, $Z^{25}$, $Z^{26}$ and $Z^{27}$ may be independently chosen from H, $C_{1-6}$alkyl optionally substituted by 1-6 $R^{139}$, $C_{6-11}$aryl optionally substituted by 1-7 $R^{139}$, $C_{7-16}$arylalkyl optionally substituted by 1-6 $R^{139}$, $C_{3-11}$cycloalkyl optionally substituted by 1-6 $R^{139}$, $C_{4-17}$cycloalkylalkyl optionally substituted by 1-6 $R^{139}$, 3-15 membered heterocycloalkyl optionally substituted by 1-6 $R^{139}$, 4-21 membered heterocycloalkylalkyl optionally substituted by 1-6 $R^{139}$, 5-15 membered heteroaryl optionally substituted by 1-6 $R^{139}$, 6-21 membered heteroarylalkyl optionally substituted by 1-6 $R^{139}$, halogen, $-CN$, $-C(=O)R^{130}$, $-C(=O)OR^{130}$, $-C(=O)NR^{132}R^{133}$, $-C(=O)C(=O)R^{130}$, $-C(=S)NR^{132}R^{133}$, $-NC$, $-NO_2$, $-NR^{132}R^{133}$, $-NR^{134}NR^{132}R^{133}$, $-NR^{134}C(=O)R^{130}$, $-NR^{134}C(=O)C(=O)R^{130}$, $-NR^{134}C(=O)OR^{131}$, $-NR^{134}C(=O)C(=O)OR^{131}$, $-NR^{134}C(=O)NR^{132}R^{133}$, $-NR^{134}C(=O)NR^{134}C(=O)R^{130}$, $-NR^{134}C(=O)NR^{134}C(=O)OR^{130}$, $-NR^{134}C(=NR^{135})NR^{132}R^{133}$, $-NR^{134}C(=O)C(=O)NR^{132}R^{133}$, $-NR^{134}C(=S)R^{130}$, $-NR^{134}C(=S)OR^{130}$, $-NR^{134}C(=S)NR^{132}R^{133}$, $-NR^{134}S(=O)_2R^{131}$, $-NR^{134}S(=O)_2NR^{132}R^{133}$, $-NR^{134}P(=O)R^{138}R^{138}$, $-OR^{130}$, $=O$, $-OCN$, $-OC(=O)R^{130}$, $-OC(=O)NR^{132}R^{133}$, $-OC(=O)OR^{130}$, $-OS(=O)R^{130}$, $-OS(=O)_2R^{130}$, $-OS(=O)_2OR^{130}$, $-OS(=O)_2NR^{132}R^{133}$, $-SCN$, $=S$, $-S(=O)_nR^{130}$, $-S(=O)_2OR^{130}$, $-SO_3R^{137}$, $-S(=O)_2NR^{132}R^{133}$, $-S(=O)NR^{132}R^{133}$, and $-P(=O)R^{138}R^{138}$. In another embodiment, $Z^4$ is H, $C_{1-6}$alkyl optionally substituted by 1-6 $R^{89}$, $C_{6-11}$aryl optionally substituted by 1-6 $R^{89}$, $C_{7-16}$arylalkyl optionally substituted by 1-6 $R^{89}$, $C_{3-11}$cycloalkyl optionally substituted by 1-6 $R^{89}$, $C_{4-17}$cycloalkylalkyl optionally substituted by 1-6 $R^{89}$, 3-15 membered heterocycloalkyl optionally substituted by 1-6 $R^{89}$, 4-21 membered heterocycloalkylalkyl optionally substituted by 1-6 $R^{89}$, 5-15 membered heteroaryl optionally substituted by 1-6 $R^{89}$, 6-21 membered heteroarylalkyl optionally substituted by 1-6 $R^{89}$, halogen, $-CN$, $-C(=O)R^{80}$, $-C(=O)OR^{80}$, $-C(=O)NR^{82}R^{83}$, $-C(=O)C(=O)R^{80}$, $-C(=S)NR^{82}R^{83}$, $-NC$, $-NO_2$, $-NR^{82}R^{83}$, $-NR^{84}R^{82}R^{83}$, $-NR^{84}C(=O)R^{80}$, $-NR^{84}C(=O)C(=O)R^{80}$, $-NR^{84}C(=O)OR^{81}$, $-NR^{84}C(=O)C(=O)OR^{81}$, $-NR^{84}C(=O)NR^{82}R^{83}$, $-NR^{84}C(=O)NR^{84}C(=O)R^{80}$, $-NR^{84}C(=O)OR^{80}$, $-NR^{84}C(=NR^{85})NR^{82}R^{83}$, $-NR^{84}C(=O)C(=O)NR^{82}R^{83}$, $-NR^{84}C(=S)R^{80}$, $-NR^{84}C(=S)OR^{80}$, $-NR^{84}C(=S)NR^{82}R^{83}$, $-NR^{84}S(=O)_2R^{81}$, $-NR^{84}S(=O)_2NR^{82}R^{83}$, $-OR^{80}$, $=O$, $-OCN$, $-OC(=O)R^{80}$, $-OC(=O)NR^{82}R^{83}$, $-OC(=O)OR^{80}$, $-OS(=O)R^{80}$, $-OS(=O)_2R^{80}$, $-OS(=O)_2OR^{80}$, $-OS(=O)_2NR^{82}R^{83}$, $-SCN$, $=S$, $-S(=O)_nR^{80}$, $-S(=O)_2OR^{80}$, $-SO_3R^{87}$, $-S(=O)_2NR^{82}R^{83}$, or $-S(=O)NR^{82}R^{83}$; alternatively, when $L^3$, $A^3$, $G^3$, $X^3$, $L^4$, $A^4$, $G^4$ and $X^4$ are absent, $Z^3$ and $Z^4$ can together form a group of formula $-A^{21}-A^{22}-A^{23}-$; wherein $A^{21}$, $A^{22}$, and $A^{23}$ are independently chosen from $-CZ^{21}Z^{22}-$, $-CZ^{23}Z^{24}CZ^{25}Z^{26}-$, $-C(=O)-$, $-NZ^{27}-$, $-S-$, $-S(=O)-$, $-S(=O)_2-$, or $-O-$; wherein:

(a) when any two of $Z^{21}$, $Z^{22}$, $Z^{23}$, $Z^{24}$, $Z^{25}$, $Z^{26}$ and $Z^{27}$ are located on adjacent atoms, they may together form a bond between the atoms, and (b) any of $Z^{21}$, $Z^{22}$, $Z^{23}$, $Z^{24}$, $Z^{25}$, $Z^{26}$ and $Z^{27}$ may be independently chosen from H, $C_{1-6}$alkyl optionally substituted by 1-6 $R^{99}$, $C_{6-11}$aryl optionally substituted by 1-7 $R^{99}$, $C_{7-16}$arylalkyl optionally substituted by 1-6 $R^{99}$, $C_{3-11}$cycloalkyl optionally substituted by 1-6 $R^{99}$, $C_{4-17}$cycloalkylalkyl optionally substituted by 1-6 $R^{99}$, 3-15 membered heterocycloalkyl optionally substituted by 1-6 $R^{99}$, 4-21 membered heterocycloalkylalkyl optionally substituted by 1-6 $R^{99}$, 5-15 membered heteroaryl optionally substituted by 1-6 $R^{99}$, 6-21 membered heteroarylalkyl optionally substituted by 1-6 $R^{99}$, halogen, $-CN$, $-C(=O)R^{90}$, $-C(=O)OR^{90}$, $-C(=O)NR^{92}R^{93}$, $-C(=O)C(=O)R^{90}$, $-C(=S)NR^{92}R^{93}$, $-NC$, $-NO_2$, $-NR^{92}R^{93}$, $-NR^{94}NR^{92}R^{93}$, $-NR^{94}C(=O)R^{90}$, $-NR^{94}C(=O)C(=O)R^{90}$, $-NR^{94}C(=O)OR^{91}$, $-NR^{94}C(=O)C(=O)OR^{91}$, $-NR^{94}C(=O)NR^{92}R^{93}$, $-NR^{94}C(=O)NR^{94}C(=O)R^{90}$, $-NR^{94}C(=O)OR^{90}$, $-NR^{94}C(=NR^{95})NR^{92}R^{93}$, $-NR^{94}C(=O)C(=O)NR^{92}R^{93}$, $-NR^{94}C(=S)R^{90}$, $-NR^{94}C(=S)OR^{90}$, $-NR^{94}C(=S)NR^{92}R^{93}$, $-NR^{94}S(=O)_2R^{91}$, $-NR^{94}S(=O)_2NR^{92}R^{93}$, $-OR^{90}$, $=O$, $-OCN$, $-OC(=O)R^{90}$, $-OC(=O)NR^{92}R^{93}$, $-OC(=O)OR^{90}$, $-OS(=O)R^{90}$, $-OS(=O)_2R^{90}$, $-OS(=O)_2OR^{90}$, $-OS(=O)_2NR^{92}R^{93}$, $-SCN$, $=S$, $-S(=O)_nR^{90}$, $-S(=O)_2OR^{90}$, $-SO_3R^{97}$, $-S(=O)_2NR^{92}R^{93}$, and $-S(=O)NR^{92}R^{93}$; and (c) any two of $Z^{21}$, $Z^{22}$, $Z^{23}$, $Z^{24}$, $Z^{25}$, $Z^{26}$ and $Z^{27}$ may together form a group of formula $-A^{31}-A^{32}-A^{33}-$, wherein $A^{31}$, $A^{32}$, and $A^{33}$ are independently chosen from $-CZ^{31}Z^{32}-$, $-CZ^{33}Z^{34}CZ^{35}Z^{36}-$, $-C(=O)-$, $-NZ^{37}-$, $-S-$, $-S(=O)-$, $-S(=O)_2-$, or $-O-$ wherein:

(i) when any two of $Z^{31}$, $Z^{32}$, $Z^{33}$, $Z^{34}$, $Z^{35}$, $Z^{36}$ and $Z^{37}$ are located on adjacent atoms, they may together form a bond between the atoms, and (ii) any of any of $Z^{21}$, $Z^{22}$, $Z^{23}$, $Z^{24}$, $Z^{25}$, $Z^{26}$ and $Z^{27}$ may be independently chosen from H, $C_{1-6}$alkyl optionally substituted by 1-6 $R^{139}$, $C_{6-11}$aryl optionally substituted by 1-7 $R^{139}$, $C_{7-16}$arylalkyl optionally substituted by 1-6 $R^{139}$, $C_{3-11}$cycloalkyl optionally substituted by 1-6 $R^{139}$, $C_{4-17}$cycloalkylalkyl optionally substituted by 1-6 $R^{139}$, 3-15 membered heterocycloalkyl optionally substituted by 1-6 $R^{139}$, 4-21 membered heterocycloalkylalkyl optionally substituted by 1-6 $R^{139}$, 5-15 membered heteroaryl optionally substituted by 1-6 $R^{139}$, 6-21 membered heteroarylalkyl optionally substituted by 1-6 $R^{139}$, halogen, $-CN$, $-C(=O)R^{130}$, $-C(=O)OR^{130}$, $-C(=O)NR^{132}R^{133}$, $-C(=O)C(=O)R^{130}$, $-C(=S)NR^{132}R^{133}$, $-NC$, $-NO_2$, $-NR^{132}R^{133}$, $-NR^{134}NR^{132}R^{133}$, $-NR^{134}C(=O)R^{130}$, $-NR^{134}C(=O)C(=O)R^{130}$, $-NR^{134}C(=O)OR^{131}$, $-NR^{134}C(=O)C(=O)OR^{131}$, $-NR^{134}C(=O)NR^{132}R^{133}$, $-NR^{134}C(=O)NR^{134}C(=O)R^{130}$, $-NR^{134}C(=O)NR^{134}C(=O)OR^{130}$, $-NR^{134}C(=NR^{135})NR^{132}R^{133}$, $-NR^{134}C(=O)C(=O)NR^{132}R^{133}$, $-NR^{134}C(=S)R^{130}$, $-NR^{134}C(=S)OR^{130}$, $-NR^{134}C(=S)NR^{132}R^{133}$, $-NR^{134}S(=O)_2R^{131}$, $-NR^{134}S(=O)_2NR^{132}R^{133}$, $-OR^{130}$, $=O$, $-OCN$, $-OC(=O)R^{130}$, $-OC(=O)NR^{132}R^{133}$, $-OC(=O)OR^{130}$, $-OS(=O)R^{130}$, $-OS(=O)_2R^{130}$, $-OS(=O)_2OR^{130}$, $-OS(=O)_2NR^{132}R^{133}$, $-SCN$, $=S$, $-S(=O)_nR^{130}$, $-S(=O)_2OR^{130}$, $-SO_3R^{137}$, $-S(=O)_2NR^{132}R^{133}$, and $-S(=O)NR^{132}R^{133}$. In another embodiment, $Z^4$ is H, $C_{1-6}$alkyl optionally substituted by 1-6 $R^{89}$, $C_{6-11}$aryl optionally substituted by 1-7 $R^{89}$, $C_{7-16}$arylalkyl optionally substituted by 1-6 $R^{89}$, $C_{3-11}$cycloalkyl optionally substituted by 1-6 $R^{89}$, $C_{4-17}$cycloalkylalkyl optionally substituted by 1-6 $R^{89}$, 3-15 membered heterocycloalkyl optionally substituted by 1-6 $R^{89}$, 4-21 membered heterocycloalkylalkyl optionally substituted by 1-6 $R^{89}$, 5-15 membered heteroaryl optionally substituted by 1-6 $R^{89}$, 6-21 membered heteroarylalkyl optionally substituted by 1-6 $R^{89}$, halogen, —CN, —C(=O)$R^{80}$, —C(=O)O$R^{80}$, —C(=O)N$R^{82}R^{83}$, —C(=S)N$R^{82}R^{83}$, —NC, —NO$_2$, —N$R^{82}R^{83}$, —N$R^{84}$N$R^{82}R^{83}$, —N$R^{84}$C(=O)$R^{80}$, —N$R^{84}$C(=O)O$R^{81}$, —N$R^{84}$C(=O)N$R^{82}R^{83}$, —N$R^{84}$C(=O)N$R^{84}$C(=O)$R^{80}$, —N$R^{84}$C(=O)N$R^{84}$C(=O)O$R^{80}$, —N$R^{84}$C(=N$R^{85}$)N$R^{82}R^{83}$, —N$R^{84}$C(=S)$R^{80}$, —N$R^{84}$C(=S)N$R^{82}R^{83}$, —N$R^{84}$S(=O)$_2R^{81}$, —O$R^{80}$, =O, —OCN, —OC(=O)$R^{80}$, —OC(=O)N$R^{82}R^{83}$, —SCN, =S, —S(=O)$_n R^{80}$, —S(=O)$_2$O$R^{80}$, or —S(=O)$_2$N$R^{82}R^{83}$; alternatively, when $L^3$, $A^3$, $G^3$, $X^3$, $L^4$, $A^4$, $G^4$ and $X^4$ are absent, $Z^3$ and $Z^4$ can together form a group of formula -$A^{21}$-$A^{22}$-$A^{23}$-; wherein $A^{21}$, $A^{22}$, and $A^{23}$ are independently chosen from —C$Z^{21}Z^{22}$—, —C$Z^{23}Z^{24}$C$Z^{25}Z^{26}$—, —C(=O)—, —N$Z^{27}$—, —S—, —S(=O)—, —S(=O)$_2$—, or —O—; wherein:

(a) when any two of $Z^{21}$, $Z^{22}$, $Z^{23}$, $Z^{24}$, $Z^{25}$, $Z^{26}$ and $Z^{27}$ are located on adjacent atoms, they may together form a bond between the atoms, and (b) any of $Z^{21}$, $Z^{22}$, $Z^{23}$, $Z^{24}$, $Z^{25}$, $Z^{26}$ and $Z^{27}$ may be independently chosen from H, $C_{1-6}$alkyl optionally substituted by 1-6 $R^{99}$, $C_{6-11}$aryl optionally substituted by 1-7 $R^{99}$, $C_{7-16}$arylalkyl optionally substituted by 1-6 $R^{99}$, $C_{3-11}$cycloalkyl optionally substituted by 1-6 $R^{99}$, $C_{4-17}$cycloalkylalkyl optionally substituted by 1-6 $R^{99}$, 3-15 membered heterocycloalkyl optionally substituted by 1-6 $R^{99}$, 4-21 membered heterocycloalkylalkyl optionally substituted by 1-6 $R^{99}$, 5-15 membered heteroaryl optionally substituted by 1-6 $R^{99}$, 6-21 membered heteroarylalkyl optionally substituted by 1-6 $R^{99}$, halogen, —CN, —C(=O)$R^{90}$, —C(=O)O$R^{90}$, —C(=O)N$R^{92}R^{93}$, —C(=S)N$R^{92}R^{93}$, —NC, —NO$_2$, —N$R^{92}R^{93}$, —N$R^{94}$N$R^{92}R^{93}$, —N$R^{94}$C(=O)$R^{90}$, —N$R^{94}$C(=O)O$R^{91}$, —N$R^{94}$C(=O)N$R^{92}R^{93}$, —N$R^{94}$C(=O)N$R^{94}$C(=O)$R^{90}$, —N$R^{94}$C(=O)N$R^{94}$C(=O)O$R^{90}$, —N$R^{94}$C(=N$R^{95}$)N$R^{92}R^{93}$, —N$R^{94}$C(=S)$R^{90}$, —N$R^{94}$C(=S)N$R^{92}R^{93}$, —N$R^{94}$S(=O)$_2R^{91}$, —O$R^{90}$, =O, —OCN, —OC(=O)N$R^{92}R^{93}$, —SCN, =S, —S(=O)$_n R^{90}$, and —S(=O)$_2$N$R^{92}R^{93}$; and (c) any two of $Z^{21}$, $Z^{22}$, $Z^{23}$, $Z^{24}$, $Z^{25}$, $Z^{26}$ and $Z^{27}$ may together form a group of formula -$A^{31}$-$A^{32}$-$A^{33}$-, wherein $A^{31}$, $A^{32}$, and $A^{33}$ are independently chosen from —C$Z^{31}Z^{32}$—, —C$Z^{33}Z^{34}$C$Z^{35}Z^{36}$—, —C(=O)—, —N$Z^{37}$—, —S—, —S(=O)$_2$—, —S(=O)$_2$—, or —O— wherein:

(i) when any two of $Z^{31}$, $Z^{32}$, $Z^{33}$, $Z^{34}$, $Z^{35}$, $Z^{36}$ and $Z^{37}$ are located on adjacent atoms, they may together form a bond between the atoms, and (ii) any of any of $Z^{21}$, $Z^{22}$, $Z^{23}$, $Z^{24}$, $Z^{25}$, $Z^{26}$ and $Z^{27}$ may be independently chosen from H, $C_{1-6}$alkyl optionally substituted by 1-6 $R^{139}$, $C_{6-11}$aryl optionally substituted by 1-7 $R^{139}$, $C_{7-16}$arylalkyl optionally substituted by 1-6 $R^{139}$, $C_{3-11}$cycloalkyl optionally substituted by 1-6 $R^{139}$, $C_{4-17}$cycloalkylalkyl optionally substituted by 1-6 $R^{139}$, 3-15 membered heterocycloalkyl optionally substituted by 1-6 $R^{139}$, 4-21 membered heterocycloalkylalkyl optionally substituted by 1-6 $R^{139}$, 5-15 membered heteroaryl optionally substituted by 1-6 $R^{139}$, 6-21 membered heteroarylalkyl optionally substituted by 1-6 $R^{139}$, halogen, —CN, —C(=O)O$R^{130}$, —C(=O)O$R^{130}$, —C(=O)N$R^{132}R^{133}$, —C(=S)N$R^{132}R^{133}$, —NC, —NO$_2$, —N$R^{132}R^{133}$, —N$R^{134}$N$R^{132}R^{133}$, —N$R^{134}$C(=O)$R^{130}$, —N$R^{134}$(=O)O$R^{131}$, N$R^{134}$C(=O)N$R^{132}R^{133}$, —N$R^{134}$C(=O)N$R^{134}$C(=O)$R^{130}$, —N$R^{134}$C(=N$R^{135}$)N$R^{132}R^{133}$, —N$R^{134}$C(=S)$R^{130}$, —N$R^{134}$C(=S)N$R^{132}R^{133}$, —N$R^{134}$S(=O)$_2R^{131}$, —O$R^{130}$, =O, —OCN, —OC(=O)$R^{130}$, —OC(=O)N$R^{132}R^{133}$, —SCN, =S, —S(=O)$_n R^{130}$, and —S(=O)$_2$N$R^{132}R^{133}$. In another embodiment, $Z^4$ is H, $C_{1-6}$alkyl optionally substituted by 1-6 $R^{89}$, $C_{6-11}$aryl optionally substituted by 1-7 $R^{89}$, $C_{7-16}$arylalkyl optionally substituted by 1-6 $R^{89}$, $C_{3-11}$cycloalkyl optionally substituted by 1-6 $R^{89}$, $C_{4-17}$cycloalkylalkyl optionally substituted by 1-6 $R^{89}$, 3-15 membered heterocycloalkyl optionally substituted by 1-6 $R^{89}$, 4-21 membered heterocycloalkylalkyl optionally substituted by 1-6 $R^{89}$, 5-15 membered heteroaryl optionally substituted by 1-6 $R^{89}$, 6-21 membered heteroarylalkyl optionally substituted by 1-6 $R^{89}$, halogen, —CN, —C(=O)$R^{80}$, —C(=O)O$R^{80}$, —C(=O)N$R^{82}R^{83}$, —C(=S)N$R^{82}R^{83}$, —N$R^{82}R^{83}$, —N$R^{84}$C(=O)$R^{80}$, —N$R^{84}$C(=O)O$R^{81}$, —N$R^{84}$C(=O)N$R^{82}R^{83}$, —N$R^{84}$C(=O)N$R^{84}$C(=O)$R^{80}$, —N$R^{84}$C(=O)N$R^{84}$C(=O)O$R^{80}$, —N$R^{84}$C(=S)$R^{80}$, —N$R^{84}$S(=O)$_2R^{81}$, —N$R^{84}$P(=O)$R^{88}R^{88}$, —O$R^{80}$, =O, —OC(=O)$R^{80}$, —OC(=O)N$R^{82}R^{83}$, =S, —S(=O)$_n R^{80}$, —S(=O)$_2$N$R^{82}R^{83}$, or —P(=O)$R^{88}R^{88}$; alternatively, when $L^3$, $A^3$, $G^3$, $X^3$, $L^4$, $A^4$, $G^4$ and $X^4$ are absent, $Z^3$ and $Z^4$ can together form a group of formula -$A^{21}$-$A^{22}$-$A^{23}$-; wherein $A^{21}$, $A^{22}$, and $A^{23}$ are independently chosen from —C$Z^{21}Z^{22}$—, —C$Z^{23}Z^{24}$C$Z^{25}Z^{26}$—, —C(=O)—, —N$Z^{27}$—, —S—, —S(=O)—, —S(=O)$_2$—, or —O—; wherein:

(a) when an two of $Z^{21}$, $Z^{22}$, $Z^{23}$, $Z^{24}$, $Z^{25}$, $Z^{26}$ and $Z^{27}$ are located on adjacent atoms, they may together form a bond between the atoms, and (b) any of $Z^{21}$, $Z^{22}$, $Z^{23}$, $Z^{24}$, $Z^{25}$, $Z^{26}$ and $Z^{27}$ may be independently chosen from H, $C_{1-6}$alkyl optionally substituted by 1-6 $R^{99}$, $C_{6-11}$aryl optionally substituted by 1-7 $R^{99}$, $C_{7-16}$arylalkyl optionally substituted by 1-6 $R^{99}$, $C_{3-11}$cycloalkyl optionally substituted by 1-6 $R^{99}$, $C_{4-17}$cycloalkylalkyl optionally substituted by 1-6 $R^{99}$, 3-15 membered heterocycloalkyl optionally substituted by 1-6 $R^{99}$, 4-21 membered heterocycloalkylalkyl optionally substituted by 1-6 $R^{99}$, 5-15 membered heteroaryl optionally substituted by 1-6 $R^{99}$, 6-21 membered heteroarylalkyl optionally substituted by 1-6 $R^{99}$, halogen, —CN, —C(=O)$R^{90}$, —C(=O)O$R^{90}$, —C(=O)N$R^{92}R^{93}$, —C(=S)N$R^{92}R^{93}$, —N$R^{92}R^{93}$, —N$R^{94}$C(=O)$R^{90}$, —N$R^{94}$C(=O)O$R^{91}$, —N$R^{94}$C(=O)N$R^{92}R^{93}$, —N$R^{94}$C(=O)N$R^{94}$C(=O)$R^{90}$, —N$R^{94}$C(=O)N$R^{94}$C(=O)O$R^{90}$, —N$R^{94}$C(=S)$R^{90}$, —N$R^{94}$S(=O)$_2R^{91}$, —N$R^{94}$P(=O)$R^{98}R^{98}$, —O$R^{90}$, =O, —OC(=O)$R^{90}$, —OC(=O)N$R^{92}R^{93}$, =S, —S(=O)$_n R^{90}$, —S(=O)$_2$N$R^{92}R^{93}$, and —P(=O)$R^{98}R^{98}$; and (c) any two of $Z^{21}$, $Z^{22}$, $Z^{23}$, $Z^{24}$, $Z^{25}$, $Z^{26}$ and $Z^{27}$ may together form a group of formula -$A^{31}$-$A^{32}$-$A^{33}$-, wherein $A^{31}$, $A^{32}$, and $A^{33}$ are independently chosen from —C$Z^{31}Z^{32}$—, —C$Z^{33}Z^{34}$C$Z^{35}Z^{36}$—, —C(=O)—, —N$Z^{37}$—, —S—, —S(=O)—, —S(=O)$_2$—, or —O— wherein:

(i) when any two of $Z^{31}$, $Z^{32}$, $Z^{33}$, $Z^{34}$, $Z^{35}$, $Z^{36}$ and $Z^{37}$ are located on adjacent atoms, they may together form a bond between the atoms, and (ii) any of any of $Z^{21}$, $Z^{22}$, $Z^{23}$, $Z^{24}$, $Z^{25}$, $Z^{26}$ and $Z^{27}$ may be independently chosen from H, $C_{1-6}$alkyl optionally substituted by 1-6 $R^{139}$, $C_{6-11}$aryl optionally substituted by 1-7 $R^{139}$, $C_{7-16}$arylalkyl optionally substituted by 1-6 $R^{139}$, $C_{3-11}$cycloalkyl optionally substituted by 1-6 $R^{139}$, $C_{4-17}$cycloalkylalkyl optionally substituted by 1-6 $R^{139}$, 3-15 membered heterocycloalkyl optionally substituted by 1-6 $R^{139}$, 4-21 membered heterocycloalkylalkyl optionally substituted by 1-6 $R^{139}$, 5-15 membered heteroaryl optionally substituted by 1-6 $R^{139}$, 6-21 membered heteroarylalkyl optionally substituted by 1-6 $R^{139}$, halogen, —CN, —C(=O)$R^{130}$, —C(=O)O$R^{130}$, —C(=O)N$R^{132}R^{133}$, —C(=S)N$R^{132}R^{133}$, —N$R^{132}R^{133}$, —N$R^{134}$C(=O)$R^{130}$, —N$R^{134}$C(=O)O$R^{131}$, —N$R^{134}$C(=O)N$R^{132}R^{133}$, —N$R^{134}$C(=O)N$R^{134}$C(=O)$R^{130}$, —N$R^{134}$C(=S)$R^{130}$, —N$R^{134}$S(=O)$_2$$R^{131}$, —N$R^{134}$P(=O)$R^{138}R^{138}$, —O$R^{130}$, =O, —OCN, —OC(=O)$R^{130}$, —OC(=O)N$R^{132}R^{133}$, =S, —S(=O)$_n$$R^{130}$, —S(=O)$_2$N$R^{132}R^{133}$, and —P(=O)$R^{138}R^{138}$. In another embodiment, $Z^4$ is H, $C_{1-6}$alkyl optionally substituted by 1-6 $R^{89}$, $C_{6-11}$ aryl optionally substituted by 1-7 $R^{89}$, $C_{7-16}$arylalkyl optionally substituted by 1-6 $R^{89}$, $C_{3-11}$cycloalkyl optionally substituted by 1-6 $R^{89}$, $C_{4-17}$cycloalkylalkyl optionally substituted by 1-6 $R^{89}$, 3-15 membered heterocycloalkyl optionally substituted by 1-6 $R^{89}$, 4-21 membered heterocycloalkylalkyl optionally substituted by 1-6 $R^{89}$, 5-15 membered heteroaryl optionally substituted by 1-6 $R^{89}$, 6-21 membered heteroarylalkyl optionally substituted by 1-6 $R^{89}$, halogen, —CN, —C(=O)$R^{80}$, —C(=O)O$R^{80}$, —C(=O)N$R^{82}R^{83}$, —C(=S)N$R^{82}R^{83}$, —N$R^{84}$C(=O)$R^{80}$, —N$R^{84}$C(=O)O$R^{81}$, —N$R^{84}$C(=O)N$R^{82}R^{83}$, —N$R^{84}$C(=O)N$R^{84}$C(=O)$R^{80}$, —N$R^{84}$C(=O)N$R^{84}$C(=O)O$R^{80}$, —N$R^{84}$C(=S)$R^{80}$, —N$R^{84}$S(=O)$_2$$R^{81}$, —O$R^{80}$, =O, —OC(=O)$R^{80}$, —OC(=O)N$R^{82}R^{83}$, =S, —S(=O)$_n$$R^{80}$, or —S(=O)$_2$N$R^{82}R^{83}$; alternatively, when $L^3$, $A^3$, $G^3$, $X^3$, $L^4$, $A^4$, $G^4$ and $X^4$ are absent, $Z^3$ and $Z^4$ can together form a group of formula -$A^{21}$-$A^{22}$-$A^{23}$-; wherein $A^{21}$, $A^{22}$, and $A^{23}$ are independently chosen from —C$Z^{21}Z^{22}$—, —C$Z^{23}Z^{24}$C$Z^{25}Z^{26}$—, —C(=O)—, —N$Z^{27}$—, —S—, —S(=O)—, —S(=O)$_2$—, or —O—; wherein:

(a) when any two of $Z^{21}$, $Z^{22}$, $Z^{23}$, $Z^{24}$, $Z^{25}$, $Z^{26}$ and $Z^{27}$ are located on adjacent atoms, they may together form a bond between the atoms, and (b) any of $Z^{21}$, $Z^{22}$, $Z^{23}$, $Z^{24}$, $Z^{25}$, $Z^{26}$ and $Z^{27}$ may be independently chosen from H, $C_{1-6}$alkyl optionally substituted by 1-6 $R^{99}$, $C_{6-11}$aryl optionally substituted by 1-7 $R^{99}$, $C_{7-16}$arylalkyl optionally substituted by 1-6 $R^{99}$, $C_{3-11}$cycloalkyl optionally substituted by 1-6 $R^{99}$, $C_{4-17}$cycloalkylalkyl optionally substituted by 1-6 $R^{99}$, 3-15 membered heterocycloalkyl optionally substituted by 1-6 $R^{99}$, 4-21 membered heterocycloalkylalkyl optionally substituted by 1-6 $R^{99}$, 5-15 membered heteroaryl optionally substituted by 1-6 $R^{99}$, 6-21 membered heteroarylalkyl optionally substituted by 1-6 $R^{99}$, halogen, —CN, —C(=O)$R^{90}$, —C(=O)O$R^{90}$, —C(=O)N$R^{92}R^{93}$, —C(=S)N$R^{92}R^{93}$, —N$R^{92}R^{93}$, —N$R^{94}$C(=O)$R^{90}$, —N$R^{94}$C(=O)O$R^{91}$, —N$R^{94}$C(=O)N$R^{92}R^{93}$, —N$R^{94}$C(=O)N$R^{94}$C(=O)$R^{90}$, —N$R^{94}$C(=O)N$R^{94}$C(=O)O$R^{90}$, —N$R^{94}$C(=S)$R^{90}$, —N$R^{94}$S(=O)$_2$$R^{91}$, —O$R^{90}$, =O, —OC(=O)$R^{90}$, —OC(=O)N$R^{92}R^{93}$, =S, —S(=O)$_n$$R^{90}$, and —S(=O)$_2$N$R^{92}R^{93}$; and (c) any two of $Z^{21}$, $Z^{22}$, $Z^{23}$, $Z^{24}$, $Z^{25}$, $Z^{26}$ and $Z^{27}$ may together form a group of formula -$A^{31}$-$A^{32}$-$A^{33}$-5 wherein $A^{31}$, $A^{32}$, and $A^{33}$ are independently chosen from —C$Z^{31}Z^{32}$—, —C$Z^{33}Z^{34}$C$Z^{35}Z^{36}$—, —C(=O)—, —N$Z^{37}$—, —S—, —S(=O)—, —S(=O)$_2$—, or —O— wherein:

(i) when any two of $Z^{31}$, $Z^{32}$, $Z^{33}$, $Z^{34}$, $Z^{35}$, $Z^{36}$ and $Z^{37}$ are located on adjacent atoms, they may together form a bond between the atoms, and (ii) any of any of $Z^{21}$, $Z^{22}$, $Z^{23}$, $Z^{24}$, $Z^{25}$, $Z^{26}$ and $Z^{27}$ may be independently chosen from H, $C_{1-6}$alkyl optionally substituted by 1-6 $R^{139}$, $C_{6-11}$aryl optionally substituted by 1-7 $R^{139}$, $C_{7-16}$arylalkyl optionally substituted by 1-6 $R^{139}$, $C_{3-11}$cycloalkyl optionally substituted by 1-6 $R^{139}$, $C_{4-17}$cycloalkylalkyl optionally substituted by 1-6 $R^{139}$, 3-15 membered heterocycloalkyl optionally substituted by 1-6 $R^{139}$, 4-21 membered heterocycloalkylalkyl optionally substituted by 1-6 $R^{139}$, 5-15 membered heteroaryl optionally substituted by 1-6 $R^{139}$, 6-21 membered heteroarylalkyl optionally substituted by 1-6 $R^{139}$, halogen, —CN, —C(=O)$R^{130}$, —C(=O)O$R^{130}$, —C(=O)N$R^{132}R^{133}$, —C(=S)N$R^{132}R^{133}$, —N$R^{132}R^{133}$, —N$R^{134}$C(=O)$R^{130}$, —N$R^{134}$C(=O)O$R^{131}$, —N$R^{134}$C(=O)N$R^{132}R^{133}$, —N$R^{134}$C(=O)N$R^{134}$C(=O)$R^{130}$, —N$R^{134}$C(=S)$R^{130}$, —N$R^{134}$S(=O)$_2$$R^{131}$, —O$R^{130}$, =O, —OCN, —OC(=O)$R^{130}$, —OC(=O)N$R^{132}R^{133}$, =S, —S(=O)$_n$$R^{130}$, and —S(=O)$_2$N$R^{132}R^{133}$.

In another embodiment, $Z^4$ is H, $C_{1-6}$alkyl optionally substituted by 1-6 $R^{89}$, $C_{6-11}$aryl optionally substituted by 1-7 $R^{89}$, $C_{7-16}$arylalkyl optionally substituted by 1-6 $R^{89}$, $C_{3-11}$cycloalkyl optionally substituted by 1-6 $R^{89}$, $C_{4-17}$cycloalkylalkyl optionally substituted by 1-6 $R^{89}$, 3-15 membered heterocycloalkyl optionally substituted by 1-6 $R^{89}$, 4-21 membered heterocycloalkylalkyl optionally substituted by 1-6 $R^{89}$, 5-15 membered heteroaryl optionally substituted by 1-6 $R^{89}$, 6-21 membered heteroarylalkyl optionally substituted by 1-6 $R^{89}$, halogen, —CN, —C(=O)$R^{80}$, —C(=O)O$R^{80}$, —C(=O)N$R^{82}R^{83}$, —N$R^{82}R^{83}$, —N$R^{84}$C(=O)$R^{80}$, —N$R^{84}$C(=O)O$R^{81}$, —N$R^{84}$C(=O)N$R^{82}R^{83}$, —N$R^{84}$S(=O)$_2$$R^{81}$, —O$R^{80}$, =O, —OC(=O)$R^{80}$, —OC(=O)N$R^{82}R^{83}$, =S, —S(=O)$_n$$R^{80}$, or —S(=O)$_2$N$R^{82}R^{83}$; alternatively, when $L^3$, $A^3$, $G^3$, $X^3$, $L^4$, $A^4$, $G^4$ and $X^4$ are absent, $Z^3$ and $Z^4$ can together form a group of formula -$A^{21}$-$A^{22}$-$A^{23}$-; wherein $A^{21}$, $A^{22}$, and $A^{23}$ are independently chosen from —C$Z^{21}Z^{22}$—, —C$Z^{23}Z^{24}$C$Z^{25}Z^{26}$—, or —N$Z^{27}$—; wherein:

(a) when any two of $Z^{21}$, $Z^{22}$, $Z^{23}$, $Z^{24}$, $Z^{25}$, $Z^{26}$ and $Z^{27}$ are located on adjacent atoms, they may together form a bond between the atoms, and (b) any of $Z^{21}$, $Z^{22}$, $Z^{23}$, $Z^{24}$, $Z^{25}$, $Z^{26}$ and $Z^{27}$ may be independently chosen from H, $C_{1-6}$alkyl optionally substituted by 1-6 $R^{99}$, $C_{6-11}$aryl optionally substituted by 1-7 $R^{99}$, $C_{7-16}$arylalkyl optionally substituted by 1-6 $R^{99}$, $C_{3-11}$cycloalkyl optionally substituted by 1-6 $R^{99}$, $C_{4-17}$cycloalkylalkyl optionally substituted by 1-6 $R^{99}$, 3-15 membered heterocycloalkyl optionally substituted by 1-6 $R^{99}$, 4-21 membered heterocycloalkylalkyl optionally substituted by 1-6 $R^{99}$, 5-15 membered heteroaryl optionally substituted by 1-6 $R^{99}$, 6-21 membered heteroarylalkyl optionally substituted by 1-6 $R^{99}$, halogen, —CN, —C(=O)$R^{90}$, —C(=O)O$R^{90}$, —C(=O)N$R^{92}R^{93}$, —N$R^{92}R^{93}$, —N$R^{94}$C(=O)$R^{90}$, —N$R^{94}$C(=O)O$R^{91}$, —N$R^{94}$C(=O)N$R^{92}R^{93}$, —N$R^{94}$S(=O)$_2$$R^{91}$, —O$R^{90}$, =O, —OC(=O)$R^{90}$, —OC(=O)N$R^{92}R^{93}$, =S, —S(=O)$_n$$R^{90}$, and —S(=O)$_2$N$R^{92}R^{93}$; and (c) any two of $Z^{21}$, $Z^{22}$, $Z^{23}$, $Z^{24}$, $Z^{25}$, $Z^{26}$ and $Z^{27}$ may together form a group of formula -$A^{31}$-$A^{32}$-$A^{33}$-, wherein $A^{31}$, $A^{32}$, and $A^{33}$ are independently chosen from —C$Z^{31}Z^{32}$—, —C$Z^{33}Z^{34}$C$Z^{35}Z^{36}$—, or —N$Z^{37}$— wherein:

(i) when any two of $Z^{31}$, $Z^{32}$, $Z^{33}$, $Z^{34}$, $Z^{35}$, $Z^{36}$ and $Z^{37}$ are located on adjacent atoms, they may together form a bond between the atoms, and (ii) any of any of $Z^{21}$, $Z^{22}$, $Z^{23}$, $Z^{24}$, $Z^{25}$, $Z^{26}$ and $Z^{27}$ may be independently chosen from H, $C_{1-6}$alkyl optionally substituted by 1-6 $R^{139}$, $C_{6-11}$aryl optionally substituted by 1-7 $R^{139}$, $C_{7-16}$arylalkyl optionally substituted by 1-6 $R^{139}$, $C_{3-11}$cycloalkyl optionally substituted by 1-6 $R^{139}$, $C_{4-17}$cycloalkylalkyl optionally substituted by 1-6 $R^{139}$, 3-15 membered heterocycloalkyl optionally substituted by 1-6 $R^{139}$, 4-21 membered heterocycloalkylalkyl optionally substituted by 1-6 $R^{139}$, 5-15 membered heteroaryl optionally substituted by 1-6 $R^{139}$, 6-21 membered heteroarylalkyl optionally substituted by 1-6 $R^{139}$, halogen, —CN, —C(=O)$R^{130}$, —C(=O)O$R^{130}$, —C(=O)N$R^{132}R^{133}$, —N$R^{132}R^{133}$, —N$R^{134}$C(=O)$R^{130}$, —N$R^{134}$C(=O)O$R^{131}$, —N$R^{134}$C(=O)N$R^{132}R^{133}$, —N$R^{134}$S(=O)$_2$$R^{131}$, —O$R^{130}$, =O, —OCN, —OC(=O)R$^{130}$, —OC(=O)NR$^{132}$R$^{133}$, =S, —S(=O)$_n$$^{130}$, and —S(=O)$_2$NR$^{132}$R$^{133}$. In another embodiment, Z$^4$ is H, C$_{1-6}$alkyl optionally substituted by 1-6 R$^{89}$, C$_{6-11}$aryl optionally substituted by 1-7 R$^{89}$, C$_{7-16}$arylalkyl optionally substituted by 1-6 R$^{89}$, C$_{3-11}$cycloalkyl optionally substituted by 1-6 R$^{89}$, C$_{4-17}$cycloalkylalkyl optionally substituted by 1-6 R$^{89}$, 3-15 membered heterocycloalkyl optionally substituted by 1-6 R$^{89}$, 4-21 membered heterocycloalkylalkyl optionally substituted by 1-6 R$^{89}$, 5-15 membered heteroaryl optionally substituted by 1-6 R$^{89}$, 6-21 membered heteroarylalkyl optionally substituted by 1-6 R$^{89}$, halogen, —CN, —C(=O)R$^{80}$, —C(=O)OR$^{80}$, —C(=O)NR$^{82}$R$^{83}$, —C(=S)NR$^{82}$R$^{83}$, —NR$^{82}$R$^{83}$, —NR$^{84}$C(=O)R$^{80}$, —NR$^{84}$C(=O)OR$^{81}$, —NR$^{84}$C(=O)NR$^{82}$R$^{83}$, —NR$^{84}$C(=O)NR$^{84}$C(=O)R$^{80}$, —NR$^{84}$C(=O)NR$^{84}$C(=O)OR$^{80}$, —NR$^{84}$C(=S)R$^{80}$, —NR$^{84}$S(=O)$_2$R$^{81}$, —NR$^{84}$P(=O)R$^{88}$R$^{88}$, —OR$^{80}$, =O, —OC(=O)R$^{80}$, —OC(=O)NR$^{82}$R$^{83}$, =S, —S(=O)$_n$R$^{80}$, —S(=O)$_2$NR$^{82}$R$^{83}$, or —P(=O)R$^{88}$R$^{88}$; alternatively, when L$^3$, A$^3$, G$^3$, X$^3$, L$^4$, A$^4$, G$^4$ and X$^4$ are absent, Z$^3$ and Z$^4$ can together form a group of formula -A$^{21}$-A$^{22}$-A$^{23}$-; wherein A$^{21}$, A$^{22}$, and A$^{23}$ are independently chosen from —CZ$^{21}$Z$^{22}$—, —CZ$^{23}$Z$^{24}$CZ$^{25}$Z$^{26}$—, C(=O)—, —NZ$^{27}$—, —S—, —S(=O)—, —S(=O)$_2$—, or —O—; wherein:

(a) when any two of Z$^{21}$, Z$^{22}$, Z$^{23}$, Z$^{24}$, Z$^{25}$, Z$^{26}$ and Z$^{27}$ are located on adjacent atoms, they may together form a bond between the atoms, and (b) any of Z$^{21}$, Z$^{22}$, Z$^{23}$, Z$^{24}$, Z$^{25}$, Z$^{26}$ and Z$^{27}$ may be independently chosen from H, C$_{1-6}$alkyl optionally substituted by 1-6 R$^{99}$, C$_{6-11}$aryl optionally substituted by 1-7 R$^{99}$, C$_{7-16}$arylalkyl optionally substituted by 1-6 R$^{99}$, C$_{3-11}$cycloalkyl optionally substituted by 1-6 R$^{99}$, C$_{4-17}$cycloalkylalkyl optionally substituted by 1-6 R$^{99}$, 3-15 membered heterocycloalkyl optionally substituted by 1-6 R$^{99}$, 4-21 membered heterocycloalkylalkyl optionally substituted by 1-6 R$^{99}$, 5-15 membered heteroaryl optionally substituted by 1-6 R$^{99}$, 6-21 membered heteroarylalkyl optionally substituted by 1-6 R$^{99}$, halogen, —CN, —C(=O)R$^{90}$, —C(=O)OR$^{90}$, —C(=O)NR$^{92}$R$^{93}$, —C(=S)NR$^{92}$R$^{93}$, —NR$^{92}$R$^{93}$, —NR$^{94}$C(=O)R$^{90}$, —NR$^{94}$C(=O)OR$^{91}$, —NR$^{94}$C(=O)NR$^{92}$R$^{93}$, —NR$^{94}$C(=O)NR$^{94}$C(=O)R$^{90}$, —NR$^{94}$C(=O)NR$^{94}$C(=O)OR$^{90}$, —NR$^{94}$C(=S)R$^{90}$, —NR$^{94}$S(=O)$_2$R$^{91}$, —NR$^{94}$P(=O)R$^{98}$R$^{98}$, —OR$^{90}$, =O, —OC(=O)R$^{90}$, —OC(=O)NR$^{92}$R$^{93}$, =S, —S(=O)$_n$R$^{90}$, —S(=O)$_2$NR$^{92}$R$^{93}$, and —P(=O)R$^{98}$R$^{98}$; and (c) any two of Z$^{21}$, Z$^{22}$, Z$^{23}$, Z$^{24}$, Z$^{25}$, Z$^{26}$ and Z$^{27}$ may together form a group of formula -A$^{31}$-A$^{32}$-A$^{33}$-, wherein A$^{31}$, A$^{32}$, and A$^{33}$ are independently chosen from —CZ$^{31}$Z$^{32}$—, —CZ$^{33}$Z$^{34}$CZ$^{35}$Z$^{36}$—, —C(=O)—, —NZ$^{37}$—, —S—, —S(=O)—, —S(=O)$_2$—, or —O— wherein:

(i) when any two of Z$^{31}$, Z$^{32}$, Z$^{33}$, Z$^{34}$, Z$^{35}$, Z$^{36}$ and Z$^{37}$ are located on adjacent atoms, they may together form a bond between the atoms, and (ii) any of any of Z$^{21}$, Z$^{22}$, Z$^{23}$, Z$^{24}$, Z$^{25}$, Z$^{26}$ and Z$^{27}$ may be independently chosen from H, C$_{1-6}$alkyl optionally substituted by 1-6 R$^{139}$, C$_{6-11}$aryl optionally substituted by 1-7 R$^{139}$, C$_{7-16}$arylalkyl optionally substituted by 1-6 R$^{139}$, C$_{3-11}$cycloalkyl optionally substituted by 1-6 R$^{139}$, C$_{4-17}$cycloalkylalkyl optionally substituted by 1-6 R$^{139}$, 3-15 membered heterocycloalkyl optionally substituted by 1-6 R$^{139}$, 4-21 membered heterocycloalkylalkyl optionally substituted by 1-6 R$^{139}$, 5-15 membered heteroaryl optionally substituted by 1-6 R$^{139}$, 6-21 membered heteroarylalkyl optionally substituted by 1-6 R$^{139}$, halogen, —CN, —C(=O)R$^{130}$, —C(=O)OR$^{130}$, —C(=O)NR$^{132}$R$^{133}$, —C(=S)NR$^{132}$R$^{133}$, —NR$^{132}$R$^{133}$, —NR$^{134}$C(=O)R$^{130}$, —NR$^{134}$C(=O)OR$^{131}$, —NR$^{134}$C(=O)NR$^{132}$R$^{133}$, —NR$^{134}$C(=O)NR$^{134}$C(=O)R$^{130}$, —NR$^{134}$C(=O)NR$^{134}$C(=O)OR$^{130}$, —NR$^{134}$C(=S)R$^{130}$, —NR$^{134}$S(=O)$_2$R$^{131}$, —NR$^{134}$P(=O)R$^{138}$R$^{138}$, —OR$^{130}$, =O, —OCN, —OC(=O)R$^{130}$, —OC(=O)NR$^{132}$R$^{133}$, =S, —S(=O)$_n$R$^{130}$, —S(=O)$_2$NR$^{132}$R$^{133}$, and —P(=O)R$^{138}$R$^{138}$. In another embodiment, Z$^4$ is H, C$_{1-6}$alkyl optionally substituted by 1-6 R$^{89}$, C$_{6-11}$aryl optionally substituted by 1-7 R$^{89}$, C$_{7-16}$arylalkyl optionally substituted by 1-6 R$^{89}$, C$_{3-41}$cycloalkyl optionally substituted by 1-6 R$^{89}$, C$_{4-17}$cycloalkylalkyl optionally substituted by 1-6 R$^{89}$, 3-15 membered heterocycloalkyl optionally substituted by 1-6 R$^{89}$, 4-21 membered heterocycloalkylalkyl optionally substituted by 1-6 R$^{89}$, 5-15 membered heteroaryl optionally substituted by 1-6 R$^{89}$, 6-21 membered heteroarylalkyl optionally substituted by 1-6 R$^{89}$, halogen, —CN, —C(=O)R$^{80}$, —C(=O)OR$^{80}$, —C(=O)NR$^{82}$R$^{83}$, —C(=S)NR$^{82}$R$^{83}$, —NR$^{84}$C(=O)R$^{80}$, —NR$^{84}$C(=O)OR$^{81}$, —NR$^{84}$C(=O)NR$^{82}$R$^{83}$, —NR$^{84}$C(=O)NR$^{84}$C(=O)R$^{80}$, —NR$^{84}$C(=O)NR$^{84}$C(=O)OR$^{80}$, —NR$^{84}$C(=S)R$^{80}$, —NR$^{84}$S(=O)$_2$R$^{81}$, —OR$^{80}$, =O, —OC(=O)R$^{80}$, —OC(=O)NR$^{82}$R$^{83}$, =S, —S(=O)$_n$R$^{80}$, or —S(=O)$_2$NR$^{82}$R$^{83}$; alternatively, when L$^3$, A$^3$, G$^3$, X$^3$, L$^4$, A$^4$, G$^4$ and X$^4$ are absent, Z$^3$ and Z$^4$ can together form a group of formula -A$^{21}$-A$^{22}$-A$^{23}$-; wherein A$^{21}$, A$^{22}$, and A$^{23}$ are independently chosen from —CZ$^{21}$Z$^{22}$—, —CZ$^{23}$Z$^{24}$CZ$^{25}$Z$^{26}$—, —C(=O)—, —NZ$^{27}$—, —S—, —S(=O)—, —S(=O)$_2$—, or —O—; wherein:

(a) when any two of Z$^{21}$, Z$^{22}$, Z$^{23}$, Z$^{24}$, Z$^{25}$, Z$^{26}$ and Z$^{27}$ are located on adjacent atoms, they may together form a bond between the atoms, and (b) any of Z$^{21}$, Z$^{22}$, Z$^{23}$, Z$^{24}$, Z$^{25}$, Z$^{26}$ and Z$^{27}$ may be independently chosen from H, C$_{1-6}$alkyl optionally substituted by 1-6 R$^{99}$, C$_{6-11}$aryl optionally substituted by 1-7 R$^{99}$, C$_{7-16}$arylalkyl optionally substituted by 1-6 R$^{99}$, C$_{3-11}$cycloalkyl optionally substituted by 1-6 R$^{99}$, C$_{4-17}$cycloalkylalkyl optionally substituted by 1-6 R$^{99}$, 3-15 membered heterocycloalkyl optionally substituted by 1-6 R$^{99}$, 4-21 membered heterocycloalkylalkyl optionally substituted by 1-6 R$^{99}$, 5-15 membered heteroaryl optionally substituted by 1-6 R$^{99}$, 6-21 membered heteroarylalkyl optionally substituted by 1-6 R$^{99}$, halogen, —CN, —C(=O)R$^{90}$, —C(=O)OR$^{90}$, —C(=O)NR$^{92}$R$^{93}$, —C(=S)NR$^{92}$R$^{93}$, —NR$^{92}$R$^{93}$, —NR$^{94}$C(=O)R$^{90}$, —NR$^{94}$C(=O)OR$^{91}$, —NR$^{94}$C(=O)NR$^{92}$R$^{93}$, —NR$^{94}$C(=O)NR$^{94}$C(=O)R$^{90}$, —NR$^{94}$C(=O)NR$^{94}$C(=O)OR$^{90}$, —NR$^{94}$C(=S)R$^{90}$, —NR$^{94}$S(=O)$_2$R$^{91}$, —OR$^{90}$, =O, —OC(=O)R$^{90}$, —OC(=O)NR$^{92}$R$^{93}$, =S, —S(=O)$_n$R$^{90}$, and —S(=O)$_2$NR$^{92}$R$^{93}$; and (c) any two of Z$^{21}$, Z$^{22}$, Z$^{23}$, Z$^{24}$, Z$^{25}$, Z$^{26}$ and Z$^{27}$ may together form a group of formula -A$^{31}$-A$^{32}$-A$^{33}$-, wherein A$^{31}$, A$^{32}$, and A$^{33}$ are independently chosen from —CZ$^{31}$Z$^{32}$—, —CZ$^{33}$Z$^{34}$CZ$^{35}$Z$^{36}$—, —C(=O)—, —NZ$^{37}$—, —S—, —S(=O)—, —S(=O)$_2$—, or —O— wherein:

(i) when any two of Z$^{31}$, Z$^{32}$, Z$^{33}$, Z$^{34}$, Z$^{35}$, Z$^{36}$ and Z$^{37}$ are located on adjacent atoms, they may together form a bond between the atoms, and (ii) any of any of Z$^{21}$, Z$^{22}$, Z$^{23}$, Z$^{24}$, Z$^{25}$, Z$^{26}$ and Z$^{27}$ may be independently chosen from H, C$_{1-6}$alkyl optionally substituted by 1-6 R$^{139}$, C$_{6-11}$aryl optionally substituted by 1-7 R$^{139}$, C$_{7-16}$arylalkyl optionally substituted by 1-6 R$^{139}$, C$_{3-11}$cycloalkyl optionally substituted by 1-6 R$^{139}$, C$_{4-17}$cycloalkylalkyl optionally substituted by 1-6 R$^{139}$, 3-15 membered heterocycloalkyl optionally substituted by 1-6 R$^{139}$, 4-21 membered heterocycloalkylalkyl optionally substituted by 1-6 R$^{139}$, 5-15 membered heteroaryl optionally substituted by 1-6 R$^{139}$, 6-21 membered heteroarylalkyl optionally substituted by 1-6 R$^{139}$, halogen, —CN, —C(=O)R$^{130}$, —C(=O)OR$^{130}$, —C(=O)NR$^{132}$R$^{133}$, —C(=S)NR$^{132}$R$^{133}$, —NR$^{132}$R$^{133}$, —NR$^{134}$C(=O)R$^{130}$, —NR$^{134}$C(=O)R$^{131}$, —NR$^{134}$C(=O)NR$^{132}$R$^{133}$, —NR$^{134}$C(=O)NR$^{134}$C(=O)R$^{130}$, —NR$^{134}$C(=O)OR$^{131}$, —NR$^{134}$S(=O)$_2$R$^{131}$, —OR$^{130}$, =O, —OCN, —OC(=O)R$^{130}$, —OC(=O)NR$^{132}$R$^{133}$, =S, —S(=O)$_n$R$^{130}$, and —S(=O)$_2$NR$^{132}$R$^{133}$. In another embodiment, Z$^4$ is H, C$_{1-6}$alkyl optionally substituted by 1-6 R$^{89}$, C$_{6-11}$aryl optionally substituted by 1-7 R$^{89}$, C$_{7-16}$arylalkyl optionally substituted by 1-6 R$^{89}$, C$_{3-11}$cycloalkyl optionally substituted by 1-6 R$^{89}$, 3-15 membered heterocycloalkyl optionally substituted by 1-6 R$^{89}$, 5-15 membered heteroaryl optionally substituted by 1-6 R$^{89}$, halogen, —CN, —C(=O)R$^{80}$, —C(=O)OR$^{80}$, —C(=O)NR$^{82}$R$^{83}$, —NR$^{82}$R$^{83}$, —NR$^{84}$C(=O)R$^{80}$, —NR$^{84}$C(=O)OR$^{81}$, —NR$^{84}$C(=O)NR$^{82}$R$^{83}$, —NR$^{84}$S(=O)$_2$R$^{81}$, —OR$^{80}$, =O, —OC(=O)R$^{80}$, —OC(=O)NR$^{82}$R$^{83}$, =S, —S(=O)$_n$R$^{80}$, or —S(=O)$_2$NR$^{82}$R$^{83}$; alternatively, when L$^3$, A$^3$, G$^3$, X$^3$, L$^4$, A$^4$, G$^4$ and X$^4$ are absent, Z$^3$ and Z$^4$ can together form a group of formula -A$^{21}$-A$^{22}$-A$^{23}$; wherein A$^{21}$, A$^{22}$, and A$^{23}$ are independently chosen from —CZ$^{21}$Z$^{22}$—, —CZ$^{23}$Z$^{24}$CZ$^{25}$Z$^{26}$—, or —NZ$^{27}$—; wherein:

(a) when any two of Z$^{21}$, Z$^{22}$, Z$^{23}$, Z$^{24}$, Z$^{25}$, Z$^{26}$ and Z$^{27}$ are located on adjacent atoms, they may together form a bond between the atoms, and (b) any of Z$^{21}$, Z$^{22}$, Z$^{23}$, Z$^{24}$, Z$^{25}$, Z$^{26}$ and Z$^{27}$ may be independently chosen from H, C$_{1-6}$alkyl optionally substituted by 1-6 R$^{99}$, C$_{6-11}$aryl optionally substituted by 1-7 R$^{99}$, C$_{3-11}$cycloalkyl optionally substituted by 1-6 R$^{99}$, 3-15 membered heterocycloalkyl optionally substituted by 1-6 R$^{99}$, 5-15 membered heteroaryl optionally substituted by 1-6 R$^{99}$, halogen, —CN, —C(=O)R$^{90}$, —C(=O)OR$^{90}$, —C(=O)NR$^{92}$R$^{93}$, —NR$^{92}$R$^{93}$, —NR$^{94}$C(=O)R$^{90}$, —NR$^{94}$C(=O)OR$^{91}$, —NR$^{94}$C(=O)NR$^{92}$R$^{93}$, —NR$^{94}$S(=O)$_2$R$^{91}$, —OR$^{90}$, =O, —OC(=O)R$^{90}$, —OC(=O)NR$^{92}$R$^{93}$, =S, —S(=O)$_n$R$^{90}$, and —S(=O)$_2$NR$^{92}$R$^{93}$. In another embodiment, Z$^4$ is H, C$_{1-6}$alkyl optionally substituted by 1-13 R$^{89}$, C$_{2-6}$alkenyl optionally substituted by 1-11 R$^{89}$, halogen, —OR$^{80}$, or —CN. In another embodiment, Z$^4$ is H, C$_{1-6}$alkyl optionally substituted by 1-13 R$^{89}$, C$_{2-6}$alkenyl optionally substituted by 1-11 R$^{89}$, halogen, or —CN. In another embodiment, Z$^4$ is H, C$_{1-6}$alkyl optionally substituted by 1-3 R$^{89}$, C$_{2-6}$alkenyl optionally substituted by 1-3 R$^{89}$, halogen, —OR$^{80}$, or —CN. In another embodiment, Z$^4$ is H, C$_{1-6}$alkyl optionally substituted by 1-3 R$^{89}$, C$_{2-6}$alkenyl optionally substituted by 1-3 R$^{89}$, halogen, or —CN. In another embodiment, Z$^4$ is H, C$_{1-6}$alkyl, C$_{2-6}$alkenyl, halogen, —OR$^{80}$, or —CN. In another embodiment, Z$^4$ is H, C$_{1-6}$alkyl, C$_{2-6}$alkenyl, halogen, or —CN. In another embodiment, Z$^4$ is H, methyl, ethyl, vinyl, chloro, bromo, —OR$^{80}$, or —CN. In another embodiment, Z$^4$ is H, methyl, ethyl, vinyl, chloro, bromo, or —CN. In another embodiment, Z$^4$ is H.

In each embodiment of the present invention that is described in the paragraphs that precede or follow this paragraph, the definitions of R$^9$, R$^{19}$, R$^{29}$R$^{39}$, R$^{49}$, R$^{59}$R$^{69}$, R$^{79}$, R$^{89}$, R$^{99}$, and R$^{139}$ may be chosen from any of the embodiments that are described in this paragraph. In one embodiment, R$^9$, R$^{19}$, R$^{29}$, R$^{39}$, R$^{49}$, R$^{59}$, R$^{69}$, R$^{79}$, R$^{89}$, R$^{99}$, and R$^{139}$ at each occurrence is independently chosen from C$_{1-6}$alkyl optionally substituted by 1-13 R$^{179}$, C$_{2-6}$alkenyl optionally substituted by 1-11 R$^{179}$, C$_{2-6}$alkynyl optionally substituted by 1-9 R$^{179}$, C$_{6-11}$aryl optionally substituted by 1-11 R$^{179}$, C$_{7-16}$arylalkyl optionally substituted by 1-19 R$^{179}$, C$_{3-11}$cycloalkyl optionally substituted by 1-21 R$^{179}$, C$_{4-17}$cycloalkylalkyl optionally substituted by 1-32 R$^{179}$, 3-15 membered heterocycloalkyl optionally substituted by 1-28 R$^{171}$, 4-21 membered heterocycloalkylalkyl optionally substituted by 1-40 R$^{179}$, 5-15 membered heteroaryl optionally substituted by 1-15 R$^{179}$, 6-21 membered heteroarylalkyl optionally substituted by 1-27 R$^{179}$, halogen, —CN, —C(=O)R$^{170}$, —C(=O)OR$^{170}$, —C(=O)NR$^{172}$R$^{173}$, —C(=O)C(=O)R$^{170}$, —C(=NR$^{175}$)R$^{170}$, —C(=NR$^{175}$)NR$^{172}$R$^{173}$, —C(=NOH)NR$^{172}$R$^{173}$, —C(=NOR$^{176}$)R$^{170}$, —C(=NNR$^{172}$R$^{173}$)R$^{170}$, —C(=NNR$^{174}$C(=O)R$^{171}$)R$^{170}$, —C(=NNR$^{174}$C(=O)OR$^{171}$)R$^{170}$, —C(=S)NR$^{172}$R$^{173}$, —NC, —NO$_2$, —NR$^{172}$R$^{173}$, —NR$^{174}$NR$^{172}$R$^{173}$, —N=NR$^{174}$, =NR$^{170}$, =NOR$^{170}$, —NR$^{174}$OR$^{176}$, —NR$^{174}$C(=O)R$^{170}$, —NR$^{174}$C(=O)C(=O)R$^{170}$, —NR$^{174}$C(=O)OR$^{171}$, —NR$^{174}$C(=O)C(=O)OR$^{171}$, —NR$^{174}$C(=O)NR$^{172}$R$^{173}$, —NR$^{174}$C(=O)NR$^{174}$C(=O)R$^{170}$, —NR$^{174}$C(=O)NR$^{174}$C(=O)OR$^{10}$, —NR$^{174}$C(=NR$^{175}$)NR$^{172}$R$^{173}$, —NR$^{174}$C(=O)C(=O)NR$^{172}$R$^{173}$, —NR$^{174}$C(=S)R$^{170}$, —NR$^{174}$C(=S)OR$^{170}$, —NR$^{174}$C(=S)NR$^{172}$R$^{173}$, —NR$^{174}$S(=O)$_2$R$^{171}$, —NR$^{174}$S(=O)$_2$NR$^{172}$R$^{173}$, —NR$^{174}$P(=O)R$^{178}$R$^{178}$, —NR$^{174}$P(=O)(NR$^{172}$R$^{173}$)(NR$^{172}$R$^{173}$), —NR$^{174}$P(=O)(OR$^{170}$)(OR$^{170}$), —NR$^{174}$P(=O)(SR$^{170}$)(SR$^{170}$), —OR$^{170}$, =O, —OCN, —OC(=O)R$^{170}$, —OC(=O)NR$^{172}$R$^{173}$, —OC(=O)OR$^{170}$, —OC(=NR$^{175}$)NR$^{172}$R$^{173}$, —OS(=O)R$^{170}$, —OS(=O)$_2$R$^{170}$, —OS(=O)$_2$OR$^{170}$, —OS(=O)$_2$NR$^{172}$R$^{173}$, —OP(=O)R$^{178}$R$^{178}$, —OP(=O)(NR$^{172}$R$^{173}$)(NR$^{172}$R$^{173}$), —OP(=O)(OR$^{170}$)(OR$^{170}$), —OP(=O)(SR$^{170}$)(SR$^{170}$), —SCN, =S, —S(=O)$_n$R$^{170}$, —S(=O)$_2$OR$^{170}$, —SO$_3$R$^{177}$, —S(=O)$_2$NR$^{172}$R$^{173}$, —S(=O)NR$^{172}$R$^{173}$, —SP(=O)R$^{178}$R$^{178}$, —SP(=O)(NR$^{172}$R$^{173}$)(NR$^{172}$R$^{173}$), —SP(=O)(OR$^{170}$)(OR$^{170}$), —SP(=O)(SR$^{170}$)(SR$^{170}$), —O(=O)R$^{178}$R$^{178}$, —P(=O)(NR$^{172}$R$^{173}$)(NR$^{172}$R$^{173}$), —P(=O)(OR$^{170}$)(OR$^{170}$), and —P(=O)(SR$^{170}$)(SR$^{170}$). In another embodiment, R$^9$, R$^{19}$, R$^{29}$, R$^{39}$, R$^{49}$, R$^{59}$, R$^{69}$, R$^{79}$, R$^{89}$, R$^{99}$, and R$^{139}$ at each occurrence is independently chosen from C$_{1-6}$alkyl optionally substituted by 1-13 R$^{179}$, C$_{2-6}$alkenyl optionally substituted by 1-11 R$^{179}$, C$_{2-6}$alkynyl optionally substituted by 1-9 R$^{179}$, C$_{6-11}$aryl optionally substituted by 1-11 R$^{179}$, C$_{7-16}$arylalkyl optionally substituted by 1-19 R$^{179}$, C$_{3-11}$cycloalkyl optionally substituted by 1-21 R$^{179}$, C$_{4-17}$cycloalkylalkyl optionally substituted by 1-32 R$^{179}$, 3-15 membered heterocycloalkyl optionally substituted by 1-28 R$^{179}$, 4-21 membered heterocycloalkylalkyl optionally substituted by 1-40 R$^{179}$, 5-15 membered heteroaryl optionally substituted by 1-15 R$^{179}$, 6-21 membered heteroarylalkyl optionally substituted by 1-27 R$^{179}$, halogen, —CN, —C(=O)R$^{170}$, —C(=O)OR$^{170}$, —C(=O)NR$^{172}$R$^{173}$, —C(=O)C(=O)R$^{170}$, —C(=NR$^{175}$)R$^{170}$, —C(=NR$^{175}$)NR$^{172}$R$^{173}$, —C(=NOH)NR$^{172}$R$^{173}$, —C(=NOR$^{176}$)R$^{170}$, —C(NNR$^{172}$R$^{173}$)R$^{170}$, —C(NNR$^{174}$C(=O)R$^{171}$)R$^{170}$, —C(=NNR$^{174}$C(=O)OR$^{171}$)R$^{170}$, —C(=S)NR$^{172}$R$^{173}$, —NC, —NO$_2$, —NR$^{172}$R$^{173}$, —NR$^{174}$NR$^{172}$R$^{173}$, —N=NR$^{174}$, =NR$^{170}$, =NOR$^{170}$, —NR$^{174}$OR$^{176}$, —NR$^{174}$C(=O)R$^{170}$, —NR$^{174}$C(=O)C(=O)R$^{170}$, —NR$^{174}$C(=O)OR$^{171}$, —NR$^{174}$C(=O)C(=O)OR$^{171}$, —NR$^{174}$C(=O)NR$^{172}$R$^{173}$, —NR$^{174}$C(=O)NR$^{174}$C(=O)R$^{170}$, —NR$^{174}$C(=O)NR$^{174}$C(=O)OR$^{170}$, —NR$^{174}$C(=NR$^{175}$)NR$^{172}$R$^{173}$, —NR$^{174}$C(=O)C(=O)NR$^{172}$R$^{173}$, —NR$^{174}$C(=S)R$^{170}$, —NR$^{174}$C(=S)OR$^{170}$, —NR$^{174}$C(=S)NR$^{172}$R$^{173}$, —NR$^{174}$S(=O)$_2$R$^{171}$, —NR$^{174}$S(=O)$_2$NR$^{172}$R$^{173}$, —NR$^{174}$P(=O)R$^{178}$R$^{178}$, —OR$^{170}$, =O, —OCN, —OC(=O)R$^{170}$, —OC(=O)NR$^{172}$R$^{173}$, —OC(=O)OR$^{170}$, —OC(=NR$^{175}$)NR$^{172}$R$^{173}$, —OS(=O)R$^{170}$, —OS(=O)$_2$R$^{170}$, —OS(=O)$_2$OR$^{170}$, —OS(=O)$_2$NR$^{172}$R$^{173}$, —SCN, =S, —S(=O)$_n$R$^{170}$, —S(=O)$_2$OR$^{170}$, —SO$_3$R$^{177}$, —S(=O)$_2$NR$^{172}$R$^{173}$, —S(=O)NR$^{172}$R$^{173}$, and —P(=O)R$^{178}$R$^{178}$. In another embodiment, R$^9$, R$^{19}$, R$^{29}$, R$^{39}$, R$^{49}$, R$^{59}$, R$^{69}$, R$^{79}$, R$^{89}$, R$^{99}$, and R$^{139}$ at each occurrence is independently chosen from C$_{1-6}$alkyl optionally substituted by 1-13 $R^{179}$, $C_{2-6}$alkenyl optionally substituted by 1-11 $R^{179}$, $C_{2-6}$alkynyl optionally substituted by 1-9 $R^{179}$, $C_{6-11}$aryl optionally substituted by 1-11 $R^{179}$, $C_{7-16}$arylalkyl optionally substituted by 1-19 $R^{179}$, $C_{3-11}$cycloalkyl optionally substituted by 1-21 $R^{179}$, $C_{4-17}$cycloalkylalkyl optionally substituted by 1-32 $R^{179}$, 3-15 membered heterocycloalkyl optionally substituted by 1-28 $R^{179}$, 4-21 membered heterocycloalkylalkyl optionally substituted by 1-40 $R^{179}$, 5-15 membered heteroaryl optionally substituted by 1-15 $R^{179}$, 6-21 membered heteroarylalkyl optionally substituted by 1-27 $R^{179}$, halogen, —CN, —C(=O)$R^{170}$, —C(=O)O$R^{170}$, —C(=O)N$R^{172}R^{173}$, —C(=O)C(=O)$R^{170}$, —C(=N$R^{175}$)$R^{170}$, —C(=N$R^{175}$)N$R^{172}R^{173}$, —C(=NOH)N$R^{172}R^{173}$, —C(=NO$R^{176}$)$R^{170}$, —C(=NN$R^{172}R^{173}$)$R^{170}$, —C(=NN$R^{174}$C(=O)$R^{171}$)$R^{170}$, —C(=NN$R^{174}$C(=O)O$R^{171}$)$R^{170}$, —C(=S)N$R^{172}R^{173}$, —NC, —NO$_2$, —N$R^{172}R^{173}$, —N$R^{174}$N$R^{172}R^{173}$, —N=N$R^{174}$, =N$R^{170}$, =NO$R^{170}$, —N$R^{174}$O$R^{176}$, —N$R^{174}$C(=O)$R^{170}$, —N$R^{174}$C(=O)C(=O)$R^{170}$, —N$R^{174}$C(=O)O$R^{171}$, —N$R^{174}$C(=O)C(=O)O$R^{171}$, —N$R^{174}$C(=O)N$R^{172}R^{173}$, —N$R^{174}$C(=O)N$R^{174}$C(=O)$R^{170}$, —N$R^{174}$C(=O)N$R^{174}$C(=O)O$R^{170}$, —N$R^{174}$C(=N$R^{175}$)N$R^{172}R^{173}$, —N$R^{174}$C(=O)C(=O)N$R^{172}R^{173}$, —N$R^{174}$C(=S)$R^{170}$, —N$R^{174}$C(=S)O$R^{170}$, —N$R^{174}$C(=S)N$R^{172}R^{173}$, —N$R^{174}$S(=O)$_2R^{171}$, —N$R^{174}$S(=O)$_2$N$R^{172}R^{173}$, —O$R^{170}$, =O, —OCN, —OC(=O)$R^{170}$, —OC(=O)N$R^{172}R^{173}$, —OC(=O)O$R^{170}$, —OC(=N$R^{175}$)N$R^{172}R^{173}$, —OS(=O)$R^{170}$, —OS(=O)$_2R^{170}$, —OS(=O)$_2$O$R^{170}$, —OS(=O)$_2$N$R^{172}R^{173}$, —SCN, =S, —S(=O)$_nR^{170}$, —S(=O)$_2$O$R^{170}$, —SO$_3R^{177}$, —S(=O)$_2$N$R^{172}R^{173}$, and —S(=O)N$R^{172}R^{173}$. In another embodiment, $R^9$, $R^{19}$, $R^{29}$, $R^{39}$, $R^{49}$, $R^{59}$, $R^{69}$, $R^{79}$, $R^{89}$, $R^{99}$, and $R^{139}$ at each occurrence is independently chosen from $C_{1-6}$alkyl optionally substituted by 1-13 $R^{179}$, $C_{6-11}$aryl optionally substituted by 1-7 $R^{179}$, $C_{7-16}$arylalkyl optionally substituted by 1-19 $R^{179}$, $C_{3-11}$cycloalkyl optionally substituted by 1-21 $R^{179}$, $C_{4-17}$cycloalkylalkyl optionally substituted by 1-32 $R^{179}$, 3-15 membered heterocycloalkyl optionally substituted by 1-28 $R^{179}$, 4-21 membered heterocycloalkylalkyl optionally substituted by 1-40 $R^{179}$, 5-15 membered heteroaryl optionally substituted by 1-15 $R^{179}$, 6-21 membered heteroarylalkyl optionally substituted by 1-27 $R^{179}$, halogen, —CN, —C(=O)$R^{170}$, —C(=O)O$R^{170}$, —C(=O)N$R^{172}R^{173}$, —C(=O)C(=O)$R^{170}$, —C(=S)N$R^{172}R^{173}$, —NC, —NO$_2$, —N$R^{172}R^{173}$, —N$R^{174}$N$R^{172}R^{173}$, —N$R^{174}$C(=O)$R^{170}$, —N$R^{174}$C(=O)C(=O)$R^{170}$, —N$R^{174}$C(=O)O$R^{171}$, —N$R^{174}$C(=O)C(=O)O$R^{171}$, —N$R^{174}$C(=O)N$R^{172}R^{173}$, —N$R^{174}$C(=O)N$R^{174}$C(=O)$R^{170}$, —N$R^{174}$C(=O)N$R^{174}$C(=O)O$R^{170}$, —N$R^{174}$C(=N$R^{175}$)N$R^{172}R^{173}$, —N$R^{174}$C(=O)C(=O)N$R^{172}R^{173}$, —N$R^{174}$C(=S)$R^{170}$, —N$R^{174}$C(=S)O$R^{170}$, —N$R^{174}$C(=S)N$R^{172}R^{173}$, —N$R^{174}$S(=O)$_2R^{171}$, —N$R^{174}$S(=O)$_2$N$R^{172}R^{173}$, —O$R^{170}$, =O, —OCN, —OC(=O)$R^{170}$, —OC(=O)N$R^{172}R^{173}$, —OC(=O)O$R^{170}$, —OS(=O)$R^{170}$, —OS(=O)$_2R^{170}$, —OS(=O)$_2$O$R^{170}$, —OS(=O)$_2$N$R^{172}R^{173}$, —SCN, =S, —S(=O)$_nR^{170}$, —S(=O)$_2$O$R^{170}$, —SO$_3R^{177}$, —S(=O)$_2$N$R^{172}R^{173}$, and —S(=O)N$R^{172}R^{173}$. In another embodiment, $R^9$, $R^{19}$, $R^{29}$, $R^{39}$, $R^{49}$, $R^{59}$, $R^{69}$, $R^{79}$, $R^{89}$, $R^{99}$, and $R^{139}$ at each occurrence is independently chosen from $C_{1-6}$alkyl optionally substituted by 1-13 $R^{179}$, $C_{6-11}$aryl optionally substituted by 1-7 $R^{179}$, $C_{7-16}$arylalkyl optionally substituted by 1-19 $R^{179}$, $C_{3-11}$cycloalkyl optionally substituted by 1-21 $R^{179}$, $C_{4-17}$cycloalkylalkyl optionally substituted by 1-32 $R^{179}$, 3-15 membered heterocycloalkyl optionally substituted by 1-28 $R^{179}$, 4-21 membered heterocycloalkylalkyl optionally substituted by 1-40 $R^{179}$, 5-15 membered heteroaryl optionally substituted by 1-15 $R^{179}$, 6-21 membered heteroarylalkyl optionally substituted by 1-27 $R^{179}$, halogen, —CN, —C(=O)$R^{170}$, —C(=O)O$R^{170}$, —C(=O)N$R^{172}R^{173}$, —C(=O)C(=O)$R^{170}$, —C(=S)N$R^{172}R^{173}$, —NC, —NO$_2$, —N$R^{172}R^{173}$, —N$R^{174}$N$R^{172}R^{173}$, —N$R^{174}$C(=O)$R^{170}$, —N$R^{174}$C(=O)C(=O)$R^{170}$, —N$R^{174}$C(=O)O$R^{171}$, —N$R^{174}$C(=O)N$R^{172}R^{173}$, —N$R^{174}$C(=O)N$R^{174}$C(=O)$R^{170}$, —N$R^{174}$C(=N$R^{175}$)N$R^{172}R^{173}$, —N$R^{174}$C(=S)$R^{170}$, —N$R^{174}$C(=S)N$R^{172}R^{173}$, —N$R^{174}$S(=O)$_2R^{171}$, —O$R^{170}$, =O, —OCN, —OC(=O)$R^{170}$, —OC(=O)N$R^{172}R^{173}$, —OS(=O)$_2$N$R^{172}R^{173}$, —SCN, =S, —S(=O)$_nR^{170}$, —SO$_3R^{177}$, —S(=O)$_2$N$R^{172}R^{173}$, and —P(=O)$R^{178}R^{178}$. In another embodiment, $R^9$, $R^{19}$, $R^{29}$, $R^{39}$, $R^{49}$, $R^{59}$, $R^{69}$, $R^{79}$, $R^{89}$, $R^{99}$, and $R^{139}$ at each occurrence is independently chosen from $C_{1-6}$alkyl optionally substituted by 1-13 $R^{179}$, $C_{6-11}$aryl optionally substituted by 1-7 $R^{179}$, $C_{7-16}$arylalkyl optionally substituted by 1-19 $R^{179}$, $C_{3-11}$cycloalkyl optionally substituted by 1-21 $R^{179}$, $C_{4-17}$cycloalkylalkyl optionally substituted by 1-32 $R^{179}$, 3-15 membered heterocycloalkyl optionally substituted by 1-28 $R^{179}$, 4-21 membered heterocycloalkylalkyl optionally substituted by 1-40 $R^{179}$, 5-15 membered heteroaryl optionally substituted by 1-15 $R^{179}$, 6-21 membered heteroarylalkyl optionally substituted by 1-27 $R^{179}$, halogen, —CN, —C(=O)$R^{170}$, —C(=O)O$R^{170}$, —C(=O)N$R^{172}R^{173}$, —C(=S)N$R^{172}R^{173}$, —N$R^{172}R^{173}$, —N$R^{174}$C(=O)$R^{170}$, —N$R^{174}$C(=O)O$R^{171}$, —N$R^{174}$C(=O)N$R^{172}R^{173}$, —N$R^{174}$C(=S)$R^{170}$, —N$R^{174}$S(O)$_2R^{171}$, —O$R^{170}$, =O, —OC(=O)$R^{170}$, —OC(=O)N$R^{172}R^{173}$, —OS(=O)$_2$N$R^{172}R^{173}$, =S, —S(=O)$_nR^{170}$, and —S(=O)$_2$N$R^{172}R^{173}$. In another embodiment, $R^9$, $R^{19}$, $R^{29}$, $R^{39}$, $R^{49}$, $R^{59}$, $R^{69}$, $R^{79}$, $R^{89}$, $R^{99}$, and $R^{139}$ at each occurrence is independently chosen from $C_{1-6}$alkyl optionally substituted by 1-13 $R^{179}$, $C_{6-11}$aryl optionally substituted by 1-7 $R^{179}$, $C_{7-16}$arylalkyl optionally substituted by 1-19 $R^{179}$, $C_{3-11}$cycloalkyl optionally substituted by 1-21 $R^{179}$, 3-15 membered heterocycloalkyl optionally substituted by 1-28 $R^{179}$, 5-15 membered heteroaryl optionally substituted by 1-15 $R^{179}$, halogen, —CN, —C(=O)$R^{170}$, —C(=O)O$R^{170}$, —C(=O)N$R^{172}R^{173}$, —N$R^{172}R^{173}$, —N$R^{174}$C(=O)$R^{170}$, —N$R^{174}$C(=O)O$R^{171}$, —N$R^{174}$C(=O)N$R^{172}R^{173}$, —N$R^{174}$S(=O)$_2R^{171}$, —N$R^{174}$P(=O)$R^{178}R^{178}$, —O$R^{170}$, =O, —OC(=O)$R^{170}$, —OC(=O)N$R^{172}R^{173}$, —OS(=O)$_2$N$R^{172}R^{173}$, =S, —S(=O)$_nR^{170}$, —S(=O)$_2$N$R^{172}R^{173}$, and —P(=O)$R^{178}R^{178}$. In another embodiment, $R^9$, $R^{19}$, $R^{29}$, $R^{39}$, $R^{49}$, $R^{59}$, $R^{69}$, $R^{79}$, $R^{89}$, $R^{99}$, and $R^{139}$ at each occurrence is independently chosen from $C_{1-6}$alkyl optionally substituted by 1-13 $R^{179}$, $C_{6-11}$aryl optionally substituted by 1-7 $R^{179}$, $C_{7-16}$arylalkyl optionally substituted by 1-19 $R^{179}$, $C_{3-11}$cycloalkyl optionally substituted by 1-21 $R^{179}$, 3-15 membered heterocycloalkyl optionally substituted by 1-28 $R^{179}$, 5-15 membered heteroaryl optionally substituted by 1-15 $R^{179}$, halogen, —CN, —C(=O)$R^{170}$, —C(=O)O$R^{170}$, —C(=O)N$R^{172}R^{173}$, —N$R^{172}R^{173}$, —N$R^{174}$C(=O)$R^{170}$, —N$R^{174}$C(=O)O$R^{171}$, —N$R^{174}$C(=O)N$R^{172}R^{173}$, —N$R^{174}$S(=O)$_2R^{171}$, —O$R^{170}$, =O, —OC(=O)$R^{170}$, —OC(=O)N$R^{172}R^{173}$, —OS(=O)$_2$N$R^{172}R^{173}$, =S, —S(=O)$_nR^{170}$, and —S(=O)$_2$N$R^{172}R^{173}$. In another embodiment, $R^9$, $R^{19}$, $R^{29}$, $R^{39}$, $R^{49}$, $R^{59}$, $R^{69}$, $R^{79}$, $R^{89}$, $R^{99}$, and $R^{139}$ at each occurrence is independently chosen from $C_{1-6}$alkyl optionally substituted by 1-6 $R^{179}$, $C_{6-11}$aryl optionally substituted by 1-6 $R^{179}$, $C_{7-16}$arylalkyl optionally substituted by 1-6 $R^{179}$, $C_{3-11}$cycloalkyl optionally substituted by 1-6 $R^{179}$, $C_{4-17}$cycloalkylalkyl optionally substituted by 1-6 $R^{179}$, 3-15 membered heterocycloalkyl optionally substituted by 1-6 $R^{179}$, 4-21 membered heterocycloalkylalkyl optionally substituted by 1-6 $R^{179}$, 5-15 membered heteroaryl optionally substituted by 1-6 $R^{179}$, 6-21 membered heteroarylalkyl optionally substituted by 1-6 $R^{179}$, halogen, —CN, —C(=O)$R^{170}$, —C(=O)O$R^{170}$, —C(=O)N$R^{172}R^{173}$, —C(=O)C(=O)$R^{170}$, —C(=S)N$R^{172}R^{173}$, —NC, —NO$_2$, —N$R^{172}R^{173}$, —N$R^{174}$N$R^{172}R^{173}$, —N$R^{174}$C(=O)$R^{170}$, —N$R^{174}$C(=O)C(=O)$R^{170}$, —N$R^{174}$C(=O)O$R^{171}$, —N$R^{174}$C(=O)C(=O)O$R^{171}$, —N$R^{174}$C(=O)N$R^{172}R^{173}$, —N$R^{174}$C(=O)N$R^{174}$C(=O)$R^{170}$, —N$R^{174}$C(=O)N$R^{174}$C(=O)O$R^{170}$, —N$R^{174}$C(=N$R^{175}$)N$R^{172}R^{173}$, —N$R^{174}$C(=O)C(=O)N$R^{172}R^{173}$, —N$R^{174}$C(=S)$R^{170}$, —N$R^{174}$C(=S)O$R^{170}$, —N$R^{174}$C(=S)N$R^{172}R^{173}$, —N$R^{174}$S(=O)$_2R^{171}$, —N$R^{174}$S(=O)$_2$N$R^{172}R^{173}$, —N$R^{174}$P(=O)$R^{178}R^{178}$, —O$R^{170}$, =O, —OCN, —OC(=O)$R^{170}$, —OC(=O)N$R^{172}R^{173}$, —OC(=O)O$R^{170}$, —OS(=O)$R^{170}$, —OS(=O)$_2R^{170}$, —OS(=O)$_2$O$R^{170}$, —OS(=O)$_2$N$R^{172}R^{173}$, —SCN, =S, —S(=O)$_nR^{170}$, —S(=O)$_2$O$R^{170}$, —SO$_3R^{177}$, —S(=O)$_2$N$R^{172}R^{173}$, and —S(=O)N$R^{172}R^{173}$, and —P(=O)$R^{178}R^{178}$. In another embodiment, $R^9$, $R^{19}$, $R^{29}$, $R^{39}$, $R^{49}$, $R^{59}$, $R^{69}$, $R^{79}$, $R^{89}$, $R^{99}$, and $R^{139}$ at each occurrence is independently chosen from $C_{1-6}$alkyl optionally substituted by 1-6 $R^{179}$, $C_{6-11}$aryl optionally substituted by 1-6 $R^{179}$, $C_{7-16}$arylalkyl optionally substituted by 1-6 $R^{179}$, $C_{3-11}$cycloalkyl optionally substituted by 1-6 $R^{179}$, $C_{4-17}$cycloalkylalkyl optionally substituted by 1-6 $R^{179}$, 3-15 membered heterocycloalkyl optionally substituted by 1-6 $R^{179}$, 4-21 membered heterocycloalkylalkyl optionally substituted by 1-6 $R^{179}$, 5-15 membered heteroaryl optionally substituted by 1-6 $R^{179}$, 6-21 membered heteroarylalkyl optionally substituted by 1-6 $R^{179}$, halogen, —CN, —C(=O)$R^{170}$, —C(=O)O$R^{170}$, —C(=O)N$R^{172}R^{173}$, —C(=O)C(=O)$R^{170}$, —C(=S)N$R^{172}R^{173}$, —NC, —NO$_2$, —N$R^{172}R^{173}$, —N$R^{174}$N$R^{172}R^{173}$, —N$R^{174}$C(=O)$R^{170}$, —N$R^{174}$C(=O)C(=O)$R^{170}$, —N$R^{174}$C(=O)O$R^{171}$, —N$R^{174}$C(=O)C(=O)O$R^{171}$, —N$R^{174}$C(=O)N$R^{172}R^{173}$, —N$R^{174}$C(=O)N$R^{174}$C(=O)$R^{170}$, —N$R^{174}$C(=O)N$R^{174}$C(=O)O$R^{170}$, —N$R^{174}$C(=N$R^{175}$)N$R^{172}R^{173}$, —N$R^{174}$C(=O)C(=O)N$R^{172}R^{173}$, —N$R^{174}$C(=S)$R^{170}$, —N$R^{174}$C(=S)O$R^{170}$, —N$R^{174}$C(=S)N$R^{172}R^{173}$, —N$R^{174}$S(=O)$_2R^{171}$, —N$R^{174}$S(=O)$_2$N$R^{172}R^{173}$, —O$R^{170}$, =O, —OCN, —OC(=O)$R^{170}$, —OC(=O)N$R^{172}R^{173}$, —OC(=O)O$R^{170}$, —OS(=O)$R^{170}$, —OS(=O)$_2R^{170}$, —OS(=O)$_2$O$R^{170}$, —OS(=O)$_2$N$R^{172}R^{173}$, —SCN, =S, —S(=O)$_nR^{170}$, —S(=O)$_2$O$R^{170}$, —SO$_3R^{177}$, —S(=O)$_2$N$R^{172}R^{173}$, and —S(=O)N$R^{172}R^{173}$. In another embodiment, $R^9$, $R^{19}$, $R^{29}$, $R^{39}$, $R^{49}$, $R^{59}$, $R^{69}$, $R^{79}$, $R^{89}$, $R^{99}$, and $R^{139}$ at each occurrence is independently chosen from $C_{1-6}$alkyl optionally substituted by 1-6 $R^{179}$, $C_{6-11}$aryl optionally substituted by 1-7 $R^{179}$, $C_{7-16}$arylalkyl optionally substituted by 1-6 $R^{179}$, $C_{3-11}$cycloalkyl optionally substituted by 1-6 $R^{179}$, $C_{4-17}$cycloalkylalkyl optionally substituted by 1-6 $R^{179}$, 3-15 membered heterocycloalkyl optionally substituted by 1-6 $R^{179}$, 4-21 membered heterocycloalkylalkyl optionally substituted by 1-6 $R^{179}$, 5-15 membered heteroaryl optionally substituted by 1-6 $R^{179}$, 6-21 membered heteroarylalkyl optionally substituted by 1-6 $R^{179}$, halogen, —CN, —C(=O)$R^{170}$, —C(=O)O$R^{170}$, —C(=O)N$R^{172}R^{173}$, —C(=O)C(=O)$R^{170}$, —C(=S)N$R^{172}R^{173}$, —NC, —NO$_2$, —N$R^{172}R^{173}$, —N$R^{174}$N$R^{172}R^{173}$, —N$R^{174}$C(=O)$R^{170}$, —N$R^{174}$c(=O)c(=O)$R^{170}$, —N$R^{174}$C(=O)O$R^{171}$, —N$R^{174}$C(=O)N$R^{172}R^{173}$, —N$R^{174}$C(=O)N$R^{174}$C(=O)$R^{170}$, —N$R^{174}$C(=N$R^{175}$)N$R^{172}R^{173}$, —N$R^{174}$C(=S)$R^{170}$, —N$R^{174}$C(=S)N$R^{172}R^{173}$, —N$R^{174}$S(=O)$_2R^{171}$, —O$R^{170}$, =O, —OCN, —OC(=O)$R^{170}$, —OC(=O)N$R^{172}R^{173}$, —OS(=O)$_2$N$R^{172}R^{173}$, —SCN, =S, —S(=O)$_nR^{170}$, —SO$_3R^{177}$, and —S(=O)$_2$N$R^{172}R^{173}$. In another embodiment $R^9$, $R^{19}$, $R^{29}$, $R^{39}$, $R^{49}$, $R^{59}$, $R^{69}$, $R^{79}$, $R^{89}$, $R^{99}$, and $R^{139}$ at each occurrence is independently chosen from $C_{1-6}$alkyl optionally substituted by 1-6 $R^{179}$, $C_{6-11}$aryl optionally substituted by 1-7 $R^{179}$, $C_{7-16}$arylalkyl optionally substituted by 1-6 $R^{179}$, $C_{3-41}$cycloalkyl optionally substituted by 1-6 $R^{179}$, $C_{4-17}$cycloalkylalkyl optionally substituted by 1-6 $R^{179}$, 3-15 membered heterocycloalkyl optionally substituted by 1-6 $R^{179}$, 4-21 membered heterocycloalkylalkyl optionally substituted by 1-6 $R^{179}$, 5-15 membered heteroaryl optionally substituted by 1-6 $R^{179}$, 6-21 membered heteroarylalkyl optionally substituted by 1-6 $R^{179}$, halogen, —CN, —C(=O)$R^{170}$, —C(=O)O$R^{170}$, —C(=O)N$R^{172}R^{173}$, —C(=S)N$R^{172}R^{173}$, —N$R^{172}R^{173}$, —N$R^{174}$C(=O)$R^{170}$, —N$R^{174}$C(=O)O$R^{171}$, —N$R^{174}$C(=O)N$R^{172}R^{173}$, —N$R^{174}$C(=O)N$R^{174}$C(=O)$R^{170}$, —N$R^{174}$C(=S)$R^{170}$, —N$R^{174}$S(=O)$_2R^{171}$, —N$R^{174}$P(=O)$R^{178}R^{178}$, —O$R^{170}$, =O, —OC(=O)$R^{170}$, —OC(=O)N$R^{172}R^{173}$, —OS(=O)$_2$N$R^{172}R^{173}$, =S, —S(=O)$_nR^{170}$, —S(=O)$_2$N$R^{172}R^{173}$, and —P(=O)$R^{178}R^{178}$. In another embodiment, $R^9$, $R^{19}$, $R^{29}$, $R^{39}$, $R^{49}$, $R^{59}$, $R^{69}$, $R^{79}$, $R^{89}$, $R^{99}$, and $R^{139}$ at each occurrence is independently chosen from $C_{1-6}$alkyl optionally substituted by 1-6 $R^{179}$, $C_{6-11}$aryl optionally substituted by 1-7 $R^{179}$, $C_{7-16}$arylalkyl optionally substituted by 1-6 $R^{179}$, $C_{3-11}$cycloalkyl optionally substituted by 1-6 $R^{179}$, $C_{4-17}$cycloalkylalkyl optionally substituted by 1-6 $R^{179}$, 3-15 membered heterocycloalkyl optionally substituted by 1-6 $R^{179}$, 4-21 membered heterocycloalkylalkyl optionally substituted by 1-6 $R^{179}$, 5-15 membered heteroaryl optionally substituted by 1-6 $R^{179}$, 6-21 membered heteroarylalkyl optionally substituted by 1-6 $R^{179}$, halogen, —CN, —C(=O)$R^{170}$, —C(=O)O$R^{170}$, —C(=O)N$R^{172}R^{173}$, —C(=S)N$R^{172}R^{173}$, —N$R^{172}R^{173}$, —N$R^{174}$C(=O)$R^{170}$, —N$R^{174}$C(=O)O$R^{171}$, —N$R^{174}$C(=O)N$R^{172}R^{173}$, —N$R^{174}$C(=O)N$R^{174}$C(=O)$R^{170}$, —N$R^{174}$C(=S)$R^{170}$, —N$R^{174}$S(=O)$_2R^{171}$, —O$R^{170}$, =O, —OC(=O)$R^{170}$, —OC(=O)N$R^{172}R^{173}$, —OS(=O)$_2$N$R^{172}R^{173}$, =S, —S(=O)$_nR^{170}$, and —S(=O)$_2$N$R^{172}R^{173}$. In another embodiment, $R^9$, $R^{19}$, $R^{29}$, $R^{39}$, $R^{49}$, $R^{59}$, $R^{69}$, $R^{79}$, $R^{89}$, $R^{99}$, and $R^{139}$ at each occurrence is independently chosen from $C_{1-6}$alkyl optionally substituted by 1-6 $R^{179}$, $C_{6-11}$aryl optionally substituted by 1-7 $R^{179}$, $C_{7-16}$arylalkyl optionally substituted by 1-6 $R^{179}$, $C_{3-11}$cycloalkyl optionally substituted by 1-6 $R^{179}$, 3-15 membered heterocycloalkyl optionally substituted by 1-6 $R^{179}$, 5-15 membered heteroaryl optionally substituted by 1-6 $R^{179}$, halogen, —CN, —C(=O)$R^{170}$, —C(=O)O$R^{170}$, —C(=O)N$R^{172}R^{173}$, —N$R^{172}R^{173}$, —N$R^{174}$C(=O)$R^{170}$, —N$R^{174}$C(=O)O$R^{171}$, —N$R^{174}$C(=O)N$R^{172}R^{173}$, —NR$^{174}$S(=O)$_2$R$^{171}$, —OR$^{170}$, =O, —OC(=O)R$^{170}$, —OC(=O)NR$^{172}$R$^{173}$, —OS(=O)$_2$NR$^{172}$R$^{173}$, =S, —S(=O)$_n$R$^{170}$, and —S(=O)$_2$NR$^{172}$R$^{173}$.

In each embodiment of the present invention that is described in the paragraphs that precede or follow this paragraph, the definitions of R$^{18}$, R$^{58}$, R$^{108}$, and R$^{178}$ may be chosen from any of the embodiments that are described in this paragraph. In one embodiment, R$^{18}$, R$^{58}$, R$^{88}$, R$^{108}$, and R$^{178}$ at each occurrence is independently chosen from C$_{1-6}$alkyl optionally substituted by 1-13 R$^{189}$, C$_{2-6}$alkenyl optionally substituted by 1-11 R$^{189}$, C$_{2-6}$alkynyl optionally substituted by 1-9 R$^{189}$, C$_{6-11}$aryl optionally substituted by 1-11 R$^{189}$, C$_{7-16}$arylalkyl optionally substituted by 1-19 R$^{189}$, C$_{3-11}$cycloalkyl optionally substituted by 1-21 R$^{189}$, C$_{4-17}$cycloalkylalkyl optionally substituted by 1-32 R$^{189}$, 3-15 membered heterocycloalkyl optionally substituted by 1-28 R$^{189}$, 4-21 membered heterocycloalkylalkyl optionally substituted by 1-40 R$^{189}$, 5-15 membered heteroaryl optionally substituted by 1-15 R$^{189}$, and 6-21 membered heteroarylalkyl optionally substituted by 1-27 R$^{189}$. In another embodiment, R$^{18}$, R$^{58}$, R$^{88}$, R$^{108}$, and R$^{178}$ at each occurrence is chosen from C$_{1-6}$alkyl optionally substituted by 1-13 R$^{189}$, C$_{6-11}$aryl optionally substituted by 1-11 R$^{189}$, C$_{7-16}$arylalkyl optionally substituted by 1-19 R$^{189}$, C$_{3-11}$cycloalkyl optionally substituted by 1-21 R$^{189}$, C$_{4-17}$cycloalkylalkyl optionally substituted by 1-32 R$^{189}$, 3-15 membered heterocycloalkyl optionally substituted by 1-28 R$^{189}$, 4-21 membered heterocycloalkylalkyl optionally substituted by 1-40 R$^{189}$, 5-15 membered heteroaryl optionally substituted by 1-15 R$^{189}$, and 6-21 membered heteroarylalkyl optionally substituted by 1-27 R$^{189}$. In another embodiment, R$^{18}$, R$^{58}$, R$^{88}$, R$^{198}$, and R$^{178}$ at each occurrence is independently chosen from C$_{1-6}$alkyl optionally substituted by 1-13 R$^{189}$, C$_{6-11}$aryl optionally substituted by 1-11 R$^{189}$, C$_{7-16}$arylalkyl optionally substituted by 1-19 R$^{189}$, C$_{3-11}$cycloalkyl optionally substituted by 1-21 R$^{189}$, 3-15 membered heterocycloalkyl optionally substituted by 1-28 R$^{189}$, 5-15 membered heteroaryl optionally substituted by 1-15 R$^{189}$, and 6-21 membered heteroarylalkyl optionally substituted by 1-27 R$^{189}$. In another embodiment, R$^{18}$, R$^{58}$, R$^{88}$, R$^{108}$, and R$^{178}$ at each occurrence is independently chosen from C$_{1-6}$alkyl optionally substituted by 1-13 R$^{189}$ and C$_{7-16}$arylalkyl optionally substituted by 1-19 R$^{189}$. In another embodiment, R$^{18}$, R$^{58}$, R$^{88}$, R$^{108}$, and R$^{178}$ at each occurrence is independently C$_{1-6}$alkyl optionally substituted by 1-13 R$^{189}$. In another embodiment, R$^{18}$, R$^{58}$, R$^{88}$, R$^{108}$, and R$^{178}$ at each occurrence is independently chosen from C$_{1-6}$alkyl optionally substituted by 1-6 R$^{189}$, C$_{2-6}$alkenyl optionally substituted by 1-6 R$^{189}$, C$_{2-6}$alkynyl optionally substituted by 1-6 R$^{189}$, C$_{6-11}$aryl optionally substituted by 1-6 R$^{189}$, C$_{7-16}$arylalkyl optionally substituted by 1-6 R$^{189}$, C$_{3-11}$cycloalkyl optionally substituted by 1-6 R$^{189}$, C$_{4-17}$cycloalkylalkyl optionally substituted by 1-6 R$^{189}$, 3-15 membered heterocycloalkyl optionally substituted by 1-6 R$^{189}$, 4-21 membered heterocycloalkylalkyl optionally substituted by 1-6 R$^{189}$, 5-15 membered heteroaryl optionally substituted by 1-6 R$^{189}$, and 6-21 membered heteroarylalkyl optionally substituted by 1-6 R$^{189}$. In another embodiment, R$^{18}$, R$^{58}$, R$^{88}$, R$^{108}$, and R$^{178}$ at each occurrence is independently chosen from C$_{1-6}$alkyl optionally substituted by 1-6 R$^{189}$, C$_{6-11}$aryl optionally substituted by 1-6 R$^{189}$, C$_{7-16}$arylalkyl optionally substituted by 1-6 R$^{189}$, C$_{3-11}$cycloalkyl optionally substituted by 1-6 R$^{189}$, 3-15 membered heterocycloalkyl optionally substituted by 1-6 R$^{189}$, 5-15 membered heteroaryl optionally substituted by 1-6 R$^{189}$, and 6-21 membered heteroarylalkyl optionally substituted by 1-6 R$^{189}$. In another embodiment, R$^{18}$, R$^{58}$, R$^{88}$, R$^{108}$, and R$^{178}$ at each occurrence is independently chosen from C$_{1-6}$alkyl optionally substituted by 1-6 R$^{189}$ and C$_{7-16}$arylalkyl optionally substituted by 1-6 R$^{189}$. In another embodiment, R$^{18}$, R$^{58}$, R$^{88}$, R$^{108}$, and R$^{178}$ at each occurrence is independently C$_{1-6}$alkyl optionally substituted by 1-6 R$^{189}$. In another embodiment, R$^{18}$, R$^{58}$, R$^{88}$, R$^{108}$, and R$^{178}$ at each occurrence is independently C$_{1-6}$alkyl.

In each embodiment of the present invention that is described in the paragraphs that precede or follow this paragraph, the definitions of R$^1$, R$^4$, R$^5$, R$^{10}$, R$^{11}$, R$^{14}$, R$^{15}$, R$^{16}$, R$^{17}$, R$^{21}$, R$^{24}$, R$^{25}$, R$^{26}$, R$^{31}$, R$^{34}$, R$^{35}$, R$^{36}$, R$^{41}$, R$^{44}$, R$^{45}$, R$^{46}$, R$^{50}$, R$^{51}$, R$^{54}$, R$^{55}$, R$^{56}$, R$^{57}$, R$^{61}$, R$^{64}$, R$^{65}$, R$^{66}$, R$^{71}$, R$^{74}$, R$^{75}$, R$^{76}$, R$^{80}$, R$^{81}$, R$^{84}$, R$^{85}$, R$^{86}$, R$^{87}$, R$^{90}$, R$^{91}$, R$^{94}$, R$^{95}$, R$^{96}$, R$^{97}$, R$^{100}$, R$^{101}$, R$^{104}$, R$^{105}$, R$^{106}$, R$^{107}$, R$^{130}$, R$^{131}$, R$^{134}$, R$^{135}$, R$^{136}$, R$^{137}$, R$^{170}$, R$^{171}$, R$^{174}$, R$^{175}$, R$^{176}$ and R$^{177}$ may be chosen from any of the embodiments that are described in this paragraph. In one embodiment, R$^1$, R$^4$, R$^5$, R$^6$, R$^{10}$, R$^{11}$, R$^{14}$, R$^{15}$, R$^{16}$, R$^{17}$, R$^{21}$, R$^{24}$, R$^{25}$, R$^{26}$, R$^{31}$, R$^{34}$, R$^{35}$, R$^{36}$, R$^{41}$, R$^{44}$, R$^{45}$, R$^{46}$, R$^{50}$, R$^{51}$, R$^{54}$, R$^{55}$, R$^{56}$, R$^{57}$, R$^{61}$, R$^{64}$, R$^{65}$, R$^{66}$, R$^{71}$, R$^{74}$, R$^{75}$, R$^{76}$, R$^{80}$, R$^{81}$, R$^{84}$, R$^{85}$, R$^{86}$, R$^{87}$, R$^{90}$, R$^{91}$, R$^{94}$, R$^{95}$, R$^{96}$, R$^{97}$, R$^{100}$, R$^{101}$, R$^{104}$, R$^{105}$, R$^{106}$, R$^{107}$, R$^{130}$, R$^{131}$, R$^{134}$, R$^{135}$, R$^{136}$, R$^{137}$, R$^{170}$, R$^{171}$, R$^{174}$, R$^{175}$, R$^{176}$ and R$^{177}$ at each occurrence is independently chosen from H, C$_{1-6}$alkyl optionally substituted by 1-11 R$^{189}$, C$_{2-6}$alkenyl optionally substituted by 1-11 R$^{189}$, C$_{2-6}$alkynyl optionally substituted by 1-9 R$^{189}$, C$_{6-11}$aryl optionally substituted by 1-11 R$^{189}$, C$_{7-16}$arylalkyl optionally substituted by 1-19 R$^{189}$, C$_{3-11}$cycloalkyl optionally substituted by 1-21 R$^{189}$, C$_{4-17}$cycloalkylalkyl optionally substituted by 1-32 R$^{189}$, 3-15 membered heterocycloalkyl optionally substituted by 1-28 R$^{189}$, 4-21 membered heterocycloalkylalkyl optionally substituted by 1-40 R$^{189}$, 5-15 membered heteroaryl optionally substituted by 1-15 R$^{189}$, and 6-21 membered heteroarylalkyl optionally substituted by 1-27 R$^{189}$. In another embodiment, R$^1$, R$^4$, R$^5$, R$^6$, R$^{10}$, R$^{11}$, R$^{14}$, R$^{15}$, R$^{16}$, R$^{17}$, R$^{21}$, R$^{24}$, R$^{25}$, R$^{26}$, R$^{31}$, R$^{34}$, R$^{35}$, R$^{36}$, R$^{41}$, R$^{44}$, R$^{45}$, R$^{46}$, R$^{50}$, R$^{51}$, R$^{54}$, R$^{55}$, R$^{56}$, R$^{57}$, R$^{61}$, R$^{64}$, R$^{65}$, R$^{66}$, R$^{71}$, R$^{74}$, R$^{75}$, R$^{76}$, R$^{80}$, R$^{81}$, R$^{84}$, R$^{85}$, R$^{86}$, R$^{87}$, R$^{90}$, R$^{91}$, R$^{94}$, R$^{95}$, R$^{96}$, R$^{97}$, R$^{100}$, R$^{101}$, R$^{104}$, R$^{105}$, R$^{106}$, R$^{107}$, R$^{130}$, R$^{131}$, R$^{134}$, R$^{135}$, R$^{136}$, R$^{137}$, R$^{170}$, R$^{171}$, R$^{174}$, R$^{175}$, R$^{176}$ and R$^{177}$ at each occurrence is chosen from H, C$_{1-6}$alkyl optionally substituted by 1-13 R$^{189}$, C$_{6-11}$ aryl optionally substituted by 1-7 R$^{189}$, C$_{7-16}$arylalkyl optionally substituted by 1-19 R$^{189}$, C$_{3-11}$cycloalkyl optionally substituted by 1-21 R$^{189}$, C$_{4-17}$cycloalkylalkyl optionally substituted by 1-32 R$^{189}$, 3-15 membered heterocycloalkyl optionally substituted by 1-28 R$^{189}$, 4-21 membered heterocycloalkylalkyl optionally substituted by 1-40 R$^{189}$, 5-15 membered heteroaryl optionally substituted by 1-15 R$^{189}$, and 6-21 membered heteroarylalkyl optionally substituted by 1-27 R$^{189}$. In another embodiment, R$^1$, R$^4$, R$^5$, R$^6$, R$^{10}$, R$^{11}$, R$^{14}$, R$^{15}$, R$^{16}$, R$^{17}$, R$^{21}$, R$^{24}$, R$^{25}$, R$^{26}$, R$^{31}$, R$^{34}$, R$^{35}$, R$^{36}$, R$^{41}$, R$^{44}$, R$^{45}$, R$^{46}$, R$^{50}$, R$^{51}$, R$^{54}$, R$^{55}$, R$^{56}$, R$^{57}$, R$^{61}$, R$^{64}$, R$^{65}$, R$^{66}$, R$^{71}$, R$^{74}$, R$^{75}$, R$^{76}$, R$^{80}$, R$^{81}$, R$^{84}$, R$^{85}$, R$^{86}$, R$^{87}$, R$^{90}$, R$^{91}$, R$^{94}$, R$^{95}$, R$^{96}$, R$^{97}$, R$^{100}$, R$^{101}$, R$^{104}$, R$^{105}$, R$^{106}$, R$^{107}$, R$^{130}$, R$^{131}$, R$^{134}$, R$^{135}$, R$^{136}$, R$^{137}$, R$^{170}$, R$^{171}$, R$^{174}$, R$^{175}$, R$^{176}$ and R$^{177}$ at each occurrence is independently chosen from H, C$_{1-6}$alkyl optionally substituted by 1-13 R$^{189}$, C$_{6-11}$aryl optionally substituted by 1-7 $R^{189}$, $C_{7-16}$arylalkyl optionally substituted by 1-19 $R^{189}$, $C_{3-11}$cycloalkyl optionally substituted by 1-21 $R^{189}$, $C_{4-17}$cycloalkylalkyl optionally substituted by 1-32 $R^{189}$, 3-15 membered heterocycloalkyl optionally substituted by 1-28 $R^{189}$, 4-21 membered heterocycloalkylalkyl optionally substituted by 1-40 $R^{189}$, and 6-21 membered heteroarylalkyl optionally substituted by 1-27 $R^{189}$. In another embodiment $R^1$, $R^4$, $R^5$, $R^6$, $R^{10}$, $R^{11}$, $R^{14}$, $R^{15}$, $R^{16}$, $R^{17}$, $R^{21}$, $R^{24}$, $R^{25}$, $R^{26}$, $R^{31}$, $R^{34}$, $R^{35}$, $R^{36}$, $R^{41}$, $R^{44}$, $R^{45}$, $R^{46}$, $R^{50}$, $R^{51}$, $R^{54}$, $R^{55}$, $R^{56}$, $R^{57}$, $R^{61}$, $R^{64}$, $R^{65}$, $R^{66}$, $R^{71}$, $R^{74}$, $R^{75}$, $R^{76}$, $R^{80}$, $R^{81}$, $R^{84}$, $R^{85}$, $R^{86}$, $R^{87}$, $R^{90}$, $R^{91}$, $R^{94}$, $R^{95}$, $R^{96}$, $R^{97}$, $R^{100}$, $R^{101}$, $R^{104}$, $R^{105}$, $R^{106}$, $R^{107}$, $R^{130}$, $R^{131}$, $R^{134}$, $R^{135}$, $R^{136}$, $R^{137}$, $R^{170}$, $R^{171}$, $R^{174}$, $R^{175}$, $R^{176}$ and $R^{177}$ at each occurrence is independently chosen from H, $C_{1-6}$alkyl optionally substituted by 1-13 $R^{189}$, $C_{7-16}$arylalkyl optionally substituted by 1-19 $R^{189}$, $C_{4-17}$cycloalkylalkyl optionally substituted by 1-32 $R^{189}$, 4-21 membered heterocycloalkylalkyl optionally substituted by 1-40 $R^{189}$, and 6-21 membered heteroarylalkyl optionally substituted by 1-27 $R^{189}$. In another embodiment $R^1$, $R^4$, $R^5$, $R^6$, $R^{10}$, $R^{11}$, $R^{14}$, $R^{15}$, $R^{16}$, $R^{17}$, $R^{21}$, $R^{24}$, $R^{25}$, $R^{26}$, $R^{31}$, $R^{34}$, $R^{35}$, $R^{36}$, $R^{41}$, $R^{44}$, $R^{45}$, $R^{46}$, $R^{50}$, $R^{51}$, $R^{54}$, $R^{55}$, $R^{56}$, $R^{57}$, $R^{61}$, $R^{64}$, $R^{65}$, $R^{66}$, $R^{71}$, $R^{74}$, $R^{75}$, $R^{76}$, $R^{80}$, $R^{81}$, $R^{84}$, $R^{85}$, $R^{86}$, $R^{87}$, $R^{90}$, $R^{91}$, $R^{94}$, $R^{95}$, $R^{96}$, $R^{97}$, $R^{100}$, $R^{101}$, $R^{104}$, $R^{105}$, $R^{106}$, $R^{107}$, $R^{130}$, $R^{131}$, $R^{134}$, $R^{135}$, $R^{136}$, $R^{137}$, $R^{170}$, $R^{171}$, $R^{174}$, $R^{175}$, $R^{176}$ and $R^{177}$, at each occurrence is independently chosen from H, $C_{1-6}$alkyl optionally substituted by 1-6 $R^{189}$, $C_{6-11}$ aryl optionally substituted by 1-6 $R^{189}$, $C_{7-16}$arylalkyl optionally substituted by 1-6 $R^{189}$, $C_{3-11}$cycloalkyl optionally substituted by 1-6 $R^{189}$, $C_{4-17}$cycloalkylalkyl optionally substituted by 1-6 $R^{189}$, 3-15 membered heterocycloalkyl optionally substituted by 1-6 $R^{189}$, 4-21 membered heterocycloalkylalkyl optionally substituted by 1-6 $R^{189}$, 5-15 membered heteroaryl optionally substituted by 1-6 $R^{189}$, and 6-21 membered heteroarylalkyl optionally substituted by 1-6 $R^{189}$. In another embodiment, $R^1$, $R^4$, $R^5$, $R^6$, $R^{10}$, $R^{11}$, $R^{14}$, $R^{15}$, $R^{16}$, $R^{17}$, $R^{21}$, $R^{24}$, $R^{25}$, $R^{26}$, $R^{31}$, $R^{34}$, $R^{35}$, $R^{36}$, $R^{41}$, $R^{44}$, $R^{45}$, $R^{46}$, $R^{50}$, $R^{51}$, $R^{54}$, $R^{55}$, $R^{56}$, $R^{57}$, $R^{61}$, $R^{64}$, $R^{65}$, $R^{66}$, $R^{71}$, $R^{74}$, $R^{75}$, $R^{76}$, $R^{80}$, $R^{81}$, $R^{84}$, $R^{85}$, $R^{86}$, $R^{87}$, $R^{90}$, $R^{91}$, $R^{94}$, $R^{95}$, $R^{96}$, $R^{97}$, $R^{100}$, $R^{101}$, $R^{104}$, $R^{105}$, $R^{106}$, $R^{107}$, $R^{130}$, $R^{131}$, $R^{134}$, $R^{135}$, $R^{136}$, $R^{137}$, $R^{170}$, $R^{171}$, $R^{174}$, $R^{175}$, $R^{176}$ and $R^{177}$ at each occurrence is independently chosen from H, $C_{1-6}$alkyl optionally substituted by 1-6 $R^{189}$, $C_{6-11}$aryl optionally substituted by 1-7 $R^{189}$, $C_{7-16}$arylalkyl optionally substituted by 1-6 $R^{189}$, $C_{3-11}$cycloalkyl optionally substituted by 1-6 $R^{189}$, $C_{4-17}$cycloalkylalkyl optionally substituted by 1-6 $R^{189}$, 3-15 membered heterocycloalkyl optionally substituted by 1-6 $R^{189}$, 4-21 membered heterocycloalkylalkyl optionally substituted by 1-6 $R^{189}$, and 6-21 membered heteroarylalkyl optionally substituted by 1-6 $R^{189}$. In another embodiment, $R^1$, $R^4$, $R^5$, $R^6$, $R^{10}$, $R^{11}$, $R^{14}$, $R^{15}$, $R^{16}$, $R^{17}$, $R^{21}$, $R^{24}$, $R^{25}$, $R^{26}$, $R^{31}$, $R^{34}$, $R^{35}$, $R^{36}$, $R^{41}$, $R^{44}$, $R^{45}$, $R^{46}$, $R^{50}$, $R^{51}$, $R^{54}$, $R^{55}$, $R^{56}$, $R^{57}$, $R^{61}$, $R^{64}$, $R^{65}$, $R^{66}$, $R^{71}$, $R^{74}$, $R^{75}$, $R^{76}$, $R^{80}$, $R^{81}$, $R^{84}$, $R^{85}$, $R^{86}$, $R^{87}$, $R^{90}$, $R^{91}$, $R^{94}$, $R^{95}$, $R^{96}$, $R^{97}$, $R^{100}$, $R^{101}$, $R^{104}$, $R^{105}$, $R^{106}$, $R^{107}$, $R^{130}$, $R^{131}$, $R^{134}$, $R^{135}$, $R^{136}$, $R^{137}$, $R^{170}$, $R^{171}$, $R^{174}$, $R^{175}$, $R^{176}$ and $R^{177}$ at each occurrence is independently chosen from H, $C_{1-6}$alkyl optionally substituted by 1-6 $R^{189}$, $C_{7-16}$arylalkyl optionally substituted by 1-6 $R^{189}$, $C_{4-17}$cycloalkylalkyl optionally substituted by 1-6 $R^{189}$, 4-21 membered heterocycloalkylalkyl optionally substituted by 1-6 $R^{189}$, and 6-21 membered heteroarylalkyl optionally substituted by 1-6 $R^{189}$. In another embodiment, $R^4$ is $C_{1-6}$alkyl or H. In another embodiment, $R^4$ is H. In another embodiment, $R^{10}$ at each occurrence is independently chosen from H and $C_{1-6}$alkyl optionally substituted by 1-13 $R^{189}$. In another embodiment, $R^{10}$ at each occurrence is independently chosen from $C_{1-6}$alkyl optionally substituted by 1-13 $R^{189}$. In another embodiment, $R^{10}$ at each occurrence is independently chosen from $C_{1-6}$alkyl. In another embodiment, $R^{10}$ is methyl. In another embodiment, $R^{24}$ is $C_{1-6}$alkyl or H. In another embodiment, $R^{24}$ is $C_{1-6}$alkyl. In another embodiment, $R^{24}$ is methyl. In another embodiment, $R^{44}$ is H. In another embodiment, $R^{64}$ at each occurrence is independently chosen from H and $C_{1-6}$alkyl optionally substituted by 1-13 $R^{189}$. In another embodiment, $R^{64}$ at each occurrence is independently chosen from H and $C_{1-6}$alkyl optionally substituted by 1-13 $R^{189}$. In another embodiment, $R^{64}$ at each occurrence is independently chosen from H and $C_{1-6}$alkyl. In another embodiment, $R^{64}$ at each occurrence is independently chosen from H and methyl. In another embodiment, $R^{100}$ at each occurrence is independently chosen from H, $C_{1-6}$alkyl optionally substituted by 1-13 $R^{189}$, and $C_{7-16}$arylalkyl optionally substituted by 1-19 $R^{189}$. In another embodiment, $R^{100}$ at each occurrence is independently chosen from H, $C_{1-6}$alkyl optionally substituted by 1-3 $R^{189}$, and $C_{7-16}$arylalkyl optionally substituted by 1-3 $R^{189}$. In another embodiment, $R^{100}$ at each occurrence is independently chosen from H, $C_{1-6}$alkyl optionally substituted by 1-3 $R^{189}$, and $C_{7-12}$arylalkyl optionally substituted by 1-3 $R^{189}$. In another embodiment, $R^{100}$ at each occurrence is independently chosen from H, $C_{1-6}$alkyl, and $C_{7-12}$arylalkyl. In another embodiment, $R^{100}$ at each occurrence is independently chosen from $C_{1-6}$alkyl, and $C_{7-12}$arylalkyl. In another embodiment, $R^{100}$ at each occurrence is independently chosen from methyl and benzyl. In another embodiment, $R^{102}$ and $R^{103}$ are H.

In each embodiment of the present invention that is described in the paragraphs that precede or follow this paragraph, the definitions of, $R^2$, $R^3$, $R^{12}$, $R^{13}$, $R^{22}$, $R^{23}$, $R^{32}$, $R^{33}$, $R^{42}$, $R^{43}$, $R^{52}$, $R^{53}$, $R^{62}$, $R^{63}$, $R^{72}$, $R^{73}$, $R^{82}$, $R^{83}$, $R^{92}$, $R^{93}$, $R^{102}$, $R^{103}$, $R^{132}$, $R^{133}$, $R^{172}$ and $R^{173}$ may be chosen from any of the embodiments that are described in this paragraph. In one embodiment, $R^2$, $R^3$, $R^{12}$, $R^{13}$, $R^{22}$, $R^{23}$, $R^{32}$, $R^{33}$, $R^{42}$, $R^{43}$, $R^{52}$, $R^{53}$, $R^{62}$, $R^{63}$, $R^{72}$, $R^{73}$, $R^{82}$, $R^{83}$, $R^{92}$, $R^{93}$, $R^{102}$, $R^{103}$, $R^{132}$, $R^{133}$, $R^{172}$ and $R^{173}$, at each occurrence is independently chosen from H, $C_{1-6}$alkyl optionally substituted by 1-13 $R^{199}$, $C_{2-6}$alkenyl optionally substituted by 1-11 $R^{199}$, $C_{2-6}$alkynyl optionally substituted by 1-9 $R^{199}$, $C_{6-11}$ aryl optionally substituted by 1-7 $R^{199}$, $C_{7-16}$arylalkyl optionally substituted by 1-19 $R^{199}$, $C_{3-11}$cycloalkyl optionally substituted by 1-21 $R^{199}$, $C_{4-17}$cycloalkylalkyl optionally substituted by 1-32 $R^{199}$, 3-15 membered heterocycloalkyl optionally substituted by 1-28 $R^{199}$, 4-21 membered heterocycloalkylalkyl optionally substituted by 1-40 $R^{199}$, 5-15 membered heteroaryl optionally substituted by 1-15 $R^{199}$, and 6-21 membered heteroarylalkyl optionally substituted by 1-27 $R^{199}$; or any $R^2$ and $R^3$, $R^{12}$ and $R^{13}$, $R^{22}$ and $R^{23}$, $R^{32}$ and $R^{33}$, $R^{42}$ and $R^{43}$, $R^{52}$ and $R^{53}$, $R^{62}$ and $R^{63}$, $R^{72}$ and $R^{73}$, $R^{82}$ and $R^{83}$, $R^{92}$ and $R^{93}$, $R^{102}$ and $R^{103}$, $R^{132}$ and $R^{133}$, or $R^{172}$ and $R^{173}$ may form, together with the nitrogen atom to which they are attached, a 3-15 membered heterocycloalkyl optionally substituted by 1-28 $R^{209}$ or a 5-15 membered heteroaryl optionally substituted by 1-15 $R^{209}$. In another embodiment, $R^2$, $R^3$, $R^{12}$, $R^{13}$, $R^{22}$, $R^{23}$, $R^{32}$, $R^{33}$, $R^{42}$, $R^{43}$, $R^{52}$, $R^{53}$, $R^{62}$, $R^{63}$, $R^{72}$, $R^{73}$, $R^{82}$, $R^{83}$, $R^{92}$, $R^{93}$, $R^{102}$, $R^{103}$, $R^{132}$, $R^{133}$, $R^{172}$ and $R^{173}$ at each occurrence is independently chosen from H, $C_{1-6}$alkyl optionally substituted by 1-13 $R^{199}$, $C_{6-11}$aryl optionally substituted by 1-7 $R^{199}$, $C_{7-16}$arylalkyl optionally substituted by 1-19 $R^{199}$, $C_{3-11}$cycloalkyl optionally substituted by 1-21 $R^{199}$, $C_{4-17}$cycloalkylalkyl optionally substituted by 1-32 $R^{199}$, 3-15 membered heterocycloalkyl optionally substituted by 1-28 $R^{199}$, 4-21 membered heterocycloalkylalkyl optionally substituted by 1-40 $R^{199}$, 5-15 membered heteroaryl optionally substituted by 1-15 $R^{199}$, and 6-21 membered heteroarylalkyl optionally substituted by 1-27 $R^{199}$; or any $R^2$ and $R^3$, $R^{12}$ and $R^{13}$, $R^{22}$ and $R^{23}$, $R^{32}$ and $R^{33}$, $R^{42}$ and $R^{43}$, $R^{52}$ and $R^{53}$, $R^{62}$ and $R^{63}$, $R^{72}$ and $R^{73}$, $R^{82}$ and $R^{83}$, $R^{92}$ and $R^{93}$, $R^{102}$ and $R^{103}$, $R^{132}$ and $R^{133}$, or $R^{172}$ and $R^{173}$ may form, together with the nitrogen atom to which they are attached, a 3-15 membered heterocycloalkyl optionally substituted by 1-28 $R^{209}$ or a 5-15 membered heteroaryl optionally substituted by 1-15 $R^{209}$. In another embodiment, $R^2$, $R^3$, $R^{12}$, $R^{13}$, $R^{22}$, $R^{23}$, $R^{32}$, $R^{33}$, $R^{42}$, $R^{43}$, $R^{52}$, $R^{53}$, $R^{62}$, $R^{63}$, $R^{72}$, $R^{73}$, $R^{82}$, $R^{83}$, $R^{92}$, $R^{93}$, $R^{102}$, $R^{103}$, $R^{132}$, $R^{133}$, $R^{172}$ and $R^{173}$ at each occurrence is independently chosen from H, $C_{1-6}$alkyl optionally substituted by 1-13 $R^{199}$, $C_{7-16}$arylalkyl optionally substituted by 1-19 $R^{199}$, $C_{4-17}$cycloalkylalkyl optionally substituted by 1-32 $R^{199}$, 4-21 membered heterocycloalkylalkyl optionally substituted by 1-40 $R^{199}$, and 6-21 membered heteroarylalkyl optionally substituted by 1-27 $R^{199}$; or any $R^2$ and $R^3$, $R^{12}$ and $R^{13}$, $R^{22}$ and $R^{23}$, $R^{32}$ and $R^{33}$, $R^{42}$ and $R^{43}$, $R^{52}$ and $R^{53}$, $R^{62}$ and $R^{63}$, $R^{72}$ and $R^{73}$, $R^{82}$ and $R^{83}$, $R^{92}$ and $R^{93}$, $R^{102}$ and $R^{103}$, $R^{132}$ and $R^{133}$, or $R^{172}$ and $R^{173}$ may form, together with the nitrogen atom to which they are attached, a 3-15 membered heterocycloalkyl optionally substituted by 1-28 $R^{209}$ or a 5-15 membered heteroaryl optionally substituted by 1-15 $R^{209}$. In another embodiment, $R^2$, $R^3$, $R^{12}$, $R^{13}$, $R^{22}$, $R^{23}$, $R^{32}$, $R^{33}$, $R^{42}$, $R^{43}$, $R^{52}$, $R^{53}$, $R^{62}$, $R^{63}$, $R^{72}$, $R^{73}$, $R^{82}$, $R^{83}$, $R^{92}$, $R^{93}$, $R^{102}$, $R^{103}$, $R^{132}$, $R^{133}$, $R^{172}$ and $R^{173}$ at each occurrence is independently chosen from H, $C_{1-6}$alkyl optionally substituted by 1-13 $R^{199}$, $C_{7-16}$arylalkyl optionally substituted by 1-19 $R^{199}$, $C_{4-17}$cycloalkylalkyl optionally substituted by 1-32 $R^{199}$, 4-21 membered heterocycloalkylalkyl optionally substituted by 1-40 $R^{199}$, and 6-21 membered heteroarylalkyl optionally substituted by 1-27 $R^{199}$. In another embodiment, $R^2$, $R^3$, $R^{12}$, $R^{13}$, $R^{22}$, $R^{23}$, $R^{32}$, $R^{33}$, $R^{42}$, $R^{43}$, $R^{52}$, $R^{53}$, $R^{62}$, $R^{63}$, $R^{72}$, $R^{73}$, $R^{82}$, $R^{83}$, $R^{92}$, $R^{93}$, $R^{102}$, $R^{103}$, $R^{132}$, $R^{133}$, $R^{172}$ and $R^{173}$ at each occurrence is independently chosen from H, $C_{1-6}$alkyl optionally substituted by 1-6 $R^{199}$, $C_{6-11}$aryl optionally substituted by 1-7 $R^{199}$, $C_{7-16}$arylalkyl optionally substituted by 1-6 $R^{199}$, $C_{3-11}$cycloalkyl optionally substituted by 1-6 $R^{199}$, $C_{4-17}$cycloalkylalkyl optionally substituted by 1-6 $R^{199}$, 3-15 membered heterocycloalkyl optionally substituted by 1-6 $R^{199}$, 4-21 membered heterocycloalkylalkyl optionally substituted by 1-6 $R^{199}$, 5-15 membered heteroaryl optionally substituted by 1-6 $R^{199}$, and 6-21 membered heteroarylalkyl optionally substituted by 1-6 $R^{199}$; or any $R^2$ and $R^3$, $R^{12}$ and $R^{13}$, $R^{22}$ and $R^{23}$, $R^{32}$ and $R^{33}$, $R^{42}$ and $R^{43}$, $R^{52}$ and $R^{53}$, $R^{62}$ and $R^{63}$, $R^{72}$ and $R^{73}$, $R^{82}$ and $R^{83}$, $R^{92}$ and $R^{93}$, $R^{102}$ and $R^{103}$, $R^{132}$ and $R^{133}$, or $R^{172}$ and $R^{173}$ may form, together with the nitrogen atom to which they are attached, a 3-15 membered heterocycloalkyl optionally substituted by 1-6 $R^{209}$ or a 5-15 membered heteroaryl optionally substituted by 1-6 $R^{209}$. In another embodiment, $R^2$, $R^3$, $R^{12}$, $R^{13}$, $R^{22}$, $R^{23}$, $R^{32}$, $R^{33}$, $R^{42}$, $R^{43}$, $R^{52}$, $R^{53}$, $R^{62}$, $R^{63}$, $R^{72}$, $R^{73}$, $R^{82}$, $R^{83}$, $R^{92}$, $R^{93}$, $R^{102}$, $R^{103}$, $R^{132}$, $R^{133}$, $R^{172}$ and $R^{173}$ at each occurrence is independently chosen from H, $C_{1-6}$alkyl optionally substituted by 1-6 $R^{199}$, $C_{7-16}$arylalkyl optionally substituted by 1-6 $R^{199}$, $C_{4-17}$cycloalkylalkyl optionally substituted by 1-6 $R^{199}$, 4-21 membered heterocycloalkylalkyl optionally substituted by 1-6 $R^{199}$, and 6-21 membered heteroarylalkyl optionally substituted by 1-6 $R^{199}$.

In each embodiment of the present invention that is described in the paragraphs that precede or follow this paragraph, the definitions of $R^{179}$, $R^{189}$, $R^{199}$ and $R^{209}$ may be chosen from any of the embodiments that are described in this paragraph. In one embodiment, $R^{179}$, $R^{189}$, $R^{199}$ and $R^{209}$ at each occurrence is independently chosen from $C_{1-6}$alkyl optionally substituted by 1-13 $R^{219}$, $C_{2-6}$alkenyl optionally substituted by 1-11 $R^{219}$, $C_{2-6}$alkynyl optionally substituted by 1-9 $R^{219}$, $C_{6-11}$ aryl optionally substituted by 1-11 $R^{219}$, $C_{7-16}$arylalkyl optionally substituted by 1-19 $R^{219}$, $C_{3-11}$cycloalkyl optionally substituted by 1-21 $R^{219}$, $C_{4-17}$cycloalkylalkyl optionally substituted by 1-32 $R^{219}$, 3-15 membered heterocycloalkyl optionally substituted by 1-28 $R^{219}$, 4-21 membered heterocycloalkylalkyl optionally substituted by 1-40 $R^{219}$, 5-15 membered heteroaryl optionally substituted by 1-15 $R^{219}$, 6-21 membered heteroarylalkyl optionally substituted by 1-27 $R^{219}$, halogen, —CN, —C(=O)$R^{210}$, —C(=O)O$R^{210}$, —C(=O)N$R^{212}R^{213}$, —C(=O)C(=O)$R^{210}$, —C(=N$R^{215}$)$R^{210}$, —C(=N$R^{215}$)N$R^{212}R^{213}$, —C(=NOH)N$R^{212}R^{213}$, —C(=NO$R^{216}$)$R^{210}$, —C(=NN$R^{212}R^{213}$)$R^{210}$, —C(NN$R^{214}$C(=O)$R^{211}$)$R^{210}$, C(=NN$R^{214}$C(=O)O$R^{211}$)$R^{210}$, —C(=S)N$R^{212}R^{213}$, —NC, —NO$_2$, —N$R^{212}R^{213}$, —N$R^{214}$N$R^{212}R^{213}$, —N=N$R^{214}$, =N$R^{219}$, =NO$R^{219}$, —N$R^{214}$O$R^{216}$, —N$R^{214}$C(=O)$R^{219}$, —N$R^{214}$C(=O)C(=O)$R^{210}$, —N$R^{214}$C(=O)O$R^{211}$, —N$R^{214}$C(=O)C(=O)O$R^{211}$, —N$R^{214}$C(=O)N$R^{212}R^{213}$, —N$R^{214}$C(=O)N$R^{214}$C(=O)$R^{210}$, —N$R^{214}$C(=O)N$R^{214}$C(=O)O$R^{210}$, —N$R^{214}$C(=N$R^{215}$)N$R^{212}R^{213}$, —N$R^{214}$C(=O)C(=O)N$R^{212}R^{213}$, —N$R^{214}$C(=S)$R^{210}$, —N$R^{214}$C(=S)O$R^{210}$, —N$R^{214}$C(=S)N$R^{212}R^{213}$, —N$R^{214}$S(=O)$_2R^{211}$, —N$R^{214}$S(=O)$_2$N$R^{212}R^{213}$, —N$R^{214}$P(=O)$R^{218}R^{218}$, —N$R^{214}$P(=O)(N$R^{212}R^{213}$)(N$R^{212}R^{213}$), —N$R^{214}$P(=O)(O$R^{210}$)(O$R^{210}$), —N$R^{214}$P(=O)(S$R^{210}$)(S$R^{210}$), —O$R^{210}$, =O, —OCN, —OC(=O)$R^{210}$, —OC(=O)N$R^{212}R^{213}$, —OC(=O)O$R^{210}$, —OC(=N$R^{215}$)N$R^{212}R^{213}$, —OS(=O)$R^{210}$, —OS(=O)$_2R^{210}$, —OS(=O)$_2$O$R^{210}$, —OS(=O)$_2$N$R^{212}R^{213}$, —OP(=O)$R^{218}$, —OP(=O)(O$R^{210}$)(O$R^{210}$), —OP(=O)(S$R^{210}$)(S$R^{210}$), —SCN, =S, —S(=O)$_nR^{210}$, —S(=)$_2$O$R^{210}$, —SO$_3R^{217}$, —S(=O)$_2$N$R^{212}R^{213}$, —SP(=O)$R^{218}R^{218}$, SP(=O)(N$R^{212}R^{213}$)(N$R^{212}R^{213}$), —SP(=O)(O$R^{210}$)(O$R^{210}$), —SP(=O)(S$R^{210}$)(S$R^{210}$), —P(=O)$R^{218}R^{218}$, —P(=O)(N$R^{212}R^{213}$)(N$R^{212}R^{213}$), —P(=O)(O$R^{210}$)(O$R^{210}$), and —P(=O)(S$R^{210}$)(S$R^{210}$). In another embodiment, $R^{179}$, $R^{189}$, $R^{199}$ and $R^{209}$ at each occurrence is independently chosen from $C_{1-6}$alkyl optionally substituted by 1-13 $R^{219}$, $C_{2-6}$alkenyl optionally substituted by 1-11 $R^{219}$, $C_{2-6}$alkynyl optionally substituted by 1-9 $R^{219}$, $C_{6-11}$ aryl optionally substituted by 1-11 $R^{219}$, $C_{7-16}$arylalkyl optionally substituted by 1-19 $R^{219}$, $C_{3-11}$cycloalkyl optionally substituted by 1-21 $R^{219}$, $C_{4-17}$cycloalkylalkyl optionally substituted by 1-32 $R^{219}$, 3-15 membered heterocycloalkyl optionally substituted by 1-28 $R^{219}$, 4-21 membered heterocycloalkylalkyl optionally substituted by 1-40 $R^{219}$, 5-15 membered heteroaryl optionally substituted by 1-15 $R^{219}$, 6-21 membered heteroarylalkyl optionally substituted by 1-27 $R^{219}$, halogen, —CN, —C(=O)$R^{210}$, —C(=O)O$R^{210}$, —C(=O)N$R^{212}R^{213}$, —C(=O)C(=O)$R^{210}$, —C(=N$R^{215}$)$R^{210}$, C(=N$R^{215}$)N$R^{212}R^{213}$, —C(=NOH)N$R^{212}R^{213}$, —C(=NO$R^{216}$)$R^{210}$, —C(=NN$R^{212}R^{213}$)$R^{210}$, —C(=NN$R^{214}$C(=O)$R^{211}$)$R^{210}$, —C(=NN$R^{214}$C(=O)O$R^{211}$)$R^{210}$, —C(=S)N$R^{212}R^{213}$, —NC, —NO$_2$, —$NR^{212}R^{213}$, —$NR^{214}NR^{212}R^{213}$, —N=$NR^{214}$, =$NR^{210}$, =$NOR^{210}$, —$NR^{214}OR^{216}$, —$NR^{214}C(=O)R^{210}$, —$NR^{214}C(=O)C(=O)R^{210}$, —$NR^{214}C(=O)OR^{211}$, —$NR^{214}C(=O)C(=O)OR^{211}$, —$NR^{214}C(=O)NR^{212}R^{213}$, —$NR^{214}C(=O)NR^{214}C(=O)R^{210}$, —$NR^{214}C(=O)NR^{214}C(=O)OR^{210}$, $NR^{214}C(NR^{215})NR^{212}R^{213}$, $NR^{214}C(=O)C(=O)NR^{212}R^{213}$, $NR^{214}C(S)R^{219}$, $NR^{214}C(S)OR^{210}$, —$NR^{214}C(=S)NR^{212}R^{213}$, —$NR^{214}S(=O)_2R^{211}$, —$NR^{214}S(=O)_2NR^{212}R^{213}$, —$NR^{214}P(=O)R^{218}R^{218}$, —$OR^{210}$, =O, —OCN, —OC(=O)$R^{210}$, —OC(=O)$NR^{212}R^{213}$, —OC(=O)$OR^{210}$, —OC(=$NR^{215}$)$NR^{212}R^{213}$, —OS(=O)$R^{210}$, —OS(=O)$_2R^{210}$, —OS(=O)$_2OR^{210}$, —OS(=O)$_2NR^{212}R^{213}$, —SCN, =S, —S(=O)$_nR^{210}$, —S(=O)$_2OR^{210}$, —$SO_3R^{217}$, —S(=O)$_2NR^{212}R^{213}$, —S(=O)$NR^{212}R^{213}$, and —P(=O)$R^{218}R^{218}$. In another embodiment, $R^{179}$, $R^{189}$, $R^{199}$ and $R^{209}$ at each occurrence is independently chosen from $C_{1-6}$alkyl optionally substituted by 1-13 $R^{219}$, $C_{2-6}$alkenyl optionally substituted by 1-6 $R^{219}$, $C_{2-6}$alkynyl optionally substituted by 1-9 $R^{219}$, $C_{6-11}$aryl optionally substituted by 1-6 $R^{219}$, $C_{7-16}$arylalkyl optionally substituted by 1-19 $R^{219}$, $C_{3-11}$cycloalkyl optionally substituted by 1-6 $R^{219}$, $C_{4-17}$cycloalkylalkyl optionally substituted by 1-32 $R^{219}$, 3-15 membered heterocycloalkyl optionally substituted by 1-28 $R^{219}$, 4-21 membered heterocycloalkylalkyl optionally substituted by 1-40 $R^{219}$, 5-15 membered heteroaryl optionally substituted by 1-15 $R^{219}$, 6-21 membered heteroarylalkyl optionally substituted by 1-27 $R^{219}$, halogen, —CN, —C(=O)$R^{210}$, —C(=O)$OR^{210}$, —C(=O)$NR^{212}R^{213}$, —C(=O)C(=O)$R^{210}$, —C(=$NR^{215}$)$R^{210}$, —C(=$NR^{215}$)$NR^{212}R^{213}$, —C(=NOH)$NR^{212}R^{213}$, —C(=$NOR^{216}$)$R^{210}$, —C(=$NNR^{212}R^{213}$)$R^{210}$, —C(=$NNR^{214}C(=O)R^{211}$)$R^{210}$, C(=$NNR^{214}C(=O)OR^{211}$)$R^{210}$, —C(=S)$NR^{212}R^{213}$, —NC, —$NO_2$, —$NR^{212}R^{213}$, —$NR^{214}NR^{212}R^{213}$, —N=$NR^{214}$, =$NR^{210}$, =$NOR^{210}$, —$NR^{214}OR^{216}$, —$NR^{214}C(=O)R^{210}$, —$NR^{214}C(=O)C(=O)R^{210}$, —$NR^{214}C(=O)OR^{211}$, —$NR^{214}C(=O)C(=O)OR^{211}$, —$NR^{214}C(=O)NR^{212}R^{213}$, —$NR^{214}C(=O)NR^{214}C(=O)R^{210}$, —$NR^{214}C(=O)NR^{214}C(=O)OR^{210}$, —$NR^{214}C(=NR^{215})NR^{212}R^{213}$, —$NR^{214}C(=O)C(=O)NR^{212}R^{213}$, —$NR^{214}C(=S)R^{210}$, —$NR^{214}C(=S)OR^{210}$, —$NR^{214}C(=S)NR^{212}R^{213}$, —$NR^{214}S(=O)_2R^{211}$, —$NR^{214}S(=O)_2NR^{212}R^{213}$, —$OR^{210}$, =O, —OCN, —OC(=O)$R^{210}$, —OC(=O)$NR^{212}R^{213}$, —OC(=O)$OR^{210}$, —OC(=$NR^{215}$)$NR^{212}R^{213}$, —OS(=O)$R^{210}$, —OS(=O)$_2R^{210}$, —OS(=O)$_2OR^{210}$, —OS(=O)$_2NR^{212}R^{213}$, —SCN, =S, —S(=O)$_nR^{210}$, —S(=O)$_2OR^{210}$, —$SO_3R^{217}$, —S(=O)$_2NR^{212}R^{213}$, and —S(=O)$NR^{212}R^{213}$. In another embodiment, $R^{179}$, $R^{189}$, $R^{199}$ and $R^{209}$ at each occurrence is independently chosen from $C_{1-6}$alkyl optionally substituted by 1-13 $R^{219}$, $C_{6-11}$aryl optionally substituted by 1-7 $R^{219}$, $C_{7-16}$arylalkyl optionally substituted by 1-19 $R^{219}$, $C_{3-11}$cycloalkyl optionally substituted by 1-21 $R^{219}$, $C_{4-17}$cycloalkylalkyl optionally substituted by 1-32 $R^{219}$, 3-15 membered heterocycloalkyl optionally substituted by 1-28 $R^{219}$, 4-21 membered heterocycloalkylalkyl optionally substituted by 1-40 $R^{219}$, 5-15 membered heteroaryl optionally substituted by 1-15 $R^{219}$, 6-21 membered heteroarylalkyl optionally substituted by 1-27 $R^{219}$, halogen, —CN, —C(=O)$R^{210}$, —C(=O)$OR^{210}$, —C(=O)$NR^{212}R^{213}$, —C(=S)$NR^{212}R^{213}$, —NC, —$NO_2$, —$NR^{212}R^{213}$, —$NR^{214}NR^{212}R^{213}$, —$NR^{214}C(=O)R^{210}$, $NR^{214}C(=O)OR^{211}$, —$NR^{214}C(=O)NR^{212}R^{213}$, —$NR^{214}C(=O)NR^{214}C(=O)R^{210}$, —$NR^{214}C(=O)NR^{214}C(=O)OR^{210}$, —$NR^{214}C(NR^{215})NR^{212}R^{213}$, —$NR^{214}C(=S)R^{210}$, —$NR^{214}C(=S)NR^{212}R^{213}$, —$NR^{214}S(O)_2R^{211}$, $NR^{214}S(O)_2NR^{212}R^{213}$, —$OR^{210}$, =O, —OCN, —OC(=O)$R^{210}$, —OC(=O)$NR^{212}R^{213}$, —OC(=O)$OR^{210}$, —OS(=O)$R^{210}$, —OS(=O)$_2R^{210}$, —OS(=O)$_2OR^{210}$, —OS(=O)$_2NR^{212}R^{213}$, —SCN, =S, —S(=O)$_nR^{210}$, —S(=O)$_2OR^{210}$, —$SO_3R^{217}$, —S(=O)$_2NR^{212}R^{213}$, and —S(=O)$NR^{212}R^{213}$. In another embodiment, $R^{179}$, $R^{189}$, $R^{199}$ and $R^{209}$ at each occurrence is independently chosen from $C_{1-6}$alkyl optionally substituted by 1-13 $R^{219}$, $C_{6-11}$aryl optionally substituted by 1-7 $R^{219}$, $C_{7-16}$arylalkyl optionally substituted by 1-19 $R^{219}$, $C_{3-11}$cycloalkyl optionally substituted by 1-21 $R^{219}$, $C_{4-17}$cycloalkylalkyl optionally substituted by 1-32 $R^{219}$, 3-15 membered heterocycloalkyl optionally substituted by 1-28 $R^{219}$, 4-21 membered heterocycloalkylalkyl optionally substituted by 1-40 $R^{219}$, 5-15 membered heteroaryl optionally substituted by 1-15 $R^{219}$, 6-21 membered heteroarylalkyl optionally substituted by 1-27 $R^{219}$, halogen, —CN, —C(=O)$R^{210}$, —C(=O)$OR^{210}$, —C(=O)$NR^{212}R^{213}$, C(=S)$NR^{212}R^{213}$, —NC, —$NO_2$, —$NR^{212}R^{213}$, —$NR^{214}NR^{212}R^{213}$, —$NR^{214}C(=O)R^{210}$, $NR^{214}C(=O)OR^{211}$, —$NR^{214}C(=O)NR^{212}R^{213}$, —$NR^{214}C(=O)NR^{214}C(=O)R^{210}$, —$NR^{214}C(=NR^{215})NR^{212}R^{213}$, —$NR^{214}C(=S)R^{210}$, —$NR^{214}S(=O)_2R^{211}$, —$OR^{210}$, =O, —OCN, —OC(=O)$R^{210}$, —OC(=O)$NR^{212}R^{213}$, —OS(=O)$R^{210}$, —OS(=O)$_2OR^{210}$, —OS(=O)$_2NR^{212}R^{213}$, —SCN, =S, —S(=O)$_nR^{210}$, and —S(=O)$_2NR^{212}R^{213}$. In another embodiment, $R^{179}$, $R^{189}$, $R^{199}$ and $R^{209}$ at each occurrence is independently chosen from $C_{1-6}$alkyl optionally substituted by 1-13 $R^{219}$, $C_{6-11}$aryl optionally substituted by 1-7 $R^{219}$, $C_{7-16}$arylalkyl optionally substituted by 1-19 $R^{219}$, $C_{3-11}$cycloalkyl optionally substituted by 1-21 $R^{219}$, $C_{4-17}$cycloalkylalkyl optionally substituted by 1-32 $R^{219}$, 3-15 membered heterocycloalkyl optionally substituted by 1-28 $R^{219}$, 4-21 membered heterocycloalkylalkyl optionally substituted by 1-40 $R^{219}$, 5-15 membered heteroaryl optionally substituted by 1-15 $R^{219}$, 6-21 membered heteroarylalkyl optionally substituted by 1-27 $R^{219}$, halogen, —CN, —C(=O)$R^{210}$, —C(=O)$OR^{210}$, —C(=O)$NR^{212}R^{213}$, —C(=S)$NR^{212}R^{213}$, —$NR^{212}R^{213}$, —$NR^{214}C(=O)R^{210}$, —$NR^{214}C(=O)OR^{211}$, —$NR^{214}C(=O)NR^{212}R^{213}$, —$NR^{214}C(=O)NR^{214}C(=O)R^{210}$, —$NR^{214}C(=S)R^{210}$, $NR^{214}S(=O)_2R^{211}$, —$OR^{210}$, =O, —OC(=O)$R^{210}$, —OC(=O)$NR^{212}R^{213}$, =S, —S(=O)$_nR^{210}$, and —S(=O)$_2NR^{212}R^{213}$. In another embodiment, $R^{179}$, $R^{189}$, $R^{199}$ and $R^{209}$ at each occurrence is independently chosen from $C_{1-6}$alkyl optionally substituted by 1-13 $R^{219}$, $C_{6-11}$aryl optionally substituted by 1-7 $R^{219}$, $C_{7-16}$arylalkyl optionally substituted by 1-19

$R^{219}$, $C_{3-11}$cycloalkyl optionally substituted by 1-21 $R^{219}$, $C_{4-17}$cycloalkylalkyl optionally substituted by 1-32 $R^{219}$, 3-15 membered heterocycloalkyl optionally substituted by 1-28 $R^{219}$, 4-21 membered heterocycloalkylalkyl optionally substituted by 1-40 $R^{219}$, 5-15 membered heteroaryl optionally substituted by 1-15 $R^{219}$, 6-21 membered heteroarylalkyl optionally substituted by 1-27 $R^{219}$, halogen, —CN, —C(=O)$R^{210}$, —C(=O)O$R^{210}$, —C(=O)N$R^{212}R^{213}$, —N$R^{212}R^{213}$, —N$R^{214}$C(=O)$R^{210}$, —N$R^{214}$C(=O)O$R^{211}$, —N$R^{214}$C(O)N$R^{212}R^{213}$, —N$R^{214}$S(=O)$_2R^{211}$, N$R^{214}$P(=O)$R^{218}R^{218}$, —O$R^{210}$, =O, —OC(=O)$R^{210}$, —OC(=O)N$R^{212}R^{213}$, =S, —S(=O)$_nR^{210}$, —S(=O)$_2$N$R^{212}R^{213}$, and P(=O)$R^{218}R^{218}$. In another embodiment, $R^{179}$, $R^{189}$, $R^{199}$ and $R^{209}$ at each occurrence is independently chosen from $C_{1-6}$alkyl optionally substituted by 1-13 $R^{219}$, $C_{6-11}$aryl optionally substituted by 1-7 $R^{219}$, $C_{7-16}$arylalkyl optionally substituted by 1-19 $R^{219}$, $C_{3-11}$cycloalkyl optionally substituted by 1-21 $R^{219}$, $C_{4-17}$cycloalkylalkyl optionally substituted by 1-32 $R^{219}$, 3-15 membered heterocycloalkyl optionally substituted by 1-28 $R^{219}$, 4-21 membered heterocycloalkylalkyl optionally substituted by 1-40 $R^{219}$, 5-15 membered heteroaryl optionally substituted by 1-15 $R^{219}$, 6-21 membered heteroarylalkyl optionally substituted by 1-27 $R^{219}$, halogen, —CN, —C(=O)$R^{210}$, —C(=O)O$R^{210}$, —C(=O)N$R^{212}R^{213}$, —N$R^{212}R^{213}$, —N$R^{214}$C(=O)$R^{210}$, —N$R^{214}$C(=O)O$R^{211}$, —N$R^{214}$C(=O)N$R^{212}R^{213}$, —N$R^{214}$S(=O)$_2R^{211}$, —O$R^{210}$, =O, —OC(=O)$R^{210}$, —OC(=O)N$R^{212}R^{213}$, =S, —S(=O)$_nR^{210}$, and —S(=O)$_2$N$R^{212}R^{213}$. In another embodiment, $R^{179}$, $R^{189}$, $R^{199}$ and $R^{209}$ at each occurrence is independently chosen from $C_{1-6}$alkyl optionally substituted by 1-6 $R^{219}$, $C_{6-11}$aryl optionally substituted by 1-7 $R^{219}$, $C_{7-16}$arylalkyl optionally substituted by 1-6 $R^{219}$, $C_{3-11}$cycloalkyl optionally substituted by 1-6 $R^{219}$, $C_{4-17}$cycloalkylalkyl optionally substituted by 1-6 $R^{219}$, 3-15 membered heterocycloalkyl optionally substituted by 1-6 $R^{219}$, 4-21 membered heterocycloalkylalkyl optionally substituted by 1-6 $R^{219}$, 5-15 membered heteroaryl optionally substituted by 1-6 $R^{219}$, 6-21 membered heteroarylalkyl optionally substituted by 1-6 $R^{219}$, halogen, —CN, —C(=O)$R^{210}$, —C(=O)O$R^{210}$, —(=O)N$R^{212}R^{213}$, —C(=O)C(=O)$R^{210}$, —C(=S)N$R^{212}R^{213}$, —NC, —NO$_2$, —N$R^{212}R^{213}$, —N$R^{214}$N$R^{212}R^{213}$, —N$R^{214}$C(=O)$R^{210}$, —N$R^{214}$C(=O)C(=O)$R^{210}$, —N$R^{214}$C(=O)O$R^{211}$, —N$R^{214}$C(=O)C(=O)O$R^{211}$, —N$R^{214}$C(=O)N$R^{212}R^{213}$, —N$R^{214}$C(=O)N$R^{214}$C(=O) $R^{210}$, —N$R^{214}$C(=O)N$R^{214}$C(=O)O$R^{210}$, —N$R^{214}$C (N$R^{215}$)N$R^{212}R^{213}$, —N$R^{214}$C(=O)C(=O)N$R^{212}R^{213}$, —N$R^{214}$C(S)$R^{210}$, —N$R^{214}$C(S)O$R^{210}$, —N$R^{214}$C(=S) N$R^{212}R^{213}$, —N$R^{214}$S(=O)$_2R^{211}$, —N$R^{214}$S(=O)$_2$ N$R^{212}R^{213}$, —N$R^{214}$P(=O)$R^{218}R^{218}$, —O$R^{210}$, =O, —OCN, —OC(=O)$R^{210}$, —OC(=O)N$R^{212}R^{213}$, —OC (=O)O$R^{210}$, —OS(=O)$R^{210}$, —OS(=O)$_2R^{210}$, —OS (=O)$_2$O$R^{210}$, —OS(=O)$_2$N$R^{212}R^{213}$, —SCN, =S, —S(=O)$_nR^{210}$, —S(=O)$_2$O$R^{210}$, —SO$_3R^{217}$, —S(=O)$_2$ N$R^{212}R^{213}$, —S(=O)N$R^{212}R^{213}$, and —P(=O)$R^{218}R^{218}$. In another embodiment, $R^{179}$, $R^{189}$, $R^{199}$ and $R^{209}$ at each occurrence is independently chosen from $C_{1-6}$alkyl optionally substituted by 1-6 $R^{219}$, $C_{6-11}$aryl optionally substituted by 1-7 $R^{219}$, $C_{7-16}$arylalkyl optionally substituted by 1-6 $R^{219}$, $C_{3-11}$cycloalkyl optionally substituted by 1-6 $R^{219}$, $C_{4-17}$cycloalkylalkyl optionally substituted by 1-6 $R^{219}$, 3-15 membered heterocycloalkyl optionally substituted by 1-6 $R^{219}$, 4-21 membered heterocycloalkylalkyl optionally substituted by 1-6 $R^{219}$, 5-15 membered heteroaryl optionally substituted by 1-6 $R^{219}$, 6-21 membered heteroarylalkyl optionally substituted by 1-6 $R^{219}$, halogen, —CN, —C(=O)$R^{210}$, —C(=O)O$R^{210}$, —C(=O)C (=O)$R^{210}$, —C(=S)N$R^{212}R^{213}$, —NC, —NO$_2$, —N$R^{212}R^{213}$, —N$R^{214}$N$R^{212}R^{213}$, —N$R^{214}$C(=O)$R^{210}$, —N$R^{214}$C(=O)C(=O)$R^{210}$, —N$R^{214}$C(=O)O$R^{211}$, —N$R^{214}$C(=O)C(=O)O$R^{211}$, —N$R^{214}$C(=O)N$R^{212}R^{213}$, —N$R^{214}$C(=O)N$R^{214}$C(=O)$R^{210}$, —N$R^{214}$C(=O) N$R^{214}$C(=O)O$R^{210}$, —N$R^{214}$C(N$R^{215}$)N$R^{212}R^{213}$, —N$R^{214}$C(=O)C(=O)N$R^{212}R^{213}$, —N$R^{214}$C(=S)$R^{210}$, —N$R^{214}$C(=S)O$R^{210}$, —N$R^{214}$C(=S)N$R^{212}R^{213}$, —N$R^{214}$S(=O)$_2R^{211}$, —N$R^{214}$S(=O)$_2$N$R^{212}R^{213}$, —O$R^{210}$, =O, —OCN, —OC(=O)$R^{210}$, —OC(=O) N$R^{212}R^{213}$, —OC(=O)O$R^{210}$, —OS(=O)$R^{210}$, —OS (=O)$_2R^{210}$, —OS(=O)$_2$O$R^{210}$, —OS(=O)$_2$N$R^{212}R^{213}$, —SCN, =S, —S(=O)$_nR^{210}$, —S(=O)$_2$O$R^{210}$, —SO$_3R^{217}$, —S(=O)$_2$N$R^{212}R^{213}$, and —S(=O)N$R^{212}R^{213}$. In another embodiment, $R^{179}$, $R^{189}$, $R^{199}$ and $R^{209}$ at each occurrence is independently chosen from $C_{1-6}$alkyl optionally substituted by 1-6 $R^{219}$, $C_{6-11}$aryl optionally substituted by 1-7 $R^{219}$, $C_{7-16}$arylalkyl optionally substituted by 1-6 $R^{219}$, $C_{3-11}$cycloalkyl optionally substituted by 1-6 $R^{219}$, $C_{4-17}$cycloalkylalkyl optionally substituted by 1-6 $R^{219}$, 3-15 membered heterocycloalkyl optionally substituted by 1-6 $R^{219}$, 4-21 membered heterocycloalkylalkyl optionally substituted by 1-6 $R^{219}$, 5-15 membered heteroaryl optionally substituted by 1-6 $R^{219}$, 6-21 membered heteroarylalkyl optionally substituted by 1-6 $R^{219}$, halogen, —CN, —C(=O)$R^{210}$, —C(=O) O$R^{210}$, —C(=O)N$R^{212}R^{213}$, —C(=S)N$R^{212}R^{213}$, —NC, —NO$_2$, —N$R^{212}R^{213}$, —N$R^{214}$N$R^{212}R^{213}$, —N$R^{214}$C(=O) $R^{210}$, —N$R^{214}$C(=O)O$R^{211}$, —N$R^{214}$C(=O)N$R^{212}R^{213}$, —N$R^{214}$C(=O)N$R^{214}$C(=O)$R^{210}$, —N$R^{214}$C(N$R^{215}$) N$R^{212}R^{213}$, —N$R^{214}$C(=S)$R^{210}$, —N$R^{214}$C(=S) N$R^{212}R^{213}$, —N$R^{214}$S(=O)$_2R^{211}$, —O$R^{210}$, =O, —OCN, —OC(=O)$R^{210}$, —C(=O)N$R^{212}R^{213}$, —OS(=O)$R^{210}$, —SCN, =S, —S(=O)$_nR^{210}$, and —S(=O)$_2$N$R^{212}R^{213}$. In another embodiment, $R^{179}$, $R^{189}$, $R^{199}$ and $R^{209}$ at each occurrence is independently chosen from $C_{1-6}$alkyl optionally substituted by 1-6 $R^{219}$, $C_{6-11}$aryl optionally substituted by 1-7 $R^{219}$, $C_{7-16}$arylalkyl optionally substituted by 1-6 $R^{219}$, $C_{3-11}$cycloalkyl optionally substituted by 1-6 $R^{219}$, $C_{4-17}$cycloalkylalkyl optionally substituted by 1-6 $R^{219}$, 3-15 membered heterocycloalkyl optionally substituted by 1-6 $R^{219}$, 4-21 membered heterocycloalkylalkyl optionally substituted by 1-6 $R^{219}$, 5-15 membered heteroaryl optionally substituted by 1-6 $R^{219}$, 6-21 membered heteroarylalkyl optionally substituted by 1-6 $R^{219}$, halogen, —CN, —C(=O)$R^{210}$, —C(=O)O$R^{210}$, —C(=O)N$R^{212}R^{213}$, —C(=S) N$R^{212}R^{213}$, —N$R^{212}R^{213}$, —N$R^{214}$C(=O)$R^{210}$, —N$R^{214}$ C(=O)O$R^{211}$, —N$R^{214}$C(=O)N$R^{212}R^{213}$, —N$R^{214}$C (=O)N$R^{214}$C(=O)$R^{210}$, —N$R^{214}$C(=S)$R^{210}$, —N$R^{214}$S (=O)$_2R^{211}$, —N$R^{214}$P(=O)$R^{218}R^{218}$, —O$R^{210}$, =O, —OC(=O)$R^{210}$, —OC(=O)N$R^{212}R^{213}$, =S, —S(=O)$_n$ $R^{210}$, —S(=O)$_2$N$R^{212}R^{213}$, and —P(=O)$R^{218}R^{218}$. In another embodiment, $R^{179}$, $R^{189}$, $R^{199}$ and $R^{209}$ at each occurrence is independently chosen from $C_{1-6}$alkyl optionally substituted by 1-6 $R^{219}$, $C_{6-11}$aryl optionally substituted by 1-7 $R^{219}$, $C_{7-16}$arylalkyl optionally substituted by 1-6 $R^{219}$, $C_{3-11}$cycloalkyl optionally substituted by 1-6 $R^{219}$, $C_{4-17}$cycloalkylalkyl optionally substituted by 1-6 $R^{219}$, 3-15 membered heterocycloalkyl optionally substituted by 1-6 $R^{219}$, 4-21 membered heterocycloalkylalkyl optionally substituted by 1-6 $R^{219}$, 5-15 membered heteroaryl optionally substituted by 1-6 $R^{219}$, 6-21 membered heteroarylalkyl optionally substituted by 1-6 $R^{219}$, halogen, —CN, —C(=O)$R^{210}$, —C(=S)N$R^{212}R^{213}$, —N$R^{212}R^{213}$, —N$R^{214}$C(=O) $R^{210}$, —C(=O)O$R^{210}$, —C(=O)N$R^{212}R^{213}$, —N$R^{214}$C(=O) O$R^{211}$, —N$R^{214}$C(=O)N$R^{212}R^{213}$, —N$R^{214}$C(O)N$R^{214}$C (=O)$R^{210}$, —N$R^{214}$C(=S)$R^{210}$, —N$R^{214}$S(=O)$_2R^{211}$, —O$R^{210}$, =O, —OC(=O)$R^{210}$, —OC(=O)N$R^{212}R^{213}$, =S, —S(=O)$_n$R$^{210}$, and —S(=O)$_2$NR$^{212}$R$^{213}$. In another embodiment, R$^{179}$, R$^{189}$, R$^{199}$ and R$^{209}$ at each occurrence is independently chosen from C$_{1-6}$alkyl optionally substituted by 1-6 R$^{219}$, C$_{6-11}$aryl optionally substituted by 1-7 R$^{219}$, C$_{7-16}$arylalkyl optionally substituted by 1-6 R$^{219}$, C$_{3-11}$cycloalkyl optionally substituted by 1-6 R$^{219}$, C$_{4-17}$cycloalkylalkyl optionally substituted by 1-6 R$^{219}$, 3-15 membered heterocycloalkyl optionally substituted by 1-6 R$^{219}$, 4-21 membered heterocycloalkylalkyl optionally substituted by 1-6 R$^{219}$, 5-15 membered heteroaryl optionally substituted by 1-6 R$^{219}$, 6-21 membered heteroarylalkyl optionally substituted by 1-6 R$^{219}$, halogen, —CN, —C(=O)R$^{210}$, —C(=O)OR$^{210}$, —C(=O)NR$^{212}$R$^{213}$, —NR$^{212}$R$^{213}$, —NR$^{214}$C(=O)R$^{210}$, —NR$^{214}$C(=O)OR$^{211}$, —NR$^{214}$C(=O)NR$^{212}$R$^{213}$, —NR$^{214}$S(=O)$_2$R$^{211}$, —OR$^{210}$, =O, —OC(=O)R$^{210}$, —OC(=O)NR$^{212}$R$^{213}$, =S, —S(=O)$_n$R$^{210}$, and —S(=O)$_2$NR$^{212}$R$^{213}$.

In each embodiment of the present invention that is described in the paragraphs that precede or follow this paragraph, the definitions of, R$^{210}$, R$^{211}$, R$^{214}$, R$^{215}$, R$^{216}$ and R$^{217}$ may be chosen from any of the embodiments that are described in this paragraph. In one embodiment, R$^{210}$, R$^{211}$, R$^{214}$, R$^{215}$, R$^{216}$ and R$^{217}$ at each occurrence is independently chosen from H, C$_{1-6}$alkyl optionally substituted by 1-13 R$^{229}$, C$_{2-6}$alkenyl optionally substituted by 1-6 R$^{229}$, C$_{2-6}$alkynyl optionally substituted by 1-9 R$^{229}$, C$_{6-11}$aryl optionally substituted by 1-6 R$^{229}$, C$_{7-16}$arylalkyl optionally substituted by 1-19 R$^{229}$, C$_{3-11}$cycloalkyl optionally substituted by 1-21 R$^{229}$, C$_{4-17}$cycloalkylalkyl optionally substituted by 1-32 R$^{229}$, 3-15 membered heterocycloalkyl optionally substituted by 1-28 R$^{229}$, 4-21 membered heterocycloalkylalkyl optionally substituted by 1-40 R$^{229}$, 5-15 membered heteroaryl optionally substituted by 1-15 R$^{229}$, and 6-21 membered heteroarylalkyl optionally substituted by 1-27 R$^{229}$. In another embodiment, R$^{210}$, R$^{211}$, R$^{214}$, R$^{215}$, R$^{216}$ and R$^{217}$ at each occurrence is independently chosen from H, C$_{1-6}$alkyl optionally substituted by 1-13 R$^{229}$, C$_{6-11}$aryl optionally substituted by 1-7 R$^{229}$, C$_{7-16}$arylalkyl optionally substituted by 1-19 R$^{229}$, C$_{3-11}$cycloalkyl optionally substituted by 1-21 R$^{229}$, C$_{4-17}$cycloalkylalkyl optionally substituted by 1-32 R$^{229}$, 3-15 membered heterocycloalkyl optionally substituted by 1-28 R$^{229}$, 4-21 membered heterocycloalkylalkyl optionally substituted by 1-40 R$^{229}$, 5-15 membered heteroaryl optionally substituted by 1-15 R$^{229}$, and 6-21 membered heteroarylalkyl optionally substituted by 1-27 R$^{229}$. In another embodiment, R$^{210}$, R$^{211}$, R$^{214}$, R$^{215}$, R$^{216}$ and R$^{217}$ at each occurrence is independently chosen from H, C$_{1-6}$alkyl optionally substituted by 1-13 R$^{229}$, C$_{6-11}$aryl optionally substituted by 1-7 R$^{229}$, C$_{3-11}$cycloalkyl optionally substituted by 1-21 R$^{229}$, 3-15 membered heterocycloalkyl optionally substituted by 1-28 R$^{229}$, and 5-15 membered heteroaryl optionally substituted by 1-15 R$^{229}$. In another embodiment, R$^{210}$, R$^{211}$, R$^{214}$, R$^{215}$, R$^{216}$ and R$^{217}$ at each occurrence is independently chosen from H, C$_{1-6}$alkyl optionally substituted by 1-6 R$^{229}$, C$_{6-11}$ aryl optionally substituted by 1-7 R$^{229}$, C$_{7-16}$arylalkyl optionally substituted by 1-6 R$^{229}$, C$_{3-11}$cycloalkyl optionally substituted by 1-6 R$^{229}$, C$_{4-17}$cycloalkylalkyl optionally substituted by 1-6 R$^{229}$, 3-15 membered heterocycloalkyl optionally substituted by 1-6 R$^{229}$, 4-21 membered heterocycloalkylalkyl optionally substituted by 1-6 R$^{229}$, 5-15 membered heteroaryl optionally substituted by 1-6 R$^{229}$, and 6-21 membered R$^{210}$, R$^{211}$, R$^{214}$, R$^{215}$, R$^{216}$ and R$^{217}$ at each occurrence is independently chosen from H, C$_{1-6}$alkyl heteroarylalkyl optionally substituted by 1-6 R$^{229}$. In another embodiment, R$^{210}$, optionally substituted by 1-6 R$^{229}$, C$_{6-11}$ aryl optionally substituted by 1-7 R$^{229}$, C$_{3-11}$cycloalkyl optionally substituted by 1-6 R$^{229}$, 3-15 membered heterocycloalkyl optionally substituted by 1-6 R$^{229}$, and 5-15 membered heteroaryl optionally substituted by 1-6 R$^{229}$.

In each embodiment of the present invention that is described in the paragraphs that precede or follow this paragraph, the definitions of R$^{212}$ and R$^{213}$ may be chosen from any of the embodiments that are described in this paragraph. In one embodiment, R$^{212}$ and R$^{213}$ at each occurrence is independently chosen from H, C$_{1-6}$alkyl optionally substituted by 1-13 R$^{239}$, C$_{2-6}$alkenyl optionally substituted by 1-11 R$^{239}$, C$_{2-6}$alkynyl optionally substituted by 1-9 R$^{239}$, C$_{6-11}$ aryl optionally substituted by 1-11 R$^{239}$, C$_{7-16}$arylalkyl optionally substituted by 1-19 R$^{239}$, C$_{3-11}$cycloalkyl optionally substituted by 1-21 R$^{239}$, C$_{4-6}$cycloalkylalkyl optionally substituted by 1-32 R$^{239}$, 3-15 membered heterocycloalkyl optionally substituted by 1-28 R$^{239}$, 4-21 membered heterocycloalkylalkyl optionally substituted by 1-40 R$^{239}$, 5-15 membered heteroaryl optionally substituted by 1-15 R$^{239}$, and 6-21 membered heteroarylalkyl optionally substituted by 1-27 R$^{239}$; or any R$^{212}$ and R$^{213}$ may form, together with the nitrogen atom to which they are attached, a 3-15 membered heterocycloalkyl optionally substituted by 1-28 R$^{249}$ or a 5-15 membered heteroaryl optionally substituted by 1-15 R$^{249}$. In another embodiment, R$^{212}$ and R$^{213}$ at each occurrence is independently chosen from H, C$_{1-6}$alkyl optionally substituted by 1-13 R$^{239}$, C$_{6-11}$ aryl optionally substituted by 1-7 R$^{239}$, C$_{7-16}$arylalkyl optionally substituted by 1-19 R$^{239}$, C$_{3-11}$cycloalkyl optionally substituted by 1-21 R$^{239}$, C$_{4-17}$cycloalkylalkyl optionally substituted by 1-32 R$^{239}$, 3-15 membered heterocycloalkyl optionally substituted by 1-28 R$^{239}$, 4-21 membered heterocycloalkylalkyl optionally substituted by 1-40 R$^{239}$, 5-15 membered heteroaryl optionally substituted by 1-15 R$^{239}$, and 6-21 membered heteroarylalkyl optionally substituted by 1-27 R$^{239}$; or any R$^{212}$ and R$^{213}$ may form, together with the nitrogen atom to which they are attached, a 3-15 membered heterocycloalkyl optionally substituted by 1-28 R$^{249}$ or a 5-15 membered heteroaryl optionally substituted by 1-15 R$^{249}$. In another embodiment, R$^{212}$ and R$^{213}$ at each occurrence is independently chosen from H, C$_{1-6}$alkyl optionally substituted by 1-13 R$^{239}$, C$_{7-16}$arylalkyl optionally substituted by 1-19 R$^{239}$, C$_{4-17}$cycloalkylalkyl optionally substituted by 1-32 R$^{239}$, 4-21 membered heterocycloalkylalkyl optionally substituted by 1-40 R$^{239}$, and 6-21 membered heteroarylalkyl optionally substituted by 1-27 R$^{239}$; or any R$^{212}$ and R$^{213}$ may form, together with the nitrogen atom to which they are attached, a 3-15 membered heterocycloalkyl optionally substituted by 1-28 R$^{249}$ or a 5-15 membered heteroaryl optionally substituted by 1-15 R$^{249}$. In another embodiment, R$^{212}$ and R$^{213}$ at each occurrence is independently chosen from H, C$_{1-6}$alkyl optionally substituted by 1-6 R$^{239}$, C$_{6-11}$ aryl optionally substituted by 1-7 R$^{239}$, C$_{7-16}$arylalkyl optionally substituted by 1-6 R$^{239}$, C$_{3-11}$cycloalkyl optionally substituted by 1-6 R$^{239}$, C$_{4-17}$cycloalkylalkyl optionally substituted by 1-6 R$^{239}$, 3-15 membered heterocycloalkyl optionally substituted by 1-6 R$^{239}$, 4-21 membered heterocycloalkylalkyl optionally substituted by 1-6 R$^{239}$, 5-15 membered heteroaryl optionally substituted by 1-6 R$^{239}$, and 6-21 membered heteroarylalkyl optionally substituted by 1-6 R$^{239}$; or any R$^{212}$ and R$^{213}$ may form, together with the nitrogen atom to which they are attached, a 3-15 membered heterocycloalkyl optionally substituted by 1-6 R$^{249}$ or a 5-15 membered heteroaryl optionally substituted by 1-6 R$^{249}$. In another embodiment, R$^{212}$ and R$^{213}$ at each occurrence is independently chosen from H, C$_{1-6}$alkyl optionally substituted by 1-6 R$^{239}$, C$_{7-16}$arylalkyl optionally substituted by 1-6 R$^{239}$, C$_{4-17}$cycloalkylalkyl optionally substituted by 1-6 R$^{239}$, 4-21 membered heterocycloalkylalkyl optionally substituted by 1-6 R$^{239}$, and 6-21 membered heteroarylalkyl optionally substituted by 1-6 $R^{239}$; or any $R^{212}$ and $R^{213}$ may form, together with the nitrogen atom to which they are attached, a 3-15 membered heterocycloalkyl optionally substituted by 1-6 $R^{249}$ or a 5-15 membered heteroaryl optionally substituted by 1-6 $R^{249}$.

In each embodiment of the present invention that is described in the paragraphs that precede or follow this paragraph, the definition of $R^{218}$ may be chosen from any of the embodiments that are described in this paragraph. In one embodiment, $R^{218}$ at each occurrence is independently chosen from $C_{1-6}$alkyl optionally substituted by 1-13 $R^{229}$, $C_{2-6}$alkenyl optionally substituted by 1-11 $R^{229}$, $C_{2-6}$alkynyl optionally substituted by 1-9 $R^{229}$, $C_{6-11}$ aryl optionally substituted by 1-11 $R^{229}$, $C_{7-16}$arylalkyl optionally substituted by 1-19 $R^{229}$, $C_{3-11}$cycloalkyl optionally substituted by 1-21 $R^{229}$, $C_{4-17}$cycloalkylalkyl optionally substituted by 1-32 $R^{229}$, 3-15 membered heterocycloalkyl optionally substituted by 1-28 $R^{229}$, 4-21 membered heterocycloalkylalkyl optionally substituted by 1-40 $R^{229}$, 5-15 membered heteroaryl optionally substituted by 1-15 $R^{229}$, and 6-21 membered heteroarylalkyl optionally substituted by 1-27 $R^{229}$. In another embodiment, $R^{218}$ at each occurrence is independently chosen from $C_{1-6}$alkyl optionally substituted by 1-13 $R^{229}$, $C_{6-11}$aryl optionally substituted by 1-11 $R^{229}$, $C_{7-16}$arylalkyl optionally substituted by 1-19 $R^{229}$, $C_{3-11}$cycloalkyl optionally substituted by 1-21 $R^{229}$, $C_{4-17}$cycloalkylalkyl optionally substituted by 1-32 $R^{229}$, 3-15 membered heterocycloalkyl optionally substituted by 1-28 $R^{229}$, 4-21 membered heterocycloalkylalkyl optionally substituted by 1-40 $R^{229}$, 5-15 membered heteroaryl optionally substituted by 1-15 $R^{229}$, and 6-21 membered heteroarylalkyl optionally substituted by 1-27 $R^{229}$. In another embodiment, $R^{218}$ at each occurrence is independently chosen from $C_{1-6}$alkyl optionally substituted by 1-13 $R^{229}$, $C_{7-16}$arylalkyl optionally substituted by 1-19 $R^{229}$, $C_{3-11}$cycloalkyl optionally substituted by 1-21 $R^{229}$, 3-15 membered heterocycloalkyl optionally substituted by 1-28 $R^{229}$, 5-15 membered heteroaryl optionally substituted by 1-15 $R^{229}$, and 6-21 membered heteroarylalkyl optionally substituted by 1-27 $R^{229}$. In another embodiment, $R^{218}$ at each occurrence is independently chosen from $C_{1-6}$alkyl optionally substituted by 1-13 $R^{229}$ and $C_{7-16}$arylalkyl optionally substituted by 1-19 $R^{229}$. In another embodiment, $R^{218}$ at each occurrence is independently $C_{1-6}$alkyl optionally substituted by 1-13 $R^{229}$. In another embodiment, $R^{218}$ at each occurrence is independently chosen from $C_{1-6}$alkyl optionally substituted by 1-6 $R^{229}$, $C_{2-6}$alkenyl optionally substituted by 1-6 $R^{229}$, $C_{2-6}$alkynyl optionally substituted by 1-6 $R^{229}$, $C_{6-11}$aryl optionally substituted by 1-6 $R^{229}$, $C_{7-16}$arylalkyl optionally substituted by 1-6 $R^{229}$, $C_{3-11}$cycloalkyl optionally substituted by 1-6 $R^{229}$, $C_{4-17}$cycloalkylalkyl optionally substituted by 1-6 $R^{229}$, 3-15 membered heterocycloalkyl optionally substituted by 1-6 $R^{229}$, 4-21 membered heterocycloalkylalkyl optionally substituted by 1-6 $R^{229}$, 5-15 membered heteroaryl optionally substituted by 1-6 $R^{229}$, and 6-21 membered heteroarylalkyl optionally substituted by 1-6 $R^{229}$. In another embodiment, $R^{218}$ at each occurrence is independently chosen from $C_{1-6}$alkyl optionally substituted by 1-6 $R^{229}$, $C_{6-11}$ aryl optionally substituted by 1-6 $R^{229}$, $C_{7-16}$arylalkyl optionally substituted by 1-6 $R^{229}$, $C_{3-11}$cycloalkyl optionally substituted by 1-6 $R^{229}$, $C_{4-6}$cycloalkylalkyl optionally substituted by 1-6 $R^{229}$, 3-15 membered heterocycloalkyl optionally substituted by 1-6 $R^{229}$, 4-21 membered heterocycloalkylalkyl optionally substituted by 1-6 $R^{229}$, 5-15 membered heteroaryl optionally substituted by 1-6 $R^{229}$, and 6-21 membered heteroarylalkyl optionally substituted by 1-6 $R^{229}$. In another embodiment, $R^{218}$ at each occurrence is independently chosen from $C_{1-6}$alkyl optionally substituted by 1-6 $R^{229}$, $C_{6-11}$aryl optionally substituted by 1-6 $R^{229}$, $C_{7-16}$arylalkyl optionally substituted by 1-6 $R^{229}$, $C_{3-11}$cycloalkyl optionally substituted by 1-6 $R^{229}$, 3-15 membered heterocycloalkyl optionally substituted by 1-6 $R^{229}$, 5-15 membered heteroaryl optionally substituted by 1-6 $R^{229}$, and 6-21 membered heteroarylalkyl optionally substituted by 1-6 $R^{229}$. In another embodiment, $R^{218}$ at each occurrence is independently chosen from $C_{1-6}$alkyl optionally substituted by 1-6 $R^{229}$ and $C_{7-16}$arylalkyl optionally substituted by 1-6 $R^{229}$. In another embodiment, $R^{218}$ at each occurrence is independently $C_{1-6}$alkyl optionally substituted by 1-6 $R^{229}$. In another embodiment, $R^{218}$ at each occurrence is independently $C_{1-6}$alkyl.

In each embodiment of the present invention that is described in the paragraphs that precede or follow this paragraph, the definitions of $R^{219}$, $R^{229}$, $R^{239}$ and $R^{249}$ may be chosen from any of the embodiments that are described in this paragraph. In one embodiment, $R^{219}$, $R^{229}$, $R^{239}$ and $R^{249}$ at each occurrence is independently chosen from $C_{1-6}$alkyl optionally substituted by 1-13 halogen, $C_{2-6}$alkenyl, $C_{2-6}$alkynyl, $C_{6-11}$ aryl, $C_{7-16}$arylalkyl, $C_{3-11}$cycloalkyl, $C_{4-17}$cycloalkylalkyl, 3-15 membered heterocycloalkyl, 4-21 membered heterocycloalkylalkyl, 5-15 membered heteroaryl, 6-21 membered heteroarylalkyl, halogen, —CN, —C(=O)$R^{250}$, —C(=O)O$R^{250}$, —C(=O)N$R^{250}R^{250}$, —C(=O)C(=O)$R^{250}$, —C(=N$R^{250}$)$R^{250}$, C(=N$R^{250}$)N$R^{250}R^{250}$, —C(=NOH)N$R^{250}R^{250}$, C(=NO$R^{25}$)$R^{250}$, —C(=NN$R^{250}R^{250}$)$R^{250}$, —C(=NN$R^{250}$C(=O)$R^{250}$)$R^{250}$, —C(=NN$R^{250}$C(=O)O$R^{250}$)$R^{250}$, —C(=S)N$R^{250}R^{250}$, —NC, —NO$_2$, —N$R^{250}R^{250}$, —N$R^{250}$N$R^{250}R^{250}$, N=N$R^{250}$, =N$R^{250}$, =NO$R^{250}$, N$R^{250}$O$R^{250}$, N$R^{250}$C(=O)$R^{250}$, —N$R^{250}$C(=O)C(=O) $R^{250}$, —N$R^{250}$C(O)O$R^{250}$, —N$R^{250}$C(=O)C(=O)O$R^{250}$, —N$R^{250}$C(=O)N$R^{250}R^{250}$, —N$R^{250}$C(=O)N$R^{250}$C(O) $R^{250}$, —N$R^{250}$C(=O)N$R^{250}$C(=O)O$R^{250}$, —N$R^{250}$C (=N$R^{250}$)N$R^{250}R^{250}$, —N$R^{250}$C(=O)C(=O)N$R^{250}$, $R^{250}$, —N$R^{250}$C(=S)$R^{250}$, —N$R^{250}$C(=S)O$R^{250}$, —N$R^{250}$C (=S)N$R^{250}R^{250}$, —N$R^{250}$S(=O)$_2R^{250}$, —N$R^{250}$S(=O)$_2$ N$R^{250}R^{250}$, —N$R^{250}$P(=O)$R^{251}R^{251}$, —N$R^{250}$P(=O) (N$R^{250}R^{250}$)(N$R^{250}R^{25}$), —N$R^{250}$P(=O)(O$R^{250}$)(O$R^{250}$), —N$R^{250}$P(=O)(S$R^{250}$(S$R^{250}$, —O$R^{250}$, =O, —OCN, —OC(=O)$R^{250}$, —OC(=O)N$R^{250}R^{250}$, —OC(=O) O$R^{250}$, —OC(=N$R^{250}$)N$R^{250}R^{250}$, —OS(=O)$R^{250}$, —OS (=O)$_2R^{250}$, —OS(=O)$_2$O$R^{250}$, —OS(=O)$_2$N$R^{250}R^{250}$, —OP(=O)$R^{251}R^{251}$, —OP(=O)(N$R^{250}R^{250}$)(N$R^{250}R^{250}$), —OP(=O)(O$R^{250}$(O$R^{250}$, —OP(=O)(S$R^{250}$)(S$R^{250}$), —SCN, =S, —S(=O)$_nR^{250}$, —S(=O)$_2$O$R^{250}$, —SO$_3R^{250}$, —S(=O)$_2$N$R^{250}R^{250}$, —S(=O)N$R^{250}R^{250}$, —SP(=O) $R^{251}R^{251}$, —SP(=O)(N$R^{250}R^{250}$)(N$R^{250}R^{250}$), —SP(=O) (O$R^{250}$)(O$R^{250}$), —SP(=O)(S$R^{250}$)(S$R^{250}$), —P(=O) $R^{251}R^{251}$, —P(=O)(N$R^{250}R^{250}$)(N$R^{250}R^{250}$), —P(=O) (O$R^{250}$)(O$R^{250}$), and —P(=O)(S$R^{250}$)(S$R^{250}$). In another embodiment, $R^{219}$, $R^{229}$, $R^{239}$ and $R^{249}$ at each occurrence is independently chosen from $C_{1-6}$alkyl optionally substituted by 1-13 halogen, $C_{2-6}$alkenyl, $C_{2-6}$alkynyl, $C_{6-11}$aryl, $C_{7-16}$arylalkyl, $C_{3-11}$cycloalkyl, $C_{4-17}$cycloalkylalkyl, 3-15 membered heterocycloalkyl, 4-21 membered heterocycloalkylalkyl, 5-15 membered heteroaryl, 6-21 membered heteroarylalkyl, halogen, —CN, —C(=O)$R^{250}$, —C(=O) O$R^{250}$, —C(=O)N$R^{250}R^{250}$, —C(=O)C(=O)$R^{250}$, —C(=N$R^{250}$)$R^{250}$, —C(=N$R^{250}$)N$R^{250}R^{250}$, —C(=NOH)N$R^{250}R^{250}$, —C(=NO$R^{250}$)$R^{250}$, —C(=NN$R^{250}R^{250}$)$R^{250}$, —C(=NN$R^{250}$C(=O)$R^{250}$)$R^{250}$, —C(=NN$R^{250}$C(=O)O$R^{250}$)$R^{250}$, —C(=S)N$R^{250}R^{250}$, —NC, —NO$_2$, —N$R^{250}R^{250}$, —N$R^{250}$N$R^{250}R^{250}$, —N=N$R^{250}$, =N$R^{250}$, =NO$R^{250}$, —N$R^{250}$O$R^{250}$, —NR²⁵⁰C(=O)R²⁵⁰, —NR²⁵⁰C(=O)C(=O)R²⁵⁰, —NR²⁵⁰C(=O)OR²⁵⁰, —NR²⁵⁰C(=O)C(=O)OR²⁵⁰, —NR²⁵⁰C(=O)NR²⁵⁰R²⁵⁰, —NR²⁵⁰C(=O)NR²⁵⁰C(=O)R²⁵⁰, —NR²⁵⁰C(=O)NR²⁵⁰C(=O)OR²⁵⁰, —NR²⁵⁰C(=NR²⁵⁰)NR²⁵⁰R²⁵⁰, —NR²⁵⁰C(=O)C(=O)NR²⁵⁰R²⁵⁰, —NR²⁵⁰C(=S)R²⁵⁰, —NR²⁵⁰C(=S)OR²⁵⁰, —NR²⁵⁰C(=S)NR²⁵⁰R²⁵⁰, —NR²⁵⁰S(=O)₂R²⁵⁰, —NR²⁵⁰S(=O)₂NR²⁵⁰R²⁵⁰, —NR²⁵⁰P(=O)R²⁵¹R²⁵¹, —OR²⁵⁰, =O, —OCN, —OC(=O)R²⁵⁰, —OC(=O)NR²⁵⁰R²⁵⁰, —OC(=O)OR²⁵⁰, —OC(=NR²⁵⁰)NR²⁵⁰R²⁵⁰, —OS(=O)R²⁵⁰, —OS(=O)₂R²⁵⁰, —OS(=O)₂OR²⁵⁰, —OS(=O)₂NR²⁵⁰R²⁵⁰, —SCN, =S, —S(=O)ₙR²⁵⁰, —S(=O)₂OR²⁵⁰, —SO₃R²⁵⁰, —S(=O)₂NR²⁵⁰R²⁵⁰, —S(=O)NR²⁵⁰R²⁵⁰, and —P(=O)R²⁵¹R²⁵¹. In another embodiment, R²¹⁹, R²²⁹, R²³⁹ and R²⁴⁹ at each occurrence is independently chosen from $C_{1-6}$alkyl optionally substituted by 1-13 halogen, $C_{2-6}$alkenyl, $C_{2-6}$alkynyl, $C_{6-11}$ aryl, $C_{7-16}$arylalkyl, $C_{3-11}$cycloalkyl, $C_{4-17}$cycloalkylalkyl, 3-15 membered heterocycloalkyl, 4-21 membered heterocycloalkylalkyl, 5-15 membered heteroaryl, 6-21 membered heteroarylalkyl, halogen, —CN, —C(=O)R²⁵⁰, —C(=O)OR²⁵⁰, —C(=O)NR²⁵⁰R²⁵⁰, —C(=O)C(=O)R²⁵⁰, —C(=NR²⁵⁰)R²⁵⁰, —C(=NR²⁵⁰)NR²⁵⁰R²⁵⁰, —C(=NOH)NR²⁵⁰R²⁵⁰, —C(=NOR²⁵⁰)R²⁵⁰, —C(=NNR²⁵⁰R²⁵⁰)R²⁵⁰, —C(=NNR²⁵⁰C(=O)R²⁵⁰)R²⁵⁰, —C(=NNR²⁵⁰C(=O)OR²⁵⁰)R²⁵⁰, —C(=S)NR²⁵⁰R²⁵⁰, —NC, —NO₂, —NR²⁵⁰R²⁵⁰, —NR²⁵⁰NR²⁵⁰R²⁵⁰, —N=NR²⁵⁰, =NR²⁵⁰, =NOR²⁵⁰, —NR²⁵⁰OR²⁵⁰, —NR²⁵⁰C(=O)R²⁵⁰, —NR²⁵⁰C(=O)C(=O)R²⁵⁰, —NR²⁵⁰C(=O)OR²⁵⁰, —NR²⁵⁰C(=O)C(=O)OR²⁵⁰, —NR²⁵⁰C(=O)NR²⁵⁰R²⁵⁰, —NR²⁵⁰C(=O)NR²⁵⁰C(=O)R²⁵⁰, —NR²⁵⁰C(=O)NR²⁵⁰C(=O)OR²⁵⁰, —NR²⁵⁰C(=O)NR²⁵⁰C(=O)R²⁵⁰, —NR²⁵⁰C(=O)OR²⁵⁰, —NR²⁵⁰C(=NR²⁵⁰)NR²⁵⁰R²⁵⁰, —NR²⁵⁰C(=O)C(=O)NR²⁵⁰R²⁵⁰, —NR²⁵⁰C(=S)R²⁵⁰, —NR²⁵⁰C(=S)OR²⁵⁰, —NR²⁵⁰C(=S)NR²⁵⁰R²⁵⁰, —NR²⁵⁰S(=O)₂R²⁵⁰, —NR²⁵⁰S(=O)₂NR²⁵⁰R²⁵⁰, —OR²⁵⁰, =O, —OCN, —OC(=O)R²⁵⁰, —OC(=O)NR²⁵⁰R²⁵⁰, —OC(=O)OR²⁵⁰, —OC(=NR²⁵⁰)NR²⁵⁰R²⁵⁰, —OS(=O)R²⁵⁰, —OS(=O)₂R²⁵⁰, —OS(=O)₂OR²⁵⁰, —OS(=O)₂NR²⁵⁰R²⁵⁰, —SCN, =S, —S(=O)ₙR²⁵⁰, —S(=O)₂OR²⁵⁰, —SO₃R²⁵⁰, —S(=O)₂NR²⁵⁰R²⁵⁰, and —S(=O)NR²⁵⁰R²⁵⁰. In another embodiment, R²¹⁹, R²²⁹, R²³⁹ and R²⁴⁹ at each occurrence is independently chosen from $C_{1-6}$alkyl optionally substituted by 1-13 halogen, $C_{2-6}$alkenyl, $C_{2-6}$alkynyl, $C_{6-11}$ aryl, $C_{7-16}$arylalkyl, $C_{3-11}$cycloalkyl, $C_{4-17}$cycloalkylalkyl, 3-15 membered heterocycloalkyl, 4-21 membered heterocycloalkylalkyl, 5-15 membered heteroaryl, 6-21 membered heteroarylalkyl, halogen, —CN, —C(=O)R²⁵⁰, —C(=O)OR²⁵⁰, —C(=O)NR²⁵⁰R²⁵⁰, —C(=O)C(=O)R²⁵⁰, —C(=S)NR²⁵⁰R²⁵⁰, —NC, —NO₂, —NR²⁵⁰R²⁵⁰, —NR²⁵⁰NR²⁵⁰R²⁵⁰, —NR²⁵⁰C(=O)R²⁵⁰, —NR²⁵⁰C(=O)C(=O)R²⁵⁰, —NR²⁵⁰C(=O)OR²⁵⁰, —NR²⁵⁰C(=O)C(=O)OR²⁵⁰, —NR²⁵⁰C(=O)NR²⁵⁰R²⁵⁰, —NR²⁵⁰C(=O)NR²⁵⁰C(=O)R²⁵⁰, —NR²⁵⁰C(=O)NR²⁵⁰C(=O)OR²⁵⁰, —NR²⁵⁰C(=NR²⁵⁰)NR²⁵⁰R²⁵⁰, —NR²⁵⁰C(=O)C(=O)NR²⁵⁰R²⁵⁰, —NR²⁵⁰C(S)R²⁵⁰, —NR²⁵⁰C(S)OR²⁵⁰, —NR²⁵⁰C(=S)NR²⁵⁰R²⁵⁰, —NR²⁵⁰S(=O)₂R²⁵⁰, —NR²⁵⁰S(=O)₂NR²⁵⁰R²⁵⁰, —OR²⁵⁰, =O, —OCN, —OC(=O)R²⁵⁰, —OC(=O)NR²⁵⁰R²⁵⁰, OC(=O)OR²⁵⁰, —OS(=O)R²⁵⁰, —OS(=O)₂R²⁵⁰, —OS(=O)₂OR²⁵⁰, —OS(=O)₂ NR²⁵⁰R²⁵⁰, —SCN, =S, —S(=O)ₙR²⁵⁰, —S(=O)₂ OR²⁵⁰, —SO₃R²⁵⁰, —S(=O)₂NR²⁵⁰R²⁵⁰, and —S(=O)NR²⁵⁰R²⁵⁰. In another embodiment, R²¹⁹, R²²⁹, R²³⁹ and R²⁴⁹ at each occurrence is independently chosen from $C_{1-6}$alkyl optionally substituted by 1-13 halogen, $C_{6-11}$aryl, $C_{7-16}$arylalkyl, $C_{3-11}$cycloalkyl, $C_{4-17}$cycloalkylalkyl, 3-15 membered heterocycloalkyl, 4-21 membered heterocycloalkylalkyl, 5-15 membered heteroaryl, 6-21 membered heteroarylalkyl, halogen, —CN, —C(=O)R²⁵⁰, —C(=O)OR²⁵⁰, —C(=O)NR²⁵⁰R²⁵⁰, —C(=S)NR²⁵⁰R²⁵⁰, —NC, —NO₂, —NR²⁵⁰R²⁵⁰, —NR²⁵⁰NR²⁵⁰R²⁵⁰, —C(=O)NR²⁵⁰R²⁵⁰, —NR²⁵⁰C(=O)OR²⁵⁰, —NR²⁵⁰C(=O)NR²⁵⁰R²⁵⁰, —NR²⁵⁰C(=O)C(=O)R²⁵⁰, —NR²⁵⁰C(=NR²⁵⁰)NR²⁵⁰R²⁵⁰, —NR²⁵⁰C(=S)R²⁵⁰, —NR²⁵⁰C(=S)NR²⁵⁰R²⁵⁰, —NR²⁵⁰S(=O)₂R²⁵⁰, —NR²⁵⁰P(=O)R²⁵¹R²⁵¹, —OR²⁵⁰, =O, —OCN, —OC(=O)R²⁵⁰, —OC(=O)NR²⁵⁰R²⁵⁰, —SCN, =S, —S(=O)ₙR²⁵⁰, —S(=O)₂NR²⁵⁰R²⁵⁰, and —P(=O)R²⁵¹R²⁵¹. In another embodiment, R²¹⁹, R²²⁹, R²³⁹ and R²⁴⁹ at each occurrence is independently chosen from $C_{1-6}$alkyl optionally substituted by 1-13 halogen, $C_{6-11}$aryl, $C_{7-16}$arylalkyl, $C_{3-11}$cycloalkyl, $C_{4-17}$cycloalkylalkyl, 3-15 membered heterocycloalkyl, 4-21 membered heterocycloalkylalkyl, 5-15 membered heteroaryl, 6-21 membered heteroarylalkyl, halogen, —CN, —C(=O)R²⁵⁰, —C(=O)OR²⁵⁰, —C(=O)NR²⁵⁰R²⁵⁰, —C(=S)NR²⁵⁰R²⁵⁰, —NC, —NO₂, —NR²⁵⁰R²⁵⁰, —NR²⁵⁰NR²⁵⁰R²⁵⁰, —NR²⁵⁰C(O)R²⁵⁰, —NR²⁵⁰C(=O)OR²⁵⁰, —NR²⁵⁰C(=O)NR²⁵⁰C(=O)R²⁵⁰, —NR²⁵⁰C(=NR²⁵⁰)NR²⁵⁰R²⁵⁰, —NR²⁵⁰C(=S)R²⁵⁰)₂R²⁵⁰S(=O)₂R²⁵⁰, —OR²⁵⁰, =O, —OCN, —OC(=O)R²⁵⁰, —OC(=O)NR²⁵⁰R²⁵⁰, —SCN, =S, —S(=O)ₙR²⁵⁰, and —S(=O)₂NR²⁵⁰R²⁵⁰. In another embodiment, R²¹⁹, R²²⁹, R²³⁹ and R²⁴⁹ at each occurrence is independently chosen from $C_{1-6}$alkyl optionally substituted by 1-13 halogen, $C_{6-11}$ aryl, $C_{7-16}$arylalkyl, $C_{3-11}$cycloalkyl, $C_{4-17}$cycloalkylalkyl, 3-15 membered heterocycloalkyl, 4-21 membered heterocycloalkylalkyl, 5-15 membered heteroaryl, 6-21 membered heteroarylalkyl, halogen, —CN, —C(=O)R²⁵⁰, —C(=O)OR²⁵⁰, —C(=O)NR²⁵⁰R²⁵⁰, —C(=S)NR²⁵⁰R²⁵⁰, —NR²⁵⁰R²⁵⁰, —NR²⁵⁰C(=O)R²⁵⁰, —NR²⁵⁰C(=O)OR²⁵⁰, —NR²⁵⁰C(=O)NR²⁵⁰C(=O)R²⁵⁰, —NR²⁵⁰C(=S)R²⁵⁰, —NR²⁵⁰S(=O)₂R²⁵⁰, —OR²⁵⁰, =O, —OC(=O)R²⁵⁰, —OC(=O)NR²⁵⁰R²⁵⁰, =S, —S(=O)ₙR²⁵⁰, and —S(=O)₂NR²⁵⁰R²⁵⁰. In another embodiment, R²¹⁹, R²²⁹, R²³⁹ and R²⁴⁹ at each occurrence is independently chosen from $C_{1-6}$alkyl optionally substituted by 1-6 halogen, $C_{2-6}$alkenyl, $C_{2-6}$alkynyl, $C_{6-11}$aryl, $C_{7-16}$arylalkyl, $C_{3-11}$cycloalkyl, $C_{4-17}$cycloalkylalkyl, 3-15 membered heterocycloalkyl, 4-21 membered heterocycloalkylalkyl, 5-15 membered heteroaryl, 6-21 membered heteroarylalkyl, —CN, —C(=O)R²⁵⁰, —C(=O)OR²⁵⁰, —C(=O)NR²⁵⁰R²⁵⁰, —C(=O)C(=O)R²⁵⁰, —C(=S)NR²⁵⁰R²⁵⁰, —NC, —NO₂, —NR²⁵⁰R²⁵⁰, —NR²⁵⁰NR²⁵⁰R²⁵⁰, —NR$^{250}$C(=O)R$^{250}$, —NR$^{250}$C(=O)C(=O)R$^{250}$, —NR$^{250}$C(=O)OR$^{250}$, —NR$^{250}$C(=O)C(=O)OR$^{250}$, —NR$^{250}$C(=O)NR$^{250}$R$^{250}$, —NR$^{250}$C(=O)R$^{250}$C(=O)R$^{250}$, —NR$^{250}$C(=O)NR$^{250}$C(=O)OR$^{250}$, —NR$^{250}$C(=NR$^{250}$NR$^{250}$R$^{250}$, —NR$^{250}$C(=O)C(=O)NR$^{250}$R$^{250}$, —NR$^{250}$C(=S)R$^{250}$, —NR$^{250}$C(S)OR$^{250}$, —NR$^{250}$C(=S)NR$^{250}$R$^{250}$, —NR$^{250}$S(=O)$_2$R$^{250}$, —NR$^{259}$S(=O)$_2$NR$^{259}$R$^{259}$, —NR$^{250}$P(=O)R$^{251}$R$^{251}$, —OR$^{250}$, =O, —OCN, —OC(=O)R$^{250}$, —OC(=O)NR$^{250}$R$^{250}$, —OC(=O)OR$^{250}$, —OS(=O)R$^{250}$, —OS(=O)$_2$R$^{250}$, —OS(=O)$_2$OR$^{250}$, —OS(=O)$_2$NR$^{250}$R$^{250}$, —SCN, =S, —S(=O)$_n$R$^{250}$, —S(=O)OR$^{250}$, —SO$_3$R$^{250}$, —S(=O)$_2$NR$^{250}$R$^{250}$, —S(=O)NR$^{250}$R$^{250}$, and —P(=O)R$^{251}$R$^{251}$. In another embodiment, R$^{219}$, R$^{229}$, R$^{239}$ and R$^{249}$ at each occurrence is independently chosen from C$_{1-6}$alkyl optionally substituted by 1-6 halogen, C$_{2-6}$alkenyl, C$_{2-6}$alkynyl, C$_{6-11}$aryl, C$_{7-16}$arylalkyl, C$_{3-11}$cycloalkyl, C$_{4-17}$cycloalkylalkyl, 3-15 membered heterocycloalkyl, 4-21 membered heterocycloalkylalkyl, 5-15 membered heteroaryl, 6-21 membered heteroarylalkyl, halogen, —CN, —C(=O)R$^{250}$, —C(=O)OR$^{250}$, —C(=O)NR$^{250}$R$^{250}$, —C(=O)C(=O)R$^{250}$, —C(=S)NR$^{250}$R$^{250}$, —NC, —NO$_2$, —NR$^{250}$R$^{250}$, —NR$^{250}$NR$^{250}$R$^{250}$, —NR$^{250}$C(=O)R$^{250}$, —NR$^{250}$C(=O)C(=O)R$^{250}$, —NR$^{250}$C(=O)OR$^{250}$, —NR$^{250}$C(=O)C(=O)OR$^{250}$, —NR$^{250}$C(=O)NR$^{250}$R$^{250}$, —NR$^{250}$C(=O)NR$^{250}$C(=O)R$^{250}$, —NR$^{250}$C(=O)NR$^{250}$C(=O)OR$^{250}$, —NR$^{250}$C(=NR$^{250}$)NR$^{250}$R$^{250}$, —NR$^{250}$C(=O)C(=O)NR$^{250}$R$^{250}$, —NR$^{250}$C(=S)R$^{250}$, —NR$^{250}$C(=S)OR$^{209}$, —NR$^{250}$C(=S)NR$^{250}$R$^{250}$, —NR$^{250}$S(=O)$_2$R$^{250}$, —NR$^{250}$S(=O)$_2$NR$^{250}$R$^{250}$, —OR$^{250}$, =O, —OCN, —OC(=O)R$^{250}$, —OC(=O)NR$^{250}$R$^{250}$, —C(=O)OR$^{250}$, —OS(=O)R$^{250}$, —OS(=O)$_2$R$^{250}$, —OS(=O)$_2$OR$^{250}$, —OS(=O)$_2$NR$^{250}$R$^{250}$, —SCN, =S, —S(=O)$_n$R$^{250}$, —S(=O)$_2$OR$^{250}$, —SO$_3$R$^{250}$, —S(=O)$_2$NR$^{250}$R$^{250}$, and —S(=O)NR$^{250}$R$^{250}$. In another embodiment, R$^{219}$, R$^{229}$, R$^{239}$ and R$^{249}$ at each occurrence is independently chosen from C$_{1-6}$alkyl optionally substituted by 1-6 halogen, C$_{6-11}$aryl, C$_{7-16}$arylalkyl, C$_{3-11}$cycloalkyl, C$_{4-17}$cycloalkylalkyl, 3-15 membered heterocycloalkyl, 4-21 membered heterocycloalkylalkyl, 5-15 membered heteroaryl, 6-21 membered heteroarylalkyl, halogen, —CN, —C(=O)R$^{250}$, —C(=O)OR$^{250}$, —C(=O)NR$^{250}$R$^{250}$, —C(=S)NR$^{250}$R$^{250}$, —NC, —NO$_2$, —NR$^{250}$R$^{250}$, —NR$^{250}$NR$^{250}$R$^{250}$, —NR$^{250}$C(=O)R$^{250}$, —NR$^{250}$C(=O)OR$^{250}$, —NR$^{250}$C(=O)NR$^{250}$C(=O)R$^{250}$, —NR$^{250}$C(=NR$^{250}$)NR$^{250}$R$^{250}$, —NR$^{250}$C(=S)R$^{250}$, —NR$^{250}$C(=S)NR$^{250}$R$^{250}$, —NR$^{250}$S(=O)$_2$R$^{250}$, —OR$^{250}$, =O, —OCN, —OC(=O)R$^{250}$, —OC(=O)NR$^{250}$R$^{250}$, —SCN, =S, —S(=O)$_n$R$^{250}$, and —S(=O)$_2$NR$^{250}$R$^{250}$. In another embodiment, R$^{219}$, R$^{229}$, R$^{239}$ and R$^{249}$ at each occurrence is independently chosen from C$_{1-6}$alkyl optionally substituted by 1-6 halogen, C$_{6-11}$ aryl, C$_{7-16}$arylalkyl, C$_{3-11}$cycloalkyl, C$_{4-17}$cycloalkylalkyl, 3-15 membered heterocycloalkyl, 4-21 membered heterocycloalkylalkyl, 5-15 membered heteroaryl, 6-21 membered heteroarylalkyl, halogen, —CN, —C(=O)R$^{250}$, —C(=O)OR$^{250}$, —C(=O)NR$^{250}$R$^{250}$, —C(=S)NR$^{250}$R$^{250}$, —NR$^{250}$R$^{250}$, —NR$^{250}$C(=O)R$^{250}$, —NR$^{250}$C(=O)OR$^{250}$, —NR$^{250}$C(=O)NR$^{250}$C(=O)R$^{250}$, —NR$^{250}$C(=S)R$^{250}$, —NR$^{250}$S(=O)$_2$R$^{250}$, —NR$^{250}$P(=O)R$^{251}$R$^{251}$, —OR$^{250}$, =O, —OC(=O)R$^{250}$, —OC(=O)NR$^{250}$R$^{250}$, =S, —S(=O)$_n$R$^{250}$, —S(=O)$_2$NR$^{250}$R$^{250}$, and —P(=O)R$^{251}$R$^{251}$. In another embodiment, R$^{219}$, R$^{229}$, R$^{239}$ and R$^{249}$ at each occurrence is independently chosen from C$_{1-6}$alkyl optionally substituted by 1-6 halogen, C$_{6-11}$aryl, C$_{7-16}$arylalkyl, C$_{3-11}$ cycloalkyl, C$_{4-17}$cycloalkylalkyl, 3-15 membered heterocycloalkyl, 4-21 membered heterocycloalkylalkyl, 5-15 membered heteroaryl, 6-21 membered heteroarylalkyl, halogen, —CN, —C(=O)R$^{250}$, C(O)OR$^{250}$, —C(=O)NR$^{250}$R$^{250}$, —C(=S)NR$^{250}$R$^{250}$, —NR$^{250}$R$^{250}$, —NR$^{250}$C(=O)R$^{250}$, —NR$^{250}$C(=O)OR$^{250}$, —NR$^{250}$C(=O)NR$^{250}$R$^{250}$, —NR$^{250}$C(=O)NR$^{250}$C(=O)R$^{250}$, —NR$^{250}$C(=S)R$^{250}$, —NR$^{250}$S(=O)$_2$R$^{250}$, —OR$^{250}$, =O, —OC(=O)R$^{250}$, —OC(=O)NR$^{250}$R$^{250}$, =S, —S(=O)$_n$R$^{250}$, and —S(=O)$_2$NR$^{250}$R$^{250}$. In another embodiment, R$^{219}$, R$^{229}$, R$^{239}$ and R$^{249}$ at each occurrence is independently chosen from C$_{1-6}$alkyl optionally substituted by 1-6 halogen, C$_{6-11}$ aryl, C$_{7-16}$ arylalkyl, C$_{3-11}$ cycloalkyl, C$_{4-17}$cycloalkylalkyl, 3-15 membered heterocycloalkyl, 4-21 membered heterocycloalkylalkyl, 5-15 membered heteroaryl, 6-21 membered heteroarylalkyl, halogen, —CN, —C(=O)R$^{250}$, —C(=O)OR$^{250}$, —C(=O)NR$^{250}$R$^{250}$, —NR$^{250}$R$^{250}$, —NR$^{250}$C(=O)R$^{250}$, —NR$^{250}$C(=O)OR$^{250}$, —NR$^{250}$S(=O)$_2$R$^{250}$, —OR$^{250}$, =O, —OC(=O)R$^{250}$, —OC(=O)NR$^{250}$R$^{250}$, =S, —S(=O)$_n$R$^{250}$, and —S(=O)$_2$NR$^{250}$R$^{250}$.

In each embodiment of the present invention that is described in the paragraphs that precede or follow this paragraph, the definition of R$^{250}$ may be chosen from any of the embodiments that are described in this paragraph. In one embodiment, R$^{250}$ at each occurrence is independently chosen from H, C$_{1-6}$alkyl and C$_{1-6}$-haloalkyl. In another embodiment, R$^{250}$ at each occurrence is independently chosen from H and C$_{1-6}$alkyl. In another embodiment, R$^{250}$ at each occurrence is H.

In each embodiment of the present invention that is described in the paragraphs that precede or follow this paragraph, the definition of R$^{251}$ may be chosen from any of the embodiments that are described in this paragraph. In one embodiment, R$^{251}$ at each occurrence is independently chosen from C$_{1-6}$alkyl and C$_{1-6}$-haloalkyl. In another embodiment, R$^{251}$ at each occurrence is independently C$_{1-6}$alkyl.

In each embodiment of the present invention that is described in the paragraphs that precede or follow this paragraph, the definition of n may be chosen from any of the embodiments that are described in this paragraph. In one embodiment, n at each occurrence is independently chosen from 0, 1, and 2. In another embodiment, n at each occurrence is independently chosen from 0 and 2. In another embodiment, n at each occurrence is 2.

According to the present invention, any combination of the above-recited embodiments may be combined to define the variables Q$^1$, Q$^2$, Q$^3$, Q$^4$, L$^1$, A$^1$, R$^a$, G$^1$, X$^1$, Z$^1$, L$^2$, L$^3$, L$^4$, A$^2$, A$^3$, A$^4$, R$^b$, G$^2$, G$^2$, G$^3$, G$^4$, X$^2$, X$^3$, X$^4$, Z$^2$, Z$^3$, Z$^4$, A$^{21}$, A$^{22}$, A$^{23}$, Z$^{21}$, Z$^{22}$, Z$^{23}$, Z$^{24}$, Z$^{25}$, Z$^{26}$, Z$^{27}$, A$^{31}$, A$^{32}$, A$^{33}$, Z$^{31}$, Z$^{32}$, Z$^{33}$, Z$^{34}$, Z$^{35}$, Z$^{36}$, Z$^{37}$, R$^9$, R$^{19}$, R$^{29}$, R$^{39}$, R$^{49}$, R$^{59}$, R$_{69}$, R$^{79}$, R$^{89}$, R$^{99}$, R$^{139}$, R$^1$, R$^4$, R$^5$, R$^6$, R$^{10}$, R$^{11}$, R$^{14}$, R$^{15}$, R$^{16}$, R$^{17}$, R$^{21}$, R$^{24}$, R$^{25}$, R$^{26}$, R$^{31}$, R$^{34}$, R$^{35}$, R$^{36}$, R$^{41}$, R$^{44}$, R$^{45}$, R$^{46}$, R$^{50}$, R$^{51}$, R$^{54}$, R$^{55}$, R$^{56}$, R$^{57}$, R$^{61}$, R$^{64}$, R$^{65}$, R$^{66}$, R$_{71}$, R$_{74}$, R$^{75}$, R$^{76}$, R$^{80}$, R$^{81}$, R$^{84}$, R$^{85}$, R$^{86}$, R$^{87}$, R$^{90}$, R$^{91}$, R$^{94}$, R$^{95}$, R$^{96}$, R$^{97}$, R$^{100}$, R$^{101}$, R$^{104}$, R$^{105}$, R$_{106}$, R$^{107}$, R$^{130}$, R$^{131}$, R$^{134}$, R$^{135}$, R$^{136}$, R$^{137}$, R$^{170}$, R$^{171}$, R$^{174}$, R$^{175}$, R$^{176}$, R$^{177}$, R$^2$, R$^3$, R$^{12}$, R$^{13}$, R$^{22}$, R$^{23}$, R$^{32}$, R$^{33}$, R$^{42}$, R$^{43}$, R$^{52}$, R$^{53}$, R$^{62}$, R$^{63}$, R$^{72}$, R$^{73}$, R$^{82}$, R$^{83}$, R$^{92}$, R$^{93}$, R$^{102}$, R$^{103}$, R$^{132}$, R$^{133}$, R$^{172}$, R$^{173}$, R$^{179}$, R$^{189}$, R$^{199}$, R$^{209}$, R$^{210}$, R$^{211}$, R$^{214}$, R$^{215}$, R$^{216}$, R$^{217}$, R$^{212}$, R$^{213}$, R$^{219}$, R$^{229}$, R$^{239}$, R$^{249}$, R$^{250}$, and n in the compound of formula I. Therefore, the present invention provides a compound of formula I and pharmaceutically acceptable salts thereof in which Q$^1$, Q$^2$, Q$^3$, Q$^4$, L$^1$, A$^1$, R$^a$, G$^1$, X$^1$, Z$^1$, L$^2$, L$^3$, L$^4$, A$^2$, A$^3$, A$^4$, R$^b$, G$^2$, G$^3$, G$^4$, X$^2$X$^3$, X$^4$, Z$^2$, Z$^3$, Z$^4$, A$^{21}$, A$^{22}$, A$^{23}$, Z$^{21}$, Z$^{22}$, Z$^{23}$, Z$^{24}$, Z$^{25}$, Z$^{26}$, Z$^{27}$, A$^{31}$, A$^{32}$, A$^{33}$, Z$^{31}$, Z$^{32}$, Z$^{33}$, Z$^{34}$, Z$^{35}$, Z$^{36}$, Z$^{37}$, R$^9$, R$^{19}$, R$^{29}$, R$^{39}$, R$^{49}$, R$^{59}$, R$^{69}$, R$^{79}$, R$^{89}$, R$^{99}$, R$^{139}$, R$^1$, R$^4$, R$^5$, R$^6$, R$^{10}$, R$^{11}$, R$^{14}$, R$^{15}$, R$^{16}$, R$^{17}$, R$^{21}$, R$^{24}$, R$^{25}$, R$^{26}$, R$^{31}$, R$^{34}$, R$^{35}$, R$^{36}$, R$^{41}$, R$^{44}$, R$_{45}$, R$_{46}$, R$^{50}$, R$^{51}$, R$^{54}$, R$^{55}$, R$^{56}$, R$^{57}$, R$^{61}$, R$^{64}$, R$^{65}$, R$^{66}$, R$^{71}$, R$^{74}$, R$^{75}$, R$^{76}$, R$^{80}$, R$^{81}$, R$^{84}$, R$^{85}$, R$^{86}$, R$_{87}$, R$^{90}$, R$^{91}$, R$^{94}$, R$^{95}$, R$^{96}$, R$^{97}$, $R^{100}$, $R^{101}$, $R^{104}$, $R^{105}$, $R^{106}$, $R^{107}$, $R^{130}$, $R^{131}$, $R^{134}$, $R^{135}$, $R^{136}$, $R^{137}$, $R^{170}$, $R^{171}$, $R^{174}$, $R^{175}$, $R^{176}$, $R^{177}$, $R^2$, $R^3$, $R^{12}$, $R^{13}$, $R^{22}$, $R^{23}$, $R^{32}$, $R^{33}$, $R^{42}$, $R^{43}$, $R^{52}$, $R^{53}$, $R^{62}$, $R^{63}$, $R^{72}$, $R^{73}$, $R^{82}$, $R^{83}$, $R^{92}$, $R^{93}$, $R^{102}$, $R^{103}$, $R^{132}$, $R^{133}$, $R^{172}$, $R^{173}$, $R^{179}$, $R^{189}$, $R^{199}$, $R^{209}$, $R^{210}$, $R^{211}$, $R^{214}$, $R^{215}$, $R^{216}$, $R^{217}$, $R^{212}$, $R^{213}$, $R^{219}$, $R^{229}$, $R^{239}$, $R^{249}$, $R^{250}$, and n are independently selected from any of the above-recited embodiments. In other words, the present invention includes a compound of formula I and pharmaceutically acceptable salts thereof in which $Q^1$, $Q^2$, $Q^3$, $Q^4$, $L^1$, $A^1$, $R^a$, $G^1$, $X^1$, $Z^1$, $L^2$, $L^3$, $L^4$, $A^2$, $A^3$, $A^4$, $R^b$, $G^2$, $G^3$, $G^4$, $X^2$, $X^3$, $X^4$, $Z^2$, $Z^3$, $Z^4$, $A^{21}$, $A^{22}$, $A^{23}$, $Z^{21}$, $Z^{22}$, $Z^{23}$, $Z^{24}$, $Z^{25}$, $Z^{26}$, $Z^{27}$, $A^{31}$, $A^{32}$, $A^{33}$, $Z^{31}$, $Z^{32}$, $Z^{33}$, $Z^{34}$, $Z^{35}$, $Z^{36}$, $Z^{37}$, $R^9$, $R^{19}$, $R^{29}$, $R^{39}$, $R^{49}$, $R^{59}$, $R^{69}$, $R^{79}$, $R^{89}$, $R^{99}$, $R^{139}$, $R^1$, $R^4$, $R^6$, $R^{10}$, $R^{11}$, $R^{14}$, $R^{15}$, $R^{16}$, $R^{17}$, $R^{21}$, $R^{24}$, $R^{25}$, $R^{26}$, $R^{31}$, $R^{34}$, $R^{35}$, $R^{36}$, $R^{41}$, $R^{44}$, $R^{45}$, $R^{46}$, $R^{50}$, $R^{51}$, $R^{54}$, $R^{55}$, $R^{56}$, $R^{57}$, $R^{61}$, $R^{64}$, $R^{65}$, $R^{66}$, $R^{71}$, $R^{74}$, $R^{75}$, $R^{76}$, $R^{80}$, $R^{81}$, $R^{84}$, $R^{85}$, $R^{86}$, $R_{87}$, $R^{90}$, $R^{91}$, $R^{94}$, $R^{95}$, $R^{96}$, $R^{97}$, $R^{100}$, $R^{101}$, $R^{104}$, $R^{105}$, $R^{106}$, $R^{107}$, $R^{130}$, $R^{131}$, $R^{134}$, $R^{135}$, $R^{136}$, $R^{137}$, $R^{170}$, $R^{171}$, $R^{174}$, $R^{175}$, $R^{176}$, $R^{177}$, $R^2$, $R^3$, $R^{12}$, $R^{13}$, $R^{22}$, $R^{23}$, $R^{32}$, $R^{33}$, $R^{42}$, $R^{43}$, $R^{52}$, $R^{53}$, $R^{62}$, $R^{63}$, $R^{72}$, $R^{73}$, $R^{82}$, $R^{83}$, $R^{92}$, $R^{93}$, $R^{102}$, $R^{103}$, $R^{132}$, $R^{133}$, $R^{172}$, $R^{173}$, $R^{179}$, $R^{189}$, $R^{199}$, $R^{209}$, $R^{210}$, $R^{211}$, $R^{214}$, $R^{215}$, $R^{216}$, $R^{217}$, $R^{212}$, $R^{213}$, $R^{219}$, $R^{229}$, $R^{239}$, $R^{249}$, $R^{250}$, and n are defined by any combination of the broader and narrower definitions of these variables as recited in any of the above embodiments. For example, included within the scope of the present invention are compounds of formula I and pharmaceutically acceptable salts thereof in which $Q^1$ is -$L^1$-$A^1$-$G^1$-$X^1$—$Z^1$; $Q^2$ is -$L^2$-$A^2$-$G^2$-$X^2$—$Z^2$; $Q^3$ is -$L^3$-$A^3$-$G^3$-$X^3$—$Z^3$; $Q^4$ is -$L^4$-$A^4$-$G^4$-$X^4$—$Z^4$; $L^1$ is $C_{1-6}$alkylene optionally substituted by 1-12 $R^9$, $C_{7-16}$aralkylene optionally substituted by 1-18 $R^9$, $C_{3-11}$cycloalkylene optionally substituted by 1-20 $R^9$, $C_{4-6}$cycloalkylalkylene optionally substituted by 1-31 $R^9$, 3-15 membered heterocycloalkylene optionally substituted by 1-27 $R^9$, 4-21 membered heterocycloalkylalkylene optionally substituted by 1-39 $R^9$, 5-15 membered heteroarylene optionally substituted by 1-14 $R^9$, 6-21 membered heteroarylalkylene optionally substituted by 1-26 $R^9$, —$C_{0-3}$alkylC(=O)$C_{0-3}$alkyl-, —$C_{0-3}$alkylC(=O)O$C_{0-3}$alkyl-, —$C_{0-3}$alkylC(=O)NR$^4$$C_{0-3}$alkyl-, —$C_{0-3}$alkylC(=S)NR$^4$$C_{0-3}$alkyl-, —$C_{0-3}$alkylNR$^4$$C_{0-3}$alkyl-, —$C_{0-3}$alkylNR$^4$NR$^4$$C_{0-3}$alkyl-, —$C_{0-3}$alkylNR$^4$C(=O)$C_{0-3}$alkyl-, —$C_{0-3}$alkylNR$^4$C(=O)C(=O)$C_{0-3}$alkyl-, —$C_{0-3}$alkylNR$^4$C(=O)O$C_{0-3}$alkyl-, —$C_{0-3}$alkylNR$^4$C(=O)C(=O)O$C_{0-3}$alkyl-, —$C_{0-3}$alkylNR$^4$C(=O)NR$^4$$C_{0-3}$alkyl-, —$C_{0-3}$alkylNR$^4$C(=O)NR$^4$C(=O)$C_{0-3}$alkyl-, —$C_{0-3}$alkylNR$^4$C(=O)NR$^4$C(=O)O$C_{0-3}$alkyl-, —$C_{0-3}$alkylNR$^4$C(=O)C(=O)NR$^4$$C_{0-3}$alkyl-, —$C_{0-3}$alkylNR$^4$C(=S)$C_{0-3}$alkyl-, —$C_{0-3}$alkylNR$^4$C(=S)O$C_{0-3}$alkyl-, —$C_{0-3}$alkylNR$^4$C(=S)NR$^4$$C_{0-3}$alkyl-, —$C_{0-3}$alkylNR$^4$S(=O)$_2$$C_{0-3}$alkyl-, —$C_{0-3}$alkylNR$^4$S(=O)$_2$NR$^4$$C_{0-3}$alkyl-, —$C_{0-3}$alkylO$C_{0-3}$alkyl-, —$C_{0-3}$alkylOC(=O)$C_{0-3}$alkyl-, —$C_{0-3}$alkylOC(=O)NR$^4$$C_{0-3}$alkyl-, —$C_{0-3}$alkylOC(=O)O$C_{0-3}$alkyl-, —$C_{0-3}$alkylOS(=O)$C_{0-3}$alkyl-, —$C_{0-3}$alkylOS(=O)$_2$$C_{0-3}$alkyl-, —$C_{0-3}$alkylOS(=O)$_2$O$C_{0-3}$alkyl-, —$C_{0-3}$alkylOS(=O)$_2$NR$^4$$C_{0-3}$alkyl-, —$C_{0-3}$alkylS(=O)$_n$$C_{0-3}$alkyl-, —$C_{0-3}$alkylS(=O)$_2$O$C_{0-3}$alkyl-, —$C_{0-3}$alkylSO$_3$$C_{0-3}$alkyl-, —$C_{0-3}$alkylS(=O)$_2$NR$^4$$C_{0-3}$alkyl-, —$C_{0-3}$alkylS(=O)NR$^4$$C_{0-3}$alkyl-, or absent; $A^1$ is $C_{1-6}$alkylene optionally substituted by 1-12 $R^a$, $C_{6-11}$arylene optionally substituted by 1-6 $R^a$, $C_{7-16}$arylalkylene optionally substituted by 1-18 $R^a$, $C_{3-11}$cycloalkylene optionally substituted by 1-20 $R^a$, $C_{4-17}$cycloalkylalkylene optionally substituted by 1-31 $R^a$, 3-15 membered heterocycloalkylene optionally substituted by 1-27 $R^a$, 4-21 membered heterocycloalkylalkylene optionally substituted by 1-39 $R^a$, 5-15 membered heteroarylene optionally substituted by 1-14 $R^a$, or 6-21 membered heteroarylalkylene optionally substituted by 1-26 $R^a$, wherein each $R^a$ is independently chosen from $C_{1-6}$alkyl optionally substituted by 1-13 $R^{19}$, $C_{2-6}$alkenyl optionally substituted by 1-11 $R^{19}$, $C_{2-6}$alkynyl optionally substituted by 1-9 $R^{19}$, $C_{6-11}$ aryl optionally substituted by 1-7 $R^{19}$, $C_{7-16}$arylalkyl optionally substituted by 1-19 $R^{19}$, $C_{3-11}$cycloalkyl optionally substituted by 1-21 $R^{19}$, $C_{4-17}$cycloalkylalkyl optionally substituted by 1-32 $R^{19}$, 3-15 membered heterocycloalkyl optionally substituted by 1-28 $R^{19}$, 4-21 membered heterocycloalkylalkyl optionally substituted by 1-40 $R^{19}$, 5-15 membered heteroaryl optionally substituted by 1-15 $R^{19}$, 6-21 membered heteroarylalkyl optionally substituted by 1-27 $R^{19}$, halogen, —CN, —C(=O)R$^{10}$, —C(=O)OR$^{10}$, —C(=O)NR$^{12}$R$^{13}$, —C(=O)C(O)R$^{10}$, —C(=S)NR$^{12}$R$^{13}$, —NC, —NO$_2$, —NR$^{12}$R$^{13}$, —NR$^{14}$NR$^{12}$R$^{13}$, —NR$^{14}$OR$^{16}$, —NR$^{14}$C(=O)R$^{10}$, —NR$^{14}$C(=O)C(=O)R$^{10}$, —NR$^{14}$C(=O)OR$^{11}$, —NR$^{14}$C(=O)C(=O)OR$^{11}$, —NR$^{14}$C(=O)NR$^{12}$R$^{13}$, —NR$^{14}$C(=O)NR$^{14}$C(=O)R$^{10}$, —NR$^{14}$C(=O)NR$^{14}$C(=O)OR$^{10}$, —NR$^{14}$C(=NR$^{15}$)NR$^{12}$R$^{13}$, —NR$^{14}$C(=O)C(=O)NR$^{12}$R$^{13}$, —NR$^{14}$C(=S)R$^{10}$, —NR$^{14}$C(=S)OR$^{10}$, —NR$^{14}$C(=S)NR$^{12}$R$^{13}$, —NR$^{14}$S(=O)$_2$R$^{11}$, —NR$^{14}$S(=O)$_2$NR$^{12}$R$^{13}$, —OR$^{10}$, =O, —OCN, —OC(=O)R$^{10}$, —OC(=O)NR$^{12}$R$^{13}$, —OC(=O)OR$^{10}$, —OS(=O)R$^{10}$, —OS(=O)$_2$R$^{10}$, —OS(=O)$_2$OR$^{10}$, —OS(=O)$_2$NR$^{12}$R$^{13}$, —SCN, =S, —S(=O)$_n$R$^{10}$, —S(=O)$_2$OR$^{10}$, —SO$_3$R$^{17}$, —S(=O)$_2$NR$^{12}$R$^{13}$, and —S(=O)NR$^{12}$R$^{13}$; $G^1$ is $C_{1-6}$alkylene optionally substituted by 1-12 $R^{29}$, $C_{6-11}$arylene optionally substituted by 1-6 $R^{29}$, $C_{7-16}$arylalkylene optionally substituted by 1-18 $R^{29}$, $C_{3-11}$cycloalkylene optionally substituted by 1-20 $R^{29}$, $C_{4-17}$cycloalkylalkylene optionally substituted by 1-31 $R^{29}$, 3-15 membered heterocycloalkylene optionally substituted by 1-27 $R^{29}$, 4-21 membered heterocycloalkylalkylene optionally substituted by 1-39 $R^{29}$, 5-15 membered heteroarylene optionally substituted by 1-14 $R^{29}$, 6-21 membered heteroarylalkylene optionally substituted by 1-26 $R^{29}$, —$C_{0-3}$alkylC(=O)$C_{0-3}$alkyl-, —$C_{0-3}$alkylC(=O)O$C_{0-3}$alkyl-, —$C_{0-3}$alkylC(=O)NR$^{24}$$C_{0-3}$alkyl-, —$C_{0-3}$alkylC(=O)C(=O)$C_{0-3}$alkyl-, —$C_{0-3}$alkylC(=S)NR$^{24}$$C_{0-3}$alkyl-, —$C_{0-3}$alkylNR$^{24}$$C_{0-3}$alkyl-, —$C_{0-3}$lkylNR$^{24}$NR$^{24}$$C_{0-3}$alkyl-, —$C_{0-3}$alkylNR$^{24}$C(=O)$C_{0-3}$alkyl-, —$C_{0-3}$alkylNR$^{24}$C(=O)C(=O)$C_{0-3}$alkyl-, —$C_{0-3}$alkylNR$^{24}$C(=O)O$C_{0-3}$alkyl-, —$C_{0-3}$alkylNR$^{24}$C(=O)C(=O)O$C_{0-3}$alkyl-, —$C_{0-3}$alkylNR$^{24}$C(=O)NR$^{24}$$C_{0-3}$alkyl-, —$C_{0-3}$alkylNR$^{24}$C(=O)NR$^{24}$C(=O)$C_{0-3}$alkyl-, —$C_{0-3}$alkylNR$^{24}$C(=O)NR$^{24}$C(=O)O$C_{0-3}$alkyl-, —$C_{0-3}$alkylNR$^{24}$C(=O)C(=O)NR$^{24}$$C_{0-3}$alkyl-, —$C_{0-3}$alkylNR$^{24}$C(=S)$C_{0-3}$alkyl-, —$C_{0-3}$alkylNR$^{24}$C(=S)O$C_{0-3}$alkyl-, —$C_{0-3}$alkylNR$^{24}$C(=S)NR$^{24}$$C_{0-3}$alkyl-, —$C_{0-3}$alkylNR$^{24}$S(=O)$_2$$C_{0-3}$alkyl-, —$C_{0-3}$alkylNR$^{24}$S(=O)$_2$NR$^{24}$$C_{0-3}$alkyl-, —$C_{0-3}$alkylO$C_{0-3}$alkyl-—$C_{0-3}$alkylOC(=O)$C_{0-3}$alkyl-, —$C_{0-3}$alkylOC(=O)NR$^{24}$$C_{0-3}$alkyl-, —$C_{0-3}$alkylOC(=O)O$C_{0-3}$alkyl-, —$C_{0-3}$alkylOS(=O)$C_{0-3}$alkyl-, —$C_{0-3}$alkylOS(=O)$_2$$C_{0-3}$alkyl-, —$C_{0-3}$alkylOS(=O)$_2$O$C_{0-3}$alkyl-, —$C_{0-3}$alkylOS(=O)$_2$NR$^{24}$$C_{0-3}$alkyl-, —$C_{0-3}$alkylS(=O)$_n$$C_{0-3}$alkyl-, —$C_{0-3}$alkylS(=O)$_2$O$C_{0-3}$alkyl-, —$C_{0-3}$alkylSO$_3$$C_{0-3}$alkyl-, —$C_{0-3}$alkylS(=O)$_2$NR$^{24}$$C_{0-3}$alkyl-, —$C_{0-3}$alkylS(=O)NR$^{24}$$C_{0-3}$alkyl-, or absent; $X^1$ is $C_{1-6}$alkylene optionally substituted by 1-12 $R^{39}$, $C_{6-11}$arylene optionally substituted by 1-6 $R^{39}$, $C_{7-16}$arylalkylene optionally substituted by 1-18 $R^{39}$, $C_{3-11}$cycloalkylene optionally substituted by 1-20 $R^{39}$, $C_{4-17}$cycloalkylalkylene optionally substituted by 1-31 $R^{39}$, 3-15 membered heterocycloalkylene optionally substituted by 1-27 $R^{39}$, 4-21 membered heterocycloalkylalkylene optionally substituted by 1-39 $R^{39}$, 5-15 membered heteroarylene optionally substituted by 1-14 $R^{39}$, 6-21 membered heteroarylalkylene optionally substituted by 1-26 $R^{39}$, —$C_{0-3}$alkylC(=O)$C_{0-3}$ alkyl-, —C$_{0-3}$alkylC(=O)OC$_{0-3}$alkyl-, —C$_{0-3}$alkylC(=O)NR$^{34}$C$_{0-3}$alkyl-, —C$_{0-3}$alkylC(=O)C(=O)C$_{0-3}$alkyl-, —C$_{0-3}$alkylC(=S)NR$^{34}$C$_{0-3}$alkyl-, —C$_{0-3}$alkylNR$^{34}$C$_{0-3}$alkyl-, —C$_{0-3}$alkylNR$^{34}$NR$^{34}$C$_{0-3}$alkyl-, —C$_{0-3}$ alkylNR$^{34}$C(=O)C$_{0-3}$alkyl-, —C$_{0-3}$alkylNR$^{34}$C(=O)C(=O)C$_{0-3}$alkyl-, —C$_{0-3}$alkylNR$^{34}$C(=O)OC$_{0-3}$alkyl-, —C$_{0-3}$alkylNR$^{34}$C(=O)C(=O)OC$_{0-3}$alkyl-, —C$_{0-3}$ alkylNR$^{34}$C(=O)NR$^{34}$C$_{0-3}$alkyl-, —C$_{0-3}$alkylNR$^{34}$C(=O)NR$^{34}$C(=O)C$_{0-3}$alkyl-, —C$_{0-3}$alkylNR$^{34}$C(=O)NR$^{34}$C(=O)OC$_{0-3}$ alkyl-, —C$_{0-3}$alkylNR$^{34}$C(=NR$^{35}$)NR$^{34}$C$_{0-3}$alkyl-, —C$_{0-3}$ alkylNR$^{34}$C(=O)C(=O)NR$^{34}$C$_{0-3}$ alkyl-, —C$_{0-3}$alkylNR$^{34}$C(=S)C$_{0-3}$alkyl-, —C$_{0-3}$ alkylNR$^{34}$C(=S)OC$_{0-3}$ alkyl-, —C$_{0-3}$alkylNR$^{34}$C(=S)NR$^{34}$C$_{0-3}$alkyl-, —C$_{0-3}$alkylNR$^{34}$S(=O)$_2$C$_{0-3}$alkyl-, —C$_{0-3}$ alkylNR$^{34}$S(=O)$_2$NR$^{34}$C$_{0-3}$alkyl-, —C$_{0-3}$alkylOC$_{0-3}$ alkyl- —C$_{0-3}$alkylOC(=O)C$_{0-3}$alkyl-, —C$_{0-3}$alkylOC(=O)NR$^{34}$C$_{0-3}$alkyl-, —C$_{0-3}$alkylOC(=O)OC$_{0-3}$alkyl-, —C$_{0-3}$alkylOS(=O)C$_{0-3}$ alkyl-, —C$_{0-3}$alkylOS(=O)$_2$C$_{0-3}$ alkyl-, —C$_{0-3}$alkylOS(=O)$_2$OC$_{0-3}$alkyl-, —C$_{0-3}$alkylOS(=O)$_2$NR$^{34}$C$_{0-3}$alkyl-, —C$_{0-3}$alkylS(=O)$_n$C$_{0-3}$alkyl-, —C$_{0-3}$alkylS(=O)$_2$OC$_{0-3}$ alkyl-, —C$_{0-3}$alkylSO$_3$C$_{0-3}$alkyl-, —C$_{0-3}$alkylS(=O)$_2$NR$^{34}$C$_{0-3}$alkyl-, —C$_{0-3}$alkylS(=O)NR$^{34}$C$_{0-3}$alkyl-, or absent; $Z^1$ is H, C$_{1-6}$alkyl optionally substituted by 1-13 R$^{49}$, C$_{7-16}$arylalkyl optionally substituted by 1-19 R$^{49}$, C$_{3-11}$cycloalkyl optionally substituted by 1-21 R$^{49}$, C$_{4-17}$cycloalkylalkyl optionally substituted by 1-32 R$^{49}$, 3-15 membered heterocycloalkyl optionally substituted by 1-28 R$^{49}$, 4-21 membered heterocycloalkylalkyl optionally substituted by 1-40 R$^{49}$, 5-15 membered heteroaryl optionally substituted by 1-15 R$^{49}$, 6-21 membered heteroarylalkyl optionally substituted by 1-27 R$^{49}$, halogen, —CN, —C(=O)R$^{100}$, C(=O)OR$^{100}$, —C(=O)NR$^{102}$R$^{103}$, —C(=O)C(=O)R$^{100}$, —C(=S)NR$^{102}$R$^{103}$, —NC, —NO$_2$, —NR$^{102}$R$^{103}$NR$^{104}$NR$^{102}$R$^{103}$, —NR$^{104}$C(=O)R$^{100}$, —NR$^{104}$C(=O)C(=O)R$^{100}$, —NR$^{104}$C(=O)OR$^{101}$, —NR$^{104}$C(=O)C(=O)OR$^{101}$, —NR$^{104}$C(=)NR$^{102}$R$^{103}$, —NR$^{104}$C(=O)NR$^{104}$C(=O)R$^{100}$, —NR$^{104}$C(=O)NR$^{104}$C(=O)OR$^{100}$, —NR$^{104}$C(=NR$^{105}$)NR$^{102}$R$^{103}$, —NR$^{104}$C(=O)C(=O)NR$^{102}$R$^{103}$, —NR$^{104}$C(=S)R$^{100}$, —NR$^{104}$C(=S)OR$^{100}$, —NR$^{104}$C(=S)NR$^{102}$R$^{103}$, —NR$^{104}$S(=O)$_2$R$^{101}$, —NR$^{104}$S(=O)$_2$NR$^{102}$R$^{103}$, —OR$^{100}$, =O, —OCN, —OC(=O)R$^{100}$, —OC(=O)NR$^{102}$R$^{103}$, —OC(=O)OR$^{100}$, —OS(=O)R$^{100}$, —OS(=O)$_2$R$^{100}$, —OS(=O)OR$^{100}$, —OS(=O)$_2$NR$^{102}$R$^{103}$, —SCN, =S, —S(=O)$_n$R$^{100}$, —S(=O)$_2$OR$^{100}$, —SO$_3$R$^{107}$, —S(=O)$_2$NR$^{102}$R$^{103}$, or —S(=O)NR$^{102}$R$^{103}$; L$^2$, L$^3$, and L$^4$ are independently present or absent, and if present each is independently chosen from —C$_{0-3}$alkylC(=O)C$_{0-3}$alkyl-, —C$_{0-3}$alkylC(=O)OC$_{0-3}$alkyl-, —C$_{0-3}$alkylC(=O)NR$^{44}$C$_{0-3}$alkyl-, —C$_{0-3}$alkylC(=O)C(=O)C$_{0-3}$alkyl-, —C$_{0-3}$alkylC(=S)NR$^{44}$C$_{0-3}$alkyl-, —C$_{0-3}$alkylNR$^{44}$C$_{0-3}$alkyl-, —C$_{0-3}$alkylNR$^{44}$NR$^{44}$C$_{0-3}$alkyl-, —C$_{0-3}$ alkylNR$^{44}$C(=O)C$_{0-3}$alkyl-, —C$_{0-3}$alkylNR$^{44}$C(=O)C(=O)C$_{0-3}$alkyl-, —C$_{0-3}$alkylNR$^{44}$C(=O)OC$_{0-3}$alkyl-, —C$_{0-3}$alkylNR$^{44}$C(=O)C(=O)OC$_{0-3}$alkyl-, —C$_{0-3}$ alkylNR$^{44}$C(=O)NR$^{44}$C$_{0-3}$alkyl-, —C$_{0-3}$alkylNR$^{44}$C(=O)NR$^{44}$C(=O)C$_{0-3}$alkyl-, —C$_{0-3}$alkylNR$^{44}$C(=O)NR$^{44}$C(=O)OC$_{0-3}$ alkyl-, —C$_{0-3}$alkylNR$^{44}$C(=NR$^{45}$)NR$^{44}$C$_{0-3}$alkyl-, —C$_{0-3}$ alkylNR$^{44}$C(=O)C(=O)NR$^{44}$C$_{0-3}$ alkyl-, —C$_{0-3}$alkylNR$^{44}$C(=S)C$_{0-3}$alkyl-, —C$_{0-3}$ lkylNR$^{44}$C(=S)OC$_{0-3}$ alkyl-, —C$_{0-3}$alkylNR$^{44}$C(=S)NR$^{44}$C$_{0-3}$alkyl-, —C$_{0-3}$alkylNR$^{44}$S(=O)$_2$C$_{0-3}$alkyl-, —C$_{0-3}$ alkylNR$^{44}$S(=O)$_2$NR$^{44}$C$_{0-3}$alkyl-, —C$_{0-3}$alkylOC$_{0-3}$ alkyl-, —C$_{0-3}$alkylOC(=O)C$_{0-3}$alkyl-, —C$_{0-3}$alkylOC(=O)NR$^{44}$C$_{0-3}$alkyl-, —C$_{0-3}$alkylOC(=O)OC$_{0-3}$alkyl-, —C$_{0-3}$alkylOS(=O)C$_{0-3}$ alkyl-, —C$_{0-3}$alkylOS(=O)$_2$C$_{0-3}$ alkyl-, —C$_{0-3}$alkylOS(=O)$_2$OC$_{0-3}$alkyl-, —C$_{0-3}$alkylOS(=O)$_2$NR$^{44}$C$_{0-3}$alkyl-, —C$_{0-3}$alkylS(=O)—C$_{0-3}$alkyl-, —C$_{0-3}$alkylS(=O)$_2$OC$_{0-3}$ alkyl-, —C$_{0-3}$alkylSO$_3$C$_{0-3}$alkyl-, —C$_{0-3}$alkylS(=O)$_2$NR$^{44}$C$_{0-3}$alkyl-, and —C$_{0-3}$alkylS(=O)NR$^{44}$C$_{0-3}$alkyl-; A$^2$, A$^3$, and A$^4$ are independently present or absent, and if present each is independently chosen from C$_{1-6}$alkylene optionally substituted by 1-12 R$^b$, C$_{6-11}$ arylene optionally substituted by 1-6 R$^b$, C$_{7-16}$arylalkylene optionally substituted by 1-18 R$^b$, C$_{3-11}$cycloalkylene optionally substituted by 1-20 R$^b$, C$_{4-17}$cycloalkylalkylene optionally substituted by 1-31 R$^b$, 3-15 membered heterocycloalkylene optionally substituted by 1-27 R$^b$, 4-21 membered heterocycloalkylalkylene optionally substituted by 1-39 R$^b$, 5-15 membered heteroarylene optionally substituted by 1-14 R$^b$, or 6-21 membered heteroarylalkylene optionally substituted by 1-26 R$^b$; wherein each R$^b$ is independently chosen from C$_{1-6}$alkyl optionally substituted by 1-13 R$^{59}$, C$_{2-6}$alkenyl optionally substituted by 1-11 R$^{59}$, C$_{2-6}$alkynyl optionally substituted by 1-9 R$^{59}$, C$_{6-11}$ aryl optionally substituted by 1-7 R$^{59}$, C$_{7-16}$arylalkyl optionally substituted by 1-19 R$^{59}$, C$_{3-11}$cycloalkyl optionally substituted by 1-21 R$^{59}$, C$_{4-17}$cycloalkylalkyl optionally substituted by 1-32 R$^{59}$, 3-15 membered heterocycloalkyl optionally substituted by 1-28 R$^{59}$, 4-21 membered heterocycloalkylalkyl optionally substituted by 1-40 R$^{59}$, 5-15 membered heteroaryl optionally substituted by 1-15 R$^{59}$, 6-21 membered heteroarylalkyl optionally substituted by 1-27 R$^{59}$, halogen, —CN, —C(=O)R$^{50}$, —C(=O)OR$^{50}$, —C(=O)NR$^{52}$R$^{53}$, —C(=O)C(=O)R$^{50}$, —C(=S)NR$^{52}$R$^{53}$, —NC, —NO$_2$, —NR$^{52}$R$^{53}$, —NR$^{54}$NR$^{52}$R$^{53}$, —NR$^{54}$C(=O)R$^{50}$, —NR$^{54}$C(=O)C(=O)R$^{50}$, —NR$^{54}$C(=O)OR$^{51}$, —NR$^{54}$C(=O)C(=O)OR$^{51}$, —NR$^{54}$C(=O)NR$^{52}$R$^{53}$, —NR$^{54}$C(=O)NR$^{54}$C(=O)R$^{50}$, —NR$^{54}$C(=O)NR$^{54}$C(=O)OR$^{50}$, —NR$^{54}$C(=NR$^{55}$)NR$^{52}$R$^{53}$, —NR$^{54}$C(=O)C(=O)NR$^{52}$R$^{53}$, —NR$^{54}$C(=S)R$^{50}$, —NR$^{54}$C(=S)OR$^{50}$, —NR$^{54}$C(=S)NR$^{52}$R$^{53}$, —NR$^{54}$S(=O)$_2$R$^{51}$, —NR$^{54}$S(=O)$_2$NR$^{52}$R$^{53}$, —OR$^{50}$, =O, —OCN, —OC(=O)R$^{50}$, —OC(=O)NR$^{52}$R$^{53}$, —OC(=O)OR$^{50}$, —OS(=O)R$^{50}$, —OS(=O)$_2$R$^{50}$, —OS(=O)$_2$OR$^{50}$, —OS(=O)$_2$NR$^{52}$R$^{53}$, —SCN, =S, —S(=O)$_n$R$^{50}$, —S(=O)$_2$OR$^{50}$, —SO$_3$R$^{57}$, —S(=O)$_2$NR$^{52}$R$^{53}$, and —S(=O)NR$^{52}$R$^{53}$; G$^2$, G$^3$, and G$^4$ are independently present or absent, and if present each is independently chosen from C$_{1-6}$alkylene optionally substituted by 1-12 R$^{69}$, C$_{6-11}$arylene optionally substituted by 1-6 R$^{69}$, C$_{7-16}$arylalkylene optionally substituted by 1-18 R$^{69}$, C$_{3-11}$cycloalkylene optionally substituted by 1-20 R$^{69}$, C$_{4-17}$cycloalkylalkylene optionally substituted by 1-31 R$^{69}$, 3-15 membered heterocycloalkylene optionally substituted by 1-27 R$^{69}$, 4-21 membered heterocycloalkylalkylene optionally substituted by 1-39 R$^{69}$, 5-15 membered heteroarylene optionally substituted by 1-14 R$^{69}$, 6-21 membered heteroarylalkylene optionally substituted by 1-26 R$^{69}$, —C$_{0-3}$alkylC(=O)C$_{0-3}$alkyl-, —C$_{0-3}$alkylC(=O)OC$_{0-3}$alkyl-, —C$_{0-3}$alkylC(=O)NR$^{64}$C$_{0-3}$alkyl-, —C$_{0-3}$alkylC(=O)C(=O)C$_{0-3}$alkyl-, —C$_{0-3}$alkylC(=S)NR$^{64}$C$_{0-3}$alkyl-, —C$_{0-3}$alkylNR$^{64}$C$_{0-3}$alkyl-, —C$_{0-3}$alkylNR$^{64}$NR$^{64}$C$_{0-3}$ alkyl-, —C$_{0-3}$alkylNR$^{64}$C(=O)C$_{0-3}$alkyl-, —C$_{0-3}$alkylNR$^{64}$C(=O)C(=O)C$_{0-3}$alkyl-, —C$_{0-3}$alkylNR$^{64}$C(=O)OC$_{0-3}$alkyl-, —C$_{0-3}$alkylNR$^{64}$C(=O)C(=O)OC$_{0-3}$alkyl-, —C$_{0-3}$alkylNR$^{64}$C(=O)NR$^{64}$C$_{0-3}$alkyl-, —C$_{0-3}$alkylNR$^{64}$C(=O)NR$^{64}$C(=O)C$_{0-3}$alkyl-, —C$_{0-3}$alkylNR$^{64}$C(=O)NR$^{64}$C(=O)OC$_{0-3}$alkyl-, —C$_{0-3}$alkylNR$^{64}$C(=NR$^{65}$)NR$^{64}$C$_{0-3}$alkyl-, —C$_{0-3}$alkylNR$^{64}$C(=O)C(=O)NR$^{64}$C$_{0-3}$alkyl-, —C$_{0-3}$alkylNR$^{64}$C(=S)C$_{0-3}$ alkyl-, —C$_{0-3}$alkylNR$^{64}$C(=S)OC$_{0-3}$alkyl-, —C$_{0-3}$alkylNR$^{64}$C(=S)NR$^{64}$C$_{0-3}$alkyl-, —C$_{0-3}$alkylNR$^{64}$S(=O)$_2$C$_{0-3}$alkyl-, —C$_{0-3}$alkylNR$^{64}$S(=O)$_2$NR$^{64}$C$_{0-3}$alkyl-, —C$_{0-3}$alkylOC$_{0-3}$alkyl-, —C$_{0-3}$alkylOC(=O)C$_{0-3}$alkyl-, —C$_{0-3}$alkylOC(=O)NR$^{64}$C$_{0-3}$alkyl-, —C$_{0-3}$alkylOC(=O)OC$_{0-3}$ alkyl-, —C$_{0-3}$alkylOS(=O)C$_{0-3}$alkyl-, —C$_{0-3}$alkylOS(=O)$_2$C$_{0-3}$alkyl-, —C$_{0-3}$alkylOS(=O)$_2$OC$_{0-3}$alkyl-, —C$_{0-3}$alkylOS(=O)$_2$NR$^{64}$C$_{0-3}$alkyl-, —C$_{0-3}$alkylS(=O)—C$_{0-3}$alkyl-, —C$_{0-3}$alkylS(=O)$_2$C$_{0-3}$alkyl-, —C$_{0-3}$alkylS(=O)$_2$OC$_{0-3}$alkyl-, —C$_{0-3}$alkylSO$_3$C$_{0-3}$alkyl-, —C$_{0-3}$alkylS(=O)$_2$NR$^{64}$C$_{0-3}$alkyl-, and —C$_{0-3}$alkylS(=O)NR$^{64}$C$_{0-3}$alkyl-; X$^2$, X$^3$, and X$^4$ are independently present or absent, and if present each is independently chosen from C$_{1-6}$alkylene optionally substituted by 1-12 R$^{79}$, C$_{6-11}$ arylene optionally substituted by 1-6 R$^{79}$, C$_{7-16}$arylalkylene optionally substituted by 1-18 R$^{79}$, C$_{3-11}$cycloalkylene optionally substituted by 1-20 R$^{79}$, C$_{4-17}$cycloalkylalkylene optionally substituted by 1-31 R$^{79}$, 3-15 membered heterocycloalkylene optionally substituted by 1-27 R$^{79}$, 4-21 membered heterocycloalkylalkylene optionally substituted by 1-39 R$^{79}$, 5-15 membered heteroarylene optionally substituted by 1-14 R$^{79}$, 6-21 membered heteroarylalkylene optionally substituted by 1-26 R$^{79}$, —C$_{0-3}$alkylC(=O)C$_{0-3}$alkyl-, —C$_{0-3}$alkylC(=O)OC$_{0-3}$ alkyl-, —C$_{0-3}$alkylC(=O)NR$^{74}$C$_{0-3}$alkyl-, —C$_{0-3}$alkylC(=O)C(=O)C$_{0-3}$alkyl-, —C$_{0-3}$alkylC(=S)NR$^{74}$C$_{0-3}$alkyl-, —C$_{0-3}$alkylNR$^{74}$C$_{0-3}$alkyl-, —C$_{0-3}$alkylNR$^{74}$NR$^{74}$C$_{0-3}$ alkyl-, —C$_{0-3}$ alkylNR$^{74}$C(=O)C$_{0-3}$alkyl-, —C$_{0-3}$ lkylNR$^{74}$C(=O)C(=O)C$_{0-3}$alkyl-, —C$_{0-3}$alkylNR$^{74}$C(=O)OC$_{0-3}$alkyl-, —C$_{0-3}$alkylNR$^{74}$C(=O)C(=O)OC$_{0-3}$ alkyl-, —C$_{0-3}$ lkylNR$^{74}$C(=O)NR$^{74}$C$_{0-3}$ alkyl-, —C$_{0-3}$ alkylNR$^{74}$C(=O)NR$^{74}$C(=O)C$_{0-3}$ alkyl-, —C$_{0-3}$ alkylNR$^{74}$C(=O)NR$^{74}$C(=O)OC$_{0-3}$alkyl-, —C$_{0-3}$ alkylNR$^{74}$C(=NR$^{75}$)NR$^{74}$C$_{0-3}$alkyl-, —C$_{0-3}$ alkylNR$^{74}$C(=O)C(=O)NR$^{74}$C$_{0-3}$ alkyl-, —C$_{0-3}$alkylNR$^{74}$C(=S)C$_{0-3}$ alkyl-, —C$_{0-3}$ alkylNR$^{74}$C(=S)OC$_{0-3}$ alkyl-, —C$_{0-3}$ alkylNR$^{74}$C(=S)NR$^{74}$C$_{0-3}$alkyl-, —C$_{0-3}$ alkylNR$^{74}$S(=O)$_2$ C$_{0-3}$alkyl-, —C$_{0-3}$ alkylNR$^{74}$S(=O)$_2$NR$^{74}$C$_{0-3}$alkyl-, —C$_{0-3}$ alkylOC$_{0-3}$ alkyl-, —C$_{0-3}$alkylOC(=O)C$_{0-3}$alkyl-, —C$_{0-3}$ alkylOC(=O)NR$^{74}$C$_{0-3}$alkyl-, —C$_{0-3}$alkylOC(=O)OC$_{0-3}$alkyl-, —C$_{0-3}$alkylOS(=O)C$_{0-3}$alkyl-, —C$_{0-3}$alkylOS(=O)$_2$C$_{0-3}$ alkyl-, —C$_{0-3}$alkylOS(=O)$_2$OC$_{0-3}$alkyl-, —C$_{0-3}$ alkylOS(=O)$_2$NR$^{74}$C$_{0-3}$alkyl-, —C$_{0-3}$alkylS(=O)—C$_{0-3}$ alkyl-, —C$_{0-3}$alkylS(=O)$_2$OC$_{0-3}$ alkyl-, —C$_{0-3}$alkylSO$_3$C$_{0-3}$ alkyl-, —C$_{0-3}$alkylS(=O)$_2$NR$^{74}$C$_{0-3}$alkyl-, and —C$_{0-3}$ alkylS(=O)NR$^{74}$C$_{0-3}$alkyl-; Z$^2$, Z$^3$, and Z$^4$ are independently chosen from H, C$_{1-6}$alkyl optionally substituted by 1-13 R$^{89}$, C$_{6-11}$ aryl optionally substituted by 1-7 R$^{89}$, C$_{7-16}$arylalkyl optionally substituted by 1-19 R$^{89}$, C$_{3-11}$cycloalkyl optionally substituted by 1-21 R$^{89}$, C$_{4-17}$cycloalkylalkyl optionally substituted by 1-32 R$^{89}$, 3-15 membered heterocycloalkyl optionally substituted by 1-28 R$^{89}$, 4-21 membered heterocycloalkylalkyl optionally substituted by 1-40 R$^{89}$, 5-15 membered heteroaryl optionally substituted by 1-15 R$^{89}$, 6-21 membered heteroarylalkyl optionally substituted by 1-27 R$^{89}$, halogen, —CN, —C(=O)R$^{80}$, —C(=O)OR$^{80}$, —C(=O)NR$^{82}$R$^{83}$, —C(=O)C(=O)R$^{80}$, —C(=S)NR$^{82}$R$^{83}$, —NC, —NO$_2$, —NR$^{82}$R$^{83}$, —NR$^{84}$NR$^{82}$R$^{83}$, —NR$^{84}$C(=O)R$^{80}$, —NR$^{84}$C(=O)C(=O)R$^{80}$, —NR$^{84}$C(=O)OR$^{81}$, —NR$^{84}$C(=O)C(=O)OR$^{81}$, —NR$^{84}$C(=O)NR$^{82}$R$^{83}$, —NR$^{84}$C(=O)NR$^{84}$C(=O)R$^{80}$, —NR$^{84}$C(=O)NR$^{84}$C(=O)OR$^{80}$, —NR$^{84}$C(=NR$^{85}$)NR$^{82}$R$^{83}$, —NR$^{84}$C(=O)C(=O)NR$^{82}$R$^{83}$, —NR$^{84}$C(=S)R$^{80}$, —NR$^{84}$C(=S)OR$^{80}$, —NR$^{84}$C(=S)NR$^{82}$R$^{83}$, —NR$^{84}$S(=O)$_2$R$^{81}$, —NR$^{84}$S(=O)$_2$NR$^{82}$R$^{83}$, —OR$^{80}$, =O, —OCN, —OC(=O)R$^{80}$, —OC(=O)NR$^{82}$R$^{83}$, —OC(=O)OR$^{80}$, —OS(=O)R$^{80}$, —OS(=O)$_2$R$^{80}$, —OS(=O)$_2$OR$^{80}$, —OS(=O)$_2$NR$^{82}$R$^{83}$, —SCN, =S, —S(=O)$_n$R$^{80}$, —S(=O)$_2$OR$^{80}$, —SO$_3$R$^{87}$, —S(=O)$_2$NR$^{82}$R$^{83}$, and —S(=O)NR$^{82}$R$^{83}$; alternatively, when L$^2$, A$^2$, G$^2$, X$^2$, L$^3$, A$^3$, G$^3$ and X$^3$ are absent, Z$^2$ and Z$^3$ can together form a group of formula -A$^{21}$-A$^{22}$-A$^{23}$-, or when L$^3$, A$^3$, G$^3$, X$^3$, L$^4$, A$^4$, G$^4$ and X$^4$ are absent, Z$^3$ and Z$^4$ can together form a group of formula -A$^{21}$-A$^{22}$-A$^{23}$-; wherein A$^{21}$, A$^{22}$, and A$^{23}$ are independently chosen from —CZ$^{21}$Z$^{22}$—, —CZ$^{23}$Z$^{24}$CZ$^{25}$Z$^{26}$—, —C(=O)—, —NZ$^{27}$—, —S—, —S(=O)—, —S(=O)$_2$—, or —O—; wherein:

(a) when any two of Z$^{21}$, Z$^{22}$, Z$^{23}$, Z$^{24}$, Z$^{25}$, Z$^{26}$ and Z$^{27}$ are located on adjacent atoms, they may together form a bond between the atoms, and (b) any of Z$^{21}$, Z$^{22}$, Z$^{23}$, Z$^{24}$, Z$^{25}$, Z$^{26}$ and Z$^{27}$ may be independently chosen from H, C$_{1-6}$alkyl optionally substituted by 1-13 R$^{99}$, C$_{6-11}$ aryl optionally substituted by 1-7 R$^{99}$, C$_{7-16}$arylalkyl optionally substituted by 1-19 R$^{99}$, C$_{3-11}$cycloalkyl optionally substituted by 1-21 R$^{99}$, C$_{4-17}$cycloalkylalkyl optionally substituted by 1-32 R$^{99}$, 3-15 membered heterocycloalkyl optionally substituted by 1-28 R$^{99}$, 4-21 membered heterocycloalkylalkyl optionally substituted by 1-40 R$^{99}$, 5-15 membered heteroaryl optionally substituted by 1-15 R$^{99}$, 6-21 membered heteroarylalkyl optionally substituted by 1-27 R$^{99}$, halogen, —CN, —C(=O)R$^{90}$, —C(=O)OR$^{90}$, —C(=O)NR$^{92}$R$^{93}$, —C(=O)C(=O)R$^{90}$, —C(=S)NR$^{92}$R$^{93}$, —NC, —NO$_2$, —NR$^{92}$R$^{93}$, —NR$^{94}$NR$^{92}$R$^{93}$, —NR$^{94}$C(=O)R$^{90}$, —NR$^{94}$C(=O)C(=O)R$^{90}$, —NR$^{94}$C(=O)OR$^{91}$, —NR$^{94}$C(=O)C(=O)OR$^{91}$, —NR$^{94}$C(=O)NR$^{92}$R$^{93}$, —NR$^{94}$C(=O)NR$^{94}$C(=O)R$^{90}$, —NR$^{94}$C(=O)NR$^{94}$C(=O)OR$^{90}$, —NR$^{94}$C(=NR$^{95}$)NR$^{92}$R$^{93}$, —NR$^{94}$C(=O)C(=O)NR$^{92}$R$^{93}$, —NR$^{94}$C(=S)R$^{90}$, —NR$^{94}$C(=S)OR$^{90}$, —NR$^{94}$C(=S)NR$^{92}$R$^{93}$, —NR$^{94}$S(=O)$_2$R$^{91}$, —NR$^{94}$S(=O)$_2$NR$^{92}$R$^{93}$, —OR$^{90}$, =O, —OCN, —OC(=O)R$^{90}$, —OC(=O)NR$^{92}$R$^{93}$, —OC(=O)OR$^{90}$, —OS(=O)R$^{90}$, —OS(=O)$_2$R$^{90}$, —OS(=O)$_2$OR$^{90}$, —OS(=O)$_2$NR$^{92}$R$^{93}$, —SCN, =S, —S(=O)$_n$R$^{90}$, —S(=O)$_2$OR$^{90}$, —SO$_3$R$^{97}$, —S(=O)$_2$NR$^{92}$R$^{93}$, and —S(=O)NR$^{92}$R$^{93}$; and (c) any two of Z$^{21}$, Z$^{22}$, Z$^{23}$, Z$^{24}$, Z$^{25}$, Z$^{26}$ and Z$^{27}$ may together form a group of formula -A$^{31}$-A$^{32}$-A$^{33}$-, wherein A$^{31}$, A$^{32}$, and A$^{33}$ are independently chosen from —CZ$^{31}$Z$^{32}$—, —CZ$^{33}$Z$^{34}$CZ$^{35}$Z$^{36}$—, —C(=O)—, —NZ$^{37}$—, —S—, —S(=O)—, —S(=O)$_2$—, or —O— wherein:

(i) when any two of Z$^{31}$, Z$^{32}$, Z$^{33}$, Z$^{34}$, Z$^{35}$, Z$^{36}$ and Z$^{37}$ are located on adjacent atoms, they may together form a bond between the atoms, and (ii) any of any of Z$^{21}$, Z$^{22}$, Z$^{23}$, Z$^{24}$, Z$^{25}$, Z$^{26}$ and Z$^{27}$ may be independently chosen from H, C$_{1-6}$alkyl optionally substituted by 1-13 R$^{139}$, C$_{6-11}$ aryl optionally substituted by 1-7 R$^{139}$, C$_{7-16}$arylalkyl optionally substituted by 1-19 R$^{139}$, C$_{3-11}$cycloalkyl optionally substituted by 1-21 R$^{139}$, C$_{4-17}$cycloalkylalkyl optionally substituted by 1-32 R$^{139}$, 3-15 membered heterocycloalkyl optionally substituted by 1-28 R$^{139}$, 4-21 membered heterocycloalkylalkyl optionally substituted by 1-40 R$^{139}$, 5-15 membered heteroaryl optionally substituted by 1-15 R$^{139}$, 6-21 membered heteroarylalkyl optionally substituted by 1-27 R$^{139}$, halogen, —CN, —C(=O)R$^{130}$, —C(=O)OR$^{130}$, —C(=O)NR$^{132}$R$^{133}$, —C(=O)C(=O)R$^{130}$, —C(=S)NR$^{132}$R$^{133}$, —NC, —NO$_2$, —NR$^{132}$R$^{133}$, —NR$^{134}$NR$^{132}$R$^{133}$, —NR$^{134}$C(=O)R$^{130}$, —NR$^{134}$C(=O)C(=O)R$^{130}$, —NR$^{134}$C(=O)OR$^{131}$, —NR$^{134}$C(=O)C(=O)OR$^{131}$, —NR$^{134}$C(=O)NR$^{132}$R$^{133}$, —NR$^{134}$C(=O)NR$^{134}$C(=O)R$^{130}$, —NR$^{134}$C(=O)NR$^{134}$C(=O)OR$^{130}$, —NR$^{134}$C(=NR$^{135}$)NR$^{132}$R$^{133}$, —NR$^{134}$C(=O)C(=O)NR$^{132}$R$^{133}$, —NR$^{134}$C(=S)R$^{130}$, —NR$^{134}$C(=S)OR$^{130}$, —NR$^{134}$C(=S)NR$^{132}$R$^{133}$, —NR$^{134}$S(=O)$_2$R$^{131}$, —NR$^{134}$S(=O)$_2$NR$^{132}$R$^{133}$, —OR$^{130}$, =O, —OCN, —OC(=O)R$^{130}$, —OC(=O)NR$^{132}$R$^{133}$, —OC(=O)OR$^{130}$, —OS(=O)R$^{130}$, —OS(=O)$_2$R$^{130}$, —OS(=O)$_2$OR$^{130}$, —OS(=O)$_2$NR$^{132}$R$^{133}$, —SCN, =S, —S(=O)$_n$R$^{130}$, —S(=O)$_2$OR$^{130}$, —SO$_3$R$^{137}$, —S(=O)$_2$NR$^{132}$R$^{133}$, and —S(=O)NR$^{132}$R$^{133}$;

$R^9$, $R^{19}$, $R^{29}$, $R^{39}$, $R^{49}$, $R^{59}$, $R^{69}$, $R^{79}$, $R^{89}$, $R^{99}$, and $R^{139}$ at each occurrence is independently chosen from $C_{1-6}$alkyl optionally substituted by 1-13 $R^{179}$, $C_{6-11}$ aryl optionally substituted by 1-7 $R^{179}$, $C_{7-16}$arylalkyl optionally substituted by 1-19 $R^{179}$, $C_{3-11}$cycloalkyl optionally substituted by 1-21 $R^{179}$, $C_{4-17}$cycloalkylalkyl optionally substituted by 1-32 $R^{179}$, 3-15 membered heterocycloalkyl optionally substituted by 1-28 $R^{179}$, 4-21 membered heterocycloalkylalkyl optionally substituted by 1-40 $R^{179}$, 5-15 membered heteroaryl optionally substituted by 1-15 $R^{179}$, 6-21 membered heteroarylalkyl optionally substituted by 1-27 $R^{179}$, halogen, —CN, —C(=O)$R^{170}$, —C(=O)O$R^{170}$, —C(=O)N$R^{172}R^{173}$, —C(=O)C(=O)$R^{170}$, —C(=S)N$R^{172}R^{173}$, —NC, —NO$_2$, —N$R^{172}R^{173}$, —N$R^{174}$N$R^{172}R^{173}$, —N$R^{174}$C(=O)$R^{170}$, —N$R^{174}$C(=O)C(=O)$R^{170}$, —N$R^{174}$C(=O)O$R^{171}$, —N$R^{174}$C(=O)C(=O)$R^{171}$, —N$R^{174}$C(=O)N$R^{172}R^{173}$, —N$R^{174}$C(=O)N$R^{174}$C(=O)$R^{170}$, —N$R^{174}$C(=O)N$R^{174}$C(=O)O$R^{170}$, —N$R^{174}$C(=N$R^{175}$)N$R^{172}R^{173}$, —N$R^{174}$C(=O)C(=O)N$R^{172}R^{173}$, —N$R^{174}$C(=S)$R^{170}$, —N$R^{174}$C(=S)O$R^{170}$, —N$R^{174}$C(=S)N$R^{172}R^{173}$, —N$R^{174}$S(=O)$_2R^{171}$, —N$R^{174}$S(=O)$_2$N$R^{172}R^{173}$, —O$R^{170}$, =O, —OCN, —OC(=O)$R^{170}$, —OC(=O)N$R^{172}R^{173}$, —OC(=O)O$R^{170}$, —OS(=O)$R^{170}$, —OS(=O)$_2R^{170}$, —OS(=O)$_2$O$R^{170}$, —OS(=O)$_2$N$R^{172}R^{173}$, —SCN, =S, —S(=O)$_nR^{170}$, —S(=O)$_2$O$R^{170}$, —SO$_3R^{177}$, —S(=O)$_2$N$R^{172}R^{173}$, and —S(=O)N$R^{172}R^{173}$; $R^1$, $R^4$, $R^5$, $R^6$, $R^{10}$, $R^{11}$, $R^{14}$, $R^{15}$, $R^{16}$, $R^{17}$, $R^{21}$, $R^{24}$, $R^{25}$, $R^{26}$, $R^{31}$, $R^{34}$, $R^{35}$, $R^{36}$, $R^{41}$, $R^{44}$, $R^{45}$, $R^{46}$, $R^{50}$, $R^{51}$, $R^{54}$, $R^{55}$, $R^{56}$, $R^{57}$, $R^{61}$, $R^{64}$, $R^{65}$, $R^{66}$, $R^{71}$, $R^{74}$, $R^{75}$, $R^{76}$, $R^{80}$, $R^{81}$, $R^{84}$, $R^{85}$, $R^{86}$, $R^{87}$, $R^{90}$, $R^{91}$, $R^{94}$, $R^{95}$, $R^{96}$, $R^{97}$, $R^{100}$, $R^{101}$, $R^{104}$, $R^{105}$, $R^{106}$, $R^{107}$, $R^{130}$, $R^{131}$, $R^{134}$, $R^{135}$, $R^{136}$, $R^{137}$, $R^{170}$, $R^{171}$, $R^{174}$, $R^{175}$, $R^{176}$ and $R^{177}$ at each occurrence is independently chosen from H, $C_{1-6}$alkyl optionally substituted by 1-13 $R^{189}$, $C_{6-11}$aryl optionally substituted by 1-7 $R^{189}$, $C_{7-16}$arylalkyl optionally substituted by 1-19 $R^{189}$, $C_{3-11}$cycloalkyl optionally substituted by 1-21 $R^{189}$, $C_{4-17}$cycloalkylalkyl optionally substituted by 1-32 $R^{189}$, 3-15 membered heterocycloalkyl optionally substituted by 1-28 $R^{189}$, 4-21 membered heterocycloalkylalkyl optionally substituted by 1-40 $R^{189}$, 5-15 membered heteroaryl optionally substituted by 1-15 $R^{189}$, and 6-21 membered heteroarylalkyl optionally substituted by 1-27 $R^{189}$; $R^2$, $R^3$, $R^{12}$, $R^{13}$, $R^{22}$, $R^{23}$, $R^{32}$, $R^{33}$, $R^{42}$, $R^{43}$, $R^{52}$, $R^{53}$, $R^{62}$, $R^{63}$, $R^{72}$, $R^{73}$, $R^{82}$, $R^{83}$, $R^{92}$, $R^{93}$, $R^{102}$, $R^{103}$, $R^{132}$, $R^{133}$, $R^{172}$ and $R^{173}$ at each occurrence is independently chosen from H, $C_{1-6}$alkyl optionally substituted by 1-13 $R^{199}$, $C_{6-11}$aryl optionally substituted by 1-7 $R^{199}$, $C_{7-16}$arylalkyl optionally substituted by 1-19 $R^{199}$, $C_{3-11}$cycloalkyl optionally substituted by 1-21 $R^{199}$, $C_{4-17}$cycloalkylalkyl optionally substituted by 1-32 $R^{199}$, 3-15 membered heterocycloalkyl optionally substituted by 1-28 $R^{199}$, 4-21 membered heterocycloalkylalkyl optionally substituted by 1-40 $R^{199}$, 5-15 membered heteroaryl optionally substituted by 1-15 $R^{199}$, and 6-21 membered heteroarylalkyl optionally substituted by 1-27 $R^{199}$; or any $R^2$ and $R^3$, $R^{12}$ and $R^{13}$, $R^{22}$ and $R^{23}$, $R^{32}$ and $R^{33}$, $R^{42}$ and $R^{43}$, $R^{52}$ and $R^{53}$, $R^{62}$ and $R^{63}$, $R^{72}$ and $R^{73}$, $R^{82}$ and $R^{83}$, $R^{92}$ and $R^{93}$, $R^{192}$ and $R^{103}$, $R^{132}$ and $R^{133}$, or $R^{172}$ and $R^{173}$ may form, together with the nitrogen atom to which they are attached, a 3-15 membered heterocycloalkyl optionally substituted by 1-28 $R^{209}$ or a 5-15 membered heteroaryl optionally substituted by 1-15 $R^{299}$; $R^{179}$, $R^{189}$, $R^{199}$ and $R^{209}$ at each occurrence is independently chosen from $C_{1-6}$alkyl optionally substituted by 1-13 $R^{219}$, $C_{6-11}$aryl optionally substituted by 1-7 $R^{219}$, $C_{7-16}$arylalkyl optionally substituted by 1-19 $R^{219}$, $C_{3-11}$cycloalkyl optionally substituted by 1-21 $R^{219}$, $C_{4-17}$cycloalkylalkyl optionally substituted by 1-32 $R^{219}$, 3-15 membered heterocycloalkyl optionally substituted by 1-28 $R^{219}$, 4-21 membered heterocycloalkylalkyl optionally substituted by 1-40 $R^{219}$, 5-15 membered heteroaryl optionally substituted by 1-15 $R^{219}$, 6-21 membered heteroarylalkyl optionally substituted by 1-27 $R^{219}$, halogen, —CN, —C(=O)$R^{210}$, —C(=O)O$R^{210}$, —C(=O)N$R^{212}R^{213}$, —C(=O)C(=O)$R^{210}$, —C(=S)N$R^{212}R^{213}$, —NC, —NO$_2$, —N$R^{212}R^{213}$, —N$R^{214}$N$R^{212}R^{213}$, —N$R^{214}$C(=O)$R^{210}$, —N$R^{214}$C(=O)C(=O)$R^{210}$, —N$R^{214}$C(=O)O$R^{211}$, —N$R^{214}$C(=O)C(=O)O$R^{211}$, —N$R^{214}$C(=O)N$R^{212}R^{213}$, —N$R^{214}$C(=O)N$R^{214}$C(=O)$R^{210}$, —N$R^{214}$C(=O)N$R^{214}$C(=O)O$R^{210}$, —N$R^{214}$C(=N$R^{215}$)N$R^{212}R^{213}$, —N$R^{214}$C(=O)C(=O)N$R^{212}R^{213}$, —N$R^{214}$C(S)$R^{219}$, —N$R^{214}$C(S)O$R^{219}$, —N$R^{214}$C(=S)N$R^{212}R^{213}$, —N$R^{214}$S(=O)$_2R^{211}$, —N$R^{214}$S(=O)$_2$N$R^{212}R^{213}$, —O$R^{219}$, =O, —OCN, —OC(=O)$R^{210}$, —OC(=O)N$R^{212}R^{213}$, —OC(=O)O$R^{210}$, —OS(=O)$R^{210}$, —OS(=O)$_2R^{210}$, —OS(=O)$_2$O$R^{210}$, —OS(=O)$_2$N$R^{212}R^{213}$, —SCN, =S, —S(=O)$_nR^{210}$, —S(=O)$_2$O$R^{210}$, —SO$_3R^{217}$, —S(=O)$_2$N$R^{212}R^{213}$, and —S(=O)N$R^{212}R^{213}$; $R^{210}$, $R^{211}$, $R^{214}$, $R^{215}$, $R^{216}$ and $R^{217}$ at each occurrence is independently chosen from H, $C_{1-6}$alkyl optionally substituted by 1-13 $R^{229}$, $C_{6-11}$aryl optionally substituted by 1-7 $R^{229}$, $C_{4-16}$arylalkyl optionally substituted by 1-19 $R^{229}$, $C_{3-11}$cycloalkyl optionally substituted by 1-21 $R^{229}$, $C_{4-17}$cycloalkylalkyl optionally substituted by 1-32 $R^{229}$, 3-15 membered heterocycloalkyl optionally substituted by 1-28 $R^{229}$, 4-21 membered heterocycloalkylalkyl optionally substituted by 1-40 $R^{229}$, 5-15 membered heteroaryl optionally substituted by 1-15 $R^{229}$, and 6-21 membered heteroarylalkyl optionally substituted by 1-27 $R^{229}$; $R^{212}$ and $R^{213}$ at each occurrence is independently chosen from H, $C_{1-6}$alkyl optionally substituted by 1-13 $R^{239}$, $C_{6-11}$aryl optionally substituted by 1-7 $R^{239}$, $C_{7-16}$arylalkyl optionally substituted by 1-19 $R^{239}$, $C_{3-11}$cycloalkyl optionally substituted by 1-21 $R^{239}$, $C_{4-17}$cycloalkylalkyl optionally substituted by 1-32 $R^{239}$, 3-15 membered heterocycloalkyl optionally substituted by 1-28 $R^{239}$, 4-21 membered heterocycloalkylalkyl optionally substituted by 1-40 $R^{239}$, 5-15 membered heteroaryl optionally substituted by 1-15 $R^{239}$, and 6-21 membered heteroarylalkyl optionally substituted by 1-27 $R^{239}$; or any $R^{212}$ and $R^{213}$ may form, together with the nitrogen atom to which they are attached, a 3-15 membered heterocycloalkyl optionally substituted by 1-28 $R^{249}$ or a 5-15 membered heteroaryl optionally substituted by 1-15 $R^{249}$; $R^{219}$, $R^{229}$, $R^{239}$ and $R^{249}$ at each occurrence is independently chosen from $C_{1-6}$alkyl optionally substituted by 1-13 halogen, $C_{2-6}$alkenyl, $C_{2-6}$alkynyl, $C_{6-11}$ aryl, $C_{7-16}$arylalkyl, $C_{3-11}$cycloalkyl, $C_{4-17}$cycloalkylalkyl, 3-15 membered heterocycloalkyl, 4-21 membered heterocycloalkylalkyl, 5-15 membered heteroaryl, 6-21 membered heteroarylalkyl, halogen, —CN, —C(=O)$R^{250}$, —C(=O)O$R^{250}$, —C(=O)N$R^{250}R^{250}$, —C(=O)C(=O)$R^{250}$, —C(=S)N$R^{250}R^{250}$, —NC, —NO$_2$, —N$R^{250}R^{250}$, —N$R^{250}$N$R^{250}R^{250}$, —N$R^{250}$C(O)$R^{250}$, —N$R^{250}$C(=O)C(=O)$R^{250}$, —N$R^{250}$C(=O)O$R^{250}$, —N$R^{250}$C(=O)C(=O)O$R^{250}$, —N$R^{250}$C(=O)N$R^{250}R^{250}$, —N$R^{250}$C(=O)N$R^{250}$C(=O)N$R^{250}$, —N$R^{250}$C(=O)N$R^{250}$C(=O)O$R^{250}$, —N$R^{250}$C(=N$R^{250}$)N$R^{250}R^{250}$, —N$R^{250}$C(=O)C(=O)N$R^{250}R^{250}$, —N$R^{250}$C(=S)$R^{250}$, —N$R^{250}$C(=S)O$R^{250}$, —N$R^{250}$C(=S)N$R^{250}R^{250}$, —N$R^{250}$S(=O)$_2R^{250}$, —N$R^{250}$S(=O)$_2$N$R^{250}R^{250}$, —O$R^{250}$, =O, —OCN, —OC(=O)$R^{250}$, —OC(=O)N$R^{250}R^{250}$, —OC(=O)O$R^{250}$, —OS(=O)$R^{250}$, —OS(=O)$_2R^{250}$, —OS(=O)$_2$O$R^{250}$, —OS(=O)$_2$N$R^{250}R^{250}$, —SCN, =S, —S(=O)$_nR^{250}$, —S(=O)$_2$O$R^{250}$, —SO$_3R^{250}$, —S(=O)$_2$N$R^{250}R^{250}$, and —S(=O)N$R^{250}R^{250}$; $R^{250}$ at each occurrence is independently chosen from H, $C_{1-6}$alkyl and $C_{1-6}$-haloalkyl; and n at each occurrence is independently chosen from 0, 1, and 2; with the proviso that the compound is not:

(a)
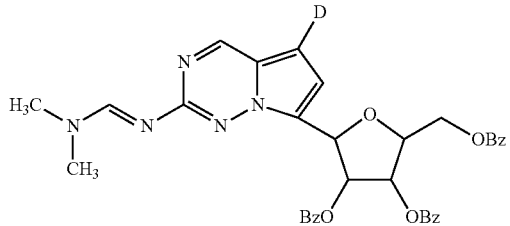

wherein
Bz is benzoyl, and
D is —C(=O)H or H, (b)
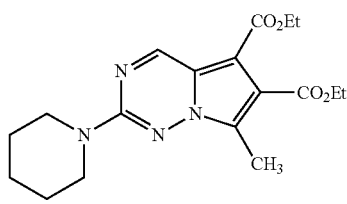

wherein Et is ethyl, or (c)
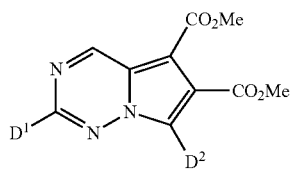

wherein
$D^1$ is methoxy, phenyl, or 4-methylphenyl,
$D^2$ is —$CH_2$C(=O)OMe or —C(=O)OMe, and
Me is methyl.

As another example, also included within the scope of the present invention are compounds of formula I and pharmaceutically acceptable salts thereof in which $Q^1$ is -$L^1$-$A^1$-$G^1$-$X^1$—$Z^1$; $Q^2$ is -$L^2$-$A^2$-$G^2$-$X^2$—$Z^2$; $Q^3$ is -$L^3$-$A^3$-$G^3$-$X^3$—$Z^3$; $Q^4$ is -$L^4$-$A^4$-$G^4$-$X^4$—$Z^4$; $L^1$ is $C_{1-6}$alkylene optionally substituted by 1-12 $R^9$, $C_{7-16}$arylalkylene optionally substituted by 1-18 $R^9$, $C_{3-11}$cycloalkylene optionally substituted by 1-20 $R^9$, $C_{4-17}$cycloalkylalkylene optionally substituted by 1-31 $R^9$, 3-15 membered heterocycloalkylene optionally substituted by 1-27 $R^9$, 4-21 membered heterocycloalkylalkylene optionally substituted by 1-39 $R^9$, 5-15 membered heteroarylene optionally substituted by 1-14 $R^9$, 6-21 membered heteroarylalkylene optionally substituted by 1-26 $R^9$, —$C_{0-3}$alkylC(=O)$C_{0-3}$alkyl-, —$C_{0-3}$alkylC(=O)O$C_{0-3}$alkyl-, —$C_{0-3}$alkylC(=O)$NR^4C_{0-3}$alkyl-, —$C_{0-3}$alkylC(=S)$NR^4C_{0-3}$alkyl-, —$C_{0-3}$alkyl$NR^4C_{0-3}$alkyl-, —$C_{0-3}$alkyl$NR^4NR^4C_{0-3}$alkyl-, —$C_{0-3}$alkyl$NR^4$C(=O)$C_{0-3}$alkyl-, —$C_{0-3}$alkyl$NR^4$C(=O)O$C_{0-3}$alkyl-, —$C_{0-3}$alkyl$NR^4$C(=O)$NR^4C_{0-3}$alkyl-, —$C_{0-3}$alkyl$NR^4$C(=O)$NR^4$C(=O)$C_{0-3}$alkyl-, —$C_{0-3}$alkyl$NR^4$C(=S)$C_{0-3}$alkyl-, —$C_{0-3}$alkyl$NR^4$C(=S)O$C_{0-3}$alkyl-, —$C_{0-3}$alkyl$NR^4$C(=S)$NR^4C_{0-3}$alkyl-, —$C_{0-3}$alkyl$NR^4$S(=O)$_2C_{0-3}$alkyl-, —$C_{0-3}$alkylO$C_{0-3}$alkyl-, —$C_{0-3}$alkylOC(=O)$C_{0-3}$alkyl-, —$C_{0-3}$alkylOC(=O)$NR^4C_{0-3}$alkyl-, —$C_{0-3}$alkylS(=O)—$C_{0-3}$alkyl-, —$C_{0-3}$alkylS(=O)$_2NR^4C_{0-3}$alkyl-, —$C_{0-3}$alkylS(=O)$NR^4C_{0-3}$alkyl-, or absent; $A^1$ is $C_{1-6}$alkylene optionally substituted by 1-12 $R^a$, $C_{6-11}$arylene optionally substituted by 1-6 $R^a$, $C_{7-16}$arylalkylene optionally substituted by 1-18 $R^a$, $C_{3-11}$cycloalkylene optionally substituted by 1-20 $R^a$, $C_{4-17}$cycloalkylalkylene optionally substituted by 1-31 $R^a$, 3-15 membered heterocycloalkylene optionally substituted by 1-27 $R^a$, 4-21 membered heterocycloalkylalkylene optionally substituted by 1-39 $R^a$, 5-15 membered heteroarylene optionally substituted by 1-14 $R^a$, or 6-21 membered heteroarylalkylene optionally substituted by 1-26 $R^a$, wherein each $R^a$ is independently chosen from $C_{1-6}$alkyl optionally substituted by 1-13 $R^{19}$, $C_{6-11}$aryl optionally substituted by 1-7 $R^{19}$, $C_{7-16}$arylalkyl optionally substituted by 1-19 $R^{19}$, $C_{3-11}$cycloalkyl optionally substituted by 1-21 $R^{19}$, $C_{4-17}$cycloalkylalkyl optionally substituted by 1-32 $R^{19}$, 3-15 membered heterocycloalkyl optionally substituted by 1-28 $R^{19}$, 4-21 membered heterocycloalkylalkyl optionally substituted by 1-40 $R^{19}$, 5-15 membered heteroaryl optionally substituted by 1-15 $R^{19}$, 6-21 membered heteroarylalkyl optionally substituted by 1-27 $R^{19}$, halogen, —CN, —C(=O)$R^{10}$, —C(=O)$OR^{10}$, —C(=O)$NR^{12}R^{13}$, —C(=S)$NR^{12}R^{13}$, —NC, —$NO_2$, —$NR^{12}R^{13}$, —$NR^{14}NR^{12}R^{13}$, —$NR^{14}OR^{16}$, —$NR^{14}$C(=O)$R^{10}$, —$NR^{14}$C(=O)$OR^{11}$, —$NR^{14}$C(=O)$NR^{12}R^{13}$, —$NR^{14}$C(=O)$NR^{14}$C(=O)$R^{10}$, —$NR^{14}$C(=O)$NR^{14}$C(=O)$OR^{10}$, —$NR^{14}$C(=$NR^{15}$)$NR^{12}R^{13}$, —$NR^{14}$C(=S)$R^{10}$, —$NR^{14}$C(=S)$NR^{12}R^{13}$, —$NR^{14}$S(=O)$_2R^{11}$, —$OR^{10}$, =O, —OCN, —OC(=O)$R^{10}$, —OC(=O)$NR^{12}R^{13}$, —SCN, =S, —S(=O)$_nR^{10}$, and —S(=O)$_2NR^{12}R^{13}$; $G^1$ is $C_{1-6}$alkylene optionally substituted by 1-12 $R^{29}$, $C_{6-11}$arylene optionally substituted by 1-6 $R^{29}$, $C_{7-16}$arylalkylene optionally substituted by 1-18 $R^{29}$, $C_{3-11}$cycloalkylene optionally substituted by 1-20 $R^{29}$, $C_{4-17}$cycloalkylalkylene optionally substituted by 1-31 $R^{29}$, 3-15 membered heterocycloalkylene optionally substituted by 1-27 $R^{29}$, 4-21 membered heterocycloalkylalkylene optionally substituted by 1-39 $R^{29}$, 5-15 membered heteroarylene optionally substituted by 1-14 $R^{29}$, 6-21 membered heteroarylalkylene optionally substituted by 1-26 $R^{29}$, —$C_{0-3}$alkylC(=O)$C_{0-3}$alkyl-, —$C_{0-3}$alkylC(=O)O$C_{0-3}$alkyl-, —$C_{0-3}$alkylC(=O)$NR^{24}C_{0-3}$alkyl-, —$C_{0-3}$alkylC(=S)$NR^{24}C_{0-3}$alkyl-, —$C_{0-3}$alkyl$NR^{24}C_{0-3}$alkyl-, —$C_{0-3}$alkyl$NR^{24}NR^{24}C_{0-3}$alkyl-, —$C_{0-3}$alkyl$NR^{24}$C(=O)$C_{0-3}$alkyl-, —$C_{0-3}$alkyl$NR^{24}$C(=O)O$C_{0-3}$alkyl-, —$C_{0-3}$alkyl$NR^{24}$C(=O)$NR^{24}C_{0-3}$alkyl-, —$C_{0-3}$alkyl$NR^{24}$C(=O)$NR^{24}$C(=O)$C_{0-3}$alkyl-, —$C_{0-3}$alkyl$NR^{24}$C(=O)$NR^{24}$C(=O)O$C_{0-3}$alkyl-, —$C_{0-3}$alkyl$NR^{24}$C(=S)$C_{0-3}$alkyl-, —$C_{0-3}$alkyl$NR^{24}$C(=S)$NR^{24}C_{0-3}$alkyl-, —$C_{0-3}$alkyl$NR^{24}$S(=O)$_2C_{0-3}$alkyl-, —$C_{0-3}$alkylO$C_{0-3}$alkyl-, —$C_{0-3}$alkylOC(=O)$C_{0-3}$alkyl-, —$C_{0-3}$alkylOC(=O)$NR^{24}C_{0-3}$alkyl-, —$C_{0-3}$alkylS(=O)—$C_{0-3}$alkyl-, —$C_{0-3}$alkylS(=O)$_2NR^{24}C_{0-3}$alkyl-, or absent; $X^1$ is $C_{1-6}$alkylene optionally substituted by 1-12 $R^{39}$, $C_{6-11}$arylene optionally substituted by 1-6 $R^{39}$, $C_{7-16}$arylalkylene optionally substituted by 1-18 $R^{39}$, $C_{3-11}$cycloalkylene optionally substituted by 1-20 $R^{39}$, $C_{4-17}$cycloalkylalkylene optionally substituted by 1-31 $R^{39}$, 3-15 membered heterocycloalkylene optionally substituted by 1-27 $R^{39}$, 4-21 membered heterocycloalkylalkylene optionally substituted by 1-39 $R^{39}$, 5-15 membered heteroarylene optionally substituted by 1-14 $R^{39}$, 6-21 membered heteroarylalkylene optionally substituted by 1-26 $R^{39}$, —$C_{0-3}$alkylC(=O)$C_{0-3}$alkyl-, —$C_{0-3}$alkylC(=O)O$C_{0-3}$alkyl-, —$C_{0-3}$alkylC(=O)$NR^{34}C_{0-3}$alkyl-, —$C_{0-3}$alkylC(=S)$NR^{34}C_{0-3}$alkyl-, —$C_{0-3}$alkyl$NR^{34}C_{0-3}$alkyl-, —$C_{0-3}$alkyl$NR^{34}NR^{34}C_{0-3}$alkyl-, —$C_{0-3}$alkyl$NR^{34}$C(=O)$C_{0-3}$alkyl-, —$C_{0-3}$alkyl$NR^{34}$C(=O)O$C_{0-3}$alkyl-, —$C_{0-3}$ alkylNR$^{34}$C(=O)NR$^{34}$C$_{0-3}$alkyl-, —C$_{0-3}$alkylNR$^{34}$C(=O)NR$^{34}$C(=O)C$_{0-3}$alkyl-, —C$_{0-3}$alkylNR$^{34}$C(=O)NR$^{34}$C(=O)OC$_{0-3}$alkyl-, —C$_{0-3}$alkylNR$^{34}$C(=NR$^{35}$)NR$^{34}$C$_{0-3}$alkyl-, —C$_{0-3}$alkylNR$^{34}$C(=S)NR$^{34}$C$_{0-3}$alkyl-, —C$_{0-3}$alkylNR$^{34}$S(=O)$_2$C$_{0-3}$alkyl-, —C$_{0-3}$alkylOC$_{0-3}$alkyl-, —C$_{0-3}$alkylOC(=O)C$_{0-3}$alkyl-, —C$_{0-3}$alkylOC(=O)NR$^{34}$C$_{0-3}$alkyl-, —C$_{0-3}$alkylS(=O)—C$_{0-3}$alkyl-, —C$_{0-3}$alkylS(=O)$_2$NR$^{34}$C$_{0-3}$alkyl-, or absent; Z$^1$ is H, C$_{1-6}$alkyl optionally substituted by 1-13 R$^{49}$, C$_{7-16}$arylalkyl optionally substituted by 1-19 R$^{49}$, C$_{3-11}$cycloalkyl optionally substituted by 1-21 R$^{49}$, C$_{4-17}$cycloalkylalkyl optionally substituted by 1-32 R$^{49}$, 3-15 membered heterocycloalkyl optionally substituted by 1-28 R$^{49}$, 4-21 membered heterocycloalkylalkyl optionally substituted by 1-40 R$^{49}$, 5-15 membered heteroaryl optionally substituted by 1-15 R$^{49}$, 6-21 membered heteroarylalkyl optionally substituted by 1-27 R$^{49}$, halogen, —CN, —C(=O)R$^{100}$, —C(=O)OR$^{100}$, —C(=O)NR$^{102}$R$^{103}$, —C(=S)NR$^{102}$R$^{103}$, —NC, —NO$_2$, —NR$^{102}$R$^{103}$, —NR$^{104}$NR$^{102}$R$^{103}$, NR$^{104}$C(=O)R$^{100}$, —NR$^{104}$C(=O)OR$^{101}$, —NR$^{104}$C(=O)NR$^{102}$R$^{103}$, —NR$^{104}$C(=O)NR$^{104}$C(=O)R$^{100}$, —NR$^{104}$C(=NR$^{105}$)NR$^{102}$R$^{103}$, —NR$^{104}$C(=S)R$^{100}$, —NR$^{104}$C(=S)NR$^{102}$R$^{103}$, —NR$^{104}$S(=O)$_2$R$^{101}$, —OR$^{100}$, =O, —OCN, —OC(=O)R$^{100}$, —OC(=O)NR$^{102}$R$^{103}$, —SCN, =S, —S(=O)$_n$R$^{100}$, or —S(=O)$_2$NR$^{102}$R$^{103}$; L$^2$, L$^3$, and L$^4$ are independently present or absent, and if present each is independently chosen from —C$_{0-3}$alkylC(=O)C$_{0-3}$alkyl-, —C$_{0-3}$alkylC(=O)OC$_{0-3}$alkyl-, —C$_{0-3}$alkylC(=O)NR$^{44}$C$_{0-3}$alkyl-, —C$_{0-3}$alkylC(=S)NR$^{44}$C$_{0-3}$alkyl-, —C$_{0-3}$alkylNR$^{44}$C$_{0-3}$alkyl-, —C$_{0-3}$alkylNR$^{44}$NR$^{44}$C$_{0-3}$alkyl-, —C$_{0-3}$alkylNR$^{44}$C(=O)C$_{0-3}$alkyl-, —C$_{0-3}$alkylNR$^{44}$C(=O)OC$_{0-3}$alkyl-, —C$_{0-3}$alkylNR$^{44}$C(=O)NR$^{44}$C$_{0-3}$alkyl-, —C$_{0-3}$alkylNR$^{44}$C(=O)NR$^{44}$C(=O)C$_{0-3}$alkyl-, —C$_{0-3}$alkylNR$^{44}$C(=O)NR$^{44}$C(=O)OC$_{0-3}$alkyl-, —C$_{0-3}$alkylNR$^{44}$C(=NR$^{45}$)NR$^{44}$C$_{0-3}$alkyl-, —C$_{0-3}$alkylNR$^{44}$C(=S)NR$^{44}$C$_{0-3}$alkyl-, —C$_{0-3}$alkylNR$^{44}$S(=O)$_2$C$_{0-3}$alkyl-, —C$_{0-3}$alkylOC$_{0-3}$alkyl-, —C$_{0-3}$alkylOC(=O)C$_{0-3}$alkyl-, —C$_{0-3}$alkylOC(=O)NR$^{44}$C$_{0-3}$alkyl-, —C$_{0-3}$alkylS(=O)—C$_{0-3}$alkyl-, and —C$_{0-3}$alkylS(=O)$_2$NR$^{44}$C$_{0-3}$alkyl-; A$^2$, A$^3$, and A$^4$ are independently present or absent, and if present each is independently chosen from C$_{1-6}$alkylene optionally substituted by 1-12 R$^b$, C$_{6-11}$ arylene optionally substituted by 1-6 R$^b$, —C$_{7-16}$arylalkylene optionally substituted by 1-18 R$^b$, C$_{3-11}$ cycloalkylene optionally substituted by 1-20 R$^b$, C$_{4-17}$cycloalkylalkylene optionally substituted by 1-31 R$^b$, 3-15 membered heterocycloalkylene optionally substituted by 1-27 R$^b$, 4-21 membered heterocycloalkylalkylene optionally substituted by 1-39 R$^b$, 5-15 membered heteroarylene optionally substituted by 1-14 R$^b$, or 6-21 membered heteroarylalkylene optionally substituted by 1-26 R$^b$; wherein each R$^b$ is independently chosen from C$_{1-6}$alkyl optionally substituted by 1-13 R$^{59}$, C$_{2-6}$alkenyl optionally substituted by 1-11 R$^{59}$, C$_{2-6}$alkynyl optionally substituted by 1-9 R$^{59}$, C$_{6-11}$aryl optionally substituted by 1-7 R$^{59}$, C$_{7-16}$arylalkyl optionally substituted by 1-19 R$^{59}$, C$_{3-11}$cycloalkyl optionally substituted by 1-21 R$^{59}$, C$_{4-6}$cycloalkylalkyl optionally substituted by 1-32 R$^{59}$, 3-15 membered heterocycloalkyl optionally substituted by 1-28 R$^{59}$, 4-21 membered heterocycloalkylalkyl optionally substituted by 1-40 R$^{59}$, 5-15 membered heteroaryl optionally substituted by 1-15 R$^{59}$, 6-21 membered heteroarylalkyl optionally substituted by 1-27 R$^{59}$, halogen, —CN, —C(=O)R$^{50}$, —C(=O)OR$^{50}$, —C(=O)NR$^{52}$R$^{53}$, —C(=S)NR$^{52}$R$^{53}$, —NC, —NO$_2$, —NR$^{52}$R$^{53}$, —NR$^{54}$NR$^{52}$R$^{53}$, —NR$^{54}$C(=O)R$^{50}$, —NR$^{54}$C(=O)OR$^{51}$, —NR$^{54}$C(=O)NR$^{52}$R$^{53}$, —NR$^{54}$C(=O)NR$^{54}$C(=O)R$^{50}$, —NR$^{54}$C(=O)NR$^{54}$C(=O)OR$^{50}$, —NR$^{54}$C(=NR$^{55}$)NR$^{52}$R$^{53}$, —NR$^{54}$C(=S)NR$^{52}$R$^{53}$, —NR$^{54}$S(=O)$_2$R$^{51}$, —OR$^{50}$, =O, —OCN, —OC(=O)R$^{50}$, —OC(=O)NR$^{52}$R$^{53}$, —SCN, =S, —S(=O)$_n$R$^{50}$, and —S(=O)$_2$NR$^{52}$R$^{53}$; G$^2$, G$^3$, and G$^4$ are independently present or absent, and if present each is independently chosen from C$_{1-6}$alkylene optionally substituted by 1-12 R$^{69}$, C$_{6-11}$arylene optionally substituted by 1-6 R$^{69}$, C$_{7-16}$arylalkylene optionally substituted by 1-18 R$^{69}$, C$_{3-11}$cycloalkylene optionally substituted by 1-20 R$^{69}$, C$_{4-17}$cycloalkylalkylene optionally substituted by 1-31 R$^{69}$, 3-15 membered heterocycloalkylene optionally substituted by 1-27 R$^{69}$, 4-21 membered heterocycloalkylalkylene optionally substituted by 1-39 R$^{69}$, 5-15 membered heteroarylene optionally substituted by 1-14 R$^{69}$, 6-21 membered heteroarylalkylene optionally substituted by 1-26 R$^{69}$, —C$_{0-3}$alkylC(=O)C$_{0-3}$alkyl-, —C$_{0-3}$alkylC(=O)OC$_{0-3}$alkyl-, —C$_{0-3}$alkylC(=O)NR$^{64}$C$_{0-3}$alkyl-, —C$_{0-3}$alkylC(=S)NR$^{64}$C$_{0-3}$alkyl-, —C$_{0-3}$alkylNR$^{64}$C$_{0-3}$alkyl-, —C$_{0-3}$alkylNR$^{64}$NR$^{64}$C$_{0-3}$alkyl-, —C$_{0-3}$alkylNR$^{64}$C(=O)C$_{0-3}$alkyl-, —C$_{0-3}$alkylNR$^{64}$C(=O)OC$_{0-3}$alkyl-, —C$_{0-3}$alkylNR$^{64}$C(=O)NR$^{64}$C$_{0-3}$alkyl-, —C$_{0-3}$alkylNR$^{64}$C(=O)NR$^{64}$C(=O)C$_{0-3}$alkyl-, —C$_{0-3}$alkylNR$^{64}$C(=NR$^{65}$)NR$^{64}$C$_{0-3}$alkyl-, —C$_{0-3}$alkylNR$^{64}$C(=S)C$_{0-3}$alkyl-, —C$_{0-3}$alkylNR$^{64}$C(=S)NR$^{64}$C$_{0-3}$alkyl-, —C$_{0-3}$alkylNR$^{64}$S(=O)$_2$C$_{0-3}$alkyl-, —C$_{0-3}$alkylOC$_{0-3}$alkyl-, —C$_{0-3}$alkylOC(=O)C$_{0-3}$alkyl-, —C$_{0-3}$alkylOC(=O)NR$^{64}$C$_{0-3}$alkyl-, —C$_{0-3}$alkylS(=O)—C$_{0-3}$alkyl-, and —C$_{0-3}$alkylS(=O)$_2$NR$^{64}$C$_{0-3}$alkyl-; X$^2$, X$^3$, and X$^4$ are independently present or absent, and if present each is independently chosen from C$_{1-6}$alkylene optionally substituted by 1-12 R$^{79}$, C$_{6-11}$arylene optionally substituted by 1-6 R$^{79}$, C$_{7-16}$arylalkylene optionally substituted by 1-18 R$^{79}$, C$_{3-11}$cycloalkylene optionally substituted by 1-20 R$^{79}$, C$_{4-17}$cycloalkylalkylene optionally substituted by 1-31 R$^{79}$, 3-15 membered heterocycloalkylene optionally substituted by 1-27 R$^{79}$, 4-21 membered heterocycloalkylalkylene optionally substituted by 1-39 R$^{79}$, 5-15 membered heteroarylene optionally substituted by 1-14 R$^{79}$, 6-21 membered heteroarylalkylene optionally substituted by 1-26 R$^{79}$, —C$_{0-3}$alkylC(=O)C$_{0-3}$alkyl-, —C$_{0-3}$alkylC(=O)OC$_{0-3}$alkyl-, —C$_{0-3}$alkylC(=O)NR$^{74}$C$_{0-3}$alkyl-, —C$_{0-3}$alkylC(=S)NR$^{74}$C$_{0-3}$alkyl-, —C$_{0-3}$alkylNR$^{74}$C$_{0-3}$alkyl-, —C$_{0-3}$alkylNR$^{74}$NR$^{74}$C$_{0-3}$alkyl-, —C$_{0-3}$alkylNR$^{74}$C(=O)C$_{0-3}$alkyl-, —C$_{0-3}$alkylNR$^{74}$C(=O)OC$_{0-3}$alkyl-, —C$_{0-3}$alkylNR$^{74}$C(=O)NR$^{74}$C$_{0-3}$alkyl-, —C$_{0-3}$alkylNR$^{74}$C(=O)NR$^{74}$C(=O)NR$^{74}$C(=O)C$_{0-3}$alkyl-, —C$_{0-3}$alkylNR$^{74}$C(=O)NR$^{74}$C(=O)OC$_{0-3}$alkyl-, —C$_{0-3}$alkylNR$^{74}$C(=NR$^{75}$)NR$^{74}$C$_{0-3}$alkyl-, —C$_{0-3}$alkylNR$^{74}$C(=S)C$_{0-3}$alkyl-, —C$_{0-3}$alkylNR$^{74}$C(=S)NR$^{74}$C$_{0-3}$alkyl-, —C$_{0-3}$alkylNR$^{74}$S(=O)$_2$C$_{0-3}$alkyl-, —C$_{0-3}$alkylOC$_{0-3}$alkyl-, —C$_{0-3}$alkylOC(=O)C$_{0-3}$alkyl-, —C$_{0-3}$alkylOC(=O)NR$^{74}$C$_{0-3}$alkyl-, —C$_{0-3}$alkylS(=O)—C$_{0-3}$alkyl-, and —C$_{0-3}$alkylS(=O)$_2$NR$^{74}$C$_{0-3}$alkyl-; Z$^2$, Z$^3$, and Z$^4$ are independently chosen from H, C$_{1-6}$alkyl optionally substituted by 1-13 R$^{89}$, C$_{6-11}$aryl optionally substituted by 1-7 R$^{89}$, C$_{7-16}$arylalkyl optionally substituted by 1-19 R$^{89}$, C$_{3-11}$cycloalkyl optionally substituted by 1-21 R$^{89}$, C$_{4-17}$cycloalkylalkyl optionally substituted by 1-32 R$^{89}$, 3-15 membered heterocycloalkyl optionally substituted by 1-28 R$^{89}$, 4-21 membered heterocycloalkylalkyl optionally substituted by 1-40 R$^{89}$, 5-15 membered heteroaryl optionally substituted by 1-15 R$^{89}$, 6-21 membered heteroarylalkyl optionally substituted by 1-27 R$^{89}$, halogen, —CN, —C(=O)R$^{80}$, —C(=O)OR$^{80}$, —C(=O)NR$^{82}$R$^{83}$, —C(=S)NR$^{82}$R$^{83}$, —NC, —NO$_2$, —NR$^{82}$R$^{83}$, —NR$^{84}$NR$^{82}$R$^{83}$, —NR$^{84}$C(=O)R$^{80}$, —NR$^{84}$C(=O)OR$^{81}$, —NR$^{84}$C(=O)NR$^{82}$R$^{83}$, —NR$^{84}$C(=O)NR$^{84}$C(=O)R$^{80}$, —NR$^{84}$C(=O)NR$^{84}$C(=O)OR$^{80}$, —NR$^{84}$C(=NR$^{85}$)NR$^{82}$R$^{83}$, —NR$^{84}$C(=S)R$^{80}$, —NR$^{84}$C(=S)NR$^{82}$R$^{83}$, —NR$^{84}$S(=O)$_2$R$^{81}$, —OR$^{80}$, =O, —OCN, —OC(=O)R$^{80}$, —OC(=O)NR$^{82}$R$^{83}$, —SCN, =S, —S(=O)$_n$R$^{80}$, —S(=O)$_2$OR$^{80}$, and —S(=O)$_2$NR$^{82}$R$^{83}$; alternatively, when L$^2$, A$^2$, G$^2$, X$^2$, L$^3$, A$^3$, G$^3$ and X$^3$ are absent, Z$^2$ and Z$^3$ can together form a group of formula -A$^{21}$-A$^{22}$-A$^{23}$-, or when L$^3$, A$^3$, G$^3$, X$^3$, L$^4$, A$^4$, G$^4$ and X$^4$ are absent, Z$^3$ and Z$^4$ can together form a group of formula -A$^{21}$-A$^{22}$-A$^{23}$-; wherein A$^{21}$, A$^{22}$, and A$^{23}$ are independently chosen from —CZ$^{21}$Z$^{22}$—, —CZ$^{23}$Z$^{24}$CZ$^{25}$Z$^{26}$—, —C(=O)—, —NZ$^{27}$—, —S—, —S(=O)—, —S(=O)$_2$—, or —O—; wherein:

(a) when any two of Z$^{21}$, Z$^{22}$, Z$^{23}$, Z$^{24}$, Z$^{25}$, Z$^{26}$ and Z$^{27}$ are located on adjacent atoms, they may together form a bond between the atoms, and (b) any of Z$^{21}$, Z$^{22}$, Z$^{23}$, Z$^{24}$, Z$^{25}$, Z$^{26}$ and Z$^{27}$ may be independently chosen from H, C$_{1-6}$alkyl optionally substituted by 1-13 R$^{99}$, C$_{6-11}$ aryl optionally substituted by 1-7 R$^{99}$, C$_{7-16}$arylalkyl optionally substituted by 1-19 R$^{99}$, C$_{3-11}$cycloalkyl optionally substituted by 1-21 R$^{99}$, C$_{4-17}$cycloalkylalkyl optionally substituted by 1-32 R$^{99}$, 3-15 membered heterocycloalkyl optionally substituted by 1-28 R$^{99}$, 4-21 membered heterocycloalkylalkyl optionally substituted by 1-40 R$^{99}$, 5-15 membered heteroaryl optionally substituted by 1-15 R$^{99}$, 6-21 membered heteroarylalkyl optionally substituted by 1-27 R$^{99}$, halogen, —CN, —C(=O)R$^{90}$, —C(=O)OR$^{90}$, —C(=O)NR$^{92}$R$^{93}$, —C(=S)NR$^{92}$R$^{93}$, —NC, —NO$_2$, —NR$^{92}$R$^{93}$, —NR$^{94}$NR$^{92}$R$^{93}$, —NR$^{94}$C(=O)R$^{90}$, —NR$^{94}$C(=O)OR$^{91}$, —NR$^{94}$C(=O)NR$^{92}$R$^{93}$, —NR$^{94}$C(=O)NR$^{94}$C(=O)R$^{90}$, —NR$^{94}$C(=O)NR$^{94}$C(=O)OR$^{90}$, —NR$^{94}$C(=NR$^{95}$)NR$^{92}$R$^{93}$, —NR$^{94}$C(=S)R$^{90}$, —NR$^{94}$C(=S)NR$^{92}$R$^{93}$, —NR$^{94}$S(=O)$_2$R$^{91}$, —OR$^{90}$, =O, —OCN, —OC(=O)NR$^{92}$R$^{93}$, —SCN, =S, —S(=O)$_n$R$^{90}$, and —S(=O)$_2$NR$^{92}$R$^{93}$; and (c) any two of Z$^{21}$, Z$^{22}$, Z$^{23}$, Z$^{24}$, Z$^{25}$, Z$^{26}$ and Z$^{27}$ may together form a group of formula -A$^{31}$-A$^{32}$-A$^{33}$-, wherein A$^{31}$, A$^{32}$, and A$^{33}$ are independently chosen from —CZ$^{31}$Z$^{32}$—, —CZ$^{33}$Z$^{34}$CZ$^{35}$Z$^{36}$—, —C(=O)—, —NZ$^{37}$—, —S—, —S(=O)—, —S(=O)$_2$—, or —O— wherein:

(i) when any two of Z$^{31}$, Z$^{32}$, Z$^{33}$, Z$^{34}$, Z$^{35}$, Z$^{36}$ and Z$^{37}$ are located on adjacent atoms, they may together form a bond between the atoms, and (ii) any of any of Z$^{21}$, Z$^{22}$, Z$^{23}$, Z$^{24}$, Z$^{25}$, Z$^{26}$ and Z$^{27}$ may be independently chosen from H, C$_{1-6}$alkyl optionally substituted by 1-13 R$^{139}$, C$_{6-11}$ aryl optionally substituted by 1-7 R$^{139}$, C$_{7-16}$arylalkyl optionally substituted by 1-19 R$^{139}$, C$_{3-11}$cycloalkyl optionally substituted by 1-21 R$^{139}$, C$_{4-17}$cycloalkylalkyl optionally substituted by 1-32 R$^{139}$, 3-15 membered heterocycloalkyl optionally substituted by 1-28 R$^{139}$, 4-21 membered heterocycloalkylalkyl optionally substituted by 1-40 R$^{139}$, 5-15 membered heteroaryl optionally substituted by 1-15 R$^{139}$, 6-21 membered heteroarylalkyl optionally substituted by 1-27 R$^{139}$, halogen, —CN, —C(=O)R$^{130}$, —C(=O)OR$^{130}$, —C(=O)NR$^{132}$R$^{133}$, —C(=S)NR$^{132}$R$^{133}$, —NC, —NO$_2$, —NR$^{132}$R$^{133}$, —NR$^{134}$NR$^{132}$R$^{133}$, —NR$^{134}$C(=O)R$^{130}$, —NR$^{134}$C(=O)OR$^{131}$, —NR$^{134}$C(=O)NR$^{132}$R$^{133}$, —NR$^{134}$C(=O)NR$^{134}$C(=O)R$^{130}$, —NR$^{134}$C(=NR$^{135}$)NR$^{132}$R$^{133}$, —NR$^{134}$C(=S)R$^{130}$, —NR$^{134}$C(=S)NR$^{132}$R$^{133}$, —NR$^{134}$S(=O)$_2$R$^{131}$, —OR$^{130}$, =O, —OCN, —OC(=O)R$^{130}$, —OC(=O)NR$^{132}$R$^{133}$, —SCN, =S, —S(=O)$_n$R$^{130}$, and —S(=O)$_2$NR$^{132}$R$^{133}$; R$^9$, R$^{19}$, R$^{29}$, R$^{39}$, R$^{49}$, R$^{59}$, R$^{69}$, R$^{79}$, R$^{89}$, R$^{99}$, and R$^{139}$ at each occurrence is independently chosen from C$_{1-6}$alkyl optionally substituted by 1-13 R$^{179}$, C$_{6-11}$aryl optionally substituted by 1-7 R$^{179}$, C$_{7-16}$arylalkyl optionally substituted by 1-19 R$^{179}$, C$_{3-11}$cycloalkyl optionally substituted by 1-21 R$^{179}$, C$_{4-17}$cycloalkylalkyl optionally substituted by 1-32 R$^{179}$, 3-15 membered heterocycloalkyl optionally substituted by 1-28 R$^{179}$, 4-21 membered heterocycloalkylalkyl optionally substituted by 1-40 R$^{179}$, 5-15 membered heteroaryl optionally substituted by 1-15 R$^{179}$, 6-21 membered heteroarylalkyl optionally substituted by 1-27 R$^{179}$, halogen, —CN, —C(=O)R$^{170}$, —C(=O)OR$^{170}$, —C(=O)NR$^{172}$R$^{173}$, —C(=O)C(=O)R$^{170}$, —C(=S)NR$^{172}$R$^{173}$, —NC, —NO$_2$, —NR$^{172}$R$^{173}$, —NR$^{174}$NR$^{172}$R$^{173}$, —NR$^{174}$C(=O)R$^{179}$, —NR$^{174}$C(=O)C(=O)R$^{179}$, —NR$^{174}$C(=O)OR$^{171}$, —NR$^{174}$C(=O)NR$^{172}$R$^{173}$, —NR$^{174}$C(=O)NR$^{174}$C(=O)R$^{179}$, —NR$^{174}$C(=NR$^{175}$)NR$^{172}$R$^{173}$, —NR$^{174}$C(=S)R$^{170}$, —NR$^{174}$C(=S)NR$^{172}$R$^{173}$, —NR$^{174}$S(=O)$_2$R$^{171}$, —OR$^{170}$, =O, —OCN, —OC(=O)R$^{170}$, —OC(=O)NR$^{172}$R$^{173}$, —OS(=O)$_2$NR$^{172}$R$^{173}$, —SCN, =S, —S(=O)$_n$R$^{170}$, —SO$_3$R$^{177}$, and —S(=O)$_2$NR$^{172}$R$^{173}$; R$^1$, R$^4$, R$^5$, R$^6$, R$^{10}$, R$^{11}$, R$^{14}$, R$^{15}$, R$^{16}$, R$^{17}$, R$^{21}$, R$^{24}$, R$^{25}$, R$^{26}$, R$^{31}$, R$^{34}$, R$^{35}$, R$^{36}$, R$^{41}$, R$^{44}$, R$^{45}$, R$^{46}$, R$^{50}$, R$^{51}$, R$^{54}$, R$^{55}$, R$^{56}$, R$^{57}$, R$^{61}$, R$^{64}$, R$^{65}$, R$^{66}$, R$^{71}$, R$^{74}$, R$^{75}$, R$^{76}$, R$^{80}$, R$^{81}$, R$^{84}$, R$^{85}$, R$^{86}$, R$^{87}$, R$^{90}$, R$^{91}$, R$^{94}$, R$^{95}$, R$^{96}$, R$^{97}$, R$^{100}$, R$^{101}$, R$^{104}$, R$^{105}$, R$^{106}$, R$^{107}$, R$^{130}$, R$^{131}$, R$^{134}$, R$^{135}$, R$^{136}$, R$^{137}$, R$^{170}$, R$^{171}$, R$^{174}$, R$^{175}$, R$^{176}$ and R$^{177}$ at each occurrence is independently chosen from H, C$_{1-6}$alkyl optionally substituted by 1-13 R$^{189}$, C$_{6-11}$aryl optionally substituted by 1-7 R$^{189}$, C$_{7-16}$arylalkyl optionally substituted by 1-19 R$^{189}$, C$_{3-11}$cycloalkyl optionally substituted by 1-21 R$^{189}$, C$_{4-17}$cycloalkylalkyl optionally substituted by 1-32 R$^{189}$, 3-15 membered heterocycloalkyl optionally substituted by 1-28 R$^{189}$, 4-21 membered heterocycloalkylalkyl optionally substituted by 1-40 R$^{189}$, 5-15 membered heteroaryl optionally substituted by 1-15 R$^{189}$, and 6-21 membered heteroarylalkyl optionally substituted by 1-27 R$^{189}$; R$^2$, R$^3$, R$^{12}$, R$^{13}$, R$^{22}$, R$^{23}$, R$^{32}$, R$^{33}$, R$^{42}$, R$^{43}$, R$^{52}$, R$^{53}$, R$^{62}$, R$^{63}$, R$^{72}$, R$^{73}$, R$^{82}$, R$^{83}$, R$^{92}$, R$^{93}$, R$^{102}$, R$^{103}$, R$^{132}$, R$^{133}$, R$^{172}$, and R$^{173}$ at each occurrence is independently chosen from H, C$_{1-6}$alkyl optionally substituted by 1-13 R$^{199}$, C$_{6-11}$aryl optionally substituted by 1-7 R$^{199}$, C$_{7-16}$arylalkyl optionally substituted by 1-19 R$^{199}$, C$_{3-11}$cycloalkyl optionally substituted by 1-21 R$^{199}$, C$_{4-6}$cycloalkylalkyl optionally substituted by 1-32 R$^{199}$, 3-15 membered heterocycloalkyl optionally substituted by 1-28 R$^{199}$, 4-21 membered heterocycloalkylalkyl optionally substituted by 1-40 R$^{199}$, 5-15 membered heteroaryl optionally substituted by 1-15 R$^{199}$, and 6-21 membered heteroarylalkyl optionally substituted by 1-27 R$^{199}$; or any R$^2$ and R$^3$, R$^{12}$ and R$^{13}$, R$^{22}$ and R$^{23}$, R$^{32}$ and R$^{33}$, R$^{42}$ and R$^{43}$, R$^{52}$ and R$^{53}$, R$^{62}$ and R$^{63}$, R$^{72}$ and R$^{73}$, R$^{82}$ and R$^{83}$, R$^{92}$ and R$^{93}$, R$^{192}$ and R$^{103}$, R$^{132}$ and R$^{133}$, or R$^{172}$ and R$^{173}$ may form, together with the nitrogen atom to which they are attached, a 3-15 membered heterocycloalkyl optionally substituted by 1-28 R$^{209}$ or a 5-15 membered heteroaryl optionally substituted by 1-15 R$^{209}$; R$^{179}$, R$^{189}$, R$^{199}$ and R$^{209}$ at each occurrence is independently chosen from C$_{1-6}$alkyl optionally substituted by 1-13 R$^{219}$, C$_{6-11}$ aryl optionally substituted by 1-7 R$^{219}$, C$_{7-16}$arylalkyl optionally substituted by 1-19 R$^{219}$, C$_{3-11}$cycloalkyl optionally substituted by 1-21 R$^{219}$, C$_{4-17}$cycloalkylalkyl optionally substituted by 1-32 R$^{219}$, 3-15 membered heterocycloalkyl optionally substituted by 1-28 R$^{219}$, 4-21 membered heterocycloalkylalkyl optionally substituted by 1-40 R$^{219}$, 5-15 membered heteroaryl optionally substituted by 1-15 R$^{219}$, 6-21 membered heteroarylalkyl optionally substituted by 1-27 R$^{219}$, halogen, —CN, —C(=O)OR$^{210}$, —C(=O)OR$^{210}$, —C(=O)NR$^{212}$R$^{213}$, —C(=S)NR$^{212}$R$^{213}$, —NC, —NO$_2$, —NR$^{212}$R$^{213}$, —NR$^{214}$NR$^{212}$R$^{213}$; NR$^{214}$C(=O)R$^{210}$, —NR$^{214}$C(=O)OR$^{211}$, —NR$^{214}$C(=O)NR$^{212}$R$^{213}$, —NR$^{214}$C(=O)NR$^{212}$R$^{213}$, —R$^{214}$C(=O)NR$^{214}$C(=O)R$^{210}$, —NR$^{214}$C(=NR$^{215}$)NR$^{212}$R$^{213}$, —NR$^{214}$C(=S)R$^{210}$, —NR$^{214}$C(=S)NR$^{212}$R$^{213}$; —NR$^{214}$S(=O)$_2$R$^{211}$, —OR$^{210}$, =O, —OCN, —OC(=O)R$^{210}$, —OC(=O)

$NR^{212}R^{213}$, —OS(=O)$R^{210}$, —SCN, =S, —S(=O)$_n R^{210}$, and —S(=O)$_2 NR^{212}R^{213}$; $R^{210}$, $R^{211}$, $R^{214}$, $R^{215}$, $R^{216}$ and $R^{217}$ at each occurrence is independently chosen from H, $C_{1-6}$alkyl optionally substituted by 1-13 $R^{229}$, $C_{6-11}$aryl optionally substituted by 1-7 $R^{229}$, $C_{7-16}$arylalkyl optionally substituted by 1-19 $R^{229}$, $C_{3-11}$cycloalkyl optionally substituted by 1-21 $R^{229}$, $C_{4-17}$cycloalkylalkyl optionally substituted by 1-32 $R^{229}$, 3-15 membered heterocycloalkyl optionally substituted by 1-28 $R^{229}$, 4-21 membered heterocycloalkylalkyl optionally substituted by 1-40 $R^{229}$, 5-15 membered heteroaryl optionally substituted by 1-15 $R^{229}$, and 6-21 membered heteroarylalkyl optionally substituted by 1-27 $R^{229}$; $R^{212}$ and $R^{213}$ at each occurrence is independently chosen from H, $C_{1-6}$alkyl optionally substituted by 1-13 $R^{239}$, $C_{6-11}$aryl optionally substituted by 1-7 $R^{239}$, $C_{7-16}$arylalkyl optionally substituted by 1-19 $R^{239}$, $C_{3-11}$cycloalkyl optionally substituted by 1-21 $R^{239}$, $C_{4-17}$cycloalkylalkyl optionally substituted by 1-32 $R^{239}$, 3-15 membered heterocycloalkyl optionally substituted by 1-28 $R^{239}$, 4-21 membered heterocycloalkylalkyl optionally substituted by 1-40 $R^{239}$, 5-15 membered heteroaryl optionally substituted by 1-15 $R^{239}$, and 6-21 membered heteroarylalkyl optionally substituted by 1-27 $R^{239}$; or any $R^{212}$ and $R^{213}$ may form, together with the nitrogen atom to which they are attached, a 3-15 membered heterocycloalkyl optionally substituted by 1-28 $R^{249}$ or a 5-15 membered heteroaryl optionally substituted by 1-15 $R^{249}$; $R^{219}$, $R^{229}$, $R^{239}$ and $R^{249}$ at each occurrence is independently chosen from $C_{1-6}$alkyl optionally substituted by 1-13 halogen, $C_{2-6}$ alkenyl, $C_{2-6}$ alkynyl, $C_{6-11}$aryl, $C_{7-16}$arylalkyl, $C_{3-11}$cycloalkyl, $C_{4-17}$cycloalkylalkyl, 3-15 membered heterocycloalkyl, 4-21 membered heterocycloalkylalkyl, 5-15 membered heteroaryl, 6-21 membered heteroarylalkyl, halogen, —CN, —C(=O)$R^{250}$, —C(=O)O$R^{250}$, —C(=O)NR$^{250}$R$^{250}$, —C(=S)NR$^{250}$R$^{250}$, —NC, —NO$_2$, —NR$^{250}$R$^{250}$, —NR$^{250}$NR$^{250}$R$^{250}$, —NR$^{250}$C(O)OR$^{250}$, —NR$^{250}$C(=O)OR$^{250}$, —NR$^{250}$C(=O)NR$^{250}$C(=O)R$^{250}$, —NR$^{250}$C(=NR$^{250}$)NR$^{250}$R$^{250}$, —NR$^{250}$C(=S)R$^{250}$, —NR$^{250}$C(=S)NR$^{250}$R$^{250}$, —NR$^{250}$S(=O)$_2$R$^{250}$, —OR$^{250}$, =O, —OCN, —OC(=O)R$^{250}$, —OC(=O)NR$^{250}$R$^{250}$, —SCN, =S, —S(=O)$_n$R$^{250}$, and —S(=O)$_2$NR$^{250}$R$^{250}$; R$^{250}$ at each occurrence is independently chosen from H, $C_{1-6}$alkyl and $C_{1-6}$-haloalkyl; and n at each occurrence is independently chosen from 0, 1, and 2; with the proviso that the compound is not:

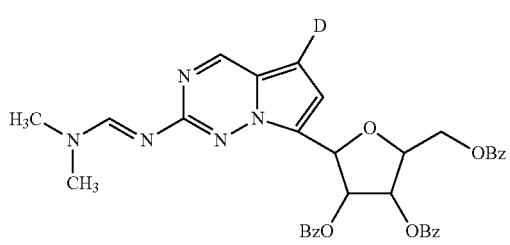

(a)

wherein

Bz is benzoyl, and

D is —C(=O)H or H,

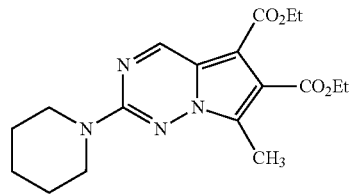

(b)

wherein Et is ethyl, or

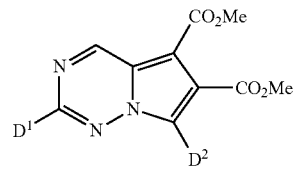

(c)

wherein $D^1$ is methoxy, phenyl, or 4-methylphenyl, $D^2$ is —CH$_2$C(=O)OMe or —C(=O)OMe, and Me is methyl.

As another example, also included within the scope of the present invention are compounds of formula I and pharmaceutically acceptable salts thereof in which $Q^1$ is -L$^1$-A$^1$-G$^1$-X$^1$—Z$^1$; $Q^2$ is L$^2$-A$^2$-G$^2$-X$^2$—Z$^2$; $Q^3$ is -L$^3$-A$^3$-G$^3$-X$^3$—Z$^3$; $Q^4$ is L$^4$-A$^4$-G$^4$A$^4$-Z$^4$; L$^1$ is $C_{1-6}$alkylene optionally substituted by 1-12 $R^9$, 3-15 membered heterocycloalkylene optionally substituted by 1-27 $R^9$, 4-21 membered heterocycloalkylalkylene optionally substituted by 1-39 $R^9$, 5-15 membered heteroarylene optionally substituted by 1-14 $R^9$, 6-21 membered heteroarylalkylene optionally substituted by 1-26 $R^9$, —C$_{0-3}$alkylNR$^4$C$_{0-3}$alkyl-, —C$_{0-3}$alkylNR$^4$NR$^4$C$_{0-3}$ alkyl-, —C$_{0-3}$alkylNR$^4$C(=O)C$_{0-3}$ alkyl-, —C$_{0-3}$ alkylNR$^4$C(=O)OC$_{0-3}$alkyl-, —C$_{0-3}$ alkylNR$^4$C(=O)NR$^4$C$_{0-3}$alkyl-, —C$_{0-3}$alkylNR$^4$C(=O)NR$^4$C(=O)C$_{0-3}$ alkyl-, —C$_{0-3}$alkylNR$^4$C(=S)C$_{0-3}$alkyl-, —C$_{0-3}$ alkylNR$^4$C(=S)NR$^4$C$_{0-3}$alkyl-, —C$_{0-3}$alkylNR$^4$S(=O)$_2$ C$_{0-3}$alkyl-, —C$_{0-3}$alkylOC$_{0-3}$alkyl-, or —C$_{0-3}$alkylS(=O)—C$_{0-3}$alkyl-; A$^1$ is $C_{1-6}$alkylene optionally substituted by 1-12 $R^a$, $C_{6-11}$arylene optionally substituted by 1-6 $R^a$, $C_{7-16}$arylalkylene optionally substituted by 1-18 $R^a$, 5-15 membered heteroarylene optionally substituted by 1-14 $R^a$, or 6-21 membered heteroarylalkylene optionally substituted by 1-26 $R^a$, wherein each $R^a$ is independently chosen from $C_{1-6}$alkyl optionally substituted by 1-13 $R^{19}$, $C_{6-11}$aryl optionally substituted by 1-7 $R^{19}$, $C_{7-16}$arylalkyl optionally substituted by 1-19 $R^{19}$, $C_{3-11}$cycloalkyl optionally substituted by 1-21 $R^{19}$, $C_{4-17}$cycloalkylalkyl optionally substituted by 1-32 $R^{19}$, 3-15 membered heterocycloalkyl optionally substituted by 1-28 $R^{19}$, 4-21 membered heterocycloalkylalkyl optionally substituted by 1-40 $R^{19}$, 5-15 membered heteroaryl optionally substituted by 1-15 $R^{19}$, 6-21 membered heteroarylalkyl optionally substituted by 1-27 $R^{19}$, halogen, —CN, —C(=O)R$^{10}$, —C(=O)OR$^{10}$, —C(=O)NR$^{12}$R$^{13}$, —C(=S)NR$^{12}$R$^{13}$, —NO$_2$, —NR$^{12}$R$^{13}$, —NR$^{14}$C(=O)R$^{10}$, —NR$^{14}$C(=O)OR$^{11}$, —NR$^{14}$C(=O)NR$^{12}$R$^{13}$, —NR$^{14}$C(=O)NR$^{14}$C(=O)R$^{10}$, —NR$^{14}$C(=O)NR$^{14}$C(=O)OR$^{10}$, —NR$^{14}$C(=S)R$^{10}$, —NR$^{14}$S(=O)$_2$R$^{11}$, —OR$^{10}$, =O, —OC(=O)R$^{10}$, —OC(=O)NR$^{12}$R$^{13}$, =S, —S(=O)$_n$R$^{10}$, and —S(=O)$_2$NR$^{12}$R$^{13}$; $G^1$ is $C_{1-6}$alkylene optionally substituted by 1-12 $R^{29}$, $C_{6-11}$ arylene optionally substituted by 1-6 $R^{29}$, $C_{7-16}$arylalkylene optionally substituted by 1-18 $R^{29}$, $C_{3-11}$cycloalkylene optionally substituted by 1-20 $R^{29}$, $C_{4-17}$cycloalkylalkylene optionally substituted by 1-31 $R^{29}$, 3-15 membered heterocycloalkylene optionally substituted by 1-27 $R^{29}$, 4-21 membered heterocycloalkylalkylene optionally substituted by 1-39 $R^{29}$, 5-15 membered heteroarylene optionally substituted by 1-14 $R^{29}$, 6-21 membered heteroarylalkylene optionally substituted by 1-26 $R^{29}$, —$C_{0-3}$alkylC(=O)$C_{0-3}$alkyl-, —$C_{0-3}$alkylC(=O)O$C_{0-3}$alkyl-, —$C_{0-3}$alkylC(=O)NR$^{24}C_{0-3}$alkyl-, —$C_{0-3}$alkylC(=S)NR$^{24}C_{0-3}$alkyl-, —$C_{0-3}$alkylNR$^{24}C_{0-3}$alkyl-, —$C_{0-3}$alkylNR$^{24}$C(=O)$C_{0-3}$alkyl-, —$C_{0-3}$alkylNR$^{24}$C(=O)O$C_{0-3}$alkyl-, —$C_{0-3}$alkylNR$^{24}$C(=O)NR$^{24}C_{0-3}$alkyl-, —$C_{0-3}$alkylNR$^{24}$C(=O)NR$^{24}$C(=O)$C_{0-3}$alkyl-, —$C_{0-3}$alkylNR$^{24}$C(=O)NR$^{24}$C(=O)O$C_{0-3}$alkyl-, —$C_{0-3}$alkylNR$^{24}$C(=S)$C_{0-3}$alkyl-, —$C_{0-3}$alkylNR$^{24}$S(=O)$_2C_{0-3}$alkyl-, —$C_{0-3}$alkylO$C_{0-3}$alkyl-, —$C_{0-3}$alkylOC(=O)$C_{0-3}$alkyl-, —$C_{0-3}$alkylOC(=O)NR$^{24}C_{0-3}$alkyl-, —$C_{0-3}$alkylS(=O)—$C_{0-3}$alkyl-, —$C_{0-3}$alkylS(=O)$_2$NR$^{24}C_{0-3}$alkyl-, —$C_{0-3}$alkylS(=O)NR$^{24}C_{0-3}$alkyl-, or absent; $X^1$ is $C_{1-6}$alkylene optionally substituted by 1-12 $R^{39}$, $C_{6-11}$arylene optionally substituted by 1-6 $R^{39}$, $C_{7-16}$arylalkylene optionally substituted by 1-18 $R^{39}$, $C_{3-11}$cycloalkylene optionally substituted by 1-20 $R^{39}$, $C_{4-17}$cycloalkylalkylene optionally substituted by 1-31 $R^{39}$, 3-15 membered heterocycloalkylene optionally substituted by 1-27 $R^{39}$, 4-21 membered heterocycloalkylalkylene optionally substituted by 1-39 $R^{39}$, 5-15 membered heteroarylene optionally substituted by 1-14 $R^{39}$, 6-21 membered heteroarylalkylene optionally substituted by 1-26 $R^{39}$, —$C_{0-3}$alkylC(=O)$C_{0-3}$alkyl-, —$C_{0-3}$alkylC(=O)O$C_{0-3}$alkyl-, —$C_{0-3}$alkylC(=O)NR$^{34}C_{0-3}$alkyl-, —$C_{0-3}$alkylC(=S)NR$^{34}C_{0-3}$alkyl-, —$C_{0-3}$alkylNR$^{34}C_{0-3}$alkyl-, —$C_{0-3}$alkylNR$^{34}$C(=O)$C_{0-3}$alkyl-, —$C_{0-3}$alkylNR$^{34}$C(=O)O$C_{0-3}$alkyl-, —$C_{0-3}$alkylNR$^{34}$C(=O)NR$^{34}C_{0-3}$alkyl-, —$C_{0-3}$alkylNR$^{34}$C(=O)NR$^{34}$C(=O)$C_{0-3}$alkyl-, —$C_{0-3}$alkylNR$^{34}$C(=O)NR$^{34}$C(=O)O$C_{0-3}$alkyl-, —$C_{0-3}$alkylNR$^{34}$S(=O)$_2C_{0-3}$alkyl-, —$C_{0-3}$alkylO$C_{0-3}$alkyl-, —$C_{0-3}$alkylOC(=O)$C_{0-3}$alkyl-, —$C_{0-3}$alkylOC(=O)NR$^{34}C_{0-3}$alkyl-, —$C_{0-3}$alkylS(=O)$_n C_{0-3}$alkyl-, —$C_{0-3}$alkylS(=O)$_2$NR$^{34}C_{0-3}$alkyl-, or absent; $Z^1$ is H, $C_{1-6}$alkyl optionally substituted by 1-13 $R^{49}$, $C_{7-16}$arylalkyl optionally substituted by 1-19 $R^{49}$, $C_{3-11}$cycloalkyl optionally substituted by 1-21 $R^{49}$, $C_{4-17}$cycloalkylalkyl optionally substituted by 1-32 $R^{49}$, 3-15 membered heterocycloalkyl optionally substituted by 1-28 $R^{49}$, 4-21 membered heterocycloalkylalkyl optionally substituted by 1-40 $R^{49}$, 5-15 membered heteroaryl optionally substituted by 1-15 $R^{49}$, 6-21 membered heteroarylalkyl optionally substituted by 1-27 $R^{49}$, halogen, —CN, —C(=O)$R^{100}$, —C(=O)OR$^{100}$, —C(=O)NR$^{102}R^{103}$, —C(=S)NR$^{102}R^{103}$, —NR$^{102}R^{103}$, —NR$^{104}$C(=O)$R^{100}$, —NR$^{104}$C(=O)OR$^{101}$, —NR$^{104}$C(=O)NR$^{102}R^{103}$, —NR$^{104}$C(=O)NR$^{104}$C(=O)$R^{100}$, —NR$^{104}$C(=S)$R^{100}$, —NR$^{104}$S(=O)$_2R^{101}$, —OR$^{100}$, =O, —OC(=O)$R^{100}$, —OC(=O)NR$^{102}R^{103}$, =S, —S(=O)$_n R^{100}$, or —S(=O)$_2$NR$^{102}R^{103}$; $L^2$, $L^3$, and $L^4$ are independently present or absent, and if present each is independently chosen from —$C_{0-3}$alkylC(=O)$C_{0-3}$alkyl-, —$C_{0-3}$alkylC(=O)O$C_{0-3}$alkyl-, —$C_{0-3}$alkylC(=O)NR$^{44}C_{0-3}$alkyl-, —$C_{0-3}$alkylC(=S)NR$^{44}C_{0-3}$alkyl-, —$C_{0-3}$alkylNR$^{44}C_{0-3}$alkyl-, —$C_{0-3}$alkylNR$^{44}$NR$^{44}C_{0-3}$alkyl-, —$C_{0-3}$alkylNR$^{44}$C(=O)$C_{0-3}$alkyl-, —$C_{0-3}$alkylNR$^{44}$C(=O)O$C_{0-3}$alkyl-, —$C_{0-3}$alkylNR$^{44}$C(=O)NR$^{44}C_{0-3}$alkyl-, —$C_{0-3}$alkylNR$^{44}$C(=O)NR$^{44}$C(=O)$C_{0-3}$alkyl-, —$C_{0-3}$alkylNR$^{44}$C(=O)NR$^{44}$C(=O)O$C_{0-3}$alkyl-, —$C_{0-3}$alkylNR$^{44}$C(=S)$C_{0-3}$alkyl-, —$C_{0-3}$alkylNR$^{44}$S(=O)$_2C_{0-3}$alkyl-, —$C_{0-3}$alkylO$C_{0-3}$alkyl-, —$C_{0-3}$alkylOC(=O)$C_{0-3}$alkyl-, —$C_{0-3}$alkylOC(=O)NR$^{44}C_{0-3}$alkyl-, —$C_{0-3}$alkylS(=O)—$C_{0-3}$alkyl-, —$C_{0-3}$alkylS(=O)$_2$NR$^{44}C_{0-3}$alkyl-, and —$C_{0-3}$alkylS(=O)$_2$NR$^{44}C_{0-3}$alkyl-; $A^2$, $A^3$, and $A^4$ are independently present or absent, and if present each is independently chosen from $C_{1-6}$alkyl optionally substituted by 1-12 $R^b$, $C_{6-11}$arylene optionally substituted by 1-6 $R^b$, $C_{7-16}$arylalkylene optionally substituted by 1-18 $R^b$, $C_{3-11}$cycloalkylene optionally substituted by 1-20 $R^b$, $C_{4-17}$cycloalkylalkylene optionally substituted by 1-31 $R^b$, 3-15 membered heterocycloalkylene optionally substituted by 1-27 $R^b$, 4-21 membered heterocycloalkylalkylene optionally substituted by 1-39 $R^b$, 5-15 membered heteroarylene optionally substituted by 1-14 $R^b$, or 6-21 membered heteroarylalkylene optionally substituted by 1-26 $R^b$; wherein each $R^b$ is independently chosen from $C_{1-6}$alkyl optionally substituted by 1-13 $R^{59}$, $C_{2-6}$alkenyl optionally substituted by 1-11 $R^{59}$, $C_{2-6}$alkynyl optionally substituted by 1-9 $R^{59}$, $C_{6-11}$aryl optionally substituted by 1-7 $R^{59}$, $C_{7-16}$arylalkyl optionally substituted by 1-19 $R^{59}$, $C_{3-11}$cycloalkyl optionally substituted by 1-21 $R^{59}$, $C_{4-17}$cycloalkylalkyl optionally substituted by 1-32 $R^{59}$, 3-15 membered heterocycloalkyl optionally substituted by 1-28 $R^{59}$, 4-21 membered heterocycloalkylalkyl optionally substituted by 1-40 $R^{59}$, 5-15 membered heteroaryl optionally substituted by 1-15 $R^{59}$, 6-21 membered heteroarylalkyl optionally substituted by 1-27 $R^{59}$, halogen, —CN, —C(=O)$R^{50}$, —C(=O)OR$^{50}$, —C(=O)NR$^{52}R^{53}$, —C(=S)NR$^{52}R^{53}$, —NR$^{52}R^{53}$, —NR$^{54}$C(=O)$R^{50}$, —NR$^{54}$C(=O)OR$^{51}$, —NR$^{54}$C(=O)NR$^{52}R^{53}$, —NR$^{54}$C(=O)NR$^{54}$C(=O)$R^{50}$, —NR$^{54}$C(=O)NR$^{54}$C(=O)OR$^{50}$, —NR$^{54}$C(=S)$R^{50}$, —NR$^{54}$S(=O)$_2R^{51}$, —OR$^{50}$, =O, —OCN, —OC(=O)$R^{50}$, —OC(=O)NR$^{52}R^{53}$, =S, —S(=O)$_n R^{50}$, and —S(=O)$_2$NR$^{52}R^{53}$; $G^2$, $G^3$, and $G^4$ are independently present or absent, and if present each is independently chosen from $C_{1-6}$alkylene optionally substituted by 1-12 $R^{69}$, $C_{6-11}$arylene optionally substituted by 1-6 $R^{69}$, $C_{7-16}$arylalkylene optionally substituted by 1-18 $R^{69}$, $C_{3-11}$cycloalkylene optionally substituted by 1-20 $R^{69}$, $C_{4-17}$cycloalkylalkylene optionally substituted by 1-31 $R^{69}$, 3-15 membered heterocycloalkylene optionally substituted by 1-27 $R^{69}$, 4-21 membered heterocycloalkylalkylene optionally substituted by 1-39 $R^{69}$, 5-15 membered heteroarylene optionally substituted by 1-14 $R^{69}$, 6-21 membered heteroarylalkylene optionally substituted by 1-26 $R^{69}$, —$C_{0-3}$alkylC(=O)$C_{0-3}$alkyl-, —$C_{0-3}$alkylC(=O)O$C_{0-3}$alkyl-, —$C_{0-3}$alkylC(=O)NR$^{64}C_{0-3}$alkyl-, —$C_{0-3}$alkylC(=S)NR$^{64}C_{0-3}$alkyl-, —$C_{0-3}$alkylNR$^{64}C_{0-3}$alkyl-, —$C_{0-3}$alkylNR$^{64}$C(=O)$C_{0-3}$alkyl-, —$C_{0-3}$alkylNR$^{64}$C(=O)O$C_{0-3}$alkyl-, —$C_{0-3}$alkylNR$^{64}$C(=O)NR$^{64}C_{0-3}$alkyl-, —$C_{0-3}$alkylNR$^{64}$C(=O)NR$^{64}$C(=O)$C_{0-3}$alkyl-, —$C_{0-3}$alkylNR$^{64}$C(=S)$C_{0-3}$alkyl-, —$C_{0-3}$alkylNR$^{64}$S(=O)$_2C_{0-3}$alkyl-, —$C_{0-3}$alkylO$C_{0-3}$alkyl-, —$C_{0-3}$alkylOC(=O)$C_{0-3}$alkyl-, —$C_{0-3}$alkylOC(=O)NR$^{64}C_{0-3}$alkyl-, —$C_{0-3}$alkylS(=O)—$C_{0-3}$alkyl-, and —$C_{0-3}$alkylS(=O)$_2$NR$^{64}C_{0-3}$alkyl-; $X^2$, $X^3$, and $X^4$ are independently present or absent, and if present each is independently chosen from $C_{1-6}$alkylene optionally substituted by 1-12 $R^{79}$, $C_{6-11}$ arylene optionally substituted by 1-6 $R^{79}$, $C_{7-16}$arylalkylene optionally substituted by 1-18 $R^{79}$, $C_{3-11}$cycloalkylene optionally substituted by 1-20 $R^{79}$, $C_{4-17}$cycloalkylalkylene optionally substituted by 1-31 $R^{79}$, 3-15 membered heterocycloalkylene optionally substituted by 1-27 $R^{79}$, 4-21 membered heterocycloalkylalkylene optionally substituted by 1-39 $R^{79}$, 5-15 membered heteroarylene optionally substituted by 1-14 $R^{79}$, 6-21 membered heteroarylalkylene optionally substituted by 1-26 $R^{79}$, —$C_{0-3}$alkylC(=O)$C_{0-3}$alkyl-, —$C_{0-3}$alkylC(=O)O$C_{0-3}$alkyl-, —$C_{0-3}$alkylC(=O)NR$^{74}C_{0-3}$alkyl-, —$C_{0-3}$alkylC(=S)NR$^{74}C_{0-3}$alkyl-, —$C_{0-3}$alkylNR$^{74}C_{0-3}$alkyl-, —$C_{0-3}$alkylNR$^{74}$C(=O)$C_{0-3}$alkyl-, —$C_{0-3}$alkylNR$^{74}$C(=O)O$C_{0-3}$ alkyl-, —C$_{0-3}$alkylNR$^{74}$C(=O)NR$^{74}$C$_{0-3}$alkyl-, —C$_{0-3}$alkylNR$^{74}$C(=O)NR$^{74}$C(=O)C$_{0-3}$alkyl-, —C$_{0-3}$alkylNR$^{74}$C(=O)NR$^{74}$C(=O)OC$_{0-3}$alkyl-, —C$_{0-3}$alkylNR$^{74}$C(=S)C$_{0-3}$alkyl-, —C$_{0-3}$alkylNR$^{74}$S(=O)$_2$C$_{0-3}$alkyl-, —C$_{0-3}$alkylOC$_{0-3}$alkyl-, —C$_{0-3}$alkylOC(=O)C$_{0-3}$alkyl-, —C$_{0-3}$alkylOC(=O)NR$^{74}$C$_{0-3}$alkyl-, —C$_{0-3}$alkylS(=O)—C$_{0-3}$alkyl-, and —C$_{0-3}$alkylS(=O)$_2$NR$^{74}$C$_{0-3}$alkyl-; Z$^2$, Z$^3$, and Z$^4$ are independently chosen from H, C$_{1-6}$alkyl optionally substituted by 1-13 R$^{89}$, C$_{6-11}$aryl optionally substituted by 1-7 R$^{89}$, C$_{7-16}$arylalkyl optionally substituted by 1-19 R$^{89}$, C$_{3-11}$cycloalkyl optionally substituted by 1-21 R$^{89}$, C$_{4-17}$cycloalkylalkyl optionally substituted by 1-32 R$^{89}$, 3-15 membered heterocycloalkyl optionally substituted by 1-28 R$^{89}$, 4-21 membered heterocycloalkylalkyl optionally substituted by 1-40 R$^{89}$, 5-15 membered heteroaryl optionally substituted by 1-15 R$^{89}$, 6-21 membered heteroarylalkyl optionally substituted by 1-27 R$^{89}$, halogen, —CN, —C(=O)R$^{80}$, —C(=O)OR$^{80}$, —C(=O)NR$^{82}$R$^{83}$, —C(=S)NR$^{82}$R$^{83}$, —NR$^{84}$C(=O)R$^{80}$, —NR$^{84}$C(=O)OR$^{81}$, —NR$^{84}$C(=O)NR$^{82}$R$^{83}$, —NR$^{84}$C(=O)NR$^{84}$C(=O)R$^{80}$, —NR$^{84}$C(=O)NR$^{84}$C(=O)OR$^{80}$, —NR$^{84}$C(=S)R$^{80}$, —NR$^{84}$S(=O)$_2$R$^{81}$, —OR$^{80}$, =O, —OC(=O)R$^{80}$, —OC(=O)NR$^{82}$R$^{83}$, =S, —S(=O)$_n$R$^{80}$, and —S(=O)$_2$NR$^{82}$R$^{83}$; alternatively, when L$^2$, A$^2$, G$^2$, X$^2$, L$^3$, A$^3$, G$^3$ and X$^3$ are absent, Z$^2$ and Z$^3$ can together form a group of formula -A$^{21}$-A$^{22}$-A$^{23}$-, or when L$^3$, A$^3$, G$^3$, X$^3$, L$^4$, A$^4$, G$^4$ and X$^4$ are absent, Z$^3$ and Z$^4$ can together form a group of formula -A$^{21}$-A$^{22}$-A$^{23}$-; wherein A$^{21}$, A$^{22}$, and A$^{23}$ are independently chosen from —CZ$^{21}$Z$^{22}$—, —CZ$^{23}$Z$^{24}$CZ$^{25}$Z$^{26}$—, —C(=O)—, —NZ$^{27}$—, —S—, —S(=O)—, —S(=O)$_2$—, or —O—; wherein:

(a) when any two of Z$^{21}$, Z$^{22}$, Z$^{23}$, Z$^{24}$, Z$^{25}$, Z$^{26}$ and Z$^{27}$ are located on adjacent atoms, they may together form a bond between the atoms, and (b) any of Z$^{21}$, Z$^{22}$, Z$^{23}$, Z$^{24}$, Z$^{25}$, Z$^{26}$ and Z$^{27}$ may be independently chosen from H, C$_{1-6}$alkyl optionally substituted by 1-13 R$^{99}$, C$_{6-11}$aryl optionally substituted by 1-7 R$^{99}$, C$_{7-16}$arylalkyl optionally substituted by 1-19 R$^{99}$, C$_{3-11}$cycloalkyl optionally substituted by 1-21 R$^{99}$, C$_{4-17}$cycloalkylalkyl optionally substituted by 1-32 R$^{99}$, 3-15 membered heterocycloalkyl optionally substituted by 1-28 R$^{99}$, 4-21 membered heterocycloalkylalkyl optionally substituted by 1-40 R$^{99}$, 5-15 membered heteroaryl optionally substituted by 1-15 R$^{99}$, 6-21 membered heteroarylalkyl optionally substituted by 1-27 R$^{99}$, halogen, —CN, —C(=O)R$^{90}$, —C(=O)OR$^{90}$, —C(=O)NR$^{92}$R$^{93}$, —C(=S)NR$^{92}$R$^{93}$, —NR$^{92}$R$^{93}$, —NR$^{94}$C(=O)R$^{90}$, —NR$^{94}$C(=O)OR$^{91}$, —NR$^{94}$C(=O)NR$^{92}$R$^{93}$, —NR$^{94}$C(=O)NR$^{94}$C(=O)R$^{90}$, —NR$^{94}$C(=O)NR$^{94}$C(=O)OR$^{90}$, —NR$^{94}$C(=S)R$^{90}$, —NR$^{94}$S(=O)$_2$R$^{91}$, —OR$^{90}$, =O, —OC(=O)R$^{90}$, —OC(=O)NR$^{92}$R$^{93}$, =S, —S(=O)$_n$R$^{90}$, and —S(=O)$_2$NR$^{92}$R$^{93}$; and (c) any two of Z$^{21}$, Z$^{22}$, Z$^{23}$, Z$^{24}$, Z$^{25}$, Z$^{26}$ and Z$^{27}$ may together form a group of formula -A$^{31}$-A$^{32}$-A$^{33}$-, wherein A$^{31}$, A$^{32}$, and A$^{33}$ are independently chosen from —CZ$^{31}$Z$^{32}$—, —CZ$^{33}$Z$^{34}$CZ$^{35}$Z$^{36}$—, —C(=O)—, —NZ$^{37}$—, —S—, —S(=O)—, —S(=O)$_2$—, or —O— wherein:

(i) when any two of Z$^{31}$, Z$^{32}$, Z$^{33}$, Z$^{34}$, Z$^{35}$, Z$^{36}$ and Z$^{37}$ are located on adjacent atoms, they may together form a bond between the atoms, and (ii) any of any of Z$^{21}$, Z$^{22}$, Z$^{23}$, Z$^{24}$, Z$^{25}$, Z$^{26}$ and Z$^{27}$ may be independently chosen from H, C$_{1-6}$alkyl optionally substituted by 1-13 R$^{139}$, C$_{6-11}$aryl optionally substituted by 1-7 R$^{139}$, C$_{7-16}$arylalkyl optionally substituted by 1-19 R$^{139}$, C$_{3-11}$cycloalkyl optionally substituted by 1-21 R$^{139}$, C$_{4-17}$cycloalkylalkyl optionally substituted by 1-32 R$^{139}$, 3-15 membered heterocycloalkyl optionally substituted by 1-28 R$^{139}$, 4-21 membered heterocycloalkylalkyl optionally substituted by 1-40 R$^{139}$, 5-15 membered heteroaryl optionally substituted by 1-15 R$^{139}$, 6-21 membered heteroarylalkyl optionally substituted by 1-27 R$^{139}$, halogen, —CN, —C(=O)R$^{130}$, —C(=O)OR$^{130}$, —C(=O)NR$^{132}$R$^{133}$, —C(=S)NR$^{132}$R$^{133}$, —NR$^{132}$R$^{133}$, —NR$^{134}$C(=O)R$^{130}$, —NR$^{134}$C(=O)OR$^{131}$, —NR$^{134}$C(=O)NR$^{132}$R$^{133}$, —NR$^{134}$C(=O)NR$^{134}$C(=O)R$^{130}$, —NR$^{134}$C(=S)R$^{130}$, —NR$^{134}$S(=O)$_2$R$^{131}$, —OR$^{130}$, =O, —OCN, —OC(=O)R$^{130}$, —OC(=O)NR$^{132}$R$^{133}$, =S, —S(=O)$_n$R$^{130}$, and —S(=O)$_2$NR$^{132}$R$^{133}$; R$^9$, R$^{19}$, R$^{29}$, R$^{39}$, R$^{49}$, R$^{59}$, R$^{69}$, R$^{79}$, R$^{89}$, R$^{99}$, and R$^{139}$ at each occurrence is independently chosen from C$_{1-6}$alkyl optionally substituted by 1-13 R$^{179}$, C$_{6-11}$aryl optionally substituted by 1-7 R$^{179}$, C$_{7-16}$arylalkyl optionally substituted by 1-19 R$^{179}$, C$_{3-11}$cycloalkyl optionally substituted by 1-21 R$^{179}$, C$_{4-17}$cycloalkylalkyl optionally substituted by 1-32 R$^{179}$, 3-15 membered heterocycloalkyl optionally substituted by 1-28 R$^{179}$, 4-21 membered heterocycloalkylalkyl optionally substituted by 1-40 R$^{179}$, 5-15 membered heteroaryl optionally substituted by 1-15 R$^{179}$, 6-21 membered heteroarylalkyl optionally substituted by 1-27 R$^{179}$, halogen, —CN, —C(=O)R$^{170}$, —C(=O)OR$^{170}$, —C(=O)NR$^{172}$R$^{173}$, —C(=S)NR$^{172}$R$^{173}$, —NR$^{172}$R$^{173}$, —NR$^{174}$C(=O)R$^{179}$, —NR$^{174}$C(=O)OR$^{171}$, —NR$^{174}$C(=O)NR$^{172}$R$^{173}$, —NR$^{174}$C(=O)NR$^{174}$C(=O)R$^{170}$, —NR$^{174}$C(=S)R$^{170}$, —NR$^{174}$S(=O)$_2$R$^{171}$, —OR$^{170}$, =O, —OC(=O)R$^{170}$, —OC(=O)NR$^{172}$R$^{173}$, —OS(=O)$_2$NR$^{172}$R$^{173}$, =S, —S(=O)$_n$R$^{170}$, and —S(=O)$_2$NR$^{172}$R$^{173}$; R$^1$, R$^4$, R$^5$, R$^6$, R$^{10}$, R$^{11}$, R$^{14}$, R$^{15}$, R$^{16}$, R$^{17}$, R$^{21}$, R$^{24}$, R$^{25}$, R$^{26}$, R$^{31}$, R$^{34}$, R$^{35}$, R$^{36}$, R$^{41}$, R$^{44}$, R$^{45}$, R$^{46}$, R$^{50}$, R$^{51}$, R$^{54}$, R$^{55}$, R$^{56}$, R$^{57}$, R$^{61}$, R$^{64}$, R$^{65}$, R$^{66}$, R$^{71}$, R$^{74}$, R$^{75}$, R$^{76}$, R$^{80}$, R$^{81}$, R$^{84}$, R$^{85}$, R$^{86}$, R$^{87}$, R$^{90}$, R$^{91}$, R$^{94}$, R$^{95}$, R$^{96}$, R$^{97}$, R$^{100}$, R$^{101}$, R$^{104}$, R$^{105}$, R$^{106}$, R$^{107}$, R$^{130}$, R$^{131}$, R$^{134}$, R$^{135}$, R$^{136}$, R$^{137}$, R$^{170}$, R$^{171}$, R$^{174}$, R$^{175}$, R$^{176}$ and R$^{177}$ each occurrence is independently chosen from H, C$_{1-6}$alkyl optionally substituted by 1-13 R$^{189}$, C$_{6-11}$aryl optionally substituted by 1-7 R$^{189}$, C$_{7-16}$arylalkyl optionally substituted by 1-19 R$^{189}$, C$_{3-11}$cycloalkyl optionally substituted by 1-21 R$^{189}$, C$_{4-17}$cycloalkylalkyl optionally substituted by 1-32 R$^{189}$, 3-15 membered heterocycloalkyl optionally substituted by 1-28 R$^{189}$, 4-21 membered heterocycloalkylalkyl optionally substituted by 1-40 R$^{189}$, 5-15 membered heteroaryl optionally substituted by 1-15 R$^{189}$, and 6-21 membered heteroarylalkyl optionally substituted by 1-27 R$^{189}$; R$^2$, R$^3$, R$^{12}$, R$^{13}$, R$^{22}$, R$^{23}$, R$^{32}$, R$^{33}$, R$^{42}$, R$^{43}$, R$^{52}$, R$^{53}$, R$^{62}$, R$^{63}$, R$^{72}$, R$^{73}$, R$^{82}$, R$^{83}$, R$^{92}$, R$^{93}$, R$^{102}$, R$^{103}$, R$^{132}$, R$^{133}$, R$^{172}$ and R$^{173}$ at each occurrence is independently chosen from H, C$_{1-6}$alkyl optionally substituted by 1-13 R$^{199}$, C$_{6-11}$aryl optionally substituted by 1-7 R$^{199}$, C$_{7-16}$arylalkyl optionally substituted by 1-19 R$^{199}$, C$_{3-11}$cycloalkyl optionally substituted by 1-21 R$^{199}$, C$_{4-17}$cycloalkylalkyl optionally substituted by 1-32 R$^{199}$, 3-15 membered heterocycloalkyl optionally substituted by 1-28 R$^{199}$, 4-21 membered heterocycloalkylalkyl optionally substituted by 1-40 R$^{199}$, 5-15 membered heteroaryl optionally substituted by 1-15 R$^{199}$, and 6-21 membered heteroarylalkyl optionally substituted by 1-27 R$^{199}$; or any R$^2$ and R$^3$, R$^{12}$ and R$^{13}$, R$^{22}$ and R$^{23}$, R$^{32}$ and R$^{33}$, R$^{42}$ and R$^{43}$, R$^{52}$ and R$^{53}$, R$^{62}$ and R$^{63}$, R$^{72}$ and R$^{73}$, R$^{82}$ and R$^{83}$, R$^{92}$ and R$^{93}$, R$^{102}$ and R$^{103}$, R$^{132}$ and R$^{133}$, or R$^{172}$ and R$^{173}$ may form, together with the nitrogen atom to which they are attached, a 3-15 membered heterocycloalkyl optionally substituted by 1-28 R$^{209}$ or a 5-15 membered heteroaryl optionally substituted by 1-15 R$^{209}$; R$^{179}$, R$^{189}$, R$^{199}$ and R$^{209}$ at each occurrence is independently chosen from C$_{1-6}$alkyl optionally substituted by 1-13 R$^{219}$, C$_{6-11}$aryl optionally substituted by 1-7 R$^{219}$, C$_{7-16}$arylalkyl optionally substituted by 1-19 R$^{219}$, C$_{3-11}$cycloalkyl optionally substituted by 1-21 $R^{219}$, $C_{4-17}$cycloalkylalkyl optionally substituted by 1-32 $R^{219}$, 3-15 membered heterocycloalkyl optionally substituted by 1-28 $R^{219}$, 4-21 membered heterocycloalkylalkyl optionally substituted by 1-40 $R^{219}$, 5-15 membered heteroaryl optionally substituted by 1-15 $R^{219}$, 6-21 membered heteroarylalkyl optionally substituted by 1-27 $R^{219}$, halogen, —CN, —C(=O)$R^{210}$, —C(=O)O$R^{210}$, —C(=O)N$R^{212}R^{213}$, —C(=S)N$R^{212}R^{213}$, —N$R^{212}R^{213}$, —N$R^{214}$C(=O)$R^{210}$, —N$R^{214}$C(=O)O$R^{211}$, —N$R^{214}$C(=O)N$R^{212}R^{213}$, —N$R^{214}$C(=O)N$R^{214}$C(=O)$R^{210}$, —N$R^{214}$C(=S)$R^{210}$, —N$R^{214}$S(=O)$_2$$R^{211}$, —O$R^{210}$, =O, —OC(=O)$R^{210}$, —OC(=O)$R^{210}$, —S(=O)$_n$$R^{210}$, and —S(=O)$_2$N$R^{212}R^{213}$; $R^{210}$, $R^{211}$, $R^{214}$, $R^{215}$, $R^{216}$ and $R^{217}$ at each occurrence is independently chosen from H, $C_{1-6}$alkyl optionally substituted by 1-13 $R^{229}$, $C_{6-11}$ aryl optionally substituted by 1-7 $R^{229}$, $C_{7-16}$arylalkyl optionally substituted by 1-19 $R^{229}$, $C_{3-11}$cycloalkyl optionally substituted by 1-21 $R^{229}$, $C_{4-17}$cycloalkylalkyl optionally substituted by 1-32 $R^{229}$, 3-15 membered heterocycloalkyl optionally substituted by 1-28 $R^{229}$, 4-21 membered heterocycloalkylalkyl optionally substituted by 1-40 $R^{229}$, 5-15 membered heteroaryl optionally substituted by 1-15 $R^{229}$, and 6-21 membered heteroarylalkyl optionally substituted by 1-27 $R^{229}$; $R^{212}$ and $R^{213}$ at each occurrence is independently chosen from H, $C_{1-6}$alkyl optionally substituted by 1-13 $R^{239}$, $C_{6-11}$aryl optionally substituted by 1-7 $R^{239}$, $C_{7-16}$arylalkyl optionally substituted by 1-19 $R^{239}$, $C_{3-11}$cycloalkyl optionally substituted by 1-21 $R^{239}$, $C_{4-17}$cycloalkylalkyl optionally substituted by 1-32 $R^{239}$, 3-15 membered heterocycloalkyl optionally substituted by 1-28 $R^{239}$, 4-21 membered heterocycloalkylalkyl optionally substituted by 1-40 $R^{239}$, 5-15 membered heteroaryl optionally substituted by 1-15 $R^{239}$, and 6-21 membered heteroarylalkyl optionally substituted by 1-27 $R^{239}$; or any $R^{212}$ and $R^{213}$ may form, together with the nitrogen atom to which they are attached, a 3-15 membered heterocycloalkyl optionally substituted by 1-28 $R^{249}$ or a 5-15 membered heteroaryl optionally substituted by 1-15 $R^{249}$; $R^{219}$, $R^{229}$, $R^{239}$ and $R^{249}$ at each occurrence is independently chosen from $C_{1-6}$alkyl optionally substituted by 1-13 halogen, $C_{2-6}$alkenyl, $C_{2-6}$alkynyl, $C_{6-11}$ aryl, $C_{7-16}$arylalkyl, $C_{3-11}$cycloalkyl, $C_{4-17}$cycloalkylalkyl, 3-15 membered heterocycloalkyl, 4-21 membered heterocycloalkylalkyl, 5-15 membered heteroaryl, 6-21 membered heteroarylalkyl, halogen, —CN, —C(=O)$R^{250}$, —C(=O)O$R^{250}$, —C(=O)N$R^{250}R^{250}$, —C(=S)N$R^{250}R^{250}$, —N$R^{250}$C(=S)$R^{250}$, —N$R^{250}$S(=O)$_2$$R^{250}$, —O$R^{250}$, =O, —OC(=O)$R^{250}$, —OC(=O)N$R^{250}R^{250}$; =S, —S(=O)$_n$$R^{250}$, and —S(=O)$_2$ N$R^{250}R^{250}$; $R^{250}$ at each occurrence is independently chosen from H, $C_{1-6}$alkyl and $C_{1-6}$-haloalkyl; and n at each occurrence is independently chosen from 0, 1, and 2; with the proviso that the compound is not:

(a)

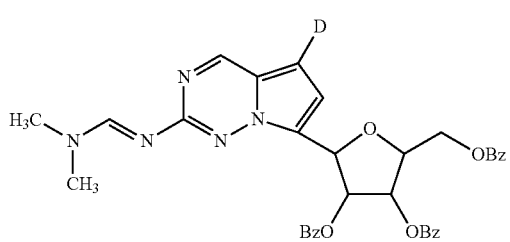

wherein
Bz is benzoyl, and
D is —C(=O)H or H, (b)

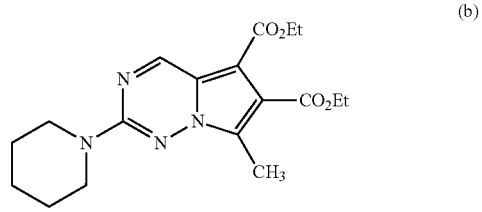

wherein Et is ethyl, or (c)

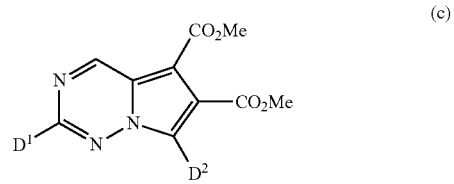

wherein
$D^1$ is methoxy, phenyl, or 4-methylphenyl,
$D^2$ is —CH$_2$C(=O)OMe or —C(=O)OMe, and
Me is methyl.

As another example, also included within the scope of the present invention are compounds of formula I and pharmaceutically acceptable salts thereof in which $Q^1$ is -$L^1$-$A^1$-$G^1$-$X^1$—$Z^1$; $Q^2$ is -$L^2$-$A^2$-$G^2$-$X^2$—$Z^2$; $Q^3$ is -$L^3$-$A^3$-$G^3$-$X^3$—$Z^3$; $Q^4$ is -$L^4$-$A^4$-$G^4$-$X^4$—$Z^4$; $L^1$ is $C_{1-6}$alkylene optionally substituted by 1-6 $R^9$, $C_{7-16}$arylalkylene optionally substituted by 1-6 $R^9$, $C_{3-11}$cycloalkylene optionally substituted by 1-6 $R^9$, $C_{4-17}$cycloalkylalkylene optionally substituted by 1-6 $R^9$, 3-15 membered heterocycloalkylene optionally substituted by 1-6 $R^9$, 4-21 membered heterocycloalkylalkylene optionally substituted by 1-6 $R^9$, 5-15 membered heteroarylene optionally substituted by 1-6 $R^9$, 6-21 membered heteroarylalkylene optionally substituted by 1-6 $R^9$, —C(=O)—, —C(=O)O—, —C(=O)N$R^4$—, —C(=O)C(=O)—, —C(=S)N$R^4$—, —N$R^4$—, —N$R^4$N$R^4$—, —N$R^4$C(=O)—, —N$R^4$C(=O)C(=O)—, —N$R^4$C(=O)O—, —N$R^4$C(=O)C(=O)O—, —N$R^4$C(=O)N$R^4$—, —N$R^4$C(=O)N$R^4$C(=O)—, —N$R^4$C(=O)N$R^4$C(=O)O—, —N$R^4$C(=O)C(=O)N$R^4$—, —N$R^4$C(=S)—, —N$R^4$C(=S)O—, —N$R^4$C(=S)N$R^4$—, —N$R^4$S(=O)$_2$—, —N$R^4$S(=O)$_2$N$R^4$—, —O—, —OC(=O)—, —OC(=O)N$R^4$—, —OC(=O)O—, —OS(=O)—, —OS(=O)$_2$—, —OS(=O)$_2$O—, —OS(=O)$_2$N$R^4$—, —S(=O)$_n$—, —S(=O)$_2$O—, —SO$_3$—, —S(=O)$_2$N$R^4$—, —S(=O)N$R^4$—, or absent; $A^1$ is $C_{1-6}$alkylene optionally substituted by 1-6 $R^a$, $C_{6-11}$ arylene optionally substituted by 1-6 $R^a$, $C_{7-16}$arylalkylene optionally substituted by 1-6 $R^a$, $C_{3-11}$cycloalkylene optionally substituted by 1-6 $R^a$, $C_{4-17}$cycloalkylalkylene optionally substituted by 1-6 $R^a$, 3-15 membered heterocycloalkylene optionally substituted by 1-6 $R^a$, 4-21 membered heterocycloalkylalkylene optionally substituted by 1-6 $R^a$, 5-15 membered heteroarylene optionally substituted by 1-6 $R^a$, or 6-21 membered heteroarylalkylene optionally substituted by 1-6 $R^a$; each $R^a$ is independently chosen from $C_{1-6}$alkyl optionally substituted by 1-6 $R^{19}$, $C_{2-6}$alkenyl optionally substituted by 1-6 $R^{19}$, $C_{2-6}$alkynyl optionally substituted by 1-6 $R^{19}$, $C_{6-11}$ aryl optionally substituted by 1-6 $R^{19}$, $C_{7-16}$arylalkyl optionally substituted by 1-6 $R^{19}$, $C_{3-11}$cycloalkyl optionally substituted by 1-6 $R^{19}$, $C_{4-17}$cycloalkylalkyl optionally substituted by 1-6 $R^{19}$, 3-15 membered heterocycloalkyl optionally substituted by 1-6

$R^{19}$, 4-21 membered heterocycloalkylalkyl optionally substituted by 1-6 $R^{19}$, 5-15 membered heteroaryl optionally substituted by 1-6 $R^{19}$, 6-21 membered heteroarylalkyl optionally substituted by 1-6 $R^{19}$, halogen, —CN, —C(=O)$R^{10}$, —C(=O)O$R^{10}$, —C(=O)N$R^{12}R^{13}$, —C(=O)C(=O)$R^{10}$, —C(=S)N$R^{12}R^{13}$, —NC, —NO$_2$, —N$R^{12}R^{13}$, —N$R^{14}$N$R^{12}R^{13}$, —N$R^{14}$O$R^{16}$, —N$R^{14}$C(=O)$R^{10}$, —N$R^{14}$C(=O)C(=O)$R^{10}$, —N$R^{14}$C(=O)O$R^{11}$, —N$R^{14}$C(=O)C(=O)O$R^{11}$, —N$R^{14}$C(=O)N$R^{12}R^{13}$, —N$R^{14}$C(=O)N$R^{14}$C(=O)$R^{10}$, —N$R^{14}$C(=O)N$R^{14}$C(=O)O$R^{10}$, —N$R^{14}$C(=N$R^{15}$)N$R^{12}R^{13}$, —N$R^{14}$C(=O)C(=O)N$R^{12}R^{13}$, —N$R^{14}$C(=S)$R^{10}$, —N$R^{14}$C(=S)O$R^{10}$, —N$R^{14}$C(=S)N$R^{12}R^{13}$, —N$R^{14}$S(=O)$_2R^{11}$, —N$R^{14}$S(=O)$_2$N$R^{12}R^{13}$, —O$R^{10}$, =O, —OCN, —OC(=O)$R^{10}$, —OC(=O)N$R^{12}R^{13}$, —OC(=O)O$R^{10}$, —OS(=O)$R^{10}$, —OS(=O)$_2R^{10}$, —OS(=O)$_2$O$R^{10}$, —OS(=O)$_2$N$R^{12}R^{13}$, —SCN, =S, —S(=O)$_nR^{10}$, —S(=O)$_2$O$R^{10}$, —SO$_3R^{17}$, —S(=O)$_2$N$R^{12}R^{13}$, and —S(=O)N$R^{12}R^{13}$; $G^1$ is $C_{1-6}$alkylene optionally substituted by 1-6 $R^{29}$, $C_{6-11}$arylene optionally substituted by 1-6 $R^{29}$, $C_{7-16}$arylalkylene optionally substituted by 1-6 $R^{29}$, $C_{3-11}$cycloalkylene optionally substituted by 1-6 $R^{29}$, $C_{4-17}$cycloalkylalkylene optionally substituted by 1-6 $R^{29}$, 3-15 membered heterocycloalkylene optionally substituted by 1-6 $R^{29}$, 4-21 membered heterocycloalkylalkylene optionally substituted by 1-6 $R^{29}$, 5-15 membered heteroarylene optionally substituted by 1-6 $R^{29}$, 6-21 membered heteroarylalkylene optionally substituted by 1-6 $R^{29}$, —C(=O)—, —C(=O)O—, —C(=O)N$R^{24}$—, —C(=O)C(=O)—, —C(=S)N$R^{24}$—, —N$R^{24}$—, —N$R^{24}$N$R^{24}$—, —N$R^{24}$C(=O)—, —N$R^{24}$C(=O)C(=O)—, —N$R^{24}$C(=O)O—, —N$R^{24}$C(=O)C(=O)O—, —N$R^{24}$C(=O)N$R^{24}$—, —N$R^{24}$C(=O)N$R^{24}$C(=O)—, —N$R^{24}$C(=O)N$R^{24}$C(=O)O—, —N$R^{24}$C(=O)C(=O)N$R^{24}$—, —NR—, —NR—, —N$R^{24}$C(=S)N$R^{24}$—, —N$R^{24}$S(=O)$_2$N$R^{24}$—, —O—, —OC(=O)—, —OC(=O)N$R^{24}$—, —OC(=O)O—, —OS(=O)—, —OS(=O)$_2$—, —OS(=O)$_2$O—, —OS(=O)$_2$N$R^{24}$—, —S(=O)$_n$—, —S(=O)$_2$O—, —SO$_3$—, —S(=O)$_2$N$R^{24}$—, —S(=O)N$R^{24}$—, or absent; $X^1$ is $C_{1-6}$alkylene optionally substituted by 1-6 $R^{39}$, $C_{6-11}$arylene optionally substituted by 1-6 $R^{39}$, $C_{7-16}$arylalkylene optionally substituted by 1-6 $R^{39}$, $C_{3-11}$cycloalkylene optionally substituted by 1-6 $R^{39}$, $C_{4-17}$cycloalkylalkylene optionally substituted by 1-6 $R^{39}$, 3-15 membered heterocycloalkylene optionally substituted by 1-6 $R^{39}$, 4-21 membered heterocycloalkylalkylene optionally substituted by 1-6 $R^{39}$, 5-15 membered heteroarylene optionally substituted by 1-6 $R^{39}$, 6-21 membered heteroarylalkylene optionally substituted by 1-6 $R^{39}$, —C(=O)—, —C(=O)O—, —C(=O)N$R^{34}$—, —C(=O)C(=O)—, —C(=S)N$R^{34}$—, —N$R^{34}$—, —N$R^{34}$N$R^{34}$—, —N$R^{34}$C(=O)—, —N$R^{34}$C(=O)C(=O)—, —N$R^{34}$C(=O)O—, —N$R^{34}$C(=O)C(=O)O—, —N$R^{34}$C(=O)N$R^{34}$—, —N$R^{34}$C(=O)N$R^{34}$C(=O)—, —N$R^{34}$C(=O)N$R^{34}$C(=O)O—, —N$R^{34}$C(=N$R^{35}$)N$R^{34}$—, —N$R^{34}$C(=O)C(=O)N$R^{34}$—, —N$R^{34}$C(=S)—, —N$R^{34}$C(=S)O—, —N$R^{34}$C(=S)N$R^{34}$—, —N$R^{34}$S(=O)$_2$—, —N$R^{34}$S(=O)$_2$N$R^{34}$—, —O—, —OC(=O)—, —OC(=O)N$R^{34}$—, —OC(=O)O—, —OS(=O)—, —OS(=O)$_2$—, —OS(=O)$_2$O—, —OS(=O)$_2$N$R^{34}$—, —S(=O)$_n$—, —S(=O)$_2$O—, —SO$_3$—, —S(=O)$_2$N$R^{34}$—, —S(=O)N$R^{34}$—, or absent; $Z^1$ is H, $C_{1-6}$alkyl optionally substituted by 1-6 $R^{49}$, $C_{7-16}$arylalkyl optionally substituted by 1-6 $R^{49}$, $C_{3-11}$cycloalkyl optionally substituted by 1-6 $R^{49}$, $C_{4-17}$cycloalkylalkyl optionally substituted by 1-6 $R^{49}$, 3-15 membered heterocycloalkyl optionally substituted by 1-6 $R^{49}$, 4-21 membered heterocycloalkylalkyl optionally substituted by 1-6 $R^{49}$, 5-15 membered heteroaryl optionally substituted by 1-6 $R^{49}$, 6-21 membered heteroarylalkyl optionally substituted by 1-6 $R^{49}$, halogen, —CN, —C(=O)$R^{100}$, —C(=O)O$R^{100}$, —C(=O)N$R^{102}R^{103}$, —C(=O)C(=O)$R^{100}$, —C(=S)N$R^{102}R^{103}$, —NC, —NO$_2$, —N$R^{102}R^{103}$, —N$R^{104}$N$R^{102}R^{103}$, —N$R^{104}$C(=O)$R^{100}$, —N$R^{104}$C(=O)C(=O)$R^{100}$, —N$R^{104}$C(=O)O$R^{101}$, —N$R^{104}$C(=O)C(=O)O$R^{101}$, —N$R^{104}$C(=O)N$R^{102}R^{103}$, —N$R^{104}$C(=O)N$R^{104}$C(=O)$R^{100}$, —N$R^{104}$C(=O)N$R^{104}$C(=O)O$R^{100}$, —N$R^{104}$C(=N$R^{105}$)N$R^{102}R^{103}$, —N$R^{104}$C(=O)C(=O)N$R^{102}R^{103}$, —N$R^{104}$C(=S)$R^{100}$, —N$R^{104}$C(=S)O$R^{100}$, —N$R^{104}$C(=S)N$R^{102}R^{103}$, —N$R^{104}$S(=O)$_2R^{101}$, —N$R^{104}$S(=O)$_2$N$R^{102}R^{103}$, —O$R^{100}$, =O, —OCN, —OC(=O)$R^{100}$, —OC(=O)N$R^{102}R^{103}$, —OC(=O)O$R^{100}$, —OS(=O)$R^{100}$, —OS(=O)$_2R^{100}$, —OS(=O)$_2$O$R^{100}$, —OS(=O)$_2$N$R^{102}R^{103}$, —SCN, =S, —S(=O)$_nR^{100}$, —S(=O)$_2$O$R^{100}$, —SO$_3R^{107}$, —S(=O)$_2$N$R^{102}R^{103}$, or —S(=O)N$R^{102}R^{103}$; $L^2$, $L^3$, and $L^4$ are independently —C(=O)—, —C(=O)O—, —C(=O)N$R^{44}$—, —C(=O)C(=O)—, —C(=S)N$R^{44}$—, —N$R^{44}$—, —N$R^{44}$N$R^{44}$—, —N$R^{44}$C(=O)—, —N$R^{44}$C(=O)C(=O)—, —N$R^{44}$C(=O)O—, —N$R^{44}$C(=O)C(=O)O—, —N$R^{44}$C(=O)N$R^{44}$—, —N$R^{44}$C(=O)N$R^{44}$C(=O)—, —N$R^{44}$C(=O)N$R^{44}$C(=O)O—, —N$R^{44}$C(=N$R^{45}$)N$R^{44}$—, —N$R^{44}$C(=O)C(=O)N$R^{44}$—, —N$R^{44}$C(=S)—, —N$R^{44}$C(=S)O—, —N$R^{44}$C(=S)N$R^{44}$—, —N$R^{44}$S(=O)$_2$N$R^{44}$—, —O—, —OC(=O)—, —OC(=O)N$R^{44}$—, —OC(=O)O—, —OS(=O)—, —OS(=O)$_2$—, —OS(=O)$_2$O—, —OS(=O)$_2$N$R^{44}$—, —S(=O)$_n$—, —S(=O)$_2$O—, —SO$_3$—, —S(=O)$_2$N$R^{44}$—, —S(=O)N$R^{44}$—, or absent; $A^2$, $A^3$, and $A^4$ are independently $C_{1-6}$alkylene optionally substituted by 1-6 $R^b$, $C_{6-11}$arylene optionally substituted by 1-6 $R^b$, $C_{7-16}$arylalkylene optionally substituted by 1-6 $R^b$, $C_{3-11}$cycloalkylene optionally substituted by 1-6 $R^b$, $C_{4-17}$cycloalkylalkylene optionally substituted by 1-6 $R^b$, 3-15 membered heterocycloalkylene optionally substituted by 1-6 $R^b$, 4-21 membered heterocycloalkylalkylene optionally substituted by 1-6 $R^b$, 5-15 membered heteroarylene optionally substituted by 1-6 $R^b$, 6-21 membered heteroarylalkylene optionally substituted by 1-6 $R^b$, or absent; each $R^b$ is independently chosen from $C_{1-6}$alkyl optionally substituted by 1-6 $R^{59}$, $C_{2-6}$alkenyl optionally substituted by 1-6 $R^{59}$, $C_{2-6}$alkynyl optionally substituted by 1-6 $R^{59}$, $C_{6-11}$aryl optionally substituted by 1-6 $R^{59}$, $C_{7-16}$arylalkyl optionally substituted by 1-6 $R^{59}$, $C_{3-11}$cycloalkyl optionally substituted by 1-6 $R^{59}$, $C_{4-17}$cycloalkylalkyl optionally substituted by 1-6 $R^{59}$, 3-15 membered heterocycloalkyl optionally substituted by 1-6 $R^{59}$, 4-21 membered heterocycloalkylalkyl optionally substituted by 1-6 $R^{59}$, 5-15 membered heteroaryl optionally substituted by 1-6 $R^{59}$, 6-21 membered heteroarylalkyl optionally substituted by 1-6 $R^{59}$, halogen, —CN, —C(=O)$R^{50}$, —C(=O)O$R^{50}$, —C(=O)N$R^{52}R^{53}$, —C(=O)C(=O)$R^{50}$, —C(=S)N$R^{52}R^{53}$, —NC, —NO$_2$, —N$R^{52}R^{53}$, —N$R^{54}$N$R^{52}R^{53}$, —N$R^{54}$C(=O)$R^{50}$, —N$R^{54}$C(=O)C(=O)$R^{50}$, —N$R^{54}$C(=O)O$R^{51}$, —N$R^{54}$C(=O)C(=O)O$R^{51}$, —N$R^{54}$C(=O)N$R^{52}R^{53}$, —N$R^{54}$C(=O)N$R^{54}$C(=O)$R^{50}$, —N$R^{54}$C(=O)N$R^{54}$C(=O)O$R^{50}$, —N$R^{54}$C(=N$R^{55}$)N$R^{52}R^{53}$, —N$R^{54}$C(=O)C(=O)N$R^{52}R^{53}$, —N$R^{54}$C(=S)$R^{50}$, —N$R^{54}$C(=S)O$R^{50}$, —N$R^{54}$C(=S)N$R^{52}R^{53}$, —N$R^{54}$S(=O)$_2R^{51}$, —N$R^{54}$S(=O)$_2$N$R^{52}R^{53}$, —O$R^{50}$, =O, —OCN, —OC(=O)$R^{50}$, —OC(=O)N$R^{52}R^{53}$, —OC(=O)O$R^{50}$, —OS(=O)$R^{50}$, —OS(=O)$_2R^{50}$, —OS(=O)$_2$O$R^{50}$, —OS(=O)$_2$N$R^{52}R^{53}$, —SCN, =S, —S(=O)$_nR^{50}$, —S(=O)$_2$O$R^{50}$, —SO$_3R^{57}$, —S(=O)$_2$N$R^{52}R^{53}$, and —S(=O)N$R^{52}R^{53}$; $G^2$, $G^3$, and $G^4$ are independently $C_{1-6}$alkylene optionally substituted by 1-6 $R^{69}$, $C_{6-11}$arylene optionally substituted by 1-6 $R^{69}$, $C_{7-16}$arylalkylene optionally substituted by 1-6 $R^{69}$, $C_{3-11}$cycloalkylene optionally substituted by 1-6 $R^{69}$, $C_{4-17}$cycloalkylalkylene optionally substituted by 1-6 $R^{69}$, 3-15 membered heterocycloalkylene optionally substituted by 1-6 $R^{69}$, 4-21 membered heterocycloalkylalkylene optionally substituted by 1-6 $R^{69}$, 5-15 membered heteroarylene optionally substituted by 1-6 $R^{69}$, 6-21 membered heteroarylalkylene optionally substituted by 1-6 $R^{69}$, —C(=O)—, —C(=O)O—, —C(=O)NR$^{64}$—, —C(=O)C(=O)—, —C(=S)NR$^{64}$—, —NR$^{64}$—, —NR$^{64}$NR$^{64}$—, —NR$^{64}$C(=O)—, —NR$^{64}$C(=O)C(=O)—, —NR$^{64}$C(=O)O—, —NR$^{64}$C(=O)C(=O)O—, —NR$^{64}$C(=O)NR$^{64}$—, —NR$^{64}$C(=O)NR$^{64}$C(=O)—, —NR$^{64}$C(=O)NR$^{64}$C(=O)O—, —NR$^{64}$C(=NR$^{65}$)NR$^{64}$—, —NR$^{64}$C(=O)C(=O)NR$^{64}$—, —NR$^{64}$C(=S)—, —NR$^{64}$C(=S)O—, —NR$^{64}$C(=S)NR$^{64}$—, —NR$^{64}$S(=O)$_2$—, —NR$^{64}$S(=O)$_2$NR$^{64}$—, —O—, —OC(=O)—, —OC(=O)NR$^{64}$—, —OC(=O)O—, —OS(=O)—, —OS(=O)$_2$—, —OS(=O)$_2$O—, —OS(=O)$_2$NR$^{64}$—, —S(=O)$_n$—, —S(=O)$_2$O—, —SO$_3$—, —S(=O)$_2$NR$^{64}$—, —S(=O)NR$^{64}$— or absent; $X^2$, $X^3$, and $X^4$ are independently $C_{1-6}$alkylene optionally substituted by 1-6 $R^{79}$, $C_{6-11}$arylene optionally substituted by 1-6 $R^{79}$, $C_{7-16}$arylalkylene optionally substituted by 1-6 $R^{79}$, $C_{3-11}$cycloalkylene optionally substituted by 1-6 $R^{79}$, $C_{4-17}$cycloalkylalkylene optionally substituted by 1-6 $R^{79}$, 3-15 membered heterocycloalkylene optionally substituted by 1-6 $R^{79}$, 4-21 membered heterocycloalkylalkylene optionally substituted by 1-6 $R^{79}$, 5-15 membered heteroarylene optionally substituted by 1-6 $R^{79}$, 6-21 membered heteroarylalkylene optionally substituted by 1-6 $R^{79}$, —C(=O)—, —C(=O)O—, —C(=O)NR$^{74}$—, —C(=O)C(=O)—, —C(=S)NR$^{74}$—, —NR$^{74}$NR$^{74}$—, —NR$^{74}$C(=O)—, —NR$^{74}$C(=O)C(=O)—, —NR$^{74}$C(=O)O—, —NR$^{74}$C(=O)C(=O)O—, —NR$^{74}$C(=O)NR$^{74}$—, —NR$^{74}$C(=O)NR$^{74}$C(=O)—, —NR$^{74}$C(=O)NR$^{74}$C(=O)O—, —NR$^{74}$C(=NR$^{75}$)NR$^{74}$—, —NR$^{74}$C(=O)C(=O)NR$^{74}$—, —NR$^{74}$C(=S)—, —NR$^{74}$C(=S)O—, —NR$^{74}$C(=S)NR$^{74}$—, —NR$^{74}$S(=O)$_2$—, —NR—, —O—, —OC(=O)—, —OC(=O)NR$^{74}$—, —OC(=O)O—, —OS(=O)—, —OS(=O)$_2$—, —OS(=O)$_2$O—, —OS(=O)$_2$NR$^{74}$—, —S(=O)$_n$—, —S(=O)$_2$O—, —SO$_3$—, —S(=O)$_2$NR$^{74}$—, —S(=O)NR$^{74}$—, or absent; $Z^2$, $Z^3$, and $Z^4$ are independently H, $C_{1-6}$alkyl optionally substituted by 1-6 $R^{89}$, $C_{6-11}$ aryl optionally substituted by 1-6 $R^{89}$, $C_{7-16}$arylalkyl optionally substituted by 1-6 $R^{89}$, $C_{3-11}$cycloalkyl optionally substituted by 1-6 $R^{89}$, $C_{4-17}$cycloalkylalkyl optionally substituted by 1-6 $R^{89}$, 3-15 membered heterocycloalkyl optionally substituted by 1-6 $R^{89}$, 4-21 membered heterocycloalkylalkyl optionally substituted by 1-6 $R^{89}$, 5-15 membered heteroaryl optionally substituted by 1-6 $R^{89}$, 6-21 membered heteroarylalkyl optionally substituted by 1-6 $R^{89}$, halogen, —CN, —C(=O)R$^{80}$, —C(=O)OR$^{80}$, —C(=O)NR$^{82}$R$^{83}$, —C(=O)C(=O)R$^{80}$, —C(=S)NR$^{82}$R$^{83}$, —NC, —NO$_2$, —NR$^{82}$R$^{83}$, —NR$^{84}$NR$^{82}$R$^{83}$, —NR$^{84}$C(=O)R$^{80}$, —NR$^{84}$C(=O)C(=O)R$^{80}$, —NR$^{84}$C(=O)OR$^{81}$, —NR$^{84}$C(=O)C(=O)OR$^{81}$, —NR$^{84}$C(=O)NR$^{82}$R$^{83}$, —NR$^{84}$C(=O)NR$^{84}$C(=O)R$^{80}$, —NR$^{84}$C(=O)NR$^{84}$C(=O)OR$^{80}$, —NR$^{84}$C(=NR$^{85}$)NR$^{82}$R$^{83}$, —NR$^{84}$C(=O)C(=O)NR$^{82}$R$^{83}$, —NR$^{84}$C(=S)R$^{80}$, —NR$^{84}$C(=S)OR$^{80}$, —NR$^{84}$C(=S)NR$^{82}$R$^{83}$, —NR$^{84}$S(=O)$_2$R$^{81}$, —NR$^{84}$S(=O)$_2$NR$^{82}$R$^{83}$, —OR$^{80}$, =O, —OCN, —OC(=O)R$^{80}$, —OC(=O)NR$^{82}$R$^{83}$, —OC(=O)OR$^{80}$, —OS(=O)R$^{80}$, —OS(=O)$_2$R$^{80}$, —OS(=O)$_2$OR$^{80}$, —OS(=O)$_2$NR$^{82}$R$^{83}$, —SCN, =S, —S(=O)$_n$R$^{80}$, —S(=O)$_2$OR$^{80}$, —SO$_3$R$^{87}$, —S(=O)$_2$NR$^{82}$R$^{83}$, or —S(=O)NR$^{82}$R$^{83}$; alternatively, when $L^2$, $A^2$, $G^2$, $X^2$, $L^3$, $A^3$, $G^3$ and $X^3$ are absent, $Z^2$ and $Z^3$ can together form a group of formula -A$^{21}$-A$^{22}$-A$^{23}$-; wherein A$^{21}$, A$^{22}$, and A$^{23}$ are independently chosen from —CZ$^{21}$Z$^{22}$—, —CZ$^{23}$Z$^{24}$CZ$^{25}$Z$^{26}$—, —C(=O)—, —NZ$^{27}$—, —S—, —S(=O)—, —S(=O)$_2$—, or —O—; wherein:

(a) when any two of $Z^{21}$, $Z^{22}$, $Z^{23}$, $Z^{24}$, $Z^{25}$, $Z^{26}$ and $Z^{27}$ are located on adjacent atoms, they may together form a bond between the atoms, and (b) any of $Z^{21}$, $Z^{22}$, $Z^{23}$, $Z^{24}$, $Z^{25}$, $Z^{26}$ and $Z^{27}$ may be independently chosen from H, $C_{1-6}$alkyl optionally substituted by 1-6 $R^{99}$, $C_{6-11}$ aryl optionally substituted by 1-7 $R^{99}$, $C_{7-16}$arylalkyl optionally substituted by 1-6 $R^{99}$, $C_{3-11}$cycloalkyl optionally substituted by 1-6 $R^{99}$, $C_{4-17}$cycloalkylalkyl optionally substituted by 1-6 $R^{99}$, 3-15 membered heterocycloalkyl optionally substituted by 1-6 $R^{99}$, 4-21 membered heterocycloalkylalkyl optionally substituted by 1-6 $R^{99}$, 5-15 membered heteroaryl optionally substituted by 1-6 $R^{99}$, 6-21 membered heteroarylalkyl optionally substituted by 1-6 $R^{99}$, halogen, —CN, —C(=O)R$^{90}$, —C(=O)OR$^{90}$, —C(=O)NR$^{92}$R$^{93}$, —C(=O)C(=O)R$^{90}$, —C(=S)NR$^{92}$R$^{93}$, —NC, —NO$_2$, —NR$^{92}$R$^{93}$, —NR$^{94}$NR$^{92}$R$^{93}$, —NR$^{94}$C(=O)R$^{90}$, —NR$^{94}$C(=O)C(=O)R$^{90}$, —NR$^{94}$C(=O)OR$^{91}$, —NR$^{94}$C(=O)C(=O)OR$^{91}$, —NR$^{94}$C(=O)NR$^{92}$R$^{93}$, —NR$^{94}$C(=O)NR$^{94}$C(=O)R$^{90}$, —NR$^{94}$C(=O)NR$^{94}$C(=O)OR$^{90}$, —NR$^{94}$C(=NR$^{95}$)NR$^{92}$R$^{93}$, —NR$^{94}$C(=O)C(=O)NR$^{92}$R$^{93}$, —NR$^{94}$C(=S)R$^{90}$, —NR$^{94}$C(=S)OR$^{90}$, —NR$^{94}$C(=S)NR$^{92}$R$^{93}$, —NR$^{94}$S(=O)$_2$R$^{91}$, —NR$^{94}$S(=O)$_2$NR$^{92}$R$^{93}$, —OR$^{90}$, =O, —OCN, —OC(=O)R$^{90}$, —OC(=O)NR$^{92}$R$^{93}$, —OC(=O)OR$^{90}$, —OS(=O)R$^{90}$, —OS(=O)$_2$R$^{90}$, —OS(=O)$_2$OR$^{90}$, —OS(=O)$_2$NR$^{92}$R$^{93}$, —SCN, =S, —S(=O)$_n$R$^{90}$, —S(=O)$_2$OR$^{90}$, —SO$_3$R$^{97}$, —S(=O)$_2$NR$^{92}$R$^{93}$, and —S(=O)NR$^{92}$R$^{93}$; and (c) any two of $Z^{21}$, $Z^{22}$, $Z^{23}$, $Z^{24}$, $Z^{25}$, $Z^{26}$ and $Z^{27}$ may together form a group of formula -A$^{31}$-A$^{32}$-A$^{33}$-, wherein A$^{31}$, A$^{32}$, and A$^{33}$ are independently chosen from —CZ$^{31}$Z$^{32}$—, —CZ$^{33}$Z$^{34}$CZ$^{35}$Z$^{36}$—, —C(=O)—, —NZ$^{37}$—, —S—, —S(=O)—, —S(=O)$_2$—, or —O— wherein:

(i) when any two of $Z^{31}$, $Z^{32}$, $Z^{33}$, $Z^{34}$, $Z^{35}$, $Z^{36}$ and $Z^{37}$ are located on adjacent atoms, they may together form a bond between the atoms, and (ii) any of any of $Z^{21}$, $Z^{22}$, $Z^{23}$, $Z^{24}$, $Z^{25}$, $Z^{26}$ and $Z^{27}$ may be independently chosen from H, $C_{1-6}$alkyl optionally substituted by 1-6 $R^{139}$, $C_{6-11}$aryl optionally substituted by 1-7 $R^{139}$, $C_{7-16}$arylalkyl optionally substituted by 1-6 $R^{139}$, $C_{3-11}$cycloalkyl optionally substituted by 1-6 $R^{139}$, $C_{4-17}$cycloalkylalkyl optionally substituted by 1-6 $R^{139}$, 3-15 membered heterocycloalkyl optionally substituted by 1-6 $R^{139}$, 4-21 membered heterocycloalkylalkyl optionally substituted by 1-6 $R^{139}$, 5-15 membered heteroaryl optionally substituted by 1-6 $R^{139}$, 6-21 membered heteroarylalkyl optionally substituted by 1-6 $R^{139}$, halogen, —CN, —C(=O)R$^{130}$, —C(=O)OR$^{130}$, —C(=O)NR$^{132}$R$^{133}$, —C(=O)C(=O)R$^{130}$, —C(=S)NR$^{132}$R$^{133}$, —NC, —NO$_2$, —NR$^{132}$R$^{133}$, —NR$^{134}$NR$^{132}$R$^{133}$, —NR$^{134}$C(=O)R$^{130}$, —NR$^{134}$C(=O)C(=O)R$^{130}$, —NR$^{134}$C(=O)OR$^{131}$, —NR$^{134}$C(=O)C(=O)OR$^{131}$, —NR$^{134}$C(=O)NR$^{132}$R$^{133}$, —NR$^{134}$C(=O)NR$^{134}$C(=O)R$^{130}$, —NR$^{134}$C(=O)NR$^{134}$C(=O)OR$^{130}$, —NR$^{134}$C(=NR$^{135}$)NR$^{132}$R$^{133}$, —NR$^{134}$C(=O)C(=O)NR$^{132}$R$^{133}$, —NR$^{134}$C(=S)R$^{130}$, —NR$^{134}$C(=S)OR$^{130}$, —NR$^{134}$C(=S)NR$^{132}$R$^{133}$, —NR$^{134}$S(=O)$_2$R$^{131}$, —NR$^{134}$S(=O)$_2$NR$^{132}$R$^{133}$, —OR$^{130}$, =O, —OCN, —OC(=O)R$^{130}$, —OC(=O)NR$^{132}$R$^{133}$, —OC(=O)OR$^{130}$, —OS(=O)R$^{130}$, —OS(=O)$_2$R$^{130}$, —OS(=O)$_2$OR$^{130}$, —OS(=O)$_2$NR$^{132}$R$^{133}$, —SCN, =S, —S(=O)$_n$R$^{130}$, —S(=O)$_2$OR$^{130}$, —SO$_3$R$^{137}$, —S(=O)$_2$NR$^{132}$R$^{133}$, and —S(=O)NR$^{132}$R$^{133}$; R$^9$, R$^{19}$, R$^{29}$, R$^{39}$, R$^{49}$, R$^{59}$, R$^{69}$, R$^{79}$, R$^{89}$, R$^{99}$, and R$^{139}$ at each occurrence is independently chosen from $C_{1-6}$alkyl optionally substituted by 1-6 $R^{179}$, $C_{6-11}$aryl optionally substituted by 1-6 $R^{179}$, $C_{7-16}$arylalkyl optionally substituted by 1-6 $R^{179}$, $C_{3-11}$cycloalkyl optionally substituted by 1-6 $R^{179}$, $C_{4-17}$cycloalkylalkyl optionally substituted by 1-6 $R^{179}$, 3-15 membered heterocycloalkyl optionally substituted by 1-6 $R^{179}$, 4-21 membered heterocycloalkylalkyl optionally substituted by 1-6 $R^{179}$, 5-15 membered heteroaryl optionally substituted by 1-6 $R^{179}$, 6-21 membered heteroarylalkyl optionally substituted by 1-6 $R^{179}$, halogen, —CN, —C(=O)$R^{170}$, —C(=O)O$R^{170}$, —C(=O)N$R^{172}R^{173}$, —C(=O)C(=O)$R^{170}$, —C(=S)N$R^{172}R^{173}$, —NC, —NO$_2$, —N$R^{172}R^{173}$, —N$R^{174}$N$R^{172}R^{173}$, —N$R^{174}$C(=O)$R^{170}$, —N$R^{174}$C(=O)C(=O)$R^{170}$, —N$R^{174}$C(=O)O$R^{171}$, —N$R^{174}$C(=O)C(=O)O$R^{171}$, —N$R^{174}$C(=O)N$R^{172}R^{173}$, —N$R^{174}$C(=O)N$R^{174}$C(=O)$R^{170}$, —N$R^{174}$C(=O)N$R^{174}$C(=O)O$R^{170}$, —N$R^{174}$C(=N$R^{175}$)N$R^{172}R^{173}$, —N$R^{174}$C(=O)C(=O)N$R^{172}R^{173}$, —N$R^{174}$C(=S)$R^{170}$, —N$R^{174}$C(=S)O$R^{170}$, —N$R^{174}$C(=S)N$R^{172}R^{173}$, —N$R^{174}$S(=O)$_2R^{171}$, —N$R^{174}$S(=O)$_2$N$R^{172}R^{173}$, —O$R^{170}$, =O, —OCN, —OC(=O)$R^{170}$, —OC(=O)N$R^{172}R^{173}$, —OC(=O)O$R^{170}$, —OS(=O)$R^{170}$, —OS(=O)$_2R^{170}$, —OS(=O)$_2$O$R^{170}$, —OS(=O)$_2$N$R^{172}R^{173}$, —SCN, =S, —S(=O)$_nR^{170}$, —S(=O)$_2$O$R^{170}$, —SO$_3R^{177}$, —S(=O)$_2$N$R^{172}R^{173}$, and —S(=O)N$R^{172}R^{173}$; $R^1$, $R^4$, $R^5$, $R^6$, $R^{19}$, $R^{11}$, $R^{14}$, $R^{15}$, $R^{16}$, $R^{17}$, $R^{21}$, $R^{24}$, $R^{25}$, $R^{26}$, $R^{31}$, $R^{34}$, $R^{35}$, $R^{36}$, $R^{41}$, $R^{44}$, $R^{45}$, $R^{46}$, $R^{59}$, $R^{51}$, $R^{54}$, $R^{55}$, $R^{56}$, $R^{57}$, $R^{61}$, $R^{64}$, $R^{65}$, $R^{66}$, $R^{71}$, $R^{74}$, $R^{75}$, $R^{76}$, $R^{89}$, $R^{81}$, $R^{84}$, $R^{85}$, $R^{86}$, $R^{87}$, $R^{90}$, $R^{91}$, $R^{94}$, $R^{95}$, $R^{96}$, $R^{97}$, $R^{100}$, $R^{101}$, $R^{104}$, $R^{105}$, $R^{106}$, $R^{107}$, $R^{130}$, $R^{131}$, $R^{134}$, $R^{135}$, $R^{136}$, $R^{137}$, $R^{170}$, $R^{171}$, $R^{174}$, $R^{175}$, $R^{176}$ and $R^{177}$ at each occurrence is independently chosen from H, $C_{1-6}$alkyl optionally substituted by 1-6 $R^{189}$, $C_{6-11}$aryl optionally substituted by 1-6 $R^{189}$, $C_{7-16}$arylalkyl optionally substituted by 1-6 $R^{189}$, $C_{3-11}$cycloalkyl optionally substituted by 1-6 $R^{189}$, $C_{4-17}$cycloalkylalkyl optionally substituted by 1-6 $R^{189}$, 3-15 membered heterocycloalkyl optionally substituted by 1-6 $R^{189}$, 4-21 membered heterocycloalkylalkyl optionally substituted by 1-6 $R^{189}$, 5-15 membered heteroaryl optionally substituted by 1-6 $R^2$, $R^3$, $R^{12}$, $R^{189}$, and 6-21 membered heteroarylalkyl optionally substituted by 1-6 $R^{189}$; $R^{13}$, $R^{22}$, $R^{23}$, $R^{32}$, $R^{33}$, $R^{42}$, $R^{43}$, $R^{52}$, $R^{53}$, $R^{62}$, $R^{63}$, $R^{72}$, $R^{73}$, $R^{82}$, $R^{83}$, $R^{92}$, $R^{93}$, $R^{102}$, $R^{103}$, $R^{132}$, $R^{133}$, $R^{172}$ and $R^{173}$ at each occurrence is independently chosen from H, $C_{1-6}$alkyl optionally substituted by 1-6 $R^{199}$, $C_{6-11}$ aryl optionally substituted by 1-7 $R^{199}$, $C_{7-16}$arylalkyl optionally substituted by 1-6 $R^{199}$, $C_{3-11}$cycloalkyl optionally substituted by 1-6 $R^{199}$, $C_{4-17}$cycloalkylalkyl optionally substituted by 1-6 $R^{199}$, 3-15 membered heterocycloalkyl optionally substituted by 1-6 $R^{199}$, 4-21 membered heterocycloalkylalkyl optionally substituted by 1-6 $R^{199}$, 5-15 membered heteroaryl optionally substituted by 1-6 $R^{199}$, and 6-21 membered heteroarylalkyl optionally substituted by 1-6 $R^{199}$; or any $R^2$ and $R^3$, $R^{12}$ and $R^{13}$, $R^{22}$ and $R^{23}$, $R^{32}$ and $R^{33}$, $R^{42}$ and $R^{43}$, $R^{52}$ and $R^{53}$, $R^{62}$ and $R^{63}$, $R^{72}$ and $R^{73}$, $R^{82}$ and $R^{83}$, $R^{92}$ and $R^{93}$, $R^{102}$ and $R^{103}$, $R^{132}$ and $R^{133}$, or $R^{172}$ and $R^{173}$ may form, together with the nitrogen atom to which they are attached, a 3-15 membered heterocycloalkyl optionally substituted by 1-6 $R^{209}$ or a 5-15 membered heteroaryl optionally substituted by 1-6, $R^{209}$; $R^{179}$, $R^{189}$, $R^{199}$ and $R^{209}$ at each occurrence is independently chosen from $C_{1-6}$alkyl optionally substituted by 1-6 $R^{219}$, $C_{6-11}$aryl optionally substituted by 1-7 $R^{219}$, $C_{7-16}$arylalkyl optionally substituted by 1-6 $R^{219}$, $C_{3-11}$cycloalkyl optionally substituted by 1-6 $R^{219}$, $C_{4-17}$cycloalkylalkyl optionally substituted by 1-6 $R^{219}$, 3-15 membered heterocycloalkyl optionally substituted by 1-6 $R^{219}$, 4-21 membered heterocycloalkylalkyl optionally substituted by 1-6 $R^{219}$, 5-15 membered heteroaryl optionally substituted by 1-6 $R^{219}$, 6-21 membered heteroarylalkyl optionally) substituted by 1-6 $R^{219}$, halogen, —CN, —C(=O)$R^{210}$, —C(=O)O$R^{212}R^{213}$, —C(=O)C(=O)$R^{210}$, —C(=S)N$R^{212}R^{213}$, —NC, —NO$_2$, —N$R^{212}R^{213}$, —N$R^{214}$N$R^{212}R^{213}$, —N$R^{214}$C(=O)$R^{210}$, —N$R^{214}$C(=O)C(=O)$R^{210}$, —N$R^{214}$C(=O)O$R^{211}$, —N$R^{214}$C(=O)C(=O)O$R^{211}$, —N$R^{214}$C(O)N$R^{212}R^{213}$, —N$R^{214}$C(=O)N$R^{214}$C(=O)$R^{210}$, —N$R^{214}$C(=O)N$R^{214}$C(=O)O$R^{210}$, —N$R^{214}$C(=N$R^{215}$)N$R^{212}R^{213}$, —N$R^{214}$C(=O)C(=O)N$R^{212}R^{213}$, —N$R^{214}$C(=S)$R^{210}$, —N$R^{214}$C(=S)O$R^{210}$, —N$R^{214}$C(=S)N$R^{212}R^{213}$, —N$R^{214}$S(=O)$_2R^{211}$, —N$R^{214}$S(=O)$_2$N$R^{212}R^{213}$, —O$R^{210}$, =O, —OCN, —OC(=O)$R^{210}$, —OC(=O)N$R^{212}R^{213}$, —C(=O)O$R^{210}$, —OS(=O)$R^{210}$, —OS(=O)$_2R^{210}$, —OS(=O)$_2$O$R^{210}$, —OS(=O)$_2$N$R^{212}R^{213}$, —SCN, =S, —S(=O)$_nR^{210}$, —S(=O)$_2$O$R^{210}$, —SO$_3R^{217}$, —S(=O)$_2$N$R^{212}R^{213}$, and —S(=O)N$R^{212}R^{213}$; $R^{210}$, $R^{211}$, $R^{214}$, $R^{215}$, $R^{216}$ and $R^{217}$ at each occurrence is independently chosen from H, $C_{1-6}$alkyl optionally substituted by 1-6 $R^{229}$, $C_{6-11}$ aryl optionally substituted by 1-7 $R^{229}$, $C_{7-16}$arylalkyl optionally substituted by 1-6 $R^{229}$, $C_{3-11}$cycloalkyl optionally substituted by 1-6 $R^{229}$, $C_{4-17}$cycloalkylalkyl optionally substituted by 1-6 $R^{229}$, 3-15 membered heterocycloalkyl optionally substituted by 1-6 $R^{229}$, 4-21 membered heterocycloalkylalkyl optionally substituted by 1-6 $R^{229}$, 5-15 membered heteroaryl optionally substituted by 1-6 $R^{229}$, and 6-21 membered heteroarylalkyl optionally substituted by 1-6 $R^{229}$; $R^{212}$ and $R^{213}$ at each occurrence is independently chosen from H, $C_{1-6}$alkyl optionally substituted by 1-6 $R^{239}$, $C_{6-11}$aryl optionally substituted by 1-7 $R^{239}$, $C_{7-16}$arylalkyl optionally substituted by 1-6 $R^{239}$, $C_{3-11}$cycloalkyl optionally substituted by 1-6 $R^{239}$, $C_{4-17}$cycloalkylalkyl optionally substituted by 1-6 $R^{239}$, 3-15 membered heterocycloalkyl optionally substituted by 1-6 $R^{239}$, 4-21 membered heterocycloalkylalkyl optionally substituted by 1-6 $R^{239}$, 5-15 membered heteroaryl optionally substituted by 1-6 $R^{239}$, and 6-21 membered heteroarylalkyl optionally substituted by 1-6 $R^{239}$; or any $R^{212}$ and $R^{213}$ may form, together with the nitrogen atom to which they are attached, a 3-15 membered heterocycloalkyl optionally substituted by 1-6 $R^{249}$ or a 5-15 membered heteroaryl optionally substituted by 1-6 $R^{249}$; $R^{219}$, $R^{229}$, $R^{239}$ and $R^{249}$ at each occurrence is independently chosen from $C_{1-6}$alkyl optionally substituted by 1-6 halogen, $C_{2-6}$alkenyl, $C_{2-6}$alkynyl, $C_{6-11}$ aryl, $C_{7-16}$arylalkyl, $C_{3-11}$cycloalkyl, $C_{4-17}$cycloalkylalkyl, 3-15 membered heterocycloalkyl, 4-21 membered heterocycloalkylalkyl, 5-15 membered heteroaryl, 6-21 membered heteroarylalkyl, halogen, —CN, —C(=O)$R^{250}$, —C(=O)O$R^{250}$, —C(=O)N$R^{250}R^{250}$, —C(=O)C(=O)$R^{250}$, —C(=S)N$R^{250}R^{250}$, —NC, —NO$_2$, —N$R^{250}R^{250}$, —N$R^{250}R^{250}$, —C(=O)C(=O)$R^{250}$, —N$R^{250}$C(=O)C(=O)$R^{250}$, —N$R^{250}$C(=O)O$R^{250}$, —N$R^{250}$C(=O)C(=O)O$R^{250}$, —N$R^{250}$C(=O)N$R^{250}R^{250}$, —N$R^{250}$C(=O)N$R^{250}$C(=O)$R^{250}$, —N$R^{250}$C(=O)N$R^{250}$C(=O)O$R^{250}$, —N$R^{250}$C(=N$R^{250}$)N$R^{250}R^{250}$, —N$R^{250}$C(=O)C(=O)N$R^{250}R^{250}$, —N$R^{250}$C(=S)$R^{250}$, —N$R^{250}$C(=S)O$R^{250}$, —N$R^{250}$C(=S)N$R^{250}R^{250}$, —N$R^{250}$S(=O)$_2R^{250}$, —N$R^{250}$S(=O)$_2$N$R^{250}R^{250}$, —O$R^{250}$, =O, —OCN, —OC(=O)$R^{250}$, —OC(=O)N$R^{250}R^{250}$, —OC(=O)O$R^{250}$, —OS(=O)$R^{250}$, —OS(=O)$_2R^{250}$, —OS(=O)$_2$O$R^{250}$, —OS(=O)$_2$N$R^{250}R^{250}$, —SCN, =S, —S(=O)$_nR^{250}$, —S(=O)$_2$O$R^{250}$, —SO$_3R^{250}$, —S(=O)$_2$N$R^{250}R^{250}$, and —S(=O)N$R^{250}R^{250}$; $R^{250}$ at each occurrence is independently chosen from H, $C_{1-6}$alkyl, and $C_{1-6}$haloalkyl; and n at each occurrence is independently chosen from 0, 1, and 2; with the proviso that the compound is not:

(a)

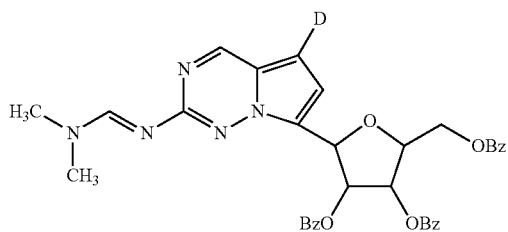

wherein
Bz is benzoyl, and
D is —C(=O)H or H, (b)

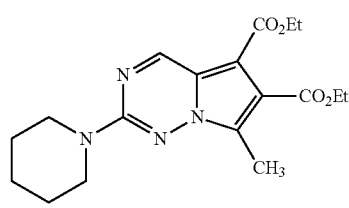

wherein Et is ethyl, or (c)

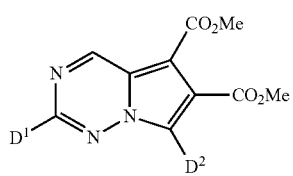

wherein
$D^1$ is methoxy, phenyl, or 4-methylphenyl,
$D^2$ is —CH$_2$C(=O)OMe or —C(=O)OMe, and
Me is methyl.

As another example, also included within the scope of the present invention are compounds of formula I and pharmaceutically acceptable salts thereof in which $Q^1$ is -L$^1$-A$^1$-G$^1$-X$^1$—Z$^1$; $Q^2$ is -L$^2$-A$^2$-G$^2$-X$^2$—Z$^2$; $Q^3$ is -L$^3$-A$^3$-G$^3$-X$^3$—Z$^3$; $Q^4$ is -L$^4$-A$^4$-G$^4$-X$^4$—Z$^4$; L$^1$ is C$_{1-6}$alkylene optionally substituted by 1-6 R$^9$, C$_{7-16}$arylalkylene optionally substituted by 1-6 R$^9$, C$_{3-11}$cycloalkylene optionally substituted by 1-6 R$^9$, C$_{4-17}$cycloalkylalkylene optionally substituted by 1-6 R$^9$, 3-15 membered heterocycloalkylene optionally substituted by 1-6 R$^9$, 4-21 membered heterocycloalkylalkylene optionally substituted by 1-6 R$^9$, 5-15 membered heteroarylene optionally substituted by 1-6 R$^9$, 6-21 membered heteroarylalkylene optionally substituted by 1-6 R$^9$, —C(=O)—, —C(=O)O—, —C(=O)NR$^4$—, —C(=S)NR$^4$—, —NR$^4$—, —NR$^4$NR$^4$—, —NR$^4$C(=O)—, —NR$^4$C(=O)O—, —NR$^4$C(=O)NR$^4$—, —NR$^4$C(=O)NR$^4$C(=O)—, —NR$^4$C(=S)—, —NR$^4$C(=S)O—, —NR$^4$C(=S)NR$^4$—, —NR$^4$S(=O)$_2$—, —O—, —OC(=O)—, —OC(=O)NR$^4$—, —S(=O)$_n$—, —S(=O)$_2$NR$^4$—, —S(=O)NR$^4$—, or absent; A$^1$ is C$_{1-6}$alkylene optionally substituted by 1-6 R$^a$, C$_{6-11}$arylene optionally substituted by 1-6 R$^a$, C$_{7-16}$arylalkylene optionally substituted by 1-6 R$^a$, C$_{3-11}$cycloalkylene optionally substituted by 1-6 R$^a$, C$_{4-17}$cycloalkylalkylene optionally substituted by 1-6 R$^a$, 3-15 membered heterocycloalkylene optionally substituted by 1-6 R$^a$, 4-21 membered heterocycloalkylalkylene optionally substituted by 1-6 R$^a$, 5-15 membered heteroarylene optionally substituted by 1-6 R$^a$, or 6-21 membered heteroarylalkylene optionally substituted by 1-6 R$^a$; each R$^a$ is independently chosen from C$_{1-6}$alkyl optionally substituted by 1-6 R$^{19}$, C$_{6-11}$aryl optionally substituted by 1-6 R$^{19}$, C$_{7-16}$arylalkyl optionally substituted by 1-6 R$^{19}$, C$_{3-11}$cycloalkyl optionally substituted by 1-6 R$^{19}$, C$_{4-17}$cycloalkylalkyl optionally substituted by 1-6 R$^{19}$, 3-15 membered heterocycloalkyl optionally substituted by 1-6 R$^{19}$, 4-21 membered heterocycloalkylalkyl optionally substituted by 1-6 R$^{19}$, 5-15 membered heteroaryl optionally substituted by 1-6 R$^{19}$, 6-21 membered heteroarylalkyl optionally substituted by 1-6 R$^{19}$, halogen, —CN, —C(=O)R$^{10}$, —C(=O)OR$^{10}$, —C(=O)NR$^{12}$R$^{13}$, —C(=S)NR$^{12}$R$^{13}$, —NC, —NO$_2$, —NR$^{12}$R$^{13}$, —NR$^{14}$NR$^{12}$R$^{13}$, —NR$^{14}$OR$^{16}$, —NR$^{14}$C(=O)R$^{10}$, —NR$^{14}$C(=O)OR$^{11}$, —NR$^{14}$C(=O)NR$^{12}$R$^{13}$, —NR$^{14}$C(=O)NR$^{14}$C(=O)R$^{10}$, —NR$^{14}$C(=O)NR$^{14}$C(=O)OR$^{10}$, —NR$^{14}$C(=NR$^{15}$)NR$^{12}$R$^{13}$, —NR$^{14}$C(=S)R$^{10}$, —NR$^{14}$C(=S)NR$^{12}$R$^{13}$, —NR$^{14}$S(=O)$_2$R$^{11}$, —OR$^{10}$, =O, —OCN, —OC(=O)R$^{10}$, —OC(=O)NR$^{12}$R$^{13}$, —SCN, =S, —S(=O)$_n$R$^{10}$, and —S(=O)$_2$NR$^{12}$R$^{13}$; G$^1$ is C$_{1-6}$alkylene optionally substituted by 1-6 R$^{29}$, C$_{6-11}$arylene optionally substituted by 1-6 R$^{29}$, C$_{7-16}$arylalkylene optionally substituted by 1-6 R$^{29}$, C$_{3-11}$cycloalkylene optionally substituted by 1-6 R$^{29}$, C$_{4-17}$cycloalkylalkylene optionally substituted by 1-6 R$^{29}$, 3-15 membered heterocycloalkylene optionally substituted by 1-6 R$^{29}$, 4-21 membered heterocycloalkylalkylene optionally substituted by 1-6 R$^{29}$, 5-15 membered heteroarylene optionally substituted by 1-6 R$^{29}$, 6-21 membered heteroarylalkylene optionally substituted by 1-6 R$^{29}$, —C(=O)—, —C(=O)O—, —C(=O)NR$^{24}$—, —C(=S)NR$^{24}$—, —NR$^{24}$—, —NR$^{24}$—, —NR$^{24}$NR$^{24}$—, —NR$^{24}$C(=O)—, —NR$^{24}$C(=O)O—, —NR$^{24}$C(=O)NR$^{24}$—, —NR$^{24}$C(=O)NR$^{24}$C(=O)—, —NR$^{24}$C(=O)NR$^{24}$C(=O)O—, —NR$^{24}$C(=S)—, —NR$^{24}$C(=S)NR$^{24}$—, —NR$^{24}$S(=O)$_2$—, —O—, —OC(=O)—, —OC(=O)NR$^{24}$—, —S(=O)$_n$—, —S(=O)$_2$NR$^{24}$—, or absent; X$^1$ is C$_{1-6}$alkylene optionally substituted by 1-6 R$^{39}$, C$_{6-11}$arylene optionally substituted by 1-6 R$^{39}$, C$_{7-16}$arylalkylene optionally substituted by 1-6 R$^{39}$, C$_{3-11}$cycloalkylene optionally substituted by 1-6 R$^{39}$, C$_{4-17}$cycloalkylalkylene optionally substituted by 1-6 R$^{39}$, 3-15 membered heterocycloalkylene optionally substituted by 1-6 R$^{39}$, 4-21 membered heterocycloalkylalkylene optionally substituted by 1-6 R$^{39}$, 5-15 membered heteroarylene optionally substituted by 1-6 R$^{39}$, 6-21 membered heteroarylalkylene optionally substituted by 1-6 R$^{39}$, —C(=O)—, —C(=O)O—, —C(=O)NR$^{34}$—, —C(=S)NR$^{34}$—, —NR$^{34}$—, —NR$^{34}$NR$^{34}$—, —NR$^{34}$C(=O)—, —NR$^{34}$C(=O)O—, —NR$^{34}$C(=O)NR$^{34}$—, —NR$^{34}$C(=O)NR$^{34}$C(=O)—, —NR$^{34}$C(=O)NR$^{34}$C(=O)O—, —NR$^{34}$C(=NR$^{35}$)NR$^{34}$—, —NR$^{34}$C(=S)NR$^{34}$—, —NR$^{34}$S(=O)$_2$—, —O—, —OC(=O)—, —OC(=O)NR$^{34}$—, —S(=O)$_n$—, —S(=O)$_2$NR$^{34}$—, or absent; Z$^1$ is H, C$_{1-6}$alkyl optionally substituted by 1-6 R$^{49}$, C$_{7-16}$arylalkyl optionally substituted by 1-6 R$^{49}$, C$_{3-11}$cycloalkyl optionally substituted by 1-6 R$^{49}$, C$_{4-17}$cycloalkylalkyl optionally substituted by 1-6 R$^{49}$, 3-15 membered heterocycloalkyl optionally substituted by 1-6 R$^{49}$, 4-21 membered heterocycloalkylalkyl optionally substituted by 1-6 R$^{49}$, 5-15 membered heteroaryl optionally substituted by 1-6 R$^{49}$, 6-21 membered heteroarylalkyl optionally substituted by 1-6 R$^{49}$, halogen, —CN, —C(=O)R$^{100}$, —C(=O)OR$^{100}$, —C(=O)NR$^{102}$R$^{103}$, —C(=S)NR$^{102}$R$^{103}$, —NC, —NO$_2$, —NR$^{102}$R$^{103}$, —NR$^{104}$NR$^{102}$R$^{103}$, —NR$^{104}$C(=O)R$^{100}$, —NR$^{104}$C(=O)OR$^{101}$, —NR$^{104}$C(=O)NR$^{102}$R$^{103}$, —NR$^{104}$C(=O)NR$^{104}$C(O)R$^{100}$, —NR$^{104}$C(=NR$^{105}$)

$NR^{102}R^{103}$, $-NR^{104}C(=S)R^{100}$, $-NR^{104}C(=S)NR^{102}R^{103}$, $-NR^{104}S(O)_2R^{101}$, $-OR^{100}$, $=O$, $-OCN$, $-OC(=O)R^{100}$, $-OC(=O)NR^{102}R^{103}$, $-SCN$, $=S$, $-S(=O)_nR^{100}$, $-S(=O)_2NR^{102}R^{103}$, or absent; $L^2$, $L^3$, and $L^4$ are independently $-C(=O)-$, $-C(=O)O-$, $-C(=O)NR^{44}-$, $-C(=S)NR^{44}-$, $-NR^{44}-$, $-NR^{44}NR^{44}-$, $-NR^{44}C(=O)-$, $-NR^{44}C(=O)O-$, $-NR-$, $-NR^{44}C(=O)NR^{44}C(=O)-$, $-NR^{44}C(=O)NR^{44}C(=O)O-$, $-NR^{44}C(=NR^{45})NR^{44}-$, $-NR^{44}C(=S)NR^{44}-$, $-NR^{44}S(=O)_2-$, $-O-$, $-OC(=O)-$, $-OC(=O)NR^{44}-$, $-S(=O)_n-$, or $-S(=O)_2NR^{44}-$; $A^2$, $A^3$, and $A^4$ are independently $C_{1-6}$alkylene optionally substituted by 1-6 $R^b$, $C_{6-11}$arylene optionally substituted by 1-6 $R^b$, $C_{3-11}$cycloalkylene optionally substituted by 1-6 $R^b$, 3-15 membered heterocycloalkylene optionally substituted by 1-6 $R^b$, 5-15 membered heteroarylene optionally substituted by 1-6 $R^b$, or absent; each $R^b$ is independently chosen from $C_{1-6}$alkyl optionally substituted by 1-6 $R^{59}$, $C_{2-6}$alkenyl optionally substituted by 1-6 $R^{59}$, $C_{2-6}$alkynyl optionally substituted by 1-9 $R^{59}$, $C_{6-11}$ aryl optionally substituted by 1-7 $R^{59}$, $C_{7-16}$arylalkyl optionally substituted by 1-6 $R^{59}$, $C_{3-11}$cycloalkyl optionally substituted by 1-6 $R^{59}$, $C_{4-17}$cycloalkylalkyl optionally substituted by 1-6 $R^{59}$, 3-15 membered heterocycloalkyl optionally substituted by 1-6 $R^{59}$, 4-21 membered heterocycloalkylalkyl optionally substituted by 1-6 $R^{59}$, 5-15 membered heteroaryl optionally substituted by 1-6 $R^{59}$, 6-21 membered heteroarylalkyl optionally substituted by 1-6 $R^{59}$, halogen, $-CN$, $-C(=O)R^{50}$, $-C(=O)OR^{50}$, $-C(=O)NR^{52}R^{53}$, $-C(=S)NR^{52}R^{53}$, $-NC$, $-NO_2$, $-NR^{52}R^{53}$, $-NR^{54}NR^{52}R^{53}$, $-NR^{54}C(=O)R^{50}$, $-NR^{54}C(=O)OR^{51}$, $-NR^{54}C(=O)NR^{52}R^{53}$, $-NR^{54}NR^{25}R^{53}$, $-NR^{54}C(=O)R^{50}$, $-NR^{54}C(=O)NR^{54}C(=O)OR^{50}$, $-NR^{54}C(=NR^{55})NR^{52}R^{53}$, $-NR^{54}C(=S)NR^{52}R^{53}$, $-NR^{54}S(=O)_2R^{51}$, $-OR^{50}$, $=O$, $-OCN$, $-OC(=O)R^{50}$, $-OC(=O)NR^{52}R^{53}$, $-SCN$, $=S$, $-S(=O)_nR^{50}$, and $-S(=O)_2NR^{52}R^{53}$; $G^2$, $G^3$, and $G^4$ are independently $C_{1-6}$alkylene optionally substituted by 1-6 $R^{69}$, $C_{6-11}$ arylene optionally substituted by 1-6 $R^{69}$, $C_{7-16}$arylalkylene optionally substituted by 1-6 $R^{69}$, $C_{3-11}$cycloalkylene optionally substituted by 1-6 $R^{69}$, $C_{4-17}$cycloalkylalkylene optionally substituted by 1-6 $R^{69}$, 3-15 membered heterocycloalkylene optionally substituted by 1-6 $R^{69}$, 4-21 membered heterocycloalkylalkylene optionally substituted by 1-6 $R^{69}$, 5-15 membered heteroarylene optionally substituted by 1-6 $R^{69}$, 6-21 membered heteroarylalkylene optionally substituted by 1-6 $R^{69}$, $-C(=O)-$, $-C(=O)O-$, $-C(=O)NR^{64}-$, $-C(=S)NR^{64}-$, $-NR^{64}-$, $-NR^{64}NR^{64}-$, $-NR^{64}C(=O)-$, $-NR^{64}C(=O)O-$, $-NR^{64}C(=S)NR^{64}-$, $-NR^{64}C(=O)NR^{64}C(=O)-$, $-NR^{64}C(=NR^{65})NR^{64}-$, $-NR-$, $-NR-$, $-NR^{64}S(=O)_2-$, $-O-$, $-OC(=O)-$, $-OC(=O)NR^{64}-$, $-S(=O)_n-$, $-S(=O)_2NR^{64}-$, or absent; $X^2$, $X^3$, and $X^4$ are independently $C_{1-6}$alkylene optionally substituted by 1-6 $R^{79}$, $C_{6-11}$ arylene optionally substituted by 1-6 $R^{79}$, $C_{7-16}$arylalkylene optionally substituted by 1-6 $R^{79}$, $C_{3-11}$cycloalkylene optionally substituted by 1-6 $R^{79}$, $C_{4-17}$cycloalkylalkylene optionally substituted by 1-6 $R^{79}$, 3-15 membered heterocycloalkylene optionally substituted by 1-6 $R^{79}$, 4-21 membered heterocycloalkylalkylene optionally substituted by 1-6 $R^{79}$, 5-15 membered heteroarylene optionally substituted by 1-6 $R^{79}$, 6-21 membered heteroarylalkylene optionally substituted by 1-6 $R^{79}$, $-C(=O)-$, $-C(=O)O-$, $-C(=O)NR^{74}-$, $-C(=S)NR^{74}-$, $-NR-$, $-NR^{74}NR^{74}-$, $-NR^{74}C(=O)-$, $-NR^{74}C(=O)O-$, $-NR^{74}C(=O)NR^{74}-$, $-NR^{74}C(=O)NR^{74}C(=O)-$, $-NR^{74}C(=O)NR^{74}C(=O)O-$, $-NR^{74}C(=NR^{75})NR^{74}-$, $-NR^{74}C(=S)-$, $-NR^{74}C(=S)NR^{74}-$, $-NR^{74}S(=O)_2-$, $-O-$, $-OC(=O)-$, $-OC(=O)NR^{74}-$, $-S(=O)_n-$, $-S(=O)_2NR^{74}-$, or absent; $Z^2$, $Z^3$, and $Z^4$ are independently H, $C_{1-6}$alkyl optionally substituted by 1-6 $R^{89}$, $C_{6-11}$ aryl optionally substituted by 1-7 $R^{89}$, $C_{7-16}$arylalkyl optionally substituted by 1-6 $R^{89}$, $C_{3-11}$cycloalkyl optionally substituted by 1-6 $R^{89}$, $C_{4-17}$cycloalkylalkyl optionally substituted by 1-6 $R^{89}$, 3-15 membered heterocycloalkyl optionally substituted by 1-6 $R^{89}$, 4-21 membered heterocycloalkylalkyl optionally substituted by 1-6 $R^{89}$, 5-15 membered heteroaryl optionally substituted by 1-6 $R^{89}$, 6-21 membered heteroarylalkyl optionally substituted by 1-6 $R^{89}$, halogen, $-CN$, $-C(=O)R^{80}$, $-C(=O)OR^{80}$, $-C(=O)NR^{82}R^{83}$, $-C(=S)NR^{82}R^{83}$, $-NC$, $-NO_2$, $-NR^{82}R^{83}$, $-NR^{84}NR^{82}R^{83}$, $-NR^{84}C(=O)R^{80}$, $-NR^{84}C(=O)OR^{81}$, $-NR^{84}C(=O)NR^{82}R^{83}$, $-NR^{84}C(=O)NR^{84}C(=O)R^{80}$, $-NR^{84}C(=O)NR^{84}C(=O)OR^{80}$, $-NR^{84}C(=NR^{85})NR^{82}R^{83}$, $-NR^{84}C(=S)R^{80}$, $-NR^{84}C(=S)NR^{82}R^{83}$, $-NR^{84}S(=O)_2R^{81}$, $-OR^{80}$, $=O$, $-OCN$, $-OC(=O)R^{80}$, $-OC(=O)NR^{82}R^{83}$, $-SCN$, $=S$, $-S(=O)_nR^{80}$, $-S(=O)_2OR^{80}$, or $-S(=O)_2NR^{82}R^{83}$; alternatively, when $L^2$, $A^2$, $G^2$, $X^2$, $L^3$, $A^3$, $G^3$ and $X^3$ are absent, $Z^2$ and $Z^3$ can together form a group of formula $-A^{21}-A^{22}-A^{23}-$; wherein $A^{21}$, $A^{22}$, and $A^{23}$ are independently chosen from $-CZ^{21}Z^{22}-$, $-CZ^{23}Z^{24}CZ^{25}Z^{26}-$, $-NZ^{27}-$, $-S-$, $-S(=O)-$, $-S(=O)_2-$, or $-O-$; wherein:

(a) when any two of $Z^{21}$, $Z^{22}$, $Z^{23}$, $Z^{24}$, $Z^{25}$, $Z^{26}$ and $Z^{27}$ are located on adjacent atoms, they may together form a bond between the atoms, and (b) any of $Z^{21}$, $Z^{22}$, $Z^{23}$, $Z^{24}$, $Z^{25}$, $Z^{26}$ and $Z^{27}$ may be independently chosen from H, $C_{1-6}$alkyl optionally substituted by 1-6 $R^{99}$, $C_{6-11}$aryl optionally substituted by 1-7 $R^{99}$, $C_{7-16}$arylalkyl optionally substituted by 1-6 $R^{99}$, $C_{3-11}$cycloalkyl optionally substituted by 1-6 $R^{99}$, $C_{4-17}$cycloalkylalkyl optionally substituted by 1-6 $R^{99}$, 3-15 membered heterocycloalkyl optionally substituted by 1-6 $R^{99}$, 4-21 membered heterocycloalkylalkyl optionally substituted by 1-6 $R^{99}$, 5-15 membered heteroaryl optionally substituted by 1-6 $R^{99}$, 6-21 membered heteroarylalkyl optionally substituted by 1-6 $R^{99}$, halogen, $-CN$, $-C(=O)R^{90}$, $-C(=O)OR^{90}$, $-C(=O)NR^{92}R^{93}$, $-C(=S)NR^{92}R^{93}$, $-NC$, $-NO_2$, $-NR^{92}R^{93}$, $-NR^{94}NR^{92}R^{93}$, $-NR^{94}C(=O)R^{90}$, $-NR^{94}C(=O)OR^{91}$, $-NR^{94}C(=O)NR^{92}R^{93}$, $-NR^{94}C(=O)NR^{94}C(=O)R^{90}$, $-NR^{94}C(=O)NR^{94}C(=O)OR^{90}$, $-NR^{94}C(=NR^{95})NR^{92}R^{93}$, $-NR^{94}C(=S)R^{90}$, $-NR^{94}C(=S)NR^{92}R^{93}$, $-NR^{94}S(=O)_2R^{91}$, $-OR^{90}$, $=O$, $-OCN$, $-OC(=O)NR^{92}R^{93}$, $-SCN$, $=S$, $-S(=O)_nR^{90}$, and $-S(=O)_2NR^{92}R^{93}$; and (c) any two of $Z^{21}$, $Z^{22}$, $Z^{23}$, $Z^{24}$, $Z^{25}$, $Z^{26}$ and $Z^{27}$ may together form a group of formula $-A^{31}-A^{32}-A^{33}-$, wherein $A^{31}$, $A^{32}$, and $A^{33}$ are independently chosen from $-CZ^{31}Z^{32}-$, $-CZ^{33}Z^{34}CZ^{35}Z^{36}-$, $-C(=O)-$, $-NZ^{37}-$, $-S-$, $-S(=O)-$, $-S(=O)_2-$, or $-O-$ wherein:

(i) when any two of $Z^{31}$, $Z^{32}$, $Z^{33}$, $Z^{34}$, $Z^{35}$, $Z^{36}$ and $Z^{37}$ are located on adjacent atoms, they may together form a bond between the atoms, and (ii) any of any of $Z^{21}$, $Z^{22}$, $Z^{23}$, $Z^{24}$, $Z^{25}$, $Z^{26}$ and $Z^{27}$ may be independently chosen from H, $C_{1-6}$alkyl optionally substituted by 1-6 $R^{139}$, $C_{6-11}$aryl optionally substituted by 1-7 $R^{139}$, $C_{7-16}$arylalkyl optionally substituted by 1-6 $R^{139}$, $C_{3-11}$cycloalkyl optionally substituted by 1-6 $R^{139}$, $C_{4-17}$cycloalkylalkyl optionally substituted by 1-6 $R^{139}$, 3-15 membered heterocycloalkyl optionally substituted by 1-6 $R^{139}$, 4-21 membered heterocycloalkylalkyl optionally substituted by 1-6 $R^{139}$, 5-15 membered heteroaryl optionally substituted by 1-6 $R^{139}$, 6-21 membered heteroarylalkyl optionally substituted by 1-6 $R^{139}$, halogen, $-CN$, $-C(=O)R^{130}$, $-C(=O)OR^{130}$, $-C(=O)NR^{132}R^{133}$, $-C(=S)$ $NR^{132}R^{133}$, —NC, —$NO_2$, —$NR^{132}R^{133}$, —$NR^{134}NR^{132}R^{133}$, —$NR^{134}C(=O)R^{130}$, —$NR^{134}C(=O)OR^{131}$, —$NR^{134}C(=O)NR^{132}R^{133}$, —$NR^{134}C(=O)NR^{134}C(=O)R^{130}$, —$NR^{134}C(=NR^{135})NR^{132}R^{133}$, —$NR^{134}C(=S)R^{130}$, —$NR^{134}C(=S)NR^{132}R^{133}$, —$NR^{134}S(=O)_2R^{131}$, —$OR^{130}$, =O, —OCN, —$OC(=O)R^{130}$, —$OC(=O)NR^{132}R^{133}$, —SCN, =S, —$S(=O)_nR^{130}$, and —$S(=O)_2NR^{132}R^{133}$; $R^9$, $R^{19}$, $R^{29}$, $R^{39}$, $R^{49}$, $R^{59}$, $R^{69}$, $R^{79}$, $R^{89}$, $R^{99}$, and $R^{139}$ at each occurrence is independently chosen from $C_{1-6}$alkyl optionally substituted by 1-6 $R^{179}$, $C_{6-11}$aryl optionally substituted by 1-7 $R^{179}$, $C_{7-16}$arylalkyl optionally substituted by 1-6 $R^{179}$, $C_{3-11}$cycloalkyl optionally substituted by 1-6 $R^{179}$, $C_{4-17}$cycloalkylalkyl optionally substituted by 1-6 $R^{179}$, 3-15 membered heterocycloalkyl optionally substituted by 1-6 $R^{179}$, 4-21 membered heterocycloalkylalkyl optionally substituted by 1-6 $R^{179}$, 5-15 membered heteroaryl optionally substituted by 1-6 $R^{179}$, 6-21 membered heteroarylalkyl optionally substituted by 1-6 $R^{179}$, halogen, —CN, —$C(=O)R^{170}$, —$C(=O)OR^{170}$, —$C(=O)NR^{172}R^{173}$, —$C(=O)C(=O)R^{170}$, —$C(=S)NR^{172}R^{173}$, —NC, —$NO_2$, —$NR^{172}R^{173}$, —$NR^{174}NR^{172}R^{173}$, —$NR^{174}C(=O)R^{170}$, —$NR^{174}C(=O)C(=O)R^{170}$, —$NR^{174}C(=O)OR^{171}$, —$NR^{174}C(=O)NR^{172}R^{173}$, —$NR^{174}C(=O)NR^{174}C(=O)R^{170}$, —$NR^{174}C(=NR^{175})NR^{172}R^{173}$, —$NR^{174}C(=S)R^{170}$, —$NR^{174}C(=S)NR^{172}R^{173}$, —$NR^{174}S(=O)_2R^{171}$, —$OR^{170}$, =O, —OCN, —$OC(=O)R^{170}$, —$OC(=O)NR^{172}R^{173}$, —$OS(=O)_2NR^{172}R^{173}$, —SCN, =S, —$S(=O)_nR^{170}$, —$SO_3R^{177}$, and —$S(=O)_2NR^{172}R^{173}$; $R^1$; $R^4$; $R^5$; $R^6$; $R^{10}$, $R^{11}$, $R^{14}$, $R^{15}$, $R^{16}$, $R^{17}$, $R^{21}$, $R^{24}$, $R^{25}$, $R^{26}$, $R^{31}$, $R^{34}$, $R^{35}$, $R^{36}$, $R^{41}$, $R^{44}$, $R^{45}$, $R^{46}$, $R^{50}$, $R^{51}$, $R^{54}$, $R^{55}$, $R^{56}$, $R^{57}$, $R^{61}$, $R^{64}$, $R^{65}$, $R^{66}$, $R^{71}$, $R^{74}$, $R^{75}$, $R^{76}$, $R^{80}$, $R^{81}$, $R^{84}$, $R^{85}$, $R^{86}$, $R^{87}$, $R^{90}$, $R^{91}$, $R^{94}$, $R^{95}$, $R^{96}$, $R^{97}$, $R^{100}$, $R^{101}$, $R^{104}$, $R^{105}$, $R^{106}$, $R^{107}$, $R^{130}$, $R^{131}$, $R^{134}$, $R^{135}$, $R^{136}$, $R^{137}$, $R^{170}$, $R^{171}$, $R^{174}$, $R^{175}$, $R^{176}$, and $R^{177}$ at each occurrence is independently chosen from H, $C_{1-6}$alkyl optionally substituted by 1-6 $R^{189}$, $C_{6-11}$ aryl optionally substituted by 1-7 $R^{189}$, $C_{7-16}$arylalkyl optionally substituted by 1-6 $R^{189}$, $C_{3-11}$cycloalkyl optionally substituted by 1-6 $R^{189}$, $C_{4-17}$cycloalkylalkyl optionally substituted by 1-6 $R^{189}$, 3-15 membered heterocycloalkyl optionally substituted by 1-6 $R^{189}$, 4-21 membered heterocycloalkylalkyl optionally substituted by 1-6 $R^{189}$, and 6-21 membered heteroarylalkyl optionally substituted by 1-6 $R^{189}$; $R^2$, $R^3$, $R^{12}$, $R^{13}$, $R^{22}$, $R^{23}$, $R^{32}$, $R^{33}$, $R^{42}$, $R^{43}$, $R^{52}$, $R^{53}$, $R^{62}$, $R^{63}$, $R^{72}$, $R^{73}$, $R^{82}$, $R^{83}$, $R^{92}$, $R^{93}$, $R^{102}$, $R^{103}$, $R^{132}$, $R^{133}$, $R^{172}$ and $R^{173}$ at each occurrence is independently chosen from H, $C_{1-6}$alkyl optionally substituted by 1-6 $R^{199}$, $C_{7-16}$arylalkyl optionally substituted by 1-6 $R^{199}$, $C_{4-17}$cycloalkylalkyl optionally substituted by 1-6 $R^{199}$, 4-21 membered heterocycloalkylalkyl optionally substituted by 1-6 $R^{199}$, and 6-21 membered heteroarylalkyl optionally substituted by 1-6 $R^{199}$; or any $R^2$ and $R^3$, $R^{12}$ and $R^{13}$, $R^{22}$ and $R^{23}$, $R^{32}$ and $R^{33}$, $R^{42}$ and $R^{43}$, $R^{52}$ and $R^{53}$, $R^{62}$ and $R^{63}$, $R^{72}$ and $R^{73}$, $R^{82}$ and $R^{83}$, $R^{92}$ and $R^{93}$, $R^{102}$ and $R^{103}$, $R^{132}$ and $R^{133}$, or $R^{172}$ and $R^{173}$ may form, together with the nitrogen atom to which they are attached, a 3-15 membered heterocycloalkyl optionally substituted by 1-6 $R^{209}$ or a 5-15 membered heteroaryl optionally substituted by 1-6 $R^{209}$; $R^{179}$; $R^{189}$; $R^{199}$ and $R^{209}$ at each occurrence is independently chosen from $C_{1-6}$alkyl optionally substituted by 1-6 $R^{219}$, $C_{6-11}$aryl optionally substituted by 1-7 $R^{219}$, $C_{7-16}$arylalkyl optionally substituted by 1-6 $R^{219}$, $C_{3-11}$cycloalkyl optionally substituted by 1-6 $R^{219}$, $C_{4-17}$cycloalkylalkyl optionally substituted by 1-6 $R^{219}$, 3-15 membered heterocycloalkyl optionally substituted by 1-6 $R^{219}$, 4-21 membered heterocycloalkylalkyl optionally substituted by 1-6 $R^{219}$, 5-15 membered heteroaryl optionally substituted by 1-6 $R^{219}$, 6-21 membered heteroarylalkyl optionally substituted by 1-6 $R^{219}$, halogen, —CN, —$C(=O)R^{210}$, —$C(=O)OR^{210}$, —$C(=O)NR^{212}R^{213}$, —$C(=S)NR^{212}R^{213}$, —NC, —$NO_2$, —$NR^{212}R^{213}$, —$NR^{214}NR^{212}R^{213}$, —$NR^{214}C(=O)R^{210}$, —$NR^{214}C(=O)OR^{211}$, —$NR^{214}C(=O)NR^{212}R^{213}$, —$NR^{214}C(=O)NR^{214}C(=O)R^{210}$, —$NR^{214}C(=NR^{215})NR^{212}R^{213}$, —$NR^{214}C(=S)R^{210}$, —$NR^{214}C(=S)NR^{212}R^{213}$, —$NR^{214}S(=O)_2R^{211}$, —$OR^{210}$, =O, —OCN, —$OC(=O)R^{210}$, —$OC(=O)NR^{212}R^{213}$, —$OS(=O)R^{210}$, —SCN, =S, —$S(=O)_nR^{210}$, and —$S(=O)_2NR^{212}R^{213}$; $R^{210}$, $R^{211}$, $R^{214}$, $R^{215}$, $R^{216}$ and $R^{217}$ at each occurrence is independently chosen from H, $C_{1-6}$alkyl optionally substituted by 1-6 $R^{229}$, $C_{6-11}$aryl optionally substituted by 1-7 $R^{229}$, $C_{3-11}$cycloalkyl optionally substituted by 1-6 $R^{229}$, 3-15 membered heterocycloalkyl optionally substituted by 1-6 $R^{229}$, and 5-15 membered heteroaryl optionally substituted by 1-6 $R^{229}$; $R^{212}$ and $R^{213}$ at each occurrence is independently chosen from H, $C_{1-6}$alkyl optionally substituted by 1-6 $R^{239}$, $C_{7-16}$arylalkyl optionally substituted by 1-6 $R^{239}$, $C_{4-17}$cycloalkylalkyl optionally substituted by 1-6 $R^{239}$, 4-21 membered heterocycloalkylalkyl optionally substituted by 1-6 $R^{239}$, and 6-21 membered heteroarylalkyl optionally substituted by 1-6 $R^{239}$; or any $R^{212}$ and $R^{213}$ may form, together with the nitrogen atom to which they are attached, a 3-15 membered heterocycloalkyl optionally substituted by 1-6 $R^{249}$ or a 5-15 membered heteroaryl optionally substituted by 1-6 $R^{249}$; $R^{219}$, $R^{229}$, $R^{239}$ and $R^{249}$ at each occurrence is independently chosen from $C_{1-6}$alkyl optionally substituted by 1-6 halogen, $C_{6-11}$ aryl, $C_{7-16}$ arylalkyl, $C_{3-11}$ cycloalkyl, $C_{4-17}$cycloalkylalkyl, 3-15 membered heterocycloalkyl, 4-21 membered heterocycloalkylalkyl, 5-15 membered heteroaryl, 6-21 membered heteroarylalkyl, halogen, —CN, —$C(=O)R^{250}$, —$C(=O)OR^{250}$, —$C(=O)NR^{250}R^{250}$; —$C(=S)NR^{250}R^{250}$; —NC, —$NO_2$, —$NR^{250}R^{250}$, —$NR^{250}NR^{250}R^{250}$, —$NR^{250}C(=O)R^{250}$, —$NR^{250}C(=O)OR^{250}$, —$NR^{250}C(=O)NR^{250}C(=O)R^{250}$, —$NR^{250}(=NR^{250})NR^{250}R^{250}$, —$NR^{250}C(=S)R^{250}$, —$NR^{250}C(=S)NR^{250}R^{250}$; —$NR^{250}S(=O)_2R^{250}$; —$OR^{250}$, =O, —OCN, —$OC(=O)R^{250}$, —$OC(=O)NR^{250}R^{250}$, —SCN, =S, —$S(=O)_nR^{250}$, and —$S(=O)_2NR^{250}R^{250}$; $R^{250}$ at each occurrence is independently chosen from H and $C_{1-6}$alkyl; and n at each occurrence is independently chosen from 0 and 2; with the proviso that the compound is not:

(a)

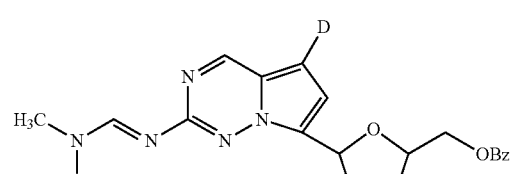

wherein
Bz is benzoyl, and
D is —C(=O)H or H, (b)

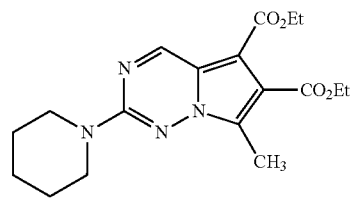

wherein Et is ethyl, or

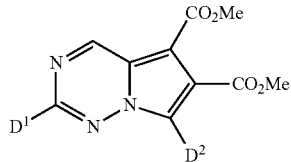

wherein
D¹ is methoxy, phenyl, or 4-methylphenyl,
D² is —CH$_2$C(=O)OMe or —C(=O)OMe, and
Me is methyl.

In one embodiment, the present invention provides one or more of the following compounds of formula I:

[7-(3-Chloro-phenyl)-pyrrolo[2,1-f][1,2,4]triazin-2-yl]-(4-morpholin-4-yl-phenyl)-amine;
(4-Morpholin-4-yl-phenyl)-(7-phenyl-pyrrolo[2,1-f][1,2,4]triazin-2-yl)amine;
[7-(5-Chloro-2-methoxy-phenyl)-pyrrolo[2,1-f][1,2,4]triazin-2-yl]-(4-morpholin-4-yl-phenyl)-amine;
(4-Morpholin-4-yl-phenyl)-(7-pyridin-4-yl-pyrrolo[2,1-f][1,2,4]triazin-2-yl)-amine;
[7-(2,3-Dihydro-benzo[1,4]dioxin-6-yl)-pyrrolo[2,1-f][1,2,4]triazin-2-yl]-(4-morpholin-4-yl-phenyl)-amine;
3-[2-(4-Morpholin-4-yl-phenylamino)-pyrrolo[2,1-f][1,2,4]triazin-7-yl]-benzoic acid methyl ester;
[4-(4-Methyl-piperazin-1-yl)-phenyl]-(7-phenyl-pyrrolo[2,1-f][1,2,4]triazin-2-yl)-amine;
[7-(2,3-Dihydro-benzo[1,4]dioxin-6-yl)-pyrrolo[2,1-f][1,2,4]triazin-2-yl]-[4-(4-methyl-piperazin-1-yl)-phenyl]-amine;
[3-(2-Methoxy-ethyl)-2,3,4,5-tetrahydro-1H-benzo[d]azepin-7-yl]-(7-phenyl-pyrrolo[2,1-f][1,2,4]triazin-2-yl)-amine;
[7-(1-Methyl-1H-pyrazol-4-yl)-pyrrolo[2,1-f][1,2,4]triazin-2-yl]-(4-morpholin-4-yl-phenyl)-amine;
(4-Morpholin-4-yl-phenyl)-(7-pyridin-3-yl-pyrrolo[2,1-f][1,2,4]triazin-2-yl)-amine;
(7-Phenyl-pyrrolo[2,1-f][1,2,4]triazin-2-yl)-pyridin-3-ylmethyl-amine;
(7-Phenyl-pyrrolo[2,1-f][1,2,4]triazin-2-yl)-(3,4,5-trimethoxy-phenyl)amine;
Morpholin-4-yl-{4-[2-(4-morpholin-4-yl-phenylamino)-pyrrolo[2,1-f][1,2,4]triazin-7-yl]-phenyl}-methanone;
{3-[2-(4-Morpholin-4-yl-phenylamino)-pyrrolo[2,1-f][1,2,4]triazin-7-yl]-phenyl}-pyrrolidin-1-yl-methanone;
[7-(2-Methoxy-pyridin-3-yl)-pyrrolo[2,1-f][1,2,4]triazin-2-yl]-(4-morpholin-4-yl-phenyl)-amine;
[7-(5-Chloro-2-methoxy-phenyl)-pyrrolo[2,1-f][1,2,4]triazin-2-yl]-[4-(4-methyl-piperazin-1-yl)-phenyl]-amine;
[4-(4-Methyl-piperazin-1-yl)-phenyl]-[7-(1-methyl-1H-pyrazol-4-yl)-pyrrolo[2,1-f][1,2,4]triazin-2-yl]-amine;
(4-{2-[4-(4-Methyl-piperazin-1-yl)-phenylamino]-pyrrolo[2,1-f][1,2,4]triazin-7-yl}-phenyl)-morpholin-4-yl-methanone;
[7-(2-Methoxy-phenyl)-pyrrolo[2,1-f][1,2,4]triazin-2-yl]-[4-(4-methyl-piperazin-1-1)-phenyl]-amine;
(3-{2-[4-(4-Methyl-piperazin-1-yl)-phenylamino]-pyrrolo[2,1-f][1,2,4]triazin-7-yl}-phenyl)-pyrrolidin-1-yl-methanone;
[7-(2-Methoxy-pyridin-3-yl)-pyrrolo[2,1-f][1,2,4]triazin-2-yl]-[4-(4-methyl-piperazin-1-yl)-phenyl]-amine;
N-tert-Butyl-3-{2-[4-(4-methyl-piperazin-1-yl)-phenylamino]-pyrrolo[2,1-f][1,2,4]triazin-7-yl}-benzenesulfonamide;
N(2)-[4-(4-Methyl-piperazin-1-yl)-phenyl]-N(7)-phenyl-pyrrolo[2,1-f][1,2,4]triazine-2,7-diamine;
[7-(2-Chloro-phenyl)-pyrrolo[2,1-f][1,2,4]triazin-2-yl]-[4-(4-methyl-piperazin-1-yl)-phenyl]-amine;
[7-(3-Chloro-phenyl)-pyrrolo[2,1-f][1,2,4]triazin-2-yl]-[4-(4-methyl-piperazin-1-yl)-phenyl]-amine;
[4-(4-Methyl-piperazin-1-yl)-phenyl]-(7-pyridin-3-yl-pyrrolo[2,1-f][1,2,4]triazin-2-yl)-amine;
(2-Morpholin-4-yl-ethyl)-(7-phenyl-pyrrolo[2,1-f][1,2,4]triazin-2-yl)-amine;
(3-Morpholin-4-yl-propyl)-(7-phenyl-pyrrolo[2,1-f][1,2,4]triazin-2-yl)-amine;
[3-(2-Methoxy-ethyl)-2,3,4,5-tetrahydro-1H-benzo[d]azepin-7-yl]-[7-(2-methoxy-phenyl)-pyrrolo[2,1-f][1,2,4]triazin-2-yl]-amine;
2-{2-[3-(2-Methoxy-ethyl)-2,3,4,5-tetrahydro-1H-benzo[d]azepin-7-ylamino]-pyrrolo[2,1-f][1,2,4]triazin-7-yl}-N,N-dimethyl-benzenesulfonamide;
[3-(2-Methoxy-ethyl)-2,3,4,5-tetrahydro-1H-benzo[d]azepin-7-yl]-{7-[2-(pyrrolidine-1-sulfonyl)-phenyl]-pyrrolo[2,1-f][1,2,4]triazin-2-yl}-amine;
[2-Methoxy-4-(4-methyl-piperazin-1-yl)-phenyl]-[7-(2-methoxy-phenyl)-pyrrolo[2,1-f][1,2,4]triazin-2-yl]-amine;
[2-Methoxy-4-(4-methyl-piperazin-1-yl)-phenyl]-[7-(2-methoxy-pyridin-3-yl)-pyrrolo[2,1-f][1,2,4]triazin-2-yl]-amine;
2-{2-[2-Methoxy-4-(4-methyl-piperazin-1-yl)-phenylamino]-pyrrolo[2,1-f][1,2,4]triazin-7-yl}-N,N-dimethyl-benzenesulfonamide;
2-[2-(4-Morpholin-4-yl-phenylamino)-pyrrolo[2,1-f][1,2,4]triazin-7-yl]-benzamide;
5-[2-(4-Morpholin-4-yl-phenylamino)-pyrrolo[2,1-f][1,2,4]triazin-7-yl]-pyridine-2-carbonitrile;
[7-(4-Methanesulfonyl-phenyl)-pyrrolo[2,1-f][1,2,4]triazin-2-yl]-(4-morpholin-4-yl-phenyl)-amine;
3-[2-(4-Morpholin-4-yl-phenylamino)-pyrrolo[2,1-f][1,2,4]triazin-7-yl]-benzonitrile;
[5-(2-Chloro-phenyl)-pyrrolo[2,1-f][1,2,4]triazin-2-yl]-[4-(4-methyl-piperazin-1-yl)-phenyl]-amine;
[4-(4-Methyl-piperazin-1-yl)-phenyl]-(5-phenyl-pyrrolo[2,1-f][1,2,4]triazin-2-yl)-amine;
[5-(2-Methoxy-phenyl)-pyrrolo[2,1-f][1,2,4]triazin-2-yl]-[4-(4-methyl-piperazin-1-yl)-phenyl]-amine;
[7-(3-Methanesulfonyl-phenyl)-pyrrolo[2,1-f][1,2,4]triazin-2-yl]-(4-morpholin-4-yl-phenyl)-amine;
4-[2-(4-Morpholin-4-yl-phenylamino)-pyrrolo[2,1-f][1,2,4]triazin-7-yl]-benzoic acid tert-butyl ester;
4-[2-(4-Morpholin-4-yl-phenylamino)-pyrrolo[2,1-f][1,2,4]triazin-7-yl]-benzoic acid;
(6-Morpholin-4-yl-pyridin-3-yl)-(7-phenyl-pyrrolo[2,1-f][1,2,4]triazin-2-yl)-amine;
[7-(2-Methoxy-phenyl)-pyrrolo[2,1-f][1,2,4]triazin-2-yl]-(6-morpholin-4-yl-pyridin-3-yl)-amine;
[8-Methoxy-3-(2-methoxy-ethyl)-2,3,4,5-tetrahydro-1H-benzo[d]azepin-7-yl]-[7-(2-methoxy-phenyl)-pyrrolo[2,1-f][1,2,4]triazin-2-yl]-amine;
[7-(3-Chloro-phenyl)-pyrrolo[2,1-f][1,2,4]triazin-2-yl]-(4-piperidin-1-yl-phenyl)-amine;
(4-Morpholin-4-yl-phenyl)-pyrrolo[2,1-f][1,2,4]triazin-2-yl-amine;
2-(4-Morpholin-4-yl-phenylamino)-pyrrolo[2,1-f][1,2,4]triazine-7-carbonitrile;

N-(2-Dimethylamino-ethyl)-4-[2-(4-morpholin-4-yl-phenylamino)-pyrrolo[2,1-f][1,2,4]triazin-7-yl]-benzamide;
2-Pyrrolidin-1-yl-ethylamine to give 4-[2-(4-Morpholin-4-yl-phenylamino)-pyrrolo[2,1-f][1,2,4]triazin-7-yl]-N-(2-pyrrolidin-1-yl-ethyl)-benzamide;
4-[2-(4-Morpholin-4-yl-phenylamino)-pyrrolo[2,1-f][1,2,4]triazin-7-yl]-N-(3-pyrrolidin-1-yl-propyl)-benzamide;
N-Methyl-4-[2-(4-morpholin-4-yl-phenylamino)-pyrrolo[2,1-f][1,2,4]triazin-7-yl]-benzamide;
N-(2-Morpholin-4-yl-ethyl)-4-[2-(4-morpholin-4-yl-phenylamino)-pyrrolo[2,1-f][1,2,4]triazin-7-yl]-benzamide;
4-[2-(4-Morpholin-4-yl-phenylamino)-pyrrolo[2,1-f][1,2,4]triazin-7-yl]-N-(3-morpholin-4-yl-propyl)-benzamide;
[7-(4-Chloro-3-trifluoromethyl-phenyl)-pyrrolo[2,1-f][1,2,4]triazin-2-yl]-(4-morpholin-4-yl-phenyl)-amine;
[7-(4-Methanesulfonyl-phenyl)-pyrrolo[2,1-f][1,2,4]triazin-2-yl]-[4-(4-methyl-piperazin-1-yl)-phenyl]-amine;
[7-(4-Methanesulfonyl-phenyl)-pyrrolo[2,1-f][1,2,4]triazin-2-yl]-(6-morpholin-4-yl-pyridin-3-yl)-amine;
[7-(4-Methanesulfonyl-phenyl)-pyrrolo[2,1-f][1,2,4]triazin-2-yl]-(4-piperidin-1-yl-phenyl)-amine;
[7-(4-Methanesulfonyl-phenyl)-pyrrolo[2,1-f][1,2,4]triazin-2-yl]-[2-methoxy-4-(4-methyl-piperazin-1-yl)-phenyl]-amine;
(4-Morpholin-4-yl-phenyl)-{7-[4-(pyrrolidine-1-sulfonyl)-phenyl]-pyrrolo[2,1-f][1,2,4]triazin-2-yl}-amine;
[7-(3-Chloro-phenyl)-pyrrolo[2,1-f][1,2,4]triazin-2-yl]-[3-methoxy-4-(4-methyl-piperazin-1-yl)-phenyl]-amine;
[7-(3-Chloro-phenyl)-pyrrolo[2,1-f][1,2,4]triazin-2-yl]-(3-methoxy-4-morpholin-4-yl-phenyl)-amine;
[7-(3-Chloro-phenyl)-pyrrolo[2,1-f][1,2,4]triazin-2-yl]-(3-methyl-4-morpholin-4-yl-phenyl)-amine;
[7-(4-Methanesulfonyl-phenyl)-pyrrolo[2,1-f][1,2,4]triazin-2-yl]-[2-methyl-4-(4-methyl-piperazin-1-yl)-phenyl]-amine;
[7-(3-Chloro-phenyl)-pyrrolo[2,1-f][1,2,4]triazin-2-yl]-[2-methyl-4-(4-methyl-piperazin-1-yl)-phenyl]-amine;
[7-(3-Chloro-phenyl)-pyrrolo[2,1-f][1,2,4]triazin-2-yl]-[3-methyl-4-(4-methyl-piperazin-1-yl)-phenyl]-amine;
[7-(2-Chloro-5-trifluoromethyl-phenyl)-pyrrolo[2,1-f][1,2,4]triazin-2-yl]-(4-morpholin-4-yl-phenyl)-amine;
N,N-Dimethylsulfonamide-4-benzeneboronic acid to give N,N-Dimethyl-4-[2-(4-morpholin-4-yl-phenylamino)-pyrrolo[2,1-f][1,2,4]triazin-7-yl]-benzenesulfonamide;
[2-(4-Morpholin-4-yl-phenylamino)-pyrrolo[2,1-f][1,2,4]triazin-7-yl]-phenyl-methanone;
[2-Methoxy-4-(4-methyl-piperazin-1-yl)-phenyl]-[7-(6-methoxy-pyridin-3-yl)-pyrrolo[2,1-f][1,2,4]triazin-2-yl]-amine;
4,N,N-Trimethyl-3-{2-[4-(4-methyl-piperazin-1-yl)-phenylamino]-pyrrolo[2,1-f][1,2,4]triazin-7-yl}-benzenesulfonamide;
3-{2-[2-Methoxy-4-(4-methyl-piperazin-1-yl)-phenylamino]-pyrrolo[2,1-f][1,2,4]triazin-7-yl}-4,N,N-trimethyl-benzenesulfonamide;
[7-(3-Methanesulfonyl-phenyl)-pyrrolo[2,1-f][1,2,4]triazin-2-yl]-[2-methoxy-4-(4-methyl-piperazin-1-yl)-phenyl]-amine;
5-{2-[2-Methoxy-4-(4-methyl-piperazin-1-yl)-phenylamino]-pyrrolo[2,1-f][1,2,4]triazin-7-yl}-pyridine-2-carbonitrile;
[4-(4-Methyl-piperazin-1-yl)-phenyl]-(7-phenylsulfanyl-pyrrolo[2,1-f][1,2,4]triazin-2-yl)-amine;
[7-(3-Chloro-phenyl)-pyrrolo[2,1-f][1,2,4]triazin-2-yl]-(6-morpholin-4-yl-pyridin-3-yl)-amine;
(2-Chloro-4-morpholin-4-yl-phenyl)-(5-chloro-7-phenyl-pyrrolo[2,1-f][1,2,4]triazin-2-yl)-amine;
[7-(6-Methoxy-pyridin-3-yl)-pyrrolo[2,1-f][1,2,4]triazin-2-yl]-[4-(4-methyl-piperazin-1-yl)-phenyl]-amine;
[7-(3-Methanesulfonyl-phenyl)-pyrrolo[2,1-f][1,2,4]triazin-2-yl]-[4-(4-methyl-piperazin-1-yl)-phenyl]-amine;
N,N-Dimethyl-4-{2-[4-(4-methyl-piperazin-1-yl)-phenylamino]-pyrrolo[2,1-f][1,2,4]triazin-7-yl}-benzenesulfonamide;
(5,7-Dibromo-pyrrolo[2,1-f][1,2,4]triazin-2-yl)-[4-(4-methyl-piperazin-1-yl)-phenyl]-amine;
[7-(4-Methanesulfonyl-phenyl)-pyrrolo[2,1-f][1,2,4]triazin-2-yl]-(4-piperidin-1-yl-phenyl)-amine;
N,N-Dimethyl-4-[2-(4-piperidin-1-yl-phenylamino)-pyrrolo[2,1-f][1,2,4]triazin-7-yl]-benzenesulfonamide;
(1-{4-[7-(4-Methanesulfonyl-phenyl)-pyrrolo[2,1-f][1,2,4]triazin-2-ylamino]-phenyl}-piperidin-4-yl)-methanol; compound with trifluoro-acetic acid;
2-(4-{4-[7-(4-Methanesulfonyl-phenyl)-pyrrolo[2,1-f][1,2,4]triazin-2-ylamino]-phenyl}-piperazin-1-yl)-ethanol;
[7-(4-Methanesulfonyl-phenyl)-pyrrolo[2,1-f][1,2,4]triazin-2-yl]-[3-(2-methoxy-ethyl)-2,3,4,5-tetrahydro-1H-benzo[d]azepin-7-yl]-amine;
[3-Fluoro-4-(4-methyl-piperazin-1-yl)-phenyl]-[7-(2-methoxy-phenyl)-pyrrolo[2,1-f][1,2,4]triazin-2-yl]-amine;
[5-Bromo-7-(4-methanesulfonyl-phenyl)-pyrrolo[2,1-f][1,2,4]triazin-2-yl]-[4-(4-methyl-piperazin-1-yl)-phenyl]-amine;
8-[7-(4-Methanesulfonyl-phenyl)-pyrrolo[2,1-f][1,2,4]triazin-2-ylamino]-5,5-dimethyl-1,3,4,5-tetrahydro-benzo[b]azepin-2-one;
[7-(3-Chloro-phenyl)-pyrrolo[2,1-f][1,2,4]triazin-2-yl]-{4-[2-(4-ethyl-piperazin-1-yl)-ethoxy]-phenyl}-amine;
[7-(2-Methoxy-phenyl)-pyrrolo[2,1-f][1,2,4]triazin-2-yl]-{4-[2-(4-methyl-piperazin-1-yl)-ethoxy]-phenyl}-amine;
2-[4-(4-Amino-phenyl)-piperazin-1-yl]-ethanol to give 2-(4-{4-[7-(3-Methanesulfonyl-phenyl)-pyrrolo[2,1-f][1,2,4]triazin-2-ylamino]-phenyl}-piperazin-1-yl)-ethanol;
(1-{4-[7-(3-Methanesulfonyl-phenyl)-pyrrolo[2,1-f][1,2,4]triazin-2-ylamino]-phenyl}-piperidin-4-yl)-methanol;
(4-Morpholin-4-yl-phenyl)-(7-phenylsulfanyl-pyrrolo[2,1-f][1,2,4]triazin-2-yl)-amine;
[7-(2-Methoxy-phenylsulfanyl)-pyrrolo[2,1-f][1,2,4]triazin-2-yl]-[4-(4-methyl-piperazin-1-yl)-phenyl]-amine;
[5-Bromo-7-(4-methanesulfonyl-phenyl)-pyrrolo[2,1-f][1,2,4]triazin-2-yl]-(4-morpholin-4-yl-phenyl)-amine;
(5-Bromo-7-phenyl-pyrrolo[2,1-f][1,2,4]triazin-2-yl)-[4-(4-methyl-piperazin-1-yl)-phenyl]-amine;
[5-Bromo-7-(2-methoxy-phenyl)-pyrrolo[2,1-f][1,2,4]triazin-2-yl]-[4-(4-methyl-piperazin-1-yl)-phenyl]-amine;
[7-Bromo-5-(2-methoxy-phenyl)-pyrrolo[2,1-f][1,2,4]triazin-2-yl]-[4-(4-methyl-piperazin-1-yl)-phenyl]-amine;
[7-(2-Methoxy-phenyl)-5-vinyl-pyrrolo[2,1-f][1,2,4]triazin-2-yl]-[4-(4-methyl-piperazin-1-yl)-phenyl]-amine;
[7-(4-Methanesulfonyl-phenyl)-5-vinyl-pyrrolo[2,1-f][1,2,4]triazin-2-yl]-[4-(4-methyl-piperazin-1-yl)-phenyl]-amine;
[7-(2-Methoxy-phenyl)-5-methyl-pyrrolo[2,1-f][1,2,4]triazin-2-yl]-[4-(4-methyl-piperazin-1-yl)-phenyl]-amine;
[5-Ethyl-7-(2-methoxy-phenyl)-pyrrolo[2,1-f][1,2,4]triazin-2-yl]-[4-(4-methyl-piperazin-1-yl)-phenyl]-amine;
[7-(4-Methanesulfonyl-phenyl)-5-methyl-pyrrolo[2,1-f][1,2,4]triazin-2-yl]-(4-morpholin-4-yl-phenyl)-amine;
[7-(4-Methanesulfonyl-phenyl)-5-methyl-pyrrolo[2,1-f][1,2,4]triazin-2-yl]-[4-(4-methyl-piperazin-1-yl)-phenyl]-amine;
[7-(2-Ethoxy-phenyl)-pyrrolo[2,1-f][1,2,4]triazin-2-yl]-[4-(4-methyl-piperazin-1-yl)-phenyl]-amine;

[5,6-Dibromo-7-(2-methoxy-phenyl)-pyrrolo[2,1-f][1,2,4]triazin-2-yl]-(4-morpholin-4-yl-phenyl)-amine;
(7-Benzenesulfonyl-pyrrolo[2,1-f][1,2,4]triazin-2-yl)-(4-morpholin-4-yl-phenyl)-amine;
[7-(2-Methoxy-phenyl)-5,6-dimethyl-pyrrolo[2,1-f][1,2,4]triazin-2-yl]-(4-morpholin-4-yl-phenyl)-amine;
7-(4-Methanesulfonyl-phenyl)-2-(2-methoxy-1-methyl-ethoxy)-pyrrolo[2,1-f][1,2,4]triazine;
7-(2-Methoxy-phenyl)-2-[4-(4-methyl-piperazin-1-yl)-phenylamino]-pyrrolo[2,1-f][1,2,4]triazine-5-carbonitrile;
2-{4-[4-(7-Pyridin-3-yl-pyrrolo[2,1-f][1,2,4]triazin-2-ylamino)-phenyl]-piperazin-1-yl}-ethanol;
{1-[4-(7-Pyridin-3-yl-pyrrolo[2,1-f][1,2,4]triazin-2-ylamino)-phenyl]-piperidin-4-yl}-methanol;
N-(2-Methanesulfonyl-ethyl)-4-[2-(4-morpholin-4-yl-phenylamino)-pyrrolo[2,1-f][1,2,4]triazin-7-yl]-benzamide;
N-tert-Butyl-3-{2-[4-(2-pyrrolidin-1-yl-ethoxy)-phenylamino]-pyrrolo[2,1-f][1,2,4]triazin-7-yl}-benzenesulfonamide;
{4-[2-(4-Methyl-piperazin-1-yl)-ethoxy]-phenyl}-(7-pyridin-3-yl-pyrrolo[2,1-f][1,2,4]triazin-2-yl)-amine;
{4-[3-(4-Methyl-piperazin-1-yl)-propoxy]-phenyl}-(7-pyridin-3-yl-pyrrolo[2,1-f][1,2,4]triazin-2-yl)-amine;
[7-(2-Methoxy-phenyl)-pyrrolo[2,1-f][1,2,4]triazin-2-yl]-[4-(2-pyrrolidin-1-yl-ethoxy)-phenyl]-amine;
[7-(2-Methoxy-phenyl)-pyrrolo[2,1-f][1,2,4]triazin-2-yl]-(1H-pyrazol-3-yl)-amine;
(7-Cyclohexyl-pyrrolo[2,1-f][1,2,4]triazin-2-yl)-[4-(4-methyl-piperazin-1-yl)-phenyl]-amine;
(1H-Pyrazol-3-yl)-(7-pyridin-3-yl-pyrrolo[2,1-f][1,2,4]triazin-2-yl)-amine;
[4-(2-Morpholin-4-yl-ethoxy)-phenyl]-(7-pyridin-3-yl-pyrrolo[2,1-f][1,2,4]triazin-2-yl)-amine;
(7-Pyridin-3-yl-pyrrolo[2,1-f][1,2,4]triazin-2-yl)-[4-(2-pyrrolidin-1-yl-ethoxy)-phenyl]-amine;
(7-Cyclohexyl-pyrrolo[2,1-f][1,2,4]triazin-2-yl)-(4-morpholin-4-yl-phenyl)-amine;
[7-(2-Methoxy-phenyl)-pyrrolo[2,1-f][1,2,4]triazin-2-yl]-[4-(2-morpholin-4-yl-ethoxy)-phenyl]-amine;
[7-(5-Chloro-2-methoxy-phenyl)-pyrrolo[2,1-f][1,2,4]triazin-2-yl]-(3,4,5-trimethoxy-phenyl)-amine;
[7-(2-Methoxy-phenyl)-pyrrolo[2,1-f][1,2,4]triazin-2-yl]-(3,4,5-trimethoxy-phenyl)-amine;
[7-(3-Chloro-phenyl)-pyrrolo[2,1-f][1,2,4]triazin-2-yl]-(3,4,5-trimethoxy-phenyl)-amine;
[7-(5-Chloro-2-methoxy-phenyl)-pyrrolo[2,1-f][1,2,4]triazin-2-yl]-(3-methoxy-phenyl)-amine;
(3-Methoxy-phenyl)-[7-(2-methoxy-phenyl)-pyrrolo[2,1-f][1,2,4]triazin-2-yl]-amine;
[7-(3-Chloro-phenyl)-pyrrolo[2,1-f][1,2,4]triazin-2-yl]-(3-methoxy-phenyl)-amine;
[7-(2-Methoxy-phenyl)-pyrrolo[2,1-f][1,2,4]triazin-2-yl]-(3-morpholin-4-yl-phenyl)-amine;
[7-(3-Chloro-phenyl)-pyrrolo[2,1-f][1,2,4]triazin-2-yl]-(3-morpholin-4-yl-phenyl)-amine;
1,3-Benzodioxol-5-yl-[7-(2-methoxy-phenyl)-pyrrolo[2,1-f][1,2,4]triazin-2-yl]-amine;
1,3-Benzodioxol-5-yl-[7-(3-chloro-phenyl)-pyrrolo[2,1-f][1,2,4]triazin-2-yl]-amine;
[7-(5-Chloro-2-methoxy-phenyl)-pyrrolo[2,1-f][1,2,4]triazin-2-yl]-(3,4-dimethoxy-phenyl)-amine;
[7-(3-Chloro-phenyl)-pyrrolo[2,1-f][1,2,4]triazin-2-yl]-(3,4-dimethoxy-phenyl)-amine;
[7-(5-Chloro-2-methoxy-phenyl)-pyrrolo[2,1-f][1,2,4]triazin-2-yl]-(4-methoxy-phenyl)-amine;
(4-Methoxy-phenyl)-[7-(2-methoxy-phenyl)-pyrrolo[2,1-f][1,2,4]triazin-2-yl]-amine;
[7-(3-Chloro-phenyl)-pyrrolo[2,1-f][1,2,4]triazin-2-yl]-(4-methoxy-phenyl)-amine;
[7-(3-Chloro-phenyl)-pyrrolo[2,1-f][1,2,4]triazin-2-yl]-(3,5-dimethoxy-phenyl)-amine;
[7-(5-Chloro-2-methoxy-phenyl)-pyrrolo[2,1-f][1,2,4]triazin-2-yl]-(3,5-dimethoxy-phenyl)-amine;
(3,5-Dimethoxy-phenyl)-[7-(2-methoxy-phenyl)-pyrrolo[2,1-f][1,2,4]triazin-2-yl]-amine;
N-[7-(3-Chloro-phenyl)-pyrrolo[2,1-f][1,2,4]triazin-2-yl]-N',N'-dimethyl-benzene-1,3-diamine;
[7-(2-Methoxy-phenyl)-pyrrolo[2,1-f][1,2,4]triazin-2-yl]-[3-(4-methyl-piperazin-1-yl)-phenyl]-amine;
[7-(3-Chloro-phenyl)-pyrrolo[2,1-f][1,2,4]triazin-2-yl]-[3-(4-methyl-piperazin-1-yl)-phenyl]-amine;
[7-(4-Methanesulfonyl-phenyl)-pyrrolo[2,1-f][1,2,4]triazin-2-yl]-(3,4,5-trimethoxy-phenyl)-amine;
[7-(4-Methanesulfonyl-phenyl)-pyrrolo[2,1-f][1,2,4]triazin-2-yl]-(3-morpholin-4-yl-phenyl)-amine;
3-[7-(2-Methoxy-phenyl)-pyrrolo[2,1-f][1,2,4]triazin-2-ylamino]-benzamide;
3-[7-(3-Chloro-phenyl)-pyrrolo[2,1-f][1,2,4]triazin-2-ylamino]-benzamide;
3-[7-(5-Chloro-2-methoxy-phenyl)-pyrrolo[2,1-f][1,2,4]triazin-2-ylamino]-benzamide;
[7-(3-Chloro-phenyl)-pyrrolo[2,1-f][1,2,4]triazin-2-yl]-(4-pyrrolidin-1-yl-phenyl)-amine;
[7-(5-Chloro-2-methoxy-phenyl)-pyrrolo[2,1-f][1,2,4]triazin-2-yl]-(4-pyrrolidin-1-yl-phenyl)-amine;
[7-(2-Methoxy-phenyl)-pyrrolo[2,1-f][1,2,4]triazin-2-yl]-(4-pyrrolidin-1-yl-phenyl)-amine;
(1H-Indol-5-yl)-[7-(2-methoxy-phenyl)-pyrrolo[2,1-f][1,2,4]triazin-2-yl]-amine;
[7-(5-Chloro-2-methoxy-phenyl)-pyrrolo[2,1-f][1,2,4]triazin-2-yl]-(1H-indol-5-yl)-amine;
[7-(2-Methoxy-phenyl)-pyrrolo[2,1-f][1,2,4]triazin-2-yl]-quinolin-6-yl-amine;
[7-(5-Chloro-2-methoxy-phenyl)-pyrrolo[2,1-f][1,2,4]triazin-2-yl]-quinolin-6-yl-amine;
(3-Morpholin-4-yl-phenyl)-pyrrolo[2,1-f][1,2,4]triazin-2-yl-amine;
[7-(3-Fluoro-phenyl)-pyrrolo[2,1-f][1,2,4]triazin-2-yl]-(3-morpholin-4-yl-phenyl)-amine;
[7-(3-Chloro-phenyl)-pyrrolo[2,1-f][1,2,4]triazin-2-yl]-(1H-indol-5-yl)-amine;
[7-(3-Chloro-phenyl)-pyrrolo[2,1-f][1,2,4]triazin-2-yl]-quinolin-6-yl-amine;
2-(4-{3-[7-(2-Methoxy-phenyl)-pyrrolo[2,1-f][1,2,4]triazin-2-ylamino]-phenyl}-piperazin-1-yl)-ethanol;
2-(4-{3-[7-(3-Chloro-phenyl)-pyrrolo[2,1-f][1,2,4]triazin-2-ylamino]-phenyl}-piperazin-1-yl)-ethanol;
2-(4-{3-[7-(5-Chloro-2-methoxy-phenyl)-pyrrolo[2,1-f][1,2,4]triazin-2-ylamino]-phenyl}-piperazin-1-yl)-ethanol;
2-(4-{3-[7-(4-Methanesulfonyl-phenyl)-pyrrolo[2,1-f][1,2,4]triazin-2-ylamino]-phenyl}-piperazin-1-yl)-ethanol;
N-{4-[2-(3-Morpholin-4-yl-phenylamino)-pyrrolo[2,1-f][1,2,4]triazin-7-yl]-phenyl}-methanesulfonamide;
N-{3-[2-(3-Morpholin-4-yl-phenylamino)-pyrrolo[2,1-f][1,2,4]triazin-7-yl]-phenyl}-methanesulfonamide;
[7-(3-Methanesulfonyl-phenyl)-pyrrolo[2,1-f][1,2,4]triazin-2-yl]-(3-morpholin-4-yl-phenyl)-amine;
[7-(3-Methanesulfonyl-phenyl)-pyrrolo[2,1-f][1,2,4]triazin-2-yl]-(3,4,5-trimethoxy-phenyl)-amine;
(3-Fluoro-4-morpholin-4-yl-phenyl)-[7-(2-methoxy-phenyl)-pyrrolo[2,1-f][1,2,4]triazin-2-yl]-amine;
[7-(3-Chloro-phenyl)-pyrrolo[2,1-f][1,2,4]triazin-2-yl]-(3-fluoro-4-morpholin-4-yl-phenyl)-amine;

[7-(5-Chloro-2-methoxy-phenyl)-pyrrolo[2,1-f][1,2,4]triazin-2-yl]-(3-fluoro-4-morpholin-4-yl-phenyl)-amine;

(3-Fluoro-4-morpholin-4-yl-phenyl)-[7-(4-methanesulfonyl-phenyl)-pyrrolo[2,1-f][1,2,4]triazin-2-yl]-amine;

7-(3-Chloro-phenyl)-2-(2-methoxy-ethoxy)-pyrrolo[2,1-f][1,2,4]triazine;

7-(5-Chloro-2-methoxy-phenyl)-2-(2-methoxy-ethoxy)-pyrrolo[2,1-f][1,2,4]triazine;

(3-Morpholin-4-yl-phenyl)-{7-[4-(propane-2-sulfonyl)-phenyl]-pyrrolo[2,1-f][1,2,4]triazin-2-yl}-amine;

[7-(3-Fluoro-4-methanesulfonyl-phenyl)-pyrrolo[2,1-f][1,2,4]triazin-2-yl]-(3-morpholin-4-yl-phenyl)-amine;

N-Methyl-4-[2-(3-morpholin-4-yl-phenylamino)-pyrrolo[2,1-f][1,2,4]triazin-7-yl]-benzamide;

[7-(2-Methoxy-phenyl)-pyrrolo[2,1-f][1,2,4]triazin-2-yl]-[3-(4-morpholin-4-yl-piperidin-1-yl)-phenyl]-amine;

[7-(5-Chloro-2-methoxy-phenyl)-pyrrolo[2,1-f][1,2,4]triazin-2-yl]-[3-(4-morpholin-4-yl-piperidin-1-yl)-phenyl]-amine;

7-(4-Methanesulfonyl-phenyl)-2-(2-methoxy-ethoxy)-pyrrolo[2,1-f][1,2,4]triazine;

[7-(1-Methyl-1H-pyrazol-4-yl)-pyrrolo[2,1-f][1,2,4]triazin-2-yl]-(3-morpholin-4-yl-phenyl)-amine;

(4-Morpholin-4-yl-phenyl)-{7-[4-(propane-2-sulfonyl)-phenyl]-pyrrolo[2,1-f][1,2,4]triazin-2-yl}-amine;

N-{4-[2-(4-Morpholin-4-yl-phenylamino)-pyrrolo[2,1-f][1,2,4]triazin-7-yl]-phenyl}-methanesulfonamide;

N-{3-[2-(4-Morpholin-4-yl-phenylamino)-pyrrolo[2,1-f][1,2,4]triazin-7-yl]-phenyl}-methanesulfonamide;

(S)-1-(4-{4-[7-(2-Methoxy-phenyl)-pyrrolo[2,1-f][1,2,4]triazin-2-ylamino]-phenyl}-piperazin-1-yl)-propan-2-ol;

(S)-1-(4-{4-[7-(5-Chloro-2-methoxy-phenyl)-pyrrolo[2,1-f][1,2,4]triazin-2-ylamino]-phenyl}-piperazin-1-yl)-propan-2-ol;

(S)-1-(4-{4-[7-(3-Chloro-phenyl)-pyrrolo[2,1-f][1,2,4]triazin-2-ylamino]-phenyl}-piperazin-1-yl)-propan-2-ol;

(S)-1-(4-{4-[7-(4-Methanesulfonyl-phenyl)-pyrrolo[2,1-f][1,2,4]triazin-2-ylamino]-phenyl}-piperazin-1-yl)-propan-2-ol;

(R)-1-(4-{4-[7-(2-Methoxy-phenyl)-pyrrolo[2,1-f][1,2,4]triazin-2-ylamino]-phenyl}-piperazin-1-yl)-propan-2-ol;

(R)-1-(4-{4-[7-(5-Chloro-2-methoxy-phenyl)-pyrrolo[2,1-f][1,2,4]triazin-2-ylamino]-phenyl}-piperazin-1-yl)-propan-2-ol;

(R)-1-(4-{4-[7-(3-Chloro-phenyl)-pyrrolo[2,1-f][1,2,4]triazin-2-ylamino]-phenyl}-piperazin-1-yl)-propan-2-ol;

(R)-1-(4-{4-[7-(4-Methanesulfonyl-phenyl)-pyrrolo[2,1-f][1,2,4]triazin-2-ylamino]-phenyl}-piperazin-1-yl)-propan-2-ol;

(S)-1-(4-{3-[7-(2-Methoxy-phenyl)-pyrrolo[2,1-f][1,2,4]triazin-2-ylamino]-phenyl}-piperazin-1-yl)-propan-2-ol;

(S)-1-(4-{3-[7-(5-Chloro-2-methoxy-phenyl)-pyrrolo[2,1-f][1,2,4]triazin-2-ylamino]-phenyl}-piperazin-1-yl)-propan-2-ol;

(S)-1-(4-{3-[7-(3-Chloro-phenyl)-pyrrolo[2,1-f][1,2,4]triazin-2-ylamino]-phenyl}-piperazin-1-yl)-propan-2-ol;

(R)-1-(4-{3-[7-(2-Methoxy-phenyl)-pyrrolo[2,1-f][1,2,4]triazin-2-ylamino]-phenyl}-piperazin-1-yl)-propan-2-ol;

(R)-1-(4-{3-[7-(5-Chloro-2-methoxy-phenyl)-pyrrolo[2,1-f][1,2,4]triazin-2-ylamino]-phenyl}-piperazin-1-yl)-propan-2-ol;

(R)-1-(4-{3-[7-(3-Chloro-phenyl)-pyrrolo[2,1-f][1,2,4]triazin-2-ylamino]-phenyl}-piperazin-1-yl)-propan-2-ol;

(S)-1-(4-{3-[7-(4-Methanesulfonyl-phenyl)-pyrrolo[2,1-f][1,2,4]triazin-2-ylamino]-phenyl}-piperazin-1-yl)-propan-2-ol;

(R)-1-(4-{3-[7-(4-Methanesulfonyl-phenyl)-pyrrolo[2,1-f][1,2,4]triazin-2-ylamino]-phenyl}-piperazin-1-yl)-propan-2-ol;

1-(4-{3-[7-(2-Methoxy-phenyl)-pyrrolo[2,1-f][1,2,4]triazin-2-ylamino]-phenyl}-piperazin-1-yl)-2-methyl-propan-2-ol;

1-(4-{3-[7-(5-Chloro-2-methoxy-phenyl)-pyrrolo[2,1-f][1,2,4]triazin-2-ylamino]-phenyl}-piperazin-1-yl)-2-methyl-propan-2-ol;

1-(4-{3-[7-(3-Chloro-phenyl)-pyrrolo[2,1-f][1,2,4]triazin-2-ylamino]-phenyl}-piperazin-1-yl)-2-methyl-propan-2-ol;

1-(4-{4-[7-(2-Methoxy-phenyl)-pyrrolo[2,1-f][1,2,4]triazin-2-ylamino]-phenyl}-piperazin-1-yl)-2-methyl-propan-2-ol;

1-(4-{4-[7-(5-Chloro-2-methoxy-phenyl)-pyrrolo[2,1-f][1,2,4]triazin-2-ylamino]-phenyl}-piperazin-1-yl)-2-methyl-propan-2-ol;

1-(4-{4-[7-(3-Chloro-phenyl)-pyrrolo[2,1-f][1,2,4]triazin-2-ylamino]-phenyl}-piperazin-1-yl)-2-methyl-propan-2-ol;

{2-Methoxy-4-[4-(1-methyl-piperidin-4-yl)-piperazin-1-yl]-phenyl}-[7-(2-methoxy-phenyl)-pyrrolo[2,1-f][1,2,4]triazin-2-yl]-amine;

1-[4-(1-{3-Methoxy-4-[7-(2-methoxy-phenyl)-pyrrolo[2,1-f][1,2,4]triazin-2-ylamino]-phenyl}-piperidin-3-yl)-piperazin-1-yl]-ethanone;

{4-[3-(4-Methanesulfonyl-piperazin-1-yl)-piperidin-1-yl]-2-methoxy-phenyl}-[7-(2-methoxy-phenyl)-pyrrolo[2,1-f][1,2,4]triazin-2-yl]-amine;

4-(1-{3-Methoxy-4-[7-(2-methoxy-phenyl)-pyrrolo[2,1-f][1,2,4]triazin-2-ylamino]-phenyl}-piperidin-3-yl)-piperazine-1-carboxylic acid benzyl ester;

{2-Methoxy-4-[3-(4-methyl-piperazin-1-yl)-piperidin-1-yl]-phenyl}-[7-(2-methoxy-phenyl)-pyrrolo[2,1-f][1,2,4]triazin-2-yl]-amine;

[2-Methoxy-4-(4-morpholin-4-yl-piperidin-1-yl)-phenyl]-[7-(2-methoxy-phenyl)-pyrrolo[2,1-f][1,2,4]triazin-2-yl]-amine;

2-Methoxy-4-[4-(4-methyl-piperazin-1-yl)-piperidin-1-yl]-phenyl}-(7-pyridin-3-yl-pyrrolo[2,1-f][1,2,4]triazin-2-yl)-amine;

4-(2-{2-Methoxy-4-[4-(4-methyl-piperazin-1-yl)-piperidin-1-yl]-phenylamino}-pyrrolo[2,1-f][1,2,4]triazin-7-yl)-N-methyl-benzamide;

{2-Methoxy-4-[4-(4-methyl-piperazin-1-yl)-piperidin-1-yl]-phenyl}-[7-(2-methoxy-phenyl)-pyrrolo[2,1-f][1,2,4]triazin-2-yl]-amine;

[4-(4-Ethyl-morpholin-2-yl)-phenyl]-[7-(2-methoxy-phenyl)-pyrrolo[2,1-f][1,2,4]triazin-2-yl]-amine;

[7-(5-Chloro-2-methoxy-phenyl)-pyrrolo[2,1-f][1,2,4]triazin-2-yl]-[4-(4-ethyl-morpholin-2-yl)-phenyl]-amine;

(4-Morpholin-4-yl-phenyl)-[1,2,4]triazino[1,6-a]indol-2-yl-amine;

{2-Methoxy-4-[4-(4-methyl-piperazin-1-yl)-piperidin-1-yl]-phenyl}-[1,2,4]triazino[1,6-a]indol-2-yl-amine;

[4-(4-Methyl-piperazin-1-yl)-phenyl]-[1,2,4]triazino[1,6-a]indol-2-yl-amine;

{4-[4-(4-Methyl-piperazin-1-yl)-piperidin-1-yl]-phenyl}-[1,2,4]triazino[1,6-a]indol-2-yl-amine;

5,5-Dimethyl-8-([1,2,4]triazino[1,6-a]indol-2-ylamino)-1,3,4,5-tetrahydro-benzo[b]azepin-2-one;

(2-Methoxy-4-morpholin-4-yl-phenyl)-[1,2,4]triazino[1,6-a]indol-2-yl-amine;

[2-Methoxy-4-(4-methyl-piperazin-1-yl)-phenyl]-[1,2,4]triazino[1,6-a]indol-2-yl-amine;

(7-Methoxy-[1,2,4]triazino[1,6-a]indol-2-yl)-(4-morpholin-4-yl-phenyl)-amine;
(2-Methoxy-4-morpholin-4-yl-phenyl)-(7-methoxy-[1,2,4]triazino[1,6-a]indol-2-yl)-amine;
Phenyl-[1,2,4]triazino[1,6-a]indol-2-yl-amine;
(3-Chloro-phenyl)-[1,2,4]triazino[1,6-a]indol-2-yl-amine;
(3-Methoxy-phenyl)-[1,2,4]triazino[1,6-a]indol-2-yl-amine; and
N,N-Dimethyl-3-([1,2,4]triazino[1,6-a]indol-2-ylamino)-benzenesulfonamide;
and salt forms thereof.

In another embodiment, the present invention provides any of the compounds as described in the Examples.

The present invention provides salts of the compounds of formula I. Preferably, the salts are pharmaceutically acceptable. Pharmaceutically acceptable acid addition salts of the compounds of formula I include, but are not limited to, salts derived from inorganic acids such as hydrochloric, nitric, phosphoric, sulfuric, hydrobromic, hydriodic, and phosphorus, as well as the salts derived from organic acids, such as aliphatic mono- and dicarboxylic acids, phenyl-substituted alkanoic acids, hydroxy alkanoic acids, alkanedioic acids, aromatic acids, and aliphatic and aromatic sulfonic acids. Such salts thus include, but are not limited to, sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, and methanesulfonate. Also contemplated are the salts of amino acids such as arginate, gluconate, galacturonate, and the like; see, for example, Berge et al., "Pharmaceutical Salts," J. of Pharmaceutical Science, 1977; 66:1-19.

The acid addition salts of the basic compounds may be prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are in general equivalent to their respective free base for purposes of the present invention.

Pharmaceutically acceptable base addition salts of compounds of formula I are formed with metals or amines, such as alkali and alkaline earth metal hydroxides, or of organic amines. Examples of metals used as cations include, but are not limited to, sodium, potassium, magnesium, and calcium. Examples of suitable amines include, but are not limited to, N,N'-dibenzylethylenediamine, chloroprocaine, choline, diethanolamine, ethylenediamine (ethane-1,2-diamine), N-methylglucamine, and procaine; see, for example, Berge et al., supra., 1977.

The base addition salts of acidic compounds may be prepared by contacting the free acid form with a sufficient amount of the desired base to produce the salt in the conventional manner. The free acid form may be regenerated by contacting the salt form with an acid and isolating the free acid in a conventional manner. The free acid forms differ from their respective salt forms somewhat in certain physical properties such as solubility in polar solvents, but otherwise the salts are in general equivalent to their respective free acid for purposes of the present invention.

Some of the compounds in the present invention may exist as stereoisomers, including enantiomers, diastereomers, and geometric isomers. Geometric isomers include compounds of the present invention that have alkenyl groups, which may exist as entgegen or zusammen conformations, in which case all geometric forms thereof, both entgegen and zusammen, cis and trans, and mixtures thereof, are within the scope of the present invention. Some compounds of the present invention have cycloalkyl groups, which may be substituted at more than one carbon atom, in which case all geometric forms thereof, both cis and trans, and mixtures thereof, are within the scope of the present invention. All of these forms, including (R), (S), epimers, diastereomers, cis, trans, syn, anti, (E), (Z), tautomers, and mixtures thereof, are contemplated in the compounds of the present invention.

The compounds to be used in the present invention can exist in unsolvated forms as well as solvated forms, including hydrated forms. In general, the solvated forms, including hydrated forms, are equivalent to unsolvated forms and are intended to be encompassed within the scope of the present invention.

III. Pharmaceutical Compositions

The present invention further provides pharmaceutical compositions comprising a compound of the present invention (e.g., a compound of formula I or a pharmaceutically acceptable salt thereof), together with a pharmaceutically acceptable carrier, diluent, or excipient therefor. The pharmaceutical composition may contain two or more compounds of the present invention (i.e., two or more compounds of the present invention may be used together in the pharmaceutical composition). Preferably, the pharmaceutical composition contains a therapeutically effective amount of at least one compound of the present invention. In another embodiment, these compositions are useful in the treatment of an ALK- or JAK2-mediated disorder or condition. The compounds of the invention can also be combined in a pharmaceutical composition that also comprises compounds that are useful for the treatment of cancer or another ALK- or JAK2-mediated disorder.

A compound of the present invention can be formulated as a pharmaceutical composition in the form of a syrup, an elixir, a suspension, a powder, a granule, a tablet, a capsule, a lozenge, a troche, an aqueous solution, a cream, an ointment, a lotion, a gel, an emulsion, etc. Preferably, a compound of the present invention will cause a decrease in symptoms or a disease indicia associated with an ALK- or JAK2-mediated disorder as measured quantitatively or qualitatively.

For preparing a pharmaceutical composition from a compound of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, binders, preservatives, tablet disintegrating agents, or an encapsulating material.

In powders, the carrier is a finely divided solid which is in a mixture with the finely divided active component (i.e., compound of the present invention). In tablets, the active component is mixed with the carrier having the necessary binding properties in suitable proportions and compacted in the shape and size desired.

The powders and tablets contain from 1% to 95% (w/w) of the active compound (i.e., compound of the present invention). In another embodiment, the active compound ranges from 5% to 70% (w/w). Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 1000 mg, preferably 1.0 mg to 100 mg, or from 1% to 95% (w/w) of a unit dose, according to the particular application and the potency of the active component. The composition can, if desired, also contain other compatible therapeutic agents.

Pharmaceutically acceptable carriers are determined in part by the particular composition being administered, as well as by the particular method used to administer the composition. Accordingly, there is a wide variety of suitable formulations of pharmaceutical compositions of the present invention (see, e.g., *Remington: The Science and Practice of Pharmacy*, 20th ed., Gennaro et al. Eds., Lippincott Williams and Wilkins, 2000).

A compound of the present invention, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations suitable for parenteral administration, such as, for example, by intravenous, intramuscular, intradermal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and nonaqueous sterile suspensions that can include suspending agents, solubilizers, thickening agents, stabilizers, and preservatives. In the practice of this invention, compositions can be administered, for example, by intravenous infusion, orally, topically, intraperitoneally, intravesically or intrathecally. The formulations of compounds can be presented in unit-dose or multi-dose sealed containers, such as ampoules and vials. Injection solutions and suspensions can be prepared from sterile powders, granules, and tablets of the kind previously described.

The dose administered to a subject, in the context of the present invention should be sufficient to effect a beneficial therapeutic response in the subject over time. The dose will be determined by the efficacy of the particular compound employed and the condition of the subject, as well as the body weight or surface area of the subject to be treated. The size of the dose also will be determined by the existence, nature, and extent of any adverse side-effects that accompany the administration of a particular compound in a particular subject. In determining the effective amount of the compound to be administered in the treatment or prophylaxis of the disorder being treated, the physician can evaluate factors such as the circulating plasma levels of the compound, compound toxicities, and/or the progression of the disease, etc. In general, the dose equivalent of a compound is from about 1 µg/kg to 10 mg/kg for a typical subject. Many different administration methods are known to those of skill in the art.

For administration, compounds of the present invention can be administered at a rate determined by factors that can include, but are not limited to, the $LD_{50}$ of the compound, the pharmacokinetic profile of the compound, contraindicated drugs, and the side-effects of the compound at various concentrations, as applied to the mass and overall health of the subject. Administration can be accomplished via single or divided doses.

IV. Methods of Treatment

In another aspect, the present invention provides a method of treating a subject suffering from an ALK- or JAK2-mediated disorder or condition comprising: administering to the subject a therapeutically effective amount of a compound of formula I or a pharmaceutically acceptable salt form thereof. In another aspect, the present invention provides a compound of formula I or a pharmaceutically acceptable salt form thereof for use in treating a subject suffering from an ALK- or JAK2-mediated disorder or condition. Preferably, the compound of formula I or a pharmaceutically acceptable salt form thereof is administered to the subject in a pharmaceutical composition comprising a pharmaceutically acceptable carrier. In another aspect, the present invention provides a pharmaceutical composition comprising a compound of formula I or a pharmaceutically acceptable salt form thereof for use in treating a subject suffering from an ALK- or JAK2-mediated disorder or condition. In another embodiment, the ALK- or JAK2-mediated condition or disorder is cancer. In another embodiment, the ALK- or JAK2-mediated condition is selected from anaplastic large cell lymphoma, inflammatory myofibroblastic tumor, glioblastoma, and other solid tumors. In another embodiment, the ALK- or JAK2-mediated condition is selected from colon cancer, breast cancer, renal cancer, lung cancer, hemangioma, squamous cell myeloid leukemia, melanoma, glioblastoma, and astrocytoma.

The ALK- or JAK2-mediated disorder or condition can be treated prophylactically, acutely, and chronically using compounds of the present invention, depending on the nature of the disorder or condition. Typically, the host or subject in each of these methods is human, although other mammals can also benefit from the administration of a compound of the present invention.

In another embodiment, the present invention provides a method of treating a proliferative disorder in a subject, comprising administering to the subject a therapeutically effective amount of a compound of formula I or a pharmaceutically acceptable salt form thereof. In another aspect, the present invention provides a compound of formula I or a pharmaceutically acceptable salt form thereof for use in treating a proliferative disorder in a subject. Preferably, the compound of formula I or a pharmaceutically acceptable salt form thereof is administered to the subject in a pharmaceutical composition comprising a pharmaceutically acceptable carrier. In another aspect, the present invention provides a pharmaceutical composition comprising a compound of formula I or a pharmaceutically acceptable salt form thereof for use in treating a proliferative disorder in a subject. In certain embodiments, the proliferative disorder is ALK- or JAK2-mediated. In certain embodiments, the proliferative disorder is cancer. In certain embodiments, the proliferative disorder is selected from anaplastic large cell lymphoma, inflammatory myofibroblastic tumor, glioblastoma, and other solid tumors. In certain embodiments, the proliferative disorder is selected from colon cancer, breast cancer, renal cancer, lung cancer, hemangioma, squamous cell myeloid leukemia, melanoma, glioblastoma, and astrocytoma.

The proliferative disorder can be treated prophylactically, acutely, and chronically using compounds of the present invention, depending on the nature of the disorder or condition. Typically, the host or subject in each of these methods is human, although other mammals can also benefit from the administration of a compound of the present invention.

The compounds of formula I share a common utility in treating ALK- or JAK2-mediated disorders and a common core structure essential to that utility (i.e., the compounds of formula I are all pyrrolo[2,1-f][1,2,4]triazine derivatives).

In therapeutic applications, the compounds of the present invention can be prepared and administered in a wide variety of oral and parenteral dosage forms. Thus, the compounds of the present invention can be administered by injection, that is, intravenously, intramuscularly, intracutaneously, subcutaneously, intraduodenally, or intraperitoneally. Also, the compounds described herein can be administered by inhalation, for example, intranasally. Additionally, the compounds of the present invention can be administered transdermally. In another embodiment, the compounds of the present invention are delivered orally. The compounds can also be delivered rectally, bucally or by insufflation.

The compounds utilized in the pharmaceutical method of the invention can be administered at the initial dosage of about 0.001 mg/kg to about 100 mg/kg daily. In another embodiment, the daily dose range is from about 0.1 mg/kg to about 10 mg/kg. The dosages, however, may be varied depending upon the requirements of the subject, the severity of the condition being treated, and the compound being employed. Determination of the proper dosage for a particular situation is within the skill of the practitioner. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day, if desired.

V. Chemistry

Unless otherwise indicated, all reagents and solvents were obtained from commercial sources and used as received. $^1$H NMRs were obtained on a Bruker Avance at 400 MHz in the solvent indicated with tetramethylsilane as an internal standard. Analytical HPLC was run using a Zorbax RX-C8, 5×150 mm column eluting with a mixture of acetonitrile and water containing 0.1% trifluoroacetic acid with a gradient of 10-100%. LCMS results were obtained on either of two instruments. First, in Examples that indicate LCMS retention times, analysis was performed on a Waters Aquity Ultra Performance LC with a 2.1 mm×50 mm Waters Aquity HPLC BEH C18 1.7 µm column. The target column temperature was 45° C., with a run time of two (2) minutes, a flow rate of 0.600 mL/min, and a solvent mixture of 5% (0.1% formic acid/water):95% (acetonitrile/0.1% formic acid). The mass spectrometry data was acquired on a Micromass LC-ZQ 2000 quadrupole mass spectrometer. Second, in Examples that do not indicate LCMS retention times, analysis was performed on a Bruker Esquire 200 ion trap. Automated column chromatography was performed on a CombiFlash Companion (ISCO, Inc.). Melting points were taken on a Mel-Temp apparatus and are uncorrected.

Synthesis

The compounds of the present invention can be prepared in a number of ways well known to one skilled in the art of organic synthesis. The compounds of the present invention can be synthesized using the methods described below as well as using methods known to one skilled in the art of organic chemistry or variations thereon as appreciated by those skilled in the art. The preferred methods include, but are not limited to or by, those described below. Unless otherwise stated, compounds are of commercial origin or readily synthesized by standard methods well known to one skilled in the art of organic synthesis.

The compounds of this invention may be prepared using the reactions and techniques described in this section. The reactions are performed in solvents appropriate to the reagents, and materials employed are suitable for the transformations being effected. Also, in the description of the synthetic methods below, it is to be understood that all proposed reaction conditions, including choice of solvent, reaction atmosphere, reaction temperature, duration of experiment and workup procedures are chosen to be conditions standard for that reaction which should be readily recognized by one skilled in the art of organic synthesis.

It is understood that the examples and embodiments described herein are for illustrative purposes only and that various modifications or changes in light thereof will be suggested to persons skilled in the art and are to be included within the spirit and purview of this application and the scope of the appended claims. Specific chemical transformations are listed in the ensuing schemes and one skilled in the art appreciates that a variety of different reagents may be used in place of those listed. Common replacements for such reagents can be found in, but not limited to, texts such as "Encyclopedia of Reagents for Organic Synthesis" Leo A. Paquette, John Wiley & Son Ltd (1995) or "Comprehensive Organic Transformations: A Guide to Functional Group Preparations" Richard C. Larock. Wiley-VCH and "Strategic Applications of Named Reactions in Organic Synthesis" Kurd and Czako, Elsevier, 2005 and references therein.

One embodiment for the synthesis of compounds of formula I as illustrated in Scheme 1 is the syntheses of key intermediates, compounds of formula 10, 11 and 12. Ethyl-2-pyrrole carboxylate (compound of formula I) may be N-aminated (for conditions for N-amination of pyrroles and indoles see: Hynes, J., Jr.; et al. *J. Org. Chem.* 2004, 69, 1368, and references cited therein; Friestad, et al. *J. Org. Chem,* 2002, 67, 6236 and references cited therein; Bhattacharya, A. et al. *Tetrahedron Letters,* 2006, 47(30), 5341 and references cited therein) and then condensed with benzoyl thioisocyanate to deliver compounds of formula 3. Cyclization with base (NaOH) provides compounds of formula 4. Methylation of the thio group followed by chlorination gives compounds of formula 6. Bromination provides compounds of formula 7-9 which can be taken on as a mixture. Reduction of the chlorine and triazine and re-aromatization via DDQ oxidation gives compounds of formula 10-12, which can be separated using standard chromatography conditions.

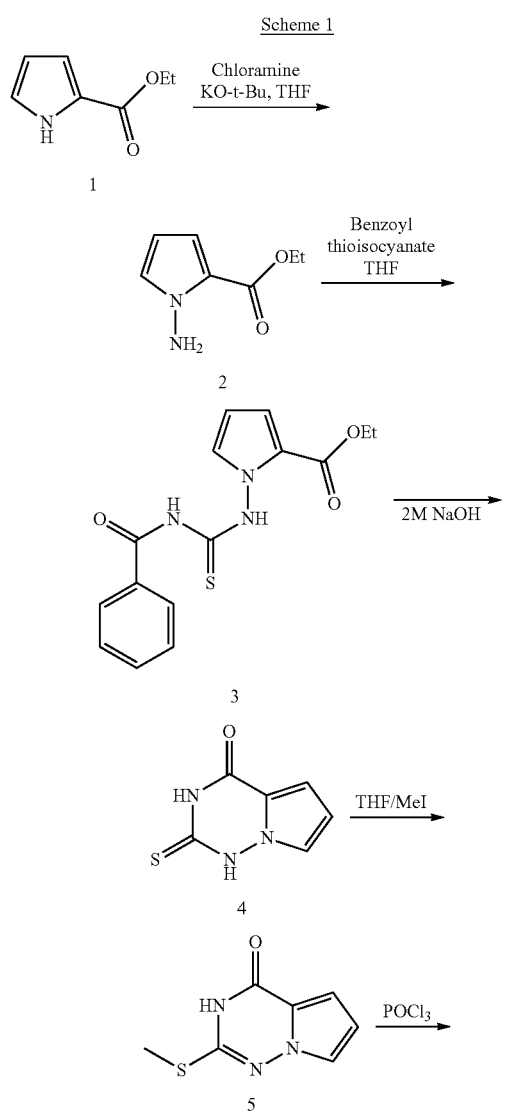

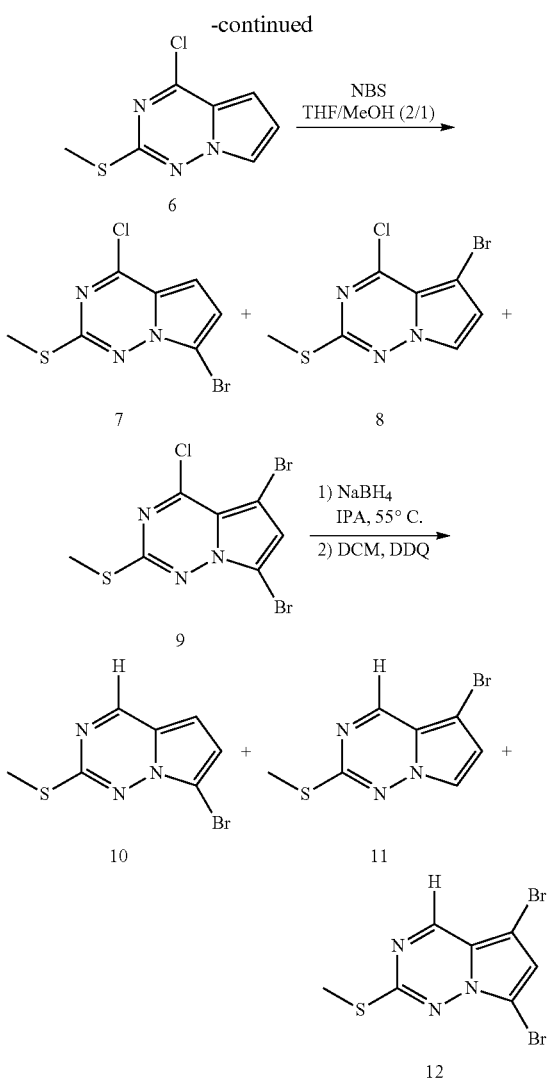

Scheme 2 illustrates how compounds of formula 10 are converted to compounds of formula I in which $Q^3, Q^4$=H. Two methods are shown in which the $Q^2$ group is installed, followed by oxidation of the sulfur to activate it as a leaving group, then installation of $Q^1$ Alternatively, the converse, oxidation of the sulfur to activate it as a leaving group to install $Q^1$ is followed by installation of $Q^2$. For $Q^2$ in which $L^2$ is absent and $Q^2$ is represented by aryl-$G^2$-$X^2$—$Z^2$ or heteroaryl-$G^2$-$X^2$—$Z^2$ (i.e. $A^2$=$C_{6-11}$ aryl, $C_{6-11}$ arylene or 5-15 membered heteroaryl, 5-15 membered heteroarylene), a transition metal-mediated coupling reaction between compounds of formula 10 or 17 and an appropriately modified aryl or heteroaryl group provides compounds of formula 13. Most commonly used conditions include Suzuki-Miyaura aryl-boronic acid/ester/fluoroborates with palladium as a catalyst. Other aryl or heteroaryl derivatives such as aryl/heteroaryl-tin, -chromium, zinc-halide or ionic metal species (Li/Mg/K/Na) may be used with other transition metal catalysts (most typified by Pd, Pt, Ni, Cu). For installation of $Q^1$ in which $Q^1$ is —NH-Aryl-$G^2$-$X^2$—$Z^2$ or —NH-heteroaryl-$G^1$-$X^1$—$Z^1$ (i.e. $L^1$ is NH and $A^1$=$C_{6-11}$arylene or 5-15 membered heteroarylene), compounds of formula 10 or 13 are oxidized with m-CPBA to a methanesulfinyl leaving group and then treated with the $Q^1$ amine. The reaction can be performed in the presence or absence of an acid or a base. Typical acids include, but are not limited to, hydrochloric acid, p-toluenesulfonic acid (p-TsOH), methanesulfonic and camphorsulfonic acid. Typical bases include, but are not limited to, potassium or cesium carbonate, diisopropylethylamine and triethylamine. Solvents that are typically used include, but are not limited to alcoholic solvents such as ethanol, isopropanol, methoxyethanol, 1-methoxy-2-propanol and t-butanol using either thermal or microwave heating. Examples 1-11, 13-23, 25-27, 30-39, 43-49, 52-57, 79-83, 85-96, 109, 11, 115-122, 124-126, 128-173, 175-189, 192-196, 198-253 illustrate, but do not limit, the syntheses of $Q^1$ nucleophiles and $Q^2$-M substrates for the synthesis of compounds of formula I in which $Q^3$, $Q^4$=H, $Q^1$=NH-Aryl-$G^2$-$X^2$—$Z^2$ or NH-heteroaryl-$G^1$-$X^1$—$Z^1$ (i.e. $L^1$ is —$C_{0-3}$alkylNR$^4C_{0-3}$alkyl- and $A^1$=$C_{6-11}$arylene or 5-15 membered heteroarylene) and $Q^2$=aryl-$G^2$-$X^2$—$Z^2$ or heteroaryl-$G^2$-$X^2$—$Z^2$ (i.e. $L^2$ is absent, $A^2$=$C_{6-11}$arylene or 5-15 membered heteroarylene). This method may also be used to prepare compounds of formula I in which $Q^3$, $Q^4$=H, $Q^1$=NH-alkyl-$G^2$-$X^2$—$Z^2$ (i.e. $L^1$ is —$C_{0-3}$alkylNR$^4C_{0-3}$alkyl- and $A^1$=$C_{1-6}$alkylene optionally substituted by 1-12 $R^a$) and $Q^2$=aryl-$G^2$-$X^2$—$Z^2$ or heteroaryl-$G^2$-$X^2$—$Z^2$ (i.e. $L^2$ is absent, $A^2$=$C_{6-11}$arylene or 5-15 membered heteroarylene), as demonstrated in Examples 21, 28, 29. Furthermore, this method may also be used to prepare compounds of formula I in which $Q^3$, $Q^4$=H, $Q^1$=Oxygen-$A^1$-$G^2$-$X^2$—$Z^2$ (i.e. $L^1$ is —$C_{0-3}$alkyl-O—$C_{0-3}$alkyl- and $A^1$=$C_{1-6}$alkylene optionally substituted by 1-12 $R^a$) and $Q^2$=aryl-$G^2$-$X^2$—$Z^2$ or heteroaryl-$G^2$-$X^2$—$Z^2$ (i.e. $L^2$ is absent, $A^2$=$C_{6-11}$arylene or 5-15 membered heteroarylene), as demonstrated in Examples 113, 190, 191, 197.

For compounds of formula I in which $Q^3$, $Q^4$=H and $Q^2$=cycloalkyl-$G^2$-$X^2$—$Z^2$ or alkyl-alkyl-$G^2$-$X^2$-$L^2$ (i.e. $L^2$ is absent, $A^2$=$C_{3-11}$cycloalkylene optionally substituted by 1-20 $R^b$ or $G^2$-$X^2$—$Z^2$ $A^2$=$C_{1-6}$alkylene optionally substituted by 1-12 $R^b$), and $Q^1$=NH-Aryl-$G^2$-$X^2$—$Z^2$ or NH-heteroaryl-$G^1$-$X^1$—$Z^1$ (i.e. $L^1$ is —$C_{0-3}$alkylNR$^4C_{0-3}$alkyl- and $A^1$=$C_{6-11}$arylene or 5-15 membered heteroarylene), scheme 3 illustrates the synthesis of cyclohexyl derivative using cycloalkyl-zinc bromide compounds of formula 18 which undergo a Pd-catalyzed coupling to 10 to give compounds of formula 19, which following a sequence similar to that in Scheme 2 provide compounds of formula 20. This is illustrated with Examples 123 and 127. Also, alkyl-zinc halides are also able to undergo this type of process to give compounds of formula 25. One skilled in the art would recognize that a variety of cycloalkylzinc halides alkyl-zinc halides are commercially available or readily synthesized from cycloalkyl halides or alkyl halides by treatment with elemental Zn in a Grignard-type reaction would be effective for the synthesis of compounds of formula 22.

Scheme 3

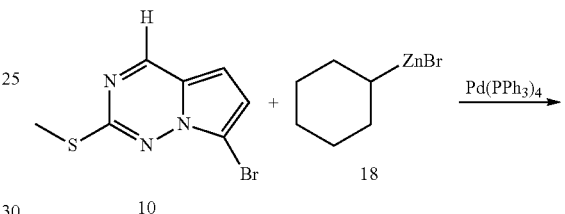

Scheme 2

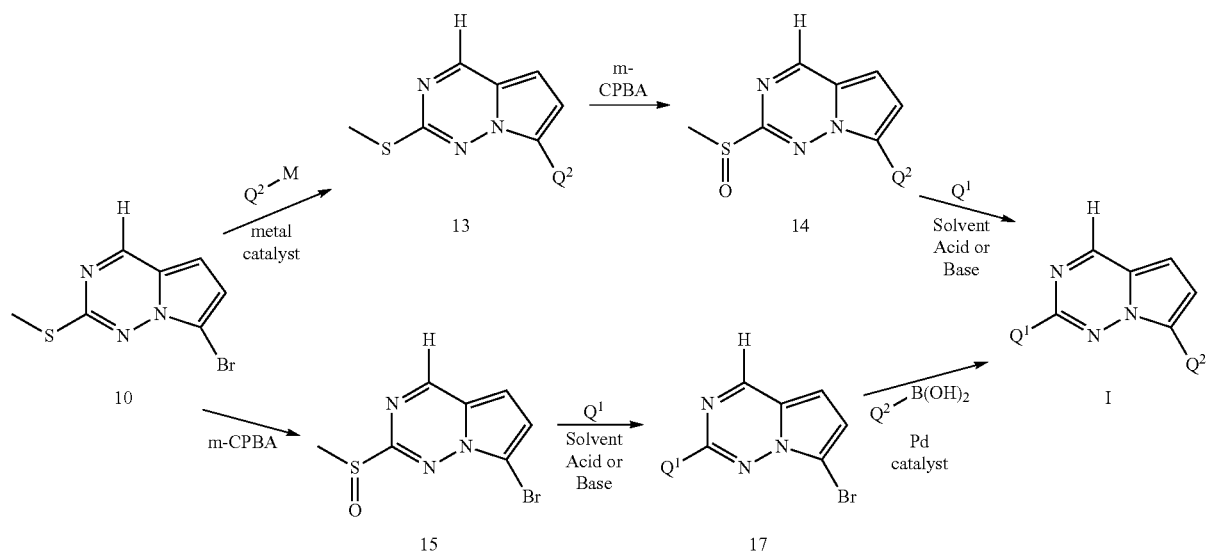

M = B(OH)$_2$, B(OR)$_2$, BF$_3$K, SnAlkyl$_3$, CrCl$_2$, ZnBr, Li, Mg, K, Na
Metal Catalyst = Pd, Pt, Ni, Cr, Au, Zn, Cu

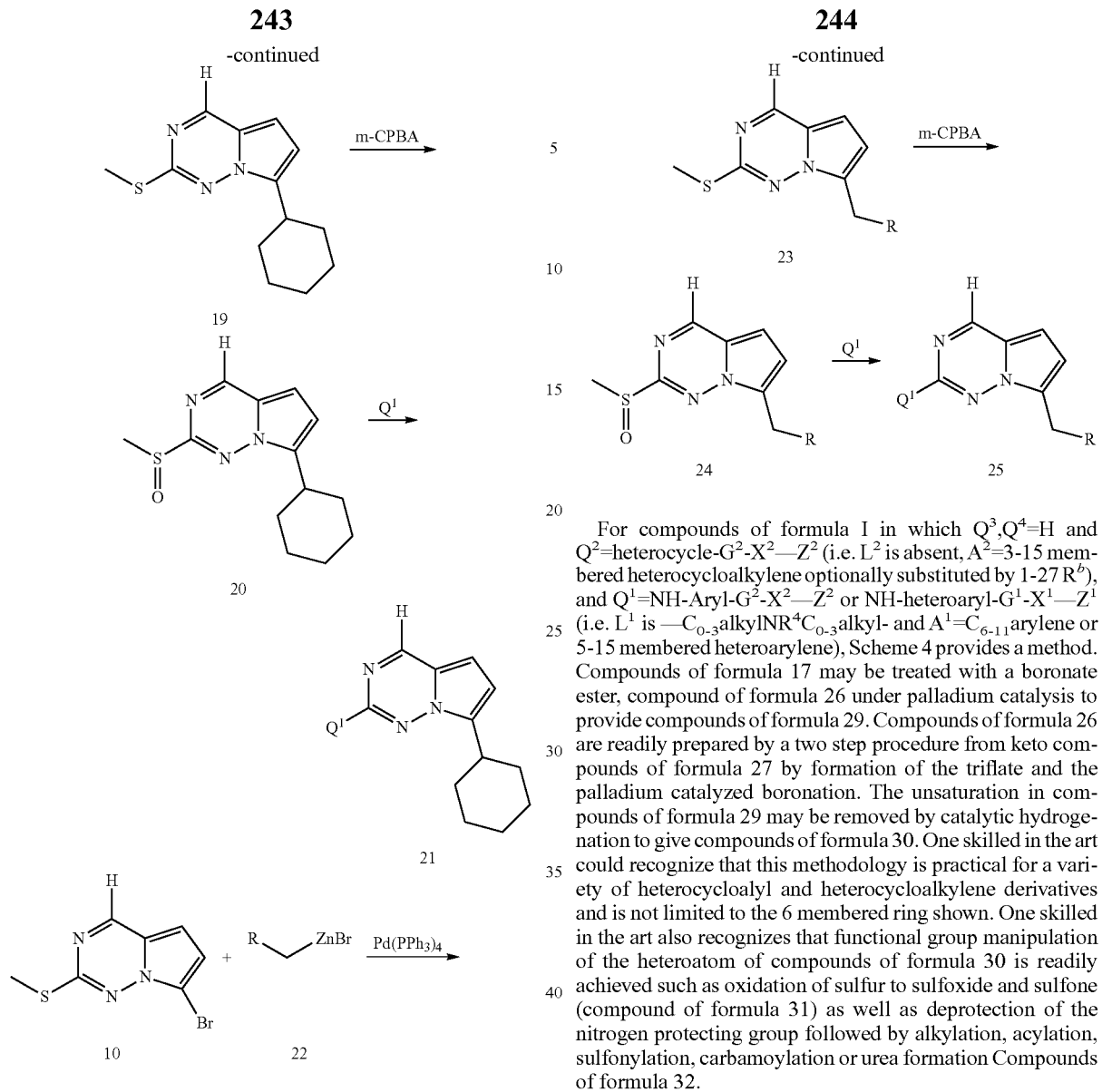

For compounds of formula I in which $Q^3, Q^4=H$ and $Q^2$=heterocycle-$G^2$-$X^2$—$Z^2$ (i.e. $L^2$ is absent, $A^2$=3-15 membered heterocycloalkylene optionally substituted by 1-27 $R^b$), and $Q^1$=NH-Aryl-$G^2$-$X^2$—$Z^2$ or NH-heteroaryl-$G^1$-$X^1$—$Z^1$ (i.e. $L^1$ is —$C_{0-3}$alkyl$NR^4C_{0-3}$alkyl- and $A^1=C_{6-11}$arylene or 5-15 membered heteroarylene), Scheme 4 provides a method. Compounds of formula 17 may be treated with a boronate ester, compound of formula 26 under palladium catalysis to provide compounds of formula 29. Compounds of formula 26 are readily prepared by a two step procedure from keto compounds of formula 27 by formation of the triflate and the palladium catalyzed boronation. The unsaturation in compounds of formula 29 may be removed by catalytic hydrogenation to give compounds of formula 30. One skilled in the art could recognize that this methodology is practical for a variety of heterocycloalyl and heterocycloalkylene derivatives and is not limited to the 6 membered ring shown. One skilled in the art also recognizes that functional group manipulation of the heteroatom of compounds of formula 30 is readily achieved such as oxidation of sulfur to sulfoxide and sulfone (compound of formula 31) as well as deprotection of the nitrogen protecting group followed by alkylation, acylation, sulfonylation, carbamoylation or urea formation Compounds of formula 32.

Scheme 4

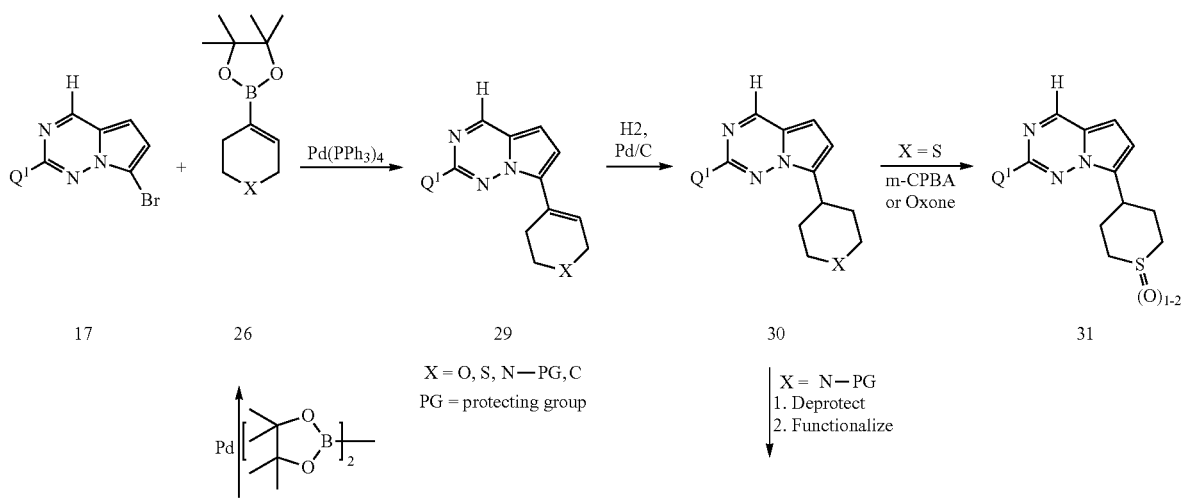

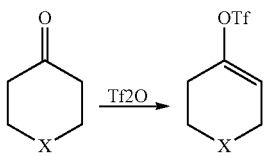

27　28

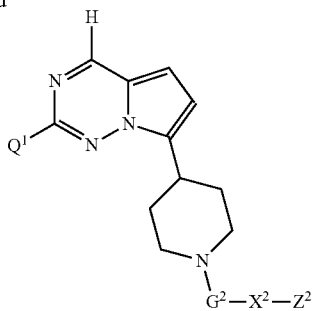

32

For compounds of formula I in which $Q^3, Q^4$=H and $Q^2$=CN, and $Q^1$=NH-Aryl-$G^2$-$X^2$—$Z^2$ or NH-heteroaryl-$G^1$-$X^1$—$Z^1$ (i.e. $L^1$ is —$C_{0-3}$alkylN$R^4C_{0-3}$alkyl- and $A^1$=$C_{6-11}$ arylene or 5-15 membered heteroarylene), Scheme 5 provides a method. Treatment of compounds of formula 17 with Zinc cyanide using palladium and copper catalysis provides compounds of formula 34. Example 51 describes this embodiment. Furthermore, for compounds of formula I in which $Q^3, Q^4$=H and $Q^2$=—$C_{0-3}$alkylC(=O)N$R^{44}C_{0-3}$alkyl-$A^1$-$G^1$-$X^1$—$Z^1$ (i.e. $L^2$ is —$C_{0-3}$alkylC(=O)N$R^{44}C_{0-3}$alkyl,), and $Q^1$=NH-Aryl-$G^2$-$X^2$—$Z^2$ or NH-heteroaryl-$G^1$-$X^1$—$Z^1$ (i.e. $L^1$ is NH and $A^1$=$C_{6-11}$ arylene or 5-15 membered heteroarylene) may be synthesized from compounds of formula 34 by hydrolysis to compounds of formula 35, which in turn are converted to the desired amide via standard peptide coupling procedures and an appropriate amine. One skilled in the art recognizes that a variety of alkyl and aromatic amines would be applicable to this chemistry.

Scheme 5

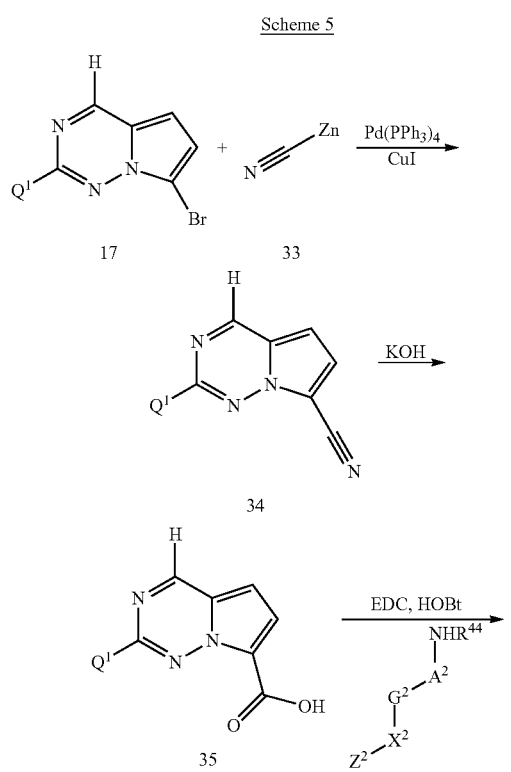

-continued

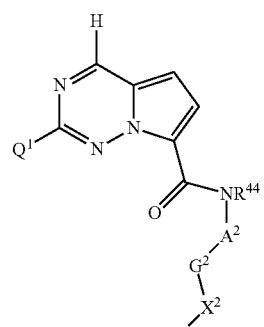

36

For compounds of formula I in which $Q^3, Q^4$=H and $Q^2$=amino-aryl-$G^2$-$X^2$—$Z^2$ (i.e. $L^2$ is —$C_{0-3}$alkylN$R^{44}C_{0-3}$ alkyl-, $A^2$=$C_{6-11}$arylene optionally substituted by 1-6 $R^b$), and $Q^1$=NH-Aryl- or NH-heteroaryl-$G^1$-$X^1$—$Z^1$ (i.e. $L^1$ is —$C_{0-3}$alkylN$R^4C_{0-3}$alkyl- and $A^1$=$C_{6-11}$arylene or 5-15 membered heteroarylene), Scheme 6 provides a method using a Buchwald palladium-catalyzed amination reaction between compounds of formula 17 and 37 to give compounds of formula 38. This is typified by Example 24. One skilled in the art recognizes that this methodology will be acceptable to form heteroarylamines (i.e. $L^2$ is —$C_{0-3}$alkylN$R^{44}C_{0-3}$alkyl-, $A^2$=5-15 membered heteroarylene optionally substituted by 1-14 $R^b$) as well as alkylamines $L^2$ is —$C_{0-3}$alkylN$R^{44}C_{0-3}$ alkyl-, $A^2$=$C_{1-6}$alkylene optionally substituted by 1-12 $R^b$, cycloalkylamines $L^2$ is —$C_{0-3}$alkylN$R^{44}C_{0-3}$alkyl-, $A^2$= $C_{3-11}$ cycloalkylene optionally substituted by 1-20 $R^b$, $C_{4-17}$cycloalkylalkylene optionally substituted by 1-31 $R^b$) and heterocycloalkylamines (i.e. $L^2$ is —$C_{0-3}$alkylN$R^{44}C_{0-3}$ alkyl-, $A^2$=3-15 membered heterocycloalkylene optionally substituted by 1-27 $R^b$, 4-21 membered heterocycloalkylalkylene optionally substituted by 1-39 $R^b$). One skilled in the art recognizes that the exact conditions may vary from substrate to substrate and guidelines for chemical reactivity may be found in (but not limited to) such reviews as Surry, David S.; Buchwald, Stephen L. Biaryl phosphane ligands in palladium-catalyzed amination. *Angewandte Chemie, International Edition*, 2008, 47(34), 6338-6361 and references therein.

Scheme 6

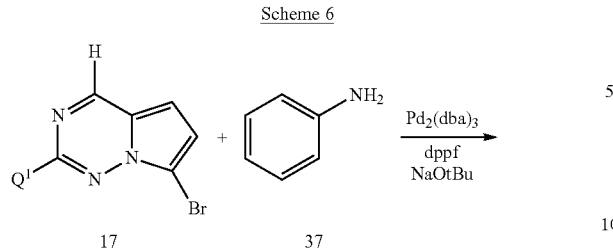

Scheme 7

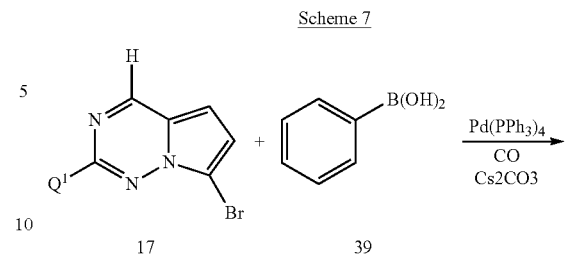

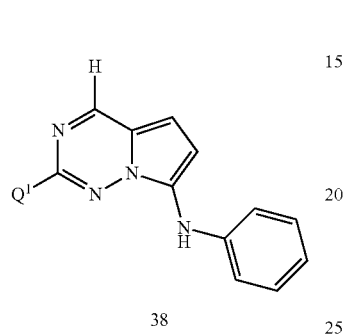

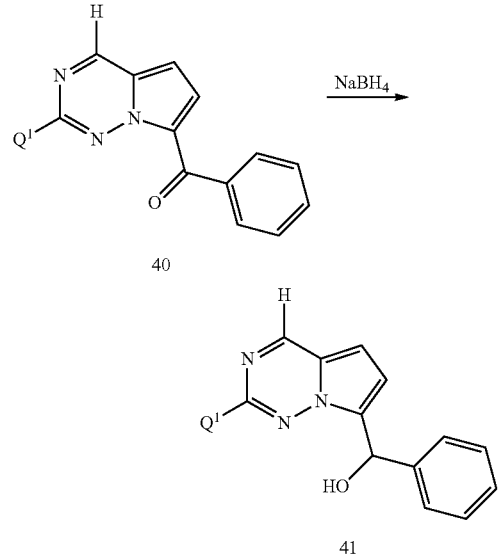

For compounds of formula I in which $Q^3, Q^4$=H and $Q^2$=carbonyl-aryl-$G^2$-$X^2$—$Z^2$ (i.e. $L^2$ is —$C_{0-3}$alkylC(=O)$C_{0-3}$alkyl-, $A^2$=$C_{6-11}$ arylene optionally substituted by 1-6 $R^b$), and $Q^1$=NH-Aryl- or NH-heteroaryl-$G^1$-$X^1$—$Z^1$ (i.e. $L^1$ is —$C_{0-3}$alkylNR$^4C_{0-3}$alkyl- and $A^1$=$C_{6-11}$arylene or 5-15 membered heteroarylene), Scheme 7 provides a method using a palladium catalyzed CO-insertion reaction with boronic acid compounds of formula 39 and aryl halide compounds of formula 17 to give compounds of formula 40. Example 72 demonstrates this methodology. One skilled in the art also recognizes that compounds of formula 40 may be transformed via reduction into compounds of formula I such as 41 in which $Q^3, Q^4$=H and $Q^2$=carbinol-aryl-$G^2$-$X^2$—$Z^2$ (i.e. $L^2$ is —$C_{0-3}$alkylCH(OH)$C_{0-3}$alkyl-, $A^2$=$C_{6-11}$arylene optionally substituted by 1-6 $R^b$, $C_{7-16}$arylalkylene optionally substituted by 1-18 $R^b$). Furthermore, more generally, compounds of formula I in which $Q^3, Q^4$=H and $Q^2$=carbinol-$A^2$-$G^2$-$X^2$—$Z^2$ (i.e. $L^2$ is —$C_{0-3}$alkylCH(OH)$C_{0-3}$alkyl-, $A^2$=$C_{1-6}$alkylene optionally substituted by 1-12 $R^b$, $C_{2-6}$alkenylene optionally substituted by 1-10 $R^b$, $C_{2-6}$alkynylene optionally substituted by 1-8 $R^b$, $C_{6-11}$arylene optionally substituted by 1-6 $R^b$, $C_{7-16}$arylalkylene optionally substituted by 1-18 $R^b$, $C_{3-11}$cycloalkylene optionally substituted by 1-20 $R^b$, $C_{4-17}$cycloalkylalkylene optionally substituted by 1-31 $R^b$, 3-15 membered heterocycloalkylene optionally substituted by 1-27 $R^b$, 4-21 membered heterocycloalkylalkylene optionally substituted by 1-39 $R^b$, 5-15 membered heteroarylene optionally substituted by 1-14 $R^b$, or 6-21 membered heteroarylalkylene optionally substituted by 1-26 $R^b$) may be formed via compounds of formula 43 which is derived from compounds of formula 6 via reduction/oxidation to produce compounds of formula 42 and a Vilsmeier reaction. This intermediate of formula 43 can be treated with a Grignard reagent (or any reactive metal species such as $L^1$ or Zn anions) to produce compounds of formula 46. One skilled in the art recognizes that a variety of Grignard species of formula 44 are available from halo compounds of formula 45 via metal insertion reactions. Following Scheme 2, compounds of formula 46 may be transformed into compounds of formula 47.

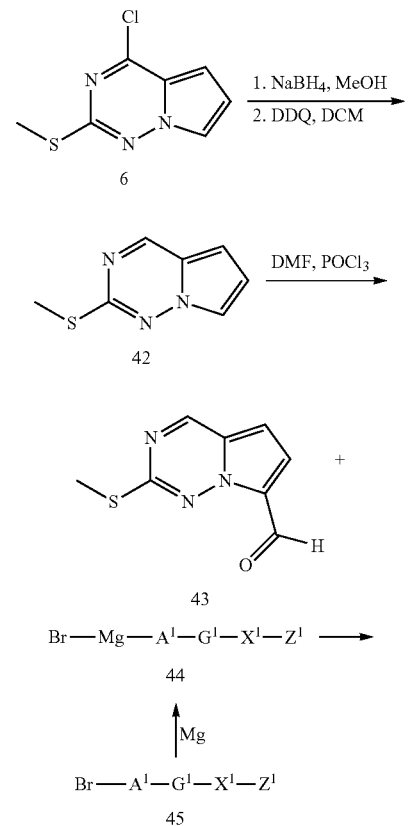

249

-continued

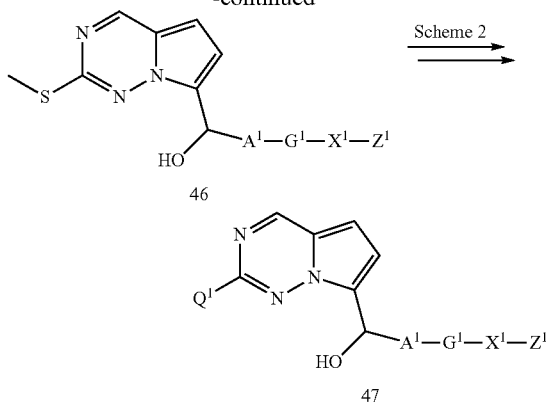

Scheme 2 →

250 tuted by 1-12 $R^b$, $C_{2-6}$alkenylene optionally substituted by 1-10 $R^b$, $C_{2-6}$alkynylene optionally substituted by 1-8 $R^b$, $C_{6-11}$ arylene optionally substituted by 1-6 $R^b$, $C_{7-16}$arylalkylene optionally substituted by 1-18 $R^b$, $C_{3-11}$cycloalkylene optionally substituted by 1-20 $R^b$, $C_{4-17}$cycloalkylalkylene optionally substituted by 1-31 $R^b$, 3-15 membered heterocycloalkylene optionally substituted by 1-27 $R^b$, 4-21 membered heterocycloalkylalkylene optionally substituted by 1-39 $R^b$, 5-15 membered heteroarylene optionally substituted by 1-14 $R^b$, or 6-21 membered heteroarylalkylene optionally substituted by 1-26 $R^b$, respectively), Scheme 9 provides a method using reductive amination reaction between compounds of formula 43 and amines of formula 51 to give compounds of formula 52. One skilled in the art recognizes that the a variety of conditions exist for reductive amination reactions and that a variety of syntheses are available for amines of formula 51.

For compounds of formula I in which $Q^3,Q^4$=H and $Q^2$=thio-aryl-$G^2$-$X^2$—$Z^2$ (i.e. $L^2$ is $C_{0-3}$alkylS(O)$_n$$C_{0-3}$alkyl- where n=0-2, and $A^2$=$C_{6-11}$arylene optionally substituted by 1-6 $R^b$), and $Q^1$=NH-Aryl- or NH-heteroaryl-$G^1$-$X^1$—$Z^1$ (i.e. $L^1$ is —$C_{0-3}$alkylNR$^4$$C_{0-3}$alkyl- and $A^1$=$C_{6-11}$arylene or 5-15 membered heteroarylene), Scheme 8 provides a method using an Ullman-type coupling with compounds of formula 17 and thiophenol compounds of formula 48 to provide compounds of formula 49 which can be oxidized with mCPBA to compounds of formula 50. Examples 78, 97, 98, 111 demonstrate this methodology.

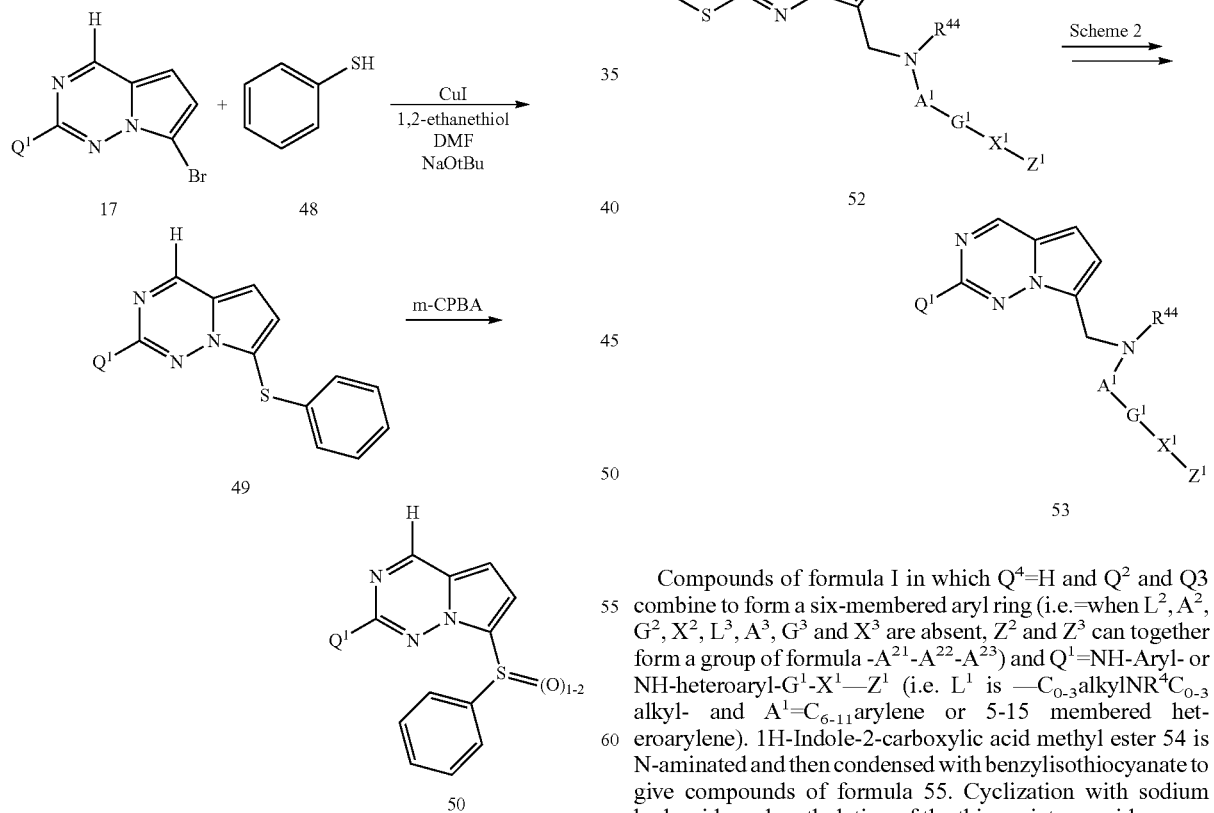

For compounds of formula I in which $Q^3,Q^4$=H and $Q^2$=methyleneamino-$A^2$-$G^2$-$X^2$—$Z^2$ (i.e. $L^2$ is —$C_{0-3}$alkylNR$^{44}$$C_{0-3}$alkyl-, $A^2$=$C_{1-6}$alkylene optionally substi- Compounds of formula I in which $Q^4$=H and $Q^2$ and Q3 combine to form a six-membered aryl ring (i.e.=when $L^2$, $A^2$, $G^2$, $X^2$, $L^3$, $A^3$, $G^3$ and $X^3$ are absent, $Z^2$ and $Z^3$ can together form a group of formula -$A^{21}$-$A^{22}$-$A^{23}$) and $Q^1$=NH-Aryl- or NH-heteroaryl-$G^1$-$X^1$—$Z^1$ (i.e. $L^1$ is —$C_{0-3}$alkylNR$^4$$C_{0-3}$alkyl- and $A^1$=$C_{6-11}$arylene or 5-15 membered heteroarylene). 1H-Indole-2-carboxylic acid methyl ester 54 is N-aminated and then condensed with benzylisothiocyanate to give compounds of formula 55. Cyclization with sodium hydroxide and methylation of the thio moiety provides compounds of formula 58. Chlorination followed by a two step reduction/oxidation provides compounds of formula 59. Oxidation gives compounds of formula 61. These can be reacted with an appropriate $Q^1$ group (via Scheme 2) to provide compounds of formula I with a [1,2,4]triazino[1,6-a]indole substructure. One skilled in the art would recognize that the 1H-Indole-2-carboxylic acid methyl ester 19 starting material may be substituted or not to provide [1,2,4]triazino[1,6-a] indole compounds with corresponding substituents at $Q^4$ and on the $Q^2/Q^3$ phenyl ring. Examples 261-273 describe suitable procedures to provide the desired compounds of formula I described above.

Scheme 10

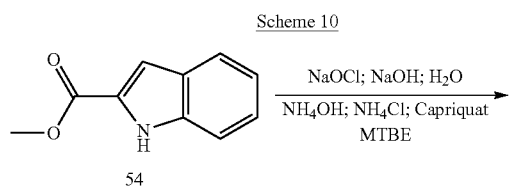

54

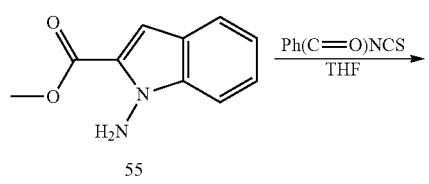

55

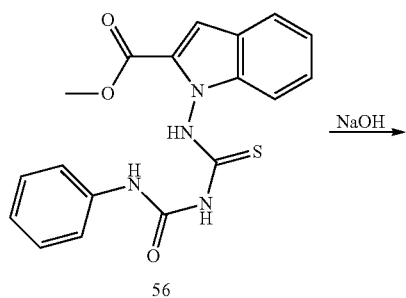

56

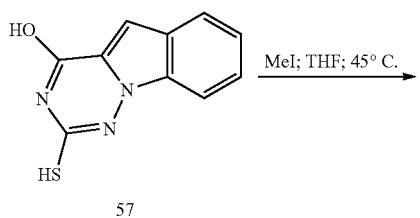

57

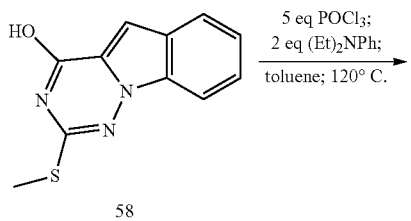

58

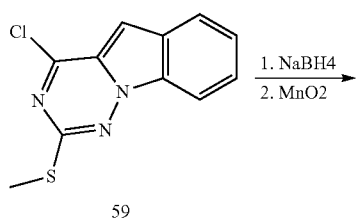

59

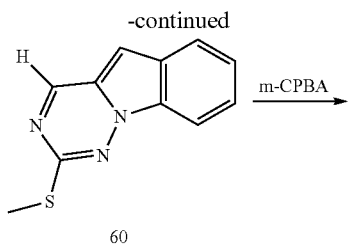

60

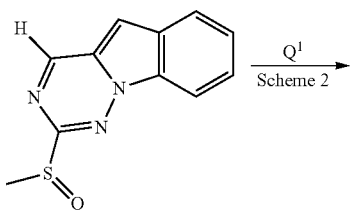

61

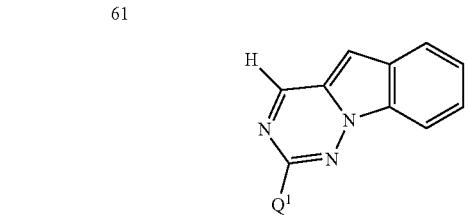

62

Analogously, Compounds of formula I in which $Q^2$=H and $Q^3$ and $Q^4$ combine to form a six-membered aryl ring (i.e.=when $L^3$, $A^3$, $G^3$, $X^3$, $L^4$, $A^4$, $G^4$ and $X^4$ are absent, $Z^3$ and $Z^4$ can together form a group of formula -$A^{21}$-$A^{22}$-$A^{23}$- and $Q^1$=NH-Aryl- or NH-heteroaryl-$G^1$-$X^1$—$Z^1$ (i.e. $L^1$ is —$C_{0-3}$alkyl$NR^4C_{0-3}$alkyl- and $A^1$=$C_{6-11}$arylene or 5-15 membered heteroarylene). compounds of formula I in which the ring system is a 1,3,9a-triaza-fluorene (i.e., $Q^3$ and $Q^4$ combine to form a aryl ring) can be prepared using sequence according to that described generally in Scheme 11. Isoindole compounds of formula 28 (which can be synthesized according to procedures in Cignarella, G. et al. *Synthesis*, 1975, 4, 252-3 "Isoindole derivatives. IX. New approach to isoindole-carboxylic esters") can be treated analogous to the indole derivatives of Scheme 10, N-amination and condensation with benzylisothiocyanate to give followed by cyclization then methylation, Chlorination followed by the two step reduction/oxidation provides which is then oxidized at sulfur gives compounds of formula 64. These can be reacted with an appropriate $Q^1$ group to provide compounds of formula I with a 1,3,9a-triaza-fluorene substructure. One skilled in the art would recognize that the isoindole compound of formula 28 starting material may be substituted or not to provide 1,3,9a-triaza-fluorene compounds with corresponding substituents at $Q^2$ and on the $Q^3/Q^4$ phenyl ring.

Scheme 11

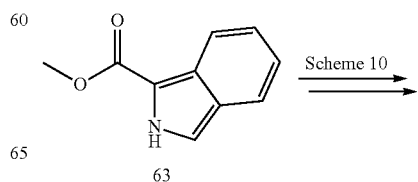

63

253
-continued

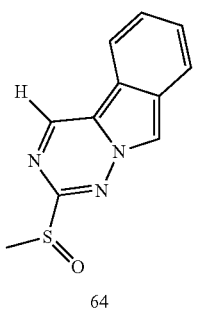
64

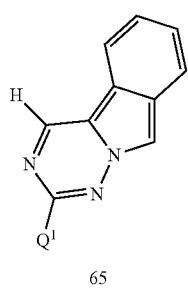
65

Scheme 12 illustrates how compounds of formula 11 are converted to compounds of formula I in which $Q^2$, $Q^3$=H, $Q^1$ is —NH-Aryl-$G^1$-$X^1$—$Z^1$ or —NH-heteroaryl-$G^1$-$X^1$—$Z^1$ (i.e. $L^1$ is NH and $A^1$=$C_{6-11}$arylene or 5-15 membered heteroarylene) and $Q^4$ in which $L^4$ is absent and $Q^4$ is represented by aryl-$G^4$-$X^4$—$Z^4$ or heteroaryl-$G^4$-$X^4$—$Z^4$ (i.e. $A^4$=$C_{6-11}$arylene or 5-15 membered heteroarylene). Oxidation of the sulfur of compounds of formula 11 activate it as a leaving group to install $Q^1$ which can be accomplished using conditions described in Scheme 2. Installation of $Q^4$ uses a transition metal-mediated coupling reaction between compounds of formula 67 and an appropriately modified aryl or heteroaryl group (i.e. aryl or heteroaryl bornic acids) provides compounds of formula 68 using conditions described for Scheme 2. Examples 40-42, illustrate these syntheses.

Scheme 12

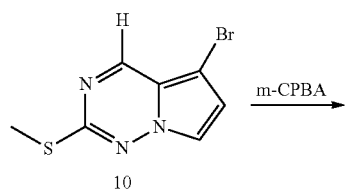
10

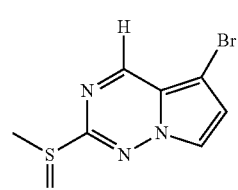
66

254
-continued

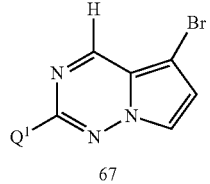
67 → 68

Scheme 13 illustrates how compounds of formula 12 are converted to compounds of formula I in which $Q^2$=Br, $Q^3$=H, $Q^1$ is —NH-Aryl-$G^1$-$X^1$—$Z^1$ or —NH-heteroaryl-$G^1$-$X^1$—$Z^1$ (i.e. $L^1$ is NH and $A^1$=$C_{6-11}$arylene or 5-15 membered heteroarylene) and $Q^4$ in which $L^4$ is absent and $Q^4$ is represented by aryl-$G^4$-$X^4$—$Z^4$ or heteroaryl-$G^4$-$X^4$—$Z^4$ (i.e. $A^4$=$C_{6-11}$arylene or 5-15 membered heteroarylene). Oxidation of the sulfur of compounds of formula 12 activate it as a leaving group to install $Q^1$ which can be accomplished using conditions described in Scheme 2, which is illustrated by Example 84. Installation of $Q^4$ uses a transition metal-mediated coupling reaction between compounds of formula 70 and an appropriately modified aryl or heteroaryl group (i.e. aryl or heteroaryl bornic acids) provides compounds of formula 71 using conditions described for Scheme 2. Also illustrated are compounds of formula 72 which are also isolated from the reaction of compounds of formula 70 in which Compounds of formula I in which $Q^4$=Br, $Q^3$=H, $Q^1$ is —NH-Aryl-$G^1$-$X^1$—$Z^1$ or —NH-heteroaryl-$G^1$-$X^1$—$Z^1$ (i.e. $L^1$ is NH and $A^1$=$C_{6-11}$arylene or 5-15 membered heteroarylene) and $Q^2$ in which $L^2$ is absent and $Q^2$ is represented by aryl-$G^2$-$X^2$—$Z^2$ or heteroaryl-$G^2$-$X^2$—$Z^2$ (i.e. $A^2$=$C_{6-11}$arylene or 5-15 membered heteroarylene). Examples 101 and 102 illustrate this sequence.

Scheme 13

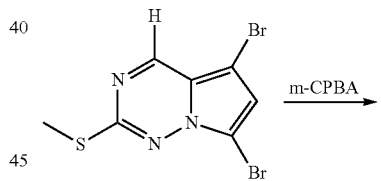
12

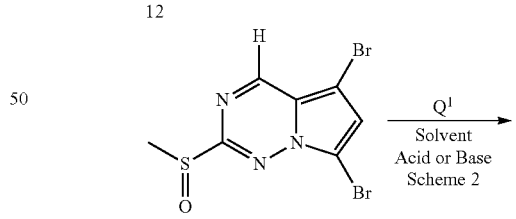
69

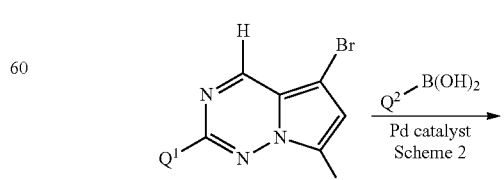
70

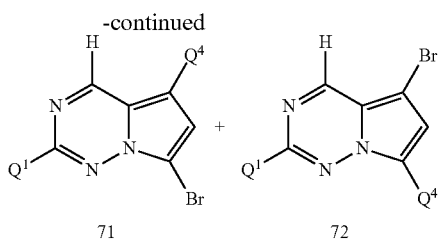

Compounds of formula 72 [i.e. Compounds of formula I in which $Q^4$=Br, $Q^3$=H, $Q^1$ is —NH-Aryl-$G^1$-$X^1$—$Z^1$ or —NH-heteroaryl-$G^1$-$X^1$—$Z^1$ (i.e. $L^1$ is NH and $A^1$=$C_{6-11}$arylene or 5-15 membered heteroarylene) and $Q^2$ in which $L^2$ is absent and $Q^2$ is represented by aryl-$G^2$-$X^2$—$Z^2$ or heteroaryl-$G^2$-$X^2$—$Z^2$ (i.e. $A^2$=$C_{6-11}$arylene or 5-15 membered heteroarylene] can also be prepared according to the sequence in Scheme 14 in which compounds of formula 13 are brominated with NBS and then the sulfur oxidized to give compounds of formula 73 which are converted to compounds of formula 72 by conditions outlined in Scheme 2. Examples 91, 99, 100 illustrate this sequence. Furthermore, compounds of formula I in which $Q^3$,$Q^4$=Br, $Q^1$ is —NH-Aryl-$G^1$-$X^1$—$Z^1$ or —NH-heteroaryl-$G^1$-$X^1$—$Z^1$ (i.e. $L^1$ is NH and $A^1$=$C_{6-11}$arylene or 5-15 membered heteroarylene) and $Q^2$ in which $L^2$ is absent and $Q^2$ is represented by aryl-$G^2$-$X^2$—$Z^2$ or heteroaryl-$G^2$-$X^2$—$Z^2$ (i.e. $A^2$=$C_{6-11}$arylene or 5-15 membered heteroarylene] can also be prepared from compounds of formula 13 except that 2.2 eq of N-bromosuccinimide are used in the first step which will lead to compounds of formula 75 following the previously described chemistry. This is illustrated by Example 110.

substituent is unsaturated, catalytic hydrogenation will reduce the species to the corresponding saturated derivative. For compounds of formula I. $Q^3$,$Q^4$=alkyl or alkylene (i.e. $L^3$, $L^4$ is absent, $A^2$=$C_{1-6}$alkylene optionally substituted by 1-12 $R^b$) and $Q^2$ in which $L^2$ is absent and $Q^2$ is represented by aryl-$G^2$-$X^2$—$Z^2$ or heteroaryl-$G^2$-$X^2$—$Z^2$ (i.e. $A^2$=$C_{6-11}$arylene or 5-15 membered heteroarylene] can be synthesized from compounds of formula 75 (Scheme 15) using a metal catalyzed coupling of a trimethylboroxine to give compounds of formula 76. Examples 103, 104, 105, 106, 107, 108, 112, 114. Also, for compounds of formula I in which $Q^3$=H, $Q^4$=—CN (i.e. $L^4$, $A^4$, $G^4$, $X^4$ are absent and $Z^4$=CN) and $Q^1$ is —NH-Aryl-$G^1$-$X^1$—$Z^1$ or —NH-heteroaryl-$G^1$-$X^1$—$Z^1$ (i.e. $L^1$ is NH and $A^1$=$C_{6-11}$ aryl, $C_{6-11}$ arylene or 5-15 membered heteroaryl, 5-15 membered heteroarylene) and $Q^2$ in which $L^2$ is absent and $Q^2$ is represented by aryl-$G^2$-$X^2$—$Z^2$ or heteroaryl-$G^2$-$X^2$—$Z^2$ (i.e. $A^2$=$C_{6-11}$arylene or 5-15 membered heteroarylene] can be synthesized from compounds of formula 72 using a Pd-catalyzed coupling of zinc cyanide in the presence of copper iodide to give compounds of formula 78. The is illustrated with Example 114.

Scheme 15

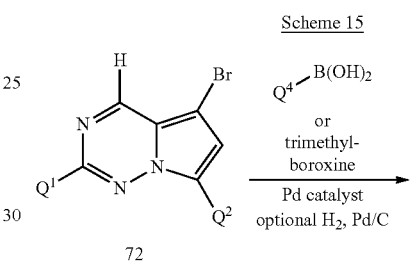

Scheme 14

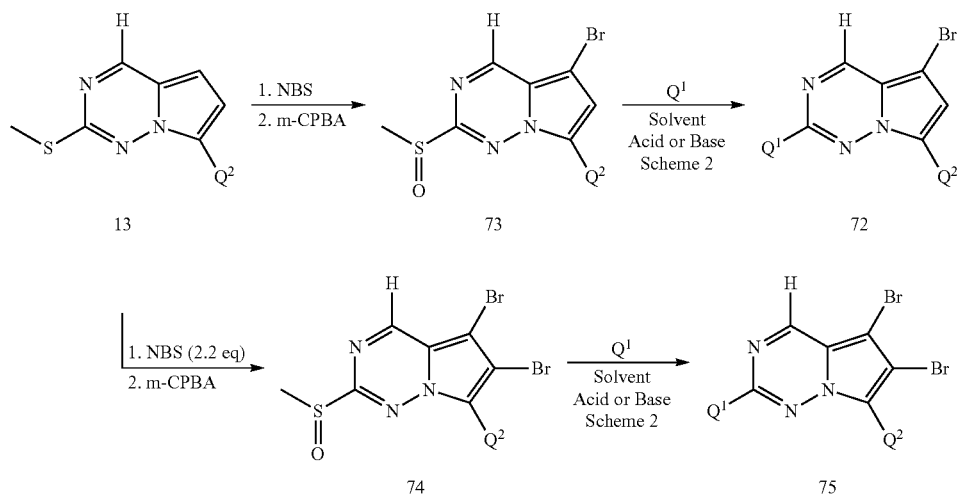

Compounds of formula I in which $Q^3$=H, $Q^4$=alkyl or alkylene (i.e. $L^4$ is absent, $A^4$=$C_{1-6}$alkylene optionally substituted by 1-12 $R^b$, $C_{2-6}$alkenylene optionally substituted by 1-10 $R^b$) and $Q^1$ is —NH-Aryl-$G^1$-$X^1$—$Z^1$ or —NH-heteroaryl-$G^1$-$X^1$—$Z^1$ (i.e. $L^1$ is NH and $A^1$=$C_{6-11}$arylene or 5-15 membered heteroarylene) and $Q^2$ in which $L^2$ is absent and $Q^2$ is represented by aryl-$G^2$-$X^2$—$Z^2$ or heteroaryl-$G^2$-$X^2$—$Z^2$ (i.e. $A^2$=$C_{6-11}$arylene or 5-15 membered heteroarylene] can be synthesized from compounds of formula 72 (Scheme 15) using a metal catalyzed coupling of a vinylboronic acid or trimethylboroxine to give compounds of formula 76. If the Q4

-continued

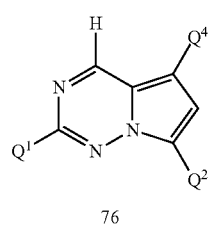

76

-continued

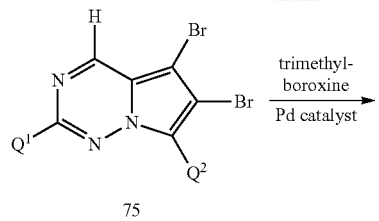
75

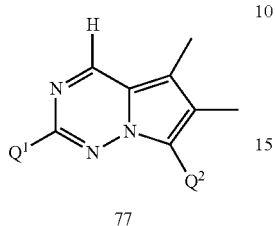
77

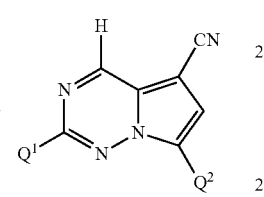
72    78

For compounds of formula I in which $Q^3, Q^4=H$, $Q^1=$urea-$A^1$-$G^2$-$X^2$—$Z^2$ (i.e. $L^1$ is —$C_{0-3}$alkylNR$^4$C(=O)NR$^4$C$_{0-3}$alkyl-) and $Q^2=$aryl-$G^2$-$X^2$—$Z^2$ or heteroaryl-$G^2$-$X^2$—$Z^2$ (i.e. $L^2$ is absent, $A^2=C_{6-11}$ aryl, $C_{6-11}$arylene or 5-15 membered heteroaryl, 5-15 membered heteroarylene) can be prepared according to Scheme 16 in which compounds of formula 14 are converted to the veratryl amine addict of formula 79. Treatment with trifluoroacetic acid (TFA) gives compounds of formula 80. These, in turn can be treated with an isocyanate to provide the urea derivatives of formula 81. For compounds of formula I in which $Q^3, Q^4=H$, $Q^1=$amide-$A^1$-$G^2$-$X^2$—$Z^2$ (i.e. $L^1$ is —$C_{0-3}$alkylNR$^4$C(=O)C$_{0-3}$alkyl-) and $Q^2=$aryl-$G^2$-$X^2$—$Z^2$ or heteroaryl-$G^2$-$X^2$—$Z^2$ (i.e. $L^2$ is absent, $A^2=C_{6-11}$aryl, $C_{6-11}$arylene or 5-15 membered heteroaryl, 5-15 membered heteroarylene) as well as $Q^3, Q^4=H$, $Q^1=$thiourea-$A^1$-$G^2$-$X^2$—$Z^2$ (i.e. $L^1$ is —$C_{0-3}$alkylNR$^4$C(=S)NR$^4$C$_{0-3}$alkyl-) and $Q^2=$aryl-$G^2$-$X^2$—$Z^2$ or heteroaryl-$G^2$-$X^2$—$Z^2$ (i.e. $L^2$ is absent, $A^2=C_{6-11}$ aryl, $C_{6-11}$arylene or 5-15 membered heteroaryl, 5-15 membered heteroarylene) may be prepared by reacting compounds of formula 80 with an appropriate acid (or acid chloride) to give amide compounds of formula 82. One skilled in the art recognizes that the isocycanates, acids/acid chlorides and isothiocyanates depicted in Scheme 16 are available from commercial sources or readily synthesized using known procedures to one skilled in the art.

Scheme 16

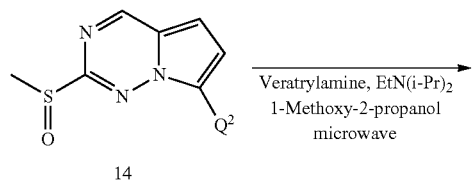
14

-continued

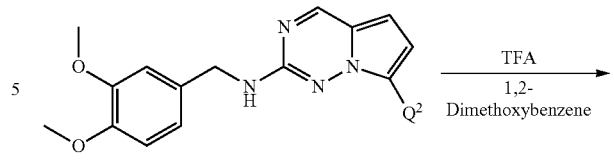
79

80

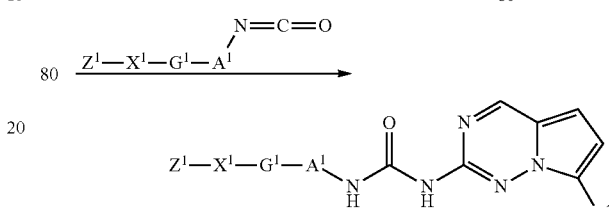
81

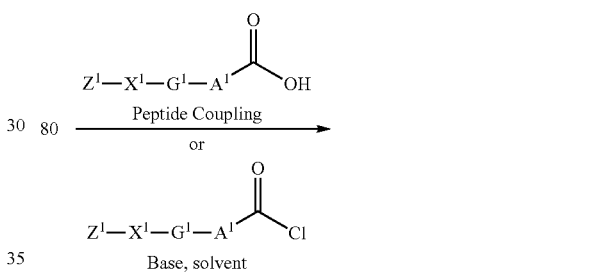
82

For synthesis of compounds of formula I in which $Q^1=$NH-Aryl-$G^2$-$X^2$—$Z^2$ or NH-heteroaryl-$G^1$-$X^1$—$Z^1$ (i.e. L is —$C_{0-3}$alkylNR$^4$C$_{0-3}$alkyl- and $A^1=C_{6-11}$arylene or 5-15 membered heteroarylene). The $Q^1$ aromatic amines may be available from commercial sources as depicted by, but not limited to those, in Scheme 17

Scheme 17

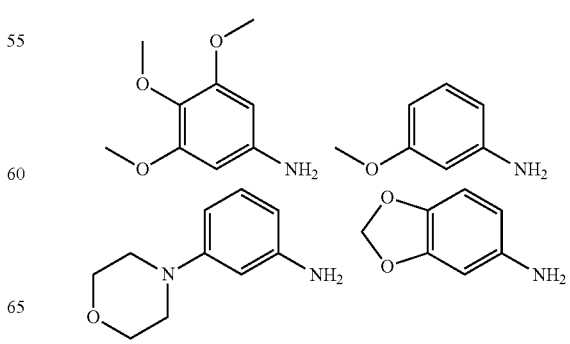

-continued

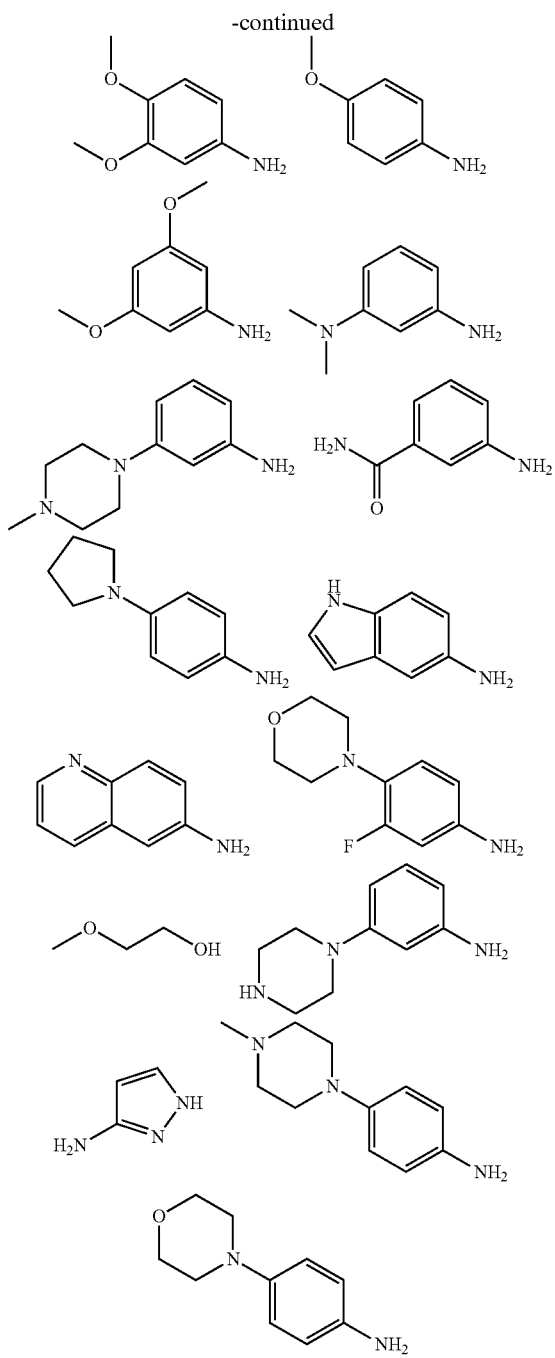

Alternatively, one skilled in the art recognizes that the synthesis of compounds that are depicted by $Q^1$ nucleophiles in Scheme 2 are available via a variety of chemistries well known to one skilled in the art of organic synthesis. Depicted in Scheme 18 are the syntheses of aromatic amines that are of the formula of a Q1 nucleophile (as depicted in Scheme 2), i.e. $Q^1=NH_2$-Aryl/heteroaryl-$G^1$-$X^1$—$Z^1$ (i.e. $A^1=C_{6-11}$arylene or 5-15 membered heteroarylene, $G^1$=3-15 membered heterocycloalkylene optionally substituted by 1-27 $R^{29}$, 4-21 membered heterocycloalkylalkylene optionally substituted by 1-39 $R^{29}$, $X^1$=$C_{1-6}$alkylene optionally substituted by 1-12 $R^{39}$ or 3-15 membered heterocycloalkylene optionally substituted by 1-27 $R^{39}$, 4-21 membered heterocycloalkylalkylene optionally substituted by 1-39 $R^{39}$ and $Z^1$=H or $C_{1-6}$alkyl optionally substituted by 1-13 $R^{49}$ or —$OR^{100}$)

Equations AA-C, E-F depict alkylations (via halide displacement or epoxide opening or reductive alkylation) to provide the desired amines after reduction of a nitro-aromatic group. Equations D and H provide a method of displacement of an aromatic fluoride to give, following reduction of the nitro the desired aromatic amine. The equations represented in Scheme 18 are effective for of a variety of different electrophiles (alkyl halides, epoxides and aldehydes or ketones, Eq. A-C, E-F) as well as a variety of heterocycles (Eq. D, G).

Scheme 18

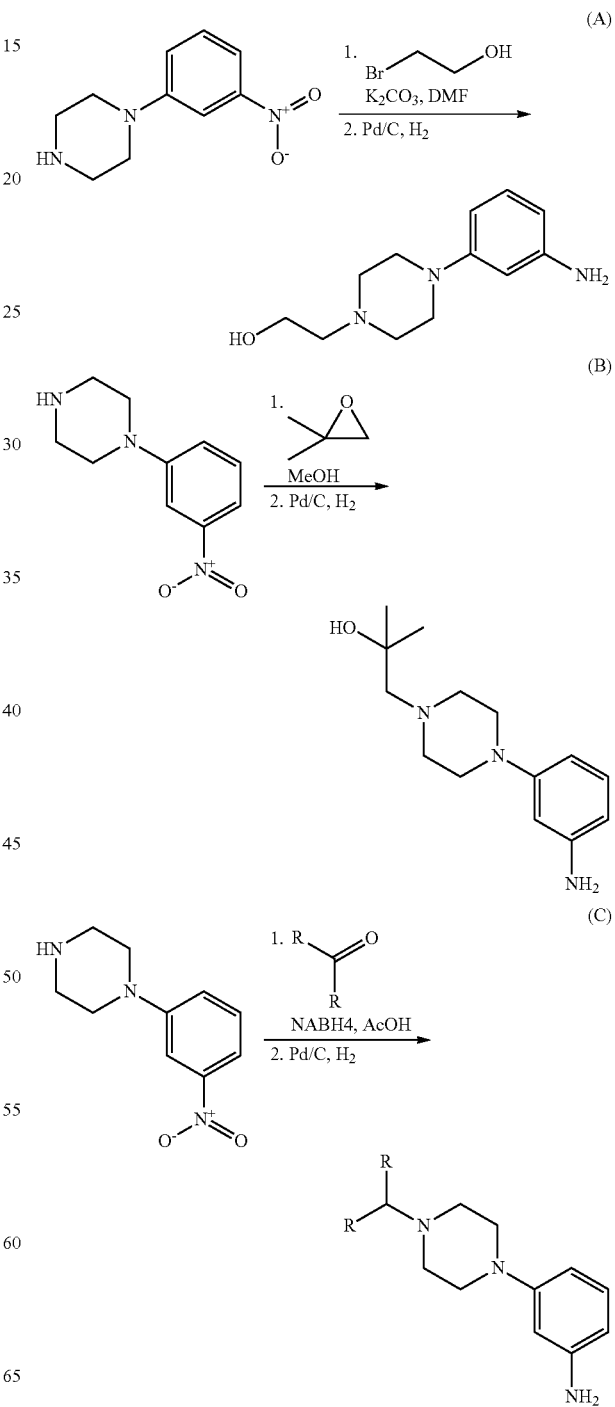

-continued (D)

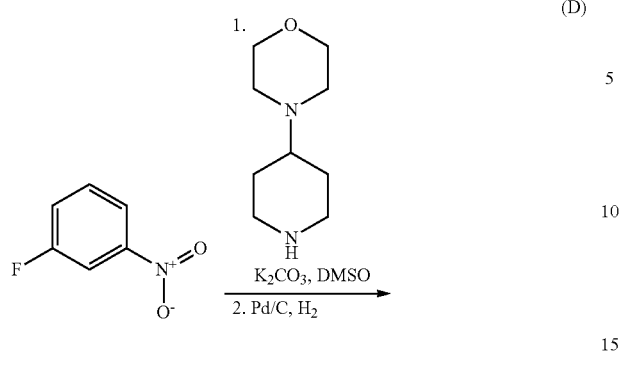

(E)

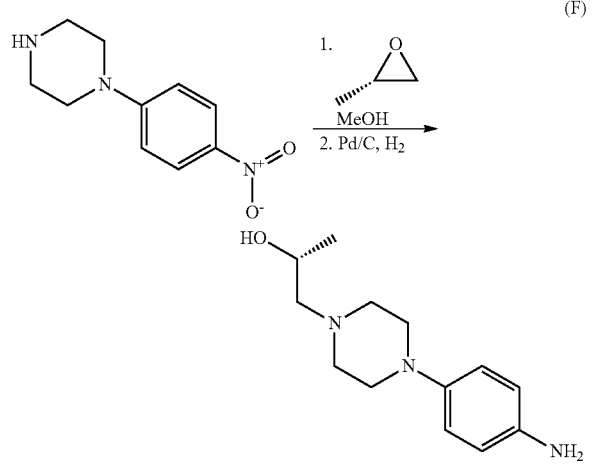

(F)

(G)

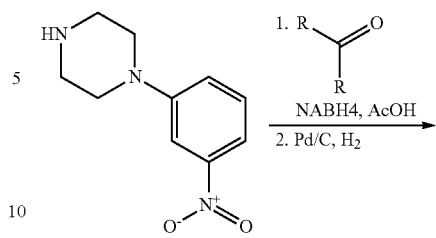

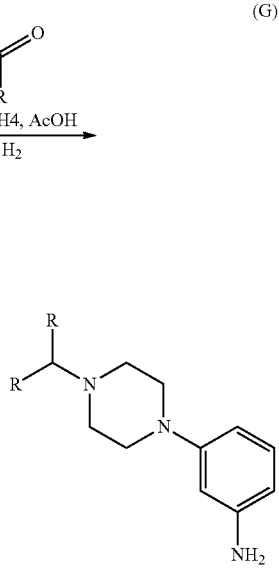

(H)

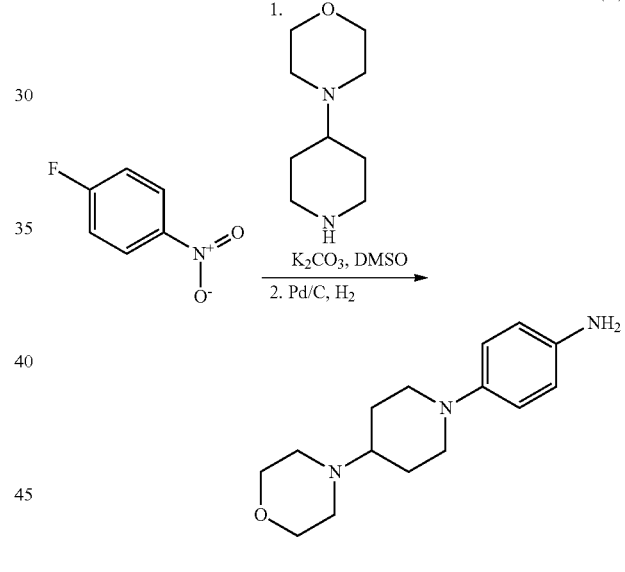

Scheme 19 illustrates how compounds of formula 83 (commercially available) are converted to compounds of formula I in which $Q^1, Q^2, Q^4$ are defined below. Conversion of compounds of formula 83 follows a similar protocol to that outlined in Scheme 1 to give the regioisomeric bromides of formula 84 and 85 which are separable via chromatography. Several sequences can convert these to compounds of formula I in which $Q^2$ is disposed in the 7-position or $Q^4$ is disposed in the 5-position, which involves (Sequence A) hydrolysis of the chloride to the hydroxyl, conversion to a leaving group (such as triflate) and then addition of $Q^1$ (using acid or base and an appropriate solvent). This is followed by coupling of $Q^2$ to this product. The order may be reversed (Sequence B) or alternatively (Sequence C) directly add $Q^1$ to the chloride followed by coupling of $Q^2$. The sequences A-C may be applied to compounds of formula 85 as well. Examples that illustrate these synthesis include but are not limited to Examples 582, 588, 714, 721-31, 847, 857, 1220

Scheme 19

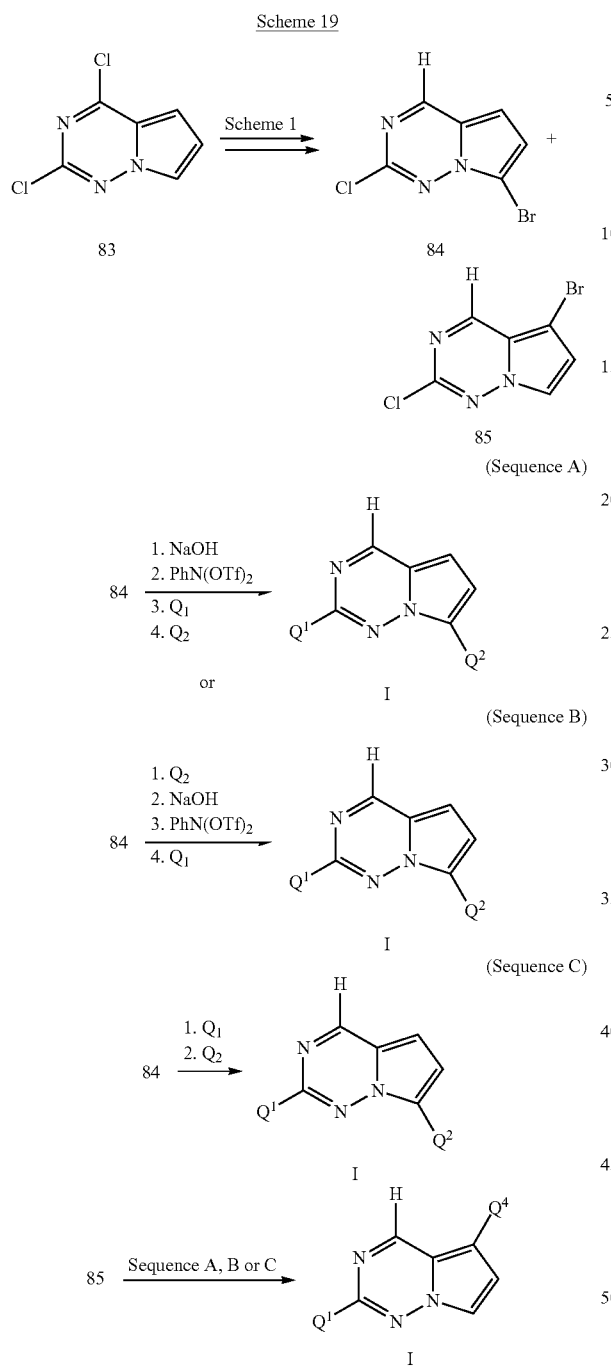

$Q^1 = H_2N-A^1-G^1-X^1-Z^1$
$Q^n = B^n-A^n-G^n-X^n-Z^n$
$B^1 = B(OH)_2$, SnAlkyl$_3$, CrCl$_2$, ZnBr, Li, Mg, K, Na
n = 2 or 4

Scheme 20 illustrates how compounds of formula I are synthesized in which $Q^2, Q^4$=H, $Q^1$ is —NH-Aryl-$G^1$-$X^1$—$Z^1$ or —NH-heteroaryl-$G^1$-$X^1$—$Z^1$ (i.e. $L^1$ is NH and $A^1$=$C_{6-11}$arylene or 5-15 membered heteroarylene) and $Q^3$ in which $L^4$ is absent and $Q^3$ is represented by aryl-$G^3$-$X^3$—$Z^3$ or heteroaryl-$G^3$-$X^3$—$Z^3$ (i.e. $A^3$=$C_{6-11}$arylene or 5-15 membered heteroarylene). Commercially available Methyl 4-bromo-1H-pyrrole-2-carboxylate (86) can be converted to compounds of formula 87 following a protocol similar to that described in Scheme 1. Following protocols similar to those described in Scheme 2, this may be converted to the desired compounds of formula I. Examples 1155-1158 illustrate these syntheses.

Scheme 20

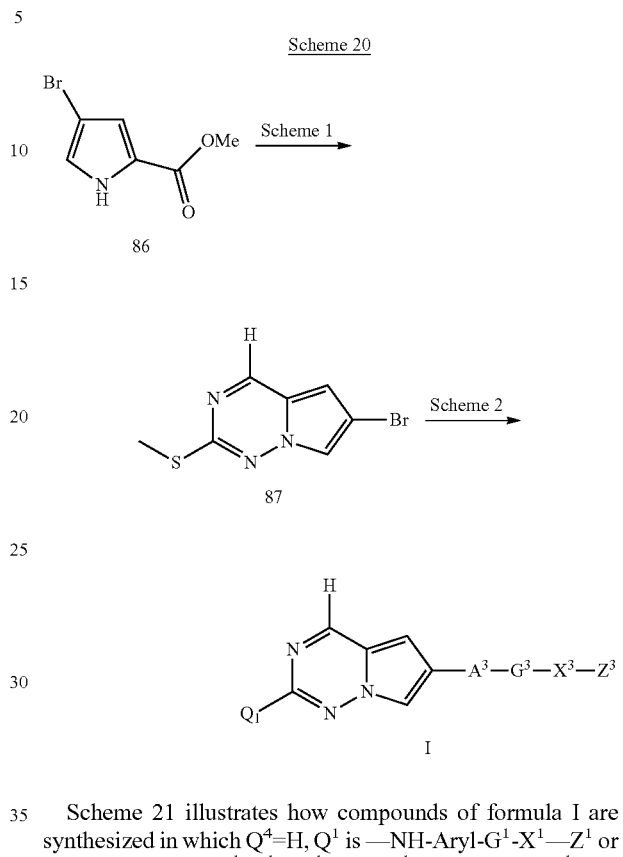

Scheme 21 illustrates how compounds of formula I are synthesized in which $Q^4$=H, $Q^1$ is —NH-Aryl-$G^1$-$X^1$—$Z^1$ or —NH-heteroaryl-$G^1$-$X^1$—$Z^1$ (i.e. $L^1$ is NH and $A^1$=$C_{6-11}$arylene or 5-15 membered heteroarylene) and $Q^3$ in which $L^4$ is absent and $Q^3$ is represented by -$L^3$-$A^3$-$G^3$-$X^3$—$Z^3$ and $Q^2$ is represented by -$A^2$-$G^2$-$X^2$—$Z^2$ or heteroaryl-$G^2$-$X^2$—$Z^2$ (i.e. $A^2$=$C_{6-11}$arylene or 5-15 membered heteroarylene). Compounds of formula 87 can be converted to compounds of formula 88 via coupling as described in Scheme 2 followed by bromination to give compounds of formula 89. Following a protocol similar to that described in Scheme 2, this may be converted to the desired compounds of formula 90. Examples 515, 1160 illustrate these syntheses.

Scheme 21

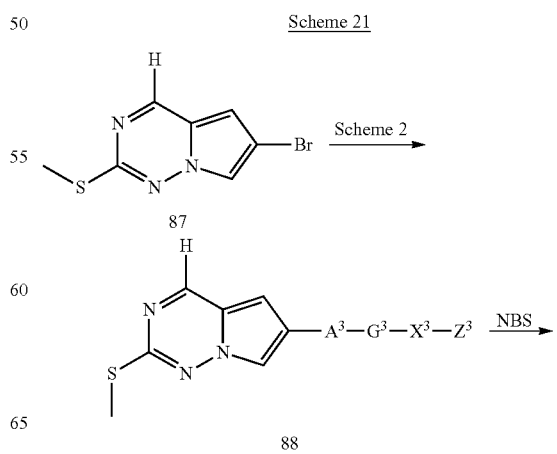

-continued

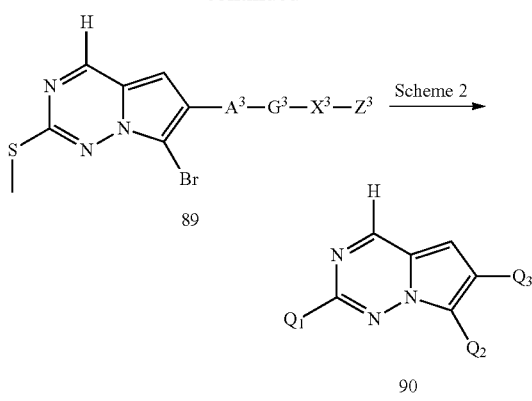

Scheme 22 illustrates how compounds of formula I are synthesized in which Q¹=Cyano, Carboxamide, or Q¹ is Azole-G¹-X¹—Z¹ (i.e. L¹ is absent and A¹=5-15 membered heteroarylene) where the azole is triazolyl, tetrazolyl or benzimidazolyl. Compounds of formula 13 can be oxidized to compounds of formula 91 and then treated with KCN to give compounds of formula 92. Hydrolysis gives compounds of formula 93. Compounds of formula 93 can also be treated with an acylhydrazine to give compounds of formula 94, or with TMS-azide to give compounds of formula 95 or hydrolysed to the acid of formula 96, which in turn is converted to the benzimidazole of formula 97. In another synthesis of an azole, compounds of formula 13 can be oxidized to compounds of formula 14 and then treated with an azole, to give compounds of formula 98. Examples 322-325, 330, 1494, 1495, 1501, 1502, 1505, 1160 illustrate these syntheses.

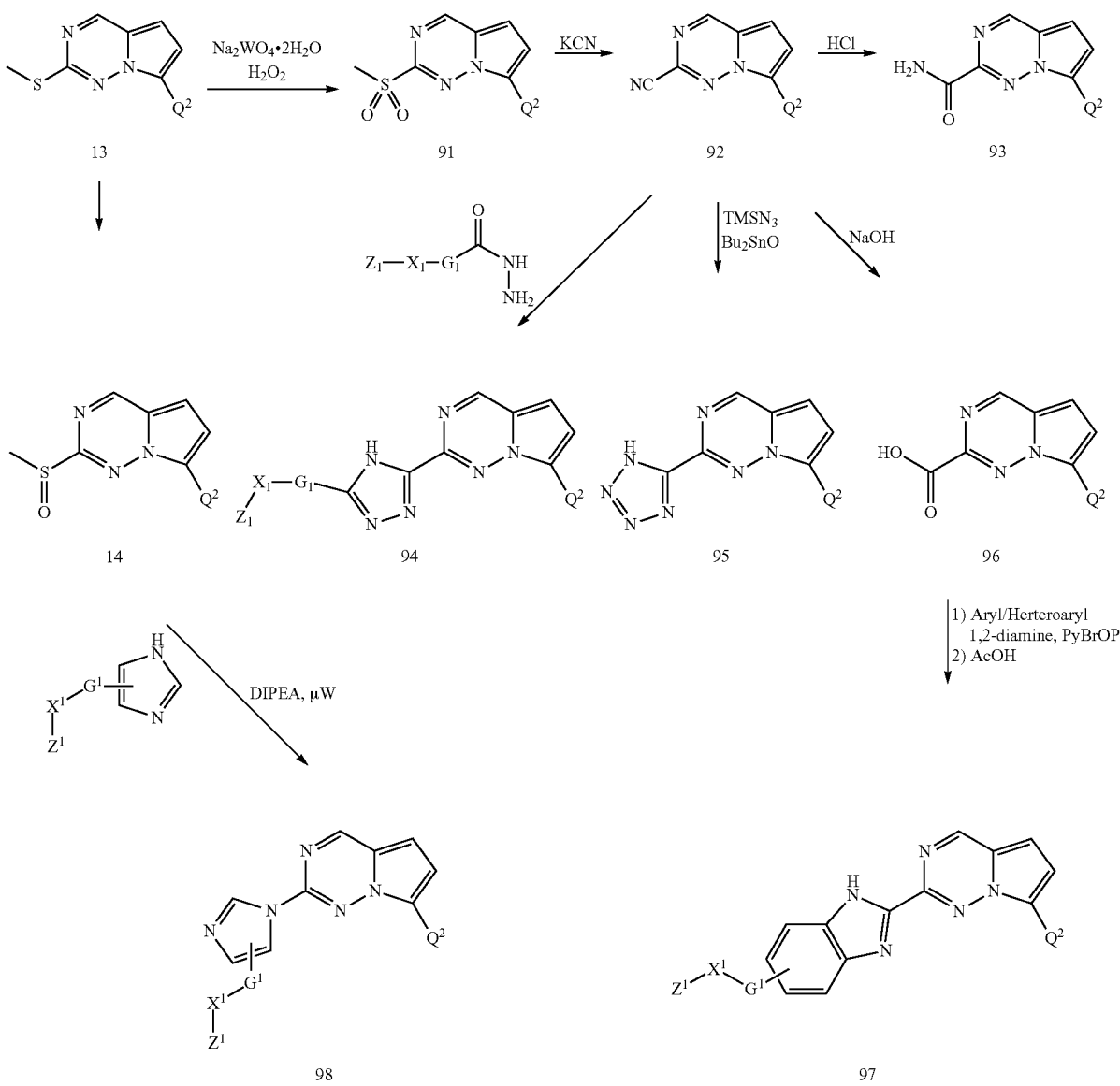

Scheme 23 illustrates how compounds of formula I are synthesized in which $Q^1$ contains a moiety such as —$C_{0-3}$alkylP(O)alkyl$_2$, and $Q^1$ is —NH-Aryl-$G^1$-$X^1$—$Z^1$ or NHCH$_2$-Aryl-$G^1$-$X^1$—$Z^1$ or —NH-heteroaryl-$G^1$-$X^1$—$Z^1$ or NHCH$_2$-heteroaryl-$G^1$-$X^1$—$Z^1$ (i.e. $L^1$ is NH or NHCH$_2$ and $A^1$=$C_{6-11}$arylene or 5-15 membered heteroarylene) wherein the —P(O)alkyl$_2$ may be an attachment on $A^1$ or an attachment on/or act as $G^1$ and/or $X^1$ and/or $Z^1$. For clarity purposes shown are sequences in which $Q^3$, $Q^4$=H. Using similar methods described hereinbefore, compounds of formula 101 may be converted to compounds of formula I in which $Q^3$ is represented by -$L^3$-$A^3$-$G^3$-$X^3$—$Z^3$ and $Q^4$ by $L^4$-$A^4$-$G^4$-$X^4$—$Z^4$. To one skilled in the art, the method of attachment of the phosphinoyl group to an aryl bromide or Arylalkyl bromide is a general method and may be applied to not only $A^1$ but $G^1$, $X^1$, $Z^1$. Bromides of formula 99 can be treated under palladium catalysis to give compounds of formula 100. This type of reaction is well precedented as desribed by Xu, Yuanyao; Li, Zhong; Xia, Jiazhi; Guo, Huiju; Huang, Yaozeng in "Palladium-catalyzed synthesis of alkylarylphenylphosphine oxides." *Synthesis*, 1984, 9, 781-2. Further elaboration to compounds of formula 101 and using methods described hereinbefore would give compounds of formula 102. Likewise Compounds of formula 104 available via benzylic bromide of formula 103 would yield compounds of formula I such as compounds of formula 105. Aminomethyl derivatives of formula 109 would be able to be achieved from compounds of formula 106 through a similar sequence.

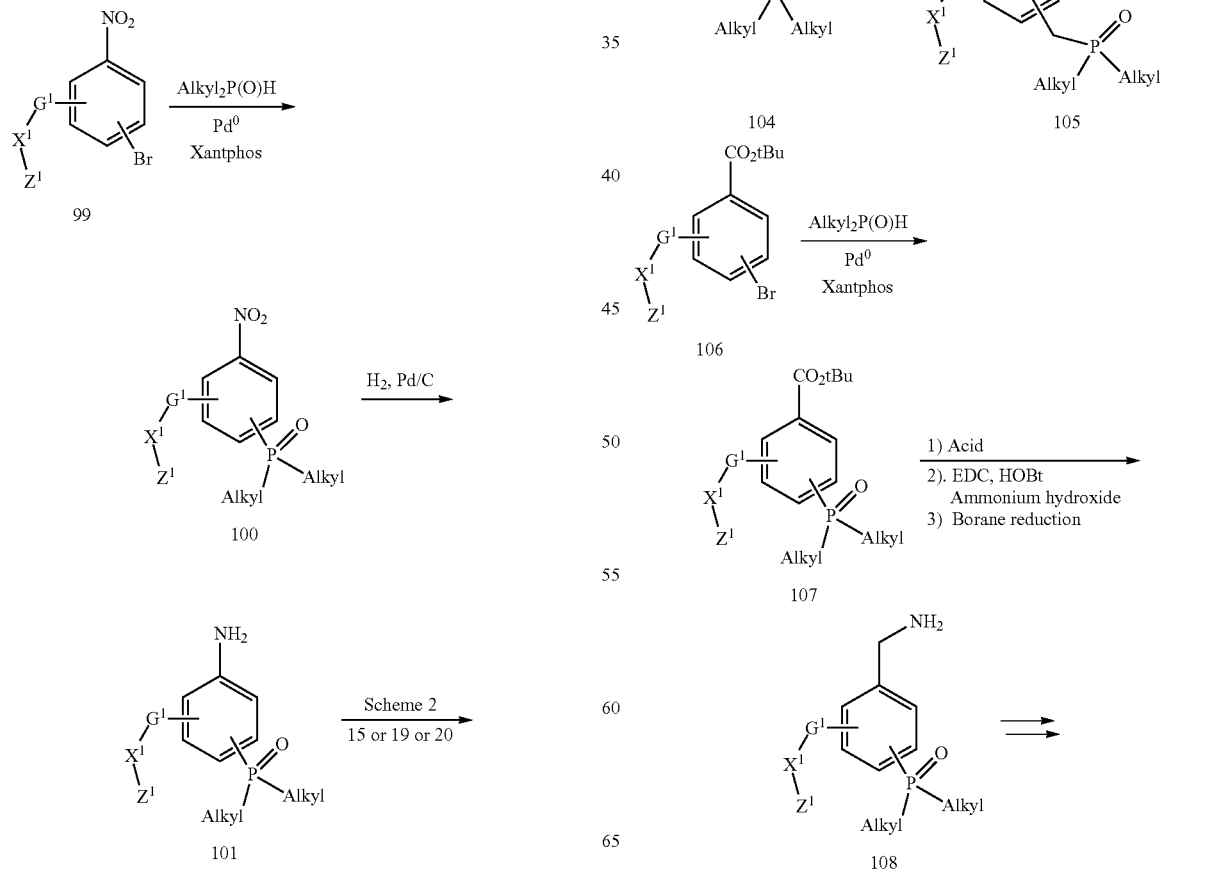

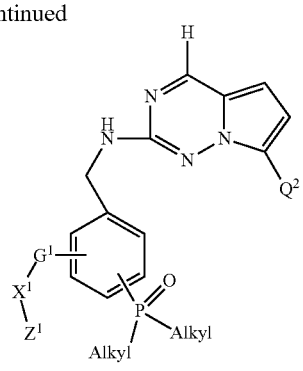

109

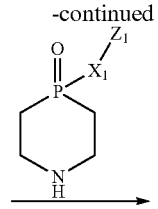

114

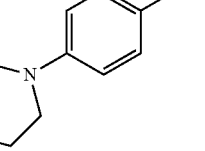

115

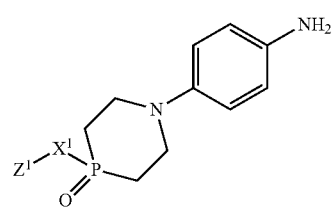

116

Scheme 24 illustrates how compounds of formula I are synthesized in which $Q^1$ contains a ring system containing the moiety —P(=O)(alkyl)- as a ring member. A method for the synthesis this type of ring system in which the ring system is a [1,4]azaphosphinane 4-oxide is shown. Compounds of formula 110 (commercially available or synthesized by known methods to one skilled in the art) can be treated with vinylmagnesium bromide and then benzylamine to give compounds of formula 112. Debenzylation would provide the [1,4]azaphosphinane 4-oxide ring system of formula 113. One skilled in the Art recognizes that a variety of phosphinane ring systems are available through methods known to one skilled in the art. For compounds of formula I in which and Q1 is —NH-Aryl-phosphinane-$X^1$—$Z^1$ or —NH-heteroaryl-phosphinane-$X^1$—$Z^1$ (i.e. $L^1$ is NH and $A^1$=$C_{6-11}$arylene or 5-15 membered heteroarylene, $G^1$=—P(=O)(alkyl)- as a ring member) may be synthesized from compounds of formula 114 through addition of the phophinane to give compounds of formula 115. Following previously described methods, this would give compounds of formula 117. Likewise, compounds of formula 120 in which $Q^1$ is —NH-Aryl-heterocycle-phophinane-$Z^1$ or —NH-heteroaryl-heterocycle-phosphinane —$Z^1$ (i.e. $L^1$ is NH and $A^1$=$C_{6-11}$arylene or 5-15 membered heteroarylene, $G^1$=3-15 membered heterocycloalkylene or 3-15 membered heterocycloalkylene, $X^1$=—P(=O)(alkyl)- as a ring member) can be prepared from compounds of formula 118 or 121 and the phosphinane.

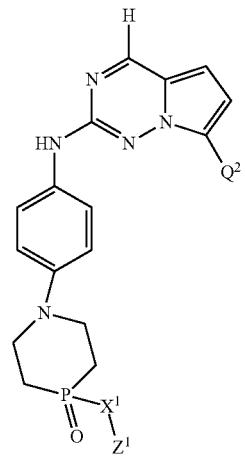

117

Scheme 24

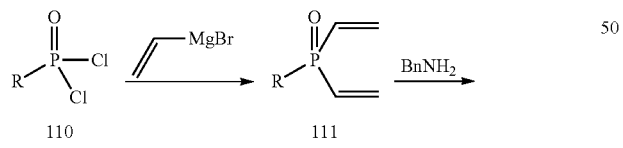

110  111

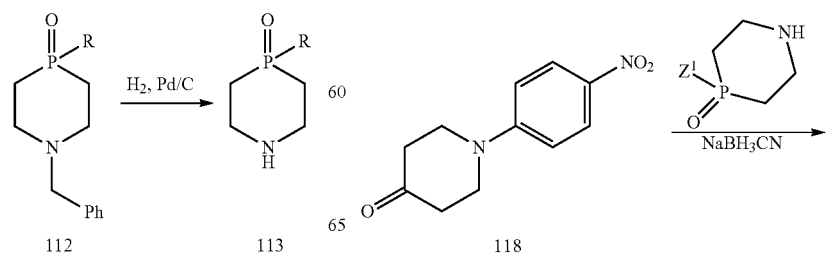

112  113  118

271
-continued

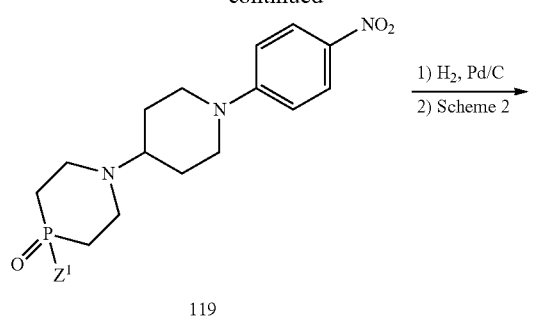
119

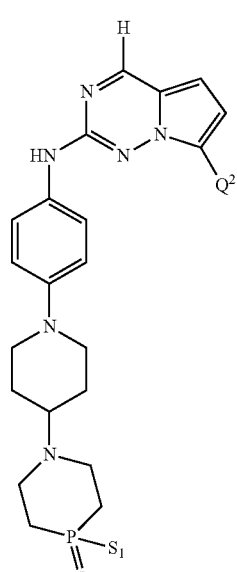
120

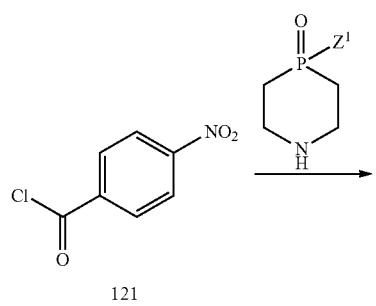
121

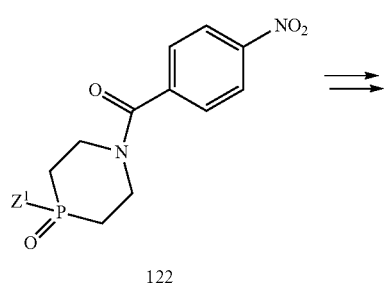
122

272
-continued

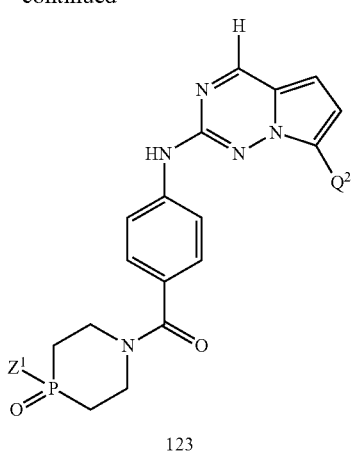
123

Scheme 25 illustrates methods to synthesize compounds of formula I in which and Q1 is —NH-Aryl-phosphinane-$X^1$—$Z^1$ or —NH-heteroaryl-phosphinane-$X^1$—$Z^1$ (i.e. $L^1$ is NH and $A^1$=$C_{6-11}$arylene or 5-15 membered heteroarylene, $G^1$=—P(=O)(alkyl)- as a ring member) may be synthesized from compounds of formula 124 via palladium catalyzed addition of the Phosphous containing moiety. Hydrolysis, chlorination and Grignard addition would give compounds of formula 126. Following the sequence similar to that of Scheme 24 would provide compounds of formula 130.

Scheme 25

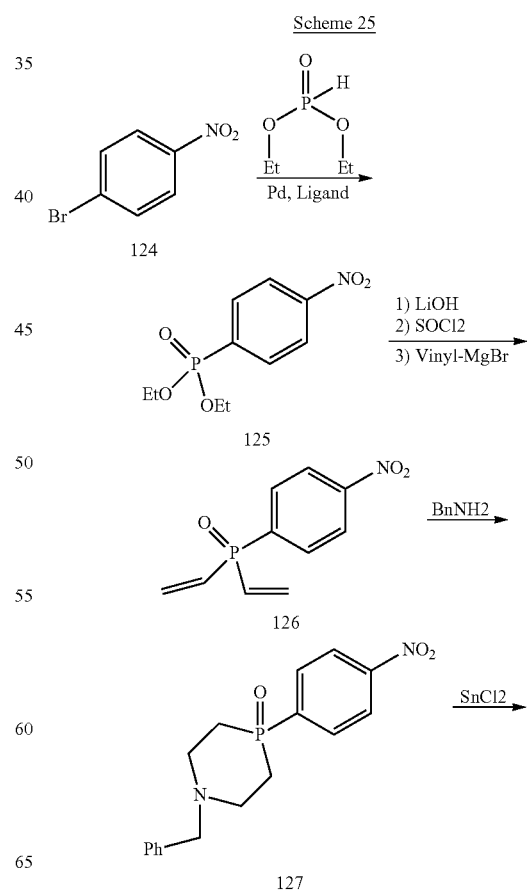

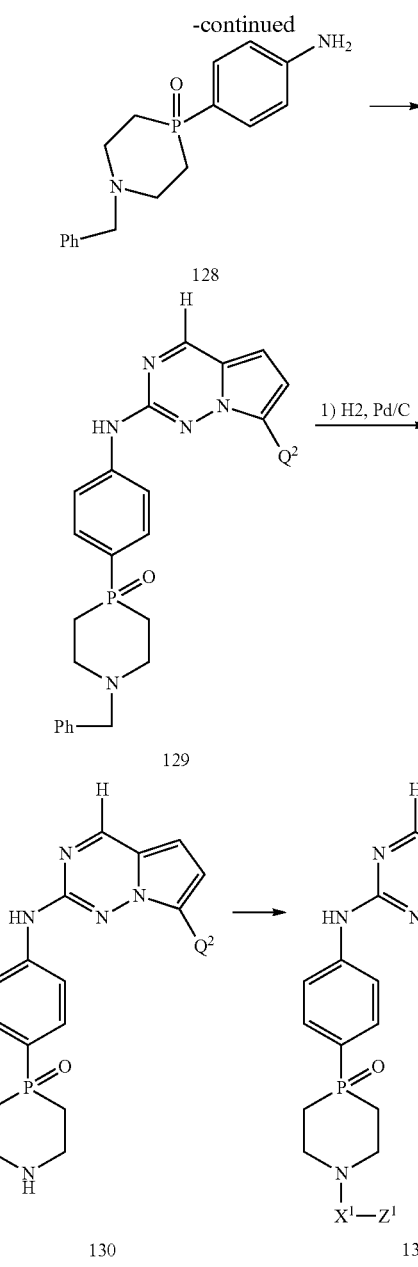
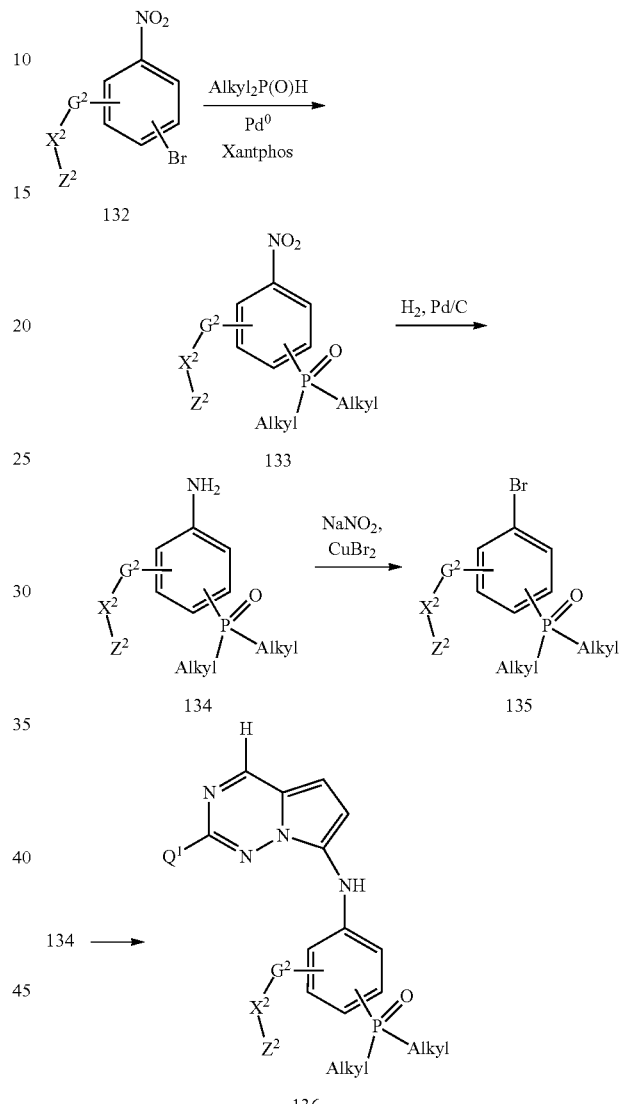

Scheme 26 illustrates how compounds of formula I are synthesized in which $Q^2$ contains a moiety such as —$C_{0-3}$alkylP(O)alkyl$_2$, and $Q^2$ is —NH or NHCH$_2$-Aryl-$G^2$-$X^2$—$Z^2$ or —NH— or NHCH$_2$-heteroaryl-$G^2$-$X^2$—$Z^2$ (i.e. $L^2$ is NH or NHCH$_2$ or absent and $A^2$=$C_{6-11}$ arylene or 5-15 membered heteroarylene) wherein the —P(O)alkyl$_2$ may be an attachment on $A^2$ or an attachment on/or act as $G^2$ and/or $X^2$ and/or $Z^2$. For clarity purposes shown are sequences in which $Q^3$, $Q^4$=H. Using similar methods described hereinbefore, compounds of formula 101 may be converted to compounds of formula I in which $Q^3$ is represented by -$L^3$-$A^3$-$G^3$-$X^3$—$Z^3$ and $Q^4$ by -$L^4$-$A^4$-$G^4$-$X^4$—$Z^4$. As previously described in Scheme 23, compounds of formula 134 could be available from compounds of formula 132. Direct coupling of compounds of formula 134 to the pyrrolotriazine as described hereinbefore in Scheme 6 would give compounds of formula 136. Also, compounds of formula 140 would be available from bromide 135 through a sequence in which compounds of formula 134 are converted, via diazotization chemistry to give compounds of formula 135 which could be coupled directly to the stannyl derivative of formula 139, via the bromide of formula 138.

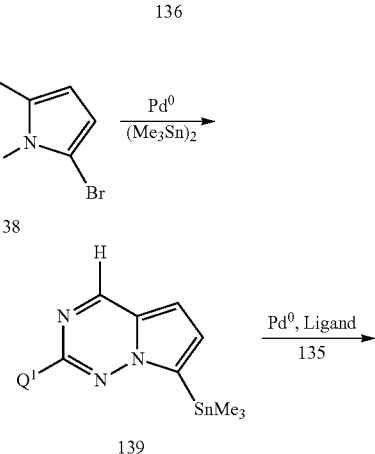

275
-continued

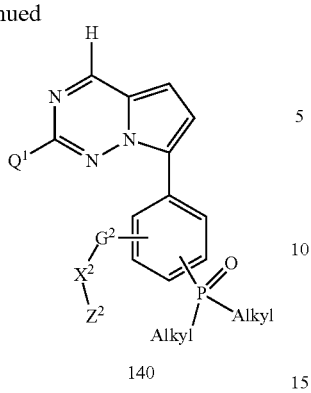

140

Scheme 27 illustrates how compounds of formula I are synthesized in which $Q^2$ contains a ring system containing the moiety —P(=O)(alkyl)- as a ring member. For compounds of formula I in which and $Q^2$ is —NH-Aryl-phosphinane-$X^2$—$Z^2$ or —NH-heteroaryl-phosphinane-$X^2$—$Z^2$ (i.e. $L^2$ is absent and $A^2$=$C_{6-11}$aryl, $C_{6-11}$arylene or 5-15 membered heteroaryl, 5-15 membered heteroarylene, $G^2$=—P(=O)(alkyl)- as a ring member) may be synthesized from compounds of formula 141 via a sequence similar to Scheme 26 to give compounds of formula 142. Following previously described methods, this would give compounds of formula 143. Likewise, compounds of formula 146 in which $Q^2$ is Aryl-heterocycle-phophinane-$Z^2$ or -heteroaryl-heterocycle-phosphinane —$Z^2$ (i.e. $L^2$ is absent and $A^2$=$C_{6-11}$ aryl, $C_{6-11}$arylene or 5-15 membered heteroaryl, 5-15 membered heteroarylene, $G^2$=3-15 membered heterocycloalkylene or 3-15 membered heterocycloalkylene, $X^2$=—P(=O)(alkyl)- as a ring member) can be prepared from compounds of formula 144. One skilled in the Art recognizes that using methods described hereinbefore, the chemistry presented in Schemes 26 and 27 not only applies to $Q^2$ but may equally be effective for $Q^3$ and $Q^4$ following sequences presented hereinbefore in Schemes 14, 15, 19 and 20.

Scheme 27

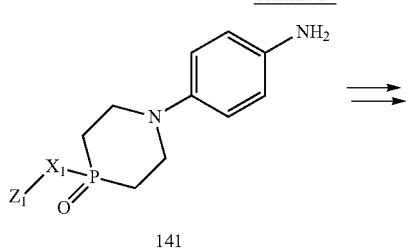

141

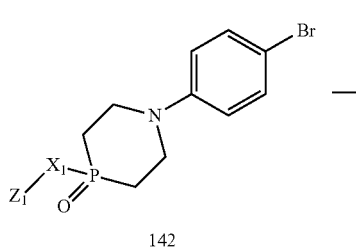

142

276
-continued

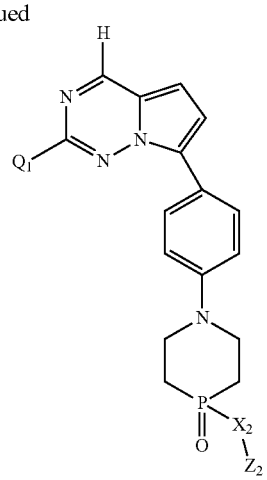

143

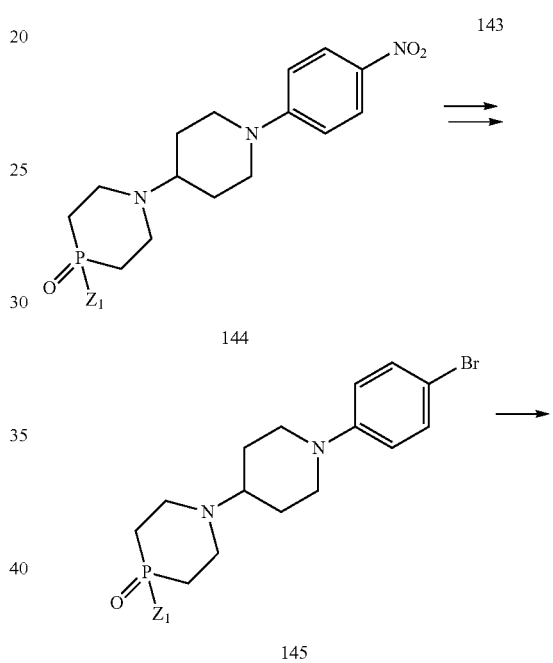

144

145

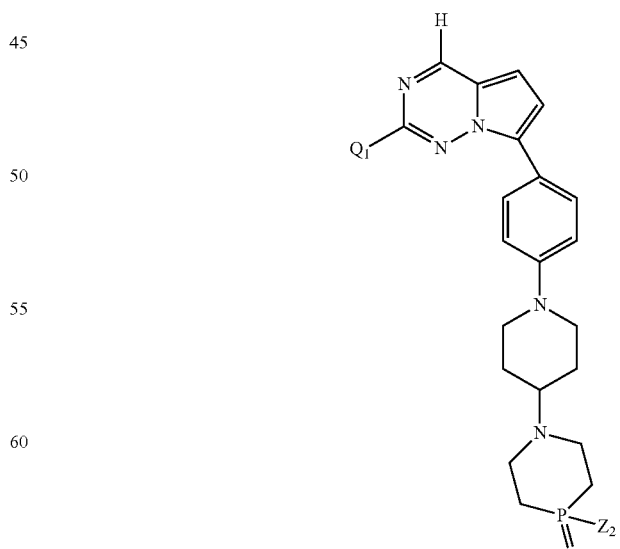

146

VI. Biology

ALK Kinase Assay

Example compounds were tested for their ability to inhibit the kinase activity of baculovirus-expressed ALK using a modification of the ELISA protocol reported for trkA in Angeles, T. S. et al., *Anal. Biochem.* 1996, 236, 49-55, which is incorporated herein by reference in its entirety. Phosphorylation of the substrate, phospholipase C-gamma (PLC-γ) generated as a fusion protein with glutathione S-transferase (GST) as reported in Rotin, D. et al., *EMBO J.* 1992, 11, 559-567, which is incorporated herein by reference in its entirety, was detected with a europium-labeled anti-phosphotyrosine antibody and measured by time-resolved fluorescence (TRF). Briefly, each 96-well plate was coated with 100 4/well of 10 μg/mL substrate (phospholipase C-γ) in Tris-buffered saline (TBS). The assay mixture (total volume=100 μL/well) consisting of 20 mM HEPES (pH 7.2), 1 μM ATP ($K_m$ level), 5 mM $MnCl_2$, 0.1% BSA, 2.5% DMSO, and various concentrations of test compound was then added to the assay plate. The reaction was initiated by adding enzyme (30 ng/ml ALK) and was allowed to proceed at 37° C. for 15 minutes. Detection of the phosphorylated product was performed by adding 100 μl/well of Eu—N1 labeled PT66 antibody (Perkin Elmer # AD0041). Incubation at 37° C. then proceeded for one (1) hour, followed by addition of 100 μL enhancement solution (Wallac #1244-105). The plate was gently agitated and after thirty minutes, the fluorescence of the resulting solution was measured using the EnVision 2100 (or 2102) multilabel plate reader (Perkin Elmer).

Data analysis was performed using ActivityBase (IDBS, Guilford, UK). $IC_{50}$ values were calculated by plotting percent inhibition versus $log_{10}$ of the concentration of compound and fitting to the nonlinear regression sigmoidal dose-response (variable slope) equation in XLFit (IDBS, Guilford, UK).

Recombinant Human JAK2 Kinase Assay

Compounds were tested for their ability to inhibit the kinase activity of baculovirus-expressed JAK2 using the TRF detection system. $IC_{50}$ runs were conducted in 96-well Costar high binding plates (Corning Costar #3922, Corning, N.Y.). The plates were coated first with 100 μL/well of 10 μg/mL Neutravidin (Pierce #31000, Rockford, Ill.) in TBS at 37° C. for 2 hours, followed by 100 μL/well of 1 μg/mL 15-mer peptide substrate (biotinyl-amino-hexanoyl-EQEDE-PEGDYFEWLE-amide, Infinity Biotech Research and Resource, Aston, Pa.) at 37° C. for another hour. The JAK2 assay mixture (total volume=100 μL/well) consisting of 20 mM HEPES (pH 7.2), 0.2 μM ATP, 1 mM $MnCl_2$, 0.1% BSA, and test compound (diluted in DMSO; 2.5% DMSO final in assay) was then added to the assay plate. Enzyme (15 ng/ml JAK2) was added and the reaction was allowed to proceed at room temperature for 20 minutes. Detection of the phosphorylated product was performed by adding 100 μL/well of Eu—N1 labeled PY100 antibody (PerkinElmer Life Sciences #AD0041, Boston, Mass.). Incubation at the room temperature then proceeded for 1 hour, followed by addition of 100 μl enhancement solution (PerkinElmer Life Sciences #1244-105, Boston, Mass.). The plate was gently agitated and after thirty minutes, the fluorescence of the resulting solution was measured using the PerkinElmer EnVision 2100 (or 2102)

Results

Biological data for the Example compounds is presented in the following Table 1.

TABLE 1

ALK, JAK2 Kinase Inhibition

| Example | ALK Potency | JAK2 Potency |
|---------|-------------|--------------|
| 1 | + | ++++ |
| 2 | +++ | ++++ |
| 3 | +++ | ++++ |
| 4 | ++ | ++++ |
| 5 | ++ | ++++ |
| 6 | + | ++++ |
| 7 | ++++ | ++++ |
| 8 | ++++ | ++++ |
| 9 | ++++ | ++++ |
| 10 | ++ | ++++ |
| 11 | ++ | ++++ |
| 12 | ++ | ++ |
| 13 | +++ | ++++ |
| 14 | +++ | ++++ |
| 15 | +++ | ++++ |
| 16 | +++ | ++++ |
| 17 | ++++ | ++++ |
| 18 | +++ | ++++ |
| 19 | +++ | ++++ |
| 20 | ++++ | ++++ |
| 21 | +++ | ++++ |
| 22 | ++++ | ++++ |
| 23 | ++++ | ++++ |
| 24 | ++ | ++++ |
| 25 | ++++ | ++++ |
| 26 | ++++ | ++++ |
| 27 | +++ | ++++ |
| 28 | + | ++ |
| 29 | + | ++ |
| 30 | ++++ | ++++ |
| 31 | +++ | ++++ |
| 32 | +++ | ++++ |
| 33 | ++++ | ++++ |
| 34 | ++++ | ++++ |
| 35 | +++ | ++ |
| 36 | ++ | ++++ |
| 37 | ++ | ++++ |
| 38 | +++ | ++++ |
| 39 | + | ++++ |
| 40 | + | ++ |
| 41 | + | ++++ |
| 42 | + | +++ |
| 43 | +++ | ++++ |
| 44 | + | ++++ |
| 45 | + | ++++ |
| 46 | ++ | ++++ |
| 47 | +++ | ++++ |
| 48 | ++++ | +++ |
| 49 | + | ++++ |
| 50 | + | ++++ |
| 51 | + | ++++ |
| 52 | +++ | ++++ |
| 53 | +++ | ++++ |
| 54 | +++ | ++++ |
| 55 | ++ | ++++ |
| 56 | ++ | ++++ |
| 57 | ++ | ++++ |
| 58 | ++ | ++++ |
| 59 | +++ | ++++ |
| 60 | ++ | ++++ |
| 61 | + | ++++ |
| 62 | +++ | ++++ |
| 63 | + | ++++ |
| 64 | ++++ | ++++ |
| 65 | +++ | ++++ |
| 66 | ++ | ++++ |
| 67 | +++ | ++++ |
| 68 | ++++ | ++++ |
| 69 | ++++ | ++++ |
| 70 | ++ | ++++ |
| 71 | + | ++++ |
| 72 | ++ | ++++ |
| 73 | ++++ | ++++ |
| 74 | +++ | ++++ |
| 75 | +++ | +++ |

TABLE 1-continued

ALK, JAK2 Kinase Inhibition

| Example | ALK Potency | JAK2 Potency |
|---|---|---|
| 76 | ++++ | ++++ |
| 77 | +++ | ++++ |
| 78 | ++++ | ++++ |
| 79 | + | ++++ |
| 80 | + | ++++ |
| 81 | +++ | ++++ |
| 82 | +++ | ++++ |
| 83 | +++ | ++++ |
| 84 | ++ | ++++ |
| 85 | + | ++++ |
| 86 | + | ++++ |
| 87 | ++ | ++++ |
| 88 | +++ | ++++ |
| 89 | +++ | ++++ |
| 90 | ++++ | ++++ |
| 91 | +++ | ++++ |
| 92 | ++ | ++++ |
| 93 | ++++ | ++++ |
| 94 | ++++ | ++++ |
| 95 | +++ | ++++ |
| 96 | +++ | ++++ |
| 97 | +++ | ++++ |
| 98 | +++ | ++++ |
| 99 | + | ++++ |
| 100 | +++ | ++++ |
| 101 | ++++ | ++++ |
| 102 | + | ++ |
| 103 | +++ | ++++ |
| 104 | ++ | ++++ |
| 105 | ++++ | ++++ |
| 106 | +++ | ++++ |
| 107 | +++ | ++++ |
| 108 | +++ | ++++ |
| 109 | ++++ | ++++ |
| 110 | + | ++++ |
| 111 | +++ | ++++ |
| 112 | +++ | ++++ |
| 113 | + | ++ |
| 114 | +++ | ++++ |
| 115 | +++ | ++++ |
| 116 | ++ | ++++ |
| 117 | ++ | ++++ |
| 118 | +++ | ++++ |
| 119 | +++ | ++++ |
| 120 | +++ | ++++ |
| 121 | ++++ | ++++ |
| 122 | +++ | ++++ |
| 123 | +++ | ++++ |
| 124 | ++ | ++++ |
| 125 | +++ | ++++ |
| 126 | +++ | ++++ |
| 127 | + | ++++ |
| 128 | ++++ | ++++ |
| 141 | +++ | ++++ |
| 142 | +++ | ++++ |
| 143 | +++ | ++++ |
| 144 | ++ | ++++ |
| 145 | ++ | ++++ |
| 146 | + | ++++ |
| 147 | +++ | ++++ |
| 148 | ++ | ++++ |
| 149 | +++ | ++++ |
| 150 | + | ++++ |
| 151 | +++ | ++++ |
| 152 | ++ | ++++ |
| 153 | + | ++++ |
| 154 | +++ | ++++ |
| 155 | + | ++++ |
| 156 | + | ++++ |
| 157 | +++ | ++++ |
| 158 | +++ | ++++ |
| 159 | + | ++ |
| 160 | ++++ | ++++ |
| 161 | +++ | ++++ |
| 162 | +++ | ++++ |
| 163 | ++ | ++++ |
| 164 | +++ | ++++ |
| 165 | ++ | ++++ |
| 166 | ++ | ++++ |
| 167 | ++ | ++++ |
| 168 | ++ | ++++ |
| 169 | +++ | ++++ |
| 170 | ++ | ++++ |
| 171 | +++ | ++++ |
| 172 | ++ | ++++ |
| 173 | +++ | ++++ |
| 174 | + | +++ |
| 175 | +++ | ++++ |
| 176 | + | ++++ |
| 177 | +++ | ++++ |
| 178 | ++++ | ++++ |
| 179 | ++++ | ++++ |
| 180 | ++++ | ++++ |
| 181 | +++ | ++++ |
| 182 | +++ | ++++ |
| 183 | +++ | ++++ |
| 184 | ++ | ++++ |
| 185 | +++ | ++++ |
| 186 | +++ | ++++ |
| 187 | + | ++++ |
| 188 | ++ | ++++ |
| 189 | + | ++++ |
| 190 | + | ++++ |
| 191 | + | ++++ |
| 192 | ++ | ++++ |
| 193 | ++ | ++++ |
| 194 | +++ | ++++ |
| 195 | ++++ | ++++ |
| 196 | ++++ | ++++ |
| 197 | + | +++ |
| 198 | +++ | ++++ |
| 199 | ++ | ++++ |
| 200 | +++ | ++++ |
| 201 | +++ | ++++ |
| 202 | ++++ | ++++ |
| 203 | ++++ | ++++ |
| 204 | ++++ | ++++ |
| 205 | +++ | ++++ |
| 206 | ++++ | ++++ |
| 207 | ++++ | ++++ |
| 208 | +++ | ++++ |
| 209 | +++ | ++++ |
| 210 | ++++ | ++++ |
| 211 | ++++ | ++++ |
| 212 | ++++ | ++++ |
| 213 | ++++ | ++++ |
| 214 | ++++ | ++++ |
| 215 | ++++ | ++++ |
| 216 | +++ | ++++ |
| 217 | +++ | ++++ |
| 218 | ++++ | ++++ |
| 219 | ++++ | ++++ |
| 220 | +++ | ++++ |
| 221 | ++++ | ++++ |
| 222 | ++++ | ++++ |
| 223 | ++++ | ++++ |
| 231 | ++++ | ++++ |
| 232 | ++++ | ++++ |
| 233 | ++++ | ++++ |
| 234 | +++ | ++ |
| 235 | ++++ | +++ |
| 241 | ++++ | +++ |
| 242 | ++++ | ++++ |
| 251 | ++++ | ++++ |
| 252 | ++++ | ++++ |
| 253 | ++++ | ++++ |
| 261 | +++ | ++++ |
| 262 | +++ | ++ |
| 263 | +++ | ++++ |
| 264 | ++ | ++++ |

TABLE 1-continued

ALK, JAK2 Kinase Inhibition

| Example | ALK Potency | JAK2 Potency |
|---|---|---|
| 265 | + | ++++ |
| 266 | ++ | + |
| 267 | +++ | ++ |
| 268 | + | ++++ |
| 269 | ++ | ++ |
| 270 | + | +++ |
| 271 | + | +++ |
| 272 | + | ++++ |
| 273 | + | +++ |
| 301 | +++ | ++++ |
| 302 | NT | ++++ |
| 303 | ++ | ++++ |
| 304 | ++ | ++++ |
| 305 | +++ | ++++ |
| 306 | +++ | ++++ |
| 307 | + | ++++ |
| 308 | +++ | ++++ |
| 309 | ++ | ++++ |
| 310 | ++++ | ++++ |
| 311 | ++++ | ++++ |
| 312 | ++++ | ++++ |
| 313 | +++ | ++++ |
| 314 | +++ | ++++ |
| 315 | +++ | ++++ |
| 316 | +++ | ++++ |
| 317 | ++ | ++++ |
| 318 | +++ | ++++ |
| 319 | +++ | ++++ |
| 320 | +++ | ++++ |
| 321 | +++ | ++++ |
| 322 | ++ | +++ |
| 323 | ++ | +++ |
| 324 | ++ | ++ |
| 325 | ++ | ++ |
| 326 | + | ++++ |
| 327 | ++ | ++++ |
| 328 | +++ | ++++ |
| 329 | +++ | ++++ |
| 330 | ++ | ++ |
| 331 | ++ | ++++ |
| 332 | + | + |
| 333 | +++ | ++++ |
| 334 | ++++ | ++++ |
| 335 | +++ | ++++ |
| 336 | +++ | ++++ |
| 337 | +++ | ++++ |
| 338 | +++ | ++++ |
| 339 | +++ | ++++ |
| 340 | +++ | ++++ |
| 341 | ++ | ++++ |
| 342 | ++ | ++++ |
| 343 | ++++ | ++++ |
| 344 | ++++ | ++++ |
| 345 | +++ | ++++ |
| 346 | +++ | ++++ |
| 347 | +++ | ++++ |
| 348 | ++++ | ++++ |
| 349 | ++++ | ++++ |
| 350 | ++++ | ++++ |
| 351 | +++ | ++++ |
| 352 | +++ | ++++ |
| 353 | ++++ | ++++ |
| 354 | ++++ | ++++ |
| 355 | ++ | ++++ |
| 356 | +++ | ++++ |
| 357 | +++ | ++++ |
| 358 | +++ | ++++ |
| 359 | +++ | ++++ |
| 360 | +++ | ++++ |
| 361 | +++ | ++++ |
| 362 | ++ | ++++ |
| 363 | ++ | ++++ |
| 364 | + | ++++ |
| 365 | ++ | ++++ |
| 366 | +++ | ++++ |
| 367 | +++ | ++++ |
| 368 | +++ | ++++ |
| 369 | +++ | ++++ |
| 370 | +++ | ++++ |
| 371 | ++ | ++++ |
| 372 | +++ | ++++ |
| 373 | ++ | ++++ |
| 374 | ++ | ++++ |
| 375 | +++ | ++++ |
| 376 | +++ | ++++ |
| 377 | ++++ | ++++ |
| 378 | ++++ | ++++ |
| 379 | +++ | ++++ |
| 380 | ++++ | ++++ |
| 381 | +++ | ++++ |
| 382 | +++ | ++++ |
| 383 | ++ | ++++ |
| 384 | ++ | ++++ |
| 385 | ++ | ++++ |
| 386 | +++ | ++++ |
| 387 | ++ | ++++ |
| 388 | +++ | ++++ |
| 389 | +++ | ++++ |
| 390 | +++ | ++++ |
| 391 | ++ | ++++ |
| 392 | ++ | ++++ |
| 393 | ++++ | ++++ |
| 394 | ++++ | ++++ |
| 395 | +++ | ++++ |
| 396 | +++ | ++++ |
| 397 | +++ | ++++ |
| 398 | ++++ | ++++ |
| 399 | ++++ | ++++ |
| 400 | ++ | ++++ |
| 401 | + | ++++ |
| 402 | +++ | ++++ |
| 403 | + | ++ |
| 404 | +++ | ++++ |
| 405 | ++ | ++++ |
| 406 | ++ | ++++ |
| 407 | +++ | ++++ |
| 408 | +++ | ++++ |
| 409 | +++ | ++++ |
| 410 | +++ | ++++ |
| 411 | ++++ | ++++ |
| 412 | +++ | +++ |
| 413 | +++ | ++++ |
| 414 | +++ | ++++ |
| 415 | +++ | ++++ |
| 416 | +++ | ++++ |
| 417 | ++++ | ++++ |
| 418 | +++ | ++++ |
| 419 | +++ | ++++ |
| 420 | ++ | ++++ |
| 421 | +++ | ++++ |
| 422 | + | ++++ |
| 423 | +++ | ++++ |
| 424 | +++ | ++++ |
| 425 | +++ | ++++ |
| 426 | +++ | ++++ |
| 427 | ++++ | ++++ |
| 428 | ++ | ++++ |
| 429 | +++ | ++++ |
| 430 | +++ | ++++ |
| 431 | ++ | ++++ |
| 432 | +++ | ++++ |
| 442 | + | ++ |
| 443 | ++++ | ++++ |
| 444 | ++++ | ++++ |
| 445 | +++ | ++++ |
| 446 | ++ | ++++ |
| 447 | ++++ | ++++ |
| 448 | ++++ | ++++ |
| 449 | +++ | ++++ |
| 450 | ++++ | ++++ |

TABLE 1-continued

ALK, JAK2 Kinase Inhibition

| Example | ALK Potency | JAK2 Potency |
|---|---|---|
| 451 | ++++ | ++++ |
| 452 | +++ | ++++ |
| 453 | +++ | ++ |
| 454 | +++ | ++++ |
| 455 | ++++ | ++++ |
| 456 | ++++ | ++++ |
| 457 | +++ | ++++ |
| 458 | ++++ | +++ |
| 459 | ++++ | +++ |
| 460 | ++++ | +++ |
| 461 | ++++ | +++ |
| 462 | ++++ | +++ |
| 463 | ++++ | +++ |
| 464 | +++ | ++++ |
| 465 | ++++ | +++ |
| 466 | ++++ | +++ |
| 467 | ++++ | +++ |
| 468 | ++++ | +++ |
| 469 | ++++ | +++ |
| 470 | ++++ | +++ |
| 471 | +++ | ++ |
| 472 | ++++ | +++ |
| 473 | ++++ | ++ |
| 474 | ++++ | ++ |
| 475 | ++++ | +++ |
| 476 | ++++ | ++++ |
| 477 | ++++ | ++++ |
| 478 | ++++ | ++++ |
| 479 | ++++ | ++++ |
| 480 | ++++ | ++ |
| 481 | ++++ | +++ |
| 482 | +++ | +++ |
| 483 | ++++ | +++ |
| 484 | ++++ | ++++ |
| 485 | +++ | ++++ |
| 486 | ++++ | ++++ |
| 487 | ++++ | +++ |
| 488 | ++++ | +++ |
| 489 | +++ | +++ |
| 490 | +++ | ++ |
| 491 | ++++ | +++ |
| 492 | ++++ | +++ |
| 493 | ++++ | +++ |
| 494 | ++ | + |
| 495 | ++ | ++++ |
| 496 | ++ | + |
| 497 | ++ | ++ |
| 498 | ++ | ++ |
| 499 | ++ | +++ |
| 500 | ++++ | ++++ |
| 501 | ++++ | ++++ |
| 502 | ++++ | ++++ |
| 503 | ++++ | ++++ |
| 505 | ++++ | ++ |
| 506 | ++++ | +++ |
| 507 | ++++ | +++ |
| 508 | ++++ | ++++ |
| 509 | ++++ | ++++ |
| 510 | ++++ | ++++ |
| 511 | ++++ | ++++ |
| 512 | +++ | ++ |
| 513 | ++++ | ++++ |
| 514 | ++ | ++++ |
| 515 | ++ | ++ |
| 516 | ++ | ++++ |
| 517 | ++++ | +++ |
| 522 | ++++ | +++ |
| 523 | ++++ | +++ |
| 524 | ++++ | +++ |
| 531 | ++++ | +++ |
| 532 | ++++ | ++ |
| 533 | ++++ | ++++ |
| 534 | ++++ | ++++ |
| 535 | ++++ | ++++ |
| 536 | ++++ | NT |
| 537 | ++++ | NT |
| 538 | ++++ | ++++ |
| 539 | ++++ | ++++ |
| 540 | ++ | ++ |
| 541 | +++ | ++ |
| 542 | +++ | ++ |
| 543 | ++++ | ++ |
| 544 | +++ | +++ |
| 545 | +++ | +++ |
| 546 | ++++ | ++++ |
| 547 | ++++ | ++++ |
| 548 | ++++ | ++++ |
| 549 | +++ | ++ |
| 550 | ++++ | +++ |
| 551 | ++++ | ++ |
| 561 | +++ | ++++ |
| 562 | +++ | ++++ |
| 563 | + | ++ |
| 564 | +++ | ++++ |
| 565 | +++ | ++++ |
| 566 | +++ | ++++ |
| 567 | +++ | ++++ |
| 568 | +++ | ++++ |
| 569 | +++ | ++++ |
| 570 | +++ | ++++ |
| 571 | + | ++++ |
| 572 | + | ++++ |
| 573 | + | ++++ |
| 574 | ++ | ++++ |
| 575 | ++ | ++++ |
| 576 | ++ | ++++ |
| 577 | +++ | ++++ |
| 578 | +++ | ++++ |
| 579 | ++ | ++++ |
| 580 | +++ | ++++ |
| 581 | +++ | ++++ |
| 582 | ++ | ++++ |
| 583 | +++ | ++++ |
| 584 | +++ | ++++ |
| 585 | +++ | ++++ |
| 586 | ++++ | ++++ |
| 587 | ++++ | ++++ |
| 588 | +++ | ++++ |
| 589 | ++++ | ++++ |
| 590 | ++ | ++++ |
| 591 | ++ | ++++ |
| 592 | ++ | ++++ |
| 593 | + | ++++ |
| 594 | ++ | ++++ |
| 595 | ++ | ++++ |
| 596 | ++ | ++++ |
| 597 | + | ++++ |
| 598 | + | +++ |
| 599 | ++ | ++++ |
| 600 | ++ | ++++ |
| 601 | +++ | ++++ |
| 611 | +++ | ++++ |
| 612 | +++ | ++++ |
| 613 | ++ | ++++ |
| 614 | ++++ | ++++ |
| 615 | ++++ | ++++ |
| 616 | +++ | ++++ |
| 617 | ++ | ++++ |
| 618 | +++ | ++++ |
| 619 | +++ | ++++ |
| 620 | +++ | ++++ |
| 621 | ++++ | ++++ |
| 622 | ++ | ++++ |
| 623 | ++++ | ++++ |
| 624 | ++++ | ++++ |
| 625 | +++ | ++++ |
| 626 | +++ | ++++ |
| 627 | ++++ | ++++ |
| 628 | +++ | ++++ |
| 629 | +++ | ++++ |

TABLE 1-continued

ALK, JAK2 Kinase Inhibition

| Example | ALK Potency | JAK2 Potency |
|---|---|---|
| 630 | ++ | ++++ |
| 631 | + | ++++ |
| 632 | ++++ | ++++ |
| 633 | ++ | ++++ |
| 634 | ++ | +++ |
| 635 | +++ | ++++ |
| 636 | +++ | ++++ |
| 637 | ++ | ++++ |
| 638 | +++ | ++++ |
| 639 | ++ | ++++ |
| 640 | +++ | ++++ |
| 641 | +++ | ++++ |
| 642 | ++ | ++++ |
| 643 | +++ | ++++ |
| 644 | ++ | ++++ |
| 645 | +++ | ++++ |
| 646 | ++ | ++++ |
| 647 | +++ | ++++ |
| 648 | +++ | ++++ |
| 649 | ++ | ++++ |
| 650 | +++ | ++++ |
| 651 | +++ | ++++ |
| 652 | ++ | ++++ |
| 653 | +++ | ++++ |
| 654 | ++++ | ++++ |
| 655 | +++ | ++++ |
| 656 | +++ | ++++ |
| 657 | +++ | ++++ |
| 658 | + | ++++ |
| 659 | ++++ | ++++ |
| 660 | ++++ | ++++ |
| 661 | +++ | ++++ |
| 662 | ++++ | ++++ |
| 663 | +++ | ++++ |
| 664 | +++ | ++++ |
| 665 | + | ++++ |
| 666 | ++ | ++++ |
| 667 | +++ | ++++ |
| 668 | ++++ | ++++ |
| 669 | ++++ | ++++ |
| 670 | +++ | ++++ |
| 671 | +++ | ++++ |
| 672 | +++ | ++++ |
| 673 | +++ | ++++ |
| 674 | + | +++ |
| 675 | ++ | ++++ |
| 676 | +++ | ++++ |
| 677 | +++ | ++++ |
| 678 | +++ | ++++ |
| 679 | ++++ | ++++ |
| 680 | +++ | ++++ |
| 681 | +++ | ++++ |
| 682 | ++++ | ++++ |
| 691 | ++++ | +++ |
| 692 | ++++ | ++++ |
| 693 | ++++ | +++ |
| 694 | ++++ | +++ |
| 695 | ++++ | +++ |
| 696 | ++++ | +++ |
| 697 | ++++ | +++ |
| 698 | ++++ | +++ |
| 699 | ++++ | +++ |
| 700 | ++++ | +++ |
| 701 | ++++ | +++ |
| 702 | ++++ | +++ |
| 703 | ++++ | +++ |
| 704 | ++++ | ++++ |
| 705 | ++++ | +++ |
| 706 | ++++ | ++++ |
| 707 | ++++ | +++ |
| 708 | ++++ | +++ |
| 709 | ++++ | ++++ |
| 710 | + | ++ |
| 714 | ++ | ++ |
| 715 | +++ | ++++ |
| 716 | ++++ | ++++ |
| 717 | +++ | ++++ |
| 718 | ++++ | ++++ |
| 719 | +++ | ++ |
| 721 | + | ++ |
| 722 | + | ++ |
| 723 | + | +++ |
| 724 | + | + |
| 725 | + | + |
| 726 | ++ | + |
| 727 | + | + |
| 728 | + | ++ |
| 729 | + | ++ |
| 730 | + | ++ |
| 741 | +++ | +++ |
| 742 | ++++ | +++ |
| 743 | ++++ | ++ |
| 744 | ++++ | ++ |
| 745 | ++++ | ++ |
| 746 | ++++ | ++ |
| 751 | + | + |
| 752 | + | ++++ |
| 753 | ++++ | ++++ |
| 754 | ++++ | ++++ |
| 755 | ++++ | ++++ |
| 756 | ++++ | ++++ |
| 757 | ++++ | +++ |
| 758 | ++++ | NT |
| 759 | ++++ | NT |
| 760 | ++++ | NT |
| 761 | ++++ | +++ |
| 762 | ++++ | ++++ |
| 763 | ++++ | ++++ |
| 764 | ++++ | ++++ |
| 765 | ++++ | +++ |
| 766 | ++++ | ++++ |
| 767 | ++++ | NT |
| 768 | +++ | +++ |
| 769 | ++++ | +++ |
| 770 | ++++ | NT |
| 771 | ++++ | +++ |
| 772 | ++++ | +++ |
| 773 | ++++ | +++ |
| 774 | ++++ | +++ |
| 775 | ++++ | ++++ |
| 776 | ++++ | ++++ |
| 777 | ++++ | ++++ |
| 778 | ++++ | ++++ |
| 779 | +++ | +++ |
| 780 | ++++ | ++++ |
| 781 | ++++ | ++++ |
| 782 | ++++ | +++ |
| 783 | ++++ | +++ |
| 784 | ++++ | +++ |
| 785 | + | + |
| 786 | + | + |
| 787 | ++++ | +++ |
| 788 | ++++ | +++ |
| 789 | ++++ | +++ |
| 790 | ++++ | +++ |
| 791 | ++++ | +++ |
| 792 | ++++ | +++ |
| 793 | ++++ | +++ |
| 794 | ++++ | +++ |
| 795 | ++++ | +++ |
| 796 | ++++ | ++++ |
| 797 | ++++ | ++++ |
| 798 | ++++ | +++ |
| 799 | ++++ | +++ |
| 800 | ++++ | +++ |
| 801 | ++++ | ++++ |
| 802 | ++++ | ++ |
| 803 | ++++ | +++ |
| 804 | ++++ | +++ |
| 805 | ++++ | +++ |

TABLE 1-continued

ALK, JAK2 Kinase Inhibition

| Example | ALK Potency | JAK2 Potency |
|---|---|---|
| 806 | ++++ | +++ |
| 807 | ++ | + |
| 808 | +++ | + |
| 809 | ++++ | +++ |
| 810 | ++++ | +++ |
| 811 | ++++ | +++ |
| 812 | ++++ | +++ |
| 813 | ++++ | ++ |
| 814 | ++++ | +++ |
| 815 | ++++ | +++ |
| 816 | ++++ | ++++ |
| 817 | + | + |
| 818 | +++ | + |
| 819 | ++++ | ++ |
| 820 | ++++ | +++ |
| 821 | ++++ | +++ |
| 822 | ++++ | +++ |
| 823 | ++++ | +++ |
| 824 | ++++ | ++ |
| 825 | ++++ | +++ |
| 826 | ++++ | +++ |
| 827 | ++++ | +++ |
| 828 | ++++ | ++ |
| 829 | ++++ | ++++ |
| 830 | ++++ | ++++ |
| 831 | ++++ | +++ |
| 832 | ++++ | ++++ |
| 833 | ++++ | ++++ |
| 834 | +++ | +++ |
| 835 | ++++ | +++ |
| 836 | ++++ | ++++ |
| 837 | ++++ | +++ |
| 838 | ++++ | ++++ |
| 839 | ++++ | +++ |
| 840 | ++++ | ++ |
| 841 | ++++ | ++ |
| 842 | ++++ | +++ |
| 843 | ++++ | +++ |
| 844 | ++++ | +++ |
| 845 | ++++ | +++ |
| 846 | ++++ | +++ |
| 847 | ++++ | +++ |
| 848 | ++++ | ++++ |
| 849 | ++++ | ++++ |
| 850 | ++++ | ++++ |
| 851 | +++ | +++ |
| 852 | ++++ | ++++ |
| 853 | ++++ | +++ |
| 854 | ++++ | + |
| 855 | ++++ | +++ |
| 856 | ++++ | ++++ |
| 857 | ++++ | +++ |
| 858 | ++++ | +++ |
| 859 | ++++ | ++++ |
| 860 | ++++ | ++++ |
| 861 | ++++ | +++ |
| 862 | ++++ | +++ |
| 863 | ++++ | ++ |
| 864 | ++++ | ++++ |
| 865 | ++++ | +++ |
| 866 | ++++ | +++ |
| 867 | ++++ | +++ |
| 868 | ++++ | +++ |
| 869 | ++++ | +++ |
| 870 | ++++ | +++ |
| 871 | ++++ | ++ |
| 872 | ++++ | +++ |
| 873 | ++++ | +++ |
| 874 | ++ | ++ |
| 875 | ++ | + |
| 876 | ++++ | +++ |
| 877 | ++++ | ++++ |
| 878 | ++++ | ++++ |
| 879 | ++++ | +++ |
| 881 | ++ | ++++ |
| 882 | + | ++++ |
| 883 | ++++ | ++++ |
| 884 | ++ | ++++ |
| 885 | ++ | ++++ |
| 886 | ++ | ++++ |
| 887 | + | +++ |
| 888 | +++ | ++++ |
| 889 | +++ | ++++ |
| 890 | + | ++++ |
| 891 | +++ | ++++ |
| 892 | ++ | ++++ |
| 893 | ++ | ++++ |
| 894 | +++ | ++++ |
| 895 | ++ | ++++ |
| 896 | +++ | ++++ |
| 897 | ++++ | ++++ |
| 898 | ++ | ++++ |
| 899 | +++ | ++++ |
| 900 | +++ | ++++ |
| 901 | + | ++++ |
| 902 | +++ | ++++ |
| 903 | +++ | ++++ |
| 904 | +++ | ++++ |
| 905 | +++ | ++++ |
| 906 | ++++ | ++++ |
| 907 | ++++ | ++++ |
| 908 | ++++ | ++++ |
| 909 | ++ | ++++ |
| 910 | ++++ | ++++ |
| 911 | ++++ | ++++ |
| 912 | ++++ | ++++ |
| 913 | ++++ | ++++ |
| 914 | ++++ | ++++ |
| 915 | ++++ | ++++ |
| 916 | + | ++++ |
| 917 | +++ | ++++ |
| 918 | +++ | ++++ |
| 919 | +++ | ++++ |
| 920 | +++ | ++++ |
| 921 | ++++ | ++++ |
| 922 | ++ | ++++ |
| 923 | +++ | ++++ |
| 924 | ++++ | ++++ |
| 925 | +++ | ++++ |
| 926 | ++ | ++++ |
| 927 | +++ | ++++ |
| 928 | +++ | ++++ |
| 929 | ++++ | ++++ |
| 930 | ++++ | ++++ |
| 931 | +++ | ++++ |
| 932 | +++ | ++++ |
| 933 | +++ | ++++ |
| 934 | ++++ | ++++ |
| 935 | ++++ | ++++ |
| 936 | +++ | ++++ |
| 937 | ++ | ++++ |
| 938 | ++++ | ++++ |
| 939 | +++ | ++++ |
| 940 | ++++ | ++++ |
| 941 | ++++ | ++++ |
| 942 | ++++ | ++++ |
| 943 | +++ | ++++ |
| 944 | +++ | ++++ |
| 945 | ++++ | ++++ |
| 946 | ++++ | ++++ |
| 947 | ++++ | ++++ |
| 948 | ++++ | ++++ |
| 949 | ++++ | ++++ |
| 950 | +++ | ++++ |
| 951 | +++ | ++++ |
| 952 | +++ | ++++ |
| 953 | ++ | ++++ |
| 954 | +++ | ++++ |
| 955 | +++ | ++++ |
| 956 | +++ | ++++ |

TABLE 1-continued

ALK, JAK2 Kinase Inhibition

| Example | ALK Potency | JAK2 Potency |
|---|---|---|
| 957 | ++++ | ++++ |
| 958 | ++++ | ++++ |
| 959 | +++ | ++++ |
| 960 | +++ | ++++ |
| 961 | +++ | ++++ |
| 962 | ++ | ++++ |
| 963 | ++ | ++++ |
| 964 | ++ | ++++ |
| 965 | ++ | ++++ |
| 966 | ++ | ++++ |
| 967 | ++ | ++++ |
| 968 | +++ | ++++ |
| 969 | ++ | ++++ |
| 970 | +++ | ++++ |
| 971 | ++ | ++++ |
| 972 | ++ | ++++ |
| 973 | + | ++++ |
| 974 | ++ | ++++ |
| 975 | ++ | ++++ |
| 976 | +++ | ++++ |
| 977 | +++ | ++++ |
| 978 | +++ | ++++ |
| 979 | ++ | ++++ |
| 980 | + | ++++ |
| 981 | +++ | ++++ |
| 982 | ++ | ++++ |
| 983 | + | ++++ |
| 984 | +++ | ++++ |
| 985 | ++++ | ++++ |
| 986 | ++ | ++++ |
| 987 | +++ | ++++ |
| 988 | ++ | ++++ |
| 991 | ++++ | +++ |
| 992 | ++++ | NT |
| 993 | ++++ | +++ |
| 994 | +++ | +++ |
| 995 | ++++ | ++++ |
| 996 | ++++ | ++ |
| 997 | ++++ | +++ |
| 998 | ++++ | ++++ |
| 999 | ++++ | +++ |
| 1001 | +++ | ++++ |
| 1002 | ++ | ++++ |
| 1003 | +++ | ++++ |
| 1004 | ++ | ++++ |
| 1005 | ++++ | ++++ |
| 1006 | ++++ | ++++ |
| 1007 | +++ | ++++ |
| 1008 | +++ | ++++ |
| 1009 | +++ | ++++ |
| 1010 | +++ | ++++ |
| 1011 | +++ | ++++ |
| 1012 | ++++ | ++++ |
| 1013 | ++ | ++++ |
| 1014 | ++++ | ++++ |
| 1015 | +++ | ++++ |
| 1016 | +++ | ++++ |
| 1018 | +++ | ++++ |
| 1020 | ++ | ++++ |
| 1021 | ++ | ++++ |
| 1024 | ++++ | ++++ |
| 1025 | +++ | ++++ |
| 1026 | ++++ | ++++ |
| 1031 | ++++ | ++++ |
| 1032 | +++ | ++++ |
| 1033 | ++ | ++++ |
| 1034 | ++ | ++++ |
| 1035 | ++ | +++ |
| 1036 | +++ | ++++ |
| 1037 | ++++ | ++++ |
| 1038 | ++ | ++++ |
| 1039 | +++ | ++++ |
| 1040 | +++ | ++++ |
| 1041 | +++ | ++++ |
| 1042 | +++ | ++++ |
| 1043 | +++ | ++++ |
| 1044 | ++ | ++++ |
| 1045 | ++ | ++++ |
| 1046 | +++ | ++++ |
| 1047 | ++ | ++++ |
| 1048 | +++ | ++++ |
| 1049 | ++ | ++++ |
| 1050 | ++ | ++++ |
| 1051 | + | ++++ |
| 1052 | +++ | ++++ |
| 1053 | ++ | ++++ |
| 1054 | + | ++++ |
| 1055 | +++ | ++++ |
| 1056 | +++ | ++++ |
| 1057 | +++ | ++++ |
| 1058 | + | ++++ |
| 1059 | +++ | ++++ |
| 1060 | ++ | ++++ |
| 1061 | + | ++++ |
| 1062 | +++ | ++++ |
| 1063 | ++ | ++++ |
| 1064 | + | ++++ |
| 1065 | +++ | ++++ |
| 1066 | ++ | ++++ |
| 1067 | +++ | ++++ |
| 1068 | ++ | ++++ |
| 1069 | ++ | ++++ |
| 1070 | ++ | ++++ |
| 1071 | +++ | ++++ |
| 1072 | ++ | ++++ |
| 1073 | +++ | ++++ |
| 1074 | ++ | ++++ |
| 1075 | + | ++++ |
| 1076 | ++ | ++++ |
| 1077 | ++ | ++++ |
| 1078 | + | ++++ |
| 1079 | ++ | ++++ |
| 1080 | ++ | ++++ |
| 1081 | + | ++++ |
| 1082 | ++ | ++++ |
| 1083 | ++ | ++++ |
| 1084 | + | ++++ |
| 1085 | + | ++++ |
| 1086 | + | ++++ |
| 1087 | ++ | ++++ |
| 1088 | ++ | ++++ |
| 1089 | ++ | ++++ |
| 1090 | ++ | ++++ |
| 1091 | ++ | ++++ |
| 1092 | +++ | ++++ |
| 1101 | ++++ | ++++ |
| 1102 | +++ | ++++ |
| 1103 | +++ | ++++ |
| 1104 | +++ | ++++ |
| 1105 | ++ | ++++ |
| 1106 | ++ | ++++ |
| 1107 | ++++ | ++++ |
| 1108 | +++ | ++++ |
| 1109 | +++ | ++++ |
| 1110 | +++ | ++++ |
| 1111 | +++ | ++++ |
| 1112 | + | ++++ |
| 1113 | ++ | ++++ |
| 1114 | +++ | ++++ |
| 1115 | ++ | ++++ |
| 1116 | ++ | ++++ |
| 1117 | ++ | ++++ |
| 1118 | +++ | ++++ |
| 1119 | ++++ | ++++ |
| 1120 | +++ | ++++ |
| 1121 | ++++ | ++++ |
| 1122 | +++ | ++++ |
| 1123 | +++ | ++++ |
| 1124 | + | + |
| 1125 | ++++ | ++++ |

TABLE 1-continued

ALK, JAK2 Kinase Inhibition

| Example | ALK Potency | JAK2 Potency |
|---|---|---|
| 1126 | ++++ | ++++ |
| 1127 | +++ | ++++ |
| 1128 | + | ++++ |
| 1129 | ++ | ++++ |
| 1130 | ++++ | ++++ |
| 1131 | ++++ | ++++ |
| 1132 | ++++ | ++++ |
| 1133 | +++ | ++++ |
| 1134 | ++++ | ++++ |
| 1135 | +++ | ++++ |
| 1136 | +++ | ++++ |
| 1137 | +++ | ++++ |
| 1138 | ++++ | ++++ |
| 1139 | +++ | ++++ |
| 1140 | ++++ | ++++ |
| 1141 | ++++ | ++++ |
| 1142 | ++++ | ++++ |
| 1143 | +++ | ++++ |
| 1144 | ++++ | ++++ |
| 1145 | +++ | ++++ |
| 1146 | +++ | ++++ |
| 1147 | +++ | ++++ |
| 1148 | ++++ | ++++ |
| 1149 | ++++ | ++++ |
| 1150 | ++++ | ++++ |
| 1151 | ++++ | ++++ |
| 1152 | ++++ | ++++ |
| 1153 | ++++ | ++++ |
| 1154 | ++++ | ++++ |
| 1155 | ++ | +++ |
| 1156 | ++ | +++ |
| 1157 | + | +++ |
| 1158 | + | ++++ |
| 1159 | ++++ | ++++ |
| 1160 | ++++ | NT |
| 1161 | +++ | ++++ |
| 1162 | +++ | ++++ |
| 1163 | +++ | ++++ |
| 1164 | +++ | ++++ |
| 1165 | ++ | ++++ |
| 1166 | ++ | ++++ |
| 1167 | + | +++ |
| 1168 | ++ | ++++ |
| 1169 | +++ | ++++ |
| 1170 | +++ | ++++ |
| 1171 | ++++ | ++++ |
| 1172 | + | ++ |
| 1173 | ++ | ++++ |
| 1174 | + | ++++ |
| 1175 | ++++ | ++++ |
| 1176 | ++ | ++++ |
| 1177 | +++ | ++++ |
| 1178 | ++++ | ++++ |
| 1179 | +++ | ++++ |
| 1180 | +++ | ++++ |
| 1181 | +++ | ++++ |
| 1182 | +++ | ++++ |
| 1183 | +++ | ++++ |
| 1184 | + | ++++ |
| 1185 | ++ | ++++ |
| 1186 | +++ | ++++ |
| 1187 | +++ | ++++ |
| 1188 | +++ | ++++ |
| 1189 | +++ | ++++ |
| 1190 | ++ | ++++ |
| 1191 | + | ++++ |
| 1192 | ++ | ++++ |
| 1193 | ++ | ++++ |
| 1194 | +++ | ++++ |
| 1195 | ++ | ++++ |
| 1196 | +++ | ++++ |
| 1197 | +++ | ++++ |
| 1198 | ++ | ++++ |
| 1199 | ++ | ++++ |
| 1200 | +++ | ++++ |
| 1201 | +++ | ++++ |
| 1202 | ++ | ++++ |
| 1203 | +++ | ++++ |
| 1204 | ++++ | ++++ |
| 1205 | +++ | ++++ |
| 1206 | +++ | ++++ |
| 1207 | +++ | ++++ |
| 1208 | +++ | ++++ |
| 1209 | +++ | ++++ |
| 1210 | +++ | ++++ |
| 1211 | ++ | ++++ |
| 1212 | +++ | ++++ |
| 1213 | +++ | ++++ |
| 1214 | +++ | ++++ |
| 1215 | +++ | ++++ |
| 1216 | +++ | ++++ |
| 1217 | ++++ | ++++ |
| 1218 | ++ | +++ |
| 1219 | ++ | +++ |
| 1220 | ++++ | +++ |
| 1221 | ++++ | ++ |
| 1222 | ++++ | ++ |
| 1223 | ++++ | ++ |
| 1224 | ++++ | ++ |
| 1225 | ++++ | ++ |
| 1226 | ++++ | +++ |
| 1227 | ++++ | +++ |
| 1228 | ++++ | +++ |
| 1229 | +++ | ++++ |
| 1230 | +++ | + |
| 1231 | +++ | ++ |
| 1232 | +++ | + |
| 1233 | +++ | ++ |
| 1234 | ++++ | ++ |
| 1235 | ++++ | +++ |
| 1236 | ++++ | ++ |
| 1237 | ++++ | +++ |
| 1238 | ++++ | +++ |
| 1239 | ++++ | +++ |
| 1240 | ++++ | +++ |
| 1241 | ++++ | ++ |
| 1242 | +++ | +++ |
| 1243 | ++++ | +++ |
| 1244 | ++++ | +++ |
| 1245 | ++++ | +++ |
| 1246 | ++++ | +++ |
| 1247 | ++++ | +++ |
| 1248 | ++++ | +++ |
| 1249 | ++++ | ++ |
| 1250 | ++ | +++ |
| 1251 | ++++ | ++ |
| 1252 | ++++ | +++ |
| 1253 | ++++ | +++ |
| 1254 | +++ | ++ |
| 1255 | ++++ | +++ |
| 1256 | ++++ | ++ |
| 1257 | ++++ | ++ |
| 1258 | ++++ | ++++ |
| 1259 | ++++ | ++ |
| 1260 | +++ | ++++ |
| 1261 | ++++ | ++++ |
| 1262 | ++++ | +++ |
| 1263 | ++++ | +++ |
| 1271 | +++ | ++ |
| 1272 | +++ | ++ |
| 1273 | ++++ | ++ |
| 1274 | ++++ | +++ |
| 1275 | ++++ | +++ |
| 1276 | ++++ | +++ |
| 1277 | +++ | ++ |
| 1278 | ++++ | +++ |
| 1279 | ++++ | +++ |
| 1280 | ++++ | +++ |
| 1281 | ++++ | +++ |
| 1282 | ++++ | ++ |

TABLE 1-continued

ALK, JAK2 Kinase Inhibition

| Example | ALK Potency | JAK2 Potency |
|---|---|---|
| 1283 | +++ | + |
| 1291 | ++ | ++++ |
| 1292 | ++ | ++++ |
| 1293 | +++ | ++++ |
| 1294 | ++ | ++++ |
| 1295 | + | +++ |
| 1296 | ++ | ++++ |
| 1297 | + | ++++ |
| 1298 | +++ | ++++ |
| 1299 | +++ | ++++ |
| 1300 | +++ | ++++ |
| 1301 | +++ | ++++ |
| 1302 | + | ++++ |
| 1303 | ++ | ++++ |
| 1304 | +++ | ++++ |
| 1305 | ++ | ++++ |
| 1306 | +++ | ++++ |
| 1307 | ++ | ++++ |
| 1308 | + | ++++ |
| 1309 | ++ | ++++ |
| 1310 | +++ | ++++ |
| 1311 | ++ | ++++ |
| 1312 | ++ | ++++ |
| 1313 | + | ++++ |
| 1314 | ++ | ++++ |
| 1315 | ++ | ++++ |
| 1316 | +++ | ++++ |
| 1317 | ++ | ++++ |
| 1318 | + | ++++ |
| 1319 | ++ | ++++ |
| 1320 | +++ | ++++ |
| 1321 | ++ | ++++ |
| 1322 | ++ | ++++ |
| 1323 | +++ | ++++ |
| 1324 | ++ | ++++ |
| 1325 | +++ | ++++ |
| 1326 | +++ | ++++ |
| 1327 | ++ | ++++ |
| 1328 | +++ | ++++ |
| 1329 | ++ | ++++ |
| 1330 | ++ | ++++ |
| 1331 | +++ | ++++ |
| 1332 | + | ++++ |
| 1333 | +++ | ++++ |
| 1334 | ++ | ++++ |
| 1335 | +++ | ++++ |
| 1336 | ++ | ++++ |
| 1337 | +++ | ++++ |
| 1338 | +++ | ++++ |
| 1339 | +++ | ++++ |
| 1340 | +++ | ++++ |
| 1341 | +++ | ++++ |
| 1342 | +++ | ++++ |
| 1343 | ++++ | ++++ |
| 1344 | +++ | ++++ |
| 1345 | +++ | ++++ |
| 1346 | +++ | ++++ |
| 1347 | ++ | ++++ |
| 1348 | +++ | ++++ |
| 1349 | +++ | ++++ |
| 1350 | ++ | ++++ |
| 1351 | +++ | ++++ |
| 1352 | +++ | ++++ |
| 1353 | ++++ | ++++ |
| 1361 | ++ | ++++ |
| 1362 | ++ | +++ |
| 1363 | ++ | ++++ |
| 1364 | ++ | ++++ |
| 1365 | ++ | ++++ |
| 1366 | +++ | ++++ |
| 1367 | ++ | ++++ |
| 1368 | +++ | ++++ |
| 1369 | ++ | ++++ |
| 1370 | +++ | ++++ |
| 1371 | +++ | ++++ |
| 1372 | + | ++++ |
| 1373 | ++++ | ++++ |
| 1374 | +++ | ++++ |
| 1375 | +++ | ++++ |
| 1376 | ++ | ++++ |
| 1377 | +++ | ++++ |
| 1378 | ++ | ++++ |
| 1379 | +++ | ++++ |
| 1380 | ++ | ++++ |
| 1381 | ++ | ++++ |
| 1382 | ++ | ++++ |
| 1383 | ++ | ++++ |
| 1384 | ++ | ++++ |
| 1385 | ++ | ++++ |
| 1386 | ++ | ++++ |
| 1387 | +++ | ++++ |
| 1388 | +++ | ++++ |
| 1389 | ++ | ++++ |
| 1390 | ++ | ++++ |
| 1391 | +++ | ++++ |
| 1392 | +++ | ++++ |
| 1393 | +++ | ++++ |
| 1394 | +++ | ++++ |
| 1395 | +++ | ++++ |
| 1396 | ++ | ++++ |
| 1397 | ++ | ++++ |
| 1398 | +++ | ++++ |
| 1399 | ++ | ++++ |
| 1400 | ++ | ++++ |
| 1401 | +++ | ++++ |
| 1402 | ++ | ++++ |
| 1403 | +++ | ++++ |
| 1404 | +++ | ++++ |
| 1405 | ++ | ++++ |
| 1406 | + | ++++ |
| 1407 | +++ | ++++ |
| 1408 | ++++ | ++++ |
| 1409 | +++ | ++++ |
| 1410 | +++ | ++++ |
| 1411 | ++++ | ++++ |
| 1412 | ++++ | ++++ |
| 1413 | +++ | ++++ |
| 1414 | ++ | ++++ |
| 1415 | +++ | ++++ |
| 1416 | +++ | ++++ |
| 1417 | ++++ | ++++ |
| 1418 | ++++ | ++++ |
| 1419 | +++ | ++++ |
| 1420 | ++ | ++++ |
| 1421 | ++++ | ++++ |
| 1422 | +++ | ++++ |
| 1423 | ++++ | ++++ |
| 1424 | ++++ | ++++ |
| 1425 | +++ | ++++ |
| 1426 | ++++ | ++++ |
| 1427 | +++ | ++++ |
| 1428 | +++ | ++++ |
| 1429 | +++ | ++++ |
| 1430 | ++++ | ++++ |
| 1431 | +++ | ++++ |
| 1432 | ++++ | ++++ |
| 1433 | ++ | ++ |
| 1434 | +++ | ++++ |
| 1435 | +++ | ++++ |
| 1436 | ++++ | ++++ |
| 1437 | +++ | ++++ |
| 1441 | ++++ | ++++ |
| 1442 | ++++ | +++ |
| 1443 | ++++ | NT |
| 1444 | ++++ | +++ |
| 1445 | ++++ | +++ |
| 1446 | ++++ | NT |
| 1447 | ++++ | NT |
| 1448 | ++++ | NT |
| 1449 | ++++ | NT |

TABLE 1-continued

ALK, JAK2 Kinase Inhibition

| Example | ALK Potency | JAK2 Potency |
|---|---|---|
| 1450 | +++ | +++ |
| 1451 | ++++ | ++++ |
| 1452 | ++++ | +++ |
| 1453 | ++++ | +++ |
| 1454 | ++++ | +++ |
| 1455 | ++++ | ++++ |
| 1456 | ++++ | ++++ |
| 1457 | ++++ | +++ |
| 1458 | ++++ | +++ |
| 1459 | ++++ | +++ |
| 1460 | ++++ | ++++ |
| 1461 | ++++ | ++++ |
| 1462 | +++ | +++ |
| 1463 | ++++ | ++++ |
| 1464 | ++++ | +++ |
| 1465 | ++++ | ++++ |
| 1466 | ++++ | ++++ |
| 1467 | ++++ | ++++ |
| 1468 | ++++ | +++ |
| 1469 | ++++ | +++ |
| 1470 | +++ | ++++ |
| 1471 | ++++ | +++ |
| 1472 | ++++ | ++++ |
| 1473 | ++++ | ++++ |
| 1474 | ++++ | +++ |
| 1475 | ++++ | +++ |
| 1476 | ++++ | +++ |
| 1477 | ++++ | ++ |
| 1478 | ++++ | ++ |
| 1479 | ++++ | +++ |
| 1480 | ++++ | +++ |
| 1481 | ++++ | ++++ |
| 1482 | +++ | ++++ |
| 1483 | ++++ | ++ |
| 1484 | ++++ | ++++ |
| 1485 | +++ | ++++ |
| 1491 | ++++ | +++ |
| 1492 | +++ | +++ |
| 1493 | +++ | +++ |
| 1494 | + | + |
| 1495 | + | + |
| 1496 | ++++ | ++ |
| 1497 | ++++ | ++++ |
| 1498 | ++++ | ++++ |
| 1499 | +++ | ++++ |
| 1500 | ++++ | ++++ |
| 1501 | + | + |
| 1502 | + | + |
| 1503 | +++ | ++++ |
| 1504 | +++ | ++++ |
| 1505 | ++ | ++ |
| 1506 | + | ++++ |
| 1507 | +++ | ++++ |
| 1508 | ++ | ++++ |
| 1509 | +++ | ++++ |
| 1510 | ++ | ++++ |
| 1511 | ++ | ++++ |
| 1512 | +++ | ++++ |
| 1513 | ++ | ++++ |
| 1514 | +++ | ++++ |
| 1515 | +++ | ++++ |
| 1516 | ++ | ++++ |
| 1517 | +++ | ++++ |
| 1518 | +++ | ++++ |
| 1519 | ++ | ++++ |
| 1520 | +++ | ++++ |
| 1521 | +++ | ++++ |
| 1522 | +++ | ++++ |
| 1523 | ++ | ++++ |
| 1524 | +++ | ++++ |
| 1525 | +++ | ++++ |
| 1526 | +++ | ++++ |
| 1527 | +++ | ++++ |
| 1528 | +++ | ++++ |
| 1529 | +++ | ++++ |
| 1530 | +++ | ++++ |
| 1531 | ++ | ++++ |
| 1532 | ++ | ++ |
| 1533 | ++++ | ++ |
| 1534 | +++ | ++++ |
| 1535 | ++ | ++++ |
| 1536 | +++ | ++++ |
| 1537 | ++ | ++++ |
| 1538 | +++ | ++++ |
| 1539 | ++ | ++++ |
| 1540 | +++ | ++++ |
| 1541 | + | ++++ |
| 1542 | ++ | ++++ |
| 1543 | ++ | ++++ |
| 1544 | +++ | ++++ |
| 1545 | +++ | ++++ |
| 1546 | ++ | ++++ |
| 1547 | ++ | ++++ |
| 1548 | +++ | ++++ |
| 1549 | ++++ | ++++ |
| 1550 | ++++ | ++++ |
| 1551 | +++ | ++++ |
| 1552 | +++ | ++++ |
| 1553 | ++++ | ++++ |
| 1554 | ++++ | ++ |
| 1555 | +++ | ++++ |
| 1556 | ++++ | ++++ |
| 1557 | ++++ | ++++ |
| 1558 | +++ | ++++ |
| 1559 | ++ | ++++ |
| 1560 | + | ++++ |
| 1561 | ++ | ++++ |
| 1562 | ++ | ++++ |
| 1563 | +++ | ++++ |
| 1564 | ++ | ++++ |
| 1565 | ++++ | ++++ |
| 1566 | ++ | ++++ |
| 1567 | +++ | ++++ |
| 1568 | ++ | ++++ |
| 1571 | +++ | ++++ |
| 1572 | +++ | ++++ |
| 1573 | +++ | ++++ |
| 1574 | ++ | ++++ |
| 1575 | +++ | ++++ |

$IC_{50} > 10\ \mu M$ +
$IC_{50}\ 10\ \mu M - 1\ \mu M$ ++
$IC_{50}\ 1\ \mu M - 0.1\ \mu M$ +++
$IC_{50} < 0.1\ \mu M$ ++++

Preferably, a compound of the present invention (i.e., a compound of formula I or a pharmaceutically acceptable salt thereof) has an ALK kinase $IC_{50}$ of <10 μM. In one embodiment, a compound of the present invention has an ALK kinase $IC_{50}$ of 10 μM-1 μM. More preferably, a compound of the present invention has an ALK kinase $IC_{50}$ of <1 μM. In one embodiment, a compound of the present invention has an ALK kinase $IC_{50}$ of 1 μM-0.1 μM. More preferably, a compound of the present invention has an ALK kinase $IC_{50}$ of <0.1 μM.

Preferably, a compound of the present invention has a JAK2 kinase $IC_{50}$ of <10 μM. In one embodiment, a compound of the present invention has a JAK2 kinase $IC_{50}$ of 10 μM-1 μM. More preferably, a compound of the present invention has a JAK2 kinase $IC_{50}$ of <1 μM. In one embodiment, a compound of the present invention has a JAK2 kinase $IC_{50}$ of 1 μM-0.1 μM. More preferably, a compound of the present invention has a JAK2 kinase $IC_{50}$ of <0.1 μM.

In one embodiment, a compound of the present invention has an ALK kinase $IC_{50}$ of <10 μM and a JAK2 kinase $IC_{50}$ of <10 μM. In one embodiment, a compound of the present invention has an ALK kinase $IC_{50}$ of 10 μM-1 μM and a JAK2 kinase $IC_{50}$ of 10 μM-1 μM. In one embodiment, a compound of the present invention has an ALK kinase $IC_{50}$ of <1 μM and a JAK2 kinase $IC_{50}$ of <1 μM. In one embodiment, a compound of the present invention has an ALK kinase $IC_{50}$ of 1 μM-0.1 μM and a JAK2 kinase $IC_{50}$ of 1 μM-0.1 μM. In one embodiment, a compound of the present invention has an ALK kinase $IC_{50}$ of <0.1 μM and a JAK2 kinase $IC_{50}$ of <0.1 μM.

In one embodiment, a compound of formula I has an $IC_{50}$ in the ALK kinase assay of 10 μM-1 μM. In another embodiment, a compound of formula I has an $IC_{50}$ in the ALK kinase assay of 1 μM-0.1 μM. In another embodiment, a compound of formula I has an $IC_{50}$ in the ALK kinase assay of <0.1 μM.

In one embodiment, a compound of formula I has an $IC_{50}$ in the JAK2 kinase assay of 10 μM-1 μM. In another embodiment, a compound of formula I has an $IC_{50}$ in the JAK2 kinase assay of 1 μM-0.1 μM. In another embodiment, a compound of formula I has an $IC_{50}$ in the JAK2 kinase assay of <0.1 μM.

EXAMPLES

Example 1

[7-(3-Chloro-phenyl)-pyrrolo[2,1-f][1,2,4]triazin-2-yl]-(4-morpholin-4-yl-phenyl)-amine 1a) 1-(3-Benzoyl-thioureido)-1H-pyrrole-2-carboxylic acid methyl ester.

Chloramine was made according to J. Org. Chem., Vol 69 (4), 1368-1371. Into 4 L Erlenmyer flask, 1H-Pyrrole-2-carboxylic acid methyl ester (25.00 g, 0.1938 mol) and Tetrahydrofuran (1000 mL, 10 mol) were added and stirred at room temperature for 20 minutes under an atmosphere of Nitrogen. 1.00 M of Potassium tert-Butoxide in Tetrahydrofuran (500.0 mL, 0.5000 mol) was added and stirred for 30 minutes at room temperature. 0.15 M of Chloramine in Ether (2100 mL, 0.31 mol) was added to the reaction mixture at 10° C. over 20 minutes with nitrogen bubbling into the reaction mixture. The reaction was stirred at room temperature for 2 hours. HPLC suggested 72% conversion (18% SM remained). Saturated $Na_2S_2O_3$ (500 mL) was added at 10° C. over 30 minutes. The mixture was stirred for one hour. The organic was separated, washed with water, then subsequently with Brine, and dried over $Na_2SO_4$. The solid was filtered and washed with DCM. The solvent was concentrated to approximately 500 mL. Benzoyl isothiocyanate (22.75 g, 0.1394 mol) in Tetrahydrofuran (100 mL, 1 mol) was added dropwise to the residual organic. The reaction mixture was stirred at room temperature overnight. The solvent was removed under vacuum. The solid was partitioned with $Et_2O$ (200 mL) and stirred for 30 minutes. The solid was filtered and washed with hexane/$Et_2O$ (9 to 1) to give 1-(3-Benzoyl-thioureido)-1H-pyrrole-2-carboxylic acid ethyl ester (38.20 g) as an off white solid. NMR $^1$H (DSMO-$d_6$) 12.89 (s, 1H), 11.92 (s, 1H), 7.99 (d, 2H, J=7.46 Hz), 7.68 (t, 1H, J=7.37 Hz), 7.55 (t, 1H, J=7.81 Hz), 7.19 (dd, 1H, JJ=2.04, 1.64 Hz), 6.89 (dd, 1H, JJ=1.76, 1.60 Hz), 6.20 (dd, 1H, J=3.00, 1.04 Hz), 3.68 (s, 3H).

1b) 2-Thioxo-2,3-dihydro-1H-pyrrolo[2,1-f][1,2,4]triazin-4-one. Into a 500 mL beaker, 1-(3-Benzoyl-thioureido)-1H-pyrrole-2-carboxylic acid methyl ester (38.20 g, 0.1259 mol) and 2.00 M of Sodium hydroxide in Water (252 mL, 0.504 mol) were added. The mixture was heated at 85° C. for 75 minutes. The reaction was cooled to room temperature. The solid was dissolved with Ethanol (100 mL). Acetic acid (29.0 mL, 0.510 mol) was added at 0° C. and stirred for 30 minutes. The solid was filtered and washed with cold EtOH (50 mL) to afforded a white solid. The white solid was stirred in $Et_2O$ (300 mL) for 20 minutes. The solid was filtered and washed with $Et_2O$ (200 mL) to give 2-Thioxo-2,3-dihydro-1H-pyrrolo[2,1-f][1,2,4]triazin-4-one as a white solid. The desired product was dried under vacuum overnight (17.5 g, 83%). NMR $^1$H (DSMO-$d_6$)-9.78 (bs, 1H), 7.26 (bs, 1H), 7.02-7.15 (m, 1H), 6.73-77 (m, 1H), 6.58-6.65 (m, 1H).

1c) 2-Methylsulfanyl-3H-pyrrolo[2,1-f][1,2,4]triazin-4-one: Into a Round bottom flask, 2-Thioxo-2,3-dihydro-1H-pyrrolo[2,1-f][1,2,4]triazin-4-one (17.50 g, 0.1047 mol), Tetrahydrofuran (500 mL, 6 mol) and Methyl iodide (8.40 mL, 0.135 mol) were added, respectively. The reaction was stirred at 45° C. for one hour. The solid was filtered. The solvent was removed under vacuum to give a solid. The combined solid was partitioned with water (500 mL) and saturated NaHCO3 (500 mL). The mixture was stirred for 30 minutes. The solid was filtered and washed with water to give 2-methylsulfanyl-3H-pyrrolo[2,1-f][1,2,4]triazin-4-one as a white solid (17.70 g, 93%). NMR $^1$H (DSMO-$d_6$)-12.02 (bs, 1H), 7.50 (t, 1H, J=2.36 Hz), 6.79 (dd, 1H, JJ=1.52, 2.60 Hz), 6.45 (dd, 1H, JJ=2.64, 2.50 Hz)

1d) 4-Chloro-2-methylsulfanyl-pyrrolo[2,1-f][1,2,4]triazine: Into a Round bottom flask, 2-Methylsulfanyl-3H-pyrrolo[2,1-f][1,2,4]triazin-4-one (17.60 g, 0.09712 mol) and Phosphoryl chloride (110 mL, 1.2 mol) were added and heated at 100° C. for 4 hours. The solvent was removed under vacuum to give a solid. Ice water was added and stirred for 5 minutes. $NH_4OH$ (25 mL) in ice water was added and stirred at room temperature for 1 hour. The solid was filtered and washed with generous amount of water. The solid was then dissolved in DCM (1 L). The organic was washed with Brine and dried over $Na_2SO_4$. The solid was filtered. The solvent was removed under vacuum to give a yellow solid 4-Chloro-2-methylsulfanyl-pyrrolo[2,1-f][1,2,4]triazine (17.40 g, 90%). HPLC suggested >90% pure. NMR $^1$H (DSMO-$d_6$) 8.15 (bs, 1H), 7.04 (dd, 1H, JJ=1.22, 3.44 Hz), 6.98 (dd, 1H, JJ=2.52, 2.04 Hz), 2.50 (s, 3H)

1e). 7-Bromo-4-chloro-2-methylsulfanyl-pyrrolo[2,1-f][1,2,4]triazine: Into a Round bottom flask, 4-Chloro-2-methylsulfanyl-pyrrolo[2,1-f][1,2,4]triazine (10.0 g, 0.0501 mol), Tetrahydrofuran (500 mL, 6 mol), and Methanol (250 mL, 6.2 mol) were added. N-Bromosuccinimide (8.91 g, 0.0501 mol) was added portion wise to the reaction for 1 hour at 0° C. The reaction was stirred at room temperature for 1 hour. The solvent was removed under vacuum. The solid was partitioned with water and DCM (500 mL). The organic was separated, washed with Brine, and dried over magnesium sulfate. The solid was filtered and washed with DCM. The solvent was removed under vacuum to afford a yellow solid. The yellow solid was suspended in Isopropyl alcohol (160 mL, 2.1 mol) at 55° C. Sodium borohydride (3.98 g, 0.105 mol) was added and heated at 60° C. for 3 hours. The reaction was allowed to cool to RT. The solid was filtered and washed with DCM. The solvent was removed under vacuum to a viscous oil.

Methylene chloride (300 mL, 5 mol) was added to the viscous oil.

Dichlorodicyanoquinone (12.5 g, 0.0551 mol) was then added portion wise over 15 minutes. The mixture was stirred for 30 minutes. The solid was filtered through Celite and washed with DCM. The solvent was removed under vacuum to give a mixture of three brominated products. The reaction was purified via ISCO column chromatography with hexane and EtOAc as eluant (0 to 8% EtOAc). The collected fractions afforded a mixture of 7-Bromo-4-chloro-2-methylsulfanyl-pyrrolo[2,1-f][1,2,4]triazine (9.80 g, 74.3%), 5-Bromo-2-methylsulfanyl-pyrrolo[2,1-f][1,2,4]triazine (0.80 g, 7%)

and 5,7-Dibromo-2-methylsulfanyl-pyrrolo[2,1-f][1,2,4]triazine (1.20 g, 7%). 7-Bromo-4-chloro-2-methylsulfanyl-pyrrolo[2,1-f][1,2,4]triazine NMR $^1$H (DSMO-d$_6$)-8.95 (s, 1H), 7.09 (s, 2H), 2.50 (s, 3H). 5-Bromo-2-methylsulfanyl-pyrrolo[2,1-f][1,2,4]triazine NMR $^1$H (DSMO-d$_6$)-8.91 (s, 1H), 8.06 (d, 1H, J=2.40 Hz), 7.08 (d, 1H, J=2.74 Hz), 2.50 (s, 3H). 5,7-Dibromo-2-methylsulfanyl-pyrrolo[2,1-f][1,2,4]triazine NMR $^1$H (DSMO-d$_6$)-8.99 (s, 1H), 7.64 (s, 1H), 2.50 (s, 3H).

1f) 7-Bromo-2-methanesulfinyl-pyrrolo[2,1-f][1,2,4]triazine: Into a Round bottom flask, m-Chloroperbenzoic acid (2.89 g, 0.0129 mol) was added to a solution of 7-Bromo-2-methylsulfanyl-pyrrolo[2,1-f][1,2,4]triazine (3.00 g, 0.0123 mol) in Methylene chloride (70 mL, 1 mol) at 0° C. The reaction was stirred for 1 hour at room temperature. Sat. NaHCO$_3$ was added and stirred for 30 minutes. The organic was separated, washed with Brine, and dried over magnesium sulfate. The solid was filtered and washed with EtOAc. The solvent was removed under vacuum to afforded a yellow solid. The solid was triturated with Et$_2$O to give 7-Bromo-2-methanesulfinyl-pyrrolo[2,1-f][1,2,4]triazine as a yellow powder (3.10 g, 97%). NMR $^1$H (DSMO-d$_6$)-9.25 (s, 1H), 7.39 (d, 1H, J=4.80 Hz), 7.32 (d, 1H, J=4.76 Hz), 2.97 (s, 3H)

1g) (7-Bromo-pyrrolo[2,1-f][1,2,4]triazin-2-yl)-(4-morpholin-4-yl-phenyl)-amine Into a 30 mL vial, [A] 7-Bromo-2-methanesulfinyl-pyrrolo[2,1-f][1,2,4]triazine (2.20 g, 0.00846 mol), [B] 4-(4-morpholino)aniline (3.32 g, 0.0186 mol), and N-Methylpyrrolidinone (3.52 mL, 0.0365 mol) were combined and heated to 145° C. for 2 hours. The reaction was cooled to RT. The reaction mixture was purified via ISCO column chromatography with DCM and methanol as eluant (0 to 10% methanol). The collected fractions were concentrated to afford (7-Bromo-pyrrolo[2,1-f][1,2,4]triazin-2-yl)-(4-morpholin-4-yl-phenyl)-amine as a brown solid (1.14 g, 71%). NMR $^1$H (DSMO-d$_6$)-9.42 (s, 1H), 8.89 (s, 1H), 7.76 (d, 1H, J=8.96 Hz), 6.82-6.98 (m, 4H), 3.73 (t, 4H, J=4.57 Hz), 3.05 (t, 4H, J=4.77 Hz)

1h) [7-(3-Chloro-phenyl)-pyrrolo[2,1-f][1,2,4]triazin-2-yl]-(4-morpholin-4-yl-phenyl)-amine: Into a Round bottom flask, Palladium Acetate (2 mg, 0.008 mmol), Triphenylphosphine (6.7 mg, 0.026 mmol) were added and purged under an atmosphere of Nitrogen for 10 minutes. 1,4-Dioxane (2.00 mL, 25.6 mmol) was added and stirred for 10 minutes. [A] (7-Bromo-pyrrolo[2,1-f][1,2,4]triazin-2-yl)-(4-morpholin-4-yl-phenyl)-amine (32 mg, 0.086 mmol) and [B] 3-chlorophenyl boronic acid (20.0 mg, 0.128 mmol) in N,N-Dimethylformamide (3.00 mL, 38.7 mmol) and 1.50 M of Sodium carbonate in Water (0.171 mL, 0.256 mmol) were added and heated at 90° C. for 2 hours. The solvent was removed under vacuum. The solid was partitioned with water and DCM. The organic was separated, washed with Brine, and dried over magnesium sulfate. The solid was filtered and washed with EtOAc. The solvent was removed under vacuum. The reaction mixture was purified via ISCO column chromatography with DCM and methanol as eluant (0 to 10% Methanol). The collected fractions afforded a yellow solid. The solid was then triturated with cold methanol to give [7-(3-Chloro-phenyl)-pyrrolo[2,1-f][1,2,4]triazin-2-yl]-(4-morpholin-4-yl-phenyl)-amine as a bright yellow solid (5 mg, 14%). LCMS (E/I+) 406.09 (M+H). NMR $^1$H (DSMO-d$_6$)-9.31 (s, 1H), 8.79 (s, 1H), 8.47 (s, 1H), 8.04 (d, 1H, J=7.84 Hz), 7.63 (d, 1H, J=8.73), 7.53 (t, 1H, J=8.08), 7.42 (d, 1H, J=6.92), 7.25 (d, 1H, J=4.97 Hz), 6.98-6.80 (m, 3H), 3.75 (t, 4H, J=4.66 Hz), 3.06 (t, 4H, J=4.80 Hz).

Example 2

(4-Morpholin-4-yl-phenyl)-(7-phenyl-pyrrolo[2,1-f][1,2,4]triazin-2-yl)amine

The titled compound was prepared in an analogous fashion to Example 1 replacing 3-chlorophenyl boronic acid with phenylboronic acid to give (4-Morpholin-4-yl-phenyl)-(7-phenyl-pyrrolo[2,1-f][1,2,4]triazin-2-yl)amine as a yellow solid (78 mg, 45%). MP—219-220° C. LCMS (E/I+) 372.20 (M+H). NMR $^1$H (DSMO-d$_6$)-8.68 (s, 1H), 8.14 (d, 1H, J=7.42 Hz), 7.58 (d, 1H, J=8.78 Hz), 7.49 (t, 1H, J=7.57 Hz), 6.99 (d, 1H, J=4.72 Hz), 6.92 (d, 2H, J=9.12 Hz), 6.82 (d, 1H, J=5.32 Hz), 6.68 (bs, 1H), 3.88 (t, 4H, J=4.68 Hz), 3.13 (t, 4H, J=4.64 Hz).

Example 3

[7-(5-Chloro-2-methoxy-phenyl)-pyrrolo[2,1-f][1,2,4]triazin-2-yl]-(4-morpholin-4-yl-phenyl)-amine The titled compound was prepared in an analogous fashion to Example 1 replacing 3-chlorophenyl boronic acid with 5-Chloro-2-methoxyphenyl boronic acid to give [7-(5-Chloro-2-methoxy-phenyl)-pyrrolo[2,1-f][1,2,4]triazin-2-yl]-(4-morpholin-4-yl-phenyl)-amine as a yellow solid (30 mg, 42%). MP—206-210° C. LCMS (E/I+) 436.24 (M+H). NMR $^1$H (DSMO-d$_6$)-9.24 (s, 1H), 8.93 (s, 1H), 8.06 (d, 1H, J=2.60 Hz), 7.61 (d, 1H, J=8.92 Hz), 7.46 (dd, 1H, JJ=2.72, 8.84 Hz), 7.23 (d, 1H, J=1.12 Hz), 7.03 (d, 1H, J=4.72 Hz), 6.89 (d, 1H, J=4.72 Hz), 6.87 (d, 1H, J=9.09 Hz), 3.82 (s, 3H), 3.73 (t, 4H, J=4.56 Hz), 3.00 (t, 4H, J=4.86 Hz).

Example 4

(4-Morpholin-4-yl-phenyl)-(7-pyridin-4-yl-pyrrolo[2,1-f][1,2,4]triazin-2-yl)-amine The titled compound was prepared in an analogous fashion to Example 1 replacing 3-chlorophenyl boronic acid with 4-Pyridylboronic acid to give (4-Morpholin-4-yl-phenyl)-(7-pyridin-4-yl-pyrrolo[2,1-f][1,2,4]triazin-2-yl)-amine as a yellow solid (31 mg, 52%). MP 246-248° C. LCMS (E/I+) 373.22 (M+H). NMR $^1$H (DSMO-d$_6$)-9.36 (s, 1H), 9.02 (s, 1H), 8.68 (d, 1H, J=1.09 Hz), 8.21 (d, 2H, J=6.04 Hz), 7.61 (d, 2H, J=8.93 Hz), 7.38 (d, 1H, J=4.80 Hz), 6.98 (d, 2H, J=8.96 Hz), 6.96 (d, 1H, J=4.12 Hz), 3.75 (t, 4H, J=4.52 Hz), 3.09 (t, 4H, J=4.63 Hz).

Example 5

[7-(2,3-Dihydro-benzo[1,4]dioxin-6-yl)-pyrrolo[2,1-f][1,2,4]triazin-2-yl]-(4-morpholin-4-yl-phenyl)-amine The titled compound was prepared in an analogous fashion to Example 1 replacing 3-chlorophenyl boronic acid with 2,3-Dihydro-1,4-benzodioxine-6-ylboronic acid to give [7-(2,3-Dihydro-benzo[1,4]dioxin-6-yl)-pyrrolo[2,1-f][1,2,4]triazin-2-yl]-(4-morpholin-4-yl-phenyl)amine as a yellow solid (33 mg, 48%). MP 205-208° C. LCMS 430.25 (M+H). NMR $^1$H (DSMO-d$_6$)-9.19 (s, 1H), 8.88 (d, 1H, J=1.09 Hz), 7.85 (d, 1H, J=1.92 Hz), 7.64 (d, 3H, J=8.76 Hz), 7.09 (d, 1H, J=4.76 Hz), 7.00 (d, 1H, J=7.53 Hz), 6.93 (d, 2H, J=8.93 Hz), 6.88 (d, 1H, J=4.77 Hz). 4.32 (s, 4H), 3.75 (t, 4H, J=4.40 Hz), 3.06 (t, 4H, J=4.77 Hz)

Example 6

3-[2-(4-Morpholin-4-yl-phenylamino)-pyrrolo[2,1-f][1,2,4]triazin-7-yl]-benzoic acid methyl ester The titled compound was prepared in an analogous fashion to Example 1 replacing 3-chlorophenyl boronic acid with 3-methoxycarbonyl phenyl boronic give 3-[2-(4-Morpholin-4-yl-phenylamino)-pyrrolo[2,1-f][1,2,4]triazin-7-yl]-benzoic acid methyl ester as a yellow solid. MP 178-184° C. LCMS (E/I+) 430.24 (M+H). NMR $^1$H (DSMO-d$_6$)-9.31 (s, 1H), 8.97 (s, 1H), 8.79 (s, 1H), 8.34 (d, 1H, J=8.00 Hz), 7.97 (d, 1H, J=8.04 Hz), 7.60-7.75 (m, 3H), 7.20 (d, 1H, J=468 Hz), 6.95 (d, 1H, J=4.68 Hz), 6.87 (d, 2H, J=9.01 Hz), 3.87 (s, 3H), 3.74 (t, 4H, J=4.48 Hz), 3.03 (t, 4H, J=4.64 Hz).

Example 7

[4-(4-Methyl-piperazin-1-yl)-phenyl]-(7-phenyl-pyrrolo[2,1-f][1,2,4]triazin-2-yl)-amine 7a) (7-Bromo-pyrrolo[2,1-f][1,2,4]triazin-2-yl)-[4-(4-methyl-piperazin-1-yl)-phenyl]-amine: Into a 30 mL vial, [B] 4-(4-Methyl-piperazin-1-yl)-phenylamine (0.485 g, 0.00254 mol), [A] 7-Bromo-2-methanesulfinyl-pyrrolo[2,1-f][1,2,4]triazine (0.300 g, 0.00115 mol), and N-Methylpyrrolidinone (1.0 mL, 0.010 mol) were added. The reaction mixture was heated at 135° C. for 7 hours. The reaction mixture was purified via ISCO column chromatography with EtOAc and methanol as eluant (0 to 15% methanol). The collected fractions afforded (7-Bromo-pyrrolo[2,1-f][1,2,4]triazin-2-yl)-[4-(4-methyl-piperazin-1-yl)-phenyl]-amine as a yellow solid (220 mg, 49%). NMR $^1$H (DSMO-d$_6$)-9.40 (s, 1H), 8.85 (s, 1H), 7.75 (d, 2H, J=8.97 Hz), 6.88-6.98 (m, 4H), 3.02-3.07 (bs, 4H), 2.37-2.2.47 (bs, 4H), 2.21 (s, 3H)

7b) [4-(4-Methyl-piperazin-1-yl)-phenyl]-(7-phenyl-pyrrolo[2,1-f][1,2,4]triazin-2-yl)-amine: Into a 30 mL vial, Palladium Acetate (6 mg, 0.00003 mol) and Triphenylphosphine (20 mg, 0.00008 mol) were added and purged under an atmosphere of Nitrogen for 5 minutes. 1,4-Dioxane (1.5 mL, 0.019 mol) was added and stirred for 10 minutes. [A] (7-Bromo-pyrrolo[2,1-f][1,2,4]triazin-2-yl)-[4-(4-methyl-piperazin-1-yl)-phenyl]-amine (62.1 mg, 0.000160 mol) and [B] Phenylboronic acid (39.1 mg, 0.000321 mol) in N,N-Dimethylformamide (1.5 mL, 0.019 mol) and 1.50 M of Sodium carbonate in Water (1.00 mL, 0.00150 mol) were added, respectively. The reaction mixture was heated at 100° C. for 30 minutes. The solvent was removed under vacuum. The solid was washed with DCM. The organic was removed under vacuum. The reaction mixture was purified via ISCO column chromatography with DCM and methanol as eluant (0 to 10% methanol). The collected fractions afforded a solid. The solid was washed with methanol to give a [4-(4-Methyl-piperazin-1-yl)-phenyl]-(7-phenyl-pyrrolo[2,1-f][1,2,4]triazin-2-yl)-amine as a yellow solid (18 mg, 29%). MP—246-248° C. LCMS (E/I+) 385.28 (M+H). NMR $^1$H (DSMO-d$_6$)-9.22 (s, 1H), 8.23 (s, 1H), 8.19 (d, 2H, J=8.40 Hz), 7.63 (d, 2H, J=9.05 Hz), 7.53 (t, 2H, J=7.88 Hz), 7.38 (t, 1H, J=7.40 Hz), 7.15 (d, 1H, J=4.72 Hz), 6.85-6.95 (m, 3H), 3.10-3.17 (m, 4H), 2.42-2.60 (m, 4H), 2.27 (s, 3H)

Example 8

[7-(2,3-Dihydro-benzo[1,4]dioxin-6-yl)-pyrrolo[2,1-f][1,2,4]triazin-2-yl]-[4-(4-methyl-piperazin-1-yl)-phenyl]-amine The titled compound was prepared in an analogous fashion to Example 7 replacing phenylboronic acid with 2,3-Dihydro-1,4-benzodioxine-6-ylboronic acid to give [7-(2,3-Dihydro-benzo[1,4]dioxin-6-yl)-pyrrolo[2,1-f][1,2,4]triazin-2-yl]-[4-(4-methyl-piperazin-1-yl)-phenyl]-amine as a yellow solid (60 mg, 40%). MP—222-224° C. LCMS (E/I+) 443.25 (M+H). NMR $^1$H (DSMO-d$_6$)-9.17 (s, 1H), 8.88 (s, 1H), 7.85 (s, 1H), 7.58-7.77 (m, 3H), 7.08 (d, 1H, J=8.36 Hz), 7.00 (d, 1H, J=8.41 Hz), 6.95 (d, 2H, J=8.44 Hz), 6.87 (d, 1H, J=6.73 Hz), 4.32 (s, 4H), 3.03-3.15 (bm, 4H), 2.43-2.55 (bm, 4H), 2.22 (s, 3H).

Example 9

[3-(2-Methoxy-ethyl)-2,3,4,5-tetrahydro-1H-benzo[d]azepin-7-yl]-(7-phenyl-pyrrolo[2,1-f][1,2,4]triazin-2-yl)-amine 9a) Into a 30 ml, vial, [A] 3-(2-Methoxy-ethyl)-2,3,4,5-tetrahydro-1H-benzo[d]azepin-7-ylamine (0.242 g, 0.00110 mol), [B] 7-Bromo-2-methanesulfinyl-pyrrolo[2,1-f][1,2,4]triazine (0.130 g, 0.000500 mol), and N-Methylpyrrolidinone (0.39 mL, 0.0041 mol) were added. The reaction mixture was heated at 135° C. for 7 hours. The reaction mixture was purified via ISCO column chromatography with EtOAc and methanol as eluant (5 to 20% methanol). The collected fractions afforded (7-Bromo-pyrrolo[2,1-f][1,2,4]triazin-2-yl)-[3-(2-methoxy-ethyl)-2,3,4,5-tetrahydro-1H-benzo[d]azepin-7-yl]-amine as a yellow solid (130 mg, 65%). NMR $^1$H (CDCl$_3$-d)-8.57 (s, 1H), 7.54 (s, 1H), 7.48 (dd, 1H, JJ=1.96, 6.04 Hz), 7.69 (s, 1H), 7.09 (d, 1H, J=8.04 Hz), 6.93 (s, 1H), 6.78 (d, 1H, J=4.72 Hz), 6.73 (d, 1H, J=4.72 Hz), 3.54 (t, 2H, J=5.68 Hz), 3.36 (s, 3H), 2.65-3.00 (m, 10H)

9b) Into a 30 mL vial, Palladium Acetate (14.0 mg, 0.0624 mmol) and Triphenylphosphine (41.0 mg, 0.156 mmol) were added and purged under an atmosphere of Nitrogen for 5 minutes. 1,4-Dioxane (2.9 mL, 37 mmol) was added and stirred for 10 minutes. (7-Bromo-pyrrolo[2,1-f][1,2,4]triazin-2-yl)-[3-(2-methoxy-ethyl)-2,3,4,5-tetrahydro-1H-benzo[d]azepin-7-yl]-amine (0.130 g, 0.312 mmol) and [B] Phenylboronic acid (0.0761 g, 0.624 mmol) in N,N-Dimethylformamide (2.9 mL, 38 mmol) and 1.50 M of Sodium carbonate in Water (0.624 mL, 0.937 mmol) were added, respectively. The reaction mixture was heated at 100° C. for 30 minutes. The solvent was removed under vacuum. The solid was washed with DCM. The organic was removed under vacuum. The reaction mixture was purified via ISCO column chromatography with DCM and methanol as eluant (0 to 20% methanol). The collected fractions afforded a solid. The solid was washed with 10% Et$_2$O/hexane to give [3-(2-Methoxy-ethyl)-2,3,4,5-tetrahydro-1H-benzo[d]azepin-7-yl]-(7-phenyl-pyrrolo[2,1-f][1,2,4]triazin-2-yl)-amine as a yellow solid (48 mg, 37%). MP 116-118° C. LCMS (E/I+) 414.26 (M+H). NMR $^1$H (DSMO-d$_6$) 9.36 (s, 1H), 8.96 (s, 1H), 8.11 (d, 1H, J=7.57 Hz), 7.69 (s, 1H), 7.51 (t, 2H, J=7.48 Hz), 7.41 (t, 1H, J=7.28 Hz), 7.34 (d, 1H, J=8.04 Hz), 7.17 (d, 1H, J=4.72 Hz), 7.02 (d, 1H, J=8.16 Hz), 6.94 (d, 1H, J=4.72 Hz), 3.46 (t, 2H, J=5.80 Hz), 3.24 (s, 3H), 2.79 (bs, 4H), 2.50-2.70 (m, 6H).

Example 10

[7-(1-Methyl-1H-pyrazol-4-yl)-pyrrolo[2,1-f][1,2,4]triazin-2-yl]-(4-morpholin-4-yl-phenyl)-amine The titled compound was prepared in an analogous fashion to Example 1 replacing 3-chlorophenyl boronic acid with 1-Methyl-4-(4,4,5,5-tetramethyl-[1,3,2]dioxaborolan-2-yl)-1H-pyrazole to give [7-(1-Methyl-1H-pyrazol-4-yl)-pyrrolo[2,1-f][1,2,4]triazin-2-yl]-(4-morpholin-4-yl-phenyl)-amine as a yellow solid (18 mg, 17%). MP 253-254° C. LCMS 376.21 (M+H). NMR $^1$H (DSMO-d$_6$)-9.10 (s, 1H), 8.83 (s, 1H), 8.39 (s, 1H), 8.14 (s, 1H), 7.59 (d, 1H, J=8.88 Hz), 6.94-7.07 (m, 3H), 6.86 (d, 1H, J=4.68 Hz), 3.92 (s, 3H), 3.75 (t, 4H, J=4.72 Hz), 3.0 (t, 4H, J=4.76 Hz).

Example 11

(4-Morpholin-4-yl-phenyl)-(7-pyridin-3-yl-pyrrolo[2,1-f][1,2,4]triazin-2-yl)-amine The titled compound was prepared in an analogous fashion to Example 1 replacing 3-chlorophenyl boronic acid 3-Pyridylboronic acid to give (4-Morpholin-4-yl-phenyl)-(7-pyridin-3-yl-pyrrolo[2,1-f][1,2,4]triazin-2-yl)-amine as a yellow solid (32 mg, 29%). MP 240-241° C. LCMS (E/I+) 373.18 (M+H). NMR $^1$H (DSMO-$d_6$)-9.28-9.34 (m, 2H), 8.98 (s, 1H), 8.51-8.60 (m, 2H), 7.53-7.63 (m, 3H), 7.27 (d, 1H, J=4.78 Hz), 6.85-6.95 (m, 3H), 3.75 (t, 4H, J=4.64 Hz), 3.06 (t, 4H, J=4.49 Hz).

Example 12

(7-Phenyl-pyrrolo[2,1-f][1,2,4]triazin-2-yl)-pyridin-3-ylmethyl-amine 12a) 2-Methylsulfanyl-7-phenyl-pyrrolo[2,1-f][1,2,4]triazine: Into a 30 mL vial, Palladium Acetate (193 mg, 0.860 mmol) and Triphenylphosphine (564 mg, 2.15 mmol) were added and purged under an atmosphere of Nitrogen for 5 minutes. 1,4-Dioxane (4.0E1 mL, 520 mmol) was added and stirred for 10 minutes. [A] 7-Bromo-2-methylsulfanyl-pyrrolo[2,1-f][1,2,4]triazine (1.05 g, 4.30 mmol) and [B] Phenylboronic acid (1.05 g, 8.60 mmol) in N,N-Dimethylformamide (4.0E1 mL, 520 mmol) and 1.50 M of Sodium carbonate in Water (8.60 mL, 12.9 mmol) were added, respectively. The reaction mixture was heated at 100° C. for 30 minutes. The solvent was removed under vacuum. The solid was washed with DCM. The organic was removed under vacuum. The reaction was purified via ISCO column chromatography with DCM and methanol as eluant (0 to 20% methanol). The collected fraction afforded a solid. The solid was washed with 10% Et2O/hexane to give 2-Methylsulfanyl-7-phenyl-pyrrolo[2,1-f][1,2,4]triazine a yellow solid (621 mg, 60%). NMR $^1$H (DSMO-$d_6$)-9.03 (s, 1H), 8.23 (d, 2H, J=7.80 Hz), 7.53 (t, 2H, J=7.80), 7.30-7.45 (m, 2H), 7.11 (d, 1H, J=4.70 Hz), 2.60 (s, 3H) 12b) 2-Methanesulfinyl-7-phenyl-pyrrolo[2,1-f][1,2,4]triazine: Into a round bottom flask, 2-Methylsulfanyl-7-phenyl-pyrrolo[2,1-f][1,2,4]triazine (0.621 g, 0.00257 mol) and Methylene chloride (7 mL, 0.08 mol) were added. m-Chloroperbenzoic acid (0.488 g, 0.00283 mol) was added portion wise over 20 minutes. The reaction was stirred at room temperature for one hour. The reaction was partitioned with DCM (200 mL) and saturated NaHCO$_3$ (200 mL). The organic was separated, washed with Brine and dried over Na$_2$SO$_4$. The solid was filtered and washed with DCM. The solvent was removed under vacuum to give 2-Methanesulfinyl-7-phenyl-pyrrolo[2,1-f][1,2,4]triazine a yellow solid. The solid was washed with hexane (610 mg, 92%). NMR $^1$H (DSMO-$d_6$)-9.32 (s, 1H), 8.27 (d, 2H, J=7.44 Hz), 7.71 (d, 2H, J=4.84 Hz), 7.56 (d, 2H, J=7.81 Hz), 7.45 (t, 1H, J=7.37 Hz), 7.34 (d, 1H, J=4.24H), 2.99 (s, 3H)

12c) (7-Phenyl-pyrrolo[2,1-f][1,2,4]triazin-2-yl)-pyridin-3-ylmethyl-amine: Into a 30 mL vial, 3-(Aminomethyl)-pyridine (0.0906 g, 0.000838 mol), 2-Methanesulfinyl-7-phenyl-pyrrolo[2,1-f][1,2,4]triazine (0.098 g, 0.00038 mol), and N-Methylpyrrolidinone (0.20 mL, 0.0021 mol) were added. The reaction was heated at 140° C. for 2 hours. The reaction was cooled to room temperature. Methanol was added. The precipitate was filtered and washed with methanol to afford (7-Phenyl-pyrrolo[2,1-f][1,2,4]triazin-2-yl)-pyridin-3-ylmethyl-amine as a yellow solid (52 mg, 45%). MP201-203° C. LCMS (E/I+) 302.15 (M+H). NMR $^1$H (DSMO-$d_6$)-8.84 (s, 1H), 8.62 (s, 1H), 8.43 (d, 1H, J=4.57 Hz), 7.97 (d, 2H, J=8.40 Hz), 7.79 (d, 1H, J=7.88 Hz), 7.75 (t, 1H, J=8.20 Hz), 7.25-7.45 (m, 4H), 7.08 (d, 1H, J=4.76 Hz), 6.83 (d, 1H, J=4.76 Hz), 4.46 (d, 2H, J=6.6.04 Hz).

Example 13

(7-Phenyl-pyrrolo[2,1-f][1,2,4]triazin-2-yl)-(3,4,5-trimethoxy-phenyl)amine

The titled compound was prepared in an analogous fashion to Example 12 replacing 3-(aminomethylpyridine with 3,4,5-trimethoxyaniline to give (7-Phenyl-pyrrolo[2,1-f][1,2,4]triazin-2-yl)-(3,4,5-trimethoxy-phenyl)amine as a yellow solid (31 mg, 30%). MP 155-157° C. LCMS (E/I+) 377.22 (M+H). NMR $^1$H (DSMO-$d_6$)-9.29 (s, 1H), 8.92 (s, 1H), 8.10 (d, 1H, J=7.40 Hz), 7.46 (t, 2H, J=7.64 Hz), 7.36 (t, 1H, J=6.45 Hz), 7.12 (d, 1H, J=4.65 Hz), 7.07 (s, 2H), 6.96 (d, 1H, J=4.72 Hz), 3.63 (s, 6H), 3.61 (s, 3H).

Example 14

Morpholin-4-yl-{4-[2-(4-morpholin-4-yl-phenylamino)-pyrrolo[2,1-f][1,2,4]triazin-7-yl]-phenyl}-methanone The titled compound was prepared in an analogous fashion to Example 1 replacing 3-chlorophenyl boronic acid with 4-(morpholino-4-carbonyl)phenyl boronic acid to give Morpholin-4-yl-{4-[2-(4-morpholin-4-yl-phenylamino)-pyrrolo[2,1-f][1,2,4]triazin-7-yl]-phenyl}-methanone as a yellow solid. MP 192-193° C. LCMS (E/I+) 485.13 (M+H). NMR $^1$H (DSMO-$d_6$)-9.28 (s, 1H), 8.96 (s, 1H), 8.29 (d, 1H, J=8.32 Hz), 7.63 (d, 2H, J=8.97 Hz), 7.61 (d, 2H, J=8.93 Hz), 7.56 (d, 2H, J=8.33 Hz), 7.23 (d, 1H, J=4.72 Hz), 6.90-7.00 (m, 3H), 3.75 (t, 4H, J=4.48 Hz), 3.36-3.72 (bm, 8H), 3.06 (t, 4H, J=4.64 Hz).

Example 15

{3-[2-(4-Morpholin-4-yl-phenylamino)-pyrrolo[2,1-f][1,2,4]triazin-7-yl]-phenyl}-pyrrolidin-1-yl-methanone The titled compound was prepared in an analogous fashion to Example 1 replacing 3-chlorophenyl boronic with 3-(pyrrolocarbonyl)phenyl boronic acid to give {3-[2-(4-Morpholin-4-yl-phenylamino)-pyrrolo[2,1-f][1,2,4]triazin-7-yl]-phenyl}-pyrrolidin-1-yl-methanone as a yellow solid (42 mg, 48%). MP218-220. LCMS 469.16 (M+H). NMR $^1$H (DSMO-$d_6$)-9.29 (s, 1H), 8.95 (s, 1H), 8.44 (s, 1H), 8.21 (d, 1H, J=8.04 Hz), 7.63 (d, 2H, J=8.93 Hz), 7.58 (t, 1H, J=7.94 Hz), 7.49 (d, 1H, J=7.61 Hz), 7.23 (d, 1H, J=4.72 Hz), 6.87-6.98 (m, 3H), 3.76 (t, 4H, J=4.40 Hz), 3.51 (t, 2H, J=6.80 Hz), 3.37 (t, 2H, J=6.61 Hz), 3.04 (t, 4H, J=4.48 Hz), 1.70-1.90 (m, 4H).

Example 16

[7-(2-Methoxy-pyridin-3-yl)-pyrrolo[2,1-f][1,2,4]triazin-2-yl]-(4-morpholin-4-yl-phenyl)-amine The titled compound was prepared in an analogous fashion to Example 1 replacing 3-chlorophenyl boronic with 2-methoxy-3-pyridineboronic acid to give [7-(2-Methoxy-pyridin- 3-yl)-pyrrolo[2,1-f][1,2,4]triazin-2-yl]-(4-morpholin-4-yl-phenyl)-amine as a yellow solid (30 mg, 40%). MP 239-240. LCMS 403.12 (M+H). NMR $^1$H (DSMO-d$_6$)-9.22 (s, 1H), 8.95 (s, 1H), 8.41 (d, 1H, J=7.48 Hz), 8.25 (dd, 1H, J=1.64, 4.92 Hz), 7.56 (d, 2H, J=8.93 Hz), 7.21 (dd, 1H, J=4.92, 7.32 Hz), 7.05 (d, 1H, J=4.68 Hz), 6.91 (d, 1H, J=4.68 Hz), 6.84 (d, 2H, J=8.93), 3.92 (s, 3H), 3.73 (t, 4H, J=4.48 Hz), 3.02 (t, 4H, J=4.52 Hz).

Example 17

[7-(5-Chloro-2-methoxy-phenyl)-pyrrolo[2,1-f][1,2,4]triazin-2-yl]-[4-(4-methyl-piperazin-1-yl)-phenyl]-amine The titled compound was prepared in an analogous fashion to Example 7 replacing phenyl boronic with 5-Chloro-3-methoxyphenylboronic acid to give [7-(5-Chloro-2-methoxy-phenyl)-pyrrolo[2,1-f][1,2,4]triazin-2-yl]-[4-(4-methyl-piperazin-1-yl)-phenyl]-amine (44 mg, 49%). MP 193-195° C. LCMS (E/I+) 449.11 (M+H). NMR $^1$H (DSMO-d$_6$)-9.22 (s, 1H), 8.93 (s, 1H), 8.06 (d, 1H, J=2.57 Hz), 7.69 (s, 1H), 7.57 (d, 2H, J=8.88 Hz), 7.47 (dd, 1H, JJ=6.42, 8.92 Hz), 7.23 (d, 1H, J=8.96 Hz), 7.02 (d, 1H, J=4.64 Hz), 6.89 (d, 1H, J=4.60 Hz), 6.85 (d, 2H, J=8.96 Hz), 3.82 (s, 3H), 3.02 (t, 4H, J=4.56 Hz), 2.44 (t, 4H, J=4.64 Hz), 2.21 (s, 3H).

Example 18

[4-(4-Methyl-piperazin-1-yl)-phenyl]-[7-(1-methyl-1H-pyrazol-4-yl)-pyrrolo[2,1-f][1,2,4]triazin-2-yl]-amine The titled compound was prepared in an analogous fashion to Example 7 replacing phenyl boronic with 1-Methyl-4-(4,4,5,5-tetramethyl-[1,3,2]dioxaborolan-2-yl)-1H-pyrazole to give [4-(4-Methyl-piperazin-1-yl)-phenyl]-[7-(1-methyl-1H-pyrazol-4-yl)-pyrrolo[2,1-f][1,2,4]triazin-2-yl]-amine as a yellow solid (30 mg, 38%). MP 205-208° C. LCMS (E/I+) 389.13 (M+H). NMR $^1$H (DSMO-d$_6$)-9.07 (s, 1H), 8.82 (s, 1H), 8.39 (s, 1H), 8.14 (s, 1H), 7.56 (d, 2H, J=8.85 Hz), 7.01 (d, 1H, J=4.68 Hz), 6.97 (d, 2H, J=8.92 Hz), 6.85 (d, 1H, J=4.64 Hz), 3.92 (s, 3H), 3.10 (t, 4H, J=4.66 Hz), 2.47 (t, 4H, J=4.64 Hz), 2.23 (s, 3H).

Example 19

(4-{2-[4-(4-Methyl-piperazin-1-yl)-phenylamino]-pyrrolo[2,1-f][1,2,4]triazin-7-yl}-phenyl)-morpholin-4-yl-methanone The titled compound was prepared in an analogous fashion to Example 7 replacing phenyl boronic with 4-(morpholino-4-carbonyl)phenyl boronic acid to give (4-{2-[4-(4-Methyl-piperazin-1-yl)-phenylamino]-pyrrolo[2,1-f][1,2,4]triazin-7-yl}-phenyl)-morpholin-4-yl-methanone as a yellow solid (38 mg, 38%). MP 187-188° C. LCMS (E/I+) 498.32 (M+H). NMR $^1$H (DSMO-d$_6$)-9.26 (s, 1H), 8.96 (s, 1H), 8.28 (d, 2H, J=8.24 Hz), 7.60 (d, 2H, J=8.88 Hz), 7.56 (d, 2H, J=8.21 Hz), 7.22 (d, 1H, J=4.80 Hz), 6.89-6.99 (m, 3H), 3.35-3.80 (bm, 8H), 3.00-3.15 (m, 4H), 2.40-2.60 (bm, 4H), 2.25 (s, 3H)

Example 20

[7-(2-Methoxy-phenyl)-pyrrolo[2,1-f][1,2,4]triazin-2-yl]-[4-(4-methyl-piperazin-1-1)-phenyl]-amine The titled compound was prepared in an analogous fashion to Example 7 replacing 3-phenyl boronic with 2-methoxyphenyl boronic acid to give [7-(2-Methoxy-phenyl)-pyrrolo[2,1-f][1,2,4]triazin-2-yl]-[4-(4-methyl-piperazin-1-1)-phenyl]-amine as a yellow solid. MP 199-200° C. LCMS (E/I+) 415.21 (M+H). NMR $^1$H (DSMO-d$_6$)-9.12 (s, 1H), 8.89 (s, 1H), 7.81 (d, 1H, J=7.77 Hz), 7.56 (d, 2H, J=8.93 Hz), 7.45 (t, 1H, J=7.44 Hz), 7.21 (d, 1H, J=8.28 Hz), 7.12 (t, 1H, J=7.53 Hz), 6.91 (t, 1H, J=4.56 Hz), 6.88 (d, 1H, J=4.61 Hz), 6.79 (d, 2H, J=8.92 Hz), 3.79 (s, 3H), 2.97-3.10 (bm, 4H), 2.42-2.53 (bm, 4H),), 2.22 (s, 3H).

Example 21

(3-{2-[4-(4-Methyl-piperazin-1-yl)-phenylamino]-pyrrolo[2,1-f][1,2,4]triazin-7-yl}-phenyl)-pyrrolidin-1-yl-methanone The titled compound was prepared in an analogous fashion to Example 7 replacing 3-phenyl boronic with 3-(pyrrolocarbonyl)phenyl boronic acid to give (3-{2-[4-(4-Methyl-piperazin-1-yl)-phenylamino]-pyrrolo[2,1-f][1,2,4]triazin-7-yl}-phenyl)-pyrrolidin-1-yl-methanone as a yellow solid (21 mg, 22%). MP 219-222° C. LCMS (E/I+) 482.28 (M+H). NMR $^1$H (DSMO-d$_6$)-9.26 (s, 1H), 8.95 (s, 1H), 8.47 (s, 1H), 8.19 (d, 1H, J=8.13 Hz), 7.53-7.65 (m, 3H), 7.49 (d, 1H, J=7.57 Hz), 7.23 (d, 1H, J=4.76 Hz), 6.93 (d, 1H, J=4.77 Hz), 6.89 (d, 2H, J=8.96 Hz), 3.51 (t, 2H, J=6.68 Hz), 3.36 (t, 2H, J=6.37 Hz), 3.06 (t, 4H, J=4.49 Hz), 2.46 (t, 4H, J=4.88 Hz), 2.23 (s, 3H), 1.72-1.90 (m, 4H).

Example 22

[7-(2-Methoxy-pyridin-3-yl)-pyrrolo[2,1-f][1,2,4]triazin-2-yl]-[4-(4-methyl-piperazin-1-yl)-phenyl]-amine The titled compound was prepared in an analogous fashion to Example 7 replacing 3-phenyl boronic with 2-methoxy-3-pyridineboronic acid to give [7-(2-Methoxy-pyridin-3-yl)-pyrrolo[2,1-f][1,2,4]triazin-2-yl]-[4-(4-methyl-piperazin-1-yl)-phenyl]-amine as a yellow solid (35 mg, 42%). MP 206-208° C. LCMS (E/I+) 416.19 (M+H). NMR $^1$H (DSMO-d$_6$)-9.20 (s, 1H), 8.94 (s, 1H), 8.41 (d, 1H, J=7.44 Hz), 8.25 (d, 1H, J=3.20 Hz), 7.53 (d, 2H, J=8.92 Hz), 7.22 (dd, 1H, JJ=5.00, 7.44 Hz), 7.05 (d, 1H, J=4.68 Hz), 6.90 (d, 1H, J=4.64 Hz), 6.82 (d, 2H, J=8.96 Hz), 3.92 (s, 3H), 3.00-3.10 (bm, 4H), 2.40-2.50 (bm, 4H), ), 2.22 (s, 3H).

Example 23

N-tert-Butyl-3-{2-[4-(4-methyl-piperazin-1-yl)-phenylamino]-pyrrolo[2,1-f][1,2,4]triazin-7-yl}-benzenesulfonamide The titled compound was prepared in an analogous fashion to Example 7 replacing 3-phenyl boronic with 3-t-Butylsulfamoylphenylboronic acid to give N-tert-Butyl-3-{2-[4-(4-methyl-piperazin-1-yl)-phenylamino]-pyrrolo[2,1-f][1,2,4]triazin-7-yl}-benzenesulfonamide as a yellow solid (58 mg, 55%). MP 240-241° C. LCMS (E/I+) 520.25 (M+H). 9.28 (s, 1H), 8.96 (s, 1H), 8.53 (s, 1H), 8.38 (d, 1H, J=8.01 Hz), 7.83 (d, 1H, J=7.60 Hz), 7.73 (t, 1H, J=7.84 Hz), 7.56-7.68 (m, 3H), 7.17 (d, 1H, J=4.72 Hz), 6.90-7.05 (m, 3H), 3.00-3.13 (bm, 4H), 2.45-2.56 (bm, 4H), 2.23 (s, 3H), 1.16 (s, 9H).

Example 24

N(2)-[4-(4-Methyl-piperazin-1-yl)-phenyl]-N(7)-phenyl-pyrrolo[2,1-f][1,2,4]triazine-2,7-diamine Into a Microwave vial, (7-Bromo-pyrrolo[2,1-f][1,2,4]triazin-2-yl)-[4-(4-methyl-piperazin-1-yl)-phenyl]-amine (0.12 g, 0.30 mmol), Aniline (0.0470 g, 0.504 mmol), 1,1'-Bis(diphenylphosphino)ferrocene (0.0050 g, 0.0091 mmol), Tris(dibenzylideneacetone)dipalladium(0) (0.0051 g, 0.0055 mmol), Sodium tert-butoxide (0.0349 g, 0.363 mmol) were added and purged under an atmosphere of Nitrogen for 10 minutes. Toluene (1.00 mL, 9.39 mmol) was then added and stirred at room temperature for one minute. The reaction was microwaved on 300 watts, 150° C. for 20 minutes. HPLC suggested 50% conversion. DCM and methanol was added and purified via flash column chromatography with DCM and methanol as eluant (10% methanol). The solvent was removed under vacuum to afford a semi-solid. The semi-solid was purified via HPLC with water and ACN as eluant (5 to 45% ACN). The collected fractions afforded N(2)-[4-(4-Methyl-piperazin-1-yl)-phenyl]-N(7)-phenyl-pyrrolo[2,1-f][1,2,4]triazine-2,7-diamine as a yellow solid. MP 152-157° C. LCMS (E/I+) 400.18 (M+H). NMR $^1$H (DSMO-$d_6$)-8.99 (s, 1H), 8.68 (s, 1H), 8.17 (s, 1H), 7.52 (d, 2H, J=8.96 Hz), 7.22 (t, 1H, J=7.92 Hz), 6.78-6.85 (m, 2H), 6.73 (d, 1H, J=9.00 Hz), 6.56 (d, 1H, J=4.65 Hz), 3.00 (t, 1H, J=4.25 Hz), 2.44 (bs, 4H), 2.23 (s, 3H), 1.16 (s, 9H).

Example 25

[7-(2-Chloro-phenyl)-pyrrolo[2,1-f][1,2,4]triazin-2-yl]-[4-(4-methyl-piperazin-1-yl)-phenyl]-amine The titled compound was prepared in an analogous fashion to Example 7 replacing phenyl boronic with 2-Chlorophenylboronic acid to give [7-(2-Chloro-phenyl)-pyrrolo[2,1-f][1,2,4]triazin-2-yl]-[4-(4-methyl-piperazin-1-yl)-phenyl]-amine as a yellow solid (35 mg, 41%). MP 176-178° C. LCMS (E/I+) 419.19 (M+H). NMR $^1$H (DSMO-$d_6$)-9.21 (s, 1H), 8.96 (s, 1H), 7.75-7.83 (m, 1H), 7.64-7.72 (m, 1H), 7.44-7.58 (m, 4H), 6.87-6.95 (m, 2H), 6.75 (d, 2H, J=8.97 Hz), 3.01 (bm, 4H), 2.44 (bm, 4H), 2.22 (s, 3H).

Example 26

[7-(3-Chloro-phenyl)-pyrrolo[2,1-f][1,2,4]triazin-2-yl]-[4-(4-methyl-piperazin-1-yl)-phenyl]-amine The titled compound was prepared in an analogous fashion to Example 7 replacing phenyl boronic with 3-Chlorophenylboronic acid to give [7-(3-Chloro-phenyl)-pyrrolo[2,1-f][1,2,4]triazin-2-yl]-[4-(4-methyl-piperazin-1-yl)-phenyl]-amine as a yellow solid (41 mg, 48%). MP 187-190° C. LCMS (E/I+) 419.19 (M+H). NMR $^1$H (DSMO-$d_6$)-9.29 (s, 1H), 8.96 (s, 1H), 8.47 (s, 1H), 8.04 (d, 1H, J=7.88 Hz), 7.61 (d, 2H, J=8.84 Hz), 7.53 (t, 1H, J=7.80 Hz), 7.42 (d, 1H, J=8.13 Hz), 7.25 (d, 1H, J=4.81 Hz), 6.90-7.00 (m, 3H), 3.08 (bm, 4H), 2.45-2.56 (bm, 4H), 2.24 (s, 3H).

Example 27

[4-(4-Methyl-piperazin-1-yl)-phenyl]-(7-pyridin-3-yl-pyrrolo[2,1-f][1,2,4]triazin-2-yl)-amine The titled compound was prepared in an analogous fashion to Example 7 replacing phenyl boronic with 3-pyridineboronic acid to give a yellow solid 38 mg, 49%). MP 218-219° C. LCMS (E/I+) 386.22 (M+H). NMR $^1$H (DSMO-$d_6$)-9.32 (s, 1H), 9.28 (s, 1H), 8.93 (s, 1H), 8.69 (d, 1H, J=8.17 Hz), 8.56 (dd, 1H, JJ=3.33, 4.65 Hz), 7.54-7.65 (m, 3H), 7.53 (t, 1H, J=7.80 Hz), 7.27 (d, 1H, J=4.72 Hz), 6.95 (d, 1H, J=4.72 Hz), 6.91 (d, 2H, J=9.00 Hz), 3.08 (t, 4H, J=4.60 Hz), 2.45-2.56 (bm, 4H), 2.23 (s, 3H).

Example 28

(2-Morpholin-4-yl-ethyl)-(7-phenyl-pyrrolo[2,1-f][1,2,4]triazin-2-yl)-amine

The titled compound was prepared in an analogous fashion to Example 12 replacing 3-(Aminomethyl)pyridine with N-(2-Aminoethyl)morpholine to give (2-Morpholin-4-yl-ethyl)-(7-phenyl-pyrrolo[2,1-f][1,2,4]triazin-2-yl)-amine as a yellow solid (35 mg, 25%). MP 101-111° C. LCMS (E/I+) 324.20 (M+H). NMR $^1$H (DSMO-$d_6$)-8.81 (s, 1H), 8.25 (d, 2H, J=7.59 Hz), 7.45 (t, 2H, J=7.60 Hz), 7.33 (t, 1H, J=7.28 Hz), 7.12 (d, 1H, J=4.77 Hz), 6.84 (d, 1H, J=4.76 Hz), 6.79 (t, 1H, J=5.80 Hz), 3.58 (t, 4H, J=4.52 Hz), 3.39 (q, 2H, J=6.60 Hz), 2.57 (t, 2H, J=7.08 Hz), 2.44 (bs, 4H).

Example 29

(3-Morpholin-4-yl-propyl)-(7-phenyl-pyrrolo[2,1-f][1,2,4]triazin-2-yl)-amine

The titled compound was prepared in an analogous fashion to Example 12 replacing 3-(Aminomethyl)pyridine with 4-Morpholinepropanamine to give (3-Morpholin-4-yl-propyl)-(7-phenyl-pyrrolo[2,1-f][1,2,4]triazin-2-yl)-amine as an off white solid (20 mg, 14%). MP 92-94° C. LCMS (E/I+) 338.19 (M+H). NMR $^1$H (DSMO-$d_6$)-8.80 (s, 1H), 8.25 (d, 2H, J=7.40 Hz), 7.48 (t, 2H, J=7.64 Hz), 7.33 (t, 1H, J=7.32 Hz), 7.11 (d, 1H, J=4.76 Hz), 6.98 (t, 1H, J=5.12 Hz), 6.83 (d, 1H, J=4.72 Hz), 3.55 (t, 4H, J=4.67 Hz), 3.24-3.37 (m, 2H), 2.30-2.53 (m, 6H), 1.78 (m, 2H).

Example 30

[3-(2-Methoxy-ethyl)-2,3,4,5-tetrahydro-1H-benzo[d]azepin-7-yl]-[7-(2-methoxy-phenyl)-pyrrolo[2,1-f][1,2,4]triazin-2-yl]-amine The titled compound was prepared in an analogous fashion to Example 9 replacing phenylboronic acid with 3-methoxyphenyl boronic acid to give [3-(2-Methoxy-ethyl)-2,3,4,5-tetrahydro-1H-benzo[d]azepin-7-yl]-[7-(2-methoxy-phenyl)-pyrrolo[2,1-f][1,2,4]triazin-2-yl]-amine as a yellow solid (18 mg, 18%). MP216-219° C. LCMS (E/I+) 444.20 (M+H). NMR $^1$H (DSMO-$d_6$)-9.26 (s, 1H), 8.93 (s, 1H), 7.79 (d, 1H, J=7.52 Hz), 7.56 (s, 1H), 7.46 (t, 1H, J=7.44 Hz), 7.31 (d, 1H, J=7.05 Hz), 7.21 (d, 1H, J=8.34 Hz), 7.09 (t, 2H, J=7.32 Hz), 6.85-6.97 (m, 3H), 3.25 (s, 3H), 2.50-2.80 (bm, 10H).

Example 31

2-{2-[3-(2-Methoxy-ethyl)-2,3,4,5-tetrahydro-1H-benzo[d]azepin-7-ylamino]-pyrrolo[2,1-f][1,2,4]triazin-7-yl}-N,N-dimethyl-benzenesulfonamide The above compound was prepared in an analogous fashion to Example 9 replacing phenylboronic acid with N,N-dimethylsulfonamide-2-benzeneboronic acid 2-{2-[3-(2-

Methoxy-ethyl)-2,3,4,5-tetrahydro-1H-benzo[d]azepin-7-ylamino]-pyrrolo[2,1-f][1,2,4]triazin-7-yl}-N,N-dimethyl-benzenesulfonamide as a yellow solid (22 mg, 18%). LCMS (E/I+) 521.20 (M+H). NMR $^1$H (DSMO-d$_6$)-9.28 (s, 1H), 8.95 (s, 1H), 8.06 (d, 1H, J=7.53 Hz), 7.75-7.85 (m, 2H), 7.62 (d, 1H, J=8.57 Hz), 7.41 (s, 1H), 7.06 (d, 1H, J=8.25 Hz), 6.91 (d, 1H, J=4.60 Hz), 6.86 (d, 1H, J=4.56 Hz), 6.81 (d, 1H, J=8.09 Hz), 3.44 (t, 2H, J=5.64 Hz), 3.25 (s, 3H), 2.40-2.80 (bm, 10H), 2.32 (s, 3H).

Example 32

[3-(2-Methoxy-ethyl)-2,3,4,5-tetrahydro-1H-benzo[d]azepin-7-yl]-{7-[2-(pyrrolidine-1-sulfonyl)-phenyl]-pyrrolo[2,1-f][1,2,4]triazin-2-yl}-amine The titled compound was prepared in an analogous fashion to Example 9 replacing phenylboronic acid with 2-(Pyrrolidinylsulfonyl)phenylboronic acid to give [3-(2-Methoxy-ethyl)-2,3,4,5-tetrahydro-1H-benzo[d]azepin-7-yl]-{7-[2-(pyrrolidine-1-sulfonyl)-phenyl]-pyrrolo[2,1-f][1,2,4]triazin-2-yl}-amine as a yellow solid (25 mg, 20%). LCMS (E/I+) 547.24 (M+H). NMR $^1$H (DSMO-d$_6$)-9.33 (s, 1H), 8.98 (s, 1H), 8.11 (d, 1H, J=6.80 Hz), 7.70-7.87 (m, 2H), 7.64 (d, 1H, J=6.24 Hz), 7.42 (s, 1H), 7.08 (bs, 1H), 6.80-6.97 (m, 3H), 3.52 (bs, 2H), 3.28 (s, 3H), 2.00-2.85 (bm, 10H), 2.40-2.55 (bm, 4H), 1.40 (bm, 4H).

Example 33

[2-Methoxy-4-(4-methyl-piperazin-1-yl)-phenyl]-[7-(2-methoxy-phenyl)-pyrrolo[2,1-f][1,2,4]triazin-2-yl]-amine 33a) 2-Methoxy-4-(4-methyl-piperazin-1-yl)-phenylamine: In, 200 mL round bottom flask, 4-Fluoro-2-methoxy-1-nitro-benzene (2.00 g, 0.0117 mol) was treated with piperazine, 1-methyl-(2.59 mL, 0.0234 mol), Dimethyl sulfoxide (20 mL, 0.3 mol) and Potassium carbonate (4.84 g, 0.0351 mol) heated to 90° C. for 8 hours. The reaction was cooled to room temperature and added into ice water. The solid was filtered and dried under vacuum overnight. The solid was treated with Ethanol (50 mL, 0.8 mol) and 10% Pd/C (10:90, Palladium:carbon black, 500 mg, 0.0005 mol) in a parr bottle. The reaction was placed into par shaker, evacuated and charged with hydrogen at 50 pSi The reaction mixture was shaken for 3 hours. The solid was filtered and stipped tove a gummy solid. The solid was partitioned with hexane/Et$_2$O (9/1). The resulting solid was decanted and dried under vacuum to give 2-Methoxy-4-(4-methyl-piperazin-1-yl)-phenylamine as a white solid (1.35 g, 53%). NMR $^1$H (DSMO-d$_6$)-6.50 (d, 1H, J=8.37 Hz), 6.48 (d, 1H, J=1.96 Hz), 6.27 (dd, 1H, JJ=2.20, 6.92 Hz), 4.18 (s, 3H), 3.73 (s, 3H), 2.93 (t, 4H, J=4.41 Hz), 2.42 (t, 4H, J=4.56 Hz), 2.20 (s, 3H)

33b) Into a 30 mL vial, 2-Methoxy-4-(4-methyl-piperazin-1-yl)-phenylamine (1.08 g, 0.00490 mol), 7-Bromo-2-methanesulfinyl-pyrrolo[2,1-f][1,2,4]triazine (0.580 g, 0.00223 mol) and N-Methylpyrrolidinone (3.50 mL, 0.0363 mol) were added. The reaction mixture was heated at 145° C. for 2.5 hours. The solvent was removed under vacuum. The desired product was isolated via ISCO column chromatography with DCM and MeOH as eluant (3 to 10% methanol). The collected fractions afforded (7-Bromo-pyrrolo[2,1-f][1,2,4]triazin-2-yl)-[2-methoxy-4-(4-methyl-piperazin-1-yl)-phenyl]-amine as a yellow solid (0.58 g, 62%). NMR $^1$H (DSMO-d$_6$)-8.83 (s, 1H), 8.03 (d, 1H, J=8.74 Hz), 7.75 (s, 1H), 6.91 (d, 1H, J=4.68 Hz), 6.66 (d, 1H, J=2.24 Hz), 6.51 (dd, 1H, JJ=2.23, 6.44 Hz), 3.85 (s, 3H), 3.13 (t, 4H, J=4.54 Hz), 2.46 (t, 4H, J=4.84 Hz), 2.22 (s, 3H)

33c) Into a 30 mL vial, Palladium Acetate (0.010 g, 0.000046 mol) and Triphenylphosphine (0.030 g, 0.00011 mol) were added and purged under an atmosphere of Nitrogen for 5 minutes 1,4-Dioxane (1.00 mL, 0.0128 mol) was added and stirred for 10 minutes. (7-Bromo-pyrrolo[2,1-f][1,2,4]triazin-2-yl)-[2-methoxy-4-(4-methyl-piperazin-1-yl)-phenyl]-amine (0.0952 g, 0.000228 mol), 2-methoxybenzeneboronic acid (0.0694 g, 0.000456 mol), N,N-Dimethylformamide (2.20 mL, 0.0284 mol) and 1.50 M of Sodium carbonate in Water (1.00 mL, 0.00150 mol) were added, respectively. The reaction mixture was heated at 80° C. overnight. The solvent was removed under vacuum. The solid was washed with DCM. The organic was removed under vacuum. The reaction was purified via ISCO column chromatography with DCM and methanol as eluant (0 to 10% methanol). The collected fraction afforded a solid. The solid was washed with 10% Et$_2$O/hexane to give [2-Methoxy-4-(4-methyl-piperazin-1-yl)-phenyl]-[7-(2-methoxy-phenyl)-pyrrolo[2,1-f][1,2,4]triazin-2-yl]-amine a yellow solid (38 mg, 37%). LCMS (E/I+) 445.19 (M+H). NMR $^1$H (DSMO-d$_6$)-8.88 (s, 1H), 7.83 (t, 2H, J=8.76 Hz), 7.48 (s, 1H), 7.43 (t, 1H, J=7.16 Hz), 7.19 (d, 1H, J=8.36 Hz), 7.08 (t, 1H, J=7.52 Hz), 6.94 (d, 1H, J=4.68 Hz), 6.90 (d, 1H, J=4.60 Hz), 6.63 (s, 1H), 6.35 (d, 1H, J=9.04 Hz), 3.84 (s, 3H), 3.78 (s, 3H), 3.05-3.16 (bm, 4H), 2.46 (bs, 4H), 2.23 (s, 3H).

Example 34

[2-Methoxy-4-(4-methyl-piperazin-1-yl)-phenyl]-[7-(2-methoxy-pyridin-3-yl)-pyrrolo[2,1-f][1,2,4]triazin-2-yl]-amine The titled compound was prepared in an analogous fashion to Example 33 replacing 3-methoxyphenyl boronic acid with 2-methoxy-3-pyridine boronic acid to give [2-Methoxy-4-(4-methyl-piperazin-1-yl)-phenyl]-[7-(2-methoxy-pyridin-3-yl)-pyrrolo[2,1-f][1,2,4]triazin-2-yl]-amine as a yellow solid (40 mg, 39%). LCMS (E/I+) 446.18 (M+H). NMR $^1$H (DSMO-d$_6$)-8.92 (s, 1H), 8.43 (dd, 1H, JJ=1.72, 5.69 Hz), 8.22 (dd, 1H, JJ=1.84, 3.04 Hz), 7.72 (d, 1H, J=8.68 Hz), 7.11-7.18 (m, 1H), 7.08 (td 1H, J=4.72 Hz), 6.91 (d, 1H, J=4.64 Hz), 6.65 (s, 1H), 6.35-6.47 (m, 1H), 3.91 (s, 3H), 3.83 (s, 3H), 3.11 (t, 4H, J=4.16 Hz), 2.40-2.56 (bm, 4H), 2.23 (s, 3H).

Example 35

2-{2-[2-Methoxy-4-(4-methyl-piperazin-1-yl)-phenylamino]-pyrrolo[2,1-f][1,2,4]triazin-7-yl}-N,N-dimethyl-benzenesulfonamide The titled compound was prepared in an analogous fashion to Example 33 replacing 3-methoxyphenyl boronic acid with N,N-dimethylsulfonamide-2-benzeneboronic acid to give 2-{2-[2-Methoxy-4-(4-methyl-piperazin-1-yl)-phenylamino]-pyrrolo[2,1-f][1,2,4]triazin-7-yl}-N,N-dimethyl-benzenesulfonamide as a yellow solid. MP 216-219° C. LCMS (E/I+) 522.16 (M+H). NMR $^1$H (DSMO-d$_6$)-8.91 (s, 1H), 8.02 (d, 1H, J=8.36 Hz), 7.81 (t, 1H, J=7.09 Hz), 7.75 (t, 1H, J=6.81 Hz), 7.64 (d, 1H, J=7.80 Hz), 7.54 (d, 1H, J=8.80 Hz), 7.46 (s, 1H), 6.91 (d, 1H, J=3.32 Hz), 6.86 (d, 1H, J=4.48 Hz), 6.13 (d, 1H, J=9.17 Hz), 3.81 (s, 3H), 3.03 (t, 4H, J=4.80 Hz), 2.43 (t, 4H, J=4.65 Hz), 2.35 (s, 6H), 2.21 (s, 3H).

Example 36

2-[2-(4-Morpholin-4-yl-phenylamino)-pyrrolo[2,1-f][1,2,4]triazin-7-yl]-benzamide Into a 30 mL vial, Palladium Acetate (18.5 mg, 0.0824 mmol) and Triphenylphosphine (54.0 mg, 0.206 mmol) were added and purged under an atmosphere of Nitrogen for 5 minutes. 1,4-Dioxane (3.8 mL, 49 mmol) was added and stirred for 10 minutes. and 2-Cyanophenyl boronic acid (0.0989 g, 0.673 mmol) in N,N-Dimethylformamide (3.8 mL, 5.0E1 mmol) and 1.50 M of Sodium carbonate in Water (0.824 mL, 1.24 mmol) were added, respectively. The reaction mixture was heated at 100° C. for 30 minutes. The solvent was removed under vacuum. The solid was washed with DCM. The organic was removed under vacuum. The reaction was purified via ISCO column chromatography with DCM and methanol as eluant (0 to 10% methanol). The collected fraction afforded a solid. The solid was washed with methanol to give 2-[2-(4-Morpholin-4-yl-phenylamino)-pyrrolo[2,1-f][1,2,4]triazin-7-yl]-benzamide as a yellow solid (78 mg, 56%). LCMS (E/I+) 415.13. NMR $^1$H (CDCl$_3$-d)-8.37 (s, 1H), 7.77 (d, 1H, J=7.52 Hz), 7.67 (d, 1H, J=7.68 Hz), 7.60 (t, 1H, J=6.68 Hz), 7.50-7.58 (m, 2H) 7.21 (d, 2H, J=8.32 Hz), 6.91 (d, 1H, J=6.40 Hz), 6.80 (d, 1H, J=4.60 Hz) 6.72 (d, 2H, J=8.52 Hz) 6.59 (bs, 1H), 5.50 (bs, 1H), 3.88 (t, 4H, J=5.13 Hz), 3.07 (t, 4H, J=4.46 Hz).

Example 37

5-[2-(4-Morpholin-4-yl-phenylamino)-pyrrolo[2,1-f][1,2,4]triazin-7-yl]-pyridine-2-carbonitrile The titled compound was prepared in an analogous fashion to Example 1 replacing 3-Chlorophenylboronic acid with 4-Cyano-3-pyridine boronic acid to give 5-[2-(4-Morpholin-4-yl-phenylamino)-pyrrolo[2,1-f][1,2,4]triazin-7-yl]-pyridine-2-carbonitrile MP 280-283° C. LCMS (E/I+) 398.14 (M+H). NMR $^1$H (DSMO-d$_6$)-9.50 (d, 1H, J=1.32 7.56 Hz), 9.41 (s, 1H), 9.05 (s, 1H), 8.95 (dd, 1H, JJ=2.04, 6.28 Hz), 8.20 (d, 1H, J=8.24 Hz), 7.56 (d, 1H, J=8.89 Hz), 7.48 (d, 1H, J=4.88 Hz), 6.95-7.07 (m, 3H), 3.76 (t, 4H, J=4.40 Hz), 3.09 (t, 4H, J=4.52 Hz).

Example 38

[7-(4-Methanesulfonyl-phenyl)-pyrrolo[2,1-f][1,2,4]triazin-2-yl]-(4-morpholin-4-yl-phenyl)-amine The titled compound was prepared in an analogous fashion to Example 1 replacing 3-Chlorophenylboronic acid with (4-Methylsulfonylphenyl)boronic acid to give [7-(4-Methanesulfonyl-phenyl)-pyrrolo[2,1-f][1,2,4]triazin-2-yl]-(4-morpholin-4-yl-phenyl)-amine as a yellow solid (48 mg, 32%). MP 235-237° C. LCMS (E/I+) 373.18 (M+H). NMR $^1$H (DSMO-d$_6$)-9.34 (s, 1H), 9.05 (s, 1H), 8.49 (dd, 1H, J=8.57 Hz), 8.02 (d, 2H, J=8.60 Hz), 7.60 (d, 2H, J=8.96 Hz), 7.33 (d, 1H, J=4.80 Hz), 6.95-7.03 (m, 3H), 3.76 (t, 4H, J=4.44 Hz), 3.07 (t, 4H, J=4.72 Hz).

Example 39

3-[2-(4-Morpholin-4-yl-phenylamino)-pyrrolo[2,1-f][1,2,4]triazin-7-yl]-benzonitrile The titled compound was prepared in an analogous fashion to Example 1 replacing 3-Chlorophenylboronic acid with 3-Cyanophenylboronic acid to give 3-[2-(4-Morpholin-4-yl-phenylamino)-pyrrolo[2,1-f][1,2,4]triazin-7-yl]-benzonitrile as a yellow solid (28 mg, 21%). MP 244-246° C. LCMS (E/I+) 397.14 (M+H). NMR $^1$H (DSMO-d$_6$)-9.34 (s, 1H), 9.05 (s, 1H), 8.86 (s, 1H), 8.39 (d, 1H, J=7.92 Hz), 7.82 (d, 1H, J=7.73 Hz), 7.71 (d, 1H, J=8.00 Hz), 7.62 (d, 1H, J=8.93 Hz), 7.32 (d, 1H, J=4.80 Hz), 7.00 (d, 1H, J=9.01 Hz), 6.95 (d, 1H, J=4.76 Hz), 3.74 (t, 4H, J=4.61 Hz), 3.06 (t, 4H, J=4.72 Hz).

Example 40

[5-(2-Chloro-phenyl)-pyrrolo[2,1-f][1,2,4]triazin-2-yl]-[4-(4-methyl-piperazin-1-yl)-phenyl]-amine 40a) 5-Bromo-2-methanesulfinyl-pyrrolo[2,1-f][1,2,4]triazine: Into a Round bottom flask, 5-Bromo-2-methylsulfanyl-pyrrolo[2,1-f][1,2,4]triazine (0.800 g, 0.00328 mol) and Methylene chloride (9 mL, 0.1 mol) were added. m-Chloroperbenzoic acid (0.622 g, 0.00360 mol) was added portion wise over 20 minutes. The reaction was stirred at room temperature for one hour. The reaction was partitioned with DCM (200 mL) and saturated NaHCO$_3$ (200 mL). The organic was separated, washed with Brine and dried over Na$_2$SO$_4$.

The solid was filtered and washed with DCM. The solvent was removed under vacuum to give a yellow solid. The solid was washed with hexane to give 5-Bromo-2-methanesulfinyl-pyrrolo[2,1-f][1,2,4]triazine as a yellow solid (750 mg, 88%). NMR $^1$H (DSMO-d$_6$)-9.23 (s, 1H), 8.28 (d, 1H, J=2.40 Hz), 7.32 (d, 1H, J=2.74 Hz), 3.00 (s, 3H).

40b) The titled compound was prepared in an analogous fashion to Example 25 replacing 7-Bromo-2-methane sulfinyl-pyrrolo[2,1-f][1,2,4]triazine with 5-Bromo-2-methanesulfinyl-pyrrolo[2,1-f][1,2,4]triazine to give [5-(2-Chlorophenyl)-pyrrolo[2,1-f][1,2,4]triazin-2-yl]-[4-(4-methyl-piperazin-1-yl)-phenyl]-amine (45 mg, 32%). MP 165-167° C. LCMS (E/I+) 419.15 (M+H). NMR $^1$H (DSMO-d$_6$)-9.26 (s, 1H), 8.79 (s, 1H), 7.84 (d, 1H, J=2.24 Hz), 7.54-7.70 (m, 4H), 7.35-7.50 (m, 2H), 6.92 (d, 2H, J=8.96 Hz), 6.89 (d, 1H, J=2.54 Hz), 3.07 (t, 4H, J=4.53 Hz), 2.45 (t, 4H, J=4.60 Hz), 2.23 (s, 3H).

Example 41

[4-(4-Methyl-piperazin-1-yl)-phenyl]-(5-phenyl-pyrrolo[2,1-f][1,2,4]triazin-2-yl)-amine The titled compound was prepared in an analogous fashion to Example 1 replacing 7-Bromo-2-methanesulfinyl-pyrrolo[2,1-f][1,2,4]triazine with 5-Bromo-2-methanesulfinyl-pyrrolo[2,1-f][1,2,4]triazine to give [4-(4-Methyl-piperazin-1-yl)-phenyl]-(5-phenyl-pyrrolo[2,1-f][1,2,4]triazin-2-yl)-amine as a yellow solid (42 mg, 32%). LCMS (E/I+) 385.19 (M+H). NMR $^1$H (DSMO-d$_6$)-9.24 (s, 1H), 9.11 (s, 1H), 7.80 (d, 1H, J=2.36 Hz), 7.70 (d, 2H, J=7.44 Hz), 7.61 (d, 2H, J=8.73 Hz), 7.45 (t, 2H, J=7.70 Hz), 7.31 (t, 1H, J=7.16 Hz), 6.99 (d, 1H, J=2.44 Hz), 6.91 (d, 2H, J=9.00 Hz), 3.07 (t, 4H, J=4.45 Hz), 2.45 (t, 4H, J=4.60 Hz), 2.24 (s, 3H).

Example 42

[5-(2-Methoxy-phenyl)-pyrrolo[2,1-f][1,2,4]triazin-2-yl]-[4-(4-methyl-piperazin-1-yl)-phenyl]-amine The titled compound was prepared in an analogous fashion to Example 20 replacing 7-Bromo-2-methanesulfinyl-pyrrolo[2,1-f][1,2,4]triazine with 5-Bromo-2-methane sulfinyl-pyrrolo[2,1-f][1,2,4]triazine to give [5-(2-Methoxy-phenyl)-pyrrolo[2,1-f][1,2,4]triazin-2-yl]-[4-(4-methyl-piperazin-1-yl)-phenyl]-amine as a yellow solid (52 mg, 37%). MP 169-170° C. LCMS (E/I+) 415.19 (M+H). NMR $^1$H (DSMO-d$_6$)-9.14 (s, 1H), 8.82 (s, 1H), 7.88 (d, 1H, J=2.28 Hz), 7.61 (d, 2H, J=8.88 Hz), 7.45 (d, 2H, J=8.68 Hz), 7.33 (t, 1H, J=8.44 Hz), 7.13 (d, 1H, J=8.12 Hz), 7.04 (t, 1H, J=7.54 Hz), 6.91 (d, 2H, J=8.96 Hz), 6.84 (d, 1H, J=2.52 Hz), 3.81 (s, 3H), 3.06 (t, 4H, J=4.49 Hz), 2.45 (t, 4H, J=4.88 Hz), 2.23 (s, 3H).

Example 43

[7-(3-Methanesulfonyl-phenyl)-pyrrolo[2,1-f][1,2,4]triazin-2-yl]-(4-morpholin-4-yl-phenyl)-amine The titled compound was prepared in an analogous fashion to Example 1 replacing 3-Chlorophenylboronic acid with 3-(Methanesulfonyl) phenyl boronic acid to give [7-(3-Methanesulfonyl-phenyl)-pyrrolo[2,1-f][1,2,4]triazin-2-yl]-(4-morpholin-4-yl-phenyl)-amine as a yellow solid (50 mg, 33%). MP 251-254° C. LCMS (E/I+) 450.10 (M+H). NMR $^1$H (DSMO-d$_6$)-9.32 (s, 1H), 9.00 (s, 1H), 8.60 (s, 1H), 8.48 (d, 1H, J=7.84 Hz), 7.93 (d, 2H, J=8.05 Hz), 7.81 (t, 1H, J=7.84 Hz), 7.61 (d, 2H, J=8.96 Hz), 7.26 (d, 1H, J=4.77 Hz), 6.90-7.00 (m, 3H), 3.74 (t, 4H, J=4.53 Hz), 3.03 (t, 4H, J=4.72 Hz).

Example 44

4-[2-(4-Morpholin-4-yl-phenylamino)-pyrrolo[2,1-f][1,2,4]triazin-7-yl]-benzoic acid tert-butyl ester The titled compound was prepared in an analogous fashion to Example 1 replacing 3-Chlorophenylboronic acid with 4-(tert-Butoxycarbonyl)phenyl boronic acid to give 4-[2-(4-Morpholin-4-yl-phenylamino)-pyrrolo[2,1-f][1,2,4]triazin-7-yl]-benzoic acid tert-butyl ester as a yellow solid (40 mg, 25% yield). MP 208-209° C. LCMS (E/I+) 472.22 (M+H). NMR $^1$H (DSMO-d$_6$)-9.28 (s, 1H), 8.99 (s, 1H), 8.37 (d, 1H, J=8.44 Hz), 7.99 (d, 1H, J=8.44 Hz), 7.60 (d, 2H, J=9.08 Hz), 7.28 (d, 1H, J=4.76 Hz), 6.90-7.00 (m, 3H), 3.76 (t, 4H, J=4.44 Hz), 3.08 (t, 4H, J=4.60 Hz).

Example 45

4-[2-(4-Morpholin-4-yl-phenylamino)-pyrrolo[2,1-f][1,2,4]triazin-7-yl]-benzoic acid Into a 1-neck round-bottom flask, [A] 4-[2-(4-Morpholin-4-yl-phenylamino)-pyrrolo[2,1-f][1,2,4]triazin-7-yl]-benzoic acid tert-butyl ester (0.34 g, 0.72 mmol), Methylene chloride (10 mL, 200 mmol) and Trifluoroacetic Acid (5.0 mL, 65 mmol) were added and stirred at room temperature overnight. The solvent was removed under vacuum. The resulting solid was washed with DCM to give 4-[2-(4-Morpholin-4-yl-phenylamino)-pyrrolo[2,1-f][1,2,4]triazin-7-yl]-benzoic acid; compound with trifluoro-acetic acid as a yellow solid. LCMS (E/I+) 416.16 (M+H). NMR $^1$H (DSMO-d$_6$)-9.45 (s, 1H), 9.01 (s, 1H), 8.35 (d, 2H, J=8.40 Hz), 8.07 (d, 2H, J=8.41 Hz), 7.88 (s, 1H), 7.71 (d, 1, J=8.80 Hz), 7.30 (d 1H, J=4.76 Hz), 7.17 (d, 2H, J=8.44 Hz), 6.98 (d, 1H, J=4.80 Hz), 3.83 (t, 4H, J=4.78 Hz), 3.24 (bs, 4H).

Example 46

(6-Morpholin-4-yl-pyridin-3-yl)-(7-phenyl-pyrrolo[2,1-f][1,2,4]triazin-2-yl)-amine The titled compound was prepared in an analogous fashion to Example 12 replacing 3-(aminomethyl)pyridine with 6-Morpholin-4-yl-pyridin-3-ylamine to give (6-Morpholin-4-yl-pyridin-3-yl)-(7-phenyl-pyrrolo[2,1-f][1,2,4]triazin-2-yl)-amine as a yellow solid (22 mg, 17%). MP 210-211° C. LCMS (E/I+) 373.18 (M+H). NMR $^1$H (DSMO-d$_6$)-9.25 (s, 1H), 8.95 (s, 1H), 8.48 (d, 2H, J=2.40 Hz), 8.15 (d, 2H, J=7.96 Hz), 8.00 (dd, 1H, JJ=2.48, 6.53 Hz), 7.52 (t, 1H, J=6.96 Hz), 7.38 (t 1H, J=7.44 Hz), 7.16 (d, 2H, J=4.72 Hz), 6.93 (d, 1H, J=4.69 Hz), 6.86 (d, 1H, J=9.13 Hz), 3.72 (t, 4H, J=4.44 Hz), 3.38 (t, 4H, J=4.24 Hz).

Example 47

[7-(2-Methoxy-phenyl)-pyrrolo[2,1-f][1,2,4]triazin-2-yl]-(6-morpholin-4-yl-pyridin-3-yl)-amine 47a) 7-(2-Methoxy-phenyl)-2-methylsulfanyl-pyrrolo[2,1-f][1,2,4]: Into a 200 mL round bottom flask, Palladium Acetate (0.20 g, 0.00088 mol) and Triphenylphosphine (0.65 g, 0.0025 mol) were added. The mixture was purged under an atmosphere of Nitrogen for 10 minutes. 1,4-Dioxane (66.8 mL, 0.856 mol) was added and stirred for 10 minutes at room temperature. 7-Bromo-2-methylsulfanyl-pyrrolo[2,1-f][1,2,4]triazine (2.150 g, 0.008807 mol), 2-methoxybenzeneboronic acid (2.68 g, 0.0176 mol), N,N-Dimethylformamide (130 mL, 1.7 mol), and 1.50 M of Sodium carbonate in Water (52.8 mL, 0.0793 mol) were added. The reaction was heated at 90° C. for 3 hours. The reaction was partitioned with water and EtOAc. The organic was separated, washed with Brine, and dried over magnesium sulfate. The solid was filtered and washed with EtOAc. The solvent was removed under vacuum. The desired product was purified via ISCO column chromatography with DCM and methanol as eluant (0 to 3% methanol). The collected fractions afforded 7-(2-Methoxy-phenyl)-2-methylsulfanyl-pyrrolo[2,1-f][1,2,4]triazine as a yellow solid (1.85 g, 78%). NMR $^1$H (DSMO-d$_6$)-8.89 (s, 1H), 7.81 (dd, 1H, JJ=2.74, 6.01 Hz), 7.42 (td, 1H, JJ=1.68, 6.92 Hz), 7.07-7.25 (m, 4H), 3.81 (s, 3H), 2.43 (s, 3H)

47b) 2-Methanesulfinyl-7-(2-methoxy-phenyl)-pyrrolo[2,1-f][1,2,4]triazine: Into a Round bottom flask, 7-(2-Methoxy-phenyl)-2-methylsulfanyl-pyrrolo[2,1-f][1,2,4]triazine (1.80 g, 0.00663 mol) and Methylene chloride (20 mL, 0.2 mol) were added. m-Chloroperbenzoic acid (1.26 g, 0.00730 mol) was added portion wise over 20 minutes. The reaction was stirred at room temperature for one hour. The reaction was partitioned with DCM (200 mL) and saturated NaHCO$_3$ (200 mL). The organic was separated, washed with Brine and dried over Na$_2$SO$_4$. The solid was filtered and washed with DCM. The solvent was removed under vacuum to give a gummy solid. The solid was triturated with Et$_2$O. The solid was filtered and washed with cold Et$_2$O to give 2-Methanesulfinyl-7-(2-methoxy-phenyl)-pyrrolo[2,1-f][1,2,4]triazine as a yellow solid. NMR $^1$H (DSMO-d$_6$)-9.30 (s, 1H), 7.75 (dd, 1H, JJ=1.64, 5.97 Hz), 7.49 (dt, 1H, JJ=1.68, 6.97 Hz), 7.39 (d, 1H, J=4.72 Hz), 7.30 (d, 1H, J=4.86 Hz), 7.24 (d, 1H, J=8.28 Hz), 7.11 (d 1H, J=7.45 Hz), 3.82 (s, 3H), 2.94 (s, 3H).

47c) Into a 30 mL seal tube, 2-Methanesulfinyl-7-(2-methoxy-phenyl)-pyrrolo[2,1-f][1,2,4]triazine (0.11 g, 0.00037 mol), [B] 6-Morpholin-4-yl-pyridin-3-ylamine (0.146 g, 0.000812 mol), and N-Methylpyrrolidinone (1.20 mL, 0.0124 mol) were added. The reaction was heated at 150° C. for 3 hours The reaction was partitioned with water and DCM. The organic was separated, washed with Brine and dried over Na$_2$SO$_4$. The solid was filtered and washed with DCM. The Solvent was removed under vacuum to afford a semi solid. The reaction mixture was purified via HPLC reverse phase chromatography with 0.1% TFA in Water and 0.1% TFA in ACN. The collected fractions were lyophilized to give [7-(2-

Methoxy-phenyl)-pyrrolo[2,1-f][1,2,4]triazin-2-yl]-(6-morpholin-4-yl-pyridin-3-yl)-amine; compound with trifluoro-acetic acid as a yellow powder. LCMS (E/I+) 403.21 (M+H). NMR $^1$H (DSMO-d$_6$)-9.18 (s, 1H), 8.91 (s, 1H), 8.43 (d, 2H, J=3.56 Hz), 7.94 (dd, 1H, JJ=2.68, 6.37 Hz), 7.40-7.50 (m, 1H), 7.19 (d, 2H, J=8.44 Hz), 7.09 (t, 1H, J=7.56 Hz), 6.90 (dd, 1H, JJ=2.92, 4.68 Hz), 6.73 (d 1H, J=9.12 Hz), 3.79 (t, 4H, J=4.52 Hz), 3.32 (t, 4H, J=3.92 Hz).

Example 48

[8-Methoxy-3-(2-methoxy-ethyl)-2,3,4,5-tetrahydro-1H-benzo[d]azepin-7-yl]-[7-(2-methoxy-phenyl)-pyrrolo[2,1-f][1,2,4]triazin-2-yl]-amine The titled compound was prepared in an analogous fashion to Example 47 replacing 6-Morpholin-4-yl-pyridin-3-ylamine with 8-Methoxy-3-(2-methoxy-ethyl)-2,3,4,5-tetrahydro-1H-benzo[d]azepin-7-ylamine to give [8-Methoxy-3-(2-methoxy-ethyl)-2,3,4,5-tetrahydro-1H-benzo[d]azepin-7-yl]-[7-(2-methoxy-phenyl)-pyrrolo[2,1-f][1,2,4]triazin-2-yl]-amine; compound with trifluoro-acetic acid as a yellow powder (18 mg, 14%). LCMS (E/I+) 474.22 (M+H). NMR $^1$H (DSMO-d$_6$)-8.95 (s, 1H), 7.96 (s, 1H), 7.82 (d, 1H, J=7.44 Hz), 7.60 (s, 1H), 7.47 (t, 1H, J=7.44 Hz), 7.24 (d, 1H, J=8.00 Hz), 7.11 (t, 1H, J=7.97 Hz), 6.90-7.00 (m, 2H), 3.85 (s, 3H), 3.77 (s, 3H), 3.50-3.73 (m, 6H), 3.30-3.45 (m, 5H), 2.90-3.20 (m, 4H).

Example 49

[7-(3-Chloro-phenyl)-pyrrolo[2,1-f][1,2,4]triazin-2-yl]-(4-piperidin-1-yl-phenyl)-amine 49a) 7-(3-Chloro-phenyl)-2-methylsulfanyl-pyrrolo[2,1-f][1,2,4]triazine Into a round bottom flask with condensor, Palladium Acetate (0.014 g, 0.000064 mol), and Triphenylphosphine (0.056 g, 0.00021 mol) were added and purged under an atmosphere of Nitrogen for 10 minutes. 1,4-Dioxane (3.0 mL, 0.038 mol) was added and stirred for 10 minutes. 7-Bromo-2-methylsulfanyl-pyrrolo[2,1-f][1,2,4]triazine (0.260 g, 0.00106 mol) and 3-chlorophenyl boronic acid (0.200 g, 0.00128 mol) in N,N-Dimethylformamide (5.0 mL, 0.064 mol) were added. 1.50 M of Sodium carbonate in Water (2.13 mL, 0.00320 mol) were added and heated at 90° C. for 2 hours. The solvent was removed under vacuum. The reaction was partitioned with water and DCM. The organic was separated, washed with Brine, and dried over magnesium sulfate. The solid was filtered and washed with EtOAc. The solvent was removed under vacuum. The product was isolated via ISCO column chromatography with hexane and EtOAc as eluant (0 to 25% EtOAc) Note UV lamp was set at 215 nM. The collected fractions afforded 7-(3-Chloro-phenyl)-2-methylsulfanyl-pyrrolo[2,1-f][1,2,4]triazine as a yellow solid (180 mg, 61%). LCMS 276.06 (M+H).

49b) Into a 100 mL round bottom flask, [7-(3-Chloro-phenyl)-2-methylsulfanyl-pyrrolo[2,1-f][1,2,4]triazine (1.60 g, 0.00580 mol) was dissolved in Methylene chloride (60 mL, 1 mol) and the mixture was treated with m-Chloroperbenzoic acid (1.35 g, 0.00783 mol). The reaction was allowed to stir at room temperature until HPLC showed consumption of starting material. The reaction was partitioned between sodium bicarbinate and DCM. The organic layer was separated, washed with water subsequently with Brine and dried over sodium sulfate. The solution was filtered and reduced. The solid was then triturated with ether to afford 7-(3-Chlorophenyl)-2-methanesulfinyl-pyrrolo[2,1-f][1,2,4]triazine as a yellow solid. The product was used as is with mixture of sulfone by-product.

49c) The titled compound was prepared in an analogous fashion to Example 12 replacing 3-(aminomethylpyridine with 4-Piperidin-1-yl-phenylamine to give [7-(3-Chloro-phenyl)-pyrrolo[2,1-f][1,2,4]triazin-2-yl]-(4-piperidin-1-yl-phenyl)-amine; compound with trifluoro-acetic acid as a yellow solid (16 mg, 14%). LCMS (E/I+) 404.14 (M+H). NMR $^1$H (DSMO-d$_6$)-9.05 (s, 1H), 8.44 (s, 1H), 8.04 (d, 1H, J=7.72 Hz), 7.75-795 (m, 2H), 7.40-7.65 (m, 4H), 7.31 (d, 1H, J=4.77 Hz), 7.01 (d, 1H, J=4.70 Hz), 3.00-3.60 (m, 4H), 1.70-2.00 (m, 6H).

Example 50

(4-Morpholin-4-yl-phenyl)-pyrrolo[2,1-f][1,2,4]triazin-2-yl-amine

Into a Microwave vial, (7-Bromo-pyrrolo[2,1-f][1,2,4]triazin-2-yl)-(4-morpholin-4-yl-phenyl)-amine (0.114 g, 0.000306 mol), Zinc Cyanide (0.0719 g, 0.000612 mol), Copper(I) iodide (5.8 mg, 0.000031 mol), and Tetrakis(triphenylphosphine)palladium(0) (35 mg, 0.000031 mol) were added. The mixture was purged with nitrogen for 10 minutes. N,N-Dimethylformamide (3.00 mL, 0.0387 mol) was added. The reaction was microwaved on 300 watts, 120° C. for 2 hours. The solvent was removed under vacuum. The reaction was partitioned with water and DCM. The organic was separated, washed with Brine and dried over Na2SO4. The solid was filtered and washed with DCM. The solvent was removed under vacuum to give a solid. The reaction mixture was purified via HPLC reverse phase chromatography with 0.1% TFA in Water and 0.1% TFA in ACN. The collected fractions were lyophilized to give (4-Morpholin-4-yl-phenyl)-pyrrolo[2,1-f][1,2,4]triazin-2-yl-amine; compound with trifluoro-acetic acid as a yellow solid (45 mg, 36%). LCMS (E/I+) 296.15 (M+H). NMR $^1$H (DSMO-d$_6$)-9.21 (s, 1H), 8.90 (s, 1H), 7.76 (s, 1H), 7.66 (d, 2H, J=8.68 Hz), 6.99 (d, 2H, J=7.17 Hz), 6.71 (d, 1H, J=2.28 Hz), 6.57-6.63 (m, 1H), 3.73-3.82 (bm, 4H), 3.10 (bs, 4H).

Example 51

2-(4-Morpholin-4-yl-phenylamino)-pyrrolo[2,1-f][1,2,4]triazine-7-carbonitrile

Into a Microwave vial, (7-Bromo-pyrrolo[2,1-f][1,2,4]triazin-2-yl)-(4-morpholin-4-yl-phenyl)-amine (0.114 g, 0.000306 mol), Zinc Cyanide (0.0719 g, 0.000612 mol), Copper(I) iodide (5.8 mg, 0.000031 mol), and Tetrakis(triphenylphosphine)palladium(0) (35 mg, 0.000031 mol) were added. The mixture was purged with nitrogen for 10 minutes. N,N-Dimethylformamide (3.00 mL, 0.0387 mol) was added. The reaction was microwaved on 300 watts, 120° C. for 2 hours. The solvent was removed under vacuum. The reaction was partitioned with water and DCM. The organic was separated, washed with Brine and dried over Na2SO4. The solid was filtered and washed with DCM. The solvent was removed under vacuum to give a solid. The reaction mixture was purified via HPLC reverse phase chromatography with 0.1% TFA in Water and 0.1% TFA in ACN. The collected fractions were lyophilized to give 2-(4-Morpholin-4-yl-phenylamino)-pyrrolo[2,1-f][1,2,4]triazine-7-carbonitrile; compound with trifluoro-acetic acid as a yellow solid (16 mg, 12%). LCMS (E/I+) 321.11 (M+H). NMR $^1$H (DSMO-d$_6$)-9.77 (s, 1H), 9.14 (s, 1H), 7.76 (s, 1H), 7.70 (d, 2H, J=8.93 Hz), 7.34 (d, 1H, J=4.84 Hz), 7.01 (d, 2H, J=8.60 Hz), 6.89 (d, 1H, J=4.84 Hz), 6.57-6.63 (m, 1H), 3.71 (t, 4H, J=3.96 Hz), 3.12 (bs, 4H).

Example 52

N-(2-Dimethylamino-ethyl)-4-[2-(4-morpholin-4-yl-phenylamino)-pyrrolo[2,1-f][1,2,4]triazin-7-yl]-benzamide Into a 30 mL vial, [A] 4-[2-(4-Morpholin-4-yl-phenylamino)-pyrrolo[2,1-f][1,2,4]triazin-7-yl]-benzoic acid (0.10 g, 0.00024 mol), [B] N,N-dimethyl-1,2-Ethanediamine (0.0424 g, 0.000481 mol), 1-Hydroxybenzotriazole (0.0325 g, 0.000241 mol), N-(3-Dimethylaminopropyl)-N'-ethylcarbodiimide hydrochloride (0.0554 g, 0.000289 mol), N,N-Dimethylformamide (2.00 mL, 0.0258 mol) and N,N-Diisopropylethylamine (0.0933 g, 0.000722 mol) were added and stirred at RT overnight. The reaction was partitioned with water and DCM. The organic was separated, washed with Brine and dried over Na2SO4. The solid was filtered and washed with DCM the solvent was removed under vacuum. The reaction mixture was purified via HPLC reverse phase chromatography with 0.1% TFA in Water and 0.1% TFA in ACN. The collected fractions were lyophilized to give to give N-(2-Dimethylamino-ethyl)-4-[2-(4-morpholin-4-yl-phenylamino)-pyrrolo[2,1-f][1,2,4]triazin-7-yl]-benzamide; compound with trifluoro-acetic acid as a yellow powder (40 mg, 34%). MP 240-241° C. LCMS (E/I+) 486.27 (M+H). NMR $^1$H (DSMO-d$_6$)-9.52 (s, 1H), 9.37 (s, 1H), 8.99 (s, 1H), 8.80 (t, 1H, J=5.09 Hz), 8.36 (d, 2H, J=8.29 Hz), 8.01 (d, 2H, J=8.28 Hz), 7.67 (d, 2H, J=8.68 Hz), 7.29 (d, 1H, J=4.64 Hz), 7.01 (d, 2H, J=8.64 Hz), 6.97 (d, 1H, J=4.64 Hz), 3.78 (bs, 4H), 3.60-3.70 (bm, 2H), 3.25-3.35 (bm, 2H), 3.12 (bs, 4H), 2.88 (s, 3H), 2.87 (s, 3H).

Example 53

2-Pyrrolidin-1-yl-ethylamine to give 4-[2-(4-Morpholin-4-yl-phenylamino)-pyrrolo[2,1-f][1,2,4]triazin-7-yl]-N-(2-pyrrolidin-1-yl-ethyl)-benzamide The titled compound was prepared in an analogous fashion to Example 52 replacing N,N-dimethyl-1,2-Ethanediamine with 2-Pyrrolidin-1-yl-ethylamine to give 4-[2-(4-Morpholin-4-yl-phenylamino)-pyrrolo[2,1-f][1,2,4]triazin-7-yl]-N-(2-pyrrolidin-1-yl-ethyl)-benzamide; compound with trifluoro-acetic acid as a yellow powder (40 mg, 32%). LCMS (E/I+) 512.29 (M+H). NMR $^1$H (DSMO-d$_6$)-9.54 (s, 1H), 9.36 (s, 1H), 8.99 (s, 1H), 8.80 (t, 1H, J=5.40 Hz), 8.37 (d, 2H, J=8.41 Hz), 8.01 (d, 2H, J=8.44 Hz), 7.67 (d, 2H, J=8.92 Hz), 7.28 (d, 1H, J=4.76 Hz), 7.01 (d, 2H, J=8.89 Hz), 6.97 (d, 1H, J=4.76 Hz), 3.77 (t, 4H, J=4.36 Hz), 3.55-3.62 (m, 4H), 3.38 (q, 2H, JJ=5.28, 5.69 Hz), 1.80-2.12 (m, 4H).

Example 54

4-[2-(4-Morpholin-4-yl-phenylamino)-pyrrolo[2,1-f][1,2,4]triazin-7-yl]-N-(3-pyrrolidin-1-yl-propyl)-benzamide; compound with trifluoro-acetic acid The titled compound was prepared in an analogous fashion to Example 52 replacing N,N-dimethyl-1,2-Ethanediamine with 3-Pyrrolidin-1-yl-propylamine to give 4-[2-(4-Morpholin-4-yl-phenylamino)-pyrrolo[2,1-f][1,2,4]triazin-7-yl]-N-(3-pyrrolidin-1-yl-propyl)-benzamide; compound with trifluoro-acetic acid as a yellow powder (43 mg, 34%). LCMS (E/I+) 526.19 (M+H). NMR $^1$H (DSMO-d$_6$)-9.56 (s, 1H), 9.34 (s, 1H), 8.98 (s, 1H), 8.69 (t, 1H, J=5.61 Hz), 8.34 (d, 2H, J=8.40 Hz), 8.00 (d, 2H, J=8.45 Hz), 7.66 (d, 2H, J=8.76 Hz), 7.28 (d, 1H, J=4.60 Hz), 7.00 (d, 2H, J=8.65 Hz), 6.95 (d, 1H, J=4.80 Hz), 3.77 (t, 4H, J=4.04 Hz), 3.53-3.58 (bm, 2H), 3.38 (q, 2H, JJ=6.04, 5.92 Hz), 3.15-3.27 (m, 2H), 3.10 (bs, 4H), 2.96-3.07 (m, 2H), 1.80-2.10 (m, 6H).

Example 55

N-Methyl-4-[2-(4-morpholin-4-yl-phenylamino)-pyrrolo[2,1-f][1,2,4]triazin-7-yl]-benzamide The titled compound was prepared in an analogous fashion to Example 52 replacing N,N-dimethyl-1,2-Ethanediamine with 2.00 M of Methylamine in Tetrahydrofuran to give N-Methyl-4-[2-(4-morpholin-4-yl-phenylamino)-pyrrolo[2,1-f][1,2,4]triazin-7-yl]-benzamide; compound with trifluoro-acetic acid as a yellow powder (32 mg, 31%). LCMS (E/I+) 429.11 (M+H). NMR $^1$H (DSMO-d$_6$)-9.35 (s, 1H), 8.98 (s, 1H), 8.51 (d, 1H, J=4.21 Hz), 8.32 (d, 1H, J=8.44 Hz), 7.96 (d, 2H, J=8.40 Hz), 7.66 (d, 2H, J=8.00 Hz), 7.27 (d, 1H, J=4.40 Hz), 7.01 (d, 2H, J=6.92 Hz), 6.95 (d, 1H, J=4.76 Hz), 3.78 (s, 4H), 3.12 (s, 4H), 2.83 (d, 2H, J=4.36 Hz).

Example 56

N-(2-Morpholin-4-yl-ethyl)-4-[2-(4-morpholin-4-yl-phenylamino)-pyrrolo[2,1-f][1,2,4]triazin-7-yl]-benzamide The titled compound was prepared in an analogous fashion to Example 52 replacing N,N-dimethyl-1,2-Ethanediamine with N-(2-aminoethyl)morpholine to give N-(2-Morpholin-4-yl-ethyl)-4-[2-(4-morpholin-4-yl-phenylamino)-pyrrolo[2,1-f][1,2,4]triazin-7-yl]-benzamide; compound with trifluoro-acetic acid (7 mg, 5.5%). LCMS (E/I+) 528.10 (M+H). NMR $^1$H (DSMO-d$_6$)-9.72 (s, 1H), 9.34 (s, 1H), 8.99 (s, 1H), 8.82 (bs, 1H), 8.37 (d, 2H, J=8.57 Hz), 8.01 (d, 2H, J=8.28 Hz), 7.65 (d, 2H, J=8.88 Hz), 7.29 (d, 1H, J=4.80 Hz), 6.95-7.03 (m, 3H), 3.50-4.20 (bm, 14H), 3.30-3.42 (m, 2H), 3.08-3.25 (m, 4H).

Example 57

4-[2-(4-Morpholin-4-yl-phenylamino)-pyrrolo[2,1-f][1,2,4]triazin-7-yl]-N-(3-morpholin-4-yl-propyl)-benzamide The titled compound was prepared in an analogous fashion to Example 52 replacing N,N-dimethyl-1,2-Ethanediamine with 4-Morpholinepropanamine to give 4-[2-(4-Morpholin-4-yl-phenylamino)-pyrrolo[2,1-f][1,2,4]triazin-7-yl]-N-(3-morpholin-4-yl-propyl)-benzamide; compound with trifluoro-acetic acid as a yellow powder (50 mg, 38%). LCMS (E/I+) 542.16 (M+H). NMR $^1$H (DSMO-d$_6$)-9.68 (s, 1H), 9.33 (s, 1H), 8.98 (s, 1H), 8.71 (t, 1H, J=5.84 Hz), 8.35 (d, 2H, J=8.36 Hz), 8.00 (d, 2H, J=8.44 Hz), 7.65 (d, 2H, J=8.84 Hz), 7.28 (d, 1H, J=4.72 Hz), 6.98 (d, 2H, J=8.89 Hz), 6.96 (d, 1H, J=4.80 Hz), 3.98 (d, 2H, J=12.37 Hz), 3.72-3.85 (bm, 4H), 3.65 (t, 2H, J=12.00 Hz), 3.46 (d, 2H, J=12.28 Hz), 3.30-3.44 (m, 2H), 3.19 (bs, 2H), 3.09 (bs, 4H), 1.89-2.03 (m, 2H).

Example 58

[7-(4-Chloro-3-trifluoromethyl-phenyl)-pyrrolo[2,1-f][1,2,4]triazin-2-yl]-(4-morpholin-4-yl-phenyl)-amine The titled compound was prepared in an analogous fashion to Example 1 replacing 3-Chlorophenylboronic acid with 4-chloro-3-trifluoromethylphenylboronic acid to give [7-(4-Chloro-3-trifluoromethyl-phenyl)-pyrrolo[2,1-f][1,2,4]triazin-2-yl]-(4-morpholin-4-yl-phenyl)-amine as a yellow solid (65 mg, 45%). MP 177-178° C. LCMS (E/I+) 474.09 NMR $^1$H (DSMO-d$_6$)-9.35 (s, 1H), 9.00 (s, 1H), 8.68 (s, 1H), 8.33 (d, 1H, J=8.48 Hz), 7.87 (d, 1H, J=8.53 Hz), 7.58 (d, 2H, J=8.98 Hz), 7.28 (d, 1H, J=4.80 Hz), 6.95 (d, 1H, J=4.76 Hz), 6.90 (d, 2H, J=8.92 Hz), 3.75 (t, 4H, J=4.60 Hz), 3.04 (d, 4H, J=4.60 Hz).

Example 59

[7-(4-Methanesulfonyl-phenyl)-pyrrolo[2,1-f][1,2,4]triazin-2-yl]-[4-(4-methyl-piperazin-1-yl)-phenyl]-amine 59a) Into a 30 ml, vial, Palladium Acetate (0.11 g, 0.00049 mol) and Triphenylphosphine (0.32 g, 0.0012 mol) were added and purged under an atmosphere of Nitrogen for 5 minutes 1,4-Dioxane (10.8 mL, 0.138 mol) was added and stirred for 10 minutes. 7-Bromo-2-methylsulfanyl-pyrrolo[2,1-f][1,2,4]triazine (0.600 g, 0.00246 mol), (4-Methylsulfonylphenyl)boronic acid (0.983 g, 0.00492 mol), N,N-Dimethylformamide (23.7 mL, 0.306 mol) and 1.50 M of Sodium carbonate in Water (4.92 mL, 0.00737 mol) were added, respectively. The reaction mixture was heated at 80° C. overnight. The solvent was removed under vacuum. The solid was washed with DCM. The organic was removed under vacuum. The reaction was purified via ISCO column chromatography with hexane and EtOAc as eluant (0 to 100% EtOAc). The collected fraction afforded 7-(4-Methanesulfonyl-phenyl)-2-methylsulfanyl-pyrrolo[2,1-f][1,2,4]triazine a yellow solid (0.63 g, 83%). NMR $^1$H (DSMO-d$_6$)-9.09 (s, 1H), 8.51 (d, 2H, J=8.48 Hz), 8.05 (d, 2H, J=8.49 Hz), 7.58 (d, 1H, J=4.84 Hz), 7.15 (d, 1H, J=4.84 Hz), 3.27 (s, 3H), 2.62 (s, 3H).

59b) Into a Round bottom flask, 7-(4-Methanesulfonyl-phenyl)-2-methylsulfanyl-pyrrolo[2,1-f][1,2,4]triazine (0.630 g, 0.00197 mol) and Methylene chloride (50 mL, 0.8 mol) were added. m-Chloroperbenzoic acid (0.464 g, 0.00207 mol) was added portion wise. The reaction was stirred at room temperature for 30 minutes. Saturated NaHCO3 was added. The organic layer was separated, washed with Brine and dried over Na2SO4. The solid was filtered and washed with DCM. The organic was removed under vacuum. to give 2-Methanesulfinyl-7-(4-methanesulfonyl-phenyl)-pyrrolo[2,1-f][1,2,4]triazine a yellow solid (0.63 g, 93%). NMR $^1$H (DSMO-d$_6$)-9.40 (s, 1H), 8.54 (d, 2H, J=8.60 Hz), 8.09 (d, 2H, J=7.56 Hz), 7.85 (d, 1H, J=4.84 Hz), 7.39 (d, 1H, J=4.88 Hz), 3.29 (s, 3H), 3.00 (s, 3H)

59c) Into a 30 mL vial, 2-Methanesulfinyl-7-(4-methanesulfonyl-phenyl)-pyrrolo[2,1-f][1,2,4]triazine (80 mg, 0.0002 mol), 4-(4-Methyl-piperazin-1-yl)-phenylamine (0.100 g, 0.000525 mol) and N-Methylpyrrolidinone (0.25 mL, 0.0026 mol) were added. The reaction mixture was heated at 150° C. for 90 minutes. The reaction was cool to room temperature. Methanol (15 mL) was added. The solid was filtered and washed with hot MeOH (10 mL) to afford [7-(4-Methanesulfonyl-phenyl)-pyrrolo[2,1-f][1,2,4]triazin-2-yl]-[4-(4-methyl-piperazin-1-yl)-phenyl]-amine as a light brown solid. MP 234-238° C. LCMS (E/I+) 373.18 (M+H). NMR $^1$H (DSMO-d$_6$)-9.31 (s, 1H), 9.00 (s, 1H), 8.48 (d, 2H, J=8.48 Hz), 8.02 (d, 2H, J=8.16 Hz), 7.57 (d, 2H, J=8.79 Hz), 7.33 (d, 1H, J=4.77 Hz), 6.95 (d, 1H, J=4.76 Hz), 6.95-7.04 (m, 3H), 3.28 (s, 3H), 3.09 (bs, 4H), 2.40-2.56 (m, 4H), 2.22 (s, 3H).

Example 60

[7-(4-Methanesulfonyl-phenyl)-pyrrolo[2,1-f][1,2,4]triazin-2-yl]-(6-morpholin-4-yl-pyridin-3-yl)-amine The titled compound was prepared in an analogous fashion to Example 59 replacing 4-(4-Methyl-piperazin-1-yl)-phenylamine with 6-Morpholin-4-yl-pyridin-3-ylamine to give [7-(4-Methanesulfonyl-phenyl)-pyrrolo[2,1-f][1,2,4]triazin-2-yl]-(6-morpholin-4-yl-pyridin-3-yl)-amine as a yellow solid (40 mg, 37%. MP 238-240° C. LCMS (E/I+) 373.18 (M+H). NMR $^1$H (DSMO-d$_6$)-9.33 (s, 1H), 9.02 (s, 1H), 8.38-8.47 (m, 3H), 7.88-8.04 (m, 3H), 7.34 (d, 1H, J=4.88 Hz), 6.99 (d, 1H, J=4.72 Hz), 6.92 (d, 1H, J=9.04 Hz), 3.73 (t, 4H, J=4.40 Hz), 3.40 (t, 4H, J=4.60 Hz), 3.27 (s, 3H).

Example 61

[7-(4-Methanesulfonyl-phenyl)-pyrrolo[2,1-f][1,2,4]triazin-2-yl]-(4-piperidin-1-yl-phenyl)-amine The titled compound was prepared in an analogous fashion to Example 594-(4-Methyl-piperazin-1-yl)-phenylamine with 4-Piperidin-1-yl-phenylamine to give [7-(4-Methanesulfonyl-phenyl)-pyrrolo[2,1-f][1,2,4]triazin-2-yl]-(4-piperidin-1-yl-phenyl)-amine MP 230-234° C. LCMS (E/I+) 448.11 (M+H). NMR $^1$H (DSMO-d$_6$)-9.29 (s, 1H), 9.00 (s, 1H), 8.48 (d, 2H, J=8.33 Hz), 8.02 (d, 2H, J=8.44 Hz), 7.56 (d, 2H, J=8.77 Hz), 7.33 (d, 1H, J=4.66 Hz), 6.93-7.05 (m, 3H), 3.29 (s, 2H), 3.08 (t, 4H, J=4.88 Hz), 1.50-1.73 (m, 6H).

Example 62

[7-(4-Methanesulfonyl-phenyl)-pyrrolo[2,1-f][1,2,4]triazin-2-yl]-[2-methoxy-4-(4-methyl-piperazin-1-yl)-phenyl]-amine The titled compound was prepared in an analogous fashion to Example 59 replacing 4-(4-Methyl-piperazin-1-yl)-phenylamine with 2-Methoxy-4-(4-methyl-piperazin-1-yl)-phenylamine to give [7-(4-Methanesulfonyl-phenyl)-pyrrolo[2,1-f][1,2,4]triazin-2-yl]-[2-methoxy-4-(4-methyl-piperazin-1-yl)-phenyl]-amine; compound with trifluoro-acetic acid (7 mg, 6%) MP 240-241° C. LCMS (E/I+) 373.18 (M+H). NMR $^1$H (DSMO-d$_6$)-9.72 (s, 1H), 8.99 (s, 1H), 8.43 (d, 2H, J=8.53 Hz), 8.08 (s, 1H), 7.94 (d, 2H, J=8.48 Hz), 7.67 (d, 1H, J=8.60 Hz), 7.34 (d, 1H, J=4.80 Hz), 6.96 (d, 1H, J=4.40 Hz), 6.79 (s, 1H), 6.64 (d, 2H, J=7.70 Hz), 3.80-3.95 (m, 5H), 3.50-3.63 (m, 2H), 3.14-3.34 (bm, 7H), 2.98 (bm, 2H), 2.89 (s, 3H).

Example 63

(4-Morpholin-4-yl-phenyl)-{7-[4-(pyrrolidine-1-sulfonyl)-phenyl]-pyrrolo[2,1-f][1,2,4]triazin-2-yl}-amine The titled compound was prepared in an analogous fashion to Example 49 replacing 3-chlorophenylboronic acid with 4-Boronophenyl-N-pyrrolosulfonamide to give (4-Morpholin-4-yl-phenyl)-{7-[4-(pyrrolidine-1-sulfonyl)-phenyl]-pyrrolo[2,1-f][1,2,4]triazin-2-yl}-amine (100 mg, 91%) MP 182-184° C. LCMS (E/I+) 505.18 (M+H). NMR $^1$H (DSMO-d$_6$)-9.32 (s, 1H), 9.00 (s, 1H), 8.41 (d, 2H, J=8.32 Hz), 7.91 (d, 2H, J=8.32 Hz), 7.59 (d, 2H, J=9.24 Hz), 7.28 (d, 1H, J=4.40 Hz), 6.90-7.00 (m, 3H), 3.75 (t, 4H, J=4.32 Hz), 3.15-3.25 (m, 4H), 3.05 (t, 4H, J=4.45 Hz), 1.63-1.73 (m, 4H).

Example 64

[7-(3-Chloro-phenyl)-pyrrolo[2,1-f][1,2,4]triazin-2-yl]-[3-methoxy-4-(4-methyl-piperazin-1-yl)-phenyl]-amine The titled compound was prepared in an analogous fashion to Example 12 replacing 4-Piperidin-1-yl-phenylamine with 3-Methoxy-4-(4-methyl-piperazin-1-yl)-phenylamine to give [7-(3-Chloro-phenyl)-pyrrolo[2,1-f][1,2,4]triazin-2-yl]-[3-methoxy-4-(4-methyl-piperazin-1-yl)-phenyl]-amine; compound with trifluoro-acetic acid as a yellow powder (18 mg, 31%). LCMS (E/I+) 449.17 (M+H). NMR $^1$H (DSMO-$d_6$)-9.00 (s, 1H), 8.38 (s, 1H), 8.10 (d, 1H, J=7.72 Hz), 7.61 (d, 1H, J=8.60 Hz), 750-7.60 (m, 2H), 7.44 (d, 1H, J=8.84 Hz), 7.26 (d, 1H, J=4.76 Hz), 7.06 (d, 2H, J=8.41 Hz), 3.52 (d, 2H, J=11.63 Hz), 3.10-3.30 (bm, 4H), 2.80-3.00 (m, 5H), 2.26 (s, 3H).

Example 65

[7-(3-Chloro-phenyl)-pyrrolo[2,1-f][1,2,4]triazin-2-yl]-(3-methoxy-4-morpholin-4-yl-phenyl)-amine The titled compound was prepared in an analogous fashion to Example 49 replacing 4-Piperidin-1-yl-phenylamine with 3-Methoxy-4-morpholin-4-yl-phenylamine to give [7-(3-Chloro-phenyl)-pyrrolo[2,1-f][1,2,4]triazin-2-yl]-(3-methoxy-4-morpholin-4-yl-phenyl)-amine; compound with trifluoro-acetic acid as a yellow solid (23 mg, 25%). LCMS (E/I+) 436.08 (M+H). NMR $^1$H (DSMO-$d_6$)-9.44 (bs, 1H), 9.01 (bs, 1H), 8.40 (s, 1H), 8.06 (d, 1H, J=7.69 Hz), 7.53 (t, 1H, J=7.96 Hz), 7.40-7.50 (m, 1H), 7.30 (s, 1H), 7.26 (d, 1H, J=4.80 Hz), 6.96 (d, 1H, J=4.72 Hz), 3.68 (bs, 4H), 3.63 (s, 3H), 3.06 (bs, 4H).

Example 66

[7-(3-Chloro-phenyl)-pyrrolo[2,1-f][1,2,4]triazin-2-yl]-(3-methyl-4-morpholin-4-yl-phenyl)-amine The titled compound was prepared in an analogous fashion to Example 49 replacing 4-Piperidin-1-yl-phenylamine with 3-Methyl-4-morpholin-4-yl-phenylamine to give [7-(3-Chloro-phenyl)-pyrrolo[2,1-f][1,2,4]triazin-2-yl]-(3-methyl-4-morpholin-4-yl-phenyl)-amine; compound with trifluoro-acetic acid as a yellow powder (28 mg, 24%). LCMS (E/I+) 420.05 (M+H). NMR $^1$H (DSMO-$d_6$)-8.94 (s, 1H), 8.51 (bs, 1H), 8.34 (s, 1H), 7.97 (d, 1H, J=8.00 Hz), 7.43 (d, 1H, J=8.53 Hz), 7.38 (t, 1H, J=7.92 Hz), 7.31 (d, 1H, J=8.01 Hz), 7.26 (d, 1H, J=4.80 Hz), 6.85-7.03 (m, 3H), 3.78 (t, 4H, J=4.20 Hz), 3.16 (t, 4H, J=4.32 Hz), 2.24 (s, 3H).

Example 67

[7-(4-Methanesulfonyl-phenyl)-pyrrolo[2,1-f][1,2,4]triazin-2-yl]-[2-methyl-4-(4-methyl-piperazin-1-yl)-phenyl]-amine The titled compound was prepared in an analogous fashion to Example 59 replacing 4-(4-Methyl-piperazin-1-yl)-phenylamine with 2-Methyl-4-(4-methyl-piperazin-1-yl)-phenylamine to give [7-(4-Methanesulfonyl-phenyl)-pyrrolo[2,1-f][1,2,4]triazin-2-yl]-[2-methyl-4-(4-methyl-piperazin-1-yl)-phenyl]-amine; compound with trifluoro-acetic acid as a yellow powder (42 mg, 38%). LCMS (E/I+) 477.19 (M+H). NMR $^1$H (DSMO-$d_6$)-9.67 (s, 1H), 8.99 (bs, 1H), 8.61 (s, 1H), 8.39 (d, 2H, J=8.52 Hz), 7.83 (d, 2H, J=8.60 Hz), 7.43 (d, 1H, J=9.21 Hz), 7.35 (d, 1H, J=4.84 Hz), 6.92-7.05 (m, 3H), 3.78 (bd, 2H, J=12.29 Hz), 3.54 (d, 2H, J=11.16 Hz), 3.07-3.25 (m, 5H), 3.00 (t, 2H, J=12.61 Hz), 2.88 (s, 3H), 2.24 (s, 3H).

Example 68

[7-(3-Chloro-phenyl)-pyrrolo[2,1-f][1,2,4]triazin-2-yl]-[2-methyl-4-(4-methyl-piperazin-1-yl)-phenyl]-amine The titled compound was prepared in an analogous fashion to Example 49 replacing 4-Piperidin-1-yl-phenylamine with 2-Methyl-4-(4-methyl-piperazin-1-yl)-phenylamine to give [7-(3-Chloro-phenyl)-pyrrolo[2,1-f][1,2,4]triazin-2-yl]-[2-methyl-4-(4-methyl-piperazin-1-yl)-phenyl]-amine; compound with trifluoro-acetic acid as a yellow powder (18 mg, 17%). LCMS (E/I+) 433.18 (M+H). NMR $^1$H (DSMO-$d_6$)-9.73 (s, 1H), 8.95 (bs, 1H), 8.53 (s, 1H), 8.35 (s, 1H), 7.97 (d, 1H, J=7.76 Hz), 7.90 (s, 1H), 7.30-7.50 (m, 2H), 7.26 (d, 1H, J=4.46 Hz), 6.83-6.99 (m, 2H), 3.81 (d, 2H, J=12.31 Hz), 3.54 (d, 2H, J=11.28 Hz), 3.10-3.27 (bm, 2H), 2.87-3.00 (m, 5H), 2.25 (s, 3H).

Example 69

[7-(3-Chloro-phenyl)-pyrrolo[2,1-f][1,2,4]triazin-2-yl]-[3-methyl-4-(4-methyl-piperazin-1-yl)-phenyl]-amine The titled compound was prepared in an analogous fashion to Example 49 replacing 4-Piperidin-1-yl-phenylamine with 3-Methyl-4-(4-methyl-piperazin-1-yl)-phenylamine to give [7-(3-Chloro-phenyl)-pyrrolo[2,1-f][1,2,4]triazin-2-yl]-[3-methyl-4-(4-methyl-piperazin-1-yl)-phenyl]-amine; compound with trifluoro-acetic acid as a yellow powder (18 mg, 17%). LCMS (E/I+) 433.18 (M+H). NMR $^1$H (DSMO-$d_6$)-9.55 (s, 1H), 9.42 (bs, 1H), 9.00 (s, 1H), 8.38 (s, 1H), 8.10 (d, 1H, J=7.44 Hz), 7.61 (d, 1H, J=7.80 Hz), 7.50-7.60 (m, 2H), 7.44 (d, 1H, J=7.96 Hz), 7.26 (d, 1H, J=4.72 Hz), 7.06 (d, 1H, J=8.41 Hz), 6.96 (d, 1H, J=4.68 Hz), 3.52 (d, 2H, J=11.53 Hz), 3.10-3.30 (m, 4H), 2.80-3.00 (m, 5H), 2.26 (s, 3H).

Example 70

[7-(2-Chloro-5-trifluoromethyl-phenyl)-pyrrolo[2,1-f][1,2,4]triazin-2-yl]-(4-morpholin-4-yl-phenyl)-amine The titled compound was prepared in an analogous fashion to Example 1 replacing 3chlorophenylbornonic acid with 2-chloro-5-trifluorophenyl boronic acid to give [7-(2-Chloro-5-trifluoromethyl-phenyl)-pyrrolo[2,1-f][1,2,4]triazin-2-yl]-(4-morpholin-4-yl-phenyl)-amine; compound with trifluoro-acetic acid as a yellow powder (3.5 mg, 17%). LCMS (E/I+) 447.06 (M+H). NMR $^1$H (DSMO-$d_6$)-9.02 (s, 1H), 8.21 (s, 1H), 7.94 (d, 1H, J=8.41 Hz), 7.86 (d, 1H, J=7.89 Hz), 7.52 (d, 2H, J=8.84 Hz), 7.05 (d, 1H, J=4.65 Hz), 6.96 (d, 1H, J=4.68 Hz), 6.83 (d, 1H, J=8.12 Hz), 3.74 (bs, 4H), 3.04 (bs, 4H).

Example 71

N,N-Dimethylsulfonamide-4-benzeneboronic acid to give N,N-Dimethyl-4-[2-(4-morpholin-4-yl-phenylamino)-pyrrolo[2,1-f][1,2,4]triazin-7-yl]-benzenesulfonamide The titled compound was prepared in an analogous fashion to Example 1 replacing 3-chlorophenylbornonic acid with N,N-Dimethylsulfonamide-4-benzeneboronic acid to give N,N-Dimethyl-4-[2-(4-morpholin-4-yl-phenylamino)-pyrrolo[2,1-f][1,2,4]triazin-7-yl]-benzenesulfonamide; compound with trifluoro-acetic acid as a yellow powder (10 mg, 8%). LCMS (E/I+) 479.06 (M+H). NMR $^1$H (DSMO-$d_6$)-9.40 (s, 1H), 9.02 (s, 1H), 8.44 (d, 2H, J=8.49 Hz), 7.85 (d, 2H, J=8.48 Hz), 7.64 (d, 1H, J=8.32 Hz), 7.31 (d, 1H, J=4.53 Hz), 7.04 (d, 2H, J=7.64 Hz), 6.98 (d, 1H, J=4.84 Hz), 3.78 (bs, 4H), 3.13 (bs, 4H), 2.66 (s, 6H).

Example 72

[2-(4-Morpholin-4-yl-phenylamino)-pyrrolo[2,1-f][1,2,4]triazin-7-yl]-phenyl-methanone Into a 30 mL vial, (7-Bromo-pyrrolo[2,1-f][1,2,4]triazin-2-yl)-(4-morpholin-4-yl-phenyl)-amine (0.0986 g, 0.000264 mol), [B] Phenylboronic acid (0.0643 g, 0.000527 mol), Cesium Carbonate (0.429 g, 0.00132 mol), Tetrakis(triphenylphosphine)palladium (0) (0.0305 g, 0.0000264 mol), and Anisole (1.0 mL, 0.0092 mol) were added. The mixture was bubbled with carbon monoxide for 10 minutes. The reaction was heated at 110° C. for 6 hours. The reaction was partitioned with water and EtOAc. The organic was separated, washed with Brine, and dried over magnesium sulfate. The solid was filtered and washed with EtOAc. The solvent was removed under vacuum to give a solid. T The reaction mixture was purified via HPLC reverse phase chromatography with 0.1% TFA in Water and 0.1% TFA in ACN. The collected fractions were lyophilized to give [2-(4-Morpholin-4-yl-phenylamino)-pyrrolo[2,1-f][1,2,4]triazin-7-yl]-phenyl-methanone; compound with trifluoro-acetic acid as a yellow powder (0.75 mg, 1%). LCMS (E/I+) 400.01 (M+H). NMR $^1$H (DSMO-$d_6$)-9.52 (s, 1H), 9.17 (s, 1H), 7.81 (d, 2H, J=7.84 Hz), 7.68 (d, 1H, J=9.13 Hz), 7.58 (t, 2H, J=7.28 Hz), 7.52 (d, 2H, J=8.88 Hz), 7.11 (d, 1H, J=5.08 Hz), 6.91 (d, 1H, J=4.80 Hz), 6.79 (d, 2H, J=8.68 Hz), 3.20-4.00 (bm, 4H), 3.04 (bs, 4H).

Example 73

[2-Methoxy-4-(4-methyl-piperazin-1-yl)-phenyl]-[7-(6-methoxy-pyridin-3-yl)-pyrrolo[2,1-f][1,2,4]triazin-2-yl]-amine 73a) (7-Bromo-pyrrolo[2,1-f][1,2,4]triazin-2-yl)-[2-methoxy-4-(4-methyl-piperazin-1-yl)-phenyl]-amine: Into a 30 mL vial, [A] 2-Methoxy-4-(4-methyl-piperazin-1-yl)-phenylamine (1.08 g, 0.00490 mol), [B] 7-Bromo-2-methanesulfinyl-pyrrolo[2,1-f][1,2,4]triazine (0.580 g, 0.00223 mol) and N-Methylpyrrolidinone (3.50 mL, 0.0363 mol) were added. The reaction mixture was heated at 145° C. for 2.5 hours. The solvent was removed under vacuum to give a solid. The solid was partitioned with water and DCM. The organic was separated, washed with Brine and dried over sodium sulfate. The solid was filtered and washed with DCM. The solvent was removed under vacuum. The desired product was isolated via ISCO column chromatography with DCM and MeOH as eluant (3 to 10% methanol). The collected fractions afforded (7-Bromo-pyrrolo[2,1-f][1,2,4]triazin-2-yl)-[2-methoxy-4-(4-methyl-piperazin-1-yl)-phenyl]-amine as a yellow solid (0.58 g, 62%). NMR $^1$H (DSMO-$d_6$)-8.83 (s, 1H), 8.03 (d, 1H, J=8.76 Hz), 7.75 (s, 1H), 6.92 (d, 1H, J=4.58 Hz), 6.86 (d, 1H, J=4.68 Hz), 6.67 (d, 1H, J=2.24 Hz), 6.49 (dd, 1H, JJ=2.32, 6.44 Hz), 3.85 (s, 3H), 3.12 (t, 4H, J=4.64 Hz), 2.46 (t, 4H, J=4.84 Hz), 2.22 (s, 3H)

73b) Into a 30 mL vial, Palladium Acetate (12.5 mg, 0.0557 mmol) and Triphenylphosphine (36.5 mg, 0.139 mmol) were added and purged under an atmosphere of Nitrogen for 5 minutes. 1,4-Dioxane (2.6 mL, 33 mmol) was added and stirred for 10 minutes. and 2-Methoxypyridine-5-boronic acid (0.0696 g, 0.455 mmol) in N,N-Dimethylformamide (2.6 mL, 34 mmol) and 1.50 M of Sodium carbonate in Water (0.557 mL, 0.836 mmol) were added, respectively. The reaction mixture was heated at 100° C. for 30 minutes. The solvent was removed under vacuum. The solid was washed with DCM. The organic was removed under vacuum. The reaction was purified via ISCO column chromatography with DCM and methanol as eluant (0 to 10% methanol). The collected fraction afforded a solid. The solid was washed with methanol to give [2-Methoxy-4-(4-methyl-piperazin-1-yl)-phenyl]-[7-(6-methoxy-pyridin-3-yl)-pyrrolo[2,1-f][1,2,4]triazin-2-yl]-amine a yellow solid. MP 170-173° C. LCMS (E/I+) 446.18 (M+H). NMR $^1$H (DSMO-$d_6$)-8.89 (s, 1H), 8.87 (d, 1H, J=1.73 Hz), 8.48 (dd, 1H, JJ=2.04, 6.72 Hz), 7.80 (s, 1H), 7.68 (d, 1H, J=8.65 Hz), 7.15 (d, 1H, J=4.66 Hz), 6.90-7.00 (m, 2H), 6.67 (bs, 1H), 6.52 (dd, 1H, JJ=1.88, 6.76 Hz), 3.91 (s, 3H), 3.82 (s, 3H), 3.14 (bs, 4H), 2.47 (bs, 4H), 2.23 (s, 3H).

Example 74

4,N,N-Trimethyl-3-{2-[4-(4-methyl-piperazin-1-yl)-phenylamino]-pyrrolo[2,1-f][1,2,4]triazin-7-yl}-benzenesulfonamide The titled compound was prepared in an analogous fashion to Example 7 replacing phenylboronic acid with N,N-Dimethyl 4-methyl-3-boronobenzenesulfonamide to give N,N-Dimethyl-4-[2-(4-morpholin-4-yl-phenylamino)-pyrrolo[2,1-f][1,2,4]triazin-7-yl]-benzenesulfonamide as a yellow solid (80 mg, 70%). MP 235-237° C. LCMS (E/I+) 506.20 (M+H). NMR $^1$H (DSMO-$d_6$)-9.20 (s, 1H), 8.97 (s, 1H), 7.84 (s, 1H), 7.76 (d, 1H, J=7.93 Hz), 7.69 (d, 1H, J=8.13 Hz), 7.41 (d, 2H, J=8.84 Hz), 6.95 (d, 1H, J=4.52 Hz), 6.93 (d, 1H, J=4.56 Hz), 6.75 (d, 2H, J=7.89 Hz), 2.98 (bs, 4H), 2.61 (s, 6H), 2.42 (bs, 4H), 2.34 (s, 3H), 2.20 (s, 3H).

Example 75

3-{2-[2-Methoxy-4-(4-methyl-piperazin-1-yl)-phenylamino]-pyrrolo[2,1-f][1,2,4]triazin-7-yl}-4,N,N-trimethyl-benzenesulfonamide The titled compound was prepared in an analogous fashion to Example 73 replacing 2-Methoxypyridine-5-boronic acid with N,N-Dimethylsulfonamide-4-benzeneboronic acid to give 3-{2-[2-Methoxy-4-(4-methyl-piperazin-1-yl)-phenylamino]-pyrrolo[2,1-f][1,2,4]triazin-7-yl}-4,N,N-trimethyl-benzenesulfonamide as a yellow solid (70 mg, 57%). MP 210-212° C. LCMS (E/I+) 536.21 (M+H). NMR $^1$H (DSMO-$d_6$)-8.96 (s, 1H), 7.84 (s, 1H), 7.70-7.78 (m, 1H), 7.73 (d, 1H, J=8.00 Hz), 7.57 (d, 1H, J=7.77 Hz), 7.56 (s, 1H), 6.96 (d, 1H, J=4.64 Hz), 6.93 (d, 1H, J=4.41 Hz), 6.58 (s, 1H), 6.30 (d, 1H, J=8.96 Hz), 5.75 (s, 1H), 3.79 (s, 3H), 3.05 (bs, 4H), 2.60 (s, 6H), 2.43 (bs, 4H), 2.32 (s, 3H), 2.21 (s, 3H).

Example 76

[7-(3-Methanesulfonyl-phenyl)-pyrrolo[2,1-f][1,2,4]triazin-2-yl]-[2-methoxy-4-(4-methyl-piperazin-1-yl)-phenyl]-amine The titled compound was prepared in an analogous fashion to Example 73 replacing 2-Methoxypyridine-5-boronic acid with 3-(Methanesulfonyl) phenyl boronic acid to give [7-(3-M ethanesulfonyl-phenyl)-pyrrolo[2,1-f][1,2,4]triazin-2-yl]-[2-methoxy-4-(4-methyl-piperazin-1-yl)-phenyl]-amine as a yellow solid (40 mg, 34%). MP 147-150° C. LCMS (E/I+) 493.21 (M+H). NMR $^1$H (DSMO-d$_6$)-8.97 (s, 1H), 8.56 (s, 1H), 8.46 (d, 1H, J=7.56 Hz), 7.89 (d, 1H, J=7.96 Hz), 7.68-7.79 (m, 2H), 7.27 (d, 1H, J=4.80 Hz), 6.96 (d, 1H, J=4.76 Hz), 6.66 (s, 1H), 6.56 (dd, 1H, J=2.24, 6.57 Hz), 3.83 (s, 3H), 3.23 (s, 3H), 3.13 (t, 4H, J=4.73 Hz), 2.23 (s, 3H).

Example 77

5-{2-[2-Methoxy-4-(4-methyl-piperazin-1-yl)-phenylamino]-pyrrolo[2,1-f][1,2,4]triazin-7-yl}-pyridine-2-carbonitrile The titled compound was prepared in an analogous fashion to Example 73 replacing 2-Methoxypyridine-5-boronic acid with 4-Cyano-3-pyridine boronic acid to give [7-(3-Methanesulfonyl-phenyl)-pyrrolo[2,1-f][1,2,4]triazin-2-yl]-[2-methoxy-4-(4-methyl-piperazin-1-yl)-phenyl]-amine as a yellow solid (40 mg, 40%). MP 177-179° C. LCMS (E/I+) 441.17 (M+H). NMR $^1$H (DSMO-d$_6$)-9.48 (s, 1H), 9.01 (s, 1H), 8.85 (dd, 1H, JJ=2.00, 6.36 Hz), 8.14 (s, 1H), 8.08 (d, 1H, J=8.24 Hz), 7.54 (d, 1H, J=8.56 Hz), 7.47 (d, 1H, J=4.88 Hz), 6.97 (d, 1H, J=4.84 Hz), 6.69 (d, 1H, J=2.26 Hz), 6.56 (d, 1H, J=8.97 Hz), 3.81 (s, 3H), 3.18 (t, 4H, J=4.60 Hz), 2.23 (s, 3H).

Example 78

[4-(4-Methyl-piperazin-1-yl)-phenyl]-(7-phenylsulfanyl-pyrrolo[2,1-f][1,2,4]triazin-2-yl)-amine Into a sealed tube was added (7-Bromo-pyrrolo[2,1-f][1,2,4]triazin-2-yl)-[4-(4-methyl-piperazin-1-yl)-phenyl]-amine (0.120 g, 0.310 mmol), Sodium tert-butoxide (89.5 mg, 0.931 mmol), Copper(I) iodide (4 mg, 0.02 mmol), 1,2-Ethanediol (34.7 uL, 0.623 mmol), N,N-Dimethylformamide (4.4 mL, 56 mmol), and finally Benzenethiol (32.1 uL, 0.313 mmol). The reaction was heated at 120° C. overnight. An HPLC showed 40% starting material remaining The reaction was partitioned with water and DCM. The organic was separated, washed with Brine and dried over Na2SO4. The solid was filtered and washed with DCM. The Solvent was removed under vacuum. The desired product was purified via ISCO column chromatography with DCM and methanol as eluant (0 to 8% methanol). The collected fractions afforded [4-(4-Methyl-piperazin-1-yl)-phenyl]-(7-phenylsulfanyl-pyrrolo[2,1-f][1,2,4]triazin-2-yl)-amine as a yellow solid (35 mg, 27%). MP 155-157° C. LCMS (E/I+) 417.13 (M+H). NMR $^1$H (DSMO-d$_6$)-9.33 (s, 1H), 8.97 (s, 1H), 7.43 (d, 2H, J=9.04 Hz), 7.30 (t, 2H, J=7.57 Hz), 7.18 (t, 1H, J=7.33 Hz), 7.13 (d, 2H, J=8.33 Hz), 7.01 (d, 1H, J=4.60 Hz), 6.92 (d, 1H, J=4.60 Hz), 6.74 (d, 2H, J=9.09 Hz), 3.03 (t, 4H, J=5.96 Hz), 2.44 (t, 4H, J=5.21 Hz), 2.23 (s, 3H).

Example 79

[7-(3-Chloro-phenyl)-pyrrolo[2,1-f][1,2,4]triazin-2-yl]-(6-morpholin-4-yl-pyridin-3-yl)-amine 79a) Into a 30 mL vial, 7-Bromo-2-methanesulfinyl-pyrrolo[2,1-f][1,2,4]triazine (0.858 g, 0.00330 mol), [B] 6-Morpholin-4-yl-pyridin-3-ylamine (1.300 g, 0.007254 mol) and N-Methylpyrrolidinone (2.00 mL, 0.0207 mol) were added and heated at 150° C. for 8 hours. The solvent was removed under vacuum. The desired product was isolated via ISCO column chromatography with DCM and methanol as eluant (0 to 7% methanol). The collected fractions afforded (7-Bromo-pyrrolo[2,1-f][1,2,4]triazin-2-yl)-(6-morpholin-4-yl-pyridin-3-yl)-amine as a yellow solid (0.636 g, 51%). NMR $^1$H (DSMO-d$_6$)-9.47 (s, 1H), 8.87 (s, 1H), 8.74 (d, 1H, J=2.24 Hz), 8.00 (dd, 1H, JJ=2.20, 6.81 Hz), 6.93 (d, 1H, J=4.65 Hz), 6.82-6.90 (m, 2H), 3.71 (t, 4H, J=4.32 Hz), 3.36 (t, 4H, J=4.57 Hz)

79b) Into a 30 mL vial, Palladium Acetate (12 mg, 0.000053 mol) and Triphenylphosphine (40 mg, 0.0002 mol) were added and purged under an atmosphere of Nitrogen for 10 minutes. 1,4-Dioxane (2.0 mL, 0.026 mol) was added and stirred for 10 minutes. (7-Bromo-pyrrolo[2,1-f][1,2,4]triazin-2-yl)-(6-morpholin-4-yl-pyridin-3-yl)-amine (0.085 g, 0.00023 mol), 3-chlorophenyl boronic acid (0.0712 g, 0.000455 mol), N,N-Dimethylformamide (2.0 mL, 0.026 mol) and 1.50 M of Sodium carbonate in Water (0.842 mL, 0.00126 mol) were added and heated at 85° C. for 8 hours. The reaction was partitioned with DCM. The solid was filtered and washed with DCM. The organic solvent was removed under vacuum. The desired product was isolated via ISCO column chromatography with DCM and methanol as eluant (0 to 10% methanol). The collected fractions afforded [7-(3-Chloro-phenyl)-pyrrolo[2,1-f][1,2,4]triazin-2-yl]-(6-morpholin-4-yl-pyridin-3-yl)-amine as a yellow solid. MP 221-222° C. LCMS (E/I+) 407.19 (M+H). NMR $^1$H (DSMO-d$_6$)-9.29 (s, 1H), 8.98 (s, 1H), 8.41 (d, 1H, J=2.48 Hz), 8.37 (s, 1H), 8.03 (d, 1H, J=7.52 Hz), 7.99 (dd, 2H, JJ=2.68, 6.41 Hz), 7.50 (t, 1H, J=7.88 Hz), 7.40 (d, 1H, J=8.00 Hz), 7.26 (d, 1H, J=4.84 Hz), 6.94 (d, 1H, J=4.74 Hz), 6.86 (d, 1H, J=9.12 Hz), 3.71 (t, 4H, J=4.64 Hz), 3.37 (t, 4H, J=4.92 Hz).

Example 80

(2-Chloro-4-morpholin-4-yl-phenyl)-(5-chloro-7-phenyl-pyrrolo[2,1-f][1,2,4]triazin-2-yl)-amine Into a 1 dram vial, (4-Morpholin-4-yl-phenyl)-(7-phenyl-pyrrolo[2,1-f][1,2,4]triazin-2-yl)-amine (40 mg, 0.0001 mol; Supplier=Cephalon), N-Chlorosuccinimide (0.014 g, 0.00011 mol), Tetrahydrofuran (2.00 mL, 0.0246 mol), and Methanol (0.50 mL, 0.012 mol) were added. The reaction was stirred at room temperature overnight. The reaction was purified via ISCO column chromatography with hexane and EtOAc as eluant (0 to 75% EtOAc). The collected fractions afforded (2-Chloro-4-morpholin-4-yl-phenyl)-(5-chloro-7-phenyl-pyrrolo[2,1-f][1,2,4]triazin-2-yl)-amine as a yellow solid. MP 242-244° C. LCMS (E/I+) 440.06 (M+H). NMR $^1$H (DSMO-d$_6$)-9.75 (s, 1H), 9.02 (s, 1H), 8.14 (d, 2H, J=9.56 Hz), 8.08 (d, 1H, J=2.75 Hz), 7.56 (d, 2H, J=9.56 Hz), 7.50 (dd, 2H, JJ=2.74, 6.04 Hz), 7.43 (d, 1H, J=7.41 Hz), 7.33 (s, 1H), 7.15 (d, 1H, J=9.56 Hz), 3.74 (t, 4H, J=6.25 Hz), 2.93 (t, 4H, J=7.53 Hz).

Example 81

[7-(6-Methoxy-pyridin-3-yl)-pyrrolo[2,1-f][1,2,4]triazin-2-yl]-[4-(4-methyl-piperazin-1-yl)-phenyl]-amine The titled compound was prepared in an analogous fashion to Example 7 replacing 2-Phenylboronic acid with 2-Methoxypyridine-5-boronic acid to give [7-(6-Methoxy-pyridin-3-yl)-pyrrolo[2,1-f][1,2,4]triazin-2-yl]-[4-(4-methyl-piperazin-1-yl)-phenyl]-amine as a yellow solid (38 mg, 38%). MP 169-171° C. LCMS (E/I+) 416.19 (M+H). NMR $^1$H (DSMO-d$_6$)-9.22 (s, 1H), 8.93 (s, 1H), 8.89 (d, 1H, J=2.28 Hz), 8.53

(dd, 1H, JJ=2.20, 6.52 Hz), 7.80 (s, 1H), 7.56 (d, 2H, J=9.05 Hz), 7.15 (d, 1H, J=4.68 Hz), 7.02 (d, 1H, J=8.72 Hz), 6.87-7.95 (m, 3H), 3.93 (s, 3H), 3.08 (t, 4H, J=4.60 Hz), 2.38-2.58 (m, 4H), 2.22 (s, 3H).

Example 82

[7-(3-Methanesulfonyl-phenyl)-pyrrolo[2,1-f][1,2,4]triazin-2-yl]-[4-(4-methyl-piperazin-1-yl)-phenyl]-amine The titled compound was prepared in an analogous fashion to Example 7 replacing 2-Phenylboronic acid with 3-(Methanesulfonyl) phenyl boronic acid to give [7-(3-Methanesulfonyl-phenyl)-pyrrolo[2,1-f][1,2,4]triazin-2-yl]-[4-(4-methyl-piperazin-1-yl)-phenyl]-amine as a yellow solid (38 mg, 38%). MP 198-201° C. LCMS (E/I+) 462.10 (M+H). NMR $^1$H (DSMO-$d_6$)-8.72 (s, 1H), 8.66 (s, 1H), 8.43 (d, 1H, J=5.40 Hz), 7.91 (d, 1H, J=5.21 Hz), 7.65 (bs, 1H), 7.50 (d, 1H, J=6.25 Hz), 6.85-7.15 (m, 5H), 3.22 (bs, 4H), 3.05 (bs, 3H), 2.63 (s, 4H), 2.39 (s, 3H).

Example 83

N,N-Dimethyl-4-{2-[4-(4-methyl-piperazin-1-yl)-phenylamino]-pyrrolo[2,1-f][1,2,4]triazin-7-yl}-benzenesulfonamide The titled compound was prepared in an analogous fashion to Example 7 replacing 2-Phenylboronic acid with N,N-Dimethylsulfonamide-4-benzeneboronic acid to give N,N-Dimethyl-4-{2-[4-(4-methyl-piperazin-1-yl)-phenylamino]-pyrrolo[2,1-f][1,2,4]triazin-7-yl}-benzenesulfonamide as a yellow solid (100 mg, 85%). MP 217-219° C. LCMS (E/I+) 492.21 (M+H). NMR $^1$H (DSMO-$d_6$)-9.29 (s, 1H), 9.00 (s, 1H), 8.43 (d, 2H, J=8.57 Hz), 7.85 (d, 2H, J=8.52 Hz), 7.56 (s, 1H), 7.56 (d, 2H, J=8.97 Hz), 7.28 (d, 1H, J=4.80 Hz), 6.95 (d, 1H, J=4.76 Hz), 6.92 (d, 2H, J=9.09 Hz), 3.07 (t, 4H, J=4.68 Hz), 2.66 (s, 6H), 2.46 (t, 4H, J=4.92 Hz), 2.22 (s, 3H).

Example 84

(5,7-Dibromo-pyrrolo[2,1-f][1,2,4]triazin-2-yl)-[4-(4-methyl-piperazin-1-yl)-phenyl]-amine The titled compound was prepared in an analogous fashion to Example 1G replacing 7-Bromo-2-methylsulfanyl-pyrrolo[2,1-f][1,2,4]triazine with 5,7-Dibromo-2-methylsulfanyl-pyrrolo[2,1-f][1,2,4]triazine to give (5,7-Dibromo-pyrrolo[2,1-f][1,2,4]triazin-2-yl)-[4-(4-methyl-piperazin-1-yl)-phenyl]-amine as a yellow solid (33 mg, 28%). LCMS (E/I+) 446.96 (M+H). NMR $^1$H (DSMO-$d_6$)-8.54 (s, 1H), 7.63 (d, 2H, J=8.97 Hz), 7.00 (d, 2H, J=9.01 Hz), 6.82 (s, 1H), 6.75 (s, 1H), 3.21 (t, 4H, J=4.88 Hz), 2.61 (t, 4H, J=5.01 Hz), 2.38 (s, 3H).

Example 85

[7-(4-Methanesulfonyl-phenyl)-pyrrolo[2,1-f][1,2,4]triazin-2-yl]-(4-piperidin-1-yl-phenyl)-amine 85a) 2-Methanesulfinyl-7-(3-methanesulfonyl-phenyl)-pyrrolo[2,1-f][1,2,4]triazine Into a 30 mL vial, Palladium Acetate (0.059 g, 0.26 mmol) and Triphenylphosphine (0.19 g, 0.74 mmol) were added. The mixture was purged under an atmosphere of Nitrogen for 10 minutes. 1,4-Dioxane (20.0 mL, 256 mmol) was added and stirred for 10 minutes at room temperature. 7-Bromo-2-methylsulfanyl-pyrrolo[2,1-f][1,2,4]triazine (0.643 g, 2.63 mmol), 3-(Methanesulfonyl) phenyl boronic acid (1.05 g, 5.27 mmol), N,N-Dimethylformamide (4.0E1 mL, 520 mmol), and 1.50 M of Sodium carbonate in Water (15.8 mL, 23.7 mmol) were added. The reaction was heated at 90° C. for 3 hours. The reaction was partitioned with water and DCM. The organic was separated, washed with Brine, and dried over magnesium sulfate. The solid was filtered and washed with EtOAc. The solvent was removed under vacuum to give a solid the solid was triturated with methanol. The solid was filtered and washed with cold methanol to give a yellow solid (420 mg). The solid was treated with Methylene chloride (200 mL, 3000 mmol) and m-Chloroperbenzoic acid (0.250 g, 1.45 mmol) at room temperature. The reaction was stirred at room temperature for 2 hours. The reaction was partitioned with saturated NaHCO3 and DCM. The organic was separated, washed with water subsequently with Brine and dried over sodium sulfate. The solid was filtered and washed with DCM. The solvent was removed under vacuum to give a solid. The solid was washed with Et2O to give 2-Methanesulfinyl-7-(3-methanesulfonyl-phenyl)-pyrrolo[2,1-f][1,2,4]triazine as a yellow solid (0.32 g, 36%). LCMS 336.18 (M+H).

85b) Into a 30 mL vial, 2-Methanesulfinyl-7-(3-methanesulfonyl-phenyl)-pyrrolo[2,1-f][1,2,4]triazine (0.120 g, 0.000358 mol), 4-Piperidin-1-yl-phenylamine (0.1387 g, 0.0007871 mol) and N-Methylpyrrolidinone (1.50 mL, 0.0156 mol) were added and heated at 150° C. for 8 hours. The solvent was removed under vacuum. The desired product was isolated via ISCO column chromatography with DCM and methanol as eluant (0 to 7% methanol). The collected fractions afforded [7-(4-Methanesulfonyl-phenyl)-pyrrolo[2,1-f][1,2,4]triazin-2-yl]-(4-piperidin-1-yl-phenyl)-amine as a yellow solid (36 mg, 18%). MP 204-209° C. LCMS (E/I+) 448.21 (M+H). NMR $^1$H (DSMO-$d_6$)-9.28 (s, 1H), 8.99 (s, 1H), 8.59 (s, 1H), 8.48 (d, 1H, J=7.92 Hz), 7.93 (d, 2H, J=7.85 Hz), 7.81 (t, 1H, J=7.88 Hz), 7.57 (d, 2H, J=8.96 Hz), 7.25 (d, 1H, J=4.77 Hz), 6.95 (d, 1H, J=4.80 Hz), 6.93 (d, 2H, J=9.01 Hz), 3.28 (s, 3H), 3.04 (t, 4H, J=5.24 Hz), 1.47-1.70 (m, 6H).

Example 86

N,N-Dimethyl-4-[2-(4-piperidin-1-yl-phenylamino)-pyrrolo[2,1-f][1,2,4]triazin-7-yl]-benzenesulfonamide The titled compound was prepared in analogous fashion as Example 85 replacing 3-(Methanesulfonyl) phenyl boronic acid with N,N-Dimethylsulfonamide-4-benzeneboronic acid to give N,N-Dimethyl-4-[2-(4-piperidin-1-yl-phenylamino)-pyrrolo[2,1-f][1,2,4]triazin-7-yl]-benzenesulfonamide as a yellow solid (56 mg, 24%). MP 197-203. LCMS (E/I+) 477.12 (M+H)NMR $^1$H (DSMO-$d_6$)-9.27 (s, 1H), 9.00 (s, 1H), 8.43 (d, 2H, J=8.49 Hz), 7.92 (d, 2H, J=8.48 Hz), 7.56 (s, 1H), 7.56 (d, 2H, J=8.97 Hz), 7.28 (d, 1H, J=4.76 Hz), 6.95 (d, 1H, J=4.76 Hz), 6.91 (d, 2H, J=9.00 Hz), 3.06 (t, 4H, J=5.16 Hz), 2.66 (s, 6H), 1.45-1.72 (m, 6H).

Example 87

(1-{4-[7-(4-Methanesulfonyl-phenyl)-pyrrolo[2,1-f][1,2,4]triazin-2-ylamino]-phenyl}-piperidin-4-yl)-methanol 87a) Into a 1-Neck round-bottom flask 4-(Hydroxymethyl)piperidine (6.53 g, 56.7 mmol), Potassium carbonate (7.84 g, 56.7 mmol), Acetonitrile (50 mL, 1000 mmol), and [A]

4-Fluoronitrobenzene (4.00 g, 28.3 mmol)were added. The reaction was heated at 60° C. overnight. The reaction content was poured into ice water and stirred for 30 minutes. The solid was filtered, washed with water and dried under vacuum to give [1-(4-Nitro-phenyl)-piperidin-4-yl]-methanol as an off-white solid (5.20 g, 78%). NMR $^1$H (DSMO-d$_6$)-8.02 (d, 2H, J=9.40 Hz), 7.00 (d, 2H J=9.49 Hz), 4.50 (bs, 1H), 4.07 (bd, 1H, J=13.33 Hz), 3.27 (d, 1H, J=5.84 Hz), 2.94 (t, 2H), 1.80-1.95 (m, 3H), 1.02-1.13 (m, 2H)

87b) Into a Round bottom flask, [A] [1-(4-Nitro-phenyl)-piperidin-4-yl]-methanol (5.021 g, 0.02125 mol), Ethanol (150 mL, 2.6 mol) and 10% Pd/C (10:90, Palladium:carbon black, 2.3 g, 0.0021 mol). The mixture was evacuated and charged with hydrogen via a balloon (3×). The reaction was stirred at RT under an atmosphere of Hydrogen over night. The solid was filtered and washed with Ethanol. The solvent was removed under vacuum to give [1-(4-Amino-phenyl)-piperidin-4-yl]-methanol a brown solid. The solid was triturated with Et2O to give a pink solid. NMR $^1$H (DSMO-d$_6$)-6.68 (d, 2H, J=8.72 Hz), 6.47 (d, 2H J=8.68 Hz), 4.51 (bs, 2H), 4.43 (t, 1H, J=4.25 Hz), 3.22-3.40 (m, 4H), 2.43 (dt, 2H, JJ=2.24, 9.61 Hz) 1.70 (bd, 2H, J=11.15 Hz), 1.25-1.47 (m, 3H)

87c) Into 30 mL vial, 2-Methanesulfinyl-7-(4-methanesulfonyl-phenyl)-pyrrolo[2,1-f][1,2,4]triazine (80 mg, 0.0002 mol), [1-(4-Amino-phenyl)-piperidin-4-yl]-methanol (0.108 g, 0.000525 mol), and N-Methylpyrrolidinone (0.30 mL, 0.0031 mol) were added. The reaction mixture was heated at 150° C. for 5 hours. DCM was added. The solvent was removed under vacuum. The reaction was purified via reverse phase HPLC with ACN and water as eluant (20 to 50 ACN). The collected fractions afforded (1-{4-[7-(4-Methanesulfonyl-phenyl)-pyrrolo[2,1-f][1,2,4]triazin-2-ylamino]-phenyl}-piperidin-4-yl)-methanol; compound with trifluoro-acetic acid as a yellow powder (18 mg, 16%). LCMS (E/I+) 478.22 (M+H). NMR $^1$H (DSMO-d$_6$)-9.29 (s, 1H), 9.00 (s, 1H), 8.59 (s, 1H), 8.49 (d, 2H, J=8.61 Hz), 8.02 (d, 2H, J=8.60 Hz), 7.56 (d, 2H, J=8.96 Hz), 7.32 (d, 1H, J=4.80 Hz), 6.90-7.00 (m, 3H), 4.46 (t, 1H, J=5.28 Hz), 3.63 (d, 2H, J=12.21 Hz), 3.18-3.36 (m, 5H), 2.60 (t, 2H, J=9.81 Hz), 1.78 (t, 2H, J=11.68 Hz), 1.40-1.55 (m, 1H), 1.18-1.35 (m, 2H).

Example 88

2-(4-{4-[7-(4-Methanesulfonyl-phenyl)-pyrrolo[2,1-f][1,2,4]triazin-2-ylamino]-phenyl}-piperazin-1-yl)-ethanol The titled compound was prepared in an analogous fashion to Example 87 replacing 4-(Hydroxymethyl)piperidine with 2-piperazin-1-yl-ethanol to give 2-(4-{4-[7-(4-Methanesulfonyl-phenyl)-pyrrolo[2,1-f][1,2,4]triazin-2-ylamino]-phenyl}-piperazin-1-yl)-ethanol as a yellow solid (30 mg, 25%). MP 253-255° C. LCMS (E/I+) 493.21 (M+H). NMR $^1$H (DSMO-d$_6$)-9.31 (s, 1H), 9.01 (s, 1H), 8.48 (d, 2H, J=8.57 Hz), 8.02 (d, 2H, J=8.56 Hz), 7.58 (d, 2H, J=9.00 Hz), 7.33 (d, 1H, J=4.84 Hz), 6.93-7.02 (m, 3H), 4.43 (bs, 1H), 3.55 (q, 2H, JJ=5.85, 5.72 Hz), 3.29 (s, 3H), 3.09 (bs, 4H), 2.58 (bs, 4H), 2.35-2.55 (bm, 2H).

Example 89

[7-(4-Methanesulfonyl-phenyl)-pyrrolo[2,1-f][1,2,4]triazin-2-yl]-[3-(2-methoxy-ethyl)-2,3,4,5-tetrahydro-1H-benzo[d]azepin-7-yl]-amine The above compound was prepared in an analogous fashion to Example 59 replacing 4-(4-Methyl-piperazin-1-yl)-phenylamine with 3-(2-Methoxy-ethyl)-2,3,4,5-tetrahydro-1H-benzo[d]azepin-7-ylamine to give [7-(4-Methanesulfonyl-phenyl)-pyrrolo[2,1-f][1,2,4]triazin-2-yl]-(6-morpholin-4-yl-pyridin-3-yl)-amine as a yellow solid (38 mg, 32%). MP 240-241° C. LCMS (E/I+) 373.18 (M+H). MP 171-177° C. LCMS (E/I+) 492.22 (M+H). NMR $^1$H (DSMO-d$_6$)-9.47 (s, 1H), 9.04 (s, 1H), 8.47 (d, 2H, J=8.48 Hz), 8.01 (d, 2H, J=8.49 Hz), 7.67 (d, 1H, J=1.69 Hz), 7.26-7.45 (m, 2H), 7.06 (d, 1H, J=8.09 Hz), 6.98 (d, 1H, J=4.80 Hz), 3.47 (t, 2H, J=5.96 Hz), 3.25 (s, 3H), 2.70-2.90 (m, 4H), 2.57-2.70 (m, 6H).

Example 90

[3-Fluoro-4-(4-methyl-piperazin-1-yl)-phenyl]-[7-(2-methoxy-phenyl)-pyrrolo[2,1-f][1,2,4]triazin-2-yl]-amine The above compound was prepared in an analogous fashion to Example 47 replacing 6-Morpholin-4-yl-pyridin-3-ylamine with 3-Fluoro-4-(4-methyl-piperazin-1-yl)-phenylamine to give [8-Methoxy-3-(2-methoxy-ethyl)-2,3,4,5-tetrahydro-1H-benzo[d]azepin-7-yl]-[7-(2-methoxy-phenyl)-pyrrolo[2,1-f][1,2,4]triazin-2-yl]-amine; compound with trifluoro-acetic acid as a yellow powder (27 mg, 19%). MP 205-206° C. LCMS (E/I+) 433.25 (M+H). NMR $^1$H (CDCl$_3$-d)-8.67 (s, 1H), 7.88 (dd, 1H, JJ=1.64, 5.96 Hz), 7.77 (dd, 1H, JJ=2.40, 12.64 Hz), 7.44 (dt, 1H, JJ=1.68, 7.98 Hz), 7.13 (t, 1H, J=7.48 Hz), 7.08 (d, 1H, J=8.32 Hz), 7.01 (d, 1H, J=4.72 Hz), 6.94 (dd, 1H, J=2.56, 6.28 Hz), 6.83-6.90 (m, 2H), 6.68 (bs, 1H), 3.85 (s, 3H), 3.06 (s, 4H), 2.60 (s, 4H), 2.35 (s, 3H).

Example 91

[5-Bromo-7-(4-methanesulfonyl-phenyl)-pyrrolo[2,1-f][1,2,4]triazin-2-yl]-[4-(4-methyl-piperazin-1-yl)-phenyl]-amine 91a) Into a 30 mL vial, 7-(4-Methanesulfonyl-phenyl)-2-methylsulfanyl-pyrrolo[2,1-f][1,2,4]triazine (0.205 g, 0.000642 mol), Methanol (4 mL, 0.1 mol) and Tetrahydrofuran (9 mL, 0.1 mol) were added. N-Bromosuccinimide (0.137 g, 0.000770 mol) was added portion wise over 5 minutes. The reaction was stirred at room temperature over night. The solvent was removed under vacuum. The solid was partitioned with water and filtered to give a yellow solid. The solid was washed with cold methanol to give 5-Bromo-7-(4-methanesulfonyl-phenyl)-2-methylsulfanyl-pyrrolo[2,1-f][1,2,4]triazine as a yellow solid (140 mg, 55%). NMR $^1$H (DSMO-d$_6$)-9.01 (s, 1H), 8.48 (d, 2H, J=8.48 Hz), 8.07 (d, 2H, J=8.53 Hz), 7.79 (s, 1H), 3.28 (s, 3H), 2.62 (s, 3H)

91b) Into a 30 mL vial, 5-Bromo-7-(4-methanesulfonyl-phenyl)-2-methylsulfanyl-pyrrolo[2,1-f][1,2,4]triazine (0.140 g, 0.000351 mol) and Methylene chloride (4 mL, 0.07 mol). m-CPBA 70-75% (70:30, m-Chloroperbenzoic acid:3-Chlorobenzoic acid, 0.0910 g, 0.000369 mol) was added portion wise over 10 minutes. The reaction was stirred at room temperature for 2 hours. HPLC suggested no starting material. The reaction was partitioned with DCM and NaHCO$_3$. The organic was separated, washed with water, subsequently Brine and dried over Na$_2$SO$_4$. The solid was filtered and washed with DCM. The organic was removed under vacuum to give 5-Bromo-2-methanesulfinyl-7-(4-methanesulfonyl-phenyl)-pyrrolo[2,1-f][1,2,4]triazine as a yellow solid (140 mg, 96%). The solid was used as is without further purification.

91c) Into a 30 mL vial, 5-Bromo-2-methanesulfinyl-7-(4-methanesulfonyl-phenyl)-pyrrolo[2,1-f][1,2,4]triazine (0.14 g, 0.00034 mol), 4-(4-Methyl-piperazin-1-yl)-phenylamine (0.194 g, 0.00101 mol), and N-Methylpyrrolidinone (0.22 mL, 0.0023 mol) were added. The mixture was heated at 150° C. for 3 hours. The mixture was purified via ISCO column chromatography with DCM and MeOH as eluant (0 to 15% methanol). The collected fractions afforded [5-Bromo-7-(4-methanesulfonyl-phenyl)-pyrrolo[2,1-f][1,2,4]triazin-2-yl]-[4-(4-methyl-piperazin-1-yl)-phenyl]-amine as a yellow solid (80 mg, 44%). MP 265-266° C. LCMS (E/I+) 543.11 (M+H). NMR $^1$H (DSMO-$d_6$)-9.49 (s, 1H), 8.93 (s, 1H), 8.45 (d, 2H, J=8.56 Hz), 8.03 (d, 2H, J=8.60 Hz), 7.55 (d, 2H, J=9.01 Hz), 7.35 (s, 1H), 6.96 (d, 2H, J=9.08 Hz), 3.39 (s, 3H), 3.10 (t, 4H, J=5.00 Hz), 2.47 (t, 4H, J=5.13 Hz), 2.23 (s, 3H).

Example 92

8-[7-(4-Methanesulfonyl-phenyl)-pyrrolo[2,1-f][1,2,4]triazin-2-ylamino]-5,5-dimethyl-1,3,4,5-tetrahydro-benzo[b]azepin-2-one The above compound was prepared in an analogous fashion to Example 47 replacing 4-(4-Methyl-piperazin-1-yl)-phenylamine with 8-Amino-5,5-dimethyl-1,3,4,5-tetrahydro-benzo[b]azepin-2-one to give 8-[7-(4-Methanesulfonyl-phenyl)-pyrrolo[2,1-f][1,2,4]triazin-2-ylamino]-5,5-dimethyl-1,3,4,5-tetrahydro-benzo[b]azepin-2-one; compound with trifluoro-acetic acid as a yellow powder (6 mg, 5%). LCMS (E/I+) 476.22 (M+H). NMR $^1$H (DSMO-$d_6$)-9.63 (s, 1H), 9.48 (s, 1H), 9.06 (s, 1H), 8.45 (d, 2H, J=8.41 Hz), 8.01 (d, 2H, J=8.44 Hz), 7.26-7.38 (m, 3H), 7.01 (d, 2H, J=4.80 Hz), 3.29 (s, 3H), 2.23 (t, 2H, J=7.00 Hz), 1.99 (t, 2H, J=6.84 Hz), 1.34 (s, 6H).

Example 93

[7-(3-Chloro-phenyl)-pyrrolo[2,1-f][1,2,4]triazin-2-yl]-{4-[2-(4-ethyl-piperazin-1-yl)-ethoxy]-phenyl}-amine 93a) Into a 30 mL vial, 1-(2-Bromo-ethoxy)-4-nitro-benzene (5.00 g, 0.0203 mol), piperazine, 1-methyl-(4.51 mL, 0.0406 mol), Acetonitrile (15.0 mL, 0.287 mol) and Potassium carbonate (5.62 g, 0.0406 mol) were added. The reaction was heated at 80° C. for 4 hours. The reaction was partitioned with water and extracted with Et2O (3×100 mL). The Combined organic was washed with Brine, and dried over magnesium sulfate. The solid was filtered and washed with EtOAc. The solvent was removed under vacuum to afford 1-Methyl-4-[2-(4-nitro-phenoxy)-ethyl]-piperazine as an off white solid (3.89 g, 73%). NMR $^1$H (DSMO-$d_6$-8.20 (dd, 2H, JJ=2.04, 5.12 Hz), 7.16 (dd, 2H, JJ=2.04, 5.08 Hz), 4.22 (t, 2H, J=5.76 Hz), 2.71 (t, 2H, J=5.72 Hz), 2.18-2.6 (bm, 8H), 2.13 (s, 3H)

93b) Into a Round bottom flask, 1-Methyl-4-[2-(4-nitrophenoxy)-ethyl]-piperazine (3.89 g, 0.0147 mol), 10% Pd/C (10:90, Palladium:carbon black, 1.6 g, 0.0015 mol), and Ethanol (100 mL, 2 mol) were added. The mixture was evacuated under house vacuum and charged with a hydrogen balloon (3×). The reaction was stirred at room temperature under an atmosphere of Hydrogen via a balloon. The solid was filtered. The solvent was removed under vacuum. The desired product was purified via ISCO column chromatography with DCM and methanol as eluant (0 to 10%). The collected fractions afforded 4-[2-(4-Methyl-piperazin-1-yl)-ethoxy]-phenylamine as a red solid (2.35 g, 68%). NMR $^1$H (DSMO-$d_6$-6.63 (dd, 2H, JJ=1.92, 4.72 Hz), 6.48 (dd, 2H, JJ=1.96, 4.72 Hz), 4.52 (bs, 2H), 3.89 (t, 2H, J=5.92 Hz), 2.59 (t, 2H, J=5.92 Hz), 2.44 (bs, 4H), 2.29 (bs, 4H), 2.13 (s, 3H)

93c) The titled compound was prepared in an analogous fashion to Example 49 replacing 4-Piperidin-1-yl-phenylamine with 4-[2-(4-Methyl-piperazin-1-yl)-ethoxy]-phenylamine to give [7-(3-Chloro-phenyl)-pyrrolo[2,1-f][1,2,4]triazin-2-yl]-{4-[2-(4-ethyl-piperazin-1-yl)-ethoxy]-phenyl}-amine; compound with trifluoro-acetic acid as a yellow powder (16 mg, 14%). LCMS (E/I+) 463.23 (M+H). NMR $^1$H (DSMO-$d_6$)-9.41 (s, 1H), 8.99 (s, 1H), 8.48 (s, 1H), 8.02 (d, 1H, J=7.80 Hz), 7.69 (d, 2H, J=8.97 Hz), 7.54 (t, 1H, J=7.93 Hz), 7.44 (d, 2H, J=9.77 Hz), 7.27 (d, 1H, J=4.76 Hz), 6.90-7.00 (m, 3H), 4.15 (t, 2H, J=5.20 Hz), 2.50-3.50 (bm, 13H).

Example 94

[7-(2-Methoxy-phenyl)-pyrrolo[2,1-f][1,2,4]triazin-2-yl]-{4-[2-(4-methyl-piperazin-1-yl)-ethoxy]-phenyl}-amine The titled compound was prepared in an analogous fashion to Example 47 replacing 6-Morpholin-4-yl-pyridin-3-ylamine with 4-[2-(4-Methyl-piperazin-1-yl)-ethoxy]-phenylamine to [7-(2-Methoxy-phenyl)-pyrrolo[2,1-f][1,2,4]triazin-2-yl]-{4-[2-(4-methyl-piperazin-1-yl)-ethoxy]-phenyl}-amine; compound with trifluoro-acetic acid as a yellow powder. LCMS (E/I+) 459.9 (M+H). NMR $^1$H (DSMO-$d_6$)-9.27 (s, 1H), 8.93 (s, 1H7.81 (dd, 1H, Jj=1.40, 6.17 Hz), 7.65 (d, 2H, J=9.00 Hz), 7.45 (t, 1H, J=9.72 Hz), 7.21 (d, 1H, J=8.32 Hz), 7.12 (t, 1H, J=7.49 Hz), 6.94 (d, 1H, J=4.61 hz), 6.91 (d, 1H, J=4.64), 6.84 (d, 2H, J=9.00 Hz), 4.19 (t, 2H, J=4.72 Hz), 3.78 (s, 3H), 2.90-3.70 (bm, 10), 2.84 (s, 3H).

Example 95

2-[4-(4-Amino-phenyl)-piperazin-1-yl]-ethanol to give 2-(4-{4-[7-(3-Methanesulfonyl-phenyl)-pyrrolo[2,1-f][1,2,4]triazin-2-ylamino]-phenyl}-piperazin-1-yl)-ethanol The titled compound was prepared in analogous fashion as Example 85 replacing 4-Piperidin-1-yl-phenylamine with 2-[4-(4-Amino-phenyl)-piperazin-1-yl]-ethanol to give 2-(4-{4-[7-(3-Methanesulfonyl-phenyl)-pyrrolo[2,1-f][1,2,4]triazin-2-ylamino]-phenyl}-piperazin-1-yl)-ethanol as a yellow solid (28 mg, 24%). LCMS (E/I+) 493.18 (M+H). NMR $^1$H (DSMO-$d_6$)-9.29 (s, 1H), 8.99 (s, 1H), 8.59 (s, 1H), 8.48 (d, 1H, J=7.88 Hz), 7.93 (d, 1H, J=7.93 Hz), 7.81 (t, 1H, J=7.84 Hz), 7.58 (d, 2H, J=8.96 Hz), 7.25 (d, 1H, J=4.77 Hz), 6.96 (d, 1H, J=4.80 Hz), 6.94 (d, 2H, J=9.09 Hz), 4.42 (t, 1H, J=5.44 Hz), 3.53 (q, 2H, JJ=6.08, 5.72 Hz), 3.28 (s, 3H), 3.06 (t, 4H, J=4.45 Hz), 2.56 (t, 4H, J=4.52 Hz), 2.11 (t, 2H, J=6.28 Hz).

Example 96

(1-{4-[7-(3-Methanesulfonyl-phenyl)-pyrrolo[2,1-f][1,2,4]triazin-2-ylamino]-phenyl}-piperidin-4-yl)-methanol The titled compound was prepared in analogous fashion as Example 85 replacing 4-Piperidin-1-yl-phenylamine with [1-(4-Amino-phenyl)-piperidin-4-yl]-methanol to give (1-{4-[7-(3-Methanesulfonyl-phenyl)-pyrrolo[2,1-f][1,2,4]triazin-2-ylamino]-phenyl}-piperidin-4-yl)-methanol as a yellow solid (42 mg, 35%). LCMS (E/I+) 487.16 (M+H). NMR $^1$H (DSMO-d$_6$)-9.27 (s, 1H), 8.99 (s, 1H), 8.58 (s, 1H), 8.50 (d, 1H, J=7.85 Hz), 7.93 (d, 1H, J=7.89 Hz), 7.81 (t, 1H, J=7.88 Hz), 7.57 (d, 2H, J=8.96 Hz), 7.25 (d, 1H, J=4.73 Hz), 6.90-7.00 (m, 3H), 4.46 (t, 1H, J=5.40 Hz), 3.60 (d, 2H, J=12.32 Hz), 3.28 (s, 3H), 2.56 (dt, 4H, JJ=2.40, 9.52 Hz), 1.75 (d, 2H, J=12.17 Hz), 1.50 (bs, 1H), 1.25 (dt, 2H, JJ=3.84, 8.32 Hz).

Example 97

(4-Morpholin-4-yl-phenyl)-(7-phenylsulfanyl-pyrrolo[2,1-f][1,2,4]triazin-2-yl)-amine Into a sealed tube was added (7-Bromo-pyrrolo[2,1-f][1,2,4]triazin-2-yl)-(4-morpholin-4-yl-phenyl)-amine (0.125 g, 0.334 mmol), Sodium tert-butoxide (96.4 mg, 1.00 mmol), Copper(I) iodide (6.4 mg, 0.033 mmol), 1,2-Ethanediol (37.4 uL, 0.671 mmol), N,N-Dimethylformamide (4.7 mL, 6.0E1 mmol), and finally Benzenethiol (51.4 uL, 0.501 mmol). The reaction was heated at 120° C. overnight. The reaction was partitioned with DCM and water. The organic was separated, washed with Brine, and dried over magnesium sulfate. The solid was filtered and washed with DCM. The solvent was removed under vacuum. The product was isolated via ISCO column chromatography with DCM and methanol as eluant (0 to 10% methanol) the collected fractions afforded (4-Morpholin-4-yl-phenyl)-(7-phenylsulfanyl-pyrrolo[2,1-f][1,2,4]triazin-2-yl)-amine an orange solid (72 mg, 53%). MP 143-145° C. LCMS (E/I+) 404.17 (M+H). NMR $^1$H (DSMO-d$_6$)-9.33 (s, 1H), 8.97 (s, 1H), 7.45 (d, 2H, J=9.05 Hz), 7.30 (t, 2H, J=7.57 Hz), 7.18 (t, 1H, J=7.29), 7.12 (d, 2H, J=7.37 Hz), 7.01 (d, 1H, J=4.40 Hz), 6.93 (d, 1H, J=4.60 Hz), 6.75 (d, 2H, J=9.05 Hz), 3.73 (t, 4H, J=4.48 Hz), 3.00 (t, 4H, J=4.72 Hz).

Example 98

[7-(2-Methoxy-phenylsulfanyl)-pyrrolo[2,1-f][1,2,4]triazin-2-yl]-[4-(4-methyl-piperazin-1-yl)-phenyl]-amine Into a sealed tube was added (7-Bromo-pyrrolo[2,1-f][1,2,4]triazin-2-yl)-[4-(4-methyl-piperazin-1-yl)-phenyl]-amine (0.320 g, 0.826 mmol), Sodium tert-butoxide (238 mg, 2.48 mmol), Copper(I) iodide (16 mg, 0.083 mmol), 1,2-Ethanediol (92.6 uL, 1.66 mmol), N,N-Dimethylformamide (12 mL, 150 mmol), and finally 2-Methoxy-benzenethiol (0.174 g, 1.24 mmol). The reaction was heated at 120° C. overnight. The reaction was partitioned with DCM and water. The organic was separated, washed with Brine, and dried over magnesium sulfate. The solid was filtered and washed with DCM. The solvent was removed under vacuum. The product was isolated via ISCO column chromatography with DCM and methanol as eluant (0 to 10% methanol). The collected fractions afforded [7-(2-Methoxy-phenylsulfanyl)-pyrrolo[2,1-f][1,2,4]triazin-2-yl]-[4-(4-methyl-piperazin-1-yl)-phenyl]-amine an orange solid (9 mg, 2.5%). MP 171-172° C. LCMS (E/I+) 447.24 (M+H). NMR $^1$H (DSMO-d$_6$)-9.27 (s, 1H), 8.97 (s, 1H), 7.35 (d, 2H, J=9.00 Hz), 7.08-7.20 (m, 2H), 6.97 (d, 1H, J=4.68 Hz), 6.92 (d, 1H, J=4.57 Hz), 6.75 (t, 1H, J=6.72 Hz), 6.68 (d, 2H, J=9.08 Hz), 6.36 (dd, 1H, JJ=1.40, 6.41 Hz), 3.91 (s, 3H), 3.01 (t, 4H, J=4.72 Hz), 2.43 (t, 4H, J=4.68 Hz), 2.21 (s, 3H).

Example 99

[5-Bromo-7-(4-methanesulfonyl-phenyl)-pyrrolo[2,1-f][1,2,4]triazin-2-yl]-(4-morpholin-4-yl-phenyl)-amine 99a) Into a 30 mL vial, Palladium Acetate (123 mg, 0.546 mmol) and Triphenylphosphine (409 mg, 1.56 mmol) were added and purged under an atmosphere of Nitrogen for 10 minutes. 1,4-Dioxane (20.4 mL, 262 mmol) was added and stirred for 10 minutes. 7-Bromo-2-methylsulfanyl-pyrrolo[2,1-f][1,2,4]triazine (480 mg, 2.0 mmol), Phenylboronic acid (527 mg, 4.32 mmol), N,N-Dimethylformamide (16.4 mL, 211 mmol) and 1.50 M of Sodium carbonate in Water (16.4 mL, 24.5 mmol) were added. The mixture was heated at 90° C. for 4 hours. The solvent was removed under vacuum to give a brown solid. The solid was partitioned with DCM, filtered and washed with DCM. The filtrate was concentrated to give a semi-solid. The product was isolated via ISCO column chromatography with DCM and MeOH as eluant (0 to 5% methanol). The collected fractions afforded 2-Methylsulfanyl-7-phenyl-pyrrolo[2,1-f][1,2,4]triazine as a yellow solid (295 mg, 62%). NMR $^1$H (DSMO-d$_6$)-9.01 (s, 1H), 8.22 (d, 2H, J=9.08 Hz), 7.53 (t, 2H, J=7.56 Hz), 7.34-7.45 (m, 2H), 7.11 (d, 1H, J=4.20), 2.58 (s, 3H)

99b) Into a 30 mL vial, 2-Methylsulfanyl-7-phenyl-pyrrolo[2,1-f][1,2,4]triazine (0.295 g, 0.00122 mol), Tetrahydrofuran (10 mL, 0.1 mol) and Methanol (5 mL, 0.1 mol) were added. N-Bromosuccinimide (0.239 g, 0.00134 mol) was added over 10 minutes. The reaction was stirred at room temperature overnight. The solvent was removed under vacuum. The solid was partitioned with water, filtered and washed with water to give a yellow solid. The solid was dried under vacuum over night to give 5-Bromo-2-methylsulfanyl-7-phenyl-pyrrolo[2,1-f][1,2,4]triazine as a yellow solid (0.34 g, 87%). NMR $^1$H (DSMO-d$_6$)-8.93 (s, 1H), 8.19 (d, 2H, J=7.61 Hz), 7.61 (s, 1H), 7.53 (t, 2H, J=8.60 Hz), 7.42 (t, 1H, J=7.37), 2.58 (s, 3H)

99c) Into a Round bottom flask, [A] 5-Bromo-2-methylsulfanyl-7-phenyl-pyrrolo[2,1-f][1,2,4]triazine (0.30 g, 0.00094 mol) and Methylene chloride (2 mL, 0.03 mol) were added. m-Chloroperbenzoic acid (0.178 g, 0.00103 mol) was added portion wise over 20 minutes. The reaction was stirred at room temperature for one hour. The reaction was partitioned with DCM (200 mL) and saturated NaHCO$_3$ (200 mL). The organic was separated, washed with Brine and dried over Na$_2$SO$_4$. The solid was filtered and washed with DCM. The solvent was removed under vacuum to give a yellow solid. The solid was washed with hexane to give 5-Bromo-2-methanesulfinyl-7-phenyl-pyrrolo[2,1-f][1,2,4]triazine as a yellow solid (270 mg, 86%). NMR $^1$H (DSMO-d$_6$)-9.24 (s, 1H), 8.24 (d, 2H, J=7.44 Hz), 7.92 (s, 1H), 7.56 (t, 2H, J=7.93 Hz), 7.47 (t, 1H, J=7.32 Hz), 2.98 (s, 3H)

99d) Into a 30 mL vial, [A] 5-Bromo-2-methanesulfinyl-7-(4-methanesulfonyl-phenyl)-pyrrolo[2,1-f][1,2,4]triazine (0.14 g, 0.00034 mol), 4-(4-morpholino)aniline (0.181 g, 0.00101 mol), and N-Methylpyrrolidinone (0.22 mL, 0.0023 mol) were added. The mixture was heated at 150° C. for 3 hours. The mixture was purified via ISCO column chromatography with DCM and MeOH as eluant (0 to 15% methanol). The collected fractions afforded [5-Bromo-7-(4-methanesulfonyl-phenyl)-pyrrolo[2,1-f][1,2,4]triazin-2-yl]-(4-morpholin-4-yl-phenyl)-amine as a yellow solid (120 mg, 67%). MP 242-244° C. LCMS (E/I+) 451.23 (M+H). NMR $^1$H (DSMO-d$_6$)-9.43 (s, 1H), 8.86 (s, 1H), 8.16 (d, 2H, J=7.76 Hz), 7.62 (d, 2H, J=8.93 Hz), 7.54 (t, 1H, J=7.77 Hz), 7.41 (t, 1H, J=7.16 Hz), 7.34 (s, 1H), 6.93 (d, 2H, J=8.97 Hz), 3.74 (t, 4H, J=4.29 Hz), 3.06 (t, 4H, J=4.64 Hz).

Example 100

(5-Bromo-7-phenyl-pyrrolo[2,1-f][1,2,4]triazin-2-yl)-[4-(4-methyl-piperazin-1-yl)-phenyl]-amine The titled compound was prepared in an analogous fashion to Example 99 replacing 4-(4-morpholino)aniline with 4-(4-

Methyl-piperazin-1-yl)-phenylamine to give (5-Bromo-7-phenyl-pyrrolo[2,1-f][1,2,4]triazin-2-yl)-[4-(4-methyl-piperazin-1-yl)-phenyl]-amine as a yellow solid (125 mg, 60%). MP 223-225° C. LCMS (E/I+) 463.16 (M+H). NMR $^1$H (DSMO-d$_6$)-9.41 (s, 1H), 8.86 (s, 1H), 8.17 (d, 2H, J=8.48 Hz), 7.66 (d, 2H, J=9.04 Hz), 7.54 (t, 2H, J=7.65 Hz), 7.41 (t, 1H, J=7.32 Hz), 7.34 (s, 1H), 6.92 (d, 2H, J=9.00 Hz), 3.08 (t, 4H, J=4.76 Hz), 2.46 (t, 4H, J=4.88 Hz), 2.22 (s, 3H).

Example 101

[5-Bromo-7-(2-methoxy-phenyl)-pyrrolo[2,1-f][1,2,4]triazin-2-yl]-[4-(4-methyl-piperazin-1-yl)-phenyl]-amine Into a 30 mL vial, Palladium Acetate (1.28 mg, 5.69E-6 mol) and Triphenylphosphine (4 mg, 0.00002 mol) were added and purged under an atmosphere of Nitrogen for 10 minutes. 1,4-Dioxane (0.08 mL, 0.001 mol) was added and stirred for 10 minutes. 2-methoxybenzeneboronic acid (0.0217 g, 0.000143 mol) N,N-Dimethylformamide (0.3 mL, 0.004 mol) and 1.50 M of Sodium carbonate in Water (0.429 mL, 0.000644 mol) were added and heated at 85° C. overnight. The reaction was partitioned with water and EtOAc. The organic was separated, washed with Brine, and dried over magnesium sulfate. The solid was filtered and washed with EtOAc. The solvent was removed under vacuum. The product was isolated via ISCO column chromatography with DCM and MeOH as eluant (0 to 5%). The collected fractions afforded a yellow solid. NMR suggested mixture of regioisomers. The regioisomers were isolated via critical fluid chromatography to give [5-Bromo-7-(2-methoxy-phenyl)-pyrrolo[2,1-f][1,2,4]triazin-2-yl]-[4-(4-methyl-piperazin-1-yl)-phenyl]-amine as an off white solid (5 mg, 7%). LCMS (E/I+) 495.21 (M+H). NMR $^1$H (DSMO-d$_6$)-9.32 (s, 1H), 8.83 (s, 1H), 7.78 (dd, 1H, JJ=1.48, 5.16 Hz), 7.52 (d, 2H, J=8.96 Hz), 7.48 (t, 1H, J=7.16 Hz), 7.22 (d, 1H, J=8.36 Hz), 7.12 (t, 1H, J=7.56 Hz), 7.03 (s, 1H), 6.79 (d, 2H, J=9.04 Hz), 3.80 (s, 3H), 3.03 (t, 4H, J=4.56 Hz), 2.43 (t, 4H, J=4.76 Hz), 2.21 (s, 3H).

Example 102

[7-Bromo-5-(2-methoxy-phenyl)-pyrrolo[2,1-f][1,2,4]triazin-2-yl]-[4-(4-methyl-piperazin-1-yl)-phenyl]-amine Into a 30 mL vial, Palladium Acetate (1.28 mg, 5.69E-6 mol) and Triphenylphosphine (4 mg, 0.00002 mol) were added and purged under an atmosphere of Nitrogen for 10 minutes. 1,4-Dioxane (0.08 mL, 0.001 mol) was added and stirred for 10 minutes. 2-methoxybenzeneboronic acid (0.0217 g, 0.000143 mol) N,N-Dimethylformamide (0.3 mL, 0.004 mol) and 1.50 M of Sodium carbonate in Water (0.429 mL, 0.000644 mol) were added and heated at 85° C. overnight. The reaction was partitioned with water and EtOAc. The organic was separated, washed with Brine, and dried over magnesium sulfate. The solid was filtered and washed with EtOAc. The solvent was removed under vacuum. The product was isolated via ISCO column chromatography with DCM and MeOH as eluant (0 to 5%). The collected fractions afforded a yellow solid. NMR suggested mixture of regioisomers. The regioisomers were isolated via critical fluid chromatography to give [[7-Bromo-5-(2-methoxy-phenyl)-pyrrolo[2,1-f][1,2,4]triazin-2-yl]-[4-(4-methyl-piperazin-1-yl)-phenyl]-amine as an off white solid (3.7 mg, 5%). LCMS (E/I+) 495.20 (M+H). NMR $^1$H (DSMO-d$_6$)-9.43 (s, 1H), 8.78 (s, 1H), 7.76 (d, 2H, J=8.97 Hz), 7.49 (d, 1H, J=6.44 Hz), 7.36 (t, 1H, J=8.01 Hz), 7.16 (d, 1H, J=8.60 Hz), 7.05 (t, 1H, J=7.77 Hz), 7.00 (s, 1H), 6.92 (d, 2H, J=8.97 Hz), 3.82 (s, 3H), 3.08 (t, 4H, J=4.70 Hz), 2.40-2.05 (m, 4H), 2.22 (s, 3H).

Example 103

[7-(2-Methoxy-phenyl)-5-vinyl-pyrrolo[2,1-f][1,2,4]triazin-2-yl]-[4-(4-methyl-piperazin-1-yl)-phenyl]-amine Into a 30 mL vial [5-Bromo-7-(2-methoxy-phenyl)-pyrrolo[2,1-f][1,2,4]triazin-2-yl]-[4-(4-methyl-piperazin-1-yl)-phenyl]-amine (90.0 mg, 0.000182 mol), Vinyl boronic acid (100 mg, 0.002 mol), Potassium carbonate (1.12 g, 0.00814 mol), and Tetrakis(triphenylphosphine)palladium (0) (21.3 mg, 0.0000184 mol) were added and purged under an atmosphere of Nitrogen for 10 minutes. N,N-Dimethylformamide (5 mL, 0.06 mol) was added. The reaction mixture was heated at 140° C. for 4 hours. The reaction was partitioned with water and EtOAc. The organic was separated and washed with water. Subsequently the organic was washed with Brine, and dried over magnesium sulfate. The solid was filtered and washed with EtOAc. The solvent was removed under vacuum. The product was isolated via ISCO column chromatography with DCM and Methanol as eluant (0 to 10% methanol). The collected fractions afforded [7-(2-Methoxy-phenyl)-5-vinyl-pyrrolo[2,1-f][1,2,4]triazin-2-yl]-[4-(4-methyl-piperazin-1-yl)-phenyl]-amine a yellow solid (68 mg, 85%). MP 150-151° C. LCMS (E/I+) 441.24 (M+H). NMR $^1$H (DSMO-d$_6$)-9.17 (s, 1H), 9.14 (s, 1H), 7.75 (dd, 1H, JJ=1.60, 6.04 Hz), 7.53 (d, 2H, J=8.96 Hz), 7.48 (dt, 1H, JJ=1.52, 6.92 Hz), 7.22 (d, 1H, J=8.36 Hz), 7.00-7.18 (m, 3H), 6.78 (d, 2H, J=9.04 Hz), 5.78 (d, 1H, J=17.56 Hz), 5.24 (d, 1H, J=11.81 Hz), 3.80 (s, 3H), 3.02 (t, 4H, J=4.56 Hz), 2.44 (t, 4H, J=4.68 Hz), 2.21 (s, 3H).

Example 104

[7-(4-Methanesulfonyl-phenyl)-5-vinyl-pyrrolo[2,1-f][1,2,4]triazin-2-yl]-[4-(4-methyl-piperazin-1-yl)-phenyl]-amine The tited compound was prepare in an analogous fashion to Example 103 replacing [5-Bromo-7-(2-methoxy-phenyl)-pyrrolo[2,1-f][1,2,4]triazin-2-yl]-[4-(4-methyl-piperazin-1-yl)-phenyl]-amine with [5-Bromo-7-(4-methanesulfonyl-phenyl)-pyrrolo[2,1-f][1,2,4]triazin-2-yl]-[4-(4-methyl-piperazin-1-yl)-phenyl]-amine to give [7-(4-Methanesulfonyl-phenyl)-5-vinyl-pyrrolo[2,1-f][1,2,4]triazin-2-yl]-[4-(4-methyl-piperazin-1-yl)-phenyl]-amine (45 mg, 63%). LCMS (E/I+) 489.21 (M+H). NMR $^1$H (DSMO-d$_6$)-9.23 (s, 1H), 8.99 (s, 1H), 8.48 (d, 2H, J=8.44 Hz), 8.07 (d, 2H, J=8.56 Hz), 7.66 (d, 2H, J=9.01 Hz), 7.00-7.18 (m, 2H), 7.00 (d, 2H, J=8.88 Hz), 5.82 (d, 1H, J=16.95 Hz), 5.21 (d, 1H, J=12.21 Hz), 3.80 (s, 3H), 3.02 (t, 4H, J=4.60 Hz), 2.44 (t, 4H, J=4.72 Hz), 2.21 (s, 3H).

Example 105

[7-(2-Methoxy-phenyl)-5-methyl-pyrrolo[2,1-f][1,2,4]triazin-2-yl]-[4-(4-methyl-piperazin-1-yl)-phenyl]-amine; compound with trifluoro-acetic acid Into a 30 mL vial, [5-Bromo-7-(2-methoxy-phenyl)-pyrrolo[2,1-f][1,2,4]triazin-2-yl]-[4-(4-methyl-piperazin-1-yl)-phenyl]-amine (0.110 g, 0.000223 mol)(Note: [5-Bromo-7-

(2-methoxy-phenyl)-pyrrolo[2,1-f][1,2,4]triazin-2-yl]-[4-(4-methyl-piperazin-1-yl)-phenyl]-amine was prepared in an analogous fashion to Example 100 replacing phenyl boronic acid with 2-methoxyphenyl boronic acid), Trimethylboroxine (0.252 g, 0.00201 mol), and Potassium carbonate (1.39 g, 0.0100 mol) were added and purged under an atmosphere of Nitrogen for 10 minutes. N,N-Dimethylformamide (5 mL, 0.06 mol) was added. The reaction mixture was then heated at 140° C. for 4 hours. LCMS suggested a mixture product and reductive eliminated product. The reaction was partitioned with EtOAc and washed with water (2×). The organic was separated, washed with Brine, and dried over magnesium sulfate. The solid was filtered and washed with EtOAc. The solvent was removed under vacuum. The product was isolated via reverse phase HPLC column chromatography with 0.1% TFA in ACN and 0.1% TFA in Water as eluant (15% to 55% ACN). The collected fractions afforded [7-(2-Methoxy-phenyl)-5-methyl-pyrrolo[2,1-f][1,2,4]triazin-2-yl]-[4-(4-methyl-piperazin-1-yl)-phenyl]-amine; compound with trifluoro-acetic acid as a red powder (10 mg, 10%). LCMS (E/I+) 429.25 (M+H). NMR $^1$H (CDCl$_3$-d)-10.58 (s, 1H), 8.40 (s, 1H), 7.96 (d, 1H, J=8.60 Hz), 7.62 (d, 2H, J=8.61 Hz), 7.55 (t, 1H, J=8.61 Hz), 7.06-7.18 (m, 3), 6.83 (d, 2H, J=8.89 Hz), 3.87s, 3H), 2.90-3.75 (m, 8H), 2.87 (s, 3H), 2.47 (s, 3H).

Example 106

[5-Ethyl-7-(2-methoxy-phenyl)-pyrrolo[2,1-f][1,2,4]triazin-2-yl]-[4-(4-methyl-piperazin-1-yl)-phenyl]-amine Into a par bottle, [7-(2-Methoxy-phenyl)-5-vinyl-pyrrolo[2,1-f][1,2,4]triazin-2-yl]-[4-(4-methyl-piperazin-1-yl)-phenyl]-amine (50.00 mg, 0.0001135 mol), and Ethanol (20 mL, 0.3 mol) were added. Raney-Nickel (0.9:0.1, Nickel:Aluminum, 10 mg, 0.0002 mol) was washed with Ethanol prior to adding to the reaction mixture. The mixture was evacuated and charged with hydrogen at 30 pSi. The reaction was shaken on the parr at 30 pSi for one hour. The solid was filtered through Celite. The organic was evaporated under vacuum to give a yellow solid. The solid was purified via ISCO column chromatography with DCM and MeOH as eluant (0 to 10% methanol). The collected fractions afforded [5-Ethyl-7-(2-methoxy-phenyl)-pyrrolo[2,1-f][1,2,4]triazin-2-yl]-[4-(4-methyl-piperazin-1-yl)-phenyl]-amine as a yellow solid (18 mg, 36%). MP 154-156° C. LCMS (E/I+) 443.31 (M+H). NMR $^1$H (DSMO-d$_6$)-9.05 (s, 1H), 8.92 (s, 1H), 7.80 (dd, 1H, JJ=1.57, 6.50 Hz), 7.55 (d, 2H, J=8.96 Hz), 7.43 (dt, 1H, JJ=1.60, 7.00 Hz), 7.20 (d, 1H, J=8.40) 7.10 (t, 1H, J=7.57 Hz, 6.73-6.85 (m, 3H), 3.79 (s, 3H), 3.02 (t, 4H, J=4.60), 2.83 (q, 2H, JJ=7.52, 7.56 Hz), 2.44 (t, 4H, J=5.84), 2.21 (s, 3H), 1.28 (t, 3H, J=7.56 Hz).

Example 107

[7-(4-Methanesulfonyl-phenyl)-5-methyl-pyrrolo[2,1-f][1,2,4]triazin-2-yl]-(4-morpholin-4-yl-phenyl)-amine 107a) Into a 30 mL vial, 5-Bromo-7-(4-methanesulfonyl-phenyl)-2-methylsulfanyl-pyrrolo[2,1-f][1,2,4]triazine (0.480 g, 0.00120 mol) (Note: 5-Bromo-7-(4-methanesulfonyl-phenyl)-2-methylsulfanyl-pyrrolo[2,1-f][1,2,4]triazine was prepared in an analogous fashion as Example 99b replacing Phenylboronic acid with $-methylsulfonuphenylboronic acid), Trimethylboroxine (1.37 g, 0.0109 mol), Tetrakis(triphenylphosphine)palladium (0) (0.14 g, 0.00012 mol) and Potassium carbonate (7.49 g, 0.0542 mol) were added and purged under an atmosphere of Nitrogen for 10 minutes. N,N-Dimethylformamide (25.0 mL, 0.323 mol) was then added and heated at 130° C. for 4 hours. The reaction was partitioned with water and EtOAc. The organic was separated, washed with Brine, and dried over magnesium sulfate. The solid was filtered and washed with EtOAc. The solvent was removed under vacuum. The product was isolated via ISCO column chromatography with DCM and MeOH as eluant (0 to 5% MeOH). The collected fractions afforded 7-(4-Methanesulfonyl-phenyl)-5-methyl-2-methylsulfanyl-pyrrolo[2,1-f][1,2,4]triazine as a yellow solid (0.26 g, 65%).

107b) Into a 30 mL vial, [A] 7-(4-Methanesulfonyl-phenyl)-5-methyl-2-methylsulfanyl-pyrrolo[2,1-f][1,2,4]triazine (0.260 g, 0.000780 mol) and Methylene chloride (20 mL, 0.3 mol) were added. m-CPBA 70-75% (70:30, m-Chloroperbenzoic acid:3-Chlorobenzoic acid, 0.211 g, 0.000858 mol) was added and stirred at room temperature overnight. The reaction was partitioned with DCM and saturated NaHCO$_3$. The organic was separated and washed with water then Brine and dried over Na$_2$SO$_4$. The solid was filtered and washed with DCM. The organic was removed under vacuum to give a solid. The solid was triturated with Et2O and filtered to give 2-Methanesulfinyl-7-(4-methanesulfonyl-phenyl)-5-methyl-pyrrolo[2,1-f][1,2,4]triazine as a yellow solid (0.20 g, 73%) NMR $^1$H (CDCl$_3$-d)-8.99 (s, 1H), 8.24 (d, 2H, J=8.45 Hz), 8.08 (d, 2H, J=8.40 Hz), 7.28 (s, 1H), 3.10 (s, 3H), 3.02 (bs, 4H), 2.54 (s, 3H)

107c) Into a Microwave vial, [A] 2-Methanesulfinyl-7-(4-methanesulfonyl-phenyl)-5-methyl-pyrrolo[2,1-f][1,2,4]triazine (90.0 mg, 0.000258 mol), [B] 4-(4-morpholino)aniline (0.275 g, 0.00154 mol), and N-Methylpyrrolidinone (0.5 mL, 0.005 mol) were added. The mixture was heated at 180° C. for 3 hours The solvent was removed under vacuum. The reaction was partitioned with water and DCM. The organic was separated, washed with Brine and dried over sodium sulfate. The solid was filtered and washed with DCM. The solvent was removed under vacuum to give a semi-solid. The mixture was purified via HPLC with 0.1% TFA in ACN and 0.1% TFA in water. The collected fractions afforded [7-(4-Methanesulfonyl-phenyl)-5-methyl-pyrrolo[2,1-f][1,2,4]triazin-2-yl]-(4-morpholin-4-yl-phenyl)-amine; compound with trifluoroacetic acid as a red powder as a yellow powder (36 mg, 30%). LCMS (E/I+) 464.00 (M+H). NMR $^1$H (DSMO-d$_6$)-9.33 (s, 1H), 9.04 (s, 1H), 8.47 (d, 2H, J=8.48 Hz), 8.01 (d, 2H, J=8.56 Hz), 7.62 (d, 2H, J=8.89 Hz), 7.15 (s, 1H), 7.02 (d, 2H, J=8.48 Hz), 3.79 (t, 4H, J=7.12 Hz), 3.28 (s, 3H), 3.11 (bs, 4H), 2.41 (s, 3H).

Example 108

[7-(4-Methanesulfonyl-phenyl)-5-methyl-pyrrolo[2,1-f][1,2,4]triazin-2-yl]-[4-(4-methyl-piperazin-1-yl)-phenyl]-amine The above compound was prepared in an analogous fashion to Example 107 replacing 4-(4-morpholino)aniline with 4-(4-Methyl-piperazin-1-yl)-phenylamine to give [7-(4-Methanesulfonyl-phenyl)-5-methyl-pyrrolo[2,1-f][1,2,4]triazin-2-yl]-[4-(4-methyl-piperazin-1-yl)-phenyl]-amine as a yellow powder. LCMS (E/I+) 477.07 (M+H). NMR $^1$H (DSMO-d$_6$)-9.34 (s, 1H), 9.05 (s, 1H), 8.47 (d, 1H, J=8.56 Hz), 8.01 (d, 2H, J=8.56 Hz), 7.63 (d, 2H, J=8.89 Hz), 7.16 (s, 1H), 7.03 (d, 2H, J=9.00 Hz), 3.79 (d, 2H, J=12.68 Hz), 3.28 (s, 3H), 3.15-3.20 (m, 2H), 2.84-3.00 (m, 4H), 2.50 (s, 3H), 2.41 (s, 3H).

Example 109

[7-(2-Ethoxy-phenyl)-pyrrolo[2,1-f][1,2,4]triazin-2-yl]-[4-(4-methyl-piperazin-1-yl)-phenyl]-amine The above compound was prepared in an analogous fashion to Example 7 replacing phenylboronic acid with 2-Ethoxyphenyl boronic acid to give [7-(2-Ethoxy-phenyl)-pyrrolo[2,1-f][1,2,4]triazin-2-yl]-[4-(4-methyl-piperazin-1-yl)-phenyl]-amine as a yellow solid. MP 164-165° C. LCMS (E/I+) 429.21 (M+H). NMR $^1$H (DSMO-$d_6$)-9.12 (s, 1H), 8.89 (s, 1H), 7.90 (dd, 1H, J=1.52, 6.08 Hz), 7.58 (d, 2H, J=9.00 Hz), 7.41 (td, 1H, J=1.53, 7.04 Hz), 7.18 (d, 1H, J=8.25 Hz), 7.11 (t, 1H, J=7.49 Hz), 6.96 (d, 1H, J=4.64 Hz), 6.87 (d, 1H, J=4.64 Hz), 6.80 (d, 2H, J=9.04 Hz), 4.07 (q, 2H, JJ=6.96, 6.84 Hz), 3.03 (t, 4H, J=4.64 Hz), 2.44 (t, 4H, J=4.76 Hz), 2.21 (s, 3H), 1.22 (t, 3H, J, 6.92 Hz).

Example 110

[5,6-Dibromo-7-(2-methoxy-phenyl)-pyrrolo[2,1-f][1,2,4]triazin-2-yl]-(4-morpholin-4-yl-phenyl)-amine 110a) Into a 1-Neck round-bottom flask, [A] 7-(2-Methoxy-phenyl)-2-methylsulfanyl-pyrrolo[2,1-f][1,2,4]triazine (0.450 g, 1.66 mmol), Tetrahydrofuran (50 mL, 600 mmol), and Methanol (25 mL, 620 mmol) were added. N-Bromosuccinimide (0.649 g, 3.65 mmol) was added portion wise over 20 minutes. The reaction was stirred at room temperature for one hour. The reaction was partitioned with water and DCM. The organic was separated, washed with Brine and dried over Na2SO4. The solid was filtered and washed with DCM. The Solvent was removed under vacuum. The desired product was purified via ISCO column chromatography with hexane and EtOAc as eluant (0 to 100% EtOAc). The collected fractions afforded 5,6-Dibromo-7-(2-methoxy-phenyl)-2-methylsulfanyl-pyrrolo[2,1-f][1,2,4]triazine as a yellow solid (0.463, 65%). NMR $^1$H (DSMO-$d_6$)-8.92 (s, 1H), 7.53 (dt, 1H, JJ=1.64, 7.20 Hz), 7.43 (dd, 1H, JJ=1.69, 5.92 Hz), 7.23 (d, 1H, J=8.40 Hz), 7.11 (t, 1H, J=7.45 Hz), 3.76 (s, 3H), 2.37 (s, 3H)

110b) Into a Round bottom flask, [A] 5,6-Dibromo-7-(2-methoxy-phenyl)-2-methylsulfanyl-pyrrolo[2,1-f][1,2,4]triazine (0.460 g, 0.00107 mol) and Methylene chloride (2 mL, 0.03 mol) were added. m-CPBA 70-75% (70:30, m-Chloroperbenzoic acid:3-Chlorobenzoic acid, 0.291 g, 0.00118 mol) was added portion wise over 20 minutes. The reaction was stirred at room temperature for one hour. The reaction was partitioned with DCM (200 mL) and saturated NaHCO3 (200 mL). The organic was separated, washed with Brine and dried over Na2SO4. The solid was filtered and washed with DCM. The solvent was removed under vacuum to give a yellow solid. The solid was washed with hexane to give 5,6-Dibromo-2-methanesulfinyl-7-(2-methoxy-phenyl)-pyrrolo[2,1-f][1,2,4]triazine as a yellow solid (0.465 g, 97%). NMR $^1$H (DSMO-$d_6$)-9.27 (s, 1H), 7.50-7.62 (m, 2H), 7.40-7.48 (m, 2H), 3.80 (s, 3H), 2.90 (s, 3H)

110c) Into a Microwave vial, 5,6-Dibromo-2-methanesulfinyl-7-(2-methoxy-phenyl)-pyrrolo[2,1-f][1,2,4]triazine (0.480 g, 0.00108 mol), 1-Methoxy-2-propanol (4.0 mL, 0.041 mol), 4-(4-morpholino)aniline (0.423 g, 0.00237 mol), and N,N-Diisopropylethylamine (0.376 mL, 0.00216 mol) were added. The reaction was microwaved on 300 watts, 180° C. for 60 minutes. The solvent was removed under vacuum. The desired product was isolated via HPLC with 0.1% TFA in ACN and 0.1% TFA in water as eluant (20 to 50% ACN). The collected fraction afforded [5,6-Dibromo-7-(2-methoxy-phenyl)-pyrrolo[2,1-f][1,2,4]triazin-2-yl]-(4-morpholin-4-yl-phenyl)-amine; compound with trifluoro-acetic acid a yellow solid. (100 mg, 16%). LCMS (E/I+) 559.86 (M+H). NMR $^1$H (DSMO-$d_6$)-9.52 (s, 1H), 8.88 (s, 1H), 7.57 (dt, 1H, J=1.56, 7.12 Hz), 7.49 (d, 2H, J=8.73 Hz), 7.42 (dd, 1H, J=1.53, 6.00 Hz), 7.27 (d, 1H, J=8.40 Hz), 7.13 (t, 1H, J=7.48 Hz), 6.80-7.00 (bm, 2H), 3.70-3.05 (bm, 7H), 3.09 (bs, 4H).

Example 111

(7-Benzenesulfonyl-pyrrolo[2,1-f][1,2,4]triazin-2-yl)-(4-morpholin-4-yl-phenyl)-amine Into a Round bottom flask, and Methylene chloride (15 mL, 0.18 mol) were added. m-Chloroperbenzoic acid (0.0677 g, 0.000392 mol) was added portion wise over 20 minutes. The reaction was stirred at room temperature for one hour. The reaction was partitioned with DCM (200 mL) and saturated NaHCO$_3$ (200 mL). The organic was separated, washed with Brine and dried over Na$_2$SO$_4$. The solid was filtered and washed with DCM. The solvent was removed under vacuum to give a yellow solid. The desired product was purified via ISCO column chromatography with DCM and methano as eluant (0 to 5% methanol). The collected fraction afforded (7-Benzenesulfonyl-pyrrolo[2,1-f][1,2,4]triazin-2-yl)-(4-morpholin-4-yl-phenyl)-amine a yellow solid. MP 110-115° C. LCMS (E/I+) 458.03 (M+Na). NMR $^1$H (DSMO-$d_6$)-8.65 (s, 1H), 7.67-7.80 (m, 2H), 7.49 (d, 2H, J=7.04 Hz), 7.37-7.45 (m, 3H), 7.19 (s, 1H), 6.92 (d, 2H, J=8.96 Hz), 6.61 (s, 2H), 3.82 (td, 1H, J=4.68 Hz), 3.09 (t, 1H, J=4.81 Hz).

Example 112

[7-(2-Methoxy-phenyl)-5,6-dimethyl-pyrrolo[2,1-f][1,2,4]triazin-2-yl]-(4-morpholin-4-yl-phenyl)-amine Into a 30 mL vial, [5,6-Dibromo-7-(2-methoxy-phenyl)-pyrrolo[2,1-f][1,2,4]triazin-2-yl]-(4-morpholin-4-yl-phenyl)-amine (0.068 g, 0.00012 mol), Trimethylboroxine (0.138 g, 0.00110 mol), and Potassium carbonate (0.756 g, 0.00547 mol) were added and purged under an atmosphere of Nitrogen for 10 minutes. N,N-Dimethylformamide (2.52 mL, 0.0326 mol) was then added and heated at 130° C. for 64 hours. The reaction was partitioned with water and EtOAc. The organic was separated, washed with Brine, and dried over magnesium sulfate. The solid was filtered and washed with EtOAc. The solvent was removed under vacuum. The product was isolated via ISCO column chromatography with DCM and MeOH as eluant (0 to 5% MeOH). The collected fractions afforded solid. The solid was triturated with hexane and EtOAc to give [7-(2-Methoxy-phenyl)-5,6-dimethyl-pyrrolo[2,1-f][1,2,4]triazin-2-yl]-(4-morpholin-4-yl-phenyl)-amine as a yellow solid (12 mg, 23%). MP 169-172° C. LCMS (E/I+) 430.06 (M+H). NMR $^1$H (CDCl$_3$-d)-8.55 (s, 1H), 7.45-7.55 (m, 2H), 7.41 (d, 2H, J=8.92 Hz), 7.03-7.15 9 m, 2H), 6.77 (d, 2H, J=9.00 Hz), 3.82-3.90 (m, 4H), 3.79 (s, 3H), 3.05 (t, 4H, J=4.77 Hz), 2.35 (s, 3H), 2.13 (s, 3H).

Example 113

7-(4-Methanesulfonyl-phenyl)-2-(2-methoxy-1-methyl-ethoxy)-pyrrolo[2,1-f][1,2,4]triazine; compound with trifluoro-acetic acid Into a Microwave vial, 2-Methanesulfinyl-7-(4-methanesulfonyl-phenyl)-pyrrolo[2,1-f][1,2,4]triazine (0.135 g, 0.000404 mol), 8-Amino-5,5-dimethyl-1,3,4,5-tetrahydrobenzo[b]azepin-2-one (0.181 g, 0.000888 mol), 1-Methoxy-2-propanol (0.971 mL, 0.00993 mol) and N,N-Diisopropylethylamine (0.155 mL, 0.000888 mol) were added. The reaction was microwaved on 300 watts, 170° C. for 50 minutes. The solvent was removed under vacuum. The reaction mixture was purified via HPLC reverse phase chromatography with 0.1% TFA in Water and 0.1% TFA in ACN. The collected fractions were lyophilized to give 7-(4-Methanesulfonyl-phenyl)-2-(2-methoxy-1-methyl-ethoxy)-pyrrolo[2,1-f][1,2,4]triazine; compound with trifluoro-acetic acid a yellow powder (13 mg, 6%). LCMS (E/I+) 362.03 (M+H). NMR $^1$H (DSMO-$d_6$)-9.14 (s, 1H), 8.50 (d, 2H, J=8.53 Hz), 8.06 (d, 2H, J=8.57 Hz), 7.54 (d, 1H, J=4.88 Hz), 7.13 (d, 1H, J=4.84 Hz), 5.20-5.30 (, 1H), 3.54-3.65 (m, 2H), 3.27 (s, 3H), 1.38 (d, 3H, J=6.37 Hz).

Example 114

7-(2-Methoxy-phenyl)-2-[4-(4-methyl-piperazin-1-yl)-phenylamino]-pyrrolo[2,1-f][1,2,4]triazine-5-carbonitrile Into a Microwave vial, [5-Bromo-7-(2-methoxy-phenyl)-pyrrolo[2,1-f][1,2,4]triazin-2-yl]-[4-(4-methyl-piperazin-1-yl)-phenyl]-amine (0.151 g, 0.000306 mol), Zinc Cyanide (0.0719 g, 0.000612 mol), Copper(I) iodide (5.8 mg, 0.000031 mol) and Tetrakis(triphenylphosphine)palladium (0) (35 mg, 0.000031 mol) were added and purged with nitrogen for 10 minutes. N,N-Dimethylformamide (3.00 mL, 0.0387 mol) was added. The reaction was microwaved on 300 watts, 150° C. for 60 minutes. The solvent was removed under vacuum. The reaction was purified via ISCO column chromatography with DCM and MeOH as eluant (0 to 10% methanol). The collected fractions afforded 7-(2-Methoxy-phenyl)-2-[4-(4-methyl-piperazin-1-yl)-phenylamino]-pyrrolo[2,1-f][1,2,4]triazine-5-carbonitrile a yellow solid (62 mg, 46%). LCMS (E/I+) 440.18M+H). NMR $^1$H (DSMO-$d_6$)-9.59 (s, 1H), 9.20 (s, 1H), 7.72 (dd, 1H, J=1.64, 6.00 Hz), 7.46-7.57 (m, 3H), 7.43 (s, 1H), 7.42 (d, 1H, J=8.33 Hz), 7.13 (t, 1H, J=7.56 Hz), 6.80 (d, 2H, J=9.13 Hz), 3.79 (s, 3H), 3.04 (t, 4H, J=4.64, 2.43 (t, 4H, J=4.84), 2.21 (s, 3H).

Example 115

2-{4-[4-(7-Pyridin-3-yl-pyrrolo[2,1-f][1,2,4]triazin-2-ylamino)-phenyl]-piperazin-1-yl}-ethanol 115a) Into a Microwave vial, 7-Bromo-2-methanesulfinyl-pyrrolo[2,1-f][1,2,4]triazine (0.480 g, 0.00184 mol), 2-[4-(4-Amino-phenyl)-piperazin-1-yl]-ethanol (0.8984 g, 0.004060 mol) and 1-Methoxy-2-propanol (3.50 mL, 0.0358 mol) were added. The reaction was microwaved on 300 watts, 180° C. for 60 minutes. The solvent was removed under vacuum. The desired product was isolated via ISCO column chromatography with DCM and methanol as eluant (0 to 7% methanol). The collected fractions afforded 2-{4-[4-(7-Bromo-pyrrolo[2,1-f][1,2,4]triazin-2-ylamino)-phenyl]-piperazin-1-yl}-ethanol as a yellow solid (280 mg, 36%).

115b) Into a 30 mL vial, Palladium Acetate (0.0059 g, 0.000026 mol) and Triphenylphosphine (0.019 g, 0.000074 mol) were added. The mixture was purged under an atmosphere of Nitrogen for 10 minutes. 1,4-Dioxane (2.00 mL, 0.0256 mol) was added and stirred for 10 minutes at room temperature. 2-{4-[4-(7-Bromo-pyrrolo[2,1-f][1,2,4]triazin-2-ylamino)-phenyl]-piperazin-1-yl}-ethanol (0.110 g, 0.000264 mol), 3-Pyridylboronic acid (0.0648 g, 0.000527 mol), N,N-Dimethylformamide (4.0 mL, 0.052 mol), and 1.50 M of Sodium carbonate in Water (1.58 mL, 0.00237 mol) were added. The reaction was heated at 90° C. for 3 hours. The reaction was partitioned with water and EtOAc. The organic was separated, washed with Brine, and dried over magnesium sulfate. The solid was filtered and washed with EtOAc. The solvent was removed under vacuum. The product was isolated via column chromatography with DCM and NH3 in Methanol as eluant (0 to 10% NH3 in MeOH). The collected fractions afforded a solid. The solid was triturated with Et2O and filtered to give 2-{4-[4-(7-Pyridin-3-yl-pyrrolo[2,1-f][1,2,4]triazin-2-ylamino)-phenyl]-piperazin-1-yl}-ethanol as a yellow solid (52 mg, 47%). MP 189-190° C. LCMS (E/I+) 416.05 (M+H). NMR $^1$H (DSMO-$d_6$)-9.32 (d, 1H, J=2.00), 9.27 (s, 1H), 8.96 (s, 1H), 8.60 (d, 1H, J=8.21 Hz), 8.56 (dd, 2H, JJ=1.40, 3.19 Hz), 7.52-7.65 (m, 3H), 7.26 (d, 1H, J=4.00 Hz), 6.94 (d, 1H, J=5.43 Hz), 6.90 (d, 2H, J=9.36 Hz), 4.40 (t, 1H, J=5.37 Hz), 3.53 (q, 2H, JJ=6.13, 5.62 Hz), 3.07 (t, 4H, J=4.68 Hz), 2.56 (t, 4H, J=4.32 Hz), 2.44 (t, 2H, J=6.32 Hz).

Example 116

{1-[4-(7-Pyridin-3-yl-pyrrolo[2,1-f][1,2,4]triazin-2-ylamino)-phenyl]-piperidin-4-yl}-methanol The titled compound was prepared in an analogous fashion to Example 115 replacing 2-[4-(4-Amino-phenyl)-piperazin-1-yl]-ethanol with [1-(4-Amino-phenyl)-piperidin-4-yl]-methanol to give {1-[4-(7-Pyridin-3-yl-pyrrolo[2,1-f][1,2,4]triazin-2-ylamino)-phenyl]-piperidin-4-yl}-methanol a yellow solid (49 mg, 45%). MP 206-207° C. LCMS (E/I+) 401.04 (M+H). NMR $^1$H (DSMO-$d_6$)-9.32 (d, 1H, J=2.00), 9.26 (s, 1H), 8.96 (s, 1H), 8.60-8.68 (m, 1H), 8.56 (dd, 1H, JJ=1.44, 4.25 Hz), 7.54-7.63 (m, 3H), 7.26 (d, 2H, J=4.38 Hz), 6.95 (d, 1H, J=5.28 Hz), 6.90 (d, 2H, J=9.36 Hz), 4.47 (t, 1H, J=4.56 Hz), 3.62 (bd, 2H, J=12.15 Hz), 3.25-3.35 (m, 2H), 2.60 (dt, 4H, JJ=1.49, 13.36 Hz), 1.76 (d, 2H, J=16.05 Hz), 1.18-1.58 (bm, 3H).

Example 117

N-(2-Methanesulfonyl-ethyl)-4-[2-(4-morpholin-4-yl-phenylamino)-pyrrolo[2,1-f][1,2,4]triazin-7-yl]-benzamide Into a 30 mL vial, 4-[2-(4-Morpholin-4-yl-phenylamino)-pyrrolo[2,1-f][1,2,4]triazin-7-yl]-benzoic acid (104 mg, 0.251 mmol), N,N-Dimethylformamide (2.08 mL, 26.9 mmol; Supplier=EMD), 1-Hydroxybenzotriazole (41 mg, 0.30 mmol), 4-Methylmorpholine (33.1 uL, 0.301 mmol), [B] 2-Methanesulfonyl-ethylamine; hydrochloride (0.0601 g, 0.376 mmol), and N-(3-Dimethylaminopropyl)-N'-ethylcarbodiimide hydrochloride (0.0577 g, 0.301 mmol) were added. The reaction was stirred at room temperature overnight. The reaction was partitioned with sat'd NaHCO3. The precipitate was filtered and washed with water to afford N-(2-Methanesulfonyl-ethyl)-4-[2-(4-morpholin-4-yl-phenylamino)-pyrrolo[2,1-f][1,2,4]triazin-7-yl]-benzamide as a yellow solid. MP 241-242° C. LCMS (E/I+) 521.00M+H). NMR $^1$H (DSMO-$d_6$)-9.34 (d, 1H, J=2.00), 8.97 (s, 1H), 8.60 (d, 1H, J=8.21 Hz), 8.79 (t, 1H, J=5.72 Hz), 8.34 (d, 2H, J=8.52 Hz), 7.97 (d, 2H, J=8.52 Hz), 7.65 (d, 2H, J=9.00 Hz), 7.28 (d, 1H, J=4.80 Hz), 6.94-7.00 (m, 3H), 3.65-3.80 (m, 6H), 3.41 (t, 2H, J=6.88 Hz), 3.03-3.12 (m, 7H).

Example 118

N-tert-Butyl-3-{2-[4-(2-pyrrolidin-1-yl-ethoxy)-phenylamino]-pyrrolo[2,1-f][1,2,4]triazin-7-yl}-benzenesulfonamide 118a) To a Parr bottle was added [A] 1-[2-(4-Nitro-phenoxy)-ethyl]-pyrrolidine; hydrochloride (10 g, 0.04 mol; Supplier=Cephalon) in Ethanol (200 mL, 3 mol; Supplier=Pharmco Products Inc.). The bottle was purged with Argon and 10% Palladium on Carbon (50% Wet)(5:45:50, Palladium:carbon black:Water, 100 mg, 0.00005 mol; Supplier=Aldrich) added. The mixture was placed under an atmosphere of Hydrogen at 50 psi for 2 h. HPLC indicated no starting material remaining.

Workup involved filtering the mixture through celite and flushing with ethyl acetate and DMF. NOTE: Product appeared to crash out of solution so DMF was used to dissolve the material for filtering. The filtrate was concentrated in vacuo, triturated with ether and collected by filtration. 1H NMR of the solid showed desired product as the HCl salt. Some DMF and water were present. The material was suspended in ethyl acetate and washed with saturated aqueous bicarbonate. The ethyl acetate layer was dried over magnesium sulfate, filtered and concentrated in vacuo to a dark brown oil. The oil was redissolved in ethyl acetate and 2 M HCl in ether (15 mL) was added dropwise to reform the salt. The solid was collected by filtration and dried in vacuo to give 4-(2-Pyrrolidin-1-yl-ethoxy)-phenylamine; hydrochloride (7.6 g, 80%). NMR $^1$H (DSMO-$d_6$)-6.80 (d, 2H, J=8.8 Hz), 6.67 (d, 2H, J=8.7 Hz), 6.0 (broad s, 1H), 4.19 (t, 2H, J=5 Hz), 3.49-3.54 (m, 4H), 3.1 (broad s, 2H), 1.94 (broad s, 4H).

118b) Into a 30 mL vial, Palladium Acetate (0.0059 g, 0.000026 mol) and Triphenylphosphine (0.019 g, 0.000074 mol) were added. The mixture was purged under an atmosphere of Nitrogen for 10 minutes. 1,4-Dioxane (2.00 mL, 0.0256 mol) was added and stirred for 10 minutes at room temperature. (7-Bromo-pyrrolo[2,1-f][1,2,4]triazin-2-yl)-[4-(2-pyrrolidin-1-yl-ethoxy)-phenyl]-amine (0.106 g, 0.000264 mol)—Note (7-Bromo-pyrrolo[2,1-f][1,2,4]triazin-2-yl)-[4-(2-pyrrolidin-1-yl-ethoxy)-phenyl]-amine was prepared in analogous fashion to Example 1G, N,N-Dimethylformamide (4.0 mL, 0.052 mol), and 1.50 M of Sodium carbonate in Water (1.58 mL, 0.00237 mol) were added. The reaction was heated at 90° C. for 3 hours. The reaction was partitioned with water and EtOAc. The organic was separated, washed with Brine, and dried over magnesium sulfate. The solid was filtered and washed with EtOAc. The solvent was removed under vacuum. The product was isolated via reverse phase HPLC chromatography with 015 TFA in ACN and 0.1% TFA in water as eluant. The collected fractions afforded N-tert-Butyl-3-{2-[4-(2-pyrrolidin-1-yl-ethoxy)-phenylamino]-pyrrolo[2,1-f][1,2,4]triazin-7-yl}-benzenesulfonamide as a yellow solid (13 mg, 9%). LCMS (E/I+) 535.16 (M+H). NMR $^1$H (DSMO-$d_6$)-9.69 (d, 1H, J=2.00), 9.44 (s, 1H), 9.02 (s, 1H), 8.59 (s, 1H), 8.31 (d, 1H, J=8.97 Hz), 7.86 (d, 1H, J=7.80 Hz), 7.68-7.78 (m, 3H), 7.16 (s, 1H), 7.18 (d, 1H, J=4.73 Hz), 7.03 (d, 2H, J=9.04 Hz), 7.98 (d, 1H, J=4.72 Hz), 4.25 (t, 2H, J=4.68 Hz), 3.00-3.80 (m, 6H), 2.00-2.23 (m, 2H), 1.78-1.98 (m, 2H), 1.10 (s, 9H).

Example 119

{4-[2-(4-Methyl-piperazin-1-yl)-ethoxy]-phenyl}-(7-pyridin-3-yl-pyrrolo[2,1-f][1,2,4]triazin-2-yl)-amine 119a) Into a round bottom flask, Palladium Acetate (0.052 g, 0.00023 mol) and Triphenylphosphine (0.076 g, 0.00029 mol) were dissolved in dioxane (3.5 mL, 0.043 mol) and the mixture was allowed to stir at room temperature for 10 minutes. DMF (5 mL), 7-Bromo-2-methanesulfinyl-pyrrolo[2,1-f][1,2,4]triazine (0.300 g, 0.00115 mol) was then added and the reaction was again allowed to stir for 10 minutes. [B] 3-Pyridylboronic acid (0.284 g, 0.00231 mol) was added followed by 0.9 M of Sodium carbonate in water (1 mL, 0.001 mol) and Ethanol (3.5 mL, 0.060 mol). The reaction mixture was then heated at 80° C. overnight. The reaction was partitioned with water and DCM. The organic was separated, washed with Brine and dried over sodium sulfate. The solid was filtered and washed. The solvent was removed under vacuum. The reaction mixture was purified by ISCO column chromatography with DCM and methanol as eluant (0 to 10%). The collected fractions afforded 2-Methanesulfinyl-7-pyridin-3-yl-pyrrolo[2,1-f][1,2,4]triazine as a yellow solid (0.19 g, 61%). LCMS (E/I+) 259.8 (M+H)

119b) Into a microwave vial, 2-Methanesulfinyl-7-pyridin-3-yl-pyrrolo[2,1-f][1,2,4]triazine (0.104 g, 0.000404 mol), 4-[2-(4-Methyl-piperazin-1-yl)-ethoxy]-phenylamine (0.209 g, 0.000888 mol), 1-Methoxy-2-propanol (0.971 mL, 0.00993 mol) and N,N-Diisopropylethylamine (0.155 mL, 0.000888 mol) were added. The reaction was microwaved on 300 watts, 170° C. for 50 minutes. The solvent was removed under vacuum. The desired product was isolated via ISCO column chromatography with DCM and methanol as eluant (0 to 12% methanol). The collected fractions afforded {4-[2-(4-Methyl-piperazin-1-yl)-ethoxy]-phenyl}-(7-pyridin-3-yl-pyrrolo[2,1-f][1,2,4]triazin-2-yl)-amine as a yellow solid (28 mg, 16%). MP 107-110° C. LCMS (E/I+) 430.8 (M+H). NMR $^1$H (DSMO-$d_6$)-9.42 (d, 1H, J=2.00), 9.39 (s, 1H), 9.04 (s, 1H), 8.66 (d, 1H, J=7.76 Hz), 8.61 (d, 1H, J=6.56 Hz), 7.60-7.70 (m, 3H), 7.32 (d, 1H, J=4.77 Hz), 6.98 (d, 1H, J=4.76 Hz), 6.95 (d, 2H, J=9.00 Hz), 4.16 (t, 2H, J=5.26 Hz), 2.40-3.50 (m, 13H).

Example 120

{4-[3-(4-Methyl-piperazin-1-yl)-propoxy]-phenyl}-(7-pyridin-3-yl-pyrrolo[2,1-f][1,2,4]triazin-2-yl)-amine 120a) Into a 30 mL vial, 1-(3-Bromo-propoxy)-4-nitro-benzene (5.28 g, 0.0203 mol), piperazine, 1-methyl-(4.51 mL, 0.0406 mol), Acetonitrile (15.0 mL, 0.287 mol) and Potassium carbonate (5.62 g, 0.0406 mol) were added. The reaction was heated at 80° C. for 4 hours. The reaction was partitioned with water and extracted with Et2O (3×100 mL). The Combined organic was washed with Brine, and dried over magnesium sulfate. The solid was filtered and washed with EtOAc. The solvent was removed under vacuum to afford an oil. The desired product was obtained via column chromatography with DCM and Methanol as eluant (0 to 10% methanol). The collected fractions afforded 1-Methyl-4-[3-(4-nitro-phenoxy)-propyl]-piperazine as a yellow oil (4.86 g, 86%). NMR $^1$H (DSMO-$d_6$)-8.20 (dd, 1H, J=1.76, 5.56 Hz), 7.13 (dd, 2H, J=1.88, 7.32 Hz), 4.14 (t, 2H, J=6.36 Hz), 2.20-2.60 (m, 10H), 2.14 (s, 3H), 1.80-1.95 (m, 2H)

120b) Into a Round bottom flask, 1-Methyl-4-[3-(4-nitrophenoxy)-propyl]-piperazine (4.10 g, 0.0147 mol), 10% Pd/C (10:90, Palladium:carbon black, 1.6 g, 0.0015 mol), and Ethanol (100 mL, 2 mol) were added. The mixture was evacuated under house vacuum and charged with a hydrogen balloon (3×). The reaction was stirred at room temperature under an atmosphere of Hydrogen via a balloon. The solid was filtered. The solvent was removed under vacuum to give 4-[3-(4-Methyl-piperazin-1-yl)-propoxy]-phenylamine a white solid (2.86, 78%). $^1$H (DSMO-d$_6$)-6.62 (dd, 1H, J=2.08, 4.57 Hz), 6.49 (dd, 2H, J=2.16, 5.64 Hz), 4.56 (bs, 2H), 3.82 (t, 2H, J=6.40 Hz), 2.20-2.45 (m, 10H), 2.13 (s, 3H), 1.70-1.83 (m, 2H)

120c) Into a Microwave vial, 2-Methanesulfinyl-7-pyridin-3-yl-pyrrolo[2,1-f][1,2,4]triazine (0.104 g, 0.000404 mol), 4-[3-(4-Methyl-piperazin-1-yl)-propoxy]-phenylamine (0.221 g, 0.000888 mol), 1-Methoxy-2-propanol (0.971 mL, 0.00993 mol) and N,N-Diisopropylethylamine (0.155 mL, 0.000888 mol) were added. The reaction was microwaved on 300 watts, 170° C. for 50 minutes. The solvent was removed under vacuum. The desired product was isolated via ISCO column chromatography with DCM and methanol as eluant (0 to 15% methanol). The collected fractions afforded {4-[3-(4-Methyl-piperazin-1-yl)-propoxy]-phenyl}-(7-pyridin-3-yl-pyrrolo[2,1-f][1,2,4]triazin-2-yl)-amine as a yellow solid (25 mg, 14%). MP 135-139° C. LCMS (E/I+) 444.8 (M+H). NMR $^1$H (DSMO-d$_6$)-9.38-9.46 (m, 2H), 9.03 (s, 1H), 8.66 (d, 1H, J=8.08 Hz), 8.61 (d, 1H, J=4.67 Hz), 7.60-7.70 (m, 3H), 7.32 (d, 1H, J=4.81 Hz), 6.98 (d, 1H, J=4.80 Hz), 6.93 (d, 2H, J=9.00 Hz), 4.03 (t, 2H, J=5.26 Hz), 2.30-3.60 (m, 13H), 1.95-2.10 (bm, 2H).

Example 121

[7-(2-Methoxy-phenyl)-pyrrolo[2,1-f][1,2,4]triazin-2-yl]-[4-(2-pyrrolidin-1-yl-ethoxy)-phenyl]-amine; compound with trifluoro-acetic acid Into a Microwave vial, 2-Methanesulfinyl-7-(2-methoxy-phenyl)-pyrrolo[2,1-f][1,2,4]triazine (0.116 g, 0.000404 mol), 4-(2-Pyrrolidin-1-yl-ethoxy)-phenylamine (0.183 g, 0.000888 mol), 1-Methoxy-2-propanol (0.971 mL, 0.00993 mol) and N,N-Diisopropylethylamine (0.155 mL, 0.000888 mol) were added. The reaction was microwaved on 300 watts, 170° C. for 50 minutes. The solvent was removed under vacuum. The desired product was isolated via HPLC column chromatography with 0.1% TFA in water and 0.1% TFA in ACN as eluant. The collected fractions were lyophilized to afford [7-(2-Methoxy-phenyl)-pyrrolo[2,1-f][1,2,4]triazin-2-yl]-[4-(2-pyrrolidin-1-yl-ethoxy)-phenyl]-amine; compound with trifluoro-acetic acid as a yellow solid (42 mg, 19%). LCMS (E/I+) 430.8 (M+H). NMR $^1$H (DSMO-d$_6$)-9.75 (bs, 1H), 9.29 (s, 1H), 8.93 (s, 1H), 7.82 (dd, 1H, JJ=1.60, 6.01 Hz), 7.67 (d, 2H, J=9.04 Hz), 7.46 (dt, 1H, JJ=1.60, 7.00 Hz), 7.21 (d, 1H, J=8.24 Hz), 7.19 (t, 1H, J=7.37 Hz), 6.83-7.00 (m, 4H), 4.23 (t, 2H, J=4.73 Hz), 3.80 (s, 3H), 3.50-3.68 (m, 4H), 3.07-3.20 (m , 2H), 1.96-2.10 (m, 2H), 1.80-1.93 (m, 2H).

Example 122

[7-(2-Methoxy-phenyl)-pyrrolo[2,1-f][1,2,4]triazin-2-yl]-(1H-pyrazol-3-yl)-amine; compound with trifluoro-acetic acid Into a Microwave vial, 2-Methanesulfinyl-7-(2-methoxy-phenyl)-pyrrolo[2,1-f][1,2,4]triazine (0.116 g, 0.404 mmol), 1H-Pyrazol-3-ylamine (0.0738 g, 0.888 mmol), 1-Methoxy-2-propanol (0.971 mL, 9.93 mmol) and N,N-Diisopropylethylamine (0.155 mL, 0.888 mmol) were added. The reaction was microwaved on 300 watts, 170° C. for 50 minutes. The solvent was removed under vacuum. The desired product was isolated via HPLC column chromatography with 0.1% TFA in water and 0.1% TFA in ACN as eluant. The collected fractions were lyophilized to afford [7-(2-Methoxy-phenyl)-pyrrolo[2,1-f][1,2,4]triazin-2-yl]-(1H-pyrazol-3-yl)-amine; compound with trifluoro-acetic acid as a yellow solid (45 mg, 26%). LCMS (E/I+) 307.6 (M+H). NMR $^1$H (DSMO-d$_6$)-9.58 (bs, 1H), 8.91 (s, 1H), 7.80 (dd, 1H, JJ=1.56, 6.01 Hz), 7.53 (d, 1H, J=1.16 Hz), 7.44 (dt, 1H, JJ=1.38, 7.08 Hz), 7.20 (t, 1H, J=8.29 Hz), 7.08 (t, 1H, J=7.44 Hz), 6.93-6.98 (m, 2H), 4.40 (d, 2H, J=2.08 Hz), 3.78 (s, 3H).

Example 123

(7-Cyclohexyl-pyrrolo[2,1-f][1,2,4]triazin-2-yl)-[4-(4-methyl-piperazin-1-yl)-phenyl]-amine 123a) Cyclohexyl zinc bromide was purchase in 0.5 M solution in THF from aldrich. Into a 30 mL vial [1,1'-Bis(diphenylphosphino)ferrocene]dichloropalladium(II) (0.20 g, 0.00028 mol), [A] 7-Bromo-2-methylsulfanyl-pyrrolo[2,1-f][1,2,4]triazine (0.68 g, 0.0028 mol), Copper(I) iodide (0.053 g, 0.00028 mol) were added. The mixture was purged under under an atmosphere of Nitrogen for 10 minutes. Tetrahydrofuran (10 mL, 0.1 mol) and Cyclohexyl zinc bromide (1.27 g, 0.00557 mol) were added. The reaction was heated at 78° C. overnight. The solvent was removed under vacuum. The desired product was isolated via ISCO column chromatography with hexand and EtOAsc as eluant (0 to 10% EtoAc). The collected fractions afforded 7-Cyclohexyl-2-methylsulfanyl-pyrrolo[2,1-f][1,2,4]triazine a semi solid (0.32 g, 46% with <90% purity). The product was used as is.

123b) Into a Round bottom flask, 7-Cyclohexyl-2-methylsulfanyl-pyrrolo[2,1-f][1,2,4]triazine (0.32 g, 0.0013 mol) and Methylene chloride (50 mL, 0.8 mol) were added. 77% MCPBA (77:23, m-Chloroperbenzoic acid:3-Chlorobenzoic acid, 0.319 g, 0.00142 mol) was then added portion wise over 10 minutes. The reaction was stirred for 30 minutes at RT. The reaction was partitioned with Sat. NaHCO3 and DCM. The organic was separated, washed with water, subsequently with Brine, and dried over magnesium sulfate. The solid was filtered and washed with DCM. The solvent was removed under vacuum to give a viscous oil (280 mg, 82%). The product was used as is with some sulfone impurity.

123c) Into a Microwave vial, 7-Cyclohexyl-2-methanesulfinyl-pyrrolo[2,1-f][1,2,4]triazine (0.140 g, 0.000532 mol), 4-(4-Methyl-piperazin-1-yl)-phenylamine (0.224 g, 0.00117 mol), 1-Methoxy-2-propanol (1.49 mL, 0.0152 mol) and N,N-Diisopropylethylamine (0.204 mL, 0.00117 mol) were added. The reaction was microwaved on 300 watts, 170° C. for 50 minutes. The solvent was removed under vacuum. The desired product was isolated via HPLC column chromatography with 0.1% TFA in water and 0.1% TFA in ACN as eluant. The collected fractions was lyophilized to afford (7-Cyclohexyl-pyrrolo[2,1-f][1,2,4]triazin-2-yl)-[4-(4-methyl-piperazin-1-yl)-phenyl]-amine; compound with trifluoro-acetic acid a yellow solid (50 mg, 20%). LCMS (E/I+) 391.8 (M+H). NMR $^1$H (DSMO-d$_6$)-9.74 (bs, 1H), 9.22 (s, 1H), 8.90 (s, 1H), 7.75 (d, 2H, J=9.01 Hz), 6.98 (d, 2H, J=9.08 Hz), 6.75 (d, 1H, J=4.57 Hz), 6.56 (d, 1H, J=4.53 Hz), 3.77 (d 2H, J=13.1, 3.52 (d, 2H, J=11.88), 3.02-3.30 (m, 3H), 2.80-2.95 (m, 5H), 2.00-2.18 (m, 2H), 1.70-1.92 (m, 3H), 1.20-1.60 (m, 5H).

Example 124

(1H-Pyrazol-3-yl)-(7-pyridin-3-yl-pyrrolo[2,1-f][1,2,4]triazin-2-yl)-amine; compound with trifluoro-acetic acid Into a Microwave vial, 2-Methanesulfinyl-7-pyridin-3-yl-pyrrolo[2,1-f][1,2,4]triazine (0.120 g, 0.000464 mol), 1H-Pyrazol-3-ylamine (0.0849 g, 0.00102 mol), 1-Methoxy-2-propanol (1.12 mL, 0.0114 mol) and N,N-Diisopropylethylamine (0.178 mL, 0.00102 mol) were added. The reaction was microwaved on 300 watts, 170° C. for 50 minutes. The solvent was removed under vacuum. The desired product was isolated via HPLC column chromatography with 0.1% TFA in water and 0.1% TFA in ACN as eluant. The collected fractions was lyophilized to afford (1H-Pyrazol-3-yl)-(7-pyridin-3-yl-pyrrolo[2,1-f][1,2,4]triazin-2-yl)-amine; compound with trifluoro-acetic acid a yellow solid (57 mg, 31%). LCMS (E/I+) 286.6 (M+H). NMR $^1$H (DSMO-d$_6$)-9.80 (s, 1H), 9.72 (d, 1H, J=1.80 Hz), 9.05 (s, 2H), 9.03 (s, 1H), 7.8.70 (dd, 1H, JJ=1.26, 4.92 Hz), 7.90-7.95 (m, 1H), 7.67 (d, 1H, J=2.28 Hz), 7.43 (d, 1H, J=4.85 Hz), 7.01 (d, 1H, J=4.84 Hz), 6.43 (d, 1H, J=2.28 Hz).

Example 125

[4-(2-Morpholin-4-yl-ethoxy)-phenyl]-(7-pyridin-3-yl-pyrrolo[2,1-f][1,2,4]triazin-2-yl)-amine 125a) Into a 30 mL vial, [A] 1-(2-Bromo-ethoxy)-4-nitrobenzene (5.00 g, 0.0203 mol), Morpholine (3.54 mL, 0.0406 mol), Acetonitrile (15.0 mL, 0.287 mol) and Potassium carbonate (5.62 g, 0.0406 mol) were added. The reaction was heated at 80° C. for 4 hours. The reaction was partitioned with water (250 mL). The solid was filtered and washed with water. The resulting solid was dried under vacuum overnight to give 4-[2-(4-Nitrophenoxy)-ethyl]-morpholine as an off-white solid (4.30 g, 84%). NMR $^1$H (DSMO-d$_6$)-8.20 (d, 1H, J=9.34 Hz), 7.17 (d, 2H, J=9.34 Hz), 4.24 (t, 2H, J=5.65 Hz), 3.57 (t, 4H, J=4.60 Hz), 2.72 (t, 2H, J=4.68 Hz), 2.47 (t, 4H, J=4.52 Hz), 125b) Into a Round bottom flask, [A] 4-[2-(4-Nitro-phenoxy)-ethyl]-morpholine (3.70 g, 0.0147 mol), 10% Pd/C (10:90, Palladium:carbon black, 1.6 g, 0.0015 mol), and Ethanol (100 mL, 2 mol) were added. The mixture was evacuated under house vacuum and charged with a hydrogen balloon (3×). The reaction was stirred at room temperature under an atmosphere of Hydrogen via a balloon. The solid was filtered. The solvent was removed under vacuum to give 4-(2-Morpholin-4-yl-ethoxy)-phenylamine a white solid (3.00 g, 92%). NMR $^1$H (DSMO-d$_6$)-6.63 (dd, 1H, J=1.92, 4.76 Hz), 6.49 (dd, 2H, J=1.97, 4.72 Hz), 4.52 (bs, 2H), 3.91 (t, 2H, J=5.84 Hz), 3.56 (t, 4H, J=4.60 Hz), 2.60 (t, 2H, J=4.580 Hz), 2.47 (t, 4H, J=4.48 Hz)

125c) The titled compound was prepared in an analogous fashion as Example 124 replacing 1H-Pyrazol-3-ylamine with 4-(2-Morpholin-4-yl-ethoxy)-phenylamine to give [4-(2-Morpholin-4-yl-ethoxy)-phenyl]-(7-pyridin-3-yl-pyrrolo[2,1-f][1,2,4]triazin-2-yl)-amine; compound with trifluoro-acetic acid (45 mg, 21%). LCMS (E/I+) 417.7 (M+H). NMR $^1$H (DSMO-d$_6$)-10.00 (bs, 1H), 9.45 (s, 1H), 9.38 (d, 1H, J=1.44 Hz), 9.02 (s, 1H), 8.56-8.68 (m, 2H), 7.68 (d, 2H, J=9.01 Hz), 7.58-7.63 (m, 1H), 7.31 (d, 1H, J=4.81 Hz), 6.95-7.04 (m, 3H), 4.34 (t, 2H, J=4.80 Hz), 3.90-4.05 (m, 4H), 3.63-3.80 (m, 2H), 3.40-3.62 (m, 4H), 3.10-3.20 (m, 2H).

Example 126

(7-Pyridin-3-yl-pyrrolo[2,1-f][1,2,4]triazin-2-yl)-[4-(2-pyrrolidin-1-yl-ethoxy)-phenyl]-amine The titled compound was prepared in an analogous fashion as Example 124 replacing 1H-Pyrazol-3-ylamine with 4-(2-Pyrrolidin-1-yl-ethoxy)-phenylamine to give (7-Pyridin-3-yl-pyrrolo[2,1-f][1,2,4]triazin-2-yl)-[4-(2-pyrrolidin-1-yl-ethoxy)-phenyl]-amine; compound with trifluoro-acetic acid (42 mg, 20%). MP 240-241° C. LCMS (E/I+) 373.18 (M+H). NMR $^1$H (DSMO-d$_6$)-9.75 (bs, 1H), 9.45 (s, 1H), 9.36 (d, 1H, J=1.08 Hz), 9.04 (s, 1H), 8.58-8.70 (m, 2H), 7.68 (d, 2H, J=9.04 Hz), 7.59-7.65 (m, 1H), 7.31 (d, 1H, J=4.77 Hz), 6.95-7.06 (m, 3H), 4.30 (t, 2H, J=5.12 Hz), 3.52-3.70 (m, 4H), 3.06-3.21 (m, 2H), 1.80-2.15 (m, 4H).

Example 127

(7-Cyclohexyl-pyrrolo[2,1-f][1,2,4]triazin-2-yl)-(4-morpholin-4-yl-phenyl)-amine Into a Microwave vial, [A] 7-Cyclohexyl-2-methanesulfinyl-pyrrolo[2,1-f][1,2,4]triazine (0.140 g, 0.000532 mol), [B] 4-(4-morpholino)aniline (0.208 g, 0.00117 mol), 1-Methoxy-2-propanol (1.49 mL, 0.0152 mol) and N,N-Diisopropylethylamine (0.204 mL, 0.00117 mol) were added. The reaction was microwaved on 300 watts, 170° C. for 50 minutes. The solvent was removed under vacuum. The desired product was isolated via HPLC column chromatography with 0.1% TFA in water and 0.1% TFA in ACN as eluant. The collected fractions were lyophilized to afford (7-Cyclohexyl-pyrrolo[2,1-f][1,2,4]triazin-2-yl)-(4-morpholin-4-yl-phenyl)-amine; compound with trifluoro-acetic acid a yellow solid (47 mg, 18%). MP 240-241° C. LCMS (E/I+) 378.8 (M+H). NMR $^1$H (DSMO-d$_6$)-9.26 (s, 1H), 8.81 (s, 1H), 7.76 (d, 2H, J=11.49 Hz), 7.05 (bd, 2H, J=8.44 Hz), 6.75 (d, 1H, J=4.73 Hz), 6.55 (d, 1H, J=5.09 Hz), 3.70-4.30 (m, 1H), 3.03-3.23 (m, 5H), 2.06-2.17 (m, 2H), 1.23-1.90 (m, 8H).

Example 128

[7-(2-Methoxy-phenyl)-pyrrolo[2,1-f][1,2,4]triazin-2-yl]-[4-(2-morpholin-4-yl-ethoxy)-phenyl]-amine Into a Microwave vial, [A] 2-Methanesulfinyl-7-(2-methoxy-phenyl)-pyrrolo[2,1-f][1,2,4]triazine (0.116 g, 0.000404 mol), [B] 4-(2-Morpholin-4-yl-ethoxy)-phenylamine (0.197 g, 0.000888 mol), 1-Methoxy-2-propanol (0.971 mL, 0.00993 mol) and N,N-Diisopropylethylamine (0.155 mL, 0.000888 mol) were added. The reaction was microwaved on 300 watts, 170° C. for 50 minutes. The solvent was removed under vacuum. The desired product was isolated via ISCO column chromatography with DCM and methanol as eluant (0 to 12% methanol). The collected fractions afforded [7-(2-Methoxy-phenyl)-pyrrolo[2,1-f][1,2,4]triazin-2-yl]-[4-(2-morpholin-4-yl-ethoxy)-phenyl]-amine a yellow solid (22 mg, 12%). MP 125-126° C. LCMS (E/I+) 446.8 (M+H). NMR $^1$H (DSMO-d$_6$)-9.20 (s, 1H), 8.91 (s, 1H), 7.79 (dd, 1H, JJ=1.60, 6.04 Hz), 7.61 (d, 2H, J=9.00 Hz), 7.45 (dt, 1H, JJ=1.40, 7.12 Hz), 7.21 (d, 1H, J=8.36 Hz), 7.12 (t, 1H, J=7.53 Hz), 6.92 (d, 1H, J=4.56 Hz), 6.89 n (d, 1H, J=4.64 Hz), 6.80 (d, 2H, J=9.00 Hz), 4.02 (t, 2H, J=5.80 Hz), 3.79 (s, 3H), 3.3.58 (t, 4H, J=4.68 Hz), 2.65 (t, 2H, J=5.68 Hz), 2.46 (t, 4H, J=4.48 Hz).

Example 141

[7-(5-Chloro-2-methoxy-phenyl)-pyrrolo[2,1-f][1,2,4]triazin-2-yl]-(3,4,5-trimethoxy-phenyl)-amine 141a) 1-Amino-1H-pyrrole-2-carboxylic acid ethyl ester. 2 M of Sodium hypochlorite in Water (750 mL) (10-14% solution) was added dropwise to a solution of 1H-Pyrrole-2-carboxylic acid ethyl ester (50.0 g, 359 mmol), 2-Methoxy- 2-methylpropane (1000 mL), Aliquot 336 (12 g, 31 mmol), 7 M of Sodium hydroxide in Water (1030 mL), 8 M of Ammonium hydroxide in Water (330 mL) and Ammonium chloride (120 g, 2200 mmol). The reaction was immediately worked up upon complete addition of sodium hypochlorite. The organic layer was separated and was washed with saturated sodium thiosulfate (3×500 mL). Organic extracts (3×500 mL) were dried over magnesium sulfate, filtered and reduced to afford 53.0 grams 1-Amino-1H-pyrrole-2-carboxylic acid ethyl ester as a brown oil without further purification.

141b) 1-(3-Benzoyl-thioureido)-1H-pyrrole-2-carboxylic acid ethyl ester.

1-Amino-1H-pyrrole-2-carboxylic acid ethyl ester (53.0 g, 0.344 mol) was dissolved in Tetrahydrofuran (2000 mL). Benzoyl isothiocyanate (56.1 g, 0.344 mol) was added and the reaction was allowed to stir overnight. The reaction mixture was reduced and 55.47 grams of 1-(3-Benzoyl-thioureido)-1H-pyrrole-2-carboxylic acid ethyl ester was isolated as a white solid via trituration with ether. (M+Na)=339.98. $^1$H NMR (400 MHz, DMSO, $d_6$) δ 12.91 (s, 1H), 11.94 (s, 1H), 7.98 (d, 1H, J=7.32 Hz), 7.68 (t, 1H, J=7.52 Hz), 7.56 (t, 2H, J=7.64 Hz), 7.16 (m, 1H), 6.89 (m, 1H), 6.19 (m, 1H), 4.14 (q, 2H, J=7.12 Hz), 1.18 (d, 3H, J=14.17 Hz).

141c) 2-Thioxo-2,3-dihydro-1H-pyrrolo[2,1-f][1,2,4]triazin-4-one

Into a 1000 mL beaker was added 1-(3-Benzoyl-thioureido)-1H-pyrrole-2-carboxylic acid ethyl ester (55.47 g, 0.1748 mol) and 2M of Sodium hydroxide in Water (350 mL). The mixture was heated at 85° C. for 75 minutes. After cooling to room temperature, the solid was dissolved with Ethanol (100 mL). Acetic acid (41.7 mL, 0.734 mol) was added at 0° C. and stirred for 30 minutes. The solid was filtered and washed with cold EtOH (50 mL) to afforded a white solid. The white solid was stirred in Ether (300 mL) for 20 minutes. The solid was filtered and washed with Ether (200 mL) to give a white solid. Because a large amount of desired product was water soluble, the water filtrate was reduced and the product was triturated with water to afford an additional amount of desired product. After drying under vacuum overnight, 43 grams of 2-Thioxo-2,3-dihydro-1H-pyrrolo[2,1-f][1,2,4]triazin-4-one was isolated as a white powder. Note. The product contained a significant amount of water but was carried on without further drying. $^1$H NMR (400 MHz, DMSO, $d_6$) δ 9.91 (s, 1H), 7.09 (m, 1H), 6.53 (m, 1H), 6.21 (m, 1H).

141d) 2-Methylsulfanyl-3H-pyrrolo[2,1-f][1,2,4]triazin-4-one

Into a Round bottom flask, 2-Thioxo-2,3-dihydro-1H-pyrrolo[2,1-f][1,2,4]triazin-4-one (29.22 g, 0.1748 mol), Tetrahydrofuran (800 mL) and Methyl iodide (14.0 mL, 0.225 mol) were added, respectively. The reaction was stirred at room temperature overnight. The solvent was removed under vacuum to give a solid. The combined solid was washed with water (500 mL) and saturated $NaHCO_3$ (500 mL). The mixture was stirred for 30 minutes. The solid was filtered and washed with water to give 2-Methylsulfanyl-3H-pyrrolo[2,1-f][1,2,4]triazin-4-one as a white solid which was allowed to dry under vacuum overnight, affording 23.23 grams. $^1$H NMR (400 MHz, DMSO, $d_6$) δ 12.02 (s, 1H), 7.52 (m, 1H), 6.84 (m, 1H), 6.47 (m, 1H), 2.53 (s, 3H).

141e) 4-Chloro-2-methylsulfanyl-pyrrolo[2,1-f][1,2,4]triazine

2-Methylsulfanyl-3H-pyrrolo[2,1-f][1,2,4]triazin-4-one (23.25 g, 0.1283 mol) was dissolved in Phosphoryl chloride (114 mL, 1.22 mol) and the reaction was then heated at 75° C. until HPLC showed consumption of starting material. The mixture was reduced and the solution was poured over ice. The solid was then filtered and washed with water to afford the desired product. The product was then allowed to dry under vacuum overnight to provide 25.47 grams of 4-Chloro-2-methylsulfanyl-pyrrolo[2,1-f][1,2,4]triazine as a yellow solid. $^1$H NMR (400 MHz, DMSO, $d_6$) δ 8.16 (s, 1H), 7.05 (m, 1H), 6.98 (m, 1H), 2.55 (s, 3H).

141f) 7-Bromo-4-chloro-2-methylsulfanyl-pyrrolo[2,1-f][1,2,4]triazine

Into a Round bottom flask, [A] 4-Chloro-2-methylsulfanyl-pyrrolo[2,1-f][1,2,4]triazine (25.47 g, 0.1276 mol), Tetrahydrofuran (1000 mL), and Methanol (640 mL) were added. N-Bromosuccinimide (22.7 g, 0.128 mol) was added portionwise to the reaction for 1 hour at 0° C. The reaction was stirred at room temperature for 1 hour and the solvent was removed under vacuum. The solid was partitioned with water and DCM (500 mL). The organic was separated, washed with Brine, and dried over magnesium sulfate. The solid was filtered and washed with DCM. The filtrate was then reduced under vacuum to afford 7-Bromo-4-chloro-2-methylsulfanyl-pyrrolo[2,1-f][1,2,4]triazine as a yellow solid. 7-Bromo-4-chloro-2-methylsulfanyl-pyrrolo[2,1-f][1,2,4]triazine was suspended in Isopropyl alcohol (410 mL) at 55° C. Sodium borohydride (10.1 g, 0.268 mol) was added and heated at 60° C. for 3 hours. The reaction was allowed to cool to RT. The solid was filtered and washed with DCM. The solvent was partially removed to ensure the intermediate stayed in solution. (The intermediate is not stable out of solution). Methylene chloride (800 mL) was added to the viscous oil. Dichlorodicyanoquinone (31.8 g, 0.140 mol) was then added portion wise over 15 minutes. The mixture was stirred for 30 minutes. The solid was filtered through Celite, washed with DCM and the filtrate was removed under vacuum. The crude reaction mixture was purified via ISCO column chromatography with hexane and EtOAc as an eluant (0 to 8% EtOAc). The collected fractions afforded 12.2 grams of 7-Bromo-4-chloro-2-methylsulfanyl-pyrrolo[2,1-f][1,2,4]triazine as a light yellow solid. $^1$H NMR (400 MHz, DMSO, $d_6$) δ 8.95 (s, 1H), 7.09 (s, 2H), 2.55 (s, 3H).

141g) 7-(5-Chloro-2-methoxy-phenyl)-2-methylsulfanyl-pyrrolo[2,1-f][1,2,4]triazine Palladium Acetate (0.37 g, 0.0016 mol) and Triphenylphosphine (0.54 g, 0.0020 mol) were dissolved in Tetrahydrofuran (25 mL, 0.31 mol) and the mixture was allowed to stir at room temperature for 10 minutes. 7-Bromo-2-methylsulfanyl-pyrrolo[2,1-f][1,2,4]triazine (2.00 g, 0.00819 mol) was then added and the reaction was again allowed to stir for 10 minutes. 5-Chloro-2-methoxyphenyl boronic acid (3.05 g, 0.0164 mol) was added followed by 0.9 M of Sodium carbonate in water (20 mL, 0.02 mol) and Ethanol (25 mL, 0.43 mol). The reaction mixture was then heated at 80° C. and was allowed to stir overnight. The reaction mixture was then poured over saturated sodium chloride, and organics were extracted with ethyl acetate/dichloromethane. Combined organics were dried over sodium sulfate, filtered and reduced en vacuo. The crude mixture was purified by Isco flash column chromatography (Hexane/Ethyl Acetate). Combined fractions were reduced en vacuo to afford 1.16 g of 7-(5-Chloro-2-methoxy-phenyl)-2-methylsulfanyl-pyrrolo[2,1-f][1,2,4]triazine as a yellow solid.

141h) 7-(5-Chloro-2-methoxy-phenyl)-2-methanesulfinyl-pyrrolo[2,1-f][1,2,4]triazine 7-(5-Chloro-2-methoxyphenyl)-2-methylsulfanyl-pyrrolo[2,1-f][1,2,4]triazine (0.730 g, 0.00239 mol) was dissolved in Methylene chloride (20 mL, 0.4 mol) and the mixture was treated with m-Chloroperbenzoic acid (0.556 g, 0.00322 mol). The reaction was allowed to stir at room temperature until HPLC showed consumption of starting material. The reaction was partitioned between sodium thiosulfate and DCM and the combined organic layers were dried over saturated sodium sulfate. The solution was filtered and reduced. The solid was then triturated with ether to afford 700 mg of 7-(5-Chloro-2-methoxy-phenyl)-2-methanesulfinyl-pyrrolo[2,1-f][1,2,4]triazine as a yellow powder. (M+H)=322.6.

141i) 7-(5-Chloro-2-methoxy-phenyl)-2-methanesulfinyl-pyrrolo[2,1-f][1,2,4]triazine (75.0 mg, 0.000233 mol) and 3,4,5-Trimethoxyaniline (51 mg, 0.00028 mol) were dissolved in N-Methylpyrrolidinone (5.00 mL) and the reaction was heated at 140° C. until HPLC showed consumption of starting material. The reaction mixture was then reduced en vacuo and the product was isolated and purified by Gilson prep HPLC to afford 29.22 mg of [7-(5-Chloro-2-methoxy-phenyl)-pyrrolo[2,1-f][1,2,4]triazin-2-yl]-(3,4,5-trimethoxy-phenyl)-amine as a lyophilated powder. (M+H)=441.09. $^1$H NMR (400 MHz, DMSO, $d_6$) δ 9.29 (s, 1H), 8.97 (s, 1H), 7.73 (s, 1H), 7.45 (m, 1H), 7.22 (d, 1H, J=8.84 Hz), 7.02 (s, 2H), 6.92 (m, 2H), 3.76 (s, 3H), 3.57 (s, 3H), 3.49 (s, 6H).

Example 142

[7-(2-Methoxy-phenyl)-pyrrolo[2,1-f][1,2,4]triazin-2-yl]-(3,4,5-trimethoxy-phenyl)-amine 142a) 7-(2-Methoxy-phenyl)-2-methylsulfanyl-pyrrolo[2,1-f][1,2,4]triazine The compound was prepared in an analogous fashion to Example 1G replacing 5-Chloro-2-methoxyphenyl boronic acid with 2-methoxyphenylboronic acid to afford 7-(2-Methoxy-phenyl)-2-methylsulfanyl-pyrrolo[2,1-f][1,2,4]triazine as a yellow powder.

142b) 7-(2-Methoxy-phenyl)-2-methylsulfinyl-pyrrolo[2,1-f][1,2,4]triazine

The compound was prepared in an analogous fashion to Example 1H replacing 7-(5-Chloro-2-methoxy-phenyl)-2-methylsulfanyl-pyrrolo[2,1-f][1,2,4]triazine with 7-(2-Methoxy-phenyl)-2-methylsulfanyl-pyrrolo[2,1-f][1,2,4]triazine to afford 7-(2-Methoxy-phenyl)-2-methylsulfinyl-pyrrolo[2,1-f][1,2,4]triazine as a yellow powder. (M+H)=288.6.

142c) The compound was prepared in an analogous fashion to Example 11 replacing 7-(5-Chloro-2-methoxy-phenyl)-2-methanesulfinyl-pyrrolo[2,1-f][1,2,4]triazine with 7-(2-Methoxy-phenyl)-2-methylsulfinyl-pyrrolo[2,1-f][1,2,4]triazine to afford 11.36 mg of [7-(2-Methoxy-phenyl)-pyrrolo[2,1-f][1,2,4]triazin-2-yl]-(3,4,5-trimethoxy-phenyl)-amine as a lyophilated powder. (M+H)=407.12. $^1$H NMR (400 MHz, DMSO, $d_6$) δ 9.23 (s, 1H), 8.94 (s, 1H), 7.62 (d, 1H, J=7.33 Hz), 7.42 (m, 1H), 7.17 (d, 1H, J=8.09 Hz), 7.05 (m, 3H), 6.92 (d, 1H, J=4.54 Hz), 6.84 (d, 1H, J=4.54 Hz), 3.73 (s, 3H), 3.56 (s, 3H), 3.46 (s, 6H).

Example 143

[7-(3-Chloro-phenyl)-pyrrolo[2,1-f][1,2,4]triazin-2-yl]-(3,4,5-trimethoxy-phenyl)-amine 143a). 7-(3-Chloro-phenyl)-2-methanesulfinyl-pyrrolo[2,1-f][1,2,4]triazine The compound was prepared in an analogous fashion to Example 1G replacing 5-Chloro-2-methoxyphenyl boronic acid with 3-chlorophenylboronic acid to afford 7-(3-Chloro-phenyl)-2-methanesulfinyl-pyrrolo[2,1-f][1,2,4]triazine as a yellow powder.

143b) 7-(3-Chloro-phenyl)-2-methylsulfinyl-pyrrolo[2,1-f][1,2,4]triazine

The compound was prepared in an analogous fashion to Example 1H replacing 7-(5-Chloro-2-methoxy-phenyl)-2-methylsulfanyl-pyrrolo[2,1-f][1,2,4]triazine with 7-(3-Chloro-phenyl)-2-methanesulfinyl-pyrrolo[2,1-f][1,2,4]triazine to afford 7-(3-Chloro-phenyl)-2-methylsulfinyl-pyrrolo[2,1-f][1,2,4]triazine as a yellow powder. (M+H)=292.5.

143c) The compound was prepared in an analogous fashion to Example 11 replacing 7-(5-Chloro-2-methoxy-phenyl)-2-methanesulfinyl-pyrrolo[2,1-f][1,2,4]triazine with 7-(3-Chloro-phenyl)-2-methanesulfinyl-pyrrolo[2,1-f][1,2,4]triazine to afford 8.94 mg of [7-(3-Chloro-phenyl)-pyrrolo[2,1-f][1,2,4]triazin-2-yl]-(3,4,5-trimethoxy-phenyl)-amine as a lyophilated powder. (M+H)=411.09. $^1$H NMR (400 MHz, DMSO, $d_6$) δ 9.33 (s, 1H), 9.01 (s, 1H), 8.25 (s, 1H), 8.10 (d, 1H, J=7.83 Hz), 7.50 (m, 1H), 7.43 (m, 1H), 7.24 (d, 1H, J=4.80 Hz), 7.02 (s, 2H), 6.98 (d, 1H, J=4.80 Hz), 3.64 (s, 6H), 3.62 (s, 3H).

Example 144

[7-(5-Chloro-2-methoxy-phenyl)-pyrrolo[2,1-f][1,2,4]triazin-2-yl]-(3-methoxy-phenyl)-amine 7-(5-Chloro-2-methoxy-phenyl)-2-methanesulfinyl-pyrrolo[2,1-f][1,2,4]triazine (75.0 mg, 0.000233 mol) and [B] 3-methoxyaniline (57.4 mg, 0.000466 mol) were dissolved in N-Methylpyrrolidinone (2.0 mL) and the reaction was heated at 140° C. until HPLC showed consumption of starting material. The reaction mixture was then reduced en vacuo and the product was isolated and purified by Gilson prep HPLC to afford 8.08 mg of [7-(5-Chloro-2-methoxy-phenyl)-pyrrolo[2,1-f][1,2,4]triazin-2-yl]-(3-methoxy-phenyl)-amine as a lyophilated powder. (M+H)=381.09. $^1$H NMR (400 MHz, DMSO, $d_6$) δ 9.44 (s, 1H), 8.98 (s, 1H), 7.89 (s, 1H), 7.49 (m, 1H), 7.37 (m, 1H), 7.24 (m, 3H), 7.01 (d, 1H, J=4.55 Hz), 6.94 (d, 1H, J=4.55 Hz), 6.50 (d, 1H, J=8.34 Hz), 3.80 (s, 3H), 3.60 (s, 3H).

Example 145

(3-Methoxy-phenyl)-[7-(2-methoxy-phenyl)-pyrrolo[2,1-f][1,2,4]triazin-2-yl]-amine The compound was prepared in an analogous fashion to Example 11 replacing 745-Chloro-2-methoxy-phenyl)-2-methanesulfinyl-pyrrolo[2,1-f][1,2,4]triazine with 7-(2-Methoxy-phenyl)-2-methylsulfanyl-pyrrolo[2,1-f][1,2,4]triazine to afford 8.94 mg of (3-Methoxy-phenyl)-[7-(2-methoxy-phenyl)-pyrrolo[2,1-f][1,2,4]triazin-2-yl]-amine as a lyophilated powder. (M+H)=347.13. $^1$H NMR (400 MHz, DMSO, $d_6$) δ 9.38 (s, 1H), 8.96 (s, 1H), 7.74 (d, 1H, J=7.58 Hz), 7.45 (m, 2H), 7.19 (m, 2H), 7.06 (m, 2H), 6.95 (m, 2H), 6.45 (d, 1H, J=8.08 Hz), 3.78 (s, 3H), 3.55 (s, 3H).

Example 146

[7-(3-Chloro-phenyl)-pyrrolo[2,1-f][1,2,4]triazin-2-yl]-(3-methoxy-phenyl)-amine The compound was prepared in an analogous fashion to Example 11 replacing 745-Chloro-2-methoxy-phenyl)-2-methanesulfinyl-pyrrolo[2,1-f][1,2,4]triazine with 7-(3-Chloro-phenyl)-2-methanesulfinyl-pyrrolo[2,1-f][1,2,4]triazine to afford 6.91 mg of [7-(3-Chloro-phenyl)-pyrrolo[2,1-f][1,2,4]triazin-2-yl]-(3-methoxy-phenyl)-amine as a lyophilated powder. (M+H)=351.12. $^1$H NMR (400 MHz, DMSO, d$_6$) δ 9.53 (s, 1H), 9.02 (s, 1H), 8.38 (s, 1H), 8.09 (d, 1H, J=7.83 Hz), 7.51 (m, 1H), 7.30 (m, 2H), 7.26 (m, 3H), 6.97 (d, 1H, J=4.80 Hz), 6.57 (d, 1H, J=8.08 Hz), 3.70 (s, 3H).

Example 147

[7-(2-Methoxy-phenyl)-pyrrolo[2,1-f][1,2,4]triazin-2-yl]-(3-morpholin-4-yl-phenyl)-amine 2-Methane sulfinyl-7-(2-methoxy-phenyl)-pyrrolo[2,1-f][1,2,4]triazine (75.0 mg, 0.000261 mol) and 3-Morpholin-4-yl-phenylamine (93.0 mg, 0.000522 mol) were dissolved in N-Methylpyrrolidinone (2.0 mL) and the reaction was heated at 140° C. until HPLC showed consumption of starting material. The reaction mixture was then reduced en vacuo and the product was isolated and purified by Gilson prep HPLC to afford 9.70 mg of [7-(2-Methoxy-phenyl)-pyrrolo[2,1-f][1,2,4]triazin-2-yl]-(3-morpholin-4-yl-phenyl)-amine as a lyophilated powder. (M+H)=402.20. $^1$H NMR (400 MHz, DMSO, d$_6$) δ 9.23 (s, 1H), 8.94 (s, 1H), 7.70 (d, 1H, J=7.84 Hz), 7.46 (m, 1H), 7.34 (s, 1H), 7.19 (d, 1H, J=7.83 Hz), 7.08 (m, 3H), 6.90 (m, 2H), 6.87 (m, 1H), 3.75 (s, 3H), 3.63 (m, 4H), 2.83 (m, 4H).

Example 148

[7-(3-Chloro-phenyl)-pyrrolo[2,1-f][1,2,4]triazin-2-yl]-(3-morpholin-4-yl-phenyl)-amine The compound was prepared in an analogous fashion to Example 14 replacing 2-Methanesulfinyl-7-(2-methoxy-phenyl)-pyrrolo[2,1-f][1,2,4]triazine with 7-(3-Chloro-phenyl)-2-methanesulfinyl-pyrrolo[2,1-f][1,2,4]triazine to afford 6.53 mg of [7-(3-Chloro-phenyl)-pyrrolo[2,1-f][1,2,4]triazin-2-yl]-(3-morpholin-4-yl-phenyl)-amine as a lyophilated powder. (M+H)=406.13. $^1$H NMR (400 MHz, DMSO, d$_6$) δ 9.38 (s, 1H), 9.01 (s, 1H), 8.35 (s, 1H), 8.05 (d, 1H, J=7.83 Hz), 7.52 (m, 1H), 7.45 (d, 1H, J=7.32 Hz), 7.36 (d, 1H, J=8.34 Hz), 7.34 (m, 3H), 6.96 (d, 1H, J=4.80 Hz), 6.60 (d, 1H, J=7.83 Hz), 3.67 (m, 4H), 3.01 (m, 4H).

Example 149

1,3-Benzodioxol-5-yl-[7-(2-methoxy-phenyl)-pyrrolo[2,1-f][1,2,4]triazin-2-yl]-amine 2-Methane sulfinyl-7-(2-methoxy-phenyl)-pyrrolo[2,1-f][1,2,4]triazine (67.0 mg, 0.000233 mol) and 1,3-Benzodioxol-5-ylamine (63.9 mg, 0.000466 mol) were dissolved in 2-Methoxyethanol (1.64 mL) and the reaction was heated at 180° C. until HPLC showed consumption of starting material. The reaction mixture was then reduced en vacuo and the product was isolated and purified by Gilson prep HPLC to afford 2.65 mg 1,3-Benzodioxol-5-yl-[7-(2-methoxy-phenyl)-pyrrolo[2,1-f][1,2,4]triazin-2-yl]-amine as a lyophilated powder. (M+H)=361.20. $^1$H NMR (400 MHz, DMSO, d$_6$) δ 9.29 (s, 1H), 8.93 (s, 1H), 7.75 (d, 1H, J=7.07 Hz), 7.51 (s, 1H), 7.46 (m, 1H), 7.20 (m, 1H), 7.10 (m, 2H), 7.05 (s, 2H), 6.76 (d, 1H, J=8.34 Hz), 5.94 (s, 2H), 3.79 (s, 3H).

Example 150

1,3-Benzodioxol-5-yl-[7-(3-chloro-phenyl)-pyrrolo[2,1-f][1,2,4]triazin-2-yl]-amine The compound was prepared in an analogous manner to Example 16 replacing 2-Methanesulfinyl-7-(2-methoxy-phenyl)-pyrrolo[2,1-f][1,2,4]triazine with 7-(3-Chloro-phenyl)-2-methanesulfinyl-pyrrolo[2,1-f][1,2,4]triazine to afford 2.33 mg of 1,3-Benzodioxol-5-yl-[7-(3-chloro-phenyl)-pyrrolo[2,1-f][1,2,4]triazin-2-yl]-amine as a lyophilated powder. (M+H)=365.14. $^1$H NMR (400 MHz, DMSO, d$_6$) δ 9.42 (s, 1H), 8.99 (s, 1H), 8.38 (s, 1H), 8.07 (d, 1H, J=7.58 Hz), 7.51 (m, 1H), 7.44 (m, 1H), 7.34 (s, 1 h), 7.26 (m, 2H), 6.95 (d, 1H, J=4.54 Hz), 6.87 (d, 1H, J=8.59 Hz), 5.98 (s, 2H).

Example 151

[7-(5-Chloro-2-methoxy-phenyl)-pyrrolo[2,1-f][1,2,4]triazin-2-yl]-(3,4-dimethoxy-phenyl)-amine

[7-(5-Chloro-2-methoxy-phenyl)-2-methanesulfinyl-pyrrolo[2,1-f][1,2,4]triazine (75.0 mg, 0.000233 mol) and 3,4-dimethoxyaniline (71.4 mg, 0.000466 mol) were dissolved in 2-Methoxyethanol (1.64 mL) and the reaction was heated at 180° C. until HPLC showed consumption of starting material. The reaction mixture was then reduced en vacuo and the product was isolated and purified by Gilson prep HPLC to afford 32.66 mg of [7-(5-Chloro-2-methoxy-phenyl)-pyrrolo[2,1-f][1,2,4]triazin-2-yl]-(3,4-dimethoxy-phenyl)-amine as a lyophilized powder. (M+H)=411.12. $^1$H NMR (400 MHz, DMSO, d$_6$) δ 9.24 (s, 1H), 8.95 (s, 1H), 7.93 (s, 1H), 7.48 (m, 1H), 7.31 (m, 2H), 6.97 (d, 1H, J=4.80 Hz), 6.82 (d, 1H, J=8.34 Hz), 6.26 (m, 1H), 6.05 (dd, 1H, J=2.52, 6.07 Hz), 3.79 (s, 3H), 3.69 (s, 3H), 3.65 (s, 3H).

Example 152

[7-(3-Chloro-phenyl)-pyrrolo[2,1-f][1,2,4]triazin-2-yl]-(3,4-dimethoxy-phenyl)-amine The compound was prepared in an analogous manner to Example 18 replacing [7-(5-Chloro-2-methoxy-phenyl)-2-methanesulfinyl-pyrrolo[2,1-f][1,2,4]triazine with 7-(3-Chloro-phenyl)-2-methanesulfinyl-pyrrolo[2,1-f][1,2,4]triazine to afford 13.28 mg of [7-(3-Chloro-phenyl)-pyrrolo[2,1-f][1,2,4]triazin-2-yl]-(3,4-dimethoxy-phenyl)-amine as a lyophilized powder. (M+H)=381.10. $^1$H NMR (400 MHz, DMSO, d$_6$) δ 9.29 (s, 1H), 8.98 (s, 1H), 8.39 (s, 1H), 8.06 (d, 1H, J=8.34 Hz), 7.52 (m, 1H), 7.44 (m, 2H), 7.25 (m, 2H), 6.95 (m, 2H), 3.74 (s, 3H), 3.66 (s, 3H).

Example 153

[7-(5-Chloro-2-methoxy-phenyl)-pyrrolo[2,1-f][1,2,4]triazin-2-yl]-(4-methoxy-phenyl)-amine 7-(5-Chloro-2-methoxy-phenyl)-2-methanesulfinyl-pyrrolo[2,1-f][1,2,4]triazine (75.0 mg, 0.000233 mol) and 4-Methoxybenzenamine (57.4 mg, 0.000466 mol) were dissolved in 2-Methoxyethanol (1.64 mL) and the reaction was heated at 180° C. until HPLC showed consumption of starting material. The reaction mixture was then reduced en vacuo and the product was isolated and purified by Gilson prep HPLC to afford 12.41 mg of [7-(5-Chloro-2-methoxy-phenyl)-pyrrolo[2,1-f][1,2,4]triazin-2-yl]-(4-methoxy-phenyl)-amine as a lyophilized powder. (M+H)=381.11. $^1$H NMR (400 MHz, DMSO, d$_6$) δ 9.29 (s, 1H), 8.95 (s, 1H), 8.05 (m, 1H), 7.63 (d, 2H, J=9.09 Hz), 7.46 (m, 1H), 7.23 (d, 1H, J=8.84 Hz), 7.03 (d, 1H, J=4.55 Hz), 6.90 (d, 1H, J=4.55 Hz), 6.85 (m, 2H), 3.82 (s, 3H), 3.70 (s, 3H).

Example 154

(4-Methoxy-phenyl)-[7-(2-methoxy-phenyl)-pyrrolo[2,1-f][1,2,4]triazin-2-yl]-amine The compound was prepared in an analogous fashion to Example 20 replacing 745-Chloro-2-methoxy-phenyl)-2-methanesulfinyl-pyrrolo[2,1-f][1,2,4]triazine with 7-(2-Methoxy-phenyl)-2-methylsulfanyl-pyrrolo[2,1-f][1,2,4]triazine to afford 8.61 mg of (4-Methoxy-phenyl)-[7-(2-methoxy-phenyl)-pyrrolo[2,1-f][1,2,4]triazin-2-yl]-amine as a lyophilated powder. (M+H)=347.19. $^1$H NMR (400 MHz, DMSO, $d_6$) δ 9.19 (s, 1H), 8.92 (s, 1H), 7.80 (d, 1H, J=7.58 Hz), 7.61 (d, 2H, J=9.10 Hz), 7.45 (m, 1H), 7.21 (m, 1H), 7.11 (m, 1H), 6.91 (m, 2H), 6.79 (m, 2H), 3.79 (s, 3H), 3.70 (s, 3H).

Example 155

[7-(3-Chloro-phenyl)-pyrrolo[2,1-f][1,2,4]triazin-2-yl]-(4-methoxy-phenyl)-amine The compound was prepared in an analogous fashion to Example 20 replacing 745-Chloro-2-methoxy-phenyl)-2-methanesulfinyl-pyrrolo[2,1-f][1,2,4]triazine with 7-(3-Chloro-phenyl)-2-methanesulfinyl-pyrrolo[2,1-f][1,2,4]triazine to afford 14.52 mg of [7-(3-Chloro-phenyl)-pyrrolo[2,1-f][1,2,4]triazin-2-yl]-(4-methoxy-phenyl)-amine as a lyophilated powder. (M+H)=351.13. $^1$H NMR (400 MHz, DMSO, $d_6$) δ 9.36 (s, 1H), 8.98 (s, 1H), 8.47 (s, 1H), 8.03 (d, 1H, J=7.58 Hz), 7.66 (d, 2H, J=9.10 Hz), 7.53 (m, 1H), 7.44 (m, 1H), 7.26 (m, 1H), 6.93 (m, 3H), 3.74 (s, 3H).

Example 156

[7-(3-Chloro-phenyl)-pyrrolo[2,1-f][1,2,4]triazin-2-yl]-(3,5-dimethoxy-phenyl)-amine 7-(3-Chloro-phenyl)-2-methanesulfinyl-pyrrolo[2,1-f][1,2,4]triazine (75.0 mg, 0.000257 mol) and Benzenamine, 3,5-dimethoxy- (78.8 mg, 0.000514 mol) were dissolved in 2-Methoxyethanol (1.80 mL) and the reaction was heated at 180° C. until HPLC showed consumption of starting material. The reaction mixture was then reduced en vacuo and the product was isolated and purified by Gilson prep HPLC to afford 3.89 mg of [7-(3-Chloro-phenyl)-pyrrolo[2,1-f][1,2,4]triazin-2-yl]-(3,5-dimethoxy-phenyl)-amine as a lyophilated powder. (M+H)=381.11. $^1$H NMR (400 MHz, DMSO, $d_6$) δ 9.46 (s, 1H), 9.02 (s, 1H), 8.24 (s, 1H), 8.17 (d, 1H, J=7.83 Hz), 7.51 (m, 1H), 7.44 (m, 1H), 7.28 (d, 1H, J=4.80 Hz), 6.97 (m, 3H), 6.15 (s, 1H), 3.67 (s, 6H).

Example 157

[7-(5-Chloro-2-methoxy-phenyl)-pyrrolo[2,1-f][1,2,4]triazin-2-yl]-(3,5-dimethoxy-phenyl)-amine The compound was made in an analogous fashion to Example 23 replacing 7-(3-Chloro-phenyl)-2-methanesulfinyl-pyrrolo[2,1-f][1,2,4]triazine with 7-(5-Chloro-2-methoxy-phenyl)-2-methanesulfinyl-pyrrolo[2,1-f][1,2,4]triazine to afford 13.34 mg of [7-(5-Chloro-2-methoxy-phenyl)-pyrrolo[2,1-f][1,2,4]triazin-2-yl]-(3,5-dimethoxy-phenyl)-amine as a lyophilated powder. (M+H)=411.12. $^1$H NMR (400 MHz, CDCl$_3$) δ 9.28 (m, 1H), 8.59 (s, 1H), 7.77 (m, 1H), 7.43 (m, 1H), 7.13 (s, 2H), 7.00 (d, 1H, J=8.84 Hz), 6.82 (s, 2H), 6.16 (s, 1H), 3.82 (s, 3H), 3.66 (s, 6H).

Example 158

(3,5-Dimethoxy-phenyl)-[7-(2-methoxy-phenyl)-pyrrolo[2,1-f][1,2,4]triazin-2-yl]-amine The compound was made in an analogous fashion to Example 23 replacing 7-(3-Chloro-phenyl)-2-methanesulfinyl-pyrrolo[2,1-f][1,2,4]triazine with 7-(2-Methoxy-phenyl)-2-methylsulfanyl-pyrrolo[2,1-f][1,2,4]triazine to afford 3.25 mg of [7-(5-Chloro-2-methoxy-phenyl)-pyrrolo[2,1-f][1,2,4]triazin-2-yl]-(3,5-dimethoxy-phenyl)-amine as a lyophilated powder. (M+H)=377.16. $^1$H NMR (400 MHz, CDCl$_3$) δ 8.59 (s, 1H), 7.84 (d, 1H, J=7.58 Hz), 7.43 (t, 1H, J=8.59 Hz), 7.10 (m, 4H), 6.83 (s, 2H), 6.13 (s, 1H), 3.83 (s, 3H), 3.62 (s, 6H).

Example 159

N-[7-(3-Chloro-phenyl)-pyrrolo[2,1-f][1,2,4]triazin-2-yl]-N',N'-dimethyl-benzene-1,3-diamine 7-(3-Chloro-phenyl)-2-methanesulfinyl-pyrrolo[2,1-f][1,2,4]triazine (76.2 mg, 0.000261 mol), N,N-Diisopropylethylamine (0.0682 mL, 0.000392 mol) and N,N-Dimethyl-benzene-1,3-diamine (71.1 mg, 0.000522 mol) were dissolved in 2-Methoxyethanol (1.83 mL, 0.0232 mol) and the reaction was heated at 180° C. until HPLC showed consumption of starting material. The reaction mixture was then reduced en vacuo and the product was isolated and purified by Gilson prep HPLC to afford 3.73 mg of N-[7-(3-Chloro-phenyl)-pyrrolo[2,1-f][1,2,4]triazin-2-yl]-N',N'-dimethyl-benzene-1,3-diamine as a lyophilated powder. (M+H)=364.11. $^1$H NMR (400 MHz, CDCl$_3$) δ 9.08 (s, 1H), 8.37 (d, 1H, J=9.60 Hz), 8.10 (s, 1H), 7.89 (d, 1H, J=7.58 Hz), 7.44 (m, 3H), 7.20 (d, 1H, J=4.80 Hz), 7.03 (d, 1H, J=4.54 Hz), 6.61 (m, 2H), 3.11 (s, 6H).

Example 160

[7-(2-Methoxy-phenyl)-pyrrolo[2,1-f][1,2,4]triazin-2-yl]-[3-(4-methyl-piperazin-1-yl)-phenyl]-amine 2-Methanesulfinyl-7-(2-methoxy-phenyl)-pyrrolo[2,1-f][1,2,4]triazine (75.0 mg, 0.000261 mol), N,N-Diisopropylethylamine (0.0682 mL, 0.000392 mol) and 3-(4-Methylpiperazin-1-yl)aniline (99.8 mg, 0.000522 mol) were dissolved in 2-Methoxyethanol (1.83 mL) and the reaction was heated under 300 W microwave conditions at 180° C. until HPLC showed consumption of starting material. The reaction mixture was then reduced en vacuo and the product was isolated and purified by Gilson prep HPLC to afford 8.59 mg of [7-(2-Methoxy-phenyl)-pyrrolo[2,1-f][1,2,4]triazin-2-yl]-[3-(4-methyl-piperazin-1-yl)-phenyl]-amine as lyophilated powder. (M+H)=415.18. $^1$H NMR (400 MHz, CDCl$_3$) δ 10.42 (s, 1H), 8.55 (s, 1H), 7.87 (d, 1H, J=6.57 Hz), 7.52 (s, 1H), 7.30 (m, 3H), 7.18 (m, 2H), 7.09 (m, 2H), 6.57 (s, 1H), 3.84 (s, 3H), 3.55 (d, 2H, J=11.12 Hz), 3.45 (d, 2H, J=13.64 Hz), 3.18 (m, 2H), 2.90 (m, 2H), 2.86 (s, 3H).

Example 161

[7-(3-Chloro-phenyl)-pyrrolo[2,1-f][1,2,4]triazin-2-yl]-[3-(4-methyl-piperazin-1-yl)-phenyl]-amine The compound was made in an analogous fashion to Example 27 replacing 2-Methanesulfinyl-7-(2-methoxy-phenyl)-pyrrolo[2,1-f][1,2,4]triazine with 7-(3-Chloro-phenyl)-2-methanesulfinyl-pyrrolo[2,1-f][1,2,4]triazine to afford 9.75 mg of [7-(3-Chloro-phenyl)-pyrrolo[2,1-f][1,2,4]triazin-2-yl]-[3-(4-methyl-piperazin-1-yl)-phenyl]-amine as a lyophilated powder. (M+H)=419.11. $^1$H NMR (400 MHz, CDCl$_3$) δ 8.66 (s, 1H), 8.52 (m, 1H), 8.25 (s, 1H), 7.89 (d, 1H, J=7.58 Hz), 7.45 (m, 2H), 7.32 (m, 2H), 7.20 (s, 1H), 7.11 (d, 1H, J=5.05 Hz), 7.05 (d, 1H, J=5.05 Hz), 6.63 (m, 1H), 3.58 (m, 4H), 3.28 (m, 2H), 2.94 (m, 2H), 2.86 (s, 3H).

Example 162

[7-(4-Methanesulfonyl-phenyl)-pyrrolo[2,1-f][1,2,4]triazin-2-yl]-(3,4,5-trimethoxy-phenyl)-amine 2-Methanesulfinyl-7-(4-methanesulfonyl-phenyl)-pyrrolo[2,1-f][1,2,4]triazine (125 mg, 0.000373 mol), N,N-Diisopropylethylamine (0.0974 mL, 0.000559 mol) and 3,4,5-Trimethoxyaniline (81.9 mg, 0.000447 mol) were dissolved in 2-Methoxyethanol (2.2 mL) and the reaction was heated at 180° C. under 300 W microwave conditions until HPLC showed consumption of starting material. The reaction mixture was then reduced en vacuo and the product was isolated and purified by Gilson prep HPLC to afford 24.45 mg of [7-(4-Methanesulfonyl-phenyl)-pyrrolo[2,1-f][1,2,4]triazin-2-yl]-(3,4,5-trimethoxy-phenyl)-amine as a lyophilated powder. (M+H)=455.14. $^1$H NMR (400 MHz, CDCl$_3$) δ 9.11 (m, 1H), 8.73 (s, 1H), 8.34 (d, 2H, J=8.59 Hz), 8.05 (d, 2H, J=8.34 Hz), 7.23 (m, 1H), 7.18 (d, 1H, J=5.05 Hz), 6.87 (s, 2H), 3.86 (s, 3H), 3.77 (s, 6H), 3.25 (s, 3H).

Example 163

[7-(4-Methanesulfonyl-phenyl)-pyrrolo[2,1-f][1,2,4]triazin-2-yl]-(3-morpholin-4-yl-phenyl)-amine The compound was prepared in an analogous manner to Example 29 replacing 3,4,5-Trimethoxyaniline with 3-Morpholin-4-yl-phenylamine to afford 16.06 mg of [7-(4-Methanesulfonyl-phenyl)-pyrrolo[2,1-f][1,2,4]triazin-2-yl]-(3-morpholin-4-yl-phenyl)-amine as a lyophilized powder. (M+H)=450.15. $^1$H NMR (400 MHz, CDCl$_3$) δ 8.76 (s, 1H), 8.48 (m, 1H), 8.37 (d, 2H, J=8.58 Hz), 8.06 (d, 2H, J=8.58 Hz), 7.38 (m, 3H), 7.21 (d, 1H, J=5.06 Hz), 7.08 (d, 1H, J=5.06 Hz), 6.89 (d, 1H, J=7.58 Hz), 3.93 (m, 4H), 3.26 (m, 4H), 3.13 (s, 3H).

Example 164

3-[7-(2-Methoxy-phenyl)-pyrrolo[2,1-f][1,2,4]triazin-2-ylamino]-benzamide

2-Methane sulfinyl-7-(2-methoxy-phenyl)-pyrrolo[2,1-f][1,2,4]triazine (125.0 mg, 0.0004350 mol), N,N-Diisopropylethylamine (0.114 mL, 0.000652 mol) and 3-Amino-benzamide (118 mg, 0.000870 mol) were dissolved in 2-Methoxyethanol (3.05 mL) and the reaction was microwaved on 300 watts, 180° C. for 40 minutes or until HPLC showed consumption of starting material. The reaction mixture was then reduced en vacuo and the product was isolated and purified by Gilson prep HPLC to afford 23.30 mg of 3-[7-(2-Methoxy-phenyl)-pyrrolo[2,1-f][1,2,4]triazin-2-ylamino]-benzamide as a lyophilized powder. (M+H)=360.11. $^1$H NMR (400 MHz, CDCl$_3$) δ 9.39 (m, 1H), 8.60 (s, 1H), 8.17 (s, 1H), 7.86 (d, 1H, J=7.64 Hz), 7.63 (d, 1H, J=8.00 Hz), 7.57 (d, 1H, J=7.80 Hz), 7.50 (t, 1H, J=7.56 Hz), 7.36 (t, 1H, J=7.88 Hz), 7.19 (d, 1H, J=5.00 Hz), 7.13 (m, 3H), 3.83 (s, 3H).

Example 165

3-[7-(3-Chloro-phenyl)-pyrrolo[2,1-f][1,2,4]triazin-2-ylamino]-benzamide

The compound was prepared in an analogous fashion to Example 31 replacing 2-Methanesulfinyl-7-(2-methoxyphenyl)-pyrrolo[2,1-f][1,2,4]triazine with 7-(3-Chloro-phenyl)-2-methanesulfinyl-pyrrolo[2,1-f][1,2,4]triazine to afford 2.88 mg of 3-[7-(3-Chloro-phenyl)-pyrrolo[2,1-f][1,2,4]triazin-2-ylamino]-benzamide as a lyophilized powder. (M+H)=364.11. $^1$H NMR (400 MHz, CDCl$_3$) δ 9.10 (s, 1H), 8.67 (s, 1H), 8.16 (m, 1H), 8.12 (m, 1H), 8.06 (d, 1H, J=6.76 Hz), 7.98 (m, 1H), 7.88 (d, 1H, J=7.92 Hz), 7.47 (m, 4H), 7.16 (m, 1H), 3.40 (s, 2H).

Example 166

3-[7-(5-Chloro-2-methoxy-phenyl)-pyrrolo[2,1-f][1,2,4]triazin-2-ylamino]-benzamide The compound was prepared in an analogous fashion to Example 31 replacing 2-Methanesulfinyl-7-(2-methoxyphenyl)-pyrrolo[2,1-f][1,2,4]triazine with 7-(5-Chloro-2-methoxy-phenyl)-2-methanesulfinyl-pyrrolo[2,1-f][1,2,4]triazine to afford 2.88 mg of 3-[7-(5-Chloro-2-methoxyphenyl)-pyrrolo[2,1-f][1,2,4]triazin-2-ylamino]-benzamide as a lyophilized powder. (M+H)=394.07. $^1$H NMR (400 MHz, CDCl$_3$) δ 8.64 (s, 1H), 8.03 (m, 1H), 7.93 (m, 1H), 7.52 (m, 1H), 7.44 (m, 4H), 7.19 (d, 1H, J=5.00 Hz), 7.09 (m, 1H), 7.00 (m, 1H), 3.84 (s, 3H).

Example 167

[7-(3-Chloro-phenyl)-pyrrolo[2,1-f][1,2,4]triazin-2-yl]-(4-pyrrolidin-1-yl-phenyl)-amine 7-(3-Chloro-phenyl)-2-methanesulfinyl-pyrrolo[2,1-f][1,2,4]triazine (125.0 mg, 0.0004284 mol), N,N-Diisopropylethylamine (0.112 mL, 0.000643 mol) and 4-Pyrrolidin-1-yl-phenylamine (139 mg, 0.000857 mol) were dissolved in 2-Methoxyethanol (3.01 mL) and The reaction was microwaved on 300 watts, 180° C. for 40 minutes or until HPLC showed consumption of starting material. The reaction mixture was then reduced en vacuo and the product was isolated and purified by Gilson prep HPLC to afford 26.91 mg of [7-(3-Chloro-phenyl)-pyrrolo[2,1-f][1,2,4]triazin-2-yl]-(4-pyrrolidin-1-yl-phenyl)-amine as a lyophilized powder. (M+H)=390.09. $^1$H NMR (400 MHz, CDCl$_3$) δ 9.63 (s, 1H), 8.63 (s, 1H), 8.32 (s, 1H), 7.84 (m, 1H), 7.76 (d, 2H, J=8.93 Hz), 7.48 (m, 2H), 7.34 (d, 2H, J=8.93 Hz), 7.21 (m, 1H), 7.18 (m, 1H), 3.66 (m, 4H), 2.25 (m, 4H).

Example 168

[7-(5-Chloro-2-methoxy-phenyl)-pyrrolo[2,1-f][1,2,4]triazin-2-yl]-(4-pyrrolidin-1-yl-phenyl)-amine The compound was prepared in an analogous fashion to Example 34 replacing 7-(3-Chloro-phenyl)-2-methanesulfinyl-pyrrolo[2,1-f][1,2,4]triazine with 7-(5-Chloro-2-methoxy-phenyl)-2-methanesulfinyl-pyrrolo[2,1-f][1,2,4]triazine to afford 10.71 mg of [7-(5-Chloro-2-methoxy-phenyl)-pyrrolo[2,1-f][1,2,4]triazin-2-yl]-(4-pyrrolidin-1-yl-phenyl)-amine as a lyophilized powder. (M+H)=420.11. $^1$H NMR (400 MHz, CDCl$_3$) δ 10.21 (m, 1H), 8.59 (s, 1H), 8.06 (s, 1H), 7.76 (d, 2H, J=9.00 Hz), 7.48 (m, 1H), 7.33 (m, 3H), 7.22 (m, 1H), 7.04 (d, 1H, J=8.86 Hz), 3.86 (s, 3H), 3.65 (m, 4H), 2.25 (m, 4H).

Example 169

[7-(2-Methoxy-phenyl)-pyrrolo[2,1-f][1,2,4]triazin-2-yl]-(4-pyrrolidin-1-yl-phenyl)-amine The compound was prepared in an analogous fashion to Example 34 replacing 7-(3-Chloro-phenyl)-2-methanesulfinyl-pyrrolo[2,1-f][1,2,4]triazine with 2-Methanesulfinyl-7-(2-methoxy-phenyl)-pyrrolo[2,1-f][1,2,4]triazine to afford 16.87 mg of [7-(2-Methoxy-phenyl)-pyrrolo[2,1-f][1,2,4]triazin-2-yl]-(4-pyrrolidin-1-yl-phenyl)-amine as a lyophilized powder. (M+H)=386.10. $^1$H NMR (400 MHz, CDCl$_3$) δ 8.50 (s, 1H), 7.94 (d, 1H, J=6.16 Hz), 7.66 (d, 2H, J=8.93 Hz), 7.51 (t, 1H, J=7.24 Hz), 7.27 (m, 1H), 7.19 (m, 2H), 7.12 (m, 2H), 6.97 (d, 2H, J=9.01 Hz), 3.86 (s, 3H), 3.50 (m, 4H), 2.16 (m, 4H).

Example 170

(1H-Indol-5-yl)-[7-(2-methoxy-phenyl)-pyrrolo[2,1-f][1,2,4]triazin-2-yl]-amine

2-Methane sulfinyl-7-(2-methoxy-phenyl)-pyrrolo[2,1-f][1,2,4]triazine (125.0 mg, 0.0004350 mol), N,N-Diisopropylethylamine (0.114 mL, 0.000652 mol) and 5-Aminoindole (115 mg, 0.000870 mol) were dissolved in 2-Methoxyethanol (3.05 mL) and the The reaction was microwaved on 300 watts, 180° C. for 40 minutes or until HPLC showed consumption of starting material. The reaction mixture was then reduced en vacuo and the product was isolated and purified by Gilson prep HPLC to afford 35.70 mg of (1H-Indol-5-yl)-[7-(2-methoxy-phenyl)-pyrrolo[2,1-f][1,2,4]triazin-2-yl]-amine as a lyophilized powder. (M+H)=356.18. $^1$H NMR (400 MHz, CDCl$_3$) δ 10.41 (s, 1H), 8.41 (s, 1H), 8.17 (m, 2H), 8.05 (d, 1H, J=6.13 Hz), 7.54 (m, 1H), 7.29 (m, 4H), 7.22 (m, 3H), 6.41 (m, 1H), 3.85 (s, 3H).

Example 171

[7-(5-Chloro-2-methoxy-phenyl)-pyrrolo[2,1-f][1,2,4]triazin-2-yl]-(1H-indol-5-yl)-amine The compound was prepared in an analogous fashion to Example 37 replacing 2-Methanesulfinyl-7-(2-methoxy-phenyl)-pyrrolo[2,1-f][1,2,4]triazine with 7-(5-Chloro-2-methoxy-phenyl)-2-methanesulfinyl-pyrrolo[2,1-f][1,2,4]triazine to afford 22.49 mg of [7-(5-Chloro-2-methoxy-phenyl)-pyrrolo[2,1-f][1,2,4]triazin-2-yl]-(1H-indol-5-yl)-amine as a lyophilized powder. (M+H)=390.14. $^1$H NMR (400 MHz, CDCl$_3$) δ 10.34 (s, 1H), 8.55 (s, 1H), 8.13 (s, 1H), 8.04 (m, 1H), 8.01 (m, 1H), 7.48 (d, 1H, J=6.23 Hz), 7.38 (m, 2H), 7.30 (d, 1H, J=5.29 Hz), 7.25 (d, 2H, J=5.44 Hz), 7.20 (m, 1H), 7.02 (d, 2H, J=8.92 Hz), 6.51 (m, 1H), 3.82 (s, 3H).

Example 172

[7-(2-Methoxy-phenyl)-pyrrolo[2,1-f][1,2,4]triazin-2-yl]-quinolin-6-yl-amine

The compound was prepared in an analogous fashion to Example 37 replacing 5-Aminoindole with Quinolin-6-yl amine to afford 8.28 mg of [7-(2-Methoxy-phenyl)-pyrrolo[2,1-f][1,2,4]triazin-2-yl]-quinolin-6-yl-amine as a lyophilized powder. (M+H)=368.23. $^1$H NMR (400 MHz, CDCl$_3$) δ 8.76 (m, 2H), 8.50 (m, 1H), 8.01 (m, 2H), 7.89 (d, 1H, J=8.04 Hz), 7.50 (m, 2H), 7.35 (m, 1H), 7.20 (t, 1H, J=7.52 Hz), 7.15 (d, 1H, J=8.32 Hz), 7.07 (m, 2H), 6.91 (d, 1H, J=4.68 Hz), 3.84 (s, 3H).

Example 173

[7-(5-Chloro-2-methoxy-phenyl)-pyrrolo[2,1-f][1,2,4]triazin-2-yl]-quinolin-6-yl-amine The compound was prepared in an analogous fashion to Example 20 replacing 4-Methoxybenzenamine with Quinolin-6-yl amine to afford 11.16 mg of [7-(5-Chloro-2-methoxy-phenyl)-pyrrolo[2,1-f][1,2,4]triazin-2-yl]-quinolin-6-yl-amine as a lyophilized powder. (M+H)=402.12. $^1$H NMR (400 MHz, CDCl$_3$) δ 9.01 (m, 1H), 8.77 (s, 1H), 8.73 (m, 1H), 8.47 (m, 2H), 8.10 (m, 1H), 7.86 (dd, 1H, J=6.96, 2.25 Hz), 7.72 (m, 1H), 7.52 (m, 1H), 7.43 (t, 1H, J=7.88 Hz), 7.19 (d, 1H, J=4.80 Hz), 7.09 (d, 1H, J=8.89 Hz), 7.03 (d, 1H, J=4.81 Hz), 3.87 (s, 3H).

Example 174

(3-Morpholin-4-yl-phenyl)-pyrrolo[2,1-f][1,2,4]triazin-2-yl-amine 174a) 7-Bromo-2-methanesulfinyl-pyrrolo[2,1-f][1,2,4]triazine Into a Round bottom flask, 7-Bromo-2-methylsulfanyl-pyrrolo[2,1-f][1,2,4]triazine (4.00 g, 0.0164 mol) and Methylene chloride (100 mL) were added. m-Chloroperbenzoic acid (77% max)(5.14 g, 0.0229 mol) was added portion wise over 20 minutes and the reaction was stirred at room temperature for one hour. The mixture was partitioned with DCM (200 mL) and saturated NaHCO$_3$ (200 mL). Organic extracts were washed with Brine and dried over Na$_2$SO$_4$. The solid was filtered and washed with DCM. The solvent was removed under vacuum to give a yellow solid. The solid was washed with hexane to afford 3.27 grams of 7-Bromo-2-methanesulfinyl-pyrrolo[2,1-f][1,2,4]triazine as a yellow powder. $^1$H NMR (400 MHz, DMSO, d$_6$) δ 9.34 (s, 1H), 7.51 (m, 1H), 7.41 (d, 1H, J=4.71 Hz), 3.43 (s, 3H).

174b) (7-Bromo-pyrrolo[2,1-f][1,2,4]triazin-2-yl)-(3-morpholin-4-yl-phenyl)-amine 7-Bromo-2-methanesulfinyl-pyrrolo[2,1-f][1,2,4]triazine (2.00 g, 0.00769 mol), 3-Morpholin-4-yl-phenylamine (1.37 g, 0.00769 mol) and N,N-Diisopropylethylamine (1.49 g, 0.0115 mol) were dissolved in 2-Methoxyethanol (13.7 mL). The reaction was microwaved on 300 watts, 180° C. for 80 minutes. The solvent was then removed en vacuo. The crude mixture was purified by Isco flash column chromatography (Hexane/Ethyl Acetate). Combined fractions were reduced en vacuo to afford 1.40 g of (7-Bromo-pyrrolo[2,1-f][1,2,4]triazin-2-yl)-(3-morpholin-4-yl-phenyl)-amine as a brown solid. (M+H)=376.05.

174c) (3-Morpholin-4-yl-phenyl)-pyrrolo[2,1-f][1,2,4]triazin-2-yl-amine Palladium Acetate (0.029 g, 0.00013 mol) and Triphenylphosphine (0.042 g, 0.00016 mol) were dissolved in Tetrahydrofuran (2.0 mL) and the mixture was allowed to stir at room temperature for 10 minutes. (7-Bromo-pyrrolo[2,1-f][1,2,4]triazin-2-yl)-(3-morpholin-4-yl-phenyl)-amine (0.240 g, 0.000641 mol) was then added and the reaction was again allowed to stir for 10 minutes. 2-chloro-5-trifluoromethylphenylboronic acid (0.288 g, 0.00128 mol) was added followed by 0.9 M of Sodium carbonate in water (2 mL) and Ethanol (2.0 mL). The reaction mixture was then heated at 80° C. and was allowed to stir overnight. The reaction mixture was poured over saturated sodium chloride, and organics were extracted with ethyl acetate/dichloromethane. Combined organics were dried over sodium sulfate, filtered and reduced en vacuo. Because the desired product was not formed, 22.96 mg of (3-Morpholin-4-yl-phenyl)-pyrrolo[2,1-f][1,2,4]triazin-2-yl-amine was purified by Gilson prep HPLC as a byproduct. (M+H)=296.14. $^1$H NMR (400 MHz, CDCl$_3$) δ 9.47 (s, 1H), 8.62 (s, 1H), 7.98 (s, 1H), 7.88 (s, 1H), 7.36 (m, 2H), 7.08 (d, 1H, J=4.85 Hz), 6.91 (m, 2H), 4.02 (m, 4H), 3.41 (m, 2H).

Example 175

[7-(3-Fluoro-phenyl)-pyrrolo[2,1-f][1,2,4]triazin-2-yl]-(3-morpholin-4-yl-phenyl)-amine Palladium Acetate (0.029 g, 0.00013 mol) and Triphenylphosphine (0.042 g, 0.00016 mol) were dissolved in Tetrahydrofuran (2.0 mL) and the mixture was allowed to stir at room temperature for 10 minutes. (7-Bromo-pyrrolo[2,1-f][1,2,4]triazin-2-yl)-(3-morpholin-4-yl-phenyl)-amine (0.240 g, 0.000641 mol) was then added and the reaction was again allowed to stir for 10 minutes. 3-fluorophenylboronic acid (0.179 g, 0.00128 mol) was added followed by 0.9 M of Sodium carbonate in water (2 mL) and Ethanol (2.0 mL). The reaction mixture was then heated at 80° C. and was allowed to stir overnight. The reaction mixture was poured over saturated sodium chloride, and organics were extracted with ethyl acetate/dichloromethane. Combined organics were dried over sodium sulfate, filtered and reduced en vacuo. The crude mixture was purified by Gilson prep HPLC to afford 40.32 mg of [7-(3-Fluoro-phenyl)-pyrrolo[2,1-f][1,2,4]triazin-2-yl]-(3-morpholin-4-yl-phenyl)-amine as a lyophilated powder. (M+H)=390.14. $^1$H NMR (400 MHz, CDCl$_3$) δ 8.67 (s, 1H), 7.93 (m, 1H), 7.83 (m, 1H), 7.35-7.55 (m, 5H), 7.18 (m, 3H), 6.99 (m, 1H), 3.92 (m, 4H), 3.26 (m, 4H).

Example 176

[7-(3-Chloro-phenyl)-pyrrolo[2,1-f][1,2,4]triazin-2-yl]-(1H-indol-5-yl)-amine

The compound was prepared in an analogous fashion to Example 37 replacing 2-Methanesulfinyl-7-(2-methoxy-phenyl)-pyrrolo[2,1-f][1,2,4]triazine with 7-(3-Chloro-phenyl)-2-methanesulfinyl-pyrrolo[2,1-f][1,2,4]triazine to afford 31.13 mg of [7-(3-Chloro-phenyl)-pyrrolo[2,1-f][1,2,4]triazin-2-yl]-(1H-indol-5-yl)-amine as a lyophilized powder. (M+H)=360.18. $^1$H NMR (400 MHz, DMSO, d$_6$) δ 9.29 (s, 1H), 8.98 (s, 1H), 8.42 (s, 1H), 8.41 (s, 1H), 8.15 (d, 1H, J=7.92 Hz), 8.01 (s, 1H), 7.52 (t, 1H, J=7.92 Hz), 7.42 (m, 2H), 7.40 (m, 1H), 7.30 (m, 1H), 7.24 (d, 1H, J=4.76 Hz), 6.93 (d, 1H, J=4.80 Hz), 6.39 (s, 1H).

Example 177

[7-(3-Chloro-phenyl)-pyrrolo[2,1-f][1,2,4]triazin-2-yl]-quinolin-6-yl-amine

The compound was prepared in an analogous fashion to Example 34 replacing 4-Pyrrolidin-1-yl-phenylamine with Quinolin-6-yl amine to afford 15.11 mg of [7-(3-Chloro-phenyl)-pyrrolo[2,1-f][1,2,4]triazin-2-yl]-quinolin-6-yl-amine as a lyophilized powder. (M+H)=372.16. $^1$H NMR (400 MHz, DMSO, d$_6$) δ 10.00 (s, 1H), 9.09 (s, 1H), 8.74 (m, 1H), 8.47 (s, 1H), 8.34 (s, 1H), 8.18 (d, 1H, J=8.16 Hz), 8.09 (d, 1H, J=8.28 Hz), 7.97 (s, 2H), 7.62 (m, 1H), 7.48 (m, 2H), 7.32 (d, 1H, J=4.80 Hz), 7.03 (d, 1H, J=4.69 Hz).

Example 178

2-(4-{3-[7-(2-Methoxy-phenyl)-pyrrolo[2,1-f][1,2,4]triazin-2-ylamino]-phenyl}-piperazin-1-yl)-ethanol 178a) 2-[4-(3-Nitro-phenyl)-piperazin-1-yl]-ethanol: 1-(3-Nitro-phenyl)-piperazine (2.00 g, 0.00965 mol), [B] 2-Bromoethanol (1.21 g, 0.00965 mol) and Potassium carbonate (2.67 g, 0.0193 mol) were dissolved in N,N-Dimethylformamide (100 mL) and the reaction mixture was heated at 80° C. and was allowed to stir overnight. The reaction mixture was poured over saturated ammonium chloride, and organics were extracted with ethyl acetate/dichloromethane. Combined organics were dried over sodium sulfate, filtered and reduced en vacuo. The crude mixture was purified by Isco flash column chromatography (DCM/MeOH). Combined fractions were reduced en vacuo to afford 2.30 g of 2-[4-(3-Nitro-phenyl)-piperazin-1-yl]-ethanol as a yellow solid. (M+H)=252.16. $^1$H NMR (400 MHz, DMSO, d$_6$) δ 8.09 (s, 1H), 7.70 (m, 1H), 7.60 (m, 1H), 7.44 (m, 2H), 3.53 (m, 6H), 3.31 (m, 4H), 3.25 (m, 2H).

178b) 2-[4-(3-Amino-phenyl)-piperazin-1-yl]-ethanol: 2-[4-(3-Nitro-phenyl)-piperazin-1-yl]-ethanol (2.40 g, 0.00955 mol) was dissolved in Ethanol (45.0 mL) and the solution was carefully added to Palladium on Carbon 10% (90.10, carbon black. Palladium, 0.750 g) in a Parr vessel under nitrogen. The reaction was then hydrogenated on a Parr reactor until uptake of hydrogen had ceased (~4 hours). The catalyst was then filtered and the filtrate was reduced to yield 2.25 g of 2-[4-(3-Amino-phenyl)-piperazin-1-yl]-ethanol without further purification as a light brown powder. (M+H)=222.21.

178c) 2-(4-{3-[7-(2-Methoxy-phenyl)-pyrrolo[2,1-f][1,2,4]triazin-2-ylamino]-phenyl}-piperazin-1-yl)-ethanol 2-Methanesulfinyl-7-(2-methoxy-phenyl)-pyrrolo[2,1-f][1,2,4]triazine (150.0 mg, 0.0005220 mol), N,N-Diisopropylethylamine (0.136 mL, 0.000783 mol) and 2-[4-(3-Amino-phenyl)-piperazin-1-yl]-ethanol (231.0 mg, 0.001044 mol) were dissolved in 2-Methoxyethanol (3.66 mL) and the The reaction was microwaved on 300 watts, 180° C. for 40 minutes or until HPLC showed consumption of starting material. The reaction mixture was then reduced en vacuo and the product was isolated and purified by Gilson prep HPLC to provide 55.38 mg of 2-(4-{3-[7-(2-Methoxy-phenyl)-pyrrolo[2,1-f][1,2,4]triazin-2-ylamino]-phenyl}-piperazin-1-yl)-ethanol as a lyophilated powder. (M+H)=445.21. $^1$H NMR (400 MHz, DMSO, d$_6$) δ 9.16 (s, 1H), 8.94 (s, 1H), 7.72 (d, 1H, J=5.85 Hz), 7.44 (t, 1H, J=7.64 Hz), 7.26 (s, 1H), 7.19 (d, 1H, J=7.68 Hz), 7.08 (m, 2H), 7.01 (t, 1H, J=7.80 Hz), 6.90 (q, 2H, J=4.61 Hz), 6.46 (d, 1H, J=6.89 Hz), 3.76 (s, 3H), 3.53 (m, 4H), 3.04 (m, 2H), 2.87 (m, 2H), 2.67 (m, 2H), 2.44 (m, 2H).

Example 179

2-(4-{3-[7-(3-Chloro-phenyl)-pyrrolo[2,1-f][1,2,4]triazin-2-ylamino]-phenyl}-piperazin-1-yl)-ethanol The compound was prepared in an analogous fashion to Example 46 replacing 2-Methanesulfinyl-7-(2-methoxy-phenyl)-pyrrolo[2,1-f][1,2,4]triazine with 7-(3-Chloro-phenyl)-2-methanesulfinyl-pyrrolo[2,1-f][1,2,4]triazine to afford 13.22 mg of 2-(4-{3-[7-(3-Chloro-phenyl)-pyrrolo[2,1-f][1,2,4]triazin-2-ylamino]-phenyl}-piperazin-1-yl)-ethanol as a lyophilized powder. (M+H)=449.16. ¹H NMR (400 MHz, DMSO, d₆) δ 9.32 (s, 1H), 9.00 (s, 1H), 8.36 (s, 1H), 8.05 (d, 1H, J=7.36 Hz), 7.52 (t, 1H, J=8.00 Hz), 7.44 (d, 1H, J=8.81 Hz), 7.35 (d, 1H, J=9.24 Hz), 7.25 (d, 1H, J=4.68 Hz), 7.17 (m, 2H), 6.95 (d, 1H, J=4.76 Hz), 6.59 (d, 1H, J=9.13 Hz), 3.53 (m, 4H), 3.03 (m, 6H), 2.42 (m, 2H).

Example 180

2-(4-{3-[7-(5-Chloro-2-methoxy-phenyl)-pyrrolo[2,1-f][1,2,4]triazin-2-ylamino]-phenyl}-piperazin-1-yl)-ethanol The compound was prepared in an analogous fashion to Example 46 replacing 2-Methanesulfinyl-7-(2-methoxy-phenyl)-pyrrolo[2,1-f][1,2,4]triazine with 7-(5-Chloro-2-methoxy-phenyl)-2-methanesulfinyl-pyrrolo[2,1-f][1,2,4]triazine to afford 4.33 mg of 2-(4-{3-[7-(3-Chloro-phenyl)-pyrrolo[2,1-f][1,2,4]triazin-2-ylamino]-phenyl}-piperazin-1-yl)-ethanol as a lyophilized powder. (M+H)=479.19. ¹H NMR (400 MHz, DMSO, d₆) δ 9.33 (s, 1H), 8.98 (s, 1H), 7.94 (m, 1H), 7.50 (dd, 1H, J=2.84 Hz, 6.09 Hz), 7.40 (d, 1H, J=8.53 Hz), 7.23 (d, 1H, J=8.92 Hz), 7.15 (m, 2H), 7.01 (d, 1H, J=4.64 Hz), 6.93 (d, 1H, J=4.57 Hz), 6.59 (d, 1H, J=6.21 Hz), 3.80 (s, 3H), 3.58 (m, 6H), 3.25 (m, 2H), 3.15 (m, 3H), 2.97 (m, 2H).

Example 181

2-(4-{3-[7-(4-Methanesulfonyl-phenyl)-pyrrolo[2,1-f][1,2,4]triazin-2-ylamino]-phenyl}-piperazin-1-yl)-ethanol The compound was prepared in an analogous fashion to Example 46 replacing 2-Methanesulfinyl-7-(2-methoxy-phenyl)-pyrrolo[2,1-f][1,2,4]triazine with 2-Methanesulfinyl-7-(4-methanesulfonyl-phenyl)-pyrrolo[2,1-f][1,2,4]triazine to afford 35.01 mg of 2-(4-{3-[7-(3-Chloro-phenyl)-pyrrolo[2,1-f][1,2,4]triazin-2-ylamino]-phenyl}-piperazin-1-yl)-ethanol as a lyophilized powder. (M+H)=493.13. ¹H NMR (400 MHz, DMSO, d₆) δ 9.49 (s, 1H), 9.07 (s, 1H), 8.52 (d, 2H, J=8.52 Hz), 8.03 (d, 2H, J=8.45 Hz), 7.40 (m, 2H), 7.26 (m, 2H), 7.01 (d, 1H, J=4.84 Hz), 6.67 (d, 1H, J=6.57 Hz), 3.76 (m, 2H), 3.66 (m, 4H), 3.31 (s, 3H), 3.25 (m, 2H), 3.23 (m, 2H), 3.02 (m, 2H).

Example 182

N-{4-[2-(3-Morpholin-4-yl-phenylamino)-pyrrolo[2,1-f][1,2,4]triazin-7-yl]-phenyl}-methanesulfonamide The compound was prepared in an analogous fashion to Example 43 replacing 3-fluorophenylboronic acid with 4-(methanesulfonylamino)phenyl boronic acid to afford 40.89 mg of N-{4-[2-(3-Morpholin-4-yl-phenylamino)-pyrrolo[2,1-f][1,2,4]triazin-7-yl]-phenyl}-methanesulfonamide as a lyophilized powder. (M+H)=465.12. ¹H NMR (400 MHz, DMSO, d₆) δ 9.85 (s, 1H), 9.34 (s, 1H), 9.00 (s, 1H), 7.89 (d, 1H, J=7.85 Hz), 7.76 (m, 1H), 7.47 (t, 1H, J=8.00 Hz), 7.38 (m, 1H), 7.25 (m, 2H), 7.15 (t, 1H, J=8.05 Hz), 7.02 (d, 1H, J=4.69 Hz), 6.95 (d, 1H, J=4.76 Hz), 6.58 (d, 1H, J=6.36 Hz), 3.67 (m, 4H), 2.99 (s, 3H), 2.96 (m, 4H).

Example 183

N-{3-[2-(3-Morpholin-4-yl-phenylamino)-pyrrolo[2,1-f][1,2,4]triazin-7-yl]-phenyl}-methanesulfonamide The compound was prepared in an analogous fashion to Example 43 replacing 3-fluorophenylboronic acid with 3-(methanesulfonylamino)phenyl boronic acid to afford 74.96 mg of N-{3-[2-(3-Morpholin-4-yl-phenylamino)-pyrrolo[2,1-f][1,2,4]triazin-7-yl]-phenyl}-methanesulfonamide as a lyophilized powder. (M+H)=465.13. ¹H NMR (400 MHz, DMSO, d₆) δ 9.99 (s, 1H), 9.30 (s, 1H), 8.96 (s, 1H), 8.13 (d, 2H, J=8.68 Hz), 7.41 (s, 1H), 7.32 (d, 2H, J=8.68 Hz), 7.14 (m, 3H), 6.93 (d, 1H, J=4.72 Hz), 6.59 (d, 1H, J=7.45 Hz), 3.69 (m, 4H), 3.06 (s, 3H), 3.01 (m, 4H).

Example 184

[7-(3-Methanesulfonyl-phenyl)-pyrrolo[2,1-f][1,2,4]triazin-2-yl]-(3-morpholin-4-yl-phenyl)-amine 2-Methanesulfinyl-7-(3-methanesulfonyl-phenyl)-pyrrolo[2,1-f][1,2,4]triazine (125.0 mg, 0.0003727 mol) and 3-Morpholin-4-yl-phenylamine (183 mg, 0.00103 mol) were dissolved in 2-Methoxyethanol (3.2 mL) and the reaction was microwaved at 300 W at 180° C. until HPLC showed consumption of starting material. The reaction mixture was then reduced en vacuo and the product was isolated and purified by Gilson prep HPLC to provide 50.00 mg of [7-(3-Methanesulfonyl-phenyl)-pyrrolo[2,1-f][1,2,4]triazin-2-yl]-(3-morpholin-4-yl-phenyl)-amine as a lyophilated powder. (M+H)=450.15. ¹H NMR (400 MHz, DMSO, d₆) δ 9.40 (s, 1H), 9.04 (s, 1H), 8.51 (m, 2H), 7.95 (d, 1H, J=7.88 Hz), 7.80 (d, 1H, J=8.05 Hz), 7.34 (d, 1H, J=8.09 Hz), 7.26 (d, 1H, J=4.72 Hz), 7.22 (m, 2H), 6.99 (d, 1H, J=4.72 Hz), 6.61 (m, 1H), 3.68 (m, 4H), 3.28 (s, 3H), 2.99 (m, 4H).

Example 185

[7-(3-Methanesulfonyl-phenyl)-pyrrolo[2,1-f][1,2,4]triazin-2-yl]-(3,4,5-trimethoxy-phenyl)-amine The compound was prepared in an analogous fashion to Example 52 replacing 3-Morpholin-4-yl-phenylamine with 3,4,5-trimethoxyaniline to afford 30.22 mg of [7-(3-Methanesulfonyl-phenyl)-pyrrolo[2,1-f][1,2,4]triazin-2-yl]-(3,4,5-trimethoxy-phenyl)-amine as a lyophilized powder. (M+H)= 455.14. ¹H NMR (400 MHz, DMSO, d₆) δ 9.37 (s, 1H), 9.05 (s, 1H), 8.57 (d, 1H, J=7.84 Hz), 8.37 (m, 1H), 7.92 (d, 1H, J=7.87 Hz), 7.75 (t, 1H, J=7.84 Hz), 7.25 (d, 1H, J=4.73 Hz), 7.03 (s, 2H), 6.99 (d, 1H, J=4.72 Hz), 3.61 (s, 3H), 3.59 (s, 6H), 3.26 (s, 3H).

Example 186

(3-Fluoro-4-morpholin-4-yl-phenyl)-[7-(2-methoxy-phenyl)-pyrrolo[2,1-f][1,2,4]triazin-2-yl]-amine The compound was made in an analogous fashion to Example 37 replacing 5-Aminoindole with 3-Fluoro-4-morpholin-4-yl-phenylamine to afford 42.25 mg of (3-Fluoro-4-morpholin-4-yl-phenyl)-[7-(2-methoxy-phenyl)-pyrrolo[2,1-f][1,2,4]triazin-2-yl]-amine as a lyophilized powder. (M+H)=420.18. ¹H NMR (400 MHz, DMSO, d₆) δ 9.47 (s, 1H), 8.95 (s, 1H), 7.75 (m, 2H), 7.45 (m, 1H), 7.27 (m, 2H), 7.22 (t, 1H, J=8.96 Hz), 7.02 (m, 3H), 3.80 (s, 3H), 3.72 (m, 4H), 2.91 (m, 4H).

Example 187

[7-(3-Chloro-phenyl)-pyrrolo[2,1-f][1,2,4]triazin-2-yl]-(3-fluoro-4-morpholin-4-yl-phenyl)-amine The compound was made in an analogous fashion to Example 34 replacing 4-Pyrrolidin-1-yl-phenylamine with 3-Fluoro-4-morpholin-4-yl-phenylamine to afford 31.30 mg of [7-(3-Chloro-phenyl)-pyrrolo[2,1-f][1,2,4]triazin-2-yl]-(3-fluoro-4-morpholin-4-yl-phenyl)-amine as a lyophilized powder. (M+H)=424.11. $^1$H NMR (400 MHz, DMSO, d$_6$) δ 9.60 (s, 1H), 9.01 (s, 1H), 8.35 (m, 1H), 8.07 (d, 1H, J=7.88 Hz), 7.64 (m, 1H), 7.54 (t, 1H, J=7.97 Hz), 7.47 (m, 2H), 7.27 (d, 1H, J=4.80 Hz), 7.02 (t, 1H, J=9.60 Hz), 6.98 (d, 1H, J=4.80 Hz), 3.74 (m, 4H), 2.95 (m, 4H).

Example 188

[7-(5-Chloro-2-methoxy-phenyl)-pyrrolo[2,1-f][1,2,4]triazin-2-yl]-(3-fluoro-4-morpholin-4-yl-phenyl)-amine The compound was made in an analogous fashion to Example 20 replacing 4-Methoxybenzenamine with 3-Fluoro-4-morpholin-4-yl-phenylamine to afford 39.50 mg of [7-(5-Chloro-2-methoxy-phenyl)-pyrrolo[2,1-f][1,2,4]triazin-2-yl]-(3-fluoro-4-morpholin-4-yl-phenyl)-amine as a lyophilized powder. (M+H)=454.08. $^1$H NMR (400 MHz, DMSO, d$_6$) δ 9.53 (s, 1H), 8.98 (s, 1H), 7.88 (m, 1H), 7.61 (m, 1H), 7.50 (m, 1H), 7.38 (m, 1H), 7.23 (d, 1H, J=8.96 Hz), 7.00 (d, 1H, J=4.68 Hz), 6.93 (m, 2H), 3.81 (s, 3H), 3.72 (m, 4H), 2.92 (m, 4H).

Example 189

(3-Fluoro-4-morpholin-4-yl-phenyl)-[7-(4-methanesulfonyl-phenyl)-pyrrolo[2,1-f][1,2,4]triazin-2-yl]-amine The compound was made in an analogous fashion to Example 29 replacing 3,4,5-Trimethoxyaniline with 3-Fluoro-4-morpholin-4-yl-phenylamine to afford 31.76 mg of [7-(5-Chloro-2-methoxy-phenyl)-pyrrolo[2,1-f][1,2,4]triazin-2-yl]-(3-fluoro-4-morpholin-4-yl-phenyl)-amine as a lyophilized powder. (M+H)=468.13. $^1$H NMR (400 MHz, DMSO, d$_6$) δ 9.67 (s, 1H), 9.06 (s, 1H), 8.46 (d, 2H, J=8.48 Hz), 8.03 (d, 2H, J=8.64 Hz), 7.79 (m, 1H), 7.34 (m, 2H), 7.01 (d, 2H, J=4.80 Hz), 3.75 (m, 4H), 3.28 (s, 3H), 2.97 (m, 4H).

Example 190

7-(3-Chloro-phenyl)-2-(2-methoxy-ethoxy)-pyrrolo[2,1-f][1,2,4]triazine 7-(3-Chloro-phenyl)-2-methanesulfinyl-pyrrolo[2,1-f][1,2,4]triazine (126.9 mg, 0.0004350 mol), N,N-Diisopropylethylamine (0.114 mL, 0.000652 mol) and 4-Methanesulfonyl-3-morpholin-4-yl-phenylamine (223 mg, 0.000870 mol) were dissolved in 2-Methoxyethanol (3.05 mL) and The reaction was microwaved on 300 watts, 180° C. for 40 minutes or until HPLC showed consumption of starting material. LC/MS and NMR data showed that the solvent underwent addition to the sulfoxide rather than the aniline. The reaction mixture was then reduced en vacuo and 7.48 mg of 7-(3-Chloro-phenyl)-2-(2-methoxy-ethoxy)-pyrrolo[2,1-f][1,2,4]triazine was isolated and purified by Gilson prep HPLC. The product was then lyophilized to a powder. (M+H)=304.08. $^1$H NMR (400 MHz, DMSO, d$_6$) δ 9.09 (s, 1H), 8.36 (s, 1H), 8.19 (d, 1H, J=7.88 Hz), 7.55 (t, 1H, J=7.97 Hz), 7.45 (m, 2H), 7.10 (d, 1H, J=4.84 Hz), 4.47 (m, 2H), 3.75 (m, 2H), 3.64 (s, 3H).

Example 191

7-(5-Chloro-2-methoxy-phenyl)-2-(2-methoxy-ethoxy)-pyrrolo[2,1-f][1,2,4]triazine The compound was prepared in an analogous fashion to Example 58 replacing 7-(3-Chloro-phenyl)-2-methanesulfinyl-pyrrolo[2,1-f][1,2,4]triazine with 7-(5-Chloro-2-methoxy-phenyl)-2-methanesulfinyl-pyrrolo[2,1-f][1,2,4]triazine to afford 3.87 mg of 7-(5-Chloro-2-methoxy-phenyl)-2-(2-methoxy-ethoxy)-pyrrolo[2,1-f][1,2,4]triazine as a lyophilized powder. (M+H)=334.08. $^1$H NMR (400 MHz, DMSO, d$_6$) δ 9.06 (s, 1H), 7.95 (m, 1H), 7.47 (m, 1H), 7.21 (d, 1H, J=8.93 Hz), 7.16 (d, 1H, J=4.75 Hz), 7.05 (d, 1H, J=4.77 Hz), 4.33 (m, 2H), 3.82 (s, 3H), 3.69 (m, 2H), 3.29 (s, 3H).

Example 192

(3-Morpholin-4-yl-phenyl)-{7-[4-(propane-2-sulfonyl)-phenyl]-pyrrolo[2,1-f][1,2,4]triazin-2-yl}-amine The compound was prepared in an analogous fashion to Example 43 replacing 3-fluorophenylboronic acid with (4-isopropylsulfonyl)phenyl boronic acid to afford 11.36 mg of (3-Morpholin-4-yl-phenyl)-{7-[4-(propane-2-sulfonyl)-phenyl]-pyrrolo[2,1-f][1,2,4]triazin-2-yl}-amine as a lyophilized powder. (M+H)=478.14. $^1$H NMR (400 MHz, DMSO, d$_6$) δ 9.41 (s, 1H), 9.06 (s, 1H), 8.51 (d, 2H, J=8.44 Hz), 7.92 (d, 2H, J=8.49 Hz), 7.37 (d, 1H, J=4.81 Hz), 7.31 (m, 1H), 7.18 (m, 2H), 7.00 (d, 1H, J=4.77 Hz), 6.62 (m, 1H), 3.69 (m, 4H), 3.47 (sept., 1H, J=6.80 Hz), 3.02 (m, 4H), 1.19 (d, 6H, J=6.80 Hz).

Example 193

[7-(3-Fluoro-4-methanesulfonyl-phenyl)-pyrrolo[2,1-f][1,2,4]triazin-2-yl]-(3-morpholin-4-yl-phenyl)-amine The compound was prepared in an analogous fashion to Example 43 replacing 3-fluorophenylboronic acid with 3-Fluoro-(4-methylsulfonyl)phenyl boronic acid to afford 19.99 mg of [7-(3-Fluoro-4-methanesulfonyl-phenyl)-pyrrolo[2,1-f][1,2,4]triazin-2-yl]-(3-morpholin-4-yl-phenyl)-amine as a lyophilized powder. (M+H)=468.13. $^1$H NMR (400 MHz, DMSO, d$_6$) δ 9.47 (s, 1H), 9.08 (s, 1H), 8.45 (d, 1H, J=12.48 Hz), 8.32 (d, 1H, J=7.00 Hz), 7.91 (t, 1H, J=8.05 Hz), 7.45 (d, 1H, J=4.88 Hz), 7.21 (m, 3H), 7.01 (d, 1H, J=4.88 Hz), 6.65 (m, 1H), 3.70 (m, 4H), 3.37 (s, 3H), 3.04 (m, 4H).

Example 194

N-Methyl-4-[2-(3-morpholin-4-yl-phenylamino)-pyrrolo[2,1-f][1,2,4]triazin-7-yl]-benzamide The compound was prepared in an analogous fashion to Example 43 replacing 3-fluorophenylboronic acid with 4-(N-methylaminocarbonyl)phenyl boronic acid to afford 31.46 mg of N-Methyl-4-[2-(3-morpholin-4-yl-phenylamino)-pyrrolo[2,1-f][1,2,4]triazin-7-yl]-benzamide as a lyophilized powder. (M+H)=429.17. $^1$H NMR (400 MHz, DMSO, d$_6$) δ 9.38 (s, 1H), 9.02 (s, 1H), 8.51 (m, 1H), 8.28 (d, 2H, J=8.45 Hz), 7.97 (d, 2H, J=8.48 Hz), 7.37 (m, 1H), 7.23 (m, 3H), 6.98 (d, 1H, J=4.76 Hz), 6.60 (d, 1H, J=8.00 Hz), 3.65 (m, 4H), 2.99 (m, 4H), 2.83 (d, 3H, J=4.48 Hz).

Example 195

[7-(2-Methoxy-phenyl)-pyrrolo[2,1-f][1,2,4]triazin-2-yl]-[3-(4-morpholin-4-yl-piperidin-1-yl)-phenyl]-amine 195a) 4-[1-(3-Nitro-phenyl)-piperidin-4-yl]-morpholine 1-Fluoro-3-nitro-benzene (1.00 g, 0.00709 mol) and Potassium carbonate (1.47 g, 0.0106 mol) were dissolved in Dimethyl sulfoxide (7.50 mL) and 4-Piperidin-4-yl-morpholine (2.41 g, 0.0142 mol) was added. The reaction was allowed to stir overnight at 90° C. Upon completion of the reaction, the mixture was diluted with ethyl acetate and was poured over water. Combined extracts were then washed with brine and the organics were dried over magnesium sulfate, filtered and reduced. The crude mixture was purified by Isco flash column chromatography (Hexane/Ethyl Acetate). Combined fractions were reduced en vacuo to afford 1.60 g of 4-[1-(3-Nitro-phenyl)-piperidin-4-yl]-morpholine.

195b) 3-(4-Morpholin-4-yl-piperidin-1-yl)-phenylamine

4-[1-(3-Nitro-phenyl)-piperidin-4-yl]-morpholine (1.60 g, 0.00549 mol) was dissolved in Methanol (45 mL) and the solution was carefully added to Palladium on Carbon 10% (90.10, carbon black. Palladium, 0.750 g) in a Parr vessel under nitrogen. The mixture was then placed on a Parr hydrogenator and was allowed to shake until uptake of hydrogen had ceased (~3 hours). The catalyst was then removed via filtration and the filtrate was reduced to afford 615 mg of 3-(4-Morpholin-4-yl-piperidin-1-yl)-phenylamine without further purification. $^1$H NMR (400 MHz, DMSO, $d_6$) δ 6.81 (t, 1H, J=7.88 Hz), 6.14 (m, 1H), 6.11 (m, 1H), 6.00 (m, 1H), 4.80 (s, 2H), 3.57 (m, 6H), 2.46 (m, 5H), 1.82 (m, 2H), 1.43 (m, 2H).

195c) [7-(2-Methoxy-phenyl)-pyrrolo[2,1-f][1,2,4]triazin-2-yl]-[3-(4-morpholin-4-yl-piperidin-1-yl)-phenyl]-amine 2-Methanesulfinyl-7-(2-methoxy-phenyl)-pyrrolo[2,1-f][1,2,4]triazine (85.0 mg, 0.000296 mol), N,N-Diisopropylethylamine (0.0773 mL, 0.000444 mol) and 3-(4-Morpholin-4-yl-piperidin-1-yl)-phenylamine (155 mg, 0.000592 mol) were dissolved in 2-Methoxyethanol (2.08 mL) and The reaction was microwaved on 300 watts, 180° C. for 40 minutes or until HPLC showed consumption of starting material. The reaction mixture was then reduced en vacuo and the product was isolated and purified by Gilson prep HPLC to provide 19.65 mg of [7-(2-Methoxy-phenyl)-pyrrolo[2,1-f][1,2,4]triazin-2-yl]-[3-(4-morpholin-4-yl-piperidin-1-yl)-phenyl]-amine as a lyophilized powder. (M+H)=485.25. $^1$H NMR (400 MHz, DMSO, $d_6$) δ 9.22 (s, 1H), 8.95 (s, 1H), 7.71 (m, 1H), 7.50 (t, 1H, J=6.88 Hz), 7.32 (m, 1H), 7.21 (m, 1H), 7.09 (m, 3H), 6.90 (q, 2H, J=5.65 Hz), 6.53 (m, 1H), 4.02 (m, 2H), 3.76 (s, 3H), 3.68 (t, 2H, J=12.16 Hz), 3.56 (m, 2H), 3.48 (m, 2H), 3.21 (m, 1H), 3.10 (m, 2H), 2.53 (m, 2H), 2.04 (m, 2H), 1.60 (m, 2H).

Example 196

[7-(5-Chloro-2-methoxy-phenyl)-pyrrolo[2,1-f][1,2,4]triazin-2-yl]-[3-(4-morpholin-4-yl-piperidin-1-yl)-phenyl]-amine The compound was prepared in an analogous fashion to Example 63 replacing 2-Methanesulfinyl-7-(2-methoxy-phenyl)-pyrrolo[2,1-f][1,2,4]triazine with 7-(5-Chloro-2-methoxy-phenyl)-2-methanesulfinyl-pyrrolo[2,1-f][1,2,4]triazine to afford 16.53 mg of [7-(5-Chloro-2-methoxy-phenyl)-pyrrolo[2,1-f][1,2,4]triazin-2-yl]-[3-(4-morpholin-4-yl-piperidin-1-yl)-phenyl]-amine as a lyophilized powder. (M+H)=519.22. $^1$H NMR (400 MHz, DMSO, $d_6$) δ 9.29 (s, 1H), 8.98 (s, 1H), 7.92 (m, 1H), 7.53 (m, 1H), 7.30 (d, 1H, J=7.68 Hz), 7.22 (m, 2H), 7.10 (t, 1H, J=8.09 Hz), 7.00 (d, 1H, J=4.69 Hz), 6.92 (d, 1H, J=4.33 Hz), 6.56 (m, 1H), 4.02 (m, 2H), 3.80 (s, 3H), 3.67 (m, 4H), 3.47 (m, 2H), 3.31 (m, 1H), 3.09 (m, 2H), 2.59 (m, 2H), 2.03 (m, 2H), 1.61 (m, 2H).

Example 197

7-(4-Methanesulfonyl-phenyl)-2-(2-methoxy-ethoxy)-pyrrolo[2,1-f][1,2,4]triazine

The compound was prepared in an analogous fashion to Example 58 replacing 7-(3-Chloro-phenyl)-2-methanesulfinyl-pyrrolo[2,1-f][1,2,4]triazine with 2-M ethanesulfinyl-7-(4-methanesulfonyl-phenyl)-pyrrolo[2,1-f][1,2,4]triazine to afford 33.42 mg of 7-(4-Methanesulfonyl-phenyl)-2-(2-methoxy-ethoxy)-pyrrolo[2,1-f][1,2,4]triazine as a lyophilized powder. (M+H)=348.13. $^1$H NMR (400 MHz, DMSO, $d_6$) δ 9.14 (s, 1H), 8.51 (d, 2H, J=8.56 Hz), 8.05 (d, 2H, J=8.53 Hz), 7.54 (d, 1H, J=4.87 Hz), 7.14 (d, 1H, J=4.92 Hz), 4.49 (m, 2H), 3.75 (m, 2H), 3.34 (s, 3H), 3.27 (s, 3H).

Example 198

[7-(1-Methyl-1H-pyrazol-4-yl)-pyrrolo[2,1-f][1,2,4]triazin-2-yl]-(3-morpholin-4-yl-phenyl)-amine The compound was prepared in an analogous fashion to Example 43 replacing 3-fluorophenylboronic acid with (1-Methyl-1H-pyrazol-4-yl)boronic acid to afford 16.65 mg of [7-(1-Methyl-1H-pyrazol-4-yl)-pyrrolo[2,1-f][1,2,4]triazin-2-yl]-(3-morpholin-4-yl-phenyl)-amine as a lyophilized powder. (M+H)=376.23. $^1$H NMR (400 MHz, DMSO, $d_6$) δ 9.22 (s, 1H), 8.88 (s, 1H), 8.39 (s, 1H), 8.19 (s, 1H), 7.30 (m, 1H), 7.24 (m, 2H), 7.04 (d, 1H, J=4.69 Hz), 6.90 (d, 1H, J=4.68 Hz), 6.65 (m, 1H), 3.93 (s, 3H), 3.74 (m, 4H), 3.09 (m, 4H).

Example 199

(4-Morpholin-4-yl-phenyl)-{7-[4-(propane-2-sulfonyl)-phenyl]-pyrrolo[2,1-f][1,2,4]triazin-2-yl}-amine The compound was prepared in an analogous fashion to Example 43 replacing 3-fluorophenylboronic acid with (4-isopropylsulfonyl)phenyl boronic acid and (7-Bromo-pyrrolo[2,1-f][1,2,4]triazin-2-yl)-(3-morpholin-4-yl-phenyl)-amine with (7-Bromo-pyrrolo[2,1-f][1,2,4]triazin-2-yl)-(4-morpholin-4-yl-phenyl)-amine to afford 23.94 mg of (4-Morpholin-4-yl-phenyl)-{7-[4-(propane-2-sulfonyl)-phenyl]-pyrrolo[2,1-f][1,2,4]triazin-2-yl}-amine as a lyophilized powder. (M+H)=478.19. $^1$H NMR (400 MHz, DMSO, $d_6$) δ 9.40 (s, 1H), 9.03 (s, 1H), 8.47 (d, 2H, J=8.53 Hz), 7.95 (d, 2H, J=8.56 Hz), 7.62 (d, 2H, J=8.92 Hz), 7.33 (d, 1H, J=4.80 Hz), 7.02 (m, 2H), 6.98 (d, 1H, J=4.80 Hz), 3.78 (m, 4H), 3.48 (sept., 1H, J=6.77 Hz), 3.11 (m, 4H). 1.20 (d, 6H, J=6.80 Hz).

Example 200

N-{4-[2-(4-Morpholin-4-yl-phenylamino)-pyrrolo[2,1-f][1,2,4]triazin-7-yl]-phenyl}-methanesulfonamide The compound was prepared in an analogous fashion to Example 43 replacing 3-fluorophenylboronic acid with (4-methanesulfonylamino)phenyl boronic acid and (7-Bromo-pyrrolo[2,1-f][1,2,4]triazin-2-yl)-(3-morpholin-4-yl-phenyl)-amine with (7-Bromo-pyrrolo[2,1-f][1,2,4]triazin-2-yl)-(4-morpholin-4-yl-phenyl)-amine to afford 72.44 mg of N-{4-[2-(4-Morpholin-4-yl-phenylamino)-pyrrolo[2,1-f][1,2,4]triazin-7-yl]-phenyl}-methanesulfonamide as a lyophilized powder. (M+H)=465.16. $^1$H NMR (400 MHz, DMSO, d$_6$) δ 9.92 (s, 1H), 9.28 (m, 1H), 8.93 (s, 1H), 8.16 (d, 2H, J=8.69 Hz), 7.65 (d, 2H, J=8.92 Hz), 7.34 (d, 2H, J=8.72 Hz), 7.12 (d, 1H, J=4.73 Hz), 7.00 (d, 2H, J=8.20 Hz), 6.92 (d, 1H, J=4.73 Hz), 3.79 (m, 4H), 3.13 (m, 4H), 3.07 (s, 3H).

Example 201

N-{3-[2-(4-Morpholin-4-yl-phenylamino)-pyrrolo[2,1-f][1,2,4]triazin-7-yl]-phenyl}-methanesulfonamide The compound was prepared in an analogous fashion to Example 43 replacing 3-fluorophenylboronic acid with (3-methanesulfonylamino)phenyl boronic acid and (7-Bromo-pyrrolo[2,1-f][1,2,4]triazin-2-yl)-(3-morpholin-4-yl-phenyl)-amine with (7-Bromo-pyrrolo[2,1-f][1,2,4]triazin-2-yl)-(4-morpholin-4-yl-phenyl)-amine to afford 72.44 mg of N-{3-[2-(4-Morpholin-4-yl-phenylamino)-pyrrolo[2,1-f][1,2,4]triazin-7-yl]-phenyl}-methanesulfonamide as a lyophilized powder. (M+H)=465.17. $^1$H NMR (400 MHz, DMSO, d$_6$) δ 9.83 (s, 1H), 9.29 (s, 1H), 8.96 (s, 1H), 7.90 (m, 2H), 7.66 (d, 2H, J=9.01 Hz), 7.50 (t, 1H, J=7.84 Hz), 7.25 (d, 1H, J=8.56 Hz), 7.05 (d, 1H, J=4.72 Hz), 7.00 (d, 2H, J=8.37 Hz), 6.93 (d, 1H, J=4.76 Hz), 3.76 (m, 4H), 3.10 (m, 4H), 3.02 (s, 3H).

Example 202

(S)-1-(4-{4-[7-(2-Methoxy-phenyl)-pyrrolo[2,1-f][1,2,4]triazin-2-ylamino]-phenyl}-piperazin-1-yl)-propan-2-ol 202a) (S)-1-[4-(4-Nitro-phenyl)-piperazin-1-yl]-propan-2-ol 1-(4-Nitro-phenyl)-piperazine (2.0 g, 0.0096 mol) was dissolved in Methanol (50.0 mL) and the reaction mixture was placed in a sealed tube. (S)-(−)-Propylene Oxide (0.841 g, 0.0145 mol) was then added at room temperature and the reaction was allowed to stir overnight. The mixture was then reduced en vacuo and the product was isolated by Isco flash column chromatography (DCM/MeOH) to afford 1.63 grams of (S)-1-[4-(4-Nitro-phenyl)-piperazin-1-yl]-propan-2-ol as a yellow solid. (M+H)=266.20.

202b) (S)-1-[4-(4-Amino-phenyl)-piperazin-1-yl]-propan-2-ol (S)-1-[4-(4-Nitro-phenyl)-piperazin-1-yl]-propan-2-ol (1.60 g, 0.00603 mol) was dissolved in Methanol (35.0 mL) and the solution was carefully added to a Parr vessel containing 10% Palladium on Carbon (90.10, carbon black. Palladium, 0.500 g, 0.0375 mol) under nitrogen. The reaction was then placed on a Parr hydrogenator and was allowed to shake until uptake of hydrogen had ceased (overnight). Catalyst was removed via filtration and filtrate was reduced en vacuo to afford 1.25 g of (5)-1-[4-(4-Amino-phenyl)-piperazin-1-yl]-propan-2-ol as a white powder. (M+H)=236.21. $^1$H NMR (400 MHz, DMSO, d$_6$) δ 6.66 (d, 2H, J=8.72 Hz), 6.48 (d, 2H, J=8.72 Hz), 4.53 (s, 2H), 4.26 (d, 1H, J=4.00 Hz), 3.77 (m, 1H), 2.88 (m, 4H), 2.54 (m, 4H), 2.26 (m, 1H), 2.18 (m, 1H), 1.04 (d, 3H, J=6.17 Hz).

202c) (S)-1-(4-{4-[7-(2-Methoxy-phenyl)-pyrrolo[2,1-f][1,2,4]triazin-2-ylamino]-phenyl}-piperazin-1-yl)-propan-2-ol 2-Methane sulfinyl-7-(2-methoxy-phenyl)-pyrrolo[2,1-f][1,2,4]triazine (125.0 mg, 0.0004350 mol), N,N-Diisopropylethylamine (0.114 mL, 0.000652 mol) and (S)-1-[4-(4-Amino-phenyl)-piperazin-1-yl]-propan-2-ol (0.205 g, 0.000870 mol) were dissolved in 2-Methoxyethanol (1.0 mL) and The reaction was microwaved on 300 watts, 180° C. for 40 minutes or until HPLC showed consumption of starting material. The reaction mixture was then reduced en vacuo and the product was isolated and purified by Gilson prep HPLC to provide 110.96 mg of (S)-1-(4-{4-[7-(2-Methoxy-phenyl)-pyrrolo[2,1-f][1,2,4]triazin-2-ylamino]-phenyl}-piperazin-1-yl)-propan-2-ol as a lyophilized powder. (M+H)=459.20. $^1$H NMR (400 MHz, DMSO, d$_6$) δ 9.22 (s, 1H), 8.92 (s, 1H), 7.82 (dd, 1H, J=1.44, 6.16 Hz), 7.61 (d, 2H, J=8.96 Hz), 7.43 (t, 1H, J=7.36 Hz), 6.90 (m, 4H), 4.11 (m, 2H), 3.80 (s, 3H), 3.60 (m, 3H), 3.18 (m, 3H), 3.03 (m, 3H), 1.14 (d, 3H, J=6.16 Hz).

Example 203

(S)-1-(4-{4-[7-(5-Chloro-2-methoxy-phenyl)-pyrrolo[2,1-f][1,2,4]triazin-2-ylamino]-phenyl}-piperazin-1-yl)-propan-2-ol The compound was prepared in an analogous fashion to Example 69 replacing 2-Methanesulfinyl-7-(2-methoxy-phenyl)-pyrrolo[2,1-f][1,2,4]triazine with 7-(5-Chloro-2-methoxy-phenyl)-2-methanesulfinyl-pyrrolo[2,1-f][1,2,4]triazine to afford 107.37 mg of (S)-1-(4-{4-[7-(5-Chloro-2-methoxy-phenyl)-pyrrolo[2,1-f][1,2,4]triazin-2-ylamino]-phenyl}-piperazin-1-yl)-propan-2-ol as a lyophilized powder. (M+H)=493.17. $^1$H NMR (400 MHz, DMSO, d$_6$) δ 9.32 (s, 1H), 8.95 (s, 1H), 8.08 (m, 1H), 7.63 (d, 2H, J=9.00 Hz), 7.45 (m, 1H), 7.23 (d, 1H, J=8.96 Hz), 7.04 (d, 1H, J=4.72 Hz), 6.91 (m, 3H), 4.12 (m, 2H), 3.83 (s, 3H), 3.63 (m, 3H), 3.18 (m, 3H), 3.05 (m, 3H), 1.14 (d, 3H, J=6.12 Hz).

Example 204

(S)-1-(4-{4-[7-(3-Chloro-phenyl)-pyrrolo[2,1-f][1,2,4]triazin-2-ylamino]-phenyl}-piperazin-1-yl)-propan-2-ol The compound was prepared in an analogous fashion to Example 69 replacing 2-Methanesulfinyl-7-(2-methoxy-phenyl)-pyrrolo[2,1-f][1,2,4]triazine with 7-(3-Chloro-phenyl)-2-methanesulfinyl-pyrrolo[2,1-f][1,2,4]triazine to afford 106.47 mg of (S)-1-(4-{4-[7-(3-Chloro-phenyl)-pyrrolo[2,1-f][1,2,4]triazin-2-ylamino]-phenyl}-piperazin-1-yl)-propan-2-ol as a lyophilized powder. (M+H)=463.14. $^1$H NMR (400 MHz, DMSO, d$_6$) δ 9.38 (s, 1H), 8.98 (s, 1H), 8.49 (s, 1H), 8.03 (d, 1H, J=7.93 Hz), 7.66 (d, 2H, J=8.97 Hz), 7.54 (t, 1H, J=8.01 Hz), 7.43 (m, 1H), 7.26 (d, 1H, J=4.80 Hz), 7.01 (d, 2H, J=8.96 Hz), 6.95 (d, 1H, J=4.80 Hz), 4.12 (m, 2H), 3.60 (m, 3H), 3.11 (m, 3H), 3.04 (m, 3H), 1.14 (d, 3H, J=6.16 Hz).

Example 205

(S)-1-(4-{4-[7-(4-Methanesulfonyl-phenyl)-pyrrolo[2,1-f][1,2,4]triazin-2-ylamino]-phenyl}-piperazin-1-yl)-propan-2-ol The compound was prepared in an analogous fashion to Example 69 replacing 2-Methanesulfinyl-7-(2-methoxyphenyl)-pyrrolo[2,1-f][1,2,4]triazine with 2-Methanesulfinyl-7-(4-methanesulfonyl-phenyl)-pyrrolo[2,1-f][1,2,4]triazine to afford 68.72 mg of (S)-1-(4-{4-[7-(4-Methanesulfonyl-phenyl)-pyrrolo[2,1-f][1,2,4]triazin-2-ylamino]-phenyl}-piperazin-1-yl)-propan-2-ol as a lyophilized powder. (M+H)=507.16. $^1$H NMR (400 MHz, DMSO, d$_6$) δ 9.41 (s, 1H), 9.03 (s, 1H), 8.49 (d, 2H, J=8.52 Hz), 8.03 (d, 2H, J=8.52 Hz), 7.64 (d, 2H, J=8.92 Hz), 7.34 (d, 1H, J=4.85 Hz), 7.04 (d, 2H, J=9.01 Hz), 6.98 (d, 1H, J=4.81 Hz), 4.14 (m, 2H), 3.75 (m, 2H), 3.60 (m, 2H), 3.29 (s, 3H), 3.21 (m, 3H), 3.10 (m, 2H), 1.15 (d, 3H, J=6.12 Hz).

Example 206

(R)-1-(4-{4-[7-(2-Methoxy-phenyl)-pyrrolo[2,1-f][1,2,4]triazin-2-ylamino]-phenyl}-piperazin-1-yl)-propan-2-ol 206a) (R)-1-[4-(4-Nitro-phenyl)-piperazin-1-yl]-propan-2-ol: The compound was prepared in an analogous fashion to Example 69A replacing (S)-(−)-Propylene Oxide with (R)-(−)-Propylene Oxide to afford 1.79 grams of (R)-1-[4-(4-Nitro-phenyl)-piperazin-1-yl]-propan-2-ol as a yellow solid. (M+H)=266.02.

206b) (R)-1-[4-(4-Amino-phenyl)-piperazin-1-yl]-propan-2-ol: The compound was prepared in an analogous fashion to 69B replacing (S)-1-[4-(4-Nitro-phenyl)-piperazin-1-yl]-propan-2-ol with (R)-1-[4-(4-Nitro-phenyl)-piperazin-1-yl]-propan-2-ol to afford 1.20 grams of (R)-1-[4-(4-Amino-phenyl)-piperazin-1-yl]-propan-2-ol as a white powder. (M+H)=236.21.

206c) (R)-1-(4-{4-[7-(2-Methoxy-phenyl)-pyrrolo[2,1-f][1,2,4]triazin-2-ylamino]-phenyl}-piperazin-1-yl)-propan-2-ol: The compound was prepared in an analogous fashion to Example 69C replacing (S)-1-[4-(4-Amino-phenyl)-piperazin-1-yl]-propan-2-ol with (R)-1-[4-(4-Amino-phenyl)-piperazin-1-yl]-propan-2-ol to afford 101.55 mg of (R)-1-(4-{4-[7-(2-Methoxy-phenyl)-pyrrolo[2,1-f][1,2,4]triazin-2-ylamino]-phenyl}-piperazin-1-yl)-propan-2-ol as a lyophilized powder. (M+H)=459.20. $^1$H NMR (400 MHz, DMSO, d$_6$) δ 9.22 (s, 1H), 8.92 (s, 1H), 7.82 (dd, 1H, J=1.40, 6.16 Hz), 7.61 (d, 2H, J=8.97 Hz), 7.45 (m, 1H), 7.22 (d, 1H, J=8.28 Hz), 7.12 (t, 1H, J=7.40 Hz), 6.89 (m, 4H), 4.12 (m, 2H), 3.80 (s, 3H), 3.62 (m, 4H), 3.19 (m, 3H), 3.04 (m, 2H), 1.14 (d, 3H, J=6.12 Hz).

Example 207

(R)-1-(4-{4-[7-(5-Chloro-2-methoxy-phenyl)-pyrrolo[2,1-f][1,2,4]triazin-2-ylamino]-phenyl}-piperazin-1-yl)-propan-2-ol The compound was prepared in an analogous fashion to Example 73 replacing 2-Methanesulfinyl-7-(2-methoxy-phenyl)-pyrrolo[2,1-f][1,2,4]triazine with 7-(5-Chloro-2-methoxy-phenyl)-2-methanesulfinyl-pyrrolo[2,1-f][1,2,4]triazine to afford 118.92 mg of (R)-1-(4-{4-[7-(5-Chloro-2-methoxy-phenyl)-pyrrolo[2,1-f][1,2,4]triazin-2-ylamino]-phenyl}-piperazin-1-yl)-propan-2-ol as a lyophilized powder. (M+H)=493.17. $^1$H NMR (400 MHz, DMSO, d$_6$) δ 9.32 (s, 1H), 8.96 (s, 1H), 8.09 (s, 1H), 7.63 (d, 2H, J=8.96 Hz), 7.47 (dd, 2H, J=2.69, 8.96 Hz), 7.23 (d, 1H, J=8.97 Hz), 7.04 (d, 1H, J=4.69 Hz), 6.91 (m, 3H), 4.11 (m, 2H), 3.83 (s, 3H), 3.60 (m, 4H), 3.18 (m, 3H), 3.02 (m, 2H), 1.14 (d, 3H, J=6.16 Hz).

Example 208

(R)-1-(4-{4-[7-(3-Chloro-phenyl)-pyrrolo[2,1-f][1,2,4]triazin-2-ylamino]-phenyl}-piperazin-1-yl)-propan-2-ol The compound was prepared in an analogous fashion to Example 73 replacing 2-Methanesulfinyl-7-(2-methoxy-phenyl)-pyrrolo[2,1-f][1,2,4]triazine with 7-(3-Chloro-phenyl)-2-methanesulfinyl-pyrrolo[2,1-f][1,2,4]triazine to afford 116.01 mg of (R)-1-(4-{4-[7-(3-Chloro-phenyl)-pyrrolo[2,1-f][1,2,4]triazin-2-ylamino]-phenyl}-piperazin-1-yl)-propan-2-ol as a lyophilized powder. (M+H)=463.14. $^1$H NMR (400 MHz, DMSO, d$_6$) δ 9.38 (s, 1H), 8.98 (s, 1H), 8.49 (m, 1H), 8.03 (d, 1H, J=7.92 Hz), 7.67 (d, 2H, J=9.01 Hz), 7.54 (t, 1H, J=7.97 Hz), 7.43 (d, 1H, J=6.16 Hz), 7.26 (d, 1H, J=4.80 Hz), 7.01 (d, 2H, J=9.00 Hz), 6.95 (d, 1H, J=4.76 Hz), 4.12 (m, 2H), 3.66 (m, 4H), 3.19 (m, 3H), 3.05 (m, 2H), 1.14 (d, 3H, J=6.16 Hz).

Example 209

(R)-1-(4-{4-[7-(4-Methanesulfonyl-phenyl)-pyrrolo[2,1-f][1,2,4]triazin-2-ylamino]-phenyl}-piperazin-1-yl)-propan-2-ol The compound was prepared in an analogous fashion to Example 73 replacing 2-Methanesulfinyl-7-(2-methoxy-phenyl)-pyrrolo[2,1-f][1,2,4]triazine with 2-Methanesulfinyl-7-(4-methanesulfonyl-phenyl)-pyrrolo[2,1-f][1,2,4]triazine to afford 7.85 mg of (R)-1-(4-{4-[7-(4-Methanesulfonyl-phenyl)-pyrrolo[2,1-f][1,2,4]triazin-2-ylamino]-phenyl}-piperazin-1-yl)-propan-2-ol as a lyophilized powder. (M+H)=507.15. $^1$H NMR (400 MHz, DMSO, d$_6$) δ 9.40 (s, 1H), 9.03 (s, 1H), 8.49 (d, 2H, J=8.48 Hz), 8.03 (d, 2H, J=8.61 Hz), 7.63 (d, 2H, J=9.00 Hz), 7.34 (d, 1H, J=4.85 Hz), 7.03 (d, 2H, J=9.00 Hz), 6.98 (d, 1H, J=4.83 Hz), 4.14 (m, 2H), 3.65 (m, 4H), 3.23 (m, 3H), 3.15 (m, 2H), 1.15 (d, 3H, J=6.17 Hz).

Example 210

(S)-1-(4-{3-[7-(2-Methoxy-phenyl)-pyrrolo[2,1-f][1,2,4]triazin-2-ylamino]-phenyl}-piperazin-1-yl)-propan-2-ol The compound was prepared in an analogous fashion to Example 69 replacing 1-(4-Nitro-phenyl)-piperazine with 1-(3-Nitro-phenyl)-piperazine to afford 9.81 mg of (S)-1-(4-{3-[7-(2-Methoxy-phenyl)-pyrrolo[2,1-f][1,2,4]triazin-2-ylamino]-phenyl}-piperazin-1-yl)-propan-2-ol as a lyophilized powder. (M+H)=459.15. $^1$H NMR (400 MHz, DMSO, d$_6$) δ 9.28 (s, 1H), 8.95 (s, 1H), 7.74 (m, 1H), 7.49 (m, 1H), 7.32 (m, 1H), 7.19 (m, 2H), 7.09 (m, 2H), 6.91 (m, 2H), 6.55 (m, 1H), 4.13 (m, 2H), 3.77 (s, 3H), 3.40 (m, 4H), 3.12 (m, 3H), 3.01 (m, 2H), 1.15 (d, 3H, J=6.12 Hz).

Example 211

(S)-1-(4-{3-[7-(5-Chloro-2-methoxy-phenyl)-pyrrolo[2,1-f][1,2,4]triazin-2-ylamino]-phenyl}-piperazin-1-yl)-propan-2-ol The compound was prepared in an analogous fashion to Example 69 replacing 1-(4-Nitro-phenyl)-piperazine with 1-(3-Nitro-phenyl)-piperazine and 2-Methanesulfinyl-7-(2-methoxy-phenyl)-pyrrolo[2,1-f][1,2,4]triazine with 7-(5-

Chloro-2-methoxy-phenyl)-2-methanesulfinyl-pyrrolo[2,1-f][1,2,4]triazine to afford 25.13 mg of (S)-1-(4-{3-[7-(5-Chloro-2-methoxy-phenyl)-pyrrolo[2,1-f][1,2,4]triazin-2-ylamino]-phenyl}-piperazin-1-yl)-propan-2-ol as a lyophilized powder. (M+H)=493.11. $^1$H NMR (400 MHz, DMSO, d$_6$) δ 9.34 (s, 1H), 8.98 (s, 1H), 7.94 (m, 1H), 7.50 (dd, 1H, J=2.68, 6.20 Hz), 7.39 (d, 1H, J=8.20 Hz), 7.23 (d, 1H, J=8.96 Hz), 7.14 (m, 2H), 7.01 (d, 1H, J=4.68 Hz), 6.93 (d, 1H, J=4.64 Hz), 6.59 (dd, 1H, J=1.80, 6.32 Hz), 4.11 (m, 2H), 3.80 (s, 3H), 3.73 (m, 4H), 3.16 (m, 3H), 3.02 (m, 2H), 1.15 (d, 3H, J=6.16 Hz).

Example 212

(S)-1-(4-{3-[7-(3-Chloro-phenyl)-pyrrolo[2,1-f][1,2,4]triazin-2-ylamino]-phenyl}-piperazin-1-yl)-propan-2-ol The compound was prepared in an analogous fashion to Example 69 replacing 1-(4-Nitro-phenyl)-piperazine with 1-(3-Nitro-phenyl)-piperazine and 2-Methanesulfinyl-7-(2-methoxy-phenyl)-pyrrolo[2,1-f][1,2,4]triazine with 7-(3-Chloro-phenyl)-2-methanesulfinyl-pyrrolo[2,1-f][1,2,4]triazine to afford 28.66 mg of (S)-1-(4-{3-[7-(3-Chloro-phenyl)-pyrrolo[2,1-f][1,2,4]triazin-2-ylamino]-phenyl}-piperazin-1-yl)-propan-2-ol as a lyophilized powder. (M+H)= 463.12. $^1$H NMR (400 MHz, DMSO, d$_6$) δ 9.41 (s, 1H), 9.02 (s, 1H), 8.39 (m, 1H), 8.06 (d, 1H, J=7.85 Hz), 7.48 (m, 3H), 7.26 (m, 3H), 6.98 (d, 1H, J=4.81 Hz), 6.67 (dd, 1H, J=2.00, 6.16 Hz), 4.12 (m, 2H), 3.66 (m, 2H), 3.53 (m, 2H), 3.17 (m, 3H), 3.11 (m, 2H), 1.14 (d, 3H, J=6.16 Hz).

Example 213

(R)-1-(4-{3-[7-(2-Methoxy-phenyl)-pyrrolo[2,1-f][1,2,4]triazin-2-ylamino]-phenyl}-piperazin-1-yl)-propan-2-ol The compound was prepared in an analogous fashion to Example 73 replacing 1-(4-Nitro-phenyl)-piperazine with 1-(3-Nitro-phenyl)-piperazine to afford 5.76 mg of (R)-1-(4-{3-[7-(2-Methoxy-phenyl)-pyrrolo[2,1-f][1,2,4]triazin-2-ylamino]-phenyl}-piperazin-1-yl)-propan-2-ol as a lyophilized powder. (M+H)=459.15. $^1$H NMR (400 MHz, DMSO, d$_6$) δ 9.28 (s, 1H), 8.96 (s, 1H), 7.89 (m, 1H), 7.74 (m, 1H), 7.71 (m, 1H), 7.55 (m, 1H), 7.49 (m, 1H), 7.16 (m, 2H), 6.91 (q, 2H, J=6.64 Hz), 6.54 (d, 1H, J=8.15 Hz), 4.15 (m, 2H), 3.77 (s, 3H), 3.46 (m, 4H), 2.98-3.15 (m, 5H), 1.15 (d, 3H, J=6.16 Hz).

Example 214

(R)-1-(4-{3-[7-(5-Chloro-2-methoxy-phenyl)-pyrrolo[2,1-f][1,2,4]triazin-2-ylamino]-phenyl}-piperazin-1-yl)-propan-2-ol The compound was prepared in an analogous fashion to Example 73 replacing 1-(4-Nitro-phenyl)-piperazine with 1-(3-Nitro-phenyl)-piperazine and 2-Methanesulfinyl-7-(2-methoxy-phenyl)-pyrrolo[2,1-f][1,2,4]triazine with 7-(5-Chloro-2-methoxy-phenyl)-2-methanesulfinyl-pyrrolo[2,1-f][1,2,4]triazine to afford 19.24 mg of (R)-1-(4-{3-[7-(5-Chloro-2-methoxy-phenyl)-pyrrolo[2,1-f][1,2,4]triazin-2-ylamino]-phenyl}-piperazin-1-yl)-propan-2-ol as a lyophilized powder. (M+H)=493.09. $^1$H NMR (400 MHz, DMSO, d$_6$) δ 9.34 (s, 1H), 8.98 (s, 1H), 7.94 (m, 1H), 7.50 (dd, 1H, J=2.64, 6.24 Hz), 7.39 (d, 1H, J=8.12 Hz), 7.24 (d, 1H, J=8.96 Hz), 7.14 (m, 2H), 7.01 (d, 1H, J=4.68 Hz), 6.93 (d, 1H, J=4.68 Hz), 6.59 (dd, 1H, J=1.80, 6.48 Hz), 4.12 (m, 2H), 3.80 (s, 3H), 3.53 (m, 4H), 3.15 (m, 3H), 3.02 (m, 2H), 1.15 (d, 2H, J=6.16 Hz).

Example 215

(R)-1-(4-{3-[7-(3-Chloro-phenyl)-pyrrolo[2,1-f][1,2,4]triazin-2-ylamino]-phenyl}-piperazin-1-yl)-propan-2-ol The compound was prepared in an analogous fashion to Example 73 replacing 1-(4-Nitro-phenyl)-piperazine with 1-(3-Nitro-phenyl)-piperazine and 2-Methanesulfinyl-7-(2-methoxy-phenyl)-pyrrolo[2,1-f][1,2,4]triazine with 7-(3-Chloro-phenyl)-2-methanesulfinyl-pyrrolo[2,1-f][1,2,4]triazine to afford 22.28 mg of (R)-1-(4-{3-[7-(3-Chloro-phenyl)-pyrrolo[2,1-f][1,2,4]triazin-2-ylamino]-phenyl}-piperazin-1-yl)-propan-2-ol as a lyophilized powder. (M+H)= 463.12. $^1$H NMR (400 MHz, DMSO, d$_6$) δ 9.52 (m, 1H), 9.41 (s, 1H), 8.39 (m, 1H), 8.06 (d, 1H, J=7.68 Hz), 7.50 (m, 3H), 7.25 (m, 2H), 7.18 (m, 1H), 6.97 (d, 1H, J=4.76 Hz), 6.67 (d, 1H, J=8.00 Hz), 4.11 (m, 2H), 3.66 (m, 2H), 3.53 (m, 2H), 3.14 (m, 3H), 3.03 (m, 2H), 1.15 (d, 3H, J=6.16 Hz).

Example 216

(S)-1-(4-{3-[7-(4-Methanesulfonyl-phenyl)-pyrrolo[2,1-f][1,2,4]triazin-2-ylamino]-phenyl}-piperazin-1-yl)-propan-2-ol The compound was prepared in an analogous fashion to Example 69 replacing 1-(4-Nitro-phenyl)-piperazine with 1-(3-Nitro-phenyl)-piperazine and 2-Methanesulfinyl-7-(2-methoxy-phenyl)-pyrrolo[2,1-f][1,2,4]triazine with 2-Methanesulfinyl-7-(4-methanesulfonyl-phenyl)-pyrrolo[2,1-f][1,2,4]triazine to afford 44.32 mg of (S)-1-(4-{3-[7-(4-Methanesulfonyl-phenyl)-pyrrolo[2,1-f][1,2,4]triazin-2-ylamino]-phenyl}-piperazin-1-yl)-propan-2-ol as a lyophilized powder. (M+H)=507.10. $^1$H NMR (400 MHz, DMSO, d$_6$) δ 9.49 (s, 2H), 9.08 (s, 1H), 8.51 (d, 2H, J=8.56 Hz), 8.03 (d, 2H, J=8.60 Hz), 7.41 (m, 1H), 7.37 (d, 1H, J=4.81 Hz), 7.25 (m, 2H), 7.01 (d, 1H, J=4.84 Hz), 6.67 (d, 1H, J=6.64 Hz), 4.15 (m, 2H), 3.75 (m, 2H), 3.53 (m, 2H), 3.31 (s, 3H), 3.11 (m, 3H), 3.03 (m, 2H), 1.13 (d, 3H, J=6.12 Hz).

Example 217

(R)-1-(4-{3-[7-(4-Methanesulfonyl-phenyl)-pyrrolo[2,1-f][1,2,4]triazin-2-ylamino]-phenyl}-piperazin-1-yl)-propan-2-ol The compound was prepared in an analogous fashion to Example 73 replacing 1-(4-Nitro-phenyl)-piperazine with 1-(3-Nitro-phenyl)-piperazine and 2-Methanesulfinyl-7-(2-methoxy-phenyl)-pyrrolo[2,1-f][1,2,4]triazine with 2-Methanesulfinyl-7-(4-methanesulfonyl-phenyl)-pyrrolo[2,1-f][1,2,4]triazine to afford 44.32 mg of (R)-1-(4-{3-[7-(4-Methanesulfonyl-phenyl)-pyrrolo[2,1-f][1,2,4]triazin-2-ylamino]-phenyl}-piperazin-1-yl)-propan-2-ol as a lyophilized powder. (M+H)=507.10. $^1$H NMR (400 MHz, DMSO, d$_6$) δ 9.49 (s, 2H), 9.08 (s, 1H), 8.51 (d, 2H, J=8.52 Hz), 8.03 (d, 2H, J=8.56 Hz), 7.42 (m, 1H), 7.37 (d, 1H, J=4.80 Hz), 7.26 (m, 2H), 7.01 (d, 1H, J=4.80 Hz), 6.67 (d, 1H, J=6.72 Hz), 4.15 (m, 2H), 3.70 (m, 4H), 3.31 (s, 3H), 3.13 (m, 5H), 1.13 (d, 3H, J=6.16 Hz).

Example 218

1-(4-{3-[7-(2-Methoxy-phenyl)-pyrrolo[2,1-f][1,2,4]triazin-2-ylamino]-phenyl}-piperazin-1-yl)-2-methyl-propan-2-ol 218a) 2-Methyl-1-[4-(3-nitro-phenyl)-piperazin-1-yl]-propan-2-ol 1-(3-Nitro-phenyl)-piperazine; hydrochloride (2.0 g, 0.0082 mol) was dissolved in Methanol (42.5 mL) and the reaction mixture was placed in a sealed tube. 1,2-epoxy-2-methylpropane (0.888 g, 0.0123 mol) was then added at room temperature and the reaction was allowed to stir overnight. The mixture was then reduced en vacuo and the product was isolated by Isco flash column chromatography (DCM/MeOH) to afford 1.60 grams of 2-Methyl-1-[4-(3-nitro-phenyl)-piperazin-1-yl]-propan-2-ol as a yellow powder.

218b) 1-[4-(3-Amino-phenyl)-piperazin-1-yl]-2-methyl-propan-2-ol

2-Methyl-1-[4-(3-nitro-phenyl)-piperazin-1-yl]-propan-2-ol (1.60 g, 0.00573 mol) was dissolved in Methanol (40 mL) and the solution was carefully added to a Parr vessel containing 10% Palladium on Carbon (90.10, carbon black. Palladium, 0.750 g, 0.0562 mol) under nitrogen. The reaction was then placed on a Parr apparatus and was allowed to shake until uptake of hydrogen ceased (overnight). Catalyst was filtered and the filtrate was reduced to provide 1.20 grams of 1-[4-(3-Amino-phenyl)-piperazin-1-yl]-2-methyl-propan-2-ol without further purification as a light purple solid. (M+H)= 250.06.

c) 1-(4-{3-[7-(2-Methoxy-phenyl)-pyrrolo[2,1-f][1,2,4]triazin-2-ylamino]-phenyl}-piperazin-1-yl)-2-methyl-propan-2-ol 2-Methanesulfinyl-7-(2-methoxy-phenyl)-pyrrolo[2,1-f][1,2,4]triazine (125.0 mg, 0.0004350 mol), N,N-Diisopropylethylamine (0.114 mL, 0.000652 mol) and 1-[4-(3-Amino-phenyl)-piperazin-1-yl]-2-methyl-propan-2-ol (0.217 g, 0.000870 mol) were dissolved in 1-Methoxy-2-propanol (1.2 mL) and the reaction was microwaved on 300 watts, 180° C. for 40 minutes or until HPLC showed consumption of starting material. The reaction mixture was then reduced en vacuo and the product was isolated and purified by Gilson prep HPLC to provide 29.84 mg of 1-(4-{3-[7-(2-Methoxy-phenyl)-pyrrolo[2,1-f][1,2,4]triazin-2-ylamino]-phenyl}-piperazin-1-yl)-2-methyl-propan-2-ol as a lyophilized powder. (M+H)=473.8. $^1$H NMR (400 MHz, DMSO, d$_6$) δ 9.29 (s, 1H), 8.96 (s, 1H), 7.72 (dd, 1H, J=1.64, 5.93 Hz), 7.46 (m, 1H), 7.33 (m, 1H), 7.18 (m, 2H), 7.08 (m, 2H), 6.91 (m, 2H), 6.53 (dd, 1H, J=1.84, 6.29 Hz), 3.77 (s, 3H), 3.55 (m, 2H), 3.34 (m, 2H), 3.19 (m, 4H), 3.05 (m, 2H), 1.29 (s, 6H).

Example 219

1-(4-{3-[7-(5-Chloro-2-methoxy-phenyl)-pyrrolo[2,1-f][1,2,4]triazin-2-ylamino]-phenyl}-piperazin-1-yl)-2-methyl-propan-2-ol The compound was prepared in an analogous fashion to Example 85 replacing 2-Methanesulfinyl-7-(2-methoxy-phenyl)-pyrrolo[2,1-f][1,2,4]triazine with 7-(5-Chloro-2-methoxy-phenyl)-2-methanesulfinyl-pyrrolo[2,1-f][1,2,4]triazine to afford 42.47 mg of 1-(4-{3-[7-(5-Chloro-2-methoxy-phenyl)-pyrrolo[2,1-f][1,2,4]triazin-2-ylamino]-phenyl}-piperazin-1-yl)-2-methyl-propan-2-ol as a lyophilized powder. (M+H)=507.8. $^1$H NMR (400 MHz, DMSO, d$_6$) δ 9.35 (s, 1H), 8.98 (s, 1H), 7.93 (m, 1H), 7.38 (m, 1H), 7.23 (d, 1H, J=8.93 Hz), 7.19 (m, 2H), 7.15 (m, 1H), 7.00 (d, 1H, J=4.68 Hz), 6.94 (d, 1H, J=4.68 Hz), 6.61 (m, 1H), 3.81 (s, 3H), 3.60 (m, 2H), 3.28 (m, 4H), 3.16 (m, 4H), 1.29 (s, 6H).

Example 220

1-(4-{3-[7-(3-Chloro-phenyl)-pyrrolo[2,1-f][1,2,4]triazin-2-ylamino]-phenyl}-piperazin-1-yl)-2-methyl-propan-2-ol The compound was prepared in an analogous fashion to Example 85 replacing 2-Methanesulfinyl-7-(2-methoxy-phenyl)-pyrrolo[2,1-f][1,2,4]triazine with 7-(3-Chloro-phenyl)-2-methanesulfinyl-pyrrolo[2,1-f][1,2,4]triazine to afford 27.38 mg of 1-(4-{3-[7-(3-Chloro-phenyl)-pyrrolo[2,1-f][1,2,4]triazin-2-ylamino]-phenyl}-piperazin-1-yl)-2-methyl-propan-2-ol as a lyophilized powder. (M+H)=477.8. $^1$H NMR (400 MHz, DMSO, d$_6$) δ 9.43 (s, 1H), 9.03 (s, 1H), 8.38 (m, 1H), 8.06 (d, 1H, J=7.89 Hz), 7.54 (t, 1H, J=7.97 Hz), 7.46 (m, 2H), 7.24 (m, 3H), 6.98 (d, 1H, J=4.76 Hz), 6.66 (dd, 1H, J=1.83, 6.41 Hz), 3.58 (m, 4H), 3.21 (m, 6H), 1.28 (s, 6H).

Example 221

1-(4-{4-[7-(2-Methoxy-phenyl)-pyrrolo[2,1-f][1,2,4]triazin-2-ylamino]-phenyl}-piperazin-1-yl)-2-methyl-propan-2-ol The compound was prepared in an analogous fashion to Example 85 replacing 1-(3-Nitro-phenyl)-piperazine with 1-(4-Nitro-phenyl)-piperazine to afford 88.32 mg of 1-(4-{4-[7-(2-Methoxy-phenyl)-pyrrolo[2,1-f][1,2,4]triazin-2-ylamino]-phenyl}-piperazin-1-yl)-2-methyl-propan-2-ol as a lyophilized powder. (M+H)=473.8. $^1$H NMR (400 MHz, DMSO, d$_6$) δ 9.22 (s, 1H), 8.92 (s, 1H), 7.83 (dd, 1H, J=1.53, 6.08 Hz), 7.61 (d, 2H, J=9.01 Hz), 7.45 (m, 1H), 7.21 (d, 1H, J=8.28 Hz), 7.13 (t, 1H, J=7.52 Hz), 6.89 (m, 4H), 3.80 (s, 3H), 3.58 (m, 6H), 3.08 (m, 4H), 1.28 (s, 6H).

Example 222

1-(4-{4-[7-(5-Chloro-2-methoxy-phenyl)-pyrrolo[2,1-f][1,2,4]triazin-2-ylamino]-phenyl}-piperazin-1-yl)-2-methyl-propan-2-ol The compound was prepared in an analogous fashion to Example 85 replacing 1-(3-Nitro-phenyl)-piperazine with 1-(4-Nitro-phenyl)-piperazine and 2-Methanesulfinyl-7-(2-methoxy-phenyl)-pyrrolo[2,1-f][1,2,4]triazine with 7-(5-Chloro-2-methoxy-phenyl)-2-methanesulfinyl-pyrrolo[2,1-f][1,2,4]triazine to afford 89.29 mg of 1-(4-{4-[7-(5-Chloro-2-methoxy-phenyl)-pyrrolo[2,1-f][1,2,4]triazin-2-ylamino]-phenyl}-piperazin-1-yl)-2-methyl-propan-2-ol as a lyophilized powder. (M+H)=507.8. $^1$H NMR (400 MHz, DMSO, d$_6$) δ 9.32 (s, 1H), 8.96 (s, 1H), 8.08 (m, 1H), 7.64 (d, 2H, J=9.00 Hz), 7.48 (m, 1H), 7.23 (d, 1H, J=8.96 Hz), 7.05 (d, 1H, J=4.67 Hz), 6.91 (m, 3H), 3.83 (s, 3H), 3.58 (m, 4H), 3.19 (m, 6H), 1.28 (s, 6H).

Example 223

1-(4-{4-[7-(3-Chloro-phenyl)-pyrrolo[2,1-f][1,2,4]triazin-2-ylamino]-phenyl}-piperazin-1-yl)-2-methyl-propan-2-ol The compound was prepared in an analogous fashion to Example 85 replacing 1-(3-Nitro-phenyl)-piperazine with 1-(4-Nitro-phenyl)-piperazine and 2-Methanesulfinyl-7-(2-methoxy-phenyl)-pyrrolo[2,1-f][1,2,4]triazine with 7-(3-Chloro-phenyl)-2-methanesulfinyl-pyrrolo[2,1-f][1,2,4]triazine to afford 22.28 mg of 1-(4-{4-[7-(3-Chloro-phenyl)-pyrrolo[2,1-f][1,2,4]triazin-2-ylamino]-phenyl}-piperazin-1-yl)-2-methyl-propan-2-ol as a lyophilized powder. (M+H)= 477.8. $^1$H NMR (400 MHz, DMSO, $d_6$) δ 9.39 (s, 1H), 8.99 (s, 1H), 8.49 (s, 1H), 8.03 (d, 1H, J=7.93 Hz), 7.67 (d, 2H, J=8.92 Hz), 7.54 (t, 1H, J=7.97 Hz), 7.44 (m, 1H), 7.26 (d, 1H, J=4.76 Hz), 7.01 (d, 2H, J=8.96 Hz), 6.95 (d, 1H, J=4.76 Hz), 3.63 (m, 4H), 3.25 (m, 6H), 1.31 (s, 6H).

Example 231

{2-Methoxy-4-[4-(1-methyl-piperidin-4-yl)-piperazin-1-yl]-phenyl}-[7-(2-methoxy-phenyl)-pyrrolo[2,1-f][1,2,4]triazin-2-yl]-amine A solution of 2-methoxy-4-[4-(1-methyl-piperidin-4-yl)-piperazin-1-yl]-phenylamine (140 mg, 0.45 mmol) and 2-methanesulfinyl-7-(2-methoxy-phenyl)-pyrrolo[2,1-f][1,2,4]triazine (65 mg, 0.23 mmol) in 2-methoxyethanol (0.50 mL) was treated with N,N-diisopropylethylamine (59 uL, 0.34 mmol). The reaction was heated under microwave conditions at 300 watts at 180° C. for 90 minutes. The mixture was diluted with methanol (10 mL), filtered and concentrated. The residue was purified by preparative RP-HPLC to give 65 mg of an amber amorphous powder. MS=528 (M-TFA+H); NMR (DMSO-$d_6$, ppm): 10.15 (s, 1H), 9.83 (s, 1H), 8.92 (s, 1H), 7.92 (d, J=9 Hz, 1H), 7.85 (d, J=8 Hz, 1H), 7.57 (s, 1H), 7.43 (t, J=8 Hz, 1H), 7.19 (d, J=8 Hz, 1H), 7.09 (t, J=8 Hz, 1H), 6.95 (q, J=5 Hz, 14 Hz, 1H), 6.73 (s, 1H), 6.45 (d, J=9 Hz, 1H), 3.87 (s, 3H), 3.80 (s, 3H), 3.61 (m, 4H), 3.48 (m, 2H), 3.22 (m, 2H), 3.00 (m, 4H), 2.80 (s, 3H), 2.67 (m, 1H), 2.37 (m, 2H), 1.88 (m, 2H).

Example 232

1-[4-(1-{3-Methoxy-4-[7-(2-methoxy-phenyl)-pyrrolo[2,1-f][1,2,4]triazin-2-ylamino]-phenyl}-piperidin-3-yl)-piperazin-1-yl]-ethanone 232a) 4-(1-tert-Butoxycarbonyl-piperidin-3-yl)-piperazine-1-carboxylic acid benzyl ester: To a solution of 3-oxo-piperidine-1-carboxylic acid tert-butyl ester (15.0 g, 75.3 mmol) and piperazine-1-carboxylic acid benzyl ester (16.6 g, 75.3 mmol) in methylene chloride (500 mL) was added acetic acid (0.43 mL, 7.5 mmol). The mixture was stirred for one hour and sodium triacetoxyborohydride (48 g, 220 mmol) was added. The mixture was stirred overnight at room temperature. The mixture was treated with water and stirred until cessation of gas evolution. The organic phase was washed with sat'd aq. sodium bicarbonate and brine, dried (MgSO4), filtered and concentrated. Flash chromatography over silica gel (EtOAc-hexane eluent) gave 24.6 g of the title compound as a pale yellow oil. MS=404 (M+1).

232b) 4-Piperidin-3-yl-piperazine-1-carboxylic acid benzyl ester; compound with trifluoro-acetic acid: A solution of 4-(1-tert-butoxycarbonyl-piperidin-3-yl)-piperazine-1-carboxylic acid benzyl ester (24.5 g, 60.7 mmol) in methylene chloride (250 mL) was cooled in an ice-water bath and to this was added trifluoroacetic acid (250 mL). The mixture was stirred at 0-5° C. and allowed to slowly warm to room temperature overnight. The mixture was concentrated to a viscous oil. Dropwise addition of ethyl acetate (150 mL) with stirring produced a precipitate which was stirred further for several hours. The solid was collected by vacuum filtration with applied house vacuum, washed with ethyl acetate and dried to constant weight to provide 18.7 g of the title product as a white solid, used without further purification. MS=304 (M-TFA+1).

232c) 4-[1-(3-Methoxy-4-nitro-phenyl)-piperidin-3-yl]-piperazine-1-carboxylic acid benzyl ester: To a mixture of 4-piperidin-3-yl-piperazine-1-carboxylic acid benzyl ester; compound with trifluoro-acetic acid (10.0 g, 24.0 mmol) and potassium carbonate (8.3 g, 60 mmol) in dimethylformamide (100 mL) was added 4-fluoro-2-methoxy-1-nitro-benzene (4.1 g, 24 mmol) with stirring. The mixture was heated at 60° C. for 18 hours. The solvent was removed on the rotovap and the residue was partitioned between dichloromethane and water, the organic phase was washed with saturated aqueous sodium bicarbonate and brine, dried (MgSO4), filtered and concentrated. Flash chromatography over silica gel (5% MeOH-DCM eluant) gave 9.2 g of the title compound as a viscous oil.

232d) 1-[1-(3-Methoxy-4-nitro-phenyl)-piperidin-3-yl]-piperazine hydrobromide

A solution of 4-[1-(3-methoxy-4-nitro-phenyl)-piperidin-3-yl]-piperazine-1-carboxylic acid benzyl ester (300 mg, 0.66 mmol) in 4 M of hydrogen bromide in acetic acid (6 mL, 20 mmol) was heated at 40-45° C. for 45 min, then allowed to cool to room temperature while being stirred overnight. The orange homogenous solution was added dropwise to a vigorously stirred flask of EtOAc (50 mL) and the resulting precipitate was filtered, washed with EtOAc and dried in-vacuo to give 294 mg of an orange solid, used without further purification. MS=322 (M-HBr+1).

232e) 1-{4-[1-(3-Methoxy-4-nitro-phenyl)-piperidin-3-yl]-piperazin-1-yl}-ethanone. To a mixture of 1-[1-(3-methoxy-4-nitro-phenyl)-piperidin-3-yl]-piperazine; hydrobromide (300 mg, 0.75 mmol) and N,N-diisopropylethylamine (390 uL, 2.2 mmol) in methylene chloride (15 mL) cooled in an ice-water bath was added acetic anhydride (85 uL, 0.90 mmol) with stirring. The mixture was stirred while being allowed to warm to room temperature over 1.5 hours. The mixture was diluted with DCM, washed with saturated aqueous sodium bicarbonate and brine, dried (MgSO4), filtered and concentrated. Flash chromatography over silica gel gave 180 mg of the title compound as a yellow semi-solid. MS=363 (M+1).

232f) 1-{4-[1-(4-Amino-3-methoxy-phenyl)-piperidin-3-yl]-piperazin-1-yl}-ethanone. To a solution of 1-{4-[1-(3-methoxy-4-nitro-phenyl)-piperidin-3-yl]-piperazin-1-yl}-ethanone (175 mg, 0.48 mmol) in ethyl acetate (5 mL) and ethanol (5 mL) in a Paar bottle was added 10% Pd—C. The mixture was placed on a Paar shaker under 50 psi $H_2$ and shaken at room temperature. The mixture was filtered and concentrated to afford 80 mg of the title compound, used without further purification. MS=333 (M+1).

232g) 1-[4-(1-{3-Methoxy-4-[7-(2-methoxy-phenyl)-pyrrolo[2,1-f][1,2,4]triazin-2-ylamino]-phenyl}-piperidin-3-yl)-piperazin-1-yl]-ethanone.

A mixture of 1-{4-[1-(4-amino-3-methoxy-phenyl)-piperidin-3-yl]-piperazin-1-yl}-ethanone (80 mg, 0.24 mmol) and 2-methanesulfinyl-7-(2-methoxy-phenyl)-pyrrolo[2,1-f][1,2,4]triazine (46 mg, 0.16 mmol) in 2-methoxyethanol (0.50 mL) and treated with N,N-Diisopropylethylamine (56 µL, 0.32 mmol). The reaction was microwaved on 300 watts, 200 C for 9.5 hours. The sample was diluted with methanol (10 mL), filtered and concentrated. The crude product was purified by RF-HPLC to afford 34 mg of the title compound as an amber powder after lyophyllization. MS=556 (M-TFA+1); NMR (DMSO-$d_6$, ppm): 9.83 (br, 1H), 8.91 (s, 1H), 7.86 (m, 2H), 7.56 (s, 1H), 7.45 (t, J=7 Hz, 1H), 7.20 (d, J=7 Hz, 1H), 7.10 (t, J=7 Hz, 1H), 6.95 (q, J=5 Hz, 14 Hz, 2H), 6.69 (s, 1H), 6.46 (d, J=7 Hz, 1H), 3.87 (s, 3H), 3.80 (s, 3H), 3.50 (m, 4H), 2.91 (t, J=12 Hz, 2H), 2.70 (t, J=10 Hz, 2H), 2.33 (m, 1H), 2.13 (m, 2H), 2.07 (s, 3H), 1.89 (m, 1H), 1.64 (t, J=10 Hz, 2H).

Example 233

{4-[3-(4-Methanesulfonyl-piperazin-1-yl)-piperidin-1-yl]-2-methoxy-phenyl}-[7-(2-methoxy-phenyl)-pyrrolo[2,1-f][1,2,4]triazin-2-yl]-amine 233a) 1-Methanesulfonyl-4-[1-(3-methoxy-4-nitro-phenyl)-piperidin-3-yl]-piperazine: To a mixture of 1-[1-(3-methoxy-4-nitro-phenyl)-piperidin-3-yl]-piperazine; hydrobromide (300 mg, 0.75 mmol) and N,N-diisopropylethylamine (390 µL, 2.2 mmol) in methylene chloride (15 mL) cooled in an ice-water bath was added methanesulfonyl chloride (69 µL, 0.90 mmol) with stirring. The mixture was stirred while being allowed to warm to room temperature over 1.5 hours. The mixture was diluted with dichloromethane, washed with saturated aqueous sodium bicarbonate and brine, dried (MgSO4), filtered and concentrated. The crude product was flash chromatographed over silica gel (5% MeOH-DCM) to provide 145 mg of the title compound as a yellow solid. MS=399 (M+1).

233b) 4-[3-(4-Methanesulfonyl-piperazin-1-yl)-piperidin-1-yl]-2-methoxy-phenylamine: To a solution of 1-methanesulfonyl-4-[1-(3-methoxy-4-nitro-phenyl)-piperidin-3-yl]-piperazine (140 mg, 0.35 mmol) in ethyl acetate (10 mL) and ethanol (10 mL) in a Paar bottle was added 10% Pd—C (50 mg). The mixture was placed on a Paar apparatus under 50 psi $H_2$ and shaken at room temperature for one hour. The mixture was filtered and concentrated to afford 123 mg of the title compound, used without further purification. MS=369 (M+1).

233c) {4-[3-(4-Methanesulfonyl-piperazin-1-yl)-piperidin-1-yl]-2-methoxy-phenyl}-[7-(2-methoxy-phenyl)-pyrrolo[2,1-f][1,2,4]triazin-2-yl]-amine: A mixture of 4-[3-(4-methanesulfonyl-piperazin-1-yl)-piperidin-1-yl]-2-methoxy-phenylamine (120 mg, 0.33 mmol) and 2-methanesulfinyl-7-(2-methoxy-phenyl)-pyrrolo[2,1-f][1,2,4]triazine (62 mg, 0.22 mmol) in 2-methoxyethanol (0.50 mL) was treated with N,N-diisopropylethylamine (76 uL, 0.43 mmol). The reaction was microwaved at 300 watts at 200° C. for 10.5 hours. The sample was diluted with methanol (10 mL), filtered and concentrated. The crude product was purified by preparative RF-HPLC to afford 36 mg of the title compound as an amorphous amber powder following lyophillization. MS=556 (M-TFA+1); NMR (DMSO-$d_6$, ppm): 9.80 (br, 1H), 8.91 (s, 1H), 7.86 (m, 2H), 7.56 (s, 1H), 7.45 (t, J=7 Hz, 1H), 7.20 (d, J=7 Hz, 1H), 7.10 (t, J=7 Hz, 1H), 6.95 (q, J=5 Hz, 14 Hz, 2H), 6.69 (s, 1H), 6.46 (d, J=7 Hz, 1H), 3.87 (s, 3H), 3.80 (s, 3H), 3.50 (m, 4H), 3.05 (s, 3H), 2.91 (t, J=12 Hz, 2H), 2.70 (t, J=10 Hz, 2H), 2.33 (m, 1H), 2.13 (m, 2H), 1.89 (m, 1H), 1.65 (t, J=10 Hz, 2H).

Example 234

4-(1-{3-Methoxy-4-[7-(2-methoxy-phenyl)-pyrrolo[2,1-f][1,2,4]triazin-2-ylamino]-phenyl}-piperidin-3-yl)-piperazine-1-carboxylic acid benzyl ester 234a) 4-[1-(4-Amino-3-methoxy-phenyl)-piperidin-3-yl]-piperazine-1-carboxylic acid benzyl ester: To a solution of 4-[1-(3-methoxy-4-nitro-phenyl)-piperidin-3-yl]-piperazine-1-carboxylic acid benzyl ester (2.50 g, 5.50 mmol) in ethanol (20 mL) and acetic acid (20 mL) was added Zinc dust (2.50 g, 38.2 mmol). The mixture was stirred for three hours at room temperature at which time MS analysis showed complete and clean conversion to the desired aniline. The mixture was filtered and concentrated. The residue was dissolved into dichloromethane, washed with saturated aqueous sodium bicarbonate and brine, dried (MgSO4), filtered and concentrated to give 2.1 g of an amber viscous oil, used without further purification. MS=425 (M+1).

234b) 4-(1-{3-Methoxy-4-[7-(2-methoxy-phenyl)-pyrrolo[2,1-f][1,2,4]triazin-2-ylamino]-phenyl}-piperidin-3-yl)-piperazine-1-carboxylic acid benzyl ester: A mixture of 4-[1-(4-Amino-3-methoxy-phenyl)-piperidin-3-yl]-piperazine-1-carboxylic acid benzyl ester (90 mg, 0.20 mmol) and 2-methanesulfinyl-7-(2-methoxyphenyl)-pyrrolo[2,1-f][1,2,4]triazine (30.4 mg, 0.11 mmol) in 2-methoxyethanol (0.50 mL) was treated with N,N-diisopropylethylamine (28 uL, 0.16 mol). The reaction was microwaved at 300 watts at 180° C. for three hours. The mixture was diluted with methanol (10 mL), filtered and concentrated. Preparative RF-HPLC gave 13 mg of the title compound. MS=648 (M-TFA+1); NMR (DMSO-$d_6$, ppm): 9.80 (br, 1H), 8.91 (s, 1H), 7.86 (m, 2H), 7.56 (s, 1H), 7.45 (t, J=7 Hz, 1H), 7.40 (m, 5H), 7.20 (d, J=7 Hz, 1H), 7.10 (t, J=7 Hz, 1H), 6.95 (q, J=5 Hz, 14 Hz, 2H), 6.69 (s, 1H), 6.46 (d, J=7 Hz, 1H), 5.13 (s, 2H), 3.87 (s, 3H), 3.80 (s, 3H), 3.50 (m, 4H), 2.91 (t, J=12 Hz, 2H), 2.70 (t, J=10 Hz, 2H), 2.33 (m, 1H), 2.13 (m, 2H), 1.89 (m, 1H), 1.65 (t, J=10 Hz, 2H).

Example 235

{2-Methoxy-4-[3-(4-methyl-piperazin-1-yl)-piperidin-1-yl]-phenyl}-[7-(2-methoxy-phenyl)-pyrrolo[2,1-f][1,2,4]triazin-2-yl]-amine 235a) 1-[1-(3-Methoxy-4-nitro-phenyl)-piperidin-3-yl]-4-methyl-piperazine: To a solution of 1-[1-(3-methoxy-4-nitro-phenyl)-piperidin-3-yl]-piperazine hydrobromide (500 mg, 1.25 mmol) in acetonitrile (20 mL) and methanol (20 mL) was added 10M of formaldehyde in water (4.0 mL) with stirring. After 10 minutes sodium cyanoborohydride (86 mg, 1.4 mmol) was added and the mixture was stirred for two hours at room temperature. The mixture was concentrated and the residue was dissolved in dichloromethane, washed with saturated aqueous sodium bicarbonate and brine, dried (MgSO4), filtered and concentrated to give 315 mg of the title compound of sufficient purity (97%, HPLC) to carry on without further purification. MS=335 (M+1);

235b) 2-Methoxy-4-[3-(4-methyl-piperazin-1-yl)-piperidin-1-yl]-phenylamine: To a solution of 1-[1-(3-methoxy-4-nitro-phenyl)-piperidin-3-yl]-4-methyl-piperazine (310 mg, 0.93 mmol) in ethyl acetate (15 mL) and ethanol (15 mL) in a Paar bottle was added 10% Pd—C catalyst (75 mg). The mixture was placed on a Paar apparatus under 50 psi $H_2$ and shaken at room temperature for two hours. The mixture was filtered and concentrated to give 242 mg of the title compound as a viscous oil which was used without further purification. MS=305 (M+1).

235c) {2-Methoxy-4-[3-(4-methyl-piperazin-1-yl)-piperidin-1-yl]-phenyl}-[7-(2-methoxy-phenyl)-pyrrolo[2,1-f][1,2,4]triazin-2-yl]-amine: To a solution of 2-methoxy-4-[3-(4-methyl-piperazin-1-yl)-piperidin-1-yl]-phenylamine (240 mg, 0.79 mmol) and 2-methanesulfinyl-7-(2-methoxy-phenyl)-pyrrolo[2,1-f][1,2,4]triazine (151 mg, 0.53 mmol) in 2-methoxyethanol (1.5 mL) was added N,N-diisopropylethylamine (183 uL, 1.05 mmol). The mixture was submitted to microwave irradiation at 300 watts at 200° C. for 8 hrs. The mixture was diluted with methanol (10 mL), filtered and concentrated. Preparative RF-HPLC gave 117 mg of the title compound as an amber amorphous powder upon lyophilization. MS=528 (M-TFA+1); NMR (DMSO-$d_6$, ppm): 9.80 (br, 1H), 8.91 (s, 1H), 7.86 (m, 2H), 7.56 (s, 1H), 7.45 (t, J=7 Hz, 1H), 7.20 (d, J=7 Hz, 1H), 7.10 (t, J=7 Hz, 1H), 6.95 (q, J=5 Hz, 14 Hz, 2H), 6.69 (s, 1H), 6.46 (d, J=7 Hz, 1H), 3.87 (s, 3H), 3.80 (s, 3H), 3.50 (m, 4H), 2.83 (s, 3H), 2.91 (t, J=12 Hz, 2H), 2.70 (t, J=10 Hz, 2H), 2.33 (m, 1H), 2.13 (m, 2H), 1.89 (m, 1H), 1.65 (t, J=10 Hz, 2H).

Example 236

[2-Methoxy-4-(4-morpholin-4-yl-piperidin-1-yl)-phenyl]-[7-(2-methoxy-phenyl)-pyrrolo[2,1-f][1,2,4]triazin-2-yl]-amine 236a) 4-[1-(3-Methoxy-4-nitro-phenyl)-piperidin-4-yl]-morpholine: To a mixture of 4-piperidin-4-yl-morpholine (1.80 g, 10.6 mmol) and anhydrous powdered potassium carbonate (3.65 g, 26.4 mmol) in N,N-dimethylformamide (35 mL) was added 4-fluoro-2-methoxy-1-nitrobenzene (1.90 g, 11.1 mmol. The mixture was heated at 60° C. for 18 hours with stirring. The mixture was filtered and concentrated. The residue was dissolved in methylene chloride, washed with saturated aqueous sodium bicarbonate and brine, dried (MgSO4), filtered and concentrated. Flash chromatography over silica gel gave 3.12 g of the title compound as a yellow solid. MS=322 (M+1).

236b) 2-Methoxy-4-(4-morpholin-4-yl-piperidin-1-yl)-phenylamine: To a solution of 4-[1-(3-methoxy-4-nitro-phenyl)-piperidin-4-yl]-morpholine (1.50 g, 4.67 mmol) in ethyl acetate (50 mL) and ethanol (50 mL) in a Paar bottle was added 10% Pd—C catalyst (100 mg). The mixture was placed on a Paar shaker under 50 psi $H_2$ and shaken at room temperature for 90 minutes. The mixture was filtered and concentrated to afford 1.30 g of the title compound which was used without further purification. MS=292 (M+1).

236c) [2-Methoxy-4-(4-morpholin-4-yl-piperidin-1-yl)-phenyl]-[7-(2-methoxy-phenyl)-pyrrolo[2,1-f][1,2,4]triazin-2-yl]-amine: To a solution of 2-methoxy-4-(4-morpholin-4-yl-piperidin-1-yl)-phenylamine (230 mg, 0.79 mmol) and 2-methanesulfinyl-7-(2-methoxy-phenyl)-pyrrolo[2,1-f][1,2,4]triazine (151 mg, 0.53 mmol) in 2-methoxyethanol (1.5 mL) was added N,N-diisopropyl-ethylamine (183 uL, 1.05 mmol). The mixture was submitted to microwave irradiation at 300 watts, at 200° C. for 8 hrs. The mixture was diluted with methanol (10 mL), filtered and concentrated. Preparative RF-HPLC gave 140 mg of the title compound upon lyophillization. MS=515 (M+1); NMR (DMSO-$d_6$, ppm): 9.90 (br, 1H), 8.91 (s, 1H), 7.90 (d, J=8 Hz, 1H), 7.85 (d, J=8 Hz, 1H), 7.56 (s, 1H), 7.45 (t, J=7 Hz, 1H), 7.20 (d, J=7 Hz, 1H), 7.10 (t, J=7 Hz, 1H), 6.95 (q, J=5 Hz, 14 Hz, 2H), 6.73 (s, 1H), 6.46 (d, J=7 Hz, 1H), 4.03 (d, J=10 Hz, 2H), 3.87 (s, 3H), 3.80 (s, 3H), 3.70 (m, 2H), 3.50 (m, 2H), 3.36 (m, 1H), 3.13 (m, 2H), 2.73 (t, J=10 Hz, 2H), 2.16 (d. J=10 Hz, 2H), 2.13 (m, 2H), 1.76 (m, 2H).

Example 241

2-Methoxy-4-[4-(4-methyl-piperazin-1-yl)-piperidin-1-yl]-phenyl}-(7-pyridin-3-yl-pyrrolo[2,1-f][1,2,4]triazin-2-yl)-amine Palladium Acetate (0.009 g, 0.00004 mol) and Triphenylphosphine (0.013 g, 0.000050 mol) were dissolved in Tetrahydrofuran (4 mL, 0.05 mol) and the mixture was allowed to stir at room temperature for 10 minutes. (7-Bromo-pyrrolo[2,1-f][1,2,4]triazin-2-yl)-{2-methoxy-4-[4-(4-methyl-piperazin-1-yl)-piperidin-1-yl]-phenyl}-amine (0.10 g, 0.00020 mol) (For preparation see Example 242) was then added and the reaction was again allowed to stir for 10 minutes. 3-Pyridylboronic acid (0.034 g, 0.00028 mol) was added followed by 1 M of Sodium carbonate in Water (0.70 mL, 0.0007 mol) and Ethanol (2 mL, 0.03 mol). The reaction mixture was then heated at 80° C. overnight. The solvent was removed under vacuum. The product was worked up with brine and DCM. Purification by prep plate chromatography gave 2-Methoxy-4-[4-(4-methyl-piperazin-1-yl)-piperidin-1-yl]-phenyl}-(7-pyridin-3-yl-pyrrolo[2,1-f][1,2,4]triazin-2-yl)-amine as a tan solid (0.0565 g, 56%). MP: 68-70° C.; $^1$H-NMR (DMSO, 400 MHz) δ 9.30 (d, 1H, J=2.16 Hz), 8.95 (s, 1H), 8.56 (d, 1H, J=8.08 Hz), 8.52 (d, 1H, J=4.76 Hz), 7.89 (s, 1H), 7.64 (d, 1H, J=5.97Hz), 7.47 (q, 1H, J=4.76 Hz), 7.29 (d, 1H, J=4.80 Hz), 6.95 (d, 1H, J=4.80 Hz), 6.67 (d, 1H, J=2.36 Hz) 6.51 (q, 1H, J=2.48 Hz), 3.82 (s, 3H), 3.72 (d, 2H, J=12.48 Hz), 2.7 (t, 1H, J=11.44 Hz), 2.33-2.30 (m, 4H, J=10.32 Hz), 1.54 (q, 2H).

Example 242

4-(2-{2-Methoxy-4-[4-(4-methyl-piperazin-1-yl)-piperidin-1-yl]-phenylamino}-pyrrolo[2,1-f][1,2,4]triazin-7-yl)-N-methyl-benzamide 242a) A mixture of 2-Methoxy-4-[4-(4-methyl-piperazin-1-yl)-piperidin-1-yl]-phenylamine (1.25 g, 0.00411 mol) (For preparation see Example 251), 7-Bromo-2-methanesulfinyl-pyrrolo[2,1-f][1,2,4]triazine (0.75 g, 0.0029 mol) and N,N-Diisopropylethylamine (2.02 mL, 0.0116 mol) in 2-Methoxyethanol (10 mL, 0.1 mol) was heated in the microwave at 170° C. for 90 minutes. Purification by Isco chromatography gave (7-Bromo-pyrrolo[2,1-f][1,2,4]triazin-2-yl)-{2-methoxy-4-[4-(4-methyl-piperazin-1-yl)-piperidin-1-yl]-phenyl}-amine as a tan solid (0.36 g, 255). MP: 171-173° C.; LCMS (m/e) 500 (M); $^1$H-NMR (DMSO, 400 MHz) δ 8.83 (s, 1H), 8.02 (d, 1H, J=8.76 Hz), 7.74 (s, 1H), 6.89 (q, 2H, J=4.76 Hz), 6.67 (s, 1H), 6.51 (d, 1H, J=6.40 Hz), 3.85 (s, 3H), 3.70 (d, 2H, J=12.20 Hz), 2.64 (t, 2H, J=11.80 Hz), 2.31-2.28 (br s, 4H), 1.83 (s, 3H), 1.85 (m, 2H), 1.55-1.50 (m, 2H).

242b) Following a procedure similar to Example 241, (7-Bromo-pyrrolo[2,1-f][1,2,4]triazin-2-yl)-{2-methoxy-4-[4-(4-methyl-piperazin-1-yl)-piperidin-1-yl]-phenyl}-amine (0.10 g, 0.00020 mol) and 4-(N-Methylaminocarbonyl)phenylboronic acid (0.039 g, 0.00022 mol). Purification by Isco chromatography gave 4-(2-{2-Methoxy-4-[4-(4-methyl-piperazin-1-yl)-piperidin-1-yl]-phenylamino}-pyrrolo[2,1-f][1,2,4]triazin-7-yl)-N-methyl-benzamide as a tan solid (0.06 g, 50%). MP 112-114° C.; LCMS (m/e) 555 (M+1); $^1$H-NMR (DMSO, 400 MHz) δ 8.94 (s, 1H), 8.28 (d, 1H, J=8.53 Hz), 7.90 (d, 1H, J=8.52 Hz), 7.85 (s, 1H), 7.71 (d, 1H, J=8.68 Hz), 7.28 (d, 1H, J=4.80 Hz), 6.94 (d, 1H, J=4.80 Hz), 6.69 (d, 1H, J=2.40 Hz), 3.83 (s, 3H), 3.74 (d, 1H, J=2.00 Hz), 2.82 (d, 2H, J=4.52 Hz), 2.68 (m, 3H), 2.33 (m, 4H), 2.15 (s, 3H), 1.90-1.75 (m, 2H), 1.60-1.48 (m, 2H), 1.25 (s, 1H), 1.18 (br s, 2H).

Example 251

{2-Methoxy-4-[4-(4-methyl-piperazin-1-yl)-piperidin-1-yl]-phenyl}-[7-(2-methoxy-phenyl)-pyrrolo[2,1-f][1,2,4]triazin-2-yl]-amine 251a) To a suspension of 5-Fluoro-2-nitro-phenol (0.85 g, 0.0054 mol) and Potassium carbonate (1.6 g, 0.012 mol) in N,N-Dimethylformamide (10 mL, 0.1 mol) was added Dimethyl sulfate (0.56 mL, 0.0060 mol). The mixture was allowed to stir at room temperature for 18 hours. To the yellow suspension was added 1-Methyl-4-piperidin-4-yl-piperazine (1.0 g, 0.0054 mol). The suspension was stirred at room temperature for 1 hour. Reaction mixture was heated to 60° C. for 18 hours. The reaction was monitored by HPLC. The mixture was allowed to cool to room temperature then cooled to 0°-5° C. in a ice/salt/water bath. To the vigorously stirring mixture was added aqueous saturated sodium chloride and stirred for 1 hour. The mixture was filtered and rinsed with a minimum of cold aqueous saturated sodium chloride. The yellow filter cake was dissolved in methanol and evaporated to dryness. The yellow solids were partially dissolved in dichloromethane (100 ml), filtered, dried over magnesium sulfate, filtered and evaporated to yield yellow solids. The solids were triturated with ether (30 mL) with stirring for 72 hours. The solids were filtered, rinsed with ether and dried by suction. 1-[1-(3-Methoxy-4-nitro-phenyl)-piperidin-4-yl]-4-methyl-piperazine was recovered as a yellow solid (0.95 g). mp=140-143° C. $^1$H NMR (400 MHz, CDCl3, δ, ppm): 8.00 (d, 1H, J=9.3 Hz), 6.42 (dd, 1H, J=9.5 Hz and 1.6 Hz), 6.32-6.29 (m, 1H), 3.98-3.91 (m, 5H), 3.02-2.95 (m, 2H), 2.70-2.55 (m, 4H), 2.55-2.40 (m, 5H), 2.29 (s, 3H), 2.01-1.93 (m, 2H), 1.68-1.56 (m, 2H). LC/MS=335.20 (MH)+

251b) To a Paar bottle (250 mL) was added 10% Palladium on Carbon (50% Wet) followed by a solution of 1-[1-(3-Methoxy-4-nitro-phenyl)-piperidin-4-yl]-4-methyl-piperazine (0.90 g, 0.0027 mol) in 2:1 Ethyl acetate:Methanol (100 mL). The mixture was degassed and charged with Hydrogen (50 psi). The reaction was shaken until equilibrium had been reached. A total of 25 psi of Hydrogen was adsorbed. The mixture was degassed and kept under an atmosphere of Nitrogen. The suspension was filtered through a plug of diatomaceous earth and rinsed with dichloromethane. The filtrate was evaporated to yield a light purple solid 2-Methoxy-4-[4-(4-methyl-piperazin-1-yl)-piperidin-1-yl]-phenylamine. (0.82 g). mp=94-99° C. $^1$H NMR (400 MHz, CDCl3, δ, ppm): 6.63 (d, 1H, J=8.3 Hz), 6.52 (d, 1H, J=1.5 Hz), 6.44-6.39 (m, 1H), 3.83 (s, 3H), 3.75-3.25 (m, 4H), 2.80-2.25 (m, 14H), 1.96-1.87 (m, 2H), 1.78-1.65 (m, 2H). LC/MS=305.16 (MH)+

251c) A solution of 2-Methoxy-4-[4-(4-methyl-piperazin-1-yl)-piperidin-1-yl]-phenylamine (0.18 g, 0.00059 mol) with 2-methanesulfinyl-7-(2-methoxy-phenyl)-pyrrolo[2,1-f][1,2,4]triazine (85 mg, 0.30 mol) and N,N-diisopropylethylamine (0.057 g, 0.44 mmol) in 2-methoxyethanol (1.0 mL, 0.013 mol) in a microwave vessel was microwaved on 300 watts, 180° C. for 30 minutes. Repeated microwave for 30 minutes more to get to completion. Filtered through 0.45μ filter and purified by reverse phase HPLC. Concentrated and dissolved in DCM/MeOH and free-based with solid MP-carbonate. Filtered and concentrated {2-methoxy-4-[4-(4-methyl-piperazin-1-yl)-piperidin-1-yl]-phenyl}-[7-(2-methoxy-phenyl)-pyrrolo[2,1-f][1,2,4]triazin-2-yl]-amineisolated as a brownish film (12 mg, 8%). $^1$H-NMR (CDCl$_3$) δ 8.69 (s, 1H), 8.24 (d, J=8.8 Hz, 1H), 8.03 (d, J=7.6 Hz, 1H), 7.44 (t, J=8.0, 1H), 7.31 (s, 1H), 7.14 (t, J=7.5, 1H), 7.08 (d, J=8.0, 1H), 7.03 (d, J=4.7 Hz, 1H), 6.83 (d, J=4.6 Hz, 1H), 6.57-6.45 (m, 1H), 6.46-6.43 (m, 1H), 3.89 (s, 3H), 3.62 (s, 3H), 3.64 (broad d, J=12.3 Hz, 2H), 2.72-2.66 (m, 4H), 2.55-2.51 (broad m, 3H), 1.97 (broad d, J=12.4 Hz, 2H), 1.78-1.72 (m, 2H), 1.32-1.20 (m, 2H), 0.94-0.85 (m, 2H); LC/MS (ESI+): 528 (M+H).

Example 252

[4-(4-Ethyl-morpholin-2-yl)-phenyl]-[7-(2-methoxy-phenyl)-pyrrolo[2,1-f][1,2,4]triazin-2-yl]-amine 252a) Combined 2-Bromo-1-(4-nitro-phenyl)-ethanone (5.0 g, 0.020 mol) with Methylene chloride (100 mL, 2 mol) and treated with 2-Ethylamino-ethanol (2.0 mL, 0.020 mol) and N,N-Diisopropylethylamine (3.6 mL, 0.021 mol), stirred at rt, 3 h. Treated the mixture with Triethylsilane (10.33 mL, 0.06468 mol) and then Trifluoroacetic Acid (52.5 mL, 0.681 mol) and heated to 40° C. and stirred under nitrogen overnight. Concentrated and partitioned between ice/water and heptane, stirred vigorously for 10 min. Decanted off the heptane to remove silyl byproducts, repeated. Basified with solid K2CO3. Extracted with EtOAc, the organics were washed with brine, dried (MgSO4), filtered and concentrated onto Celite and purified by ISCO chromatography (80 g, SiO2, gradient elution: 100% Hex to 100% EtOAc to 10% MeOH/EtOac), (+/−)-4-Ethyl-2-(4-nitro-phenyl)-morpholine was isolated as red waxy solid (2.45 grams). $^1$H-NMR (CDCl$_3$) δ 8.22 (d, J=8.8 Hz, 2H), 7.76 (d, J=8.8 Hz, 2H), 4.69 (dd, J=10.5, 2.3 Hz, 1H), 4.10 (dd, J=11.5, 2.0, 1H), 3.90-3.84 (m, 1H), 4.11-4.08 (m, 1H), 3.00 (d, J=11.5 Hz, 1H), 2.87 (d, J=9.9 Hz, 1H), 2.48 (dd, J=7.2, 14.4 Hz, 2H), 2.27-2.20 (m, 1H), 1.99 (t, J=10.7 Hz, 1H), 1.13 (t, J=7.2 Hz, 3H); LC/MS (ESI+): 237 (M+H).

252b) Combined 4-Ethyl-2-(4-nitro-phenyl)-morpholine (3.00 g, 0.0127 mol) with Methanol (300 mL, 6 mol) and add Ammonium formate (5.6 g, 0.089 mol) then 10% Pd/C, 50% wet (0.88 g, 0.00041 mol). Stir under N2 overnight. Filtered through Celite and concentrated. Partitioned between aq. Na2CO3 and EtOAc, the organics were dried (MgSO4), filtered. To give 4-(4-Ethyl-morpholin-2-yl)-phenylamine as yellowish oil which solidified upon standing (2.45 grams). $^1$H-NMR (CDCl$_3$) δ 7.17 (d, J=8.4 Hz, 2H), 6.68-6.65 (m, 2H), 4.47 (dd, J=10.4, 2.3 Hz, 1H), 4.05-4.01 (m, 1H), 3.90-3.84 (m, 1H), 3.84 (dt, J=11.6, 2.4 Hz, 1H), 3.66 (broad s, 2H), 2.94-2.90 (m, 1H), 2.84-2.81 (m, 1H), 2.46 (q, J=7.2, 2H), 2.2 (dt, J=8.1, 11.5 Hz, 1H), 2.05 (t, J=11.0 Hz, 1H), 1.12 (t, J=7.2 Hz, 1H); LC/MS (ESI+): 207 (M+H).

252c) Following a procedure analogous to 251c, 4-(4-Ethyl-morpholin-2-yl)-phenylamine (0.13 g, 0.626 mmol) and 2-methanesulfinyl-7-(2-methoxy-phenyl)-pyrrolo[2,1-f][1,2,4]triazine (90 mg, 0.31 mol) were converted to [4-(4-Ethyl-morpholin-2-yl)-phenyl]-[7-(2-methoxy-phenyl)-pyrrolo[2,1-f][1,2,4]triazin-2-yl]-amine (25.42 mgs) as a TFA salt. $^1$H-NMR (CDCl$_3$) δ 8.91 (s, 1H), 8.64 (s, 2H), 8.06 (d, J=2.6 Hz, 1H), 7.68 (d, J=8.6 Hz, 2H), 7.48-7.45 (m, 1H), 7.35 (d, J=8.6 Hz, 2H), 7.25 (d, J=5.0 Hz, 1H), 7.08 (d, J=5.0 Hz, 1H), 7.05 (d, J=8.9 Hz, 1H), 4.94 (d, J=9.3, 1H), 4.22 (d, J=7.4 Hz, 2H), 3.87 (s, 3H), 3.65 (t, J=10.7 Hz, 2H), 3.22-3.13 (m, 2H), 2.90-2.85 (m, 1H), 2.65-2.60 (m, 1H), 1.41 (t, J=7.3 Hz, 3H); LC/MS (ESI+): 430.16 (M+H).

Example 253

[7-(5-Chloro-2-methoxy-phenyl)-pyrrolo[2,1-f][1,2,4]triazin-2-yl]-[4-(4-ethyl-morpholin-2-yl)-phenyl]-amine 253a) Following a procedure analogous to 251c, 4-(4-Ethyl-morpholin-2-yl)-phenylamine (0.10 g, 0.51 mmol) and 7-(5-Chloro-2-methoxy-phenyl)-2-methanesulfinyl-pyrrolo[2,1-f][1,2,4]triazine (66 mg, 0.20 mol) were converted to [7-(5-Chloro-2-methoxy-phenyl)-pyrrolo[2,1-f][1,2,4]triazin-2-yl]-[4-(4-ethyl-morpholin-2-yl)-phenyl]-amine (28.36 mgs) as a TFA salt. $^1$H-NMR (CDCl$_3$) δ 9.67 (s, 1H), 8.58 (s, 2H), 7.96 (d, J=7.7 Hz, 1H), 7.71 (d, J=8.6 Hz, 2H), 7.57 (t, J=8.4 Hz 1H), 7.25-7.21 (m, 2H), 7.19-7.14 (m, 2H), 4.93 (d, J=9.5, 1H), 4.22 (d, J=7.4 Hz, 2H), 3.88 (s, 3H), 3.64

(t, J=12.8 Hz, 2H), 3.22-3.12 (m, 2H), 2.90-2.85 (m, 1H), 2.65-2.60 (m, 1H), 1.41 (t, J=7.3 Hz, 3H); LC/MS (ESI+): 464.11 (M+H).

Example 261

(4-Morpholin-4-yl-phenyl)-[1,2,4]triazino[1,6-a]indol-2-yl-amine

261a) A 2 M solution of sodium hypochlorite in water (200 mL, 0.40 mol) was added dropwise to a biphasic mixture of commercially available 1H-indole-2-carboxylic acid methyl ester (20.00 g, 0.11 mol), capriquat (4.5 mL, 0.01 mol), 7 M of sodium hydroxide in water (326 mL, 2.28 mol), 8 M of ammonium hydroxide in water (100 mL, 0.80 mol), ammonium chloride (37 g, 0.68 mmol), and 2-methoxy-2-methylpropane (318 mL). The reaction was worked up about 20 min after the addition was completed. The organic layer was separated and was washed with saturated aqueous sodium thiosulfate. Organic extracts were dried over magnesium sulfate, then filtered, and the solvent was evaporated in vacuum to afford 1-amino-1H-indole-2-carboxylic acid methyl ester (18.56 g, 85%), which was used in the next step without further purification. $^1$H-NMR (CDCl$_3$) δ 7.62 (m, 2H), 7.36 (m, 1H), 7.18 (s, 1H), 7.13 (s, 1H), 5.32 (br s, 2H), 3.93 (s, 3H).

261b) 1-Amino-1H-indole-2-carboxylic acid methyl ester (18.56 g, 0.098 mol) was dissolved in tetrahydrofuran (800 mL). Benzoyl isothiocyanate (13.1 mL, 0.098 mol) was added and the reaction was allowed to stir overnight. The solvent was removed in vacuum and the solid residue was triturated with ether. The solid was collected by filtration to yield the 1-(3-benzoyl-thioureido)-1H-indole-2-carboxylic acid methyl ester (24.27 g, 70%), which was used in the next step without further purification. $^1$H-NMR (CDCl$_3$) δ 12.81 (br s, 1H), 9.29 (br s, 1H), 7.95 (d, J=7.2 Hz, 2H), 7.68 (m, 2H), 7.57 (m, 2H), 7.42 (m, 2H), 7.38 (s, 1H), 7.24 (m, 1H), 3.89 (s, 3H).

261c) Into a 1 L beaker, 1-(3-benzoyl-thioureido)-1H-indole-2-carboxylic acid methyl ester (24.27 g, 0.07 mol) and a 2 M solution of sodium hydroxide in water (140 mL, 0.28 mol) were added. The mixture was heated at 85° C. for 75 minutes. The reaction was cooled to room temperature. Acetic acid (16.7 mL, 0.29 mol) was added at 0° C. and the mixture was stirred for 30 minutes. The solid was filtered and dried on filter overnight to afford a white solid, which was further dried under vacuum overnight. NMR indicated about 1:1 molar ratio of product to benzoic acid. Trituration and filtration from hot benzene removed the benzoic acid and afforded 2-thioxo-2,3-dihydro-1H-[1,2,4]triazino[1,6-a]indol-4-one (14.50 g, 96%), which was used in the next step without further purification. $^1$H-NMR (DMSO-d$_6$) δ 10.29 (br s, 1H), 7.76 (d, J=8.4 Hz, 1H), 7.66 (d, J=8.1 Hz, 1H), 7.3 (br s, 1H), 7.27 (m, 1H), 7.12 (m, 1H), 6.88 (s, 1H).

261d) Into a round-bottom flask 2-thioxo-2,3-dihydro-1H-[1,2,4]triazino[1,6-a]indol-4-one (9.25 g, 0.04 mol) and methyl iodide (3.42 mL, 0.0549 mol) were combined in tetrahydrofuran (200 mL). The reaction was stirred at 45° C. for one hour. The solvent was removed under vacuum to give a solid, which was next stirred for 30 minutes with saturated aqueous NaHCO$_3$ (100 mL). The solid was filtered and washed with water, then dried on high vacuum and further by azeotrop distillation with toluene to give 2-methylsulfanyl-3H-[1,2,4]triazino[1,6-a]indol-4-one (7 g, 71%), which was used in the next step without further purification. $^1$H-NMR (DMSO-d$_6$) δ 12.28 (br s, 1H), 7.87 (d, J=8.4 Hz, 1H), 7.80 (d, J=8.1 Hz, 1H), 7.43 (m, 1H), 7.28 (m, 1H), 7.18 (s, 1H), 2.64 (s, 3H).

261e) A mixture of 2-methylsulfanyl-3H-[1,2,4]triazino[1,6-a]indol-4-one (3.00 g, 13.0 mmol), phosphoryl chloride (6.04 mL, 64.8 mmol), and N,N-diethylaniline (4.0 mL, 25.0 mmol) was allowed to sit for 30 min at room temperature and then refluxed for 1 hour. The mixture was then concentrated and the residue was azeotroped with toluene, cooled, and poured over ice. The resulting mixture was transferred to a separation funnel and the product was extracted in ether with 10-20% dichloromethane. The combined organic extracts were washed with dilute and cold aqueous HCl. then with dilute cold NaHCO$_3$, and finally with cold water, dried over magnesium sulfate and concentrated. The product was purified by flash chromatography (ISCO, Silicagel, EtOAc/Hexanes 10-15%) to provide 4-chloro-2-methylsulfanyl-[1,2,4]triazino[1,6-a]indole (2.30 g, 71%). $^1$H-NMR (CDCl$_3$) δ 8.11 (d, J=8.5 Hz, 1H), 7.86 (d, J=8.2 Hz, 1H), 7.49 (m, 1H), 7.41 (m, 1H), 7.14 (s, 1H), 2.68 (s, 3H); LC/MS (ESI+): 250.5 (M+H).

261f) 4-Chloro-2-methylsulfanyl-[1,2,4]triazino[1,6-a]indole (1.00 g, 4.00 mmol) was suspended in isopropyl alcohol (13 mL) at room temperature. Sodium borohydride (0.318 g, 8.41 mmol) was added and the reaction mixture was heated at 55° C. for 3 hours. The reaction was allowed to cool to room temperature, then aqueous NaHCO$_3$/dichloromethane extraction work-up, drying and evaporation of solvent afforded 2-methylsulfanyl-3,4-dihydro-[1,2,4]triazino[1,6-a]indole. $^1$H-NMR (CDCl$_3$) δ 7.63 (d, J=8.1 Hz, 1H), 7.52 (d, J=8.0 Hz, 1H), 7.18 (m, 1H), 7.08 (m, 1H), 6.15 (s, 1H), 4.73 (s, 2H), 4.63 (br s, 1H), 2.60 (s, 3H); LC/MS (ESI+): 218.5 (M+H). Benzene (30 mL) was added, and the solution was treated with manganese(IV) oxide (1.39 g, 16.0 mmol). The reaction mixture was stirred overnight. The solids were removed by filtration through Celite and were washed with dichloromethane. The solvent was removed under vacuum to afford 2-methylsulfanyl-[1,2,4]triazino[1,6-a]indole (0.79 g, 92% over two steps), which was used in the next step without further purification. $^1$H-NMR (CDCl$_3$) δ 9.05 (s, 1H), 8.15 (dd, J=8.5, 0.8 Hz, 1H), 7.86 (d, J=8.2 Hz, 1H), 7.47 (m, 1H), 7.39 (m, 1H), 6.99 (s, 1H), 2.68 (s, 3H); LC/MS (ESI+): 216.5 (M+H).

261g) Into a round-bottom flask, m-chloroperbenzoic acid (77% by weight in benzoic acid, 853 mg, 3.80 mmol) was added to a solution of 2-methylsulfanyl-[1,2,4]triazino[1,6-a]indole (780 mg, 3.60 mmol) in dichloromethane (20 mL), at 0° C. The reaction was stirred for 1 hour at room temperature. Saturated NaHCO$_3$ in water was added and the reaction mixture was stirred for 30 minutes. The organic phase was separated, washed with brine, and dried over magnesium sulfate, then filtered. The solvent was removed under vacuum to afford 2-methanesulfinyl-[1,2,4]triazino[1,6-a]indole (820 mg, 98%) as an orange solid, which was used without further purification. $^1$H-NMR (CDCl$_3$) δ 9.28 (s, 1H), 8.34 (d, J=8.5 Hz, 1H), 7.95 (d, J=8.1 Hz, 1H), 7.60 (m, 1H), 7.52 (m, 1H), 7.21 (s, 1H), 3.06 (s, 3H); LC/MS (ESI+): 254.5 (M+Na).

261h) Into a 30 ml vial 2-methanesulfinyl-[1,2,4]triazino[1,6-a]indole (50.00 mg, 0.216 mol), 4-(4-morpholino)aniline (84.8 mg, 0.476 mol), and N-methylpyrrolidinone (0.10 mL) were combined and heated at 145° C. for 2 hours. The reaction was cooled to room temperature and the product was isolated by flash chromatography (ISCO, Silicagel, methanol/dichloromethane 0-10%) to provide (4-morpholin-4-yl-phenyl)-[1,2,4]triazino[1,6-a]indol-2-yl-amine as a brown solid (14 mg, 19%). MP: 205-210° C.; $^1$H-NMR (CDCl$_3$) δ 9.00 (s, 1H), 8.10 (d, J=8.5 Hz, 1H), 7.81 (d, J=8.4

Hz, 1H), 7.68 (d, J=8.8 Hz, 2H), 7.42 (m, 1H), 7.31 (m, 1H), 6.99 (d, J=8.8 Hz, 2H), 6.94 (s, 1H), 6.80 (s, 1H), 3.89 (m, 4H), 3.16 (m, 4H); LC/MS (ESI+): 346.7 (M+H).

Example 262

{2-Methoxy-4-[4-(4-methyl-piperazin-1-yl)-piperidin-1-yl]-phenyl}-[1,2,4]triazino[1,6-a]indol-2-yl-amine 2-Methanesulfinyl-[1,2,4]triazino[1,6-a]indole (50.00 mg, 0.216 mmol), prepared as in example 261g, 2-methoxy-4-[4-(4-methyl-piperazin-1-yl)-piperidin-1-yl]-phenylamine (132 mg, 0.432 mmol), and 2-methoxyethanol (0.7 mL) were combined in a microwave tube and the reaction mixture was microwaved on 300 watts, at 180° C. for 90 minutes. The reaction was cooled to room temperature and the product was isolated by preparative reverse phase hplc (Gilson, 0.1% TFA water/acetonitrile gradient) to afford {2-methoxy-4-[4-(4-methyl-piperazin-1-yl)-piperidin-1-yl]-phenyl}-[1,2,4]triazino[1,6-a]indol-2-yl-amine as a red solid (34 mg, 33%). MP: 176-179° C.; $^1$H-NMR (CDCl$_3$) δ 9.00 (s, 1H), 8.51 (d, J=8.8 Hz, 1H), 8.13 (d, J=8.5 Hz, 1H), 7.81 (d, J=8.4 Hz, 1H), 7.42 (m, 1H), 7.40 (s, 1H), 7.31 (m, 1H), 6.92 (s, 1H), 6.68 (dd, J=8.4, 2.5 Hz, 1H), 6.61 (d, J=2.5 Hz, 1H), 3.92 (s, 3H), 3.69 (m, 2H), 2.77-2.33 (m, 10H), 2.32 (s, 3H), 1.97 (m, 2H), 1.74 (m, 3H); LC/MS (ESI+): 472.15 (M+H).

Example 263

[4-(4-Methyl-piperazin-1-yl)-phenyl]-[1,2,4]triazino[1,6-a]indol-2-yl-amine

Following a procedure similar to example 262, 2-methanesulfinyl-[1,2,4]triazino[1,6-a]indole and 4-(4-methyl-piperazin-1-yl)-phenylamine were converted to [4-(4-methyl-piperazin-1-yl)-phenyl]-[1,2,4]triazino[1,6-a]indol-2-yl-amine as a mustard yellow solid (40 mg, 51%). MP: 217-222° C.; $^1$H-NMR (CDCl$_3$) δ 8.98 (s, 1H), 8.09 (d, J=8.5 Hz, 1H), 7.80 (d, J=8.2 Hz, 1H), 7.66 (d, J=8.5 Hz, 2H), 7.41 (m, 1H), 7.30 (s, 1H), 7.00 (d, J=8.5 Hz, 2H), 6.92 (s, 1H), 6.84 (s, 1H), 3.21 (m, 4H), 2.62 (m, 4H), 2.38 (s, 3H); LC/MS (ESI+): 359.7 (M+H).

Example 264

{4-[4-(4-Methyl-piperazin-1-yl)-piperidin-1-yl]-phenyl}-[1,2,4]triazino[1,6-a]indol-2-yl-amine Following a procedure similar to example 262, 2-methanesulfinyl-[1,2,4]triazino[1,6-a]indole and 4-[4-(4-methyl-piperazin-1-yl)-piperidin-1-yl]-phenylamine were converted to {4-[4-(4-methyl-piperazin-1-yl)-piperidin-1-yl]-phenyl}-[1,2,4]triazino[1,6-a]indol-2-yl-amine as an orange solid (41 mg, 43%). MP: 226-229° C.; $^1$H-NMR (CDCl$_3$) δ 8.95 (s, 1H), 8.10 (d, J=8.4 Hz, 1H), 7.80 (d, J=8.4 Hz, 1H), 7.64 (m, 2H), 7.41 (m, 1H), 7.30 (m, 1H), 7.00 (m, 2H), 6.92 (s, 1H), 6.80 (s, 1H), 3.70 (m, 2H), 2.68 (m, 6H), 2.50 (m, 3H), 2.38 (m, 1H), 2.31 (s, 3H), 1.97 (m, 3H), 1.72 (m, 2H); LC/MS (ESI+): 442.9 (M+H).

Example 265

5,5-Dimethyl-8-([1,2,4]triazino[1,6-a]indol-2-ylamino)-1,3,4,5-tetrahydro-benzo[b]azepin-2-one Following a procedure similar to example 262, 2-methanesulfinyl-[1,2,4]triazino[1,6-a]indole and 8-amino-5,5-dimethyl-1,3,4,5-tetrahydro-benzo[b]azepin-2-one were converted to 5,5-dimethyl-8-([1,2,4]triazino[1,6-a]indol-2-ylamino)-1,3,4,5-tetrahydro-benzo[b]azepin-2-one as a brown solid (19 mg, 24%). MP: 230-240° C.; $^1$H-NMR (CDCl$_3$) δ 9.04 (s, 1H), 8.10 (d, J=8.4 Hz, 1H), 7.82 (d, J=8.4 Hz, 1H), 7.64 (d, J=2.2 Hz, 1H), 7.56 (s, 1H), 7.44 (m, 2H), 7.35 (m, 2H), 7.05 (s, 1H), 6.96 (s, 1H), 2.47 (m, 2H), 2.14 (m, 2H), 1.44 (s, 6H); LC/MS (ESI+): 372.7 (M+H).

Example 266

(2-Methoxy-4-morpholin-4-yl-phenyl)-[1,2,4]triazino[1,6-a]indol-2-yl-amine

Following a procedure similar to example 262, 2-methanesulfinyl-[1,2,4]triazino[1,6-a]indole and 2-methoxy-4-morpholin-4-yl-phenylamine were converted to (2-methoxy-4-morpholin-4-yl-phenyl)-[1,2,4]triazino[1,6-a]indol-2-yl-amine as a brown solid (32 mg, 39%). MP: 169-173° C.; $^1$H-NMR (CDCl$_3$) δ 9.01 (s, 1H), 8.55 (d, J=8.8 Hz, 1H), 8.13 (d, J=8.4 Hz, 1H), 7.82 (d, J=8.4 Hz, 1H), 7.42 (m, 2H), 7.31 (m, 1H), 6.93 (s, 1H), 6.67 (d, J=8.8; 2.4 Hz, 1H), 6.59 (d, J=2.4 Hz, 1H), 3.93 (s, 3H), 3.90 (m, 4H), 3.16 (m, 4H); LC/MS (ESI+): 376.7 (M+H).

Example 267

[2-Methoxy-4-(4-methyl-piperazin-1-yl)-phenyl]-[1,2,4]triazino[1,6-a]indol-2-yl-amine Following a procedure similar to example 262, 2-methanesulfinyl-[1,2,4]triazino[1,6-a]indole and 2-methoxy-4-(4-methyl-piperazin-1-yl)-phenylamine were converted to [2-methoxy-4-(4-methyl-piperazin-1-yl)-phenyl]-[1,2,4]triazino[1,6-a]indol-2-yl-amine as an orange solid (19 mg, 23%). MP: 150-153° C.; $^1$H-NMR (CDCl$_3$) δ 9.00 (s, 1H), 8.54 (d, J=8.8 Hz, 1H), 8.13 (d, J=8.5 Hz, 1H), 7.81 (d, J=8.4 Hz, 1H), 7.41 (m, 2H), 7.31 (m, 1H), 6.92 (s, 1H), 6.69 (dd, J=8.4; 2.5 Hz, 1H), 6.60 (d, J=2.5 Hz, 1H), 3.92 (s, 3H), 3.22 (m, 4H), 2.63 (m, 4H), 2.38 (s, 3H); LC/MS (ESI+): 389.8 (M+H).

Example 268

(7-Methoxy-[1,2,4]triazino[1,6-a]indol-2-yl)-(4-morpholin-4-yl-phenyl)-amine

2-Methanesulfinyl-7-methoxy-[1,2,4]triazino[1,6-a]indole was prepared from commercially available 5-methoxy-1H-indole-2-carboxylic acid ethyl ester by a reaction sequence similar to example 261a-g and then reacted with 4-(4-morpholino)aniline by a procedure similar to example 262 to provide (7-methoxy-[1,2,4]triazino[1,6-a]indol-2-yl)-(4-morpholin-4-yl-phenyl)-amine as a yellow solid (19 mg, 26%). MP: 228-233° C.; $^1$H-NMR (CDCl$_3$) δ 8.94 (s, 1H), 8.00 (d, J=8.8 Hz, 1H), 7.66 (d, J=8.8 Hz, 2H), 7.11 (s, 1H), 7.09 (m, 1H), 6.99 (d, J=8.8 Hz, 2H), 6.84 (s, 1H), 6.73 (s, 1H), 3.90 (s, 3H), 3.89 (m, 4H), 3.15 (m, 4H); LC/MS (ESI+): 376.7 (M+H).

Example 269

(2-Methoxy-4-morpholin-4-yl-phenyl)-(7-methoxy-[1,2,4]triazino[1,6-a]indol-2-yl)-amine Following a procedure similar to example 268, 2-methanesulfinyl-7-methoxy-[1,2,4]triazino[1,6-a]indole and 2-methoxy-4-morpholin-4-yl-phenylamine were converted to (2-Methoxy-4-morpholin-4-yl-phenyl)-(7-methoxy-[1,2,4]triazino[1,6-a]indol-2-yl)-amine as an orange solid (14 mg, 18%). MP: 152-164° C.; $^1$H-NMR (CDCl$_3$) δ 8.94 (s, 1H), 8.51 (d, J=8.8 Hz, 1H), 8.03 (d, J=9.2 Hz, 1H), 7.38 (s, 1H), 7.11 (s, 1H), 7.10 (m, 1H), 6.82 (s, 1H), 6.65 (m, 1H), 6.58 (d, J=2.4 Hz, 1H), 3.92 (s, 3H), 3.90 (s, 3H), 3.90 (m, 4H), 3.16 (m, 4H); LC/MS (ESI+): 406.7 (M+H).

Example 270

Phenyl-[1,2,4]triazino[1,6-a]indol-2-yl-amine

Following a procedure similar to example 262, 2-methanesulfinyl-[1,2,4]triazino[1,6-a]indole and aniline were converted to phenyl-[1,2,4]triazino[1,6-a]indol-2-yl-amine as an orange solid (20 mg, 35%). MP: 188-193° C.; $^1$H-NMR (CDCl$_3$) δ 9.04 (s, 1H), 8.15 (d, J=8.5 Hz, 1H), 7.83 (d, J=8.2 Hz, 1H), 7.77 (d, J=8.00 Hz, 2H), 7.43 (m, 3H), 7.33 (m, 1H), 7.08 (m, 1H), 6.97 (s, 1H), 6.91 (s, 1H); LC/MS (ESI+): 261.6 (M+H).

Example 271

(3-Chloro-phenyl)-[1,2,4]triazino[1,6-a]indol-2-yl-amine

Following a procedure similar to example 262, 2-methanesulfinyl-[1,2,4]triazino[1,6-a]indole and m-chloroaniline were converted to (3-chloro-phenyl)-[1,2,4]triazino[1,6-a]indol-2-yl-amine as a yellow/brown solid (5.44 mg, 9%). MP: 174-176° C.; $^1$H-NMR (CDCl$_3$) δ 9.03 (s, 1H), 8.12 (d, J=8.6 Hz, 1H), 7.99 (m, 1H), 7.84 (d, J=8.2 Hz, 1H), 7.49 (m, (m, 2H), 7.33 (m, 2H), 7.02 (d, J=8.6 Hz, 1H), 6.98 (m, 1H), 6.93 (s, 1H); LC/MS (ESI+): 295.6 (M+H).

Example 272

(3-Methoxy-phenyl)-[1,2,4]triazino[1,6-a]indol-2-yl-amine

Following a procedure similar to example 262, 2-methanesulfinyl-[1,2,4]triazino[1,6-a]indole and m-methoxyaniline were converted to (3-methoxy-phenyl)-[1,2,4]triazino[1,6-a]indol-2-yl-amine as a yellow solid (19 mg, 30%). MP: 191-193° C.; $^1$H-NMR (CDCl$_3$) δ 9.04 (s, 1H), 8.12 (d, J=8.5 Hz, 1H), 7.83 (d, J=8.3 Hz, 1H), 7.65 (m, 1H), 7.45 (m, 1H), 7.32 (m, 2H), 7.17 (m, 1H), 6.97 (s, 1H), 6.91 (s, 1H), 6.64 (dd, J=8.3, 2.4 Hz, 1H), 3.93 (s, 3H); LC/MS (ESI+): 291.6 (M+H).

Example 273

N,N-Dimethyl-3-([1,2,4]triazino[1,6-a]indol-2-ylamino)-benzenesulfonamide

Following a procedure similar to example 262, 2-methanesulfinyl-[1,2,4]triazino[1,6-a]indole and 3-amino-N,N-dimethyl-benzenesulfonamide were converted to N,N-dimethyl-3-([1,2,4]triazino[1,6-a]indol-2-ylamino)-benzenesulfonamide as a yellow/brown solid (5 mg, 6%). MP: 191-193° C.; $^1$H-NMR (CDCl$_3$) δ 9.07 (s, 1H), 8.58 (s, 1H), 8.16 (d, J=8.6 Hz, 1H), 7.85 (d, J=8.3 Hz, 1H), 7.77 (dd, J=8.2, 1.6 Hz, 1H), 7.55 (m, 1H), 7.48 (m, 2H), 7.36 (m, 1H), 7.11 (s, 1H), 7.01 (s, 1H), 2.80 (s, 6H); LC/MS (ESI+): 368.7 (M+H).

Example 301

N-{2-Isopropyl-5-[7-(2-methoxy-phenyl)-pyrrolo[2,1-f][1,2,4]triazin-2-ylamino]-phenyl}-acetamide 301a. 2-Isopropyl-5-nitro-phenylamine: 2-Isopropylaniline (1.0 g, 0.0074 mol) was dissolved in Sulfuric acid (10.0 mL, 0.188 mol) at −5° C. Potassium nitrate (0.75 g, 0.0074 mol) was then added keeping the temperature below 0° C. The reaction was then allowed to stir gradually warming to room temperature until HPLC showed consumption of starting material. The mixture was then poured over water and the solid product was collected via filtration. The filtrate was then neutralized with 2M sodium hydroxide and the product was extracted with ethyl acetate. Combined organic extracts were dried over sodium sulfate, filtered and reduced to afford 1.10 grams of 2-Isopropyl-5-nitro-phenylamine. $^1$H NMR (400 MHz, DMSO, d$_6$) δ 7.56 (s, 1H), 7.46 (dd, 1H, J=2.40, 6.04 Hz), 7.30 (d, 1H, J=8.52 Hz), 5.63 (s, 2H), 3.05 (sept., 1H, J=6.76 Hz), 1.17 (d, 6H, J=6.76 Hz).

301b. N-(2-Isopropyl-5-nitro-phenyl)-acetamide: 2-Isopropyl-5-nitro-phenylamine (1.00 g, 0.00555 mol) was dissolved in Methylene chloride (20 mL, 0.3 mol) and the solution was treated with Triethylamine (1.16 mL, 0.00832 mol). After stirring at room temperature for 10 minutes, Acetyl chloride (0.436 g, 0.00555 mol) was added and the reaction was allowed to stir overnight at room temperature. The reaction mixture was poured over saturated sodium bicarbonate, and organics were extracted with ethyl acetate/dichloromethane. Combined organics were dried over sodium sulfate, filtered and reduced en vacuo to afford 1.35 grams of N-(2-Isopropyl-5-nitro-phenyl)-acetamide without further purification. $^1$H NMR (400 MHz, DMSO, d$_6$) δ 9.65 (s, 1H), 8.29 (s, 1H), 8.00 (dd, 1H, J=2.44, 6.20 Hz), 7.61 (d, 1H, J=8.69 Hz), 3.30 (sept., 1H, J=6.85 Hz), 2.12 (s, 3H), 1.17 (d, 6H, J=6.80 Hz).

301c. N-(5-Amino-2-isopropyl-phenyl)-acetamide: N-(2-Isopropyl-5-nitro-phenyl)-acetamide (1.23 g, 0.00553 mol) was dissolved in Methanol (40 mL, 1 mol) and the solution was carefully added to 10% Palladium on Carbon (0.500 g, 0.0375 mol) in a Parr vessel under nitrogen. The mixture was then placed on a Parr apparatus and was allowed to stir until uptake of hydrogen had ceased (−3 hours). The catalyst was then removed via filtration and the filtrate was reduced to afford 1.00 grams N-(5-Amino-2-isopropyl-phenyl)-acetamide. $^1$H NMR (400 MHz, DMSO, d$_6$) δ 9.05 (s, 1H), 6.90 (d, 1H, J=8.29 Hz), 6.47 (s, 1H), 6.39 (dd, 1H, J=2.03, 6.25 Hz), 4.83 (s, 2H), 2.95 (sept., 1H, J=6.81 Hz), 1.99 (s, 3H), 1.07 (d, 6H, J=6.84 Hz).

301d. N-{2-Isopropyl-5-[7-(2-methoxy-phenyl)-pyrrolo[2,1-f][1,2,4]triazin-2-ylamino]-phenyl}-acetamide: 2-Methanesulfinyl-7-(2-methoxy-phenyl)-pyrrolo[2,1-f][1,2,4]triazine (125.0 mg, 0.0004350 mol), N,N-Diisopropylethylamine (0.114 mL, 0.000652 mol) and N-(5-Amino-2-isopropyl-phenyl)-acetamide (0.167 g, 0.000870 mol) were dissolved in 1-Methoxy-2-propanol (1.2 mL, 0.013 mol) and the reaction was irradiated at 300 watts, 180° C. for 40 minutes or until HPLC showed consumption of starting material. The reaction mixture was then reduced en vacuo and the product was isolated and purified by Gilson prep HPLC to afford 58.52 mg of N-{2-Isopropyl-5-[7-(2-methoxy-phenyl)-pyrrolo[2,1-f][1,2,4]triazin-2-ylamino]-phenyl}-acetamide as a lyophilized powder. (M+H)=416.8. $^1$H NMR (400 MHz, DMSO, d$_6$) δ 9.34 (s, 1H), 9.24 (s, 1H), 8.94 (s, 1H), 7.83 (d, 1H, J=6.32 Hz), 7.59 (m, 1H), 7.47 (m, 2H), 7.19 (d, 1H, J=8.28 Hz), 7.12 (m, 2H), 6.95 (d, 1H, J=4.60 Hz), 6.91

(d, 1H, J=4.64 Hz), 3.71 (s, 3H), 3.00 (sept., 1H, J=6.84 Hz), 2.02 (s, 3H), 1.18 (d, 6H, J=6.32 Hz).

Example 302

N-{5-[7-(5-Chloro-2-methoxy-phenyl)-pyrrolo[2,1-f][1,2,4]triazin-2-ylamino]-2-isopropyl-phenyl}-acetamide The compound was made in an analogous fashion to Example 301 replacing 2-Methanesulfinyl-7-(2-methoxy-phenyl)-pyrrolo[2,1-f][1,2,4]triazine with 7-(5-Chloro-2-methoxy-phenyl)-2-methanesulfinyl-pyrrolo[2,1-f][1,2,4]triazine to afford 16.94 mg of N-{5-[7-(5-Chloro-2-methoxy-phenyl)-pyrrolo[2,1-f][1,2,4]triazin-2-ylamino]-2-isopropyl-phenyl}-acetamide as a lyophilized powder. (M+H)=450.7. $^1$H NMR (400 MHz, DMSO, $d_6$) δ 9.39 (s, 1H), 9.24 (s, 1H), 8.97 (s, 1H), 7.94 (m, 1H), 7.72 (dd, 1H, J=2.31, 6.16 Hz), 7.50 (dd, 1H, J=2.60, 6.12 Hz), 7.35 (m, 1H), 7.19 (m, 2H), 7.01 (d, 1H, J=4.68 Hz), 6.91 (d, 1H, J=4.69 Hz), 3.80 (s, 3H), 3.00 (sept., 1H, J=6.88 Hz), 2.02 (s, 3H), 1.09 (d, 6H, J=6.85 Hz).

Example 303

N-{5-[7-(3-Chloro-phenyl)-pyrrolo[2,1-f][1,2,4]triazin-2-ylamino]-2-isopropyl-phenyl}-acetamide The compound was made in an analogous fashion to Example 301 replacing 2-Methanesulfinyl-7-(2-methoxy-phenyl)-pyrrolo[2,1-f][1,2,4]triazine with 7-(3-Chloro-phenyl)-2-methanesulfinyl-pyrrolo[2,1-f][1,2,4]triazine to afford 27.96 mg of N-{5-[7-(3-Chloro-phenyl)-pyrrolo[2,1-f][1,2,4]triazin-2-ylamino]-2-isopropyl-phenyl}-acetamide as a lyophilized powder. (M+H)=420.7. $^1$H NMR (400 MHz, DMSO, $d_6$) δ 9.49 (s, 1H), 9.33 (s, 1H), 9.00 (s, 1H), 8.36 (m, 1H), 8.15 (d, 1H, J=7.93 Hz), 7.53 (d, 1H, J=7.89 Hz), 7.46 (m, 2H), 7.39 (m, 1H), 7.26 (m, 2H), 6.96 (d, 1H, J=4.80 Hz), 3.09 (sept., 1H, J=6.88 Hz), 2.04 (s, 3H), 1.13 (d, 6H, J=6.84 Hz).

Example 304

N-[2-Isopropyl-5-(7-pyridin-3-yl-pyrrolo[2,1-f][1,2,4]triazin-2-ylamino)-phenyl]-acetamide The compound was made in an analogous fashion to Example 301 replacing 2-Methanesulfinyl-7-(2-methoxy-phenyl)-pyrrolo[2,1-f][1,2,4]triazine with 2-Methanesulfinyl-7-pyridin-3-yl-pyrrolo[2,1-f][1,2,4]triazine to afford 62.13 mg of N-[2-Isopropyl-5-(7-pyridin-3-yl-pyrrolo[2,1-f][1,2,4]triazin-2-ylamino)-phenyl]-acetamide as a lyophilized powder. (M+H)=387.8. $^1$H NMR (400 MHz, DMSO, $d_6$) δ 9.56 (s, 1H), 9.40 (s, 1H), 9.36 (s, 1H), 9.06 (s, 1H), 8.86 (d, 1H, J=8.12 Hz), 8.70 (d, 1H, J=4.04 Hz), 7.76 (m, 1H), 7.70 (s, 1H), 7.47 (dd, 1H, J=1.92, 6.56 Hz), 7.38 (d, 1H, J=4.77 Hz), 7.25 (d, 1H, J=8.56 Hz), 7.01 (d, 1H, J=4.75 Hz), 3.09 (sept., 1H, J=6.85 Hz), 2.05 (s, 3H), 1.14 (d, 6H, J=6.84 Hz).

Example 305

N-{2-tert-Butyl-5-[7-(5-chloro-2-methoxy-phenyl)-pyrrolo[2,1-f][1,2,4]triazin-2-ylamino]-phenyl}-acetamide 305a. 2-tert-Butyl-5-nitro-phenylamine: 2-tert-Butyl-phenylamine (1.0 g, 0.0067 mol) was dissolved in Sulfuric acid (9.06 mL, 0.170 mol) at −5° C. Potassium nitrate (0.68 g, 0.0067 mol) was then added keeping the temperature below 0° C. The reaction was then allowed to stir gradually warming to room temperature until HPLC showed consumption of starting material. The mixture was then poured over water and the solution was neutralized with 2M sodium bicarbonate. The product was extracted with ethyl acetate and combined extracts were dried over sodium bicarbonate, filtered and reduced to afford 1.15 g of 2-tert-Butyl-5-nitro-phenylamine without further purification. $^1$H NMR (400 MHz, DMSO, $d_6$) δ 7.52 (s, 1H), 7.29 (m, 2H), 5.52 (m, 2H), 1.31 (s, 9H).

305b. N-(2-tert-Butyl-5-nitro-phenyl)-acetamide: 2-tert-Butyl-5-nitro-phenylamine (1.25 g, 0.00644 mol) was dissolved in Methylene chloride (20 mL, 0.4 mol) and the solution was treated with Triethylamine (1.34 mL, 0.00965 mol). After stirring at room temperature for 10 minutes, Acetyl chloride (0.505 g, 0.00644 mol) was added and the reaction was allowed to stir overnight at room temperature. The reaction mixture was poured over saturated sodium bicarbonate, and organics were extracted with ethyl acetate/dichloromethane. Combined organics were dried over sodium sulfate, filtered and reduced en vacuo to afford 1.50 g of N-(2-tert-Butyl-5-nitro-phenyl)-acetamide without further purification. $^1$H NMR (400 MHz, DMSO, $d_6$) δ 9.49 (s, 1H), 8.07 (m, 1H), 7.91 (s, 1H), 7.68 (d, 1H, J=8.89 Hz), 2.09 (s, 3H), 1.37 (s, 9H).

305c. N-(5-Amino-2-tert-butyl-phenyl)-acetamide: N-(2-tert-Butyl-5-nitro-phenyl)-acetamide (1.51 g, 0.00639 mol) was dissolved in Methanol (40 mL, 1 mol) and the solution was carefully added to 10% Palladium on Carbon (0.700 g, 0.0524 mol) in a Parr vessel under nitrogen. The mixture was then placed on a Parr apparatus and was allowed to stir until uptake of hydrogen had ceased (~3 hours). The catalyst was then removed via filtration and the filtrate was reduced to afford 1.25 g of N-(5-Amino-2-tert-butyl-phenyl)-acetamide without further purification. $^1$H NMR (400 MHz, DMSO, $d_6$) δ 8.96 (s, 1H), 6.99 (d, 1H, J=8.52 Hz), 6.39 (m, 1H), 6.25 (m, 1H), 4.87 (m, 2H), 1.97 (s, 3H), 1.25 (s, 9H).

305d. N-{2-tert-Butyl-5-[7-(5-chloro-2-methoxy-phenyl)-pyrrolo[2,1-f][1,2,4]triazin-2-ylamino]-phenyl}-acetamide: 2-Methanesulfinyl-7-(2-methoxy-phenyl)-pyrrolo[2,1-f][1,2,4]triazine (125.0 mg, 0.0004350 mol), N,N-Diisopropylethylamine (0.114 mL, 0.000652 mol) and N-(5-Amino-2-tert-butyl-phenyl)-acetamide (0.179 g, 0.000870 mol) were dissolved in 1-Methoxy-2-propanol (1.2 mL, 0.013 mol) and The reaction was irradiated at 300 watts, 180° C. for 40 minutes or until HPLC showed consumption of starting material. The reaction mixture was then reduced en vacuo and the product was isolated and purified by Gilson prep HPLC to afford 46.28 mg of N-{2-tert-Butyl-5-[7-(5-chloro-2-methoxy-phenyl)-pyrrolo[2,1-f][1,2,4]triazin-2-ylamino]-phenyl}-acetamide as a lyophilized powder. (M+H)=430.8. $^1$H NMR (400 MHz, DMSO, $d_6$) δ 9.35 (s, 1H), 9.13 (s, 1H), 8.94 (s, 1H), 7.83 (d, 1H, J=6.37 Hz), 7.42-7.52 (m, 3H), 7.17 (m, 3H), 6.93 (m, 2H), 3.80 (s, 3H), 1.99 (s, 3H), 1.27 (s, 9H).

Example 306

N-{2-tert-Butyl-5-[7-(5-chloro-2-methoxy-phenyl)-pyrrolo[2,1-f][1,2,4]triazin-2-ylamino]-phenyl}-acetamide The compound was made in an analogous fashion to Example 305 replacing 2-Methanesulfinyl-7-(2-methoxy-phenyl)-pyrrolo[2,1-f][1,2,4]triazine with 7-(5-Chloro-2-methoxy-phenyl)-2-methanesulfinyl-pyrrolo[2,1-f][1,2,4]

triazine to afford 44.33 mg of N-{2-tert-Butyl-5-[7-(5-chloro-2-methoxy-phenyl)-pyrrolo[2,1-f][1,2,4]triazin-2-ylamino]-phenyl}-acetamide as a lyophilized powder. (M+H)=464.8. $^1$H NMR (400 MHz, DMSO, d$_6$) δ 9.40 (s, 1H), 9.13 (s, 1H), 8.97 (s, 1H), 7.97 (m, 1H), 7.81 (d, 1H, J=8.81 Hz), 7.50 (m, 1H), 7.28 (d, 1H, J=8.84 Hz), 7.22 (m, 1H), 7.16 (d, 1H, J=4.72 Hz), 7.12 (m, 1H), 7.03 (dd, 1H, J=2.6, 4.77 Hz), 3.82 (s, 3H), 2.11 (s, 3H), 1.30 (s, 9H).

Example 307

N-{2-tert-Butyl-5-[7-(3-chloro-phenyl)-pyrrolo[2,1-f][1,2,4]triazin-2-ylamino]-phenyl}-acetamide The compound was made in an analogous fashion to Example 305 replacing 2-Methanesulfinyl-7-(2-methoxy-phenyl)-pyrrolo[2,1-f][1,2,4]triazine with 7-(3-Chloro-phenyl)-2-methanesulfinyl-pyrrolo[2,1-f][1,2,4]triazine to afford 13.86 mg of N-{2-tert-Butyl-5-[7-(3-chloro-phenyl)-pyrrolo[2,1-f][1,2,4]triazin-2-ylamino]-phenyl}-acetamide as a lyophilized powder. (M+H)=434.7. $^1$H NMR (400 MHz, DMSO, d$_6$) δ 9.51 (s, 1H), 9.21 (m, 1H), 9.01 (s, 1H), 8.37 (m, 1H), 8.18 (m, 1H), 7.72 (m, 1H), 7.60 (m, 1H), 7.53 (m, 1H), 7.38 (m, 1H), 7.30 (m, 2H), 6.97 (d, 1H, J=4.76 Hz), 2.01 (s, 3H), 1.32 (s, 9H).

Example 308

N-[2-tert-Butyl-5-(7-pyridin-3-yl-pyrrolo[2,1-f][1,2,4]triazin-2-ylamino)-phenyl]-acetamide The compound was made in an analogous fashion to Example 305 replacing 2-Methanesulfinyl-7-(2-methoxy-phenyl)-pyrrolo[2,1-f][1,2,4]triazine with 2-Methanesulfinyl-7-pyridin-3-yl-pyrrolo[2,1-f][1,2,4]triazine to afford 24.90 mg of N-[2-tert-Butyl-5-(7-pyridin-3-yl-pyrrolo[2,1-f][1,2,4]triazin-2-ylamino)-phenyl]-acetamide as a lyophilized powder. (M+H)=401.8. $^1$H NMR (400 MHz, DMSO, d$_6$) δ 9.58 (s, 1H), 9.37 (s, 1H), 9.24 (s, 1H), 9.01 (s, 1H), 8.81 (d, 1H, J=8.16 Hz), 8.68 (d, 1H, J=4.01 Hz), 7.80 (m, 1H), 7.50 (m, 2H), 7.36 (d, 1H, J=4.77 Hz), 7.31 (m, 1H), 7.01 (d, 1H, J=4.80 Hz), 2.02 (s, 3H), 1.34 (s, 9H).

Example 309

(3-Morpholin-4-yl-phenyl)-(7-pyridin-3-yl-pyrrolo[2,1-f][1,2,4]triazin-2-yl)-amine 2-Methanesulfinyl-7-pyridin-3-yl-pyrrolo[2,1-f][1,2,4]triazine (125.0 mg, 0.0004839 mol), N,N-Diisopropylethylamine (0.126 mL, 0.000726 mol) and 3-Morpholin-4-yl-phenylamine (0.172 g, 0.000968 mol) were dissolved in 1-Methoxy-2-propanol (1.0 mL, 0.010 mol) and the reaction was irradiated at 300 watts, 200° C. for 20 minutes or until HPLC showed consumption of starting material. The reaction mixture was then reduced en vacuo and the product was isolated and purified by Gilson prep HPLC to afford 73.26 mg of (3-Morpholin-4-yl-phenyl)-(7-pyridin-3-yl-pyrrolo[2,1-f][1,2,4]triazin-2-yl)-amine as a lyophilized powder. (M+H)=373.7. $^1$H NMR (400 MHz, DMSO, d$_6$) δ 9.45 (s, 2H), 9.07 (s, 1H), 8.81 (d, 1H, J=8.00 Hz), 8.70 (d, 1H, J=3.76 Hz), 7.78 (m, 1H), 7.35 (d, 1H, J=4.76 Hz), 7.30 (s, 1H), 7.18 (m, 2H), 7.02 (d, 1H, J=4.80 Hz), 6.62 (m, 1H), 3.69 (m, 4H), 3.02 (m, 4H).

Example 310

[7-(2-Methoxy-phenyl)-pyrrolo[2,1-f][1,2,4]triazin-2-yl]-{4-[4-(4-methyl-piperazin-1-yl)-piperidin-1-yl]-phenyl}-amine 2-Methane sulfinyl-7-(2-methoxy-phenyl)-pyrrolo[2,1-f][1,2,4]triazine (125.0 mg, 0.0004350 mol), N,N-Diisopropylethylamine (0.114 mL, 0.000652 mol) and 4-[4-(4-Methyl-piperazin-1-yl)-piperidin-1-yl]-phenylamine (0.239 g, 0.000870 mol) were dissolved in 1-Methoxy-2-propanol (1.2 mL, 0.013 mol) and the reaction was irradiated at 300 watts, 180° C. for 40 minutes or until HPLC showed consumption of starting material. The reaction mixture was then reduced en vacuo and the product was isolated and purified by Gilson prep HPLC to afford 164.97 mg of [7-(2-Methoxy-phenyl)-pyrrolo[2,1-f][1,2,4]triazin-2-yl]-{4-[4-(4-methyl-piperazin-1-yl)-piperidin-1-yl]-phenyl}-amine as a lyophilized powder. (M+H)=498.9. $^1$H NMR (400 MHz, DMSO, d$_6$) δ 9.42 (s, 1H), 8.94 (s, 1H), 7.80 (dd, 1H, J=1.60, 6.00 Hz), 7.69 (d, 2H, J=8.93 Hz), 7.46 (m, 1H), 7.20 (d, 1H, J=8.28 Hz), 7.13 (m, 3H), 6.94 (m, 2H), 3.70 (s, 3H), 3.67 (m, 7H), 3.01 (m, 6H), 2.83 (s, 3H), 2.07 (m, 2H), 1.79 (m, 2H).

Example 311

[7-(5-Chloro-2-methoxy-phenyl)-pyrrolo[2,1-f][1,2,4]triazin-2-yl]-{4-[4-(4-methyl-piperazin-1-yl)-piperidin-1-yl]-phenyl}-amine The compound was made in an analogous fashion to Example 310 replacing 2-Methanesulfinyl-7-(2-methoxy-phenyl)-pyrrolo[2,1-f][1,2,4]triazine with 745-Chloro-2-methoxy-phenyl)-2-methanesulfinyl-pyrrolo[2,1-f][1,2,4]triazine to afford 147.27 mg of [7-(5-Chloro-2-methoxy-phenyl)-pyrrolo[2,1-f][1,2,4]triazin-2-yl]-{4-[4-(4-methyl-piperazin-1-yl)-piperidin-1-yl]-phenyl}-amine as a lyophilized powder. (M+H)=532.9. $^1$H NMR (400 MHz, DMSO, d$_6$) δ 9.44 (s, 1H), 8.97 (s, 1H), 8.07 (m, 1H), 7.67 (d, 2H, J=8.77 Hz), 7.48 (dd, 1H, J=2.68, 6.20 Hz), 7.23 (d, 1H, J=8.95 Hz), 7.10 (m, 2H), 7.06 (d, 1H, J=4.68 Hz), 6.92 (d, 1H, J=4.73 Hz), 3.95 (s, 3H), 3.69 (m, 11H), 3.02 (m, 2H), 2.91 (s, 3H), 2.05 (m, 2H), 1.74 (m, 2H).

Example 312

[7-(3-Chloro-phenyl)-pyrrolo[2,1-f][1,2,4]triazin-2-yl]-{4-[4-(4-methyl-piperazin-1-yl)-piperidin-1-yl]-phenyl}-amine The compound was made in an analogous fashion to Example 310 replacing 2-Methanesulfinyl-7-(2-methoxy-phenyl)-pyrrolo[2,1-f][1,2,4]triazine with 7-(3-Chloro-phenyl)-2-methanesulfinyl-pyrrolo[2,1-f][1,2,4]triazine to afford 81.07 mg of [7-(3-Chloro-phenyl)-pyrrolo[2,1-f][1,2,4]triazin-2-yl]-{4-[4-(4-methyl-piperazin-1-yl)-piperidin-1-yl]-phenyl}-amine as a lyophilized powder. (M+H)=434.7. $^1$H NMR (400 MHz, DMSO, d$_6$) δ 9.27 (s, 1H), 8.96 (s, 1H), 8.48 (m, 1H), 8.10 (m, 1H), 7.60 (d, 2H, J=9.00 Hz), 7.51 (m, 2H), 7.24 (d, 1H, J=4.80 Hz), 6.93 (m, 3H), 3.63 (d, 2H, J=12.55 Hz), 3.38 (m, 2H), 2.61 (m, 2H), 2.49 (m, 2H), 2.32 (m, 5H), 2.27 (s, 3H), 1.83 (m, 2H), 1.49 (m, 2H).

Example 313

{4-[4-(4-Methyl-piperazin-1-yl)-piperidin-1-yl]-phenyl}-(7-pyridin-3-yl-pyrrolo[2,1-f][1,2,4]triazin-2-yl)-amine The compound was made in an analogous fashion to Example 305 replacing 2-Methanesulfinyl-7-(2-methoxyphenyl)-pyrrolo[2,1-f][1,2,4]triazine with 2-Methanesulfinyl-7-pyridin-3-yl-pyrrolo[2,1-f][1,2,4]triazine to afford 55.89 mg of {4-[4-(4-Methyl-piperazin-1-yl)-piperidin-1-yl]-phenyl}-(7-pyridin-3-yl-pyrrolo[2,1-f][1,2,4]triazin-2-yl)-amine as a lyophilized powder. (M+H)=469.8. $^1$H NMR (400 MHz, DMSO, $d_6$) δ 9.32 (m, 1H), 9.27 (s, 1H), 8.98 (s, 1H), 8.61 (m, 1H), 8.56 (m, 1H), 7.55 (m, 3H), 7.26 (d, 1H, J=4.80 Hz), 6.94 (d, 1H, J=4.76 Hz), 6.91 (d, 2H, J=9.05 Hz), 4.09 (m, 1H), 3.62 (m, 2H), 3.17 (m, 3H), 2.63 (m, 2H), 2.33 (m, 4H), 2.28 (m, 4H), 1.86 (m, 2H), 1.50 (m, 2H).

Example 314

{4-[7-(2-Methoxy-phenyl)-pyrrolo[2,1-f][1,2,4]triazin-2-ylamino]-phenyl}-morpholin-4-yl-methanone 314a. Morpholin-4-yl-(4-nitro-phenyl)-methanone: 4-Nitrobenzoic acid (2.00 g, 0.0120 mol), Morpholine (1.25 g, 0.0144 mol), N-(3-Dimethylaminopropyl)-N'-ethylcarbodiimide hydrochloride (2.29 g, 0.0120 mol) and 1-Hydroxybenzotriazole (0.40 g, 0.0030 mol) were dissolved in Tetrahydrofuran (35 mL, 0.43 mol) and the reaction was allowed to stir overnight at room temperature. The reaction mixture was poured over saturated sodium bicarbonate, and organics were extracted with ethyl acetate/dichloromethane. Combined organics were dried over sodium sulfate, filtered and reduced en vacuo. The crude mixture was purified by Isco flash column chromatography (Hexane/Ethyl Acetate). Combined fractions were reduced en vacuo to afford 2.01 g of Morpholin-4-yl-(4-nitro-phenyl)-methanone. $^1$H NMR (400 MHz, DMSO, $d_6$) δ 8.29 (d, 2H, J=8.65 Hz), 7.69 (d, 2H, J=8.64 Hz), 3.65 (m, 4H), 3.54 (m, 2H), 3.28 (m, 2H).

314b. (4-Amino-phenyl)-morpholin-4-yl-methanone: Morpholin-4-yl-(4-nitro-phenyl)-methanone (2.01 g, 8.51 mmol) was dissolved in Methanol (35 mL, 860 mmol) and the solution was carefully added to a Parr vessel containing 10% Palladium on Carbon (0.650 g, 48.7 mmol) under nitrogen. The mixture was then placed on a Parr hydrogenation apparatus and was allowed to shake at 55 psi until uptake of hydrogen ceased. The catalyst was then filtered to afford 1.75 g of (4-Amino-phenyl)-morpholin-4-yl-methanone without further purification. (M+H)=207.6. $^1$H NMR (400 MHz, DMSO, $d_6$) δ 7.12 (d, 2H, J=8.40 Hz), 6.52 (d, 2H, J=8.42 Hz), 5.51 (s, 2H), 3.58 (m, 4H), 3.46 (m, 4H).

314c. {4-[7-(2-Methoxy-phenyl)-pyrrolo[2,1-f][1,2,4]triazin-2-ylamino]-phenyl}-morpholin-4-yl-methanone: 2-Methanesulfinyl-7-(2-methoxy-phenyl)-pyrrolo[2,1-f][1,2,4]triazine (125.0 mg, 0.0004350 mol), N,N-Diisopropylethylamine (0.114 mL, 0.000652 mol) and (4-Amino-phenyl)-morpholin-4-yl-methanone (0.179 g, 0.000870 mol) were dissolved in 1-Methoxy-2-propanol (1.2 mL, 0.013 mol) and the reaction was irradiated at 300 watts, 180° C. for 40 minutes or until HPLC showed consumption of starting material. The reaction mixture was then reduced en vacuo and the product was isolated and purified by Gilson prep HPLC to afford 45.33 mg of 4-[7-(2-Methoxy-phenyl)-pyrrolo[2,1-f][1,2,4]triazin-2-ylamino]-phenyl}-morpholin-4-yl-methanone as a lyophilized powder. (M+H)=430.8. $^1$H NMR (400 MHz, DMSO, $d_6$) δ 9.68 (s, 1H), 8.99 (s, 1H), 7.76 (d, 3H, J=8.44 Hz), 7.47 (m, 1H), 7.26 (m, 3H), 7.12 (m, 1H), 6.96 (m, 2H), 3.80 (s, 3H), 3.59 (m, 4H), 3.49 (m, 4H).

Example 315

{4-[7-(5-Chloro-2-methoxy-phenyl)-pyrrolo[2,1-f][1,2,4]triazin-2-ylamino]-phenyl}-morpholin-4-yl-methanone The compound was made in an analogous fashion to Example 314 replacing 2-Methanesulfinyl-7-(2-methoxy-phenyl)-pyrrolo[2,1-f][1,2,4]triazine with 7-(5-Chloro-2-methoxy-phenyl)-2-methanesulfinyl-pyrrolo[2,1-f][1,2,4]triazine to afford 51.19 mg of {4-[7-(5-Chloro-2-methoxy-phenyl)-pyrrolo[2,1-f][1,2,4]triazin-2-ylamino]-phenyl}-morpholin-4-yl-methanone as a lyophilized powder. (M+H)=464.7. $^1$H NMR (400 MHz, DMSO, $d_6$) δ 9.78 (s, 1H), 9.03 (s, 1H), 8.03 (d, 1H, J=2.69 Hz), 7.78 (d, 2H, J=8.60 Hz), 7.51 (dd, 1H, J=2.68, 6.20 Hz), 7.34 (d, 2H, J=8.61 Hz), 7.26 (d, 1H, J=8.96 Hz), 7.07 (d, 1H, J=4.72 Hz), 6.96 (d, 1H, J=4.72 Hz), 3.83 (s, 3H), 3.64 (m, 4H), 3.50 (m, 4H).

Example 316

{4-[7-(3-Chloro-phenyl)-pyrrolo[2,1-f][1,2,4]triazin-2-ylamino]-phenyl}-morpholin-4-yl-methanone The compound was made in an analogous fashion to Example 314 replacing 2-Methanesulfinyl-7-(2-methoxy-phenyl)-pyrrolo[2,1-f][1,2,4]triazine with 7-(3-Chloro-phenyl)-2-methanesulfinyl-pyrrolo[2,1-f][1,2,4]triazine to afford 43.57 mg of {4-[7-(3-Chloro-phenyl)-pyrrolo[2,1-f][1,2,4]triazin-2-ylamino]-phenyl}-morpholin-4-yl-methanone as a lyophilized powder. (M+H)=434.7. $^1$H NMR (400 MHz, DMSO, $d_6$) δ 9.85 (s, 1H), 9.06 (s, 1H), 8.48 (m, 1H), 8.02 (d, 1H, J=7.92 Hz), 7.84 (d, 2H, J=8.64 Hz), 7.57 (t, 1H, J=7.92 Hz), 7.48 (m, 1H), 7.41 (d, 2H, J=8.60 Hz), 7.31 (d, 1H, J=4.80 Hz), 7.01 (d, 1H, J=4.80 Hz), 3.61 (m, 4H), 3.52 (m, 4H).

Example 317

Morpholin-4-yl-[4-(7-pyridin-3-yl-pyrrolo[2,1-f][1,2,4]triazin-2-ylamino)-phenyl]-methanone The compound was made in an analogous fashion to Example 314 replacing 2-Methanesulfinyl-7-(2-methoxy-phenyl)-pyrrolo[2,1-f][1,2,4]triazine with 2-Methanesulfinyl-7-pyridin-3-yl-pyrrolo[2,1-f][1,2,4]triazine to afford 28.78 mg of Morpholin-4-yl-[4-(7-pyridin-3-yl-pyrrolo[2,1-f][1,2,4]triazin-2-ylamino)-phenyl]-methanone as a lyophilized powder. (M+H)=401.7. $^1$H NMR (400 MHz, DMSO, $d_6$) δ 9.88 (s, 1H), 9.42 (s, 1H), 9.11 (s, 1H), 8.80 (d, 1H, J=8.25 Hz), 8.70 (d, 1H, J=3.80 Hz), 7.79 (m, 3H), 7.40 (m, 3H), 7.06 (d, 1H, J=4.80 Hz), 3.61 (m, 4H), 3.52 (m, 4H).

Example 318

{4-[7-(2-Methoxy-phenyl)-pyrrolo[2,1-f][1,2,4]triazin-2-ylamino]-phenyl}-(4-methyl-piperazin-1-yl)-methanone 318a. (4-Methyl-piperazin-1-yl)-(4-nitro-phenyl)-methanone 4-Nitrobenzoic acid (2.00 g, 0.0120 mol), piperazine, 1-methyl- (1.44 g, 0.0144 mol), N-(3-Dimethylaminopropyl)-N'-ethylcarbodiimide hydrochloride (2.29 g, 0.0120 mol) and 1-Hydroxybenzotriazole (0.40 g, 0.0030 mol) were dissolved in Tetrahydrofuran (35 mL, 0.43 mol) and the reaction was allowed to stir overnight at room temperature. The reaction mixture was poured over saturated sodium bicarbonate, and organics were extracted with ethyl acetate/dichloromethane. Combined organics were dried over sodium sulfate, filtered and reduced en vacuo. The crude mixture was purified by Isco flash column chromatography (Hexane/Ethyl Acetate). Combined fractions were reduced en vacuo to afford (4-Methyl-piperazin-1-yl)-(4-nitro-phenyl)-methanone. (M+H)=250.6. $^1$H NMR (400 MHz, DMSO, $d_6$) δ 8.28

(d, 2H, J=8.40 Hz), 7.67 (d, 2H, J=8.42 Hz), 3.64 (m, 2H), 3.25 (m, 2H), 2.38 (m, 2H), 2.26 (m, 2H), 2.20 (s, 3H).

318b. (4-Amino-phenyl)-(4-methyl-piperazin-1-yl)-methanone (4-Methyl-piperazin-1-yl)-(4-nitro-phenyl)-methanone (2.12 g, 8.51 mmol) was dissolved in Methanol (35 mL, 860 mmol) and the solution was carefully added to a Parr vessel containing 10% Palladium on Carbon (0.650 g, 48.7 mmol) under nitrogen. The mixture was then placed on a Parr hydrogenation apparatus and was allowed to shake at 55 psi until uptake of hydrogen ceased. The catalyst was then filtered to afford 1.86 g of (4-Amino-phenyl)-(4-methyl-piperazin-1-yl)-methanone without further purification. (M+H)=220.6. $^1$H NMR (400 MHz, DMSO, $d_6$) δ 7.09 (d, 2H, J=8.41 Hz), 6.53 (d, 2H J=8.41 Hz), 5.48 (s, 2H), 3.46 (m, 4H), 2.28 (m, 4H), 2.17 (s, 3H).

318c. {4-[7-(2-Methoxy-phenyl)-pyrrolo[2,1-f][1,2,4]triazin-2-ylamino]-phenyl}-(4-methyl-piperazin-1-yl)-methanone 2-Methanesulfinyl-7-(2-methoxy-phenyl)-pyrrolo[2,1-f][1,2,4]triazine (125.0 mg, 0.0004350 mol), N,N-Diisopropylethylamine (0.114 mL, 0.000652 mol) and (4-Amino-phenyl)-(4-methyl-piperazin-1-yl)-methanone (0.191 g, 0.000870 mol) were dissolved in 1-Methoxy-2-propanol (1.2 mL, 0.013 mol) and the reaction was irradiated at 300 watts, 180° C. for 40 minutes or until HPLC showed consumption of starting material. The reaction mixture was then reduced en vacuo and the product was isolated and purified by Gilson prep HPLC to afford 73.56 mg of {4-[7-(2-Methoxy-phenyl)-pyrrolo[2,1-f][1,2,4]triazin-2-ylamino]-phenyl}-(4-methyl-piperazin-1-yl)-methanone as a lyophilized powder. (M+H)=443.8. $^1$H NMR (400 MHz, DMSO, $d_6$) δ 9.74 (s, 1H), 9.00 (s, 1H), 7.76 (m, 3H), 7.48 (m, 1H), 7.33 (d, 2H, J=8.64 Hz), 7.23 (d, 1H, J=8.28 Hz), 7.13 (t, 1H, J=7.48 Hz), 6.97 (m, 2H), 3.81 (s, 3H), 3.06 (m, 4H), 3.26 (m, 2H), 3.07 (m, 2H), 2.83 (s, 3H).

Example 319

{4-[7-(5-Chloro-2-methoxy-phenyl)-pyrrolo[2,1-f][1,2,4]triazin-2-ylamino]-phenyl}-(4-methyl-piperazin-1-yl)-methanone The compound was made in an analogous fashion to Example 318 replacing 2-Methanesulfinyl-7-(2-methoxy-phenyl)-pyrrolo[2,1-f][1,2,4]triazine with 7-(5-Chloro-2-methoxy-phenyl)-2-methanesulfinyl-pyrrolo[2,1-f][1,2,4]triazine to afford 54.93 mg of {4-[7-(5-Chloro-2-methoxy-phenyl)-pyrrolo[2,1-f][1,2,4]triazin-2-ylamino]-phenyl}-(4-methyl-piperazin-1-yl)-methanone as a lyophilized powder. (M+H)=477.7. $^1$H NMR (400 MHz, DMSO, $d_6$) δ 9.83 (s, 1H), 9.03 (s, 1H), 8.04 (m, 1H), 7.81 (d, 2H, J=8.65 Hz), 7.50 (dd, 1H, J=2.68, 6.20 Hz), 7.39 (d, 2H, J=8.60 Hz), 7.26 (d, 1H, J=8.97 Hz), 7.09 (d, 1H, J=4.72 Hz), 6.98 (d, 1H, J=4.69 Hz), 3.90 (s, 3H), 3.75 (m, 2H), 3.42 (m, 2H), 3.30 (m, 2H), 3.08 (m, 2H), 2.83 (s, 3H).

Example 320

{4-[7-(3-Chloro-phenyl)-pyrrolo[2,1-f][1,2,4]triazin-2-ylamino]-phenyl}-(4-methyl-piperazin-1-yl)-methanone The compound was made in an analogous fashion to Example 318 replacing 2-Methanesulfinyl-7-(2-methoxy-phenyl)-pyrrolo[2,1-f][1,2,4]triazine with 7-(3-Chloro-phenyl)-2-methanesulfinyl-pyrrolo[2,1-f][1,2,4]triazine to afford 78.10 mg of {4-[7-(3-Chloro-phenyl)-pyrrolo[2,1-f][1,2,4]triazin-2-ylamino]-phenyl}-(4-methyl-piperazin-1-yl)-methanone as a lyophilized powder. (M+H)=447.7. $^1$H NMR (400 MHz, DMSO, $d_6$) δ 9.91 (s, 1H), 9.07 (s, 1H), 8.48 (s, 1H), 7.87 (d, 1H, J=8.60 Hz), 7.57 (m, 2H), 7.48 (m, 1H), 7.45 (m, 3H), 7.32 (d, 1H, J=4.80 Hz), 7.02 (d, 1H, J=4.81 Hz), 3.34 (m, 4H), 3.28 (m, 2H), 3.09 (m, 2H), 2.83 (s, 3H).

Example 321

(4-Methyl-piperazin-1-yl)-[4-(7-pyridin-3-yl-pyrrolo[2,1-f][1,2,4]triazin-2-ylamino)-phenyl]-methanone The compound was made in an analogous fashion to Example 318 replacing 2-Methanesulfinyl-7-(2-methoxy-phenyl)-pyrrolo[2,1-f][1,2,4]triazine with 2-Methanesulfinyl-7-pyridin-3-yl-pyrrolo[2,1-f][1,2,4]triazine to afford 14.17 mg of (4-Methyl-piperazin-1-yl)-[4-(7-pyridin-3-yl-pyrrolo[2,1-f][1,2,4]triazin-2-ylamino)-phenyl]-methanone as a lyophilized powder. (M+H)=414.8. $^1$H NMR (400 MHz, DMSO, $d_6$) δ 9.90 (s, 1H), 9.40 (s, 1H), 9.10 (s, 1H), 8.64 (m, 2H), 7.82 (d, 2H, J=8.64 Hz), 7.67 (m, 1H), 7.45 (d, 2H, J=8.60 Hz), 7.37 (d, 1H, J=4.76 Hz), 7.05 (d, 1H, J=4.80 Hz), 3.43 (m, 2H), 3.29 (m, 2H), 3.16 (m, 2H), 3.09 (m, 2H), 2.84 (s, 3H).

Example 322

1-[7-(2-Methoxy-phenyl)-pyrrolo[2,1-f][1,2,4]triazin-2-yl]-1H-imidazo[4,5-c]pyridine 2-Methanesulfinyl-7-(2-methoxy-phenyl)-pyrrolo[2,1-f][1,2,4]triazine (125.0 mg, 0.0004350 mol), N,N-Diisopropylethylamine (0.114 mL, 0.000652 mol) and 1H-Imidazo[4,5-c]pyridine (0.104 g, 0.000870 mol) were dissolved in 1-Methoxy-2-propanol (1.2 mL, 0.013 mol) and the reaction was irradiated at 300 watts, 180° C. for 40 minutes or until HPLC showed consumption of starting material. The reaction mixture was then reduced en vacuo and the product was isolated and purified by Gilson prep HPLC to afford 43.80 mg of 1-[7-(2-Methoxy-phenyl)-pyrrolo[2,1-f][1,2,4]triazin-2-yl]-1H-imidazo[4,5-c]pyridine (mixture of regioisomers) as a lyophilized powder. (M+H)=343.7. $^1$H NMR (400 MHz, DMSO, $d_6$) δ 9.35 (s, 1H), 9.15 (s, 1H), 8.47 (d, 1H, J=5.52 Hz), 8.09 (d, 1H, J=5.45 Hz), 7.81 (m, 2H), 7.57 (m, 1H), 7.32 (m, 3H), 7.23 (m, 1H), 3.82 (s, 3H).

Example 323

1-[7-(5-Chloro-2-methoxy-phenyl)-pyrrolo[2,1-f][1,2,4]triazin-2-yl]-1H-imidazo[4,5-c]pyridine The compound was made in an analogous fashion to Example 322 replacing 2-Methanesulfinyl-7-(2-methoxy-phenyl)-pyrrolo[2,1-f][1,2,4]triazine with 7-(5-Chloro-2-methoxy-phenyl)-2-methanesulfinyl-pyrrolo[2,1-f][1,2,4]triazine to afford 67.32 mg of 1-[7-(5-Chloro-2-methoxy-phenyl)-pyrrolo[2,1-f][1,2,4]triazin-2-yl]-1H-imidazo[4,5-c]pyridine as a lyophilized powder. (M+H)=377.6. $^1$H NMR (400 MHz, DMSO, $d_6$) δ 9.38 (s, 1H), 9.17 (s, 1H), 8.50 (m, 1H), 8.21 (m, 1H), 8.07 (m, 1H), 7.41 (m, 1H), 7.36 (m, 1H), 7.32 (m, 3H), 3.85 (s, 3H).

Example 324

1-[7-(3-Chloro-phenyl)-pyrrolo[2,1-f][1,2,4]triazin-2-yl]-1H-imidazo[4,5-c]pyridine The compound was made in an analogous fashion to Example 322 replacing 2-Methanesulfinyl-7-(2-methoxyphenyl)-pyrrolo[2,1-f][1,2,4]triazine with 7-(3-Chloro-phenyl)-2-methanesulfinyl-pyrrolo[2,1-f][1,2,4]triazine to afford 90.14 mg of 1-[7-(3-Chloro-phenyl)-pyrrolo[2,1-f][1,2,4]triazin-2-yl]-1H-imidazo[4,5-c]pyridine as a lyophilized powder. (M+H)=347.6. $^1$H NMR (400 MHz, DMSO, d$_6$) δ 9.42 (s, 1H), 9.21 (s, 1H), 8.61 (m, 1H), 8.53 (m, 1H), 8.35 (m, 1H), 8.15 (m, 1H), 7.63 (m, 4H), 7.36 (d, 1H, J=4.89 Hz).

Example 325

1-(7-Pyridin-3-yl-pyrrolo[2,1-f][1,2,4]triazin-2-yl)-1H-imidazo[4,5-c]pyridine

The compound was made in an analogous fashion to Example 322 replacing 2-Methanesulfinyl-7-(2-methoxy-phenyl)-pyrrolo[2,1-f][1,2,4]triazine with 2-Methanesulfinyl-7-pyridin-3-yl-pyrrolo[2,1-f][1,2,4]triazine to afford 60.57 mg of 1-(7-Pyridin-3-yl-pyrrolo[2,1-f][1,2,4]triazin-2-yl)-1H-imidazo[4,5-c]pyridine as a lyophilized powder. (M+H)=314.6. $^1$H NMR (400 MHz, DMSO, d$_6$) δ 9.43 (s, 1H), 9.36 (s, 1H), 9.29 (s, 1H), 8.69 (m, 2H), 8.50 (m, 2H), 8.23 (m, 1H), 7.65 (m, 2H), 7.38 (d, 1H, J=4.84 Hz).

Example 326

N-{2-tert-Butyl-5-[7-(4-methanesulfonyl-phenyl)-pyrrolo[2,1-f][1,2,4]triazin-2-ylamino]-phenyl}-acetamide The compound was made in an analogous fashion to Example 305 replacing 2-Methanesulfinyl-7-(2-methoxy-phenyl)-pyrrolo[2,1-f][1,2,4]triazine with 2-Methanesulfinyl-7-(4-methanesulfonyl-phenyl)-pyrrolo[2,1-f][1,2,4]triazine to afford 16.33 mg of N-[2-tert-Butyl-5-(7-pyridin-3-yl-pyrrolo[2,1-f][1,2,4]triazin-2-ylamino)-phenyl]-acetamide as a lyophilized powder. (M+H)=478.8. $^1$H NMR (400 MHz, DMSO, d$_6$) δ 9.60 (m, 1H), 9.29 (m, 1H), 9.06 (s, 1H), 8.49 (d, 2H, J=8.52 Hz), 8.11 (d, 2H, J=8.48 Hz), 7.64 (m, 1H), 7.47 (m, 1H), 7.39 (m, 2H), 7.01 (d, 1H, J=4.84 Hz), 3.29 (s, 3H), 2.02 (s, 3H), 1.32 (s, 9H).

Example 327

{3-[7-(2-Methoxy-phenyl)-pyrrolo[2,1-f][1,2,4]triazin-2-ylamino]-phenyl}-morpholin-4-yl-methanone 327a. Morpholin-4-yl-(3-nitro-phenyl)-methanone m-Nitrobenzoic acid (2.00 g, 0.0120 mol), Morpholine (1.25 g, 0.0144 mol), N-(3-Dimethylaminopropyl)-N'-ethylcarbodiimide hydrochloride (2.29 g, 0.0120 mol) and 1-Hydroxybenzotriazole (0.40 g, 0.0030 mol) were dissolved in Tetrahydrofuran (35 mL, 0.43 mol) and the reaction was allowed to stir overnight at room temperature. The reaction mixture was poured over saturated sodium bicarbonate, and organics were extracted with ethyl acetate/dichloromethane. Combined organics were dried over sodium sulfate, filtered and reduced en vacuo. The crude mixture was purified by Isco flash column chromatography (Hexane/Ethyl Acetate). Combined fractions were reduced en vacuo to afford 2.79 g of Morpholin-4-yl-(3-nitro-phenyl)-methanone. (M+H)=237.5.

327b. (3-Amino-phenyl)-morpholin-4-yl-methanone

Morpholin-4-yl-(3-nitro-phenyl)-methanone (2.74 g, 11.6 mmol) was dissolved in Ethanol (30.0 mL, 514 mmol) and the solution was carefully added to a Parr vessel containing 10% Palladium on Carbon (0.750 g, 56.2 mmol) under nitrogen. The mixture was then placed on a Parr hydrogenation apparatus and was allowed to shake at 55 psi until uptake of hydrogen ceased. The catalyst was then filtered to afford (3-Amino-phenyl)-morpholin-4-yl-methanone without further purification. (M+H)=207.6.

327c. {3-[7-(2-Methoxy-phenyl)-pyrrolo[2,1-f][1,2,4]triazin-2-ylamino]-phenyl}-morpholin-4-yl-methanone 2-Methanesulfinyl-7-(2-methoxy-phenyl)-pyrrolo[2,1-f][1,2,4]triazine (125.0 mg, 0.0004350 mol), N,N-Diisopropylethylamine (0.114 mL, 0.000652 mol) and (3-Amino-phenyl)-morpholin-4-yl-methanone (0.179 g, 0.000870 mol) were dissolved in 1-Methoxy-2-propanol (1.2 mL, 0.013 mol) and the reaction was irradiated at 300 watts, 180° C. for 40 minutes or until HPLC showed consumption of starting material. The reaction mixture was then reduced en vacuo and the product was isolated and purified by Gilson prep HPLC to afford 22.40 mg of {3-[7-(2-Methoxy-phenyl)-pyrrolo[2,1-f][1,2,4]triazin-2-ylamino]-phenyl}-morpholin-4-yl-methanone as a lyophilized powder. (M+H)=430.8. $^1$H NMR (400 MHz, DMSO, d$_6$) δ 9.58 (s, 1H), 8.95 (s, 1H), 7.78 (m, 2H), 7.71 (m, 1H), 7.48 (m, 1H), 7.26 (m, 1H), 7.18 (m, 1H), 7.07 (t, 1H, J=7.48 Hz), 6.94 (m, 2H), 6.89 (m, 1H), 3.96 (s, 3H), 3.73 (m, 2H), 3.36 (m, 4H), 3.17 (m, 2H).

Example 328

{3-[7-(5-Chloro-2-methoxy-phenyl)-pyrrolo[2,1-f][1,2,4]triazin-2-ylamino]-phenyl}-morpholin-4-yl-methanone The compound was made in an analogous fashion to Example 327 replacing 2-Methanesulfinyl-7-(2-methoxy-phenyl)-pyrrolo[2,1-f][1,2,4]triazine with 7-(5-Chloro-2-methoxy-phenyl)-2-methanesulfinyl-pyrrolo[2,1-f][1,2,4]triazine to afford 31.81 mg of {3-[7-(5-Chloro-2-methoxy-phenyl)-pyrrolo[2,1-f][1,2,4]triazin-2-ylamino]-phenyl}-morpholin-4-yl-methanone as a lyophilized powder. (M+H)=464.7. $^1$H NMR (400 MHz, DMSO, d$_6$) δ 9.64 (s, 1H), 9.01 (s, 1H), 7.87 (m, 2H), 7.59 (m, 1H), 7.50 (dd, 1H, J=2.64, 6.20 Hz), 7.32 (t, 1H, J=7.88 Hz), 7.21 (d, 1H, J=8.96 Hz), 7.01 (d, 1H, J=4.68 Hz), 6.93 (m, 2H), 3.80 (s, 3H), 3.61 (m, 4H), 3.31 (m, 2H), 3.26 (m, 2H).

Example 329

{3-[7-(3-Chloro-phenyl)-pyrrolo[2,1-f][1,2,4]triazin-2-ylamino]-phenyl}-morpholin-4-yl-methanone The compound was made in an analogous fashion to Example 327 replacing 2-Methanesulfinyl-7-(2-methoxy-phenyl)-pyrrolo[2,1-f][1,2,4]triazine with 7-(3-Chloro-phenyl)-2-methanesulfinyl-pyrrolo[2,1-f][1,2,4]triazine to afford 7.52 mg of {3-[7-(3-Chloro-phenyl)-pyrrolo[2,1-f][1,2,4]triazin-2-ylamino]-phenyl}-morpholin-4-yl-methanone as a lyophilized powder. (M+H)=434.7. $^1$H NMR (400 MHz, DMSO, d$_6$) δ 9.75 (s, 1H), 9.01 (s, 1H), 8.30 (s, 1H), 8.14 (d, 1H, J=7.88 Hz), 7.94 (m, 1H), 7.56 (s, 1H), 7.49 (m, 2H), 7.40 (m, 1H), 7.30 (d, 1H, J=4.76 Hz), 7.01 (m, 2H), 3.59 (m, 4H), 3.31 (m, 4H).

Example 330

1-[7-(4-Methanesulfonyl-phenyl)-pyrrolo[2,1-f][1,2,4]triazin-2-yl]-1H-imidazo[4,5-c]pyridine The compound was made in an analogous fashion to Example 322 replacing 2-Methanesulfinyl-7-(2-methoxy-phenyl)-pyrrolo[2,1-f][1,2,4]triazine with 2-Methanesulfinyl-7-(4-methanesulfonyl-phenyl)-pyrrolo[2,1-f][1,2,4]triazine to afford 16.33 mg of 1-[7-(4-Methanesulfonyl-phenyl)-pyrrolo[2,1-f][1,2,4]triazin-2-yl]-1H-imidazo[4,5-c]pyridine as a lyophilized powder. (M+H)=391.6. $^1$H NMR (400 MHz, DMSO, d$_6$) δ 9.53 (m, 3H), 8.81 (m, 1H), 8.62 (d, 1H, J=6.32 Hz), 8.54 (m, 2H), 8.18 (m, 2H), 7.81 (d, 1H, J=4.92 Hz), 7.46 (d, 1H, J=4.93 Hz), 2.50 (s, 3H).

Example 331

5-[2-(4-Morpholin-4-yl-phenylamino)-pyrrolo[2,1-f][1,2,4]triazin-7-yl]-pyridin-2-ol Palladium Acetate (0.018 g, 0.000080 mol) and Triphenylphosphine (0.026 g, 0.00010 mol) were dissolved in Tetrahydrofuran (1.2 mL, 0.015 mol) and the mixture was allowed to stir at room temperature for 10 minutes. (7-Bromo-pyrrolo[2,1-f][1,2,4]triazin-2-yl)-(4-morpholin-4-yl-phenyl)-amine (0.150 g, 0.000401 mol) was then added and the reaction was again allowed to stir for 10 minutes. 6-hydroxy-3-pyridine boronic acid (0.111 g, 0.000802 mol) was added followed by 0.9 M of Sodium carbonate in water (1 mL, 0.0009 mol) and Ethanol (1.2 mL, 0.021 mol). The reaction mixture was then heated at 80° C. and was allowed to stir overnight. The reaction mixture was poured over saturated sodium chloride, and organics were extracted with ethyl acetate. Combined organics were dried over sodium sulfate, filtered and reduced en vacuo. The crude mixture was purified by Gilson prep HPLC to afford 8.16 mg of 5-[2-(4-Morpholin-4-yl-phenylamino)-pyrrolo[2,1-f][1,2,4]triazin-7-yl]-pyridin-2-ol as a lyophilized powder. (M+H)=389.7. $^1$H NMR (400 MHz, DMSO, d$_6$) δ 9.27 (s, 1H), 8.89 (s, 1H), 8.42 (m, 1H), 8.13 (dd, 1H, J=2.60, 7.00 Hz), 7.58 (d, 2H, J=8.92 Hz), 7.06 (m, 3H), 6.90 (d, 1H, J=4.76 Hz), 6.52 (d, 1H, J=9.61 Hz), 3.77 (m, 4H), 3.11 (m, 4H).

Example 332

5-[2-(3-Morpholin-4-yl-phenylamino)-pyrrolo[2,1-f][1,2,4]triazin-7-yl]-pyridin-2-ol The compound was made in an analogous fashion to Example 331 replacing (7-Bromo-pyrrolo[2,1-f][1,2,4]triazin-2-yl)-(4-morpholin-4-yl-phenyl)-amine with (7-Bromo-pyrrolo[2,1-f][1,2,4]triazin-2-yl)-(3-morpholin-4-yl-phenyl)-amine to afford 2.16 mg of 5-[2-(3-Morpholin-4-yl-phenylamino)-pyrrolo[2,1-f][1,2,4]triazin-7-yl]-pyridin-2-ol as a lyophilized powder. (M+H)=389.7. $^1$H NMR (400 MHz, DMSO, d$_6$) δ 8.65 (m, 1H), 8.63 (s, 1H), 8.05 (dd, 1H, J=2.36, 7.16 Hz), 7.25 (m, 2H), 7.09 (m, 2H), 6.87 (d, 1H, J=4.88 Hz), 6.82 (d, 1H, J=4.80 Hz), 6.75 (d, 1H, J=9.60 Hz), 6.64 (d, 1H, J=8.09 Hz), 3.80 (m, 4H), 3.11 (m, 4H).

Example 333

[7-(2-Methoxy-phenyl)-pyrrolo[2,1-f][1,2,4]triazin-2-yl]-(4-morpholin-4-yl-phenyl)-amine 2-Methanesulfinyl-7-(2-methoxy-phenyl)-pyrrolo[2,1-f][1,2,4]triazine (125.0 mg, 0.0004350 mol), N,N-Diisopropylethylamine (0.114 mL, 0.000652 mol) and 4-(4-morpholino) aniline (0.155 g, 0.000870 mol) were dissolved in 1-Methoxy-2-propanol (1.2 mL, 0.013 mol) and The reaction was irradiated at 300 watts, 180° C. for 40 minutes or until HPLC showed consumption of starting material. The reaction mixture was then reduced en vacuo and the product was isolated and purified by Gilson prep HPLC to afford 12.51 mg of [7-(2-Methoxy-phenyl)-pyrrolo[2,1-f][1,2,4]triazin-2-yl]-(4-morpholin-4-yl-phenyl)-amine as a lyophilized powder. (M+H)=402.8. $^1$H NMR (400 MHz, DMSO, d$_6$) δ 9.23 (m, 1H), 8.91 (s, 1H), 7.81 (dd, 1H, J=1.60, 6.01 Hz), 7.62 (d, 2H, J=8.88 Hz), 7.45 (m, 1H), 7.21 (d, 1H, J=8.13 Hz), 7.12 (t, 1H, J=7.60 Hz), 6.91 (m, 4H), 3.80 (s, 3H), 3.75 (m, 4H), 3.09 (m, 4H).

Example 334

[7-(2-Methoxy-phenyl)-pyrrolo[2,1-f][1,2,4]triazin-2-yl]-[4-(4-morpholin-4-yl-piperidin-1-yl)-phenyl]-amine 2-Methanesulfinyl-7-(2-methoxy-phenyl)-pyrrolo[2,1-f][1,2,4]triazine (125.0 mg, 0.0004350 mol), N,N-Diisopropylethylamine (0.114 mL, 0.000652 mol) and 4-(4-Morpholin-4-yl-piperidin-1-yl)-phenylamine (0.227 g, 0.000870 mol) were dissolved in 1-Methoxy-2-propanol (1.2 mL, 0.013 mol) and The reaction was irradiated at 300 watts, 180° C. for 40 minutes or until HPLC showed consumption of starting material. The reaction mixture was then reduced en vacuo and the product was isolated and purified by Gilson prep HPLC to afford 44.36 mg of [7-(2-Methoxy-phenyl)-pyrrolo[2,1-f][1,2,4]triazin-2-yl]-[4-(4-morpholin-4-yl-piperidin-1-yl)-phenyl]-amine as a lyophilized powder. (M+H)=485.8. $^1$H NMR (400 MHz, DMSO, d$_6$) δ 9.20 (s, 1H), 8.91 (s, 1H), 7.82 (dd, 1H, J=1.56, 6.16 Hz), 7.60 (d, 2H, J=9.01 Hz), 7.45 (m, 1H), 7.21 (d, 1H, J=8.17 Hz), 7.12 (t, 1H, J=7.28 Hz), 6.90 (m, 4H), 4.02 (m, 2H), 3.80 (s, 3H), 3.50 (m, 5H), 3.35 (m, 2H), 3.24 (m, 2H), 2.71 (m, 2H), 2.12 (m, 2H), 1.70 (m, 2H).

Example 335

[7-(5-Chloro-2-methoxy-phenyl)-pyrrolo[2,1-f][1,2,4]triazin-2-yl]-[4-(4-morpholin-4-yl-piperidin-1-yl)-phenyl]-amine The compound was made in an analogous fashion to Example 334 replacing 2-Methanesulfinyl-7-(2-methoxy-phenyl)-pyrrolo[2,1-f][1,2,4]triazine with 7-(5-Chloro-2-methoxy-phenyl)-2-methanesulfinyl-pyrrolo[2,1-f][1,2,4]triazine to afford 2.89 mg of [7-(5-Chloro-2-methoxy-phenyl)-pyrrolo[2,1-f][1,2,4]triazin-2-yl]-[4-(4-morpholin-4-yl-piperidin-1-yl)-phenyl]-amine as a lyophilized powder. (M+H)=519.8. $^1$H NMR (400 MHz, DMSO, d$_6$) δ 9.28 (s, 1H), 8.95 (s, 1H), 8.09 (s, 1H), 7.60 (d, 2H, J=9.00 Hz), 7.48 (dd, 1H, J=2.60, 6.25 Hz), 7.23 (d, 1H, J=8.85 Hz), 7.03 (d, 1H, J=4.72 Hz), 6.91 (m, 3H), 4.00 (m, 2H), 3.83 (s, 3H), 3.73 (m, 4H), 3.51 (m, 5H), 3.12 (m, 2H), 2.66 (m, 2H), 2.16 (m, 2H), 1.74 (m, 2H).

Example 336

[7-(3-Chloro-phenyl)-pyrrolo[2,1-f][1,2,4]triazin-2-yl]-[4-(4-morpholin-4-yl-piperidin-1-yl)-phenyl]-amine The compound was made in an analogous fashion to Example 334 replacing 2-Methanesulfinyl-7-(2-methoxy-phenyl)-pyrrolo[2,1-f][1,2,4]triazine with 7-(3-Chloro-phenyl)-2-methanesulfinyl-pyrrolo[2,1-f][1,2,4]triazine to afford 4.02 mg of [7-(3-Chloro-phenyl)-pyrrolo[2,1-f][1,2,4]triazin-2-yl]-[4-(4-morpholin-4-yl-piperidin-1-yl)-phenyl]-amine as a lyophilized powder. (M+H)=489.8. $^1$H NMR (400 MHz, DMSO, d$_6$) δ 9.36 (s, 1H), 8.98 (s, 1H), 8.49 (s, 1H), 8.03 (d, 1H, J=7.85 Hz), 7.64 (d, 2H, J=8.97 Hz), 7.55 (t, 1H, J=8.00 Hz), 7.43 (m, 1H), 7.26 (d, 1H, J=4.72 Hz), 7.01 (d, 2H, J=8.85 Hz), 6.94 (d, 1H, J=4.76 Hz), 4.01 (m, 2H), 3.80 (m, 2H), 3.57 (m, 3H), 3.48 (m, 2H), 3.13 (m, 2H), 2.70 (m, 2H), 2.17 (m, 2H), 1.74 (m, 2H).

Example 337

[4-(4-Morpholin-4-yl-piperidin-1-yl)-phenyl]-(7-pyridin-3-yl-pyrrolo[2,1-f][1,2,4]triazin-2-yl)-amine The compound was made in an analogous fashion to Example 334 replacing 2-Methanesulfinyl-7-(2-methoxy-phenyl)-pyrrolo[2,1-f][1,2,4]triazine with 2-Methanesulfinyl-7-pyridin-3-yl-pyrrolo[2,1-f][1,2,4]triazine to afford 21.43 mg of [4-(4-Morpholin-4-yl-piperidin-1-yl)-phenyl]-(7-pyridin-3-yl-pyrrolo[2,1-f][1,2,4]triazin-2-yl)-amine as a lyophilized powder. (M+H)=456.8. $^1$H NMR (400 MHz, DMSO, $d_6$) δ 9.45 (m, 1H), 9.03 (s, 1H), 8.81 (m, 1H), 8.66 (d, 2H, J=4.97 Hz), 7.75 (m, 1H), 7.61 (d, 2H, J=9.00 Hz), 7.34 (d, 1H, J=4.80 Hz), 7.13 (d, 1H, J=4.88 Hz), 7.05 (m, 1H), 6.99 (d, 1H, J=4.80 Hz), 4.48 (m, 2H), 3.82 (m, 2H), 3.75 (m, 2H), 3.49 (m, 2H), 3.37 (m, 1H), 3.13 (m, 2H), 2.75 (m, 2H), 2.18 (m, 2H), 1.75 (m, 2H).

Example 338

{3-[7-(2-Methoxy-phenyl)-pyrrolo[2,1-f][1,2,4]triazin-2-ylamino]-phenyl}-(4-methyl-piperazin-1-yl)-methanone 338a. (4-Methyl-piperazin-1-yl)-(3-nitro-phenyl)-methanone m-Nitrobenzoic acid (2.00 g, 0.0120 mol), piperazine, 1-methyl- (1.44 g, 0.0144 mol), N-(3-Dimethylaminopropyl)-N'-ethylcarbodiimide hydrochloride (2.29 g, 0.0120 mol) and 1-Hydroxybenzotriazole (0.40 g, 0.0030 mol) were dissolved in Tetrahydrofuran (35 mL, 0.43 mol) and the reaction was allowed to stir overnight at room temperature. The reaction mixture was poured over saturated sodium bicarbonate, and organics were extracted with ethyl acetate/dichloromethane. Combined organics were dried over sodium sulfate, filtered and reduced en vacuo. The crude mixture was purified by Isco flash column chromatography (Hexane/Ethyl Acetate). Combined fractions were reduced en vacuo to afford 2.46 g of (4-Methyl-piperazin-1-yl)-(3-nitro-phenyl)-methanone. (M+H)=250.6.

338b. (3-Amino-phenyl)-(4-methyl-piperazin-1-yl)-methanone (4-Methyl-piperazin-1-yl)-(3-nitro-phenyl)-methanone (2.46 g, 9.87 mmol) was dissolved in Ethanol (30.0 mL, 514 mmol) and the solution was carefully added to a Parr vessel containing 10% Palladium on Carbon (0.750 g, 56.2 mmol) under nitrogen. The mixture was then placed on a Parr hydrogenation apparatus and was allowed to shake at 55 psi until uptake of hydrogen ceased. The catalyst was then filtered to afford 1.75 g of (3-Amino-phenyl)-(4-methyl-piperazin-1-yl)-methanone without further purification. (M+H)=220.6.

338c. {3-[7-(2-Methoxy-phenyl)-pyrrolo[2,1-f][1,2,4]triazin-2-ylamino]-phenyl}-(4-methyl-piperazin-1-yl)-methanone 2-Methanesulfinyl-7-(2-methoxy-phenyl)-pyrrolo[2,1-f][1,2,4]triazine (125.0 mg, 0.0004350 mol), N,N-Diisopropylethylamine (0.114 mL, 0.000652 mol) and (3-Amino-phenyl)-(4-methyl-piperazin-1-yl)-methanone (0.191 g, 0.000870 mol) were dissolved in 1-Methoxy-2-propanol (1.2 mL, 0.013 mol) and the reaction was irradiated at 300 watts, 180° C. for 40 minutes or until HPLC showed consumption of starting material. The reaction mixture was then reduced en vacuo and the product was isolated and purified by Gilson prep HPLC to afford 40.55 mg of {3-[7-(2-Methoxy-phenyl)-pyrrolo[2,1-f][1,2,4]triazin-2-ylamino]-phenyl}-(4-methyl-piperazin-1-yl)-methanone as a lyophilized powder. (M+H)= 443.9. $^1$H NMR (400 MHz, DMSO, $d_6$) δ 9.63 (s, 1H), 8.99 (s, 1H), 7.76 (m, 3H), 7.45 (t, 1H, J=7.12 Hz), 7.30 (t, 1H, 7.84 Hz), 7.18 (d, 1H, J=8.25 Hz), 7.08 (t, 1H, J=7.45 Hz), 6.96 (m, 3H), 4.05 (m, 2H), 3.81 (s, 3H), 3.44 (m, 2H), 3.19 (m, 2H), 2.99 (m, 2H), 2.82 (s, 3H).

Example 339

{3-[7-(5-Chloro-2-methoxy-phenyl)-pyrrolo[2,1-f][1,2,4]triazin-2-ylamino]-phenyl}-(4-methyl-piperazin-1-yl)-methanone The compound was made in an analogous fashion to Example 338 replacing 2-Methanesulfinyl-7-(2-methoxy-phenyl)-pyrrolo[2,1-f][1,2,4]triazine with 7-(5-Chloro-2-methoxy-phenyl)-2-methanesulfinyl-pyrrolo[2,1-f][1,2,4]triazine to afford 2.89 mg of {3-[7-(5-Chloro-2-methoxy-phenyl)-pyrrolo[2,1-f][1,2,4]triazin-2-ylamino]-phenyl}-(4-methyl-piperazin-1-yl)-methanone as a lyophilized powder. (M+H)=477.8. $^1$H NMR (400 MHz, DMSO, $d_6$) δ 9.69 (s, 1H), 9.02 (s, 1H), 8.02 (m, 1H), 7.92 (m, 1H), 7.57 (m, 1H), 7.48 (dd, 1H, J=2.72, 6.16 Hz), 7.35 (t, 1H, J=7.84 Hz), 7.21 (d, 1H, J=8.97 Hz), 7.05 (d, 1H, J=4.68 Hz), 6.97 (m, 2H), 3.81 (s, 3H), 3.79 (m, 2H), 3.48 (m, 2H), 3.21 (m, 2H), 3.05 (m, 2H), 2.82 (s, 3H).

Example 340

{3-[7-(3-Chloro-phenyl)-pyrrolo[2,1-f][1,2,4]triazin-2-ylamino]-phenyl}-(4-methyl-piperazin-1-yl)-methanone The compound was made in an analogous fashion to Example 338 replacing 2-Methanesulfinyl-7-(2-methoxy-phenyl)-pyrrolo[2,1-f][1,2,4]triazine with 7-(3-Chloro-phenyl)-2-methane sulfinyl-pyrrolo[2,1-f][1,2,4]triazine to afford 34.13 mg of {3-[7-(3-Chloro-phenyl)-pyrrolo[2,1-f][1,2,4]triazin-2-ylamino]-phenyl}-(4-methyl-piperazin-1-yl)-methanone as a lyophilized powder. (M+H)=447.8. $^1$H NMR (400 MHz, DMSO, $d_6$) δ 9.78 (s, 1H), 9.06 (s, 1H), 8.33 (m, 1H), 8.13 (d, 1H, J=7.88 Hz), 8.02 (d, 1H, J=9.53 Hz), 7.72 (m, 1H), 7.55 (t, 1H, J=7.88 Hz), 7.45 (m, 2H), 7.33 (d, 1H, J=4.80 Hz), 7.07 (d, 1H, J=7.64 Hz), 7.01 (d, 1H, J=4.80 Hz), 3.68 (m, 4H), 3.46 (m, 2H), 3.04 (m, 2H), 2.82 (s, 3H).

Example 341

(4-Methyl-piperazin-1-yl)-[3-(7-pyridin-3-yl-pyrrolo[2,1-f][1,2,4]triazin-2-ylamino)-phenyl]-methanone The compound was made in an analogous fashion to Example 338 replacing 2-Methanesulfinyl-7-(2-methoxy-phenyl)-pyrrolo[2,1-f][1,2,4]triazine with 2-Methanesulfinyl-7-pyridin-3-yl-pyrrolo[2,1-f][1,2,4]triazine to afford 37.81 mg of {(4-Methyl-piperazin-1-yl)-[$_3$-(7-pyridin-3-yl-pyrrolo[2,1-f][1,2,4]triazin-2-ylamino)-phenyl]-methanone as a lyophilized powder. (M+H)=414.8. $^1$H NMR (400 MHz, DMSO, $d_6$) δ 9.82 (s, 1H), 9.38 (s, 1H), 9.09 (s, 1H), 8.65 (m, 2H), 7.91 (m, 1H), 7.53 (m, 1H), 7.45 (m, 1H), 7.37 (m, 2H), 7.05 (m, 2H), 4.48 (m, 4H), 3.74 (m, 2H), 3.28 (m, 2H), 2.83 (s, 3H).

Example 342

{3-[7-(4-Methanesulfonyl-phenyl)-pyrrolo[2,1-f][1,2,4]triazin-2-ylamino]-phenyl}-(4-methyl-piperazin-1-yl)-methanone The compound was made in an analogous fashion to Example 338 replacing 2-Methanesulfinyl-7-(2-methoxyphenyl)-pyrrolo[2,1-f][1,2,4]triazine with 2-Methanesulfinyl-7-(4-methanesulfonyl-phenyl)-pyrrolo[2,1-f][1,2,4]triazine to afford 11.25 mg of {3-[7-(4-Methanesulfonyl-phenyl)-pyrrolo[2,1-f][1,2,4]triazin-2-ylamino]-phenyl}-(4-methyl-piperazin-1-yl)-methanone as a lyophilized powder. (M+H)=492.2. $^1$H NMR (400 MHz, DMSO, $d_6$) δ 9.85 (s, 1H), 9.10 (s, 1H), 8.45 (dd, 2H, J=1.77, 5.08 Hz), 8.06 (m, 3H), 7.71 (dd, 1H, J=1.28, 6.89 Hz), 7.48 (m, 1H), 7.40 (d, 1H, J=4.80 Hz), 7.09 (m, 1H), 7.04 (d, 1H, J=4.79 Hz), 3.52 (m, 4H), 3.27 (s, 3H), 3.00 (m, 2H), 2.82 (s, 3H), 2.56 (m, 2H).

Example 343

[7-(2-Methoxy-phenyl)-pyrrolo[2,1-f][1,2,4]triazin-2-yl]-[4-(3-morpholin-4-yl-piperidin-1-yl)-phenyl]-amine 343a. 3-Morpholin-4-yl-piperidine-1-carboxylic acid tert-butyl ester 3-Oxo-piperidine-1-carboxylic acid tert-butyl ester (2.0 g, 1.0E1 mmol) and Morpholine (0.962 g, 11.0 mmol) were dissolved in a solution of Acetic acid (0.500 mL, 8.79 mmol) and Methylene chloride (50.0 mL, 7.80E2 mmol). After stirring at room temperature for 15 minutes, Sodium triacetoxyborohydride (4.2 g, 2.0E1 mmol) was added and the reaction was allowed to stir overnight at room temperature. The reaction mixture was poured over saturated sodium bicarbonate and organics were extracted with dichloromethane/ethyl acetate. Combined extracts were then dried over sodium sulfate, filtered and reduced. TLC (visualized with iodine) showed evidence of a new product. Crude 3-Morpholin-4-yl-piperidine-1-carboxylic acid tert-butyl ester (3.67 g) was used in the next synthetic step without further purification.

343b. 4-Piperidin-3-yl-morpholine

3-Morpholin-4-yl-piperidine-1-carboxylic acid tert-butyl ester (2.70 g, 9.99 mmol) was dissolved in Methylene chloride (50.0 mL, 7.80E2 mmol) and the reaction mixture was treated with Trifluoroacetic Acid (6.0 mL, 78 mmol). The reaction was allowed to stir overnight at room temperature. The solvent was then removed en vacuo to afford the -Piperidin-3-yl-morpholine as a TFA salt. (M+H)=171.06. The crude product contained TFA which was neutralized in the next step. Crude NMR showed evidence of product formation. $^1$H NMR (400 MHz, DMSO, $d_6$) δ 8.99 (m, 1H), 3.68 (m, 2H), 3.48 (m, 2H), 3.28 (m, 5H), 3.10 (m, 2H), 2.81 (m, 2H), 1.97 (m, 2H), 1.66 (m, 2H).

343c. 4-[1-(4-Nitro-phenyl)-piperidin-3-yl]-morpholine

4-Piperidin-3-yl-morpholine (1.70 g, 9.98 mmol), 4-Fluoronitrobenzene (1.3 g, 9.1 mmol) and Potassium carbonate (3.14 g, 22.7 mmol) were dissolved in N,N-Dimethylformamide (60 mL, 800 mmol). The reaction mixture was then heated at 100° C. and was allowed to stir overnight. The reaction mixture was poured over saturated ammonium chloride and organics were extracted with dichloromethane/ethyl acetate. Combined extracts were then dried over sodium sulfate, filtered and reduced. The crude reaction mixture was then purified by Isco flash column chromatography (hexanes/ethyl acetate eluent). Combined fractions were reduced and dried under vacuum to afford 4-[1-(4-Nitro-phenyl)-piperidin-3-yl]-morpholine. (M+H)=292.6. $^1$H NMR (400 MHz, DMSO, $d_6$) δ 8.02 (d, 2H, J=9.45 Hz), 6.99 (d, 2H, J=9.48 Hz), 4.08 (m, 1H), 3.98 (m, 1H), 3.56 (t, 4H, J=4.56 Hz), 2.96 (m, 2H), 2.62 (m, 2H), 2.52 (m, 2H), 2.31 (m, 1H), 1.93 (m, 1H), 1.80 (m, 1H), 1.50 (m, 2H).

343d. 4-(3-Morpholin-4-yl-piperidin-1-yl)-phenylamine

4-[1-(4-Nitro-phenyl)-piperidin-3-yl]-morpholine (1.30 g, 4.46 mmol) was dissolved in Ethanol (35.0 mL, 599 mmol) and the solution was carefully added to 10% Palladium on Carbon (0.500 g, 37.5 mmol) under nitrogen. The mixture was then placed on a Parr hydrogenation apparatus and was allowed to shake at 55 psi until uptake of hydrogen ceased. The catalyst was then filtered to afford 1.16 g of 4-(3-Morpholin-4-yl-piperidin-1-yl)-phenylamine without further purification. (M+H)=262.7. $^1$H NMR (400 MHz, DMSO, $d_6$) δ 6.67 (d, 2H, J=8.72 Hz), 6.47 (d, 2H, J=10.09 Hz), 4.54 (s, 2H), 3.55 (m, 4H), 3.41 (m, 1H), 3.22 (m, 1H), 2.51 (m, 4H), 2.40 (m, 3H), 1.86 (m, 1H), 1.76 (m, 1H), 1.56 (m, 1H), 1.18 (m, 1H).

343e. [7-(2-Methoxy-phenyl)-pyrrolo[2,1-f][1,2,4]triazin-2-yl]-[4-(3-morpholin-4-yl-piperidin-1-yl)-phenyl]-amine 2-Methanesulfinyl-7-(2-methoxy-phenyl)-pyrrolo[2,1-f][1,2,4]triazine (100.0 mg, 0.0003480 mol), N,N-Diisopropylethylamine (0.0909 mL, 0.000522 mol) and 4-(3-Morpholin-4-yl-piperidin-1-yl)-phenylamine (0.182 g, 0.000696 mol) were dissolved in 1-Methoxy-2-propanol (0.99 mL, 0.010 mol) and the reaction was irradiated at 300 watts, 180° C. for 40 minutes or until HPLC showed consumption of starting material. The reaction mixture was then reduced en vacuo and the product was isolated and purified by Gilson prep HPLC to afford 61.16 mg of [7-(2-Methoxy-phenyl)-pyrrolo[2,1-f][1,2,4]triazin-2-yl]-[4-(3-morpholin-4-yl-piperidin-1-yl)-phenyl]-amine as a lyophilized powder. (M+H)=486.3. $^1$H NMR (400 MHz, DMSO, $d_6$) δ 9.20 (m, 1H), 8.92 (s, 1H), 7.84 (dd, 1H, J=1.67, 5.97 Hz), 7.61 (d, 2H, J=9.00 Hz), 7.45 (m, 1H), 7.21 (d, 1H, J=8.00 Hz), 7.15 (m, 1H), 6.91 (m, 4H), 4.33 (m, 2H), 3.77 (s, 3H), 3.74 (m, 2H), 3.42 (m, 3H), 2.90 (m, 2H), 2.67 (m, 2H), 2.13 (m, 2H), 1.75 (m, 2H), 1.61 (m, 2H).

Example 344

[7-(5-Chloro-2-methoxy-phenyl)-pyrrolo[2,1-f][1,2,4]triazin-2-yl]-[4-(3-morpholin-4-yl-piperidin-1-yl)-phenyl]-amine The compound was made in an analogous fashion to Example 343 replacing 2-Methanesulfinyl-7-(2-methoxyphenyl)-pyrrolo[2,1-f][1,2,4]triazine with 7-(5-Chloro-2-methoxy-phenyl)-2-methanesulfinyl-pyrrolo[2,1-f][1,2,4]triazine to afford 110.52 mg of 7-(5-Chloro-2-methoxyphenyl)-pyrrolo[2,1-f][1,2,4]triazin-2-yl]-[4-(3-morpholin-4-yl-piperidin-1-yl)-phenyl]-amine as a lyophilized powder. (M+H)=519.8. $^1$H NMR (400 MHz, DMSO, $d_6$) δ 9.29 (s, 1H), 8.98 (s, 1H), 8.08 (s, 1H), 7.62 (d, 2H, J=9.05 Hz), 7.47 (dd, 1H, J=2.73, 6.11 Hz), 7.23 (d, 1H, J=9.00 Hz), 7.03 (d, 1H, J=4.68 Hz), 6.95 (d, 2H, J=9.04 Hz), 6.90 (d, 1H, J=4.73 Hz), 3.88 (s, 3H), 3.81 (m, 4H), 3.72 (m, 4H), 2.88 (m, 2H), 2.66 (m, 1H), 2.15 (m, 2H), 1.87 (m, 2H), 1.62 (m, 2H).

Example 345

[7-(3-Chloro-phenyl)-pyrrolo[2,1-f][1,2,4]triazin-2-yl]-[4-(3-morpholin-4-yl-piperidin-1-yl)-phenyl]-amine The compound was made in an analogous fashion to Example 343 replacing 2-Methanesulfinyl-7-(2-methoxyphenyl)-pyrrolo[2,1-f][1,2,4]triazine with 7-(3-Chloro-phenyl)-2-methanesulfinyl-pyrrolo[2,1-f][1,2,4]triazine to afford 75.31 mg of [7-(3-Chloro-phenyl)-pyrrolo[2,1-f][1,2,4]triazin-2-yl]-[4-(3-morpholin-4-yl-piperidin-1-yl)-phenyl]-amine as a lyophilized powder. (M+H)=489.8. $^1$H NMR (400 MHz, DMSO, $d_6$) δ 9.37 (s, 1H), 9.04 (s, 1H), 8.46 (s, 1H), 8.00 (m, 1H), 7.73 (d, 2H, J=6.32 Hz), 7.61 (m, 1H), 7.48 (m, 1H), 7.34 (m, 1H), 7.18 (m, 2H), 6.88 (m, 1H), 3.92 (m, 3H), 3.85 (m, 4H), 3.49 (m, 4H), 2.92 (m, 1H), 2.71 (m, 1H), 2.25 (m, 1H), 1.80 (m, 1H), 1.70 (m, 2H).

Example 346

[7-(4-Methanesulfonyl-phenyl)-pyrrolo[2,1-f][1,2,4]triazin-2-yl]-[4-(3-morpholin-4-yl-piperidin-1-yl)-phenyl]-amine The compound was made in an analogous fashion to Example 343 replacing 2-Methanesulfinyl-7-(2-methoxyphenyl)-pyrrolo[2,1-f][1,2,4]triazine with 2-Methanesulfinyl-7-(4-methanesulfonyl-phenyl)-pyrrolo[2,1-f][1,2,4]triazine to afford 39.97 mg of [7-(4-Methanesulfonyl-phenyl)-pyrrolo[2,1-f][1,2,4]triazin-2-yl]-[4-(3-morpholin-4-yl-piperidin-1-yl)-phenyl]-amine as a lyophilized powder. (M+H)=533.8. $^1$H NMR (400 MHz, DMSO, $d_6$) δ 9.31 (s, 1H), 9.01 (s, 1H), 8.47 (m, 2H), 8.03 (m, 2H), 7.55 (m, 2H), 7.33 (m, 1H), 6.95 (m, 3H), 3.71 (m, 1H), 3.59 (m, 5H), 3.29 (s, 3H), 2.59 (m, 5H), 2.38 (m, 2H), 1.94 (m, 1H), 1.79 (m, 1H), 1.57 (m, 1H), 1.31 (m, 1H).

Example 347

[4-(3-Morpholin-4-yl-piperidin-1-yl)-phenyl]-(7-pyridin-3-yl-pyrrolo[2,1-f][1,2,4]triazin-2-yl)-amine The compound was made in an analogous fashion to Example 343 replacing 2-Methanesulfinyl-7-(2-methoxyphenyl)-pyrrolo[2,1-f][1,2,4]triazine with 2-Methanesulfinyl-7-pyridin-3-yl-pyrrolo[2,1-f][1,2,4]triazine to afford 150.42 mg of [4-(3-Morpholin-4-yl-piperidin-1-yl)-phenyl]-(7-pyridin-3-yl-pyrrolo[2,1-f][1,2,4]triazin-2-yl)-amine as a lyophilized powder. (M+H)=456.8. $^1$H NMR (400 MHz, DMSO, $d_6$) δ 9.54 (s, 1H), 9.46 (s, 1H), 9.10 (s, 1H), 8.95 (m, 1H), 8.72 (m, 1H), 7.80 (m, 1H), 7.63 (m, 2H), 7.43 (m, 1H), 7.01 (m, 2H), 6.97 (m, 1H), 3.97 (m, 2H), 3.92 (m, 2H), 3.61 (m, 2H), 3.45 (m, 2H), 3.17 (m, 3H), 2.91 (m, 1H), 2.70 (m, 1H), 2.21 (m, 1H), 1.90 (m, 1H), 1.58 (m, 2H).

Example 348

[7-(2-Methoxy-phenyl)-pyrrolo[2,1-f][1,2,4]triazin-2-yl]-{4-[3-(4-methyl-piperazin-1-yl)-piperidin-1-yl]-phenyl}-amine 348a. 3-(4-Methyl-piperazin-1-yl)-piperidine-1-carboxylic acid tert-butyl ester 3-Oxo-piperidine-1-carboxylic acid tert-butyl ester (2.0 g, 1.0E1 mmol) and piperazine, 1-methyl- (1.10 g, 11.0 mmol) were dissolved in a solution of Acetic acid (0.500 mL, 8.79 mmol) and Methylene chloride (50.0 mL, 7.80E2 mmol). After stirring at room temperature for 15 minutes, Sodium triacetoxyborohydride (4.2 g, 2.0E1 mmol) was added and the reaction was allowed to stir overnight at room temperature. The reaction mixture was poured over saturated sodium bicarbonate and organics were extracted with dichloromethane/ethyl acetate. Combined extracts were then dried over sodium sulfate, filtered and reduced. TLC showed evidence of a new product (iodine visualization). 2.25 g of crude 3-(4-Methyl-piperazin-1-yl)-piperidine-1-carboxylic acid tert-butyl ester was used without further purification.

348b. 1-Methyl-4-piperidin-3-yl-piperazine 3-(4-Methyl-piperazin-1-yl)-piperidine-1-carboxylic acid tert-butyl ester (2.25 g, 7.94 mmol) was dissolved in Methylene chloride (50.0 mL, 7.80E2 mmol) and the reaction mixture was treated with Trifluoroacetic Acid (6.0 mL, 78 mmol). The reaction was allowed to stir overnight at room temperature. The solvent was then removed en vacuo to afford 1-Methyl-4-piperidin-3-yl-piperazine as a TFA salt. The crude product contained excess TFA, which was neutralized in the next synthetic step. (M+H)=184.09.

348c. 1-Methyl-4-[1-(4-nitro-phenyl)-piperidin-3-yl]-piperazine

1-Methyl-4-piperidin-3-yl-piperazine (1.46 g, 7.96 mmol), 4-Fluoronitrobenzene (1.0 g, 7.2 mmol) and Potassium carbonate (2.50 g, 18.1 mmol) were dissolved in N,N-Dimethylformamide (50 mL, 600 mmol). The reaction mixture was then heated at 100° C. and was allowed to stir overnight. The reaction mixture was poured over saturated ammonium chloride and organics were extracted with dichloromethane/ethyl acetate. Combined extracts were then dried over sodium sulfate, filtered and reduced. The crude reaction mixture was then purified by Isco flash column chromatography (hexanes/ethyl acetate eluent). Combined fractions were reduced and dried under vacuum to afford 1.40 g of 1-Methyl-4-[1-(4-nitro-phenyl)-piperidin-3-yl]-piperazine.

348d. 4-[3-(4-Methyl-piperazin-1-yl)-piperidin-1-yl]-phenylamine

1-Methyl-4-[1-(4-nitro-phenyl)-piperidin-3-yl]-piperazine (1.40 g, 4.60 mmol) was dissolved in Ethanol (36.1 mL, 618 mmol) and the solution was carefully added to 10% Palladium on Carbon (0.515 g, 38.6 mmol) under nitrogen. The mixture was then placed on a Parr hydrogenation apparatus and was allowed to shake at 55 psi until uptake of hydrogen ceased. The catalyst was then filtered to afford 0.960 g of 4-[3-(4-Methyl-piperazin-1-yl)-piperidin-1-yl]-phenylamine without further purification. (M+H)=275.7. $^1$H NMR (400 MHz, DMSO, $d_6$) δ 6.67 (d, 2H, J=8.56 Hz), 6.47 (d, 2H, J=8.51 Hz), 4.54 (s, 2H), 3.39 (m, 2H), 3.20 (m, 1H), 2.62 (m, 4H), 2.33 (m, 6H), 2.12 (s, 3H), 1.85 (m, 1H), 1.74 (m, 1H), 1.52 (m, 1H), 1.18 (m, 1H).

348e. [7-(2-Methoxy-phenyl)-pyrrolo[2,1-f][1,2,4]triazin-2-yl]-{4-[3-(4-methyl-piperazin-1-yl)-piperidin-1-yl]-phenyl}-amine 2-Methanesulfinyl-7-(2-methoxy-phenyl)-pyrrolo[2,1-f][1,2,4]triazine (100.0 mg, 0.0003480 mol), N,N-Diisopropylethylamine (0.0909 mL, 0.000522 mol) and 4-[3-(4-Methyl-piperazin-1-yl)-piperidin-1-yl]-phenylamine (0.191 g, 0.000696 mol) were dissolved in 1-Methoxy-2-propanol (0.99 mL, 0.010 mol) and the reaction was irradiated at 300 watts, 180° C. for 40 minutes or until HPLC showed consumption of starting material. The reaction mixture was then reduced en vacuo and the product was isolated and purified by Gilson prep HPLC to afford 78.00 mg of [7-(2-Methoxy-phenyl)-pyrrolo[2,1-f][1,2,4]triazin-2-yl]-{4-[3-(4-methyl-piperazin-1-yl)-piperidin-1-yl]-phenyl}-amine as a lyophilized powder. (M+H)=498.3. $^1$H NMR (400 MHz, DMSO, $d_6$) δ 9.37 (s, 1H), 8.93 (s, 1H), 7.81 (dd, 1H, J=1.62, 5.96 Hz), 7.67 (d, 2H, J=8.56 Hz), 7.45 (m, 1H), 7.21 (d, 1H, J=8.05 Hz), 7.11 (m, 3H), 6.92 (m, 2H), 3.92 (m, 4H), 3.79 (s, 3H), 3.62 (m, 2H), 3.45 (m, 3H), 3.31 (m, 2H), 3.13 (m, 2H), 2.79 (m, 3H), 1.99 (m, 1H), 1.88 (m, 1H), 1.67 (m, 1H), 1.51 (m, 1H).

Example 349

[7-(5-Chloro-2-methoxy-phenyl)-pyrrolo[2,1-f][1,2,4]triazin-2-yl]-{4-[3-(4-methyl-piperazin-1-yl)-piperidin-1-yl]-phenyl}-amine The compound was made in an analogous fashion to Example 348 replacing 2-Methanesulfinyl-7-(2-methoxy-phenyl)-pyrrolo[2,1-f][1,2,4]triazine with 7-(5-Chloro-2-methoxy-phenyl)-2-methanesulfinyl-pyrrolo[2,1-f][1,2,4]triazine to afford 82.62 mg of [7-(5-Chloro-2-methoxy-phenyl)-pyrrolo[2,1-f][1,2,4]triazin-2-yl]-{4-[3-(4-methyl-piperazin-1-yl)-piperidin-1-yl]-phenyl}-amine as a lyophilized powder. (M+H)=532.2. $^1$H NMR (400 MHz, DMSO, $d_6$) δ 9.43 (s, 1H), 8.96 (s, 1H), 8.07 (s, 1H), 7.68 (d, 2H, J=8.92 Hz), 7.47 (dd, 1H, J=2.72, 6.17 Hz), 7.23 (d, 1H, J=9.00 Hz), 7.19 (m, 2H), 7.12 (d, 1H, J=4.60 Hz), 6.92 (d, 1H, J=4.64 Hz), 3.78 (s, 3H), 3.64 (m, 6H), 3.44 (m, 3H), 3.10 (m, 2H), 2.96 (m, 2H), 2.83 (s, 3H), 1.99 (m, 1H), 1.88 (m, 1H), 1.69 (m, 1H), 1.52 (m, 1H).

Example 350

[7-(3-Chloro-phenyl)-pyrrolo[2,1-f][1,2,4]triazin-2-yl]-{4-[3-(4-methyl-piperazin-1-yl)-piperidin-1-yl]-phenyl}-amine The compound was made in an analogous fashion to Example 348 replacing 2-Methanesulfinyl-7-(2-methoxy-phenyl)-pyrrolo[2,1-f][1,2,4]triazine with 7-(3-Chloro-phenyl)-2-methanesulfinyl-pyrrolo[2,1-f][1,2,4]triazine to afford 82.13 mg of [7-(3-Chloro-phenyl)-pyrrolo[2,1-f][1,2,4]triazin-2-yl]-{4-[3-(4-methyl-piperazin-1-yl)-piperidin-1-yl]-phenyl}-amine as a lyophilized powder. (M+H)=502.2. $^1$H NMR (400 MHz, DMSO, $d_6$) δ 9.46 (s, 1H), 8.98 (s, 1H), 8.49 (s, 1H), 8.05 (m, 1H), 7.69 (d, 2H, J=8.88 Hz), 7.54 (t, 1H, J=7.96 Hz), 7.43 (m, 1H), 7.28 (d, 1H, J=4.80 Hz), 7.15 (m, 2H), 6.96 (d, 1H, J=4.80 Hz), 3.57 (m, 2H), 3.46 (m, 5H), 3.28 (m, 2H), 3.15 (m, 2H), 3.06 (m, 2H), 2.92 (s, 3H), 2.01 (m, 1H), 1.87 (m, 1H), 1.65 (m, 1H), 1.49 (m, 1H).

Example 351

[7-(4-Methanesulfonyl-phenyl)-pyrrolo[2,1-f][1,2,4]triazin-2-yl]-{4-[3-(4-methyl-piperazin-1-yl)-piperidin-1-yl]-phenyl}-amine The compound was made in an analogous fashion to Example 348 replacing 2-Methanesulfinyl-7-(2-methoxy-phenyl)-pyrrolo[2,1-f][1,2,4]triazine with 2-Methanesulfinyl-7-(4-methanesulfonyl-phenyl)-pyrrolo[2,1-f][1,2,4]triazine to afford 44.53 mg of [7-(4-Methanesulfonyl-phenyl)-pyrrolo[2,1-f][1,2,4]triazin-2-yl]-{4-[3-(4-methyl-piperazin-1-yl)-piperidin-1-yl]-phenyl}-amine as a lyophilized powder. (M+H)=546.2. $^1$H NMR (400 MHz, DMSO, $d_6$) δ 9.45 (s, 1H), 9.05 (s, 1H), 8.50 (m, 2H), 8.09 (m, 2H), 7.65 (d, 2H, J=8.73 Hz), 7.35 (d, 1H, J=4.80 Hz), 7.13 (m, 2H), 6.98 (d, 1H, J=4.84 Hz), 3.94 (m, 2H), 3.89 (m, 4H), 3.53 (m, 3H), 3.31 (s, 3h), 2.81 (s, 3H), 2.62 (m, 2H), 2.35 (m, 2H), 2.06 (m, 1H), 1.82 (m, 1H), 1.72 (m, 1H), 1.52 (m, 1H).

Example 352

{4-[3-(4-Methyl-piperazin-1-yl)-piperidin-1-yl]-phenyl}-(7-pyridin-3-yl-pyrrolo[2,1-f][1,2,4]triazin-2-yl)-amine The compound was made in an analogous fashion to Example 348 replacing 2-Methanesulfinyl-7-(2-methoxy-phenyl)-pyrrolo[2,1-f][1,2,4]triazine with 2-Methanesulfinyl-7-pyridin-3-yl-pyrrolo[2,1-f][1,2,4]triazine to afford 107.22 mg of {4-[3-(4-Methyl-piperazin-1-yl)-piperidin-1-yl]-phenyl}-(7-pyridin-3-yl-pyrrolo[2,1-f][1,2,4]triazin-2-yl)-amine as a lyophilized powder. (M+H)=469.3. $^1$H NMR (400 MHz, DMSO, $d_6$) δ 9.54 (s, 1H), 9.43 (s, 1H), 9.03 (s, 1H), 8.77 (m, 1H), 8.68 (m, 1H), 7.75 (m, 1H), 7.62 (m, 2H), 7.35 (d, 1H, J=4.80 Hz), 7.17 (m, 2H), 7.03 (d, 1H, J=4.80 Hz), 4.12 (m, 2H), 3.73 (m, 2H), 3.54 (m, 2H), 3.45 (m, 3H), 3.41 (m, 2H), 3.02 (m, 2H), 2.96 (s, 3H), 2.07 (m, 1H), 1.90 (m, 1H), 1.60 (m, 1H), 1.54 (m, 1H).

Example 353

[7-(2-Methoxy-phenyl)-pyrrolo[2,1-f][1,2,4]triazin-2-yl]-[4-(4-methyl-piperazin-1-ylmethyl)-phenyl]-amine 353a. 1-Methyl-4-(4-nitro-benzyl)-piperazine p-Nitrobenzaldehyde (2.50 g, 16.5 mmol) and piperazine, 1-methyl- (3.31 g, 33.1 mmol) were dissolved in Acetic acid (2.0 mL, 35 mmol) and Methylene chloride (100 mL, 2000 mmol) and the solution was allowed to stir at room temperature for approximately 15 minutes. Sodium triacetoxyborohydride (5.26 g, 24.8 mmol) was then added and the reaction was allowed to stir overnight. The reaction mixture was poured over saturated sodium bicarbonate and organics were extracted with dichloromethane. Combined extracts were then dried over sodium sulfate, filtered and reduced. The crude reaction mixture was then purified by Isco flash column chromatography (hexanes/ethyl acetate eluent). Combined fractions were reduced and dried under vacuum to afford 3.77 g of 1-Methyl-4-(4-nitro-benzyl)-piperazine. (M+H)=236.6.

353b. 4-(4-Methyl-piperazin-1-ylmethyl)-phenylamine

1-Methyl-4-(4-nitro-benzyl)-piperazine (3.70 g, 15.7 mmol) was dissolved in Methanol (40.0 mL, 987 mmol) and was carefully added to a Parr vessel containing 10% Palladium on Carbon (1.00 g, 74.9 mmol) under nitrogen. The mixture was then placed on a Parr hydrogenation apparatus and was allowed to shake at 55 psi until uptake of hydrogen ceased. The catalyst was then filtered to afford 3.00 g of 4-(4-Methyl-piperazin-1-ylmethyl)-phenylamine without further purification. (M+H)=205.96.

353c. [7-(2-Methoxy-phenyl)-pyrrolo[2,1-f][1,2,4]triazin-2-yl]-[4-(4-methyl-piperazin-1-ylmethyl)-phenyl]-amine 2-Methanesulfinyl-7-(2-methoxy-phenyl)-pyrrolo[2,1-f][1,2,4]triazine (125.0 mg, 0.0004350 mol), N,N-Diisopropylethylamine (0.3789 mL, 0.002175 mol) and 4-(4-Methyl-piperazin-1-ylmethyl)-phenylamine (0.179 g, 0.000870 mol) were dissolved in 1-Methoxy-2-propanol (0.500 mL, 0.00512 mol) and the reaction was irradiated at 300 watts, 180° C. for 40 minutes or until HPLC showed consumption of starting material. The reaction mixture was then reduced en vacuo and the product was isolated and purified by Gilson prep HPLC to afford 46.12 mg of [7-(2-Methoxy-phenyl)-pyrrolo[2,1-f][1,2,4]triazin-2-yl]-[4-(4-methyl-piperazin-1-ylmethyl)-phenyl]-amine as a lyophilized powder. (M+H)=429.07. $^1$H NMR (400 MHz, DMSO, $d_6$) δ 9.55 (s, 1H), 8.97 (s, 1H), 7.79 (dd, 1H, J=1.64, 5.97 Hz), 7.73 (d, 2H, J=8.36 Hz), 7.48 (m, 1H), 7.22 (d, 3H, J=7.96 Hz), 7.12 (t, 1H, J=7.45 Hz), 6.95 (m, 2H), 3.85 (s, 3H), 3.72 (m, 6H), 3.40 (m, 4H), 2.76 (s, 3H).

Example 354

[7-(5-Chloro-2-methoxy-phenyl)-pyrrolo[2,1-f][1,2,4]triazin-2-yl]-[4-(4-methyl-piperazin-1-ylmethyl)-phenyl]-amine The compound was made in an analogous fashion to Example 353 replacing 2-Methanesulfinyl-7-(2-methoxy-phenyl)-pyrrolo[2,1-f][1,2,4]triazine with 7-(5-Chloro-2-methoxy-phenyl)-2-methanesulfinyl-pyrrolo[2,1-f][1,2,4]triazine to afford 46.68 mg of [7-(5-Chloro-2-methoxy-phenyl)-pyrrolo[2,1-f][1,2,4]triazin-2-yl]-[4-(4-methyl-piperazin-1-ylmethyl)-phenyl]-amine as a lyophilized powder. (M+H)=463.06. $^1$H NMR (400 MHz, DMSO, $d_6$) δ 9.64 (s, 1H), 9.01 (s, 1H), 8.05 (s, 1H), 7.75 (d, 2H, J=8.45 Hz), 7.50 (dd, 1H, J=2.68, 6.16 Hz), 7.28 (m, 2H), 7.25 (d, 1H, J=9.00 Hz), 7.06 (d, 1H, J=4.72 Hz), 6.95 (d, 1H, J=4.68 Hz), 4.07 (m, 4H), 3.83 (s, 3H), 3.42 (m, 3H), 3.16 (m, 3H), 2.67 (s, 3H).

Example 355

[7-(4-Methanesulfonyl-phenyl)-pyrrolo[2,1-f][1,2,4]triazin-2-yl]-[4-(4-methyl-piperazin-1-ylmethyl)-phenyl]-amine The compound was made in an analogous fashion to Example 348 replacing 2-Methanesulfinyl-7-(2-methoxy-phenyl)-pyrrolo[2,1-f][1,2,4]triazine with 2-Methanesulfinyl-7-(4-methanesulfonyl-phenyl)-pyrrolo[2,1-f][1,2,4]triazine to afford 16.46 mg of [7-(4-Methanesulfonyl-phenyl)-pyrrolo[2,1-f][1,2,4]triazin-2-yl]-[4-(4-methyl-piperazin-1-ylmethyl)-phenyl]-amine as a lyophilized powder. (M+H)=477.13. $^1$H NMR (400 MHz, DMSO, $d_6$) δ 9.08 (s, 1H), 8.51 (m, 4H), 8.04 (d, 4H, J=8.68 Hz), 7.44 (d, 1H, J=4.88 Hz), 7.37 (d, 1H, J=4.80 Hz), 7.03 (d, 1H, J=5.00 Hz), 4.60 (m, 2H), 3.72 (m, 3H), 3.55 (m, 3H), 3.30 (s, 3H), 3.16 (m, 2H), 2.86 (s, 3H).

Example 356

N-Cyclopropyl-3-[2-(4-morpholin-4-yl-phenylamino)-pyrrolo[2,1-f][1,2,4]triazin-7-yl]-benzenesulfonamide The compound was made in an analogous fashion to Example 331 replacing 6-hydroxy-3-pyridine boronic acid with N-Cyclopropyl-3-boronobenzenesulfonamide to afford 20.00 mg of N-Cyclopropyl-3-[2-(4-morpholin-4-yl-phenylamino)-pyrrolo[2,1-f][1,2,4]triazin-7-yl]-benzenesulfonamide as a lyophilized powder. (M+H)=491.1. $^1$H NMR (400 MHz, DMSO, $d_6$) δ 9.38 (s, 1H), 9.01 (s, 1H), 8.45 (m, 2H), 7.99 (m, 1H), 7.81 (m, 2H), 7.65 (d, 2H, J=8.21 Hz), 7.19 (m, 1H), 7.04 (m, 2H), 6.97 (m, 1H), 3.77 (m, 4H), 3.10 (m, 4H), 2.13 (m, 1H), 0.46 (m, 2H), 0.40 (m, 2H).

Example 357

N-Methyl-3-[2-(4-morpholin-4-yl-phenylamino)-pyrrolo[2,1-f][1,2,4]triazin-7-yl]-benzenesulfonamide The compound was made in an analogous fashion to Example 331 replacing 6-hydroxy-3-pyridine boronic acid with N-methyl-3-boronobenzenesulfonamide to afford 28.13 mg of N-Methyl-3-[2-(4-morpholin-4-yl-phenylamino)-pyrrolo[2,1-f][1,2,4]triazin-7-yl]-benzenesulfonamide as a lyophilized powder. (M+H)=465.1. $^1$H NMR (400 MHz, DMSO, $d_6$) δ 9.40 (s, 1H), 9.03 (s, 1H), 8.43 (m, 2H), 7.71 (m, 2H), 7.59 (m, 2H), 7.54 (m, 1H), 7.20 (m, 1H), 7.07 (m, 2H), 6.96 (m, 1H), 3.80 (m, 4H), 3.13 (m, 4H), 2.39 (s, 3H).

Example 358

(4-Morpholin-4-yl-phenyl)-{7-[3-(pyrrolidine-1-sulfonyl)-phenyl]-pyrrolo[2,1-f][1,2,4]triazin-2-yl}-amine The compound was made in an analogous fashion to Example 331 replacing 6-hydroxy-3-pyridine boronic acid with 3-(Pyrrolidinylsulfonyl)phenylboronic acid to afford 46.55 mg of (4-Morpholin-4-yl-phenyl)-{7-[3-(pyrrolidine-1-sulfonyl)-phenyl]-pyrrolo[2,1-f][1,2,4]triazin-2-yl}-amine as a lyophilized powder. (M+H)=505.1. $^1$H NMR (400 MHz, DMSO, $d_6$) δ 9.33 (s, 1H), 9.01 (s, 1H), 8.51 (s, 1H), 8.41 (s, 1H), 7.77 (m, 2H), 7.62 (d, 2H, J=8.04 Hz), 7.25 (m, 1H), 6.96 (m, 3H), 3.75 (m, 4H), 3.18 (m, 4H), 3.06 (m, 4H), 1.65 (m, 4H).

Example 359

5-[7-(2-Methoxy-phenyl)-pyrrolo[2,1-f][1,2,4]triazin-2-ylamino]-1-methyl-1,3-dihydro-indol-2-one 2-Methanesulfinyl-7-(2-methoxy-phenyl)-pyrrolo[2,1-f][1,2,4]triazine (125.0 mg, 0.0004350 mol), N,N-Diisopropylethylamine (0.250 mL, 0.00144 mol) and 5-Amino-1-methyl-1,3-dihydro-indol-2-one (0.141 g, 0.000870 mol) were dissolved in 1-Methoxy-2-propanol (0.500 mL, 0.00512 mol) and the reaction was irradiated at 300 watts, 180° C. for 40 minutes or until HPLC showed consumption of starting material. The reaction mixture was then reduced en vacuo and the product was isolated and purified by Gilson prep HPLC to afford 5-[7-(2-Methoxy-phenyl)-pyrrolo[2,1-f][1,2,4]triazin-2-ylamino]-1-methyl-1,3-dihydro-indol-2-one as a lyophilized powder. (M+H)=386.1. $^1$H NMR (400 MHz, DMSO, $d_6$) δ 9.33 (s, 1H), 8.93 (s, 1H), 7.78 (m, 2H), 7.50 (m, 2H), 7.24 (d, 1H, J=8.28 Hz), 7.15 (t, 1H, J=7.61 Hz), 6.91 (m, 2H), 6.82 (d, 1H, J=8.28 Hz), 3.78 (s, 3H), 3.46 (s, 2H), 3.08 (s, 3H).

Example 360

5-[7-(5-Chloro-2-methoxy-phenyl)-pyrrolo[2,1-f][1,2,4]triazin-2-ylamino]-1-methyl-1,3-dihydro-indol-2-one The compound was made in an analogous fashion to Example 359 replacing 2-Methanesulfinyl-7-(2-methoxy-phenyl)-pyrrolo[2,1-f][1,2,4]triazine with 7-(5-Chloro-2-methoxy-phenyl)-2-methanesulfinyl-pyrrolo[2,1-f][1,2,4]triazine to afford 28.53 mg of 5-[7-(5-Chloro-2-methoxy-phenyl)-pyrrolo[2,1-f][1,2,4]triazin-2-ylamino]-1-methyl-1,3-dihydro-indol-2-one as a lyophilized powder. (M+H)=420.1. $^1$H NMR (400 MHz, DMSO, $d_6$) δ 9.39 (s, 1H), 8.96 (s, 1H), 7.92 (s, 1H), 7.68 (s, 1H), 7.59 (d, 1H, J=8.49 Hz), 7.51 (d, 1H, J=8.96 Hz), 7.26 (d, 1H, J=8.84 Hz), 6.99 (m, 1H), 6.90 (m 1H), 6.84 (d, 1H, J=8.29 Hz), 3.82 (s, 3H), 3.49 (s, 2H), 3.09 (s, 3H).

Example 361

N-{3-[2-(1-Methyl-2-oxo-2,3-dihydro-1H-indol-5-ylamino)-pyrrolo[2,1-f][1,2,4]triazin-7-yl]-phenyl}-methanesulfonamide The compound was made in an analogous fashion to Example 359 replacing 2-Methanesulfinyl-7-(2-methoxyphenyl)-pyrrolo[2,1-f][1,2,4]triazine with N-[3-(2-Methanesulfinyl-pyrrolo[2,1-f][1,2,4]triazin-7-yl)-phenyl]-methanesulfonamide to afford 24.04 mg of N-{3-[2-(1-Methyl-2-oxo-2,3-dihydro-1H-indol-5-ylamino)-pyrrolo[2,1-f][1,2,4]triazin-7-yl]-phenyl}-methanesulfonamide as a lyophilized powder. (M+H)=449.1. $^1$H NMR (400 MHz, DMSO, $d_6$) δ 9.87 (s, 1H), 9.42 (s, 1H), 8.98 (s, 1H), 7.92 (d, 1H, J=7.88 Hz), 7.88 (m, 1H), 7.80 (m, 1H), 7.63 (d, 1H, J=8.48 Hz), 7.54 (t, 1H, J=7.84 Hz), 7.26 (d, 1H, 7.88 Hz), 7.05 (m, 1H), 6.94 (m, 2H), 3.56 (s, 2H), 3.11 (s, 3H), 3.01 (s, 3H).

Example 362

(4-Morpholin-4-yl-phenyl)-(7-phenylaminomethyl-pyrrolo[2,1-f][1,2,4]triazin-2-yl)-amine 362a. 2-Methylsulfanyl-pyrrolo[2,1-f][1,2,4]triazine
4-Chloro-2-methylsulfanyl-pyrrolo[2,1-f][1,2,4]triazine (5.0 g, 25 mmol) was dissolved in Isopropyl alcohol (2.50E2 mL, 3260 mmol) and the solution was treated with Sodium borohydride (1.9 g, 5.0E1 mmol). The mixture was then allowed to stir overnight at room temperature. The solid was filtered and washed with dichloromethane. The filtrate was then partially reduced leaving approximately 20 mL of solvent. The crude material was further diluted with Methylene chloride (200 mL, 3000 mmol). Dichlorodicyanoquinone (6.25 g, 27.5 mmol) was then added portion-wise over 15 minutes and the reaction was allowed to stir for 1 hour at room temperature. The mixture was then filtered through Celite and the pad was washed with dichloromethane. The filtrate was reduced en vacuo. The crude reaction mixture was then purified by Isco flash column chromatography (hexanes/ethyl acetate eluent) and combined fractions were reduced and dried under vacuum to afford 3.10 g of 2-Methylsulfanyl-pyrrolo[2,1-f][1,2,4]triazine as a yellow solid. $^1$H NMR (400 MHz, CDCl$_3$) δ 8.72 (s, 1H), 7.70 (s, 1H), 6.79 (m, 2H), 2.56 (s, 3H). 3 62b. 2-Methylsulfanyl-pyrrolo[2,1-f][1,2,4]triazine-7-carbaldehyde To a cooled (0° C.) mixture of Phosphoryl chloride (55 mL, 0.59 mol) and N,N-Dimethylformamide (27 mL, 0.35 mol) was added 2-Methylsulfanyl-pyrrolo[2,1-f][1,2,4]triazine (3.70 g, 0.0224 mol) in N,N-Dimethylformamide (55 mL, 0.71 mol). The addition was added to ensure that the temperature of the reaction stayed below 20° C. After complete addition of 7-Bromo-2-methylsulfanyl-pyrrolo[2,1-f][1,2,4]triazine, the mixture was heated at 80° C. and was allowed to stir until HPLC showed consumption of starting material (~1 hour). The reaction was then poured over ice water and was neutralized with saturated sodium bicarbonate. Organics were then extracted with ethyl acetate and combined extracts were dried over magnesium sulfate, filtered and reduced to afford 3.40 g of 2-Methylsulfanyl-pyrrolo[2,1-f][1,2,4]triazine-7-carbaldehyde which was used without further purification. $^1$H NMR (400 MHz, DMSO, $d_6$) δ 10.41 (s, 1H), 9.25 (s, 1H), 7.43 (d, 1H, J=4.96 Hz), 7.05 (d, 1H, J=5.00 Hz), 2.59 (s, 3H).

362c. (2-Methylsulfanyl-pyrrolo[2,1-f][1,2,4]triazin-7-ylmethyl)-phenyl-amine
2-Methylsulfanyl-pyrrolo[2,1-f][1,2,4]triazine-7-carbaldehyde (0.200 g, 1.04 mmol) and Aniline (0.104 mL, 1.14 mmol) were dissolved in a solution of Acetic acid (0.100 mL, 1.76 mmol) and Methylene chloride (10 mL, 200 mmol) and the reaction was allowed to stir at room temperature for 1 hour. Sodium triacetoxyborohydride (0.439 g, 2.07 mmol) was then added and the reaction was allowed to continue stirring at room temperature until HPLC showed consumption of starting material. The reaction mixture was poured over saturated sodium bicarbonate and organics were extracted with dichloromethane. Combined extracts were then dried over sodium sulfate, filtered and reduced. The crude reaction mixture was then purified by Isco flash column chromatography (hexanes/ethyl acetate eluent) and combined fractions were reduced and dried under vacuum to afford 0.280 g of (2-Methylsulfanyl-pyrrolo[2,1-f][1,2,4]triazin-7-ylmethyl)-phenyl-amine. $^1$H NMR (400 MHz, DMSO, $d_6$) δ 8.92 (s, 1H), 7.06 (m, 2H), 6.90 (d, 1H, J=4.61 Hz), 6.83 (d, 1H, J=4.61 Hz), 6.65 (m, 2H), 6.54 (t, 1H, J=7.28 Hz), 6.13 (t, 1H, J=6.16 Hz), 4.61 (d, 2H, J=6.16 hz), 2.56 (s, 3H).

362d. (2-Methanesulfinyl-pyrrolo[2,1-f][1,2,4]triazin-7-ylmethyl)-phenyl-amine
(2-Methylsulfanyl-pyrrolo[2,1-f][1,2,4]triazin-7-ylmethyl)-phenyl-amine (0.280 g, 1.04 mmol) was dissolved in Methylene chloride (5 mL, 80 mmol) and the solution was treated with m-Chloroperbenzoic acid (0.313 g, 1.40 mmol) at room temperature. The reaction was allowed to stir until HPLC showed consumption of starting materials. The reaction mixture was poured over saturated sodium bicarbonate and organics were extracted with dichloromethane. Combined extracts were then dried over sodium sulfate, filtered and reduced. The crude reaction mixture was purified by Isco flash column chromatography (hexanes/ethyl acetate eluent) and combined fractions were reduced and dried under vacuum to afford 83 mg of (2-Methanesulfinyl-pyrrolo[2,1-f][1,2,4]triazin-7-ylmethyl)-phenyl-amine. (M+H)=287.0. $^1$H NMR (400 MHz, DMSO, $d_6$) δ 9.24 (s, 1H), 7.25 (m, 1H), 7.10 (m, 3H), 6.64 (d, 2H, J=8.08 Hz), 6.55 (t, 1H, J=7.12 Hz), 6.22 (m, 1H), 4.68 (m, 2H), 2.92 (s, 3H).

362e. (4-Morpholin-4-yl-phenyl)-(7-phenylaminomethyl-pyrrolo[2,1-f][1,2,4]triazin-2-yl)-amine
(2-Methanesulfinyl-pyrrolo[2,1-f][1,2,4]triazin-7-ylmethyl)-phenyl-amine (40.0 mg, 0.140 mmol), 4-(4-morpholino)aniline (49.8 mg, 0.279 mmol) and N,N-Diisopropylethylamine (0.0730 mL, 0.419 mmol) were dissolved in 1-Methoxy-2-propanol (0.50 mL, 5.1 mmol) and the reaction was irradiated at 300 watts, 200° C. for 20 minutes or longer depending on HPLC monitoring. The reaction was then reduced under nitrogen. The crude reaction mixture was purified via Gilson reverse phase chromatography. Combined fractions were lyophilized to afford 17.12 mg of (4-Morpholin-4-yl-phenyl)-(7-phenylaminomethyl-pyrrolo[2,1-f][1,2,4]triazin-2-yl)-amine as a TFA salt. (M+H)=401.16. $^1$H NMR (400 MHz, DMSO, $d_6$) δ 9.32 (s, 1H), 8.87 (s, 1H), 7.72 (d, 2H, J=8.29 Hz), 7.09 (t, 2H, J=7.32 Hz), 6.97 (m, 2H), 6.76 (m, 1H), 6.67 (m, 3H), 6.60 (t, 1H, J=7.32 Hz), 4.59 (s, 2H), 3.77 (m, 4H), 3.12 (m, 4H).

Example 363

[4-(4-Methyl-piperazin-1-yl)-phenyl]-(7-phenylaminomethyl-pyrrolo[2,1-f][1,2,4]triazin-2-yl)-amine The compound was made in an analogous fashion as Example 362 replacing 4-(4-morpholino)aniline with 4-(4-Methyl-piperazin-1-yl)-phenylamine to afford 29.80 mg of [4-(4-Methyl-piperazin-1-yl)-phenyl]-(7-phenylaminomethyl-pyrrolo[2,1-f][1,2,4]triazin-2-yl)-amine as a lyophilized powder. (M+H)=414.17. $^1$H NMR (400 MHz, DMSO, $d_6$) δ 9.51 (m, 1H), 9.28 (s, 1H), 8.86 (s, 1H), 7.71 (d, 2H, J=8.13 Hz), 7.07 (t, 2H, J=7.40 Hz), 6.89 (d, 2H, J=8.16 Hz), 6.75 (m, 1H), 6.65 (m, 3H), 6.56 (t, 1H, J=7.32 Hz), 4.58 (s, 2H), 3.71 (m, 2H), 3.51 (m, 2H), 3.16 (m, 2H), 2.86 (m, 5H).

Example 364

{7-[(2-Methoxy-phenylamino)-methyl]-pyrrolo[2,1-f][1,2,4]triazin-2-yl}-(4-morpholin-4-yl-phenyl)-amine 364a. (2-Methoxy-phenyl)-(2-methylsulfanyl-pyrrolo[2,1-f][1,2,4]triazin-7-ylmethyl)-amine The compound was made in an analogous fashion to Example 362C replacing Aniline with 2-Methoxyphenylamine to afford 230 mg of (2-Methoxy-phenyl)-(2-methylsulfanyl-pyrrolo[2,1-f][1,2,4]triazin-7-ylmethyl)-amine. (M+H)=301.1. $^1$H NMR (400 MHz, DMSO, d$_6$) δ 8.92 (s, 1H), 6.88 (d, 1H, J=4.61 Hz), 6.80 (m, 2H), 6.71 (m, 1H), 6.63 (m, 1H), 6.54 (m, 1H), 5.56 (m, 1H), 4.69 (d, 2H, J=6.64 Hz), 3.77 (s, 3H), 2.59 (s, 3H).

364b. (2-Methanesulfinyl-pyrrolo[2,1-f][1,2,4]triazin-7-ylmethyl)-(2-methoxy-phenyl)-amine 364b. The compound was made in an analogous fashion to Example 362D replacing (2-Methylsulfanyl-pyrrolo[2,1-f][1,2,4]triazin-7-ylmethyl)-phenyl-amine with (2-Methoxy-phenyl)-(2-methylsulfanyl-pyrrolo[2,1-f][1,2,4]triazin-7-ylmethyl)-amine to afford 90 mg of (2-Methanesulfinyl-pyrrolo[2,1-f][1,2,4]triazin-7-ylmethyl)-(2-methoxy-phenyl)-amine.

364c. {7-[(2-Methoxy-phenylamino)-methyl]-pyrrolo[2,1-f][1,2,4]triazin-2-yl}-(4-morpholin-4-yl-phenyl)-amine The compound was made in an analogous fashion to Example 362E replacing (2-Methanesulfinyl-pyrrolo[2,1-f][1,2,4]triazin-7-ylmethyl)-phenyl-amine with (2-Methanesulfinyl-pyrrolo[2,1-f][1,2,4]triazin-7-ylmethyl)-(2-methoxy-phenyl)-amine to afford 12.72 mg of {7-[(2-Methoxy-phenylamino)-methyl]-pyrrolo[2,1-f][1,2,4]triazin-2-yl}-(4-morpholin-4-yl-phenyl)-amine as a lyophilized powder. (M+H)=431.10. $^1$H NMR (400 MHz, DMSO, d$_6$) δ 9.52 (s, 1H), 9.31 (s, 1H), 8.85 (s, 1H), 7.71 (d, 2H, J=8.57 Hz), 6.97 (m, 2H), 6.82 (d, 1H, J=7.84 Hz), 6.73 (m, 2H), 6.65 (m, 3H), 4.64 (s, 2H), 3.77 (m, 4H), 3.72 (s, 3H), 3.11 (m, 4H).

Example 365

{7-[(2-Methoxy-phenylamino)-methyl]-pyrrolo[2,1-f][1,2,4]triazin-2-yl}-[4-(4-methyl-piperazin-1-yl)-phenyl]-amine The compound was made in an analogous fashion as Example 364C replacing 4-(4-morpholino)aniline with 4-(4-Methyl-piperazin-1-yl)-phenylamine to afford 21.70 mg of {7-[(2-Methoxy-phenylamino)-methyl]-pyrrolo[2,1-f][1,2,4]triazin-2-yl}-[4-(4-methyl-piperazin-1-yl)-phenyl]-amine as a lyophilized powder. (M+H)=444.18. $^1$H NMR (400 MHz, DMSO, d$_6$) δ 9.54 (s, 1H), 9.29 (s, 1H), 8.85 (s, 1H), 7.71 (d, 2H, J=8.29 Hz), 6.93 (d, 2H, J=8.44 Hz), 6.81 (d, 1H, J=7.76 Hz), 6.71 (m, 2H), 6.63 (m, 2H), 6.57 (m, 1H), 4.63 (s, 2H), 3.71 (m, 5H), 3.53 (m, 2H), 3.16 (m, 2H), 2.89 (m, 5H).

Example 366

N-Methyl-3-{2-[4-(4-methyl-piperazin-1-yl)-phenylamino]-pyrrolo[2,1-f][1,2,4]triazin-7-yl}-benzenesulfonamide Palladium Acetate (0.017 g, 0.000077 mol) and Triphenylphosphine (0.025 g, 0.000097 mol) were dissolved in Tetrahydrofuran (1.2 mL, 0.014 mol) and the mixture was allowed to stir at room temperature for 10 minutes. (7-Bromo-pyrrolo[2,1-f][1,2,4]triazin-2-yl)-[4-(4-methyl-piperazin-1-yl)-phenyl]-amine (0.125 g, 0.000323 mol) was then added and the reaction was again allowed to stir for 10 minutes. N-methyl-3-boronobenzenesulfonamide (0.166 g, 0.000775 mol) was added followed by 0.9 M of Sodium carbonate in water (0.9 mL, 0.0008 mol) and Ethanol (1.2 mL, 0.020 mol). The reaction mixture was then heated at 80° C. and was allowed to stir overnight. The reaction mixture was poured over saturated sodium chloride, and organics were extracted with ethyl acetate. Combined organics were dried over sodium sulfate, filtered and reduced en vacuo. The crude mixture was purified by Gilson prep HPLC to afford 38.12 mg of N-Methyl-3-{2-[4-(4-methyl-piperazin-1-yl)-phenylamino]-pyrrolo[2,1-f][1,2,4]triazin-7-yl}-benzenesulfonamide as a lyophilized powder. (M+H)=478.1. $^1$H NMR (400 MHz, DMSO, d$_6$) δ 9.74 (s, 1H), 9.40 (s, 1H), 9.02 (s, 1H), 8.53 (s, 1H), 8.40 (m, 1H), 7.76 (m, 2H), 7.68 (m, 2H), 7.55 (m, 1H), 7.19 (d, 1H, J=4.28 Hz), 7.04 (m, 1H), 6.98 (d, 1H, J=4.32 Hz), 3.72 (m, 2H), 3.53 (m, 2H), 3.20 (m, 2H), 2.94 (m, 2H), 2.91 (s, 3H), 2.40 (s, 3H).

Example 367

[4-(4-Methyl-piperazin-1-yl)-phenyl]-{7-[3-(pyrrolidine-1-sulfonyl)-phenyl]-pyrrolo[2,1-f][1,2,4]triazin-2-yl}-amine The compound was made in an analogous fashion to Example 366 replacing N-methyl-3-boronobenzenesulfonamide with 3-(Pyrrolidinylsulfonyl)phenylboronic acid to afford 12.22 mg of [4-(4-Methyl-piperazin-1-yl)-phenyl]-{7-[3-(pyrrolidine-1-sulfonyl)-phenyl]-pyrrolo[2,1-f][1,2,4]triazin-2-yl}-amine as a lyophilized powder. (M+H)=518.1. $^1$H NMR (400 MHz, DMSO, d$_6$) δ 9.38 (s, 1H), 9.01 (s, 1H), 8.46 (m, 2H), 7.80 (m, 2H), 7.64 (d, 2H, J=7.88 Hz), 7.26 (m, 1H), 6.98 (m, 3H), 3.71 (m, 2H), 3.51 (m, 2H), 3.17 (m, 6H), 2.86 (m, 5H), 1.65 (m, 4H).

Example 368

N-(2-Hydroxy-ethyl)-3-[2-(4-morpholin-4-yl-phenylamino)-pyrrolo[2,1-f][1,2,4]triazin-7-yl]-benzenesulfonamide The compound was made in an analogous fashion to Example 331 replacing 6-hydroxy-3-pyridine boronic acid with N-(2-Hydroxyethyl) 3-boronobenzenesulfonamide to afford 23.85 mg of N-(2-Hydroxy-ethyl)-3-[2-(4-morpholin-4-yl-phenylamino)-pyrrolo[2,1-f][1,2,4]triazin-7-yl]-benzenesulfonamide as a lyophilized powder. (M+H)=495.1. $^1$H NMR (400 MHz, DMSO, d$_6$) δ 9.37 (s, 1H), 9.01 (s, 1H), 8.48 (s, 1H), 8.42 (d, 1H, J=7.28 Hz), 7.80 (m, 2H), 7.67 (m, 3H), 7.19 (m, 1H), 7.02 (m, 2H), 6.97 (m, 1H), 4.34 (m, 1H), 3.77 (m, 4H), 3.37 (m, 2H), 3.09 (m, 4H), 2.82 (m, 2H).

Example 369

N-(2-Hydroxy-ethyl)-3-{2-[4-(4-methyl-piperazin-1-yl)-phenylamino]-pyrrolo[2,1-f][1,2,4]triazin-7-yl}-benzenesulfonamide The compound was made in an analogous fashion to Example 366 replacing N-methyl-3-boronobenzenesulfonamide with N-(2-Hydroxyethyl) 3-boronobenzenesulfonamide to afford 5.29 mg of N-(2-Hydroxy-ethyl)-3-{2-[4-(4-methyl-piperazin-1-yl)-phenylamino]-pyrrolo[2,1-f][1,2,4]triazin-7-yl}-benzenesulfonamide as a lyophilized powder. (M+H)=508.1. $^1$H NMR (400 MHz, DMSO, d$_6$) δ 9.73 (s, 1H), 9.38 (s, 1H), 9.01 (s, 1H), 8.51 (s, 1H), 8.39 (d, 1H, J=7.72 Hz), 7.70 (m, 4H), 7.19 (m, 1H), 7.01 (m, 2H), 6.97 (m, 1H), 4.21 (m, 1H), 3.72 (m, 2H), 3.53 (m, 2H), 3.40 (m, 2H), 3.20 (m, 2H), 2.92 (m, 2H), 2.83 (m, 5H).

Example 370

(2-Fluoro-4-morpholin-4-yl-phenyl)-[7-(2-methoxy-phenyl)-pyrrolo[2,1-f][1,2,4]triazin-2-yl]-amine 2-Methanesulfinyl-7-(2-methoxy-phenyl)-pyrrolo[2,1-f][1,2,4]triazine (125.0 mg, 0.0004350 mol), N,N-Diisopropylethylamine (0.250 mL, 0.00144 mol) and 2-Fluoro-4-morpholin-4-yl-phenylamine (0.171 g, 0.000870 mol) were dissolved in 1-Methoxy-2-propanol (0.500 mL, 0.00512 mol) and the reaction was irradiated at 300 watts, 180° C. for 40 minutes or until HPLC showed consumption of starting material. The reaction mixture was then reduced en vacuo and the product was isolated and purified by Gilson prep HPLC to afford 36.52 mg of (2-Fluoro-4-morpholin-4-yl-phenyl)-[7-(2-methoxy-phenyl)-pyrrolo[2,1-f][1,2,4]triazin-2-yl]-amine as a lyophilized powder. (M+H)=420.1. $^1$H NMR (400 MHz, DMSO, $d_6$) δ 8.90 (s, 1H), 8.48 (s, 1H), 7.84 (d, 1H, J=7.56 Hz), 7.56 (t, 1H, J=9.00 Hz), 7.38 (m, 1H), 7.14 (m, 1H), 7.01 (m, 2H), 6.88 (m, 2H), 6.67 (m, 1H), 3.78 (s, 3H), 3.74 (m, 4H), 3.09 (m, 4H).

Example 371

N-{3-[2-(2-Fluoro-4-morpholin-4-yl-phenylamino)-pyrrolo[2,1-f][1,2,4]triazin-7-yl]-phenyl}-methanesulfonamide The compound was prepared in an analogous fashion to Example 370 replacing 2-Methanesulfinyl-7-(2-methoxy-phenyl)-pyrrolo[2,1-f][1,2,4]triazine with N-[3-(2-Methanesulfinyl-pyrrolo[2,1-f][1,2,4]triazin-7-yl)-phenyl]-methanesulfonamide to afford 50.00 mg of N-{3-[2-(2-Fluoro-4-morpholin-4-yl-phenylamino)-pyrrolo[2,1-f][1,2,4]triazin-7-yl]-phenyl}-methanesulfonamide as a lyophilized powder. (M+H)=483.0. $^1$H NMR (400 MHz, DMSO, $d_6$) δ 9.72 (s, 1H), 8.95 (s, 1H), 8.64 (s, 1H), 7.91 (d, 1H, J=7.96 Hz), 7.81 (m, 1H), 7.59 (t, 1H, J=9.07 Hz), 7.37 (t, 1H, J=7.68 Hz), 7.18 (m, 1H), 7.05 (m, 1H), 6.92 (m, 2H), 6.82 (m, 1H), 3.75 (m, 4H), 3.13 (m, 4H), 2.98 (s, 3H).

Example 372

(2-Fluoro-4-morpholin-4-yl-phenyl)-(7-pyridin-3-yl-pyrrolo[2,1-f][1,2,4]triazin-2-yl)-amine The compound was made in an analogous fashion to Example 370 replacing 2-Methanesulfinyl-7-(2-methoxy-phenyl)-pyrrolo[2,1-f][1,2,4]triazine with 2-Methanesulfinyl-7-pyridin-3-yl-pyrrolo[2,1-f][1,2,4]triazine to afford 6.79 mg of (2-Fluoro-4-morpholin-4-yl-phenyl)-(7-pyridin-3-yl-pyrrolo[2,1-f][1,2,4]triazin-2-yl)-amine as a lyophilized powder. (M+H)=391.1. $^1$H NMR (400 MHz, DMSO, $d_6$) δ 9.37 (s, 1H), 9.02 (s, 1H), 8.88 (s, 1H), 8.79 (d, 1H, J=8.59 Hz), 8.60 (m, 1H), 7.65 (m, 1H), 7.47 (m, 1H), 7.39 (m, 1H), 6.98 (m, 1H), 6.90 (m, 1H), 6.81 (m, 1H), 3.75 (m, 4H), 3.14 (m, 4H).

Example 373

5-[7-(4-Methanesulfonyl-phenyl)-pyrrolo[2,1-f][1,2,4]triazin-2-ylamino]-1-methyl-1,3-dihydro-indol-2-one The compound was made in an analogous fashion to Example 359 replacing 2-Methanesulfinyl-7-(2-methoxy-phenyl)-pyrrolo[2,1-f][1,2,4]triazine with 2-Methanesulfinyl-7-(4-methanesulfonyl-phenyl)-pyrrolo[2,1-f][1,2,4]triazine to afford 18.13 mg of 5-[7-(4-Methanesulfonyl-phenyl)-pyrrolo[2,1-f][1,2,4]triazin-2-ylamino]-1-methyl-1,3-dihydro-indol-2-one as a lyophilized powder. (M+H)=434.2. $^1$H NMR (400 MHz, DMSO, $d_6$) δ 9.51 (s, 1H), 9.03 (s, 1H), 8.45 (d, 2H, J=7.84 Hz), 8.06 (d, 2H, J=7.68 Hz), 7.82 (s, 1H), 7.56 (d, 1H, J=8.24 Hz), 7.33 (m, 1H), 6.96 (m, 2H), 3.58 (m, 2H), 3.13 (s, 3H), 2.51 (s, 3H).

Example 374

1-Methyl-5-(7-pyridin-3-yl-pyrrolo[2,1-f][1,2,4]triazin-2-ylamino)-1,3-dihydro-indol-2-one The compound was made in an analogous fashion to Example 359 replacing 2-Methanesulfinyl-7-(2-methoxy-phenyl)-pyrrolo[2,1-f][1,2,4]triazine with 2-Methanesulfinyl-7-pyridin-3-yl-pyrrolo[2,1-f][1,2,4]triazine to afford 15.80 mg of 1-Methyl-5-(7-pyridin-3-yl-pyrrolo[2,1-f][1,2,4]triazin-2-ylamino)-1,3-dihydro-indol-2-one as lyophilized powder. (M+H)=357.1. $^1$H NMR (400 MHz, DMSO, $d_6$) δ 9.46 (s, 1H), 9.34 (s, 1H), 9.02 (s, 1H), 8.58 (d, 2H, J=6.32 Hz), 7.78 (s, 1H), 7.60 (m, 2H), 7.28 (m, 1H), 6.96 (m, 2H), 3.57 (s, 2H), 3.12 (s, 3H).

Example 375

N-Methyl-N-{2-[2-(1-methyl-2-oxo-2,3-dihydro-1H-indol-5-ylamino)-pyrrolo[2,1-f][1,2,4]triazin-7-yl]-phenyl}-methanesulfonamide The compound was made in an analogous fashion to Example 359 replacing 2-Methanesulfinyl-7-(2-methoxy-phenyl)-pyrrolo[2,1-f][1,2,4]triazine with N-[2-(2-Methanesulfinyl-pyrrolo[2,1-f][1,2,4]triazin-7-yl)-phenyl]-N-methyl-methanesulfonamide to afford 51.40 mg of N-Methyl-N-{2-[2-(1-methyl-2-oxo-2,3-dihydro-1H-indol-5-ylamino)-pyrrolo[2,1-f][1,2,4]triazin-7-yl]-phenyl}-methanesulfonamide as lyophilized powder. (M+H)=463.1. $^1$H NMR (400 MHz, DMSO, $d_6$) δ 9.33 (s, 1H), 8.94 (s, 1H), 7.99 (d, 1H, J=7.56 Hz), 7.61 (m, 2H), 7.46 (m, 2H), 6.98 (m, 1H), 6.91 (m, 2H), 6.80 (m, 1H), 3.44 (s, 2H), 3.08 (s, 3H), 3.03 (s, 3H), 2.89 (s, 3H).

Example 376

7-(2-methoxy-phenyl)-pyrrolo(2,1-f)(1,2,4)triazin-2-yl-6-amino-1'-methyl-spiro(2H-1-benzopyran-2,4'-piperidin-4-(3H)-one 2-Methanesulfinyl-7-(2-methoxy-phenyl)-pyrrolo[2,1-f][1,2,4]triazine (87.49 mg, 0.0003045 mol), N,N-Diisopropylethylamine (0.175 mL, 0.00100 mol) and 6-Amino-1'-methyl-spiro(2H-1-benzopyran-2,4'-piperidin]-4-(3H)-one (0.150 g, 0.000609 mol) were dissolved in 1-Methoxy-2-propanol (0.350 mL, 0.00358 mol) and the reaction was irradiated at 300 watts, 180° C. for 40 minutes or until HPLC showed consumption of starting material. The reaction mixture was then reduced en vacuo and the product was isolated and purified by Gilson prep HPLC to afford 23.40 mg of 7-(2-methoxy-phenyl)-pyrrolo(2,1-f)(1,2,4)triazin-2-yl-6-amino-1'-methyl-spiro(2H-1-benzopyran-2,4'-piperidin-4 (3H)-one as a lyophilized powder. (M+H)=470.1. $^1$H NMR (400 MHz, DMSO, $d_6$) δ 9.42 (m, 1H), 8.95 (s, 1H), 8.05 (d, 1H, J=8.93 Hz), 7.93 (m, 1H), 7.81 (d, 1H, J=7.32 Hz), 7.43 (m, 1H), 7.21 (d, 1H, J=8.25 Hz), 7.11 (m, 1H), 7.01 (m, 1H), 6.94 (m, 2H), 3.79 (s, 3H), 3.31 (m, 2H), 3.20 (m, 2H), 2.85 (m, 5H), 2.19 (m, 2H), 1.84 (m, 2H).

Example 377

7-(2-methoxy-phenyl)-pyrrolo(2,1-f)(1,2,4)triazin-2-yl-6-amino-1'-methyl-spiro(2H-1-benzopyran-2,4'-piperidine)

2-Methanesulfinyl-7-(2-methoxy-phenyl)-pyrrolo[2,1-f][1,2,4]triazine (87.49 mg, 0.0003045 mol), N,N-Diisopropylethylamine (0.175 mL, 0.00100 mol) and 6-amino-1'-methyl-spiro(2H-1-benzopyran-2,4'-piperidine) (0.141 g, 0.000609 mol) were dissolved in 1-Methoxy-2-propanol (0.350 mL, 0.00358 mol) and the reaction was irradiated at 300 watts, 180° C. for 40 minutes or until HPLC showed consumption of starting material. The reaction mixture was then reduced en vacuo and the product was isolated and purified by Gilson prep HPLC to afford 17.67 mg of 7-(2-methoxy-phenyl)-pyrrolo(2,1-f)(1,2,4)triazin-2-yl-6-amino-1'-methyl-spiro(2H-1-benzopyran-2,4'-piperidine) as a lyophilized powder. (M+H)=456.1. $^1$H NMR (400 MHz, DMSO, d$_6$) δ 9.19 (s, 1H), 8.91 (s, 1H), 7.81 (d, 1H, J=7.24 Hz), 7.57 (m, 1H), 7.45 (m, 1H), 7.34 (m, 1H), 7.21 (m, 1H), 7.11 (m, 1H), 6.90 (d, 2H, J=7.65 Hz), 6.70 (d, 1H, J=8.56 Hz), 3.79 (s, 3H), 3.33 (m, 2H), 3.18 (m, 2H), 2.83 (m, 3H), 2.62 (m, 2H), 1.92 (m, 2H), 1.79 (m, 4H).

Example 378

N-(3-(2-(6-amino-1'-methyl-spiro(2H-1-benzopyran-2,4'-piperidine)-pyrrolo(2,1-f)(1,2,4)trazin-7-yl)phenyl)-methanesulfonamide The compound was prepared in an analogous fashion to Example 376 replacing 2-Methanesulfinyl-7-(2-methoxy-phenyl)-pyrrolo[2,1-f][1,2,4]triazine with N-[3-(2-Methanesulfinyl-pyrrolo[2,1-f][1,2,4]triazin-7-yl)-phenyl]-methanesulfonamide to afford 21.89 mg of N-(3-(2-(6-amino-1'-methyl-spiro(2H-1-benzopyran-2,4'-piperidine)-pyrrolo(2,1-f)(1,2,4)trazin-7-yl)phenyl)-methanesulfonamide as a lyophilized powder. (M+H)=519.1. $^1$H NMR (400 MHz, DMSO, d$_6$) δ 9.85 (s, 1H), 9.29 (s, 1H), 8.97 (s, 1H), 7.98 (d, 1H, J=7.56 Hz), 7.78 (m, 1H), 7.68 (m, 1H), 7.48 (m, 1H), 7.37 (d, 1H, J=9.08 Hz), 7.27 (d, 1H, J=8.00 Hz), 7.01 (m, 1H), 6.94 (m, 1H), 6.80 (d, 1H, J=8.88 Hz), 3.37 (m, 2H), 3.17 (m, 2H), 3.02 (s, 3H), 2.85 (m, 3H), 2.75 (m, 2H), 1.99 (m, 2H), 1.81 (m, 4H).

Example 379

N-(3-{2-[4-(4-Methyl-piperazin-1-yl)-phenylamino]-pyrrolo[2,1-f][1,2,4]triazin-7-yl}-phenyl)-methanesulfonamide N-[3-(2-Methanesulfinyl-pyrrolo[2,1-f][1,2,4]triazin-7-yl)-phenyl]-methanesulfonamide (125.0 mg, 0.0003567 mol), N,N-Diisopropylethylamine (0.205 mL, 0.00118 mol) and 4-(4-Methyl-piperazin-1-yl)-phenylamine (0.136 g, 0.000713 mol) were dissolved in 1-Methoxy-2-propanol (0.410 mL, 0.00419 mol) and the reaction was irradiated at 300 watts, 180° C. for 40 minutes or until HPLC showed consumption of starting material. The reaction mixture was then reduced en vacuo and the product was isolated and purified by Gilson prep HPLC to afford 113.55 mg of N-(3-{2-[4-(4-Methyl-piperazin-1-yl)-phenylamino]-pyrrolo[2,1-f][1,2,4]triazin-7-yl}-phenyl)-methanesulfonamide as a lyophilized powder. (M+H)=478.1. $^1$H NMR (400 MHz, DMSO, d$_6$) δ 9.78 (m, 1H), 9.32 (s, 1H), 8.98 (s, 1H), 7.90 (m, 2H), 7.67 (m, 2H), 7.53 (m, 1H), 7.27 (d, 1H, J=7.97 Hz), 7.06 (m, 1H), 6.94 (m, 2H), 6.89 (m, 1H), 3.76 (m, 2H), 3.53 (m, 2H), 3.19 (m, 2H), 3.04 (s, 3H), 2.96 (m, 5H).

Example 380

N-[3-(2-{4-[4-(2-Hydroxy-ethyl)-piperazin-1-yl]-phenylamino}-pyrrolo[2,1-f][1,2,4]triazin-7-yl)-phenyl]-methanesulfonamide The compound was made in an analogous fashion to Example 378 replacing 4-(4-Methyl-piperazin-1-yl)-phenylamine with 2-[4-(4-Amino-phenyl)-piperazin-1-yl]-ethanol to afford 67.81 mg of N-[3-(2-{4-[4-(2-Hydroxy-ethyl)-piperazin-1-yl]-phenylamino}-pyrrolo[2,1-f][1,2,4]triazin-7-yl)-phenyl]-methanesulfonamide as a lyophilized powder. (M+H)=508.1. $^1$H NMR (400 MHz, DMSO, d$_6$) δ 9.84 (s, 1H), 9.63 (s, 1H), 9.31 (s, 1H), 8.98 (s, 1H), 7.92 (m, 2H), 7.68 (d, 2H, J=7.92 Hz), 7.51 (t, 1H, J=7.72 Hz), 7.27 (d, 1H, J=8.05 Hz), 7.05 (m, 1H), 7.01 (m, 2H), 6.95 (m, 1H), 3.77 (m, 4H), 6.31 (m, 2H), 3.25 (m, 4H), 3.06 (m, 5H).

Example 381

N-{3-[2-(5,5-Dimethyl-2-oxo-2,3,4,5-tetrahydro-1H-1-benzazepin-8-ylamino)-pyrrolo[2,1-f][1,2,4]triazin-7-yl]-phenyl}-methanesulfonamide The compound was made in an analogous fashion to Example 378 replacing 4-(4-Methyl-piperazin-1-yl)-phenylamine with 8-Amino-5,5-dimethyl-1,3,4,5-tetrahydro-benzo[b]azepin-2-one to afford 19.51 mg of N-{3-[2-(5,5-Dimethyl-2-oxo-2,3,4,5-tetrahydro-1H-1-benzazepin-8-ylamino)-pyrrolo[2,1-f][1,2,4]triazin-7-yl]-phenyl}-methanesulfonamide as a lyophilized powder. (M+H)=491.1. $^1$H NMR (400 MHz, DMSO, d$_6$) δ 9.83 (s, 1H), 9.51 (s, 1H), 9.42 (s, 1H), 9.00 (s, 1H), 8.00 (d, 1H, J=7.68 Hz), 7.83 (m, 1H), 7.62 (d, 1H, J=7.68 Hz), 7.51 (m, 1H), 7.32 (m, 3H), 7.08 (m, 1H), 6.97 (m, 1H), 3.02 (s, 3H), 2.18 (m, 2H), 1.99 (m, 2H), 1.84 (s, 6H).

Example 382

N-{3-[2-(7-Morpholin-4-yl-6,7,8,9-tetrahydro-5H-benzocyclohepten-2-ylamino)-pyrrolo[2,1-f][1,2,4]triazin-7-yl]-phenyl}-methanesulfonamide The compound was made in an analogous fashion to Example 378 replacing 4-(4-Methyl-piperazin-1-yl)-phenylamine with 7-Morpholin-4-yl-6,7,8,9-tetrahydro-5H-benzocyclohepten-2-ylamine to afford 22.95 mg of N-{3-[2-(7-Morpholin-4-yl-6,7,8,9-tetrahydro-5H-benzocyclohepten-2-ylamino)-pyrrolo[2,1-f][1,2,4]triazin-7-yl]-phenyl}-methanesulfonamide as a lyophilized powder. (M+H)=533.1. $^1$H NMR (400 MHz, DMSO, d$_6$) δ 9.87 (s, 1H), 9.45 (s, 1H), 8.99 (s, 1H), 7.99 (d, 1H, J=7.69 Hz), 7.80 (m, 2H), 7.52 (t, 1H, J=7.97 Hz), 7.41 (d, 1H, J=7.97 Hz), 7.30 (m, 1H), 7.11 (m, 1H), 7.06 (m, 1H), 6.97 (m, 1H), 3.97 (m, 2H), 3.70 (m, 3H), 3.56 (m, 1H), 3.24 (m, 2H), 3.18 (m, 2H), 3.03 (s, 3H), 2.77 (m, 3H), 2.38 (m, 2H), 1.49 (m, 2H).

Example 383

[2-(4-Morpholin-4-yl-phenylamino)-pyrrolo[2,1-f][1,2,4]triazin-7-yl]-phenyl-methanol 383a. (2-Methylsulfanyl-pyrrolo[2,1-f][1,2,4]triazin-7-yl)-phenyl-methanol 1.00 M of Phenylmagnesium bromide in Tetrahydrofuran (1.552 mL, 1.552 mmol) was added to a solution of 2-Methylsulfanyl-pyrrolo[2,1-f][1,2,4]triazine-7-carbaldehyde (250.0 mg, 1.294 mmol) in Tetrahydrofuran (8.0 mL, 99 mmol) at 0° C. The reaction mixture was allowed to warm to room temperature with stirring for 3 hours. The mixture was then diluted with ethyl acetate and quenched with saturated ammonium chloride. The resulting mixture was washed with water and the organic layer was extracted, dried over sodium sulfate and reduced. The resulting oil was then purified via Isco flash column chromatography (hexanes/ethyl acetate) to afford 340 mg of (2-Methylsulfanyl-pyrrolo[2,1-f][1,2,4]triazin-7-yl)-phenyl-methanol. $^1$H NMR (400 MHz, DMSO, $d_6$) δ 8.90 (s, 1H), 7.43 (m, 2H), 7.32 (m, 2H), 6.93 (m, 1H), 6.88 (m, 1H), 6.24 (m, 1H), 6.14 (m, 1H), 3.29 (s, 4H).

383b. (2-Methanesulfinyl-pyrrolo[2,1-f][1,2,4]triazin-7-yl)-phenyl-methanol (2-Methylsulfanyl-pyrrolo[2,1-f][1,2,4]triazin-7-yl)-phenyl-methanol (0.340 g, 1.25 mmol) was dissolved in Methylene chloride (6 mL, 90 mmol) and the solution was treated with m-Chloroperbenzoic acid (0.379 g, 1.69 mmol) at room temperature. The reaction was allowed to stir until HPLC showed consumption of starting materials. The mixture was poured over saturated sodium bicarbonate and organics were extracted with dichloromethane. Combined extracts were then dried over sodium sulfate, filtered and reduced. The crude reaction mixture was then purified by Isco flash column chromatography (hexanes/ethyl acetate eluent) and combined fractions were reduced and dried under vacuum to afford 173 mg of (2-Methanesulfinyl-pyrrolo[2,1-f][1,2,4]triazin-7-yl)-phenyl-methanol. $^1$H NMR (400 MHz, CDCl$_3$) δ 8.91 (s, 1H), 7.48 (m, 2H), 7.33 (m, 3H), 6.92 (m, 1H), 6.84 (m, 1H), 6.50 (m, 1H).

383c. [2-(4-Morpholin-4-yl-phenylamino)-pyrrolo[2,1-f][1,2,4]triazin-7-yl]-phenyl-methanol (2-Methanesulfinyl-pyrrolo[2,1-f][1,2,4]triazin-7-yl)-phenyl-methanol (86.0 mg, 0.299 mmol), 4-(4-morpholino)aniline (107 mg, 0.598 mmol) and N,N-Diisopropylethylamine (0.156 mL, 0.898 mmol) were suspended in 1-Methoxy-2-propanol (0.750 mL, 7.67 mmol) and the reaction was irradiated at 300 watts, 200° C. for 20 minutes or until HPLC showed consumption of starting material. The reaction mixture was then reduced under nitrogen. The crude reaction mixture was purified via Gilson reverse phase chromatography to afford 5.69 mg of [2-(4-Morpholin-4-yl-phenylamino)-pyrrolo[2,1-f][1,2,4]triazin-7-yl]-phenyl-methanol as a lyophilized powder. (M+H)=402.1. $^1$H NMR (400 MHz, DMSO, $d_6$) δ 9.49 (s, 1H), 9.16 (s, 1H), 7.79 (d, 2H, J=7.12 Hz), 7.67 (m, 1H), 7.58 (m, 2H), 7.50 (d, 2H, J=7.89 Hz), 7.11 (m, 1H), 6.89 (m, 1H), 6.75 (d, 2H, J=8.44 Hz), 3.73 (m, 4H), 3.30 (m, 1H), 3.02 (m, 4H).

Example 384

5-[7-(6-Methoxy-pyridin-3-yl)-pyrrolo[2,1-f][1,2,4]triazin-2-ylamino]-1-methyl-1,3-dihydro-indol-2-one 2-Methanesulfinyl-7-(6-methoxy-pyridin-3-yl)-pyrrolo[2,1-f][1,2,4]triazine (125.0 mg, 0.0004335 mol), N,N-Diisopropylethylamine (0.249 mL, 0.00143 mol) and 5-Amino-1-methyl-1,3-dihydro-indol-2-one (0.141 g, 0.000867 mol) were dissolved in 1-Methoxy-2-propanol (0.498 mL, 0.00510 mol) and the reaction was irradiated at 300 watts, 180° C. for 40 minutes or until HPLC showed consumption of starting material. The reaction mixture was then reduced en vacuo and the product was isolated and purified by Gilson prep HPLC to afford 13.85 mg of 5-[7-(6-Methoxy-pyridin-3-yl)-pyrrolo[2,1-f][1,2,4]triazin-2-ylamino]-1-methyl-1,3-dihydro-indol-2-one as a lyophilized powder. (M+H)=387.1. $^1$H NMR (400 MHz, DMSO, $d_6$) δ 9.40 (s, 1H), 8.96 (s, 2H), 8.47 (d, 1H, J=8.73 Hz), 7.82 (s, 1H), 7.51 (d, 1H, J=8.40 Hz), 7.16 (d, 1H, J=4.37 Hz), 7.04 (d, 1H, J=8.65 Hz), 6.91 (m, 2H), 3.95 (s, 3H), 3.59 (s, 2H), 3.12 (s, 3H).

Example 385

N-Methyl-N-{3-[2-(4-morpholin-4-yl-phenylamino)-pyrrolo[2,1-f][1,2,4]triazin-7-ylamino]-pyridin-2-yl}-methanesulfonamide 385a. N-Methyl-N-[3-(2-methylsulfanyl-pyrrolo[2,1-f][1,2,4]triazin-7-ylamino)-pyridin-2-yl]-methanesulfonamide 7-Bromo-2-methylsulfanyl-pyrrolo[2,1-f][1,2,4]triazine (100.0 mg, 0.4096 mmol), Palladium Acetate (10 mg, 0.04 mmol), 9,9-Dimethyl-4,5-bis(diphenylphosphino)xanthene (25 mg, 0.044 mmol), and Cesium Carbonate (266.9 mg, 0.8193 mmol) were added to an oven-dried glass tube, equipped with a stirrbar and a septum. The tube was evacuated and backfilled with nitrogen 3 times, then 1,4-Dioxane (0.8 mL, 10 mmol) and N-(3-Amino-pyridin-2-yl)-N-methyl-methanesulfonamide (116.2 mg, 0.5777 mmol) were added via syringe and the reaction vessel was lowered in a preheated bath at 110° C. The reaction was stirred at this temperature for 8 hours under nitrogen. The reaction was partitioned between dichloromethane and water, and the aqueous layer was extracted twice with dichloromethane. The combined organic extracts were dried (MgSO4), filtered, concentrated under reduced pressure The product was isolated by Isco flash column chromatography (hexanes/ethyl acetate eluent) to afford 125.0 mg of N-Methyl-N-[3-(2-methylsulfanyl-pyrrolo[2,1-f][1,2,4]triazin-7-ylamino)-pyridin-2-yl]-methanesulfonamide. (M+H)=365.0. $^1$H NMR (400 MHz, DMSO, $d_6$) δ 8.80 (s, 1H), 8.23 (s, 1H), 8.03 (m, 1H), 7.51 (d, 1H, J=8.20 Hz), 7.35 (m, 1H), 7.03 (m, 1H), 6.94 (m, 1H), 3.21 (s, 3H), 3.19 (s, 3H), 2.40 (s, 3H).

385b. N-[3-(2-Methanesulfinyl-pyrrolo[2,1-f][1,2,4]triazin-7-ylamino)-pyridin-2-yl]-N-methyl-methanesulfonamide N-Methyl-N-[3-(2-methylsulfanyl-pyrrolo[2,1-f][1,2,4]triazin-7-ylamino)-pyridin-2-yl]-methanesulfonamide (125.0 mg, 0.3430 mmol) was dissolved in Methylene chloride (5.00 mL, 78.0 mmol) and the solution was treated with m-Chloroperbenzoic acid (76.87 mg, 0.3430 mmol). The reaction was then allowed to stir overnight at room temperature. The reaction mixture was poured over saturated sodium bicarbonate and organics were extracted with dichloromethane. Combined extracts were then dried over sodium sulfate, filtered and reduced. The crude reaction mixture was purified by Isco flash column chromatography (hexanes/ethyl acetate eluent) and combined fractions were reduced and dried under vacuum to afford 100 mg of N-[3-(2-Methanesulfinyl-pyrrolo[2,1-f][1,2,4]triazin-7-ylamino)-pyridin-2-yl]-N-methyl-methanesulfonamide. $^1$H NMR (400 MHz, DMSO, $d_6$) δ 9.11 (s, 1H), 8.24 (m, 1H), 8.07 (m, 1H), 7.46 (d, 1H, J=7.93 Hz), 7.33 (m, 1H), 7.26 (m, 1H), 7.14 (m, 1H), 3.23 (s, 3H), 3.18 (s, 3H), 2.89 (s, 3H).

385c. N-Methyl-N-{3-[2-(4-morpholin-4-yl-phenylamino)-pyrrolo[2,1-f][1,2,4]triazin-7-ylamino]-pyridin-2-yl}-methanesulfonamide N-[3-(2-Methanesulfinyl-pyrrolo[2,1-f][1,2,4]triazin-7-ylamino)-pyridin-2-yl]-N-methyl-methanesulfonamide (50.0 mg, 0.131 mmol), 4-(4-morpholino)aniline (46.8 mg, 0.263 mmol) and N,N-Diisopropylethylamine (0.0687 mL, 0.394 mmol) were dissolved in 1-Methoxy-2-propanol (0.500 mL, 5.12 mmol). The reaction was irradiated at 300 watts, 200° C. for 20 minutes. The reaction was then reduced en vacuo and the resulting residue was isolated and purified by Gilson prep HPLC to afford N-Methyl-N-{3-[2-(4-morpholin-4-yl-phenylamino)-pyrrolo[2,1-f][1,2,4]triazin-7-ylamino]-pyridin-2-yl}-methanesulfonamide as a lyophilized powder. (M+H)=495.1. $^1$H NMR (400 MHz, DMSO, $d_6$) δ 9.26 (s, 1H), 8.77 (s, 1H), 8.03 (m, 2H), 7.52 (d, 2H, J=8.05 Hz), 7.41 (d, 1H, J=8.24 Hz), 7.33 (m, 1H), 6.91 (m, 3H), 6.76 (m, 1H), 3.78 (m, 4H), 3.25 (s, 3H), 3.21 (s, 3H), 3.07 (m, 4H).

Example 386

N-{2-[2-(2-Fluoro-4-morpholin-4-yl-phenylamino)-pyrrolo[2,1-f][1,2,4]triazin-7-yl]-phenyl}-N-methyl-methanesulfonamide The compound was made in an analogous fashion to Example 370 replacing 2-Methanesulfinyl-7-(2-methoxy-phenyl)-pyrrolo[2,1-f][1,2,4]triazine with N-[2-(2-Methanesulfinyl-pyrrolo[2,1-f][1,2,4]triazin-7-yl)-phenyl]-N-methyl-methanesulfonamide to afford 33.88 mg of N-{2-[2-(2-Fluoro-4-morpholin-4-yl-phenylamino)-pyrrolo[2,1-f][1,2,4]triazin-7-yl]-phenyl}-N-methyl-methanesulfonamide as a lyophilized powder. (M+H)=497.1. $^1$H NMR (400 MHz, DMSO, $d_6$) δ 8.91 (s, 1H), 8.52 (s, 1H), 7.92 (m, 1H), 7.58 (m, 1H), 7.47 (m, 3H), 6.95 (m, 2H), 6.82 (m, 1H), 6.67 (m, 1H), 3.73 (m, 4H), 3.09 (m, 4H), 3.01 (s, 3H), 2.86 (s, 3H).

Example 387

N-Methyl-N-{3-[2-(1-methyl-2-oxo-2,3-dihydro-1H-indol-5-ylamino)-pyrrolo[2,1-f][1,2,4]triazin-7-ylamino]-pyridin-2-yl}-methanesulfonamide The compound was made in an analogous fashion to Example 384 replacing 4-(4-morpholino)aniline with 5-Amino-1-methyl-1,3-dihydro-indol-2-one to afford 14.17 mg of N-Methyl-N-{3-[2-(1-methyl-2-oxo-2,3-dihydro-1H-indol-5-ylamino)-pyrrolo[2,1-f][1,2,4]triazin-7-ylamino]-pyridin-2-yl}-methanesulfonamide as a lyophilized powder. (M+H)=479.1. $^1$H NMR (400 MHz, DMSO, $d_6$) δ 9.32 (s, 1H), 8.79 (s, 1H), 8.08 (s, 1H), 8.01 (m, 1H), 7.49 (m, 2H), 7.26 (m, 1H), 7.20 (m, 1H), 6.90 (m, 1H), 6.78 (d, 1H, J=8.13 Hz), 6.70 (m, 1H), 3.37 (s, 2H), 3.27 (s, 3H), 3.21 (s, 3H), 3.07 (s, 3H).

Example 388

N-{2-[2-(4-Fluoro-3-morpholin-4-yl-phenylamino)-pyrrolo[2,1-f][1,2,4]triazin-7-yl]-phenyl}-N-methyl-methanesulfonamide 388a. 4-(2-Fluoro-5-nitro-phenyl)-morpholine
2-Bromo-1-fluoro-4-nitro-benzene (750.0 mg, 3.409 mmol), Palladium Acetate (80 mg, 0.4 mmol), 9,9-Dimethyl-4,5-bis(diphenylphosphino)xanthene (210 mg, 0.37 mmol), and Cesium Carbonate (2222 mg, 6.818 mmol) were added to an oven-dried glass tube, equipped with a stir bar and a septum. The tube was evacuated and backfilled with nitrogen 3 times, then 1,4-Dioxane (7 mL, 90 mmol) and Morpholine (418.8 mg, 4.807 mmol) were added via syringe and the reaction vessel was lowered in a preheated bath at 110° C. The reaction was stirred at this temperature for 8 hours under nitrogen. The reaction was partitioned between dichloromethane and water, and the aqueous layer was extracted twice with dichloromethane. The combined organic extracts were dried (MgSO4), filtered, concentrated under reduced pressure, and the product was isolated by Isco flash column (hexanes/ethyl acetate) to afford 335 mg of 4-(2-Fluoro-5-nitro-phenyl)-morpholine. (M+H)=227.01. $^1$H NMR (400 MHz, DMSO, $d_6$) δ 7.89 (m, 1H), 7.79 (d, 1H, J=7.52 Hz), 7.45 (t, 1H, J=10.77 Hz), 3.75 (m, 4H), 3.11 (m, 4H).

388b. 4-Fluoro-3-morpholin-4-yl-phenylamine
4-(2-Fluoro-5-nitro-phenyl)-morpholine (335.0 mg, 1.481 mmol) was dissolved in Ethanol (10.0 mL, 171 mmol) and the reaction was treated with Tin(II) chloride dihydrate (1671 mg, 7.405 mmol). The reaction was then heated at 70° C. until HPLC showed consumption of starting material. The mixture was then made basic with 10% NaOH and the product was extracted with ethyl acetate. Note: When adding the NaOH, solid precipitate formed and was filtered and washed with ethyl acetate. The solid was discarded and the combined organics were then washed with water and dried over sodium sulfate, filtered and reduced to afford 235 mg of 4-Fluoro-3-morpholin-4-yl-phenylamine. $^1$H NMR (400 MHz, DMSO, $d_6$) δ 6.75 (m, 1H), 6.21 (d, 1H, J=7.56 Hz), 6.10 (m, 1H), 4.84 (s, 2H), 3.70 (m, 4H), 2.92 (m, 4H).

388c. N-{2-[2-(4-Fluoro-3-morpholin-4-yl-phenylamino)-pyrrolo[2,1-f][1,2,4]triazin-7-yl]-phenyl}-N-methyl-methanesulfonamide
4-Fluoro-3-morpholin-4-yl-phenylamine (50.0 mg, 0.255 mmol), N-[2-(2-Methanesulfinyl-pyrrolo[2,1-f][1,2,4]triazin-7-yl)-phenyl]-N-methyl-methanesulfonamide (46.4 mg, 0.127 mmol) and N,N-Diisopropylethylamine (0.0666 mL, 0.382 mmol) were dissolved in 1-Methoxy-2-propanol (0.50 mL, 5.1 mmol). The reaction was irradiated at 300 watts, 200° C. for 20 minutes or until HPLC showed consumption of starting material. The reaction mixture was then reduced and the crude residue was isolated and purified by Gilson prep HPLC to afford 23.77 mg of N-{2-[2-(4-Fluoro-3-morpholin-4-yl-phenylamino)-pyrrolo[2,1-f][1,2,4]triazin-7-yl]-phenyl}-N-methyl-methanesulfonamide as a lyophilized powder. (M+H)=497.1. $^1$H NMR (400 MHz, DMSO, $d_6$) δ 9.36 (s, 1H), 8.97 (s, 1H), 7.72 (m, 1H), 7.67 (m, 1H), 7.54 (m, 3H), 6.96 (m, 3H), 6.87 (m, 1H), 3.59 (m, 4H), 3.07 (s, 3H), 2.79 (s, 3H), 2.55 (m, 4H).

Example 389

(4-Fluoro-3-morpholin-4-yl-phenyl)-[7-(2-methoxy-phenyl)-pyrrolo[2,1-f][1,2,4]triazin-2-yl]-amine The compound was made in an analogous fashion to Example 387 replacing N-[2-(2-Methanesulfinyl-pyrrolo[2,1-f][1,2,4]triazin-7-yl)-phenyl]-N-methyl-methanesulfonamide with 2-Methanesulfinyl-7-(2-methoxy-phenyl)-pyrrolo[2,1-f][1,2,4]triazine to afford 22.19 mg of (4-Fluoro-3-morpholin-4-yl-phenyl)-[7-(2-methoxy-phenyl)-pyrrolo[2,1-f][1,2,4]triazin-2-yl]-amine as a lyophilized powder. (M+H)=420.1. $^1$H NMR (400 MHz, DMSO, $d_6$) δ 9.32 (s, 1H), 8.94 (s, 1H), 7.66 (d, 1H, 7.48 Hz), 7.44 (m, 1H), 7.39 (m, 1H), 7.20 (d, 2H, J=8.12 Hz), 7.08 (m, 1H), 6.90 (m, 3H), 3.74 (s, 3H), 3.64 (m, 4H), 2.71 (m, 4H).

Example 390

N-{3-[2-(4-Fluoro-3-morpholin-4-yl-phenylamino)-pyrrolo[2,1-f][1,2,4]triazin-7-yl]-phenyl}-methane-sulfonamide The compound was made in an analogous fashion to Example 387 replacing N-[2-(2-Methanesulfinyl-pyrrolo[2, 1-f][1,2,4]triazin-7-yl)-phenyl]-N-methyl-methanesulfonamide with N-[3-(2-Methanesulfinyl-pyrrolo[2,1-f][1,2,4]triazin-7-yl)-phenyl]-methanesulfonamide to afford 17.59 mg of N-{3-[2-(4-Fluoro-3-morpholin-4-yl-phenylamino)-pyrrolo[2,1-f][1,2,4]triazin-7-yl]-phenyl}-methanesulfonamide as a lyophilized powder. (M+H)=483.1. $^1$H NMR (400 MHz, DMSO, d$_6$) δ 9.87 (s, 1H), 9.41 (s, 1H), 9.01 (s, 1H), 7.84 (d, 1H, J=7.65 Hz), 7.77 (s, 1H), 7.48 (m, 1H), 7.38 (m, 2H), 7.25 (m, 1H), 7.03 (m, 2H), 6.95 (m, 1H), 3.67 (m, 4H), 3.00 (s, 3H), 2.86 (m, 4H).

Example 391

(4-Fluoro-3-morpholin-4-yl-phenyl)-(7-pyridin-3-yl-pyrrolo[2,1-f][1,2,4]triazin-2-yl)-amine The compound was made in an analogous fashion to Example 387 replacing N-[2-(2-Methanesulfinyl-pyrrolo[2,1-f][1,2,4]triazin-7-yl)-phenyl]-N-methyl-methanesulfonamide with 2-Methanesulfinyl-7-pyridin-3-yl-pyrrolo[2,1-f][1,2,4]triazine to afford 6.64 mg of (4-Fluoro-3-morpholin-4-yl-phenyl)-(7-pyridin-3-yl-pyrrolo[2,1-f][1,2,4]triazin-2-yl)-amine as a lyophilized powder. (M+H)=391.1. $^1$H NMR (400 MHz, DMSO, d$_6$) δ 9.49 (s, 1H), 9.39 (s, 1H), 9.06 (s, 1H), 8.66 (m, 2H), 7.70 (m, 1H), 7.36 (m, 1H), 7.32 (m, 2H), 7.14 (m, 1H), 7.01 (m, 1H), 3.69 (m, 4H), 2.90 (m, 4H).

Example 392

(4-Fluoro-3-morpholin-4-yl-phenyl)-[7-(6-methoxy-pyridin-3-yl)-pyrrolo[2,1-f][1,2,4]triazin-2-yl]-amine The compound was made in an analogous fashion to Example 387 replacing N-[2-(2-Methanesulfinyl-pyrrolo[2,1-f][1,2,4]triazin-7-yl)-phenyl]-N-methyl-methanesulfonamide with 2-M ethanesulfinyl-7-(6-methoxy-pyridin-3-yl)-pyrrolo[2,1-f][1,2,4]triazine to afford 12.34 mg of (4-Fluoro-3-morpholin-4-yl-phenyl)-[7-(6-methoxy-pyridin-3-yl)-pyrrolo[2,1-f][1,2,4]triazin-2-yl]-amine as a lyophilized powder. (M+H)=421.1. $^1$H NMR (400 MHz, DMSO, d$_6$) δ 9.40 (s, 1H), 8.99 (d, 2H, J=10.77 Hz), 8.35 (d, 1H, J=8.69 Hz), 7.47 (d, 1H, J=7.93 Hz), 7.16 (m, 2H), 7.07 (m, 1H), 6.97 (m, 2H), 3.94 (s, 3H), 3.68 (m, 4H), 2.92 (m, 4H).

Example 393

N-{2-[2-(4-Methoxy-3-morpholin-4-yl-phenylamino)-pyrrolo[2,1-f][1,2,4]triazin-7-yl]-phenyl}-N-methyl-methanesulfonamide 393a. 4-(2-Methoxy-5-nitro-phenyl)-morpholine
2-Bromo-1-methoxy-4-nitro-benzene (791.0 mg, 3.409 mmol), Palladium Acetate (80 mg, 0.4 mmol), 9,9-Dimethyl-4,5-bis(diphenylphosphino)xanthene (210 mg, 0.37 mmol), and Cesium Carbonate (2222 mg, 6.818 mmol) were added to an oven-dried glass tube, equipped with a stir bar and a septum. The tube was evacuated and backfilled with nitrogen 3 times, then 1,4-Dioxane (7 mL, 90 mmol) and Morpholine (418.8 mg, 4.807 mmol) were added via syringe and the reaction vessel was lowered in a preheated bath at 110° C. The reaction was stirred at this temperature for 8 hours under nitrogen. The reaction was partitioned between dichloromethane and water, and the aqueous layer was extracted twice with dichloromethane. The combined organic extracts were dried (MgSO4), filtered, concentrated under reduced pressure, and the product was isolated by Isco flash column chromatography (hexanes/ethyl acetate eluent) to afford 600 mg of 4-(2-Methoxy-5-nitro-phenyl)-morpholine. (M+H)=239.1. $^1$H NMR (400 MHz, DMSO, d$_6$) δ 7.94 (d, 1H, J=8.96 Hz), 7.65 (m, 1H), 7.17 (d, 1H, J=8.96 Hz), 3.93 (s, 3H), 3.74 (m, 4H), 3.03 (m, 4H).

393b. 4-Methoxy-3-morpholin-4-yl-phenylamine
4-(2-Methoxy-5-nitro-phenyl)-morpholine (0.600 g, 2.52 mmol) was dissolved in Ethanol (35.0 mL, 599 mmol) and the solution was carefully poured over 10% Palladium on Carbon (0.300 g, 22.5 mmol) under nitrogen. The mixture was then placed on a Parr hydrogenation apparatus and was allowed to shake at 55 psi until uptake of hydrogen ceased. The catalyst was then filtered to afford 460 mg of 4-Methoxy-3-morpholin-4-yl-phenylamine without further purification. (M+H)=209.2. $^1$H NMR (400 MHz, DMSO, d$_6$) δ 6.62 (d, 1H, J=8.36 Hz), 6.15 (m, 1H), 6.13 (m, 1H), 4.56 (s, 2H), 3.69 (m, 4H), 3.65 (s, 3H), 2.89 (m, 4H).

393c. N-{2-[2-(4-Methoxy-3-morpholin-4-yl-phenylamino)-pyrrolo[2,1-f][1,2,4]triazin-7-yl]-phenyl}-N-methyl-methanesulfonamide
4-Methoxy-3-morpholin-4-yl-phenylamine (80.0 mg, 0.384 mmol), N-[2-(2-Methanesulfinyl-pyrrolo[2,1-f][1,2,4]triazin-7-yl)-phenyl]-N-methyl-methanesulfonamide (70.0 mg, 0.192 mmol) and N,N-Diisopropylethylamine (0.100 mL, 0.576 mmol) were dissolved in 1-Methoxy-2-propanol (0.75 mL, 7.7 mmol). The reaction was irradiated at 300 watts, 200° C. for 20 minutes or until HPLC showed consumption of starting material. The reaction mixture was then reduced and the crude residue was isolated and purified by Gilson prep HPLC to afford 37.80 mg of N-{2-[2-(4-Methoxy-3-morpholin-4-yl-phenylamino)-pyrrolo[2,1-f][1,2,4]triazin-7-yl]-phenyl}-N-methyl-methanesulfonamide as a lyophilized powder. (M+H)=509.0. $^1$H NMR (400 MHz, DMSO, d$_6$) δ 9.18 (s, 1H), 8.94 (s, 1H), 7.73 (m, 1H), 7.65 (m, 1H), 7.52 (m, 2H), 7.41 (m, 1H), 7.05 (d, 1H, J=8.80 Hz), 6.91 (m, 1H), 6.83 (m, 2H), 3.72 (s, 3H), 3.61 (m, 4H), 3.06 (s, 3H), 2.79 (s, 3H), 2.60 (m, 4H).

Example 394

(4-Methoxy-3-morpholin-4-yl-phenyl)-[7-(2-methoxy-phenyl)-pyrrolo[2,1-f][1,2,4]triazin-2-yl]-amine The compound was made in an analogous fashion to Example 392 replacing N-[2-(2-Methanesulfinyl-pyrrolo[2,1-f][1,2,4]triazin-7-yl)-phenyl]-N-methyl-methanesulfonamide with 2-Methanesulfinyl-7-(2-methoxy-phenyl)-pyrrolo[2,1-f][1,2,4]triazine to afford 32.53 mg of (4-Methoxy-3-morpholin-4-yl-phenyl)-[7-(2-methoxy-phenyl)-pyrrolo[2,1-f][1,2,4]triazin-2-yl]-amine as a lyophilized powder. (M+H)=432.1. $^1$H NMR (400 MHz, DMSO, d$_6$) δ 9.14 (s, 1H), 8.92 (s, 1H), 7.71 (d, 1H, J=7.49 Hz), 7.43 (t, 1H, J=7.68 Hz), 7.30 (m, 2H), 7.19 (d, 1H, J=8.36 Hz), 7.09 (t, 1H, J=7.29 Hz), 6.88 (m, 2H), 6.81 (d, 1H, J=8.45 Hz), 3.75 (s, 6H), 3.67 (m, 4H), 2.78 (m, 4H).

Example 395

N-{3-[2-(4-Methoxy-3-morpholin-4-yl-phenylamino)-pyrrolo[2,1-f][1,2,4]triazin-7-yl]-phenyl}-methanesulfonamide The compound was made in an analogous fashion to Example 392 replacing N-[2-(2-Methanesulfinyl-pyrrolo[2,1-f][1,2,4]triazin-7-yl)-phenyl]-N-methyl-methanesulfonamide with N-[3-(2-Methanesulfinyl-pyrrolo[2,1-f][1,2,4]triazin-7-yl)-phenyl]-methanesulfonamide to afford 30.19 mg of N-{3-[2-(4-Methoxy-3-morpholin-4-yl-phenylamino)- pyrrolo[2,1-f][1,2,4]triazin-7-yl]-phenyl}-methanesulfonamide as a lyophilized powder. (M+H)=495.1. ¹H NMR (400 MHz, DMSO, d₆) δ 9.85 (s, 1H), 9.22 (s, 1H), 8.96 (s, 1H), 7.86 (d, 1H, J=7.89 Hz), 7.81 (m, 1H), 7.47 (m, 2H), 7.24 (m, 2H), 7.01 (m, 1H), 6.93 (m, 2H), 3.78 (s, 3H), 3.68 (m, 4H), 2.99 (s, 3H), 2.89 (m, 4H).

Example 396

(4-Methoxy-3-morpholin-4-yl-phenyl)-(7-pyridin-3-yl-pyrrolo[2,1-f][1,2,4]triazin-2-yl)-amine The compound was made in an analogous fashion to Example 392 replacing N-[2-(2-Methanesulfinyl-pyrrolo[2,1-f][1,2,4]triazin-7-yl)-phenyl]-N-methyl-methanesulfonamide with 2-Methanesulfinyl-7-pyridin-3-yl-pyrrolo[2,1-f][1,2,4]triazine to afford 20.68 mg of (4-Methoxy-3-morpholin-4-yl-phenyl)-(7-pyridin-3-yl-pyrrolo[2,1-f][1,2,4]triazin-2-yl)-amine as a lyophilized powder. (M+H)=403.1. ¹H NMR (400 MHz, DMSO, d₆) δ 9.45 (s, 1H), 9.34 (s, 1H), 9.04 (s, 1H), 8.80 (m, 1H), 8.69 (m, 1H), 7.80 (m, 1H), 7.35 (m, 2H), 7.22 (m, 1H), 6.96 (m, 2H), 3.79 (s, 3H), 3.70 (m, 4H), 2.92 (m, 4H).

Example 397

(4-Methoxy-3-morpholin-4-yl-phenyl)-[7-(6-methoxy-pyridin-3-yl)-pyrrolo[2,1-f][1,2,4]triazin-2-yl]-amine The compound was made in an analogous fashion to Example 392 replacing N-[2-(2-Methanesulfinyl-pyrrolo[2,1-f][1,2,4]triazin-7-yl)-phenyl]-N-methyl-methanesulfonamide with 2-M ethanesulfinyl-7-(6-methoxy-pyridin-3-yl)-pyrrolo[2,1-f][1,2,4]triazine to afford 26.09 mg of (4-Methoxy-3-morpholin-4-yl-phenyl)-[7-(6-methoxy-pyridin-3-yl)-pyrrolo[2,1-f][1,2,4]triazin-2-yl]-amine as a lyophilized powder. (M+H)=433.1. ¹H NMR (400 MHz, DMSO, d₆) δ 9.21 (s, 1H), 9.02 (s, 1H), 8.95 (s, 1H), 8.38 (d, 1H, J=8.64 Hz), 7.37 (s, 1H), 7.22 (m, 1H), 7.14 (d, 1H, J=4.36 Hz), 6.96 (m, 1H), 6.92 (m, 2H), 3.92 (s, 3H), 3.78 (s, 3H), 3.69 (m, 4H), 2.96 (m, 4H).

Example 398

N-[2-(2-{4-[4-((S)-2-Hydroxy-propyl)-piperazin-1-yl]-phenylamino}-pyrrolo[2,1-f][1,2,4]triazin-7-yl)-phenyl]-N-methyl-methanesulfonamide (S)-1-[4-(4-Amino-phenyl)-piperazin-1-yl]-propan-2-ol (129.1 mg, 0.5488 mmol), N-[2-(2-M ethanesulfinyl-pyrrolo[2,1-f][1,2,4]triazin-7-yl)-phenyl]-N-methyl-methanesulfonamide (100.0 mg, 0.2744 mmol) and N,N-Diisopropylethylamine (0.1434 mL, 0.8232 mmol) were dissolved in 1-Methoxy-2-propanol (1.00 mL, 10.2 mmol). The reaction was irradiated at 300 watts, 200° C. for 20 minutes or until HPLC showed consumption of starting material. The mixture was then reduced under nitrogen and the product was isolated and purified by Gilson prep HPLC to afford 82.63 mg of N-[2-(2-{4-[4-((S)-2-Hydroxy-propyl)-piperazin-1-yl]-phenylamino}-pyrrolo[2,1-f][1,2,4]triazin-7-yl)-phenyl]-N-methyl-methanesulfonamide as a lyophilized powder. (M+H)=536.1. ¹H NMR (400 MHz, DMSO, d₆) δ 9.51 (s, 1H), 9.24 (s, 1H), 8.95 (s, 1H), 8.01 (d, 1H, J=7.52 Hz), 7.65 (d, 1H, J=7.65 Hz), 7.50 (m, 4H), 6.97 (m, 2H), 6.85 (m, 2H), 4.12 (m, 1H), 3.66 (m, 4H), 3.17 (m, 3H), 3.08 (s, 3H), 2.95 (m, 3H), 2.89 (s, 3H), 1.13 (d, 3H, J=5.08 Hz).

Example 399

N-[2-(2-{4-[4-((R)-2-Hydroxy-propyl)-piperazin-1-yl]-phenylamino}-pyrrolo[2,1-f][1,2,4]triazin-7-yl)-phenyl]-N-methyl-methanesulfonamide (R)-1-[4-(4-Amino-phenyl)-piperazin-1-yl]-propan-2-ol (129.1 mg, 0.5488 mmol), N-[2-(2-Methanesulfinyl-pyrrolo[2,1-f][1,2,4]triazin-7-yl)-phenyl]-N-methyl-methanesulfonamide (100.0 mg, 0.2744 mmol) and N,N-Diisopropylethylamine (0.1434 mL, 0.8232 mmol) were dissolved in 1-Methoxy-2-propanol (1.00 mL, 10.2 mmol). The reaction was irradiated at 300 watts, 200° C. for 20 minutes or until HPLC showed consumption of starting material. The mixture was then reduced under nitrogen and the product was isolated and purified by Gilson prep HPLC to afford 61.36 mg of N-[2-(2-{4-[4-((R)-2-Hydroxy-propyl)-piperazin-1-yl]-phenylamino}-pyrrolo[2,1-f][1,2,4]triazin-7-yl)-phenyl]-N-methyl-methanesulfonamide as a lyophilized powder. (M+H)=536.1. ¹H NMR (400 MHz, DMSO, d₆) δ 9.51 (s, 1H), 9.24 (s, 1H), 8.95 (s, 1H), 8.01 (d, 1H, J=7.52 Hz), 7.65 (d, 1H, J=7.65 Hz), 7.50 (m, 4H), 6.97 (m, 2H), 6.85 (m, 2H), 4.12 (m, 1H), 3.66 (m, 4H), 3.17 (m, 3H), 3.08 (s, 3H), 2.95 (m, 3H), 2.89 (s, 3H), 1.13 (d, 3H, J=5.08 Hz).

Example 400

1-{2-[2-(4-Morpholin-4-yl-phenylamino)-pyrrolo[2,1-f][1,2,4]triazin-7-yl]-phenyl}-ethanone The compound was made in an analogous fashion to Example 331 replacing 6-hydroxy-3-pyridine boronic acid with 2-Acetylbenzeneboronic acid to afford 40.66 mg of 1-{2-[2-(4-Morpholin-4-yl-phenylamino)-pyrrolo[2,1-f][1,2,4]triazin-7-yl]-phenyl}-ethanone as a lyophilized powder. (M+H)=414.2. ¹H NMR (400 MHz, DMSO, d₆) δ 9.12 (s, 1H), 8.91 (s, 1H), 7.87 (m, 1H), 7.64 (m, 1H), 7.60 (m, 2H), 7.39 (d, 2H, J=7.57 Hz), 6.89 (m, 1H), 6.76 (m, 3H), 3.72 (m, 4H), 2.99 (m, 4H), 2.17 (s, 3H).

Example 401

2,2-Dimethyl-N-{2-[2-(4-morpholin-4-yl-phenylamino)-pyrrolo[2,1-f][1,2,4]triazin-7-yl]-phenyl}-propionamide The compound was made in an analogous fashion to Example 331 replacing 6-hydroxy-3-pyridine boronic acid with 2-(tert-butylcarbonylamino)phenylboronic acid to afford 85.91 mg of 2,2-Dimethyl-N-{2-[2-(4-morpholin-4-yl-phenylamino)-pyrrolo[2,1-f][1,2,4]triazin-7-yl]-phenyl}-propionamide as a lyophilized powder. (M+H)=471.2. ¹H NMR (400 MHz, DMSO, d₆) δ 9.51 (s, 1H), 8.99 (s, 1H), 8.79 (s, 1H), 7.68 (m, 2H), 7.56 (m, 3H), 7.38 (m, 1H), 6.98 (m, 1H), 6.88 (m, 3H), 3.75 (m, 4H), 3.07 (m, 4H), 0.90 (s, 9H).

Example 402

1-(2-{2-[4-(4-Methyl-piperazin-1-yl)-phenylamino]-pyrrolo[2,1-f][1,2,4]triazin-7-yl}-phenyl)-ethanone The compound was made in an analogous fashion to Example 366 replacing N-methyl-3-boronobenzenesulfonamide with 2-Acetylbenzeneboronic acid to afford 39.79 mg of 1-(2-{2-[4-(4-Methyl-piperazin-1-yl)-phenylamino]-pyrrolo[2,1-f][1,2,4]triazin-7-yl}-phenyl)-ethanone as a lyophilized powder. (M+H)=427.3. $^1$H NMR (400 MHz, DMSO, d$_6$) δ 9.09 (s, 1H), 8.91 (s, 1H), 7.88 (d, 1H, J=7.64 Hz), 7.68 (m, 1H), 7.62 (m, 2H), 7.37 (d, 2H, J=7.68 Hz), 6.89 (m, 1H), 6.80 (m, 1H), 6.74 (d, 2H, J=7.73 Hz), 3.01 (m, 4H), 2.43 (m, 4H), 2.21 (s, 3H), 2.17 (s, 3H).

Example 403

2,2-Dimethyl-N-(2-{2-[4-(4-methyl-piperazin-1-yl)-phenylamino]-pyrrolo[2,1-f][1,2,4]triazin-7-yl}-phenyl)-propionamide The compound was made in an analogous fashion to Example 366 replacing N-methyl-3-boronobenzenesulfonamide with 2-(tert-butylcarbonylamino)phenylboronic acid to afford 76.42 mg of 2,2-Dimethyl-N-(2-{2-[4-(4-methyl-piperazin-1-yl)-phenylamino]-pyrrolo[2,1-f][1,2,4]triazin-7-yl}-phenyl)-propionamide as a lyophilized powder. (M+H)=484.3. $^1$H NMR (400 MHz, DMSO, d$_6$) δ 9.42 (s, 1H), 8.97 (s, 1H), 8.81 (s, 1H), 7.67 (m, 2H), 7.48 (d, 3H, J=7.91 Hz), 7.34 (t, 1H, J=7.52 Hz), 6.96 (d, 1H, J=3.97 Hz), 6.86 (d, 1H J=4.40 Hz), 6.78 (d, 2H, J=8.01 Hz), 3.02 (m, 4H), 2.43 (m, 4H), 2.21 (s, 3H), 0.87 (s, 9H).

Example 404

[7-(2-Methanesulfinyl-phenyl)-pyrrolo[2,1-f][1,2,4]triazin-2-yl]-[4-(4-methyl-piperazin-1-yl)-phenyl]-amine The compound was made in an analogous fashion to Example 366 replacing N-methyl-3-boronobenzenesulfonamide with 2-Methylsulfinyl phenylboronic acid to afford 35.01 mg of [7-(2-Methanesulfinyl-phenyl)-pyrrolo[2,1-f][1,2,4]triazin-2-yl]-[4-(4-methyl-piperazin-1-yl)-phenyl]-amine as a lyophilized powder. (M+H)=447.2. $^1$H NMR (400 MHz, DMSO, d$_6$) δ 9.23 (s, 1H), 8.98 (s, 1H), 8.08 (d, 1H, J=7.60 Hz), 7.75 (m, 3H), 7.41 (d, 2H, J=7.89 Hz), 6.93 (d, 1H, J=4.00 Hz), 6.88 (d, 1H, J=4.08 Hz), 6.72 (d, 2H, J=7.97 Hz), 3.00 (m, 4H), 2.41 (m, 7H), 2.20 (s, 3H).

Example 405

[7-(2-Methanesulfinyl-phenyl)-pyrrolo[2,1-f][1,2,4]triazin-2-yl]-(4-morpholin-4-yl-phenyl)-amine The compound was made in an analogous fashion to Example 331 replacing 6-hydroxy-3-pyridine boronic acid with 2-Methylsulfinyl phenylboronic acid to afford 49.99 mg of [7-(2-M ethanesulfinyl-phenyl)-pyrrolo[2,1-f][1,2,4]triazin-2-yl]-(4-morpholin-4-yl-phenyl)-amine as a lyophilized powder. (M+H)=434.1. $^1$H NMR (400 MHz, DMSO, d$_6$) δ 9.26 (s, 1H), 8.99 (s, 1H), 8.08 (d, 1H, J=7.69 Hz), 7.75 (m, 3H), 7.43 (d, 2H, J=8.00 Hz), 6.93 (d, 1H, J=4.12 Hz), 6.88 (d, 1H, J=3.96 Hz), 6.73 (d, 2H, J=7.99 Hz), 3.71 (m, 4H), 2.97 (m, 4H), 2.41 (s, 3H).

Example 406

[7-(2-Methanesulfonyl-phenyl)-pyrrolo[2,1-f][1,2,4]triazin-2-yl]-[4-(4-methyl-piperazin-1-yl)-phenyl]-amine The compound was made in an analogous fashion to Example 366 replacing N-methyl-3-boronobenzenesulfonamide with 2-(Methylsulfonyl)phenylboronic acid to afford 28.19 mg of [7-(2-Methanesulfonyl-phenyl)-pyrrolo[2,1-f][1,2,4]triazin-2-yl]-[4-(4-methyl-piperazin-1-yl)-phenyl]-amine as a lyophilized powder. (M+H)=463.2. $^1$H NMR (400 MHz, DMSO, d$_6$) δ 9.17 (s, 1H), 8.96 (s, 1H), 8.17 (d, 1H, J=7.88 Hz), 7.90 (m, 1H), 7.79 (m, 1H), 7.73 (m, 1H), 7.33 (d, 2H, J=7.97 Hz), 6.93 (dd, 2H, J=3.68, 9.97 Hz), 6.67 (d, 2H, J=7.96 Hz), 2.98 (m, 4H), 2.86 (s, 3H), 2.42 (m, 4H), 2.20 (s, 3H).

Example 407

N,N-Diethyl-2-{2-[4-(4-methyl-piperazin-1-yl)-phenylamino]-pyrrolo[2,1-f][1,2,4]triazin-7-yl}-benzamide The compound was made in an analogous fashion to Example 366 replacing N-methyl-3-boronobenzenesulfonamide with 2-(N,N-diethylaminocarbonyl)pheylboronic acid to afford 58.49 mg of N,N-Diethyl-2-{2-[4-(4-methyl-piperazin-1-yl)-phenylamino]-pyrrolo[2,1-f][1,2,4]triazin-7-yl}-benzamide as a lyophilized powder. (M+H)=484.3. $^1$H NMR (400 MHz, DMSO, d$_6$) δ 9.22 (s, 1H), 8.94 (s, 1H), 8.09 (d, 1H, J=7.41 Hz), 7.63 (m, 1H), 7.55 (m, 3H), 7.37 (m, 1H), 6.84 (m, 3H), 6.71 (d, 1H, J=4.73 Hz), 3.05 (m, 4H), 2.71 (m, 4H), 2.45 (m, 4H), 2.21 (s, 3H), 0.95 (t, 3H, J=7.05 Hz), 0.61 (t, 3H, J=7.00 Hz).

Example 408

N,N-Diethyl-2-[2-(4-morpholin-4-yl-phenylamino)-pyrrolo[2,1-f][1,2,4]triazin-7-yl]-benzamide The compound was made in an analogous fashion to Example 331 replacing 6-hydroxy-3-pyridine boronic acid with 2-(N,N-diethylaminocarbonyl)phenylboronic acid to afford 55.23 mg of N,N-Diethyl-2-[2-(4-morpholin-4-yl-phenylamino)-pyrrolo[2,1-f][1,2,4]triazin-7-yl]-benzamide as a lyophilized powder. (M+H)=471.2. $^1$H NMR (400 MHz, DMSO, d$_6$) δ 9.25 (s, 1H), 8.95 (s, 1H), 8.09 (d, 1H, J=7.41 Hz), 7.63 (m, 1H), 7.57 (d, 2H, J=9.04 Hz), 7.50 (m, 1H), 7.37 (m, 1H), 6.84 (m, 3H), 6.71 (d, 1H, J=4.68 Hz), 3.73 (m, 4H), 3.29 (m, 4H), 3.01 (m, 4H), 0.95 (t, 3H, J=7.05 Hz), 0.61 (t, 3H, J=7.00 Hz).

Example 409

2-{2-[4-(4-Methyl-piperazin-1-yl)-phenylamino]-pyrrolo[2,1-f][1,2,4]triazin-7-yl}-benzamide The compound was made in an analogous fashion to Example 366 replacing N-methyl-3-boronobenzenesulfonamide with 2-aminocarbonylphenylboronic acid to afford 52.56 mg of 2-{2-[4-(4-Methyl-piperazin-1-yl)-phenylamino]-pyrrolo[2,1-f][1,2,4]triazin-7-yl}-benzamide as a lyophilized powder. (M+H)=428.2. $^1$H NMR (400 MHz, DMSO, d$_6$) δ 9.13 (s, 1H), 8.90 (s, 1H), 7.94 (d, 1H, J=7.80 Hz), 7.66 (m, 1H), 7.57 (m, 4H), 7.49 (m, 1H), 7.31 (m, 1H), 6.84 (m, 4H), 3.02 (m, 4H), 2.44 (m, 4H), 2.21 (s, 3H).

Example 410

N-Methyl-N-{2-[2-(3-morpholin-4-yl-phenylamino)-pyrrolo[2,1-f][1,2,4]triazin-7-yl]-phenyl}-methanesulfonamide 3-Morpholin-4-yl-phenylamine (122.3 mg, 0.6860 mmol), N-[2-(2-Methanesulfinyl-pyrrolo[2,1-f][1,2,4]triazin-7-yl)- phenyl]-N-methyl-methanesulfonamide (125.0 mg, 0.3430 mmol) and N,N-Diisopropylethylamine (0.1792 mL, 1.029 mmol) were dissolved in 1-Methoxy-2-propanol (1.25 mL, 12.8 mmol). The reaction was irradiated at 300 watts, 200° C. for 20 minutes or until HPLC showed consumption of starting material. The mixture was then reduced under nitrogen and the product was isolated and purified by Gilson prep HPLC to afford 35.51 mg of N-Methyl-N-{2-[2-(3-morpholin-4-yl-phenylamino)-pyrrolo[2,1-f][1,2,4]triazin-7-yl]-phenyl}-methanesulfonamide as a lyophilized powder. (M+H)=479.1. $^1$H NMR (400 MHz, DMSO, d$_6$) δ 9.26 (s, 1H), 8.97 (s, 1H), 7.73 (m, 1H), 7.66 (m, 1H), 7.55 (m, 2H), 7.48 (m, 1H), 7.02 (t, 1H, J=8.09 Hz), 6.93 (d, 1H, J=4.64 Hz), 6.87 (m, 2H), 6.45 (m, 1H), 3.57 (m, 4H), 3.08 (s, 3H), 2.71 (s, 3H), 2.67 (m, 4H).

Example 411

2-Methyl-propane-2-sulfonic acid (2-{2-[4-(4-methyl-piperazin-1-yl)-phenylamino]-pyrrolo[2,1-f][1,2,4]triazin-7-yl}-phenyl)-amide The compound was made in an analogous fashion to Example 366 replacing N-methyl-3-boronobenzenesulfonamide with 2-(tert-butylamino)sulfonylphenylboronic acid to afford 59.67 mg of 2-Methyl-propane-2-sulfonic acid (2-{2-[4-(4-methyl-piperazin-1-yl)-phenylamino]-pyrrolo[2,1-f][1,2,4]triazin-7-yl}-phenyl)-amide as a lyophilized powder. (M+H)=520.2. $^1$H NMR (400 MHz, DMSO, d$_6$) δ 9.14 (s, 1H), 8.95 (s, 1H), 8.12 (d, 1H, J=6.97 Hz), 7.75 (m, 1H), 7.70 (m 2H), 7.41 (d, 2H, J=9.08 Hz), 6.93 (d, 1H, 4.64 Hz), 6.88 (d, 1H, J=4.64 Hz), 6.65 (d, 2H, J=9.12 Hz), 6.27 (s, 1H), 2.97 (m, 4H), 2.41 (m, 4H), 2.20 (s, 3H), 0.85 (s, 9H).

Example 412

2-Methyl-propane-2-sulfonic acid {2-[2-(4-morpholin-4-yl-phenylamino)-pyrrolo[2,1-f][1,2,4]triazin-7-yl]-phenyl}-amide The compound was made in an analogous fashion to Example 331 replacing 6-hydroxy-3-pyridine boronic acid with 2-(tert-butylamino)sulfonylphenylboronic acid to afford 34.39 mg of 2-Methyl-propane-2-sulfonic acid {2-[2-(4-morpholin-4-yl-phenylamino)-pyrrolo[2,1-f][1,2,4]triazin-7-yl]-phenyl}-amide as a lyophilized powder. (M+H)=507.2. $^1$H NMR (400 MHz, DMSO, d$_6$) δ 9.16 (s, 1H), 8.96 (s, 1H), 8.13 (d, 1H, J=7.00 Hz), 7.72 (m, 3H), 7.43 (d, 2H, J=9.08 Hz), 6.94 (d, 1H, J=4.64 Hz), 6.88 (d, 1H, J=4.64 Hz), 6.66 (d, 2H, J=9.13 Hz), 6.28 (s, 1H), 3.70 (m, 4H), 2.95 (m, 4H), 0.84 (s, 9H).

Example 413

Cyclopropanesulfonic acid (3-{2-[4-(4-methyl-piperazin-1-yl)-phenylamino]-pyrrolo[2,1-f][1,2,4]triazin-7-yl}-phenyl)-amide The compound was made in an analogous fashion to Example 366 replacing N-methyl-3-boronobenzenesulfonamide with 3-(Cyclopropanesulfonamido)phenylboronic acid to afford 75.80 mg of Cyclopropanesulfonic acid (3-{2-[4-(4-methyl-piperazin-1-yl)-phenylamino]-pyrrolo[2,1-f][1,2,4]triazin-7-yl}-phenyl)-amide as a lyophilized powder. (M+H)=504.2. $^1$H NMR (400 MHz, DMSO, d$_6$) δ 9.63 (s, 1H), 9.22 (s, 1H), 8.95 (s, 1H), 7.95 (m, 1H), 7.93 (d, 1H, J=10.57 Hz), 7.62 (d, 2H, J=9.04 Hz), 7.49 (t, 1H, J=7.96 Hz), 7.27 (m, 1H), 7.03 (d, 1H, J=4.73 Hz), 6.92 (m, 3H), 3.06 (m, 4H), 2.63 (m, 1H), 2.45 (m, 4H), 2.22 (s, 3H), 0.93 (m, 4H).

Example 414

Cyclopropanesulfonic acid {3-[2-(4-morpholin-4-yl-phenylamino)-pyrrolo[2,1-f][1,2,4]triazin-7-yl]-phenyl}-amide The compound was made in an analogous fashion to Example 331 replacing 6-hydroxy-3-pyridine boronic acid with 3-(Cyclopropanesulfonamido)phenylboronic acid to afford 64.99 mg of Cyclopropanesulfonic acid {3-[2-(4-morpholin-4-yl-phenylamino)-pyrrolo[2,1-f][1,2,4]triazin-7-yl]-phenyl}-amide as a lyophilized powder. (M+H)=491.1. $^1$H NMR (400 MHz, DMSO, d$_6$) δ 9.82 (s, 1H), 9.25 (s, 1H), 8.95 (s, 1H), 7.96 (m, 1H), 7.94 (m, 1H), 7.64 (d, 2H, J=9.05 Hz), 7.49 (m 1H), 7.22 (m, 1H), 7.04 (d, 1H, J=4.75 Hz), 6.93 (m, 3H), 3.74 (m, 4H), 3.05 (m, 4H), 2.61 (m, 1H), 0.92 (m, 4H).

Example 415

Ethanesulfonic acid (3-{2-[4-(4-methyl-piperazin-1-yl)-phenylamino]-pyrrolo[2,1-f][1,2,4]triazin-7-yl}-phenyl)-amide The compound was made in an analogous fashion to Example 366 replacing N-methyl-3-boronobenzenesulfonamide with 3-(Ethylsulfonamido)phenylboronic acid to afford 88.03 mg of Ethanesulfonic acid (3-{2-[4-(4-methyl-piperazin-1-yl)-phenylamino]-pyrrolo[2,1-f][1,2,4]triazin-7-yl}-phenyl)-amide as a lyophilized powder. (M+H)=492.2. $^1$H NMR (400 MHz, DMSO, d$_6$) δ 9.86 (s, 1H), 9.22 (s, 1H), 8.95 (s, 1H), 7.90 (m, 2H), 7.62 (d, 2H, J=9.00 Hz), 7.48 (t, 1H, J=7.84 Hz), 7.23 (m, 1H), 7.01 (d, 1H, J=4.72 Hz), 6.91 (m, 3H), 3.11 (q, 2H, J=7.36 Hz), 3.07 (m, 4H), 2.46 (m, 4H), 2.22 (s, 3H), 1.21 (t, 3H, J=7.33 Hz).

Example 416

Ethanesulfonic acid {3-[2-(4-morpholin-4-yl-phenylamino)-pyrrolo[2,1-f][1,2,4]triazin-7-yl]-phenyl}-amide The compound was made in an analogous fashion to Example 331 replacing 6-hydroxy-3-pyridine boronic acid with 3-(Ethylsulfonamido)phenylboronic acid to afford 50.38 mg of Ethanesulfonic acid {3-[2-(4-morpholin-4-yl-phenylamino)-pyrrolo[2,1-f][1,2,4]triazin-7-yl]-phenyl}-amide as a lyophilized powder. (M+H)=491.1. $^1$H NMR (400 MHz, DMSO, d$_6$) δ 9.88 (s, 1H), 9.25 (s, 1H), 8.96 (s, 1H), 7.91 (m, 2H), 7.64 (d, 2H, J=9.01 Hz), 7.49 (t, 1H, J=7.89 Hz), 7.23 (m, 1H), 7.02 (d, 1H, J=4.72 Hz), 6.92 (m, 3H), 3.74 (m, 4H), 3.12 (q, 2H, J=7.32 Hz), 3.04 (m, 4H), 1.21 (t, 3H, J=7.33 Hz).

Example 417

Propane-1-sulfonic acid (3-{2-[4-(4-methyl-piperazin-1-yl)-phenylamino]-pyrrolo[2,1-f][1,2,4]triazin-7-yl}-phenyl)-amide The compound was made in an analogous fashion to Example 366 replacing N-methyl-3-boronobenzenesulfonamide with 3-(n-Propylsulfonamido)phenylboronic acid to afford 73.02 mg of Propane-1-sulfonic acid (3-{2-[4-(4-methyl-piperazin-1-yl)-phenylamino]-pyrrolo[2,1-f][1,2,4]triazin-7-yl}-phenyl)-amide as a lyophilized powder. (M+H)= 506.2. $^1$H NMR (400 MHz, DMSO, d$_6$) δ 9.74 (s, 1H), 9.22 (s, 1H), 8.94 (s, 1H), 7.89 (m, 2H), 7.62 (d, 2H, J=9.04 Hz), 7.49 (t, 1H, J=7.92 Hz), 7.22 (m, 1H), 7.01 (d, 1H, J=4.68 Hz), 6.92 (m, 3H), 3.08 (m, 6H), 2.45 (m, 4H), 2.22 (s, 3H), 1.71 (m, 2H), 0.93 (t, 3H, J=7.40 Hz).

Example 418

Propane-1-sulfonic acid {3-[2-(4-morpholin-4-yl-phenylamino)-pyrrolo[2,1-f][1,2,4]triazin-7-yl]-phenyl}-amide The compound was made in an analogous fashion to Example 331 replacing 6-hydroxy-3-pyridine boronic acid with 3-(n-Propylsulfonamido)phenylboronic acid to afford 34.33 mg of Propane-1-sulfonic acid {3-[2-(4-morpholin-4-yl-phenylamino)-pyrrolo[2,1-f][1,2,4]triazin-7-yl]-phenyl}-amide as a lyophilized powder. (M+H)=493.1. $^1$H NMR (400 MHz, DMSO, d$_6$) δ 9.73 (s, 1H), 9.22 (s, 1H), 8.94 (s, 1H), 7.83 (m, 2H), 7.66 (d, 2H, J=7.77 Hz), 7.42 (m, 1H), 7.19 (m, 1H), 7.00 (m, 1H), 6.91 (m, 3H), 3.74 (m, 4H), 3.05 (m, 4H), 2.99 (m, 2H), 1.67 (m, 2H), 0.92 (t, 3H, J=7.44 Hz).

Example 419

N-Methyl-N-(3-{2-[4-(4-methyl-piperazin-1-yl)-phenylamino]-pyrrolo[2,1-f][1,2,4]triazin-7-yl}-phenyl)-methanesulfonamide 419a. N-Methyl-N-[3-(4,4,5,5-tetramethyl-1,3,2-dioxaborolan-2-yl)-phenyl]-methanesulfonamide A round bottom flask was charged with Potassium carbonate (1.1 g, 8.1 mmol) and Acetone (40 mL, 500 mmol). To the suspension was added N-[3-(4,4,5,5-Tetramethyl-1,3,2-dioxaborolan-2-yl)-phenyl]-methanesulfonamide (2.0 g, 6.7 mmol) followed by Methyl iodide (0.50 mL, 8.1 mmol). The mixture was stirred at room temperature for 18 hours. The reaction was then diluted with dichloromethane (20 mL), filtered through a plug of diatomaceous earth, rinsed with dichloromethane and evaporated to a viscous oil. The material was subjected to high vacuum for 18 hours. The resulting white solid (2.00 g) was consistent for desired N-Methyl-N-[3-(4,4,5,5-tetramethyl-1,3,2-dioxaborolan-2-yl)-phenyl]-methanesulfonamide and was used without further purification. $^1$H NMR (400 MHz, DMSO, d$_6$) δ 7.63 (m, 1H), 7.60 (m, 1H), 7.49 (m, 1H), 3.24 (s, 3H), 2.97 (s, 3H), 1.30 (s, 12H).

419b. N-Methyl-N-(3-{2-[4-(4-methyl-piperazin-1-yl)-phenylamino]-pyrrolo[2,1-f][1,2,4]triazin-7-yl}-phenyl)-methanesulfonamide The compound was made in an analogous fashion to Example 366 replacing N-methyl-3-boronobenzenesulfonamide with N-Methyl-N-[3-(4,4,5,5-tetramethyl-1,3,2-dioxaborolan-2-yl)-phenyl]-methanesulfonamide to afford 14.10 mg of N-Methyl-N-(3-{2-[4-(4-methyl-piperazin-1-yl)-phenylamino]-pyrrolo[2,1-f][1,2,4]triazin-7-yl}-phenyl)-methanesulfonamide as a lyophilized powder. (M+H)=492.2. $^1$H NMR (400 MHz, DMSO, d$_6$) δ 9.34 (s, 1H), 8.98 (s, 1H), 8.26 (s, 1H), 8.09 (d, 1H, J=7.97 Hz), 7.66 (d, 2H, J=9.00 Hz), 7.57 (t, 1H, J=7.97 Hz), 7.46 (m, 1H), 7.21 (d, 1H, J=4.77 Hz), 7.02 (d, 2H, J=9.05 Hz), 6.95 (d, 1H, J=4.76 Hz), 3.75 (m, 2H), 3.54 (m, 5H), 3.15 (m, 2H), 2.98 (s, 3H), 2.92 (m, 2H), 2.87 (s, 3H).

Example 420

N-Methyl-N-{3-[2-(4-morpholin-4-yl-phenylamino)-pyrrolo[2,1-f][1,2,4]triazin-7-yl]-phenyl}-methanesulfonamide The compound was made in an analogous fashion to Example 331 replacing 6-hydroxy-3-pyridine boronic acid with N-Methyl-N-[3-(4,4,5,5-tetramethyl-1,3,2-dioxaborolan-2-yl)-phenyl]-methanesulfonamide to afford 40.80 mg of N-Methyl-N-{3-[2-(4-morpholin-4-yl-phenylamino)-pyrrolo[2,1-f][1,2,4]triazin-7-yl]-phenyl}-methane sulfonamide as a lyophilized powder. (M+H)=479.2. $^1$H NMR (400 MHz, DMSO, d$_6$) δ 9.29 (s, 1H), 8.96 (s, 1H), 8.24 (m, 1H), 8.10 (d, 1H, J=7.88 Hz), 7.64 (d, 2H, J=8.96), 7.57 (t, 1H, J=7.97 Hz), 7.45 (m, 1H), 7.21 (d, 1H, J=4.76 Hz), 6.99 (m, 2H), 6.93 (d, 1H, J=4.76 Hz), 3.75 (m, 4H), 3.31 (s, 3H), 3.08 (m, 4H), 2.98 (s, 3H).

Example 421

[7-(4-Methoxy-phenyl)-pyrrolo[2,1-f][1,2,4]triazin-2-yl]-[4-(4-methyl-piperazin-1-yl)-phenyl]-amine The compound was made in an analogous fashion to Example 366 replacing N-methyl-3-boronobenzenesulfonamide with 4-methoxyphenylboronic acid to afford 56.68 mg of [7-(4-Methoxy-phenyl)-pyrrolo[2,1-f][1,2,4]triazin-2-yl]-[4-(4-methyl-piperazin-1-yl)-phenyl]-amine as a lyophilized powder. (M+H)=415.2. $^1$H NMR (400 MHz, DMSO, d$_6$) δ 9.27 (s, 1H), 8.90 (s, 1H), 8.14 (d, 2H, J=8.84 Hz), 7.67 (d, 2H, J=8.96 Hz), 7.09 (m, 3H), 6.99 (m, 2H), 6.91 (d, 1H, J=4.72 Hz), 3.85 (s, 3H), 3.53 (m, 4H), 3.18 (m, 2H), 2.92 (m, 2H), 2.88 (s, 3H).

Example 422

[7-(3-Methoxy-phenyl)-pyrrolo[2,1-f][1,2,4]triazin-2-yl]-(4-morpholin-4-yl-phenyl)-amine The compound was made in an analogous fashion to Example 331 replacing 6-hydroxy-3-pyridine boronic acid with 3-methoxyphenylboronic acid to afford 34.97 mg of [7-(3-Methoxy-phenyl)-pyrrolo[2,1-f][1,2,4]triazin-2-yl]-(4-morpholin-4-yl-phenyl)-amine as a lyophilized powder. (M+H)=402.1. $^1$H NMR (400 MHz, DMSO, d$_6$) δ 9.26 (s, 1H), 8.94 (s, 1H), 7.80 (s, 1H), 7.72 (d, 1H, J=7.88 Hz), 7.66 (d, 2H, J=8.89 Hz), 7.44 (t, 1H, J=8.04 Hz), 7.16 (d, 1H, J=4.72 Hz), 6.98 (m, 1H), 6.93 (m, 3H), 3.81 (s, 3H), 3.75 (m, 4H), 3.07 (m, 4H).

Example 423

[7-(3-Methoxy-phenyl)-pyrrolo[2,1-f][1,2,4]triazin-2-yl]-[4-(4-methyl-piperazin-1-yl)-phenyl]-amine The compound was made in an analogous fashion to Example 366 replacing N-methyl-3-boronobenzenesulfonamide with 3-methoxyphenylboronic acid to afford 108.74 mg of [7-(3-Methoxy-phenyl)-pyrrolo[2,1-f][1,2,4]triazin-2-yl]-[4-(4-methyl-piperazin-1-yl)-phenyl]-amine as a lyophilized powder. (M+H)=415.2. $^1$H NMR (400 MHz, DMSO, d$_6$) δ 9.32 (s, 1H), 8.95 (s, 1H), 7.79 (m, 1H), 7.72 (m, 3H), 7.45 (t, 1H, J=8.05 Hz), 7.17 (d, 1H, J=4.72 Hz), 6.96 (m, 4H), 3.74 (s, 3H), 3.62 (m, 2H), 3.55 (m, 2H), 3.20 (m, 2H), 2.95 (m, 2H), 2.88 (s, 3H).

Example 424

[7-(2,5-Dimethoxy-phenyl)-pyrrolo[2,1-f][1,2,4]triazin-2-yl]-(4-morpholin-4-yl-phenyl)-amine The compound was made in an analogous fashion to Example 331 replacing 6-hydroxy-3-pyridine boronic acid with 2,5-dimethoxyphenylboronic acid to afford 48.21 mg of [7-(2,5-Dimethoxy-phenyl)-pyrrolo[2,1-f][1,2,4]triazin-2-yl]-(4-morpholin-4-yl-phenyl)-amine as a lyophilized powder. (M+H)=432.2. $^1$H NMR (400 MHz, DMSO, $d_6$) δ 9.21 (s, 1H), 8.93 (s, 1H), 7.65 (m, 2H), 7.47 (d, 1H, J=3.09 Hz), 7.13 (d, 1H, J=9.04 Hz), 7.03 (m, 1H), 6.95 (m, 3H), 6.89 (d, 1H, J=4.64 Hz), 3.78 (m 4H), 3.74 (s, 6H), 3.12 (m, 4H).

Example 425

[7-(2,5-Dimethoxy-phenyl)-pyrrolo[2,1-f][1,2,4]triazin-2-yl]-[4-(4-methyl-piperazin-1-yl)-phenyl]-amine The compound was made in an analogous fashion to Example 366 replacing N-methyl-3-boronobenzenesulfonamide with 2,5-dimethoxyphenylboronic acid to afford 52.33 mg of [7-(2,5-Dimethoxy-phenyl)-pyrrolo[2,1-f][1,2,4]triazin-2-yl]-[4-(4-methyl-piperazin-1-yl)-phenyl]-amine as a lyophilized powder. (M+H)=445.2. $^1$H NMR (400 MHz, DMSO, $d_6$) δ 9.25 (s, 1H), 8.93 (s, 1H), 7.64 (d, 2H, J=8.96 Hz), 7.48 (d, 1H, J=3.07 Hz), 7.13 (d, 1H, J=9.04 Hz), 7.03 (m, 1H), 6.96 (d, 1H, J=4.64 Hz), 6.87 (m, 3H), 3.75 (s, 6H), 3.53 (m, 4H), 3.18 (m, 2H), 2.90 (m, 5H).

Example 426

N-tert-Butyl-3-(2-{4-[4-((R)-2-hydroxy-propyl)-piperazin-1-yl]-phenylamino}-pyrrolo[2,1-f][1,2,4]triazin-7-yl)-benzenesulfonamide N-tert-Butyl-3-(2-methanesulfinyl-pyrrolo[2,1-f][1,2,4]triazin-7-yl)-benzenesulfonamide (125.1 mg, 0.0003187 mol), N,N-Diisopropylethylamine (0.1665 mL, 0.0009561 mol) and (R)-1-[4-(4-Amino-phenyl)-piperazin-1-yl]-propan-2-ol (150 mg, 0.00064 mol) were dissolved in 2-Methoxyethanol (2.24 mL, 0.0284 mol) and the reaction was irradiated at 300 watts, 180° C. for 40 minutes or until HPLC showed consumption of starting material. The reaction mixture was then reduced en vacuo and the product was isolated and purified by Gilson prep HPLC to afford 107.72 mg of N-tert-Butyl-3-(2-{4-[4-((R)-2-hydroxy-propyl)-piperazin-1-yl]-phenylamino}-pyrrolo[2,1-f][1,2,4]triazin-7-yl)-benzenesulfonamide as a lyophilized powder. (M+H)=564.2. $^1$H NMR (400 MHz, DMSO, $d_6$) δ 9.38 (s, 1H), 9.01 (s, 1H), 8.56 (s, 1H), 8.35 (d, 1H, J=7.92 Hz), 7.85 (d, 1H, J=8.12 Hz), 7.73 (m, 1H), 7.66 (d, 2H, J=9.00 Hz), 7.60 (s, 1H), 7.18 (d, 1H, J=4.76 Hz), 7.02 (d, 2H, J=9.01 Hz), 6.97 (d, 1H, J=4.76 Hz), 4.13 (m, 1H), 3.61 (m, 5H), 3.18 (m, 3H), 3.04 (m, 3H), 1.14 (d, 3H, J=6.16 Hz), 1.12 (s, 9H).

Example 427

N-tert-Butyl-3-(2-{4-[4-((S)-2-hydroxy-propyl)-piperazin-1-yl]-phenylamino}-pyrrolo[2,1-f][1,2,4]triazin-7-yl)-benzenesulfonamide The compound was made in an analogous fashion as Example 425 replacing (R)-1-[4-(4-Amino-phenyl)-piperazin-1-yl]-propan-2-ol with (S)-1-[4-(4-Amino-phenyl)-piperazin-1-yl]-propan-2-ol to afford 153.93 mg of N-tert-Butyl-3-(2-{4-[4-((S)-2-hydroxy-propyl)-piperazin-1-yl]-phenylamino}-pyrrolo[2,1-f][1,2,4]triazin-7-yl)-benzenesulfonamide as a lyophilized powder. (M+H)=564.2. $^1$H NMR (400 MHz, DMSO, $d_6$) δ 9.38 (s, 1H), 9.00 (s, 1H), 8.56 (s, 1H), 8.35 (d, 1H, J=7.92 Hz), 7.85 (d, 1H, J=7.96 Hz), 7.73 (t, 1H, J=7.85 Hz), 7.67 (d, 2H, J=8.96 Hz), 7.61 (s, 1H), 7.17 (d, 1H, J=4.76 Hz), 7.03 (d, 2H, J=9.05 Hz), 6.97 (d, 1H, J=4.75 Hz), 4.13 (m, 1H), 3.64 (m, 5H), 3.13 (m, 3H), 3.05 (m, 3H), 1.14 (d, 3H, J=6.17 Hz), 1.07 (s, 9H).

Example 428

N-{2-[2-(4-Morpholin-4-yl-phenylamino)-pyrrolo[2,1-f][1,2,4]triazin-7-yl]-phenyl}-methanesulfonamide N-[2-(2-Methanesulfinyl-pyrrolo[2,1-f][1,2,4]triazin-7-yl)-phenyl]-methanesulfonamide (100.0 mg, 0.2854 mmol), 4-(4-morpholino)aniline (102 mg, 0.571 mmol) and N,N-Diisopropylethylamine (0.149 mL, 0.856 mmol) were dissolved in 1-Methoxy-2-propanol (1.08 mL, 11.1 mmol). The reaction was irradiated at 300 watts, 200° C. for 20 minutes. The reaction was then reduced en vacuo and the resulting residue was isolated and purified by Gilson prep HPLC to afford 102.60 mg of N-{2-[2-(4-Morpholin-4-yl-phenylamino)-pyrrolo[2,1-f][1,2,4]triazin-7-yl]-phenyl}-methanesulfonamide as a lyophilized powder. (M+H)=465.1. $^1$H NMR (400 MHz, DMSO, $d_6$) δ 9.43 (s, 1H), 8.98 (s, 1H), 8.83 (s, 1H), 7.72 (d, 1H, J=7.80 Hz), 7.55 (m, 4H), 7.45 (m, 1H), 7.00 (m, 4H), 3.78 (m, 4H), 3.14 (m, 4H), 2.68 (s, 3H).

Example 429

N-(2-{2-[4-(4-Methyl-piperazin-1-yl)-phenylamino]-pyrrolo[2,1-f][1,2,4]triazin-7-yl}-phenyl)-methanesulfonamide The compound was made in an analogous fashion to Example 428 replacing 4-(4-morpholino)aniline with 4-(4-Methyl-piperazin-1-yl)-phenylamine to afford 36.23 mg of N-(2-{2-[4-(4-Methyl-piperazin-1-yl)-phenylamino]-pyrrolo[2,1-f][1,2,4]triazin-7-yl}-phenyl)-methanesulfonamide as a lyophilized powder. (M+H)=478.1. $^1$H NMR (400 MHz, DMSO, $d_6$) δ 9.37 (s, 1H), 8.98 (s, 1H), 8.82 (s, 1H), 7.72 (d, 1H, J=6.81 Hz), 7.53 (m, 4H), 7.43 (m, 1H), 6.97 (d, 1H, J=4.64 Hz), 6.93 (d, 1H, J=4.60 Hz), 6.87 (d, 2H, J=9.08 Hz), 3.70 (m, 2H), 3.51 (m, 2H), 3.15 (m, 2H), 2.86 (m, 5H), 2.67 (s, 3H).

Example 430

N-[2-(2-{4-[4-((S)-2-Hydroxy-propyl)-piperazin-1-yl]-phenylamino}-pyrrolo[2,1-f][1,2,4]triazin-7-yl)-phenyl]-methanesulfonamide The compound was made in an analogous fashion to Example 428 replacing 4-(4-morpholino)aniline with (S)-1-[4-(4-Amino-phenyl)-piperazin-1-yl]-propan-2-ol to afford 105.85 mg of -[2-(2-{4-[4-((S)-2-Hydroxy-propyl)-piperazin-1-yl]-phenylamino}-pyrrolo[2,1-f][1,2,4]triazin-7-yl)-phenyl]-methanesulfonamide as a lyophilized powder. (M+H)=522.2. $^1$H NMR (400 MHz, DMSO, $d_6$) δ 9.37 (s, 1H), 8.97 (s, 1H), 8.82 (s, 1H), 7.71 (d, 1H, J=7.77 Hz), 7.51 (m, 4H), 7.45 (m, 1H), 7.01 (d, 1H, J=4.68 Hz), 6.99 (d, 1H, J=4.64 Hz), 6.87 (d, 2H, J=9.04 Hz), 4.10 (m, 1H), 3.70 (m, 5H), 3.18 (m, 3H), 3.03 (m, 3H), 2.65 (s, 3H), 1.14 (d, 3H, J=6.12 Hz).

Example 431

N-{2-[2-(3-Morpholin-4-yl-phenylamino)-pyrrolo[2,1-f][1,2,4]triazin-7-yl]-phenyl}-methanesulfonamide The compound was made in an analogous fashion to Example 428 replacing 4-(4-morpholino)aniline with 3-Morpholin-4-yl-phenylamine to afford 51.74 mg of N-{2-[2-(3-Morpholin-4-yl-phenylamino)-pyrrolo[2,1-f][1,2,4]triazin-7-yl]-phenyl}-methanesulfonamide as a lyophilized powder. (M+H)=465.1. $^1$H NMR (400 MHz, DMSO, $d_6$) δ 9.42 (s, 1H), 9.00 (s, 1H), 8.79 (s, 1H), 7.63 (d, 1H, J=7.68 Hz), 7.52 (d, 1H, J=3.76 Hz), 7.38 (m, 2H), 7.06 (m, 1H), 7.00 (m, 1H), 6.94 (m, 2H), 6.50 (dd, 1H, J=1.80, 6.36 Hz), 3.60 (m, 4H), 2.77 (m, 4H), 2.63 (s, 3H).

Example 432

5-[7-(2-Methoxy-phenyl)-pyrrolo[2,1-f][1,2,4]triazin-2-ylamino]-1,3-dihydro-indol-2-one 2-Methanesulfinyl-7-(2-methoxy-phenyl)-pyrrolo[2,1-f][1,2,4]triazine (75.0 mg, 0.000261 mol), Methanesulfonic acid (0.03388 mL, 0.0005220 mol) and [B] 5-Amino-1,3-dihydro-indol-2-one (77.3 mg, 0.000522 mol) were dissolved in 1-Methoxy-2-propanol (0.74 mL, 0.0076 mol) and the reaction was irradiated at 300 watts, 200° C. for 40 minutes or until HPLC showed consumption of starting material. The reaction mixture was then reduced en vacuo and the product was isolated and purified by Gilson prep HPLC to afford 5.40 mg of 5-[7-(2-Methoxy-phenyl)-pyrrolo[2,1-f][1,2,4]triazin-2-ylamino]-1,3-dihydro-indol-2-one as a lyophilized powder. (M+H)=371.9. $^1$H NMR (400 MHz, DMSO, $d_6$) δ 10.19 (s, 1H), 9.25 (s, 1H), 8.91 (s, 1H), 7.78 (d, 1H, J=7.53 Hz), 7.74 (s, 1H), 7.47 (t, 1H, J=7.53 Hz), 7.39 (d, 1H, J=7.88 Hz), 7.23 (d, 1H, J=8.09 Hz), 7.13 (t, 1H, J=7.28 Hz), 6.90 (dd, 2H, J=4.61, 6.41 Hz), 6.64 (d, 1H, J=8.37 Hz), 3.78 (s, 3H), 3.38 (s, 2H).

Example 442

(3,4-Dimethoxy-benzyl)-[7-(2-methoxy-phenyl)-pyrrolo[2,1-f][1,2,4]triazin-2-yl]-amine; compound with trifluoro-acetic acid The titled compound was prepared in an analogous fashion to Example 12 replacing 3-(Aminomethyl)pyridine with Veratrylamine to give after purification via reverse phase HPLC (3,4-Dimethoxy-benzyl)-[7-(2-methoxy-phenyl)-pyrrolo[2,1-f][1,2,4]triazin-2-yl]-amine; compound with trifluoro-acetic acid as a yellow lyophylate (21 mg, 16%). LC/MS (E/I+) 391.10 (M+H). NMR $^1$H (DMSO-$d_6$)-8.80 (s, 1H), 7.82-7.80 (m, 2H), 7.39-7.36 (m, 2H), 7.15-7.13 (d, 1H, J=7.63 Hz), 7.01-6.98 (m, 1H), 6.91-6.89 (m, 2H), 6.83-6.79 (m, 3H), 4.25 (s, 2H), 3.78 (s, 3H), 3.69 (s, 3H), 3.58 (s, 3H).

Example 443

(1-{4-[7-(2-Methoxy-phenyl)-pyrrolo[2,1-f][1,2,4]triazin-2-ylamino]-phenyl}-piperidin-3-yl)-(4-methyl-piperazin-1-yl)-methanone; compound with trifluoro-acetic acid a) (4-Methyl-piperazin-1-yl)-[1-(4-nitro-phenyl)-piperidin-3-yl]-methanone was prepared in a similar manner as N-(2-Dimethylamino-ethyl)-4-[2-(4-morpholin-4-yl-phenylamino)-pyrrolo[2,1-f][1,2,4]triazin-7-yl]-benzamide of Example 52 after: substituting N-Me-piperazine for N,N-dimethyl-1,2-Ethanediamine, substituting 1-(4-Nitro-phenyl)-piperidine-3-carboxylic acid for 4-[2-(4-Morpholin-4-yl-phenylamino)-pyrrolo[2,1-f][1,2,4]triazin-7-yl]-benzoic acid, and substituting chloroform as the solvent in place of DMF. (4-Methyl-piperazin-1-yl)-[1-(4-nitro-phenyl)-piperidin-3-yl]-methanone from this procedure was also purified differently; after workup the crude oil was triturated in water to yield a solid, which was filtered, rinsed with water, and air dried to give (4-Methyl-piperazin-1-yl)-[1-(4-nitro-phenyl)-piperidin-3-yl]-methanone as a yellow solid (267 mg, 80%). LC: 100%; LC/MS (E/I+) 333.13 (M+H).

b) [1-(4-Amino-phenyl)-piperidin-3-yl]-(4-methyl-piperazin-1-yl)-methanone was prepared in a similar manner as 2-Methoxy-4-(4-methyl-piperazin-1-yl)-phenylamine of Example 33 after substituting (4-Methyl-piperazin-1-yl)-[1-(4-nitro-phenyl)-piperidin-3-yl]-methanone for 1-(3-Methoxy-4-nitro-phenyl)-4-methyl-piperazine, and using EtOH as the solvent rather than MeOH (75 mg, 99%). LC/MS (E/I+) 303.19 (M+H).

c) The titled compound (1-{4-[7-(2-Methoxy-phenyl)-pyrrolo[2,1-f][1,2,4]triazin-2-ylamino]-phenyl}-piperidin-3-yl)-(4-methyl-piperazin-1-yl)-methanone; compound with trifluoro-acetic acid was prepared in an analogous fashion to [7-(4-Methanesulfonyl-phenyl)-5-methyl-pyrrolo[2,1-f][1,2,4]triazin-2-yl]-(4-morpholin-4-yl-phenyl)-amine of Example 107 after: replacing 4-(4-morpholino)aniline with [1-(4-Amino-phenyl)-piperidin-3-yl]-(4-methyl-piperazin-1-yl)-methanone, replacing 2-Methanesulfinyl-7-(4-methanesulfonyl-phenyl)-5-methyl-pyrrolo[2,1-f][1,2,4]triazine with 2-Methanesulfinyl-7-(2-methoxy-phenyl)-5-methyl-pyrrolo[2,1-f][1,2,4]triazine (of Example 47), and replacing the solvent N-Methylpyrrolidinone with 1-Methoxy-2-propanol, to give after purification via reverse phase HPLC (1-{4-[7-(2-Methoxy-phenyl)-pyrrolo[2,1-f][1,2,4]triazin-2-ylamino]-phenyl}-piperidin-3-yl)-(4-methyl-piperazin-1-yl)-methanone; compound with trifluoro-acetic acid as a brown lyophylate (29 mg, 22%). LC/MS (E/I+) 526.22 (M+H). NMR $^1$H (DMSO-$d_6$)-10.01 (bs, 1H), 9.45 (bs, 1H), 8.96 (s, 1H), 7.81-7.79 (m, 1H), 7.72-7.69 (d, 2H, J=8.58 Hz), 7.50-7.46 (m, 1H), 7.23-7.11 (m, 4H), 6.96-6.93 (m, 2H), 4.46-4.19 (bm, TFA salt and water provided poor resolution), 3.81 (s, 3H), 3.58-2.93 (bm; smeared as TFA salt), 2.83 (s, 3H), 1.86 (bs, 3H), 1.75 (bs, 1H).

Example 444

(1-{4-[7-(2-Methoxy-phenyl)-pyrrolo[2,1-f][1,2,4]triazin-2-ylamino]-phenyl}-piperidin-4-yl)-(4-methyl-piperazin-1-yl)-methanone; compound with trifluoro-acetic acid a) (4-Methyl-piperazin-1-yl)-[1-(4-nitro-phenyl)-piperidin-4-yl]-methanone was prepared in a similar manner as (4-Methyl-piperazin-1-yl)-[1-(4-nitro-phenyl)-piperidin-3-yl]-methanone of Example 443a after substituting 1-(4-Nitro-phenyl)-piperidine-4-carboxylic acid for 1-(4-Nitro-phenyl)-piperidine-3-carboxylic acid. (4-Methyl-piperazin-1-yl)-[1-(4-nitro-phenyl)-piperidin-3-yl]-methanone was isolated as a yellow solid from water (570 mg, 86%). LC: 100%; LC/MS (E/I+) 333.13 (M+H).

b) [1-(4-Amino-phenyl)-piperidin-4-yl]-(4-methyl-piperazin-1-yl)-methanone was prepared in a similar manner as [1-(4-Amino-phenyl)-piperidin-3-yl]-(4-methyl-piperazin-1-yl)-methanone of Example 443b after substituting (4-Methyl-piperazin-1-yl)-[1-(4-nitro-phenyl)-piperidin-4-yl]- methanone for (4-Methyl-piperazin-1-yl)-[1-(4-nitro-phenyl)-piperidin-3-yl]-methanone (250 mg, 98%). LC/MS (E/I+) 303.19 (M+H).

c) The titled compound (1-{4-[7-(2-Methoxy-phenyl)-pyrrolo[2,1-f][1,2,4]triazin-2-ylamino]-phenyl}-piperidin-4-yl)-(4-methyl-piperazin-1-yl)-methanone; compound with trifluoro-acetic acid was prepared in an analogous fashion to (1-{4-[7-(2-Methoxy-phenyl)-pyrrolo[2,1-f][1,2,4]triazin-2-ylamino]-phenyl}-piperidin-3-yl)-(4-methyl-piperazin-1-yl)-methanone; compound with trifluoro-acetic acid of Example 443c after replacing [1-(4-Amino-phenyl)-piperidin-3-yl]-(4-methyl-piperazin-1-yl)-methanone with [1-(4-Amino-phenyl)-piperidin-4-yl]-(4-methyl-piperazin-1-yl)-methanone, to give after purification via reverse phase HPLC (1-{4-[7-(2-Methoxy-phenyl)-pyrrolo[2,1-f][1,2,4]triazin-2-ylamino]-phenyl}-piperidin-4-yl)-(4-methyl-piperazin-1-yl)-methanone; compound with trifluoro-acetic acid as a brown lyophylate (38 mg, 42%). LC/MS (E/I+) 526.21 (M+H). NMR $^1$H (DMSO-d$_6$)-10.0 (bs, 1H), 9.5 (bs, 1H), 8.97 (s, 1H), 7.81-7.74 (m, 3H), 7.50-7.11 (m, 5H), 6.97-6.93 (m, 2H), 4.2-3.85 (bm, TFA salt and water provided poor resolution), 3.81 (s, 3H), 3.62-2.85 (bm; smeared as TFA salt), 2.83 (s, 3H), 1.88 (bs, 4H).

Example 445

(1-{4-[7-(4-Methanesulfonyl-phenyl)-pyrrolo[2,1-f][1,2,4]triazin-2-ylamino]-phenyl}-piperidin-4-yl)-(4-methyl-piperazin-1-yl)-methanone; compound with trifluoro-acetic acid The titled compound was prepared in an analogous fashion to Example 444 replacing 2-Methanesulfinyl-7-(2-methoxy-phenyl)-5-methyl-pyrrolo[2,1-f][1,2,4]triazine with 2-Methanesulfinyl-7-(4-methanesulfonyl-phenyl)-5-methyl-pyrrolo[2,1-f][1,2,4]triazine (Example 107) to give after purification via reverse phase HPLC (1-{4-[7-(4-Methanesulfonyl-phenyl)-pyrrolo[2,1-f][1,2,4]triazin-2-ylamino]-phenyl}-piperidin-4-yl)-(4-methyl-piperazin-1-yl)-methanone; compound with trifluoro-acetic acid as a brown lyophylate (13 mg, 26%). LC/MS (E/I+) 574.23 (M+H). NMR $^1$H (DMSO-d$_6$)-10.0 (bs, 1H), 9.5 (bs, 1H), 9.07 (s, 1H), 8.50-8.48 (d, 2H, J=8.05 Hz), 8.06-8.04 (d, 2H, J=8.10 Hz), 7.73 (bs, 2H), 7.37-7.01 (m, 4H), 4.48-3.47 (bm, TFA salt and water provided poor resolution), 3.30 (s, 3H), 3.17-2.94 (bm; smeared as TFA salt), 2.84 (s, 3H), 1.86 (bs, 4H).

Example 446

(1-{4-[7-(4-Methanesulfonyl-phenyl)-pyrrolo[2,1-f][1,2,4]triazin-2-ylamino]-phenyl}-piperidin-3-yl)-(4-methyl-piperazin-1-yl)-methanone; compound with trifluoro-acetic acid The titled compound was prepared in an analogous fashion to Example 445 replacing [1-(4-Amino-phenyl)-piperidin-4-yl]-(4-methyl-piperazin-1-yl)-methanone with [1-(4-Amino-phenyl)-piperidin-3-yl]-(4-methyl-piperazin-1-yl)-methanone to give after purification via reverse phase HPLC (1-{4-[7-(4-Methanesulfonyl-phenyl)-pyrrolo[2,1-f][1,2,4]triazin-2-ylamino]-phenyl}-piperidin-3-yl)-(4-methyl-piperazin-1-yl)-methanone; compound with trifluoro-acetic acid as a brown lyophylate (9 mg, 20%). LC/MS (E/I+) 574.23 (M+H). NMR $^1$H (DMSO-d$_6$)-9.86 (bs, 1H), 9.45 (bs, 1H), 9.04 (s, 1H), 8.50-8.48 (d, 2H, J=7.72 Hz), 8.04-8.02 (d, 2H, J=7.62 Hz), 7.66-7.64 (d, 2H, J=7.86 Hz), 7.36-7.35 (d, 2H, J=4.22 Hz), 7.13 (bs, 2H), 7.00-6.99 (d, 2H, J=4.43 Hz), 4.48-3.47 (bm, TFA salt and water provided poor resolution), 3.29 (s, 3H), 3.17-2.94 (bm; smeared as TFA salt), 2.83 (s, 3H), 1.88-1.80 (m, 3H), 1.51 (bs, 1H).

Example 447

N-Methyl-N-[2-(2-{4-[3-(4-methyl-piperazine-1-carbonyl)-piperidin-1-yl]-phenylamino}-pyrrolo[2,1-f][1,2,4]triazin-7-yl)-phenyl]-methanesulfonamide; compound with trifluoro-acetic acid The titled compound was prepared in an analogous fashion to Example 446 replacing 2-Methanesulfinyl-7-(4-methanesulfonyl-phenyl)-5-methyl-pyrrolo[2,1-f][1,2,4]triazine with N-[2-(2-Methanesulfinyl-pyrrolo[2,1-f][1,2,4]triazin-7-yl)-phenyl]-N-methyl-methanesulfonamide to give after purification via reverse phase HPLC N-Methyl-N-[2-(2-{4-[3-(4-methyl-piperazine-1-carbonyl)-piperidin-1-yl]-phenylamino}-pyrrolo[2,1-f][1,2,4]triazin-7-yl)-phenyl]-methanesulfonamide; compound with trifluoro-acetic acid as a brown lyophylate (17 mg, 28%). LC/MS (E/I+) 603.25 (M+H). NMR $^1$H (DMSO-d$_6$)-9.91 (bs, 1H), 9.39 (bs, 1H), 8.97 (s, 1H), 8.01-8.00 (d, 2H, J=7.30 Hz), 7.67-7.55 (m, 5H), 7.07 (bs, 2H), 6.99-6.96 (d, 2H, J=12.84 Hz), 4.47-3.44 (bm, TFA salt and water provided poor resolution), 3.08 (s, 3H), 3.07-2.91 (bm, smeared as TFA salt), 2.89 (s, 3H), 2.83 (s, 3H), 1.85-1.80 (m, 3H), 1.51 (bs, 1H).

Example 448

N-Methyl-N-[2-(2-{4-[4-(4-methyl-piperazine-1-carbonyl)-piperidin-1-yl]-phenylamino}-pyrrolo[2,1-f][1,2,4]triazin-7-yl)-phenyl]-methanesulfonamide; compound with trifluoro-acetic acid The titled compound was prepared in an analogous fashion to Example 447 replacing [1-(4-Amino-phenyl)-piperidin-3-yl]-(4-methyl-piperazin-1-yl)-methanone with [1-(4-Amino-phenyl)-piperidin-4-yl]-(4-methyl-piperazin-1-yl)-methanone to give after purification via reverse phase HPLC N-Methyl-N-[2-(2-{4-[4-(4-methyl-piperazine-1-carbonyl)-piperidin-1-yl]-phenylamino}-pyrrolo[2,1-f][1,2,4]triazin-7-yl)-phenyl]-methanesulfonamide; compound with trifluoro-acetic acid as a brown lyophylate (23 mg, 31%). LC/MS (E/I+) 603.25 (M+H). NMR $^1$H (DMSO-d$_6$)-10.0 (bs, 1H), 9.50 (bs, 1H), 8.99 (s, 1H), 8.01-7.99 (d, 1H, J=7.17 Hz), 7.68-7.55 (m, 5H), 7.19 (bs, 2H), 7.00-6.98 (d, 2H, J=10.71 Hz), 4.47-3.17 (bm, TFA salt and water provided poor resolution), 3.08 (s, 3H), 3.07-2.94 (bm, smeared as TFA salt), 2.89 (s, 3H), 2.83 (s, 3H), 1.86 (bs, 4H).

Example 449

1-[7-(2-Methoxy-phenyl)-pyrrolo[2,1-f][1,2,4]triazin-2-yl]-3-[4-(4-methyl-piperazin-1-yl)-phenyl]-urea The titled compound was prepared by reacting the free base of 7-(2-Methoxy-phenyl)-pyrrolo[2,1-f][1,2,4]triazin-2-ylamine of Example 41 with 1-(4-Isocyanato-phenyl)-4-methyl-piperazine (10 eqvts) in THF at room temperature. The resulting mixture was treated with CHCl$_3$ and warmed to reflux. The resulting mixture was concentrated under reduced pressure and the residue treated with DMSO. The resulting solid was filtered and rinsed with a small amount of DMSO. The remaining solid was then triturated multiple times with warmed methanol. The resulting white solid proved to be 1-[7-(2-Methoxy-phenyl)-pyrrolo[2,1-f][1,2,4]triazin-2-yl]-3-[4-(4-methyl-piperazin-1-yl)-phenyl]-urea (15 mg, 33%). MP: 229-231° C. LC/MS (E/I+) 458.17 (M+H). NMR $^1$H (DMSO-d$_6$)-10.20 (s, 1H), 9.83 (s, 1H), 9.07 (s, 1H), 7.65-7.64 (d, 1H, J=7.44 Hz), 7.60-7.56 (m, 1H), 7.28-6.80 (m, 9H), 3.71 (s, 3H), 3.07 (s, 4H), 2.45 (s, 4H), 2.22 (s, 3H).

Example 450

N-Methyl-N-[2-(2-{4-[4-(4-methyl-piperazin-1-ylmethyl)-piperidin-1-yl]-phenylamino}-pyrrolo[2,1-f][1,2,4]triazin-7-yl)-phenyl]-methanesulfonamide; compound with trifluoro-acetic acid a) 1-Methyl-4-[1-(4-nitro-phenyl)-piperidin-4-ylmethyl]-piperazine was prepared by warming (4-Methyl-piperazin-1-yl)-[1-(4-nitro-phenyl)-piperidin-4-yl]-methanone of Example 444a with borane.THF (10 equivalents) at 60° C. for 16 hours, followed by a standard aqueous HCl workup. The resulting aqueous phase was neutralized with NaHCO3 and extracted with EtOAc (2×). The organics were combined, dried over Na2SO4, filtered, and concentrated under reduced pressure to give 1-Methyl-4-[1-(4-nitro-phenyl)-piperidin-4-ylmethyl]-piperazine as an orange solid, which was used for subsequent step without further manipulation. LC/MS (E/I+) 319.15 (M+H).

b) 4-[4-(4-Methyl-piperazin-1-ylmethyl)-piperidin-1-yl]-phenylamine was prepared in an analogous fashion to Example 443b replacing [1-(4-Amino-phenyl)-piperidin-3-yl]-(4-methyl-piperazin-1-yl)-methanone with 1-Methyl-4-[1-(4-nitro-phenyl)-piperidin-4-ylmethyl]-piperazine (250 mg, 95%).

c) The titled compound was prepared in an analogous fashion to Example 448 replacing [1-(4-Amino-phenyl)-piperidin-4-yl]-(4-methyl-piperazin-1-yl)-methanone with 4-[4-(4-Methyl-piperazin-1-ylmethyl)-piperidin-1-yl]-phenylamine to give after purification via reverse phase HPLC N-Methyl-N-[2-(2-{4-[4-(4-methyl-piperazin-1-ylmethyl)-piperidin-1-yl]-phenylamino}-pyrrolo[2,1-f][1,2,4]triazin-7-yl)-phenyl]-methanesulfonamide; compound with trifluoro-acetic acid as a brown lyophylate (14 mg, 19%). LC/MS (E/I+) 589.24 (M+H). NMR $^1$H (DMSO-d$_6$)-9.5 (bs, 1H), 9.00 (s, 1H), 8.01-7.99 (d, 1H, J=7.44 Hz), 7.68-7.55 (m, 5H), 7.19 (bs, 2H), 7.02-6.98 (m, 2H), 4.25-3.10 (bm, TFA salt and water provided poor resolution), 3.09 (s, 3H), 3.07-2.94 (bm, smeared as TFA salt), 2.89 (s, 3H), 2.80 (s, 3H), 1.94-1.92 (bm, 4H), 1.48 (bm, 2H).

Example 451

[7-(2-Methoxy-phenyl)-pyrrolo[2,1-f][1,2,4]triazin-2-yl]-{4-[4-(4-methyl-piperazin-1-ylmethyl)-piperidin-1-yl]-phenyl}-amine; compound with trifluoro-acetic acid The titled compound was prepared in an analogous fashion to Example 443c replacing [1-(4-Amino-phenyl)-piperidin-3-yl]-(4-methyl-piperazin-1-yl)-methanone with 4-[4-(4-Methyl-piperazin-1-ylmethyl)-piperidin-1-yl]-phenylamine to give after purification via reverse phase HPLC [7-(2-Methoxy-phenyl)-pyrrolo[2,1-f][1,2,4]triazin-2-yl]-{4-[4-(4-methyl-piperazin-1-ylmethyl)-piperidin-1-yl]-phenyl}-amine; compound with trifluoro-acetic acid as a brown lyophylate (16 mg, 25%). LC/MS (E/I+) 512.23 (M+H). NMR $^1$H (DMSO-d$_6$)-9.55 (bs, 1H), 8.98 (s, 1H), 7.80-7.76 (m, 1H, 3H), 7.50-7.11 (m, 5H), 6.96 (s, 2H), 4.25-3.85 (bm, TFA salt and water provided poor resolution), 3.81 (s, 3H), 3.79-2.83 (bm, smeared as TFA salt), 2.81 (s, 3H), 1.97-1.94 (bm, 4H), 1.50 (bm, 2H).

Example 452

[7-(4-Methanesulfonyl-phenyl)-pyrrolo[2,1-f][1,2,4]triazin-2-yl]-{4-[4-(4-methyl-piperazin-1-ylmethyl)-piperidin-1-yl]-phenyl}-amine; compound with trifluoro-acetic acid The titled compound was prepared in an analogous fashion to Example 445 replacing [1-(4-Amino-phenyl)-piperidin-4-yl]-(4-methyl-piperazin-1-yl)-methanone with 4-[4-(4-Methyl-piperazin-1-ylmethyl)-piperidin-1-yl]-phenylamine to give after purification via reverse phase HPLC [7-(4-Methanesulfonyl-phenyl)-pyrrolo[2,1-f][1,2,4]triazin-2-yl]-{4-[4-(4-methyl-piperazin-1-ylmethyl)-piperidin-1-yl]-phenyl}-amine; compound with trifluoro-acetic acid as a brown lyophylate (13 mg, 19%). LC/MS (E/I+) 560.20 (M+H). NMR $^1$H (DMSO-d$_6$)-9.75 (bs, 1H), 9.08 (s, 1H), 8.49-8.47 (d, 2H, J=7.92 Hz), 8.06-8.04 (d, 2H, J=8.04 Hz), 7.76 (bs, 2H), 7.38-7.01 (m, 5H), 4.48-3.47 (bm, TFA salt and water provided poor resolution), 3.30 (s, 3H), 3.27-2.85 (bm; smeared as TFA salt), 2.81 (s, 3H), 1.96-1.92 (bm, 4H), 1.45 (bm, 2H).

Example 453

N-(2-{2-[2-Methoxy-4-(morpholin-4-yl-piperidin-1-yl)-phenylamino]-pyrrolo[2,1-f][1,2,4]triazin-7-yl}-phenyl)-acetamide; compound with trifluoro-acetic acid a) N-[2-(2-Methylsulfanyl-pyrrolo[2,1-f][1,2,4]triazin-7-yl)-phenyl]-acetamide was prepared in an analogous fashion to Example 47a replacing 2-methoxybenzeneboronic acid with 2-Acetylaminophenylboronic acid to give after purification via normal phase chromatography (EtOAc/hexane as eluant) N-[2-(2-Methylsulfanyl-pyrrolo[2,1-f][1,2,4]triazin-7-yl)-phenyl]-acetamide as a yellow oil (400 mg, 54%). LC/MS (E/I+) 299.07 (M+H).

b) N-[2-(2-Methanesulfinyl-pyrrolo[2,1-f][1,2,4]triazin-7-yl)-phenyl]-acetamide was prepared in an analogous fashion to Example 47b replacing 7-(2-Methoxy-phenyl)-2-methylsulfanyl-pyrrolo[2,1-f][1,2,4]triazine with N-[2-(2-Methylsulfanyl-pyrrolo[2,1-f][1,2,4]triazin-7-yl)-phenyl]-acetamide to give N-[2-(2-Methanesulfinyl-pyrrolo[2,1-f][1,2,4]triazin-7-yl)-phenyl]-acetamide as a foamy material, which was used without further manipulation (390 mg, 92%). LC/MS (E/I+) 337.01 (M+Na).

c) The title compound N-(2-{2-[2-Methoxy-4-(morpholin-4-yl-piperidin-1-yl)-phenylamino]-pyrrolo[2,1-f][1,2,4]triazin-7-yl}-phenyl)-acetamide; compound with trifluoro-acetic acid was prepared in an analogous fashion to Example 443c after: replacing 2-Methanesulfinyl-7-(2-methoxy-phenyl)-5-methyl-pyrrolo[2,1-f][1,2,4]triazine with N-[2-(2-Methanesulfinyl-pyrrolo[2,1-f][1,2,4]triazin-7-yl)-phenyl]-acetamide , and replacing [1-(4-Amino-phenyl)-piperidin-4-yl]-(4-methyl-piperazin-1-yl)-methanone with 2-Methoxy-4-(morpholin-4-yl-piperidin-1-yl)-phenylamine to give after purification via reverse phase HPLC N-(2-{2-[2-Methoxy-4-(morpholin-4-yl-piperidin-1-yl)-phenylamino]-pyrrolo[2,1-f][1,2,4]triazin-7-yl}-phenyl)-acetamide; compound with trifluoro-acetic acid as a brown lyophylate (29 mg, 44%). LC/MS (E/I+) 542.24 (M+H). NMR $^1$H (DMSO-d$_6$)-9.76 (bs, 1H), 9.28 (s, 1H), 8.94 (s, 1H), 7.82-7.71 (m, 4H), 7.45-7.41 (m, 1H), 7.32-7.28 (m, 1H), 6.98-6.97 (d, 1H, J=4.18 Hz), 6.88-6.87 (d, 1H, J=4.16 Hz), 6.70 (s, 1H), 6.43-6.41 (d, 1H, 8.55 Hz), 5.2-4.0 (bm, TFA salt and water provided poor resolution), 3.81 (s, 3H), 3.67-3.65 (m, 2H), 3.51-3.48 (m, 2H), 3.37 (m, 1H), 3.14 (bm, 2H), 2.73-2.67 (m, 2H), 2.16-2.13 (m, 2H), 1.81 (s, 3H), 1.76-1.71 (m, 2H).

Example 454

N-(2-{2-[4-(4-Morpholin-4-yl-piperidin-1-yl)-phenylamino]-pyrrolo[2,1-f][1,2,4]triazin-7-yl}-phenyl)-acetamide; compound with trifluoro-acetic acid The titled compound was prepared in an analogous fashion to Example 453c replacing 2-Methoxy-4-(4-morpholin-4-yl-piperidin-1-yl)-phenylamine with 4-(4-morpholin-4-yl-piperidin-1-yl)-phenylamine to give after purification via reverse phase HPLC N-(2-{2-[4-(4-Morpholin-4-yl-piperidin-1-yl)-phenylamino]-pyrrolo[2,1-f][1,2,4]triazin-7-yl}-phenyl)-acetamide; compound with trifluoro-acetic acid as a brown lyophylate (26 mg, 41%). LC/MS (E/I+) 512.22 (M+H). NMR $^1$H (DMSO-d$_6$)-9.67 (bs, 1H), 9.30 (s, 1H), 9.27 (s, 1H), 8.96 (s, 1H), 7.88-7.86 (d, 1H, J=7.69 Hz), 7.75-7.74 (d, 1H, J=7.36 Hz), 7.57-7.55 (d, 2H, J=8.16 Hz), 7.46-7.7.43 (m, 1H), 7.35-7.33 (m, 1H), 6.97-6.96 (d, 1H, J=4.17 Hz), 6.89-6.87 (m, 2H), 4.01 (bm, 2H), 3.75-3.67 (bm, 4H), 3.47 (bm, 2H), 3.35 (bm, 1H), 3.12 (bm, 2H), 2.67 (bm, 2H), 2.15-2.13 (d, 2H, J=10.38 Hz), 1.80 (s, 3H), 1.73-1.70 (bm, 2H).

Example 455

N-Methyl-N-[2-(2-{4-[3-(4-methyl-piperazin-1-ylmethyl)-piperidin-1-yl]-phenylamino}-pyrrolo[2,1-f][1,2,4]triazin-7-yl)-phenyl]-methanesulfonamide; compound with trifluoro-acetic acid a) 1-Methyl-4-[1-(4-nitro-phenyl)-piperidin-3-ylmethyl]-piperazine was prepared by warming (4-Methyl-piperazin-1-yl)-[1-(4-nitro-phenyl)-piperidin-3-yl]-methanone of Example 443a with borane.THF (10 equivalents) at 60° C. for 16 hours, followed by a standard aqueous HCl workup. The resulting aqueous phase was neutralized with NaHCO3 and extracted with EtOAc (2x). The organics were combined, dried over Na2SO4, filtered, and concentrated under reduced pressure to give 1-Methyl-4-[1-(4-nitro-phenyl)-piperidin-4-ylmethyl]-piperazine as an orange oil, which was used for subsequent step without further manipulation. LC/MS (E/I+) 319.18 (M+H).

b) 4-[3-(4-Methyl-piperazin-1-ylmethyl)-piperidin-1-yl]-phenylamine was prepared in an analogous fashion to Example 443b replacing (4-Methyl-piperazin-1-yl)-[1-(4-nitro-phenyl)-piperidin-3-yl]-methanone with 1-Methyl-4-[1-(4-nitro-phenyl)-piperidin-3-ylmethyl]-piperazine (180 mg, 99%).

c) The titled compound was prepared in an analogous fashion to Example 450 replacing 4-[4-(4-Methyl-piperazin-1-ylmethyl)-piperidin-1-yl]-phenylamine with 4-[3-(4-Methyl-piperazin-1-ylmethyl)-piperidin-1-yl]-phenylamine to give after purification via reverse phase HPLC N-Methyl-N-[2-(2-{4-[3-(4-methyl-piperazin-1-ylmethyl)-piperidin-1-yl]-phenylamino}-pyrrolo[2,1-f][1,2,4]triazin-7-yl)-phenyl]-methanesulfonamide; compound with trifluoro-acetic acid as a brown lyophylate (17 mg, 23%). LC/MS (E/I+) 589.24 (M+H). NMR $^1$H (DMSO-d$_6$)-9.5 (bs, 2H), 8.98 (s, 1H), 8.01-7.99 (d, 1H, J=7.19 Hz), 7.68-7.55 (m, 6H), 6.99-6.97 (m, 3H), 3.47-3.10 (bm, TFA salt and water provided poor resolution), 3.09 (s, 3H), 3.07-2.94 (bm, smeared as TFA salt), 2.89 (s, 3H), 2.77 (s, 3H), 1.94-1.92 (bm, 4H), 1.48 (bm, 2H).

Example 456

[7-(2-Methoxy-phenyl)-pyrrolo[2,1-f][1,2,4]triazin-2-yl]-{4-[3-(4-methyl-piperazin-1-ylmethyl)-piperidin-1-yl]-phenyl}-amine; compound with trifluoro-acetic acid The titled compound was prepared in an analogous fashion to Example 455c replacing N-[2-(2-Methanesulfinyl-pyrrolo[2,1-f][1,2,4]triazin-7-yl)-phenyl]-N-methyl-methanesulfonamide with 2-Methanesulfinyl-7-(2-methoxy-phenyl)-5-methyl-pyrrolo[2,1-f][1,2,4]triazine to give after purification via reverse phase HPLC [7-(2-Methoxy-phenyl)-pyrrolo[2,1-f][1,2,4]triazin-2-yl]-{4-[3-(4-methyl-piperazin-1-ylmethyl)-piperidin-1-yl]-phenyl}-amine; compound with trifluoro-acetic acid as a brown lyophylate (30 mg, 47%). LC/MS (E/I+) 512.24 (M+H). NMR $^1$H (DMSO-d$_6$)-9.5 (bs, 2H), 8.98 (s, 1H), 7.81-7.76 (m, 3H), 7.50-7.12 (m, 5H), 6.96 (s, 2H), 3.81 (s, 3H), 3.52-3.05 (bm, TFA salt and water provided poor resolution), 2.20 (bs, 2H), 1.89-1.79 (m, 3H), 1.23 (m, 1H).

Example 457

[7-(4-Methanesulfonyl-phenyl)-pyrrolo[2,1-f][1,2,4]triazin-2-yl]-{4-[3-(4-methyl-piperazin-1-ylmethyl)-piperidin-1-yl]-phenyl}-amine; compound with trifluoro-acetic acid The titled compound was prepared in an analogous fashion to Example 455c replacing N-[2-(2-Methanesulfinyl-pyrrolo[2,1-f][1,2,4]triazin-7-yl)-phenyl]-N-methyl-methanesulfonamide with 2-Methanesulfinyl-7-(4-methanesulfonyl-phenyl)-5-methyl-pyrrolo[2,1-f][1,2,4]triazine to give after purification via reverse phase HPLC [7-(4-Methanesulfonyl-phenyl)-pyrrolo[2,1-f][1,2,4]triazin-2-yl]-{4-[3-(4-methyl-piperazin-1-ylmethyl)-piperidin-1-yl]-phenyl}-amine; compound with trifluoro-acetic acid as a brown lyophylate (15 mg, 22%). LC/MS (E/I+) 560.23 (M+H). NMR $^1$H (DMSO-d$_6$)-9.5 (bs, 2H), 9.07 (s, 1H), 8.50-8.48 (d, 2H, J=7.58 Hz), 8.06-8.04 (d, 2H, J=7.54 Hz), 7.74 (bm, 2H), 7.37-7.25 (m, 3H), 7.03 (s, 1H), 3.61-3.35 (bm, TFA salt and water provided poor resolution), 3.31 (s, 3H), 3.27-3.00 (bm, TFA salt provided poor resolution), 2.79 (s, 3H), 2.17 (bm, 1H), 1.89-1.79 (m, 3H), 1.23-1.19 (m, 1H).

Example 458

(1-{3-Methoxy-4-[7-(2-methoxy-phenyl)-pyrrolo[2,1-f][1,2,4]triazin-2-ylamino]-phenyl}-piperidin-4-yl)-(4-methyl-piperazin-1-yl)-methanone; compound with trifluoro-acetic acid a) [1-(3-Methoxy-4-nitro-phenyl)-piperidin-4-yl]-(4-methyl-piperazin-1-yl)-methanone was prepared in an analogous fashion to Example 443a replacing 1-(4-Nitro-phenyl)-piperidine-3-carboxylic acid with 1-(3-Methoxy-4-nitro-phenyl)-piperidine-4-carboxylic acid. Crystallization was accomplished with Et$_2$O rather than water to give a solid, which was further triturated with EtOH to give desired [1-(3-Methoxy-4-nitro-phenyl)-piperidin-4-yl]-(4-methyl-piperazin-1-yl)-methanone as a yellow solid, mp 133-135° C. LC/MS (E/I+) 363.17 (M+H).

b) [1-(4-Amino-3-methoxy-phenyl)-piperidin-4-yl]-(4-methyl-piperazin-1-yl)-methanone was prepared in an analogous fashion to Example 443b replacing (4-Methyl-piperazin-1-yl)-[1-(4-nitro-phenyl)-piperidin-3-yl]-methanone with [1-(3-Methoxy-4-nitro-phenyl)-piperidin-4-yl]-(4-methyl-piperazin-1-yl)-methanone. (290 mg, 93%). LC/MS (E/I+) 333.24 (M+H).

c) The titled compound was prepared in an analogous fashion to Example 444 replacing [1-(4-Amino-phenyl)-piperidin-4-yl]-(4-methyl-piperazin-1-yl)-methanone with [1-(4-Amino-3-methoxy-phenyl)-piperidin-4-yl]-(4-methyl-piperazin-1-yl)-methanone to give after purification via reverse phase HPLC (1-{3-Methoxy-4-[7-(2-methoxy-phenyl)-pyrrolo[2,1-f][1,2,4]triazin-2-ylamino]-phenyl}-piperidin-4-yl)-(4-methyl-piperazin-1-yl)-methanone; compound with trifluoro-acetic acid as a brown lyophylate (66 mg, 43%). LC/MS (E/I+) 556.23 (M+H). NMR $^1$H (DMSO-$d_6$)-9.8 (bs, 1H), 8.94 (s, 1H), 8.01 (bs, 1H), 7.83-7.81 (d, 1H, J=7.55 Hz), 7.66 (bs, 1H), 7.47-7.44 (m, 1H), 7.22-7.20 (d, 1H, J=8.33 Hz), 7.12-7.08 (m, 1H), 6.97-6.75 (m, 4H), 4.50 (bm, 1H), 4.25 (bm, 1H), 3.89 (s, 3H), 3.79 (s, 3H), 3.68-2.85 (bm, TFA salt and water provided poor resolution), 2.84 (s, 3H), 1.84 (bs, 4H).

Example 459

N-[2-(2-{2-Methoxy-4-[4-(4-methyl-piperazine-1-carbonyl)-piperidin1-yl]-phenylamino}-pyrrolo[2,1-f][1,2,4]triazin-7-yl)-phenyl]-N-methyl-methanesulfonamide; compound with trifluoro-acetic acid The titled compound was prepared in an analogous fashion to Example 458c replacing 7-(2-Methoxy-phenyl)-2-methylsulfanyl-pyrrolo[2,1-f][1,2,4]triazine with N-[2-(2-Methanesulfinyl-pyrrolo[2,1-f][1,2,4]triazin-7-yl)-phenyl]-N-methyl-methanesulfonamide to give after purification via reverse phase HPLC N-[2-(2-{2-Methoxy-4-[4-(4-methyl-piperazine-1-carbonyl)-piperidin1-yl]-phenylamino}-pyrrolo[2,1-f][1,2,4]triazin-7-yl)-phenyl]-N-methyl-methanesulfonamide; compound with trifluoro-acetic acid as a brown lyophylate (34 mg, 22%). LC/MS (E/I+) 633.24 (M+H). NMR $^1$H (DMSO-$d_6$)-10 (bs, 1H), 8.94 (s, 1H), 7.96-7.53 (m, 6H), 6.98 (s, 1H), 6.96 (s, 1H), 6.87 (bs, 1H), 6.61 (bs, 1H), 4.48 (bm, 1H), 4.21 (bm, 1H), 3.84 (s, 3H), 3.80-3.46 (bm, TFA salt and water provided poor resolution), 3.06 (s, 3H), 3.0-2.9 (bm, TFA salt provided poor resolution), 2.87 (s, 3H), 2.83 (s, 3H), 1.82 (bs, 4H).

Example 460

N-[2-(2-{2-Methoxy-4-[(S)-3-(4-methyl-piperazine-1-carbonyl)-piperidin-1-yl]-phenylamino}-pyrrolo[2,1-f][1,2,4]triazin-7-yl)-phenyl]-N-methyl-methanesulfonamide; compound with trifluoro-acetic acid a) (S)-1-(3-Methoxy-4-nitro-phenyl)-piperidine-3-carboxylic acid was prepared by reacting 4-fluoro-2-methoxy-1-nitro-benzene (342 mg, 2.0 mmol) with (S)-Piperidine-3-carboxylic acid (258 mg, 2.0 mmol) at 80° C. in DMF using $K_2CO_3$ (608 mg, 2.20 mmol) as a base scavenger. After 16 h the reaction was concentrated under reduced pressure and the residue was partitioned between EtOAc and water. The aqueous phase was acidified with 1N HCl to pH 4-5. The resulting yellow solid was filtered, rinsed with water, and air dried overnight to yield 352 mg (63%) of (S)-1-(3-Methoxy-4-nitro-phenyl)-piperidine-3-carboxylic acid as a yellow solid. LC/MS (E/I+) 281.08 (M+H).

b) [(S)-1-(3-Methoxy-4-nitro-phenyl)-piperidin-3-yl]-(4-methyl-piperazin-1-yl)-methanone was prepared in an analogous fashion to Example 443a replacing 1-(4-Nitro-phenyl)-piperidine-3-carboxylic acid with (S)-1-(3-Methoxy-4-nitro-phenyl)-piperidine-3-carboxylic acid. [(S)-1-(3-Methoxy-4-nitro-phenyl)-piperidin-3-yl]-(4-methyl-piperazin-1-yl)-methanone was isolated as a yellow oil after described extractive workup and was used without further manipulation. LC/MS (E/I+) 363.17 (M+H).

c) [(S)-1-(4-Amino-3-methoxy-phenyl)-piperidin-3-yl]-(4-methyl-piperazin-1-yl)-methanone was prepared in an analogous fashion to Example 443b replacing (4-Methyl-piperazin-1-yl)-[1-(4-nitro-phenyl)-piperidin-3-yl]-methanone with [(S)-1-(3-Methoxy-4-nitro-phenyl)-piperidin-3-yl]-(4-methyl-piperazin-1-yl)-methanone. (125 mg, 98%). LC/MS (E/I+) 333.20 (M+H).

d) The titled compound was prepared in an analogous fashion to Example 459 replacing [1-(4-Amino-3-methoxy-phenyl)-piperidin-4-yl]-(4-methyl-piperazin-1-yl)-methanone with [(S)-1-(4-Amino-3-methoxy-phenyl)-piperidin-3-yl]-(4-methyl-piperazin-1-yl)-methanone to give after purification via reverse phase HPLC N-[2-(2-{2-Methoxy-4-[(S)-3-(4-methyl-piperazine-1-carbonyl)-piperidin-1-yl]-phenylamino}-pyrrolo[2,1-f][1,2,4]triazin-7-yl)-phenyl]-N-methyl-methanesulfonamide; compound with trifluoro-acetic acid as a brown lyophylate (18 mg, 15%). LC/MS (E/I+) 633.22 (M+H). NMR $^1$H (DMSO-$d_6$)-9.82 (bs, 1H), 8.93 (s, 1H), 7.98-7.54 (m, 6H), 6.97 (s, 1H), 6.94 (s, 1H), 6.72 (bs, 1H), 6.47 (bs, 1H), 4.48 (bm, 1H), 4.20 (bm, 1H), 3.83 (s, 3H), 3.66-3.43 (bm, TFA salt and water provided poor resolution), 3.07 (s, 3H), 3.0-2.9 (bm, TFA salt provided poor resolution), 2.88 (s, 3H), 2.83 (s, 3H), 1.87-1.51 (bm, 4H).

Example 461

((S)-1-{3-Methoxy-4-[7-(2-methoxy-phenyl)-pyrrolo[2,1-f][1,2,4]triazin-2-ylamino]-phenyl}-piperidin-3-yl)-(4-methyl-piperazin-1-yl)-methanone; compound with trifluoro-acetic acid The titled compound was prepared in an analogous fashion to Example 460d replacing N-[2-(2-Methanesulfinyl-pyrrolo[2,1-f][1,2,4]triazin-7-yl)-phenyl]-N-methyl-methanesulfonamide with 7-(2-Methoxy-phenyl)-2-methylsulfanyl-pyrrolo[2,1-f][1,2,4]triazine to give after purification via reverse phase HPLC ((S)-1-{3-Methoxy-4-[7-(2-methoxy-phenyl)-pyrrolo[2,1-f][1,2,4]triazin-2-ylamino]-phenyl}-piperidin-3-yl)-(4-methyl-piperazin-1-yl)-methanone; compound with trifluoro-acetic acid as a brown lyophylate (23 mg, 22%). LC/MS (E/I+) 556.22 (M+H). NMR $^1$H (DMSO-$d_6$)-9.9 (bs, 1H), 8.92 (s, 1H), 7.96 (bm, 1H), 7.84-7.82 (d, 1H, J=7.51 Hz), 7.59 (bs, 1H), 7.48-7.44 (m, 1H), 7.22-7.20 (d, 1H, J=8.39 Hz), 7.12-7.08 (m, 1H), 6.96 (s, 1H), 6.93 (s, 1H), 6.82 (bs, 1H), 6.55 (bs, 1H), 5.0-3.9 (bm, TFA salt and water provided poor resolution), 3.87 (s, 3H), 3.80 (s, 3H), 3.65-2.93 (bm, TFA salt provided poor resolution), 2.83 (s, 3H), 1.88-1.79 (bm, 3H), 1.52 (bm, 1H).

Example 462

N-[2-(2-{2-Methoxy-4-[(R)-3-(4-methyl-piperazine-1-carbonyl)-piperidin-1-yl]-phenylamino}-pyrrolo[2,1-f][1,2,4]triazin-7-yl)-phenyl]-N-methyl-methanesulfonamide; compound with trifluoro-acetic acid a) (R)-1-(3-Methoxy-4-nitro-phenyl)-piperidine-3-carboxylic acid was prepared in a in an analogous fashion to (S)-1-(3-Methoxy-4-nitro-phenyl)-piperidine-3-carboxylic acid of Example 460a replacing (S)-Piperidine-3-carboxylic acid with (R)-Piperidine-3-carboxylic acid. (R)-1-(3-Methoxy-4-nitro-phenyl)-piperidine-3-carboxylic acid was isolated as a yellow solid (955 mg, 88%).

b) [(R)-1-(3-Methoxy-4-nitro-phenyl)-piperidin-3-yl]-(4-methyl-piperazin-1-yl)-methanone was prepared in an analogous fashion to) [(S)-1-(3-Methoxy-4-nitro-phenyl)-piperidin-3-yl]-(4-methyl-piperazin-1-yl)-methanone of Example 460b replacing (S)-1-(3-Methoxy-4-nitro-phenyl)-piperidine-3-carboxylic acid with (R)-1-(3-Methoxy-4-nitro-phenyl)-piperidine-3-carboxylic acid. [(R)-1-(3-Methoxy-4-nitro-phenyl)-piperidin-3-yl]-(4-methyl-piperazin-1-yl)-methanone was isolated as a yellow oil after described extractive workup and was used without further manipulation. LC: 88% pure.

c) [(R)-1-(4-Amino-3-methoxy-phenyl)-piperidin-3-yl]-(4-methyl-piperazin-1-yl)-methanone was prepared in an analogous fashion to [(S)-1-(4-Amino-3-methoxy-phenyl)-piperidin-3-yl]-(4-methyl-piperazin-1-yl)-methanone of Example 460c replacing [(S)-1-(3-Methoxy-4-nitro-phenyl)-piperidin-3-yl]-(4-methyl-piperazin-1-yl)-methanone with [(R)-1-(3-Methoxy-4-nitro-phenyl)-piperidin-3-yl]-(4-methyl-piperazin-1-yl)-methanone. (390 mg, 98%). LC/MS (E/I+) 333.20 (M+H).

d) The titled compound was prepared in an analogous fashion to Example 460d replacing [(S)-1-(4-Amino-3-methoxy-phenyl)-piperidin-3-yl]-(4-methyl-piperazin-1-yl)-methanone with [(R)-1-(4-Amino-3-methoxy-phenyl)-piperidin-3-yl]-(4-methyl-piperazin-1-yl)-methanone to give after purification via reverse phase HPLC N-[2-(2-{2-Methoxy-4-[(R)-3-(4-methyl-piperazine-1-carbonyl)-piperidin-1-yl]-phenylamino}-pyrrolo[2,1-f][1,2,4]triazin-7-yl)-phenyl]-N-methyl-methanesulfonamide; compound with trifluoro-acetic acid as a brown lyophylate (26 mg, 14%). LC/MS (E/I+) 633.24 (M+H). NMR $^1$H (DMSO-$d_6$)-9.82 (bs, 1H), 8.93 (s, 1H), 7.98-7.54 (m, 6H), 6.98 (s, 1H), 6.95 (s, 1H), 6.74 (bs, 1H), 6.48 (bs, 1H), 4.48 (bm, 1H), 4.20 (bm, 1H), 3.83 (s, 3H), 3.66-3.44 (bm, TFA salt and water provided poor resolution), 3.07 (s, 3H), 3.0-2.9 (bm, TFA salt provided poor resolution), 2.88 (s, 3H), 2.83 (s, 3H), 1.87-1.51 (bm, 4H).

Example 463

((R)-1-{3-Methoxy-4-[7-(2-methoxy-phenyl)-pyrrolo[2,1-f][1,2,4]triazin-2-ylamino]-phenyl}-piperidin-3-yl)-(4-methyl-piperazin-1-yl)-methanone; compound with trifluoro-acetic acid The titled compound was prepared in an analogous fashion to Example 461 replacing [(S)-1-(4-Amino-3-methoxy-phenyl)-piperidin-3-yl]-(4-methyl-piperazin-1-yl)-methanone with [(R)-1-(4-Amino-3-methoxy-phenyl)-piperidin-3-yl]-(4-methyl-piperazin-1-yl)-methanone to give after purification via reverse phase HPLC ((R)-1-{3-Methoxy-4-[7-(2-methoxy-phenyl)-pyrrolo[2,1-f][1,2,4]triazin-2-ylamino]-phenyl}-piperidin-3-yl)-(4-methyl-piperazin-1-yl)-methanone; compound with trifluoro-acetic acid as a brown lyophylate (29 mg, 18%). LC/MS (E/I+) 556.24 (M+H). NMR $^1$H (DMSO-$d_6$)-9.9 (bs, 1H), 8.92 (s, 1H), 7.94 (bm, 1H), 7.83-7.82 (d, 1H, J=7.49 Hz), 7.59 (bs, 1H), 7.47-7.43 (m, 1H), 7.22-7.20 (d, 1H, J=8.37 Hz), 7.12-7.08 (m, 1H), 6.97 (s, 1H), 6.94 (s, 1H), 6.82 (bs, 1H), 6.55 (bs, 1H), 5.0-3.9 (bm, TFA salt and water provided poor resolution), 3.87 (s, 3H), 3.79 (s, 3H), 3.65-2.93 (bm, TFA salt provided poor resolution), 2.83 (s, 3H), 1.88-1.79 (bm, 3H), 1.52 (bm, 1H).

Example 464

((R)-1-{3-Methoxy-4-[7-(6-methoxy-pyridin-3-yl)-pyrrolo[2,1-f][1,2,4]triazin-2-ylamino]-phenyl}-piperidin-3-yl)-(4-methyl-piperazin-1-yl)-methanone; compound with trifluoro-acetic acid The titled compound was prepared in an analogous fashion to Example 462d replacing N-[2-(2-Methanesulfinyl-pyrrolo[2,1-f][1,2,4]triazin-7-yl)-phenyl]-N-methyl-methanesulfonamide with 2-Methanesulfinyl-7-(6-methoxy-pyridin-3-yl)-pyrrolo[2,1-f][1,2,4]triazine to give after purification via reverse phase HPLC ((R)-1-{3-Methoxy-4-[7-(6-methoxy-pyridin-3-yl)-pyrrolo[2,1-f][1,2,4]triazin-2-ylamino]-phenyl}-piperidin-3-yl)-(4-methyl-piperazin-1-yl)-methanone; compound with trifluoro-acetic acid as a brown lyophylate (16 mg, 10%). LC/MS (E/I+) 557.26 (M+H). NMR $^1$H (DMSO-$d_6$)-9.76 (bs, 1H), 8.92 (s, 1H), 8.89 (s, 1H), 8.50-8.48 (d, 1H, J=8.91 Hz), 7.87 (s, 1H), 7.74 (bm, 1H), 7.18 (s, 1H), 6.94 (s, 2H), 6.77 (bs, 1H), 6.63 (bs, 1H), 5.5-4.0 (bm, TFA salt and water provided poor resolution), 3.92 (s, 3H), 3.85 (s, 3H), 3.72-2.92 (bm, TFA salt provided poor resolution), 2.83 (s, 3H), 1.87-1.53 (bm, 4H).

Example 465

N-[2-(2-{2-Methoxy-4-[(R)-3-(4-methyl-piperazin-1-ylmethyl)-piperidin-1-yl]-phenylamino}-pyrrolo[2,1-f][1,2,4]triazin-7-yl)-phenyl]-N-methyl-methanesulfonamide; compound with trifluoro-acetic acid a) 1-[(R)-1-(3-Methoxy-4-nitro-phenyl)-piperidin-3-ylmethyl]-4-methyl-piperazine was prepared in an analogous fashion to 1-Methyl-4-[1-(4-nitro-phenyl)-piperidin-3-ylmethyl]-piperazine of Example 455a replacing (4-Methyl-piperazin-1-yl)-[1-(4-nitro-phenyl)-piperidin-3-yl]-methanone with [(S)-1-(3-Methoxy-4-nitro-phenyl)-piperidin-3-yl]-(4-methyl-piperazin-1-yl)-methanone. 1-[(R)-1-(3-Methoxy-4-nitro-phenyl)-piperidin-3-ylmethyl]-4-methyl-piperazine was isolated as an orange oil (170 mg, 77%). LC/MS (E/I+) 349.20 (M+H).

b) 2-Methoxy-4-[(R)-3-(4-methyl-piperazin-1-ylmethyl)-piperidin-1-yl]-phenylamine was prepared in an analogous fashion to [(S)-1-(4-Amino-3-methoxy-phenyl)-piperidin-3-yl]-(4-methyl-piperazin-1-yl)-methanone of Example 460c replacing [(S)-1-(3-Methoxy-4-nitro-phenyl)-piperidin-3-yl]-(4-methyl-piperazin-1-yl)-methanone with 1-[(R)-1-(3-Methoxy-4-nitro-phenyl)-piperidin-3-ylmethyl]-4-methyl-piperazine. (160 mg, 100%). LC/MS (E/I+) 319.22 (M+H).

c) The titled compound was prepared in an analogous fashion to Example 460d replacing [(S)-1-(4-Amino-3-methoxy-phenyl)-piperidin-3-yl]-(4-methyl-piperazin-1-yl)-methanone with 2-Methoxy-4-[(R)-3-(4-methyl-piperazin-1-ylmethyl)-piperidin-1-yl]-phenylamine to give after purification via reverse phase HPLC N-[2-(2-{2-Methoxy-4-[(R)-3-(4-methyl-piperazin-1-ylmethyl)-piperidin-1-yl]-phenylamino}-pyrrolo[2,1-f][1,2,4]triazin-7-yl)-phenyl]-N-methyl-methanesulfonamide; compound with trifluoro-acetic acid as a brown lyophylate (24 mg, 16%). LC/MS (E/I+) 619.24 (M+H). NMR $^1$H (DMSO-$d_6$)-8.95 (s, 1H), 7.97-7.54 (m, 6H), 6.99 (s, 1H), 6.96 (s, 1H), 6.95-6.5 (bs, 1H), 5.0-4.0 (bm, TFA salt and water provided poor resolution), 3.86 (s, 3H), 3.51-3.41 (bm, TFA salt provided poor resolution), 3.08 (s, 3H), 2.87 (s, 3H), 2.78 (s, 3H), 2.0 (bm, 1H), 1.82 (bm, 3H), 1.15 (bm, 1H).

Example 466

{2-Methoxy-4-[(R)-3-(4-methyl-piperazin-1-ylmethyl)-piperidin-1-yl]-phenyl}-[7-(2-methoxy-phenyl)-pyrrolo[2,1-f][1,2,4]triazin-2-yl]-amine; compound with trifluoro-acetic acid The titled compound was prepared in an analogous fashion to Example 465c replacing N-[2-(2-Methanesulfinyl-pyrrolo[2,1-f][1,2,4]triazin-7-yl)-phenyl]-N-methyl-methanesulfonamide with 7-(2-Methoxy-phenyl)-2-methylsulfanyl-pyrrolo[2,1-f][1,2,4]triazine to give after purification via reverse phase HPLC {2-Methoxy-4-[(R)-3-(4-methyl-piperazin-1-ylmethyl)-piperidin-1-yl]-phenyl}-[7-(2-methoxy-phenyl)-pyrrolo[2,1-f][1,2,4]triazin-2-yl]-amine; compound with trifluoro-acetic acid as a brown lyophylate (22 mg, 18%). LC/MS (E/I+) 542.24 (M+H). NMR $^1$H (DMSO-d$_6$)-8.96 (s, 1H), 8.07 (bs, 1H), 7.83-7.81 (d, 1H, J=7.50 Hz), 7.70 (bs, 1H), 7.48-7.44 (m, 1H), 7.22-7.20 (d, 1H, J=8.51 Hz), 7.13-7.09 (m, 1H), 6.99-6.75 (m, 4H), 3.90 (s, 3H), 3.80 (s, 3H), 3.54-2.80 (bm, TFA salt provided poor resolution), 2.79 (s, 3H), 2.15 (bm, 1H), 1.84-1.81 (bm, 3H), 1.22-1.19 (bm, 1H).

Example 467

N-[2-(2-{2-Methoxy-4-[4-(4-methyl-piperazin-1-ylmethyl)-piperidin-1-yl]-phenylamino}-pyrrolo[2,1-f][1,2,4]triazin-7-yl)-phenyl]-N-methyl-methanesulfonamide; compound with trifluoro-acetic acid a) Methoxy-4-nitro-phenyl)-piperidin-4-ylmethyl]-4-methyl-piperazine was prepared in an analogous fashion to 1-Methyl-4-[1-(4-nitro-phenyl)-piperidin-3-ylmethyl]-piperazine of Example 455a replacing (4-Methyl-piperazin-1-yl)-[1-(4-nitro-phenyl)-piperidin-3-yl]-methanone with [1-(3-Methoxy-4-nitro-phenyl)-piperidin-4-yl]-(4-methyl-piperazin-1-yl)-methanone. Methoxy-4-nitro-phenyl)-piperidin-4-ylmethyl]-4-methyl-piperazine was isolated as an orange residue (200 mg, 70%). LC/MS (E/I+) 349.19 (M+H).

b) 2-Methoxy-4-[4-(4-methyl-piperazin-1-ylmethyl)-piperidin-1-yl]-phenylamine was prepared in an analogous fashion to [(S)-1-(4-Amino-3-methoxy-phenyl)-piperidin-3-yl]-(4-methyl-piperazin-1-yl)-methanone of Example 460c replacing [(S)-1-(3-Methoxy-4-nitro-phenyl)-piperidin-3-yl]-(4-methyl-piperazin-1-yl)-methanone with 1-[1-(3-Methoxy-4-nitro-phenyl)-piperidin-4-ylmethyl]-4-methyl-piperazine. (200 mg, 100%). LC/MS (E/I+) 319.16 (M+H).

c) The titled compound was prepared in an analogous fashion to Example 465c replacing 2-Methoxy-4-[(R)-3-(4-methyl-piperazin-1-ylmethyl)-piperidin-1-yl]-phenylamine with 2-Methoxy-4-[4-(4-methyl-piperazin-1-ylmethyl)-piperidin-1-yl]-phenylamine to give after purification via reverse phase HPLC N-[2-(2-{2-Methoxy-4-[4-(4-methyl-piperazin-1-ylmethyl)-piperidin-1-yl]-phenylamino}-pyrrolo[2,1-f][1,2,4]triazin-7-yl)-phenyl]-N-methyl-methanesulfonamide; compound with trifluoro-acetic acid as a brown lyophylate (31 mg, 18%). LC/MS (E/I+) 619.24 (M+H). NMR $^1$H (DMSO-d$_6$)-8.96 (s, 1H), 8.02-7.54 (m, 6H), 7.00-6.5 (bm, 4H), 3.87 (s, 3H), 3.64-3.10 (bm, TFA salt provided poor resolution), 3.08 (s, 3H), 2.88 (s, 3H), 2.81 (s, 3H), 1.90 (bm, 4H), 1.40 (bm, 2H).

Example 468

{2-Methoxy-4-[4-(4-methyl-piperazin-1-ylmethyl)-piperidin-1-yl]-phenyl}-[7-(2-methoxy-phenyl)-pyrrolo[2,1-f][1,2,4]triazin-2-yl]-amine; compound with trifluoro-acetic acid The titled compound was prepared in an analogous fashion to Example 467c replacing N-[2-(2-Methanesulfinyl-pyrrolo[2,1-f][1,2,4]triazin-7-yl)-phenyl]-N-methyl-methanesulfonamide with 7-(2-Methoxy-phenyl)-2-methylsulfanyl-pyrrolo[2,1-f][1,2,4]triazine to give after purification via reverse phase HPLC {2-Methoxy-4-[4-(4-methyl-piperazin-1-ylmethyl)-piperidin-1-yl]-phenyl}-[7-(2-methoxy-phenyl)-pyrrolo[2,1-f][1,2,4]triazin-2-yl]-amine; compound with trifluoro-acetic acid as a brown lyophylate (45 mg, 28%). LC/MS (E/I+) 542.23 (M+H). NMR $^1$H (DMSO-d$_6$)-8.96 (s, 1H), 8.09 (bs, 1H), 7.82-7.80 (d, 1H, J=7.49), 7.71 (bs, 1H), 7.48-7.44 (m, 1H), 7.22-7.20 (d, 1H, J=8.36 Hz), 7.12-7.09 (m, 1H), 7.05 (bs, 1H), 6.98 (s, 1H), 6.97 (s, 1H), 6.8 (bs, 1H), 6.0-5.0 (bm, TFA salt and water provided poor resolution), 3.90 (s, 3H), 3.80 (s, 3H), 3.64-3.15 (bm, TFA salt provided poor resolution), 2.82 (s, 3H), 1.93 (bm, 4H), 1.44 (bm, 2H).

Example 469

N-[2-(2-{2-Methoxy-4-[(S)-3-(4-methyl-piperazin-1-ylmethyl)-piperidin-1-yl]-phenylamino}-pyrrolo[2,1-f][1,2,4]triazin-7-yl)-phenyl]-N-methyl-methanesulfonamide; compound with trifluoro-acetic acid a) 1-[(S)-1-(3-Methoxy-4-nitro-phenyl)-piperidin-3-ylmethyl]-4-methyl-piperazine was prepared in an analogous fashion to 1-Methyl-4-[1-(4-nitro-phenyl)-piperidin-3-ylmethyl]-piperazine of Example 455a replacing (4-Methyl-piperazin-1-yl)-[1-(4-nitro-phenyl)-piperidin-3-yl]-methanone with [(R)-1-(3-Methoxy-4-nitro-phenyl)-piperidin-3-yl]-(4-methyl-piperazin-1-yl)-methanone. 1-[(S)-1-(3-Methoxy-4-nitro-phenyl)-piperidin-3-ylmethyl]-4-methyl-piperazine was isolated as an orange oil (170 mg, 43%). LC/MS (E/I+) 349.24 (M+H).

b) 2-Methoxy-4-[(S)-3-(4-methyl-piperazin-1-ylmethyl)-piperidin-1-yl]-phenylamine was prepared in an analogous fashion to [(S)-1-(4-Amino-3-methoxy-phenyl)-piperidin-3-yl]-(4-methyl-piperazin-1-yl)-methanone of Example 460c replacing [(S)-1-(3-Methoxy-4-nitro-phenyl)-piperidin-3-yl]-(4-methyl-piperazin-1-yl)-methanone with 1-[(S)-1-(3-Methoxy-4-nitro-phenyl)-piperidin-3-ylmethyl]-4-methyl-piperazine. (160 mg, 97%). LC/MS (E/I+) 319.21 (M+H).

c) The titled compound was prepared in an analogous fashion to Example 460d replacing [(S)-1-(4-Amino-3-methoxy-phenyl)-piperidin-3-yl]-(4-methyl-piperazin-1-yl)-methanone with 2-Methoxy-4-[(S)-3-(4-methyl-piperazin-1-ylmethyl)-piperidin-1-yl]-phenylamine to give after purification via reverse phase HPLC N-[2-(2-{2-Methoxy-4-[(S)-3-(4-methyl-piperazin-1-ylmethyl)-piperidin-1-yl]-phenylamino}-pyrrolo[2,1-f][1,2,4]triazin-7-yl)-phenyl]-N-methyl-methanesulfonamide; compound with trifluoro-acetic acid as a brown lyophylate (29 mg, 18%). LC/MS (E/I+) 619.24 (M+H). NMR $^1$H (DMSO-d$_6$)-8.95 (s, 1H), 7.97-7.53 (m, 6H), 6.99 (s, 1H), 6.96 (s, 1H), 6.95-6.5 (bs, 2H), 5.0-4.0 (bm, TFA salt and water provided poor resolution), 3.86 (s, 3H), 3.53-3.40 (bm, TFA salt provided poor resolution), 3.08 (s, 3H), 2.87 (s, 3H), 2.78 (s, 3H), 2.0 (bm, 1H), 1.82 (bm, 3H), 1.15 (bm, 1H).

Example 470

{2-Methoxy-4-[(S)-3-(4-methyl-piperazin-1-ylmethyl)-piperidin-1-yl]-phenyl}-[7-(2-methoxy-phenyl)-pyrrolo[2,1-f][1,2,4]triazin-2-yl]-amine; compound with trifluoro-acetic acid The titled compound was prepared in an analogous fashion to Example 465c replacing N-[2-(2-Methanesulfinyl-pyrrolo[2,1-f][1,2,4]triazin-7-yl)-phenyl]-N-methyl-methanesulfonamide with 7-(2-Methoxy-phenyl)-2-methylsulfanyl-pyrrolo[2,1-f][1,2,4]triazine and replacing 2-Methoxy-4-[(R)-3-(4-methyl-piperazin-1-ylmethyl)-piperidin-1-yl]-phenylamine with 2-Methoxy-4-[(S)-3-(4-methyl-piperazin-1-ylmethyl)-piperidin-1-yl]-phenylamine to give after purification via reverse phase HPLC {2-Methoxy-4-[(S)-3-(4-methyl-piperazin-1-ylmethyl)-piperidin-1-yl]-phenyl}-[7-(2-methoxy-phenyl)-pyrrolo[2,1-f][1,2,4]triazin-2-yl]-amine; compound with trifluoro-acetic acid as a brown lyophylate (43 mg, 32%). LC/MS (E/I+) 542.25 (M+H). NMR $^1$H (DMSO-d$_6$)-8.96 (s, 1H), 8.07 (bm, 1H), 7.82-7.80 (d, 1H, J=7.53 Hz), 7.72 (bs, 1H), 7.48-7.44 (m, 1H), 7.22-7.20 (d, 1H, J=8.34 Hz), 7.13-7.09 (m, 1H), 6.99-6.75 (m, 4H), 3.91 (s, 3H), 3.80 (s, 3H), 3.54-2.85 (bm, TFA salt provided poor resolution), 2.80 (s, 3H), 2.58 (bm, 3H), 2.21 (bm, 1H), 1.85-1.82 (bm, 3H), 1.24-1.21 (bm, 1H).

Example 471

N-(4-{7-[2-(Methanesulfonyl-methyl-amino)-phenyl]-pyrrolo[2,1-f][1,2,4]triazin-2-ylamino}-3-methoxy-phenyl)-N-methyl-2-(4-methyl-piperazin-1-yl)-acetamide; compound with trifluoro-acetic acid a) N-(3-Methoxy-4-nitro-phenyl)-N-methyl-2-(4-methyl-piperazin-1-yl)-acetamide. (3-Methoxy-4-nitro-phenyl)-methyl-amine (0.364 g, 2.0 mmol) in CH$_2$Cl$_2$ (10 mL) was treated with Et$_3$N (0.42 mL, 3 mmol) and then chloroacetyl chloride (0.18 mL, 2.20 mmol). After 16 hours the reaction mixture was treated with second portions of Et$_3$N (0.42 mL, 3 mmol) and then chloroacetyl chloride (0.18 mL, 2.20 mmol). The resulting 2-Chloro-N-(3-methoxy-4-nitro-phenyl)-N-methyl-acetamide was treated in situ with neat 1-Methyl-piperazine (2 mL, 20 mmol). After stirring 20 minutes the reaction mixture was extracted with water followed by saturated aqueous NaHCO$_3$. The organic phase was dried over Na2SO4, filtered, and concentrated under reduced pressure to give 460 mg (71%) of desired N-(3-Methoxy-4-nitro-phenyl)-N-methyl-2-(4-methyl-piperazin-1-yl)-acetamide as a yellow residue, which was used for subsequent step without further manipulation. LC/MS (E/I+) 323.15 (M+H).

b) N-(4-Amino-3-methoxy-phenyl)-N-methyl-2-(4-methyl-piperazin-1-yl)-acetamide was prepared in an analogous fashion to [(S)-1-(4-Amino-3-methoxy-phenyl)-piperidin-3-yl]-(4-methyl-piperazin-1-yl)-methanone of Example 460c replacing [(S)-1-(3-Methoxy-4-nitro-phenyl)-piperidin-3-yl]-(4-methyl-piperazin-1-yl)-methanone with N-(3-Methoxy-4-nitro-phenyl)-N-methyl-2-(4-methyl-piperazin-1-yl)-acetamide. N-(4-Amino-3-methoxy-phenyl)-N-methyl-2-(4-methyl-piperazin-1-yl)-acetamide was purified by trituration with Et$_2$O to give pure product as a brown solid, MP 115-118° C. (390 mg, 93%). LC/MS (E/I+) 293 (M−15).

c) The titled compound was prepared in an analogous fashion to Example 460d replacing: 1) [(S)-1-(4-Amino-3-methoxy-phenyl)-piperidin-3-yl]-(4-methyl-piperazin-1-yl)-methanone with N-(4-Amino-3-methoxy-phenyl)-N-methyl-2-(4-methyl-piperazin-1-yl)-acetamide, 2) 1-Methoxy-2-propanol with N-Methylpyrrolidinone, and 3) adding 2 eqvts of CsF, to give after purification via reverse phase HPLC N-(4-{7-[2-(Methanesulfonyl-methyl-amino)-phenyl]-pyrrolo[2,1-f][1,2,4]triazin-2-ylamino}-3-methoxy-phenyl)-N-methyl-2-(4-methyl-piperazin-1-yl)-acetamide; compound with trifluoro-acetic acid as a brown lyophylate (4 mg, 2%). LC/MS (E/I+) 593.19 (M+H). NMR $^1$H (DMSO-d$_6$)-9.50 (bs, 1H), 9.00 (s, 1H), 8.05-7.99 (m, 2H), 7.87 (s, 1H), 7.67-7.65 (d, 1H, J=7.40 Hz), 7.58-7.54 (m, 2H), 7.04-7.00 (m, 3H), 6.83 (m, 1H), 4.25-3.90 (bm, TFA salt provided poor resolution), 3.88 (s, 3H), 3.27 (bm, 4H), 3.16 (s, 2H), 3.09 (s, 3H), 3.05-2.90 (bm, 4H), 2.89 (s, 3H), 2.73 (s, 3H).

Example 472

N-{3-Methoxy-4-[7-(2-methoxy-phenyl)-pyrrolo[2,1-f][1,2,4]triazin-2-ylamino]-phenyl}-N-methyl-2-morpholin-4-yl-acetamide; compound with trifluoro-acetic acid a) N-(3-Methoxy-4-nitro-phenyl)-N-methyl-2-morpholin-4-yl-acetamide was prepared in an analogous fashion to N-(3-Methoxy-4-nitro-phenyl)-N-methyl-2-(4-methyl-piperazin-1-yl)-acetamide of Example 471a by treating the in situ generated 2-Chloro-N-(3-methoxy-4-nitro-phenyl)-N-methyl-acetamide with morpholine rather than 1-methyl piperazine. After workup the crude product was pumped under high vacuum to remove majority of morpholine, as some carried along in organic phase after extraction. Small residual amounts were separated after subsequent reduction via trituration with Et$_2$O. (1.19 g, 73%). LC/MS (E/I+) 310.11 (M+H).

b) N-(4-Amino-3-methoxy-phenyl)-N-methyl-2-morpholin-4-yl-acetamide was prepared in an analogous fashion to [(S)-1-(4-Amino-3-methoxy-phenyl)-piperidin-3-yl]-(4-methyl-piperazin-1-yl)-methanone of Example 460c replacing [(S)-1-(3-Methoxy-4-nitro-phenyl)-piperidin-3-yl]-(4-methyl-piperazin-1-yl)-methanone with N-(3-Methoxy-4-nitro-phenyl)-N-methyl-2-morpholin-4-yl-acetamide. N-(4-Amino-3-methoxy-phenyl)-N-methyl-2-morpholin-4-yl-acetamide was purified by trituration with Et$_2$O to yield this desired product as a white solid, MP 198-201° C. (870 mg, 93%). LC/MS (E/I+) 280.11 (M+H).

c) The titled compound was prepared in an analogous fashion to Example 471c replacing N-[2-(2-Methanesulfinyl-pyrrolo[2,1-f][1,2,4]triazin-7-yl)-phenyl]-N-methyl-methanesulfonamide with 7-(2-Methoxy-phenyl)-2-methylsulfanyl-pyrrolo[2,1-f][1,2,4]triazine and replacing N-(4-Amino-3-methoxy-phenyl)-N-methyl-2-(4-methyl-piperazin-1-yl)-acetamide with N-(4-Amino-3-methoxy-phenyl)-N-methyl-2-morpholin-4-yl-acetamide to give after purification via reverse phase HPLC N-{3-Methoxy-4-[7-(2-methoxy-phenyl)-pyrrolo[2,1-f][1,2,4]triazin-2-ylamino]-phenyl}-N-methyl-2-morpholin-4-yl-acetamide; compound with trifluoro-acetic acid as a brown lyophylate (15 mg, 11%). LC/MS (E/I+) 503.16 (M+H). NMR $^1$H (DMSO-d$_6$)-10.0 (bs, 1H), 9.00 (s, 1H), 8.28-8.26 (d, 1H, J=8.59 Hz), 7.82-7.79 (m, 2H), 7.50-7.46 (m, 1H), 7.25-7.23 (d, 1H, J=8.31 Hz), 7.17-7.13 (m, 1H), 7.09 (s, 1H), 7.00 (s, 2H), 6.90-6.88 (d, 1H, J=8.71 Hz), 3.95 (s, 3H), 3.87 (s, 2H), 3.80 (s, 7H), 3.32 (m, 2H), 3.24 (s, 3H), 3.08 (bm, 2H).

Example 473

N-(4-{7-[2-(Methanesulfonyl-methyl-amino)-phenyl]-pyrrolo[2,1-f][1,2,4]triazin-2-ylamino}-3-methoxy-phenyl)-N-methyl-2-morpholin-4-yl-acetamide; compound with trifluoro-acetic acid The titled compound was prepared in an analogous fashion to Example 471c replacing N-(4-Amino-3-methoxy-phenyl)-N-methyl-2-(4-methyl-piperazin-1-yl)-acetamide with N-(4-Amino-3-methoxy-phenyl)-N-methyl-2-morpholin-4-yl-acetamide to give after purification via reverse phase HPLC N-(4-{7-[2-(Methanesulfonyl-methyl-amino)-phenyl]-pyrrolo[2,1-f][1,2,4]triazin-2-ylamino}-3-methoxy-phenyl)-N-methyl-2-morpholin-4-yl-acetamide; compound with trifluoro-acetic acid as a brown lyophylate (14 mg, 9%). LC/MS (E/I+) 580.19 (M+H). NMR $^1$H (DMSO-$d_6$)-10.1 (bs, 1H), 9.02 (s, 1H), 8.18 (d, 1H, J=8.28 Hz), 8.03-8.02 (d, 1H, J=7.37 Hz), 7.88 (s, 1H), 7.69-7.67 (d, 1H, J=7.52 Hz), 7.62-7.54 (m, 2H), 7.10 (s, 1H), 7.05-7.02 (m, 2H), 6.90-6.88 (d, 1H, J=8.40 Hz), 3.93 (s, 3H), 3.87-3.77 (m, 6H), 3.32-3.29 (m, 2H), 3.24 (s, 3H), 3.11 (s, 3H), 3.08 (m, 2H), 2.91 (s, 3H).

Example 474

N-{3-Methoxy-4-[7-(2-methoxy-phenyl)-pyrrolo[2,1-f][1,2,4]triazin-2-ylamino]-phenyl}-N-methyl-2-(4-methyl-piperazin-1-yl)-acetamide; compound with trifluoro-acetic acid The titled compound was prepared in an analogous fashion to Example 471c replacing N-[2-(2-Methanesulfinyl-pyrrolo[2,1-f][1,2,4]triazin-7-yl)-phenyl]-N-methyl-methanesulfonamide with 7-(2-Methoxy-phenyl)-2-methylsulfanyl-pyrrolo[2,1-f][1,2,4]triazine to give after purification via reverse phase HPLC N-{3-Methoxy-4-[7-(2-methoxy-phenyl)-pyrrolo[2,1-f][1,2,4]triazin-2-ylamino]-phenyl}-N-methyl-2-(4-methyl-piperazin-1-yl)-acetamide; compound with trifluoro-acetic acid as a brown lyophylate (8 mg, 6%). LC/MS (E/I+) 516.22 (M+H). NMR $^1$H (DMSO-$d_6$)-8.99 (s, 1H), 8.21-8.19 (d, 1H, J=8.33 Hz), 7.81-7.78 (m, 2H), 7.49-7.45 (m, 1H), 7.24-7.22 (d, 1H, J=8.12 Hz), 7.14-7.11 (m, 1H), 7.06 (s, 1H), 7.00 (m, 2H), 6.86-6.84 (d, 1H, J=8.15 Hz), 3.91 (s, 3H), 3.80 (s, 3H), 3.40 (bm, 4H), 3.18 (s, 3H), 3.08-3.04 (bm, 6H), 2.75 (s, 3H).

Example 475

N-(2-{2-[4-(4-Dimethylamino-piperidin-1-yl)-2-methoxy-phenylamino]-pyrrolo[2,1-f][1,2,4]triazin-7-yl}-phenyl)-N-methyl-methanesulfonamide; compound with trifluoro-acetic acid a) [1-(3-Methoxy-4-nitro-phenyl)-piperidine-4-yl]dimethyl-amine.
1-(3-Methoxy-4-nitro-phenyl)-piperidine-4-one (300 mg, 1.20 mmol) in dichloroethane (6 mL) was treated with 2 M Dimethylamine in THF (3 mL, 6 mmol) followed by sodium triacetoxyborohydride (420 mg, 2 mmol) at rt. After 16 h the mixture was treated with saturated aqueous NaHCO3, stirred 45 minutes. The layers were then separated, and the organic phase was dried over Na2SO4, filtered, and concentrated under reduced pressure to give 305 mg (91%) of desired [1-(3-Methoxy-4-nitro-phenyl)-piperidine-4-yl]dimethyl-amine, which was used without further manipulation. LC/MS (E/I+) 280.12 (M+H).

b) [1-(4-Amino-3-methoxy-phenyl)-piperidin-4-yl]-dimethyl-amine was prepared in an analogous fashion to [(S)-1-(4-Amino-3-methoxy-phenyl)-piperidin-3-yl]-(4-methyl-piperazin-1-yl)-methanone of Example 460c replacing [(S)-1-(3-Methoxy-4-nitro-phenyl)-piperidin-3-yl]-(4-methyl-piperazin-1-yl)-methanone with [1-(3-Methoxy-4-nitro-phenyl)-piperidine-4-yl]dimethyl-amine (280 mg, 100%). LC/MS (E/I+) 249 (M+H).
c) The titled compound was prepared in an analogous fashion to Example 467c replacing 2-Methoxy-4-[4-(4-methyl-piperazin-1-ylmethyl)-piperidin-1-yl]-phenylamine with [1-(4-Amino-3-methoxy-phenyl)-piperidin-4-yl]-dimethyl-amine to give after purification via reverse phase HPLC N-(2-{2-[4-(4-Dimethylamino-piperidin-1-yl)-2-methoxy-phenylamino]-pyrrolo[2,1-f][1,2,4]triazin-7-yl}-phenyl)-N-methyl-methanesulfonamide; compound with trifluoro-acetic acid as a brown lyophylate (59 mg, 38%). LC/MS (E/I+) 550.17 (M+H). NMR $^1$H (DMSO-$d_6$)-9.59 (bs, 1H), 8.92 (s, 1H), 7.99-7.97 (d, 1H, J=6.69 Hz), 7.72-7.70 (d, 1H, J=8.64 Hz), 7.64-7.62 (m, 2H), 7.53 (m, 2H), 6.98-6.92 (m, 2H), 6.68 (s, 1H), 6.43-6.41 (d, 1H, J=8.75 Hz), 3.83-3.78 (m, 5H), 3.29 (m, 1H), 3.07 (s, 3H), 2.88 (s, 3H), 2.80-2.79 (m, 6H), 2.72-2.66 (m, 2H), 2.08-2.05 (m, 2H), 1.75-1.70 (m, 2H).

Example 476

[4-(4-Dimethylamino-piperidin-1-yl)-2-methoxy-phenyl]-[7-(2-methoxy-phenyl)-pyrrolo[2,1-f][1,2,4]triazin-2-yl]-amine; compound with trifluoro-acetic acid The titled compound was prepared in an analogous fashion to Example 475c replacing N-[2-(2-Methanesulfinyl-pyrrolo[2,1-f][1,2,4]triazin-7-yl)-phenyl]-N-methyl-methanesulfonamide with 7-(2-Methoxy-phenyl)-2-methylsulfanyl-pyrrolo[2,1-f][1,2,4]triazine to give after purification via reverse phase HPLC [4-(4-Dimethylamino-piperidin-1-yl)-2-methoxy-phenyl]-[7-(2-methoxy-phenyl)-pyrrolo[2,1-f][1,2,4]triazin-2-yl]-amine; compound with trifluoro-acetic acid as a brown lyophylate (45 mg, 34%). LC/MS (E/I+) 473.19 (M+H). NMR $^1$H (DMSO-$d_6$)-9.76 (bs, 1H), 8.91 (s, 1H), 7.91-7.89 (d, 1H, J=8.60 Hz), 7.85-7.83 (d, 1H, J=7.52 Hz), 7.56 (s, 1H), 7.46-7.42 (m, 1H), 7.21-7.19 (d, 1H, J=8.25 Hz), 7.11-7.08 (m, 1H), 6.96-6.93 (m, 2H), 6.73 (s, 1H), 6.48-6.45 (d, 1H, J=8.69 Hz), 3.86 (s, 3H), 3.79-3.78 (m, 5H), 3.31 (m, 1H), 2.80 (s, 6H), 2.77-2.71 (m, 2H), 2.10-2.07 (m, 2H), 1.78-1.70 (m, 2H).

Example 477

[4-(4-Dimethylamino-piperidin-1-yl)-2-methoxy-phenyl]-[7-(4-methanesulfonyl-phenyl)-pyrrolo[2,1-f][1,2,4]triazin-2-yl]-amine; compound with trifluoro-acetic acid The titled compound was prepared in an analogous fashion to Example 475c replacing N-[2-(2-Methanesulfinyl-pyrrolo[2,1-f][1,2,4]triazin-7-yl)-phenyl]-N-methyl-methanesulfonamide with 2-Methanesulfinyl-7-(4-methanesulfonyl-phenyl)-5-methyl-pyrrolo[2,1-f][1,2,4]triazine to give after purification via reverse phase HPLC [4-(4-Dimethylamino-piperidin-1-yl)-2-methoxy-phenyl]-[7-(4-methanesulfonyl-phenyl)-pyrrolo[2,1-f][1,2,4]triazin-2-yl]-amine; compound with trifluoro-acetic acid as a brown lyophylate (21 mg, 14%). LC/MS (E/I+) 521.15 (M+H). NMR $^1$H (DMSO-$d_6$)-9.62 (bs, 1H), 8.99 (s, 1H), 8.61 (s, 1H), 8.45-8.43 (d, 2H, J=7.66 Hz), 7.91-7.73 (m, 6H), 7.29-7.28 (d, 1H, J=3.10 Hz), 6.98-6.97 (d, 1H, J=3.20 Hz), 6.72 (s, 1H), 6.63-6.61 (d, 2H, J=8.46 Hz), 4.25-3.85 (bm, TFA salt and water provided poor resolution), 3.82 (s, 3H), 3.32 (m, 1H), 3.24 (s, 3H), 2.81 (s, 6H), 2.79-2.72 (m, 2H), 2.10-2.08 (m, 2H), 1.77-1.72 (m, 2H).

Example 478

N-[2-(2-{4-[4-((R)-3-Hydroxy-pyrrolidin-1-yl)-piperidin-1-yl]-2-methoxy-phenylamino}-pyrrolo[2,1-f][1,2,4]triazin-7-yl)-phenyl]-N-methyl-methanesulfonamide; compound with trifluoro-acetic acid a) (R)-1-[1-(3-Methoxy-4-nitro-phenyl)-piperidin-4-yl]-pyrrolidin-3-ol was prepared in an analogous fashion to [1-(3-Methoxy-4-nitro-phenyl)-piperidine-4-yl]dimethyl-amine of Example 475a replacing Dimethylamine with (R)-Pyrrolidin-3-ol. The crude material was purified via trituration with Et$_2$O to yield a yellow solid, MP 137-139° C. (248 mg, 64%). LC/MS (E/I+) 322.16 (M+H).

b) (R)-1-[1-(4-Amino-3-methoxy-phenyl)-piperidin-4-yl]-pyrrolidin-3-ol was prepared in an analogous fashion to [(S)-1-(4-Amino-3-methoxy-phenyl)-piperidin-3-yl]-(4-methyl-piperazin-1-yl)-methanone of Example 460c replacing [(S)-1-(3-Methoxy-4-nitro-phenyl)-piperidin-3-yl]-(4-methyl-piperazin-1-yl)-methanone with (R)-1-[1-(3-Methoxy-4-nitro-phenyl)-piperidin-4-yl]-pyrrolidin-3-ol (180 mg, 99%). LC/MS (E/I+) 292.16 (M+H).

c) The titled compound was prepared in an analogous fashion to Example 467c replacing 2-Methoxy-4-[4-(4-methyl-piperazin-1-ylmethyl)-piperidin-1-yl]-phenylamine with (R)-1-[1-(4-Amino-3-methoxy-phenyl)-piperidin-4-yl]-pyrrolidin-3-ol to give after purification via reverse phase HPLC N-[2-(2-{4-[4-((R)-3-Hydroxy-pyrrolidin-1-yl)-piperidin-1-yl]-2-methoxy-phenylamino}-pyrrolo[2,1-f][1,2,4]triazin-7-yl)-phenyl]-N-methyl-methanesulfonamide; compound with trifluoro-acetic acid as a brown lyophylate (25 mg, 18%). LC/MS (E/I+) 592.23 (M+H). NMR $^1$H (DMSO-d$_6$)-10.0-9.75 (bm, 1H), 8.91 (s, 1H), 7.99-7.97 (d, 1H, J=6.36 Hz), 7.72-7.52 (m, 5H), 6.97 (s, 1H), 6.93 (s, 1H), 6.42-6.40 (d, 1H, J=8.48 Hz), 5.5 (bs, 1H), 4.48-3.50 (bm, TFA salt and water provided poor resolution), 3.4-3.2 (m, 4H), 3.07 (s, 3H), 2.88 (s, 3H), 2.77-2.60 (m, 2H), 2.22-2.07 (m, 3H), 1.93-1.66 (m, 4H).

Example 479

(R)-1-(1-{3-Methoxy-4-[7-(2-methoxy-phenyl)-pyrrolo[2,1-f][1,2,4]triazin-2-ylamino]-phenyl}-piperidin-4-yl)-pyrrolidin-3-ol; compound with trifluoro-acetic acid The titled compound was prepared in an analogous fashion to Example 478 replacing N-[2-(2-Methanesulfinyl-pyrrolo[2,1-f][1,2,4]triazin-7-yl)-phenyl]-N-methyl-methanesulfonamide with 7-(2-Methoxy-phenyl)-2-methylsulfanyl-pyrrolo[2,1-f][1,2,4]triazine to give after purification via reverse phase HPLC (R)-1-(1-{3-Methoxy-4-[7-(2-methoxy-phenyl)-pyrrolo[2,1-f][1,2,4]triazin-2-ylamino]-phenyl}-piperidin-4-yl)-pyrrolidin-3-ol; compound with trifluoro-acetic acid as a brown lyophylate (15 mg, 12%). LC/MS (E/I+) 515.20 (M+H). NMR $^1$H (DMSO-d$_6$)-9.94 (bs, 0.7H), 9.8 (bs, 0.3H), 8.91 (s, 1H), 7.89-7.83 (m, 2H), 7.54 (s, 1H), 7.46-7.42 (m, 1H), 7.21-7.19 (d, 1H, J=8.27 Hz), 7.11-7.08 (m, 1H), 6.96 (s, 1H), 6.92 (s, 1H), 6.70 (s, 1H), 6.44-6.42 (d, 1H, J=8.15 Hz), 4.9-3.9 (bm, TFA salt and water provided poor resolution), 3.86 (s, 3H), 3.80-3.58 (m, 8H), 3.38-3.10 (m, 4H), 2.72-2.61 (m, 2H), 2.26-2.08 (m, 3H), 1.94-1.68 (m, 4H).

Example 480

N-(2-{2-[2-Methoxy-4-(4-pyrrolidin-1-yl-piperidin-1-yl)-phenylamino]-pyrrolo[2,1-f][1,2,4]triazin-7-yl}-phenyl)-N-methyl-methanesulfonamide; compound with trifluoro-acetic acid a) 1-(3-Methoxy-4-nitro-phenyl)-4-pyrrolidin-1-yl-piperidine was prepared in an analogous fashion to [1-(3-Methoxy-4-nitro-phenyl)-piperidine-4-yl]dimethyl-amine of Example 475a replacing Dimethylamine with Pyrrolidine. The crude material was used after workup without further manipulation (350 mg, 96%).

b) 2-Methoxy-4-(4-pyrrolidin-1-yl-piperidin-1-yl)-phenylamine was prepared in an analogous fashion to [(S)-1-(4-Amino-3-methoxy-phenyl)-piperidin-3-yl]-(4-methyl-piperazin-1-yl)-methanone of Example 460c replacing [(S)-1-(3-Methoxy-4-nitro-phenyl)-piperidin-3-yl]-(4-methyl-piperazin-1-yl)-methanone with 1-(3-Methoxy-4-nitro-phenyl)-4-pyrrolidin-1-yl-piperidine (280 mg, 89%). LC/MS (E/I+) 276.16 (M+H).

c) The titled compound was prepared in an analogous fashion to Example 467c replacing 2-Methoxy-4-[4-(4-methyl-piperazin-1-ylmethyl)-piperidin-1-yl]-phenylamine with 2-Methoxy-4-(4-pyrrolidin-1-yl-piperidin-1-yl)-phenylamine to give after purification via reverse phase HPLC N-(2-{2-[2-Methoxy-4-(4-pyrrolidin-1-yl-piperidin-1-yl)-phenylamino]-pyrrolo[2,1-f][1,2,4]triazin-7-yl}-phenyl)-N-methyl-methanesulfonamide; compound with trifluoro-acetic acid as a brown lyophylate (5 mg, 3%). LC/MS (E/I+) 576.24 (M+H). NMR $^1$H (DMSO-d$_6$)-9.57 (bs, 1H), 8.95 (s, 1H), 7.99-7.97 (d, 1H, J=6.28 Hz), 7.71-7.53 (m, 5H), 6.97 (s, 1H), 6.93 (s, 1H), 6.67 (s, 1H), 6.42-6.40 (d, 1H, J=8.72 Hz), 3.83 (s, 3H), 3.79-3.56 (bm, TFA salt and water provided poor resolution), 3.25 (m, 1H), 3.10-3.07 (m, 5H), 2.88 (s, 3H), 2.70-2.64 (m, 2H), 2.12-2.03 (m, 4H), 1.86 (m, 2H), 1.70-1.67 (m, 2H).

Example 481

[7-(2-Methoxy-phenyl)-pyrrolo[2,1-f][1,2,4]triazin-2-yl]-[2-methoxy-4-(4-pyrrolidin-1-yl-piperidin-1-yl)-phenyl]-amine; compound with trifluoro-acetic acid The titled compound was prepared in an analogous fashion to Example 480 replacing N-[2-(2-Methanesulfinyl-pyrrolo[2,1-f][1,2,4]triazin-7-yl)-phenyl]-N-methyl-methanesulfonamide with 7-(2-Methoxy-phenyl)-2-methylsulfanyl-pyrrolo[2,1-f][1,2,4]triazine to give after purification via reverse phase HPLC [7-(2-Methoxy-phenyl)-pyrrolo[2,1-f][1,2,4]triazin-2-yl]-[2-methoxy-4-(4-pyrrolidin-1-yl-piperidin-1-yl)-phenyl]-amine; compound with trifluoro-acetic acid as a brown lyophylate (4 mg, 3%). LC/MS (E/I+) 499.19 (M+H). NMR $^1$H (DMSO-d$_6$)-9.52 (bs, 1H), 8.90 (s, 1H), 7.88-7.84 (m, 2H), 7.53 (s, 1H), 7.44-7.42 (m, 1H), 7.21-7.19 (d, 1H, 8.16 Hz), 7.11-7.09 (m, 1H), 6.96 (s, 1H), 6.92 (s, 1H), 6.69 (s, 1H), 6.43-6.40 (d, 1H, J=8.92 Hz), 3.86 (s, 3H), 3.80 (s, 3H), 3.75-3.3 (bm, TFA salt and water provided poor resolution), 3.25 (m, 1H), 3.11 (m, 2H), 2.70-2.64 (m, 2H), 2.13-1.99 (m, 7H), 1.71-1.68 (m, 2H), 1.71-1.68 (m, 2H).

Example 482

[4-(1,4-Dioxa-8-aza-spiro[4.5]dec-8-yl)-2-methoxy-phenyl]-[7-(2-methoxy-phenyl)-pyrrolo[2,1-f][1,2,4]triazin-2-yl]-amine; compound with trifluoro-acetic acid a) 8-(3-Methoxy-4-nitro-phenyl)-1,4-dioxa-8-aza-spiro[4.5]decane was prepared in an analogous fashion to Example 460a replacing (S)-Piperidine-3-carboxylic acid with 1,4-Dioxa-8-aza-spiro[4.5]decane. The workup varied in that post-reaction, the reaction was simply poured into water and the resulting solid was filtered and rinsed liberally with water. The resulting desired product solid was air dried (3.30 g, 96%). LC/MS (E/I+) 295.10 (M+H).

b) 4-(1,4-Dioxa-8-aza-spiro[4.5]dec-8-yl)-2-methoxy-phenylamine was prepared in an analogous fashion to [(S)-1-(4-Amino-3-methoxy-phenyl)-piperidin-3-yl]-(4-methyl-piperazin-1-yl)-methanone of Example 460c replacing [(S)-1-(3-Methoxy-4-nitro-phenyl)-piperidin-3-yl]-(4-methyl-piperazin-1-yl)-methanone with 8-(3-Methoxy-4-nitro-phenyl)-1,4-dioxa-8-aza-spiro[4.5]decane (1.25 g, 93%). LC/MS (E/I+) 265.08 (M+H).

c) The titled compound was prepared in an analogous fashion to Example 481 replacing 2-Methoxy-4-(4-pyrrolidin-1-yl-piperidin-1-yl)-phenylamine with 4-(1,4-Dioxa-8-aza-spiro[4.5]dec-8-yl)-2-methoxy-phenylamine to give after purification via reverse phase HPLC [4-(1,4-Dioxa-8-aza-spiro[4.5]dec-8-yl)-2-methoxy-phenyl]-[7-(2-methoxy-phenyl)-pyrrolo[2,1-f][1,2,4]triazin-2-yl]-amine; compound with trifluoro-acetic acid as a brown lyophylate (202 mg, 55%). LC/MS (E/I+) 488.17 (M+H). NMR $^1$H (DMSO-$d_6$)-8.93 (s, 1H), 7.95 (bm, 1H), 7.82-7.80 (d, 1H, J=7.42 Hz), 7.60 (bs, 1H), 7.47-7.43 (m, 1H), 7.22-7.20 (d, 1H, J=8.15 Hz), 7.12-7.09 (m, 1H), 6.96 (bm, 1H), 6.94 (bm, 1H), 6.85 (bm, 1H), 6.75 (bm, 1H), 3.94 (s, 4H), 3.88 (s, 3H), 3.79 (s, 3H), 3.34 (bs, 4H), 1.83 (bs, 4H).

Example 483

(S)-1-(1-{3-Methoxy-4-[7-(2-methoxy-phenyl)-pyrrolo[2,1-f][1,2,4]triazin-2-ylamino]-phenyl}-piperidin-4-yl)-pyrrolidin-3-ol; compound with trifluoro-acetic acid a) (S)-1-[1-(3-Methoxy-4-nitro-phenyl)-piperidin-4-yl]-pyrrolidin-3-ol was prepared in an analogous fashion to [1-(3-Methoxy-4-nitro-phenyl)-piperidine-4-yl]dimethyl-amine of Example 475a replacing Dimethylamine with (S)-Pyrrolidin-3-ol. The crude material was purified via trituration with $Et_2O$ to yield a yellow solid, MP 137-139° C. (197 mg, 51%). LC/MS (E/I+) 322.14 (M+H).

b) (S)-1-[1-(4-Amino-3-methoxy-phenyl)-piperidin-4-yl]-pyrrolidin-3-ol was prepared in an analogous fashion to [(S)-1-(4-Amino-3-methoxy-phenyl)-piperidin-3-yl]-(4-methyl-piperazin-1-yl)-methanone of Example 460c replacing [(S)-1-(3-Methoxy-4-nitro-phenyl)-piperidin-3-yl]-(4-methyl-piperazin-1-yl)-methanone with (S)-1-[1-(3-Methoxy-4-nitro-phenyl)-piperidin-4-yl]-pyrrolidin-3-ol (150 mg, 99%). LC/MS (E/I+) 292.15 (M+H).

c) The titled compound was prepared in an analogous fashion to Example 479 replacing (R)-1-[1-(4-Amino-3-methoxy-phenyl)-piperidin-4-yl]-pyrrolidin-3-ol with (S)-1-[1-(4-Amino-3-methoxy-phenyl)-piperidin-4-yl]-pyrrolidin-3-ol to give after purification via reverse phase HPLC (S)-1-[1-(4-Amino-3-methoxy-phenyl)-piperidin-4-yl]-pyrrolidin-3-ol as a brown lyophylate (3 mg, 3%). LC/MS (E/I+) 515.21 (M+H). NMR $^1$H (DMSO-$d_6$)-9.8 (bs, 0.5H), 9.65 (bs, 0.5H), 8.90 (s, 1H), 7.89-7.83 (m, 2H), 7.53 (s, 1H), 7.46-7.42 (m, 1H), 7.21-7.19 (d, 1H, J=8.38 Hz), 7.11-7.08 (m, 1H), 6.96 (s, 1H), 6.92 (s, 1H), 6.69 (s, 1H), 6.43 (bm, 1H), 5.75 (bs, 1H), 4.48-4.40 (m, 1H), 3.86 (s, 3H), 3.80 (s, 3H), 3.70-3.20 (bm, TFA salt and water provided poor resolution), 2.67-2.50 (bm, 2H), 2.33-1.70 (m, 6H).

Example 484

(1-{4-[7-(4-Chloro-2-methoxy-phenyl)-pyrrolo[2,1-f][1,2,4]triazin-2-ylamino]-phenyl}-piperidin-4-yl)-(4-methyl-piperazin-1-yl)-methanone; compound with trifluoro-acetic acid a) 7-(4-Chloro-2-methoxy-phenyl)-2-methanesulfanyl-pyrrolo[2,1-f][1,2,4]triazine was prepared in an analogous fashion to Example 47a replacing 2-methoxybenzeneboronic acid with 2-Methoxy-4-chlorobenzeneboronic acid to give after purification via normal phase chromatography (EtOAc/hexane as eluant) 7-(4-Chloro-2-methoxy-phenyl)-2-methanesulfanyl-pyrrolo[2,1-f][1,2,4]triazine as a yellow solid (1.81 g, 71%). LC/MS (E/I+) 306.07 (M+H).

b) 7-(4-Chloro-2-methoxy-phenyl)-2-methanesulfinyl-pyrrolo[2,1-f][1,2,4]triazine was prepared in an analogous fashion to Example 47b replacing 7-(2-Methoxy-phenyl)-2-methylsulfanyl-pyrrolo[2,1-f][1,2,4]triazine with 7-(4-Chloro-2-methoxy-phenyl)-2-methanesulfanyl-pyrrolo[2,1-f][1,2,4]triazine to give 7-(4-Chloro-2-methoxy-phenyl)-2-methanesulfinyl-pyrrolo[2,1-f][1,2,4]triazine as a foamy material, which was used without further manipulation (1.74 g, 100%). LC/MS (E/I+) 322.05 (M+H).

c) The title compound was prepared in an analogous fashion to Example 444c after replacing 2-Methanesulfinyl-7-(2-methoxy-phenyl)-5-methyl-pyrrolo[2,1-f][1,2,4]triazine with 7-(4-Chloro-2-methoxy-phenyl)-2-methanesulfinyl-pyrrolo[2,1-f][1,2,4]triazine to give after purification via reverse phase HPLC (1-{4-[7-(4-Chloro-2-methoxy-phenyl)-pyrrolo[2,1-f][1,2,4]triazin-2-ylamino]-phenyl}-piperidin-4-yl)-(4-methyl-piperazin-1-yl)-methanone; compound with trifluoro-acetic acid as a brown lyophylate (3 mg, 3%). LC/MS (E/I+) 515.21 (M+H). NMR $^1$H (DMSO-$d_6$)-9.8 (bs, 1H), 9.5 (bs, 1H), 8.98 (s, 1H), 7.88-7.86 (d, 1H, J=8.27 Hz), 7.70 (bm, 3H), 7.31 (s, 1H), 7.21-7.19 (m, 2H), 6.98-6.97 (d, 1H, 4.63 Hz), 6.95-6.94 (d, 1H, 4.58 Hz), 4.5-3.9 (bm, TFA salt and water provided poor resolution), 3.85 (s, 3H), 3.64-3.2 (bm, TFA salt provided poor resolution), 2.94 (bm, 4H), 2.84 (s, 3H), 1.88 (bs, 4H).

Example 485

(1-{4-[7-(4-Chloro-2-hydroxy-phenyl)-pyrrolo[2,1-f][1,2,4]triazin-2-ylamino]-phenyl}-piperidin-4-yl)-(4-methyl-piperazin-1-yl)-methanone; compound with trifluoro-acetic acid The title compound came off as a side product in the reaction for Example 484c to give after purification via reverse phase HPLC (1-{4-[7-(4-Chloro-2-hydroxy-phenyl)-pyrrolo[2,1-f][1,2,4]triazin-2-ylamino]-phenyl}-piperidin-4-yl)-(4-methyl-piperazin-1-yl)-methanone; compound with trifluoro-acetic acid as a brown lyophylate (18 mg, 8%). LC/MS (E/I+) 546.21 (M+H). NMR $^1$H (DMSO-$d_6$)-10.4 (bs, 1H), 9.8 (bs, 1H), 8.96 (s, 1H), 7.96-7.94 (d, 1H, J=8.33 Hz), 7.73 (bm, 2H), 7.2 (bm, 1H), 7.08-7.04 (m, 4H), 6.94-

6.93 (d, 2H, J=4.47 Hz), 5.0-2.93 (bm, TFA salt and water provided poor resolution), 2.84 (s, 3H), 1.86 (bs, 4H).

Example 486

[7-(4-Chloro-2-methoxy-phenyl)-pyrrolo[2,1-f][1,2,4]triazin-2-yl]-[2-methoxy-4-(4-morpholin-4-yl-piperidin-1-yl)-phenyl]-amine; compound with trifluoro-acetic acid The titled compound was prepared in an analogous fashion to Example 484c replacing [1-(4-Amino-phenyl)-piperidin-4-yl]-(4-methyl-piperazin-1-yl)-methanone with 2-Methoxy-4-(4-morpholin-4-yl-piperidin-1-yl)-phenylamine to give after purification via reverse phase HPLC [7-(4-Chloro-2-methoxy-phenyl)-pyrrolo[2,1-f][1,2,4]triazin-2-yl]-[2-methoxy-4-(4-morpholin-4-yl-piperidin-1-yl)-phenyl]-amine; compound with trifluoro-acetic acid as a brown lyophylate (71 mg, 32%). LC/MS (E/I+) 549.19 (M+H). NMR $^1$H (DMSO-d$_6$)-9.75 (bs, 1H), 8.92 (s, 1H), 7.92-7.90 (d, 1H, J=8.31 Hz), 7.79-7.77 (d, 1H, J=8.76 Hz), 7.63 (s, 1H), 7.27 (s, 1H), 7.16-7.14 (d, 1H, J=8.32 Hz), 6.98-6.97 (d, 1H, J=4.67 Hz), 6.92-6.90 (d, 1H, J=4.70 Hz), 6.71 (s, 1H), 6.51-6.49 (d, 1H, J=7.85 Hz), 5-4.1 (bm, TFA salt and water provided poor resolution), 4.05-4.02 (d, 2H, J=12.65 Hz), 3.85-3.83 (m, 8H), 3.70-3.65 (m, 2H), 3.51-3.48 (d, 2H, J=11.85 Hz), 3.30 (m, 1H), 3.13 (m, 2H), 2.76-2.70 (m, 2H), 2.17-2.15 (d, 2H, J=11.10 Hz), 1.74-1.72 (m, 2H).

Example 487

(S)-1-(4-{4-[7-(4-Chloro-2-methoxy-phenyl)-pyrrolo[2,1-f][1,2,4]triazin-2-ylamino]-3-methoxy-phenyl}-piperazin-1-yl)-propan-2-ol; compound with trifluoro-acetic acid The titled compound was prepared in an analogous fashion to Example 484c replacing [1-(4-Amino-phenyl)-piperidin-4-yl]-(4-methyl-piperazin-1-yl)-methanone with (S)-1-[4-(4-Amino-3-methoxy-phenyl)-piperazin-1-yl]-propan-2-ol to give after purification via reverse phase HPLC [7-(4-Chloro-2-methoxy-phenyl)-pyrrolo[2,1-f][1,2,4]triazin-2-yl]-[2-methoxy-4-(4-morpholin-4-yl-piperidin-1-yl)-phenyl]-amine; compound with trifluoro-acetic acid as a brown lyophylate (71 mg, 32%). LC/MS (E/I+) 549.19 (M+H). NMR $^1$H (DMSO-d$_6$)-9.5 (bs, 1H), 8.92 (s, 1H), 7.91-7.89 (d, 1H, J=8.31 Hz), 7.83-7.81 (d, 1H, J=8.74 Hz), 7.64 (s, 1H), 7.27 (s, 1H), 7.16-7.14 (m, 1H), 6.99-6.97 (d, 1H, 4.67 Hz), 6.92-6.91 (d, 1H, 4.68 Hz), 6.73-6.72 (d, 1H, J=2.42 Hz), 6.50-6.47 (m, 1H), 4.14-4.12 (m, 1H), 3.86 (s, 3H), 3.83 (s, 3H), 3.78-3.74 (m, 4H), 3.6-3.3 (bm, TFA salt and water provided poor resolution), 3.22-2.99 (m, 7H), 1.16-1.14 (d, 3H, J=6.16H).

Example 488

{2-Methoxy-4-[2-(4-methyl-piperazin-1-yl)-ethyl]-phenyl}-[7-(2-methoxy-phenyl)-pyrrolo[2,1-f][1,2,4]triazin-2-yl]-amine; compound with trifluoro-acetic acid The title compound was prepared by warming a mixture of 2-Methanesulfinyl-7-(2-methoxy-phenyl)-pyrrolo[2,1-f][1,2,4]triazine (93 mg, 0.324 mmol), 2-Methoxy-4-[2-(4-methyl-piperazin-1-yl)-ethyl]-phenylamine (161 mg, 0.547 mmol) (prepared in similar manner as described in WO2008150799), and Methanesulfonic acid (63uL, 0.97 mmol) in 1-Methoxy-2-propanol (1.90 mL) at 135° C. in a sealed flask for 10 days. The mixture was then cooled and partitioned between CHCl$_3$ and saturated aqueous NaHCO$_3$. The organic phase was dried over Na$_2$SO$_4$, filtered, and concentrated under reduced pressure. The crude product gave after purification via reverse phase HPLC {2-Methoxy-4-[2-(4-methyl-piperazin-1-yl)-ethyl]-phenyl}-[7-(2-methoxy-phenyl)-pyrrolo[2,1-f][1,2,4]triazin-2-yl]-amine; compound with trifluoro-acetic acid as a brown lyophylate (42 mg, 27%). LC/MS (E/I+) 473.20 (M+H). NMR $^1$H (DMSO-d$_6$)-8.95 (s, 1H), 8.09-8.07 (d, 1H, J=8.18 Hz), 7.81-7.79 (m, 1H), 7.64 (s, 1H), 7.49-7.45 (m, 1H), 7.22-7.20 (d, 1H, J=8.21 Hz), 7.13-7.09 (m, 1H), 6.99-6.95 (m, 3H), 6.75-6.73 (d, 1H, J=8.24 Hz), 4.5-4.0 (broad hump, TFA salt and water provided poor resolution), 3.89 (s, 3H), 3.79 (s, 3H), 3.6-3.4 (broad hump, TFA salt provided poor resolution), 3.26-3.22 (bm, 2H), 2.92-2.88 (m, 2H), 2.85 (s, 3H).

Example 489

{3-Methoxy-4-[7-(2-methoxy-phenyl)-pyrrolo[2,1-f][1,2,4]triazin-2-ylamino]-phenyl}-(4-methyl-piperazin-1-yl)-methanone; compound with trifluoro-acetic acid a) (3-Methoxy-4-nitro-phenyl)-(4-methyl-piperazin-1-yl)-methanone was prepared in a similar manner as N-(2-Dimethylamino-ethyl)-4-[2-(4-morpholin-4-yl-phenylamino)-pyrrolo[2,1-f][1,2,4]triazin-7-yl]-benzamide of Example 52 after: substituting N-Me-piperazine for N,N-dimethyl-1,2-Ethanediamine, and substituting 3-Methoxy-4-nitro-benzoic acid for 4-[2-(4-Morpholin-4-yl-phenylamino)-pyrrolo[2,1-f][1,2,4]triazin-7-yl]-benzoic acid.

b) (4-Amino-3-methoxy-phenyl)-(4-methyl-piperazin-1-yl)-methanone was prepared in an analogous fashion to [(S)-1-(4-Amino-3-methoxy-phenyl)-piperidin-3-yl]-(4-methyl-piperazin-1-yl)-methanone of Example 460c replacing [(S)-1-(3-Methoxy-4-nitro-phenyl)-piperidin-3-yl]-(4-methyl-piperazin-1-yl)-methanone with (3-Methoxy-4-nitro-phenyl)-(4-methyl-piperazin-1-yl)-methanone.

c) The titled compound was prepared in an analogous fashion to Example 487 replacing 2-Methoxy-4-[2-(4-methyl-piperazin-1-yl)-ethyl]-phenylamine with (4-Amino-3-methoxy-phenyl)-(4-methyl-piperazin-1-yl)-methanone to give after purification via reverse phase HPLC {3-Methoxy-4-[7-(2-methoxy-phenyl)-pyrrolo[2,1-f][1,2,4]triazin-2-ylamino]-phenyl}-(4-methyl-piperazin-1-yl)-methanone; compound with trifluoro-acetic acid as a brown lyophylate (7 mg, 4%). LC/MS (E/I+) 473.18 (M+H). NMR $^1$H (DMSO-d$_6$)-9.9 (bs, 1H), 9.00 (s, 1H), 8.25-8.23 (d, 1H, J=8.28 Hz), 7.84 (s, 1H), 7.79-7.77 (m, 1H), 7.55-7.45 (m, 1H), 7.25-7.22 (d, 1H, J=8.32 Hz), 7.13-7.09 (m, 2H), 7.01-6.94 (m, 3H), 4.25 (broad hump, TFA salt provided poor resolution), 3.93 (s, 3H), 3.80 (s, 3H), 3.75-3.3 (bm, TFA salt and water provided poor resolution), 3.09 (bs, 2H), 2.84 (s, 3H).

Example 490

N-(2-{2-[2-Methoxy-4-(4-methyl-piperazine-1-carbonyl)-phenylamino]-pyrrolo[2,1-f][1,2,4]triazin-7-yl}-phenyl)-N-methyl-methanesulfonamide; compound with trifluoro-acetic acid The titled compound was prepared in an analogous fashion to Example 489c replacing 7-(2-Methoxy-phenyl)-2-methylsulfanyl-pyrrolo[2,1-f][1,2,4]triazine with N-[2-(2-Methanesulfinyl-pyrrolo[2,1-f][1,2,4]triazin-7-yl)-phenyl]-N-methyl-methanesulfonamide to give after purification via reverse phase HPLC N-(2-{2-[2-Methoxy-4-(4-methyl-piperazine-1-carbonyl)-phenylamino]-pyrrolo[2,1-f][1,2,4]triazin-7-yl}-phenyl)-N-methyl-methanesulfonamide; compound with trifluoro-acetic acid as a brown lyophylate (6 mg, 4%). LC/MS (E/I+) 550.15 (M+H). NMR $^1$H (DMSO-d$_6$)-9.95 (bs, 1H), 9.02 (s, 1H), 8.13-8.11 (d, 1H, J=8.25 Hz), 8.01-7.88 (m, 1H), 7.91 (s, 1H), 7.67-7.58 (m, 1H), 7.58-7.55 (m, 2H), 7.09-7.01 (m, 3H), 6.95-6.93 (m, 1H), 4.25 (broad hump, TFA salt provided poor resolution), 3.91 (s, 3H), 3.5-3.2 (broad hump, TFA salt and water provided poor resolution), 3.09 (s, 3H), 3.05-2.95 (broad hump, TFA salt provided poor resolution), 2.90 (s, 3H), 2.83 (s, 3H).

Example 491

N-[2-(2-{2-Methoxy-4-[2-(4-methyl-piperazin-1-yl)-ethyl]-phenylamino}-pyrrolo[2,1-f][1,2,4]triazin-7-yl)-phenyl]-N-methyl-methanesulfonamide; compound with trifluoro-acetic acid The titled compound was prepared in an analogous fashion to Example 488 replacing 7-(2-Methoxy-phenyl)-2-methyl-sulfanyl-pyrrolo[2,1-f][1,2,4]triazine with N-[2-(2-Methane-sulfinyl-pyrrolo[2,1-f][1,2,4]triazin-7-yl)-phenyl]-N-methyl-methanesulfonamide to give after purification via reverse phase HPLC N-[2-(2-{2-Methoxy-4-[2-(4-methyl-piperazin-1-yl)-ethyl]-phenylamino}-pyrrolo[2,1-f][1,2,4]triazin-7-yl)-phenyl]-N-methyl-methanesulfonamide; compound with trifluoro-acetic acid as a brown lyophylate (42 mg, 28%). LC/MS (E/I+) 550.19 (M+H). NMR $^1$H (DMSO-d$_6$)-8.97 (s, 1H), 7.99-7.96 (m, 1H), 7.93-7.91 (d, 1H, J=8.15 Hz), 7.71 (s, 1H), 7.67-7.65 (m, 1H), 7.56-7.53 (m, 2H), 7.02-6.94 (m, 3H), 6.72-6.70 (d, 1H, J=8.15 Hz), 4.75-3.90 (broad hump, TFA salt provided poor resolution), 3.87 (s, 3H), 3.75-3.10 (broad hump, TFA salt provided poor resolution), 3.08 (s, 3H), 2.88 (s, 3H), 2.85-2.83 (bm, TFA salt provided poor resolution), 2.80 (s, 3H).

Example 492

[2-Methoxy-4-(2-morpholin-4-yl-ethyl)-phenyl]-[7-(2-methoxy-phenyl)-pyrrolo[2,1-f][1,2,4]triazin-2-yl]-amine; compound with trifluoro-acetic acid a) 2-Methoxy-4-(2-morpholin-4-yl-ethyl)-phenylamine was prepared in a similar manner as 2-Methoxy-4-[2-(4-methyl-piperazin-1-yl)-ethyl]-phenylamine of Example 488 replacing 1-Methyl-piperazine with morpholine. LC/MS (E/I+) 237.07 (M+H).

b) The titled compound was prepared in an analogous fashion to Example 488 replacing 2-Methoxy-4-[2-(4-methyl-piperazin-1-yl)-ethyl]-phenylamine with 2-Methoxy-4-(2-morpholin-4-yl-ethyl)-phenylamine to give after purification via reverse phase HPLC [2-Methoxy-4-(2-morpholin-4-yl-ethyl)-phenyl]-[7-(2-methoxy-phenyl)-pyrrolo[2,1-f][1,2,4]triazin-2-yl]-amine; compound with trifluoro-acetic acid as a brown lyophylate (21 mg, 17%). LC/MS (E/I+) 460.20 (M+H). NMR $^1$H (DMSO-d$_6$)-10.05 (bs, 1H), 8.96 (s, 1H), 8.10-8.08 (d, 1H, J=8.19 Hz), 7.82-7.79 (m, 1H), 7.65 (s, 1H), 7.49-7.45 (m, 1H), 7.23-7.21 (d, 1H, J=8.21 Hz), 7.13-7.09 (m, 1H), 6.99-6.96 (m, 3H), 6.76-6.73 (m, 1H), 4.02-3.90 (broad hump, TFA salt and water provided poor resolution), 3.89 (s, 3H), 3.80 (s, 3H), 3.71-3.65 (m, 2H), 3.52-3.49 (m, 2H), 3.38-3.34 (m, 2H), 3.12 (bm, 2H), 2.97-2.93 (m, 2H).

Example 493

N-(2-{2-[2-Methoxy-4-(2-morpholin-4-yl-ethyl)-phenylamino]-pyrrolo[2,1-f][1,2,4]triazin-7-yl}-phenyl)-N-methyl-methanesulfonamide; compound with trifluoro-acetic acid The titled compound was prepared in an analogous fashion to Example 492 replacing 7-(2-Methoxy-phenyl)-2-methyl-sulfanyl-pyrrolo[2,1-f][1,2,4]triazine with N-[2-(2-Methane-sulfinyl-pyrrolo[2,1-f][1,2,4]triazin-7-yl)-phenyl]-N-methyl-methanesulfonamide to give after purification via reverse phase HPLC N-(2-{2-[2-Methoxy-4-(2-morpholin-4-yl-ethyl)-phenylamino]-pyrrolo[2,1-f][1,2,4]triazin-7-yl}-phenyl)-N-methyl-methanesulfonamide; compound with trifluoro-acetic acid as a brown lyophylate (18 mg, 14%). LC/MS (E/I+) 537.17 (M+H). NMR $^1$H (DMSO-d$_6$)-10.10 (bs, 1H), 8.97 (s, 1H), 7.99-7.94 (m, 2H), 7.73 (s, 1H), 7.68-7.65 (m, 1H), 7.56-7.54 (m, 2H), 7.02-6.96 (m, 3H), 6.74-6.72 (d, 1H, J=8.25 Hz), 4.75-4.10 (broad hump, TFA salt and water provided poor resolution), 4.03-4.00 (m, 2H), 3.88 (s, 3H), 3.71-3.65 (m, 2H), 3.52-3.49 (m, 2H), 3.38-3.34 (m, 2H), 3.12 (bm, 2H), 3.08 (s, 3H), 2.97-2.93 (m, 3H), 2.88 (s, 3H).

Example 494

{4-Methoxy-3-[7-(2-methoxy-phenyl)-pyrrolo[2,1-f][1,2,4]triazin-2-ylamino]-phenyl}-(4-methyl-piperazin-1-yl)-methanone; compound with trifluoro-acetic acid a) (4-Methoxy-3-nitro-phenyl)-(4-methyl-piperazin-1-yl)-methanone was prepared in a similar manner as N-(2-Dimethylamino-ethyl)-4-[2-(4-morpholin-4-yl-phenylamino)-pyrrolo[2,1-f][1,2,4]triazin-7-yl]-benzamide of Example 52 after: substituting N-Me-piperazine for N,N-dimethyl-1,2-Ethanediamine, and substituting 4-Methoxy-3-nitro-benzoic acid for 4-[2-(4-Morpholin-4-yl-phenylamino)-pyrrolo[2,1-f][1,2,4]triazin-7-yl]-benzoic acid. LC/MS (E/I+) 280.08 (M+H).

b) (3-Amino-4-methoxy-phenyl)-(4-methyl-piperazin-1-yl)-methanone was prepared in an analogous fashion to [(S)-1-(4-Amino-3-methoxy-phenyl)-piperidin-3-yl]-(4-methyl-piperazin-1-yl)-methanone of Example 460c replacing [(S)-1-(3-Methoxy-4-nitro-phenyl)-piperidin-3-yl]-(4-methyl-piperazin-1-yl)-methanone with (4-Methoxy-3-nitro-phenyl)-(4-methyl-piperazin-1-yl)-methanone. LC/MS (E/I+) 250.08 (M+H).

c) The titled compound was prepared in an analogous fashion to Example 1231 replacing (3-Amino-2-methoxy-phenyl)-(4-methyl-piperazin-1-yl)-methanone with (3-Amino-4-methoxy-phenyl)-(4-methyl-piperazin-1-yl)-methanone to give after purification via reverse phase HPLC {4-Methoxy-3-[7-(2-methoxy-phenyl)-pyrrolo[2,1-f][1,2,4]triazin-2-ylamino]-phenyl}-(4-methyl-piperazin-1-yl)-methanone; compound with trifluoro-acetic acid as a yellow lyophylate (4.1 mg, 46%). LC/MS (E/I+) 473.18 (M+H). NMR $^1$H (DMSO-d$_6$)-10.0 (bs, 1H), 8.98 (s, 1H), 8.13 (s, 1H), 7.81-7.77 (m, 2H), 7.47-7.43 (m, 1H), 7.15-6.98 (m, 6H), 3.93 (s, 3H), 3.90-3.80 (broad hump, TFA salt and water provided poor resolution), 3.77 (s, 3H), 3.5-3.2 (broad hump, 3H), 3.15-3.11 (bm, 2H), 2.90 (broad hump, 2H), 2.81 (s, 3H).

Example 495

[2-Methoxy-5-(4-methyl-piperazin-1-ylmethyl)-phenyl]-[7-(2-methoxy-phenyl)-pyrrolo[2,1-f][1,2,4]triazin-2-yl]-amine; compound with trifluoro-acetic acid a) 2-Methoxy-5-(4-methyl-piperazin-1-ylmethyl)-phenylamine. (3-Amino-4-methoxy-phenyl)-(4-methyl-piperazin-1-yl)-methanone (499 mg, 2.0 mmol) was added slowly to a room temperature mixture of LAH (455 mg, 12 mmol) in THF (12 mL). The resulting heterogeneous mixture was warmed to 60° C. for 16 hours. After cooling to 0° C., the mixture was treated carefully with 0.45 mL water in 2 mL of THF, followed by 0.45 mL of 15% NaOH, followed by 1.35 mL of water. The mixture was then warmed to rt and stirred for two days. The Al salts were filtered, rinsed with a small amount of THF, and the filtrate was then concentrated under reduced pressure to give desired 2-Methoxy-5-(4-methyl-piperazin-1-ylmethyl)-phenylamine as a brown oil (0.39 g, 83%) which was used for subsequent step without further manipulation. LC/MS (E/I+) 236.08 (M+H).

b) The titled compound was prepared in an analogous fashion to Example 1231 replacing (3-Amino-2-methoxy-phenyl)-(4-methyl-piperazin-1-yl)-methanone with 2-Methoxy-5-(4-methyl-piperazin-1-ylmethyl)-phenylamine to give after purification via reverse phase HPLC [2-Methoxy-5-(4-methyl-piperazin-1-ylmethyl)-phenyl]-[7-(2-methoxy-phenyl)-pyrrolo[2,1-f][1,2,4]triazin-2-yl]-amine; compound with trifluoro-acetic acid as a yellow lyophylate (21 mg, 24%). LC/MS (E/I+) 459.16 (M+H). NMR $^1$H (DMSO-d$_6$)-8.97 (s, 1H), 8.07-8.06 (d, 1H, J=1.71 Hz), 7.79-7.77 (d, 1H, J=7.56 Hz), 7.69 (s, 1H), 7.50 (m, 1H), 7.25-7.23 (d, 1H, J=8.30 Hz), 7.17-7.15 (m, 1H), 7.04-7.02 (d, 1H, J=8.32 Hz), 6.98-6.94 (m, 3H), 3.89 (s, 3H), 3.78 (s, 3H), 3.75-3.2 (bm, TFA salt and water provided poor resolution), 3.0-2.8 (bm, TFA salt provided poor resolution), 2.74 (s, 3H).

Example 496

N-(2-{2-[2-Methoxy-5-(4-methyl-piperazine-1-carbonyl)-phenylamino]-pyrrolo[2,1-f][1,2,4]triazin-7-yl}-phenyl)-N-methyl-methanesulfonamide; compound with trifluoro-acetic acid The titled compound was prepared in an analogous fashion to Example 1230 replacing (3-Amino-2-methoxy-phenyl)-(4-methyl-piperazin-1-yl)-methanone with (3-Amino-4-methoxy-phenyl)-(4-methyl-piperazin-1-yl)-methanone to give after purification via reverse phase HPLC N-(2-{2-[2-Methoxy-5-(4-methyl-piperazine-1-carbonyl)-phenylamino]-pyrrolo[2,1-f][1,2,4]triazin-7-yl}-phenyl)-N-methyl-methanesulfonamide; compound with trifluoro-acetic acid as a yellow lyophylate (39 mg, 38%). LC/MS (E/I+) 550.16 (M+H). NMR $^1$H (DMSO-d$_6$)-9.95 (bs, 1H), 9.00 (s, 1H), 8.02 (s, 1H), 7.91-7.89 (m, 2H), 7.64-7.62 (d, 1H, J=7.75 Hz), 7.54-7.51 (m, 1H), 7.47-7.43 (m, 1H), 7.10 (m, 2H), 7.02-6.99 (m, 2H), 3.90 (s, 3H), 3.85-3.5 (broad hump, TFA salt and water provided poor resolution), 3.40 (bs, 2H), 3.15 (bm, 2H), 3.09 (s, 3H), 2.96 (bs, 2H), 2.86 (s, 3H), 2.82 (s, 3H).

Example 497

N-(2-{2-[2-Methoxy-5-(4-methyl-piperazin-1-ylmethyl)-phenylamino]-pyrrolo[2,1-f][1,2,4]triazin-7-yl}-phenyl)-N-methyl-methanesulfonamide; compound with trifluoro-acetic acid The titled compound was prepared in an analogous fashion to Example 1230 replacing (3-Amino-2-methoxy-phenyl)-(4-methyl-piperazin-1-yl)-methanone with 2-Methoxy-5-(4-methyl-piperazin-1-ylmethyl)-phenylamine to give after purification via reverse phase HPLC N-(2-{2-[2-Methoxy-5-(4-methyl-piperazin-1-ylmethyl)-phenylamino]-pyrrolo[2,1-f][1,2,4]triazin-7-yl}-phenyl)-N-methyl-methanesulfonamide; compound with trifluoro-acetic acid as a yellow lyophylate (36 mg, 36%). LC/MS (E/I+) 536.16 (M+H). NMR $^1$H (DMSO-d$_6$)-9.00 (s, 1H), 7.96 (s, 1H), 7.89-7.87 (m, 1H), 7.76 (s, 1H), 7.69-7.68 (m, 1H), 7.59-7.58 (m, 2H), 7.03-6.92 (m, 4H), 4.2-3.2 (bm, TFA salt and water provided poor resolution), 3.09 (s, 3H), 3.0-2.85 (bm, TFA salt and water provided poor resolution), 2.81 (s, 3H), 2.74 (s, 3H).

Example 498

N-{2-[2-(2-Methoxy-5-morpholin-4-ylmethyl-phenylamino)-pyrrolo[2,1-f][1,2,4]triazin-7-yl]-phenyl}-N-methyl-methanesulfonamide; compound with trifluoro-acetic acid a) (4-Methoxy-3-nitro-phenyl)-morpholin-4-yl-methanone was prepared in an analogous fashion to N-(2-Dimethylamino-ethyl)-4-[2-(4-morpholin-4-yl-phenylamino)-pyrrolo[2,1-f][1,2,4]triazin-7-yl]-benzamide of Example 52 after: substituting morpholine for N,N-dimethyl-1,2-Ethanediamine, and substituting 4-Methoxy-3-nitro-benzoic acid for 4-[2-(4-Morpholin-4-yl-phenylamino)-pyrrolo[2,1-f][1,2,4]triazin-7-yl]-benzoic acid (2.14 g, 80%).

b) (3-Amino-4-methoxy-phenyl)-morpholin-4-yl-methanone was prepared in an analogous fashion to [(S)-1-(4-Amino-3-methoxy-phenyl)-piperidin-3-yl]-(4-methyl-piperazin-1-yl)-methanone of Example 460c replacing [(S)-1-(3-Methoxy-4-nitro-phenyl)-piperidin-3-yl]-(4-methyl-piperazin-1-yl)-methanone with (4-Methoxy-3-nitro-phenyl)-morpholin-4-yl-methanone. LC/MS (E/I+) 237.05 (M+H).

c) 2-Methoxy-5-morpholin-4-ylmethyl-phenylamine was prepared in an analogous fashion to 2-Methoxy-5-(4-methyl-piperazin-1-ylmethyl)-phenylamine of Example 495a replacing (3-Amino-4-methoxy-phenyl)-(4-methyl-piperazin-1-yl)-methanone with (3-Amino-4-methoxy-phenyl)-morpholin-4-yl-methanone (1.31 g, 73%). LC/MS (E/I+) 223.05 (M+H).

d) The titled compound was prepared in an analogous fashion to Example 1230 replacing (3-Amino-2-methoxy-phenyl)-(4-methyl-piperazin-1-yl)-methanone with 2-Methoxy-5-morpholin-4-ylmethyl-phenylamine to give after purification via reverse phase HPLC N-{2-[2-(2-Methoxy-5-morpholin-4-ylmethyl-phenylamino)-pyrrolo[2,1-f][1,2,4]triazin-7-yl]-phenyl}-N-methyl-methanesulfonamide; compound with trifluoro-acetic acid as a yellow lyophylate (43 mg, 44%). LC/MS (E/I+) 523.15 (M+H). NMR $^1$H (DMSO-d$_6$)-9.95 (bs, 1H), 9.01 (s, 1H), 8.09 (s, 1H), 7.94-7.91 (m, 2H), 7.70-7.68 (m, 1H), 7.68-7.61 (m, 2H), 7.15-7.12 (m, 2H), 7.01-6.99 (m, 2H), 4.02 (bs, 2H), 3.89 (s, 3H), 3.86 (bs, 2H), 3.75-3.25 (broad hump, TFA salt and water provided poor resolution), 3.12 (s, 3H), 3.09 (bs, 2H), 2.82 (s, 3H), 2.67 (bm, 2H).

Example 499

(2-Methoxy-5-morpholin-4-ylmethyl-phenyl)-[7-(2-methoxy-phenyl)-pyrrolo[2,1-f][1,2,4]triazin-2-yl]-amine; compound with trifluoro-acetic acid The titled compound was prepared in an analogous fashion to Example 1231 replacing (3-Amino-2-methoxy-phenyl)-

(4-methyl-piperazin-1-yl)-methanone with 2-Methoxy-5-morpholin-4-ylmethyl-phenylamine to give after purification via reverse phase HPLC (2-Methoxy-5-morpholin-4-ylmethyl-phenyl)-[7-(2-methoxy-phenyl)-pyrrolo[2,1-f][1,2,4]triazin-2-yl]-amine; compound with trifluoro-acetic acid as a yellow lyophylate (42 mg, 41%). LC/MS (E/I+) 446.16 (M+H). NMR $^1$H (DMSO-$d_6$)-9.90 (bs, 1H), 8.91 (s, 1H), 8.15 (s, 1H), 7.84-7.81 (m, 2H), 7.55-7.52 (m, 1H), 7.28-7.26 (d, 1H, J=8.27 Hz), 7.20-7.13 (m, 3H), 6.99 (s, 2H), 4.06 (bs, 2H), 3.91 (s, 3H), 3.88-3.85 (bm, 2H), 3.77 (s, 3H), 3.7-3.3 (broad hump, TFA salt and water provided poor resolution), 3.12-3.09 (bm, 2H), 2.8-2.65 (bm, 2H).

Example 500

(4-{4-[7-(2-Methoxy-phenyl)-pyrrolo[2,1-f][1,2,4]triazin-2-ylamino]-phenyl}-piperidin-1-yl)-(1-methyl-piperidin-4-yl)-methanone; compound with trifluoro-acetic acid a) (1-Methyl-piperidin-4-yl)-[4-(4-nitro-phenyl)-piperidin-1-yl]-methanone was prepared in an analogous fashion to N-(2-Dimethylamino-ethyl)-4-[2-(4-morpholin-4-yl-phenylamino)-pyrrolo[2,1-f][1,2,4]triazin-7-yl]-benzamide of Example 52 after: substituting 4-(4-nitrophenyl)-piperidine for N,N-dimethyl-1,2-Ethanediamine, and substituting 1-Methyl-4-piperidinecarboxylic acid for 4-[2-(4-Morpholin-4-yl-phenylamino)-pyrrolo[2,1-f][1,2,4]triazin-7-yl]-benzoic acid (0.40 g, 88%).

b) [4-(4-Amino-phenyl)-piperidin-1-yl]-(1-methyl-piperidin-4-yl)-methanone was prepared in an analogous fashion to [(S)-1-(4-Amino-3-methoxy-phenyl)-piperidin-3-yl]-(4-methyl-piperazin-1-yl)-methanone of Example 460c replacing [(S)-1-(3-Methoxy-4-nitro-phenyl)-piperidin-3-yl]-(4-methyl-piperazin-1-yl)-methanone with (1-Methyl-piperidin-4-yl)-[4-(4-nitro-phenyl)-piperidin-1-yl]-methanone. LC/MS (E/I+) 302.15 (M+H).

c) The titled compound was prepared in an analogous fashion to Example 1231 replacing (3-Amino-2-methoxy-phenyl)-(4-methyl-piperazin-1-yl)-methanone with [4-(4-Amino-phenyl)-piperidin-1-yl]-(1-methyl-piperidin-4-yl)-methanone to give after purification via reverse phase HPLC (4-{4-[7-(2-Methoxy-phenyl)-pyrrolo[2,1-f][1,2,4]triazin-2-ylamino]-phenyl}-piperidin-1-yl)-(1-methyl-piperidin-4-yl)-methanone; compound with trifluoro-acetic acid as a yellow lyophylate (54 mg, 41%). LC/MS (E/I+) 525.25 (M+H). NMR $^1$H (DMSO-$d_6$)-9.33 (s, 1H), 9.25 (bs, 1H), 8.95 (s, 1H), 7.82-7.80 (d, 1H, J=7.57 Hz), 7.65-7.62 (d, 2H, J=8.54 Hz), 7.49-7.45 (m, 1H), 7.24-7.21 (d, 1H, J=8.30 Hz), 7.14-7.11 (m, 1H), 7.09-7.06 (d, 2H, J=8.52 Hz), 6.95-6.91 (m, 2H), 4.55-4.52 (m, 1H), 4.4-3.9 (bm, TFA salt and water provided poor resolution), 3.80 (s, 3H), 3.47-3.44 (m, 2H), 3.12-2.92 (m, 4H), 2.81-2.60 (m, 5H), 1.87-1.80 (m, 6H), 1.6-1.35 (m, 2H).

Example 501

(4-{4-[7-(2-Methoxy-phenyl)-pyrrolo[2,1-f][1,2,4]triazin-2-ylamino]-phenyl}-piperidin-1-yl)-(4-methyl-piperazin-1-yl)-methanone; compound with trifluoro-acetic acid a) (4-Methyl-piperazin-1-yl)-[4-(4-nitro-phenyl)-piperidin-1-yl]-methanone. 4-(4-nitrophenyl)piperidine (4 g, 9.69 mmol) was taken in a mixture of toluene/methanol (5:2) and cooled to 0° C. when triethyl amine (2.9 mL, 21.3 mmol) was added dropwise followed by portion wise addition of 4-methylpiperazine-1-carbonyl chloride (2) (3.7 ml, 16.3 mmol) and the reaction was stirred at rt for 2 h. The reaction mixture was then concentrated, diluted with water, and extracted with DCM. The organic extract was dried, concentrated, and purified by column chromatography using silica gel (100-200 mesh) to afford (4-Methyl-piperazin-1-yl)-[4-(4-nitro-phenyl)-piperidin-1-yl]-methanone (4.9 g, 77%) as a white solid.

b) [4-(4-Amino-phenyl)-piperidin-1-yl]-(4-methyl-piperazin-1-yl)-methanone was prepared in an analogous fashion to [(S)-1-(4-Amino-3-methoxy-phenyl)-piperidin-3-yl]-(4-methyl-piperazin-1-yl)-methanone of Example 460c replacing [(S)-1-(3-Methoxy-4-nitro-phenyl)-piperidin-3-yl]-(4-methyl-piperazin-1-yl)-methanone with (4-Methyl-piperazin-1-yl)-[4-(4-nitro-phenyl)-piperidin-1-yl]-methanone.

c) The titled compound was prepared in an analogous fashion to Example 1231 replacing (3-Amino-2-methoxy-phenyl)-(4-methyl-piperazin-1-yl)-methanone with [4-(4-Amino-phenyl)-piperidin-1-yl]-(4-methyl-piperazin-1-yl)-methanone to give after purification via reverse phase HPLC (4-{4-[7-(2-Methoxy-phenyl)-pyrrolo[2,1-f][1,2,4]triazin-2-ylamino]-phenyl}-piperidin-1-yl)-(4-methyl-piperazin-1-yl)-methanone; compound with trifluoro-acetic acid as a yellow lyophylate (106 mg, 81%). LC/MS (E/I+) 526.23 (M+H). NMR $^1$H (DMSO-$d_6$)-9.78 (bs, 1H), 9.33 (s, 1H), 8.94 (s, 1H), 7.81-7.79 (m, 1H), 7.65-7.62 (d, 2H, J=8.51 Hz), 7.49-7.45 (m, 1H), 7.24-7.22 (d, 1H, J=8.31 Hz), 7.14-7.11 (m, 1H), 7.08-7.06 (d, 2H, J=8.51 Hz), 6.95-6.91 (m, 2H), 3.80 (s, 3H), 3.77-3.67 (m, 4H), 3.41-3.40 (m, 2H), 3.10-3.05 (m, 4H), 2.91-2.88 (m, 2H), 2.83 (s, 3H), 2.7-2.6 (m, 1H), 1.75-1.72 (m, 2H), 1.56-1.52 (m, 2H).

Example 502

N-Methyl-N-[2-(2-{4-[1-(1-methyl-piperidine-4-carbonyl)-piperidin-4-yl]-phenylamino}-pyrrolo[2,1-f][1,2,4]triazin-7-yl)-phenyl]-methanesulfonamide; compound with trifluoro-acetic acid The titled compound was prepared in an analogous fashion to Example 1230 replacing (3-Amino-2-methoxy-phenyl)-(4-methyl-piperazin-1-yl)-methanone with [4-(4-Amino-phenyl)-piperidin-1-yl]-(1-methyl-piperidin-4-yl)-methanone to give after purification via reverse phase HPLC N-Methyl-N-[2-(2-{4-[1-(1-methyl-piperidine-4-carbonyl)-piperidin-4-yl]-phenylamino}-pyrrolo[2,1-f][1,2,4]triazin-7-yl)-phenyl]-methanesulfonamide; compound with trifluoro-acetic acid as a yellow lyophylate (47 mg, 31%). LC/MS (E/I+) 602.22 (M+H). NMR $^1$H (DMSO-$d_6$)-9.36 (bs, 2H), 8.97 (s, 1H), 8.01-7.99 (d, 1H, J=7.41 Hz), 7.67-7.65 (d, 1H, J=8.72 Hz), 7.59-7.54 (m, 4H), 7.08-7.06 (d, 2H, J=8.49 Hz), 7.00-6.94 (m, 2H), 4.55-4.52 (m, 1H), 4.08-4.05 (m, 1H), 3.9-3.6 (broad hump, TFA salt and water provided poor resolution), 3.47-3.44 (m, 2H), 3.12-2.99 (m, 5H), 2.96-2.88 (m, 5H), 2.81-2.71 (m, 4H), 2.60 (m, 1H), 1.87-1.75 (m, 6H, 1.52 (m, 2H).

Example 503

N-Methyl-N-[2-(2-{4-[1-(4-methyl-piperazine-1-carbonyl)-piperidin-4-yl]-phenylamino}-pyrrolo[2,1-f][1,2,4]triazin-7-yl)-phenyl]-methanesulfonamide; compound with trifluoro-acetic acid The titled compound was prepared in an analogous fashion to Example 1230 replacing (3-Amino-2-methoxy-phenyl)-(4-methyl-piperazin-1-yl)-methanone with [4-(4-Aminophenyl)-piperidin-1-yl]-(4-methyl-piperazin-1-yl)-methanone to give after purification via reverse phase HPLC N-Methyl-N-[2-(2-{4-[1-(4-methyl-piperazine-1-carbonyl)-piperidin-4-yl]-phenylamino}-pyrrolo[2,1-f][1,2,4]triazin-7-yl)-phenyl]-methanesulfonamide; compound with trifluoro-acetic acid as a yellow lyophylate (55 mg, 36%). LC/MS (E/I+) 603.23 (M+H). NMR $^1$H (DMSO-d$_6$)-9.7 (bs, 1H), 9.36 (s, 1H), 8.97 (s, 1H), 8.01-7.99 (d, 1H, J=7.32 Hz), 7.67-7.65 (d, 1H, J=7.64 Hz), 7.59-7.55 (m, 4H), 7.07-7.05 (d, 2H, J=8.48 Hz), 7.00-6.99 (d, 1H, J=4.70 Hz), 6.95-6.94 (d, 1H, J=4.68 Hz), 3.76-3.66 (m, 4H), 3.41-3.39 (m, 2H), 3.10-3.05 (m, 7H), 2.90-2.87 (m, 5H), 2.83 (s, 3H), 2.63 (m, 1H), 1.75-1.71 (m, 2H), 1.54-1.52 (m, 2H).

Example 505

N-(2-{2-[2-Methoxy-4-(2-methyl-imidazol-1-ylmethyl)-phenylamino]-pyrrolo[2,1-f][1,2,4]triazin-7-yl}-phenyl)-N-methyl-methanesulfonamide; compound with trifluoro-acetic acid a) 1-(3-Methoxy-4-nitro-benzyl)-2-methyl-1H-imidazole.

At room temperature 2-Methyl-1H-imidazole (0.718 g, 8.75 mmol) was added to a solution of 4-Bromomethyl-2-methoxy-1-nitro-benzene (0.861 g, 3.50 mmol) in Chloroform (10 mL). After two days the mixture was extracted with saturated aqueous NaHCO$_3$. Washed aqueous phase with a second portion of CHCl$_3$, then dried combined organic phases over Na$_2$SO$_4$, filtered, and concentrated under reduced pressure. The residual solid was (0.68 g; 78%) used without further manipulation. LC/MS (E/I+) 248.02 (M+H).

b) 2-Methoxy-4-(2-methyl-imidazol-1-ylmethyl)-phenylamine was prepared in an analogous fashion to [(S)-1-(4-Amino-3-methoxy-phenyl)-piperidin-3-yl]-(4-methyl-piperazin-1-yl)-methanone of Example 460c replacing [(S)-1-(3-Methoxy-4-nitro-phenyl)-piperidin-3-yl]-(4-methyl-piperazin-1-yl)-methanone with 1-(3-Methoxy-4-nitro-benzyl)-2-methyl-1H-imidazole.

c) The titled compound was prepared in an analogous fashion to Example 1230 replacing (3-Amino-2-methoxy-phenyl)-(4-methyl-piperazin-1-yl)-methanone with 2-Methoxy-4-(2-methyl-imidazol-1-ylmethyl)-phenylamine to give after purification via reverse phase HPLC N-(2-{2-[2-Methoxy-4-(2-methyl-imidazol-1-ylmethyl)-phenylamino]-pyrrolo[2,1-f][1,2,4]triazin-7-yl}-phenyl)-N-methyl-methanesulfonamide; compound with trifluoro-acetic acid as a yellow lyophylate (56 mg, 58%). LC/MS (E/I+) 518.07 (M+H). NMR $^1$H (DMSO-d$_6$)-8.98 (s, 1H), 8.00-7.95 (m, 2H), 7.84 (s, 1H), 7.68-7.64 (m, 2H), 7.59-7.50 (m, 3H), 7.09 (s, 1H), 7.02-6.98 (m, 2H), 6.86-6.84 (d, 1H, J=8.36 Hz), 5.28 (s, 2H), 3.86 (s, 3H), 3.07 (s, 3H), 2.88 (s, 3H), 2.63 (s, 3H).

Example 506

[2-Methoxy-4-(2-methyl-imidazol-1-ylmethyl)-phenyl]-[7-(2-methoxy-phenyl)-pyrrolo[2,1-f][1,2,4]triazin-2-yl]-amine; compound with trifluoro-acetic acid The titled compound was prepared in an analogous fashion to Example 1231 replacing (3-Amino-2-methoxy-phenyl)-(4-methyl-piperazin-1-yl)-methanone with 2-Methoxy-4-(2-methyl-imidazol-1-ylmethyl)-phenylamine to give after purification via reverse phase [2-Methoxy-4-(2-methyl-imidazol-1-ylmethyl)-phenyl]-[7-(2-methoxy-phenyl)-pyrrolo[2,1-f][1,2,4]triazin-2-yl]-amine; compound with trifluoro-acetic acid as a yellow lyophylate (24 mg, 29%). LC/MS (E/I+) 441.06 (M+H). NMR $^1$H (DMSO-d$_6$)-8.97 (s, 1H), 8.13-8.12 (d, 1H, J=8.25 Hz), 7.80-7.78 (m, 1H), 7.76 (s, 1H), 7.68-7.67 (d, 1H, J=1.92 Hz), 7.58-7.57 (d, 1H, J=1.93 Hz), 7.48-7.44 (m, 1H), 7.21-7.19 (d, 1H, J=8.28 Hz), 7.10-7.07 (m, 2H), 7.00-6.97 (m, 2H), 6.90-6.88 (d, 1H, J=8.28 Hz), 5.28 (s, 2H), 3.88 (s, 3H), 3.78 (s, 3H), 2.64 (s, 3H).

Example 507

N-(2-{2-[2-Chloro-4-(4-methyl-piperazin-1-yl)-phenylamino]-pyrrolo[2,1-f][1,2,4]triazin-7-yl}-phenyl)-N-methyl-methanesulfonamide; compound with trifluoro-acetic acid a) 5-(4-Methyl-piperazin-1-yl)-2-nitro-phenylamine.

5-Fluoro-2-nitro-phenylamine (4.68 g, 30.0 mmol) and 1-Methylpiperazine (13.30 mL, 119.9 mmol) were combined at room temperature, then warmed to 60° C. After 30 minutes cooled reaction mixture to room temperature, then combined with 300 mL of water while stirring. The resulting solid was filtered and washed liberally with water. After air drying there remained 7.08 g (100%) of desired 5-(4-Methyl-piperazin-1-yl)-2-nitro-phenylamine as a yellow solid, which was used for subsequent step without further manipulation. LC/MS (E/I+) 237.06 (M+H).

b) 1-(3-Chloro-4-nitro-phenyl)-4-methyl-piperazine.

To room temperature Sulfuric acid (10 mL, 200 mmol) was added Sodium nitrite (1.14 g, 16.5 mmol) with vigorous stirring over two minutes (reaction warmed significantly and appeared got dissolution rather quickly). After 30 minutes the mixture had cooled to rt, and 5-(4-Methyl-piperazin-1-yl)-2-nitro-phenylamine (3.54 g, 15.0 mmol) was added portionwise, maintaining a temperature below 40° C. by cooling in a cooled water bath at ~15° C. After completion of addition, the red mixture was stirred at rt for 1.5 h. The dark red solution was added over 10 minutes to an ice cooled, pre-mixed solution of Cuprous monochloride (3.27 g, 33.0 mmol) in 12 M of Hydrogen Chloride in Water (30 mL, 400 mmol), focusing on maintaining a controlled effervescence. Upon completion of addition, the ice bath was removed and the reaction was stirred. After 1.5 h cooled reaction mixture in an ice bath, then treated with 40% NaOH. Was very viscous, so treated mix with 100 mL of water. The resulting solid was filtered and rinsed with water. After air drying there remained 6.42 g (167%) of crude 1-(3-Chloro-4-nitro-phenyl)-4-methyl-piperazine, which was used for subsequent step without further manipulation. LC/MS (E/I+) 256.04 (M+H).

c) 2-Chloro-4-(4-methyl-piperazin-1-yl)-phenylamine 1-(3-Chloro-4-nitro-phenyl)-4-methyl-piperazine (2.016 g, 7.885 mmol) was combined with Tetrahydrofuran (30 mL). The resulting mixture was filtered. The filtrate was combined with Acetic acid (40 mL, 700 mmol), then at room temperature Iron (2932 mg, 52.50 mmol) was added neat and the mixture was warmed to 35° C. under a nitrogen atmosphere. After 16 h filtered mixture and concentrated resulting filtrate under reduced pressure. The concentrated residue was partitioned between CHCl$_3$ (2×) and saturated aqueous NaHCO$_3$. Combined organics, dried over Na$_2$SO$_4$, filtered, and concentrated under reduced pressure to yield 0.44 g (25%) of 2-Chloro-4-(4-methyl-piperazin-1-yl)-phenylamine as a yellow tinted oil, which crystallized on sitting. This material was used without further manipulation for the subsequent step. LC/MS (E/I+) 226.05 (M+H).

d) The titled compound was prepared in an analogous fashion to Example 1230 replacing (3-Amino-2-methoxy-phenyl)-(4-methyl-piperazin-1-yl)-methanone with 2-Chloro-4-(4-methyl-piperazin-1-yl)-phenylamine to give after purification via reverse phase HPLC N-(2-{2-[2-Chloro-4-(4-methyl-piperazin-1-yl)-phenylamino]-pyrrolo[2,1-f][1,2,4]triazin-7-yl}-phenyl)-N-methyl-methanesulfonamide; compound with trifluoro-acetic acid as a yellow lyophylate (24 mg, 27%). LC/MS (E/I+) 526.14 (M+H). NMR $^1$H (DMSO-d$_6$)-9.75 (bs, 1H), 8.92 (s, 1H), 8.33 (s, 1H), 7.94-7.92 (m, 1H), 7.60-7.58 (d, 2H, J=8.64 Hz), 7.47-7.45 (m, 2H), 7.13-7.12 (m, 1H), 6.97-6.93 (m, 3H), 3.87-3.84 (m, 2H), 3.53-3.50 (m, 2H), 3.18 (bm, 2H), 3.08 (s, 3H), 2.96 (m, 3H), 2.87 (s, 3H), 2.85 (s, 3H).

Example 508

[2-Chloro-4-(4-methyl-piperazin-1-yl)-phenyl]-[7-(2-methoxy-phenyl)-pyrrolo[2,1-f][1,2,4]triazin-2-yl]-amine; compound with trifluoro-acetic acid The titled compound was prepared in an analogous fashion to Example 1231 replacing (3-Amino-2-methoxy-phenyl)-(4-methyl-piperazin-1-yl)-methanone with 2-Chloro-4-(4-methyl-piperazin-1-yl)-phenylamine to give after purification via reverse phase HPLC [2-Chloro-4-(4-methyl-piperazin-1-yl)-phenyl]-[7-(2-methoxy-phenyl)-pyrrolo[2,1-f][1,2,4]triazin-2-yl]-amine; compound with trifluoro-acetic acid as a tan lyophylate (22 mg, 23%). LC/MS (E/I+) 449.17 (M+H). NMR $^1$H (DMSO-d$_6$)-9.8 (bs, 1H), 8.22 (s, 1H), 8.19 (s, 1H), 7.84-7.82 (d, 1H, J=7.63 Hz), 7.74-7.72 (d, 1H, J=8.94 Hz), 7.39-7.35 (m, 1H), 7.16-7.14 (m, 2H), 7.03-6.91 (m, 4H), 4.4-3.82 (bm, TFA salt and water provided poor resolution), 3.79 (s, 3H), 3.54-3.51 (m, 2H), 3.19-3.16 (m, 2H), 2.98-2.92 (m, 2H), 2.87 (s, 3H).

Example 509

[7-(2-Fluoro-6-methoxy-phenyl)-pyrrolo[2,1-f][1,2,4]triazin-2-yl]-[2-methoxy-4-(4-morpholin-4-yl-piperidin-1-yl)-phenyl]-amine; compound with trifluoro-acetic acid a) 7-(2-Fluoro-6-methoxy-phenyl)-2-methanesulfanyl-pyrrolo[2,1-f][1,2,4]triazine was prepared in an analogous fashion to Example 47a replacing 2-methoxybenzeneboronic acid with (2-Fluoro-6-methoxy-phenyl)-boronic acid.
b) 7-(2-Fluoro-6-methoxy-phenyl)-2-methanesulfinyl-pyrrolo[2,1-f][1,2,4]triazine was prepared in an analogous fashion to Example 47b replacing 7-(2-Methoxy-phenyl)-2-methylsulfanyl-pyrrolo[2,1-f][1,2,4]triazine with 7-(2-Fluoro-6-methoxy-phenyl)-2-methanesulfanyl-pyrrolo[2,1-f][1,2,4]triazine.
c) The title compound was prepared in an analogous fashion to Example 486 after replacing 7-(4-Chloro-2-methoxy-phenyl)-2-methanesulfinyl-pyrrolo[2,1-f][1,2,4]triazine with 7-(2-Fluoro-6-methoxy-phenyl)-2-methanesulfinyl-pyrrolo[2,1-f][1,2,4]triazine to give after purification via reverse phase HPLC [7-(2-Fluoro-6-methoxy-phenyl)-pyrrolo[2,1-f][1,2,4]triazin-2-yl]-[2-methoxy-4-(4-morpholin-4-yl-piperidin-1-yl)-phenyl]-amine; compound with trifluoro-acetic acid as a brown lyophylate (77 mg, 52%). LC/MS (E/I+) 533.0 (M+H). NMR $^1$H (DMSO-d$_6$)-8.93 (s, 1H), 7.81-7.79 (d, 1H, J=8.78 Hz), 7.57-7.51 (m, 2H), 7.07-7.05 (d, 1H, J=8.48 Hz), 7.03-6.99 (m, 1H), 6.95-6.93 (d, 1H, J=4.60 Hz), 6.84-6.83 (d, 1H, J=4.59 Hz), 6.70 (s, 1H), 6.39-6.37 (d, 1H, 7.75 Hz), 4.8-4.1 (broad hump, TFA salt and water provided poor resolution), 4.05-4.02 (m, 2H), 3.85 (s, 3H), 3.81-3.68 (m, 7H), 3.51-3.46 (m, 2H), 3.35 (m, 1H), 3.13 (bm, 2H), 2.73-2.67 (m, 2H), 2.16-2.13 (m, 2H), 1.74-1.71 (m, 2H).

Example 510

[7-(4-Fluoro-2-methoxy-phenyl)-pyrrolo[2,1-f][1,2,4]triazin-2-yl]-[2-methoxy-4-(4-morpholin-4-yl-piperidin-1-yl)-phenyl]-amine; compound with trifluoro-acetic acid a) 7-(4-Fluoro-2-methoxy-phenyl)-2-methanesulfanyl-pyrrolo[2,1-f][1,2,4]triazine was prepared in an analogous fashion to Example 47a replacing 2-methoxybenzeneboronic acid with (4-Fluoro-2-methoxy-phenyl)-boronic acid.
b) 7-(2-Fluoro-6-methoxy-phenyl)-2-methanesulfinyl-pyrrolo[2,1-f][1,2,4]triazine was prepared in an analogous fashion to Example 47b replacing 7-(2-Methoxy-phenyl)-2-methylsulfanyl-pyrrolo[2,1-f][1,2,4]triazine with 7-(4-Fluoro-2-methoxy-phenyl)-2-methanesulfanyl-pyrrolo[2,1-f][1,2,4]triazine.
c) The title compound was prepared in an analogous fashion to Example 486 after replacing 7-(4-Chloro-2-methoxy-phenyl)-2-methanesulfinyl-pyrrolo[2,1-f][1,2,4]triazine with 7-(4-Fluoro-2-methoxy-phenyl)-2-methanesulfinyl-pyrrolo[2,1-f][1,2,4]triazine to give after purification via reverse phase HPLC [7-(4-Fluoro-2-methoxy-phenyl)-pyrrolo[2,1-f][1,2,4]triazin-2-yl]-[2-methoxy-4-(4-morpholin-4-yl-piperidin-1-yl)-phenyl]-amine; compound with trifluoro-acetic acid as a brown lyophylate (91 mg, 61%). LC/MS (E/I+) 533.07 (M+H). NMR $^1$H (DMSO-d$_6$)-8.90 (s, 1H), 7.88-7.81 (m, 2H), 7.57 (s, 1H), 7.13-7.10 (d, 1H), 6.95-6.90 (m, 3H), 6.70 (s, 1H), 6.50-6.48 (d, 1H, J=7.93 Hz), 4.8-4.0 (bm, TFA salt and water provided poor resolution), 3.86-3.77 (m, 8H), 3.71-3.64 (m, 2H), 3.51-3.48 (m, 2H), 3.36 (m, 1H), 3.15 (m, 2H), 2.73-2.67 (m, 2H), 2.16-2.13 (m, 2H), 1.73-1.70 (m, 2H).

Example 511

2-{2-[2-Methoxy-4-(4-morpholin-4-yl-piperidin-1-yl)-phenylamino]-pyrrolo[2,1-f][1,2,4]triazin-7-yl}-benzonitrile; compound with trifluoro-acetic acid a) 2-(2-Methanesulfanyl-pyrrolo[2,1-f][1,2,4]triazin-7-yl)-benzonitrile.
To a stirred and degassed suspension of Palladium acetate (0.128 g, 0.573 mmol) and triphenylphosphine (0.097 g, 0.373 mmol) in 1,4-dioxane (20 mL), 7-bromo-2-(methylthio)pyrrolo[1,2-f][1,2,4]triazine (700 mg, 2.87 mmol), 2-(4,4,5,5-tetramethyl-1,3,2-dioxaborolan-2-yl)benzonitrile (1.18 g, 5.16 mmol)) and K$_3$PO$_4$ (0.973 g, 4.59 mmol) were added successively. The reaction mixture was then heated at 120° C. for 15 h. The reaction mixture was filtered through a bed of celite, washed well with ethyl acetate, concentrated, and purified by column chromatography using silica gel (100-200 mesh) to afford 2-(2-Methanesulfanyl-pyrrolo[2,1-f][1,2,4]triazin-7-yl)-benzonitrile (0.41 g, 54%) as a yellow solid.
b) 2-(2-Methanesulfinyl-pyrrolo[2,1-f][1,2,4]triazin-7-yl)-benzonitrile was prepared in an analogous fashion to Example 47b replacing 7-(2-Methoxy-phenyl)-2-methylsulfanyl-pyrrolo[2,1-f][1,2,4]triazine with 2-(2-Methanesulfanyl-pyrrolo[2,1-f][1,2,4]triazin-7-yl)-benzonitrile.
c) The title compound was prepared in an analogous fashion to Example 486 after replacing 7-(4-Chloro-2-methoxy-phenyl)-2-methanesulfinyl-pyrrolo[2,1-f][1,2,4]triazine with 2-(2-Methanesulfinyl-pyrrolo[2,1-f][1,2,4]triazin-7-yl)-benzonitrile to give after purification via reverse phase HPLC 2-{2-[2-Methoxy-4-(4-morpholin-4-yl-piperidin-1-yl)-phenylamino]-pyrrolo[2,1-f][1,2,4]triazin-7-yl}-benzonitrile; compound with trifluoro-acetic acid as a brown lyophylate (30 mg, 20%). LC/MS (E/I+) 510.05 (M+H). NMR $^1$H (DMSO-d$_6$)-9.03 (s, 1H), 8.10-8.08 (d, 1H, J=7.91 Hz), 8.03-8.01 (d, 1H, J=7.61 Hz), 7.88-7.84 (m, 1H), 7.79 (s, 1H), 7.76-7.74 (d, 1H, J=8.77 Hz), 7.64-7.61 (m, 1H), 7.14-7.13 (d, 1H), 7.00-6.99 (d, 1H, J=4.73 Hz), 6.69 (s, 1H), 6.46-6.44 (d, 1H, J=8.73 Hz), 4.04-3.64 (bm, TFA salt and water provided poor resolution), 3.51-3.48 (m, 2H), 3.36 (m, 1H), 3.14 (m, 2H), 2.71-2.65 (m, 2H), 2.15-2.12 (m, 2H), 1.71-1.69 (m, 2H).

Example 512

[2-Methoxy-4-(4-morpholin-4-yl-piperidin-1-yl)-phenyl]-(7-quinolin-8-yl-pyrrolo[2,1-f][1,2,4]triazin-2-yl)-amine; compound with trifluoro-acetic acid a) 8-(2-Methanesulfanyl-pyrrolo[2,1-f][1,2,4]triazin-7-yl)-quinoline was prepared in an analogous fashion to Example 47a replacing 2-methoxybenzeneboronic acid with 8-quinolinylboronic acid.

b) 8-(2-Methanesulfinyl-pyrrolo[2,1-f][1,2,4]triazin-7-yl)-quinoline was prepared in an analogous fashion to Example 47b replacing 7-(2-Methoxy-phenyl)-2-methylsulfanyl-pyrrolo[2,1-f][1,2,4]triazine with 8-(2-Methanesulfanyl-pyrrolo[2,1-f][1,2,4]triazin-7-yl)-quinoline.

c) The title compound was prepared in an analogous fashion to Example 486 after replacing 7-(4-Chloro-2-methoxy-phenyl)-2-methanesulfinyl-pyrrolo[2,1-f][1,2,4]triazine with 8-(2-Methanesulfinyl-pyrrolo[2,1-f][1,2,4]triazin-7-yl)-quinoline to give after purification via reverse phase HPLC [2-Methoxy-4-(4-morpholin-4-yl-piperidin-1-yl)-phenyl]-(7-quinolin-8-yl-pyrrolo[2,1-f][1,2,4]triazin-2-yl)-amine; compound with trifluoro-acetic acid as a brown lyophylate (56 mg, 38%). LC/MS (E/I+) 536.0 (M+H). NMR $^1$H (DMSO-d$_6$)-8.99 (s, 1H), 8.93-8.92 (m, 1H), 8.58-8.56 (d, 1H, J=8.17 Hz), 8.30-8.28 (d, 1H, J=7.08 Hz), 8.14-8.12 (d, 1H, J=8.02 Hz), 7.82-7.78 (m, 1H), 7.68-7.65 (m, 1H), 7.57 (s, 1H), 7.42-7.40 (d, 1H, J=8.73 Hz), 7.26-7.25 (d, 1H, J=4.62 Hz), 7.03-7.02 (d, 1H, J=4.62 Hz), 6.69 (s, 1H), 6.14-6.12 (d, 1H, J=8.25 Hz), 5.75-4.5 (broad hump, TFA salt and water provided poor resolution), 4.05-4.02 (m, 2H), 3.83 (s, 3H), 3.76-3.66 (m, 4H), 3.50-3.47 (m, 2H), 3.35 (m, 1H), 3.12 (bs, 2H), 2.74-2.68 (m, 2H), 2.16-2.13 (d, 2H, J=11.33 Hz), 1.73-1.71 (m, 2H).

Example 513

2-(4-{4-[7-(2-Cyano-phenyl)-pyrrolo[2,1-f][1,2,4]triazin-2-ylamino]-phenyl}-piperidin-1-yl)-acetamide; compound with trifluoro-acetic acid The title compound was prepared in an analogous fashion to Example 511 after replacing 2-Methoxy-4-(4-morpholin-4-yl-piperidin-1-yl)-phenylamine with 2-[4-(4-Amino-phenyl)-piperidin-1-yl]-acetamide to give after purification via reverse phase HPLC 2-(4-{4-[7-(2-Cyano-phenyl)-pyrrolo[2,1-f][1,2,4]triazin-2-ylamino]-phenyl}-piperidin-1-yl)-acetamide; compound with trifluoro-acetic acid as a brown lyophylate (12 mg, 9%). LC/MS (E/I+) 452.13 (M+H). NMR $^1$H (DMSO-d$_6$)-9.57 (s, 1H), 9.52 (bs, 1H), 9.09 (s, 1H), 8.11-8.09 (d, 1H, J=7.92 Hz), 8.07-8.05 (d, 1H, J=7.73 Hz), 7.93 (s, 1H), 7.93-7.89 (m, 1H), 7.75 (s, 1H), 7.71-7.63 (m, 3H), 7.16-7.15 (d, 1H, J=4.16 Hz), 7.09-7.07 (d, 2H, J=8.40 Hz), 7.01-6.99 (d, 1H, J=10.45 Hz), 3.98 (s, 2H), 3.7-3.3 (bm, TFA salt and water provided poor resolution), 3.14-3.12 (m, 2H), 2.74-2.68 (m, 1H), 2.08-1.93 (m, 4H).

Example 514

2-{4-[4-(7-Quinolin-8-yl-pyrrolo[2,1-f][1,2,4]triazin-2-ylamino)-phenyl]-piperidin-1-yl}-acetamide; compound with trifluoro-acetic acid The title compound was prepared in an analogous fashion to Example 512 after replacing 2-Methoxy-4-(4-morpholin-4-yl-piperidin-1-yl)-phenylamine with 2-[4-(4-Amino-phenyl)-piperidin-1-yl]-acetamide to give after purification via reverse phase HPLC 2-{4-[4-(7-Quinolin-8-yl-pyrrolo[2,1-f][1,2,4]triazin-2-ylamino)-phenyl]-piperidin-1-yl}-acetamide; compound with trifluoro-acetic acid as a yellow lyophylate (33 mg, 25%). LC/MS (E/I+) 478.12 (M+H). NMR $^1$H (DMSO-d$_6$)-9.52 (bs, 1H), 9.34 (s, 1H), 9.02 (s, 1H), 8.93-8.92 (d, 1H, J=2.80 Hz), 8.56-8.54 (d, 1H, J=8.17 Hz), 8.26-8.24 (d, 1H, J=7.17 Hz), 8.16-8.14 (d, 1H, J=8.04 Hz), 7.97 (s, 1H), 7.83-7.79 (m, 1H), 7.72 (s, 1H), 7.67-7.63 (m, 1H), 7.36-7.34 (d, 2H, J=8.36 Hz), 7.22-7.21 (d, 1H, J=4.60 Hz), 7.02-7.01 (d, 1H, J=4.60 Hz), 6.84-6.82 (d, 2H, J=8.40 Hz), 3.91 (s, 3H), 3.54-3.51 (d, 1H, J=11.36 Hz), 3.12-3.10 (m, 2H), 2.67-2.61 (m, 1H), 1.95-1.80 (m, 4H).

Example 515

2-[4-(4-{7-[2-(Methanesulfonyl-methyl-amino)-phenyl]-6-methyl-pyrrolo[2,1-f][1,2,4]triazin-2-ylamino}-3-methoxy-phenyl)-piperidin-1-yl]-acetamide; compound with trifluoro-acetic acid a) N-[2-(6-Methyl-2-methylsulfanyl-pyrrolo[2,1-f][1,2,4]triazin-7-yl)-phenyl]-methanesulfonamide was prepared in an analogous fashion to Example 47a after: replacing 2-methoxybenzeneboronic acid with N-[2-(4,4,5,5-Tetramethyl-1,3,2-dioxaborolan-2-yl)-phenyl]-methanesulfonamide, and replacing 7-Bromo-2-methylsulfanyl-pyrrolo[2,1-f][1,2,4]triazine with 7-Bromo-6-methyl-2-methylsulfanyl-pyrrolo[2,1-f][1,2,4]triazine, to give after purification via normal phase chromatography (EtOAc/hexane as eluant) N-[2-(6-Methyl-2-methylsulfanyl-pyrrolo[2,1-f][1,2,4]triazin-7-yl)-phenyl]-methanesulfonamide as a yellow solid (0.12 g, 44%). LC/MS (E/I+) 349.04 (M+H).

b) N-[2-(6-Methyl-2-methylsulfinyl-pyrrolo[2,1-f][1,2,4]triazin-7-yl)-phenyl]-methanesulfonamide was prepared in an analogous fashion to Example 47b replacing 7-(2-Methoxy-phenyl)-2-methylsulfanyl-pyrrolo[2,1-f][1,2,4]triazine with N-[2-(6-Methyl-2-methylsulfanyl-pyrrolo[2,1-f][1,2,4]triazin-7-yl)-phenyl]-methanesulfonamide to give N-[2-(6-Methyl-2-methylsulfinyl-pyrrolo[2,1-f][1,2,4]triazin-7-yl)-phenyl]-methanesulfonamide as a foamy material, which was used without further manipulation (0.13 g, 96%). LC/MS (E/I+) 365.02 (M+H).

c) N-[2-(2-Methanesulfinyl-6-methyl-pyrrolo[2,1-f][1,2,4]triazin-7-yl)-phenyl]-N-methyl-methanesulfonamide was prepared in an analogous fashion to Example 1220 replacing N-[2-(2-methylsulfinyl-pyrrolo[2,1-f][1,2,4]triazin-7-yl)-phenyl]-methanesulfonamide with N-[2-(6-Methyl-2-methylsulfinyl-pyrrolo[2,1-f][1,2,4]triazin-7-yl)-phenyl]-methanesulfonamide to give N-[2-(6-Methyl-2-methylsulfinyl-pyrrolo[2,1-f][1,2,4]triazin-7-yl)-phenyl]-methanesulfonamide as an orange residue, which was used without further manipulation (0.13 g, 96%). LC/MS (E/I+) 379.05 (M+H).

d) N-[2-(2-Hydroxy-6-methyl-pyrrolo[2,1-f][1,2,4]triazin-7-yl)-phenyl]-N-methyl-methanesulfonamide was prepared in an analogous fashion to Example 1221a replacing N-[2-(2-Methanesulfinyl-pyrrolo[2,1-f][1,2,4]triazin-7-yl)- phenyl]-N-methyl-methanesulfonamide with N-[2-(6-Methyl-2-methylsulfinyl-pyrrolo[2,1-f][1,2,4]triazin-7-yl)-phenyl]-methanesulfonamide to give N-[2-(2-Hydroxy-6-methyl-pyrrolo[2,1-f][1,2,4]triazin-7-yl)-phenyl]-N-methyl-methanesulfonamide as an orange residue, which was used without further manipulation (0.08 g, 70%). LC/MS (E/I+) 333.05 (M+H).

e) The title compound was prepared in an analogous fashion to Example 1254e after replacing N-[2-(2-Hydroxy-pyrrolo[2,1-f][1,2,4]triazin-7-yl)-phenyl]-N-methyl-methanesulfonamide with N-[2-(2-Hydroxy-6-methyl-pyrrolo[2,1-f][1,2,4]triazin-7-yl)-phenyl]-N-methyl-methanesulfonamide to give after purification via reverse phase HPLC 2-[4-(4-{7-[2-(Methanesulfonyl-methyl-amino)-phenyl]-6-methyl-pyrrolo[2,1-f][1,2,4]triazin-2-ylamino}-3-methoxy-phenyl)-piperidin-1-yl]-acetamide; compound with trifluoro-acetic acid as a light brown lyophylate (18 mg, 21%). LC/MS (E/I+) 515.21 (M+H). NMR $^1$H (DMSO-d$_6$)-9.55 (bs, 1H), 8.20 (s, 1H), 8.08 (s, 1H), 7.76-7.59 (m, 5H), 7.54-7.29 (m, 2H), 6.82 (s, 1H), 6.78 (s, 1H), 6.53-6.51 (d, 1H, J=8.20 Hz), 4.3-3.6 (bm, TFA salt and water provided poor resolution), 3.55-3.52 (d, 2H, J=11.24 Hz), 3.14-3.11 (m, 2H), 3.00 (s, 3H), 2.71-2.63 (m, 1H), 2.59 (s, 3H), 2.16 (s, 3H), 2.10-1.90 (m, 2H).

Example 516

2-[4-(4-{7-[2-(Methanesulfonyl-methyl-amino)-phenyl]-6-methyl-pyrrolo[2,1-f][1,2,4]triazin-2-ylamino}-phenyl)-piperidin-1-yl]-acetamide; compound with trifluoro-acetic acid The title compound was prepared in an analogous fashion to Example 515e after replacing 2-[4-(4-Amino-3-methoxy-phenyl)-piperidin-1-yl]-acetamide with 2-[4-(4-Amino-phenyl)-piperidin-1-yl]-acetamide to give after purification via reverse phase HPLC 2-[4-(4-{7-[2-(Methanesulfonyl-methyl-amino)-phenyl]-6-methyl-pyrrolo[2,1-f][1,2,4]triazin-2-ylamino}-phenyl)-piperidin-1-yl]-acetamide; compound with trifluoro-acetic acid as a tan lyophylate (14 mg, 28%). LC/MS (E/I+) 548.15 (M+H). NMR $^1$H (DMSO-d$_6$)-9.52 (bs, 1H), 9.24 (s, 1H), 8.84 (s, 1H), 7.97 (s, 1H), 7.71-7.60 (m, 3H), 7.55-7.41 (m, 4H), 6.96-6.94 (d, 2H, J=8.00 Hz), 6.76 (s, 1H), 3.91 (s, 2H), 3.54-3.51 (m, 2H), 3.12-3.10 (m, 2H), 3.07 (s, 3H), 2.66-2.64 (m, 1H), 2.61 (s, 3H), 2.16 (s, 3H), 1.95-1.89 (m, 4H).

Example 517

2-(4-{4-[7-(2-Cyano-phenyl)-pyrrolo[2,1-f][1,2,4]triazin-2-ylamino]-3-methoxy-phenyl}-piperidin-1-yl)-acetamide; compound with trifluoro-acetic acid The titled compound was prepared in an analogous fashion to Example 511a after replacing 7-bromo-2-(methylthio)pyrrolo[1,2-f][1,2,4]triazine with 2-{4-[4-(7-Bromo-pyrrolo[2,1-f][1,2,4]triazin-2-ylamino)-3-methoxy-phenyl]-piperidin-1-yl}-acetamide to give after purification via reverse phase HPLC 2-(4-{4-[7-(2-Cyano-phenyl)-pyrrolo[2,1-f][1,2,4]triazin-2-ylamino]-3-methoxy-phenyl}-piperidin-1-yl)-acetamide; compound with trifluoro-acetic acid as a tan lyophylate (58 mg, 48%). LC/MS (E/I+) 482.17 (M+H). NMR $^1$H (DMSO-d$_6$)-9.51 (bs, 1H), 9.08 (s, 1H), 8.10-8.08 (d, 1H, J=7.80 Hz), 8.06-8.04 (d, 1H, J=7.80 Hz), 7.98 (s, 1H), 7.95-7.93 (d, 1H, J=8.09 Hz), 7.89-7.87 (m, 2H), 7.72 (s, 1H), 7.67-7.63 (m, 1H), 7.17-7.16 (m, 1H), 7.04-7.03 (m, 1H), 6.90 (s, 1H), 6.72-6.70 (d, 1H, J=8.20 Hz), 3.93 (s, 2H), 3.88 (s, 3H), 3.57-3.54 (d, 2H, J=11.64 Hz), 3.15-3.14 (m, 2H), 2.67 (m, 1H), 2.07-1.95 (m, 4H).

Example 522

(R)-1-{7-[7-(2,3-Dihydro-benzofuran-7-yl)-pyrrolo[2,1-f]triazin-2-ylamino]-8-methoxy-1,2,4,5-tetrahydro-benzo[d]azepin-3-yl}-propan-2-ol To a mixture of 7-(2,3-Dihydro-benzofuran-7-yl)-pyrrolo[2,1-f][1,2,4]triazin-2-ol (0.100 g, 0.395 mmol, 1.05 eqv) and N,N-Diisopropylethylamine (0.28 mL, 4.22 eqv) in anhydrous DMF (1 mL) in a 10 mL sealed tube was added N-Phenylbis(trifluoromethane-sulfonimide (0.148 g, 1.105 eqv.). The mixture was stirred at room temperature for 1 h and to it (R)-1-(7-amino-8-methoxy-1,2,4,5-tetrahydro-3-benzazepin-3-yl)-propan-2-ol (0.094 mg, 0.38 mmol, 1.00 eqv.) was added. The reaction mixture was heated at 70° C. for 2 h, concentrated in vacuo and purified via prepTLC (silica gel; eluant: 6% methanol in methylene chloride) to afford (R)-1-{7-[7-(2,3-Dihydro-benzofuran-7-yl)-pyrrolo[2,1-f]triazin-2-ylamino]-8-methoxy-1,2,4,5-tetrahydro-benzo[d]azepin-3-yl}-propan-2-ol as a dark brown solid (0.018 g, 10%). MP>200° C. (decomp.). LCMS (E/I+) 486.16 (M+H). $^1$H NMR (CDCl$_3$) δ 8.80 (s, 1H), 8.30 (d, 2H, J=6.50 Hz), 7.45 (s, 1H), 7.30 (s, 2H), 7.00 (dd, 1H, J=6.00H, 6.00 Hz), 6.80 (d, 1H, J=6.00 Hz), 6.65 (s, 1H), 4.80 (t, 2H, J=6.00 Hz), 3.90 (broad, 1H), 3.80 (s, 3H), 3.30 (t, 2H, J=6.00 Hz), 2.90-2.10 (overlapping m, 11H), 1.10 (d, 3H, J=6.00 Hz).

Example 523

N-Cyclopropyl-3-{2-[3-((R)-2-hydroxy-propyl)-8-methoxy-2,3,4,5-tetrahydro-1H-benzo[d]azepin-7-ylamino]-pyrrolo[2,1-f][1,2,4]triazin-7-yl}benzenesulfonamide This compound as a yellow solid, was prepared following the same procedure as described for the synthesis of Example 522 by coupling N-Cyclopropyl-3-(2-hydroxy-pyrrolo[2,1-f][1,2,4]triazin-7-yl)-benzenesulfonamide and (R)-1-(7-Amino-8-methoxy-1,2,4,5-tetrahydro-3-benzazepin-3-yl)-propan-2-ol. MP>150° C. (decomp.). LCMS (E/I+) 563.14 (M+H). $^1$H NMR (DMSO-d$_6$) δ 9.00 (s, 1H), 8.60 (d, 1H, J=6.50 Hz), 8.20 (s, 1H), 7.95 (s, 1H), 7.85 (m, 2H), 7.70 (t, 1H, J=6.50 Hz), 7.20 (d, 1H, J=6.00 Hz), 7.00 (d, 1H, J=6.00 Hz), 6.80 (s, 1H), 4.30 (broad, 1H), 3.80 (s, 3H), 3.70 (broad, 1H), 2.80 (broad, 2H), 2.70 (broad, 2H), 2.60 (broad, 4H), 2.40 (broad, 2H), 2.10 (broad, 1H), 1.20 (broad, 1H), 1.10 (d, 3H, J=6.00 Hz), 0.50 (broad, 2H), 0.40 (broad, 2H).

Example 524

2-{7-[7-(3-Cyclopropylsulfamoyl-phenyl)-pyrrolo[2,1-f][1,2,4]triazin-2-ylamino]-8-methoxy-1,2,4,5-tetrahydro-benzo[d]azepin-3-yl}-acetamide This compound as a yellow solid, was prepared following the same procedure as described for the synthesis of Example 522 by coupling N-Cyclopropyl-3-(2-hydroxy-pyrrolo[2,1-f][1,2,4]triazin-7-yl)-benzenesulfonamide and 2-(7-Amino-8-methoxy-1,2,4,5-tetrahydro-benzo[d]azepin-3-yl)-acetamide. MP>150° C. (decomp.). LCMS (E/I+) 562.14 (M+H). $^1$H NMR (DMSO-d$_6$) δ 9.00 (s, 1H), 8.60 (d, 1H, J=6.50 Hz), 8.20 (s, 1H), 7.95 (s, 1H), 7.85 (m, 2H), 7.70 (t, 1H, J=6.50 Hz), 7.20 (d, 1H, J=6.00 Hz), 7.00 (d, 1H, J=6.00 Hz), 6.80 (s, 1H), 4.30 (broad, 1H), 3.80 (s, 3H), 3.70 (broad, 1H), 2.80

(broad, 2H), 2.70 (broad, 2H), 2.60 (broad, 4H), 2.40 (broad, 2H), 2.10 (broad, 1H), 1.20 (broad, 1H), 0.50 (broad, 2H), 0.40 (broad, 2H).

Example 531

4-(1-{3-Methoxy-4-[7-(2-methoxy-phenyl)-pyrrolo[2,1-f][1,2,4]triazin-2-ylamino]-phenyl}-piperidin-4-yl)-piperazine-1-carboxylic acid benzyl ester a) 4-(1-tert-Butoxycarbonyl-piperidin-4-yl)-piperazine-1-carboxylic acid benzyl ester: To a solution of 4-Oxo-piperidine-1-carboxylic acid tert-butyl ester (5.0 g, 0.025 mol) and piperazine-1-carboxylic acid benzyl ester (5.6 g, 0.025 mol) in 1,2-Dichloroethane (100 mL) was added 10-Camphorsulfonic acid (0.6 g, 0.002 mol) and Magnesium sulfate (9.0 g). The reaction was heated at 50° C. overnight. To the reaction was added Sodium triacetoxyborohydride (10.17 g, 0.048 mol) and stirred at room temperature overnight. The reaction was filtered, 10% sodium carbonate solution added, separated, washed dried and evaporated to give 4-(1-tert-Butoxycarbonyl-piperidin-4-yl)-piperazine-1-carboxylic acid benzyl ester as an oil (10.77 g) (Contains solvent). LCMS (m/e) 404 (M+1); $^1$H-NMR (DMSO-$d_6$, 400 MHz) δ 7.37-7.35 (m, 5H), 5.06 (s, 2H), 3.90 (s, 3H), 3.62 (m, 1H), 3.36 (br, 3H), 2.70 (br, 2H), 2.44 (m, 4H), 1.73 (br, 2H), 1.25 (br, 2H).

b) 4-Piperidin-4-yl-piperazine-1-carboxylic acid benzyl ester ditrifluoroacetate: To a cooled solution of 4-(1-tert-Butoxycarbonyl-piperidin-4-yl)-piperazine-1-carboxylic acid benzyl ester (5.4 g, 0.013 mol) in DCM (20 mL) was added Trifluoroacetic Acid (20 mL, 0.2 mol) and Methylene chloride (20 g) and stirred at room temperature overnight. The solvent was evaporated leaving 4-Piperidin-4-yl-piperazine-1-carboxylic acid benzyl ester ditrifluoroacetate as an oil (12.9 g) (contains DCM and TFA). LCMS (m/e) 304 (M+1).

c) 4-[1-(3-Methoxy-4-nitro-phenyl)-piperidin-4-yl]-piperazine-1-carboxylic acid benzyl ester: A mixture of 4-Fluoro-2-methoxy-1-nitro-benzene (2.18 g, 0.0127 mol), 4-Piperidin-4-yl-piperazine-1-carboxylic acid benzyl ester (3.85 g, 0.0127 mol) and Potassium carbonate (8.58 g, 0.0621 mol) in N,N-Dimethylformamide (60 mL) was heated at 60° C. overnight. To the mixture was added 60 mL of saturated brine and adjusted the pH to 10. It was extracted with DCM, washed with brine, dried over potassium carbonate and evaporated to an oil. The product was purified by ISCO chromatography, followed by basic alumina column chromatography with ethyl acetate to give 4-[1-(3-Methoxy-4-nitro-phenyl)-piperidin-4-yl]-piperazine-1-carboxylic acid benzyl ester (3.75 g, 65%) as an oil. LCMS (m/e) 454 (M); $^1$H-NMR (DMSO-$d_6$, 400 MHz) δ 7.87-7.86 (d, 1H), 7.37-7.34 (m, 5H), 6.62-6.57 (d, 1H), 5.06 (s, 2H), 4.04 (m, 2H), 3.90 (s, 3H), 3.37 (br, 3H), 2.94 (t, 2H), 2.89 (s, 1H), 2.73 (s, 1H), 1.99 (s, 1H), 1.87-1.78 (br, 2H), 1.50-1.48 (br, 2H), 1.17 (t, 1H).

D) 4-[1-(4-Amino-3-methoxy-phenyl)-piperidin-4-yl]-piperazine-1-carboxylic acid benzyl ester:

A mixture of 4-[1-(3-Methoxy-4-nitro-phenyl)-piperidin-4-yl]-piperazine-1-carboxylic acid benzyl ester (0.20 g, 0.44 mmol), Acetic acid (2 mL, 30 mmol), Ethanol (2 mL) and Zinc (0.20 g, 3.0 mmol) was stirred at room temperature for 3 hours. The reaction was filtered and evaporated. To the residue was added a saturated sodium bicarbonate solution and DCM, separated, dried and evaporated to give 4-[1-(4-Amino-3-methoxy-phenyl)-piperidin-4-yl]-piperazine-1-carboxylic acid benzyl ester as a dark blue solid (0.155 g, 82%). LCMS (m/e) 424 (M); $^1$H-NMR (DMSO-$d_6$, 400 MHz) δ 7.387.36 (m, 5H), 6.48 (s, 2H), 6.13 (s, 1H), 5.07 (s, 2H), 4.20 (br, 2H), 3.73 (s, 3H), 3.39 (m, 6H), 1.80 (m, 2H, 0.80 (m, 2H).

E) 4-(1-{3-Methoxy-4-[7-(2-methoxy-phenyl)-pyrrolo[2,1-f][1,2,4]triazin-2-ylamino]-phenyl}-piperidin-4-yl)-piperazine-1-carboxylic acid benzyl ester A mixture of 4-[1-(4-Amino-3-methoxy-phenyl)-piperidin-4-yl]-piperazine-1-carboxylic acid benzyl ester (0.62 g, 0.0015 mol), 2-Methanesulfinyl-7-(2-methoxy-phenyl)-pyrrolo[2,1-f][1,2,4]triazine (0.3 g, 0.0009 mol) and Potassium acetate (0.59 g, 0.0060 mol) in N,N-Dimethylformamide (10 mL) was heated at 110° C. for 40 hr. The solvent was evaporated and the residue chromatographed on silica gel prep plates 2× with ethyl acetate-IPA (20-1) giving 4-(1-{3-Methoxy-4-[7-(2-methoxy-phenyl)-pyrrolo[2,1-f][1,2,4]triazin-2-ylamino]-phenyl}-piperidin-4-yl)-piperazine-1-carboxylic acid benzyl ester as a tan solid (0.51 g, 9%). MP: 75-76° C.; $^1$H-NMR (DMSO-$d_6$, 400 MHz) δ 8.80 (s, 1H), 7.84-7.81 (d, 1H, J=8.40 Hz), 7.48 (s, 1H), 7.45-7.35 (m, 7H), 7.20 (s, 1H), 7.18 (s, 1H), 7.12-7.02 (t, 1H), 6.95-6.89 (q, 2H, J=4.68 Hz), 6.62 (d, 1H), 6.38-6.35 (q, 1H) 5.08 (s, 2H), 3.83 (s, 3H), 3.78 (s, 3H), 3.70-3.65 (d, 2H), 3.39 (br, 8H), 2.70-2.51 (m, 3H), 1.87-1.78 (m, 2H), 1.60-1.52 (m. 2H).

Example 532

2-(2-{2-Methoxy-4-[4-(4-methyl-piperazin-1-yl)-piperidin-1-yl]-phenylamino}-pyrrolo[2,1-f][1,2,4]triazin-7-yl)-N,N-dimethyl-benzenesulfonamide a) 1-[1-(3-Methoxy-4-nitro-phenyl)-piperidin-4-yl]-4-methyl-piperazine:

A mixture of 4-Fluoro-2-methoxy-1-nitro-benzene (3.0 g, 0.018 mol), 1-Methyl-4-piperidin-4-yl-piperazine (3.52 g, 0.0192 mol) and Triethylamine (1.76 g, 0.0174 mol) in Dimethyl sulfoxide (10 mL) was stirred at room temperature overnight giving a yellow slurry. It was diluted with water (500 mL), adjusted the pH to 14 and saturated with salt. A yellow precipitate was collected, washed with a saturated salt solution. This was air dried and then extracted with DCM, dried over anhydrous potassium carbonate and evaporated to give a yellow solid (5.34 g) LCMS (m/e) 335 (M+1); $^1$H-NMR (DMSO-$d_6$, 400 MHz) δ 7.88-7.86) d, 2H, J=9.37 Hz), 6.59-6.56 (dd, 1H, J=2.28 Hz), 6.50-6.49 (d, 1H, J=2.37 Hz), 4.05-4.02 (d, 2H, J=13.04 Hz), 3.99 (s, 3H), 3.31 (s, 3H), 2.95 (t, 2H), 2.29 (br, 4H), 1.43 (m, 4H).

b) 2-Methoxy-4-[4-(4-methyl-piperazin-1-yl)-piperidin-1-yl]-phenylamine:

A mixture of 1-[1-(3-Methoxy-4-nitro-phenyl)-piperidin-4-yl]-4-methyl-piperazine (5.30 g, 0.0158 mol) and 10% Palladium on Carbon (0.53 g, 0.040 mol) in Ethanol (158 mL) and Ethyl acetate (83 mL) and was hydrogenated for 4 hr. The reaction was filtered and the filtrate evaporated to give a purple solid (4.80 g, 89%). LCMS (m/e) 305 (M+1); $^1$H-NMR (DMSO-$d_6$, 400 MHz) δ 6.50 (s, 1H), 6.48-6.47 (dd, 1H, J=2.36 Hz), 6.29-6.27 (dd, 1H, J=2.32 Hz), 4.19 (s, 2H), 3.73 (s, 3H), 3.43-3.40 (d, 2H, J=12.0 Hz), 3.31 (s, 2H), 2.30 (br, 4H), 2.02 (t, 1H), 1.82-1.79 (d, 2H, J=11.49 Hz), 1.50-1.48 (m, 2H).

c) (7-Bromo-pyrrolo[2,1-f][1,2,4]triazin-2-yl)-{2-methoxy-4-[4-(4-methyl-piperazin-1-yl)-piperidin-1-yl]-phenyl}-amine:

A mixture of 2-Methoxy-4-[4-(4-methyl-piperazin-1-yl)-piperidin-1-yl]-phenylamine (1.25 g, 0.00411 mol) (for preparation see: Ahmed, et al. WO2008051547), 7-Bromo-2-methanesulfinyl-pyrrolo[2,1-f][1,2,4]triazine (0.75 g, 0.0029 mol) and N,N-Diisopropylethylamine (2.02 mL, 0.0116 mol) in 2-Methoxyethanol (10 mL) was heated in the microwave at 170° C. for 90 minutes. Purification by Isco chromatography gave (7-Bromo-pyrrolo[2,1-f][1,2,4]triazin-2-yl)-{2-methoxy-4-[4-(4-methyl-piperazin-1-yl)-piperidin-1-yl]-phenyl}-amine as a tan solid (0.50 g, 35%). MP: 171-173° C.; LCMS (m/e) 500 (M); $^1$H-NMR (DMSO-d$_6$, 400 MHz) δ 8.83 (s, 1H), 8.02-8.00 (d, 1H, J=8.76 Hz), 7.74 (s, 1H), 6.93-6.85 (q, 2H), 6.67-6.66 (s, 1H), 6.52-6.49 (d, 1H, J=6.40 Hz), 3.85 (s, 3H), 3.71-3.68 (d, 2H, J=12.20 Hz), 2.67-2.62 (t, 2H, J=11.80 Hz), 2.31-2.28 (br, 4H), 1.83 (s3H), 1.86-1.83 (d, 2H), 1.55-1.50 (2, 2H).

D) 2-(2-{2-Methoxy-4-[4-(4-methyl-piperazin-1-yl)-piperidin-1-yl]-phenylamino}-pyrrolo[2,1-f][1,2,4]triazin-7-yl)-N,N-dimethyl-benzenesulfonamide:

A mixture of (7-Bromo-pyrrolo[2,1-f][1,2,4]triazin-2-yl)-{2-methoxy-4-[4-(4-methyl-piperazin-1-yl)-piperidin-1-yl]-phenyl}-amine (0.09 g, 0.0002 mol) and N,N-dimethylsulfonamide-2-benzeneboronic acid (0.060 g, 0.00026 mol), Tetrakis(triphenylphosphine)palladium(0) (0.023 g, 0.000020 mol), 1 M of Sodium carbonate in Water (0.7 mL, 0.0007 mol), Tetrahydrofuran (4 mL,) and ethanol (4 mL) under nitrogen was heated at 80° C. overnight. Purification by prep plate chromatography gave 2-(2-{2-Methoxy-4-[4-(4-methyl-piperazin-1-yl)-piperidin-1-yl]-phenylamino}-pyrrolo[2,1-f][1,2,4]triazin-7-yl)-N,N-dimethyl-benzenesulfonamide (0.052 g, 48%) as a tan solid. MP; 198-205° C.; $^1$H-NMR (DMSO-d$_6$, 400 MHz) δ 8.91 (s, 1H), 8.04-8.02 (d, 1H, J=7.80 Hz), 7.81-7.79 (t, 1H, J=7.44 Hz), 7.77-7.75 (t, 1H, J=7.56 Hz), 7.65-7.63 (d, 1H, J=7.48 Hz), 7.53-7.51 (d, 1H, J=8.76 Hz), 7.46 (s, 1H), 6.91-6.86 (q, 1H, J=4.56 Hz), 6.58-6.57 (d, 1H, J=2.40 Hz), 6.16-6.13 (d, 1H, J=12.44 Hz), 3.80 (s, 3H), 3.60-3.56 (d, 2H, J=12.44 Hz), 2.35 (s, 6H), 2.17 (s, 3H), 1.83-1.80 (d, 2H, J=11.88 Hz), 1.49-1.46 (q, 2H, J=8.52 Hz) 1.23 (s, 1H).

Example 533

[7-(6-Chloro-pyridin-3-yl)-pyrrolo[2,1-f][1,2,4]triazin-2-yl]-{2-methoxy-4-[4-(4-methyl-piperazin-1-yl)-piperidin-1-yl]-phenyl}-amine trifluoroacetate Following the example of 532 (D), (7-Bromo-pyrrolo[2,1-f][1,2,4]triazin-2-yl)-{2-methoxy-4-[4-(4-methyl-piperazin-1-yl)-piperidin-1-yl]-phenyl}-amine (0.088 g, 0.00018 mol) and 2-Chloro-5-pyridineboronic acid (0.028 g, 0.00018 mol) were heated at 80° C. overnight. Purification by Gilson chromatography gave [7-(6-Chloro-pyridin-3-yl)-pyrrolo[2,1-f][1,2,4]triazin-2-yl]-{2-methoxy-4-[4-(4-methyl-piperazin-1-yl)-piperidin-1-yl]-phenyl}-amine (0.022 g, 23%) as a tan solid. MP: 186-188° C.; $^1$H-NMR (DMSO-d$_6$, 400 MHz) δ 9.18-9.17 (d, 1H, J=2.40 Hz), 8.98 (s, 1H), 8.64-8.61 (d, 1H, J=5.88 Hz), 8.05 (s, 1H), 7.61 (s, 1H), 7.59 (s, 1H), 7.34-7.32 (d, 1H, J=4.80 Hz), 6.97-6.95 (d, 1H, J=4.84 Hz), 6.77 (br, 1H), 6.63 (br, 1H), 3.83 (s, 1H), 3.46 (br, 2H), 2.78 (br, 2H), 2.08-2.01 (br, 3H), 1.66 (m, 2H).

Example 534

N-tert-Butyl-3-(2-{2-methoxy-4-[4-(4-methyl-piperazin-1-yl)-piperidin-1-yl]-phenylamino}-pyrrolo[2,1-f][1,2,4]triazin-7-yl)-benzene sulfonamide Following the procedure of example 532 (D), (7-Bromo-pyrrolo[2,1-f][1,2,4]triazin-2-yl)-{2-methoxy-4-[4-(4-methyl-piperazin-1-yl)-piperidin-1-yl]-phenyl}-amine (0.050 g, 0.00010 mol) and 3-t-Butylsulfamoylphenylboronic acid (0.028 g, 0.00011 mol) were reacted. Purification by prep plate chromatography gave N-tert-Butyl-3-(2-{2-methoxy-4-[4-(4-methyl-piperazin-1-yl)-piperidin-1-yl]-phenylamino}-pyrrolo[2,1-f][1,2,4]triazin-7-yl)-benzenesulfonamide as a tan solid (0.032 g, 51%). MP: 214-216° C.; $^1$H-NMR (DMSO-d$_6$, 400 MHz) δ 8.96 (s, 1H), 8.54 (s, 1H), 8.35-8.34 (d, 1H), 7.80 (t, 1H), 7.78-7.77 (d, 1H, J=2.88 Hz), 7.66 (t, 1H), 7.58 (s, 1H), 7.20-7.19 (d, 1H, J=4.80 Hz), 6.97-6.96 (d, 1H, J=4.72 Hz), 6.66 (s, 1H), 6.62-6.60 (d, 1H), 3.83 (s, 3H), 3.73-3.70 (d, 2H), 2.70-2.63 (m, 2H), 2.38-2.25 (m, 4H), 2.14 (s, 3H), 1.89-1.81 (d, 2H), 1.60-1.45 (q, 2H).

Example 535

{4-[4-(4-Methanesulfonyl-piperazin-1-yl)-piperidin-1-yl]-2-methoxy-phenyl}-[7-(2-methoxy-phenyl)-pyrrolo[2,1-f][1,2,4]triazin-2-yl]-amine trifluoroacetate Following the procedure of example 532 (c), 2-Methanesulfinyl-7-(2-methoxy-phenyl)-pyrrolo[2,1-f][1,2,4]triazine (0.054 g, 0.00019 mol), 4-[4-(4-Methanesulfonyl-piperazin-1-yl)-piperidin-1-yl]-2-methoxy-phenylamine (0.10 g, 0.00027 mol) were heated in the microwave at 180° C. for 5 hours. Purification by Gilson chromatography gave {4-[4-(4-Methanesulfonyl-piperazin-1-yl)-piperidin-1-yl]-2-methoxy-phenyl}-[7-(2-methoxy-phenyl)-pyrrolo[2,1-f][1,2,4]triazin-2-yl]-amine trifluoroacetate as a tan solid (0.015 g, 13%). Tan solid; MP: 104-106° C.; $^1$H-NMR (DMSO-d$_6$, 400 MHz) δ 8.90 (s, 1H), 7.89-7.87 (d, 1H, J=8.64 Hz), 7.85-7.83 (d, 1H, J=6.04 Hz), 7.53 (s, 1H), 7.46-7.42 (t, 1H, J=8.48 Hz), 7.21-7.19 (d, 1H, J=8.24 Hz), 7.11-7.08 (t, 1H, J=7.80 Hz), 6.96-6.90 (q, 2H, J=4.68 Hz), 6.70 (s, 1H), 6.46-6.41 (d, 1H), 3.86 (s, 3H), 3.78 (s, 3H), 2.75-2.65 (m, 1H), 2.17-2.08 (m, 2H), 1.85-1.70 (m, 2H).

Example 536

1-[4-(1-{3-Methoxy-4-[7-(2-methoxy-phenyl)-pyrrolo[2,1-f][1,2,4]triazin-2-ylamino]-phenyl}-piperidin-4-yl)-piperazin-1-yl]-ethanone trifluoroacetate Following the procedure of example 532 (c), 2-Methanesulfinyl-7-(2-methoxy-phenyl)-pyrrolo[2,1-f][1,2,4]triazine (0.0615 g, 0.000214 mol) and 1-{4-[1-(4-Amino-3-methoxy-phenyl)-piperidin-4-yl]-piperazin-1-yl}-ethanone (0.10 g, 0.00030 mol) were heated in the microwave at 200° C. for 16 hr. Purification by Gilson chromatography gave 1-[4-(1-{3-Methoxy-4-[7-(2-methoxy-phenyl)-pyrrolo[2,1-f][1,2,4]triazin-2-ylamino]-phenyl}-piperidin-4-yl)-piperazin-1-yl]-ethanone trifluoroacetate as a tan solid (0.030 g, 25%). MP: 104-106° C.; $^1$H-NMR (DMSO-d$_6$, 400 MHz) δ 8.90 (s, 1H), 7.89-7.87 (s, 1H, J=8.72 Hz), 7.85-7.83 (d, 1H, J=604 Hz), 7.53 (s, 1H), 7.46-7.42 (t, 1H, J=8.56 Hz), 7.21-7.19 (d, 1H, J=8.32 Hz), 7.11-7.08 (t, 1H, J=7.48 Hz), 6.96-6.90 (q, 2H, J=4.64 Hz), 6.69 (s, 1H), 6.44-6.42 (d, 1H, J=9.08), 4.54-4.46 (br, 2H), 4.09-4.03 (br, 1H), 3.86 (s, 3H), 3.79 (s, 3H), 3.58-3.50 (br, 2H), 3.44-3.34 (br, 2H), 3.19-3.08 (br, 1H), 3.04-2.83 (br, 2H), 2.75-2.66 (m, 1H), 2.15-2.06 (br, 2H), 1.82-1.68 (br, 2H).

Example 537

[7-(2-Methoxy-phenyl)-pyrrolo[2,1-f][1,2,4]triazin-2-yl]-[2-methoxy-4-(4-piperazin-1-yl-piperidin-1-yl)-phenyl]-amine A mixture of 4-(1-{3-Methoxy-4-[7-(2-methoxy-phenyl)-pyrrolo[2,1-f][1,2,4]triazin-2-ylamino]-phenyl}-piperidin- 4-yl)-piperazine-1-carboxylic acid benzyl ester (0.027 g, 0.042 mmol) and 33% wt. HBr in HOAc (4 mL, 40 mmol) was stirred at room temperature for 5 hours. The reaction was evaporated under vacuum. Water (5 mL) was added and the solution filtered. The filtrate was basified, extracted with ethyl acetate, washed dried and evaporated to give a tan solid (0.009 g, 40%). MP; 65-67° C.; $^1$H-NMR (DMSO-$d_6$, 400 MHz) δ 8.88 (s, 1H), 7.84-7.81 (d, 2H, J=8.84 Hz), 7.48 (s, 1H), 7.43-7.41 (t, 1H, J=7.58 Hz), 7.21-7.19 (d, 1H, J=8.20 Hz), 7.10-7.06 (t, 1H, J=7.24 Hz), 6.95-6.89 (q, 2H, J=4.60 Hz), 6.63 (s, 1H), 6.38-6.36 (d, 1H, J=8.60 Hz), 3.83 (s, 3H), 3.78 (s, 3H), 3.69-3.62 (br, 2H), 2.76 (br, 3H) 2.67-2.57 (m, 3H), 2.35-2.25 (br, 2H), 1.90 (s, 1H), 1.89-1.78 (br, 2H), 1.53 (br, 3H), 1.23 (m, 4H), 1.19-1.18 (d, 2H, J=5.36 Hz) 1.13-1.08 (q, 4H, J=7.00 Hz), 0.95-0.83 (m, 5H).

Example 538

[7-(2-Methoxymethyl-phenyl)-pyrrolo[2,1-f][1,2,4]triazin-2-yl]-{2-methoxy-4-[4-(4-methyl-piperazin-1-yl)-piperidin-1-yl]-phenyl}-amine Following the procedure of example 532 (D), (7-Bromo-pyrrolo[2,1-f][1,2,4]triazin-2-yl)-{2-methoxy-4-[4-(4-methyl-piperazin-1-yl)-piperidin-1-yl]-phenyl}-amine (0.062 g, 0.00012 mol) and 2-Methoxymethyl phenylboronic acid (0.0226 g, 0.000132 mol) were reacted. Purification by prep plate chromatography gave [7-(2-Methoxymethyl-phenyl)-pyrrolo[2,1-f][1,2,4]triazin-2-yl]-{2-methoxy-4-[4-(4-methyl-piperazin-1-yl)-piperidin-1-yl]-phenyl}-amine (0.034 g, 51%) as a tan solid MP: 96-101 C; $^1$H-NMR (DMSO-$d_6$, 400 MHz) δ 8.92 (s, 1H), 7.65-7.62 (m, 2H), 7.55 (m, 2H), 7.47-7.45 (t, 2H, J=3.56 Hz), 6.94-6.87 (q, 2H, J=4.56 Hz), 6.61-6.60 (d, 1H, J=2.28 Hz), 6.42-6.38 (d, 1H), 6.30-6.27 (d, 1H), 4.33 (s, 2H), 3.81 (s, 3H), 3.64-3.61 (d, 2H) 3.17 (s, 3H), 2.67-2.57 (m, 6H), 2.33 (br, 5H), 2.16 (s, 3H), 1.84-1.81 (m, 2H), 1.50-1.48 (m, 2H), 1.23-1.17 (br, 3H).

Example 539

[2-Methoxy-5-methyl-4-(morpholin-4-yl-piperidin-1-yl)-phenyl]-7(2-methoxy-phenyl)-pyrrolo[2,1-f][1,2,4]triazin-2-yl]-amine trifluoroacetate Following the procedure of example 532 (c), 2-Methanesulfinyl-7-(2-methoxy-phenyl)-pyrrolo[2,1-f][1,2,4]triazine (0.10 g, 0.35 mmol) and 2-Methoxy-5-methyl-4-(4-morpholin-4-yl-piperidin-1-yl)-phenylamine (0.20 g, 0.65 mmol) were heated in the microwave at 200° C. for 18 hours. Purification by Gilson chromatography gave [2-Methoxy-5-methyl-4-(morpholin-4-yl-piperidin-1-yl)-phenyl]-7(2-methoxy-phenyl)-pyrrolo[2,1-f][1,2,4]triazin-2-yl]-amine trifluoroacetate as a tan solid (0.021 g, 9%). MP: 71-74° C.; LC/MS (m/e) 529 (M); $^1$H-NMR (DMSO-$d_6$, 400 MHz) δ 7.84-7.83 (d, 1H, J=7.48 Hz), 7.50 (s, 1H), 7.47-7.43 (1, tH, J=8.00 Hz), 7.22-7.20 (d, 1H, J=8.32 Hz), 7.13-7.09 (t, 1H, J=7.45 Hz), 6.96-6.94 (q, 1H, J=8.12 Hz), 6.71 (s, 1H), 4.05-4.03 (d, 2H, J=11.37 Hz), 3.85 (s, 3H), 3.78 (s, 3H), 3.73-3.67 (t, 1H, J=12.09 Hz), 3.52-3.49 (d, 2H, J=12.16 Hz), 3.30 (br, 1H), 3.14-3.12 (d, 4H, J=10.79 Hz), 2.66 (t, 1H), 2.17-2.14 (d, 2H, J=11.00 Hz), 2.09 (s, 3H), 1.78-1.75 (q, 2H, J=11.40 Hz).

Example 540

[7-(2-Methanesulfonyl-phenyl)-pyrrolo[2,1-f][1,2,4]triazin-2-yl]-[2-methoxy-4-(4-morpholin-4-yl-piperidin-1-yl)-phenyl]-amine Following the procedure of example 532 (c), 2-Methoxy-4-(4-morpholin-4-yl-piperidin-1-yl)-phenylamine (0.095 g, 0.33 mmol) and 2-Methanesulfinyl-7-(2-methanesulfonyl-phenyl)-pyrrolo[2,1-f][1,2,4]triazine (0.17 g, 0.51 mmol) were heated in the microwave at 190° C. for 3 hours. Purification by Gilson chromatography gave [7-(2-Methanesulfonyl-phenyl)-pyrrolo[2,1-f][1,2,4]triazin-2-yl]-[2-methoxy-4-(4-morpholin-4-yl-piperidin-1-yl)-phenyl]-amine as a tan solid; MP: 111-112° C.; LCMS (m/e) 563 (M+1); $^1$H-NMR (DMSO-$d_6$, 400 MHz) δ 8.94 (s, 1H), 8.16-8.14 (d, 1H, J=8.04 Hz), 7.887.85 (t, 1H, J=7.25 Hz), 7.807.60 (t, 1H, J=7.48 Hz), 7.707.68 (d, 1H, J=7.58 Hz), 7.60 (s, 1H), 7.43-7.41 (d, 1H, J=8.45 Hz), 6.94-6.92 (q, 2H, J=5.45 Hz), 6.56 (s, 1H), 6.21-6.19 (d, 1H, J=8.80 Hz), 5.75 (s, 1H), 3.76 (s, 3H), 3.62-3.58 (m, 4H), 3.01 (s, 3H), 2.88 (s, 3H), 2.61-2.55 (t, 1H), 2.23 (t, 1H), 1.86-1.83 (d, 2H, J=11.77 Hz), 1.48-1.45 (q, 2H, J=11.36).

Example 541

(S)-1-(4-{4-[7-(2-Methanesulfonyl-phenyl)-pyrrolo[2,1-f][1,2,4]triazin-2-ylamino]-3-methoxy-phenyl}-piperazin-1-yl)-propan-2-ol Following the procedure of example 532 (c), (S)-1-[4-(4-Amino-3-methoxy-phenyl)-piperazin-1-yl]-propan-2-ol (0.087 g, 0.33 mmol) and 2-Methanesulfinyl-7-(2-methanesulfonyl-phenyl)-pyrrolo[2,1-f][1,2,4]triazine (0.16 g, 0.48 mmol) were heated in the microwave at 190° C. for 4 hours. Purification by Gilson chromatography gave (S)-1-(4-{4-[7-(2-Methanesulfonyl-phenyl)-pyrrolo[2,1-f][1,2,4]triazin-2-ylamino]-3-methoxy-phenyl}-piperazin-1-yl)-propan-2-ol as a tan solid. MP: 98-100° C.; LCMS (m/e) 537 (M+1); $^1$H-NMR (DMSO-$d_6$, 400 MHz) δ 8.94 (s, 1H), 8.16-8.15 (d, 1H, J=6.84 Hz), 7.88-7.85 (t, 1H, J=6.24 Hz), 7.80-7.76 (t, 1H, J=7.73 Hz), 7.70-7.68 (d, 1H, J=7.56 Hz), 7.60 (s, 1H), 7.44-7.42 (d, 1H, J=8.77 Hz), 6.95-6.91 (q, 2H, J=4.64 Hz), 6.56 (s, 1H), 6.21-6.18 (dd, 1H, J=2.44 Hz), 4.30-4.29 (d, 1H), 3.77 (s, 3H), 3.29 (s, 1H), 3.05-3.03 (m, 3H), 2.87 (s, 3H), 2.55-2.52 (m, 2H), 2.28-2.21 (m, 6H).

Example 542

[7-(2,6-Dimethoxy-phenyl)-pyrrolo[2,1-f][1,2,4]triazin-2-yl]-[2-methoxy-4-(4-morpholin-4-yl-piperidin-1-yl)-phenyl]-amine trifluoroacetate Following the procedure of example 532 (c), 2-Methoxy-4-(4-morpholin-4-yl-piperidin-1-yl)-phenylamine (0.17 g, 0.59 mmol) and 7-(2,6-Dimethoxy-phenyl)-2-methanesulfinyl-pyrrolo[2,1-f][1,2,4]triazine (0.095 g, 0.30 mmol) were heated in the microwave at 190° C. for 14 hours. Purification by Gilson chromatography gave [7-(2,6-Dimethoxy-phenyl)-pyrrolo[2,1-f][1,2,4]triazin-2-yl]-[2-methoxy-4-(4-morpholin-4-yl-piperidin-1-yl)-phenyl]-amine trifluoroacetate (0.094 g, 48%) as a tan solid. MP 232-234° C.; LCMS (m/e) 545 (M+1); $^1$H-NMR (DMSO-$d_6$, 400 MHz) δ 9.72 (br, 1H), 8.85 (s, 1H), 7.81-7.79 (d, 1H, J=8.77 Hz), 7.48-7.44 (t, 1H, J=8.37 Hz), 7.38 (s, 1H), 6.89-6.88 (d, 1H, J=4.60 Hz), 6.82-6.80 (d, 2H, J=8.45 Hz), 6.73-6.71 (d, 1H, J=4.60 Hz), 6.68 (s, 1H), 6.35-6.33 (d, 1H, J=8.84 Hz), 4.05-4.02 (d, 2H, J=12.36 Hz), 3.84 (s, 3H), 3.68 (s, 6H), 3.79-3.76 (d, 2H, J=12.44 Hz), 3.65 (s, 1H), 3.50-3.47 (d, 2H, J=11.89 Hz), 3.40-3.35 (br, 1H), 3.13 (br, 2H), 2.72-2.69 (m, 2H), 2.15-2.12 (d, 2H, J=11.60 Hz), 1.73-1.71 (q, 2H, J=8.92 Hz).

Example 543

[(S)-1-(4-{4-[7-(2,6-Dimethoxy-phenyl)-pyrrolo[2,1-f][1,2,4]triazin-2-ylamino]-3-methoxy-phenyl}-piperazin-1-yl)-propan-2-ol trifluoroacetate Following the procedure of example 532 (c), (S)-1-[4-(4-Amino-3-methoxy-phenyl)-piperazin-1-yl]-propan-2-ol (0.16 g, 0.60 mmol) and 7-(2,6-Dimethoxy-phenyl)-2-methanesulfinyl-pyrrolo[2,1-f][1,2,4]triazine (0.10 g, 0.32 mmol) were heated in the microwave at 190° C. for 12 hours. Purification by Gilson chromatography gave (S)-1-(4-{4-[7-(2,6-Dimethoxy-phenyl)-pyrrolo[2,1-f][1,2,4]triazin-2-ylamino]-3-methoxy-phenyl}-piperazin-1-yl)-propan-2-ol trifluoroacetate (0.077 g, 38%) as a tan solid. MP: 179-183° C.; LCMS (m/e) 519 (M+1); $^1$H-NMR (DMSOd$_6$, 400 MHz) δ 9.46 (br, 1H), 8.85 (s, 1H), 7.83-7.80 (d, 1H, J=8.77 Hz), 7.48-7.44 (t, 1H, J=9.36 Hz), 7.38 (s, 1H), 6.89-6.88 (d, 1H, J=4.60 Hz), 6.82-6.80 (d, 2H, J=8.44 Hz), 6.72-6.71 (d, 1H, J=4.56 Hz), 6.68-6.67 (s, 1H), 6.33-6.30 (dd, 1H, J=2.28 Hz), 4.18-4.10 (br, 1H). 3.84 (s, 3H), 3.75-3.72 (m, 2H), 3.68 (s, 6H), 3.57 (m, 2H), 3.18 (m, 3H), 3.11-2.96 (m, 3H), 1.15-1.14 (d, 3H, J=6.16 Hz).

Example 544

[7-(2-Methanesulfinyl-phenyl)-pyrrolo[2,1-f][1,2,4]triazin-2-yl]-[2-methoxy-4-(4-morpholin-4-yl-piperidin-1-yl)-phenyl]-amine trifluoroacetate Following the procedure of example 532 (c), 2-Methoxy-4-(4-morpholin-4-yl-piperidin-1-yl)-phenylamine (0.18 g, 0.62 mmol) and 2-Methanesulfinyl-7-(2-methanesulfinyl-phenyl)-pyrrolo[2,1-f][1,2,4]triazine (0.10 g, 0.31 mmol)were heated in the microwave at 190° C. for 14 hours. Purification by Gilson chromatography gave [7-(2-Methanesulfinyl-phenyl)-pyrrolo[2,1-f][1,2,4]triazin-2-yl]-[2-methoxy-4-(4-morpholin-4-yl-piperidin-1-yl)-phenyl]-amine trifluoroacetate as a tan solid (0.10 g, 49%). MP: 133-138° C.; LCMS (m/e) 547 (M+1); $^1$H-NMR (DMSO-d$_6$, 400 MHz) δ 9.64 (br, 1H), 8.97 (s, 1H), 8.09-8.07 (d, 1H, J=7.72 Hz), 7.79-7.75 (t, 1H, J=7.92 Hz), 7.73-7.70 (q, 2H, J=8.92 Hz), 6.96-6.90 (q, 2H, J=4.52 Hz), 6.65 (s, 1H), 6.33-6.31 (d, 1H, J=8.84 Hz), 5.75 (s, 1H), 4.04-4.01 (d, 1H, J=11.74 Hz), 3.84 (s, 3H), 3.69-3.64 (t, 1H, J=11.65 Hz), 3.50-3.47 (d, 1H, J=12.05 Hz), 3.35 (br, 1H), 3.13 (br, 1H), 2.70-2.64 (t, 1H, J=11.69 Hz), 2.42 (s, 3H), 2.14-2.11 (d, 2H, J=12.13 Hz), 1.70-1.67 (q, 2H).

Example 545

(S)-1-(4-{4-[7-(2-Methanesulfinyl-phenyl)-pyrrolo[2,1-f][1,2,4]triazin-2-ylamino]-3-methoxy-phenyl}-piperazin-1-yl)-propan-2-ol trifluoroacetate Following the procedure of example 532 (c), (S)-1-[4-(4-Amino-3-methoxy-phenyl)-piperazin-1-yl]-propan-2-ol (0.16 g, 0.60 mmol) and 2-Methanesulfinyl-7-(2-methanesulfinyl-phenyl)-pyrrolo[2,1-f][1,2,4]triazine (0.10 g, 0.32 mmol) were heated in the microwave at 190° C. for 4 hours. Purification by Gilson chromatography gave (S)-1-(4-{4-[7-(2-Methanesulfinyl-phenyl)-pyrrolo[2,1-f][1,2,4]triazin-2-ylamino]-3-methoxy-phenyl}-piperazin-1-yl)-propan-2-ol trifluoroacetate as a tan solid (0.11 g, 48%). MP: 57° C.; LCMS (m/e) 521 (M+1); $^1$H-NMR (DMSO-d$_6$, 400 MHz) δ 9.45 (br, 1H), 8.98 (s, 3H), 8.08-8.06 (d, 1H, J=7.72 Hz), 7.79-7.75 (t, 1H, J=2.00 Hz), 7.73 (s, 1H), 7.71 (s, 1H), 7.69 (s, 1H), 7.62-7.60 (d, 2H, J=8.77 Hz), 7.55 (t, 1H), 6.96-6.90 (d, 2H, J=4.60 Hz), 6.68-6.67 (d, 2H, J=2.32 Hz), 6.33-6.30 (dd, 2H, J=2.32 Hz), 6.16 (q, 1H), 5.98-5.97 (d, 1H, J=3.72 Hz), 4.66 (s, 1H), 3.81 (s, 1H), 3.77-3.69 (m, 3H), 3.58-3.55 (d, 2H, J=12.13 Hz), 3.18 (br, 2H), 3.10-2.98 (br, 3H), 2.42 (s, 3H), 1.15-1.13 (d, 3H, J=6.16 Hz).

Example 546

[7-(2,3-Dihydro-1,4-benzodioxin-5-yl)-pyrrolo[2,1-f][1,2,4]triazin-2-yl]-[2-methoxy-4-(4-morpholin-4-yl-piperidin-1-yl)-phenyl]-amine trifluoroacetate Following the procedure of example 532(c), 2-Methoxy-4-(4-morpholin-4-yl-piperidin-1-yl)-phenylamine (0.174 g, 0.597 mmol) and 7-(2,3-Dihydro-1,4-benzodioxin-5-yl)-2-methanesulfinyl-pyrrolo[2,1-f][1,2,4]triazine (0.1 g, 0.3 mmol) were heated in the microwave at 190° C. for 12 hours. Purification by Gilson chromatography gave [7-(2,3-Dihydro-1,4-benzodioxin-5-yl)-pyrrolo[2,1-f][1,2,4]triazin-2-yl]-[2-methoxy-4-(4-morpholin-4-yl-piperidin-1-yl)-phenyl]-amine trifluoroacetate (0.096 g, 50%). MP: 225-226° C.; LCMS (m/e) 543 (M+1); $^1$H-NMR (DMSO-d$_6$, 400 MHz) δ 9.73 (br, 1H), 8.91 (s, 1H), 7.91-7.89 (d, 1H, J=8.76 Hz), 7.57 (s, 1H), 7.44-7.42 (dd, 1H, J=3.16 Hz), 6.97-6.94 (m, 3H), 6.91-6.90 (d, 1H, J=2.64 Hz), 6.71 (s, 1H), 6.44-6.42 (dd, 1H, J=8.81 Hz), 4.28-4.24 (q, 4H, J=4.80 Hz), 4.05-4.02 (d, 2H, J=11.80 Hz), 3.88 (s, 3H), 3.81 (s, 1H) 3.70-3.64 (d, 2H, J=12.29 Hz), 3.51-3.48 (d, 1H, J=12.13 Hz), 3.36 (t, 1H), 3.36 (t, 1H), 3.14 (m, 2H), 2.72-2.66 (t, 2H, J=12.24 Hz), 2.16-2.13 (d, 2H, J=11.44 Hz), 1.73-1.71 (q, 2H, J=8.72 Hz).

Example 547

(S)-1-(4-{4-[7-(2,3-Dihydro-1,4-benzodioxin-5-yl)-pyrrolo[2,1-f][1,2,4]triazin-2-ylamino]-3-methoxy-phenyl}-piperazin-1-yl)-propan-2-ol trifluoroacetate Following the procedure of example 532 (c), (S)-1-[4-(4-Amino-3-methoxy-phenyl)-piperazin-1-yl]-propan-2-ol (0.159 g, 0.599 mmol) and 7-(2,3-Dihydro-1,4-benzodioxin-5-yl)-2-methanesulfinyl-pyrrolo[2,1-f][1,2,4]triazine (0.10 g, 0.3 mmol) were heated in the microwave at 190° C. for 14 hours. Purification by Gilson chromatography gave (S)-1-(4-{4-[7-(2,3-Dihydro-1,4-benzodioxin-5-yl)-pyrrolo[2,1-f][1,2,4]triazin-2-ylamino]-3-methoxy-phenyl}-piperazin-1-yl)-propan-2-ol trifluoroacetate (0.065 g, 30%). MP: 189-191° C.; LCMS (m/e) 517 (M+1); $^1$H-NMR (DMSO-d$_6$, 400 MHz) δ 9.48 (br, 1H), 8.91 (s, 1H), 7.93-7.91 (d, 1H, J=8.72), 7.59 (s, 1H), 7.44-7.41 (dd, 1H, J=3.05 Hz), 6.97-6.93 (m, 3H), 6.92-6.90 (d, 1H, J=4.64 Hz), 6.73-6.72 (d, 1H, J=2.24 Hz), 6.44-6.42 (dd, 1H, J=2.28 Hz), 5.52 (br, 1H), 4.28-4.24 (q, 4H, J=4.84 Hz), 4.13 (br, 1H), 3.86 (s, 3H), 3.80-3.72 (t, 2H), 3.60-3.57 (d, 2H, J=11.16 Hz), 3.41-3.36 (q, 2H, J=7.00 Hz), 3.18 (br, 3H), 3.13-3.01 (m, 3H), 1.15-1.14 (d, 2H, J=6.12 Hz), 1.11-1.07 (t, 1H, J=7.00 Hz).

Example 548

[7-(2,3-Dihydro-1,4-benzodioxin-5-yl)-pyrrolo[2,1-f][1,2,4]triazin-2-yl]-[4-(4-methyl-piperazin-1-yl)-phenyl]-amine A mixture of 4-(4-Methyl-piperazin-1-yl)-phenylamine (0.086 g, 0.45 mmol), 7-(2,3-Dihydro-1,4-benzodioxin-5-yl)-2-methanesulfinyl-pyrrolo[2,1-f][1,2,4]triazine (0.08 g, 0.20 mmol) and Potassium acetate (0.12 g, 1.2 mmol) in Dimethyl sulfoxide (0.9 mL, 10 mmol) was heated in sealed tube at 140° C. for 4 hours. Dilution of the mixture with water (20 mL) and extraction with DCM, gave a brown solid. Purification by prep plate chromatography with DCM-methanol (10-1) gave [7-(2,3-Dihydro-1,4-benzodioxin-5-yl)-pyrrolo[2,1-f][1,2,4]triazin-2-yl]-[4-(4-methyl-piperazin-1-yl)-phenyl]-amine (0.057 g, 50%). MP: 212-213° C.; LCMS (m/e)

443 (M+1); ¹H-NMR (DMSO-d$_6$, 400 MHz) δ 9.16 (s, 1H), 8.91 (s, 1H), 7.60-7.58 (d, 2H, J=9.00 Hz), 7.44-7.42 (dd, 1H, J=4.97 Hz), 7.02-6.96 (q, 2H, J=8.04 Hz), 6.93-6.92 (d, 1H, J=4.65 Hz), 6.88-6.87 (d, 1H, J=4.64 Hz), 6.81-6.79 (d, 2H, J=9.01 Hz), 5.76 (s, 1H), 4.30-4.25 (d, 4H, J=4.88 Hz), 3.32 (s, 3H), 3.03 (s, 3H), 2.45-2.43 (t, 1H, J=4.76 Hz), 2.21 (s, 1H).

Example 549

[7-(2-Methanesulfonylmethyl-phenyl)-pyrrolo[2,1-f][1,2,4]triazin-2-yl]-[2-methoxy-4-(4-morpholin-4-yl-piperidin-1-yl)-phenyl]-amine trifluoroacetate Following the procedure of example 532 (c), 2-Methoxy-4-(4-morpholin-4-yl-piperidin-1-yl)-phenylamine (0.12 g, 0.41 mmol) and 2-Methanesulfinyl-7-(2-methanesulfonylmethyl-phenyl)-pyrrolo[2,1-f][1,2,4]triazine (0.080 g, 0.20 mmol) were heated in the microwave at 190° C. for 6 hours. Purification by Gilson chromatography gave [7-(2-Methanesulfonylmethyl-phenyl)-pyrrolo[2,1-f][1,2,4]triazin-2-yl]-[2-methoxy-4-(4-morpholin-4-yl-piperidin-1-yl)-phenyl]-amine trifluoroacetate (0.052 g, 30%). MP: 93-95° C.; LCMS (m/e) 577 (M+1); ¹H-NMR (DMSO-d$_6$, 400 MHz) δ 9.49 (br, 1H), 8.95 (s, 1H), 7.66 (s, 1H), 7.64 (s, 1H), 7.627.61 (t, 2H, J=4.12 Hz), 7.57-7.53 (q, 2H, J=8.85 Hz), 7.01-6.96 (q, 2H, J=4.60 Hz), 6.67 (s, 1H), 6.39-6.37 (dd, 1H), 4.49 (s, 2H), 4.05-4.02 (d, 2H, J=8.93 Hz), 3.83 (s, 3H), 3.80 (s, 1H), 3.70-3.64 (t, 2H, J=12.40 Hz), 3.50-3.48 (d, 2H, J=11.41 Hz), 3.35 (t, 1H), 3.14 (m, 1H), 2.71-2.67 (t, 1H, J=10.64 Hz), 2.68 (s, 3H), 2.15-2.12 (d, 2H, J=11.89 Hz), 1.71-1.69 (q, 2H, J=8.72 Hz).

Example 550

(R)-3-(4-{2-Fluoro-5-methoxy-4-[7-(2-methoxy-phenyl)-pyrrolo[2,1-f][1,2,4]triazin-2-ylamino]-phenyl}-piperidin-1-yl)-propane-1,2-diol trifluoroacetate Following the procedure of example 532(c), (R)-3-[4-(4-Amino-2-fluoro-5-methoxy-phenyl)-piperidin-1-yl]-propane-1,2-diol (0.055 g, 0.18 mmol) and trifluoro-methanesulfonic acid 7-(2-methoxy-phenyl)-pyrrolo[2,1-f][1,2,4]triazin-2-yl ester (0.069 g, 0.18 mmol) were heated in the microwave at 120° C. for 5 hours. Purification by Gilson chromatography gave (R)-3-(4-{2-Fluoro-5-methoxy-4-[7-(2-methoxy-phenyl)-pyrrolo[2,1-f][1,2,4]triazin-2-ylamino]-phenyl}-piperidin-1-yl)-propane-1,2-diol trifluoroacetate (0.012 g, 9%). LCMS (m/e) 522 (M+1); ¹H-NMR (DMSO-d$_6$, 400 MHz) δ 9.15 (br, 1H), 8.99 (s, 1H), 8.07-8.04 (d, 1H, J=13.17 Hz), 7.75 (s, 1H), 7.72 (s, 1H), 7.49-7.45 (t, 1H, J=7.44 Hz), 7.36-7.26 (m, 1H), 7.21-7.19 (d, 1H, J=8.28 Hz), 7.11-7.07 (t, 1H, J=7.12 Hz), 6.99 (s, 1H), 6.81-6.79 (d, 1H, J=6.64 Hz), 3.89 (s, 1H), 3.81-3.79 (s, 3H), 3.59 (br, 2H), 3.46-3.44 (m, 1H), 3.35-3.31 (q, 1H, J=6.32 Hz), 3.17-3.03 (m, 4H), 2.17-2.14 (d, 1H, J=12.44 Hz), 2.06-2.02 (d, 1H, J=13.56 Hz), 1.94-1.85 (m, 1H).

Example 551

N-[2-(2-{4-[1-((R)-2,3-Dihydroxy-propyl)-piperidin-4-yl]-5-fluoro-2-methoxy-phenylamino}-pyrrolo[2,1-f][1,2,4]triazin-7-yl)-phenyl]-N-methyl-methanesulfonamide trifluoroacetate Following the procedure of example 532 (c), trifluoromethanesulfonic acid 7-[2-(methanesulfonyl-methyl-amino)-phenyl]-pyrrolo[2,1-f][1,2,4]triazin-2-yl ester (0.055 g, 0.12 mmol) (R)-3-[4-(4-Amino-2-fluoro-5-methoxy-phenyl)-piperidin-1-yl]-propane-1,2-diol (0.083 g, 0.28 mmol) were heated in the microwave at 120° C. for 6 hr. Purification by Gilson chromatography gave N-[2-(2-{4-[1-((R)-2,3-Dihydroxy-propyl)-piperidin-4-yl]-5-fluoro-2-methoxy-phenylamino}-pyrrolo[2,1-f][1,2,4]triazin-7-yl)-phenyl]-N-methyl-methanesulfonamide trifluoroacetate (0.013 g, 14%). LCMS (m/e) 599 (M+1); ¹H-NMR (DMSO-d$_6$, 400 MHz) δ 9.14 (br, 1H), 9.00 (s, 1H), 8.00-7.98 (d, 1H, J=7.77 Hz), 7.95-7.92 (d, 1H), 7.79 (s, 1H), 7.68-7.67 (d, 1H, J=12.93 Hz), 7.57-7.49 (q, 2H, J=7.05 Hz), 7.05-7.01 (q, 2H, J=4.68 Hz), 6.81-6.79 (d, 1H, J=6.80 Hz), 3.90 (m, 3H), 3.87 (s, 3H), 3.48-3.44 (q, 2H, J=4.92 Hz), 3.33-3.31 (q, 2H, J=4.36 Hz), 3.18 (br, 2H), 3.08 (s, 3H), 3.02 (br, 2H), 2.90 (s, 3H).

Example 561

N-tert-Butyl-3-[2-(4-morpholin-4-yl-phenylamino)-pyrrolo[2,1-f][1,2,4]triazin-7-yl]-benzenesulfonamide The title compound was prepared in the following manner from N-tert-Butyl-3-(2-methylsulfanyl-pyrrolo[2,1-f][1,2,4]triazin-7-yl)-benzenesulfonamide (0.1 g, 0.3 mmol), 4-(4-morpholino)aniline (90 mg, 0.5 mmol), N,N-Diisopropylethylamine (0.124 mL, 0.712 mmol), and 1-Methoxy-2-propanol (0.5 mL, 5 mmol) were heated in the microwave at 250° C. for 30 minutes. An LCMS showed product and left over amine. The reaction was concentrated and redissolved in 3 ml of DMSO and placed onto the Gilson. The most pure fractions were combined basified with sat. sodium bicarbonate and extracted with DCM, dried filtered and concentrated to give N-tert-Butyl-3-[2-(4-morpholin-4-yl-phenylamino)-pyrrolo-[2,1-f][1,2,4]triazin-7-yl]-benzenesulfonamide as a yellow solid (30 mg, 20%). MP 225-226 C. LCMS (E/I+) 507 (M+H). NMR 1H (DMSO-d$_6$)-9.40 (bs, 1H), 8.96 (bs, 1H), 8.52 (bs, 1H), 7.77 (d, 1H, J=7.40 Hz), 7.50-7.45 (m, 2H), 7.22-7.05 (m, 4H), 6.93 (s, 2H), 6.54 (d, 1H, J=7.91 Hz), 4.45-4.40 (m, 1H), 3.18-3.25 (m, 2H), 3.04-3.11 (m, 2H), 1.98-2.06 (m, 2H), 1.74-1.84 (m, 2H).

Example 562

N-tert-Butyl-3-(2-{4-[4-(3-oxo-piperazin-1-yl)-piperidin-1-yl]-phenylamino}-pyrrolo[2,1-f][1,2,4]triazin-7-yl)-benzenesulfonamide The title compound was prepared in an analogous fashion to Example 561 to give as a yellow solid (30 mg, 20%). MP 235-236 C. LCMS (E/I+) 603 (M+H). NMR 1H (DMSO-d6)-9.77 (s, 1H), 8.98 (s, 1H), 8.54 (s, 1H), 8.39-8.35 (d, 1H, J=7.80 Hz), 7.86-7.82 (d, 1H, J=7.87 Hz), 7.70-7.76 (m, 3H), 7.62-7.68 (m, 2H), 7.16 (d, 1H, J=4.81 Hz), 6.94-6.98 (m, 2H), 3.63 (d, 2H, J=12.73 Hz), 3.11-3.15 (m, 1H), 3.05 (s, 1H), 2.56-2.68 (m, 3H), 1.85 (d, 1H, J=11.88 Hz), 1.48-1.58 (m, 1H), 1.11 (s, 9H)

Example 563

3-{1-[7-(3-Methanesulfonyl-phenyl)-pyrrolo[2,1-f][1,2,4]triazin-2-yl]-piperdin-4-yloxy}-phenylamine The title compound was prepared in an analogous fashion to Example 561 to give a yellow solid (34 mg, 10%). LCMS (E/I+) 578 (M+H). NMR 1H (DMSO-d6)-9.20 (s, 1H), 9.00 (s, 1H), 8.38 (d, 1H, J=7.96 Hz), 7.87 (d, 1H, J=7.97 Hz), 7.75

(t, 1H, J=8.04 Hz), 7.39 (d, 1H, J=4.99 Hz), 7.23 (t, 1H, J=8.10 Hz), 6.97 (d, 1H, J=4.97 Hz), 6.75 (d, 1H, J=8.13 Hz), 6.68 (s, 1H), 6.64 (d, 1H, J=8.10 Hz), 4.63-4.70 (m, 1H), 4.10-4.20 (m, 2H), 3.55-3.62 (m, 2H), 3.24 (s, 3H), 2.00-2.10 (m, 2H), 1.65-1.76 (m, 2H).

Example 564

[7-(2-Methoxy-phenyl)-pyrrolo[2,1-f][1,2,4]triazin-2-yl]-(2-methyl-benzoxazol-5-yl)-amine The Title compound was prepared in the following manner: A mixture of Trifluoro-methanesulfonic acid 7-(2-methoxy-phenyl)-pyrrolo[2,1-f][1,2,4]triazin-2-yl ester (100 mg, 0.3 mmol), 2-Methyl-benzoxazol-5-ylamine; hydrochloride (100 mg, 0.5 mmol), N,N-Diisopropylethylamine (2 mL, 10 mmol), and 1-Methoxy-2-propanol (0.3 mL, 3 mmol) were heated at 80° C. overnight. The reaction was concentrated, filtered and placed onto the Gilson. The pure fractions were lyophilized to give a yellow solid (30 mg, 20%). LCMS (E/I+) 372 (M+H). NMR 1H (DMSO-d6)-9.5 (s, 1H), 9.0 (s, 1H), 8.2 (s, 1H), 7.78 (d, 1H, J=7.80 Hz), 7.45-7.54 (m, 3H), 7.23 (d, 1H, J=8.26), 7.12 (t, 1H, J=7.51 Hz), 6.92-6.96 (m, 2H), 3.84 (s, 3H), 2.58 (s, 3H).

Example 565

N-tert-Butyl-3-{2-[4-(4-morpholin-4-yl-cyclohexyl)-phenylamino]-pyrrolo[2,1-f][1,2,4]triazin-7-yl}-benzenesulfonamide The title compound was prepared in the following manner: N-tert-Butyl-3-(2-hydroxy-pyrrolo[2,1-f][1,2,4]triazin-7-yl)-benzenesulfonamide (70 mg, 0.2 mmol), N-Phenylbis(tri-fluoromethanesulphonimide) (82.6 mg, 0.231 mmol), N,N-Diisopropylethylamine (0.11 mL, 0.62 mmol), and N,N-Dimethylformamide (2 mL, 20 mmol) and stir at room temperature for half an hour. Added 4-(4-Morpholin-4-yl-cyclohexyl)-phenylamine (280 mg, 1.1 mmol) and stir at 80° C. overnight. The mixture was concentrated and purified using the gilson. The most pure fractions were combined basified with sat. sodium bicarbonate and extracted with DCM, dried filtered and concentrated to give a yellow solid (30 mg, 20%). MP 160-163 C. LCMS (E/I+) 589 (M+H). NMR 1H (DMSO-d6)-9.44 (s, 1H), 9.02 (s, 1H), 8.57 (s, 1H), 8.33-8.40 (m, 1H), 7.86 (d, 1H, J=8.03), 7.59-7.76 (m, 3H), 7.18-7.24 (m, 2H), 6.98 (d, 1H, J=4.8 Hz), 3.60-3.64 (m, 2H), 3.55-3.59 (m, 1H), 2.55-2.64 (m, 1H), 2.49-2.51 (m, 4H), 2.36-2.42 (m, 2H), 2.14-2.19 (m, 1H), 1.89-1.98 (m, 2H), 1.78-1.88 (m, 2H), 1.44-1.54 (m, 4H), 1.11 (s, 9H).

Example 566

N-tert-Butyl-3-{2-[4-(4-pyrrolidin-1-yl-cyclohexyl)-phenylamino]-pyrrolo[2,1-f][1,2,4]triazin-7-yl}-benzenesulfonamide The title compound was prepared in an analogous fashion to Example 565 to give a yellow solid (70 mg, 60%). MP 186-189 C. LCMS (E/I+) 573 (M+H). NMR 1H (DMSO-d6)-9.43 (s, 1H), 9.02 (s, 1H), 8.54 (s, 1H), 8.37 (d, 1H, J=7.82 Hz), 7.85 (d, 1H, J=7.74 Hz), 7.70-7.78 (m, 1H), 7.59-7.68 (m, 2H), 7.17-7.22 (m, 2H), 6.98 (d, 1H, J=4.8 Hz), 2.44-2.48 (m, 2H), 2.20 (m, 1H), 2.05 (m, 1H), 1.2-1.9 (m, 11H), 1.10 (s, 9H).

Example 567

N-tert-Butyl-3-{2-[4-(4-dimethylamino-cyclohexyl)-phenylamino]-pyrrolo[2,1-f][1,2,4]triazin-7-yl}-benzenesulfonamide The title compound was prepared in an analogous fashion to Example 565 to give a yellow solid (17 mg, 20%). MP 172-174C. LCMS (E/I+) 547 (M+H). NMR 1H (DMSO-d6)-9.43-9.45 (m, 1H), 9.0 (s, 1H), 8.55 (s, 1H), 8.37 (d, 1H, J=7.91 Hz), 7.85 (d, 1H, J=7.73 Hz), 7.73 (t, 1H, J=7.85 Hz), 7.65 (d, 2H, J=8.40 Hz), 7.61 (s, 1H), 7.18-7.22 (m, 2H), 6.99 (d, 1H, J=4.7 Hz), 3.32 (s, 6H), 2.34-2.42 (m, 1H), 1.80-2.0 (m, 4H), 1.20-1.55 (m, 5H), 1.10 (s, 9H).

Example 568

N-tert-Butyl-3-{2-[4-(4-hydroxy-cyclohexyl)-phenylamino]-pyrrolo[2,1-f][1,2,4]triazin-7-yl}-benzenesulfonamide The title compound was prepared in an analogous fashion to Example 565 to give a yellow solid (57 mg, 50%). MP174-176 C. LCMS (E/I+) 520 (M+H). NMR 1H (DMSO-d6)-9.44 (s, 1H), 9.02 (s, 1H), 8.53 (s, 1H), 8.38 (d, 1H, J=7.76), 7.85 (d, 1H, J=8.09 Hz), 7.75 (t, 1H, J=8.00 Hz), 7.61-7.67 (m, 3H), 7.17-7.21 (m, 3H), 6.98 (d, 1H, J=4.65 Hz), 6.84 (d, 1H, J=8.17 Hz), 6.45 (d, 1H, J=8.3 Hz), 3.40-3.48 (m, 1H), 2.32-2.42 (m, 1H), 1.65-1.95 (m, 4H), 1.20-1.50 (m, 4H), 1.12 (s, 9H).

Example 569

N-tert-Butyl-3-{2-[3-(1-hydroxy-ethyl)-phenylamino]-pyrrolo[2,1-f][1,2,4]triazin-7-yl}-benzenesulfonamide The title compound was prepared in an analogous fashion to Example 565 to give a yellow solid (33 mg, 40%). MP114-116 C. LCMS (E/I+) 466 (M+H). NMR 1H (DMSO-d6)-9.50 (s, 1H), 9.05 (s, 1H), 8.35 (d, 1H, J=7.74 Hz), 8.40 (s, 1H), 7.84 (d, 1H, J=8.00 Hz), 7.76 (t, 1H, J=8.02 Hz), 7.65-7.69 (m, 2H), 7.62 (s, 1H), 7.30 (t, 1H, J=7.91 Hz), 7.20 (d, 1H, J=4.85), 7.05 (d, 1H, J=4.80 Hz), 6.96 (d, 1H, J=7.54 Hz), 5.13 (d, 1H, J=3.92 Hz), 4.64-4.72 (m, 1H), 1.29 (d, 3H, J=6.46 Hz), 1.11 (s, 9H).

Example 570

2-[4-(4-{7-[3-(Propane-2-sulfonyl)-phenyl]-pyrrolo[2,1-f][1,2,4]triazin-2-ylamino}-phenyl)-piperidin-1-yl]-acetamide The title compound was prepared in an analogous fashion to Example 565 to give a yellow solid (47 mg, 40%). MP 235-237 C. LCMS (E/I+) 533 (M+H). NMR 1H (DMSO-d6)-9.49 (s, 1H), 9.03 (s, 1H), 8.57 (d, 1H, J=8.02), 8.50 (s, 1H), 7.80-7.90 (m, 2H), 7.66 (d, 2H, J=8.14 Hz), 7.29 (d, 1H, J=4.69 Hz), 7.18-7.24 (m, 2H), 7.13 (s, 1H), 6.99 (d, 1H, J=4.88 Hz), 3.48-3.58 (m, 1H), 2.86-2.94 (m, 4H), 2.38-2.46 (m, 1H), 2.10-2.20 (m, 2H), 1.68-1.76 (m, 4H), 1.19 (d, 6H, J=6.60 Hz).

Example 571

N-tert-Butyl-3-{2-[4-(4-methoxyimino-cyclohexyl)-phenylamino]-pyrrolo[2,1-f][1,2,4]triazin-7-yl}-benzenesulfonamide The title compound was prepared in an analogous fashion to Example 565 to give a yellow solid (31 mg, 30%). MP172-173 C. LCMS (E/I+) 547 (M+H). NMR 1H (DMSO-d6)-9.50 (s, 1H), 9.0 (s, 1H), 8.54 (s, 1H), 8.37 (d, 1H, J=7.88), 7.85 (d, 1H, J=7.86), 7.75 (t, 1H, J=7.90), 7.67 (d, 2H, J=8.27), 7.62 (s, 1H), 7.22 (d, 1H, J=8.53), 7.19 (d, 1H, J=4.77), 6.99 (d, 1H, J=4.72), 3.74 (s, 3H), 3.15-3.21 (m, 1H), 2.68-2.78 (m, 1H), 2.15-2.40 (m, 2H), 1.85-2.00 (m, 3H), 1.45-1.65 (m, 2H), 1.11 (s, 9H).

Example 572

N-tert-Butyl-3-[2-(2-methyl-benzothiazol-6-ylamino)-pyrrolo[2,1-f][1,2,4]triazin-7-yl]-benzenesulfonamide The title compound was prepared in an analogous fashion to Example 565 to give a yellow solid (34 mg, 30%). MP 196-198 C. LCMS (E/I+) 493 (M+H). NMR 1H (DMSO-d6)-9.83 (s, 1H), 9.10 (s, 1H), 8.53 (d, 1H, J=7.84), 8.49 (s, 1H), 8.39 (s, 1H), 7.85-7.90 (m, 2H), 7.72-7.78 (m, 2H), 7.63 (s, 1H), 7.21 (d, 1H, J=4.70), 7.03 (d, 1H, J=4.77), 2.77 (s, 3H), 1.11 (s, 9H).

Example 573

3-[2-(Benzothiazol-6-ylamino)-pyrrolo[2,1-f][1,2,4]triazin-7-yl]-N-tert-butyl-benzenesulfonamide The title compound was prepared in an analogous fashion to Example 565 to give a yellow solid (38 mg, 40%). MP 214-216 C. LCMS (E/I+) 492 (M+H). NMR 1H (DMSO-d6)-9.92 (s, 1H), 9.22 (s, 1H), 9.10 (s, 1H), 8.63 (s, 1H), 8.53 (d, 1H, J=7.95), 8.41 (s, 1H), 8.40 (d, 1H, J=8.65), 7.90 (d, 1H, J=7.90), 7.75-7.83 (m, 2H), 7.63 (s, 1H), 7.22 (d, 1H, J=4.79), 7.04 (d, 1H, J=4.68), 1.11 (s, 9H).

Example 574

N-tert-Butyl-3-[2-(2-methyl-benzothiazol-5-ylamino)-pyrrolo[2,1-f][1,2,4]triazin-7-yl]-benzenesulfonamide The titled compound was prepared in an analogous fashion to Example 565c replacing 4-(4-Morpholin-4-yl-cyclohexyl)-phenylamine with 5-Amino-2-methylbenzothiazole to give N-tert-Butyl-3-[2-(2-methyl-benzothiazol-5-ylamino)-pyrrolo[2,1-f][1,2,4]triazin-7-yl]-benzenesulfonamide as a yellow solid (32 mg, 30%). MP 214-217° C. LCMS (E/I+) 493 (M+H). NMR 1H (DMSO-d6)-9.76 (s, 1H), 9.08 (s, 1H), 8.60 (d, 1H, J=7.57 Hz), 8.45 (s, 1H), 8.32 (s, 1H), 7.94 (d, 1H, J=8.63 Hz), 7.83-7.88 (m, 2H), 7.76 (t, 1H, J=7.67 Hz), 7.69 (s, 1H), 7.24 (d, 1H, J=4.67 Hz), 7.03 (d, 1H, J=4.65 Hz), 2.80 (s, 3H), 1.12 (s, 9H).

Example 575

3-[2-(Benzothiazol-5-ylamino)-pyrrolo[2,1-f][1,2,4]triazin-7-yl]-N-tert-butyl-benzenesulfonamide The titled compound was prepared in an analogous fashion to Example 565c replacing 4-(4-Morpholin-4-yl-cyclohexyl)-phenylamine with Benzothiazol-5-ylamine to give 3-[2-(Benzothiazol-5-ylamino)-pyrrolo[2,1-f][1,2,4]triazin-7-yl]-N-tert-butyl-benzenesulfonamide as a yellow solid (51 mg, 50%). MP 261-262° C. LCMS (E/I+) 479 (M+H). NMR 1H (DMSO-d6)-9.84 (s, 1H), 9.38 (s, 1H), 9.09 (s, 1H), 8.65 (d, 1H, J=7.73 Hz), 8.57 (s, 1H), 8.44 (s, 1H), 8.08 (d, 1H, J=8.69 Hz), 7.85-7.90 (m, 2H), 7.76 (t, 1H, J=8.05 Hz), 7.68 (s, 1H), 7.25 (d, 1H, J=4.78 Hz), 7.04 (d, 1H, J=4.68 Hz), 1.12 (s, 9H).

Example 576

4-(4-{7-[3-(Propane-2-sulfonyl)-phenyl]-pyrrolo[2,1-f][1,2,4]triazin-2-ylamino}-phenyl)-cyclohexanone O-methyl-oxime The titled compound was prepared in an analogous fashion to Example 565c replacing 4-(4-Morpholin-4-yl-cyclohexyl)-phenylamine with 4-(4-Amino-phenyl)-cyclohexanone O-methyl-oxime to give 4-(4-{7-[3-(Propane-2-sulfonyl)-phenyl]-pyrrolo[2,1-f][1,2,4]triazin-2-ylamino}-phenyl)-cyclohexanone O-methyl-oxime as a yellow solid (29 mg, 20%). MP 172-178° C. LCMS (E/I+) 518 (M+H). NMR 1H (DMSO-d6)-9.49 (s, 1H), 9.03 (s, 1H), 8.56 (d, 1H, J=7.43 Hz), 8.50 (s, 1H), 7.83-7.90 (m, 2H), 7.65 (d, 2H, J=8.41 Hz), 7.29 (d, 1H, J=4.80 Hz), 7.22 (d, 2H, J=8.47 Hz), 6.99 (d, 1H, J=4.73 Hz), 3.73 (s, 3H), 3.48-3.58 (m, 1H), 3.16-3.21 (m, 1H), 2.68-2.80 (m, 1H), 2.33-2.39 (m, 1H), 2.21-2.30 (m, 1H), 1.85-2.0 (m, 3H), 1.45-1.65 (m, 2H), 1.18 (d, 6H, J=6.8 Hz).

Example 577

2-(3-{4-[7-(3-tert-Butylsulfamoyl-phenyl)-pyrrolo[2,1-f][1,2,4]triazin-2-ylamino]-phenyl}-azetidin-1-yl)-acetamide 577a) Into a sealed tube was added 4-Azetidin-3-yl-phenylamine; dihydrochloride (500 mg, 0.002 mol), Iodoacetamide (418.2 mg, 0.002261 mol), Cesium Carbonate (2.210 g, 0.006783 mol) and Acetonitrile (40 mL, 0.8 mol) and the reaction was stirred overnight at 70° C. The reaction was filtered and the filtrate concentrated. Crude Yield=375 mg 577b) The titled compound was prepared in an analogous fashion to Example 565c replacing 4-(4-Morpholin-4-yl-cyclohexyl)-phenylamine with 2-[3-(4-Amino-phenyl)-azetidin-1-yl]-acetamide to give 2-(3-{4-[7-(3-tert-Butylsulfamoyl-phenyl)-pyrrolo[2,1-f][1,2,4]triazin-2-ylamino]-phenyl}-azetidin-1-yl)-acetamide as a yellow solid (12 mg, 10%). MP 202-204° C. LCMS (E/I+) 534 (M+H). NMR 1H (DMSO-d6)-9.51 (s, 1H), 9.03 (s, 1H), 8.55 (s, 1H), 8.36 (d, 1H, J=8.30 Hz), 7.87 (d, 1H, J=7.78 Hz), 7.68-7.77 (m, 3H), 7.62 (s, 1H), 7.33 (d, 2H, J=7.87 Hz), 7.19-7.21 (m, 1H), 7.20 (s, 1H), 7.06 (s, 1H), 6.99 (m, 1H), 3.69-3.75 (m, 2H), 3.55-3.64 (m, 1H), 3.14-3.20 (m, 2H) 3.03 (s, 2H), 1.12 (s, 9H).

Example 578

2-(3-{4-[7-(3-Methanesulfonyl-phenyl)-pyrrolo[2,1-f][1,2,4]triazin-2-ylamino]-phenyl}-azetidin-1-yl)-acetamide The titled compound was prepared in an analogous fashion to Example 565c replacing 4-(4-Morpholin-4-yl-cyclohexyl)-phenylamine with 2-[3-(4-Amino-phenyl)-azetidin-1-yl]-acetamide to give 2-(3-{4-[7-(3-Methanesulfonyl-phenyl)-pyrrolo[2,1-f][1,2,4]triazin-2-ylamino]-phenyl}- azetidin-1-yl)-acetamide as a yellow solid (9 mg, 8%). MP 215-217° C. LCMS (E/I+) 477 (M+H). NMR 1H (DMSO-d6)-9.53 (s, 1H), 9.04 (s, 1H), 8.61 (s, 1H), 8.47 (d, 1H, J=7.82 Hz), 7.95 (d, 1H, J=7.76 Hz), 7.83 (t, 1H, J=7.86 Hz), 7.69 (d, 2H, J=8.19 Hz), 7.33 (d, 1H, J=8.32 Hz), 7.28 (d, 1H, J=4.82 Hz), 7.12 (s, 1H), 7.06 (s, 1H), 7.00 (d, 1H, J=4.69 Hz), 3.71 (t, 2H, J=7.42 Hz), 3.54-3.64 (m, 1H), 3.30 (s, 3H), 3.17 (t, 2H, J=6.77 Hz), 3.03 (s, 2H).

Example 579

2-(4-{4-[7-(2-Methane sulfonyl-2,3-dihydro-1H-isoindol-4-yl)-pyrrolo[2,1-f][1,2,4]triazin-2-ylamino]-phenyl}-piperidin-1-yl)-acetamide 579a) To a solution of 4-Bromo-2,3-dihydro-1H-isoindole; hydrochloride (0.5 g, 2 mmol) in Methylene chloride (20 mL, 300 mmol) was added Triethylamine (0.65 mL, 4.7 mmol) and then Methanesulfonyl chloride (0.182 mL, 2.35 mmol). The reaction went from cloudy to colorless and clear. An LCMS after 2 hr at room temperature showed all product. 1NHCl was added to the reaction and the DCM separated, dried, filtered and concentrated.
Yield=0.507 gm.

579b) A mixture of 4-Bromo-2-methanesulfonyl-2,3-dihydro-1H-isoindole (0.5 g, 2 mmol), Potassium acetate (0.554 g, 5.65 mmol), 4,4,5,5,4',4',5',5'-Octamethyl-[2,2']bi[[1,3,2]]dioxaborolanyl] (0.574 g, 2.26 mmol), and [1,1'-Bis(diphenylphosphino)ferrocene]dichloropalladium(II), complex with dichloromethane (1:1) (44.4 mg, 0.0543 mmol) was slurried in N,N-Dimethylformamide (12 mL, 160 mmol), degassed by nitrogen and warmed at 80° C. overnight. Solvent was removed by rotary evaporation, the residue taken up in DCM, filtered through celite and concentrated. Purified using a 40 gm column eluting with DCM to 1:1 DCM/EtOAc. Yield=0.224 gm.

579c) 2-{4-[4-(7-Bromo-pyrrolo[2,1-f][1,2,4]triazin-2-ylamino)-phenyl]-piperidin-1-yl}-acetamide (150 mg, 0.00035 mol), 2-Methanesulfonyl-4-(4,4,5,5-tetramethyl-1,3,2-dioxaborolan-2-yl)-2,3-dihydro-1H-isoindole (169.4 mg, 0.0005241 mol), 0.9 M of Sodium carbonate in water (0.23 mL, 0.00021 mol), Tetrakis(triphenylphosphine)palladium (O) (0.040 g, 0.000035 mol) and Tetrahydrofuran (2 mL, 0.03 mol) were heated at 80° C. overnight. The reaction was cooled to RT, dissolved partially in DCM and filtered. The filtrate was placed onto a 40 gm column eluting with DCM to 5% MeOH/DCM. Dissolved in DMSO, filtered and placed onto the Gilson. Most pure fractions were free based and worked up to give 2-(4-{4-[7-(2-Methanesulfonyl-2,3-dihydro-1H-isoindol-4-yl)-pyrrolo[2,1-f][1,2,4]triazin-2-ylamino]-phenyl}-piperidin-1-yl)-acetamide as a yellow solid (3.7 mg, 1.9%). MP 244-247° C. LCMS (E/I+) 546 (M+H). NMR 1H (DMSO-d6)-9.45 (s, 1H), 9.01 (s, 1H), 7.97 (d, 1H, J=7.77 Hz), 7.62 (d, 2H, J=8.60 Hz), 7.56 (t, 1H, J=7.68 Hz), 7.44 (d, 1H, J=7.54 Hz), 7.20 (s, 1H), 7.12 (s, 1H), 7.10 (d, 1H, J=8.51 Hz), 7.06 (d, 1H, J=4.63 Hz), 6.98 (d, 1H, J=4.80 Hz), 4.74 (s, 4H), 2.91-2.92 (m, 4H), 2.86-2.89 (m, 3H), 2.38-2.42 (m, 1H), 2.10-2.20 (m, 2H), 1.65-1.74 (m, 4H).

Example 580

2-(4-{4-[7-(3,6-Dimethoxy-pyridazin-4-yl)-pyrrolo[2,1-f][1,2,4]triazin-2-ylamino]-phenyl}-piperidin-1-yl)-acetamide 580a) In a sealed tube 3,6-Dimethoxy-pyridazin-4yl boronic acid (0.9 g, 0.005 mol), [A] 7-Bromo-2-methylsulfanyl-pyrrolo[2,1-f][1,2,4]triazine (0.977 g, 0.00400 mol), 1,1'-bis(di-tert-butylphosphino)ferrocene (86.6 mg, 0.000245 mol) and Palladium Acetate (55.5 mg, 0.000247 mol) were added to degassed 1,4-Dioxane (10 mL, 0.1 mol). After 30 minutes, degassed 0.9 M of Sodium carbonate in water (14.7 mL, 0.0132 mol) was added and the reaction heated at 110° C. for 2 hr under nitrogen. An LCMS showed product and no starting material. The reaction was concentrated, divided between DCM and water. The DCM layer was separated, dried, filtered and concentrated. Upon addition of ether a precipitate formed it was filtered to give 1.1 gm (90%).

580b) Sodium Tungstate Dihydrate (120.8 mg, 0.3662 mmol) and 7-(3,6-Dimethoxy-pyridazin-4-yl)-2-methylsulfanyl-pyrrolo[2,1-f][1,2,4]triazine (1.1 g, 3.6 mmol) were combined in Methanol (50 mL, 1000 mmol) and 50% aq. Hydrogen peroxide (1:1, Hydrogen peroxide:Water, 1.333 mL, 21.76 mmol) was added and the reaction was stirred at 60° C. The compound was very insoluble so Acetic acid (50 mL, 900 mmol) was added and the temperature raised to 80 C. The compound did dissolve and after stirring overnight the reaction was done via LCMS. The reaction was cooled to RT and sat. Sodium thiosulfate (10 mL) was added and the reaction filtered and washed with water and ether. Yield=1.2 gm (99%)

580c) 10 M of Sodium hydroxide in water (20 mL, 200 mmol) was heated at 100° C. 7-(3,6-Dimethoxy-pyridazin-4-yl)-2-methanesulfonyl-pyrrolo[2,1-f][1,2,4]triazine (1.2 g, 3.6 mmol) was added portion wise. The reaction mixture was heated at 120° C. for 2 hr. LCMS showed no starting material and product was there. The reaction was cooled to room temperature. Glacial acetic acid was added to adjust pH to 4. The solid was filtered, washed with water and subsequently with ethyl ether. The resulting solid was dried under vacuum. NMR looks good. Yield=333 mg.

580d) 7-(3,6-Dimethoxy-pyridazin-4-yl)-pyrrolo[2,1-f][1,2,4]triazin-2-ol (70 mg, 0.2 mmol), N-Phenylbis(trifluoromethanesulphonimide) (95.1 mg, 0.266 mmol), N,N-Diisopropylethylamine (0.126 mL, 0.726 mmol), and N,N-Dimethylformamide (2 mL, 30 mmol) and stir at room temperature for half an hour. Add 2-[4-(4-Amino-phenyl)-piperidin-1-yl]-acetamide (90.3 mg, 0.387 mmol) and stir at 60° C. overnight. An LCMS showed product. The reaction was concentrated, DMSO added, filtered and placed onto the Gilson for purification. The most pure fractions were collected, free based with saturated sodium bicarbonate, extracted with DCM, filtered and concentrated to give 2-(4-{4-[7-(3,6-Dimethoxy-pyridazin-4-yl)-pyrrolo[2,1-f][1,2,4]triazin-2-ylamino]-phenyl}-piperidin-1-yl)-acetamide as a yellow solid (15 mg, 10%). MP 249-251° C. LCMS (E/I+) 489 (M+H). NMR 1H (DMSO-d6)-9.56 (s, 1H), 9.1 (s, 1H), 8.27 (s, 1H), 7.60 (d, 2H, J=8.30 Hz), 7.40 (d, 2H, J=4.82 Hz), 7.21 (bs, 1H), 7.18 (d, 1H, J=8.42 Hz), 7.13 (bs, 1H), 6.97 (d, 1H, J=4.87 Hz), 4.06 (s, 3H), 4.04 (s, 3H), 2.87-2.96 (m, 4H), 2.40-2.48 (m, 1H), 2.14-2.25 (m, 2H), 1.70-1.78 (m, 4H).

Example 581

2-(3-{4-[7-(3,6-Dimethoxy-pyridazin-4-yl)-pyrrolo[2,1-f][1,2,4]triazin-2-ylamino]-phenyl}-azetidin-1-yl)-acetamide The titled compound was prepared in an analogous fashion to Example 580d replacing 2-[4-(4-Amino-phenyl)-piperidin-1-yl]-acetamide with 2-[3-(4-Amino-phenyl)-azetidin-1-yl]-acetamide to give 2-(3-{4-[7-(3,6-Dimethoxy-pyridazin-4-yl)-pyrrolo[2,1-f][1,2,4]triazin-2-ylamino]-phenyl}-azetidin-1-yl)-acetamide as a yellow solid (7 mg, 6%). MP 215-217° C. LCMS (E/I+) 461 (M+H). NMR 1H (DMSO-d6)-9.62 (s, 1H), 9.11 (s, 1H), 8.29 (s, 1H), 7.63 (d, 2H, J=8.36 Hz), 7.42 (d, 1H, J=4.85 Hz), 7.30 (d, 2H, J=8.39 Hz), 7.13 (bs, 1H), 7.07 (bs, 1H), 6.98 (d, 1H, J=5.00 Hz), 4.07 (s, 3H), 4.05 (s, 3H), 3.74 (t, 2H, J=7.10 Hz), 3.59-3.64 (m, 1H), 3.19 (t, 2H, J=6.77 Hz), 3.05 (s, 2H).

Example 582

2-(3-{4-[7-(2-Methanesulfonyl-2,3-dihydro-1H-isoindol-4-yl)-pyrrolo[2,1-f][1,2,4]triazin-2-ylamino]-phenyl}-azetidin-1-yl)-acetamide 582a) 7-Bromo-pyrrolo[2,1-f][1,2,4]triazin-2-ol (200 mg, 0.001 mol), 2-Methanesulfonyl-4-(4,4,5,5-tetramethyl-1,3,2-dioxaborolan-2-yl)-2,3-dihydro-1H-isoindole (400 mg, 0.001 mol), 0.9 M of Sodium carbonate in water (10 mL, 0.01 mol), Tetrakis(triphenylphosphine)palladium (O) (120 mg, 0.00010 mol) and 1,4-Dioxane (7 mL, 0.08 mol) were heated at 110° C. 1 hr. Cooled to RT added water and EtOAc. The EtOAc layer was separated, dried, filtered and concentrated. The product was precipitated with ether and filtered. Yield=150 mg 582b) 7-(2-Methanesulfonyl-2,3-dihydro-1H-isoindol-4-yl)-pyrrolo[2,1-f][1,2,4]triazin-2-ol (80 mg, 0.2 mmol), N-Phenylbis(trifluoromethanesulphonimide) (95.1 mg, 0.266 mmol), N,N-Diisopropylethylamine (0.126 mL, 0.726 mmol), and N,N-Dimethylformamide (2 mL, 30 mmol) and stir at room temperature for half an hour. Add 2-[3-(4-Aminophenyl)-azetidin-1-yl]-acetamide (71 mg, 0.34 mmol) and stir at 60° C. overnight. The reaction was concentrated, DMSO added, filtered and placed onto the Gilson for purification. The most pure fractions were collected, basified with sat sodium bicarbonate extracted with EtOAc, dried, filtered and concentrated to give a yellow solid (8 mg, 6%). MP 216-218° C. LCMS (E/I+) 518 (M+H). NMR 1H (DMSO-d6)-9.48 (s, 1H), 9.02 (s, 1H), 7.97 (d, 1H, J=7.81 Hz), 7.64 (d, 2H, J=8.55 Hz), 7.56 (t, 1H, J=7.80 Hz), 7.44 (d, 1H, J=7.74 Hz), 7.21 (d, 2H, J=8.34 Hz), 7.12 (bs, 1H), 7.05-7.08 (m, 2H), 6.99 (d, 1H, J=4.69 Hz), 4.74 (s, 4H), 3.69 (t, 2H, J=7.40 Hz), 3.53-3.61 (m, 1H), 3.15 (t, 2H, J=6.86 Hz), 3.02 (s, 2H), 2.92 (s, 3H).

Example 583

2-(3-{4-[7-(2-Methoxy-phenyl)-pyrrolo[2,1-f][1,2,4]triazin-2-ylamino]-phenyl}-azetidin-1-yl)-acetamide The titled compound was prepared in an analogous fashion to Example 582b replacing 7-(2-Methanesulfonyl-2,3-dihydro-1H-isoindol-4-yl)-pyrrolo[2,1-f][1,2,4]triazin-2-ol with 7-(2-Methoxy-phenyl)-pyrrolo[2,1-f][1,2,4]triazin-2-ol to give 2-(3-{4-[7-(2-Methoxy-phenyl)-pyrrolo[2,1-f][1,2,4]triazin-2-ylamino]-phenyl}-azetidin-1-yl)-acetamide as a yellow solid (8 mg, 6%). MP 174-176° C. LCMS (E/I+) 429 (M+H). NMR 1H (DMSO-d6)-9.35 (s, 1H), 8.94 (s, 1H), 7.80 (d, 1H, J=7.86 Hz), 7.65 (d, 2H, J=8.37 Hz), 7.48 (t, 1H, J=8.08 Hz), 7.23 (d, 1H, J=8.50 Hz), 7.17 (d, 1H, J=8.35 Hz), 7.10-7.15 (m, 2H), 7.06 (bs, 1H), 6.92 (q, 2H, J=4.43 Hz), 3.80 (s, 3H), 3.69 (t, 2H, J=7.34 Hz), 3.52-3.60 (m, 1H), 3.14 (t, 2H, J=6.60 Hz), 3.03 (s, 2H).

Example 584

2-(3-{4-[7-(6-Methoxy-pyridin-3-yl)-pyrrolo[2,1-f][1,2,4]triazin-2-ylamino]-phenyl}-azetidin-1-yl)-acetamide The titled compound was prepared in an analogous fashion to Example 582b replacing 7-(2-Methanesulfonyl-2,3-dihydro-1H-isoindol-4-yl)-pyrrolo[2,1-f][1,2,4]triazin-2-ol with 7-(6-Methoxy-pyridin-3-yl)-pyrrolo[2,1-f][1,2,4]triazin-2-ol to give 2-(3-{4-[7-(6-Methoxy-pyridin-3-yl)-pyrrolo[2,1-f][1,2,4]triazin-2-ylamino]-phenyl}-azetidin-1-yl)-acetamide as a yellow solid (18 mg, 10%). MP 208-210° C. LCMS (E/I+) 430 (M+H). NMR 1H (DMSO-d6)-9.46 (s, 1H), 8.98 (s, 1H), 8.91 (bs, 1H), 8.51 (d, 1H, J=8.78 Hz), 7.67 (d, 2H, J=8.51 Hz), 7.30 (d, 2H, J=8.37 Hz), 7.18 (d, 1H, J=4.63 Hz), 7.13 (bs, 1H), 7.05 (bs, 1H), 7.03 (d, 1H, J=8.83 Hz), 6.96 (d, 1H, J=4.68 Hz), 3.94 (s, 3H), 3.71 (t, 2H, J=7.35 Hz), 3.56-3.64 (m, 1H), 3.18 (t, 2H, J=6.82 Hz), 3.04 (s, 2H).

Example 585

2-(3-{4-[7-(1-Methyl-1H-pyrazol-4-yl)-pyrrolo[2,1-f][1,2,4]triazin-2-ylamino]-phenyl}-azetidin-1-yl)-acetamide The titled compound was prepared in an analogous fashion to Example 582b replacing 7-(2-Methanesulfonyl-2,3-dihydro-1H-isoindol-4-yl)-pyrrolo[2,1-f][1,2,4]triazin-2-ol with 7-(1-Methyl-1H-pyrazol-4-yl)-pyrrolo[2,1-f][1,2,4]triazin-2-ol to give 2-(3-{4-[7-(1-Methyl-1H-pyrazol-4-yl)-pyrrolo[2,1-f][1,2,4]triazin-2-ylamino]-phenyl}-azetidin-1-yl)-acetamide as a yellow solid (3 mg, 2%). MP 255-257° C. LCMS (E/I+) 403 (M+H). NMR 1H (DMSO-d6)-9.33 (s, 1H), 8.87 (s, 1H), 8.42 (s, 1H), 8.17 (s, 1H), 7.69 (d, 2H, J=8.57 Hz), 7.37 (d, 2H, J=8.39 Hz), 7.14 (bs, 1H), 7.03-7.08 (m, 2H), 6.90 (d, 1H, J=4.70 Hz), 3.94 (s, 3H), 3.73 (t, 2H, J=7.49 Hz), 3.60-3.66 (m, 1H), 3.21 (t, 2H, J=6.82 Hz), 3.04 (s, 2H).

Example 586

2-[3-(4-{7-[2-(Methanesulfonyl-methyl-amino)-phenyl]-pyrrolo[2,1-f][1,2,4]triazin-2-ylamino}-phenyl)-azetidin-1-yl]-acetamide The titled compound was prepared in an analogous fashion to Example 582b replacing 7-(2-Methanesulfonyl-2,3-dihydro-1H-isoindol-4-yl)-pyrrolo[2,1-f][1,2,4]triazin-2-ol with N-[2-(2-Hydroxy-pyrrolo[2,1-f][1,2,4]triazin-7-yl)-phenyl]-N-methyl-methanesulfonamide to give 2-[3-(4-{7-[2-(Methanesulfonyl-methyl-amino)-phenyl]-pyrrolo[2,1-f][1,2,4]triazin-2-ylamino}-phenyl)-azetidin-1-yl]-acetamide as a yellow solid (19 mg, 20%). MP 155-158° C. LCMS (E/I+) 506 (M+H). NMR 1H (DMSO-d6)-9.38 (s, 1H), 8.97 (s, 1H), 7.99 (d, 1H, J=7.01 Hz), 7.67 (d, 1H, J=7.41 Hz), 7.54-7.62 (m, 4H), 7.17 (d, 1H, J=8.46 Hz), 7.11 (bs, 1H), 7.06 (bs, 1H), 6.99 (d, 1H, J=4.66 Hz), 6.95 (d, 1H, J=4.51 Hz), 3.68 (t, 2H, J=7.19 Hz), 3.52-3.60 (m, 1H), 3.13 (t, 2H, J=6.79 Hz), 3.07 (s, 3H), 3.02 (s, 2H), 2.89 (s, 3H).

Example 587

2-(3-{4-[7-(2,3-Dihydro-benzofuran-7-yl)-pyrrolo[2,1-f][1,2,4]triazin-2-ylamino]-phenyl}-azetidin-1-yl)-acetamide The titled compound was prepared in an analogous fashion to Example 582b replacing 7-(2-Methanesulfonyl-2,3-dihydro-1H-isoindol-4-yl)-pyrrolo[2,1-f][1,2,4]triazin-2-ol with 7-(2,3-Dihydro-benzofuran-7-yl)-pyrrolo[2,1-f][1,2,4]triazin-2-ol to give 2-(3-{4-[7-(2,3-Dihydro-benzofuran-7-yl)-pyrrolo[2,1-f][1,2,4]triazin-2-ylamino]-phenyl}-azetidin-1-yl)-acetamide as a yellow solid (9 mg, 7%). MP 211-214° C. LCMS (E/I+) 441 (M+H). NMR 1H (DMSO-d6)-9.41 (s, 1H), 8.96 (s, 1H), 8.09 (d, 1H, J=7.65 Hz), 7.72 (d, 2H, J=8.62

Hz), 7.31 (d, 1H, J=6.79 Hz), 7.25 (d, 2H, J=8.43 Hz), 7.12 (m, 2H), 7.06 (bs, 1H), 7.02 (t, 1H, J=7.55 Hz), 6.93 (d, 1H, J=4.56 Hz), 4.62 (t, 2H, J=8.73 Hz), 3.71 (t, 2H, J=6.84 Hz), 3.54-3.64 (m, 1H), 3.16 (t, 2H, J=6.57 Hz), 3.03 (s, 2H).

Example 588

2-(4-{4-[7-(3-Isopropoxy-phenyl)-pyrrolo[2,1-f][1,2,4]triazin-2-ylamino]-phenyl}-piperidin-1-yl)-acetamide 588a) 7-Bromo-pyrrolo[2,1-f][1,2,4]triazin-2-ol (200 mg, 0.001 mol), 3-isopropoxyphenylboronic acid (206 mg, 0.00114 mol), 0.9 M of Sodium carbonate in water (3.4 mL, 0.0031 mol), Tetrakis(triphenylphosphine)palladium (O) (120 mg, 0.00010 mol) and 1,4-Dioxane (7 mL, 0.08 mol) were heated at 110° C. 1 hr. Cooled to room temperature, added water and EtOAc. The EtOAc layer was separated, dried, filtered and concentrated. The product was precipitated with ether and filtered. Yield=80 mg (40%).

588b) 7-(3-Isopropoxy-phenyl)-pyrrolo[2,1-f][1,2,4]triazin-2-ol (100 mg, 0.4 mmol), N-Phenylbis(trifluoromethanesulphonimide) (146 mg, 0.408 mmol), N,N-Diisopropylethylamine (0.194 mL, 1.11 mmol), and N,N-Dimethylformamide (3 mL, 40 mmol) and stir at room temperature for half an hour. Add 2-[4-(4-Amino-phenyl)-piperidin-1-yl]-acetamide (139 mg, 0.594 mmol) and stir at 60° C. overnight. The reaction was concentrated, DMSO added, filtered and placed onto the Gilson for purification. The most pure fractions were basified with saturated sodium bicarbonate, extracted with ethyl acetate, dried, filtered and collected as a yellow solid (47 mg, 30%). MP 233-235° C. LCMS (E/I+) 485 (M+H). NMR 1H (DMSO-d6)-9.43 (s, 1H), 8.97 (s, 1H), 7.82 (s, 1H), 7.73 (d, 2H, J=8.04 Hz), 7.66 (d, 1H, J=7.72 Hz), 7.43 (t, 1H, J=7.80 Hz), 7.14-7.22 (m, 5H), 6.98 (d, 1H, J=8.17 Hz), 6.94 (d, 1H, J=4.50 Hz), 4.70-4.75 (m, 1H), 2.87-2.95 (m, 4H), 2.40-2.46 (m, 1H), 2.10-2.22 (m, 2H), 1.70-1.76 (m, 4H), 1.31 (d, 6H, J=5.79 Hz).

Example 589

N-tert-Butyl-3-(2-{4-[4-(4-methyl-piperazin-1-ylmethyl)-piperidin-1-yl]-phenylamino}-pyrrolo[2,1-f][1,2,4]triazin-7-yl)-benzenesulfonamide 589a) A mixture of 1-Methyl-4-[1-(4-nitro-phenyl)-piperidin-4-ylmethyl]-piperazine (1.0 g, 3.3 mmol) and 10% Palladium on Carbon (50% Wet)(5:45:50, Palladium:carbon black:Water, 0.180 g, 0.0846 mmol) and Ethanol (20.0 mL, 342 mmol) was hydrogenated using a parr apparatus at 40 psi overnight. Filtered solution through celite and rinsed celite with ethanol. Concentrated the solution using hi-vac. Yield=0.85 g.

589b) N-tert-Butyl-3-(2-methanesulfinyl-pyrrolo[2,1-f][1,2,4]triazin-7-yl)-benzenesulfonamide (0.1 g, 0.3 mmol), 4-[4-(4-Methyl-piperazin-1-ylmethyl)-piperidin-1-yl]-phenylamine (147 mg, 0.510 mmol), N,N-Diisopropylethylamine (0.124 mL, 0.712 mmol), and 1-Methoxy-2-propanol (0.5 mL, 5 mmol) were heated in the microwave at 225° C. for 30 minutes. The reaction was concentrated and redissolved in 3 ml of DMSO and placed onto the Gilson. The most pure fractions were combined basified with sat. sodium bicarbonate, extracted with DCM, dried filtered and concentrated to give a yellow solid (47 mg, 30%). MP 233-235° C. LCMS (E/I+) 485 (M+H). NMR 1H (DMSO-d6)-9.26 (s, 1H), 8.98 (s, 1H), 8.54 (s, 1H), 8.38 (d, 1H, J=8.04 Hz), 7.84 (d, 1H, J=7.90 Hz), 7.73 (t, 1H, J=7.81 Hz), 7.57-7.61 (m, 3H), 7.16 (d, 1H, J=4.52 Hz), 6.93-6.97 (m, 3H), 3.58 (d, 2H, J=11.59 Hz), 2.54-2.62 (m, 2H), 2.28-2.38 (m, 6H), 2.14 (m, 6H), 1.77 (d, 2H, J=12.50 Hz), 1.55-1.65 (m, 1H), 1.16-1.26 (m, 3H), 1.12 (s, 9H).

Example 590

N-tert-Butyl-3-[2-(6-oxo-1,6-dihydro-pyridin-3-ylamino)-pyrrolo[2,1-f][1,2,4]triazin-7-yl]-benzenesulfonamide The titled compound was prepared in an analogous fashion to Example 589b replacing 4-[4-(4-Methyl-piperazin-1-ylmethyl)-piperidin-1-yl]-phenylamine with 5-Amino-1H-pyridin-2-one
to give N-tert-Butyl-3-[2-(6-oxo-1,6-dihydro-pyridin-3-ylamino)-pyrrolo[2,1-f][1,2,4]triazin-7-yl]-benzenesulfonamide as a yellow solid (12 mg, 10%). MP 270-271° C. LCMS (E/I+) 439 (M+H). NMR 1H (DMSO-d6)-11.20 (bs, 1H), 9.18 (s, 1H), 8.99 (s, 1H), 8.41 (s, 1H), 8.38 (d, 1H, J=7.83 Hz), 7.82 (d, 2H, J=7.84 Hz), 7.70-7.76 (m, 2H), 7.64 (s, 1H), 7.18 (d, 1H, J=4.81 Hz), 6.98 (d, 1H, J=4.83 Hz), 6.42 (d, 1H, J=9.70 Hz), 1.12 (s, 9H).

Example 591

5-[7-(2-Methoxy-phenyl)-pyrrolo[2,1-f][1,2,4]triazin-2-ylamino]-1H-pyridin-2-one A mixture of 2-Methanesulfinyl-7-(2-methoxy-phenyl)-pyrrolo[2,1-f][1,2,4]triazine (0.08 g, 0.3 mmol), 5-Amino-1H-pyridin-2-one (56.1 mg, 0.510 mmol), N,N-Diisopropylethylamine (0.181 mL, 1.04 mmol), and 1-Methoxy-2-propanol (0.5 mL, 5 mmol) were heated in the microwave at 200° C. for 30 minutes. The reaction was concentrated and redissolved in 2 ml of DMSO and placed onto the Gilson. The most pure fractions were combined basified with sat. sodium bicarbonate, extracted with DCM, dried filtered and concentrated to give 5-[7-(2-Methoxy-phenyl)-pyrrolo[2,1-f][1,2,4]triazin-2-ylamino]-1H-pyridin-2-one
as a yellow solid. (5 mg, 6%). MP 205-207° C. LCMS (E/I+) 334 (M+H). NMR 1H (DMSO-d6)-11.4 (bs, 1H), 9.02 (s, 1H), 8.90 (s, 1H), 7.77 (s, 1H), 7.69 (d, 1H, J=7.71 Hz), 7.62 (d, 1H, J=9.62 Hz), 7.43 (t, 1H, J=7.89 Hz), 7.20 (d, 1H, J=8.20 Hz), 7.11 (t, 1H, J=7.53 Hz), 6.90 (s, 2H), 6.32 (d, 1H, J=9.61 Hz), 3.80 (s, 3H).

Example 592

3-({7-[3-(tert-butylsulfamoyl)phenyl]pyrrolo[2,1-f][1,2,4]triazin-2-yl}amino)-N,N-dimethylbenzenesulfonamide The titled compound was prepared in an analogous fashion to Example 589b replacing 4-[4-(4-Methyl-piperazin-1-ylmethyl)-piperidin-1-yl]-phenylamine with 3-Amino-N,N-dimethyl-benzenesulfonamide to give 3-({7-[3-(tert-butylsulfamoyl)phenyl]pyrrolo[2,1-f][1,2,4]triazin-2-yl}amino)-N,N-dimethylbenzenesulfonamide as a yellow solid (14.8 mg, 10%). LCMS (E/I+) 551 (M+H). NMR 1H (DMSO-d6)-9.92 (s, 1H), 9.10 (s, 1H), 8.50 (s, 1H), 8.38 (d, 1H, J=7.76 Hz), 8.23 (d, 1H, J=8.23 Hz), 7.94 (s, 1H), 7.86 (d, 1H, J=7.79 Hz), 7.77 (t, 1H, J=7.81 Hz), 7.60-7.66 (m, 2H), 7.30 (d, 1H, J=7.70 Hz), 7.25 (d, 1H, J=4.75 Hz), 7.06 (d, 1H, J=4.87 Hz), 2.58 (s, 6H), 1.11 (s, 9H).

Example 593

4-({7-[3-(tert-butylsulfamoyl)phenyl]pyrrolo[2,1-f]
[1,2,4]triazin-2-yl}amino)-N,N-dimethylbenzene-
sulfonamide The titled compound was prepared in an analogous fashion to Example 589b replacing 4-[4-(4-Methyl-piperazin-1-ylmethyl)-piperidin-1-yl]-phenylamine with 4-Amino-N,N-dimethyl-benzenesulfonamide to give 4-({7-[3-(tert-butylsulfamoyl)phenyl]pyrrolo[2,1-f][1,2,4]triazin-2-yl}amino)-N,N-dimethylbenzenesulfonamide as a yellow solid (8 mg, 5%). LCMS (E/I+) 529 (M+H). NMR 1H (DMSO-d6)-10.15 (s, 1H), 9.12 (s, 1H), 8.68 (s, 1H), 8.22 (d, 1H, J=7.99 Hz), 7.98 (d, 2H, J=8.76 Hz), 7.89 (d, 1H, J=8.29 Hz), 7.78 (d, 1H, J=7.98 Hz), 7.75 (s, 1H), 7.73 (d, 2H, J=8.65 Hz), 7.67 (s, 1H), 7.29 (d, 1H, 4.82 Hz), 7.07 (d, 1H, J=4.75 Hz), 2.58 (s, 6H), 1.11 (s, 9H).

Example 594

3-[7-(2-Methoxy-phenyl)-pyrrolo[2,1-f][1,2,4]triazin-2-ylamino]-N,N-dimethyl-benzenesulfonamide The titled compound was prepared in an analogous fashion to Example 591 replacing 5-Amino-1H-pyridin-2-one with 3-Amino-N,N-dimethyl-benzenesulfonamide to give 3-[7-(2-Methoxy-phenyl)-pyrrolo[2,1-f][1,2,4]triazin-2-ylamino]-N,N-dimethyl-benzenesulfonamide as a yellow solid (3.5 mg, 2%). MP 185-189° C. LCMS (E/I+) 424 (M+H). NMR 1H (DMSO-d6)-9.76 (s, 1H), 9.00 (s, 1H), 8.17 (d, 1H, J=8.51 Hz), 7.90 (s, 1H), 7.70 (d, 1H, J=7.59 Hz), 7.46 (q, 2H, J=8.15 Hz), 7.22 (d, 2H, J=8.19 Hz), 7.12 (t, 1H, J=7.63 Hz), 6.96 (q, 2H, J=4.60 Hz), 3.79 (s, 6H).

Example 595

4-[7-(2-Methoxy-phenyl)-pyrrolo[2,1-f][1,2,4]triazin-2-ylamino]-N,N-dimethyl-benzenesulfonamide The titled compound was prepared in an analogous fashion to Example 591 replacing 5-Amino-1H-pyridin-2-one with 4-Amino-N,N-dimethyl-benzenesulfonamide to give 4-[7-(2-Methoxy-phenyl)-pyrrolo[2,1-f][1,2,4]triazin-2-ylamino]-N,N-dimethyl-benzenesulfonamide as a yellow solid (3 mg, 2%). MP 175-177° C. LCMS (E/I+) 424 (M+H). NMR 1H (DMSO-d6)-10.00 (s, 1H), 9.03 (s, 1H), 7.91 (d, 2H, J=8.79 Hz), 7.75 (d, 1H, J=7.52 Hz), 7.55 (d, 2H, J=8.74), 7.50 (d, 1H, J=7.84 Hz), 7.27 (d, 1H, J=8.35 Hz), 7.15 (t, 1H, J=7.42 Hz), 7.00 (s, 2H), 3.79 (s, 3H), 2.56 (s, 6H).

Example 596

N-Methyl-N-{2-[2-(6-oxo-1,6-dihydro-pyridin-3-ylamino)-pyrrolo[2,1-f][1,2,4]triazin-7-yl]-phenyl}-methanesulfonamide The titled compound was prepared in an analogous fashion to Example 591 replacing 2-Methanesulfinyl-7-(2-methoxy-phenyl)-pyrrolo[2,1-f][1,2,4]triazine with N-[2-(2-Methanesulfinyl-pyrrolo[2,1-f][1,2,4]triazin-7-yl)-phenyl]-N-methyl-methanesulfonamide to give N-Methyl-N-{2-[2-(6-oxo-1,6-dihydro-pyridin-3-ylamino)-pyrrolo[2,1-f][1,2,4]triazin-7-yl]-phenyl}-methanesulfonamide as a yellow solid (27 mg, 20%). LCMS (E/I+) 411 (M+H). NMR 1H (DMSO-d6)-9.49 (s, 1H), 8.96 (s, 1H), 8.17 (s, 1H), 7.79 (d, 1H, J=7.62 Hz), 7.46-7.54 (m, 3H), 7.23 (d, 1H, J=8.30 Hz), 7.13 (t, 1H, J=7.63 Hz), 6.94 (s, 2H), 3.84 (s, 3H), 2.58 (s, 3H).

Example 597

(3-Chloro-4-fluoro-phenyl)-[7-(3-methanesulfonyl-phenyl)-pyrrolo[2,1-f][1,2,4]triazin-2-yl]-amine, Compound with trifluoro acetic acid 2-Methanesulfinyl-7-(3-methanesulfonyl-phenyl)-pyrrolo[2,1-f][1,2,4]triazine (100 mg, 0.0003 mol) and 3-Chloro-4-fluoro-phenylamine (86.8 mg, 0.000596 mol) were dissolved in 1-Methoxy-2-propanol (0.5 mL, 0.005 mol) and N,N-Diisopropylethylamine (0.156 mL, 0.000894 mol). The reaction was heated in the microwave for 30 min at 200° C. The reaction was concentrated and dissolved in DMSO, filtered, and placed on the Gilson. The pure fractions were collected and placed on the lyopholizer over night and collected as a yellow solid (4 mg, 3%). LCMS (E/I+) 417 (M+H). NMR 1H (DMSO-d6)-9.81 (s, 1H), 9.08 (s, 1H), 8.56 (d, 1H, J=7.93 Hz), 8.47 (s, 1H), 7.94-8.00 (m, 2H), 7.86 (t, 1H, J=7.86 Hz), 7.66-7.72 (m, 1H), 7.37 (t, 1H, J=9.24 Hz), 7.33 (d, 1H, J=4.79 Hz), 7.04 (d, 1H, J=4.81 Hz), 3.30 (s, 3H).

Example 598

3-{1-[7-(1-Methyl-1H-pyrazol-4-yl)-pyrrolo[2,1-f]
[1,2,4]triazin-2-yl]-piperdin-4-yloxy}-phenylamine; compound with trifluoro-acetic acid 2-Methanesulfinyl-7-(1-methyl-1H-pyrazol-4-yl)-pyrrolo[2,1-f][1,2,4]triazine (100.0 mg, 0.3827 mmol) was dissolved in 1-Methoxy-2-propanol (374.1 uL, 3.827 mmol) and added to 4-(3-Amino-phenoxy)-piperidine-1-carboxylic acid tert-butyl ester (223.8 mg, 0.7654 mmol) and N,N-Diisopropylethylamine (200.0 uL, 1.148 mmol). The substance was microwaved at 200 C for 15 min. The reaction was concentrated, dissolved in 1 mL of DMSO and placed onto the Gilson. Lyophilized overnight to give 3-{1-[7-(1-Methyl-1H-pyrazol-4-yl)-pyrrolo[2,1-f][1,2,4]triazin-2-yl]-piperidin-4-yloxy}-phenylamine as a yellow solid (4 mg, 3%). LCMS (E/I+) 417 (M+H). NMR 1H (DMSO-d6)-8.82 (s, 1H), 8.39 (s, 1H), 8.16 (s, 1H), 7.24 (t, 1H, J=8.05 Hz), 7.05 (d, 1H, J=4.71 Hz), 6.87 (d, 1H, J=4.76 Hz), 6.77 (d, 1H, J=8.04 Hz), 6.69 (s, 1H), 6.65 (d, 1H, J=8.04 Hz), 4.62-4.68 (m, 1H), 4.08-4.16 (m, 2H), 3.93 (s, 3H), 3.50-3.6 (m, 2H), 2.04-2.12 (m, 2H), 1.66-1.76 (m, 2H).

Example 599

[7-(3-Methanesulfonyl-phenyl)-pyrrolo[2,1-f][1,2,4]
triazin-2-yl]-(2-methyl-benzoxazol-5-yl)-amine The titled compound was prepared in an analogous fashion to Example 597 replacing 3-Chloro-4-fluoro-phenylamine with 2-Methyl-benzoxazol-5-ylamine; hydrochloride to give [7-(3-Methane sulfonyl-phenyl)-pyrrolo[2,1-f][1,2,4]triazin-2-yl]-(2-methyl-benzoxazol-5-yl)-amine as a yellow solid (52 mg, 50%). MP=223-225° C. LCMS (E/I+) 420 (M+H). NMR 1H (DMSO-d6)-9.67 (s, 1H), 9.07 (s, 1H), 8.58 (d, 1H, J=7.93 Hz), 8.55 (s, 1H), 8.06 (s, 1H), 7.97 (d, 1H, J=7.91 Hz), 7.82 (t, 1H, J=7.82 Hz), 7.68 (d, 1H, J=8.72 Hz), 7.60 (d, 1H, J=8.73 Hz), 7.30 (d, 1H, J=4.75 Hz), 7.01 (d, 1H, J=4.86 Hz), 2.59 (s, 3H).

Example 600

N-tert-Butyl-3-[2-(2-methyl-benzoxazol-5-ylamino)-pyrrolo[2,1-f][1,2,4]triazin-7-yl]-benzenesulfonamide Prepare mixture of N-tert-Butyl-3-(2-hydroxy-pyrrolo[2,1-f][1,2,4]triazin-7-yl)-benzenesulfonamide (75 mg, 0.22 mmol), N-Phenylbis(trifluoromethanesulphonimide) (77 mg, 0.22 mmol), N,N-Diisopropylethylamine (0.113 mL, 0.650 mmol), and N,N-Dimethylformamide (2.0 mL, 26 mmol) and stir at room temperature for half an hour. Add 2-Methyl-benzoxazol-5-ylamine; hydrochloride (52 mg, 0.28 mmol) and stir at 80° C. overnight. The reaction was concentrated, dissolved in 2 mL DMSO, filtered and placed onto the Gilson. The most pure fractions were combined basified with sat. sodium bicarbonate, extracted with DCM, dried filtered, and concentrated to give N-tert-Butyl-3-[2-(2-methyl-benzoxazol-5-ylamino)-pyrrolo[2,1-f][1,2,4]triazin-7-yl]-benzenesulfonamide as a yellow solid (40 mg, 40%). MP=212-214° C. LCMS (E/I+) 477 (M+H). NMR 1H (DMSO-d6)-9.64 (s, 1H), 9.06 (s, 1H), 8.55 (d, 1H, J=8.20 Hz), 8.47 (s, 1H), 8.00 (s, 1H), 7.86 (d, 1H, J=8.06 Hz), 7.68-7.85 (m, 3H), 7.60 (d, 1H, J=8.86 Hz), 7.23 (d, 1H, J=4.86 Hz), 7.01 (d, 1H, J=4.86 Hz), 2.60 (s, 3H), 1.12 (s, 9H).

Example 601

[7-(2-Methoxy-phenyl)-pyrrolo[2,1-f][1,2,4]triazin-2-yl]-[3-(piperidin-4-yloxy)-phenyl]-amine A mixture of 4-(3-Amino-phenoxy)-piperidine-1-carboxylic acid tert-butyl ester (94 mg, 0.32 mmol), Trifluoromethanesulfonic acid 7-(2-methoxy-phenyl)-pyrrolo[2,1-f][1,2,4]triazin-2-yl ester (100 mg, 0.3 mmol), 1-Methoxy-2-propanol (0.3 mL, 3 mmol), and N,N-Diisopropylethylamine (2 mL, 10 mmol) was heated and let stir overnight at 80° C. Concentrated added Hydrogen Chloride (2 mL, 60 mmol) and stir at room temperature for half and hour. The reaction was concentrated, dissolved in 2 mL DMSO, filtered and placed onto the Gilson. The pure fractions were frozen and lypholyzed over night to give [7-(2-Methoxy-phenyl)-pyrrolo[2,1-f][1,2,4]triazin-2-yl]-[3-(piperidin-4-yloxy)-phenyl]-amine a yellow solid (7 mg, 6%). LCMS (E/I+) 416 (M+H). NMR 1H (DMSO-d6)-9.41 (s, 1H), 8.96 (s, 1H), 8.50 (bs, 1H), 7.77 (d, 1H, J=7.36 Hz), 7.40-7.50 (m, 2H), 7.08-7.22 (m, 3H), 6.94 (s, 2H), 4.40 (m, 1H), 3.80 (s, 3H), 3.10-3.18 (m, 2H), 3.04-3.10 (m, 2H), 1.98-2.06 (m, 2H), 1.76-1.84 (m, 2H).

Example 611

[7-(3-Methanesulfonyl-phenyl)-pyrrolo[2,1-f][1,2,4]triazin-2-yl]-(7-morpholin-4-yl-6,7,8,9-tetrahydro-5H-benzocyclohepten-2-yl)-amine; compound with trifluoroacetic acid The titled compound was prepared in analogous fashion as Example 113 using 2-methanesulfinyl-7-(3-methanesulfonyl-phenyl)-pyrrolo[2,1-f][1,2,4]triazine and 7-morpholin-4-yl-6,7,8,9-tetrahydro-5H-benzocyclohepten-2-ylamine (WO2008051546) to give as a TFA salt (62.8 mg, 34% yield). LCMS (E/I+) 518 (M+H). $^1$H NMR (400 MHz, DMSO-d6) δ 9.53 (broad s, 1H), 9.51 (s, 1H), 8.61 (d, 1H, J=8.1 Hz), 8.5 (t, 1H, J=1.7 Hz) (7.96 (d, 1H, J=8 Hz), 7.82 (t, 1H, J=8 Hz), 7.57 (m, 1H), 7.52 (d, 1H, J=8 Hz), 7.30 (d, 1H, J=4.7 Hz), 7.15 (d, 1H, J=8 Hz), 7.00 (d, 1H, 4.7 Hz), 3.99 (d, 2H, J=12 Hz), 3.72 (t, 2H, J=12 Hz), 3.56 (m, 1H), 3.28-3.31 (m, 5H), 3.21 (m, 2H), 2.67-2.82 (m, 4H), 2.33 (m, 2H), 1.47 (m, 2H).

Example 612

[7-(4-Methanesulfonyl-phenyl)-pyrrolo[2,1-f][1,2,4]triazin-2-yl]-(7-morpholin-4-yl-6,7,8,9-tetrahydro-5H-benzocyclohepten-2-yl)-amine, compound with trifluoroacetic acid The titled compound was prepared in analogous fashion as Example 113 using 2-chloro-7-(4-methanesulfonyl-phenyl)-pyrrolo[2,1-f][1,2,4]triazine and 7-morpholin-4-yl-6,7,8,9-tetrahydro-5H-benzocyclohepten-2-ylamine to give [7-(4-methanesulfonyl-phenyl)-pyrrolo[2,1-f][1,2,4]triazin-2-yl]-(7-morpholin-4-yl-6,7,8,9-tetrahydro-5H-benzocyclohepten-2-yl)-amine (WO2008051546) as a yellow-brown TFA salt (23.9 mg, 16.9% yield). LCMS (E/I+) (M+H). $^1$H NMR (400 MHz, DMSO-d6) δ 9.54 (s, 1H), 9.06 (s, 1H), 8.48 (d, 2H, J=8.7 Hz), 8.04 (d, 2H, J=8.6 Hz), 7.79 (s, 1H), 7.32-7.35 (m, 2H), 7.15 (d, 1H, J=8.2 Hz), 7.01 (d, 1H, J=4.8 Hz), 3.99 (m, 2H), 3.72 (m, 3H), 3.61 (m, 1H), 3.18-3.5 (m, 6H), 2.67-2.88 (m, 4H), 2.32-2.39 (m, 2H), 1.52 (m, 2H).

Example 613

[7-(3,6-Dihydro-2H-thiopyran-4-yl)-pyrrolo[2,1-f][1,2,4]triazin-2-yl]-(4-morpholin-4-yl-phenyl)-amine; compound with trifluoroacetic acid The titled compound was prepared by heating (7-bromo-pyrrolo[2,1-f][1,2,4]triazin-2-yl)-(4-morpholin-4-yl-phenyl)-amine, tributyl-(3,6-dihydro-2H-thiopyran-4-yl)stannane (*J. Org. Chem,* 2007, 72, 1507-1509), bis(triphenylphosphine)palladium(II) chloride in toluene and DMF at 100° C. for 6 h. Reaction solvents were removed in vacuo and the mixture was diluted with methylene chloride and washed with water. The titled product was isolated by prep HPLC to give as a yellow lyophilate TFA salt (69.2 mg, 67% yield). LCMS (E/I+) 394 (M+H). $^1$H NMR (400 MHz, DMSO-d6) 9.25 (s, 1H), 8.88 (s, 1H), 7.63 (d, 2H, J=9 Hz), 7.26 (m, 1H), 7.04 (d, 2H, J=8 Hz), 6.81 (q, 2H, J=4.7 Hz), 3.77 (m, 4H), 3.46 (m, 2H), 3.13 (m, 4H), 2.89 (t, 2H, J=5.7 Hz), 2.77 (m, 2H).

Example 614

[7-(2-methoxy-phenyl)-pyrrolo[2,1-f][1,2,4]triazin-2-yl]-(7-morpholin-4-yl-6,7,8,9-tetrahydro-5H-benzocyclohepten-2-yl)amine; compound with trifluoroacetic acid The titled compound was prepared in analogous fashion as Example 113 using 2-methanesulfinyl-7-(2-methoxyphenyl)pyrrolo[2,1-f][1,2,4]triazine and 7-morpholin-4-yl-6,7,8,9-tetrahydro-5H-benzocyclohepten-2-ylamine (WO2008051546) to give [7-(2-methoxy-phenyl)-pyrrolo[2,1-f][1,2,4]triazin-2-yl]-(7-morpholin-4-yl-6,7,8,9-tetrahydro-5H-benzocyclohepten-2-yl)-amine, compound with trifluoroacetic acid as a yellow lyophilate TFA salt (50.01 mg, 20.5% yield). LCMS (E/I+) 470 (M+H). $^1$H NMR (400 MHz, DMSO-d6) δ 9.72 (broad s, 1H), 9.35 (s, 1H), 8.95 (s, 1H), 7.81 (d, 1H, J=6.8 Hz), 7.71 (s, 1H), 7.48 (t, 1H, J=7.4 Hz), 7.33 (d, 1H, J=6.8 Hz), 7.24 (d, 1H, J=8.3 Hz), 7.13 (t, 1H, J=7.4 Hz), 7.01 (d, 1H, J=8.1 Hz), 6.93 (dd, 2H, J=4.6, 9.7 Hz), 3.99 (d, 2H, J=12 Hz), 3.79 (s, 3H), 3.73 (t, 2H, J=12

Hz), 3.54 (t, 1H, J=11 Hz), 3.21-3.32 (m, 4H), 2.54-2.82 (m, 4H), 2.33 (m, 2H), 1.43 (m, 2H).

Example 615

N-Methyl-N-{2-[2-(7-morpholin-4-yl-6,7,8,9-tetrahydro-5H-benzocyclohepten-2-ylamino)-pyrrolo[2,1-f][1,2,4]triazin-7-yl]-phenyl}-methanesulfonamide, compound with trifluoroacetic acid The titled compound was prepared in analogous fashion as Example 113 using 7-morpholin-4-yl-6,7,8,9-tetrahydro-5H-benzocyclohepten-2-ylamine (WO2008051546) and N-[2-(2-methanesulfinyl-pyrrolo[2,1-f][1,2,4]triazin-7-yl)-phenyl]-N-methyl-methanesulfonamide to give N-methyl-N-{2-[2-(7-morpholin-4-yl-6,7,8,9-tetrahydro-5H-benzocyclohepten-2-ylamino)-pyrrolo[2,1-f][1,2,4]triazin-7-yl]-phenyl}-methanesulfonamide, compound with trifluoroacetic acid as a yellow-brown lyophilate (29.7 mg, 25.2% yield). LCMS (E/I+) 547 (M+H). $^1$H NMR (400 MHz, DMSO-d6) 9.79 (broad s, 1H), 9.36 (s, 1H), 8.97 (s, 1H), 7.94 (m, 1H), 7.68 (m, 1H), 7.61 (s, 1H), 7.58 (m, 2H), 7.27 (d, 1H, J=8 Hz), 7.00 (d, 1H, J=8 Hz), 6.96 (m, 2H), 3.71-3.99 (m, 5H), 3.53 (t, 1H, J=11 Hz), 3.30 (m, 2H), 3.21 (m, 2H), 3.07 (s, 3H), 2.86 (s, 3H), 2.78 (m, 1H), 2.67 (t, 2H), 2.32 (m, 2H), 1.42 (m, 2H).

Example 616

N-Methyl-N-{2-[2-(1-methyl-1,2,3,5-tetrahydro-benzo[e][1,4]oxazepin-7-ylamino)-pyrrolo[2,1-f][1,2,4]triazin-7-yl]-phenyl}-methanesulfonamide; compound with trifluoroacetic acid The titled compound was prepared in analogous fashion as Example 113 using N-[2-(2-methanesulfinyl-pyrrolo[2,1-f][1,2,4]triazin-7-yl)-phenyl]-N-methyl-methanesulfonamide and 1-methyl-1,2,3,5-tetrahydro-benzo[e][1,4]oxazepin-7-ylamine (WO2008051546) to give N-methyl-N-{2-[2-(1-methyl-1,2,3,5-tetrahydro-benzo[e][1,4]oxazepin-7-ylamino)-pyrrolo[2,1-f][1,2,4]triazin-7-yl]-phenyl}-methanesulfonamide; compound with trifluoroacetic acid as a yellow-brown lyophilate TFA salt (47.3 mg, 26.7%). LCMS (E/I+) 479 (M+H). $^1$H NMR (400 MHz, DMSO-d6) 9.27 (s, 1H), 8.94 (s, 1H), 7.97 (m, 1H), 7.64 (m, 2H), 7.56 (m, 2H), 7.37 (d, 1H, J=8 Hz), 6.96 (1H, d, J=4.6 Hz), 6.92 (1H, d, J=4.6 Hz), 6.83 (d, 1H, J=9 Hz), 4.34 (s, 2H), 3.76 (m, 2H), 3.06 (s, 3H), 2.92 (m, 2H), 2.89 (s, 3H), 2.84 (s, 3H).

Example 617

[7-(4-Methanesulfonyl-phenyl)-pyrrolo[2,1-f][1,2,4]triazin-2-yl]-(1-methyl-1,2,3,5-tetrahydro-benzo[e][1,4]oxazepin-7-yl)-amine; compound with trifluoro-acetic acid The titled compound was prepared in analogous fashion as Example 113 using 1-methyl-1,2,3,5-tetrahydro-benzo[e][1,4]oxazepin-7-ylamine (WO2008051546) and 2-methanesulfinyl-7-(4-methanesulfonyl-phenyl)-pyrrolo[2,1-f][1,2,4]triazine to give [7-(4-methanesulfonyl-phenyl)-pyrrolo[2,1-f][1,2,4]triazin-2-yl]-(1-methyl-1,2,3,5-tetrahydro-benzo[e][1,4]oxazepin-7-yl)-amine; compound with trifluoroacetic acid as a brown lyophilate (14.3, 11.2% yield). LCMS (E/I+) 450 (M+H) $^1$H NMR (400 MHz, DMSO-d6) δ 9.38 (s, 1H), 9.03 (s, 1H), 8.47 (d, 2H, J=7.8 Hz), 8.03 (d, 2H, J=7.8 Hz), 7.75 (s, 1H), 7.41 (d, 1H, J=8.4 Hz), 7.33 (d, 1H, J=4.5 Hz), 6.97 (m, 2H), 4.51 (S, 2H), 3.80 (s, 2H), 3.26 (s, 3H), 2.96 (s, 2H), 2.88 (s, 3H).

Example 618

[7-(2-Methoxy-phenyl)-pyrrolo[2,1-f][1,2,4]triazin-2-yl]-(1-methyl-1,2,3,5-tetrahydro-benzo[e][1,4]oxazepin-7-yl)-amine; compound with trifluoroacetic acid The titled compound was prepared in analogous fashion as Example 113 using 1-methyl-1,2,3,5-tetrahydro-benzo[e][1,4]oxazepin-7-ylamine (WO2008051546) and 2-methanesulfinyl-7-(2-methoxy-phenyl)-pyrrolo[2,1-f][1,2,4]triazine to give [7-(2-methoxy-phenyl)-pyrrolo[2,1-f][1,2,4]triazin-2-yl]-(1-methyl-1,2,3,5-tetrahydro-benzo[e][1,4]oxazepin-7-yl)-amine; compound with trifluoroacetic acid as a yellow-brown lyophilate (45.6 mg, 30.3% yield) LCMS (E/I+) 402 (M+H), $^1$H NMR (400 MHz, DMSO-d6) δ 9.27 (s, 1H), 8.92 (s, 1H), 7.84 (d, 1H, J=7.6 Hz), 7.75 (s, 1H), 7.47 (t, 1H, J=7.7 Hz), 7.41 (d, 1H, J=8.6 Hz), 7.21 (d, 1H, 8.3 Hz), 7.12 (t, 1H, 7.4 Hz), 6.92 (dd, 2H, J=8.2, 4.2 Hz), 6.86 (d, 1H, J=8.7 Hz), 4.37 (s, 2H), 3.78 (s, 3H), 3.75 (m, 2H), 2.93 (m, 2H), 2.83 (s, 3H).

Example 619

N-{3-[2-(1-Methyl-1,2,3,5-tetrahydro-benzo[e][1,4]oxazepin-7-ylamino)-pyrrolo[2,1-f][1,2,4]triazin-7-yl]-phenyl}-methanesulfonamide; compound with trifluoro-acetic acid The titled compound was prepared in analogous fashion as Example 113 using 1-Methyl-1,2,3,5-tetrahydro-benzo[e][1,4]oxazepin-7-ylamine (WO2008051546) and N-[3-(2-methanesulfinyl-pyrrolo[2,1-f][1,2,4]triazin-7-yl)-phenyl]-methanesulfonamide to give N-{3-[2-(1-methyl-1,2,3,5-tetrahydro-benzo[e][1,4]oxazepin-7-ylamino)pyrrolo[2,1-f][1,2,4]triazin-7-yl]-phenyl}methanesulfonamide; compound with trifluoroacetic acid as a yellow-brown lyophilate (25.9 mg, 15.3% yield) LCMS (E/I+) 466 (M+H), $^1$H NMR (400 MHz, DMSO-d6 δ 9.86 (s, 1H), 9.34 (s, 1H), 8.97 (s, 1H), 8.02 (d, 1H, J=7.8 Hz), 7.80 (s, 1H), 7.69 (s, 1H), 7.58 (d, 1H, J=8.7 Hz), 7.50 (t, 1H, J=8 Hz), 7.26 (d, 1H, J=8 Hz), 7.03 (s, 1H), 6.95 (m, 2H), 4.48 (s, 2H), 3.8 (m, 2H), 3.02 (s, 3H), 2.95 (broad s, 2H), 2.88 (s, 3H).

Example 620

[7-(4-Methanesulfonyl-cyclohex-1-enyl)-pyrrolo[2,1-f][1,2,4]triazin-2-yl]-[4-(4-methyl-piperazin-1-yl)-phenyl]-amine; compound with trifluoroacetic acid The titled compound was prepared in analogous fashion as Example 175 using (7-bromo-pyrrolo[2,1-f][1,2,4]triazin-2-yl)-[4-(4-methylpiperazin-1-yl)-phenyl]amine and 2-(4-methanesulfonylcyclohex-1-enyl)-4,4,5,5-tetramethyl[1,3,2]dioxaborolane (*J. Org. Chem*, 2007, 72, 1507-1509) to give [7-(4-methanesulfonylcyclohex-1-enyl)-pyrrolo[2,1-f][1,2,4]triazin-2-yl]-[4-(4-methyl-piperazin-1-yl)-phenyl]amine compound with trifluoroacetic acid as a orange-brown lyophilate (52.8 mg, 30.5% yield). LCMS (E/I+) 467 (M+H). $^1$H NMR (400 MHz, DMSO-d6) δ 9.74 (broad s, 1H), 9.24 (s, 1H), 8.89 (s, 1H), 7.61 (d, 2H, J=8.6 Hz), 7.23 (s, 1H), 7.01 (d, 2H, J=8 Hz), 6.83 (s, 2H), 3.75 (d, 3H, J=12.95 Hz), 3.53 (d, 2H, J=12.95 Hz), 3.44 (m, 1H), 3.19 (m, 2H), 3.03 (s, 3H), 2.81-2.94 (m, 5H), 2.72 (m, 1H), 2.57 (m, 2H), 2.35 (d, 1H, J=12 Hz), 1.75 (m, 1H).

Example 621

N-{2-[2-(4-Imidazol-1-ylmethylphenylamino)-pyrrolo[2,1-f][1,2,4]triazin-7-yl]phenyl}-N-methyl-methanesulfonamide; compound with trifluoroacetic acid The titled compound was prepared in analogous fashion as Example 113 using N-methyl-N-[2-(2-methylsulfanyl-pyrrolo[2,1-f][1,2,4]triazin-7-yl)-phenyl]methanesulfonamide and 4-imidazol-1-ylmethylphenylamine to give N-{2-[2-(4-imidazol-1-ylmethyl-phenylamino)-pyrrolo[2,1-f][1,2,4]triazin-7-yl]-phenyl}-N-methyl-methane sulfonamide; compound with trifluoroacetic acid as a mustard colored lyophilate (126.1 mg, 70.9% yield). LCMS (E/I+) 406 (M+H). $^1$H NMR (400 MHz, DMSO-d6) δ 9.58 (s, 1H), 9.20 (s, 1H), 8.90 (s, 1H), 7.98 (m, 1H), 7.76 (s, 1H), 7.69 (m, 4H), 7.57 (m, 2H), 7.30 (d, 2H, J=7.9 Hz), 6.99 (dd, 2H, J=4.3, 8.6 Hz), 5.32 (s, 2H), 3.08 (s, 3H), 2.89 (s, 3H).

Example 622

N-[2-(2-Imidazol-1-yl-pyrrolo[2,1-f][1,2,4]triazin-7-yl)-phenyl]-N-methyl-methanesulfonamide; compound with trifluoro-acetic acid The titled compound was prepared in analogous fashion as Example 113 using N-methyl-N-[2-(2-methylsulfanyl-pyrrolo[2,1-f][1,2,4]triazin-7-yl)-phenyl]methanesulfonamide and 4-imidazol-1-ylmethylphenylamine to give N-[2-(2-imidazol-1-yl-pyrrolo[2,1-f][1,2,4]triazin-7-yl)-phenyl]-N-methyl-methanesulfonamide; compound with trifluoro-acetic acid as a mustard colored lyophilate (44.4 mg, 30.5% yield) as a byproduct from Example 621. LCMS (E/I+) 369 (M+H). $^1$H NMR (400 MHz, DMSO-d6) δ 9.36 (s, 1H), 9.23 (s, 1H), 8.03 (s, 1H), 7.90 (d, 1H, J=7.4 Hz), 7.73 (d, 1H, J=7.8 Hz), 7.60 (m, 2H), 7.53 (s, 1H), 7.35 (dd, 2H, J=8.6, 4.6 Hz), 3.14 (s, 3H), 2.88 (s, 3H).

Example 623

N-Methyl-N-{2-[2-(2-oxo-2,3,4,5-tetrahydro-1H-benzo[b]azepin-7-ylamino)-pyrrolo[2,1-f][1,2,4]triazin-7-yl]-phenyl}-methanesulfonamide; compound with trifluoro-acetic acid The titled compound was prepared in analogous fashion as Example 113 using N-[2-(2-methanesulfinyl-pyrrolo[2,1-f][1,2,4]triazin-7-yl)-phenyl]-N-methyl-methanesulfonamide and 7-amino-1,3,4,5-tetrahydro-1-benzazepin-2-one (WO2008051546) to give N-methyl-N-{2-[2-(2-oxo-2,3,4,5-tetrahydro-1H-benzo[b]azepin-7-ylamino)-pyrrolo[2,1-f][1,2,4]triazin-7-yl]-phenyl}methanesulfonamide; compound with trifluoro-acetic acid as a brown lyophilate (43.2 mg, 28% yield). LCMS 477 (M+H). $^1$H NMR (400 MHz, DMSO-d6) δ 9.39 (s, 1H), 9.26 (s, 1H), 8.97 (s, 1H), 7.90 (d, 1H, J=7.5 Hz), 7.66 (m, 2H), 7.55 (m, 2H), 7.33 (d, 1H, J=8.6 Hz), 6.95 (s, 2H), 6.79 (d, 1H, J=8.4 Hz), 3.05 (s, 3H), 2.86 (s, 3H), 2.48 (m, 2H), 2.07 (m, 4H).

Example 624

N-{2-[2-(5,5-Dimethyl-2-oxo-2,3,4,5-tetrahydro-1H-benzo[b]azepin-7-ylamino)pyrrolo[2,1-f][1,2,4]triazin-7-yl]-phenyl]methanesulfonamide; compound with trifluoroacetic acid The titled compound was prepared in analogous fashion as Example 113 using N-[2-(2-methanesulfinyl-pyrrolo[2,1-f][1,2,4]triazin-7-yl)-phenyl]-methanesulfonamide and 7-amino-5,5-dimethyl-1,3,4,5-tetrahydrobenzo[b]azepin-2-one (WO2008051546) to give N-{2-[2-(5,5-dimethyl-2-oxo-2,3,4,5-tetrahydro-1H-benzo[b]azepin-7-ylamino)pyrrolo[2,1-f][1,2,4]triazin-7-yl]-phenyl}methanesulfonamide; compound with trifluoroacetic acid as a brown lyophilate (53.7 mg, 22% yield). LCMS (E/I+) 505 (M+H). $^1$H NMR (400 MHz) DMSO-d6) δ 9.31 (s, 1H), 9.27 (s, 1H), 8.96 (s, 1H), 7.75 (d, 1H, J=7.8 Hz), 7.68 (s, 1H), 7.63 (d, 1H, J=8 Hz), 7.51 (m, 2H), 7.36 (d, 1H, J=7.2 Hz), 6.93 (d, 1H, J=4.7 Hz), 6.88 (d, 1H, J=4.7 Hz), 6.78 (d, 1H, J=8.6 Hz), 3.02 (s, 3H), 2.80 (s, 3H), 2.11 (t, 2H, J=6.8 Hz), 1.86 (t, 2H, J=6.8 Hz), 1.02 (s, 6H).

Example 625

N-{2-[2-(1-Methyl-2-oxo-2,3,4,5-tetrahydro-1H-benzo[b]azepin-7-ylamino)pyrrolo[2,1-f][1,2,4]triazin-7-yl]-phenyl}methanesulfonamide; compound with trifluoroacetic acid The titled compound was prepared in analogous fashion as Example 113 using N-[2-(2-methanesulfinyl-pyrrolo[2,1-f][1,2,4]triazin-7-yl)-phenyl]-methanesulfonamide and 7-amino-1-methyl-1,3,4,5-tetrahydro-1-benzazepin-2-one (WO2008051546) to give N-{2-[2-(1-methyl-2-oxo-2,3,4,5-tetrahydro-1H-benzo[b]azepin-7-ylamino)pyrrolo[2,1-f][1,2,4]triazin-7-yl]-phenyl}methanesulfonamide; compound with trifluoroacetic acid as a mustard colored lyophilate (59.6 mg, 34% yield). LCMS (E/I+) 491 (M+H). $^1$H NMR (400 MHz, DMSO-d6) δ 9.48 (s, 1H), 8.98 (s, 1H), 7.91 (m, 1H), 7.66 (m, 2H), 7.56 (m, 2H), 7.43 (d, 1H, J=8.6 Hz), 7.14 (d, 1H, J=8.6 Hz), 6.96 (s, 2H), 3.17 (s, 3H), 3.06 (s, 3H), 2.87 (s, 3H), 2.42 (m, 2H), 2.11 (m, 2H), 1.99 (m, 2H)

Example 626

N-Methyl-N-{2-[2-(4-morpholin-4-yl-phenylamino)pyrrolo[2,1-f][1,2,4]triazin-7-yl]phenyl}methanesulfonamide; compound with trifluoroacetic acid The titled compound was prepared in analogous fashion as Example 113 using N-[2-(2-methanesulfinyl-pyrrolo[2,1-f][1,2,4]triazin-7-yl)-phenyl]-N-methyl-methanesulfonamide and 4-(4-morpholino)aniline to give N-methyl-N-{2-[2-(4-morpholin-4-ylphenylamino)pyrrolo[2,1-f][1,2,4]triazin-7-yl]phenyl}methanesulfonamide; compound with trifluoroacetic acid as a yellow-brown lyophilate (83.2 mg, 58.1% yield). LCMS (E/I+) 479 (M+H). $^1$H NMR (400 MHz, DMSO-d6) δ 9.29 (s, 1H), 8.94 (s, 1H), 8.0 (d, 1H, J=7.5 Hz), 7.66 (d, 1H, J=7.4 Hz), 7.57 (m, 4H), 6.95 (m, 4H), 3.77 (s, 4H), 3.12 (s, 4H), 3.07 (s, 3H), 2.90 (s, 3H).

Example 627

N-Methyl-N-(2-{2-[4-(4-methyl-piperazin-1-yl)phenylamino]pyrrolo[2,1-f][1,2,4]triazin-7-yl}phenyl)methanesulfonamide; compound with trifluoroacetic acid The titled compound was prepared in analogous fashion as Example 113 using N-[2-(2-methanesulfinylpyrrolo[2,1-f]

[1,2,4]triazin-7-yl)phenyl]-N-methylmethanesulfonamide and 4-(4-methyl-piperazin-1-yl)phenylamine to give N-methyl-N-(2-{2-[4-(4-methyl-piperazin-1-yl)phenylamino]pyrrolo[2,1-f][1,2,4]triazin-7-yl}phenyl)methanesulfonamide; compound with trifluoroacetic acid as an orange lyophilate (105.2 mg, 58% yield). LCMS (E/I+) 492 (M+H). $^1$H NMR (400 MHz, DMSO-d6) δ 9.57 (s, 1H), 9.24 (s, 1H), 8.94 (s, 1H), 8.01 (d, 1H, J=7.6 Hz), 7.56 (m, 4H), 6.97 (s, 1H), 6.93 (s, 1H), 6.87 (d, 2H, J=7.6 Hz), 3.71 (d, 2H, J=13 Hz), 3.5 (d, 2H, J=12 Hz), 3.16 (m, 2H), 3.08 (s, 3H), 2.89 (s, 3H), 2.86 (m, 5H).

Example 628

N-Methyl-N-{2-[2-(4-methyl-2-oxo-2,3-dihydrobenzooxazol-6-ylamino)-pyrrolo[2,1-f][1,2,4]triazin-7-yl]phenyl}methanesulfonamide; compound with trifluoro-acetic acid The titled compound was prepared in analogous fashion as Example 113 using N-[2-(2-methanesulfinyl-pyrrolo[2,1-f][1,2,4]triazin-7-yl)-phenyl]-N-methyl-methanesulfonamide and 6-amino-4-methyl-3H-benzoxazol-2-one to give N-methyl-N-{2-[2-(4-methyl-2-oxo-2,3-dihydrobenzooxazol-6-ylamino)-pyrrolo[2,1-f][1,2,4]triazin-7-yl]phenyl}methanesulfonamide; compound with trifluoroacetic acid as an orange lyophilate (32.8 mg, 14% yield). LCMS (E/I+) 465 (M+H). $^1$H NMR (400 MHz, TFA-d) δ 8.90 (s, 1H), 8.11 (d, 1H, J=6.8 Hz), 7.93 (m, 2H), 7.79 (m, 3H), 7.53 (s, 1H), 7.22 (s, 1H), 3.55 (s, 3H), 3.20 (s, 3H), 2.58 (s, 3H).

Example 629

N-{2-[2-(2-Oxo-2,3-dihydro-benzooxazol-6-ylamino)pyrrolo[2,1-f][1,2,4]triazin-7-yl]phenyl}methanesulfonamide; compound with trifluoroacetic acid The titled compound was prepared in analogous fashion as Example 113 using N-[2-(2-methanesulfinyl-pyrrolo[2,1-f][1,2,4]triazin-7-yl)-phenyl]-methanesulfonamide and 6-amino-3H-benzoxazol-2-one to give N-{2-[2-(2-oxo-2,3-dihydro-benzooxazol-6-ylamino)pyrrolo[2,1-f][1,2,4]triazin-7-yl]-phenyl}methanesulfonamide; compound with trifluoroacetic acid as an orange lyophilate (15.3 mg, 10% yield). LCMS (E/I+) 451 (M+H). $^1$H NMR (DMSO-d6) δ 8.91 (s, 1H), 8.13 (d, 1H, J=7.4 Hz), 7.90-7.99 (m, 3H), 7.78 (m, 3H), 7.55 (s, 2H), 7.47 (d, 1H, J=8.7 Hz), 7.39 (d, 1H, J=9 Hz), 3.56 (s, 3H), 3.21 (s, 3H).

Example 630

N-{2-[2-(1-Acetyl-2,3,4,5-tetrahydro-1H-benzo[b]azepin-8-ylamino)-pyrrolo[2,1-f][1,2,4]triazin-7-yl]phenyl}-N-methylmethanesulfonamide; compound with trifluoroacetic acid The titled compound was prepared in analogous fashion as Example 113 using N-[2-(2-methanesulfinyl-pyrrolo[2,1-f][1,2,4]triazin-7-yl)phenyl]-N-methyl-methanesulfonamide and 1-(8-amino-2,3,4,5-tetrahydro-1-benzazepin-1-yl)ethanone (WO2008051546) to give N-{2-[2-(1-acetyl-2,3,4,5-tetrahydro-1H-benzo[b]azepin-8-ylamino)-pyrrolo[2,1-f][1,2,4]triazin-7-yl]phenyl}-N-methylmethanesulfonamide; compound with trifluoroacetic acid as a yellowish-brown lyophilate (109.8 mg, 62.8% yield). LCMS (E/I+) 505 (M+H), $^1$H NMR (400 MHz, DMSO-d6) δ 9.52 (s, 1H), 8.98 (s, 1H), 7.85 d, 1H, J=7.4 Hz), 7.75 (s, 1H), 7.64 (d, 1H, J=7.4 Hz), 7.44-7.52 (m, 2H), 7.29 (d, 1H, J=8.0 Hz), 7.12 (d, 1H, J=8.0 Hz), 6.95 (s, 2H), 4.48 (d, 1H, J=13 Hz), 3.05 (s, 3H), 2.87 (s, 3H), 2.60 (m, 1H), 2.45 (m, 2H), 1.87 (m, 1H), 1.70 (m, 2H), 1.51 (s, 3H), 1.24 (m, 1H).

Example 631

1-{8-[7-(6-Methoxy-pyridin-3-yl)-pyrrolo[2,1-f][1,2,4]triazin-2-ylamino]-2,3,4,5-tetrahydro-benzo[b]azepin-1-yl}ethanone; compound with trifluoroacetic acid The titled compound was prepared in analogous fashion as Example 113 using 2-methanesulfinyl-7-(6-methoxy-pyridin-3-yl)-pyrrolo[2,1-f][1,2,4]triazine and 1-(8-amino-2,3,4,5-tetrahydro-1-benzazepin-1-yl)-ethanone (WO2008051546) to give 1-{8-[7-(6-methoxy-pyridin-3-yl)-pyrrolo[2,1-f][1,2,4]triazin-2-ylamino]-2,3,4,5-tetrahydro-benzo[b]azepin-1-yl}ethanone; compound with trifluoroacetic acid as a yellowish-brown lyophilate (129.7 mg, 67% yield). LCMS (E/I+) 429 (M+H). $^1$H NMR (400 MHz, DMSO-d6) δ 9.60 (s, 1H), 8.99 (s, 1H), 8.90 (s, 1H), 8.43 (d, 1H, J=8.6 Hz), 7.80 (s, 1H), 7.45 (d, 1H, J=8.2 Hz), 7.23 (d, 1H, J=8.2 Hz), 7.17 (m, 1H), 6.97 (m, 1H), 6.94 (d, 1H, J=8.8 Hz), 4.53 (d, 1H, J=12.7 Hz), 3.95 (s, 3H), 2.66 (m, 3H), 1.91 (m, 1H), 1.73 (m, 5H), 1.27 (m, 2H).

Example 632

N-{2-[2-(3,3-Dimethyl-2-oxo-2,3-dihydro-1H-indol-5-ylamino)-pyrrolo[2,1-f][1,2,4]triazin-7-yl]phenyl}N-methyl-methanesulfonamide; compound with trifluoroacetic acid The titled compound was prepared in analogous fashion as Example 113 using N-[2-(2-methanesulfinyl-pyrrolo[2,1-f][1,2,4]triazin-7-yl)-phenyl]-N-methyl-methanesulfonamide and 5-amino-3,3-dimethyl-1,3-dihydro-indol-2-one to give N-{2-[2-(3,3-dimethyl-2-oxo-2,3-dihydro-1H-indol-5-ylamino)-pyrrolo[2,1-f][1,2,4]triazin-7-yl]-phenyl}N-methyl-methanesulfonamide; compound with trifluoroacetic acid as a yellowish lyophilate (162 mg, 74.6% yield). LCMS (E/I+) 477 (M+H). $^1$H NMR (400 MHz, DMSO-d6) δ 10.1 (s, 1H), 9.24 (s, 1H), 8.94 (s, 1H), 7.77 (d, 1H), 7.66 (m, 2H), 7.54 (m, 2H), 7.23 (d, 1H, J=8.4 Hz), 6.92 (d, 1H, J=4 Hz), 6.87 (d, 1H, J=4 Hz), 6.68 (d, 1H, J=8.4 Hz), 3.03 (s, 3H), 2.81 (s, 3H), 1.02 (s, 6H).

Example 633

N-{3-[2-(1-Acetyl-2,3,4,5-tetrahydro-1H-benzo[b]azepin-8-ylamino)-pyrrolo[2,1-f][1,2,4]triazin-7-yl]-phenyl}methanesulfonamide; compound with trifluoroacetic acid The titled compound was prepared in analogous fashion as Example 113 using N-[3-(2-methanesulfinyl-pyrrolo[2,1-f][1,2,4]triazin-7-yl)-phenyl]-methanesulfonamide and 1-(8-amino-2,3,4,5-tetrahydro-1-benzazepin-1-yl)-ethanone (WO2008051546) to give N-{3-[2-(1-acetyl-2,3,4,5-tetrahydro-1H-benzo[b]azepin-8-ylamino)-pyrrolo[2,1-f][1,2,4]triazin-7-yl]-phenyl}methanesulfonamide; compound with trifluoroacetic acid as a yellowish lyophilate (56.9 mg, 37.2% yield). LCMS (E/I+) 491 (M+H). $^1$H NMR (400 MHz, DMSO-d6) δ 9.83 (s, 1H), 9.59 (s, 1H), 9.01 (s, 1H), 7.97 (d, 1H, J=7.8 Hz), 7.76 (s, 1H), 7.69 (s, 1H), 7.57 (d, 1H, J=8.2 Hz), 7.44 (dd, 1H, J=8.1, 7.8 Hz), 7.24 (d, 2H, J=8.1 Hz), 7.05 (d, 1H, J=4.2 Hz), 6.98 (d, 1H, J=4.4 Hz), 4.53 (d, 1H, J=13.6 Hz), 3.03 (s, 3H), 2.60 (m, 3H), 1.90 (m, 1H), 1.74 (m, 2H), 1.67 (s, 3H), 1.28 (m, 1H).

Example 634

N-(2-{2-[1-(4-Amino-phenyl)-piperidin-4-yloxy]-pyrrolo[2,1-f][1,2,4]triazin-7-yl}-phenyl)-N-methyl-methanesulfonamide; compound with trifluoro-acetic acid The titled compound was prepared in analogous fashion as Example 113 using N-[2-(2-methanesulfinyl-pyrrolo[2,1-f][1,2,4]triazin-7-yl)-phenyl]-N-methyl-methanesulfonamide and 1-(4-amino-phenyl)-piperidin-4-ol to give N-(2-{2-[1-(4-amino-phenyl)-piperidin-4-yloxy]-pyrrolo[2,1-f][1,2,4]triazin-7-yl}-phenyl)-N-methyl-methanesulfonamide; compound with trifluoroacetic acid as a brown lyophilate (113 mg, 47.8% yield). LCMS (E/I+) 493 (M+H). $^1$H NMR (400 MHz, DMSO-d6) δ 9.07 (s, 1H), 7.89 (d, 1H, J=6.8 Hz), 7.67 (d, 2H, J=6.7 Hz), 7.53 (m, 6 Hz), 5.02 (s, 1H), 3.55 (m, 2H), 3.17 (m, 2H), 3.13 (s, 3H), 2.90 (s, 3H), 2.07 (m, 1H), 1.87 (m, 2H).

Example 635

N-(2-{2-[4-(4-Hydroxy-piperidin-1-yl)-phenylamino]pyrrolo[2,1-f][1,2,4]triazin-7-yl}phenyl)-N-methylmethanesulfonamide; compound with trifluoro-acetic acid The titled compound was prepared in analogous fashion as Example 113 using N-[2-(2-methanesulfinyl-pyrrolo[2,1-f][1,2,4]triazin-7-yl)phenyl]-N-methyl-methanesulfonamide and 1-(4-amino-phenyl)piperidin-4-ol to give N-(2-{2-[4-(4-hydroxy-piperidin-1-yl)-phenylamino]pyrrolo[2,1-f][1,2,4]triazin-7-yl}phenyl)-N-methylmethanesulfonamide; compound with trifluoroacetic acid as a brown lyophilate (113 mg, 47.8% yield). LCMS (E/I+) 493 (M+H). $^1$H NMR (400 MHz, DMSO-d6) δ 9.72 (s, 1H), 9.01 (s, 1H), 7.99 (d, 1H, J=7.8 Hz), 7.76 (d, 2H, J=7.8 Hz), 7.68 (d, 1H, J=7.8 Hz), 7.59 (m, 2H), 7.44 (broad s, 2H), 7.01 (d, 2H, J=8.9 Hz), 3.86 (m, 2H), 3.55 (m, 3H), 3.39 (m, 2H), 3.09 (s, 3H), 2.90 (s, 3H), 2.05 (m, 2H), 1.79 (m, 2H).

Example 636

N-(3-{2-[4-(4-Morpholin-4-yl-piperidin-1-yl)-phenylamino]-pyrrolo[2,1-f][1,2,4]triazin-7-yl}-phenyl)-methanesulfonamide; compound with trifluoroacetic acid The titled compound was prepared in analogous fashion as Example 113 using N-[3-(2-methanesulfinyl-pyrrolo[2,1-f][1,2,4]triazin-7-yl)phenyl]-methanesulfonamide and 4-(4-morpholin-4-yl-piperidin-1-yl)-phenylamine [prepared in the same fashion as Example 236a and 236b replacing 2-methoxy-4-(4-morpholin-4-yl-piperidin-1-yl)-phenylamine with 4-[1-(4-nitro-phenyl)-piperidin-4-yl]-morpholine] to give N-(3-{2-[4-(4-morpholin-4-yl-piperidin-1-yl)phenylamino]-pyrrolo[2,1-f][1,2,4]triazin-7-yl}-phenyl)methanesulfonamide; compound with trifluoroacetic acid as a yellow lyophilate (160 mg, 60% yield). LCMS (E/I+) 548 (M+H). $^1$H NMR (400 MHz, DMSO-d6) δ 9.84 (s, 1H), 9.72 (broad s, 1H), 9.29 (s, 1H), 8.96 (s, 1H), 7.93 (s, 1H), 7.90 (d, 1H, J=7.9 Hz), 7.66 (d, 2H, J=8.2 Hz), 7.51 (t, 1H, J=7.9 Hz), 7.27 (d, 1H, J=7.9 Hz), 7.06 (d, 1H, J=4 Hz), 7.02 (d, 2H, J=8 Hz), 6.94 (d, 1H, J=4 Hz), 4.02 (d, 2H, J=12 Hz), 3.82 (d, 2H, J=12 Hz), 3.67 (t, 2H, J=12 Hz), 3.50 (d, 2H, J=11 Hz), 3.36 (m, 1H), 3.13 (m, 2H), 3.03 (s, 3H), 2.71 (t, 2H, J=12 Hz), 2.15 (d, 2H, J=11 Hz), 1.73 (dd, 2H, J=23, 10 Hz).

Example 637

[7-(6-Methoxy-pyridin-3-yl)-pyrrolo[2,1-f][1,2,4]triazin-2-yl]-(1-methyl-1,2,3,5-tetrahydro-benzo[e][1,4]oxazepin-7-yl)-amine; compound with trifluoro-acetic acid The titled compound was prepared in analogous fashion as Example 113 using 2-methanesulfinyl-7-(6-methoxy-pyridin-3-yl)-pyrrolo[2,1-f][1,2,4]triazine and 1-methyl-1,2,3,5-tetrahydro-benzo[e][1,4]oxazepin-7-ylamine to give [7-(6-methoxy-pyridin-3-yl)-pyrrolo[2,1-f][1,2,4]triazin-2-yl]-(1-methyl-1,2,3,5-tetrahydrobenzo[e][1,4]oxazepin-7-yl)-amine; compound with trifluoroacetic acid as a greenish-brown lyophilate (96.6 mg, 44.2% yield). LCMS (E/I+) 403 (M+H). $^1$H NMR (400 MHz; DMSO-d6) δ 9.34 (s, 1H), 8.95 (s, 2H), 8.51 (d, 1H, J=8.7 Hz), 7.81 (s, 1H), 7.41 (d, 1H, J=8.6 Hz), 7.16 (d, 1H, J=3.8 Hz), 6.99 (d, 1H, J=8.8 Hz), 6.93 (m, 2H), 4.54 (s, 2H), 3.94 (s, 3H), 3.79 (s, 2H), 2.95 (s, 2H), 2.87 (s, 3H).

Example 638

N-{3-[2-(4-Methyl-3-oxo-3,4-dihydro-2H-benzo[1,4]oxazin-7-ylamino)-pyrrolo[2,1-f][1,2,4]triazin-7-yl]-phenyl}methanesulfonamide, compound with trifluoroacetic acid The titled compound was prepared in analogous fashion as Example 113 using N-[3-(2-methanesulfinyl-pyrrolo[2,1-f][1,2,4]triazin-7-yl)-phenyl]methanesulfonamide and 7-amino-4-methyl-4H-benzo[1,4]oxazin-3-one to give N-{3-[2-(4-methyl-3-oxo-3,4-dihydro-2H-benzo[1,4]oxazin-7-ylamino)pyrrolo[2,1-f][1,2,4]triazin-7-yl]-phenyl}methanesulfonamide, compound with trifluoroacetic acid as a lyophilate (139 mg, 80% yield). LCMS (E/I+) 465 (M+H). HPLC purity=86% (10-100% acetonitrile-water with 0.1% TFA over 6 min, r.t.=2.83 min). $^1$H NMR (400 MHz, DMSO-d6) δ 8.86 (s, 1H), 9.44 (s, 1H), 9.00 (s, 1H), 7.86 (d, 1H, J=7.6 Hz), 7.80 (s, 1H), 7.52 (s, 1H), 7.47 (t, 1H, J=8 Hz), 7.39 (d, 1H, J=8.8 Hz), 7.25 (d, 1H, J=8 Hz), 7.03 (m, 1H), 6.96 (d, 2H, J=6.3 Hz), 4.59 (s, 2H), 3.07 (s, 3H), 3.00 (s, 3H).

Example 639

1-{8-[7-(2-Methoxyphenyl)-pyrrolo[2,1-f][1,2,4]triazin-2-ylamino]-2,3,4,5-tetrahydrobenzo[b]azepin-1-yl}ethanone; compound with trifluoroacetic acid. The titled compound was prepared in analogous fashion as Example 113 using 2-methanesulfinyl-7-(2-methoxy-phenyl)-pyrrolo[2,1-f][1,2,4]triazine and 1-(8-amino-2,3,4,5-tetrahydro-1-benzazepin-1-yl)ethanone (WO2008051546) to give 1-{8-[7-(2-methoxyphenyl)-pyrrolo[2,1-f][1,2,4]triazin-2-ylamino]-2,3,4,5-tetrahydrobenzo[b]azepin-1-yl}-ethanone; compound with trifluoroacetic acid as a yellowish-brown lyophilate (101 mg, 46.1% yield). LCMS (E/I+) 428 (M+H). $^1$H NMR (400 MHz, DMSO-d6) δ 9.50 (s, 1H), 8.96 (s, 1H), 7.79 (s, 1H), 7.65 (d, 1H, J=7.4 Hz), 7.42 (t, 1H, J=7.9 Hz), 7.36 (d, 1H, J=8.3 Hz), 7.13 (d, 2H, J=8.2 Hz), 7.04 (t, 1H, J=7.6 Hz), 6.92 (dd, 2H, J=8.9, 4.6 Hz), 4.51 (d, 1H, J=13 Hz), 3.76 (s, 3H), 2.58-2.67 (m, 3H), 1.87 (m, 1H), 1.73 (m, 2H), 1.49 (s, 3H), 1.25 (m, 1H).

Example 640

N-Methyl-N-{2-[2-(4-methyl-3-oxo-3,4-dihydro-2H-benzo[1,4]oxazin-7-ylamino)-pyrrolo[2,1-f][1,2,4]triazin-7-yl]-phenyl}-methanesulfonamide; compound with trifluoroacetic acid The titled compound was prepared in analogous fashion as Example 113 using N-[2-(2-methanesulfinyl-pyrrolo[2,1-f][1,2,4]triazin-7-yl)-phenyl]-N-methyl-methanesulfonamide and 7-amino-4-methyl-4H-benzo[1,4]oxazin-3-one to give N-methyl-N-{2-[2-(4-methyl-3-oxo-3,4-dihydro-2H-benzo[1,4]oxazin-7-ylamino)-pyrrolo[2,1-f][1,2,4]triazin-7-yl]-phenyl}-methanesulfonamide; compound with trifluoroacetic acid as a yellow lyophilate (59.7 mg, 35.6% yield). LCMS (E/I+) 479 (M+H). $^1$H NMR (400 MHz, DMSO-d6) δ 9.42 (s, 1H), 8.98 (s, 1H), 7.73 (d, 1H, J=7.7 Hz), 7.67 (d, 2H, J=8 Hz), 7.56 (t, 1H, J=7.6 Hz), 7.51 (t, 1H, J=7.6 Hz), 7.05 (d, 1H, J=8.8 Hz), 6.95 (d, 1H, J=4 Hz), 6.86 (m, 2H), 4.53 (s, 2H), 3.08 (s, 3H), 2.80 (s, 3H), 2.66 (s, 3H).

Example 641

N-Methyl-N-{2-[2-(4-methyl-3,4-dihydro-2H-benzo[1,4]oxazin-6-ylamino)-pyrrolo[2,1-f][1,2,4]triazin-7-yl]-phenyl}methanesulfonamide; compound with trifluoroacetic acid The titled compound was prepared in analogous fashion as Example 113 using N-[2-(2-methanesulfinyl-pyrrolo[2,1-f][1,2,4]triazin-7-yl)-phenyl]-N-methyl-methanesulfonamide and 4-methyl-3,4-dihydro-2H-benzo[1,4]oxazin-6-ylamine to give N-methyl-N-{2-[2-(4-methyl-3,4-dihydro-2H-benzo[1,4]oxazin-6-ylamino)-pyrrolo[2,1-f][1,2,4]triazin-7-yl]-phenyl}methanesulfonamide; compound with trifluoroacetic acid as a reddish-brown lyophilate (63.1 mg, 18% yield). LCMS (E/I+) 465 (M+H). $^1$H NMR (400 MHz, DMSO-d6) δ 9.03 (s, 1H), 8.92 (s, 1H), 7.76 (d, 1H, J=7 Hz), 7.63 (d, 1H, J=7.4 Hz), 7.51 (m, 2H), 7.17 (s, 1H), 6.89 (s, 1H), 6.84 (s, 1H), 6.70 (d, 1H, J=8.4 Hz), 6.47 (d, 1H, J=8.4 Hz), 4.12 (m, 2H), 3.11 (m, 2H), 3.06 (s, 3H), 2.79 (s, 3H), 2.33 (3H).

Example 642

(4-Methyl-3,4-dihydro-2H-benzo[1,4]oxazin-6-yl)-(7-pyridin-3-yl-pyrrolo[2,1-f][1,2,4]triazin-2-yl)-amine; compound with trifluoro-acetic acid The titled compound was prepared in analogous fashion as Example 113 using 2-methanesulfinyl-7-pyridin-3-yl-pyrrolo[2,1-f][1,2,4]triazine and 4-methyl-3,4-dihydro-2H-benzo[1,4]oxazine to give (4-Methyl-3,4-dihydro-2H-benzo[1,4]oxazin-6-yl)-(7-pyridin-3-yl-pyrrolo[2,1-f][1,2,4]triazin-2-yl)-amine; compound with trifluoro-acetic acid as a brown lyophilate (44.8 mg, 23.4% yield). LCMS (E/I+) 359 (M+H). $^1$H NMR (400 MHz, DMSO-d6) δ 9.43 (s, 1H), 9.18 (s, 1H), 9.02 (s, 1H), 8.78 (d, 1H, J=8 Hz), 8.64 (s, 1H), 7.70 (m, 1H), 7.32 (s, 1H), 6.96 (m, 3H), 6.64 (d, 1H, J=8.5 Hz), 4.2 (s, 2H), 3.23 (s, 2H), 2.72 (s, 3H).

Example 643

N-{3-[2-(4-Methyl-3,4-dihydro-2H-benzo[1,4]oxazin-6-ylamino)-pyrrolo[2,1-f][1,2,4]triazin-7-yl]-phenyl}methanesulfonamide ; compound with trifluoroacetic acid The titled compound was prepared in analogous fashion as Example 113 using N-[3-(2-methanesulfinyl-pyrrolo[2,1-f][1,2,4]triazin-7-yl)-phenyl]-methanesulfonamide and 4-methyl-3,4-dihydro-2H-benzo[1,4]oxazin-6-ylamine to give N-{3-[2-(4-methyl-3,4-dihydro-2H-benzo[1,4]oxazin-6-ylamino)-pyrrolo[2,1-f][1,2,4]triazin-7-yl]-phenyl}methanesulfonamide; compound with trifluoroacetic acid as a brown lyophilate (47.5 mg, 27% yield). LCMS (E/I+) 451 (M+H). $^1$H NMR (400 MHz, DMSO-d6) δ 9.81 (s, 1H), 9.07 (s, 1H), 8.95 (s, 1H), 7.94 (d, 1H, J=7.9 Hz), 7.77 (s, 1H), 7.45 (t, 1H, J=7.5 Hz), 7.24 (d, 1H, J=8.2 Hz), 7.03 (s, 1H), 7.00 (d, 2H, J=5.2 Hz), 6.92 (d, 1H, J=5 Hz), 6.61 (d, 1H, J=8.1 Hz), 4.18 (s, 2H), 3.2 (s, 2H), 3.00 (s, 3H), 2.67 (s, 3H).

Example 644

[7-(6-Methoxy-pyridin-3-yl)-pyrrolo[2,1-f][1,2,4]triazin-2-yl]-(4-methyl-3,4-dihydro-2H-benzo[1,4]oxazin-6-yl)-amine; compound with trifluoroacetic acid The titled compound was prepared in analogous fashion as Example 113 using 2-methanesulfinyl-7-(6-methoxy-pyridin-3-yl)-pyrrolo[2,1-f][1,2,4]triazine and 4-methyl-3,4-dihydro-2H-benzo[1,4]oxazin-6-ylamine to give [7-(6-methoxy-pyridin-3-yl)-pyrrolo[2,1-f][1,2,4]triazin-2-yl]-(4-methyl-3,4-dihydro-2H-benzo[1,4]oxazin-6-yl)-amine; compound with trifluoroacetic acid as a brown lyophilate (34.9 mg, 15% yield). LCMS (E/I+) 389 (M+H). $^1$H NMR (400 MHz, DMSO-d6) δ 9.07 (s, 1H), 8.96 (s, 1H), 8.93 (s, 1H), 8.43 (d, 1H, J=8.6 Hz), 7.13 (s, 1H), 7.08 (s, 1H), 6.92 (m, 3H), 6.60 (d, 1H, J=8 Hz), 4.19 (s, 2H), 3.92 (s, 3H), 3.23 (s, 2H), 2.73 (s, 3H).

Example 645

[7-(2-Methoxy-phenyl)-pyrrolo[2,1-f][1,2,4]triazin-2-yl]-(4-methyl-3,4-dihydro-2H-benzo[1,4]oxazin-6-yl)-amine The titled compound was prepared in analogous fashion as Example 113 using 2-methanesulfinyl-7-(2-methoxy-phenyl)-pyrrolo[2,1-f][1,2,4]triazine and 4-methyl-3,4-dihydro-2H-benzo[1,4]oxazin-6-ylamine to give 645 [7-(2-methoxy-phenyl)-pyrrolo[2,1-f][1,2,4]triazin-2-yl]-(4-methyl-3,4-dihydro-2H-benzo[1,4]oxazin-6-yl)-amine as a brown lyophilate. LCMS (E/I+) 388 (M+H). $^1$H NMR (400 MHz, CDCl$_3$) δ 8.65 (s, 1H), 7.88 (d, 1H, J=7.5 Hz), 7.27 (t, 1H, J=8 Hz), 7.04 (m, 3H), 6.95 (d, 1H, J=3.6 Hz), 6.81 (d, 1H, J=3.8 Hz), 6.72 (d, 1H, J=8.5 Hz), 6.65 (m, 2H), 4.24 (s, 2H), 3.81 (s, 3H), 3.20 (s, 2H), 2.56 (s, 3H).

Example 646

6-[7-(1-Methyl-1H-pyrazol-4-yl)-pyrrolo[2,1-f][1,2,4]triazin-2-ylamino]-1,3-dihydro-indol-2-one; compound with trifluoroacetic acid The titled compound was prepared in analogous fashion as Example 113 using 2-methanesulfinyl-7-(1-methyl-1H- pyrazol-4-yl)-pyrrolo[2,1-f][1,2,4]triazine and 6-amino-1,3-dihydro-indol-2-one to give 6-[7-(1-methyl-1H-pyrazol-4-yl)-pyrrolo[2,1-f][1,2,4]triazin-2-ylamino]-1,3-dihydro-indol-2-one; compound with trifluoroacetic acid as a brown lyophilate. LCMS (E/I+) 346 (M+H). $^1$H NMR δ 10.4 (s, 1H), 9.3 (s, 1H), 8.87 (s, 1H), 8.42 (s, 1H), 8.15 (s, 1H), 7.3 (d, 1H, J=8.2 Hz), 7.24 (s, 1H), 7.18 (d, 1H, J=8.2 Hz), 7.08 (d, 1H, 4.8 Hz), 6.90 (d, 1H, 4.7 Hz), 3.92 (s, 3H), 3.44 (s, 2H).

Example 647

7-[7-(2-Methoxy-phenyl)-pyrrolo[2,1-f][1,2,4]triazin-2-ylamino]-4-methyl-4H-benzo[1,4]oxazin-3-one The titled compound was prepared in analogous fashion as Example 113 using 2-methanesulfinyl-7-(2-methoxy-phenyl)-pyrrolo[2,1-f][1,2,4]triazine and 7-amino-4-methyl-4H-benzo[1,4]oxazin-3-one to give 7-[7-(2-methoxy-phenyl)-pyrrolo[2,1-f][1,2,4]triazin-2-ylamino]-4-methyl-4H-benzo[1,4]oxazin-3-one as a pale yellow foam. LCMS (E/I+) 402 (M+H). $^1$H NMR (400 MHz, CDCl$_3$) δ 8.69 (s, 1H), 7.75 (dd, 1H, J=1.5, 7.5 Hz), 7.64 (s, 1H), 7.41 (td, 1H, J=2, 8.2 Hz), 7.05 (m, 2H), 6.94 (d, 1H, J=4.6 Hz), 6.86 (m, 4H), 4.55 (s, 2H), 2.79 (s, 3H), 2.89 (s, 3H).

Example 648

N-tert-Butyl-3-[2-(4-methyl-3-oxo-3,4-dihydro-2H-benzo[1,4]oxazin-7-ylamino)-pyrrolo[2,1-f][1,2,4]triazin-7-yl]-benzenesulfonamide The titled compound was prepared in analogous fashion as Example 113 using N-tert-butyl-3-(2-methanesulfinyl-pyrrolo[2,1-f][1,2,4]triazin-7-yl)-benzenesulfonamide and 7-amino-4-methyl-4H-benzo[1,4]oxazin-3-one to give N-tert-butyl-3-[2-(4-methyl-3-oxo-3,4-dihydro-2H-benzo[1,4]oxazin-7-ylamino)-pyrrolo[2,1-f][1,2,4]triazin-7-yl]-benzenesulfonamide as a light tan solid (51.6 mg, 35.7% yield). M.p=242-246° C. LCMS (E/I+) 507 (M+H). $^1$H NMR (400 MHz, CDCl$_3$) δ 8.68 (d, 2H, J=6.8 Hz), 8.20 (d, 1H, J=8 Hz), 7.84 (d, 1H, J=8.1 Hz), 7.49 (t, 1H, J=7.9 Hz), 7.21 (m, 2H), 7.10 (s, 1H), 6.99 (m, 2H), 6.82 (d, 1H, J=4.8 Hz), 5.13 (s, 1H), 4.59 (s, 2H), 3.17 (s, 3H), 1.24 (s, 9H).

Example 649

4-Methyl-7-(7-pyridin-3-yl-pyrrolo[2,1-f][1,2,4]triazin-2-ylamino)-4H-benzo[1,4]oxazin-3-one. The titled compound was prepared in analogous fashion as Example 113 using 2-methanesulfinyl-7-pyridin-3-yl-pyrrolo[2,1-f][1,2,4]triazine and 7-amino-4-methyl-4H-benzo[1,4]oxazin-3-one to give 4-methyl-7-(7-pyridin-3-yl-pyrrolo[2,1-f][1,2,4]triazin-2-ylamino)-4H-benzo[1,4]oxazin-3-one as a yellow lyophilate (29.4, 13.3% yield). LCMS (E/I+) 373 (M+H). $^1$H NMR (400 MHz, CDCl$_3$) δ 9.27 (s, 1H), 8.70 (s, 1H), 8.60 (d, 1H, J=3.8 Hz), 8.37 (d, 1H, J=7.7 Hz), 7.52 (s, 1H), 7.39 (dd, 1H, J=4.6, 7.5 Hz), 7.01 (m, 2H), 6.96 (d, 1H, J=8.4 Hz), 6.79 (s, 1H), 4.5 (s, 2H), 3.2 (s, 3H).

Example 650

N-tert-Butyl-3-[2-(4-methyl-3,4-dihydro-2H-benzo[1,4]oxazin-6-ylamino)-pyrrolo[2,1-f][1,2,4]triazin-7-yl]-benzenesulfonamide The titled compound was prepared in analogous fashion as Example 113 using N-tert-butyl-3-(2-methanesulfinyl-pyrrolo[2,1-f][1,2,4]triazin-7-yl)-benzene sulfonamide and 4-methyl-3,4-dihydro-2H-benzo[1,4]oxazin-6-ylamine to give N-tert-butyl-3-[2-(4-methyl-3,4-dihydro-2H-benzo[1,4]oxazin-6-ylamino)-pyrrolo[2,1-f][1,2,4]triazin-7-yl]-benzenesulfonamide as a light tan foam (45.5 mg, 33% yield). LCMS (E/I+) 493 (M+H). $^1$H NMR (CDCl3; 400 MHz) δ 8.71 (s, 1H), 8.59 (s, 1H), 8.43 (d, 1H, J=8.0 Hz), 7.83 (d, 1H, J=8 Hz), 7.54 (t, 1H, J=8 Hz), 7.04 (d, 1H, J=4.8 Hz), 6.88 (m, 2H), 6.82 (m, 2H), 6.66 (s, 1H), 4.64 (s, 1H), 4.3 (t, 2H, J=4.4 Hz), 3.29 (t, 2H, J=4.4 Hz), 2.76 (s, 3H), 1.21 (s, 9H).

Example 651

N-(3-{2-[4-(4-Ethyl-morpholin-2-yl)-phenylamino]-pyrrolo[2,1-f][1,2,4]triazin-7-yl}phenyl)methane-sulfonamide The titled compound was prepared in analogous fashion as Example 113 using N-[3-(2-methanesulfinyl-pyrrolo[2,1-f][1,2,4]triazin-7-yl)-phenyl]-methanesulfonamide and 4-(4-ethyl-morpholin-2-yl)-phenylamine to give N-(3-{2-[4-(4-ethyl-morpholin-2-yl)-phenylamino]-pyrrolo[2,1-f][1,2,4]triazin-7-yl}phenyl)methanesulfonamide as a yellow foam (47.3, 31.4% yield). LCMS (E/I+) 493 (M+H). $^1$H NMR (400 MHz, CDCl$_3$) δ 8.71 (s, 1H), 8.01 (s, 1H), 7.89 (d, 1H, J=7.8 Hz), 7.58 (d, 2H, J=8 Hz), 7.49 (t, 1H, J=7.8 Hz), 7.36 (m, 3H), 7.02 (m, 1H), 6.94 (s, 1H), 6.84 (s, 1H), 4.57 (d, 1H, J=10.2 Hz), 4.05 (d, 1H, J=11.4 Hz), 3.85 (t, 1H, J=11.4 Hz), 3.03 (s, 3H), 2.98 (d, 2H, J=11.6 Hz), 2.83 (d, 1H, J=11.5 Hz), 2.47 (q, 2H, J=7 Hz), 2.23 (t, 1H, J=11.5 Hz), 2.08 (t, 1H, J=10.5 Hz), 1.12 (t, 3H, J=7 Hz).

Example 652

N-tert-Butyl-3-[2-(2-oxo-2,3-dihydro-1H-indol-6-ylamino)-pyrrolo[2,1-f][1,2,4]triazin-7-yl]-benzene-sulfonamide; compound with trifluoroacetic acid The titled compound was prepared in analogous fashion as Example 113 using N-tert-butyl-3-(2-methanesulfinyl-pyrrolo[2,1-f][1,2,4]triazin-7-yl)-benzenesulfonamide and 6-amino-1,3-dihydro-indol-2-one to give N-tert-butyl-3-[2-(2-oxo-2,3-dihydro-1H-indol-6-ylamino)-pyrrolo[2,1-f][1,2,4]triazin-7-yl]-benzenesulfonamide; compound with trifluoroacetic acid as a brown lyophilate (20.1 mg, 15% yield). LCMS (E/I+) 477 (M+H). $^1$H NMR (400 MHz, DMSO) δ 10.3 (s, 1H), 9.51 (s, 1H), 9.04 (s, 1H), 8.51 (s, 1H), 8.44 (d, 1H, J=8.3 Hz), 7.84 (d, 1H, J=8 Hz), 7.73 (t, 1H, J=7.8 Hz), 7.63 (s, 1H), 7.52 (d, 1H, J=8.2 Hz), 7.22 (d, 1H, J=4.8 Hz), 7.17 (d, 1H, J=8.1 Hz), 7.07 (s, 1H), 7.00 (d, 1H, J=4.8 Hz), 3.41 (s, 2H), 1.11 (s, 9H).

Example 653

N-tert-Butyl-3-{2-[4-(4-ethyl-morpholin-2-yl)-phenylamino]-pyrrolo[2,1-f][1,2,4]triazin-7-yl}benzenesulfonamide; compound with trifluoro-acetic acid The titled compound was prepared in analogous fashion as Example 113 using N-tert-butyl-3-(2-methanesulfinyl-pyrrolo[2,1-f][1,2,4]triazin-7-yl)-benzenesulfonamide and 4-(4-ethyl-morpholin-2-yl)-phenylamine to give N-tert-butyl-3-{2-[4-(4-ethyl-morpholin-2-yl)-phenylamino]-pyrrolo[2,1-f][1,2,4]triazin-7-yl}-benzenesulfonamide; compound with trifluoroacetic acid as a yellow lyophilate (50.1 mg, 26.1% yield). LCMS (E/I+) 535 (M+H). $^1$H NMR (400 MHz, CDCl₃) δ 8.78 (s, 1H), 8.71 (s, 1H), 8.19 (d, 1H, J=7.8 Hz), 8.10 (s, 1H), 7.92 (d, 1H, J=7.8 Hz), 7.64 (m, 3H), 7.44 (d, 2H, J=8.9 Hz), 7.17 (d, 1H, J=5 Hz), 7.02 (d, 1H, J=4.5 Hz), 4.94 (d, 1H, J=9 Hz), 4.5 (s, 1H), 4.18 (d, 2H, J=7 Hz), 3.70 (d, 1H, J=12.1 Hz), 3.64 (d, 1H, J=12.1 Hz), 3.16 (m, 2H), 2.93 (m, 1H), 2.82 (t, 1H, J=11.5 Hz), 1.41 (t, 3H, J=7.4 Hz), 1.16 (s, 9H).

Example 654

N-tert-Butyl-3-(2-{4-[1-((S)-2-hydroxy-propyl)-piperidin-4-yl]-phenylamino}-pyrrolo[2,1-f][1,2,4]triazin-7-yl)-benzenesulfonamide; compound with trifluoroacetic acid The titled compound was prepared in analogous fashion as Example 113 using N-tert-butyl-3-(2-methanesulfinyl-pyrrolo[2,1-f][1,2,4]triazin-7-yl)-benzenesulfonamide and (S)-1-[4-(4-amino-phenyl)-piperidin-1-yl]-propan-2-ol to give N-tert-butyl-3-(2-{4-[1-((S)-2-hydroxy-propyl)-piperidin-4-yl]-phenylamino}-pyrrolo[2,1-f][1,2,4]triazin-7-yl)-benzenesulfonamide; compound with trifluoroacetic acid as a yellow lyophilate (23.5 mg, 14% yield). LCMS (E/I+) 563 (M+H). ¹H NMR (400 MHz, CDCl₃) δ 8.72 (s, 1H), 8.67 (s, 1H), 8.45 (s, 1H), 8.29 (d, 1H, J=8.3 Hz), 7.93 (d, 1H), 7.64 (m, 3H), 7.28 (m, 2H), 7.19 (d, 1H, J=4.9 Hz), 7.05 (d, 1H, J=4.9 Hz), 4.58 (s, 1H), 4.42 (m, 1H), 3.95 (d, 1H, J=11.4 Hz), 3.84 (d, 1H, J=11.7 Hz), 3.09 (t, 1H, J=11.4 Hz), 2.88 (m, 2H), 2.3-2.4 (m, 6H), 2.06 (t, 2H, J=14 Hz), 1.29 (d, 3H, J=6 Hz), 1.19 (s, 9H).

Example 655

N-tert-Butyl-3-[2-(3,3-dimethyl-2-oxo-2,3-dihydro-1H-indol-6-ylamino)-pyrrolo[2,1-f][1,2,4]triazin-7-yl]-benzenesulfonamide; compound with trifluoroacetic acid The titled compound was prepared in analogous fashion as Example 113 using N-tert-butyl-3-(2-methanesulfinyl-pyrrolo[2,1-f][1,2,4]triazin-7-yl)-benzenesulfonamide and 6-amino-3,3-dimethyl-1,3-dihydro-indol-2-one to give N-tert-butyl-3-[2-(3,3-dimethyl-2-oxo-2,3-dihydro-1H-indol-6-ylamino)-pyrrolo[2,1-f][1,2,4]triazin-7-yl]-benzenesulfonamide; compound with trifluoroacetic acid as a yellow-brown lyophilate (40.8 mg, 20% yield). LCMS (E/I+) 505 (M+H). ¹H NMR (400 MHz, CDCl₃) δ 8.82 (m, 2H), 8.68 (m, 2H), 7.98 (t, 2H, J=8.2 Hz), 7.66 (t, 2H, J=7.8 Hz), 7.12 (m, 3H), 6.95 (d, 1H, J=8 Hz), 4.89 (s, 1H), 1.36 (s, 6H), 1.25 (s, 9H).

Example 656

6-[7-(2-Methoxy-phenyl)-pyrrolo[2,1-f][1,2,4]triazin-2-ylamino]-3,3-dimethyl-1,3-dihydro-indol-2-one; compound with trifluoroacetic acid The titled compound was prepared in analogous fashion as Example 113 using 2-methanesulfinyl-7-(2-methoxy-phenyl)-pyrrolo[2,1-f][1,2,4]triazine and 6-amino-3,3-dimethyl-1,3-dihydro-indol-2-one to give 6-[7-(2-methoxy-phenyl)-pyrrolo[2,1-f][1,2,4]triazin-2-ylamino]-3,3-dimethyl-1,3-dihydro-indol-2-one; compound with trifluoroacetic acid as a light brown lyophilate (39.3 mg, 30% yield). LCMS (E/I+) 400 (M+H). ¹H NMR (400 MHz, CDCl₃) δ 8.98 (broad s, 1H), 8.58 (s, 1H), 7.98 (d, 1H, J=7.7 Hz), 7.61 (s, 1H), 7.54 (t, 1H, J=8.8 Hz), 7.21 (d, 1H, J=5 Hz), 7.15-7.09 (m, 4H), 7.06 (s, 2H), 3.86 (s, 3H), 2.49 (broad peak for water and TFA), 1.38 (s, 6H).

Example 657

(S)-1-(4-{4-[7-(6-Methoxy-pyridin-3-yl)-pyrrolo[2,1-f][1,2,4]triazin-2-ylamino]-phenyl}-piperidin-1-yl)-propan-2-ol; compound with trifluoroacetic acid The titled compound was prepared in analogous fashion as Example 113 using 2-methanesulfinyl-7-(6-methoxy-pyridin-3-yl)-pyrrolo[2,1-f][1,2,4]triazine and (S)-1-[4-(4-amino-phenyl)-piperidin-1-yl]-propan-2-ol to give (S)-1-(4-{4-[7-(6-methoxy-pyridin-3-yl)-pyrrolo[2,1-f][1,2,4]triazin-2-ylamino]-phenyl}-piperidin-1-yl)-propan-2-ol; compound with trifluoroacetic acid as a yellow-brown lyophilate (21.3 mg, 13.4% yield). LCMS (E/I+) 459 (M+H). ¹H NMR (400 MHz, DMSO-d6) δ 9.49 (s, 1H), 9.02 (s, 1H), 8.99 (s, 1H), 8.91 (s, 1H), 8.52 (d, 1H, J=8.7 Hz), 7.69 (d, 2H, J=8.5 Hz), 7.18 (s, 1H), 7.17 (d, 1H, J=4 Hz), 7.00 (d, 1H, J=8.8 Hz), 6.97 (d, 1H, J=4.7 Hz), 4.11 (m, 1H), 3.94 (s, 3H), 3.60 (m, 3H), 2.96-3.12 (m, 4H), 2.77 (m, 1H), 1.96 (m, 4H), 1.14 (d, 3H, J=6 Hz).

Example 658

6-[7-(6-Methoxy-pyridin-3-yl)-pyrrolo[2,1-f][1,2,4]triazin-2-ylamino]-3,3-dimethyl-1,3-dihydro-indol-2-one; compound with trifluoroacetic acid The titled compound was prepared in analogous fashion as Example 113 using 2-methanesulfinyl-7-(6-methoxy-pyridin-3-yl)-pyrrolo[2,1-f][1,2,4]triazine and 6-amino-3,3-dimethyl-1,3-dihydro-indol-2-one to give 6-[7-(6-methoxy-pyridin-3-yl)-pyrrolo[2,1-f][1,2,4]triazin-2-ylamino]-3,3-dimethyl-1,3-dihydro-indol-2-one; compound with trifluoroacetic acid as a yellow-brown lyophilate (18.6 mg, 12.5% yield). LCMS (E/I+) 401 (M+H). ¹H NMR (400 MHz, DMSO-d6) δ 10.28 (s, 1H), 9.45 (s, 1H), 8.98 (s, 1H), 8.90 (d, 1H, J=2.1 Hz), 8.54 (dd, 1H, J=8.8, 2.4 Hz), 7.45 (dd, 1H, J=8.1, 1.7 Hz), 7.2 (s, 1H), 7.18 (d, 1H, J=2.5 Hz), 7.13 (d, 1H, J=1.6 Hz), 7.02 (d, 1H, J=8.8 Hz), 6.96 (d, 1H, J=4.8 Hz), 3.94 (s, 3H), 1.25 (s, 6H).

Example 659

(2,2-Dioxo-2,3-dihydro-1H-2$1(6)-benzo[c]thiophen-5-yl)-[7-(2-methoxy-phenyl)-pyrrolo[2,1-f][1,2,4]triazin-2-yl]-amine; compound with trifluoroacetic acid The titled compound was prepared in analogous fashion as Example 113 using trifluoro-methanesulfonic acid 7-(2-methoxy-phenyl)-pyrrolo[2,1-f][1,2,4]triazin-2-yl ester and 2,2-dioxo-2,3-dihydro-1H-2$1(6)-benzo[c]thiophen-5-ylamine to give (2,2-dioxo-2,3-dihydro-1H-2$1(6)-benzo[c]thiophen-5-yl)-[7-(2-methoxy-phenyl)-pyrrolo[2,1-f][1,2,4]triazin-2-yl]-amine; compound with trifluoroacetic acid as a orange lyophilate (40.4 mg, 20% yield). LCMS (E/I+) 407 (M+H). ¹H NMR (400 MHz, DMSO-d6) δ 9.62 (s, 1H), 8.98 (s, 1H), 7.82 (s, 1H), 7.76 (d, 1H, J=7.6 Hz), 7.57 (d, 1H, J=8.5 Hz), 7.51 (t, 1H, J=8.3 Hz), 7.2-7.27 (m, 2H), 7.16 (t, 1H, J=7.5 Hz), 6.95 (m, 2H), 4.39 (s, 2H), 4.32 (s, 2H), 3.78 (s, 3H).

Example 660

2-(4-{4-[7-(2-Methoxy-phenyl)-pyrrolo[2,1-f][1,2,4]triazin-2-ylamino]-phenyl}-piperidin-1-yl)-acetamide; compound with trifluoroacetic acid The titled compound was prepared in analogous fashion as Example 113 using trifluoro-methanesulfonic acid 7-(2-methoxy-phenyl)pyrrolo[2,1-f][1,2,4]triazin-2-yl ester and 2-[4-(4-amino-phenyl)-piperidin-1-yl]-acetamide to give 2-(4-{4-[7-(2-methoxy-phenyl)-pyrrolo[2,1-f][1,2,4]triazin-2-ylamino]-phenyl}piperidin-1-yl)-acetamide; compound with trifluoroacetic acid as a yellow lyophilate (73.8 mg, 75% yield). LCMS (E/I+) 457 (M+H). $^1$H NMR (DMSO-d6, 400 MHz) δ 9.54 (s, 1H), 9.39 (s, 1H), 8.95 (s, 1H), 7.98 (s, 1H), 7.82 (d, 1H, J=7.6 Hz), 7.72 (s, 1H), 7.67 (d, 2H, J=8.4 Hz), 7.47 (dd, 1H, J=7.4, 8.2 Hz), 7.22 (d, 1H, J=8.4 Hz), 7.13 (dd, 1H, J=7.5 Hz), 7.07 (d, 2H, J=8.4 Hz), 6.94 (dd, 2H, J=4.6, 9.8 Hz), 3.92 (s, 2H), 3.81 (s, 3H), 3.52 (m, 2H), 3.13 (m, 2H), 2.71 (m, 1H), 1.94 (m, 4H).

Example 661

N-{2-[2-(3,3-Dimethyl-2-oxo-2,3-dihydro-1H-indol-6-ylmethyl)-pyrrolo[2,1-f][1,2,4]triazin-7-yl]-phenyl}-N-methyl-methanesulfonamide; compound with trifluoro-acetic acid The titled compound was prepared in analogous fashion as Example 113 using trifluoro-methanesulfonic acid 7-[2-(methanesulfonyl-methyl-amino)-phenyl]-pyrrolo[2,1-f][1,2,4]triazin-2-yl ester and 6-amino-3,3-dimethyl-1,3-dihydro-indol-2-one to give N-{2-[2-(3,3-dimethyl-2-oxo-2,3-dihydro-1H-indol-6-ylmethyl)-pyrrolo[2,1-f][1,2,4]triazin-7-yl]-phenyl}-N-methyl-methanesulfonamide as a yellow lyophilate (110 mg, 75% yield). LCMS (E/I+) 477 (M+H). $^1$H NMR (DMSO-d6; 400 MHz) δ 10.23 (s, 1H), 9.37 (s, 1H), 8.97 (s, 1H), 7.98 (d, 1H, J=7.7 Hz), 7.63 (m, 2H), 7.54 (t, 1H, J=7.7 Hz), 7.43 (d, 1H, J=8.1 Hz), 7.05 (d, 1H, J=8.1 Hz), 6.99 (m, 2H), 6.95 (d, 1H, J=4.6 Hz), 3.08 (s, 3H), 2.90 (s, 3H), 1.21 (s, 6H).

Example 662

[7-(3-Dimethylamino-phenyl)-pyrrolo[2,1-f][1,2,4]triazin-2-yl]-[4-(1-methyl-piperidin-4-yl)-phenyl]-amine; compound with trifluoroacetic acid The titled compound was prepared in analogous fashion as Example 175 using (7-bromo-pyrrolo[2,1-f][1,2,4]triazin-2-yl)-[4-(1-methyl-piperidin-4-yl)-phenyl]-amine and 3-(N,N-dimethylamino)phenyl boronic acid to give [7-(3-dimethylamino-phenyl)-pyrrolo[2,1-f][1,2,4]triazin-2-yl]-[4-(1-methyl-piperidin-4-yl)-phenyl]-amine; compound with trifluoroacetic acid as a red lyophilate (93 mg, 72% yield). LCMS (E/I+)=427 (M+H). $^1$H NMR (400 MHz, DMSO-d6) δ 9.52 (broad s, 1H), 9.47 (s. 1H), 7.76 (d, 2H, J=8.4 Hz), 7.45 (m, 2H), 7.35 (t, 1H, J=8 Hz) 7.12 (m, 3H), 6.95 (d, 1H, J=4.7 Hz), 6.83 (d, 1H, J=8.2 Hz), 3.52 (d, 2H, J=11.6 Hz), 3.07 (q, 2H, J=12 Hz), 2.95 (s, 6H), 2.82 (d, 3H, J=4.4 Hz), 2.75 (t, 1H, J=12 Hz), 2.0 (d, 2H, J=13.6 Hz), 1.81 (q, 2H, J=13.6 Hz).

Example 663

N-tert-Butyl-3-[2-(2,2-dioxo-2,3-dihydro-1H-2$1 (6)-benzo[c]thiophen-5-ylamino)-pyrrolo[2,1-f][1,2,4]triazin-7-yl]-benzenesulfonamide; compound with trifluoroacetic acid The titled compound was prepared in analogous fashion as Example 522 using N-tert-butyl-3-(2-hydroxy-pyrrolo[2,1-f][1,2,4]triazin-7-yl)-benzenesulfonamide, N-phenylbis(trifluoromethanesulphonimide) and 2,2-Dioxo-2,3-dihydro-1H-2lambda*6*benzo[c]thiophen-5-ylamine to give N-tert-Butyl-3-[2-(2,2-dioxo-2,3-dihydro-1H-2$1(6)-benzo[c]thiophen-5-ylamino)-pyrrolo[2,1-f][1,2,4]triazin-7-yl]-benzenesulfonamide; compound with trifluoroacetic acid as a brown lyophilate (30.7 mg, 28.3% yield). LCMS (E/I+) 512 (M+H). $^1$H NMR (DMSO-d6, 400 MHz) δ 9.75 (s, 1H), 9.07 (s, 1H), 8.46 (s, 1H), 8.40 (d, 1H, J=7.6 Hz), 7.87 (d, 1H, J=7.9 Hz), 7.78 (m, 2H), 7.71 (d, 1H, J=8.5 Hz), 7.63 (s, 1H), 7.34 (d, 1H, J=8.5 Hz), 7.22 (d, 1H, J=4.7 Hz), 7.03 (d, 1H, J=4.7 Hz), 4.44 (d, 4H, J=13 Hz), 1.11 (s, 9H).

Example 664

2-(4-{4-[7-(1,2,3,6-Tetrahydro-pyridin-4-yl)-pyrrolo[2,1-f][1,2,4]triazin-2-ylamino]-phenyl}-piperidin-1-yl)-acetamide The titled compound was prepared in analogous fashion as Example 175 using 2-{4-[4-(7-bromo-pyrrolo[2,1-f][1,2,4]triazin-2-ylamino)-phenyl]-piperidin-1-yl}-acetamide and 4-(4,4,5,5-tetramethyl-[1,3,2]dioxaborolan-2-yl)-3,6-dihydro-2H-pyridine-1-carboxylic acid tert-butyl ester to give 4-{2-[4-(1-carbamoylmethyl-piperidin-4-yl)-phenylamino]-pyrrolo[2,1-f][1,2,4]triazin-7-yl}-3,6-dihydro-2H-pyridine-1-carboxylic acid tert-butyl ester as a TFA salt. Deprotection of aforementioned material using TFA in methylene chloride at 0° C. and neutralized to give product as a yellow solid (93 mg, 70.7% yield). M.p.=228-231° C. LCMS (E/I+) 432 (M+H). $^1$H NMR (DMSO-d6) δ 9.41 (s, 2H), 8.96 (s, 1H), 7.61 (d, 2H, J=8.4 Hz), 7.19 (m, 3H), 7.15 (s, 1H), 6.88 (m, 2H), 3.84 (m, 2H), 3.33 (m, 2H), 2.89-2.94 (m, 4H), 2.75 (m, 2H), 2.43 (m, 2H), 2.16 (m, 2H), 1.73 (m, 4H).

Example 665

5-[7-(3-tert-Butylsulfamoyl-phenyl)-pyrrolo[2,1-f][1,2,4]triazin-2-ylamino]-nicotinamide; compound with trifluoroacetic acid The titled compound was prepared in analogous fashion as Example 522 using N-tert-butyl-3-(2-hydroxy-pyrrolo[2,1-f][1,2,4]triazin-7-yl)-benzenesulfonamide, N-phenylbis(trifluoromethanesulphonimide) and 5-amino-nicotinamide to give 5-[7-(3-tert-butylsulfamoyl-phenyl)-pyrrolo[2,1-f][1,2,4]triazin-2-ylamino]-nicotinamide; compound with trifluoroacetic acid as a yellow lyophilate (61.6, 41% yield). LCMS (E/I+) 465.99 (M+H). $^1$H NMR (400 MHz, DMSO-d6) δ 10.04 (s, 1H), 9.24 (s, 1H), 9.12 (s, 1H), 8.68 (s, 1H), 8.56 (s, 1H), 8.53 (m, 3H), 9.19 (s, 1H), 7.99 (s, 1H), 7.84 (d, 1H, J=7.8 Hz), 7.75 (t, 1H, J=7.80 Hz), 7.69 (s, 1H), 7.34 (d, 1H, J=4.8 Hz), 7.09 (d, 1H, J=4.8 Hz), 1.16 (s, 9H).

Example 666

5-{7-[2-(Methanesulfonyl-methyl-amino)-phenyl]-pyrrolo[2,1-f][1,2,4]triazin-2-ylamino}-nicotinamide; compound with trifluoroacetic acid The titled compound was prepared in analogous fashion as Example 522 using trifluoro-methanesulfonic acid 7-[2-(methanesulfonyl-methyl-amino)-phenyl]-pyrrolo[2,1-f][1,2,4]triazin-2-yl ester and 5-amino-nicotinamide to give 5-{7-[2-(methanesulfonyl-methyl-amino)-phenyl]-pyrrolo[2,1-f][1,2,4]triazin-2-ylamino}nicotinamide; compound with trifluoroacetic acid as a yellow lyophilate (53.5 mg, 60% yield). LCMS (E/I+) 437.9 (M+H). ¹H NMR (400 MHz, DMSO-d6) δ 9.88 (s, 1H), 9.05 (s, 1H), 8.95 (s, 1H), 857 (s, 1H), 8.47 (s, 1H), 8.01 (s, 1H), 7.96 (d, 1H, J=7.3 Hz), 7.65 (m, 2H), 7.55 (p, 2H, J=7.3 Hz), 7.03 (s, 2H), 3.09 (s, 3H), 2.88 (s, 3H).

Example 667

5-[7-(6-Methoxy-pyridin-3-yl)-pyrrolo[2,1-f][1,2,4]triazin-2-ylamino]-nicotinamide The titled compound was prepared in analogous fashion as Example 522 using 7-(6-methoxy-pyridin-3-yl)-pyrrolo[2,1-f][1,2,4]triazin-2-ol, N-phenylbis(trifluoromethanesulphonimide) and 5-amino-nicotinamide to give 5-[7-(6-methoxy-pyridin-3-yl)-pyrrolo[2,1-f][1,2,4]triazin-2-ylamino]-nicotinamide as a light brown solid (23.9 mg, 40% yield). M.p.=>250° C. LCMS (E/I+) 361 (M+H). ¹H NMR (400 MHz, DMSO-d6) δ 9.85 (s, 1H), 9.05 (s, 1H), 8.92 (s, 1H), 8.83 (s, 1H), 8.60 (m, 3H), 8.09 (s, 1H), 7.62 (s, 1H), 7.25 (d, 1H, J=4.7 Hz), 7.02 (m, 2H), 3.92 (s, 3H).

Example 668 2-(4-{4-[7-(2-Methoxy-phenyl)-pyrrolo[2,1-f][1,2,4]triazin-2-ylamino]-phenyl}-piperidin-1-yl)-ethanol; compound with trifluoroacetic acid The titled compound was prepared in analogous fashion as Example 522 using 7-(2-methoxy-phenyl)-pyrrolo[2,1-f][1,2,4]triazin-2-ol, N-phenylbis(trifluoromethanesulphonimide) and 2-[4-(4-amino-phenyl)-piperidin-1-yl]-ethanol to give 2-(4-{4-[7-(2-methoxy-phenyl)-pyrrolo[2,1-f][1,2,4]triazin-2-ylamino]-phenyl}-piperidin-1-yl)-ethanol; compound with trifluoroacetic acid as a light orange lyophilate (81.2 mg, 52% yield). LCMS (E/I+) 444 (M+H). ¹H NMR (400 MHz; DMSO-d6) δ 9.41 (s, 1H), 9.35 (broad s, 1H), 8.96 (s, 1H), 7.82 (d, 1H, J=7.4 Hz), 7.67 (d, 2H, J=8.1 Hz), 7.47 (t, 1H, J=7.5 Hz), 7.22 (d, 1H, J=8.3 Hz), 7.12 (t, 1H, J=7.5 Hz), 7.07 (d, 1H, J=8.1 Hz), 6.94 (dd, 2H, J=4.4, 10 Hz), 3.81 (s, 3H), 3.78 (m, 2H), 3.60 (d, 2H, J=12 Hz), 3.37 (d, 1H, J=12.9 Hz), 3.19 (d, 2H, J=4 Hz), 3.06 (m, 2H), 2.73 (m, 1H), 1.93 (m, 4H), 1.73 (p, 1H, J=14 Hz).

Example 669

N-[2-(2-{4-[1-(2-Hydroxy-ethyl)-piperidin-4-yl]-phenylamino}-pyrrolo[2,1-f][1,2,4]triazin-7-yl)-phenyl]-N-methyl-methanesulfonamide; compound with trifluoroacetic acid The titled compound was prepared in analogous fashion as Example 522 using trifluoro-methanesulfonic acid 7-[2-(methanesulfonyl-methyl-amino)-phenyl]-pyrrolo[2,1-f][1,2,4]triazin-2-yl ester and 2-[4-(4-amino-phenyl)-piperidin-1-yl]-ethanol to give N-[2-(2-{4-[1-(2-Hydroxy-ethyl)-piperidin-4-yl]-phenylamino}-pyrrolo[2,1-f][1,2,4]triazin-7-yl)-phenyl]-N-methyl-methanesulfonamide; compound with trifluoroacetic acid as a yellow lyophilate (103.8 mg, 85% yield). LCMS (E/I+) 521 (M+H). ¹H NMR (400 MHz, DMSO-d6) δ 9.42 (s, 1H), 9.24 (broad s, 1H), 8.98 (s, 1H), 8.01 (d, 1H, J=7.2 Hz), 7.67 (d, 1H, J=7.7 Hz), 7.62 (d, 2H, J=8.3 Hz), 7.56 (m, 2H), 7.06 (d, 2H, J=8.4 Hz), 7.00 (d, 1H, J=4.7 Hz), 6.96 (d, 1H, J=4.7 Hz), 3.77 (t, 2H, J=5 Hz), 3.6 (m, 2H), 3.38 (m, 2H), 3.19 (m, 2H), 3.08 (s, 3H), 3.03 (m, 1H), 2.90 (s, 3H), 2.73 (m, 1H), 1.93 (m, 3H).

Example 670

N-tert-Butyl-3-(2-{4-[1-(2-hydroxy-ethyl)-piperidin-4-yl]-phenylamino}-pyrrolo[2,1-f][1,2,4]triazin-7-yl)-benzenesulfonamide The titled compound was prepared in analogous fashion as Example 522 using N-tert-butyl-3-(2-hydroxy-pyrrolo[2,1-f][1,2,4]triazin-7-yl)-benzenesulfonamide, 2-[4-(4-amino-phenyl)-piperidin-1-yl]-ethanol and N-phenylbis(trifluoromethanesulphonimide) to give N-tert-butyl-3-(2-{4-[1-(2-hydroxy-ethyl)-piperidin-4-yl]-phenylamino}-pyrrolo[2,1-f][1,2,4]triazin-7-yl)-benzenesulfonamide as a orange lyophilate (150.9 mg, 82% yield). LCMS (E/I+) 549 (M+H). ¹H NMR (400 MHz, DMSO-d6) δ 9.53 (s, 1H), 9.27 (s, 1H), 9.04 (s, 1H), 8.58 (s, 1H), 8.33 (d, 1H, J=7.8 Hz), 7.87 (d, 1H, J=7.8 Hz), 7.72 (d, 2H, J=7.6 Hz), 7.60 (s, 1H), 7.21 (m, 3H), 7.0 (d, 1H, J=4.5 Hz), 3.78 (t, 2H, J=5 Hz), 3.61 (d, 2H, J=11 Hz), 3.38 (m, 1H), 3.18 (m, 2H), 3.12 (m, 2H), 2.76 (m, 1H), 1.97 (m, 4H), 1.11 (s, 9H).

Example 671

2-(4-{4-[7-(6-Methoxy-pyridin-3-yl)-pyrrolo[2,1-f][1,2,4]triazin-2-ylamino]-phenyl}-piperidin-1-yl)-ethanol The titled compound was prepared in analogous fashion as Example 522 using 7-(6-methoxy-pyridin-3-yl)-pyrrolo[2,1-f][1,2,4]triazin-2-ol, 2-[4-(4-amino-phenyl)-piperidin-1-yl]-ethanol and N-phenylbis(trifluoromethanesulphonimide) to give 2-(4-{4-[7-(6-methoxy-pyridin-3-yl)-pyrrolo[2,1-f][1,2,4]triazin-2-ylamino]-phenyl}-piperidin-1-yl)-ethanol; compound with trifluoroacetic acid as a yellow lyophilate (133.8 mg, 63% yield). LCMS (E/I+) 445 (M+H). ¹H NMR (400 MHz, DMSO-d6) δ 9.49 (s, 1H), 9.20 (m, 1H), 8.98 (s, 1H), 8.91 (s, 1H), 8.51 (d, 1H, J=6.7 Hz), 7.69 (d, 2H, J=8.5 Hz), 7.17 (m, 3H), 7.01 (d, 1H, J=8.7 Hz), 6.96 (d, 1H, J=4.7 Hz), 3.95 (s, 3H), 3.78 (m, 2H), 3.37 (m, 2H), 3.2 (m, 2H), 3.07 (m, 2H), 2.78 (m, 1H), 1.96 (m, 4H).

Example 672

{6-[7-(3-tert-Butylsulfamoyl-phenyl)-pyrrolo[2,1-f][1,2,4]triazin-2-yl amino]-2-hydroxy-indan-1-yl}-carbamic acid tert-butyl ester, compound as a trifluoroacetic acid salt The compound was prepared in an analogous fashion to Example 522 using (2-hydroxy-6-methylamino-indan-1-yl)-carbamic acid tert-butyl ester and N-tert-butyl-3-(2-methanesulfinyl-pyrrolo[2,1-f][1,2,4]triazin-7-yl)-benzenesulfonamide to afford {6-[7-(3-tert-butylsulfamoyl-phenyl)-pyrrolo[2,1-f][1,2,4]triazin-2-ylamino]-2-hydroxy-indan-1-yl}-carbamic acid tert-butyl ester, trifluoroacetic acid salt as a yellow lyophilate (210 mg, 56% yield). LCMS (E/I+) 477 (M+H). ¹H NMR (400 MHz, DMSO-d6) δ 10.27 (s, 1H), 9.51 (s, 1H), 9.04 (s, 1H), 8.51 (s, 1H), 8.44 (d, 1H, J=8.3 Hz), 7.84 (d, 1H, J=8 Hz), 7.73 (t, 1H, J=7.8 Hz), 7.63 (s, 1H), 7.52 (d, 1H, J=8.2 Hz), 7.22 (d, 1H, J=4.8 Hz), 7.18 (d, 1H, J=8.1 Hz), 7.07 (s, 1H), 7.00 (d, 1H, J=4.8 Hz), 4.2 (m, 1H), 3.41 (s, 2H), 3.05 (m, 1H), 2.52 (m, 1H), 1.14 (s, 9H), 1.11 (s, 9H).

Example 673

{2-Hydroxy-6-[7-(2-methoxy-phenyl)-pyrrolo[2,1-f][1,2,4]triazin-2-ylamino]-indan-1-yl}-carbamic acid tert-butyl ester, compound as a trifluoroacetic acid salt The compound was prepared in an analogous fashion to Example 522 using (2-Hydroxy-6-methylamino-indan-1-yl)- carbamic acid tert-butyl ester and 2-methanesulfinyl-7-(2-methoxy-phenyl)-pyrrolo[2,1-f][1,2,4]triazine to afford {2-hydroxy-6-[7-(2-methoxy-phenyl)-pyrrolo[2,1-f][1,2,4]triazin-2-ylamino]-indan-1-yl}-carbamic acid tert-butyl ester, compound as a trifluoroacetic acid salt as a yellow lyophilate (182 mg, 68% yield). LCMS (E/I+) 488 (M+H). $^1$H NMR (400 MHz, DMSO-d6) δ 9.34 (s, 1H), 8.93 (s, 1H), 7.80 (d, 2H, J=7.7 Hz), 7.44 (t, 1H, J=7.9 Hz), 7.21 (m, 2H), 7.11 (m, 2H), 6.96 (d, 1H, J=8.3 Hz), 6.92 (dd, 2H, J=9, 4.6 Hz), 4.65 (t, 1H, J=7.5 Hz), 4.12 (m, 1H), 3.79 (s, 3H), 3.00 (dd, 1H, J=7, 15 Hz), 2.55 (dd, 1H, J=7, 15 Hz), 1.44 (s, 9H).

Example 674

5-{2-[4-(1-Carbamoylmethyl-piperidin-4-yl)-phenylamino]-pyrrolo[2,1-f]

[1,2,4]triazin-7-yl}-3,4-dihydro-2H-pyridine-1-carboxylic acid tert-butyl ester, compound as a trifluoroacetic acid salt The compound was prepared in an analogous fashion to Example 522 using 2-{4-[4-(7-bromo-pyrrolo[2,1-f][1,2,4]triazin-2-ylamino)-phenyl]-piperidin-1-yl}-acetamide and 5-(4,4,5,5-Tetramethyl-[1,3,2]dioxaborolan-2-yl)-3,6-dihydro-2H-pyridine-1-carboxylic acid tert-butyl ester to provide 5-{2-[4-(1-Carbamoylmethyl-piperidin-4-yl)-phenylamino]-pyrrolo[2,1-f][1,2,4]triazin-7-yl}-3,4-dihydro-2H-pyridine-1-carboxylic acid tert-butyl ester, compound as a trifluoroacetic acid salt (189 mg, 59.7% yield). LCMS (E/I+) 532 (M+H). $^1$H NMR (400 MHz, CDCl$_3$) δ 8.29 (s, 1H), 8.22 (s, 1H), 7.70 (d, 2H, J=8 Hz), 7.23 (m, 2H), 7.10 (d, 1H, J=5 Hz), 6.94 (d, 1H, J=5 Hz), 5.61 (s, 1H), 3.74 (m, 4H), 3.07 (m, 2H), 2.66 (m, 2H), 2.65 (m, 2H), 2.24 (m, 3H), 2.03-2.31 (m, 4H), 1.55 (s, 9H), 0.88 (m, 2H).

Example 675

5-{2-[4-(1-Carbamoylmethyl-piperidin-4-yl)-phenylamino]-pyrrolo[2,1-f][1,2,4]triazin-7-yl}-3,6-dihydro-2H-pyridine-1-carboxylic acid tert-butyl ester, compound as a trifluoroacetic acid salt The compound was prepared in an analogous fashion to Example 522 using 2-{4-[4-(7-bromo-pyrrolo[2,1-f][1,2,4]triazin-2-ylamino)-phenyl]-piperidin-1-yl}-acetamide and 5-(4,4,5,5-tetramethyl-[1,3,2]dioxaborolan-2-yl)-3,6-dihydro-2H-pyridine-1-carboxylic acid tert-butyl ester to provide 5-{2-[4-(1-carbamoylmethyl-piperidin-4-yl)-phenylamino]-pyrrolo[2,1-f][1,2,4]triazin-7-yl}-3,6-dihydro-2H-pyridine-1-carboxylic acid tert-butyl ester, compound as a trifluoroacetic acid salt as a yellow lyophilate (230 mg, 57% yield). LCMS (E/I+) 532 (M+H); $^1$H NMR (400 MHz, DMSO-d6) δ 9.53 (s, 1H), 9.43 (s, 1H), 8.94 (s, 1H), 7.97 (s, 1H), 7.72 (s, 1H), 7.68 (d, 2H, J=8.2 Hz), 7.19 (d, 3H, J=8.4 Hz), 6.87 (d, 1H, J=4.8 Hz), 6.81 (d, 1H, J=4.7 Hz), 4.35 (s, 2H), 3.92 (s, 2H), 3.55 (m, 3H), 3.14 (m, 2H), 2.74 (m, 1H), 2.40 (m, 2H), 1.98 (m, 4H), 1.43 (s, 9H).

Example 676

[7-(2-Methoxy-pyridin-4-yl)-pyrrolo[2,1-f][1,2,4]triazin-2-yl]-[4-(1-methyl-piperidin-4-yl)-phenyl]-amine; compound with trifluoroacetic acid The compound was prepared in an analogous fashion to Example 175 using 2-{4-[4-(7-bromo-pyrrolo[2,1-f][1,2,4]triazin-2-ylamino)-phenyl]-piperidin-1-yl}-acetamide and 5-(4,4,5,5-tetramethyl-[1,3,2]dioxaborolan-2-yl)-3,6-dihy-dro-2H-pyridine-1-carboxylic acid tert-butyl ester to provide 5-{2-[4-(1-carbamoylmethyl-piperidin-4-yl)-phenylamino]-pyrrolo[2,1-f][1,2,4]triazin-7-yl}-3,6-dihydro-2H-pyridine-1-carboxylic acid tert-butyl ester, compound as a trifluoro-acetic acid salt as a yellow lyophilate (21.5 mg, 18% yield). LCMS (E/I+) 415 (M+H). $^1$H NMR (400 MHz, DMSO-d6) δ 9.60 (s, 1H), 9.55 (broad s, 1H), 9.07 (s, 1H), 8.26 (d, 1H, J=5.5 Hz), 7.85 (s, 1H), 7.72 (s, 1H), 7.70 (s, 1H), 7.41 (d, 1H, J=4.8 Hz), 7.22 (d, 2H, J=8.4 Hz), 6.98 (d, 1H, J=4.8 Hz), 3.94 (s, 3H), 3.55 (d, 2H, J=11.5 Hz), 3.10 (dd, 2H, J=10.7, 12 Hz), 2.83 (d, 2H, J=4.6 Hz), 2.76 (m, 2H), 2.04 (2H, J=13.8 Hz), 1.86 (q, 2H, J=12 Hz).

Example 677

2-[4-(4-{7-[3-(Morpholine-4-sulfonyl)-phenyl]-pyrrolo[2,1-f][1,2,4]triazin-2-ylamino}-phenyl)-piperidin-1-yl]-ethanol; compound with trifluoro-acetic acid The compound was prepared in an analogous fashion to Example 522 using 2-[4-(4-amino-phenyl)-piperidin-1-yl]-ethanol and 7-[3-(morpholine-4-sulfonyl)-phenyl]-pyrrolo[2,1-f][1,2,4]triazin-2-ol to provide 2-[4-(4-{7-[3-(morpholine-4-sulfonyl)-phenyl]-pyrrolo[2,1-f][1,2,4]triazin-2-ylamino}-phenyl)-piperidin-1-yl]-ethanol; compound with trifluoro-acetic acid as a brown lyophilate (91.6 mg, 38.5% yield). LCMS (E/I+) 563 (M+H). $^1$H NMR (400 MHz, DMSO-d6) δ 9.54 (s, 1H), 9.25 (s, 1H), 9.05 (s, 1H), 8.51 (s, 1H), 8.44 (d, 2H, J=7.8 Hz), 7.82 (t, 1H, J=7.8 Hz), 7.75 (d, 1H, J=7.8 Hz), 7.69 (d, 2H, J=8.3 Hz), 7.30 (d, 1H, J=4.8 Hz), 7.22 (d, 2H, J=8.3 Hz), 7.01 (d, 1H, J=4.7 Hz), 3.77 (m, 2H), 3.61 (m, 4H), 3.38 (m, 1H), 3.19 (m, 2H), 3.09 (m, 2H), 2.89 (m, 4H), 2.76 (m, 1H), 1.95 (m, 4H).

Example 678

2-[4-(4-{7-[3-(Pyrrolidine-1-sulfonyl)-phenyl]-pyrrolo[2,1-f][1,2,4]triazin-2-ylamino}-phenyl)-piperidin-1-yl]ethanol The compound was prepared in an analogous fashion to Example 522 using 7-[3-(pyrrolidine-1-sulfonyl)-phenyl]-pyrrolo[2,1-f][1,2,4]triazin-2-ol and 2-[4-(4-amino-phenyl)-piperidin-1-yl]-ethanol to provide 2-[4-(4-{7-[3-(pyrrolidine-1-sulfonyl)-phenyl]-pyrrolo[2,1-f][1,2,4]triazin-2-ylamino}phenyl)-piperidin-1-yl]ethanol as a brown lyophilate (49.2 mg, 25% yield). LCMS (E/I+) 547 (M+H). $^1$H NMR (400 MHz, DMSO-d6) δ 9.53 (s, 1H), 9.22 (broad s, 1H), 9.04 (s, 1H), 8.53 (s, 1H), 8.42 (d, 1H, J=7.6 Hz), 7.82 (m, 2H), 7.70 (d, 2H, J=8.5 Hz), 7.29 (d, 1H, J=4.7 Hz), 7.22 (d, 2H, J=8.4 Hz), 7.00 (d, 1H, J=4.7 Hz), 3.77 (t, 2H, J=5 Hz), 3.42 (d, 2H, J=11.9 Hz), 3.37 (m, 1H), 3.18 (m, 6H), 3.09 (m, 2H), 2.75 (m, 1H), 1.95 (m, 3H), 1.65 (m, 4H).

Example 679

2-(4-{4-[7-(4-Methanesulfonyl-phenyl)-pyrrolo[2,1-f][1,2,4]triazin-2-ylamino]-phenyl}-piperidin-1-yl)-ethanol; compound with trifluoroacetic acid The compound was prepared in an analogous fashion to Example 522 using 7-(4-methanesulfonyl-phenyl)-pyrrolo[2,1-f][1,2,4]triazin-2-ol and 2-[4-(4-amino-phenyl)-piperidin-1-yl]-ethanol to provide 2-(4-{4-[7-(4-methanesulfonyl-phenyl)-pyrrolo[2,1-f][1,2,4]triazin-2-ylamino]-phenyl}-piperidin-1-yl)-ethanol; compound with trifluoro-acetic acid as a brown lyophilate (23.4 mg, 19.4% yield). LCMS (E/I+) 492 (M+H). $^1$H NMR (400 MHz, DMSO-d6) δ 9.60 (s, 1H), 9.19 (s, 1H), 9.07 (s, 1H), 8.49 (d, 2H, J=8.4 Hz), 8.05 (d, 2H, J=8.4 Hz), 7.72 (d, 2H, J=8.4 Hz), 7.37 (d, 1H, J=4.8 Hz), 7.22 (d, 1H, J=4.8 Hz), 7.01 (d. 1H, J=4.8 Hz), 3.77 (m, 2H), 3.62 (m, 3H), 3.30 (s, 3H), 3.19 (m, 2H), 3.08 (m, 2H), 2.82 (m, 1H), 1.99 (m, 4H).

Example 680

3-[2-(3-Amino-2-hydroxy-indan-5-ylamino)-pyrrolo [2,1-f][1,2,4]triazin-7-yl]-N-tert-butyl-benzenesulfonamide; compound with trifluoro-acetic acid The titled compound was prepared through an acid catalyzed deprotection using {6-[7-(3-tert-butylsulfamoyl-phenyl)-pyrrolo[2,1-f][1,2,4]triazin-2-ylamino]-2-hydroxy-indan-1-yl}-carbamic acid tert-butyl ester and trifluoroacetic acid in methylene chloride to provide as a light brown lyophilate. LCMS (E/I+) 493 (M+H). $^1$H NMR (400 MHz, DMSO-d6) δ 9.64 (s, 1H), 9.05 (s, 1H), 8.50 (s, 1H), 8.45 (d, 1H, J=7.7 Hz), 8.38 (s, 3H), 7.88 (d, 1H, J=8.2 Hz), 7.83 (dd, 1H, J=7.8 Hz), 7.70 (t, 1H, J=7.8 Hz), 7.62 (broad s, 2H), 7.31 (d, 1H, J=8.3 Hz), 7.24 (d, 1H, J=4.7 Hz), 7.02 (d, 1H, J=4.7 Hz), 5.56 (s, 1H), 4.37 (s, 2H), 3.25 (dd, 1H, J=5.8, 16 Hz), 2.75 (d, 1H, J=16, 20 Hz), 1.11 (s, 9H).

Example 681

1-Amino-6-[7-(2-methoxy-phenyl)-pyrrolo[2,1-f][1,2,4]triazin-2-ylamino]-indan-2-ol; compound with trifluoroacetic acid The titled compound was prepared through an acid catalyzed deprotection using {2-hydroxy-6-[7-(2-methoxy-phenyl)-pyrrolo[2,1-f][1,2,4]triazin-2-ylamino]-indan-1-yl}-carbamic acid tert-butyl ester and trifluoroacetic acid in methylene chloride to provide 1-amino-6-[7-(2-methoxy-phenyl)-pyrrolo[2,1-f][1,2,4]triazin-2-ylamino]-indan-2-ol; compound with trifluoroacetic acid as a tan lyophilate. LCMS (E/I+) 371 (M+H). $^1$H NMR (400 MHz, DMSO-d6) δ 9.51 (s, 1H), 8.97 (s, 1H), 8.33 (m, 3H), 7.86 (d, 2H, J=7.6 Hz), 7.56 (s, 1H), 7.44 (t, 1H, J=8 Hz), 7.21 (d, 1H, J=8 Hz), 7.13 (m, 2H), 6.98 (d, 1H, J=4.5 Hz), 6.94 (d, 1H, J=4.5 Hz), 5.55 (broad s, 1H), 4.31 (d, 2H, J=23 Hz), 3.79 (s, 3H), 3.22 (dd, 1H, J=5.8, 15.4 Hz), 2.71 (dd, 1H, J=4.5, 15.7 Hz).

Example 682

2-(4-{4-[7-(2,6-Dimethoxy-pyridin-3-yl)-pyrrolo[2,1-f][1,2,4]triazin-2-ylamino]-phenyl}-piperidin-1-yl)-acetamide. compound with trifluoroacetic acid The titled compound was prepared in analogous fashion as Example 175 using 2-{4-[4-(7-bromo-pyrrolo[2,1-f][1,2,4]triazin-2-ylamino)-phenyl]-piperidin-1-yl}-acetamide and 2,6-dimethoxy-3-(4,4,5,5-tetramethyl-[1,3,2]dioxaborolan-2-yl)-pyridine to give 2-(4-{4-[7-(2,6-dimethoxy-pyridin-3-yl)-pyrrolo[2,1-f][1,2,4]triazin-2-ylamino]-phenyl}-piperidin-1-yl)-acetamide; compound with trifluoroacetic acid as a orange lyophilate (59.8 mg, 57% yield). LCMS (E/I+) 488 (M+H). $^1$H NMR (DMSO-d6; 400 MHz) δ 9.33 (s, 1H), 8.93 (s, 1H), 8.33 (d, 1H, J=8.3 Hz), 7.61 (d, 2H, J=8.2 Hz), 7.21 (s, 1H), 7.11 (d, 3H, J=7.7 Hz), 6.98 (d, 1H, J=4.5 Hz), 6.90 (d, 1H, J=4.2 Hz), 6.60 (d, 1H, J=8.2 Hz), 3.97 (s, 3H), 3.95 (s, 3H), 2.87-2.91 (m, 4H), 2.43 (m, 1H), 2.14 (m, 2H), 1.71 (m, 4H).

Example 691

N-tert-Butyl-3-[2-(2-methoxy-4-piperidin-4-yl-phenylamino)-pyrrolo[2,1-f][1,2,4]triazin-7-yl]-benzenesulfonamide 4-{4-[7-(3-tert-Butylsulfamoyl-phenyl)-pyrrolo[2,1-f][1,2,4]triazin-2-ylamino]-3-methoxy-phenyl}-piperidine-1-carboxylic acid tert-butyl ester In a 10 mL sealed tube, to N-tert-Butyl-3-(2-hydroxy-pyrrolo[2,1-f][1,2,4]triazin-7-yl)-benzenesulfonamide (120 mg, 0.3464 mmol) and N,N-Diisopropylethylamine (0.242 mL, 1.39 mmol) in 3.0 mL of anhydrous DMF was added N-Phenylbis(trifluoromethane-sulfonimide (136 mg, 0.381 mmol). After stirring at room temperature for 30 minutes, 4-(4-Amino-3-methoxy-phenyl)-piperidine-1-carboxylic acid tert-butyl ester (140 mg, 0.460 mmol) was added. The reaction mixture was heated at 65° C. for 2.5 days. The reaction mixture was purified via silica gel column chromatography using 100:1 DCM:MeOH as the eluant. The collected fractions afforded impure 4-{4-[7-(3-tert-Butylsulfamoyl-phenyl)-pyrrolo[2,1-f][1,2,4]triazin-2-ylamino]-3-methoxy-phenyl}-piperidine-1-carboxylic acid tert-butyl ester as a sticky brown solid.

To 4-{4-[7-(3-tert-Butylsulfamoyl-phenyl)-pyrrolo[2,1-f][1,2,4]triazin-2-ylamino]-3-methoxy-phenyl}-piperidine-1-carboxylic acid tert-butyl ester (207.0 mg, 0.31 mmol) in 6.0 mL of DCM at room temperature was added hydrogen chloride gas. When deprotection was complete, ethyl acetate was added, and the precipitate was filtered and washed with ethyl acetate. The orange solid was taken up in water, treated with sat. NaHCO$_3$ until aq. layer pH=13, and extracted with DCM. The organic layers were combined, dried with sodium sulfate, filtered, and conc. in vacuo to afford N-tert-Butyl-3-[2-(2-methoxy-4-piperidin-4-yl-phenylamino)-pyrrolo[2,1-f][1,2,4]triazin-7-yl]-benzenesulfonamide as a burnt orange solid (65 mg, 39%). MP 201-202° C. LCMS (E/I+) 535.21 (M+H). $^1$H NMR (DMSO-d$_6$)-9.01 (s, 1H), 8.56 (s, 1H), 8.36 (d, 1H, J=7.76 Hz), 7.99 (d, 1H, J=8.56 Hz), 7.85 (s, 1H), 7.83 (s, 1H), 7.69 (t, 1H, J=7.84 Hz), 7.23 (d, 1H, J=4.76 Hz), 7.01 (d, 1H, J=4.72 Hz), 6.95-6.89 (m, 2H), 3.32 (s, 3H), 3.10-2.98 (m, 2H), 2.69-2.52 (m, 2H), 1.78-1.69 (m, 2H), 1.69-1.44 (m, 2H), 1.12 (s, 9H).

Example 692

N-tert-Butyl-3-{2-[2-methoxy-4-(1-methyl-piperidin-4-yl)-phenylamino]-pyrrolo[2,1-f][1,2,4]triazin-7-yl}-benzenesulfonamide In a 10 mL sealed tube, to N-tert-Butyl-3-(2-hydroxy-pyrrolo[2,1-f][1,2,4]triazin-7-yl)-benzenesulfonamide (100 mg, 0.289 mmol) and N,N-Diisopropylethylamine (0.202 mL, 1.16 mmol) in 3.0 mL of anhydrous DMF was added N-Phenylbis(trifluoromethane-sulfonimide (113 mg, 0.318 mmol). After stirring at room temperature for 30 minutes, 2-Methoxy-4-(1-methyl-piperidin-4-yl)-phenylamine (84 mg, 0.36 mmol) was added. The reaction mixture was heated at 65° C. overnight. The reaction was conc. in vacuo. The reaction mixture was purified via silica gel column chromatography using 500:12:8 DCM:MeOH:7N NH$_3$/MeOH as the eluant. The collected fractions afforded N-tert-Butyl-3-{2-[2-methoxy-4-(1-methyl-piperidin-4-yl)-phenylamino]-pyrrolo[2,1-f][1,2,4]triazin-7-yl}-benzenesulfonamide as a yellow solid (19.66 mg, 11%). MP 189-198° C. LCMS (E/I+) 549.21 (M+H). $^1$H NMR (DMSO-d$_6$)-9.01 (s, 1H), 8.56 (s, 1H), 8.35 (d, 1H, J=7.88 Hz), 7.99 (d, 1H, J=8.56 Hz), 7.85 (s, 1H), 7.83

(s, 1H), 7.69 (t, 1H, J=7.82 Hz), 7.62 (s, 1H), 7.23 (d, 1H, J=4.72 Hz), 7.01 (d, 1H, J=4.76 Hz), 6.94 (s, 1H), 6.92 (s, 1H), 3.87 (s, 3H), 2.96-2.83 (m, 2H), 2.28-2.17 (s, 3H), 2.10-1.94 (m, 2H), 1.80-1.58 (m, 3H), 1.32-1.21 (m, 1H), 1.12 (s, 9H).

Example 693

2-(4-{4-[7-(3-tert-Butylsulfamoylphenyl)pyrrolo[2,1-f][1,2,4]triazin-2-ylamino]-3-methoxyphenyl)piperidin-1-yl)-acetamide In a 10 mL sealed tube, to N-tert-Butyl-3-(2-hydroxy-pyrrolo[2,1-f][1,2,4]triazin-7-yl)-benzenesulfonamide (127.4 mg, 0.368 mmol) and N,N-Diisopropylethylamine (0.257 mL, 1.47 mmol) in 3.2 mL of anhydrous DMF was added N-Phenylbis(trifluoromethane-sulfonimide (113 mg, 0.318 mmol). After stirring at room temperature for 1 hour, 2-[4-(4-Amino-3-methoxy-phenyl)-piperidin-1-yl]-acetamide (92 mg, 0.349 mmol) was added. The reaction mixture was heated at 65° C. overnight. The reaction was conc. in vacuo. The reaction mixture was purified via silica gel column chromatography using DCM then 500:15:10 DCM:MeOH:7N NH$_3$/MeOH as the eluant. The collected fractions afforded 2-(4-{4-[7-(3-tert-Butylsulfamoylphenyl)pyrrolo[2,1-f][1,2,4]triazin-2-ylamino]-3-methoxyphenyl)piperidin-1-yl)-acetamide as a yellow solid (23.0 mg, 11%). MP 250-252° C. LCMS (E/I+) 592.25 (M+H). $^1$H NMR (DMSO-d$_6$)-9.02 (s, 1H), 8.55 (s, 1H), 8.37 (d, 1H, J=7.84 Hz), 7.99 (d, 1H, J=7.96 Hz), 7.85 (s, 1H), 7.83 (s, 1H), 7.69 (t, 1H, J=7.86 Hz), 7.63 (s, 1H), 7.23 (d, 1H, J=4.80 Hz), 7.21 (br s, 1H), 7.15 (br s, 1H), 7.01 (d, 1H, J=4.72 Hz), 6.95 (s, 1H), 6.92 (s, 1H), 3.88 (s, 3H), 2.97-2.90 (m, 2H), 2.88 (s, 2H), 2.49-2.41 (m, 1H), 2.22-2.11 (m, 2H), 1.84-1.72 (m, 4H), 1.12 (s, 9H).

Example 694

N-tert-Butyl-3-(2-{4-[1-(2-hydroxy-ethyl)-piperidin-4-yl]-2-methoxy-phenylamino}-pyrrolo[2,1-f][1,2,4]triazin-7-yl)-benzenesulfonamide In a 10 mL sealed tube, to N-tert-Butyl-3-(2-hydroxy-pyrrolo[2,1-f][1,2,4]triazin-7-yl)-benzenesulfonamide (100.0 mg, 0.289 mmol) and N,N-Diisopropylethylamine (0.202 mL, 1.16 mmol) in 2.5 mL of anhydrous DMF was added N-Phenylbis(trifluoromethane-sulfonimide (108.3 mg, 0.303 mmol). After stirring at room temperature for 1 hour, 2-[4-(4-Amino-3-methoxy-phenyl)-piperidin-1-yl]-ethanol (76.3 mg, 0.274 mmol) was added. The reaction mixture was heated at 65° C. overnight. The reaction was conc. in vacuo. The reaction mixture was purified via silica gel column chromatography using DCM then 500:15:10 DCM:MeOH:7N NH$_3$/MeOH as the eluant to afford a crude product which was purified on a Gilson to provide N-tert-Butyl-3-(2-{4-[1-(2-hydroxy-ethyl)-piperidin-4-yl]-2-methoxy-phenylamino}-pyrrolo[2,1-f][1,2,4]triazin-7-yl)-benzenesulfonamide (after freebasing) as a yellow solid (32.0 mg, 20%). MP 220-224.5° C. LCMS (E/I+) 579.26 (M+H). $^1$H NMR (DMSO-d$_6$)-9.01 (s, 1H), 8.56 (s, 1H), 8.36 (d, 1H, J=7.8 Hz), 7.99 (d, 1H, J=8.44 Hz), 7.86-7.81 (m, 2H), 7.70 (t, 1H, J=7.84 Hz), 7.62 (s, 1H), 7.23 (d, 1H, J=4.76 Hz), 7.01 (d, 1H, J=4.76 Hz), 6.94 (s, 1H), 6.92 (s, 1H), 4.41 (br s, 1H), 3.87 (s, 3H), 3.57-3.49 (m, 2H), 3.07-2.95 (m, 2H), 2.48-2.39 (m, 3H), 2.15-2.01 (m, 2H), 1.79-1.63 (m, 4H), 1.12 (s, 9H).

Example 695

N-tert-Butyl-3-(2-{4-[1-((S)-2,3-dihydroxy-propyl)-piperidin-4-yl]-2-methoxy-phenylamino}-pyrrolo[2,1-f][1,2,4]triazin-7-yl)-benzenesulfonamide In a 10 mL sealed tube, to N-tert-Butyl-3-(2-hydroxy-pyrrolo[2,1-f][1,2,4]triazin-7-yl)-benzenesulfonamide (100.0 mg, 0.289 mmol) and N,N-Diisopropylethylamine (0.202 mL, 1.16 mmol) in 2.5 mL of anhydrous DMF was added N-Phenylbis(trifluoromethane-sulfonimide (108.3 mg, 0.303 mmol). After stirring at 65° C. for 1 hour, (S)-3-[4-(4-Amino-3-methoxy-phenyl)-piperidin-1-yl]-propane-1,2-diol (85.4 mg, 0.274 mmol) was added. The reaction mixture was heated at 65° C. for 3 hours. The reaction was conc. in vacuo. The reaction mixture was purified via silica gel column chromatography using DCM then 500:15:10 DCM:MeOH:7N NH$_3$/MeOH as the eluant to afford a crude product which was purified on a Gilson to provide (after freebasing) N-tert-Butyl-3-(2-{4-[1-((S)-2,3-dihydroxy-propyl)-piperidin-4-yl]-2-methoxy-phenylamino}-pyrrolo[2,1-f][1,2,4]triazin-7-yl)-benzenesulfonamide as a yellow solid (15.0 mg, 9%). MP 192-220° C. LCMS (E/I+) 609.27 (M+H). $^1$H NMR (DMSO-d$_6$)-9.01 (s, 1H), 8.56 (s, 1H), 8.36 (d, 1H, J=7.84 Hz), 7.99 (d, 1H, J=8.48 Hz), 7.87-7.81 (m, 2H), 7.70 (t, 1H, J=7.84 Hz), 7.62 (s, 1H), 7.23 (d, 1H, J=4.76 Hz), 7.01 (d, 1H, J=4.76 Hz), 6.95-6.90 (m, 1H), 6.92 (s, 1H), 4.60 (br s, 1H), 4.40 (br s, 1H), 3.87 (s, 3H), 3.64 (br s, 1H), 3.41-3.31 (m, 2H), 3.02 (dd, 1H, J=10.20 Hz), 2.99 (d, 1H, J=11.09 Hz), 2.48-2.36 (m, 2H), 2.35-2.24 (m, 1H), 2.15-2.03 (m, 2H), 1.80-1.61 (m, 4H), 1.12 (s, 9H).

Example 696

N-Cyclopropyl-3-{2-[2-methoxy-4-(1-methyl-piperidin-4-yl)phenylamino]pyrrolo[2,1-f][1,2,4]triazin-7-ylbenzenesulfonamide hydrochloride In a 10 mL sealed tube, to N-Cyclopropyl-3-(2-hydroxy-pyrrolo[2,1-f][1,2,4]triazin-7-yl)-benzenesulfonamide (65.0 mg, 0.197 mmol) and N,N-Diisopropylethylamine (0.137 mL, 0.789 mmol) in 1.5 mL of anhydrous DMF was added N-Phenylbis(trifluoromethane-sulfonimide (73.8 mg, 0.207 mmol). After stirring at room temperature for 1 hour, 2-Methoxy-4-(1-methyl-piperidin-4-yl)-phenylamine (41.2 mg, 0.187 mmol) was added. The reaction mixture was heated at 65° C. overnight. The reaction was conc. in vacuo. The reaction mixture was purified via silica gel column chromatography using DCM then 500:15:10 DCM:MeOH:7N NH$_3$/MeOH as the eluant to afford a crude product which was purified on a Gilson to provide (after freebasing then converting to the HCl salt) the title compound as a yellow solid (10.0 mg, 9%). LCMS (E/I+) 533.08 (M+H). $^1$H NMR (DMSO-d$_6$)-9.72 (br s, 1H), 9.03 (s, 1H), 8.57 (s, 1H), 8.37 (d, 1H, J=7.88 Hz), 8.05 (d, 1H, J=8.48 Hz), 8.01-7.96 (m, 1H), 7.89 (s, 1H), 7.82 (d, 1H, J=7.64 Hz), 7.74 (t, 1H, J=7.86 Hz), 7.26 (d, 1H, J=4.72 Hz), 7.03 (d, 1H, J=4.80 Hz), 6.94 (s, 1H), 6.92 (s, 1H), 3.91 (s, 3H), 3.52 (d, 2H, J=11.53 Hz), 3.13-3.00 (m, 2H), 2.85-2.73 (m, 4H), 2.19-2.09 (m, 1H), 2.09-2.00 (m, 2H), 1.97-1.84 (m, 2H), 0.51-0.43 (m, 2H), 0.43-0.36 (m, 2H).

Example 697

2-(4-{4-[7-(3-Cyclopropylsulfamoyl-phenyl)-pyrrolo[2,1-f][1,2,4]triazin-2-ylamino]-3-methoxy-phenyl}-piperidin-1-yl)-acetamide In a 10 mL sealed tube, to N-Cyclopropyl-3-(2-hydroxy-pyrrolo[2,1-f][1,2,4]triazin-7-yl)-benzenesulfonamide (65.0 mg, 0.197 mmol) and N,N-Diisopropylethylamine (0.137 mL, 0.789 mmol) in 1.5 mL of anhydrous DMF was added N-Phenylbis(trifluoro-methanesulfonimide (73.8 mg, 0.207 mmol). After stirring at room temperature for 1 hour, 2-[4-(4-Amino-3-methoxy-phenyl)-piperidin-1-yl]-acetamide (49.2 mg, 0.187 mmol) was added. The reaction mixture was heated at 65° C. overnight. The reaction was conc. in vacuo. The reaction mixture was purified via silica gel column chromatography using DCM then 500:15:10 DCM:MeOH:7N NH$_3$/MeOH as the eluant to afford a crude product which was purified on a Gilson to provide (after freebasing) the title compound as a yellow solid (6.5 mg, 6%). LCMS (E/I+) 576.12 (M+H). $^1$H NMR (DMSO-d$_6$)-9.02 (s, 1H), 8.49 (s, 1H), 8.44 (d, 1H, J=7.72 Hz), 8.03-7.96 (m, 2H), 7.85 (s, 1H), 7.82 (d, 1H, J=7.88 Hz), 7.74 (t, 1H, J=7.84 Hz), 7.24 (d, 1H, J=4.80 Hz), 7.22 (br s, 1H), 7.15 (br s, 1H), 7.01 (d, 1H, J=4.76 Hz), 6.95 (s, 1H), 6.92 (d, 1H, J=8.56 Hz), 3.88 (s, 3H), 3.00-2.82 (m, 4H), 2.24-2.08 (m, 3H), 1.86-1.70 (m, 4H), 0.50-0.43 (m, 2H), 0.43-0.35 (m, 2H).

Example 698

N-Cyclopropyl-3-(2-{4-[1-(2-hydroxy-ethyl)-piperidin-4-yl]-2-methoxyphenylaminopyrrolo[2,1-f][1,2,4]triazin-7-yl)benzenesulfonamide In a 10 mL sealed tube, to N-Cyclopropyl-3-(2-hydroxy-pyrrolo[2,1-f][1,2,4]triazin-7-yl)-benzenesulfonamide (65.0 mg, 0.197 mmol) and N,N-Diisopropylethylamine (0.137 mL, 0.789 mmol) in 1.5 mL of anhydrous DMF was added N-Phenylbis(trifluoro-methanesulfonimide (73.8 mg, 0.207 mmol). After stirring at room temperature for 1 hour, 2-[4-(4-Amino-3-methoxy-phenyl)-piperidin-1-yl]-ethanol (68.6 mg, 0.187 mmol) was added. The reaction mixture was heated at 65° C. overnight. The reaction was conc. in vacuo. The reaction mixture was purified via silica gel column chromatography using DCM then 500:15:10 DCM:MeOH:7N NH$_3$/MeOH as the eluant to afford a crude product which was purified on a Gilson to provide (after freebasing) the title compound as a yellow solid (8.0, 7%). LCMS (E/I+) 563.08 (M+H). $^1$H NMR (DMSO-d$_6$)-9.02 (s, 1H), 8.50 (s, 1H), 8.42 (d, 1H, J=7.80 Hz), 8.01-7.97 (m, 2H), 7.86-7.79 (m, 2H), 7.75 (t, 1H, J=7.80 Hz), 7.24 (d, 1H, J=4.72 Hz), 7.01 (d, 1H, J=4.72 Hz), 6.95-6.89 (m, 2H), 4.42 (br s, 1H), 3.87 (s, 3H), 3.58-3.48 (m, 2H), 3.08-2.95 (m, 2H), 2.45-2.38 (m, 2H), 2.18-2.00 (m, 3H), 1.80-1.63 (m, 4H), 0.50-0.43 (m, 2H), 0.43-0.36 (m, 2H).

Example 699

N-tert-Butyl-3{2-[3-(2-hydroxyethyl)-8-methoxy-2,3,4,5-tetrahydro-1H-3-benzazepin-7-ylamino]pyrrolo[2,1-f][1,2,4]triazin-7-ylbenzenesulfonamide In a 10 mL sealed tube, to N-tert-butyl-3-(2-hydroxy-pyrrolo[2,1-f][1,2,4]triazin-7-yl)-benzenesulfonamide (100.0 mg, 0.289 mmol) and N,N-Diisopropylethylamine (0.202 mL, 1.16 mmol) in 2.5 mL of anhydrous DMF was added N-Phenylbis(trifluoromethane-sulfonimide (108.3 mg, 0.303 mmol). After stirring at room temperature for 1 hour, 2-(7-Amino-8-methoxy-1,2,4,5-tetrahydro-3-benzazepin-3-yl)-ethanol (64.8 mg, 0.274 mmol) was added. The reaction mixture was heated at 65° C. overnight. The reaction was conc. in vacuo. The reaction mixture was purified via silica gel column chromatography using DCM then 500:15:10 DCM:MeOH:7N NH$_3$/MeOH as the eluant to afford a crude product which was purified on a Gilson to provide (after freebasing) N-tert-Butyl-3{2-[3-(2-hydroxyethyl)-8-methoxy-2,3,4,5-tetrahydro-1H-3-benzazepin-7-ylamino]pyrrolo[2,1-f][1,2,4]triazin-7-ylbenzenesulfonamide as a yellow solid (30.0, 20%). LCMS (E/I+) 565.14 (M+H). $^1$H NMR (DMSO-d$_6$)-9.01 (s, 1H), 8.58 (d, 1H, J=7.84 Hz), 8.31 (s, 1H), 7.86-7.75 (m, 2H), 7.65 (t, 1H, J=7.86 Hz), 7.60 (s, 1H), 7.20 (d, 1H, J=4.72 Hz), 7.01 (d, 1H, J=4.72 Hz), 6.86 (s, 1H), 4.37 (br s, 1H), 3.83 (s, 3H), 3.57-3.49 (m, 2H), 2.87-2.78 (m, 2H), 2.78-2.71 (m, 2H), 2.69-2.58 (m, 4H), 2.56 (t, 2H, J=6.14 Hz), 1.11 (s, 9H).

Example 700

N-tert-Butyl-3-{2-[3-((R)-2-hydroxypropyl)-8-methoxy-2,3,4,5-tetrahydro-1H-3-benzazepin-7-ylamino]pyrrolo[2,1-f][1,2,4]triazin-7-ylbenzene sulfonamide In a 10 mL sealed tube, to N-tert-butyl-3-(2-hydroxy-pyrrolo[2,1-f][1,2,4]triazin-7-yl)-benzenesulfonamide (100.0 mg, 0.289 mmol) and N,N-Diisopropylethylamine (0.201 mL, 1.16 mmol) in 2.5 mL of anhydrous DMF was added N-Phenylbis(trifluoromethane-sulfonimide (108.3 mg, 0.303 mmol). After stirring at room temperature for 1 hour, (R)-1-(7-Amino-8-methoxy-1,2,4,5-tetrahydro-3-benzazepin-3-yl)-propan-2-ol (72.3 mg, 0.289 mmol) was added. The reaction mixture was heated at 65° C. overnight. The reaction was conc. in vacuo. The reaction mixture was purified via silica gel column chromatography using DCM then 500:15:10 DCM:MeOH:7N NH$_3$/MeOH as the eluant to afford a crude product which was purified on a Gilson to provide (after freebasing) the title compound as a yellow solid (36.0, 21%). LCMS (E/I+) 579.16 (M+H). $^1$H NMR (DMSO-d$_6$)-9.01 (s, 1H), 8.58 (d, 1H, J=7.92 Hz), 8.31 (s, 1H), 7.86-7.77 (m, 2H), 7.65 (t, 1H, J=7.84 Hz), 7.60 (s, 1H), 7.20 (d, 1H, J=4.76 Hz), 7.01 (d, 1H, J=4.76 Hz), 6.85 (s, 1H), 4.26 (br s, 1H), 3.83 (s, 3H), 3.79 (br s, 1H), 2.86-2.80 (m, 2H), 2.78-2.72 (m, 2H), 2.67-2.57 (m, 4H), 2.42-2.28 (m, 2H), 1.11 (s, 9H), 1.08 (d, 3H, J=6.08).

Example 701

N-tert-Butyl-3-{2-[3-((S)-2-hydroxypropyl)-8-methoxy-2,3,4,5-tetrahydro-1H-3-benzazepin-7-ylamino]-pyrrolo[2,1-f][1,2,4]triazin-7-ylbenzenesulfonamide The title compound was prepared in an analogous fashion to Example 700 replacing (R)-1-(7-Amino-8-methoxy-1,2,4,5-tetrahydro-3-benzazepin-3-yl)-propan-2-ol with (S)-1-(7-Amino-8-methoxy-1,2,4,5-tetrahydro-3-benzazepin-3-yl)-propan-2-ol to give N-tert-Butyl-3{2-[3-((S)-2-hydroxypropyl)-8-methoxy-2,3,4,5-tetrahydro-1H-3-benzazepin-7-ylamino]-pyrrolo[2,1-f][1,2,4]triazin-7-ylbenzenesulfonamide as a yellow solid (29 mg, 17%). LCMS (E/I+) 579.11 (M+H). $^1$H NMR (DMSO-d$_6$)-9.01 (s, 1H), 8.58 (d, 1H, J=7.84 Hz), 8.31 (s, 1H), 7.86-7.76 (m, 2H), 7.65 (t, 1H, J=7.86 Hz), 7.60 (s, 1H), 7.20 (d, 1H, J=4.76 Hz), 7.01 (d, 1H, J=4.72 Hz), 6.85 (s, 1H), 4.26 (br s, 1H), 3.83 (s, 3H), 3.79 (br s, 2H), 2.86-2.80 (m, 2H), 2.78-2.72 (m, 2H), 2.69-2.56 (m, 4H), 2.42-2.28 (m, 2H), 1.11 (s, 9H), 1.08 (d, 1H, J=6.08).

Example 702

2-(4-{4-[7-(2,3-Dihydro-benzofuran-7-yl)-pyrrolo[2,1-f][1,2,4]triazin-2-ylamino]-3-methoxy-phenyl}-piperidin-1-yl)-ethanol hydrochloride In a 10 mL sealed tube, to 7-(2,3-dihydrobenzofuran-7-yl)-pyrrolo[2,1-f][1,2,4]triazin-2-ol (85.0 mg, 0.211 mmol) and N,N-Diisopropylethylamine (0.147 mL, 0.846 mmol) in 1.5 mL of anhydrous DMF was added N-Phenylbis(trifluoromethanesulfonimide (79.3 mg, 0.222 mmol). After stirring at room temperature for 1 hour, 2-[4-(4-Amino-3-methoxy-phenyl)-piperidin-1-yl]-ethanol (52.93 mg, 0.211 mmol) was added. The reaction mixture was heated at 65° C. overnight. The reaction was conc. in vacuo. The reaction mixture was purified via silica gel column chromatography using DCM then 500:15:10 DCM:MeOH:7N NH$_3$/MeOH as the eluant to afford a crude product which was purified on a Gilson to provide (after freebasing then converting to the HCl salt) the title compound as a burnt yellow solid (13.0, 12%). MP 215-225° C. LCMS (E/I+) 486.11 (M+H). $^1$H NMR (DMSO-d$_6$)-9.85 (br s, 1H), 8.96 (s, 1H), 8.10 (d, 1H, J=8.28 Hz), 8.07 (d, 1H, J=7.95 Hz), 7.79 (br s, 1H), 7.30 (d, 1H, J=7.08 Hz), 7.16 (d, 1H, J=4.72 Hz), 6.99-6.92 (m, 3H), 6.79 (d, 1H, J=8.28 Hz), 4.62 (t, 1H, J=8.72 Hz), 3.88 (s, 3H), 3.84-3.76 (m, 2H), 3.62 (d, 2H, J=11.85 Hz), 3.30 (t, 1H, J=8.66 Hz), 3.22-3.15 (m, 2H), 3.15-3.01 (m, 1H), 2.86-2.76 (m, 1H), 2.16-1.94 (m, 4H).

Example 703

2-(4-{4-[7-(2,3-Dihydro-benzofuran-7-yl)-pyrrolo[2,1-f][1,2,4]triazin-2-ylamino]-3-methoxy-phenyl}-piperidin-1-yl)-acetamide hydrochloride The title compound was prepared in an analogous fashion to Example 702 replacing 2-[4-(4-Amino-3-methoxy-phenyl)-piperidin-1-yl]-ethanol with 2-[4-(4-Amino-3-methoxy-phenyl)-piperidin-1-yl]-acetamide to give 2-(4-{4-[7-(2,3-Dihydro-benzofuran-7-yl)-pyrrolo[2,1-f][1,2,4]triazin-2-ylamino]-3-methoxy-phenyl}-piperidin-1-yl)-acetamide hydrochloride as a yellow solid (19 mg, 13%). MP 160-173° C. LCMS (E/I+) 499.14 (M+H). $^1$H NMR (DMSO-d$_6$)-9.59 (br s, 1H), 8.96 (s, 1H), 8.09 (t, 1H, J=8.88 Hz), 8.02 (s, 1H), 7.77 (s, 1H), 7.73 (s, 1H), 7.29 (d, 1H, J=7.28 Hz), 7.16 (d, 1H, J=4.68 Hz), 6.69 (m, 3H), 6.79 (d, 1H, J=8.00 Hz), 4.62 (t, 2H, J=8.76 Hz), 3.97-3.92 (m, 2H), 3.89 (s, 3H), 3.57 (d, 2H, J=11.20), 3.30 (t, 2H, J=8.70 Hz), 3.23-3.11 (m, 2H), 2.85-2.74 (m, 1H), 2.13-1.95 (m, 4H).

Example 704

2-{7-[7-(2,3-Dihydro-benzofuran-7-yl)-pyrrolo[2,1-f][1,2,4]triazin-2-ylamino]-8-methoxy-1,2,4,5-tetrahydro-3-benzazepin-3-yl}-ethanol hydrochloride The title compound was prepared in an analogous fashion to Example 702 replacing 2-[4-(4-Amino-3-methoxy-phenyl)-piperidin-1-yl]-ethanol with 2-(7-Amino-8-methoxy-1,2,4,5-tetrahydro-3-benzazepin-3-yl)-ethanol to give 2-{7-[7-(2,3-Dihydro-benzofuran-7-yl)-pyrrolo[2,1-f][1,2,4]triazin-2-ylamino]-8-methoxy-1,2,4,5-tetrahydro-3-benzazepin-3-yl}-ethanol hydrochloride as a yellow solid (14 mg, 11%). MP 157-166° C. LCMS (E/I+) 472.18 (M+H). $^1$H NMR (DMSO-d$_6$)-9.89 (br s, 1H), 8.97 (s, 1H), 8.15 (d, 1H, J=7.76 Hz), 8.05 (s, 1H), 7.72 (s, 1H), 7.31 (d, 1H, J=7.36 Hz), 7.18 (d, 1H, J=4.68 Hz), 7.00-6.95 (m, 3H), 5.36 (br s, 1H), 4.62 (t, 2H, J=8.76 Hz), 3.87 (s, 3H), 3.84-3.77 (m, 2H), 3.75-3.63 (m, 2H), 3.33-3.21 (m, 7H), 3.15-3.04 (m, 2H), 3.04-2.94 (m, 2H), 2.82-2.72 (m, 1H).

Example 705

[7-(2,3-Dihydro-benzofuran-7-yl)-pyrrolo[2,1-f][1,2,4]triazin-2-yl]-[2-methoxy-4-(1-methyl-piperidin-4-yl)-phenyl]-amine hydrochloride The title compound was prepared in an analogous fashion to Example 702 replacing 2-[4-(4-Amino-3-methoxy-phenyl)-piperidin-1-yl]-ethanol with 2-Methoxy-4-(1-methyl-piperidin-4-yl)-phenylamine to give [7-(2,3-Dihydro-benzofuran-7-yl)-pyrrolo[2,1-f][1,2,4]triazin-2-yl]-[2-methoxy-4-(1-methyl-piperidin-4-yl)-phenyl]-amine hydrochloride as a yellow solid (6.0 mg, 6%). LCMS (E/I+) 456.21 (M+H). $^1$H NMR (DMSO-d$_6$)-9.74 (br s, 1H), 8.96 (s, 1H), 8.10 (t, 2H, J=8.52 Hz), 7.77 (s, 1H), 7.29 (d, 1H, J=7.36 Hz), 7.16 (d, 1H, J=4.68 Hz), 6.99-6.91 (m, 2H), 6.98 (d, 1H, J=8.40 Hz), 4.61 (t, 2H, J=8.72), 3.90 (s, 3H), 3.55-3.47 (m, 2H), 3.33-3.26 (m, 3H), 3.12-3.00 (m, 2H), 2.84-2.74 (m, 4H), 2.08-2.00 (m, 2H), 1.98-1.83 (m, 2H).

Example 706

2-(4-{4-[7-(2,3-Dihydro-benzofuran-7-yl)-pyrrolo[2,1-f][1,2,4]triazin-2-ylamino]-phenyl}-piperidin-1-yl)-acetamide The title compound was prepared in an analogous fashion to Example 702 replacing 2-[4-(4-Amino-3-methoxy-phenyl)-piperidin-1-yl]-ethanol with 2-[4-(4-Aminophenyl)-piperidin-1-yl]-acetamide to give 2-(4-{4-[7-(2,3-Dihydro-benzofuran-7-yl)-pyrrolo[2,1-f][1,2,4]triazin-2-ylamino]-phenyl}-piperidin-1-yl)-acetamide as a yellow solid (16.0 mg, 8.45%). MP 242-244.5° C. LCMS (E/I+) 469.17 (M+H). $^1$H NMR (DMSO-d$_6$)-9.38 (s, 1H), 8.96 (s, 1H), 8.10 (d, 1H, J=7.80 Hz), 7.70 (d, 2H, J=8.32 Hz), 7.31 (d, 1H, J=7.32 Hz), 7.23 (br s, 1H), 7.17-7.10 (m, 4H), 7.02 (t, 1H, J=7.56 Hz), 6.93 (d, 1H, J=4.68 Hz), 4.62 (t, 2H, J=8.76 Hz), 3.29 (s, 1H), 3.05-2.79 (m, 3H), 2.28-2.07 (m, 2H), 1.85-1.65 (m, 4H), 1.29-1.20 (br s, 1H).

Example 707

2-(4-{2-[7-(2,3-Dihydro-benzofuran-7-yl)-pyrrolo[2,1-f][1,2,4]triazin-2-ylamino]-3-methoxy-6,7,8,9-tetrahydro-5H-benzocyclohepten-6-yl}-piperazin-1-yl)-ethanol dihydrochloride The title compound was prepared in an analogous fashion to Example 702 replacing 2-[4-(4-Amino-3-methoxy-phenyl)-piperidin-1-yl]-ethanol with 2-[4-Amino-3-methoxy-6,7,8,9-tetrahydro-5H-benzocyclohepten-6-yl)-piperazin-1-yl]-ethanol to give 2-(4-{2-[7-(2,3-Dihydro-benzofuran-7-yl)-pyrrolo[2,1-f][1,2,4]triazin-2-ylamino]-3-methoxy-6,7,8,9-tetrahydro-5H-benzocyclohepten-6-yl}-piperazin-1-yl)-ethanol dihydrochloride as a yellow solid (15.0 mg, 9.42%). MP 173-203° C. LCMS (E/I+) 555.21 (M+H). $^1$H NMR (DMSO-d$_6$)-11.59 (br s, 1H), 10.88 (br s, 1H), 8.96 (s, 1H), 8.14 (d, 1H, J=7.64 Hz), 8.03 (s, 1H), 7.67 (s, 1H), 7.31 (d, 1H, J=7.36 Hz), 7.18 (d, 1H, J=4.72 Hz), 6.98-6.89 (m, 3H), 4.62 (t, 2H, J=8.76 Hz), 3.87 (s, 3H), 3.83-3.08 (m, 16H), 3.29 (t, 2H, J=8.70 Hz), 2.80-2.70 (m, 1H), 2.63-2.54 (m, 1H), 2.35-2.20 (m, 1H), 2.16-2.02 (m, 1H), 2.00-1.85 (m, 1H), 1.43-1.28 (m, 1H).

Example 708

2-{7-[7-(2,3-Dihydro-benzo furan-7-yl)-pyrrolo[2,1-f][1,2,4]triazin-2-ylamino]-8-methoxy-1,2,4,5-tetrahydro-3-benzazepin-3-yl}-acetamide hydrochloride The title compound was prepared in an analogous fashion to Example 702 replacing 2-[4-(4-Amino-3-methoxy-phenyl)-piperidin-1-yl]-ethanol with 2-Amino-1-(7-amino-8-methoxy 1,2,4,5-tetrahydro-3-benzazepin-3-yl)-ethanone to give 2-{7-[7-(2,3-Dihydro-benzo furan-7-yl)-pyrrolo[2,1-f][1,2,4]triazin-2-ylamino]-8-methoxy-1,2,4,5-tetrahydro-3-benzazepin-3-yl}-acetamide hydrochloride as a yellow solid (10.0 mg, 7.56%). MP 232-234° C. LCMS (E/I+) 485.19 (M+H). $^1$H NMR (DMSO-d$_6$)-8.95 (s, 1H), 8.15 (d, 1H, J=7.84 Hz), 7.98 (s, 1H), 7.61 (s, 1H), 7.33 (br s, 1H), 7.31 (d, 1H, J=7.36 Hz), 7.17 (d, 2H, J=4.52 Hz), 6.96-6.90 (m, 2H), 6.85 (s, 1H), 4.61 (t, 2H, J=8.74 Hz), 3.85 (s, 3H), 3.28 (t, 2H, J=8.70 Hz), 2.99 (s, 2H), 2.90-2.84 (m, 2H), 2.82-2.75 (m, 2H), 2.65-2.57 (m, 4H).

Example 709

[7-(2,3-Dihydro-benzofuran-7-yl)-pyrrolo[2,1-f][1,2,4]triazin-2-yl]-(8-methoxy-2,3,4,5-tetrahydro-1H-3-benzazepin-7-yl)-amine hydrochloride In a 10 mL sealed tube, to 7-(2,3-dihydrobenzofuran-7-yl)-pyrrolo[2,1-f][1,2,4]triazin-2-ol (214.0 mg, 0.761 mmol) and N,N-Diisopropylethylamine (0.371 mL, 2.13 mmol) in 3.0 mL of anhydrous DMF was added N-Phenylbis(trifluoromethanesulfonimide) (211.1 mg, 0.591 mmol). After stirring at room temperature for 1 hour, 7-Amino-8-methoxy-1,2,4,5-tetrahydro-3-benzazepine-3-carboxylic acid tert-butyl ester (173 mg, 0.592 mmol) was added. The reaction mixture was heated at 65° C. overnight. The reaction was conc. in vacuo. The reaction mixture was purified via silica gel column chromatography using DCM then 100:1 DCM:MeOH to afford a crude product which was dissolved in DCM and treated with HCl gas. When deprotection was complete, the reaction was conc. in vacuo and purified on a Gilson to provide (after freebasing then converting to the HCl salt) [7-(2,3-Dihydro-benzofuran-7-yl)-pyrrolo[2,1-f][1,2,4]triazin-2-yl]-(8-methoxy-2,3,4,5-tetrahydro-1H-3-benzazepin-7-yl)-amine hydrochloride as a burnt yellow solid (21.0, 7.51%). MP 182-194° C. LCMS (E/I+) 428.17 (M+H). $^1$H NMR (DMSO-d$_6$)-9.08 (br s, 2H), 8.97 (s, 1H), 8.15 (d, 1H, J=7.80 Hz), 8.04 (s, 1H), 7.72 (s, 1H), 7.31 (d, 1H, J=7.12 Hz), 7.18 (d, 1H, J=4.72 Hz), 6.99-6.93 (m, 3H), 4.62 (t, 2H, J=8.74 Hz), 3.87 (s, 3H), 3.82-3.58 (m, 6H), 3.28 (t, 2H, J=8.68 Hz), 3.24-3.15 (m, 4H), 3.09-3.04 (m, 2H), 2.99-2.93 (m, 2H).

Example 710

[7-(2,3-Dihydro-benzofuran-7-yl)-pyrrolo[2,1-f][1,2,4]triazin-2-yl]-(8-piperazin-1-yl-quinolin-3-yl)-amine 4-(3-Aminoquinolin-8-yl)-piperazine-1-carboxylic acid tert-butyl ester In a 10-mL sealed tube was heated 4-(3-Iodoquinolin-8-yl)piperazine-1-carboxylic acid tert-butyl ester (520.0 mg, 1.184 mmol), 9,9-Dimethyl-4,5-bis(diphenylphosphino)-xanthene (137 mg, 0.2367 mmol), tris(dibenzylideneacetone)dipalladium(0) (108.4 mg, 0.1184 mmol), sodium tert-butoxide (341.3 mg, 3.551 mmol), and benzophenone imine (218 L, 1.30 mmol) in 13 mL toluene at 100° C. for 5 hours. The reaction was cooled and water and sodium chloride were added. The product was extracted with DCM, dried with sodium sulfate, filtered, and conc. in vacuo. Purification via silica gel chromatography eluting with 100:1 DCM:MeOH afforded the crude imine which was dissolved in 10 THF and treated with 10 drops of 12.1M aq. HCl at room temperature. Upon reaction completion, water and sat. NaHCO$_3$ were added to the reaction whose contents were extracted with DCM. The combined extracts were dried with sodium sulfate, filtered, and conc. in vacuo. The crude material was purified via silica gel chromatography eluting with 50:1 DCM:MeOH to provide 4-(3-Aminoquinolin-8-yl)-piperazine-1-carboxylic acid tert-butyl ester as an off-white solid (182 mg, 44.5%). MP 168-173° C. LCMS (E/I+) 329.13 (M+H). $^1$H NMR (DMSO-d$_6$)-8.37 (d, 1H, J=2.56 Hz), 7.23 (t, 1H, J=7.71 Hz), 7.18 (d, 1H, J=7.76 Hz), 7.08 (d, 1H, J=2.52 Hz), 6.74 (d, 1H, J=7.12 Hz), 5.58 (s, 2H), 3.59-3.51 (m, 4H), 3.25-3.19 (m, 4H), 1.43 (s, 9H).

[7-(2,3-Dihydro-benzofuran-7-yl)-pyrrolo[2,1-f][1,2,4]triazin-2-yl]-(8-piperazin-1-yl-quinolin-3-yl)-amine The title compound was prepared in an analogous fashion to Example 709 replacing 7-Amino-8-methoxy-1,2,4,5-tetrahydro-3-benzazepine-3-carboxylic acid tert-butyl ester with 4-(3-Aminoquinolin-8-yl)-piperazine-1-carboxylic acid tert-butyl ester to give [7-(2,3-Dihydro-benzofuran-7-yl)-pyrrolo[2,1-f][1,2,4]triazin-2-yl]-(8-piperazin-1-yl-quinolin-3-yl)-amine as a red-brown solid (4.0 mg, 3%). LCMS (E/I+) 464.15 (M+H). $^1$H NMR (DMSO-d$_6$)-10.04 (s, 1H), 9.06 (s, 1H), 8.99 (d, 1H, J=2.40 Hz), 8.74 (d, 1H, J=2.32 Hz), 8.07 (d, 1H, J=7.60 Hz), 7.45-7.37 (m, 2H), 7.19-7.14 (m, 2H), 7.08 (d, 1H, J=7.54 Hz), 7.01 (d, 1H, J=4.68 Hz), 6.93 (d, 1H, J=7.60 Hz), 4.61 (t, 2H, J=8.74 Hz), 3.37-3.32 (m, 4H), 3.28-3.19 (m, 4H), 3.00-2.90 (m, 4H).

Example 711

4-{4-[7-(2-Methoxy-phenyl)-pyrrolo[2,1-f][1,2,4]triazin-2-ylamino]-pyrazol-1-yl}-piperidine-1-carboxylic acid tert-butyl ester In a 10 mL sealed tube, to 7-(2-Methoxyphenyl)-pyrrolo[2,1-f][1,2,4]triazin-2-ol (90.58 mg, 0.376 mmol) and N,N-Diisopropylethylamine (0.262 mL, 1.50 mmol) in 2.0 mL of anhydrous DMF was added N-Phenylbis(trifluoromethane)sulfonamide) (211.1 mg, 0.591 mmol). After stirring at room temperature for 2 hours, 4-(4-Amino-pyrazol-1-yl)-piperidine-1-carboxylic acid tert-butyl ester (100 mg, 0.376 mmol) (synthesized according to literature procedure, Tet. Lett. 2008, 49, 2996) was added. The reaction mixture was heated at 65° C. overnight. The reaction was conc. in vacuo. The reaction mixture was purified via silica gel column chromatography using 100:1 DCM:MeOH then 500:15:10 DCM:MeOH:7N NH$_3$/MeOH to afford the title compound as an orange foam. MP 95-100° C. LCMS (E/I+) 490.19 (M+H). $^1$H NMR (DMSO-d$_6$)-9.32 (s, 1H), 8.88 (s, 1H), 7.72 (d, 1H, J=7.32 Hz), 7.69 (s, 1H), 7.48 (t, 1H, J=7.78 Hz), 7.36 (s, 1H), 7.20 (d, 1H, J=8.32 Hz), 7.11 (t, 1H, J=7.44 Hz), 6.88 (d, 1H, J=4.60 Hz), 6.85 (d, 1H, J=4.60 Hz), 4.22-4.11 (m, 1H), 4.11-3.98 (m, 2H), 3.76 (s, 3H), 3.00-2.76 (m, 2H), 1.93-1.84 (m, 2H), 1.58-1.49 (m, 2H), 1.47 (9H).

Example 712

4-(4-{7-[2-Methanesulfonyl-methyl-amino)-phenyl]-pyrrolo[2,1-f][1,2,4]triazin-2-ylamino}-pyrazol-1-yl)-piperidine-1-carboxylic acid tert-butyl ester The title compound was prepared in an analogous fashion to Example 711 replacing 7-(2-Methoxyphenyl)-pyrrolo[2,1-f][1,2,4]triazin-2-ol with N-[2-(2-Hydroxypyrrolo[2,1-f][1,2,4]triazin-7-yl)phenyl]-N-methyl-methanesulfonamide to give 4-(4-{7-[2-Methanesulfonyl-methyl-amino)-phenyl]-pyrrolo[2,1-f][1,2,4]triazin-2-ylamino}-pyrazol-1-yl)-piperidine-1-carboxylic acid tert-butyl ester as a yellow-orange solid. MP 233-234° C. LCMS (E/I+) 567.17 (M+H). $^1$H NMR (DMSO-$d_6$)-9.35 (s, 1H), 8.90 (s, 1H), 7.81 (d, 1H, J=7.44 Hz), 7.67 (d, 1H, J=7.64 Hz), 7.61-7.50 (m, 3H), 7.34 (s, 1H), 6.90 (d, 1H, J=4.60H), 6.88 (d, 1H, J=4.64 Hz), 4.19-4.09 (m, 1H), 4.09-3.95 (m, 2H), 3.01 (s, 3H), 2.96-2.85 (m, 1H), 2.84 (s, 3H), 2.00-1.92 (m, 1H), 1.47 (s, 9H).

Example 713

4-{4-[7-(2,3-Dihydro-benzofuran-7-yl)-pyrrolo[2,1-f][1,2,4]triazin-2-ylamino]-pyrazol-1-yl}-piperidine-1-carboxylic acid tert-butyl ester The title compound was prepared in an analogous fashion to Example 711 replacing 7-(2-Methoxyphenyl)-pyrrolo[2,1-f][1,2,4]triazin-2-ol with 7-(2,3-dihydrobenzofuran-7-yl)-pyrrolo[2,1-f][1,2,4]triazin-2-ol to give 4-{4-[7-(2,3-Dihydro-benzofuran-7-yl)-pyrrolo[2,1-f][1,2,4]triazin-2-ylamino]-pyrazol-1-yl}-piperidine-1-carboxylic acid tert-butyl ester as a red-orange solid. MP 84-95° C. LCMS (E/I+) 502.17 (M+H). $^1$H NMR (DMSO-$d_6$)-9.36 (s, 1H), 8.89 (s, 1H), 7.94 (d, 1H, J=7.68 Hz), 7.88 (s, 1H), 7.66-7.59 (m, 1H), 7.58-7.52 (m, 1H), 7.45 (s, 1H), 7.29 (d, 1H, J=7.16 Hz), 7.02-6.69 (m, 2H), 6.88 (d, 1H, J=4.64 Hz), 4.57 (t, 2H, J=8.72 Hz), 4.28-4.18 (m, 1H), 4.11-3.98 (m, 2H), 3.28 (t, 2H, J=8.76 Hz), 2.98-2.92 (m, 2H), 1.96 (d, 2H, J=11.65 Hz), 1.69-1.56 (m, 2H), 1.45 (s, 9H).

Example 714

7-[2-(2-Methoxy-4-piperidin-4-ylphenylamino)pyrrolo[2,1-f][1,2,4]triazin-7-yl]-1,3-dihydro-indol-2-one hydrochloride 4-[4-(7-Bromo-pyrrolo[2,1-f][1,2,4]triazin-2-ylamino)-3-methoxy-phenyl]-piperidine-1-carboxylic acid tert-butyl ester In a 10 mL sealed tube, to 7-Bromo-pyrrolo[2,1-f][1,2,4]triazin-2-ol (150.0 mg, 0.701 mmol) and N,N-Diisopropyl-ethylamine (0.488 mL, 2.80 mmol) in 3.8 mL of anhydrous DMF was added N-Phenylbis(trifluoromethanesulfonimide (263 mg, 0.736 mmol). After stirring at room temperature for 2 hours, 4-(4-Amino-3-methoxy-phenyl)-piperidin-1-carboxylic acid tert-butyl ester (214.7 mg, 0.701 mmol) was added. The reaction mixture was heated at 65° C. for 4 hours. The reaction was conc. in vacuo. Water and brine were added and the contents were extracted with DCM. The combined organic layers were dried with sodium sulfate, filtered, and conc. in vacuo. The reaction mixture was purified via silica gel column chromatography using 100:1 DCM:MeOH as the eluant to afford a the title compound as a red oil (52%). $^1$H NMR (DMSO-$d_6$)-8.89 (s, 1H), 8.23 (d, 1H, J=8.20 Hz), 7.83 (s, 1H), 6.98-6.95 (m, 2H), 6.91 (d, 1H, J=4.72 Hz), 6.85 (d, 1H, J=8.52 Hz), 4.66-4.55 (br s, 1H), 4.16-3.99 (m, 3H), 3.89 (s, 3H), 2.87-2.75 (m, 2H), 1.78 (d, 2H, J=12.93 Hz), 1.70 (d, 1H, J=12.57 Hz), 1.42 (s, 9H).

Heated 4-[4-(7-Bromo-pyrrolo[2,1-f][1,2,4]triazin-2-ylamino)-3-methoxy-phenyl]-piperidine-1-carboxylic acid tert-butyl ester (150.0 mg, 0.179 mmol), 7-(4,4,5,5-tetramethyl-[1,3,2]dioxaborolan-2-yl)-1,3-dihydro-indol-2-one (46.42 mg, 0.179 mmol), tetrakis(triphenylphosphine)palladium(0) (41.40 mg, 0.0358 mmol), and sodium bicarbonate (75.24 mg, 0.896 mmol), in 1,4-dioxane (4.5 mL) at 90° C. for 2 hours whereupon sodium carbonate (50 mg, 0.472 mmol) was added. The reaction was heated at 100° C. overnight. After addition of 1.0 mL water, tetrakis(triphenylphosphine)-palladium(0) (50.0, 0.0433 mmol), and 7-(4,4,5,5-tetramethyl-[1,3,2]dioxaborolan-2-yl)-1,3-dihydro-indol-2-one (40.0 mg, 0.154 mmol) and heating for an additional 7 hours, product formation was significant by LC/MS. The reaction was cooled to room temp. and water and brine were added. The contents were extracted with EtOAc and the combined organic layers were dried with sodium sulfate, filtered, and conc. in vacuo. Purified via silica gel chromatography eluting with 100:1 then 50:1 DCM:MeOH to provide an impure product which was dissolved in DCM and treated with HCl gas at room temperature. When deprotection was complete, the contents were conc. in vacuo, dissolved in DMSO, and purified on a Gilson RP-HPLC system. The TFA product was converted into the HCl salt to provide. 7-[2-(2-Methoxy-4-piperidin-4-ylphenylamino)pyrrolo[2,1-f][1,2,4]triazin-7-yl]-1,3-dihydro-indol-2-one hydrochloride as a yellow solid (4.0 mg, 4.1% over 2 steps). LCMS (E/I+) 455.16 (M+H). $^1$H NMR (DMSO-$d_6$)-10.10 (s, 1H), 8.95 (s, 1H), 8.85-8.75 (m, 1H), 8.57-8.43 (m, 1H), 8.00 (d, 1H, J=8.24 Hz), 7.61 (s, 1H), 7.33 (d, 2H, J=7.60 Hz), 7.07 (t, 1H, J=7.60 Hz), 6.95 (d, 1H, J=4.60 Hz), 6.89 (d, 1H, J=4.56 Hz), 6.83 (s, 1H), 6.60 (d, 1H, J=8.32 Hz), 3.86 (s, 3H), 3.62 (s, 2H), 3.36 (d, 2H, J=11.37 Hz), 3.03-2.90 (m, 2H), 2.83-2.73 (m, 1H), 1.92 (d, 2H, J=12.97 Hz), 1.87-1.74 (m, 2H).

Example 715

[7-(2,3-Dihydrobenzofuran-7-yl)pyrrolo[2,1-f][1,2,4]triazin-2-yl]-(1-piperidin-4-yl-1H-pyrazol-4-yl) amine dihydrochloride The compound in Example 713 was dissolved in DCM and treated with HCl gas. When deprotection was complete, the reaction was conc. in vacuo to provide 7-[2-(2-Methoxy-4-piperidin-4-ylphenylamino)pyrrolo[2,1-f][1,2,4]triazin-7-yl]-1,3-dihydro-indol-2-one hydrochloride as a yellow solid (73 mg, 42% over 2 steps). MP 160-170° C. LCMS (E/I+) 402.13 (M+H). $^1$H NMR (DMSO-$d_6$)-9.37 (s, 1H), 9.09-8.93 (m, 1H), 8.90 (s, 1H), 8.76-8.62 (m, 1H), 8.04 (1, d, J=7.80 Hz), 7.85 (s, 1H), 7.66-7.52 (m, 3H), 7.33 (d, 1H, J=7.24 Hz), 7.09-7.03 (m, 2H), 6.90 (d, 1H, J=4.68 Hz), 4.61 (t, 2H, J=8.76 Hz), 4.40-4.31 (m, 1H), 3.38 (d, 2H, J=12.13 Hz), 3.27 (t, 2H, J=8.74 Hz), 3.13-3.00 (m, 2H), 2.22-2.13 (m, 2H), 2.13-1.99 (m, 2H).

Example 716

4-{4-[7-(2-Methoxy-phenyl)-pyrrolo[2,1-f][1,2,4]triazin-2-ylamino]-pyrazol-1-yl}-piperidine dihydrochloride The compound in Example 711 was dissolved in DCM and treated with HCl gas. When deprotection was complete, the reaction was conc. in vacuo to provide [7-(2,3-Dihydro-benzofuran-7-yl)-pyrrolo[2,1-f][1,2,4]triazin-2-yl]-(8-methoxy-2,3,4,5-tetrahydro-1H-3-benzazepin-7-yl)-amine hydrochloride as a burnt orange solid (108 mg, 59% over 2 steps). MP 148° C. LCMS (E/I+) 390.12 (M+H). $^1$H NMR (DMSO-d$_6$)-9.33 (s, 1H), 9.10-8.98 (m, 1H), 8.89 (s, 1H), 8.80-8.66 (m, 1H), 7.75 (d, 1H, J=7.52 Hz), 7.67 (s, 1H), 7.54-7.47 (m, 2H), 7.27 (d, 1H, J=8.28 Hz), 7.17 (t, 1H), J=7.40 Hz), 6.90-6.85 (m, 2H), 4.34-4.23 (m, 1H), 3.78 (s, 3H), 3.37 (d, 2H, J=12.49 Hz), 3.13-3.00 (m, 2H), 2.11 (d, 1H, J=13.09 Hz), 2.04-1.92 (m, 2H).

Example 717

N-Methyl-N-{2-[2-(1-piperidin-4-yl-1H-pyrazol-4-ylamino)-pyrrolo[2,1-f][1,2,4]triazin-7-yl]-phenyl}-methanesulfonamide dihydrochloride The compound in Example 712 was dissolved in DCM and treated with HCl gas. When deprotection was complete, the reaction was conc. in vacuo to provide as a burnt orange solid (118 mg, 53% over 2 steps). MP 150° C. LCMS (E/I+) 467.11 (M+H). $^1$H NMR (DMSO-d$_6$)-9.36 (s, 1H), 9.16-8.99 (m, 1H), 8.91 (s, 1H), 8.89-8.71 (m, 1H), 7.88-7.82 (m, 1H), 7.73-7.67 (m, 1H), 7.65-7.57 (m, 3H), 7.49-7.44 (m, 2H), 6.91 (s, 2H), 4.31-4.21 (m, 1H), 3.36 (d, 2H, J=12.17 Hz), 3.12-2.99 (m, 6H), 2.85 (2, 3H), 2.20-2.04 (m, 2H), 2.01-1.88 (m, 2H).

Example 718

4-{4-[7-(2,3-Dihydro-benzofuran-7-yl)-pyrrolo[2,1-f][1,2,4]triazin-2-ylamino]-3-methoxy-phenyl}-piperidin-3-ol; hydrochloride In a 10 mL sealed tube, to 7-(2,3-dihydrobenzofuran-7-yl)-pyrrolo[2,1-f][1,2,4]triazin-2-ol (100.0 mg, 0.355 mmol) and N,N-Diisopropylethylamine (0.248 mL, 1.42 mmol) in 3.0 mL of anhydrous DMF was added N-Phenylbis(trifluoromethanesulfonimide) (133 mg, 0.373 mmol). After stirring at room temperature for 2 hours, 4-(4-Amino-3-methoxyphenyl)-3-hydroxy-piperidine-1-carboxylic acid tert-butyl ester (114.6 mg, 0.355 mmol) was added. The reaction mixture was heated at 65° C. overnight. The reaction was conc. in vacuo. The reaction mixture was purified via silica gel column chromatography using 100:1 then 50:1 DCM:MeOH then 500:15:10 DCM:MeOH:7N NH$_3$/MeOH to afford a crude product which was dissolved in DCM and treated with HCl gas. When deprotection was complete, the reaction was conc. in vacuo and purified on a Gilson to provide (after freebasing then converting to the HCl salt) [7-(2,3-Dihydro-benzofuran-7-yl)-pyrrolo[2,1-f][1,2,4]triazin-2-yl]-(8-methoxy-2,3,4,5-tetrahydro-1H-3-benzazepin-7-yl)-amine hydrochloride as a brown solid (13.0, 7%). MP 178-192° C. LCMS (E/I+) 458.15 (M+H). $^1$H NMR (DMSO-d$_6$)-9.00-8.89 (m, 2H), 8.39-8.26 (m, 1H), 8.13 (d, 1H, J=8.68 Hz), 8.08 (d, 1H, J=7.64), 7.74 (s, 1H), 7.31 (d, 1H, J=7.20 Hz), 7.17-7.13 (m, 1H), 7.00-6.93 (m, 3H), 6.83 (d, 1H, J=8.12 Hz), 5.45 (br s, 1H), 4.62 (t, 2H, J=8.54 Hz), 4.20-3.76 (m, 5H), 3.35-3.24 (m, 3H), 3.22-3.10 (m, 2H), 3.09-2.98 (m, 2H), 2.98-2.91 (m, 2H), 2.38-2.24 (m, 1H), 1.78-1.70 (m, 1H).

Example 719

1-[2-(2-Methoxy-4-piperidin-4-yl-phenylamino)-pyrrolo[2,1-f][1,2,4]triazin-7-yl]-4-phenyl-pyrrolidin-2-one In a 10 mL sealed tube, heated 7-(2,3-dihydrobenzofuran-7-yl)-pyrrolo[2,1-f][1,2,4]triazin-2-ol (150.0 mg, 0.299 mmol), copper(I) iodide (39.8 mg, 0.209 mmol), potassium carbonate (82.5 mg, 0.597 mmol), potassium phosphate (127 mg, 0.597 mmol), and (1R,2R)—N,N'-dimethyl-cyclohexane-1,2-diamine (0.0094 mL, 0.060 mmol) in 1.5 mL 1,4-dioxane at 100° C. for 4 hours. Cooled reaction, added water, and extracted with DCM. Dried the combined organic layers with sodium sulfate, filtered, and conc. in vacuo. Purified via silica gel column chromatography eluting with 100:1 DCM:MeOH to provide the title compound as a free base which was dissolved in DCM and treated with HCl gas. When deprotection was complete, the reaction was conc. in vacuo, dissolved in DMSO, and purified via Gilson RP-HPLC system to provide (after freebasing) 1-[2-(2-Methoxy-4-piperidin-4-yl-phenylamino)-pyrrolo[2,1-f][1,2,4]triazin-7-yl]-4-phenyl-pyrrolidin-2-one as a brown solid (13.0 mg, 8.5%). MP 178-183° C. LCMS (E/I+) 483.13 (M+H). $^1$H NMR (DMSO-d$_6$)-8.89 (s, 1H), 7.98 (d, 1H, J=8.24 Hz), 7.72 (s, 1H), 7.47-7.41 (m, 2H), 7.37 (t, 2H, J=7.20 Hz), 7.33-7.26 (m, 1H), 6.90-6.85 (m, 2H), 6.81-6.77 (m, 1H), 6.68-6.62 (m, 1H), 4.30 (t, 1H, J=8.58 Hz), 3.97 (t, 1H, J=8.88 Hz), 3.89-3.79 (m, 1H), 3.85 (s, 3H), 3.13-3.04 (m, 2H), 2.98-286 (m, 1H), 2.81-2.71 (m, 1H), 2.70-2.60 (m, 2H), 2.60-2.53 (m, 1H), 1.75-1.66 (m, 2H), 1.60-1.47 (m, 2H).

Example 721

(3-Dimethylamino-benzyl)-[5-(2-methoxy-phenyl)-pyrrolo[2,1-f][1,2,4]triazin-2-yl]-amine; compound with trifluoro-acetic acid Into a round bottom flask, Palladium Acetate (0.18 g, 0.72 mmol), Triphenylphosphine (0.85 g, 3.3 mmol) were added and purged under an atmosphere of Nitrogen for 10 minutes. 1,4-Dioxane (10 mL) was added and stirred for 10 minutes. 2-chloro-5-bromo-pyrrolo[1,2-f][1,2,4]triazine (1.0 g, 4.3 mmol) and 2-methoxy-phenyl boronic acid (1.0 g, 5.2 mmol) in N,N-Dimethylformamide (20 mL) and 1.50 M of Sodium carbonate in Water (7 mL, 14 mmol) were added and heated at 90° C. for 2 hours. The solvent was removed under vacuum. The solid was partitioned with water and DCM. The organic was separated, washed with Brine, and dried over magnesium sulfate. The solid was filtered and washed with EtOAc. The solvent was removed under vacuum. The reaction mixture was purified via ISCO column chromatography with DCM and methanol as eluant (0 to 10% Methanol). The collected fractions afforded 2-chloro-5-(2-methoxy-phenyl)-pyrrolo[2,1-f][1,2,4]triazine as a yellow solid. In a round bottom flask, the 2-chloro-5-(2-methoxy-phenyl)-pyrrolo[2,1-f][1,2,4]triazine (50.0 mg, 0.19 mmol) and (3-Aminomethyl-phenyl)-dimethyl-amine (32 mg, 0.21 mmol) were then slurried in 1,4-dioxane (5.0 mL). The mixture was heated at 100° C. for 16 hr. After cooling, the solvent was removed under vacuum and the resulting semi-solid was purified via HPLC reverse phase chromatography with 0.1% TFA in Water and 0.1% TFA in ACN. The collected fractions were lyophilized to give (3-dimethylamino-benzyl)-[5-(2-methoxy-phenyl)-pyrrolo[2,1-f][1,2,4]triazin-2-yl]-amine; compound with trifluoro-acetic acid as an amber amorphous solid (24 mg, 12%). LCMS (E/I+) 374 (M+H). NMR $^1$H (DMSO-d$_6$)-8.74 (s, 1H), 7.63 (s, 1H), 7.41 (d, 1H, J=7.31 Hz), 7.32 (dd, 2H, $J_1=J_2=8.58$ Hz), 7.17 (t, 1H, J=8.47 Hz), 7.12 (dd, 1H, J=7.32 Hz), 7.02 (t, 1H, J=7.26 Hz), 6.90 (bs, 1H), 6.79 (bs, 1H), 6.75 (s, 1H), 6.72 (bs, 1H), 4.40 (s, 2H), 3.80 (s, 3H), 2.92 (s, 6H).

Example 722

[5-(2-Methoxy-phenyl)-pyrrolo[2,1-f][1,2,4]triazin-2-yl]-(2-methyl-1,2,3,4-tetrahydro-isoquinolin-7-yl)-amine; compound with trifluoro-acetic acid Into a round bottom flask, 2-chloro-5-(2-methoxy-phenyl)-pyrrolo[2,1-f][1,2,4]triazine (0.060 g, 0.23 mmol), 2-methyl-1,2,3,4-tetrahydro-isoquinolin-7-ylamine (0.045 g, 0.28 mmol), palladium acetate (0.0114 g, 0.0508 mmol), 2,2'-bis-dicyclohexylphosphanyl-biphenyl (0.0316 g, 0.0578 mmol), and cesium carbonate (0.188 g, 0.578 mmol) were added in 1,4-dioxane (2 mL, 20 mmol). After degassing, the mixture was heated at 100° C. for 16 hr. The mixture was filtered, the solvent was removed under vacuum, and the resulting semi-solid was purified via HPLC reverse phase chromatography with 0.1% TFA in Water and 0.1% TFA in ACN. The collected fractions were lyophilized to give [542-methoxy-phenyl)-pyrrolo[2,1-f][1,2,4]triazin-2-yl]-(2-methyl-1,2,3,4-tetrahydro-isoquinolin-7-yl)-amine; compound with trifluoro-acetic acid as a brown amorphous solid (32 mg, 28%). LCMS (E/I+) 386 (M+H). NMR $^1$H (DMSO-$d_6$)-10.00 (bs, 1H), 9.54 (s, 1H), 8.90 (s, 1H), 7.84 (d, 1H, J=1.92 Hz), 7.66 (d, 1H, J=7.56 Hz), 7.65 (s, 1H), 7.47 (d, 1H, J=7.44 Hz), 7.35 (t, 1H, J=7.44 Hz), 7.20 (d, 1H, J=8.23 Hz), 7.15 (d, 1H, J=8.02 Hz), 7.05 (t, 1H, J=7.11 Hz), 6.91 (d, 1H, J=2.23 Hz), 4.53 (d, 1H, J=16.74 Hz), 4.32 (dd, 1H, $J_1$=8.08 Hz, $J_2$=15.40 Hz), 3.83 (s, 3H), 6.68 (m, 1H), 3.34 (m, 1H), 3.07 (m, 1H), 3.02 (m, 1H), 2.96 (bs, 3H).

Example 723

(4-Ethyl-piperazin-1-yl)-{4-[5-(2-methoxy-phenyl)-pyrrolo[2,1-f][1,2,4]triazin-2-ylamino]-phenyl}-methanone; compound with trifluoro-acetic acid The titled compound was prepared in an analogous fashion to Example 722 replacing 2-methyl-1,2,3,4-tetrahydro-isoquinolin-7-ylamine with (4-amino-phenyl)-(4-ethyl-piperazin-1-yl)-methanone to give (4-ethyl-piperazin-1-yl)-{4-[5-(2-methoxy-phenyl)-pyrrolo[2,1-f][1,2,4]triazin-2-ylamino]-phenyl}-methanone; compound with trifluoro-acetic acid as a yellow amorphous solid (50 mg, 55%). LCMS (E/I+) 457 (M+H). NMR $^1$H (DMSO-$d_6$)-9.80 (s, 1H), 9.60 (bs, 1H), 8.93 (s, 1H), 7.90 (d, 1H, J=2.32 Hz), 7.88 (d, 2H, J=8.85 Hz), 7.49 (d, 1H, J=5.30 Hz), 7.47 (d, 2H, J=8.42 Hz), 7.36 (t, 1H, J=7.55 Hz)), 7.16 (d, 1H, J=8.82 Hz), 7.06 (t, 1H, J=7.64 Hz), 6.94 (d, 1H, J=2.35 Hz), 4.25 (m, 2H), 3.83 (s, 3H), 3.51 (m, 2H), 3.30 (m, 2H), 3.18 (m, 2H), 3.07 (m, 2H), 1.23 (t, 3H, J=7.31 Hz).

Example 724

[5-(4-Methoxy-phenyl)-pyrrolo[2,1-f][1,2,4]triazin-2-yl]-[4-(4-methyl-piperazin-1-yl)-phenyl]-amine; compound with trifluoro-acetic acid The titled compound was prepared in an analogous fashion to Example 722 replacing 2-methoxy-phenyl boronic acid with 4-methoxy-phenylboronic acid and 2-methyl-1,2,3,4-tetrahydro-isoquinoline-7-ylamine with 4-(4-methyl-piperazin-1-yl)-phenylamine to give [5-(4-methoxy-phenyl)-pyrrolo[2,1-f][1,2,4]triazin-2-yl]-[4-(4-methyl-piperazin-1-yl)-phenyl]-amine; compound with trifluoro-acetic acid as a brown amorphous solid (13 mg, 16%). LCMS (E/I+) 415 (M+H). NMR $^1$H (DMSO-$d_6$)-9.54 (bs, 1H), 9.28 (s, 1H), 9.07 (s, 1H), 7.77 (d, 1H, J=1.94 Hz), 7.65 (m, 4H), 7.01 (m, 4H), 6.92 (d, 1H, J=2.04 Hz), 3.80 (s, 3H), 3.75 (m, 2H), 3.52 (m, 2H), 3.19 (m, 2H), 2.91 (m, 2H), 2.87 (s, 3H).

Example 725

[5-(3-Methoxy-phenyl)-pyrrolo[2,1-f][1,2,4]triazin-2-yl]-[4-(4-methyl-piperazin-1-yl)-phenyl]-amine; compound with trifluoro-acetic acid The titled compound was prepared in an analogous fashion to Example 722 replacing 2-methoxy-phenyl boronic acid with 3-methoxy-phenylboronic acid and 2-methyl-1,2,3,4-tetrahydro-isoquinolin-7-ylamine with 4-(4-methyl-piperazin-1-yl)-phenylamine to give [5-(3-Methoxy-phenyl)-pyrrolo[2,1-f][1,2,4]triazin-2-yl]-[4-(4-methyl-piperazin-1-yl)-phenyl]-amine; compound with trifluoro-acetic acid as a brown amorphous solid (16 mg, 19%). LCMS (E/I+) 415 (M+H). NMR $^1$H (DMSO-$d_6$)-9.74 (bs, 1H), 9.33 (s, 1H), 9.12 (s, 1H), 7.80 (d, 1H, J=1.92 Hz), 7.68 (d, 2H, J=8.88 Hz), 7.38 (t, 1H, J=7.88 Hz), 7.28 (d, 1H, J=7.48 Hz), 7.20 (s, 1H), 7.02 (m, 3H), 6.90 (d, 1H, J=7.17 Hz), 3.84 (s, 3H), 3.75 (m, 2H), 3.53 (m, 2H), 3.18 (m, 2H), 2.91 (m, 2H), 2.88 (s, 3H).

Example 726

[5-(4-Fluoro-phenyl)-pyrrolo[2,1-f][1,2,4]triazin-2-yl]-[4-(4-methyl-piperazin-1-yl)-phenyl]-amine; compound with trifluoro-acetic acid The titled compound was prepared in an analogous fashion to Example 722 replacing 2-methoxy-phenyl boronic acid with 4-fluoro-phenylboronic acid and 2-methyl-1,2,3,4-tetrahydro-isoquinolin-7-ylamine with 4-(4-methyl-piperazin-1-yl)-phenylamine to give [5-(4-Fluoro-phenyl)-pyrrolo[2,1-f][1,2,4]triazin-2-yl]-[4-(4-methyl-piperazin-1-yl)-phenyl]-amine; compound with trifluoro-acetic acid as a brown amorphous solid (11 mg, 14%). LCMS (E/I+) 403 (M+H). NMR $^1$H (DMSO-$d_6$)-9.59 (bs, 1H), 9.33 (s, 1H), 9.11 (s, 1H), 7.80 (d, 1H, J=1.97 Hz), 7.75 (m, 2H), 7.67 (d, 2H, J=8.97 Hz), 7.29 (m, 2H), 6.99 (m, 3H), 3.75 (m, 2H), 3.52 (m, 2H), 3.16 (m, 2H), 2.91 (m, 2H), 2.87 (s, 3H).

Example 727

(4-Ethyl-piperazin-1-yl)-{4-[5-(4-fluoro-phenyl)-pyrrolo[2,1-f][1,2,4]triazin-2-ylamino]-phenyl}-methanone; compound with trifluoro-acetic acid The titled compound was prepared in an analogous fashion to Example 722 replacing 2-methoxy-phenyl boronic acid with 4-fluoro-phenylboronic acid and 2-methyl-1,2,3,4-tetrahydro-isoquinolin-7-ylamine with (4-amino-phenyl)-(4-ethyl-piperazin-1-yl)-methanone to give (4-ethyl-piperazin-1-yl)-{4-[5-(4-fluoro-phenyl)-pyrrolo[2,1-f][1,2,4]triazin-2-ylamino]-phenyl}-methanone; compound with trifluoro-acetic acid as a orange amorphous solid (34 mg, 45%). LCMS (E/I+) 445 (M+H). NMR $^1$H (DMSO-$d_6$)-9.87 (s, 1H), 9.73 (bs, 1H), 9.20 (s, 1H), 7.90 (m, 3H), 7.76 (m, 2H), 7.46 (d, 2H, J=8.49 Hz), 7.30 (t, 2H, J=8.77 Hz), 7.08 (d, 1H, J=2.02 Hz), 4.25 (m, 2H), 3.51 (m, 2H), 3.30 (m, 2H), 3.18 (m, 2H), 3.07 (m, 2H), 1.23 (t, 3H, J=7.42 Hz).

Example 728

[5-(4-Fluoro-phenyl)-pyrrolo[2,1-f][1,2,4]triazin-2-yl]-(2-methyl-1,2,3,4-tetrahydro-isoquinolin-7-yl)-amine; compound with trifluoro-acetic acid The titled compound was prepared in an analogous fashion to Example 722 replacing 2-methoxy-phenyl boronic acid with 4-fluoro-phenylboronic acid to give [5-(4-fluoro-phenyl)-pyrrolo[2,1-f][1,2,4]triazin-2-yl]-(2-methyl-1,2,3,4-tetrahydro-isoquinolin-7-yl)-amine; compound with trifluoro-acetic acid as a brown amorphous solid (16 mg, 20%). LCMS (E/I+) 374 (M+H). NMR $^1$H (DMSO-d$_6$)-9.92 (bs, 1H), 9.62 (s, 1H), 9.16 (s, 1H), 7.86 (d, 1H, J=2.16 Hz), 7.75 (dd, 2H, J$_1$=5.65 Hz, J$_2$=8.25 Hz), 7.67 (d, 1H, J=6.59 Hz), 7.64 (s, 1H), 7.29 (t, 2H, J=8.64 Hz), 7.21 (d, 1H, J=8.46 Hz), 7.05 (d, 1H, J=2.20 Hz), 4.52 (d, 1H, J=15.30 Hz), 4.32 (dd, 1H, J$_1$=8.10 Hz, J$_2$=15.20 Hz), 3.69 (m, 1H), 3.50 (m, 1H), 3.06 (m, 2H), 2.96 (bs, 3H).

Example 729

(3-Dimethylamino-benzyl)-[5-(4-fluoro-phenyl)-pyrrolo[2,1-f][1,2,4]triazin-2-yl]-amine; compound with trifluoro-acetic acid The titled compound was prepared in an analogous fashion to Example 721 replacing 2-methoxyphenyl boronic acid with 4-fluorophenylboronic acid to give (3-Dimethylamino-benzyl)-[5-(4-fluoro-phenyl)-pyrrolo[2,1-f][1,2,4]triazin-2-yl]-amine; compound with trifluoro-acetic acid as a red amorphous solid (13 mg, 16%). LCMS (E/I+) 362 (M+H). NMR $^1$H (DMSO-d$_6$)-9.01 (s, 1H), 7.69 (t, 2H, J=6.24 Hz), 7.65 (s, 1H), 7.46 (bs, 1H), 7.26 (m, 3H), 7.10 (bs, 1H), 6.95 (dd, 2H, J$_1$=7.48 Hz , J$_2$=13.1 Hz), 6.89 (s, 1H), 4.43 (s, 2H), 2.99 (s, 6H).

Example 730

[5-(3-Fluoro-phenyl)-pyrrolo[2,1-f][1,2,4]triazin-2-yl]-[4-(4-methyl-piperazin-1-yl)-phenyl]-amine; compound with trifluoro-acetic acid The titled compound was prepared in an analogous fashion to Example 722 replacing 2-methoxy-phenyl boronic acid with 3-fluoro-phenylboronic acid and 2-methyl-1,2,3,4-tetrahydro-isoquinolin-7-ylamine with 4-(4-methyl-piperazin-1-yl)-phenylamine to give [5-(3-fluoro-phenyl)-pyrrolo[2,1-f][1,2,4]triazin-2-yl]-[4-(4-methyl-piperazin-1-yl)-phenyl]-amine; compound with trifluoro-acetic acid as a tan amorphous solid (16 mg, 20%). LCMS (E/I+) 403 (M+H). NMR $^1$H (DMSO-d$_6$)-9.64 (bs, 1H), 9.38 (s, 1H), 9.19 (s, 1H), 7.82 (s, 1H), 7.67 (d, 2H, J=8.45 Hz), 7.53 (m, 3H), 7.14 (t, 1H, J=7.55 Hz), 7.09 (s, 1H), 6.99 (d, 2H, J=8.56 Hz), 3.75 (m, 2H), 3.53 (m, 2H), 3.16 (m, 2H), 2.91 (m, 2H), 2.88 (s, 3H).

Example 741

4-Hydroxy-4-(4-{7-[2-(methanesulfonyl-methyl-amino)-phenyl]-pyrrolo[2,1-f][1,2,4]triazin-2-ylamino}-3-methoxy-phenyl)-piperidine-1-carboxylic acid tert-butyl ester 741a) 1-(4-Bromo-2-methoxy-phenyl)-2,2,5,5-tetramethyl-[1,2,5]azadisilolidine Prepared as in J. Org. Chem., Vol. 65, No. 26, 2000, pp. 9268-9271. 4-Bromo-2-methoxy-phenylamine (1.08 g, 1 eq) was dissolved in THF (10 ml) and cooled to −78° C. A solution of 1.8M lithium diisopropylamide in THF (6.24 ml, 2.1 equiv) was added dropwise. Stirred 10 minutes at −78° C. 1,2-bis(chlorodimethylsilyl)ethane (2.30 g, 2.0 equiv) was then added, and the solution was allowed to warm to room temperature while stirring overnight. Partitioned between EtOAc/water. Washed once with water. Dried over sodium sulfate. Concentrated to a dark brown oil. Distilled under high vacuum. Product came over at 115° C. Passed through a short pad of silica gel which had been pre-treated with 1% triethylamine/EtOAc, eluting with 1% triethylamine/hexane. Obtained 1-(4-bromo-2-methoxy-phenyl)-2,2,5,5-tetramethyl-[1,2,5]azadisilolidine as a clear oil which solidified slowly, 250 mg. NMR $^1$H (CDCl$_3$) 7.34 (s, 1H), 6.91 (m, 2H), 3.81 (s, 3H), 0.90 (s, 4H), 0.04 (s, 12H).

741b) 4-(4-Amino-3-methoxy-phenyl)-4-hydroxy-piperidine-1-carboxylic acid tert-butyl ester 1-(4-Bromo-2-methoxy-phenyl)-2,2,5,5-tetramethyl-[1,2,5]azadisilolidine (250 mg, 1.0 equiv) was dissolved in anhydrous THF (4 ml) under an argon atmosphere. A 1M suspension of magnesium in THF (0.941 ml, 1.33 equiv) was added dropwise at room temperature, and the mixture was stirred for 2 hours. It was then transferred via cannula to a room temperature solution of 4-oxo-piperidine-1-carboxylic acid tert-butyl ester (145 mg, 1.0 equiv), and the mixture was heated to reflux 2 hours. Cooled to room temperature and quenched with water. Partitioned between EtOAc/water. Dried over sodium sulfate and concentrated. Purified by preparative TLC, 40% EtOAc/hexane. Obtained 4-(4-amino-3-methoxy-phenyl)-4-hydroxy-piperidine-1-carboxylic acid tert-butyl ester as a purple foam, 52 mg. LCMS (E/I+) 323 (M+H). NMR $^1$H (CDCl$_3$) 6.95 (s, 1H), 6.83 (d, J=5.82 Hz, 1H), 6.62 (d, J=5.73 Hz, 1H), 3.92-4.05 (m, 2H), 3.88 (s, 3H), 3.17-3.30 (m, 2H), 1.89-2.10 (m, 2H), 1.68-1.74 (m, 2H), 1.46 (s, 9H), 1.23 (s, 1H).

741c) 4-Hydroxy-4-(4-{7-[2-(methanesulfonyl-methyl-amino)-phenyl]-pyrrolo[2,1-f][1,2,4]triazin-2-ylamino}-3-methoxy-phenyl)-piperidine-1-carboxylic acid tert-butyl ester 4-(4-Amino-3-methoxy-phenyl)-4-hydroxy-piperidine-1-carboxylic acid tert-butyl ester (50 mg, 1.0 equiv), trifluoromethanesulfonic acid 7-[2-(methanesulfonyl-methyl-amino)-phenyl]pyrrolo[2,1-f][1,2,4]triazin-2-yl ester (70 mg, 1.0 equiv) and N,N-diisopropylethylamine (54 1, 2.0 equiv) were dissolved in 1-methoxy-2-propanol, and heated to 100° C. overnight. Concentrated, and purified by preparative TLC, 60% EtOAc/hexane containing 1% triethylamine. Obtained 4-hydroxy-4-(4-{7-[2-(methanesulfonyl-methyl-amino)-phenyl]-pyrrolo[2,1-f][1,2,4]triazin-2-ylamino}-3-methoxy-phenyl)-piperidine-1-carboxylic acid tert-butyl ester as a brown solid, 43 mg. mp 111-112° C. LCMS (E/I+) 623 (M+H). NMR $^1$H (CDCl$_3$) 8.71 (s, 1H), 8.12 (d, J=4.74 Hz, 1H), 7.90-7.96 (m, 1H), 7.46-7.58 (m, 3H), 7.00-7.05 (m, 2H), 6.79-6.89 (m, 2H), 3.96-4.11 (m, 2H), 3.89 (s, 3H), 3.17-3.29 (m, 2H), 3.12 (s, 3H), 2.66 (s, 3H), 1.85-2.01 (m, 2H), 1.58-1.67 (m, 2H), 1.60 (s, 1H), 1.50 (s, 9H).

Example 742

N-(2-{2-[2-Methoxy-4-(1,2,3,6-tetrahydro-pyridin-4-yl)-phenylamino]-pyrrolo[2,1-f][1,2,4]triazin-7-yl}-phenyl)-N-methyl-methanesulfonamide 4-Hydroxy-4-(4-{7-[2-(methanesulfonyl-methyl-amino)-phenyl]-pyrrolo[2,1-f][1,2,4]triazin-2-ylamino}-3-methoxy-phenyl)-piperidine-1-carboxylic acid tert-butyl ester (41 mg) was dissolved in dichloromethane (1 ml), and trifluoroacetic acid (1 ml) was added. The solution was stirred 2 hours at room temperature, and then concentrated. Purification on Gilson reverse phase chromatograph (15% to 45% acetonitrile/water gradient) and lyophilization afforded N-(2-{2-[2-methoxy-4-(1,2,3,6-tetrahydro-pyridin-4-yl)-phenylamino]-pyrrolo[2,1-f][1,2,4]triazin-7-yl}-phenyl)-N-methyl-methanesulfonamide, compound with trifluoroacetic acid as an orange solid, 16 mg. mp 204-205° C. LCMS (E/I+) 505

(M+H). NMR ¹H (DMSO-d₆) 9.01 (s, 1H), 8.85 (br s, 1H), 7.98-8.05 (m, 2H), 7.80 (s, 1H), 7.64-7.70 (m, 1H), 7.51-7.62 (m, 2H), 7.24-7.48 (m, 1H), 7.11 (s, 1H), 6.98-7.05 (m, 2H), 6.91-6.96 (d, J=4.56, 1H), 6.21 (s, 1H), 3.88 (s, 3H), 3.65-3.82 (m, 2H), 3.39-3.48 (m, 2H), 3.12 (s, 3H), 2.87 (s, 3H), 2.55-2.64 (m, 2H), 2.32 (s, 1H).

Example 743

N-(2-{2-[4-(1-Ethyl-4-hydroxy-piperidin-4-yl)-2-methoxy-phenylamino]-pyrrolo[2,1-f][1,2,4]triazin-7-yl}-phenyl)-N-methyl-methanesulfonamide The titled compound was prepared in an analogous fashion to Example 741, replacing 4-oxo-piperidine-1-carboxylic acid tert-butyl ester with 1-ethylpiperidone to give N-(2-{2-[4-(1-Ethyl-4-hydroxy-piperidin-4-yl)-2-methoxy-phenylamino]-pyrrolo[2,1-f][1,2,4]triazin-7-yl}-phenyl)-N-methyl-methanesulfonamide, compound with trifluoroacetic acid as an orange solid, 46 mg. (38% yield, mp 107-108° C.). LCMS (E/I+) 551 (M+H). NMR ¹H (DMSO-d₆) 9.52 (br s, 1H), 8.98 (s, 1H), 7.94-8.02 (m, 2H), 7.74 (s, 1H), 7.62-7.69 (m, 1H), 7.51-7.59 (m, 2H), 7.11 (s, 1H), 6.95-7.03 (m, 2H), 6.86 (d, J=4.64, 1H), 5.42 (br s, 1H), 3.87 (s, 3H), 3.39-3.46 (m, 2H), 3.15-3.27 (m, 4H), 3.08 (s, 3H), 2.86 (s, 3H), 2.66 (s, 1H), 2.18-2.28 (m, 2H), 1.78-1.86 (m, 2H), 1.24 (t, J=4.66 Hz, 3H).

Example 744

N-(2-{2-[4-(1-Ethyl-1,2,3,6-tetrahydro-pyridin-4-yl)-2-methoxy-phenylamino]-pyrrolo[2,1-f][1,2,4]triazin-7-yl}-phenyl)-N-methyl-methanesulfonamide The titled compound was prepared from N-(2-{2-[4-(1-Ethyl-4-hydroxy-piperidin-4-yl)-2-methoxy-phenylamino]-pyrrolo[2,1-f][1,2,4]triazin-7-yl}-phenyl)-N-methyl-methanesulfonamide in an analogous fashion to Example 742. Obtained N-(2-{2-[4-(1-Ethyl-1,2,3,6-tetrahydro-pyridin-4-yl)-2-methoxy-phenylamino]-pyrrolo[2,1-f][1,2,4]triazin-7-yl}-phenyl)-N-methyl-methanesulfonamide, compound with trifluoroacetic acid as a yellow solid, 4 mg. (10% yield, mp 121-123° C.). LCMS (E/I+) 533 (M+H). NMR ¹H (DMSO-d₆) 9.63 (br s, 1H), 8.99 (s, 1H), 7.95-8.03 (m, 2H), 7.80 (s, 1H), 7.64-7.69 (m, 1H), 7.50-7.60 (m, 2H), 7.12 (s, 1H), 6.98-7.06 (m, 2H), 6.92 (d, J=4.62 Hz, 1H), 6.20 (s, 1H), 3.95-4.04 (m, 2H), 3.91 (s, 3H), 3.60-3.82 (m, 4H), 3.17-3.28 (m, 2H), 3.10 (s, 3H), 2.88 (s, 3H), 1.38 (t, J=4.71, 3H).

Example 745

2-(4-{4-[7-(2,4-Dimethoxy-phenyl)-pyrrolo[2,1-f][1,2,4]triazin-2-ylamino]-3-methoxy-phenyl}-piperidin-1-yl)-acetamide 745a) 7-(2,4-Dimethoxy-phenyl)-2-methylsulfanyl-pyrrolo[2,1-f][1,2,4]triazine
7-Bromo-2-methylsulfanyl-pyrrolo[2,1-f][1,2,4]triazine (500 mg, 1.0 equiv) and 2,4-dimethoxyboronic acid (559 mg, 1.5 equiv) were suspended in dioxane (6 ml) and 2M aqueous sodium carbonate (2.56 ml). The mixture was degassed with argon. Tetrakis(triphenylphosphine)palladium(0) (118 mg, 0.05 equiv) was added, and the mixture was heated at 80° C. overnight. Partitioned between EtOAc/water. Washed once with water. Dried over magnesium sulfate and concentrated. Purified by flash chromatography, 20% EtOAc/hexane. Obtained 7-(2,4-Dimethoxy-phenyl)-2-methylsulfanyl-pyrrolo[2,1-f][1,2,4]triazine as a yellow solid, 592 mg. LCMS (E/I+) 302 (M+H). NMR ¹H (CDCl₃) 8.80 (s, 1H), 7.30-7.41 (m, 2H), 7.00 (s, 1H), 6.64-6.76 (m, 2H), 3.87 (s, 3H), 3.83 (s, 3H), 2.53 (s, 3H).

745b) 7-(2,4-Dimethoxy-phenyl)-2-methanesulfinyl-pyrrolo[2,1-f][1,2,4]triazine
7-(2,4-Dimethoxy-phenyl)-2-methylsulfanyl-pyrrolo[2,1-f][1,2,4]triazine (592 mg, 1.00 equiv) and m-chloroperoxybenzoic acid (77%, 462 mg, 1.05 equiv) were dissolved in methylene chloride and stirred for 2 hours at room temperature. Partitioned between methylene chloride and saturated aqueous sodium bicarbonate. Dried over magnesium sulfate. Triturated with ether to afford 7-(2,4-dimethoxy-phenyl)-2-methanesulfinyl-pyrrolo[2,1-f][1,2,4]triazine as a yellow solid, 605 mg. LCMS (E/I+) 318 (M+H). NMR ¹H (CDCl₃) 9.02 (s, 1H), 7.22-7.34 (m, 2H), 7.03 (s, 1H), 6.67-6.77 (m, 2H), 3.93 (s, 3H), 3.86 (s, 3H), 3.02 (s, 3H).

745c) 7-(2,4-Dimethoxy-phenyl)-pyrrolo[2,1-f][1,2,4]triazin-2-ol
7-(2,4-Dimethoxy-phenyl)-2-methanesulfinyl-pyrrolo[2,1-f][1,2,4]triazine (605 mg) was suspended in 5M NaOH (20 ml) and heated to 80° C. for 3 hours. Cooled to room temperature and acidified with concentrated HCl. Extracted with dichloromethane. Dried over magnesium sulfate. Concentrated to afford 7-(2,4-dimethoxy-phenyl)-pyrrolo[2,1-f][1,2,4]triazin-2-ol as a brown solid (245 mg) that was used without further purification.

745d) 2-(4-{4-[7-(2,4-Dimethoxy-phenyl)-pyrrolo[2,1-f][1,2,4]triazin-2-ylamino]-3-methoxy-phenyl}-piperidin-1-yl)-acetamide
7-(2,4-dimethoxy-phenyl)-pyrrolo[2,1-f][1,2,4]triazin-2-ol (100 mg, 1.0 equiv) was dissolved in anhydrous DMF (6 ml). N,N-diisopropylethylamine (0.614 ml, 9.56 equiv) was added, and the solution was stirred at room temperature for 30 minutes. N-phenylbis(trifluoromethanesulfonimide) (138 mg, 1.05 equiv) was added, and the solution was stirred 1 hour at room temperature. 2-[4-(4-Amino-3-methoxy-phenyl)-piperidin-1-yl]-acetamide (146 mg, 1.50 equiv) was then added, and the mixture was heated to 80° C. for 2 hours. Partitioned between EtOAc/water. Washed once with water. Dried, filtered and concentrated. Purification on Gilson reverse phase chromatograph (10% to 55% acetonitrile/water gradient) and lyophilization afforded 2-(4-{4-[7-(2,4-dimethoxy-phenyl)-pyrrolo[2,1-f][1,2,4]triazin-2-ylamino]-3-methoxy-phenyl}-piperidin-1-yl)-acetamide, compound with trifluoroacetic acid as a brown solid, 5.2 mg. mp 119-121° C. LCMS (E/I+) 517 (M+H). NMR ¹H (CD₃OD) 8.78 (br s, 1H), 8.22 (d, J=4.83 Hz, 1H), 7.77 (d, J=4.87 Hz, 1H), 6.98 (s, 2H), 6.89 (s, 1H), 6.64-6.78 (m, 3H), 3.97 (s, 2H), 3.91 (s, 3H), 3.87 (s, 3H), 3.78 (s, 3H), 3.66-3.74 (m, 2H), 3.15-3.28 (m, 2H), 2.03-2.15 (m, 4H).

Example 746

2-[4-(4-{7-[4,5-Difluoro-2-(methanesulfonyl-methyl-amino)-phenyl]-pyrrolo[2,1-f][1,2,4]triazin-2-ylamino}-3-methoxy-phenyl)-piperidin-1-yl]-acetamide The titled compound was prepared in an analogous fashion to Example 745, replacing 7-(2,4-dimethoxy-phenyl)-pyrrolo[2,1-f][1,2,4]triazin-2-ol with N-[4,5-difluoro-2-(2-hydroxy-pyrrolo[2,1-f][1,2,4]triazin-7-yl)-phenyl]-N-methyl-methanesulfonamide to give 2-[4-(4-{7-[4,5-Difluoro-2-(methanesulfonyl-methyl-amino)-phenyl]-pyrrolo[2,1-f][1,2,4]triazin-2-ylamino}-3-methoxy-phenyl)-piperidin-1-yl]-acetamide, compound with trifluoroacetic acid as an orange solid, 4.5 mg. mp 114-116° C. LCMS (E/I+) 600 (M+H). NMR ¹H (CD₃OD) 8.84 (s, 1H), 8.18 (d, J=4.53, 1H), 7.91-8.00 (m, 1H), 7.62-7.68 (m, 1H), 7.10 (s, 1H), 6.98 (s, 1H), 6.90 (s, 1H), 6.73 (d, J=4.51, 1H), 3.97 (s, 2H), 3.94 (s, 3H), 3.58-3.68 (m, 1H), 3.15-3.29 (m, 3H), 3.12 (s, 3H), 2.78 (s, 3H), 2.02-2.15 (m, 4H).

Example 751

(4-Bromo-phenyl)-[1,2,4]triazino[1,6-a]indol-2-yl-amine

Following the experimental procedure described in Example 262, 2-methanesulfinyl-[1,2,4]triazino[1,6-a]indole and p-bromoaniline were converted to (4-Bromo-phenyl)-[1,2,4]triazino[1,6-a]indol-2-yl-amine as a red solid (8 mg, 11%). MP: 237-243° C.; ¹H-NMR (CDCl₃) δ 9.04 (s, 1H), 8.11 (d, J=8.4 Hz, 1H), 7.84 (d, J=8.4 Hz, 1H), 7.67 (d, J=8.8 Hz, 2H), 7.51 (d, J=8.8 Hz, 2H), 7.46 (m, 1H), 7.36 (m, 1H), 6.98 (s, 1H), 6.89 (s, 1H); LC/MS (ESI+): 341.5 (M+H).

Example 752

(4-Methoxy-phenyl)-[1,2,4]triazino[1,6-a]indol-2-yl-amine

Following the experimental procedure described in Example 262, 2-methanesulfinyl-[1,2,4]triazino[1,6-a]indole and 4-methoxybenzenamine were converted to (4-methoxy-phenyl)-[1,2,4]triazino[1,6-a]indol-2-yl-amine as a yellow solid (6 mg, 10%). MP: 197-200° C.; ¹H-NMR (CDCl₃) δ 8.99 (s, 1H), 8.09 (d, J=8.4 Hz, 1H), 7.81 (d, J=8.4 Hz, 1H), 7.67 (d, J=8.8 Hz, 2H), 7.41 (m, 1H), 7.31 (m, 1H), 6.96 (d, J=8.8 Hz, 2H), 6.93 (s, 1H), 6.82 (br s, 1H), 3.84 (s, 3H); LC/MS (ESI+): 291.6 (M+H).

Example 753

(S)-1-(4-{3-Methoxy-4-[7-(2-methoxy-phenyl)-pyrrolo[2,1-f][1,2,4]triazin-2-ylamino]-phenyl}-piperazin-1-yl)-propan-2-ol 2-Methanesulfinyl-7-(2-methoxy-phenyl)-pyrrolo[2,1-f][1,2,4]triazine (100.00 mg, 0.348 mmol), N,N-diisopropylethylamine (0.1818 mL, 1.044 mmol), and (S)-1-[4-(4-amino-3-methoxyphenyl)-piperazin-1-yl]-propan-2-ol (0.185 g, 0.696 mmol) were dissolved in 1-methoxy-2-propanol (0.224 mL) and the reaction was microwaved on 300 watts, at 180° C. for 40 minutes, when HPLC showed consumption of starting material. The solvent was then evaporated under reduced pressure and the product was isolated by preparative reverse phase HPLC (Gilson, 0.1% TFA water/acetonitrile gradient) followed by neutralization of the resulting TFA salt to afford (S)-1-(4-{3-methoxy-4-[7-(2-methoxy-phenyl)-pyrrolo[2,1-f][1,2,4]triazin-2-ylamino]-phenyl}-piperazin-1-yl)-propan-2-ol as a yellow solid (61 mg, 36%). MP: 79-88° C.; ¹H-NMR (CDCl₃) δ 8.67 (s, 1H), 8.24 (d, J=8.8 Hz, 1H), 8.01 (m, 1H), 7.42 (m, 1H), 7.31 (br s, 1H), 7.12 (m, 1H), 7.06 (d, J=8.8 Hz, 1H), 7.00 (s, 1H), 6.80 (d, J=4.7 Hz, 1H), 6.53 (s, 1H), 6.42 (m, 1H), 3.89 (m, 1H), 3.88 (s, 3H), 3.84 (s, 3H), 3.14 (m, 4H), 2.84 (m, 2H), 2.56 (m, 2H), 2.35 (m, 2H), 2.00 (s, 1H), 1.16 (d, J=7.1 Hz, 3H); LC/MS (ESI+): 489.22 (M+H).

Example 754

(R)-1-(4-{3-Methoxy-4-[7-(2-methoxy-phenyl)-pyrrolo[2,1-f][1,2,4]triazin-2-ylamino]-phenyl}-piperazin-1-yl)-propan-2-ol Following the experimental procedure described in Example 753, 2-Methanesulfinyl-7-(2-methoxy-phenyl)-pyrrolo[2,1-f][1,2,4]triazine and (R)-1-[4-(4-Amino-3-methoxy-phenyl)-piperazin-1-yl]-propan-2-ol were converted to (R)-1-(4-{3-methoxy-4-[7-(2-methoxy-phenyl)-pyrrolo[2,1-f][1,2,4]triazin-2-ylamino]-phenyl}-piperazin-1-yl)-propan-2-ol as a yellow solid (50 mg, 30%). MP: 76-85° C.; ¹H-NMR (CDCl₃) δ 8.67 (s, 1H), 8.24 (d, J=8.8 Hz, 1H), 8.01 (m, 1H), 7.42 (m, 1H), 7.31 (br s, 1H), 7.12 (m, 1H), 7.06 (d, J=8.8 Hz, 1H), 7.00 (s, 1H), 6.80 (d, J=4.7 Hz, 1H), 6.53 (s, 1H), 6.42 (m, 1H), 3.89 (m, 1H), 3.88 (s, 3H), 3.84 (s, 3H), 3.14 (m, 4H), 2.84 (m, 2H), 2.56 (m, 2H), 2.35 (m, 2H), 2.00 (s, 1H), 1.16 (d, J=7.1 Hz, 3H); LC/MS (ESI+): 489.22 (M+H).

Example 755

(S)-1-(4-{4-[7-(5-Chloro-2-methoxy-phenyl)-pyrrolo[2,1-f][1,2,4]triazin-2-ylamino]-3-methoxy-phenyl}-piperazin-1-yl)-propan-2-ol Following the experimental procedure described in Example 753, 7-(5-chloro-2-methoxy-phenyl)-2-methanesulfinyl-pyrrolo[2,1-f][1,2,4]triazine and (S)-1-[4-(4-amino-3-methoxy-phenyl)-piperazin-1-yl]-propan-2-ol were converted to (S)-1-(4-{4-[7-(5-chloro-2-methoxy-phenyl)-pyrrolo[2,1-f][1,2,4]triazin-2-ylamino]-3-methoxy-phenyl}-piperazin-1-yl)-propan-2-ol as a yellow solid (69 mg, 42%). MP: 163-166° C.; ¹H-NMR (CDCl₃) δ 8.68 (s, 1H), 8.26 (d, J=8.8 Hz, 1H), 8.20 (d, J=2.4 Hz, 1H), 7.34 (m, 2H), 7.06 (d, J=4.8 Hz, 1H), 6.96 (d, J=8.8 Hz, 1H), 6.80 (s, 1H), 6.61 (m, 1H), 6.54 (s, 1H), 3.90 (m, 1H), 3.89 (s, 3H), 3.83 (s, 3H), 3.16 (m, 4H), 2.85 (m, 2H), 2.58 (m, 2H), 2.36 (m, 2H), 1.99 (s, 1H), 1.17 (d, J=7.0 Hz, 3H); LC/MS (ESI+): 523.8 (M+H).

Example 756

(R)-1-(4-{4-[7-(5-Chloro-2-methoxy-phenyl)-pyrrolo[2,1-f][1,2,4]triazin-2-ylamino]-3-methoxy-phenyl}-piperazin-1-yl)-propan-2-ol Following the experimental procedure described in Example 753, 7-(5-chloro-2-methoxy-phenyl)-2-methanesulfinyl-pyrrolo[2,1-f][1,2,4]triazine and (R)-1-[4-(4-amino-3-methoxy-phenyl)-piperazin-1-yl]-propan-2-ol were converted to (R)-1-(4-{4-[7-(5-chloro-2-methoxy-phenyl)-pyrrolo[2,1-f][1,2,4]triazin-2-ylamino]-3-methoxy-phenyl}-piperazin-1-yl)-propan-2-ol as a yellow solid (34 mg, 42%). MP: 163-166° C.; ¹H-NMR (CDCl₃) δ 8.68 (s, 1H), 8.26 (d, J=8.8 Hz, 1H), 8.20 (d, J=2.4 Hz, 1H), 7.34 (m, 2H), 7.06 (d, J=4.8 Hz, 1H), 6.96 (d, J=8.8 Hz, 1H), 6.80 (s, 1H), 6.61 (m, 1H), 6.54 (s, 1H), 3.90 (m, 1H), 3.89 (s, 3H), 3.83 (s, 3H), 3.16 (m, 4H), 2.85 (m, 2H), 2.58 (m, 2H), 2.36 (m, 2H), 1.99 (s, 1H), 1.17 (d, J=7.0 Hz, 3H); LC/MS (ESI+): 523.8 (M+H).

Example 757

(R)-3-(4-{4-[7-(5-Chloro-2-methoxy-phenyl)-pyrrolo[2,1-f][1,2,4]triazin-2-ylamino]-3-methoxy-phenyl}-piperazin-1-yl)-propane-1,2-diol Following the experimental procedure described in Example 753, 7-(5-chloro-2-methoxy-phenyl)-2-methanesulfinyl-pyrrolo[2,1-f][1,2,4]triazine and (R)-3-[4-(4-amino-3-methoxy-phenyl)-piperazin-1-yl]-propane-1,2-diol were converted to (R)-3-(4-{4-[7-(5-chloro-2-methoxy-phenyl)-pyrrolo[2,1-f][1,2,4]triazin-2-ylamino]-3-methoxy-phenyl}-piperazin-1-yl)-propane-1,2-diol as a yellow solid (21 mg, 25%). MP: 173-176° C.; $^1$H-NMR (CDCl$_3$) δ 8.68 (s, 1H), 8.26 (d, J=8.8 Hz, 1H), 8.21 (d, J=2.5 Hz, 1H), 7.34 (m, 2H), 7.07 (d, J=4.8 Hz, 1H), 6.97 (d, J=8.8 Hz, 1H), 6.80 (d, J=4.8 Hz, 1H), 6.60 (m, 1H), 6.55 (d, J=2.5 Hz, 1H), 3.90 (m, 1H), 3.89 (s, 3H), 3.84 (s, 3H), 3.79 (m, 1H), 3.54 (m, 1H), 3.16 (m, 4H), 2.86 (m, 2H), 2.65 (m, 4H), 2.44 (m, 1H), 2.30 (br s, 2H); LC/MS (ESI+): 539.17 (M+H).

Example 758

(R)-3-(4-{3-Methoxy-4-[7-(2-methoxy-phenyl)-pyrrolo[2,1-f][1,2,4]triazin-2-ylamino]-phenyl}-piperazin-1-yl)-propane-1,2-diol Following the experimental procedure described in Example 753, 2-Methanesulfinyl-7-(2-methoxy-phenyl)-pyrrolo[2,1-f][1,2,4]triazine and (R)-3-[4-(4-amino-3-methoxy-phenyl)-piperazin-1-yl]-propane-1,2-diol were converted to (R)-3-(4-{3-methoxy-4-[7-(2-methoxy-phenyl)-pyrrolo[2,1-f][1,2,4]triazin-2-ylamino]-phenyl}-piperazin-1-yl)-propane-1,2-diol as a yellow solid (28 mg, 32%). MP: 83-90° C.; $^1$H-NMR (CDCl$_3$) δ 8.67 (s, 1H), 8.24 (d, J=8.8 Hz, 1H), 8.00 (m, 1H), 7.43 (m, 1H), 7.32 (br s, 1H), 7.12 (m, 1H), 7.06 (d, J=8.2 Hz, 1H), 7.01 (d, J=4.6 Hz, 1H), 6.81 (d, J=4.6 Hz, 1H), 6.53 (d, J=2.5 Hz, 1H), 6.42 (m, 1H), 3.90 (m, 1H), 3.89 (s, 3H), 3.84 (s, 3H), 3.78 (m, 1H), 3.54 (m, 1H), 3.15 (m, 4H), 2.86 (m, 2H), 2.65 (m, 4H), 2.60 (br s, 1H), 2.48 (m, 1H); LC/MS (ESI+): 505.17 (M+H).

Example 759

(S)-3-(4-{4-[7-(5-Chloro-2-methoxy-phenyl)-pyrrolo[2,1-f][1,2,4]triazin-2-ylamino]-3-methoxy-phenyl}-piperazin-1-yl)-propane-1,2-diol Following the experimental procedure described in Example 753, 7-(5-chloro-2-methoxy-phenyl)-2-methanesulfinyl-pyrrolo[2,1-f][1,2,4]triazine and (S)-3-[4-(4-amino-3-methoxy-phenyl)-piperazin-1-yl]-propane-1,2-diol were converted to (S)-3-(4-{4-[7-(5-chloro-2-methoxy-phenyl)-pyrrolo[2,1-f][1,2,4]triazin-2-ylamino]-3-methoxy-phenyl}-piperazin-1-yl)-propane-1,2-diol as a yellow solid (27 mg, 32%). MP: 101-104° C.; $^1$H-NMR (CDCl$_3$) δ 8.68 (s, 1H), 8.26 (d, J=8.8 Hz, 1H), 8.21 (d, J=2.5 Hz, 1H), 7.34 (m, 2H), 7.07 (d, J=4.8 Hz, 1H), 6.97 (d, J=8.8 Hz, 1H), 6.80 (d, J=4.8 Hz, 1H), 6.60 (m, 1H), 6.55 (d, J=2.5 Hz, 1H), 3.90 (m, 1H), 3.89 (s, 3H), 3.84 (s, 3H), 3.79 (m, 1H), 3.54 (m, 1H), 3.16 (m, 4H), 2.86 (m, 2H), 2.65 (m, 4H), 2.44 (m, 1H), 2.30 (br s, 2H); LC/MS (ESI+): 539.15 (M+H).

Example 760

(S)-3-(4-{3-Methoxy-4-[7-(2-methoxy-phenyl)-pyrrolo[2,1-f][1,2,4]triazin-2-ylamino]-phenyl}-piperazin-1-yl)-propane-1,2-diol Following the experimental procedure described in Example 753, 2-Methanesulfinyl-7-(2-methoxy-phenyl)-pyrrolo[2,1-f][1,2,4]triazine and (R)-3-[4-(4-amino-3-methoxy-phenyl)-piperazin-1-yl]-propane-1,2-diol were converted to (S)-3-(4-{3-methoxy-4-[7-(2-methoxy-phenyl)-pyrrolo[2,1-f][1,2,4]triazin-2-ylamino]-phenyl}-piperazin-1-yl)-propane-1,2-diol as a yellow foam (32 mg, 36%). $^1$H-NMR (CDCl$_3$) δ 8.67 (s, 1H), 8.24 (d, J=8.8 Hz, 1H), 8.00 (m, 1H), 7.43 (m, 1H), 7.32 (br s, 1H), 7.12 (m, 1H), 7.06 (d, J=8.2 Hz, 1H), 7.01 (d, J=4.6 Hz, 1H), 6.81 (d, J=4.6 Hz, 1H), 6.53 (d, J=2.5 Hz, 1H), 6.42 (m, 1H), 3.90 (m, 1H), 3.89 (s, 3H), 3.84 (s, 3H), 3.78 (m, 1H), 3.54 (m, 1H), 3.15 (m, 4H), 2.86 (m, 2H), 2.65 (m, 4H), 2.60 (br s, 1H), 2.48 (m, 1H); LC/MS (ESI+): 505.16 (M+H).

Example 761

(S)-3-(4-{3-Methoxy-4-[7-(2-methoxy-phenyl)-pyrrolo[2,1-f][1,2,4]triazin-2-ylamino]-phenyl}-piperidin-1-yl)-propane-1,2-diol Trifluoro-methanesulfonic acid 7-(2-methoxy-phenyl)-pyrrolo[2,1-f][1,2,4]triazin-2-yl ester (320.00 mg, 0.857 mmol), N,N-Diisopropylethylamine (0.779 mL, 4.47 mmol), and (S)-3-[4-(4-Amino-3-methoxy-phenyl)-piperidin-1-yl]-propane-1,2-diol (600.65 mg, 2.142 mmol) were dissolved in 1-methoxy-2-propanol (2.3 mL) and the reaction mixture was heated at 100° C. for 8 h. The reaction mixture was partitioned between dichloromethane and saturated aqueous NaHCO$_3$, and the organic layer was separated and dried over MgSO$_4$, then filtered. The solvent was evaporated under reduced pressure and the product was isolated by column chromatography (ISCO, Silicagel, methanol/dichloromethane 0-10%). The product needed to be further purified by preparative reverse phase HPLC (Gilson, 0.1% TFA water/acetonitrile gradient) followed by neutralization of the resulting TFA salt to afford (S)-3-(4-{3-methoxy-4-[7-(2-methoxy-phenyl)-pyrrolo[2,1-f][1,2,4]triazin-2-ylamino]-phenyl}-piperidin-1-yl)-propane-1,2-diol as a light orange solid (115 mg, 27%). MP: 66-80° C.; $^1$H-NMR (CDCl$_3$) δ 8.69 (s, 1H), 8.29 (d, J=8.0 Hz, 1H), 8.99 (dd, J=8.0, 1.6 Hz, 1H), 7.44 (m, 2H), 7.13 (m, 1H), 7.07 (d, J=8.0 Hz, 1H), 7.02 (d, J=4.7 Hz, 1H), 6.83 (d, J=4.7 Hz, 1H), 6.72 (s, 1H), 6.71 (d, J=8.0 Hz, 1H), 3.90 (s, 3H), 3.86 (m, 1H), 3.85 (s, 3H), 3.77 (m, 1H), 3.55 (m, 1H), 3.22 (d, J=10.6 Hz, 1H), 3.08 (d, J=10.6 Hz, 1H), 2.77 (br s, 2H), 2.69 (m, 1H), 2.48 (m, 3H), 2.20 (m, 1H), 1.85 (m, 4H); LC/MS (ESI+): 504.19 (M+H).

Example 762

[2-Methoxy-4-(1-methyl-piperidin-4-yl)-phenyl]-[7-(2-methoxy-phenyl)-pyrrolo[2,1-f][1,2,4]triazin-2-yl]-amine Following the experimental procedure described in Example 753, 2-Methanesulfinyl-7-(2-methoxy-phenyl)-pyrrolo[2,1-f][1,2,4]triazine and 2-methoxy-4-(1-methyl-piperidin-4-yl)-phenylamine were converted to [2-methoxy-4-(1-methyl-piperidin-4-yl)-phenyl]-[7-(2-methoxy-phenyl)-pyrrolo[2,1-f][1,2,4]triazin-2-yl]-amine as a yellow solid (22 mg, 18%). MP: 71-84° C.; $^1$H-NMR (CDCl$_3$) δ 8.69 (s, 1H), 8.29 (d, J=8.8 Hz, 1H), 7.98 (dd, J=8.0; 1.7 Hz, 1H), 7.42 (m, 2H), 7.12 (m, 1H), 7.07 (d, J=8.4 Hz, 1H), 7.01 (d, J=5.6 Hz, 1H), 6.83 (d, J=5.6 Hz, 1H), 6.74 (s, 1H), 6.73 (m, 1H), 3.88 (s, 3H), 3.84 (s, 3H), 3.07 (m, 2H), 2.45 (m, 1H), 2.41 (s, 3H), 2.15 (m, 2H), 1.87 (m, 4H); LC/MS (ESI+): 444.22 (M+H).

Example 763

[4-(3-Dimethylamino-pyrrolidin-1-yl)-2-methoxy-phenyl]-[7-(2-methoxy-phenyl)-pyrrolo[2,1-f][1,2,4]triazin-2-yl]-amine Following the experimental procedure described in Example 753, 2-Methanesulfinyl-7-(2-methoxy-phenyl)- pyrrolo[2,1-f][1,2,4]triazine and [1-(4-amino-3-methoxy-phenyl)-pyrrolidin-3-yl]-dimethyl-amine were converted to [4-(3-dimethylamino-pyrrolidin-1-yl)-2-methoxy-phenyl]-[7-(2-methoxy-phenyl)-pyrrolo[2,1-f][1,2,4]triazin-2-yl]-amine as a yellow solid (48 mg, 38%). MP: 70-78° C.; $^1$H-NMR (CDCl$_3$) δ 8.64 (s, 1H), 8.17 (d, J=8.8 Hz, 1H), 8.05 (dd, J=7.6, 1.7 Hz, 1H), 7.41 (m, 1H), 7.17 (s, 1H), 7.12 (m, 1H), 7.05 (m, 1H), 6.99 (d, J=4.7 Hz, 1H), 6.79 (d, J=4.7 Hz, 1H), 6.14 (d, J=2.5 Hz, 1H), 6.04 (dd, J=8.8, 2.5 Hz, 1H), 3.88 (s, 3H), 3.84 (s, 3H), 3.47 (m, 1H), 3.42 (m, 1H), 3.31 (m, 1H), 3.17 (m, 1H), 2.92 (m, 1H), 2.35 (s, 6H), 2.21 (m, 1H), 1.95 (m, 1H); LC/MS (ESI+): 459.17 (M+H).

Example 764

(3,4-Dihydro-2H-1,4-ethano-quinolin-7-yl)-[7-(2-methoxy-phenyl)-pyrrolo[2,1-f][1,2,4]triazin-2-yl]-amine Following the experimental procedure described in Example 753, 2-Methanesulfinyl-7-(2-methoxy-phenyl)-pyrrolo[2,1-f][1,2,4]triazine and 3,4-dihydro-2H-1,4-ethano-quinolin-7-ylamine were converted to (3,4-dihydro-2H-1,4-ethano-quinolin-7-yl)-[7-(2-methoxy-phenyl)-pyrrolo[2,1-f][1,2,4]triazin-2-yl]-amine as a yellow solid (19 mg, 17%). MP: 89-95° C.; $^1$H-NMR (CDCl$_3$) δ 8.69 (s, 1H), 7.98 (dd, J=7.6, 1.7 Hz, 1H), 7.71 (dd, J=8.0, 2.2 Hz, 1H), 7.40 (m, 1H), 7.15 (d, J=2.2 Hz, 1H), 7.12 (m, 1H), 7.07 (s, 1H), 7.05 (s, 1H), 7.03 (d, J=4.7 Hz, 1H), 6.84 (d, J=4.7 Hz, 1H), 6.82 (br s, 1H), 3.87 (s, 3H), 3.18 (m, 2H), 3.07 (m, 1H), 2.70 (m, 2H), 1.84 (m, 2H), 1.51 (m, 2H); LC/MS (ESI+): 398.2 (M+H).

Example 765

[2-Methoxy-4-(4-methyl-[1,4]diazepan-1-yl)-phenyl]-[7-(2-methoxy-phenyl)-pyrrolo[2,1-f][1,2,4]triazin-2-yl]-amine Following the experimental procedure described in Example 753, 2-Methanesulfinyl-7-(2-methoxy-phenyl)-pyrrolo[2,1-f][1,2,4]triazine and 3,4-dihydro-2H-1,4-ethano-quinolin-7-ylamine were converted to (3,4-dihydro-2H-1,4-ethano-quinolin-7-yl)-[7-(2-methoxy-phenyl)-pyrrolo[2,1-f][1,2,4]triazin-2-yl]-amine as an orange solid (19 mg, 17%). MP: 69-77° C.; $^1$H-NMR (CDCl$_3$) δ 8.65 (s, 1H), 8.15 (d, J=8.8 Hz, 1H), 8.06 (d, J=7.6 Hz, 1H), 7.41 (m, 1H), 7.17 (s, 1H), 7.11 (s, 1H), 7.06 (d, J=8.4 Hz, 1H), 7.00 (d, J=4.4 Hz, 1H), 6.79 (d, J=4.4 Hz, 1H), 6.28 (s, 1H), 6.18 (d, J=8.9 Hz, 1H), 3.87 (s, 3H), 3.84 (s, 3H), 3.57 (m, 2H), 3.47 (m, 2H), 2.76 (br s, 2H), 2.61 (m, 2H), 2.42 (s, 3H), 2.05 (m, 2H); LC/MS (ESI+): 459.2 (M+H).

Example 766

(R)-1-(4-{3-Methoxy-4-[7-(2-methoxy-phenyl)-pyrrolo[2,1-f][1,2,4]triazin-2-ylamino]-phenyl}-[1,4]diazepan-1-yl)-propan-2-ol Following the experimental procedure described in Example 753, 2-methanesulfinyl-7-(2-methoxy-phenyl)-pyrrolo[2,1-f][1,2,4]triazine and (R)-1-[4-(4-amino-3-methoxy-phenyl)-perhydro-1,4-diazepin-1-yl]-propan-2-ol were converted to (R)-1-(4-{3-methoxy-4-[7-(2-methoxy-phenyl)-pyrrolo[2,1-f][1,2,4]triazin-2-ylamino]-phenyl}-[1,4]diazepan-1-yl)-propan-2-ol as an orange solid (16 mg, 11%). MP: 70-79° C.; $^1$H-NMR (CDCl$_3$) δ 8.65 (s, 1H), 8.16 (d, J=8.8 Hz, 1H), 8.06 (dd, J=7.6, 1.7 Hz, 1H), 7.41 (m, 1H), 7.17 (s, 1H), 7.11 (m, 1H), 7.06 (d, J=8.3 Hz, 1H), 7.00 (d, J=4.6 Hz, 1H), 6.79 (d, J=4.6 Hz, 1H), 6.28 (d, J=2.6 Hz, 1H), 6.18 (dd, J=8.9, 2.6 Hz, 1H), 3.87 (s, 3H), 3.85 (s, 3H), 3.76 (m, 2H), 3.52 (m, 4H), 2.94 (m, 1H), 2.78 (m, 2H), 2.63 (m, 1H), 2.56 (dd, J=12.4, 2.8 Hz, 1H), 2.23 (m, 1H), 1.97 (m, 2H), 1.12 (d, J=6.3 Hz, 3H); LC/MS (ESI+): 503.2 (M+H).

Example 767

(S)-3-(4-{3-Methoxy-4-[7-(2-methoxy-phenyl)-pyrrolo[2,1-f][1,2,4]triazin-2-ylamino]-phenyl}-[1,4]diazepan-1-yl)-propane-1,2-diol Following the experimental procedure described in Example 753, 2-methanesulfinyl-7-(2-methoxy-phenyl)-pyrrolo[2,1-f][1,2,4]triazine and (S)-3-[4-(4-Amino-3-methoxy-phenyl)-perhydro-1,4-diazepin-1-yl]-propane-1,2-diol were converted to (S)-3-(4-{3-methoxy-4-[7-(2-methoxy-phenyl)-pyrrolo[2,1-f][1,2,4]triazin-2-ylamino]-phenyl}-[1,4]diazepan-1-yl)-propane-1,2-diol as an orange solid (9 mg, 6%). MP: 93-99° C.; $^1$H-NMR (CDCl$_3$) δ 8.65 (s, 1H), 8.16 (d, J=8.4 Hz, 1H), 8.06 (d, J=7.6 Hz, 1H), 7.41 (m, 1H), 7.17 (s, 1H), 7.11 (m, 1H), 7.05 (d, J=8.0 Hz, 1H), 7.00 (d, J=4.2 Hz, 1H), 6.79 (d, J=4.2 Hz, 1H), 6.28 (s, 1H), 6.18 (d, J=9.0 Hz, 1H), 3.87 (s, 3H), 3.85 (s, 3H), 3.75 (m, 2H), 3.52 (m, 5H), 2.95 (m, 1H), 2.81 (m, 2H), 2.69 (m, 1H), 2.59 (m, 2H), 2.34 (m, 2H), 1.98 (m, 2H); LC/MS (ESI+): 519.2 (M+H).

Example 768

(±)-1-Methoxy-8-morpholin-4-yl-6,7,8,9-tetrahydro-5H-enzocyclohepten-2-yl)-[7-(2-methoxy-phenyl)-pyrrolo[2,1-f][1,2,4]triazin-2-yl]-amine Following the experimental procedure described in Example 753, 2-methanesulfinyl-7-(2-methoxy-phenyl)-pyrrolo[2,1-f][1,2,4]triazine and (±)-1-methoxy-8-morpholin-4-yl-6,7,8,9-tetrahydro-5H-benzocyclohepten-2-ylamine were converted to (±)-1-methoxy-8-morpholin-4-yl-6,7,8,9-tetrahydro-5H-enzocyclohepten-2-yl)-[7-(2-methoxy-phenyl)-pyrrolo[2,1-f][1,2,4]triazin-2-yl]-amine as a yellow solid (11 mg, 8%). MP: 90-97° C.; $^1$H-NMR (CDCl$_3$) δ 8.70 (s, 1H), 8.12 (d, J=8.3 Hz, 1H), 7.98 (dd, J=7.6, 1.7 Hz, 1H), 7.42 (m, 1H), 7.35 (s, 1H), 7.12 (m, 1H), 7.06 (d, J=8.3 Hz, 1H), 7.03 (d, J=4.8 Hz, 1H), 6.84 (d, J=4.8 Hz, 1H), 6.76 (d, J=8.3 Hz, 1H), 3.85 (s, 3H), 3.78 (s, 3H), 3.74 (br s, 4H), 3.42 (m, 1H), 2.71 (m, 4H), 2.59 (m, 2H), 2.48 (m, 2H), 2.32 (m, 1H), 2.06 (m, 1H), 1.78 (m, 1H), 1.67 (br s, 1H), 1.35 (m, 1H); LC/MS (ESI+): 500.2 (M+H).

Example 769

N-[2-(2-{4-[1-((S)-2,3-Dihydroxy-propyl)-piperidin-4-yl]-2-methoxy-phenylamino}-pyrrolo[2,1-f][1,2,4]triazin-7-yl)-phenyl]-N-methyl-methanesulfonamide Following the experimental procedure described in Example 761, trifluoro-methanesulfonic acid 7-[2-(methane-sulfonyl-methyl-amino)-phenyl]-pyrrolo[2,1-f][1,2,4]triazin-2-yl ester and (S)-3-[4-(4-amino-3-methoxy-phenyl)-piperidin-1-yl]-propane-1,2-diol were converted to N-[2-(2-{4-[1-((S)-2,3-dihydroxy-propyl)-piperidin-4-yl]-2-methoxy-phenylamino}-pyrrolo[2,1-f][1,2,4]triazin-7-yl)-phenyl]-N-methyl-methanesulfonamide as an yellow solid (20 mg, 26%). MP: 108-116° C.; $^1$H-NMR (CDCl$_3$) δ 8.72 (s, 1H), 8.08 (d, J=8.0 Hz, 1H), 7.95 (m, 1H), 7.53 (m, 3H), 7.45

(s, 1H), 7.03 (d, J=4.6 Hz, 1H), 6.86 (d, J=4.6 Hz, 1H), 6.72 (s, 1H), 6.63 (d, J=8.0 Hz, 1H), 3.90 (s, 3H), 3.87 (m, 1H), 3.78 (m, 1H), 3.54 (m, 1H), 3.13 (m, 1H), 3.12 (s, 3H), 2.98 (m, 1H), 2.67 (s, 2H), 2.62 (m, 1H), 2.42 (m, 4H), 2.12 (m, 2H), 1.82 (m, 5H); LC/MS (ESI+): 581.2 (M+H).

Example 770

[2-Methoxy-5-(1-methyl-piperidin-4-yl)-phenyl]-[7-(2-methoxy-phenyl)-pyrrolo[2,1-f][1,2,4]triazin-2-yl]-amine Following the experimental procedure described in Example 753, 2-methanesulfinyl-7-(2-methoxy-phenyl)-pyrrolo[2,1-f][1,2,4]triazine and 2-methoxy-5-(1-methyl-piperidin-4-yl)-phenylamine were converted to [2-methoxy-5-(1-methyl-piperidin-4-yl)-phenyl]-[7-(2-methoxy-phenyl)-pyrrolo[2,1-f][1,2,4]triazin-2-yl]-amine as a yellow solid (27 mg, 18%). MP: 64-69° C.; $^1$H-NMR (CDCl$_3$) δ 8.69 (s, 1H), 8.20 (s, 1H), 7.92 (d, J=8.0 Hz, 1H), 7.51 (s, 1H), 7.44 (m, 1H), 7.12 (m, 1H), 7.08 (d, J=8.0 Hz, 1H), 6.98 (d, J=4.6 Hz, 1H), 6.83-6.78 (m, 3H), 3.87 (s, 3H), 3.83 (s, 3H), 2.94 (m, 2H), 2.36 (s, 3H), 2.27 (m, 1H), 2.02 (m, 2H), 1.69 (m, 4H); LC/MS (ESI+): 444.2 (M+H).

Example 771

N-(2-{2-[2-Methoxy-4-(4-methyl-[1,4]diazepan-1-yl)-phenylamino]-pyrrolo[2,1-f][1,2,4]triazin-7-yl}-phenyl)-N-methyl-methanesulfonamide Following the experimental procedure described in Example 753, N-[2-(2-methanesulfinyl-pyrrolo[2,1-f][1,2,4]triazin-7-yl)-phenyl]-N-methyl-methanesulfonamide and 2-methoxy-4-(4-methyl-perhydro-1,4-diazepin-1-yl)-phenylamine were converted to N-(2-{2-[2-methoxy-4-(4-methyl-[1,4]diazepan-1-yl)-phenylamino]-pyrrolo[2,1-f][1,2,4]triazin-7-yl}-phenyl)-N-methyl-methanesulfonamide as an orange solid (33 mg, 25%). MP: 98-105° C.; $^1$H-NMR (CDCl$_3$) δ 8.68 (s, 1H), 7.92 (m, 1H), 7.90 (d, J=8.8 Hz, 1H), 7.51 (br s, 3H), 7.15 (s, 1H), 6.97 (d, J=4.4 Hz, 1H), 6.81 (d, J=4.4 Hz, 1H), 6.26 (s, 1H), 6.09 (d, J=8.8 Hz, 1H), 3.86 (s, 3H), 3.56 (m, 2H), 3.46 (m, 2H), 3.13 (s, 3H), 2.75 (m, 2H), 2.62 (s, 6H), 2.42 (s, 3H), 2.04 (m, 2H); LC/MS (ESI+): 536.2 (M+H).

Example 772

N-[2-(2-{4-[4-((R)-2-Hydroxy-propyl)-[1,4]diazepan-1-yl]-2-methoxy-phenylamino}-pyrrolo[2,1-f][1,2,4]triazin-7-yl)-phenyl]-N-methyl-methanesulfonamide Following the experimental procedure described in Example 753, N-[2-(2-methanesulfinyl-pyrrolo[2,1-f][1,2,4]triazin-7-yl)-phenyl]-N-methyl-methanesulfonamide and (R)-1-[4-(4-amino-3-methoxy-phenyl)-perhydro-1,4-diazepin-1-yl]-propan-2-ol were converted to N-[2-(2-{4-[4-((R)-2-hydroxy-propyl)-[1,4]diazepan-1-yl]-2-methoxy-phenylamino}-pyrrolo[2,1-f][1,2,4]triazin-7-yl)-phenyl]-N-methyl-methanesulfonamide as a light brown solid (52 mg, 37%). MP: 93-99° C.; $^1$H-NMR (CDCl$_3$) δ 8.68 (s, 1H), 7.94 (m, 1H), 7.92 (d, J=8.8 Hz, 1H), 7.51 (m, 3H), 7.15 (s, 1H), 6.96 (d, J=4.5 Hz, 1H), 6.81 (d, J=4.5 Hz, 1H), 6.26 (s, 1H), 6.09 (d, J=8.8 Hz, 1H), 3.86 (s, 3H), 3.75 (m, 1H), 3.49 (m, 5H), 3.13 (s, 3H), 2.96 (m, 1H), 2.76 (m, 2H), 2.62 (s, 3H), 2.57 (m, 2H), 2.23 (m, 1H), 1.95 (m, 2H), 1.11 (d, J=6.0 Hz, 3H); LC/MS (ESI+): 580.2 (M+H).

Example 773

N-[2-(2-{4-[4-((S)-2,3-Dihydroxy-propyl)-[1,4]diazepan-1-yl]-2-methoxy-phenylamino}-pyrrolo[2,1-f][1,2,4]triazin-7-yl)-phenyl]-N-methyl-methanesulfonamide Following the experimental procedure described in Example 753, N-[2-(2-methanesulfinyl-pyrrolo[2,1-f][1,2,4]triazin-7-yl)-phenyl]-N-methyl-methanesulfonamide and (S)-3-[4-(4-amino-3-methoxy-phenyl)-perhydro-1,4-diazepin-1-yl]-propane-1,2-diol were converted to N-[2-(2-{4-[4-((S)-2,3-dihydroxy-propyl)-[1,4]diazepan-1-yl]-2-methoxy-phenylamino}-pyrrolo[2,1-f][1,2,4]triazin-7-yl)-phenyl]-N-methyl-methanesulfonamide as an orange solid (17 mg, 11%). MP: 93-99° C.; $^1$H-NMR (CDCl$_3$) δ 8.68 (s, 1H), 7.93 (m, 1H), 7.92 (d, J=8.8 Hz, 1H), 7.51 (s, 3H), 7.16 (s, 1H), 6.96 (d, J=4.4 Hz, 1H), 6.82 (d, J=4.4 Hz, 1H), 6.26 (s, 1H), 6.09 (d, J=8.8 Hz, 1H), 3.86 (s, 3H), 3.74 (m, 2H), 3.50 (m, 5H), 3.13 (s, 3H), 2.96 (m, 1H), 2.79 (m, 2H), 2.68-2.58 (m, 5H), 2.62 (s, 3H), 1.96 (m, 2H); LC/MS (ESI+): 696.2 (M+H).

Example 774

N-(2-{2-[2-Methoxy-5-(1-methyl-piperidin-4-yl)-phenylamino]-pyrrolo-[2,1-f][1,2,4]triazin-7-yl}-phenyl)-N-methyl-methanesulfonamide Following the experimental procedure described in Example 753, N-[2-(2-methanesulfinyl-pyrrolo[2,1-f][1,2,4]triazin-7-yl)-phenyl]-N-methyl-methanesulfonamide and 2-methoxy-5-(1-methyl-piperidin-4-yl)-phenylamine were converted to N-(2-{2-[2-methoxy-5-(1-methyl-piperidin-4-yl)-phenylamino]-pyrrolo-[2,1-f][1,2,4]triazin-7-yl}-phenyl)-N-methyl-methanesulfonamide as a light tan solid (25 mg, 14%). MP: 93-99° C.; $^1$H-NMR (CDCl$_3$) δ 8.73 (s, 1H), 7.97 (s, 1H), 7.77 (d, J=7.2 Hz, 1H), 7.53 (m, 4H), 6.93 (d, J=4.6 Hz, 1H), 6.86 (d, J=4.6 Hz, 1H), 6.77 (m, 2H), 3.87 (s, 3H), 3.11 (s, 3H), 2.92 (m, 2H), 2.58 (s, 3H), 2.35 (s, 3H), 2.10 (m, 1H), 2.00 (m, 2H), 1.58 (m, 4H); LC/MS (ESI+): 521.2 (M+H).

Example 775

[2-Methoxy-3-(1-methyl-piperidin-4-yl)-phenyl]-[7-(2-methoxy-phenyl)-pyrrolo[2,1-f][1,2,4]triazin-2-yl]-amine Following the experimental procedure described in Example 753, 2-methanesulfinyl-7-(2-methoxy-phenyl)-pyrrolo[2,1-f][1,2,4]triazine and 2-methoxy-3-(1-methyl-piperidin-4-yl)-phenylamine were converted to [2-methoxy-3-(1-methyl-piperidin-4-yl)-phenyl]-[7-(2-methoxy-phenyl)-pyrrolo[2,1-f][1,2,4]triazin-2-yl]-amine as a yellow solid (21 mg, 14%). MP: 74-89° C.; $^1$H-NMR (CDCl$_3$) δ 8.71 (s, 1H), 8.25 (d, J=8.5 Hz, 1H), 7.97 (d, J=7.6 Hz, 1H), 7.40 (m, 2H), 4.05 (m, 4H), 6.86 (m, 4H), 3.85 (s, 3H), 3.79 (s, 3H), 2.99 (m, 2H), 2.91 (m, 1H), 2.34 (s, 3H), 2.10 (m, 2H), 1.81 (m, 4H); LC/MS (ESI+): 444.2 (M+H).

Example 776

N-(2-{2-[2-Methoxy-3-(1-methyl-piperidin-4-yl)-phenylamino]-pyrrolo [2,1-f][1,2,4]triazin-7-yl}-phenyl)-N-methyl-methanesulfonamide Following the experimental procedure described in Example 753, N-[2-(2-methanesulfinyl-pyrrolo[2,1-f][1,2,4]triazin-7-yl)-phenyl]-N-methyl-methanesulfonamide and 2-methoxy-3-(1-methyl-piperidin-4-yl)-phenylamine were converted to N-(2-{2-[2-methoxy-3-(1-methyl-piperidin-4-yl)-phenylamino]-pyrrolo[2,1-f][1,2,4]triazin-7-yl}-phenyl)-N-methyl-methanesulfonamide as a light tan solid (13 mg, 7%). MP: 92-101° C.; $^1$H-NMR (CDCl$_3$) δ 8.74 (s, 1H), 8.03 (d, J=8.0 Hz, 1H), 7.95 (m, 1H), 7.50 (m, 3H), 7.39 (s, 1H), 7.05 (d, J=4.5 Hz, 1H), 6.93 (m, 1H), 6.89 (m, 2H), 3.78 (s, 3H), 3.12 (s, 3H), 2.99 (m, 2H), 2.90 (m, 1H), 2.71 (s, 3H), 2.35 (s, 3H), 2.11 (m, 2H), 1.80 (m, 4H); LC/MS (ESI+): 521.2 (M+H).

Example 777

(±)-[4-(1,3-Diethyl-piperidin-3-yl)-phenyl]-[7-(2-methoxy-phenyl) pyrrolo-[2,1-f][1,2,4]triazin-2-yl]-amine Following the experimental procedure described in Example 753, 2-methanesulfinyl-7-(2-methoxy-phenyl)-pyrrolo[2,1-f][1,2,4]triazine and 4-(1,3-diethyl-piperidin-3-yl)-phenylamine were converted to (±)-[4-(1,3-diethyl-piperidin-3-yl)-phenyl]-[7-(2-methoxy-phenyl)-pyrrolo-[2,1-f][1,2,4]triazin-2-yl]-amine as a yellow solid (39 mg, 25%). MP: 69-78° C.; $^1$H-NMR (CDCl$_3$) δ 8.68 (s, 1H), 8.02 (d, J=7.6 Hz, 1H), 7.53 (d, J=8.0 Hz, 2H), 7.42 (m, 1H), 7.21 (d, J=8.0 Hz, 2H), 7.12 (m, 1H), 7.07 (m, 2H), 6.83 (br s, 2H), 3.84 (s, 3H), 2.80 (br s, 1H), 2.41 (m, 5H), 1.88 (br s, 1H), 1.72 (m, 1H), 1.60 (m, 4H), 1.13 (t, J=7.0 Hz, 3H), 0.56 (t, J=7.36 Hz, 3H); LC/MS (ESI+): 456.2 (M+H).

Example 778

(±)-N-(2-{2-[4-(1,3-Diethyl-piperidin-3-yl)-phenylamino]-pyrrolo[2,1-f][1,2,4]triazin-7-yl}-phenyl)-N-methyl-methanesulfonamide Following the experimental procedure described in Example 753, N-[2-(2-methanesulfinyl-pyrrolo[2,1-f][1,2,4]triazin-7-yl)-phenyl]-N-methyl-methanesulfonamide and 4-(1,3-diethyl-piperidin-3-yl)-phenylamine were converted to (±)-N-(2-{2-[4-(1,3-diethyl-piperidin-3-yl)-phenylamino]-pyrrolo[2,1-f][1,2,4]triazin-7-yl}-phenyl)-N-methyl-methanesulfonamide as a tan solid (29 mg, 17%). MP: 93-101° C.; $^1$H-NMR (CDCl$_3$) δ 8.71 (s, 1H), 7.95 (m, 1H), 7.50 (m, 3H), 7.42 (d, J=8.0 Hz, 2H), 7.17 (d, J=8.0 Hz, 2H), 7.03 (d, J=4.2 Hz, 1H), 6.86 (d, J=4.2 Hz, 1H), 6.83 (s, 1H), 3.10 (s, 3H), 2.80 (m, 1H), 2.67 (s, 3H), 2.43 (m, 5H), 1.88 (m, 1H), 1.70 (m, 1H), 1.58 (m, 4H), 1.13 (t, J=6.92 Hz, 3H), 0.55 (t, J=7.2 Hz, 3H); LC/MS (ESI+): 533.1 (M+H).

Example 779

(±)-[2-Methoxy-4-(3-morpholin-4-yl-pyrrolidin-1-yl)-phenyl]-[7-(2-methoxyphenyl)-pyrrolo[2,1-f][1,2,4]triazin-2-yl]-amine Following the experimental procedure described in Example 753, 2-methanesulfinyl-7-(2-methoxy-phenyl)-pyrrolo[2,1-f][1,2,4]triazine and 2-methoxy-4-(3-morpholin-4-yl-pyrrolidin-1-yl)-phenylamine were converted to (±)-[2-methoxy-4-(3-morpholin-4-yl-pyrrolidin-1-yl)-phenyl]-[7-(2-methoxy-phenyl)-pyrrolo[2,1-f][1,2,4]triazin-2-yl]-amine as a yellow solid (60 mg, 35%). MP: 80-87° C.; $^1$H-NMR (CDCl$_3$) δ 8.65 (s, 1H), 8.18 (d, J=8.6 Hz, 1H), 8.06 (d, J=7.6 Hz, 1H), 7.40 (m, 1H), 7.17 (s, 1H), 7.11 (m, 1H), 7.06 (d, J=8.2 Hz, 1H), 7.00 (d, J=2.8 Hz, 1H), 6.79 (d, J=2.8 Hz, 1H), 6.14 (s, 1H), 6.04 (d, J=8.8 Hz, 1H), 3.88 (s, 3H), 3.84 (s, 3H), 3.76 (br s, 4H), 3.49 (m, 1H), 3.42 (m, 1H), 3.32 (m, 1H), 3.18 (m, 1H), 2.99 (m, 1H), 2.56 (m, 4H), 2.20 (m, 1H), 1.95 (m, 1H); LC/MS (ESI+): 501.1 (M+H).

Example 780

[2-Methoxy-4-(4-[1,4]oxazepan-4-yl-piperidin-1-yl)-phenyl]-[7-(2-methoxy-phenyl)-pyrrolo[2,1-f][1,2,4]triazin-2-yl]-amine Following the experimental procedure described in Example 753, 2-methanesulfinyl-7-(2-methoxy-phenyl)-pyrrolo[2,1-f][1,2,4]triazine and 2-methoxy-4-(4-perhydro-1,4-oxazepin-4-yl-piperidin-1-yl)-phenylamine were converted to [2-methoxy-4-(4-[1,4]oxazepan-4-yl-piperidin-1-yl)-phenyl]-[7-(2-methoxy-phenyl)-pyrrolo[2,1-f][1,2,4]triazin-2-yl]-amine as a brown/yellow solid (75 mg, 41%). MP: 75-82° C.; $^1$H-NMR (CDCl$_3$) δ 8.66 (s, 1H), 8.22 (d, J=8.7 Hz, 1H), 8.01 (d, J=7.6 Hz, 1H), 7.42 (m, 1H), 7.30 (s, 1H), 7.12 (m, 1H), 7.06 (d, J=8.3 Hz, 1H), 7.00 (d, J=4.6 Hz, 1H), 6.81 (d, J=4.6 Hz, 1H), 6.55 (s, 1H), 6.44 (d, J=8.8 Hz, 1H), 3.87 (s, 3H), 3.84 (s, 3H), 3.81 (m, 2H), 3.73 (m, 2H), 3.61 (m, 2H), 2.83 (br s, 4H), 2.66 (m, 3H), 1.89 (m, 4H), 1.73 (m, 2H); LC/MS (ESI+): 529.2 (M+H).

Example 781

{2-Methoxy-4-[4-(4-methyl-[1,4]diazepan-1-yl)-piperidin-1-yl]-phenyl}-[7-(2-methoxy-phenyl)-pyrrolo[2,1-f][1,2,4]triazin-2-yl]-amine Following the experimental procedure described in Example 753, 2-methanesulfinyl-7-(2-methoxy-phenyl)-pyrrolo[2,1-f][1,2,4]triazine and 2-methoxy-4-[4-(4-methyl-perhydro-1,4-diazepin-1-yl)-piperidin-1-yl]-phenylamine were converted to {2-methoxy-4-[4-(4-methyl-[1,4]diazepan-1-yl)-piperidin-1-yl]-phenyl}-[7-(2-methoxy-phenyl)-pyrrolo[2,1-f][1,2,4]triazin-2-yl]-amine as a yellow solid (38 mg, 20%). MP: 69-76° C.; $^1$H-NMR (CDCl$_3$) δ 8.66 (s, 1H), 8.21 (d, J=8.6 Hz, 1H), 8.01 (d, J=7.6 Hz, 1H), 7.42 (m, 1H), 7.29 (s, 1H), 7.12 (m, 1H), 7.06 (d, J=8.4 Hz, 1H), 7.00 (d, J=4.0 Hz, 1H), 6.81 (d, J=4.0 Hz, 1H), 6.54 (s, 1H), 6.42 (d, J=8.56 Hz, 1H), 3.87 (s, 3H), 3.84 (s, 3H), 3.61 (m, 2H), 2.83 (m, 4H), 2.63 (m, 6H), 2.57 (m, 1H), 2.38 (s, 3H), 1.84 (m, 4H), 1.70 (m, 2H); LC/MS (ESI+): 542.3 (M+H).

Example 782

(±)-N-(2-{2-[2-Methoxy-4-(3-morpholin-4-yl-pyrrolidin-1-yl)-phenylamino]-pyrrolo[2,1-f][1,2,4]triazin-7-yl}-phenyl)-N-methyl-methanesulfonamide Following the experimental procedure described in Example 753, N-[2-(2-methanesulfinyl-pyrrolo[2,1-f][1,2,4]triazin-7-yl)-phenyl]-N-methyl-methanesulfonamide and (±)-2-methoxy-4-(3-morpholin-4-yl-pyrrolidin-1-yl)-phenylamine were converted to (±)-N-(2-{2-[2-methoxy-4-(3-morpholin-4-yl-pyrrolidin-1-yl)-phenylamino]-pyrrolo[2,1- f][1,2,4]triazin-7-yl}-phenyl)-N-methyl-methanesulfonamide as an orange solid (46 mg, 23%). MP: 110-119° C.; $^1$H-NMR (CDCl$_3$) δ 8.70 (s, 1H), 7.95 (d, J=8.4 Hz, 2H), 7.52 (br s, 3H), 7.17 (s, 1H), 6.97 (m, 1H), 6.83 (m, 1H), 6.14 (s, 1H), 5.97 (d, J=8.4 Hz, 1H), 3.89 (s, 3H), 3.78 (br s, 4H), 3.49 (m, 1H), 3.43 (m, 1H), 3.34 (m, 1H), 3.19 (m, 1H), 3.14 (s, 3H), 3.01 (m, 1H), 2.63 (s, 3H), 2.58 (m, 4H), 2.22 (m, 1H), 1.96 (m, 1H); LC/MS (ESI+): 578.2 (M+H).

Example 783

N-(2-{2-[2-Methoxy-4-(4-[1,4]oxazepan-4-yl-piperidin-1-yl)-henylamino]-pyrrolo[2,1-f][1,2,4]triazin-7-yl}-phenyl)-N-methyl-methanesulfonamide Following the experimental procedure described in Example 753, N-[2-(2-methanesulfinyl-pyrrolo[2,1-f][1,2,4]triazin-7-yl)-phenyl]-N-methyl-methanesulfonamide and 2-methoxy-4-(4-perhydro-1,4-oxazepin-4-yl-piperidin-1-yl)-phenylamine were converted to N-(2-{2-[2-methoxy-4-(4-[1,4]oxazepan-4-yl-piperidin-1-yl)-henylamino]-pyrrolo[2,1-f][1,2,4]triazin-7-yl}-phenyl)-N-methyl-methanesulfonamide as a yellow solid (29 mg, 14%). MP: 105-113° C.; $^1$H-NMR (CDCl$_3$) δ 8.72 (s, 1H), 8.00 (d, J=8.6 Hz, 1H), 7.95 (m, 1H), 7.53 (br s, 3H), 7.31 (s, 1H), 7.01 (d, J=4.0 Hz, 1H), 6.85 (d, J=4.0 Hz, 1H), 6.55 (s, 1H), 6.36 (d, J=8.8 Hz, 1H), 3.89 (s, 3H), 3.83 (m, 2H), 3.75 (br s, 2H), 3.63 (m, 2H), 3.14 (s, 3H), 2.85 (br s, 4H), 2.67 (m, 3H), 2.66 (s, 3H), 1.90 (m, 4H), 1.74 (m, 2H); LC/MS (ESI+): 606.2 (M+H).

Example 784

N-[2-(2-{2-Methoxy-4-[4-(4-methyl-[1,4]diazepan-1-yl)-piperidin-1-yl]-phenylamino}-pyrrolo[2,1-f][1,2,4]triazin-7-yl)-phenyl]-N-methyl-methanesulfonamide Following the experimental procedure described in Example 753, N-[2-(2-methanesulfinyl-pyrrolo[2,1-f][1,2,4]triazin-7-yl)-phenyl]-N-methyl-methanesulfonamide and 2-methoxy-4-[4-(4-methyl-perhydro-1,4-diazepin-1-yl)-piperidin-1-yl]-phenylamine were converted to N-[2-(2-{2-methoxy-4-[4-(4-methyl-[1,4]diazepan-1-yl)-piperidin-1-yl]-phenylamino}-pyrrolo[2,1-f][1,2,4]triazin-7-yl)-phenyl]-N-methyl-methanesulfonamide as a yellow solid (45 mg, 21%). MP: 100-109° C.; $^1$H-NMR (CDCl$_3$) δ 8.71 (s, 1H), 8.00 (d, J=8.8 Hz, 1H), 7.95 (m, 1H), 7.52 (br s, 3H), 7.30 (s, 1H), 7.00 (d, J=4.2 Hz, 1H), 6.85 (d, J=4.2 Hz, 1H), 6.54 (s, 1H), 6.35 (d, J=8.8 Hz, 1H), 3.88 (s, 3H), 3.61 (m, 2H), 3.13 (s, 3H), 2.84 (m, 4H), 2.65 (s, 3H), 2.64 (m, 8H), 2.40 (s, 3H), 1.85 (m, 4H), 1.70 (m, 1H); LC/MS (ESI+): 619.3 (M+H).

Example 785

N-[2-(2-{(S)-1-[4-(4-Amino-3-methoxy-phenyl)-piperidin-1-ylmethyl]-2,2,2-trifluoro-ethoxy}-pyrrolo[2,1-f][1,2,4]triazin-7-yl)-phenyl]-N-methyl-methanesulfonamide Following the experimental procedure described in Example 753, N-[2-(2-methanesulfinyl-pyrrolo[2,1-f][1,2,4]triazin-7-yl)-phenyl]-N-methyl-methanesulfonamide and (S)-3-[4-(4-amino-3-methoxy-phenyl)-piperidin-1-yl]-1,1,1-trifluoro-propan-2-ol were converted to N-[2-(2-{(S)-1-[4-(4-amino-3-methoxy-phenyl)-piperidin-1-ylmethyl]-2,2,2-trifluoro-ethoxy}-pyrrolo[2,1-f][1,2,4]triazin-7-yl)-phenyl]-N-methyl-methanesulfonamide as a tan solid (46 mg, 27%). MP: 85-96° C.; $^1$H-NMR (CDCl$_3$) δ 8.82 (s, 1H), 7.69 (d, J=7.2 Hz, 1H), 7.47 (m, 3H), 7.12 (d, J=4.4 Hz, 1H), 7.01 (d, J=4.4 Hz, 1H), 6.60 (d, J=8.0 Hz, 1H), 6.53 (m, 2H), 5.79 (m, 1H), 3.80 (s, 3H), 3.65 (br s, 2H), 3.19 (s, 3H), 3.01-2.83 (m, 4H), 2.63 (s, 3H), 2.29 (m, 1H), 2.19 (m, 1H), 2.08 (m, 1H), 1.65 (m, 2H), 1.45 (m, 1H); LC/MS (ESI+): 619.1 (M+H).

Example 786

2-Methoxy-4-(1-{(S)-3,3,3-trifluoro-2-[7-(2-methoxy-phenyl)-pyrrolo[2,1-f][1,2,4]triazin-2-yloxy]-propyl}-piperidin-4-yl)-phenylamine Following the experimental procedure described in Example 753, 2-methanesulfinyl-7-(2-methoxy-phenyl)-pyrrolo[2,1-f][1,2,4]triazine and (S)-3-[4-(4-amino-3-methoxy-phenyl)-piperidin-1-yl]-1,1,1-trifluoro-propan-2-ol were converted to 2-methoxy-4-(1-{(S)-3,3,3-trifluoro-2-[7-(2-methoxy-phenyl)-pyrrolo[2,1-f][1,2,4]triazin-2-yloxy]-propyl}-piperidin-4-yl)-phenylamine as a tan solid (19 mg, 13%). MP: 73-82° C.; $^1$H-NMR (CDCl$_3$) δ 8.79 (s, 1H), 7.79 (d, J=7.6 Hz, 1H), 7.39 (m, 1H), 7.12 (br s, 1H), 7.04 (m, 2H), 6.97 (d, J=3.2 Hz, 1H), 6.60 (d, J=7.6 Hz, 1H), 6.53 (m, 2H), 5.76 (m, 1H), 3.82 (s, 3H), 3.80 (s, 3H), 3.65 (br s, 2H), 2.92 (m, 4H), 2.10 (m, 3H), 1.50 (m, 2H); LC/MS (ESI+): 542.2 (M+H).

Example 787

(R)-1-(4-{3-Methoxy-4-[7-(2-methoxy-phenyl)-pyrrolo[2,1-f][1,2,4]triazin-2-ylamino]-phenyl}-piperidin-1-yl)-propan-2-ol a). Following the experimental procedure described in Example 761, trifluoro-methanesulfonic acid 7-(2-methoxy-phenyl)-pyrrolo[2,1-f][1,2,4]triazin-2-yl ester and 4-(4-amino-3-methoxy-phenyl)-piperidine-1-carboxylic acid tert-butyl ester (prepared as described in WO08150799) were converted to 4-{3-methoxy-4-[7-(2-methoxy-phenyl)-pyrrolo[2,1-f][1,2,4]triazin-2-ylamino]-phenyl}-piperidine-1-carboxylic acid tert-butyl ester as a yellow foam (650 mg, 92%).

b). 4-{3-Methoxy-4-[7-(2-methoxy-phenyl)-pyrrolo[2,1-f][1,2,4]triazin-2-ylamino]-phenyl}-piperidine-1-carboxylic acid tert-butyl ester (650.00 mg, 1.227 mmol) was treated with trifluoroacetic acid (0.473 mL, 6.136 mmol) in methylene chloride (3 mL) at room temperature until complete reaction of starting material was observed by hplc analysis of reaction mixture. The reaction was quenched with minimum amount of saturated aqueous sodium carbonate, and was extracted extensively in dichloromethane. The combined organic extracts were dried over MgSO4 and then filtered. Evaporation of solvent under reduced pressure afforded [7-(2-methoxy-phenyl)-pyrrolo[2,1-f][1,2,4]triazin-2-yl]-(2-methoxy-4-piperidin-4-yl-phenyl)-amine as a yellow foam (504 mg, 96%) which was used without further purification in the next step.

c). [7-(2-Methoxy-phenyl)-pyrrolo[2,1-f][1,2,4]triazin-2-yl]-(2-methoxy-4-piperidin-4-yl-phenyl)-amine (70.00 mg, 0.163 mmol) was dissolved in tetrahydrofuran (0.300 mL) and the reaction mixture was placed in a sealed tube. (R)-(−)-Propylene oxide (14.2 mg, 0.244 mmol) was then added at room temperature and the reaction was next stirred overnight at 50° C. The solvent was evaporated under reduced pressure and the product was isolated by flash column chromatography (Silicagel, methanol/dichloromethane 0-10% gradient) to afford (R)-1-(4-{3-methoxy-4-[7-(2-methoxy-phenyl)-pyrrolo[2,1-f][1,2,4]triazin-2-ylamino]-phenyl}-piperidin-1-yl)-propan-2-ol as a tan solid (39 mg, 49%). MP: 67-74° C.; $^1$H-NMR (CDCl$_3$) δ 8.69 (s, 1H), 8.29 (d, J=8.1 Hz, 1H), 7.99 (d, J=7.7 Hz, 1H), 7.43 (m, 2H), 7.14 (m, 1H), 7.07 (d, J=8.4 Hz, 1H), 7.02 (d, J=4.4 Hz, 1H), 6.83 (d, J=4.4 Hz, 1H), 6.73 (s, 1H), 6.71 (d, J=8.1 Hz, 1H), 3.90 (s, 3H), 3.89 (m, 1H), 3.84 (s, 3H), 3.15 (m, 1H), 2.94 (m, 1H), 2.35 (m, 4H), 2.06 (m, 1H), 1.79 (m, 4H), 1.30 (br s, 1H), 1.16 (d, J=5.8 Hz, 3H); LC/MS (ESI+): 488.2 (M+H).

Example 788

N-[2-(2-{4-[1-((R)-2-Hydroxy-propyl)-piperidin-4-yl]-2-methoxy-phenylamino}-pyrrolo[2,1-f][1,2,4]triazin-7-yl)-phenyl]-N-methyl-methanesulfonamide Following the experimental procedure described in Example 753, N-[2-(2-methanesulfinyl-pyrrolo[2,1-f][1,2,4]triazin-7-yl)-phenyl]-N-methyl-methanesulfonamide and (R)-1-[4-(4-amino-3-methoxy-phenyl)-piperidin-1-yl]-propan-2-ol were converted to N-[2-(2-{4-[1-((R)-2-hydroxy-propyl)-piperidin-4-yl]-2-methoxy-phenylamino}-pyrrolo[2,1-f][1,2,4]triazin-7-yl)-phenyl]-N-methyl-methanesulfonamide as a tan solid (18 mg, 14%). MP: 91-103° C.; $^1$H-NMR (CDCl$_3$) δ 8.72 (s, 1H), 8.07 (d, J=8.4 Hz, 1H), 7.95 (d, J=3.9 Hz, 1H), 7.53 (br s, 3H), 7.45 (s, 1H), 7.02 (d, J=4.0 Hz, 1H), 6.86 (d, J=3.9 Hz, 1H), 6.72 (s, 1H), 6.64 (d, J=8.3 Hz, 1H), 3.90 (s, 3H), 3.89 (m, 1H), 3.15 (m, 1H), 3.12 (s, 3H), 2.95 (m, 1H), 2.67 (s, 3H), 2.37 (m, 4H), 2.05 (m, 1H), 1.79 (m, 4H), 1.26 (br s, 1H), 1.16 (d, J=7.0 Hz, 3H); LC/MS (ESI+): 565.2 (M+H).

Example 789

{2-Methoxy-4-[4-(1-methyl-piperidin-4-yl)-[1,4]diazepan-1-yl]-phenyl}-[7-(2-methoxy-phenyl)-pyrrolo[2,1-f][1,2,4]triazin-2-yl]-amine Following the experimental procedure described in Example 753, 2-methanesulfinyl-7-(2-methoxy-phenyl)-pyrrolo[2,1-f][1,2,4]triazine and 2-methoxy-4-[4-(1-methyl-piperidin-4-yl)-perhydro-1,4-diazepin-1-yl]-phenylamine were converted to 2-methoxy-4-(1-{(S)-3,3,3-trifluoro-2-[7-(2-methoxy-phenyl)-pyrrolo[2,1-f][1,2,4]triazin-2-yloxy]-propyl}-piperidin-4-yl)-phenylamine as a yellow solid (61 mg, 46%). MP: 71-80° C.; $^1$H-NMR (CDCl$_3$) δ 8.64 (s, 1H), 8.13 (d, J=8.7 Hz, 1H), 8.06 (d, J=7.6 Hz, 1H), 7.40 (m, 1H), 7.15 (s, 1H), 7.11 (m, 1H), 7.05 (d, J=8.4 Hz, 1H), 7.00 (d, J=2.5 Hz, 1H), 6.78 (d, J=3.2 Hz, 1H), 6.27 (s, 1H), 6.18 (d, J=8.8 Hz, 1H), 3.86 (s, 3H), 3.84 (s, 3H), 3.50 (br s, 4H), 2.87 (m, 4H), 2.64 (br s, 2H), 2.47 (m, 1H), 2.25 (s, 3H), 1.93 (m, 4H), 1.72 (m, 2H), 1.61 (m, 2H); LC/MS (ESI+): 542.3 (M+H).

Example 790

N-[2-(2-{2-Methoxy-4-[4-(1-methyl-piperidin-4-yl)-[1,4]diazepan-1-yl]-phenylamino}-pyrrolo[2,1-f][1,2,4]triazin-7-yl)-phenyl]-N-methyl-methanesulfonamide Following the experimental procedure described in Example 753, N-[2-(2-methanesulfinyl-pyrrolo[2,1-f][1,2,4]triazin-7-yl)-phenyl]-N-methyl-methanesulfonamide and 2-methoxy-4-[4-(1-methyl-piperidin-4-yl)-perhydro-1,4-di-azepin-1-yl]-phenylamine were converted to N-[2-(2-{2-methoxy-4-[4-(1-methyl-piperidin-4-yl)-[1,4]diazepan-1-yl]-phenylamino}-pyrrolo[2,1-f][1,2,4]triazin-7-yl)-phenyl]-N-methyl-methanesulfonamide as a yellow solid (61 mg, 45%). MP: 90-97° C.; $^1$H-NMR (CDCl$_3$) δ 8.67 (s, 1H), 7.94 (s, 1H), 7.88 (d, J=8.4 Hz, 1H), 7.50 (s, 3H), 7.13 (s, 1H), 7.96 (br s, 1H), 6.81 (br s, 1H), 6.26 (s, 1H), 6.08 (d, J=8.4 Hz, 1H), 3.85 (s, 3H), 3.49 (br s, 4H), 3.12 (s, 3H), 2.89 (m, 2H), 2.83 (br s, 2H), 2.64 (br s, 2H), 2.62 (s, 3H), 2.48 (m, 1H), 2.26 (s, 3H), 1.94 (m, 4H), 1.73 (m, 2H), 1.62 (m, 2H); LC/MS (ESI+): 619.4 (M+H).

Example 791

{4-[1-(2-Fluoro-ethyl)-piperidin-4-yl]-2-methoxy-phenyl}-[7-(2-methoxy-phenyl)-pyrrolo[2,1-f][1,2,4]triazin-2-yl]-amine Following the experimental procedure described in Example 753, 2-methanesulfinyl-7-(2-methoxy-phenyl)-pyrrolo[2,1-f][1,2,4]triazine and 4-[1-(2-fluoro-ethyl)-piperidin-4-yl]-2-methoxy-phenylamine were converted to {4-[1-(2-Fluoro-ethyl)-piperidin-4-yl]-2-methoxy-phenyl}-[7-(2-methoxy-phenyl)-pyrrolo[2,1-f][1,2,4]triazin-2-yl]-amine as an orange solid foam (5 mg, 8%). $^1$H-NMR (CDCl$_3$) δ 8.69 (s, 1H), 8.29 (d, J=8.1 Hz, 1H), 7.98 (d, J=7.9 Hz, 1H), 7.43 (m, 2H), 7.12 (m, 1H), 7.07 (d, J=8.3 Hz, 1H), 7.01 (d, J=4.1 Hz, 1H), 6.83 (d, J=4.1 Hz, 1H), 6.74 (m, 2H), 4.68 (m, 1H), 4.56 (m, 1H), 3.88 (s, 3H), 3.84 (s, 3H), 3.09 (m, 2H), 2.79 (m, 1H), 2.72 (m, 1H), 2.46 (m, 1H), 2.18 (m, 2H), 1.84 (br s, 4H); LC/MS (ESI+): 476.1 (M+H).

Example 792

N-[2-(2-{4-[1-(2-Fluoro-ethyl)-piperidin-4-yl]-2-methoxy-phenylamino}-pyrrolo[2,1-f][1,2,4]triazin-7-yl)-phenyl]-N-methyl-methanesulfonamide Following the experimental procedure described in Example 753, N-[2-(2-methanesulfinyl-pyrrolo[2,1-f][1,2,4]triazin-7-yl)-phenyl]-N-methyl-methanesulfonamide and 4-[1-(2-fluoro-ethyl)-piperidin-4-yl]-2-methoxy-phenylamine were converted to N-[2-(2-{4-[1-(2-fluoro-ethyl)-piperidin-4-yl]-2-methoxy-phenylamino}-pyrrolo[2,1-f][1,2,4]triazin-7-yl)-phenyl]-N-methyl-methanesulfonamide as a yellow solid (26 mg, 19%). MP: 90-97° C.; $^1$H-NMR (CDCl$_3$) δ 8.72 (s, 1H), 8.07 (d, J=8.4 Hz, 1H), 7.94 (m, 1H), 7.51 (m, 3H), 7.44 (br s, 1H), 7.03 (d, J=4.7 Hz, 1H), 6.85 (d, J=4.7 Hz, 1H), 6.74 (d, J=1.6 Hz, 1H), 6.66 (dd, J=8.4 Hz, 1.6 Hz, 1H), 4.67 (m, 1H), 4.55 (m, 1H), 3.87 (s, 3H), 3.11 (s, 3H), 3.08 (m, 2H), 2.78 (m, 1H), 2.71 (m, 1H), 2.68 (s, 3H), 2.45 (m, 1H), 2.17 (m, 2H), 1.18 (m, 4H); LC/MS (ESI+): 553.2 (M+H).

Example 793

N-[2-(2-{4-[1-(2-Hydroxy-ethyl)-piperidin-4-yl]-2-methoxy-henylamino}-pyrrolo[2,1-f][1,2,4]triazin-7-yl)-phenyl]-N-methyl-methanesulfonamide Following the experimental procedure described in Example 753, N-[2-(2-methanesulfinyl-pyrrolo[2,1-f][1,2,4]triazin-7-yl)-phenyl]-N-methyl-methanesulfonamide and 2-[4-(4-amino-3-methoxy-phenyl)-piperidin-1-yl]-ethanol were converted to N-[2-(2-{4-[1-(2-hydroxy-ethyl)-piperidin-4-yl]-2-methoxy-henylamino}-pyrrolo[2,1-f][1,2,4]triazin-7-yl)-phenyl]-N-methyl-methanesulfonamide as a yellow solid (48 mg, 25%). MP: 99-111° C.; $^1$H-NMR (CDCl$_3$) δ 8.72 (s, 1H), 8.07 (d, J=8.4 Hz, 1H), 7.95 (m, 1H), 7.53 (m, 3H), 7.45 (s, 1H), 7.03 (d, J=4.8 Hz, 1H), 6.86 d, J=4.8 Hz, 1H), 6.73 (d, J=1.6 Hz, 1H), 6.64 (dd, J=8.4, 1.6 Hz, 1H), 3.90 (s, 3H), 3.65 (m, 2H), 3.12 (s, 3H), 3.05 (m, 2H), 2.67 (s, 3H), 2.59 (m, 2H), 2.47 (m, 1H), 2.19 (m, 3H), 1.78 (m, 4H); LC/MS (ESI+): 551.2 (M+H).

Example 794

(R)-1-(4-{4-[7-(5-Chloro-2-methoxy-phenyl)-pyrrolo[2,1-f][1,2,4]triazin-2-ylamino]-3-methoxy-phenyl}-piperidin-1-yl)-propan-2-ol Following the experimental procedure described in Example 753, 7-(5-chloro-2-methoxy-phenyl)-2-methanesulfinyl-pyrrolo[2,1-f][1,2,4]triazine and (R)-1-[4-(4-amino-3-methoxy-phenyl)-piperidin-1-yl]-propan-2-ol were converted to (R)-1-(4-{4-[7-(5-chloro-2-methoxy-phenyl)-pyrrolo[2,1-f][1,2,4]triazin-2-ylamino]-3-methoxy-phenyl}-piperidin-1-yl)-propan-2-ol as a yellow solid (4 mg, 3%). MP: 94-108° C.; $^1$H-NMR (CDCl$_3$) δ 8.70 (s, 1H), 8.29 (d, J=7.8 Hz, 1H), 8.17 (s, 1H), 7.48 (s, 1H), 7.36 (d, J=8.4 Hz, 1H), 7.07 (d, J=2.6 Hz, 1H), 6.98 (d, J=8.8 Hz, 1H), 6.88 (d, J=8.0 Hz, 1H), 6.82 (d, J=3.2 Hz, 1H), 6.75 (s, 1H), 3.91 (s, 3H), 3.90 (m, 1H), 3.84 (s, 3H), 3.15 (m, 1H), 2.95 (m, 1H), 2.41 (m, 4H), 2.07 (m, 1H), 1.84 (m, 4H), 1.26 (br s, 1H), 1.16 (d, J=5.7 Hz, 3H); LC/MS (ESI+): 522.1 (M+H).

Example 795

N-{2-[2-(4-{4-[(2-Hydroxy-ethyl)-methyl-amino]-piperidin-1-yl}-2-ethoxy-phenylamino)-pyrrolo[2,1-f][1,2,4]triazin-7-yl]-phenyl}-N-methyl-methanesulfonamide Following the experimental procedure described in Example 753, N-[2-(2-methanesulfinyl-pyrrolo[2,1-f][1,2,4]triazin-7-yl)-phenyl]-N-methyl-methanesulfonamide and 2-{[1-(4-amino-3-methoxy-phenyl)-piperidin-4-yl]-methyl-amino}-ethanol were converted to N-{2-[2-(4-{4-[(2-hydroxy-ethyl)-methyl-amino]-piperidin-1-yl}-2-ethoxy-phenylamino)-pyrrolo[2,1-f][1,2,4]triazin-7-yl]-phenyl}-N-methyl-methanesulfonamide, isolated as the trifluoroacetic acid salt (35 mg, 26%). Light brown lyophilate; $^1$H-NMR (dmso-d$_6$) δ 9.29 (br s, 1H), 8.92 (s, 1H), 7.97 (d, J=7.5 Hz, 1H), 7.72 (d, J=8.1 Hz, 1H), 7.63 (m, 2H), 7.53 (m, 2H), 6.98 (br s, 1H), 6.94 (br s, 1H), 6.69 (s, 1H), 6.43 (d, J=8.4 Hz, 1H), 3.83 (s, 3H), 3.77 (m, 4H), 3.41 (m, 1H), 3.31 (m, 1H), 3.10 (m, 1H), 3.07 (s, 3H), 2.89 (m, 1H), 2.88 (s, 3H), 2.79 (s, 3H), 2.73 (m, 2H), 2.07 (m, 2H), 1.77 (m, 2H); LC/MS (ESI+): 580.2 (M+H).

Example 796

2-[(1-{3-Methoxy-4-[7-(2-methoxy-phenyl)-pyrrolo[2,1-f][1,2,4]triazin-2-ylamino]-phenyl}-piperidin-4-yl)-methyl-amino]-ethanol Following the experimental procedure described in Example 753, 2-methanesulfinyl-7-(2-methoxy-phenyl)-pyrrolo[2,1-f][1,2,4]triazine and 2-{[1-(4-amino-3-methoxy-phenyl)-piperidin-4-yl]-methyl-amino}-ethanol were converted to 2-[(1-{3-methoxy-4-[7-(2-methoxy-phenyl)-pyrrolo[2,1-f][1,2,4]triazin-2-ylamino]-phenyl}-piperidin-4-yl)-methyl-amino]-ethanol, isolated as the trifluoroacetic acid salt (42 mg, 28%). Light brown lyophilate; $^1$H-NMR (dmso-d$_6$) δ 9.31 (br s, 1H), 8.91 (s, 1H), 7.89 (d, J=8.7 Hz, 1H), 7.83 (d, J=7.6 Hz, 1H), 7.56 (br s, 1H), 7.44 (m, 1H), 7.20 (d, J=7.6 Hz, 1H), 7.10 (m, 1H), 6.96 (d, J=4.0 Hz, 1H), 6.92 (d, J=4.0 Hz, 1H), 6.72 (s, 1H), 6.46 (d, J=8.7 Hz, 1H), 3.86 (s, 3H), 3.79 (s, 3H), 3.77 (m, 5H), 3.42 (m, 1H), 3.31 (m, 1H), 3.10 (m, 1H), 2.79 (s, 3H), 2.75 (m, 2H), 2.08 (m, 2H), 1.80 (m, 2H); LC/MS (ESI+): 503.22 (M+H).

Example 797

2-(1-{3-Methoxy-4-[7-(2-methoxy-phenyl)-pyrrolo[2,1-f][1,2,4]triazin-2-ylamino]-phenyl}-piperidin-4-ylamino)-ethanol Following the experimental procedure described in Example 753, 2-methanesulfinyl-7-(2-methoxy-phenyl)-pyrrolo[2,1-f][1,2,4]triazine and 2-[1-(4-amino-3-methoxy-phenyl)-piperidin-4-ylamino]-ethanol were converted to 2-(1-{3-methoxy-4-[7-(2-methoxy-phenyl)-pyrrolo[2,1-f][1,2,4]triazin-2-ylamino]-phenyl}-piperidin-4-ylamino)-ethanol as a yellow foam (20 mg, 24%). $^1$H-NMR (CDCl$_3$) δ 8.67 (s, 1H), 8.22 (d, J=8.7 Hz, 1H), 8.01 (d, J=7.7 Hz, 1H), 7.42 (m, 1H), 7.30 (s, 1H), 7.12 (m, 1H), 7.06 (d, J=8.3 Hz, 1H), 7.00 (d, J=4.3 Hz, 1H), 6.81 (d, J=4.3 Hz, 1H), 6.55 (s, 1H), 6.43 (d, J=8.7 Hz, 1H), 3.88 (s, 3H), 3.84 (s, 3H), 3.66 (br s, 2H), 3.53 (m, 2H), 2.86 (br s, 2H), 2.73 (m, 2H), 2.62 (m, 1H), 2.02 (m, 4H), 1.55 (m, 2H); LC/MS (ESI+): 489.3 (M+H).

Example 798

N-[2-(2-{4-[4-(2-Hydroxy-ethylamino)-piperidin-1-yl]-2-methoxy-phenylamino}-pyrrolo[2,1-f][1,2,4]triazin-7-yl)-phenyl]-N-methyl-methanesulfonamide Following the experimental procedure described in Example 753, N-[2-(2-methanesulfinyl-pyrrolo[2,1-f][1,2,4]triazin-7-yl)-phenyl]-N-methyl-methanesulfonamide and 2-[1-(4-amino-3-methoxy-phenyl)-piperidin-4-ylamino]-ethanol were converted to N-[2-(2-{4-[4-(2-hydroxy-ethylamino)-piperidin-1-yl]-2-methoxy-phenylamino}-pyrrolo[2,1-f][1,2,4]triazin-7-yl)-phenyl]-N-methyl-methanesulfonamide as a yellow foam (8 mg, 9%). $^1$H-NMR (CDCl$_3$) δ 8.70 (s, 1H), 7.98 (d, J=8.4 Hz, 1H), 7.94 (m, 1H), 7.51 (br s, 3H), 7.29 (br s, 1H), 6.99 (d, J=3.1 Hz, 1H), 6.84 (d, J=3.1 Hz, 1H), 6.54 (s, 1H), 6.34 (d, J=8.8 Hz, 1H), 3.88 (s, 3H), 3.66 (br s, 2H), 3.53 (m, 2H), 3.12 (s, 3H), 2.86 (br s, 2H), 2.73 (m, 2H), 2.64 (s, 3H), 2.63 (m, 1H), 2.01 (d, J=12.0 Hz, 2H), 1.81 (br s, 2H), 1.53 (m, 2H); LC/MS (ESI+): 592.2 (M+H).

Example 799

(S)-1,1,1-Trifluoro-3-(4-{3-methoxy-4-[7-(2-methoxy-phenyl)-pyrrolo[2,1-f][1,2,4]triazin-2-ylamino]-phenyl}-piperidin-1-yl)-propan-2-ol 2-Methanesulfinyl-7-(2-methoxy-phenyl)-pyrrolo[2,1-f][1,2,4]triazine (50.00 mg, 0.174 mmol), methanesulfonic acid (0.034 mL, 0.52 mmol) and (S)-3-[4-(4-amino-3-methoxy-phenyl)-piperidin-1-yl]-1,1,1-trifluoro-propan-2-ol (109 mg, 0.342 mmol) were combined in 1-methoxy-2-propanol (1.02 mL) in a capped tube and the reaction was stirred at 135° C. for 48 h. The product was isolated by reverse phase preparative hplc (Gilson) followed by neutralization of the trifluoroacetic acid salt to afford (S)-1,1,1-trifluoro-3-(4-{3-methoxy-4-[7-(2-methoxy-phenyl)-pyrrolo[2,1-f][1,2,4]triazin-2-ylamino]-phenyl}-piperidin-1-yl)-propan-2-ol as a brown solid (17 mg, 18%). MP: 77-94° C.; $^1$H-NMR (CDCl$_3$) δ 8.69 (s, 1H), 8.30 (d, J=8.1 Hz, 1H), 7.99 (d, J=7.6 Hz, 1H), 7.44 (m, 2H), 7.14 (m, 1H), 7.08 (d, J=8.4 Hz, 1H), 7.02 (4.4 Hz, 1H), 6.83 (d, J=4.5 Hz, 1H), 6.71 (m, 2H), 4.08 (m, 1H), 3.90 (s, 3H), 3.85 (s, 3H), 3.02 (m, 2H), 2.67 (m, 2H), 2.52 (m, 2H), 2.23 (m, 1H), 1.77 (m, 3H); LC/MS (ESI+): 542.3 (M+H).

Example 800

2-[4-(4-{3-Methoxy-4-[7-(2-methoxy-phenyl)-pyrrolo[2,1-f][1,2,4]triazin-2-ylamino]-phenyl}-[1,4]diazepan-1-yl)-piperidin-1-yl]-ethanol Following the experimental procedure described in Example 753, 2-methanesulfinyl-7-(2-methoxy-phenyl)-pyrrolo[2,1-f][1,2,4]triazine and 2-{4-[4-(4-amino-3-methoxy-phenyl)-perhydro-1,4-diazepin-1-yl]-piperidin-1-yl}-ethanol were converted to 2-[4-(4-{3-methoxy-4-[7-(2-methoxy-phenyl)-pyrrolo[2,1-f][1,2,4]triazin-2-ylamino]-phenyl}-[1,4]diazepan-1-yl)-piperidin-1-yl]-ethanol as a light brown solid (21 mg, 15%). MP: 77-94° C.; $^1$H-NMR (CDCl$_3$) δ 8.64 (s, 1H), 8.14 (d, J=8.8 Hz, 1H), 7.6 Hz, 1H), 7.41 (m, 1H), 7.16 (s, 1H), 7.11 (m, 1H), 7.05 (d, J=8.4 Hz, 1H), 7.00 (d, J=4.3 Hz, 1H), 6.79 (d, J=4.3 Hz, 1H), 6.28 (br s, 1H), 6.18 (d, J=8.8 Hz, 1H), 3.86 (s, 3H), 3.84 (s, 3H), 3.50 (m, 1H), 3.47 (m, 5H), 3.11 (m, 1H), 2.93 (m, 1H), 2.84 (br s, 2H), 2.65 (br s, 2H), 2.56 (m, 1H), 2.48 (m, 1H), 2.24 (s, 1H), 2.04 (m, 1H), 1.91 (m, 3H), 1.75 (m, 3H), 1.56 (m, 1H), 1.42 (m, 1H); LC/MS (ESI+): 572.24 (M+H).

Example 801

2-[4-(1-{3-Methoxy-4-[7-(2-methoxy-phenyl)-pyrrolo[2,1-f][1,2,4]triazin-2-ylamino]-phenyl}-piperidin-4-yl)-[1,4]diazepan-1-yl]-ethanol Following the experimental procedure described in Example 753, 2-methanesulfinyl-7-(2-methoxy-phenyl)-pyrrolo[2,1-f][1,2,4]triazine and 2-{4-[1-(4-amino-3-methoxy-phenyl)-piperidin-4-yl]-perhydro-1,4-diazepin-1-yl}-ethanol were converted to 2-[4-(1-{3-methoxy-4-[7-(2-methoxy-phenyl)-pyrrolo[2,1-f][1,2,4]triazin-2-ylamino]-phenyl}-piperidin-4-yl)-[1,4]diazepan-1-yl]-ethanol as a brown solid (18 mg, 13%). MP: 72-80° C.; $^1$H-NMR (CDCl$_3$) δ 8.67 (s, 1H), 8.22 (d, J=8.7 Hz, 1H), 8.01 (d, J=7.8 Hz, 1H), 7.42 (m, 1H), 7.30 (s, 1H), 7.12 (m, 1H), 7.06 (d, J=8.4 Hz, 1H), 7.00 (br s, 1H), 6.81 (br s, 1H), 6.55 (s, 1H), 6.43 (d, J=8.7 Hz, 1H), 3.88 (s, 3H), 3.84 (s, 3H), 3.58 (m, 4H), 2.78 (m, 14H), 1.80 (m, 6H); LC/MS (ESI+): 572.3 (M+H).

Example 802

N-{2-[2-(4-{4-[1-(2-Hydroxy-ethyl)-piperidin-4-yl]-[1,4]diazepan-1-yl}-2-methoxy-phenylamino)-pyrrolo[2,1-f][1,2,4]triazin-7-yl]-phenyl}-N-methyl-methanesulfonamide Following the experimental procedure described in Example 753, N-[2-(2-methanesulfinyl-pyrrolo[2,1-f][1,2,4]triazin-7-yl)-phenyl]-N-methyl-methanesulfonamide and 2-[1-(4-amino-3-methoxy-phenyl)-piperidin-4-ylamino]-ethanol were converted to N-[2-(2-{4-[4-(2-hydroxy-ethylamino)-piperidin-1-yl]-2-methoxy-phenylamino}-pyrrolo[2,1-f][1,2,4]triazin-7-yl)-phenyl]-N-methyl-methanesulfonamide as a yellow foam (8 mg, 9%). $^1$H-NMR (CDCl$_3$) δ 8.70 (s, 1H), 7.98 (d, J=8.4 Hz, 1H), 7.94 (m, 1H), 7.51 (br s, 3H), 7.29 (br s, 1H), 6.99 (d, J=3.1 Hz, 1H), 6.84 (d, J=3.1 Hz, 1H), 6.54 (s, 1H), 6.34 (d, J=8.8 Hz, 1H), 3.88 (s, 3H), 3.66 (br s, 2H), 3.53 (m, 2H), 3.12 (s, 3H), 2.86 (br s, 2H), 2.73 (m, 2H), 2.64 (s, 3H), 2.63 (m, 1H), 2.01 (d, J=12.0 Hz, 2H), 1.81 (br s, 2H), 1.53 (m, 2H); LC/MS (ESI+): 592.2 (M+H).

Example 803

N-{2-[2-(4-{4-[4-(2-Hydroxy-ethyl)-[1,4]diazepan-1-yl]-piperidin-1-yl}-2-methoxy-phenylamino)-pyrrolo[2,1-f][1,2,4]triazin-7-yl]-phenyl}-N-methyl-methanesulfonamide Following the experimental procedure described in Example 753, N-[2-(2-methanesulfinyl-pyrrolo[2,1-f][1,2,4]triazin-7-yl)-phenyl]-N-methyl-methanesulfonamide and 2-{4-[1-(4-amino-3-methoxy-phenyl)-piperidin-4-yl]-perhydro-1,4-diazepin-1-yl}-ethanol were converted to N-{2-[2-(4-{4-[4-(2-hydroxy-ethyl)-[1,4]diazepan-1-yl]-piperidin-1-yl}-2-methoxy-phenylamino)-pyrrolo[2,1-f][1,2,4]triazin-7-yl]-phenyl}-N-methyl-methanesulfonamide as a brown solid (12 mg, 10%). MP: 91-104° C.; $^1$H-NMR (CDCl$_3$) δ 8.70 (s, 1H), 7.98 (d, J=8.7 Hz, 1H), 7.93 (s, 1H), 7.51 (br s, 3H), 7.29 (s, 1H), 6.99 (d, J=2.7 Hz, 1H), 6.83 (d, J=2.7 Hz, 1H), 6.53 (s, 1H), 6.34 (d, J=8.7 Hz, 1H), 3.87 (s, 3H), 3.83 (m, 1H), 3.57 (m, 4H), 3.12 (s, 3H), 2.78 (m, 8H), 2.69 (m, 3H), 2.64 (s, 3H), 1.80 (m, 8H); LC/MS (ESI+): 649.3 (M+H).

Example 804

N-[2-(2-{2-Methoxy-4-[1-((S)-3,3,3-trifluoro-2-hydroxy-propyl)-piperidin-4-yl]-phenylamino}-pyrrolo[2,1-f][1,2,4]triazin-7-yl)-phenyl]-N-methyl-methanesulfonamide Following the experimental procedure described in Example 753, N-[2-(2-methanesulfinyl-pyrrolo[2,1-f][1,2,4]triazin-7-yl)-phenyl]-N-methyl-methanesulfonamide and 4-{1-[(S)-2-(tert-butyl-dimethyl-silanyloxy)-3,3,3-trifluoro-propyl]-piperidin-4-yl}-2-methoxy-phenylamine were converted to provide an intermediate that was next deprotected by heating it in methanol in presence of aqueous 36% HCl (~5-10% v/v). The solvent was evaporated and the product was isolated by reverse phase hplc (Gilson) to afford alcohol N-[2-(2-{2-methoxy-4-[1-((S)-3,3,3-trifluoro-2-hydroxy-propyl)-piperidin-4-yl]-phenylamino}-pyrrolo[2,1-f][1,2,4]triazin-7-yl)-phenyl]-N-methyl-methanesulfonamide as a yellow foam (12 mg, 14%). $^1$H-NMR (CDCl$_3$) δ 8.73 (s, 1H), 8.08 (d, J=8.4 Hz, 1H), 7.95 (m, 1H), 7.53 (m, 3H), 7.46 (s, 1H), 7.03 (d, J=4.7 Hz, 1H), 6.86 (d, J=4.7 Hz, 1H), 6.71 (s, 1H), 6.63 (dd, J=8.4, 1.1.6 Hz, 1H), 4.06 (m, 1H), 3.90 (s, 3H), 3.13 (s, 3H), 3.02 (m, 2H), 2.66 (s, 3H), 2.65 (m, 2H), 2.53 (m, 2H), 2.20 (m, 1H), 2.00 (br s, 1H), 1.81 (m, 5H); LC/MS (ESI+): 619.2 (M+H).

Example 805

[2-Methoxy-4-(1-methyl-piperidin-3-yl)-phenyl]-[7-(2-methoxy-phenyl)-pyrrolo[2,1-f][1,2,4]triazin-2-yl]-amine Following the experimental procedure described in Example 753, 2-methanesulfinyl-7-(2-methoxy-phenyl)-pyrrolo[2,1-f][1,2,4]triazine and 2-methoxy-4-(1-methyl-piperidin-3-yl)-phenylamine were converted to [2-methoxy-4-(1-methyl-piperidin-3-yl)-phenyl]-[7-(2-methoxy-phenyl)-pyrrolo[2,1-f][1,2,4]triazin-2-yl]-amine as a brown amorphous solid (35 mg, 23%). $^1$H-NMR (CDCl$_3$) δ 8.68 (s, 1H), 8.28 (d, J=8.3 Hz, 1H), 8.99 (dd, J=7.6, 1.6 Hz, 1H), 7.44 (m, 2H), 7.13 (m, 1H), 7.07 (d, J=8.3 Hz, 1H), 7.02 (d, J=4.5 Hz, 1H), 6.83 (d, J=4.5 Hz, 1H), 6.71 (m, 2H), 3.89 (s, 3H), 3.84 (s, 3H), 2.93 (m, 2H), 2.77 (m, 1H), 2.30 (s, 3H), 1.92 (m, 3H), 1.77 (m, 2H), 1.40 (m, 1H); LC/MS (ESI+): 443.54 (M+H).

Example 806

N-(2-{2-[2-Methoxy-4-(1-methyl-piperidin-3-yl)-phenylamino]-pyrrolo[2,1-f][1,2,4]triazin-7-yl}-phenyl)-N-methyl-methanesulfonamide Following the experimental procedure described in Example 753, N-[2-(2-methanesulfinyl-pyrrolo[2,1-f][1,2,4]triazin-7-yl)-phenyl]-N-methyl-methanesulfonamide and 2-methoxy-4-(1-methyl-piperidin-3-yl)-phenylamine were converted to N-(2-{2-[2-methoxy-4-(1-methyl-piperidin-3-yl)-phenylamino]-pyrrolo[2,1-f][1,2,4]triazin-7-yl}-phenyl)-N-methyl-methanesulfonamide as a tan amorphous solid (23 mg, 13%). $^1$H-NMR (CDCl$_3$) δ 8.72 (s, 1H), 8.06 (d, J=8.4 Hz, 1H), 7.94 (m, 1H), 7.53 (m, 3H), 7.45 (s, 1H), 7.02 (d, J=4.6 Hz, 1H), 6.86 (d, J=4.6 Hz, 1H), 6.72 (d, J=1.4 Hz, 1H), 6.64 (dd, J=8.4, 1.4 Hz, 1H), 3.89 (s, 3H), 3.12 (s, 3H), 2.95 (m, 2H), 2.79 (m, 1H), 2.67 (s, 3H), 2.32 (s, 3H), 1.95 (m, 3H), 1.78 (m, 2H), 1.40 (m, 1H); LC/MS (ESI+): 521.2 (M+H).

Example 807

[7-(2-Methoxy-phenyl)-pyrrolo[2,1-f][1,2,4]triazin-2-yl]-(2-methoxy-4-pyridin-3-yl-phenyl)-amine Following the experimental procedure described in Example 753, 2-methanesulfinyl-7-(2-methoxy-phenyl)-pyrrolo[2,1-f][1,2,4]triazine and 2-methoxy-4-pyridin-3-yl-phenylamine were converted to [7-(2-methoxy-phenyl)-pyrrolo[2,1-f][1,2,4]triazin-2-yl]-(2-methoxy-4-pyridin-3-yl-phenyl)-amine as a brown amorphous solid (4 mg, 3%). $^1$H-NMR (CDCl$_3$) δ 8.84 (d, J=2.1 Hz, 1H), 8.73 (s, 1H), 8.55 (dd, J=4.4, 1.4 Hz, 1H), 8.49 (d, J=8.4 Hz, 1H), 7.98 (dd, J=7.6, 1.6 Hz, 1H), 7.85 (d, J=8.2 Hz, 1H), 7.58 (br s, 1H), 7.45 (m, 1H), 7.34 (m, 1H), 7.15 (m, 1H), 7.07 (m, 4H), 6.87 (d, J=8.6 Hz, 1H), 3.99 (s, 3H), 3.86 (s, 3H); LC/MS (ESI+): 424.2 (M+H).

Example 808

N-{2-[2-(2-Methoxy-4-pyridin-3-yl-phenylamino)-pyrrolo[2,1-f][1,2,4]triazin-7-yl]-phenyl}-N-methyl-methanesulfonamide Following the experimental procedure described in Example 753, N-[2-(2-methanesulfinyl-pyrrolo[2,1-f][1,2,4]triazin-7-yl)-phenyl]-N-methyl-methanesulfonamide and 2-methoxy-4-pyridin-3-yl-phenylamine were converted to N-{2-[2-(2-methoxy-4-pyridin-3-yl-phenylamino)-pyrrolo[2,1-f][1,2,4]triazin-7-yl]-phenyl}-N-methyl-methanesulfonamide as a brown amorphous solid (11 mg, 6%). $^1$H-NMR (CDCl$_3$) δ 8.82 (d, J=2.0 Hz, 1H), 8.76 (s, 1H), 8.55 (dd, J=4.8, 1.4 Hz, 1H), 8.28 (d, J=8.4 Hz, 1H), 7.97 (m, 1H), 7.84 (d, J=8.3 Hz, 1H), 7.59 (br s, 1H), 7.54 (m, 3H), 7.34 (m, 1H), 7.06 (m, 2H), 7.01 (m, 1H), 6.90 (d, J=4.56 Hz, 1H), 3.99 (s, 3H), 3.15 (s, 3H), 2.70 (s, 3H); LC/MS (ESI+): 501.1 (M+H).

Example 809

N-{2-[2-(6-Methoxy-2-methyl-2,3-dihydro-1H-isoindol-5-ylamino)-pyrrolo[2,1-f][1,2,4]triazin-7-yl]-phenyl}-N-methyl-methanesulfonamide N-[2-(2-Methanesulfinyl-pyrrolo[2,1-f][1,2,4]triazin-7-yl)-phenyl]-N-methyl-methanesulfonamide (90.00 mg, 0.247), methanesulfonic acid (0.048 mL, 0.74 mmol) and 6-methoxy-2-methyl-2,3-dihydro-1H-isoindol-5-ylamine (88.03 mg, 0.494 mmol) were combined in 1-methoxy-2-propanol (1.45 mL) in a capped tube and the reaction was stirred at 135° C. for 24 h. The product was isolated by reverse phase hplc and neutralization to the free amine to afford N-{2-[2-(6-methoxy-2-methyl-2,3-dihydro-1H-isoindol-5-ylamino)-pyrrolo[2,1-f][1,2,4]triazin-7-yl]-phenyl}-N-methyl-methanesulfonamide as a brown amorphous solid (5 mg, 4%). $^1$H-NMR (CDCl$_3$) δ 8.72 (s, 1H), 8.02 (s, 1H), 7.90 (m, 1H), 7.52 (m, 4H), 7.03 (d, J=4.5 Hz, 1H), 6.86 (d, J=4.5 Hz, 1H), 6.72 (s, 1H), 3.89 (m, 2H), 3.88 (s, 3H), 3.74 (m, 2H), 3.11 (s, 3H), 2.67 (s, 3H), 2.60 (s, 3H); LC/MS (ESI+): 479.1 (M+H).

Example 810

2-[4-(4-{7-[2-(Methanesulfonyl-methyl-amino)-phenyl]-pyrrolo[2,1-f][1,2,4]triazin-2-ylamino}-3-methoxy-phenyl)-piperidin-1-yl]-N,N-dimethyl-acetamide Following the experimental procedure described in Example 753, N-[2-(2-methanesulfinyl-pyrrolo[2,1-f][1,2,4]triazin-7-yl)-phenyl]-N-methyl-methanesulfonamide and 2-[4-(4-amino-3-methoxy-phenyl)-piperidin-1-yl]-N,N-dimethyl-acetamide were converted to 2-[4-(4-{7-[2-(methanesulfonyl-methyl-amino)-phenyl]-pyrrolo[2,1-f][1,2,4]triazin-2-ylamino}-3-methoxy-phenyl)-piperidin-1-yl]-N,N-dimethyl-acetamide as a brown amorphous solid (18 mg, 11%). $^1$H-NMR (CDCl$_3$) δ 8.72 (s, 1H), 8.06 (d, J=8.4 Hz, 1H), 7.94 (m, 1H), 7.53 (m, 3H), 7.44 (s, 1H), 7.02 (d, J=4.4 Hz, 1H), 6.85 (d, J=4.4 Hz, 1H), 6.73 (d, J=1.6 Hz, 1H), 6.65 (dd, J=8.4, 1.6 Hz, 1H), 3.88 (s, 3H), 3.21 (s, 2H), 3.12 (s, 3H), 3.11 (s, 3H), 3.04 (m, 2H), 2.97 (s, 3H), 2.67 (s, 3H), 2.44 (m, 1H), 2.20 (m, 2H), 1.88 (m, 4H); LC/MS (ESI+): 592.2 (M+H).

Example 811

2-(4-{3-Methoxy-4-[7-(2-methoxy-phenyl)-pyrrolo[2,1-f][1,2,4]triazin-2-ylamino]-phenyl}-piperidin-1-yl)-N,N-dimethyl-acetamide Following the experimental procedure described in Example 753, 2-methanesulfinyl-7-(2-methoxy-phenyl)-pyrrolo[2,1-f][1,2,4]triazine and 2-[4-(4-amino-3-methoxy-phenyl)-piperidin-1-yl]-N,N-dimethyl-acetamide were converted to 2-(4-{3-methoxy-4-[7-(2-methoxy-phenyl)-pyrrolo[2,1-f][1,2,4]triazin-2-ylamino]-phenyl}-piperidin-1-yl)-N,N-dimethyl-acetamide as a brown amorphous solid (3 mg, 2%). $^1$H-NMR (CDCl$_3$) δ 8.69 (s, 1H), 8.28 (d, J=8.2 Hz, 1H), 7.99 (dd, J=7.6, 1.6 Hz, 1H), 7.43 (m, 2H), 7.13 (m, 1H), 7.07 (d, J=8.2 Hz, 1H), 7.01 (d, J=4.7 Hz, 1H), 6.83 (d, J=4.7 Hz, 1H), 6.74 (s, 1H), 6.72 (m, 1H), 3.89 (s, 3H), 3.84

(s, 3H), 3.23 (s, 2H), 3.12 (s, 3H), 3.06 (d, J=11.3 Hz, 2H), 2.97 (s, 3H), 2.44 (m, 1H), 2.36 (m, 1H), 2.24 (m, 3H), 2.03 (m, 2H); LC/MS (ESI+): 515.23 (M+H).

Example 812

2-[4-(4-{7-[2-(Methanesulfonyl-methyl-amino)-phenyl]-pyrrolo[2,1-f][1,2,4]triazin-2-ylamino}-3-methoxy-phenyl)-piperidin-1-yl]-acetamide Following the experimental procedure described in Example 753, N-[2-(2-methanesulfinyl-pyrrolo[2,1-f][1,2,4]triazin-7-yl)-phenyl]-N-methyl-methanesulfonamide and 2-[4-(4-amino-3-methoxy-phenyl)-piperidin-1-yl]-acetamide were converted to 2-[4-(4-{7-[2-(methanesulfonyl-methyl-amino)-phenyl]-pyrrolo[2,1-f][1,2,4]triazin-2-ylamino}-3-methoxy-phenyl)-piperidin-1-yl]-acetamide as a yellow solid (15 mg, 10%). MP: 103-112° C.; $^1$H-NMR (CDCl$_3$) δ 8.73 (s, 1H), 8.08 (d, J=8.3 Hz, 1H), 7.95 (m, 1H), 7.53 (m, 3H), 7.46 (s, 1H), 7.12 (br s, 1H), 7.02 (d, J=4.7 Hz, 1H), 6.86 (d, J=4.7 Hz, 1H), 6.72 (d, J=1.3 Hz, 1H), 6.64 (dd, J=8.3, 1.3 Hz, 1H), 5.53 (br s, 1H), 3.90 (s, 3H), 3.13 (s, 3H), 3.04 (s, 2H), 2.99 (m, 2H), 2.66 (s, 3H), 2.46 (m, 1H), 2.29 (m, 2H), 1.85 (m, 2H), 1.75 (m, 2H); LC/MS (ESI+): 564.17 (M+H).

Example 813

N-[2-(2-{4-[1-(2-Dimethylamino-acetyl)-piperidin-4-yl]-2-methoxy-phenylamino}-pyrrolo[2,1-f][1,2,4]triazin-7-yl)-phenyl]-N-methyl-methanesulfonamide Following the experimental procedure described in Example 753, N-[2-(2-methanesulfinyl-pyrrolo[2,1-f][1,2,4]triazin-7-yl)-phenyl]-N-methyl-methanesulfonamide and 1-[4-(4-amino-3-methoxy-phenyl)-piperidin-1-yl]-2-dimethylamino-ethanone were converted to N-[2-(2-{4-[1-(2-dimethylamino-acetyl)-piperidin-4-yl]-2-methoxy-phenylamino}-pyrrolo[2,1-f][1,2,4]triazin-7-yl)-phenyl]-N-methyl-methanesulfonamide as a light brown solid (43 mg, 27%). MP: 99-110° C.; $^1$H-NMR (CDCl$_3$) δ 8.72 (s, 1H), 8.08 (d, J=8.4 Hz, 1H), 7.95 (m, 1H), 7.53 (m, 3H), 7.46 (s, 1H), 7.03 (d, J=4.7 Hz, 1H), 6.86 (d, J=4.7 Hz, 1H), 6.68 (br s, 1H), 6.61 (m, 1H), 4.75 (m, 1H), 4.21 (m, 1H), 3.89 (s, 3H), 3.13 (s, 3H), 3.11 (m, 2H), 2.69 (s, 3H), 2.67 (m, 2H), 2.32 (s, 6H), 1.88 (m, 3H), 1.60 (m, 2H); LC/MS (ESI+): 592.19 (M+H).

Example 814

2-(4-{3-Methoxy-4-[7-(2-methoxy-phenyl)-pyrrolo[2,1-f][1,2,4]triazin-2-ylamino]-phenyl}-piperidin-1-yl)-acetamide Following the experimental procedure described in Example 761, trifluoro-methanesulfonic acid 7-(2-methoxy-phenyl)-pyrrolo[2,1-f][1,2,4]triazin-2-yl ester and 2-[4-(4-amino-3-methoxy-phenyl)-piperidin-1-yl]-acetamide were converted to 2-(4-{3-methoxy-4-[7-(2-methoxy-phenyl)-pyrrolo[2,1-f][1,2,4]triazin-2-ylamino]-phenyl}-piperidin-1-yl)-acetamide as a yellow solid (71 mg, 78%). MP: 88-95° C.; $^1$H-NMR (CDCl$_3$) δ 8.69 (s, 1H), 8.30 (d, J=8.7 Hz, 1H), 8.00 (dd, J=7.6, 1.5 Hz, 1H), 7.44 (m, 2H), 7.13 (m, 2H), 7.07 (d, J=8.7 Hz, 1H), 7.03 (d, J=4.6 Hz, 1H), 6.84 (d, J=4.6 Hz, 1H), 6.72 (m, 2H), 5.42 (br s, 1H), 3.91 (s, 3H), 3.85 (s, 3H), 3.04 (s, 2H), 3.00 (m, 2H), 2.48 (m, 1H), 2.29 (m, 2H), 1.85 (m, 2H), 1.77 (m, 2H); LC/MS (ESI+): 487.3 (M+H).

Example 815

2-Dimethylamino-1-(4-{3-methoxy-4-[7-(2-methoxy-phenyl)-pyrrolo[2,1-f][1,2,4]triazin-2-ylamino]-phenyl}-piperidin-1-yl)-ethanone Following the experimental procedure described in Example 761, trifluoro-methanesulfonic acid 7-(2-methoxy-phenyl)-pyrrolo[2,1-f][1,2,4]triazin-2-yl ester and 1-[4-(4-amino-3-methoxy-phenyl)-piperidin-1-yl]-2-dimethylamino-ethanone were converted to 2-dimethylamino-1-(4-{3-methoxy-4-[7-(2-methoxy-phenyl)-pyrrolo[2,1-f][1,2,4]triazin-2-ylamino]-phenyl}-piperidin-1-yl)-ethanone as a yellow solid (40 mg, 42%). MP: 78-87° C.; $^1$H-NMR (CDCl$_3$) δ 8.69 (s, 1H), 8.30 (d, J=8.7 Hz, 1H), 7.99 (dd, J=7.6, 1.5 Hz, 1H), 7.44 (m, 2H), 7.13 (m, 1H), 7.07 (d, J=8.3 Hz, 1H), 7.02 (d, J=4.6 Hz, 1H), 6.83 (d, J=4.6 Hz, 1H), 6.69 (m, 2H), 4.75 (m, 1H), 4.21 (m, 1H), 3.89 (s, 3H), 3.84 (s, 3H), 3.16 (s, 2H), 3.09 (m, 1H), 2.67 (m, 2H), 2.32 (s, 6H), 1.89 (m, 2H), 1.62 (m, 2H); LC/MS (ESI+): 515.2 (M+H).

Example 816

(6-Methoxy-2-methyl-2,3-dihydro-1H-isoindol-5-yl)-[7-(2-methoxy-phenyl)-pyrrolo[2,1-f][1,2,4]triazin-2-yl]-amine Following the experimental procedure described in Example 761, trifluoro-methanesulfonic acid 7-(2-methoxy-phenyl)-pyrrolo[2,1-f][1,2,4]triazin-2-yl ester and 6-methoxy-2-methyl-2,3-dihydro-1H-isoindol-5-ylamine were converted to (6-methoxy-2-methyl-2,3-dihydro-1H-isoindol-5-yl)-[7-(2-methoxy-phenyl)-pyrrolo[2,1-f][1,2,4]triazin-2-yl]-amine as a yellow solid (13 mg, 17%). MP: 136-141° C.; $^1$H-NMR (CDCl$_3$) δ 8.69 (s, 1H), 8.25 (s, 1H), 7.95 (dd, J=7.6 Hz, 1.3 Hz, 1H), 7.50 (s, 1H), 7.44 (m, 1H), 7.11 (m, 1H), 7.06 (d, J=8.4 Hz, 1H), 7.01 (d, J=4.7 Hz, 1H), 6.83 (d, J=4.7 Hz, 1H), 6.72 (s, 1H), 3.89 (br s, 2H), 3.88 (s, 3H), 3.83 (s, 3H), 3.82 (br s, 2H), 2.61 (s, 3H); LC/MS (ESI+): 402.2 (M+H).

Example 817

4-{3-Methoxy-4-[7-(2-methoxy-phenyl)-pyrrolo[2,1-f][1,2,4]triazin-2-ylamino]-phenyl}-piperidine-1-carboxylic acid tert-butyl ester 4-{3-Methoxy-4-[7-(2-methoxy-phenyl)-pyrrolo[2,1-f][1,2,4]triazin-2-ylamino]-phenyl}-piperidine-1-carboxylic acid tert-butyl ester was prepared as described in Example 787a). $^1$H-NMR (CDCl$_3$) δ 8.69 (s, 1H), 8.30 (d, J=8.8 Hz, 1H), 7.99 (dd, J=7.6; 1.6 Hz, 1H), 7.44 (m, 2H), 7.13 (m, 1H), 7.07 (d, J=8.4 Hz, 1H), 7.02 (d, J=4.8 Hz, 1H), 6.83 (d, J=4.8 Hz, 1H), 6.70 (m, 2H), 4.24 (br s, 2H), 3.89 (s, 3H), 3.84 (s, 3H), 2.79 (m, 2H), 2.59 (m, 1H), 1.81 (m, 2H), 1.62 (m, 2H), 1.49 (s, 9H); LC/MS (ESI+): 530.0 (M+H).

Example 818

4-(4-{7-[2-(Methanesulfonyl-methyl-amino)-phenyl]-pyrrolo[2,1-f][1,2,4]triazin-2-ylamino}-3-methoxy-phenyl)-piperidine-1-carboxylic acid tert-butyl ester Following the experimental procedure described in Example 761, trifluoro-methanesulfonic acid 7-[2-(methanesulfonyl-methyl-amino)-phenyl]-pyrrolo[2,1-f][1,2,4]triazin-2-yl ester and 4-(4-amino-3-methoxy-phenyl)-piperidine-1-carboxylic acid tert-butyl ester were converted to 4-(4-{7-[2-(methanesulfonyl-methyl-amino)-phenyl]-pyrrolo[2,1-f][1,2,4]triazin-2-ylamino}-3-methoxy-phenyl)-piperidine-1-carboxylic acid tert-butyl ester as a yellow foam (573 mg, 71%). $^1$H-NMR (CDCl$_3$) δ 8.72 (s, 1H), 8.08 (d, J=8.3 Hz, 1H), 7.95 (m, 1H), 7.53 (m, 3H), 7.45 (s, 1H), 7.03 (d, J=4.7 Hz, 1H), 6.86 (d, J=4.7 Hz, 1H), 6.69 (s, 1H), 6.62 (d, J=8.4 Hz, 1H), 4.24 (br s, 2H), 3.89 (s, 3H), 3.12 (s, 3H), 2.79 (m, 2H), 2.67 (s, 3H), 2.58 (m, 1H), 1.79 (m, 2H), 1.61 (m, 2H), 1.49 (s, 9H); LC/MS (ESI+): 607.0 (M+H).

Example 819

N-{2-[2-(2-Methoxy-4-piperidin-4-yl-phenylamino)-pyrrolo[2,1-f][1,2,4]triazin-7-yl]-phenyl}-N-methyl-methanesulfonamide Following the experimental procedure described in Example 787b), 4-(4-{7-[2-(methanesulfonyl-methyl-amino)-phenyl]-pyrrolo[2,1-f][1,2,4]triazin-2-ylamino}-3-methoxy-phenyl)-piperidine-1-carboxylic acid tert-butyl ester was converted to N-{2-[2-(2-methoxy-4-piperidin-4-yl-phenylamino)-pyrrolo[2,1-f][1,2,4]triazin-7-yl]-phenyl}-N-methyl-methanesulfonamide as a yellow foam (433 mg, 93%). $^1$H-NMR (CDCl$_3$) δ 8.72 (s, 1H), 8.08 (d, J=8.4 Hz, 1H), 7.95 (m, 1H), 7.53 (m, 3H), 7.45 (s, 1H), 7.03 (d, J=4.7 Hz, 1H), 6.86 (d, J=4.7 Hz, 1H), 6.74 (s, 1H), 6.65 (d, J=8.0 Hz, 1H), 3.89 (s, 3H), 3.23 (m, 2H), 3.12 (s, 3H), 2.76 (m, 2H), 2.67 (s, 3H), 2.57 (m, 1H), 2.30 (br s, 1H), 1.84 (m, 2H), 1.70 (m, 2H); LC/MS (ESI+): 507.0 (M+H).

Example 820

[7-(2-Methoxy-phenyl)-pyrrolo[2,1-f][1,2,4]triazin-2-yl]-(2-methoxy-4-piperidin-4-yl-phenyl)-amine

[7-(2-Methoxy-phenyl)-pyrrolo[2,1-f][1,2,4]triazin-2-yl]-(2-methoxy-4-piperidin-4-yl-phenyl)-amine was prepared as described in Example 787b). $^1$H-NMR (CDCl$_3$) δ 8.69 (s, 1H), 8.30 (d, J=8.0 Hz, 1H), 7.97 (dd, J=7.6; 1.5 Hz, 1H), 7.45 (m, 2H), 7.14 (m, 1H), 7.08 (d, J=8.3 Hz, 1H), 7.02 (d, J=4.7 Hz, 1H), 6.84 (d, J=4.7 Hz, 1H), 6.73 (s, 1H), 6.72 (d, J=8.4 Hz, 1H), 3.90 (s, 3H), 3.84 (s, 3H), 3.50 (m, 2H), 2.92 (m, 2H), 2.67 (m, 1H), 2.03 (m, 4H); LC/MS (ESI+): 430.0 (M+H).

Example 821

2-Amino-1-(4-{3-methoxy-4-[7-(2-methoxy-phenyl)-pyrrolo[2,1-f][1,2,4]triazin-2-ylamino]-phenyl}-piperidin-1-yl)-2-methyl-propan-1-one

[7-(2-Methoxy-phenyl)-pyrrolo[2,1-f][1,2,4]triazin-2-yl]-(2-methoxy-4-piperidin-4-yl-phenyl)-amine (80.00 mg, 0.186 mmol), 2-tert-butoxycarbonylamino-2-methyl-propionic acid (0.045 g, 0.22 mmol), N-(3-dimethylaminopropyl)-N'-ethylcarbodiimide hydrochloride (0.043 g, 0.22 mmol) and N,N-dimethylformamide (1.54 mL, 20.0 mmol) were combined in a round-bottom flask and stirred at room temperature overnight. The reaction mixture was diluted with saturated aqueous NaHCO$_3$ and the resulting precipitate was collected by filtration and was washed twice with water, then dried under vacuum and used in the next step without further purification. Following the experimental procedure described in Example 787b), this precipitate was converted to 2-amino-1-(4-{3-methoxy-4-[7-(2-methoxy-phenyl)-pyrrolo[2,1-f][1,2,4]triazin-2-ylamino]-phenyl}-piperidin-1-yl)-2-methyl-propan-1-one as a yellow solid (58 mg, 61%). MP: 81-89° C.; $^1$H-NMR (CDCl$_3$) δ 8.69 (s, 1H), 8.30 (d, J=8.8 Hz, 1H), 7.99 (dd, J=7.6; 1.6 Hz, 1H), 7.44 (m, 2H), 7.13 (m, 1H), 7.08 (d, J=8.4 Hz, 1H), 7.02 (d, J=4.7 Hz, 1H), 6.83 (d, J=4.7 Hz, 1H), 6.70 (m, 2H), 4.84 (m, 2H), 3.89 (s, 3H), 3.84 (s, 3H), 2.88 (m, 2H), 2.72 (m, 1H), 1.90 (m, 2H), 1.63 (m, 4H), 1.45 (s, 6H); LC/MS (ESI+): 515.0 (M+H).

Example 822

N-[2-(2-{4-[1-(2-Amino-2-methyl-propionyl)-piperidin-4-yl]-2-methoxy-phenylamino}-pyrrolo[2,1-f][1,2,4]triazin-7-yl)-phenyl]-N-methyl-methanesulfonamide Following the experimental procedure described in Example 821, N-{2-[2-(2-methoxy-4-piperidin-4-yl-phenylamino)-pyrrolo[2,1-f][1,2,4]triazin-7-yl]-phenyl}-N-methyl-methanesulfonamide was converted to N-[2-(2-{4-[1-(2-Amino-2-methyl-propionyl)-piperidin-4-yl]-2-methoxy-phenylamino}-pyrrolo[2,1-f][1,2,4]triazin-7-yl)-phenyl]-N-methyl-methanesulfonamide as a yellow solid (42 mg, 60%). MP: 92-100° C.; $^1$H-NMR (CDCl$_3$) δ 8.72 (s, 1H), 8.08 (d, J=8.3 Hz, 1H), 7.94 (m, 1H), 7.53 (m, 3H), 7.46 (s, 1H), 7.02 (d, J=4.7 Hz, 1H), 6.86 (d, J=4.7 Hz, 1H), 6.69 (br s, 1H), 6.62 (d, J=9.2 Hz, 1H), 4.84 (m, 2H), 3.89 (s, 3H), 3.13 (s, 3H), 2.87 (m, 2H), 2.71 (m, 1H), 2.67 (s, 3H), 1.87 (m, 2H), 1.62 (m, 4H), 1.45 (s, 6H); LC/MS (ESI+): 593.0 (M+H).

Example 823

2-Amino-1-(4-{3-methoxy-4-[7-(2-methoxy-phenyl)-pyrrolo[2,1-f][1,2,4]triazin-2-ylamino]-phenyl}-piperidin-1-yl)-ethanone Following the experimental procedure described in Example 821, [7-(2-methoxy-phenyl)-pyrrolo[2,1-f][1,2,4]triazin-2-yl]-(2-methoxy-4-piperidin-4-yl-phenyl)-amine was converted to 2-amino-1-(4-{3-methoxy-4-[7-(2-methoxy-phenyl)-pyrrolo[2,1-f][1,2,4]triazin-2-ylamino]-phenyl}-piperidin-1-yl)-ethanone as a yellow solid (40 mg, 50%). MP: 86-99° C.; $^1$H-NMR (CDCl$_3$) δ 8.69 (s, 1H), 8.30 (d, J=8.7 Hz, 1H), 7.98 (dd, J=7.6 ; 1.4 Hz, 1H), 7.44 (m, 2H), 7.13 (m, 1H), 7.08 (d, J=8.0 Hz, 1H), 7.02 (d, J=4.7 Hz, 1H), 6.84 (d, J=4.7 Hz, 1H), 4.79 (m, 2H), 3.89 (s, 3H), 3.84 (s, 3H), 3.80 (br s, 1H), 3.51 (s, 2H), 3.08 (m, 1H), 2.69 (m, 2H), 1.90 (m, 2H), 1.62 (m, 5H); LC/MS (ESI+): 487.0 (M+H).

Example 824

N-[2-(2-{4-[1-(2-Amino-acetyl)-piperidin-4-yl]-2-methoxy-phenylamino}-pyrrolo[2,1-f][1,2,4]triazin-7-yl)-phenyl]-N-methyl-methanesulfonamide Following the experimental procedure described in Example 821, N-{2-[2-(2-methoxy-4-piperidin-4-yl-phenylamino)-pyrrolo[2,1-f][1,2,4]triazin-7-yl]-phenyl}-N-methyl-methanesulfonamide was converted to N-[2-(2-{4-[1-(2-amino-acetyl)-piperidin-4-yl]-2-methoxy-phenylamino}-pyrrolo[2,1-f][1,2,4]triazin-7-yl)-phenyl]-N-methyl-methanesulfonamide as a yellow solid (38 mg, 49%). MP: 106-119° C.; $^1$H-NMR (CDCl$_3$) δ 8.73 (s, 1H), 8.09 (d, J=8.3 Hz, 1H), 7.95 (m, 1H), 7.53 (m, 3H), 7.46 (s, 1H), 7.03 (d, J=4.7 Hz, 1H), 6.86 (d, J=4.7 Hz, 1H), 6.67 (d, J=1.3 Hz, 1H), 6.60 (dd, J=8.3; 1.4 Hz, 1H), 4.78 (m, 1H), 3.89 (s, 3H), 3.82

(m, 1H), 3.51 (br s, 2H), 3.13 (s, 3H), 3.08 (m, 1H), 2.69 (m, 2H), 2.67 (s, 3H), 1.88 (m, 2H), 1.62 (m, 4H); LC/MS (ESI+): 564.0 (M+H).

Example 825

(±)-1-Fluoro-3-(4-{3-methoxy-4-[7-(2-methoxy-phenyl)-pyrrolo[2,1-f][1,2,4]triazin-2-ylamino]-phenyl}-piperidin-1-yl)-propan-2-ol Following the experimental procedure described in Example 787c), [7-(2-methoxy-phenyl)-pyrrolo[2,1-f][1,2,4]triazin-2-yl]-(2-methoxy-4-piperidin-4-yl-phenyl)-amine was converted to (±)-1-fluoro-3-(4-{3-methoxy-4-[7-(2-methoxy-phenyl)-pyrrolo[2,1-f][1,2,4]triazin-2-ylamino]-phenyl}-piperidin-1-yl)-propan-2-ol as a yellow solid (24 mg, 41%). MP: 73-79° C.; $^1$H-NMR (CDCl$_3$) δ 8.69 (s, 1H), 8.29 (d, J=8.8 Hz, 1H), 8.00 (dd, J=7.6 Hz; 1.5 Hz, 1H), 7.44 (m, 2H), 7.14 (m, 1H), 7.08 (d, J=8.3 Hz, 1H), 7.02 (d, J=4.6 Hz, 1H), 6.83 (d, J=4.6 Hz, 1H), 6.73 (s, 1H), 6.72 (d, J=7.6 Hz, 1H), 4.44 (m, 2H), 3.95 (m, 1H), 3.91 (s, 3H), 3.85 (s, 3H), 3.10 (m, 1H), 2.95 (m, 1H), 2.47 (m, 4H), 2.10 (m, 1H), 1.80 (m, 4H), 1.59 (br s, 1 OH, and water peak); LC/MS (ESI+): 519.14 (M+H).

Example 826

(±)-N-[2-(2-{4-[1-(3-Fluoro-2-hydroxy-propyl)-piperidin-4-yl]-2-methoxy-phenylamino}-pyrrolo[2,1-f][1,2,4]triazin-7-yl)-phenyl]-N-methyl-methane-sulfonamide Following the experimental procedure described in Example 787c), N-{2-[2-(2-methoxy-4-piperidin-4-yl-phenylamino)-pyrrolo[2,1-f][1,2,4]triazin-7-yl]-phenyl}-N-methyl-methanesulfonamide was converted to (±)-N-[2-(2-{4-[1-(3-fluoro-2-hydroxy-propyl)-piperidin-4-yl]-2-methoxy-phenylamino}-pyrrolo[2,1-f][1,2,4]triazin-7-yl)-phenyl]-N-methyl-methanesulfonamide as a yellow solid (42 mg, 62%). MP: 82-95° C.; $^1$H-NMR (CDCl$_3$) δ 8.72 (s, 1H), 8.08 (d, J=8.3 Hz, 1H), 7.96 (m, 1H), 7.53 (m, 3H), 7.46 (s, 1H), 7.03 (d, J=4.7 Hz, 1H), 6.86 (d, J=4.7 Hz, 1H), 6.72 (s, 1H), 6.64 (d, J=8.3 Hz, 1H), 4.44 (m, 2H), 3.96 (m, 1H), 3.90 (s, 3H), 3.13 (s, 3H), 3.09 (m, 1H), 2.95 (m, 1H), 2.68 (s, 3H), 2.50 (m, 4H), 2.10 (m, 1H), 1.77 (m, 4H); LC/MS (ESI+): 583.0 (M+H).

Example 827

[2-Methoxy-4-(1-oxetan-3-yl-piperidin-4-yl)-phenyl]-[7-(2-methoxy-phenyl)-pyrrolo[2,1-f][1,2,4]triazin-2-yl]-amine To [7-(2-methoxy-phenyl)-pyrrolo[2,1-f][1,2,4]triazin-2-yl]-(2-methoxy-4-piperidin-4-yl-phenyl)-amine (60.00 mg, 0.140 mmol) in N,N-dimethylformamide (0.52 mL)/Methanol (2.00 mL)/Acetic acid (0.26 mL) was added oxetan-3-one (30.06 mg, 0.417 mmol) and the reaction mixture was cooled to 0° C. Sodium cyanoborohydride (43.64 mg, 0.695 mmol) was added and the reaction was heated at 60° C. overnight, and then at room temperature in air for 10 h to re-aromatize the pyrrolo[2,1-f][1,2,4]triazine core, which underwent partial reduction. The reaction mixture was concentrated, and the residue was partitioned between dichloromethane/1N sodium carbonate, washed with brine, dried over sodium sulfate, and concentrated. The product was isolated by flash chromatography (ISCO, SIlicagel, MeOH/DCM 0-10%) to afford [2-methoxy-4-(1-oxetan-3-yl-piperidin-4-yl)-phenyl]-[7-(2-methoxy-phenyl)-pyrrolo[2,1-f][1,2,4]triazin-2-yl]-amine as a yellow solid (40 mg, 59%). MP: 78-85° C.; $^1$H-NMR (CDCl$_3$) δ 8.69 (s, 1H), 8.30 (d, J=8.7 Hz, 1H), 7.99 (dd, J=7.6 ; 1.4 Hz, 1H), 7.42 (m, 2H), 7.12 (m, 1H), 7.07 (d, J=8.4 Hz, 1H), 7.02 (d, J=4.6 Hz, 1H), 6.83 (d, J=4.6 Hz, 1H), 6.74 (m, 2H), 4.68 (m, 4H), 3.88 (s, 3H), 3.84 (s, 3H), 3.51 (m, 1H), 2.88 (m, 2H), 2.47 (m, 1H), 1.90 (m, 6H); LC/MS (ESI+): 485.9 (M+H).

Example 828

N-(2-{2-[2-Methoxy-4-(1-oxetan-3-yl-piperidin-4-yl)-phenylamino]-pyrrolo[2,1-f][1,2,4]triazin-7-yl}-phenyl)-N-methyl-methanesulfonamide Following the experimental procedure described in Example 827, except that re-aromatization required treatment with MnO$_4$, N-{2-[2-(2-methoxy-4-piperidin-4-yl-phenylamino)-pyrrolo[2,1-f][1,2,4]triazin-7-yl]-phenyl}-N-methyl-methanesulfonamide was converted to N-(2-{2-[2-methoxy-4-(1-oxetan-3-yl-piperidin-4-yl)-phenylamino]-pyrrolo[2,1-f][1,2,4]triazin-7-yl}-phenyl)-N-methyl-methanesulfonamide as a yellow foam (26 mg, 33%). $^1$H-NMR (CDCl$_3$) δ 8.72 (s, 1H), 8.08 (d, J=8.4 Hz, 1H), 7.95 (m, 1H), 7.52 (m, 3H), 7.45 (s, 1H), 7.03 (d, J=4.7 Hz, 1H), 6.86 (d, J=4.7 Hz, 1H), 6.74 (s, 1H), 6.66 (d, J=8.4 Hz, 1H), 4.67 (m, 4H), 3.88 (s, 3H), 3.51 (m, 1H), 3.12 (s, 3H), 2.87 (m, 2H), 2.67 (s, 3H), 2.46 (m, 1H), 1.89 (m, 6H); LC/MS (ESI+): 563.0 (M+H).

Example 829

(±)-(3S,4S)-4-{3-Methoxy-4-[7-(2-methoxy-phenyl)-pyrrolo[2,1-f][1,2,4]triazin-2-ylamino]-phenyl}-1-methyl-piperidine-3,4-diol a). A solution of 4-(3-methoxy-4-nitro-phenyl)-3,6-dihydro-2H-pyridine-1-carboxylic acid tert-butyl ester (500.00 mg, 1.495 mmol) in acetone (13.50 mL)/water (1.50 mL) was treated with N-methylmorpholine N-oxide (262.76 mg, 2.243 mmol) and osmium tetraoxide (19.01 mg, 0.075 mmol) and the reaction mixture was stirred overnight at room temperature. The reaction was quenched by addition of aqueous sodium thiosulfate, and the product was extracted in ethyl acetate. The combined extracts were dried over Na$_2$SO$_4$, and then filtered, and the solvent was evaporated under reduced pressure. The product was isolated by flash chromatography (Isco, Silicagel, Methanol/DCM 0-5%) to afford (±)-(3S,4S)-3,4-dihydroxy-4-(3-methoxy-4-nitro-phenyl)-piperidine-1-carboxylic acid tert-butyl ester (540 mg, 98%).

b). To a solution of (±)-(3S,4S)-3,4-dihydroxy-4-(3-methoxy-4-nitro-phenyl)-piperidine-1-carboxylicacid tert-butyl ester (540 mg) in ethanol (30 mL) was added palladium on carbon 10% (78.00 mg). The mixture was shaken in a Parr apparatus under an atmosphere of hydrogen (~max 25-30 PSI) for 5 h. Filtration through Celite and evaporation of the solvent provided (±)-(3S,4S)-4-(4-amino-3-methoxy-phenyl)-3,4-dihydroxy-piperidine-1-carboxylic acid tert-butyl ester in quantitative yield.

c). To a suspension of lithium tetrahydroaluminate (500.54 mg, 13.188 mmol) in tetrahydrofuran (14 mL) at 0° C. was added a solution of (±)-(3S,4S)-4-(4-amino-3-methoxy-phenyl)-3,4-dihydroxy-piperidine-1-carboxylic acid tert-butyl ester (450.00 mg, 1.330 mmol) in tetrahydrofuran (14.8 mL), and the reaction was allowed first to warm to room temperature and then was heated to reflux for 3 hours. The reaction mixture was cooled, then Na₂SO₄×10H₂O (3 g) was slowly added (gas evolution!), and the reaction was stirred at room temperature for 0.5 h. The suspension was filtered, and the solids were extensively washed with DCM. The combined organics were dried (MgSO4), and the solvent was evaporated in vacuum to afford a mixture of products with (±)-(3S, 4S)-4-(4-amino-3-methoxy-phenyl)-1-methyl-piperidine-3,4-diol and (±)-4-(4-amino-3-methoxy-phenyl)-1-methyl-piperidin-3-ol as major components (212 mg, —63%).

d). Following the experimental procedure described in Example 761, trifluoro-methanesulfonic acid 7-(2-methoxy-phenyl)-pyrrolo[2,1-f][1,2,4]triazin-2-yl ester and the inseparable mixture of (±)-(3S,4S)-4-(4-amino-3-methoxy-phenyl)-1-methyl-piperidine-3,4-diol and (±)-4-(4-amino-3-methoxy-phenyl)-1-methyl-piperidin-3-ol were converted to (±)-(3S,4S)-4-{3-methoxy-4-[7-(2-methoxy-phenyl)-pyrrolo[2,1-f][1,2,4]triazin-2-ylamino]-phenyl}-1-methyl-piperidine-3,4-diol as a yellow foam (14 mg, 14%). ¹H-NMR (CDCl₃) δ 8.67 (s, 1H), 8.36 (d, J=8.4 Hz, 1H), 7.93 (d, J=7.6 Hz, 1H), 7.47 (s, 1H), 7.44 (m, 1H), 7.11 (m, 1H), 7.06 (m, 2H), 7.01 (d, J=4.7 Hz, 1H), 6.94 (dd, J=8.4, 1.4 Hz, 1H), 6.83 (d, J=4.7 Hz, 1H), 4.19 (broad dd, J=10.0, 4.8 Hz, 1H), 3.90 (s, 3H), 3.83 (s, 3H), 2.89 (m, 1H), 2.66 (m, 1H), 2.46 (m, 1H), 2.40 (s, 3H), 2.37 (m, 1H), 2.07 (m, 1H), 1.87 (m, 1H), 1.80 (br s, exchangeable H); LC/MS (ESI+): 476.14 (M+H).

Example 830

(±)-4-{3-Methoxy-4-[7-(2-methoxy-phenyl)-pyrrolo[2,1-f][1,2,4]triazin-2-ylamino]-phenyl}-1-methyl-piperidin-3-ol (±)-4-{3-Methoxy-4-[7-(2-methoxy-phenyl)-pyrrolo[2,1-f][1,2,4]triazin-2-ylamino]-phenyl}-1-methyl-piperidin-3-ol was the other product of the reaction described in Example 829d): yellow foam (14 mg, 14%). ¹H-NMR (CDCl₃) δ 8.69 (s, 1H), 8.35 (d, J=8.0 Hz, 1H), 7.95 (dd, J=7.6; 1.3 Hz, 1H), 7.43 (m, 2H), 7.11 (m, 1H) 7.06 (d, J=8.0 Hz, 1H), 7.01 (d, J=4.6 Hz, 1H), 6.83 (d, J=4.6 Hz, 1H), 6.78 (m, 2H), 3.88 (s, 3H), 3.84 (s, 3H), 3.82 (m, 1H), 3.19 (dd, J=10.6; 4.0 Hz, 1H), 2.93 (br d, J=11.0 Hz, 1H), 2.39 (s, 3H), 2.32 (m, 1H), 2.07 (m, 1H), 1.98 (m, 1H), 1.89 (m, 2H), 1.78 (br s, exchangeable H); LC/MS (ESI+): 460.19 (M+H).

Example 831

(±)-(3S,4S)-3,4-Dihydroxy-4-{3-methoxy-4-[7-(2-methoxy-phenyl)-pyrrolo[2,1-f][1,2,4]triazin-2-ylamino]-phenyl}-piperidine-1-carboxylic acid tert-butyl ester Following the experimental procedure described in Example 761, trifluoro-methanesulfonic acid 7-(2-methoxy-phenyl)-pyrrolo[2,1-f][1,2,4]triazin-2-yl ester and (±)-(3S, 4S)-4-(4-amino-3-methoxy-phenyl)-3,4-dihydroxy-piperidine-1-carboxylic acid tert-butyl ester were converted to (±)-(3S,4S)-3,4-dihydroxy-4-{3-methoxy-4-[7-(2-methoxy-phenyl)-pyrrolo[2,1-f][1,2,4]triazin-2-ylamino]-phenyl}-piperidine-1-carboxylic acid tert-butyl ester as a yellow foam (91 mg, 76%). ¹H-NMR (CDCl₃) δ 8.64 (s, 1H), 8.35 (d, J=8.4 Hz, 1H), 7.93 (m, 1H), 7.47 (br s, 1H), 7.45 (m, 1H), 7.12 (m, 1H), 7.08 (d, J=8.4 Hz, 1H), 7.03 (br s, 1H), 7.01 (d, J=4.8 Hz, 1H), 6.88 (dd, J=8.4; 1.3 Hz, 1H), 6.83 (d, J=4.8 Hz, 1H), 4.19 (br s, 1H), 4.04 (m, 2H), 3.90 (s, 3H), 3.84 (s, 3H), 3.15 (m, 1H), 3.00 (m, 1H), 2.78 (br s, 1H), 2.03 (br s, 1H), 1.84 (br s, 2H), 1.51 (s, 9H); LC/MS (ESI+): 562.0 (M+H).

Example 832

(±)-(3S,4S)-4-{3-Methoxy-4-[7-(2-methoxy-phenyl)-pyrrolo[2,1-f][1,2,4]triazin-2-ylamino]-phenyl}-piperidine-3,4-diol Following the experimental procedure described in Example 787b), (±)-(3S,4S)-3,4-dihydroxy-4-{3-methoxy-4-[7-(2-methoxy-phenyl)-pyrrolo[2,1-f][1,2,4]triazin-2-ylamino]-phenyl}-piperidine-1-carboxylic acid tert-butyl ester was converted to (±)-(3S,4S)-4-{3-Methoxy-4-[7-(2-methoxy-phenyl)-pyrrolo[2,1-f][1,2,4]triazin-2-ylamino]-phenyl}-piperidine-3,4-diol as a yellow foam (45 mg, 60%). ¹H-NMR (CDCl₃) δ 8.64 (s, 1H), 8.34 (d, J=8.3 Hz, 1H), 7.93 (d, J=7.6 Hz, 1H), 7.43 (m, 2H), 7.11 (m, 1H), 7.08 (m, 2H), 7.01 (d, J=4.7 Hz, 1H), 6.93 (d, J=8.5 Hz, 1H), 6.82 (d, J=4.7 Hz, 1H), 4.02 (dd, J=10.0; 4.9 Hz, 1H), 3.89 (s, 3H), 3.83 (s, 3H), 3.03 (m, 2H), 2.88 (d, J=10.8 Hz, 1H), 2.82 (m, 1H), 1.86 (m, 3H), 1.80 (br s, 2OH and water peak); LC/MS (ESI+): 462.0 (M+H).

Example 833

(±)-(3S,4S)-1-(2-Fluoro-ethyl)-4-{3-methoxy-4-[7-(2-methoxy-phenyl)-pyrrolo[2,1-f][1,2,4]triazin-2-ylamino]-phenyl}-piperidine-3,4-diol A mixture of (±)-(3S,4S)-4-{3-methoxy-4-[7-(2-methoxy-phenyl)-pyrrolo[2,1-f][1,2,4]triazin-2-ylamino]-phenyl}-piperidine-3,4-diol (42.00 mg, 0.0910 mmol), 1-fluoro-2-iodo-ethane (18.99 mg, 0.109 mmol), and sodium bicarbonate (9.174 mg, 0.109 mmol) in acetonitrile (1.000 mL, 19.15 mmol) was heated to reflux for overnight. After evaporation of volatiles under reduced pressure, the product was isolated by preparative reverse phase hplc (Gilson). Free base was obtained by catch/release work-up on acidic resin cartridge (Strata-X-C from Phenomenex) to afford (±)-(3S,4S)-1-(2-fluoro-ethyl)-4-{3-methoxy-4-[7-(2-methoxy-phenyl)-pyrrolo[2,1-f][1,2,4]triazin-2-ylamino]-phenyl}-piperidine-3,4-diol as a yellow foam (19 mg, 41%). ¹H-NMR (CDCl₃) δ 8.66 (s, 1H), 8.36 (d, J=8.4 Hz, 1H), 7.93 (d, J=7.6 Hz, 1H), 7.45 (m, 2H), 7.11 (m, 3H), 7.01 (d, J=4.6 Hz, 1H), 6.95 (d, J=8.5 Hz, 1H), 6.83 (d, J=4.6 Hz, 1H), 4.67 (m, 1H), 4.56 (m, 1H), 4.19 (dd, J=10.0; 4.8 Hz, 1H), 3.90 (s, 3H), 3.84 (s, 3H), 3.00 (m, 1H), 2.85 (m, 1H), 2.75 (m, 3H), 2.55 (m, 1H), 2.44 (m, 1H), 2.07 (m, 1H), 1.90 (br s, 1H), 1.87 (m, 1H); LC/MS (ESI+): 508.0 (M+H).

Example 834

(±)-(3R,4S)-3-Hydroxy-4-{3-methoxy-4-[7-(2-methoxy-phenyl)-pyrrolo[2,1-f][1,2,4]triazin-2-ylamino]-phenyl}-piperidine-1-carboxylic acid tert-butyl ester a). 4-(3-Methoxy-4-nitro-phenyl)-3,6-dihydro-2H-pyridine-1-carboxylic acid tert-butyl ester (200.00 mg, 0.598 mmol) in methylene chloride (2.50 mL, 39.0 mmol) was treated with m-CPBA 70-75% in m-chloroperbenzoic acid (206.44 mg, 0.837 mmol) at room temperature overnight. The reaction was quenched by addition of aqueous sodium thiosulfate solution and saturated NaHCO₃ solution. The product was extracted in methylene chloride, the extracts were dried (MgSO₄), the solvent was evaporated under reduced pressure, and the product was isolated by flash chromatography (ISCO, Silicagel, EtOAc/Hexanes) to afford 6-(3-methoxy-4-nitro-phenyl)-7-oxa-3-aza-bicyclo[4.1.0]heptane-3-carboxylic acid tert-butyl ester (190 mg, 91%).

b). To a solution of 6-(3-methoxy-4-nitro-phenyl)-7-oxa-3-aza-bicyclo[4.1.0]heptane-3-carboxylic acid tert-butyl ester (190 mg, 0.542 mmol) in methanol (10.00 mL) was added palladium on carbon 10% (40.00 mg), and the mixture was shaken in a Parr apparatus under an atmosphere of hydrogen (35 PSI) for 2 h. Filtration through Celite and evaporation of the solvent provided crude (±)-(3R,4S)-4-(4-amino-3-methoxy-phenyl)-3-hydroxy-piperidine-1-carboxylic acid tert-butyl ester (173 mg, 99%), which was used without further purification.

c). Following the experimental procedure described in Example 761, trifluoro-methanesulfonic acid 7-(2-methoxy-phenyl)-pyrrolo[2,1-f][1,2,4]triazin-2-yl ester and (±)-(3R,4S)-4-(4-amino-3-methoxy-phenyl)-3-hydroxy-piperidine-1-carboxylic acid tert-butyl ester were converted to (±)-(3R,4S)-3-hydroxy-4-{3-methoxy-4-[7-(2-methoxy-phenyl)-pyrrolo[2,1-f][1,2,4]triazin-2-ylamino]-phenyl}-piperidine-1-carboxylic acid tert-butyl ester as a yellow foam (163 mg, 74%). $^1$H-NMR (CDCl$_3$) δ 8.68 (s, 1H), 8.33 (d, J=8.2 Hz, 1H), 7.97 (d, J=6.8 Hz, 1H), 7.47 (s, 1H), 7.44 (m, 1H), 7.13 (m, 1H), 7.07 (d, J=8.3 Hz, 1H), 7.02 (d, J=7.6 Hz, 1H), 6.84 (d, J=4.6 Hz, 1H), 6.79 (s, 1H), 6.75 (d, J=8.4 Hz, 1H), 4.31 (br s, 2H), 3.92 (br s, 1H), 3.89 (s, 3H), 3.84 (s, 3H), 2.99 (m, 1H), 2.78 (m, 2H), 2.24 (m, 1H), 1.62 (m, 2H), 1.49 (s, 9H); LC/MS (ESI+): 546.0 (M+H).

Example 835

(±)-(3R,4S)-4-{3-Methoxy-4-[7-(2-methoxy-phenyl)-pyrrolo[2,1-f][1,2,4]triazin-2-ylamino]-phenyl}-piperidin-3-ol Following the experimental procedure described in Example 787b), (±)-(3R,4S)-3-hydroxy-4-{3-methoxy-4-[7-(2-methoxy-phenyl)-pyrrolo[2,1-f][1,2,4]triazin-2-ylamino]-phenyl}-piperidine-1-carboxylic acid tert-butyl ester was converted to (±)-(3R,4S)-4-{3-methoxy-4-[7-(2-methoxy-phenyl)-pyrrolo[2,1-f][1,2,4]triazin-2-ylamino]-phenyl}-piperidin-3-ol as a yellow foam (80 mg, 58%). $^1$H-NMR (CDCl$_3$) δ 8.70 (s, 1H), 8.33 (d, J=8.3 Hz, 1H), 7.99 (d, J=6.8 Hz, 1H), 7.47 (s, 1H), 7.44 (m, 1H), 7.14 (m, 1H), 7.07 (d, J=8.3 Hz, 1H), 7.02 (d, J=4.6 Hz, 1H), 6.84 (d, J=4.6 Hz, 1H), 6.83 (s, 1H), 6.77 (d, J=8.4 Hz, 1H), 3.91 (s, 3H), 3.85 (s, 3H), 3.84 (br s, 1H), 3.19 (m, 2H), 2.88 (d, J=12.5 Hz, 1H), 2.75 (m, 2H), 2.13 (m, 1H), 1.62 (m* overlapped by a br s, 1H, * 1 NH, 1OH, and water peak). Observed upon D$_2$O exchange; LC/MS (ESI+): 446.0 (M+H).

Example 836

(±)-2-(3-{3-Methoxy-4-[7-(2-methoxy-phenyl)-pyrrolo[2,1-f][1,2,4]triazin-2-ylamino]-phenyl}-pyrrolidin-1-yl)-acetamide Following the experimental procedure described in Example 761, trifluoro-methanesulfonic acid 7-(2-methoxy-phenyl)-pyrrolo[2,1-f][1,2,4]triazin-2-yl ester and (±)-2-[3-(4-amino-3-methoxy-phenyl)-pyrrolidin-1-yl]-acetamide were converted to (±)-2-(3-{3-methoxy-4-[7-(2-methoxy-phenyl)-pyrrolo[2,1-f][1,2,4]triazin-2-ylamino]-phenyl}-pyrrolidin-1-yl)-acetamide as a light brown foam (54 mg, 53%). $^1$H-NMR (CDCl$_3$) δ 8.70 (s, 1H), 8.29 (d, J=8.8 Hz, 1H), 8.00 (dd, J=7.6; 1.2 Hz, 1H), 7.43 (m, 2H), 7.13 (m, 1H), 7.08 (d, J=8.3 Hz, 1H), 7.03 (d, J=4.7 Hz, 1H), 7.02 (br s, 1H), 6.84 (d, J=4.7 Hz, 1H), 6.75 (d, J=8.4 Hz, 1H), 6.74 (m, 1H), 5.54 (br s, 1H), 3.90 (s, 3H), 3.85 (s, 3H), 3.35 (m, 1H), 3.28 (d, J=16.5 Hz, 1H), 3.19 (d, J=16.5 Hz, 1H), 3.06 (m, 1H), 2.87 (m, 2H), 2.69 (m, 1H), 2.32 (m, 1H), 1.93 (m, 1H); LC/MS (ESI+): 473.0 (M+H).

Example 837

(±)-2-[3-(4-{7-[2-(Methanesulfonyl-methyl-amino)-phenyl]-pyrrolo[2,1-f][1,2,4]triazin-2-ylamino}-3-methoxy-phenyl)-pyrrolidin-1-yl]-acetamide Following the experimental procedure described in Example 761, trifluoro-methanesulfonic acid 7-[2-(methanesulfonyl-methyl-amino)-phenyl]-pyrrolo[2,1-f][1,2,4]triazin-2-yl ester and (±)-2-[3-(4-amino-3-methoxy-phenyl)-pyrrolidin-1-yl]-acetamide were converted to (±)-2-[3-(4-{7-[2-(methanesulfonyl-methyl-amino)-phenyl]-pyrrolo[2,1-f][1,2,4]triazin-2-ylamino}-3-methoxy-phenyl)-pyrrolidin-1-yl]-acetamide as a light brown foam (75 mg, 62%). $^1$H-NMR (CDCl$_3$) δ 8.72 (s, 1H), 8.73 (s, 1H), 8.07 (d, J=8.3 Hz, 1H), 7.95 (m, 1H), 7.53 (m, 3H), 7.46 (s, 1H), 7.02 (d, J=4.7 Hz, 1H), 6.99 (br s, 1H), 6.86 (d, J=4.7 Hz, 1H), 6.74 (s, 1H), 6.66 (d, J=8.3 Hz, 1H), 5.79 (br s, 1H), 3.89 (s, 3H), 3.33 (m, 1H), 3.27 (d, J=16.6 Hz, 1H), 3.18 (d, J=16.6 Hz, 1H), 3.14 (s, 3H), 3.06 (m, 1H), 2.87 (m, 2H), 2.68 (m, 1H), 2.67 (s, 3H), 2.31 (m, 1H), 1.91 (m, 1H); LC/MS (ESI+): 550.0 (M+H).

Example 838

(±)-(3R,4S)-1-(2-Fluoro-ethyl)-4-{3-methoxy-4-[7-(2-methoxy-phenyl)-pyrrolo[2,1-f][1,2,4]triazin-2-ylamino]-phenyl}-piperidin-3-ol Following the experimental procedure described in Example 833, (±)-(3R,4S)-4-{3-methoxy-4-[7-(2-methoxy-phenyl)-pyrrolo[2,1-f][1,2,4]triazin-2-ylamino]-phenyl}-piperidin-3-ol was converted to (±)-(3R,4S)-1-(2-fluoro-ethyl)-4-{3-methoxy-4-[7-(2-methoxy-phenyl)-pyrrolo[2,1-f][1,2,4]triazin-2-ylamino]-phenyl}-piperidin-3-ol as a yellow foam (24 mg, 57%). $^1$H-NMR (CDCl$_3$) δ 8.69 (s, 1H), 8.31 (d, J=8.3 Hz, 1H), 7.98 (d, J=7.6 Hz, 1H), 7.46 (s, 1H), 7.42 (m, 1H), 7.12 (m, 1H), 7.06 (d, J=8.3 Hz, 1H), 7.01 (d, J=4.6 Hz, 1H), 6.88 (s, 1H), 6.83 (d, J=4.6 Hz, 1H), 6.79 (d, J=8.4 Hz, 1H), 4.65 (m, 1H), 4.54 (m, 1H), 3.92 (br s, 1H), 3.90 (s, 3H), 3.84 (s, 3H), 3.09 (m, 2H), 2.81 (m, 1H), 2.74 (m, 1H), 2.62 (m, 1H), 2.43 (d, J=11.3 Hz, 1H), 2.29 (m, 1H), 2.25 (m, 1H), 1.85 (br s, 1OH), 1.69 (m, 1H); LC/MS (ESI+): 492.0 (M+H).

Example 839

(±)-2-43R,4S)-3-Hydroxy-4-{3-methoxy-4-[7-(2-methoxy-phenyl)-pyrrolo[2,1-f][1,2,4]triazin-2-ylamino]-phenyl}-piperidin-1-yl)-acetamide Following the experimental procedure described in Example 833, (±)-(3R,4S)-4-{3-methoxy-4-[7-(2-methoxy-phenyl)-pyrrolo[2,1-f][1,2,4]triazin-2-ylamino]-phenyl}-piperidin-3-ol was converted to (±)-2-((3R,4S)-3-hydroxy-4-{3-methoxy-4-[7-(2-methoxy-phenyl)-pyrrolo[2,1-f][1,2,4]triazin-2-ylamino]-phenyl}-piperidin-1-yl)-acetamide as a yellow foam (30 mg, 70%). $^1$H-NMR (CDCl$_3$) δ 8.69 (s, 1H), 8.34 (d, J=8.2 Hz, 1H), 7.98 (d, J=7.6 Hz, 1H), 7.47 (s, 1H), 7.43 (m, 1H), 7.26 (br s-overlapping with the solvent signal, 1H), 7.13 (m, 1H), 7.07 (d, J=8.3 Hz, 1H), 7.03 (d, J=4.6 Hz, 1H), 6.84 (d, J=4.6 Hz, 1H), 6.79 (s, 1H), 6.77 (d, J=8.6 Hz, 1H), 5.51 (br s, 1H), 3.94 (br s, 1H), 3.91 (s, 3H), 3.85 (s, 3H), 3.06 (m, 4H), 2.70 (m, 1H), 2.48 (d, J=11.5 Hz, 1H), 2.38 (m, 1H), 2.33 (m, 1H), 1.77 (br s, OH and water peak), 1.71 (m, 1H); LC/MS (ESI+): 503.0 (M+H).

Example 840

(±)-N-(2-{2-[4-((3S,4S)-3,4-Dihydroxy-piperidin-4-yl)-2-methoxy-phenylamino]-pyrrolo[2,1-f][1,2,4]triazin-7-yl}-phenyl)-N-methyl-methanesulfonamide Following the experimental procedures described in Example 761 and 787b), trifluoro-methanesulfonic acid 7-[2-(methanesulfonyl-methyl-amino)-phenyl]-pyrrolo[2,1-f][1,2,4]triazin-2-yl ester and (±)-(3S,4S)-4-(4-amino-3-methoxy-phenyl)-3,4-dihydroxy-piperidine-1-carboxylic acid tert-butyl ester were converted to (±)-N-(2-{2-[4-((3S,4S)-3,4-dihydroxy-piperidin-4-yl)-2-methoxy-phenylamino]-pyrrolo[2,1-f][1,2,4]triazin-7-yl}-phenyl)-N-methyl-methanesulfonamide as a yellow foam (200 mg, 50%). $^1$H-NMR (CDCl$_3$) δ 8.73 (s, 1H), 8.17 (d, J=8.4 Hz, 1H), 7.95 (m, 1H), 7.53 (m, 4H), 7.09 (s, 1H), 7.04 (d, J=4.7 Hz, 1H), 6.90 (s, 1H), 6.87 (d, J=4.7 Hz, 1H), 4.06 (dd, J=10.0; 4.8 Hz, 1H), 3.92 (s, 3H), 3.14 (s, 3H), 3.06 (m, 2H), 2.89 (m, 2H), 2.69 (s, 3H), 1.90 (m, 2H), 1.64 (br s, 2 OH; 1 NH, and water peak); LC/MS (ESI+): 539.0 (M+H).

Example 841

(±)-N-(2-{2-[4-((3R,4S)-3-Hydroxy-piperidin-4-yl)-2-methoxy-phenylamino]-pyrrolo[2,1-f][1,2,4]triazin-7-yl}-phenyl)-N-methyl-methanesulfonamide Following the experimental procedures described in Example 761 and then 787b), trifluoro-methanesulfonic acid 7-[2-(methanesulfonyl-methyl-amino)-phenyl]-pyrrolo[2,1-f][1,2,4]triazin-2-yl ester and (±)-(3R,4S)-4-(4-amino-3-methoxy-phenyl)-3-hydroxy-piperidine-1-carboxylic acid tert-butyl ester were converted to (±)-N-(2-{2-[4-((3R,4S)-3-hydroxy-piperidin-4-yl)-2-methoxy-phenylamino]-pyrrolo[2,1-f][1,2,4]triazin-7-yl}-phenyl)-N-methyl-methanesulfonamide as a yellow foam (250 mg, 50%). $^1$H-NMR (CDCl$_3$) δ 8.72 (s, 1H), 8.10 (d, J=8.3 Hz, 1H), 7.95 (m, 1H), 7.52 (m, 3H), 7.47 (s, 1H), 7.02 (d, J=4.7 Hz, 1H), 6.86 (d, J=4.7 Hz, 1H), 6.82 (s, 1H), 6.69 (d, J=8.4 Hz, 1H), 3.90 (s, 3H), 3.86 (br s, 1H), 3.23 (m, 2H), 3.13 (s, 3H), 2.89 (d, J=12.6 Hz, 1H), 2.75 (m, 2H), 2.68 (s, 3H), 2.01 (br s, NH, OH and water peak), 2.14 (m, 1H), 1.63 (m, 1H); LC/MS (ESI+): 522.9 (M+H).

Example 842

(±)-2-[(3R,4S)-3-Hydroxy-4-(4-{7-[2-(methanesulfonyl-methyl-amino)-phenyl]-pyrrolo[2,1-f][1,2,4]triazin-2-ylamino}-3-methoxy-phenyl)-piperidin-1-yl]-acetamide Following the experimental procedure described in Example 833, (±)-N-(2-{2-[4-((3R,4S)-3-hydroxy-piperidin-4-yl)-2-methoxy-phenylamino]-pyrrolo[2,1-f][1,2,4]triazin-7-yl}-phenyl)-N-methyl-methanesulfonamide was converted to (±)-2-[(3R,4S)-3-hydroxy-4-(4-{7-[2-(methanesulfonyl-methyl-amino)-phenyl]-pyrrolo[2,1-f][1,2,4]triazin-2-ylamino}-3-methoxy-phenyl)-piperidin-1-yl]-acetamide as a yellow foam (44 mg, 66%). $^1$H-NMR (CDCl$_3$) δ 8.71 (s, 1H), 8.11 (d, J=8.3 Hz, 1H), 7.95 (m, 1H), 7.52 (m, 3H), 7.48 (s, 1H), 7.24 (br s, 1H), 7.02 (d, J=4.6 Hz, 1H), 6.86 (d, J=4.6 Hz, 1H), 6.79 (s, 1H), 6.69 (d, J=8.3 Hz, 1H), 5.60 (br s, 1H), 3.92 (br s, 1H), 3.89 (s, 3H), 3.14 (s, 3H), 3.04 (m, 4H), 2.67 (br overlapped* s, 1H), 2.67 (overlapped* s, 3H), 2.47 (d, J=11.3 Hz, 1H), 2.35 (m, 1H), 2.27 (m, 1H), 1.83 (br s, 1H), 1.68 (m, 1H); LC/MS (ESI+): 580.0 (M+H).

Example 843

(±)-N-[2-(2-{4-[(3R,4S)-1-(2-Fluoro-ethyl)-3-hydroxy-piperidin-4-yl]-2-methoxy-phenylamino}-pyrrolo[2,1-f][1,2,4]triazin-7-yl)-phenyl]-N-methyl-methanesulfonamide Following the experimental procedure described in Example 833, (±)-N-(2-{2-[4-((3R,4S)-3-hydroxy-piperidin-4-yl)-2-methoxy-phenylamino]-pyrrolo[2,1-f][1,2,4]triazin-7-yl}-phenyl)-N-methyl-methanesulfonamide was converted to (±)-N-[2-(2-{4-[(3R,4S)-1-(2-Fluoro-ethyl)-3-hydroxy-piperidin-4-yl]-2-methoxy-phenylamino}-pyrrolo[2,1-f][1,2,4]triazin-7-yl)-phenyl]-N-methyl-methanesulfonamide as a yellow foam (43 mg, 66%). $^1$H-NMR (CDCl$_3$) δ 8.72 (s, 1H), 8.09 (d, J=8.3 Hz, 1H), 7.95 (m, 1H), 7.51 (m, 3H), 7.47 (s, 1H), 7.02 (d, J=4.7 Hz, 1H), 6.87 (br s, 1H), 6.85 (d, J=4.7 Hz, 1H), 6.71 (d, J=8.3 Hz, 1H), 4.65 (m, 1H), 4.53 (m, 1H), 3.89 (br overlapped* s, 1H), 3.89 (overlapped* s, 3H), 3.12 (s, 3H), 3.09 (m, 2H), 2.81 (m, 1H), 2.75 (m, 1H), 2.68 (s, 3H), 2.62 (br s, 1H), 2.59 (s, 1H), 2.44 (d, J=11.2 Hz, 1H), 2.29 (m, 1H), 2.23 (m, 1H), 1.70 (br s, 1H); LC/MS (ESI+): 569.0 (M+H).

Example 844

(±)-2-[(3S,4S)-3,4-Dihydroxy-4-(4-{7-[2-(methanesulfonyl-methyl-amino)-phenyl]-pyrrolo[2,1-f][1,2,4]triazin-2-ylamino}-3-methoxy-phenyl)-piperidin-1-yl]-acetamide Following the experimental procedure described in Example 833, (±)-N-(2-{2-[4-((3S,4S)-3,4-dihydroxy-piperidin-4-yl)-2-methoxy-phenylamino]-pyrrolo[2,1-f][1,2,4]triazin-7-yl}-phenyl)-N-methyl-methanesulfonamide was converted to (±)-2-[(3S,4S)-3,4-dihydroxy-4-(4-{7-[2-(methanesulfonyl-methyl-amino)-phenyl]-pyrrolo[2,1-f][1,2,4]triazin-2-ylamino}-3-methoxy-phenyl)-piperidin-1-yl]-acetamide as a yellow foam (35 mg, 53%). $^1$H-NMR (CDCl$_3$) δ 8.71 (s, 1H), 8.17 (d, J=8.4 Hz, 1H), 7.96 (m, 1H), 7.53 (m, 4H), 7.06 (s, 1H), 7.02 (d, J=4.6 Hz, 1H), 6.96 (br s, 1H), 5.47 (br s, 1H), 4.13 (dd, J=10.2; 4.8 Hz, 1H), 3.92 (s, 3H), 3.16 (s, 3H), 3.10 (s, 2H), 2.92 (m, 1H), 2.67 (s, 3H), 2.64 (m, 3H), 2.54 (m, 1H), 1.98 (br s, 1H), 1.95 (m, 1H), 1.87 (m, 1H), 1.60 (br s, 2 OH and water peak); LC/MS (ESI+): 596.0 (M+H).

Example 845

(±)-N-[2-(2-{4-[(3S,4S)-1-(2-Fluoro-ethyl)-3,4-dihydroxy-piperidin-4-yl]-2-methoxy-phenylamino}-pyrrolo[2,1-f][1,2,4]triazin-7-yl)-phenyl]-N-methyl-methanesulfonamide Following the experimental procedure described in Example 833, (±)-N-(2-{2-[4-((3S,4S)-3,4-dihydroxy-piperidin-4-yl)-2-methoxy-phenylamino]-pyrrolo[2,1-f][1,2,4]triazin-7-yl}-phenyl)-N-methyl-methanesulfonamide was converted to (±)-N-[2-(2-{4-[(3S,4S)-1-(2-fluoro-ethyl)-3,4-dihydroxy-piperidin-4-yl]-2-methoxy-phenylamino}-pyrrolo[2,1-f][1,2,4]triazin-7-yl)-phenyl]-N-methyl-methanesulfonamide as a yellow foam (45 mg, 67%). $^1$H-NMR (CDCl$_3$) δ 8.67 (s, 1H), 8.15 (d, J=8.5 Hz, 1H), 7.93 (m, 1H), 7.50 (m, 4H), 7.07 (s, 1H), 7.02 (d, J=4.6 Hz, 1H), 6.87 (d, J=8.6 Hz, 1H), 6.85 (d, J=4.6 Hz, 1H), 4.66 (m, 1H), 4.54 (m, 1H), 4.16 (dd, J=10.0; 4.8 Hz, 1H), 3.88 (s, 3H), 3.12 (s, 3H), 2.97 (m, 1H), 2.83 (m, 1H), 2.76 (m, 3H), 2.68 (s, 3H), 2.53 (m, 1H), 2.42 (m, 1H), 2.16 (br s, 1H), 2.03 (m, 1H), 1.84 (m, 1H); LC/MS (ESI+): 585.0 (M+H).

Example 846

(±)-N-[2-(2-{4-[(3S,4S)-3,4-Dihydroxy-1-(2-methoxy-ethyl)-piperidin-4-yl]-2-methoxy-phenylamino}-pyrrolo[2,1-f][1,2,4]triazin-7-yl)-phenyl]-N-methyl-methanesulfonamide Following the experimental procedure described in Example 833, (±)-N-(2-{2-[4-((3S,4S)-3,4-dihydroxy-piperidin-4-yl)-2-methoxy-phenylamino]-pyrrolo[2,1-f][1,2,4]triazin-7-yl}-phenyl)-N-methyl-methanesulfonamide was converted to (±)-N-[2-(2-{4-[(3S,4S)-3,4-dihydroxy-1-(2-methoxy-ethyl)-piperidin-4-yl]-2-methoxy-phenylamino}-pyrrolo[2,1-f][1,2,4]triazin-7-yl)-phenyl]-N-methyl-methanesulfonamide as a yellow foam (47 mg, 61%). $^1$H-NMR (CDCl$_3$) δ 8.67 (s, 1H), 8.14 (d, J=8.4 Hz, 1H), 7.93 (m, 1H), 7.50 (m, 4H), 7.07 (s, 1H), 7.02 (d, J=4.6 Hz, 1H), 6.88 (d, J=8.5 Hz, 1H), 6.85 (d, J=4.6 Hz, 1H), 4.18 (dd, J=10.0; 4.8 Hz, 1H), 3.88 (s, 3H), 3.55 (m, 2H), 3.38 (s, 3H), 3.11 (s, 3H), 3.98 (m, 1H), 2.69 (m, 3H), 2.68 (s, 3H), 2.44 (m, 1H), 2.33 (m, 1H), 2.30 (br s, 2H), 2.06 (m, 1H), 1.82 (m, 1H); LC/MS (ESI+): 597.0 (M+H).

Example 847

(±)-N-[2-(2-{4-[(3R,4S)-3-Hydroxy-1-(2-hydroxyethyl)-piperidin-4-yl]-2-methoxy-phenylamino}-pyrrolo[2,1-f][1,2,4]triazin-7-yl)-phenyl]-N-methyl-methanesulfonamide Following the experimental procedure described in Example 787c), (±)-N-(2-{2-[4-((3R,4S)-3-hydroxy-piperidin-4-yl)-2-methoxy-phenylamino]-pyrrolo[2,1-f][1,2,4]triazin-7-yl}-phenyl)-N-methyl-methanesulfonamide was converted to (±)-N-[2-(2-{4-[(3R,4S)-3-hydroxy-1-(2-hydroxyethyl)-piperidin-4-yl]-2-methoxy-phenylamino}-pyrrolo[2,1-f][1,2,4]triazin-7-yl)-phenyl]-N-methyl-methanesulfonamide as a yellow foam (33 mg, 44%). $^1$H-NMR (CDCl$_3$) δ 8.72 (br s, 1H), 8.09 (d, J=8.3 Hz, 1H), 7.94 (m, 1H), 7.52 (m, 3H), 7.47 (s, 1H), 7.02 (d, J=4.7 Hz, 1H), 6.85 (d, J=4.7 Hz, 1H), 6.84 (s, 1H), 6.69 (d, J=8.3 Hz, 1H), 3.93 (br s, 1H), 3.89 (s, 3H), 3.69 (m, 2H), 3.13 (m, 1H), 3.12 (s, 3H), 3.09 (m, 1H), 2.67 (s, 3H), 2.66 (m, 3H), 2.37 (d, J=12.0 Hz, 1H), 2.20 (m, 4H), 1.69 (m, 1H); LC/MS (ESI+): 567.0 (M+H).

Example 848

(±)-(3R,4S)-1-(2-Hydroxy-ethyl)-4-{3-methoxy-4-[7-(2-methoxy-phenyl)-pyrrolo[2,1-f][1,2,4]triazin-2-ylamino]-phenyl}-piperidin-3-ol Following the experimental procedure described in Example 787c), (±)-(3R,4S)-4-{3-methoxy-4-[7-(2-methoxy-phenyl)-pyrrolo[2,1-f][1,2,4]triazin-2-ylamino]-phenyl}-piperidin-3-ol was converted to (±)-(3R,4S)-1-(2-hydroxy-ethyl)-4-{3-methoxy-4-[7-(2-methoxy-phenyl)-pyrrolo[2,1-f][1,2,4]triazin-2-ylamino]-phenyl}-piperidin-3-ol as a yellow solid (106 mg, 69%). MP: 88-96° C.; $^1$H-NMR (CDCl$_3$) δ 8.67 (s, 1H), 8.30 (d, J=8.3 Hz, 1H), 7.98 (d, J=7.3 Hz, 1H), 7.46 (s, 1H), 7.42 (m, 1H), 7.12 (m, 1H), 7.06 (d, J=8.3 Hz, 1H), 7.01 (d, J=4.7 Hz, 1H), 6.84 (s, 1H), 6.82 (d, J=4.7 Hz, 1H), 6.77 (d, J=8.3 Hz, 1H), 3.93 (br s, 1H), 3.88 (s, 3H), 3.83 (s, 3H), 3.68 (m, 2H), 3.13 (m, 1H), 3.07 (m, 1H), 2.60 (m, 3H), 2.41 (br s, 2H), 2.35 (d, J=11.3 Hz, 1H), 2.23 (m, 2H), 1.68 (m, 1H); LC/MS (ESI+): 490.17 (M+H).

Example 849

(±)-2-43S,4S)-3,4-Dihydroxy-4-{3-methoxy-4-[7-(2-methoxy-phenyl)-pyrrolo[2,1-f][1,2,4]triazin-2-ylamino]-phenyl}-piperidin-1-yl)-acetamide Following the experimental procedure described in Example 833, (±)-(3S,4S)-4-{3-Methoxy-4-[7-(2-methoxy-phenyl)-pyrrolo[2,1-f][1,2,4]triazin-2-ylamino]-phenyl}-piperidine-3,4-diol was converted to (±)-2-43S,4S)-3,4-dihydroxy-4-{3-methoxy-4-[7-(2-methoxy-phenyl)-pyrrolo[2,1-f][1,2,4]triazin-2-ylamino]-phenyl}-piperidin-1-yl)-acetamide as a yellow solid (80 mg, 71%). MP: 126-133° C.; $^1$H-NMR (CDCl$_3$) δ 8.61 (s, 1H), 8.34 (d, J=8.4 Hz, 1H), 7.96 (d, J=7.6 Hz, 1H), 7.49 (s, 1H), 7.44 (m, 1H), 7.13 (m, 1H), 7.07 (d, J=8.4 Hz, 1H), 7.03 (s, 1H), 7.02 (d, J=5.0 Hz, 1H), 6.96 (br s, 1H), 6.92 (d, J=8.5 Hz, 1H), 6.82 (d, J=4.6 Hz, 1H), 5.66 (br s, 1H), 4.10 (dd, J=10.2; 4.9 Hz, 1H), 3.89 (s, 3H), 3.84 (s, 3H), 3.07 (m, 2H), 2.89 (m, 1H), 2.83 (br s, 1H), 2.64 (m, 2H), 2.53 (m, 1H), 1.93 (m, 1H), 1.87 (m, 1H), 1.84 (br s, 1H); LC/MS (ESI+): 519.14 (M+H).

Example 850

(6-Methoxy-2-oxetan-3-yl-2,3-dihydro-1H-isoindol-5-yl)-[7-(2-methoxy-phenyl)-pyrrolo[2,1-f][1,2,4]triazin-2-yl]-amine 7-(2-Methoxy-phenyl)-pyrrolo[2,1-f][1,2,4]triazin-2-ol (50.00 mg, 0.207) was dissolved in N,N-Dimethylformamide (4.0 mL) at 0° C. and sodium hydride (60% dispersion in mineral oil; 10.4 mg, 0.259 mmol) was added and the reaction was let to stir for 30 minutes. Then, N-phenylbis(trifluoromethanesulphonimide) (81.4 mg, 0.228 mmol) was added and the reaction was allowed to warm to room temperature. After 100% conversion to the triflate, 6-methoxy-2-oxetan-3-yl-2,3-dihydro-1H-isoindol-5-ylamine (57.1 mg, 0.259 mmol 1) was added the reaction was allowed to stir at room temperature. The reaction mixture was partitioned between dichloromethane and saturated aqueous Na$_2$CO$_3$. The aqueous layer was extracted with dichloromethane, the combined organics were dried over sodium sulfate and filtered. The solvent was evaporated under reduced pressure and the product was isolated by preparative reverse phase hplc (Gilson) as a brown foam (11 mg, 12%). $^1$H-NMR (CDCl$_3$) δ 8.70 (s, 1H), 8.27 (s, 1H), 7.96 (d, J=7.2 Hz, 1H), 7.51 (br s, 1H), 7.42 (m, 1H), 7.08 (m, 2H), 7.02 (d, J=4.6 Hz, 1H), 6.84 (d, J=4.6 Hz, 1H) 6.74 (br s, 1H), 4.78 (m, 4H), 4.09 (m, 1H), 3.95 (br s, 2H), 3.89 (s, 3H), 3.85 (br s, 2H), 3.83 (s, 3H); LC/MS (ESI+): 444.0 (M+H).

Example 851

(4-Methoxy-2-oxetan-3-yl-2,3-dihydro-1H-isoindol-5-yl)-[7-(2-methoxy-phenyl)-pyrrolo[2,1-f][1,2,4]triazin-2-yl]-amine Following the experimental procedure described in Example 850, 7-(2-methoxy-phenyl)-pyrrolo[2,1-f][1,2,4]triazin-2-ol and 4-methoxy-2-oxetan-3-yl-2,3-dihydro-1H-isoindol-5-ylamine were converted to (4-methoxy-2-oxetan- 3-yl-2,3-dihydro-1H-isoindol-5-yl)-[7-(2-methoxy-phenyl)-pyrrolo[2,1-f][1,2,4]triazin-2-yl]-amine as a brown foam (11 mg, 12%). $^1$H-NMR (CDCl$_3$) δ 8.71 (s, 1H), 8.30 (d, J=8.2 Hz, 1H), 7.97 (d, J=7.6 Hz, 1H), 7.44 (s, 1H), 7.42 (m, 1H), 7.12 (m, 1H), 7.07 (d, J=8.3 Hz, 1H), 7.03 (d, J=4.6 Hz, 1H), 6.85 (m, 2H), 4.77 (m, 4H), 4.09 (s, 2H), 4.06 (m, 1H), 3.90 (s, 2H), 3.87 (s, 3H), 3.84 (s, 3H); LC/MS (ESI+): 444.1 (M+H).

Example 852

[6-Methoxy-2-(1-methyl-piperidin-4-yl)-2,3-dihydro-1H-isoindol-5-yl]-[7-(2-methoxy-phenyl)-pyrrolo[2,1-f][1,2,4]triazin-2-yl]-amine Following the experimental procedure described in Example 850, 7-(2-methoxy-phenyl)-pyrrolo[2,1-f][1,2,4]triazin-2-ol and 6-methoxy-2-(1-methyl-piperidin-4-yl)-2,3-dihydro-1H-isoindol-5-ylamine were converted to [6-methoxy-2-(1-methyl-piperidin-4-yl)-2,3-dihydro-1H-isoindol-5-yl]-[7-(2-methoxy-phenyl)-pyrrolo[2,1-f][1,2,4]triazin-2-yl]-amine as a yellow foam (26 mg, 26%). $^1$H-NMR (CDCl$_3$) δ 8.69 (s, 1H), 8.26 (s, 1H), 7.96 (d, J=7.3 Hz, 1H), 7.50 (s, 1H), 7.43 (m, 1H), 7.08 (m, 2H), 7.01 (d, J=4.6 Hz, 1H), 6.83 (d, J=4.6 Hz, 1H), 6.73 (s, 1H), 3.93 (s, 2H), 3.87 (s, 3H), 3.85 (s, 2H), 3.83 (s, 3H), 2.90 (m, 2H), 2.42 (m, 1H), 2.31 (s, 3H), 2.10 (m, 2H), 1.95 (m, 2H), 1.70 (m, 2H); LC/MS (ESI+): 485.1 (M+H).

Example 853

[4-Methoxy-2-(1-methyl-piperidin-4-yl)-2,3-dihydro-1H-isoindol-5-yl]-[7-(2-methoxy-phenyl)-pyrrolo[2,1-f][1,2,4]triazin-2-yl]-amine Following the experimental procedure described in Example 850, 7-(2-methoxy-phenyl)-pyrrolo[2,1-f][1,2,4]triazin-2-ol and 4-methoxy-2-(1-methyl-piperidin-4-yl)-2,3-dihydro-1H-isoindol-5-ylamine were converted to [4-methoxy-2-(1-methyl-piperidin-4-yl)-2,3-dihydro-1H-isoindol-5-yl]-[7-(2-methoxy-phenyl)-pyrrolo[2,1-f][1,2,4]triazin-2-yl]-amine as a yellow foam (30 mg, 30%). $^1$H-NMR (CDCl$_3$) δ 8.70 (s, 1H), 8.27 (d, J=8.2 Hz, 1H), 7.96 (d, J=7.6 Hz, 1H), 7.44 (s, 1H), 7.40 (m, 1H), 7.11 (m, 1H), 7.06 (d, J=8.3 Hz, 1H), 7.02 (d, J=4.6 Hz, 1H), 6.84 (d, J=4.6 Hz, 1H), 6.83 (m, 1H), 4.09 (s, 2H), 3.90 (s, 2H), 3.87 (s, 3H), 3.83 (s, 3H), 2.88 (m, 2H), 2.41 (m, 1H), 2.29 (s, 3H), 2.06 (m, 2H), 1.96 (m, 2H), 1.68 (m, 2H); LC/MS (ESI+): 485.1 (M+H).

Example 854

2-(4-{3-Methoxy-4-[7-(2-pyrazol-1-yl-phenyl)-pyrrolo[2,1-f][1,2,4]triazin-2-ylamino]-phenyl}-piperidin-1-yl)-acetamide To a solution of tetrakis(triphenylphosphine)palladium(0) (126.00 mg, 0.109 mmol) were in 1,4-dioxane (1.02 mL) were added 2-{4-[4-(7-bromo-pyrrolo[2,1-f][1,2,4]triazin-2-ylamino)-3-methoxy-phenyl]-piperidin-1-yl}-acetamide (100.00 mg, 0.218 mmol), 1-[2-(4,4,5,5-tetramethyl-[1,3,2]dioxaborolan-2-yl)-phenyl]-1H-pyrazole (0.082 g, 0.305 mmol), N,N-dimethylformamide (1.58 mL) and a 1.50 M solution of sodium carbonate in water (1.23 mL, 1.85 mmol). The reaction was heated overnight at 80° C. under Argon. The solvents were removed under reduced pressure and the residue was partitioned between ethyl acetate and water. The organic phase was with water and brine, dried (MgSO$_4$) and filtered, and the solvent was evaporated under reduced pressure. The product was isolated by flash chromatography (Isco, silicagel, gradient EtOAc/Hexanes) to provide a yellow foam (41 mg, 36%). $^1$H-NMR (CDCl$_3$) δ 8.66 (s, 1H), 8.17 (d, J=8.2 Hz, 1H), 8.08 (m, 1H), 7.69 (m, 1H), 7.60 (s, 1H), 7.56 (m, 2H), 7.42 (s, 1H), 7.17 (s, 1H), 7.13 (br s, 1H), 6.73 (m, 2H), 6.68 (d, J=4.7 Hz, 1H), 6.21 (m, 2H), 5.67 (br s, 1H), 3.91 (s, 3H), 3.04 (s, 2H), 3.01 (m, 2H), 2.48 (m, 1H), 2.29 (m, 2H), 1.80 (m, 4H); LC/MS (ESI+): 523.1 (M+H).

Example 855

(±)-(3S,4S)-4-{3-Methoxy-4-[7-(2-methoxy-phenyl)-pyrrolo[2,1-f][1,2,4]triazin-2-ylamino]-phenyl}-piperidin-3-ol Following the experimental procedure described in Examples 850, and then 787b), but using N,N-diisopropylethylamine instead of sodium hydride, 7-(2-methoxy-phenyl)-pyrrolo[2,1-f][1,2,4]triazin-2-ol and (±)-(3S,4S)-4-(4-amino-3-methoxy-phenyl)-3-hydroxy-piperidine-1-carboxylic acid tert-butyl ester were converted to (±)-(3S,4S)-4-{3-methoxy-4-[7-(2-methoxy-phenyl)-pyrrolo[2,1-f][1,2,4]triazin-2-ylamino]-phenyl}-piperidin-3-ol as a yellow foam (54 mg, 49%). $^1$H-NMR (CDCl$_3$) δ 8.69 (s, 1H), 8.35 (d, J=8.0 Hz, 1H), 7.96 (d, J=3.6 Hz, 1H), 7.46 (s, 1H), 7.44 (m, 1H), 7.12 (m, 1H), 7.07 (d, J=8.3 Hz, 1H), 7.02 (d, J=4.6 Hz, 1H), 6.84 (d, J=4.6 Hz, 1H), 6.79 (d, J=8.3 Hz, 1H), 5.78 (s, 1H), 3.90 (s, 3H), 3.84 (s, 3H), 3.69 (m, 1H), 3.37 (dd, J=11.8; 4.0 Hz, 1H), 3.10 (d, J=11.8 Hz, 1H), 2.68 (m, 1H), 2.56 (m, 1H), 2.45 (m, 1H), 1.85 (m, 1H), 1.75 (m, 1H), 1.64 (br s, OH, NH and water peak); LC/MS (ESI+): 446.1 (M+H).

Example 856

(±)-(3S,4S)-1-(2-Hydroxy-ethyl)-4-{3-methoxy-4-[7-(2-methoxy-phenyl)-pyrrolo[2,1-f][1,2,4]triazin-2-ylamino]-phenyl}-piperidin-3-ol Following the experimental procedure described in Example 787c), (±)-(3S,4S)-4-{3-methoxy-4-[7-(2-methoxy-phenyl)-pyrrolo[2,1-f][1,2,4]triazin-2-ylamino]-phenyl}-piperidin-3-ol was converted to (±)-(3S,4S)-1-(2-hydroxy-ethyl)-4-{3-methoxy-4-[7-(2-methoxy-phenyl)-pyrrolo[2,1-f][1,2,4]triazin-2-ylamino]-phenyl}-piperidin-3-ol as a yellow foam (36 mg, 61%). $^1$H-NMR (CDCl$_3$) δ 8.68 (s, 1H), 8.34 (d, J=8.0 Hz, 1H), 7.96 (d, J=7.6 Hz, 1H), 7.47 (s, 1H), 7.44 (m, 1H), 7.13 (m, 1H), 7.07 (8.3 Hz, 1H), 7.02 (d, J=3.2 Hz, 1H), 6.84 (d, J=3.2 Hz, 1H), 6.77 (d, J=8.3 Hz, 1H), 6.76 (s, 1H), 3.90 (s, 3H), 3.84 (s, 3H), 3.77 (m, 1H), 3.74 (m, 2H), 3.66 (m, 2H), 3.25 (br d, J=8.0 Hz, 1H), 2.97 (d, J=10.8 Hz, 1H), 2.63 (m, 2H), 2.36 (m, 1H), 2.17 (m, 1H), 2.07 (m, 1H), 1.85 (br s, 2OH's and water peak); LC/MS (ESI+): 490.0 (M+H).

Example 857

2-(4-{3-Methoxy-4-[7-(3-methoxy-pyridin-4-yl)-pyrrolo[2,1-f][1,2,4]triazin-2-ylamino]-phenyl}-piperidin-1-yl)-acetamide Following the experimental procedure described in Example 854, 2-{4-[4-(7-bromo-pyrrolo[2,1-f][1,2,4]triazin-2-ylamino)-3-methoxy-phenyl]-piperidin-1-yl}-acetamide was converted to 2-(4-{3-methoxy-4-[7-(3-methoxy-pyridin-4-yl)-pyrrolo[2,1-f][1,2,4]triazin-2-ylamino]-phenyl}-piperidin-1-yl)-acetamide as a yellow foam (30 mg, 57%). ¹H-NMR (CDCl₃) δ 8.75 (s, 1H), 8.48 (s, 1H), 8.43 (d, J=4.0 Hz, 1H), 8.27 (d, J=8.2 Hz, 1H), 8.21 (d, J=4.0 Hz, 1H), 7.49 (s, 1H), 7.20 (d, J=4.0 Hz, 1H), 7.19 (br s, 1H), 6.84 (d, J=3.8 Hz, 1H), 6.79 (d, J=8.3 Hz, 1H), 6.76 (s, 1H), 5.56 (br s, 1H), 3.99 (s, 3H), 3.92 (s, 3H), 3.05 (s, 2H), 3.02 (m, 2H), 2.49 (m, 1H), 2.31 (m, 2H), 1.79 (m, 4H); LC/MS (ESI+): 488.0 (M+H).

Example 858

(±)-[4-(1,3-Dimethyl-piperidin-4-yl)-2-methoxy-phenyl]-[7-(2-methoxy-phenyl)-pyrrolo[2,1-f][1,2,4]triazin-2-yl]-amine Following the experimental procedure described in Example 850, except using N,N-diisopropylethylamine instead of sodium hydride, 7-(2-methoxy-phenyl)-pyrrolo[2,1-f][1,2,4]triazin-2-ol and (±)-4-(1,3-dimethyl-piperidin-4-yl)-2-methoxy-phenylamine were converted to (±)-[4-(1,3-dimethyl-piperidin-4-yl)-2-methoxy-phenyl]-[7-(2-methoxy-phenyl)-pyrrolo[2,1-f][1,2,4]triazin-2-yl]-amine as a yellow foam (35 mg, 37%). ¹H-NMR (CDCl₃) δ 8.69 (s, 1H), 8.28 (d, J=8.1 Hz, 1H), 8.00 (d, J=7.6 Hz, 1H), 7.44 (m, 2H), 7.13 (m, 1H), 7.06 (d, J=8.3 Hz, 1H), 7.02 (d, J=4.5 Hz, 1H), 6.83 (d, J=4.5 Hz, 1H), 6.68 (s, 1H), 6.67 (d, J=8.3 Hz, 1H), 3.89 (s, 3H), 3.84 (s, 3H), 3.00 (m, 1H), 2.76 (m, 2H), 2.27 (s, 3H), 2.14 (m, 1H), 1.99 (m, 2H), 1.81 (br s, 1H), 1.65 (m, 1H), 0.82 (d, J=7.8 Hz, 3H); LC/MS (ESI+): 458.0 (M+H).

Example 859

(±)-[2-Methoxy-4-(3-methoxy-1-methyl-piperidin-4-yl)-phenyl]-[7-(2-methoxy-phenyl)-pyrrolo[2,1-f][1,2,4]triazin-2-yl]-amine Following the experimental procedure described in Example 858, 7-(2-methoxy-phenyl)-pyrrolo[2,1-f][1,2,4]triazin-2-ol and (±)-4-(1,3-dimethyl-piperidin-4-yl)-2-methoxy-phenylamine were converted to (±)-[2-methoxy-4-(3-methoxy-1-methyl-piperidin-4-yl)-phenyl]-[7-(2-methoxy-phenyl)-pyrrolo[2,1-f][1,2,4]triazin-2-yl]-amine as a yellow foam (7.5 mg, 6%). ¹H-NMR (CDCl₃) δ 8.69 (s, 1H), 8.29 (d, J=8.1 Hz, 1H), 8.00 (d, J=7.6 Hz, 1H), 7.46 (s, 1H), 7.42 (m, 1H), 7.12 (m, 1H), 7.07 (d, J=8.2 Hz, 1H), 7.02 (d, J=3.0 Hz, 1H), 6.94 (s, 1H), 6.82 (m, 2H), 3.89 (s, 3H), 3.84 (s, 3H), 3.36 (br s, 1H), 3.17 (m, 1H), 3.16 (s, 3H), 3.02 (m, 1H), 2.56 (m, 2H), 2.33 (m, 4H), 2.08 (m, 1H), 1.62 (m, 1H); LC/MS (ESI+): 474.1 (M+H).

Example 860

(±)-2-(3-{3-Methoxy-4-[7-(2-methoxy-phenyl)-pyrrolo[2,1-f][1,2,4]triazin-2-ylamino]-phenyl}-piperidin-1-yl)-acetamide Following the experimental procedure described in Example 858, 7-(2-methoxy-phenyl)-pyrrolo[2,1-f][1,2,4]triazin-2-ol and (±)-2-[3-(4-amino-3-methoxy-phenyl)-piperidin-1-yl]-acetamide were converted to (±)-2-(3-{3-methoxy-4-[7-(2-methoxy-phenyl)-pyrrolo[2,1-f][1,2,4]triazin-2-ylamino]-phenyl}-piperidin-1-yl)-acetamide as a yellow foam (65 mg, 54%). ¹H-NMR (CDCl₃) δ 8.69 (s, 1H), 8.29 (d, J=8.2 Hz, 1H), 7.98 (d, J=7.6 Hz, 1H), 7.45 (m, 1H), 7.43 (m, 1H), 7.13 (m, 2H), 7.08 (d, J=8.3 Hz, 1H), 7.02 (d, J=4.6 Hz, 1H), 6.83 (d, J=4.6 Hz, 1H), 6.70 (br s, 2H), 5.64 (br s, 1H), 3.90 (s, 3H), 3.84 (s, 3H), 3.03 (s, 2H), 2.95 (m, 2H), 2.75 (m, 1H), 2.21 (m, 2H), 1.93 (m, 1H), 1.74 (m, 2H), 1.44 (m, 1H); LC/MS (ESI+): 487.0 (M+H).

Example 861

(±)-2-[3-(4-{7-[2-(Methanesulfonyl-methyl-amino)-phenyl]-pyrrolo[2,1-f][1,2,4]triazin-2-ylamino}-3-methoxy-phenyl)-piperidin-1-yl]-acetamide Following the experimental procedure described in Example 858, trifluoro-methanesulfonic acid 7-[2-(methanesulfonyl-methyl-amino)-phenyl]-pyrrolo[2,1-f][1,2,4]triazin-2-yl ester and (±)-2-[3-(4-amino-3-methoxy-phenyl)-piperidin-1-yl]-acetamide were converted to (±)-2-[3-(4-{7-[2-(methanesulfonyl-methyl-amino)-phenyl]-pyrrolo[2,1-f][1,2,4]triazin-2-ylamino}-3-methoxy-phenyl)-piperidin-1-yl]-acetamide as a yellow foam (41 mg, 29%). ¹H-NMR (CDCl₃) δ 8.72 (s, 1H), 8.07 (d, J=8.2 Hz, 1H), 7.94 (br s, 1H), 7.53 (br s, 3H), 7.46 (s, 1H), 7.11 (br s, 1H), 7.02 (d, J=3.8 Hz, 1H), 6.87 (br s, 1H), 6.70 (s, 1H), 6.62 (d, J=8.3 Hz, 1H), 5.57 (br s, 1H), 3.90 (s, 3H), 3.13 (s, 3H), 3.03 (s, 2H), 2.94 (m, 2H), 2.74 (m, 1H), 2.67 (s, 3H), 2.20 (m, 2H), 1.93 (m, 1H), 1.82 (m, 1H), 1.69 (m, 1H), 1.44 (m, 1H); LC/MS (ESI+): 564.0 (M+H).

Example 862

(±)-Azetidin-2-yl-(4-{3-methoxy-4-[7-(2-methoxy-phenyl)-pyrrolo[2,1-f][1,2,4]triazin-2-ylamino]-phenyl}-piperidin-1-yl)-methanone Following the experimental procedure described in Example 821, [7-(2-methoxy-phenyl)-pyrrolo[2,1-f][1,2,4]triazin-2-yl]-(2-methoxy-4-piperidin-4-yl-phenyl)-amine was converted to (±)-azetidin-2-yl-(4-{3-methoxy-4-[7-(2-methoxy-phenyl)-pyrrolo[2,1-f][1,2,4]triazin-2-ylamino]-phenyl}-piperidin-1-yl)-methanone as a yellow solid (38 mg, 51%). MP: 103-112° C.; ¹H-NMR (CDCl₃) δ 8.69 (s, 1H), 8.30 (m, 1H), 7.98 (m, 1H), 7.44 (m, 2H), 7.13 (m, 1H), 7.07 (d, J=8.3 Hz, 1H), 7.03 (m, 1H), 6.84 (d, J=4.6 Hz, 1H), 6.67 (m, 2H), 4.80 (m, 1H), 4.39 (m, 1H), 3.90 (s, 3H), 3.89* (s, 3H. amide rotamer), 3.84 (s, 3H), 3.68 (m, 1H), 3.56 (m, 1H), 3.45 (m, 1H), 3.07 (m, 1H), 2.88 (m, 1H), 2.70 (m, 2H), 2.32 (m, 2H), 1.91 (m, 2H), 1.63 (m, 2H); LC/MS (ESI+): 513.0 (M+H).

Example 863

(±)-N-[2-(2-{4-[1-(Azetidine-2-carbonyl)-piperidin-4-yl]-2-methoxy-phenylamino}-pyrrolo[2,1-f][1,2,4]triazin-7-yl)-phenyl]-N-methyl-methanesulfonamide Following the experimental procedure described in Example 821, N-{2-[2-(2-methoxy-4-piperidin-4-yl-phenylamino)-pyrrolo[2,1-f][1,2,4]triazin-7-yl]-phenyl}-N-methyl-methanesulfonamide was converted to (±)-N-[2-(2-{4-[1-(azetidine-2-carbonyl)-piperidin-4-yl]-2-methoxy-phenylamino}-pyrrolo[2,1-f][1,2,4]triazin-7-yl)-phenyl]-N-methyl-methanesulfonamide as a yellow solid (33 mg, 47%). MP: 111-116° C.; ¹H-NMR (CDCl₃) δ 8.72 (s, 1H), 8.08 (m, 1H), 7.95 (m, 1H), 7.52 (m, 3H), 7.46 (s, 1H), 7.03 (d, J=3.9 Hz, 1H), 6.86 (d, J=4.6 Hz, 1H), 6.68 (m, 1H), 6.60 (m, 1H), 4.78 (d, J=13.2 Hz, 1H), 4.38 (m, 1H), 3.90 (s, 3H), 3.89* (s, 3H, amide rotamer), 3.68 (m, 1H), 3.55 (m, 2H), 3.45 (m, 1H), 3.13 (s, 3H), 3.12* (s, 3H, amide rotamer), 3.05 (m, 1H), 2.86 (m, 1H), 2.67 (s, 3H), 2.65*(s, 3H, amide rotamer), 2.32 (m, 3H), 1.88 (m, 2H), 1.60 (m, 2H); LC/MS (ESI+): 590.0 (M+H).

Example 864

2-{5-Methoxy-6-[7-(2-methoxy-phenyl)-pyrrolo[2,1-f][1,2,4]triazin-2-ylamino]-1,3-dihydro-isoindol-2-yl}-acetamide Following the experimental procedure described in Example 761, trifluoro-methanesulfonic acid 7-(2-methoxy-phenyl)-pyrrolo[2,1-f][1,2,4]triazin-2-yl ester and 2-(5-amino-6-methoxy-1,3-dihydro-isoindol-2-yl)-acetamide were converted to 2-{5-methoxy-6-[7-(2-methoxy-phenyl)-pyrrolo[2,1-f][1,2,4]triazin-2-ylamino]-1,3-dihydro-isoindol-2-yl}-acetamide as a yellow foam (15 mg, 25%). $^1$H-NMR (CDCl$_3$) δ 8.70 (s, 1H), 8.28 (s, 1H), 7.96 (d, J=6.2 Hz, 1H), 7.52 (s, 1H), 7.44 (m, 1H), 7.14 (s, 1H), 7.05 (m, 3H), 6.85 (d, J=4.7 Hz, 1H), 6.73 (s, 1H), 4.03 (s, 2H), 3.95 (s, 2H), 3.89 (s, 3H), 3.84 (s, 3H), 3.45 (s, 3H); LC/MS (ESI+): 445.0 (M+H).

Example 865

1-(4-{3-Methoxy-4-[7-(2-methoxy-phenyl)-pyrrolo[2,1-f][1,2,4]triazin-2-ylamino]-phenyl}-piperidin-1-yl)-2-methyl-propan-2-ol Following the experimental procedure described in Example 787c), [7-(2-methoxy-phenyl)-pyrrolo[2,1-f][1,2,4]triazin-2-yl]-(2-methoxy-4-piperidin-4-yl-phenyl)-amine was converted to 1-(4-{3-methoxy-4-[7-(2-methoxy-phenyl)-pyrrolo[2,1-f][1,2,4]triazin-2-ylamino]-phenyl}-piperidin-1-yl)-2-methyl-propan-2-ol as a yellow foam (25 mg, 42%). $^1$H-NMR (CDCl$_3$) δ 8.69 (s, 1H), 8.29 (d, J=8.20 Hz, 1H), 7.99 (d, J=6.4 Hz, 1H), 7.45 (m, 2H), 7.14 (m, 1H), 7.07 (d, J=8.3 Hz, 1H), 7.01 (d, J=4.64 Hz, 1H), 6.84 (d, J=4.6 Hz, 1H), 6.73 (s, 2H), 3.91 (s, 3H), 3.84 (s, 3H), 3.02 (d, J=11.3 Hz, 2H), 2.44 (m, 3H), 2.36 (s, 2H), 1.78 (m, 4H), 1.19 (s, 6H); LC/MS (ESI+): 502.0 (M+H).

Example 866

N-[2-(2-{4-[1-(2-Hydroxy-2-methyl-propyl)-piperidin-4-yl]-2-methoxy-phenylamino}-pyrrolo[2,1-f][1,2,4]triazin-7-yl)-phenyl]-N-methyl-methanesulfonamide Following the experimental procedure described in Example 787c), N-{2-[2-(2-methoxy-4-piperidin-4-yl-phenylamino)-pyrrolo[2,1-f][1,2,4]triazin-7-yl]-phenyl}-N-methyl-methanesulfonamide was converted to N-[2-(2-{4-[1-(2-hydroxy-2-methyl-propyl)-piperidin-4-yl]-2-methoxy-phenylamino}-pyrrolo[2,1-f][1,2,4]triazin-7-yl)-phenyl]-N-methyl-methanesulfonamide as a yellow foam (26 mg, 36%). $^1$H-NMR (CDCl$_3$) δ 8.72 (s, 1H), 8.07 (d, J=8.3 Hz, 1H), 7.95 (m, 1H), 7.53 (m, 3H), 7.46 (s, 1H), 7.02 (d, J=4.76 Hz, 1H), 6.85 (d, J=4.7 Hz, 1H), 6.72 (m, 1H), 6.64 (d, J=7.2 Hz, 1H), 3.90 (s, 3H), 3.12 (s, 1H), 3.02 (d, J=11.4 Hz, 2H), 2.67 (s, 3H), 2.44 (m, 4H), 2.36 (s, 3H), 1.77 (m, 4H), 1.19 (s, 6H); LC/MS (ESI+): 579.0 (M+H).

Example 867

2-(4-{3-Methoxy-4-[7-(2-methoxy-phenyl)-pyrrolo[2,1-f][1,2,4]triazin-2-ylamino]-phenyl}-piperidin-1-yl)-N-methyl-acetamide Following the experimental procedure described in Example 761, trifluoro-methanesulfonic acid 7-(2-methoxy-phenyl)-pyrrolo[2,1-f][1,2,4]triazin-2-yl ester and 2-[4-(4-amino-3-methoxy-phenyl)-piperidin-1-yl]-N-methyl-acetamide were converted to 2-(4-{3-methoxy-4-[7-(2-methoxy-phenyl)-pyrrolo[2,1-f][1,2,4]triazin-2-ylamino]-phenyl}-piperidin-1-yl)-N-methyl-acetamide as a yellow foam (11 mg, 13%). $^1$H-NMR (CDCl$_3$) δ 8.69 (s, 1H), 8.30 (d, J=8.7 Hz, 1H), 8.00 (d, J=6.3 Hz, 1H), 7.45 (m, 2H), 7.24 (m, 1H), 7.14 (m, 1H), 7.05 (d, J=13.0 Hz, 1H), 7.03 (m, 1H), 6.84 (d, J=4.7 Hz, 1H), 6.73 (m, 2H), 3.91 (s, 3H), 3.85 (s, 3H), 3.04 (s, 2H), 2.96 (m, 2H), 2.87 (d, J=5.0 Hz, 3H), 2.47 (m, 1H), 2.29 (m, 2H), 1.73 (m, 4H); LC/MS (ESI+): 501.0 (M+H).

Example 868

{4-[1-(1H-Imidazol-2-ylmethyl)-piperidin-4-yl]-2-methoxy-phenyl}-[7-(2-methoxy-phenyl)-pyrrolo[2,1-f][1,2,4]triazin-2-yl]-amine Imidazole-2-carboxaldehyde (0.011 g, 0.112 mmol) and [7-(2-methoxy-phenyl)-pyrrolo[2,1-f][1,2,4]triazin-2-yl]-(2-methoxy-4-piperidin-4-yl-phenyl)-amine (53 mg, 0.12 mmol) were treated with sodium triacetoxyborohydride (0.033 g, 0.157 mmol) and acetic acid (0.064 mL, 0.112 mmol) in tetrahydrofuran (0.900 mL) at room temperature overnight. The reaction mixture was then concentrated and partitioned between dichloromethane and a saturated aqueous sodium bicarbonate solution. It was dried on NaSO$_4$, filtered and concentrated. The product was isolated by reverse phase hplc (Gilson) to afford {4-[1-(1H-imidazol-2-ylmethyl)-piperidin-4-yl]-2-methoxy-phenyl}-[7-(2-methoxy-phenyl)-pyrrolo[2,1-f][1,2,4]triazin-2-yl]-amine as a yellow foam (5 mg, 9%). $^1$H-NMR (CDCl$_3$) δ 9.63 (s, 1H), 8.69 (s, 1H), 8.29 (d, J=8.7 Hz, 1H), 8.00 (d, J=6.2 Hz, 1H), 7.44 (m, 2H), 7.13 (m, 1H), 7.07 (d, J=8.3 Hz, 1H), 7.02 (s, 2H), 6.83 (d, J=4.7 Hz, 1H), 6.73 (m, 2H), 3.89 (s, 3H), 3.84 (s, 3H), 3.71 (s, 2H), 2.97 (d, J=11.4 Hz, 2H), 2.49 (m, 1H), 2.25 (m, 2H), 1.85 (m, 5H); LC/MS (ESI+): 510.2 (M+H).

Example 869

2-(5-{7-[2-(Methanesulfonyl-methyl-amino)-phenyl]-pyrrolo[2,1-f][1,2,4]triazin-2-ylamino}-6-methoxy-1,3-dihydro-isoindol-2-yl)-acetamide Following the experimental procedure described in Example 761, trifluoro-methanesulfonic acid 7-[2-(methanesulfonyl-methyl-amino)-phenyl]-pyrrolo[2,1-f][1,2,4]triazin-2-yl ester and 2-(5-amino-6-methoxy-1,3-dihydro-isoindol-2-yl)-acetamide were converted to 2-(5-{7-[2-(methanesulfonyl-methyl-amino)-phenyl]-pyrrolo[2,1-f][1,2,4]triazin-2-ylamino}-6-methoxy-1,3-dihydro-isoindol-2-yl)-acetamide as a brown foam (15 mg, 13%). $^1$H-NMR (CDCl$_3$) δ 8.74 (s, 1H), 8.07 (d, J=7.4 Hz, 1H), 7.53 (m, 4H), 7.16 (s, 1H), 7.04 (d, J=4.7 Hz, 1H), 6.88 (d, J=4.7 Hz, 1H), 6.72 (s, 1H), 5.54 (br s, 1H), 4.05 (s, 2H), 3.89 (s, 5H), 3.47 (s, 2H), 3.13 (s, 3H), 2.69 (s, 3H); LC/MS (ESI+): 522.0 (M+H).

Example 870

2-[4-(4-{7-[2-(Methanesulfonyl-methyl-amino)-phenyl]-pyrrolo[2,1-f][1,2,4]triazin-2-ylamino}-3-methoxy-phenyl)-piperidin-1-yl]-N-methyl-acetamide Following the experimental procedure described in Example 761, trifluoro-methanesulfonic acid 7-[2-(methanesulfonyl-methyl-amino)-phenyl]-pyrrolo[2,1-f][1,2,4]triazin-2-yl ester and 2-[4-(4-amino-3-methoxy-phenyl)-piperidin-1-yl]-N-methyl-acetamide were converted to 2-[4-(4-{7-[2-(methanesulfonyl-methyl-amino)-phenyl]-pyrrolo[2,1-f][1,2,4]triazin-2-ylamino}-3-methoxy-phenyl)-piperidin-1-yl]-N-methyl-acetamide as a yellow foam (157 mg, 76%). $^1$H-NMR (CDCl$_3$) δ 8.73 (s, 1H), 8.10 (d, J=8.3 Hz, 1H), 7.95 (m, 1H), 7.53 (m, 3H), 7.46 (s, 1H), 7.36 (s, 1H), 7.02 (d, J=8.3 Hz, 1H), 6.86 (d, J=4.6 Hz, 1H), 6.72 (s, 1H), 6.64 (d, J=8.3 Hz, 1H), 3.91 (s, 3H), 3.16 (s, 5H), 3.02 (s, 2H), 2.87 (d, 3H), 2.67 (s, 3H), 2.48 (m, 3H), 1.85 (m, 4H); LC/MS (ESI+) 578.0 (M+H).

Example 871

(±)-N-[2-(2-{2-Methoxy-4-[1-(1-methyl-azetidin-2-ylmethyl)-piperidin-4-yl]-phenylamino}-pyrrolo[2,1-f][1,2,4]triazin-7-yl)-phenyl]-N-methyl-methanesulfonamide Following the experimental procedure described in Example 761, trifluoro-methanesulfonic acid 7-[2-(methanesulfonyl-methyl-amino)-phenyl]-pyrrolo[2,1-f][1,2,4]triazin-2-yl ester and (±)-2-methoxy-4-[1-(1-methyl-azetidin-2-ylmethyl)-piperidin-4-yl]-phenylamine were converted to (±)-N-[2-(2-{2-methoxy-4-[1-(1-methyl-azetidin-2-ylmethyl)-piperidin-4-yl]-phenylamino}-pyrrolo[2,1-f][1,2,4]triazin-7-yl)-phenyl]-N-methyl-methanesulfonamide as a brown foam (8 mg, 10%). $^1$H-NMR (CDCl$_3$) δ 8.72 (s, 1H), 8.08 (m, 1H), 7.95 (m, 1H), 7.52 (m, 3H), 7.46 (s, 1H), 7.03 (d, J=4.6 Hz, 1H), 6.86 (d, J=4.7 Hz, 1H), 6.71 (m, 1H), 6.61 (m, 1H), 3.88 (s, 4H), 3.66 (s, 1H), 3.12 (m, 9H), 2.85 (s, 2H), 2.67 (s, 6H), 2.61 (m, 6H); LC/MS (ESI+): 590 (M+H).

Example 872

N-[2-(2-{4-[1-((S)-2,3-Dihydroxy-propyl)-piperidin-4-yl]-2-methoxy-phenylamino}-pyrrolo[2,1-f][1,2,4]triazin-7-yl)-phenyl]-N-ethyl-methanesulfonamide Following the experimental procedure described in Example 787c), N-ethyl-N-{2-[2-(2-methoxy-4-piperidin-4-yl-phenylamino)-pyrrolo[2,1-f][1,2,4]triazin-7-yl]-phenyl}-methanesulfonamide was converted to N-[2-(2-{4-[1-((S)-2,3-dihydroxy-propyl)-piperidin-4-yl]-2-methoxy-phenylamino}-pyrrolo[2,1-f][1,2,4]triazin-7-yl)-phenyl]-N-ethyl-methanesulfonamide as a yellow foam (26 mg, 32%). $^1$H-NMR (CDCl$_3$) δ 8.72 (s, 1H), 8.10 (d, J=8.3 Hz, 1H), 8.01 (m, 1H), 7.56 (m, 2H), 7.48 (m, 2H), 7.20 (d, J=4.7 Hz, 1H), 6.86 (d, J=4.7 Hz, 1H), 6.72 (s, 1H), 6.64 (d, J=8.3 Hz, 1H), 3.95 (m, 1H), 3.89 (s, 3H), 3.73 (m, 1H), 3.73 (m, 1H), 3.59 (m, 3H), 3.44 (m, 2H), 3.25 (m, 2H), 2.89 (s, 3H), 2.79 (m, 1H), 2.53 (m, 2H), 2.35 (m, 1H), 1.88 (m, 4H), 0.89 (m, 3H); LC/MS: 593.3 (M+H).

Example 873

N-Ethyl-N-[2-(2-{4-[1-((R)-2-hydroxy-propyl)-piperidin-4-yl]-2-methoxy-phenylamino}-pyrrolo[2,1-f][1,2,4]triazin-7-yl)-phenyl]-methanesulfonamide Following the experimental procedure described in Example 787c), N-ethyl-N-{2-[2-(2-methoxy-4-piperidin-4-yl-phenylamino)-pyrrolo[2,1-f][1,2,4]triazin-7-yl]-phenyl}-methanesulfonamide was converted to N-ethyl-N-[2-(2-{4-[1-((R)-2-hydroxy-propyl)-piperidin-4-yl]-2-methoxy-phenylamino}-pyrrolo[2,1-f][1,2,4]triazin-7-yl)-phenyl]-methanesulfonamide as a yellow foam (4 mg, 5%). $^1$H-NMR (CDCl$_3$) δ 8.72 (s, 1H) 8.12 (d, J=8.2 Hz, 1H), 7.98 (m, 1H), 7.52 (m, 2H), 7.49 (m, 2H), 7.19 (m, 1H), 6.88 (d, J=4.7 Hz, 1H), 6.72 (s, 1H), 6.63 (d, J=7.9 Hz, 1H), 4.42 (m, 1H), 3.95 (d, J=12.0 Hz, 1H), 3.89 (s, 3H), 3.77 (d, J=11.2 Hz, 1H), 3.45 (m, 2H), 3.02 (m, 1H), 2.89 (m, 6H), 2.34 (m, 2H), 2.01 (m, 3H), 1.27 (d, J=6.3 Hz, 3H), 0.89 (m, 3H); LC/MS (ESI+) 579.25 (M+H).

Example 874

5-Methoxy-6-[7-(2-methoxy-phenyl)-pyrrolo[2,1-f][1,2,4]triazin-2-ylamino]-1,3-dihydro-isoindole-2-carboxylic acid tert-butyl ester Following the experimental procedure described in Example 761, trifluoro-methanesulfonic acid 7-(2-methoxy-phenyl)-pyrrolo[2,1-f][1,2,4]triazin-2-yl ester and 5-amino-6-methoxy-1,3-dihydro-isoindole-2-carboxylic acid tert-butyl ester were converted to 5-methoxy-6-[7-(2-methoxy-phenyl)-pyrrolo[2,1-f][1,2,4]triazin-2-ylamino]-1,3-dihydro-isoindole-2-carboxylic acid tert-butyl ester as a brown foam (112 mg, 36%). $^1$H-NMR (CDCl$_3$) δ 8.69 (d, J=4.0 Hz, 1H), 8.31 (d, J=3.9 Hz, 1H), 7.89 (m, 1H), 7.52 (m, 2H), 7.12 (m, 1H), 7.08 (d, J=8.3 Hz, 1H), 7.01 (m, 1H), 6.85 (d, J=4.6 Hz, 1H), 6.75 (m, 1H), 4.59 (m, 4H), 3.89 (s, 3H), 3.88*(s, 3H, amide rotamer), 3.83 (s, 3H), 3.82*(s, 3H, amide rotamer), 1.56 (s, 9H), 1.53* (s, 9H, amide rotamer); LC/MS (ESI+) 488.25 (M+H).

Example 875

5-{7-[2-(Methanesulfonyl-methyl-amino)-phenyl]-pyrrolo[2,1-f][1,2,4]triazin-2-ylamino}-6-methoxy-1,3-dihydro-isoindole-2-carboxylic acid tert-butyl ester Following the experimental procedure described in Example 761, trifluoro-methanesulfonic acid 7-[2-(methanesulfonyl-methyl-amino)-phenyl]-pyrrolo[2,1-f][1,2,4]triazin-2-yl ester and 5-amino-6-methoxy-1,3-dihydro-isoindole-2-carboxylic acid tert-butyl ester were converted to 5-{7-[2-(methanesulfonyl-methyl-amino)-phenyl]-pyrrolo[2,1-f][1,2,4]triazin-2-ylamino}-6-methoxy-1,3-dihydro-isoindole-2-carboxylic acid tert-butyl ester as a brown foam (30 mg, 8%). $^1$H-NMR (CDCl$_3$) δ 8.74 (d, J=5.3 Hz, 1H), 8.08 (d, J=7.3 Hz, 1H), 7.90 (d, J=6.5 Hz, 1H), 7.53 (m, 4H), 7.05 (m, 1H), 6.88 (d, J=4.6 Hz, 1H), 6.74 (m, 1H), 4.58 (m, 4H), 3.89 (s, 3H), 3.88* (s, 3H, amide rotamer), 3.11 (s, 3H), 2.72 (s, 2H), 2.67 (s, 1H), 1.56 (s, 9H), 1.53* (s, 9H, amide rotamer); LC/MS: 565.25 (M+H).

Example 876

N-{2-[2-(2-Isopropyl-6-methoxy-2,3-dihydro-1H-isoindol-5-ylamino)-pyrrolo[2,1-f][1,2,4]triazin-7-yl]-phenyl}-N-methyl-methanesulfonamide Following the experimental procedure described in Example 761, trifluoro-methanesulfonic acid 7-[2-(methanesulfonyl-methyl-amino)-phenyl]-pyrrolo[2,1-f][1,2,4]triazin-2-yl ester and 2-isopropyl-6-methoxy-2,3-dihydro-1H-isoindol-5-ylamine were converted to N-{2-[2-(2-isopropyl-6-methoxy-2,3-dihydro-1H-isoindol-5-ylamino)-pyrrolo[2,1-f][1,2,4]triazin-7-yl]-phenyl}-N-methyl-methanesulfonamide as a brown foam (40 mg, 36%). $^1$H-NMR (CDCl$_3$) δ 8.72 (s, 1H). 8.02 (s, 1H), 7.90 (m, 1H), 7.51 (m, 4H), 7.02 (d, J=4.6 Hz, 1H), 6.86 (d, J=4.7 Hz, 1H), 6.71 (s, 1H), 3.91 (s, 2H), 3.85 (s, 3H), 3.75 (s, 2H), 3.10 (s, 3H), 2.74 (m, 1H), 2.66 (s, 3H), 1.20 (d, J=6.2, 6H); LC/MS (ESI+): 507.0 (M+H).

Example 877

(2-Isopropyl-6-methoxy-2,3-dihydro-1H-isoindol-5-yl)-[7-(2-methoxy-phenyl)-pyrrolo[2,1-f][1,2,4]triazin-2-yl]-amine Following the experimental procedure described in Example 761, trifluoro-methanesulfonic acid 7-(2-methoxy-phenyl)-pyrrolo[2,1-f][1,2,4]triazin-2-yl ester and 2-isopropyl-6-methoxy-2,3-dihydro-1H-isoindol-5-ylamine were converted to (2-isopropyl-6-methoxy-2,3-dihydro-1H-isoindol-5-yl)-[7-(2-methoxy-phenyl)-pyrrolo[2,1-f][1,2,4]triazin-2-yl]-amine as a brown foam (20 mg, 12%). $^1$H-NMR (CDCl$_3$) δ 8.69 (s, 1H), 8.26 (s, 1H), 7.95 (d, J=6.8 Hz, 1H), 7.49 (s, 1H), 7.42 (m, 1H), 7.10 (m, 2H), 7.01 (d, J=4.6 Hz, 1H), 6.83 (d, J=4.6 Hz, 1H), 6.72 (s, 1H), 3.93 (s, 2H), 3.87 (s, 3H), 3.85 (s, 2H), 3.83 (s, 3H), 2.75 (m, 1H), 1.21 (d, J=6.3 Hz, 6H); LC/MS (ESI+): 430.04 (M+H).

Example 878

2-Amino-1-{5-methoxy-6-[7-(2-methoxy-phenyl)-pyrrolo[2,1-f][1,2,4]triazin-2-ylamino]-1,3-dihydro-isoindol-2-yl}-ethanone Following the experimental procedures described in Example 761 and 787b), trifluoro-methanesulfonic acid 7-(2-methoxy-phenyl)-pyrrolo[2,1-f][1,2,4]triazin-2-yl ester and [2-(5-amino-6-methoxy-1,3-dihydro-isoindol-2-yl)-2-oxo-ethyl]-carbamic acid tert-butyl ester were converted to 2-amino-1-{5-methoxy-6-[7-(2-methoxy-phenyl)-pyrrolo[2,1-f][1,2,4]triazin-2-ylamino]-1,3-dihydro-isoindol-2-yl}-ethanone as a yellow foam (13 mg, 21%). $^1$H-NMR (CDCl$_3$) δ 8.71 (d, J=2.6 Hz, 1H), 8.33 (s, 1H), 7.91 (m, 1H), 7.50 (m, 2H), 7.06 (m, 3H), 6.88 (d, J=4.6 Hz, 1H), 6.74 (m, 1H), 4.68 (m, 4H), 3.91 (s, 3H), 3.90*(s, 3H, amide rotamer), 3.85 (s, 3H), 3.83*(s, 3H, amide rotamer), 3.49 (s, 2H), NH$_2$ protons exchanged with H$_2$O; LC/MS (ESI+): 445.0 (M+H).

Example 879

N-(2-{2-[2-(2-Amino-acetyl)-6-methoxy-2,3-dihydro-1H-isoindol-5-ylamino]-pyrrolo[2,1-f][1,2,4]triazin-7-yl}-phenyl)-N-methyl-methanesulfonamide Following the experimental procedures described in Example 761 and 787b), trifluoro-methanesulfonic acid 7-[2-(methanesulfonyl-methyl-amino)-phenyl]-pyrrolo[2,1-f][1,2,4]triazin-2-yl ester and [2-(5-amino-6-methoxy-1,3-dihydro-isoindol-2-yl)-2-oxo-ethyl]-carbamic acid tert-butyl ester were converted to N-(2-{2-[2-(2-amino-acetyl)-6-methoxy-2,3-dihydro-1H-isoindol-5-ylamino]-pyrrolo[2,1-f][1,2,4]triazin-7-yl}-phenyl)-N-methyl-methanesulfonamide as a yellow foam (32 mg, 21%). $^1$H-NMR (CDCl$_3$) δ 8.74 (s, 1H), 8.13 (d, J=10.9 Hz, 1H), 7.92 (d, J=7.7 Hz, 1H), 7.58 (m, 4H), 7.05 (m, 1H), 6.88 (m, 1H), 6.77 (m, 1H), 4.60 (m, 4H), 3.91 (s, 3H), 3.89*(s, 3H, amide rotamer), 3.49 (s, 2H), 3.13 (s, 3H), 3.12*(s, 3H, amide rotamer), 2.71 (s, 3H), 2.68*(s, 3H, amide rotamer), NH$_2$ protons exchanged with H$_2$O; LC/MS (ESI+): 522.0 (M+H).

Example 881

N-{3-[2-(3-Acetylamino-phenylamino)-pyrrolo[2,1-f][1,2,4]triazin-7-yl]-phenyl}-2,2-dimethyl-propionamide 881A. 3-(2-Methylsulfanyl-pyrrolo[2,1-f][1,2,4]triazin-7-yl)-phenylamine. Palladium Acetate (0.20 eq) and Triphenylphosphine (0.25 eq) were dissolved in dioxane and the mixture was allowed to stir at room temperature for 10 minutes. 7-Bromo-2-methylsulfanyl-pyrrolo[2,1-f][1,2,4]triazine (2.00 g, 1.0 eq) was then added and the reaction was again allowed to stir at rt for 10 minutes. 3-Aminophenylboronic acid monohydrate (2.0 eq) was added followed by 1.5 M of Sodium carbonate in water (1.0 eq). The reaction mixture was then heated at 80° C. and was allowed to stir for 3 to 16 hrs. The reaction mixture was poured over saturated sodium chloride, and organics were extracted with dichloromethane. Combined organics were dried over magnesium sulfate, filtered and concentrated. The crude mixture was purified by Isco flash column chromatography (Hexane/Ethyl Acetate) to afford title compound. LCMS 257.1 (M+H), HPLC purity=85%, rt=1.929 min.

881B. 2,2-Dimethyl-N-[3-(2-methylsulfanyl-pyrrolo[2,1-f][1,2,4]triazin-7-yl)-phenyl]-propionamide. 3-(2-Methylsulfanyl-pyrrolo[2,1-f][1,2,4]triazin-7-yl)-phenylamine (0.200 g, 0.780 mmol) was dissolved in Methylene chloride (10.0 mL, 156 mmol) and cooled to 0° C. Triethylamine (0.130 mL, 0.936 mmol) was added followed by 2,2-Dimethylpropanoyl chloride (0.106 mL, 0.858 mmol). The reaction mixture was allowed to warm to rt. LCMS after 30 min indicated mass of title compound. Reaction mixture was washed with water, dried over MgSO4, filtered, and concentrated. HPLC rt=3.436, purity=90%, LCMS=341.2 (M+H).

881C. N-[3-(2-Methanesulfinyl-pyrrolo[2,1-f][1,2,4]triazin-7-yl)-phenyl]-2,2-dimethyl-propionamide. 2,2-Dimethyl-N-[3-(2-methylsulfanyl-pyrrolo[2,1-f][1,2,4]triazin-7-yl)-phenyl]-propionamide (1.0 eq) was dissolved in Methylene chloride (10 mL, 200 mmol) and a solution of m-Chloroperbenzoic acid (1.1 eq) in Methylene chloride (3 mL, 50 mmol) was added. The reaction was allowed to proceed at room temperature until HPLC showed consumption of starting material (30 min). The reaction mixture was poured over saturated sodium bicarbonate and organics were extracted with dichloromethane. Combined extracts were then dried over magnesium sulfate, filtered and concentrated. The crude reaction mixture was then purified by Isco flash column chromatography (hexanes/ethyl acetate eluent).

881D. N-{3-[2-(3-Acetylamino-phenylamino)-pyrrolo[2,1-f][1,2,4]triazin-7-yl]-phenyl}-2,2-dimethyl-propionamide. 3'-aminoacetanilide (2.0 eq) and N-[3-(2-Methanesulfinyl-pyrrolo[2,1-f][1,2,4]triazin-7-yl)-phenyl]-2,2-dimethyl-propionamide (1.0 eq) were combined in a minimal amount of 1-Methoxy-2-propanol. The reaction was heated to 180° C. under microwave conditions for 4 hours. The mixture was then taken up in DMSO and purified by Gilson prep HPLC to afford the title compound as a TFA salt (29 mg, 19%). HPLC rt=2.959 min, 95% purity, LCMS=443.2 (M+H). $^1$H NMR (400 MHz, (D3C)2SO, δ, ppm): 9.82 (s, 1H), 9.49 (s, 1H), 9.28 (s, 1H), 8.99 (s, 1H), 8.21 (s, 1H), 7.96 (d, J=7.5 Hz, 1H), 7.72-7.65 (m, 3H), 7.40 (dd, J=8.0 Hz, 8.0 Hz, 1H), 7.15-7.14 (d, J=4.9 Hz, 2H), 7.06 (d, J=4.5 Hz, 1H), 6.96 (d, J=4.5 Hz, 1H), 2.03 (s, 3H), 1.24 (s, 9H).

Example 882

N-{3-[2-(1-Acetyl-2,3-dihydro-1H-indol-6-ylamino)-pyrrolo[2,1-f][1,2,4]triazin-7-yl]-phenyl}-2,2-dimethyl-propionamide 1-acetyl-6-aminoindoline and N-[3-(2-Methanesulfinyl-pyrrolo[2,1-f][1,2,4]triazin-7-yl)-phenyl]-2,2-dimethyl-propionamide were combined in an analogous fashion to Example 881D. The mixture was then taken up in DMSO and purified by Gilson prep HPLC to afford the title compound as a TFA salt (35 mg, 38%). HPLC purity=98%, rt=3.18 min, LCMS=465.2 (M−3). $^1$H NMR (400 MHz, (D3C)2SO, δ, ppm): 9.47 (s, 1H), 9.39 (s, 1H), 8.96 (s, 1H), 8.20 (d, J=4.7 Hz, 2H0, 7.96 (d, J=7.9 Hz, 1H), 7.72 (d, J=7.9 Hz, 1H), 7.68 (d, J=8.4 Hz, 1H), 7.39 (dd, J=7.9 Hz, 1H), 7.08 (d, J=8.4 Hz, 1H), 7.05 (d, J=4.8 Hz, 1H), 6.94 (d, J=4.8 Hz, 1H), 4.10 (dd, J=8.5 Hz, 2H), 3.06 (dd, J=8.5 Hz, 2H), 2.17 (s, 3H), 1.24 (s, 9H).

Example 883

N-tert-Butyl-3-{2-[3-(4-methyl-piperazin-1-yl)-phenylamino]-pyrrolo[2,1-f][1,2,4]triazin-7-yl}-benzenesulfonamide 3-(4-Methylpiperazin-1-yl)aniline and N-tert-Butyl-3-(2-methanesulfinyl-pyrrolo[2,1-f][1,2,4]triazin-7-yl)-benzenesulfonamide were combined in an analogous fashion to Example 881D. The mixture was purified by Gilson prep HPLC to afford title compound as a TFA salt (35 mg, 34%). HPLC purity=95%, rt=2.696 min, LCMS=520.3 (M+1). 1H NMR (400 MHz, (D3C)2SO, δ, ppm): 9.63 (bs, 1H), 9.39 (s, 1H), 9.09 (s, 1H0, 8.48 (s, 1H0, 8.42 (d, J=7.8 Hz, 1H), 7.86 (d, J=7.8 Hz, 1H), 7.71 (dd, J=7.8 Hz, 7.8 Hz, 1H), 7.61 (s, 1H0, 7.46 (d, j=8.3 Hz, 1H), 7.25 (dd, J=7.8 Hz, 7.8 Hz, 1H), 7.21-7.16 (m, 2H), 7.01 (d, J=4.7 Hz, 1H), 6.65 (dd, J=8.3 Hz, 1.6 Hz, 2H), 3.69 (d, J=12.7 Hz, 2H), 3.46 (d, J=12.2 Hz, 2H), 3.15-3.11 (m, 2H), 2.92 (d, J=13.1 Hz, 2H), 2.86 (d, J=3.7 Hz, 3H), 1.11 (s, 9H).

Example 884

N-(3-{7-[3-((S)-3-Hydroxy-pyrrolidine-1-sulfonyl)-phenyl]-pyrrolo[2,1-f][1,2,4]triazin-2-ylamino}-phenyl)-acetamide 884A. 3-(2-Methylsulfanyl-pyrrolo[2,1-f][1,2,4]triazin-7-yl)-benzenesulfonyl chloride Sodium nitrite (56.5 mg, 0.819 mmol) in water (0.5 ml) was added to a solution of 3-(2-Methylsulfanyl-pyrrolo[2,1-f][1,2,4]triazin-7-yl)-phenylamine (from Example 1A) (0.200 g, 0.780 mmol) in 12.00 M of Hydrogen Chloride in Water (1.34 mL, 16.0 mmol) at 0° C., and the solution was stirred at 0° C. for 1.5 h. Sulfur dioxide (5.00 g, 78.0 mmol) gas was bubbled into a mixture of Copper(II)Chloride Dihydrate (29.0 mg, 0.170 mmol) in 17.40 M of Acetic acid in Water (2.23 mL, 38.8 mmol) at 0° C. for 10 min. The diazonium salt suspension was added dropwise to the sulfur dioxide mixture and it was allowed to warm to rt and stir 16 hrs. LCMS showed 3/1 product (322.0-mass of sulfonic acid) to SM. The reaction mixture was diluted with water and the resulting ppt was filtered. SM remained in solution and recovered pure product: with LCMS rt of 0.66 minutes. The yellow solid was dried under vacuum and used in the next step without further purification.

884B. (S)-1-[3-(2-Methylsulfanyl-pyrrolo[2,1-f][1,2,4]triazin-7-yl)-benzenesulfonyl]-pyrrolidin-3-ol. 3-(2-Methylsulfanyl-pyrrolo[2,1-f][1,2,4]triazin-7-yl)-benzenesulfonyl chloride (0.138 g, 0.406 mmol) was dissolved in Methylene chloride (3.45 mL, 53.8 mmol) and cooled to 0° C. N,N-Diisopropylethylamine (148 uL, 0.853 mmol) was added followed by (S)-Pyrrolidin-3-ol (37.1 uL, 0.447 mmol). The reaction was allowed to warm to rt. Stirred at rt for 30 min. Yellow solid ppt'd. LCMS showed new peak of 391.1 (M+1). Reaction mixture was diluted with CH$_2$Cl$_2$ and washed with water. CH$_2$Cl$_2$ layer was dried over MgSO4, filtered, and concentrated. Recovered yellow solid corresponding to title compound. Product was taken on to next step without further purification.

884C. S)-1-[3-(2-Methanesulfinyl-pyrrolo[2,1-f][1,2,4]triazin-7-yl)-benzenesulfonyl]-pyrrolidin-3-ol. (S)-1-[3-(2-Methylsulfanyl-pyrrolo[2,1-f][1,2,4]triazin-7-yl)-benzenesulfonyl]-pyrrolidin-3-ol was oxidized in an analogous manner to Example 881C for 30 mins to afford title compound. The crude reaction mixture was taken forward to the next step. HPLC rt=1.939 min, LCMS=407.0 (M+H).

884D. N-(3-{7-[3-((S)-3-Hydroxy-pyrrolidine-1-sulfonyl)-phenyl]-pyrrolo[2,1-f][1,2,4]triazin-2-ylamino}-phenyl)-acetamide. 3'-aminoacetanilide and (S)-1-[3-(2-Methanesulfinyl-pyrrolo[2,1-f][1,2,4]triazin-7-yl)-benzenesulfonyl]-pyrrolidin-3-ol (from Example 4C) were reacted in an analogous manner to Example 881D. The mixture was then taken up in DMSO and purified by Gilson prep HPLC to afford the product as a TFA salt, 18 mg, 21%). HPLC rt=2.460 min, 93% purity, LCMS=493.1 (M+H). $^1$H NMR (400 MHz, (D3C)2SO, δ, ppm): 9.84 (s, 1H), 9.52 (s, 1H), 9.04 (s, 1H0, 8.59 (d, J=8.0 Hz, 1H), 8.32 (s, 1H), 7.80-7.78 (m, 2H), 7.71 (dd, J=7.2 Hz, 7.2 Hz, 1H), 7.56 (d, J=8.0 Hz, 1H), 7.29 (d, J=4.9 Hz, 1H), 7.25 (dd, J=8.1 Hz, 8.1 Hz, 1H), 7.14 9 d, J=8.4 Hz, 1H0, 6.99 (d, J=4.7 Hz, 1H), 4.16 (s, 1H), 3.31-3.20 (m, 4H), 3.08 (d, J=10.2 Hz, 1H), 2.04 (s, 3H), 1.80-1.72 (m, 1H), 1.68-1.58 (m, 1H).

Example 885

1-(6-{7-[3-((S)-3-Hydroxy-pyrrolidine-1-sulfonyl)-phenyl]-pyrrolo[2,1-f][1,2,4]triazin-2-ylamino}-2,3-dihydro-indol-1-yl)-ethanone 1-acetyl-6-aminoindoline and (S)-1-[3-(2-Methanesulfinyl-pyrrolo[2,1-f][1,2,4]triazin-7-yl)-benzenesulfonyl]-pyrrolidin-3-ol were reacted in an analogous manner to Example 881D. The mixture was then taken up in DMSO and purified by Gilson prep HPLC to afford the product as a TFA salt (16 mg, 17%). HPLC purity=94%, rt=2.636 min, LCMS=519.2 (M+H). $^1$H NMR (400 MHz, (D3C)2SO, δ, ppm): 9.41 (s, 1H0, 9.01 (s, 1H), 8.58 (d, J=8.3 Hz, 1H), 8.31 (s, 1H), 8.26 (s, 1H0, 7.76 (d, J=8.1 Hz, 1H), 7.68 (dd, J=8.1 Hz, 8.1 Hz, 1H), 7.52 (dd, J=8.3 Hz, 1.8 Hz, 1H), 7.27 (d, J=4.7 Hz, 1H), 7.19 (d, J=8.3 Hz, 1H), 6.97 (d, J=4.9 Hz, 1H), 4.18-4.08 (m, 4H), 3.31-3.20 (m, 3H), 3.12-3.02 (m, 3H), 2.17 (s, 3H), 1.80-1.70 (m, 1H), 1.68-1.60 (m, 1H).

Example 886

3-[2-(3-Acetylamino-phenylamino)-pyrrolo[2,1-f][1,2,4]triazin-7-yl]-N-tert-butyl-benzamide 886A. N-tert-Butyl-3-(2-methylsulfanyl-pyrrolo[2,1-f][1,2,4]triazin-7-yl)-benzamide. 7-Bromo-2-methylsulfanyl-pyrrolo[2,1-f][1,2,4]triazine and 3-(t-Butylaminocarbonyl)phenylboronic acid were reacted in an analogous manner to Example 881A for 16 hrs. The crude mixture was purified by Isco flash column chromatography (Hexane/EthylAcetate) to afford title compound (1.28 g, 55%). LCMS=341.1 (M+H), HPLC rt=3.420 min, purity=92%

886B. N-tert-Butyl-3-(2-methanesulfinyl-pyrrolo[2,1-f][1,2,4]triazin-7-yl)-benzamide. 2,2-Dimethyl-N-[3-(2-methylsulfanyl-pyrrolo[2,1-f][1,2,4]triazin-7-yl)-phenyl]-propionamide was oxidized in an analogous manner to Example 881C for 30 mins to afford title compound after silica gel chromatography. LCMS=379 (M+Na).

886C. 3-[2-(3-Acetylamino-phenylamino)-pyrrolo[2,1-f][1,2,4]triazin-7-yl]-N-tert-butyl-benzamide. 3'-aminoacetanilide and N-[3-(2-Methanesulfinyl-pyrrolo[2,1-f][1,2,4]triazin-7-yl)-phenyl]-2,2-dimethyl-propionamide were reacted in an analogous manner to Example 881D. The mixture was then taken up in DMSO and purified by Gilson prep HPLC to afford the product as a TFA salt (38 mg, 31%). HPLC rt=3.010 min, 96% purity, LCMS=443.3 (M+H). $^1$H NMR (400 MHz, (D3C)2SO, δ, ppm): 9.82 (s, 1H), 9.51 (s, 1H), 9.01 (s, 1H), 8.39 (s, 1H), 8.33 (d, j=8.2 Hz, 1H0, 7.85 (s, 1H), 7.78 (d, J=7.6 Hz, 1H), 7.74 (s, 1H), 7.64 (d, J=7.6 Hz, 1H), 7.54 (dd, J=8.2 Hz, 8.2 Hz, 1H), 7.24 (d, j=4.6 Hz, 1H), 7.22-7.14 (m, 2H), 6.98 (d, J=4.7 Hz, 1H0, 2.03 (s, 3H), 1.39 (s, 9H).

Example 887

3-[2-(1-Acetyl-2,3-dihydro-1H-indol-6-ylamino)-pyrrolo[2,1-f][1,2,4]triazin-7-yl]-N-tert-butyl-benzamide 1-acetyl-6-aminoindoline and N-[3-(2-Methanesulfinyl-pyrrolo[2,1-f][1,2,4]triazin-7-yl)-phenyl]-2,2-dimethyl-propionamide were reacted in an analogous manner to Example 881D. The mixture was then taken up in DMSO and purified by Gilson prep HPLC to afford the product as a TFA salt (38 mg, 29%). HPLC rt=3.194 min, 96% purity, LCMS=469.3 (M+H). $^1$H NMR (400 MHz, (D3C)2SO, δ, ppm): 9.41 (s, 1H), 8.98 (s, 1H), 8.41 (s, 1H), 8.53 (d, J=8.5 Hz, 1H), 8.21 (s, 1H0, 7.83 (s, 1H0, 7.76 (d, J=7.2 Hz, 1H0, 7.68 (d, J=8.5 Hz, 1H), 7.52 (dd, J=7.9 Hz, 7.9 Hz, 1H), 7.22 (d, J=4.8 Hz, 1H), 7.12 (d, J=8.5 Hz, 1H), 6.96 (d, J=4.8 Hz, 1H), 4.10 (dd, J=8.4 Hz, 8.4 Hz, 2H), 3.06 (dd, J=8.4 Hz. 8.4 Hz, 2H), 2.16 (s, 3H, 1.39 (s, 9H).

Example 888

N-{5-[7-(3-tert-Butylsulfamoyl-phenyl)-pyrrolo[2,1-f][1,2,4]triazin-2-ylamino]-2-chloro-phenyl}-acetamide 8A. N-(2-Chloro-5-nitro-phenyl)-acetamide. 2-Chloro-5-nitro-phenylamine (2.00 g, 11.6 mmol) was dissolved in 1,2-Dichloroethane (20 mL, 300 mmol) at room temperature. N,N-Diisopropylethylamine (2.22 mL, 12.7 mmol) was added followed by Acetyl chloride (1.81 mL, 25.5 mmol). Reaction mixture was warmed to 45° C. for 16 hrs. Precipitate formed. Organics were dissolved in dichloromethane and washed with saturated sodium bicarbonate. Organics were dried over magnesium sulfate and filtered and reduced in vacuo. For LCMS, product did not ionize; elution time was 0.82 minutes. 2.49 g , quant yield.

888B. N-(5-Amino-2-chloro-phenyl)-acetamide.

A suspension of N-(2-Chloro-5-nitro-phenyl)-acetamide (5.00E2 mg, 2.33 mmol), Tin(II) chloride (1.33 g, 7.01 mmol), and Ethanol (8.32 mL, 142 mmol) was heated to 75° C. for 16 hrs. The reaction mixture was treated with an aqueous solution of potassium carbonate, filtered, and filtrate was concentrated. The resulting residue was dissolved in ethyl acetate and washed with 1 N sodium hydroxide and water. The crude product was taken up in DMSO and purified using Gilson RP-HPLC. For LCMS, product did not ionize; elution time was 0.57 minutes. HPLC retention time 0.778 minutes.

8C. N-{5-[7-(3-tert-Butylsulfamoyl-phenyl)-pyrrolo[2,1-f][1,2,4]triazin-2-ylamino]-2-chloro-phenyl}-acetamide . N-(5-Amino-2-chloro-phenyl)-acetamide and N-tert-Butyl-3-(2-methanesulfinyl-pyrrolo[2,1-f][1,2,4]triazin-7-yl)-benzenesulfonamide were reacted in an analogous manner to Example 881D. The mixture was then taken up in DMSO and purified by Gilson prep HPLC to afford title compound as a TFA salt (29 mg, 22%). LCMS=514.9 (M+H), HPLC rt=3.33 min, 99% purity. $^1$H NMR (400 MHz, (D3C)2SO, δ, ppm): 9.73 (s, 1H), 9.47 (s, 1H), 9.06 (s, 1H0, 8.45 (s, 1H), 8.40 (d, J=7.9 Hz, 1H), 7.96 (s, 1H0, 7.85 (d, J=7.9 Hz, 1H), 7.76 (dd, J=7.2 Hz, 7.2 Hz, 2H), 7.63 (s, 1H), 7.44 (d, J=8.5 Hz, 1H), 7.23 (d, J=4.5 Hz, 1H0, 7.03 (d, J=4.5 Hz, 1H), 2.06 (s, 3H0, 1.12 (s, 9H).

Example 889

N-tert-Butyl-3-[2-(3-methanesulfonylamino-phenylamino)-pyrrolo[2,1-f][1,2,4]triazin-7-yl]-benzenesulfonamide N-(3-Amino-phenyl)-methanesulfonamide and N-tert-Butyl-3-(2-methanesulfinyl-pyrrolo[2,1-f][1,2,4]triazin-7-yl)-benzenesulfonamide were reacted in an analogous manner to Example 881D. The mixture was then taken up in DMSO and purified by Gilson prep HPLC to afford title compound as a TFA salt (50 mg, 30%) LCMS=514.9 (M+H), HPLC rt=3.26 min, 95% purity, $^1$H NMR (400 MHz, (D3C)2SO, δ, ppm) 9.65 (s, 1H), 9.59 (s, 1H), 9.05 (s, 1H), 8.48 (s, 1H), 8.46 (d, J=7.9 Hz, 1H), 7.83 (d, J=7.9 Hz, 1H), 7.75-7.72 (m, 2H), 7.62 (s, 1H), 7.40 (bs, 1H0, 7.32 (dd, J=8.1 Hz, 8.1 Hz, 1H), 2.97 (s, 3H), 1.11 (s, 9H).

Example 890

3-[7-(3-tert-Butylsulfamoyl-phenyl)-pyrrolo[2,1f][1,2,4]triazin-2-ylamino]-benzoic acid ethyl ester 3-Amino-benzoic acid ethyl ester and N-tert-Butyl-3-(2-methanesulfinyl-pyrrolo[2,1-f][1,2,4]triazin-7-yl)-benzenesulfonamide were reacted in an analogous manner to Example 881D. Purified by ISCO silica gel chromatography with a gradient of 0-50% EtOAc in hexanes to obtain 77 mg, 17% yield. LCMS=493.9 (M+H), HPLC 3.881 min, purity 90%. $^1$H NMR (400 MHz, (D3C)2SO, δ, ppm) 9.77 (s, 1H), 9.08 (s, 1H), 8.48-8.46 (m, 2H), 8.28 (s, 1H), 8.19 (d, J=8.1 Hz, 1H), 7.83 (d, J=7.8 Hz, 1H), 7.70 (dd, J=8.2 Hz, 8.2 Hz, 1H), 7.60 (s, 1H), 7.55 (d, J=7.4 Hz, 1H), 7.50 (dd, J=7.8 Hz, 7.8 Hz, 1H), 7.25 (d, J=4.7 Hz, 1H), 7.04 (d, J=4.7 Hz, 1H), 4.28 (q, J=7.2 Hz, 2H), 1.25 (t, J=7.2 Hz, 3H), 1.11 (s, 9H).

Example 891

N-tert-Butyl-3-{2-[3-(4-methyl-piperazine-1-carbonyl)-phenylamino]-pyrrolo[2,1-f][1,2,4]triazin-7-yl}-benzenesulfonamide (3-Amino-phenyl)-(4-methyl-piperazin-1-yl)-methanone and N-tert-Butyl-3-(2-methanesulfinyl-pyrrolo[2,1-f][1,2,4]triazin-7-yl)-benzenesulfonamide were reacted in an analogous manner to Example 881D. The mixture was then taken up in DMSO and purified by Gilson prep HPLC to afford title compound as a TFA salt (24 mg, 19%) LCMS=548.0 (M+H), HPLC rt=2.525 min, 99% purity, ¹H NMR (400 MHz, (D3C)2SO, δ, ppm): 9.81 (bs, 1H), 9.76 (s, 1H), 9.08 (s, 1H), 8.50 (s, 1H), 8.43 (d, J=7.88 Hz, 1H), 7.98 (d, J=8.8 Hz, 1H), 7.85 (d, J=7.8 Hz, 1H), 7.74-7.70 (m, 2H), 7.62 (s, 1H), 7.47 (dd, J=7.2 Hz, 7.8 Hz, 1H), 7.24 (d, J=5.2 Hz, 1H), 7.05-7.03 (m, 2H), 2.82 (s, 3H), 1.11 (s, 9H).

Example 892

N-tert-Butyl-3-{2-[3-(morpholine-4-carbonyl)-phenylamino]-pyrrolo[2,1-f][1,2,4]triazin-7-yl}-benzenesulfonamide (3-Amino-phenyl)-morpholin-4-yl-methanone and N-tert-Butyl-3-(2-methanesulfinyl-pyrrolo[2,1-f][1,2,4]triazin-7-yl)-benzenesulfonamide were reacted in an analogous manner to Example 881D. The mixture was then taken up in DMSO and purified by Gilson prep HPLC to afford title compound as a TFA salt (20 mg, 20%) LCMS=534.6 (M+H), HPLC rt=3.111 min, 99% purity, ¹H NMR (400 MHz, (D3C)2SO, δ, ppm): 9.74 (s, 1H), 9.07 (s, 1H), 8.48 (d, J=7.9 Hz, 1H), 8.42 (s, 1H), 7.87-7.84 (m, 2H), 7.79 (s, 1H), 7.71 (dd, J=7.9 Hz, 7.9 Hz, 1H), 7.62 (s, 1H), 7.42 (dd, J=7.9 Hz, 7.9 Hz, 1H), 7.22 (d, J=5.5 Hz, 1H), 7.02 (d, J=5.5 Hz, 1H), 6.98 (d, J=7.1 Hz, 1H), 3.62-3.30 (bm, 8H), 1.11 (s, 9H).

Example 893

N-(3-{7-[3-(2-Methanesulfonyl-ethylamino)-phenyl]-pyrrolo[2,1-f][1,2,4]triazin-2-ylamino}-phenyl)-acetamide 893A. (2-Methanesulfonyl-ethyl)-[3-(2-methylsulfanyl-pyrrolo[2,1-f][1,2,4]triazin-7-yl)-phenyl]-amine. 3-(2-Methylsulfanyl-pyrrolo[2,1-f][1,2,4]triazin-7-yl)-phenylamine (2.30E2 mg, 0.897 mmol), Methanesulfonyl-ethene (95.2 mg, 0.897 mmol), and 17.40 M of Acetic acid in Water (5.16 uL, 0.0897 mmol) were placed in a microwave vial and the reaction was heated under microwave to 200° C. for 20 minutes. LCMS 362.9 (1.02 min rt). Diluted black solid with CH₂Cl₂ and purified by ISCO silica gel chromatography 0-100% EtOAc in hexanes to recover 128 mg, 39% of title product.

893B. [3-(2-Methanesulfinyl-pyrrolo[2,1-f][1,2,4]triazin-7-yl)-phenyl]-(2methanesulfonyl-ethyl)-amine. (2-Methanesulfonyl-ethyl)-[3-(2-methylsulfanyl-pyrrolo[2,1-f][1,2,4]triazin-7-yl)-phenyl]-amine was oxidized in an analogous manner to Example 881C for 30 mins Reaction was quenched with sat'd aqueous NaHCO₃ and partitioned into CH₂Cl₂. Organic layer was dried, filtered, and concentrated to afford title compound. (128 mg, 99% yield)

893C. 3'-aminoacetanilide and [3-(2-Methanesulfinyl-pyrrolo[2,1-f][1,2,4]triazin-7-yl)-phenyl]-(2-methanesulfonyl-ethyl)-amine were combined in an analogous manner to Example 881D. The mixture was then taken up in DMSO and purified by Gilson prep HPLC to afford the title compound as a TFA salt (0.37 mg mg, 0.5%: lost product due to Gilson error). LCMS=464.9 (M+H), HPLC rt=2.435 min, purity=99%. ¹H NMR (400 MHz, (D3C)2SO, δ, ppm): 8.61 (s, 1H), 7.85 (s, 1H), 7.71 (s, 1H), 7.56 (d, J=8.4 Hz, 1H), 7.51 (s, 1H), 7.38-7.36 (m, 2H), 7.32 (m, 1H), 7.28 (m, 1H), 7.14 (d, J=5.4 Hz, 1H), 7.07 (d, J=5.4 Hz, 1H), 6.99 (s, 1H), 6.78 (m, 1H), 3.68 (m, 2H), 3.25 (m, 2H), 2.91 (s, 3H), 2.17 (s, 3H).

Example 894

{7-[3-(2-Methanesulfonyl-ethylamino)-phenyl]-pyrrolo[2,1-f][1,2,4]triazin-2-yl}-[3-(4-methyl-piperazin-1-yl)-phenyl]-amine 3-(4-Methylpiperazin-1-yl)aniline and [3-(2-M ethanesulfinyl-pyrrolo[2,1-f][1,2,4]triazin-7-yl)-phenyl]-(2-methanesulfonyl-ethyl)-amine were combined in an analogous manner to Example 881D for 6 hours. The mixture was then taken up in DMSO and purified by Gilson prep HPLC to afford the title compound as a TFA salt (2.5 mg mg, 3.3%: lost product due to Gilson error). LCMS=506.0 (M+H), HPLC rt=2.226, 99% purity, ¹H NMR (400 MHz, (D3C)2SO, δ, ppm): 8.63 (s, 1H), 7.82 (bm, 1H), 7.67 (m, 1H), 7.41 (m, 1H), 7.34-7.30 (m, 1H), 7.22-7.20 (m, 3H), 7.04 (d, J=1.8 Hz, 1H), 6.88 (d, J=8.0 Hz, 1H), 6.77 (d, J=8.3 Hz, 1H), 6.55 d, J=8.0 Hz, 1H), 3.66 (dd, J=5.3 Hz, 6.8 Hz, 2H), 3.52-3.41 (m, 4H), 3.24 (dd, J=5.4 Hz, 6.3 Hz, 2H), 3.19-3.13 (m, 2H), 2.88 (m, 5H), 2.82 (m, 3H).

Example 895

3-[7-(3-tert-Butylsulfamoyl-phenyl)-pyrrolo[2,1-f][1,2,4]triazin-2-ylamino]-benzoic acid 3-[7-(3-tert-Butylsulfamoyl-phenyl)-pyrrolo[2,1-f][1,2,4]triazin-2-ylamino]-benzoic acid ethyl ester (77.0 mg, 0.156 mmol) was taken up in 2 M of Sodium hydroxide in water (2.00 mL, 5.00 mmol) and 2 ml THF, heated for 72 h at 60° C. Concentrated down THF, neutralized aq layer, and extracted with CH₂Cl₂. Dried, filtered, and concentrated. Took residue up in DMSO and purified by Gilson RP-HPLC. LCMS=465.9 (M+H), HPLC rt=3.199, purity=98%. ¹H NMR (400 MHz, CDCl3, δ, ppm): 12.95 (bs, 1H), 9.74 (s, 1H), 9.07 (s, 1H), 8.42 (d, J=7.6 Hz, 1H), 8.44 (s, 1H), 8.26 (s, 1H), 8.07 (d, J=8.3 Hz, 1H), 7.72 (dd, J=8.3 Hz, 7.6 Hz, 1H), 7.61 (s, 1H), 7.55 (d, J=8.3 Hz, 1H), 7.47 (dd, J=7.6 Hz, 8.3 Hz, 1H), 7.24 (d, J=4.6 Hz, 1H), 7.04 (d, J=4.9 Hz, 1H), 1.1 (s, 9H).

Example 896

3-[2-(3-Amino-phenylamino)-pyrrolo[2,1-f][1,2,4]triazin-7-yl]-N-tert-butyl-benzenesulfonamide (3-Amino-phenyl)-urea and N-tert-Butyl-3-(2-methanesulfinyl-pyrrolo[2,1-f][1,2,4]triazin-7-yl)-benzenesulfonamide were reacted in an analogous manner to Example 881D (200° C. for 1 hr). The mixture was then taken up in DMSO and purified by Gilson prep HPLC to afford title compound as a TFA salt (30 mg, 30%) LCMS=436.9 (M+H), HPLC rt=2.546, 98% purity. ¹H NMR (400 MHz, (D3C)2SO, δ, ppm): 9.85 (s, 1H), 9.09 (s, 1H), 8.55 (s, 1H), 8.39 (d, J=8.5 Hz, 1H), 7.88-7.84 (m, 2H), 7.78 (dd, J=7.7 Hz, 7.7 Hz, 1H), 7.68 (s, 1H), 7.44-7.39 (m, 2H), 7.26 (d, J=4.6 Hz, 1H), 7.04 (d, J=4.6 Hz, 1H), 6.83 (d, J=7.0 Hz, 1H), 1.11 (s, 9H).

Example 897

N-{3-[7-(3-tert-Butylsulfamoyl-phenyl)-pyrrolo[2,1-f][1,2,4]triazin-2-ylamino]-phenyl}-2-dimethylamino-acetamide

[3-(2-Dimethylamino-acetylamino)-phenyl]-carbamic acid tert-butyl ester and N-tert-Butyl-3-(2-methanesulfinyl-pyrrolo[2,1-f][1,2,4]triazin-7-yl)-benzenesulfonamide were reacted in an analogous manner to Example 881D (200° C. for 1 hr). The mixture was then taken up in DMSO and purified by Gilson prep HPLC to afford title compound as a TFA salt (10 mg, 8%) LCMS=521.9 (M+H), HPLC rt=2.645 min, 94% purity, $^1$H NMR (400 MHz, (CDCl$_3$), δ, ppm): 9.30 (s, 1H), 8.82 (s, 1H), 8.70 (s, 1H), 8.07 (s, 1H), 7.98 (d, J=7.5 Hz, 1H), 7.82 (d, J=7.5 Hz, 1H), 7.68-7.63 (m, 3H), 7.26-7.24 (m, 1H), 7.04-7.00 (m, 2H), 6.90 (d, J=8.2 Hz, 1H), 6.42 (s, 1H), 4.06 (s, 2H), 3.04 (s, 6H), 1.27 (s, 9H).

Example 898

N-[7-(6-Methoxy-pyridin-3-yl)-pyrrolo[2,1-f][1,2,4]triazin-2-yl]-benzene-1,3-diamine m-Phenylenediamine and 2-Methanesulfinyl-7-(6-methoxy-pyridin-3-yl)-pyrrolo[2,1-f][1,2,4]triazine were reacted in an analogous manner to Example 881D at 200° C. for 1 hr, taken up in DMSO, purified by Gilson prep HPLC to afford title compound as a TFA salt (34 mg, 50% yield). LCMS=332.9 (M+H), HPLC rt=2.067 min, 98% purity, $^1$H NMR (400 MHz, (D3C)2SO, δ, ppm): 9.78 (s, 1H), 9.02 (s, 1H), 8.92 (d, J=2.0 Hz, 1H), 8.50 (dd, J=8.86 Hz, 2.45 Hz, 1H), 7.68 (d, J=7.9 Hz, 1H), 7.61 (s, 1H), 7.36 (dd, J=8.4 Hz, 7.9 Hz, 1H), 7.22 (d, J=4.5 Hz, 1H), 7.06 (d, J=8.4 Hz, 1H), 7.00 (d, J=4.5 Hz, 1H), 6.84 (d, J=7.4 Hz, 1H), 3.95 (s, 3H).

Example 899

2-Dimethylamino-N-{3-[7-(6-methoxy-pyridin-3-yl)-pyrrolo[2,1-f][1,2,4]triazin-2-ylamino]-phenyl}-acetamide N-[7-(6-Methoxy-pyridin-3-yl)-pyrrolo[2,1-f][1,2,4]triazin-2-yl]-benzene-1,3-diamine (50.0 mg, 0.150 mmol; N,N-Dimethylglycine (18.6 mg, 0.180 mmol) N-(3-Dimethylaminopropyl)-N'-ethylcarbodiimide hydrochloride (34.6 mg, 0.180 mmol; and N,N-Dimethylformamide (0.999 mL, 12.9 mmol) were combined in a vial and stirred at rt for 1 hour. LCMS showed partial conversion to product. Stirred an additional 2 hours. Added 5 extra eq of acid, DIEA, HOBT, and EDCI and stirred for 18 h. Reaction went to completion. Diluted reaction mixture with sat'd NaHCO3 and filtered off resulting ppt. Ppt was purified by ISCO silica gel chromatography (0-100% EtOAc in hexanes). Conc down to recover title compound as a yellow solid (11 mg, 13%). LCMS=418.0 (M+H), HPLC purity=93%, rt=2.218 min. $^1$H NMR (400 MHz, CDCl3, δ, ppm): 9.03 (s, 1H), 8.72 (s, 2H), 8.52 (dd, J=2.4 Hz, 8.7 Hz, 1H), 7.85 (s, 1H), 7.42 (d, J=7.3 Hz, 1H), 7.32-7.28 (m, 2H), 6.95 (d, J=4.6 Hz, 1H), 6.90-6.87 (m, 2H), 6.85 (d, J=4.5 Hz, 1H), 4.00 (s, 3H), 3.09 (s, 2H), 2.37 (s, 6H).

Example 900

(R)-2-Methoxy-N-{3-[7-(6-methoxy-pyridin-3-yl)-pyrrolo[2,1-f][1,2,4]triazin-2-ylamino]-phenyl}-propionamide N-[7-(6-Methoxy-pyridin-3-yl)-pyrrolo[2,1-f][1,2,4]triazin-2-yl]-benzene-1,3-diamine (50.0 mg, 0.150 mmol), (R)-(+)-2-Methoxypropionic acid (18.8 mg, 0.180 mmol) N-(3-Dimethylaminopropyl)-N'-ethylcarbodiimide hydrochloride (34.6 mg, 0.180 mmol) and N,N-Dimethylformamide (0.999 mL, 12.9 mmol) were combined in a vial and stirred at rt for 1 hour. LCMS showed complete conversion to product. Diluted reaction mixture with sat'd NaHCO3 and filtered off resulting ppt. Took ppt up in CH$_2$Cl$_2$ and purified by ISCO silica gel chromatography (0-100%) EtOAc in hexanes to afford title compound (12 mg, 15%) LCMS=419.0 (M+H), HPLC rt=2.935 min, purity=99%. $^1$H NMR (400 MHz, CDCl3, δ, ppm): 8.74 (d, J=2.1 Hz, 1H), 8.72 (s, 1H), 8.48 (dd, J=2.6 Hz, 8.9H, 1H), 8.31 (s, 1H), 7.89 (s, 1H), 7.38-7.36 (m, 1H), 7.32-7.29 (m, 2H), 6.95-6.92 (m, 2H), 6.89 (d, J=8.6 Hz, 1H), 6.85 (d, J=4.5 Hz, 1H), 4.01 (s, 3H), 3.90-3.85 (m, 1H), 3.45 (s, 3H), 1.48 (d, J=7.1 Hz, 3H).

Example 901

1-Ethyl-3-{3-[7-(6-methoxy-pyridin-3-yl)-pyrrolo[2,1-f][1,2,4]triazin-2-ylamino]-phenyl}-urea To a solution of N-[7-(6-Methoxy-pyridin-3-yl)-pyrrolo[2,1-f][1,2,4]triazin-2-yl]-benzene-1,3-diamine (0.075 g, 0.22 mmol) in Methylene chloride (1.3 mL, 21 mmol) and Triethylamine (62.9 uL, 0.451 mmol) was added Ethane, isocyanato- (21.4 uL, 0.271 mmol) at 0° C. The reaction was stirred at 0° C. for 1 h. About 5% conversion. Allowed to stir at rt o/n—about 50% conversion. Heated to 50° C. for 3 hours and added additional 3.0 eq isocyanate. Reaction went to completion. Filtered off title compound as a beige ppt (34 mg, 35%). $^1$H NMR (400 MHz, (D3C)2SO, δ, ppm): 9.37 (s, 1H), 8.97 (s, 1H), 89.1 (j, J=2.3 Hz, 1 h), 8.55 (dd, J=8.7 Hz, 2.5 Hz, 1H), 8.29 (s, 1 h), 7.65 (s, 1H), 7.30 (d, J=8.1 Hz, 1H), 7.20 (d, J=4.6 Hz, 1H), 7.14 (dd, J=8.2 Hz, 8.2 Hz, 1H), 7.03 (d, J=8.6 Hz, 1H), 6.95 (d, J=4.8 Hz, 1H), 6.92 (d, J=8.4 Hz, 1H), 6.09 t, J=5.4 Hz, 1H) 3.92 (s, 3H), 3.09 (m, 2H), 1.04 (t, J=8.14 Hz, 3H). HPLC purity=90%, rt=2.029 min, LCMS=403.9 (M+H).

Example 902

N,N-Dimethyl-3-{2-[4-(1-methyl-piperidin-4-yl)phenylamino]-pyrrolo[2,1-f][1,2,4]triazin-7-yl}-benzenesulfonamide (7-Bromo-pyrrolo[2,1-f][1,2,4]triazin-2-yl)-[4-(1-methyl-piperidin-4-yl)-phenyl]-amine (84.3 mg, 0.000218 mol and N,N-dimethylaminosulfonyl-3-boronic acid (1.00E2 mg, 0.000436 mol) were reacted in an analogous manner to Example 881A for 8 hrs. The crude mixture was purified by Isco flash column chromatography (DCM/MeOH) to afford title compound (30 mg, 28% yield) LCMS=491.0 (M+H), HPLC purity=90%, rt=2.534. $^1$H NMR (400 MHz, (CDCl3, δ, ppm): 8.74 (s, 1H)m 8.48 (d, J=8.0 Hz, 1H), 8.37 (s, 1H), 7.73 (d, J=7.6 Hz, 1H), 7.65 (dd, J=8.1 Hz, 7.6 Hz, 1H), 7.53 (d, J=8.5 Hz, 2H), 7.23 (d, J=8.0 Hz, 2H), 7.04 (d, J=5.0 Hz, 1H), 6.91 (s, 1H), 6.86 (d, J=4.5 Hz, 1H), 3.06 (d, J=10.7 Hz, 2H), 2.73 (s, 6H), 2.54-2.50 (m, 1H), 2.40 (s, 3H), 2.21-2.14 (m, 2H), 1.88-1.85 (m, 4H).

Example 903

[4-(1-Methyl-piperidin-4-yl)-phenyl]-{7-[3-(pyrrolidine-1-sulfonyl)-phenyl]-pyrrolo[2,1-f][1,2,4]triazin-2-yl}-amine (7-Bromo-pyrrolo[2,1-f][1,2,4]triazin-2-yl)-[4-(1-methyl-piperidin-4-yl)-phenyl]-amine (84.3 mg, 0.000218 mol and pyrrolidineaminosulfonyl-3-boronic acid (110 mg, 0.000436 mol) were reacted in an analogous manner to Example 881A 8 hrs. The product was isolated via Gilson RP-HPLC. LCMS=517.0 (M+H), HPLC rt=2.128, purity=89%. 1H NMR (400 MHz, (D3C)2SO, δ, ppm): 9.53 (s, 1H), 9.28 (bs, 1H), 9.04 (s, 1H), 8.54 (s, 1H), 8.40 (d, J=6.8 Hz, 1H), 7.83-7.78 (m, 2H), 7.70 (d, J=8.3 Hz, 2H), 7.28 (d, J=4.6 Hz, 1H), 7.21 (d, J=8.3 Hz, 2H), 6.69 (d, J=4.6 Hz, 1H), 3.52 (d, J=11.7 Hz, 2H), 3.19-3.15 (m, 4H), 3.11-3.07 (m, 2H), 2.81 (d, J=3.5 Hz, 3H), 2.74-2.64 (m, 1H), 2.00 (d, J=11.7 Hz, 2H), 1.83-1.77 (m, 2H), 1.70-1.63 (m, 4H).

Example 904

N-Benzyl-3-{2-[4-(1-methyl-piperidin-4-yl)-phenylamino]-pyrrolo[2,1-f][1,2,4]triazin-7-yl}-benzenesulfonamide (7-Bromo-pyrrolo[2,1-f][1,2,4]triazin-2-yl)-[4-(1-methyl-piperidin-4-yl)-phenyl]-amine (84.3 mg, 0.000218 mol and benzylaminosulfonyl-3-boronic acid (120 mg, 0.000436 mol) were reacted in an analogous manner to Example 881A for 8 hrs. The product was isolated via Gilson RP-HPLC. LCMS=552.9 (M+H), HPLC rt=2.224 min, purity=99%. NMR (400 MHz, (D3C)2SO, δ, ppm): 9.53 (s, 1H), 9.28 (bs, 1H), 9.04 (s, 1H), 8.54 (s, 1H), 8.32 (d, J=7.9 Hz, 1H0, 8.23 (d, J=6.9 Hz, 1H), 7.82 (d, J=7.6 Hz, 1H), 7.74-7.70 (m, 3H), 7.23=7.18 (m, 8H), 7.00 (d, J=4.8 Hz, 1H), 4.02 (d, J=6.9 Hz, 3H), 3.50 (d, J=10.3 Hz, 2H), 3.08-3.03 (m, 2H), 2.81 (d, J=4.3 Hz, 2H), 2.73-2.66 (m, 1H), 1.97 (d, J=13 Hz, 2H), 1.78 (d, J=13 Hz, 2H).

Example 905

[4-(1-Methyl-piperidin-4-yl)-phenyl]-{7-[3-(piperidine-1-sulfonyl)-phenyl]-pyrrolo[2,1-f][1,2,4]triazin-2-yl}-amine (7-Bromo-pyrrolo[2,1-f][1,2,4]triazin-2-yl)-[4-(1-methyl-piperidin-4-yl)-phenyl]-amine (84.3 mg, 0.000218 mol) and piperidyl 3 boronic acid benzene sulfonamide (111 mg, 0.000414 mol), were reacted in an analogous manner to Example 881A for 8 hrs. The product was isolated via Gilson RP-HPLC (45 mg, 41%). LCMS=531.0 (M+H), HPLC rt=2.337 min, purity=98%, NMR (400 MHz, (D3C)2SO, δ, ppm): 9.53 (s, 1H), 9.28 (bs, 1H), 9.04 (s, 1H), 8.48 (s, 1H), 8.39 (d, J=8.4 Hz, 1H), 7.79-7.72 (m, 2H), 7.69 (d, J=8.4 Hz, 2H), 7.28 (d, J=4.3 Hz, 1H), 7.22 (d, J=8.4 Hz, 2H), 7.00 (d, J=4.3 Hz, 1H), 3.52 (d, J=10.7 Hz, 2H), 3.12-3.02 (m, 2H), 2.94-2.88 (m, 4H), 2.81 (d, 3.5 Hz, 3H), 2.78-2.65 (m, 1H), 1.98 (d, J=13 Hz, 2H), 1.87-1.75 (m, 2H), 1.55-1.46 (m, 4H), 1.35-1.23 (m, 2H).

Example 906

N-Cyclopropyl-3-{2-[4-(1-methyl-piperidin-4-yl)-phenylamino]-pyrrolo[2,1-f][1,2,4]triazin-7-yl}-benzenesulfonamide (7-Bromo-pyrrolo[2,1-f][1,2,4]triazin-2-yl)-[4-(1-methyl-piperidin-4-yl)-phenyl]-amine (84.3 mg, 0.000218 mol) and cyclopropyl 3 boronic acid benzene sulfonamide (99 mg, 0.000414 mol), were reacted in an analogous manner to Example 881A for 8 hrs. The product was isolated via Gilson RP-HPLC (15 mg, 14%). LCMS=502.9 (M+H), HPLC rt=1.910 min, purity=95%, NMR (400 MHz, (D3C)2SO, δ, ppm): 9.53 (s, 1H), 9.28 (bs, 1H), 9.04 (s, 1H), 8.58 (s, 1H), 8.35 (d, J=7.4 Hz, 1H), 7.97 (d, J=2.6 Hz, 1H), 7.84 (d, J=7.8 Hz, 1H), 7.79-7.75, (m, 1H), 7.71 (d, J=8.4 Hz, 2H), 7.23-7.20 (m, 3H), 7.00 (d, J=5.2 Hz, 1H), 3.51 (d, J=11.8 Hz, 2H), 3.09-3.05 (m, 2H), 2.81 (d, J=4.6 Hz, 3H), 2.77-2.65 (m, 1H), 2.15-2.12 (m, 1H), 2.00 (d, J=14 Hz, 2H), 1.82-1.76 (m, 2H), 0.47-0.43 (m, 2H), 0.40-0.38 (m, 2H).

Example 907

N-Ethyl-3-{2-[4-(1-methyl-piperidin-4-yl)-phenylamino]-pyrrolo[2,1-f][1,2,4]triazin-7-yl}-benzenesulfonamide (7-Bromo-pyrrolo[2,1-f][1,2,4]triazin-2-yl)-[4-(1-methyl-piperidin-4-yl)-phenyl]-amine (84.3 mg, 0.000218 mol) and N-ethyl-3-Boronic acid-benzenesulfonamide (107 mg, 0.466 mmol) were reacted in an analogous manner to Example 881A for 8 hrs. The product was isolated via Gilson RP-HPLC (21 mg, 24%). LCMS=491.0 (M+H), HPLC rt=2.532 min, 97% purity. $^1$H NMR (400 MHz, (D3C)2SO, δ, ppm): 9.55 (s, 1H), 9.30 (bs, 1H), 9.04 (s, 1H), 8.56 (s, 1H), 8.33 (d, J=7.8 Hz, 1H), 7.80 (d, 7.4 Hz, 1H), 7.76 (d, J=7.9 Hz, 1H), 7.73-7.70 (m, 2H), 7.64 (dd, J=5.4 Hz, 5.4 Hz, 1H), 7.22 (d, J=6.1 Hz, 3H), 7.00 (d, J=4.5 Hz, 1H), 3.52 (d, J=12.1 Hz, 2H), 3.12-3.02 (m, 2H), 2.81 (d, J=5.3 Hz, 3H), 2.80-2.65 (m, 3H), 1.99 (d, J=14.5 Hz, 2H), 1.86-1.74 (m, 2H), 0.97 (t, J=7.2 Hz, 3H).

Example 908

[3-Methoxy-4-(1-methyl-piperidin-4-yl)-phenyl]-[7-(2-methoxy-phenyl)-pyrrolo[2,1-f][1,2,4]triazin-2-yl]-amine 908A. 4-(2-Methoxy-4-nitro-phenyl)-3,6-dihydro-2H-pyridine-1-carboxylic acid tert-butyl ester. 1-Chloro-2-methoxy-4-nitro-benzene (1.11681 g, 5.95377 mmol), 4-(4,4,5,5-Tetramethyl-[1,3,2]dioxaborolan-2-yl)-3,6-dihydro-2H-pyridine-1-carboxylic acid tert-butyl ester (1.84 g, 5.95 mmol), Tetrakis(triphenylphosphine)palladium(0) (379.43 mg, 0.32835 mmol), 1.50 M of Sodium carbonate in Water (9.9230 mL, 14.884 mmol;), and 1,4-Dioxane (17.87 mL, 229.0 mmol) were combined in a sealed tube, and the mixture was heated at 80° C. for 16 h. HPLC indicated complete conversion. The reaction mixture was diluted with EtOAc and washed with H2O, dried over MgSO4, filtered, and concentrated. The product was isolated by flash chromatography (Silicagel, EtOAc/Hexanes 0-50%). HPLC rt=4.030 min, LCMS=335.0 (M+H) Obtained title compound as a pale yellow solid (1.72 g, 86%)

908B. 4-(4-Amino-2-methoxy-phenyl)-piperidine-1-carboxylic acid tert-butyl ester. 4-(2-Methoxy-4-nitro-phenyl)-3,6-dihydro-2H-pyridine-1-carboxylic acid tert-butyl ester was suspended in methanol and 10% Palladium on Carbon (50% Wet) (0.1 eq) was added. The mixture was shaken in a Parr apparatus under an atmosphere of Hydrogen (50 PSI) for 3 hours to overnight. The reaction mixture was filtered through Celite and solvent was removed under vacuum to afford title compound (764 mg, 97%). LCMS=251.0 (M-tert butyl).

908C. 3-Methoxy-4-(1-methyl-piperidin-4-yl)-phenylamine. To a suspension of Lithium tetrahydroaluminate (946 mg, 24.9 mmol) in Tetrahydrofuran (27.8 mL, 342 mmol) at 0° C. was added a solution of 4-(4-Amino-2-methoxy-phenyl)-piperidine-1-carboxylic acid tert-butyl ester (764 mg, 2.49 mmol) in Tetrahydrofuran (27.8 mL, 342 mmol), and then the reaction was allowed first to warm to room temperature and then to 70° C. for 3 hours. LCMS indicated 85% desired product. Continued heating 2 h. Cooled, then Na2SO4×10H2O (1 g) was slowly added (gas evolution!), and the reaction was stirred at room temperature for 0.5 h. The suspension was filtered, and the solids were extensively washed with DCM. The combined organics were dried (MgSO4), and the solvent was evaporated in vacuum to afford title compound (500 mg, 91%). LCMS=221.0 (M+H).

908D. [3-Methoxy-4-(1-methyl-piperidin-4-yl)-phenyl]-[7-(2-methoxy-phenyl)-pyrrolo[2,1-f][1,2,4]triazin-2-yl]-amine. Trifluoro-methanesulfonic acid 7-(2-methoxy-phenyl)-pyrrolo[2,1-f][1,2,4]triazin-2-yl ester (0.100 g, 0.268 mmol) and 3-Methoxy-4-(1-methyl-piperidin-4-yl)-phenylamine (0.0738 g, 0.335 mmol)(1.25 eq) were combined in DMF and DIEA (2.0 eq) and stirred at room temp for 72 h. Alternatively, the triflate was formed in situ from the respective 2-hydroxy pyrrolotriazine and N-Phenylbis(trifluoromethanesulphonimide) (1.1 eq). The reaction mixture was concentrated, taken up in EtOAc, and washed with brine. The EtOAc layer was dried, filtered over MgSO4, and concentrated. The resulting residue was purified by Gilson RP-HPLC and lyophilized. HPLC rt=2.625 min, purity=99%, LCMS=444.0 (M+H). $^1$H NMR (400 MHz, (D3C)2SO, δ, ppm): 9.37 (s, 1H), 9.28 (bs, 1H), 8.96 (s, 1H), 7.70 (d, J=7.8 Hz, 1H), 7.46-7.42 (m, 2H), 7.21-7.16 (m, 2H), 7.07 (dd, J=7.3 Hz, 7.3 Hz, 1H), 6.93-6.88 (m, 3H), 3.76 (s, 3H), 3.46 (d, J=11.2 Hz, 2H), 3.42 (s, 3H), 3.11-2.86 (m, 3H), 2.78 (d, J=4.6 Hz, 3H), 1.90-1.72 (m, 4H).

Example 909

[7-(6-Methoxy-pyridin-3-yl)-pyrrolo[2,1-f][1,2,4]triazin-2-yl]-(4-[1,2,3]thiadiazol-4-yl-phenyl)-amine Trifluoro-methanesulfonic acid 7-(6-methoxy-pyridin-3-yl)-pyrrolo[2,1-f][1,2,4]triazin-2-yl ester (0.138 g, 0.369 mmol and 4-[1,2,3]Thiadiazol-4-yl-phenylamine (0.0817 g, 0.461 mmol) were reacted in an analogous manner to Example 908D at 50° overnight. The reaction mixture was filtered and the resulting solid was washed with acetone to give the title compound as a pale yellow solid (36 mg, 24%). HPLC rt=3.347, purity=99%. LCMS=401.9 (M+H). $^1$H NMR (400 MHz, (D3C)2SO, δ, ppm): 9.81 (s, 1H), 9.52 (s, 1H), 9.04 (s, 1H), 8.93 (d, J=2.0 Hz, 1H), 8.54 (dd, J=8.7 Hz, 2.3 Hz, 1H), 8.08 (d, J=7.9 Hz, 2H), 7.91 (d, J=8.6 Hz, 2H), 7.21 (d, J=4.4 Hz, 1H), 7.08 (d, J=8.7 Hz, 1H), 7.00 (d, J=4.3 Hz, 1H), 3.96 (s, 3H).

Example 910

[3-Methoxy-4-(1-methyl-piperidin-4-yl)-phenyl]-[7-(6-methoxy-pyridin-3-yl)-pyrrolo[2,1-f][1,2,4]triazin-2-yl]-amine. Trifluoro-methanesulfonic acid 7-(6-methoxy-pyridin-3-yl)-pyrrolo[2,1-f][1,2,4]triazin-2-yl ester (0.138 g, 0.369 mmol) and 3-Methoxy-4-(1-methyl-piperidin-4-yl)-phenylamine (0.102 g, 0.461 mmol) were reacted in an analogous manner to Example 908D at room temp for 72 h. The reaction mixture was concentrated, taken up in EtOAc, and washed with brine. The EtOAc layer was dried, filtered over MgSO4, and concentrated. The resulting residue was purified by Gilson RP-HPLC and lyophilized. HPLC rt=2.455 min, purity=98%, LCMS=445.0 (M+H). $^1$H NMR (400 MHz, (D3C)2SO, δ, ppm): 9.47 (s, 1H), 9.29 (bs, 1H), 9.02 (s, 1H), 8.99 (d, 1H), 7.47 (s, 1H0, 7.23 (d, J=7.5 Hz, 1H), 7.17 (d, J=4.8 Hz, 1H), 7.03 (d, J=8.2 Hz, 1H), 7.17 (d, J=4.8 Hz, 1H), 7.03 (d, J=8.2 Hz, 1H), 6.98 (s, 1H), 6.96 A (d, J=4.1 Hz, 1H), 3.93 (s, 3H), 3.71 (s, 3H), 3.49 (d, J=11.7 Hz, 2H), 3.11-3.05 (m, 3H), 2.80 (d, J=4.0 Hz, 3H), 1.95-1.76 (m, 4H).

Example 911

2-(4-{2-Methoxy-4-[7-(6-methoxy-pyridin-3-yl)-pyrrolo[2,1-f][1,2,4]triazin-2-ylamino]-phenyl}-piperidin-1-yl)-acetamide 911A. 4-(2-Methoxy-4-nitro-phenyl)-1,2,3,6-tetrahydro-pyridine. 4-(2-Methoxy-4-nitro-phenyl)-3,6-dihydro-2H-pyridine-1-carboxylic acid tert-butyl ester (0.860 g, 2.57 mmol) was treated with Trifluoroacetic Acid (0.7746 mL, 10.05 mmol) in Methylene chloride (5 mL, 80 mmol). Stirred at rt for 4 hours. HPLC rt=1.719 min. Minimum amount of saturated sodium carbonate added, and extensive extraction (DCM) to afford title compound, after drying (MgSO4) and evaporation of solvent. Product was taken forward without purification.

911B. 2-[4-(2-Methoxy-4-nitro-phenyl)-3,6-dihydro-2H-pyridin-1-yl]-acetamide. Into a 1-Neck round-bottom flask was added 4-(2-Methoxy-4-nitro-phenyl)-1,2,3,6-tetrahydro-pyridine (0.599 g, 0.00256 mol), Iodoacetamide (0.473 g, 0.00256 mol), and Cesium Carbonate (1.25 g, 0.00384 mol), in Acetonitrile (24 mL, 0.47 mol), and the reaction was stirred 16 h at reflux. The reaction mixture was cooled and water was added to dissolve inorganics. The reaction mixture was concentrated until a yellow ppt formed. The ppt was collected by filtration, was washed with water, then dried under high vacuum. LCMS=291.9 (M+H)

911C. 2-[4-(4-Amino-2-methoxy-phenyl)-piperidin-1-yl]-acetamide. 2-[4-(2-Methoxy-4-nitro-phenyl)-3,6-dihydro-2H-pyridin-1-yl]-acetamide was reduced in an analogous manner to Example 908B for 16 h. Title compound was afforded and was used without further purification. LCMS=264.0 (M+H)

911D. 2-(4-{2-Methoxy-4-[7-(6-methoxy-pyridin-3-yl)-pyrrolo[2,1-f][1,2,4]triazin-2-ylamino]-phenyl}-piperidin-1-yl)-acetamide. Trifluoro-methanesulfonic acid 7-(6-methoxy-pyridin-3-yl)-pyrrolo[2,1-f][1,2,4]triazin-2-yl ester (0.138 g, 0.369 mmol; and 2-[4-(4-Amino-2-methoxy-phenyl)-piperidin-1-yl]-acetamide (0.121 g, 0.461 mmol) were reacted in an analogous manner to Example 908D at room temp for 72 h. The reaction mixture was concentrated, taken up in EtOAc, and washed with brine. The EtOAc layer was dried, filtered over MgSO4, and concentrated. The resulting residue was purified by Gilson RP-HPLC and lyophilized to afford title compound as a TFA salt (59 mg, 33%). LCMS=488.0 (M+H), HPLC rt=2.329, purity=99%. $^1$H NMR (400 MHz, (D3C)2SO, δ, ppm): 9.53 (bs, 1H), 9.47 (s, 1H), 9.02 (s, 1H), 9.00 (d, J=8.2 Hz, 1H), 8.40 (dd, J=8.7 Hz, 2.3 Hz, 1H), 7.98 (s, 1H), 7.71 (s, 1H), 7.46 (s, 1H), 7.24 (d, J=8.5 Hz, 1H), 7.17 (d, J=4.9 Hz, 1H), 7.04 (d, J=8.3 Hz, 1H0, 6.97 (d, J=4.7 Hz, 1H), 6.93 (s, 1H), 3.93 (s, 3H), 3.89 (m, 2H), 3.70 (s, 3H), 3.54 (d, J=11.7 Hz, 2H), 3.23-3.05 (m, 3H), 2.05-1.95 (m, 2H), 1.85-1.88 (m, 2H).

Example 912

2-(4-{2-Methoxy-4-[7-(2-methoxy-phenyl)-pyrrolo[2,1-f][1,2,4]triazin-2-ylamino]-phenyl}-piperidin-1-yl)-acetamide Trifluoro-methanesulfonic acid 7-(2-methoxy-phenyl)-pyrrolo[2,1-f][1,2,4]triazin-2-yl ester (0.100 g, 0.268 mmol)

and 2-[4-(4-Amino-2-methoxy-phenyl)-piperidin-1-yl]-acetamide (0.0882 g, 0.335 mmol) were reacted in an analogous manner to Example 908D at 50° C. for 16 h. The reaction mixture was concentrated, taken up in EtOAc, and washed with brine. The EtOAc layer was dried, filtered over MgSO4, and concentrated. The resulting residue was purified by Gilson RP-HPLC and lyophilized. The product was taken up in EtOAc and washed with NaHCO3 to free-base it to afford title compound (44 mg, 32%). LCMS=487.0 (M+H), HPLC rt=2.500, purity=98%. $^1$H NMR (400 MHz, (D3C)2SO, δ, ppm): 9.29 (s, 1H), 8.94 (s, 1H), 7.70 (d, J=7.3 Hz, 1H), 7.45 (dd, J=7.3, 7.7 Hz, 1H), 7.37 (s, 1H), 7.19 (d, J=8.3 Hz, 2H), 7.08 (d, J=7.4 Hz, 1H), 6.97 (d, J=8.3 Hz, 1H0, 6.91 (d, J=4.3 Hz, 1H), 6.88 (d, J=4.3 Hz, 1H), 3.76 (s, 3H), 3.42 (s, 3H), 3.31 (s, 2H), 2.89-2.82 (m, 3H), 2.80-2.68 (m, 1H), 2.20-2.05 (m, 2H), 1.72-1.58 (m, 4H).

Example 913

N-(2-{2-[3-Methoxy-4-(1-methyl-piperidin-4-yl)-phenylamino]-pyrrolo[2,1-f][1,2,4]triazin-7-yl}-phenyl)-N-methyl-methanesulfonamide Trifluoro-methanesulfonic acid 7-[2-(methanesulfonyl-methyl-amino)-phenyl]-pyrrolo[2,1-f][1,2,4]triazin-2-yl ester (0.121 g, 0.268 mmol) and 3-Methoxy-4-(1-methyl-piperidin-4-yl)-phenylamine (0.0738 g, 0.335 mmol) were reacted in an analogous manner to Example 908D rt for 72 h. The reaction mixture was concentrated, taken up in EtOAc, and washed with brine. The EtOAc layer was dried, filtered over MgSO4, and concentrated. The resulting residue was purified by Gilson RP-HPLC and lyophilized to afford title compound as a TFA salt (84 mg, 62%). LCMS=521.0 (M+H), HPLC=2.319 min, purity=99%, $^1$H NMR (400 MHz, (D3C)2SO, δ, ppm): 9.42 (s, 1H), 9.28 (bs, 1H), 8.98 (s, 1H), 7.76 (dd, J=7.1 Hz, 1.7 Hz, 1H), 7.64 (d, J=7.6 Hz, 1H), 7.55-7.48 (m, 3H), 7.04 (dd, J=8.4 Hz, 1.4 Hz, 1H), 6.95 (d, J=4.6 Hz, 1H), 6.92-6.88 (m, 2H), 3.45 (d, J=11.0 z, 2H), 3.24 (s, 3H), 3.08 (s, 3H), 3.07-2.88 (m, 2H), 2.80-2.78 (m, 6H), 1.83-1.70 (m, 4H).

Example 914

2-[4-(4-{7-[2-(Methanesulfonyl-methyl-amino)-phenyl]-pyrrolo[2,1-f][1,2,4]triazin-2-ylamino}-2-methoxy-phenyl)-piperidin-1-yl]-acetamide Trifluoro-methanesulfonic acid 7-[2-(methanesulfonyl-methyl-amino)-phenyl]-pyrrolo[2,1-f][1,2,4]triazin-2-yl ester (0.121 g, 0.268 mmol) and 2-[4-(4-Amino-2-methoxy-phenyl)-piperidin-1-yl]-acetamide (0.0882 g, 0.335 mmol) were reacted in an analogous manner to Example 908D for 72 h at rt. The reaction mixture was concentrated, taken up in EtOAc, and washed with brine. The EtOAc layer was dried, filtered over MgSO4, and concentrated. The resulting residue was purified by Gilson RP-HPLC and lyophilized to afford title compound as a TFA salt (86 mg, 62%). LCMS=564.0 (M+H), HPLC=2.210 min, purity=97%. $^1$H NMR (400 MHz, (D3C)2SO, δ, ppm): 9.49 (bs, 1H), 9.42 (s, 1H), 8.98 (s, 1H), 7.96 (s, 1H), 7.76 (dd, J=7.3 Hz, 1.8 Hz, 1H), 7.70 (s, 1H), 7.64 (dd, J=7.6 Hz, 1.4 Hz, 1H), 7.56-7.48 (m, 3H), 3.88 (d, J=3.4 Hz, 2H), 3.51 (d, J=8.7 Hz, 2H), 3.25 (s, 3H), 3.17-3.12 (m, 2H), 3.08 (s, 3H), 3.03-2.96 (m, 1H), 2.79 (s, 3H), 1.95-1.88 (m, 2H), 1.81-1.77 (m, 2H).

Example 915

[7-(2-Methoxy-phenyl)-pyrrolo[2,1-f][1,2,4]triazin-2-yl]-(2-methyl-1,2,3,4-tetrahydro-isoquinolin-6-yl)-amine 915A. 2-Methyl-1,2,3,4-tetrahydro-isoquinolin-6-ylamine. 6-Amino-3,4-dihydro-1H-isoquinoline-2-carboxylic acid tert-butyl ester was reacted in an analogous manner to Example 908c and was taken forward to the next step without further purification.

915B. [7-(2-Methoxy-phenyl)-pyrrolo[2,1-f][1,2,4]triazin-2-yl]-(2-methyl-1,2,3,4-tetrahydro-isoquinolin-6-yl)-amine 915B. Trifluoro-methanesulfonic acid 7-(2-methoxy-phenyl)-pyrrolo[2,1-f][1,2,4]triazin-2-yl ester (0.0939 g, 0.251 mmol) and 2-Methyl-1,2,3,4-tetrahydro-isoquinolin-6-ylamine (0.051 g, 0.31 mmol) were reacted in an analogous manner to Example 908D. The resulting residue was purified by Gilson RP-HPLC and lyophilized to afford title compound as a TFA salt (81 mg, 84%). HPLC rt=2.396 min, purity=98%, LCMS=386.0 (M+H). $^1$H NMR (400 MHz, (D3C)2SO, δ, ppm): 9.91 (bs, 1H), 9.52 (s, 1H), 8.97 (s, 1H), 7.80 (dd, J=7.8 Hz, 1.4 Hz, 1H), 7.73 (s, 1H), 7.45 (m, 2H), 7.23 (d, J=8.7 Hz, 1H), 7.14 (dd, J=7.3 Hz, 7.3 Hz, 1H), 7.04 (d, J=8.7 Hz, 1H), 6.95 (m, 2H), 4.40 (d, J=14.5 Hz, 1H), 4.21-4.16 (m, 1H), 3.79 (s, 3H), 3.66-3.62 (m, 1H), 3.31-3.29 (m, 1H), 3.08-2.95 (m, 1H), 2.91 (d, J=3.9 Hz, 3H), 2.90-2.83 (m, 1H).

Example 916

2-{6-[7-(6-Methoxy-pyridin-3-yl)-pyrrolo[2,1-f][1,2,4]triazin-2-ylamino]-3,4-dihydro-1H-isoquinolin-2-yl}-acetamide 916A 1,2,3,4-Tetrahydro-isoquinolin-6-ylamine. 6-Amino-3,4-dihydro-1H-isoquinoline-2-carboxylic acid tert-butyl ester (0.345 g, 1.39 mmol) was treated with Trifluoroacetic Acid (0.418 mL, 5.42 mmol) in Methylene chloride (3.00 mL). Partial conversion after 3 h, added additional 1 ml TFA and allowed to stir at rt for 16 h. Complete conversion to more polar peak on LCMS. Reaction mixture was concentrated to an orange film which was used without purification in the next reaction.

916B. 2-(6-Amino-3,4-dihydro-1H-isoquinolin-2-yl)-acetamide. 1,2,3,4-Tetrahydro-isoquinolin-6-ylamine (0.206 g, 0.00139) was reacted in an analogous manner to 911B. DMF (3 ml) was added to solubilize reactant. The reaction was heated to 80° C. for several hours and allowed to stir at rt over the weekend. LCMS showed very polar peak with mass of 206.0 (M+H). HPLC rt=0.404 min. After filtration and concentration, the resulting residue was taken up in DMF and used in the next step without purification.

916C. 7-(6-Methoxy-pyridin-3-yl)-pyrrolo[2,1-f][1,2,4]triazin-2-ol (0.0609 g, 0.251 mmol) and 2-(6-Amino-3,4-dihydro-1H-isoquinolin-2-yl)-acetamide (0.064 g, 0.31) were reacted in an analogous manner to Example 908D at 50° C. for 16 h. The reaction mixture was concentrated and purified by Gilson RP-HPLC. HPLC rt=2.083 min, purity=91%. $^1$H NMR (400 MHz, (D3C)2SO, δ, ppm): 10.23 (bs, 1H), 9.63 (s, 1H), 9.10 (s, 1H), 9.01 (s, 1H), 8.44 (dd, J=8.9 Hz, 2.2 Hz, 1H), 7.96 (s, 1H), 7.91 (s, 1H), 7.75 (s, 1H), 7.40 (d, J=8.9 Hz, 1H), 7.21 (d, J=4.4 Hz, 1H), 7.13 (d, J=8.9 Hz, 1H), 7.04

(d, J=8.6 Hz, 1H), 6.98 (d, J=4.5 Hz, 1H), 4.50 (m, 1H), 4.33 (m, 1H), 4.05 (m, 2H), 3.95 (s, 3H), 3.70 (m, 1H), 3.43 (m, 1H), 3.23 (m, 1H), 3.08 (m, 1H).

Example 917

2-{6-[7-(2-Methoxy-phenyl)-pyrrolo[2,1-f][1,2,4]triazin-2-ylamino]-3,4-dihydro-1H-isoquinolin-2-yl}-acetamide Trifluoro-methanesulfonic acid 7-(2-methoxy-phenyl)-pyrrolo[2,1-f][1,2,4]triazin-2-yl ester (0.0939 g, 0.251 mmol) and 2-(6-Amino-3,4-dihydro-1H-isoquinolin-2-yl)-acetamide (0.064 g, 0.31 mmol) were reacted in an analogous manner to Example 908D at room temp for 16 h. The resulting residue was purified by Gilson RP-HPLC and lyophilized to afford title compound as a TFA salt (29 mg, 26%). HPLC rt=2.283 min, purity=98%, LCMS=429.0 (M+H). $^1$H NMR (400 MHz, (D3C)2SO, δ, ppm): 10.20 (bs, 1H), 9.52 (s, 1H), 8.97 (s, 1H), 7.94 (s, 1H), 7.79 (d, J=7.7 Hz, 1H), 7.74 (s, 2H), 7.48-7.42 (m, 2H), 7.23 (d, J=8.7 Hz, 1H), 7.14 (dd, J=7.7 Hz, 7.7 Hz, 1H), 7.06 (d, J=8.2 Hz, 1H), 6.97-6.93 (m, 2H), 4.42 (m, 1H), 4.27 (m, 1H), 7.00 (d, J=9.5 Hz, 2H), 3.79 (s, 3H), 3.65 (m, 1H), 3.39 (m, 1H), 3.04 (m, 1H), 2.83 (m, 1H).

Example 918

2-(6-{7-[2-(Methanesulfonyl-methyl-amino)-phenyl]-pyrrolo[2,1-f][1,2,4]triazin-2-ylamino}-3,4-dihydro-1H-isoquinolin-2-yl)-acetamide Trifluoro-methanesulfonic acid 7-[2-(methanesulfonyl-methyl-amino)-phenyl]-pyrrolo[2,1-f][1,2,4]triazin-2-yl ester (0.113 g, 0.251 mmol) and 2-(6-Amino-3,4-dihydro-1H-isoquinolin-2-yl)-acetamide (0.064 g, 0.31 mmol) were reacted in an analogous manner to Example 908D at rt for 16 h. The resulting residue was purified by Gilson RP-HPLC and lyophilized to afford title compound as a TFA salt (17 mg, 11%). HPLC rt=1.989 min, purity=98%, LCMS=506.0 (M+H). $^1$H NMR (400 MHz, (D3C)2SO, δ, ppm): 10.28 (bs, 1H), 9.54 (s, 1H), 8.88 (s, 1H), 7.97-7.93 (m, 2H), 7.74 (s, 1H), 7.67-7.64 (m, 2H), 7.59-7.55 (m, 2H), 7.38 (d, J=8.2 Hz, 1H), 7.05 (d, J=8.8 Hz, 1H), 6.99-6.96 (m, 2H), 4.46-4.42 (m, 1H), 4.27-4.25 (m, 1H), 4.00 (d, J=8.1 Hz, 2H), 3.66-3.62 (m, 1H), 3.40-3.38 (m, 1H), 3.07 (s, 3H), 3.02-3.00 (m, 1H), 2.88 (s, 3H), 2.82-2.80 (m, 1H).

Example 919

[7-(6-Methoxy-pyridin-3-yl)-pyrrolo[2,1-f][1,2,4]triazin-2-yl]-(2-methyl-1,2,3,4-tetrahydro-isoquinolin-6-yl)-amine 919A. (2-methyl-1,2,3,4-tetrahydro-isoquinolin-6-yl)-amine. 6-Amino-3,4-dihydro-1H-isoquinoline-2-carboxylic acid tert-butyl ester (0.345 g, 1.39 mmol) was reacted in an analogous manner to Example 908C to afford title compound which was taken forward to the next step without further purification (154 mg, 68%).

919B. [7-(6-Methoxy-pyridin-3-yl)-pyrrolo[2,1-f][1,2,4]triazin-2-yl]-(2-methyl-1,2,3,4-tetrahydro-isoquinolin-6-yl)-amine. Trifluoro-methanesulfonic acid 7-(6-methoxy-pyridin-3-yl)-pyrrolo[2,1-f][1,2,4]triazin-2-yl ester (0.0738 g, 0.197 mmol) and 2-Methyl-1,2,3,4-tetrahydro-isoquinolin-6-ylamine (0.040 g, 0.25 mmol) were reacted in an analogous manner to Example 908D at 50° C. for 16 h. The reaction mixture was purified by Gilson RP-HPLC and lyophilized to afford title compound as a TFA salt (15 mg, 16%) LCMS=387.0 (M+H), HPLC rt=2.239 min, purity=97%. $^1$H NMR (400 MHz, (D3C)2SO, δ, ppm): $^1$H NMR (400 MHz, (D3C)2SO, δ, ppm): 9.86 (bs, 1H), 9.64 (s, 1H), 9.05 (s, 1H), 8.01 (s, 1H), 8.42 (dd, J=8.6 Hz, 2.4 Hz, 1H), 7.94 (s, 1H), 7.39 (d, J=8.7 Hz, 1H), 7.21 (d, J=4.7 Hz, 1H), 7.13 (d, J=8.7 Hz, 1H), 7.02 (d, J=8.8 Hz, 1H), 6.99 (d, J=4.7 Hz, 1H), 4.45 (d, J=16.7 Hz, 1H), 4.28-4.24 (m, 1H), 3.94 (s, 3H), 3.75-3.70 (m, 1H), 3.45-3.33 (m, 2H), 3.25-3.08 (m, 3H), 2.95 (d, J=4.3 Hz, 3H).

Example 920

2-{6-[7-(3-tert-Butylsulfamoyl-phenyl)-pyrrolo[2,1-f][1,2,4]triazin-2-ylamino]-3,4-dihydro-1H-isoquinolin-2-yl}-acetamide N-tert-Butyl-3-(2-hydroxy-pyrrolo[2,1-f][1,2,4]triazin-7-yl)-benzenesulfonamide (0.0822 g, 0.237 mmol) and 2-(6-Amino-3,4-dihydro-1H-isoquinolin-2-yl)-acetamide (0.0609 g, 0.297 mmol) were reacted in an analogous manner to Example 908D at 50° C. for 16 h. The reaction mixture was concentrated, taken up in DMSO, and purified by Gilson RP-HPLC and lyophilized to afford title compound as a TFA salt (26 mg, 20%). LCMS=534.0, HPLC rt=2.518, purity=96%. $^1$H NMR (400 MHz, (D3C)2SO, δ, ppm): 10.22 (bs, 1H), 9.67 (s, 1H), 9.07 (s, 1H), 8.46 (d, J=8.2 Hz, 1H), 8.43 (s, 1H), 7.96 (s, 1H), 7.85 (d, J=6.5 Hz, 1H), 7.78-7.74 (m, 2H), 7.70 (s, 1H), 7.63 (s, 1H), 7.58 (d, j=8.2 Hz, 1H), 7.21 (d, J=4.8 Hz, 1H), 7.17 (d, J=8.4 Hz, 1H), 7.02 (d, J=4.6 Hz, 1H), 4.47-4.45 (m, 1H), 4.33-4.31 (m, 1H), 4.04-s, 2H), 3.67-3.65 (m, 1H), 3.42-3.41 (m, 1H), 3.15-3.13 (m, 1H), 2.98-2.96 (m, 1H), 1.11 (s, 9H).

Example 921

N-tert-Butyl-3-[2-(2-methyl-1,2,3,4-tetrahydro-isoquinolin-6-ylamino)-pyrrolo[2,1-f][1,2,4]triazin-7-yl]-benzenesulfonamide N-tert-Butyl-3-(2-hydroxy-pyrrolo[2,1-f][1,2,4]triazin-7-yl)-benzenesulfonamide (0.109 g, 0.316 mmol) and 2-Methyl-1,2,3,4-tetrahydro-isoquinolin-6-ylamine (0.064 g, 0.39 mmol) were reacted in an analogous manner to Example 908D at rt for 16 h. The reaction mixture was concentrated, taken up in EtoAc, and washed with water. The organic layer was dried over MgSO4, filtered, and concentrated. The resulting solid was purified by ISCO silica gel chromatography (0-10% MeOH in CH$_2$Cl$_2$) to afford title compound (81 mg, 52%). HPLC purity=96%, rt=2.654, LCMS=491.0 (M+H) $^1$H NMR (400 MHz, (D3C)2SO, δ, ppm): 9.48 (s, 1H), 9.04 (s, 1H), 8.50 (d, J=7.9 Hz, 1H), 8.39 (s, 1H), 7.84 (d, J+7.4 Hz, 1H), 7.73 (dd, J=7.9 Hz, 7.9 Hz, 1H), 7.61 (s, 1H), 7.58 (s, 1H0, 7.48 (dd, J=8.3 Hz, 1.67 Hz, 1H), 7.18 (d, J=4.7 Hz, 1H), 7.03 (d, J=8.3 Hz, 1H), 7.00 (d, J=4.8 Hz, 1H), 3.67-3.61 (m, 2H), 2.85 (s, 3H), 2.80-2.70 (m, 2H), 2.48-2.42 (m, 2H), 1.11 (s, 9H).

Example 922

6-Fluoro-7-[7-(2-methoxy-phenyl)-pyrrolo[2,1-f][1,2,4]triazin-2-ylamino]-3,4-dihydro-1H-quinolin-2-one Trifluoro-methanesulfonic acid 7-(2-methoxy-phenyl)-pyrrolo[2,1-f][1,2,4]triazin-2-yl ester (0.080 g, 0.21 mmol) and 7-Amino-6-fluoro-3,4-dihydro-1H-quinolin-2-one (0.045 g, 0.25 mmol) were reacted in an analogous manner to Example 908D at 50° C. for 16 h. The product was triturated and washed with acetone. LC/MS: 403.9 (M+H)HPLC: 2.966 min, 99% purity. MP: 300-305° C. $^1$H NMR (400 MHz, CDCl3, δ, ppm): 8.57 (s, 1H), 7.91 (d, J=7.6 Hz, 1H) 7.62-7.53 (m, 2 h), 7.44 (s, 1H), 7.24-7.23 (m, 1H), 7.19-7.01 (m, 6H), 7.17-7.10 (m, 3H), 7.08 (s, 1H), 8.89 (s, 3H), 2.94 (t, 2H), 2.66, (t, 2H).

Example 923

2-(4-{4-[7-(3-Methanesulfonyl-phenyl)-pyrrolo[2,1-f][1,2,4]triazin-2-ylamino]-2-methoxy-phenyl}-piperidin-1-yl)-acetamide Trifluoro-methanesulfonic acid 7-(3-methanesulfonyl-phenyl)-pyrrolo[2,1-f][1,2,4]triazin-2-yl ester (0.070 g, 0.17 mmol) and 2-[4-(4-Amino-2-methoxy-phenyl)-piperidin-1-yl]-acetamide (0.0547 g, 0.208 mmol) were reacted in an analogous manner to Example 908D at 50° C. for 16 h. The resulting residue was purified by Gilson RP-HPLC and lyophilized to afford title compound as a TFA salt (39 mg, 44%). LCMS=535.0 (M+H), HPLC=2.304 min, purity=97%. $^1$H NMR (400 MHz, (D3C)2SO, δ, ppm): 9.56 (bs, 1H), 9.51 (s, 1H), 9.06 (s, 1H), 8.63 (s, 1H), 8.44 (d, J=7.8 Hz, 1H), 7.98 (s, 1H), 7.94 (d, J=7.8 Hz, 1H), 7.79 (dd, J=7.8 Hz, 7.8 Hz, 1H), 7.72 (s, 1H), 7.51 (d, J=7.8 Hz, 1H), 7.29 (d, J=4.6 Hz, 1H), 7.20 (d. J=1, 1 Hz, 1H), 7.14 (d, J=8.5 Hz, 1H), 7.01 (d, J=4.7 Hz, 1H), 3.90 (d, J=3.4 Hz, 2H), 3.65 (s, 3H), 3.54 (d, J=11.3 Hz, 1H), 3.28 (s, 3H), 3.23-3.15 (m, 2H), 3.04-3.12 (m, 1H), 1.99-1.84 (m, 4H).

Example 924

2-(4-{4-[7-(3-tert-Butylsulfamoyl-phenyl)-pyrrolo[2,1-f][1,2,4]triazin-2-ylamino]-2-methoxy-phenyl}-piperidin-1-yl)-acetamide N-tert-Butyl-3-(2-hydroxy-pyrrolo[2,1-f][1,2,4]triazin-7-yl)-benzenesulfonamide (0.0747 g, 0.216 mmol) and 2-[4-(4-Amino-2-methoxy-phenyl)-piperidin-1-yl]-acetamide (0.0710 g, 0.270 mmol) were reacted in an analogous manner to Example 908D at 50° C. overnight. The reaction mixture was concentrated and purified by Gilson RP-HPLC followed by lyophilization to afford title compound as a TFA salt (78 mg, 61%). HPLC rt=2.728 min, purity=99%. LCMS=592.1 (M+H), $^1$H NMR (400 MHz, (D3C)2SO, δ, ppm): 9.57 (bs, 1H), 9.49 (s, 1H), 9.05 (s, 1H), 8.49 (s, 1H), 8.36 (d, J=7.7 Hz, 1H), 7.97 (s, 1H), 7.84 (d, J=7.7 Hz, 1H), 7.97 (s, 1H), 7.84 (d, J=7.7 Hz, 1H), 7.71-7.69 (m, 2H), 7.60 (s, 1H), 7.47 (d, J=8.6 Hz, 1H), 7.26 (s, 1H), 7.18 (d, J=4.4 Hz, 1H), 7.13 (d, J=8.5 Hz, 1H), 7.01 (d, J=4.4 Hz, 1H), 3.89 (d, J=4.2 Hz, 2H), 3.63 (s, 3H), 3.55-3.52 (m, 2H), 3.19-3.16 (m, 2H), 3.07-3.03 (m, 1H), 1.97-1.89 (m, 2H), 1.88-1.84 (m, 2H), 1.09 (s, 9H).

Example 925

2-{5-[7-(2-Methoxy-phenyl)-pyrrolo[2,1-f][1,2,4]triazin-2-ylamino]-1,3-dihydro-isoindol-2-yl}-acetamide 925A. 2-(5-Amino-1,3-dihydro-isoindol-2-yl)-acetamide. 2,3-Dihydro-1H-isoindol-5-ylamine dihydrochloride (0.500 g, 0.00241 mol) was reacted in an analogous manner to Example 911B. DMF (3 ml) was added to solubilize reactant. The reaction was heated to 80° C. for 6 h and allowed to stir at rt for 72 h. The resulting residue was taken up in DMF and used in the next step without purification. LCMS 192 (M+H).

925B. Trifluoro-methanesulfonic acid 7-(2-methoxy-phenyl)-pyrrolo[2,1-f][1,2,4]triazin-2-yl ester (0.111 g, 0.298 mmol) and 2-(5-Amino-1,3-dihydro-isoindol-2-yl)-acetamide (0.077 g, 0.40 mmol) were reacted in an analogous manner to Example 908D at 50° C. for 16 h in methoxypropanol. Pale yellow solid was filtered off, washed with water. Found to be pure product (35 mg, 28%). LCMS=414.9 (M+H), HPLC rt=2.256 min, purity=99%. $^1$H NMR (400 MHz, (D3C)2SO, δ, ppm): 9.40 (s, 1H), 8.95 (s, 1H), 7.78 (d, J=7.4 Hz, 1H), 7.75 (s, 1H), 7.47 (dd, J=7.6 Hz, 1H), 7.39 (d, J=8.6 Hz, 1H), 7.32 (s, 1H), 7.21 (d, J=8.6 Hz, 1H), 7.13-7.05 (m, 3H), 6.94 (d, J=4.6 Hz, 1H), 6.90 (d, J=4.6 Hz, 1H), 3.89 (s, 4H0, 3.78 (s, 3H), 3.27 (s, 2H).

Example 926

2-{5-[7-(6-Methoxy-pyridin-3-yl)-pyrrolo[2,1-f][1,2,4]triazin-2-ylamino]-1,3-dihydro-isoindol-2-yl}-acetamide Trifluoro-methanesulfonic acid 7-(6-methoxy-pyridin-3-yl)-pyrrolo[2,1-f][1,2,4]triazin-2-yl ester (0.112 g, 0.298 mmol) and 2-(5-Amino-1,3-dihydro-isoindol-2-yl)-acetamide (0.077 g, 0.40 mmol) were reacted in an analogous manner to Example 908D at 50° C. for 16 h in methoxypropanol. Yellow solid precipitated out which was filtered off and washed with water (47 mg, 38%). Found to be pure desired product. LCMS=415.9 (M+H), HPLC rt=2.039 min, purity=96%. $^1$H NMR (400 MHz, (D3C)2SO, δ, ppm): 9.51 (s, 1H), 9.02 (s, 1H), 8.98 (s, 1H), 8.42 (dd, J=8.7 Hz, 2.3 Hz, 1H), 7.89 (s, 1H), 7.37 (d, J=8.6 Hz, 1H), 7.34 (s, 1H), 7.18-7.10 (m, 3H), 6.99-6.95 (m, 2H), 4.01 (s, 2H), 3.94 (s, 5H), 3.29 (s, 2H).

Example 927

2-{5-[7-(3-tert-Butylsulfamoyl-phenyl)-pyrrolo[2,1-f][1,2,4]triazin-2-ylamino]-1,3-dihydro-isoindol-2-yl}-acetamide N-tert-Butyl-3-(2-hydroxy-pyrrolo[2,1-f][1,2,4]triazin-7-yl)-benzenesulfonamide (0.112 g, 0.322 mmol and 2-(5-Amino-1,3-dihydro-isoindol-2-yl)-acetamide (0.077 g, 0.40 mmol) were reacted in an analogous manner to Example 908D at 50° C. for 16 h. The reaction was dried under vacuum and purified by Gilson RP HPLC and lyophilized to afford title compound as a TFA salt (64 mg, 38%). LCMS=519.9 (M+H), HPLC rt=2.466 min, purity=98%, $^1$H NMR (400 MHz, (D3C)2SO, δ, ppm): 10.86 (bs, 1H), 9.77 (s, 1H), 9.07 (s, 1H), 8.50 (s, 1H), 8.40 (d, J=7.2 Hz, 1H), 7.94 (s, 1H), 7.85 (d, J=7.5 Hz, 1H), 7.79 (s, 1H), 7.75 (d, J=8.0 Hz, 1H), 7.72-7.68 (m, 2H), 7.64 (s, 1H), 7.36 (d, j=8.4 Hz, 1H), 7.23 (d, J=4.8 Hz, 1H), 7.03 (d, J=4.8 Hz, 1H), 4.79-4.77 (m, 2H), 4.56-4.49 (m, 2H), 4.23 (s, 2H), 1.11 (s, 9H).

Example 928

2-[4-(4-{7-[3-(Pyrrolidine-1-sulfonyl)-phenyl]-pyrrolo[2,1-f][1,2,4]triazin-2-ylamino}-phenyl)-piperidin-1-yl]-acetamide 928A. 2-{4-[4-(7-Bromo-pyrrolo[2,1-f][1,2,4]triazin-2-ylamino)-phenyl]-piperidin-1-yl}-acetamide. 7-Bromo-pyrrolo[2,1-f][1,2,4]triazin-2-ol (0.550 g, 2.57 mmol) and 2-[4-(4-Amino-phenyl)-piperidin-1-yl]-acetamide (0.750 g, 3.21 mmol) were reacted in an analogous manner to Example 908D at 50° C. for 6 h. The reaction mixture was concentrated, diluted with water, and extracted with ethyl acetate. The organic layer was dried over MgSO4, filtered, concentrated and purified by ISCO chromatography using dichloromethane/methanol (0-15%). (670 mg, 58%) LC/MS: 430.9 (M+H); HPLC: retention time 2.307 min $^1$H NMR (400 MHz, DMSO, δ, ppm): 9.60 (s, 1H), 8.90 (s, 1H), 7.81 (d, J=8.5 Hz, 2H), 7.21 (d, J=8.5 Hz, 1H), 7.25-7.08 (m, 2H), 6.94 (d, J=4.7 Hz, 1H), 6.89 (d, J=4.6 Hz, 1H), 3.03-2.77 (m, 4H), 2.25-1.99 (m, 2H), 1.83-1.74 (m, 4H) (37%, 43 mg)

928B. 2-{4-[4-(7-Bromo-pyrrolo[2,1-f][1,2,4]triazin-2-ylamino)-phenyl]-piperidin-1-yl}-acetamide (88.9 mg, 0.207 mmol) and 3-(Pyrrolidine-1-sulfonyl)-boronic acid (106 mg, 0.000414 mol), were reacted in an analogous manner to Example 881A at 80° C. for 4 h. The product was isolated via Gilson RP-HPLC to afford title compound as a TFA salt (43 mg, 37%). LCMS=560. 0 (M+H), HPLC rt=2.062, 97% purity. $^1$H NMR (400 MHz, (D3C)2SO, δ, ppm): 9.60 (bs, 1H), 9.55 (s, 1H), 9.04 (s, 1H), 8.52 (s, 1H), 8.42 (d, J=6.8 Hz, 1H), 7.98 (s, 1H), 7.83-7.77 (m, 2H), 7.73-7.69 (m, 3H), 7.29 (d, J=4.6 Hz, 1H), 7.22 (d, J=7.6 Hz, 2H), 6.99 (d, J=4.6 Hz, 1H), 3.91 (d, J=2.9 Hz, 2H), 3.55 (d, J=11.4 Hz, 2H), 3.13-3.09 (m, 4H), 2.76-2.72 (m, 1H), 1.97-1.93 (m, 4H), 1.66-1.64 (m, 6H).

Example 929

2-(4-{4-[7-(3-Ethylsulfamoyl-phenyl)-pyrrolo[2,1f][1,2,4]triazin-2-ylamino]-phenyl}-piperidin-1-yl)-acetamide 2-{4-[4-(7-Bromo-pyrrolo[2,1-f][1,2,4]triazin-2-ylamino)-phenyl]-piperidin-1-yl}-acetamide (88.9 mg, 0.207 mmol), and N-ethyl-3-Boronic acid-benzenesulfonamide (94.9 mg, 0.414 mmol), were reacted in an analogous manner to Example 881A at 80° C. for 4 hours. The product was isolated via Gilson RP-HPLC (54 mg, 50%). LCMS=534.0 (M+H), HPLC rt=2.386, 99% purity, $^1$H NMR (400 MHz, (D3C)2SO, δ, ppm): 9.62 (bs, 1H), 9.55 (s, 1H), 9.04 (s, 1H), 8.55 (s, 1H), 8.34 (d, J=7.6 Hz, 1H), 7.98 (d, J=7.6 Hz, 1H), 7.76 (d, J=6.9 Hz, 1H), 7.72-7.70 (m, 3H), 7.64 (dd, J=5.5 Hz, 5.5 Hz, 1H), 7.23-7.20 (m, 3H), 7.00 (d, J=4.5 Hz, 1H), 3.91 (d, J=3.5 Hz, 2H), 3.55 (d, J=9.4 Hz, 2H), 3.18-3.14 (m, 2H), 2.80 (q, J=6.7 Hz, 2H), 2.77-2.69 (m, 1H), 2.01-1.95 (m, 4H), 0.97 (t, J=7.2 Hz, 3H).

Example 930

2-(4-{4-[7-(3-Cyclopropylsulfamoyl-phenyl)-pyrrolo[2,1-f][1,2,4]triazin-2-ylamino]-phenyl}-piperidin-1-yl)-acetamide 2-{4-[4-(7-Bromo-pyrrolo[2,1-f][1,2,4]triazin-2-ylamino)-phenyl]-piperidin-1-yl}-acetamide (88.9 mg, 0.207 mmol), and 3-(cyclopropyl-1-sulfonyl)-boronic acid (99.8 mg, 0.414 mmol) were reacted in an analogous manner to Example 881A at 80° C. for 4 hours. The product was isolated via Gilson RP-HPLC (38 mg, 34%). LCMS=546.0 (M+H), HPLC rt=2.437, purity=99%, $^1$H NMR (400 MHz, (D3C)2SO, δ, ppm): 9.62 (bs, 1H), 9.55 (s, 1H0, 9.04 (s, 1H), 8.54 (s, 1H), 8.37 (d, J=8.4 Hz, 1H), 7.99-7.96 (m, 2H), 7.83 (d, J=7.3 Hz, 1H), 7.79-7.77 (m, 2H), 7.73-7.70 (m, 3H) 7.23-7.20 (m, 3H), 7.01 (d, J=4.7 Hz, 1H), 3.91 (d, J=4.1 Hz, 2H), 3.52-3.51 (m, 2H), 3.18-3.16 (m, 2H), 2.74-2.72 (m, 1H), 2.14-2.12 (m, 1H), 2.03-1.95 (m, 4H), 0.47-0.44 (m, 2H), 0.40-0.38 (m, 2H).

Example 931

N-tert-Butyl-3-[2-(2-methyl-1,2,3,4-tetrahydro-isoquinolin-7-ylamino)-pyrrolo[2,1-f][1,2,4]triazin-7-yl]-benzenesulfonamide 931A. 2-Methyl-1,2,3,4-tetrahydro-isoquinolin-7-ylamine. 7-Amino-3,4-dihydro-1H-isoquinoline-2-carboxylic acid tert-butyl ester (0.500 g, 2.01 mmol) was reacted in an analogous manner to Example 908C. Product was used without further purification. (327 mg, 75%). LC/MS: 163 (M+H) HNMR: $^1$H NMR (400 MHz, DMSO, δ, ppm): 6.72 (d, J=7.9 Hz, 1H), 6.34 (d, J=8.3 Hz, 1H), 6.21 (s, 1H), 4.76 (s, 2H), 2.27 (t, 2H), 3.33 (s, 2H), 2.62 (t, 2H), 2.28 (s, 3H)

931B. N-tert-Butyl-3-[2-(2-methyl-1,2,3,4-tetrahydro-isoquinolin-7-ylamino)-pyrrolo[2,1-f][1,2,4]triazin-7-yl]-benzenesulfonamide N-tert-Butyl-3-(2-hydroxy-pyrrolo[2,1-f][1,2,4]triazin-7-yl)-benzenesulfonamide (0.109 g, 0.316 mmol) and 2-Methyl-1,2,3,4-tetrahydro-isoquinolin-7-ylamine (0.064 g, 0.39 mmol) were reacted in an analogous manner to Example 908D at 50° C. for 16 h. The reaction mixture was concentrated, taken up in DMSO, purified by Gilson RP HPLC and lyophilized to afford title compound as a TFA salt (38 mg, 25%). LCMS=491 (M+H), HPLC rt=2.649 min, 95% purity. $^1$H NMR (400 MHz, (D3C)2SO, δ, ppm): 9.90 (bs, 1H), 9.68 (s, 1H), 9.06 (s, 1H), 8.50 (s, 1H), 8.37 (d, J=8.5 Hz, 1H), 7.88 (d, J=8.5 Hz, 1H), 7.79 (dd, J=7.6 Hz, 7.6 Hz, 1H), 7.66-7.58 (m, 3H), 7.24-7.20 (m, 2H), 7.02 (m, 4.6 Hz, 1H), 4.37 (d, J=14.9 Hz, 1H), 4.32-4.24 (m, 1H), 3.68-3.65 (m, 1H), 3.35-3.28 (m, 1H), 3.15 (s, 1H), 3.12-3.00 (m, 1H), 2.95 (d, J=4.3 Hz, 3H), 1.10 (s, 9H).

Example 932

3-(4-{2-[4-(1-Methyl-piperidin-4-yl)-phenylamino]-pyrrolo[2,1-f][1,2,4]triazin-7-yl}-pyrazol-1-yl)-propionitrile 932A. 3-[4-(4,4,5,5-Tetramethyl-1,3,2-dioxaborolan-2-yl)-pyrazol-1-yl]-propionitrile To a suspension of 4-(4,4,5,5-Tetramethyl-1,3,2-dioxaborolan-2-yl)-1H-pyrazole (1.882 g, 9.699 mmol) and Potassium carbonate (2.0 g, 14 mmol) in Acetone (20 mL, 300 mmol) was added 3-Bromo-propionitrile (0.96 mL, 12 mmol). The mixture was stirred at 60° C. overnight. Filtering off the Potassium carbonate and concentration of the acetone gave an orange oil. HNMR analysis showed desired product (2.30 g, 96%). The product was used without further purification.

932B. (7-Bromo-pyrrolo[2,1-f][1,2,4]triazin-2-yl)-[4-(1-methyl-piperidin-4-yl)-phenyl]-amine (1.00E2 mg, 0.259 mmol), and 3-[4-(4,4,5,5-Tetramethyl-1,3,2-dioxaborolan-2-yl)-pyrazol-1-yl]-propionitrile (128 mg, 0.518 mmol) were reacted in an analogous manner to Example 881A at 80° C. for 8 h. The reaction mixture was purified via ISCO silica gel chromatography using an amine capped column 50-100% EtOAc in hexanes (32 mg, 29%). LCMS=427.0 (M+H), HPLC rt=1.889 min, 96% purity. $^1$H NMR (400 MHz, (D3C)2SO, δ, ppm): 9.32 (s, 1H), 8.88 (s, 1H), 8.54 (s, 1H), 8.27 (s, 1H), 7.65 (d, J=7.6 Hz, 2H), 7.25 (d, J=8.5 Hz, 2H), 7.08 (d, J=4.3 Hz, 1H), 6.91 (d, J=4.7 Hz, 1H), 4.47 (t, J=6.4 Hz, 2H), 3.16 (t, J=6.5 Hz, 2H), 2.87 (d, J=10.8 Hz, 2H), 2.46-2.40 (m, 1H), 2.19 (s, 3H), 1.96 (t, J=10.8 Hz, 2H), 1.76-1.62 (m, 4H).

Example 933

2-[4-(4-{7-[1-(2-Cyano-ethyl)-1H-pyrazol-4-yl]-pyrrolo[2,1-f][1,2,4]triazin-2-ylamino}-phenyl)-piperidin-1-yl]-acetamide 2-{4-[4-(7-Bromo-pyrrolo[2,1-f][1,2,4]triazin-2-ylamino)-phenyl]-piperidin-1-yl}-acetamide (111 mg, 0.259 mmol) and 3-[4-(4,4,5,5-Tetramethyl-1,3,2-dioxaborolan-2-yl)-pyrazol-1-yl]-propionitrile (128 mg, 0.518 mmol) were reacted in an analogous manner to Example 881A. The resulting crude product was purified by ISCO chromatography (amine capped silica gel) with a gradient of 50-100% EtOAc in hexanes-30% MeOH in EtOAc (41 mg, 34%). LCMS=470.0 (M+H), HPLC rt=1.825 min, 95% purity. $^1$H NMR (400 MHz, (D3C)2SO, δ, ppm): 9.32 (s, 1H), 8.89 (s, 1H), 8.54 (s, 1H), 8.28 (s, 1H), 7.66 (d, J=8.5 Hz, 2H), 7.26 (d, J=8.5 Hz, 2H), 7.22 (bs, 1H), 7.14 (bs, 1H), 7.07 (d, J=4.3 Hz, 1H), 6.91 (d, J=4.3 Hz, 1H), 4.48 (t, J=6.4 Hz, 2H), 3.16 (t, J=6.4 Hz, 2H), 2.92 (d, J=10.5 Hz, 2H), 2.88 (s, 2H), 2.47-2.44 (m, 1H), 2.18-2.13 (m, 2H), 1.76-1.74 (m, 4H).

Example 934

2-(4-{4-[7-(6-Methoxy-pyridin-3-yl)-pyrrolo[2,1-f][1,2,4]triazin-2-ylamino]-2-methyl-phenyl}-piperidin-1-yl)-acetamide 934A. 4-(2-Methyl-4-nitro-phenyl)-3,6-dihydro-2H-pyridine-1-carboxylic acid tert-butyl ester. 1-Chloro-2-methyl-4-nitro-benzene (1.21 g, 7.05 mmol) was reacted in an analogous manner to Example 908A at 65° C. for 16 h. The product was purified by ISCO chromatography using ethyl acetate/hexane (0-100%). LCMS=418.2 and 304.0. HNMR consistent. (1.00 g, 45%)

934B. 4-(2-Methyl-4-nitro-phenyl)-1,2,3,6-tetrahydropyridine. 4-(2-Methyl-4-nitro-phenyl)-3,6-dihydro-2H-pyridine-1-carboxylic acid tert-butyl ester (0.500 g, 0.00157 mol) was reacted in an analogous manner to Example 911A at rt for 16 h. Complete conversion to a new peak (LCMS=219.1). Reaction was concentrated to off-white solid and used in the next step without further purification.

934C. 2-[4-(2-Methyl-4-nitro-phenyl)-3,6-dihydro-2H-pyridin-1-yl]-acetamide. 4-(2-Methyl-4-nitro-phenyl)-1,2,3,6-tetrahydro-pyridine (0.343 g, 0.00157 mol), was reacted in an analogous manner to Example 911B at reflux for 16 h. Product ppt'd out. The reaction mixture was cooled, diluted with water, and partially concentrated. The reaction mixture was filtered and the resulting ppt was washed with water. LCMS=276.0 (M+H). HPLC rt=1.774 min. White solid (386 mg, 89%). Product was taken through without further purification.

934D. 2-[4-(4-Amino-2-methyl-phenyl)-piperidin-1-yl]-acetamide was reduced in an analogous manner to Example 908B for 6 h. Title compound was afforded and was used without further purification. (303 mg, 87%) 6 hours. LCMS=248.0 (M+H).

934E. 2-(4-{4-[7-(6-Methoxy-pyridin-3-yl)-pyrrolo[2,1-f][1,2,4]triazin-2-ylamino]-2-methyl-phenyl}-piperidin-1-yl)-acetamide. Trifluoro-methanesulfonic acid 7-(6-methoxy-pyridin-3-yl)-pyrrolo[2,1-f][1,2,4]triazin-2-yl ester (0.112 g, 0.298 mmol) and 2-[4-(4-Amino-2-methyl-phenyl)-piperidin-1-yl]-acetamide (0.10 g, 0.40 mmol) were reacted in an analogous manner to Example 908D at 50° C. for 16 h in methoxypropanol. Filtered off yellow ppt and washed with methoxy propanol. Obtained pure product (26 mg, 18%). LCMS=472.0 (M+H), HPLC rt=2.351 min, purity=93%, $^1$H NMR (400 MHz, (D3C)2SO, δ, ppm): 9.36 (s, 1H), 9.02 (s, 1H), 8.96 (s, 1H), 8.46 (dd, J=8.7 Hz, 2.2 Hz, 1H), 7.77 (s, 1H), 7.33 (d, J=8.7 Hz, 1H), 7.23 (s, 1H), 7.18-7.12 (m, 3H), 6.99 (d, J=8.5 Hz, 1H), 6.95 (d, J=4.6 Hz, 1H), 3.93 (s, 3H), 2.92 (d, J=11.4 Hz, 1H), 2.88 (s, 2H), 2.63-2.61 (m, 1H), 2.32 (s, 3H), 2.19-2.17 (m, 2H), 1.78-1.62 (m, 4H).

Example 935

2-(4-{4-[7-(2-Methoxy-phenyl)-pyrrolo[2,1-f][1,2,4]triazin-2-ylamino]-2-methyl-phenyl}-piperidin-1-yl)-acetamide 7-(2-Methoxy-phenyl)-pyrrolo[2,1-f][1,2,4]triazin-2-ol (0.0573 g, 0.237 mmol) and 2-[4-(4-Amino-2-methyl-phenyl)-piperidin-1-yl]-acetamide (0.0734 g, 0.297 mmol) were reacted in an analogous manner to Example 908D at 50° C. for 16 h. Concentrated reaction mixture, took up in DMSO, and purified by Gilson RP-HPLC. The fractions containing desired product were lyophilized to afford title compound as a TFA salt (75 mg, 67%). LCMS=471.0 (M+H), HPLC rt=2.468 min, purity=99%, $^1$H NMR (400 MHz, (D3C)2SO, δ, ppm): 9.52 (bs, 1H), 9.31 (s, 1H), 8.94 (s, 1H), 7.97 (s, 1H), 7.84 (d, J=7.1 Hz, 1H), 7.72 (s, 1H), 7.60 (s, 1H0, 7.47-7.43 (m, 2H), 7.21 (d, J=7.7 Hz, 1H), 7.12 (dd, J=7.7 Hz, 7.7 Hz, 1H), 6.98 (d, J=8.7 Hz, 1H), 6.95 (d, J=4.6 Hz, 1H), 6.91 (d, J=4.6 Hz, 1H), 3.91 (d, J=4.3 Hz, 2H), 3.79 (s, 3H), 3.53 (d, J=10.9 Hz, 2H), 3.20-3.15 (m, 2H), 2.91-2.89 (m, 1H), 2.20 (s, 3H), 1.99-1.95 (m, 2H), 1.83-1.80 (m, 2H).

Example 936

N-tert-Butyl-3-[2-(2-methyl-2,3-dihydro-1H-isoindol-5-ylamino)-pyrrolo[2,1-f][1,2,4]triazin-7-yl]-benzenesulfonamide 936A. 2-Methyl-2,3-dihydro-1H-isoindol-5-ylamine. 5-Amino-1,3-dihydro-isoindole-2-carboxylic acid tert-butyl ester (0.500 g, 2.13 mmol) was reacted in an analogous manner to Example 908C to afford title compound (246 mg, 78%) which was taken forward without further purification.

936B. N-tert-Butyl-3-[2-(2-methyl-2,3-dihydro-1H-isoindol-5-ylamino)-pyrrolo[2,1-f][1,2,4]triazin-7-yl]-benzenesulfonamide. N-tert-Butyl-3-(2-hydroxy-pyrrolo[2,1-f][1,2,4]triazin-7-yl)-benzenesulfonamide (0.0822 g, 0.237 mmol) and 2-Methyl-2,3-dihydro-1H-isoindol-5-ylamine (0.0440 g, 0.297 mmol) were reacted in an analogous manner to Example 908D at 50° C. for 16 h. Concentrated reaction mixture, took up in DMSO, and purified by Gilson RP-HPLC. The fractions containing desired product were lyophilized to afford title compound as a TFA salt (18 mg, 16%). LCMS=477.0 (M+H), HPLC rt=2.643 min, purity=95%, $^1$H NMR (400 MHz, (D3C)2SO, δ, ppm) 10.55 (bs, 1H), 9.79 (s, 1H), 9.08 (s, 1H), 8.53 (d, J=7.8 Hz, 1H), 8.38-8.36 (m, 1H), 7.87 (d, j=7.6 Hz, 1H), 7.82 (s, 1H), 7.78-7.67 (m, 2H), 7.64 (s, 1H), 7.42-7.35 (m, 1H), 7.23 (d, J=4.7 Hz, 1H), 7.03 (d, J=4.3 Hz, 1H), 4.81-4.94 (m, 2H), 4.47-4.42 (m, 1H), 3.28 (m, 2H), 3.03 (m, 2H).

Example 937

[7-(6-Methoxy-pyridin-3-yl)-pyrrolo[2,1-f][1,2,4]triazin-2-yl]-(2-methyl-2,3-dihydro-1H-isoindol-5-yl)-amine Trifluoro-methanesulfonic acid 7-(6-methoxy-pyridin-3-yl)-pyrrolo[2,1-f][1,2,4]triazin-2-yl ester (0.112 g, 0.298 mmol) and 2-Methyl-2,3-dihydro-1H-isoindol-5-ylamine (0.060 g, 0.40 mmol) were reacted in an analogous manner to Example 908D at 50° C. for 16 h. Concentrated reaction mixture, took up in DMSO, and purified by Gilson RP-HPLC. The fractions containing desired product were lyophilized to afford title compound as a TFA salt (11 mg, 10%). LCMS=373.0 (M+H), HPLC rt=2.175 min, purity=96%, $^1$H NMR (400 MHz, (D3C)2SO, δ, ppm): 9.80 (s, 1H), 9.06 (s, 1H), 8.96 (d, J=1.9 Hz, 1H), 8.48 (dd, J=8.8 Hz, 2.2 Hz, 1H), 7.48 (s, 1H), 7.62 (d, J=8.4 Hz, 1H), 7.39 (d, J=8.0 Hz, 1H), 7.23 (d, J=4.4 Hz, 1H), 7.05 (d, J=8.7 Hz, 1H), 7.00 (d, J=4.7 Hz, 1H), 4.87 (s, 2H), 4.80 (s, 2H), 3.96 (s, 3H), 3.31 (s, 3H).

Example 938

2-(4-{4-[7-(3-tert-Butylsulfamoyl-phenyl)-pyrrolo[2,1-f][1,2,4]triazin-2-ylamino]-2-methyl-phenyl}-piperidin-1-yl)-acetamide N-tert-Butyl-3-(2-hydroxy-pyrrolo[2,1-f][1,2,4]triazin-7-yl)-benzenesulfonamide (0.0822 g, 0.237 mmol) and 2-[4-(4-Amino-2-methyl-phenyl)-piperidin-1-yl]-acetamide (0.0734 g, 0.297 mmol) were reacted in an analogous manner to Example 908D at 50° C. for 16 h. Concentrated reaction mixture, took up in DMSO, and purified by Gilson RP-HPLC. The fractions containing desired product were lyophilized to afford title compound as a TFA salt (90 mg, 66%). LCMS=576.1 (M+H), HPLC rt=2.724, purity=93%, $^1$H NMR (400 MHz, (D3C)2SO, δ, ppm): 9.60 (bs, 1H), 9.45 (s, 1H), 9.04 (s, 1H), 8.48 (d, J=8.11 Hz, 1H), 8.44 (s, 1H), 7.98 (s, 1H), 7.85 (d, J=7.7 Hz, 1H), 7.72-7.69 (m, 2H), 7.60 (d, J=7.7 Hz, 1H), 7.72-7.69 (m, 2H), 7.60 (d, J=7.7 Hz, 1H), 7.59 (s, 1H), 7.54 (s, 1H), 7.19 (d, J=4.6 Hz, 1H), 7.16 (d, J=8.3 Hz, 1H), 6.99 (d, J=4.6 Hz, 1H), 3.90 (s, 2H), 3.56-3.54 (m, 2H), 3.21-3.18 (m, 2H), 2.94-2.92 (m, 1H), 2.23 (s, 3H), 2.00-1.98 (m, 2H), 1.88-1.86 (m, 2H), 1.11 (s, 9H).

Example 939

2-(4-{2-Acetylamino-4-[7-(6-methoxy-pyridin-3-yl)-pyrrolo[2,1-f][1,2,4]triazin-2-ylamino]-phenyl}-piperidin-1-yl)-acetamide 939A. N-(2-Chloro-5-nitro-phenyl)-acetamide. 2-Chloro-5-nitro-phenylamine (1.410 g, 8.171 mmol) was dissolved in 1,2-Dichloroethane (20 mL,) at room temperature. N,N-Diisopropylethylamine (1.56 mL, 8.99 mmol) was added followed by Acetyl chloride (1.28 mL, 18.0 mmol). Reaction mixture was stirred at 45° C. for 16 h. Reaction mixture was diluted with CH$_2$Cl$_2$ and washed with sat'd NaHCO3, dried over magnesium sulfate and filtered and reduced in vacuo (1.62, 92%).

939B. 4-(2-Acetylamino-4-nitro-phenyl)-3,6-dihydro-2H-pyridine-1-carboxylic acid tert-butyl ester. N-(2-Chloro-5-nitro-phenyl)-acetamide (1.617 g, 7.535 mmol) and 4-(4,4,5,5-Tetramethyl-[1,3,2]dioxaborolan-2-yl)-3,6-dihydro-2H-pyridine-1-carboxylic acid tert-butyl ester (2.33 g, 7.55) were reacted in an analogous manner to Example 881A at 65° C. for 16 h. The product was purified by ISCO chromatography using ethyl acetate/hexane (0-100%). LCMS=262.0 (M-BOC). (70%, 1.90 g).

938C. N-[5-Nitro-2-(1,2,3,6-tetrahydro-pyridin-4-yl)-phenyl]-acetamide. 4-(2-Acetylamino-4-nitro-phenyl)-3,6-dihydro-2H-pyridine-1-carboxylic acid tert-butyl ester (1.90 g, 0.00526 mol) was reacted in an analogous manner to Example 911A. LCMS=262.0 (M+H), rt=0.54 min. (905 mg, 66%). 939D. 2-[4-(2-Acetylamino-4-nitro-phenyl)-3,6-dihydro-2H-pyridin-1-yl]-acetamide. N-[5-Nitro-2-(1,2,3,6-tetrahydro-pyridin-4-yl)-phenyl]-acetamide (0.500 g, 0.00191 mol) was reacted in an analogous manner to Example 911B at rt for 16 h. The product was purified by ICSO silica gel chromatography 0-20% MeOH in CH2Cl2 (446 mg, 73%). LCMS=318.9 (M+H).

939E. 2-[4-((2-Acetylamino-4-amino-phenyl)-piperidin-1-yl]-acetamide. 2-[4-(2-Acetylamino-4-nitro-phenyl)-3,6-dihydro-2H-pyridin-1-yl]-acetamide (0.446 g, 1.40 mmol) was reacted in an analogous manner to Example 908B for 6 hours. LCMS=291.0 (M+H) white foam (74 mg, 18%).

939F. 2-(4-{2-Acetylamino-4-[7-(6-methoxy-pyridin-3-yl)-pyrrolo[2,1-f][1,2,4]triazin-2-ylamino]-phenyl}-piperidin-1-yl)-acetamide. Trifluoro-methanesulfonic acid 7-(6-methoxy-pyridin-3-yl)-pyrrolo[2,1-f][1,2,4]triazin-2-yl ester (70.7 mg, 0.189 mmol) and 2-[4-((2-Acetylamino-4-amino-phenyl)-piperidin-1-yl]-acetamide (0.074 g, 0.25 mmol) were reacted in an analogous manner to Example 908D at 50° C. for 16 h. The reaction mixture was concentrated, taken up in DMSO, and purified by Gilson RP-HPLC to afford title compound as a TFA salt (38 mg, 39%). LCMS=515.1 (M+H), HPLC rt=1.948 min, purity=97%, $^1$H NMR (400 MHz, (D3C)2SO, δ, ppm): 9.56 (s, 1H), 9.50 (bs, 1H), 9.44 (s, 1H), 8.99 (s, 1H), 8.82 (d, J=2.3 Hz, 1H), 8.55 (dd, J=8.8 Hz, 1.8 Hz, 1H), 7.97 (s, 1H), 7.71 (s, 2H), 7.53 (d, J=8.6 Hz, 1H), 7.19 (d, J=4.5 Hz, 1H), 7.15 (d, J=8.6 Hz, 1H), 7.00-6.96 (m, 2H), 3.95 (s, 3H), 3.91 (d, J=4.0 Hz, 2H), 3.54 (d, J=11.1 Hz, 2H), 3.16-3.11 (m, 2H), 2.89-2.84 (m, 1H), 2.00 (s, 3H), 2.01-1.97 (m, 2H), 1.86-1.83 (m, 2H).

Example 940

N-tert-Butyl-3-{2-[3-methyl-4-(1-methyl-piperidin-4-yl)-phenylamino]-pyrrolo[2,1-f][1,2,4]triazin-7-yl}-benzenesulfonamide 940A. 1-Methyl-4-(2-methyl-4-nitro-phenyl)-1,2,3,6-tetrahydro-pyridine. 4-(2-Methyl-4-nitro-phenyl)-3,6-dihydro-2H-pyridine-1-carboxylic acid tert-butyl ester (0.500 g, 1.57 mmol) was reacted in an analogous manner to Example 908C and was taken forward to the next step without further purification (330 mg, 90%). HPLC rt=1.703 min.

940B. 3-Methyl-4-(1-methyl-piperidin-4-yl)-phenylamine. 1-Methyl-4-(2-methyl-4-nitro-phenyl)-1,2,3,6-tetrahydro-pyridine (0.326 g, 1.40 mmol) was reacted in an analogous manner to Example 911C. (225 mg, 75%). LCMS=205.2 (M+H).

940C. N-tert-Butyl-3-{2-[3-methyl-4-(1-methyl-piperidin-4-yl)-phenylamino]-pyrrolo[2,1-f][1,2,4]triazin-7-yl}-benzenesulfonamide. N-tert-Butyl-3-(2-hydroxy-pyrrolo[2,1-f][1,2,4]triazin-7-yl)-benzenesulfonamide (0.102 g, 0.294 mmol) and 3-Methyl-4-(1-methyl-piperidin-4-yl)-phenylamine (0.0750 g, 0.367 mmol) were reacted in an analogous manner to Example 908D at 50° C. for 16 h. Concentrated reaction mixture, took up in DMSO, and purified by Gilson RP-HPLC. The fractions containing desired product were lyophilized to afford title compound as a TFA salt (64 mg, 41%). LCMS=533.1 (M+H), HPLC rt=2.822, purity=95%, $^1$H NMR (400 MHz, (D3C)2SO, δ, ppm): 9.45 (s, 1H), 9.32 (bs, 1H0, 9.03 (s, 1H), 8.46 (d, J=8.2 Hz, 1H), 7.85 (d, J=8.2 Hz, 1H), 7.71 (dd, J=7.1 Hz, 7.1 Hz, 1H), 7.60-7.54 (m, 3H), 7.19 9 d, J=4.6 Hz, 1H), 7.13 (d, J=8.6 Hz, 1H), 7.00 (d, J=4.6 Hz, 1H), 3.52 (d, J=11.4 Hz, 2H0, 3.15-3.09 (m, 2H), 2.96-2.93 (m, 1H), 2.82 (d, J=4.7 Hz, 3H), 2.28 (s, 3H), 1.92-1.88 (m, 2H), 1.87-1.78 (m, 2H), 1.10 (s, 9H).

Example 941

[7-(6-Methoxy-pyridin-3-yl)-pyrrolo[2,1-f][1,2,4]triazin-2-yl]-[3-methyl-4-(1-methyl-piperidin-4-yl)-phenyl]-amine Trifluoro-methanesulfonic acid 7-(6-methoxy-pyridin-3-yl)-pyrrolo[2,1-f][1,2,4]triazin-2-yl ester (0.102 g, 0.272 mmol) and 3-Methyl-4-(1-methyl-piperidin-4-yl)-phenylamine (0.075 g, 0.37 mmol) were reacted in an analogous manner to Example at 50° C. for 16 h. The reaction was concentrated, taken up in DMSO, and purified by Gilson RP-HPLC to afford title compound as a TFA salt (5 mg, 4%). There was an issue with the prep HPLC and most of the sample was lost. The poor yield was not due to the reaction. LCMS=429.1 (M+H), HPLC rt=2.490 min, purity=91%, $^1$H NMR (400 MHz, (D3C)2SO, δ, ppm): 9.43 (s, 1H), 9.30 (bs, 1H), 9.03 (d, J=1.9 Hz, 1H), 8.98 (s, 1H), 8.45 (dd, j=8.7 Hz, 2.3 Hz, 1H0, 7.83 (s, 1H), 7.38 (dd, J=8.4 Hz, 1.9 Hz, 1H), 7.18 (d, J=4.6 Hz, 1H), 7.06 (d, J=8.4 Hz, 1H), 7.01-6.97 (m, 2H), 3.94 (s, 3H), 3.52 (d, J=11.2 Hz, 2H), 3.14-3.09 (m, 2H), 3.00-2.92 (m, 1H), 2.82 (d, J=4.8 Hz, 3H), 2.35 (s, 3H), 1.93-1.90 (m, 2H), 1.82-1.76 (m, 2H).

Example 942

[7-(2-Methoxy-phenyl)-pyrrolo[2,1-f][1,2,4]triazin-2-yl]-[3-methyl-4-(1-methyl-piperidin-4-yl)-phenyl]-amine 7-(2-Methoxy-phenyl)-pyrrolo[2,1-f][1,2,4]triazin-2-ol (0.0709 g, 0.294 mmol) and 3-Methyl-4-(1-methyl-piperidin-4-yl)-phenylamine (0.0750 g, 0.367 mmol) were reacted in an analogous manner to Example 908D at 50° C. for 16 h. Concentrated reaction mixture, took up in DMSO, and purified by Gilson RP-HPLC to afford title compound as a TFA salt (55 mg, 44%). The fractions containing desired product were lyophilized. LCMS=428.1 (M+H), HPLC rt=2.621 min, purity=99%, $^1$H NMR (400 MHz, (D3C)2SO, δ, ppm): 9.30 (s, 1H), 9.29 (bs, 1H), 8.94 (s, 1H), 7.84 (d, J=7.7 Hz, 1H), 7.63 (s, 1H), 7.47-7.39 (m, 2H), 7.21 (d, J=8.6 Hz, 1H), 7.12 (dd, J=7.2 Hz, 7.2 Hz, 1H), 6.97-6.91 (m, 3H), 3.79 (s, 3H), 3.50 (d, J=12.1 Hz, 2H), 3.14-3.06 (m, 2H), 2.96-2.86 (m, 1H), 2.81 (d, J=4.7 Hz, 3H), 2.21 (s, 3H), 1.90-1.75 (m, 4H).

Example 943

N-tert-Butyl-3-{2-[4-(8-methyl-8-aza-bicyclo[3.2.1]oct-3-yl)-phenylamino]-pyrrolo[2,1-f][1,2,4]triazin-7-yl}-benzenesulfonamide 943A. Trifluoro-methanesulfonic acid 8-methyl-8-aza-bicyclo[3.2.1]oct-2-en-3-yl ester. 8-Methyl-8-aza-bicyclo[3.2.1]octan-3-one (1.40 g, 10.0 mmol) was dissolved in Tetrahydrofuran (12.5 mL) and the reaction mixture was cooled to −20° C. 1.00 M of Sodium hexamethyldisilazane in Tetrahydrofuran (10.7 mL, 10.7 mmol) was added to the flask over 15 min. The reaction mixture was stirred at −20° C. for 1 hour. N-Phenylbis(trifluoromethanesulphonimide) (3.82 g, 10.7 mmol) was added to the reaction mixture in portions over 5 min and the mixture was stirred at −20° C. to −10° C. for 1 hour. To the reaction mixture was added 1.00 M of Sodium hydroxide in water (9.29 mL, 9.29 mmol) and the mixture was allowed to warm to rt with stirring. Solvent was partially removed by rotary evaporation at 30° C. To the remaining reaction mixture was added Ethyl acetate (13.9 mL, 143 mmol) and Heptane (6.97 mL, 47.6 mmol). The mixture was stirred at rt for 5 min. The layers were separated and the aqueous layer was discarded. The organic layer was washed with 1 N NaOH. The aqueous layers were discarded. The organic layer was concentrated, and the resulting oil was taken forward to the next step without purification. (2.73 g, 99% yield)

943B. 8-Methyl-3-(4-nitro-phenyl)-8-aza-bicyclo[3.2.1]oct-2-ene. Trifluoro-methanesulfonic acid 8-methyl-8-aza-bicyclo[3.2.1]oct-2-en-3-yl ester (2.70 g, 9.96 mmol) was dissolved in Tetrahydrofuran (18.9 mL) and the reaction mixture was purged with N2 for 5 min. In a separate flask, 4-nitrophenyl boronic acid (1.50 g, 8.98 mmol), 1,1'-Bis(diphenylphosphino)ferrocene (0.0494 g, 0.0891 mmol), Palladium Acetate (0.0207 g, 0.0920 mmol), and Potassium fluoride (1.57 g, 27.0 mmol) were added followed by the solution of Trifluoro-methanesulfonic acid 8-benzyl-8-aza-bicyclo[3.2.1]oct-2-en-3-yl ester in THF. The resulting mixture was purged with N2 for 5 minutes and heated to reflux (67° C.) under nitrogen and stirred for 2 hr. The reaction mixture was allowed to cool to rt overnight. Ethyl acetate (22.5 mL, 2.30E2 mmol) and 1.00 M of Sodium hydroxide in water (22.5 mL, 22.5 mmol) were added and the mixture was stirred at rt for 10 min. The layers were separated and the aqueous layer discarded. The organic layer was washed with brine, then water, and dried over MgSO4, filtered, and the solvent was removed. Purified by ISCO silica gel chromatography (0-15% MeOH in DCM). NMR indicates desired product (500 mg, 23%). LCMS=245.1 (M+H), rt=0.66 min. HPLC rt=1.809 min, 99% purity.

943C. 4-(8-Methyl-8-aza-bicyclo[3.2.1]oct-3-yl)-phenylamine . 8-Methyl-3-(4-nitro-phenyl)-8-aza-bicyclo[3.2.1]oct-2-ene (0.342 g, 1.40 mmol) was reacted in an analogous manner to Example 911C overnight. The reaction mixture was filtered through celite and concentrated to a clear oil which crystallized under vacuum. HNMR consistent with desired product. (283 mg, 93%)

943D. N-tert-Butyl-3-{2-[4-(8-methyl-8-aza-bicyclo[3.2.1]oct-3-yl)-phenylamino]-pyrrolo[2,1-f][1,2,4]triazin-7-yl}-benzenesulfonamide. N-tert-Butyl-3-(2-hydroxy-pyrrolo[2,1-f][1,2,4]triazin-7-yl)-benzenesulfonamide (0.102 g, 0.294 mmol) and 4-(8-Methyl-8-aza-bicyclo[3.2.1]oct-3-yl)-phenylamine (0.0794 g, 0.367 mmol) were reacted in an analogous manner to Example 908D at 50° C. for 16 h. Concentrated reaction mixture, took up in DMSO, and purified by Gilson RP-HPLC. The fractions containing desired product were lyophilized to afford title compound as a TFA salt (17 mg, 11%) Low yield is due to loss of product upon loading though syringe filter. LCMS=545.0 (M+H), HPLC rt=2.864, purity=99% , $^1$H NMR (400 MHz, (D3C)2SO, δ, ppm): 9.57 (s, 1H), 9.25 (bs, 1H), 9.04 (s, 1H), 8.64 (s, 1H), 8.29 (d, J=8.0 Hz, 1H), 7.87 (d, J=8.1 Hz, 1H), 7.76-7.72 (m, 3H), 7.63 (s, 1H), 7.49 (d, J=8.3 Hz, 2H), 7.21 (d, j=4.7 Hz, 1H), 7.00 (d, J=4.7 Hz, 1H), 3.87 (s, 2H), 3.11-3.13 (m, 1H), 2.65 (d, j=5.0 Hz, 3H), 2.43-2.32 (m, 4H), 2.01-1.99 (m, 2H), 1.66-1.64 (m, 2H), 1.12 (s, 9H).

Example 944

[7-(6-Methoxy-pyridin-3-yl)-pyrrolo[2,1-f][1,2,4]triazin-2-yl]-[4-(8-methyl-8-aza-bicyclo[3.2.1]oct-3-yl)-phenyl]-amine Trifluoro-methanesulfonic acid 7-(6-methoxy-pyridin-3-yl)-pyrrolo[2,1-f][1,2,4]triazin-2-yl ester (0.102 g, 0.272 mmol) and 4-(8-Methyl-8-aza-bicyclo[3.2.1]oct-3-yl)-phenylamine (0.079 g, 0.37 mmol) were reacted in an analogous manner to Example 908D at 50° C. for 16 h. The reaction mixture was concentrated, diluted with DMSO, and purified by Gilson RP-HPLC to afford title compound as a TFA salt (70 mg, 58%). LCMS=441.1 (M+H), HPLC rt=2.423 min, purity=99%, $^1$H NMR (400 MHz, (D3C)2SO, δ, ppm): 9.50 (s, 1H), 9.24 (bs, 1H), 8.99 (s, 1H), 8.92 (d, J=1.9 Hz, 1H), 8.54 (dd, J=8.7 Hz, 2.3 Hz, 1H), 7.69 (d, J=8.6 Hz, 2H), 7.46 (d, J=8.6 Hz, 2H), 7.20 (d, J=4.7 Hz, 1H), 7.03 (d, J=8.9 Hz, 1H), 6.97 (d, J=4.7 Hz, 1H), 3.94 (s, 3H), 3.86-3.88 (m, 2H), 3.15-3.13 (m, 1H), 2.65 (d, J=5.0 Hz, 3H), 2.42-2.37 (m, 4H), 2.03-1.99 (m, 2H).

Example 945

[7-(2-Methoxy-phenyl)-pyrrolo[2,1-f][1,2,4]triazin-2-yl]-[4-(8-methyl-8-azabicyclo[3.2.1]oct-3-yl)-phenyl]-amine 7-(2-Methoxy-phenyl)-pyrrolo[2,1-f][1,2,4]triazin-2-ol (0.0709 g, 0.294 mmol) and 4-(8-Methyl-8-aza-bicyclo[3.2.1]oct-3-yl)-phenylamine (0.0794 g, 0.367 mmol) were reacted in an analogous manner to Example 908D at 50° C. for 16 h. Concentrated reaction mixture, took up in DMSO, and purified by Gilson RP-HPLC to afford title compound as a TFA salt . The fractions containing desired product were lyophilized (82 mg, 64%). LCMS=440.1 (M+H), HPLC rt=2.604 min, purity=99%, $^1$H NMR (400 MHz, (D3C)2SO, δ, ppm): 9.40 (s, 1H), 9.23 (bs, 1H), 8.96 (s, 1H), 7.83 (d, J=7.5 Hz, 1H), 7.66 (d, j=8.4 hz, 2H), 7.47 (dd, J=7.9 Hz, 7.9 Hz, 1H), 7.33 (d, J=8.4 Hz, 2H), 7.22 (d, J=8.4 Hz, 1H), 7.14 (dd, J=7.6 Hz, 7.6 Hz, 1H), 6.96 (d, J=4.6 Hz, 1H), 6.93 (d, j=4.6 Hz, 1H), 3.86-3.84 (m, 2H, 3.80 (s, 3H), 3.11-3.09 (m, 1H), 2.64 (d, J=5.0 Hz, 3H), 2.49-2.45 (m, 2H), 2.40-2.35 (m, 2H), 2.01-1.98 (m, 2H), 1.61-1.58 (m, 2H). (82 mg, 64%).

Example 946

[7-(3-Methanesulfonyl-phenyl)-pyrrolo[2,1-f][1,2,4]triazin-2-yl]-[3-methyl-4-(1-methyl-piperidin-4-yl)-phenyl]-amine 7-(3-Methanesulfonyl-phenyl)-pyrrolo[2,1-f][1,2,4]triazin-2-ol (0.0702 g, 0.243 mmol) and 3-Methyl-4-(1-methyl-piperidin-4-yl)-phenylamine (0.0620 g, 0.303 mmol) were reacted in an analogous manner to Example 908D at 50° C. for 16 h. Concentrated reaction mixture, took up in DMSO, and purified by Gilson RP-HPLC. The fractions containing desired product were lyophilized to afford title compound as a TFA salt (55 mg, 48%). LCMS=476.1 (M+H), HPLC rt=2.396, purity=99%, $^1$H NMR (400 MHz, (D3C)2SO, δ, ppm): 9.46 (s, 1H), 9.41 (bs, 1H), 9.04 (s, 1H), 8.58 (s, 1H), 8.55 (d, J=8.3 Hz, 1H), 7.94 (d, J=8.3 Hz, 1H), 7.80 (dd, J=8.3 Hz, 8.3 Hz, 1H0, 7.64 (d, J=8.3 Hz, 1H), 7.48 (s, 1H), 7.30 (d, J=4.6 Hz, 1H), 7.15 (d, J=8.6 Hz, 1H), 7.00 (d, J=4.6 hz, 1H), 3.52 (d, J=11.7 Hz, 2H), 3.29 (s, 3H), 3.15-3.10 (m, 2H), 2.95-2.92 (m, 1H), 2.82 (d, J=4.5 Hz, 3H), 2.29 (s, 3H), 1.92-1.75 (m, 4H).

Example 947

[7-(4-Methanesulfonyl-phenyl)-pyrrolo[2,1-f][1,2,4]triazin-2-yl]-[3-methyl-4-(1-methyl-piperidin-4-yl)-phenyl]-amine 7-(4-Methanesulfonyl-phenyl)-pyrrolo[2,1-f][1,2,4]triazin-2-ol (0.0702 g, 0.243 mmol) and 3-Methyl-4-(1-methyl-piperidin-4-yl)-phenylamine (0.0620 g, 0.303 mmol) were reacted in an analogous manner to Example 908D at 50° C. for 16 h. Concentrated reaction mixture, took up in DMSO, and purified by Gilson RP-HPLC to afford title compound as a TFA salt (38 mg, 33%). The fractions containing desired product were lyophilized. LCMS=476.0 (M+H), HPLC rt=2.434, purity=98% , $^1$H NMR (400 MHz, (D3C)2SO, δ, ppm): 9.52 (s, 1H), 9.39 (bs, 1H), 9.06 (s, 1H), 8.47 (d, J=7.3 Hz, 2H), 8.03 (d, J=7.3 Hz, 2H), 7.76 (s, 1H), 7.43 (d, J=8.0 Hz, 1H), 7.34 (d, J=4.7 Hz, 1H), 7.09 (d, J=8.4 Hz, 1H), 7.00 (d, J=4.7 Hz, 1H), 3.52 (d, J=11.7 Hz, 2H), 3.28 (s, 3H), 3.15-3.10 (m, 2H), 2.99-2.95 (m, 1H), 2.82 (d, J=4.6 Hz, 3H), 2.34 (s, 3H), 1.95-1.80 (m, 4H).

Example 948

2-(4-{4-[7-(3-Methanesulfonyl-phenyl)-pyrrolo[2,1-f][1,2,4]triazin-2-ylamino]-2-methyl-phenyl}-piperidin-1-yl)-acetamide 7-(3-Methanesulfonyl-phenyl)-pyrrolo[2,1-f][1,2,4]triazin-2-ol (0.0533 g, 0.184 mmol) and 2-[4-(4-Amino-2-methyl-phenyl)-piperidin-1-yl]-acetamide (0.0570 g, 0.230 mmol) were reacted in an analogous manner to Example 908D at 50° C. for 16 h. Concentrated reaction mixture, took up in DMSO, and purified by Gilson RP-HPLC. The fractions containing desired product were lyophilized to afford title compound as a TFA salt (84 mg, 88%). LCMS=519.0 (M+H), HPLC rt=2.290, purity=99% , $^1$H NMR (400 MHz, (D3C)2SO, δ, ppm): 9.60 (bs, 1H), 9.46 (s, 1H), 9.04 (s, 1H), 8.58 (s, 1H), 8.56 (d, J=8.0 Hz, 1H0, 7.98 (s, 1H), 7.94 (d, J=8.0 Hz, 1H), 7.81 (dd, J=8.0 Hz, 8.0 Hz, 1H), 7.72 (s, 1H), 7.64 (d, J=8.5 Hz, 1H), 7.47 (s, 1H), 7.30 (d, J=4.7 Hz, 1H), 3.91 (s, 2H), 3.56 (d, J=11.5 Hz, 2H), 3.29 (s, 3H), 3.23-3.18 (m, 2H), 2.95-2.93 (m, 1H), 2.29 (s, 3H), 2.02-1.97 (m, 2H), 1.88-1.84 (m, 2H).

Example 949

2-(4-{4-[7-(4-Methanesulfonyl-phenyl)-pyrrolo[2,1-f][1,2,4]triazin-2-ylamino]-2-methyl-phenyl}-piperidin-1-yl)-acetamide 7-(4-Methanesulfonyl-phenyl)-pyrrolo[2,1-f][1,2,4]triazin-2-ol (0.0533 g, 0.184 mmol) and 2-[4-(4-Amino-2-methyl-phenyl)-piperidin-1-yl]-acetamide (0.0570 g, 0.230 mmol) were reacted in an analogous manner to Example at 50° C. for 16 h. Concentrated reaction mixture, took up in DMSO, and purified by Gilson RP-HPLC. The fractions containing desired product were lyophilized to afford title compound as a TFA salt (85 mg, 89%). LCMS=519.1 (M+H), HPLC rt=2.349, purity=91% , $^1$H NMR (400 MHz, (D3C)2SO, δ, ppm): 9.54 (bs, 1H), 9.52 (s, 1H), 9.06 (s, 1H), 8.47 (d, J=8.6 Hz, 1H), 8.03 (d, J=7.9 Hz, 1H), 7.97 (s, 1H), 7.76 (s, 1H), 7.72 (s, 1H), 7.42 (d, J=7.9 Hz, 1H), 7.34 (d, J=4.7 Hz, 1H), 7.11 (d, J=8.6 Hz, 1H), 7.00 (d, =4.7 Hz, 1H), 3.91 (m, 2H), 3.55 (d, J=11.3 Hz, 1H), 3.28 (s, 3H), 3.25-3.19 (m, 2H), 2.99-2.97 (m, 1H), 2.33 (s, 3H), 2.04-2.00 (m, 2H), 1.90-1.84 (m, 2H).

Example 950

[7-(1-Methanesulfonyl-1H-pyrazol-4-yl)-pyrrolo[2,1-f][1,2,4]triazin-2-yl]-[3-(4-methyl-piperazin-1-yl)-phenyl]-amine To a solution of [3-(4-Methyl-piperazin-1-yl)-phenyl]-[7-(1H-pyrazol-4-yl)-pyrrolo[2,1-f][1,2,4]triazin-2-yl]-amine (1.00E2 mg, 0.267 mmol) and N,N-Diisopropylethylamine (48.8 uL, 0.280 mmol) in N,N-Dimethylformamide (12.1 mL, 156 mmol) was added Methanesulfonyl chloride (21.7 uL, 0.280 mmol). The reaction was stirred at rt overnight. LCMS 453.0 (M+H), HPLC rt=2.180 min, 97% purity. The reaction mixture was concentrated to remove DMF, diluted with CH$_2$Cl$_2$, and washed with sat'd aqueous NaHCO3. The organic layer was dried over MgSO4, filtered, and concentrated. Product was isolated as a yellow solid (29 mg, 24%). $^1$H NMR (400 MHz, (D3C)2SO, δ, ppm): 9.30 (s, 1H), 9.03 (s, 1H0, 8.97 (s, 1H), 8.71 (s, 1H), 7.39 (d, J=8.3 Hz, 1H), 7.29 (d, J=4.6 Hz, 1H0, 7.22 (dd, J=8.3 Hz, 8.3 Hz, 1H), 7.05 (bm, 1H), 6.95 (d, J=4.6 Hz, 1H), 6.63 (dd, J=8.4 Hz, 1.4 Hz, 1H0, 3.62 (s, 3H), 3.12-3.10 (m, 4H), 2.45-2.43 (m, 4H), 2.21 (s, 3H).

Example 951

2-(4-{4-[7-(3-Methanesulfonyl-phenyl)-pyrrolo[2,1-f][1,2,4]triazin-2-ylamino]-2-trifluoromethyl-phenyl}-3,6-dihydro-2H pyridin-1-yl) acetamide 951A. 4-(4-Nitro-2-trifluoromethyl-phenyl)-3,6-dihydro-2H-pyridine-1-carboxylic acid tert-butyl ester 1-Chloro-4-nitro-2-trifluoromethyl-benzene (2.00 g, 8.87 mmol) was reacted in an analogous manner to Example 908A The product was purified by ISCO chromatography using ethyl acetate/hexane (0-50%) (2.03 g, 62%). LCMS did not ionize, rt=1.44 min.

951B. 4-(4-Nitro-2-trifluoromethyl-phenyl)-1,2,3,6-tetrahydro-pyridine. 4-(4-Nitro-2-trifluoromethyl-phenyl)-3,6-dihydro-2H-pyridine-1-carboxylic acid tert-butyl ester (1.00 g, 0.00268 mol) was reacted in an analogous manner to Example 911A. Concentrated reaction mixture, diluted with CH$_2$Cl$_2$, and washed with sat'd NaHCO3. Dried organics and concentrated to a white solid (708 mg, 97%). LCMS 314, 315, rt=0.71 min. HNMR consistent.

951C. 2-[4-(4-Nitro-2-trifluoromethyl-phenyl)-3,6-dihydro-2H-pyridin-1-yl]-acetamide (850 mg, 99%) 4-(4-Nitro-2-trifluoromethyl-phenyl)-1,2,3,6-tetrahydro-pyridine (0.708 g, 0.00260 mol was reacted in an analogous manner to Example 911B for 90 mins at 50° C. LCMS=330 (M+H), rt - 0.68 min. Obtained yellow foam. (850 mg, 99%).

951D. 2-[4-(4-Amino-2-trifluoromethyl-phenyl)-3,6-dihydro-2H-pyridin-1-yl]-acetamide. (180 mg, 43%) 2-[4-(4-Nitro-2-trifluoromethyl-phenyl)-3,6-dihydro-2H-pyridin-1-yl]-acetamide (0.462 g, 1.40 mmol) was reacted in an analogous manner to Example 911C for 48 h. LCMS showed mass of unreduced double bond, 300.0, 301.1 (M+H). Filtered reaction mixture through celite and concentrated.

951E. 2-(4-{4-[7-(3-Methanesulfonyl-phenyl)-pyrrolo[2,1-f][1,2,4]triazin-2-ylamino]-2-trifluoromethyl-phenyl}-3,6-dihydro-2H pyridin-1-yl) acetamide. 7-(3-Methanesulfonyl-phenyl)-pyrrolo[2,1-f][1,2,4]triazin-2-ol (46.1 mg, 0.159 mmol) and 2-[4-(4-Amino-2-trifluoromethyl-phenyl)-3,6-dihydro-2H-pyridin-1-yl]-acetamide (0.0596 g, 0.199 mmol) were reacted in an analogous manner to Example 908D at 50° C. for 16 h. Concentrated reaction mixture, took up in DMSO, and purified by Gilson RP-HPLC. The fractions containing desired product were lyophilized to afford title compound as a TFA salt (65 mg, 72%). LCMS=570.9 (M+H), HPLC rt=2.435, purity=95% , $^1$H NMR (400 MHz, (D3C)2SO, δ, ppm): 10.14 (bs, 1H), 9.60 (s, 1H), 9.11 (s, 1H), 8.56 (s, 1H), 8.49 (d J=7.8 Hz, 1H), 8.11 (d, J=8.8 Hz, 1H), 8.01 (s, 2H), 7.95 (d, J=7.9 Hz, 1H) 7.80-7.73 (m, 2H), 7.36-7.34 (m, 2H), 7.07 (d, J=4.7 Hz, 1H), 5.60 (s, 1H), 4.02 (s, 2H), 4.01-3.95 (m, 1H), 3.90-3.80 (m, 1H), 3.65-3.55 (m, 1H), 3.44-3.34 (m, 1H), 3.20 (s, 3H), 2.82-2.70 (m, 1H), 2.45-2.38 (m, 1H).

Example 952

2-(4-{4-[7-(2-Methoxy-phenyl)-pyrrolo[2,1-f][1,2,4]triazin-2-ylamino]-2-trifluoromethyl-phenyl}-3,6-dihydro-2H-pyridin-1-yl)-acetamide 7-(2-Methoxy-phenyl)-pyrrolo[2,1-f][1,2,4]triazin-2-ol (38.4 mg, 0.159 mmol) and 2-[4-(4-Amino-2-trifluoromethyl-phenyl)-3,6-dihydro-2H-pyridin-1-yl]-acetamide (0.0596 g, 0.199 mmol) were reacted in an analogous manner to Example 908D at 50° C. for 16 h. Concentrated reaction mixture, took up in DMSO, and purified by Gilson RP-HPLC. The fractions containing desired product were lyophilized to afford title compound as a TFA salt (29 mg, 35%). LCMS=523.0 (M+H), HPLC rt=2.728, purity=95% , $^1$H NMR (400 MHz, (D3C)2SO, δ, ppm): 10.06 (bs, 1H), 9.82 (s, 1H), 9.01 (s, 1H), 8.03 (s, 1H), 8.00-7.97 (m, 2H), 7.76-7.72 (m, 2H), 7.46 (dd, J=7.6 Hz, 7.6 Hz, 1H), 7.00 (dd, J=7.6 Hz, 7.6 Hz, 1H), 6.99-6.96 (m, 2H), 5.55 (s, 1H), 4.00 (s, 2H), 3.90-3.80 (m, 1H), 3.78 (s, 3H), 3.58-3.52 (m, 2H), 3.40-3.30 (m, 1H), 2.68-2.64 (m, 1H), 2.39-2.30 (m, 2H).

Example 953

2-(4-{4-[7-(6-Methoxy-pyridin-3-yl)-pyrrolo[2,1-f][1,2,4]triazin-2-ylamino]-2-trifluoromethyl-phenyl}-3,6-dihydro-2H-pyridin-1-yl)-acetamide Trifluoro-methanesulfonic acid 7-(6-methoxy-pyridin-3-yl)-pyrrolo[2,1-f][1,2,4]triazin-2-yl ester (55.2 mg, 0.148 mmol) and 2-[4-(4-Amino-2-trifluoromethyl-phenyl)-3,6-dihydro-2H-pyridin-1-yl]-acetamide (59.6 mg, 0.199 mmol) were stirred at 50° C. overnight. The reaction mixture was concentrated, diluted with DMSO, and purified by Gilson RP-HPLC to afford title compound as a TFA salt (27 mg, 35%). LCMS=524.0 (M+H), HPLC rt=2.527 min, purity=97%, $^1$H NMR (400 MHz, (D3C)2SO, δ, ppm): 10.10 (bs, 1H), 9.92 (s, 1H), 9.05 (s, 1H), 8.88 (d, J=1.9 Hz, 1H), 8.45 (dd, J=8.65 Hz, 1.9 Hz, 1H), 8.21 (s, 1H0, 8.00 (s, 1H), 7.88 (d, J=8.6 Hz, 1H), 7.74 (s, 1H), 7.29 (d, J=8.6 Hz, 1H), 7.22 (d, J=4.7 Hz, 1H), 6.94 (d, J=8.6 Hz, 1H), 5.60 (s, 1H), 4.02 (s, 2H), 4.01-3.99 (m, 1H), 3.93 (s, 3H), 3.86-3.82 (m, 1H), 3.61-3.55 (m, 1H), 3.39-3.34 (m, 1H), 2.78-2.70 (m, 1H), 2.45-2.38 (m, 1H).

Example 954

[4-(1-Methyl-piperidin-4-yl)-phenyl]-[7-(1-methyl-1H-pyrazol-3-yl)-pyrrolo[2,1-f][1,2,4]triazin-2-yl]-amine (7-Bromo-pyrrolo[2,1-f][1,2,4]triazin-2-yl)-[4-(1-methyl-piperidin-4-yl)-phenyl]-amine (46.8 mg, 0.000121 mol) and 1-Methyl-3-(4,4,5,5-tetramethyl-1,3,2-dioxaborolan-2-yl)-1H-pyrazole (50.4 mg, 0.000242 mol) were reacted in an analogous manner to Example 881A at 80° C. for 4 hours. The product was isolated via Gilson RP-HPLC to afford title compound as a TFA salt (10 mg, 21%). LCMS=388.1 (M+H), HPLC rt=1.917 min , 99% purity, $^1$H NMR (400 MHz, (D3C) 2SO, δ, ppm): 9.43 (s, 1H), 9.30 (bs, 1H), 8.93 (s, 1H), 7.85 (d, J=1.9 Hz, 1H), 7.80 (d, J=8.4 Hz, 2H), 7.19 (d, J=8.4 Hz, 2H), 7.13 (d, J=1.9 Hz, 1H), 7.11 (d, J=4.7 Hz, 1H), 6.91 (d, J=4.7 Hz, 1H), 3.97 (s, 3H), 3.52 (d, J=12.8 Hz, 2H), 3.10-

3.05 (m, 2H), 2.83 (d, J=4.6 Hz, 3H), 2.78-2.72 (m, 1H), 2.03 (d, J=14.1 Hz, 2H), 1.90-1.79 (m, 2H).

Example 955

2-(4-{4-[7-(1-Methyl-1H-pyrazol-3-yl)-pyrrolo[2,1-f][1,2,4]triazinylaminophenyl}-piperidin-1-yl)-acetamide 2-{4-[4-(7-Bromo-pyrrolo[2,1-f][1,2,4]triazin-2-ylamino)-phenyl]-piperidin-1-yl}-acetamide (101 mg, 0.235 mmol) and 1-Methyl-3-(4,4,5,5-tetramethyl-1,3,2-dioxaborolan-2-yl)-1H-pyrazole (97.9 mg, 0.470 mmol) were reacted in an analogous manner to Example 881A at 80° C. for 4 hours. The product was isolated via Gilson RP-HPLC to afford title compound as a TFA salt (32 mg, 32%). LCMS=431.1 (M+H), HPLC rt=2.287 min , 99% purity, $^1$H NMR (400 MHz, (D3C)2SO, δ, ppm): 9.54 (bs, 1H), 9.42 (s, 1H), 8.93 (s, 1H), 7.97 (s, 1H), 7.86 (s, 1H0, 7.80 (d, J=8.4 Hz, 2H), 7.72 (s, 1H), 7.20 (d, J=8.4 Hz, 2H), 7.14 (s, 1H), 7.10 (d, J=4.7 Hz, 1H), 6.91 (d, J=4.7 Hz, 1H), 3.97 (s, 3H), 3.92 (s, 2H), 3.55 (d, J=1.6 Hz, 2H), 3.22-3.12 (m, 2H), 2.79-2.54 (m, 1H), 2.02-1.95 (m, 4H).

Example 956

2-(4-{4-[7-(3-Methanesulfonylamino-phenyl)-pyrrolo[2,1-f][1,2,4]triazin-2-ylamino]-phenyl}-piperidin-1-yl)-acetamide N-[3-(2-Hydroxy-pyrrolo[2,1-f][1,2,4]triazin-7-yl)-phenyl]-methanesulfonamide (80.0 mg, 0.263 mmol) and 2-[4-(4-Amino-phenyl)-piperidin-1-yl]-acetamide (0.0766 g, 0.328 mmol) were reacted in an analogous manner to Example 908D at 50° C. for 16 h. Concentrated reaction mixture, took up in DMSO, and purified by Gilson RP-HPLC. The fractions containing desired product were lyophilized to afford title compound as a TFA salt (84 mg, 61%). LCMS=520.0 (M+H), HPLC rt=2.221 min, purity=93%, $^1$H NMR (400 MHz, (D3C)2SO, δ, ppm): 9.86 (s, 1H), 9.55 (bs, 1H), 9.49 (s, 1H), 9.01 (s, 1H), 7.98 (s, 1H), 7.93 (d, J=7.9 Hz, 1H), 7.87 (s, 1H), 7.72-7.72 (m, 2H), 7.51 (dd, J=7.9 Hz, 7.9 Hz, 1H), 7.28 (d, J=7.4 Hz, 1H), 7.18 (d, J=7.9 Hz, 2H), 7.07 (d, J=4.7 Hz, 1H), 6.97 (d, J=4.7 Hz, 1H), 3.92 (m, 2H), 3.56 (d, J=11.9 Hz, 2H), 3.19-3.12 (m, 2H), 3.03 (s, 3H), 2.77-2.71 (m, 1H), 1.99-1.97 (m, 4H).

Example 957

N-[3-(2-{4-[1-((S)-2-Hydroxy-propyl)-piperidin-4-yl]-phenylamino}-pyrrolo[2,1-f][1,2,4]triazin-7-yl)-phenyl]-methanesulfonamide N-[3-(2-Hydroxy-pyrrolo[2,1-f][1,2,4]triazin-7-yl)-phenyl]-methanesulfonamide (0.0800 g, 0.263 mmol) and (S)-1-[4-(4-Amino-phenyl)-piperidin-1-yl]-propan-2-ol (0.0770 g, 0.328 mmol) were reacted in an analogous manner to Example 908D at 50° C. for 16 h. Concentrated reaction mixture, took up in DMSO, and purified by Gilson RP-HPLC. The fractions containing desired product were lyophilized to afford title compound as a TFA salt (42 mg, 31%). LCMS=521.0 (M+H), HPLC rt=2.323 min, purity=95%, $^1$H NMR (400 MHz, (D3C)2SO, δ, ppm): 9.85 (s, 1H), 9.49 (s, 1H), 9.05 (bs, 1H), 9.00 (s, 1H), 7.93 (d, J=7.2 Hz, 1H), 7.86 (s, 1H), 7.72 (d, J=7.6 Hz, 2H), 7.50 (dd, J=7.2 Hz, 7.2 Hz, 1H), 7.28 (d, j=7.6 Hz, 1H), 7.18 (d, J=7.6 Hz, 2H), 7.07 (d, J=4.4 Hz, 1H), 6.97 (d, J=4.4 Hz, 1H), 5.47 (s, 1H), 4.12 (s, 1H), 3.59-3.56 (m, 2H), 3.11-2.98 (m, 3H), 3.02 (s, 3H), 2.08-1.95 (m, 5H), 1.14 (d, J=5.6 Hz, 3H).

Example 958

N-[3-(2-{4-[1-(2-Hydroxy-ethyl)-piperidin-4-yl]-phenylamino}-pyrrolo[2,1-f][1,2,4]triazin-7-yl)-phenyl]-methanesulfonamide N-[3-(2-Hydroxy-pyrrolo[2,1-f][1,2,4]triazin-7-yl)-phenyl]-methanesulfonamide (0.0800 g, 0.263 mmol) and 2-[4-(4-Amino-phenyl)-piperidin-1-yl]-ethanol (0.0869 g, 0.394 mmol) were reacted in an analogous manner to Example 908D at 50° C. for 16 h. Concentrated reaction mixture, took up in DMSO, and purified by Gilson RP-HPLC. The fractions containing desired product were lyophilized to afford title compound as a TFA salt (72 mg, 54%). LCMS=507.0 (M+H), HPLC rt=2.241 min, purity=96%, $^1$H NMR (400 MHz, (D3C)2SO, δ, ppm): 9.85 (s, 1 h), 9.50 (s, 1 h), 9.19 (bs, 1H), 9.01 (s, 1H), 7.92 (d, j=7.7 Hz, 1H), 7.87 (s, 1H), 7.73 (d, J=7.7 Hz, 2H), 7.50 (dd, J=7.7 Hz, 1H), 7.28 (d, J=8.2 Hz, 1H), 7.18 (d, J=8.2 Hz, 2H), 7.07 (d, j=4.4 Hz, 1H), 6.97 (d, J=4.4 Hz, 1H), 3.76-3.74 (m, 2H), 3.61-3.58 (m, 2H), 3.20-3.18 (m, 2H), 3.10-3.07 (m, 2H), 3.02 (s, 3H), 2.77-2.76 (m, 1H), 2.01-1.91 (m, 4H).

Example 959

2-[4-(4-{7-[3-(Methanesulfonyl-methyl-amino)-phenyl]-pyrrolo[2,1-f][1,2,4]triazin-2-ylamino}-phenyl)-piperidin-1-yl]-acetamide N-[3-(2-Hydroxy-pyrrolo[2,1-f][1,2,4]triazin-7-yl)-phenyl]-N-methyl-methanesulfonamide (83.7 mg, 0.263 mmol) and 2-[4-(4-Amino-phenyl)-piperidin-1-yl]-acetamide (0.0766 g, 0.328 mmol) were reacted in an analogous manner to Example 908D at 50° C. for 16 h. Concentrated reaction mixture, took up in DMSO, and purified by Gilson RP-HPLC. The fractions containing desired product were lyophilized to afford title compound as a TFA salt (46 mg, 33%). LCMS=534 (M+H), HPLC rt=2.332 min, purity=96%, $^1$H NMR (400 MHz, (D3C)2SO, δ, ppm): 9.55 (bs, 1H), 9.51 (s, 1H), 9.01 (s, 1H), 8.21 (s, 1H), 8.10 (d, J=8.2 Hz, 1H), 7.97 (s, 1H), 7.72-7.70 (m, 3H), 7.57 (dd, J=8.0 Hz, 8.0 Hz, 1H), 7.46 (d, J=8.2 Hz, 1H), 7.23-7.19 (m, 3H), 6.98 (d, J=4.4 Hz, 1H), 3.92 (s, 2H), 3.56 (d, J=12.2 Hz, 2H), 3.34 (s, 3H), 3.19-3.14 (m, 2H), 2.98 (s, 3H), 2.77-2.73 (m, 1H), 1.99-1.96 (m, 4H).

Example 960

N-[3-(2-{4-[1-((S)-2-Hydroxy-propyl)-piperidin-4-yl]-phenylamino}-pyrrolo[2,1-f][1,2,4]triazin-7-yl)-phenyl]-N-methyl-methanesulfonamide N-[3-(2-Hydroxy-pyrrolo[2,1-f][1,2,4]triazin-7-yl)-phenyl]-N-methyl-methanesulfonamide (0.0837 g, 0.263 mmol) and (S)-1-[4-(4-Amino-phenyl)-piperidin-1-yl]-propan-2-ol (0.0770 g, 0.328 mmol) were reacted in an analogous manner to Example 908D at 50° C. for 16 h. Concentrated reaction mixture, took up in DMSO, and purified by Gilson RP-HPLC. The fractions containing desired product were lyophilized to afford title compound as a TFA salt (8 mg, 6%). LCMS=535.0 (M+H), HPLC rt=2.448 min, purity=99%, $^1$H NMR (400 MHz, (D3C)2SO, δ, ppm): 9.50 (s, 1H), 9.06 (bs, 1H), 9.00 (s, 1H), 8.20 (s, 1H), 8.10 (d, J=7.8 Hz, 1H), 7.71 (d, J=7.8 Hz, 2H), 7.57 (dd, J=7.8 Hz. 7.8 Hz, 1H), 7.46 (d, J=7.2 Hz, 1H), 7.22-7.18 (m, 3H), 6.98 (j, J=4.4 Hz, 1H), 5.47 (s, 1H), 4.13

(s, 1H), 3.64-3.59 (m, 2H), 3.32 (s, 3H), 3.11-3.07 (m, 4H), 2.97 (s, 3H), 2.81-2.78 (m, 1H), 2.02-1.94 (m, 4H), 1.14 (d, J=5.7 Hz, 3H).

Example 961

N-[3-(2-{4-[1-(2-Hydroxy-ethyl)-piperidin-4-yl]-phenylamino}-pyrrolo[2,1-f][1,2,4]triazin-7-yl)-phenyl]-N-methyl-methanesulfonamide N-[3-(2-Hydroxy-pyrrolo[2,1-f][1,2,4]triazin-7-yl)-phenyl]-N-methyl-methanesulfonamide (0.0837 g, 0.263 mmol) and 2-[4-(4-Amino-phenyl)-piperidin-1-yl]-ethanol (0.0869 g, 0.394 mmol) were reacted in an analogous manner to Example 908D at 50° C. for 16 h. Concentrated reaction mixture, took up in DMSO, and purified by Gilson RP-HPLC. The fractions containing desired product were lyophilized to afford title compound as a TFA salt (28 mg, 20%). LCMS=521.0 (M+H), HPLC rt=2.364 min, purity=96%, $^1$H NMR (400 MHz, (D3C)2SO, δ, ppm): 9.51 (s, 1H), 9.19 (bs, 1H), 9.08 (s, 1H), 8.22 (s, 1H), 8.10 (d, J=7.8 Hz, 1H), 7.70 (d, J=8.0 Hz, 2H), 7.57 (dd, J=8.0 Hz, 8.0 Hz, 1H), 7.47 (d, J=8.0 Hz, 1H), 7.24-7.19 (m, 3H), 6.98 (d, J=4.4 Hz, 1H), 4.86-4.84 (m, 2H), 5.25-5.23 (m, 2H), 3.33 (s, 3H), 3.22-3.18 (m, 2H), 3.15-3.05 (m, 2H), 2.94 (s, 3H), 2.79-2.73 (m, 1H), 2.06-1.90 (m, 4H). (28 mg, 20%).

Example 962

N-{2-Chloro-5-[7-(1-methyl-1H-pyrazol-4-yl)pyrrolo[2,1f][1,2,4]triazin-2-ylamino]-phenyl}-acetamide N-(5-Amino-2-chloro-phenyl)-acetamide, and 2-Methanesulfinyl-7-(1-methyl-1H-pyrazol-4-yl)-pyrrolo[2,1-f][1,2,4]triazine were reacted in an analogous manner to Example 881D. The mixture was then taken up in DMSO and purified by Gilson prep HPLC to afford title compound as a TFA salt (96 mg, 65%). LCMS=382 (M+H); HPLC rt=2.33 min, 99% purity. $^1$H NMR (400 MHz, (D3C)2SO, δ, ppm) 8.71 (br s, 1H), 8.47 (s, 1H), 8.40 (s, 1H), 8.06 (s, 1H), 7.69 (br s, 1H). 7.38 (s, 2H), 7.08 (s, 2H), 3.96 (s, 3H), 2.26 (s, 3H).

Example 963

N-{3-[7-(1-Methyl-1H-pyrazol-4-yl)-pyrrolo[2,1-f][1,2,4]triazin-2-ylamino]-phenyl}-isobutyramide N-(3-Amino-phenyl)-isobutyramide and 2-Methanesulfinyl-7-(1-methyl-1H-pyrazol-4-yl)-pyrrolo[2,1-f][1,2,4]triazine were reacted in an analogous manner to Example 881D. The mixture was then taken up in DMSO and purified by Gilson prep HPLC to afford title compound as a TFA salt (24 mg, 23%). LCMS: 376 (M+H); HPLC rt=2.408 min, 97% purity. $^1$H NMR (400 MHz, CDCl$_3$, δ, ppm) 9.92 (br s, 1H), 8.41 (s, 2H), 8.08 (s, 1H), 7.71 (s, 1H), 7.50-7.45 (m, 2H), 7.37 (d, J=8.0 Hz, 1H), 7.33 (d, J=2.7 Hz, 1H), 7.17-7.13 (m, 2H), 3.96 (s, 3H), 2.58-2.51 (m, 1H), 1.27 (d, J=6.8 Hz, 6H).

Example 964

[7-(1-Methyl-1H-pyrazol-4-yl) pyrrolo[2,1f][1,2,4]triazin-2-yl]-(3-pyrazol-1-yl-phenyl)-amine 3-Pyrazol-1-yl-phenylamine and 2-Methanesulfinyl-7-(1-methyl-1H-pyrazol-4-yl)-pyrrolo[2,1-f][1,2,4]triazine were reacted in an analogous manner to Example 881D. The mixture was then taken up in DMSO and purified by Gilson prep HPLC to afford title compound as a TFA salt (12 mg, 9%). LCMS: 357 (M+H); HPLC rt=3.214 min, 99% purity. $^1$H NMR (400 MHz, CDCl3, δ, ppm) 10.28 (br s, 1H), 8.53 (s, 1H), 8.46 (br s, 1H), 8.43 (s, 1H), 8.02 (s, 1H), 7.98 (d, J=2.3 Hz, 1H), 7.71 (d, J=1.24 Hz, 1H), 7.52-7.42 (m, 2H), 7.36 (d, J=7.8 Hz, 1H), 7.22-7.19 (m, 2H), 6.49 (m, J=2.1, 2.1 Hz, 1H), 3.67 (s, 3H).

Example 965

N-Methyl-3-[7-(1-methyl-1H-pyrazol-4-yl)-pyrrolo[2,1-f][1,2,4]triazin-2-ylamino]-benzamide 3-Amino-N-methyl-benzamide and 2-Methanesulfinyl-7-(1-methyl-1H-pyrazol-4-yl)-pyrrolo[2,1-f][1,2,4]triazine were reacted in an analogous manner to Example 881D. The mixture was then taken up in DMSO and purified by Gilson prep HPLC to afford title compound as a TFA salt (10 mg, 8%). LCMS: 347.9 (M+H); HPLC: retention time 2.038 minutes, purity=99%. $^1$H NMR (400 MHz, DMSO, δ, ppm): 10.15 (br s, 1H), 6.67 (s, 1H), 8.52 (s, 1H), 8.41 (s, 1H), 8.03 (s, 1H), 7.59-7.57 (m, 1H), 7.47-7.43 (m, 2H), 7.19 (s, 2H), 6.27 (br s, 1H), 4.10 (s, 3H), 3.04 (d, J=4.84 Hz, 3H).

Example 966

1-{6-[7-(1-Methyl-1H-pyrazol-4-yl)-pyrrolo[2,1-f][1,2,4]triazin-2-ylamino]-2,3-dihydro-indol-1-yl}-ethanone 1-acetyl-6-aminoindoline and 2-Methanesulfinyl-7-(1-methyl-1H-pyrazol-4-yl)-pyrrolo[2,1-f][1,2,4]triazine were reacted in an analogous manner to Example 881D for 8 h. The mixture was then taken up in DMSO and purified by Gilson prep HPLC to afford title compound as a TFA salt (34 mg, 23%). LCMS: 373.9 (M+H); HPLC: retention time 2.137 min. $^1$H NMR (400 MHz, DMSO, δ, ppm): 9.25 (s, 1H), 8.85 (s, 1H), 8.49 (s, 1H), 8.10 (s, 1H), 7.28-7.26 (m, 1H), 7.19 (d, J=7.69 Hz, 1H), 7.07 (d, J=4.70 Hz, 1H), 6.88 (d, J=4.70, 1H), 4.15 (dd, J=8.58, 8.58 Hz, 2H), 3.86 (s, 3H0, 3.12 (dd, J=8.64, 8.11 Hz, 2H), 2.20 (s, 3H).

Example 967

1-{3-[7-(1-Methyl-1H-pyrazol-4-yl)-\pyrrolo[2,1-f][1,2,4]triazin-2-ylamino]-phenyl}-pyrrolidin-2-one 1-(3-Amino-phenyl)-pyrrolidin-2-one and 2-Methanesulfinyl-7-(1-methyl-1H-pyrazol-4-yl)-pyrrolo[2,1-f][1,2,4]triazine were reacted in an analogous manner to Example 881D for 6 h. The mixture was then taken up in DMSO and purified by Gilson prep HPLC to afford title compound as a TFA salt (17 mg, 11%). LCMS: 373.9 (M+H); HPLC: 2.198 min, $^1$H NMR (400 MHz, DMSO, δ, ppm): 9.39 (s, 1H), 8.89 (s, 1H), 8.40 (s, 1H), 8.16 (s, 1H), 8.00 (s, 1H), 7.52 (d, J=8.39 Hz, 1H), 7.35 (dd, J=8.20, 8.00 Hz, 1H), 7.29-7.25 (m, 1H), 7.06 (d, J=4.60 Hz, 1H), 6.91 (d, J=4.60 Hz, 1H), 3.91 (s, 3H), 3.82 (dd, J=7.13, 7.03 Hz, 2H), 2.53 (s, 2H), 2.11-2.04 (m, 2H).

Example 968

1-{3,3-Dimethyl-6-[7-(1-methyl-1H-pyrazol-4-yl)-pyrrolo[2,1-f][1,2,4]triazin-2-ylamino]-2,3-dihydro-indol-1-yl}-ethanone 1-(6-Amino-3,3-dimethyl-2,3-dihydro-indol-1-yl)-ethanone and 2-Methanesulfinyl-7-(1-methyl-1H-pyrazol-4-yl)- pyrrolo[2,1-f][1,2,4]triazine were reacted in an analogous manner to Example 881D for 4 h. The mixture was then taken up in DMSO and purified by Gilson prep HPLC to afford title compound as a TFA salt (36 mg, 23%). LCMS: 402 (M+H); HPLC: retention time 2.527 minutes, 97% purity. $^1$H NMR (400 MHz, DMSO, δ, ppm): 9.24 (s, 1H), 8.85 (s, 1H), 8.51 (s, 1H), 8.45 (s, 1H), 8.09 (s, 1H), 9.24 (s, 1H), 7.30-7.28 (m, 1H), 7.21 (d, J=8.78 Hz, 1H), 7.06 (d, J=5.27 Hz, 1H), 6.89 (d, J=4.68 Hz, 1H), 3.90 (s, 2H), 3.86 (s, 3H), 2.20 (s, 3H), 1.33 (s, 6H).

Example 969

[3-(4-Methyl-piperazin-1-yl)-phenyl]-[7-(1-methyl-1H-pyrazol-4-yl)-pyrrolo[2,1-f][1,2,4]triazin-2-yl]-amine 3-(4-Methylpiperazin-1-yl)aniline (0.110 g, 0.574 mmol) and 2-Methanesulfinyl-7-(1-methyl-1H-pyrazol-4-yl)-pyrrolo[2,1-f][1,2,4]triazine (0.100 g, 0.383 mmol) were reacted in an analogous manner to Example 881D at 170° C. for 4 hours. Product was purified on Gilson HPLC, lyophilized and free-based with NaHCO$_3$ to afford title compound as a yellow solid (44 mg, 27%) LC/MS: 389 (M+H)HPLC: retention time 1.781 minutes, purity=90%. $^1$H NMR (400 MHz, DMSO, δ, ppm): 9.65 (br s, 1H), 9.26 (s, 1H), 8.88 (s, 1H), 8.39 (s, 1H), 8.21 (s, 1H), 7.32 (d, J=6.69 Hz, 2H), 7.26 (dd, J=8.61, 8.13 Hz, 1H), 7.04 (d, J=4.8 Hz, 1H), 6.91 (d, J=4.8 Hz, 1H), 6.68 (d, J=7.4 Hz, 1H), 3.94 (s, 3H), 3.78 (d, J=13.0 Hz, 2H), 3.52 (d, J=12.0 Hz, 2H), 3.18-3.16 (m, 2H), 3.00-2.93 (m, 2H), 2.88 (d, J=4.0 Hz, 3H).

Example 970

[3-(4-Methyl-piperazin-1-yl)-phenyl]-[7-(1H-pyrazol-4yl)-pyrrolo[2,1-f][1,2,4]triazin-2-yl]-amine 4-(4,4,5,5-Tetramethyl-1,3,2-dioxaborolan-2-yl)-pyrazole-1-carboxylic acid tert-butyl ester (0.911 g) and (7-Bromo-pyrrolo[2,1-f][1,2,4]triazin-2-yl)-3-(4-methyl-piperazin-1-yl)-phenyl]-amine (0.800 g, 0.00206 mol) were reacted in an analogous manner to Example 881A. The reaction mixture was purified by ISCO silica gel column chromatography (DCM/MeOH) to afford title compound (250 mg, 31%) (LC/MS: 375 (M+H); HPLC: 0.777 min, 97% purity) MP: 195° C. $^1$H NMR (400 MHz, DMSO, δ, ppm): 13.17 (br s, 1H), 9.16 (s, 1H), 8.87 (s, 1H), 8.47 (s, 1H), 8.25 (s, 1H), 7.29 (s, 1H), 7.21-7.14 (m, 2H), 7.07 (d, J=4.9, 1H), 6.90 (d, J=4.9 Hz, 1H), 6.59 (d, J=7.6 Hz, 1H), 3.11 (dd, J=4.5, 4.8 Hz, 4H), 2.45 (dd, J=4.5, 4.5 Hz, 4H), 2.22 (s, 3H).

Example 971

{7-[1-(3-Methyl-butyl)-1H-pyrazol-4-yl]-pyrrolo[2,1-f][1,2,4]triazin-2-yl}-[3-(4-methyl-piperazin-1-yl)-phenyl]-amine (7-Bromo-pyrrolo[2,1-f][1,2,4]triazin-2-yl)-[3-(4-methyl-piperazin-1-yl)-phenyl]-amine (0.080 g, 0.00021 mol) and 1-(3-Methyl-butyl)-4-(4,4,5,5-tetramethyl-1,3,2-dioxaborolan-2-yl)-1H-pyrazole (0.140 g, 0.000530 mol) were reacted in an analogous manner to Example 881A. The reaction mixture was purified by Gilson RP-HPLC to afford title compound as a TFA salt (40 mg, 40%). LC/MS: 445 (M+H); HPLC 2.461 min, 97% purity). $^1$H NMR (400 MHz, DMSO, δ, ppm): 9.63 br s, 1H), 9.31 (s, 1H), 8.95 (s, 1H), 7.84 (s, 1H), 7.49 (s, 1H), 7.30 (d, J=7.9 Hz, 1H), 7.19 (dd, J=7.9, 8.6 Hz, 1H), 6.81 (d, J=4.6 Hz, 1H), 6.76-6.75 (m, 1H), 6.63 (d, J=9.6 Hz, 1H), 3.81 (d, J=13.1 Hz, 4H), 3.54 (d, J=11.8 Hz, 4H), 3.23-3.15 (m, 2H), 2.98 (dd, J=11.1, 12.5 Hz, 2H), 2.88 (d, J=3.9 Hz, 3H).

Example 972

{7-[1-(2-Methoxy-ethyl)-1H-pyrazol-4-yl]-pyrrolo[2,1-f][1,2,4]triazin-2-yl}-[3-(4-methyl-piperazin-1-yl)-phenyl]-amine

[3-(4-Methyl-piperazin-1-yl)-phenyl]-[7-(1H-pyrazol-4-yl)-pyrrolo[2,1-f][1,2,4]triazin-2-yl]-amine (0.080 g, 0.00021 mol) and Ethane, 1-bromo-2-methoxy (0.0201 mL, 0.000214 mol) were reacted in an analogous manner to Example 932A. Product was purified using Gilson chromography and lyophilized to afford title compound as a TFA salt (10 mg, 11%). LC/MS: 433 (M+H)HPLC: 1.657 min, 99% purity) $^1$H NMR (400 MHz, DMSO, δ, ppm): 9.72 (br s, 1H), 9.25 (s, 1H), 8.88 (s, 1H), 8.43 (s, 1H), 8.25 (s, 1H), 7.38 (d, J=8.3 Hz, 1H), 7.29-7.25 (m, 2H), 7.06 (d, J=4.5 Hz, 1H), 6.91 (d, J=4.5 Hz, 1H), 6.68 (dd, J=1.3, 8 Hz, 1H), 4.35 (dd, J=5.2, 5.2 Hz, 2H), 3.79-3.73 (m, 4H), 3.52 (d, J=12.4 Hz, 2H), 3.22 (s, 3H), 3.21-3.17 (m, 2H), 2.97 (dd, J=12.2, 11.7 Hz, 2H), 2.87 (d, J=3.1 Hz, 3H).

Example 973

(4-Chloro-3-morpholin-4-ylmethyl-phenyl)-[7-(6-methoxy-pyridin-3-yl)-pyrrolo[2,1-f][1,2,4]triazin-2-yl]-amine 973A. 4-(2-Chloro-5-nitro-benzyl)-morpholine. 2-Chloro-5-nitro-benzaldehyde (1.00 g, 5.39 mmol) and Morpholine (0.470 g, 5.39 mmol) were dissolved in CH$_2$Cl$_2$ (18.3 mL). Sodium triacetoxyborohydride (1.60 g, 7.54 mmol) was added, and the reaction mixture was stirred for 48 at rt. 2 M of Sodium hydroxide in water (45.7 mL, 114 mmol) was added and the mixture was stirred at rt for 10 min. The reaction mixture was further diluted with NaOH and extracted with CH$_2$Cl$_2$. The combined organics were extracted with 2 N HCl. The aqueous layer was then basified to pH>12 by treatment with solid NaOH. This aqueous layer was extracted with ethyl acetate. The organics were combined, washed with brine, dried over MgSO4, filtered and concentrated. (878 mg, 61%). LC/MS: 256.9 (M+H)HPLC: 0.535 minutes, purity=96%. $^1$H NMR (400 MHz, DMSO, δ, ppm): 8.32 (d, J=2.6 Hz, 1H), 8.15-8.12 (m, 1H), 7.75 (d, J=8.8 Hz, 1H), 3.66 (s, 2H), 3.61 (dd, J=4.6, 4.3 Hz, 4H), 2.47 (dd, J=4.2, 4.2 Hz, 4H)

973B. 4-Chloro-3-morpholin-4-ylmethyl-phenylamine. 4-(2-Chloro-5-nitro-benzyl)-morpholine (0.878 g, 3.42 mmol), Tin(II) chloride (1.95 g, 10.3 mmol), and Ethanol (12.2 mL, 209 mmol) were heated to 75° C. for 16 h. The reaction was treated with aq K2CO3. The mixture was vacuum filtered and the solids were washed with ethyl acetate and dichloromethane. The aqueous solution was extracted with CH$_2$Cl$_2$. The combined organics were washed with brine, dried over magnesium sulfate, filtered and concentrated. Product was used without purification. LC/MS: 227 (M+H); HPLC: 0.487 minutes 675 mg (73%) 84% purity.

973C. (4-Chloro-3-morpholin-4-ylmethyl-phenyl)-[7-(6-methoxy-pyridin-3-yl)-pyrrolo[2,1-f][1,2,4]triazin-2-yl]-amine. 4-Chloro-3-morpholin-4-ylmethyl-phenylamine (0.060 g, 0.00022 mol) and 2-Methanesulfinyl-7-(6-methoxy-pyridin-3-yl)-pyrrolo[2,1-f][1,2,4]triazine (0.060 g, 0.00021 mol) were reacted in an analogous manner to Example 881D at 200° C. for 1 h. Product was purified on Gilson HPLC and lyophilized to afford title compound as a TFA salt (37 mg, 38%). LC/MS: 451 (M+H HPLC: 2.93 min purity=96%) HNMR: $^1$H NMR (400 MHz, DMSO, δ, ppm): 9.87 (br s, 1H), 9.09 (s, 1H), 9.04 (s, 1H), 8.36 (dd, J=2.3, 8.8 Hz, 1H), 8.17 (s, 1H), 7.70 (d, J=7.8 Hz, 1H), 7.53 (d, J=8.4 Hz, 1H), 7.23 (d, J=5.2 Hz, 1H), 7.05 (d, J=8.7 Hz, 1H), 7.03 (d, J=4.7 Hz, 1H), 4.50 (s, 2H), 3.97 (s, 3H), 3.91 (s, 2H), 3.6 (s, 2H), 3.26 (s, 4H).

Example 974

3-[7-(6-Methoxy-pyridin-3-yl)pyrrolo[2,1f][1,2,4]triazin-2-ylamino]-benzonitrile 7-(6-Methoxy-pyridin-3-yl)-pyrrolo[2,1-f][1,2,4]triazin-2-ol (75.0 mg, 0.310 mmol) and 3-Amino-benzonitrile (45.72 mg, 0.3870 mmol) were reacted in an analogous manner to Example 908D at rt for 72 h. The solvent was reduced under pressure, the resulting residue taken up in DMSO and purified by Gilson chromotography and lyophilized to afford title compound as a TFA salt (6 mg, 6% yield). LC/MS 342.9 (M+H); $^1$H NMR (400 MHz, DMSO, δ, ppm): 9.95 (s, 1H), 9.05 (s, 1H), 8.87 (d, J=1.72 Hz, 1H), 8.49 (d. J=8.65 Hz, 1H), 8.36 (s, 1H), 7.83 (d, J=8.0 Hz, 1H), 7.51 (dd, J=8.19, 7.41 Hz, 1H), 7.40 (d, J=7.41 Hz, 1H), 7.20 (d, J=4.42 Hz, 1H), 7.05-7.02 (m, 2H), 3.95 (s, 3H).

Example 975

2-{3-[7-(6-Methoxy-pyridin-3-yl)-pyrrolo[2,1-f][1,2,4]triazin-2-ylamino]-phenylamino}-acetamide N-[7-(6-Methoxy-pyridin-3-yl)-pyrrolo[2,1-f][1,2,4]triazin-2-yl]-benzene-1,3-diamine (0.055 g, 0.00016 mol), Iodoacetamide (0.306 g, 0.00165 mol), and Cesium Carbonate (0.809 g, 0.00248 mol) were dissolved in DMF (5 mL, 0.4 mol), and the reaction was heated to 85° C. for 96 h. The reaction mixture was concentrated and extracted with ethyl acetate and water. The combined organics were dried over magnesium sulfate, filtered, and concentrated. Product was purified by Gilson chromotography and lyophilized to afford title compound as a TFA salt (5 mg, 8%). LC/MS: 390 (M+H); HPLC: 2.302 minutes, 98% purity) $^1$H NMR (400 MHz, DMSO, δ, ppm): 9.29 (br s, 1H), 9.01 (d, J=1.87 Hz, 1H), 8.96 (s, 1H), 8.51 (dd, J=2.4, 6.29 Hz, 1H), 7.31 (br s, 1H), 7.05-7.00 (m, 4H), 6.95 (d, J=4.5 Hz, 1H), 6.23 (d, J=6.5 Hz, 1H), 3.92 (s, 3H), 3.60 (s, 2H).

Example 976

3-(4-{2-[3-(4-Methyl-piperazin-1-yl)-phenylamino]-pyrrolo[2,1-f][1,2,4]triazin-7-yl}-pyrazol-1-yl)-propan-1-ol

[3-(4-Methyl-piperazin-1-yl)-phenyl]-[7-(1H-pyrazol-4-yl)-pyrrolo[2,1-f][1,2,4]triazin-2-yl]-amine (0.100 g, 0.000267 mol) and 3-Bromo-1-propanol (0.0483 mL, 0.000534 mol)were reacted in an analogous manner to Example 932A. Product was purified using Gilson chromography and lyophilized to afford title compound as a TFA salt (17 mg, 15%). LC/MS: 433 (M+H); retention time 0.69 minutes HPLC: retention time 1.648 min. $^1$H NMR (400 MHz, DMSO, δ, ppm): 9.73 (br s, 1H), 9.27 (d, J=12.9 Hz, 1H), 8.88 (s, 1H), 8.44 (s, 1H), 8.25 (d, J=14.3 Hz, 1H0, 7.38-7.25 (m, 3H), 7.05 (d, J=4.8 Hz, 1H), 6.91 (d, J=4.8 Hz, 1H), 6.69 (dd, J=8.8, 9.6 Hz, 1H), 4.25 (t, 2H), 3.42 (t, 2H), 3.18 (dd, J=10.1, 10.6 Hz, 4 h)<2.97 (dd, J=12.2, 11.8 Hz, 4H), 2.02-1.96 (m, 2H).

Example 977

3-(4-{2-[3-(4-Methyl-piperazin-1-yl)-phenylamino]-pyrrolo[2,1-f][1,2,4]triazin-7-yl}-pyrazol-1-yl)-propionitrile

[3-(4-Methyl-piperazin-1-yl)-phenyl]-[7-(1H-pyrazol-4-yl)-pyrrolo[2,1-f][1,2,4]triazin-2-yl]-amine (0.100 g, 0.000267 mol) and 3-Bromo-propionitrile (0.0443 mL, 0.000534 mol) were reacted in an analogous manner to Example 932A. Product was purified using Gilson chromography and lyophilized to afford title compound as a TFA salt (86 mg, 74%). LC/MS: 428 (M+H); HPLC: 1.828 minutes, 98% purity. $^1$H NMR (400 MHz, CDCl3, δ, ppm): 8.66 (s, 1H), 8.41 (s, 1H), 8.10 (s, 1H), 8.02 (s, 1H) 7.31 (dd, J=8.1, 8.1 Hz, 1H), 7.19 (d, J=7.7 Hz, 1H), 7.10 (s, 1H), 6.90 (d, J=5.0 Hz, 1H), 6.81 (d, J=4.6 Hz, 1H), 6.74-6.72 (m, 2H), 4.46 (t, 2H), 3.24 (dd, J=4.7, 5.4 Hz, 4H), 2.57 (dd, J=4.9, 4.9 Hz, 4H), 2.35 (s, 3H).

Example 978

2-(4-{2-[3-(4-Methyl-piperazin-1-yl)-phenylamino]-pyrrolo[2,1-f][1,2,4]triazin-7-yl}-pyrazol-1-yl)-acetamide

[3-(4-Methyl-piperazin-1-yl)-phenyl]-[7-(1H-pyrazol-4-yl)-pyrrolo[2,1-f][1,2,4]triazin-2-yl]-amine and Iodoacetamide (0.0988 g, 0.534 mmol) were reacted in an analogous manner to Example 932A. Product was purified using Gilson chromography and lyophilized to afford title compound as a TFA salt (34 mg, 29%). LC/MS: 432 (M+H) HPLC: 1.641 min, 97% purity. $^1$H NMR (400 MHz, DMSO, δ, ppm): 9.31 (s, 1H), 8.89 (s, 1H0, 8.39 (s, 1H), 7.96 (s, 1H-7.77 (s, 1H), 7.41 (s, 1H), 7.28-7.22 (m, 2H), 7.09 (d, J=4.6 Hz, 1H), 6.92 (d, J=4.6 Hz, 1H), 6.68 (d, J=7.4 Hz, 1H), 4.24 (s, 2H), 3.77 (dd, J=11.3, 14.3 Hz, 4H), 3.51 (dd, J=17.8, 10.4 Hz, 4H), 3.35 (s, 3H).

Example 979

7-[7-(6-Methoxy-pyridin-3-yl)-pyrrolo[2,1-f][1,2,4]triazin-2-ylamino]-3,4-dihydro-1H-quinolin-2-one 7-(6-Methoxy-pyridin-3-yl)-pyrrolo[2,1-f][1,2,4]triazin-2-ol (75.0 mg, 0.310 mmol) and 7-Amino-3,4-dihydro-1H-quinolin-2-one (62.77 mg, 0.3870 mmol) were reacted in an analogous manner to Example 908D at rt for 16 h. The solvent was reduced under pressure and the resulting residue was taken up in DMSO, purified by Gilson RP-HPLC to afford title compound as a TFA salt (5 mg, 4%) LC/MS 387 (M+H) HPLC 2.701 min, 95% purity) $^1$H NMR (400 MHz, CDCl3, δ, ppm): 9.20 (s, 1H), 7.97 (s, 1H), 7.91-7.89 (m, 2H), 7.19 (s, 1H), 7.01 (d, J=7.9 Hz, 1H), 6.95 (s, 1H), 6.87 (d, J=4.8 Hz, 1H), 6.82 (d, J=8.6 Hz, 1H), 6.78 (d, J=4.6 Hz, 1H), 6.65 (d, J=7.9 Hz, 1H), 4.10 (s, 3H), 2.87 (t, 2H), 2.58 (t, 2H).

Example 980

[7-(6-Methoxy-pyridin-3-yl)-pyrrolo[2,1-f][1,2,4]triazin-2-yl]-(1-methyl-1,2,3,4-tetrahydro-quinolin-7-yl)-amine 7-(6-Methoxy-pyridin-3-yl)-pyrrolo[2,1-f][1,2,4]triazin-2-ol (75.0 mg, 0.310 mmol) and 1-Methyl-1,2,3,4-tetrahydro-quinolin-7-ylamine (62.79 mg, 0.3870 mmol) were reacted in an analogous manner to Example 908D at rt for 16 h. The solvent was reduced under pressure and the resulting residue was taken up in DMSO, purified by Gilson RP-HPLC to afford title compound as a TFA salt (20 mg, 17%). LC/MS: 387 (M+H); HPLC 2.58 min. $^1$H NMR (400 MHz, CDCl3, δ, ppm): 9.91 (br s, 1H), 8.91 (s, 1H), 8.56 (s, 1H), 8.26 (d, J=9.0 Hz, 1H), 7.58 (s, 1H), 7.29 (d, J=8.5 Hz, 1H), 7.19-7.17 (m, 1H), 7.11 (d, J=5.0, 1H), 7.07 (d, J=8.4 Hz, 1H), 6.90 (d, J=8.7 Hz, 1H), 3.95 (s, 3H), 3.44 (t, 2H), 3.03 (s, 3H), 2.82 (t, 2H), 2.12-2.06 (m, 2H).

Example 981

7-[7-(2-Methoxy-phenyl)-pyrrolo[2,1-f][1,2,4]triazin-2-ylamino]-3,4-dihydro-1H-quinolin-2-one Trifluoro-methanesulfonic acid 7-(2-methoxy-phenyl)-pyrrolo[2,1-f][1,2,4]triazin-2-yl ester (0.080 g, 0.21 mmol) and 7-Amino-3,4-dihydro-1H-quinolin-2-one (0.043 g, 0.27 mmol) were reacted in an analogous manner to Example 908D at 50° C. for 16 h. Upon completion, the product was triturated and washed with acetone. LC/MS: 386 (M+H); HPLC: 2.920 minutes, 99% purity, MP: 310-313° C. $^1$H NMR (400 MHz, CDCl$_3$, $_6$, ppm): 8.56 (s, 1H), 7.97 (d, J=8.6 Hz, 1H), 7.65 (dd, J=7.8, 8.3 Hz, 1H), 7.47 (s, 1H), 7.23-7.16 (m, 3H), 7.07 (d, J=8.0 Hz, 1H), 7.02 (s, 1H), 6.96 (d, J=5.9 Hz, 1H), 3.88 (s, 3H), 2.93 (t, 2H), 2.64 (t, 2H).

Example 982

[7-(2-Methoxy-phenyl)-pyrrolo[2,1-f][1,2,4]triazin-2-yl]-(1-methyl-1,2,3,4-tetrahydro-quinolin-7-yl)-amine Trifluoro-methanesulfonic acid 7-(2-methoxy-phenyl)-pyrrolo[2,1-f][1,2,4]triazin-2-yl ester (0.080 g, 0.21 mmol) and 1-Methyl-1,2,3,4-tetrahydro-quinolin-7-ylamine (0.043 g, 0.27 mmol) were reacted in an analogous manner to Example 908D at 50° C. for 16 h. The reaction mixture was concentrated, taken up in DMSO, purified by Gilson RP-HPLC and lyophilized to afford title compound as a TFA salt (25 mg, 29%). LC/MS: 386 (M+H); HPLC: 2.793 minutes, 95% purity. $^1$H NMR (400 MHz, CDCl$_3$, δ, ppm): 9.74 (br s, 1H), 8.45 (s, 1H), 7.75 (d, J=7.3 Hz, 1H), 7.41 (dd, J=7.3, 8.4 Hz, 1H), 7.28 (s, 1H), 7.07-7.00 (m, 3H), 6.87 (d, J=8.4 Hz, 1H), 3.76 (s, 3H), 3.22 (t, 2H), 2.69 (t, 2H), 2.56 (s, 3H), 1.99-193 (m, 2H).

Example 983

6-Fluoro-7-[7-(6-methoxy-pyridin-3-yl)-pyrrolo[2,1-f][1,2,4]triazin-2-ylamino]-3,4-dihydro-1H-quinolin-2-one Trifluoro-methanesulfonic acid 7-(6-methoxy-pyridin-3-yl)-pyrrolo[2,1-f][1,2,4]triazin-2-yl ester (0.080 g, 0.21 mmol) and 7-Amino-6-fluoro-3,4-dihydro-1H-quinolin-2-one were reacted in an analogous manner to Example 908D at 50° C. for 32 h. Upon completion, the product was triturated and washed with acetone. LC/MS: 404.9 (M+H); HPLC: 2.770 minutes, 99% purity. MP: 295° C. $^1$H NMR (400 MHz, CDCl$_3$, δ, ppm): 8.91 (s, 1H), 8.65 (s, 1H), 8.34 (d, J=9.9 Hz, 1H), 7.48-7.42 (m, 2H), 7.10-7.05 (m, 2H), 6.94-6.90 (m, 2H), 4.05 (s, 3H), 3.06 (t, 2H), 2.71 (t, 2H).

Example 984

[7-(2-Methoxy-phenyl)-pyrrolo[2,1-f][1,2,4]triazin-2-yl]-(2-methyl-1,2,3,4-tetrahydro-isoquinolin-7-yl)-amine 984A. 2-Methyl-1,2,3,4-tetrahydro-isoquinolin-7-ylamine. 7-Amino-3,4-dihydro-1H-isoquinoline-2-carboxylic acid tert-butyl ester (0.500 g, 2.01 mmol) was reacted in an analogous manner to Example 908C. Product was used without further purification. LC/MS: 163 (M+H), $^1$H NMR (400 MHz, DMSO, δ, ppm): 6.72 (d, J=7.9 Hz, 1H), 6.34 (d, J=8.3 Hz, 1H), 6.21 (s, 1H), 4.76 (s, 2H), 2.27 (t, 2H), 3.33 (s, 2H), 2.62 (t, 2H), 2.28 (s, 3H)

984B. Trifluoro-methanesulfonic acid 7-(6-methoxy-pyridin-3-yl)-pyrrolo[2,1-f][1,2,4]triazin-2-yl ester (0.085 g, 0.23 mmol) and 2-Methyl-1,2,3,4-tetrahydro-isoquinolin-7-ylamine (0.062 g, 0.28 mmol) were reacted in an analogous manner to Example 908D at 50° C. for 16 h. The reaction mixture was concentrated, taken up in DMSO, purified by Gilson RP-HPLC and lyophilized. LC/MS: 387.0 (M+H); HPLC: 2.214 minutes, purity=99%) $^1$H NMR (400 MHz, DMSO, δ, ppm): 9.95 (br s, 1H), 9.65 (s, 1H), 9.04 (s, 1H), 9.01 (s, 1H), 8.43 (d, J=8.6 Hz, 1H), 7.81 (s, 1H), 7.46 (d, J=8.3 Hz, 1H), 7.22-7.20 (m, 2H), 7.07 (d, J=8.8 Hz, 1H), 6.99 (d, J=4.4 Hz, 1H), 4.48 (d, 15.2 Hz, 1H) 4.40-4.34 (m, 1H), 3.97 (s, 3H), 3.73-3.65 (m, 1H), 3.45-3.31 (m, 1H), 3.17-3.06 (m, 2H), 3.22 (s, 3H).

Example 985

[7-(6-Methoxy-pyridin-3-yl)-pyrrolo[2,1-f][1,2,4]triazin-2-yl]-(2-methyl-1,2,3,4-tetrahydro-isoquinolin-7-yl)-amine Trifluoro-methanesulfonic acid 7-(2-methoxy-phenyl)-pyrrolo[2,1-f][1,2,4]triazin-2-yl ester (0.085 g, 0.23 mmol) and 2-Methyl-1,2,3,4-tetrahydro-isoquinolin-7-ylamine (0.062 g, 0.28 mmol) were reacted in an analogous manner to Example 908D rt for 16 h. The reaction mixture was concentrated, purified by Gilson RP-HPLC and lyophilized to afford title compound as a TFA salt (45 mg, 51%) LC/MS: 386.0 (M+H); HPLC: 2.416 min, 99% purity. $^1$H NMR (400 MHz, DMSO, δ, ppm): 9.82 (br s, 1H), 9.55 (s, 1H), 8.97 (s, 1H) 7.79 (d, J=7.4 Hz, 1H), 7.60 (s, 1H), 7.53-7.49 (m, 2H), 7.25 (d, J=8.3 Hz, 1H), 7.18 (dd, J=7.9, 7.9 Hz, 1H), 7.10 (d, J=8.3, 1H), 6.97-6.94 (m, 2H), 4.23-4.18 (m, 2H), 3.79 (s, 3H), 3.69-3.61 (m, 1H), 3.36-3.24 (m, 1H), 3.04-3.01 (m, 1H), 2.95 (d, J=4.4 Hz, 3H).

Example 986

2-{7-[7-(6-Methoxy-pyridin-3-yl)-pyrrolo[2,1-f][1,2,4]triazin-2-ylamino]-3,4-dihydro-1H-isoquinolin-2-yl}-acetamide 986A. 2-(7-Amino-3,4-dihydro-1H-isoquinolin-2-yl)-acetamide. 1,2,3,4-Tetrahydro-isoquinolin-7-ylamine (0.300 g, 0.00202 mol) was reacted in an analogous manner to Example 911B at 80° C. for 48 h, after which the reaction mixture was filtered to remove cesium carbonate and the resulting filtrate was concentrated under high vacuum. The product was used without further purification. LC/MS: 206 (M+H)HPLC: retention time 0.429 min.

986B. Trifluoro-methanesulfonic acid 7-(6-methoxy-pyridin-3-yl)-pyrrolo[2,1-f][1,2,4]triazin-2-yl ester (0.075 g, 0.20 mmol) and 2-(7-Amino-3,4-dihydro-1H-isoquinolin-2- yl)-acetamide (0.0617 g, 0.300 mmol) were reacted in an analogous manner to Example 908D for 2 days at 50° C. at which time additional 3 eq 2-(7-Amino-3,4-dihydro-1H-isoquinolin-2-yl)-acetamide were added and the reaction mixture heated an additional 5 days. The reaction mixture was concentrated, purified by Gilson RP-HPLC and lyophilized to afford title compound as a TFA salt (3 mg, 3%). LC/MS: 430.0 (M+H); HPLC: 2.091 min, 90% purity). $^1$H NMR (400 MHz, DMSO, δ, ppm): 10.33 (br s, 1H), 9.63 (s, 1H), 9.00 (s, 1H), 8.98 (d, J=2.0 Hz, 1H), 8.47 (d, J=8.8 Hz, 1H), 7.98 (s, 1H), 7.76 (d, J=8.4 Hz, 2H), 7.47 (d, J=8.4 Hz, 1H), 7.22-7.19 (m, 2H), 7.05 (d, J=9.0 Hz, 1H), 6.98 (d, J=4.9 Hz, 1H), 4.60-4.47 (m, 1H), 4.47-4.45 (m, 1H), 4.08.400 (m, 2H), 3.97 (s, 3H), 3.19=3.02 (m, 2H), 3.02-2.90 (m, 2H).

Example 987

2-{7-[7-(2-Methoxy-phenyl)-pyrrolo[2,1-f][1,2,4]triazin-2-ylamino]-3,4-dihydro-1H-isoquinolin-2-yl}-acetamide Trifluoro-methanesulfonic acid 7-(2-methoxy-phenyl)-pyrrolo[2,1-f][1,2,4]triazin-2-yl ester (0.075 g, 0.20 mmol) and 2-(7-Amino-3,4-dihydro-1H-isoquinolin-2-yl)-acetamide (0.0884 g, 0.301 mmol)) were reacted in an analogous manner to Example 908D for 48 h at 50° C. at which time additional 3 eq 2-(7-Amino-3,4-dihydro-1H-isoquinolin-2-yl)-acetamide were added and the reaction mixture heated an additional 5 days. The reaction mixture was concentrated, purified by Gilson RP-HPLC and lyophilized to afford title compound as a TFA salt (2 mg, 2%). LC/MS: 429 (M+H); HPLC: 2.277 minutes, 98% purity). $^1$H NMR (400 MHz, CDCl3, δ, ppm): 10.68 (br s, 1H), 8.46 (s, 1H), 8.19 (br s, 1H), 7.78 (d, J=8.0 Hz, 1H), 7.64 (s, 1H), &.53 (dd, J=7.3, 7.5 Hz, 1H), 7.37 (d, J=8.3 Hz, 1H), 7.26-7.23 (m, 2H), 7.11-7.03 (m, 3H), 5.84 (br s, 1H), 4.26-4.13 (m, 2H), 3.83 (s, 2H), 3.78 (s, 3H), 3.57-3.46 (m, 2H), 3.20-3.04 (m, 2H).

Example 988

N-(3-{7-[3-(2-Methoxy-ethylamino)-phenyl]-pyrrolo[2,1-f][1,2,4]triazin-2-ylamino}-phenyl)-acetamide 988A. (2-Methoxy-ethyl)-[3-(2-methylsulfanyl-pyrrolo[2,1-f][1,2,4]triazin-7-yl)-phenyl]-amine. 3-(2-Methylsulfanyl-pyrrolo[2,1-f][1,2,4]triazin-7-yl)-phenylamine (0.500 g, 0.00195 mol), Ethane, 1-bromo-2-methoxy (0.271 g, 0.00195 mol) and Potassium carbonate (0.577 g, 0.00418 mol) were dissolved in N,N-Dimethylformamide (13 mL, 0.17 mol) and the reaction mixture was heated at 80° C. for 16 h. Solvent was reduced in vacuo. Residue was washed with saturated ammonium chloride, and organics were extracted with diethyl ether. Combined organics were dried over magnesium sulfate, filtered, and reduced. Product was purified using Gilson HPLC to afford title compound as a TFA salt (274 mg , 43%) LC/MS: 314.9 (M+H); HPLC: 2.468 min, 96%. $^1$H NMR (400 MHz, DMSO, δ, ppm): 8.97 (s, 1H), 7.47 (s, 1H), 7.35 (d, J=7.4 Hz, 1H), 7.35 (d, J=4.5 Hz, 1H), 7.20 (d, J=4.5 Hz, 1H), 7.22 (dd, J=7.9, 7.9 Hz, 1H), 7.07 (d, J=4.9, 1H), 6.68 (d, J=6.9, 1H), 3.52 (dd, J=5.3, 6.0 Hz, 2H), 3.29-3.26 (m, 5H), 2.59 (s, 3H)

988B. [3-(2-Methanesulfinyl-pyrrolo[2,1-f][1,2,4]triazin-7-yl)-phenyl]-(2-methoxy-ethyl)-amine (2-Methoxy-ethyl)-[3-(2-methylsulfanyl-pyrrolo[2,1-f][1,2,4]triazin-7-yl)-phenyl]-amine (0.275 g, 0.000875 mol) was reacted in an analogous manner to Example 881C. Sample was purified using Gilson chromotography and lyophilized to afford title compound as a TFA salt (125 mg, 43%). LCMS: 330.9 (M+H); HPLC: rt 1.683 min, 96% purity.

988C. N-(3-{7-[3-(2-Methoxy-ethylamino)-phenyl]-pyrrolo[2,1-f][1,2,4]triazin-2-ylamino}-phenyl)-acetamide. 3'-aminoacetanilide (0.033 g, 0.00022 mol) and [3-(2-Methanesulfinyl-pyrrolo[2,1-f][1,2,4]triazin-7-yl)-phenyl]-(2-methoxy-ethyl)-amine (0.068 g, 0.00021 mol), were reacted in an analogous manner to Example 881D at 200° C. for 1 h. Product was purified on Gilson HPLC and lyophilized to afford title compound as a TFA salt (8 mg, 8%). LCMS: 417 (M+H)HPLC 2.282 min, 91% purity) $^1$H NMR (400 MHz, DMSO, δ, ppm): 9.79 (br s, 1H), 9.43 (s, 1H), 8.95 (s, 1H), 7.71 (s, 1H), 7.66 (d, J=6.5 Hz, 1H), 7.42 (d, J=8.3, 1H), 7.33 (br s, 1H), 7.23-7.18 (m, 3H), 7.07 (d, J=4.7 Hz, 1H), 6.93 (d, J=4.7 Hz, 1H), 6.68 (d, J=7.0 Hz, 1H), 3.50 (dd, J=5.5, 5.5 Hz, 2H), 3.28 (s, 3H), 3.24 (dd, J=5.5, 5.7 Hz, 2H), 2.04 (s, 3H).

Example 991

(R)-1-{7-Methoxy-8-[7-(2-methoxy-phenyl)-pyrrolo[2,1-f][1,2,4]triazin-2-ylamino]-1,2,4,5-tetrahydro-benzo[d]azepin-3-yl}-propan-2-ol Following a procedure analogous to 251c, (R)-1-(7-Amino-8-methoxy-1,2,4,5-tetrahydro-3-benzazepin-3-yl)-propan-2-ol (0.139 g, 0.557 mmol) and 2-methanesulfinyl-7-(2-methoxy-phenyl)-pyrrolo[2,1-f][1,2,4]triazine (64 mg, 0.22 mol) were converted to the title compounds (22.66 mgs) as a TFA salt. H-NMR (CDCl$_3$) δ 9.30 (broad s, 1H, TFA), 8.96 (s, 1H), 7.97 (s, 1H), 7.82 (d, J=7.6 Hz, 1H), 7.61 (s, 1H), 7.50-7.45 (m, 1H), 7.26-7.21 (m, 1H), 7.14-7.09 (m, 1H), 6.99-6.93 (m, 2H), 6.93 (s, 1H), 4.22-4.12 (m, 1H), 3.86 (s, 3H), 3.78 (s, 3H), 3.69-3.60 (m, 2H), 3.29-2.93 (complex series of m, 8H), 1.16 (d, J=6.0 Hz, 3H); LC/MS (ESI+): 474.6 (M+H).

Example 992

(3-Methoxy-6-morpholin-4-yl-6,7,8,9-tetrahydro-5H-benzocyclohepten-2-yl)-[7-(2-methoxy-phenyl)-pyrrolo[2,1-f][1,2,4]triazin-2-yl]-amine Following a procedure analogous to 251c, 3-Methoxy-6-morpholin-4-yl-6,7,8,9-tetrahydro-5H-benzocyclohepten-2-ylamine (0.164 g, 0.59 mmol) and 2-methanesulfinyl-7-(2-methoxy-phenyl)-pyrrolo[2,1-f][1,2,4]triazine (85 mg, 0.30 mol) were converted to the title compound (19.6 mgs). $^1$H-NMR (DMSO-d6) δ 8.70 (s, 1H), 8.16 (s, 1H), 8.02 (d, J=7.4 Hz, 1H), 7.45-7.41 (m, 2H), 7.50-7.45 (m, 2H), 7.14-7.07 (m, 2H), 7.03 (d, J=4.9 Hz, 1H), 6.71 (s, 1H), 3.90 (s, 3H), 3.86 (s, 3H), 3.79-3.74 (m, 4H), 2.91-2.50 (complex series of m, 7H), 2.40 (t, J=10.6 Hz, 1H), 2.16-2.00 (m, 2H), 1.80-1.70 (m, 1H), 1.43-1.33 (m, 1H); LC/MS (ESI+): 500.17 (M+H).

Example 993

N-{2-[2-(3-Methoxy-6-morpholin-4-yl-6,7,8,9-tetrahydro-5H-benzocyclohepten-2-ylamino)-pyrrolo[2,1-f][1,2,4]triazin-7-yl]-phenyl}-N-methyl-methanesulfonamide Following a procedure analogous to 251c, 3-Methoxy-6-morpholin-4-yl-6,7,8,9-tetrahydro-5H-benzocyclohepten-2-ylamine (0.095 g, 0.34 mmol) and N-[2-(2-Methanesulfinyl-pyrrolo[2,1-f][1,2,4]triazin-7-yl)-phenyl]-N-methyl-methanesulfonamide (63 mg, 0.17 mol) were converted to the title compound (25.89 mgs) as a TFA salt. H-NMR (CDCl$_3$) δ 9.59 (broad s, 1H-TFA), 8.96 (s, 1H), 7.90 (d, J=8.5 Hz, 1H), 7.81 (s, 1H), 7.68-7.49 (m, 4H), 6.98-6.95 (m, 3H), 4.06-4.00 (m, 2H), 3.85 (s, 3H), 3.78-3.69 (m, 2H), 3.44-3.14 (complex series of m, 7H), 3.90-3.04 (m, 5H), 2.86 (s, 3H), 2.68-2.58 (m, 1H), 2.39-2.19 (m, 3H) 2.09-1.87 (m, 2H); LC/MS (ESI+): 577.2 (M+H).

Example 994

[7-(2-Methoxy-phenyl)-pyrrolo[2,1-f][1,2,4]triazin-2-yl]-[2-methoxy-4-(4-pyridin-2-yl-piperazin-1-yl)-phenyl]-amine Following a procedure analogous to 33a, 1-Pyridin-2-yl-piperazine (0.33 g) was converted to 2-Methoxy-4-(4-pyridin-2-yl-piperazin-1-yl)-phenylamine which following a procedure analogous to 251c was converted to the title compound (47.87 mg) as a TFA salt. H-NMR (DMSO-d6) δ 8.90 (s, 1H), 8.11 (d, J=5.5 Hz, 1H), 7.94-7.83 (m, 3H), 7.57 (s, 1H), 7.45 (t, J=7.6 Hz, 1H), 7.29 (d, J=10.2 Hz, 1H), 7.20 (d, J=7.8 Hz, 1H), 7.10 (t, J=7.1 Hz, 1H), 6.97-6.87 (m, 3H), 6.78 (s, 1H), 6.49 (d, J=9.9 Hz, 1H), 3.82 (s, 3H), 3.81-3.76 (m, 8H); LC/MS (ESI+): 508.14 (M+H).

Example 995

N-(2-{2-[4-(4-Ethyl-morpholin-2-yl)-phenylamino]-pyrrolo[2,1-f][1,2,4]triazin-7-yl}-phenyl)-N-methyl-methanesulfonamide Following a procedure analogous to 251c, 4-(4-Ethyl-morpholin-2-yl)-phenylamine (0.16 g, 78 mmol) and N-[2-(2-Methanesulfinyl-pyrrolo[2,1-f][1,2,4]triazin-7-yl)-phenyl]-N-methyl-methanesulfonamide (94 mg, 26 mmol) were converted to the title compound (35 mgs, 22%) isolated as a TFA salt. H-NMR (DMSO-d6) δ 9.89 (broad s, 1H), 9.56 (s, 1H), 9.00 (s, 1H), 7.79 (d, J=3.3 Hz, 1H), 7.69-7.66 (m, 3H), 7.59-7.58 (m, 2H), 7.20 (d, J=7.8 Hz, 2H), 6.99 (d, J=7.8 Hz, 2H), 4.63 (d, J=11.1 Hz, 1H), 4.18 (d, J=12.9 Hz, 1H), 3.85 (t, J=8.3 Hz, 1H), 3.59-3.32 (m, 2H), 3.12-2.98 (m, 4H), 2.86 (s, 3H), 1.25 (t, J=7.8 Hz, 3H); LC/MS (ESI+): 507.1 (M+H).

Example 996

N-(2-{2-[(7-methoxy-1'-methyl-3,4-dihydrospiro[chromene-2,4'-piperidin]-6-yl)amino]pyrrolo[2,1-f][1,2,4]triazin-7-yl}phenyl)-N-methylmethanesulfonamide Following a procedure analogous to 251c, 7-methoxy-1'-methyl-3,4-dihydrospiro[chromene-2,4'-piperidin]-6-amine (0.15 g, 57 mmol) and N-[2-(2-Methanesulfinyl-pyrrolo[2,1-f][1,2,4]triazin-7-yl)-phenyl]-N-methyl-methanesulfonamide (69 mg, 19 mmol) were converted to the title compound (23 mgs, 18%) isolated as a TFA salt. H-NMR (DMSO-d6) δ 9.49 (broad s, 1H), 8.92 (s, 1H), 7.94 (s, 1H), 7.65 (s, 2H), 7.69-7.66 (m, 3H), 6.98-6.94 (m, 2H), 6.52 (s, 1H), 3.80 (s, 3H), 3.39-3.31 (m, 2H), 3.23-3.13 (m, 2H), 3.06 (s, 3H), 2.87-2.81 (m, 7H), 2.55-2.51 (m, 2H), 2.00-1.91 (m, 2H), 1.84-1.76 (m, 32H); LC/MS (ESI+): 563.17 (M+H).

Example 997

7-methoxy-N-[7-(2-methoxyphenyl)pyrrolo[2,1-f][1,2,4]triazin-2-yl]-1'-methyl-3,4-dihydrospiro[chromene-2,4'-piperidin]-6-amine Following a procedure analogous to 251c, 7-methoxy-1'-methyl-3,4-dihydrospiro[chromene-2,4'-piperidin]-6-amine (0.15 g, 57 mmol) and 2-Methanesulfinyl-7-(2-methoxy-phenyl)-pyrrolo[2,1-f][1,2,4]triazine (55 mg, 19 mmol) were converted to the title compound (15 mgs, 13%) isolated as a TFA salt. H-NMR (DMSO-d6) δ 9.47 (broad s, 1H), 8.91 (s, 1H), 7.85-7.80 (m, 2H), 7.48-7.42 (m, 2H), 7.21 (d, J=9.2 Hz, 1H), 7.13-7.09 (m, 1H), 6.97-9.92 (m, 2H), 6.54 (s, 1H), 3.83 (s, 3H), 3.78 (s, 3H), 3.39-3.32 (m, 2H), 3.23-3.13 (m, 2H), 2.85 (s, 3H), 2.59-2.55 (m, 2H), 1.95-1.77 (m, 65H); LC/MS (ESI+): 486.18 (M+H).

Example 998

[2-Methoxy-4-(1-methyl-piperidin-4-yloxy)-phenyl]-[7-(2-methoxy-phenyl)-pyrrolo[2,1-f][1,2,4]triazin-2-yl]-amine Following a procedure analogous to Example 45, 4-(3-Methoxy-4-nitro-phenoxy)-piperidine-1-carboxylic acid tert-butyl ester (2.9 g) was converted to 4-(3-Methoxy-4-nitro-phenoxy)-piperidine as the trifluoroacetic acid salt (3.0 grams) which was converted, using a procedure analogous to 232a, with formaldehyde to 4-(3-Methoxy-4-nitro-phenoxy)-1-methyl-piperidine (76%), which was converted to 2-Methoxy-4-(1-methyl-piperidin-4-yloxy)-phenylamine (100%) using a procedure analogous to 251b, which was converted, using a 2-Methanesulfinyl-7-(2-methoxy-phenyl)-pyrrolo[2,1-f][1,2,4]triazine (100 mg, 0.36 mmol), to the title compound (27 mgs, 16%). H-NMR (CDCl$_3$) δ 8.70 (s, 1H), 8.25 (d, J=10.7 Hz, 1H), 8.03 (d, J=10.7 Hz, 1H), 7.44 (t, J=9.2 Hz, 1H), 7.30 (s, 1H), 7.16-7.02 (m, 3H), 6.85-96.82 (m, 1H), 6.53 (s, 1H), 6.42 (d, J=10.4 Hz, 1H), 4.27 (Broad s, 1H), 3.89 (s, 3H), 3.86 (s, 3H), 2.75-2.69 (m, 2H), 2.33 (s, 3H), 2.33-2.26 (m, 2H), 2.04-1.98 (m, 2H), 1.90-1.81 (m, 2H); LC/MS (ESI+): 460 (M+H).

Example 999

N-(2-{2-[2-Methoxy-4-(1-methyl-piperidin-4-yloxy)-phenylamino]-pyrrolo[2,1-f][1,2,4]triazin-7-yl}-phenyl)-N-methyl-methanesulfonamide Following a procedure analogous to 251c, 2-Methoxy-4-(1-methyl-piperidin-4-yloxy)-phenylamine (0.17 g, 0.72 mmol) and N-[2-(2-Methanesulfinyl-pyrrolo[2,1-f][1,2,4]triazin-7-yl)-phenyl]-N-methyl-methanesulfonamide (130 mg, 0.36 mmol) were converted to the title compound (14 mgs, 7%). (CDCl$_3$) δ 8.73 (s, 1H), 8.02 (d, J=10.7 Hz, 1H), 7.97-7.94 (m, 1H), 7.30 (s, 1H), 7.02-7.00 (m, 1H), 6.87-6.83 (m, 1H), 6.52 (s, 1H), 6.33 (d, J=10.6 Hz, 1H), 4.25 (Broad s, 1H), 3.89 (s, 3H), 3.15 (s, 3H), 2.75-2.68 (m, 2H), 2.66 (s, 3H), 2.32 (s, 3H), 2.31-2.26 (m, 2H), 2.04-1.98 (m, 2H), 1.87-1.81 (m, 2H); LC/MS (ESI+): 537 (M+H).

Example 1001

N-tert-Butyl-3-{2-[3-(2-morpholin-4-yl-ethoxy)-phenylamino]-pyrrolo[2,1-f][1,2,4]triazin-7-yl}-benzenesulfonamide Prepared by following a procedure analagous to Example 251c by using 3-(2-Morpholin-4-yl-ethoxy)-phenylamine and N-tert-Butyl-3-(2-methanesulfinyl-pyrrolo[2,1-f][1,2,4]triazin-7-yl)-benzenesulfonamide as a triflate salt. $^1$H-NMR (DMSO) δ 9.9 (br s, 1H), 9.6 (s, 1H), 9.15 (s, 1H), 8.5 (s, 1H), 8.4 (d, J=8.0 Hz, 1H), 7.9 (d, J=8.0 Hz, 1H), 7.75 (m, 1H), 7.6 (s, 1H), 7.55 (d, J=8.3 Hz, 1H), 7.3 (m, 2H), 7.2 (d, J=4.7 Hz, 1H), 7 (d, J=4.7 Hz, 1H), 6.7 (d, J=10.4 Hz, 1H), 4.3-3.3 (m, 12H), 1.1 (s, 9H); LC/MS (ESI+): 551 (M+H).

Example 1002

N-(2-{2-[3-(2-Morpholin-4-yl-ethoxy)-phenylamino]-pyrrolo[2,1-f][1,2,4]triazin-7-yl}-phenyl)-methanesulfonamide Prepared by following a procedure analagous to Example 251c by using 3-(2-Morpholin-4-yl-ethoxy)-phenylamine and N-[2-(2-Methanesulfinyl-pyrrolo[2,1-f][1,2,4]triazin-7-yl)-phenyl]-methanesulfonamide. $^1$H-NMR (DMSO) δ 9.9 (br s, 1H), 9.6 (s, 1H), 9 (s, 1H), 8.8 (s, 1H), 7.7 (d, J=8.0 Hz, 1H), 7.6 (m, 2H), 7.5 (m, 1H), 7.4 (brs, 1H), 7.2 (m, 1H), 7.1 (t, J=8.0 Hz, 1H), 7 (s, 2H), 6.6 (d, J=7.2 Hz, 1H), 4.1-3 (m, 12H), 2.7 (s, 3H); LC/MS (ESI+): 509 (M+H).

Example 1003

[7-(2-Methoxy-phenyl)-pyrrolo[2,1-f][1,2,4]triazin-2-yl]-[3-(2-morpholin-4-yl-ethoxy)-phenyl]-amine Prepared by following a procedure analagous to Example 251c by using 3-(2-Morpholin-4-yl-ethoxy)-phenylamine and 2-Methanesulfinyl-7-(2-methoxy-phenyl)-pyrrolo[2,1-f][1,2,4]triazine. $^1$H-NMR (DMSO) δ 9.9 (br s, 1H), 9.46 (s, 1H), 8.97 (s, 1H), 7.77 (d, J=7.5 Hz, 1H), 7.5 (t, 1H), 7.4 (brs, 1H), 7.35 (d, J=7.8 Hz, 1H), 7.23 (d, J=8.3 Hz, 1H), 7.15 (m, 2H), 6.9 (s, 2H), 6.6 (d, J=7.8 Hz, 1H), 4.4-3.3 (m, 12H), 3.8 (s, 3H); LC/MS (ESI+): 446 (M+H).

Example 1004

[7-(1-Methyl-1H-pyrazol-4-yl)-pyrrolo[2,1-f][1,2,4]triazin-2-yl]-[3-(2-morpholin-4-yl-ethoxy)-phenyl]-amine Prepared by following a procedure analagous to Example 251c by using 3-(2-Morpholin-4-yl-ethoxy)-phenylamine and 2-Methanesulfinyl-7-(1-methyl-1H-pyrazol-4-yl)-pyrrolo[2,1-f][1,2,4]triazine. $^1$H-NMR (DMSO) δ 10 (brs, 1H), 9.4 (s, 1H), 8.9 (s, 1H), 8.4 (s, 1H), 8.2 (s, 1H), 7.5 (brs, 1H), 7.3 (m, 2H), 7.06 (d, J=4.6 Hz, 1H), 6.9 (d, J=4.6 Hz, 1H), 6.7 (d, J=8.0 Hz, 1H), 4.3 (m, 2H), 4-3.1 (m, 10H), 3.9 (s, 3H); LC/MS (ESI+): 420 (M+H).

Example 1005

N-tert-Butyl-3-{2-[3-(1-methyl-pyrrolidin-2-yl-methoxy)-phenylamino]-pyrrolo[2,1-f][1,2,4]triazin-7-yl}-benzenesulfonamide Prepared by following a procedure analagous to Example 251c by using 3-(1-Methyl-pyrrolidin-2-ylmethoxy)-phenylamine and N-tert-Butyl-3-(2-methanesulfinyl-pyrrolo[2,1-f][1,2,4]triazin-7-yl)-benzenesulfonamide. $^1$H-NMR (DMSO) δ, 9.8 (brs, 1H), 9.4 (9.6, 1H), 9.1 (s, 1H), 8.4 (m, 2H), 7.9 (d, J=7.9 Hz, 1H), 7.7 (t, 1H), 7.6 (s, 1H), 7.5 (d, J=7.9 Hz, 1H), 7.4 (s, 1H), 7.3 (t, 1H), 7.2 (d, J=4.8 Hz, 1H), 7 (d, J=4.8 Hz, 1H), 6.6 (d, 1H), 4.2 (m, 1H), 4.1 (m, 1H), 3.8 (m, 1H), 3.6 (m, 1H), 3.1 (m, 1H), 3.0 (s, 3H), 2.2 (m, 1H), 2.0 (m, 1H), 1.9 (m, 1H), 1.8 (m, 1H), 1.1 (s, 9H); LC/MS (ESI+): 535 (M+H).

Example 1006

7-(2-Methoxy-phenyl)-pyrrolo[2,1-f][1,2,4]triazin-2-yl]-[3-(1-methyl-pyrrolidin-2-ylmethoxy)-phenyl]-amine Prepared by following a procedure analagous to Example 251c by using 3-(1-Methyl-pyrrolidin-2-ylmethoxy)-phenylamine and 2-Methanesulfinyl-7-(2-methoxy-phenyl)-pyrrolo[2,1-f][1,2,4]triazine. $^1$H-NMR (DMSO) δ 9.6 (brs, 1H), 9.4 (s, 1H), 8.9 (s, 1H), 7.8 (d, J=7.5 Hz, 1H), 7.5 (t, 1H), 7.4 (s, 1H), 7.3 (d, J=8.1 Hz, 1H), 7.1 (m, 3H), 6.9 (s, 2H), 6.5 (d, J=8.0 Hz, 1H), 4.1 (m, 2H), 3.8 (s, 3H), 3.7 (m, 1H), 3.6 (m, 1H), 3.1 (m, 1H), 2.9 (s, 3H), 2.2 (m, 1H), 2.0 (m, 1H), 1.9 (m, 1H), 1.8 (m, 1H); LC/MS (ESI+): 430 (M+H).

Example 1007

[7-(1-Methyl-1H-pyrazol-4-yl)-pyrrolo[2,1-f][1,2,4]triazin-2-yl]-[3-(1-methyl-pyrrolidin-2-ylmethoxy)-phenyl]-amine Prepared by following a procedure analagous to Example 251c by using 3-(1-Methyl-pyrrolidin-2-ylmethoxy)-phenylamine and 2-Methanesulfinyl-7-(1-methyl-1H-pyrazol-4-yl)-pyrrolo[2,1-f][1,2,4]triazine. $^1$H-NMR (DMSO) δ 9.7 (brs, 1H), 9.4 (s, 1H), 8.9 (s, 1H), 8.4 (s, 1H), 8.2 (s, 1H), 7.5 (m, 1H), 7.3 (m, 2H), 7 (d, J=4.6 Hz, 1H), 6.9 (d, J=4.6 Hz, 1H), 6.6 (d, J=7.2 Hz, 1H), 4.3 (m, 1H), 4.2 (m, 1H), 3.9 (s, 3H), 3.8 (m, 1H), 3.6 (m, 1H), 3.1 (m, 1H), 2.9 (s, 3H), 2.2 (m, 1H), 2.0 (m, 1H), 1.9 (m, 1H), 1.8 (m, 1H); LC/MS (ESI+): 401 (M+H).

Example 1008

3-{4-[7-(2-Methoxy-phenyl)-pyrrolo[2,1-f][1,2,4]triazin-2-ylamino]-phenyl}-pyrrolidine-1-carboxylic acid tert-butyl ester Prepared by following a procedure analagous to Example 1220c by using 3-(4-Amino-phenyl)-pyrrolidine-1-carboxylic acid tert-butyl ester and Trifluoro-methanesulfonic acid 7-(2-methoxy-phenyl)-pyrrolo[2,1-f][1,2,4]triazin-2-yl ester. $^1$H-NMR (DMSO) δ 9.4 (s, 1H), 8.9 (s, 1H), 7.8 (d, J=7.5 Hz, 1H), 7.6 (d, J=8.5 Hz, 2H), 7.45 (t, 1H), 7.2 (d, J=8.5 Hz, 1H), 7.1 (m, 3H), 6.9 (dd, J1=J2=4.6 Hz, 2H), 3.8 (s, 3H), 3.6 (m, 1H), 3.4 (m, 1H), 3.2 (m, 2H), 3.2 (t, 1H), 2.1 (m, 1H), 1.9 (m, 1H), 1.4 (s, 9H).

Example 1009

N-tert-Butyl-3-{2-[4-chloro-3-(1-methyl-pyrrolidin-2-ylmethoxy)-phenylamino]-pyrrolo[2,1-f][1,2,4]triazin-7-yl}-benzenesulfonamide Prepared by following a procedure analagous to Example 1255c by using 4-Chloro-3-(1-methyl-pyrrolidin-2-ylmethoxy)-phenylamine and N-tert-Butyl-3-(2-hydroxy-pyrrolo[2,1-f][1,2,4]triazin-7-yl)-benzenesulfonamide.
$^1$H-NMR (DMSO) δ 9.8 (brs, 1H), 9.7 (s, 1H), 9 (s, 1H), 8.6 (s, 1H), 8.3 (d, J=8.0 Hz, 1H), 7.8 (d, J=8.0 Hz, 1H), 7.7 (t, 1H), 7.6 (s, 1H), 7.5 (d, J=8.7 Hz, 1H), 7.4 (m, 2H), 7.2 (d, J=4.7 Hz, 1H), 7.0 (d, J=4.7 Hz, 1H), 4.2 (m, 1H), 4.0 (m, 1H), 3.8 (m, 1H), 3.6 (m, 1H), 3.1 (m, 1H), 3.0 (s, 3H), 2.2 (m, 1H), 2.0 (m, 1H), 1.9 (m, 1H), 1.6 (m, 1H); LC/MS (ESI+): 569 (M+H).

Example 1010

N-(2-{2-[4-Chloro-3-(1-methyl-pyrrolidin-2-yl-methoxy)-phenylamino]-pyrrolo[2,1-f][1,2,4]triazin-7-yl}-phenyl)-N-methyl-methanesulfonamide Prepared by following a procedure analagous to Example 1220c by using 4-Chloro-3-(1-methyl-pyrrolidin-2-yl-methoxy)-phenylamine and Trifluoro-methanesulfonic acid 7-[2-(methanesulfonyl-methyl-amino)-phenyl]-pyrrolo[2,1-f][1,2,4]triazin-2-yl ester. $^1$H-NMR (DMSO) δ 9.7 (brs, 1H), 9.6 (s, 1H), 9 (s, 1H), 7.8 (m, 1H), 7.7 (m, 1H), 7.5 (m, 3H), 7.3 (d, 1H), 7.2 (d, J=8.7 Hz , 1H), 7.0 (m, 2H), 3.8 (m, 1H), 3.6 (m, 1H), 3.5 (m, 1H), 3.1 (s, 3H), 3 (s, 3H), 2.8 (s, 3H), 2.2 (m, 1H), 2.0 (m, 1H), 1.9 (m, 1H), 1.7 (m, 1H); LC/MS (ESI+): 541 (M+H).

Example 1011

[4-Chloro-3-(1-methyl-pyrrolidin-2-ylmethoxy)-phenyl]-[7-(2-methoxy-phenyl)-pyrrolo[2,1-f][1,2,4]triazin-2-yl]-amine Prepared by following a procedure analagous to Example 1220c by using 4-Chloro-3-(1-methyl-pyrrolidin-2-yl-methoxy)-phenylamine and Trifluoro-methanesulfonic acid 7-(2-methoxy-phenyl)-pyrrolo[2,1-f][1,2,4]triazin-2-yl ester. $^1$H-NMR (DMSO) 69.7 (br s, 1H), 9.6 (s, 1H), 8.9 (s, 1H), 7.75 (d, J=7.5 Hz, 1H), 7.5 (m, 2H), 7.35 (d, J=9.1 Hz, 1H), 7.28 (d, J=9.2 Hz 1H), 7.2 (d, J=8.3 Hz, 1H), 7.1 (t, 1H), 7 (s, 2H), 3.97 (d, 1H), 3.85 (m, 2H), 3.77 (s, 3H), 3.6 (m, 1H), 3.1 (m, 1H), 3 (s, 3H), 2.2 (m, 1H), 2.0 (m, 1H), 1.9 (m, 1H), 1.65 (m, 1H); LC/MS (ESI+): 464 (M+H).

Example 1012

[7-(2-Methoxy-phenyl)-pyrrolo[2,1-f][1,2,4]triazin-2-yl]-(4-pyrrolidin-3-yl-phenyl)-amine Prepared by following a procedure analagous to Example 1223 by using 3-(4-Amino-phenyl)-pyrrolidine-1-carboxylic acid tert-butyl ester. $^1$H-NMR (DMSO) δ 9.4 (s, 1H), 9.2 (brs, 1H), 8.9 (s, 1H), 7.8 (d, J=7.5 Hz, 1H), 7.7 (d, J=8.6 Hz, 2H), 7.48 (m, 1H), 7.2 (d, 1H), 7.1 (m, 3H), 6.9 (m, 2H), 3.8 (s, 3H), 3.7-3.0 (m, 7H), 2.3 (m, 1H), 1.9 (m, 1H). LC/MS (ESI+): 385 (M+H).

Example 1013

[4-Chloro-3-(1-methyl-pyrrolidin-2-ylmethoxy)-phenyl]-[7-(3-methanesulfonyl-phenyl)-pyrrolo[2,1-f][1,2,4]triazin-2-yl]-amine Prepared by following a procedure analagous to Example 1220c by using 4-Chloro-3-(1-methyl-pyrrolidin-2-yl-methoxy)-phenylamine and Trifluoro-methanesulfonic acid 7-(3-methanesulfonyl-phenyl)-pyrrolo[2,1-f][1,2,4]triazin-2-yl ester. $^1$H-NMR (DMSO) 69.8 (brs, 1H), 9.7 (s, 1H), 9 (s, 1H), 8.6 (s, 1H), 8.4 (d, J=7.9 Hz, 1H), 7.95 (d, J=7.9 Hz, 1H), 7.8 (t, 1H), 7.5 (d, J=8.9 Hz, 1H), 7.4 (m, 2H), 7.3 (d, J=4.7 Hz, 1H), 7 (d, J=4.7 Hz, 1H), 4.2 (m, 2H), 4.0 (m, 1H), 3.8 (m, 1H), 3.6 (m, 1H), 3.3 (s, 3H), 3.1 (m, 1H), 3.0 (s, 3H), 2.2 (m, 1H), 2.0 (m, 1H), 1.9 (m, 1H), 1.6 (m, 1H); LC/MS (ESI+): 512 (M+H).

Example 1014

N-tert-Butyl-3-{2-[4-(3-hydroxy-piperidin-4-yl)-phenylamino]-pyrrolo[2,1-f][1,2,4]triazin-7-yl}-benzenesulfonamide This example was prepared by following a procedure described for Example 1223 by using 4-{4-[7-(3-tert-Butyl-sulfamoyl-phenyl)-pyrrolo[2,1-f][1,2,4]triazin-2-ylamino]-phenyl}-3-hydroxy-piperidine-1-carboxylic acid tert-butyl ester. $^1$H-NMR (DMSO) 69.5 (s, 1H), 9 (s, 1H), 8.7 (brs, 1H), 8.6 (brs, 1H), 8.5 (s, 1H), 8.36 (d, J=7.9 Hz, 1H), 7.8 (d, J=7.9 Hz, 1H), 7.7 (m, 2H), 7.6 (s, 1H), 7.2 (m, 2H), 7 (d, J=4.7 Hz, 1H), 3.8 (m, 1H), 3.3 (m, 2H), 2.96 (m, 1H), 2.7 (m, 1H), 2.6 (m, 1H), 1.8 (m, 2H), 1.5 (s, 9H); LC/MS (ESI+): 512 (M+H).

Example 1015

[4-Chloro-3-((S)-1-pyrrolidin-2-ylmethoxy)-phenyl]-{7-[3-(propane-2-sulfonyl)-phenyl]-pyrrolo[2,1-f][1,2,4]triazin-2-yl}-amine This example was prepared by using (S)-2-(5-Amino-2-chloro-phenoxymethyl)-pyrrolidine-1-carboxylic acid tert-butyl ester (J. Med. Chem. 2007, 50, 4353) and 7-[3-(Propane-2-sulfonyl)-phenyl]-pyrrolo[2,1-f][1,2,4]triazin-2-ol as described in Example 1255c followed by deprotection as described in Example 1223. $^1$H-NMR (DMSO) δ 9.7 (s, 1H), 9.35 (brs, 1H), 9.0 (s, 1H), 8.9 (brs, 1H), 8.5 (s, 1H), 8.45 (d, J=7.5 Hz, 1H), 7.8 (m, 2H), 7.5 (d, J=8.7 Hz, 1H), 7.4 (m, 2H), 7.3 (d, J=4.8 Hz, 1H), 7 (d, J=4.8 Hz, 1H), 4.1 (m, 1H), 4.0 (m, 1H), 3.5 (m, 1H), 3.2 (m, 1H), 2.0 (m, 2H), 1.9 (m, 1H), 1.7 (m, 1H), 1.1 (d, J=6.5 Hz, 6H). LC/MS (ESI+): 526 (M+H).

Example 1016

[4-Chloro-3-((R)-1-pyrrolidin-2-ylmethoxy)-phenyl]-{7-[3-(propane-2-sulfonyl)-phenyl]-pyrrolo[2,1-f][1,2,4]triazin-2-yl}-amine This example was prepared by using (R)-2-(5-Amino-2-chloro-phenoxymethyl)-pyrrolidine-1-carboxylic acid tert-butyl ester (J. Med. Chem. 2007, 50, 4353) and 7-[3-(Propane-2-sulfonyl)-phenyl]-pyrrolo[2,1-f][1,2,4]triazin-2-ol as described in Example 1255c followed by deprotection as described in Example 1223. $^1$H-NMR (DMSO) δ 9.7 (s, 1H), 9.5 (brs, 1H), 9 (s, 1H), 8.9 (brs, 1H), 8.5 (s, 1H), 8.4 (d, J=7.5 Hz, 1H), 7.8 (m, 2H), 7.5 (d, J=8.7 Hz, 1H), 7.4 (m, 2H), 7.3 (d, J=4.8 Hz, 1H), 7 (d, J=4.8 Hz, 1H), 4.1 (m, 1H), 4.0 (m, 1H), 3.0 (brs, 1H), 3.5 (m, 2H), 3.2 (m, 2H), 2.0 (m, 2H), 1.9 (m, 1H), 1.7 (m, 1H), 1.1 (d, J=6.5 Hz, 6H); LC/MS (ESI+): 526 (M+H).

Example 1017

4-{4-[7-(3-tert-Butylsulfamoyl-phenyl)-pyrrolo[2,1-f][1,2,4]triazin-2-ylamino]-phenyl}-3-hydroxy-piperidine-1-carboxylic acid tert-butyl ester 1017a. 3-Hydroxy-4-(4-nitro-phenyl)-piperidine-1-carboxylic acid tert-butyl ester prepared as described in the literature (J. Heterocyclic chem. 24, 1317, 1987) was hydrogenated as described in example 251b to provide 3-Hydroxy-4-(4-amino-phenyl)-piperidine-1-carboxylic acid tert-butyl ester. $^1$H-NMR (CDCl$_3$) δ7.0 (d, 2H), 6.7 (d, 2H), 4.4 (brs, 1H), 4.2 (brs, 1H), 3.7-3.5 (m, 3H), 2.7 (m, 1H), 2.6 (m, 1H), 2.4 (m, 1H), 1.8 (m, 1H), 1.7 (m, 1H), 1.5 (s, 9H).

1017b. By following the procedure for Example 1255c using 3-Hydroxy-4-(4-amino-phenyl)-piperidine-1-carboxylic acid tert-butyl ester and N-tert-Butyl-3-(2-hydroxy-pyrrolo[2,1-f][1,2,4]triazin-7-yl)-benzenesulfonamide was obtained 4-{4-[7-(3-tert-Butylsulfamoyl-phenyl)-pyrrolo[2,1-f][1,2,4]triazin-2-ylamino]-phenyl}-3-hydroxy-piperidine-1-carboxylic acid tert-butyl ester as a brownish yellow solid. $^1$H-NMR (CDCl$_3$) δ 9.8 (brs, 1H), 8.8 (s, 1H), 8.6 (s, 1H), 8.2 (d, J=7.9 Hz, 1H), 8.0 (d, J=7.9 Hz, 1H), 7.6 (m, 3H), 7.3 (m, 4H), 4.5 (m, 1H), 4.4 (m, 1H), 4.2 (brs, 1H), 3.8 (m, 1H), 2.8-2.5 (m, 3H), 1.9-1.6 (m, 2H), 1.5 (s, 9H), 1.2 (s, 9H); LC/MS (ESI+): 565 (M+H).

Example 1018

4-{4-[7-(3-methanesulfonyl-phenyl)-pyrrolo[2,1-f][1,2,4]triazin-2-ylamino]-phenyl}-piperidine-3-ol This example was prepared by following a procedure described for Example 1223 by using 3-Hydroxy-4-{4-[7-(3-methanesulfonyl-phenyl)-pyrrolo[2,1-f][1,2,4]triazin-2-ylamino]-phenyl}-piperidine-1-carboxylic acid tert-butyl ester. $^1$H-NMR (DMSO) δ 9.5 (s, 1H), 9.0 (s, 1H), 8.7 (m, 1H), 8.7 (s, 1H), 8.6 (m, 1H), 8.45 (d, J=7.9 Hz, 1H), 7.95 (d, J=7.9 Hz, 1H), 7.8 (t, 1H), 7.7 (d, J=8.3 Hz, 2H), 7.3 (d, J=4.7 Hz, 1H), 7.2 (d, J=7.6 Hz, 2H), 7.0 (d, J=4.7 Hz, 1H), 3.7 (m, 1H), 3.35 (m, 2H), 3.3 (s, 3H), 2.9 (m, 1H), 2.7 (m, 1H), 2.6 (m, 1H), 2.5 (s, 3H), 1.85 (m, 2H). LC/MS (ESI+): 464 (M+H).

Example 1019

3-Hydroxy-4-{4-[7-(3-methanesulfonyl-phenyl)-pyrrolo[2,1-f]][1,2,4]triazin-2-ylamino]-phenyl}-piperidine-1-carboxylic acid tert-butyl ester This example was prepared by following the procedure described for 1017 by using 3-Hydroxy-4-(4-amino-phenyl)-piperidine-1-carboxylic acid tert-butyl ester. $^1$H-NMR (DMSO) δ 9.4 (s, 1H), 9.0 (s, 1H), 8.6 (brs, 1H), 8.5 (d, J=8.0 Hz, 1H), 7.9 (d, J=8.0 Hz, 1H), 7.8 (t, 1H), 7.6 (d, J=8.3 Hz, 2H), 7.3 (d, J=4.7 Hz, 1H), 7.2 (d, J=8.3 Hz, 2H), 7.0 (d, J=4.7 Hz, 1H), 4.1 (m, 1H), 4.0 (m, 1H), 3.4 (m, 1H), 3.3 (s, 3H), 2.7 (m, 1H), 2.4 (m, 2H), 1.7 (m, 1H), 1.5 (m, 1H), 1.4 (s, 9H); LC/MS (ESI+): 586 (M+Na).

Example 1020

[4-Chloro-3-((S)-1-pyrrolidin-2-ylmethoxy)-phenyl]-[7-(3-methanesulfonyl-phenyl)-pyrrolo[2,1-f][1,2,4]triazin-2-yl]-amine This example was made by TFA deprotection of (S)-2-{2-Chloro-5-[7-(3-methanesulfonyl-phenyl)-pyrrolo[2,1-f][1,2,4]triazin-2-ylamino]-phenoxymethyl}-pyrrolidine-1-carboxylic acid tert-butyl ester as described in Example 1223. $^1$H-NMR (DMSO) δ 9.7 (s, 1H), 9.5 (brs, 1H), 9.0 (s, 1H), 8.7 (brs, 1H), 8.6 (s, 1H), 8.4 (d, J=8.0 Hz, 1H), 7.95 (d, J=8.0 Hz, 1H), 7.8 (t, 1H), 7.6 (d, J=8.7 Hz, 1H), 7.4 (m, 2H), 7.3 (d, J=4.7 Hz, 1H), 7.0 (d, J=4.7 Hz, 1H), 4.1 (m, 1H), 3.95 (m, 2H), 3.3 (s, 3H), 3.2 (m, 2H), 2.0 (m, 2H), 1.9 (m, 1H), 1.7 (m, 1H); LC/MS (ESI+): 498 (M+H).

Example 1021

[4-Chloro-3-((R)-1-pyrrolidin-2-ylmethoxy)-phenyl]-[7-(3-methanesulfonyl-phenyl)-pyrrolo[2,1-f][1,2,4]triazin-2-yl]-amine This example was made by TFA deprotection of (R)-2-{2-Chloro-5-[7-(3-methanesulfonyl-phenyl)-pyrrolo[2,1-f][1,2,4]triazin-2-ylamino]-phenoxymethyl}-pyrrolidine-1-carboxylic acid tert-butyl ester as described in Example 1223. $^1$H-NMR (DMSO) δ 9.7 (s, 1H), 9.5 (brs, 1H), 9.0 (s, 1H), 8.7 (brs, 1H), 8.6 (s, 1H), 8.4 (d, J=8.0 Hz, 1H), 7.95 (d, J=8.0 Hz, 1H), 7.8 (t, 1H), 7.6 (d, J=8.7 Hz, 1H), 7.4 (m, 2H), 7.3 (d, J=4.7 Hz, 1H), 7.0 (d, J=4.7 Hz, 1H), 4.1 (m, 1H), 3.95 (m, 2H), 3.3 (s, 3H), 3.2 (m, 2H), 2.0 (m, 2H), 1.9 (m, 1H), 1.7 (m, 1H); LC/MS (ESI+): 498 (M+H).

Example 1022

(S)-2-{2-Chloro-5-[7-(3-methanesulfonyl-phenyl)-pyrrolo[2,1-f][1,2,4]triazin-2-ylamino]-phenoxymethyl}-pyrrolidine-1-carboxylic acid tert-butyl ester This example was prepared by using (S)-2-(5-Amino-2-chloro-phenoxymethyl)-pyrrolidine-1-carboxylic acid tert-butyl ester (J. Med. Chem. 2007, 50, 4353) and 7-(3-Methanesulfonyl-phenyl)-pyrrolo[2,1-f][1,2,4]triazin-2-ol as described in Example 1255c. $^1$H-NMR (CDCl$_3$) δ 8.7 (brs, 1H), 8.6 (m, 1H), 8.4 (d, J=8.0 Hz, 1H), 8.0 (d, J=8.0 Hz, 1H), 7.7 (t, 1H), 7.5-7.0 (m, 5H), 4.1-3.9 (m, 3H), 3.5-3.2 (m, 2H), 3.0 (s, 3H), 2.2 (m, 3H), 1.9 (m, 1H); LC/MS (ESI+): 598 (M+H).

Example 1023

(R)-2-{2-Chloro-5-[7-(3-methanesulfonyl-phenyl)-pyrrolo[2,1-f][1,2,4]triazin-2-ylamino]-phenoxymethyl}-pyrrolidine-1-carboxylic acid tert-butyl ester This example was prepared by using (R)-2-(5-Amino-2-chloro-phenoxymethyl)-pyrrolidine-1-carboxylic acid tert-butyl ester (J. Med. Chem. 2007, 50, 4353) and 7-(3-Methanesulfonyl-phenyl)-pyrrolo[2,1-f][1,2,4]triazin-2-ol as described in Example 1255c. $^1$H-NMR (CDCl$_3$) δ 8.7 (brs, 1H), 8.6 (m, 1H), 8.4 (d, J=8.0 Hz, 1H), 8.0 (d, J=8.0 Hz, 1H), 7.7 (t, 1H), 7.5-7.0 (m, 5H), 4.1-3.9 (m, 3H), 3.5-3.2 (m, 2H), 3.0 (s, 3H), 2.2 (m, 3H), 1.9 (m, 1H); LC/MS (ESI+): 598 (M+H).

Example 1024

2-(4-{4-[7-(5-Chloro-2-methoxy-phenyl)-pyrrolo[2,1-f]][1,2,4]triazin-2-ylamino]-phenyl}-piperidin-1-yl)-acetamide This example was prepared by using 7-(5-Chloro-2-methoxy-phenyl)-2-methanesulfinyl-pyrrolo[2,1-f][1,2,4]triazine and 2-[4-(4-Amino-phenyl)-piperidin-1-yl]-acetamide by following the procedure described for Example 251c. $^1$H-NMR (DMSO) δ 9.55 (brs, 1H), 9.5 (s, 1H), 8.9 (s, 1H), 8.1 (d, J=2.5 Hz, 1H), 7.96 (brs, 1H), 7.7 (m, 3H), 7.5 (dd, J1=8.9 Hz, J2=2.5 Hz, 1H), 7.23 (d, J=8.9 Hz, 1H), 7.1 (d, J=8.4 Hz, 2H), 7.0 (d, J=4.7 Hz, 1H), 6.9 (d, J=4.7 Hz, 1H), 3.9 (brs, 2H), 3.8 (s, 3H), 3.5 (m, 2H), 3.1 (m, 2H), 2.7 (m, 1H), 1.9 (m, 4H); LC/MS (ESI+): 491 (M+H).

Example 1025

(1',2',3',4',5',6'-Hexahydro-[2,4']bipyridinyl-5-yl)-[7-(3-methanesulfonyl-phenyl)-pyrrolo[2,1-f][1,2,4]triazin-2-yl]-amine This example was prepared by using 5-Amino-3',4',5',6'-tetrahydro-2'H-[2,4]bipyridinyl-1'-carboxylic acid tert-butyl ester (WO2006/047277) and 7-(3-Methanesulfonyl-phenyl)-pyrrolo[2,1-f][1,2,4]triazin-2-ol as described in Example 1255c followed by deprotection as described in Example 1223. $^1$H-NMR (DMSO) δ 9.9 (s, 1H), 9.1 (s, 1H), 8.8 (s, 1H), 8.7 (s, 1H), 8.6 (brs, 1H), 8.4 (d, J=7.9 Hz, 2H), 8.2 (d, J=8.9 Hz, 1H), 8 (d, J=7.9 Hz, 1H), 7.8 (t, 1H), 7.3 (m, 2H), 7 (d, J=4.4 Hz, 1H), 3.4 (m, 2H), 3.36 (s, 3H), 3.0 (m, 3H), 2.0 (m, 2H), 1.85 (m, 2H); LC/MS (ESI+): 449 (M+H).

Example 1026

(1',2',3',4',5',6'-Hexahydro-[2,4]bipyridinyl-5-yl)-[7-(2-methoxy-phenyl)-pyrrolo[2,1-f][1,2,4]triazin-2-yl]-amine This example was prepared by using 5-Amino-3',4',5',6'-tetrahydro-2'H-[2,4]bipyridinyl-1'-carboxylic acid tert-butyl ester (WO2006/047277) and 7-(2-Methoxy-phenyl)-pyrrolo[2,1-f][1,2,4]triazin-2-ol as described in Example 1255c followed by deprotection as described in Example 1223. $^1$H-NMR (DMSO) δ 9.7 (s, 1H), 9.0 (s, 1H), 8.8 (s, 1H), 8.6 (m, 1H), 8.3 (m, 1H), 8.1 (d, J=8.5 Hz, 1H), 7.7 (d, J=7.5 Hz, 1H), 7.5 (t, 1H), 7.2 (m, 2H), 7.1 (t, 1H), 7.0 (m, 2H), 3.8 (s, 3H), 3.4 (m, 2H), 3.0 (m, 3H), 2.0 (m, 2H), 1.85 (m, 2H); LC/MS (ESI+): 401 (M+H).

Example 1031

{7-[4-(1,1-Dioxo-1$1(6)-thiomorpholin-4-ylmethyl)-phenyl]-pyrrolo[2,1-f][1,2,4]triazin-2-yl}-[4-(4-methyl-piperazin-1-yl)-phenyl]-amine 1031a) A suspension of (4-bromomethylphenyl)boronic acid (2.00 g, 9.31 mmol), thiomorpholine 1,1-dioxide (1.50 g, 11.1 mmol), and potassium carbonate (2.60 g, 18.8 mmol) in acetone (25 mL) was stirred at 40° C. for 18 hours. The mixture was cooled to room temperature and the volatiles were evaporated. The residue was suspended in saturated aqueous ammonium chloride (100 mL). The aqueous phase was decanted from the waxy solid, rinsed with water (50 mL), and decanted again. The waxy solid was dissolved in methanol (50 mL), filtered to remove insoluble salts and evaporated to obtain 4-[(4-boronophenyl)methyl]-thiomorpholine 1,1-dioxide as a tan foam (2.48 g). The recovered material was crude by $^1$HNMR but was used without further purification.

1031b) Palladium acetate (25.5 mg, 0.114 mmol) and triphenylphosphine (65.6 mg, 0.250 mmol) were dissolved in 1,4-dioxane (2.00 mL) and the mixture was purged with nitrogen for 10 minutes. (7-Bromo-pyrrolo[2,1-f][1,2,4]triazin-2-yl)-[4-(4-methyl-piperazin-1-yl)-phenyl]-amine (110 mg, 0.284 mmol), 4-[(4-boronophenyl)methyl]-thiomorpholine 1,1-dioxide (306 mg, 1.14 mmol), N,N-dimethylformamide (2.00 mL) and 1.50 M sodium carbonate in water (0.379 mL, 0.568 mmol) were added. The reaction mixture was heated at 90° C. overnight and then partitioned between water (50 mL) and dichloromethane (50 mL). The organic layer was washed with water (50 mL) and brine (25 mL) and then dried over Na$_2$SO$_4$. Purification by silica gel chromatography using a gradient of 0-10% MeOH/DCM as the eluting solvent to obtain the title compound as a yellow-brown foam (151 mg, 100%). LCMS (m/e) 532 (M+H); $^1$H-NMR (CDCl$_3$, 400 MHz) δ 8.69 (s, 1H), 8.13 (d, 2H, J=7.4 Hz), 7.54 (d, 2H, J=7.8 Hz), 7.41 (d, 2H, J=7.8 Hz), 7.02-6.90 (m, 3H), 6.84-6.78 (m, 1H), 6.70-6.62 (m, 1H), 3.73 (s, 2H), 3.23-3.15 (m, 4H), 3.13-3.00 (m, 8H), 2.66-2.57 (m, 4H), 2.38 (s, 3H).

Example 1032

{7-[4-(1,1-Dioxo-1$1(6)-thiomorpholin-4-ylmethyl)-phenyl]-pyrrolo[2,1-f][1,2,4]triazin-2-yl}-(4-morpholin-4-yl-phenyl)-amine {7-[4-(1,1-Dioxo-1$1(6)-thiomorpholin-4-ylmethyl)-phenyl]-pyrrolo[2,1-f][1,2,4]triazin-2-yl}-(4-morpholin-4-yl-phenyl)-amine was prepared from (7-bromo-pyrrolo[2,1-f][1,2,4]triazin-2-yl)-(4-morpholin-4-yl-phenyl)-amine and 4-[(4-boronophenyl)methyl]-thiomorpholine 1,1-dioxide in an analogous manner to Example 1031b. Product isolated as a yellow solid (36 mg, 24%). m.p.=251-255° C.; LCMS (m/e) 519 (M+H); $^1$H-NMR (CDCl$_3$, 400 MHz) δ 8.69 (s, 1H), 8.13 (d, 2H, J=7.8 Hz), 7.55 (d, 2H, J=7.4 Hz), 7.42 (d, 2H, J=7.8 Hz), 7.02-6.97 (m, 1H), 6.92 (d, 2H, J=7.0 Hz), 6.85-6.80 (m, 1H), 6.73-6.64 (m, 1H), 3.93-3.85 (m, 4H), 3.73 (s, 2H), 3.17-3.00 (m, 12H).

Example 1033

(4-Morpholin-4-yl-phenyl)-(7-quinolin-3-yl-pyrrolo[2,1-f][1,2,4]triazin-2-yl)-amine (4-Morpholin-4-yl-phenyl)-(7-quinolin-3-yl-pyrrolo[2,1-f][1,2,4]triazin-2-yl)-amine was prepared from (7-bromo-pyrrolo[2,1-f][1,2,4]triazin-2-yl)-(4-morpholin-4-yl-phenyl)-amine and 3-quinolineboronic acid in an analogous manner to Example 1031b. Product isolated as a yellow solid (21 mg, 17%). m.p.=decomposed at 268° C.; LCMS (m/e) 423 (M+H); $^1$H-NMR (CDCl$_3$, 400 MHz) δ 9.40 (s, 1H), 9.30 (s, 1H), 8.77 (s, 1H), 8.14 (d, 1H, J=8.7 Hz), 7.85 (d, 1H, J=7.7 Hz), 7.77-7.68 (m, 2H), 7.63-7.55 (m, 2H), 7.24-7.19 (m, 1H), 6.96 (d, 2H, J=7.6 Hz), 6.93-6.86 (m, 1H), 6.70 (s, 1H), 3.95-3.87 (m, 4H), 3.22-3.14 (m, 4H).

Example 1034

[7-(2-Chloro-pyridin-3-yl)-pyrrolo[2,1-f][1,2,4]triazin-2-yl]-(4-morpholin-4-yl-phenyl)-amine

[7-(2-Chloro-pyridin-3-yl)-pyrrolo[2,1-f][1,2,4]triazin-2-yl]-(4-morpholin-4-yl-phenyl)-amine was prepared from (7-bromo-pyrrolo[2,1-f][1,2,4]triazin-2-yl)-(4-morpholin-4-yl-phenyl)-amine and 2-chloro-3-pyridineboronic acid in an analogous manner to Example 1031b. Product isolated as a yellow foam (48 mg, 40%). LCMS (m/e) 407 (M+H); $^1$H-NMR (CDCl$_3$, 400 MHz) δ 8.74 (s, 1H), 8.50-8.44 (m, 1H), 8.23 (d, 1H, J=7.6 Hz), 7.43 (d, 2H, J=7.8 Hz), 7.41-7.34 (m, 1H), 7.10-7.05 (m, 1H), 6.88-6.80 (m, 3H), 6.67 (s, 1H), 3.91-3.82 (m, 4H), 3.13-3.06 (m, 4H).

Example 1035

[7-(2-Dimethylaminomethyl-phenyl)-pyrrolo[2,1-f][1,2,4]triazin-2-yl]-(4-morpholin-4-yl-phenyl)-amine

[7-(2-Dimethylaminomethyl-phenyl)-pyrrolo[2,1-f][1,2,4]triazin-2-yl]-(4-morpholin-4-yl-phenyl)-amine was prepared from (7-bromo-pyrrolo[2,1-f][1,2,4]triazin-2-yl)-(4-morpholin-4-yl-phenyl)-amine and 2-chloro-3-pyridineboronic acid in an analogous manner to Example 1031b. Product isolated as a yellow foam (20 mg, 16%). LCMS (m/e) 429 (M+H); $^1$H-NMR (CDCl$_3$, 400 MHz) δ 8.69 (s, 1H), 7.63 (d, 1H, J=7.6 Hz), 7.58 (d, 1H, J=7.6 Hz), 7.49-7.42 (m, 1H), 7.42-7.33 (m, 3H), 6.92-6.86 (m, 1H), 6.86-6.81 (m, 1H), 6.77 (d, 2H, J=8.1 Hz), 6.63 (s, 1H), 3.89-3.82 (m, 4H), 3.35 (s, 2H), 3.11-3.03 (m, 4H), 2.09 (s, 6H).

Example 1036

[7-(2-Chloro-pyridin-3-yl)-pyrrolo[2,1-f][1,2,4]triazin-2-yl]-[4-(4-methyl-piperazin-1-yl)-phenyl]-amine

[7-(2-Chloro-pyridin-3-yl)-pyrrolo[2,1-f][1,2,4]triazin-2-yl]-[4-(4-methyl-piperazin-1-yl)-phenyl]-amine was prepared from (7-bromo-pyrrolo[2,1-f][1,2,4]triazin-2-yl)-[4-(4-methyl-piperazin-1-yl)-phenyl]-amine and 2-(N,N-dimethylaminomethyl)phenylboronic acid in an analogous manner to Example 1031b. Product isolated as a yellow solid (115 mg, 96%). m.p.=166-168° C.; LCMS (m/e) 420 (M+H); $^1$H-NMR (CDCl$_3$, 400 MHz) 6 8.74 (s, 1H), 8.50-8.43 (m, 1H), 8.25 (d, 1H, J=6.9 Hz), 7.45-7.34 (m, 3H), 7.10-7.05 (m, 1H), 6.89-6.81 (m, 3H), 6.66 (s, 1H), 3.19-3.11 (m, 4H), 2.63-2.55 (m, 4H), 2.36 (s, 3H).

Example 1037

[4-(4-Methyl-piperazin-1-yl)-phenyl]-(7-quinolin-3-yl-pyrrolo[2,1-f][1,2,4]triazin-2-yl)-amine

[4-(4-Methyl-piperazin-1-yl)-phenyl]-(7-quinolin-3-yl-pyrrolo[2,1-f][1,2,4]triazin-2-yl)-amine was prepared from (7-bromo-pyrrolo[2,1-f][1,2,4]triazin-2-yl)-[4-(4-methyl-piperazin-1-yl)-phenyl]-amine and 3-quinolineboronic acid in an analogous manner to Example 1031b. Product isolated as a yellow solid (49 mg, 40%). m.p.=235-241° C.; LCMS (m/e) 436 (M+H); $^1$H-NMR (CDCl$_3$, 400 MHz) δ 9.38 (s, 1H), 9.34 (s, 1H), 8.76 (s, 1H), 8.13 (d, 1H, J=9.1 Hz), 7.85 (d, 1H, J=7.0 Hz), 7.80-7.69 (m, 1H), 7.63-7.52 (m, 3H), 7.25-7.17 (m, 1H), 6.98 (d, 2H, J=7.9 Hz), 6.93-6.86 (m, 1H), 6.70 (s, 1H), 3.29-3.19 (m, 4H), 2.69-2.57 (m, 4H), 2.39 (s, 3H).

Example 1038

[7-(4-Methyl-pyridin-3-yl)-pyrrolo[2,1-f][1,2,4]triazin-2-yl]-(4-morpholin-4-yl-phenyl)-amine

[7-(4-Methyl-pyridin-3-yl)-pyrrolo[2,1-f][1,2,4]triazin-2-yl]-(4-morpholin-4-yl-phenyl)-amine was prepared from (7-bromo-pyrrolo[2,1-f][1,2,4]triazin-2-yl)-(4-morpholin-4-yl-phenyl)-amine and 4-methylpyridine-3-boronic acid in an analogous manner to Example 1031b. Product isolated as a yellow solid (55 mg, 48%). m.p.=191-193° C.; LCMS (m/e) 387 (M+H); $^1$H-NMR (CDCl$_3$, 400 MHz) δ 8.76-8.69 (m, 2H), 8.59-8.52 (m, 1H), 7.37 (d, 2H, J=7.40 Hz), 7.31-7.26 (m, 1H), 6.88-6.84 (m, 1H), 6.84-6.75 (m, 3H), 6.67 (s, 1H), 3.89-3.81 (m, 4H), 3.12-3.04 (m, 4H), 2.31 (s, 3H).

Example 1039

[4-(4-Methyl-piperazin-1-yl)-phenyl]-[7-(4-methyl-pyridin-3-yl)-pyrrolo[2,1-f][1,2,4]triazin-2-yl]-amine

[4-(4-Methyl-piperazin-1-yl)-phenyl]-[7-(4-methyl-pyridin-3-yl)-pyrrolo[2,1-f][1,2,4]triazin-2-yl]-amine was prepared from (7-bromo-pyrrolo[2,1-f][1,2,4]triazin-2-yl)-[4-(4-methyl-piperazin-1-yl)-phenyl]-amine and 4-methylpyridine-3-boronic acid in an analogous manner to Example 1031b. Product isolated as a yellow foam (28 mg, 25%). LCMS (m/e) 400 (M+H); $^1$H-NMR (CDCl$_3$, 400 MHz) δ 8.75-8.69 (m, 2H), 8.58-8.52 (m, 1H), 7.35 (d, 2H, J=7.5 Hz), 7.31-7.25 (m, 1H), 6.88-6.79 (m, 3H), 6.79-6.74 (m, 1H), 6.65 (s, 1H), 3.17-3.10 (m, 4H), 2.61-2.54 (m, 4H), 2.35 (s, 3H), 2.30 (s, 3H).

Example 1040

[7-(2-Fluoro-pyridin-3-yl)-pyrrolo[2,1-f][1,2,4]triazin-2-yl]-(4-morpholin-4-yl-phenyl)-amine

[7-(2-Fluoro-pyridin-3-yl)-pyrrolo[2,1-f][1,2,4]triazin-2-yl]-(4-morpholin-4-yl-phenyl)-amine was prepared from (7-bromo-pyrrolo[2,1-f][1,2,4]triazin-2-yl)-(4-morpholin-4-yl-phenyl)-amine and 2-fluoro-3-pyridineboronic acid in an analogous manner to Example 1031b. Product isolated as a yellow solid (93 mg, 81%). m.p.=215-221° C.; LCMS (m/e) 391 (M+H); $^1$H-NMR (CDCl$_3$, 400 MHz) δ 8.94-8.85 (m, 1H), 8.75 (s, 1H), 8.24-8.17 (m, 1H), 7.49 (d, 2H, J=7.6 Hz), 7.36-7.27 (m, 1H), 7.19-7.12 (m, 1H), 6.90 (m, 2H, J=7.6 Hz), 6.85 (m, 1H, J=4.2 Hz), 6.70 (s, 1H), 3.92-3.85 (m, 4H), 3.17-3.10 (m, 4H).

Example 1041

[7-(2-Fluoro-pyridin-3-yl)-pyrrolo[2,1-f][1,2,4]triazin-2-yl]-[4-(4-methyl-piperazin-1-yl)-phenyl]-amine

[7-(2-Fluoro-pyridin-3-yl)-pyrrolo[2,1-f][1,2,4]triazin-2-yl]-[4-(4-methyl-piperazin-1-yl)-phenyl]-amine was prepared from (7-bromo-pyrrolo[2,1-f][1,2,4]triazin-2-yl)-[4-(4-methyl-piperazin-1-yl)-phenyl]-amine and 2-fluoro-3-pyridineboronic acid in an analogous manner to Example 1031b. Product isolated as a yellow solid (78 mg, 68%). m.p.=201-203° C.; LCMS (m/e) 404 (M+H); $^1$H-NMR (CDCl$_3$, 400 MHz) δ 8.95-8.87 (m, 1H), 8.74 (s, 1H), 8.23-8.17 (m, 1H), 7.47 (d, 2H, J=7.7 Hz), 7.34-7.27 (m, 1H), 7.19-7.12 (m, 1H), 6.92 (d, 2H, J=8.0 Hz), 6.85 (d, 1H, J=4.7 Hz), 6.68 (s, 1H), 3.23-3.15 (m, 4H), 2.64-2.56 (m, 4H), 2.37 (s, 3H).

Example 1042

[7-(1,2-Dimethyl-1H-imidazol-4-yl)-pyrrolo[2,1-f][1,2,4]triazin-2-yl]-[4-(4-methyl-piperazin-1-yl)-phenyl]-amine 1042a) A mixture of (7-bromo-pyrrolo[2,1-f][1,2,4]triazin-2-yl)-[4-(4-methyl-piperazin-1-yl)-phenyl]-amine (250 mg, 0.646 mmol), 4,4,5,5,4',4',5',5'-octamethyl-[2,2']bi[[1,3,2]dioxaborolanyl] (311 mg, 1.23 mmol), potassium acetate (184 mg, 1.87 mmol), and bis(tricyclohexylphosphine)palladium (0) (40.9 mg, 0.0613 mmol) in 1,4-dioxane (10.0 mL) was heated in a sealed tube at 110° C. for 6 hours. The reaction was filtered through celite and the celite was washed with DCM (20 mL). The solution was then concentrated under reduced pressure to obtain [4-(4-methyl-piperazin-1-yl)-phenyl]-[7-(4,4,5,5-tetramethyl-[1,3,2]dioxaborolan-2-yl)-pyrrolo[2,1-f][1,2,4]triazin-2-yl]-amine (210 mg, 75%). The product was carried through to the next reaction without further purification.

1042b) Palladium acetate (13.0 mg, 0.0580 mmol) and triphenylphosphine (19.0 mg, 0.0725 mmol) were placed in tetrahydrofuran (2.00 mL). The mixture was allowed to stir at room temperature for 10 minutes. 4-Bromo-1,2-dimethyl-1H-imidazole (102 mg, 0.580) was then added and the reaction was again allowed to stir for 10 minutes. [4-(4-Methyl-piperazin-1-yl)-phenyl]-[7-(4,4,5,5-tetramethyl-[1,3,2]dioxaborolan-2-yl)-pyrrolo[2,1-f][1,2,4]triazin-2-yl]-amine (105 mg, 0.242 mmol) was added followed by 1.50 M sodium carbonate in water (0.645 mL, 0.967 mmol) and ethanol (2.00 mL). The reaction mixture was then heated at 80° C. overnight. The reaction was partitioned between DCM (50 mL) and water (50 mL). The organic layer was washed twice with water (50 mL) and then dried over sodium sulfate, filtered, and concentrated under reduced pressure. Purification by prep-HPLC using a gradient of 10-45% AcN/water both containing 0.1% TFA as the eluting solvent. The product was then free based to obtain the title compound as a yellow solid (22 mg, 23%). m.p.=242-244° C.; LCMS (m/e) 403 (M+H); $^1$H-NMR (CDCl$_3$, 400 MHz) δ 8.61 (s, 1H), 7.84 (s, 1H), 7.57-7.50 (m, 2H), 7.24 (d, 1H, J=4.8 Hz), 7.02-6.95 (m, 2H), 6.80 (d, 1H, J=4.8 Hz), 6.55 (bs, 1H), 3.62 (s, 3H), 3.24-3.16 (m, 4H), 2.65-2.57 (m, 4H), 2.46 (s, 3H), 2.38 (s, 3H).

Example 1043

[7-(1-Methyl-1H-imidazol-4-yl)-pyrrolo[2,1-f][1,2,4]triazin-2-yl]-[4-(4-methyl-piperazin-1-yl)-phenyl]-amine

[7-(1-Methyl-1H-imidazol-4-yl)-pyrrolo[2,1-f][1,2,4]triazin-2-yl]-[4-(4-methyl-piperazin-1-yl)-phenyl]-amine was prepared from 4-bromo-1-methyl-1H-imidazole and [4-(4-methyl-piperazin-1-yl)-phenyl]-[7-(4,4,5,5-tetramethyl-[1,3,2]dioxaborolan-2-yl)-pyrrolo[2,1-f][1,2,4]triazin-2-yl]-amine in an analogous manner to Example 1042b. Product isolated as a yellow solid (16 mg, 17%). m.p.=200-202° C.; LCMS (m/e) 389 (M+H); $^1$H-NMR (CDCl$_3$, 400 MHz) δ 8.63 (s, 1H), 7.92 (d, 1H, J=1.3 Hz), 7.57-7.47 (m, 3H), 7.30-7.24 (m, 1H), 7.02-6.96 (m, 2H), 6.81 (d, 1H, J=4.8 Hz), 6.57 (bs, 1H), 3.74 (s, 3H), 3.24-3.18 (m, 4H), 2.66-2.57 (m, 4H), 2.38 (s, 3H).

Example 1044

[7-(1,2-Dimethyl-1H-imidazol-4-yl)-pyrrolo[2,1-f][1,2,4]triazin-2-yl]-(4-morpholin-4-yl-phenyl)-amine 1044a) (4-Morpholin-4-yl-phenyl)-[7-(4,4,5,5-tetramethyl-[1,3,2]dioxaborolan-2-yl)-pyrrolo[2,1-f][1,2,4]triazin-2-yl]-amine was prepared from 4-bromo-1,2-dimethyl-1H-imidazole and (7-bromo-pyrrolo[2,1-f][1,2,4]triazin-2-yl)-(4-morpholin-4-yl-phenyl)-amine in an analogous manner to Example 1042a (237 mg, 70%).

1044b) [7-(1,2-Dimethyl-1H-imidazol-4-yl)-pyrrolo[2,1-f][1,2,4]triazin-2-yl]-(4-morpholin-4-yl-phenyl)-amine was prepared from 4-bromo-1,2-dimethyl-1H-imidazole and (4-morpholin-4-yl-phenyl)-[7-(4,4,5,5-tetramethyl-[1,3,2]dioxaborolan-2-yl)-pyrrolo[2,1-f][1,2,4]triazin-2-yl]-amine in an analogous manner to Example 1042b. Product isolated as a yellow solid (11 mg, 10%). m.p.=decomposed at 250° C.; LCMS (m/e) 390 (M+H); $^1$H-NMR (CDCl$_3$, 400 MHz) δ 8.62 (s, 1H), 7.85 (s, 1H), 7.55 (d, 2H, J=8.9 Hz), 7.27-7.23 (m, 1H), 6.97 (d, 2H, J=8.9 Hz), 6.81 (d, 1H, J=4.8 Hz), 6.56 (bs, 1H), 3.93-3.87 (m, 4H), 3.64 (s, 3H), 3.18-3.12 (m, 4H), 2.46 (s, 3H).

Example 1045

[7-(1-Methyl-1H-imidazol-4-yl)-pyrrolo[2,1-f][1,2,4]triazin-2-yl]-(4-morpholin-4-yl-phenyl)-amine

[7-(1-Methyl-1H-imidazol-4-yl)-pyrrolo[2,1-f][1,2,4]triazin-2-yl]-(4-morpholin-4-yl-phenyl)-amine was prepared from 4-bromo-1-methyl-1H-imidazole and (4-morpholin-4-yl-phenyl)-[7-(4,4,5,5-tetramethyl-[1,3,2]dioxaborolan-2-yl)-pyrrolo[2,1-f][1,2,4]triazin-2-yl]-amine in an analogous manner to Example 1042b. Product isolated as a yellow foam (7 mg, 7%). LCMS (m/e) 376 (M+H); $^1$H-NMR (CDCl$_3$, 400 MHz) δ 8.64 (s, 1H), 7.92 (d, 1H, J=1.2 Hz), 7.55 (d, 2H, J=8.9 Hz), 5.52 (s, 1H), 7.27 (d, 1H, J=4.8 Hz), 6.97 (d, 2H, J=8.9 Hz), 6.82 (d, 1H, J=4.8 Hz), 6.59 (bs, 1H), 3.93-3.87 (m, 4H), 3.76 (s, 3H), 3.18-3.13 (m, 4H).

Example 1046

[7-(6-Fluoro-5-methyl-pyridin-3-yl)-pyrrolo[2,1-f][1,2,4]triazin-2-yl]-[4-(4-methyl-piperazin-1-yl)-phenyl]-amine

[7-(6-Fluoro-5-methyl-pyridin-3-yl)-pyrrolo[2,1-f][1,2,4]triazin-2-yl]-[4-(4-methyl-piperazin-1-yl)-phenyl]-amine was prepared from (7-bromo-pyrrolo[2,1-f][1,2,4]triazin-2-yl)-[4-(4-methyl-piperazin-1-yl)-phenyl]-amine and 2-fluoro-3-methylpyridine-5-boronic acid in an analogous manner to Example 1031b. Product isolated as a yellow solid (66 mg, 56%). m.p.=210° C.; LCMS (m/e) 418 (M+H); $^1$H-NMR (CDCl$_3$, 400 MHz) δ 8.71 (s, 1H), 8.61-8.53 (m, 2H), 7.52-7.45 (m, 2H), 6.99-6.92 (m, 3H), 6.82 (d, 1H, J=4.8 Hz), 6.66 (bs, 1H), 3.22-3.16 (m, 4H), 2.63-2.57 (m, 4H), 2.37 (s, 3H), 2.37 (s, 3H).

Example 1047

[7-(6-Fluoro-5-methyl-pyridin-3-yl)-pyrrolo[2,1-f][1,2,4]triazin-2-yl]-(4-morpholin-4-yl-phenyl)-amine

[7-(6-Fluoro-5-methyl-pyridin-3-yl)-pyrrolo[2,1-f][1,2,4]triazin-2-yl]-(4-morpholin-4-yl-phenyl)-amine was prepared from (7-bromo-pyrrolo[2,1-f][1,2,4]triazin-2-yl)-(4-morpholin-4-yl-phenyl)-amine and 2-fluoro-3-methylpyridine-5-boronic acid in an analogous manner to Example 1031b. Product isolated as a yellow solid (79 mg, 66%). m.p.=227-230° C.; LCMS (m/e) 405 (M+H); $^1$H-NMR (CDCl$_3$, 400 MHz) δ 8.71 (s, 1H), 8.62 (s, 1H), 8.56-8.49 (m, 1H), 7.51 (d, 2H, J=8.9 Hz), 6.99-6.90 (m, 3H), 6.83 (d, 1H, J=4.8 Hz), 6.68 (bs, 1H), 3.92-3.85 (m, 4H), 3.17-3.10 (m, 4H), 2.38 (s, 3H).

Example 1048

N-Methyl-N-(3-{2-[4-(4-methyl-piperazin-1-yl)-phenylamino]-pyrrolo[2,1-f][1,2,4]triazin-7-yl}-benzyl)-methanesulfonamide (3-{2-[4-(4-Methyl-piperazin-1-yl)-phenylamino]-pyrrolo[2,1-f][1,2,4]triazin-7-yl}-phenyl)-methanol (63.0 mg, 0.152 mmol) was dissolved in N,N-dimethylformamide (3.00 mL) and triethylamine (27.5 µL, 0.198 mmol). Methanesulfonyl chloride (14.1 µL, 0.182 mmol) was added and the reaction was stirred at room temperature for 40 minutes. LCMS analysis showed complete conversion to the mesylate. In a clean round bottomed flask was added N-methyl-methanesulfonamide (332 mg, 3.04 mmol) in N,N-dimethylformamide (5.00 mL). Sodium hydride (29.2 mg, 1.22 mmol) was added and the reaction was stirred at room temperature for 5 minutes. The mesylate solution was then added and the reaction was stirred at room temperature for 2 hours. The reaction was partitioned between EtOAc (25 mL) and water (25 mL). The organic layer was washed twice with water (15 mL) and dried over sodium sulfate, filtered, and concentrated under reduced pressure. Purification by prep-HPLC using a gradient of 10-55% AcN/water both containing 0.1% TFA as the eluting solvent. The product was then free based to obtain the title compound as a yellow solid (42 mg, 55%). m.p.=229-230° C.; LCMS (m/e) 506 (M+H); $^1$H-NMR (CDCl$_3$, 400 MHz) δ 8.69 (s, 1H), 8.15-8.08 (m, 2H), 7.56-7.46 (m, 3H), 7.38 (d, 1H, J=7.6 Hz), 7.00 (d, 1H, J=4.7 Hz), 6.93 (d, 2H, J=9.0 Hz), 6.82 (d, 1H, J=4.8 Hz), 6.68 (s, 1H), 4.40 (s, 2H), 3.22-3.15 (m, 4H), 2.86 (s, 3H), 2.79 (s, 3H), 2.63-2.56 (m, 4H), 2.37 (s, 3H).

Example 1049

[4-(1,1-Dioxo-1$1(6)-thiomorpholin-4-ylmethyl)-phenyl]-[7-(3-methanesulfonyl-phenyl)-pyrrolo[2,1-f][1,2,4]triazin-2-yl]-amine 2-Methanesulfinyl-7-(3-methanesulfonyl-phenyl)-pyrrolo[2,1-f][1,2,4]triazine (100 mg, 0.298 mmol), 4-(1,1-dioxo-1$1(6)-thiomorpholin-4-ylmethyl)-phenylamine (158 mg, 0.656 mmol), and N,N-diisopropylethylamine (114 μL, 0.656 mmol) were placed in 1-methoxy-2-propanol (728 μL). The reaction was microwaved on 300 watts, 170° C. for 8 hours. Purification by prep-HPLC using a gradient of 10-70% AcN/water both containing 0.1% TFA as the eluting solvent. The product was then free based to obtain the title compound as an orange foam (18 mg, 12%). LCMS (m/e) 512 (M+H); $^1$H-NMR (CDCl$_3$, 400 MHz) δ 8.76 (s, 1H), 8.71 (s, 1H), 8.34 (d, 1H, J=7.9 Hz), 7.94 (d, 1H, J=7.8 Hz), 7.73-7.66 (m, 1H), 7.58 (d, 2H, J=8.3 Hz), 7.31 (d, 2H, J=8.3 Hz), 7.05 (d, 1H, J=4.8 Hz), 6.99 (s, 1H), 6.87 (d, 1H, J=4.8 Hz), 3.63 (s, 2H), 3.09 (s, 3H), 3.09-3.03 (m, 4H), 3.03-2.94 (m, 4H).

Example 1050

[4-(1,1-Dioxo-1$1(6)-thiomorpholin-4-ylmethyl)-phenyl]-(7-pyridin-3-yl-pyrrolo[2,1-f][1,2,4]triazin-2-yl)-amine

[4-(1,1-Dioxo-1$1(6)-thiomorpholin-4-ylmethyl)-phenyl]-(7-pyridin-3-yl-pyrrolo[2,1-f][1,2,4]triazin-2-yl)-amine was prepared from 2-methanesulfinyl-7-pyridin-3-yl-pyrrolo[2,1-f][1,2,4]triazine and 4-(1,1-dioxo-1$1(6)-thiomorpholin-4-ylmethyl)-phenylamine in an analogous manner to Example 1049. Product isolated as an orange foam (19 mg, 11%). LCMS (m/e) 435 (M+H); $^1$H-NMR (CDCl$_3$, 400 MHz) δ 9.30 (s, 1H), 8.76 (s, 1H), 8.62 (d, 1H, J=3.8 Hz), 8.49-8.42 (m, 1H), 7.59 (d, 2H, J=8.4 Hz), 7.42 (dd, 1H, J=8.0 and 4.8 MHz), 7.29 (d, 2H, J=8.4 Hz), 7.04 (d, 1H, J=4.8 Hz), 6.95 (s, 1H), 6.88 (d, 1H, J=4.8 Hz), 3.62 (s, 2H), 3.10-3.03 (m, 4H), 3.02-2.96 (m, 4H).

Example 1051

[4-(1,1-Dioxo-1$1(6)-thiomorpholin-4-ylmethyl)-phenyl]-[7-(6-methoxy-pyridin-3-yl)-pyrrolo[2,1-f][1,2,4]triazin-2-yl]-amine

[4-(1,1-Dioxo-1$1(6)-thiomorpholin-4-ylmethyl)-phenyl]-[7-(6-methoxy-pyridin-3-yl)-pyrrolo[2,1-f][1,2,4]triazin-2-yl]-amine was prepared from 2-methanesulfinyl-7-(6-methoxy-pyridin-3-yl)-pyrrolo[2,1-f][1,2,4]triazine and 4-(1,1-dioxo-1$1(6)-thiomorpholin-4-ylmethyl)-phenylamine in an analogous manner to Example 1049. Product isolated as a yellow foam (10 mg, 6%). LCMS (m/e) 465 (M+H); $^1$H-NMR (CDCl$_3$, 400 MHz) δ 8.77 (d, 1H, J=2.1 Hz), 8.72 (s, 1H), 8.40 (dd, 1H, J=8.7 and 2.4 Hz), 7.58 (d, 2H, J=8.4 Hz), 7.26 (d, 2H, J=8.4 Hz), 6.94 (d, 1H, J=4.7 Hz), 6.92-6.84 (m, 2H), 6.82 (s, 1H), 4.04 (s, 3H), 3.62 (s, 2H), 3.10-3.03 (m, 4H), 3.03-2.96 (m, 4H).

Example 1052

N-(3-{2-[4-(1,1-Dioxo-1 $1(6)-thiomorpholin-4-ylmethyl)-phenylamino]-pyrrolo[2,1-f][1,2,4]triazin-7-yl}-phenyl)-methanesulfonamide 1052a) 7-Bromo-pyrrolo[2,1-f][1,2,4]triazin-2-ol (100 mg, 0.467 mmol) was dissolved in N,N-dimethylformamide (9.00 mL) at 0° C. and N,N-diisopropylethylamine (244 μL, 1.40 mmol) was added and the reaction was let stir for 30 minutes. N-Phenylbis(trifluoromethanesulphonimide) (184 mg, 0.514 mmol) was added and the reaction was let warm to room temperature. After 100% conversion to the triflate, 4-(1,1-dioxo-1$1(6)-thiomorpholin-4-ylmethyl)-phenylamine (140 mg, 0.584 mmol) was added and the reaction was stirred at room temperature overnight. The reaction mixture was taken up in EtOAc (30 mL) and washed three times with water (20 mL). The organic layer was dried over sodium sulfate, filtered, and concentrated under reduced pressure. Purification by silica gel chromatography using a gradient of 0-100% EtOAc/hex as the eluting solvent to obtain (7-bromo-pyrrolo[2,1-f][1,2,4]triazin-2-yl)-[4-(1,1-dioxo-1$1(6)-thiomorpholin-4-ylmethyl)-phenyl]-amine as a yellow foam (134 mg, 66%). LCMS (m/e) 301 (M—N(CH2)4SO2); $^1$H-NMR (CDCl$_3$, 400 MHz) δ 8.60 (s, 1H), 7.73 (d, 2H, J=8.5 Hz), 7.31 (d, 2H, J=8.5 Hz), 6.92 (s, 1H), 6.81 (d, 1H, J=4.8 Hz), 6.76 (d, 1H, J=4.8 Hz), 3.63 (s, 2H), 3.10-3.03 (m, 4H), 3.03-2.97 (m, 4H).

1052b) N-(3-{2-[4-(1,1-Dioxo-1$1(6)-thiomorpholin-4-ylmethyl)-phenylamino]-pyrrolo[2,1-f][1,2,4]triazin-7-yl}-phenyl)-methanesulfonamide was prepared from obtain (7-bromo-pyrrolo[2,1-f][1,2,4]triazin-2-yl)-[4-(1,1-dioxo-1$1(6)-thiomorpholin-4-ylmethyl)-phenyl]-amine and 3-methylsulfonylaminophenyl boronic acid in an analogous manner to Example 1031b. Product isolated as a yellow foam (91 mg, 63%). LCMS (m/e) 527 (M+H); $^1$H-NMR (CDCl$_3$, 400 MHz) δ 8.73 (s, 1H), 8.20 (s, 1H), 7.81 (d, 1H, J=7.9 Hz), 7.60 (d, 2H, J=8.4 Hz), 7.51-7.44 (m, 1H), 7.36-7.28 (m, 3H), 7.04 (d, 1H, J=4.8 Hz), 6.92 (s, 1H), 6.85 (d, 1H, J=4.8 Hz), 6.68 (bs, 1H), 3.65 (s, 2H), 3.11-3.04 (m, 4H), 3.04-2.97 (m, 4H), 3.02 (s, 3H).

Example 1053

N-[3-(7-{3-[(Methanesulfonyl-methyl-amino)-methyl]-phenyl}-pyrrolo[2,1-f][1,2,4]triazin-2-ylamino)-phenyl]-acetamide N-[3-(7-{3-[(Methanesulfonyl-methyl-amino)-methyl]-phenyl}-pyrrolo[2,1-f][1,2,4]triazin-2-ylamino)-phenyl]-acetamide was prepared from N-[3-(2-methanesulfinyl-pyrrolo[2,1-f][1,2,4]triazin-7-yl)-benzyl]-N-methyl-methanesulfonamide and 3'-aminoacetanilide in an analogous manner to Example 1049. Product isolated as a yellow foam (25 mg, 22%). LCMS (m/e) 465 (M+H); $^1$H-NMR (CDCl$_3$, 400 MHz) δ 8.71 (s, 1H), 8.11 (d, 1H, J=7.7 Hz), 8.07 (s, 1H), 7.80 (s, 1H), 7.53-7.45 (m, 1H), 7.43-7.34 (m, 2H), 7.30 (s, 1H), 7.28-7.21 (m, 2H), 7.09 (s, 1H), 7.00 (d, 1H, J=4.8 Hz), 6.83 (d, 1H, J=4.8 Hz), 4.38 (s, 2H), 2.86 (s, 3H), 2.79 (s, 3H), 2.16 (s, 3H).

Example 1054

N-{3-[2-(3,3-Dimethyl-2-oxo-2,3-dihydro-1H-indol-6-ylamino)-pyrrolo[2,1-f][1,2,4]triazin-7-yl]-benzyl}-N-methyl-methanesulfonamide N-{3-[2-(3,3-Dimethyl-2-oxo-2,3-dihydro-1H-indol-6-ylamino)-pyrrolo[2,1-f][1,2,4]triazin-7-yl]-benzyl}-N-methyl-methanesulfonamide was prepared from N-[3-(2-methanesulfinyl-pyrrolo[2,1-f][1,2,4]triazin-7-yl)-benzyl]-N-methyl-methanesulfonamide and 6-amino-3,3-dimethyl-1,3-dihydro-indol-2-one in an analogous manner to Example 1049. Product isolated as a yellow foam (23 mg, 19%). LCMS (m/e) 491 (M+H), $^1$H-NMR (CDCl$_3$, 400 MHz) δ 8.73 (s, 1H), 8.11 (d, 1H, J=8.0 Hz), 8.09 (s, 1H), 7.56-7.52 (m, 1H), 7.52-7.46 (m, 1H), 7.44 (s, 1H), 7.35 (d, 1H, J=7.6 Hz), 7.10 (d, 1H, J=8.0 Hz), 7.05-6.98 (m, 2H), 6.93 (s, 1H), 6.86 (d, 1H, J=4.8 Hz), 4.41 (s, 2H), 2.90 (s, 3H), 2.83 (s, 3H), 1.40 (s, 6H).

Example 1055

2-(4-{4-[7-(3-tert-Butylsulfamoyl-phenyl)-pyrrolo[2,1-f][1,2,4]triazin-2-ylamino]-phenyl}-piperidin-1-yl)-acetamide 2-(4-{4-[7-(3-tert-Butylsulfamoyl-phenyl)-pyrrolo[2,1-f][1,2,4]triazin-2-ylamino]-phenyl}-piperidin-1-yl)-acetamide was prepared from N-tert-butyl-3-(2-hydroxy-pyrrolo[2,1-f][1,2,4]triazin-7-yl)-benzenesulfonamide and 2-[4-(4-amino-phenyl)-piperidin-1-yl]-acetamide in an analogous manner to Example 1052a. Product isolated as a red foam (68 mg, 70%). LCMS (m/e) 562 (M+H); $^1$H-NMR (CDCl$_3$, 400 MHz) δ 8.85 (s, 1H), 8.73 (s, 1H), 8.24 (d, 1H, J=8.0 Hz), 7.87 (d, 1H, J=7.9 Hz), 7.62-7.54 (m, 3H), 7.29 (d, 2H, J=8.4 Hz), 7.17 (bs, 1H), 7.07 (d, 1H, J=4.8 Hz), 6.98 (s, 1H), 6.85 (d, 1H, J=4.8 Hz), 5.65 (bs, 1H), 4.72 (s, 1H), 3.08-2.95 (m, 4H), 2.59-2.48 (m, 1H), 2.37-2.25 (m, 2H), 1.94-1.73 (m, 4H).

Example 1056

{7-[6-(1,1-Dioxo-1$1(6)-thiomorpholin-4-ylmethyl)-pyridin-3-yl]-pyrrolo[2,1-f][1,2,4]triazin-2-yl}-[4-(4-methyl-piperazin-1-yl)-phenyl]-amine 1056a) 5-Bromo-2-methyl-pyridine (3.00 g, 17.4 mmol) was dissolved in Carbon tetrachloride (40.0 mL) and N-Bromosuccinimide (3.41 g, 19.2 mmol) was added. Benzoyl peroxide (0.23 g, 0.95 mmol) was added and the mixture was heated at 80° C. overnight. The reaction was cooled to room temperature and filtered to remove the succinimide. The filtrate was concentrated under reduced pressure. Purification by silica gel chromatography using 10% EtOAc/hex as the eluting solvent to obtain 5-bromo-2-bromomethyl-pyridine as a lachrymatory lilac oil (1.34 g, 31%). LCMS (m/e) 251 (M+H); $^1$H-NMR (CDCl$_3$, 400 MHz) δ 8.63 (d, 1H, J=2.2 Hz), 7.81 (dd, 1H, J=2.2 and 8.3 Hz), 7.34 (d, 1H, J=8.3 Hz), 4.50 (s, 2H).

1056b) A suspension of 5-bromo-2-bromomethyl-pyridine (1.34 g, 5.34 mmol), thiomorpholine 1,1-dioxide (0.860 g, 6.36 mmol), and potassium carbonate (1.49 g, 10.8 mmol) in acetone (15.0 mL) was stirred at 40° C. overnight. The mixture was cooled to room temperature and the volatiles were evaporated. The residue was partitioned between EtOAc (100 mL) and saturated aqueous ammonium chloride (50 mL). The organic layer was dried over sodium sulfate, filtered, and concentrated under reduced pressure. Purification by silica gel chromatography using a gradient of 0-100% EtOAc/hex as the eluting solvent to obtain 4-(5-bromo-pyridin-2-ylmethyl)-thiomorpholine 1,1-dioxide as a white solid (1.37 g, 84%). m.p.=129-131° C.; LCMS (m/e) 305 (M+H); $^1$H-NMR (CDCl$_3$, 400 MHz) δ 8.64 (d, 1H, J=2.3 Hz), 8.82 (dd, 1H, J=2.3 and 8.3 Hz), 7.29 (d, 1H, J=8.3 Hz), 3.78 (s, 2H), 3.13-3.02 (m, 8H).

1056c) {7-[6-(1,1-Dioxo-1$1(6)-thiomorpholin-4-ylmethyl)-pyridin-3-yl]-pyrrolo[2,1-f][1,2,4]triazin-2-yl}-[4-(4-methyl-piperazin-1-yl)-phenyl]-amine was prepared from 445-bromo-pyridin-2-ylmethyl)-thiomorpholine 1,1-dioxide and [4-(4-methyl-piperazin-1-yl)-phenyl]-[7-(4,4,5,5-tetramethyl-[1,3,2]dioxaborolan-2-yl)-pyrrolo[2,1-f][1,2,4]triazin-2-yl]-amine in an analogous manner to Example 1042b. Product isolated as a yellow foam (16 mg, 12%). LCMS (m/e) 533 (M+H); $^1$H-NMR (CDCl$_3$, 400 MHz) δ 9.16 (d, 1H, J=1.6 Hz), 8.73 (s, 1H), 8.57 (dd, 1H, J=2.1 and 8.2 Hz), 7.53-7.40 (m, 3H), 7.02 (d, 1H, J=4.8 Hz), 6.95 (d, 2H, J=8.9 Hz), 6.84 (d, 1H, J=4.8 Hz), 6.72 (s, 1H), 3.89 (s, 2H), 3.24-3.18 (m, 4H), 3.16-3.09 (m, 8H), 2.72-2.64 (m, 4H), 2.42 (s, 3H).

Example 1057

N-tert-Butyl-3-{2-[4-(1,1-dioxo-1$1(6)-thiomorpholin-4-ylmethyl)-phenylamino]-pyrrolo[2,1-f][1,2,4]triazin-7-yl}-benzenesulfonamide 1057a) (7-Bromo-pyrrolo[2,1-f][1,2,4]triazin-2-yl)-[4-(1,1-dioxo-1 $1(6)-thiomorpholin-4-ylmethyl)-phenyl]-amine was prepared from 7-bromo-pyrrolo[2,1-f][1,2,4]triazin-2-ol and 4-(1,1-dioxo-1$1(6)-thiomorpholin-4-ylmethyl)-phenylamine in an analogous manner to Example 1052a. Product isolated as a yellow foam (134 mg, 66%). LCMS (m/e) 301 (M—N(CH2)4SO2); $^1$H-NMR (CDCl$_3$, 400 MHz) δ 8.60 (s, 1H), 7.73 (d, 2H, J=8.5 Hz), 7.31 (d, 2H, J=8.5 Hz), 6.92 (s, 1H), 6.81 (d, 1H, J=4.8 Hz), 6.76 (d, 1H, J=4.8 Hz), 3.63 (s, 2H), 3.10-3.03 (m, 4H), 3.03-2.97 (m, 4H).

1057b) N-tert-Butyl-3-{2-[4-(1,1-dioxo-1$1(6)-thiomorpholin-4-ylmethyl)-phenylamino]-pyrrolo[2,1-f][1,2,4]triazin-7-yl}-benzenesulfonamide was prepared from (7-Bromo-pyrrolo[2,1-f][1,2,4]triazin-2-yl)-[4-(1,1-dioxo-1$1(6)-thiomorpholin-4-ylmethyl)-phenyl]-amine and 3-t-Butylsulfamoylphenylboronic acid in an analogous manner to Example 1031b. Product isolated as a yellow foam (90 mg, 71%). LCMS (m/e) 569 (M+H); $^1$H-NMR (CDCl$_3$, 400 MHz) δ 8.79 (s, 1H), 8.72 (s, 1H), 8.17 (d, 1H, J=7.9 Hz), 7.87 (d, 1H, J=7.9 Hz), 7.63-7.53 (m, 3H), 7.33 (d, 2H, J=8.3 Hz), 7.13 (s, 1H), 7.03 (d, 1H, J=4.8 Hz), 6.84 (d, 1H, J=4.8 Hz), 4.92 (s, 1H), 3.63 (s, 2H), 3.14-3.04 (m, 4H), 3.04-2.96 (m, 4H), 1.22 (s, 9H).

Example 1058

4-{4-[7-(3-tert-Butylsulfamoyl-phenyl)-pyrrolo[2,1-f][1,2,4]triazin-2-ylamino]-phenyl}-piperidine-1-carboxylic acid tert-butyl ester 1058a) 10 M sodium hydroxide in water (2.74 mL, 52.4 mmol) was heated at 100° C. N-tert-butyl-3-(2-methanesulfonyl-pyrrolo[2,1-f][1,2,4]triazin-7-yl)-benzenesulfonamide (780 mg, 1.91 mmol) was added portion wise over 10 minutes. The reaction mixture was heated at 120° C. for 60 minutes and then cooled to room temperature. Glacial acetic acid was added to adjust the pH to 4 and the mixture was stirred at room temperature for 30 minutes. The solid was filtered and washed sequentially with water (75 mL) and $Et_2O$ (50 mL) to obtain N-tert-butyl-3-(2-hydroxy-pyrrolo[2,1-f][1,2,4]triazin-7-yl)-benzenesulfonamide as a red-orange solid (460 mg, 70%). LCMS (m/e) 347 (M+H); $^1$H-NMR ($d_6$-DMSO, 400 MHz) δ 9.00 (s, 1H), 8.68 (s, 1H), 8.47 (d, 1H, J=8.0 Hz), 7.78 (d, 1H, J=7.7 Hz), 7.71-7.64 (m, 1H), 7.59 (s, 1H), 7.30 (d, 1H, J=4.8 Hz), 7.01 (d, 1H, J=4.8 Hz), 1.91 (s, 1H), 1.13 (s, 9H).

1058b) 4-{4-[7-(3-tert-Butylsulfamoyl-phenyl)-pyrrolo[2,1-f][1,2,4]triazin-2-ylamino]-phenyl}-piperidine-1-carboxylic acid tert-butyl ester was prepared from N-tert-butyl-3-(2-hydroxy-pyrrolo[2,1-f][1,2,4]triazin-7-yl)-benzenesulfonamide and 4-(4-amino-phenyl)-piperidine-1-carboxylic acid tert-butyl ester in an analogous manner to Example 1052a. Product isolated as an orange foam (82 mg, 47%). LCMS (m/e) 627 (M+Na); $^1$H-NMR ($CDCl_3$, 400 MHz) δ 8.79 (s, 1H), 8.74 (s, 1H), 8.29 (d, 1H, J=8.1 Hz), 7.87 (d, 1H, J=7.9 Hz), 7.62-7.53 (m, 3H), 7.31-7.24 (m, 2H), 7.08 (d, 1H, J=4.8 Hz), 6.88-6.80 (m, 2H), 4.46 (s, 1H), 4.37-4.18 (m, 2H), 2.89-2.75 (m, 2H), 2.75-2.60 (m, 1H), 1.90-1.81 (m, 2H), 1.71-1.60 (m, 2H), 1.49 (s, 9H), 1.17 (s, 9H).

Example 1059

N-tert-Butyl-3-[2-(4-piperidin-4-yl-phenylamino)-pyrrolo[2,1-f][1,2,4]triazin-7-yl]-benzenesulfonamide 4-{4-[7-(3-tert-Butylsulfamoyl-phenyl)-pyrrolo[2,1-f][1,2,4]triazin-2-ylamino]-phenyl}-piperidine-1-carboxylic acid tert-butyl ester (50.0 mg, 0.0827 mmol) was treated with trifluoroacetic acid (191 uL, 2.48 mmol) in methylene chloride (3.00 mL). The reaction was diluted with DCM (25 mL) and washed with saturated sodium bicarbonate (25 mL). The aqueous layer was extracted with DCM (25 mL) three times and the combined organic layers were dried over sodium sulfate, filtered, and concentrated under reduced pressure to obtain the title compound as an orange foam (40 mg, 96%). LCMS (m/e) 505 (M+H); $^1$H-NMR ($CDCl_3$, 400 MHz) δ 8.79 (s, 1H), 8.73 (s, 1H), 8.29 (d, 1H, J=7.8 Hz), 7.87 (d, 1H, J=7.8 Hz), 7.62-7.51 (m, 3H), 7.28 (d, 2H, J=8.3 Hz), 7.07 (d, 1H, J=4.8 Hz), 6.92 (bs, 1H), 6.84 (d, 1H, J=4.8 Hz), 4.77-4.57 (m, 1H), 3.01-3.20 (m, 2H), 2.87-2.73 (m, 2H), 2.72-2.59 (m, 1H), 1.94-1.82 (m, 2H), 1.79-1.63 (m, 2H), 1.17 (s, 9H).

Example 1060

N-tert-Butyl-3-[2-(1-methanesulfonyl-1,2,3,4-tetrahydro-quinolin-7-ylamino)-pyrrolo[2,1-f][1,2,4]triazin-7-yl]-benzenesulfonamide N-tert-Butyl-3-[2-(1-methanesulfonyl-1,2,3,4-tetrahydro-quinolin-7-ylamino)-pyrrolo[2,1-f][1,2,4]triazin-7-yl]-benzenesulfonamide was prepared from N-tert-butyl-3-(2-hydroxy-pyrrolo[2,1-f][1,2,4]triazin-7-yl)-benzenesulfonamide and 1-methanesulfonyl-1,2,3,4-tetrahydro-quinolin-7-ylamine in an analogous manner to Example 1052a. Product isolated as a yellow solid (69 mg, 57%). m.p.=187-191° C.; LCMS (m/e) 555 (M+H); $^1$H-NMR (d6-DMSO, 400 MHz) δ 9.50 (s, 1H), 9.04 (s, 1H), 8.51-8.42 (m, 2H), 7.82 (d, 1H, J=7.9 Hz), 7.76-7.65 (m, 3H), 7.62 (s, 1H), 7.20 (d, 1H, J=4.8 Hz), 7.16 (d, 1H, J=8.3 Hz), 6.99 (d, 1H, J=4.8 Hz), 3.73-3.67 (m, 2H), 3.00 (s, 3H), 2.78-2.71 (m, 2H), 1.97-1.87 (m, 2H), 1.11 (s, 9H).

Example 1061

(1-Methanesulfonyl-1,2,3,4-tetrahydro-quinolin-7-yl)-[7-(6-methoxy-pyridin-3-yl)-pyrrolo[2,1-f][1,2,4]triazin-2-yl]-amine Trifluoro-methanesulfonic acid 7-(6-methoxy-pyridin-3-yl)-pyrrolo[2,1-f][1,2,4]triazin-2-yl ester (95.0 mg, 0.254 mmol) was dissolved in N,N-dimethylformamide (3.00 mL). N,N-diisopropylethylamine (133 uL, 0.761 mmol) was added followed by 1-methanesulfonyl-1,2,3,4-tetrahydro-quinolin-7-ylamine (80.4 mg, 0.355 mmol) and the reaction was stirred overnight. The reaction was taken up in EtOAc (25 mL) and washed three times with water (25 mL). The organic layer was dried over sodium sulfate, filtered, and concentrated under reduced pressure. Purification by silica gel chromatography using a gradient of 0-70% EtOAc/hex as the eluting solvent to obtain the title compound as a yellow solid (54 mg, 47%). m.p.=202-203° C.; LCMS (m/e) 451 (M+H); $^1$H-NMR ($d_6$-DMSO, 400 MHz) δ 9.46 (s, 1H), 8.98 (s, 1H), 8.89 (s, 1H), 8.53 (dd, 1H, J=2.2 and 8.7 Hz), 7.81 (s, 1H), 7.53 (d, 1H, J=8.4 Hz), 7.19 (d, 1H, J=4.7 Hz), 7.10 (d, 1H, J=8.4 Hz), 7.02-6.93 (m, 2H), 3.93 (s, 3H), 3.74-3.68 (m, 2H), 2.99 (s, 3H), 2.79-2.72 (m, 2H), 1.97-1.88 (m, 2H).

Example 1062

N-{2-[2-(1-Methanesulfonyl-1,2,3,4-tetrahydro-quinolin-7-ylamino)-pyrrolo[2,1-f][1,2,4]triazin-7-yl]-phenyl}-N-methyl-methanesulfonamide N-{2-[2-(1-Methanesulfonyl-1,2,3,4-tetrahydro-quinolin-7-ylamino)-pyrrolo[2,1-f][1,2,4]triazin-7-yl]-phenyl}-N-methyl-methanesulfonamide was prepared from Trifluoro-methanesulfonic acid 7-[2-(methanesulfonyl-methyl-amino)-phenyl]-pyrrolo[2,1-f][1,2,4]triazin-2-yl ester and 1-methanesulfonyl-1,2,3,4-tetrahydro-quinolin-7-ylamine in an analogous manner to Example 1061. Product isolated as a yellow foam (61 mg, 55%). LCMS (m/e) 527 (M+H); $^1$H-NMR ($CDCl_3$, 400 MHz) δ 8.73 (s, 1H), 7.94-7.87 (m, 1H), 7.68-7.62 (m, 1H), 7.56-7.44 (m, 3H), 7.40 (dd, 1H, J=1.7 and 8.3 Hz), 7.00 (d, 1H, J=4.7 Hz), 6.96 (d, 1H, J=8.3 Hz), 6.87 (d, 1H, J=4.7 Hz), 6.79 (bs, 1H), 3.82-3.73 (m, 2H), 3.13 (s, 3H), 2.82-2.74 (m, 2H), 2.78 (s, 3H), 2.64 (s, 3H), 2.01-1.92 (m, 2H).

Example 1063

2-[4-(4-{7-[3-(tert-Butyl-dimethyl-silanyloxymethyl)-phenyl]-pyrrolo[2,1-f][1,2,4]triazin-2-ylamino}-phenyl)-piperidin-1-yl]-acetamide 1063a) [3-(2-Methylsulfanyl-pyrrolo[2,1-f][1,2,4]triazin-7-yl)-phenyl]-methanol (830 mg, 3.06 mmol) was dissolved in methylene chloride (25.0 mL) and cooled to 0° C. Triethylamine (938 uL, 6.73 mmol) and 4-dimethylaminopyridine (785 mg, 6.42 mmol) was added and the mixture was stirred for 10 minutes. tert-Butyldimethylsilyl chloride (507 mg, 3.36 mmol) was added and the mixture was stirred for 30 minutes and then allowed to warm to room temperature and stirred for 3 hours. The reaction was washed twice with 10% citric acid (100 mL) and the organic layer was dried over sodium sulfate, filtered, and concentrated under reduced pressure. Purification by silica gel chromatography using a gradient of 0-20% EtOAc/hex as the eluting solvent to obtain 7-[3-(tert-butyl-dimethyl-silanyloxymethyl)-phenyl]-2-methylsulfanyl-pyrrolo[2,1-f][1,2,4]triazine as a yellow oil (1.12 g, 95%). LCMS (m/e) 386 (M+H); $^1$H-NMR (CDCl$_3$, 400 MHz) δ 8.73 (s, 1H), 8.08-8.02 (m, 2H), 7.50-7.42 (m, 1H), 7.35 (d, 1H, J=7.7 Hz), 7.11 (d, 1H, J=4.8 Hz), 6.89 (d, 1H, J=4.8 Hz), 4.82 (s, 2H), 2.61 (s, 3H), 0.97 (s, 9H), 0.13 (s, 6H).

1063b) 7-[3-(tert-Butyl-dimethyl-silanyloxymethyl)-phenyl]-2-methylsulfanyl-pyrrolo[2,1-f][1,2,4]triazine (1.12 g, 2.90 mmol) was dissolved in methanol (20 mL) and sodium tungstate dihydrate (77.3 mg, 0.234 mmol), acetic acid (1.37 mL, 24.2 mmol) and 50% hydrogen peroxide (610 uL, 10.7 mmol) were added. The reaction mixture was then stirred and heated at 65° C. for 4 hours. Once the reaction was complete, 25 mL of 10% Na$_2$S$_2$O$_3$ was added and the reaction was stirred for 5 minutes. The reaction was diluted with saturated NaHCO$_3$ and the product was collected by filtration to obtain 7-[3-(tert-butyl-dimethyl-silanyloxymethyl)-phenyl]-2-methanesulfonyl-pyrrolo[2,1-f][1,2,4]triazine as a yellow solid (818 mg, 67%). m.p.=61-65° C.; LCMS (m/e)=418 (M+H); $^1$H-NMR (d$_6$-DMSO, 400 MHz) δ 9.40 (s, 1H), 8.21-8.06 (m, 2H), 7.77 (d, 1H, J=4.6 Hz), 7.60-7.50 (m, 1H), 7.48-7.37 (m, 2H), 4.81 (s, 2H), 3.46 (s, 3H), 0.91 (s, 9H), 0.11 (s, 6H).

1063c) 7-[3-(tert-Butyl-dimethyl-silanyloxymethyl)-phenyl]-2-methanesulfonyl-pyrrolo[2,1-f][1,2,4]triazine (800 mg, 1.92 mmol) was dissolved in 1,4-dioxane (5.00 mL) and 5.00 M sodium hydroxide in water (5.00 mL, 25.0 mmol) was added. The reaction was heated at 80° C. for 2 hours and then acidified to pH 6 with conc. HCl. The product was then extracted with DCM (100 mL) and the organic layer was dried over sodium sulfate, filtered, and concentrated under reduced pressure. Purification by silica gel chromatography using a gradient of 0-100% EtOAc/hex as the eluting solvent to obtain 7-[3-(tert-butyl-dimethyl-silanyloxymethyl)-phenyl]-pyrrolo[2,1-f][1,2,4]triazin-2-ol as a yellow solid (252 mg, 37%). m.p.=194-195° C.; LCMS (m/e) 356 (M+H); $^1$H-NMR (CDCl$_3$, 400 MHz) δ 8.48 (s, 1H), 8.27 (d, 1H, J=7.7 Hz), 8.07 (s, 1H), 7.52-7.44 (m, 1H), 7.40 (d, 1H, J=7.6 Hz), 7.17 (d, 1H, J=5.1 Hz), 7.05 (d, 1H, J=5.1 Hz), 4.84 (s, 2H), 0.97 (s, 9H), 0.13 (s, 6H).

1063d) 2-[4-(4-{7-[3-(tert-Butyl-dimethyl-silanyloxymethyl)-phenyl]-pyrrolo[2,1-f][1,2,4]triazin-2-ylamino}-phenyl)-piperidin-1-yl]-acetamide was prepared from 7-[3-(tert-butyl-dimethyl-silanyloxymethyl)-phenyl]-pyrrolo[2,1-f][1,2,4]triazin-2-ol and 2-[4-(4-Amino-phenyl)-piperidin-1-yl]-acetamide in an analogous manner to Example 1052a. Product isolated as an orange solid (104 mg, 54%). m.p.=170-173° C.; LCMS (m/e) 571 (M+H); $^1$H-NMR (CDCl$_3$, 400 MHz) δ 8.70 (s, 1H), 8.07 (s, 1H), 8.03 (d, 1H, J=7.8 Hz), 7.61 (d, 2H, J=8.3 Hz), 7.52-7.44 (m, 1H), 7.40 (d, 1H, J=7.5 Hz), 7.19 (d, 2H, J=8.3 Hz), 7.19-7.08 (m, 1H), 7.00 (d, 1H, J=4.7 Hz), 6.87-6.80 (m, 2H), 5.45 (bs, 1H), 4.88 (s, 2H), 3.05 (s, 2H), 3.06-2.97 (m, 2H), 2.58-2.43 (m, 1H), 2.38-2.25 (m, 2H), 1.94-1.85 (m, 2H), 1.85-1.70 (m, 2H), 0.97 (s, 9H), 0.13 (s, 6H).

Example 1064

(3H-Benzoimidazol-5-yl)-{7-[3-(tert-butyl-dimethyl-silanyloxymethyl)-phenyl]-pyrrolo[2,1-f][1,2,4]triazin-2-yl}-amine (3H-Benzoimidazol-5-yl)-{7-[3-(tert-butyl-dimethyl-silanyloxymethyl)-phenyl]-pyrrolo[2,1-f][1,2,4]triazin-2-yl}-amine was prepared from 7-[3-(tert-butyl-dimethyl-silanyloxymethyl)-phenyl]-pyrrolo[2,1-f][1,2,4]triazin-2-ol and 3H-benzimidazol-5-ylamine in an analogous manner to Example 1052a. Product isolated as an orange solid (129 mg, 81%). m.p.=70-75° C.; LCMS (m/e) 471 (M+H); $^1$H-NMR (CDCl$_3$, 400 MHz) δ 11.20-10.10 (m, 1H), 8.73 (s, 1H), 8.67-8.39 (m, 2H), 7.97 (s, 1H), 7.86-7.62 (m, 2H), 7.51-7.42 (m, 1H), 7.32 (d, 1H, J=7.5 Hz), 7.09-6.92 (m, 3H), 6.86 (d, 1H, J=4.7 Hz), 4.97 (s, 2H), 0.96 (s, 9H), 0.16 (s, 6H).

Example 1065

2-(4-{4-[7-(3-Hydroxymethyl-phenyl)-pyrrolo[2,1-f][1,2,4]triazin-2-ylamino]-phenyl}-piperidin-1-yl)-acetamide 2-[4-(4-{7-[3-(tert-Butyl-dimethyl-silanyloxymethyl)-phenyl]-pyrrolo[2,1-f][1,2,4]triazin-2-ylamino}-phenyl)-piperidin-1-yl]-acetamide (100 mg, 0.175 mmol) was dissolved in tetrahydrofuran (10.0 mL, 123 mmol) and 1.00 M tetra-n-butylammonium fluoride in tetrahydrofuran (0.193 mL, 0.193 mmol) was added. The reaction was stirred at room temperature for 3 hours and was then concentrated under reduced pressure. The residue was taken up in DMSO (2 mL) and purified by prep-HPLC using a gradient of 0-55% AcN/water both containing 0.1% TFA as the eluting solvent. The product was then taken up in MeOH (30 mL) and MP-carbonate (1.2 g) and stirred for 2 hours. The reaction was then filtered and concentrated under reduced pressure to obtain the title compound as a yellow foam (31 mg, 39%). LCMS (m/e) 457 (M+H); $^1$H-NMR (d$_6$-DMSO, 400 MHz) δ 9.42 (s, 1H), 8.97 (s, 1H), 8.18 (s, 1H), 7.98 (d, 1H, J=7.7 Hz), 7.71 (d, 2H, J=8.3 Hz), 7.54-7.46 (m, 1H), 7.38 (d, 1H, J=7.6 Hz), 7.28-7.08 (m, 5H), 6.95 (d, 1H, J=4.6 Hz), 5.31 (bs, 1H), 4.62 (s, 2H), 2.97-2.88 (m, 2H), 2.88 (s, 2H), 2.49-2.38 (m, 1H), 2.22-2.08 (m, 2H), 1.79-1.67 (m, 4H).

Example 1066

N-tert-Butyl-3-[2-(2-hydroxymethyl-3H-benzoimidazol-5-ylamino)-pyrrolo[2,1-f][1,2,4]triazin-7-yl]-benzenesulfonamide 1066a) 1,2-Diamino-4-nitrobenzene (5.00 g, 0.0326 mol), glycolic acid (3.72 g, 0.0490 mol), 4.00 M hydrogen chloride in water (13.1 mL, 0.0522 mol), water (13.1 mL, 0.725 mol), and activated charcoal (100 mg) were refluxed overnight. The reaction was cooled to room temperature, filtered and neutralized with aqueous ammonia. The product was filtered and dried in a vacuum desiccator overnight to obtain (6-nitro-1H-benzoimidazol-2-yl)-methanol as a brown solid (6.29 g, 100%). m.p.=157-162° C.; LCMS (m/e) 194 (M+H); $^1$H-NMR (d$_6$-DMSO, 400 MHz) δ 10.24 (bs, 1H), 8.39 (d, 1H, J=1.9 Hz), 8.09 (dd, 1H, J=1.9 and 8.8 Hz), 7.66 (d, 1H, J=8.8 Hz), 5.93 (bs, 1H), 4.77 (s, 2H).

1066b) (6-Nitro-1H-benzoimidazol-2-yl)-methanol (1.00 g, 5.18 mmol) was dissolved in methanol (50.0 mL) and 3.00 M hydrogen chloride in methanol (8.63 mL, 25.9 mmol). 10% Palladium on Carbon (50% wet) (55.1 mg, 0.0259 mmol) was added and the reaction was hydrogenated at 40 psi. for 3 hours. The reaction was then filtered through celite to remove the catalyst and then concentrated under reduced pressure to obtain (6-Amino-1H-benzoimidazol-2-yl)-methanol; dihydrochloride as a brown foam (1.13 g, 92%). Product is used without further purification.

1066c) N-tert-Butyl-3-[2-(2-hydroxymethyl-3H-benzoimidazol-5-ylamino)-pyrrolo[2,1-f][1,2,4]triazin-7-yl]-benzenesulfonamide was prepared from N-tert-butyl-3-(2- hydroxy-pyrrolo[2,1-f][1,2,4]triazin-7-yl)-benzenesulfonamide and (6-amino-1H-benzoimidazol-2-yl)-methanol; dihydrochloride in an analogous manner to Example 1052a. Product isolated as a yellow foam (37 mg, 26%). LCMS (m/e) 492 (M+H); $^1$H-NMR (CDCl$_3$, 400 MHz) δ 10.71 (bs, 1H), 9.00 (s, 1H), 8.68 (s, 1H), 8.17 (s, 1H), 7.90 (d, 1H, J=7.8 Hz), 7.83 (d, 1H, J=7.5 Hz), 7.65-7.54 (m, 1H), 7.44 (d, 1H, J=8.4 Hz), 7.08 (s, 1H), 6.96 (d, 1H, J=4.6 Hz), 6.82 (d, 1H, J=4.7 Hz), 6.73 (bs, 1H), 5.92 (bs, 1H), 4.89 (s, 2H), 2.62 (s, 1H), 1.24 (s, 9H).

Example 1067

{6-[7-(2-Methoxy-phenyl)-pyrrolo[2,1-f][1,2,4]triazin-2-ylamino]-1H-benzoimidazol-2-yl}-methanol {6-[7-(2-Methoxy-phenyl)-pyrrolo[2,1-f][1,2,4]triazin-2-ylamino]-1H-benzoimidazol-2-yl}-methanol was prepared from 7-(2-methoxy-phenyl)-pyrrolo[2,1-f][1,2,4]triazin-2-ol and (6-amino-1H-benzoimidazol-2-yl)-methanol; dihydrochloride in an analogous manner to Example 1052a. Product isolated as a yellow solid (55 mg, 46%). m.p.=239-243° C.; LCMS (m/e) 387 (M+H); $^1$H-NMR (d$_6$-DMSO, 400 MHz) δ 12.05 (bs, 1H), 9.23 (s, 1H), 8.93 (s, 1H), 8.15-7.42 (m, 2H), 7.87 (d, 1H, J=7.2 Hz), 7.50-7.40 (m, 1H), 7.40-7.22 (m, 1H), 7.22 (d, 1H, J=8.3 Hz), 7.19-7.07 (m, 1H), 6.99-6.85 (m, 2H), 5.60 (bs, 1H), 4.64 (s, 2H), 3.83 (s, 3H).

Example 1068

(6-{7-[3-(Morpholine-4-sulfonyl)-phenyl]-pyrrolo[2,1-f][1,2,4]triazin-2-ylamino}-1H-benzoimidazol-2-yl)-methanol (6-{7-[3-(Morpholine-4-sulfonyl)-phenyl]-pyrrolo[2,1-f][1,2,4]triazin-2-ylamino}-1H-benzoimidazol-2-yl)-methanol was prepared from 7-[3-(morpholine-4-sulfonyl)-phenyl]-pyrrolo[2,1-f][1,2,4]triazin-2-ol and (6-amino-1H-benzoimidazol-2-yl)-methanol; dihydrochloride in an analogous manner to Example 1052a. Product isolated as a yellow solid (31 mg, 21%). m.p.=232-237° C.; LCMS (m/e) 506 (M+H); $^1$H-NMR (d$_6$-DMSO, 400 MHz) δ 12.05 (bs, 1H), 9.40 (s, 1H), 9.03 (s, 1H), 8.72 (d, 1H, J=7.8 Hz), 8.28 (s, 1H), 7.86-7.74 (m, 2H), 7.72 (d, 1H, J=7.8 Hz), 7.55 (d, 1H, J=8.7 Hz), 7.46 (d, 1H, J=8.7 Hz), 7.29 (d, 1H, J=4.8 Hz), 6.97 (d, 1H, J=4.8 Hz), 4.66 (s, 2H), 3.62-3.55 (m, 4H), 2.93-2.86 (m, 4H).

Example 1069

{6-[7-(6-Methoxy-pyridin-3-yl)-pyrrolo[2,1-f][1,2,4]triazin-2-ylamino]-1H-benzoimidazol-2-yl}-methanol {6-[7-(6-Methoxy-pyridin-3-yl)-pyrrolo[2,1-f][1,2,4]triazin-2-ylamino]-1H-benzoimidazol-2-yl}-methanol was prepared from trifluoro-methanesulfonic acid 7-(6-methoxy-pyridin-3-yl)-pyrrolo[2,1-f][1,2,4]triazin-2-yl ester and (6-amino-1H-benzoimidazol-2-yl)-methanol; dihydrochloride in an analogous manner to Example 1061. Product isolated as a yellow solid (35 mg, 34%). m.p.=182-187° C.; LCMS (m/e) 388 (M+H); $^1$H-NMR (d$_6$-DMSO, 400 MHz) δ 12.16 (bs, 1H), 9.36 (s, 1H), 8.97 (s, 1H), 8.92 (s, 1H), 8.60 (dd, 1H, J=1.8 and 8.7 Hz), 7.87 (bs, 1H), 7.50-7.35 (m, 2H), 7.18 (d, 1H, J=4.6 Hz), 6.99 (d, 1H, J=8.7 Hz), 6.94 (d, 1H, J=4.6 Hz), 5.63 (bs, 1H), 4.66 (s, 2H), 3.93 (s, 3H).

Example 1070

(6-{7-[3-(Pyrrolidine-1-sulfonyl)-phenyl]-pyrrolo[2,1-f][1,2,4]triazin-2-ylamino}-1H-benzoimidazol-2-yl)-methanol (6-{7-[3-(Pyrrolidine-1-sulfonyl)-phenyl]-pyrrolo[2,1-f][1,2,4]triazin-2-ylamino}-1H-benzoimidazol-2-yl)-methanol was prepared from 7-[3-(pyrrolidine-1-sulfonyl)-phenyl]-pyrrolo[2,1-f][1,2,4]triazin-2-ol and (6-amino-1H-benzoimidazol-2-yl)-methanol; dihydrochloride in an analogous manner to Example 1052a. Product isolated as a yellow foam (57 mg, 40%). LCMS (m/e) 490 (M+H); $^1$H-NMR (d$_6$-DMSO, 400 MHz) δ 12.23-12.01 (m, 1H), 9.47-9.35 (m, 1H), 9.05-8.99 (m, 1H), 8.77-8.61 (m, 1H), 8.35-8.26 (m, 1H), 7.91-7.70 (m, 3H), 7.62-7.37 (m, 2H), 7.32-7.24 (m, 1H), 7.01-6.94 (m, 1H), 5.67-5.58 (m, 1H), 4.70-4.62 (m, 2H), 3.22-3.12 (m, 4H), 1.69-1.60 (m, 4H).

Example 1071

N-{2-[2-(2-Hydroxymethyl-3H-benzoimidazol-5-ylamino)-pyrrolo[2,1-f][1,2,4]triazin-7-yl]-phenyl}-N-methyl-methanesulfonamide N-{2-[2-(2-Hydroxymethyl-3H-benzoimidazol-5-ylamino)-pyrrolo[2,1-f][1,2,4]triazin-7-yl]-phenyl}-N-methyl-methanesulfonamide was prepared from trifluoro-methanesulfonic acid 7-[2-(methanesulfonyl-methyl-amino)-phenyl]-pyrrolo[2,1-f][1,2,4]triazin-2-yl ester and (6-amino-1H-benzoimidazol-2-yl)-methanol; dihydrochloride in an analogous manner to Example 1061. Product isolated as a yellow solid (32 mg, 31%). m.p.=250-256° C.; LCMS (m/e) 464 (M+H); $^1$H-NMR (d$_6$-DMSO, 400 MHz) δ 12.5-12.01 (m, 1H), 9.28-9.21 (m, 1H), 8.98-8.92 (m, 1H), 8.12-8.00 (m, 1H), 7.94-7.89 (m, 0.5H), 7.68-7.60 (m, 2H), 7.60-7.31 (m, 3H), 7.27-7.21 (m, 0.5H), 7.01-6.95 (m, 1H), 6.95-6.89 (m, 1H), 5.65-5.54 (m, 1H), 4.67-4.60 (m, 2H), 3.09-3.03 (m, 3H), 2.92-2.86 (m, 3H).

Example 1072

3-{4-[7-(6-Methoxy-pyridin-3-yl)-pyrrolo[2,1-f][1,2,4]triazin-2-ylamino]-phenyl}-1,4-dimethyl-piperazin-2-one 1072a) (4-Nitro-phenyl)-acetic acid methyl ester (500 mg, 2.56 mmol) was dissolved in carbon tetrachloride (6.00 mL) and N-bromosuccinimide (502 mg, 2.82 mmol) was added followed by 2,2'-azo-bis-isobutyronitrile (12.6 mg, 0.0768 mmol). The reaction was heated at 74° C. overnight. The reaction was then cooled to room temperature and poured into heptane (25 mL). The resulting suspension was filtered and the filter cake washed with heptane (15 mL). The filtrate was concentrated under reduced pressure and the resulting residue was purified by silica gel chromatography using a gradient of 0-25% EtOAc/hex as the eluting solvent to obtain bromo-(4-nitro-phenyl)-acetic acid methyl ester as a clear-colorless oil (547 mg, 78%). LCMS (m/e) 274 (M+H); $^1$H-NMR (CDCl$_3$, 400 MHz) δ 8.23 (d, 2H, J=8.6 Hz), 7.73 (d, 2H, J=8.6 Hz), 5.40 (s, 1H), 3.82 (s, 3H).

1072b) Bromo-(4-nitro-phenyl)-acetic acid methyl ester (547 mg, 2.00 mmol) was dissolved in ethanol (5.50 mL) and N,N'-dimethyl-ethane-1,2-diamine (1.07 mL, 9.98 mmol) was added. The reaction was stirred at room temperature for 30 minutes and then concentrated under reduced pressure. Purification by silica gel chromatography using a gradient of 0-10% MeOH/DCM as the eluting solvent to obtain 1,4-dimethyl-3-(4-nitro-phenyl)-piperazin-2-one as an orange solid (450 mg, 90%). m.p.=99-102° C.; LCMS (m/e) 250 (M+H); ¹H-NMR (CDCl₃, 400 MHz) δ 8.19 (d, 2H, J=8.6 Hz), 7.61 (d, 2H, J=8.6 Hz), 3.83 (s, 1H), 3.81-3.70 (m, 1H), 3.26-3.18 (m, 1H), 3.08-3.00 (m, 1H), 2.97 (s, 3H), 2.78-2.68 (m, 1H), 2.18 (s, 3H).

1072c) 1,4-Dimethyl-3-(4-nitro-phenyl)-piperazin-2-one (445 mg, 1.78 mmol) was dissolved in ethanol (11 mL) and 10% Palladium on Carbon (50% Wet) (19.0 mg, 0.00893 mmol) was added. The reaction was hydrogenated at 50 psi. overnight and then filtered through celite to remove the catalyst. The reaction was then concentrated under reduced pressure to obtain 3-(4-amino-phenyl)-1,4-dimethyl-piperazin-2-one as a yellow foam (391 mg, 100%). LCMS (m/e) 220 (M+H); ¹H-NMR (CDCl₃, 400 MHz) δ 7.12 (d, 2H, J=8.2 Hz), 6.64 (d, 2H, J=8.2 Hz), 3.76-3.66 (m, 1H), 3.68 (s, 1H), 3.26-3.18 (m, 1H), 3.05-2.97 (m, 1H), 2.97 (s, 3H), 2.71-2.61 (m, 1H), 2.19 (s, 3H).

1072d) 3-{4-[7-(6-Methoxy-pyridin-3-yl)-pyrrolo[2,1-f][1,2,4]triazin-2-ylamino]-phenyl}-1,4-dimethyl-piperazin-2-one was prepared from trifluoro-methanesulfonic acid 7-(6-methoxy-pyridin-3-yl)-pyrrolo[2,1-f][1,2,4]triazin-2-yl ester and 3-(4-amino-phenyl)-1,4-dimethyl-piperazin-2-one in an analogous manner to Example 1061. Product isolated as an orange foam (79 mg, 61%). LCMS (m/e) 444 (M+H); ¹H-NMR (CDCl₃, 400 MHz) δ 8.73-8.67 (m, 2H), 4.67 (dd, 1H, J=2.2 and 8.7 Hz), 7.58 (d, 2H, J=8.4 Hz), 7.33 (d, 2H, J=8.4 Hz), 6.95-6.81 (m, 4H), 4.03 (s, 3H), 3.79-3.67 (m, 2H), 3.26-3.18 (m, 1H), 3.07-2.98 (m, 1H), 2.99 (s, 3H), 2.73-2.64 (m, 1H), 2.20 (s, 3H).

Example 1073

N-(2-{2-[4-(1,4-Dimethyl-3-oxo-piperazin-2-yl)-phenylamino]-pyrrolo[2,1-f][1,2,4]triazin-7-yl}-phenyl)-N-methyl-methanesulfonamide N-(2-{2-[4-(1,4-Dimethyl-3-oxo-piperazin-2-yl)-phenylamino]-pyrrolo[2,1-f][1,2,4]triazin-7-yl}-phenyl)-N-methyl-methanesulfonamide was prepared from trifluoro-methanesulfonic acid 7-[2-(methanesulfonyl-methyl-amino)-phenyl]-pyrrolo[2,1-f][1,2,4]triazin-2-yl ester and 3-(4-amino-phenyl)-1,4-dimethyl-piperazin-2-one in an analogous manner to Example 1061. Product isolated as an orange foam (80 mg, 53%). LCMS (m/e) 520 (M+H); ¹H-NMR (CDCl₃, 400 MHz) δ 8.71 (s, 1H), 7.95-7.88 (m, 1H), 7.58-7.46 (m, 3H), 7.45 (d, 2H, J=8.4 Hz), 7.20 (d, 2H, J=8.4 Hz), 7.03 (d, 1H, J=4.7 Hz), 6.87 (d, 1H, J=4.7 Hz), 6.82 (bs, 1H), 3.77-3.67 (m, 1H), 3.64 (s, 1H), 3.24-3.17 (m, 1H), 3.11 (s, 3H), 3.05-2.96 (m, 1H), 2.98 (s, 3H), 2.70 (s, 3H), 2.69-2.61 (m, 1H), 2.16 (s, 3H).

Example 1074

N-tert-Butyl-3-{2-[4-(1,4-dimethyl-3-oxo-piperazin-2-yl)-phenylamino]-pyrrolo[2,1-f][1,2,4]triazin-7-yl}-benzene sulfonamide N-tert-Butyl-3-{2-[4-(1,4-dimethyl-3-oxo-piperazin-2-yl)-phenylamino]-pyrrolo[2,1-f][1,2,4]triazin-7-yl}-benzenesulfonamide was prepared from N-tert-butyl-3-(2-hydroxy-pyrrolo[2,1-f][1,2,4]triazin-7-yl)-benzenesulfonamide and 3-(4-amino-phenyl)-1,4-dimethyl-piperazin-2-one in an analogous manner to Example 1052a. Product isolated as an orange foam (90 mg, 56%). LCMS (m/e) 548 (M+H); ¹H-NMR (CDCl₃, 400 MHz) δ 8.97 (s, 1H), 8.74 (s, 1H), 8.21 (d, 1H, J=7.9 Hz), 7.89 (d, 1H, J=7.8 Hz), 7.64-7.54 (m, 3H), 7.42 (d, 2H, J=8.3 Hz), 7.10 (d, 1H, J=4.8 Hz), 6.91-6.83 (m, 2H), 4.86 (s, 1H), 3.83-3.70 (m, 2H), 3.27-3.17 (m, 1H), 3.04 (s, 3H), 3.06-2.98 (m, 1H), 2.75-2.65 (m, 1H), 2.21 (s, 3H), 1.14 (s, 9H).

Example 1075

1,4-Dimethyl-3-(4-{7-[3-(morpholine-4-sulfonyl)-phenyl]-pyrrolo[2,1-f][1,2,4]triazin-2-ylamino}-phenyl)-piperazin-2-one 1,4-Dimethyl-3-(4-{7-[3-(morpholine-4-sulfonyl)-phenyl]-pyrrolo[2,1-f][1,2,4]triazin-2-ylamino}-phenyl)-piperazin-2-one was prepared from 7-[3-(morpholine-4-sulfonyl)-phenyl]-pyrrolo[2,1-f][1,2,4]triazin-2-ol and 3-(4-amino-phenyl)-1,4-dimethyl-piperazin-2-one in an analogous manner to Example 1052a. Product isolated as an orange foam (91 mg, 55%). LCMS (m/e) 562 (M+H); ¹H-NMR (CDCl₃, 400 MHz) δ 8.75 (s, 1H), 8.57 (d, 1H, J=7.5 Hz), 8.30 (s, 1H), 7.78-7.65 (m, 2H), 7.58 (d, 2H, J=8.3 Hz), 7.38 (d, 2H, J=8.3 Hz), 7.05 (d, 1H, J=4.7 Hz), 6.90 (bs, 1H), 6.86 (d, 1H, J=4.7 Hz), 3.80-3.68 (m, 6H), 3.27-3.19 (m, 1H), 3.12-3.00 (m, 5H), 3.00 (s, 3H), 2.74-2.63 (m, 1H), 2.21 (s, 3H).

Example 1076

3-{4-[7-(2-Methoxy-phenyl)-pyrrolo[2,1-f][1,2,4]triazin-2-ylamino]-phenyl}-1,4-dimethyl-piperazin-2-one 3-{4-[7-(2-Methoxy-phenyl)-pyrrolo[2,1-f][1,2,4]triazin-2-ylamino]-phenyl}-1,4-dimethyl-piperazin-2-one was prepared from 7-(2-methoxy-phenyl)-pyrrolo[2,1-f][1,2,4]triazin-2-ol and 3-(4-amino-phenyl)-1,4-dimethyl-piperazin-2-one in an analogous manner to Example 1052a. Product isolated as a yellow solid (55 mg, 42%). m.p.=249-251° C.; LCMS (m/e) 443 (M+H); ¹H-NMR (CDCl₃, 400 MHz) δ 8.68 (s, 1H), 7.95 (d, 1H, J=7.6 Hz), 7.55 (d, 2H, J=8.4 Hz), 7.46-7.38 (m, 1H), 7.24 (d, 2H, J=8.4 Hz), 7.17-7.09 (m, 1H), 7.06 (d, 1H, J=8.3 Hz), 7.01 (d, 1H, J=4.6 Hz), 6.84 (d, 1H, J=4.6 Hz), 6.79 (bs, 1H), 3.84 (s, 3H), 3.77-3.68 (m, 1H), 3.66 (s, 1H), 3.24-3.17 (m, 1H), 3.05-2.97 (m, 1H), 2.98 (s, 3H), 2.71-2.61 (m, 1H), 2.17 (s, 3H).

Example 1077

N-tert-Butyl-3-{2-[3-(1,4-dimethyl-3-oxo-piperazin-2-yl)-phenylamino]-pyrrolo[2,1-f][1,2,4]triazin-7-yl}-benzenesulfonamide 1077a) Bromo-(3-nitro-phenyl)-acetic acid methyl ester was prepared from (3-nitro-phenyl)-acetic acid methyl ester in an analogous manner to Example 1072a. Product isolated as a clear-colorless oil (1.08 g, 77%). ¹H-NMR (CDCl₃, 400 MHz) δ 8.42 (s, 1H), 8.26-8.19 (m, 1H), 7.91 (d, 1H, J=7.8 Hz), 7.63-7.54 (m, 1H), 5.42 (s, 1H), 3.83 (s, 3H).

1077b) 1,4-Dimethyl-3-(3-nitro-phenyl)-piperazin-2-one was prepared from bromo-(3-nitro-phenyl)-acetic acid methyl ester and N,N'-dimethyl-ethane-1,2-diamine in an analogous manner to Example 1072b. Product isolated as a clear-orange oil (959 mg, 98%). LCMS (m/e) 250 (M+H); ¹H-NMR (CDCl₃, 400 MHz) δ 8.32 (s, 1H), 8.14 (d, 1H, J=8.2 Hz), 7.76 (d, 1H, J=7.6 Hz), 7.54-7.46 (m, 1H), 3.83 (s, 1H), 3.83-3.73 (m, 1H), 3.26-3.18 (m, 1H), 3.08-3.01 (m, 1H), 2.97 (s, 3H), 2.79-2.69 (m, 1H), 2.19 (s, 3H).

1077c) 3-(3-Amino-phenyl)-1,4-dimethyl-piperazin-2-one was prepared from 1,4-dimethyl-3-(3-nitro-phenyl)-piperazin-2-one in an analogous manner to Example 1072c. Product isolated as a yellow foam (843 mg, 100%). LCMS (m/e) 220 (M+H); $^1$H-NMR (CDCl$_3$, 400 MHz) δ 7.15-7.08 (m, 1H), 6.77 (d, 1H, J=7.6 Hz), 6.72 (s, 1H), 6.65-6.58 (m, 1H), 3.83-3.65 (m, 2H), 3.31-3.19 (m, 1H), 3.11-3.02 (m, 1H), 2.99 (s, 3H), 2.76-2.65 (m, 1H), 2.24 (s, 3H).

1077d) N-tert-Butyl-3-{2-[3-(1,4-dimethyl-3-oxo-piperazin-2-yl)-phenylamino]-pyrrolo[2,1-f][1,2,4]triazin-7-yl}-benzenesulfonamide was prepared from N-tert-butyl-3-(2-hydroxy-pyrrolo[2,1-f][1,2,4]triazin-7-yl)-benzenesulfonamide and 3-(3-amino-phenyl)-1,4-dimethyl-piperazin-2-one in an analogous manner to Example 1061. Product isolated as a yellow foam (74 mg, 44%). LCMS (m/e) 548 (M+H); $^1$H-NMR (CDCl$_3$, 400 MHz) δ 8.74 (s, 1H), 8.58 (s, 1H), 8.44 (d, 1H, J=7.9 Hz), 7.86 (d, 1H, J=7.8 Hz), 7.80 (d, 1H, J=8.2 Hz), 7.65-7.55 (m, 1H), 7.44-7.35 (m, 2H), 7.09 (d, 1H, J=7.6 Hz), 7.05 (d, 1H, J=4.8 Hz), 6.89 (s, 1H), 6.85 (d, 1H, J=4.8 Hz), 4.71 (s, 1H), 3.77-3.64 (m, 1H), 3.69 (s, 1H), 3.26-2.97 (m, 1H), 2.99 (s, 3H), 2.73-2.62 (m, 1H), 2.17 (s, 3H), 1.23 (s, 9H).

Example 1078

1,4-Dimethyl-3-(3-{7-[3-(morpholine-4-sulfonyl)-phenyl]-pyrrolo[2,1-f][1,2,4]triazin-2-ylamino}-phenyl)-piperazin-2-one 1,4-Dimethyl-3-(3-{7-[3-(morpholine-4-sulfonyl)-phenyl]-pyrrolo[2,1-f][1,2,4]triazin-2-ylamino}-phenyl)-piperazin-2-one was prepared from 7-[3-(morpholine-4-sulfonyl)-phenyl]-pyrrolo[2,1-f][1,2,4]triazin-2-ol and 3-(3-amino-phenyl)-1,4-dimethyl-piperazin-2-one in an analogous manner to Example 1052a. Product isolated as a yellow foam (84 mg, 49%). LCMS (m/e) 562 (M+H); $^1$H-NMR (CDCl$_3$, 400 MHz) δ 8.75 (s, 1H), 8.63 (d, 1H, J=7.5 Hz), 8.28 (s, 1H), 7.88-7.81 (m, 1H), 7.75-7.64 (m, 2H), 7.43-7.35 (m, 1H), 7.33 (s, 1H), 7.09 (d, 1H, J=7.6 Hz), 7.05 (d, 1H, J=4.8 Hz), 6.90 (s, 1H), 6.86 (d, 1H, J=4.8 Hz), 3.78-3.65 (m, 6H), 3.26-3.18 (m, 1H), 3.10-3.03 (m, 4H), 3.03-2.96 (m, 4H), 2.74-2.62 (m, 1H), 2.17 (s, 3H).

Example 1079

1,4-Dimethyl-3-(3-{7-[3-(pyrrolidine-1-sulfonyl)-phenyl]-pyrrolo[2,1-f][1,2,4]triazin-2-ylamino}-phenyl)-piperazin-2-one 1,4-Dimethyl-3-(3-{7-[3-(pyrrolidine-1-sulfonyl)-phenyl]-pyrrolo[2,1-f][1,2,4]triazin-2-ylamino}-phenyl)-piperazin-2-one was prepared from 7-[3-(pyrrolidine-1-sulfonyl)-phenyl]-pyrrolo[2,1-f][1,2,4]triazin-2-ol and 3-(3-amino-phenyl)-1,4-dimethyl-piperazin-2-one in an analogous manner to Example 1052a. Product isolated as an orange foam (82 mg, 49%). LCMS (m/e) 546 (M+H); $^1$H-NMR (CDCl$_3$, 400 MHz) δ 8.75 (s, 1H), 8.65 (d, 1H, J=8.2 Hz), 8.31 (s, 1H), 7.87-7.77 (m, 2H), 7.70-7.62 (m, 1H), 7.41-7.32 (m, 2H), 7.12-7.03 (m, 2H), 6.94 (s, 1H), 6.85 (d, 1H, J=4.7 Hz), 3.78-3.65 (m, 2H), 3.34-3.25 (m, 4H), 3.25-3.15 (m, 1H), 3.70-2.96 (m, 1H), 2.99 (s, 3H), 2.74-2.62 (m, 1H), 2.18 (s, 3H), 1.82-1.72 (m, 4H).

Example 1080

3-{3-[7-(3-Methanesulfonyl-phenyl)-pyrrolo[2,1-f][1,2,4]triazin-2-ylamino]-phenyl}-1,4-dimethyl-piperazin-2-one 3-{3-[7-(3-Methanesulfonyl-phenyl)-pyrrolo[2,1-f][1,2,4]triazin-2-ylamino]-phenyl}-1,4-dimethyl-piperazin-2-one was prepared from 7-(3-methanesulfonyl-phenyl)-pyrrolo[2,1-f][1,2,4]triazin-2-ol and 3-(3-amino-phenyl)-1,4-dimethyl-piperazin-2-one in an analogous manner to Example 1052a. Product isolated as an orange foam (69 mg, 46%). LCMS (m/e) 491 (M+H); $^1$H-NMR (CDCl$_3$, 400 MHz) δ 8.75 (s, 1H), 8.59 (d, 1H, J=8.0 Hz), 8.52 (s, 1H), 7.91 (d, 1H, J=7.8 Hz), 7.84 (d, 1H, J=8.1 Hz), 7.75-7.66 (m, 1H), 7.41-7.33 (m, 1H), 7.10 (s, 1H), 7.12-7.04 (m, 2H), 6.89-6.81 (m, 2H) 3.76-3.66 (m, 2H), 3.27-3.18 (m, 1H), 3.09 (s, 3H), 3.06-2.96 (m, 1H), 2.98 (s, 3H), 2.74-2.62 (m, 1H), 2.19 (s, 3H).

Example 1081

3-{3-[7-(6-Methoxy-pyridin-3-yl)-pyrrolo[2,1-f][1,2,4]triazin-2-ylamino]-phenyl}-1,4-dimethyl-piperazin-2-one 3-{3-[7-(6-Methoxy-pyridin-3-yl)-pyrrolo[2,1-f][1,2,4]triazin-2-ylamino]-phenyl}-1,4-dimethyl-piperazin-2-one was prepared from 7-(6-methoxy-pyridin-3-yl)-pyrrolo[2,1-f][1,2,4]triazin-2-ol and 3-(3-amino-phenyl)-1,4-dimethyl-piperazin-2-one in an analogous manner to Example 1052a. Product isolated as a brown foam (56 mg, 42%). LCMS (m/e) 444 (M+H); $^1$H-NMR (CDCl$_3$, 400 MHz) δ 8.80-8.74 (m, 1H), 8.69 (s, 1H), 8.43 (dd, 1H, J=2.2 and 8.7 Hz), 7.66 (d, 1H, J=8.1 Hz), 7.51 (s, 1H), 7.35-7.27 (m, 1H), 7.06 (d, 1H, J=7.6 Hz), 6.96-6.89 (m, 2H), 6.87 (d, 1H, J=8.7 Hz), 6.82 (d, 1H, J=4.78 Hz), 4.01 (s, 3H), 3.75-3.63 (m, 2H), 3.25-3.16 (m, 1H), 3.07-2.96 (m, 1H), 2.98 (s, 3H), 2.74-2.63 (m, 1H), 2.21 (s, 3H).

Example 1082

3-{3-[7-(2-Methoxy-phenyl)-pyrrolo[2,1-f][1,2,4]triazin-2-ylamino]-phenyl}-1,4-dimethyl-piperazin-2-one 3-{3-[7-(2-Methoxy-phenyl)-pyrrolo[2,1-f][1,2,4]triazin-2-ylamino]-phenyl}-1,4-dimethyl-piperazin-2-one was prepared from 7-(2-methoxy-phenyl)-pyrrolo[2,1-f][1,2,4]triazin-2-ol and 3-(3-amino-phenyl)-1,4-dimethyl-piperazin-2-one in an analogous manner to Example 1052a. Product isolated as a brown foam (61 mg, 45%). LCMS (m/e) 443 (M+H); $^1$H-NMR (CDCl$_3$, 400 MHz) δ 8.69 (s, 1H), 7.97-7.89 (m, 1H), 7.70 (d, 1H, J=8.1 Hz), 7.45-7.36 (m, 2H), 7.25-7.17 (m, 1H), 7.15-7.08 (m, 1H), 7.05 (d, 1H, J=8.3 Hz), 7.00 (d, 1H, J=4.6 Hz), 6.96 (d, 1H, J=7.6 Hz), 6.89 (s, 1H), 6.83 (d, 1H, J=4.6 Hz), 3.84 (s, 3H), 3.73-3.64 (m, 1H), 3.63 (s, 1H), 3.26-3.17 (m, 1H), 3.03-2.94 (m, 1H), 2.99 (s, 3H), 2.69-2.58 (m, 1H), 2.09 (s, 3H).

Example 1083

N-(2-{2-[3-(1,4-Dimethyl-3-oxo-piperazin-2-yl)-phenylamino]-pyrrolo[2,1-f][1,2,4]triazin-7-yl}-phenyl)-N-methyl-methanesulfonamide N-(2-{2-[3-(1,4-Dimethyl-3-oxo-piperazin-2-yl)-phenylamino]-pyrrolo[2,1-f][1,2,4]triazin-7-yl}-phenyl)-N-methyl-methanesulfonamide was prepared from N-[2-(2-hydroxy-pyrrolo[2,1-f][1,2,4]triazin-7-yl)-phenyl]-N-methyl-methanesulfonamide and 3-(3-amino-phenyl)-1,4-dimethyl-piperazin-2-one in an analogous manner to Example 1052a. Product isolated as a brown foam (72 mg, 46%). LCMS (m/e) 520 (M+H); $^1$H-NMR (CDCl$_3$, 400 MHz) δ 8.72 (s, 1H), 7.89-7.82 (m, 1H), 7.54-7.45 (m, 4H), 7.38 (s, 1H), 7.20-7.12

(m, 1H), 7.02-6.92 (m, 2H), 6.89-6.81 (m, 2H), 3.70-3.60 (m, 1H), 3.52 (s, 1H), 3.24-3.15 (m, 1H), 3.11 (s, 3H), 3.01-2.92 (m, 1H), 2.97 (s, 3H), 2.68-2.55 (m, 1H), 2.62 (s, 3H), 2.08 (s, 3H).

Example 1084

3-{3-[7-(4-Methanesulfonyl-phenyl)-pyrrolo[2,1-f][1,2,4]triazin-2-ylamino]-phenyl}-1,4-dimethyl-piperazin-2-one 3-{3-[7-(4-Methanesulfonyl-phenyl)-pyrrolo[2,1-f][1,2,4]triazin-2-ylamino]-phenyl}-1,4-dimethyl-piperazin-2-one was prepared from 7-(4-methanesulfonyl-phenyl)-pyrrolo[2,1-f][1,2,4]triazin-2-ol and 3-(3-amino-phenyl)-1,4-dimethyl-piperazin-2-one in an analogous manner to Example 1052a. Product isolated as a yellow foam (75 mg, 50%). LCMS (m/e) 491 (M+H); $^1$H-NMR (CDCl$_3$, 400 MHz) δ 8.76 (s, 1H), 8.38 (d, 2H, J=8.4 Hz), 8.05 (d, 2H, J=8.4 Hz), 7.68 (s, 1H), 7.51 (d, 1H, J=8.2 Hz) 7.37-7.29 (m, 1H), 7.11 (d, 1H, J=7.6 Hz), 7.08 (d, 1H, J=4.8 Hz), 6.91 (s, 1H), 6.86 (d, 1H, J=4.8 Hz), 3.75-3.65 (m, 1H), 3.66 (s, 1H), 3.25-3.18 (m, 1H), 3.10 (s, 3H), 3.08-3.00 (m, 1H), 2.99 (s, 3H), 2.77-2.67 (m, 1H), 2.18 (s, 3H).

Example 1085

N-tert-Butyl-3-[2-(4-pyridin-3-yl-phenylamino)-pyrrolo[2,1-f][1,2,4]triazin-7-yl]-benzenesulfonamide N-tert-Butyl-3-[2-(4-pyridin-3-yl-phenylamino)-pyrrolo[2,1-f][1,2,4]triazin-7-yl]-benzenesulfonamide was prepared from N-tert-butyl-3-(2-hydroxy-pyrrolo[2,1-f][1,2,4]triazin-7-yl)-benzenesulfonamide and 4-pyridin-3-yl-phenylamine in an analogous manner to Example 1052a. Product isolated as a pale yellow solid (14 mg, 9%). m.p.=250-253° C.; LCMS (m/e) 499 (M+H); $^1$H-NMR (CDCl$_3$, 400 MHz) δ 8.90 (s, 1H), 8.80 (s, 1H), 8.78 (s, 1H), 8.57 (s, 1H), 8.26 (d, 1H, J=7.8 Hz), 7.95 (d, 1H, J=7.9 Hz), 7.89 (d, 1H, J=7.9 Hz), 7.75 (d, 1H, J=8.5 Hz), 7.69 (d, 1H, J=8.5 Hz), 7.65-7.57 (m, 1H), 7.44-7.32 (m, 1H), 7.10 (d, 1H, J=4.7 Hz), 6.97 (s, 1H), 6.89 (d, 1H, J=4.7 Hz), 1.18 (s, 9H).

Example 1086

(4-Pyridin-3-yl-phenyl)-{7-[3-(pyrrolidine-1-sulfonyl)-phenyl]-pyrrolo[2,1-f][1,2,4]triazin-2-yl}-amine (4-Pyridin-3-yl-phenyl)-{7-[3-(pyrrolidine-1-sulfonyl)-phenyl]-pyrrolo[2,1-f][1,2,4]triazin-2-yl}-amine was prepared from 7-[3-(pyrrolidine-1-sulfonyl)-phenyl]-pyrrolo[2,1-f][1,2,4]triazin-2-ol and 4-pyridin-3-yl-phenylamine in an analogous manner to Example 1052a. Product isolated as a yellow solid (88 mg, 58%). m.p.=194-200° C.; LCMS (m/e) 497 (M+H); $^1$H-NMR (CDCl$_3$, 400 MHz) δ 8.87 (s, 1H), 8.78 (s, 1H), 8.56 (d, 1H, J=4.3 Hz), 8.53 (s, 1H), 8.43 (d, 1H, J=8.0 Hz), 7.91 (d, 1H, J=8.0 Hz), 7.84 (d, 1H, J=7.8 Hz), 7.74 (d, 1H, J=8.6 Hz), 7.71-7.61 (m, 3H), 7.35 (dd, 1H, J=4.9 and 7.7 Hz), 7.09 (d, 1H, J=4.8 Hz), 6.98 (s, 1H), 6.89 (d, 1H, J=4.8 Hz), 3.36-3.22 (m, 4H), 1.83-1.72 (m, 4H).

Example 1087

[7-(3-Methanesulfonyl-phenyl)-pyrrolo[2,1-f][1,2,4]triazin-2-yl]-(4-pyridin-3-yl-phenyl)-amine

[7-(3-Methanesulfonyl-phenyl)-pyrrolo[2,1-f][1,2,4]triazin-2-yl]-(4-pyridin-3-yl-phenyl)-amine was prepared from 7-(3-methanesulfonyl-phenyl)-pyrrolo[2,1-f][1,2,4]triazin-2-ol and 4-pyridin-3-yl-phenylamine in an analogous manner to Example 1052a. Product isolated as a yellow solid (66 mg, 49%). m.p.=216-218° C.; LCMS (m/e) 442 (M+H); $^1$H-NMR (CDCl$_3$, 400 MHz) δ 8.87 (s, 1H), 8.79 (s, 1H), 8.71 (s, 1H), 8.56 (d, 1H, J=4.3 Hz), 8.42 (d, 1H, J=7.9 Hz), 7.95 (d, 1H, J=7.8 Hz), 7.90 (d, 1H, J=8.0 Hz), 7.78-7.68 (m, 3H), 7.64 (d, 2H, J=8.6 Hz), 7.36 (dd, 1H, J=4.9 and 7.7 Hz), 7.09 (d, 1H, J=4.8 Hz), 6.98 (s, 1H), 6.90 (d, 1H, J=4.8 Hz), 3.08 (s, 3H).

Example 1088

[7-(6-Methoxy-pyridin-3-yl)-pyrrolo[2,1-f][1,2,4]triazin-2-yl]-(4-pyridin-3-yl-phenyl)-amine

[7-(6-Methoxy-pyridin-3-yl)-pyrrolo[2,1-f][1,2,4]triazin-2-yl]-(4-pyridin-3-yl-phenyl)-amine was prepared from 7-(6-methoxy-pyridin-3-yl)-pyrrolo[2,1-f][1,2,4]triazin-2-ol and 4-pyridin-3-yl-phenylamine in an analogous manner to Example 1052a. Product isolated as a yellow foam (31 mg, 26%). LCMS (m/e) 395 (M+H); $^1$H-NMR (CDCl$_3$, 400 MHz) δ 8.87 (s, 1H), 8.80 (s, 1H), 8.74 (s, 1H), 8.61-8.54 (m, 1H), 8.42 (d, 1H, J=8.7 Hz), 7.88 (d, 1H, J=7.8 Hz), 7.73 (d, 2H, J=8.1 Hz), 7.57 (d, 2H, J=8.1 Hz), 7.40-7.31 (m, 1H), 7.02-6.84 (m, 4H), 4.03 (s, 3H).

Example 1089

[7-(4-Methanesulfonyl-phenyl)-pyrrolo[2,1-f][1,2,4]triazin-2-yl]-(4-pyridin-3-yl-phenyl)-amine

[7-(4-Methanesulfonyl-phenyl)-pyrrolo[2,1-f][1,2,4]triazin-2-yl]-(4-pyridin-3-yl-phenyl)-amine was prepared from 7-(4-methanesulfonyl-phenyl)-pyrrolo[2,1-f][1,2,4]triazin-2-ol and 4-pyridin-3-yl-phenylamine in an analogous manner to Example 1052a. Product isolated as a yellow foam (37 mg, 28%). LCMS (m/e) 442 (M+H); $^1$H-NMR (d$_6$-DMSO, 400 MHz) δ 9.82 (s, 1H), 9.10 (s, 1H), 8.94 (s, 1H), 8.58-8.46 (m, 3H), 8.17-8.05 (m, 3H), 7.90 (d, 2H, J=7.9 Hz), 7.76 (d, 2H, J=7.9 Hz), 7.54-7.44 (m, 1H), 7.44-7.35 (m, 1H), 7.09-7.01 (m, 1H), 2.50 (s, 3H).

Example 1090

{7-[3-(Morpholine-4-sulfonyl)-phenyl]-pyrrolo[2,1-f][1,2,4]triazin-2-yl}-(4-pyridin-3-yl-phenyl)-amine {7-[3-(Morpholine-4-sulfonyl)-phenyl]-pyrrolo[2,1-f][1,2,4]triazin-2-yl}-(4-pyridin-3-yl-phenyl)-amine was prepared from 7-[3-(morpholine-4-sulfonyl)-phenyl]-pyrrolo[2,1-f][1,2,4]triazin-2-ol and 4-pyridin-3-yl-phenylamine in an analogous manner to Example 1052a. Product isolated as a yellow foam (16 mg, 10%). LCMS (m/e) 513 (M+H); $^1$H-NMR (CDCl$_3$, 400 MHz) δ 8.88 (s, 1H), 8.79 (s, 1H), 8.61-8.52 (m, 1H), 8.49 (s, 1H), 8.41 (d, 1H, J=7.6 Hz), 7.91 (d, 1H, J=7.8 Hz), 7.80-7.60 (m, 6H), 7.40-7.31 (m, 1H), 7.08 (d, 1H, J=4.6 Hz), 7.02 (s, 1H), 6.90 (d, 1H, J=4.5 Hz), 3.75-3.66 (m, 4H), 3.09-3.00 (m, 4H).

Example 1091

[7-(2-Methoxy-phenyl)-pyrrolo[2,1-f][1,2,4]triazin-2-yl]-(4-pyridin-3-yl-phenyl)-amine

[7-(2-Methoxy-phenyl)-pyrrolo[2,1-f][1,2,4]triazin-2-yl]-(4-pyridin-3-yl-phenyl)-amine was prepared from 7-(2-methoxy-phenyl)-pyrrolo[2,1-f][1,2,4]triazin-2-ol and 4-pyridin-3-yl-phenylamine in an analogous manner to Example 1052a. Product isolated as a yellow foam (35 mg, 29%). LCMS (m/e) 394 (M+H); $^1$H-NMR (CDCl$_3$, 400 MHz) δ 8.84 (s, 1H), 8.72 (s, 1H), 8.59-8.51 (m, 1H), 7.97 (d, 1H, J=7.6 Hz), 7.86 (d, 1H, J=7.6 Hz), 7.71 (d, 1H, J=7.4 Hz), 7.48 (d, 2H, J=7.7 Hz), 7.44 (d, 1H, J=7.9 Hz), 7.39-7.31 (m, 1H), 7.19-7.11 (m, 1H), 7.11-7.02 (m, 2H), 6.96-6.85 (m, 2H), 3.86 (s, 3H).

Example 1092

N-Methyl-N-{2-[2-(4-pyridin-3-yl-phenylamino)-pyrrolo[2,1-f][1,2,4]triazin-7-yl]-phenyl}-methane-sulfonamide N-Methyl-N-{2-[2-(4-pyridin-3-yl-phenylamino)-pyrrolo[2,1-f][1,2,4]triazin-7-yl]-phenyl}-methanesulfonamide was prepared from N-[2-(2-hydroxy-pyrrolo[2,1-f][1,2,4]triazin-7-yl)-phenyl]-N-methyl-methanesulfonamide and 4-pyridin-3-yl-phenylamine in an analogous manner to Example 1052a. Product isolated as a yellow foam (71 mg, 50%). LCMS (m/e) 471 (M+H); $^1$H-NMR (CDCl$_3$, 400 MHz) δ 8.82 (s, 1H), 8.75 (s, 1H), 8.55 (d, 1H, J=4.6 Hz), 8.00-7.91 (m, 1H), 7.83 (d, 1H, J=8.1 Hz), 7.60 (d, 2H, J=7.9 Hz), 7.59-7.49 (m, 3H), 7.45 (d, 2H, J=7.7 Hz), 7.39-7.30 (m, 1H), 7.07 (d, 1H, J=4.0 Hz), 6.95-6.85 (m, 2H), 3.15 (s, 3H), 2.72 (s, 3H).

Example 1101

[7-(2-Methoxy-phenyl)-pyrrolo[2,1-f][1,2,4]triazin-2-yl]-[4-(2-morpholin-4-yl-ethoxy)-phenyl]-amine Into a microwave vial, 2-Methanesulfinyl-7-(2-methoxy-phenyl)-pyrrolo[2,1-f][1,2,4]triazine (128 mg, 0.445 mmol), 4-(2-Morpholin-4-yl-ethoxy)-phenylamine (198 mg, 0.891 mmol), 1-Methoxy-2-propanol (1.50 mL, 15.3 mmol) and N,N-Diisopropylethylamine (0.171 mL, 0.980 mmol) were added. The reaction was microwaved on 300 watts, 180° C. for 3 hours. The reaction was monitored by HPLC. The reaction was partitioned with water and DCM. The organic was separated, washed with Brine and dried over Na$_2$SO$_4$. The solid was filtered and washed with DCM. The Solvent was removed under vacuum. The desired product was purified via ISCO column chromatography with DCM and methanol as eluant (0 to 10% methano). The collected fractions afforded a yellow solid (56 mg, 28%). LCMS (E/I+) 446.8 (M+H). MP 133-135° C. NMR $^1$H (DMSO-d$_6$)-9.20 (s, 1H), 8.91 (s, 1H), 7.82 (m, 1H), 7.60 (d, 2H, 8.84 Hz), 7.45 (t, 1H, J=7.88 Hz), 6.92 (d, 1H, J=5.45 Hz), 6.80 (d, 1H, J=5.45 Hz), 6.79 (d, 2H, J=9.09 Hz), 4.02 (t, 2H, J=5.45 Hz), 3.82 (s, 3H), 3.58 (t, 4H, J=4.24 Hz), 2.65 (t, 2H, J=6.06 Hz), 2.46 (m, 4H).

Example 1102

(1-{4-[7-(6-Methoxy-pyridin-3-yl)-pyrrolo[2,1-f][1,2,4]triazin-2-ylamino]-phenyl}-piperidin-4-yl)-methanol The titled compound was prepared in an analogous fashion to Example 81 replacing 4-(4-Methyl-piperazin-1-yl)-phenylamine with [1-(4-Amino-phenyl)-piperidin-4-yl]-methanol to give a yellow solid (31 mg, 17%). LCMS (E/I+) 431.8 (M+H). NMR $^1$H (DMSO-d$_6$)-9.78 (s, 1H), 8.99 (s, 1H), 8.88 (s, 1H), 8.50 (dd, 1H, JJ=8.83, 8.55 Hz), 7.82 (bs, 1H), 7.51 (bs, 1H), 7.20 (d, 1H, J=4.90 Hz), 7.04 (d, 1H, J=9.25 Hz), 7.00 (d, 1H, J=4.90 Hz), 3.95 (s, 3H0, 3.20-3.61, (bm, 7H), 1.86-1.97 (bm, 2H), 1.48-1.80 (m, 3H).

Example 1103

[7-(6-Methoxy-pyridin-3-yl)-pyrrolo[2,1-f][1,2,4]triazin-2-yl]-[4-(2-morpholin-4-yl-ethoxy)-phenyl]-amine The titled compound was prepared in an analogous fashion to Example 81 replacing 4-(4-Methyl-piperazin-1-yl)-phenylamine with 4-(2-Morpholin-4-yl-ethoxy)-phenylamine to give a yellow solid (12 mg, 6.9%). LCMS (E/I+) 447.7 (M+H). NMR $^1$H (DMSO-d$_6$)-10.00 (bs, 1H), 9.38 (s, 1H), 8.96 (s, 1H), 8.90 (d, 1H, J=2.53), 8.51 (dd, 1H, JJ=2.10, 8.84 Hz), 7.67 (d, 1H, J=2.53), 7.16 (d, 1H, J=4.63), 6.96-7.03 (m, 3H), 6.95 (d, 1H, J=5.05), 4.34 (t, 2H, J=4.63), 3.90-4.05 (m, 5H), 3.65-3.78 (m, 2H), 3.15-3.40 (m, 6H). LCMD 447.7 (M+H).

Example 1104

2-(4-{4-[7-(6-Methoxy-pyridin-3-yl)-pyrrolo[2,1-f][1,2,4]triazin-2-ylamino]-phenyl}-piperazin-1-yl)-ethanol The titled compound was prepared in an analogous fashion to Example 81 replacing 4-(4-Methyl-piperazin-1-yl)-phenylamine with 2-[4-(4-Amino-phenyl)-piperazin-1-yl]-ethanol to give a yellow solid (48 mg, 31%). LCMS (E/I+) 446.8 (M+H). NMR $^1$H (DMSO-d$_6$)-9.21 (s, 1H), 8.92 (s, 1H), 8.89 (d, 1H, J=2.62 Hz), 8.53 (dd, 1H, JJ=2.62, 8.92 Hz), 7.56 (d, 2H, J=8.92 Hz), 7.14 (d, 1H, J=4.72 Hz), 7.01 (d, 1H, J=8.40 Hz), 6.85-6.95 (m, 3H), 4.42 (t, 1H, J=5.25 Hz), 3.93 (s, 3H), 3.53 (q, 2H, J=11.54, 5.70 Hz), 3.07 (t, 4H, J=4.73 Hz), 2.56 (t, 4H, J=4.72 Hz), 2.43 (t, 2H, J=6.30 Hz). LCMS 446.8 (M+H).

Example 1105

[7-(6-Methoxy-pyridin-3-yl)-pyrrolo[2,1-f][1,2,4]triazin-2-yl]-(4-morpholin-4-yl-phenyl)-amine The titled compound was prepared in an analogous fashion to Example 81 replacing 4-(4-Methyl-piperazin-1-yl)-phenylamine with 4-(4-morpholino)aniline to give a yellow solid (55 mg, 33%). LCMS (E/I+) 403.7 (M+H). NMR $^1$H (DMSO-d$_6$)-9.34 (s, 1H), 8.53 (s, 1H), 8.89 (d, 1H, J=2.57 Hz), 8.53 (dd, 1H, JJ=2.60, 8.44 Hz), 7.64 (d, 2H, J=8.44 Hz), 7.16 (d, 1H, J=5.19 Hz), 6.98-7.09 (m, 3H), 6.94 (d, 1H, J=4.54 Hz), 3.94 (s, 3H), 3.79 (t, 4H, J=4.49 Hz), 3.06-3.22 (m, 4H). LCMS 403.7 (M+H).

Example 1106

7-(6-Methoxy-pyridin-3-yl)-pyrrolo[2,1-f][1,2,4]triazin-2-yl]-(6-morpholin-4-yl-pyridin-3-yl)-amine The titled compound was prepared in an analogous fashion to Example 81 replacing 4-(4-Methyl-piperazin-1-yl)-phenylamine with 6-Morpholin-4-yl-pyridin-3-ylamine to give a yellow solid (41 mg, 31%). MP 197-200° C. LCMS (E/I+) 404.8 (M+H). NMR $^1$H (DMSO-d$_6$)-9.25 (s, 1H), 8.94 (s, 1H), 8.88 (d, 1H, J=2.83 Hz), 8.47 (dd, 1H, JJ=2.83, 8.49 Hz), 8.42 (d, 1H, J=2.83 Hz), 7.93 (dd, 1H, JJ=2.83, 8.49 Hz), 7.15 (d, 1H, J=4.95 Hz), 6.96 (d, 1H, J=8.49 Hz), 6.94 (d, 1H, J=4.95), 6.85 (d, 1H, J=9.20 Hz), 3.72 (t, 4H, J=5.66 Hz), 3.37 (t, 4H, J=4.95). LCMS 404.8 (M+H).

Example 1107

7-(2-Methoxy-phenyl)-5,6-dimethyl-pyrrolo[2,1-f] [1,2,4]triazin-2-yl]-[4-(4-methyl-piperazin-1-yl)-phenyl]-amine The titled compound was prepared in an analogous fashion to Example 112 replacing 4-(4-morpholino)aniline with 4-(4-Methyl-piperazin-1-yl)-phenylamine to give a yellow solid (41 mg, 31%). LCMS (E/I+) 443.90 (M+H). NMR $^1$H (DMSO-$d_6$)-10.65 (s, 1H), 8.36 (s, 1H), ), 7.60 (dt, 1H, JJ=1.70, 7.81 Hz), 7.52 (d, 2H, J=9.17 Hz), 7.43 (dd (1H, JJ=1.70, 7.81 Hz), 7.18 (d, 1H, J=7.47 Hz), 7.13 (d, 1H, J=8.83 Hz), 6.77 (d, 2H, J=9.17 Hz), 3.60-3.75 (m, 2H), 3.40-3.58 (m, 2H), 3.18-0.34 (m, 2H), 2.97-3.13 (m, 2H), 2.89 (s, 3H), 2.38 (s, 3H), 2.17 (s, 3H).

Example 1108

[7-(2-Methoxy-phenyl)-pyrrolo[2,1-f][1,2,4]triazin-2-yl]-[6-(4-methyl-piperazin-1-yl)-pyridin-3-yl]-amine The titled compound was prepared in an analogous fashion to Example 1101 replacing 4-(2-Morpholin-4-yl-ethoxy)-phenylamine with 6-(4-Methyl-piperazin-1-yl)-pyridin-3-ylamine to give a yellow solid (41 mg, 31%). LCMS (E/I+) 416.8 (M+H). NMR $^1$H (DMSO-$d_6$)-9.82 (s, 1H), 9.30 (s, 1H), 8.93 (s, 1H), 8.46 (d, 1H, J=2.66 Hz), 8.02 (dd, 1H, JJ=2.66, 9.17 Hz), 7.77 (dd, 1H, J=1.48, 7.69 Hz), 7.45 (dt, 1H, JJ=1.70, 7.77 Hz), 7.20 (d, 1H, J=8.27 Hz), 7.10 (t, 1H, J=7.20 Hz), 6.82-6.95 (m, 3H), 4.27 (d, 2H, J=9.89 Hz), 3.80 (s, 3H), 3.51 (d, 1H, J=9.89 Hz), 2.94-3.16 (m, 4H), 2.85 (s, 3H).

Example 1109

[7-(6-Methoxy-pyridin-3-yl)-pyrrolo[2,1-f][1,2,4] triazin-2-yl]-[6-(4-methyl-piperazin-1-yl)-pyridin-3-yl]-amine The titled compound was prepared in an analogous fashion to Example 1106 replacing 6-Morpholin-4-yl-pyridin-3-ylamine with 6-(4-Methyl-piperazin-1-yl)-pyridin-3-ylamine to give a yellow solid (85 mg, 31%). LCMS (E/I+) 417.8 (M+H). NMR $^1$H (DMSO-$d_6$)-9.88 (s, 1H), 9.36 (s, 1H), 8.96 (s, 1H), 8.88 (d, 1H, J=2.63 Hz), 8.43-8.53 (m, 2H), 8.01 (dd, 1H, JJ=2.95, 8.86 Hz), 7.17 (d, 1H, J=4.27 Hz), 6.92-7.03 (m, 2H), 4.33 (d, 2H, J=9.84 Hz), 3.93 (s, 3H), 3.46-3.58 (m, 2H), 3.00-3.17 (m, 4H), 2.86 (s, 3H).

Example 1110

[7-(4-Methanesulfonyl-phenyl)-pyrrolo[2,1-f][1,2,4] triazin-2-yl]-[6-(4-methyl-piperazin-1-yl)-pyridin-3-yl]-amine The titled compound was prepared in an analogous fashion to Example 60 replacing 6-Morpholin-4-yl-pyridin-3-ylamine with 6-(4-Methyl-piperazin-1-yl)-pyridin-3-ylamine to give a yellow solid (85 mg, 31%). LCMS (E/I+) 464.8 (M+H). MP 229-232° C. NMR $^1$H (CDCl$_3$-d) 8.74 (s, 1H), 8.33 (d, 2H, J=8.19 Hz), 8.26 (d, 1H, J=2.73 Hz), 8.00 (d, 2H, J=8.19 Hz), 7.92 (dd, 1H, JJ=2.73, 8.73 Hz), 7.08 (d, 1H, J=4.91), 6.85 (, d, 1H, J=4.91 Hz), 6.72 (d, 1H, J=9.28 Hz), 6.67 (bs, 1H), 3.56 9 t, 4H, J=4.91 Hz), 3.10 (s, 3H), 2.57 (t, 4H, J=5.46 Hz), 2.37 (s, 3H). LCMS 464.80 (M+H).

Example 1111

2-{3-[7-(2-Methoxy-phenyl)-pyrrolo[2,1-f][1,2,4] triazin-2-ylamino]-pyrazol-1-yl}-1-morpholin-4-yl-ethanone a. Into a 1-neck round-bottom flask, 3-Nitro-1H-pyrazole (2.00 g, 17.7 mmol), Acetic acid, bromo-, 1,1-dimethylethyl ester (6.90 g, 35.4 mmol), Potassium carbonate (4.89 g, 35.4 mmol), and Acetonitrile (50 mL, 1000 mmol) were added. The reaction was at 55° C. overnight. The reaction was partitioned with water (200 mL). The solid was filtered and washed with water. The solid was dried under vacuum over the weekend to afford a white solid (3.80 g, 94%).

b. Into a 1-neck round-bottom flask, (3-Nitro-pyrazol-1-yl)-acetic acid tert-butyl ester (3.80 g, 16.7 mmol), Trifluoroacetic Acid (10.0 mL, 1.30E2 mmol), and Methylene chloride (40 mL, 600 mmol) were added and stirred at room temperature overnight. The solvent was removed under vacuum. Residual TFA was co-evaporated with DCM to afford a white solid (2.3 g, 80%).

c. (3-Nitro-pyrazol-1-yl)-acetic acid (1.00 g, 5.84 mmol), 1-Hydroxybenzotriazole hydrate (1.05 g, 7.0 mmole), Morpholine (610 mg, 7.0 mmol), N-(3-Dimethylaminopropyl)-N'-ethylcarbodiimide hydrochloride (1300 mg, 7.0 mmol) and N,N-Dimethylformamide (48.5 mL, 626 mmol) were combined in a vial and stirred at room temperature for 1 hour. LCMS showed complete conversion to product. The reaction was partitioned with saturated NaHCO$_3$ and DCM. The organic was separated, washed with water, subsequently with Brine and dried over Na$_2$SO$_4$. The solid was filtered and washed with DCM. The solvent was removed under vacuum to give an off white solid (1.10 g, 78%)

d. Into a round bottom flask, 1-Morpholin-4-yl-2-(3-nitro-pyrazol-1-yl)-ethanone (1.10 g, 0.00458 mol), 10% Pd/C (10: 90, Palladium:carbon black, 0.49 g, 0.00046 mol), and Ethanol (30 mL, 0.5 mol) were added. The mixture was evacuated under house vacuum and charged with a hydrogen balloon (3×). The reaction was stirred at room temperature under an atmosphere of Hydrogen via a balloon. The solid was filtered and washed with methanol. The solvent was removed under vacuum to give a solid.

e. Into a microwave vial, 2-Methanesulfinyl-7-(2-methoxy-phenyl)-pyrrolo[2,1-f][1,2,4]triazine (0.150 g, 0.000522 mol), 2-(3-Amino-pyrazol-1-yl)-1-morpholin-4-yl-ethanone (0.241 g, 0.00115 mol), 1-Methoxy-2-propanol (1.26 mL, 0.0128 mol) and N,N-Diisopropylethylamine (0.200 mL, 0.00115 mol) were added. The reaction was microwaved on 300 watts, 170° C. for 50 minutes. The solvent was removed under vacuum. The desired product was isolated via ISCO column chromatography with DCM and methanol as eluant (0 to 7% methanol). The collected fraction afforded a yellow solid (62 mg, 27%). LCMS (E/I+) 434.8 (M+H). MP 179-182° C. NMR $^1$H (DMSO-$d_6$)-9.54 (s, 1H), 8.90 (s, 1H), 7.82 (dd, 1H, JJ=1.60, 7.70 Hz), 7.40-7.49 (m, 2H), 7.18 (d, 1H, J=8.23 Hz), 7.08 (t, 1H, J=7.64 Hz), 6.92 (d, 1H, J=4.70 Hz), 6.88 (, d, 1H, J=4.70 Hz), 6.43 (d, 1H, J=1.76 Hz), 3.78 (s, 3H), 3.52-3.62 (m, 4H), 3.39-3.52 (m, 4H), 3.30 (s, 3H).

Example 1112

2-{3-[7-(6-Methoxy-pyridin-3-yl)-pyrrolo[2,1-f][1,2, 4]triazin-2-ylamino]-pyrazol-1-yl}-1-morpholin-4-yl-ethanone The titled compound was prepared in an analogous fashion to Example 1111a replacing 2-Methanesulfinyl-7-(2-methoxy-phenyl)-pyrrolo[2,1-f][1,2,4]triazine with 2-Methanesulfinyl-7-(6-methoxy-pyridin-3-yl)-pyrrolo[2,1-f][1,2,4]triazine to give a yellow solid (31 mg, 60%). LCMS (E/I+) 435.8 (M+H). NMR $^1$H (DMSO-d$_6$)-9.64 (s, 1H), 9.02 (d, 1H, J=2.54), 8.94 (s, 1H), 8.59 (dd, 1H, JJ=2.72, 8.88), 7.58 (d, 1H, J=2.36), 7.18 (d, 1H, J=4.71), 6.96 (d, 1H, J=8.88 Hz), 6.93 (d, 1H, J=4.89 Hz), 6.46 (d, 1H, J=2.17 Hz), 5.04 (s, 2H), 3.93 (s, 3H), 3.40-3.65 (m, 8H).

Example 1113

2-{4-[7-(2-Methoxy-phenyl)-pyrrolo[2,1-f][1,2,4]triazin-2-ylamino]-imidazol-1-yl}-1-morpholin-4-yl-ethanone The titled compound was prepared in an analogous fashion to Example 1111 replacing 3-Nitro-1H-pyrazole with 4-nitro-1H-imidazole to give a yellow solid (3.1 mg, 6%). MP 259-261° C. LCMS (E/I+) 434.8 (M+H). NMR $^1$H (DMSO-d$_6$)-(CDCl$_3$)-8.74 (s, 1H), 7.98 (dd, 1H, JJ=1.55, 7.55 Hz), 7.76 (s, 1H), 7.38 (dt, 1H, JJ=1.75, 7.75 Hz), 7.29 (d, 1H, J=1.55 Hz), 7.11 (d, 1H, J=1.55v), 7.03-7.09 (m, 1H), 7.00 (d, 1H, J=4.65 Hz), 6.83 (d, 1H, J=4.65 Hz), 4.62 (s, 2H), 3.84 (s, 3H), 3.54-3.73 (m, 6H), 3.32-3.43 (m, 2H).

Example 1114

2-{3-[7-(2-Methoxy-phenyl)-pyrrolo[2,1-f][1,2,4]triazin-2-ylamino]-pyrazol-1-yl}-1-(4-methyl-piperazin-1-yl)-ethanone The titled compound was prepared in an analogous fashion to Example 1111 replacing morpholine with N-methylpiperazine to give a yellow solid (15 mg, 25%). LCMS (E/I+) 447.8 (M+H). NMR $^1$H (DMSO-d$_6$)-8.76 (s, 1H), 7.94 (d, 1H, J=1.52, 7.62), 7.49 (s, 1H), 7.37-7.44 (m, 1H), 7.33 (d, 1H, J=2.22 Hz), 7.09 (t, 1H, J=7.62 Hz), 7.04 (d, 1H, J=8.32v), 7.01 (d, 1H, J=4.88v), 4.86 (s, 2H), 3.83 (s, 3H), 3.64 (t, 2H, J=4.88 Hz), 3.53 (t, 2H, J=4.88 Hz), 2.32-2.43 (m, 4H), 2.28 (s, 3H).

Example 1115

2-{3-[7-(6-Methoxy-pyridin-3-yl)-pyrrolo[2,1-f][1,2,4]triazin-2-ylamino]-pyrazol-1-yl}-1-(4-methyl-piperazin-1-yl)-ethanone The titled compound was prepared in an analogous fashion to Example 1112 replacing morpholine with N-methylpiperazine to give a yellow solid (15 mg, 25%). MP 206-207° C. LCMS (E/I+) 448.8 (M+H). NMR $^1$H (DMSO-d$_6$)-8.78 (d, 1H, J=2.48), 8.73 (s, 1H), 8.39 (dd, 1H, JJ=2.48, 8.87), 7.48 (bs, 1H), 7.43 (d, 1H, J=2.13 Hz), 6.91 (d, 1H, J=4.97 Hz), 6.87 (d, 1H, J=8.52 Hz), 6.83 (d, 1H, J=4.97 Hz), 6.74 (d, 1H, J=2.48v), 4.90 (s, 2H), 4.01 (s, 3H), 3.66 (t, 2H, J=5.32 Hz), 3.55 (t, 2H, J=5.32v), 2.34-2.43 (m, 4H), 2.29 (s, 3H).

Example 1116

(4-Morpholin-4-yl-phenyl)-[7-(pyridin-4-ylsulfanyl)-pyrrolo[2,1-f][1,2,4]triazin-2-yl]-amine Into a sealed tube, (7-Bromo-pyrrolo[2,1-f][1,2,4]triazin-2-yl)-(4-morpholin-4-yl-phenyl)-amine (0.174 g, 0.465 mmol), Sodium tert-butoxide (134 mg, 1.40 mmol), Copper (I) iodide (8.8 mg, 0.046 mmol), 1,2-Ethanediol (52.1 uL, 0.934 mmol), N,N-Dimethylformamide (6.5 mL, 84 mmol), and Pyridine-4-thiol (0.207 g, 1.86 mmol) were added. The reaction was heated at 135° C. for 2 days. The solvent was removed under vacuum. The reaction was partitioned with water and DCM. The organic was separated, washed with Brine and dried over Na$_2$SO$_4$. The solid was filtered and washed with DCM. The solvent was removed under vacuum to give a yellow solid. The reaction mixture was purified via HPLC reverse phase chromatography with 0.1% TFA in Water and 0.1% TFA in ACN as eluant (5 to 35% ACN). The collected fractions were lyophilized to give a yellow solid. (33 mg, 14%). LCMS (E/I+) 405.7 (M+H). NMR $^1$H (DMSO-d$_6$)-9.25 (s, 1H), 9.10 (s, 1H), 8.56 (bs, 1H), 7.40 (d, 2H, J=6.68 Hz), 7.33 (d, 2H, J=8.91 Hz), 7.19 (d, 1H, J=4.45 Hz), 7.04 (d, 1H, J=4.45 Hz), 6.70 (d, 2H, J=9.65 Hz), 3.74 (t, 4H, J=5.08 Hz), 302 (t, 4H, J=5.08 Hz).

Example 1117

[4-(4-Methyl-piperazin-1-yl)-phenyl]-[7-(pyridin-4-ylsulfanyl)-pyrrolo[2,1-f][1,2,4]triazin-2-yl]-amine The titled compound was prepared in an analogous fashion to Example 1116 replacing (7-Bromo-pyrrolo[2,1-f][1,2,4]triazin-2-yl)-(4-morpholin-4-yl-phenyl)-amine with (7-Bromo-pyrrolo[2,1-f][1,2,4]triazin-2-yl)-[4-(4-methyl-piperazin-1-yl)-phenyl]-amine to give a yellow solid (45 mg, 15%). LCMS (E/I+) 418.7 (M+H). NMR $^1$H (DMSO-d$_6$)-8.83 (s, 1H), 8.51 (d, 2H, J=6.58 Hz), 7.23-7.28 (m, 2H), 7.20 d, 2H, J=8.98 Hz), 7.09 (d, 1H, J=4.84 Hz), 6.85-6.95 (m, 2H), 6.74 d, 2H, J=8.64 Hz), 3.60-3.72 (m, 2H), 3.45-3.58 (bm, 2H), 3.24-3.41 (bm, 2H), 3.04-3.19 (m, 2H), 2.89 (s, 3H).

Example 1118

[7-(6-Amino-pyridin-3-yl)-pyrrolo[2,1-f][1,2,4]triazin-2-yl]-[4-(4-methyl-piperazin-1-yl)-phenyl]-amine The titled compound was prepared in an analogous fashion to Example 7 replacing phenyl boronic acid with 5-(4,4,5,5-Tetramethyl-1,3,2-dioxaborolan-2-yl)-pyridin-2-ylamine to give a yellow solid (55 mg, 38%). LCMS (E/I+) 401.7 (M+H). NMR $^1$H (DMSO-d$_6$)-9.37 (s, 1H), 8.97 (s, 1H), 8.79 (d, 1H, J=9.06 Hz), 8.49 (d, 1H, J=9.06 Hz), 8.67 (d, 2H, J=9.06 Hz), 7.16 (d, 1H, J=4.80 Hz), 7.02 (d, 2H, J=9.06 Hz), 6.95 (d, 1H, J=4.53 Hz), 3.72-3.80 (m, 2H), 3.44-3.58 (m, 2H), 3.10-3.25 (bm, 2H), 2.83-2.97 (m, 5H).

Example 1119

[7-(4-Methanesulfonyl-phenyl)-pyrrolo[2,1-f][1,2,4]triazin-2-yl]-[4-(1-methyl-piperidin-4-yl)-phenyl]-amine The titled compound was prepared in an analogous fashion to Example 59 replacing 4-(4-Methyl-piperazin-1-yl)-phenylamine with 4-(1-Methyl-piperidin-4-yl)-phenylamine to give a yellow solid (25 mg, 22%). LCMS (E/I+) 462.8 (M+H). NMR $^1$H (DMSO-d$_6$)-9.60 (s, 1H), 9.06 (s, 1H), 8.49 (d, 2H, J=8.53 Hz), 8.05 (d, 2H, J=8.53 Hz), 7.72 (d, 2H, J=8.53 Hz), 7.36 (d, 1H, J=4.94 Hz), 7.22 (d, 2H, J=8.53 Hz), 7.01 (d, 1H, J=4.94 Hz), 3.46-3.58 (m, 2H), 3.30 (s, 3H), 3.00-3.15 (m, 2H), 2.70-2.85 (m, 4H), 1.97-2.09 (m, 2H), 1.74-1.93 (m, 2H).

Example 1120

[7-(3-Methanesulfonyl-phenyl)-pyrrolo[2,1-f][1,2,4]
triazin-2-yl]-[4-(1-methyl-piperidin-4-yl)-phenyl]-
amine The titled compound was prepared in an analogous fashion to Example 1119 replacing 2-Methanesulfinyl-7-(4-methanesulfonyl-phenyl)-pyrrolo[2,1-f][1,2,4]triazine with 2-Methanesulfinyl-7-(3-methanesulfonyl-phenyl)-pyrrolo[2,1-f][1,2,4]triazine to give a yellow solid (35 mg, 17%). LCMS (E/I+) 462.8 (M+H). NMR $^1$H (DMSO-$d_6$)-9.55 (s, 1H), 9.43 (bs, 1H), 9.05 (s, 1H), 8.68 (bs, 1H), 8.43 (d, 1H, J=8.36 Hz), 7.95 (d, 1H, J=7.84 Hz), 7.81 (t, 1H, J=8.10 Hz), 7.70 (d, 2H, J=8.62 Hz), 7.29 (d, 1H, J=4.97 Hz), 7.21 (d, 2H, J=8.62 Hz), 7.00 (d, 1H, J=4.97 Hz), 3.40-3.60 (bm, 2H), 3.2-(s, 3H), 3.03-3.14 (m, 2H), 2.65-2.85 (m, 4H), 1.94-2.04 (m, 2H), 1.73-1.88 (m, 2H).

Example 1121

[7-(5-Chloro-2-methoxy-phenyl)-pyrrolo[2,1-f][1,2,4]triazin-2-yl]-[4-(1-methyl-piperidin-4-yl)-phenyl]-
amine The titled compound was prepared in an analogous fashion to Example 1119 replacing 2-Methanesulfinyl-7-(4-methanesulfonyl-phenyl)-pyrrolo[2,1-f][1,2,4]triazine with 7-(5-Chloro-2-methoxy-phenyl)-2-methanesulfinyl-pyrrolo[2,14][1,2,4]triazine to give a yellow solid (45 mg, 21%). LCMS (E/I+) 448.7 (M+H). NMR $^1$H (DMSO-$d_6$)-9.48 (s, 1H), 8.99 (s, 1H0, 8.10 (d, 1H, J=2.68 Hz), 7.69 (d, 2H, J=8.71 Hz), 7.48 (dd, 1H, JJ=3.35 Hz, 9.38 Hz), 7.26 (d, 1H, J=9.38 Hz), 7.14 (d, 2H, J=8.71 Hz), 7.07 (d, 1H, J=4.71 Hz), 6.93 (d, 1H, J=4.69 Hz), 3.83 (s, 3H), 3.38-3.60 (m, 2H), 3.00-3.14 (m, 2H, 2.66-2.85 (m, 4H), 1.92-2.03 (m, 2H), 1.71-1.88 (m, 2H).

Example 1122

N-(3-{2-[6-(4-Methyl-piperazin-1-yl)-pyridin-3-ylamino]-pyrrolo[2,1-f][1,2,4]triazin-7-yl}-phenyl)-methanesulfonamide The titled compound was prepared in an analogous fashion to Example 7 replacing phenylboronic acid with 3-Methylsulfonylaminophenyl boronic acid to give a yellow solid (45 mg, 33%). LCMS (E/I+) 479.8 (M+H). NMR $^1$H (DMSO-$d_6$)-9.80 (s, 1H), 9.24 (s, 1H), 8.96 (s, 1H), 8.44 (d, 1H, J=2.63 Hz), 7.99 (dd, 1H, JJ=3.06, 9.19 Hz), 7.83 (s, 1H), 7.85 (d, 1H, J=7.88 Hz), 7.47 (t, 1H, J=7.88 Hz), 7.26 (d, 1H, J=8.32 Hz), 7.05 (d, 1H, J=4.81 Hz), 6.94 (d, 1H, J=4.81 Hz), 6.87 (d, 1H, J=9.23 Hz), 3.35-3.42 (bm, 4H), 3.33 (s, 3H), 2.37-2.46 (m, 4H), 2.22 (s, 3H).

Example 1123

[7-(3-Methanesulfonyl-phenyl)-pyrrolo[2,1-f][1,2,4]triazin-2-yl]-[6-(4-methyl-piperazin-1-yl)-pyridin-3-yl]-amine The titled compound was prepared in an analogous fashion to Example 7 replacing phenylboronic acid with 3-(Methanesulfonyl) phenyl boronic acid to give a yellow solid (48 mg, 36%). LCMS (E/I+) 464.8 (M+H). NMR $^1$H (DMSO-$d_6$)-9.93 (s, 1H), 9.01 (s, 1H), 8.58 (bs, 1H), 8.46 (d, 1H, J=2.46 Hz), 8.41 (d, 1H, J=8.01 Hz), 7.89-7.96 (m, 2H), 7.78 (t, 1H, J=8.01 Hz), 7.24 (d, 1H, J=4.93 Hz), 6.97 (d, 1H, J=4.93 Hz), 6.87 (d, 1H, J=9.23 Hz), 3.35-3.42 (bm, 4H), 3.33 (s, 3H), 2.37-2.46 (m, 4H), 2.22 (s, 3H).

Example 1124

[7-(3-Methanesulfonyl-phenyl)-pyrrolo[2,1-f][1,2,4]triazin-2-yl]-[6-(4-methyl-piperazin-1-ylmethyl)-pyridin-2-yl]-amine 1124a. Into a 1-neck round-bottom flask, 6-Amino-pyridine-2-carbaldehyde (2.85 g, 23.3 mmol), 1-Methylpiperazine (5.00 mL, 45.1 mmol), 1,2-Dichloroethane (100 mL, 1000 mmol) and Acetic acid (2.50 mL, 44.0 mmol) were added and stirred at room temperature for 2 hours. Sodium triacetoxyborohydride (14.8 g, 70.0 mmol) was added portion wise over 20 minutes. The reaction mixture was stirred at room temperature over night. The reaction was partitioned with Sat. NaHCO$_3$. The organic was separated, washed with Brine and dried over Na$_2$SO$_4$. The solid was filtered and stripped to give a yellow solid. The reaction mixture was purified via ISCO column chromatography with DCM and methanol as eluant (0 to 20% methano). The collected fractions afforded 6-(4-Methyl-piperazin-1-ylmethyl)-pyridin-2-ylamine as a yellow solid (1.20, 25%)

1124b. Into a microwave vial, 6-(4-Methyl-piperazin-1-ylmethyl)-pyridin-2-ylamine (0.149 g, 0.722 mmol), 2-Methanesulfinyl-7-(3-methanesulfonyl-phenyl)-pyrrolo[2,1-f][1,2,4]triazine (0.110 g, 0.328 mmol), N,N-Diisopropylethylamine (0.126 mL, 0.722 mmol), and 1-Methoxy-2-propanol (0.5 mL, 5 mmol) were added. The reaction was microwaved on 300 watts, 180° C. for 4 hours. The reaction mixture was purified via HPLC reverse phase chromatography with 0.1% TFA in Water and 0.1% TFA in ACN. The collected fractions were lyophilized to give [7-(3-Methanesulfonyl-phenyl)-pyrrolo[2,1-f][1,2,4]triazin-2-yl]-[6-(4-methyl-piperazin-1-ylmethyl)-pyridin-2-yl]-amine a yellow solid (20 mg, 10%). LCMS (E/I+) 478.8 (M+H). NMR $^1$H (DMSO-$d_6$)-9.16 (s, 1H), 8.81 (d, 1H, J=7.82), 8.78 (s, 1H), 8.46 (dd, 1H, JJ=1.89, 5.36 Hz), 7.83-7.95 (m, 2H), 7.78 (t, 1H, J=7.57 Hz), 7.58 (d, 1H, J=5.05 Hz), 7.19 (dd, 1H, JJ=5.05, 6.94 Hz), 7.15 (d, 1H, J=5.05 Hz), 3.80 (s, 2H), 3.40-3.51 (m, 2H), 2.93-3.11 (m, 4H), 2.81 (s, 3H), 2.34-2.60 (m, 5H).

Example 1125

(S)-3-(4-{4-[7-(2-Methoxy-phenyl)-pyrrolo[2,1-f][1,2,4]triazin-2-ylamino]-phenyl}-piperidin-1-yl)-propane-1,2-diol The titled compound was prepared in an analogous fashion to Example 1101 replacing 4-(2-Morpholin-4-yl-ethoxy)-phenylamine with (S)-3-[4-(4-Amino-phenyl)-piperidin-1-yl]-propane-1,2-diol to give a yellow solid (48 mg, 36%). LCMS (E/I+) 474.9 (M+H). NMR $^1$H (DMSO-$d_6$)-9.39 (s, 1H), 9.12 (bs, 1H), 8.95 (s, 1H), 7.82 (dd, 1H, JJ=1.60, 7.64), 7.65 (d, 2H, J=8.74 Hz), 7.46 (dt, 1H, JJ=1.64, 8.74 Hz), 7.21 (d, 2H, J=8.74 Hz), 7.08-7.16 (m, 1H), 7.06 (d, 2H, J=8.74 Hz), 6.95 (d, 1H, J=4.91 Hz), 6.92 (d, 1H, J=4.91 Hz), 3.89-3.99 (m, 1H), 3.80 (s, 3H), 3.29-3.50 (m, 3H), 2.95-3.26 (m, 6H), 2.67-2.79 (m, 1H), 1.77-2.09 (m, 4H).

Example 1126

[7-(4-Methanesulfonyl-phenyl)-pyrrolo[2,1-f][1,2,4]triazin-2-yl]-[2-methoxy-4-(4-methyl-piperazin-1-yl)-phenyl]-amine The titled compound was prepared in an analogous fashion to Example 23 replacing 4-(4-Methyl-piperazin-1-yl)-phenylamine with 4-(1-Methyl-piperidin-4-yl)-phenylamine to give a yellow solid (8 mg, 5%). LCMS (E/I+) 519.9 (M+H). NMR $^1$H (DMSO-d$_6$)-9.45 (s, 1H), 9.02 (s, 1H), 8.54 (s, 1H), 8.37 (d, 1H, J=8.49), 7.86 (d, 1H, J=8.49 Hz), 7.74 (t, 1H, J=8.49 Hz), 7.67 (d, 2H, J=707 Hz), 7.60 (s, 1H), 7.21 (d, 2H, J=8.45 Hz), 7.19 (d, 1H, J=4.83 Hz), 6.98 (d, 1H, J=4.83 Hz), 3.29 (bs, 2H), 2.81-2.89 (m, 2H), 2.65-2.99 (m, 1H), 2.18 (s, 3H), 1.89-1.98 (m, 2H), 1.63-1.67 (m, 2H), 1.17 (s, 9H).

Example 1127

N-tert-Butyl-3-{2-[6-(4-methyl-piperazin-1-yl)-pyridin-3-ylamino]-pyrrolo[2,1-f][1,2,4]triazin-7-yl}-benzenesulfonamide The titled compound was prepared in an analogous fashion to Example 23 replacing 4-(4-Methyl-piperazin-1-yl)-phenylamine with 6-(4-Methyl-piperazin-1-yl)-pyridin-3-ylamine to give a yellow solid (115 mg, 66%). LCMS (E/I+) 521.9 (M+H). NMR $^1$H (DMSO-d$_6$)-9.34 (s, 1H), 9.00 (s, 1H), 8.66 (s, 1H), 8.50 (d, 1H, J=2.86), 8.35 (d, 1H, J=8.59), 7.98 (dd, 1H, JJ=2.86, 9.54 Hz), 7.24 (d, 1H, J=4.77 Hz), 6.98 (d, 1H, J=4.77 Hz), 6.92 (d, 1H, J=9.54 Hz), 3.42 (t, 4H, J=4.77 Hz), 2.42 (t, 4H, J=4.77 Hz), 2.22 (s, 3H), 1.17 (s, 9H).

Example 1128

4-[2-(4-Morpholin-4-yl-phenylamino)-pyrrolo[2,1-f][1,2,4]triazin-7-yl]-piperidine-1-carboxylic acid tert-butyl ester Into a 30 mL vial, Palladium Acetate (35 mg, 0.16 mmol) and Triphenylphosphine (100 mg, 0.4 mmol) were added and purged under an atmosphere of Nitrogen for 10 minutes. 1,4-Dioxane (5.9 mL) was added and stirred for 10 minutes. (7-Bromo-pyrrolo[2,1-f][1,2,4]triazin-2-yl)-(4-morpholin-4-yl-phenyl)-amine (0.250 g, 0.668 mmol), 4-(4,4,5,5-Tetramethyl-[1,3,2]dioxaborolan-2-yl)-3,6-dihydro-2H-pyridine-1-carboxylic acid tert-butyl ester (0.413 g, 1.34 mmol), N,N-Dimethylformamide (5.9 mL) and 1.50 M of Sodium carbonate in Water (2.47 mL, 3.70 mmol) were added and heated at 85° C. for 8 hours. The reaction was partitioned with DCM. The solid was filtered and washed with DCM. The organic solvent was removed under vacuum. The desired product was isolated via ISCO column chromatography with DCM and methanol as eluant (0 to 10% methanol). The collected fractions afforded 4-[2-(4-Morpholin-4-yl-phenylamino)-pyrrolo[2,1-f][1,2,4]triazin-7-yl]-piperidine-1-carboxylic acid tert-butyl ester as a yellow solid (180, 56%). LCMS (E/I+) 477.8 (M+H). NMR $^1$H (DMSO-d$_6$)-9.15 (s, 1H), 8.88 (s, 1H), 7.57 (d, 2H, J=8.75 Hz), 7.10 (bs, 1H), 6.91 (d, 2H, J=8.75 Hz), 6.82 (d, 1H, J=4.66 Hz), 6.79 (d, 1H, J=4.66 Hz), 4.12 (bs, 2H), 3.74 (t, 4H, J=4.66 Hz), 3.58 (t, 2H, J=5.25 Hz), 3.06 (t, 4H, J=5.25 Hz), 2.58 (bs, 2H), 1.44 (s, 9H).

Example 1129

[7-(1-Methanesulfonyl-1,2,3,6-tetrahydro-pyridin-4-yl)-pyrrolo[2,1-f][1,2,4]triazin-2-yl]-(4-morpholin-4-yl-phenyl)-amine 1129a. Into a 8 dram vial, [2-(4-Morpholin-4-yl-phenylamino)-pyrrolo[2,1-f][1,2,4]triazin-7-yl]-piperidine-1-carboxylic acid tert-butyl ester (0.150 g, 0.315 mmol), Methylene chloride (5 mL) and Trifluoroacetic Acid (1 g, 9 mmol) were added and stirred at room temperature over night. The reaction was partitioned with Sat. NaHCO$_3$ and DCM. The organic was separated, washed with Brine and dried over Na$_2$SO$_4$. The solid was filtered and washed with DCM. The solvent was removed under vacuum. The desired product was purified via ISCO column chromatography with DCM and methanol as eluant (0 to 10% methanol). The collected fractions afforded (4-Morpholin-4-yl-phenyl)-[7-(1,2,3,6-tetrahydro-pyridin-4-yl)-pyrrolo[2,1-f][1,2,4]triazin-2-yl]-amine as a yellow solid.

1129b. Into a 8-dram vial, (4-Morpholin-4-yl-phenyl)-[7-(1,2,3,6-tetrahydro-pyridin-4-yl)-pyrrolo[2,1-f][1,2,4]triazin-2-yl]-amine (0.080 g, 0.21 mmol), Acetonitrile (15 mL, 290 mmol), Potassium carbonate (0.0587 g, 0.425 mmol) were added and stirred for 5 minutes. Methanesulfonyl chloride (0.0256 g, 0.223 mmol) was added. The reaction was stirred at room temperature over night. The solvent was removed under vacuum. The reaction was partitioned with water and DCM. The organic was separated, washed with Brine and dried over Na$_2$SO$_4$. The solid was filtered and washed with DCM. The solvent was removed under vacuum. The reaction mixture was purified via ISCO column chromatography with DCM and methanol as eluant (0 to 10% methanol). The collected fractions afforded [7-(1-Methanesulfonyl-1,2,3,6-tetrahydro-pyridin-4-yl)-pyrrolo[2,1-f][1,2,4]triazin-2-yl]-(4-morpholin-4-yl-phenyl)-amine as a yellow solid (35 mg, 36%). LCMS (E/I+) 455.10 (M+H). MP 238-240° C. NMR $^1$H (DMSO-d$_6$)-9.18 (s, 1H), 8.90 (s, 1H), 7.56 (d, 2H, J=8.88 Hz), 7.19 (bs, 1H), 6.94 (d, 2H, J=8.88 Hz), 6.83 (d, 1H, J=4.72 Hz), 6.81 (d, 1H, J=4.72 Hz), 4.00 (bs, 2H), 3.75 (t, 4H, J=5.26 Hz), 3.42 (t, 2H, J=5.96 Hz), 3.05 (t, 4H, J=5.26 Hz), 2.97 (s, 3H), 2.72 (bs, 2H).

Example 1130

(S)-3-(4-{4-[7-(3-Chloro-phenyl)-pyrrolo[2,1-f][1,2,4]triazin-2-ylamino]-phenyl}-piperidin-1-yl)-propane-1,2-diol The titled compound was prepared in an analogous fashion to Example 1125 replacing 2-Methanesulfinyl-7-(2-methoxy-phenyl)-pyrrolo[2,1-f][1,2,4]triazine with 7-(3-Chloro-phenyl)-2-methanesulfinyl-pyrrolo[2,1-f][1,2,4]triazine to give a yellow solid (12 mg, 6%). LCMS (E/I+) 478.10 (M+H). NMR $^1$H (DMSO-d$_6$)-9.56 (s, 1H), 9.17 (bs, 1H), 9.02 (s, 1H), 8.53 (s, 1H), 8.00 (d, 1H, J=7.38 Hz), 7.73 (d, 2H, J=7.38 Hz), 7.54 (t, 1H, J=7.38 Hz), 7.45 (d, 1H, J=7.387 Hz), 7.28 (d, 1H, J=5.90 Hz), 7.22 (d, 2H, J=7.38 Hz), 6.97 (d, 1H, J=5.90 Hz), 3.95 (bs, 1H), 3.25-3.70 (bm, 5H), 2.94-3.24 (m, 4H), 2.68-2.84 (m, 1H), 1.71-2.11 (m, 4H).

Example 1131

[7-(3-Chloro-phenyl)-pyrrolo[2,1-f][1,2,4]triazin-2-yl]-[4-(1-methyl-piperidin-4-yl)-phenyl]-amine The titled compound was prepared in an analogous fashion to Example 49 replacing 4-Piperidin-1-yl-phenylamine with 4-(1-Methyl-piperidin-4-yl)-phenylamine to give a yellow solid (25 mg, 11%). LCMS (E/I+) 418.1 (M+H). NMR $^1$H (DMSO-d$_6$)-9.60 (s, 1H), 9.39 (bs, 1H), 9.02 (s, 1H), 8.53 (t, 1H, J=1.99), 8.01 (td, 1H, JJ=1.34, 8.31 Hz), 7.77 (d, 2H, J=8.59 Hz), 7.54 (t, 1H, J=8.02 Hz), 7.42-7.47 (m, 1H), 7.29 (d, 1H, J=4.58 Hz), 7.22 (d, 2H, J=8.78 Hz), 6.97 (d, 1H, J=4.96 Hz), 3.47-3.57 (m, 2H), 2.96-3.12 (m, 2H), 2.68-2.84 (m, 4H), 1.74-2.06 (m, 4H).

Example 1132

[7-(2-Methoxy-phenyl)-pyrrolo[2,1-f][1,2,4]triazin-2-yl]-[4-(1-methyl-piperidin-4-yl)-phenyl]-amine The titled compound was prepared in an analogous fashion to Example 1101 replacing 4-(2-Morpholin-4-yl-ethoxy)-phenylamine with 4-(1-Methyl-piperidin-4-yl)-phenylamine to give a yellow solid (38 mg, 17%). LCMS (E/I+) 414.2 (M+H). NMR $^1$H (DMSO-$d_6$)-9.39 (s, 1H), 8.95 (s, 1H), 7.82 (dd, 1H, JJ=1.95, 7.89 Hz), 7.66 (d, 2H, J=8.59 Hz), 7.46 (dt, 1H, JJ=1.95, 8.59 Hz), 7.21 (d, 1H, J=8.59 Hz), 7.09-7.15 (m, 1H), 7.06 (d, 2H, J=8.59 Hz), 6.95 (d, 1H, J=4.69 Hz), 6.92 (d, 1H, J=4.69 Hz), 3.80 (s, 3H), 3.50 (d, 2H, J=11.75), 3.04 (q, 2H, J=11.75), 2.62-285 (m, 4H), 1.98 (d, 2H, J=13.22), 1.70-1.86 (m, 2H).

Example 1133

(1-{4-[7-(3-Chloro-phenyl)-pyrrolo[2,1-f][1,2,4]triazin-2-ylamino]-phenyl}-piperidin-4-yl)-methanol The titled compound was prepared in an analogous fashion to Example 49 replacing 4-Piperidin-1-yl-phenylamine with 1-(4-Amino-phenyl)-piperidin-4-yl]-methanol to give a yellow solid (38 mg, 16%). LCMS (E/I+) 434.1 (M+H). NMR $^1$H (DMSO-$d_6$)-9.78 (s, 1H), 9.05 (s, 1H), 8.45 (t, 1H, J=1.95 Hz), 8.04 (d, 1H, J=7.80 Hz), 7.84 (bs, 2H), 7.57 (t, 2H, J=7.80 Hz), 7.47 (d, 2H, J=7.80 Hz), 7.31 (d, 1H, J=4.46 Hz), 7.00 (d, 1H, J=4.46 Hz), 3.60 (d, 2H, J=11.15 Hz), 3.35 (d, 2H, J=5.57 Hz), 1.49-2.06 (m, 2.05).

Example 1134

2-(4-{4-[7-(3-Chloro-phenyl)-pyrrolo[2,1-f][1,2,4]triazin-2-ylamino]-phenyl}-piperazin-1-yl)-ethanol The titled compound was prepared in an analogous fashion to Example 49 replacing 4-Piperidin-1-yl-phenylamine with 2-[4-(4-Amino-phenyl)-piperazin-1-yl]-ethanol to give a yellow solid (31 mg, 13%). LCMS (E/I+) 449.1 (M+H). NMR $^1$H (DMSO-$d_6$)-9.53 (bs, 1H), 9.38 (s, 1H), 8.98 (s, 1H), 8.49 (t, 1H, J=1.49 Hz), 8.07 (d, 1H, J=8.44 Hz), 7.67 (d, 2H, J=8.94 Hz), 7.54 (t, 1H, J=7.94 Hz), 7.40-746 (m, 1H), 7.27 (d, 1H, J=4.96 Hz), 7.01 (d, 2H, J=8.94 Hz), 6.94 (d, 1H, J=4.96 Hz), 3.68-3.81 (m, 4H), 3.57-3.64 (m, 2H), 3.16-3.22 (m, 4H), 2.96-3.09 (m, 2H), 2.52-2.57 (m, 1H).

Example 1135

4-{2-[4-(4-Methyl-piperazin-1-yl)-phenylamino]-pyrrolo[2,1-f][1,2,4]triazin-7-yl}-3,6-dihydro-2H-pyridine-1-carboxylic acid tert-butyl ester The titled compound was prepared in an analogous fashion to Example 1128 replacing (7-Bromo-pyrrolo[2,1-f][1,2,4]triazin-2-yl)-(4-morpholin-4-yl-phenyl)-amine with (7-Bromo-pyrrolo[2,1-f][1,2,4]triazin-2-yl)-[4-(4-methyl-piperazin-1-yl)-phenyl]-amine to give a yellow solid (522 mg, 63%). NMR $^1$H (DMSO-$d_6$)-9.13 (s, 1H), 8.87 (s, 1H), 7.54 (d, 2H, J=8.74 Hz), 7.09 (bs, 1H), 6.91 (d, 2H, J=8.94 Hz), 6.81 (d, 1H, J=4.69 Hz), 6.78 (d, 1H, J=4.09 Hz), 4.12 (bs, 2H), 3.58 (t, 2H, J=5.87 Hz), 3.08 (bs, 4H), 2.53-2.63 (m, 3H), 2.25 (s, 3H), 1.44 (s, 9H).

Example 1136

[4-(4-Diethylamino-piperidin-1-yl)-phenyl]-[7-(4-methanesulfonyl-phenyl)-pyrrolo[2,1-f][1,2,4]triazin-2-yl]-amine The titled compound was prepared in an analogous fashion to Example 59 replacing 4-(4-Methyl-piperazin-1-yl)-phenylamine with [1-(4-Amino-phenyl)-piperidin-4-yl]-diethylamine to give a yellow solid (42 mg, 32%). LCMS (E/I+) 471.2 (M+H). NMR $^1$H (DMSO-$d_6$)-9.30 (s, 1H), 9.00 (s, 1H), 8.50 (d, 2H, J=8.69 Hz), 8.02 (d, 2H, J=8.69 Hz), 7.51 (d, 2H, J=8.69 Hz), 7.32 (d, 1H, J=4.74 Hz), 6.91-7.00 (m, 3H), 3.67 (d, 2H, J=11.06 Hz), 3.28 (s, 3H), 2.30-2.70 (m, 9H), 1.77 (d, 2H, J=11.06 Hz), 1.47-1.62 (m, 2H), 0.97 (t, 6H, J=6.32 Hz).

Example 1137

[4-(4-Diethylamino-piperidin-1-yl)-phenyl]-[7-(3-methanesulfonyl-phenyl)-pyrrolo[2,1-f][1,2,4]triazin-2-yl]-amine The titled compound was prepared in an analogous fashion to Example 85 replacing 4-Piperidin-1-yl-phenylamine with [1-(4-Amino-phenyl)-piperidin-4-yl]-diethyl-amine to give a yellow solid (46 mg, 35%). LCMS (E/I+) 519.2 (M+H). MP 193-195° C. NMR $^1$H (DMSO-$d_6$)-9.28 (s, 1H), 8.99 (s, 1H), 8.60 (s, 1H), 8.47 (d, 1H, J=8.19 Hz), 7.94 (d, 1H, J=8.19 Hz), 7.81 (t, 1H, J=7.71 Hz), 7.57 (d, 2H, J=9.15 Hz), 7.25 (d, H, J=4.82 Hz), 6.89-6.98 (m, 3H), 3.63 (d, 2H, J=11.02 Hz), 3.28 (s, 3H), 2.38-2.70 (m, 9H), 1.68-1.83 (m, 2H), 1.43-1.62 (m, 2H), 0.97 (t, 6H, J=7.06 Hz).

Example 1138

[4-(4-Diethylamino-piperidin-1-yl)-phenyl]-[7-(2-methoxy-phenyl)-pyrrolo[2,1-f][1,2,4]triazin-2-yl]-amine The titled compound was prepared in an analogous fashion to Example 1101 replacing 4-(2-Morpholin-4-yl-ethoxy)-phenylamine with [1-(4-Amino-phenyl)-piperidin-4-yl]-diethyl-amine to give a yellow solid (28 mg, 23%). LCMS (E/I+) 471.2 (M+H). MP 135-137° C. NMR $^1$H (DMSO-$d_6$)-9.11 (s, 1H), 8.89 (s, 1H), 7.87 (d, 1H, J=7.60 Hz), 7.55 (d, 2H, J=8.34 Hz), 7.45 (t, 1H, J=7.89 Hz), 7.22 (d, 1H, J=8.34 Hz), 7.11 (t, 1H, J=7.30 Hz), 6.90 (d, 1H, J=4.77 Hz), 6.88 (d, 1H, J=4.77 Hz), 6.80 (d, 2H, J=8.19 Hz), 3.79 (s, 3H), 3.59 (d, 2H, J=12.08 Hz), 2.40-2.70 (m, 7H), 1.75 (d, 2H, J=12.00 Hz), 1.35 (q, 2H, J=12.16 Hz), 0.98 (t, 6H, J=6.87 Hz).

Example 1139

[7-(1-Methane sulfonyl-1,2,3,6-tetrahydro-pyridin-4-yl)-pyrrolo[2,1-f][1,2,4]triazin-2-yl]-[4-(4-methyl-piperazin-1-yl)-phenyl]-amine The titled compound was prepared in an analogous fashion to Example 1129 replacing (7-Bromo-pyrrolo[2,1-f][1,2,4]triazin-2-yl)-(4-morpholin-4-yl-phenyl)-amine with (7-Bromo-pyrrolo[2,1-f][1,2,4]triazin-2-yl-[4-(4-Methyl-piperazin-1-yl)-phenyl]-amine to give a yellow solid (42 mg, 45%). LCMS (E/I+) 468.2 (M+H). MP 246-249° C. NMR $^1$H (DMSO-d$_6$)-9.16 (s, 1H), 8.89 (s, 1H), 7.54 (d, 2H, J=8.09 Hz), 7.19 (bs, 1H), 6.93 (d, 2H, J=8.16 Hz), 6.82 (s, 2H), 3.99 (bs, 2H), 3.42 (t, 2H, J=5.44 Hz), 3.07 (bs, 4H), 2.97 (s, 3H), 2.68-2.76 (bm, 2H), 2.38-2.49 (m, 4H), 2.23 (s, 3H).

Example 1140

(7-Benzyl-pyrrolo[2,1-f][1,2,4]triazin-2-yl)-[4-(4-methyl-piperazin-1-yl)-phenyl]-amine 1140a. Benzyl zinc bromide was purchase in 0.5 M solution in THF from aldrich. Into a 30 mL vial [1,1'-Bis(diphenylphosphino)ferrocene]dichloropalladium(II) (0.20 g, 0.28 mmol), 7-Bromo-2-methylsulfanyl-pyrrolo[2,1-f][1,2,4]triazine (0.68 g, 2.8 mmol), Copper(I) iodide (0.053 g, 0.28 mmol) were added. The mixture was purged under an atmosphere of Nitrogen for 10 minutes. Tetrahydrofuran (10 mL and Benzylzinc bromide (2.63 g, 11.1 mmol) were added. The reaction was heated at 78° C. overnight. The solvent was removed under vacuum. The desired product was isolated via ISCO column chromatography using an amine column with hexan and EtOAc as eluant (0 to 10% EtoAc). The collected fractions afforded a semi solid. The solid was dissolved in Methylene chloride (10 ml). m-Chloroperbenzoic acid (0.144 g, 0.836 mmol) was added and stirred at RT for 1 hour. The reaction was partitioned with Saturated NaHCO$_3$ and DCM. The organic was separated, washed with Brine and dried over Na$_2$SO$_4$. The solid was filtered and washed with DCM. The solvent was removed under vacuum. The desired product was purified via ISCO column chromatography with Hexane and EtOAc (2 0 to 100% EtOAc). The collected fractions afforded 7-Benzyl-2-methanesulfinyl-pyrrolo[2,1-f][1,2,4]triazine as a yellow solid (127 mg, 16%).

1140b. Into a microwave vial, 7-Benzyl-2-methanesulfinyl-pyrrolo[2,1-f][1,2,4]triazine (0.120 g, 0.442 mmol), 4-(4-Methyl-piperazin-1-yl)-phenylamine (0.186 g, 0.973 mmol), N,N-Diisopropylethylamine (0.169 mL, 0.973 mmol), and 1-Methoxy-2-propanol (0.50 mL, 5.1 mmol) were added. The reaction was microwaved on 300 watts, 180° C. for 2 hours. The solvent was removed under vacuum. The reaction mixture was purified via HPLC reverse phase chromatography with 0.1% TFA in Water and 0.1% TFA in ACN. The collected fractions were lyophilized to give a yellow solid (74 mg, 42%). LCMS (E/I+) 399.3 (M+H). NMR $^1$H (DMSO-d$_6$)-9.74 (bs, 1H), 9.21 (s, 1H), 8.83 (s, 1H), 7.64 (d, 2H, J=8.09 Hz), 7.27-7.34 (m, 4H), 7.20 (bs, 1H), 6.96 (d, 2H, J=8.09 Hz), 6.78 (d, 1H, J=4.85 Hz), 6.60 (d, 1H, J=4.85 Hz), 4.27 (s, 2H), 3.74 (d, 2H, J=12.94 Hz), 3.52 (d, 2H, J=12.14 Hz), 3.09-3.24 (m, 2H), 2.77-2.97 (m, 5H).

Example 1141

(2-{2-[4-(4-Methyl-piperazin-1-yl)-phenylamino]-pyrrolo[2,1-f][1,2,4]triazin-7-yl}-phenoxy)-acetonitrile 1141a. Into a 50 mL flask, (2-Bromo-phenoxy)-acetonitrile (1.00 g, 4.72 mmol), 4,4,5,5,4',4',5',5'-Octamethyl-[2,2'] bi[[1,3,2]dioxaborolanyl] (1.80 g, 7.07 mmol), Bis(tricyclohexylphosphine)palladium (0) (160 mg, 0.24 mmol) and Potassium acetate (0.694 g, 7.07 mmol) were added. The mixture was purged under an atmosphere of Nitrogen for 10 minutes. 1,4-Dioxane (10 mL) was added and heated at 100° C. overnight. The solid was filtered through Celite. The solvent was removed under vacuum to give 2-(4,4,5,5-Tetramethyl-[1,3,2]dioxaborolan-2-yl)-phenoxy]-acetonitrile as an oil. The product was used as is with out any further purification.

1141b. Into a 30 mL vial, Palladium Acetate (10 mg, 0.04 mmol), Triphenylphosphine (33 mg, 0.12 mmol) were added. The mixture was purged with nitrogen for 10 minutes. (7-Bromo-pyrrolo[2,1-f][1,2,4]triazin-2-yl)-[4-(4-methyl-piperazin-1-yl)-phenyl]-amine (110.0 mg, 0.2840 mmol), [2-(4,4,5,5-Tetramethyl-[1,3,2]dioxaborolan-2-yl)-phenoxy]-acetonitrile (0.1472 g, 0.5681 mmol), N,N-Dimethylformamide (2.00 mL) and 1.50 M of Sodium carbonate in Water (2.0 mL, 3.0 mmol) were added. The reaction mixture was heated at 55° C. for 45 minutes. The reaction was partitioned with water and DCM. The organic was separated, washed with Brine and dried over Na$_2$SO$_4$. The solid was filtered and washed with DCM. The solvent was removed under vacuum. The desired product was isolated via ISCO column chromatography with DCM and methanol as eluant (0 to 15% methanol). The collected fractions afforded (2-{2-[4-(4-Methyl-piperazin-1-yl)-phenylamino]-pyrrolo[2,1-f][1,2,4]triazin-7-yl}-phenoxy)-acetonitrile as a yellow solid (65 mg, 52%). LCMS (E/I+) 440.2 (M+H). MP 95-101° C. NMR $^1$H (DMSO-d$_6$)-9.16 (s, 1H), 8.92 (s, 1H), 7.88-7.98 (m, 1H), 7.48-7.58 (m, 3H), 7.34 (d, 1H, J=9.43), 7.26 (t, 1H, J=8.64 Hz), 6.94 (d, 1H, J=5.50), 6.90 (d, 1H, J=4.70 Hz), 6.81 (d, 2H, J=9.43 Hz), 5.19 (s, 2H), 3.03 (bs 3H), 2.45 (bs, 3H), 2.22 (s, 3H).

Example 1142

3-(3-{2-[4-(4-Methyl-piperazin-1-yl)-phenylamino]-pyrrolo[2,1-f][1,2,4]triazin-7-yl}-phenyl)-propionitrile 1142a. Into a 50 ml, flask, 3-(3-Bromo-phenyl)-propionitrile (2.00 g, 9.52 mmol), 4,4,5,5,4',4',5',5'-Octamethyl-[2,2'] bi[[1,3,2]dioxaborolanyl] (3.63 g, 14.3 mmol), Bis(tricyclohexylphosphine)palladium (0) (320 mg, 0.48 mmol) and Potassium acetate (1.40 g, 14.3 mmol) were added. The mixture was purged under an atmosphere of Nitrogen for 10 minutes. 1,4-Dioxane (30 mL) was added and heated at 100° C. overnight. The solid was filtered through Celite. The solvent was removed under vacuum to give 3-[3-(4,4,5,5-Tetramethyl-[1,3,2]dioxaborolan-2-yl)-phenyl]-propionitrile as an oil. The product was used as is without further purification.

1142b. The titled compound was prepared in an analogous fashion to Example 1141 replacing 2-(4,4,5,5-Tetramethyl-[1,3,2]dioxaborolan-2-yl)-phenoxy)-acetonitrile with 3-[3-(4,4,5,5-Tetramethyl-[1,3,2]dioxaborolan-2-yl)-phenyl]-propionitrile to give a yellow solid (68 mg, 55%). LCMS (E/I+) 438.2 (M+H). MP 167-169° C. NMR $^1$H (DMSO-d$_6$)-9.22 (s, 1H), 8.93 (s, 1H), 8.16 (s, 1H), 8.04 (d, 1H, J=8.30), 7.62 (d, 2H, J=8.30 Hz), 7.49 (t, 1H, J=7.55), 7.32 (d, 1H=7.55 Hz), 7.163 (d, 1H, J=4.53 Hz), 6.86-6.95 (m, 3H), 3.09 (bs, 4H), 2.99 (t, 2H, J=6.79 Hz), 2.87 (t, 2H, J=6.79 Hz), 2.46 (bs, 4H), 2.22 (s, 3H).

Example 1143

3-{2-[4-(4-Methyl-piperazin-1-yl)-phenylamino]-pyrrolo[2,1-f][1,2,4]triazin-7-yl}-benzoic acid tert-butyl ester The titled compound was prepared in an analogous fashion to Example 7 replacing phenylboronic acid with 3-(tert-Butoxycarbonyl)phenyl boronic acid to give a yellow solid (145 mg, 64%). LCMS (E/I+) 485.2 (M+H). MP 105-108° C.

NMR $^1$H (DMSO-d$_6$)-9.29 (s, 1H), 8.97 (s, 1H), 8.76 (s, 1H), 8.25 (d, 1H, J=7.99 Hz), 7.93 (d, 1H, J=7.38 Hz), 7.59-7.70 (m, 3H), 7.16 (d, 1H, J=4.30 Hz), 6.94 (d, 1H, J=4.30 Hz), 6.87 (d, 2H, J=8.61 Hz), 3.03 (bs, 4H), 2.44 (bs, 4H), 2.21 (s, 3H).

Example 1144

{2-[2-(4-Morpholin-4-yl-phenylamino)-pyrrolo[2,1-f][1,2,4]triazin-7-yl]-phenoxy}-acetonitrile The titled compound was prepared in an analogous fashion to Example 1141 replacing (7-Bromo-pyrrolo[2,1-f][1,2,4]triazin-2-yl)-4-[(4-Methyl-piperazin-1-yl)-phenyl]-amine amine with (7-Bromo-pyrrolo[2,1-f][1,2,4]triazin-2-yl)-(4-morpholin-4-yl-phenyl)-amine to give a yellow solid (72 mg, 57%). LCMS (E/I+) 427.2 (M+H). MP 184-186° C. NMR $^1$H (DMSO-d$_6$)-9.19 (s, 1H), 8.93 (s, 1H), 7.92 (d, 1H, J=7.96 Hz), 7.56 (d, 2H, J=8.96 Hz), 7.51 (d, 1H, J=7.96 Hz Hz), 7.36 (d, 1H, J=8.96 Hz), 7.27 (t, 1H, J=7.96 Hz), 6.94 (d, 1H, J=4.98 Hz), 6.91 (d., 1H, J=4.98 Hz), 6.83 (d, 2H, J=7.96 Hz), 5.20 (s, 2H), 3.73 (bs, 4H), 3.01 (bs, 4H).

Example 1145

3-{3-[2-(4-Morpholin-4-yl-phenylamino)-pyrrolo[2,1-f][1,2,4]triazin-7-yl]-phenyl}-propionitrile The titled compound was prepared in an analogous fashion to Example 1142 replacing (7-Bromo-pyrrolo[2,1-f][1,2,4]triazin-2-yl)-4-[(4-Methyl-piperazin-1-yl)-phenyl]-amine amine with (7-Bromo-pyrrolo[2,1-f][1,2,4]triazin-2-yl)-(4-morpholin-4-yl-phenyl)-amine to give a yellow solid (68 mg, 54%). LCMS (E/I+) 425.2 (M+H). MP 176-180° C. NMR $^1$H (DMSO-d$_6$)-9.24 (s, 1H), 8.94 (s, 1H), 8.17 (s, 1H), 8.05 (d, 1H, J=8.26 Hz), 7.64 (d, 2H, J=8.26 Hz), 7.49 (t, 1H, J=7.71 Hz), 7.32 (d, 1H, J=7.71 Hz), 7.17 (d, 1H, J=4.96 Hz), 6.88-6.99 (m, 3H), 3.75 (bs, 4H), 3.06 (bs, 4H), 2.99 (t, 2H, J=6.88 Hz), 2.88 (t, 2H, J=6.88 Hz).

Example 1146

2-{2-[4-(4-Methyl-piperazin-1-yl)-phenylamino]-pyrrolo[2,1-f][1,2,4]triazin-7-yl}-benzoic acid ethyl ester The titled compound was prepared in an analogous fashion to Example 7 replacing phenylboronic acid with 2-(Ethoxycarbonyl)phenyl boronic acid to give a yellow solid (280 mg, 82%). LCMS (E/I+) 457.2 (M+H). MP 171-173° C. $^1$H (DMSO-d$_6$)-9.08 (s, 1H), 8.92 (s, 1H), 8.02 (d, 1H, J=7.29 Hz), 7.73 (t, 1H, J=7.29 Hz), 7.61 (t, 2H, J=7.29 Hz), 7.43 (d, 2H, J=8.44 Hz), 6.90 (d, 1H, J=4.96 Hz), 6.83 (d, 1H, J=4.96 Hz), 6.73 (d, 2H, J=8.44 Hz), 3.85 (q, 2H, J=6.91 Hz), 3.00 (bs, 4H), 2.43 (bs, 4H), 2.21 (s, 3H), 0.77 (t, 3H, J=6.91 Hz).

Example 1147

3-{2-[4-(4-Methyl-piperazin-1-yl)-phenylamino]-pyrrolo[2,1-f][1,2,4]triazin-7-yl}-N-prop-2-ynyl-benzamide 1147a. Into a 8-dram vial, 2-{2-[4-(4-Methyl-piperazin-1-yl)-phenylamino]-pyrrolo[2,1-f][1,2,4]triazin-7-yl}-benzoic acid ethyl ester (0.250 g, 0.548 mmol), Lithium hydroxide (0.0262 g, 1.10 mmol), Methanol (15 mg), and Water (3.0 mL) were added. The reaction mixture was stirred at room temperature overnight. The solvent was removed under vacuum. The solid was acidified with 1N HCl. The reaction was partitioned DCM. The organic was separated, washed with Brine and dried over Na$_2$SO$_4$. The solid was filtered and washed with DCM. The solvent was removed under vacuum to give 2-{2-[4-(4-Methyl-piperazin-1-yl)-phenylamino]-pyrrolo[2,1-f][1,2,4]triazin-7-yl}-benzoic acid as a solid (180 mg, 76%). The solid was used as is without further purification.

1147b. Into a 8-dram vial, Prop-2-ynylamine (0.0643 g, 0.00117 mol) was dissolved in N,N-Dimethylformamide (1.75 mL), and 1-Hydroxybenzotriazole hydrate (0.0429 g, 0.000280 mol), N-(3-Dimethylaminopropyl)-N'-ethylcarbodiimide hydrochloride (53.7 mg, 0.280 mmol) were added. After stirring for 5 min, 3-{2-[4-(4-Methyl-piperazin-1-yl)-phenylamino]-pyrrolo[2,1-f][1,2,4]triazin-7-yl}-benzoic acid (100 mg, 0.233 mmol) was added followed by 4-Methylmorpholine (0.0308 mL, 0.280 mmol). The reaction was stirred at rt for 1 hour. The reaction mixture was diluted with NaHCO$_3$ and the resulting ppt was filtered, washed with NaHCO$_3$ and water. The solid was dried under vacuum to give 3-{2-[4-(4-Methyl-piperazin-1-yl)-phenylamino]-pyrrolo[2,1-f][1,2,4]triazin-7-yl}-N-prop-2-ynyl-benzamide as a yellow solid (37 mg, 34%). LCMS (E/I+) 466.19 (M+H). MP 185-187° C. NMR $^1$H (DMSO-d$_6$)-9.25 (s, 1H), 9.03 (t, 1H, J=4.84 Hz), 8.96 (s, 1H), 8.57 (s, 1H), 8.39 (d, 1H, J=8.02 Hz), 7.84 (d, 1H, J=8.02 Hz), 7.65 (d, 1H, J=8.02 Hz), 7.62 (d, 2H, J=8.32 Hz), 7.20 (d, 1H, J=4.75 Hz), 6.95 (d, 1H, J=4.75 Hz), 6.89 (d, 2H, J=8.00 Hz), 4.11 (s, 2H), 3.14 (s, 1H), 3.06 (bs, 4H), 2.46 (bs, 4H), 2.22 (s, 3H).

Example 1148

3-{3-[2-(7-Morpholin-4-yl-6,7,8,9-tetrahydro-5H-benzocyclohepten-2-ylamino)-pyrrolo[2,1-f][1,2,4]triazin-7-yl]-phenyl}-propionitrile 1148a. Into a 8-dram vial, Palladium Acetate (0.057 g, 0.26 mmol) and Triphenylphosphine (0.19 g, 0.00072 mol) were added. The mixture was purged under an atmosphere of Nitrogen for 10 minutes. 1,4-Dioxane (19.4 mL) was added and stirred for 10 minutes at room temperature. 7-Bromo-2-methylsulfanyl-pyrrolo[2,1-f][1,2,4]triazine (0.623 g, 2.55 mmol), 3-[3-(4,4,5,5-Tetramethyl-[1,3,2]dioxaborolan-2-yl)-phenyl]-propionitrile (1.31 g, 5.10 mmol), N,N-Dimethylformamide (39 mL), and 1.50 M of Sodium carbonate in Water (15.3 mL, 0.0230 mol) were added. The reaction was heated at 90° C. for 3 hours. The reaction was partitioned with water and EtOAc. The organic was separated, washed with Brine, and dried over magnesium sulfate. The solid was filtered and washed with EtOAc. The solvent was removed under vacuum. The product was isolated via column chromatography with DCM and Methanol as eluant (1 to 8% MeOH). The collected fractions afforded a solid. The solid was triturated with Et$_2$O and filtered to give 3-[3-(2-Methylsulfanyl-pyrrolo[2,1-f][1,2,4]triazin-7-yl)-phenyl]-propionitrile as a yellow solid (560 mg, 64%).

1148b Into a round bottom flask, 3-[3-(2-Methylsulfanyl-pyrrolo[2,1-f][1,2,4]triazin-7-yl)-phenyl]-propionitrile and Methylene chloride (50 mL) were added. m-Chloroperbenzoic acid (0.366 g, 0.00212 mol) was added portion wise over 20 minutes. The reaction was stirred at room temperature for one hour. The reaction was partitioned with DCM (200 mL) and saturated NaHCO$_3$ (200 mL). The organic was separated, washed with Brine and dried over Na$_2$SO$_4$. The solid was filtered and washed with DCM. The solvent was removed under vacuum to give a yellow solid. The reaction mixture was purified via ISCO column chromatography with DCM and methanol as eluant (0 to 10% methanol). The collected fractions afforded 3-[3-(2-Methanesulfinyl-pyrrolo[2,1-f][1,2,4]triazin-7-yl)-phenyl]-propionitrile as a yellow solid (540 mg, 98%).

1148c. Into a microwave vial, 3-[3-(2-Methanesulfinyl-pyrrolo[2,1-f][1,2,4]triazin-7-yl)-phenyl]-propionitrile (0.0964 g, 0.310 mmol), 7-Morpholin-4-yl-6,7,8,9-tetrahydro-5H-benzocyclohepten-2-ylamine (0.168 g, 0.683 mmol), 1-Methoxy-2-propanol (0.747 mL) and N,N-Diisopropylethylamine (0.119 mL) were added. The reaction was microwaved on 300 watts, 170° C. for 50 minutes. The solvent was removed under vacuum. The desired product was isolated via ISCO column chromatography with DCM and methanol as eluant (0 to 10% methanol). The collected fractions afforded 3-{3-[2-(7-Morpholin-4-yl-6,7,8,9-tetrahydro-5H-benzocyclohepten-2-ylamino)-pyrrolo[2,1-f][1,2,4]triazin-7-yl]-phenyl}-propionitrile as a yellow solid (35 mg, 23%). LCMS (E/I+) 493.20 (M+H). MP 184-186° C. NMR $^1$H (DMSO-$d_6$)-9.34 (s, 1H), 8.97 (s, 1H), 8.18 (d, 1H, J=8.44 Hz), 8.02 (s, 1H), 7.56 (s, 1H), 7.97 (d, 2H, J=7.23 Hz), 7.35 (d, 1H, J=7.23 Hz), 7.18 (d, 1H, J=4.51 Hz), 7.05 (d, 1H, J=7.89), 6.95 (d, 1H, J=4.51 Hz), 3.54 (bs, 4H), 2.98 (t, 2H, J=7.32 Hz), 2.87 (t, 2H, J=7.04 Hz), 2.53-2.81 (m, 5H), 2.43-2.48 (m, 4H), 1.89-2.07 (m, 2H), 1.22-1.43 (m, 2H).

Example 1149

3-(3-{2-[4-(1-Methyl-piperidin-4-yl)-phenylamino]-pyrrolo[2,1-f][1,2,4]triazin-7-yl}-phenyl)-propionitrile; compound with trifluoro-acetic acid The titled compound was prepared in an analogous fashion to Example 1148 replacing Morpholin-4-yl-6,7,8,9-tetrahydro-5H-benzocyclohepten-2-ylamine with 4-(1-Methyl-piperidin-4-yl)-phenylamine to give a yellow solid (32 mg, 19%). LCMS (E/I+) 437.12 (M+H). NMR $^1$H (DMSO-$d_6$)-9.49 (s, 1H), 9.42 (bs, 1H), 8.99 (s, 1H), 8.17 (s, 1H), 8.07 (d, 1H, J=7.80 Hz), 7.74 (d, 2H, J=7.80 Hz), 7.51 (t, 1H, J=7.39 Hz), 7.35 (d, 1H, J=7.39 Hz), 7.12-7.23 (m, 3H), 6.97 (d, 1H, J=4.51 Hz), 3.52 (d, 2H, J=11.49 Hz), 2.70-3.13 (m, 10H), 2.03 (d, 2H, J=14.52 Hz), 1.82 (q, 2H, J=13.92 Hz).

Example 1150

3-(3-{2-[4-(4-Morpholin-4-yl-piperidin-1-yl)-phenylamino]-pyrrolo[2,1-f][1,2,4]triazin-7-yl}-phenyl)-propionitrile The titled compound was prepared in an analogous fashion to Example 1148 replacing Morpholin-4-yl-6,7,8,9-tetrahydro-5H-benzocyclohepten-2-ylamine with 4-(4-Morpholin-4-yl-piperidin-1-yl)-phenylamine to give a yellow solid (44 mg, 23%). LCMS (E/I+) 508.19 (M+H). NMR $^1$H (DMSO-$d_6$)-9.78 (s, 1H), 9.29 (s, 1H), 8.95 (s, 1H), 8.16 (s, 1H), 8.07 (d, 1H, J=8.11 Hz), 7.62 (d, 2H, J=8.11 Hz), 7.50 (t, 1H, J=8.11 Hz), 7.33 (d, 1H, J=7.10 Hz), 7.18 (d, 1H, J=4.06 Hz), 7.01 (d, 2H, J=8.11 Hz), 6.94 (d, 1H, J=4.06 Hz), 4.02 (d, 2H, J=11.16 Hz), 3.82 9 d, 2H, J=12.17 Hz), 3.67 (t, 2H, J=12.17 Hz), 3.51 (d, 2H, J=12.17 Hz), 3.36 (t, 1H, J=11.16 Hz), 3.12 (bs, 2H), 2.99 (t, 2H, J=7.10 Hz), 2.88 (t, 2H, J=7.10 Hz), 2.72 (t, 2H, J=12.17 Hz), 2.17 (d, 2H, J=11.16 Hz), 1.76 (q, 2H, J=11.16 Hz).

Example 1151

3-[3-(2-{4-[4-(2-Hydroxy-ethyl)-piperazin-1-yl]-phenylamino}-pyrrolo[2,1-f][1,2,4]triazin-7-yl)-phenyl]-propionitrile The titled compound was prepared in an analogous fashion to Example 1148 replacing Morpholin-4-yl-6,7,8,9-tetrahydro-5H-benzocyclohepten-2-ylamine with 2-[4-(4-Aminophenyl)-piperazin-1-yl]-ethanol to give a yellow solid (58 mg, 32%). LCMS (E/I+) 468.18 (M+H). NMR $^1$H (DMSO-$d_6$)-9.62 (bs, 1H), 9.31 (s, 1H), 8.96 (s, 1H), 8.16 (s, 1H), 8.08 (d, 1H, J=7.63 Hz), 7.69 (d, 2H, J=8.33 Hz), 7.50 (t, 1H, J=7.63 Hz), 7.34 (d, 1H, J=7.63 Hz), 7.18 (d, 1H, J=4.16 Hz), 7.00 (d, 2H, J=3.83 Hz), 6.95 (d, 1H, J=4.86 Hz), 3.68-3.84 (m, 4H), 3.60 (d, 2H, J=11.22 Hz), 3.14-3.35 (m, 4H), 2.93-3.12 (m, 4H), 2.89 (t, 2H, J=7.17 Hz).

Example 1152

3-(3-{2-[3-(2-Methoxy-ethyl)-2,3,4,5-tetrahydro-1H-benzo[d]azepin-7-ylamino]-pyrrolo[2,1-f][1,2,4]triazin-7-yl}-phenyl)-propionitrile The titled compound was prepared in an analogous fashion to Example 1148 replacing Morpholin-4-yl-6,7,8,9-tetrahydro-5H-benzocyclohepten-2-ylamine with 3-(2-Methoxy-ethyl)-2,3,4,5-tetrahydro-1H-benzo[d]azepin-7-ylamine to give a yellow solid (8 mg, 4%). LCMS (E/I+) 467.25 (M+H). NMR $^1$H (DMSO-$d_6$)-8.69 (s, 1H), 8.09 (d, 1H, J=7.75 Hz), 7.99 (s, 1H), 7.40-7.52 (m, 2H), 7.37 (s, 1H), 7.20-7.30 (m, 1H), 7.03-7.07 (m, 2H), 7.01 (d, 1H, J=3.87 Hz), 6.84 (d, 1H, J=3.87 Hz), 3.58 (t, 2H, J=4.84 Hz), 3.36 (s, 3H), 3.05 (t, 2H, J=7.26 Hz), 2.88-3.00 (m, 4H), 2.72-2.88 (m, 6H), 2.66 (t, 2H, J=7.26 Hz).

Example 1153

3-(3-{2-[3-(4-Methyl-piperazin-1-yl)-phenylamino]-pyrrolo[2,1-f][1,2,4]triazin-7-yl}-phenyl)-propionitrile The titled compound was prepared in an analogous fashion to Example 1148 replacing Morpholin-4-yl-6,7,8,9-tetrahydro-5H-benzocyclohepten-2-ylamine with 3-(4-Methylpiperazin-1-yl)aniline to give a yellow solid (72 mg, 42%). LCMS (E/I+) 438.23 (M+H). NMR $^1$H (DMSO-$d_6$)-9.70 (bs, 1H), 9.35 (s, 1H), 9.00 (s, 1H), 8.03-8.11 (m, 2H), 7.48 (t, 1H, J=7.09 Hz), 7.42 (d, 1H, J=7.09 Hz), 7.35 (d, 1H, J=7.09 Hz), 7.26 (s, 1H), 7.23 (d, 1H, J=7.87 Hz), 7.19 (d, 1H, J=4.72 Hz), 6.89 (d, 1H, J=4.72 Hz), 6.66 (d, 1H, J=7.87 Hz), 3.68 (d, 2H, J=7.28 Hz), 3.46 (d, 2H, J=7.28 Hz), 3.04-3.21 (m, 2H), 2.79-3.00 (m, 9H). 3-(3-{2-[3-(2-Methoxy-ethyl)-2,3,4,5-tetrahydro-1H-benzo[d]azepin-7-ylamino]-pyrrolo[2,1-f][1,2,4]triazin-7-yl}-phenyl)-propionitrile.

Example 1154

2-{2-[4-(4-Methyl-piperazin-1-yl)-phenylamino]-pyrrolo[2,1-f][1,2,4]triazin-7-yl}-phenol 1154a. Into a 8-dram vial, Palladium Acetate (0.050 g, 0.022 mol) and Triphenylphosphine (0.16 g, 0.063 mmol) were added. The mixture was purged under an atmosphere of Nitrogen for 10 minutes. 1,4-Dioxane (17.1 mL,) was added and stirred for 10 minutes at room temperature. 7-Bromo-2-methylsulfanyl-pyrrolo[2,1-f][1,2,4]triazine (0.550 g, 2.25 mmol), Acetic acid 2-(4,4,5,5-tetramethyl-[1,3,2]dioxaborolan-2-yl)-phenyl ester (1.18 g, 4.51 mmol), N,N-Dimethylformamide (34 mL), and 1.50 M of Sodium carbonate in Water (13.5 mL, 0.0203 mol) were added. The reaction was heated at 90° C. for 18 hours. The reaction was partitioned with water and stirred at room temperature for 2 hours. The solid was filtered and washed with water. The resulting yellow solid was dried under vacuum to give 2-(2-Methylsulfa-nyl-pyrrolo[2,1-f][1,2,4]triazin-7-yl)-phenol (0.53 g, 92%).

1153b. Into a 8-dram vial, 2-(2-Methylsulfanyl-pyrrolo[2,1-f][1,2,4]triazin-7-yl)-phenol (0.530 g, 2.06 mmol) and Methylene chloride (15 mL, 230 mmol) were added. m-CPBA 70-75% (70:30, m-Chloroperbenzoic acid:3-Chlorobenzoic acid, 0.533 g, 2.16 mmol) was added over 10 minutes. The reaction was stirred at room temperature for 1 hour. The reaction was partitioned with DCM and sat. NaHCO$_3$. The organic was separated, washed with Brine, and dried over Na$_2$SO$_4$. The solid was filtered and washed with DCM. The solvent was removed under vacuum to give 2-(2-Methanesulfinyl-pyrrolo[2,1-f][1,2,4]triazin-7-yl)-phenol as a yellow solid (0.485 g, 86%).

1154c. Into a microwave vial, 2-(2-Methanesulfinyl-pyrrolo[2,1-f][1,2,4]triazin-7-yl)-phenol (0.165 g, 0.604 mmol), 4-(4-Methyl-piperazin-1-yl)-phenylamine (0.254 g, 1.33 mmol), 1-Methoxy-2-propanol (1.20 mL) and N,N-Diisopropylethylamine (0.231 mL, 1.33 mmol) were added. The reaction was microwaved on 300 watts, 180° C. for 2 hours. The solvent was removed under vacuum. The reaction mixture was purified via ISCO column chromatography with DCM and methanol as eluant (0 to 10% methanol). The collected fractions afforded 2-{2-[4-(4-Methyl-piperazin-1-yl)-phenylamino]-pyrrolo[2,1-f][1,2,4]triazin-7-yl}-phenol as a yellow solid (125 mg, 51%). LCMS (E/I+) 401.10 (M+H). NMR $^1$H (DMSO-d$_6$)-9.73 (s, 1H), 9.13 (s, 1H), 8.88 (s, 1H), 7.92 (d, 1H, J=7.74 Hz), 7.61 (d, 2H, J=8.23 Hz), 7.25 (t, 1H, J=7.26 Hz), 6.93-7.08 (m, 3H), 6.88 (d, 1H, J=4.35 Hz), 6.81 (d, 2H, J=8.23 Hz), 3.03 (bs, 4H), 2.44 (bs, 3H), 2.21 (s, 3H).

Example 1155

(2-{2-[4-(4-Methyl-piperazin-1-yl)-phenylamino]-pyrrolo[2,1-f][1,2,4]triazin-6-yl}-phenoxy)-acetonitrile 1155a. Chloramine was made according to J. Org. Chem., Vol 69 (4), 1368-1371. Into 4 L Erlenmyer flask, 4-Bromo-1H-pyrrole-2-carboxylic acid methyl ester (30.0 g, 0.147 mol) and Tetrahydrofuran (800 mL, 9 mol) were added and stirred at RT for 20 minutes under an atmosphere of Nitrogen. 1.00 M of Potassium tert-Butoxide in Tetrahydrofuran (379 mL, 0.379 mol) was added and stirred for 30 minutes at room temperature. 0.15 M of Chloramine in Ether (1570 mL) was added to the reaction mixture at 10° C. over 20 minutes with nitrogen bubbling into the reaction mixture. The reaction was stirred at room temperature for 2 hours. HPLC suggested 72% conversion (18% SM remained). Saturated Na$_2$S$_2$O$_3$ (500 mL) was added at 10° C. over 30 minutes. The mixture was stirred for one hour. The organic was separated, washed with water, then subsequently with Brine, and dried over Na2SO4. The solid was filtered and washed with DCM. The solvent was concentrated to approximately 500 mL. Benzoyl isothiocyanate (17.26 g, 0.1058 mol) in Tetrahydrofuran (80 mL) was added dropwise to the residual organic. The reaction mixture was stirred at room temperature overnight. The solvent was removed under vacuum. The solid was partitioned with Et$_2$O (200 mL) and stirred for 30 minutes. The solid was filtered and washed with hexane/Et$_2$O (9 to 1) to give 1-(3-Benzoyl-thioureido)-4-bromo-1H-pyrrole-2-carboxylic acid methyl ester an off white solid (31.20, 55%).

1155b. Into a 500 mL beaker, 1-(3-Benzoyl-thioureido)-4-bromo-1H-pyrrole-2-carboxylic acid methyl ester (31.20 g, 0.08162 mol) and 2.00 M of Sodium hydroxide in Water (164 mL, 0.327 mol) were added. The mixture was heated at 85° C. for 75 minutes. The reaction was cooled to RT. The solid was dissolved with Ethanol (100 mL). Acetic acid (18.8 mL, 0.332 mol) was added at 0° C. and stirred for 30 minutes. The solid was filtered and washed with cold EtOH (50 mL) to afford a white solid. The white solid was stirred in Et$_2$O (300 mL) for 20 minutes. The solid was filtered and washed with Et$_2$O (200 mL) to give 6-Bromo-2-thioxo-2,3-dihydro-1H-pyrrolo[2,1-f][1,2,4]triazin-4-one as a white solid. The white solid was dried under vacuum over night (11.6, 57%).

1155c. Into a round bottom flask, 6-Bromo-2-thioxo-2,3-dihydro-1H-pyrrolo[2,1-f][1,2,4]triazin-4-one (11.20 g, 0.04551 mol), Tetrahydrofuran (200 mL) and Methyl iodide (6.517 mL, 0.1047 mol) were added, respectively. The reaction was stirred at 45° C. for one hour. The solid was filtered. The solvent was removed under vacuum to give a solid. The combined solid was partitioned with water (500 mL) and saturated NaHCO$_3$ (500 mL). The mixture was stirred for 30 minutes. The solid was filtered and washed with water to give 6-Bromo-2-methylsulfanyl-3H-pyrrolo[2,1-f][1,2,4]triazin-4-one as a white solid (5.80, 49%).

1155d. Into a round bottom flask, 6-Bromo-2-methylsulfanyl-3H-pyrrolo[2,1-f][1,2,4]triazin-4-one (5.80 g, 0.0223 mol) and Phosphoryl chloride (25 mL, 0.27 mol) were added and heated at 120° C. for 2 hours. The solvent was removed under vacuum to give a solid. Ice water was added and stirred for 5 minutes. NH$_4$OH (25 mL) in ice water was added and stirred at room temperature for 1 hour. The solid was filtered and washed with generous amount of water. The resulting solid was dried under vacuum over the weekend HPLC suggested >90%. 6-Bromo-4-chloro-2-methylsulfanyl-pyrrolo[2,1-f][1,2,4]triazine was used as is without any further purification (6.00 g, 95%).

1155e. Into a round bottom flask, 6-Bromo-4-chloro-2-methylsulfanyl-pyrrolo[2,1-f][1,2,4]triazine (6.00 g, 21.5 mmoles) was suspended in Isopropyl alcohol (69 mL) at 55° C. Sodium borohydride (1.71 g, 0.0452 mol) was added and heated at 60° C. for 3 hours. The reaction was allowed to cool to RT. The solid was filtered and washed with DCM. The solvent was removed under vacuum to a viscous oil. Methylene chloride (100 mL, 2 mol) was added to the viscous oil. Dichlorodicyanoquinone (5.38 g, 0.0237 mol) was then added portion wise over 15 minutes. The mixture was stirred for 30 minutes. The solid was filtered through Celite and washed with DCM. The solvent was removed under vacuum. The reaction was purified via ISCO column chromatography with hexane and EtOAca as eluant (0 to 8% EtOAC). The collected fractions afforded 6-Bromo-2-methylsulfanyl-pyrrolo[2,1-f][1,2,4]triazine as a light yellow solid (1.46, 27%).

1155f. Into a round bottom flask, 6-Bromo-2-methylsulfanyl-pyrrolo[2,1-f][1,2,4]triazine (0.510 g, 0.00209 mol) and Methylene chloride (6 mL) were added. m-Chloroperbenzoic acid (0.396 g, 0.00230 mol) was added portion wise over 20 minutes. The reaction was stirred at room temperature for one hour. The reaction was partitioned with DCM (200 mL) and saturated NaHCO$_3$ (200 mL). The organic was separated, washed with Brine and dried over Na$_2$SO$_4$. The solid was filtered and washed with DCM. The solvent was removed under vacuum to give 6-Bromo-2-ethanesulfinyl-pyrrolo[2,1-f][1,2,4]triazine a yellow solid. The solid was washed with hexane (0.53 g, 97%).

1155g. Into a microwave vial, 6-Bromo-2-methanesulfinyl-pyrrolo[2,1-f][1,2,4]triazine (0.343 g, 0.00132 mol), 4-(4-Methyl-piperazin-1-yl)-phenylamine (0.510 g, 0.00267 mol), 1-Methoxy-2-propanol (3.00 mL, 0.0307 mol) and N,N-Diisopropylethylamine (0.478 mL, 0.00274 mol) were added. The reaction was microwaved on 300 watts, 170° C. for 50 minutes. The solvent was removed under vacuum. The desired product was isolated via ISCO column chromatography with DCM and methanol as eluant (0 to 10% methanol). The collected fractions afforded a yellow solid 1155h. Into a 8-dram vial, Palladium Acetate (0.0059 g, 0.000026 mol) and Triphenylphosphine (0.019 g, 0.000074 mol) were added. The mixture was purged under an atmosphere of Nitrogen for 10 minutes. 1,4-Dioxane (2.00 mL, 0.0256 mol) was added and stirred for 10 minutes at room temperature. (6-Bromo-pyrrolo[2,1-f][1,2,4]triazin-2-yl)-[4-(4-methyl-piperazin-1-yl)-phenyl]-amine (0.102 g, 0.000264 mol), [2-(4,4,5,5-Tetramethyl-[1,3,2]dioxaborolan-2-yl)-phenoxy]-acetonitrile (0.137 g, 0.000527 mol), N,N-Dimethylformamide (4.0 mL, 0.052 mol), and 1.50 M of Sodium carbonate in Water (1.58 mL, 0.00237 mol) were added. The reaction was heated at 90° C. for 3 hours. The reaction was partitioned with water and EtOAc. The organic was separated, washed with Brine, and dried over magnesium sulfate. The solid was filtered and washed with EtOAc. The solvent was removed under vacuum. The reaction mixture was purified via HPLC reverse phase chromatography with 0.1% TFA in Water and 0.1% TFA in ACN. The collected fractions afforded a solid. The solid was triturated with $Et_2O$ and filtered to give (2-{2-[4-(4-Methyl-piperazin-1-yl)-phenylamino]-pyrrolo[2,1-f][1,2,4]triazin-6-yl}-phenoxy)-acetonitrile a yellow solid (5 mg, 3%). LCMS (E/I+) 440.18 (M+H). NMR $^1$H (DMSO-$d_6$)-9.57 (s, 1H), 9.29 (s, 1H), 8.93 (s, 1H), 8.18 (s, 1H), 7.81 (d, 1H, J=7.81 Hz), 7.69 (d, 2H, J=8.19 Hz), 7.34 (t, 1H, J=7.80 Hz), 7.26 (d, 1H, J=7.80 Hz), 7.21 (s, 1H), 7.14 (t, 1H, J=7.02 Hz), 7.00 (d, 2H, J=8.19 Hz), 5.32 (s, 2H), 3.75 (d, 2H, J=12.58 Hz), 3.485-3.59 (m, 2H), 3.09-3.24 (m, 2H), 2.80-2.97 (m, 5H).

Example 1156

[6-(2-Methoxy-phenyl)-pyrrolo[2,1-f][1,2,4]triazin-2-yl]-[4-(4-methyl-piperazin-1-yl)-phenyl]-amine The titled compound was prepared in an analogous fashion to Example 1155 replacing [2-(4,4,5,5-Tetramethyl-[1,3,2]dioxaborolan-2-yl)-phenoxy]-acetonitrile with 2-methoxyphenyl boronic acid to give a yellow solid (35 mg, 25%). LCMS (E/I+) 415.19 (M+H). NMR $^1$H (DMSO-$d_6$)-9.15 (s, 1H0, 8.88 (s, 1H), 8.17 (s, 1H), 7.74 (d, 1H, J=7.30), 7.63 (d, 2H, J=8.51 Hz), 7.26 (t, 1H, J=7.70 Hz), 7.20 (s, 1H), 7.12 (d, 1H, J=8.51 Hz), 7.00 (t, 1H, J=6.49 Hz), 6.92 (d, 2H, J=8.51 Hz), 3.91 (s, 3H), 3.07 (s, 4H), 2.46 (bs, 4H), 2.22 (s, 3H).

Example 1157

[4-(4-Methyl-piperazin-1-yl)-phenyl]-(6-pyridin-4-yl-pyrrolo[2,1-f][1,2,4]triazin-2-yl)-amine The titled compound was prepared in an analogous fashion to Example 1155 replacing [2-(4,4,5,5-Tetramethyl-[1,3,2]dioxaborolan-2-yl)-phenoxy]-acetonitrile with 3-pyridinyl bornic acid to give a yellow solid (31 mg, 23%). LCMS (E/I+) 386.15 (M+H). NMR $^1$H (DMSO-$d_6$)-9.24 (s, 1H), 9.03 (s, 1H), 8.93 (s, 1H), 8.45 (d, 1H, J=4.55 Hz), 8.41 (s, 1H), 8.17 (d, 1H, J=7.58 Hz), 7.62 (d, 2H, J=8.34 Hz), 7.41 (t, 1H, J=6.06 Hz), 6.92 (d, 2H, J=8.34 Hz), 3.07 (s, 4H), 2.46 (bs, 4H), 2.22 (s, 3H).

Example 1158

[4-(4-Methyl-piperazin-1-yl)-phenyl]-(6-pyridin-3-yl-pyrrolo[2,1-f][1,2,4]triazin-2-yl)-amine The titled compound was prepared in an analogous fashion to Example 1155 replacing [2-(4,4,5,5-Tetramethyl-[1,3,2]dioxaborolan-2-yl)-phenoxy]-acetonitrile with 4-pyridinyl bornic acid to give a yellow solid (28 mg, 21%). LCMS (E/I+) 386.14 (M+H). NMR $^1$H (DMSO-$d_6$)-9.72 (bs, 1H), 9.54 (s, 1H), 9.07 (s, 1H), 8.60-8.80 (m, 3H), 8.24 (d, 2H), 7.69 (d, 2H), 7.57 (s, 1H), 7.01 (d, 2H), 3.70-3.80 (bm, 2H), 3.45-3.55 (bm, 2H), 3.10-3.20 (m, 2H), 2.85-2.97 (m, 5H).

Example 1159

3-(3-{2-[2-Methoxy-4-(4-morpholin-4-yl-piperidin-1-yl)-phenylamino]-pyrrolo[2,1-f][1,2,4]triazin-7-yl}-phenyl)-propionitrile The titled compound was prepared in an analogous fashion to Example 1142 replacing 4-(4-Methyl-piperazin-1-yl)-phenylamine with 2-Methoxy-4-(4-morpholin-4-yl-piperidin-1-yl)-phenylamine LCMS (E/I+) 538.22 (M+H). NMR $^1$H (DMSO-$d_6$)-9.58 (bs, 1H), 8.92 (s, 1H), LCMS (E/I+) (M+H). 8.14 (s, 1H), 8.02 (d, 1H, J=8.04 Hz), 7.81 (d, 1H, J=9.22 Hz), 7.78 (s, 1H), 7.44 (t, 1H, J=8.40 Hz), 7.79 (d, 1H, J=7.42 Hz), 7.19 9 d, 1H0, J=4.95 Hz), 6.94 (d, 1H, J=4.95 Hz), 6.73 (s, 1H), 6.58 (d, 1H, J=8.66 Hz), 4.03 (d, 2H, J=11.75 Hz), 3.90 (d, 2H, J=11.75 Hz), 3.51 (d, 2H, J=12.98 Hz), 3.33-3.43 (m, 1H), 3.05-3.22 (m, 2H), 2.93 (t, 2H, J=7.42 Hz), 2.84 (t, 2H, J=6.80 Hz), 2.60-2.78 (m, 2H), 2.16 (d, 2H, J=11.26 Hz), 1.71 (q, 2H, J=12.36 Hz).

Example 1160

3-(3-{6-Methyl-2-[4-(4-methyl-piperazin-1-yl)-phenylamino]-pyrrolo[2,1-f][1,2,4]triazin-7-yl}-phenyl)-propionitrile 1160a. Into a 8-dram vial, 6-Bromo-2-methylsulfanyl-pyrrolo[2,1-f][1,2,4]triazine (0.542 g, 0.00222 mol), Trimethylboroxine (2.52 g, 0.0201 mol), and Potassium carbonate (1.95 g, 0.0141 mol) were added and purged under an atmosphere of Nitrogen for 10 minutes. N,N-Dimethylformamide (10.0 mL) was then added and heated at 130° C. for 4 hours. The reaction was partitioned with water and EtOAc. The organic was separated, washed with Brine, and dried over magnesium sulfate. The solid was filtered and washed with EtOAc. The solvent was removed under vacuum. The product was isolated via ISCO column chromatography with heane and EtOAc as eluant (0 to 35% EtOAc). The collected fractions afforded 6-Methyl-2-methylsulfanyl-yrrolo[2,1-f][1,2,4]triazine a yellow solid.

1160b. Into a 30 mL vial, 6-Methyl-2-methylsulfanyl-pyrrolo[2,1-f][1,2,4]triazine (0.308 g, 0.00172 mol), Tetrahydrofuran (10 mL, 0.2 mol) and Methanol (7 mL, 0.2 mol) were added. N-Bromosuccinimide (0.306 g, 0.00172 mol) was added over 10 minutes at −20° C. The reaction was stirred at room temperature overnight. The solvent was removed under vacuum. The reaction was partitioned with water and DCM. The organic was separated, washed with Brine and dried over $Na_2SO_4$. The solid was filtered and washed with DCM. The solvent was removed under vacuum. The desired product was isolated via ISCO column chromatography with hexane and EtOAc as eluant (1 to 8% EtOAc). The collected fractions afforded 7-Bromo-6-methyl-2-methylsulfanyl-pyrrolo[2,1-f][1,2,4]triazine a yellow solid (300 mg, 70%), and 5-Bromo-6-methyl-2-methylsulfanyl-pyrrolo[2,1-f][1,2,4]triazine as an off-white solid (89 mg, 20%).

1160c. The titled compound was prepared in an analogous fashion to Example 1142 replacing of 7-Bromo-2-methylsulfanyl-pyrrolo[2,1-f][1,2,4]triazine with 7-Bromo-6-methyl- 2-methylsulfanyl-pyrrolo[2,1-f][1,2,4]triazine to give a yellow solid (42 mg, 35%). LCMS (E/I+) 452.21 (M+H). NMR $^1$H (DMSO-d$_6$)-9.58 (bs, 1H), 9.21 (s, 1H), 8.85 (s, 1H), 7.72 (s, 1H), 7.69 (d, 1 h, J=7.84 Hz), 7.62 (d, 2H, J=7.84 Hz), 7.55 (t, 1H, J=7.84 Hz), 7.38 (d, 1H, J=7.84 Hz), 6.80-6.95 (m, 2H), 6.77 (s, 1H), 3.72 (d, 2H, J=13.38 Hz), 3.52 (d, 2H, J=9.49 Hz), 3.16 (q, 2H, J=9.93 Hz), 3.01 (t, 2H, J=7.31 Hz), 2.80-2.93 (m, 7H), 2.35 (s, 3H).

Example 1161

3-(3-{2-[4-(4-Methyl-piperazin-1-yl)-phenylamino]-pyrrolo[2,1-f][1,2,4]triazin-6-yl}-phenyl)-propionitrile The titled compound was prepared in an analogous fashion to Example 1155 replacing [2-(4,4,5,5-Tetramethyl-[1,3,2] dioxaborolan-2-yl)-phenoxy]-acetonitrile with 3-[3(4,4,5,5-Tetramethyl-[1,3,2]dioxaborolan-2-yl)-phenyl]-propionitrile to give a yellow solid (56 mg, 77%). LCMS (E/I+) 438.26 (M+H). NMR $^1$H (DMSO-d$_6$)-9.61 (bs, 1H), 9.30 (s, 1H), 8.92 (s, 1H), 8.31 (s, 1H), 7.74 (s, 1H), 7.60-7.72 (m, 3H), 7.36 (t, 1H, J=7.65 Hz), 7.18 (bs, 2H), 7.00 9 d, 2H, J=7.97 Hz), 3.76 (d, 2H, J=12.75 Hz), 3.53 (d, 2H, J=11.48 Hz), 3.18 (q, 2H, J=11.48 Hz), 2.78-2.99 (m, 9H).

Example 1162

(7-{3-[(2-Methanesulfonyl-ethylamino)-methyl]-phenyl}-pyrrolo[2,1-f][1,2,4]triazin-2-yl)-[4-(4-methyl-piperazin-1-yl)-phenyl]-amine 1162a. Into a 8-dram vial, Palladium Acetate (0.046 g, 0.00020 mol) and Triphenylphosphine (0.15 g, 0.00057 mol) were added. The mixture was purged under an atmosphere of Nitrogen for 10 minutes. 1,4-Dioxane (15.5 mL, 0.199 mol) was added and stirred for 10 minutes at room temperature. 7-Bromo-2-methylsulfanyl-pyrrolo[2,1-f][1,2,4]triazine (0.50 g, 0.0020 mol), [3-Formylphenyl boronic acid (0.614 g, 0.00410 mol), N,N-Dimethylformamide (31 mL, 0.40 mol), and 1.50 M of Sodium carbonate in Water (12.3 mL, 0.0184 mol) were added. The reaction was heated at 90° C. for 3 hours. The reaction was partitioned with water and EtOAc. The organic was separated, washed with Brine, and dried over magnesium sulfate. The solid was filtered and washed with EtOAc. The solvent was removed under vacuum. The product was isolated via column chromatography with DCm and NH3 in Methanol as eluant (0 to 10% NH$_3$ in MeOH). The collected fractions afforded a solid. The solid was triturated with Et2O and filtered to give a yellow solid. The solid was treated with m-CPBA 70-75% (70:30, m-Chloroperbenzoic acid:3-Chlorobenzoic acid, 0.555 g, 0.00225 mol) and Methylene chloride (400 mL, 6 mol) at room temperature. The reaction was partitioned with Sat. NaHCO$_3$ and DCM. The organic was separated, washed with Brine and dried over Na$_2$SO$_4$. The solid was filtered and washed with DCM. The solvent was removed under vacuum to give 3-(2-Methanesulfinyl-pyrrolo[2,1-f][1,2,4]triazin-7-yl)-benzaldehyde a yellow solid (280 mg, 48%).

1162b. Into a 8-dram vial, 3-(2-Methanesulfinyl-pyrrolo[2,1-f][1,2,4]triazin-7-yl)-benzaldehyde (0.270 g, 0.946 mmol), 2-Methanesulfonyl-ethylamine; hydrochloride (0.332 g, 2.08 mmol), Methylene chloride (120 mL, 1900 mmol) and Acetic acid (100 uL, 2 mmol) were added. The reaction mixture was stirred for 2 hours. Sodium triacetoxyborohydride (0.441 g, 2.08 mmol) was added. The reaction mixture was stirred at room temperature overnight. The reaction was partitioned with Saturated NaHCO$_3$ and DCM. The organic was separated, washed with Brine and dried over Na$_2$SO$_4$. The solid was filtered and washed with DCM. The Solvent was removed under vacuum. The reaction mixture was purified via ISCO column chromatography with DCM and methanol as eluant (0 to 10% methanol). The collected fractions afforded 3-(2-Methanesulfinyl-pyrrolo[2,1-f][1,2,4]triazin-7-yl)-benzyl]-(2-methanesulfonyl-ethyl)-amine as a yellow solid (0.18 g, 48%).

1162c. Into a microwave vial, [3-(2-Methanesulfinyl-pyrrolo[2,1-f][1,2,4]triazin-7-yl)-benzyl]-(2-methanesulfonyl-ethyl)-amine (0.100 g, 0.000255 mol), 4-(4-Methyl-piperazin-1-yl)-phenylamine (0.214 g, 0.00112 mol), 1-Methoxy-2-propanol (0.613 mL) and N,N-Diisopropylethylamine (0.133 mL, 0.000764 mol) were added. The reaction was microwaved on 300 watts, 170° C. for 50 minutes. The solvent was removed under vacuum. The desired product was isolated via ISCO column chromatography with DCM and methanol as eluant (0 to 15% methanol). The collected fractions afforded (7-{3-[(2-Methanesulfonyl-ethylamino)-methyl]-phenyl}-pyrrolo[2,1-f][1,2,4]triazin-2-yl)-[4-(4-methyl-piperazin-1-yl)-phenyl]-amine a yellow solid (41 mg, 31%). LCMS (E/I+) 520.16 (M+H). NMR $^1$H (DMSO-d$_6$)-9.76 (ns, 1H), 9.37 (s, 1H), 9.20 (bs, 2H), 8.99 (s, 1H), 8.42 (d, 2H, J=7.45 Hz), 8.16 (s, 1H), 7.61-7.72 (m, 3H), 7.51 (d, 1H, J=7.45 Hz), 7.15 (d, 1H, J=4.47 Hz), 6.91-7.04 (m, 4H), 4.31 (s, 2H), 3.76 (d, 2H, J=12.66 Hz), 3.34-3.63 (m, 6H0, 3.08-3.24 (m, 5H), 2.82-3.00 (m, 5H).

Example 1163

N(2)-[4-(4-Methyl-piperazin-1-yl)-phenyl]-N(7)-(3-nitro-benzyl)-pyrrolo[2,1-f][1,2,4]triazine-2,7-diamine Into a 8-dram vial, (7-Bromo-pyrrolo[2,1-f][1,2,4]triazin-2-yl)-[4-(4-methyl-piperazin-1-yl)-phenyl]-amine (66.6 mg, 0.000172 mol), 3-nitrobenzylamine (31.42 mg, 0.0002065 mol) Palladium Acetate (4.00 mg, 0.0000178 mol), 9,9-Dimethyl-4,5-bis(diphenylphosphino)xanthene (30.0 mg, 0.0518 mmol), and Cesium Carbonate (240.0 mg, 0.7366 mmol) were added. The mixture was purged with nitrogen for 15 minutes. 1,4-Dioxane (2.00 mL) was added. The reaction vessel was sealed and heated at 120° C. for 2 hours. The reaction mixture was partitioned with DCM. The solid was filtered through celite and washed with DCM. The filtrate was evaporated to give a semi-solid. The reaction mixture was purified via HPLC reverse phase chromatography with 0.1% TFA in Water and 0.1% TFA in ACN (0 to 20% ACN). The collected fractions were lyophilized to give N(2)-[4-(4-Methyl-piperazin-1-yl)-phenyl]-N(7)-(3-nitro-benzyl)-pyrrolo[2,1-f][1,2,4]triazine-2,7-diamine a solid (32 mg, 32%). The solid was triturated with Et$_2$O to give a yellow solid. LCMS (E/I+) 459.14 (M+H). NMR $^1$H (DMSO-d$_6$)-9.75 (bs, 1H), 9.31 (s, 1H), 8.36 9 s, 1H), 8.27 (s, 1H), 8.14 (d, 1H, J=8.20 Hz), 7.86 (d, 1H, J=7.60 Hz), 7.59-7.73 (m, 3H), 7.49 (bs, 1H), 7.09 (bs, 1H), 6.98 (d, 2H, J=8.20 Hz), 6.55 (bs, 1H), 4.76 (s, 2H), 3.75 (d, 2H, J=12.89 Hz), 3.54 (d, 2H, J=11.72 Hz), 3.16 (q, 2H, J=18.79 Hz), 2.79-2.99 (m, 5H).

Example 1164

N(2)-[4-(4-Methyl-piperazin-1-yl)-phenyl]-N(7)-pyridin-3-ylmethyl-pyrrolo[2,1-f][1,2,4]triazine-2,7-diamine Into a 8-dram vial, (7-Bromo-pyrrolo[2,1-f][1,2,4]triazin-2-yl)-[4-(4-methyl-piperazin-1-yl)-phenyl]-amine (66.6 mg, 0.000172 mol), [3-(Aminomethyl)-pyridine (22.33 mg, 0.2065 mmol) Palladium Acetate (4.00 mg, 0.0178 mmol), 9,9-Dimethyl-4,5-bis(diphenylphosphino)xanthene (30.0 mg, 0.0518 mmol), and Cesium Carbonate (240.0 mg, 0.7366 mmol) were added. The mixture was purged with nitrogen for 15 minutes. 1,4-Dioxane (2.00 mL) was added. The reaction vessel was sealed and heated at 120° C. for 2 hours. The reaction mixture was partitioned with DCM. The solid was filtered through celite and washed with DCM. The filtrate was evaporated to give a semi-solid. The reaction mixture was purified via HPLC reverse phase chromatography with 0.1% TFA in Water and 0.1% TFA in ACN (0 to 20% ACN). The collected fractions were lyophilized to give N(2)-[4-(4-Methyl-piperazin-1-yl)-phenyl]-N(7)-pyridin-3-ylmethyl-pyrrolo[2,1-f][1,2,4]triazine-2,7-diamine a solid. The solid was triturated with Et2O to give a yellow solid 78 mg, 85%). LCMS (E/I+) 415.17 (M+H). NMR $^1$H (DMSO-d$_6$)-9.80 (bs, 1H), 9.34 (s, 1H), 8.70 (s, 1H), 8.57 (s, 1H), 8.36 (s, 1H), 7.89 (d, 1H, J=7.04 Hz), 7.65 (d, 2H, J=8.04 Hz), 7.54 (t, 1H, J=5.53 Hz), 7.49 (bs, 1H), 7.13 (s, 1H), 6.99 (d, 2H, J=8.04 Hz), 6.33 (s, 1H), 4.72 (s, 2H), 3.75 (d, 2H, J=12.56 Hz), 3.54 (d, 2H, J=11.06 Hz), 3.18 (bs, 2H), 2.6-3.00 (m, 5H).

Example 1165

N(2)-[4-(4-Methyl-piperazin-1-yl)-phenyl]-N(7)-pyridin-4-ylmethyl-pyrrolo[2,1-f][1,2,4]triazine-2,7-diamine The titled compound was prepared in an analogous fashion to Example 1164 replacing 3-(Aminomethyl)-pyridine with 4-(Aminomethyl)-pyridine to give a yellow solid (32 mg, 20%). LCMS (E/I+) 415.19 (M+H). NMR $^1$H (DMSO-d$_6$)-9.74 (bs, 1H), 9.23 (s, 1H), 8.66 (d, 2H, J=4.96 Hz), 8.40 (s, 1H), 7.69 (d, 2H, J=8.27 Hz), 7.62 (d, 2H, J=4.14 Hz), 7.00 (s, 1H), 6.98 (d, 2H, J=8.27 Hz), 6.37 (bs, 1H), 4.76 (s, 2H), 3.74 (d, 2H, J=2.35 Hz), 3.54 (d, 2H, J=11.23 Hz), 3.12 (bs, 2H), 2.80-2.99 (m, 5H).

Example 1166

4-(3-{2-[4-(4-Methyl-piperazin-1-yl)-phenylamino]-pyrrolo[2,1-f][1,2,4]triazin-7-yl}-phenyl)-piperazine-1-carboxylic acid tert-butyl ester The titled compound was prepared in an analogous fashion to Example 7 replacing phenyboronic acid with 4-[3-(4,4,5,5-Tetramethyl-[1,3,2]dioxaborolan-2-yl)-phenyl]-piperazine-1-carboxylic acid tert-butyl ester to give a yellow solid (280 mg, 54%). LCMS (E/I+) 569.15 (M+H). NMR $^1$H (DMSO-d$_6$)-9.20 (s, 1H), 8.91 (s, 1H), 7.74, (s, 1H), 7.64 (d, 2H, J=7.90), 7.54 (d, 1H, J=7.36 Hz), 7.38 (t, 1H, J=7.90 Hz), 7.09 (d, 1H, J=4.74 Hz), 7.00 (d, 1H, J=7.90 Hz), 6.90 (d, 1H, J=4.74 Hz), 6.87 (d, 2H, J=8.42 Hz), 3.43 (bs, 4H), 3.13 (bs, 2H), 3.05 (s, 2H), 2.44 (bs, 4H), 2.21 (s, 3H), 1.41 (s, 9H).

Example 1167

N(2)-[3-(4-Methyl-piperazin-1-yl)-phenyl]-N(7)-pyridin-4-ylmethyl-pyrrolo[2,1-f][1,2,4]triazine-2,7-diamine The titled compound was prepared in an analogous fashion to Example 1165 replacing (7-Bromo-pyrrolo[2,1-f][1,2,4]triazin-2-yl)-[4-(4-methyl-piperazin-1-yl)-phenyl]-amine with (7-Bromo-pyrrolo[2,1-f][1,2,4]triazin-2-yl)-3-(4-methyl-piperazin-1-yl)-phenyl]-amine to give a yellow solid (65 mg, 60%). LCMS (E/I+) 415.20 (M+H). NMR $^1$H (DMSO-d$_6$)-9.80 (bs, 1H), 9.27 (s, 1H), 8.70 (d, 2H, J=5.31 Hz), 8.44 (s, 1H), 7.70 (d, 2H, J=4.42 Hz), 7.47 (d, 1H, J=7.96 Hz), 7.14-7.38 (m, 3H), 7.01 (d, 1H, J=4.42 Hz), 6.67 (d, 1H, J=7.96 Hz), 6.38 (bs, 1H), 4.77 (bs, 2H), 3.83 (bs, 2H), 3.47 (bs, 2H), 3.14 (bs, 2H), 2.85 (s, 3H).

Example 1168

N-(2)-[3-(4-Methyl-piperazin-1-yl)-phenyl]-N(7)-pyridin-3-ylmethyl-pyrrolo[2,1-f][1,2,4]triazine-2,7-diamine The titled compound was prepared in an analogous fashion to Example 1164 replacing (7-Bromo-pyrrolo[2,1-f][1,2,4]triazin-2-yl)-[4-(4-methyl-piperazin-1-yl)-phenyl]-amine with (7-Bromo-pyrrolo[2,1-f][1,2,4]triazin-2-yl)-[3-(4-methyl-piperazin-1-yl)-phenyl]-amine to give a yellow solid (65 mg, 60%). LCMS (E/I+) 415.19 (M+H). NMR $^1$H (DMSO-d$_6$)-9.90 (bs, 1H), 1.41 (s, 1H), 8.73 (s, 1H), 8.62 (d, 1H, J=4.97 Hz), 8.4 (s, 1H), 8.06 (d, 1H, J=7.45 Hz), 7.61 (t, 1H, J=5.79 Hz), 7.48 (bs, 1H), 7.37 (d, 1H, J=7.45 Hz), 7.24 (d, 1H, J=7.45 Hz), 7.19 (s, 1H), 7.16 (d, 1H, J=4.97 Hz), 6.70 (d, 1H, J=8.28 Hz), 6.66 (d, 1H, J=4.57 Hz), 4.71 (s, 2H), 3.86 (bs, 2H), 3.47 (bs, 2H), 3.14 (bs, 2H), 2.98 (bs, 4H), 2.86 (s, 3H).

Example 1169

[4-(4-Methyl-piperazin-1-yl)-phenyl]-[7-(3-piperazin-1-yl-phenyl)-pyrrolo[2,1-f][1,2,4]triazin-2-yl]-amine The titled compound was prepared in an analogous fashion to Example 1129 replacing [2-(4-Morpholin-4-yl-phenylamino)-pyrrolo[2,1-f][1,2,4]triazin-7-yl]-piperidine-1-carboxylic acid tert-butyl ester with 4-(3-{2-[4-(4-Methyl-piperazin-1-yl)-phenylamino]-pyrrolo[2,1-f][1,2,4]triazin-7-yl}-phenyl)-piperazine-1-carboxylic acid tert-butyl ester to give a yellow solid (180 mg, 76%). LCMS (E/I+) 469.21 (M+H). NMR $^1$H (DMSO-d$_6$)-975 (s, 1H), 9.31 (s, 1H), 8.94 (s, 1H), 8.61 (bs, 1H), 7.89 (q, 1H, J=7.30 Hz), 7.68 (d, 2H, J=7.76 Hz), 7.56 (s, 1H), 7.45 (t, 1H, J=7.76 Hz), 7.18 (d, 1H, J=4.57 Hz), 7.04 (d, 1H, J=8.22 Hz), 6.89-6.99 (m, 3H), 3.77 (d, 2H, J=13.72 Hz), 3.54 (d, 2H, J=11.76 Hz), 3.41 (bs, 4H), 3.24 (bs, 4H), 3.10-3.21 (m, 2H), 2.82-2.98 (m, 5H).

Example 1170

[2-Methoxy-4-(4-morpholin-4-yl-piperidin-1-yl)-phenyl]-(7-pyridin-3-yl-pyrrolo[2,1-f][1,2,4]triazin-2-yl)-amine Into a 8-dram vial, 2-Methoxy-4-(4-morpholin-4-yl-piperidin-1-yl)-phenylamine (40.0 mg, 0.137 mmol), 2-Methanesulfinyl-7-pyridin-3-yl-pyrrolo[2,1-f][1,2,4]triazine (80.9 mg, 0.313 mmol), Cesium fluoride (41.7 mg, 0.274 mmol), tert-Butyl alcohol (0.80 mL) and N,N-Diisopropylethylamine (0.0478 mL, 0.274 mmol) were added. The reaction mixture was heated at 130° C. overnight. HPLC suggested little if any SM. The reaction mixture was purified via HPLC reverse phase chromatography with 0.1% TFA in Water and 0.1% TFA in ACN. The collected fractions were lyophilized to give a [2-Methoxy-4-(4-morpholin-4-yl-piperidin-1-yl)-phenyl]-(7-pyridin-3-yl-pyrrolo[2,1-f][1,2,4]triazin-2-yl)-amine yellow solid (22 mg, 33%). LCMS (E/I+) 486.18 (M+H). NMR $^1$H (DMSO-d$_6$)-9.35 (s, 1H), 8.97 (s, 1H), 8.65 (d, 1H, J=8.50 Hz), 8.55 (s, 1H), 7.97 (s, 1H), 7.69 (d, 1H, J=8.50 Hz), 7.50 (t, 1H, J=5.95 Hz), 7.31 (d, 1H, J=4.25 Hz), 6.97 (d, 1H, J=4.25 Hz), 6.73 (s, 1H), 6.58 (d, 1H, J=9.35 Hz), 4.05 (d, 2H, J=11.87 Hz), 3.91 (d, 2H, J=11.87 Hz), 3.83 (s. 3H), 3.67 (t, 2H, J=11.87 Hz), 3.52 (d, 2H, J=11.87 Hz), 3.13 (d, 2H, J=11.87 Hz), 2.73 (t, 2H, J=11.87 Hz), 2.16 (d, 2H, J=11.87 Hz), 1.71 (q, 2H, J=11.87 Hz).

Example 1171

N-[2-(2-{4-[4-(2-Hydroxy-ethyl)-piperazin-1-yl]-phenylamino}-pyrrolo[2,1-f][1,2,4]triazin-7-yl)-phenyl]-N-methyl-methanesulfonamide The titled compound was prepared in an analogous fashion to Example 1170 replacing 2-Methanesulfinyl-7-pyridin-3-yl-pyrrolo[2,1-f][1,2,4]triazine with 2-Methanesulfinyl-7-(6-methoxy-pyridin-3-yl)-pyrrolo[2,1-f][1,2,4]triazine to give a yellow solid (25 mg, 35%). LCMS (E/I+) 516.17 (M+H). NMR $^1$H (DMSO-d$_6$)-9.66 (bs, 1H), 8.91 (s, 1H), 8.83 (s, 1H), 8.50 (d, 1H, J=9.50 Hz), 7.85 (s, 1H), 7.72 (d, 1H, J=9.00 Hz), 7.16 (s, 1H), 6.90-6.98 (m, 2H), 6.73 (bs, 1H), 6.58 (d, 1H, J=8.18 Hz), 4.04 (d, 2H, J=13.09 Hz), 3.86-3.96 (m, 5H), 3.84 (s, 3H), 3.67 (t, 2H, J=12.27 Hz), 3.50 (d, 2H, J=12.27 Hz), 3.30-3.42 (m, 1H), 3.05-3.21 (m, 2H), 2.73 (t, 2H, J=12.27 Hz), 2.16 (d, 2H, J=12.27) Hz, 1.73 (q, 2H, J=12.27 Hz).

Example 1172

N-[2-(2-{2-[4-(4-Amino-phenyl)-piperazin-1-yl]-ethoxy}-pyrrolo[2,1-f][1,2,4]triazin-7-yl)-phenyl]-N-methyl-methanesulfonamide The titled compound was prepared in an analogous fashion to Example 1170 replacing 2-Methanesulfinyl-7-pyridin-3-yl-pyrrolo[2,1-f][1,2,4]triazine with N-[2-(2-Methanesulfinyl-pyrrolo[2,1-f][1,2,4]triazin-7-yl)-phenyl]-N-methyl-methanesulfonamide to give a yellow solid (95 mg, 37%). LCMS (E/I+) 522.12 (M+H). NMR $^1$H (DMSO-d$_6$)-9.10 (s, 1H), 7.89 (d, 1H, J=7.54 Hz), 7.69 (d, 1H, J=7.54 Hz), 7.45-7.60 (m, 2H), 7.18 (d, 2H, J=7.54 Hz), 7.21 (bs, 2H), 7.05 (d, 2H, J=7.54 Hz), 4.60 (bs, 2H), 2.79-3.90 (m, 12H).

Example 1173

(2-{2-[4-(4-Methyl-piperazin-1-yl)-phenylamino]-pyrrolo[2,1-f][1,2,4]triazin-7-yl}-phenoxy)-acetic acid tert-butyl ester Into a 8-dram tube, 2-{2-[4-(4-Methyl-piperazin-1-yl)-phenylamino]-pyrrolo[2,1-f][1,2,4]triazin-7-yl}-phenol (0.420 g, 1.05 mmol), Acetic acid, bromo-, 1,1-dimethylethyl ester (0.245 g, 1.26 mmol), Potassium carbonate (0.290 g, 2.10 mmol), and Acetonitrile (10 mL) were added. The mixture was heated at 60° C. overnight. The solid was filtered through Celite and washed with DCM. The solvent was removed under vacuum. The reaction mixture was purified via ISCO column chromatography with DCM and methanol as eluant (0 to 10% methanol). The collected fractions afforded (2-{2-[4-(4-Methyl-piperazin-1-yl)-phenylamino]-pyrrolo[2,1-f][1,2,4]triazin-7-yl}-phenoxy)-acetic acid tert-butyl ester as a yellow solid (280 mg, 51%). LCMS (E/I+) 515.12 (M+H). MP 193-195° C. NMR $^1$H (DMSO-d$_6$)-9.13 (s, 1H), 8.90 (s, 1H), 8.03 (d, 1H, J=7.82 Hz), 7.58 (d, 2H, J=8.35 Hz), 7.40 (t, 1H, J=7.82 Hz), 7.16 (t, 1H, J=7.30 Hz), 7.05-7.13 (m, 2H), 6.89 (d, 1H, J=4.83), 6.82 (d, 2H, J=8.35 Hz), 4.70 (s, 2H), 3.03 (bs, 4H), 2.44 (bs, 4H), 2.21 (s, 3H), 1.38 (s, 9H).

Example 1174

2,2,2-Trifluoro-N-{8-[7-(4-methanesulfonyl-phenyl)-pyrrolo[2,1-f][1,2,4]triazin-2-ylamino]-2-oxo-2,3,4,5-tetrahydro-1H-benzo[b]azepin-3-yl}-acetamide Into a 8-dram vial, N-(8-Amino-2-oxo-2,3,4,5-tetrahydro-1H-1-benzazepin-3-yl)-2,2,2-trifluoro-acetamide (39.4 mg, 0.137 mmol), 2-Methanesulfinyl-7-(4-methanesulfonyl-phenyl)-pyrrolo[2,1-f][1,2,4]triazine (105 mg, 0.313 mmol), Cesium fluoride (41.7 mg, 0.274 mmol), tert-Butyl alcohol (0.80 mL) and N,N-Diisopropylethylamine (0.0478 mL, 0.274 mmol) were added. The reaction mixture was heated at 130° C. overnight. HPLC suggested no starting material. The solvent was evaporated. The reaction mixture was purified via HPLC reverse phase chromatography with 0.1% TFA in Water and 0.1% TFA in ACN. The collected fractions were lyophilized to give 2,2,2-Trifluoro-N-{8-[7-(4-methanesulfonyl-phenyl)-pyrrolo[2,1-f][1,2,4]triazin-2-ylamino]-2-oxo-2,3,4,5-tetrahydro-1H-benzo[b]azepin-3-yl}-acetamide as a yellow solid (25 mg, 32%). LCMS (E/I+) 559.07 (M+H). NMR $^1$H (DMSO-d$_6$)-9.96 (s, 1H0, 9.74 (s, 1H), 9.65 (bs, 1H), 9.08 (s, 1H), 8.46 (d, 2H, J=7.72 Hz), 8.04 (d, 2H, J=7.72 Hz), 7.59 (s, 1H), 7.54 (d, 1H, J=8.49 Hz), 7.35 (bs, 1H), 7.28 (d, 1H, J=7.72 Hz), 7.03 (d, 1H, J=4.62 Hz), 4.29 (bs, 1H), 3.22 (s, 3H), 2.63-2.72 (m, 2H), 2.24-2.35 (m, 2H).

Example 1175

N-[2-(2-{4-[4-(2-Hydroxy-ethyl)-piperazin-1-yl]-phenylamino}-pyrrolo[2,1-f][1,2,4]triazin-7-yl)-phenyl]-N-methyl-methanesulfonamide Into a 8-dram vial, 2-[4-(4-Amino-phenyl)-piperazin-1-yl]-ethanol (0.134 g, 0.604 mmol), N-[2-(2-Methanesulfinyl-pyrrolo[2,1-f][1,2,4]triazin-7-yl)-phenyl]-N-methyl-methanesulfonamide (0.100 g, 0.274 mmol), Cesium fluoride (0.104 g, 0.686 mmol), N,N-Diisopropylethylamine (0.1051 mL, 0.6036 mmol) and tert-Butyl alcohol (1.50 mL) were added. The reaction was heated at 120° C. overnight. LCMS suggested presence of desired product. The solvent was removed under vacuum. The reaction mixture was purified via HPLC reverse phase chromatography with 0.1% TFA in Water and 0.1% TFA in ACN. The collected fractions were lyophilized to give N-[2-(2-{4-[4-(2-Hydroxy-ethyl)-piperazin-1-yl]-phenylamino}-pyrrolo[2,1-f][1,2,4]triazin-7-yl)-phenyl]-N-methyl-methanesulfonamide as a yellow solid (48 mg, 34%). LCMS (E/I+) 522.16 (M+H). NMR $^1$H (DMSO-d$_6$)-9.15 (bs, 1H), 9.24 (s, 1H), 8.94 (s, 1H), 8.02 (d, 1H, J=7.91 Hz), 7.66 (d, 1H, J=7.34 Hz), 7.47-7.62 (m, 4H), 6.98 (d, 1H, J=4.52 Hz), 6.93 (d, 1H, J=4.52), 6.87 (d, 1H, J=8.47 Hz), 3.77 (bs, 2H), 3.70 (d, 2H, J=12.98 Hz), 3.58 (d, 2H, J=12.86 Hz), 3.13-3.30 (m, 2H), 3.08 (s, 1H), 2.97 (t, 2H, J=12.42 Hz), 2.89 (s, 3H).

Example 1176

N-Methyl-N-{2-[2-(5-morpholin-4-yl-pyridin-2-ylamino)-pyrrolo[2,1-f][1,2,4]triazin-7-yl]-phenyl}-methanesulfonamide 1176a. Into a 8-dram vial, 5-Bromo-2-nitro-pyridine (2.00 g, 9.85 mmol), Morpholine (1.12 g, 12.8 mmol), Triethylamine (1.37 mL, 9.85 mmol) and Dimethyl sulfoxide (10 mL, 100 mmol) were added. The reaction mixture was heated at 80° C. overnight. The reaction was cooled to RT and poured over ice. The solid was filtered and washed with water. The solid was washed with ethanol. The resulting solid was dried under vacuum to give 4-(6-Nitro-pyridin-3-yl)-morpholine as a white solid (1.60 g, 81%).

1176b. Into a round bottom flask, 4-(6-Nitro-pyridin-3-yl)-morpholine (1.67 g, 0.00798 mol), 20% Pd(OH)$_2$/C, 50% wet (10:40:50, Palladium hydroxide:carbon black:Water, 0.350 g, 0.000249 mol), and Ethanol (50 mL, 0.9 mol) were added into a parr bottle. The mixture was evacuated under house vacuum and charged with hydrogen at 35 pSi. The reaction was shaken at room temperature at 35 pSi. The solid was filtered. The solvent was removed under vacuum to afford an off white solid. The solid was triturated with Et$_2$O, Filtered and washed with Et$_2$O to give 5-Morpholin-4-yl-pyridin-2-ylamine as an off white solid (1.01, 70%).

1176c. Into a 8-dram vial, 5-Morpholin-4-yl-pyridin-2-ylamine (0.108 g, 0.604 mmol), N-[2-(2-Methanesulfinyl-pyrrolo[2,1-f][1,2,4]triazin-7-yl)-phenyl]-N-methyl-methanesulfonamide (0.100 g, 0.274 mmol), Cesium fluoride (0.104 g, 0.686 mmol), N,N-Diisopropylethylamine (0.1051 mL, 0.6036 mmol) and tert-Butyl alcohol (1.50 mL) were added. The reaction was heated at 120° C. overnight. LCMS suggested presence of desired product. The solvent was removed under vacuum. The reaction mixture was purified via HPLC reverse phase chromatography with 0.1% TFA in Water and 0.1% TFA in ACN. The collected fractions were lyophilized to give a yellow solid (40 mg, 33%). LCMS (E/I+) 480.14 (M+H). NMR $^1$H (DMSO-d$_6$)-10.49 (bs, 1H), 9.09 (s, 1H), 7.86-7.92 (m, 1H), 7.84 (bs, 1H), 7.70-7.80 (m, 1H), 7.66-7.73 (m, 1H), 7.50-7.64 (m, 3H), 7.13 (bs, 1H), 7.11 (bs, 1H), 3.75 (bs, 4H), 3.14 (s, 3H), 3.11 (bs, 4H), 2.83 (s, 3H).

Example 1177

[7-(2-Methoxy-phenyl)-pyrrolo[2,1-f][1,2,4]triazin-2-yl]-[5-(4-methyl-piperazin-1-yl)-pyridin-2-yl]-amine 1177a. Into a 8-dram vial, 5-Bromo-2-nitro-pyridine (2.00 g, 9.85 mmol), 1-Methylpiperazine (1.28 g, 12.8 mmol), Triethylamine (1.37 mL, 9.85 mmol) and Dimethyl sulfoxide (10 mL) were added. The reaction mixture was heated at 80° C. overnight. The reaction content was cooled to RT and poured over ice. The solid was filtered and washed with water. The solid was washed with Et$_2$O. The resulting solid was dried under vacuum.

1177b. Into a round bottom flask, 1-Methyl-4-(6-nitro-pyridin-3-yl)-piperazine (1.02 g, 4.59 mmol), 10% Pd/C (0.201 g, 0.000143 mol), and Ethanol (30 mL, 0.5 mol) were added into a parr bottle. The mixture was evacuated under house vacuum and charged with a hydrogenat 35 pSi. The reaction was shaken at room temperature at 35 Psi for one hour. The solid was filtered. The solvent was removed under vacuum to afford an off white solid. The solid was triturated with Et$_2$O, Filtered and washed with Et$_2$O to give an off white solid.

1177c. Into a 8-dram vial, 5-(4-Methyl-piperazin-1-yl)-pyridin-2-ylamine (0.154 g, 0.804 mmol), 2-Methanesulfinyl-7-(2-methoxy-phenyl)-pyrrolo[2,1-f][1,2,4]triazine (0.105 g, 0.365 mmol), Cesium fluoride (0.139 g, 0.914 mmol), N,N-Diisopropylethylamine (0.1400 mL, 0.8039 mmol) and tert-Butyl alcohol (2.00 mL, 20.9 mmol) were added. The reaction was heated at 120° C. overnight. LCMS suggested presence of desired product. The reaction mixture was purified via HPLC reverse phase chromatography with 0.1% TFA in Water and 0.1% TFA in ACN. The collected fractions were lyophilized to give [7-(2-Methoxy-phenyl)-pyrrolo[2,1-f][1,2,4]triazin-2-yl]-[5-(4-methyl-piperazin-1-yl)-pyridin-2-yl]-amine as a yellow solid (30 mg, 22%). LCMS (E/I+) 416.18 (M+H). NMR $^1$H (DMSO-d$_6$)-9.80 (s, 1H), 9.72 (bs, 1H), 9.01 (s, 1H), 7.99 (s, 1H), 7.90 (d, 1H, J=9.58 Hz), 7.80 (d, 1H, J=7.49), 7.53 (d, 1H, J=9.38 Hz), 7.47 (d, 1H, J=7.59 Hz), 7.24 (d, 1H, J=8.04 Hz), 7.14 (t, 1H, J=7.15 Hz), 7.01 (s, 2H), 3.80 (bs, 5H), 3.55 (d, 2H, J=11.72 Hz), 3.19 (q, 2H, J=10.34 Hz), 2.96 (t, 2H, J=11.72 Hz), 2.83 (s, 3H).

Example 1178

N-Methyl-N-(2-{2-[4-(1-methyl-piperidin-4-yl)-phenylamino]-pyrrolo[2,1-f][1,2,4]triazin-7-yl}-phenyl)-methanesulfonamide Into a 8-dram vial, 4-(1-Methyl-piperidin-4-yl)-phenylamine (0.115 g, 0.604 mmol), N-[2-(2-Methanesulfinyl-pyrrolo[2,1-f][1,2,4]triazin-7-yl)-phenyl]-N-methyl-methanesulfonamide (0.100 g, 0.274 mmol), N,N-Diisopropylethylamine (0.1051 mL, 0.6036 mmol) and were added. The reaction was heated at 120° C. overnight. LCMS suggested presence of desired product. The solvent was removed under vacuum. The reaction mixture was purified via HPLC reverse phase chromatography with 0.1% TFA in Water and 0.1% TFA in ACN. The collected fractions were lyophilized to give N-Methyl-N-(2-{2-[4-(1-methyl-piperidin-4-yl)-phenylamino]-pyrrolo[2,1-f][1,2,4]triazin-7-yl}-phenyl)-methanesulfonamide as a yellow solid (38 mg, 36%). LCMS (E/I+) 491.16 (M+H). NMR $^1$H (DMSO-d$_6$)-9.39 (s, 1H), 9.33 (s, 1H), 8.50 (d, 1H, J=7.59 Hz), 7.74 (d, 1H, J=7.59 Hz), 7.50-7.62 (m, 3H), 7.06 (d, 2H, J=7.59 Hz), 6.98 (bs, 1H), 6.93 (bs, 1H), 3.10 (s, 3H), 2.90 (s, 3H), 2.85 (d, 2H, J=11.43 Hz), 2.30-2.40 (m, 1H), 2.18 (s, 3H), 1.92 (t, 2H, J=11.43 Hz), 1.52-1.72 (m, 4H).

Example 1179

[4-(1-Methyl-piperidin-4-yl)-phenyl]-(7-pyridin-3-yl-pyrrolo[2,1-f][1,2,4]triazin-2-yl)-amine; compound with trifluoro-acetic acid The titled compound was prepared in an analogous fashion to Example 1178 replacing N-[2-(2-Methanesulfinyl-pyrrolo[2,1-f][1,2,4]triazin-7-yl)-phenyl]-N-methyl-methanesulfonamide with 2-Methanesulfinyl-7-pyridin-3-yl-pyrrolo[2,1-f][1,2,4]triazine to give a yellow solid (38 mg, 20%). LCMS (E/I+) 385.17 (M+H). NMR $^1$H (DMSO-d$_6$)-9.57 (s, 1H), 9.40 (s, 1H), 9.31 (bs, 1 h), 9.05 (s, 1H), 8.53-8.70 (m, 2H), 7.71 (d, 2H, J=7.64 Hz), 7.62 (t, 1H, J=5.94 Hz), 7.33 (d, 1H, J=4.24 Hz), 7.19 (d, 2H, J=7.64 Hz), 7.01 (d, 1H, J=4.24 Hz), 3.30 (d, 2H, J=11.08 Hz), 3.07 (q, 2H, J=11.03 Hz), 3.70-3.95 (m, 4H), 2.04 (d, 2H, J=13.58 Hz), 1.82 (q, 2H, J=13.58 Hz).

Example 1180

[7-(6-Methoxy-pyridin-3-yl)-pyrrolo[2,1-f][1,2,4]triazin-2-yl]-[4-(1-methyl-piperidin-4-yl)-phenyl]-amine The titled compound was prepared in an analogous fashion to Example 1178 replacing N-[2-(2-Methanesulfinyl-pyrrolo[2,1-f][1,2,4]triazin-7-yl)-phenyl]-N-methyl-methanesulfonamide with 2-Methanesulfinyl-7-(6-methoxy-pyridin-3-yl)-pyrrolo[2,1-f][1,2,4]triazine to give a yellow solid (55 mg, 26%). LCMS (E/I+) 415.17 (M+H). NMR $^1$H (DMSO-d$_6$)-9.49 (s, 1H), 9.30 (bs, 1H), 8.98 (s, 1H), 8.91 (s, 1H), 8.52 (d, 1H, J=8.47 Hz), 7.70 (d, 2H, J=8.47 Hz), 7.10-7.20 (m, 3H), 7.01 (d, 1H, J=8.42 Hz), 6.97 (d, 1H, J=4.21 Hz), 3.94 (s, 3H), 3.53 (d, 2H, J=12.86 Hz), 3.80 (q, 2H, J=11.79 Hz), 2.64-2.85 (m, 4H), 2.04 (d, 2H, J=13.76 Hz), 1.82 (q, 2H, J=13.04 Hz).

Example 1181

2-(4-{4-[7-(1-Methyl-1H-pyrazol-4-yl)-pyrrolo[2,1-f][1,2,4]triazin-2-ylamino]-phenyl}-piperazin-1-yl)-ethanol The titled compound was prepared in an analogous fashion to Example 1175 replacing N-[2-(2-Methanesulfinyl-pyrrolo[2,1-f][1,2,4]triazin-7-yl)-phenyl]-N-methyl-methane-sulfonamide with 2-Methanesulfinyl-7-(1-methyl-1H-pyrazol-4-yl)-pyrrolo[2,1-f][1,2,4]triazine to give a yellow solid (45 mg, 36%). LCMS (E/I+) 419.21 (M+H). NMR $^1$H (DMSO-d$_6$)-9.53 (bs, 1H), 9.17 (s, 1H), 8.86 (s, 1H), 8.40 (s, 1H), 8.16 (s, 1H), 7.64 (d, 2H, J=8.03 Hz), 6.95-7.10 (m, 3H), 6.88 (d, 1H, J=4.25 Hz), 5.40 (bs, 1H), 3.97 (s, 3H), 3.63-3.73 (m, 4H), 3.61 (d, 2H, J=12.37 Hz), 3.15-3.32 (m, 4H), 3.04 (t, 2H, J=12.32 Hz).

Example 1182

(2-{2-[4-(4-Methyl-piperazin-1-yl)-phenylamino]-pyrrolo[2,1-f][1,2,4]triazin-7-yl}-phenoxy)-acetic acid Into an 8-dram vial, (2-{2-[4-(4-Methyl-piperazin-1-yl)-phenylamino]-pyrrolo[2,1-f][1,2,4]triazin-7-yl}-phenoxy)-acetic acid tert-butyl ester (0.180 g, 0.350 mmol), Methylene chloride (5.0 mL, 78 mmol), and Trifluoroacetic Acid (1.00 mL, 13.0 mmol) were added. The reaction was stirred at room temperature overnight. The reaction was partitioned with saturated NaHCO$_3$ and DCM. The organic was separated, washed with Brine and dried over Na$_2$SO$_4$. The solid was filtered and washed with DCM. The solvent was removed under vacuum. The reaction mixture was purified via HPLC reverse phase chromatography with 0.1% TFA in Water and 0.1% TFA in ACN. The collected fractions were lyophilized to give (2-{2-[4-(4-Methyl-piperazin-1-yl)-phenylamino]-pyrrolo[2,1-f][1,2,4]triazin-7-yl}-phenoxy)-acetic acid as a yellow solid (32 mg, 20%). LCMS (E/I+) 459.14 (M+H). NMR $^1$H (DMSO-d$_6$)-13.28 (bs, 1H), 9.58 9 bs, 1H), 9.24 (s, 1H), 8.92 (s, 1H), 8.07 (d, 1H, J=7.44 Hz), 7.65 (d, 2H, J=8.12 Hz), 7.40 (t, 1H, J=8.12 Hz), 7.17-7.20 (m , 2H), 7.10 9 d, 1H, J=8.79 Hz), 6.85-6.93 (m, 3H), 4.75 (s, 2H), 3.74 (d, 2H, J=12.85 Hz), 3.53 (d, 2H, J=11.50 Hz), 3.18 (q, 2H, J=10.15 Hz), 2.80-2.93 (m, 5H).

Example 1183

[7-(2-Methoxy-phenyl)-pyrrolo[2,1-f][1,2,4]triazin-2-yl]-[1-(2-morpholin-4-yl-ethyl)-1H-pyrazol-3-yl]-amine; compound with trifluoro-acetic acid 1183a. Into an 8-dram vial, 3-Nitro-1H-pyrazole (0.50 g, 4.4 mmol), 4-(2-chloroethyl)-morpholine hydrochloride (1.23 g, 6.63 mmol), Potassium carbonate (1.83 g, 13.3 mmol), and Acetonitrile (30 mL, 600 mmol) were added. The reaction mixture was heated. The reaction was poured over ice. The reaction was partitioned with water and DCM. The organic was separated, washed with Brine and dried over Na$_2$SO$_4$. The solid was filtered and washed with DCM. The solvent was removed under vacuum. The reaction mixture was purified via ISCO column chromatography with DCM and methanol as eluant (1 to 3% methanol). The collected fractions afforded 4-[2-(3-Nitro-pyrazol-1-yl)-ethyl]-morpholine a yellow solid (0.75 g, 75%).

1183b. Into a round bottom flask, 4-[2-(3-Nitro-pyrazol-1-yl)-ethyl]-morpholine (0.495 g, 2.19 mmol), 10% Pd/C (10:90, Palladium:carbon black, 0.23 g, 0.22m mol), and Ethanol (10 mL, 0.2 mol) were added. The mixture was evacuated under house vacuum and charged with a hydrogen balloon (3×). The reaction was stirred at room temperature under an atmosphere of Hydrogen via a balloon. The solid was filtered. The solvent was removed under vacuum to afford a white solid (0.40 g, 93%).

1183c. Into a microwave vial, 1-(2-Morpholin-4-yl-ethyl)-1H-pyrazol-3-ylamine (0.100 g, 0.510 mmol), 2-Methanesulfinyl-7-(2-methoxy-phenyl)-pyrrolo[2,1-f][1,2,4]triazine (0.072 g, 0.25 mmol), N,N-Diisopropylethylamine (0.0877 mL, 0.503 mmol), and 1-Methoxy-2-propanol (0.250 mL, 2.56 mmol) were added. The reaction was microwaved on 300 watts, 180° C. for 120 minutes. The solvent was removed under vacuum. The reaction mixture was purified via HPLC reverse phase chromatography with 0.1% TFA in Water and 0.1% TFA in ACN. The collected fractions were lyophilized to give [7-(2-Methoxy-phenyl)-pyrrolo[2,1-f][1,2,4]triazin-2-yl]-[1-(2-morpholin-4-yl-ethyl)-1H-pyrazol-3-yl]-amine; compound with trifluoro-acetic acid as a yellow solid (38 mg, 28%). LCMS (E/I+) 420.16 (M+H). NMR $^1$H (DMSO-d$_6$)-9.73 (s, 1H), 8.93 (s, 1H), 7.78 (d, 1H, J=8.14 Hz), 7.63 (s, 1H), 7.45 (t, 1H, J=8.14 Hz), 7.20 (d, 1H, J=6.46 Hz), 7.02 (t, 1H, J=7.46 Hz), 6.92 (bs, 2H), 6.48 (s, 1 h), 4.40 (bs, 2H), 3.85-4.10 (m, 4H), 3.77 (s, 3H), 3.54 (bs, 2H), 3.00-3.30 (m, 4H).

Example 1184

[1-(2-Morpholin-4-yl-ethyl)-1H-pyrazol-3-yl]-(7-pyridin-3-yl-pyrrolo[2,1-f][1,2,4]triazin-2-yl)-amine The titled compound was prepared in an analogous fashion to Example 1183 replacing 2-Methanesulfinyl-7-(2-methoxy-phenyl)-pyrrolo[2,1-f][1,2,4]triazine with 2-Methanesulfinyl-7-pyridin-3-yl-pyrrolo[2,1-f][1,2,4]triazine to give a yellow solid (58 mg, 46%). LCMS (E/I+) 391.15 (M+H). NMR $^1$H (DMSO-d$_6$)-9.88 (s, 1 h), 9.60 (s, 1H), 9.03 (s, 1H), 8.57-8.67 (m, 2H), 7.76 (s, 1H), 7.60 (bs, 1H), 7.34 (bs, 1H), 7.00 (bs, 1H), 6.49 (s, 1H), 4.49 (t, 2H, J=6.29 Hz), 3.85 (bs, 4H), 3.64 (t, 2H, J=6.29 Hz), 3.30 (bs, 4H).

Example 1185

N-(3-{2-[1-(2-Morpholin-4-yl-ethyl)-1H-pyrazol-3-ylamino]-pyrrolo[2,1-f][1,2,4]triazin-7-yl}-phenyl)-methanesulfonamide The titled compound was prepared in an analogous fashion to Example 1183 replacing 2-Methanesulfinyl-7-(2-methoxy-phenyl)-pyrrolo[2,1-f][1,2,4]triazine with N-[3-(2-Methanesulfinyl-pyrrolo[2,1-f][1,2,4]triazin-7-yl)-phenyl]-methanesulfonamide to give a yellow solid (52 mg, 31%). LCMS (E/I+) 483.14 (M+H). NMR $^1$H (DMSO-d$_6$)-9.80 (s, 1H), 8.99 (s, 1H), 7.95 (d, 1H, J=7.56 Hz), 7.83 (s, 1H), 7.71 (s, 1H), 7.48 (t, 1H, J=8.14 Hz), 7.28 (d, 1H, J=8.14 Hz), 7.06

(d, 1H, J=4.65 Hz), 6.96 (d, 1H, J=4.65 Hz) Hz, 6.66 (s, 1H), 4.45 (t, 2H, J=6.84 Hz), 3.10-4.10 (m, 10H), 3.03 (s, 3H).

Example 1186

N-Methyl-N-(2-{2-[1-(2-morpholin-4-yl-ethyl)-1H-pyrazol-3-ylamino]-pyrrolo[2,1-f][1,2,4]triazin-7-yl}-phenyl)-methanesulfonamide The titled compound was prepared in an analogous fashion to Example 1183 replacing 2-Methanesulfinyl-7-(2-methoxy-phenyl)-pyrrolo[2,1-f][1,2,4]triazine with N-[2-(2-Methanesulfinyl-pyrrolo[2,1-f][1,2,4]triazin-7-yl)-phenyl]-N-methyl-methanesulfonamide to give a yellow solid (58 mg, 46%). LCMS (E/I+) 497.17 (M+H). NMR $^1$H (DMSO-$d_6$)-9.73 (s, 1H), 8.96 (s, 1H), 7.91 (d, 1H, J=6.83 Hz), 7.66 (d, 1H, J=6.83 Hz), 7.62 (s, 1H), 7.48-7.58 (m, 2H), 6.95 (bs, 2H), 6.40 (s, 1H), 4.40 (bs, 2H), 3.10-4.10 (m, 10H), 3.09 (s, 3H), 2.85 (s, 3H).

Example 1187

[7-(1-Methyl-1H-pyrazol-4-yl)-pyrrolo[2,1-f][1,2,4]triazin-2-yl]-[4-(4-morpholin-4-yl-piperidin-1-yl)-phenyl]-amine The titled compound was prepared in an analogous fashion to Example 18 replacing 4-(4-Methyl-piperazin-1-yl)-phenylamine with 4-(4-Morpholin-4-yl-piperidin-1-yl)-phenylamine to give a yellow solid (61 mg, 42%). LCMS (E/I+) 459.20 (M+H). NMR $^1$H (DMSO-$d_6$)-9.65 (bs, 1H), 9.15 (s, 1H), 8.84 (s, 1H), 8.40 (s, 1H), 8.16 (s, 1H), 7.61 (d, 2H, J=8.39 Hz), 7.07 (d, 2H, J=8.39 Hz), 7.03 (d, 1H, J=4.39 Hz), 6.88 (d, 1H, J=4.39 Hz), 4.04 (d, 2H, J=12.00 Hz), 3.93 (s, 3H), 3.85 (d, 2H, J=12.00 Hz), 3.67 (t, 2H, J=12.00 Hz), 3.52 (d, 2H, j=12.00 Hz), 3.20-3.32 (m, 1H), 3.13 (bs, 2H), 2.74 (t, 2H, J=12.00 Hz), 2.17 (d, 2H, J=12.00 Hz), 1.76 (q, 2H, J=10.80 Hz).

Example 1188

(4-Methyl-piperazin-1-yl)-(1-{4-[7-(1-methyl-1H-pyrazol-4-yl)-pyrrolo[2,1-f][1,2,4]triazin-2-ylamino]-phenyl}-piperidin-4-yl)-methanone The titled compound was prepared in an analogous fashion to Example 18 replacing 4-(4-Methyl-piperazin-1-yl)-phenylamine with [1-(4-Amino-phenyl)-piperidin-4-yl]-(4-methyl-piperazin-1-yl)-methanone to give a yellow solid (82 mg, 53%). LCMS (E/I+) 500.25 (M+H). NMR $^1$H (DMSO-$d_6$)-10.00 (bs, 1H), 9.25 (bs, 1H), 8.86 (s, 1H), 8.41 (s, 1H), 8.17 (s, 1H), 7.66 (bs, 2H), 7.25 (d, 2H, J=8.72 Hz), 7.13 (d, 2H, J=8.72 Hz), 7.03 (bs, 1H), 6.98 (s, 2H), 6.89 (s, 1H), 4.50 (bs, 1H), 4.23 (bs, 1H), 3.94 (s, 3H), 2.78-3.80 (m, 9H), 2.83 (s, 3H), 1.82 (bs, 4H).

Example 1189

[4-(4-Ethyl-morpholin-2-yl)-phenyl]-[7-(1-methyl-1H-pyrazol-4-yl)-pyrrolo[2,1-f][1,2,4]triazin-2-yl]-amine The titled compound was prepared in an analogous fashion to Example 18 replacing 4-(4-Methyl-piperazin-1-yl)-phenylamine with 4-(4-Ethyl-morpholin-2-yl)-phenylamine to give a yellow solid (82 mg, 53%). LCMS (E/I+) 404.20 (M+H). NMR $^1$H (DMSO-$d_6$)-9.77 (bs, 1H), 9.32 (s, 1H), 8.90 (s, 1H), 8.41 (s, 1H), 8.21 (s, 1H), 7.80 (d, 2H, J=8.21 Hz), 7.40 (d, 2H, J=8.21 Hz), 7.06 (d, 1H, J=4.54 Hz), 6.93 (d, 1H, J=4.54 Hz), 4.71 (d, 1H, J=10.83 Hz), 4.22 (d, 1H, J=13.32), 3.95 (s, 3H), 3.87 (t, 1H, J=12.38 Hz), 3.66 (d, 1H, J=11.61 Hz), 3.02-3.26 (m, 4H), 1.26 (t, 3H, J=6.96 Hz).

Example 1190

[7-(2-Methoxy-phenyl)-pyrrolo[2,1-f][1,2,4]triazin-2-yl]-[1-(2-morpholin-4-yl-ethyl)-1H-pyrazol-4-yl]-amine The titled compound was prepared in an analogous fashion to Example 1183 replacing 3-nitro-1H-pyrazole with 4-nitro-1H-pyrazole to give a yellow solid (91 mg, 63%). LCMS (E/I+) 420.20 (M+H). NMR $^1$H (DMSO-$d_6$)-9.87 (bs, 1H), 9.41 (s, 1H), 8.99 (s, 1H), 7.84 (d, 1H, J=7.83), 7.73 (s, 1H), 7.60 (s, 1H), 7.48 (t, 1H, J=7.83 Hz), 7.24 (d, 1H, J=8.58 Hz), 7.15 (t, 1H, J=7.09 Hz), 6.90 (bs, 2H), 4.40 (t, 2H, J=5.67 Hz), 3.70-4.10 (m, 4H), 3.78 (s, 3H), 3.60 (t, 2H, J=5.67 Hz), 3.00-3.45 (m, 4H).

Example 1191

[1-(2-Morpholin-4-yl-ethyl)-1H-pyrazol-4-yl]-(7-pyridin-3-yl-pyrrolo[2,1-f][1,2,4]triazin-2-yl)-amine The titled compound was prepared in an analogous fashion to Example 1190 replacing 2-Methanesulfinyl-7-(2-methoxy-phenyl)-pyrrolo[2,1-f][1,2,4]triazine with 2-Methanesulfinyl-7-pyridin-3-yl-pyrrolo[2,1-f][1,2,4]triazine to give a yellow solid (55 mg, 43%). LCMS (E/I+) 391.15 (M+H). NMR $^1$H (DMSO-$d_6$)-9.55 (s, 1H), 9.41 (s, 1H), 9.00 (s, 1H), 8.63 (d, 1H, J=4.29 Hz), 8.55 (d, 1H, J=7.86 Hz), 7.93 (s, 1H), 7.60-7.68 (m, 2H), 7.26 (d, 1H, J=3.57 Hz), 6.99 (d, 1H, J=3.57 Hz), 4.51 (t , 2H, J=6.04 Hz), 3.82 (bs, 4H), 3.65 (t, 2H, J=6.04 Hz), 3.28 (bs, 4H).

Example 1192

[7-(6-Methoxy-pyridin-3-yl)-pyrrolo[2,1-f][1,2,4]triazin-2-yl]-[1-(2-morpholin-4-yl-ethyl)-1H-pyrazol-4-yl]-amine The titled compound was prepared in an analogous fashion to Example 1190 replacing 2-Methanesulfinyl-7-(2-methoxy-phenyl)-pyrrolo[2,1-f][1,2,4]triazine with 2-Methanesulfinyl-7-(6-methoxy-pyridin-3-yl)-pyrrolo[2,1-f][1,2,4]triazine to give a yellow solid (65 mg, 48%). LCMS (E/I+) 421.19 (M+H). NMR $^1$H (DMSO-$d_6$)-9.48 (s, 1H), 8.93 (s, 2H), 8.44 (d, 1H, J=8.87 Hz), 7.91 (s, 1H), 7.64 (s, 1H), 7.12 (d, 1H, J=4.09 Hz), 7.06 (d, 1H, J=8.87 Hz), 6.95 (d, 1H, J=4.09 Hz), 4.51 (bs, 2H), 3.45-4.20 (m, 9H), 3.00-3.42 (m, 4H).

Example 1193

N-Methyl-N-(2-{2-[1-(2-morpholin-4-yl-ethyl)-1H-pyrazol-4-ylamino]-pyrrolo[2,1-f][1,2,4]triazin-7-yl}-phenyl)-methanesulfonamide The titled compound was prepared in an analogous fashion to Example 1190 replacing 2-Methanesulfinyl-7-(2-methoxy-phenyl)-pyrrolo[2,1-f][1,2,4]with N-[2-(2-Methanesulfinyl-pyrrolo[2,1-f][1,2,4]triazin-7-yl)-phenyl]-N-methyl-methanesulfonamide to give a yellow solid (82 mg, 53%). LCMS (E/I+) 497.16 (M+H). NMR $^1$H (DMSO-$d_6$)-

9.42 (s, 1H), 8.92 (s, 1H), 7.96 (d, 1H, J=7.51 Hz), 7.64-7.72 (m, 2H), 7.53-7.63 (m, 3H), 6.88-6.98 (m, 2H), 4.40 (t, 2H, J=6.26 Hz), 3.49-4.10 (m, 6H), 3.08-3.42 (m, 4H), 3.07 (s, 3H), 2.87 (s, 3H).

Example 1194

N-(3-{2-[5-(4-Methyl-piperazin-1-yl)-pyridin-2-ylamino]-pyrrolo[2,1-f][1,2,4]triazin-7-yl}-phenyl)-methanesulfonamide The titled compound was prepared in an analogous fashion to Example 1177 replacing 2-Methanesulfinyl-7-(2-methoxy-phenyl)-pyrrolo[2,1-f][1,2,4]triazine with N-[3-(2-Methanesulfinyl-pyrrolo[2,1-f][1,2,4]triazin-7-yl)-phenyl]-methanesulfonamide to give a yellow solid (63 mg, 42%). LCMS (E/I+) 479.15 (M+H). NMR $^1$H (DMSO-d$_6$)-9.84 (s, 1H), 9.78 (s, 1H), 9.76 (bs, 1H), 9.05 (s, 1H), 8.02 (s, 1H), 7.89-8.01 (m, 3H), 7.61 (d, 1H, J=9.28 Hz), 7.53 (t, 1H, J=7.73 Hz), 7.29 (d, 1H, J=8.25 Hz), 7.16 (bs, 1H), 7.04 (bs, 1H), 3.84 (d, 2H, J=13.04 Hz), 3.56 (d, 2H, J=12.32 Hz), 3.19 (q, 2H, J=10.51 Hz), 2.90-3.10 (m, 5H), 2.88 (s, 2H).

Example 1195

N-(3-{2-[1-(2-Morpholin-4-yl-ethyl)-1H-pyrazol-4-ylamino]-pyrrolo[2,1-f][1,2,4]triazin-7-yl}-phenyl)-methanesulfonamide The titled compound was prepared in an analogous fashion to Example 1190 replacing 2-Methanesulfinyl-7-(2-methoxy-phenyl)-pyrrolo[2,1-f][1,2,4]with N-[3-(2-Methanesulfinyl-pyrrolo[2,1-f][1,2,4]triazin-7-yl)-phenyl]-methanesulfonamide to give a yellow solid (72 mg, 48%). LCMS (E/I+) 483.15 (M+H). NMR $^1$H (DMSO-d$_6$)-9.92 (s, 1H), 9.37 (s, 1H), 8.95 (s, 1H), 7.94 (d, 2H, J=7.86 Hz), 7.84 (d, 1H, J=12.02 Hz), 7.67 (d, 1H, J=7.86 Hz), 7.54 (t, 1H, J=7.86 Hz), 7.31 (d, 1H, J=7.86 Hz), 7.03 (d, 1H, J=4.62 Hz), 6.95 (d, 1H, J=4.62 Hz) 4.51 (t, 2H, J=5.43 Hz), 3.10-4.10 (m, 10H), 3.05 (s, 3H).

Example 1196

5-{2-[4-(4-Methyl-piperazin-1-yl)-phenylamino]-pyrrolo[2,1-f][1,2,4]triazin-7-yl}-furan-2-carbaldehyde Into a 8-dram vial, Palladium Acetate (0.00988 g, 0.0440 mmol), Triphenylphosphine (0.0338 g, 0.129 mmol) and 1,4-Dioxane (2 mL) were added and stirred at room temperature for 10 minutes. (7-Bromo-pyrrolo[2,1-f][1,2,4]triazin-2-yl)-[4-(4-methyl-piperazin-1-yl)-phenyl]-amine (0.320 g, 0.826 mmol), 2-Formylfuran-5-boronic acid (0.2312 g, 1.652 mmol), N,N-Dimethylformamide (2 mL) and 1.50 M of Sodium carbonate in Water (6 mL, 10 mmol) were added. The reaction mixture was heated at 90° C. overnight. The reaction was cooled to room temperature. Solvent was removed under vacuum to give a yellow solid. The resulting solid was partitioned with water and DCM. The organic was separated, washed with Brine and dried over Na$_2$SO$_4$. The solid was filtered and washed with DCM. The solvent was removed under vacuum. The reaction mixture was purified via ISCO column chromatography with DCM and methanol as eluant (5 to 25% methanol). The collected fractions afforded 5-{2-[4-(4-Methyl-piperazin-1-yl)-phenylamino]-pyrrolo[2,1-f][1,2,4]triazin-7-yl}-furan-2-carbaldehyde as a yellow solid (110 mg, 33%). LCMS (E/I+) 403.19 (M+H). NMR $^1$H (DMSO-d$_6$)-963 (s, 1H), 9.40 (s, 1H), 9.04 (s, 1H), 7.78 (d, 1H, J=3.07 Hz), 7.62 (d, 2H, J=9.05 Hz), 7.45 (d, 1H, J=3.77 Hz), 7.21 (d, 1H, J=4.90 Hz), 7.01 (d, 2H, J=9.05 Hz), 6.97 (d, 1H, J=4.90 Hz), 3.11 (t, 4H, J=4.91 Hz), 2.47 (t, 4H, J=4.91 Hz), 2.23 (s, 3H).

Example 1197

N-Methyl-N-(2-{2-[5-(4-methyl-piperazin-1-yl)-pyridin-2-ylamino]-pyrrolo[2,1-f][1,2,4]triazin-7-yl}-phenyl)-methanesulfonamide The titled compound was prepared in an analogous fashion to Example 1177 replacing 2-Methanesulfinyl-7-(2-methoxy-phenyl)-pyrrolo[2,1-f][1,2,4]triazine with N-[2-(2-Methanesulfinyl-pyrrolo[2,1-f][1,2,4]triazin-7-yl)-phenyl]-N-methyl-methanesulfonamide to give a yellow solid (22 mg, 33%). LCMS (E/I+) 493.16 (M+H). NMR $^1$H (DMSO-d$_6$)-9.72 (bs, 1H), 9.02 (s, 1H), 8.01 (d, 1H, J=3.20 Hz), 7.98 (dd, 1H, JJ=1, 87, 7.48 Hz), 7.81 (d, 1H, J=9.08 Hz), 7.68 (dd, 1H, JJ=1.60, 7.48 Hz), 7.52-7.62 (m, 2H), 7.47 (dd, 1H, JJ=2.94, 9.08 Hz), 7.05 (d, 1H, J=5.81 Hz), 7.02 (d, 1H, J=4.81 Hz), 3.81 (d, 2H, J=14.08 Hz), 3.54 (d, 2H, J=13.05 Hz), 3.05-3.25 (m, 5H), 2.95 (t, 2H, J=14.06 Hz), 2.87 (s, 3H).

Example 1198

(7-{5-[(2-Methanesulfonyl-ethylamino)-methyl]-pyridin-3-yl}-pyrrolo[2,1-f][1,2,4]triazin-2-yl)-[4-(4-methyl-piperazin-1-yl)-phenyl]-amine 1198a. Into a 8-dram vial, Palladium Acetate (0.00772 g, 0.0344 mmol), Triphenylphosphine (0.0264 g, 0.100 mmol) and 1,4-Dioxane (1 mL) were added and stirred at room temperature for 10 minutes. (7-Bromo-pyrrolo[2,1-f][1,2,4]triazin-2-yl)-[4-(4-methyl-piperazin-1-yl)-phenyl]-amine (0.250 g, 0.646 mmol), 5-(4,4,5,5-Tetramethyl-[1,3,2]dioxaborolan-2-yl)-pyridine-3-carbaldehyde (0.3009 g, 1.291 mmol), N,N-Dimethylformamide (1 mL) and 1.50 M of Sodium carbonate in Water (5 mL, 8 mmol) were added. The reaction mixture was heated at 90° C. overnight. The reaction was cooled to room temperature. Solvent was removed under vacuum to give a yellow solid. The resulting solid was partitioned with water and DCM. The organic was separated, washed with Brine and dried over Na$_2$SO$_4$. The solid was filtered and washed with DCM. The solvent was removed under vacuum. The reaction mixture was purified via ISCO column chromatography with DCM and methanol as eluant (5 to 25% methanol). The collected fractions afforded 5-{2-[4-(4-Methyl-piperazin-1-yl)-phenylamino]-pyrrolo[2,1-f][1,2,4]triazin-7-yl}-pyridine-3-carbaldehyde as a yellow solid (65 mg, 24%).

1198b. Into a 8-dram vial, 5-{2-[4-(4-Methyl-piperazin-1-yl)-phenylamino]-pyrrolo[2,1-f][1,2,4]triazin-7-yl}-pyridine-3-carbaldehyde (100.2 mg, 0.2424 mmol), 2-Methanesulfonyl-ethylamine; hydrochloride (0.2322 g, 1.454 mmol), 1,2-Dichloroethane (15.0 mL), and Acetic acid (100.0 uL, 1.759 mmol) were added and heated at 45° C. overnight. Sodium triacetoxyborohydride (0.1541 g, 0.7273 mmol) was added. The reaction mixture was stirred at room temperature for 3 hours. The reaction was partitioned with saturated NaHCO$_3$ and DCM. The organic was separated, washed with Brine and dried over Na$_2$SO$_4$. The solid was filtered and washed with DCM. The solvent was removed under vacuum. The reaction mixture was purified via ISCO column chromatography with DCM and methanol as eluant (5 to 25% methanol). The collected fractions afforded (7-{5-[(2-Methanesulfonyl-ethylamino)-methyl]-pyridin-3-yl}-pyrrolo[2,1-f][1,2,4]triazin-2-yl)-[4-(4-methyl-piperazin-1-yl)-phenyl]-amine as a yellow solid (8 mg, 6%). LCMS (E/I+) 521.19 (M+H). NMR $^1$H (DMSO-d$_6$)-9.27 (s, 1H), 9.19 (d, 1H, J=2.25 Hz), 8.97 (s, 1H), 8.57 (t, 1H, J=1.90 Hz), 8.52 (d, 1H, J=1.61 Hz), 7.56 (d, 2H, J=8.79 Hz), 7.27 (d, 1H, J=5.28 Hz), 6.95 (d, 1H, J=5.28 Hz), 6.92 (d, 1H, J=8.79 Hz), 3.84 (d, 2H, J=5.80 Hz), 3.25 (t, 2H, J=6.63 Hz), 3.08 (t, 4H, J=4.97 Hz), 3.00 (s, 3H), 2.94 (q, 2H, J=6.63 Hz), 2.46 (t, 4H, J=4.97 Hz), 2.24 (s, 3H).

Example 1199

(7-{2-[(2-M ethanesulfonyl-ethylamino)-methyl]-phenyl}-pyrrolo[2,1-f][1,2,4]triazin-2-yl)-[4-(4-methyl-piperazin-1-yl)-phenyl]-amine The titled compound was prepared in an analogous fashion to Example 1198 replacing 5-{2-[4-(4-Methyl-piperazin-1-yl)-phenylamino]-pyrrolo[2,1-f][1,2,4]triazin-7-yl}-pyridine-3-carbaldehyde with 2-{2-[4-(4-Methyl-piperazin-1-yl)-phenylamino]-pyrrolo[2,1-f][1,2,4]triazin-7-yl}-benzaldehyde to give a yellow solid (28 mg, 22%). LCMS (E/I+) 520.17 (M+H). NMR $^1$H (DMSO-d$_6$)-9.16 (s, 1H), 8.93 (s, 1H), 7.64 (d, 1H, J=7.74 Hz), 7.59 (dd, 1H, JJ=1.37, 7.78 Hz), 7.39-7.52 (m, 4H), 6.93 (d, 1H, J=4.58 Hz), 6.91 (d, 1H, J=4.58 Hz), 6.74 (d, 2H, J=8.24 Hz), 3.64 (s, 2H), 3.07 (t, 2H, J=6.51 Hz), 3.00 (t, 4H, J=4.91 Hz), 2.77 (t, 2H, J=5.99 Hz), 2.43 (t, 4H, J=5.14 Hz), 2.21 (s, 3H).

Example 1200

(7-{5-[(2-Methanesulfonyl-ethylamino)-methyl]-furan-2-yl}-pyrrolo[2,1-f][1,2,4]triazin-2-yl)-[4-(4-methyl-piperazin-1-yl)-phenyl]-amine Into an 8-dram vial, 5-{2-[4-(4-Methyl-piperazin-1-yl)-phenylamino]-pyrrolo[2,1-f][1,2,4]triazin-7-yl}-furan-2-carbaldehyde (97.57 mg, 0.2424 mmol), 2-Methanesulfonyl-ethylamine; hydrochloride (0.2322 g, 1.454 mmol), 1,2-Dichloroethane (15.0 mL), and Acetic acid (100.0 uL, 1.759 mmol) were added and heated at 45° C. overnight. Sodium triacetoxyborohydride (0.1541 g, 0.7273 mmol) was added. The reaction mixture was stirred at room temperature for 3 hours. The reaction was partitioned with saturated NaHCO$_3$ and DCM. The organic was separated, washed with Brine and dried over Na$_2$SO$_4$. The solid was filtered and washed with DCM. The solvent was removed under vacuum. The reaction mixture was purified via ISCO column chromatography with DCM and methanol as eluant (5 to 25% methanol). The collected fractions afforded (7-{5-[(2-Methanesulfonyl-ethylamino)-methyl]-furan-2-yl}-pyrrolo[2,1-f][1,2,4]triazin-2-yl)-[4-(4-methyl-piperazin-1-yl)-phenyl]-amine as a yellow solid (45 mg, 36%). LCMS (E/I+) 510.08 (M+H). NMR $^1$H (DMSO-d$_6$)-9.23 (s, 1H), 8.91 (s, 1H), 7.63 (d, 2H, J=8.69 Hz), 7.19 (d, 1H, J=3.02 Hz), 7.00 (d, 1H, J=4.57 Hz), 6.97 (d, 2H, J=9.42 Hz), 6.90 (d, 1H, J=5.03 Hz) Hz, 6.53 (d, 1H, J=3.66 Hz), 3.81 (s, 2H) 3.25 (t, 2H, J=6.40 Hz), 3.10 (t, 4H, J=5.03 Hz), 3.02 (s, 3H), 2.97 (t, 2H, J=6.40 Hz), 2.49 (t, 4H, J=5.03), 2.23 (s, 3H).

Example 1201

[7-(1-Methyl-1H-pyrazol-4-yl)-pyrrolo[2,1-f][1,2,4]triazin-2-yl]-(7-morpholin-4-yl-6,7,8,9-tetrahydro-5H-benzocyclohepten-2-yl)-amine The titled compound was prepared in an analogous fashion to Example 1187 replacing 4-(4-Morpholin-4-yl-piperidin-1-yl)-phenylamine with 7-Morpholin-4-yl-6,7,8,9-tetrahydro-5H-benzocyclohepten-2-ylamine to give a yellow solid (72 mg, 63%). LCMS (E/I+) 444.20 (M+H). NMR $^1$H (DMSO-d$_6$)-9.55 (bs, 1H), 9.32 (s, 1H), 8.88 (s, 1H), 8.44 (s, 1H), 8.21 (s, 1H), 7.70 (d, 1H, J=1.89 Hz), 7.43 (dd, 1H, JJ=2.26, 8.30 Hz), 7.18 (d, 1H, J=8.30 Hz), 7.05 (d, 1H, J=4.90 Hz), 6.91 (d, 1H, J=4.52 Hz), 4.00 (d, 2H, J=12.56 Hz), 3.95 (s, 3H), 3.74 (t, 2H, J=12.10 Hz), 3.59 (t, 2H, J=11.63 Hz), 3.33 (d, 2H, J=12.10 Hz), 3.20 (bs, 2H), 2.65-2.90 (m, 4H), 2.29-2.42 (m, 2H), 1.41-165 (m, 2H).

Example 1202

[7-(2-Methoxy-phenyl)-pyrrolo[2,1-f][1,2,4]triazin-2-yl]-(5-morpholin-4-yl-pyridin-2-yl)-amine The titled compound was prepared in an analogous fashion to Example 1101 replacing-4-(2-Morpholin-4-yl-ethoxy)-phenylamine with 5-Morpholin-4-yl-pyridin-2-ylamine to give a yellow solid (12 mg, 8%). LCMS (E/I+) 403.21 (M+H). NMR $^1$H (DMSO-d$_6$)-9.03 (s, 1H), 7.86 (d, 1H, J=2.21 Hz), 7.75-7.85 (m, 2H), 7.62 (bs, 1H), 7.48 (dt, 1H, JJ=1.84, 8.83 Hz), 7.25 (d, 1H, J=8.46 Hz), 7.14 (d, 1H, J=8.09 Hz), 7.05 (bs, 2H), 3.80 (s, 3H), 3.75 (t, 4H, J=4.86 Hz), 3.10 (t, 4H, J=4.86 Hz).

Example 1203

4-{2-[4-(4-Methyl-piperazin-1-yl)-phenylamino]-pyrrolo[2,1-f][1,2,4]triazin-7-yl}-benzaldehyde The titled compound was prepared in an analogous fashion to Example 1196 replacing 2-Formylfuran-5-boronic acid with 3-formyphenyl boronic acid to give a yellow solid (185 mg, 62%). LCMS (E/I+) 413.21 (M+H). NMR $^1$H (DMSO-d$_6$)-10.06 (s, 1H), 9.32 (s, 1H), 9.00 (s, 1H), 8.49 (d, 2H, J=7.97 Hz), 8.04 (d, 2H, J=7.97 Hz), 7.62 (d, 2H, J=9.42 Hz), 7.34 (d, 1H, J=5.07 Hz), 6.92-7.01 (m, 3H), 3.10 (t, 4H, J=5.16 Hz), 2.47 (t, 2H, J=5.16 Hz), 2.23 (s, 3H).

Example 1204

N-(2-{2-[4-(4-Diethylamino-piperidin-1-yl)-phenylamino]-pyrrolo[2,1-f][1,2,4]triazin-7-yl}-phenyl)-N-methyl-methanesulfonamide Into a microwave vial, N-[3-(2-Methanesulfinyl-pyrrolo[2,1-f][1,2,4]triazin-7-yl)-phenyl]-methanesulfonamide (0.0995 g, 0.284 mmol), [1-(4-Amino-phenyl)-piperidin-4-yl]-diethyl-amine (0.155 g, 0.625 mmol), 1-Methoxy-2-propanol (0.683 mL) and N,N-Diisopropylethylamine (0.109 mL, 0.625 mmol) were added. The reaction was microwaved on 300 watts, 170° C. for 50 minutes. The solvent was removed under vacuum. The reaction mixture was purified via HPLC reverse phase chromatography with 0.1% TFA in Water and 0.1% TFA in ACN. The collected fractions were lyophilized to give N-(2-{2-[4-(4-Diethylamino-piperidin-1-yl)-phenylamino]-pyrrolo[2,1-f][1,2,4]triazin-7-yl}-phenyl)-N-methyl-methanesulfonamide as a brown solid (82 mg, 43%). LCMS (E/I+) 548.21 (M+H). NMR $^1$H (DMSO-d$_6$)-9.24 (bs, 1H), 8.95 (s, 1H), 8.01 (dd, 1H, JJ=1.85, 7.62 Hz), 7.65 (dd, 1H, JJ=1.38, 7.85 Hz), 7.52-7.61 (m, 4H), 6.98 (d, 1H, J=4.52 Hz), 6.93 (d, 1H, J=4.52 Hz), 6.89 (d, 2H, J=8.54 Hz), 3.72 (d, 2H, J=12.49 Hz) 3.43 (bs, 1H), 3.25 (bs, 1H), 3.01-3.19 (m, 5H), 2.89 (s, 3H), 2.76 (t, 2H, J=12.80 Hz), 2.07 (d, 2H, J=11.27 Hz), 1.67-1.85 (m, 2H), 1.24 (t, 6H, J=7.31 Hz).

Example 1205

2-Methyl-propane-2-sulfonic acid (3-{2-[4-(4-diethylamino-piperidin-1-yl)-phenylamino]-pyrrolo[2,1-f][1,2,4]triazin-7-yl}-phenyl)-amide The titled compound was prepared in an analogous fashion to Example 1204 replacing N-[3-(2-Methanesulfinyl-pyrrolo[2,1-f][1,2,4]triazin-7-yl)-phenyl]-methanesulfonamide with 2-Methyl-propane-2-sulfonic acid [3-(2-methanesulfinyl-pyrrolo[2,1-f][1,2,4]triazin-7-yl)-phenyl]-amide to give as a yellow solid (70 mg, 35%). LCMS (E/I+) 576.27 (M+H). NMR $^1$H (DMSO-$d_6$)-9.35 (bs, 1H), 9.00 (s, 1H), 8.93 (s, 1H), 8.58 (s, 1H), 8.34 (d, 1H, J=8.00 Hz), 7.86 (d, 1H, J=8.00 Hz), 7.72 (t, 1H, J=8.00 Hz), 7.61 (d, 2H, J=8.58 Hz), 7.59 (s, 1H), 7.18 (d, 1h, J=5.15 Hz), 7.04 (d, 2H, J=9.18 Hz), 6.97 (d, 1H, J=5.15 Hz), 3.76 (d, 2H, J=12.65 Hz), 3.45 (bs, 1H), 3.30-3.37 (m, 2H), 3.01-3.28 (m, 2H), 2.77 (t, 2H, J=12.65 Hz), 2.08 (d, 2H, J=11.39 Hz), 1.71-1.87 (m, 2H), 1.24 (t, 6H, J=7.45 Hz), 1.14 (s, 9H).

Example 1206

[4-(4-Diethylamino-piperidin-1-yl)-phenyl]-[7-(6-methoxy-pyridin-3-yl)-pyrrolo[2,1-f][1,2,4]triazin-2-yl]-amine The titled compound was prepared in an analogous fashion to Example 1204 replacing N-[3-(2-Methanesulfinyl-pyrrolo[2,1-f][1,2,4]triazin-7-yl)-phenyl]-methanesulfonamide with 2-Methanesulfinyl-7-(6-methoxy-pyridin-3-yl)-pyrrolo[2,1-f][1,2,4]triazine to give a yellow solid (70 mg, 42%). LCMS (E/I+) 472.24 (M+H). NMR $^1$H (DMSO-$d_6$)-9.29 (s, 1H), 8.94 (s, 1H), 8.90 (d, 1H, J=2.47 Hz), 8.54 (dd, 1H, JJ=2.47, 8.42 Hz), 7.61 (d, 2H, J=9.07v), 7.16 (d, 1H, J=4.95 Hz), 6.95-7.05 (m, 3H), 6.94 (d, 1H, J=4.95 Hz), 3.95 (s, 3H), 3.78 (d, 2H, J=11.76 Hz), 3.48 (bs, 1H), 3.20-3.35 (m, 2H), 3.04-3.19 (m, 2H), 2.77 (t, 2H, J=11.76 Hz), 2.08 (d, 2H, J=11.76 Hz), 1.77 (q, 2H, J=11.76 Hz), 1.24 (t, 6H, J=7.18 Hz).

Example 1207

[4-(4-Diethylamino-piperidin-1-yl)-phenyl]-[7-(1-methyl-1H-pyrazol-4-yl)-pyrrolo[2,1-f][1,2,4]triazin-2-yl]-amine The titled compound was prepared in an analogous fashion to Example 1204 replacing N-[3-(2-Methanesulfinyl-pyrrolo[2,1-f][1,2,4]triazin-7-yl)-phenyl]-methanesulfonamide with 2-Methanesulfinyl-7-(1-methyl-1H-pyrazol-4-yl)-pyrrolo[2,1-f][1,2,4]triazine to give a yellow solid (60 mg, 37%). LCMS (E/I+) 445.22 (M+H). NMR $^1$H (DMSO-$d_6$)-9.15 (s, 1H), 8.98 (bs, 1H), 8.84 (s, 1H), 8.40 (s, 1H), 8.16 (s, 1H), 7.61 (d, 2H, J=8.94 Hz), 7.06 (d, 2H, J=8.94 Hz), 7.02 (d, 1H, J=4.47 Hz), 6.88 (d, 1H, J=4.47 Hz), 3.96 (s, 3H), 3.81 (d, 2H, J=12.48 Hz), 3.45 (bs, 1H), 3.19-3.35 (m, 2H), 3.05-3.18 (m, 2H), 2.80 (t, 2H, J=12.03 Hz), 2.09 (d, 2H, J=12.03 Hz), 1.79 (d, 2H, J=12.03 Hz), 1.24 (t, 6H, J=7.13 Hz).

Example 1208

(7-{4-[(2-Methanesulfonyl-ethylamino)-methyl]-phenyl}-pyrrolo[2,1-f][1,2,4]triazin-2-yl)-[4-(4-methyl-piperazin-1-yl)-phenyl]-amine The titled compound was prepared in an analogous fashion to Example 1198 replacing 5-{2-[4-(4-Methyl-piperazin-1-yl)-phenylamino]-pyrrolo[2,1-f][1,2,4]triazin-7-yl}-pyridine-3-carbaldehyde with 4-{2-[4-(4-Methyl-piperazin-1-yl)-phenylamino]-pyrrolo[2,1-f][1,2,4]triazin-7-yl}-benzaldehyde to give a yellow solid (102 mg, 83%). LCMS (E/I+) 520.16 (M+H). NMR $^1$H (DMSO-$d_6$)-9.26 (s, 1H), 8.93 (s, 1H), 8.20 (d, 2H, J=7.76 Hz), 7.66 (d, 2H, J=8.92 Hz), 7.52 (d, 2H, J=8.14 Hz), 7.17 (d, 1H, J=4.65 Hz), 6.96 (d, 2H, J=8.90 Hz), 6.93 (d, 1H, J=4.71 Hz), 3.88 (bs, 2H), 2.60-3.40 (m, 11H), 2.50 (s, 3H).

Example 1209

(7-{3-[(2-Methanesulfonyl-ethylamino)-methyl]-phenyl}-pyrrolo[2,1-f][1,2,4]triazin-2-yl)-(4-morpholin-4-yl-phenyl)-amine 1209a. Into a 8-dram vial, Palladium Acetate (0.021 g, 0.000094 mol) and Triphenylphosphine (0.069 g, 0.00026 mol) were added. The mixture was purged under an atmosphere of Nitrogen for 10 minutes. 1,4-Dioxane (7.10 mL) was added and stirred for 10 minutes at room temperature. (7-Bromo-pyrrolo[2,1-f][1,2,4]triazin-2-yl)-(4-morpholin-4-yl-phenyl)-amine (0.35 g, 0.00094 mol), 3-Formylphenyl boronic acid (0.280 g, 0.00187 mol), N,N-Dimethylformamide (14 mL), and 1.50 M of Sodium carbonate in Water (5.61 mL, 8.42 mmol) were added. The reaction was heated at 90° C. for 3 hours. The reaction was partitioned with water and EtOAc. The organic was separated, washed with Brine, and dried over magnesium sulfate. The solid was filtered and washed with EtOAc. The solvent was removed under vacuum. The product was isolated via column chromatography with DCM and Methanol as eluant (0 to 10% MeOH). The collected fractions afforded a solid. The solid was triturated with Et$_2$O and filtered to give 3-[2-(4-Morpholin-4-yl-phenylamino)-pyrrolo[2,1-f][1,2,4]triazin-7-yl]-benzaldehyde as a yellow (0.20 g, 50%).

1209b. The titled compound was prepared in an analogous fashion to Example 1198 replacing 5-{2-[4-(4-Methyl-piperazin-1-yl)-phenylamino]-pyrrolo[2,1-f][1,2,4]triazin-7-yl}-pyridine-3-carbaldehyde with 3-[2-(4-Morpholin-4-yl-phenylamino)-pyrrolo[2,1-f][1,2,4]triazin-7-yl]-benzaldehyde to give a yellow solid (48 mg, 38%). LCMS (E/I+) 507.13 (M+H). NMR $^1$H (DMSO-$d_6$)-9.26 (s, 1H), 8.94 (s, 1H), 8.18 (s, 1H), 8.12 (bs, 1H), 7.66 (d, 1H, J=9.08 Hz), 7.54 (t, 1H, J=7.46 Hz), 7.42 (d, 1H, J=7.46 Hz), 7.15 (d, 1H, J=4.86 Hz), 6.87-6.95 (m, 3H), 3.97 (bs, 2H), 3.75 (t, 4H, J=4.92 Hz), 3.26-3.40 (m, 5H), 3.00-3.13 (m, 6H).

Example 1210

[7-(4-Methoxy-pyridin-3-yl)-pyrrolo[2,1-f][1,2,4]triazin-2-yl]-[4-(4-methyl-piperazin-1-yl)-phenyl]-amine The titled compound was prepared in an analogous fashion to Example 7 replacing phenyl boronic acid with 4-Methoxy-3-pyridineboronic acid to give a yellow solid (44 mg, 33%). LCMS (E/I+) 416.18 (M+H). NMR $^1$H (DMSO-$d_6$)-9.19 (s, 1H), 8.94 (s, 1H), 8.77 (s, 1H), 8.55 (d, 1H, J=5.76 Hz), 752 (d, 2H, J=8.86 Hz), 7.29 (d, 1H, J=5.76 Hz), 6.93 (d, 1H, J=4.87 Hz), 6.91 (d, 1H, J=4.87 Hz), 6.80 (d, 2H, J=8.86 Hz), 3.88 (s, 3H), 3.02 (t, 4H, J=4.86 Hz), 2.44 (t, 4H, J=4.86 Hz), 2.21 (s, 3H).

Example 1211

[7-(4-Methoxy-pyridin-3-yl)-pyrrolo[2,1-f][1,2,4]triazin-2-yl]-(4-morpholin-4-yl-phenyl)-amine The titled compound was prepared in an analogous fashion to Example 7 replacing 3-chlorophenyl boronic acid with 4-Methoxy-3-pyridineboronic acid to give a yellow solid (57 mg, 52%). LCMS (E/I+) 403.15 (M+H). NMR $^1$H (DMSO-$d_6$)-9.26 (s, 1H), 8.96 (s, 1H), 8.77 (s, 1H), 8.55 (d, 1H, J=6.00 Hz), 7.55 (d, 2H, J=9.01 Hz), 7.29 (d, 1H, J=6.00 Hz), 6.98 (d, 1H, J=4.50v), 6.93 (d, 1H, J=4.50 Hz), 6.67 (d, 2H, J=9.01 Hz), 4.10 (s, 3H), 3.72 (t, 4H, J=4.77 Hz), 3.00 (t, 4H, J=4.77 Hz).

Example 1212

N-Methyl-N-[2-(2-{1-[2-(4-methyl-piperazin-1-yl)-ethyl]-1H-pyrazol-4-ylamino}-pyrrolo[2,1-f][1,2,4]triazin-7-yl)-phenyl]-methanesulfonamide The titled compound was prepared in an analogous fashion to Example 1183 replacing with N-[2-(2-Methane sulfinyl-pyrrolo[2,1-f][1,2,4]triazin-7-yl)-phenyl]-N-methyl-methanesulfonamide to give a yellow solid (78 mg, 50%). LCMS (E/I+) 510.18 (M+H). NMR $^1$H (DMSO-$d_6$)-9.34 (s, 1H), 8.91 (s, 1H), 7.91-7.97 (m, 1H), 7.65-7.70 (m, 1H), 7.55-7.63 (m, 3H), 7.41 (s, 1H), 6.89-6.95 (m, 2H), 4.08 (t, 2H, J=6.37 Hz), 3.35 (bs, 2H), 3.06 (s, 3H), 2.60-2.98 (m, 14H).

Example 1213

{1-[2-(4-Methyl-piperazin-1-yl)-ethyl]-1H-pyrazol-4-yl}-[7-(1-methyl-1H-pyrazol-4-yl)-pyrrolo[2,1-f][1,2,4]triazin-2-yl]-amine The titled compound was prepared in an analogous fashion to Example 1201 replacing 7-Morpholin-4-yl-6,7,8,9-tetrahydro-5H-benzocyclohepten-2-ylamine with 1-[2-(4-Methyl-piperazin-1-yl)-ethyl]-1H-pyrazol-4-ylamine to give a yellow solid (85 mg, 65%). LCMS (E/I+) 407.19 (M+H). NMR $^1$H (DMSO-$d_6$)-9.16 (s, 1H), 8.81 (s, 1H), 8.38 (s, 1H), 8.16 (s, 1H), 7.95 (s, 1H), 7.56 (s, 1H), 6.97 (d, 1H, J=4.70 Hz), 6.87 (d, 1H, J=4.70), 4.27 (t, 2H, J=5.57 Hz), 3.95 (s, 3H), 3.30-3.43 (m, 2H), 2.40-3.20 (m, 11H).

Example 1214

[7-(6-Methoxy-pyridin-3-yl)-pyrrolo[2,1-f][1,2,4]triazin-2-yl]-[4-(4-methyl-piperazin-1-ylmethyl)-phenyl]-amine The titled compound was prepared in an analogous fashion to Example 81 replacing 4-(4-Methyl-piperazin-1-yl)-phenylamine with 4-(4-Methyl-piperazin-1-ylmethyl)-phenylamine to give a yellow solid (10 mg, 10%). LCMS (E/I+) 430.15 (M+H). 9.62 (bs, 1H), 9.00 (s, 1H), 8.91 (d, 1H, J=2.18 Hz), 8.51 (dd, 1H, JJ=2.55, 8.73), 7.76 (d, 2H, J=8.37 Hz), 7.25-7.35 (m, 2H), 7.19 (d, 1H, J=4.73 Hz), 7.02 (d, 1H, J=8.73 Hz), 6.99 (d, 1H, J=4.73 Hz), 3.95 (s, 3H), 2.40-3.77 (m, 13H).

Example 1215

[3-Fluoro-4-(4-methyl-piperazin-1-yl)-phenyl]-[7-(1-methyl-1H-pyrazol-4-yl)-pyrrolo[2,1-f][1,2,4]triazin-2-yl]-amine The titled compound was prepared in an analogous fashion to Example 1201 replacing 7-Morpholin-4-yl-6,7,8,9-tetrahydro-5H-benzocyclohepten-2-ylamine with 3-Fluoro-4-(4-methyl-piperazin-1-yl)-phenylamine to give a yellow solid (100 mg, 50%). LCMS (E/I+) 407.18 (M+H). NMR $^1$H (DMSO-$d_6$)-9.82 (bs, 1H), 9.52 (s, 1H), 8.90 (s, 1H), 8.43 (s, 1H), 8.16 (s, 1H), 7.82 (dd, 1H, JJ=2.25, 5.02 Hz), 7.40 (dd, 1H, JJ=2.00, 8.51 Hz), 7.16 (t, 1H, J=9.01 Hz), 7.07 (d, 1H, J=4.76 Hz), 6.92 (d, 1H, J=4.76 Hz), 3.94 (s, 3H), 3.54 (d, 2H, J=12.12 Hz), 3.47 (d, 2H, J=12.12 Hz), 3.11-3.31 (m, 4H), 3.01 (t, 2H, J=12.12 Hz), 2.88 (s, 3H).

Example 1216

N-tert-Butyl-3-{2-[3-fluoro-4-(4-methyl-piperazin-1-yl)-phenylamino]-pyrrolo[2,1-f][1,2,4]triazin-7-yl}-benzenesulfonamide The titled compound was prepared in an analogous fashion to Example 81 replacing 4-(4-Methyl-piperazin-1-yl)-phenylamine with 3-Fluoro-4-(4-methyl-piperazin-1-yl)-phenylamine to give a yellow solid (95 mg, 41%). LCMS (E/I+) 434.18 (M+H). NMR $^1$H (DMSO-$d_6$)-9.66 (bs, 1H), 9.62 (s, 1H), 8.99 (s, 1H), 8.86 (d, 1H, J=2.38 Hz), 8.51 (dd, 1H, JJ=2.38, 8.71 Hz), 7.77 (dd, 1H, JJ=2.38, 5.31 Hz), 7.39 (dd, 1H, JJ=2.38, 8.62 Hz), 7.18 (d, 1H, J=4.68 Hz), 7.07 (t, 1H, J=9.17 Hz), 6.95-7.03 (m, 3H), 3.94 (s, 3H), 3.33-3.40 (m, 4H), 2.90-3.30 (m, 4H), 2.88 (s, 3H).

Example 1217

2-Methyl-propane-2-sulfonic acid (3-{2-[4-(4-diethylamino-piperidin-1-yl)-phenylamino]-pyrrolo[2,1-f][1,2,4]triazin-7-yl}-phenyl)-amide The titled compound was prepared in an analogous fashion to Example 1205 replacing 1-(4-Amino-phenyl)-piperidin-4-yl]-diethyl-amine with 3-Fluoro-4-(4-methyl-piperazin-1-yl)-phenylamine to give a yellow solid (95 mg, 41%). LCMS (E/I+) 538.19 (M+H). NMR $^1$H (DMSO-$d_6$)-9.65 (s, 1H), 9.57 (bs, 1H), 9.05 (s, 1H), 8.47 (s, 1H), 8.41 (d, 1H, J=8.16 Hz), 7.87 (d, 1H, J=8.16 Hz), 7.72 (t, 1H, J=8.16 Hz) 7.50-7.65 (m, 3H), 7.21 (d, 1H, J=4.39 Hz), 7.13 (t, 1H, J=8.74 Hz), 7.02 (d, 1H, J=4.39 Hz), 3.13-3.90 (m, 6H), 2.83-3.05 (m, 5H), 1.11 (s, 9H).

Example 1218

N-(3-{2-[4-(4-Methyl-piperazin-1-yl)-phenylamino]-pyrrolo[2,1-f][1,2,4]triazin-7-yl}-pyridin-4-yl)-methanesulfonamide 1218a. Into a round bottom, 3-Bromo-pyridin-4-ylamine (0.800 g, 4.62 mmol), 1,2-Dichloroethane (20 mL, 200 mmol), N,N-Diisopropylethylamine (2.99 g, 23.1 mmol) and Methanesulfonyl chloride (1.32 g, 11.6 mmol) were added. The reaction was stirred at 50° C. for 2 hours. The reaction was partitioned with saturated NaHCO$_3$ water and DCM. The organic was separated, washed with Brine and dried over Na$_2$SO$_4$. The solid was filtered and washed with DCM. The solvent was removed under vacuum to give a white solid. The solid was treated with 1.00 M of Tetra-n-butylammonium fluoride in Tetrahydrofuran (13.9 mL, 13.9 mmol). The reaction was heated to reflux for 2 hours. The reaction was partitioned with water and DCM. The organic was separated, washed with Brine and dried over Na$_2$SO$_4$. The solid was filtered and washed with DCM. The solvent was removed under vacuum. The reaction mixture was purified via ISCO column chromatography with DCM and methanol as eluant (0 to 5% methanol). The collected fractions afforded a yellow solid (0.20 g, 28%).

1218b. Into a 30 mL vial, Palladium Acetate (0.0063 g, 0.028 mmol) and Triphenylphosphine (0.021 g, 0.079 mmol)

were added. The mixture was purged under an atmosphere of Nitrogen for 10 minutes. 1,4-Dioxane (2.13 mL) was added and stirred for 10 minutes at room temperature. [4-(4-Methyl-piperazin-1-yl)-phenyl]-[7-(4,4,5,5-tetramethyl-[1,3,2]dioxaborolan-2-yl)-pyrrolo[2,1-f][1,2,4]triazin-2-yl]-amine (0.210 g, 0.483 mmol), N-(3-Bromo-pyridin-4-yl)-methane-sulfonamide (0.0706 g, 0.281 mmol), N,N-Dimethylformamide (4.3 mL), and 1.50 M of Sodium carbonate in Water (1.69 mL, 0.00253 mol) were added. The reaction was heated at 90° C. for 18 hours. The reaction was partitioned with water and EtOAc. The organic was separated, washed with Brine, and dried over magnesium sulfate. The solid was filtered and washed with EtOAc. The solvent was removed under vacuum. The product was isolated via column chromatography with DCM and $NH_3$ in Methanol as eluant (0 to 10% $NH_3$ in MeOH). The collected fractions afforded a solid. The solid was triturated with $Et_2O$ and filtered to give a yellow solid. LCMS (E/I+) 479.12 (M+H). NMR $^1$H (DMSO-$d_6$)-9.29 (s, 1H), 8.93 (s, 1H), 8.71 (s, 1H), 8.01 (d, 1H, J=**), 7.56 (d, 2H, J=6.88 Hz), 7.48 (d, 1H, J=8.99 Hz), 7.43 (d, 1H, J=6.88 Hz), 7.26 (d, 1H, J=4.76 Hz), 6.82-6.92 (m, 3H), 3.05 (t, 4H, J=4.97 Hz), 2.81 (s, 3H), 2.45-2.55 (m, 4H), 2.24 (s, 3H).

Example 1219

N-{3-[2-(4-Morpholin-4-yl-phenylamino)-pyrrolo[2,1-f][1,2,4]triazin-7-yl]-pyridin-4-yl}-methanesulfonamide Into a 30 mL vial, Palladium Acetate (0.0063 g, 0.028 mmol) and Triphenylphosphine (0.021 g, 0.079 mmol) were added. The mixture was purged under an atmosphere of Nitrogen for 10 minutes. 1,4-Dioxane (2.13 mL) was added and stirred for 10 minutes at room temperature. (4-Morpholin-4-yl-phenyl)-[7-(4,4,5,5-tetramethyl-[1,3,2]dioxaborolan-2-yl)-pyrrolo[2,1-f][1,2,4]triazin-2-yl]-amine (0.280 g, 0.665 mmol), N-(3-Bromo-pyridin-4-yl)-methanesulfonamide (0.116 g, 0.462 mmol), N,N-Dimethylformamide (4.3 mL, 0.055 mol), and 1.50 M of Sodium carbonate in Water (1.69 mL, 0.00253 mol) were added. The reaction was heated at 90° C. for 18 hours. The reaction was partitioned with water and EtOAc. The organic was separated, washed with Brine, and dried over magnesium sulfate. The solid was filtered and washed with EtOAc. The solvent was removed under vacuum. The product was isolated via column chromatography with DCM and $NH_3$ in Methanol as eluant (0 to 10% $NH_3$ in MeOH). The collected fractions afforded a solid. The solid was triturated with $Et_2O$ and filtered to give N-{3-[2-(4-Morpholin-4-yl-phenylamino)-pyrrolo[2,1-f][1,2,4]triazin-7-yl]-pyridin-4-yl}-methanesulfonamide as a yellow solid. LCMS (E/I+) 466.10 (M+H). MP 178-180° C. NMR $^1$H (DMSO-$d_6$)-9.21 (s, 1H), 8.92 (s, 1H), 8.72 (d, 1H, J=5.63 Hz), 7.97 (t, 1H, J=5.98 Hz), 7.58 (d, 2H, J=8.79 Hz), 7.43 (d, 1H, J=7.04 Hz), 7.28 (d, 1H, J=4.57 Hz), 6.84-6.95 (m, 3H), 3.74 (t, 4H, J=4.79 Hz), 3.02 (t, 4H, J=4.79 Hz), 2.80 (s, 3H).

Example 1220

(2-Methoxy-4-morpholin-4-ylmethyl-phenyl)-[7-(2-methoxy-phenyl)-pyrrolo[2,1-f][1,2,4]triazin-2-yl]-amine 1220a. Into a 8-dram vial, 19.10 M of Sodium hydroxide in Water (10.0 mL, 191 mmol) and Water (10.0 mL) water were added. The mixture was heated at 100° C. 2-Methanesulfinyl-7-(2-methoxy-phenyl)-pyrrolo[2,1-f][1,2,4]triazine (2.00 g, 6.96 mmol) was added portion wise over 10 minutes. The reaction mixture was heated at 120° C. for 60 minutes. HPLC suggested no SM. The reaction was cooled to room temperature. Glacial acetic acid was added to adjust pH to 4. The mixture was stirred at room temperature for 30 minutes. The solid was filtered, washed with water and subsequently with $Et_2O$. The resulting solid was dried under vacuum overnight to give 7-(2-Methoxy-phenyl)-pyrrolo[2,1-f][1,2,4]triazin-2-ol as a yellow solid (1.50 g, 85%). LCMS 242.15 (M+H).

1220b. Into a 8-dram vial, 7-(2-Methoxy-phenyl)-pyrrolo[2,1-f][1,2,4]triazin-2-ol (1.50 g, 6.22 mmol), Methylene chloride (90.0 mL, 1.40E3 mmol), and N,N-Diisopropylethylamine (4.33 mL, 24.9 mmol) were added. The reaction was stirred for 10 minutes. Trifluoromethanesulfonic anhydride (2.51 mL, 14.9 mmol) was added dropwise to the reaction mixture. The reaction was stirred at room temperature for one hour. The solvent was removed under vacuum. The reaction mixture was purified via ISCO column chromatography with hexane and EtOAc as eluant (20 to 100% EtOAc). The collected fractions afforded Trifluoro-methanesulfonic acid 7-(2-methoxy-phenyl)-pyrrolo[2,1-f][1,2,4]triazin-2-yl ester as a red oil (0.875 g, 38%).

1220c. Into a 8-dram vial, Trifluoro-methanesulfonic acid 7-(2-methoxy-phenyl)-pyrrolo[2,1-f][1,2,4]triazin-2-yl ester (72.9 mg, 0.195 mmol), 2-Methoxy-4-morpholin-4-ylmethyl-phenylamine (0.174 g, 0.782 mmol), N,N-Diisopropylethylamine (0.136 mL, 0.782 mmol), and 1-Methoxy-2-propanol (0.250 mL, 2.56 mmol). The reaction mixture was heated at 120° C. for 60 minutes. HPLC suggested little if any triflate SM. The solvent was removed under vacuum. The reaction mixture was purified via HPLC reverse phase chromatography with 0.1% TFA in Water and 0.1% TFA in ACN. The collected fractions were lyophilized to give (2-Methoxy-4-morpholin-4-ylmethyl-phenyl)-[7-(2-methoxy-phenyl)-pyrrolo[2,1-f][1,2,4]triazin-2-yl]-amine a brown solid (11 mg, 10%). LCMS (E/I+) 445.19 (M+H). NMR $^1$H (DMSO-$d_6$)-9.81 (s, 1H), 8.99 (s, 1H), 8.24 (d, 1H, J=8.32 Hz), 7.73-7.82 (m, 2H), 7.48 (dt, 1H, JJ=1.19, 8.92 Hz), 7.22 (d, 1H, J=8.11 Hz), 7.17 (, s, 1H), 7.11 (t, 1H, J=7.40 Hz), 6.85-7.05 (m, 3H), 4.28 (bs, 2H), 3.90-4.02 (m, 5H), 3.79 (s, 3H), 3.62 (t, 2H, J=11.67 Hz), 3.26 (d, 2H, J=13.80 Hz), 3.08 (bs, 2H).

Example 1221

N-{2-[2-(2-Methoxy-4-morpholin-4-ylmethyl-phenylamino)-pyrrolo[2,1-f][1,2,4]triazin-7-yl]-phenyl}-N-methyl-methanesulfonamide 1221a. Into a 8-dram vial, 19.10 M of Sodium hydroxide in Water (7.88 mL, 1.50E2 mmol) and Water (7.88 mL, 438 mmol) water were added. The mixture was heated at 100° C. N-[2-(2-Methanesulfinyl-pyrrolo[2,1-f][1,2,4]triazin-7-yl)-phenyl]-N-methyl-methanesulfonamide (2.00 g, 5.49 mmol) was added portion wise over 10 minutes. The reaction mixture was heated at 120° C. for 60 minutes. HPLC suggested no SM. The reaction was cooled to room temperature. Glacial acetic acid was added to adjust pH to 4. The mixture was stirred at room temperature for 30 minutes. The solid was filtered, washed with water and subsequently with $Et_2O$. The resulting solid was dried under vacuum overnight to give N-[2-(2-Hydroxy-pyrrolo[2,1-f][1,2,4]triazin-7-yl)-phenyl]-N-methyl-methanesulfonamide as a yellow solid (1.60 g, 92%).

1221b. Into a 8-dram vial, N-[2-(2-Hydroxy-pyrrolo[2,1-f][1,2,4]triazin-7-yl)-phenyl]-N-methyl-methanesulfonamide (0.350 g, 1.10 mmol) was suspended in Methylene chloride (15.9 mL, 248 mmol), and N,N-Diisopropylethylamine (0.766 mL, 4.40 mmol). The mixture was stirred for 10 minutes. Trifluoromethanesulfonic anhydride (0.444 mL, 2.64 mmol) was added dropwise. The homogenous mixture was stirred at room temperature for one hour. The solvent was removed under vacuum. The reaction mixture was purified via ISCO column chromatography with hexane and EtOAc as eluant (20 to 100% EtOAc). The collected fractions afforded Trifluoro-methanesulfonic acid 7-[2-(methanesulfonyl-methyl-amino)-phenyl]-pyrrolo[2,1-f][1,2,4]triazin-2-yl ester as a yellow solid (220 mg, 44%).

1221c. Into an 8-dram vial, Trifluoro-methanesulfonic acid 7-[2-(methanesulfonyl-methyl-amino)-phenyl]-pyrrolo[2,1-f][1,2,4]triazin-2-yl ester (88.0 mg, 0.195 mmol), 2-Methoxy-4-morpholin-4-ylmethyl-phenylamine (0.174 g, 0.782 mmol), N,N-Diisopropylethylamine (0.136 mL, 0.782 mmol), and 1-Methoxy-2-propanol (0.880 mL, 9.00 mmol) were added. The reaction mixture was heated at 120° C. for 4 hours. The solvent was removed under vacuum. The reaction mixture was purified via HPLC reverse phase chromatography with 0.1% TFA in Water and 0.1% TFA in ACN. The collected fractions were concentrated under vacuum to give a glassy solid. The solid was triturated with Et$_2$O to give N-{2-[2-(2-Methoxy-4-morpholin-4-ylmethyl-phenylamino)-pyrrolo[2,1-f][1,2,4]triazin-7-yl]-phenyl}-N-methyl-methanesulfonamide as a yellow solid (46 mg, 37%). LCMS (E/I+) 523.15 (M+H). NMR $^1$H (DMSO-d$_6$)-9.61 (s, 1H), 8.13 (d, 1H, J=8.58 Hz), 7.95-8.00 (m, 1H), 7.86 (s, 1H), 7.66-7.70 (m, 1H), 7.53-7.58 (m, 1H), 7.16 (d, 1H, J=1.72 Hz), 7.04 (d, 1H, J=4.66 Hz), 7.01 (d, 1H, J=4.66 Hz), 6.96 (d, 1H, J=8.58 Hz), 4.29 (d, 2H, J=3.50 Hz), 3.86-4.04 (m, 5H), 3.61 (t, 2H, J=11.67 Hz), 3.20 (d, 2H, J=12.84 Hz), 3.00-3.15 (m, 5H), 2.88 (s, 3H).

Example 1222

4-(4-{7-[2-(Methanesulfonyl-methyl-amino)-phenyl]-pyrrolo[2,1-f][1,2,4]triazin-2-ylamino}-3-methoxy-benzyl)-piperazine-1-carboxylic acid tert-butyl ester The titled compound was prepared in an analogous fashion to Example 1221 replacing 2-Methoxy-4-morpholin-4-ylmethyl-phenylamine with 4-(4-Amino-3-methoxy-benzyl)-piperazine-1-carboxylic acid tert-butyl ester to give a yellow solid (480 mg, 87%). LCMS (E/I+) 622.02 (M+H). NMR $^1$H (DMSO-d$_6$)-8.96 (s, 1H), 7.92-7.99 (m, 1H), 7.90 (d, 1H, J=8.17 Hz), 7.72 (s, 1H), 7.61-7.67 (m, 1H), 7.49-7.57 (m, 2H), 7.00 (d, 1H, J=4.54 Hz), 6.97 (d, 1H, J=4.54 Hz), 6.94 (bs, 1H), 6.73 (d, 1H, J=8.77 Hz), 3.83 (s, 3H), 3.42 (s, 2H), 3.20-3.35 (m, 4H), 3.04 (s, 3H), 2.88 (s, 3H), 2.73-2.85 (m, 4H), 1.48 (s, 9H).

Example 1223

N-{2-[2-(2-Methoxy-4-piperazin-1-ylmethyl-phenylamino)-pyrrolo[2,1-f][1,2,4]triazin-7-yl]-phenyl}-N-methyl-methanesulfonamide Into a 8-dram vial, 4-(4-{7-[2-(Methanesulfonyl-methyl-amino)-phenyl]-pyrrolo[2,1-f][1,2,4]triazin-2-ylamino}-3-methoxy-benzyl)-piperazine-1-carboxylic acid tert-butyl ester (0.450 g, 0.724 mmol), Methylene chloride (15 mL, 230 mmol), and Trifluoroacetic Acid (3 mL, 40 mmol) were added. The reaction was stirred at room temperature overnight. The reaction was partitioned with saturated NaHCO$_3$ and DCM. The organic was separated, washed with Brine and dried over Na$_2$SO$_4$. The solid was filtered and washed with DCM. The solvent was removed under vacuum to give N-{2-[2-(2-Methoxy-4-piperazin-1-ylmethyl-phenylamino)-pyrrolo[2,1-f][1,2,4]triazin-7-yl]-phenyl}-N-methyl-methanesulfonamide as an orange solid (0.37 g, 98%). LCMS (E/I+) 522.12 (M+H). NMR $^1$H (DMSO-d$_6$)-8.95 (s, 1H), 7.95-7.99 (m, 1H), 7.87 (d, 1H, J=7.99 Hz), 7.72 (s, 1H), 7.60-7.67 (m, 1H), 7.50-7.57 (m, 2H), 7.07 (d, 1H, J=4.59 Hz), 6.96 (d, 1H, J=4.59 Hz), 6.93 (s, 1H), 6.72 (d, 1H, J=7.94 Hz), 3.83 (s, 3H), 3.37 (s, 3H), 3.04 (s, 3H), 2.88 (s, 3H), 2.73 (t, 4H, J=4.02 Hz), 2.29 (bs, 4H).

Example 1224

N-[2-(2-{4-[4-((S)-2-Hydroxy-propyl)-piperazin-1-ylmethyl]-2-methoxy-phenylamino}-pyrrolo[2,1-f][1,2,4]triazin-7-yl)-phenyl]-N-methyl-methanesulfonamide Into a 8-dram vial, N-{2-[2-(2-Methoxy-4-piperazin-1-ylmethyl-phenylamino)-pyrrolo[2,1-f][1,2,4]triazin-7-yl]-phenyl}-N-methyl-methanesulfonamide (70 mg, 0.1 mmol), Methanol (5 mL) and (S)-(−)-Propylene Oxide (0.00818 g, 0.141 mmol) were added. The reaction was stirred at room temperature over the weekend. The reaction mixture was purified via HPLC reverse phase chromatography with 0.1% TFA in Water and 0.1% TFA in ACN. The collected fractions were lyophilized to give N-[2-(2-{4-[4-((S)-2-Hydroxy-propyl)-piperazin-1-ylmethyl]-2-methoxy-phenylamino}-pyrrolo[2,1-f][1,2,4]triazin-7-yl)-phenyl]-N-methyl-methanesulfonamide as a yellow solid (10 mg, 11%). LCMS (E/I+) 580.13 (M+H). NMR $^1$H (DMSO-d$_6$)-8.99 (s, 1H), 8.05 (d, 1H, J=7.67 Hz), 7.96-8.01 (m, 1H), 7.80 (s, 1H), 7.64-7.69 (m, 1H), 7.52-7.58 (m, 2H), 7.80 (bs, 1H), 7.03 (d, 1H, J=4.69 Hz), 7.00 (d, 1H, J=4.69 Hz), 6.87 (bd, 1H, J=7.39 Hz), 4.00 (bs, 2H), 3.88 (s, 3H), 2.50-3.70 (bm, 17H), 1.05 (bs, 3H).

Example 1225

N-[2-(2-{4-[4-((R)-2-Hydroxy-3-methoxy-propyl)-piperazin-1-ylmethyl]-2-methoxy-phenylamino}-pyrrolo[2,1-f][1,2,4]triazin-7-yl)-phenyl]-N-methyl-methanesulfonamide Into an 8-dram vial, N-{2-[2-(2-Methoxy-4-piperazin-1-ylmethyl-phenylamino)-pyrrolo[2,1-f][1,2,4]triazin-7-yl]-phenyl}-N-methyl-methanesulfonamide (70.0 mg, 0.134 mmol), (R)-2-Methoxymethyl-oxirane (0.0154 g, 0.174 mmol), and Methanol (5.00 mL) were added. The reaction was stirred at room temperature over the weekend. The solvent was removed under vacuum. The reaction mixture was purified via HPLC reverse phase chromatography with 0.1% TFA in Water and 0.1% TFA in ACN. The selected fractions were concentrated. The residue was partitioned with DCM and sat. NaHCO$_3$. The organic was separated, washed with Brine and dried over Na$_2$SO$_4$. The solid was filtered wand washed with DCM. The solvent was removed under vacuum to give N-[2-(2-{4-[4-((R)-2-Hydroxy-3-methoxy-propyl)-piperazin-1-ylmethyl]-2-methoxy-phenylamino}-pyrrolo[2,1-f][1,2,4]triazin-7-yl)-phenyl]-N-methyl-methanesulfonamide a yellow solid (32 mg, 39%). LCMS (E/I+) 610.15 (M+H). NMR $^1$H (DMSO-d$_6$)-8.95 (s, 1H), 7.92-7.98 (m, 1H), 7.88 (d, 1H, J=8.26 Hz), 7.72 (s, 1H), 7.60-7.67 (m, 1H), 7.50-7.78 (m, 2H), 7.00 (d, 1H, J=4.66 Hz), 6.96 (d, 1H, J=4.66 Hz), 6.92 bs, 1H), 6.72 (d, 1H, J=8.26), 4.47 (bs, 1H), 3.82 (s, 3H) 3.71 (bs, 1H), 3.39 (bs, 2H), 3.25-3.31 (m, 2H), 3.24 (s, 3H), 3.17-3.23 (m, 1H) 3.04 (s, 3H), 2.88 (s, 3H), 2.20-2.42 (m, 9H).

Example 1226

(S)-1-(4-{3-Methoxy-4-[7-(2-methoxy-phenyl)-pyrrolo[2,1-f][1,2,4]triazin-2-ylamino]-benzyl}-piperazin-1-yl)-propan-2-ol The titled compound was prepared in an analogous fashion to Example 1224 replacing 7-[2-(methanesulfonyl-methylamino)-phenyl]-pyrrolo[2,1-f][1,2,4]triazin-2-yl ester with Trifluoro-methanesulfonic acid 7-(2-methoxy-phenyl)-pyrrolo[2,1-f][1,2,4]triazin-2-yl ester to give a yellow solid (17 mg, 20%). LCMS (E/I+) 503.04 (M+H). NMR $^1$H (DMSO-d$_6$)-8.94 (s, 1H), 8.02 (d, 1H, J=8.27), 7.80 (dd, 1H, JJ=1.59, 7.65), 7.63 (s, 1H), 7.46 (dt, 1H, J=1.59, 8.60 Hz), 7.22 (d, 1H, J=8.26 Hz), 7.09 (t, 1H, J=8.60 Hz), 6.97 (d, 1H, J=4.78 Hz), 6.90-6.95 (m, 2H), 4.21 (d, 1H, J=12.72 Hz), 3.85 (s, 3H), 3.78 (s, 3H), 3.52-3.75 (m, 1H), 3.39 (bs, 2H), 3.29 (bs, 2H), 2.10-2.45 (m, 8H), 1.01 (d, 3H, J=6.31).

Example 1227

(R)-1-Methoxy-3-(4-{3-methoxy-4-[7-(2-methoxy-phenyl)-pyrrolo[2,1-f][1,2,4]triazin-2-ylamino]-benzyl}-piperazin-1-yl)-propan-2-ol The titled compound was prepared in an analogous fashion to Example 1225 replacing 7-[2-(methanesulfonyl-methylamino)-phenyl]-pyrrolo[2,1-f][1,2,4]triazin-2-yl ester with Trifluoro-methanesulfonic acid 7-(2-methoxy-phenyl)-pyrrolo[2,1-f][1,2,4]triazin-2-yl ester to give a yellow solid (20 mg, 24%). LCMS (E/I+) 533.03 (M+H). NMR $^1$H (DMSO-d$_6$)-8.94 (s, 1H), 8.02 (d, 1H, J=8.12 Hz), 7.80 (dd, 1H, JJ=1.75, 7.67 Hz), 7.63 (s, 1H), 7.46 (dt, 1H, JJ=1.70, 8.79 Hz), 7.22 (d, 1H, J=8.34 Hz), 7.09 (t, 1H, J=7.63 Hz), 6.97 (d, 1H, J=4.62 Hz), 6.90-6.95 (m, 2H), 6.73 (d, 1H, J=8.34 Hz), 4.47 (d, 1H, J=4.61 Hz), 3.87 (s, 3H), 3.85 (s, 3H), 3.66-3.75 (m, 1H), 3.39 (bs, 2H), 3.16-0.330 (m, 7H), 2.20-2.45 (m, 8H).

Example 1228

N-[2-(2-{4-[4-((R)-2,3-Dihydroxy-propyl)-piperazin-1-ylmethyl]-2-methoxy-phenylamino}-pyrrolo[2,1-f][1,2,4]triazin-7-yl)-phenyl]-N-methyl-methanesulfonamide Into an 8-dram vial, N-{2-[2-(2-Methoxy-4-piperazin-1-ylmethyl-phenylamino)-pyrrolo[2,1-f][1,2,4]triazin-7-yl]-phenyl}-N-methyl-methanesulfonamide (80 mg, 0.2 mmol), (R)-Oxiranemethanol (0.0350 g, 0.472 mmol), and Methanol (5.87 mL, 145 mmol) were added. The reaction was stirred at room temperature over the weekend. The solvent was removed under vacuum. The reaction mixture was purified via HPLC reverse phase chromatography with 0.1% TFA in Water and 0.1% TFA in ACN. The selected fractions were concentrated. The residue was partitioned with DCM and sat. NaHCO$_3$. The organic was separated, washed with Brine and dried over Na$_2$SO$_4$. The solid was filtered wand washed with DCM. The solvent was removed under vacuum to give N-[2-(2-{4-[4-((R)-2,3-Dihydroxy-propyl)-piperazin-1-ylmethyl]-2-methoxy-phenylamino}-pyrrolo[2,1-f][1,2,4]triazin-7-yl)-phenyl]-N-methyl-methanesulfonamide as a yellow solid (20 mg, 21%). LCMS (E/I+) 596.11 (M+H). NMR $^1$H (DMSO-d$_6$)-8.97 (s, 1H), 7.90-7.98 (m, 1H), 7.88 (d, 1H, J=8.21 Hz), 7.72 (s, 1H), 7.62-7.66 (m, 1H), 7.51-7.56 (m, 1H), 7.00 (d, 1H, J=4.67 Hz), 6.96 (d, 1H, J=4.67 Hz), 6.92 (bs, 1H), 6.72 (d, 1H, J=8.01 Hz), 4.51 (t, 1H, J=5.55), 4.34 (d, 1H, J=4.34 Hz), 3.82 (s, 3H), 2.18-3.70 (bm, 21H).

Example 1229

[7-(1,3-Dimethyl-1H-pyrazol-4-yl)-pyrrolo[2,1-f][1,2,4]triazin-2-yl]-[4-(4-methyl-piperazin-1-yl)-phenyl]-amine Into a 30 mL vial, Palladium Acetate (0.0059 g, 0.026 mmol) and Triphenylphosphine (0.019 g, 0.074 mmol) were added. The mixture was purged under an atmosphere of Nitrogen for 10 minutes. 1,4-Dioxane (2.00 mL) was added and stirred for 10 minutes at room temperature. (7-Bromo-pyrrolo[2,1-f][1,2,4]triazin-2-yl)-[4-(4-methyl-piperazin-1-yl)-phenyl]-amine (100.0 mg, 0.2582 mmol), 1,3-Dimethyl-4-(4,4,5,5-tetramethyl-[1,3,2]dioxaborolan-2-yl)-1H-pyrazole (114.7 mg, 0.5164 mmol), N,N-Dimethylformamide (4.0 mL), and 1.50 M of Sodium carbonate in Water (1.58 mL, 2.37 mmol) were added. The reaction was heated at 90° C. for 3 hours. The reaction was partitioned with water and EtOAc. The organic was separated, washed with Brine, and dried over magnesium sulfate. The solid was filtered and washed with EtOAc. The solvent was removed under vacuum. The product was isolated via column chromatography with DCM and NH$_3$ in Methanol as eluant (5 to 20% NH$_3$ in MeOH). The collected fractions afforded a solid. The solid was triturated with Et2O and filtered to give a brown solid. LCMS (E/I+) 403.18 (M+H). NMR $^1$H (DMSO-d$_6$)-9.10 (s, 1H), 8.85 (s, 1H), 8.07 (s, 1H), 7.60 (d, 2H, J=9.04 Hz), 6.84-6.90 (m, 3H), 6.81 (d, 1H, J=4.59 Hz), 3.84 (s, 3H), 3.06 (t, 4H, J=5.05 Hz), 2.45 (d, 4H, J=5.05 Hz), 2.41 (d, 3H), 2.22 (s, 3H).

Example 1230

N-(2-{2-[2-Methoxy-3-(4-methyl-piperazine-1-carbonyl)-phenylamino]-pyrrolo[2,1-f][1,2,4]triazin-7-yl}-phenyl)-N-methyl-methanesulfonamide 1230a. 2-Methoxy-3-nitro-benzoic acid (1.20 g, 6.09 mmol), 1-Methylpiperazine (1.01 mL, 9.13 mmol) N-(3-Dimethylaminopropyl)-N'-ethylcarbodiimide hydrochloride (1750 mg, 9.13 mmol, 1-hydroxybenzotriazole hydrate (1.45 g, 9.13 mmole) and N,N-Dimethylformamide (40.4 mL) were combined into a vial and stirred at room temperature for 1 hour. LCMS showed complete conversion to product. Diluted reaction mixture with saturated NaHCO$_3$ and filtered off resulting ppt. The solid was filtered and washed with water. The solid was dried under vacuum overnight to give (2-Methoxy-3-nitro-phenyl)-(4-methyl-piperazin-1-yl)-methanone as a white solid (0.70 g, 44%)

1230b. Into a parr bottle, (2-Methoxy-3-nitro-phenyl)-(4-methyl-piperazin-1-yl)-methanone (0.50 g, 1.8 mmol), Ethanol (20 mL, 300 mmol) and 10% Pd/C (10:90, Palladium:carbon black, 0.20 g, 0.19 mmol) were added. The reaction mixture was evacuated and charged with hydrogen at 35 psi. The mixture was shaken for 3 hours. The solid was filtered through Celite and washed with methanol. The solvent was removed under vacuum to give (3-Amino-2-methoxy-phenyl)-(4-methyl-piperazin-1-yl)-methanone as a semi-solid (0.28 g, 63%)

1230c. Into a 8-dram vial, (3-Amino-2-methoxy-phenyl)-(4-methyl-piperazin-1-yl)-methanone (107 mg, 0.430 mmol), Trifluoro-methanesulfonic acid 7-[2-(methanesulfonyl-methyl-amino)-phenyl]-pyrrolo[2,1-f][1,2,4]triazin-2-yl ester (88.0 mg, 0.195 mmol), N,N-Diisopropylethylamine (0.0749 mL, 0.430 mmol), and 1-Methoxy-2-propanol (0.70 mL, 7.2 mmol) were added. The reaction mixture was heated at 120° C. for 6 hours. The solvent was removed under vacuum. The reaction mixture was purified via HPLC reverse phase chromatography with 0.1% TFA in Water and 0.1% TFA in ACN. The collected fractions were lyophilized to give N-(2-{2-[2-Methoxy-3-(4-methyl-piperazine-1-carbonyl)-phenylamino]-pyrrolo[2,1-f][1,2,4]triazin-7-yl}-phenyl)-N-methyl-methanesulfonamide a yellow solid (42 mg, 32%). LCMS (E/I+) 550.16 (M+H). NMR $^1$H (DMSO-$d_6$)-9.79 (bs, 1H), 9.02 (s, 1H), 8.13 (bs, 1H), 8.06 (s, 1H), 7.90-7.96 (m, 1H), 7.45-7.65 (m, 3H), 7.09 (t, 1H, J=7.80 Hz), 7.05 (d, 1H, J=4.63 Hz), 7.00 (d, 1H, J=4.63 Hz), 6.92 (bs, 1H), 2.70-4.50 (m, 20H).

Example 1231

{2-Methoxy-3-[7-(2-methoxy-phenyl)-pyrrolo[2,1-f][1,2,4]triazin-2-ylamino]-phenyl}-(4-methyl-piperazin-1-yl)-methanone The titled compound was prepared in an analogous fashion to Example 1230 replacing 7-[2-(methanesulfonyl-methyl-amino)-phenyl]-pyrrolo[2,1-f][1,2,4]triazin-2-yl ester with Trifluoro-methanesulfonic acid 7-(2-methoxy-phenyl)-pyrrolo[2,1-f][1,2,4]triazin-2-yl ester to give a yellow solid (38 mg, 33%). LCMS (E/I+) 473.18 (M+H). NMR $^1$H (DMSO-$d_6$)-9.83 (s, 1H), 8.99 (s, 1H), 8.21 (s, 1H), 7.95-8.15 (m, 1H), 7.77 (d, 1H, J=7.17 Hz), 7.41 (t, 1H, J=8.13 Hz), 7.23 (d, 1H, J=8.60 Hz), 7.12 (d, 1H, J=7.65 Hz), 7.08 (d, 1H, J=7.65 Hz), 6.95-7.03 (m, 2H), 6.90 (bs, 1H), 2.65-4.50 (m, 17H).

Example 1232

N-[2-(2-{3-[4-(2-Hydroxy-ethyl)-piperazine-1-carbonyl]-2-methoxy-phenylamino}-pyrrolo[2,1-f][1,2,4]triazin-7-yl)-phenyl]-N-methyl-methanesulfonamide The titled compound was prepared in an analogous fashion to Example 1230 replacing n-methylpiperazine with 2-piperazin-1-yl-ethanol to give a yellow solid (65 mg, 43%). LCMS (E/I+) 580.16 (M+H). NMR $^1$H (DMSO-$d_6$)-9.78 (bs, 1H), 9.00 (bs, 1H), 8.13 (bs, 1H), 8.06 (bs, 1H), 7.95 (d, 1H, J=6.95 Hz), 7.49-7.68 (m, 3H), 7.07 (t, 1H, J=7.87 Hz), 7.02 (d, 1H, J=4.51 Hz), 7.00 (d, 1H, J=4.51 Hz), 6.93 (bs, 1H), 2.70-4.70 (m, 22H).

Example 1233

[4-(2-Hydroxy-ethyl)-piperazin-1-yl]-{2-methoxy-3-[7-(2-methoxy-phenyl)-pyrrolo[2,1-f][1,2,4]triazin-2-ylamino]-phenyl}-methanone The titled compound was prepared in an analogous fashion to Example 1232 replacing 7-[2-(methanesulfonyl-methyl-amino)-phenyl]-pyrrolo[2,1-f][1,2,4]triazin-2-yl ester with Trifluoro-methanesulfonic acid 7-(2-methoxy-phenyl)-pyrrolo[2,1-f][1,2,4]triazin-2-yl ester to give a yellow solid (38 mg, 31%). LCMS (E/I+) 503.17 (M+H). NMR $^1$H (DMSO-$d_6$)-9.72 (bs, 1H), 8.99 (s, 1H), 8.21 (bs, 1 h), 7.96-8.10 (m, 2H), 7.77 (d, 1H, J=7.31 Hz), 7.46 (t, 1H, J=7.64 Hz), 7.22 (d, 1H, J=7.31 Hz), 7.11 (d, 1H, J=7.64 Hz), 7.08 (d, 1H, J=7.31 Hz), 6.85-7.03 (m, 3H), 2.50-4.70 (m, 19).

Example 1234

N-(2-{2-[4-(4-Hydroxy-piperidin-1-ylmethyl)-2-methoxy-phenylamino]-pyrrolo[2,1-f][1,2,4]triazin-7-yl}-phenyl)-N-methyl-methanesulfonamide 1234a. Into a 8-dram vial, 4-Bromomethyl-2-methoxy-1-nitro-benzene (2.44 g, 9.93 mmol), Piperidin-4-ol (2.01 g, 19.9 mmol), Potassium carbonate (5.49 g, 39.7 mmol), and N,N-Dimethylformamide (25 ml) were added. The reaction mixture was heated at 80° C. overnight. The reaction was partitioned with water and EtOAc. The organic was separated, washed with Brine and dried over $Na_2SO_4$. The solid was filtered and washed with DCM. The solvent was removed under vacuum. The reaction mixture was purified via ISCO column chromatography with hexane and EtOAc as eluant (0 to 100% EtOAc). The collected fractions afforded 1-(3-Methoxy-4-nitro-benzyl)-piperidin-4-ol as a yellow solid.

1234b. Into a par bottle, 1-(3-Methoxy-4-nitro-benzyl)-piperidin-4-ol (0.74 g, 2.8 mmol), Ethanol (20 mL) and 10% Pd/C (10:90, Palladium:carbon black, 0.30 g, 0.28 mmol) were added. The reaction mixture was evacuated and charged with hydrogen at 35 psi. The mixture was shaken for 3 hours. The solid was filtered through Celite and washed with methanol. The solvent was removed under vacuum to give 1-(4-Amino-3-methoxy-benzyl)-piperidin-4-ol as a semi-solid.

1234c. Into an 8-dram vial, [1-(4-Amino-3-methoxy-benzyl)-piperidin-4-ol (0.102 g, 0.430 mmol), Trifluoro-methanesulfonic acid 7-[2-(methanesulfonyl-methyl-amino)-phenyl]-pyrrolo[2,1-f][1,2,4]triazin-2-yl ester (88.0 mg, 0.195 mmol), N,N-Diisopropylethylamine (0.0749 mL, 0.430 mmol), and 1-Methoxy-2-propanol (0.70 mL, 7.2 mmol) were added. The reaction mixture was heated at 120° C. for 6 hours. The solvent was removed under vacuum. The reaction mixture was purified via HPLC reverse phase chromatography with 0.1% TFA in Water and 0.1% TFA in ACN. The collected fractions were lyophilized to give N-(2-{2-[4-(4-Hydroxy-piperidin-1-ylmethyl)-2-methoxy-phenylamino]-pyrrolo[2,1-f][1,2,4]triazin-7-yl}-phenyl)-N-methyl-methanesulfonamide a yellow solid (92 mg, 72%). LCMS (E/I+) 537.11 (M+H). NMR $^1$H (DMSO-$d_6$)-9.16 (bs, 1H), 9.00 (s, 1H), 8.07-8.12 (m, 1H), 7.95-8.01 (m, 1H), 7.86 (s, 1H), 7.64-7.70 (m, 1H), 7.52-7.58 (m, 1H), 7.19 (d, 1H, J=9.96 Hz), 7.03 (d, 1H, J=4.60 Hz), 7.01 (d, 1H, J=4.60 Hz), 6.90-7.00 (m, 1H), 4.24 (dd, 2H, J=4.64, 16.65 Hz), 2.80-4.00 (m, 15H), 1.40-2.00 (m, 4H).

Example 1235

1-{3-Methoxy-4-[7-(2-methoxy-phenyl)-pyrrolo[2,1-f][1,2,4]triazin-2-ylamino]-benzyl}-piperidin-4-ol The titled compound was prepared in an analogous fashion to Example 1234 replacing 7-[2-(methanesulfonyl-methyl-amino)-phenyl]-pyrrolo[2,1-f][1,2,4]triazin-2-yl ester with Trifluoro-methanesulfonic acid 7-(2-methoxy-phenyl)-pyrrolo[2,1-f][1,2,4]triazin-2-yl ester to give a yellow solid (60 mg, 42%). LCMS (E/I+) 460.07 (M+H). NMR $^1$H (DMSO-$d_6$)-9.29 (bs, 1H), 8.99 (s, 1H), 8.24 (d, 1H, J=8.40), 7.76-7.82 (m, 2H), 7.48 (t, 1H, J=7.35 Hz), 7.08-7.24 (m, 3H), 6.90-7.00 (m, 3H), 4.25 (d, 1H, J=6.96 Hz), 4.21 (d, 1H, J=4.68 Hz), 3.92 (s, 3H), 3.79 (s, 3H), 2.50-3.50 (m, 6H), 1.48-2.00 (m, 4H).

Example 1236

N-(2-{2-[4-((3R,4R)-3,4-Dihydroxy-pyrrolidin-1-ylmethyl)-2-methoxy-phenylamino]-pyrrolo[2,1-f][1,2,4]triazin-7-yl}-phenyl)-N-methyl-methanesulfonamide The titled compound was prepared in an analogous fashion to Example 1234 replacing Piperidin-4-ol with (3S,4S)-Pyrrolidine-3,4-diol to give a yellow solid (36 mg, 28%). LCMS (E/I+) 539.07 (M+H). NMR $^1$H (DMSO-d$_6$)-8.91 (s, 1H), 7.93-7.98 (m, 2H), 7.85-7.91 (d, 1H, J=8.01 Hz), 7.70 (s, 1H), 7.62-7.67 (m, 1H), 7.51-7.57 (m, 2H), 7.00 (d, 1H, J=4.72 Hz), 6.92-6.97 (m, 2H), 4.82 (bs, 2H), 3.80-3.90 (m, 5H), 3.35-3.61 (bm, 2H), 3.05 (s, 3H), 2.88 (s, 3H), 2.76 (bs, 2H).

Example 1237

(3R,4R)-1-{3-Methoxy-4-[7-(2-methoxy-phenyl)-pyrrolo[2,1-f][1,2,4]triazin-2-ylamino]-benzyl}-pyrrolidine-3,4-diol The titled compound was prepared in an analogous fashion to Example 1236 replacing 7-[2-(methanesulfonyl-methyl-amino)-phenyl]-pyrrolo[2,1-f][1,2,4]triazin-2-yl ester with Trifluoro-methanesulfonic acid 7-(2-methoxy-phenyl)-pyrrolo[2,1-f][1,2,4]triazin-2-yl ester to give a yellow solid (22 mg, 21%). LCMS (E/I+) 462.07 (M+H). NMR $^1$H (DMSO-d$_6$)-8.95 (s, 1H), 8.06 (d, 1H, J=7.49 Hz), 7.80 (dd, 1H, JJ=0.88, 7.49 Hz), 7.63 (s, 1H), 7.47 (dt, 1H, JJ=1.38, 8.38 Hz), 7.23 (d, 1H, J=8.38 Hz), 7.10 (t, 1H, J=7.38 Hz), 6.91-7.06 (m, 3H), 6.78 (bs, 1H), 4.87 (bs, 2H), 3.83-3.95 (m, 5H), 3.78 (s, 3H), 2.50-3.70 (m, 6H).

Example 1238

7-(2-Methoxy-phenyl)-2-(2-methoxy-4-piperazin-1-ylmethyl-phenoxy)-pyrrolo[2,1-f][1,2,4]triazine The titled compound was prepared in an analogous fashion to Example 1223 replacing Trifluoro-methanesulfonic acid 7-[2-(methanesulfonyl-methyl-amino)-phenyl]-pyrrolo[2,1-f][1,2,4]triazin-2-yl ester with Trifluoro-methanesulfonic acid 7-(2-methoxy-phenyl)-pyrrolo[2,1-f][1,2,4]triazin-2-yl ester to give a yellow solid (180 mg, 83%). LCMS (E/I+) 359.16 (M–84). NMR $^1$H (DMSO-d$_6$)-8.94 (s, 1H), 8.05 (d, 1H, J=8.16 Hz), 7.80 (d, 1H, J=7.96 Hz), 7.63 (s, 1H), 7.46 (t, 1H, J=8.16 Hz), 7.22 (d, 1H, J=8.29 Hz), 7.09 (t, 1H, J=7.64 Hz), 6.93-6.98 (m, 3H), 6.75 (d, 1 h, J=8.16 Hz), 3.86 (s, 3H), 3.78 (s, 3H), 3.42 (s, 2H), 2.88 (bs, 4H), 2.40 (bs, 4H).

Example 1239

{2-[4-(4-{7-[2-(Methanesulfonyl-methyl-amino)-phenyl]-pyrrolo[2,1-f][1,2,4]triazin-2-ylamino}-3-methoxy-benzyl)-piperazin-1-yl]-2-oxo-ethyl}-carbamic acid tert-butyl ester

Example 1239

{2-[4-(4-{7-[2-(Methanesulfonyl-methyl-amino)-phenyl]-pyrrolo[2,1-f][1,2,4]triazin-2-ylamino}-3-methoxy-benzyl)-piperazin-1-yl]-2-oxo-ethyl}-carbamic acid tert-butyl ester Into a 8-dram vial, N-α-(tert-Butoxycarbonyl)glycine (35.1 mg, 0.200 mmol) was dissolved in N,N-Dimethylformamide (5.00 mL), and 1-Hydroxybenzotriazole hydrate (0.0306 g, 0.200 mmol), N-(3-Dimethylaminopropyl)-N'-ethylcarbodiimide hydrochloride (38.4 mg, 0.200 mmol) were added. After stirring for 5 min, N-{2-[2-(2-Methoxy-4-piperazin-1-ylmethyl-phenylamino)-pyrrolo[2,1-f][1,2,4]triazin-7-yl]-phenyl}-N-methyl-methanesulfonamide (87 mg, 0.17 mmol) was added followed by 4-Methylmorpholine (0.0220 mL, 0.200 mmol). The reaction was stirred at room temperature for 1 hour. The reaction mixture was diluted with NaHCO$_3$ and the resulting ppt was filtered, washed with NaHCO$_3$ and water. The reaction mixture was purified via ISCO column chromatography with DCM and methanol as eluant (0 to 25% methanol). The collected fractions afforded a yellow solid (35 mg, 30%). LCMS (E/I+) 679.05 (M+H). NMR $^1$H (DSMO-d$_6$)-8.96 (s, 1H), 7.94-7.99 (m, 1H), 7.91 (d, 1H, J=8.27), 7.72 (s, 1H), 7.62-7.67 (m, 1H), 7.51-7.59 (m, 1H), 7.00 (d, 1H, J=4.65 Hz), 6.92-6.98 (m, 2H), 6.67-6.76 (m, 2H), 3.84 (s, 3H), 3.76 (d, 2H, J=5.89 Hz), 3.34-3.50 (m, 6H), 3.03 (s, 3H), 2.88 (s, 3H), 2.33 (bs, 4H), 1.37 (s, 9H).

Example 1240

N-(2-{2-[4-(4-Acetyl-piperazin-1-ylmethyl)-2-methoxy-phenylamino]-pyrrolo[2,1-f][1,2,4]triazin-7-yl}-phenyl)-N-methyl-methanesulfonamide Into an 8-dram vial, N-{2-[2-(2-Methoxy-4-piperazin-1-ylmethyl-phenylamino)-pyrrolo[2,1-f][1,2,4]triazin-7-yl]-phenyl}-N-methyl-methanesulfonamide (64.0 mg, 0.123 mmol), Methylene chloride (2.00 mL), N,N-Diisopropylethylamine (0.0352 g, 0.272 mmol), and Acetyl chloride (0.0102 g, 0.130 mmol) were added. The reaction was stirred at room temperature over the weekend. The solvent was removed under vacuum. The reaction mixture was purified via HPLC reverse phase chromatography with 0.1% TFA in Water and 0.1% TFA in ACN. The collected fractions were lyophilized to give N-(2-{2-[4-(4-Acetyl-piperazin-1-ylmethyl)-2-methoxy-phenylamino]-pyrrolo[2,14][1,2,4]triazin-7-yl}-phenyl)-N-methyl-methanesulfonamide a yellow solid (63 mg, 91%). LCMS (E/I+) 564.11 (M–84). NMR $^1$H (DMSO-d$_6$)-8.96 (s, 1H), 7.93-7.98 (m, 1H), 7.90 (d, 1H, J=8.13 Hz), 7.72 (s, 1H), 7.61-7.67 (m, 1H), 7.51-757 (m, 2H), 7.00 (d, 1H, J=4.64 Hz), 6.93-6.98 (m, 2H), 6.74 (d, 1H, J=8.13 Hz), 3.83 (s, 3H), 3.38-3.43 (m, 6H), 3.04 (s, 3H), 2.88 (s, 3H), 2.34 (t, 2H, J=4.82 Hz), 2.29 (t, 2H, J=4.82 Hz), 1.97 (s, 3H).

Example 1241

N-[2-(2-{4-[4-(2-Amino-acetyl)-piperazin-1-ylmethyl]-2-methoxy-phenylamino}-pyrrolo[2,1-f][1,2,4]triazin-7-yl)-phenyl]-N-methyl-methanesulfonamide Into an 8 dram vial, {2-[4-(4-{7-[2-(Methanesulfonyl-methyl-amino)-phenyl]-pyrrolo[2,1-f][1,2,4]triazin-2-ylamino}-3-methoxy-benzyl)-piperazin-1-yl]-2-oxo-ethyl}-carbamic acid tert-butyl ester (78 mg, 0.11 mmol), Methylene chloride (2.00 mL), and Trifluoroacetic Acid (1.00 mL, 13.0 mmol) were added. The reaction was stirred at room temperature over the weekend. The reaction was partitioned with saturated NaHCO$_3$ and DCM. The organic was separated, washed with Brine and dried over Na$_2$SO$_4$. The solid was filtered and washed with DCM. The solvent was removed under vacuum. The reaction mixture was purified via HPLC reverse phase chromatography with 0.1% TFA in Water and 0.1% TFA in ACN. The collected fractions were lyophilized to give a yellow solid The solid was partitioned with saturated NaHCO$_3$ and DCM. The organic was separated, washed with Brine and dried over Na$_2$SO$_4$. The solid was filtered and washed with DCM. The solvent was removed under vacuum. The collected fractions afforded N-[2-(2-{4-[4-(2-Amino-acetyl)-piperazin-1-ylmethyl]-2-methoxy-phenylamino}-pyrrolo[2,1-f][1,2,4]triazin-7-yl)-phenyl]-N-methyl-methanesulfonamide as a yellow solid. LCMS (E/I+) 579.09 (M+H). NMR $^1$H (DMSO-d$_6$)-8.96 (s, 1H), 7.93-7.99 (m, 1H), 7.90 (d, 1H, J=8.05 Hz), 7.72 (s, 1H), 7.63-7.73 (m, 1H), 7.52-7.58 (m, 2H), 7.00 (d, 1H, J=4.66 Hz), 6.93-6.98 (m, 2H), 6.74 (d, 1H, J=7.94 Hz), 3.84 (s, 3H), 3.35-3.46 (m, 8H), 3.05 (s, 3H), 2.88 (s, 3H), 2.32 (bs, 4H).

Example 1242

[2-(4-{3-Methoxy-4-[7-(2-methoxy-phenyl)-pyrrolo[2,1-f][1,2,4]triazin-2-ylamino]-benzyl}-piperazin-1-yl)-2-oxo-ethyl]-carbamic acid tert-butyl ester The titled compound was prepared in an analogous fashion to Example 1239 replacing N-{2-[2-(2-Methoxy-4-piperazin-1-ylmethyl-phenylamino)-pyrrolo[2,1-f][1,2,4]triazin-7-yl]-phenyl}-N-methyl-methanesulfonamide with [7-(2-Methoxy-phenyl)-pyrrolo[2,1-f][1,2,4]triazin-2-yl]-(2-methoxy-4-piperazin-1-ylmethyl-phenyl)-amin to give a yellow solid (35 mg, 31%). LCMS (E/I+) 602.10 (M+H). NMR $^1$H (DSMO-d$_6$)-8.94 (s, 1H), 8.05 (d, 1H, J=8.18), 7.80 (d, 1H, J=7.44 Hz), 7.63 (s, 1H), 7.46 (t, 1H, J=7.85 Hz), 7.22 (d, 1H, J=8.35 Hz), 7.09 (t, 1H, J=7.44 Hz), 6.90-6.98 (m, 3H), 6.76 (d, 1H, J=8.43 Hz), 6.70 (t, 1H, J=5.70 Hz), 3.86 (s, 3H), 3.78 (s, 3H), 3.76 (d, 2H, J=5.88 Hz), 3.35-3.55 (m, 6H), 2.27-2.40 (m, 4H), 1.37 (s, 9H).

Example 1243

1-Fluoro-3-(4-{3-methoxy-4-[7-(2-methoxy-phenyl)-pyrrolo[2,1-f][1,2,4]triazin-2-ylamino]-benzyl}-piperazin-1-yl)-propan-2-ol The titled compound was prepared in an analogous fashion to Example 1226 replacing (S)-(−)-Propylene Oxide with 2-fluoromethyl-oxirane to give a yellow solid (180 mg, 83%). LCMS (E/I+) 543.07 (M+Na). NMR $^1$H (DMSO-d$_6$)-8.99 (s, 1H), 8.76 (bs, 1H), 8.17 (d, 1H, J=8.09 Hz), 7.80 (d, 1H, J=7.44 Hz), 7.72 (s, 1H), 7.47 (t, 1H, J=8.09 Hz), 7.22 (d, 1H, J=8.41 Hz), 6.90-7.18 (m, 4H), 6.92 (bs, 1H), 3.94 (s, 3H), 3.79 (2, 3H), 2.00-3.60 (m, 15H).

Example 1244

2-Amino-1-(4-{3-methoxy-4-[7-(2-methoxy-phenyl)-pyrrolo[2,1-f][1,2,4]triazin-2-ylamino]-benzyl}-piperazin-1-yl)-ethanone The titled compound was prepared in an analogous fashion to Example 1241 replacing {2-[4-(4-{7-[2-(Methanesulfonyl-methyl-amino)-phenyl]-pyrrolo[2,14][1,2,4]triazin-2-ylamino}-3-methoxy-benzyl)-piperazin-1-yl]-2-oxo-ethyl}-carbamic acid tert-butyl ester with 1242[2-(4-{3-Methoxy-4-[7-(2-methoxy-phenyl)-pyrrolo[2,1-f][1,2,4]triazin-2-ylamino]-benzyl}-piperazin-1-yl)-2-oxo-ethyl]-carbamic acid tert-butyl ester to give a yellow solid (31 mg, 53%). LCMS (E/I+) 502.07 (M+Na). NMR $^1$H (DMSO-d$_6$)-8.94 (s, 1H), 8.05 (d, 1H, J=8.11), 7.80 (d, 1H, J=7.52 Hz), 7.64 (s, 1H), 7.46 (t, 1H, J=7.70 Hz), 7.22 (d, 1H, J=8.40 Hz), 7.09 (t, 1H, J=7.52 Hz), 6.90-6.98 (m, 3H), 6.76 (d, 1H, J=8.40 Hz), 4.27 (bs, 2H), 3.86 (s, 3H), 3.78 (s, 3H), 3.36-3.55 (m, 8H), 2.27-2.39 (m, 4H).

Example 1245

N-{2-[2-({4-[trans-1-cyano-4-(morpholin-4-yl)cyclohexyl]-2-methoxyphenyl}amino)pyrrolo[2,1-f][1,2,4]triazin-7-yl]phenyl}-N-methylmethanesulfonamide 1245a. Into a seal vessel, 4-Fluoro-2-methoxy-1-nitrobenzene (15.00 g, 87.65 mmol), 1.00 M of Potassium tert-Butoxide in Tetrahydrofuran (193 mL, 193 mmol), and t-Butyl cyanoacetate (24.7 g, 175 mmol) were added. The reaction mixture was heated at 80° C. for 4 hours. The reaction was cooled to room temperature. Acetic acid (10.96 mL, 192.8 mmol) was added. The reaction was partitioned with water and DCM. The organic was separated, washed with Brine and dried over Na$_2$SO$_4$. The solid was filtered and washed with DCM. The solvent was removed under vacuum. The reaction mixture was purified via ISCO column chromatography with hexane and EtOAc. The reaction mixture was purified via ISCO column chromatography with hexane and EtOAc. The collected fractions afforded an orange collected fractions afforded Cyano-(3-methoxy-4-nitro-phenyl)-acetic acid tert-butyl ester as an orange solid (12.8 g, 49%).

1245b. Into a 1-neck round-bottom flask, Cyano-(3-methoxy-4-nitro-phenyl)-acetic acid tert-butyl ester (12.80 g, 43.79 mmol), Methylene chloride (50 g, 600 mmol), and Trifluoroacetic Acid (20 mL, 200 mmol) were added and stirred at room temperature overnight. The solvent was removed under vacuum. The residual TFA was co-evaporated with DCM three times to give brown oil. The reaction was partitioned with saturated NaHCO$_3$ and DCM. The organic was separated, washed with Brine and dried over Na$_2$SO$_4$. The solid was filtered and washed with DCM. The solvent was removed under vacuum. The reaction mixture was purified via ISCO column chromatography with hexane and EtOAc as eluant. The collected fractions afforded as a light brown solid. The solid was triturated with Et$_2$O to give (3-Methoxy-4-nitro-phenyl)-acetonitrile as a light yellow solid (5.20 g, 61%).

1245c. Into a 1-Neck round-bottom flask, (3-Methoxy-4-nitro-phenyl)-acetonitrile (5.60 g, 29.1 mmol), Acetonitrile (200 mL, 4000 mmol) and Triton-B 40% in Methanol (40:60, Benzyltrimethylammonium hydroxide:Methanol, 3.05 g, 7.28 mmol) were added and heated to reflux for 2 hours. Methyl acrylate (12.5 g, 146 mmol) was added and heated to reflux overnight. 6N HCl was added to adjust pH to 2. The reaction was partitioned with water and DCM. The organic was separated, washed with Brine and dried over Na$_2$SO$_4$. The solid was filtered and washed with DCM. The solvent was removed under vacuum. The reaction mixture was purified via ISCO column chromatography with hexane and EtOAc. The collected fraction afforded 4-Cyano-4-(3-methoxy-4-nitro-phenyl)-heptanedioic acid dimethyl ester as an off white solid (4.20 g, 39%).

1245d. Into a 1-Neck round-bottom flask, 4-Cyano-4-(3-methoxy-4-nitro-phenyl)-heptanedioic acid dimethyl ester (4.20 g, 11.5 mmol), 1,2-Dimethoxyethane (80 mL, 800 mmol), and Sodium Hydride (60% dispersion mineral oil)(6:4, Sodium hydride:Mineral Oil, 1.38 g, 34.6 mmol) were added, and heated to reflux overnight. The reaction was cooled to room temperature. Water was added to quenched the excess NaH. 2N HCl was added to adjust pH to 2. The reaction was partitioned with water and DCM. The organic was separated, washed with Brine and dried over Na2SO4. The solid was filtered and washed with DCM. The solvent was removed under vacuum. The reaction mixture was purified via ISCO column chromatography with hexane and EtOAc. The collected fractions afforded 5-Cyano-5-(3-methoxy-4-nitro-phenyl)-2-oxo-cyclohexanecarboxylic acid methyl ester as an off white solid (2.00, 59%).

1245e. Into a 8-dram vial, 5-Cyano-5-(3-methoxy-4-nitrophenyl)-2-oxo-cyclohexanecarboxylic acid methyl ester (2.00 g, 6.02 mmol), Sodium chloride (1.00 g, 17.1 mmol), Water (1.00 mL, 55.5 mmol) and Dimethyl sulfoxide (5.00 g, 64.0 mmol) were added. The reaction mixture was heated at 165° C. for 6 hours. HPLC suggested no SM. The reaction was partitioned with water and EtOAc. The organic was separated, washed with Brine and dried over $Na_2SO_4$. The solid was filtered and washed with DCM. The solvent was removed under vacuum. The reaction mixture was purified via ISCO column chromatography with DCM and methanol as eluant (0 to 10% methanol). The collected fractions afforded 1-(3-Methoxy-4-nitro-phenyl)-4-oxo-cyclohexanecarbonitrile a white solid (0.80 g, 48%).

1245f. Into a 8-dram vial, 1-(3-Methoxy-4-nitro-phenyl)-4-oxo-cyclohexanecarbonitrile (0.450 g, 1.64 mmol), Morpholine (0.429 g, 4.92 mmol), Tetrahydrofuran (8.00 mL, 98.6 mmol) was added and stirred at 50° C. for 1 hour. Sodium triacetoxyborohydride (0.695 g, 3.28 mmol) was added and continued to heat at 50° C. overnight. The reaction was cooled to room temperature. The reaction was partitioned with saturated NaHCO3 and EtOAc. The organic was separated, washed with Brine and dried over Na2SO4. The solid was filtered and washed with DCM. The solvent was removed under vacuum. The reaction mixture was purified via ISCO column chromatography with hexane and EtOAc as eluant. The collected fractions afforded trans-1-(3-methoxy-4-nitrophenyl)-4-(morpholin-4-yl)cyclohexanecarbonitrile (0.38 g, 67%) and 4-Hydroxy-1-(3-methoxy-4-nitro-phenyl)-cyclohexanecarbonitrile (0.05 g, 10%).

1245g. Into a 1-Neck round-bottom flask, trans-1-(3-methoxy-4-nitrophenyl)-4-(morphol-4-yl)cyclohexanecarbonitrile (0.300 g, 0.868 mmol), 10% Pd/C (10:90, Palladium: carbon black, 0.20 g, 0.19 mmol), and Ethanol (20 mL, 300 mmol) were added. The reaction was evacuated and charged with hydrogen. The mixture was stirred at room temperature overnight. The solid was filtered through celite and washed with EtOH. The solvent was removed under vacuum to give a semi solid. The reaction mixture was purified via ISCO column chromatography with DCM and methanol as eluant to give trans-1-(4-amino-3-methoxyphenyl)-4-(morpholin-4-yl)cyclohexanecarbonitrile a semi-solid (0.22, 80%) and 4-Hydroxy-1-(3-methoxy-4-nitro-phenyl)-cyclohexanecarbonitrile (50 mg, 10%).

1245h. Into a 8-dram vial, trans-1-(4-amino-3-methoxyphenyl)-4-(morpholin-4-yl)cyclohexanecarbonitrile (0.136 g, 0.430 mmol), Trifluoro-methanesulfonic acid 7-[2-(methanesulfonyl-methyl-amino)-phenyl]-pyrrolo[2,1-f][1,2,4]triazin-2-yl ester (88.0 mg, 0.195 mmol), N,N-Diisopropylethylamine (0.0749 mL, 0.430 mmol), and 1-Methoxy-2-propanol (0.70 mL, 7.2 mmol) were added. The reaction mixture was heated at 120° C. for 6 hours. The solvent was removed under vacuum. The reaction mixture was purified via HPLC reverse phase chromatography with 0.1% TFA in Water and 0.1% TFA in ACN. The collected fractions were lyophilized to give a yellow solid. The solid was partitioned with NaHCO3 and DCM. The organic was separated, washed with Brine and dried over $Na_2SO_4$. The solid was filtered and washed with DCM. The solvent was removed under vacuum to give N-{2-[2-({4-[trans-1-cyano-4-(morpholin-4-yl)cyclohexyl]-2-methoxyphenyl}amino)pyrrolo[2,1-f][1,2,4]triazin-7-yl]phenyl}-N-methylmethanesulfonamide as a yellow solid (25 mg, 20%). LCMS (E/I+) 616.23 (M+H). NMR $^1$H (DMSO-$d_6$)-8.98 (s, 1H), 7.92-8.04 (m, 2H), 7.79 (s, 1H), 7.63-7.70 (m, 1H), 7.52-7.61 (m, 2H), 7.12 (s, 1H), 7.02 (d, 1H, J=4.64 Hz), 6.98 (d, 1H, J=4.64 Hz), 6.96 (d, 1H, J=8.46), 3.89 (s, 3H), 3.59 (bs, 4H), 3.06 (s, 3H), 2.89 (s, 3H), 2.30-2.55 (m, 5H), 2.10-2.20 (m, 2H), 1.78-2.05 (m, 4H), 1.50-1.65 (m, 2H).

Example 1246 trans-1-[3-methoxy-4-[[7-(2-methoxyphenyl)pyrrolo[2,1-f][1,2,4]triazin-2-yl]amino]phenyl]-4-morpholino-cyclohexanecarbonitrile The titled compound was prepared in an analogous fashion to Example 1245 replacing 7-[2-(methanesulfonyl-methylamino)-phenyl]-pyrrolo[2,1-f][1,2,4]triazin-2-yl ester with Trifluoro-methanesulfonic acid 7-(2-methoxy-phenyl)-pyrrolo[2,1-f][1,2,4]triazin-2-yl ester to give a yellow solid (32 mg, 30%). LCMS (E/I+) 539.23 (M+H). NMR $^1$H (DMSO-$d_6$)-9.68 (ns, 1H), 8.99 (s, 1H), 8.16 (d, 1H, J=8.47 Hz), 7.81 (d, 1H, J=7.41 Hz), 7.74 (s, 1H), 7.48 (dt 1H, JJ=1.32, 8.17 Hz), 7.23 (d, 1H, J=8.49 Hz), 7.07-7.16 (m, 2H), 6.94-7.02 (m, 3H), 4.06 (d, 2H, J=12.37 Hz), 3.29 (s, 3H), 3.79 (s, 3H), 3.69 (t, 2H, J=11.52 Hz), 3.36 (d, 2H, J=11.95 Hz), 3.10-3.40 (m, 3H), 2.33 (bs, 4H), 1.98 (t, 2H, J=11.52 Hz), 1.81 (q, 2H, J=11.89 Hz).

Example 1247

N-{2-methoxy-4-[trans-4-(morpholin-4-yl)cyclohexyl]phenyl}-7-(2-methoxyphenyl)pyrrolo[2,1-f][1,2,4]triazin-2-amine 1247a. Into a 1-neck round-bottom flask, Ammonia (15.0 mL, 526 mmol) was condensed via a dry ice condensor. Sodium (0.419 g, 18.2 mmol) solid was washed with hexane, dried with a paper towel and added portionwise to the ammonia solution at −78° C. The mixture was stirred for 30 minutes. trans-1-(3-methoxy-4-nitrophenyl)-4-(morpholin-4-yl)cyclohexanecarbonitrile (0.420 g, 1.22 mmol) in Tetrahydrofuran (5 mL) was added via a syringe over 5 minutes. The reaction was stirred at −78° C. for two hour. NH4Cl (2.00 g) suspended in NH4OH (5 mL) was added to the reaction mixture portion wise. The reaction was warm to room temperature and stirred at room temperature for two hours. The reaction was partitioned with water and EtOAc. The organic was separated, washed with Brine and dried over $Na_2SO_4$. The solid was filtered and washed with EtOAc. The solvent was removed under vacuum. The reaction mixture was purified via ISCO column chromatography with DCM and methanol as eluant (0 to 10% methanol). The collected fractions afforded 2-methoxy-4-[trans-4-(morpholin-4-yl)cyclohexyl]aniline (0.18 g, 51%) and 2-methoxy-4-[cis-4-(morpholin-4-yl)cyclohexyl]aniline (45 mg, 13%).

1247b. Into an 8-dram vial, 2-methoxy-4-[trans-4-(morpholin-4-yl)cyclohexyl]aniline (0.125 g, 0.430 mmol), Trifluoro-methanesulfonic acid 7-(2-methoxy-phenyl)-pyrrolo[2,1-f][1,2,4]triazin-2-yl ester (98 mg, 0.26 mmol), N,N-Diisopropylethylamine (0.0749 mL, 0.430 mmol), and 1-Methoxy-2-propanol (0.70 mL, 7.2 mmol) were added. The reaction mixture was heated at 120° C. for 6 hours. The solvent was removed under vacuum. The reaction mixture was purified via HPLC reverse phase chromatography with 0.1% TFA in Water and 0.1% TFA in ACN. The collected fractions were lyophilized to give N-{2-methoxy-4-[trans-4-(morpholin-4-yl)cyclohexyl]phenyl}-7-(2-methoxyphenyl)pyrrolo[2,1-f][1,2,4]triazin-2-amine as a yellow solid (65 mg, 48%). LCMS (E/I+) 514.23 (M+H). NMR $^1$H (DMSO-$d_6$)-9.71 (bs, 1H), 8.97 (s, 1H), 8.03 (d, 1H, J=8.03 Hz), 7.81 (d, 1H, J=7.74 Hz), 7.60 (s, 1H), 7.46 (t, 1H, J=7.74 Hz), 7.22 (d, 1H, J=8.32 Hz), 7.10 (t, 1H, J=7.74 Hz), 6.98 (d, 1H, J=4.64 Hz), 6.94 (d, 1H, J=4.64 Hz), 6.89 9 s, 1H), 6.69 (d, 1H, J=8.33 Hz), 4.02 (d, 2H, J=12.02 Hz), 3.87 (s, 3H), 3.79 (s, 3H), 3.70 (t, 2H, J=11.78 Hz), 3.46 (d, 2H, J=12.02v), 3.28 (bs, 1H), 3.15 (q, 2H, J=11.54 Hz), 1.97-2.10 (m, 4H), 1.47-1.64 (m, 4H).

Example 1248

N-{2-[2-({2-methoxy-4-[trans-4-(morpholin-4-yl)cyclohexyl]phenyl}amino)pyrrolo[2,1-f][1,2,4]triazin-7-yl]phenyl}-N-methylmethanesulfonamide The titled compound was prepared in an analogous fashion to Example 1247 replacing 7-[2-(methane sulfonyl-methyl-amino)-phenyl]-pyrrolo[2,1-f][1,2,4]triazin-2-yl ester with Trifluoro-methanesulfonic acid 7-(2-methoxy-phenyl)-pyrrolo[2,1-f][1,2,4]triazin-2-yl ester to give a yellow solid (35 mg, 30%). LCMS (E/I+) 591.21 (M+H). NMR $^1$H (DMSO-$d_6$)-9.72 (bs, 1H), 8.95 (s, 1H), 7.94-8.00 (m, 1H), 7.88 (d, 1H, J=8.19 Hz), 7.69 (s, 1H), 7.62-7.68 (m, 1H), 7.50-7.58 (m, 1H), 7.01 (d, 1H, J=4.78 Hz), 6.97 (d, 1H, J=4.78 Hz), 6.89 (s, 1H), 6.68 (d, 1H, J=8.28 Hz), 4.04 (d, 2H, J=11.01 Hz), 3.84 (s, 3H), 3.70 (d, 2H, J=12.01 Hz), 3.46 (d, 1H, J=12.67 Hz), 3.27 (bs, 1H), 3.15 (q, 2H, J=11.78 Hz), 3.66 (s, 3H), 2.88 (s, 3H), 2.18 (bs, 2H), 1.90-2.00 (m, 2H), 1.47-1.63 (m, 4H).

Example 1249

N-{2-[2-({2-methoxy-4-[cis-4-(morpholin-4-yl)cyclohexyl]phenyl}amino)pyrrolo[2,1-f][1,2,4]triazin-7-yl]phenyl}-N-methylmethanesulfonamide The titled compound was prepared in an analogous fashion to Example 1248 replacing 2-methoxy-4-[trans-4-(morpholin-4-yl)cyclohexyl]aniline with 2-methoxy-4-[cis-4-(morpholin-4-yl)cyclohexyl]aniline to give a yellow solid (35 mg, 30%). LCMS (E/I+) 591.23 (M+H). NMR $^1$H (DMSO-$d_6$)-9.19 (bs, 1H), 8.96 (s, 1H), 7.96-8.02 (m, 1H), 7.92 (d, 1H, J=8.30 Hz), 7.72 (s, 1H), 7.62-7.68 (m, 1H), 7.50-7.58 (m, 2H), 7.00 (d, 1H, J=4.76 Hz), 6.94-6.98 (m, 2H), 6.79 (d, 1H, J=8.37 Hz), 3.98 (d, 2H, J=11.81 Hz), 3.87 (s, 3H), 3.68 (t, 2H, J=12.27 Hz), 3.52 (d, 2H, J=12.04 Hz), 3.32 (bs, 1H), 3.09 (s, 3H), 2.80-305 (m, 3H), 2.87 (s, 3H), 2.06-2.19 (m, 2H), 1.67-2.00 (m, 6H).

Example 1250

N-Methyl-N-{2-[2-(4-methyl-piperazin-1-yl)-pyrrolo[2,1-f][1,2,4]triazin-7-yl]-phenyl}-methanesulfonamide Into a 8-dram vial, Trifluoro-methanesulfonic acid 7-[2-(methanesulfonyl-methyl-amino)-phenyl]-pyrrolo[2,1-f][1,2,4]triazin-2-yl ester (89 mg, 0.20 mmol), N,N-Diisopropyl-ethylamine (0.0757 mL, 0.435 mmol), 2-Methoxy-4-(4-methyl-piperazin-1-ylmethyl)-phenylamine (100 mg, 0.4 mmol) and 1-Methoxy-2-propanol (0.71 mL) were added. The reaction mixture was heated at 120° C. for 6 hours. The solvent was removed under vacuum. The reaction mixture was purified via HPLC reverse phase chromatography with 0.1% TFA in Water and 0.1% TFA in ACN. The collected fractions were lyophilized to give N-Methyl-N-{2-[2-(4-methyl-piperazin-1-yl)-pyrrolo[2,1-f][1,2,4]triazin-7-yl]-phenyl}-methanesulfonamide as a yellow solid. LCMS (E/I+) 401.20 (M+H). NMR $^1$H (DMSO-$d_6$)-9.90 (bs, 1H), 8.99 (s, 1H), 7.88 (d, 1H, J=7.02 Hz), 7.65 (d, 1H, J=7.48 Hz), 7.45-7.54 (m, 2H), 7.00 (d, 1H, J=4.70 Hz), 6.92 (d, 1H, J=4.70 Hz), 4.45 (d, 2H, J=12.95 Hz), 3.49 (d, 2H, J=11.09 Hz), 3.03-3.25 (m, 7H), 2.89 (s, 3H), 2.82 (s, 3H).

Example 1251

N-(2-{2-[2-Methoxy-4-(4-methyl-piperazin-1-ylmethyl)-phenylamino]-pyrrolo[2,1-f][1,2,4]triazin-7-yl}-phenyl)-N-methyl-methanesulfonamide Into a 8-dram vial, Trifluoro-methanesulfonic acid 7-[2-(methanesulfonyl-methyl-amino)-phenyl]-pyrrolo[2,1-f][1,2,4]triazin-2-yl ester (89 mg, 0.20 mmol), N,N-Diisopropyl-ethylamine (0.0757 mL, 0.435 mmol), 2-Methoxy-4-(4-methyl-piperazin-1-ylmethyl)-phenylamine and 1-Methoxy-2-propanol (0.71 mL) were added. The reaction mixture was heated at 120° C. for 6 hours. The solvent was removed under vacuum. The reaction mixture was purified via HPLC reverse phase chromatography with 0.1% TFA in Water and 0.1% TFA in CAN. The collected fraction afforded N-(2-{2-[2-Methoxy-4-(4-methyl-piperazin-1-ylmethyl)-phenylamino]-pyrrolo[2,1-f][1,2,4]triazin-7-yl}-phenyl)-N-methyl-methanesulfonamide as a yellow solid (32 mg, 30%). LCMS (E/I+) 536.16 (M+H). NMR $^1$H (DMSO-$d_6$)-8.99 (s, 1H), 8.04 (d, 1H, J=8.09 Hz), 7.95-8.01 (m, 1H), 7.79 (s, 1H), 7.62-7.70 (m, 1H), 7.51-7.59 (m, 2H), 7.06 (s, 1H), 7.02 (d, 1H, J=4.66 Hz), 7.00 (d, 1H, J=4.66 Hz), 6.86 (d, 1H, J=8.22 Hz), 3.88 (s, 3H), 3.20-3.80 (m, 10H), 3.08 (s, 3H), 2.88 (s, 3H), 2.78 (s, 3H).

Example 1252

[2-Methoxy-4-(4-methyl-piperazin-1-ylmethyl)-phenyl]-[7-(2-methoxy-phenyl)-pyrrolo[2,1-f][1,2,4]triazin-2-yl]-amine The titled compound was prepared in an analogous fashion to Example 1251 replacing Trifluoro-methanesulfonic acid 7-[2-(methanesulfonyl-methyl-amino)-phenyl]-pyrrolo[2,1-f][1,2,4]triazin-2-yl ester with Trifluoro-methanesulfonic acid 7-(2-methoxy-phenyl)-pyrrolo[2,1-f][1,2,4]triazin-2-yl ester to give a yellow solid (15 mg, 16%). LCMS (E/I+) 459.07 (M+H). NMR $^1$H (DMSO-$d_6$)-8.97 (s, 1H), 8.14 (d, 1H, J=8.16 Hz), 7.82 (d, 1H, J=7.60 Hz), 7.70 (s, 1H), 7.42 (t, 1H, J=7.82 Hz), 7.22 (d, 1H, J=8.42 Hz), 7.10 (t, 2H, J=7.36 Hz), 7.03 (bs, 1H), 6.99 (d, 1H, J=4.61 Hz), 6.97 (d, 1H, J=4.79 Hz), 6.84 (bs, 1H), 3.89 (s, 3H), 3.79 (s, 3H), 2.66-3.48 (m, 13H).

Example 1253

N-(2-{2-[4-(1-Cyano-4-hydroxy-cyclohexyl)-2-methoxy-phenylamino]-pyrrolo[2,1-f][1,2,4]triazin-7-yl}-phenyl)-N-methyl-methanesulfonamide 1253a. Into a round bottom flask, 10% Pd/C (10:90, Palladium:carbon black, 0.10 g, 0.000094 mol), and Ethanol (6 mL, 0.1 mol) were added. The mixture was evacuated under house vacuum and charged with a hydrogen balloon (3×). The reaction was stirred at room temperature under an atmosphere of Hydrogen via a balloon. The solid was filtered. The solvent was removed under vacuum to give 1-(4-Amino-3-methoxy-phenyl)-4-hydroxy-cyclohexanecarbonitrile as a semi-solid (40 mg, 90%).

1253b. Into a 8-dram vial, Trifluoro-methanesulfonic acid 7-[2-(methanesulfonyl-methyl-amino)-phenyl]-pyrrolo[2,1-f][1,2,4]triazin-2-yl ester (31.7 mg, 0.0704 mmol), N,N-Diisopropylethylamine (0.0270 mL, 0.155 mmol), and 1-Methoxy-2-propanol (0.25 mL, 2.6 mmol) were added. The reaction mixture was heated at 120° C. for 6 hours. The solvent was removed under vacuum. The reaction mixture was purified via HPLC reverse phase chromatography with 0.1% TFA in Water and 0.1% TFA in ACN. The collected fractions were lyophilized to give a yellow solid. The solid was partitioned with NaHCO$_3$ and DCM. The organic was separated, washed with Brine and dried over Na$_2$SO$_4$. The solid was filtered and washed with DCM. The solvent was removed under vacuum to give N-(2-{2-[4-(1-Cyano-4-hydroxy-cyclohexyl)-2-methoxy-phenylamino]-pyrrolo[2,1-f][1,2,4]triazin-7-yl}-phenyl)-N-methyl-methanesulfonamide as a yellow solid (10 mg, 26%). LCMS (E/I+) 547.23 (M+H). NMR $^1$H (DMSO-d$_6$)-8.98 (s, 1H), 7.93-8.00 (m, 2H), 7.80 (s, 1H), 7.62-7.70 (m, 1H), 7.50-7.60 (m, 2H), 7.11 (s, 1H), 7.02 (d, 1H, J=4.77 Hz), 6.99 (d, 1H, J=4.77 Hz), 6.95 (d, 1H, J=8.14), 3.88 (s, 3H), 3.48-3.60 (m, 1H), 3.06 (s, 3H), 2.89 (s, 3H), 2.10 (d, 2H, J=13.15 Hz), 1.86-2.00 (m 4H), 1.57 (q, 2H, J=12.79 Hz).

Example 1254

2,2,2-Trifluoro-N-[1-(4-{7-[2-(methanesulfonyl-methyl-amino)-phenyl]-pyrrolo[2,1-f][1,2,4]triazin-2-ylamino}-3-methoxy-phenyl)-cyclobutyl]-acetamide 1254a. Into a 1-neck round-bottom flask, 1-(3-Methoxy-phenyl)-cyclobutanecarboxylic acid (5.00 g, 24.2 mmol), N,N-Diisopropylethylamine (7.52 g, 58.2 mmol), tert-Butyl alcohol (100 mL, 1000 mmol) and Diphenylphosphonic azide (8.01 g, 29.1 mmol) were added. The reaction was heated at 110° C. overnight. The solvent was removed under vacuum to give a semi solid. The reaction was partitioned with water and DCM. The organic was separated, washed with Brine and dried over Na$_2$SO$_4$. The solid was filtered and washed with DCM. The solvent was removed under vacuum to give an oil. The reaction mixture was purified via ISCO column chromatography with hexane and EtOAc. The collected fractions afforded [1-(3-Methoxy-phenyl)-cyclobutyl]-carbamic acid tert-butyl ester as a clear oil (4.20 g, 65%).

1254b. Into a 1-neck round-bottom flask, [1-(3-Methoxy-phenyl)-cyclobutyl]-carbamic acid tert-butyl ester (4.20 g, 15.1 mmol), Methylene chloride (25 mL, 390 mmol), and Trifluoroacetic Acid (5 mL, 60 mmol) were added. The reaction was stirred at room temperature overnight. The reaction was partitioned with Saturated NaHCO$_3$ and DCM. The organic was separated, washed with Brine and dried over Na$_2$SO$_4$. The solid was filtered and washed with DCM. The solvent was removed under vacuum to give 1-(3-Methoxy-phenyl)-cyclobutylamine as an oil (2.60, 96%).

1254c. Into a 1-neck round-bottom flask, Potassium nitrate (1.71 g, 16.9 mmol) and Acetonitrile (40 mL, 800 mmol) were added and cooled with ice bath. Trifluoroacetic anhydride (8.89 g, 42.3 mmol) was added portionwise over 5 minutes. The mixture was stirred for 10 minutes. 1-(3-Methoxy-phenyl)-cyclobutylamine (2.50 g, 14.1 mmol) in ACN (10 mL) was added via a syringe. The reaction was stirred for 3 hours at room temperature. Saturated Na$_2$CO$_3$ was added portionwise to adjust the pH to 8. The reaction was partitioned with water and DCM. The organic was separated, washed with Brine and dried over Na$_2$SO$_4$. The solid was filtered and washed with DCM. The solvent was removed under vacuum. The reaction mixture was purified via ISCO column chromatography with Hexane and EtOAc as eluant (0 to 10% methanol). The collected fractions afforded 2,2,2-Trifluoro-N-[1-(3-methoxy-4-nitro-phenyl)-cyclobutyl]-acetamide as a white solid (1.20 g, 26%).

1254d. Into a round bottom flask, 2,2,2-Trifluoro-N-[1-(3-methoxy-4-nitro-phenyl)-cyclobutyl]-acetamide (0.480 g, 0.00151 mol), 10% Pd/C (10:90, Palladium:carbon black, 1.6 g, 0.0015 mol), and Ethanol (100 mL, 2 mol) were added. The mixture was evacuated under house vacuum and charged with a hydrogen balloon (3×). The reaction was stirred at room temperature under an atmosphere of Hydrogen via a balloon. The solid was filtered. The solvent was removed under vacuum to give a solid. The reaction mixture was purified via ISCO column chromatography with DCM and methanol as eluant (0 to 10% methanol). The collected fractions afforded a semi-solid (0.35 g, 80%).

1254e. Into a 8-dram vial, N-[2-(2-Hydroxy-pyrrolo[2,1-f][1,2,4]triazin-7-yl)-phenyl]-N-methyl-methanesulfonamide (176 mg, 0.552 mmol), N,N-Dimethylformamide (2.00 mL, 25.8 mmol), N,N-Diisopropylethylamine (0.211 mL, 1.21 mmol), and N-Phenylbis(trifluoromethanesulphonimide) (0.236 g, 0.662 mmol) were added. The reaction was stirred at room temperature for 30 minutes. N-[1-(4-Amino-3-methoxy-phenyl)-cyclobutyl]-2,2,2-trifluoro-acetamide (0.350 g, 1.21 mmol) was then added. The reaction mixture was heated at 120° C. for 4 hours. The solvent was removed under vacuum overnight. The reaction mixture was purified via HPLC reverse phase chromatography with 0.1% TFA in Water and 0.1% TFA in ACN. The collected fractions were lyophilized to give a yellow solid. The solid was partitioned with NaHCO$_3$ and DCM. The organic was separated, washed with Brine and dried over Na$_2$SO$_4$. The solid was filtered and washed with DCM. The solvent was removed under vacuum to give 2,2,2-Trifluoro-N-[1-(4-{7-[2-(methanesulfonyl-methyl-amino)-phenyl]-pyrrolo[2,1-f][1,2,4]triazin-2-ylamino}-3-methoxy-phenyl)-cyclobutyl]-acetamide as a yellow solid (180 mg, 55%). LCMS (E/I+) 589.23 (M+H). NMR $^1$H (DMSO-d$_6$)-9.98 (s, 1H), 8.96 (s, 1H), 7.93-8.00 (m, 1H), 7.90 (d, 1H, J=8.35 Hz), 7.77 (s, 1H), 7.60-7.68 (m, 1H), 7.48-7.56 (m, 2H), 7.04 (s, 1H), 7.02 (d, 1H, J=4.74 Hz), 6.95 (d, 1H, J=4.74 Hz), 6.87 (d, 1H, J=8.51 Hz), 3.84 (s, 3H), 3.03 (s, 3H), 2.09 (s, 3H), 2.54 (t, 4H, J=7.44 Hz), 1.70-2.00 (m, 2H).

Example 1255

2-[4-(4-{7-[2-(Methanesulfonyl-methyl-amino)-phenyl]-5-methyl-pyrrolo[2,1-f][1,2,4]triazin-2-ylamino}-3-methoxy-phenyl)-piperidin-1-yl]-acetamide 1255a. Into a 1-Neck round-bottom flask, N-Methyl-N-[2-(2-methylsulfanyl-pyrrolo[2,1-f][1,2,4]triazin-7-yl)-phenyl]-methanesulfonamide (0.710 g, 2.04 mmol) Tetrahydrofuran (20.0 mL, 246 mmol), and Methanol (10 mL, 200 mmol) were added under an atmosphere of Nitrogen at room temperature. Recrystallized N-Bromosuccinimide (0.381 g, 2.14 mmol) was added portion wise over 10 minutes. The reaction was stirred at room temperature for 2 hours. The solvent was removed under vacuum. The reaction mixture was purified via ISCO column chromatography with DCM and methanol as eluant (0 to 5% methanol). The collected fractions afforded N-[2-(5-Bromo-2-methylsulfanyl-pyrrolo[2,1-f][1,2,4]triazin-7-yl)-phenyl]-N-methyl-methanesulfonamide a yellow solid (0.72 g, 82%).

1255b. Into a round bottom flask, and Methylene chloride (50 mL) were added. m-Chloroperbenzoic acid (0.217 g, 0.00126 mol) was added portion wise over 20 minutes. The reaction was stirred at room temperature for one hour. The reaction was partitioned with DCM (200 mL) and saturated NaHCO3 (200 mL). The organic was separated, washed with Brine and dried over Na2SO4. The solid was filtered and washed with DCM. The solvent was removed under vacuum to give a yellow solid. Into a 8-dram vial, 19.10 M of Sodium hydroxide in Water (2.00 mL, 0.0382 mol) were added and heated at 110° C. The intermediate was added portion wise to the reaction mixture and heated at 120° C. for 3 hours. The reaction was cooled to room temperature. Acetic acid was added to adjust pH to 4. The reaction was partitioned with water and DCM. The organic was separated, washed with Brine and dried over $Na_2SO_4$. The solid was filtered and washed with DCM. The solvent was removed under vacuum to give a solid. The reaction mixture was purified via ISCO column chromatography with DCM and methanol as eluant (0 to 25% methanol). The collected fractions afforded N-[2-(2-Hydroxy-5-methyl-pyrrolo[2,1-f][1,2,4]triazin-7-yl)-phenyl]-N-methyl-methanesulfonamide as a yellow solid (175 mg, 50%).

1255c. Into an 8-dram vial, N-[2-(2-Hydroxy-5-methyl-pyrrolo[2,1-f][1,2,4]triazin-7-yl)-phenyl]-N-methyl-methanesulfonamide (87 mg, 0.26 mmol), N,N-Dimethylformamide (0.948 mL), N,N-Diisopropylethylamine (0.100 mL, 0.576 mmol), and N-Phenylbis(trifluoromethanesulphonimide) (0.112 g, 0.314 mmol) were added. The reaction was stirred at room temperature for 30 minutes. 2-[4-(4-Amino-3-methoxy-phenyl)-piperidin-1-yl]-acetamide (0.152 g, 0.576 mmol) was then added. The reaction mixture was heated at 120° C. for 4 hours. The solvent was removed under vacuum overnight. The reaction mixture was purified via HPLC reverse phase chromatography with 0.1% TFA in Water and 0.1% TFA in ACN. The collected fractions were lyophilized to give a yellow solid. The solid was partitioned with NaHCO3 and DCM. The organic was separated, washed with Brine and dried over Na2SO4. The solid was filtered and washed with DCM. The solvent was removed under vacuum to give 2-[4-(4-{7-[2-(Methanesulfonyl-methyl-amino)-phenyl]-5-methyl-pyrrolo[2,1-f][1,2,4]triazin-2-ylamino}-3-methoxy-phenyl)-piperidin-1-yl]-acetamide as a yellow solid. LCMS (E/I+) 578.16 (M+H). NMR $^1$H (DMSO-$d_6$)-8.95 (s, 1H), 7.93-7.98 (m, 1H), 7.88 (d, 1H, J=8.18 Hz), 7.61-7.67 (m, 1H), 7.57 (s, 1H), 7.51-7.56 (m, 1H), 7.21 (s, 1H), 7.14 (s, 1H), 6.89 (s, 1H), 6.81 (s, 1H), 6.68 (d, 1H, J=8.51 Hz), 3.84 (s, 3H), 3.05 (s, 3H), 2.85-2.95 (m, 7H), 2.35-2.45 (m, 4H), 2.08-2.28 (m, 2H), 1.64-1.81 (m, 4H).

Example 1256

2-[4-(4-{7-[2-(Methanesulfonyl-methyl-amino)-pyridin-3-yl]-pyrrolo[2,1-f][1,2,4]triazin-2-ylamino}-3-methoxy-phenyl)-piperidin-1-yl]-acetamide 1256a. Into a 1-neck round-bottom flask, 4-Bromo-1-methyl-1H-pyrazol-3-ylamine (3.20 g, 18.2 mmol), 1,2-Dichloroethane (50 mL, 600 mmol), and N,N-Diisopropylethylamine (11.7 g, 90.9 mmol) were added. Methanesulfonyl chloride (5.21 g, 45.4 mmol) in DCE (10 mL) was added dropwise. The reaction was heated at 50° C. for 2 hours. The reaction was partitioned with water and DCM. The organic was separated, washed with Brine and dried over Na2SO4. The solid was filtered and washed with DCM. The solvent was removed under vacuum to give an off white solid. The solid was triturated with Et2O to afford N-(methylsulfonyl)-N-(5-bromo-1-methyl-1H-pyrazol-3-yl) methanesulfonamide as a white solid (4.80 (79%).

1256b. Into a 1-neck round-bottom flask, N-(methylsulfonyl)-N-(5-bromo-1-methyl-1H-pyrazol-3-yl) methanesulfonamide (4.60 g, 13.8 mmol) and 1.00 M of Tetra-n-butylammonium fluoride in Tetrahydrofuran (50 mL, 50 mmol) was added and heated to reflux for 4 hours. The solvent was removed under vacuum. The reaction was partitioned with water and DCM. The organic was separated, washed with Brine and dried over Na2SO4. The solid was filtered and washed with DCM. The solvent was removed under vacuum to give clear oil The reaction mixture was purified via ISCO column chromatography with hexane and EtOAc as eluant. The collected fractions afforded N-(4-Bromo-1-methyl-1H-pyrazol-3-yl)-methanesulfonamide as a white solid (1.38, 39%).

1256c. Into a 8-dram vial, N-(4-Bromo-1-methyl-1H-pyrazol-3-yl)-methanesulfonamide (1.38 g, 5.43 mmol), Acetonitrile (20 mL, 400 mmol), Potassium carbonate (1.50 g, 10.9 mmol), and Dimethyl sulfate (1.03 mL, 10.9 mmol) were added. The reaction mixture was heated at 50° C. overnight. The solid was filtered and washed DCM. The solvent was removed under vacuum to give a solid. The reaction mixture was purified via ISCO column chromatography with hexane and EtOAc as eluant. The collected fractions afforded N-(4-Bromo-1-methyl-1H-pyrazol-3-yl)-N-methyl-methanesulfonamide as a white solid (1.20 (82%).

1256d. Into a 1-Neck round-bottom flask, N-(4-Bromo-1-methyl-1H-pyrazol-3-yl)-N-methyl-methanesulfonamide (1.28 g, 4.77 mmol), 4,4,5,5,4',4',5',5'-Octamethyl-[2,2']bi[[1,3,2]dioxaborolanyl] (2.42 g, 9.55 mmol), Potassium acetate (1.87 g, 19.1 mmol) and Bis(tricyclohexylphosphine)palladium(0) (0.223 g, 0.334 mmol) were added. The mixture was purged with argon. 1,4-Dioxane (40 mL, 500 mmol) was added. The reaction was heated at 110° C. for 5 hours. The reaction was cooled to RT. The solid was filtered through celite and washed with DCM. The solvent was removed under vacuum to give N-Methyl-N-[1-methyl-4-(4,4,5,5-tetramethyl-[1,3,2]dioxaborolan-2-yl)-1H-pyrazol-3-yl]-methanesulfonamide as a brown solid (1.80 g, 120%).

1256e. Into a 1-Neck round-bottom flask, 7-Bromo-2-methylsulfanyl-pyrrolo[2,1-f][1,2,4]triazine (0.580 g, 2.38 mmol), N-Methyl-N-[1-methyl-4-(4,4,5,5-tetramethyl-[1,3,2]dioxaborolan-2-yl)-1H-pyrazol-3-yl]-methanesulfonamide (1.50 g, 4.75 mmol), Tetrakis(triphenylphosphine)palladium(0) (0.274 g, 0.238 mmol), N,N-Dimethylformamide (10 mL, 100 mmol), 1,4-Dioxane (20 mL, 200 mmol), and 1.50 M of Sodium carbonate in Water (9.50 mL, 14.2 mmol) were added. The reaction mixture was heated at 95° C. overnight. The solvent was removed under vacuum. The reaction was partitioned with water and DCM. The organic was separated, washed with Brine and dried over $Na_2SO_4$. The solid was filtered and washed with DCM. The solvent was removed under vacuum to give a solid. The reaction mixture was purified via ISCO column chromatography with DCM and methanol as eluant (0 to 5% methanol). The collected fractions afforded N-Methyl-N-[1-methyl-4-(2-methylsulfanyl-pyrrolo[2,1-f][1,2,4]triazin-7-yl)-1H-pyrazol-3-yl]-methanesulfonamide as a yellow solid (0.32 g, 38%) 1256f. Into a 8-dram vial, Methylene chloride (10 mL, 200 mmol), N-Methyl-N-[1-methyl-4-(2-methylsulfanyl-pyrrolo[2,1-f][1,2,4]triazin-7-yl)-1H-pyrazol-3-yl]-methanesulfonamide (0.250 g, 0.709 mmol), and m-CPBA 70-75% (70:30, m-Chloroperbenzoic acid:3-Chlorobenzoic acid, 0.175 g, 0.709 mmol) were added. The reaction mixture was stirred at room temperature for one hour. Sat. NaHCo3 and DCM was added. The organic was separated, washed with Brine and dried over Na2SO4. The solid was filtered and washed with DCM. The solvent was removed under vacuum to afford a yellow solid.

1256g. Into a 8-dram vial, The yellow solid was treated with 19.10 M of Sodium hydroxide in Water (2.0 mL, 38 mmol) at 110° C. for 2 hours. Acetic acid was added to adjust pH to 4. The precipitate was filtered and washed with cold water, and subsequently with Et$_2$O to give a bright yellow solid (95 mg, 70% purity). The solid was used as is without any further purification.

1256h. Into a 8-dram vial, the bright yellow solid was treated with N-Phenylbis(trifluoromethanesulphonimide) (0.114 g, 0.319 mmol), N,N-Dimethylformamide (0.7 mL) and N,N-Diisopropylethylamine (0.06 mL, 0.3 mmol). The reaction was stirred at room temperature for one hour. 2-[4-(4-Amino-3-methoxy-phenyl)-piperidin-1-yl]-acetamide (0.132 g, 0.501 mmol) was added. The reaction mixture was heated at 120° C. for 4 hours. The solvent was removed under vacuum over night. The semi-solid was purified via Gilson HPLC. The collected fractions was neutralized via polymer supported sulfonic acid resin, and subsequently released with 2N NH$_3$ in methanol. The solvent was removed to afford 2-[4-(4-{7-[3-(Methanesulfonyl-methyl-amino)-1-methyl-1H-pyrazol-4-yl]-pyrrolo[2,1-f][1,2,4]triazin-2-ylamino}-3-methoxy-phenyl)-piperidin-1-yl]-acetamide as a yellow solid (42 mg, 15%). LCMS (E/I+) 568.10 (M+H). NMR $^1$H (DMSO-d$_6$)-8.90 (s, 1H), 8.42 (s, 1H), 7.97 (s, 1H), 7.81 (d, 1H, J=8.25 Hz), 7.02 (s, 1H), 7.11-7.17 (m, 2H), 7.00 (s, 1H), 6.97 (d, 1H, J=7.85 Hz), 6.92 (d, 1H, J=4.69 Hz), 3.88 (s, 3H), 3.85 (s, 3H), 3.20 (s, 3H), 3.16 (s, 3H), 2.87-2.98 (m, 4H), 2.13-2.23 (m, 2H), 1.74-1.85 (m, 4H).

Example 1257

2-[4-(4-{7-[2-(Methanesulfonyl-methyl-amino)-pyridin-3-yl]-pyrrolo[2,1-f][1,2,4]triazin-2-ylamino}-3-methoxy-phenyl)-piperidin-1-yl]-acetamide The titled compound was prepared in an analogous fashion to Example 1251 replacing 4-Bromo-1-methyl-1H-pyrazol-3-ylamine with 3-Bromo-pyridin-2-ylamine to give a yellow solid (48 mg, 48%). LCMS (E/I+) 565.14 (M+H). NMR $^1$H (DMSO-d$_6$)-8.99 (s, 1H), 8.52-8.59 (m, 2H), 7.78-7.82 (m, 2H), 7.57-7.64 (m, 1H), 7.20 (bs, 1H), 7.13 (bs, 1H), 7.12 (d, 1H, J=4.79 Hz), 6.99 (d, 1H, J=4.79 Hz), 6.92 (s, 1H), 6.75 (d, 1H, J=8.28 Hz), 3.84 (s, 3H), 3.12 (s, 3H), 2.99 (s, 3H), 2.82-2.95 (m, 4H), 2.35-2.52 (m, 1H), 2.08-2.20 (m, 2H), 1.65-1.83 (m, 4H).

Example 1258

2-[4-(4-{7-[2-(Methanesulfonyl-methyl-amino)-pyridin-3-yl]-pyrrolo[2,1-f][1,2,4]triazin-2-ylamino}-phenyl)-piperidin-1-yl]-acetamide Into a 8-dram vial, N-[3-(2-Hydroxy-pyrrolo[2,1-f][1,2,4]triazin-7-yl)-pyridin-2-yl]-N-methyl-methanesulfonamide (56 mg, 0.18 mmol), N,N-Dimethylformamide (0.50 mL, 6.4 mmol), N,N-Diisopropylethylamine (0.0672 mL, 0.386 mmol) and N-Phenylbis(trifluoromethanesulphonimide) (2.77 g, 7.75 mmol) were added. The reaction mixture was stirred at room temperature for 1 hour. 2-[4-(4-Amino-phenyl)-piperidin-1-yl]-acetamide (90.0 mg, 0.386 mmol) was added. The reaction was heated at 110° C. for 3 hours. The solvent was removed under vacuum overnight The reaction mixture was purified via HPLC reverse phase chromatography with 0.1% TFA in Water and 0.1% TFA in ACN. The collected fractions were combined and neutralized via a polymer bound sulfonic acid column with 2N NH$_3$ in methanol. The filtrate was concentrated to afford 2-[4-(4-{7-[2-(Methanesulfonyl-methyl-amino)-pyridin-3-yl]-pyrrolo[2,1-f][1,2,4]triazin-2-ylamino}-phenyl)-piperidin-1-yl]-acetamide as a yellow solid (50 mg, 50%). LCMS (E/I+) 535.16 (M+H). NMR $^1$H (DMSO-d$_6$)-9.42 (s, 1H), 9.01 (s, 1H), 8.56-8.61 (m, 2H), 7.64-7.69 (m, 1H), 7.56 (s, 1H), 7.54 (s, 1H), 7.19 (s, 1H), 7.07-7.14 (m, 2H), 6.98 (d, 2H, J=4.63 Hz), 3.13 (s, 3H), 3.00 (s, 3H), 2.84-2.96 (m, 4H), 2.32-2.44 (m, 1H), 2.08-2.19 (m, 2H), 1.64-176 (m, 4H).

Example 1259

2-[4-(4-{5-Hydroxy-7-[2-(methanesulfonyl-methyl-amino)-phenyl]-pyrrolo[2,1-f][1,2,4]triazin-2-ylamino}-3-methoxy-phenyl)-piperidin-1-yl]-acetamide 1259a. Into a 1-Neck round-bottom flask, 5-Bromo-2-methylsulfanyl-pyrrolo[2,1-f][1,2,4]triazine (6.00 g, 24.6 mmol), 4,4,5,5,4',4',5',5'-Octamethyl-[2,2']bi[[1,3,2]dioxaborolanyl] (12.5 g, 49.2 mmol), Potassium acetate (9.65 g, 98.3 mmol) and Bis(tricyclohexylphosphine)palladium (0) (1.15 g, 1.72 mmol) were added. The mixture was purged with argon. 1,4-Dioxane (200 mL, 2000 mmol) was added. The reaction was heated at 110° C. for 5 hours. The reaction was cooled to RT. The solid was filtered through celite and washed with DCM. The solvent was removed under vacuum. The reaction mixture was purified via ISCO column chromatography with hexane and EtOAc as eluant (2 to 8% EtOAc). The collected fractions afforded a semi solid. The semisolid was triturated with cold hexane, filtered and washed with more cold hexane to afford 2-Methylsulfanyl-5-(4,4,5,5-tetramethyl-[1,3,2]dioxaborolan-2-yl)-pyrrolo[2,1-f][1,2,4]triazine as an off white solid (5.80, 81%).

1259b. Into a 1-Neck round-bottom flask, 2-Methylsulfanyl-5-(4,4,5,5-tetramethyl-[1,3,2]dioxaborolan-2-yl)-pyrrolo[2,1-f][1,2,4]triazine (1.80 g, 6.18 mmol), Tetrahydrofuran (100 mL, 1000 mmol), and 50% aq. Hydrogen peroxide (1:1, Hydrogen peroxide:Water, 6.00 mL, 77.9 mmol) were added and stirred at room temperature for 2 hours. 19.10 M of Sodium hydroxide in Water (6.00 mL, 115 mmol) was added at 0° C. Vigorous gas evolution was observed for 15 minutes. The reaction was quenched with saturated sodium thiosulfate (100 mL). The reaction was partitioned with water and EtOAc. The organic was separated, washed with Brine and dried over Na2SO4. The solid was filtered and washed with DCM. The solvent was removed under vacuum. The reaction mixture was purified via ISCO column chromatography with hexane and EtOAc as eluant (0 to 100% EtOAc). The collected fractions afforded 2-Methylsulfanyl-pyrrolo[2,1-f][1,2,4]triazin-5-ol a yellow solid (1.00 g, 89%).

1259c. Into a 1-Neck round-bottom flask, 2-Methylsulfanyl-pyrrolo[2,1-f][1,2,4]triazin-5-ol (0.810 g, 4.47 mmol) and N,N-Dimethylformamide (35.00 mL, 452.0 mmol) were added. Sodium Hydride (60% dispersion mineral oil)(6:4, Sodium hydride:Mineral Oil, 0.214 g, 5.36 mmol) was added portion wise at room temperature and stirred for 30 minutes. [β-(Trimethylsilyl)ethoxy]methyl chloride (0.745 g, 4.47 mmol) in DMF (5 mL) was added dropwise over 10 minutes. The reaction mixture was stirred at room temperature for 1 hour. The reaction was partitioned with water and Et$_2$O. The organic was separated, washed with Brine and dried over Na₂SO₄. The solid was filtered and washed with DCM. The solvent was removed under vacuum. The reaction mixture was purified via ISCO column chromatography with Hexane and EtOAc as eluant (0 to 40% EtOAc). The collected fractions afforded 2-Methylsulfanyl-5-(2-trimethylsilanyl-ethoxymethoxy)-pyrrolo[2,1-f][1,2,4]triazine as a yellow solid (1.05, 75%).

1259d. Into a 1-Neck round-bottom flask, 2-Methylsulfanyl-5-(2-trimethylsilanyl-ethoxymethoxy)-pyrrolo[2,1-f][1,2,4]triazine (1.05 g, 3.37 mmol), Tetrahydrofuran (50 mL) and Methanol (25 mL) were added and stirred at room temperature. N-Bromosuccinimide (0.630 g, 3.54 mmol) in THF (20 mL) was added to the reaction mixture. The reaction was stirred at room temperature for 2 hours. LCMS suggested no SM. The solvent was removed under vacuum. The reaction was partitioned with water and Et₂O. The organic was separated, washed with Brine and dried over Na₂SO₄. The solid was filtered and washed with DCM. The solvent was removed under vacuum. The reaction mixture was purified via ISCO column chromatography with hexane and EtOAc as eluant (5 to 20% EtOAc). The collected fractions afforded 7-Bromo-2-methylsulfanyl-5-(2-trimethylsilanyl-ethoxymethoxy)-pyrrolo[2,1-f][1,2,4]triazine as an oil (1.10 g, 83%).

1259e. Into a 30 mL vial, Palladium Acetate (0.043 g, 0.19 mmol) and Triphenylphosphine (0.14 g, 0.54 mmol) were added. The mixture was purged under an atmosphere of Nitrogen for 10 minutes. 1,4-Dioxane (14.6 mL) was added and stirred for 10 minutes at room temperature. 7-Bromo-2-methylsulfanyl-5-(2-trimethylsilanyl-ethoxymethoxy)-pyrrolo[2,1-f][1,2,4]triazine (0.750 g, 1.92 mmol), N-[2-(4,4,5,5-Tetramethyl-1,3,2-dioxaborolan-2-yl)-phenyl]-methanesulfonamide (1.14 g, 3.84 mmol), N,N-Dimethylformamide (29 mL, 380 mmol), and 1.50 M of Sodium carbonate in Water (11.5 mL, 17.3 mmol) were added. The reaction was heated at 90° C. for 3 hours. The reaction was partitioned with water and EtOAc. The organic was separated, washed with Brine, and dried over magnesium sulfate. The solid was filtered and washed with EtOAc. The solvent was removed under vacuum. The product was isolated via column chromatography with DCM and Methanol as eluant (0 to 5% MeOH). The collected fractions afforded a solid. The solid was triturated with Et₂O and filtered to give N-{2-[2-Methylsulfanyl-5-(2-trimethylsilanyl-ethoxymethoxy)-pyrrolo[2,1-f][1,2,4]triazin-7-yl]-phenyl}-methanesulfonamide as a yellow solid (0.72 g, 78%).

1259f. Into a 8-dram vial, N-{2-[2-Methylsulfanyl-5-(2-trimethylsilanyl-ethoxymethoxy)-pyrrolo[2,1-f][1,2,4]triazin-7-yl]-phenyl}-methanesulfonamide (0.780 g, 1.62 mmol), Methylene chloride (25 mL, 390 mmol) were added. m-CPBA 70-75% (70:30, m-Chloroperbenzoic acid:3-Chlorobenzoic acid, 0.440 g, 1.78 mmol) was added and the reaction mixture was stirred at room temperature for 2 hours. The reaction was partitioned with NaHCO₃ and DCM. The organic was separated, washed with Brine and dried over Na₂SO₄. The solid was filtered and washed with DCM. The solvent was removed under vacuum to give a yellow solid. The yellow solid was treated dissolved in Acetonitrile (15 mL, 290 mmol). Potassium carbonate (0.673 g, 4.87 mmol) and Dimethyl sulfate (0.409 g, 3.24 mmol) were added. The reaction was stirred at room temperature overnight. The solid was filtered and washed with DCM. The solvent was removed under vacuum. The reaction mixture was purified via ISCO column chromatography with hexane and EtOAc as eluant (0 to 100% EtOAc). The collected fractions afforded N-{2-[2-Methanesulfinyl-5-(2-trimethylsilanyl-ethoxymethoxy)-pyrrolo[2,1-f][1,2,4]triazin-7-yl]-phenyl}-N-methyl-methanesulfonamide as a yellow solid (0.48 g, 72%).

1259g. Into a 8-dram vial, N-{2-[2-Methanesulfinyl-5-(2-trimethylsilanyl-ethoxymethoxy)-pyrrolo[2,1-f][1,2,4]triazin-7-yl]-phenyl}-N-methyl-methane sulfonamide (480 mg, 0.94 mmol) was added to heated solution of 19.10 M of Sodium hydroxide in Water (5.0 mL, 96 mmol) at 110° C. The reaction mixture was heated at 120° C. for 2 hours. 5 mL of Acetic acid was added to adjust pH to 5. The reaction was partitioned with water and DCM. The organic was separated, washed with Brine and dried over Na₂SO₄. The solid was filtered and washed with DCM. The solvent was removed under vacuum. The reaction mixture was purified via ISCO column chromatography with DCM and NH₃ in methanol as eluant (2 to 15% methanol). The collected fractions afforded N-{2-[2-Hydroxy-5-(2-trimethylsilanyl-ethoxymethoxy)-pyrrolo[2,1-f][1,2,4]triazin-7-yl]-phenyl}-N-methyl-methanesulfonamide as a red solid (195 mg, 45%).

1259h. Into a 8-dram vial, N-{2-[2-Hydroxy-5-(2-trimethylsilanyl-ethoxymethoxy)-pyrrolo[2,1-f][1,2,4]triazin-7-yl]-phenyl}-N-methyl-methanesulfonamide (9.0E1 mg, 0.19 mmol), N,N-Dimethylformamide (0.70 mL, 9.0 mmol) N,N-Diisopropylethylamine (0.101 mL, 0.581 mmol) and N-Phenylbis(trifluoromethanesulphonimide) (83.0 mg, 0.232 mmol) were added. The reaction mixture was stirred at room temperature for one hour. 2-[4-(4-Amino-3-methoxy-phenyl)-piperidin-1-yl]-acetamide (102 mg, 0.387 mmol) was added. The reaction was heated at 120° C. for 3 hours. The solvent was removed under vacuum. The reaction mixture was purified via ISCO column chromatography with DCM and NH₃ in methanol as eluant (2 to 15% NH₃ in methanol). The collected fractions afforded 2-(4-{4-[7-[2-(Methanesulfonyl-methyl-amino)-phenyl]-5-(2-trimethylsilanyl-ethoxymethoxy)-pyrrolo[2,1-f][1,2,4]triazin-2-ylamino]-3-methoxy-phenyl}-piperidin-1-yl)-acetamide as a red oil (89 mg, 65%)

Into a one dram vial, 2-(4-{4-[7-[2-(Methanesulfonyl-methyl-amino)-phenyl]-5-(2-trimethylsilanyl-ethoxymethoxy)-pyrrolo[2,1-f][1,2,4]triazin-2-ylamino]-3-methoxy-phenyl}-piperidin-1-yl)-acetamide (89 mg, 0.12 mmol), Methylene chloride (1.50 mL), and Trifluoroacetic Acid (0.50 mL, 6.5 mmol) was added. The reaction mixture was stirred at room temperature for 2 hours. The solvent was removed under vacuum. The reaction mixture was purified via HPLC reverse phase chromatography with 0.1% TFA in Water and 0.1% TFA in ACN. The collected fractions were lyophilized to give a yellow solid. The TFA salt was neutralized via a polymer sulfonic acid bound resin and washed with 2M NH₃ in methanol. The solvent was removed to afford a yellow solid. The solid was triturated with Et₂O to give 2-[4-(4-{5-Hydroxy-7-[2-(methanesulfonyl-methyl-amino)-phenyl]-pyrrolo[2,1-f][1,2,4]triazin-2-ylamino}-3-methoxy-phenyl)-piperidin-1-yl]-acetamide as a yellow solid (28 mg, 32%). LCMS (E/I+) 580.15 (M+H). NMR ¹H (DMSO-d₆)- 9.94 (s, 1H), 8.74 (s, 1H), 7.94-8.02 (m 1H), 7.88 (d, 1H, J=8.25 Hz), 7.59-7.67 (m, 1H), 7.48-7.56 (m, 2H), 7.40 (s, 1H), 7.21 (bs, 1H), 7.13 (bs, 1H), 6.85 (s, 1H), 6.67 (d, 1H, J=8.31 Hz), 6.35 (s, 1H), 3.83 (s, 3H), 3.05 (s, 3H), 2.77-2.99 (m, 7H), 2.32-2.45 (m, 1H), 2.06-2.23 (m, 2H), 1.60-1.87 (m, 4H).

Example 1260

2-(4-{4-[5-Hydroxy-7-(2-methoxy-phenyl)-pyrrolo[2,1-f][1,2,4]triazin-2-ylamino]-phenyl}-piperidin-1-yl)-acetamide The titled compound was prepared in an analogous fashion to Example 1259 replacing N-[2-(4,4,5,5-Tetramethyl-[1,3, 2]dioxaborolan-2-yl)-phenyl]-methanesulfonamide with 2-methoxyphenyl boronic acid to give a yellow solid. LCMS (E/I+) 473.16 (M+H). NMR $^1$H (DMSO-d$_6$)-9.16 (s, 1H), 8.75 (s, 1H), 7.96 (s, 1H), 7.85 (d, 2H, J=7.75 Hz), 7.71 (s, 1H), 7.64 (d, 2H, J=8.18 Hz), 7.43 (t, 1H, J=8.18v), 7.20 (d, 1H, J=8.39 Hz), 7.16 (t, 1H, J=7.75 Hz), 7.05 (d, 2H, J=8.39), 3.91 (bs, 2H), 3.80 9 s, 3H), 3.54 (d, 2H, J=11.97 Hz), 3.00-3.20 (m, 2H), 2.63-2.73 (m, 1H), 1.84-2.03 (m, 4H).

Example 1261

2-[4-(4-{7-[2-(Methanesulfonyl-methyl-amino)-phenyl]-5-methyl-pyrrolo[2,1-f][1,2,4]triazin-2-ylamino}-phenyl)-piperidin-1-yl]-acetamide The titled compound was prepared in an analogous fashion to Example 1255 replacing 2-[4-(4-Amino-3-methoxy-phenyl)-piperidin-1-yl]-acetamide with 2-[4-(4-Amino-phenyl)-piperidin-1-yl]-acetamide to give a yellow solid (28 mg, 20%). LCMS (E/I+) 548.15 (M+H). NMR $^1$H (DMSO-d$_6$)-9.51 (bs, 1H), 9.33 (s, 1H), 8.98 (s, 1H), 7.50-8.10 (m, 5H), 7.05 (d, 2H, J=8.51 Hz), 6.80 (s, 1H), 3.44-3.87 (m, 4H), 3.00-3.21 (m, 5H), 2.90 (s, 3H), 2.61-2.79 (m, 1H), 1.82-2.06 (m, 4H).

Example 1262

2-(4-{3-Methoxy-4-[7-(2-methoxy-phenyl)-5-methyl-pyrrolo[2,1-f][1,2,4]triazin-2-ylamino]-phenyl}-piperidin-1-yl)-acetamide The titled compound was prepared in an analogous fashion to Example 1255 replacing N-Methyl-N-[2-(2-methylsulfanyl-pyrrolo[2,1-f][1,2,4]triazin-7-yl)-phenyl]-methanesulfonamide with 7-(2-Methoxy-phenyl)-2-methylsulfanyl-pyrrolo[2,1-f][1,2,4]triazine to give a yellow solid (89 mg, 53%). LCMS (E/I+) 501.18.16 (M+H). NMR $^1$H (DMSO-d$_6$)-9.50 (bs, 1H), 8.95 (s, 1H), 8.07 (d, 1H, J=8.36 Hz), 7.98 (s, 1H), 7.82 (d, 1H, J=7.33 Hz), 7.71 (s, 1H), 7.56 (s, 1H), 7.44 (t, 1H, J=7.99 Hz), 7.21 (d, 1H, J=8.34), 7.09 (t, 1H, J=7.30 Hz), 6.88 (s, 1H), 6.79 (s, 1H), 6.69 (d, 1H, J=8.34 Hz), 3.92 (bs, 2H), 3.88 (s, 3H), 3.79 (s, 3H), 3.36 (d, 2H, J=12.12 Hz), 3.06-3.21 (m, 2H), 2.69-2.82 (m, 1H), 2.42 (s, 3H), 1.86-2.11 (m, 4H).

Example 1263

N-{2-[2-(2-Methoxy-4-piperidin-4-yl-phenylamino)-5-methyl-pyrrolo[2,1-f][1,2,4]triazin-7-yl]-phenyl}-N-methyl-methanesulfonamide Into a 8-dram vial, N-[2-(2-Hydroxy-5-methyl-pyrrolo[2,1-f][1,2,4]triazin-7-yl)-phenyl]-N-methyl-methanesulfonamide (210 mg, 0.63 mmol), N,N-Dimethylformamide (2.33 mL), N,N-Diisopropylethylamine (0.247 mL, 1.42 mmol), and N-Phenylbis(trifluoromethanesulphonimide) (0.276 g, 0.773 mmol) were added. The reaction was stirred at room temperature for 30 minutes. 4-(4-Amino-3-methoxy-phenyl)-piperidine-1-carboxylic acid tert-butyl ester (0.434 g, 1.42 mmol) was then added. The reaction mixture was heated at 120° C. for 4 hours. The solvent was removed under vacuum overnight. The resulting solid was treated with Methylene chloride (3.50 mL, 54.6 mmol) and Trifluoroacetic Acid (1.17 mL, 15.1 mmol) and stirred at room temperature overnight. The solvent was removed under vacuum. The reaction mixture was purified via HPLC reverse phase chromatography with 0.1% TFA in Water and 0.1% TFA in ACN. The collected fractions were lyophilized to give a yellow solid. The solid was partitioned with NaHCO$_3$ and DCM. The organic was separated, washed with Brine and dried over Na$_2$SO$_4$. The solid was filtered and washed with DCM. The solvent was removed under vacuum to give N-{2-[2-(2-Methoxy-4-piperidin-4-yl-phenylamino)-5-methyl-pyrrolo[2,1-f][1,2,4]triazin-7-yl]-phenyl}-N-methyl-methanesulfonamide a yellow solid (0.135 g, 41%). LCMS (E/I+) 521.13 (M+H). NMR $^1$H (DMSO-d$_6$)-8.96 (s, 1H), 8.47-8.62 (m, 1H), 8.15-8.33 (m, 1H), 7.88-8.00 (m, 2H), 7.46-7.68 (m, 4H), 6.84 (s, 1H), 6.82 (s, 1H), 6.66 (d, 1H, J=8.11 Hz), 3.86 (s, 3H), 3.39 (d, 2H, J=12.75), 3.07 (s, 3H), 2.90-3.04 (m, 2H), 2.88 (s, 3H), 2.72-2.84 (m, 1H), 1.95 (d, 2H, J=13.48 Hz), 1.68-1.84 (m, 2H).

Example 1271

2-[4-(3-Methoxy-4-{7-[2-(2-methoxy-ethoxy)-phenyl]-pyrrolo[2,1-f][1,2,4]triazin-2-ylamino}-phenyl)-piperidin-1-yl]-acetamide A mixture of 2-(2-Methanesulfinyl-pyrrolo[2,1-f][1,2,4]triazin-7-yl)-phenol (430 mg, 1.6 mmol) and cesium carbonate (100 mg, 3.1 mmol) in acetonitrile (15 mL, 290 mmol) was stirred at 70° C. overnight. After 18 h the mixture was filtered through a pad of celite and eluted with EtOAc:MeOH 90:10. After solvent evaporation, the product, 2-Methanesulfinyl-7-[2-(2-methoxy-ethoxy)-phenyl]-pyrrolo[2,1-f][1,2,4]triazine, was purified by flash chromatography (ISCO, EtOAc:MeOH 98:2) which was obtained as a syrup (139 mg, 27%). LCMS (E/I+) 332 (M+H). 7-[2-(2-Methoxy-ethoxy)-phenyl]-pyrrolo[2,1-f][1,2,4]triazin-2-ol (95 mg, 0.33 mmol) was dissolved in N,N-Dimethylformamide (4 mL). N,N-Diisopropylethylamine (174 uL, 0.999 mmol) was added followed by N-Phenylbis(trifluoromethanesulphonimide) (131 mg, 0.366 mmol) at RT. After 1 h, LC-MS showed triflate formation. 2-[4-(4-Amino-3-methoxy-phenyl)-piperidin-1-yl]-acetamide (110 mg, 0.42 mmol) was added and the mixture was heated at 80° C. After 3 days, the product was purified by reverse phase liquid chromatography (Gilson). The product, 2-[4-(3-Methoxy-4-{7-[2-(2-methoxy-ethoxy)-phenyl]-pyrrolo[2,1-f][1,2,4]triazin-2-ylamino}-phenyl)-piperidin-1-yl]-acetamide TFA salt was isolated as a solid (26 mg, 15%). LCMS (E/I+) 531 (M+H). NMR $^1$H (DMSO-d$_6$)-9.53 (br s, 1H), 8.94 (s, 1H), 8.06 (d, 1H, J=8.22 Hz), 7.98 (m, 2H), 7.72 (s, 1H), 7.67 (s, 1H), 7.42 (m, 1H), 7.20 (d, 1H, J=8.34 Hz), 7.11 (m, 2H), 6.96 (d, 1H, J=4.64 Hz), 6.89 (s, 1H), 6.89 (s, 1H), 6.71 (d, 1H, J=8.23 Hz), 4.14 (m, 2H), 3.93 (s, 2H), 3.88 (s, 3H), 3.57 (m, 4H), 3.18 (s & m, 5H), 2.76 (m, 1H), 2.05-1.94 (m, 4H).

Example 1272

[2-Methoxy-4-(4-morpholin-4-yl-piperidin-1-yl)-phenyl]-(7-pyrazol-1-yl-pyrrolo[2,1-f][1,2,4]triazin-2-yl)-amine To a RB flask under argon were introduced 7-Bromo-2-methylsulfanyl-pyrrolo[2,1-f][1,2,4]triazine (300 mg, 1 mmol), 1H-Pyrazole (88.5 mg, 1.30 mmol), Cesium carbonate (801 mg, 2.46 mmol), Copper(I) iodide (50 mg, 0.3 mmol) and DMF (5 mL). The mixture was degassed for few minutes and heated at 110° C. overnight under argon. Solvent was removed and the mixture was taken in EtOAc and was passed through a pad of celite. Solvent evaporation gave the crude product which was purified by flash chromatography (ISCO, hexane :EtOAc 3:1). 2-Methylsulfanyl-7-pyrazol-1-yl-pyrrolo[2,1-f][1,2,4]triazine was isolated as a yellow syrup (23, 8%). LCMS (E/I+) 232 (M+H). 2-Methoxy-4-(4-morpholin-4-yl-piperidin-1-yl)-phenylamine (47.1 mg, 0.162 mmol), 2-Methanesulfinyl-7-pyrazol-1-yl-pyrrolo[2,1-f][1,2,4]triazine (20 mg, 0.08 mmol), N,N-Diisopropylethylamine (30 uL, 0.2 mmol) and 1-Methoxy-2-propanol (200 uL,) were combined in a microwave vial. The reaction was microwaved at 200° C. for 2.5 hours, taken up in DMSO, purified by Gilson RP-HPLC. The product, [2-Methoxy-4-(4-morpholin-4-yl-piperidin-1-yl)-phenyl]-(7-pyrazol-1-yl-pyrrolo[2,1-f][1,2,4]triazin-2-yl)-amine was isolated as a tan solid (8 mg, 21%). LCMS (E/I+) 475 (M+H). NMR $^1$H (DMSO-d$_6$)-9.75 (br s, 1H), 8.94 (s, 1H), 8.58 (d, 1H, J=2.09 Hz), 7.94 (s, 1H), 7.83 (s, 1H), 7.67 (d, 1H, J=8.72 Hz), 6.94 (s, 2H), 6.70 (s, 1H), 6.60 (s, 1H), 6.52 (d, 1H, J=8.74 Hz), 4.04-3.13 (series of m, s along with the water peak, 14H), 2.71 (m, 2H), 2.15 (d, 2H, J=11.30 Hz), 1.72 (m, 2H).

Example 1273

2-[4-(4-{7-[2-(Methanesulfonyl-methyl-amino)-4-methoxy-phenyl]-pyrrolo[2,1-f][1,2,4]triazin-2-ylamino}-3-methoxy-phenyl)-piperidin-1-yl]-acetamide The titled compound was prepared in an analogous fashion to Example 1280 replacing 2-nitro-4-methyl-phenyboronic acid with 2-nitro-4-methoxy phenylboronic acid to give 2-[4-(4-{7-[2-(Methanesulfonyl-methyl-amino)-4-methoxy-phenyl]-pyrrolo[2,1-f][1,2,4]triazin-2-ylamino}-3-methoxy-phenyl)-piperidin-1-yl]-acetamide as a solid (29 mg, 20%). LCMS (E/I+) 594 (M+H), NMR $^1$H (DMSO-d$_6$)-9.52 (br s, 1H), 8.92 (s, 1H), 7.98 (s, 1H), 7.90 (m, 2H), 7.71 (d, 2H, J=11.43 Hz), 7.17 (s, 1H), 7.13 (d, 1H, J=8.53 Hz), 6.94 (s, 2H), 6.88 (s, 1H), 6.70 (d, 1H, J=8.21 Hz), 3.9 (s, 2H), 3.89 (s, 3H), 3.86 (s, 3H), 3.75-3.3 (m along with the water peak, 2H), 3.14 (m, 2H), 3.07 (s, 3H), 2.88 (s, 3H), 2.79 (m, 1H), 2.03-1.97 (m, 4H).

Example 1274

2-(4-{3-Methoxy-4-[7-(2-methoxy-phenyl)-pyrrolo[2,1-f][1,2,4]triazin-2-ylamino]-phenyl}-3,6-dihydro-2H-pyridin-1-yl)-acetamide A mixture of 2-[4-(3-Methoxy-4-nitro-phenyl)-3,6-dihydro-2H-pyridin-1-yl]-acetamide (240 mg, 0.82 mmol), iron (138 mg, 2.47 mmol), ammonium chloride (22.0 mg, 0.412 mmol) in ethanol (7 mL, 100 mmol) and water (3 mL, 200 mmol) was heated at 80° C. After 3 h, MS showed product with no SM. The mixture was cooled, solvent was evaporated and was diluted with aq. Na$_2$CO$_3$ solution and EtOAc. The mixture was filtered through a pad of celite, extracted from EtOAc, combined organic was washed with brine. After drying, the solvent was evaporated to give the product, 2-[4-(4-Amino-3-methoxy-phenyl)-3,6-dihydro-2H-pyridin-1-yl]-acetamide, as a foam (195 mg, 91%). The product was taken to the next step without further purification. MS: 262 (M+H).

Into an 8-dram vial was added Trifluoro-methanesulfonic acid 7-(2-methoxy-phenyl)-pyrrolo[2,1-f][1,2,4]triazin-2-yl ester (210.0 mg, 0.5625 mmol), 2-[4-(4-Amino-3-methoxy-phenyl)-3,6-dihydro-2H-pyridin-1-yl]-acetamide (180 mg, 0.69 mmol), N,N-Diisopropylethylamine (0.2940 mL, 1.688 mmol) and 1-Methoxy-2-propanol (2 mL, 20 mmol). The reaction mixture was heated at 100° C. overnight. After 18 h, the product, 2-(4-{3-Methoxy-4-[7-(2-methoxy-phenyl)-pyrrolo[2,1-f][1,2,4]triazin-2-ylamino]-phenyl}-3,6-dihydro-2H-pyridin-1-yl)-acetamide, was isolated after purification with reverse phase prep-hplc (gilson) as a brown solid (46 mg, 17%). LCMS (E/I+) 582 (M+H). NMR $^1$H (DMSO-d$_6$)-10.04 (br s, 1H), 8.97 (s, 1H), 8.15 (d, 1H, J=8.43 Hz), 7.96 (s, 1H), 7.80 (d, 1H, J=7.44 Hz), 7.72 (s, 2H), 7.48 (m, 1H), 7.23 (d, 1H, J=8.4 Hz), 7.13 (m, 2H0, 7.0-6.93 (m, 3H), 6.17 (s, 1H0, 4.01-3.2 (series of s, m along with the water peak, 12H), 2.78 (m, 2H).

Example 1275

2-(4-{3-Methoxy-4-[7-(2-methoxy-phenyl)-pyrrolo[2,1-f][1,2,4]triazin-2-ylamino]-phenyl}-piperidin-1-yl)-propionamide A mixture of 4-(3-Methoxy-4-nitro-phenyl)-1,2,3,6-tetrahydro-pyridine hydrochloride (364 mg, 1.34 mmol) (generated by 4N HCl treatment of the of BOC precursor, 450 mg, for 1 h), 2-Bromo-propionamide (204 mg, 1.34 mmol), and cesium carbonate (1095 mg, 3.362 mmol) in acetonitrile (10 mL, 200 mmol) was stirred overnight at reflux. The mixture was cooled to RT and was filtered through a pad of celite. After solvent evaporation and flash chromatography (ISCO, EtOAC: MeOH 98:3), the product, 2-[4-(3-Methoxy-4-nitro-phenyl)-3,6-dihydro-2H-pyridin-1-yl]-propionamide was isolated as a gum (101 mg, 25%). MS: 306 (M+H).

To a solution of the above compound in methanol (10 mL, 200 mmol) was added 10% Palladium on Carbon (50% Wet, 34 mg, 0.016 mmol). The mixture was shaken in a Parr apparatus under an atmosphere of Hydrogen (50 PSI) overnight. Filtration through celite and evaporation of the solvent provided crude 2-[4-(4-Amino-3-methoxy-phenyl)-piperidin-1-yl]-propionamide, which was used without further purification.

Into an 8-dram vial Trifluoro-methanesulfonic acid 7-(2-methoxy-phenyl)-pyrrolo[2,1-f][1,2,4]triazin-2-yl ester (100 mg, 0.3 mmol), 2-[4-(4-Amino-3-methoxy-phenyl)-piperidin-1-yl]-propionamide (79 mg, 0.28 mmol), N,N-Diisopropylethylamine (150 uL, 0.86 mmol) and 1-Methoxy-2-propanol (2 mL, 20 mmol) were added and the reaction mixture was heated at 100° C. overnight. After 18 h, the product was isolated by reverse phase preparative-hplc (gilson). The product, 2-(4-{3-Methoxy-4-[7-(2-methoxy-phenyl)-pyrrolo[2,1-f][1,2,4]triazin-2-ylamino]-phenyl}-piperidin-1-yl)-propionamide. TFA salt was obtained as a brown solid (41 mg, 29%). LCMS (E/I+) 501 (M+H). NMR $^1$H (DMSO-d$_6$)-9.42 (s, 1H), 8.95 (s, 1H), 8.06 (d, 2H, J=7.88 Hz), 7.84 (d, 2H, J=7.48 Hz), 7.64 (s, 1H), 7.46 (t, 1H, J=7.92 Hz), 7.21 (d, 1H, J=8.32 Hz), 7.10 (t, 1H, J=7.52 Hz), 6.96 (dd, 2H, J=4.64 & 11.8 Hz), 6.87 (s, 1H), 6.69 (d, 1H, J=8.16 Hz), 4.03-3.41 (s & m with the water peak, 9H), 3.18-3.05 (two m, 2H), 2.80 (m, 1H), 2.05 (m, 4H), 1.49 (d, J=6.88 Hz, 3H).

Example 1276

2-(4-{3-Methoxy-4-[7-(2-methoxy-phenyl)-pyrrolo[2,1-f][1,2,4]triazin-2-ylamino]-phenyl}-piperidin-1-yl)-1-piperazin-1-yl-ethanone Into a 1-Neck round-bottom flask was added 4-(3-Methoxy-4-nitro-phenyl)-1,2,3,6-tetrahydro-pyridine; hydrochloride (364 mg, 1.34 mmol) (generated by 4N HCl treatment of the 450 mg of BOC precursor for 1 h), 4-(2-Bromo-acetyl)-piperazine-1-carboxylic acid tert-butyl ester (413.0 mg, 1.345 mmol) and cesium carbonate (1095 mg, 3.362 mmol) in acetonitrile (10 mL, 200 mmol). The reaction was stirred overnight at reflux. The reaction mixture was cooled to RT, diluted with water and was extracted (twice) from EtOAc. Combined organic was washed with brine and was dried over MgSO4. After solvent evaporation and flash chromatography (ISCO, EtOAC: MeOH 98:2), the product, 4-{2-[4-(3-Methoxy-4-nitro-phenyl)-3,6-dihydro-2H-pyridin-1-yl]-acetyl}-piperazine-1-carboxylic acid tert-butyl ester, was isolated as a gum/solid (301 mg, 49%). NMR $^1$H (DMSO-d$_6$)-7.86 (d, 1H, J=8.54 Hz), 7.29 (s, 1H), 7.17 (d, 1H, J=8.58 Hz), 6.44 (s, 1H), 3.96 (s, 3H), 3.52 (br s, 2H), 3.44 (br s, 2H), 3.32 m with the water peak, 8H), 3.30 (m, 2H).

To a solution of 4-{2-[4-(3-Methoxy-4-nitro-phenyl)-3,6-dihydro-2H-pyridin-1-yl]-acetyl}-piperazine-1-carboxylic acid tert-butyl ester (250 mg, 0.54 mmol) in methanol (20 mL) was added 10% Palladium on Carbon (50% Wet, 58 mg, 0.027 mmol). The mixture was shaken in a Parr apparatus under an atmosphere of Hydrogen (50 PSI) overnight. Filtration through Celite and evaporation of the solvent provided crude 4-{2-[4-(4-Amino-3-methoxy-phenyl)-piperidin-1-yl]-acetyl}-piperazine-1-carboxylic acid tert-butyl ester, which was used without further purification.

Into an 8-dram vial Trifluoro-methanesulfonic acid 7-(2-methoxy-phenyl)-pyrrolo[2,1-f][1,2,4]triazin-2-yl ester (170 mg, 0.46 mmol), 4-{2-[4-(4-Amino-3-methoxy-phenyl)-piperidin-1-yl]-acetyl}-piperazine-1-carboxylic acid tert-butyl ester (223 mg, 0.516 mmol), N,N-Diisopropylethylamine (250 uL, 1.4 mmol) and 1-Methoxy-2-propanol (2 mL, 20 mmol). The reaction mixture was heated at 100° C. overnight. After 18 h, the mixture was cooled to RT and the product was purified by flash chromatography (ISCO, 40 g column, EtOAC-MeOH 95:5). The product was obtained as a syrup (156 mg, 52%). MS: 656 (M+H). The product was subjected to the BOC deprotection step. 4-[2-(4-{3-Methoxy-4-[7-(2-methoxy-phenyl)-pyrrolo[2,1-f][1,2,4]triazin-2-ylamino]-phenyl}-piperidin-1-yl)-acetyl]-piperazine-1-carboxylic acid tert-butyl ester (150 mg, 0.23 mmol) was treated with trifluoroacetic acid (0.5 mL, 6 mmol) in methylene chloride (10 mL, 200 mmol). The mixture was stirred at RT. After 3 days, solvent was removed and the product, 2-(4-{3-Methoxy-4-[7-(2-methoxy-phenyl)-pyrrolo[2,1-f][1,2,4]triazin-2-ylamino]-phenyl}-piperidin-1-yl)-1-piperazin-1-yl-ethanone, was purified by reverse phase liquid chromatography (Gilson) as a brown solid (61 mg, 48%, ~85% pure). LCMS (E/I+) 556 (M+H). NMR $^1$H (DMSO-d$_6$)-9.6 (br s, 1H), 9.02 (br s, 2H), 8.95 (s, 1H), 7.07 (d, 1H, J=8.27 Hz), 7.82 (d, 1H, J=6.44 Hz), 7.64 (s, 1H), 7.46 (m, 1H), 7.21 (d, 1H, J=8.37 Hz), 7.10 (m, 1H), 6.96 (m, 2H), 6.90 (s, 1H), 6.71 (d, 1H, J=8.34 Hz), 4.35 (m, 2H), 4.2-3.0 (series of m and s along with water peak, 18H), 2.84 (m, 1H), 2.08-1.99 (m, 4H).

Example 1277

(4-{3-Methoxy-4-[7-(2-methoxy-phenyl)-pyrrolo[2, 1-f][1,2,4]triazin-2-ylamino]-phenyl}-piperidin-1-yl)-acetic acid tert-butyl ester Into a 1-Neck round-bottom flask was added 4-(3-Methoxy-4-nitro-phenyl)-1,2,3,6-tetrahydro-pyridine; hydrochloride (809 mg, 2.99 mmol) (generated by 4N HCl in dioxane treatment of the 1 g of the BOC precursor for 1 h), cesium carbonate (2141 mg, 6.570 mmol), N,N-Diisopropylethylamine (624 uL, 3.584 mmol) in acetonitrile (20 mL). To it was added Acetic acid, bromo-1,1,1-dimethylethyl ester (438.0 uL, 2.986 mmol) and the reaction was stirred overnight at RT. After 18 h, the mixture was filtered through a pad of celite. Solvent was evaporated and the product, [4-(3-Methoxy-4-nitro-phenyl)-3,6-dihydro-2H-pyridin-1-yl]-acetic acid tert-butyl ester, was purified by flash chromatography (ISCO, hexane:EtOAc 3:2) as a crystalline solid (903 mg, 87%). LCMS (E/I+) 349 (M+H).

To a solution of [4-(3-Methoxy-4-nitro-phenyl)-3,6-dihydro-2H-pyridin-1-yl]-acetic acid tert-butyl ester (145 mg, 0.416 mmol) in methanol (15 mL, 370 mmol) was added 10% Palladium on Carbon (50% Wet, 44.3 mg, 0.0208 mmol). The mixture was shaken in a Parr apparatus under an atmosphere of Hydrogen (50 PSI) for 3 h. Filtration through Celite and evaporation of the solvent provided crude [4-(4-Amino-3-methoxy-phenyl)-piperidin-1-yl]-acetic acid tert-butyl ester, which was used without further purification.

Into an 8-dram vial Trifluoro-methanesulfonic acid 7-(2-methoxy-phenyl)-pyrrolo[2,1-f][1,2,4]triazin-2-yl ester (100 mg, 0.3 mmol), [4-(4-Amino-3-methoxy-phenyl)-piperidin-1-yl]-acetic acid tert-butyl ester (133 mg, 0.415 mmol), N,N-Diisopropylethylamine (150 uL, 0.86 mmol) and 1-Methoxy-2-propanol (2 mL, 20 mmol) were added. The reaction mixture was heated at 80° C. After 3 days, solvent was removed and the product, (4-{3-Methoxy-4-[7-(2-methoxy-phenyl)-pyrrolo[2,1-f][1,2,4]triazin-2-ylamino]-phenyl}-piperidin-1-yl)-acetic acid tert-butyl ester, was purified by flash chromatography (ISCO, 40 g column, hexane; EtOAc 1:1) as a gum (79 mg, 54%). LCMS (E/I+) 544 (M+H). NMR $^1$H (MeOH-d$_4$)-8.7 (s, 1H), 8.16 (d, 1H, J=8.28 Hz), 7.82 (d, 1H, J=7.56 Hz), 7.45 (m, 1H), 7.16 (d, 1H, J=8.32 Hz), 7.09 (m, 1H), 6.95 (d, 1H, J=4.67 Hz), 6.89 (d, 1H, J=4.68 Hz), 6.81 (s, 1H), 6.72 (s, 1H), 6.63 (m, 1H), 3.89 (s, 3H), 3.83 (s, 2H), 3.80 (s, 3H), 3.03 (m, 2H), 2.43 (m, 1H), 2.25 (m, 2H), 1.76 (m, 4H), 1.49 (s, 9H).

Example 1278

(4-{3-Methoxy-4-[7-(2-methoxy-phenyl)-pyrrolo[2, 1-f][1,2,4]triazin-2-ylamino]-phenyl}-piperidin-1-yl)-acetic acid A solution of] (4-{3-Methoxy-4-[7-(2-methoxy-phenyl)-pyrrolo[2,1-f][1,2,4]triazin-2-ylamino]-phenyl}-piperidin-1-yl)-acetic acid tert-butyl ester (73 mg, 0.13 mmol) in 2 mL of 4N HCl in dioxane was stirred at RT. After 18 h, solvent was evaporated and the mixture was triturated with ether. A solid was obtained which was filtered, washed with ether (twice) and dried. The product, (4-{3-Methoxy-4-[7-(2-methoxy-phenyl)-pyrrolo[2,1-f][1,2,4]triazin-2-ylamino]-phenyl}-piperidin-1-yl)-acetic acid was isolated as a pale yellow hygroscopic solid (54 mg, 82%). LCMS (E/I+) 488 (M+H). NMR $^1$H (DMSO-d$_6$)-10.1 (br s, 1H), 8.96 (s, 1H0, 8.05 (d, 1H, J=8.24 Hz), 7.81 (d, 1H, J=7.49 Hz), 7.68 (s, 1H), 7.46 (m, 1H), 7.41 (d, 1H, J=7.96 Hz), 7.21 (d, 1H, J=8.34 Hz), 7.11 (d, 1H, J=7.45 Hz), 7.08 (m, 1H), 6.98 (m, 2H), 6.70 (d, 1H, J=7.32 Hz), 4.16 (br s, 2H), 4.05-3.1 (series of m and s along with the water peak, 10H), 2.8 (m, 1H), 2.03 (m, 4H).

Example 1279

N-(2-Hydroxy-1-hydroxymethyl-ethyl)-2-(4-{3-methoxy-4-[7-(2-methoxy-phenyl)-pyrrolo[2,1-f][1, 2,4]triazin-2-ylamino]-phenyl}-piperidin-1-yl)-acetamide A mixture of (4-{3-Methoxy-4-[7-(2-methoxy-phenyl)-pyrrolo[2,1-f][1,2,4]triazin-2-ylamino]-phenyl}-piperidin-1-yl)-acetic acid (40 mg, 0.08 mmol), 4-Nitro-phenol (20 mg, 0.2 mmol), N-(3-Dimethylaminopropyl)-N'-ethylcarbodiimide hydrochloride (31 mg, 0.16 mmol), 4-Dimethylaminopyridine (5 mg, 0.04 mmol) in Methylene chloride (0.005 mL, 0.08 mmol) and N,N-Dimethylformamide (0.006 mL, 0.08 mmol) was stirred at RT and the reaction was followed by MS and HPLC. After 2 h, solvent was evaporated and to the mixture was added Methanol (2 mL, 50 mmol) and Diethanolamine (11 mg, 0.11 mmol). The mixture was stirred at RT overnight. After 18 h, solvent was removed and the product was purified by flash chromatography (ISCO, 40 g column, DCM: MeOH 95:5). 24 mg of a solid was obtained which was further purified by RP-LC (Gilson). N-(2-Hydroxy-1-hydroxymethyl-ethyl)-2-(4-{3-methoxy-4-[7-(2-methoxyphenyl)-pyrrolo[2,1-f][1,2,4]triazin-2-ylamino]-phenyl}-piperidin-1-yl)-acetamide was isolated as a yellow solid. LCMS (E/I+) 561 (M+H). NMR $^1$H (DMSO-d$_6$)-9.95 (s, 1H), 9.57 (s, 1H), 8.39 (d, 1H, J=8.09 Hz), 8.06 (d, J=8.35 Hz), 7.81 (d, 1H, J=6.85 Hz), 7.64 9 s, 1H), 7.46 (m, 1H), 7.21 (d, 1H, 8.26 Hz), 7.1 (t, 1H, J=7.55 Hz), 6.96 (d, 1H, J=8.04 Hz), 3.92-3.75 (overlapping s & m, 10H), 3.7-3.1 (m along with water peak, 8H), 2.77 (m, 1H), 2.08-1.97 (m, 4H).

Example 1280

2-[4-(4-{7-[2-(Methanesulfonyl-methyl-amino)-4-methyl-phenyl]-pyrrolo[2,1-f][1,2,4]triazin-2-ylamino}-3-methoxy-phenyl)-piperidin-1-yl]-acetamide 7-Bromo-2-methylsulfanyl-pyrrolo[2,1-f][1,2,4]triazine (600 mg, 2 mmol), 2-nitro-4-methyl-phenylboronic acid (500 mg, 3 mmol) 1.50 M of Sodium carbonate in Water (5 mL, 8 mmol) and dioxane (10 mL) were added to a RB flask. The reaction mixture was degassed with nitrogen for 10 minutes. Tetrakis(triphenylphosphine)palladium(0) (100 mg, 0.1 mmol) was added and the reaction mixture was degassed again. The reaction mixture was heated at 95° C. overnight under argon. MS showed product formation. The mixture was cooled to RT, concentrated, filtered through a pad of celite, and partitioned with water and EtOAc. The organic phase was separated, washed with brine, and dried over magnesium sulfate. After solvent evaporation, the product, 7-(4-Methyl-2-nitro-phenyl)-2-methylsulfanyl-pyrrolo[2,1-f][1,2,4]triazine, was obtained as a solid which was further purified by taking in ether followed by filtration and washing with ether (628 mg, 80%). LCMS (E/I+) 301 (M+H).

1280a) A mixture of 7-(4-Methyl-2-nitro-phenyl)-2-methylsulfanyl-pyrrolo[2,1-f][1,2,4]triazine (620 mg, 2.1 mmol), iron (346 mg, 6.19 mmol), ammonium chloride (55.2 mg, 1.03 mmol) in ethanol (12.0 mL, 206 mmol) and water (8 mL, 400 mmol) was heated at 100° C. The mixture was cooled, solvent was evaporated and was diluted with water and EtOAc. It was filtered through a pad of celite, extracted from EtOAc, combined organic was washed with brine. After drying, solvent was evaporated to give 5-Methyl-2-(2-methylsulfanyl-pyrrolo[2,1-f][1,2,4]triazin-7-yl)-phenylamine as a solid (491 mg, 88%). LCMS (E/I+) 271. The product was taken to the next step without further purification.

1280b) To a mixture of 5-Methyl-2-(2-methylsulfanyl-pyrrolo[2,1-f][1,2,4]triazin-7-yl)-phenylamine (480 mg, 1.8 mmol) in dry pyridine (4 mL, 50 mmol) was added at 0° C. methanesulfonyl chloride (160 uL, 2.1 mmol). The mixture was stirred for 2 h and was thrown to 3N HCl. The mixture was extracted from EtOAc. Combined organic was washed with brine and was dried. After solvent evaporation, the product, N-[5-Methyl-2-(2-methylsulfanyl-pyrrolo[2,1-f][1,2,4]triazin-7-yl)-phenyl]-methanesulfonamide, was obtained as a yellow solid (591 mg, 96%). The solid was used directly for the next step.

1280ca) Into a RB flask, N-[5-Methyl-2-(2-methylsulfanyl-pyrrolo[2,1-f][1,2,4]triazin-7-yl)-phenyl]-methanesulfonamide (580 mg, 1.7 mmol) and N,N-Dimethylformamide (13 mL,) were added. Resulting solution was cooled to 0° C., m-CPBA (70:30, m-Chloroperbenzoic acid:3-Chlorobenzoic acid, 431 mg, 1.75 mmol) was added in portion over 10 minutes. After 2 h, solvent was removed. The residue was partitioned with DCM and sat. NaHCO$_3$ solution. The organic phase was separated, washed with brine, and dried over Magnesium sulfate. N-[2-(2-Methanesulfinyl-pyrrolo[2,1-f][1,2,4]triazin-7-yl)-5-methyl-phenyl]-methanesulfonamide was obtained as a yellow solid (539 mg, 89%) which was taken to the next step without further purifications. LCMS (E/I+) 365 (M+H).

1280d) N-[2-(2-Methanesulfinyl-pyrrolo[2,1-f][1,2,4]triazin-7-yl)-5-methyl-phenyl]-methanesulfonamide (530 mg, 1.4 mmol) was dissolved in 20 mL of dry and warm DMF. The solution was cooled (ice bath). Potassium carbonate (0.80 g, 5.8 mmol) in N,N-Dimethylformamide (20 mL, 200 mmol) was added followed by methyl iodide (270 uL, 4.4 mmol). After 18 h, the mixture was stirred at room temperature overnight. The mixture was filtered and the solvent was evaporated. The product was purified by flash chromatography (ISCO, EtOAc to EtOAc: MeOH 90:10). The product, N-[2-(2-Methanesulfinyl-pyrrolo[2,1-f][1,2,4]triazin-7-yl)-5-methyl-phenyl]-N-methyl-methanesulfonamide, was obtained as a solid (320 mg, 58%). LCMS (E/I+) 379 (M+H).

1280e) A mixture of N-[2-(2-Methanesulfinyl-pyrrolo[2,1-f][1,2,4]triazin-7-yl)-5-methyl-phenyl]-N-methyl-methanesulfonamide (315 mg, 0.832 mmol) in 5M NaOH (10 mL, 10 mmol) was stirred at 80° C. After 3 h, HPLC and MS showed product formation with no SM. The mixture was cooled to RT and pH of the solution was adjusted to 4 by adding HCl. The mixture was repeatedly extracted from EtOAc. Combined organic was washed with brine and was dried over magnesium sulfate. After solvent evaporation, N-[2-(2-Hydroxy-pyrrolo[2,1-f][1,2,4]triazin-7-yl)-5-methyl-phenyl]-N-methyl-methanesulfonamide was isolated as a solid (153 mg, 55%). LCMS (E/I+) 333 (M+H).

1280f) N-[2-(2-Hydroxy-pyrrolo[2,1-f][1,2,4]triazin-7-yl)-5-methyl-phenyl]-N-methyl-methanesulfonamide (143 mg, 0.430 mmol) was dissolved in N,N-Dimethylformamide (5 mL). N,N-Diisopropylethylamine (250 uL, 1.4 mmol) was added followed by N-Phenylbis(trifluoromethanesulphonimide) (170 mg, 0.48 mmol) at RT. After 1 h, LC-MS showed triflate formation (no SM). 2-[4-(4-Amino-3-methoxy-phenyl)-piperidin-1-yl]-acetamide (150 mg, 0.57 mmol) was added and the mixture was heated at 80° C. After 3 days, solvent was evaporated and the mixture was taken in water-EtOAc. The mixture was extracted 3 times from EtOAc. Combined organic was washed with water followed by brine. After drying over magnesium sulfate, solvent was evaporated. The product was purified by RP-LC (Gilson). 2-[4-(4-{7-[2-(Methanesulfonyl-methyl-amino)-4-methyl-phenyl]-pyrrolo[2,1-f][1,2,4]triazin-2-ylamino}-3-methoxy-phenyl)-piperidin-1-yl]-acetamide . TFA salt was isolated as a solid (70 mg, 28%). LCMS (E/I+) 578 (M+H). $^1$H (DMSO-d$_6$)-9.56 (br, s, 1H), 8.97 (s, 1H), 8.11 (d, 1H, J=8.08 Hz), 8.05 (s, 1H), 7.98 (d, 2H, J=8.24 Hz), 7.86 (s, 1H), 7.73 (s, 1H), 7.43 (d, 1H, J=8.12 Hz), 7.23 (d, 1H, J=4.72 Hz), 6.98 (d, 1H, J=4.72 Hz), 6.94 (s, 1H), 6.85 (d, 1H, J=8.2 Hz), 3.94 (s, 2H), 3.89 (s, 3H), 3.59 (m, 2H), 3.2 (s & m, 2H), 3.04 (s, 3H), 2.83 (m, 1H), 2.35 (s, 3H0, 2.1-2.01 (m, 4H).

Example 1281

N-{2-[2-(2-Methoxy-4-piperidin-4-yl-phenylamino)-pyrrolo[2,1-f][1,2,4]triazin-7-yl]-5-methyl-phenyl}-N-methyl-methanesulfonamide The titled compound was prepared in an analogous fashion to Example 1280 replacing 2-[4-(4-Amino-3-methoxy-phenyl)-piperidin-1-yl]-acetamide with 4-(4-Amino-3-methoxy-phenyl)-piperidine-1-carboxylic acid tert-butyl ester and via hydrolysis of the resulting 4-(4-{7-[2-(M ethanesulfonyl-methyl-amino)-4-methyl-phenyl]-pyrrolo[2,1-f][1,2,4]triazin-2-ylamino}-3-methoxy-phenyl)-piperidine-1-carboxylic acid tert-butyl ester with 1:1 dichlromethane: TFA to give N-{2-[2-(2-Methoxy-4-piperidin-4-yl-phenylamino)-pyrrolo[2,1-f][1,2,4]triazin-7-yl]-5-methyl-phenyl}-N-methyl-methane sulfonamide as a solid (16 mg, 43%). LCMS (E/I+) 521 (M+H). $^1$H (DMSO-d$_6$)-8.97 (s, 1H), 8.59 (m, 1H), 8.36 (m, 1H), 8.11 (d, 1H, J=8.1 Hz, 1H), 8.05 (s, 1H), 7.97 (d, 1H, J=8.15 Hz), 7.86 (s, 1H), 7.43 (d, 1H, J=8.09 Hz), 7.24 (d, 1H, J=4.74 Hz), 6.98 (d, 1H, J=4.74 Hz), 6.92 (s, 1H), 6.84 (d, 1H, J=8.17 Hz), 3.00 (s & m, 5H), 2.85 (m, 1H), 2.37 (s, 3H), 1.98 (m, 2H), 1.83 (m, 2H).

Example 1282

2-[4-(4-{7-[5-Fluoro-2-(methanesulfonyl-methyl-amino)-phenyl]-pyrrolo[2,1-f][1,2,4]triazin-2-ylamino}-3-methoxy-phenyl)-piperidin-1-yl]-acetamide The titled compound was prepared in an analogous fashion to Example 1280 replacing 2-nitro-4-methyl-phenyboronic acid with 2-amino-5-fluoro phenylboronic acid to give 2-[4-(4-{7-[5-Fluoro-2-(methanesulfonyl-methyl-amino)-phenyl]-pyrrolo[2,1-f][1,2,4]triazin-2-ylamino}-3-methoxy-phenyl)-piperidin-1-yl]-acetamide as a solid (61 mg, 35%). LCMS (E/I+) 582 (M+H), NMR $^1$H (DMSO-d$_6$)-9.6 (brs, 1H), 8.98 (s, 1H), 7.98-7.90 (m, 3H), 7.85 (s, 1H), 7.72-7.68 (s & m, 2H), 7.35 (m, 1H), 7.08 (d, 1H, J=4.68 Hz), 6.97 (d, 1H, J=4.72 Hz), 6.90 (s, 1H), 6.71 (d, 1H, J=8.24 Hz), 3.92 (br s, 2H0, 3.87 (s, 3H0, 3.27-3.06 (s & m, 8H), 2.93 (s, 3H), 2.75 (m, 1H), 2.05-1.94 (m, 4H).

Example 1283

2-[4-(4-{7-[2-(Methanesulfonyl-methyl-amino)-5-methoxy-phenyl]-pyrrolo[2,1-f][1,2,4]triazin-2-ylamino}-3-methoxy-phenyl)-piperidin-1-yl]-acetamide The titled compound was prepared in an analogous fashion to Example 1280 replacing 2-nitro-4-methyl-phenyboronic acid with 5-methoxy-2-amino boronic acid to give 2-[4-(4-{7-[2-(Methanesulfonyl-methyl-amino)-5-methoxy-phenyl]-pyrrolo[2,1-f][1,2,4]triazin-2-ylamino}-3-methoxy-phenyl)-piperidin-1-yl]-acetamide as a solid (36 mg, 26%). LCMS (E/I+) 593 (M+H), $^1$H (DMSO-d$_6$)-9.55 (br s, 1H), 8.96 (s, 1H), 7.99 (d, 2H, J=6.64 Hz), 7.73 (s, 2H), 7.56 (d, 2H, J=7.6 Hz), 7.09 (d, 1H, J=8.80 Hz), 7.02 (s, 1H), 6.97 (d, J=3.28 Hz, 1H), 6.89 (s, 1H), 6.66 (d, 1H, J=8.08 Hz), 3.93 (br s, 2H), 3.86 (s, 3H), 3.81 (s, 3H), 3.8-3.35 (m & the water peak, 2H), 3.15 (m, 2H), 3.06 (s, 3H), 2.87 (s, 3H), 2.76 (m, 1H), 2.03 (m, 4H).

Example 1291

(4-Morpholin-4-yl-phenyl)-[7-(1H-pyrrol-2-yl)-pyrrolo[2,1-f][1,2,4]triazin-2-yl]-amine 1291a) 2-(2-Methylsulfanyl-pyrrolo[2,1-f][1,2,4]triazin-7-yl)-pyrrole-1-carboxylic acid tert-butyl ester: A mixture of 7-bromo-2-methylsulfanyl-pyrrolo[2,1-f][1,2,4]triazine (2.082 g, 8.529 mmol), 1-t-butoxycarbonylpyrrole-2-boronic acid (2.302 g, 10.91 mmol) and tetrakis(triphenylphosphine) palladium(0) (617 mg, 0.534 mmol) in 1,2-dimethoxyethane (100 mL) was evacuated and flushed with nitrogen before adding a solution of sodium carbonate (2.687 g, 25.35 mmol) in water (30 mL). This mixture was evacuated and flushed with nitrogen as well before warming to reflux for 15 h. The reaction mixture was reduced by ~75% before extracting residue into DCM. The organic layer was separated and dried by passing through a plug of Na$_2$SO$_4$. Solvent was removed by rotary evaporation and the resulting residue was purified with an ISCO chromatography unit outfitted with a silica gel column and eluted with a gradient of EtOAc/hexane. Product containing fractions were combined and evaporated to yield 2.222 g (79%) of 2-(2-methylsulfanyl-pyrrolo[2,1-f][1,2,4]triazin-7-yl)-pyrrole-1-carboxylic acid tert-butyl ester. $^1$H NMR (DMSO-d$_6$): 9.01 (s, 1H), 7.53 (dd, J=3.2, 1.8, 1H), 7.03 (d, J=4.6, 1H), 7.00 (d, J=4.6, 1H), 6.49 (dd, J=4.4, 2.0, 1H), 6.39 (t, J=3.1, 1H), 2.35 (s, 3H), 1.08 (s, 9H).

1291b) 2-(2-Methanesulfinyl-pyrrolo[2,1-f][1,2,4]triazin-7-yl)-pyrrole-1-carboxylic acid tert-butyl ester: To a mixture of above 2-(2-methylsulfanyl-pyrrolo[2,1-f][1,2,4]triazin-7-yl)-pyrrole-1-carboxylic acid tert-butyl ester (157 mg, 0.475 mmol), sodium bicarbonate (52 mg, 0.62 mmol) in methylene chloride (20 mL) was added MCPBA (123 mg, 70-75%). The mixture was stirred at RT for 2 h, poured into separatory funnel and sequentially washed with 10% aqueous solution of Na$_2$S$_2$O$_3$ and saturated, aqueous NaHCO$_3$. The organic layer was separated and dried by passing through a plug of Na$_2$SO$_4$. Solvent was removed by rotary evaporation and the resulting residue was purified with an ISCO chromatography unit outfitted with a 12 g silica gel column and eluted with a gradient of EtOAc/hexane. Product containing fractions were combined and evaporated to yield 137 mg (83%) of residue that showed a single peak by LC/MS (m/e=347); this material was used as such in subsequent transformations.

1291c) (4-Morpholin-4-yl-phenyl)-[7-(1H-pyrrol-2-yl)-pyrrolo[2,1-f][1,2,4]triazin-2-yl]-amine: A mixture of the above 2-(2-methanesulfinyl-pyrrolo[2,1-f][1,2,4]triazin-7-yl)-pyrrole-1-carboxylic acid tert-butyl ester (68 mg, 0.20 mmol), 4-(4-morpholino)aniline (70.0 mg, 0.393 mmol) and N,N-Diisopropylethylamine (76.9 uL, 0.442 mmol) in 1-Methoxy-2-propanol (150 uL) was heated in a microwave reactor at 170° C. for 2 h. The reaction mixture was evaporated and the residue diluted in DMSO before purification on a Gilson RP pHPLC (MeCN/H$_2$O containing 0.1% TFA). Appropriate fractions were combined and lyophilized to afford 14.5 mg (20%) of brown powder. LC/MS: 361 (M+H); HPLC: 97% pure, RT=2.23 min; $^1$H NMR (DMSO, δ): 11.38 (s, 1H), 9.18 (s, 1H), 8.83 (s, 1H), 7.67 (d, J=8.7, 2H), 7.11 (d, J=4.9, 1H), 7.08 (s, 1H), 7.04 (d, J=8.7, 2H), 6.98 (m, 1H), 6.89 (d, J=4.9, 1H), 6.26 (m, 1H), 3.79 (m, 4H), 3.14 (m, 4H).

Example 1292

N-{3-[7-(1H-Pyrrol-2-yl)-pyrrolo[2,1-f][1,2,4]triazin-2-ylamino]-phenyl}-acetamide Following the synthetic and purification procedures described in Example 1291c, 2-(2-methanesulfinyl-pyrrolo[2,1-f][1,2,4]triazin-7-yl)-pyrrole-1-carboxylic acid tert-butyl ester (80 mg, 0.2 mmol) was coupled with 3'-aminoacetanilide (77.0 mg, 0.513 mmol). Yield of TFA salt: 6 mg (7%); LC/MS: 333 (M+H); HPLC: 97% pure, RT=2.32 min; $^1$H NMR (DMSO, δ): 11.35 (s, 1H), 9.90 (s, 1H), 9.34 (s, 1H), 8.85 (s, 1H), 7.89 (s, 1H), 7.51 (d, J=8.5, 1H), 7.25 (t, J=8.2, 1H), 7.17 (s, 1H), 7.14 (d, J=4.7, 1H), 7.07 (s, 1H), 6.96 (m, 1H), 6.92 (d, J=4.7, 1H), 6.22 (m, 1H), 2.05 (s, 3H).

Example 1293

3-{2-[2-(4-Morpholin-4-yl-phenylamino)-pyrrolo[2,1-f][1,2,4]triazin-7-yl]-pyrrol-1-yl}-propionitrile 1293a) 2-Methylsulfanyl-7-(1H-pyrrol-2-yl)-pyrrolo[2,1-f][1,2,4]triazine bis-trifluoroacetate salt: To a solution of the pyrrole from Example 1291a (2.222 g, 6.725 mmol) in methylene chloride (140 mL) was added trifluoroacetic acid (20 mL) and the mixture was stirred at RT for 15 h. Reaction solvent was removed by rotary evaporation and the residue was repeatedly evaporated from EtOAc to afford 2-methylsulfanyl-7-(1H-pyrrol-2-yl)-pyrrolo[2,1-f][1,2,4]triazine as its bis-trifluoroacetate salt. $^1$H NMR (DMSO-d$_6$): 11.50 (s, 1H), 8.87 (s, 1H), 7.32 (d, J=4.8, 1H), 7.12 (m, 1H), 7.05 (d, J=4.81, 1H), 7.02 (m, 1H), 6.27 (m, 1H), 2.64 (s, 3H).

1293b) 3-[2-(2-Methylsulfanyl-pyrrolo[2,1-f][1,2,4]triazin-7-yl)-pyrrol-1-yl]-propionitrile: The above bis-TFA salt (92 mg) was taken up in DCM and washed with dilute, aqueous, NaOH. The organic layer was dried by passing through a plug of Na$_2$SO$_4$ and solvent evaporated to yield 2-methylsulfanyl-7-(1H-pyrrol-2-yl)-pyrrolo[2,1-f][1,2,4]triazine (46 mg, 0.20 mmol) which was taken up in acetonitrile (1.0 mL) and treated with 2-propenenitrile (19 uL, 0.29 mmol) and Triton B (5 µL). The mixture was stirred at RT for 1 h. The reaction was taken up in EtOAc and washed with water and brine. The organic layer was dried by passing through a plug of Na$_2$S0. Solvent was removed by rotary evaporation and the resulting residue was triturated with ether (2×2 mL) to yield 44 mg (78%) of product. HPLC RT: 2.93 min; LC/MS: 284 (M+H); $^1$H NMR (DMSO-d$_6$): 8.99 (s, 1H), 7.13 (m, 1H), 7.09 (s, 2H), 6.66 (dd, J=3.8, 1.7, 1H), 6.27 (dd, J=3.8, 2.9, 1H), 4.30 (t, J=6.6, 2H), 2.86 (t, 2H, J=6.6), —SMe singlet presumably under DMSO peak.

1293c) 3-{2-[2-(4-Morpholin-4-yl-phenylamino)-pyrrolo[2,1-f][1,2,4]triazin-7-yl]-pyrrol-1-yl}-propionitrile: Following the synthetic and purification procedures described in Example 1291b, 3-[2-(2-methylsulfanyl-pyrrolo[2,1-f][1,2,4]triazin-7-yl)-pyrrol-1-yl]-propionitrile (395 mg, 1.39 mmol) was oxidized to afford the titled compound (187 mg, 45%) HPLC RT: 2.92 min; LC/MS: 347 (M+H); $^1$H NMR (DMSO-d$_6$): 9.28 (s, 1H), 7.33 (d, J=4.6, 1H), 7.31 (d, J=4.6, 1H), 7.19 (m, 1H), 6.57 (dd, J=3.6, 1.6, 1H), 6.29 (t, J=3.2, 1H), 4.21 (t, J=6.8, 2H), 3.03 (m, 2H), 2.94 (s, 3H).

1293d) 3-{2-[2-(4-Morpholin-4-yl-phenylamino)-pyrrolo[2,1-f][1,2,4]triazin-7-yl]-pyrrol-1-yl}-propionitrile: A mixture of 3-[2-(2-methanesulfinyl-pyrrolo[2,1-f][1,2,4]triazin-7-yl)-pyrrol-1-yl]-propionitrile (98 mg, 0.33 mmol), 4-(4-morpholino)aniline (78 mg, 0.44 mmol) and N,N-diisopropylethylamine (71 mg, 0.55 mmol) in 1-methoxy-2-propanol (1.0 mL) was heated in a sealed vial at 120° C. for 84 h. The evaporated reaction mixture was purified as describe in Example 1291d. Yield of TFA salt: 78 mg (50%) of brown powder. LC/MS: 361 (M+H); HPLC: 97% pure, RT=2.37 min; mp: 85-89° C.; $^1$H NMR: (DMSO, δ) 9.39 (s, 1H), 8.94 (s, 1H), 7.66 (d, J=8.8, 2H), 7.15 (m, 1H), 7.04 (d, J=8.8, 2H), 6.94 (d, J=4.7, 1H), 6.89 (d, J=4.7, 1H), 6.56 (m, 1H), 6.30 (t, J=3.6, 1H), 4.25 (t, J=6.9, 2H), 3.79 (m, 4H), 3.18 (m, 4H), 2.82 (t, J=6.9, 2H).

Examples 1294

N-(3-{7-[1-(2-Cyano-ethyl)-1H-pyrrol-2-yl]-pyrrolo[2,1-f][1,2,4]triazin-2-ylamino}-phenyl)-acetamide Following the synthetic and purification procedures described in Example 1293d, 3-[2-(2-methanesulfinyl-pyrrolo[2,1-f][1,2,4]triazin-7-yl)-pyrrol-1-yl]-propionitrile (93 mg, 0.31 mmol) was coupled to 3'-aminoacetanilide (62 mg, 0.41 mmol) at 120° C. for 135 h to afford titled compound. Yield of TFA salt: 29 mg (19%) of gold powder. LC/MS: 386 (M+H); HPLC: 97% pure, RT=2.65 min; mp: 131-139° C.; $^1$H NMR: (DMSO, δ) 9.75 (s, 1H), 9.44 (s, 1H), 8.96 (s, 1H), 7.69 (s, 1H), 7.53 (d, J=7.4 ,1H), 7.12 (m, 3H), 6.95 (d, J=4.4, 1H), 6.90 (d, J=4.4, 1H), 6.58 (dd, J=7.9, 3.6, 1H) 6.26 (dd, J=3.6, 3.4, 1H), 4.24 (t, J=6.3, 2H), 2.83 (t, J=6.3, 2H), 2.04 (s, 3H).

Example 1295

3-(2-{2-[3-(2-Methoxy-1-methyl-ethoxy)-phenylamino]-pyrrolo[2,1-f][1,2,4]triazin-7-yl}-pyrrol-1-yl)-propionitrile Also isolated from the reaction described in Example 1294 was the titled compound. Yield of TFA salt: 32 mg, (23%) of brown powder. LC/MS: 326 (M+H); HPLC: 97% pure, RT=2.84 min; $^1$H NMR: (DMSO, δ) 9.03 (s, 1H), 7.13 (s, 1H), 7.07 (d, J=4.8, 1H), 7.04 (d, J=4.8, 1H), 6.59 (dd, J=3.4, 1.5, 1H) 6.26 (dd, J=3.6, 3.4, 1H), 5.14 (m, 1H), 4.28 (t, J=6.3, 2H), 3.51 (m, 2H), 3.27 (s, 3H), 2.85 (t, J=6.3, 2H), 1.29 (d, J=6.1, 3H).

Example 1296

3-(2-{2-[3-(2-oxo-pyrrolidin-1-yl)-phenylamino]-pyrrolo[2,1-f][1,2,4]triazin-7-yl}-pyrrol-1-yl)-propionitrile Following the synthetic and purification procedures described in Example 1293d, 3-[2-(2-methanesulfinyl-pyrrolo[2,1-f][1,2,4]triazin-7-yl)-pyrrol-1-yl]-propionitrile (93 mg, 0.31 mmol) was coupled to 1-(3-amino-phenyl)-pyrrolidin-2-one (77 mg, 0.44 mmol) at 120° C. for 96 h to afford the title compound. Yield of TFA salt: 23 mg (15%) of brown powder. LC/MS: 412 (M+H); HPLC: 97% pure, RT=2.16 min; mp: 60-67° C.; $^1$H NMR: (DMSO, δ) 9.55 (s, 1H), 8.99 (s, 1H), 7.89 (s, 1H), 7.51 (d, J=8.2, 1H), 7.28 (d, J=8.2, 1H), 7.20 (t, J=8.1, 1H), 7.14 (m, 1H), 6.95 (d, J=4.5, 1H), 6.88 (d, J=4.4, 1H), 6.49 (dd, J=3.6, 1.5 1H), 6.27 (t, J=3.6, 1H), 4.19 (t, J=6.3, 2H), 3.49 (t, J=7.0, 2H), 2.77 (t, J=6.3, 2H), 2.47 (t, J=7.0, 2H), 2.02 (p, J=7.0, 2H).

Example 1297

N-tert-Butyl-3-[2-(2-trifluoromethyl-3H-benzimidazol-5-ylamino)-pyrrolo[2,1-f][1,2,4]triazin-7-yl]-benzenesulfonamide Following the synthetic and purification procedures described in Example 1293d, N-tert-butyl-3-(2-methanesulfinyl-pyrrolo[2,1-f][1,2,4]triazin-7-yl)-benzenesulfonamide (103 mg, 0.262 mmol) was coupled with 2-trifluoromethyl-3H-benzimidazol-5-ylamine (91 mg, 0.45 mmol) at 105° C. for 132 h to afford the title compound. Yield of TFA salt: 15 mg (26%) of brown powder; LC/MS: 529 (M+H); HPLC: 97% pure, RT=2.16 min; $^1$H NMR: (DMSO, δ) 9.68 (s, 1H), 9.07 (s, 1H), 8.53 (m, 2H), 8.02 (s, 1H), 7.86 (d, J=8.0, 1H), 7.83 (dd, J=9.1, 1.8, 1H), 7.75 (m, 3H), 7.25 (d, J=4.7, 1H), 7.03 (d, J=4.7, 1H), 1.12 (s, 9H)-benzimidazole NH presumably underwent rapid exchange with residual water.

Example 1298

N-tert-Butyl-3-[2-(2-oxo-2,3-dihydro-1H-benzimidazol-5-ylamino)-pyrrolo[2,1-f][1,2,4]triazin-7-yl]-benzenesulfonamide Following the synthetic and purification procedures described in Example 1293d, a N-tert-butyl-3-(2-methanesulfinyl-pyrrolo[2,1-f][1,2,4]triazin-7-yl)-benzenesulfonamide (103 mg, 0.262 mmol) was coupled with 5-amino-1,3-dihydro-benzimidazol-2-one (67 mg, 0.45 mmol) at 105° C. for 72 h to afford the title compound. Yield of TFA salt: 82 mg (52%) of brown powder; LC/MS: 478 (M+H); HPLC: 97% pure, RT=2.83 min; $^1$H NMR: (DMSO, δ) 10.46 (s, 1H), 10.42 (s, 1H), 9.34 (s, 1H), 9.00 (s, 1H), 8.52 (s, 1H), 8.44 (d, J=8.0, 1H), 7.84 (d, J=8.3, 1H), 7.73 (appt, J=8.0, 1H), 7.63 (s, 1H), 7.47 (dd, J=8.1, 1.8, 1H), 7.23 (s, 1H), 7.19 (d, J=5.0, 1H), 6.98 (d, J=3.6, 1H), 6.93 (d, J=8.3, 1H), 1.11 (s, 9H).

Example 1299

3-[2-(3H-Benzimidazol-5-ylamino)-pyrrolo[2,1-f][1,2,4]triazin-7-yl]-N-tert-butyl-benzenesulfonamide Following the synthetic and purification procedures described in Example 1293d, N-tert-butyl-3-(2-methanesulfinyl-pyrrolo[2,1-f][1,2,4]triazin-7-yl)-benzenesulfonamide (103 mg, 0.262 mmol) was coupled with 3H-benzimidazol-5-ylamine (60 mg, 0.45 mmol) at 105° C. for 120 h to afford the title compound. Yield of TFA salt: 24 mg (16%) of brown powder; LC/MS: 462 (M+H); HPLC: 97% pure, RT=2.65 min; $^1$H NMR: (DMSO, δ) 9.91 (s, 1H), 9.40 (s, 1H), 9.11 (s, 1H), 8.59 (s, 1H), 8.42 (d, J=8.0, 1H), 8.09 (s, 1H), 8.01 (d, J=8.0, 1H), 7.85 (m, 2H), 7.77 (t, J=7.7, 1H), 7.65 (s, 1H), 7.28 (d, J=4.9, 1H), 7.06 (d, J=4.9, 1H), 1.10 (s, 9H)— benzimidazole NH presumably underwent rapid exchange with residual water.

Example 1300

N-tert-Butyl-3-[2-(3-methyl-3H-benzimidazol-5-ylamino)-pyrrolo[2,1-f][1,2,4]triazin-7-yl]-benzenesulfonamide Following the synthetic and purification procedures described in Example 1293d, N-tert-butyl-3-(2-methanesulfinyl-pyrrolo[2,1-f][1,2,4]triazin-7-yl)-benzenesulfonamide (103 mg, 0.262 mmol) was coupled with 3-methyl-3H-benzimidazol-5-ylamine (66 mg, 0.45 mmol) at 105° C. for 120 h to afford the title compound. Yield of TFA salt: 78 mg (50%) of brown powder; LC/MS: 476 (M+H); HPLC: 97% pure, RT=2.64 min; $^1$H NMR: (DMSO, δ) 10.04 (s, 1H), 9.38 (s, 1H), 9.12 (s, 1H), 8.49 (s, 1H), 8.41 (d, J=8.0, 1H), 8.31 (s, 1H), 7.87 (d, J=8.0, 1H), 7.79 (m, 3H), 7.61 (s, 1H), 7.24 (d, J=4.9, 1H), 7.07 (d, J=4.9, 1H), 3.81 (s, 3H), 1.08 (s, 9H).

Example 1301

[7-(4-Methanesulfonyl-phenyl)-pyrrolo[2,1-f][1,2,4]triazin-2-yl]-(3-methyl-3H-benzimidazol-5-yl)-amine Following the synthetic and purification procedures described in Example 1293d, 2-methanesulfinyl-7-(4-methanesulfonyl-phenyl)-pyrrolo[2,1-f][1,2,4]triazine (75 mg, 0.22 mmol) was coupled with 3-methyl-3H-benzimidazol-5-ylamine (57 mg, 0.38 mmol) at 105° C. for 86 h to afford the title compound. Yield of TFA salt: 12 mg (10%) of brown powder. LC/MS: 419 (M+H); HPLC: 95% pure, RT=2.21 min; mp: lyophilyte; $^1$H NMR: (DMSO, δ) 10.11 (s, 1H), 9.33 (s, 1H), 9.14 (s, 1H), 8.43 (d, J=8.6, 2H), 8.40 (s, 1H), 8.11 (d, J=8.6, 2H), 7.81 (d, J=9.0, 1H), 7.70 (d, J=9.0, 1H), 7.34 (d, J=4.9, 1H), 7.08 (d, J=4.9, 1H), 3.85 (s, 3H), 3.30 (s, 3H).

Example 1302

[7-(4-Methanesulfonyl-phenyl)-pyrrolo[2,1-f][1,2,4]triazin-2-yl]-(2-trifluoromethyl-3H-benzimidazol-5-yl)-amine Following the synthetic and purification procedures described in Example 1293d, 2-methanesulfinyl-7-(4-methanesulfonyl-phenyl)-pyrrolo[2,1-f][1,2,4]triazine (75 mg, 0.22 mmol) was coupled with 2-trifluoromethyl-3H-benzimidazol-5-ylamine (78 mg, 0.38 mmol) at 105° C. for 86 h to afford the title compound. Yield of TFA salt: 34 mg (26%) of brown powder; LC/MS: 473 (M+H); HPLC: 95% pure, RT=2.99 min; $^1$H NMR: (DMSO, δ) 9.73 (s, 1H), 9.09 (s, 1H), 8.51 (d, J=8.4, 2H), 8.40 (s, 1H), 8.13 (br s, 1H), 8.04 (d, J=8.4, 2H), 7.71 (m, 2H), 7.38 (d, J=4.9, 1H), 7.03 (d, J=4.9, 1H), 3.28 (s, 3H).

Example 1303

5-[7-(4-Methanesulfonyl-phenyl)-pyrrolo[2,1-f][1,2,4]triazin-2-ylamino]-1,3-dihydro-benzimidazol-2-one Following the synthetic and purification procedures described in Example 1293d, 2-methanesulfinyl-7-(4-methanesulfonyl-phenyl)-pyrrolo[2,1-f][1,2,4]triazine (75 mg, 0.22 mmol) was coupled with 5-amino-1,3-dihydro-benzimidazol-2-one (57 mg, 0.38 mmol) at 105° C. for 86 h to afford the title compound. Yield of TFA salt: 79 mg (67%) of brown powder. LC/MS: 421 (M+H); HPLC: 97% pure, RT=2.32 min; $^1$H NMR: (DMSO, δ) 10.65 (s, 1H), 10.48 (s, 1H), 9.38 (s, 1H), 9.02 (s, 1H), 8.49 (d, J=8.6, 2H), 8.04 (d, J=8.6, 2H), 7.35 (m, 2H), 7.29 (s, 1H), 6.98 (d, J=4.8, 1H), 6.91 (d, J=8.6, 1H), 3.27 (s, 3H).

Example 1304

(3H-Benzimidazol-5-yl)-[7-(4-methanesulfonyl-phenyl)-pyrrolo[2,1-f][1,2,4]triazin-2-yl]-amine Following the synthetic and purification procedures described in Example 1293d, 2-methanesulfinyl-7-(4-methanesulfonyl-phenyl)-pyrrolo[2,1-f][1,2,4]triazine (75 mg, 0.22 mmol) was coupled with 3H-benzimidazol-5-ylamine (51 mg, 0.38 mmol) at 105° C. in a for 86 h to afford the title compound. Yield of TFA salt: 46 mg (40%) of brown powder; LC/MS: 405 (M+H); HPLC: 90% pure, RT=2.14 min; $^1$H NMR: (DMSO, δ) 9.96 (s, 1H), 9.48 (s, 1H), 9.13 (s, 1H), 8.51 (d, J=8.6, 2H), 8.18 (s, 1H), 8.07 (d, J=8.6, 2H), 7.86 (m, 2H), 7.42 (d, J=4.8, 1H), 7.07 (d, J=4.8, 1H), 3.28 (s, 3H)-benzimidazole NH presumably underwent rapid exchange with residual water.

Example 1305

7-(2-Methoxy-phenyl)-pyrrolo[2,1-f][1,2,4]triazin-2-yl]-(2-trifluoromethyl-3H-benzimidazol-5-yl)-amine Following the synthetic and purification procedures described in Example 1293d, 2-methanesulfinyl-7-(2-methoxy-phenyl)-pyrrolo[2,1-f][1,2,4]triazine (75.4 mg, 0.262 mmol) was coupled with 2-trifluoromethyl-3H-benzimidazol-5-ylamine (91 mg, 0.45 mmol) at 105° C. for 86 h to afford the title compound. Yield of TFA salt: 43 mg (30%) of brown powder; LC/MS: 425 (M+H); HPLC: 97% pure, RT=3.28 min; $^1$H NMR: (DMSO, δ) 9.51 (s, 1H), 8.98 (s, 1H), 8.03 (br s, 1H), 7.86 (d, J=7.6, 1H), 7.74 (d, J=8.7, 1H), 7.55 (d, J=8.7, 1H), 7.47 (dd, J=7.6, 1.5, 1H), 7.23 (d, J=8.3, 1H), 7.14 (t, J=7.6, 1H), 6.98 (d, J=4.7, 1H), 6.94 (d, J=4.7, 1H), 3.82 (s, 3H)-benzimidazole NH presumably underwent rapid exchange with residual water.

Example 1306

(3H-Benzimidazol-5-yl)-[7-(2-methoxy-phenyl)-pyrrolo[2,1-f][1,2,4]triazin-2-yl]-amine Following the synthetic and purification procedures described in Example 1293d, 2-methanesulfinyl-7-(2-methoxy-phenyl)-pyrrolo[2,1-f][1,2,4]triazine (75.4 mg, 0.262 mmol) was coupled to 3H-benzimidazol-5-ylamine (60.0 mg, 0.45 mmol) at 105° C. for 86 h to afford the title compound. Yield of TFA salt: 62 mg (50%) of brown powder. LC/MS: 357 (M+H); HPLC: 95% pure, RT=2.38 min; $^1$H NMR: (DMSO, δ) 9.77 (s, 1H), 9.38 (s, 1H), 9.02 (s, 1H), 8.04 (s, 1H), 7.93 (d, J=9.2, 1H), 7.85 (d, J=7.5, 1H), 7.65 (d, J=9.2, 1H), 7.47 (t, J=8.2, 1H), 7.25 (d, J=8.2, 1H), 7.17 (t, J=7.5, 1H), 7.01 (d, J=4.8, 1H), 6.98 (d, J=4.8, 1H), 3.81 (s, 3H)-benzimidazole NH presumably underwent rapid exchange with residual water.

Example 1307

[7-(6-Methoxy-pyridin-3-yl)-pyrrolo[2,1-f][1,2,4]triazin-2-yl]-(3-methyl-3H-benzimidazol-5-yl)-amine Following the synthetic and purification procedures described in Example 1293d, 2-methanesulfinyl-7-(6-methoxy-pyridin-3-yl)-pyrrolo[2,1-f][1,2,4]triazine (60 mg, 0.2 mmol) was coupled to 3-methyl-3H-benzimidazol-5-ylamine (53 mg, 0.36 mmol) at 105° C. for 86 h to afford the title compound. Yield of TFA salt: 33 mg (34%) of brown powder. LC/MS: 372 (M+H); HPLC: 95% pure, RT=2.29 min; $^1$H NMR: (DMSO, δ) 10.04 (s, 1H), 9.34 (s, 1H), 9.22 (d, J=2.0, 1H), 9.06 (s, 1H), 8.51 (s, 1H), 8.35 (dd, J=8.9, 2.4, 1H), 7.79 (d, J=9.0, 1H), 7.64 (dd, J=9.0, 1.4, 1H), 7.24 (d, J=4.9, 1H), 7.05 (s, 1H), 7.03 (d, J=4.9, 1H), 4.06 (s, 3H), 3.95 (s, 3H).

Example 1308

[7-(6-Methoxy-pyridin-3-yl)-pyrrolo[2,1-f][1,2,4]triazin-2-yl]-(2-trifluoromethyl-3H-benzimidazol-5-yl)-amine Following the synthetic and purification procedures described in Example 1293d, 2-methanesulfinyl-7-(6-methoxy-pyridin-3-yl)-pyrrolo[2,1-f][1,2,4]triazine (60 mg, 0.2 mmol) was coupled to 2-trifluoromethyl-3H-benzimidazol-5-ylamine (72 mg, 0.36 mmol) at 105° C. for 86 h to afford the title compound. Yield of TFA salt: 32 mg (30%) of tan powder; LC/MS: 426 (M+H); HPLC: 97% pure, RT=3.06 min; $^1$H NMR: (DMSO, δ) 9.64 (s, 1H), 9.02 (s, 1H), 8.97 (d, J=2.0, 1H), 8.56 (dd, J=8.8, 2.5, 1H), 8.12 (s, 1H), 7.66 (m, 2H), 7.22 (d, J=4.9, 1H), 7.01 (d, J=8.8, 1H), 6.99 (d, J=4.9, 1H), 3.94 (s, 3H)-benzimidazole NH presumably underwent rapid exchange with residual water.

Example 1309

5-[7-(6-Methoxy-pyridin-3-yl)-pyrrolo[2,1-f][1,2,4]triazin-2-ylamino]-1,3-dihydro-benzimidazol-2-one Following the synthetic and purification procedures described in Example 1293d, 2-methanesulfinyl-7-(6-methoxy-pyridin-3-yl)-pyrrolo[2,1-f][1,2,4]triazine (60 mg, 0.2 mmol) was coupled with 5-amino-1,3-dihydro-benzimidazol-2-one (54 mg, 0.36 mmol) at 105° C. for 86 h to afford the title compound. Yield of TFA salt: 43 mg (44%) of tan powder. LC/MS: 374 (M+H); HPLC: 97% pure, RT=2.20 min; $^1$H NMR: (DMSO, δ) 10.49 (s, 1H), 10.39 (s, 1H), 9.20 (s, 1H), 8.88 (s, 1H), 8.83 (s, 1H), 8.47 (dd, J=8.4, 2.5, 1H), 7.25 (d, J=8.4, 1H), 7.21 (s, 1H), 7.10 (d, J=4.8, 1H), 6.95 (d, J=8.8, 1H), 6.87 (d, J=4.8, 1H), 6.79 (d, J=8.4, 1H), 3.86 (s, 3H).

Example 1310

N-{2-[2-(3-Methyl-3H-benzoimidazol-5-ylamino)-pyrrolo[2,1-f][1,2,4]triazin-7-yl]-phenyl}-methanesulfonamide Following the synthetic and purification procedures described in Example 1293d, N-[2-(2-methanesulfinyl-pyrrolo[2,1-f][1,2,4]triazin-7-yl)-phenyl]-methanesulfonamide (56 mg, 0.16 mmol) was coupled with 3-methyl-3H-benzimidazol-5-ylamine (40 mg, 0.28 mmol) at 105° C. for 86 h to afford the title compound. Yield of TFA salt: 19 mg (22%) of brown powder; LC/MS: 434 (M+H); HPLC: 95% pure, RT=2.19 min; $^1$H NMR: (DMSO, δ) 10.01 (s, 1H), 9.92 (s, 1H), 9.33 (s, 1H), 9.08 (s, 1H), 8.40 (s, 1H), 7.93 (d, J=7.7, 1H), 7.80 (m, 1H), 7.77 (d, J=9.0, 1H), 7.71 (d, J=9.0, 1H), 7.55 (t, J=7.8, 1H), 7.29 (d, J=7.9, 1H), 7.09 (d, J=4.8, 1H), 7.03 (d, J=4.8, 1H), 3.84 (s, 3H), 3.01 (s, 3H).

Examples 1311

(3H-Benzimidazol-5-yl)-[7-(3-ethanesulfonyl-phenyl)-pyrrolo[2,1-f][1,2,4]triazin-2-yl]-amine 1311a) 7-(3-Ethanesulfonyl-phenyl)-2-methylsulfanyl-pyrrolo[2,1-f][1,2,4]triazine: Following the procedure of 1291a, 7-bromo-2-methylsulfanyl-pyrrolo[2,1-f][1,2,4]triazine (0.8916 g, 3.653 mmol) was coupled to 3-ethylsulfonylphenylboronic acid (1.00 g, 4.67 mmol) to afford product that was purified with an ISCO chromatography unit outfitted with an 80 g silica gel column and eluted with a gradient of DCM/MeOH. The solid (1.7 g) thus obtained was triturated with ether (5×2 mL) to afford desired product (1.38 g, 113%), that was contaminated with ~10% Ph$_3$P=O as determined by $^1$H NMR spectroscopy. LC/MS: 334 (M+H); HPLC: 95% pure, RT=3.18 min; $^1$H NMR: (CDCl$_3$, δ) 8.98 (s, 1H), 8.80 (s, 1H), 8.24 (d, J=7.9, 1H), 7.88 (d, J=7.9, 1H), 7.68 (t, J=7.9, 1H), 7.22 (d, 4.9, 1H), 6.93 (d, J=4.9, 1H), 3.17 (q, J=7.5, 2H), 2.68 (s, 3H), 1.32 (t, J=7.5, 3H)-impurities at δ 7.56, 7.30 and 7.25 assigned to Ph$_3$P=O.

1311b) 7-(3-Ethanesulfonyl-phenyl)-pyrrolo[2,1-f][1,2,4]triazin-2-ol: To a mixture of Na$_2$WO$_4$.2H$_2$O (62 mg, 0.19 mmol) and 7-(3-Ethanesulfonyl-phenyl)-2-methylsulfanyl-pyrrolo[2,1-f][1,2,4]triazine (1.25 g, 3.76 mmol) in methanol (40.0 mL) was added 50% H$_2$O$_2$ (0.65 mL, 11 mmol) and the reaction was stirred at 60° C. for 5 h. The mixture was treated with HOAc (700 uL), 50% $H_2O_2$ (0.65 mL, 11 mmol) and $Na_2WO_4 \cdot 2H_2O$ (65 mg, 0.2 mmol) and warmed at 60° C. until reaction was completed as analyzed by LC/MS. At this time, the mixture was treated with 10% aqueous solution of $Na_2S_2O_3$ (5 mL) and the resultant solids were collected on a Buchner funnel, washed with water (5×5 mL) and dried in vacuo to afford 7-(3-ethanesulfonyl-phenyl)-2-methanesulfonyl-pyrrolo[2,1-f][1,2,4]triazine (1.33 g; Yield=97%, HPLC RT=2.51). To the above sulfone in 1,4-dioxane (4 mL) and DMSO (2.5 mL) was added an aqueous solution of 5N NaOH (11.1 mL, 55.4 mmol). The mixture was heated at 80° C., O/N, cooled in an ice bath and treated with 3M HCl until pH 4. The resulting solids were collected on a Buchner funnel, washed with water (5×5 mL) and dried in vacuo to afford the title compound (0.675 g; Yield=88%). LC/MS: 304 (M+H); HPLC: RT=1.81 min; $^1$H NMR: (DMSO, δ) 11.88 (br s, 1H), 9.05 (s, 1H), 8.68 (s, 1H), 8.59 (d, J=7.7, 1H), 7.87 (d, J=7.7, 1H), 7.80 (t, 1H, J=7.7), 7.45 (d, J=4.9, 1H), 7.06 (d, J=4.9, 1H), 3.39 (q, J=7.2, 2H), 1.15 (t, J=7.2, 3H).

1311c) (3H-Benzimidazol-5-yl)-[7-(3-ethanesulfonyl-phenyl)-pyrrolo[2,1-f][1,2,4]triazin-2-yl]-amine: A solution of the above phenol and phenylbis(trifluoromethanesulphonimide) (292 mg, 0.817 mmol) in N,N-dimethylformamide (5.5 mL) was treated with N,N-diisopropylethylamine (0.55 mL, 3.2 mmol) and stirred for 1.50 h. This reaction mixture was partitioned into thirds and one portion treated with 3H-benzimidazol-5-ylamine (44 mg, 0.33 mmol), the other with 3-methyl-3H-benzimidazol-5-ylamine (46 mg, 0.31 mmol), and the last with 2-trifluoromethyl-3H-benzimidazol-5-ylamine (62.2 mg, 0.309 mmol). All reactions were stirred at 65° C. overnight at which time they were processed and purified as described in Example 1291c. Yield of TFA salt: 69 mg (52%); LC/MS: 419 (M+H); HPLC: 97% pure, RT=2.27 min; $^1$H NMR: (DMSO, δ) 14.50 (br s , 1H), 9.93 (s, 1H), 9.39 (s, 1H), 9.10 (s, 1H), 8.60 (s, 1H), 8.54 (d, J=7.8, 1H), 8.09 (m, 1H), 7.97 (dd, J=9.1, 1.3, 1H), 7.91 (d, J=7.8, 1H), 7.85 (t, J=7.8, 1H), 7.82 (d, J=9.1, 1H), 7.36 (d, J=4.7, 1H), 7.06 (d, J=4.7, 1H), 3.33 (q, J=7.2, 2H), 1.11 (t, J=7.2, 3H).

Example 1312

[7-(3-Ethanesulfonyl-phenyl)-pyrrolo[2,1-f][1,2,4]triazin-2-yl]-(3-methyl-3H-benzimidazol-5-yl)-amine Isolated from Example 1311c. Yield of TFA salt: 38 mg (28%); LC/MS: 433 (M+H); HPLC: 95% pure, RT=2.28 min; $^1$H NMR: (DMSO, δ) 10.03 (s , 1H), 9.35 (s, 1H), 9.13 (s, 1H), 8.55 (s, 1H), 8.53 (d, J=7.8, 1H), 8.27 (s, 1H), 7.91 (d, J=7.8, 1H), 7.87 (d, J=7.8, 1H), 7.86 (t, J=7.8, 1H), 7.80 (m, 2H), 7.34 (d, J=4.9, 1H), 7.07 (d, J=4.9, 1H), 3.81 (s, 3H), 3.31 (q, J=7.3, 2H), 1.08 (t, J=7.3, 3H).

Example 1313

[7-(3-Ethanesulfonyl-phenyl)-pyrrolo[2,1-f][1,2,4]triazin-2-yl]-(2-trifluoromethyl-3H-benzimidazol-5-yl)-amine Isolated from Example 1311c, Yield of TFA salt: 63 mg (42%); LC/MS: 487 (M+H); HPLC: 97% pure, RT=3.20 min; $^1$H NMR: (DMSO, δ) 9.72 (s, 1H), 9.08 (s, 1H), 8.61 (d, J=7.7, 1H), 8.55 (s, 1H), 8.03 (s, 1H), 7.91 (d, J=7.7, 1H), 7.83 (t, J=7.8, 1H), 7.78 (dd, J=9.0, 1.0, 1H), 7.71 (d, J=9.0, 1H), 7.33 (d, J=4.8, 1H), 7.03 (d, J=4.8, 1H), 3.35 (q, J=7.4, 2H), 1.11 (t, J=7.4, 3H)-benzimidazole NH presumably underwent rapid exchange with residual water.

Example 1314

7-(3-Cyclopropylmethanesulfonyl-phenyl)-pyrrolo[2,1-f][1,2,4]triazin-2-yl]-(1H-indazol-5-yl)-amine 1314a) 7-(3-Cyclopropylmethanesulfonyl-phenyl)-2-methylsulfanyl-pyrrolo[2,1-f][1,2,4]triazine: A mixture of 1-bromo-3-cyclopropylmethanesulfonyl-benzene (2.05 g, 7.45 mmol), KOAc (2.285 g, 23.28 mmol), 4,4,5,5,4',4',5',5'-octamethyl-[2,2']bi[[1,3,2]dioxaborolanyl] (2.365 g, 9.313 mmol), and [1,1'-bis(diphenylphosphino)ferrocene]dichloropalladium(II),complex with dichloromethane (1:1) (0.195 g, 0.238 mmol) was slurried in N,N-Dimethylformamide (51 mL), degassed by repeated vacuum/$N_2$ exchange and warmed at 80° C. for 15 h. Solvent was removed by rotary evaporation and the residue was purified with an ISCO chromatography unit outfitted with an 40 g silica gel column and eluted with a gradient of EtOAc/hexane to afford 2-(3-cyclopropylmethanesulfonyl-phenyl)-4,4,5,5-tetramethyl-1,3,2-dioxaborolane (2.08 g, 87%). This boronate (2.042 g, 6.337 mmol) was coupled to 7-bromo-2-methylsulfanyl-pyrrolo[2,1-f][1,2,4]triazine (1.209 g, 4.954 mmol) and purified in the manner described in Example 1311a to afford the desired product (1.479 g, 83%). LC/MS: 360 (M+H); HPLC: 95% pure, RT=3.46 min; $^1$H NMR: (CDCl$_3$, δ) 9.02 (s, 1H), 8.80 (s, 1H), 8.30 (d, J=8.0, 1H), 7.91 (d, J=8.0, 1H), 7.67 (t, J=8.0, 1H), 7.22 (d, 4.8, 1H), 6.93 (d, J=4.8, 1H), 3.07 (d, J=7.2, 2H), 2.68 (s, 3H), 1.05 (m, 1H), 0.58 (m, 2H), 0.16 (m, 2H)-impurities at δ 7.56, 7.30 and 7.25 assigned to $Ph_3P=O$.

1314b) 7-(3-Cyclopropylmethanesulfonyl-phenyl)-2-methanesulfinyl-pyrrolo[2,1-f][1,2,4]triazine: Oxidation of the above sulfide (1.45 g, 4.134 mmol) according to the procedure described in Example 1291b followed by purification with an ISCO chromatography unit outfitted with an 80 g silica gel column and eluted with a gradient of DCM/MeOH gave the corresponding sulfoxide (1.334 g, 86%). LC/MS: 376 (M+H); HPLC: 95% pure, RT=2.44 min; $^1$H NMR: (DMSO, δ) 9.39 (s, 1H), 8.82 (s, 1H), 8.55 (d, J=8.0, 1H), 7.94 (d, J=8.0), 7.86 (m, 2H), 7.38 (d, 4.9, 1H), 3.38 (d, J=7.2, 2H), 3.01 (s, 3H), 0.94 (m, 1H), 0.46 (m, 2H), 0.14 (m, 2H).

1314c) 7-(3-Cyclopropylmethanesulfonyl-phenyl)-pyrrolo[2,1-f][1,2,4]triazin-2-yl]-(1H-indazol-5-yl)-amine: Following the synthetic and purification procedures described in Example 1293d, the above sulfoxide (75 mg, 0.20 mmol) was coupled with 1H-Indazol-5-ylamine (45.2 mg, 0.340 mmol) at 105° C. for 90 h to afford the title compound. Yield of TFA salt: 30 mg (27%) of brown powder; LC/MS: 445 (M+H); HPLC: 97% pure, RT=2.96 min; $^1$H NMR: (DMSO, δ) 9.45 (s, 1H), 8.94 (s, 1H), 8.50 (d, J=7.9, 1H), 8.38 (s, 1H), 8.14 (s, 1H), 7.90 (s, 1H), 7.84 (d, J=7.9, 1H), 7.75 (t, J=7.9, 1H), 7.50 (d, J=9.0, 1H), 7.41 (d, J=9.0, 1H), 7.15 (d, J=4.8, 1H), 6.89 (d, J=4.8, 1H), 3.21 (d, J=7.1, 2H), 1.98 (s, 1H), 0.77 (m, 1H), 0.33 (m, 2H), −0.01 (m, 2H).

Example 3115

N-tert-Butyl-3-[2-(1H-indazol-5-ylamino)-pyrrolo[2,1-f][1,2,4]triazin-7-yl]-benzenesulfonamide Following the procedure of Example 1311c, N-tert-butyl-3-(2-hydroxy-pyrrolo[2,1-f][1,2,4]triazin-7-yl)-benzenesulfonamide (225 mg, 0.650 mmol) was coupled in parallel fashion with 1H-indazol-5-ylamine (36 mg, 0.27 mmol), [1-methyl-1H-indazol-6-ylamine (43 mg, 0.29 mmol), and 1-methyl-1H-indazol-5-ylamine (41 mg, 0.28 mmol). After evaporation of solvent, residues were purified with ISCO chromatography unit outfitted with a 12 g silica gel column and eluted with a gradient of DCM/MeOH to afford titled products. Yield: 38 mg (13%); LC/MS: 462 (M+H); HPLC: 97% pure, RT=3.11 min; $^1$H NMR: (DMSO, δ) 12.92 (s, 1H), 9.55 (s, 1H), 9.04 (s, 1H), 8.49 (m, 2H), 8.25 (s, 1H), 8.02 (s, 1H), 7.88 (d, J=8.2, 1H), 7.77 (t, J=8.2, 1H), 7.61 (m, 2H), 7.51 (d, J=8.7, 1H), 7.18 (d, J=4.7, 1H), 6.99 (d, J=4.7, 1H), 1.10 (s, 9H).

Example 1316

N-tert-Butyl-3-[2-(1-methyl-1H-indazol-5-ylamino)-pyrrolo[2,1-f][1,2,4]triazin-7-yl]-benzenesulfonamide Isolated from Example 1315. Yield: 47 mg (15%); LC/MS: 476 (M+H); HPLC: 97% pure, RT=3.38 min; $^1$H NMR: (DMSO, δ) 9.57 (s, 1H), 9.04 (s, 1H), 8.50 (d, J=7.7, 1H), 8.47 (s, 1H), 8.25 (s, 1H), 7.98 (s, 1H), 7.88 (d, J=7.7, 1H), 7.78 (t, J=7.7, 1H), 7.61 (m, 3H), 7.19 (d, J=4.8, 1H), 7.00 (d, J=4.8, 1H), 4.02 (s, 3H), 1.10 (s, 9H).

Example 1317

N-tert-Butyl-3-[2-(1-methyl-1H-indazol-6-ylamino)-pyrrolo[2,1-f][1,2,4]triazin-7-yl]-benzenesulfonamide Isolated from Example 1315. Yield: 64 mg (21%); LC/MS: 476 (M+H); HPLC: 97% pure, RT=3.44 min; $^1$H NMR: (DMSO, δ) 9.83 (s, 1H), 9.10 (s, 1H), 8.55 (d, J=7.7, 1H), 8.40 (s, 1H), 8.12 (s, 1H), 7.90 (s, 1H), 7.86 (d, J=7.7, 1H), 7.77 (t, J=7.7, 1H), 7.65 (d, J=8.7, 1H), 7.62 (s, 1H), 7.31 (d, J=8.7, 1H), 7.19 (d, J=4.8, 1H), 7.04 (d, J=4.8, 1H), 3.77 (s, 3H), 1.09 (s, 9H).

Example 1318

[7-(3-Cyclopropylmethanesulfonyl-phenyl)-pyrrolo[2,1-f][1,2,4]triazin-2-yl]-(2-trifluoromethyl-3H-benzimidazol-5-yl)-amine Following the synthetic and purification procedures described in Example 1293d, 7-(3-cyclopropylmethanesulfonyl-phenyl)-2-methylsulfanyl-pyrrolo[2,1-f][1,2,4]triazine (75 mg, 0.20 mmol) was coupled with 2-trifluoromethyl-3H-benzimidazol-5-ylamine (68.3 mg, 0.340 mmol) at 105° C. for 86 h to afford the title compound. Yield of TFA salt: 25 mg (22%) of brown powder; LC/MS: 513 (M+H); HPLC: 97% pure, RT=3.43 min; $^1$H NMR: (DMSO, δ) 9.60 (s, 1H), 8.97 (s, 1H), 8.53 (d, J=7.9, 1H), 8.41 (s, 1H), 7.90 (s, 1H), 7.81 (d, J=7.9, 1H), 7.70 (m, 2H), 7.60 (d, J=8.8, 1H), 7.21 (d, J=4.8, 1H), 6.91 (d, J=4.8, 1H), 3.20 (d, J=7.2, 2H), 0.77 (m, 1H), 0.32 (m, 2H), −0.01 (m, 2H).

Example 1319

(3H-Benzimidazol-5-yl)-[7-(3-cyclopropylmethanesulfonyl-phenyl)-pyrrolo[2,1-f][1,2,4]triazin-2-yl]-amine Following the synthetic and purification procedures described in Example 1293d, 7-(3-cyclopropylmethanesulfonyl-phenyl)-2-methylsulfanyl-pyrrolo[2,1-f][1,2,4]triazine (75 mg, 0.20 mmol) was coupled with 3H-benzimidazol-5-ylamine (45.2 mg, 0.340 mmol) at 105° C. for 86 h to afford the title compound. Yield of TFA salt: 39 mg (43%) of brown powder; LC/MS: 445 (M+H); HPLC: 97% pure, RT=2.46 min; $^1$H NMR: (DMSO, δ) 9.85 (s, 1H), 9.33 (s, 1H), 9.02 (s, 1H), 8.51 (s, 1H), 8.45 (d, J=7.7, 1H), 8.00 (s, 1H), 7.90 (dd, J=9.2, 1.5, 1H), 7.83 (d, J=7.7, 1H), 7.75 (m, 2H), 7.27 (d, J=4.8, 1H), 6.97 (d, J=4.8, 1H), 3.21 (d, J=7.1, 2H), 0.77 (m, 1H), 0.34 (m, 2H), 0.01 (m, 2H).

Example 1320

[7-(3-Cyclopropylmethanesulfonyl-phenyl)-pyrrolo[2,1-f][1,2,4]triazin-2-yl]-(3-methyl-3H-benzimidazol-5-yl)-amine Following the synthetic and purification procedures described in Example 1293d, 7-(3-cyclopropylmethanesulfonyl-phenyl)-2-methylsulfanyl-pyrrolo[2,1-f][1,2,4]triazine (75 mg, 0.20 mmol) was coupled with 3-methyl-3H-benzimidazol-5-ylamine (50.0 mg, 0.340 mmol) at 105° C. for 90 h to afford the title compound. Yield of TFA salt: 25 mg (22%) of brown powder; LC/MS: 459 (M+H); HPLC: 97% pure, RT=2.49 min; $^1$H NMR: (DMSO, δ) 10.01 (s, 1H), 9.24 (s, 1H), 9.12 (s, 1H), 8.55 (m, 2H), 8.27 (s, 1H), 7.92 (d, J=7.8, 1H), 7.85 (t, J=7.8, 1H), 7.79 (d, J=9.0, 1H), 7.74 (d, J=9.0, 1H), 7.32 (d, J=4.7, 1H), 7.06 (d, J=4.7, 1H), 3.79 (s, 3H), 3.29 (d, J=7.0, 2H), 0.83 (m, 1H), 0.41 (m, 2H), 0.07 (m, 2H).

Example 1321

[7-(3-Cyclopropylmethanesulfonyl-phenyl)-pyrrolo[2,1-f][1,2,4]triazin-2-yl]-(1-methyl-1H-indazol-6-yl)-amine Following the synthetic and purification procedures described in Example 1293d, 7-(3-cyclopropylmethanesulfonyl-phenyl)-2-methylsulfanyl-pyrrolo[2,1-f][1,2,4]triazine (75 mg, 0.20 mmol) was coupled with 1-methyl-1H-indazol-6-ylamine (50.0 mg, 0.340 mmol) at 105° C. for 168 h to afford the titled compound. Yield of TFA salt: 11 mg (10%) of brown powder; LC/MS: 459 (M+H); HPLC: 97% pure, RT=3.29 min; $^1$H NMR: (DMSO, δ) 9.74 (s, 1H), 9.10 (s, 1H), 8.58 (d, J=7.7, 1H), 8.32 (s, 1H), 8.00 (s, 1H), 7.84 (d, J=7.9, 1H), 7.82 (s, 1H), 7.78 (t, J=7.9, 1H), 7.56 (d, J=8.7, 1H), 7.23 (d, J=8.7, 1H), 7.20 (d, J=4.9, 1H), 6.95 (d, J=4.9, 1H), 3.69 (s, 3H), 3.22 (d, J=7.3, 2H), 0.78 (m, 1H), 0.33 (m, 2H), −0.01 (m, 2H).

Example 1322

[7-(3-Cyclopropylmethanesulfonyl-phenyl)-pyrrolo[2,1-f][1,2,4]triazin-2-yl]-(1-methyl-1H-indazol-5-yl)-amine Following the synthetic and purification procedures described in Example 1293d, 7-(3-cyclopropylmethanesulfonyl-phenyl)-2-methylsulfanyl-pyrrolo[2,1-f][1,2,4]triazine (75 mg, 0.20 mmol was coupled with 1-methyl-1H-indazol-5-ylamine (50.0 mg, 0.340 mmol) and at 105° C. for 90 h to afford the title compound. Yield of TFA salt: 43 mg (38%) of brown powder; LC/MS: 459 (M+H); HPLC: 97% pure, RT=3.23 min; $^1$H NMR: (DMSO, δ) 9.47 (s, 1H), 8.94 (s, 1H), 8.51 (d, J=7.7, 1H), 8.36 (s, 1H), 8.14 (s, 1H), 7.84 (m, 2H), 7.75 (t, J=7.8, 1H), 7.50 (m, 2H), 7.16 (d, J=4.7, 1H), 6.89 (d, J=4.7, 1H), 3.92 (s, 3H), 3.21 (d, J=7.4, 2H), 0.77 (m, 1H), 0.32 (m, 2H), −0.01 (m, 2H).

Example 1323

N-tert-Butyl-3-{2-[1-(2-morpholin-4-yl-ethyl)-1H-indazol-5-ylamino]-pyrrolo[2,1-f][1,2,4]triazin-7-yl}-benzenesulfonamide 1323a) 1-(2-Morpholin-4-yl-ethyl)-5-nitro-1H-indazole and 2-(2-morpholin-4-yl-ethyl)-5-nitro-2H-indazole: A mixture of 5-nitroindazole (6.00 g, 36.8 mmol) and potassium carbonate (15.0 g, 108 mmol) in N,N-Dimethylformamide (100 mL) was stirred for 1 h before adding 4-(2-chloroethyl)-morpholine hydrochloride (10.6 g, 56.8 mmol). The reaction was warmed at 60° C. for 24 h. The reaction mixture was passed through a pad of silica gel (~75 mL), and the pad rinsed with EtOAc/Et$_3$N (4:1, 250 ml). Solvent was removed by rotary evaporation and the oily residue was purified with an ISCO chromatography unit outfitted with an 80 g silica gel column and eluted with 4% Et$_3$N in EtOAc to afford two fractions. Crystalline 1-(2-morpholin-4-yl-ethyl)-5-nitro-1H-indazole (3.750 g, 36.9%) had LC/MS: 277 (M+H); HPLC: 97% pure, RT=1.95 min; $^1$H NMR: (DMSO, δ) 8.82 (d, J=1.8, 1H), 8.41 (s, 1H), 8.22 (dd, J=9.2, 1.8, 1H), 7.92 (d, J=9.2, 1H), 4.61 (t, J=6.2, 2H), 3.45 (m, 4H), 2.77 (t, J=6.2, 2H), 2.41 (m, 4H); and oily 2-(2-morpholin-4-yl-ethyl)-5-nitro-2H-indazole 1.853 g, 18.2%) had LC/MS: 277 (M+H); HPLC: 97% pure, RT=1.95 min; $^1$H NMR: (DMSO, δ) 8.90 (d, J=1.6, 1H), 8.83 (s, 1H), 8.01 (dd, J=9.5, 1.6, 1H), 7.78 (d, J=9.5, 1H), 4.64 (t, J=6.1, 2H), 3.52 (m, 4H), 2.87 (t, J=6.1, 2H), 2.44 (m, 4H).

1323b) 1-(2-Morpholin-4-yl-ethyl)-1H-indazol-5-ylamine: A mixture of 1-(2-morpholin-4-yl-ethyl)-5-nitro-1H-indazole (2.00 g, 7.24 mmol), iron (4.042 g, 72.39 mmol), and ammonium chloride (0.1936 g, 3.619 mmol) in ethanol (26 mL) and water (8.7 mL) was warmed to reflux for 4 h, cooled to RT O/N, and solvent removed by rotary evaporation. The resulting residue was treated with EtOAc/Et$_3$N (4:1, 65 ml), heated to reflux for 15 minutes and the slightly cooled mixture was quickly passed through a plug of silica gel (~30 mL) which was rinsed with EtOAc/Et$_3$N (4:1, 200 ml) followed by 5% NH$_3$ in MeOH:DCM solution (1:10, 50 mL). Evaporation of solvent followed by trituration with ether afforded a crystalline solid (1.65 g, 93%). LC/MS: 247 (M+H); HPLC: 97% pure, RT=0.2 min; $^1$H NMR: (DMSO, δ) 7.69 (s, 1H), 7.34 (d, J=8.7, 1H), 6.79 (dd, J=8.7, 1.8, 1H), 6.72 (d, J=1.8, 1H), 4.78 (s, 2H), 4.38 (t, J=6.6, 2H), 3.50 (m, 4H), 2.70 (t, J=6.6, 2H), 2.40 (m, 4H).

1323c) 1-(2-Morpholin-4-yl-ethyl)-6-nitro-1H-indazole and 2-(2-Morpholin-4-yl-ethyl)-6-nitro-2H-indazole were prepared analogously to Example 1323a. Crystalline 1-(2-morpholin-4-yl-ethyl)-6-nitro-1H-indazole (43% yield) had LC/MS: 277 (M+H); HPLC: 97% pure, RT=1.95 min; $^1$H NMR: (DMSO, δ) 8.80 (s, 1H), 8.31 (s, 1H), 7.99 (d, J=8.9, 1H), 7.94 (dd, J=8.9, 1.8, 1H), 4.70 (t, J=6.0, 2H), 3.46 (m, 4H), 2.76 (t, J=6.0, 2H), 2.43 (m, 4H); and oily 2-(2-Morpholin-4-yl-ethyl)-6-nitro-2H-indazole (21%) had LC/MS: 277 (M+H); HPLC: 97% pure, RT=1.95 min; $^1$H NMR: (DMSO, δ) 8.67 (s, 1H), 8.62 (s, 1H), 8.98 (d, J=9.2, 1.6, 1H), 7.81 (dd, J=9.2, 1.8 1H), 4.66 (t, J=6.4, 2H), 3.52 (m, 4H), 2.89 (t, J=6.4, 2H), 2.44 (m, 4H).

1323d) 1-(2-Morpholin-4-yl-ethyl)-1H-indazol-6-ylamine was prepared in 87% yield similarly to Example 1323b and had LC/MS: 247 (M+H); HPLC: 97% pure, RT=0.2 min; $^1$H NMR: (DMSO, δ) 7.70 (s, 1H), 7.34 (d, J=9.0, 1H), 6.44 (m, 2H), 5.30 (s, 2H), 4.27 (t, J=7.0, 2H), 3.53 (m, 4H), 2.67 (t, J=7.0, 2H), 2.41 (m, 4H).

1323e) 1-(2-Morpholin-4-yl-ethyl)-6-nitro-1H-benzimidazole and 1-(2-morpholin-4-yl-ethyl)-5-nitro-1H-benzimidazole: were prepared analogously to Example 1323a by alkylation of 6-nitro-1H-benzimidazole. Regioisomers were separated by super-critical fluid chromatography instrument equipped with a ChiralPak AD-H column and eluted with 40% MeOH (0.1% Et$_2$NH)/60% CO$_2$. Crystalline 1-(2-morpholin-4-yl-ethyl)-6-nitro-1H-benzimidazole (36% yield) had LC/MS: 277 (M+H); $^1$H NMR: (DMSO, δ) 8.54 (s, 2H), 8.19 (dd, J=8.9, 2.0, 1H), 7.89 (d, J=8.9, 1H), 4.46 (t, J=6.0, 2H), 3.50 (m, 4H), 2.70 (t, J=6.0, 2H), 2.42 (m, 4H). Crystalline 1-(2-morpholin-4-yl-ethyl)-5-nitro-1H-benzimidazole (32% yield) had LC/MS: 277 (M+H); $^1$H NMR: (DMSO, δ) 8.73 (d, J=1.8, 1H), 8.58 (s, 1H), 8.10 (dd, J=8.9, 1.8, 1H), 7.83 (d, J=8.9, 1H), 4.51 (t, J=5.7, 2H), 3.52 (m, 4H), 2.69 (t, J=5.7, 2H), 2.44 (m, 4H).

1323f) 3-(2-Morpholin-4-yl-ethyl)-3H-benzimidazol-5-ylamine was prepared similarly to Example 1323b (98% yield) and had LC/MS: 247 (M+H); $^1$H NMR: (DMSO, δ) 7.84 (s, 1H), 7.26 (d, J=8.4, 1H), 6.61 (d, J=1.6, 1H), 6.51 (dd, J=8.4, 1.6 1H), 4.93 (s, 2H), 4.16 (t, J=6.6, 2H), 3.55 (m, 4H), 2.63 (t, J=6.6, 2H), 2.42 (m, 4H).

1323g) 1-(2-Morpholin-4-yl-ethyl)-1H-benzimidazol-5-ylamine was prepared similarly to Example 1323b (77% yield) and had LC/MS: 247 (M+H); $^1$H NMR: (DMSO, δ) 8.09 (s, 1H), 7.29 (d, J=8.5, 1H), 6.77 (d, J=1.5, 1H), 6.63 (dd, J=8.5, 1.6 1H), 5.42 (br s, 2H), 4.25 (t, J=6.2, 2H), 3.53 (m, 4H), 2.65 (t, J=6.2, 2H), 2.42 (m, 4H).

1323h) Following the procedure of Example 1315, N-tert-butyl-3-(2-hydroxy-pyrrolo[2,1-f][1,2,4]triazin-7-yl)-benzenesulfonamide (511 mg, 1.48 mmol) was coupled in parallel fashion to [1-(2-morpholin-4-yl-ethyl)-1H-indazol-5-ylamine (47 mg, 0.19 mmol), 1-(2-morpholin-4-yl-ethyl)-1H-indazol-6-ylamine (47 mg, 0.19 mmol), 1-(2-morpholin-4-yl-ethyl)-1H-benzimidazol-5-ylamine (47 mg, 0.19 mmol), 3-(2-morpholin-4-yl-ethyl)-3H-benzimidazol-5-ylamine (47 mg, 0.19 mmol), 1H-indazol-6-ylamine (26 mg, 0.20 mmol), 2-ethyl-3H-benzimidazol-5-ylamine (31 mg, 0.19 mmol), 2-isopropyl-3H-benzimidazol-5-ylamine, bis-hydrochloride (48 mg, 0.19 mmol) plus iPr$_2$NEt (70 uL, 0.40 mmol), 2-tert-butyl-3H-benzimidazol-5-ylamine (36 mg, 0.19 mmol), 2,3-dimethyl-3H-benzimidazol-5-ylamine, bis-hydrochloride (45 mg, 0.19 mmol) plus iPr$_2$NEt (70 uL, 0.40 mmol) and 1-methyl-1H-benzoimidazol-5-ylamine, dihydrochloride (42 mg, 0.19 mmol) plus iPr$_2$NEt (70 uL, 0.40 mmol). Unless otherwise indicated, products were purified with an ISCO chromatography unit outfitted with a 12 g silica gel column and eluted with a gradient of DCM/MeOH.

1323i) N-tert-Butyl-3-{2-[1-(2-morpholin-4-yl-ethyl)-1H-indazol-5-ylamino]-pyrrolo[2,1-f][1,2,4]triazin-7-yl}-benzenesulfonamide: Yield of HCl salt: 44 mg (49%); LC/MS: 575 (M+H); HPLC: 97% pure, RT=2.72 min; $^1$H NMR: (DMSO, δ) 10.35 (br s, 1H), 9.62 (s, 1H), 9.06 (s, 1H), 8.57 (s, 1H), 8.45 (d, J=7.5, 1H), 8.30 (s, 1H), 8.13 (s, 1H), 7.89 (d, J=7.8, 1H), 7.78 (t, J=7.9, 1H), 7.73 (d, J=9.0, 1H), 7.68 (d, J=9.0, 1H), 7.63 (s, 1H), 7.20 (d, J=4.8, 1H), 7.01 (d, J=4.8, 1H), 4.84 (t, J=6.6, 2H), 4.00 (m, 2H), 3.67 (m, 4H), 3.50 (m, 2H), 3.16 (m, 2H), 1.10 (s, 9H).

Example 1324

N-tert-Butyl-3-{2-[1-(2-morpholin-4-yl-ethyl)-1H-indazol-6-ylamino]-pyrrolo[2,1-f][1,2,4]triazin-7-yl}-benzenesulfonamide Isolated from Example 1323h Yield of HCl salt 51 mg (56%); LC/MS: 575 (M+H); HPLC: 97% pure, RT=2.77 min; $^1$H NMR: (DMSO, δ) 10.17 (br s, 1H), 9.83 (s, 1H), 9.11 (s, 1H), 8.53 (m, 2H), 8.07 (m, 2H), 7.87 (d, J=7.7, 1H), 7.75 (m, 2H), 7.73 (d, J=9.0, 1H), 7.61 (s, 1H), 7.47 (d, J=8.9, 1H), 7.25 (d, J=4.9, 1H), 7.06 (d, J=4.9, 1H), 4.59 (m, 2H), 3.93 (m, 2H), 3.62 (m, 2H), 3.54 (m, 2H), 3.30 (m, 2H), 3.05 (m, 2H), 1.10 (s, 9H).

Example 1325

N-tert-Butyl-3-{2-[1-(2-morpholin-4-yl-ethyl)-1H-benzimidazol-5-ylamino]-pyrrolo[2,1-f][1,2,4]triazin-7-yl}-benzenesulfonamide Isolated from Example 1323h. Yield of HCl salt: 43 mg (48%); LC/MS: 575 (M+H); HPLC: 97% pure, RT=2.32 min; $^1$H NMR: (DMSO, δ) 11.38 (br s, 1H), 9.91 (s, 1H), 9.47 (br s, 1H), 9.11 (s, 1H), 8.52 (m, 2H), 8.15 (s, 1H), 8.00 (m, 2H), 7.86 (d, J=7.8, 1H), 7.80 (t, J=7.8, 1H), 7.71 (s, 1H), 7.28 (d, J=4.8, 1H), 7.06 (d, J=4.8, 1H), 4.93 (m, 2H), 3.98 (m, 2H), 3.81 (m, 2H), 3.72 (m, 2H), 3.60 (m, 2H), 3.20 (m, 2H), 1.11 (s, 9H).

Example 1326

N-tert-Butyl-3-{2-[3-(2-morpholin-4-yl-ethyl)-3H-benzimidazol-5-ylamino]-pyrrolo[2,1-f][1,2,4]triazin-7-yl}-benzenesulfonamide Isolated from Example 1323h. Yield of HCl salt 87 mg (96%); LC/MS: 575 (M+H); HPLC: 97% pure, RT=2.30 min; $^1$H NMR: (DMSO, δ) 11.50 (br s, 1H), 9.92 (s, 1H), 9.56 (br s, 1H), 9.12 (s, 1H), 8.60 (s, 1H), 8.38 (d, J=7.8, 1H), 8.20 (s, 1H), 7.93 (d, J=9.0, 1H), 7.86 (m, 2H), 7.74 (t, J=7.9, 1H), 7.61 (s, 1H), 7.28 (d, J=4.7, 1H), 7.07 (d, J=4.7, 1H), 4.75 (m, 2H), 3.80 (m, 2H), 3.57 (m, 2H), 3.45 (m, 2H), 3.15 (m, 2H), 3.05 (m, 2H), 1.08 (s, 9H).

Example 1327

N-tert-Butyl-3-[2-(1H-indazol-6-ylamino)-pyrrolo[2,1-f][1,2,4]triazin-7-yl]-benzenesulfonamide Isolated from Example 1323h. Yield: 7 mg (11%); LC/MS: 462 (M+H); HPLC: 97% pure, RT=3.32 min; $^1$H NMR: (DMSO, δ) 12.63 (s, 1H), 9.70 (s, 1H), 9.08 (s, 1H), 8.55 (d, J=7.4, 1H), 8.49 (s, 1H), 7.96 (m, 2H), 7.87 (d, J=7.7, 1H), 7.82 (t, J=7.7, 1H), 7.68 (m, 2H), 7.45 (d, J=8.7, 1H), 7.24 (d, J=4.7, 1H), 7.03 (d, J=4.7, 1H), 1.12 (s, 9H).

Example 1328

N-tert-Butyl-3-[2-(2-ethyl-3H-benzimidazol-5-ylamino)-pyrrolo[2,1-f][1,2,4]triazin-7-yl]-benzenesulfonamide Isolated from Example 1323h. Yield: 57 mg (79%); LC/MS: 490 (M+H); HPLC: 97% pure, RT=2.78 min; $^1$H NMR: (DMSO, δ) 12.07 (br s, 1H), 9.42 (s, 1H), 9.02 (s, 1H), 8.57 (s, 1H), 8.52 (d, J=7.8, 1H), 7.83 (m, 2H), 7.71 (t, J=7.8, 1H), 7.53 (d, J=8.4, 1H), 7.44 (d, J=8.4, 1H), 7.23 (d, J=4.7, 1H), 6.99 (d, J=4.7, 1H), 2.83 (q, J=7.7, 2H), 1.34 (t, J=7.7, 3H), 1.13 (s, 9H).

Example 1329

N-tert-Butyl-3-[2-(2-isopropyl-3H-benzimidazol-5-ylamino)-pyrrolo[2,1-f][1,2,4]triazin-7-yl]-benzenesulfonamide Isolated from Example 1323h. Yield: 43 mg (57%); LC/MS: 504 (M+H); HPLC: 97% pure, RT=2.90 min; $^1$H NMR: (DMSO, δ) 12.05 (br s, 1H), 9.42 (s, 1H), 9.02 (s, 1H), 8.58 (s, 1H), 8.50 (d, J=7.9, 1H), 7.84 (m, 2H), 7.71 (t, J=7.9, 1H), 7.54 (d, J=8.8, 1H), 7.46 (d, J=8.8, 1H), 7.22 (d, J=4.7, 1H), 6.99 (d, J=4.7, 1H), 3.15 (p, J=6.9, 1H), 1.37 (d, J=6.9, 6H), 1.12 (s, 9H).

Example 1330

N-tert-Butyl-3-[2-(2-tert-butyl-3H-benzimidazol-5-ylamino)-pyrrolo[2,1-f][1,2,4]triazin-7-yl]-benzenesulfonamide Isolated from Example 1323h. Yield: 58 mg (76%); LC/MS: 518 (M+H); HPLC: 97% pure, RT=3.02 min; $^1$H NMR: (DMSO, δ) 11.90 (br s, 1H), 9.45 (br s, 1H), 9.03 (s, 1H), 8.60 (s, 1H), 8.47 (d, J=7.9, 1H), 7.84 (m, 2H), 7.70 (t, J=7.9, 1H), 7.57 (m, 1H), 7.49 (m, 1H), 7.22 (d, J=4.7, 1H), 6.99 (d, J=4.7, 1H), 1.42 (s, 9H), 1.12 (s, 9H).

Example 1331

N-tert-Butyl-3-[2-(2,3-dimethyl-3H-benzimidazol-5-ylamino)-pyrrolo[2,1-f][1,2,4]triazin-7-yl]-benzenesulfonamide Purified by RP pHPLC from Example 1323h. Yield of TFA salt 40 mg (45% yield); LC/MS: 490 (M+H); HPLC: 97% pure, RT=2.72 min; $^1$H NMR: (DMSO, δ) 14.50 (br s, 1H), 9.89 (s, 1H), 9.11 (s, 1H), 8.52 (s, 1H), 8.49 (d, J=7.9, 1H), 8.03 (s, 1H), 7.97 (d, J=9.0, 1H), 7.86 (m, 2H), 7.77 (t, J=7.9, 1H), 7.64 (s, 1H), 7.28 (d, J=4.8, 1H), 7.06 (d, J=4.7, 1H), 3.92 (s, 3H), 2.80 (s, 3H), 1.11 (s, 9H).

Example 1332

N-tert-Butyl-3-[2-(1-methyl-1H-benzimidazol-5-ylamino)-pyrrolo[2,1-f][1,2,4]triazin-7-yl]-benzenesulfonamide Isolated from Example 1323h. Yield: 7 mg (9%); LC/MS: 476 (M+H); HPLC: 97% pure, RT=2.69 min; $^1$H NMR: (DMSO, δ) 9.56 (br s, 1H), 9.04 (s, 1H), 8.60 (s, 1H), 8.57 (d, J=7.9, 1H), 8.29 (s, 1H), 8.23 (s, 1H), 8.20 (s, 1H), 7.85 (d, J=8.0, 1H), 7.72 (t, J=8.0, 1H), 7.63 (d, J=8.8, 1H), 7.56 (d, J=8.8, 1H), 7.26 (d, J=4.7, 1H), 7.00 (d, J=4.7, 1H), 3.86 (s, 3H), 1.17 (s, 9H).

Example 1333

N-Methyl-N-(2-{2-[1-(2-morpholin-4-yl-ethyl)-1H-indazol-5-ylamino]-pyrrolo[2,1-f][1,2,4]triazin-7-yl}-phenyl)-methanesulfonamide 1333a) Following the procedure of Example 1315, N-[2-(2-hydroxy-pyrrolo[2,1-f][1,2,4]triazin-7-yl)-phenyl]-N-methyl-methanesulfonamide (475 mg, 1.49 mmol) was coupled in parallel fashion to [1-(2-morpholin-4-yl-ethyl)-1H-indazol-5-ylamine (51 mg, 0.21 mmol); 1-(2-morpholin-4-yl-ethyl)-1H-indazol-6-ylamine (51 mg, 0.21 mmol); 1-(2-morpholin-4-yl-ethyl)-1H-benzimidazol-5-ylamine (51 mg, 0.21 mmol); 3-(2-morpholin-4-yl-ethyl)-3H-benzimidazol-5-ylamine (51 mg, 0.21 mmol); 1H-indazol-6-ylamine (28 mg, 0.21 mmol); 1H-indazol-5-ylamine (28 mg, 0.21 mmol); 1-methyl-1H-indazol-5-ylamine (31 mg, 0.21 mmol); 1-methyl-1H-indazol-6-ylamine (31 mg, 0.21 mmol); 2-tert-butyl-3H-benzimidazol-5-ylamine (39 mg, 0.21 mmol). Products were purified with an ISCO chromatography unit outfitted with a 12 g silica gel column and eluted with a gradient of DCM/MeOH or by RP pHPLC as described in Example 1291c.

1333b) N-Methyl-N-(2-{2-[1-(2-morpholin-4-yl-ethyl)-1H-indazol-5-ylamino]-pyrrolo[2,1-f][1,2,4]triazin-7-yl}-phenyl)-methanesulfonamide. Purification: ISCO; Yield of HCl salt 63 mg (65%); LC/MS: 547 (M+H); HPLC: 97% pure, RT=2.21 min; $^1$H NMR: (DMSO, δ) 10.65 (br s, 1H), 9.52 (s, 1H), 8.99 (s, 1H), 8.25 (s, 1H), 8.07 (d, J=7.8, 1H), 7.91 (s, 1H), 7.68 (m, 2H), 7.62 (d, J=7.3, 1H), 7.58 (d, J=9.2, 1H), 7.01 (d, J=4.7, 1H), 6.96 (d, J=4.7, 1H), 4.84 (t, J=7.2, 2H), 3.97 (m, 2H), 3.71 (m, 2H), 3.62 (m, 2H), 3.47 (m, 2H), 3.15 (m, 2H), 3.07 (s, 3H), 2.90 (s, 3H).

Example 1334

N-Methyl-N-(2-{2-[1-(2-morpholin-4-yl-ethyl)-1H-indazol-6-ylamino]-pyrrolo[2,1-f][1,2,4]triazin-7-yl}-phenyl)-methanesulfonamide Isolated from Example 1333a. Purification: ISCO; Yield of HCl salt: 53 mg (55%); LC/MS: 547 (M+H); HPLC: 97% pure, RT=2.33 min; $^1$H NMR: (DMSO, δ) 10.12 (br s, 1H), 9.79 (s, 1H), 9.05 (s, 1H), 8.04 (s, 1H), 8.01 (s, 1H), 7.91 (d, J=7.2, 1H), 7.71 (d, J=7.7, 1H), 7.63 (m, 2H), 7.27 (d, J=8.7, 1H), 7.01 (d, J=4.7, 1H), 6.97 (d, J=4.7, 1H), 4.34 (m, 2H), 3.93 (m, 2H), 3.65 (m, 2H), 3.37 (m, 4H), 3.14 (s, 3H), 3.06 (m, 2H), 2.83 (s, 3H).

Example 1335

N-Methyl-N-(2-{2-[1-(2-morpholin-4-yl-ethyl)-1H-benzimidazol-5-ylamino]-pyrrolo[2,1-f][1,2,4]triazin-7-yl}-phenyl)-methanesulfonamide Isolated from Example 1333a. Purification: RP pHPLC; Yield of TFA salt: 63 mg (58%); LC/MS: 547 (M+H); HPLC: 97% pure, RT=1.89 min; $^1$H NMR: (DMSO, δ) 9.70 (s, 1H), 9.22 (br s, 1H), 9.03 (s, 1H), 8.10 (s, 1H), 8.05 (d, J=7.6, 1H), 7.81 (s, 2H), 7.67 (d, J=7.7, 1H), 7.63 (d, J=7.7, 1H), 7.55 (t, J=7.6, 1H), 7.03 (d, J=4.9, 1H), 7.00 (d, J=4.9, 1H), 4.75 (t, J=6.6, 2H), 4.00-3.1 (series of m, 10H), 3.12 (s, 3H), 2.88 (s, 3H).

Example 1336

N-Methyl-N-(2-{2-[3-(2-morpholin-4-yl-ethyl)-3H-benzimidazol-5-ylamino]-pyrrolo[2,1-f][1,2,4]triazin-7-yl}-phenyl)-methanesulfonamide Isolated from Example 1333a. Purification: RP pHPLC; Yield of TFA salt: 69 mg (63%); LC/MS: 547 (M+H); HPLC: 97% pure, RT=1.91 min; $^1$H NMR: (DMSO, δ) 9.88 (s, 1H), 9.13 (br s, 1H), 9.05 (s, 1H), 8.22 (s, 1H), 7.89 (d, J=6.4, 1H), 7.71 (m, 2H), 7.60 (m, 3H), 7.02 (d, J=4.7, 1H), 6.97 (d, J=4.7, 1H), 4.6-3.3 (series of m, 10H), 3.14 (s, 3H), 3.0 (m, 2H), 2.83 (s, 3H).

Example 1337

N-{2-[2-(1H-Indazol-6-ylamino)-pyrrolo[2,1-f][1,2,4]triazin-7-yl]-phenyl}-N-methyl-methanesulfonamide Isolated from Example 1333a. Purification: ISCO; Yield: 26 mg (10%); LC/MS: 434 (M+H); HPLC: 97% pure, RT=2.58 min; $^1$H NMR: (DMSO, δ) 12.67 (s, 1H), 9.53 (s, 1H), 9.01 (s, 1H), 8.05 (d, J=8.1, 1H), 7.92 (s, 1H), 7.84 (s, 1H), 7.73 (t, J=7.3, 1H), 7.66 (d, J=8.0, 1H), 7.56 (m, 2H), 7.34 (d, J=8.0, 1H), 7.02 (d, J=4.8, 1H), 6.97 (d, J=4.8, 1H), 3.08 (s, 3H), 2.90 (s, 3H).

Example 1338

N-{2-[2-(1H-Indazol-5-ylamino)-pyrrolo[2,1-f][1,2,4]triazin-7-yl]-phenyl}-N-methyl-methanesulfonamide Isolated from Example 1333a. Purification: RP pHPLC; Yield of TFA salt: 42 mg (63%); LC/MS: 434 (M+H); HPLC: 97% pure, RT=2.48 min; $^1$H NMR: (DMSO, δ) 9.44 (s, 1H), 8.98 (s, 1H), 8.23 (s, 1H), 8.06 (d, J=7.5, 1H), 7.81 (s, 1H), 7.66 (m, 3H), 7.46 (d, J=8.8, 1H), 7.41 (d, J=8.8, 1H), 7.00 (d, J=4.7, 1H), 6.95 (d, J=4.7, 1H), 3.05 (s, 3H), 2.91 (s, 3H).

Example 1339

N-Methyl-N-{2-[2-(1-methyl-1H-indazol-5-ylamino)-pyrrolo[2,1-f][1,2,4]triazin-7-yl]-phenyl}-methanesulfonamide Isolated from Example 1333a. Purification: ISCO; Yield: 27 mg (36%); LC/MS: 434 (M+H); HPLC: 97% pure, RT=2.58 min; $^1$H NMR: (DMSO, δ) 9.46 (s, 1H), 8.98 (s, 1H), 8.21 (s, 1H), 8.05 (d, J=7.8, 1H), 7.77 (s, 1H), 7.75 (m, 3H), 7.51 (s, 2H), 7.00 (d, J=4.7, 1H), 6.95 (d, J=4.5, 1H), 4.00 (s, 3H), 3.05 (s, 3H), 2.90 (s, 3H).

Example 1340

N-Methyl-N-{2-[2-(1-methyl-1H-indazol-6-ylamino)-pyrrolo[2,1-f][1,2,4]triazin-7-yl]-phenyl}-methanesulfonamide Isolated from Example 1333a. Purification: RP pHPLC; Yield of TFA salt: 43 mg (47%); LC/MS: 448 (M+H); HPLC: 97% pure, RT=2.91 min; $^1$H NMR: (DMSO, δ) 9.73 (s, 1H), 9.03 (s, 1H), 8.04 (s, 1H), 7.82 (m, 2H), 7.71 (m, 1H), 7.58 (m, 2H), 7.54 (d, J=8.8, 1H), 7.15 (d, J=8.8, 1H), 6.99 (d, J=4.7, 1H), 6.93 (d, J=4.7, 1H), 3.52 (s, 3H), 3.08 (s, 3H), 2.80 (s, 3H).

Example 1341

N-{2-[2-(2-tert-Butyl-3H-benzimidazol-5-ylamino)-pyrrolo[2,1-f][1,2,4]triazin-7-yl]-phenyl}-N-methyl-methanesulfonamide Isolated from Example 1333a. Purification: RP pHPLC; Yield of TFA salt: 67 mg (67%); LC/MS: 490 (M+H); HPLC: 97% pure, RT=2.37 min; $^1$H NMR: (DMSO, δ) 14.27 (br s, 1H), 9.68 (s, 1H), 9.04 (s, 1H), 8.00 (d, J=7.6, 1H), 7.91 (s, 1H), 7.88 (d, J=9.0, 1H), 7.66 (d, J=7.8, 1H), 7.59 (m, 2H), 7.53 (t, J=7.6, 1H), 7.03 (d, J=4.8, 1H), 7.01 (d, J=4.8, 1H), 3.11 (s, 3H), 2.87 (s, 3H), 1.51 (s, 9H).

Example 1342

N-Methyl-N-(2-{2-[2-(2-morpholin-4-yl-ethyl)-2H-indazol-6-ylamino]-pyrrolo[2,1-f][1,2,4]triazin-7-yl}-phenyl)-methanesulfonamide 1342a) 2-(2-Morpholin-4-yl-ethyl)-2H-indazol-6-ylamine: A mixture of 2-(2-morpholin-4-yl-ethyl)-6-nitro- 2H-indazole (985 mg, 3.56 mmol, Example 1323c) and 0.5% sulfided 5% platinum on carbon (212 mg), in methanol (5 mL) was shaken on a Parr apparatus operated under hydrogen (20 psi) for 2.5 h. The reaction mixture was filtered through celite and the filtrate evaporated to yield an oily product. LC/MS: 247 (M+H); $^1$H NMR: (DMSO, δ) 8.04 (s, 1H), 7.34 (d, J=8.8, 1H), 6.50 (dd, J=8.8, 1.5, 1H), 6.45 (s, 1H), 4.99 (s, 2H), 4.35 (t, J=6.6, 2H), 3.53 (m, 4H), 2.78 (t, J=6.6, 2H), 2.41 (m, 4H).

1342b) 2-(2-Morpholin-4-yl-ethyl)-2H-indazol-5-ylamine was prepared as above from 2-(2-morpholin-4-yl-ethyl)-5-nitro-2H-indazole (Example 1323a). LC/MS: 247 (M+H); $^1$H NMR: (DMSO, δ) 7.91 (s, 1H), 7.31 (d, J=8.8, 1H), 6.72 (dd, J=8.8, 1.5, 1H), 6.55 (s, 1H), 4.75 (s, 2H), 4.40 (t, J=6.6, 2H), 3.53 (m, 4H), 2.79 (t, J=6.6, 2H), 2.41 (m, 4H).

1342c) Following the procedure of Example 1315, N-[2-(2-hydroxy-pyrrolo[2,1-f][1,2,4]triazin-7-yl)-phenyl]-N-methyl-methanesulfonamide (105 mg, 0.330 mmol) was coupled in parallel fashion to 2-(2-morpholin-4-yl-ethyl)-2H-indazol-6-ylamine (57 mg, 0.23 mmol) and 2-(2-morpholin-4-yl-ethyl)-2H-indazol-5-ylamine (57 mg, 0.23 mmol). Products were purified by RP pHPLC as described in Example 1291c. Yield of TFA salt: 51 mg (46%); LC/MS: 547 (M+H); HPLC: 97% pure, RT=2.20 min; $^1$H NMR: (DMSO, δ) 9.53 (s, 1H), 9.01 (s, 1H), 8.31 (d, J=7.6, 1H), 8.13 (d, J=7.9, 1H), 8.11 (s, 1H), 7.68 (d, J=7.8, 1H), 7.60 (m, 3H), 7.23 (d, J=8.9, 1H), 7.04 (d, J=4.8, 1H), 6.98 (d, J=4.8, 1H), 4.81 (t, J=5.9, 2H), 3.85 (m, 4H), 3.76 (m, 2H), 3.35 (m, 4H), 3.13 (s, 3H), 2.91 (s, 3H).

Example 1343

N-Methyl-N-(2-{2-[2-(2-morpholin-4-yl-ethyl)-2H-indazol-5-ylamino]-pyrrolo[2,1-f][1,2,4]triazin-7-yl}-phenyl)-methanesulfonamide Isolated from Example 1342c. Yield of TFA salt: 62 mg, (56%); LC/MS: 547 (M+H); HPLC: 97% pure, RT=2.18 min; $^1$H NMR: (DMSO, δ) 9.48 (s, 1H), 8.99 (s, 1H), 8.17 (m, 2H), 8.10 (d, J=7.5, 1H), 7.67 (m, 2H), 7.60 (t, J=7.7, 1H), 7.53 (d, J=9.1, 1H), 7.41 (d, J=9.1, 1H), 7.02 (d, J=4.7, 1H), 6.96 (d, J=4.7, 1H), 4.84 (t, J=5.9, 2H), 3.85 (m, 4H), 3.77 (m, 2H), 3.30 (m, 4H), 3.09 (s, 3H), 2.90 (s, 3H).

Example 1344

N-tert-Butyl-3-{2-[2-(2-morpholin-4-yl-ethyl)-2H-indazol-6-ylamino]-pyrrolo[2,1-f][1,2,4]triazin-7-yl}-benzenesulfonamide Following the procedure of Example 1315, N-tert-butyl-3-(2-hydroxy-pyrrolo[2,1-f][1,2,4]triazin-7-yl)-benzenesulfonamide (114 mg, 0.330 mmol) was coupled in parallel fashion to 2-(2-morpholin-4-yl-ethyl)-2H-indazol-6-ylamine (57 mg, 0.23 mmol) and 2-(2-morpholin-4-yl-ethyl)-2H-indazol-5-ylamine (57 mg, 0.23 mmol). Products were purified by RP pHPLC as described in Example 1291c. Yield of TFA salt: 71 mg (62%); LC/MS: 575 (M+H); HPLC: 97% pure, RT=2.73 min; $^1$H NMR: (DMSO, δ) 9.68 (s, 1H), 9.08 (s, 1H), 8.73 (d, J=7.9, 1H), 8.42 (s, 1H), 8.38 (s, 1H), 8.19 (s, 1H), 7.87 (d, J=7.8, 1H), 7.77 (t, J=7.7, 1H), 7.72 (s, 1H), 7.69 (d, J=9.0, 1H), 7.36 (d, J=9.0, 1H), 7.25 (d, J=4.8, 1H), 7.04 (d, J=4.8, 1H), 4.85 (t, J=5.7, 2H), 3.85 (m, 4H), 3.80 (m, 2H), 3.30 (m, 4H), 1.13 (s, 9H).

Example 1345

N-tert-Butyl-3-{2-[2-(2-morpholin-4-yl-ethyl)-2H-indazol-5-ylamino]-pyrrolo[2,1-f][1,2,4]triazin-7-yl}-benzenesulfonamide Isolated from Example 1344. Yield of TFA salt: 62%; LC/MS: 575 (M+H); HPLC: 97% pure, RT=2.68 min; $^1$H NMR: (DMSO, δ) 9.60 (s, 1H), 9.06 (s, 1H), 8.53 (d, J=7.7, 1H), 8.49 (s, 1H), 8.35 (s, 1H), 8.27 (s, 1H), 7.88 (d, J=7.8, 1H), 7.79 (t, J=7.8, 1H), 7.65 (s, 1H), 7.61 (d, J=9.2, 1H), 7.51 (d, J=9.2, 1H), 7.20 (d, J=4.8, 1H), 7.01 (d, J=4.8, 1H), 4.85 (t, J=5.7, 2H), 3.85 (m, 4H), 3.79 (m, 2H), 3.30 (m, 4H), 1.11 (s, 9H).

Example 1346

[7-(2-Methoxy-phenyl)-pyrrolo[2,1-f][1,2,4]triazin-2-yl]-[1-(2-morpholin-4-yl-ethyl)-1H-indazol-5-yl]-amine Following the procedure of Example 1315, 7-(2-methoxy-phenyl)-pyrrolo[2,1-f][1,2,4]triazin-2-ol (365 mg, 1.51 mmol)was coupled in parallel fashion to 1-(2-morpholin-4-yl-ethyl)-1H-indazol-5-ylamine (74 mg, 0.30 mmol), 1-(2-morpholin-4-yl-ethyl)-1H-indazol-6-ylamine (74 mg, 0.30 mmol), 1-(2-morpholin-4-yl-ethyl)-1H-benzimidazol-5-ylamine (74 mg, 0.30 mmol), 3-(2-morpholin-4-yl-ethyl)-3H-benzimidazol-5-ylamine (74 mg, 0.30 mmol), 2-(2-morpholin-4-yl-ethyl)-2H-indazol-6-ylamine (74 mg, 0.30 mmol), 2-(2-morpholin-4-yl-ethyl)-2H-indazol-5-ylamine (74 g, 30 mmol) and 2-tert-butyl-3H-benzimidazol-5-ylamine (57 mg, 0.30 mmol). Products were purified by RP pHPLC as described in Example 1291c. Yield of TFA salt: 103 mg (82%); LC/MS: 470 (M+H); HPLC: 97% pure, RT=2.51 min; $^1$H NMR: (DMSO, δ) 9.86 (s, 1H), 9.50 (s, 1H), 8.97 (s, 1H), 8.36 (s, 1H), 7.83 (d, J=7.5, 1H), 7.62 (m, 2H), 7.54 (t, J=7.7, 1H), 7.32 (d, J=8.3, 1H), 7.18 (t, J=7.5, 1H), 6.95 (d, J=4.8, 1H), 6.93 (d, J=4.8, 1H), 4.79 (t, J=6.3, 2H), 3.95 (m, 2H), 3.81 (s, 3H), 3.71 (m, 6H), 3.16 (m, 2H).

Example 1347

[7-(2-Methoxy-phenyl)-pyrrolo[2,1-f][1,2,4]triazin-2-yl]-[1-(2-morpholin-4-yl-ethyl)-1H-indazol-6-yl]-amine Isolated from Example 1346. Yield of TFA salt: 90 mg (71%); LC/MS: 470 (M+H); HPLC: 97% pure, RT=2.58 min; $^1$H NMR: (DMSO, δ) 9.77 (s, 1H), 9.02 (s, 1H), 8.06 (s, 1H), 8.03 (s, 1H), 7.85 (d, J=7.2, 1H), 7.64 (d, J=8.6, 1H), 7.54 (t, J=7.7, 1H), 7.35 (d, J=8.6, 1H), 7.27 (d, J=8.6, 1H), 7.18 (t, J=7.4, 1H), 6.98 (s, 2H), 4.39 (t, J=6.0, 2H), 3.90 (m, 2H), 3.78 (s, 3H), 3.73 (m, 2H), 3.4-2.9 (series of m, 6H).

Example 1348

[7-(2-Methoxy-phenyl)-pyrrolo[2,1-f][1,2,4]triazin-2-yl]-[1-(2-morpholin-4-yl-ethyl)-1H-benzimidazol-5-yl]-amine Isolated from Example 1346. Yield of TFA salt: 95 mg (75%); LC/MS: 470 (M+H); HPLC: 97% pure, RT=2.14 min; $^1$H NMR: (DMSO, δ) 9.71 (s, 1H), 9.16 (br s, 1H), 9.01 (s, 1H), 8.11 (s, 1H), 7.91 (d, J=8.9, 1H), 7.84 (d, J=7.8, 1H), 7.80 (d, J=8.6, 1H), 7.48 (t, J=7.7, 1H), 7.25 (d, J=8.6, 1H), 7.17 (t, J=7.4, 1H), 6.99 (d, J=4.8, 1H), 6.97 (d, J=4.8, 1H), 4.77 (t, J=6.0, 2H), 3.90 (m, 4H), 3.84 (s, 3H), 3.73 (m, 2H), 3.55 (m, 2H), 3.23 (m, 2H).

Example 1349

[7-(2-Methoxy-phenyl)-pyrrolo[2,1-f][1,2,4]triazin-2-yl]-[3-(2-morpholin-4-yl-ethyl)-3H-benzimidazol-5-yl]-amine Isolated from Example 1346. Yield of TFA salt: 92 mg (73%); LC/MS: 470 (M+H); HPLC: 97% pure, RT=2.13 min; $^1$H NMR: (DMSO, δ) 9.85 (s, 1H), 9.12 (br s, 1H), 9.02 (s, 1H), 8.21 (s, 1H), 7.83 (d, J=7.5, 1H), 7.70 (m, 2H), 7.52 (t, J=7.8, 1H), 7.26 (d, J=8.4, 1H), 7.17 (t, J=7.5, 1H), 6.98 (m, 2H), 4.37 (m, 2H), 3.90-3.40 (m, 6H), 3.78 (s, 3H), 3.13 (m, 2H) 2.85 (m, 2H).

Example 1350

[7-(2-Methoxy-phenyl)-pyrrolo[2,1-f][1,2,4]triazin-2-yl]-[2-(2-morpholin-4-yl-ethyl)-2H-indazol-6-yl]-amine Isolated from Example 1346. Yield of TFA salt: 78 mg (73%); LC/MS: 470 (M+H); HPLC: 97% pure, RT=2.48 min; $^1$H NMR: (DMSO, δ) 9.49 (s, 1H), 8.98 (s, 1H), 8.30 (s, 1H), 8.21 (s, 1H), 7.86 (d, J=7.4, 1H), 7.57 (d, J=9.0, 1H), 7.44 (t, J=7.8, 1H), 7.25 (m, 2H), 7.16 (t, J=7.4, 1H), 6.98 (d, J=4.8, 1H), 6.95 (d, J=4.8, 1H), 4.82 (t, J=5.9, 2H), 3.86 (s, 3H), 3.76 (m, 2H), 3.65 (m, 4H), 3.35 (m, 4H).

Example 1351

[7-(2-Methoxy-phenyl)-pyrrolo[2,1-f][1,2,4]triazin-2-yl]-[2-(2-morpholin-4-yl-ethyl)-2H-indazol-5-yl]-amine Isolated from Example 1346. Yield of TFA salt: 90 mg (71%); LC/MS: 470 (M+H); HPLC: 97% pure, RT=2.44 min; $^1$H NMR: (DMSO, δ) 9.46 (s, 1H), 8.97 (s, 1H), 8.29 (s, 1H), 8.18 (s, 1H), 7.87 (d, J=7.5, 1H), 7.53 (m, 2H), 7.41 (d, J=9.2, 1H), 7.30 (d, J=8.2, 1H), 7.20 (t, J=7.5, 1H), 6.97 (d, J=4.8, 1H), 6.94 (d, J=4.8, 1H), 4.85 (t, J=6.3, 2H), 3.81 (s, 3H), 3.77 (m, 2H), 3.70 (m, 4H), 3.30 (m, 4H).

Example 1352

(2-tert-Butyl-3H-benzimidazol-5-yl)-[7-(2-methoxy-phenyl)-pyrrolo[2,1-f][1,2,4]triazin-2-yl]-amine Isolated from Example 1346. Yield of TFA salt: 84 mg (71%); LC/MS: 413 (M+H); HPLC: 97% pure, RT=2.68 min; $^1$H NMR: (DMSO, δ) 14.4 (br s, 1H), 9.72 (s, 1H), 9.02 (br s, 1H), 8.06 (d, J=9.0, 1H), 7.88 (d, J=7.5, 1H), 7.86 (s, 1H), 7.57 (d, J=9.0, 1H), 7.45 (t, J=7.8, 1H), 7.21 (d, J=8.3, 1H), 7.13 (t, J=7.5, 1H), 7.02 (d, J=4.8, 1H), 6.98 (d, J=4.8, 1H), 3.80 (s, 3H), 1.52 (s, 9H).

Example 1353

2-(4-{4-[7-(2-Fluoro-6-methoxy-phenyl)-pyrrolo[2,1-f][1,2,4]triazin-2-ylamino]-phenyl}-piperidin-1-yl)-acetamide Following the synthetic and purification procedures of Example 1291c, 7-(2-Fluoro-6-methoxy-phenyl)-2-methanesulfinyl-pyrrolo[2,1-f][1,2,4]triazine (79 mg, 0.26 mmol) was coupled to 2-[4-(4-amino-phenyl)-piperidin-1-yl]-acetamide (91 mg, 0.39 mmol) in a sealed vial at 125° C. for 96 h followed by 6 h in a microwave reactor at 170° C. Yield of TFA salt: 25 mg (16%); LC/MS: 475 (M+H); HPLC: 97% pure, RT=2.54 min; $^1$H NMR: (DMSO, δ) 9.49 (br s, 1H), 9.39 (s, 1H), 8.97 (br s, 1H), 7.96 (s, 1H), 7.71 (s, 1H), 7.56 (m, 3H), 7.10-6.97 (series of m, 3H), 6.95 (d, J=4.8, 1H), 6.85 (d, J=4.8, 1H), 3.91 (m, 2H), 3.76 (s, 3H), 3.53 (m, 2H), 3.12 (m, 2H), 2.68 (m, 1H), 1.92 (m, 4H).

Example 1361

N-Methyl-N-{2-[2-(pyridin-3-ylamino)-pyrrolo[2,1-f][1,2,4]triazin-7-yl]-phenyl}-methanesulfonamide; compound with trifluoroacetic acid 3-aminopyridine (0.072 g, 0.00076 mol), N-[2-(2-Methanesulfinyl-pyrrolo[2,1-f][1,2,4]triazin-7-yl)-phenyl]-N-methyl-methanesulfonamide (0.112 g, 0.000307 mol), 1-Methoxy-2-propanol (1.0 mL, 0.010 mol) and N,N-Diisopropylethylamine (0.120 mL, 0.000689 mol) were combined in a microwave vial. The reaction was microwaved at 300 watts, 170° C. for 17 hours, then purified with preparatory HPLC and lyophilized to yield a yellow solid, N-Methyl-N-{2-[2-(pyridin-3-ylamino)-pyrrolo[2,1-f][1,2,4]triazin-7-yl]-phenyl}-methanesulfonamide; compound with trifluoroacetic acid (32 mg, 21%). LCMS: m/z=395.13 (M+H+); 1H NMR (400 MHz, DMSO-d6) δ 10.29 (s, 1H), 9.10 (s, 1H), 9.03 (s, 1H), 8.41 (m, 2H), 7.94 (d, 1H), 7.76 (m, 1H), 7.70 (d, 1H, J=7.2 Hz), 7.60 (m, 2H), 7.08 (s, 2H), 3.11 (s, 3H), 2.89 (s, 3H).

Example 1362

N-Methyl-N-{2-[2-(thiazol-2-ylamino)-pyrrolo[2,1-f][1,2,4]triazin-7-yl]-phenyl}-methanesulfonamide; compound with trifluoro-acetic acid The compound was prepared with a procedure analogous to example 1361 and microwaved for 6 hours to yield a brown solid, N-Methyl-N-{2-[2-(thiazol-2-ylamino)-pyrrolo[2,1-f][1,2,4]triazin-7-yl]-phenyl}-methanesulfonamide; compound with trifluoro-acetic acid (14.4 mg, 8.4%). LCMS: m/z=401.08 (M+H+); 1H NMR (400 MHz, DMSO-d6) δ 9.08 (s, 1H), 7.90 (m, 1H), 7.67 (d, 1H, J=7.0 Hz), 7.57 (m, 2H), 7.39 (m, 1H), 7.09 (m, 3H), 3.09 (s, 3H), 2.87 (s, 3H).

Example 1363

N-{3-[7-(3-Methanesulfonylamino-phenyl)-pyrrolo[2,1-f][1,2,4]triazin-2-ylamino]-phenyl}-acetamide; compound with trifluoro-acetic acid The compound was prepared with a procedure analogous to example 1361 and microwaved for 6 hours to yield a brown solid, N-{3-[7-(3-Methanesulfonylamino-phenyl)-pyrrolo[2,1-f][1,2,4]triazin-2-ylamino]-phenyl}-acetamide; compound with trifluoro-acetic acid (56 mg, 30%). LCMS: m/z=437.15 (M+H+); 1H NMR (400 MHz, DMSO-d6) δ 9.81 (m, 2H), 9.47 (s, 1H), 9.01 (s, 1H), 8.02 (d, 1H, J=7.8 Hz), 7.78 (s, 1H), 7.59 (d, 1H, J=8.1 Hz), 7.45 (m, 1H), 7.25 (m, 2H), 7.15 (m, 1H), 7.07 (m, 1H), 6.97 (m, 1H), 3.01 (s, 3H), 2.05 (s, 3H).

Example 1364

N-Methyl-N-{2-[2-(pyridin-4-ylamino)-pyrrolo[2,1-f][1,2,4]triazin-7-yl]-phenyl}-methanesulfonamide; compound with trifluoro-acetic acid The compound was prepared with a procedure analogous to example 1361 and microwaved at 170° C. for 2 hours to yield a brown solid, N-Methyl-N-{2-[2-(pyridin-4-ylamino)-pyrrolo[2,1-f][1,2,4]triazin-7-yl]-phenyl}-methanesulfonamide; compound with trifluoro-acetic acid (12.6 mg, 7%). LCMS: m/z=395.14 (M+H+); 1H NMR (400 MHz, CDCl3) δ 8.85 (s, 1H), 8.31 (d, 2H, J=6.6 Hz), 7.92 (br s, 2H), 7.82 (d, 1H, J=7.1 Hz), 7.56 (m, 3H), 7.17 (d, 1H, J=4.5 Hz), 7.06 (d, 1H, J=3.6 Hz), 3.21 (s, 3H), 2.82 (m, 3H).

Example 1365

N-{3-[2-(1-Acetyl-5,5-dimethyl-2,3,4,5-tetrahydro-1H-benzo[b]azepin-8-ylamino)-pyrrolo[2,1-f][1,2,4]triazin-7-yl]-phenyl}-methanesulfonamide; compound with trifluoro-acetic acid The compound was prepared with a procedure analogous to example 1361 and microwaved at 170° C. for 3.5 hours to yield a brown solid, N-{3-[2-(1-Acetyl-5,5-dimethyl-2,3,4,5-tetrahydro-1H-benzo[b]azepin-8-ylamino)-pyrrolo[2,1-f][1,2,4]triazin-7-yl]-phenyl}-methanesulfonamide; compound with trifluoro-acetic acid (96 mg, 42%). LCMS: m/z=519.19 (M+H+); 1H NMR (400 MHz, DMSO-d6) δ 9.85 (s, 1H), 9.58 (s, 1H), 9.01 (s, 1H), 7.90 (d, 1H, J=7.8 Hz), 7.76 (s, 1H), 7.68 (d, 1H, J=8.6 Hz), 7.61 (s, 1H), 7.46 (m, 1H), 7.37 (d, 1H, J=8.5 Hz), 7.25 (d, 1H, J=7.8 Hz), 7.05 (m, 1H), 6.98 (m, 1H), 4.56 (d, 1H, J=12.9 Hz), 3.03 (s, 3H), 2.54 (m, 1H), 1.99 (m, 1H), 1.70 (s, 3H), 1.61 (m, 2H), 1.46 (m, 1H), 1.39 (s, 3H), 1.11 (s, 3H).

Example 1366

N-{2-[2-(1-Acetyl-5,5-dimethyl-2,3,4,5-tetrahydro-1H-benzo[b]azepin-8-ylamino)-pyrrolo[2,1-f][1,2,4]triazin-7-yl]-phenyl}-N-methyl-methanesulfonamide; compound with trifluoro-acetic acid The compound was prepared with a procedure analogous to example 1361 and microwaved at 170° C. for 4 hours to yield a brown solid, N-{2-[2-(1-Acetyl-5,5-dimethyl-2,3,4,5-tetrahydro-1H-benzo[b]azepin-8-ylamino)-pyrrolo[2,1-f][1,2,4]triazin-7-yl]-phenyl}-N-methyl-methanesulfonamide; compound with trifluoro-acetic acid (38 mg, 21%). LCMS: m/z=533.20 (M+H+); 1H NMR (400 MHz, DMSO-d6) δ 9.52 (s, 1H), 8.98 (s, 1H), 7.83 (m, 1H), 7.66 (m, 2H), 7.51 (m, 1H), 7.45 (m, 1H), 7.33 (m, 1H), 7.23 (d, 1H, J=8.8 Hz), 6.95 (m, 2H), 4.50 (m, 1H), 3.06 (s, 3H), 2.87 (s, 3H), 2.43 (m, 1H), 1.97 (m, 1H), 1.61 (m, 2H), 1.52 (s, 3H), 1.42 (m, 1H), 1.34 (s, 3H), 1.06 (s, 3H).

Example 1367

N-{3-[2-(1-Acetyl-2,3-dihydro-1H-indol-6-ylamino)-pyrrolo[2,1-f][1,2,4]triazin-7-yl]-phenyl}-methanesulfonamide; compound with trifluoro-acetic acid The compound was prepared with a procedure analogous to example 1361 and microwaved at 170° C. for 6 hours to yield a yellow solid, N-{3-[2-(1-Acetyl-2,3-dihydro-1H-indol-6-ylamino)-pyrrolo[2,1-f][1,2,4]triazin-7-yl]-phenyl}-methanesulfonamide; compound with trifluoro-acetic acid (56 mg, 31%). LCMS: m/z=463.15 (M+H+); 1H NMR (400 MHz, DMSO-d6) δ 9.69 (s, 1H), 9.28 (s, 1H), 8.90 (s, 1H), 8.17 (s, 1H), 7.95 (d, 1H, J=7.8 Hz), 7.73 (s, 1H), 7.51 (m, 1H), 7.37 (m, 1H), 7.17 (m, 1H), 7.09 (d, 1H, J=8.1 Hz), 6.98 (d, 1H, J=4.7 Hz), 6.87 (d, 1H, J=4.7 Hz), 4.03 (m, 2H), 3.02 (m, 2H), 2.93 (s, 3H), 2.10 (s, 3H).

Example 1368

N-{3-[7-(3-tert-Butylsulfamoyl-phenyl)-pyrrolo[2,1-f][1,2,4]triazin-2-ylamino]-phenyl}-acetamide; compound with trifluoro-acetic acid The compound was prepared with a procedure analogous to example 1361 and microwaved at 170° C. for 4 hours to yield a brown solid, N-{3-[7-(3-tert-Butylsulfamoyl-phenyl)-pyrrolo[2,1-f][1,2,4]triazin-2-ylamino]-phenyl}-acetamide; compound with trifluoro-acetic acid (49 mg, 29%). LCMS: m/z=479.14 (M+H+); 1H NMR (400 MHz, DMSO-d6) δ 9.84 (s, 1H), 9.52 (s, 1H), 9.04 (s, 1H), 8.49 (m, 2H), 7.82 (m, 2H), 7.66 (m, 1H), 7.60 (m, 2H), 7.26 (m, 1H), 7.22 (d, 1H, J=4.8 Hz), 7.14 (d, 1H, J=8.2 Hz), 7.01 (d, 1H, J=4.8 Hz), 2.04 (s, 3H), 1.11 (s, 9H).

Example 1369

3-[2-(1-Acetyl-5,5-dimethyl-2,3,4,5-tetrahydro-1H-benzo[b]azepin-8-ylamino)-pyrrolo[2,1-f][1,2,4]triazin-7-yl]-N-tert-butyl-benzenesulfonamide; compound with trifluoro-acetic acid The compound was prepared with a procedure analogous to example 1361 and microwaved at 170° C. for 7 hours to yield a yellow solid, 3-[2-(1-Acetyl-5,5-dimethyl-2,3,4,5-tetrahydro-1H-benzo[b]azepin-8-ylamino)-pyrrolo[2,1-f][1,2,4]triazin-7-yl]-N-tert-butyl-benzenesulfonamide; compound with trifluoro-acetic acid (78 mg, 38%) LCMS: m/z=561.23 (M+H+); 1H NMR (400 MHz, DMSO-d6) δ 9.62 (s, 1H), 9.05 (s, 1H), 8.39 (m, 2H), 7.84 (d, 1H, J=8.0 Hz), 7.70 (m, 2H), 7.62 (s, 1H), 7.52 (d, 1H, J=2.4 Hz), 7.44 (d, 1H, J=8.8 Hz), 7.18 (d, 1H, J=4.8 Hz), 7.01 (d, 1H, J=4.8 Hz), 4.56 (m, 1H), 2.53 (m, 1H), 1.99 (m, 1H), 1.72 (s, 3H), 1.64 (m, 2H), 1.46 (m, 1H), 1.39 (s, 3H), 1.12 (m, 12H).

Example 1370

N-(2-{2-[4-Methoxy-3-(2-oxo-pyrrolidin-1-yl)-phenylamino]-pyrrolo[2,1-f][1,2,4]triazin-7-yl}-phenyl)-N-methyl-methanesulfonamide; compound with trifluoro-acetic acid The compound was prepared with a procedure analogous to example 1361 and microwaved at 170° C. for 4 hours to yield a yellow solid, N-(2-{2-[4-Methoxy-3-(2-oxo-pyrrolidin-1-yl)-phenylamino]-pyrrolo[2,1-f][1,2,4]triazin-7-yl}-phenyl)-N-methyl-methanesulfonamide; compound with trifluoro-acetic acid (87 mg, 47%). LCMS: m/z=507.15 (M+H+); 1H NMR (400 MHz, DMSO-d6) δ 9.34 (s, 1H), 8.95 (s, 1H), 7.82 (m, 1H), 7.65 (d, 1H, J=7.9 Hz), 7.60 (m, 1H), 7.56 (m, 1H), 7.51 (m, 1H), 7.40 (m, 1H), 6.93 (m, 3H), 3.71 (s, 3H), 3.41 (m, 2H), 3.04 (s, 3H), 2.84 (s, 3H), 2.35 (m, 2H), 2.04 (m, 2H).

Example 1371

N-{2-[2-(2,2-Dimethyl-3-oxo-3,4-dihydro-2H-1,4-benzoxazin-6-ylamino)-pyrrolo[2,1-f][1,2,4]triazin-7-yl]-phenyl}-N-methyl-methanesulfonamide; compound with trifluoro-acetic acid The compound was prepared with a procedure analogous to example 1361 and microwaved at 170° C. for 4 hours to yield a yellow solid, N-{2-[2-(2,2-Dimethyl-3-oxo-3,4-dihydro-2H-1,4-benzoxazin-6-ylamino)-pyrrolo[2,1-f][1,2,4]triazin-7-yl]-phenyl}-N-methyl-methanesulfonamide; compound with trifluoro-acetic acid (79 mg, 41%). LCMS: m/z=493.13 (M+H+); 99% pure by HPLC; 1H NMR (400 MHz, DMSO-d6) δ 10.48 (s, 1H), 9.19 (s, 1H), 8.88 (s, 1H), 7.90 (m, 1H), 7.56 (m, 1H), 7.45 (m, 2H), 7.24 (m, 1H), 6.92 (m, 2H), 6.86 (d, 1H, J=4.7 Hz), 6.68 (d, 1H, J=8.7 Hz), 2.99 (s, 3H), 2.82 (s, 3H), 1.30 (s, 6H).

Example 1372

3-[2-(1-Acetyl-2,3-dihydro-1H-indol-6-ylamino)-pyrrolo[2,1-f][1,2,4]triazin-7-yl]-N-tert-butyl-benzenesulfonamide; compound with trifluoro-acetic acid The compound was prepared with a procedure analogous to example 1361 and microwaved at 170° C. for 4 hours to yield a yellow solid, 3-[2-(1-Acetyl-2,3-dihydro-1H-indol-6-ylamino)-pyrrolo[2,1-f][1,2,4]triazin-7-yl]-N-tert-butyl-benzenesulfonamide; compound with trifluoro-acetic acid (39 mg, 26%). yellow solid; LCMS: m/z=505.17 (M+H+); 1H NMR (400 MHz, DMSO-d6) δ 9.34 (s, 1H), 8.94 (s, 1H), 8.42 (m, 2H), 8.20 (s, 1H), 7.73 (d, 1H, J=7.7 Hz), 7.52 (m, 3H), 7.13 (m, 2H), 6.91 (d, 1H, J=4.7 Hz), 4.04 (m, 2H), 3.02 (m, 2H), 2.10 (s, 3H), 1.04 (s, 9H).

Example 1373

3-[2-(4-Acetyl-3,4-dihydro-2H-benzo[1,4]oxazin-6-ylamino)-pyrrolo[2,1-f][1,2,4]triazin-7-yl]-N-tert-butyl-benzenesulfonamide; compound with trifluoro-acetic acid The compound was prepared with a procedure analogous to example 1361 and microwaved at 170° C. for 4 hours to yield an orange solid, 3-[2-(4-Acetyl-3,4-dihydro-2H-benzo[1,4]oxazin-6-ylamino)-pyrrolo[2,1-f][1,2,4]triazin-7-yl]-N-tert-butyl-benzenesulfonamide; compound with trifluoro-acetic acid (59 mg, 40%). LCMS: m/z=521.16 (M+H+); 1H NMR (400 MHz, DMSO-d6) δ 9.31 (br s, 1H), 8.94 (s, 1H), 8.37 (m, 2H), 7.75 (d, 1H, J=7.9 Hz), 7.57 (m, 2H), 7.43 (m, 1H), 7.10 (d, 1H, J=4.8 Hz), 6.91 (d, 1H, J=4.8 Hz), 6.83 (d, 1H, J=8.8 Hz), 4.16 (m, 2H), 3.81 (m, 2H), 2.06 (br s, 3H), 1.05 (s, 9H).

Example 1374

N-{2-[2-(4-Acetyl-3,4-dihydro-2H-1,4-benzoxazin-6-ylamino)-pyrrolo[2,1-f][1,2,4]triazin-7-yl]-phenyl}-N-methyl-methanesulfonamide; compound with trifluoroacetic acid The compound was prepared with a procedure analogous to example 1361 and microwaved at 170° C. for 4 hours to yield a brown solid, N-{2-[2-(4-Acetyl-3,4-dihydro-2H-1,4-benzoxazin-6-ylamino)-pyrrolo[2,1-f][1,2,4]triazin-7-yl]-phenyl}-N-methyl-methanesulfonamide; compound with trifluoro-acetic acid (51 mg, 34%). LCMS: m/z=493.13 (M+H); 1H NMR (400 MHz, DMSO-d6) δ 9.24 (br s, 1H), 8.88 (s, 1H), 7.81 (m, 2H), 7.58 (d, 1H, J=7.7 Hz), 7.39 (m, 2H), 7.14 (d, 1H, J=8.2 Hz), 6.86 (m, 2H), 6.68 (d, 1H, J=8.8 Hz), 4.10 (m, 2H), 3.75 (m, 2H), 3.00 (s, 3H), 2.81 (s, 3H), 1.67 (m, 3H).

Example 1375

N-(3-{7-[2-(Methanesulfonyl-methyl-amino)-phenyl]-pyrrolo[2,1-f][1,2,4]triazin-2-ylamino}-phenyl)-acetamide; compound with trifluoro-acetic acid The compound was prepared with a procedure analogous to example 1361 and microwaved at 170° C. for 4 hours to yield a yellow solid, N-(3-{7-[2-(Methanesulfonyl-methyl-amino)-phenyl]-pyrrolo[2,1-f][1,2,4]triazin-2-ylamino}-phenyl)-acetamide; compound with trifluoro-acetic acid (23 mg, 19%). LCMS: m/z=451.14 (M+H+); 1H NMR (400 MHz, DMSO-d6) δ 9.70 (s, 1H), 9.30 (s, 1H), 8.91 (s, 1H), 7.90 (m, 1H), 7.58 (m, 2H), 7.46 (m, 2H), 7.34 (m, 1H), 7.02 (m, 2H), 6.90 (m, 2H), 2.99 (s, 3H), 2.82 (s, 3H), 1.98 (s, 3H).

Example 1376

N-tert-Butyl-3-[2-(2,2-dimethyl-3-oxo-3,4-dihydro-2H-1,4-benzoxazin-6-ylamino)-pyrrolo[2,1-f][1,2,4]triazin-7-yl]-benzenesulfonamide; compound with trifluoro-acetic acid The compound was prepared with a procedure analogous to example 1361 and microwaved at 170° C. for 4 hours to yield an orange solid, N-tert-Butyl-3-[2-(2,2-dimethyl-3-oxo-3,4-dihydro-2H-1,4-benzoxazin-6-ylamino)-pyrrolo[2,1-f][1,2,4]triazin-7-yl]-benzenesulfonamide; compound with trifluoro-acetic acid (74 mg, 60%). LCMS: m/z=521.16 (M+H+); 1H NMR (400 MHz, DMSO-d6) δ 10.52 (br s, 1H), 9.36 (s, 1H), 8.95 (s, 1H), 8.45 (s, 1H), 8.34 (d, 1H, J=8.0 Hz), 7.75 (d, 1H, J=8.0 Hz), 7.61 (m, 1H), 7.55 (s, 1H), 7.44 (m, 1H), 7.14 (d, 1H, J=4.8 Hz), 6.97 (d, 1H, J=2.4 Hz), 6.90 (m, 2H), 1.32 (s, 6H), 1.04 (s, 9H).

Example 1377

N-tert-Butyl-3-{2-[4-methoxy-3-(2-oxo-pyrrolidin-1-yl)-phenylamino]-pyrrolo[2,1-f][1,2,4]triazin-7-yl}-benzenesulfonamide; compound with trifluoro-acetic acid The compound was prepared with a procedure analogous to example 1361 and microwaved at 170° C. for 4 hours to yield an orange solid, N-tert-Butyl-3-{2-[4-methoxy-3-(2-oxo-pyrrolidin-1-yl)-phenylamino]-pyrrolo[2,1-f][1,2,4]triazin-7-yl}-benzenesulfonamide; compound with trifluoro-acetic acid (70 mg, 54%). LCMS: m/z=535.17 (M+H+); 1H NMR (400 MHz, DMSO-d6) δ 9.39 (s, 1H), 8.95 (s, 1H), 8.36 (m, 2H), 7.79 (m, 1H), 7.60 (m, 1H), 7.63 (m, 2H), 7.55 (s, 1H), 7.51 (d, 1H, J=2.7 Hz), 7.10 (d, 1H, J=4.8 Hz), 7.05 (d, 1H, J=9.0 Hz), 6.92 (d, 1H, J=4.8 Hz), 3.69 (s, 3H), 3.55 (m, 2H), 2.30 (m, 2H), 2.00 (m, 2H), 1.05 (s, 9H).

Example 1378

N-{3-[7-(1-Methyl-1H-pyrazol-4-yl)-pyrrolo[2,1-f][1,2,4]triazin-2-ylamino]-phenyl}-acetamide; compound with trifluoro-acetic acid The compound was prepared with a procedure analogous to example 1361 and microwaved at 170° C. for 4 hours to yield a yellow solid, N-{3-[7-(1-Methyl-1H-pyrazol-4-yl)-pyrrolo[2,1-f][1,2,4]triazin-2-ylamino]-phenyl}-acetamide; compound with trifluoro-acetic acid (10 mg, 6%). LCMS: m/z=348.16 (M+H+); 1H NMR (400 MHz, DMSO-d6) δ 9.89 (s, 1H), 9.27 (s, 1H), 8.81 (s, 1H), 8.37 (s, 1H), 8.07 (s, 1H), 7.89 (s, 1H), 7.30 (d, 1H, J=7.9 Hz), 7.20 (m, 1H), 7.14 (m, 1H), 7.01 (d, 1H, J=4.7 Hz), 6.85 (d, 1H, J=4.7 Hz), 3.83 (s, 3H), 1.99 (s, 3H).

Example 1379

1-Ethyl-5,5-dimethyl-8-[7-(1-methyl-1H-pyrazol-4-yl)-pyrrolo[2,1-f][1,2,4]triazin-2-ylamino]-1,3,4,5-tetrahydro-benzo[b]azepin-2-one; compound with trifluoro-acetic acid The compound was prepared with a procedure analogous to example 1361 and microwaved at 170° C. for 4 hours to yield a yellow solid, 1-Ethyl-5,5-dimethyl-8-[7-(1-methyl-1H-pyrazol-4-yl)-pyrrolo[2,1-f][1,2,4]triazin-2-ylamino]-1,3,4,5-tetrahydro-benzo[b]azepin-2-one; compound with trifluoro-acetic acid (30 mg, 24%). LCMS: m/z=430.24 (M+H+); 98% pure by HPLC; 1H NMR (400 MHz, DMSO-d6) δ 9.42 (m, 1H), 8.83 (s, 1H), 8.835 (s, 1H), 8.08 (s, 1H), 7.69 (d, 1H, J=2.2 Hz), 7.54 (m, 1H), 7.28 (d, 1H, J=8.7 Hz), 7.00 (d, 1H, J=4.7 Hz), 6.87 (d, 1H, J=4.7 Hz), 3.82 (m, 3H), 2.14 (m, 2H), 1.89 (m, 2H), 1.22 (m, 6H), 1.06 (m, 3H).

Example 1380

N-{2-tert-Butyl-5-[7-(1-methyl-1H-pyrazol-4-yl)-pyrrolo[2,1-f][1,2,4]triazin-2-ylamino]-phenyl}-acetamide; compound with trifluoro-acetic acid The compound was prepared with a procedure analogous to example 1361 and microwaved at 170° C. for 4 hours to yield an orange solid, N-{2-tert-Butyl-5-[7-(1-methyl-1H-pyrazol-4-yl)-pyrrolo[2,1-f][1,2,4]triazin-2-ylamino]-phenyl}-acetamide; compound with trifluoro-acetic acid (32 mg, 16%). LCMS: m/z=404.23 (M+H+); 96% pure by HPLC; 1H NMR (400 MHz, DMSO-d6) δ 9.34 (s, 1H), 9.26 (s, 1H), 8.87 (s, 1H), 8.39 (s, 1H), 8.18 (s, 1H), 7.60 (m, 1H), 7.45 (m, 1H), 7.35 (m, 1H), 7.0 (d, 1H, J=4.7 Hz), 6.91 (d, 1H, J=4.7 Hz), 3.96 (s, 3H), 2.07 (s, 3H), 1.33 (s, 9H).

Example 1381

1-{5,5-Dimethyl-8-[7-(1-methyl-1H-pyrazol-4-yl)-pyrrolo[2,1-f][1,2,4]triazin-2-ylamino]-2,3,4,5-tetrahydro-benzo[b]azepin-1-yl}-ethanone; compound with trifluoro-acetic acid The compound was prepared with a procedure analogous to example 1361 and microwaved at 170° C. for 4 hours to yield a yellow solid, 1-{5,5-Dimethyl-8-[7-(1-methyl-1H-pyrazol-4-yl)-pyrrolo[2,1-f][1,2,4]triazin-2-ylamino]-2,3,4,5-tetrahydro-benzo[b]azepin-1-yl}-ethanone; compound with trifluoro-acetic acid (23 mg, 18%). LCMS: m/z=430.25 (M+H+); 1H NMR (400 MHz, DMSO-d6) δ 9.45 (s, 1H), 8.88 (s, 1H), 8.38 (s, 1H), 8.16 (s, 1H), 7.68 (m, 1H), 7.53 (d, 1H, J=2.2 Hz), 7.41 (d, 1H, J=8.8 Hz), 7.06 (d, 1H, J=4.7 Hz), 6.93 (d, 1H, J=4.7 Hz), 4.59 (m, 1H), 3.94 (s, 3H), 2.64 (m, 1H), 2.01 (m, 1H), 1.66 (m, 2H), 1.50 (m, 1H), 1.41 (s, 3H), 1.14 (s, 3H).

Example 1382

N-{3-[7-(2-Methanesulfonylamino-phenyl)-pyrrolo[2,1-f][1,2,4]triazin-2-ylamino]-phenyl}-acetamide; compound with trifluoro-acetic acid The compound was prepared with a procedure analogous to example 1361 and microwaved at 170° C. for 4 hours to yield a yellow solid, N-{3-[7-(2-Methanesulfonylamino-phenyl)-pyrrolo[2,1-f][1,2,4]triazin-2-ylamino]-phenyl}-acetamide; compound with trifluoro-acetic acid (23 mg, 18%). LCMS: m/z=437.14 (M+H+); 96% pure by HPLC; 1H NMR (400 MHz, DMSO-d6) δ 9.75 (s, 1H), 9.49 (s, 1H), 9.01 (s, 1H), 8.83 (s, 1H), 7.72 (d, 1H, J=7.5 Hz), 7.68 (s, 1H), 7.51 (m, 2H), 7.41 (m, 2H), 7.10 (m, 2H), 7.01 (m, 2H), 2.70 (s, 3H), 2.03 (s, 3H).

Example 1383

N-tert-Butyl-3-{2-[3-(2-oxo-pyrrolidin-1-yl)-phenylamino]-pyrrolo[2,1-f][1,2,4]triazin-7-yl}-benzenesulfonamide; compound with trifluoro-acetic acid The compound was prepared with a procedure analogous to example 1361 and microwaved at 170° C. for 6 hours to yield a yellow solid, N-tert-Butyl-3-{2-[3-(2-oxo-pyrrolidin-1-yl)-phenylamino]-pyrrolo[2,1-f][1,2,4]triazin-7-yl}-benzenesulfonamide; compound with trifluoro-acetic acid (25 mg, 20%). LCMS: m/z=505.17 (M+H+); 1H NMR (400 MHz, DMSO-d6) δ 9.57 (s, 1H), 9.06 (s, 1H), 8.40 (m, 2H), 7.86 (m, 2H), 7.68 (m, 1H), 7.61 (m, 1H), 7.55 (m, 1H), 7.33 (m, 2H), 7.19 (d, 1H, J=4.8 Hz), 7.01 (d, 1H, J=4.8 Hz), 3.66 (m, 2H), 2.47 (m, 2H), 2.00 (m, 2H), 1.11 (s, 9H).

Example 1384

3-[7-(3-tert-Butylsulfamoyl-phenyl)-pyrrolo[2,1-f][1,2,4]triazin-2-ylamino]-N-methyl-benzamide; compound with trifluoro-acetic acid The compound was prepared with a procedure analogous to example 1361 and microwaved at 170° C. for 6 hours to yield a yellow solid, 3-[7-(3-tert-Butylsulfamoyl-phenyl)-pyrrolo[2,1-f][1,2,4]triazin-2-ylamino]-N-methyl-benzamide; compound with trifluoro-acetic acid (41 mg, 35%). LCMS: m/z=479.13 (M+H+); 1H NMR (400 MHz, DMSO-d6) δ 9.66 (s, 1H), 9.07 (s, 1H), 8.54 (d, 1H, J=7.9 Hz), 8.44 (m, 1H), 8.32 (m, 1H), 8.12 (s, 1H), 7.93 (m, 1H), 7.83 (d, 1H, J=7.9 Hz), 7.70 (m, 1H), 7.61 (s, 1H), 7.41 (m, 2H), 7.24 (d, 1H, J=4.8 Hz), 7.03 (d, 1H, J=4.8 Hz), 2.78 (d, 3H, J=4.5 Hz), 1.11 (s, 9H).

Example 1385

N-{3-[7-(3-tert-Butylsulfamoyl-phenyl)-pyrrolo[2,1-f][1,2,4]triazin-2-ylamino]-phenyl}-isobutyramide; compound with trifluoro-acetic acid The compound was prepared with a procedure analogous to example 1361 and microwaved at 170° C. for 8 hours to yield a yellow solid, N-{3-[7-(3-tert-Butylsulfamoyl-phenyl)-pyrrolo[2,1-f][1,2,4]triazin-2-ylamino]-phenyl}-isobutyramide; compound with trifluoro-acetic acid (35 mg, 26%). LCMS: m/z=507.16 (M+H+); 1H NMR (400 MHz, DMSO-d6) δ 9.73 (s, 1H), 9.49 (s, 1H), 9.05 (s, 1H), 8.52 (d, 1H, J=8.0 Hz), 8.47 (m, 1H), 7.81 (m, 2H), 7.66 (m, 1H), 7.59 (m, 2H), 7.24 (m, 3H), 7.00 (d, 1H, J=4.8 Hz), 2.61 (m, 1H), 1.10 (m, 15H).

Example 1386

N-tert-Butyl-3-[2-(3-pyrazol-1-yl-phenylamino)-pyrrolo[2,1-f][1,2,4]triazin-7-yl]-benzenesulfonamide; compound with trifluoro-acetic acid The compound was prepared with a procedure analogous to example 1361 and microwaved at 170° C. for 8 hours to yield a yellow solid, N-tert-Butyl-3-[2-(3-pyrazol-1-yl-phenylamino)-pyrrolo[2,1-f][1,2,4]triazin-7-yl]-benzenesulfonamide; compound with trifluoro-acetic acid (27 mg, 22%). LCMS: m/z=488.14 (M+H+); 1H NMR (400 MHz, DMSO-d6) δ 9.74 (s, 1H), 9.08 (s, 1H), 8.47 (d, 1H, J=7.9 Hz), 8.43 (m, 1H), 8.29 (d, 1H, J=2.2 Hz), 8.16 (m, 1H), 7.80 (d, 1H, J=7.8 Hz), 7.75 (m, 2H), 7.61 (s, 1H), 7.53 (m, 1H), 7.46 (m, 1H), 7.39 (m, 1H), 7.22 (d, 1H, J=4.7 Hz), 7.04 (d, 1H, J=4.7 Hz), 6.53 (m, 1H), 1.11 (s, 9H).

Example 1387

N-{2-tert-Butyl-5-[7-(3-tert-butylsulfamoyl-phenyl)-pyrrolo[2,1-f][1,2,4]triazin-2-ylamino]-phenyl}-acetamide; compound with trifluoro-acetic acid The compound was prepared with a procedure analogous to example 1361 and microwaved at 170° C. for 4 hours to yield a yellow solid, N-{2-tert-Butyl-5-[7-(3-tert-butylsulfamoyl-phenyl)-pyrrolo[2,1-f][1,2,4]triazin-2-ylamino]-phenyl}-acetamide; compound with trifluoro-acetic acid (8 mg, 5%). LCMS: m/z=535.21 (M+H+); 1H NMR (400 MHz, CDCl3) δ 9.46 (br s, 1H), 9.00 (s, 1H), 8.67 (s, 1H), 8.17 (s, 1H), 8.04 (d, 1H, J=7.9 Hz), 7.95 (d, 1H, J=7.9 Hz), 7.84 (d, 1H, J=2.1 Hz), 7.64 (m, 1H), 7.43 (d, 1H, J=8.6 Hz), 7.21 (m, 1H), 7.15 (d, 1H, J=5.1 Hz), 4.34 (br s, 1H), 2.07 (s, 3H), 1.40 (s, 9H), 1.10 (s, 9H).

Example 1388

3-[2-(1-Acetyl-3,3-dimethyl-2,3-dihydro-1H-indol-6-ylamino)-pyrrolo[2,1-f][1,2,4]triazin-7-yl]-N-tert-butyl-benzenesulfonamide; compound with trifluoro-acetic acid The compound was prepared with a procedure analogous to example 1361 and microwaved at 170° C. for 6 hours to yield a brown solid, 3-[2-(1-Acetyl-3,3-dimethyl-2,3-dihydro-1H-indol-6-ylamino)-pyrrolo[2,14][1,2,4]triazin-7-yl]-N-tert-butyl-benzenesulfonamide; compound with trifluoro-acetic acid (61 mg, 44%). LCMS: m/z=533.21 (M+H+); 1H NMR (400 MHz, DMSO-d6) δ 9.42 (s, 1H), 9.02 (s, 1H), 8.51 (d, 1H, J=7.9 Hz), 8.45 (s, 1H), 8.23 (s, 1H), 7.80 (d, 1H, J=7.8 Hz), 7.65 (m, 1H), 7.59 (m, 2H), 7.21 (m, 2H), 6.99 (d, 1H, J=4.8 Hz), 3.87 (s, 2H), 2.17 (s, 3H), 1.30 (s, 6H), 1.11 (s, 9H).

Example 1389

N-{3-[7-(1-Methyl-1H-pyrazol-4-yl)-pyrrolo[2,1-f][1,2,4]triazin-2-ylamino]-phenyl}-methanesulfonamide; compound with trifluoro-acetic acid The compound was prepared with a procedure analogous to example 1361 and microwaved at 170° C. for 4 hours to yield a brown solid, N-{3-[7-(1-Methyl-1H-pyrazol-4-yl)-pyrrolo[2,1-f][1,2,4]triazin-2-ylamino]-phenyl}-methanesulfonamide; compound with trifluoro-acetic acid (53 mg, 27%). LCMS: m/z=384.14 (M+H+); 1H NMR (400 MHz, DMSO-d6) δ 9.76 (s, 1H), 9.45 (s, 1H), 8.89 (s, 1H), 8.45 (s, 1H), 8.16 (s, 1H), 7.63 (m, 1H), 7.49 (m, 1H), 7.32 (m, 1H), 7.10 (d, 1H, J=4.7 Hz), 6.93 (d, 1H, J=4.7 Hz), 6.89 (m, 1H), 3.95 (s, 3H), 3.01 (s, 3H).

Example 1390

3-[7-(3-tert-Butylsulfamoyl-phenyl)-pyrrolo[2,1-f][1,2,4]triazin-2-ylamino]-benzamide; compound with trifluoro-acetic acid The compound was prepared with a procedure analogous to example 1361 and microwaved at 170° C. for 4 hours to yield a brown solid, 3-[7-(3-tert-Butylsulfamoyl-phenyl)-pyrrolo[2,1-f][1,2,4]triazin-2-ylamino]-benzamide; compound with trifluoro-acetic acid (17 mg, 12%). LCMS: m/z=465.09 (M+H+); 1H NMR (400 MHz, DMSO-d6) δ 9.58 (s, 1H), 9.00 (s, 1H), 8.49 (d, 1H, J=7.8 Hz), 8.38 (s, 1H), 8.08 (s, 1H), 7.89 (m, 2H), 7.75 (d, 1H, J=8.0 Hz), 7.68 (m, 1H), 7.55 (s, 1H), 7.39 (m, 3H), 7.17 (d, 1H, J=4.8 Hz), 6.96 (d, 1H, J=4.8 Hz), 1.05 (s, 9H).

Example 1391

N-tert-Butyl-3-[2-(3-[1,2,4]triazol-4-yl-phenylamino)-pyrrolo[2,1-f][1,2,4]triazin-7-yl]-benzenesulfonamide; compound with trifluoro-acetic acid The compound was prepared with a procedure analogous to example 1361 and microwaved at 170° C. for 10 hours to yield a brown solid, N-tert-Butyl-3-[2-(3-[1,2,4]triazol-4-yl-phenylamino)-pyrrolo[2,1-f][1,2,4]triazin-7-yl]-benzenesulfonamide; compound with trifluoro-acetic acid (8 mg, 6%). LCMS: m/z=489.15 (M+H+); 1H NMR (400 MHz, CDCl3) δ 8.78 (s, 1H), 8.53 (m, 1H), 8.45 (s, 2H), 8.15 (m, 1H), 7.97 (m, 1H), 7.89 (d, 1H, J=7.9 Hz), 7.61 (m, 1H), 7.51 (m, 1H), 7.41 (m, 1H), 7.09 (d, 1H, J=4.8 Hz), 7.01 (m, 1H), 6.96 (d, 1H, J=4.8 Hz), 1.25 (s, 9H).

Example 1392

[3-(4-Methyl-piperazin-1-yl)-phenyl]-[7-(3-morpholin-4-yl-phenyl)-pyrrolo[2,1-f][1,2,4]triazin-2-yl]-amine; compound with 2 trifluoro-acetic acids The compound was prepared with a procedure analogous to example 1361 and microwaved at 170° C. for 5 hours to yield a brown solid, [3-(4-Methyl-piperazin-1-yl)-phenyl]-[7-(3-morpholin-4-yl-phenyl)-pyrrolo[2,1-f][1,2,4]triazin-2-yl]-amine; compound with 2 trifluoro-acetic acids (33 mg, 23%). LCMS: m/z=470.21 (M+H+); 1H NMR (400 MHz, CDCl3) δ 8.69 (s, 1H), 7.79 (s, 1H), 7.54 (d, 1H, J=7.7 Hz), 7.46 (m, 1H), 7.28 (m, 2H), 7.24 (m, 1H), 7.17 (m, 4H), 6.60 (d, 1H, J=8.0 Hz), 3.82 (m, 4H), 3.51 (m, 4H), 3.18 (m, 6H), 2.96 (m, 2H), 2.85 (s, 3H).

Example 1393

N-tert-Butyl-3-[2-(3-morpholin-4-yl-phenylamino)-pyrrolo[2,1-f][1,2,4]triazin-7-yl]-benzenesulfonamide; compound with trifluoro-acetic acid The compound was prepared with a procedure analogous to example 1361 and microwaved at 200° C. for 1 hours to yield a yellow solid, N-tert-Butyl-3-[2-(3-morpholin-4-yl-phenylamino)-pyrrolo[2,1-f][1,2,4]triazin-7-yl]-benzenesulfonamide; compound with trifluoro-acetic acid (49 mg, 38%). LCMS: m/z=507.18 (M+H+); 1H NMR (400 MHz, DMSO-d6) δ 9.40 (br s, 1H), 9.04 (s, 1H), 8.42 (m, 2H), 7.85 (d, 1H, J=7.9 Hz), 7.71 (m, 1H), 7.62 (s, 1H), 7.34 (d, 1H, J=8.1 Hz), 7.29 (s, 1H), 7.23 (m, 1H), 7.18 (d, 1H, J=4.7 Hz), 7.00 (d, 1H, J=4.7 Hz), 6.62 (m, 1H), 3.70 (m, 4H), 3.02 (m, 4H), 1.12 (s, 9H).

Example 1394

N-tert-Butyl-3-[2-(4-fluoro-3-morpholin-4-yl-phenylamino)-pyrrolo[2,1-f][1,2,4]triazin-7-yl]-benzenesulfonamide; compound with trifluoro-acetic acid The compound was prepared with a procedure analogous to example 1361 and microwaved at 200° C. for 1 hour to yield a brown solid, N-tert-Butyl-3-[2-(4-fluoro-3-morpholin-4-yl-phenylamino)-pyrrolo[2,1-f][1,2,4]triazin-7-yl]-benzenesulfonamide; compound with trifluoro-acetic acid (8 mg, 6%). LCMS: m/z=525.16 (M+H+); HPLC; 1H NMR (400 MHz, DMSO-d6) δ 9.38 (s, 1H), 8.97 (s, 1H), 8.40 (s, 1H), 8.26 (d, 1H, J=7.9 Hz), 7.78 (d, 1H, J=7.9 Hz), 7.65 (m, 1H), 7.56 (s, 1H), 7.41 (m, 1H), 7.19 (m, 1H), 7.10 (d, 1H, J=4.7 Hz), 7.05 (m, 1H), 6.93 (d, 1H, J=4.7 Hz), 3.62 (m, 4H), 2.83 (m, 4H), 1.04 (s, 9H).

Example 1395

N-tert-Butyl-3-[2-(3-fluoro-4-morpholin-4-yl-phenylamino)-pyrrolo[2,1-f][1,2,4]triazin-7-yl]-benzenesulfonamide; compound with trifluoro-acetic acid The compound was prepared with a procedure analogous to example 1361 and microwaved at 200° C. for 1.5 hours to yield a brown solid, N-tert-Butyl-3-[2-(3-fluoro-4-morpholin-4-yl-phenylamino)-pyrrolo[2,1-f][1,2,4]triazin-7-yl]-benzenesulfonamide; compound with trifluoro-acetic acid (35 mg, 28%). LCMS: m/z=525.16 (M+H+); 1H NMR (400 MHz, DMSO-d6) δ 9.53 (s, 1H), 8.97 (s, 1H), 8.37 (m, 2H), 7.79 (d, 1H, J=7.8 Hz), 7.66 (m, 1H), 7.52 (m, 3H), 7.13 (d, 1H, J=4.7 Hz), 7.01 (m, 1H), 6.94 (d, 1H, J=4.8 Hz), 3.68 (m, 4H), 2.89 (m, 4H), 1.05 (s, 9H).

Example 1396

N-tert-Butyl-3-[2-(3-methoxy-phenylamino)-pyrrolo[2,1-f][1,2,4]triazin-7-yl]-benzenesulfonamide; compound with trifluoro-acetic acid The compound was prepared with a procedure analogous to example 1361 and microwaved at 200° C. for 1 hour to yield a yellow solid, N-tert-Butyl-3-[2-(3-methoxy-phenylamino)-pyrrolo[2,1-f][1,2,4]triazin-7-yl]-benzenesulfonamide; compound with trifluoro-acetic acid (37 mg, 32%). LCMS: m/z=452.16 (M+H+); 1H NMR (400 MHz, DMSO-d6) δ 9.30 (s, 1H), 8.84 (s, 1H), 8.26 (d, 1H, J=7.9 Hz), 8.22 (s, 1H), 7.63 (d, 1H, J=8.0 Hz), 7.50 (m, 1H), 7.39 (s, 1H), 7.20 (d, 1H, J=8.1 Hz), 7.09 (m, 1H), 7.04 (m, 1H), 6.99 (d, 1H, J=4.8 Hz), 6.80 (d, 1H, J=4.8 Hz), 6.34 (m, 1H), 0.90 (s, 9H).

Example 1397

(2-{2-[3-Fluoro-4-(4-methyl-piperazin-1-yl)-phenylamino]-pyrrolo[2,1-f][1,2,4]triazin-7-yl}-phenoxy)-acetic acid 2-methoxy-1-methyl-ethyl ester; compound with 2 trifluoroacetic acids 1397a) Palladium Acetate (0.365 g, 0.00162 mol) and Triphenylphosphine (0.442 g, 0.00168 mol) were dissolved in Tetrahydrofuran (20 mL, 0.3 mol) and the mixture was stirred at room temperature for 10 minutes. 7-Bromo-2-methylsulfanyl-pyrrolo[2,1-f][1,2,4]triazine (1.943 g, 0.007959 mol) was added and the reaction was stirred for another 10 minutes. 2-hydroxyphenyl boronic acid (3.09 g, 0.022 mol) was added followed by saturated sodium carbonate solution (7.6 mL) and Ethanol (20 mL, 0.4 mol;). The reaction mixture was heated at 80° C. for 2 days. Brine was poured into the reaction mixture and organics were extracted three times into ethyl acetate. Combined organic layers were dried over sodium sulfate, filtered, concentrated and purified by normal phase silica gel chromatography eluting with ethyl acetate/heptane to yield a yellow solid, 2-(2-Methylsulfanyl-pyrrolo[2,1-f][1,2,4]triazin-7-yl)-phenol (1.92 g, 94%). LCMS: m/z=258.02 (M+H+); 1H NMR (400 MHz, DMSO-d6) δ 9.84 (s, 1H), 8.97 (s, 1H), 7.87 (m, 1H), 7.22 (d, 1H, J=4.7 Hz), 7.12 (m, 1H), 7.05 (d, 1H, J=4.7 Hz), 7.01 (d, 1H, J=7.8 Hz), 6.93 (m, 1H), 2.47 (s, 3H).

1397b) 2-(2-Methylsulfanyl-pyrrolo[2,1-f][1,2,4]triazin-7-yl)-phenol (1.915 g, 7.442 mmol) and Methylene chloride (50 mL, 800 mmol) were combined in a flask. m-CPBA 70-75% (70:30, m-Chloroperbenzoic acid:3-Chlorobenzoic acid, 1.835 g, 7.444 mmol) was added over 10 minutes. The reaction was stirred at room temperature for 10 minutes. Reaction was concentrated and purified by normal phase silica gel chromatography eluting with ethyl acetate to obtain a brown solid, 2-(2-Methanesulfinyl-pyrrolo[2,1-f][1,2,4]triazin-7-yl)-phenol (1.2 g, 60%). LCMS: m/z=274.01 (M+H+); 1H NMR (400 MHz, DMSO-d6) δ 9.98 (br s, 1H), 9.29 (s, 1H), 7.80 (m, 1H), 7.46 (d, 1H, J=4.7 Hz), 7.30 (m, 2H), 7.03 (d, 1H, J=8.2 Hz), 6.96 (m, 1H), 2.93 (s, 3H).

1397c) 2-(2-Methanesulfinyl-pyrrolo[2,1-f][1,2,4]triazin-7-yl)-phenol (1.214 g, 4.442 mmol), Acetic acid, bromo-, 1,1-dimethylethyl ester (0.780 mL, 5.32 mmol), Potassium carbonate (1.239 g, 8.965 mmol), and Acetonitrile (40 mL, 800 mmol) were combined in a round bottom flask and heated at 60° C. for 3 hours. The solid was filtered through Celite and washed with DCM. The filtrate was concentrated and purified by normal phase silica gel chromatography eluting with methanol/dichloromethane to obtain a brown solid (1.25 g, 72%). LCMS: m/z=388.06 (M+H+); 1H NMR (400 MHz, DMSO-d6) δ 9.30 (s, 1H), 9.29 (s, 1H), 7.87 (d, 1H, J=7.6 Hz), 7.54 (d, 1H, J=4.7 Hz), 7.46 (m, 1H), 7.31 (d, 1H, J=4.7 Hz), 7.15 (m, 2H), 4.74 (s, 2H), 2.91 (s, 3H), 1.40 (s, 9H).

1397d) 3-Fluoro-4-(4-methyl-piperazin-1-yl)-phenylamine and [2-(2-Methanesulfinyl-pyrrolo[2,1-f][1,2,4]triazin-7-yl)-phenoxy]-acetic acid tert-butyl ester were reacted with a procedure analogous to example 1361 and microwaved at 200° C. for 1 hour to yield a brown solid, (2-{2-[3-Fluoro-4-(4-methyl-piperazin-1-yl)-phenylamino]-pyrrolo[2,1-f][1,2,4triazin-7-yl}-phenoxy)-acetic acid 2-methoxy-1-methyl-ethyl ester; compound with 2 trifluoroacetic acids (55 mg, 14%). LCMS: m/z=549.19 (M+H+); 1H NMR (400 MHz, DMSO-d6) δ 9.74 (br s, 1H), 9.55 (s, 1H), 8.97 (s, 1H), 7.97 (m, 1H), 7.81 (m, 1H), 7.43 (m, 1H), 7.29 (d, 1H), 7.13 (m, 4H), 6.97 (m, 2H), 5.01 (m, 1H), 4.82 (s, 2H), 3.32 (d, 2H), 3.20 (m, 5H), 2.96 (m, 3H), 2.87 (m, 4H), 1.10 (d, 3H).

Example 1398

N-{5-[7-(3-tert-Butylsulfamoyl-phenyl)-pyrrolo[2,1-f][1,2,4]triazin-2-ylamino]-2-methyl-phenyl}-acetamide; compound with trifluoro-acetic acid The compound was prepared with a procedure analogous to example 1361 and microwaved at 200° C. for 1 hour to yield a brown solid, N-{5-[7-(3-tert-Butylsulfamoyl-phenyl)-pyrrolo[2,1-f][1,2,4]triazin-2-ylamino]-2-methyl-phenyl}-acetamide; compound with trifluoro-acetic acid (33 mg, 28%). LCMS: m/z=493.16 (M+H+); 1H NMR (400 MHz, DMSO-d6) δ 9.48 (s, 1H), 9.30 (s, 1H), 9.03 (s, 1H), 8.52 (d, 1H, J=7.8 Hz), 8.40 (m, 1H), 7.84 (d, 1H, J=7.9 Hz), 7.70 (m, 2H), 7.61 (s, 1H), 7.51 (d, 1H, J=8.1 Hz), 7.19 (m, 2H), 7.00 (d, 1H, J=4.8 Hz), 2.13 (s, 3H), 2.04 (s, 3H), 1.12 (s, 9H).

Example 1399

4-[7-(3-tert-Butylsulfamoyl-phenyl)-pyrrolo[2,1-f][1,2,4]triazin-2-ylamino]-benzamide; compound with trifluoro-acetic acid The compound was prepared with a procedure analogous to example 1361 and microwaved at 200° C. for 2 hours to yield a brown solid, 4-[7-(3-tert-Butylsulfamoyl-phenyl)-pyrrolo[2,1-f][1,2,4]triazin-2-ylamino]-benzamide; compound with trifluoro-acetic acid (7 mg, 6%). LCMS: m/z=465.18 (M+H+); 1H NMR (400 MHz, DMSO-d6) δ 9.83 (s, 1H), 9.08 (s, 1H), 8.46 (m, 2H), 7.82 (m, 7H), 7.62 (s, 1H), 7.24 (d, 1H, J=4.8 Hz), 7.16 (br s, 1H), 7.05 (d, 1H, J=4.8 Hz), 1.12 (s, 9H).

Example 1400

N-tert-Butyl-3-[2-(4-chloro-phenylamino)-pyrrolo[2,1-f][1,2,4]triazin-7-yl]-benzenesulfonamide; compound with trifluoro-acetic acid The compound was prepared with a procedure analogous to example 1361 and microwaved at 200° C. for 1 hour to yield a brown solid, N-tert-Butyl-3-[2-(4-chloro-phenylamino)-pyrrolo[2,1-f][1,2,4]triazin-7-yl]-benzenesulfonamide; compound with trifluoro-acetic acid (18 mg, 16%). LCMS: m/z=456.15 (M+H+); 1H NMR (400 MHz, DMSO-d6) δ 9.71 (s, 1H), 9.04 (s, 1H), 8.60 (s, 1H), 8.24 (d, 1H, J=7.9 Hz), 7.87 (d, 1H, J=8.0 Hz), 7.77 (m, 3H), 7.64 (s, 1H), 7.37 (d, 2H, J=8.9 Hz), 7.21 (d, 2H, J=4.8 Hz), 7.01 (d, 2H, J=4.8 Hz), 1.11 (s, 9H).

Example 1401

(2-{2-[3-Fluoro-4-(4-methyl-piperazin-1-yl)-phenylamino]-pyrrolo[2,1-f][1,2,4]triazin-7-yl}-phenoxy)-acetic acid; compound with 2 trifluoroacetic acids (2-{2-[3-Fluoro-4-(4-methyl-piperazin-1-yl)-phenylamino]-pyrrolo[2,1-f][1,2,4]triazin-7-yl}-phenoxy)-acetic acid 2-methoxy-1-methyl-ethyl ester; compound with 2 trifluoroacetic acids (0.040 g, 0.052 mmol), Lithium hydroxide monohydrate (0.059 g, 1.4 mmol), Water (8.0 mL, 440 mmol) and Tetrahydrofuran (8.0 mL, 99 mmol) were combined and heated at 70° C. for 17 hours. The reaction was concentrated and purified on preparatory HPLC and lyophilized to yield a brown solid, (2-{2-[3-Fluoro-4-(4-methyl-piperazin-1-yl)-phenylamino]-pyrrolo[2,1-f][1,2,4]triazin-7-yl}-phenoxy)-acetic acid; compound with 2 trifluoroacetic acids (9 mg, 24%). LCMS: m/z=477.14 (M+H+); 1H NMR (400 MHz, DMSO-d6) δ 8.68 (br s, 1H), 9.55 (s, 1H), 8.97 (s, 1H), 7.99 (d, 1H, J=7.6 Hz), 7.83 (m, 1H), 7.42 (m, 1H), 7.30 (d, 1H, J=8.8 Hz), 7.14 (m, 2H), 7.09 (d, 1H, J=8.4 Hz), 7.00 (m, 1H), 6.95 (d, 1H, J=4.6 Hz), 4.75 (s, 2H), 3.40 (m, 4H), 3.21 (m, 2H), 2.96 (m, 2H), 2.87 (s, 3H).

Example 1402

N-tert-Butyl-3-[2-(4-oxazol-5-yl-phenylamino)-pyrrolo[2,1-f][1,2,4]triazin-7-yl]-benzenesulfonamide; compound with trifluoro-acetic acid The compound was prepared with a procedure analogous to example 1361 and microwaved at 200° C. for 1 hour to yield a brown solid, N-tert-Butyl-3-[2-(4-oxazol-5-yl-phenylamino)-pyrrolo[2,1-f][1,2,4]triazin-7-yl]-benzenesulfonamide; compound with trifluoro-acetic acid (5 mg, 4%). LCMS: m/z=489.13 (M+H+); 1H NMR (400 MHz, DMSO-d6) δ 9.82 (s, 1H), 9.08 (s, 1H), 8.59 (s, 1H), 8.40 (s, 1H), 8.35 (d, 1H, J=7.9 Hz), 7.89 (m, 3H), 7.79 (m, 1H), 7.73 (m, 2H), 7.66 (s, 1H), 7.51 (m, 1H), 7.24 (d, 1H, J=4.8 Hz), 7.04 (d, 1H, J=4.8 Hz), 1.13 (s, 9H).

Example 1403

N,N-Dimethyl-2-(2-{2-[4-(4-methyl-piperazin-1-yl)-phenylamino]-pyrrolo[2,1-f][1,2,4]triazin-7-yl}-phenoxy)-acetamide; compound with 2 trifluoro-acetic acids 1403a) [2-(2-Methanesulfinyl-pyrrolo[2,1-f][1,2,4]triazin-7-yl)-phenoxy]-acetic acid tert-butyl ester (0.298 g, 0.769 mmol), Methylene chloride (11 mL, 170 mmol), and Trifluoroacetic Acid (2.20 mL, 28.5 mmol) were combined and stirred for 18 hours. The product was extracted into dichloromethane and purified by normal phase silica gel chromatography eluting with methanol/dichloromethane to yield a brown solid, [2-(2-Methanesulfinyl-pyrrolo[2,1-f][1,2,4]triazin-7-yl)-phenoxy]-acetic acid (197 mg, 77%). LCMS: m/z=332.06 (M+H+); 1H NMR (400 MHz, DMSO-d6) δ 9.30 (s, 1H), 7.86 (d, 1H, J=7.6 Hz), 7.54 (d, 1H, J=4.7 Hz), 7.46 (m, 1H), 7.31 (d, 1H, J=4.7 Hz), 7.14 (m, 2H), 4.77 (s, 2H), 2.92 (s, 3H).

1403b) [2-(2-Methanesulfinyl-pyrrolo[2,1-f][1,2,4]triazin-7-yl)-phenoxy]-acetic acid (197 mg, 0.000594 mol), 2.0 M of Dimethylamine in Tetrahydrofuran (0.400 mL, 0.000800 mol) N-(3-Dimethylaminopropyl)-N'-ethylcarbodiimide hydrochloride (0.147 g, 0.000767 mol) 1-Hydroxybenzotriazole (0.109 g, 0.000807 mol), 4-Methylmorpholine (0.0850 mL, 0.000773 mol) and N,N-Dimethylformamide (4.9 mL, 0.063 mol) were combined and stirred for 2.5 hours. The reaction was concentrated and purified by normal phase silica gel chromatography eluting with dichloromethane/methanol/ammonium hydroxide to yield a brown solid, 2-[2-(2-Methanesulfinyl-pyrrolo[2,1-f][1,2,4]triazin-7-yl)-phenoxy]-N,N-dimethyl-acetamide (162 mg, 76%). LCMS: m/z=359.13 (M+H+); 1H NMR (400 MHz, DMSO-d6) δ 9.29 (s, 1H), 7.89 (d, 1H, J=7.6 Hz), 7.62 (d, 1H, J=4.7 Hz), 7.44 (m, 1H), 7.30 (d, 1H, J=4.7 Hz), 7.18 (d, 1H, J=8.4 Hz), 7.13 (m, 1H), 4.94 (s, 2H), 2.94 (s, 3H), 2.92 (s, 3H), 2.82 (s, 3H).

1403c) The compound was prepared with a procedure analogous to example 1361 and microwaved at 200° C. for 1 hour to yield a brown solid, N,N-Dimethyl-2-(2-{2-[4-(4-methyl-piperazin-1-yl)-phenylamino]-pyrrolo[2,1-f][1,2,4]triazin-7-yl}-phenoxy)-acetamide; compound with 2 trifluoro-acetic acids (45 mg, 37%). 1H NMR (400 MHz, DMSO-d6) δ 9.76 (br s, 1H), 9.24 (s, 1H), 8.92 (s, 1H), 8.06 (d, 1H, J=6.4 Hz), 7.64 (d, 2H, J=9.0 Hz), 7.38 (m, 1H), 7.20 (d, 1H, J=4.7 Hz), 7.13 (m, 2H), 6.91 (m, 3H), 4.90 (s, 2H), 3.71 (m, 4H), 3.52 (m, 2H), 3.16 (m, 2H), 2.92 (s, 3H), 2.87 (s, 3H), 2.81 (s, 3H).

Example 1404

2-(2-{2-[3-Fluoro-4-(4-methyl-piperazin-1-yl)-phenylamino]-pyrrolo[2,1-f][1,2,4]triazin-7-yl}-phenoxy)-N,N-dimethyl-acetamide; compound with 2 trifluoroacetic acids The compound was prepared with a procedure analogous to example 1361 and microwaved at 200° C. for 1 hour to yield a yellow solid, 2-(2-{2-[3-Fluoro-4-(4-methyl-piperazin-1-yl)-phenylamino]-pyrrolo[2,1-f][1,2,4]triazin-7-yl}-phenoxy)-N,N-dimethyl-acetamide; compound with 2 trifluoroacetic acids (63 mg, 40%). LCMS: m/z=504.19 (M+H+); 1H NMR (400 MHz, DMSO-d6) δ 9.79 (br s, 1H), 9.55 (s, 1H), 8.96 (s, 1H), 8.00 (d, 1H, J=7.6 Hz), 7.82 (m, 1H), 7.40 (m, 1H), 7.31 (m, 1H), 7.20 (d, 1H, J=4.7 Hz), 7.12 (m, 2H), 7.00 (m, 1H), 6.94 (d, 1H, J=4.7 Hz), 4.90 (s, 2H), 3.50 (d, 2H, J=11.8 Hz), 3.40 (d, 2H, J=12.7 Hz), 3.21 (m, 2H), 2.96 (m, 2H), 2.92 (s, 3H), 2.87 (s, 3H), 2.80 (s, 3H).

Example 1405

[7-(6-Methoxy-pyridin-3-yl)-pyrrolo[2,1-f][1,2,4]triazin-2-yl]-(4-pyrrolidin-1-ylmethyl-phenyl)-amine; compound with 2 trifluoro-acetic acids The compound was prepared with a procedure analogous to example 1361 and microwaved at 200° C. for 1 hour to yield a yellow solid, [7-(6-Methoxy-pyridin-3-yl)-pyrrolo[2,1-f][1,2,4]triazin-2-yl]-(4-pyrrolidin-1-ylmethyl-phenyl)-amine; compound with 2 trifluoro-acetic acids (14 mg, 9%). LCMS: m/z=401.0 (M+H+); 1H NMR (400 MHz, DMSO-d6) δ 9.82 (br s, 1H), 9.74 (s, 1H), 9.03 (s, 1H), 8.90 (m, 1H), 8.49 (m, 1H), 7.81 (d, 2H, J=8.4 Hz), 7.44 (d, 2H, J=8.4 Hz), 7.20 (d, 1H, J=4.8 Hz), 7.01 (m, 2H), 4.30 (d, 1H, J=5.2 Hz), 3.96 (s, 3H), 3.37 (m, 2H), 3.11 (m, 2H), 2.04 (m, 2H), 1.85 (m, 2H).

Example 1406

{4-[7-(6-Methoxy-pyridin-3-yl)-pyrrolo[2,1-f][1,2,4]triazin-2-ylamino]-phenyl}-morpholin-4-yl-methanone; compound with trifluoro-acetic acid 7-(6-Methoxy-pyridin-3-yl)-pyrrolo[2,1-f][1,2,4]triazin-2-ol (0.0611 g, 0.252 mmol), N-Phenylbis(trifluoromethanesulphonimide) (0.106 g, 0.297 mmol), N,N-Diisopropylethylamine (0.135 mL, 0.775 mmol) and N,N-Dimethylformamide (2.5 mL, 32 mmol) were combined and stirred at room temperature for 1 hour. (4-Amino-phenyl)-morpholin-4-yl-methanone (0.068 g, 0.33 mmol) was added and the reaction was stirred at room temperature for 30 hours. The reaction was concentrated, purified on preparatory HPLC and lyophilized to yield a brown solid, {4-[7-(6-Methoxy-pyridin-3-yl)-pyrrolo[2,1-f][1,2,4]triazin-2-ylamino]-phenyl}-morpholin-4-yl-methanone; compound with trifluoro-acetic acid (4.2 mg, 3%). LCMS: m/z=431.20 (M+H+); 1H NMR (400 MHz, DMSO-d6) δ 9.71 (s, 1H), 8.96 (d, 1H, J=1.9 Hz), 8.85 (m, 1H), 8.42 (m, 1H), 7.72 (d, 2H, J=8.5 Hz), 7.32 (d, 2H, J=8.4 Hz), 7.14 (d, 1H, J=4.7 Hz), 6.98 (d, 1H, J=8.7 Hz), 6.93 (d, 1H, J=4.7 Hz), 3.88 (s, 3H), 3.54 (m, 4H), 3.45 (m, 4H).

Example 1407

2-(4-{7-[7-(3-tert-Butylsulfamoyl-phenyl)-pyrrolo[2,1-f][1,2,4]triazin-2-ylamino]-2-fluoro-phenyl}-piperazin-1-yl)-acetamide; compound with 2 trifluoroacetic acids 1407a) 1-(2-Fluoro-4-nitro-phenyl)-piperazine (0.438 g, 1.94 mmol), Iodoacetamide (0.401 g, 2.17 mmol), Cesium Carbonate (0.956 g, 2.93 mmol) and Acetonitrile (20 mL, 400 mmol) were combined and stirred at 60° C. for 20 hours. The mixture was cooled to room temperature. Water was added to the mixture and the product was extracted into ethyl acetate three times. The extracts were dried over sodium sulfate, filtered and concentrated to yield a yellow solid, 2-[4-(2-Fluoro-4-nitro-phenyl)-piperazin-1-yl]-acetamide (558 mg, 100%). LCMS: m/z=283.06 (M+H+); 1H NMR (400 MHz, DMSO-d6) δ 8.00 (d, 2H), 7.26 (br s, 1H), 7.17 (m, 2H), 2.94 (s, 2H), 2.60 (m, 2H), 2.50 (s, 6H).

1407b) 2-[4-(2-Fluoro-4-nitro-phenyl)-piperazin-1-yl]-acetamide (0.558 g, 0.00198 mol) was combined with Methanol (60 mL, 1 mol) and N,N-Dimethylformamide (10 mL, 0.1 mol). The solution was passed through a 10% Pd/C CatCart (55×4 mm) in an H-cube hydrogenator at 10 bar, 30° C. for 3.5 hours. The reaction was concentrated to yield a yellow solid, 2-[4-(4-Amino-2-fluoro-phenyl)-piperazin-1-yl]-acetamide (485 mg, 97%). LCMS: m/z=253.06 (M+H+); 1H NMR (400 MHz, DMSO-d6) δ 7.14 (d, 2H), 6.76 (m, 1H), 6.31 (m, 2H), 4.97 (br s, 2H), 2.87 (m, 6H), 2.52 (m, 4H).

1407c) N-tert-Butyl-3-(2-hydroxy-pyrrolo[2,1-f][1,2,4]triazin-7-yl)-benzenesulfonamide (0.092 g, 0.26 mmol), N-Phenylbis(trifluoromethanesulphonimide) (0.112 g, 0.314 mmol), N,N-Diisopropylethylamine (0.139 mL, 0.797 mmol) and 1-Methoxy-2-propanol (4.0 mL, 41 mmol) were combined in a tube and stirred at room temperature for 18 hours. 2-[4-(4-Amino-2-fluoro-phenyl)-piperazin-1-yl]-acetamide (0.087 g, 0.34 mmol) was added and the reaction was stirred at room temperature for 4 days to yield an orange solid, 2-(4-{4-[7-(3-tert-Butylsulfamoyl-phenyl)-pyrrolo[2,1-f][1,2,4]triazin-2-ylamino]-2-fluoro-phenyl}-piperazin-1-yl)-acetamide; compound with 2 trifluoroacetic acids (35 mg, 16%). LCMS: m/z=581.25 (M+H+); 1H NMR (400 MHz, DMSO-d6) δ 9.59 (s, 1H), 8.98 (s, 1H), 8.41 (s, 1H), 8.33 (d, 1H, J=7.9 Hz), 7.95 (s, 1H), 7.80 (d, 1H, J=7.8 Hz), 7.66 (m, 2H), 7.54 (m, 3H), 7.14 (d, 1H, J=4.7 Hz), 7.07 (m, 1H), 6.96 (d, 1H, J=4.7 Hz), 3.95 (s, 2H), 3.5 (m, 2H), 3.31 (m, 4H), 3.09 (m, 2H), 1.05 (s, 9H).

Example 1408

2-[4-(4-{7-[2-(Methanesulfonyl-methyl-amino)-phenyl]-pyrrolo[2,1-f][1,2,4]triazin-2-ylamino}-phenyl)-piperidin-1-yl]-acetamide A mixture of Trifluoro-methanesulfonic acid 7-[2-(methanesulfonyl-methyl-amino)-phenyl]-pyrrolo[2,1-f][1,2,4]triazin-2-yl ester (91 mg, 0.20 mmol), 2-[4-(4-Amino-phenyl)-piperidin-1-yl]-acetamide (192 mg, 0.40 mmol), N,N-Diisopropylethylamine (0.200 mL, 0.574 mmol), and 1-Methoxy-2-propanol (2.0 mL, 20 mmol) was stirred at 50° C. for 24 hours. The reaction was filtered to yield the product, a yellow solid, 2-[4-(4-{7-[2-(Methanesulfonyl-methyl-amino)-phenyl]-pyrrolo[2,1-f][1,2,4]triazin-2-ylamino}-phenyl)-piperidin-1-yl]-acetamide (83 mg, 77%). yellow solid; LCMS: m/z=534.19 (M+H+); 97% pure by HPLC; mp: 170° C.; 1H NMR (400 MHz, DMSO-d6) δ 9.34 (s, 1H), 8.96 (s, 1H), 7.99 (m, 1H), 7.66 (d, 1H, J=7.6 Hz), 7.57 (m, 4H), 7.22 (br s, 1H), 7.14 (br s, 1H), 7.06 (d, 2H, J=8.4 Hz), 6.96 (m, 2H), 3.07 (s, 3H), 2.89 (m, 7H), 2.39 (m, 1H), 2.13 (m, 2H), 1.69 (m, 4H).

Example 1409

2-(2-{2-[4-(1-Methyl-piperidin-4-yl)-phenylamino]-pyrrolo[2,1-f][1,2,4]triazin-7-yl}-phenoxy)-acetamide; compound with 2 trifluoro-acetic acids 1409a) 2-(2-Methanesulfinyl-pyrrolo[2,1-f][1,2,4]triazin-7-yl)-phenol (0.68 g, 2.5 mmol), 2-Bromoacetamide (0.414 g, 3.00 mmol), Potassium carbonate (0.7049 g, 5.100 mmol), and Acetonitrile (20 mL, 500 mmol) were combined in a round bottom flask and heated at 60° C. for 19 hours. The solid was filtered through Celite and washed with DCM. The filtrate was concentrated and purified via normal phase silica gel chromatography eluting with dichloromethane /methanol to yield a yellow solid, 2-[2-(2-Methanesulfinyl-pyrrolo[2,1-f][1,2,4]triazin-7-yl)-phenoxy]-acetamide (719 mg, 87%). LCMS: m/z=331.16 (M+H+); 1H NMR (400 MHz, DMSO-d6) δ 9.31 (s, 1H), 7.75 (m, 1H), 7.50 (m, 2H), 7.36 (br s, 1H), 7.32 (d, 1H, J=4.7 Hz), 7.16 (m, 2H), 7.09 (d, 1H, J=8.4 Hz), 4.52 (s, 2H), 2.92 (s, 3H).

1409b) The compound was prepared with a procedure analogous to general procedure 1 and microwaved at 200° C. for 1 hour to yield a yellow solid, 2-(2-{2-[4-(1-Methyl-piperidin-4-yl)-phenylamino]-pyrrolo[2,1-f][1,2,4]triazin-7-yl}-phenoxy)-acetamide; compound with 2 trifluoro-acetic acids (55 mg, 28%). LCMS: m/z=457.22 (M+H+); 1H NMR (400 MHz, DMSO-d6) δ 9.35 (m, 2H), 8.90 (s, 1H), 7.88 (d, 1H, J=7.6 Hz), 7.60 (d, 1H, J=8.4 Hz), 7.37 (m, 2H), 7.07 (m, 5H), 6.89 (d, 1H, J=4.6 Hz), 4.43 (s, 2H), 2.98 (m, 2H), 2.74 (m, 3H), 2.65 (m, 1H), 1.90 (m, 2H), 1.74 (m, 2H).

Example 1410

N-tert-Butyl-3-{2-[4-(4-methyl-piperazine-1-carbonyl)-phenylamino]-pyrrolo[2,1-f][1,2,4]triazin-7-yl}-benzenesulfonamide; compound with 2 trifluoroacetic acids The compound was prepared with a procedure analogous to example 1406 and heated at 50° C. for 24 hours to yield an orange solid, N-tert-Butyl-3-{2-[4-(4-methyl-piperazine-1-carbonyl)-phenylamino]-pyrrolo[2,1-f][1,2,4]triazin-7-yl}-benzenesulfonamide; compound with 2 trifluoroacetic acids (46 mg, 21%). LCMS: m/z=548.25 (M+H+); 1H NMR (400 MHz, DMSO-d6) δ 9.89 (s, 1H), 9.09 (s, 1H), 8.65 (s, 1H), 8.26 (d, 1H, J=7.8 Hz), 7.86 (m, 3H), 7.75 (m, 1H), 7.64 (s, 1H), 7.47 (d, 2H, J=8.4 Hz), 7.25 (d, 1H, J=4.7 Hz), 7.05 (d, 1H, J=4.7 Hz), 4.25 (m, 2H), 3.29 (m, 4H), 3.10 (m, 2H), 2.84 (s, 3H), 1.10 (s, 9H).

Example 1411

N-tert-Butyl-3-{2-[3-chloro-4-(4-methyl-piperazin-1-yl)-phenylamino]-pyrrolo[2,1-f][1,2,4]triazin-7-yl}-benzenesulfonamide; compound with 2 trifluoroacetic acids The compound was prepared with a procedure analogous to example 1406 and heated at 50° C. for 17 hours to yield an orange solid, N-tert-Butyl-3-{2-[3-chloro-4-(4-methyl-piperazin-1-yl)-phenylamino]-pyrrolo[2,1-f][1,2,4]triazin-7-yl}-benzenesulfonamide; compound with 2 trifluoroacetic acids (30 mg, 15%). LCMS: m/z=554.28 (M+H+); 1H NMR (400 MHz, DMSO-d6) δ 9.85 (br s, 1H), 9.68 (s, 1H), 9.05 (s, 1H), 8.44 (m, 2H), 7.88 (m, 2H), 7.75 (m, 2H), 7.63 (s, 1H), 7.23 (m, 2H), 7.02 (d, 1H, J=4.7 Hz), 3.53 (m, 2H), 3.37 (m, 2H), 3.23 (m, 2H), 2.97 (m, 2H), 2.89 (s, 3H), 1.11 (s, 9H).

Example 1412

N-tert-Butyl-3-(2-{3-fluoro-4-[4-((S)-2-hydroxy-propyl)-piperazin-1-yl]-phenylamino}-pyrrolo[2,1-f][1,2,4]triazin-7-yl)-benzenesulfonamide; compound with 2 trifluoroacetic acids 1412a) 1-(2-Fluoro-4-nitro-phenyl)-piperazine (0.500 g, 0.00222 mol) was dissolved in Methanol (11.0 mL, 0.272 mol) and the reaction mixture was placed in a sealed tube. (S)-(−)-Propylene Oxide (0.235 mL, 0.00335 mol) was then added at room temperature and the reaction was stirred for 19 hours. The reaction was concentrated to yield a yellow solid, (S)-1-[4-(2-Fluoro-4-nitro-phenyl)-piperazin-1-yl]-propan-2-ol (583 mg, 93%). LCMS: m/z=284.10 (M+H+); 1H NMR (400 MHz, DMSO-d6) δ 8.00 (d, 2H, J=11.3 Hz), 7.16 (m, 1H), 4.36 (d, 1H, J=4.0 Hz), 3.80 (m, 1H), 3.28 (m, 4H), 2.57 (m, 4H), 2.26 (m, 2H), 1.06 (d, 3H, J=6.2 Hz).

1412b) (S)-1-[4-(2-Fluoro-4-nitro-phenyl)-piperazin-1-yl]-propan-2-ol (0.583 g, 0.00206 mol) was combined with Methanol (42 mL, 1.0 mol) in a flask. The solution was passed through a 10% Pd/C CatCart (30×4 mm) in an H-cube hydrogenator at 10 bar, 30° C. for 3 hours. The reaction was concentrated and triturated with ether to yield a brown solid, (S)-1-[4-(4-Amino-2-fluoro-phenyl)-piperazin-1-yl]-propan-2-ol (425 mg, 82%). LCMS: m/z=254.09 (M+H+); 1H NMR (400 MHz, DMSO-d6) δ 6.75 (m, 1H), 6.30 (m, 2H), 4.95 (s, 2H), 4.29 (d, 1H, J=3.4 Hz), 3.77 (m, 1H), 2.81 (m, 4H), 2.22 (m, 2H), 1.04 (d, 3H, J=6.1 Hz).

1412c) The compound was prepared with a procedure analogous to example 1406 and heated at 50° C. for 17 hours to yield a yellow solid, N-tert-Butyl-3-(2-{3-fluoro-4-[((S)-2-hydroxy-propyl)-piperazin-1-yl]-phenylamino}-pyrrolo[2,1-f][1,2,4]triazin-7-yl)-benzenesulfonamide; compound with 2 trifluoroacetic acids (35 mg, 17%). LCMS: m/z=582.27 (M+H+); 1H NMR (400 MHz, DMSO-d6) δ 9.65 (m, 2H), 9.04 (s, 1H), 8.48 (s, 1H), 8.38 (d, 1H, J=7.9 Hz), 7.86 (d, 1H, J=7.9 Hz), 7.72 (m, 1H), 7.59 (m, 3H), 7.20 (d, 1H, J=4.7 Hz), 7.13 (d, 1H, J=4.8 Hz), 4.12 (m, 3H), 3.40 (m, 4H), 3.21 (m, 2H), 3.06 (m, 2H), 1.14 (d, 3H, J=6.1 Hz), 1.11 (s, 9H).

Example 1413

2-(4-{4-[7-(6-Methoxy-pyridin-3-yl)-pyrrolo[2,1-f][1,2,4]triazin-2-ylamino]-phenyl}-piperidin-1-yl)-acetamide The compound was prepared with a procedure analogous to example 1408 and heated at 50° C. for 24 hours. The solid was filtered off and dried to yield a yellow solid, 2-(4-{4-[7-(6-Methoxy-pyridin-3-yl)-pyrrolo[2,1-f][1,2,4]triazin-2-ylamino]-phenyl}-piperidin-1-yl)-acetamide (42 mg, 35%). LCMS: m/z=458.23 (M+H+); mp: 217° C.; 1H NMR (400 MHz, DMSO-d6) δ 9.41 (s, 1H), 8.97 (s, 1H), 8.90 (d, 2H, J=1.8 Hz), 8.51 (m, 1H), 7.64 (d, 2H, J=8.4 Hz), 7.17 (m, 5H), 7.01 (d, 1H, J=8.7 Hz), 6.95 (d, 1H, J=4.7 Hz), 3.94 (s, 3H), 2.89 (m, 4H), 2.44 (m, 1H), 2.15 (m, 2H), 1.72 (m, 4H).

Example 1414

2-(4-{2-Fluoro-4-[7-(6-methoxy-pyridin-3-yl)-pyrrolo[2,1-f][1,2,4]triazin-2-ylamino]-phenyl}-piperazin-1-yl)-acetamide The compound was prepared with a procedure analogous to example 1408 and heated at 50° C. for 17 hours. The solid was filtered off and dried to yield a yellow solid, 2-(4-{2-Fluoro-4-[7-(6-methoxy-pyridin-3-yl)-pyrrolo[2,1-f][1,2,4]triazin-2-ylamino]-phenyl}-piperazin-1-yl)-acetamide (62 mg, 49%). LCMS: m/z=477.21 (M+H+); mp: 217° C.; 1H NMR (400 MHz, DMSO-d6) δ 9.48 (s, 1H), 8.91 (s, 1H), 8.79 (s, 1H), 8.43 (m, 1H), 7.61 (d, 2H, J=15.4 Hz), 7.29 (d, 1H, J=8.5 Hz), 7.17 (br s, 1H), 7.09 (m, 2H), 6.91 (m, 3H), 3.87 (s, 3H), 2.94 (m, 4H), 2.87 (s, 2H), 2.54 (m, 4H).

Example 1415

2-(4-{2-Fluoro-4-[7-(6-methoxy-pyridin-3-yl)-pyrrolo[2,1-f][1,2,4]triazin-2-ylamino]-phenyl}-piperazin-1-yl)-acetamide The compound was prepared with a procedure analogous to example 1408 and heated at 50° C. for 17 hours. The solid was filtered off and dried to yield a yellow solid, 2-(4-{2-Fluoro-4-[7-(6-methoxy-pyridin-3-yl)-pyrrolo[2,1-f][1,2,4]triazin-2-ylamino]-phenyl}-piperazin-1-yl)-acetamide (62 mg, 49%). LCMS: m/z=477.21 (M+H+); mp: 217° C.; 1H NMR (400 MHz, DMSO-d6) δ 9.48 (s, 1H), 8.91 (s, 1H), 8.79 (s, 1H), 8.43 (m, 1H), 7.61 (d, 2H, J=15.4 Hz), 7.29 (d, 1H, J=8.5 Hz), 7.17 (br s, 1H), 7.09 (m, 2H), 6.91 (m, 3H), 3.87 (s, 3H), 2.94 (m, 4H), 2.87 (s, 2H), 2.54 (m, 4H).

Example 1416

2-(4-{2-Fluoro-4-[7-(2-methoxy-phenyl)-pyrrolo[2,1-f][1,2,4]triazin-2-ylamino]-phenyl}-piperazin-1-yl)-acetamide The compound was prepared with a procedure analogous to example 1408 and heated at 50° C. for 6 days. The solid was filtered off and dried to yield a yellow solid, 2-(4-{2-Fluoro-4-[7-(2-methoxy-phenyl)-pyrrolo[2,1-f][1,2,4]triazin-2-ylamino]-phenyl}-piperazin-1-yl)-acetamide (29 mg, 21%). LCMS: m/z=475.98 (M+H+); mp: 186° C.; 1H NMR (400 MHz, DMSO-d6) δ 9.39 (s, 1H), 8.88 (s, 1H), 7.67 (m, 2H), 7.42 (m, 1H), 7.16 (m, 3H), 7.04 (m, 2H), 6.87 (m, 3H), 3.73 (s, 3H), 2.87 (m, 6H), 2.52 (s, 4H).

Example 1417

(S)-1-(4-{2-Fluoro-4-[7-(2-methoxy-phenyl)-pyrrolo[2,1-f][1,2,4]triazin-2-ylamino]-phenyl}-piperazin-1-yl)-propan-2-ol; compound with 2 trifluoroacetic acids The compound was prepared with a procedure analogous to example 1408 and heated at 50° C. for 5 days to yield a yellow solid, (S)-1-(4-{2-Fluoro-4-[7-(2-methoxy-phenyl)-pyrrolo[2,1-f][1,2,4]triazin-2-ylamino]-phenyl}-piperazin-1-yl)-propan-2-ol; compound with 2 trifluoroacetic acids (57 mg, 29%). LCMS: m/z=477.06 (M+H+); 1H NMR (400 MHz, DMSO-d6) δ 9.56 (m, 2H), 8.96 (s, 1H), 7.80 (m, 2H), 7.48 (m, 1H), 7.27 (d, 1H, J=8.8 Hz), 7.21 (d, 1H, J=8.3 Hz), 7.11 (m, 1H), 6.98 (m, 3H), 4.12 (m, 1H), 3.80 (s, 3H), 3.22 (m, 10H), 1.14 (d, 3H, J=6.1 Hz).

Example 1418

[3-Chloro-4-(4-methyl-piperazin-1-yl)-phenyl]-[7-(2-methoxy-phenyl)-pyrrolo[2,1-f][1,2,4]triazin-2-yl]-amine; compound with 2 trifluoroacetic acids The compound was prepared with a procedure analogous to example 1408 and heated at 50° C. for 5 days to yield an orange solid, [3-Chloro-4-(4-methyl-piperazin-1-yl)-phenyl]-[7-(2-methoxy-phenyl)-pyrrolo[2,1-f][1,2,4]triazin-2-yl]-amine ; compound with 2 trifluoroacetic acids (33 mg, 18%). LCMS: m/z=449.02 (M+H+); 1H NMR (400 MHz, DMSO-d6) δ 9.89 (br s, 1H), 9.56 (s, 1H), 8.97 (s, 1H), 8.04 (s, 1H), 7.75 (d, 1H, J=6.7 Hz), 7.45 (m, 2H), 7.22 (d, 1H, J=8.4 Hz), 7.12 (m, 2H), 6.95 (s, 2H), 3.81 (s, 3H), 3.52 (m, 2H), 3.27 (m, 5H), 2.95 (m, 4H).

Example 1419

[3-Chloro-4-(4-methyl-piperazin-1-yl)-phenyl]-[7-(6-methoxy-pyridin-3-yl)-pyrrolo[2,1-f][1,2,4]triazin-2-yl]-amine; compound with 2 trifluoroacetic acids The compound was prepared with a procedure analogous to example 1408 and heated at 50° C. for 5 days to yield an orange solid, [3-Chloro-4-(4-methyl-piperazin-1-yl)-phenyl]-[7-(6-methoxy-pyridin-3-yl)-pyrrolo[2,1-f][1,2,4]triazin-2-yl]-amine; compound with 2 trifluoroacetic acids (21 mg, 13%). LCMS: m/z=450.00 (M+H+); 1H NMR (400 MHz, DMSO-d6) δ 9.78 (br s, 1H), 9.66 (s, 1H), 9.00 (s, 1H), 8.87 (m, 1H), 8.50 (m, 1H), 8.08 (d, 1H, J=2.0 Hz), 7.51 (m, 1H), 7.20 (m, 2H), 7.00 (m, 2H), 3.94 (s, 3H), 3.5 (m, 2H), 3.38 (m, 2H), 3.22 (m, 2H), 2.98 (m, 2H), 2.90 (s, 3H).

Example 1420

{4-[7-(6-Methoxy-pyridin-3-yl)-pyrrolo[2,1-f][1,2,4]triazin-2-ylamino]-phenyl}-(4-methyl-piperazin-1-yl)-methanone; compound with 2 trifluoroacetic acids The compound was prepared with a procedure analogous to example 1408 and heated at 50° C. for 5 days to yield a yellow solid, {4-[7-(6-Methoxy-pyridin-3-yl)-pyrrolo[2,1-f][1,2,4]triazin-2-ylamino]-phenyl}-(4-methyl-piperazin-1-yl)-methanone; compound with 2 trifluoroacetic acids (53 mg, 36%). LCMS: m/z=444.00 (M+H+); 1H NMR (400 MHz, DMSO-d6) δ 10.04 (br s, 1H), 9.85 (s, 1H), 9.04 (s, 1H), 8.92 (d, 1H, J=1.9 Hz), 8.50 (m, 1H), 7.82 (d, 2H, J=8.5 Hz), 7.44 (d, 2H, J=8.5 Hz), 7.22 (d, 1H, J=4.7 Hz), 7.02 (m, 2H), 3.95 (m, 5H), 3.29 (m, 6H), 2.84 (s, 3H).

Example 1421

N-(2-{2-[3-Fluoro-4-(4-methyl-piperazin-1-yl)-phenylamino]-pyrrolo[2,1-f][1,2,4]triazin-7-yl}-phenyl)-N-methyl-methanesulfonamide; compound with 2 trifluoroacetic acids The compound was prepared with a procedure analogous to example 1408 and heated at 50° C. for 23 hours to yield a yellow solid, N-(2-{2-[3-Fluoro-4-(4-methyl-piperazin-1-yl)-phenylamino]-pyrrolo[2,1-f][1,2,4]triazin-7-yl}-phenyl)-N-methyl-methanesulfonamide; compound with 2 trifluoroacetic acids (39 mg, 29%). LCMS: m/z=510.02 (M+H+); 1H NMR (400 MHz, DMSO-d6) δ 9.85 (br s, 1H), 9.57 (s, 1H), 8.99 (s, 1H), 7.99 (m, 1H), 7.70 (m, 2H), 7.56 (m, 2H), 7.26 (d, 1H, J=8.8 Hz), 6.98 (m, 3H), 3.50 (m, 2H), 3.38 (m, 2H), 3.20 (m, 2H), 3.09 (s, 3H), 2.97 (m, 2H), 2.90 (s, 3H), 2.87 (s, 3H).

Example 1422

2-[4-(2-Fluoro-4-{7-[2-(methanesulfonyl-methyl-amino)-phenyl]-pyrrolo[2,1-f][1,2,4]triazin-2-ylamino}-phenyl)-piperazin-1-yl]-acetamide The compound was prepared with a procedure analogous to example 1408 and heated at 50° C. for 2 days. The solid was filtered off and dried to yield a yellow solid, 2-[4-(2-Fluoro- 4-{7-[2-(methanesulfonyl-methyl-amino)-phenyl]-pyrrolo[2,1-f][1,2,4]triazin-2-ylamino}-phenyl)-piperazin-1-yl]-acetamide (16 mg, 16%). LCMS: m/z=553.05 (M+H+); mp: 148° C.; 1H NMR (400 MHz, DMSO-d6) δ 9.42 (s, 1H), 8.90 (s, 1H), 7.92 (s, 1H), 7.60 (m, 2H), 7.49 (s, 2H), 7.13 (m, 3H), 6.89 (m, 3H), 3.01 (s, 3H), 2.86 (m, 9H), 2.47 (m, 4H).

Example 1423

N-[2-(2-{3-Fluoro-4-[4-((S)-2-hydroxy-propyl)-piperazin-1-yl]-phenylamino}-pyrrolo[2,1-f][1,2,4]triazin-7-yl)-phenyl]-N-methyl-methanesulfonamide The compound was prepared with a procedure analogous to example 1408 and heated at 50° C. for 2 days. The solid was filtered off and dried to yield a yellow solid, N-[2-(2-{3-Fluoro-4-[4-((S)-2-hydroxy-propyl)-piperazin-1-yl]-phenylamino}-pyrrolo[2,1-f][1,2,4]triazin-7-yl)-phenyl]-N-methyl-methanesulfonamide (21 mg, 20%). LCMS: m/z=554.08 (M+H+); mp: 165° C.; 1H NMR (400 MHz, DMSO-d6) δ 8.48 (s, 2H), 8.97 (s, 1H), 7.98 (m, 1H), 7.66 (m, 2H), 7.56 (m, 2H), 7.23 (d, 1H, J=8.5 Hz), 6.99 (d, 1H, J=4.6 Hz), 6.96 (d, 1H, J=4.6 Hz), 6.89 (m, 1H), 4.30 (m, 1H), 3.74 (m, 1H), 3.07 (s, 3H), 2.91 (m, 7H), 2.55 (s, 3H), 2.29 (m, 1H), 2.22 (m, 1H), 1.06 (d, 3H, J=6.1 Hz).

Example 1424

N-(2-{2-[3-Chloro-4-(4-methyl-piperazin-1-yl)-phenylamino]-pyrrolo[2,1-f][1,2,4]triazin-7-yl}-phenyl)-N-methyl-methanesulfonamide; compound with 2 trifluoroacetic acids The compound was prepared with a procedure analogous to example 1408 and heated at 50° C. for 19 hours to yield a yellow solid, N-(2-{2-[3-Chloro-4-(4-methyl-piperazin-1-yl)-phenylamino]-pyrrolo[2,1-f][1,2,4]triazin-7-yl}-phenyl)-N-methyl-methanesulfonamide; compound with 2 trifluoroacetic acids (52 mg, 33%).

Example 1425

N-Methyl-N-(2-{2-[4-(4-methyl-piper azine-1-carbonyl)-phenylamino]-pyrrolo[2,1-f][1,2,4]triazin-7-yl}-phenyl)-methanesulfonamide; compound with 2 trifluoroacetic acids The compound was prepared with a procedure analogous to example 1408 and heated at 50° C. for 19 hours to yield a yellow solid, N-Methyl-N-(2-{2-[4-(4-methyl-piperazine-1-carbonyl)-phenylamino]-pyrrolo[2,1-f][1,2,4]triazin-7-yl}-phenyl)-methanesulfonamide; compound with 2 trifluoroacetic acids (36 mg, 24%). LCMS: m/z=520.01 (M+H+); 1H NMR (400 MHz, DMSO-d6) δ 9.99 (br s, 1H), 9.76 (s, 1H), 9.03 (s, 1H), 7.99 (d, 1H, J=7.2 Hz), 7.73 (d, 2H, J=8.5 Hz), 7.68 (d, 1H, J=7.6 Hz), 7.58 (m, 2H), 7.32 (d, 2H, J=8.5 Hz), 7.01 (m, 2H), 4.19 (m, 2H), 3.42 (m, 2H), 3.25 (m, 2H), 3.10 (m, 5H), 2.90 (s, 3H), 2.83 (s, 3H).

Example 1426

(S)-1-(4-{4-[7-(2-Methoxy-phenyl)-pyrrolo[2,1-f][1,2,4]triazin-2-ylamino]-phenyl}-piperidin-1-yl)-propan-2-ol; compound with 2 trifluoroacetic acids The compound was prepared with a procedure analogous to example 1408 and heated at 50° C. for 2 days to yield a yellow solid, (S)-1-(4-{4-[7-(2-Methoxy-phenyl)-pyrrolo[2,1-f][1,2,4]triazin-2-ylamino]-phenyl}-piperidin-1-yl)-propan-2-ol; compound with 2 trifluoroacetic acids (35 mg, 18%). LCMS: m/z=458.17 (M+H+); 1H NMR (400 MHz, DMSO-d6) δ 9.39 (s, 1H), 9.11 (br s, 1H), 8.95 (s, 1H), 7.83 (d, 1H, J=7.4 Hz), 7.66 (d, 1H, J=8.4 Hz), 7.47 (m, 1H), 7.21 (d, 1H, J=8.3 Hz), 7.12 (m, 1H), 7.06 (d, 2H, J=8.4 Hz), 6.94 (m, 2H), 4.11 (m, 1H), 3.80 (s, 3H), 3.03 (m, 3H), 2.73 (m, 1H), 1.92 (m, 4H), 1.14 (m, 3H).

Example 1427

2-(4-{4-[7-(2-Hydroxy-phenyl)-pyrrolo[2,1-f][1,2,4]triazin-2-ylamino]-phenyl}-piperidin-1-yl)-acetamide; compound with 2 trifluoroacetic acids The compound was prepared with a procedure analogous to example 1361 and microwaved at 200° C. for 1 hour to yield a yellow solid, 2-(4-{4-[7-(2-Hydroxy-phenyl)-pyrrolo[2,1-f][1,2,4]triazin-2-ylamino]-phenyl}-piperidin-1-yl)-acetamide; compound with 2 trifluoroacetic acids (31 mg, 11%) LCMS: m/z=443.14 (M+H+); 1H NMR (400 MHz, DMSO-d6) δ 9.80 (m, 1H), 9.53 (m, 1H), 9.38 (s, 1H), 8.94 (s, 1H), 7.97 (s, 1H), 7.88 (d, 1H, J=7.6 Hz), 7.71 (m, 3H), 7.27 (m, 1H), 7.06 (m, 4H), 6.97 (m, 1H), 6.92 (d, 1H, J=4.6 Hz), 3.92 (s, 2H), 3.90 (m, 2H), 3.14 (m, 2H), 2.73 (M, 1H), 1.94 (m, 4H).

Example 1428

N-Methyl-N-{2-[2-(4-pyrrolidin-1-yl methyl-phenylamino)-pyrrolo[2,1-f][1,2,4]triazin-7-yl]-phenyl}-methane sulfonamide; compound with 2 trifluoroacetic acids The compound was prepared with a procedure analogous to general example 1408 and heated at 50° C. for 24 hours to yield an orange solid, N-Methyl-N-{2-[2-(4-pyrrolidin-1-yl methyl-phenylamino)-pyrrolo[2,1-f][1,2,4]triazin-7-yl]-phenyl}-methane sulfonamide; compound with 2 trifluoroacetic acids (2.8 mg, 2%). LCMS: m/z=477.10 (M+H+); 1H NMR (400 MHz, DMSO-d6) δ 9.66 (m, 2H), 9.01 (s, 1H), 7.99 (m, 1H), 7.72 (d, 2H, J=8.5 Hz), 7.67 (m, 1H), 7.57 (m, 2H), 7.32 (d, 2H, J=8.5 Hz), 7.00 (m, 2H), 4.24 (d, 2H, J=5.4 Hz), 3.33 (m, 2H), 3.09 (m, 5H), 2.88 (s, 3H), 2.02 (m, 2H), 1.83 (m, 2H).

Example 1429

N-tert-Butyl-3-[2-(4-pyrrolidin-1-ylmethyl-phenylamino)-pyrrolo[2,1-f][1,2,4]triazin-7-yl]-benzenesulfonamide; compound with 2 trifluoroacetic acids The compound was prepared with a procedure analogous to example 1406 to yield an orange solid, N-tert-Butyl-3-[2-(4-pyrrolidin-1-ylmethyl-phenylamino)-pyrrolo[2,1-f][1,2,4]triazin-7-yl]-benzenesulfonamide; compound with 2 trifluoroacetic acids (43 mg, 23%). LCMS: m/z=505.17 (M+H+); 1H NMR (400 MHz, DMSO-d6) δ 9.80 (br s, 1H), 9.70 (s, 1H), 9.01 (s, 1H), 8.51 (s, 1H), 8.28 (d, 1H, J=7.8 Hz), 7.81 (d, 1H, J=7.9 Hz), 7.75 (d, 2H, J=8.5 Hz), 7.67 (m, 1H), 7.56 (s, 1H), 7.39 (d, 2H, J=8.4 Hz), 7.17 (d, 1H, J=4.8 Hz), 6.97 (d, 1H, J=4.8 Hz), 4.21 (d, 2H, J=5.2 Hz), 3.31 (m, 2H), 3.04 (m, 2H), 1.96 (m, 2H), 1.78 (m, 2H), 1.05 (s, 9H).

Example 1430

[7-(2-Methoxy-phenyl)-pyrrolo[2,1-f][1,2,4]triazin-2-yl]-(4-pyrrolidin-1-ylmethyl-phenyl)-amine; compound with 2 trifluoroacetic acids The compound was prepared with a procedure analogous to example 1406 to yield an orange solid, [7-(2-Methoxyphenyl)-pyrrolo[2,1-f][1,2,4]triazin-2-yl]-(4-pyrrolidin-1-ylmethyl-phenyl)-amine; compound with 2 trifluoroacetic acids (48 mg, 20%). LCMS: m/z=400.09 (M+H+); 1H NMR (400 MHz, DMSO-d6) δ 9.90 (br s, 1H), 9.63 (s, 1H), 8.98 (s, 1H), 7.79 (m, 3H), 7.48 (m, 1H), 7.34 (d, 2H, J=8.4 Hz), 7.21 (d, 1H, J=8.4 Hz), 7.13 (m, 1H), 6.96 (m, 2H), 4.24 (d, 2H, J=5.2 Hz), 3. (s, 3H), 3.32 (m, 2H), 3.06 (m, 2H), 2.01 (m, 2H), 1.85 (m, 2H).

Example 1431

(S)-1-(4-{4-[7-(3-Methanesulfonyl-phenyl)-pyrrolo[2,1-f][1,2,4]triazin-2-ylamino]-phenyl}-piperidin-1-yl)-propan-2-ol; compound with 2 trifluoroacetic acids The compound was prepared with a procedure analogous to example 1406 to yield an orange solid, (S)-1-(4-{4-[7-(3-Methanesulfonyl-phenyl)-pyrrolo[2,1-f][1,2,4]triazin-2-ylamino]-phenyl}-piperidin-1-yl)-propan-2-ol; compound with 2 trifluoroacetic acids (68 mg, 27%). LCMS: m/z=506.14 (M+H+); 1H NMR (400 MHz, DMSO-d6) δ 9.54 (s, 1H), 9.13 (br s, 1H), 9.05 (s, 1H), 8.69 (s, 1H), 8.42 (d, 1H, J=8.0 Hz), 7.95 (d, 1H, J=7.7 Hz), 7.81 (m, 1H), 7.69 (d, 2H, J=8.4 Hz), 7.28 (d, 1H, J=4.8 Hz), 7.22 (d, 2H, J=8.4 Hz), 7.01 (d, 1H, J=4.8 Hz), 4.13 (m, 1H), 3.29 (m, 4H), 3.03 (m, 4H), 2.76 (m, 1H), 1.96 (m, 4H), 1.15 (m, 3H).

Example 1432

(S)-1-(4-{4-[7-(4-Methanesulfonyl-phenyl)-pyrrolo[2,1-f][1,2,4]triazin-2-ylamino]-phenyl}-piperidin-1-yl)-propan-2-ol; compound with 2 trifluoroacetic acids The compound was prepared with a procedure analogous to example 1406 to yield an orange solid, (S)-1-(4-{4-[7-(4-Methanesulfonyl-phenyl)-pyrrolo[2,1-f][1,2,4]triazin-2-ylamino]-phenyl}-piperidin-1-yl)-propan-2-ol; compound with 2 trifluoroacetic acids (41 mg, 16%). LCMS: m/z=506.15 (M+H+); 1H NMR (400 MHz, DMSO-d6) δ 9.61 (s, 1H), 9.07 (s, 1H), 8.49 (d, 2H, J=8.4 Hz), 8.04 (d, 2H, J=8.4 Hz), 7.72 (d, 2H, J=8.4 Hz), 7.37 (d, 1H, J=4.8 Hz), 7.22 (d, 2H, J=8.4 Hz), 7.01 (d, 1H, J=4.8 Hz), 4.12 (m, 1H), 3.30 (s, 3H), 3.05 (m, 4H), 2.81 (m, 1H), 1.97 (m, 4H), 1.14 (m, 3H).

Example 1433

2-(4-{4-[7-(4-Dimethylaminomethyl-phenyl)-pyrrolo[2,1-f][1,2,4]triazin-2-ylamino]-phenyl}-piperidin-1-yl)-acetamide; compound with 3 trifluoroacetic acids Palladium Acetate (8.5 mg, 0.000038 mol), Triphenylphosphine (27.4 mg, 0.000105 mol) and 1,4-Dioxane (2.8 mL, 0.036 mol) were combined in a flask and stirred for 10 minutes. 2-{4-[4-(7-Bromo-pyrrolo[2,1-f][1,2,4]triazin-2-ylamino)-phenyl]-piperidin-1-yl}-acetamide (157 mg, 0.000366 mol), Dimethyl-[4-(4,4,5,5-tetramethyl-1,3,2-dioxaborolan-2-yl)-benzyl]-amine; hydrochloride (224 mg, 0.000753 mol), and 1.50 M of Sodium carbonate in Water (2.2 mL, 0.0033 mol) and Tetrahydrofuran (3.0 mL, 0.037 mol). were added. The reaction was heated at 80° C. for 3 days, then purified by preparatory HPLC and lyophilized to yield an orange solid, 2-(4-{4-[7-(4-Dimethylaminomethyl-phenyl)-pyrrolo[2,1-f][1,2,4]triazin-2-ylamino]-phenyl}-piperidin-1-yl)-acetamide; compound with 3 trifluoroacetic acids (4 mg, 1%). LCMS: m/z=484.18 (M+H+); 1H NMR (400 MHz, DMSO-d6) δ 9.95 (br s, 1H), 9.55 (m, 2H), 9.02 (s, 1H), 8.33 (d, 2H, J=8.2 Hz), 8.00 (m, 1H), 7.73 (m, 3H), 7.65 (m, 3H), 7.28 (d, 1H, J=4.8 Hz), 7.18 (d, 2H, J=8.4 Hz), 6.99 (d, 1H, J=4.8 Hz), 4.36 (m, 2H), 3.94 (m, 2H), 3.16 (m, 2H), 2.75 (m, 7H), 1.99 (m, 4H), 1.30 (s, 2H).

Example 1434

2-(4-{4-[7-(3-Methanesulfonyl-phenyl)-pyrrolo[2,1-f][1,2,4]triazin-2-ylamino]-phenyl}-piperidin-1-yl)-acetamide The compound was prepared with a procedure analogous to example 1406 and the product, a solid, was filtered off to yield 2-(4-{4-[7-(3-Methanesulfonyl-phenyl)-pyrrolo[2,1-f][1,2,4]triazin-2-ylamino]-phenyl}-piperidin-1-yl)-acetamide (102 mg, 56%). LCMS: m/z=505.12 (M+H+); mp: 254° C.; 1H NMR (400 MHz, DMSO-d6) δ 9.48 (s, 1H), 9.04 (s, 1H), 8.60 (s, 1H), 8.49 (d, 1H, J=7.9 Hz), 7.95 (d, 1H, J=7.8 Hz), 7.82 (m, 1H), 7.66 (d, 2H, J=8.4 Hz), 7.27 (d, 1H, J=4.7 Hz), 7.21 (m, 3H), 7.12 (br s, 1H), 6.99 (d, 1H, J=4.7 Hz), 3.30 (s, 3H), 2.90 (m, 4H), 2.42 (m, 1H), 2.15 (m, 2H), 1.71 (m, 4H).

Example 1435

2-(4-{4-[7-(4-Methanesulfonyl-phenyl)-pyrrolo[2,1-f][1,2,4]triazin-2-ylamino]-phenyl}-piperidin-1-yl)-acetamide The compound was prepared with a procedure analogous to example 1406 and the product, a solid, was filtered off to yield 2-(4-{4-[7-(4-Methanesulfonyl-phenyl)-pyrrolo[2,1-f][1,2,4]triazin-2-ylamino]-phenyl}-piperidin-1-yl)-acetamide (77 mg, 43%). LCMS: m/z=505.11 (M+H+); mp: 310° C.; 1H NMR (400 MHz, DMSO-d6) δ 9.52 (s, 1H), 9.05 (s, 1H), 8.48 (d, 2H, J=8.4 Hz), 8.04 (d, 1H, J=8.4 Hz), 7.67 (d, 2H, J=8.3 Hz), 7.35 (d, 1H, J=4.8 Hz), 7.24 (m, 3H), 7.13 (br s, 1H), 7.00 (d, 1H, J=4.8 Hz), 3.30 (s, 3H), 2.92 (m, 4H), 2.17 (m, 2H), 1.75 (m, 4H).

Example 1436

N-[2-(2-{4-[1-((S)-2-Hydroxy-propyl)-piperidin-4-yl]-phenylamino}-pyrrolo[2,1-f][1,2,4]triazin-7-yl)-phenyl]-N-methyl-methanesulfonamide; compound with 2 trifluoro-acetic acids The compound was prepared with a procedure analogous to example 1406 to yield an orange solid, N-[2-(2-{4-[1-((S)-2-Hydroxy-propyl)-piperidin-4-yl]-phenylamino}-pyrrolo[2,1-f][1,2,4]triazin-7-yl)-phenyl]-N-methyl-methanesulfonamide; compound with 2 trifluoro-acetic acids (23 mg, 10%). LCMS: m/z=535.14 (M+H+); 1H NMR (400 MHz, DMSO-d6) δ 9.40 (s, 1H), 9.10 (br s, 1H), 8.97 (s, 1H), 8.00 (d, 1H, J=7.0 Hz), 7.60 (m, 5H), 7.05 (d, 2H, J=8.3 Hz), 6.97

(m, 2H), 4.12 (m, 1H), 3.59 (m, 2H), 3.08 (s, 3H), 2.98 (m, 2H), 2.90 (s, 3H), 2.72 (m, 2H), 1.93 (m, 5H), 1.14 (m, 3H).

Example 1437

[3-Fluoro-4-(4-methyl-piperazin-1-yl)-phenyl]-[7-(4-methanesulfonyl-phenyl)-pyrrolo[2,1-f][1,2,4]triazin-2-yl]-amine The compound was prepared with a procedure analogous to example 1406 to yield a yellow solid, [3-Fluoro-4-(4-methyl-piperazin-1-yl)-phenyl]-[7-(4-methanesulfonyl-phenyl)-pyrrolo[2,1-f][1,2,4]triazin-2-yl]-amine (25 mg, 16%). LCMS: m/z=481.11 (M+H+); mp: 227° C.; 1H NMR (400 MHz, DMSO-d6) δ 9.64 (s, 1H), 9.05 (s, 1H), 8.45 (d, 2H, J=7.9 Hz), 8.03 (d, 2H, J=7.9 Hz), 7.75 (d, 1H, J=15.4 Hz), 7.34 (m, 2H), 7.01 (m, 2H), 3.29 (s, 3H), 2.98 (s, 4H), 2.23 (s, 3H).

Example 1441

{2-Methoxy-4-[3-(4-methyl-piperazin-1-yl)-piperidin-1-yl]-phenyl}-[7-(2-methoxy-phenyl)-pyrrolo[2,1-f][1,2,4]triazin-2-yl]-amine 1441a) 4-(1-tert-Butoxycarbonyl-piperidin-3-yl)-piperazine-1-carboxylic acid benzyl: To a solution of 3-oxo-piperidine-1-carboxylic acid tert-butyl ester (3.00 g, 15.0 mmol) and piperazine-1-carboxylic acid benzyl ester (3.32 g, 15.0 mmol) in dichloromethane (150 mL) was added acetic acid (86 uL, 1.5 mmol). The mixture was stirred for one hour and sodium triacetoxyborohydride (9.6 g, 45 mmol) was added. The mixture was stirred overnight at room temperature. The mixture was treated with water, the organic phase was washed with sat'd aq. sodium bicarbonate and brine, dried over anhydrous magnesium sulfate, filtered and concentrated. The crude product was flash chromatographed over silica gel to provide 3.5 g of the purified product as a pale viscous oil. MS=404 (M+1).

1441b) 4-Piperidin-3-yl-piperazine-1-carboxylic acid benzyl ester; compound with trifluoro-acetic acid: A solution of 4-(1-tert-butoxycarbonyl-piperidin-3-yl)-piperazine-1-carboxylic acid benzyl ester (24.5 g, 60.7 mmol) in dichloromethane (250 mL) was cooled in an ice-water bath and to this was added trifluoroacetic Acid (250 mL). The mixture was stirred at 0-5° C. and allowed to slowly warm to room temperature overnight. The mixture was concentrated to a viscous oil. Dropwise addition of ethyl acetate (150 mL) with stirring produced a precipitate, collected by vacuum filtration with applied house vacuum. The solid was washed with ethyl acetate and dried to constant weight to provide 18.7 g of the product as a white solid, used without further purification. MS=418 (M+1).

1441c) 4-[1-(3-Methoxy-4-nitro-phenyl)-piperidin-3-yl]-piperazine-1-carboxylic acid benzyl ester: To a mixture of 4-piperidin-3-yl-piperazine-1-carboxylic acid benzyl ester, compound with trifluoro-acetic acid (10.0 g, 24.0 mmol) and potassium carbonate (8.3 g, 6.0 mmol) in DMF (100 mL) was added 4-fluoro-2-methoxy-1-nitro-benzene (4.1 g, 24 mmol) with stirring. The mixture was heated at 60° C. for 18 hours. The solvent was removed on the rotovap and the residue was partitioned between dichloromethane and water, the organic phase was washed with sat'd aq. sodium bicarbonate and brine, dried over anhydrous magnesium sulfate, filtered and concentrated. Flash chromatography over silica gel provided 9.2 g of the title compound. MS=455 (M+1).

1441d) 1-[1-(3-Methoxy-4-nitro-phenyl)-piperidin-3-yl]-piperazine hydrobromide: A solution of 4-[1-(3-methoxy-4-nitro-phenyl)-piperidin-3-yl]-piperazine-1-carboxylic acid benzyl ester (300 mg, 0.66 mmol) in 4 M HBr in Acetic acid (6 mL, 20 mmol) was heated at 40-45° C. for 45 min with stirring, then allowed to cool to room temperature while being stirred overnight. The orange homogenous solution was added dropwise to a vigorously stirred flask of ethyl acetate (50 mL) and the resulting precipitate was filtered, washed with ethyl acetate and dried in-vacuo to give 294 mg of the title compound as an orange solid, used without further purification. MS=322 (M-HBr+1).

1441e) 1-[1-(3-Methoxy-4-nitro-phenyl)-piperidin-3-yl]-4-methyl-piperazine: To a solution of 1-[1-(3-methoxy-4-nitro-phenyl)-piperidin-3-yl]-piperazine, hydrobromide (500 mg, 1.25 mmol) in acetonitrile (20 mL) and methanol (20 mL) was added 10M aqueous formaldehyde (4.0 mL) with stirring. After 10 minutes sodium cyanoborohydride (86 mg, 1.4 mmol) was added and the mixture was stirred for 2 hours at room temperature. The mixture was concentrated, the residue was dissolved in dichloromethane, washed with saturated aqeuous sodium bicarbonate and brine, dried over anhydrous magnesium sulfate, filtered and concentrated to give 315 mg of the title compound, used without further purification. MS=335.

1441f) 2-Methoxy-4-[3-(4-methyl-piperazin-1-yl)-piperidin-1-yl]-phenylamine: To a solution of 1-[1-(3-methoxy-4-nitro-phenyl)-piperidin-3-yl]-4-methyl-piperazine (310 mg, 0.93 mmol) in ethyl acetate (15 mL) and ethanol (15 mL) in a Paar bottle was added 10% Palladium on Carbon (75 mg). The mixture was placed on a Paar shaker under 50 psi H₂ and shaken at room temperature for two hours. The mixture was filtered and concentrated to give 242 mg of the title compound as an oil, used without further purification. MS=305.

1441g) {2-Methoxy-4-[3-(4-methyl-piperazin-1-yl)-piperidin-1-yl]-phenyl}-[7-(2-methoxy-phenyl)-pyrrolo[2,1-f][1,2,4]triazin-2-yl]-amine: To a solution of 2-methoxy-4-[3-(4-methyl-piperazin-1-yl)-piperidin-1-yl]-phenylamine (240 mg, 0.79 mmol) and 2-methanesulfinyl-7-(2-methoxy-phenyl)-pyrrolo[2,1-f][1,2,4]triazine (151 mg, 0.53 mmol) in 2-methoxyethanol (1.50 mL) was added N,N-diisopropylethylamine (183 uL). The mixture was submitted to microwave irradiation at 300 watts, at 200° C. for eight hours. The mixture was diluted with MeOH (10 mL), filtered through a 45 micron filter, and concentrated. Preparative RF-HPLC gave the separate diastereomers. The first peak gave 10 mg of the title compound as an amber amorphous powder upon lyophillization. MS=528 (M+1); NMR (DMSO-d₆, ppm): 9.48 (br, 1H), 8.93 (s, 1H), 7.98 (d, J=8 Hz, 1H), 7.83 (d, J=8 Hz, 1H), 7.63 (s, 1H), 7.46 (t, J=8 Hz, 1H), 7.21 (d, J=8 Hz, 1H), 7.10 (t, J=8 Hz, 1H), 6.96 (q, J=5 Hz, 15 Hz, 2H), 6.88 (br, 1H), 6.63 (br, 1H), 3.89 (s, 3H), 3.80 (s+m, 4H), 3.73 (m, 2H), 3.51 (m, 4H), 2.84 (s, 3H), 2.05 (m, 2H), 1.92 (m, 2H), 1.70 (m, 2H), 1.56 (m, 2H), 1.21 (m, 2H).

Example 1442

{2-Methoxy-4-[3-(4-methyl-piperazin-1-yl)-piperidin-1-yl]-phenyl}-[7-(2-methoxy-phenyl)-pyrrolo[2,1-f][1,2,4]triazin-2-yl]-amine 1442a) {2-Methoxy-4-[3-(4-methyl-piperazin-1-yl)-piperidin-1-yl]-phenyl}-[7-(2-methoxy-phenyl)-pyrrolo[2,1-f][1,2,4]triazin-2-yl]-amine: The second eluting peak from above gave 17 mg of the other title diastereomer upon lyophillization. MS=528 (M+1); NMR (DMSO-d₆, ppm): 9.48 (br, 1H), 8.93 (s, 1H), 7.98 (d, J=8 Hz, 1H), 7.83 (d, J=8 Hz, 1H), 7.63 (s, 1H), 7.46 (t, J=8 Hz, 1H), 7.21 (d, J=8 Hz, 1H), 7.10 (t, J=8 Hz, 1H), 6.96 (q, J=5 Hz, 15 Hz, 2H), 6.88 (br, 1H), 6.63 (br, 1H), 3.89 (s, 3H), 3.80 (s+m, 4H), 3.73 (m, 2H), 3.51 (m, 4H), 2.84 (s, 3H), 2.05 (m, 2H), 1.92 (m, 2H), 1.70 (m, 2H), 1.56 (m, 2H), 1.21 (m, 2H).

Example 1443

2-[4-(1-{3-Methoxy-4-[7-(2-methoxy-phenyl)-pyrrolo[2,1-f][1,2,4]triazin-2-ylamino]-phenyl}-piperidin-3-yl)-piperazin-1-yl]-ethanol 1443a) 2-{4-[1-(3-Methoxy-4-nitro-phenyl)-piperidin-3-yl]-piperazin-1-yl}-ethanol: Into a pressure tube ethylene oxide was gently bubbled into a mixture of 1-[1-(3-Methoxy-4-nitro-phenyl)-piperidin-3-yl]-piperazine; hydrobromide (620 mg, 1.5 mmol) and N,N-diisopropylethylamine (0.350 mL, 2.01 mmol) in methanol (25 mL) with stirring for several minutes to saturation. The mixture was stirred at room temperature overnight. Additional ethylene oxide was added to saturation and the mixture was stirred for an additional day. The mixture was concentrated, dichloromethane (100 mL) was added and the organic phase was washed with sodium bicarbonate solution and brine, dried (MgSO4), filtered and concentrated. Flash chromatography gave 230 mg of the purified product as a yellow semi-solid. MS=365 (M+1).

1443b) 2-{4-[1-(4-Amino-3-methoxy-phenyl)-piperidin-3-yl]-piperazin-1-yl}-ethanol: A solution of 2-{4-[1-(3-Methoxy-4-nitro-phenyl)-piperidin-3-yl]-piperazin-1-yl}-ethanol (230 mg, 0.63 mmol) in ethyl acetate (25 mL) and ethanol (25 mL) in a Paar bottle was treated with 10% Palladium on Carbon (50 mg). The mixture was placed on a Paar shaker under an atmosphere of Hydrogen (40 psi) at room temperature for three hours. The mixture was filtered and concentrated to afford 210 mg of the title compound, used without further purification. MS=335 (M+1).

1443c) 2-[4-(1-{3-Methoxy-4-[7-(2-methoxy-phenyl)-pyrrolo[2,1-f][1,2,4]triazin-2-ylamino]-phenyl}-piperidin-3-yl)-piperazin-1-yl]-ethanol, compound with trifluoroacetic acid: A mixture of 2-{4-[1-(4-Amino-3-methoxy-phenyl)-piperidin-3-yl]-piperazin-1-yl}-ethanol (200 mg, 0.5980 mmol) and 2-methanesulfinyl-7-(2-methoxy-phenyl)-pyrrolo[2,1-f][1,2,4]triazine (90 mg, 0.313 mmol) in 2-methoxyethanol (2.0 mL, 25 mmol) was treated with N,N-diisopropylamine (1.20 uL, 0.689 mmol) in a microwave tube and heated in a microwave apparatus at 300 watts at 200° C. for eight hours. The mixture was filtered and purified by preparative RF-HPLC to give 52 mg of the title compound upon lyophillization. MS=558 (M-TFA+1); NMR (DMSO-d$_6$, ppm): 8.93 (s, 1H), 7.95 (d, J=8 Hz, 1H), 7.83 (d, J=8 Hz, 1H), 7.61 (s, 1H), 7.45 (t, J=8 Hz, 1H), 7.20 (d, J=8 Hz, 1H), 7.10 (t, J=8 Hz, 1H), 6.94 (q, J=5 Hz, 10 Hz, 2H), 6.83 (s, 1H), 6.59 (s, 1H), 3.88 (s, 3H), 3.80 (s, 3H), 3.74 (m, 2H), 3.50 (m, 2H), 3.22 (m, 2H), 2.96 (m, 4H), 2.83 (m, 4H), 2.07 (m, 1H), 1.89 (m, 2H), 1.70 (m, 2H), 1.55 (m, 2H).

Example 1444

[2-Methoxy-4-(3-morpholin-4-yl-piperidin-1-yl)-phenyl]-[7-(2-methoxy-phenyl)-pyrrolo[2,1-f][1,2,4]triazin-2-yl]-amine; compound with trifluoroacetic acid 1444a) 3-Morpholin-4-yl-piperidine-1-carboxylic acid tert-butyl ester: To a solution of 3-oxo-piperidine-1-carboxylic acid tert-butyl ester (5.00 g, 25.1 mmol) and morpholine (4.38 mL, 50.2 mmol) in methylene chloride (150 mL, 2300 mmol) was added acetic acid (0.143 mL, 2.51 mmol). The mixture was stirred for one hour when sodium triacetoxyborohydride (16.0 g, 75.3 mmol) was added. Stirring was continued overnight at room temperature. The mixture was treated with water, the organic phase was washed with sodium bicarbonate solution and brine, dried (MgSO4), filtered and concentrated to give 6.3 g of the crude product, used without further purification.

1444b) 4-Piperidin-3-yl-morpholine; compound with bis-trifluoroacetic acid: To a solution of 3-morpholin-4-yl-piperidine-1-carboxylic acid tert-butyl ester (6.50 g, 24.0 mmol) in methylene chloride (100 mL) was added trifluoroacetic acid (100 mL). The mixture was stirred for 1.5 hours at room temperature at which time gas evolution (CO$_2$) had ceased. The mixture was concentrated and the residue was dissolved in dichloromethane and concentrated repeatedly (5×200 mL) to remove excess TFA, then several times with ether (3×200 mL) to induce crystallization. The cakey semi-solid was placed on the vac line overnight to provide 7.8 g of the title compound as a pale yellow solid, used without further purification. NMR suggested a bis-TFA salt. NMR (DMSO, ppm): 9.41 (br, 1H), 9.01 (br, 2H), 3.79 (m, 4H), 3.61 (m, 2H), 3.20 (m, 2H), 2.81 (m, 2H), 2.13 (m, 2H), 1.95 (m, 2H), 1.63 (m, 4H).

1444c) 4-[1-(3-Methoxy-4-nitro-phenyl)-piperidin-3-yl]-morpholine: To a mixture of 4-piperidin-3-yl-morpholine; compound with bis-trifluoroacetic acid (3.0 g, 7.5 mmol) and potassium carbonate (3.6 g, 26 mmol) in N,N-dimethylformamide (100 mL) was added 4-fluoro-2-methoxy-1-nitrobenzene (1.3 g, 7.5 mmol) with stirring. The mixture was heated at 60° C. for 18 hours. The solvent was removed on the rotovap and the residue was partitioned between dichloromethane and water, the organic phase was washed with sodium bicarbonate solution and brine, dried (MgSO4), filtered and concentrated. Flash chromatography gave 2.4 g of the purified product as a yellow viscous oil. MS=322 (M+1).

1444d) 2-Methoxy-4-(3-morpholin-4-yl-piperidin-1-yl)-phenylamine: This compound was prepared according to Example 1442b. A mixture of 4-[1-(3-methoxy-4-nitro-phenyl)-piperidin-3-yl]-morpholine (500 mg, 2 mmol) and 10% Pd—C catalyst (100 mg) in ethyl acetate (25 mL) and ethanol (25 mL) was shaken under 50 psi Hydrogen for 3.5 h on a Paar apparatus for 3 hrs to provide 400 mg of the title compound as a pale greenish-violet solid following filtration and concentration, stored under N$_2$ at −10° C. MS=292 (M+1).

1444e) [2-Methoxy-4-(3-morpholin-4-yl-piperidin-1-yl)-phenyl]-[7-(2-methoxy-phenyl)-pyrrolo[2,1-f][1,2,4]triazin-2-yl]-amine; compound with trifluoroacetic acid: This compound was prepared according to Example 1443c. From 2-methoxy-4-(3-morpholin-4-yl-piperidin-1-yl)-phenylamine (228 mg, 0.783 mmol) and 2-methanesulfinyl-7-(2-methoxy-phenyl)-pyrrolo[2,1-f][1,2,4]triazine (150 mg, 0.52 mmol) in 2-ethoxyethanol (2.0 mL, 25 mmol) N,N-Diisopropylethylamine (182 uL, 1.04 mmol) was obtained 87 mg of the title compound as an amber, hygroscopic TFA salt following RP-HPLC. LCMS=515 (M+1-TFA); NMR (DMSO-d$_6$, ppm): 9.90 (br, 1H), 8.91 (s, 1H), 7.87 (m, 2H), 7.56 (s, 1H), 7.44 (m, 1H), 7.20 (m, 1H), 7.10 (m, 1H), 6.95 (m, 2H), 6.70 (s, 1H), 6.47 (m, 1H), 4.20 (m, 4H), 3.82 (s, 3H), 3.80 (s, 3H), 3.51 (m, 7H), 2.89 (m, 1H), 2.70 (m, 1H), 2.15 (m, 1H), 1.89 (m, 1H), 1.62 (m, 2H).

Example 1445

{4-[3-(2,6-Dimethyl-morpholin-4-yl)-piperidin-1-yl]-2-methoxy-phenyl}-[7-(2-methoxy-phenyl)-pyrrolo[2,1-f][1,2,4]triazin-2-yl]-amine 1445a) 3-(2,6-Dimethyl-morpholin-4-yl)-piperidine-1-carboxylic acid tert-butyl ester: This compound was prepared according to the procedure for Example 1444a. From 3-oxo-piperidine-1-carboxylic acid tert-butyl ester (5.00 g, 25.1 mmol) and 2,6-dimethyl-morpholine (5.78 g, 50.2 mmol) was obtained 7.4 g of the crude product as a viscous pale yellow oil, used without further purification. MS=321 (M+23).

1445b) 2,6-Dimethyl-4-piperidin-3-yl-morpholine; compound with bis-trifluoroacetic acid: This compound was prepared according to the procedure for Example 1444b. From 3-(2,6-dimethyl-morpholin-4-yl)-piperidine-1-carboxylic acid tert-butyl ester (7.17 g, 24.0 mmol) was obtained 8.05 g of the title compound as a pale yellow solid. NMR (DMSO, ppm): 9.30 (br, 1H), 8.80 (br, 2H), 3.98 (m, 1H), 3.77 (m, 2H), 3.56 (m, 2H), 3.04 (m, 2H), 2.80 (m, 2H), 2.36 (m, 1H), 2.10 (m, 2H), 1.93 (m, 2H), 1.62 (m, 2H), 1.14 (m, 6H).

1445c) 4-[1-(3-Methoxy-4-nitro-phenyl)-piperidin-3-yl]-2,6-dimethyl-morpholine: This compound was prepared according to the procedure for Example 1444c. From 2,6-dimethyl-4-piperidin-3-yl-morpholine; compound with bis-trifluoro-acetic acid (3.0 g, 7.0 mmol) and 4-fluoro-2-methoxy-1-nitro-benzene (1.2 g, 7.0 mmol) was obtained 1.2 g of the title compound as a yellow solid following flash chromatography on silica gel. MS=350 (M+1).

1445d) 4-[3-(2,6-Dimethyl-morpholin-4-yl)-piperidin-1-yl]-2-methoxy-phenylamine: This compound was prepared according to the procedure for Example 1444d. From 4-[1-(3-methoxy-4-nitro-phenyl)-piperidin-3-yl]-2,6-dimethyl-morpholine (500.0 mg, 1.431 mmol) was obtained 450 mg of the title compound, used without further purification. MS=320 (M+1).

1445e) {4-[3-(2,6-Dimethyl-morpholin-4-yl)-piperidin-1-yl]-2-methoxy-phenyl}-[7-(2-methoxy-phenyl)-pyrrolo[2,1-f][1,2,4]triazin-2-yl]-amine: This compound was prepared according to the procedure for Example 1443c. From 4-[3-(2,6-dimethyl-morpholin-4-yl)-piperidin-1-yl]-2-methoxy-phenylamine (250 mg, 0.783 mmol) and 2-methanesulfinyl-7-(2-methoxy-phenyl)-pyrrolo[2,1-f][1,2,4]triazine (150 mg, 0.52 mmol) was obtained 87 mg of the title compound following preparative RF-HPLC purification and free-basing (aq. NaHCO3/DCM) of the isolated hygroscopic TFA salt. MS=543 (M+1); NMR (DMSO-$d_6$, ppm): 8.90 (s, 1H), 7.83 (m, 2H), 7.49 (s, 1H), 7.43 (m, 1H), 7.19 (m, 1H), 7.08 (m, 1H), 6.95 (m, 2H), 6.61 (s, 1H), 6.61 (m, 1H), 3.85 (s, 3H), 3.79 (s, 3H), 3.53 (m, 4H), 3.32 (s, 2H), 2.80 (m, 2H), 1.92 (m, 3H), 1.80 (m, 1H), 1.55 (m, 1H), 1.32 (m, 2H), 1.06 (m, 6H).

Example 1446

N-(3-{2-[2-Methoxy-4-(4-morpholin-4-yl-piperidin-1-yl)-phenylamino]-pyrrolo[2,1-f][1,2,4]triazin-7-yl}-phenyl)-methanesulfonamide 1446a) 4-[1-(3-Methoxy-4-nitro-phenyl)-piperidin-4-yl]-morpholine: This compound was prepared according to Example 1444c. From 4-piperidin-4-yl-morpholine (1.80 g, 10.6 mmol) and 4-fluoro-2-methoxy-1-nitro-benzene (1.90 g, 11.1 mmol) was obtained 3.12 g of the title compound as a yellow solid following flash chromatography. MS=322 (M+1).

1446b) 2-Methoxy-4-(4-morpholin-4-yl-piperidin-1-yl)-phenylamine: This compound was prepared according to Example 1443b. From 4-[1-(3-methoxy-4-nitro-phenyl)-piperidin-4-yl]-morpholine (1.30 g, 4.04 mmol) in Ethyl acetate (50 mL, 500 mmol) and ethanol (50 mL, 800 mmol) in a Paar bottle was obtained 1.30 g of the title compound as a pale green solid, used without further purification. MS=292.

1446c) N-(3-{2-[2-Methoxy-4-(4-morpholin-4-yl-piperidin-1-yl)-phenylamino]-pyrrolo[2,1-f][1,2,4]triazin-7-yl}-phenyl)-methanesulfonamide: This compound was prepared according to the procedure for Example 1443c. From N-[3-(2-Methanesulfinyl-pyrrolo[2,1-f][1,2,4]triazin-7-yl)-phenyl]-methanesulfonamide (150 mg, 0.43 mmol) and 2-methoxy-4-(4-morpholin-4-yl-piperidin-1-yl)-phenylamine (187 mg, 0.642 mmol) was obtained 60 mg of the title compound as a mustard yellow solid following preparative RF-HPLC and free-basing (DCM/NaHCO₃). mp 190-196° C. (dec); MS=578 (M+1); NMR (DMSO-$d_6$, ppm): 9.81 (s, 1H), 8.94 (s, 1H), 7.88 (m, 3H), 7.68 (s, 1H), 7.45 (m, 1H), 7.24 (m, 1H), 7.06 (m, 1H), 6.94 (m, 1H), 6.67 (s, 1H), 6.58 (m, 1H), 3.85 (s, 3H), 3.74 (m, 6H), 3.44 (m, 1H), 3.01 (s, 4H), 2.67 (m, 3H), 2.30 (m, 2H), 1.90 (m, 2H), 1.55 (m, 2H).

Example 1447

[7-(2-Ethoxy-phenyl)-pyrrolo[2,1-f][1,2,4]triazin-2-yl]-[2-methoxy-4-(4-morpholin-4-yl-piperidin-1-yl)-phenyl]-amine, compound with trifluoroacetic acid 1447a) 7-(2-Ethoxy-phenyl)-2-methanesulfinyl-pyrrolo[2,1-f][1,2,4]triazine: Into a 30 mL vial, Palladium Acetate (52 mg, 0.23 mmol) and triphenylphosphine (151 mg, 0.58 mmol) were added and purged under an atmosphere of Nitrogen for 10 minutes. 1,4-dioxane (10 mL) was added and stirred at RT for 10 minutes. To this was added 7-bromo-2-methanesulfinyl-pyrrolo[2,1-f][1,2,4]triazine (300 mg, 1.15 mmol), 2-ethoxy-benzeneboronic acid (383 mg, 2.31 mmol), N,N-dimethylformamide (15 mL) and 1.50 M of sodium carbonate in water (6.5 mL, 9.8 mmol). The reaction was heated at 80° C. for 3 hours. The mixture was concentrated on the rotovap and the residue was partitioned between EtOAc and water. The organic phase was washed with water and brine, dried (MgSO4), filtered and concentrated to give 700 mg of dark viscous oil. The crude product was flash chromatographed to provide 260 mg of the purified product. MS=302 (M+1).

1447b) [7-(2-Ethoxy-phenyl)-pyrrolo[2,1-f][1,2,4]triazin-2-yl]-[2-methoxy-4-(4-morpholin-4-yl-piperidin-1-yl)-phenyl]-amine, compound with trifluoroacetic acid: This compound was prepared according to the procedure for 1443c. From 7-(2-ethoxy-phenyl)-2-methanesulfinyl-pyrrolo[2,1-f][1,2,4]triazine (130 mg, 0.43 mmol) and 2-methoxy-4-(4-morpholin-4-yl-piperidin-1-yl)-phenylamine (187 mg, 0.642 mmol) was obtained 131 mg of the title compound as a mustard yellow solid following preparative RF-HPLC and lyophillization. MS=529 (M-TFA+1); NMR (DMSO-$d_6$, ppm): 9.50 (br, 1H), 8.90 (s, 1H), 7.92 (m, 2H), 7.54 (s, 1H), 7.41 (t, J=7 Hz, 1H), 7.17 (d, J=8 Hz, 1H), 7.08 (t, J=7 Hz, 1H), 7.02 (d, J=7 Hz, 1H), 6.92 (d, J=5 Hz, 1H), 6.71 (s, 1H), 6.45 (d, J=8 Hz, 1H), 4.06 (m, 4H), 3.85 (s+m, 6H), 3.68 (m, 2H), 3.49 (m, 2H), 3.40 (m, 1H), 3.14 (m, 1H), 2.68 (m, 1H), 2.14 (m, 3H), 1.72 (m, 2H), 1.23 (t, J=7 Hz, 3H).

Example 1448

[7-(2-Methoxy-phenyl)-pyrrolo[2,1-f][1,2,4]triazin-2-yl]-[2-methoxy-4-(3-piperazin-1-yl-piperidin-1-yl)-phenyl]-amine 1448a) [7-(2-Methoxy-phenyl)-pyrrolo[2,1-f][1,2,4]triazin-2-yl]-[2-methoxy-4-(3-piperazin-1-yl-piperidin-1-yl)-phenyl]-amine: A solution of 4-(1-{3-Methoxy-4-[7-(2-methoxy-phenyl)-pyrrolo[2,1-f][1,2,4]triazin-2-ylamino]-phenyl}-piperidin-3-yl)-piperazine-1-carboxylic acid benzyl ester (60.0 mg, 0.093 mmol) in 4M HBr in acetic acid (0.91 mL, 3.70 mmol) was heated at 40-45° C. for 45 min, then allowed to cool to room temperature while being stirred an additional 2 hrs. The orange homogenous solution was added dropwise to a vigorously stirred flask of EtOAc (50 mL) and the resulting precipitate was filtered, washed with EtOAc and dried in-vacuo to give a hygroscopic orange sticky mass. This was treated with 1N NaOH (5 mL) and extracted with DCM (2×25 mL). The combined organic phase was washed with brine and dried (MgSO4), filtered and concentrated to constant weight to give 21 mg of the title cmpd as a yellow solid, used without further purification. MS=514 (M+1); NMR (DMSO-$d_6$, ppm): 8.89 (s, 1H), 7.80 (m, 2H), 7.50 (s, 1H), 7.45 (t, J=7 Hz, 1H), 7.20 (d, J=7 Hz, 1H), 7.10 (t, J=7 Hz, 1H), 6.95 (q, J=5 Hz, 14 Hz, 2H), 6.61 (s, 1H), 6.35 (d, J=7 Hz, 1H), 3.84 (s, 3H), 3.79 (s, 3H), 3.65 (m, 1H), 3.55 (m, 1H), 3.40 (m, 2H), 2.72 (m, 4H), 2.60 (m, 3H), 1.88 (m, 1H), 1.75 (m, 1H), 1.55 (m, 1H), 1.30 (m, 2H), 1.10 (m, 1H).

Example 1449

N-(3-{2-[2-Methoxy-4-(4-morpholin-4-yl-piperidin-1-yl)-phenylamino]-pyrrolo[2,1-f][1,2,4]triazin-7-yl}-phenyl)-N-methyl-methanesulfonamide 1449a) N-[3-(2-Methylsulfanyl-pyrrolo[2,1-f][1,2,4]triazin-7-yl)-phenyl]-methane-sulfonamide: A solution of Pd(OAc)$_2$ (92 mg, 0.41 mmol) and triphenylphosphine (269 mg, 1.02 mmol) in 1,4-dioxane was purged with nitrogen while being stirred and 7-bromo-2-methylsulfanyl-pyrrolo[2,1-f][1,2,4]triazine (500 mg, 2.0 mmol) and 3-methylsulfonyl-aminophenyl boronic acid (881 mg, 4.10 mmol) was added followed by DMF (15 mL) and 1.5M of sodium carbonate in water (12 mL, 17 mmol). After being thoroughly purged with nitrogen, the reaction was heated at 80° C. for 3 hours with stirring. The solvent was removed on the rotovap and the residue was partitioned between EtOAc and water. The organic phase was washed with water and brine, dried (MgSO4), filtered and concentrated to give the crude product as a brown viscous oil. This was flash chromatographed on silica gel to provide 560 mg of the purified product as a yellow solid. MS=335 (M+1).

1449b) N-[3-(2-Methanesulfinyl-pyrrolo[2,1-f][1,2,4]triazin-7-yl)-phenyl]-methanesulfonamide: A solution of N-[3-(2-methylsulfanyl-pyrrolo[2,1-f][1,2,4]triazin-7-yl)-phenyl]-methanesulfonamide (550 mg, 1.65 mmol) in dichloromethane (50 mL) was treated with 70% m-chloroperbenzoic acid (446.0 mg, 1.8 mmol) at room temperature with stirring for two hours. The mixture was stirred with 10% Na$_2$S$_2$O$_3$ (25 mL) for 5 minutes. The organic phase was washed with saturated aqueous NaHCO$_3$ and brine, dried (MgSO$_4$), filtered and concentrated to give 560 mg of the product as a yellow solid, used without further purification. MS=349 (M–1).

1449c) N-[3-(2-Methanesulfinyl-pyrrolo[2,1-f][1,2,4]triazin-7-yl)-phenyl]-N-methyl-methanesulfonamide: To a mixture of N-[3-(2-methanesulfinyl-pyrrolo[2,1-f][1,2,4]triazin-7-yl)-phenyl]-methanesulfonamide (200 mg, 0.57 mmol) and potassium carbonate (197 mg, 1.43 mmol) in DMF (5.0 mL) was added methyl iodide (53 uL, 0.86 mmol). The mixture was stirred at room temperature. After 24 hrs, an additional 70uL MeI was added and the mixture was stirred an additional 24 h. The mixture was filtered and concentrated. The residue was dissolved in methylene chloride, washed with saturated aqueous NaHCO3 and brine, dried (MgSO4), filtered and concentrated. Flash chromatography over silica gel gave 163 mg of the title compound as a yellow solid. MS=365.

1449d) N-(3-{2-[2-Methoxy-4-(4-morpholin-4-yl-piperidin-1-yl)-phenylamino]-pyrrolo[2,1-f][1,2,4]triazin-7-yl}-phenyl)-N-methyl-methanesulfonamide: This compound was prepared according to the procedure for Example 1443c. From N-[3-(2-methanesulfinyl-pyrrolo[2,1-f][1,2,4]triazin-7-yl)-phenyl]-N-methyl-methanesulfonamide (160 mg, 0.43 mmol) and 2-methoxy-4-(4-morpholin-4-yl-piperidin-1-yl)-phenylamine (187 mg, 0.64 mmol) was obtained 62 mg of the title cmpd as a pale yellow amorphous solid following preparative RF-HPLC and free-basing of the hygroscopic TFA salt. MS=592 (M+1); NMR (DMSO-$d_6$, ppm): 8.93 (s, 1H), 8.20 (s, 1H), 8.10 (d, J=6 Hz, 1H), 7.75 (m, 2H), 7.50 (t, J=7 Hz, 1H), 7.41 (d J=8 Hz, 1H), 7.20 (d, J=6 Hz, 1H), 6.94 (d, J=6 Hz, 1H), 6.67 (m, 1H), 6.58 (d, J=8 Hz, 1H), 3.83 (s, 3H), 3.73 (m, 2H), 3.58 (m, 4H), 3.25 (s, 3H), 2.95 (s, 3H), 2.68 (m, 2H), 2.28 (m, 2H), 1.89 (m, 2H), 1.52 (m, 2H).

Example 1450

N-(2-{2-[2-Methoxy-4-(4-morpholin-4-yl-piperidin-1-yl)-phenylamino]-pyrrolo[2,1-f][1,2,4]triazin-7-yl}-phenyl)-methanesulfonamide 1450a) N-(2-{2-[2-Methoxy-4-(4-morpholin-4-yl-piperidin-1-yl)-phenylamino]-pyrrolo[2,1-f][1,2,4]triazin-7-yl}-phenyl)-methanesulfonamide: This compound was prepared according to the procedure for 1443c. From N-[2-(2-methanesulfinyl-pyrrolo[2,1-f][1,2,4]triazin-7-yl)-phenyl]-methanesulfonamide (150 mg, 0.43 mmol) and 2-methoxy-4-(4-morpholin-4-yl-piperidin-1-yl)-phenylamine (187 mg, 0.64) was obtained 106 mg of the title compound upon preparative RF-HPLC and free-basing of the hygroscopic TFA salt. mp 201-204° C. (dec); MS=578 (M+1); NMR (DMSO-$d_6$, ppm): 8.94 (s, 1H), 8.80 (s, 1H), 7.85 (s, 1H), 7.68 (d, J=8 Hz, 1H), 7.57 (d, J=8 Hz, 1H), 7.48 (m, 2H), 7.39 (m, 1H), 6.97 (m, 2H), 6.62 (s, 1H), 6.37 (q, J=3 Hz, 8 Hz, 1H), 3.79 (s, 3H), 3.66 (m, 2H), 3.58 (t, J=5 Hz, 4H), 3.31 (s, 3H), 2.63 (m, 5H), 2.26 (m, 1H), 1.86 (m, 2H), 1.50 (m, 2H).

Example 1451

[7-(2-Isopropoxy-phenyl)-pyrrolo[2,1-f][1,2,4]triazin-2-yl]-[2-methoxy-4-(4-morpholin-4-yl-piperidin-1-yl)-phenyl]-amine 1451a) 7-(2-Isopropoxy-phenyl)-2-methylsulfanyl-pyrrolo[2,1-f][1,2,4]triazine: This compound was prepared according to Example 1446a. From 7-bromo-2-methylsulfanyl-pyrrolo[2,1-f][1,2,4]triazine (500 mg, 2.0 mmol) and 2-isopropoxybenzeneboronic acid (737 mg, 4.1 mmol) was obtained 500 mg of the title compound after flash chromatography on silica gel. MS=300 (M+1).

1451b) 7-(2-Isopropoxy-phenyl)-2-methanesulfinyl-pyrrolo[2,1-f][1,2,4]triazine: This compound was prepared according to Example 1449b. From 7-(2-Isopropoxy-phenyl)-2-methylsulfanyl-pyrrolo[2,1-f][1,2,4]triazine (475 mg, 1.59 mmol) and 70% m-CPBA (450 mg, 1.8 mmol) was obtained 358 mg of the title compound following flash chromatography on silica gel. MS=316 (M+1).

1451c) [7-(2-Isopropoxy-phenyl)-pyrrolo[2,1-f][1,2,4]triazin-2-yl]-[2-methoxy-4-(4-morpholin-4-yl-piperidin-1-yl)-phenyl]-amine: This compound was prepared according to the procedure for Example 1443c. From 7-(2-isopropoxy-phenyl)-2-methanesulfinyl-pyrrolo[2,1-f][1,2,4]triazine (140 mg, 0.43 mmol) and 2-methoxy-4-(4-morpholin-4-yl-piperidin-1-yl)-phenylamine (187 mg, 0.64 mmol) was obtained 92 mg of the title compound upon preparative RF-HPLC and free-basing. mp 149-151° C.; MS=543 (M+1); (DMSO-$d_6$, ppm): 8.87 (s, 1H), 7.98 (q, J=2 Hz, 8 Hz, 1H), 7.85 (d, J=8 Hz, 1H), 7.50 (s, 1H), 7.38 (m, 1H), 7.17 (d, J=8 Hz, 1H), 7.06 (t, J=8 Hz, 1H), 6.96 (q, J=5 Hz, 50 Hz, 2H), 6.64 (d, J=3 Hz, 1H), 6.38 (q, J=2 Hz, 9 Hz, 1H), 4.64 (m, 1H), 3.84 (s, 3H), 3.65 (m, 2H), 3.58 (m, 4H), 2.61 (m, 2H), 2.25 (m, 1H), 1.87 (m, 2H), 1.50 (m, 2H), 1.22 (d, J=6 Hz, 6H).

Example 1452

(1-Methoxy-7-morpholin-4-yl-6,7,8,9-tetrahydro-5H-benzo cyclohepten-2-yl)-[7-(2-methoxy-phenyl)-pyrrolo[2,1-f][1,2,4]triazin-2-yl]-amine 1452a) 4-(4-Bromo-1-methoxy-2-nitro-6,7,8,9-tetrahydro-5H-benzocyclohepten-7-yl)-morpholine: This compound was prepared according to the procedure for 1444a. From 4-bromo-1-methoxy-2-nitro-5,6,8,9-tetrahydro-benzocyclohepten-7-one (750 mg, 2.39 mmol) and morpholine (2.1 mL, 24 mmol was obtained 685 mg of the title compound as a yellow solid, used without further purification. MS=386 (M+1).

1452b) 1-Methoxy-7-morpholin-4-yl-6,7,8,9-tetrahydro-5H-benzocyclohepten-2-ylamine: This compound was prepared according to Example 1443b. From 4-(4-bromo-1-methoxy-2-nitro-6,7,8,9-tetrahydro-5H-benzocyclohepten-7-yl)-morpholine (500 mg, 1 mmol) was obtained 380 mg of the title compound as a yellow solid, used without further purification. MS=277 (M+1).

1452c) (1-Methoxy-7-morpholin-4-yl-6,7,8,9-tetrahydro-5H-benzocyclohepten-2-yl)-[7-(2-methoxy-phenyl)-pyrrolo[2,1-f][1,2,4]triazin-2-yl]-amine: This compound was prepared according to the procedure for Example 1443c. From 2-methanesulfinyl-7-(2-methoxy-phenyl)-pyrrolo[2,1-f][1,2,4]triazine (100 mg, 0.35 mmol) and 1-methoxy-7-morpholin-4-yl-6,7,8,9-tetrahydro-5H-benzocyclohepten-2-ylamine (144 mg, 0.52 mmol) was obtained 7 mg of the title compound following preparative RF-HPLC and free-basing. MS=500 (M+1); NMR (DMSO-$d_6$, ppm): 8.72 (s, 1H), 8.16 (d, J=8 Hz, 1H), 8.10 (s, 1H), 8.00 (q, J=2 Hz, 8 Hz, 1H), 7.45 (m, 1H), 7.39 (m, 1H), 7.15 (m, 1H), 7.10 (d, J=8 Hz, 1H), 6.86 (d, J=5 Hz, 1H), 6.83 (d, J=8 Hz, 1H), 3.87 (s, 3H), 3.77 (s, 3H), 3.73 (m, 4H), 3.34 (m, 1H), 2.83 (m, 1H), 2.60 (m, 6H), 2.39 (m, 1H), 1.43 (m, 2H), 1.28 (m, 2H).

Example 1453

N-(2-{2-[2-Methoxy-4-(4-morpholin-4-yl-piperidin-1-yl)-phenylamino]-pyrrolo[2,1-f][1,2,4]triazin-7-yl}-phenyl)-N-methyl-methanesulfonamide 1453a) N-(2-{2-[2-Methoxy-4-(4-morpholin-4-yl-piperidin-1-yl)-phenylamino]-pyrrolo[2,1-f][1,2,4]triazin-7-yl}-phenyl)-N-methyl-methanesulfonamide: This compound was prepared according to the procedure for 1443c. From N-[2-(2-methanesulfinyl-pyrrolo[2,1-f][1,2,4]triazin-7-yl)-phenyl]-N-methyl-methanesulfonamide (90 mg, 0.20 mmol) and 2-methoxy-4-(4-morpholin-4-yl-piperidin-1-yl)-phenylamine (108 mg, 0.37 mmol) was obtained 44 mg of the title compound upon preparative RF-HPLC and free-basing the isolated TFA-salt. mp 220-225° C. (dec); MS=592 (M+1); NMR (DMSO-$d_6$, ppm): 8.90 (s, 1H), 7.96 (m, 1H), 7.63 (m, 3H), 7.52 (m, 2H), 6.96 (d, J=4 Hz, 1H), 6.91 (d, J=4 Hz, 1H), 6.62 (d, J=4 Hz, 1H), 6.36 (q, J=2 Hz, 8 Hz, 1H), 3.80 (s, 3H), 3.66 (m, 2H), 3.58 (t, J=5 Hz, 4H), 3.32 (m, 4H), 3.05 (s, 3H), 2.88 (s, 3H), 2.62 (m, 2H), 2.25 (m, 1H), 1.86 (m, 2H), 1.50 (m, 2H).

Example 1454

1-(2-{2-[2-Methoxy-4-(4-morpholin-4-yl-piperidin-1-yl)-phenylamino]-pyrrolo[2,1-f][1,2,4]triazin-7-yl}-phenyl)-ethanone 1454a) 1-[2-(2-Methylsulfanyl-pyrrolo[2,1-f][1,2,4]triazin-7-yl)-phenyl]-ethanone: This compound was prepared according to Example 1447a. From 7-bromo-2-methylsulfanyl-pyrrolo[2,1-f][1,2,4]triazine (500 mg, 2.05 mmol) and 2-acetylbenzeneboronic acid (630 mg, 3.8 mmol) was obtained 780 mg of the title compound following flash chromatography on silica gel. MS=284 (M+1).

1454b) 1-[2-(2-Methanesulfinyl-pyrrolo[2,1-f][1,2,4]triazin-7-yl)-phenyl]-ethanone: This compound was prepared according to the procedure for Example 1449b. From 1-[2-(2-methylsulfanyl-pyrrolo[2,1-f][1,2,4]triazin-7-yl)-phenyl]-ethanone (375 mg, 1.32 mmol) and 70% m-CPBA (326 mg, 1.32 mmol) was obtained 254 mg of the title compound following flash chromatography on silica gel. MS=300 (M+1).

1454c) 1-(2-{2-[2-Methoxy-4-(4-morpholin-4-yl-piperidin-1-yl)-phenylamino]-pyrrolo[2,1-f][1,2,4]triazin-7-yl}-phenyl)-ethanone: This compound was prepared according to the procedure for Example 1443c. From 1-[2-(2-methanesulfinyl-pyrrolo[2,1-f][1,2,4]triazin-7-yl)-phenyl]-ethanone (89 mg, 0.30 mmol) and 2-methoxy-4-(4-morpholin-4-yl-piperidin-1-yl)-phenylamine (130 mg, 0.45 mmol) was obtained 45 mg of the title compound upon preparative RF-HPLC and free-basing of the TFA-salt. mp 170-173° C.; MS=527 (M+1); (DMSO-$d_6$, ppm): 8.89 (s, 1H), 7.84 (d, J=8 Hz, 1H), 7.67 (m, 1H), 7.58 (m, 3H), 7.46 (d, J=8 Hz, 1H), 6.90 (d, J=5 Hz, 1H), 6.82 (d, J=5 Hz, 1H), 6.58 (d, J=2 Hz, 1H), 6.33 (q, J=3 Hz, 8 Hz, 1H), 3.73 (s, 3H), 3.65 (d, J=12 Hz, 2H), 3.59 (t, J=5 Hz, 4H), 3.32 (m, 5H), 2.62 (m, 2H), 2.15 (s, 3H), 1.86 (m, 2H), 1.49 (m, 2H).

Example 1455

[2-Methoxy-4-(4-morpholin-4-yl-piperidin-1-yl)-phenyl]-[7-(2-trifluoromethoxy-phenyl)-pyrrolo[2,1-f][1,2,4]triazin-2-yl]-amine 1455a) 2-Methylsulfanyl-7-(2-trifluoromethoxy-phenyl)-pyrrolo[2,1-f][1,2,4]triazine: This compound was prepared according to the procedure for Example 1447a. From 7-bromo-2-methylsulfanyl-pyrrolo[2,1-f][1,2,4]triazine (300 mg, 1.23 mmol) and 2-(trifluoromethoxy)benzeneboronic acid (506.1 mg, 2.458 mmol) was obtained 307 mg of the title compound following work-up and flash chromatography on silica gel. MS=326 (M+1).

1455b) 2-Methanesulfinyl-7-(2-trifluoromethoxy-phenyl)-pyrrolo[2,1-f][1,2,4]triazine: This compound was prepared according to the procedure for Example 1449b. From 2-methylsulfanyl-7-(2-trifluoromethoxy-phenyl)-pyrrolo[2,1-f][1,2,4]triazine (305 mg, 0.94 mmol) and 70% m-CPBA (243 mg, 0.98 mmol) was obtained 259 mg of the purified product as a yellow solid following flash chromatography on silica gel. mp 88-93° C.; MS=342 (M+1).

1455c) [2-Methoxy-4-(4-morpholin-4-yl-piperidin-1-yl)-phenyl]-[7-(2-trifluoromethoxy-phenyl)-pyrrolo[2,1-f][1,2,4]triazin-2-yl]-amine: This compound was prepared according to the procedure for Example 1443c. From 2-methoxy-4-

(4-morpholin-4-yl-piperidin-1-yl)-phenylamine (160 mg, 0.55 mmol) and 2-methanesulfinyl-7-(2-trifluoromethoxy-phenyl)-pyrrolo[2,1-f][1,2,4]triazine (125 mg, 0.36 mmol) was obtained 57 mg of the title compound upon preparative RF-HPLC and free-basing of the TFA-salt. mp 185-191° C. (dec.); MS=568 (M+1); NMR (DMSO-d$_6$, ppm): 8.96 (s, 1H), 8.09 (m, 1H), 7.71 (d, J=8 Hz, 1H), 7.66 (s, 1H), 7.56 (m, 3H), 6.94 (q, J=2 Hz, 5 Hz, 2H), 6.64 (d, J=3 Hz, 1H), 3.83 (s, 3H), 3.67 (m, 2H), 3.58 (m, 4H), 3.31 (m, 4H), 2.61 (m, 3H), 2.25 (m, 1H), 1.86 (d, J=12 Hz, 2H), 1.50 (m, 2H).

Example 1456

N-Methyl-N-(2-{2-[4-(4-morpholin-4-yl-piperidin-1-yl)-phenylamino]-pyrrolo[2,1-f][1,2,4]triazin-7-yl}-phenyl)-methanesulfonamide, trifluoroacetic acid salt 1456a) N-Methyl-N-(2-{2-[4-(4-morpholin-4-yl-piperidin-1-yl)-phenylamino]-pyrrolo[2,1-f][1,2,4]triazin-7-yl}-phenyl)-methanesulfonamide, trifluoroacetic acid salt: This compound was prepared according to the procedure for Example 1443c. From N-[2-(2-methanesulfinyl-pyrrolo[2,1-f][1,2,4]triazin-7-yl)-phenyl]-N-methyl-methanesulfonamide (90 mg, 0.2 mmol) and 4-(4-morpholin-4-yl-piperidin-1-yl)-phenylamine (97 mg, 0.37 mmol) was obtained 25 mg of the title compound upon preparative RF-HPLC. MS=562 (M+1); NMR (DMSO-d$_6$, ppm): 9.73 (s, 1H), 9.22 (s, 1H), 8.94 (s, 1H), 8.02 (d, J=9 Hz, 1H), 7.66 (d, J=9 Hz, 1H), 7.56 (m, 4H), 6.98 (d, J=5 Hz, 1H), 6.93 (d, J=5 Hz, 1H), 6.88 (d, J=8 Hz, 2H), 4.02 (m, 2H), 3.71 (m, 4H), 3.48 (m, 2H), 3.33 (m, 1H), 3.09 (m, 6H), 2.90 (s, 3H), 2.68 (m, 2H), 2.14 (m, 2H), 1.72 (m, 2H).

Example 1457

N-(2-{2-[2-Methoxy-4-(4-methyl-piperazin-1-yl)-phenylamino]-pyrrolo[2,1-f][1,2,4]triazin-7-yl}-phenyl)-N-methyl-methanesulfonamide 1457a) N-(2-{2-[2-Methoxy-4-(4-methyl-piperazin-1-yl)-phenylamino]-pyrrolo[2,1-f][1,2,4]triazin-7-yl}-phenyl)-N-methyl-methanesulfonamide: This compound was prepared according to the procedure for Example 1443c. From N-[2-(2-methanesulfinyl-pyrrolo[2,1-f][1,2,4]triazin-7-yl)-phenyl]-N-methyl-methanesulfonamide (90 mg, 0.20 mmol) and 2-methoxy-4-(4-methyl-piperazin-1-yl)-phenylamine (82 mg, 0.37 mmol) was obtained 28 mg of the title compound upon preparative RF-HPLC. MS=522 (M+1); NMR (DMSO-d$_6$, ppm): 9.65 (br, 1H), 8.92 (s, 1H), 7.98 (d, J=8 Hz, 1H), 7.75 (d, J=9 Hz, 1H), 7.64 (m, 2H), 7.53 (m, 2H), 6.96 (q, J=5, 19 Hz, 2H), 6.71 (s, 1H), 6.43 (d, J=9 Hz, 1H), 3.84 (s, 3H), 3.79 (m, 2H), 3.53 (d, J=12 Hz, 2H), 3.17 (q, J=12 Hz, 2H), 3.08 (s, 3H), 2.93 (m, 2H), 2.88 (m, 6H).

Example 1458

N-[2-(2-{4-[4-((S)-2-Hydroxy-propyl)-piperazin-1-yl]-2-methoxy-phenylamino}-pyrrolo[2,1-f][1,2,4]triazin-7-yl)-phenyl]-N-methyl-methanesulfonamide 1458a) N-[2-(2-{4-[4-((S)-2-Hydroxy-propyl)-piperazin-1-yl]-2-methoxy-phenylamino}-pyrrolo[2,1-f][1,2,4]triazin-7-yl)-phenyl]-N-methyl-methanesulfonamide: This compound was prepared according to the procedure for Example 1443c. From N-[2-(2-methanesulfinyl-pyrrolo[2,1-f][1,2,4]triazin-7-yl)-phenyl]-N-methylmethane sulfonamide (90 mg, 0.20 mmol) and (S)-1-[4-(4-amino-3-methoxy-phenyl)-piperazin-1-yl]-propan-2-ol (98 mg, 0.37 mmol) was obtained 44 mg of the title compound upon preparative RF-HPLC and free-basing the trifluoroacetate salt. MS=566 (M+1); NMR (DMSO-d$_6$, ppm): 8.90 (s, 1H), 7.97 (m, 1H), 7.63 (m, 3H), 7.53 (m, 2H), 6.94 (dd, J=5 Hz, 22 Hz, 2H), 6.62 (m, 1H), 6.35 (d, J=9 Hz, 1H), 4.31 (m, 1H), 3.80 (m, 4H), 3.32 (s, 3H), 3.05 (s, 3H), 2.88 (s, 3H), 2.56 (m, 4H), 2.26 (m, 2H), 1.07 (d, J=6 Hz, 3H).

Example 1459

N-[2-(2-{4-[4-((R)-2-Hydroxy-propyl)-piperazin-1-yl]-2-methoxy-phenylamino}-pyrrolo[2,1-f][1,2,4]triazin-7-yl)-phenyl]-N-methyl-methanesulfonamide; compound with trifluoro-acetic acid 1459a) N-[2-(2-{4-[4-((R)-2-Hydroxy-propyl)-piperazin-1-yl]-2-methoxy-phenylamino}-pyrrolo[2,1-f][1,2,4]triazin-7-yl)-phenyl]-N-methyl-methanesulfonamide; compound with trifluoro-acetic acid: This compound was prepared according to the procedure for Example 1443c. From N-[2-(2-methanesulfinyl-pyrrolo[2,1-f][1,2,4]triazin-7-yl)-phenyl]-N-methyl-methanesulfonamide (90 mg, 0.20 mmol) and (R)-1-[4-(4-amino-3-methoxy-phenyl)-piperazin-1-yl]-propan-2-ol (98 mg, 0.37 mmol) afforded 28 mg of a burnt-orange powder upon preparative RF-HPLC. MS=566 (M-TFA+1); NMR (DMSO-d$_6$, ppm): 9.48 (br, 1H), 8.93 (s, 1H), 7.97 (m, 1H), 7.75 (d, J=8 Hz, 1H), 7.65 (m, 2H), 7.53 (m, 2H), 6.94 (dd, J=5 Hz, 22 Hz, 2H), 6.70 (m, 1H), 6.43 (d, J=9 Hz, 1H), 4.13 (m, 1H), 3.83 (m, 3H), 3.76 (m, 2H), 3.58 (m, 2H), 3.20 (m, 4H), 3.07 (s, 3H), 3.03 (s, 2H), 2.88 (s, 3H), 1.15 (d, J=6 Hz, 3H).

Example 1460

N-Ethyl-N-(2-{2-[2-methoxy-4-(4-morpholin-4-yl-piperidin-1-yl)-phenylamino]-pyrrolo[2,1-f][1,2,4]triazin-7-yl}-phenyl)-methanesulfonamide 1460a) N-Ethyl-N-[2-(2-methanesulfinyl-pyrrolo[2,1-f][1,2,4]triazin-7-yl)-phenyl]-methanesulfonamide: This compound was prepared according to the procedure for Example 1449c. From N-[2-(2-methanesulfinyl-pyrrolo[2,1-f][1,2,4]triazin-7-yl)-phenyl]-methanesulfonamide (150 mg, 0.43 mmol), potassium carbonate (237 mg, 1.7 mmol) and iodo-ethane (103 uL, 1.28 mmol) in DMF (5 mL) was obtained 112 mg of the purified product as a yellow solid following flash chromatography over silica gel. mp 186-190° C.; MS=379 (M+1).

1460b) N-Ethyl-N-(2-{2-[2-methoxy-4-(4-morpholin-4-yl-piperidin-1-yl)-phenylamino]-pyrrolo[2,1-f][1,2,4]triazin-7-yl}-phenyl)-methanesulfonamide: This compound was prepared according to the procedure for Example 1443c. From N-ethyl-N-[2-(2-methanesulfinyl-pyrrolo[2,1-f][1,2,4]triazin-7-yl)-phenyl]-methanesulfonamide (100 mg, 0.26 mmol) and 2-methoxy-4-(4-morpholin-4-yl-piperidin-1-yl)-phenylamine (163 mg, 0.56 mmol) afforded 66 mg of the title compound following preparative RF-HPLC and free-basing of the trifluoroacetate salt. mp 227-231° C. (dec); MS=606 (M=1); NMR (DMSO-d$_6$, ppm): 8.91 (s, 1H), 7.98 (d, J=7 Hz, 1H), 7.72 (d, J=7 Hz, 1H), 7.65 (m, 4H), 7.10 (d, J=5 Hz, 1H), 6.92 (d, J=5 Hz, 1H), 6.63 (s, 1H), 6.34 (d, J=8 Hz, 1H), 3.83 (s, 3H), 3.65 (d, J=12 Hz, 2H), 3.59 (m, 4H), 3.36 (q, J=8 Hz, 2H), 3.31 (m, 2H), 3.06 (s, 3H), 2.62 (t, J=12 Hz, 2H), 2.25 (m, 1H), 1.87 (d, J=12 Hz, 2H), 1.50 (q, J=12 Hz, 2H), 1.09 (m, 1H), 0.70 (t, J=7 Hz, 3H).

Example 1461

N-Cyclopropylmethyl-N-(2-{2-[2-methoxy-4-(4-morpholin-4-yl-piperidin-1-yl)-phenylamino]-pyrrolo[2,1-f][1,2,4]triazin-7-yl}-phenyl)-methanesulfonamide 1461a) N-Cyclopropylmethyl-N-[2-(2-methanesulfinyl-pyrrolo[2,1-f][1,2,4]triazin-7-yl)-phenyl]-methanesulfonamide: This compound was prepared according to the procedure for Example 1449c. From N-[2-(2-methanesulfinyl-pyrrolo[2,1-f][1,2,4]triazin-7-yl)-phenyl]-methanesulfonamide (150 mg, 0.43 mmol) and cyclopropylmethyl bromide (125 L, 1.28 mmol) was obtained 140 mg of the title compound as a yellow solid following flash chromatography. MS=405 (M+1).

1461b) N-Cyclopropylmethyl-N-(2-{2-[2-methoxy-4-(4-morpholin-4-yl-piperidin-1-yl)-phenylamino]-pyrrolo[2,1-f][1,2,4]triazin-7-yl}-phenyl)-methanesulfonamide: This compound was prepared according to the procedure for Example 1443c. From N-cyclo-propylmethyl-N-[2-(2-methanesulfinyl-pyrrolo[2,1-f][1,2,4]triazin-7-yl)-phenyl]-methanesulfonamide (74 mg, 0.18 mmol) and 2-methoxy-4-(4-morpholin-4-yl-piperidin-1-yl)-phenylamine (107 mg, 0.37 mmol) was obtained 40 mg of the title compound upon preparative RF-HPLC and free-basing. mp 202-207° C.; MS=632 (M+1); NMR (DMSO-$d_6$, ppm): 8.90 (s, 1H), 8.00 (d, J=8 Hz, 1H), 7.76 (d, J=8 Hz, 1H), 7.66 (d, J=8 Hz, 1H), 7.56 (m, 2H), 7.50 (s, 1H), 7.18 (d, J=5 Hz, 1H), 6.92 (d, J=5 Hz, 1H), 6.63 (s, 1H), 6.32 (d, J=9 Hz, 1H), 3.84 (s, 3H), 3.65 (d, J=12 Hz, 2H), 3.59 (m, 4H), 3.39 (m, 1H), 3.32 (s, 1H), 3.07 (m, 4H), 2.61 (t, J=12 Hz, 2H), 2.25 (m, 1H), 1.87 (d, J=12 Hz, 2H), 1.50 (q, J=12 Hz, 2H), 1.10 (t, J=7 Hz, 1H), 0.54 (m, 1H), 0.09 (m, 3H), −0.20 (m, 2H).

Example 1462

N-(2-Methoxy-ethyl)-N-(2-{2-[2-methoxy-4-(4-morpholin-4-yl-piperidin-1-yl)-phenylamino]-pyrrolo[2,1-f][1,2,4]triazin-7-yl}-phenyl)-methanesulfonamide 1462a) N-[2-(2-Methanesulfinyl-pyrrolo[2,1-f][1,2,4]triazin-7-yl)-phenyl]-N-(2-methoxy-ethyl)-methanesulfonamide: This compound was prepared according to the procedure for Example 1449c. From N-[2-(2-methanesulfinyl-pyrrolo[2,1-f][1,2,4]triazin-7-yl)-phenyl]-methanesulfonamide (150 mg, 0.43 mmol) and 1-bromo-2-methoxy-ethane (120 L, 1.28 mmol) was obtained 110 mg of the title compound as a yellow solid following flash chromatography on silica gel. MS=409 (M+1).

1462b) N-(2-Methoxy-ethyl)-N-(2-{2-[2-methoxy-4-(4-morpholin-4-yl-piperidin-1-yl)-phenylamino]-pyrrolo[2,1-f][1,2,4]triazin-7-yl}-phenyl)-methanesulfonamide: This compound was prepared according to the procedure for Example 1443c. From N-[2-(2-methanesulfinyl-pyrrolo[2,1-f][1,2,4]triazin-7-yl)-phenyl]-N-(2-methoxy-ethyl)-methanesulfonamide (75 mg, 0.18 mmol) and 2-methoxy-4-(4-morpholin-4-yl-piperidin-1-yl)-phenylamine (107 mg, 0.37 mmol) was obtained 50 mg of the title compound as a yellow solid upon preparative RF-HPLC and free-basing. mp 97-101° C.; MS=636 (M+1); NMR (DMSO-$d_6$, ppm): 8.91 (s, 1H), 8.02 (d, J=9 Hz, 1H), 7.71 (d, J=9 Hz, 1H), 7.56 (m, 4H), 7.18 (d, J=5 Hz, 1H), 6.92 (d, J=5 Hz, 1H), 6.63 (s, 1H), 6.34 (d, J=9 Hz, 1H), 3.83 (s, 3H), 3.65 (m, 3H), 3.58 (m, 5H), 3.31 (s, 3H), 3.11 (m, 5H), 3.00 (s, 3H), 2.62 (m, 3H), 2.25 (m, 1H), 1.87 (d, J=12 Hz, 2H), 1.50 (q, J=12 Hz, 2H).

Example 1463

N-(2-Fluoro-ethyl)-N-(2-{2-[2-methoxy-4-(4-morpholin-4-yl-piperidin-1-yl)-phenylamino]-pyrrolo[2,1-f][1,2,4]triazin-7-yl}-phenyl)-methanesulfonamide 1463a) N-(2-Fluoro-ethyl)-N-[2-(2-methanesulfinyl-pyrrolo[2,1-f][1,2,4]triazin-7-yl)-phenyl]-methanesulfonamide: This compound was prepared according to the procedure for Example 1449c. From N-[2-(2-methanesulfinyl-pyrrolo[2,1-f][1,2,4]triazin-7-yl)-phenyl]-methanesulfonamide (200 mg, 0.57 mmol) and 1-bromo-2-fluoroethane (106 L, 1.43 mmol) was obtained 156 mg of the title compound as a yellow solid following flash chromatography on silica gel. MS=397 (M+1).

1463b) N-(2-Fluoro-ethyl)-N-(2-{2-[2-methoxy-4-(4-morpholin-4-yl-piperidin-1-yl)-phenylamino]-pyrrolo[2,1-f][1,2,4]triazin-7-yl}-phenyl)-methanesulfonamide: This compound was prepared according to the procedure for 1443c. From N-(2-fluoro-ethyl)-N-[2-(2-methanesulfinyl-pyrrolo[2,1-f][1,2,4]triazin-7-yl)-phenyl]-methanesulfonamide (75 mg, 0.19 mmol) and 2-methoxy-4-(4-morpholin-4-yl-piperidin-1-yl)-phenylamine (110 mg, 0.38 mmol) was obtained 50 mg of the title compound as a yellow solid upon preparative RF-HPLC and free-basing. MS=624 (M+1); NMR (DMSO-$d_6$, ppm): 8.92 (s, 1H), 8.02 (d, J=7 Hz, 1H), 7.70 (d, J=7 Hz, 1H), 7.63 (d, J=7 Hz, 1H), 7.56 (m, 3H), 7.14 (d, J=5 Hz, 1H), 6.92 (d, J=5 Hz, 1H), 6.63 (s, 1H), 6.35 (d, J=7 Hz, 1H), 4.30 (s, 1H), 4.18 (s, 1H), 3.82 (s, 3H), 3.66 (d, J=11 Hz, 3H), 3.58 (m, 5H), 3.09 (s, 3H), 2.62 (m, 3H), 2.26 (m, 1H), 1.87 (d, J=12 Hz, 2H), 1.50 (q, J=12 Hz, 2H).

Example 1464

[2-Methoxy-4-(4-morpholin-4-yl-piperidin-1-yl)-phenyl]-[7-(2-trifluoromethyl-phenyl)-pyrrolo[2,1-f][1,2,4]triazin-2-yl]-amine 1464a) 2-Methylsulfanyl-7-(2-trifluoromethyl-phenyl)-pyrrolo[2,1-f][1,2,4]triazine: This compound was prepared according to the procedure for Example 1447a. From 7-bromo-2-methylsulfanyl-pyrrolo[2,1-f][1,2,4]triazine (300 mg, 1.23 mmol) and 2-(trifluoromethyl)benzeneboronic acid (467 mg, 2.46 mmol) was obtained 285 mg of the title compound as a yellow solid following flash chromatography on silica gel. mp 109-113° C.; MS=310 (M+1).

1464b) 2-Methanesulfinyl-7-(2-trifluoromethyl-phenyl)-pyrrolo[2,1-f][1,2,4]triazine: This compound was prepared according to the procedure for Example 1449b. From 2-methylsulfanyl-7-(2-trifluoromethyl-phenyl)-pyrrolo[2,1-f][1,2,4]triazine (270 mg, 0.87 mmol) and 70% m-CPBA (230 mg, 0.93 mmol) was obtained 128 mg of the title compound as a yellow solid following flash chromatography on silica gel. mp 164-167° C.; MS=326 (M+1).

1464c) [2-Methoxy-4-(4-morpholin-4-yl-piperidin-1-yl)-phenyl]-[7-(2-trifluoromethyl-phenyl)-pyrrolo[2,1-f][1,2,4]triazin-2-yl]-amine: This compound was prepared according to the procedure for Example 1443c. From 2-methanesulfinyl-7-(2-trifluoromethyl-phenyl)-pyrrolo[2,1-f][1,2,4]triazine (60 mg, 0.18 mmol) and 2-methoxy-4-(4-morpholin-4-yl-piperidin-1-yl)-phenylamine (107 mg, 0.37 mmol) was obtained 45 mg of the title compound as a yellow solid upon preparative RF-HPLC and free-basing. mp 191-195° C.; MS=553 (M+1); NMR (DMSO-$d_6$, ppm): 8.95 (s, 1H), 7.93

(d, J=8 Hz, 1H), 7.85 (m, 1H), 7.78 (d, J=8 Hz, 1H), 7.72 (m, 1H), 7.54 (m, 2H), 6.94 (d, J=5 Hz, 1H), 6.80 (d, 5 Hz, 1H), 6.59 (s, 1H), 6.22 (d, J=8 Hz, 1H), 3.81 (s, 3H), 3.59 (m, 6H), 3.31 (s, 4H), 2.58 (t, J=11 Hz, 2H), 2.24 (m, 1H), 1.85 (d, J=12 Hz, 2H), 1.48 (q, J=12 Hz, 2H).

Example 1465

[7-(2,3-Dimethoxy-phenyl)-pyrrolo[2,1-f][1,2,4]triazin-2-yl]-[2-methoxy-4-(4-morpholin-4-yl-piperidin-1-yl)-phenyl]-amine 1465a) 7-(2,3-Dimethoxy-phenyl)-2-methylsulfanyl-pyrrolo[2,1-f][1,2,4]triazine: This compound was prepared according to the procedure for Example 1447a. From 7-bromo-2-methylsulfanyl-pyrrolo[2,1-f][1,2,4]triazine (300 mg, 1.23 mmol) and 2,3-dimethoxybenzeneboronic acid (447 mg, 2.46 mmol) was obtained 310 mg of the purified product. following flash chromatography on silica gel. mp 74-79° C.; MS=302.

1465b) 7-(2,3-Dimethoxy-phenyl)-2-methanesulfinyl-pyrrolo[2,1-f][1,2,4]triazine: This compound was prepared according to the procedure for Example 1449b. From 7-(2,3-dimethoxy-phenyl)-2-methylsulfanyl-pyrrolo[2,1-f][1,2,4]triazine (290 mg, 0.96 mmol) and 70% m-CPBA (254 mg, 1.03 mmol) was obtained 220 mg of the purified product as a yellow solid following flash chromatography on silica gel. MS=318 (M+1).

1465c) [7-(2,3-Dimethoxy-phenyl)-pyrrolo[2,1-f][1,2,4]triazin-2-yl]-[2-methoxy-4-(4-morpholin-4-yl-piperidin-1-yl)-phenyl]-amine: This compound was prepared according to the procedure for Example 1443c. From 7-(2,3-dimethoxy-phenyl)-2-methanesulfinyl-pyrrolo[2,1-f][1,2,4]triazine (58 mg, 0.18 mmol) and 2-methoxy-4-(4-morpholin-4-yl-piperidin-1-yl)-phenylamine (107 mg, 0.37 mmol) was obtained 33 mg of the title compound as a yellow solid upon preparative RF-HPLC and free-basing. mp 143-148° C.; MS=545 (M+1); NMR (DMSO-$d_6$, ppm): 8.90 (s, 1H), 7.80 (d, J=8 Hz, 1H), 7.55 (s, 2H), 7.20 (d, J=7 Hz, 1H), 7.13 (J=7 Hz, 1H), 6.99 (d, J=6 Hz, 1H), 6.92 (d, J=6 Hz, 1H), 6.64 (s, 1H), 6.37 (d, J=7 Hz, 1H), 3.88 (s, 3H), 3.83 (s, 3H), 3.66 (d, J=12 Hz, 2H), 3.59 (s+m, 7H), 3.31 (s, 2H), 2.63 (t, J=12 Hz, 2H), 2.25 (m, 1H), 1.87 (d, J=12 Hz, 2H), 1.51 (q, J=12 Hz, 2H), 1.24 (m, 2H).

Example 1466

[7-(2-Chloro-phenyl)-pyrrolo[2,1-f][1,2,4]triazin-2-yl]-[2-methoxy-4-(4-morpholin-4-yl-piperidin-1-yl)-phenyl]-amine; compound with trifluoroacetic acid 1465a) 7-(2-Chloro-phenyl)-2-methylsulfanyl-pyrrolo[2,1-f][1,2,4]triazine: This compound was prepared according to the procedure for Example 1447a. From 7-bromo-2-methylsulfanyl-pyrrolo[2,1-f][1,2,4]triazine (250 mg, 1.0 mmol) and 2-chlorophenyl boronic acid (320 mg, 2.05 mmol) was obtained 201 mg of the purified product as a yellow solid following flash chromatography on silica gel. mp 96-100° C.; MS=276 (M+1).

1466b) 7-(2-Chloro-phenyl)-2-methanesulfinyl-pyrrolo[2,1-f][1,2,4]triazine: This compound was prepared according to the procedure for Example 1449b. From 7-(2-chloro-phenyl)-2-methylsulfanyl-pyrrolo[2,1-f][1,2,4]triazine (220 mg, 0.80 mmol) and 70% m-CPBA 70-75% (206 mg, 0.84 mmol) was obtained 186 mg of the title compound as a mustard yellow solid upon workup, used without further purification.

1466c) [7-(2-Chloro-phenyl)-pyrrolo[2,1-f][1,2,4]triazin-2-yl]-[2-methoxy-4-(4-morpholin-4-yl-piperidin-1-yl)-phenyl]-amine; compound with trifluoroacetic acid: This compound was prepared according to the procedure for Example 1443c. From 7-(2-chloro-phenyl)-2-methanesulfinyl-pyrrolo[2,1-f][1,2,4]triazine (75 mg, 0.26 mmol) and 2-methoxy-4-(4-morpholin-4-yl-piperidin-1-yl)-phenylamine (150 mg, 0.51 mmol) was obtained 66 mg of the title compound as a yellow solid upon preparative RF-HPLC and lyophilization. MS=519 (M-TFA+1); NMR (DMSO-$d_6$, ppm): 9.72 (s, 1H), 8.97 (s, 1H), 7.78 (d, J=8 Hz, 2H), 7.67 (m, 1H), 7.61 (s, 1H), 7.51 (m, 2H), 6.96 (s, 2H), 6.69 (s, 1H), 6.38 (d, J=8 Hz, 1H), 4.04 (d, J=12 Hz, 2H), 3.85 (s, 3H), 3.81 (d, J=12 Hz, 2H), 3.68 (t, J=12 Hz, 2H), 3.50 (d, J=12 Hz, 2H), 3.13 (m, 2H), 2.70 (t, J=12 Hz, 2H), 2.14 (d, J=12 Hz, 2H), 1.71 (q, J=12 Hz, 2H).

Example 1467

2-Methoxy-4-(4-methyl-4-morpholin-4-yl-piperidin-1-yl)-phenyl]-[7-(2-methoxy-phenyl)-pyrrolo[2,1-f][1,2,4]triazin-2-yl]-amine; compound with trifluoroacetic acid 1467a) 4-Methyl-4-morpholin-4-yl-piperidine-1-carboxylic acid tert-butyl ester: To a flask equipped with a Dean-Stark trap was added 4-oxo-piperidine-1-carboxylic acid tert-butyl ester (5.0 g, 25 mmol), morpholine (2.4 g, 28 mmol), and 1H-1,2,3-triazole (2.1 g, 30 mmol) in toluene (30 mL). The mixture was stirred under nitrogen while being heated to reflux over 6-8 hrs while collecting the water produced. The mixture was allowed to cool to RT overnight, giving a solid amber mass. This was dissolved with anhydrous THF (25 mL) and added to 3.0 M of methylmagnesium chloride in tetrahydrofuran (33.4 mL, 100 mmol) over 30-40 min, keeping the internal temperature below 25° C. The mixture was stirred further for 1 hr and quenched via addition of 20% NH$_4$Cl, keeping the temperature below 30° C. The organic phase was separated and the aqueous phase was extracted with ethyl acetate. The combined organic phase was washed with brine, dried (MgSO4), filtered and concentrated to give 7.0 g of the title compound, which slowly solidified to an amber wax and was used without further purification. MS=285 (M+1).

1467b) 4-(4-Methyl-piperidin-4-yl)-morpholine; compound with bis-trifluoro-acetic: To a flask containing 4-methyl-4-morpholin-4-yl-piperidine-1-carboxylic acid tert-butyl ester (7.1 g, 25 mmol) in dichloromethane (10 mL) was added 10 M of trifluoroacetic acid in dichloromethane (100 mL). The mixture was stirred at room temperature for 3 hrs when the mixture was concentrated and repeatedly triturated and concentrated with methylene chloride, then ether, and the solid produced was dried overnight in vaccuo to give 14.3 g of a tan solid. The sample was slurried in EtOAc (~75 mL) for about an hour, filtered, washed with a little EtOAc and Et2O and air-dried to give 3.1 g of the product as a white solid. The mother liquors were concentrated and the residue was slurried in a mixture of EtOAc (10 mL)/Et2O (100 mL) for several hours, filtered and the solid was washed with EtOAc/Et2O (1/1) to give an additional 5.6 g of the product as a tan solid. mp 199-208° C.; MS=185 (M−2TFA+1).

1467c) 4-[1-(3-Methoxy-4-nitro-phenyl)-4-methyl-piperidin-4-yl]-morpholine: To a mixture of 4-(4-methyl-piperidin-4-yl)-morpholine; compound with bis-trifluoroacetic acid (4.0 g, 9.7 mmol) and potassium carbonate (4.7 g, 34 mmol) in DMF (75 mL) was added 4-fluoro-2-methoxy-1-nitro-benzene (1.7 g, 10.2 mmol) with stirring. The mixture was heated at 60° C. for 18 hours, then filtered and concentrated. The residue was dissolved in dichloromethane and washed with saturated aqueous sodium bicarbonate and brine, dried (MgSO4). Flash chromatography on silica gel gave 3.27 g of the purified product as a yellow solid. mp 163-166° C.; MS=336 (M+1).

1467d) 2-Methoxy-4-(4-methyl-4-morpholin-4-yl-piperidin-1-yl)-phenylamine: This compound was prepared according to the procedure for 1443b. From 4-[1-(3-methoxy-4-nitro-phenyl)-4-methyl-piperidin-4-yl]-morpholine (3.0 g, 8.9 mmol) was obtained 2.67 g of the title compound, used without further purification. MS=306 (M+1).

1467e) 2-Methoxy-4-(4-methyl-4-morpholin-4-yl-piperidin-1-yl)-phenyl]-[7-(2-methoxy-phenyl)-pyrrolo[2,1-f][1,2,4]triazin-2-yl]-amine; compound with trifluoroacetic acid: This compound was prepared according to the procedure for Example 1443c. From 2-methanesulfinyl-7-(2-methoxy-phenyl)-pyrrolo[2,1-f][1,2,4]triazine (74 mg, 0.26 mmol) and 2-methoxy-4-(4-methyl-4-morpholin-4-yl-piperidin-1-yl)-phenylamine (157 mg, 0.51 mmol) was obtained 83 mg of the title compound as a yellow solid upon preparative RF-HPLC and lyophilization. MS=529 (M-TFA+1); NMR (DMSO-$d_6$, ppm): 9.49 (s, 1H), 8.91 (s, 1H), 7.90 (d, J=8 Hz, 1H), 7.85 (d, J=8 Hz, 1H), 7.54 (s, 1H), 7.45 (t, J=8 Hz, 1H), 7.21 (d, J=8 Hz, 1H), 7.10 (t, J=8 Hz, 1H), 6.94 (q, J=4 Hz, 20 Hz, 2H), 6.71 (s, 1H), 6.46 (d, J=8 Hz, 1H), 4.03 (d, J=12 Hz, 2H), 3.87 (s, 3H), 3.80 (s, 3H), 3.75 (d, J=12 Hz, 4H), 3.44 (d, J=12 Hz, 2H), 3.14 (m, 2H), 2.88 (t, J=12 Hz, 2H), 1.90 (m, 4H), 1.41 (s, 3H).

Example 1468

N-(2-{2-[2-Methoxy-4-(4-methyl-4-morpholin-4-yl-piperidin-1-yl)-phenylamino]-pyrrolo[2,1-f][1,2,4]triazin-7-yl}-phenyl)-N-methyl-methanesulfonamide; compound with trifluoroacetic acid 1468a) N-(2-{2-[2-Methoxy-4-(4-methyl-4-morpholin-4-yl-piperidin-1-yl)-phenylamino]-pyrrolo[2,1-f][1,2,4]triazin-7-yl}-phenyl)-N-methyl-methanesulfonamide; compound with trifluoroacetic acid: This compound was prepared according to the procedure for Example 1443c. From N-[2-(2-methanesulfinyl-pyrrolo[2,1-f][1,2,4]triazin-7-yl)-phenyl]-N-methyl-methanesulfonamide (94 mg, 0.26 mmol) and 2-methoxy-4-(4-methyl-4-morpholin-4-yl-piperidin-1-yl)-phenylamine (157 mg, 0.51 mmol) was obtained 60 mg of the title compound as an amber solid upon preparative RF-HPLC and lyophilization. MS=606 (M-TFA+1); NMR (DMSO-$d_6$, ppm): 9.35 (br, 1H), 8.91 (s, 1H), 7.98 (d, 1H), 7.71 (d, J=8 Hz, 1H), 7.63 (s, 2H), 7.53 (m, 2H), 6.95 (q, J=4 Hz, 20 Hz, 2H), 6.67 (s, 1H), 6.43 (d, J=8 Hz, 1H), 4.04 (d, J=12 Hz, 2H), 3.84 (s, 3H), 3.74 (m, 4H), 3.43 (d, J=12 Hz, 2H), 3.14 (m, 2H), 3.09 (s, 3H), 2.88 (s+m, 5H), 1.88 (m, 4H), 1.40 (s, 3H).

Example 1469

N-(2-{2-[4-(4,4-Difluoro-piperidin-1-yl)-2-methoxy-phenylamino]-pyrrolo[2,1-f][1,2,4]triazin-7-yl}-phenyl)-N-methyl-methanesulfonamide; compound with trifluoroacetic acid 1469a) 4-Fluoro-2-methoxy-1-nitro-benzene: To a solution of 5-fluoro-2-nitro-phenol (25.0 g, 0.16 mol) in DMF (250 mL) was added potassium carbonate (47 g, 0.34 mol) followed by dimethyl sulfate (12 mL, 0.13 mol). The mixture was stirred at room temperature for 18 hours and treated with additional potassium carbonate (20 g) and dimethyl sulfate (12 mL) and stirred at room temperature for a further five hours until compete by HPLC. The mixture was concentrated on the rotovap, water (250 mL) was added and the mixture was stirred at room temperature overnight. The solid was collected by vacuum filtration, washed with water to neutral pH and dried to constant weight to give 22 g of the title compound as an off-white solid. MS=172 (M+1).

1469b) 4,4-Difluoro-1-(3-methoxy-4-nitro-phenyl)-piperidine: This compound was prepared according to the procedure for Example 1467c. From 4,4-difluoropiperidine; hydrochloride (3.00 g, 19.0 mmol) and 4-fluoro-2-methoxy-1-nitrobenzene (3.3 g, 19.0 mmol) was obtained 4.50 g of the title compound as a yellow solid. MS=273 (M+1).

1469c) 4-(4,4-Difluoro-piperidin-1-yl)-2-methoxy-phenylamine: This compound was prepared according to the procedure for Example 1443b. From 4,4-difluoro-1-(3-methoxy-4-nitro-phenyl)-piperidine (2.50 g, 9.18 mmol) was obtained 2.2 g of the title compound, used without further purification. MS=243 (M+1).

1469d) N-(2-{2-[4-(4,4-Difluoro-piperidin-1-yl)-2-methoxy-phenylamino]-pyrrolo[2,1-f][1,2,4]triazin-7-yl}-phenyl)-N-methyl-methanesulfonamide; compound with trifluoro-acetic acid: This compound was prepared according to the procedure for Example 1443c. From N-[2-(2-methanesulfinyl-pyrrolo[2,1-f][1,2,4]triazin-7-yl)-phenyl]-N-methyl-methanesulfonamide (100 mg, 0.27 mmol) and 4-(4,4-difluoro-piperidin-1-yl)-2-methoxy-phenylamine (133 mg, 0.55 mmol) was obtained 46 mg of the title compound as a yellow solid upon preparative RF-HPLC and lyophilization. MS=543 (M-TFA+1); NMR (DMSO-$d_6$, ppm): 8.92 (s, 1H), 7.96 (d, J=8 Hz, 1H), 7.71 (d, J=7 Hz, 1H), 7.63 (m, 2H), 7.53 (m, 2H), 6.96 (q, J=5 Hz, 20 Hz, 2H), 6.72 (s, 1H), 6.45 (d, J=8 Hz, 1H), 3.83 (s, 3H), 3.29 (m, 4H), 3.05 (s, 3H), 2.88 (s, 3H), 2.08 (m, 4H).

Example 1470

[4-(4,4-Difluoro-piperidin-1-yl)-2-methoxy-phenyl]-[7-(2-methoxy-phenyl)-pyrrolo[2,1-f][1,2,4]triazin-2-yl]-amine; compound with trifluoroacetic acid 1470a) [4-(4,4-Difluoro-piperidin-1-yl)-2-methoxy-phenyl]-[7-(2-methoxy-phenyl)-pyrrolo[2,1-f][1,2,4]triazin-2-yl]-amine; compound with trifluoroacetic acid: This compound was prepared according to the procedure for Example 1443c. From 2-methanesulfinyl-7-(2-methoxy-phenyl)-pyrrolo[2,1-f][1,2,4]triazine (119 mg, 0.41 mmol) and 4-(4,4-difluoro-piperidin-1-yl)-2-methoxy-phenylamine (200 mg, 0.8 mmol) was obtained 105 mg of the title compound as a yellow solid upon preparative RF-HPLC and lyophilization. MS=466 (M-TFA+1); NMR (DMSO-$d_6$, ppm): 8.91 (s, 1H), 7.89 (d, J=8 Hz, 1H), 7.83 (d, J=8 Hz, 1H), 7.57 (s, 1H), 7.45 (t, J=8 Hz, 1H), 7.20 (d, J=8 Hz, 1H), 7.10 (t, J=8 Hz, 1H), 6.95 (q, J=5 Hz, 20 Hz, 2H), 6.75 (d, J=8 Hz, 1H), 6.49 (d, J=8 Hz, 1H), 3.86 (s, 3H), 3.79 (s, 3H), 3.31 (m, 4H), 2.10 (m, 4H).

Example 1471

N-[2-(2-{2-Methoxy-4-[4-(tetrahydro-pyran-4-yl)-piperazin-1-yl]-phenylamino}-pyrrolo[2,1-f][1,2,4]triazin-7-yl)-phenyl]-N-methyl-methanesulfonamide; compound with trifluoroacetic acid 1471a) 4-(Tetrahydro-pyran-4-yl)-piperazine-1-carboxylic acid benzyl ester: This compound was prepared according to the procedure for Example 1444a. From tetrahydro-4H- pyran-4-one (3.7 g, 37 mmol) and piperazine-1-carboxylic acid benzyl ester (6.6 g, 30 mmol) was obtained 8.3 g of the title compound as a pale yellow oil, used without further purification. MS=305 (M+1).

1471b) 1-(Tetrahydro-pyran-4-yl)-piperazine: This compound was prepared according to the procedure for Example 1443b. From 4-(tetrahydro-pyran-4-yl)-piperazine-1-carboxylic acid benzyl ester (4.0 g, 13 mmol) was obtained 2.2 g of the title compound as a pale yellow solid upon filtration and concentration of the reaction mixture, used without further purification. MS=171 (M+1).

1471c) 1-(3-Methoxy-4-nitro-phenyl)-4-(tetrahydro-pyran-4-yl)-piperazine: This compound was prepared according to the procedure for Example 1467c. From 1-(tetrahydro-pyran-4-yl)-piperazine (2.10 g, 12.3 mmol) and 4-fluoro-2-methoxy-1-nitro-benzene (2.22 g, 13 mmol) was obtained 2.92 g of the purified product as a yellow solid following flash chromatography on silica gel. MS=322 (M+1).

1471d) 2-Methoxy-4-[4-(tetrahydro-pyran-4-yl)-piperazin-1-yl]-phenylamine: This compound was prepared according to the procedure for Example 1443b. From 1-(3-methoxy-4-nitro-phenyl)-4-(tetrahydro-pyran-4-yl)-piperazine (2.5 g, 7.8 mmol) was obtained 2.30 g of the title compound as a pale violet-gray solid upon filtration and concentration of the reaction mixture.

1471e) N-[2-(2-{2-Methoxy-4-[4-(tetrahydro-pyran-4-yl)-piperazin-1-yl]-phenylamino}-pyrrolo[2,1-f][1,2,4]triazin-7-yl)-phenyl]-N-methyl-methanesulfonamide; compound with trifluoroacetic acid: This compound was prepared according to the procedure for Example 1443c. From N-[2-(2-methanesulfinyl-pyrrolo[2,1-f][1,2,4]triazin-7-yl)-phenyl]-N-methyl-methanesulfonamide (100 mg, 0.27 mmol) and 2-methoxy-4-[4-(tetrahydro-pyran-4-yl)-piperazin-1-yl]-phenylamine (160 mg, 0.55 mmol) was obtained 78 mg of the title compound upon preparative RF-HPLC and lyophillization. MS=592 (M-TFA+1); NMR (DMSO-$d_6$, ppm): 9.77 (s, 1H), 8.92 (s, 1H), 7.98 (d, J=8 Hz, 1H), 7.75 (d, J=8 Hz, 1H), 7.68 (s, 1H), 7.64 (d, J=8 Hz, 1H), 7.53 (m, 2H), 6.96 (q, J=5 Hz, 20 Hz, 2H), 7.73 (s, 1H), 6.45 (d, J=8 Hz, 1H), 4.01 (d, J=10 Hz, 2H), 3.84 (s+m, 5H), 3.63 (d, J=10 Hz, 2H), 3.51 (m, 1H), 3.33 (t, J=12 Hz, 2H), 3.18 (m, 2H), 3.08 (s, 3H), 2.95 (t, J=12 Hz, 2H), 2.88 (s, 3H), 2.05 (d, J=12 Hz, 2H), 1.68 (q, J=12 Hz, 2H).

Example 1472

[7-(2-Methoxy-phenyl)-pyrrolo[2,1-f][1,2,4]triazin-2-yl]-{2-methoxy-4-[4-(tetrahydro-pyran-4-yl)-piperazin-1-yl]-phenyl}-amine; compound with trifluoroacetic acid 1472a) [7-(2-Methoxy-phenyl)-pyrrolo[2,1-f][1,2,4]triazin-2-yl]-{2-methoxy-4-[4-(tetrahydro-pyran-4-yl)-piperazin-1-yl]-phenyl}-amine; compound with trifluoroacetic acid: This compound was prepared according to the procedure for Example 1443c. From 2-methanesulfinyl-7-(2-methoxy-phenyl)-pyrrolo[2,1-f][1,2,4]triazine (79 mg, 0.27 mmol) and 2-methoxy-4-[4-(tetrahydro-pyran-4-yl)-piperazin-1-yl]-phenylamine (160 mg, 0.55 mmol) was afforded 75 mg of the title compound as a yellow solid upon RF-HPLC and lyophilization. MS=515 (M-TFA+1); NMR (DMSO-$d_6$, ppm): 9.52 (s, 1H), 8.91 (s, 1H), 7.92 (d, J=8 Hz, 1H), 7.85 (d, J=8 Hz, 1H), 7.57 (s, 1H), 7.44 (t, J=8 Hz, 1H), 7.20 (d, J=8 Hz, 1H), 7.10 (t, J=8 Hz, 1H), 6.94 (q, J=5 Hz, 20 Hz, 2H), 6.74 (s, 1H), 6.45 (d, J=8 Hz, 1H), 4.01 (d, J=12 Hz, 2H), 3.87 (s, 3H), 3.84 (m, 2H), 3.80 (s, 3H), 3.63 (d, J=12 Hz, 2H), 3.53 (m, 1H), 3.34 (t, J=12 Hz, 2H), 3.19 (q, J=12 Hz, 2H), 2.94 (t, J=12 Hz, 2H), 2.05 (d, J=12 Hz, 2H), 1.68 (q, J=12 Hz, 2H).

Example 1473

[7-(2-Fluoro-phenyl)-pyrrolo[2,1-f][1,2,4]triazin-2-yl]-[2-methoxy-4-(4-morpholin-4-yl-piperidin-1-yl)-phenyl]-amine; compound with trifluoroacetic acid 1473a) 7-(2-Fluoro-phenyl)-2-methylsulfanyl-pyrrolo[2,1-f][1,2,4]triazine: This compound was prepared according to the procedure for Example 1447a. From 7-bromo-2-methylsulfanyl-pyrrolo[2,1-f][1,2,4]triazine (250 mg, 1.0 mmol) and 2-fluorophenylboronic acid (286 mg, 2.1 mmol) was obtained 250 mg of the purified product as a yellow solid following flash chromatography on silica gel. mp 76-82° C.; MS=260 (M+1).

1473b) 7-(2-Fluoro-phenyl)-2-methanesulfinyl-pyrrolo[2,1-f][1,2,4]triazine: This compound was prepared according to the procedure for Example 1449b. From 7-(2-fluoro-phenyl)-2-methylsulfanyl-pyrrolo[2,1-f][1,2,4]triazine (240 mg, 0.92 mmol) in dichloromethane (25 mL, 390 mmol) and 70% m-CPBA (240 mg, 0.97 mmol) was obtained 150 mg of the purified product as a yellow solid following flash chromatography on silica gel. MS=276 (M+1).

1473c) [7-(2-Fluoro-phenyl)-pyrrolo[2,1-f][1,2,4]triazin-2-yl]-[2-methoxy-4-(4-morpholin-4-yl-piperidin-1-yl)-phenyl]-amine; compound with trifluoroacetic acid: This compound was prepared according to the procedure for Example 1443c. From 7-(2-fluoro-phenyl)-2-methanesulfinyl-pyrrolo[2,1-f][1,2,4]triazine (71 mg, 0.26 mmol) and 2-methoxy-4-(4-morpholin-4-yl-piperidin-1-yl)-phenylamine (150 mg, 0.51 mmol) was obtained 97 mg of the title compound upon preparative RF-HPLC and lyophillization. MS=503 (M-TFA+1); NMR (DMSO-$d_6$, ppm): 9.84 (s, 1H), 8.98 (s, 1H), 8.14 (t, J=8 Hz, 1H), 7.83 (d, J=8 Hz, 1H), 7.74 (s, 1H), 7.48 (m, 1H), 7.39 (m, 2H), 7.02 (m, 1H), 6.97 (m, 1H), 6.51 (d, J=8 Hz, 1H), 4.04 (d, J=12 Hz, 2H), 3.86 (s+m, 5H), 3.69 (t, J=12 Hz, 2H), 3.50 (d, J=12 Hz, 2H), 3.37 (m, 2H), 3.14 (m, 2H), 2.73 (t, J=12 Hz, 2H), 2.16 (d, J=12 Hz, 2H), 1.74 (q, J=12 Hz, 2H).

Example 1474

N-(2-{2-[4-(4,4-Difluoro-[1,4']bipiperidinyl-1'-yl)-2-methoxy-phenylamino]-pyrrolo[2,1-f][1,2,4]triazin-7-yl}-phenyl)-N-methyl-methanesulfonamide 1474a) 4,4-Difluoro-[1,4']bipiperidinyl-1'-carboxylic acid benzyl ester: This compound was prepared according to the procedure for Example 1444a. From 4-oxo-piperidine-1-carboxylic acid benzyl ester (5.0 g, 21 mmol) and 4,4-difluoro-piperidine hydrochloride (4.4 g, 28 mmol) was obtained 3.32 g of the purified product following flash chromatography on silica gel. mp 72-74° C.; MS=339 (M+1).

1474b) 4,4-Difluoro-[1,4']bipiperidine: This compound was prepared according to the procedure for Example 1443b. From 4,4-difluoro-[1,4']bipiperidinyl-1'-carboxylic acid benzyl ester (3.20 g, 9.46 mmol) was obtained 1.84 g of the title compound as a pale-yellow oil following filtration of the reaction mixture and concentration, used without further purification. MS=205 (M+1).

1474c) 4,4-Difluoro-1'-(3-methoxy-4-nitro-phenyl)-[1,4']bipiperidine: This compound was prepared according to the procedure for Example 1467c. From 4,4-difluoro-[1,4']bipiperidine (1.79 g, 8.77 mmol) and 4-fluoro-2-methoxy-1-nitro-benzene (1.43 g, 8.36 mmol) was obtained 3.0 g of the title compound as a yellow solid following flash chromatography on silica gel. MS=356 (M+1).

1474d) 4-(4,4-Difluoro-[1,4']bipiperidinyl-1'-yl)-2-methoxy-phenylamine: This compound was prepared according to the procedure for Example 1443b. From 4,4-difluoro-1'-(3-methoxy-4-nitro-phenyl)-[1,4']bipiperidinyl (1.50 g, 4.22 mmol) was obtained 1.12 g of the title compound as a pale violet powder upon filtration and concentration of the reaction mixture, used without further purification. MS=326 (M+1).

1474e) N-(2-{2-[4-(4,4-Difluoro-[1,4']bipiperidinyl-1'-yl)-2-methoxy-phenylamino]-pyrrolo[2,1-f][1,2,4]triazin-7-yl}-phenyl)-N-methyl-methanesulfonamide: This compound was prepared according to the procedure for Example 1443c. From 4-(4,4-difluoro-[1,4']bipiperidinyl-1'-yl)-2-methoxy-phenylamine (180 mg, 0.55 mmol) and N-[2-(2-methanesulfinyl-pyrrolo[2,1-f][1,2,4]triazin-7-yl)-phenyl]-N-methyl-methanesulfonamide (100 mg, 0.27 mmol) was obtained 75 mg of the title compound following preparative RF-HPLC and lyophillization. MS=626 (M-TFA+1); NMR (DMSO-d$_6$, ppm): 9.77 (br, 1H), 8.92 (s, 1H), 7.99 (d, J=8 Hz, 1H), 7.72 (d, J=12 Hz, 1H), 7.64 (m, 2H), 7.53 (m, 2H), 6.95 (q, J=5 Hz, 20 Hz, 2H), 6.69 (s, 1H), 6.44 (d, J=8 Hz, 1H), 3.84 (s, 3H), 3.81 (m, 2H), 3.67 (m, 2H), 3.50 (t, J=12 Hz, 1H), 3.21 (m, 2H), 3.08 (s, 3H), 2.88 (s, 3H), 2.71 (t, J=12 Hz, 2H), 2.40 (m, 4H), 2.13 (d, J=12 Hz, 2H), 1.76 (q, J=12 Hz, 2H).

Example 1475

[4-(4,4-Difluoro-[1,4']bipiperidinyl-1'-yl)-2-methoxy-phenyl]-[7-(2-methoxy-phenyl)-pyrrolo[2,1-f][1,2,4]triazin-2-yl]-amine; compound with trifluoroacetic acid 1475a) [4-(4,4-Difluoro-[1,4']bipiperidinyl-1'-yl)-2-methoxy-phenyl]-[7-(2-methoxy-phenyl)-pyrrolo[2,1-f][1,2,4]triazin-2-yl]-amine; compound with trifluoroacetic acid: This compound was prepared according to the procedure for Example 1442c. From 4-(4,4-difluoro-[1,4']bipiperidinyl-1'-yl)-2-methoxy-phenylamine (226 mg, 0.70 mmol) and 2-methanesulfinyl-7-(2-methoxy-phenyl)-pyrrolo[2,1-f][1,2,4]triazine (100 mg, 0.35) was obtained 28 mg of the title compound upon preparative RF-HPLC and lyophillization. MS=549 (M-TFA+1); NMR (DMSO-d$_6$, ppm): 9.66 (br, 1H), 8.91 (s, 1H), 7.87 (m, 2H), 7.53 (s, 1H), 7.44 (t, J=8 Hz, 1H), 7.20 (d, J=8 Hz, 1H), 7.10 (t, J=8 Hz, 1H), 6.94 (q, J=5 Hz, 20 Hz, 2H), 6.70 (s, 1H), 6.43 (d, J=8 Hz, 1H), 3.86 (s+m, 4H), 3.80 (s+m, 5H), 3.66 (m, 2H), 3.49 (m, 2H), 3.21 (m, 2H), 2.70 (t, J=12 Hz, 2H), 2.43 (m, 2H), 2.13 (d, J=12 Hz, 2H), 1.77 (q, J=12 Hz, 2H).

Example 1476

[7-(2,5-Dimethoxy-phenyl)-pyrrolo[2,1-f][1,2,4]triazin-2-yl]-[2-methoxy-4-(4-morpholin-4-yl-piperidin-1-yl)-phenyl]-amine 1476a) 7-(2,5-Dimethoxy-phenyl)-2-methylsulfanyl-pyrrolo[2,1-f][1,2,4]triazine: This compound was prepared according to the procedure for Example 1447a. From 7-bromo-2-methylsulfanyl-pyrrolo[2,1-f][1,2,4]triazine (400 mg, 2.0 mmol), and 2,5-dimethoxyphenylboronic acid (600 mg, 3.3 mmol) was obtained 490 mg of the purified product as a yellow solid following flash chromatography on silica gel. mp 155-161° C.; MS=302 (M+1).

1476b) 7-(2,5-Dimethoxy-phenyl)-2-methanesulfinyl-pyrrolo[2,1-f][1,2,4]triazine: This compound was prepared according to the procedure for Example 1449b. From 7-(2,5-dimethoxy-phenyl)-2-methylsulfanyl-pyrrolo[2,1-f][1,2,4]triazine (500 mg, 2.0 mmol) and 70% m-CPBA (429 mg, 1.74 mmol) was obtained 420 mg of the purified product as a yellow solid following flash chromatography on silica gel. mp 104-108° C.; MS=318 (M+1).

1476c) [7-(2,5-Dimethoxy-phenyl)-pyrrolo[2,1-f][1,2,4]triazin-2-yl]-[2-methoxy-4-(4-morpholin-4-yl-piperidin-1-yl)-phenyl]-amine: This compound was prepared according to the procedure for Example 1443c. From 7-(2,5-dimethoxy-phenyl)-2-methanesulfinyl-pyrrolo[2,1-f][1,2,4]triazine (100 mg, 0.32 mmol) and 2-methoxy-4-(4-morpholin-4-yl-piperidin-1-yl)-phenylamine (184 mg, 0.63 mmol) was obtained 54 mg of the title compound upon preparative RF-HPLC and free-basing. mp 196-200° C.; MS=545 (M+1); NMR (DMSO-d$_6$, ppm): 8.89 (s, 1H), 7.86 (s, J=8 Hz, 1H), 7.50 (m, 2H), 7.12 (d, J=8 Hz, 1H), 6.99 (m, 2H), 6.90 (s, 1H), 6.64 (s, 1H), 6.35 (d, J=8 Hz, 1H), 3.83 (s, 3H), 3.74 (s, 3H), 3.72 (s, 3H), 3.65 (d, J=12 Hz, 2H), 3.58 (m, 4H), 3.39 (q, J=7 Hz, 2H), 2.62 (t, J=12 Hz, 2H), 2.26 (t, J=12 Hz, 1H), 1.87 (d, J=12 Hz, 2H), 1.51 (q, J=12 Hz, 2H), 1.09 (t, J=12 Hz, 2H).

Example 1477

(S)-1-(4-{4-[7-(2,5-Dimethoxy-phenyl)-pyrrolo[2,1-f][1,2,4]triazin-2-ylamino]-3-methoxy-phenyl}-piperazin-1-yl)-propan-2-ol 1477a) (S)-1-(4-{4-[7-(2,5-Dimethoxy-phenyl)-pyrrolo[2,1-f][1,2,4]triazin-2-ylamino]-3-methoxy-phenyl}-piperazin-1-yl)-propan-2-ol: This compound was prepared according to the procedure for Example 1443c. From 7-(2,5-dimethoxy-phenyl)-2-methanesulfinyl-pyrrolo[2,1-f][1,2,4]triazine (100 mg, 0.32 mmol) and (S)-1-[4-(4-amino-3-methoxy-phenyl)-piperazin-1-yl]-propan-2-ol (167 mg, 0.63 mmol) was obtained 60 mg of the title compound upon preparative RF-HPLC and free-basing. mp 121-125° C.; MS=519 (M+1); NMR (DMSO-d$_6$, ppm): 8.90 (s, 1H), 7.87 (d, J=8 Hz, 1H), 7.52 (s, 1H), 7.50 (s, 1H), 7.14 (d, J=8 Hz, 1H), 6.99 (m, 2H), 6.90 (m, 1H), 6.64 (s, 1H), 6.34 (d, J=8 Hz, 1H), 4.31 (s, 1H), 3.84 (s+m, 4H), 3.74 (s, 3H), 3.72 (s, 3H), 3.09 (m, 4H), 2.57 (m, 4H), 2.26 (m, 2H), 1.07 (d, J=7 Hz, 3H).

Example 1478

N-[2-(2-{3-Fluoro-4-[4-((S)-2-hydroxy-propyl)-piperazin-1-yl]-2-methoxy-phenylamino}-pyrrolo[2,1-f][1,2,4]triazin-7-yl)-phenyl]-N-methyl-methanesulfonamide 1478a) 1,2-Difluoro-3-methoxy-4-nitro-benzene: This compound was prepared according to the procedure for Example 1469a, using iodomethane instead of dimethyl sulfate. From 2,3-difluoro-6-nitro-phenol (5.0 g, 29 mmol), potassium carbonate (5.52 g, 40 mmol) and iodomethane (2.2 mL, 36 mmol) in DMF (40 mL) was obtained 3.2 g of the title compound as a pale yellow liquid upon standard workup in dichloromethane, used without further purification. MS=190 (M+1).

1478b) 4-(2-Fluoro-3-methoxy-4-nitro-phenyl)-piperazine-1-carboxylic acid tert-butyl ester: This compound was prepared according to the procedure for Example 1467c. From 1,2-difluoro-3-methoxy-4-nitro-benzene (3.0 g, 16 mmol) and tert-butyl 1-piperazinecarboxylate (3.3 g, 17.4 mmol) was obtained 5.18 g of the title compound as a yellow solid following flash chromatography on silica gel. mp 149-152° C.; MS=356 (M+1).

1478c) 1-(2-Fluoro-3-methoxy-4-nitro-phenyl)-piperazine; trifluoro-acetic acid: This compound was prepared according to the procedure for Example 1467b. From 4-(2-fluoro-3-methoxy-4-nitro-phenyl)-piperazine-1-carboxylic acid tert-butyl ester (5.3 g, 15 mmol) was obtained 5.4 g of the title compound as a yellow solid. mp 145-150° C.; MS=256 (M−Boc+1).

1478d) (S)-1-[4-(2-Fluoro-3-methoxy-4-nitro-phenyl)-piperazin-1-yl]-propan-2-ol: A solution of 1-(2-fluoro-3-methoxy-4-nitro-phenyl)-piperazine; compound with trifluoro-acetic acid (2.0 g, 0.54 mmol) in methanol (50 mL) was treated with N,N-diisopropylethylamine (2.8 mL, 1.62 mmol) and (S)-2-methyl-oxirane (1.14 mL, 1.62 mmol). The flask was stoppered and the mixture was stirred at room temperature for 45 h. The mixture was concentrated and flash chromatography over silica gel gave 1.40 g of the title compound as a yellow solid. mp 86-88° C.; MS=315 (M+1).

1478e) (S)-1-[4-(4-Amino-2-fluoro-3-methoxy-phenyl)-piperazin-1-yl]-propan-2-ol: This compound was prepared according to the procedure for Example 1443b. From (S)-1-[4-(2-fluoro-3-methoxy-4-nitro-phenyl)-piperazin-1-yl]-propan-2-ol (1.2 g, 3.8 mmol) was obtained 1.10 g of the title compound as a cream-colored solid, used without further purification. mp 95-100° C.; MS=284 (M+1).

1478f) N-[2-(2-{3-Fluoro-4-[4-((S)-2-hydroxy-propyl)-piperazin-1-yl]-2-methoxy-phenylamino}-pyrrolo[2,1-f][1,2,4]triazin-7-yl)-phenyl]-N-methyl-methanesulfonamide: This compound was prepared according to the procedure for Example 1443c. From N-[2-(2-methanesulfinyl-pyrrolo[2,1-f][1,2,4]triazin-7-yl)-phenyl]-N-methyl-methanesulfonamide (115 mg, 0.32 mmol) and (S)-1-[4-(4-amino-2-fluoro-3-methoxy-phenyl)-piperazin-1-yl]-propan-2-ol (180 mg, 0.63 mmol) was afforded 15 mg of the title compound upon preparative RF-HPLC and lyophilization. MS=584 (M-TFA+1); NMR (DMSO-d6, ppm): 9.48 (br, 1H), 8.97 (s, 1H), 8.14 (s, 1H), 7.96 (m, 1H), 7.62 (m, 2H), 7.53 (m, 2H), 6.99 (q, J=5 Hz, 15 Hz, 2H), 6.70 (t, J=8 Hz, 1H), 4.12 (m, 1H), 3.83 (m, 3H), 3.76 (m, 2H), 3.58 (m, 2H), 3.20 (m, 4H), 3.07 (s, 3H), 3.09 (s, 2H), 2.88 (s, 3H), 1.14 (d, J=6 Hz, 3H).

Example 1479

N-[2-(2-{5-Fluoro-4-[4-((S)-2-hydroxy-propyl)-piperazin-1-yl]-2-methoxy-phenylamino}-pyrrolo[2,1-f][1,2,4]triazin-7-yl)-phenyl]-N-methyl-methanesulfonamide 1479a) 4-(2-Fluoro-5-methoxy-4-nitro-phenyl)-piperazine-1-carboxylic acid tert-butyl ester: To a solution of tert-butyl 1-piperazinecarboxylate (6.0 g, 32.0 mmol) and 1-bromo-2-fluoro-5-methoxy-4-nitro-benzene (4.0 g, 16.0 mmol) in 1,4-dioxane (150 mL) was added cesium carbonate (10.4 g, 32.0 mmol). The mixture was purged with argon for five minutes and bis(dibenzylideneacetone)palladium(0) (0.46 g, 0.80 mmol) and 9,9-dimethyl-4,5-bis(diphenylphosphino)xanthene (0.93 g, 1.6 mmol) was added. The mixture was heated at 100° C. for 18 hours. The mixture was filtered and concentrated. The residue was dissolved in dichloromethane and washed with saturated aqueous sodium bicarbonate and brine, dried over anhydrous magnesium sulfate, filtered and concentrated. Flash chromatography over silica gel gave 3.83 g of the purified product as an amber viscous oil. MS=256 (M−Boc+1).

1479b) 1-(2-Fluoro-5-methoxy-4-nitro-phenyl)-piperazine, trifluoroacetic acid: This compound was prepared according to the procedure for Example 1467b. From 4-(2-fluoro-5-methoxy-4-nitro-phenyl)-piperazine-1-carboxylic acid tert-butyl ester (3.8 g, 10.7 mmol) was afforded 3.31 g of the title compound as a mustard yellow solid following evaporation of solvents and drying to constant weight, used without further purification. mp 185-190° C. (dec); MS=256 (M-TFA+1).

1479c) (S)-1-[4-(2-Fluoro-5-methoxy-4-nitro-phenyl)-piperazin-1-yl]-propan-2-ol: This compound was prepared according to the procedure for Example 1478d. From 1-(2-fluoro-5-methoxy-4-nitro-phenyl)-piperazine, trifluoroacetic acid (2.00 g, 5.42 mmol) was obtained 0.90 g of the title compound following flash chromatography on silica gel. MS=314 (M+1).

1479d) (S)-1-[4-(4-Amino-2-fluoro-5-methoxy-phenyl)-piperazin-1-yl]-propan-2-ol: This compound was prepared according to the procedure for Example 1443b. From (S)-1-[4-(2-fluoro-5-methoxy-4-nitro-phenyl)-piperazin-1-yl]-propan-2-ol (0.75 g, 2.4 mmol) was obtained 670 mg of the title compound as a dark amber solid, used without further purification. MS=284 (M+1).

1479e) N-[2-(2-{5-Fluoro-4-[4-((S)-2-hydroxy-propyl)-piperazin-1-yl]-2-methoxy-phenylamino}-pyrrolo[2,1-f][1,2,4]triazin-7-yl)-phenyl]-N-methyl-methanesulfonamide: A mixture of trifluoromethanesulfonic acid 7-[2-(methanesulfonyl-methyl-amino)-phenyl]-pyrrolo[2,1-f][1,2,4]triazin-2-yl ester (150 mg, 0.33 mmol) and (S)-1-[4-(4-amino-2-fluoro-5-methoxy-phenyl)-piperazin-1-yl]-propan-2-ol (189 mg, 0.67 mmol) in 1-methoxy-2-propanol (2.0 mL) was treated with N,N-diisopropylethylamine (145 uL, 0.83 mmol) and heated at 95° C. with stirring under Argon for eight hours. The mixture was diluted with methanol (10 mL) with stirring, filtered and concentrated. Preparative RF-HPLC gave 94 mg of the title compound upon lyophilization and free-basing. mp 116-120° C.; MS=584 (M+1); NMR (DMSO-d6, ppm): 8.96 (s, 1H), 7.98 (d, J=8 Hz, 1H), 7.84 (d, J=15 Hz, 1H), 7.66 (m, 2H), 7.54 (m, 2H), 7.00 (q, J=5 Hz, 17 Hz, 2H), 6.68 (d, J=8 Hz, 1H), 4.30 (m, 1H), 3.85 (s, 3H), 3.79 (m, 1H), 3.07 (s, 3H), 2.99 (m, 4H), 2.90 (s, 3H), 2.57 (m, 4H), 2.27 (m, 2H), 1.07 (d, J=6 Hz, 3H).

Example 1480

(S)-1-(4-{2-Fluoro-5-methoxy-4-[7-(2-methoxy-phenyl)-pyrrolo[2,1-f][1,2,4]triazin-2-ylamino]-phenyl}-piperazin-1-yl)-propan-2-ol 1480a) (S)-1-(4-{2-Fluoro-5-methoxy-4-[7-(2-methoxy-phenyl)-pyrrolo[2,1-f][1,2,4]triazin-2-ylamino]-phenyl}-piperazin-1-yl)-propan-2-ol: This compound was prepared according to Example 1443c. From 2-methanesulfinyl-7-(2-methoxy-phenyl)-pyrrolo[2,1-f][1,2,4]triazine (100 mg, 0.35 mmol) and (S)-1-[4-(4-Amino-2-fluoro-5-methoxy-phenyl)-piperazin-1-yl]-propan-2-ol (197 mg, 0.70 mmol) was obtained 10 mg of the title compound upon preparative RF-HPLC and lyophilization. MS=507 (M-TFA+1); NMR (DMSO-d6, ppm): 9.47 (br, 1H), 8.97 (s, 1H), 8.06 (d, J=14 Hz, 1H), 7.75 (d, J=8 Hz, 1H), 7.65 (s, 1H), 7.49 (m, 1H), 7.20 (d, J=8 Hz, 1H), 7.10 (m, 1H), 6.98 (s, 2H), 6.73 (d, J=8 Hz, 1H), 4.12 (m, 2H), 3.90 (s, 3H), 3.83 (m, 2H), 3.79 (s, 3H), 3.57 (m, 2H), 3.44 (m, 2H), 3.22 (m, 2H), 3.07 (m, 2H), 1.15 (d, J=6 Hz, 3H).

Example 1481

(S)-1-(4-{2,5-Difluoro-4-[7-(2-methoxy-phenyl)-pyrrolo[2,1-f][1,2,4]triazin-2-ylamino]-phenyl}-piperazin-1-yl)-propan-2-ol; compound with trifluoroacetic acid 1481a) 4-(2,5-Difluoro-4-nitro-phenyl)-piperazine-1-carboxylic acid tert-butyl ester: To a solution of 1,2,4-trifluoro-5-nitro-benzene (3.0 g, 17 mmol) in DMF (75 mL) was added potassium carbonate (2.5 g, 18 mmol). The mixture was cooled in an ice-water bath and tert-butyl 1-piperazinecarboxylate (3.3 g, 18 mmol) was added portionwise over 30 min. The mixture was stirred a further 15 min at 0° C., then at room temperature for one hour. The mixture was filtered and concentrated. The residue was stirred with 50 mL Et20/hexanes (1:1), filtered, washed with a little Et20/hexanes and dried in-vacuo to constant weight to give 3.7 g of the title compound as a yellow solid, used without further purification. mp 120-122° C.; LMS=366 (M+Na).

1481b) 1-(2,5-Difluoro-4-nitro-phenyl)-piperazine; trifluoroacetic acid: This compound was prepared according to the procedure for Example 1467b. From 4-(2,5-difluoro-4-nitro-phenyl)-piperazine-1-carboxylic acid tert-butyl ester (3.50 g, 10.2 mmol) was obtained 3.6 g of the title compound as a yellow solid, used without further purification. mp 197-201° C. (dec); MS=244 (M-TFA+1).

1481c) (S)-1-[4-(2,5-Difluoro-4-nitro-phenyl)-piperazin-1-yl]-propan-2-ol: This compound was prepared according to the procedure for Example 1478d. From 1-(2,5-difluoro-4-nitro-phenyl)-piperazine; compound with trifluoroacetic acid (1.0 g, 2.8 mmol) and (S)-2-methyl-oxirane (0.59 mL, 8.4 mmol) in methanol (30 mL) over 40 hours was obtained 750 mg of the title compound as a yellow solid following flash chromatography over silica gel. MS=302 (M+1).

1481d) (S)-1-[4-(4-Amino-2,5-difluoro-phenyl)-piperazin-1-yl]-propan-2-ol: This compound was prepared according to the procedure for Example 1443b. From (S)-1-[4-(2,5-difluoro-4-nitro-phenyl)-piperazin-1-yl]-propan-2-ol (0.50 g, 1.6 mmol) was obtained 430 mg of the title compound upon filtration of catalyst and concentration to constant weight, used without further purification. MS=272 (M+1).

1481e) (S)-1-(4-{2,5-Difluoro-4-[7-(2-methoxy-phenyl)-pyrrolo[2,1-f][1,2,4]triazin-2-ylamino]-phenyl}-piperazin-1-yl)-propan-2-ol; compound with trifluoroacetic acid: A mixture of 7-(2-methoxy-phenyl)-pyrrolo[2,1-f][1,2,4]triazin-2-yl-methanesulfonate (124 mg, 0.33 mmol) and (S)-1-[4-(4-amino-2,5-difluoro-phenyl)-piperazin-1-yl]-propan-2-ol (181 mg, 0.67 mmol) in 1-methoxy-2-propanol (2.0 mL) was treated with N,N-diisopropylethylamine (145 uL, 0.83 mmol) and heated at 95° C. with stirring under Argon for eight hours. The mixture was cooled to ambient temperature, diluted with MeOH (10 mL) with stirring, filtered and concentrated. Preparative RF-HPLC gave 40 mg of the title compound as a yellow amorphous solid upon lyophilization. MS=495 (M-TFA+1); NMR (DMSO-$d_6$, ppm): 9.54 (br, 1H), 8.98 (s, 1H), 8.83 (s, 1H), 7.94 (m, 1H), 7.76 (d, J=8 Hz, 1H), 7.43 (t, J=8 Hz, 1H), 7.17 (d, J=8 Hz, 1H), 7.06 (m, 2H), 6.97 (q, J=5 Hz, 2H), 4.12 (m, 1H), 3.79 (s, 3H), 3.83 (m, 2H), 3.79 (s, 3H), 3.57 (m, 2H), 3.44 (m, 2H), 3.18 (m, 2H), 3.05 (m, 2H), 1.15 (d, J=6 Hz, 3H).

Example 1482

N-[2-(2-{2,5-Difluoro-4-[4-((S)-2-hydroxy-propyl)-piperazin-1-yl]-phenylamino}-pyrrolo[2,1-f][1,2,4]triazin-7-yl)-phenyl]-N-methyl-methanesulfonamide; compound with trifluoroacetic acid 1482a) N-[2-(2-{2,5-Difluoro-4-[4-((S)-2-hydroxy-propyl)-piperazin-1-yl]-phenylamino}-pyrrolo[2,1-f][1,2,4]triazin-7-yl)-phenyl]-N-methyl-methanesulfonamide; compound with trifluoroacetic acid: This compound was prepared according to the procedure for Example 1481e. From 7-[2-(methanesulfonyl-methyl-amino)-phenyl]-pyrrolo[2,1-f][1,2,4]triazin-2-yl-trifluoromethanesulfonate (150 mg, 0.33 mmol) and (S)-1-[4-(4-amino-2,5-difluoro-phenyl)-piperazin-1-yl]-propan-2-ol (181 mg, 0.67 mmol) was obtained 71 mg of the title compound upon preparative RF-HPLC and lyophillization. MS=572 (M-TFA+1); NMR (DMSO-$d_6$, ppm): 9.54 (br, 1H), 8.99 (s, 1H), 8.88 (s, 1H), 7.96 (d, J=8 Hz, 1H), 7.76 (m, 1H), 7.64 (d, J=8 Hz, 1H), 7.49 (m, 2H), 7.06 (m, 1H), 7.00 (q, J=5 Hz, 15 Hz, 2H), 4.12 (m, 1H), 3.58 (d, J=12 Hz, 2H), 3.44 (t, J=12 Hz, 2H), 3.22 (m, 4H), 3.09 (s+m, 6H), 2.89 (s, 3H), 1.15 (d, J=6 Hz, 3H).

Example 1483

N-[2-(2-{5-Fluoro-4-[4-((S)-2-hydroxy-propyl)-piperazin-1-yl]-2-methylsulfanyl-phenylamino}-pyrrolo[2,1-f][1,2,4]triazin-7-yl)-phenyl]-N-methyl-methanesulfonamide; compound with trifluoroacetic acid 1483a) 4-(2-Fluoro-5-methylsulfanyl-4-nitro-phenyl)-piperazine-1-carboxylic acid tert-butyl ester: 4-(2,5-difluoro-4-nitro-phenyl)-piperazine-1-carboxylic acid tert-butyl ester (1.5 g, 4.4 mmol) in ethanol (25 mL) was cooled in an ice-water bath to which was added sodium methyl mercaptide (337 mg, 4.80 mmol). The mixture was stirred while being allowed to slowly warm to room temperature over five hours, at which time LCMS showed complete reaction. The mixture was concentrated on the rotovap and the residue was partitioned between dichloromethane and water. The organic phase was washed with brine, dried over anhydrous magnesium sulfate, filtered and concentrated to give 1.6 g of the title compound as a yellow solid, used without further purification. mp 149-153° C.; LCMS=272 (M-Boc+1).

1483b) 1-(2-Fluoro-5-methylsulfanyl-4-nitro-phenyl)-piperazine; trifluoroacetic acid: This compound was prepared according to the procedure for Example 1447b. From 4-(2-fluoro-5-methylsulfanyl-4-nitro-phenyl)-piperazine-1-carboxylic acid tert-butyl ester (1.50 g, 4.04 mmol) was obtained 1.50 g of the title compound as a yellow solid, used without further purification. mp 218-220° C.; LCMS=272 (M-TFA+1).

1483c) (S)-1-[4-(2-Fluoro-5-methylsulfanyl-4-nitro-phenyl)-piperazin-1-yl]-propan-2-ol: This compound was prepared according to the procedure for Example 1478d. From 1-(2-fluoro-5-methylsulfanyl-4-nitro-phenyl)-piperazine; trifluoroacetic acid (500 mg, 1.3 mmol) and (S)-2-methyl-oxirane (0.27 mL, 3.9 mmol) in methanol (10 mL) and N,N-diisopropylethylamine (0.68 mL, 3.9 mmol) over 22 hours was obtained 281 mg of the title compound as a yellow solid following flash chromatography over silica gel. mp 120-124° C.; LCMS=330 (M+1).

1483d) (S)-1-[4-(4-Amino-2-fluoro-5-methylsulfanyl-phenyl)-piperazin-1-yl]-propan-2-ol: This compound was prepared according to the procedure for Example 1443b.

From (S)-1-[4-(2-fluoro-5-methylsulfanyl-4-nitro-phenyl)-piperazin-1-yl]-propan-2-ol (250 mg, 0.76 mmol) afforded 158 mg of the title compound as an amber oil following flash chromatography over silica gel. MS=300 (M+1).

1483e) N-[2-(2-{5-Fluoro-4-[4-((S)-2-hydroxy-propyl)-piperazin-1-yl]-2-methylsulfanyl-phenylamino}-pyrrolo[2,1-f][1,2,4]triazin-7-yl)-phenyl]-N-methyl-methanesulfonamide; compound with trifluoroacetic acid: This compound was prepared according to the procedure for Example 1481e. From 7-[2-(methanesulfonyl-methyl-amino)-phenyl]-pyrrolo[2,1-f][1,2,4]triazin-2-yl-trifluoromethane sulfonate (150 mg, 0.33 mmol) and (S)-1-[4-(4-amino-2-fluoro-5-methylsulfanyl-phenyl)-piperazin-1-yl]-propan-2-ol (199 mg, 0.67 mmol) was obtained 51 mg of the title compound upon preparative RF-HPLC and lyophillization. MS=600 (M-TFA+1). NMR (DMSO-$d_6$, ppm): 9.35 (br, 1H), 8.99 (s, 1H), 8.21 (s, 1H), 7.99 (d, J=8 Hz, 1H), 7.85 (d, J=15 Hz, 1H), 7.65 (d, J=8 Hz, 1H), 7.50 (m, 2H), 7.13 (d, J=8 Hz, 1H), 7.01 (q, J=5 Hz, 15 Hz, 2H), 4.13 (m, 1H), 3.57 (m, 2H), 3.46 (m, 2H), 3.24 (m, 4H), 3.09 (s+m, 5H), 2.88 (s, 3H), 2.40 (s, 3H), 1.15 (d, J=6 Hz, 3H).

Examples 1484 and 1485

(R,S)—N-[2-(2-{5-Fluoro-4-[4-((S)-2-hydroxy-propyl)-piperazin-1-yl]-2-methanesulfinyl-phenylamino}-pyrrolo[2,1-f][1,2,4]triazin-7-yl)-phenyl]-N-methyl-methanesulfonamide; compound with trifluoroacetic acid 1484a) (R,S)—N-[2-(2-{5-Fluoro-4-[4-((S)-2-hydroxy-propyl)-piperazin-1-yl]-2-methanesulfinyl-phenylamino}-pyrrolo[2,1-f][1,2,4]triazin-7-yl)-phenyl]-N-methyl-methanesulfonamide; compound with trifluoroacetic acid: A solution of N-[2-(2-{5-fluoro-4-[4-((S)-2-hydroxy-propyl)-piperazin-1-yl]-2-methylsulfanyl-phenylamino}-pyrrolo[2,1-f][1,2,4]triazin-7-yl)-phenyl]-N-methyl-methanesulfonamide; compound with trifluoroacetic acid (30 mg, 0.042 mmol) in dichloromethane (10 mL) was treated with sodium bicarbonate (9 mg, 0.10 mmol) and cooled in an ice-water bath. The mixture was treated with 77% m-CPBA (10 mg, 0.046 mmol) and stirred while being allowed to slowly warm to room temperature over four hours. The mixture was diluted with dichloromethane (25 mL), washed with 10% aqueous sodium bisulfite, saturated aqueous sodium bicarbonate, brine, dried over anhydrous magnesium sulfate, filtered, and concentrated. The residue was purified by preparative RF-HPLC to give the two diastereomers (8 mg and 6 mg) upon lyophillization of relevant fractions. Each diastereomer gave essentially identical MS and NMR spectra. MS=616 (M-TFA+1); NMR (DMSO-$d_6$, ppm): 9.60 (s, 1H), 9.49 (br, 1H), 8.98 (s, 1H), 7.92 (d, J=8 Hz, 1H), 7.87 (s, 1H), 7.65 (d, J=8 Hz, 1H), 7.53 (t, J=8 Hz, 1H), 7.47 (t, J=8 Hz, 1H), 7.27 (d, J=8 Hz, 1H), 7.02 (m, 2H), 5.53 (br, 1H), 4.13 (m, 1H), 3.52 (m, 3H), 3.22 (m, 5H), 3.09 (s+m, 5H), 2.87 (s, 3H), 2.82 (s, 3H), 1.15 (d, J=6 Hz, 3H).

Example 1491

7-methoxy-6-{[7-(2-methoxyphenyl)pyrrolo[2,1-f][1,2,4]triazin-2-yl]amino}-1'-methylspiro[chromene-2,4'-piperidin]-4-((3H)-one 1491a) Pyrrolidine (1.15 mL, 13.8 mmol) was added to 1-(2-Hydroxy-4-methoxy-5-nitro-phenyl)-ethanone (2.57 g, 12.2 mmol) (Banks, C. K.; Hamilton, C. S. J. Am. Chem. Soc. 1938, 60, 1370) and 1-Methyl-piperidin-4-one (1.60 mL, 13.0 mmol) in Methanol (50.0 mL) and the reaction was stirred under an atmosphere of nitrogen. After overnight stirring, ~50% conversion was achieved. The mixture was heated at 50° C. for 30 h. Following basic workup, the crude material was purified on ISCO (0-12% MeOH:DCM) to afford 7-methoxy-1'-methyl-6-nitrospiro[chromene-2,4'-piperidin]-4-((3H)-one (2.42 g; Yield=64.9%).

1491b) 7-methoxy-1'-methyl-6-nitrospiro[chromene-2,4'-piperidin]-4-((3H)-one (0.474 g, 1.55 mmol) and 10% Palladium on Carbon (50% Wet) (0.201 g, 0.0944 mmol) was shaken in Methanol (15.0 mL) under an atmosphere of Hydrogen (35 psi) for 5 h. Following filtration through Celite and evaporation, the title compound was isolated as a yellow solid.

1491c) A slurry of 2-Methanesulfinyl-7-(2-methoxy-phenyl)-pyrrolo[2,1-f][1,2,4]triazine (78.0 mg, 0.271 mmol), 6-Amino-7-methoxy-1'-methyl-spiro[chromene-2,4'-piperidin]-4-((3H)-one (151 mg, 0.546 mmol)) and N,N-Diisopropylethylamine (0.150 mL, 0.861 mmol) in 1-Methoxy-2-propanol (0.300 mL, 3.07 mmol) was irradiated in a CEM microwave (200° C., 60 min). Purification by prep HPLC afforded 7-methoxy-6-{[7-(2-methoxyphenyl)pyrrolo[2,1-f][1,2,4]triazin-2-yl]amino}-1'-methylspiro[chromene-2,4'-piperidin]-4-((3H)-one trifluoroacetic acid salt (13 mg; Yield=7.8%). 1H-NMR (DMSO-d6): 9.41 (br s, 1H), 8.93 (s, 1H), 8.16 (s, 1H), 7.82 (m, 2H), 7.39 (m, 1H), 7.18 (d, 1H, J=8.3 Hz), 7.07 (m, 1H), 6.99 (d, 1H, J=4.2 Hz), 6.94 (d, 1H, J=4.2 Hz), 6.79 (s, 1H), 3.93 (s, 3H), 3.79 (s, 3H), 3.34 (m, 2H), 3.20 (m, 2H), 2.84 (s, 3H), 2.82 (s, 2H), 2.17 (m, 2H), 1.87 (m, 2H). LCMS (HPLC): m/z=550 (M+H).

Example 1492

N-Methyl-N-{2-[2-(5-methyl-2-oxo-2,3-dihydro-benzoxazol-6-ylamino)-pyrrolo[2,1-f][1,2,4]triazin-7-yl]-phenyl}-methanesulfonamide 1492a) 5-Methyl-3H-benzoxazol-2-one (1.10 g, 7.38 mmol) added to stirring Nitric acid (6.00 mL, 143 mmol). After stirring 1 h, the mixture was heated at 50° C. for 4 h, cooled and then poured into 100 mL ice and allowed to stand overnight to melt. The yellow solids were collected by filtration, washing with water. The crude nitro product was hydrogenated (25 psi) over 10% Palladium on Carbon (50% Wet) (0.240 g, 0.113 mmol) in Methanol (30.0 mL) for 3 h. The mixture was filtered through Celite and rinsed with MeOH (50 mL). After conc. in vacuo, 6-Amino-5-methyl-3H-benzoxazol-2-one (0.765 g; Yield=63.2%) was isolated as an off-white solid.

1492b) Analogous to Example 1491c, reaction of 6-Amino-5-methyl-3H-benzoxazol-2-one (131 mg, 0.798 mmol) and N-[2-(2-Methanesulfinyl-pyrrolo[2,1-f][1,2,4]triazin-7-yl)-phenyl]-N-methyl-methanesulfonamide (142 mg, 0.390 mmol) afforded N-Methyl-N-{2-[2-(5-methyl-2-oxo-2,3-dihydro-benzoxazol-6-ylamino)-pyrrolo[2,1-f][1,2,4]triazin-7-yl]-phenyl}-methanesulfonamide as the TFA salt. 1H-NMR (DMSO-d6): 11.49 (s, 1H), 8.93 (s, 1H), 8.36 (s, 1H), 7.89 (d, 1H, J=7.5 Hz), 7.58 (d, 1H, J=7.9 Hz), 7.55 (s, 1H), 7.47 (m, 1H), 7.39 (m, 1H), 6.92 (m, 2H), 6.89 (s, 1H), 3.02 (s, 3H), 2.84 (s, 3H), 2.23 (s, 3H); LCMS (HPLC): 1.03 min, m/z=465 (M+H).

Example 1493

N-Methyl-N-{2-[2-(7-methyl-2-oxo-2,3-dihydro-benzoxazol-6-ylamino)-pyrrolo[2,1-f][1,2,4]triazin-7-yl]-phenyl}-methanesulfonamide 1493a) 7-Methyl-3H-benzoxazol-2-one (5.45 g) was added with stirring to Nitric Acid (ACS, 70%, 29 mL) (Exotherm!! Venting of red fumes). After stirring 45 min, the mixture was poured onto 300 mL ice and allowed to melt. The solids were collected and washed with water (120 mL). The isolated ppt, 5.65 g, was 8.2:1 nitration regiomers by 1H-NMR. The crude ppt was partially recrystallized by suspending the solids in water (50 mL), heating to 60° C. and then adding MeOH in 10 mL portions up to 100 mL. The solids never fully dissolved, but the 2:1 solvent mixture was heated for 15 min then allowed to cool and age overnight. The solids were collected and washed with water (100 mL). Yellow powder was comingled with orange flakes (total 5.25 g, 66% yield). Separate NMR's showed the powder to be ~9:1 and the orange flakes ~7:1. A sample of the yellow powder was used in subsequent reactions.

1493b) 7-Methyl-6-nitro-3H-benzoxazol-2-one (0.895 g, 4.61 mmol) was hydrogenated in Methanol (30.0 mL) over 10% Palladium on Carbon (50% Wet) (0.135 g, 0.0634 mmol) under an atmosphere of Hydrogen (30 psi) for 2 h. The mixture was filtered through Celite, washed with MeOH and conc. in vacuo to afford 6-Amino-7-methyl-3H-benzoxazol-2-one (0.74 g, 98%).

1493c) Analogous to Example 1491c, 6-Amino-7-methyl-3H-benzoxazol-2-one (131 mg, 0.798) and N-[2-(2-Methanesulfinyl-pyrrolo[2,1-f][1,2,4]triazin-7-yl)-phenyl]-N-methyl-methanesulfonamide (142 mg, 0.390 mmol) were reacted to afford N-Methyl-N-{2-[2-(7-methyl-2-oxo-2,3-dihydro-benzoxazol-6-ylamino)-pyrrolo[2,1-f][1,2,4]triazin-7-yl]-phenyl}-methanesulfonamide as the TFA salt (14 mg, 6%). 1H-NMR (DMSO-d6): 11.47 (s, 1H), 8.91 (s, 1H), 8.55 (s, 1H), 7.80 (d, 1H, J=7.6 Hz), 7.56 (d, 1H, J=7.8 Hz), 7.45 (m, 1H), 7.39 (m, 1H), 7.24 (d, 1H, 8.8 Hz), 6.91 (m, 2H), 6.85 (d, 1H, J=8.6 Hz), 2.99 (s, 3H), 2.81 (s, 3H), 2.14 (s, 3H); LCMS (HPLC): 1.01 min, m/z=465 (M+H).

Example 1494

7-(2-Methoxy-phenyl)-pyrrolo[2,1-f][1,2,4]triazine-2-carbonitrile

1494a) Sodium Tungstate Dihydrate (62 mg, 0.19 mmol) and 7-(2-Methoxy-phenyl)-2-methylsulfanyl-pyrrolo[2,1-f][1,2,4]triazine (1.02 g, 3.76 mmol) were combined in Methanol (40.0 mL) and 50% Hydrogen Peroxide (0.65 mL, 11 mmol) was added and the reaction was stirred under an atmosphere of nitrogen at 60° C. for 5 h. The mixture was treated with 5 mL 10% Na2S2O3, generating a ppt, then allowed to cool to rt before being stored in a freezer for 30 min. The resultant solids were collected on a Buchner, washing with water (25 mL). Further drying in vacuo afforded 2-Methanesulfonyl-7-(2-methoxy-phenyl)-pyrrolo[2,1-f][1,2,4]triazine (1.00 g; Yield=87.7%). 1H-NMR (DMSO-d6): 9.38 (s, 1H), 7.75 (dd, 1H, J=1.6, 7.6 Hz), 7.51 (m, 2H), 7.40 (d, 1H, J=4.7 Hz), 7.25 (d, 1H, J=8.3 Hz), 7.13 (m, 1H), 3.83 (s, 3H), 3.37 (s, 3H).

1494b) 2-Methanesulfonyl-7-(2-methoxy-phenyl)-pyrrolo[2,1-f][1,2,4]triazine (804 mg, 2.65 mmol) and Potassium cyanide (311 mg, 4.77 mmol) in N-Methylpyrrolidinone (8.0 mL, 84 mmol) was stirred under an atmosphere of Nitrogen at 80° C. for 7 h, reaching ~90% conversion. Work up by partitioning between 50% brine (40 mL):EtOAc (60 mL); giving an emulsion, so DCM (20 mL) was added. The emulsion did not successfully break, so it was kept with the aq. The aq. and emulsion was ext. with EtOAc (3×40 mL), the emulsion was isolated by itself and solubilized with DCM:MeOH. Combining all the org. layers, the mix. was washed with satd. NaHCO3 (50 mL) and brine (2×50 mL), dried over sodium sulfate (two iterations) then conc. in vacuo. Purify on silica gel (ISCO 40 g, 0-40% EtOAc:Hex) to afford 7-(2-Methoxy-phenyl)-pyrrolo[2,1-f][1,2,4]triazine-2-carbonitrile (0.480 g, 72%). 1H-NMR (CDCl3): 8.95 (s, 1H), 7.73 (m, 1H), 7.48 (m, 1H), 7.42 (d, 1H, J=4.7 Hz), 7.1-7.2 (m, 3H), 3.87 (s, 3H).

Example 1495

7-(2-Methoxy-phenyl)-pyrrolo[2,1-f][1,2,4]triazine-2-carboxylic acid amide 7-(2-Methoxy-phenyl)-pyrrolo[2,1-f][1,2,4]triazine-2-carbonitrile (30.0 mg, 0.120 mmol) was suspended in Ethanol (3.0 mL, 51 mmol). Separately, Chlorotrimethylsilane (6.00 mL, 47.3 mmol) was added to Ethanol (9.00 mL, 154 mmol) in a vial, which was sealed and allowed to stand 20 min. The mixture of HCl/EtOH/EtOTMS was then added to the nitrile suspension. Monitoring by $^1$H-NMR (0.1 mL aliquots dried in vacuo) showed conversion overnight. Conc. in vacuo gave 7-(2-Methoxy-phenyl)-pyrrolo[2,1-f][1,2,4]triazine-2-carboxylic acid amide hydrochloride (25 mg, 68%). 1H-NMR (DMSO-d6): 9.26 (s, 1H), 8.04 (s, 1H), 7.85 (s, 1H), 7.78 (d, 1H, J=7.8 Hz), 7.49 (m, 1H), 7.37 (s, 1H), 7.23 (m, 2H), 7.12 (m, 1H), 3.09 (s, 3H); LCMS (Bruker): 3.0 min, 269 (M+H).

Example 1496

N-{2-[2-({1'-[(2S)-2-hydroxypropyl]-7-methoxy-3,4-dihydrospiro[chromene-2,4'-piperidin]-6-yl}amino)pyrrolo[2,1-f][1,2,4]triazin-7-yl]phenyl}-N-methylmethanesulfonamide 1496a) Analogous to Example 1491a, 1-(2-Hydroxy-4-methoxy-5-nitro-phenyl)-ethanone (2.30 g, 10.9 mmol) and 4-Oxo-piperidine-1-carboxylic acid tert-butyl ester (2.28 g, 11.4 mmol) were reacted and purified on silica gel to afford tert-Butyl 7-methoxy-6-nitro-4-oxo-3,4-dihydro-1'H-spiro[chromene-2,4'-piperidine]-1'-carboxylate (3.31 g; Yield=77.4) as a tan foam. 1H-NMR (CDCl3): 8.51 (s, 1H), 6.59 (s, 1H), 4.00 (s, 3H), 3.89 (m, 2H), 3.23 (t, 2H, J=12.8 Hz), 2.74 (s, 2H), 2.02 (m, 2H), 1.67 (t, 2H, J=11.0 Hz), 1.47 (s, 9H); LCMS (Bruker, Fragile): 415 (M+Na).

1496b) tert-Butyl 7-methoxy-6-nitro-4-oxo-3,4-dihydro-1'H-spiro[chromene-2,4'-piperidine]-1'-carboxylate (0.450 g, 1.15 mmol) was suspended in Methanol (12 mL) and Sodium borohydride (0.067 g, 1.8 mmol) was added. Stir at rt under an atmosphere of Nitrogen for 2.5 h, then conc. in vacuo. The residue was suspended in 12.00 M of Hydrogen Chloride in Water (4.5 mL) and heated at 70° C. under an atmosphere of Nitrogen for 3 h, then conc. in vacuo, azeotroping with toluene and DCM. $^1$H-NMR of the residue showed fairly clean intermediate. This material was suspended in Methanol (7.00 mL):N,N-Diisopropylethylamine (1.00 mL, 5.74 mmol), transferred to a sealable vial, treated with (S)-(−)-Propylene Oxide (0.200 mL, 2.85 mmol) and heated at 60° C. for 24 h. Cool and dilute with water:satd NaHCO3 (1:2, 30 mL) and extr. with DCM (2×20 mL). Wash org. with brine (20 mL) and dry, conc. in vacuo onto 2.0 g silica. Purify on ISCO (40 g, 0-10% MeOH:EtOAc) to afford (2S)-1-(7-methoxy-6-nitro-1'H-spiro[chromene-2,4'-piperidin]-1'-yl)propan-2-ol (0.214 g, 55%). 1H-NMR (DMSO-d6): 7.82 (s, 1H), 6.75 (s, 1H), 6.51 (d, 1H, J=9.9 Hz), 5.80 (d, 1H, J=9.9 Hz), 4.26 (s, 1H), 3.91 (s, 3H), 3.75 (m, 1H), 2.60 (m, 2H), 2.29 (m, 1H), 2.23 (m, 1H), 1.85 (m, 2H), 1.75 (m, 2H), 1.05 (d, 3H, J=5.7 Hz); LCMS (Bruker): 335 (M+H).

1496c) (2S)-1-(7-methoxy-6-nitro-1'H-spiro[chromene-2,4'-piperidin]-1'-yl)propan-2-ol (0.210 g, 0.628 mmol) was hydrogenated under an atmosphere of Hydrogen (40 psi) over 10% Palladium on Carbon (50% Wet) (0.080 g, 0.038 mmol) in Ethanol (15.0 mL) for 5 h. Filtration through Celite, rinsing with MeOH, followed by conc. afforded (2S)-1-(6-Amino-7-methoxy-3,4-dihydro-1'H-spiro[chromene-2,4'-piperidin]-1'-yl)propan-2-ol.

1496d) Analogous to Example 1491c, N-[2-(2-Methanesulfinyl-pyrrolo[2,1-f][1,2,4]triazin-7-yl)-phenyl]-N-methyl-methanesulfonamide (131 mg, 0.359 mmol) and (2S)-1-(6-Amino-7-methoxy-3,4-dihydro-1'H-spiro[chromene-2,4'-piperidin]-1'-yl)propan-2-ol (191 mg, 0.623 mmol) were reacted to afford N-{2-[2-({1'-[(2S)-2-hydroxypropyl]-7-methoxy-3,4-dihydrospiro[chromene-2,4'-piperidin]-6-yl}amino)pyrrolo[2,1-f][1,2,4]triazin-7-yl]phenyl}-N-methylmethanesulfonamide as the TFA salt (48 mg, 18%). 1H-NMR (DMSO-d6): 9.32 (br s, 1H), 8.93 (s, 1H), 7.94 (m, 1H), 7.66 (m, 2H), 7.54 (m, 3H), 6.97 (d, 1H, J=4.7 Hz), 6.94 (d, 1H, J=4.7 Hz), 6.50 (s, 1H), 4.12 (m, 1H), 3.80 (s, 3H), 3.44 (m, 2H), 3.20 (m, 2H), 3.06 (s, 3H), 2.99 (m, 1H), 2.87 (s, 3H), 2.54 (m, 3H), 1.95 (m, 4H), 1.78 (m, 2H), 1.14 (m, 3H). LCMS (HPLC): m/z=607 (M+H).

Example 1497

(4-{2-[4-(4-Methyl-piperazin-1-yl)-phenylamino]-pyrrolo[2,1-f][1,2,4]triazin-7-yl}-phenyl)-methanol (7-Bromo-pyrrolo[2,1-f][1,2,4]triazin-2-yl)-[4-(4-methyl-piperazin-1-yl)-phenyl]-amine (0.125 g, 0.323 mmol), (4-Hydroxymethylphenyl)boronic acid (98.1 mg, 0.646 mmol), Triphenylphosphine (24 mg, 0.090 mmol) and Palladium Acetate (7.2 mg, 0.032 mmol) were placed in a vial and purged with vac/N2. N,N-Dimethylformamide (10.0 mL, 129 mmol), 1,4-Dioxane (3.0 mL, 38 mmol) and 2.00 M of Sodium carbonate in Water (1.50 mL, 3.00 mmol) were added and the mixture again purged (vac/N2) before being heated to 90° C. for 4 h. HPLC showed complete consumption of s.m. and LCMS showed m/z=415. Cool and partition between water:DCM (1:1, 60 mL). Sept., ext. aq. with 30 mL DCM. Wash comb. org. with brine (30 mL) and dry (sodium sulfate), filt. and conc. Chromatograph residue on ISCO (DCM load, 0-15% MeOH:DCM, 2×12 g silica) to afford (4-{2-[4-(4-Methyl-piperazin-1-yl)-phenylamino]-pyrrolo[2,1-f][1,2,4]triazin-7-yl}-phenyl)-methanol (109 mg; Yield=81.5). LCMS (HPLC): 0.73 min, m/z=415 (M+H); 1H-NMR (DMSO-d6): 9.20 (s, 1H), 8.92 (s, 1H), 8.17 (d, 2H, J=8.2 Hz), 7.63 (d, 2H, J=9.0 Hz), 7.47 (d, 2H, J=8.2 Hz), 7.15 (d, 1H, J=4.8 Hz), 6.92 (m, 3H), 5.25 (t, 1H, J=5.8 Hz), 4.58 (d, 2H, J=5.8 Hz), 3.09 (m, 4H), 2.47 (m, 4H), 2.23 (s, 3H).

Example 1498

(3-{2-[4-(4-Methyl-piperazin-1-yl)-phenylamino]-pyrrolo[2,1-f][1,2,4]triazin-7-yl}-phenyl)-methanol Analogous to Example 1497, (7-Bromo-pyrrolo[2,1-f][1,2,4]triazin-2-yl)-[4-(4-methyl-piperazin-1-yl)-phenyl]-amine (0.125 g, 0.323 mmol) and (3-Hydroxymethylphenyl)-boronic acid (98.1 mg, 0.646 mmol) were reacted to afford (3-{2-[4-(4-Methyl-piperazin-1-yl)-phenylamino]-pyrrolo[2,1-f][1,2,4]triazin-7-yl}-phenyl)-methanol (109 mg; Yield=81.5%). LCMS (HPLC): 0.74 min, m/z=415 (M+H); 1H-NMR (DMSO-d6): 9.22 (s, 1H), 8.93 (s, 1H), 8.19 (s, 1H), 7.99 (d, 1H, J=7.8 Hz), 7.64 (d, 2H, J=9.0 Hz), 7.49 (m, 1H), 7.37 (d, 1H, J=7.6 Hz), 7.13 (d, 1H, J=4.7 Hz), 6.92 (m, 3H), 5.25 (t, 1H, J=5.8 Hz), 4.60 (d, 2H, J=5.8 Hz), 3.08 (m, 4H), 2.46 (m, 4H), 2.23 (s, 3H).

Example 1499

[7-(4-Methoxymethyl-phenyl)-pyrrolo[2,1-f][1,2,4]triazin-2-yl]-[4-(4-methyl-piperazin-1-yl)-phenyl]-amine (7-Bromo-pyrrolo[2,1-f][1,2,4]triazin-2-yl)-[4-(4-methyl-piperazin-1-yl)-phenyl]-amine (85 mg, 0.22 mmol), 4-Methoxymethylphenylboronic acid (72.8 mg, 0.439 mmol), Triphenylphosphine (16 mg, 0.062 mmol) and Palladium Acetate (4.9 mg, 0.022 mmol) were placed in a vial and purged with vac/N2. N,N-Dimethylformamide (4.0 mL, 52 mmol), 1,4-Dioxane (2.0 mL, 26 mmol) and 2.00 M of Sodium carbonate in Water (1.02 mL, 2.04 mmol) were added and the mixture again purged (vac/N2) before being heated to 90° C. for 3 h. The mixture was cooled, diluted with EtOAc (10 mL) and ext. w/3M HCl (3×10 mL). The aq. extr. was washed with EtOAc (10 mL), then basified with NaOH (15% w/w), giving a slurry. The slurry was extr. with DCM (3×10 mL) and the org. extr. washed with brine (10 mL), dried over sodium sulfate and conc. in vacuo to give [7-(4-Methoxymethyl-phenyl)-pyrrolo[2,1-f][1,2,4]triazin-2-yl]-[4-(4-methyl-piperazin-1-yl)-phenyl]-amine (89 mg, 94%). LCMS (HPLC): 0.87 min, m/z=429 (M+H); 1H-NMR (CDCl$_3$): 8.67 (s, 1H), 8.14 (d, 2H, J=8.2 Hz), 7.55 (d, 2H, J=8.9 Hz), 7.45 (d, 2H, J=8.2 Hz), 7.00 (d, 1H, J=4.7 Hz), 6.95 (d, 2H, J=8.9 Hz), 6.81 (d, 1H, J=4.7 Hz), 6.64 (s, 1H), 4.55 (s, 2H), 3.45 (s, 3H), 3.20 (m, 4H), 2.61 (m, 4H), 2.37 (s, 3H).

Example 1500

[7-(2-Methoxymethyl-phenyl)-pyrrolo[2,1-f][1,2,4]triazin-2-yl]-[4-(4-methyl-piperazin-1-yl)-phenyl]-amine Analogous to Example 1499, (7-Bromo-pyrrolo[2,1-f][1,2,4]triazin-2-yl)-[4-(4-methyl-piperazin-1-yl)-phenyl]-amine (85 mg, 0.22 mmol) and 2-(Methoxymethyl)phenylboronic acid (72.8 mg, 0.439 mmol) were reacted to afford 7-[2-(methoxymethyl)phenyl]-N-[4-(4-methylpiperazin-1-yl)phenyl]pyrrolo[2,1-f][1,2,4]triazin-2-amine (72 mg, 76%). LCMS (HPLC): 0.88 min, m/z=429 (M+H); 1H-NMR (DMSO-d6): 9.18 (s, 1H), 8.94 (s, 1H), 7.69 (m, 1H), 7.60 (m, 1H), 7.46-7.52 (m, 4H), 6.93 (d, 1H, J=4.6 Hz), 6.87 (d, 1H, J=4.6 Hz), 6.74 (d, 2H, J=9.0 Hz), 4.36 (s, 2H), 3.18 (s, 3H), 3.01 (m, 4H), 2.43 (m, 4H), 2.21 (s, 3H).

Example 1501

7-(2-Methoxy-phenyl)-2-(5-methyl-4H-[1,2,4]triazol-3-yl)-pyrrolo[2,1-f][1,2,4]triazine 7-(2-Methoxy-phenyl)-pyrrolo[2,1-f][1,2,4]triazine-2-carbonitrile (30.5 mg, 0.122 mmol), Potassium carbonate (24.0 mg, 0.174 mmol) and Acetic acid, hydrazide (30.0 mg, 0.405 mmol) were placed in a CEM vial, 1-Butanol (2.0 mL, 22 mmol) was added and the mixture was irradiated in a CEM microwave (150° C., 3 h). Transfer to rbf, conc. in vacuo. Purify on prep HPLC (7.5-40% MeCN:Water, 0.1% TFA) to afford a yellow lyophilate of 7-(2-Methoxy-phenyl)-2-(5-methyl-4H-[1,2,4]triazol-3-yl)-pyrrolo[2,1-f][1,2,4]triazine TFA salt (22 mg; Yield=43%). LCMS (HPLC): 0.84 min, m/z=307 (M+H); 1H-NMR (DMSO-d6): 9.28 (s, 1H), 7.77

(dd, 1H, J=1.6, 7.6 Hz), 7.49 (m, 1H), 7.30 (d, 1H, J=4.6 Hz), 7.24 (d, 1H, J=8.2 Hz), 7.19 (d, 1H, J=4.6 Hz), 7.13 (m, 1H), 3.81 (s, 3H), 2.39 (s, 3H).

Example 1502

7-(2-Methoxy-phenyl)-2-(1H-tetrazol-5-yl)-pyrrolo[2,1-f][1,2,4]triazine

Azidotrimethylsilane (0.250 mL, 1.88 mmol) was added to 7-(2-Methoxy-phenyl)-pyrrolo[2,1-f][1,2,4]triazine-2-carbonitrile (48.0 mg, 0.192 mmol) in Toluene (4.0 mL, 38 mmol) and Dibutyloxostannane (50.0 mg, 0.201 mmol) and heat at 90° C. for 4 h. Cool and conc. in vacuo, then purify by prep HPLC. The lyophilate was dissolved in MeOH, loaded onto a Phenomenex sulfonic acid resin, which was washed with MeOH and then the product eluted as the free base with 2M NH3 in MeOH. Conc. and reconc. from DCM afforded 7-(2-Methoxy-phenyl)-2-(1H-tetrazol-5-yl)-pyrrolo[2,1-f][1,2,4]triazine as a yellow film. LCMS (HPLC): 294 (M+H); 1H-NMR (DMSO-d6): 9.25 (s, 1H), 7.83 (m, 1H), 7.47 (m, 1H), 7.23 (m, 2H), 7.11 (m, 3H), 3.83 (s, 3H).

Example 1503

[7-(3-Methoxymethyl-phenyl)-pyrrolo[2,1-f][1,2,4]triazin-2-yl]-[4-(4-methyl-piperazin-1-yl)-phenyl]-amine (7-Bromo-pyrrolo[2,1-f][1,2,4]triazin-2-yl)-[4-(4-methyl-piperazin-1-yl)-phenyl]-amine (58 mg, 0.15 mmol), 3-(Methoxymethyl)phenylboronic acid (51 mg, 0.31 mmol), Cesium Carbonate (122 mg, 0.374 mmol) and Bis(tri-tert-butylphosphine)palladium (51 mg, 0.10 mmol) were placed in a vial N,N-Dimethylformamide (3.0 mL, 39 mmol) was degassed by cool/pump/thaw and added to the mixture, which was again degassed under vacuum with cooling on dry ice. The mixture was then heated in an 85° C. block. LCMS at 3 h shows conversion to the target. The mixture was transferred to a RBF (with EtOAc) and conc. in vacuo. The residue was taken up in 3N HCl (15 mL), washed with EtOAc (3×10 mL), neutralized with satd. NaHCO3 and then extracted with DCM (3×25 mL). The organic extract was washed with brine, dried and conc. in vacuo. The residue was purified by prep-HPLC (15-40% MeCN:H2O, 0.1% TFA) to afford [7-(3-Methoxymethyl-phenyl)-pyrrolo[2,1-f][1,2,4]triazin-2-yl]-[4-(4-methyl-piperazin-1-yl)-phenyl]-amine as the TFA salt (34 mg; Yield=42) as an orange lyophilate. LCMS (HPLC): 0.95 min, 429 (M+H); 1H-NMR (DMSO-d6): 9.63 (br s, 1H), 9.33 (s, 1H), 8.96 (s, 1H), 8.20 (s, 1H), 8.05 (d, 1H, J=7.9 Hz), 7.69 (d, 2H, J=8.9 Hz), 7.53 (m, 1H), 7.35 (d, 1H, J=7.6 Hz), 7.17 (d, 1H, J=4.7 Hz), 6.99 (d, 2H, J=8.9 Hz), 6.94 (d, 1H, J=4.7 Hz), 4.52 (s, 2H), 3.75 (m, 2H), 3.54 (m, 2H), 3.34 (s, 3H), 3.19 (m, 2H), 2.85-2.95 (m, 5H).

Example 1504

(2-{2-[4-(4-Methyl-piperazin-1-yl)-phenylamino]-pyrrolo[2,1-f][1,2,4]triazin-7-yl}-phenyl)-methanol (7-Bromo-pyrrolo[2,1-f][1,2,4]triazin-2-yl)-[4-(4-methyl-piperazin-1-yl)-phenyl]-amine (88 mg, 0.23 mmol), 3H-Benzo[c][1,2]oxaborol-1-ol (74 mg, 0.56 mmol), Cesium Carbonate (192 mg, 0.589 mmol) and Bis(tri-tert-butylphosphine)palladium (18 mg, 0.035 mmol) were placed in a vial. N,N-Dimethylformamide (4.0 mL, 52 mmol) was added to the mixture, which was "degassed" under vacuum with cooling on dry ice. The mixture was then heated in an 85° C. block under an atmosphere of Nitrogen for 2 h, then conc. in vacuo. The residue was purified on ISCO (24 g load cartridge with DCM:MeOH, then dried; 12 g column, 0-15% MeOH:DCM) to afford (2-{2-[4-(4-Methyl-piperazin-1-yl)-phenylamino]-pyrrolo[2,1-f][1,2,4]triazin-7-yl}-phenyl)-methanol (71 mg; Yield=75%) as an orange foam. LCMS (HPLC): 0.75 min, 415 (M+H); 1H-NMR (DMSO-d6): 9.18 (s, 1H), 8.94 (s, 1H), 7.68 (d, 1H, J=7.5 Hz), 7.63 (d, 1H, J=7.5 Hz), 7.48 (m, 3H), 7.43 (m, 1H), 6.92 (d, 1H, J=4.5 Hz), 6.88 (d, 1H, J=4.5 Hz), 6.74 (d, 2H, J=9.0 Hz), 5.11 (t, 1H, J=5.3 Hz), 4.45 (d, 2H, J=5.3 Hz), 3.01 (m, 4H), 2.44 (m, 4H), 2.22 (s, 3H).

Example 1505

7-(2-Methoxy-phenyl)-2-[5-(4-methyl-piperazin-1-yl)-1H-benzimidazol-2-yl]-pyrrolo[2,1-f][1,2,4]triazine 1505a) 7-(2-Methoxy-phenyl)-pyrrolo[2,1-f][1,2,4]triazine-2-carbonitrile (151 mg, 0.603 mmol) and 9.5 M of Sodium hydroxide in Water (0.20 mL, 1.9 mmol) were combined in Ethanol (6.0 mL) in a vial, which was then heated to reflux for 90 min. The mixture was removed from the heat and treated with 3.00 M of Hydrogen Chloride in Water (1.00 mL, 3.0 mmol), generating a precipitate, which was diluted with water (2 mL), stirred vigorously (thick suspension) then collected by filtration, washing with water (2×8 mL) and drying on the Buchner then in vacuo to afford 7-(2-Methoxy-phenyl)-pyrrolo[2,1-f][1,2,4]triazine-2-carboxylic acid (145 mg, 89%). LCMS (HPLC): 0.76 min, m/z=270 (M+H); 1H-NMR (DMSO-d6): 13.55 (br s, 1H), 9.27 (s, 1H), 7.73 (d, 1H, J=7.5 Hz), 7.49 (m, 1H), 7.39 (d, 1H, J=4.6 Hz), 7.25 (s, 1H), 7.23 (d, 1H, J=4.6 Hz), 7.12 (m, 1H), 3.81 (s, 3H).

1505b) 7-(2-Methoxy-phenyl)-pyrrolo[2,1-f][1,2,4]triazine-2-carboxylic acid (64 mg, 0.24 mmol) and 4-(4-Methyl-piperazin-1-yl)-benzene-1,2-diamine (56 mg, 0.27 mmol) in N,N-Dimethylformamide (2.0 mL, 26 mmol) and N,N-Diisopropylethylamine (0.25 mL, 1.4 mmol) was treated with Bromotris(pyrrolydino)phophonium Hexafluorophosphate (152 mg, 0.326 mmol) and stirred in a vial at rt for 30 min. LCMS (HPLC) shows m/z=458 and no s.m. Quench with 0.1 mL water and conc. in vacuo. The residue was dissolved in Acetic acid (6.0 mL) with heating and heated for 4 h. Conc. in vacuo and purify on prep-HPLC to afford 7-(2-Methoxy-phenyl)-2-[5-(4-methyl-piperazin-1-yl)-1H-benzimidazol-2-yl]-pyrrolo[2,1-f][1,2,4]triazine as the TFA salt (25 mg; Yield=19%) as the TFA salt. LCMS (HPLC): 0.79 min, m/z=440 (M+H); 1H-NMR (DMSO-d6): 9.65 (br s, 1H), 9.39 (s, 1H), 7.82 (d, 1H, J=7.6 Hz), 7.59 (m, 1H), 7.54 (m, 1H), 7.38 (d, 1H, J=4.6 Hz), 7.28 (m, 2H), 7.17 (m, 2H), 7.11 (br s, 1H), 3.84 (s, 3H), 3.82 (m, 2H), 3.55 (m, 2H), 3.22 (m, 2H), 2.99 (m, 2H), 2.89 (s, 3H).

Example 1506

7-[3-(1,1-Dioxido-1,2-thiazolidin-2-yl)phenyl]-N-[3-(1H-pyrazol-1-yl)phenyl]pyrrolo[2,1-f][1,2,4]triazin-2-amine 1506a) Palladium Acetate (0.37 g, 0.0016 mol) and Triphenylphosphine (0.54 g, 0.0020 mol) were dissolved in Tetrahydrofuran (25 mL) and the mixture was allowed to stir at room temperature for 10 minutes. 7-Bromo-2-methylsulfanyl-pyrrolo[2,1-f][1,2,4]triazine (1.95 g, 0.00799 mol) and 3-Aminophenylboronic acid hydrochloride (2.84 g, 0.0164 mol) were added followed by 2.00 M of Sodium carbonate in Water (20.0 mL, 0.0400 mol) and Ethanol (25 mL). The reaction mixture was then heated at 75° C. and was allowed to stir overnight. The reaction mixture was diluted with water (40 mL), cooled and acidified with 12M HCl, then washed twice with EtOAc (50 mL). The org. wash was extracted with 3M HCl (3×30 mL) and the combined aq. extr. washed with EtOAc (2×50 mL). The aq. was then basified with 5N NaOH to pH 9, then extracted with DCM (4×30 mL). The DCM extr. was washed with brine (50 mL) and dried over sodium sulfate before conc. in vacuo. The residue was applied to a 25 g ISCO preload cartridge and purified on the ISCO (40 g, 5-40% EtOAc:Hex). Clean product was isolated from select fractions to afford 3-(2-Methylsulfanyl-pyrrolo[2,1-f][1,2,4]triazin-7-yl)-phenylamine (0.80 g, 39%).

1506b) 3-(2-Methylsulfanyl-pyrrolo[2,1-f][1,2,4]triazin-7-yl)-phenylamine (0.795 g, 3.10 mmol) was dissolved in N,N-Dimethylformamide (12.0 mL) and N,N-Diisopropylethylamine (1.50 mL, 8.61 mmol). Potassium carbonate (1.28 g, 9.30 mmol) was added, followed by 3-Chloropropane-1-sulfonyl chloride (0.450 mL, 3.70 mmol) and stirred overnight. After 24 h, a second aliquot of N,N-Diisopropylethylamine (2.00 mL, 11.5 mmol) and 3-Chloropropane-1-sulfonyl chloride (0.50 mL, 4.1 mmol) was added and stirred additionally. When conversion had reached ca. 90%, the mixture was treated with water (40 mL) and EtOAc (40 mL). The layers were separated, the aq. extr. with EtOAc (3×20 mL) and the comb. org. diluted with hexane (20 mL) and washed with water (30 ml) and brine (30 mL). After drying over sodium sulfate, the mixture was filtered and conc. in vacuo and applied to a 25 g ISCO loading cartridge. Purification on ISCO (40 g column, 10-70% EtOAc:Hex) afforded 7-[3-(1,1-Dioxido-1,2-thiazolidin-2-yl)phenyl]-2-(methylsulfanyl)pyrrolo[2,1-f][1,2,4]triazine (0.52 g; Yield=46%) as a yellow solid. 1H-NMR (CDCl$_3$): 8.74 (s, 1H), 8.06 (s, 1H), 7.86 (d, 1H, J=7.9 Hz), 7.47 (m, 1H), 7.28 (m, 1H), 7.27 (s, 1H), 7.12 (d, 1H, J=4.8 Hz), 6.89 (d, 1H, J=4.8 Hz), 3.86 (t, 2H, J=6.5 Hz), 3.42 (t, 2H, J=7.4 Hz), 2.62 (s, 3H), 2.58 (m, 2H).

1506c) m-Chloroperbenzoic acid (0.380 g, 1.54 mmol) was added to a solution of 7-[3-(1,1-Dioxido-1,2-thiazolidin-2-yl)phenyl]-2-(methylsulfanyl)pyrrolo[2,1-f][1,2,4]triazine (0.515 g, 1.43 mmol) in Methylene chloride (30.0 mL, 468 mmol). The reaction was quenched at 30 min by the addition of satd. NaHCO3 (50 mL). The mixture was stirred vigorously, sept. and ext. with DCM (3×15 mL). The comb. org. was washed with 1:1 brine:satd. NaHCO3 (50 mL) and dried over sodium sulfate. After conc. in vacuo, the residue was purified on the ISCO (load onto 3.4 g silica, 40 g column, 20-100% EtOAc:Hex, then to 10% MeOH:EtOAc, then 10% MeOH:DCM) to afford 7-[3-(1,1-Dioxido-1,2-thiazolidin-2-yl)phenyl]-2-(methylsulfinyl)pyrrolo[2,1-f][1,2,4]triazine (0.485 g, 90%). 1H-NMR (DMSO-d6): 9.34 (s, 1H), 8.16 (s, 1H), 7.95 (d, 1H, J=7.9 Hz), 7.72 (d, 1H, J=4.9 Hz), 7.55 (m, 1H), 7.34 (m, 2H), 3.87 (t, 2H, J=6.5 Hz), 3.57 (t, 2H, J=7.4 Hz), 2.99 (s, 3H), 2.44 (m, 2H).

1506d) Analogous to Example 1491c, 7-[3-(1,1-Dioxido-1,2-thiazolidin-2-yl)phenyl]-2-(methylsulfinyl)pyrrolo[2,1-f][1,2,4]triazine (90.0 mg, 0.239 mmol) and 3-Pyrazol-1-yl-phenylamine (76.1 mg, 0.478 mmol) were reacted to afford 7-[3-(1,1-Dioxido-1,2-thiazolidin-2-yl)phenyl]-N-[3-(1H-pyrazol-1-yl)phenyl]pyrrolo[2,1-f][1,2,4]triazin-2-amine as the TFA salt (7 mg, 5%). LCMS (HPLC): 1.13 min, m/z=472 (M+H); 1H-NMR (DMSO-d6): 9.71 (s, 1H), 9.05 (s, 1H), 8.24 (s, 1H), 8.21 (s, 1H), 7.95 (d, 1H, J=7.8 Hz), 7.73 (m, 2H), 7.69 (m, 1H), 7.40 (m, 2H), 7.36 (d, 1H, J=7.9 Hz), 7.28 (d, 1H, J=8.2 Hz), 7.16 (m, 2H), 7.01 (d, 1H, J=4.7 Hz), 6.52 (s, 1H), 3.73 (t, 2H, J=6.5 Hz), 3.51 (t, 2H, J=7.3 Hz), 2.35 (m, 2H).

Example 1507

7-[3-(1,1-Dioxido-1,2-thiazolidin-2-yl)phenyl]-N-[7-(morpholin-4-yl)-6,7,8,9-tetrahydro-5H-benzo[7]annulen-2-yl]pyrrolo[2,1-f][1,2,4]triazin-2-amine Analogous to Example 1491c, 7-[3-(1,1-Dioxido-1,2-thiazolidin-2-yl)phenyl]-2-(methylsulfinyl)pyrrolo[2,1-f][1,2,4]triazine (90.0 mg, 0.239 mmol) and 7-Morpholin-4-yl-6,7,8,9-tetrahydro-5H-benzocyclohepten-2-ylamine (118 mg, 0.478 mmol) were reacted to afford 7-[3-(1,1-Dioxido-1,2-thiazolidin-2-yl)phenyl]-N-[7-(morpholin-4-yl)-6,7,8,9-tetrahydro-5H-benzo[7]annulen-2-yl]pyrrolo[2,1-f][1,2,4]triazin-2-amine as the TFA salt (37 mg, 23%). LCMS (HPLC): 0.89 min, m/z=559 (M+H); 1H-NMR (DMSO-d6): 9.47 (m, 2H), 9.00 (s, 1H), 8.06 (d, 1H, J=7.8 Hz), 7.75 (s, 1H), 7.65 (s, 1H), 7.55 (m, 1H), 7.44 (d, 1H, J=8.1 Hz), 7.35 (d, 1H, J=8.0 Hz), 7.14 (d, 1H, J=4.7 Hz), 7.10 (d, 1H, J=8.2 Hz), 6.97 (d, 1H, J=4.7 Hz), 4.00 (m, 2H), 3.81 (t, 2H, J=6.5 Hz), 3.71 (m, 2H), 3.56 (m, 3H), 3.31 (m, 2H), 3.22 (m, 2H), 2.78 (m, 4H), 2.43 (m, 2H), 2.34 (m, 2H), 1.48 (m, 2H).

Example 1508

N-[3-({7-[3-(1,1-Dioxido-1,2-thiazolidin-2-yl)phenyl]pyrrolo[2,1-f][1,2,4]triazin-2-yl}amino)phenyl]acetamide Analogous to Example 1491c, 7-[3-(1,1-Dioxido-1,2-thiazolidin-2-yl)phenyl]-2-(methylsulfinyl)pyrrolo[2,1-f][1,2,4]triazine (90.0 mg, 0.239 mmol) and 3'-aminoacetanilide (71.8 mg, 0.478 mmol) were reacted to afford N-[3-({7-[3-(1,1-Dioxido-1,2-thiazolidin-2-yl)phenyl]pyrrolo[2,1-f][1,2,4]triazin-2-yl}amino)phenyl]acetamide as the TFA salt (25 mg, 18%). LCMS (HPLC): 0.96 min, m/z=463 (M+H); 1H-NMR (DMSO-d6): 9.85 (s, 1H), 9.48 (s, 1H), 9.01 (s, 1H), 7.95 (d, 1H, J=7.8 Hz), 7.79 (s, 1H), 7.75 (s, 1H), 7.54 (m, 1H), 7.47 (m, 1H), 7.31 (d, 1H, J=8.1 Hz), 7.20 (m, 2H), 7.17 (d, 1H, J=4.7 Hz), 6.97 (d, 1H, J=4.7 Hz), 3.69 (t, 2H, J=6.5 Hz), 3.52 (t, 2H, J=7.4 Hz), 2.36 (m, 2H), 2.03 (s, 3H).

Example 1509

7-[3-(1,1-Dioxido-1,2-thiazolidin-2-yl)phenyl]-N-[3-(4-methylpiperazin-1-yl)phenyl]pyrrolo[2,1-f][1,2,4]triazin-2-amine Analogous to Example 1491c, 7-[3-(1,1-Dioxido-1,2-thiazolidin-2-yl)phenyl]-2-(methylsulfinyl)pyrrolo[2,1-f][1,2,4]triazine (90.0 mg, 0.239 mmol) and 3-(4-Methylpiperazin-1-yl)aniline (91.4 mg, 0.478 mmol) were reacted to afford 7-[3-(1,1-Dioxido-1,2-thiazolidin-2-yl)phenyl]-N-[3-(4-methylpiperazin-1-yl)phenyl]pyrrolo[2,1-f][1,2,4]triazin-2-amine (25 mg, 18%). LCMS (HPLC): 0.84 min, m/z=504 (M+H); 1H-NMR (DMSO-d6): 9.29 (s, 1H), 8.99 (s, 1H), 7.86 (d, 1H, J=7.8 Hz), 7.75 (s, 1H), 7.49 (m, 1H), 7.32 (m, 2H), 7.18 (d, 1H, J=8.0 Hz), 7.11 (m, 2H), 6.96 (d, 1H, J=4.7 Hz), 6.56 (d, 1H, J=7.8 Hz), 3.73 (t, 2H, J=6.4 Hz), 3.52 (t, 2H, J=7.4 Hz), 2.99 (m, 4H), 2.37 (m, 6H), 2.20 (s, 3H).

Example 1510

6-({7-[3-(1,1-Dioxido-1,2-thiazolidin-2-yl)phenyl]pyrrolo[2,1-f][1,2,4]triazin-2-yl}amino)-3,3-dimethyl-1,3-dihydro-2H-indol-2-one 1510a) 7-[3-(1,1-Dioxido-1,2-thiazolidin-2-yl)phenyl]-2-(methylsulfanyl)pyrrolo[2,1-f][1,2,4]triazine (0.480 g, 1.33 mmol) was suspended in Methanol (25 mL, 620 mmol), Sodium Tungstate Dihydrate (22.0 mg, 0.0666 mmol) was added followed by 50% Hydrogen Peroxide (0.250 mL, 4.40 mmol). The mixture was heated at 50° C. overnight. Little conversion occurred-due to low solubility of the sulfide. Acetic acid (5 mL, 90 mmol) was added and heating continued. After 6 h, more 50% Hydrogen Peroxide (0.400 mL, 7.04 mmol) and Acetic acid (5 mL, 90 mmol) was added, and stirring was continued at 50° C. for a second overnight. The mixture was treated dropwise with 10% Na2S2O3 (40 mL) then allowed to cool. The ppt was collected, washing with water (50 mL) to afford the sulfone:sulfoxide mixture (9:1). The sulfone:sulfoxide mixture was partially solubilized in 1,4-Dioxane (1.00 mL) and Dimethyl sulfoxide (0.600 mL), then was treated with 5.0 M of Sodium hydroxide in Water (3.00 mL, 15.0 mmol) and heated at 80° C. until a homogenous solution was obtained. The mixture was cooled, treated with 3M HCl until ppt remained and was allowed to stand 30 min. The solids were collected on a Buchner funnel, washing with water. 7-[3-(1,1-dioxo-1,2-thiazolidin-2-yl)phenyl]-pyrrolo[2,1-f][1,2,4]triazin-2-ol (0.185 g; Yield=51%) was isolated as brown solids.

1510b) 7-[3-(1,1-dioxo-1,2-thiazolidin-2-yl)phenyl]pyrrolo[2,1-f][1,2,4]triazin-2-ol (47 mg, 0.14 mmol) and N-Phenylbis(trifluoromethanesulphonimide) (55.9 mg, 0.156 mmol) were treated with N,N-Diisopropylethylamine (0.100 mL, 0.575 mmol) and N,N-Dimethylformamide (3.00 mL, 38.7 mmol) for 30 min, then 6-Amino-3,3-dimethyl-1,3-dihydro-indol-2-one (31.3 mg, 0.178 mmol) was added and the mixture was stirred at 65° C. overnight. Conc. of the reaction gave a residue, which was chromatographed (silica gel, 20-100% EtOAc:Hex) to afford 6-({7-[3-(1,1-Dioxido-1,2-thiazolidin-2-yl)phenyl]pyrrolo[2,1-f][1,2,4]triazin-2-yl}amino)-3,3-dimethyl-1,3-dihydro-2H-indol-2-one (39 mg; Yield=56%) as a yellow foam. LCMS (HPLC): 1.05 min, m/z=489 (M+H); 1H-NMR (DMSO-d6): 10.28 (s, 1H), 9.50 (s, 1H), 9.01 (s, 1H), 7.96 (d, 1H, J=7.8 Hz), 7.79 (s, 1H), 7.56 (m, 2H), 7.33 (d, 1H, J=8.3 Hz), 7.16 (m, 2H), 7.08 (s, 1H), 6.97 (d, 1H, J=4.7 Hz), 3.80 (t, 2H, J=6.5 Hz), 3.52 (t, 2H, J=7.4 Hz), 2.39 (m, 2H), 1.24 (s, 6H).

Example 1511

N-(1H-Benzimidazol-6-yl)-7-[3-(1,1-dioxido-1,2-thiazolidin-2-yl)phenyl]pyrrolo[2,14][1,2,4]triazin-2-amine Analogous to Example 1510b, 7-[3-(1,1-dioxo-1,2-thiazolidin-2-yl)phenyl]pyrrolo[2,1-f][1,2,4]triazin-2-ol (47 mg, 0.14 mmol) and 3H-Benzimidazol-5-ylamine (23.7 mg, 0.178 mmol) were reacted to afford N-(1H-Benzimidazol-6-yl)-7-[3-(1,1-dioxido-1,2-thiazolidin-2-yl)phenyl]pyrrolo[2,14][1,2,4]triazin-2-amine as the TFA salt (33 mg, 41%). LCMS (HPLC): 0.80 min, m/z=446 (M+H); 1H-NMR (DMSO-d6): 14.55 (br s, 1H), 9.86 (s, 1H), 9.36 (s, 1H), 9.07 (s, 1H), 8.14 (s, 1H), 8.02 (d, 1H, J=7.8 Hz), 7.91 (d, 1H, J=9.0 Hz), 7.80 (s, 1H), 7.76 (d, 1H, J=9.0 Hz), 7.58 (m, 1H), 7.32 (d, 1H, J=8.2 Hz), 7.22 (d, 1H, J=4.7 Hz), 7.03 (d, 1H, J=4.7 Hz), 3.75 (t, 2H, J=6.4 Hz), 3.50 (t, 2H, J=7.4 Hz), 2.34 (m, 2H).

Example 1512

2-{4-[4-({7-[3-(1,1-Dioxido-1,2-thiazolidin-2-yl)phenyl]pyrrolo[2,1-f][1,2,4]triazin-2-yl}amino)phenyl]piperidin-1-yl}acetamide Analogous to Example 1510b, 7-[3-(1,1-dioxo-1,2-thiazolidin-2-yl)phenyl]pyrrolo[2,1-f][1,2,4]triazin-2-ol (81 mg, 0.24 mmol) and 2-[4-(4-Amino-phenyl)-piperidin-1-yl]-acetamide (62.9 mg, 0.270 mmol) were reacted to afford 2-{4-[4-({7-[3-(1,1-Dioxido-1,2-thiazolidin-2-yl)phenyl]pyrrolo[2,1-f][1,2,4]triazin-2-yl}amino)phenyl]piperidin-1-yl}acetamide as the TFA salt (78 mg, 48%). LCMS (HPLC): 546 (M+H); 1H-NMR (DMSO-d6): 9.55 (br s, 1H), 9.53 (s, 1H), 9.01 (s, 1H), 7.96 (m, 2H), 7.74 (m, 4H), 7.54 (m, 1H), 7.35 (d, 1H, J=9.1 Hz), 7.15 (m, 3H), 6.98 (d, 1H, J=4.7 Hz), 3.92 (d, 2H, J=4.0 Hz), 3.80 (t, 2H, J=6.4 Hz), 3.54 (m, 4H), 3.16 (m, 2H), 2.74 (m, 1H), 2.41 (m, 2H), 1.97 (m, 4H).

Example 1513

[7-(6-Methoxy-pyridin-3-yl)-pyrrolo[2,1-f][1,2,4]triazin-2-yl]-(2-morpholin-4-ylmethyl-3H-benzimidazol-5-yl)-amine 1513a) 2-Chloromethyl-5-nitro-1H-benzimidazole (335 mg, 1.58 mmol) was treated with Morpholine (0.350 mL, 4.01 mmol) in Ethanol (6.0 mL) in a sealed vial at 65° C. for 4 h. Partition between brine:satd. NaHCO3 and DCM (10 mL:10 mL and 20 mL) and extr. aq. with DCM. Wash DCM extracts with brine and dry (sodium sulfate), conc. in vacuo to a foam. 1H-NMR shows the presence of morpholine, ~6:1 ratio of 2-Morpholin-4-ylmethyl-5-nitro-1H-benzimidazole: morpholine, which was used crude.

1513b) 2-Morpholin-4-ylmethyl-5-nitro-1H-benzimidazole (0.395 g, 1.51 mmol) in 3.00 M of Hydrogen Chloride in Methanol (3.00 mL, 9.00 mmol) and Methanol (12.0 mL) was shaken over 5% Platinum on Carbon, Sulfided (0.5%) (0.200 g, 0.0513 mmol) under an atmosphere of Hydrogen (30 psi) for 2.5 h. The mixture was filtered through Celite, washing with MeOH. 3.00 M of Hydrogen Chloride in Methanol (3 mL) was again added and the mixture before conc. in vacuo. $^1$H-NMR shows clean conversion to the aniline, but morpholine present in ~20 mol %. Free base material (1:1 DCM: MeOH, 20 mL and treat with MP-Carbonate (3.16 mmol/g loading; 2.94 g, 9.29 mmol) for 1.5 h. Filter and wash with DCM. Conc. in vacuo to a foam, dry over weekend under vacuum. Reformation of the HCl salt gave a brown foam.

1513c) Analogous to Example 1510b, 2-Morpholin-4-ylmethyl-3H-benzoimidazol-5-ylamine trihydrochloride (41 mg, 0.12 mmol) was reacted with Trifluoro-methanesulfonic acid [7-(6-Methoxy-pyridin-3-yl)-pyrrolo[2,1-f][1,2,4]triazin-2-yl]-(2-morpholin-4-ylmethyl-3H-benzimidazol-5-yl)-amine as the TFA salt (39 mg, 67%). LCMS (HPLC): 0.80 min, m/z=457 (M+H); 1H-NMR (DMSO-d6): 9.70 (s, 1H), 9.03 (s, 1H), 8.93 (s, 1H), 8.59 (dd, 1H, J=2.0, 8.8 Hz), 8.10 (s, 1H), 7.66 (m, 2H), 7.23 (d, 1H, J=4.7 Hz), 7.01 (m, 2H), 4.33 (s, 2H), 3.94 (s, 3H), 3.78 (br s, 4H), 3.00 (br s, 4H).

Example 1514

N-tert-Butyl-3-[2-(2-morpholin-4-ylmethyl-3H-benzimidazol-5-ylamino)-pyrrolo[2,1-f][1,2,4]triazin-7-yl]-benzenesulfonamide Analogous to Example 1510b, N-tert-Butyl-3-(2-hydroxy-pyrrolo[2,1-f][1,2,4]triazin-7-yl)-benzenesulfonamide (57 mg, 0.16 mmol) and 2-Morpholin-4-ylmethyl-3H-benzoimidazol-5-ylamine trihydrochloride (67.8 mg, 0.198 mmol) were reacted to afford N-tert-Butyl-3-[2-(2-morpholin-4-ylmethyl-3H-benzimidazol-5-ylamino)-pyrrolo[2,1-f][1,2,4]triazin-7-yl]-benzenesulfonamide as the TFA salt (68 mg, 61%). LCMS (HPLC): 0.91 min, m/z=561 (M+H); 1H-NMR (DMSO-d6): 9.76 (s, 1H), 9.08 (s, 1H), 8.58 (s, 1H), 8.46 (d, 1H, J=8.0 Hz), 8.01 (s, 1H), 7.85 (m, 2H), 7.73 (m, 2H), 7.64

(s, 1H), 7.26 (d, 1H, J=4.8 Hz), 7.04 (d, 1H, J=4.8 Hz), 4.32 (br s, 2H), 3.78 (br s, 4H), 2.98 (br s, 4H), 1.10 (s, 9H).

Example 1515

N-tert-Butyl-3-(2-{4-[1,1-difluoro-2-(4-methyl-piperazin-1-yl)-2-oxo-ethyl]-phenylamino}-pyrrolo[2,1-f][1,2,4]triazin-7-yl)-benzenesulfonamide 1515a) Difluoro-(4-nitro-phenyl)-acetic acid (106 mg, 0.488 mmol) was suspended in Thionyl chloride (1.00 mL, 13.7 mmol) and heated at 79° C. in a vial for 5 h. Conc. and azeotroping with toluene afforded a residue, which was dried in vacuo. 1-Methyl-piperazine (0.100 mL, 0.902 mmol), N,N-Diisopropylethylamine (0.250 mL, 1.44 mmol) and 1,2-Dichloroethane (1.00 mL, 12.7 mmol) were added to the residue. The mixture was diluted with EtOAc (10 mL) and water:brine:NaHCO3 (1:3:2, 6 mL), the layers separated and the aq. extr. with DCM (2×3 mL). The comb. org. were dried, filtered and conc. in vacuo to give an oil which very slowly crystallizes. The crude amide (124 mg) was shaken under an atmosphere of Hydrogen (15 psi) over 10% Palladium on Carbon (50% Wet) (24 mg, 0.011 mmol) in Methanol (10.0 mL) overnight. Filtration and conc. afforded 2-(4-Amino-phenyl)-2,2-difluoro-1-(4-methyl-piperazin-1-yl)-ethanone (0.113 g; Yield=86.0%) as a film.

1515b) Analogous to Example 1510b, N-tert-Butyl-3-(2-hydroxy-pyrrolo[2,1-f][1,2,4]triazin-7-yl)-benzenesulfonamide (57 mg, 0.16 mmol) in N,N-Dimethylformamide (3.00 mL, 38.7 mmol) and 2-(4-Amino-phenyl)-2,2-difluoro-1-(4-methyl-piperazin-1-yl)-ethanone (55 mg, 0.20 mmol) were reacted to afford N-tert-Butyl-3-(2-{4-[1,1-difluoro-2-(4-methyl-piperazin-1-yl)-2-oxo-ethyl]-phenylamino}-pyrrolo[2,1-f][1,2,4]triazin-7-yl)-benzenesulfonamide as the TFA salt (21 mg, 18%). LCMS (HPLC): 0.97 min, m/z=598 (M+H); 1H-NMR (DMSO-d6): 10.00 (s, 1H), 9.92 (br s, 1H), 9.11 (s, 1H), 8.68 (s, 1H), 8.21 (d, 1H, J=7.8 Hz), 7.94 (d, 2H, J=8.5 Hz), 7.89 (d, 1H, J=7.8 Hz), 7.77 (m, 1H), 7.69 (s, 1H), 7.55 (d, 2H, J=8.5 Hz), 7.27 (d, 1H, J=4.8 Hz), 7.06 (d, 1H, J=4.8 Hz), 4.51 (br s, 1H), 3.1-3.5 (m, 6H), 2.79 (m, 4H), 1.11 (s, 9H).

Example 1516

2,2-Difluoro-2-{4-[7-(6-methoxy-pyridin-3-yl)-pyrrolo[2,1-f][1,2,4]triazin-2-ylamino]-phenyl}-1-(4-methyl-piperazin-1-yl)-ethanone Analogous to Example 1510b, Trifluoro-methanesulfonic acid 7-(6-methoxy-pyridin-3-yl)-pyrrolo[2,1-f][1,2,4]triazin-2-yl ester (62 mg, 0.16 mmol) and 2-(4-Amino-phenyl)-2,2-difluoro-1-(4-methyl-piperazin-1-yl)-ethanone (55 mg, 0.20 mmol) were reacted to afford 2,2-Difluoro-2-{4-[7-(6-methoxy-pyridin-3-yl)-pyrrolo[2,1-f][1,2,4]triazin-2-ylamino]-phenyl}-1-(4-methyl-piperazin-1-yl)-ethanone as the TFA salt (35 mg, 35%). LCMS (HPLC): 0.89 min, m/z=494 (M+H); 1H-NMR (DMSO-d6): 9.95 (s, 1H), 9.81 (br s, 1H), 9.05 (s, 1H), 8.91 (d, 1H, J=1.5 Hz), 8.49 (dd, 1H, J=2.2, 8.8 Hz), 7.90 (d, 2H, J=8.5 Hz), 7.50 (d, 2H, J=8.5 Hz), 7.24 (d, 1H, J=4.8 Hz), 7.07 (d, 1H, J=8.8 Hz), 7.03 (d, 1H, J=4.8 Hz), 4.49 (br s, 1H), 3.95 (s, 3H), 3.1-3.5 (m, 6H), 2.79 (m, 4H).

Example 1517

N-Methyl-N-{2-[2-(2-morpholin-4-ylmethyl-3H-benzimidazol-5-ylamino)-pyrrolo[2,1-f][1,2,4]triazin-7-yl]-phenyl}-methanesulfonamide Analogous to Example 1510b, 2-Morpholin-4-ylmethyl-3H-benzoimidazol-5-ylamine trihydrochloride (65 mg, 0.19 mmol) and Trifluoro-methanesulfonic acid 7-[2-(methanesulfonyl-methyl-amino)-phenyl]-pyrrolo[2,1-f][1,2,4]triazin-2-yl ester (71 mg, 0.16 mmol) were reacted to afford N-Methyl-N-{2-[2-(2-morpholin-4-ylmethyl-3H-benzimidazol-5-ylamino)-pyrrolo[2,1-f][1,2,4]triazin-7-yl]-phenyl}-methanesulfonamide as the TFA salt (71 mg, 69%). LCMS (HPLC): 0.76 min, m/z=533 (M+H); 1H-NMR (DMSO-d6): 9.57 (s, 1H), 9.01 (s, 1H), 8.05 (d, 1H, J=7.6 Hz), 7.99 (s, 1H), 7.64 (m, 3H), 7.55 (m, 2H), 7.02 (d, 1H, J=4.7 Hz), 6.98 (d, 1H, J=4.7 Hz), 4.32 (s, 2H), 3.78 (m, 4H), 3.10 (s, 3H), 3.00 (m, 4H), 2.89 (s, 3H).

Example 1518

[7-(2-Methoxy-phenyl)-pyrrolo[2,1-f][1,2,4]triazin-2-yl]-(2-morpholin-4-ylmethyl-3H-benzimidazol-5-yl)-amine Analogous to Example 1510b, 2-Morpholin-4-ylmethyl-3H-benzoimidazol-5-ylamine trihydrochloride (65 mg, 0.19 mmol) and Trifluoro-methanesulfonic acid 7-(2-methoxy-phenyl)-pyrrolo[2,1-f][1,2,4]triazin-2-yl ester (61 mg, 0.16 mmol) were reacted to afford [7-(2-Methoxy-phenyl)-pyrrolo[2,1-f][1,2,4]triazin-2-yl]-(2-morpholin-4-ylmethyl-3H-benzimidazol-5-yl)-amine as the TFA salt (69 mg, 74%). LCMS (HPLC): 0.89 min, m/z=456 (M+H); 1H-NMR (DMSO-d6): 9.57 (s, 1H), 9.01 (s, 1H), 8.05 (d, 1H, J=7.6 Hz), 7.99 (s, 1H), 7.64 (m, 3H), 7.55 (m, 2H), 7.02 (d, 1H, J=4.7 Hz), 6.98 (d, 1H, J=4.7 Hz), 4.34 (s, 2H), 3.82 (s, 3H), 3.79 (m, 4H), 3.03 (m, 4H).

Example 1519

[3-(1,4-Dimethyl-piperazin-2-yl)-phenyl]-[7-(6-methoxy-pyridin-3-yl)-pyrrolo[2,1-f][1,2,4]triazin-2-yl]-amine

[7-(6-Methoxy-pyridin-3-yl)-pyrrolo[2,1-f][1,2,4]triazin-2-yl]-(3-piperazin-2-yl-phenyl)-amine TFA salt (25 mg, 0.048 mmol) was suspended in Tetrahydrofuran (2.0 mL, 25 mmol), 37% aq. Formaldehyde (0.030 mL, 0.40 mmol) was added followed by Sodium triacetoxyborohydride (25 mg, 0.12 mmol). After 20 min, the mixture was quenched with 0.10 mL satd. NaHCO3 and conc. in vacuo (high vac). The residue was taken up in DMSO/MeOH/water and purified on RP-HPLC to afford [3-(1,4-Dimethyl-piperazin-2-yl)-phenyl]-[7-(6-methoxy-pyridin-3-yl)-pyrrolo[2,1-f][1,2,4]triazin-2-yl]-amine (12 mg, 46%) as the TFA salt. LCMS (HPLC): 0.90 min, m/z=430 (M+H); 1H-NMR (DMSO-d6): 9.62 (s, 1H), 9.02 (s, 1H), 8.47 (dd, 1H, J=1.9 Hz, 8.6 Hz), 7.71 (m, 2H), 7.38 (m, 1H), 7.23 (d, 1H, J=4.7 Hz), 7.01 (m, 3H), 3.95 (s, 3H), 2.8-3.5 (m, 7H), 2.75 (s, 3H), 2.12 (s, 3H).

Example 1520

N-tert-Butyl-3-(2-{2-[4-(2-hydroxy-ethyl)-piperazin-1-ylmethyl]-3H-benzimidazol-5-ylamino}-pyrrolo[2,1-f][1,2,4]triazin-7-yl)-benzenesulfonamide 1520a) 2-[4-(5-Nitro-1H-benzimidazol-2-ylmethyl)-piperazin-1-yl]-ethanol (1.085 g, 2.587 mmol) [Goker, H.; Kus, C.; Abbasoglu, U. Arch. Pharm. (Weinheim, Ger.) 1995, 328, 425] was dissolved in Methanol (20.0 mL) and 5% Platinum on Carbon, Sulfided (0.5%) (162 mg, 0.0415 mmol) and 3.00 M of Hydrogen Chloride in Methanol (8.0 mL, 24 mmol) were added. The mixture was shaken under an atmosphere of Hydrogen (25 psi) for 2 h. The mixture was filtered through Celite with MeOH and additional 3.00 M of Hydrogen Chloride in Methanol (3 mL, 9 mmol) was added to the filtrate prior to conc. in vacuo to afford 2-[4-(5-Amino-1H-benzimidazol-2-ylmethyl)-piperazin-1-yl]-ethanol tetrahydrochloride as a foam (0.90 g, 83%). 1H-NMR (DMSO-d6): 10.41 (br s, 1H), 7.72 (d, 1H, J=8.6 Hz), 7.52 (s, 1H), 7.25 (d, 1H, J=8.6 Hz), 4.20 (s, 2H), 3.78 (t, 2H, J=4.8 Hz), 3.53 (m, 2H), 3.19 (m, 4H), 3.09 (m, 2H), 2.85 (m, 2H).

1520b) Analogous to Example 1510b, N-tert-Butyl-3-(2-hydroxy-pyrrolo[2,1-f][1,2,4]triazin-7-yl)-benzenesulfonamide (49 mg, 0.14 mmol) and 2-[4-(5-Amino-1H-benzimidazol-2-ylmethyl)-piperazin-1-yl]-ethanol tetrahydrochloride (75 mg, 0.18 mmol) were reacted to afford N-tert-Butyl-3-(2-{2-[4-(2-hydroxy-ethyl)-piperazin-1-ylmethyl]-3H-benzimidazol-5-ylamino}-pyrrolo[2,1-f][1,2,4]triazin-7-yl)-benzenesulfonamide as the TFA salt (62 mg, 63%). LCMS (HPLC): 0.81 min, m/z=604 (M+H); 1H-NMR (DMSO-d6): 9.83 (s, 1H), 9.50 (br s, 1H), 9.09 (s, 1H), 8.65 (s, 1H), 8.39 (d, 1H, J=8.0 Hz), 8.00 (s, 1H), 7.95 (m, 1H), 7.86 (d, 1H, J=7.8 Hz), 7.73 (m, 3H), 7.27 (d, 1H, J=4.8 Hz), 7.05 (d, 1H, J=4.8 Hz), 5.38 (br s, 1H), 4.10 (s, 2H), 3.75 (m, 2H), 3.52 (m, 2H), 3.22 (m, 2H), 3.10 (m, 4H), 2.70 (m, 2H), 1.10 (s, 9H).

Example 1521

N-[2-(2-{2-[4-(2-Hydroxy-ethyl)-piperazin-1-ylmethyl]-3H-benzimidazol-5-ylamino}-pyrrolo[2,1-f][1,2,4]triazin-7-yl)-phenyl]-N-methyl-methanesulfonamide Analogous to Example 1510b, 2-[4-(5-Amino-1H-benzimidazol-2-ylmethyl)-piperazin-1-yl]-ethanol tetrahydrochloride (73.2 mg, 0.174 mmol) and Trifluoro-methanesulfonic acid 7-[2-(methanesulfonyl-methyl-amino)-phenyl]-pyrrolo[2,1-f][1,2,4]triazin-2-yl ester (71 mg, 0.16 mmol) were reacted to afford the TFA salt of N-[2-(2-{2-[4-(2-Hydroxy-ethyl)-piperazin-1-ylmethyl]-3H-benzimidazol-5-ylamino}-pyrrolo[2,1-f][1,2,4]triazin-7-yl)-phenyl]-N-methyl-methanesulfonamide (65 mg, 60%). LCMS (HPLC): 0.66 min, m/z=576 (M+H); 1H-NMR (DMSO-d6): 9.66 (s, 1H), 9.49 (br s, 1H), 9.03 (s, 1H), 8.03 (d, 1H, J=7.4 Hz), 7.96 (s, 1H), 7.77 (d, 1H, J=8.7 Hz), 7.62 (m, 3H), 7.53 (m, 1H), 7.01 (m, 2H), 5.37 (br s, 1H), 4.10 (s, 2H), 3.75 (m, 2H), 3.51 (m, 2H), 3.22 (m, 2H), 3.11 (m, 7H), 2.88 (s, 3H), 2.67 (m, 2H).

Example 1522

2-(4-{6-[7-(2-Methoxy-phenyl)-pyrrolo[2,1-f][1,2,4]triazin-2-ylamino]-1H-benzimidazol-2-ylmethyl}-piperazin-1-yl)-ethanol Analogous to Example 1510b, 2-[4-(5-Amino-1H-benzimidazol-2-ylmethyl)-piperazin-1-yl]-ethanol tetrahydrochloride (73.2 mg, 0.174 mmol) and Trifluoro-methanesulfonic acid 7-(2-methoxy-phenyl)-pyrrolo[2,1-f][1,2,4]triazin-2-yl ester (59.0 mg, 0.158 mmol) were reacted to afford the TFA salt of 2-(4-{6-[7-(2-Methoxy-phenyl)-pyrrolo[2,1-f][1,2,4]triazin-2-ylamino]-1H-benzimidazol-2-ylmethyl}-piperazin-1-yl)-ethanol (43 mg, 44%). LCMS (HPLC): 0.76 min, m/z=499 (M+H); 1H-NMR (DMSO-d6): 9.66 (s, 1H), 9.47 (br s, 1H), 9.01 (s, 1H), 7.90 (m, 3H), 7.58 (d, 1H, J=8.8 Hz), 7.45 (m, 1H), 7.23 (d, 1H, J=8.3 Hz), 7.15 (m, 1H), 7.01 (d, 1H, J=4.6 Hz), 6.97 (d, 1H, J=4.6 Hz), 5.38 (br s, 1H), 4.09 (s, 2H), 3.81 (s, 3H), 3.75 (m, 2H), 3.51 (m, 2H), 3.22 (m, 2H), 3.08 (m, 4H), 2.67 (m, 2H).

Example 1523

2-(4-{6-[7-(6-Methoxy-pyridin-3-yl)-pyrrolo[2,1-f][1,2,4]triazin-2-ylamino]-1H-benzimidazol-2-ylmethyl}-piperazin-1-yl)-ethanol Analogous to Example 1510b, 2-[4-(5-Amino-1H-benzimidazol-2-ylmethyl)-piperazin-1-yl]-ethanol tetrahydrochloride (73.2 mg, 0.174 mmol) and Trifluoro-methanesulfonic acid 7-(6-methoxy-pyridin-3-yl)-pyrrolo[2,1-f][1,2,4]triazin-2-yl ester (59.2 mg, 0.158 mmol) were reacted to afford the TFA salt of 2-(4-{6-[7-(6-Methoxy-pyridin-3-yl)-pyrrolo[2,1-f][1,2,4]triazin-2-ylamino]-1H-benzimidazol-2-ylmethyl}-piperazin-1-yl)-ethanol (57 mg, 59%). LCMS (HPLC): 0.70 min, m/z=500 (M+H); 1H-NMR (DMSO-d6): 9.79 (s, 1H), 9.51 (br s, 1H), 9.04 (s, 1H), 8.94 (d, 1H, J=2.0 Hz), 8.57 (dd, 1H, J=2.0, 8.7 Hz), 8.11 (s, 1H), 7.77 (d, 1H, J=8.9 Hz), 7.71 (d, 1H, J=8.9 Hz), 7.25 (d, 1H, J=4.8 Hz), 7.02 (m, 2H), 5.40 (br s, 1H), 4.11 (s, 2H), 3.94 (s, 3H), 3.75 (m, 2H), 3.52 (m, 2H), 3.22 (m, 2H), 3.08 (m, 4H), 2.69 (m, 2H).

Example 1524

N-tert-Butyl-3-{2-[2-(4-methyl-piperazin-1-ylmethyl)-3H-benzimidazol-5-ylamino]-pyrrolo[2,1-f][1,2,4]triazin-7-yl}-benzenesulfonamide 1524a) Analogous to Example 1520a, 2-(4-Methyl-piperazin-1-ylmethyl)-5-nitro-1H-benzimidazole (1.28 g, 3.29 mmol) (Goker, H.; Kus, C.; Abbasoglu, U. Arch. Pharm. (Weinheim, Ger.) 1995, 328, 425.) was hydrogenated to give 2-[(4-methylpiperazin-1-yl)methyl]-1H-benzimidazol-5-amine tetrahydrochloride (1.21 g, 94.1%). 1H-NMR (DMSO-d6): 11.1 (br s, 1H), 7.85 (d, 1H, J=8.5 Hz), 7.79 (s, 1H), 7.43 (d, 1H, J=8.6 Hz), 4.27 (s, 2H), 3.42 (m, 2H), 3.18 (m, 4H), 2.85 (m, 2H), 2.76 (s, 3H).

1524b) Analogous to Example 1510b, N-tert-Butyl-3-(2-hydroxy-pyrrolo[2,1-f][1,2,4]triazin-7-yl)-benzenesulfonamide (49 mg, 0.14 mmol) and 2-[(4-methylpiperazin-1-yl)methyl]-1H-benzimidazol-5-amine tetrahydrochloride (71 mg, 0.18 mmol) were reacted to afford the TFA salt of N-tert-Butyl-3-{2-[2-(4-methyl-piperazin-1-ylmethyl)-3H-benzimidazol-5-ylamino]-pyrrolo[2,1-f][1,2,4]triazin-7-yl}-benzenesulfonamide (61 mg, 62%). LCMS (HPLC): 0.83 min, m/z=574 (M+H); 1H-NMR (DMSO-d6): 9.81 (s, 1H), 9.62 (br s, 1H), 9.09 (s, 1H), 8.65 (s, 1H), 8.39 (d, 1H, J=8.0 Hz), 8.00 (s, 1H), 7.93 (m, 1H), 7.86 (d, 1H, J=7.9 Hz), 7.73 (m, 3H), 7.27 (d, 1H, J=4.8 Hz), 7.05 (d, 1H, J=4.8 Hz), 4.08 (s, 2H), 3.46 (m, 2H), 3.08 (m, 4H), 2.83 (s, 3H), 2.58 (m, 2H), 1.10 (s, 9H).

Example 1525

N-Methyl-N-(2-{2-[2-(4-methyl-piperazin-1-ylmethyl)-3H-benzimidazol-5-ylamino]-pyrrolo[2,1-f][1,2,4]triazin-7-yl}-phenyl)-methanesulfonamide Analogous to Example 1510b, 2-[(4-methylpiperazin-1-yl)methyl]-1H-benzimidazol-5-amine tetrahydrochloride (68.0 mg, 0.174 mmol) was reacted with Trifluoro-methanesulfonic acid 7-[2-(methanesulfonyl-methyl-amino)-phenyl]-pyrrolo[2,1-f][1,2,4]triazin-2-yl ester (71 mg, 0.16 mmol) to afford the TFA salt of N-Methyl-N-(2-{2-[2-(4- methyl-piperazin-1-ylmethyl)-3H-benzimidazol-5-ylamino]-pyrrolo[2,1-f][1,2,4]triazin-7-yl}-phenyl)-methanesulfonamide (86 mg, 75%). LCMS (HPLC): 0.67 min, m/z=546 (M+H); 1H-NMR (DMSO-d6): 9.65 (br s, 2H), 9.03 (s, 1H), 8.03 (d, 1H, J=7.6 Hz), 7.95 (s, 1H), 7.77 (d, 1H, J=8.8 Hz), 7.62 (m, 3H), 7.53 (m, 1H), 7.01 (m, 2H), 4.08 (s, 2H), 3.45 (m, 2H), 3.11 (s, 3H), 3.06 (m, 4H), 2.88 (s, 3H), 2.83 (s, 3H), 2.57 (m, 2H).

Example 1526

[7-(2-Methoxy-phenyl)-pyrrolo[2,1-f][1,2,4]triazin-2-yl]-[2-(4-methyl-piperazin-1-ylmethyl)-3H-benzimidazol-5-yl]-amine Analogous to Example 1510b, 2-[(4-methylpiperazin-1-yl)methyl]-1H-benzimidazol-5-amine tetrahydrochloride (68.0 mg, 0.174 mmol) was reacted with Trifluoro-methanesulfonic acid 7-(2-methoxy-phenyl)-pyrrolo[2,1-f][1,2,4]triazin-2-yl ester (59.0 mg, 0.158 mmol) to afford the TFA salt of [7-(2-Methoxy-phenyl)-pyrrolo[2,1-f][1,2,4]triazin-2-yl]-[2-(4-methyl-piperazin-1-ylmethyl)-3H-benzimidazol-5-yl]-amine (67 mg, 66%). LCMS (HPLC): 0.74 min, m/z=469 (M+H); 1H-NMR (DMSO-d6): 9.72 (br s, 1H), 9.68 (s, 1H), 9.01 (s, 1H), 7.90 (m, 3H), 7.59 (d, 1H, J=8.8 Hz), 7.46 (m, 1H), 7.23 (d, 1H, J=8.4 Hz), 7.15 (m, 1H), 7.01 (d, 1H, J=4.6 Hz), 6.97 (d, 1H, J=4.6 Hz), 4.10 (s, 2H), 3.81 (s, 3H), 3.45 (m, 2H), 3.06 (m, 4H), 2.83 (s, 3H), 2.57 (m, 2H).

Example 1527

[7-(6-Methoxy-pyridin-3-yl)-pyrrolo[2,1-f][1,2,4]triazin-2-yl]-[2-(4-methyl-piperazin-1-ylmethyl)-3H-benzimidazol-5-yl]-amine Analogous to Example 1510b, 2-[(4-methylpiperazin-1-yl)methyl]-1H-benzimidazol-5-amine tetrahydrochloride (68.0 mg, 0.174 mmol) was reacted with Trifluoro-methanesulfonic acid 7-(6-methoxy-pyridin-3-yl)-pyrrolo[2,1-f][1,2,4]triazin-2-yl ester (59.2 mg, 0.158 mmol) to afford the TFA salt of [7-(6-Methoxy-pyridin-3-yl)-pyrrolo[2,1-f][1,2,4]triazin-2-yl]-[2-(4-methyl-piperazin-1-ylmethyl)-3H-benzimidazol-5-yl]-amine (59 mg, 58%). LCMS (HPLC): 0.70 min, m/z=470 (M+H); 1H-NMR (DMSO-d6): 9.79 (s, 1H), 9.68 (br s, 1H), 9.04 (s, 1H), 8.94 (d, 1H, J=2.0 Hz), 8.57 (dd, 1H, J=2.0, 8.7 Hz), 8.10 (s, 1H), 7.77 (d, 1H, J=8.8 Hz), 7.71 (d, 1H, J=8.8 Hz), 7.25 (d, 1H, J=4.7 Hz), 7.02 (m, 2H), 4.11 (s, 2H), 3.94 (s, 3H), 3.45 (m, 2H), 3.08 (m, 4H), 2.83 (s, 3H), 2.59 (m, 2H).

Example 1528

N-tert-Butyl-3-[2-(4-piperazin-2-yl-phenylamino)-pyrrolo[2,1-f][1,2,4]triazin-7-yl]-benzenesulfonamide 1528a) A solution of Ethylenediamine (0.3730 mL, 5.580 mmol) in Ethanol (5 mL) was added dropwise over 5 minutes to a stirring solution of 2,2-Dihydroxy-1-(4-nitro-phenyl)-ethanone (1.00 g, 5.07 mmol) and the reaction was left to stir for 4 hours. Sodium borohydride (0.966 g, 25.5 mmol) was added and the mixture was stirred overnight at room temperature. Water (10 mL, 600 mmol) was added and the solution was then extracted with DCM (4×, 10 mL), and the combined organics were washed with brine (2×, 10 mL), dried over sodium sulfate, and conc. in vacuo. The crude product was then taken up in minimal MeOH and recrystallized by adding it dropwise to stirring Oxalic acid (0.502 g, 5.58 mmol) in 50 mL ether. 2-(4-Nitro-phenyl)-piperazine oxalic acid salt precipitated as light brown solids (0.96 g, 64%). 1H-NMR (DMSO-d6): 8.25 (d, 2H, J=8.68 Hz), 7.69 (d, 2H, J=8.68 Hz), 4.07 (d, 2H, 10.66 Hz), 3.33 (dd, 2H, J=11.92 Hz), 3.23 (d, 2H, J=10.66 Hz), 3.13 (d, 2H, J=10.66 Hz).

1528b) 2-(4-Nitro-phenyl)-piperazine oxalic acid salt (0.500 g, 1.68 mmol) was placed in a vial, followed by MP-Carbonate (3.16 mmol/g loading; 1.60 g, 5.05 mmol) and 4-Dimethylaminopyridine (14 mg, 0.11 mmol). Methylene chloride (15 mL) was added, followed by Di-tert-Butyldicarbonate (1.00 mL, 4.35 mmol) and the mixture was stirred at rt for 6 h. The mixture was filtered, washing with DCM. The filtrate was conc. in vacuo and purified (ISCO, 40 g, 0-40% EtOAc:Hex) to afford 2-(4-Nitro-phenyl)-piperazine-1,4-dicarboxylic acid di-tert-butyl ester (0.44 g, 64%). 1H-NMR (CDCl3): 8.20 (d, 1H, J=8.6 Hz), 7.49 (d, 1H, J=8.6 Hz), 5.32 (br s, 1H), 4.44 (m, 1H), 3.7-4 (m, 2H), 3.39 (m, 1H), 2.9-3.2 (m, 2H), 1.46 (s, 9H), 1.42 (s, 9H). (most peaks show rotameric nature).

1528c) 2-(4-Nitro-phenyl)-piperazine-1,4-dicarboxylic acid di-tert-butyl ester (0.440 g, 1.08 mmol) was dissolved in Methanol (40 mL) and transferred to a Parr bottle containing 5% Platinum on Carbon, Sulfided (0.5%) (65 mg, 0.017 mmol). The mixture was shaken under an atmosphere of Hydrogen (10 psi) for 2 h, then filtered and conc. in vacuo to afford 2-(4-Amino-phenyl)-piperazine-1,4-dicarboxylic acid di-tert-butyl ester (0.37 g, 91%). 1H-NMR (DMSO-d6): 6.88 (d, 2H, J=8.0 Hz), 6.51 (d, 2H, J=8.0 Hz), 5.00 (m, 3H), 4.26 (m, 1H), 3.77 (m, 2H), 3.16 (m, 1H), 2.84 (m, 2H), 1.39 (s, 9H), 1.35 (s, 9H).

1528d) Analogous to Example 1510b, 2-(4-Amino-phenyl)-piperazine-1,4-dicarboxylic acid di-tert-butyl ester (0.180 g, 0.477 mmol) and N-tert-Butyl-3-(2-hydroxy-pyrrolo[2,1-f][1,2,4]triazin-7-yl)-benzenesulfonamide (149 mg, 0.429 mmol) were reacted to afford 2-{4-[7-(3-tert-Butylsulfamoyl-phenyl)-pyrrolo[2,1-f][1,2,4]triazin-2-ylamino]-phenyl}-piperazine-1,4-dicarboxylic acid di-tert-butyl ester, which was treated with 10% TFA in dichloromethane overnight. Conc. and purification by HPLC afforded N-tert-Butyl-3-[2-(4-piperazin-2-yl-phenylamino)-pyrrolo[2,1-f][1,2,4]triazin-7-yl]-benzenesulfonamide as the TFA salt (162 mg, 61%). LCMS (HPLC): 0.8 min, m/z=506 (M+H); 1H-NMR (DMSO-d6): 9.81 (s, 1H), 9.44 (br s, 3H), 9.09 (s, 1H), 8.57 (s, 1H), 8.34 (d, 1H, J=8.0 Hz), 7.87 (m, 3H), 7.74 (m, 1H), 7.62 (s, 1H), 7.48 (d, 2H, J=8.5 Hz), 7.24 (d, 1H, J=4.8 Hz), 7.05 (d, 1H, J=4.8 Hz), 4.46 (m, 1H), 3.59 (m, 3H), 3.27 (m, 3H), 1.11 (s, 9H).

Example 1529

[7-(6-Methoxy-pyridin-3-yl)-pyrrolo[2,1-f][1,2,4]triazin-2-yl]-(4-piperazin-2-yl-phenyl)-amine Analogous to Example 1528d, 2-(4-Amino-phenyl)-piperazine-1,4-dicarboxylic acid di-tert-butyl ester (0.180 g, 0.477 mmol) and Trifluoro-methanesulfonic acid 7-(6-methoxy-pyridin-3-yl)-pyrrolo[2,1-f][1,2,4]triazin-2-yl ester (161 mg, 0.429 mmol) were reacted to afford [7-(6-Methoxy-pyridin-3-yl)-pyrrolo[2,1-f][1,2,4]triazin-2-yl]-(4-piperazin-2-yl-phenyl)-amine as the TFA salt (123 mg, 55%). LCMS (HPLC): 0.7 min, m/z=402 (M+H); 1H-NMR (DMSO-d6): 9.78 (s, 1H), 9.40 (br s, 3H), 9.03 (s, 1H), 8.90 (s, 1H), 8.50 (dd, 1H, J=2.2, 8.8 Hz), 7.84 (d, 2H, J=8.5 Hz), 7.45 (d, 2H, J=8.5 Hz), 7.22 (d, 1H, J=4.8 Hz), 7.01 (m, 2H), 4.450 (m, 1H), 3.96 (s, 3H), 3.67 (m, 1H), 3.59 (m, 2H), 3.41 (m, 2H), 3.25 (m, 1H).

Example 1530

[4-(1,4-Dimethyl-piperazin-2-yl)-phenyl]-[7-(6-methoxy-pyridin-3-yl)-pyrrolo[2,1-f][1,2,4]triazin-2-yl]-amine Analogous to Example 1519, [7-(6-Methoxy-pyridin-3-yl)-pyrrolo[2,1-f][1,2,4]triazin-2-yl]-(4-piperazin-2-yl-phenyl)-amine was alkylated to afford [4-(1,4-Dimethyl-piperazin-2-yl)-phenyl]-[7-(6-methoxy-pyridin-3-yl)-pyrrolo[2,1-f][1,2,4]triazin-2-yl]-amine as the TFA salt (18 mg, 42%). LCMS (HPLC): 0.83 min, m/z=430 (M+H); 1H-NMR (DMSO-d6): 9.68 (s, 1H), 9.02 (s, 1H), 8.90 (s, 1H), 8.50 (dd, 1H, J=2.0, 8.7 Hz), 7.78 (d, 2H, J=8.2 Hz), 7.33 (d, 2H, J=8.2 Hz), 7.20 (d, 1H, J=4.7 Hz), 7.02 (d, 1H, J=8.7 Hz), 7.00 (d, 1H, J=4.7 Hz), 3.96 (s, 3H), 3.1-3.5 (m, 7H), 2.76 (s, 3H), 2.17 (s, 3H).

Example 1531

2-(4-{4-[7-(3-Methoxy-pyridin-2-yl)-pyrrolo[2,1-f][1,2,4]triazin-2-ylamino]-phenyl}-piperidin-1-yl)-acetamide 1531a) 3-Methoxy-2-tributylstannanyl-pyridine (1.31 g, 3.29 mmol) was dissolved in N,N-Dimethylformamide (15 mL), 7-Bromo-2-methylsulfanyl-pyrrolo[2,1-f][1,2,4]triazine (0.504 g, 2.06 mmol) and Tetrakis(triphenylphosphine)palladium(0) (161 mg, 0.139 mmol) were added, and the mixture was degassed under vacuum, then under an atmosphere of Nitrogen, was heated in a block at 80° C. for 8 h, then 110 C overnight. Bis(tri-tert-butylphosphine)palladium (45 mg, 0.088 mmol) was added and heating was continued at 110 C for 8 h. The mixture was cooled, conc. in vacuo and applied to a 25 g Isco cartridge (MeOH:DCM), dried and purified (80 g column, 0-70% EtOAc:Hex) to afford 7-(3-Methoxy-pyridin-2-yl)-2-methylsulfanyl-pyrrolo[2,1-f][1,2,4]triazine (0.192 g; Yield=34.1%). LCMS (HPLC):0.78 min, m/z=273 (M+H); 1H-NMR (DMSO-d6): 9.04 (s, 1H), 8.29 (d, 1H, J=4.4 Hz), 7.64 (d, 1H, J=8.4 Hz), 7.50 (dd, 1H, J=4.4, 8.4 Hz), 7.12 (d, 1H, J=4.6 Hz), 7.07 (d, 1H, J=4.6 Hz), 3.83 (s, 3H), 2.38 (s, 3H).

1531b) Sodium Tungstate Dihydrate (23.0 mg, 0.0698 mmol) and 50% Hydrogen Peroxide (50:50, Hydrogen peroxide:Water, 0.150 mL, 2.64 mmol) were added to 7-(3-Methoxy-pyridin-2-yl)-2-methylsulfanyl-pyrrolo[2,1-f][1,2,4]triazine (0.190 g, 0.698 mmol) in Methanol (10.0 mL) and Acetic acid (0.400 mL, 7.04 mmol). The mixture was stirred at 50° C. Formation of the sulfoxide was evident, followed by formation of the sulfone. After o.n., a 1:1 mixture of sulfoxide:sulfone was present. Additional 50% Hydrogen Peroxide (50:50, Hydrogen peroxide:Water, 0.150 mL, 2.64 mmol) was added. Further heating gave a ~2:1 mixture. Aqueous workup (10% Na2S2O3, NaHCO3, water) and extract with DCM. The crude sulfone:sulfoxide mixture was hydrolyzed by dissolving in Tetrahydrofuran (6.0 mL) and adding 5.0 M of Sodium hydroxide in Water (0.500 mL, 2.50 mmol), then heating at 50° C. for 6 h. Work up by acidifying with Acetic acid to pH 5-6. Partition between DCM and water, extract with MeOH to solubilize the ppt that forms during extraction. Dry and conc. in vacuo to afford 7-(3-Methoxy-pyridin-2-yl)-pyrrolo[2,1-f][1,2,4]triazin-2-ol (145 mg, 85%).

1531c) Analogous to Example 1510b, 7-(3-Methoxy-pyridin-2-yl)-pyrrolo[2,1-f][1,2,4]triazin-2-ol (72 mg, 0.299 mmol) and 2-[4-(4-Amino-phenyl)-piperidin-1-yl]-acetamide (74.0 mg, 0.317 mmol) were reacted to afford 2-(4-{4-[7-(3-Methoxy-pyridin-2-yl)-pyrrolo[2,1-f][1,2,4]triazin-2-ylamino]-phenyl}-piperidin-1-yl)-acetamide as the TFA salt (37 mg, 11%). LCMS (HPLC): 0.63 min, m/z=458; 1H-NMR (DMSO-d6): 9.53 (br s, 1H), 9.44 (s, 1H), 9.02 (s, 1H), 8.37 (d, 1H, J=4.4 Hz), 7.97 (s, 1H), 7.70 (m, 4H), 7.54 (dd, 1H, J=8.2, 4.8 Hz), 7.07 (m, 2H), 7.02 (d, 1H, J=4.6 Hz), 6.94 (d, 1H, J=4.6 Hz), 3.92 (s, 2H), 3.84 (s, 3H), 3.54 (m, 2H), 3.14 (m, 2H), 2.71 (m, 1H), 1.94 (m, 4H).

Example 1532

2-(4-{3-Methoxy-4-[7-(3-methoxy-pyridin-2-yl)-pyrrolo[2,1-f][1,2,4]triazin-2-ylamino]-phenyl}-piperidin-1-yl)-acetamide Analogous to Example 1510b, 7-(3-Methoxy-pyridin-2-yl)-pyrrolo[2,1-f][1,2,4]triazin-2-ol (72 mg, 0.299 mmol) and 2-[4-(4-Amino-3-methoxy-phenyl)-piperidin-1-yl]-acetamide (82.0 mg, 0.311 mmol) were reacted to afford 2-(4-{3-Methoxy-4-[7-(3-methoxy-pyridin-2-yl)-pyrrolo[2,1-f][1,2,4]triazin-2-ylamino]-phenyl}-piperidin-1-yl)-acetamide as the TFA salt (26 mg, 7%). LCMS (HPLC): 0.67 min, m/z=488; 1H-NMR (DMSO-d6): 9.48 (br s, 1H), 9.02 (s, 1H), 8.37 (d, 1H, J=4.4 Hz), 8.14 (d, 1H, J=8.2 Hz), 7.97 (s, 1H), 7.71 (m, 3H), 7.54 (dd, 1H, J=8.4, 4.6 Hz), 7.07 (d, 1H, J=4.6 Hz), 6.98 (d, 1H, J=4.6 Hz), 6.88 (s, 1H), 6.71 (d, 1H, J=8.4 Hz), 3.93 (s, 2H), 3.88 (s, 3H), 3.83 (s, 3H), 3.55 (m, 2H), 3.15 (m, 2H), 2.75 (m, 1H), 1.99 (m, 4H).

Example 1533

2-(4-{4-[7-(2,2-Difluoro-benzo[1,3]dioxol-4-yl)-pyrrolo[2,1-f][1,2,4]triazin-2-ylamino]-3-methoxy-phenyl}-piperidin-1-yl)-acetamide 1533a) 7-Bromo-2-methylsulfanyl-pyrrolo[2,1-f][1,2,4]triazine (0.531 g, 2.18 mmol), 2,2-Difluorobenzo[1,3]dioxole-4-boronic acid (0.624 g, 3.09 mmol), Tetrakis(triphenylphosphine)palladium(0) (125 mg, 0.108 mmol), 2.00 M of Sodium carbonate in Water (2.70 mL), and 1,4-Dioxane (6.6 mL) were combined in a vial, degassed (freeze-pump-thaw) and was heated under an atmosphere of Nitrogen at 80° C. overnight. Conversion was ~75%. Further heating for a second night lead to little additional product relative to bromide. The mixture was diluted with water (20 mL) then extracted with EtOAc (3×30 mL). The org. was washed with brine, dried, filtered through 7 mL silica gel, washing with EtOAc, then conc. in vacuo onto 7 g silica gel. Purification on an ISCO (80 g, 0-10% EtOAc:Hex) afforded first an impurity, then the product 7-(2,2-Difluoro-benzo[1,3]dioxol-4-yl)-2-methylsulfanyl-pyrrolo[2,1-f][1,2,4]triazine (0.440 g; Yield=63.0%). LCMS (HPLC): 1.46 min, 322 (M+H); $^1$H-NMR (DMSO-d6): 9.12 (s, 1H), 8.16 (d, 1H, J=8.1 Hz), 7.48 (d, 1H, J=7.9 Hz), 7.40 (m, 1H), 7.33 (d, 1H, J=4.8 Hz), 7.16 (d, 1H, J=4.8 Hz), 2.55 (s, 3H).

1533b) 7-(2,2-Difluoro-benzo[1,3]dioxol-4-yl)-2-methylsulfanyl-pyrrolo[2,1-f][1,2,4]triazine (0.435 g, 1.35 mmol) and Sodium Tungstate Dihydrate (59 mg, 0.18 mmol) were suspended in Methanol (15.0 mL), then 50% Hydrogen Peroxide (0.350 mL, 6.16 mmol) was added. The mixture was then heated at 55° C. overnight. A solution of sodium thiosulfate was added, stirred 10 min, then cooled to rt. The product was collected by filtration, washing the yellow solids with 1:1 MeOH:H₂O (10 mL). After drying on the Buchner funnel, 7-(2,2-Difluoro-benzo[1,3]dioxol-4-yl)-2-methanesulfonyl-pyrrolo[2,1-f][1,2,4]triazine (0.410 g; Yield=85.7%). LCMS (HPLC): 1.15 min, m/z=354 (M+H); ¹H-NMR (DMSO-d6): 9.51 (s, 1H), 8.16 (d, 1H, J=8.1 Hz), 7.73 (d, 1H, J=4.8 Hz), 7.56 (d, 1H, J=7.7 Hz), 7.49 (d, 1H, J=4.8 Hz), 7.45 (m, 1H), 3.45 (s, 3H).

1533c) 7-(2,2-Difluoro-benzo[1,3]dioxol-4-yl)-2-methanesulfonyl-pyrrolo[2,1-f][1,2,4]triazine (0.410 g) was suspended in Tetrahydrofuran (2.00 mL), 5.0 M of Sodium hydroxide in Water (1.00 mL, 5.00 mmol) was added and the mixture was heated in a vial, in a block at 60° C. for 3 h. The mixture was then treated with a solution of Acetic acid (0.500 mL, 8.79 mmol) in Water (5.50 mL), generating an orange ppt. The mixture was cooled, the solids collected, washing with 10 mL water. Dry on the Buchner to afford 7-(2,2-Difluoro-benzo[1,3]dioxol-4-yl)-pyrrolo[2,1-f][1,2,4]triazin-2-ol (0.310 g; Yield=78.6%). LCMS (HPLC): 0.97 min, m/z=292 (M+H); 1H-NMR (DMSO-d6): 11.97 (s, 1H), 9.10 (s, 1H), 8.38 (d, 1H, 8.0 Hz), 7.44 (d, 1H, J=7.9 Hz), 7.38 (m, 1H), 7.25 (d, 1H, J=4.8 Hz), 7.09 (d, 1H, J=4.8 Hz).

1533d) Analogous to Example 1510b, 7-(2,2-Difluoro-benzo[1,3]dioxol-4-yl)-pyrrolo[2,1-f][1,2,4]triazin-2-ol (40.2 mg, 0.138 mmol) and 2-[4-(4-Amino-3-methoxy-phenyl)-piperidin-1-yl]-acetamide (40.0 mg, 0.152 mmol) were reacted to afford 2-(4-{4-[7-(2,2-Difluoro-benzo[1,3]dioxol-4-yl)-pyrrolo[2,1-f][1,2,4]triazin-2-ylamino]-3-methoxy-phenyl}-piperidin-1-yl)-acetamide as the TFA salt (43 mg, 48%). LCMS (HPLC): 1.08 min, m/z=537; 1H-NMR (DMSO-d6): 9.57 (br s, 1H), 9.07 (s, 1H), 8.20 (d, 1H, J=8.2 Hz), 8.04 (s, 1H), 8.01 (s, 1H), 7.93 (d, 1H, J=8.2 Hz), 7.73 (s, 1H), 7.45 (d, 1H, J=8.0 Hz), 7.31 (m, 1H), 7.16 (d, 1H, J=4.7 Hz), 7.03 (d, 1H, J=4.7 Hz), 6.95 (s, 1H), 6.81 (d, 1H, J=8.2 Hz), 3.95 (s, 2H), 3.88 (s, 3H), 3.58 (m, 2H), 3.17 (m, 2H), 2.81 (m, 1H), 2.05 (m, 4H).

Example 1534

[7-(2,2-Difluoro-benzo[1,3]dioxol-4-yl)-pyrrolo[2,1-f][1,2,4]triazin-2-yl]-[3-(4-methyl-piperazin-1-yl)-phenyl]-amine Analogous to Example 1510b, 7-(2,2-Difluoro-benzo[1,3]dioxol-4-yl)-pyrrolo[2,1-f][1,2,4]triazin-2-ol (40.2 mg, 0.138 mmol) and 3-(4-Methylpiperazin-1-yl)aniline (29.0 mg, 0.152 mmol) were reacted to afford [7-(2,2-Difluoro-benzo[1,3]dioxol-4-yl)-pyrrolo[2,1-f][1,2,4]triazin-2-yl]-[3-(4-methyl-piperazin-1-yl)-phenyl]-amine as the TFA salt (44 mg, 55%). LCMS (HPLC): 1.05 min, m/z=465; 1H-NMR (DMSO-d6): 9.89 (br s, 1H), 9.48 (s, 1H), 9.09 (s, 1H), 8.23 (d, 1H, J=8.2 Hz), 7.48 (d, 1H, J=8.0 Hz), 7.38 (m, 1H), 7.30 (m, 2H), 7.18 (m, 1H), 7.15 (d, 1H, J=4.8 Hz), 7.03 (d, 1H, J=4.8 Hz), 6.66 (d, 1H, J=8.1 Hz), 3.67 (m, 2H), 3.46 (m, 2H), 3.11 (m, 2H), 2.90 (m, 1H), 2.87 (s, 3H).

Example 1535

[7-(2,2-Difluoro-benzo[1,3]dioxol-4-yl)-pyrrolo[2,1-f][1,2,4]triazin-2-yl]-(7-morpholin-4-yl-6,7,8,9-tetrahydro-5H-benzocyclohepten-2-yl)-amine Analogous to Example 1510b, 7-(2,2-Difluoro-benzo[1,3]dioxol-4-yl)-pyrrolo[2,1-f][1,2,4]triazin-2-ol (40.2 mg, 0.138 mmol) and 7-Morpholin-4-yl-6,7,8,9-tetrahydro-5H-benzocyclohepten-2-ylamine (37.4 mg, 0.152 mmol) were reacted to afford [7-(2,2-Difluoro-benzo[1,3]dioxol-4-yl)-pyrrolo[2,1-f][1,2,4]triazin-2-yl]-(7-morpholin-4-yl-6,7,8, 9-tetrahydro-5H-benzocyclohepten-2-yl)-amine as the TFA salt (43 mg, 49%). LCMS (HPLC): 1.09 min, m/z=520; 1H-NMR (DMSO-d6): 9.74 (br s, 1H), 9.57 (s, 1H), 9.08 (s, 1H), 8.27 (d, 1H, J=8.0 Hz), 7.71 (s, 1H), 7.48 (d, 1H, J=7.8 Hz), 7.40 (m, 2H), 7.15 (d, 1H, J=4.7 Hz), 7.10 (d, 1H, J=8.2 Hz), 7.02 (d, 1H, J=4.7 Hz), 3.99 (m, 2H), 3.73 (m, 2H), 3.56 (m, 1H), 3.2-3.3 (m, 4H), 2.6-2.8 (m, 4H), 2.35 (m, 2H), 1.46 (m, 2H).

Example 1536

[7-(2,2-Difluoro-benzo[1,3]dioxol-4-yl)-pyrrolo[2,1-f][1,2,4]triazin-2-yl]-(2-morpholin-4-ylmethyl-1H-benzoimidazol-5-yl)-amine Analogous to Example 1510b, 7-(2,2-Difluoro-benzo[1,3]dioxol-4-yl)-pyrrolo[2,1-f][1,2,4]triazin-2-ol (40.2 mg, 0.138 mmol) and 2-Morpholin-4-ylmethyl-1H-benzimidazol-5-ylamine (35.3 mg, 0.152 mmol) were reacted to afford [7-(2,2-Difluoro-benzo[1,3]dioxol-4-yl)-pyrrolo[2,1-f][1,2,4]triazin-2-yl]-(2-morpholin-4-ylmethyl-1H-benzoimidazol-5-yl)-amine as the TFA salt (41 mg, 48%). LCMS (HPLC): 1.03 min, m/z=506; 1H-NMR (DMSO-d6): 9.79 (s, 1H), 9.12 (s, 1H), 8.33 (d, 1H, J=8.1 Hz), 8.09 (s, 1H), 7.71 (d, 1H, J=8.8 Hz), 7.64 (d, 1H, J=8.8 Hz), 7.47 (d, 1H, J=7.9 Hz), 7.41 (m, 1H), 7.18 (d, 1H, J=4.8 Hz), 7.06 (d, 1H, J=4.8 Hz), 4.38 (s, 2H), 3.79 (br s, 4H), 3.04 (br s, 4H).

Example 1537

[7-(3-Methanesulfonyl-phenyl)-pyrrolo[2,1-f][1,2,4]triazin-2-yl]-(2-morpholin-4-ylmethyl-1H-benzimidazol-5-yl)-amine Analogous to Example 1510b, 7-(3-Methanesulfonyl-phenyl)-pyrrolo[2,1-f][1,2,4]triazin-2-ol (65.0 mg, 0.225 mmol) and 2-Morpholin-4-ylmethyl-1H-benzimidazol-5-ylamine (57.4 mg, 0.247 mmol) were reacted to afford [7-(3-Methanesulfonyl-phenyl)-pyrrolo[2,1-f][1,2,4]triazin-2-yl]-(2-morpholin-4-ylmethyl-1H-benzimidazol-5-yl)-amine as the TFA salt (67 mg, 48%). LCMS (HPLC): 0.78 min, m/z=504 (M+H); 1H-NMR (DMSO-d6): 9.76 (s, 1H), 9.09 (s, 1H), 8.64 (s, 1H), 8.54 (d, 1H, J=7.9 Hz), 8.02 (s, 1H), 7.95 (d, 1H, J=7.9 Hz), 7.82 (m, 2H), 7.69 (d, 1H, J=8.8 Hz), 7.34 (d, 1H, J=4.8 Hz), 7.04 (d, 1H, J=4.8 Hz), 4.31 (s, 2H), 3.77 (br s, 4H), 3.26 (s, 3H), 2.96 (br s, 4H).

Example 1538

[7-(3-Methanesulfonyl-phenyl)-pyrrolo[2,1-f][1,2,4]triazin-2-yl]-[2-(4-methyl-piperazin-1-ylmethyl)-1H-benzimidazol-5-yl]-amine Analogous to Example 1510b, 7-(3-M ethanesulfonyl-phenyl)-pyrrolo[2,1-f][1,2,4]triazin-2-ol (65.0 mg, 0.225 mmol) and 2-[(4-methylpiperazin-1-yl)methyl]-1H-benzimidazol-5-amine tetrahydrochloride (96.7 mg, 0.247 mmol) were reacted to afford [7-(3-Methanesulfonyl-phenyl)-pyrrolo[2,1-f][1,2,4]triazin-2-yl]-[2-(4-methyl-piperazin-1-ylmethyl)-1H-benzimidazol-5-yl]-amine as the TFA salt (83 mg, 58%). LCMS (HPLC): 0.69 min, m/z=517 (M+H); 1H-NMR (DMSO-d6): 9.84 (s, 1H), 9.63 (br s, 1H), 9.10 (s, 1H), 8.70 (s, 1H), 8.49 (d, 1H, J=7.9 Hz), 8.02 (s, 1H), 7.95 (d, 1H, J=8.0 Hz), 7.87 (d, 1H, J=9.0 Hz)), 7.82 (m, 1H), 7.73 (d, 1H, J=8.8 Hz), 7.35 (d, 1H, J=4.8 Hz), 7.05 (d, 1H, J=4.8 Hz), 4.08 (s, 2H), 3.46 (m, 2H), 3.27 (s, 3H), 3.06 (m, 4H), 2.83 (s, 3H), 2.58 (m, 2H).

Example 1539

2-(4-{5-[7-(3-Methanesulfonyl-phenyl)-pyrrolo[2,1-f][1,2,4]triazin-2-ylamino]-1H-benzimidazol-2-ylmethyl}-piperazin-1-yl)-ethanol Analogous to Example 1510b, 7-(3-Methanesulfonyl-phenyl)-pyrrolo[2,1-f][1,2,4]triazin-2-ol (65.0 mg, 0.225 mmol) and 2-[4-(5-Amino-1H-benzimidazol-2-ylmethyl)-piperazin-1-yl]-ethanol tetrahydrochloride (104 mg, 0.247 mmol) were reacted to 2-(4-{5-[7-(3-Methanesulfonyl-phenyl)-pyrrolo[2,1-f][1,2,4]triazin-2-ylamino]-1H-benzimidazol-2-ylmethyl}-piperazin-1-yl)-ethanol as the TFA salt (86 mg, 58%). LCMS (HPLC): 0.67 min, m/z=547 (M+H); 1H-NMR (DMSO-d6): 9.85 (s, 1H), 9.50 (br s, 1H), 9.10 (s, 1H), 8.70 (s, 1H), 8.49 (d, 1H, J=7.8 Hz), 8.02 (s, 1H), 7.95 (d, 1H, J=7.8 Hz), 7.89 (d, 1H, J=8.9 Hz), 7.82 (m, 1H), 7.74 (d, 1H, J=8.8 Hz), 7.35 (d, 1H, J=4.8 Hz), 7.05 (d, 1H, J=4.8 Hz), 4.10 (s, 2H), 3.76 (t, 2H, J=4.9 Hz), 3.51 (m, 2H), 3.26 (s, 3H), 3.22 (m, 2H), 3.02-3.18 (m, 4H), 2.68 (m, 2H).

Example 1540

2-(4-{4-[7-(2,2-Difluoro-benzo[1,3]dioxol-4-yl)-pyrrolo[2,1-f][1,2,4]triazin-2-ylamino]-phenyl}-piperidin-1-yl)-acetamide Analogous to Example 1510b, 7-(2,2-Difluoro-benzo[1,3]dioxol-4-yl)-pyrrolo[2,1-f][1,2,4]triazin-2-ol (45.0 mg, 0.154 mmol) and 2-[4-(4-Amino-phenyl)-piperidin-1-yl]-acetamide (39.0 mg, 0.167 mmol) were reacted to afford 2-(4-{4-[7-(2,2-Difluoro-benzo [1,3]dioxol-4-yl)-pyrrolo[2,1-f][1,2,4]triazin-2-ylamino]-phenyl}-piperidin-1-yl)-acetamide as the TFA salt (62 mg, 65%). LCMS (HPLC): 1.05 min, m/z=507 (M+H); 1H-NMR (DMSO-d6): 9.60 (s, 1H), 9.54 (br s, 1H), 9.09 (s, 1H), 8.22 (d, 1H, J=8.0 Hz), 7.97 (s, 1H), 7.70 (m, 3H), 7.48 (d, 1H, J=7.9 Hz), 7.39 (m, 1H), 7.71 (m, 3H), 7.02 (d, 1H, J=4.7 Hz), 3.92 (s, 2H), 3.56 (m, 2H), 3.15 (m, 2H), 2.75 (m, 1H), 1.99 (m, 4H).

Example 1541

[7-(4-Methanesulfonyl-phenyl)-pyrrolo[2,1-f][1,2,4]triazin-2-yl]-(2-morpholin-4-ylmethyl-1H-benzimidazol-5-yl)-amine Analogous to Example 1510b, 7-(4-Methanesulfonyl-phenyl)-pyrrolo[2,1-f][1,2,4]triazin-2-ol (65.0 mg, 0.225 mmol) and 2-Morpholin-4-ylmethyl-1H-benzimidazol-5-ylamine (57.4 mg, 0.247 mmol) were reacted to afford [7-(4-Methanesulfonyl-phenyl)-pyrrolo[2,1-f][1,2,4]triazin-2-yl]-(2-morpholin-4-ylmethyl-1H-benzimidazol-5-yl)-amine as the TFA salt (59 mg, 42%). LCMS (HPLC): 0.79 min, m/z=504 (M+H); 1H-NMR (DMSO-d6): 9.75 (s, 1H), 9.10 (s, 1H), 8.53 (d, 2H, J=8.5 Hz), 8.10 (s, 1H), 8.03 (d, 2H, J=8.5 Hz), 7.70 (s, 2H), 7.41 (d, 1H, J=4.8 Hz), 7.04 (d, 1H, J=4.8 Hz), 4.36 (s, 2H), 3.79 (m, 4H), 3.28 (s, 3H), 3.05 (m, 4H).

Example 1542

[7-(4-Methanesulfonyl-phenyl)-pyrrolo[2,1-f][1,2,4]triazin-2-yl]-[2-(4-methyl-piperazin-1-ylmethyl)-1H-benzimidazol-5-yl]-amine Analogous to Example 1510b, 7-(4-Methanesulfonyl-phenyl)-pyrrolo[2,1-f][1,2,4]triazin-2-ol (65.0 mg, 0.225 mmol) and 2-[(4-methylpiperazin-1-yl)methyl]-1H-benzimidazol-5-amine tetrahydrochloride (96.7 mg, 0.247 mmol) were reacted to afford [7-(4-Methanesulfonyl-phenyl)-pyrrolo[2,1-f][1,2,4]triazin-2-yl]-[2-(4-methyl-piperazin-1-ylmethyl)-1H-benzimidazol-5-yl]-amine as the TFA salt (81 mg, 57%). LCMS (HPLC): 0.69 min, m/z=517 (M+H); 1H-NMR (DMSO-d6): 9.83 (s, 1H), 9.59 (br s, 1H), 9.11 (s, 1H), 8.53 (d, 2H, J=8.5 Hz), 8.15 (s, 1H), 8.05 (d, 2H, J=8.5 Hz), 7.71 (m, 2H), 7.42 (d, 1H, J=4.8 Hz), 7.05 (d, 1H, J=4.8 Hz), 4.08 (s, 2H), 3.46 (m, 2H), 3.30 (s, 3H), 3.09 (m, 4H), 2.84 (s, 3H), 2.59 (m, 2H).

Example 1543

2-(4-{5-[7-(4-Methanesulfonyl-phenyl)-pyrrolo[2,1-f][1,2,4]triazin-2-ylamino]-1H-benzimidazol-2-ylmethyl}-piperazin-1-yl)-ethanol Analogous to Example 1510b, 7-(4-Methanesulfonyl-phenyl)-pyrrolo[2,1-f][1,2,4]triazin-2-ol (65.0 mg, 0.225 mmol) and 2-[4-(5-Amino-1H-benzimidazol-2-ylmethyl)-piperazin-1-yl]-ethanol tetrahydrochloride (104 mg, 0.247 mmol) were reacted to afford 2-(4-{5-[7-(4-M ethanesulfonyl-phenyl)-pyrrolo[2,1-f][1,2,4]triazin-2-ylamino]-1H-benzimidazol-2-ylmethyl}-piperazin-1-yl)-ethanol as the TFA salt (99 mg, 67%). LCMS (HPLC): 0.67 min, m/z=547 (M+H); 1H-NMR (DMSO-d6): 9.83 (s, 1H), 9.59 (br s, 1H), 9.11 (s, 1H), 8.53 (d, 2H, J=8.5 Hz), 8.15 (s, 1H), 8.05 (d, 2H, J=8.5 Hz), 7.71 (m, 2H), 7.42 (d, 1H, J=4.8 Hz), 7.05 (d, 1H, J=4.8 Hz), 4.08 (s, 2H), 3.75 (t, 2H, J=4.8 Hz), 3.52 (m, 2H), 3.29 (s, 3H), 3.22 (m, 2H), 3.08-3.18 (m, 4H), 2.69 (m, 2H).

Example 1544

2-(4-{4-[7-(3-tert-Butylsulfamoyl-phenyl)-pyrrolo[2,1-f][1,2,4]triazin-2-ylamino]-phenyl}-4-cyano-piperidin-1-yl)-acetamide 1544a) 4-Phenyl-piperidine-4-carbonitrile; hydrochloride (2.80 g, 12.6 mmol) was dissolved in Methylene chloride (50.0 mL) and N,N-Diisopropylethylamine (6.00 mL, 34.4 mmol). The reaction was then treated with Trifluoroacetic anhydride (2.20 mL, 15.6 mmol) and the reaction was allowed to stir overnight at room temperature. The mixture was washed with 10% citric acid (aq, 50 mL) and 4:1 brine: 3N HCl (50 mL). After drying over sodium sulfate, the org. was filtered through 4 ml silica gel, eluting with 50 mL EtOAc. After conc. in vacuo, the oil was dried on high vacuum, slowly generating 4-phenyl-1-(2,2,2-trifluoroacetyl)-piperidine-4-carbonitrile as a semisolid. 1H-NMR (DMSO-d6): 7.58 (d, 2H, J=7.6 Hz), 7.46 (m, 2H), 7.39 (t, 1H, J=7.2 Hz), 4.50 (m, 1H), 4.05 (m, 1H), 3.54 (m, 1H), 3.17 (m, 1H), 2.27 (m, 2H), 2.14 (m, 2H).

1544b) 4-Phenyl-1-(2,2,2-trifluoro-acetyl)-piperidine-4-carbonitrile was dissolved in Acetonitrile (12.0 mL), Trifluoroacetic anhydride (4.00 mL, 28.3 mmol) was added and the mixture was cooled in an ice bath. Potassium nitrate (1.58 g, 15.6 mmol) was then added and the reaction was stirred at 0° C. for 2 h, then water (100 mL) was added at 0° C. The mixture was extracted with EtOAc (2×50 mL), the organics were washed with 1:1 brine:satd. NaHCO3 (2×50 mL), dried over sodium sulfate and then filtered through 8 mL silica gel, washing with 100 mL EtOAc. The filtrate was conc. in vacuo. 1H-NMR indicated a mixture of nitration products and starting material. Resubjection to the nitration conditions (12 mL MeCN, 4 mL TFAA, 1.59 g KNO3, rt, overnight). Work up as before, conc. in vacuo to afford an oil, 1H-NMR showing -2.6:1 ratio of nitration products. The crude oil was dried in vacuo and then dissolved in DCM, loaded onto a 25 g ISCO cartridge and purified (120 g column, 0%, then 5-30% EtOAc:Hex) to afford partial separation of the nitro products, the major eluting first. Clean fractions were conc. in vacuo to afford 4-(4-Nitro-phenyl)-1-(2,2,2-trifluoro-acetyl)-piperidine-4-carbonitrile (1.29 g; Yield=31.4%) as a white solid. 1H-NMR (DMSO-d6): 8.31 (d, 2H, J=8.8 Hz), 7.91 (d, 2H, J=8.8 Hz), 4.52 (m, 1H), 4.07 (m, 1H), 3.55 (m, 1H), 3.17 (m, 1H), 2.27 (m, 4H).

1544c) 4-(4-Nitro-phenyl)-1-(2,2,2-trifluoro-acetyl)-piperidine-4-carbonitrile (1.28 g, 3.91 mmol) was suspended in Methanol (50.0 mL) and treated with 2.00 M of Sodium carbonate in Water (20.0 mL, 40.0 mmol) at rt overnight. Water was added to the heterogenous mixture to achieve a solution, then the mixture was partitioned between DCM and brine (50 mL each). Ext. of the aq. with DCM (3×50 mL), followed by washing the org. with brine (50 mL), drying and conc. in vacuo afforded 4-(4-Nitro-phenyl)-piperidine-4-carbonitrile (0.800 g; Yield=88.4) as a white solid. 1H-NMR (DMSO-d6): 8.30 (d, 2H, J=8.8 Hz), 7.83 (d, 2H, J=8.8 Hz), 3.07 (m, 2H), 2.82 (m, 2H), 2.36 (br s, 1H), 2.05 (m, 2H), 1.92 (m, 2H).

1544d) 4-(4-Nitro-phenyl)-piperidine-4-carbonitrile (0.795 g, 3.44 mmol) and MP-Carbonate resin (3.16 mmol/g loading; 2.18 g, 6.88 mmol) were combined in Acetonitrile (24.0 mL) and Iodoacetamide (0.720 g, 3.70 mmol) was then added and then stirred overnight. After 24 h, conversion was not complete, so additional MP-Carbonate resin (1.21 g, 3.82 mmol), Iodoacetamide (0.405 g, 2.08 mmol) and Acetonitrile (30.0 mL, 574 mmol) were added. After 8 h, the reaction was complete. Solubilize the precipitated product with DCM:MeOH, filter off resin and wash with DCM:MeOH. Conc. onto 10 g silica gel. ISCO (40 g, 0-20% MeOH:EtOAc) to afford 2-[4-Cyano-4-(4-nitro-phenyl)-piperidin-1-yl]-acetamide (1.09 g; Yield=100) as a white solid. 1H-NMR (DMSO-d6): 8.31 (d, 2H, J=8.7 Hz), 7.87 (d, 2H, J=8.7 Hz), 7.35 (br s, 1H), 7.18 (br s, 1H), 2.97 (m, 4H), 2.50 (m, 2H), 2.22 (m, 2H), 2.13 (m, 2H).

1544e) 2-[4-Cyano-4-(4-nitro-phenyl)-piperidin-1-yl]-acetamide (0.644 g, 2.23 mmol) was shaken over 5% Platinum on Carbon, Sulfided (0.5%) (94 mg, 0.024 mmol) in Methanol (10.0 mL) under an atmosphere of Hydrogen (40 psi) for 5 h. The precipitate was solubilized in DCM and then filtered to remove catalyst, washing with DCM. Conc. in vacuo to give 2-[4-(4-Amino-phenyl)-4-cyano-piperidin-1-yl]-acetamide (0.570 g; Yield=98.8) as an off white solid. ¹H-NMR (DMSO-d6): 7.29 (s, 1H), 7.14 (m, 3H), 6.58 (d, 2H, J=8.4 Hz), 5.17 (s, 2H), 3.17 (d, 1H, J=5.2 Hz), 2.92 (s, 2H), 2.90 (m, 2H), 2.39 (m, 2H), 2.00 (m, 4H).

1544f) Analogous to Example 1510b, N-tert-Butyl-3-(2-hydroxy-pyrrolo[2,1-f][1,2,4]triazin-7-yl)-benzenesulfonamide (81.1 mg, 0.234 mmol) and 2-[4-(4-Amino-phenyl)-4-cyano-piperidin-1-yl]-acetamide (66.6 mg, 0.258 mmol) were reacted to afford 2-(4-{4-[7-(3-tert-Butylsulfamoyl-phenyl)-pyrrolo[2,1-f][1,2,4]triazin-2-ylamino]-phenyl}-4-cyano-piperidin-1-yl)-acetamide as the TFA salt (71 mg, 43%). LCMS (UPLC): 0.97 min, m/z=587 (M+H); 1H-NMR (DMSO-d6): 9.87 (br s, 1H), 9.76 (s, 1H), 9.08 (s, 1H), 8.60 (s, 1H), 8.32 (d, 1H, J=7.9 Hz), 7.99 (s, 1H), 7.86 (m, 3H), 7.75 (m, 2H), 7.63 (s, 1H), 7.50 (d, 1H, J=8.3 Hz), 7.23 (d, 1H, J=4.7 Hz), 7.03 (d, 1H, J=4.7 Hz), 4.09 (s, 2H), 3.70 (m, 2H), 3.34 (m, 2H), 2.42 (m, 4H), 1.11 (s, 9H).

Example 1545

2-(4-Cyano-4-{4-[7-(6-methoxy-pyridin-3-yl)-pyrrolo[2,1-f][1,2,4]triazin-2-ylamino]-phenyl}-piperidin-1-yl)-acetamide Analogous to Example 1510b, 7-(6-Methoxy-pyridin-3-yl)-pyrrolo[2,1-f][1,2,4]triazin-2-ol (56.7 mg, 0.234 mmol) and 2-[4-(4-Amino-phenyl)-4-cyano-piperidin-1-yl]-acetamide (66.6 mg, 0.258 mmol) were reacted to afford 2-(4-Cyano-4-{4-[7-(6-methoxy-pyridin-3-yl)-pyrrolo[2,1-f][1,2,4]triazin-2-ylamino]-phenyl}-piperidin-1-yl)-acetamide as the TFA salt (59 mg, 42%). LCMS (HPLC): 0.89 min, m/z=483 (M+H); 1H-NMR (DMSO-d6): 9.81 (br s, 1H), 9.72 (s, 1H), 9.01 (s, 1H), 8.90 (s, 1H), 8.53 (d, 1H, J=8.7 Hz), 7.99 (s, 1H), 7.82 (d, 2H, J=8.6 Hz), 7.74 (s, 1H), 7.45 (d, 2H, J=8.3 Hz), 7.21 (d, 1H, J=4.7 Hz), 7.04 (d, 1H, J=8.7 Hz), 6.99 (d, 1H, J=4.7 Hz), 4.09 (s, 2H), 3.95 (s, 3H), 3.69 (m, 2H), 3.33 (m, 2H), 2.39 (m, 4H).

Example 1546

2-(4-Cyano-4-{4-[7-(3-methanesulfonyl-phenyl)-pyrrolo[2,1-f][1,2,4]triazin-2-ylamino]-phenyl}-piperidin-1-yl)-acetamide Analogous to Example 1510b, 7-(3-Methanesulfonyl-phenyl)-pyrrolo[2,1-f][1,2,4]triazin-2-ol (67.8 mg, 0.234 mmol) and 2-[4-(4-Amino-phenyl)-4-cyano-piperidin-1-yl]-acetamide (66.6 mg, 0.258 mmol) were reacted to afford 2-(4-Cyano-4-{4-[7-(3-methanesulfonyl-phenyl)-pyrrolo[2,1-f][1,2,4]triazin-2-ylamino]-phenyl}-piperidin-1-yl)-acetamide as the TFA salt (73 mg, 48%). LCMS (HPLC): 0.82 min, m/z=530 (M+H); 1H-NMR (DMSO-d6): 9.88 (br s, 1H), 9.78 (s, 1H), 9.09 (s, 1H), 8.70 (s, 1H), 8.43 (d, 1H, J=7.9 Hz), 7.98 (m, 2H), 7.83 (m, 3H), 7.75 (s, 1H), 7.50 (d, 2H, J=8.3 Hz), 7.33 (d, 1H, J=4.8 Hz), 7.04 (d, 1H, J=4.8 Hz), 4.09 (s, 2H), 3.71 (m, 2H), 3.33 (m, 2H), 3.31 (s, 3H), 2.39 (m, 4H).

Example 1547

2-(4-Cyano-4-{4-[7-(4-methanesulfonyl-phenyl)-pyrrolo[2,1-f][1,2,4]triazin-2-ylamino]-phenyl}-piperidin-1-yl)-acetamide Analogous to Example 1510b, 7-(4-Methanesulfonyl-phenyl)-pyrrolo[2,1-f][1,2,4]triazin-2-ol (67.8 mg, 0.234 mmol) and 2-[4-(4-Amino-phenyl)-4-cyano-piperidin-1-yl]-acetamide (66.6 mg, 0.258 mmol) were reacted to afford 2-(4-Cyano-4-{4-[7-(4-methanesulfonyl-phenyl)-pyrrolo[2,1-f][1,2,4]triazin-2-ylamino]-phenyl}-piperidin-1-yl)-acetamide as the TFA salt (73 mg, 48%). LCMS (HPLC): 0.82 min, m/z=530 (M+H); 1H-NMR (DMSO-d6): 9.85 (br s, 1H), 9.81 (s, 1H), 9.10 (s, 1H), 8.48 (d, 2H, J=8.5 Hz), 8.07 (d, 2H, J=8.5 Hz), 7.99 (s, 1H), 7.84 (d, 2H, J=8.5 Hz), 7.75 (s, 1H), 7.50 (d, 2H, J=8.4 Hz), 7.39 (d, 1H, J=4.8 Hz), 7.05 (d, 1H, J=4.8 Hz), 4.10 (s, 2H), 3.71 (m, 2H), 3.34 (m, 2H), 3.30 (s, 3H), 2.41 (m, 4H).

Example 1548

2-(4-Cyano-4-{4-[7-(2-methoxy-phenyl)-pyrrolo[2,1-f][1,2,4]triazin-2-ylamino]-phenyl}-piperidin-1-yl)-acetamide Analogous to Example 1510b, 7-(2-Methoxy-phenyl)-pyrrolo[2,1-f][1,2,4]triazin-2-ol (56.5 mg, 0.234 mmol) and 2-[4-(4-Amino-phenyl)-4-cyano-piperidin-1-yl]-acetamide (66.6 mg, 0.258 mmol) were reacted to afford 2-(4-Cyano-4-{4-[7-(2-methoxy-phenyl)-pyrrolo[2,1-f][1,2,4]triazin-2-ylamino]-phenyl}-piperidin-1-yl)-acetamide as the TFA salt (72 mg, 52%). LCMS (HPLC): 0.93 min, m/z=482 (M+H); 1H-NMR (DMSO-d6): 9.82 (br s, 1H), 9.63 (s, 1H), 8.99 (s, 1H), 8.00 (s, 1H), 7.80 (m, 3H), 7.75 (s, 1H), 7.49 (m, 1H), 7.34 (d, 2H, J=8.2 Hz), 7.24 (d, 1H, J=8.3 Hz), 7.14 (m, 1H), 6.97 (m, 2H), 4.09 (s, 2H), 3.81 (s, 3H), 3.69 (m, 2H), 3.33 (m, 2H), 2.38 (m, 4H).

Example 1549

2-[4-Cyano-4-(4-{7-[2-(methanesulfonyl-methyl-amino)-phenyl]-pyrrolo[2,1-f][1,2,4]triazin-2-ylamino}-phenyl)-piperidin-1-yl]-acetamide Analogous to Example 1510b, N-[2-(2-Hydroxy-pyrrolo[2,1-f][1,2,4]triazin-7-yl)-phenyl]-N-methyl-methanesulfonamide (74.6 mg, 0.234 mmol) and 2-[4-(4-Amino-phenyl)-4-cyano-piperidin-1-yl]-acetamide (66.6 mg, 0.258 mmol) were reacted to afford 2-[4-Cyano-4-(4-{7-[2-(methanesulfonyl-methyl-amino)-phenyl]-pyrrolo[2,1-f][1,2,4]triazin-2-ylamino}-phenyl)-piperidin-1-yl]-acetamide as the TFA salt (74 mg, 47%). LCMS (HPLC): 0.82 min, m/z=559 (M+H); 1H-NMR (DMSO-d6): 9.81 (br s, 1H), 9.64 (s, 1H), 9.01 (s, 1H), 8.00 (m, 2H), 7.74 (m, 3H), 7.68 (d, 1H, J=8.4 Hz), 7.58 (m, 2H), 7.33 (d, 2H, J=8.4 Hz), 7.02 (d, 1H, J=4.7 Hz), 6.99 (d, 1H, J=4.7 Hz), 4.09 (s, 2H), 3.69 (m, 2H), 3.33 (m, 2H), 3.09 (s, 3H), 2.90 (s, 3H), 2.38 (m, 4H).

Example 1550

N-tert-Butyl-3-{2-[3-(4-hydroxy-piperidin-4-yl)-phenylamino]-pyrrolo[2,1-f][1,2,4]triazin-7-yl}-benzenesulfonamide Analogous to Example 1528d, N-tert-Butyl-3-(2-hydroxy-pyrrolo[2,1-f][1,2,4]triazin-7-yl)-benzenesulfonamide (95 mg, 0.27 mmol) and 4-(3-Amino-phenyl)-4-hydroxy-piperidine-1-carboxylic acid tert-butyl ester (89 mg, 0.30 mmol) were reacted to afford N-tert-Butyl-3-{2-[3-(4-hydroxy-piperidin-4-yl)-phenylamino]-pyrrolo[2,1-f][1,2,4]triazin-7-yl}-benzenesulfonamide as the TFA salt (95 mg, 54%). LCMS (HPLC): 0.95 min, m/z=521 (M+H); 1H-NMR (DMSO-d6): 9.55 (s, 1H), 9.05 (s, 1H), 8.46 (m, 3H), 8.26 (br s, 1H), 7.90 (d, 1H, J=7.7 Hz), 7.84 (d, 1H, J=7.8 Hz), 7.73 (m, 1H), 7.63 (s, 1H), 7.61 (s, 1H), 7.38 (m, 1H), 7.22 (d, 1H, J=4.7 Hz), 7.02 (m, 2H), 5.37 (s, 1H), 3.22 (m, 4H), 2.05 (m, 2H), 1.79 (m 2H), 1.11 (s, 9H).

Example 1551

4-{3-[7-(6-Methoxy-pyridin-3-yl)-pyrrolo[2,1-f][1,2,4]triazin-2-ylamino]-phenyl}-piperidin-4-ol Analogous to Example 1528d, 7-(6-Methoxy-pyridin-3-yl)-pyrrolo[2,1-f][1,2,4]triazin-2-ol (67 mg, 0.28 mmol) and 4-(3-Amino-phenyl)-4-hydroxy-piperidine-1-carboxylic acid tert-butyl ester (89 mg, 0.30 mmol) were reacted to afford 4-{3-[7-(6-Methoxy-pyridin-3-yl)-pyrrolo[2,1-f][1,2,4]triazin-2-ylamino]-phenyl}-piperidin-4-ol as the TFA salt (77 mg, 53%). LCMS (HPLC): 0.84 min, m/z=417 (M+H); 1H-NMR (DMSO-d6): 9.50 (s, 1H), 9.00 (s, 1H), 8.97 (d, 1H, J=1.6 Hz), 8.49 (dd, 1H, J=1.6, 8.7 Hz), 8.45 (br s, 1H), 8.28 (br s, 1H), 7.76 (s, 1H), 7.67 (d, 1H, J=8.7 Hz), 7.32 (m, 1H), 7.21 (d, 1H, J=4.7 Hz), 7.06 (d, 1H, J=7.8 Hz), 6.99 (m, 2H), 5.37 (s, 1H), 3.92 (s, 3H), 3.21 (m, 4H), 2.05 (m, 2H), 1.81 (m 2H).

Example 1552

4-{3-[7-(3-Methanesulfonyl-phenyl)-pyrrolo[2,1-f][1,2,4]triazin-2-ylamino]-phenyl}-piperidin-4-ol Analogous to Example 1528d, 7-(3-Methanesulfonyl-phenyl)-pyrrolo[2,1-f][1,2,4]triazin-2-ol (79 mg, 0.27 mmol) and 4-(3-Amino-phenyl)-4-hydroxy-piperidine-1-carboxylic acid tert-butyl ester (89 mg, 0.30 mmol) were reacted to afford 4-{3-[7-(3-Methanesulfonyl-phenyl)-pyrrolo[2,1-f][1,2,4]triazin-2-ylamino]-phenyl}-piperidin-4-ol as the TFA salt (107 mg, 68%). LCMS (HPLC): 0.79 min, m/z=464 (M+H); 1H-NMR (DMSO-d6): 9.57 (s, 1H), 9.06 (s, 1H), 8.54 (m, 2H), 8.47 (br s, 1H), 8.27 (br s, 1H), 7.94 (d, 1H, J=7.9 Hz), 7.90 (d, 1H, J=8.1 Hz), 7.81 (m, 1H), 7.61 (s, 1H), 7.37 (m, 1H), 7.31 (d, 1H, J=4.8 Hz), 7.02 (m, 2H), 5.38 (s, 1H), 3.29 (s, 3H), 3.21 (m, 4H), 2.05 (m, 2H), 1.78 (m 2H).

Example 1553

2-[4-(4-{5-Chloro-7-[2-(methanesulfonyl-methyl-amino)-phenyl]-pyrrolo[2,1-f][1,2,4]triazin-2-ylamino}-phenyl)-piperidin-1-yl]-acetamide 1553a) 5-Bromo-2-methylsulfanyl-pyrrolo[2,1-f][1,2,4]triazine (244 mg, 1.00 mmol) and Nickel Chloride Hexahydrate (356 mg, 1.50 mmol) were combined in a CEM reaction vial and charged with N,N-Dimethylformamide (2.00 mL), then heated in a CEM microwave at 170° C. for two 10 min cycles. The reaction was partitioned between EtOAc:Hex (9:1, 20 mL) and water (10 mL), separated and the aq. extracted with 9:1 EtOAc:Hex (2×20 mL). The comb. organics were washed with water (2×10 mL), dried over sodium sulfate and conc. in vacuo. The residue was applied to a 5 g ISCO cartridge and purified on an ISCO (12 g col, 0-10% EtOAc:Hex) to furnish 5-Chloro-2-methylsulfanyl-pyrrolo[2,1-f][1,2,4]triazine (0.150 g; Yield=75.2%) as a yellow solid. m.p. 107-108° C.; LCMS (Bruker, fragile): 3.5 min, m/z=200 (M+H); 1H-NMR (DMSO-d6): 9.01 (s, 1H), 8.05 (d, 1H, J=2.6 Hz), 7.02 (d, 1H, J=2.6 Hz), 2.53 (s, 3H).

1553b) 5-Chloro-2-methylsulfanyl-pyrrolo[2,1-f][1,2,4]triazine (54 mg, 0.27 mmol) was dissolved in 1,2-Dichloroethane (2.0 mL and then N-Iodosuccinimide (75 mg, 0.33 mmol) was added in one portion and the reaction was stirred in a vial at 60° C. overnight. The heterogenous mixture was powdered onto silica gel (0.75 g) and purified on ISCO (12 g, 0-5% EtOAc:Hex) to afford 5-Chloro-7-iodo-2-methylsulfanyl-pyrrolo[2,1-f][1,2,4]triazine (49 mg; Yield=56%) as a yellow solid. m.p. 216-220° C.; LCMS (Bruker, Fragile): 4.0 min, m/z=326; 1H-NMR (CDCl3): 8.55 (s, 1H), 6.90 (s, 1H), 2.63 (s, 3H).

1553c) 5-Chloro-7-iodo-2-methylsulfanyl-pyrrolo[2,1-f][1,2,4]triazine (0.252 g, 0.774 mmol), N-[2-(4,4,5,5-Tetramethyl-1,3,2-dioxaborolan-2-yl)-phenyl]-methanesulfonamide (0.333 g, 1.12 mmol) and Tetrakis(triphenylphosphine) palladium(0) (72 mg, 0.062 mmol) were placed in a vial, followed by N,N-Dimethylformamide (8.0 mL) and 2.00 M of Sodium carbonate in Water (2.00 mL, 4.00 mmol). The sample was partially evacuated, placed under nitrogen and then heated in a 80° C. block for 20 h. Dimethyl sulfate (0.100 mL, 1.06 mmol) was then added to the mixture and heating continued for 7 h. The mixture was then added to water (50 mL) with stirring, portionwise. The resultant ppt was collected, washed with water and dried on the Buchner to afford N-[2-(5-Chloro-2-methylsulfanyl-pyrrolo[2,1-f][1,2,4]triazin-7-yl)-phenyl]-N-methyl-methanesulfonamide.

1553d) N-[2-(5-Chloro-2-methylsulfanyl-pyrrolo[2,1-f][1,2,4]triazin-7-yl)-phenyl]-N-methyl-methanesulfonamide was dissolved in Methylene chloride (10 mL, 200 mmol) and m-Chloroperbenzoic acid (235 mg, 1.05 mmol) was added. After 90 min, additional m-Chloroperbenzoic acid (135 mg, 0.602 mmol) was added. Formation of the sulfoxide was concomitant with sulfone formation. After 1 h, the mixture was partitioned between satd. NaHCO3 (20 mL) and EtOAc (50 mL); the aq. was extracted with EtOAc (2×20 mL) and the comb. org. washed with brine:satd. NaHCO3 (40 mL). After drying, the mixture was conc. in vacuo. The crude N-[2-(5-Chloro-2-methanesulfinyl-pyrrolo[2,1-f][1,2,4]triazin-7-yl)-phenyl]-N-methyl-methanesulfonamide was dissolved in 1,4-Dioxane (4.00 mL) then treated with 5.0 M of Sodium hydroxide in Water (1.00 mL, 5.00 mmol) and heated to 60° C. for 2 h. The mixture was cooled, treated with Acetic acid (0.400 mL, 7.04 mmol) and water (2 mL), then partitioned between water and DCM (30 mL each), sept. and extr. with DCM (3×20 mL), dried and conc. in vacuo. The residue was applied to a 5 g ISCO cartridge, then purified (24 g SiO2, 10-100% EtOAc:Hex) to afford N-[2-(5-Chloro-2-hydroxy-pyrrolo[2,1-f][1,2,4]triazin-7-yl)-phenyl]-N-methyl-methanesulfonamide (0.129 g; Yield=47.2% over 4 steps) as an orange foam. LCMS (HPLC): 0.76 min, m/z=353 (M+H); 1H-NMR (DMSO-d6): 11.87 (br s, 1H), 9.01 (s, 1H), 7.69 (m, 2H), 7.59 (m, 2H), 7.50 (m, 1H), 6.99 (s, 1H), 3.19 (s, 3H), 2.84 (s, 3H).

1553e) Analogous to Example 1510b, N-[2-(5-Chloro-2-hydroxy-pyrrolo[2,1-f][1,2,4]triazin-7-yl)-phenyl]-N-methyl-methanesulfonamide (64 mg, 0.18 mmol) and 2-[4-(4-Amino-phenyl)-piperidin-1-yl]-acetamide (48 mg, 0.20 mmol) were reacted to afford 2-[4-(4-{5-Chloro-7-[2-(methanesulfonyl-methyl-amino)-phenyl]-pyrrolo[2,1-f][1,2,4]triazin-2-ylamino}-phenyl)-piperidin-1-yl]-acetamide as the TFA salt (75 mg; Yield=61%) as a yellow lyophilate. LCMS (HPLC): 0.91 min, m/z=568 (M+H); 1H-NMR (DMSO-d6): 9.58 (s, 1H), 9.51 (br s, 1H), 9.01 (s, 1H), 7.96 (m, 2H), 7.70 (m, 2H), 7.58 (m, 4H), 7.06 (d, 2H, J=7.6 Hz), 7.01 (s, 1H), 3.91 (s, 2H), 2.54 (m, 2H), 3.11 (m, 5H), 2.93 (s, 3H), 2.70 (m, 1H), 1.93 (m, 4H).

Example 1554

2-[4-(4-{5-Chloro-7-[2-(methanesulfonyl-methyl-amino)-phenyl]-pyrrolo[2,1-f][1,2,4]triazin-2-ylamino}-3-methoxy-phenyl)-piperidin-1-yl]-acetamide Analogous to Example 1510b, N-[2-(5-Chloro-2-hydroxy-pyrrolo[2,1-f][1,2,4]triazin-7-yl)-phenyl]-N-methyl-methanesulfonamide (64 mg, 0.18 mmol) and 2-[4-(4-Amino-3-methoxy-phenyl)-piperidin-1-yl]-acetamide (52.5 mg, 0.200 mmol) were reacted to afford 2-[4-(4-{5-Chloro-7-[2-(methanesulfonyl-methyl-amino)-phenyl]-pyrrolo[2,1-f][1,2,4]triazin-2-ylamino}-3-methoxy-phenyl)-piperidin-1-yl]-acetamide as the TFA salt (74 mg; Yield=57%) as a yellow lyophilate. LCMS (HPLC): 0.97 min, m/z=598 (M+H); 1H-NMR (DMSO-d6): 9.48 (br s, 1H), 8.98 (s, 1H), 7.95 (m, 3H), 7.79 (d, 1H, J=8.1 Hz), 7.72 (s, 1H), 7.67 (d, 1H, J=7.2 Hz), 7.55 (m, 2H), 7.01 (s, 1H), 6.88 (s, 1H), 6.68 (d, 1H, J=8.2 Hz), 3.92 (s, 2H), 3.84 (s, 3H), 3.55 (m, 2H), 3.15 (m, 2H), 3.09 (s, 3H), 2.91 (s, 3H), 2.76 (m, 1H), 1.99 (m, 4H).

Example 1555

2-(4-{4-[5-Chloro-7-(6-methoxy-pyridin-3-yl)-pyrrolo[2,1-f][1,2,4]triazin-2-ylamino]-phenyl}-piperidin-1-yl)-acetamide 1555a) 2-Methoxypyridine-5-boronic acid (116 mg, 0.758 mmol), Tetrakis(triphenylphosphine)palladium(0) (46 mg, 0.040 mmol) and 5-Chloro-7-iodo-2-methylsulfanyl-pyrrolo[2,1-f][1,2,4]triazine (0.152 g, 0.467 mmol) were placed in a vial, followed by 1,4-Dioxane (3.00 mL) and 2.00 M of Sodium carbonate in Water (1.00 mL, 2.00 mmol). The sample was frozen, placed under vacuum, sealed, warmed, refrozen, evacuated, then placed under nitrogen and heated in a 60° C. block. When complete, the sample was partitioned between EtOAc and water (30 mL each), the aq. extracted (EtOAc 3×20 mL) and the comb. organics washed with brine. Purification (ISCO, 12 g, 0-30% EtOAc:Hex) afforded 5-Chloro-7-(6-methoxy-pyridin-3-yl)-2-methylsulfanyl-pyrrolo[2,1-f][1,2,4]triazine (0.116 g, 81%).

1555b) 5-Chloro-7-(6-methoxy-pyridin-3-yl)-2-methyl-sulfanyl-pyrrolo[2,1-f][1,2,4]triazine (114 mg, 0.372 mmol) was dissolved in Methanol (12.0 mL): Tetrahydrofuran (8.0 mL), Acetic acid (0.200 mL, 3.52 mmol) was added followed by Sodium Tungstate Dihydrate (7.0 mg, 0.021 mmol) and 50% Hydrogen Peroxide (0.100 mL, 1.76 mmol) and the mixture was heated at 60-80° C. overnight in a vial. LCMS shows conversion to a mixture of sulfoxide and sulfone. The mixture was cooled, added portionwise to stirring water (60 mL) and let stand. The solids were collected, washing with water. The crude 5-Chloro-2-methanesulfonyl-7-(6-methoxy-pyridin-3-yl)-pyrrolo[2,1-f][1,2,4]triazine was suspended in 1,4-Dioxane (3.00 mL): 5.0 M of Sodium hydroxide in Water (0.50 mL, 2.5 mmol) and heated at 60° C. for 2 h, then cooled and treated with Acetic acid (0.200 mL, 3.52 mmol) and water (1 mL). The solids were let stand 1 h, then collected. Product was also in the aq. layer, which was extr. with DCM (3×20 mL), comb. with the solids and conc. in vacuo onto 3 g silica gel. Purification (ISCO, 0-80% EtOAc:Hex) afforded 5-Chloro-7-(6-methoxy-pyridin-3-yl)-pyrrolo[2,1-f][1,2,4]triazin-2-ol (31 mg; Yield=30%) as yellow solids.

155c) Analogous to Example 1510b, 5-Chloro-7-(6-methoxy-pyridin-3-yl)-pyrrolo[2,1-f][1,2,4]triazin-2-ol (30.0 mg, 0.108 mmol) and 2-[4-(4-Amino-phenyl)-piperidin-1-yl]-acetamide (27.8 mg, 0.119 mmol) were reacted to afford 2-(4-{4-[5-Chloro-7-(6-methoxy-pyridin-3-yl)-pyrrolo[2,1-f][1,2,4]triazin-2-ylamino]-phenyl}-piperidin-1-yl)-acetamide as the TFA salt (48 mg; Yield=73%) as a yellow lyophilate.

Example 1556

5-({7-[2-(1,1-Dioxido-1,2-thiazolidin-2-yl)phenyl]pyrrolo[2,1-f][1,2,4]triazin-2-yl}amino)-3,3-dimethyl-1,3-dihydro-2H-indol-2-one 1556a) 7-Bromo-2-methylsulfanyl-pyrrolo[2,1-f][1,2,4]triazine (1.00 g, 4.10 mmol), 2-aminophenylboronic acid pinocl ester (1.84 g, 8.40 mmol), and Tetrakis(triphenylphosphine)palladium(0) (0.710 g, 0.614 mmol) were dissolved in Ethanol (15 mL) and Tetrahydrofuran (15 mL) followed by addition of 2.00 M of Sodium carbonate in Water (5.0 mL, 10 mmol). The reaction mixture was then heated at 75° C. and was allowed to stir overnight. After cooling to room temperature, the reaction mixture was acidified with ~2 mL concentrated HCl and then extracted with EtOAc (2×, 30 mL). The organics were then back extracted with 3M HCl (2×, 20 mL) and the aqueous layers combined and washed with EtOAc (2×, 20 mL). The combined HCl was then basified while stirring with 5N NaOH followed by extraction with DCM (3×, 30 mL) and brine, drying with sodium sulfate, and conc. in vacuo. The product was then purified by ISCO column chromatography (50/50 EtOAc/Hex, 40 g column) to afford 2-(2-Methylsulfanyl-pyrrolo[2,1-f][1,2,4]triazin-7-yl)-phenylamine as a white solid (0.78 g, 74%). LCMS: 257 (M+H). 1H-NMR (CDCl3): 8.74 (s, 1H), 7.44 (d, 1H, J=7.72 Hz), 6.98 (d, 1H, J=4.82 Hz), 6.94 (d, 1H, J=4.82 Hz), 6.88 (d, 1H, J=7.78 Hz), 6.84 (d, 1H, J=7.78 Hz), 4.12 (m, 2H), 2.50 (s, 3H).

1556b) Analogous to Example 1506b, 2-(2-Methylsulfanyl-pyrrolo[2,1-f][1,2,4]triazin-7-yl)-phenylamine (0.777 g, 3.03 mmol) was reacted with 3-Chloropropane-1-sulfonyl chloride to afford 7-[2-(1,1-Dioxido-1,2-thiazolidin-2-yl)phenyl]-2-(methylsulfanyl)pyrrolo[2,1-f][1,2,4]triazine as a yellow solid (83 mg, 8%). 1H-NMR (DMSO-d6): 8.79 (s, 1H), 7.84 (dd, 1H, J=5.04 Hz), 7.72 (dd, 1H, J=5.04 Hz), 7.46 (m, 2H), 7.29 (d, 1H, J=4.72 Hz), 6.91 (d, 1H, J=4.72 Hz), 3.38 (t, 2H, J=6.81), 3.19 (t, 2H, J=7.49), 2.48 (s, 3H), 2.27 (quin, 2H, J=7.49).

1556c) Analogous to Example 1506c, 7-[2-(1,1-Dioxido-1,2-thiazolidin-2-yl)phenyl]-2-(methylsulfanyl)pyrrolo[2,1-f][1,2,4]triazine (83 mg, 0.230 mmol) was oxidized to afford 7-[2-(1,1-Dioxido-1,2-thiazolidin-2-yl)phenyl]-2-(methylsulfinyl)pyrrolo[2,1-f][1,2,4]triazine (68 mg, 79%) as a yellow oil. 1H-NMR (CDCl3): 9.05 (s, 1H), 7.65 (dt, 2H, J=6.55 Hz), 7.54 (dt, 1H, J=6.55 Hz), 7.47 (dt, 1H, J=6.55 Hz), 7.41 (d, 1H, J=5.09 Hz), 7.15 (d, 1H, J=5.09 Hz), 3.86 (m, 2H), 3.07 (d, 2H, J=7.04 Hz), 2.99 (s, 3H), 2.29 (m, 2H).

1556d) Analogous to Example 1491c, 7-[2-(1,1-Dioxido-1,2-thiazolidin-2-yl)phenyl]-2-(methylsulfinyl)pyrrolo[2,1-f][1,2,4]triazine (68 mg, 0.18 mmol) and 5-Amino-3,3-dimethyl-1,3-dihydro-indol-2-one (0.0637 g, 0.361 mmol) were reacted to afford 5-({7-[2-(1,1-Dioxido-1,2-thiazolidin-2-yl)phenyl]pyrrolo[2,1-f][1,2,4]triazin-2-yl}amino)-3,3-dimethyl-1,3-dihydro-2H-indol-2-one as a yellow solid (21 mg, 24%). LCMS: 489 (M+H); 1H-NMR (DMSO-d6): 10.12 (s, 1H), 9.24 (s, 1H), 8.94 (s, 1H), 7.86 (m, 1H), 7.63 (m, 1H), 7.53 (m, 1H), 7.28 (dd, 1H, J=8.53 Hz), 6.98 (d, 1H, J=4.93 Hz), 6.91 (d, 1H, J=4.93 Hz), 6.69 (d, 1H, J=8.53 Hz), 3.29 (s, 2H), 3.24 (t, 2H, J=7.69 Hz), 2.14 (quin, 2H, J=7.69 Hz), 1.05 (s, 6H).

Example 1557

(3-{2-[3-(4-Methyl-piperazin-1-yl)-phenylamino]-pyrrolo[2,1-f][1,2,4]triazin-7-yl}-phenyl)-methanol Analogous to Example 1504, (7-Bromo-pyrrolo[2,1-f][1,2,4]triazin-2-yl)-[3-(4-methyl-piperazin-1-yl)-phenyl]-amine (0.0731 g, 0.189 mmol) and (3-Hydroxymethylphenyl)boronic acid (0.0513 g, 0.338 mmol) were reacted to afford (3-{2-[3-(4-Methyl-piperazin-1-yl)-phenylamino]-pyrrolo[2,1-f][1,2,4]triazin-7-yl}-phenyl)-methanol as a yellow powder (15 mg, 20%). LCMS: 415 (M+H); 1H-NMR (CDCl3): 8.70 (s, 1H), 8.21 (s, 1H), 7.92 (s, 1H), 7.62 (d, 1H, J=6.96 Hz), 7.49 (m, 2H), 7.20 (t, 1H, J=8.19 Hz), 6.93 (d, 1H, J=4.50 Hz), 6.88 (s, 1H), 6.84 (d, 1H, J=4.50 Hz), 6.87 (d, 1H, J=8.19 Hz), 4.77 (s, 2H), 2.98 (t, 4H, J=4.96 Hz), 2.44 (t, 4H, J=4.96 Hz), 2.34 (s, 3H).

Example 1558

[7-(3-tert-Butoxymethyl-phenyl)-pyrrolo[2,1-f][1,2,4]triazin-2-yl]-[3-(4-methyl-piperazin-1-yl)-phenyl]-amine 1558a) 7-Bromo-2-methylsulfanyl-pyrrolo[2,1-f][1,2,4]triazine (0.370 g, 1.52 mmol), 3-(tert-Butoxymethyl)phenylboronic acid (0.564 g, 2.71 mmol), Bis(tri-tert-butylphosphine)palladium (47 mg, 0.092 mmol), 2.00 M of Sodium Carbonate in Water (3.0 mL, 6.0 mmol), and N,N-Dimethylformamide (12.0 mL, 155 mmol) were combined in a reaction vial, partially degassed and backfilled with Nitrogen, and the mixture was heated at 60° C. overnight under an atmosphere of Nitrogen. The reaction mixture was diluted with water (25 mL) and DCM (25 mL). The aqueous was extracted with DCM (2×, 10 mL) and combined organics diluted with 1:1 EtOAc:hexane (50 mL), followed by washes with water (2×, 25 mL) and brine (25 mL). The organics were dried over sodium sulfate and conc. in vacuo to afford 7-(3-tert-Butoxymethyl-phenyl)-2-methylsulfanyl-pyrrolo[2,1-f][1,2,4]triazine which was then oxidized, analogous to Example 1504a, to afford 7-(3-tert-Butoxymethyl-phenyl)-2-methanesulfonyl-pyrrolo[2,1-f][1,2,4]triazine (398 mg, 73%). 1H-NMR (DMSO-d6): 9.37 (s, 1H), 8.22 (s, 1H), 8.10 (d, 1H, J=7.77 Hz), 7.81 (d, 1H, J=4.97 Hz), 7.53 (t, 1H, J=7.77 Hz), 7.44 (d, 1H, J=4.97 Hz), 7.41 (d, 1H, J=7.77 Hz), 4.50 (s, 2H), 3.46 (s, 3H), 1.26 (s, 9H).

1558b) 5M NaOH (4 mL, 20 mmol) was added to 7-(3-tert-Butoxymethyl-phenyl)-2-methanesulfonyl-pyrrolo[2,1-f][1,2,4]triazine (0.398 g, 1.11 mmol) and the reaction was stirred and heated at 80° C. for 2 hours. The reaction was let cool to room temperature and HCl (~2 mL) was then added dropwise to the reaction mixture to precipitate the product (pH 1), which was filtered immediately and washed with water and dried in vacuo to afford 7-(3-tert-Butoxymethyl-phenyl)-pyrrolo[2,1-f][1,2,4]triazin-2-ol (340 mg, 100%) as a brown solid. 1H-NMR (DMSO-d6): 8.64 (s, 1H), 8.21 (d, 1H, J=7.59 Hz), 8.14 (s, 1H), 7.31 (t, 1H, J=7.59 Hz), 7.18 (d, 1H, J=7.59 Hz), 6.88 (s, 1H), 6.56 (s, 1H), 4.47 (s, 2H), 1.25 (s, 9H).

1558c) Analogous to Example 1510b, 7-(3-tert-Butoxymethyl-phenyl)-pyrrolo[2,1-f][1,2,4]triazin-2-ol (109 mg, 0.37 mmol) and 3-(4-Methylpiperazin-1-yl)aniline (0.0878 g, 0.459 mmol) were reacted to afford [7-(3-tert-Butoxymethyl-phenyl)-pyrrolo[2,1-f][1,2,4]triazin-2-yl]-[3-(4-methyl-piperazin-1-yl)-phenyl]-amine (78 mg, 45%). LCMS: 471 (M+H); $^1$H-NMR (DMSO-d6): 9.26 (s, 1H), 9.26 (s, 1H), 8.97 (s, 1H), 8.08 (s, 1H), 7.99 (d, 1H, J=7.83 Hz), 7.46 (t, 1H, J=7.83 Hz), 7.35 (d, 1H, J=7.83 Hz), 7.27 (m, 2H), 7.13 (m, 2H), 6.95 (d, 1H, J=4.38 Hz), 6.57 (d, 1H, J=8.50 Hz), 4.48 (s, 2H), 3.01 (s, 4H), 2.40 (s, 4H), 2.22 (s, 3H), 1.22 (s, 9H).

Example 1559

N-{3-[7-(3-tert-Butoxymethyl-phenyl)-pyrrolo[2,1-f][1,2,4]triazin-2-ylamino]-phenyl}-acetamide Analogous to Example 1510b, 7-(3-tert-Butoxymethyl-phenyl)-pyrrolo[2,1-f][1,2,4]triazin-2-ol (109 mg, 0.37 mmol) and 3'-aminoacetanilide (0.0689 g, 0.459 mmol) were reacted to afford N-{3-[7-(3-tert-Butoxymethyl-phenyl)-pyrrolo[2,1-f][1,2,4]triazin-2-ylamino]-phenyl}-acetamide as an orange foam (62 mg, 39%). LCMS: 430 (M+H); 1H-NMR (DMSO-d6): 9.84 (s, 1H), 9.46 (s, 1H), 8.98 (s, 1H), 8.12 (s, 1H), 8.06 (d, 1H, J=7.71 Hz), 7.72 (s, 1H), 7.63 (d, 1H, J=7.71 Hz), 7.44 (t, 1H, J=7.71 Hz), 7.35 (d, 1H, J=7.71 Hz), 7.22 (m, 2H), 7.19 (d, 1H, 4.65 Hz), 6.96 (d, 1H, J=4.65 Hz), 4.46 (s, 2H), 2.03 (s, 3H), 1.22 (s, 9H).

Example 1560

[7-(3-tert-Butoxymethyl-phenyl)-pyrrolo[2,1-f][1,2,4]triazin-2-yl]-(3-morpholin-4-yl-phenyl)-amine Analogous to Example 1510b, 7-(3-tert-Butoxymethyl-phenyl)-pyrrolo[2,1-f][1,2,4]triazin-2-ol (109 mg, 0.37 mmol) and 3-Morpholin-4-yl-phenylamine (0.0818 g, 0.459 mmol) were reacted to afford [7-(3-tert-Butoxymethyl-phenyl)-pyrrolo[2,1-f][1,2,4]triazin-2-yl]-(3-morpholin-4-yl-phenyl)-amine as an orange foam (95 mg, 56%). LCMS: 458 (M+H); 1H-NMR (DMSO-d6): 9.30 (s, 1H), 8.97 (s, 1H), 8.06 (s, 1H), 7.98 (d, 1H, J=7.74 Hz), 7.46 (t, 1H, J=7.74, 7.36 (d, 1H, 7.74 Hz), 7.30 (s, 1H), 7.28 (d, 1H, J=9.68 Hz), 7.15 (d, 1H, J=8.07 Hz), 7.12 (d, 1H, J=4.84 Hz), 6.95 (d, 1H, J=4.84 Hz), 4.48 (s, 2H), 3.65 (t, 4H, J=4.58 Hz), 2.95 (t, 4H, J=4.58 Hz), 1.22 (s, 9H).

Example 1561

{3-[2-(3-Morpholin-4-yl-phenylamino)-pyrrolo[2,1-f][1,2,4]triazin-7-yl]-phenyl}-methanol Trifluoroacetic Acid (1.00 mL, 13.0 mmol), Triisopropylsilane (0.100 mL, 0.488 mmol), and Water (0.1 mL, 6 mmol) were combined and added to 7-(3-tert-Butoxymethyl-phenyl)-pyrrolo[2,1-f][1,2,4]triazin-2-yl]-(3-morpholin-4-yl-phenyl)-amine (0.069 g, 0.15 mmol) in a vial. The reaction mixture was let stir at room temperature for 2 days. Saturated aqueous NaHCO3 (5 mL) was added to the reaction mixture followed by dilution with water (5 mL) and DCM (5 mL). The aqueous layer was then extracted with DCM (2×, 5 mL), and the combined organics were diluted with 1:1 EtOAc/Hexane (10 mL). Solids formed in the organic layer and were filtered and washed with ether. The organics were further washed with water (1×, 10 mL) and brine (1×, 10 mL), dried over sodium sulfate, and conc. in vacuo and purified by preparative HPLC to afford {3-[2-(3-Morpholin-4-yl-phenylamino)-pyrrolo[2,1-f][1,2,4]triazin-7-yl]-phenyl}-methanol (24 mg, 30%). LCMS: 402 (M+H); 1H-NMR (DMSO-d6): 9.31 (s, 1H), 8.97 (s, 1H), 8.07 (s, 1H), 7.99 (d, 1H, J=7.70 Hz), 7.46 (t, 1H, J=7.50 Hz), 7.34 (m, 3H), 7.14 (m, 2H), 6.96 (d, 1H, J=4.68 Hz), 6.57 (d, 1H, J=8.32 Hz), 4.59 (s, 2H), 3.67 (t, 8H, J=4.43 Hz), 2.97 (t, 4H, J=4.43 Hz).

Example 1562

(3H-Benzimidazol-5-yl)-(7-pyridin-2-yl-pyrrolo[2,1-f][1,2,4]triazin-2-yl)-amine 1562a) 2-Trimethylstannanyl-pyridine (0.557 g, 2.30 mmol) in N,N-Dimethylformamide (7.6 mL, 98 mmol) was added 7-Bromo-2-methylsulfanyl-pyrrolo[2,1-f][1,2,4]triazine (0.250 g, 1.02 mmol) and Tetrakis(triphenylphosphine)palladium(0) (67 mg, 0.058 mmol) in a vial, and the mixture was heated in a block at 80° C. The reaction mixture was then diluted with EtOAc (30 mL) and washed with water (1×, 10 mL), 2.5M KF (2×, 10 mL), and brine (1×, 10 mL), followed by drying with sodium sulfate, filtering, and conc. in vacuo. The crude product was purified by ISCO column chromatography (0-25, 25-100% EtOAc/Hex) to give 2-Methylsulfanyl-7-pyridin-2-yl-pyrrolo[2,1-f][1,2,4]triazine (0.173 g, 70%). 1H-NMR (DMSO-d6): 9.09 (s, 1H), 8.71 (m, 2H), 7.98 (dt, 1H, J=7.80 Hz), 7.63 (d, 1H, J=4.74 Hz), 7.38 (dt, 1H, J=6.40), 7.12 (d, 1H, 4.98 Hz), 2.65 (s, 3H).

1562b) 2-Methylsulfanyl-7-pyridin-2-yl-pyrrolo[2,1-f][1,2,4]triazine (0.173 g, 0.714 mmol) was dissolved in Methanol (5.00 mL) and Sodium Tungstate Dihydrate (19.0 mg, 0.0576 mmol), Acetic acid (0.338 mL, 5.94 mmol) and 50% Hydrogen Peroxide (0.150 mL, 2.64 mmol) were added. The reaction mixture was then stirred and heated at 65° C. overnight. More 50% Hydrogen Peroxide (0.1 mL) was added and the reaction continued stirring. Once the reaction was complete, 5 mL of 10% Na2S2O3 and 2 mL 50% sat. NaHCO3 were added and the reaction was let cool to room temperature followed by refrigeration. The precipitate was then filtered and placed on the high vac to afford 2-Methanesulfonyl-7-pyridin-2-yl-pyrrolo[2,1-f][1,2,4]triazine.

1562c) 5M NaOH (2 mL, 10 mmol) was added to 2-Methanesulfonyl-7-pyridin-2-yl-pyrrolo[2,1-f][1,2,4]triazine and the reaction was stirred and heated at 80° C. overnight. The reaction was let cool to room temperature and HCl was then added dropwise to the reaction mixture to precipitate the product (pH 1), which was filtered immediately and washed with water and left on vacuum overnight to give 7-Pyridin-2-yl-pyrrolo[2,1-f][1,2,4]triazin-2-ol (100 mg, 66% over two steps). 1H-NMR (DMSO-d6): 11.89 (s, 1H), 9.05 (s, 1H), 8.83 (d, 1H, J=7.91 Hz), 8.69 (d, 1H, J=4.74 Hz), 7.96 (t, 1H, J=7.69 Hz), 7.53 (d, 1H, J=4.86 Hz), 7.35 (t, 1H, J=4.86 Hz), 7.04 (d, 1H, J=4.86 Hz).

1562d) Analogous to Example 1510b, 7-Pyridin-2-yl-pyrrolo[2,1-f][1,2,4]triazin-2-ol (50.0 mg, 0.236 mmol) and 3H-Benzimidazol-5-ylamine (39.2 mg, 0.294 mmol) were reacted to afford (3H-Benzimidazol-5-yl)-(7-pyridin-2-yl-pyrrolo[2,1-f][1,2,4]triazin-2-yl)-amine as the TFA salt (50 mg, 48%). LCMS: 328 (M+H); 1H-NMR (DMSO-d6): 9.95 (s, 1H), 9.40 (s, 1H), 9.12 (s, 1H), 8.74 (m, 2H), 8.28 (s, 1H), 7.99 (t, 1H, J=7.81 Hz), 7.83 (m, 2H), 7.49 (d, 1H, J=4.77 Hz), 7.39 (dt, 1H, J=5.37 Hz), 7.04 (d, 1H, J=4.70 Hz).

Example 1563

3,3-Dimethyl-6-(7-pyridin-2-yl-pyrrolo[2,1-f][1,2,4]triazin-2-ylamino)-1,3-dihydro-indol-2-one Analogous to Example 1510b, 7-Pyridin-2-yl-pyrrolo[2,1-f][1,2,4]triazin-2-ol (50.0 mg, 0.236 mmol) and 6-Amino-3,3-dimethyl-1,3-dihydro-indol-2-one (51.9 mg, 0.294 mmol) were reacted to afford 3,3-Dimethyl-6-(7-pyridin-2-yl-pyrrolo[2,1-f][1,2,4]triazin-2-ylamino)-1,3-dihydro-indol-2-one as the TFA salt (32 mg, 28%). LCMS: 371 (M+H); 1H-NMR (DMSO-d6): 10.34 (s, 1H), 9.54 (s, 1H), 9.05 (s, 1H), 8.73 (m, 2H), 7.97 (t, 1H, J=7.92 Hz), 7.44 (m, 2H), 7.37 (m, 1H), 7.25 (d, 1H, J=7.92 Hz), 7.20 (s, 1H), 6.98 (d, 1H, J=4.84 Hz), 1.25 (s, 6H).

Example 1564

2-{4-[4-(7-Pyrazin-2-yl-pyrrolo[2,1-f][1,2,4]triazin-2-ylamino)-phenyl]-piperidin-1-yl}-acetamide 1564a) Analogous to Example 1562a, 2-Tributylstannanyl-pyrazine (0.650 mL, 2.06 mmol) and 7-Bromo-2-methylsulfanyl-pyrrolo[2,1-f][1,2,4]triazine (0.224 g, 0.916 mmol) were reacted to afford 2-Methylsulfanyl-7-pyrazin-2-yl-pyrrolo[2,1-f][1,2,4]triazine (0.100 g, 44%). 1H-NMR (DMSO-d6): 9.87 (s, 1H), 9.50 (s, 2H), 9.15 (s, 1H), 8.80 (m, 6H), 8.62 (s, 1H), 7.64 (d, 1H, J=4.96 Hz), 7.17 (d, 1H, J=4.96 Hz), 2.66 (s, 4H).

1564b) Analogous to Example 1562b, 2-Methylsulfanyl-7-pyrazin-2-yl-pyrrolo[2,1-f][1,2,4]triazine (0.100 g, 0.411 mmol) was oxidized to give 2-Methanesulfonyl-7-pyrazin-2-yl-pyrrolo[2,1-f][1,2,4]triazine, which was used in the next reaction without purification.

1564c) Analogous to Example 1562c, 2-Methanesulfonyl-7-pyrazin-2-yl-pyrrolo[2,1-f][1,2,4]triazine was oxidized to give 7-Pyrazin-2-yl-pyrrolo[2,1-f][1,2,4]triazin-2-ol (32 mg, 36% over two steps).

1564d) Analogous to Example 1510b, 7-Pyrazin-2-yl-pyrrolo[2,1-f][1,2,4]triazin-2-ol (0.0300 g, 0.141 mmol) and 2-[4-(4-Amino-phenyl)-piperidin-1-yl]-acetamide (41.0 mg, 0.176 mmol) were reacted to 2-{4-[4-(7-Pyrazin-2-yl-pyrrolo[2,1-f][1,2,4]triazin-2-ylamino)-phenyl]-piperidin-1-yl}-acetamide as the TFA salt (16 mg, 21%). LCMS: 429 (M+H); $^1$H-NMR (DMSO-d6): 9.89 (s, 1H), 9.66 (s, 1H), 9.11 (s, 1H), 8.77 (s, 1H), 8.58 (s, 1H), 7.97 (s, 1H), 7.73 (d, 2H, J=8.24 Hz), 7.47 (d, 1H, J=4.80 Hz), 7.22 (d, 2H, J=8.58 Hz), 7.02 (d, 1H, J=5.15 Hz), 3.92 (m, 2H), 3.56 (m, 2H), 1.98 (m, 4H).

Example 1565

4-{3-[7-(2-Methoxy-phenyl)-pyrrolo[2,1-f][1,2,4]triazin-2-ylamino]-phenyl}-piperidin-4-ol 1565a) 4-Oxo-piperidine-1-carboxylic acid tert-butyl ester (1.00 g, 5.02 mmol) in Tetrahydrofuran (5 mL) was cooled at −20° C. and 1.00 M of 3-[Bis(trimethylsilyl)-amino]phenyl-magnesium chloride in Tetrahydrofuran (5.52 mL, 5.52 mmol) was added dropwise via syringe. The reaction was let stir at −20° C. for 20 minutes and then allowed to warm to room temperature for 15 minutes until complete. The reaction mixture was then cooled in an ice bath and 3M HCl was added to quench excess Grignard reagent and magnesium (pH no less than 3). Aqueous sodium bicarbonate was then added to bring to pH 8 and the product was extracted with EtOAc (2×, 25 mL), combined organics extracted with brine (25 mL), dried over sodium sulfate, and conc. in vacuo. The crude product was recrystallized with hexane and cooled in the refrigerator overnight, forming crystals. The solvent was decanted and the product dried on the high vac. 1H-NMR (DMSO-d6): 6.93 (t, 1H, J=7.94 Hz), 6.69 (s, 1H), 6.58 (d, 1H, J=7.94 Hz), 6.39 (d, 1H, J=7.94 Hz), 4.93 (s, 2H), 4.83 (s, 1H), 3.80 (s, 2H), 3.09 (s, 2H), 1.70 (m, 2H), 1.53 (m, 2H), 1.41 (s, 3H).

1565b) Analogous to Example 1528d, 4-(3-Amino-phenyl)-4-hydroxy-piperidine-1-carboxylic acid tert-butyl ester (80.0 mg, 0.274 mmol) and Trifluoro-methanesulfonic acid 7-(2-methoxy-phenyl)-pyrrolo[2,1-f][1,2,4]triazin-2-yl ester (81.7 mg, 0.219 mmol) were reacted to afford 4-{3-[7-(2-Methoxy-phenyl)-pyrrolo[2,1-f][1,2,4]triazin-2-ylamino]-phenyl}-piperidin-4-ol as the TFA salt (30 mg, 25%). LCMS: 416 (M+H); 1H-NMR (DMSO-d6): 9.41 (s, 1H), 8.96 (s, 1H), 8.41 (s, 1H), 8.19 (s, 1H), 7.83 (d, 1H, J=8.42 Hz), 7.77 (d, 1H, J=7.58 Hz), 7.55 (s, 1H), 7.44 (t, 1H, J=8.00 Hz), 7.19 (m, 2H), 7.09 (t, 1H, J=7.58 Hz), 6.97 (d, 1H, J=8.00 Hz), 6.93 (m, 2H), 5.31 (s, 1H), 3.78 (s, 3H), 3.18 (s, 5H), 1.97 (s, 2H), 1.72 (m, 2H).

Example 1566

[7-(6-Methoxy-pyridin-3-yl)-pyrrolo[2,1-f][1,2,4]triazin-2-yl]-(3-piperazin-2-yl-phenyl)-amine 1566a) To a solution of Selenium dioxide (9.4 g, 85 mmol) in 1,4-Dioxane (50.0 mL) and Water (1.70 mL, 94.4 mmol), was added 3-Nitroacetophenone (12.0 g, 72.9 mmol). The reaction mixture was refluxed for 4 hours with stirring, then taken up with EtOAc (100 mL) and washed with water (2×50 mL), brine (1×50 mL), dried over sodium sulfate, filtered and conc. in vacuo. Purification was by ISCO column chromatography (20-70% EtOAc/Hex) to afford (3-Nitro-phenyl)-oxo-acetaldehyde (9.98 g, 76%).

1566b) Analogous to Example 1528a, (3-Nitro-phenyl)-oxo-acetaldehyde (7.47 g, 41.7 mmol) was converted to 2-(3-Nitro-phenyl)-piperazine oxalic acid salt (7.57 g, 61%). 1H-NMR (DMSO-d6): 8.29 (s, 1H), 8.19 (d, 1H, J=7.98 Hz), 7.85 (d, 1H, J=7.98 Hz), 7.68 (t, 1H, J=7.87), 4.06 (d, 2H, J=11.26 Hz), 3.32 (d, 1H, J=12.38 Hz), 3.18 (d, 1H, J=10.34 Hz), 3.11 (d, 1H, J=10.34 Hz), 2.93 (t, 2H, J=10.27 Hz), 2.78 (t, 1H, J=11.59 Hz), 1.03 (d, 2H, J=6.28 Hz).

1566c) Analogous to Example 1528b, 2-(3-Nitro-phenyl)-piperazine oxalic acid salt (0.500 g, 1.68 mmol) was reacted with Di-tert-Butyldicarbonate (1.00 mL, 4.35 mmol) to give 2-(3-Nitro-phenyl)-piperazine-1,4-dicarboxylic acid di-tert-butyl ester (276 mg, 40%). 1H-NMR (CDCl3): 8.22 (s, 1H), 8.14 (d, 1H, J=8.56 Hz), 7.64 (s, 1H), 7.52 (t, 1H, J=8.56 Hz), 5.35 (s, 1H), 4.54 (s, 1H), 3.97 (d, 2H, J=10.13 Hz), 3.36 (m, 1H), 2.94 (s, 2H), 1.48 (s, 9H), 1.44 (s, 9H).

1566d) Analogous to Example 1528c, reduction of 2-(3-Nitro-phenyl)-piperazine-1,4-dicarboxylic acid di-tert-butyl ester (108 mg, 0.265 mmol) gave 2-(3-Amino-phenyl)-piperazine-1,4-dicarboxylic acid di-tert-butyl ester (79 mg, 79%).

1566e) Analogous to Example 1528d, 2-(3-Amino-phenyl)-piperazine-1,4-dicarboxylic acid di-tert-butyl ester (204 mg, 0.540 mmol) and Trifluoro-methanesulfonic acid 7-(6-methoxy-pyridin-3-yl)-pyrrolo[2,1-f][1,2,4]triazin-2-yl ester (162 mg, 0.432 mmol) were reacted to afford [7-(6-Methoxy-pyridin-3-yl)-pyrrolo[2,1-f][1,2,4]triazin-2-yl]-(3-piperazin-2-yl-phenyl)-amine (75 mg, 33%) as the TFA salt. LCMS: 402 (M+H); 1H-NMR (DMSO-d6): 9.74 (s, 1H), 9.5 (br s, 3H), 9.03 (s, 1H), 9.00 (s, 1H), 8.50 (m, 1H), 7.93 (d, 1H, J=8.1 Hz), 7.65 (s, 1H), 7.48 (m, 1H), 7.26 (d, 1H, J=4.8 Hz), 7.19 (d, 1H, J=7.9 Hz), 7.03 (m, 2H), 1.41 (m, 1H), 3.94 (s, 3H), 3.71 (m, 1H), 3.60 (m, 2H), 3.2-3.4 (m, 3H).

Example 1567

N-tert-Butyl-3-{2-[4-(1,4-dimethyl-piperazin-2-yl)-phenylamino]-pyrrolo[2,1-f][1,2,4]triazin-7-yl}-benzenesulfonamide Analogous to Example 1519, N-tert-Butyl-3-[2-(4-piperazin-2-yl-phenylamino)-pyrrolo[2,1-f][1,2,4]triazin-7-yl]-benzenesulfonamide (41 mg, 0.066 mmol) was methylated to afford N-tert-Butyl-3-{2-[4-(1,4-dimethyl-piperazin-2-yl)-phenylamino]-pyrrolo[2,1-f][1,2,4]triazin-7-yl}-benzenesulfonamide as the TFA salt (26 mg, 61%). LCMS: 533 (M+H); 1H-NMR (DMSO-d6): 9.70 (s, 1H), 9.07 (s, 1H), 8.57 (s, 1H), 8.34 (d, 1H, J=7.6 Hz), 7.87 (d, 1H, J=7.9 Hz), 7.80 (d, 2H, J=8.2 Hz), 7.74 (m, 1H), 7.62 (s, 1H), 7.36 (d, 2H, J=8.2 Hz), 7.22 (d, 1H, J=4.8 Hz), 7.03 (d, 1H, J=4.8 Hz), 3.2-3.5 (m, 4H), 3.08 (m, 2H), 2.77 (m, 4H), 2.16 (br s, 3H), 1.12 (s, 9H).

Example 1568

2-{4-[4-(7-Pyrimidin-2-yl-pyrrolo[2,1-f][1,2,4]triazin-2-ylamino)-phenyl]-piperidin-1-yl}-acetamide 1568a) Analogous to Example 1562a, 2-Tributylstannanyl-pyrimidine (0.761 g, 2.06 mmol) and 7-Bromo-2-methylsulfanyl-pyrrolo[2,1-f][1,2,4]triazine (0.224 g, 0.916 mmol) were reacted to afford 2-Methylsulfanyl-7-pyrimidin-2-yl-pyrrolo[2,1-f][1,2,4]triazine (46 mg, 20%). 1H-NMR (DMSO-d6): 9.14 (s, 1H), 8.95 (d, 2H, J=4.94 Hz), 7.58 (m, 1H), 7.44 (t, 1H, J=4.83 Hz), 7.10 (d, 1H, J=4.83 Hz), 2.59 (s, 3H).

1568b) Analogous to Example 1562b, 2-Methylsulfanyl-7-pyrimidin-2-yl-pyrrolo[2,1-f][1,2,4]triazine (45.6 mg, 0.187 mmol) was oxidized to afford 2-Methanesulfonyl-7-pyrimidin-2-yl-pyrrolo[2,1-f][1,2,4]triazine.

1568c) Analogous to Example 1562c, 2-Methanesulfonyl-7-pyrimidin-2-yl-pyrrolo[2,1-f][1,2,4]triazine was hydrolyzed to afford 7-Pyrimidin-2-yl-pyrrolo[2,1-f][1,2,4]triazin-2-ol (23 mg, 58% over two steps).

1568d) Analogous to Example 1510b, 7-Pyrimidin-2-yl-pyrrolo[2,1-f][1,2,4]triazin-2-ol (23.0 mg, 0.108 mmol) and 2-[4-(4-Amino-phenyl)-piperidin-1-yl]-acetamide (31.5 mg, 0.135 mmol) were reacted to afford 2-{4-[4-(7-Pyrimidin-2-yl-pyrrolo[2,1-f][1,2,4]triazin-2-ylamino)-phenyl]-piperidin-1-yl}-acetamide as the TFA salt (2 mg, 3%). LCMS: 429 (M+H); 1H-NMR (DMSO-d6): 9.63 (s, 1H), 9.55 (br s, 1H), 9.10 (s, 1H), 9.03 (d, 2H, J=4.8 Hz), 8.18 (d, 2H, J=8.4 Hz), 7.98 (s, 1H), 7.73 (s, 1H), 7.48 (d, 1H, J=4.8 Hz), 7.44 (m, 1H), 7.23 (d, 2H, J=8.4 Hz), 6.97 (d, 1H, J=4.8 Hz), 3.92 (s, 2H), 3.15 (m, 4H), 2.76 (m, 1H), 2.00 (m, 4H).

Example 1571

[7-(4-Methanesulfonyl-phenyl)-pyrrolo[2,1-f][1,2,4]triazin-2-yl]-(4-piperidin-4-yl-phenyl)-amine 1571a) 7-Bromo-pyrrolo[2,1-f][1,2,4]triazin-2-ol: Into a round bottom flask, 7-Bromo-2-chloro-pyrrolo[2,1-f][1,2,4]triazine (5.00 g, 0.0215 mol), 50% Sodium Hydroxide (1:1 Sodium Hydroxide: Water, 50 mL, 1.0 mol) and Water (100 mL, 6 mol) were added. The reaction was stirred and heated at 120° C. for one hour. The mixture was allowed to cool to room temperature and stirred overnight. The mixture was acidified to pH2 by careful addition of concentrated Hydrochloric acid and the resulting dark brown solid was collected by filtration. The solid was washed with water then hexane to give 7-Bromo-pyrrolo[2,1-f][1,2,4]triazin-2-ol as a dark brown solid (4.60 g, 90%). LCMS (E/I+) 215 (M+H). NMR $^1$H (DSMO-d$_6$)-12.1 (s, 1H), 8.93 (s, 1H), 7.02 (d, 2H, J=5.1 Hz), 6.96 (d, 1H, J=4.88 Hz), 2.98 (s, 3H)

1571b) 2-(7-amino-1,2,4,5-tetrahydro-benzo[d]azepin-3-yl)-N,N-dimethyl-acetamide Into a round bottom flask, 7-Nitro-2,3,4,5-tetrahydro-1H-benzo[d]azepine nitric acid salt (3.80 g, 0.0149 mol), Potassium Carbonate (6.22 g, 0.0450 mol), 2-Chloro-N,N-dimethyl-acetamide (2.30 mL, 0.00224 mol), Sodium Iodide (2.28 g, 0.0152 mol) and DMF (60 mL, 0.8 mol) were added. The mixture was heated at 60° C. overnight. The reaction was partitioned with EtOAc and washed with Water (2×). The organic was separated, washed with Brine, and dried over Sodium Sulfate. The solid was filtered and washed with EtOAc. The solvent was removed under vacuum. The product was isolated via ISCO column chromatography with DCM and Methanol as eluant (0 to 10% Methanol). The collected fractions afforded 2-(7-nitro-1,2,4,5-tetrahydro-benzo[d]azepin-3-yl)-N,N-dimethyl-acetamide as an orange solid (2.31 g, 56%). MP 102-104° C. LCMS (E/I+) 278 (M+H). NMR $^1$H (CDCl$_3$)-7.95 (m, 2H), 7.24 (d, 1H, J=7.76 Hz), 3.34 st, 2H), 3.12 (s, 3H), 3.03 (m, 4H), 2.97 (s, 3H), 2.76 (m, 4H).

1571c) Into a Parr bottle, N,N-Dimethyl-2-(7-nitro-1,2,4,5-tetrahydro-benzo[d]azepin-3-yl)-acetamide (2.20 g, 0.0079 mol), 10% Palladium on Carbon (50% Wet)(5:45:50, Palladium:carbon black:Water, 0.84 g, 0.0004 mol) and Methanol (50 mL, 1 mol) were added. The mixture was evacuated and charged with hydrogen at 40 psi. The reaction was shaken on the parr at 40 psi for one hour. The mixture was filtered through Celite and the Celite washed with EtOAc. The organic was evaporated under vacuum to give N,N-Dimethyl-2-(7-amino-1,2,4,5-tetrahydro-benzo[d]azepin-3-yl)-acetamide as a brown gum/foam (1.96 g, 112%). LCMS (E/I+) 248 (M+H). NMR $^1$H (DSMO-d$_6$)-9.90 (br. s, 2H), 7.22 (d, 1H, J=8.14 Hz), 7.06 (m, 2H), 4.36 (s, 2H), 3.66 (br. m, 4H), 3.12 (br. m, 4H), 2.96 (s, 3H), 2.91 (s, 3H).

1571d) To a round bottom flask, 7-Bromo-pyrrolo[2,1-f][1,2,4]triazin-2-ol (0.593 g, 0.00277 mol), DIEA (1.50 mL, 0.0086 mol) and DMF (25 mL, 0.32 mol) were added. The mixture was stirred at room temperature and N-Phenylbis(trifluoromethanesulfonimide) (1.14 g, 0.00320 mol) was added. The mixture was stirred at room temperature for 1 h then 4-(4-Amino-phenyl)-piperidine-1-carboxylic acid tert butyl ester (0.995 g, 0.00361 mol) was added and the mixture stirred at 60° C. for 4 h. The solvent was removed under vacuum. The product was isolated via ISCO column chromatography with a 2:1 Hexane/DCM and Methanol as eluant (0 to 10% Methanol). The collected fractions gave 4-[4-(7-Bromo-pyrrolo[2,1-f][1,2,4]-triazin-2ylamino)-phenyl]-piperidine-1-carboxylic acid tert butyl ester as a pale solid (~2:1 P: SM by NMR). LCMS (E/I+) 472 (M+H). ii) To a round bottom flask, Palladium Acetate (0.083 g, 0.000368 mol) and Triphenylphosphine (0.144 g, 0.000551 mol) and THF (6 mL, 0.070 mol) were added and purged under an atmosphere of Nitrogen for 10 minutes. A solution of 4-[4-(7-Bromo-pyrrolo[2,1-f][1,2,4]-triazin-2ylamino)-phenyl]-piperidine-1-carboxylic acid tert butyl ester (70% pure, 1.24 g, 0.00184 mol) in THF (4 mL, 0.050 mol) was added and the reaction was stirred for a further 10 minutes. 4-(Methylsulfonylphenyl)boronic acid (0.735 g, 0.00368 mol), Ethanol (10 mL, 0.20 mol) and 0.90 M Sodium carbonate in Water (6.12 mL, 0.00551 mol) were added and the mixture was heated at 80° C. overnight. The reaction was partitioned with aqueous Sodium Carbonate and EtOAc. The organic was separated, washed with Brine, and dried over Sodium Sulfate. The solid was filtered and washed with EtOAc. The solvent was removed under vacuum. The product was isolated via ISCO column chromatography with DCM and MeOH as eluant (0 to 10%). The collected fractions afforded 4-{4-[7-(4-Methanesulfonyl-phenyl)-pyrrolo[2,1-f][1,2,4]-triazin-2ylamino)-phenyl}-piperidine-1-carboxylic acid tert butyl ester as a yellow solid (0.762 g, 75% pure by NMR). LCMS (E/I+) 570 (M+Na).

1571e) To a round bottom flask 4-{4-[7-(4-Methanesulfonyl-phenyl)-pyrrolo[2,1-f][1,2,4]-triazin-2ylamino)-phenyl}-piperidine-1-carboxylic acid tert butyl ester (7-% pure, 0.762 g, 0.00135 mol) and 3.0 M Trifluoroacetic acid in DCM (10 mL, 0.030 mol) were added. The mixture was stirred at room temperature for 1 h then the solvent was removed by rotary evaporation. The crude product was purified via HPLC reverse phase chromatography with 0.1% TFA in Water and 0.1% TFA in ACN. The collected fractions were lyophilized to give [7-(4-Methanesulfonyl-phenyl)-pyrrolo[2,1-f][1,2,4]triazin-2-yl]-(4-piperidin-4-yl-phenyl)-amine; compound with trifluoro-acetic acid as a yellow fluffy solid (0.06 g, 10%). LCMS (E/I+) 448.1 (M+H). NMR $^1$H (CDCl$_3$/DSMO-d$_6$)-9.97 (s, 1H), 9.50 (s, 1H), 8.41 (d, 2H, J=8.52 Hz), 8.20 (s, 1H), 8.02 (d, 2H, J=8.51 Hz), 7.67 (d, 2H, J=8.67 Hz), 7.20 (d, 2H, J=7.6 Hz), 7.11 (d, 1H, J=4.90 Hz), 6.88 (d, 1H, J=4.88 Hz), 3.54 (d, 2H, J=12.06 Hz), 3.14 (s, 3H), 3.02 (m, 3H), 2.59 (m, 2H), 2.05 (m, 4H).

Example 1572

2-{7-[7-(2-Methoxy-pyridin-3-yl)-pyrrolo[2,1-f][1,2,4]triazin-2-yl]-amino]-1,2,4,5-tetrahydro-benzo[d]azepin-3-yl)-N,N-dimethyl-acetamide To a round bottom flask, Palladium Acetate (0.009 g, 0.00002 mol) and Triphenylphosphine (0.016 g, 0.00003 mol) and THF (2 mL, 0.02 mol) were added and purged under an atmosphere of Nitrogen for 10 minutes. A solution of 2-[7-(7-Bromo-pyrrolo[2,1-f][1,2,4]triazin-2-yl]-amino)-1,2,4,5-tetrahydro-benzo[d]azepin-3-yl]-N,N-dimethyl-acetamide (0.089 g, 0.0002 mol) in THF (1 mL, 0.010 mol) was added and the reaction was stirred for a further 10 minutes. 2-Methoxy-3-pyridineboronic acid (0.046 g, 0.0003 mol), Ethanol (2.5 mL, 0.043 mol) and 0.90 M Sodium carbonate in Water (0.67 mL, 0.0006 mol) were added and the mixture was heated at 80° C. overnight. The mixture was filtered through celite and washed with EtOAc. The filtrate was concentrated by rotary evaporation and the crude product was purified via HPLC reverse phase chromatography with 0.1% TFA in Water and 0.1% TFA in ACN. The collected fractions were lyophilized to give 2-{7-[7-(2-Methoxy-pyridin-3-yl)-pyrrolo[2,1-f][1,2,4]triazin-2-yl]-amino]-1,2,4,5-tetrahydro-benzo[d]azepin-3-yl)-N,N-dimethyl-acetamide; compound with TFA as a yellow orange solid (0.025 g, 26%). LCMS (E/I+) 472 (M+H). NMR $^1$H (DSMO-$d_6$)-9.85 (s, 1H), 9.51 (s, 1H), 9.01 (s, 1H), 8.34 (d, 1H, J=7.32 Hz), 8.28 (s, 1H), 7.61 (s, 1H), 7.43 (d, 1H, J=9.1 Hz), 7.18 (m, 1H), 7.06 (m, 2H), 6.96 (m, 1H (, 4.30 (s, 2H), 3.91 (s, 3H), 3.62 (m, 2H), 3.26 (m, 2H). 3.08 (m, 3H), 2.95 (s, 6H), 2.81 (m, 1H).

Example 1573

2-{7-[7-(2-Methoxy-pyridin-3-yl)-pyrrolo[2,1-f][1,2,4]triazin-2-yl]-amino]-1,2,4,5-tetrahydro-benzo[d]azepin-3-yl)-N,N-dimethyl-acetamide The titled compound was prepared in an analogous fashion to Example 1572 replacing 2-Methoxy-3-pyridineboronic acid with 2-Methoxy-4-pyridineboronic acid to give 2-{7-[7-(2-Methoxy-pyridin-3-yl)-pyrrolo[2,1-f][1,2,4]triazin-2-yl]-amino]-1,2,4,5-tetrahydro-benzo[d]azepin-3-yl)-N,N-dimethyl-acetamide as a fluffy yellow solid (0.034 g, 34%). LCMS (E/I+) 472 (M+H). NMR $^1$H (DSMO-$d_6$)-9.85 (s, 1H), 9.66 (s, 1H), 9.08 (s, 1H), 8.26 (d, 1H, J=4.8 Hz), 7.81 (d, 1H, J=6.13 Hz), 7.73 (d, 1H, J=5.6 Hz), 7.40 (m, 1H), 7.17 (d, 1H, J=7.80 Hz), 7.00 (d, 1H, J=4.0 Hz), 4.36 (s, 2H), 3.94 (s, 3H), 3.66 (m, 2H), 3.22 (m, 6H), 2.95 (s, 6H).

Example 1574

2-[7-(7-Bromo-pyrrolo[2,1-f][1,2,4]triazin-2-yl]-amino)-1,2,4,5-tetrahydro-benzo[d]azepin-3-yl]-N,N-dimethyl-acetamide To a round bottom flask, 7-Bromo-pyrrolo[2,1-f][1,2,4]triazin-2-ol (1.070 g, 0.005 mol), DIEA (2.61 mL, 0.015 mol) and DMF (40 mL, 0.50 mol) were added. The mixture was stirred at room temperature and N-Phenylbis(trifluoromethanesulfonimide) (1.965 g, 0.0055 mol) was added. The mixture was stirred at room temperature for 1 h then 2-(7-amino-1,2,4,5-tetrahydro-benzo[d]azepin-3-yl)-N,N-dimethyl-acetamide (1.36 g, 0.0055 mol) was added and the mixture stirred at 60° C. for 4 h. The solvent was removed under vacuum. The product was isolated via ISCO column chromatography with a 2:1 Hexane/DCM and Methanol as eluant (0 to 20% Methanol). The collected fractions gave 2-[7-(7-Bromo-pyrrolo[2,1-f][1,2,4]triazin-2-yl]-amino)-1,2,4,5-tetrahydro-benzo[d]azepin-3-yl]-N,N-dimethyl-acetamide as an orange solid/foam (2.217 g, 77%). LCMS (E/I+) 443 (M+H). NMR $^1$H (CDCl$_3$)-8.56 (s, 1H), 7.56 (s, 1H), 7.48 (d, 1H, J=7.05 Hz), 7.11 (s, 1H), 7.08 (d, 1H, J=8.30 Hz), 6.74 (dd, 2H, JJ=3.84, 12.82 Hz), 3.30 (s, 2H), 3.14 (s, 3H), 2.95 (m, 7H), 2.59 (m, 2H), 2.73 (m, 4H).

Example 1575

2-{7-[7-(5-Methoxy-pyridin-3-yl)-pyrrolo[2,1-f][1,2,4]triazin-2-yl]-amino]-1,2,4,5-tetrahydro-benzo[d]azepin-3-yl)-N,N-dimethyl-acetamide The titled compound was prepared in an analogous fashion to Example 1572 replacing 2-Methoxy-3-pyridineboronic acid with 3-Methoxy-5-(4,4,5,5-tetramethyl-1,3,2-dioxaborolan-2-yl)-pyridine to give 2-{7-[7-(5-Methoxy-pyridin-3-yl)-pyrrolo[2,1-f][1,2,4]triazin-2-yl]-amino]-1,2,4,5-tetrahydro-benzo[d]azepin-3-yl)-N,N-dimethyl-acetamide as a fluffy yellow orange solid (0.060 g, 63%). LCMS (E/I+) 472 (M+H). NMR $^1$H (DSMO-$d_6$)-9.85 (s, 1H), 9.61 (s, 1H), 9.05 (s, 1H), 8.35 (s, 1H), 8.14 (s, 1H), 7.76 (s, 1H), 7.44 (d, 1H, J=7.66 Hz), 7.36 (d, 1H, J=4.80 Hz), 7.14 (d, 1H, J=8.32 Hz), 7.01 (d, 1H, J=4.48 Hz), 4.34 (s, 2H), 3.91 (s, 3H), 3.63 (m, 2H), 3.33 (m, 2H), 3.05 (m, 4H), 2.95 (s, 6H).

It is understood that the examples and embodiments described herein are for illustrative purposes only and that various modifications or changes in light thereof will be suggested to persons skilled in the art and are to be included within the spirit and purview of this application and the scope of the appended claims. All publications, patents, and patent applications cited herein are hereby incorporated by reference in their entirety for all purposes.

What is claimed is:

1. A compound of formula (I)

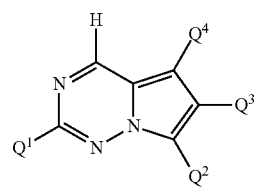

or a pharmaceutically acceptable salt form thereof,
wherein the compound has an ALK kinase $IC_{50}$ of <0.1 μM and/or a JAK2 kinase $IC_{50}$ of <0.1 μM,
and wherein
$Q^1$ is -$L^1$-$A^1$-$G^1$-$X^1$—$Z^1$;
$Q^2$ is -$L^2$-$A^2$-$G^2$-$X^2$—$Z^2$;
$Q^3$ is -$L^3$-$A^3$-$G^3$-$X^3$—$Z^3$;
$Q^4$ is -$L^4$-$A^4$-$G^4$-$X^4$—$Z^4$;
$L^1$ is $C_{1-6}$alkylene optionally substituted by 1-12 $R^9$, $C_{2-6}$alkenylene optionally substituted by 1-10 $R^9$, $C_{2-6}$alkynylene optionally substituted by 1-8 $R^9$, $C_{6-11}$arylene optionally substituted by 1-10 $R^9$, $C_{7-16}$arylalkylene optionally substituted by 1-18 $R^9$, $C_{3-11}$cycloalkylene optionally substituted by 1-20 $R^9$, $C_{4-17}$cycloalkylalkylene optionally substituted by 1-31 $R^9$, 3-15 membered heterocycloalkylene optionally substituted by 1-27 $R^9$, 4-21 membered heterocycloalkylalkylene optionally substituted by 1-39 $R^9$, 5-15 membered heteroarylene optionally substituted by 1-14 $R^9$, 6-21 membered heteroarylalkylene optionally substituted by 1-26 $R^9$, —$C_{0-3}$alkylC(=O)$C_{0-3}$alkyl-, —$C_{0-3}$alkylC(=O)O$C_{0-3}$alkyl-, —$C_{0-3}$alkylC(=O)NR$^4$$C_{0-3}$alkyl-, —$C_{0-3}$alkylC(=O)C(=O)$C_{0-3}$alkyl-, —$C_{0-3}$alkylC(=NR$^5$)$C_{0-3}$alkyl-, —$C_{0-3}$alkylC(=NR$^5$)NR$^4$$C_{0-3}$alkyl-, —$C_{0-3}$alkylC(=NOH)NR$^4$$C_{0-3}$alkyl-, —$C_{0-3}$alkylC(=NOR$^6$)$C_{0-3}$alkyl-, —$C_{0-3}$alkylC(=NNR$^2$R$^3$)$C_{0-3}$alkyl-, —$C_{0-3}$alkylC(=NNR$^4$C(=O)R$^1$)$C_{0-3}$ alkyl-, —$C_{0-3}$alkylC(=NNR$^4$C(=O)OR$^1$)$C_{0-3}$ alkyl-, —$C_{0-3}$alkylC(=S)NR$^4$$C_{0-3}$alkyl-, —$C_{0-3}$alkylNR$^4$$C_{0-3}$alkyl-, —$C_{0-3}$alkylNR$^4$NR$^4$$C_{0-3}$ alkyl-, —$C_{0-3}$alkylN=N$C_{0-3}$alkyl-, —$C_{0-3}$ alkylNR$^4$C(=O)$C_{0-3}$alkyl-, —$C_{0-3}$alkylNR$^4$C(=O)C(=O) $C_{0-3}$ alkyl-, —$C_{0-3}$alkylNR$^4$C(=O)O$C_{0-3}$alkyl-, —$C_{0-3}$ alkylNR$^4$C(=O)C(=O)O$C_{0-3}$ alkyl-, —$C_{0-3}$ alkylNR$^4$C(=O)NR$^4$$C_{0-3}$alkyl-, —$C_{0-3}$alkylNR$^4$C (=O)NR⁴C(=O)C₀₋₃alkyl-, —C₀₋₃alkylNR⁴C(=O)NR⁴C(=O)OC₀₋₃alkyl-, —C₀₋₃alkylNR⁴C(=NR⁵)NR⁴C₀₋₃alkyl-, —C₀₋₃alkylNR⁴C(=O)NR⁴C₀₋₃alkyl-, —C₀₋₃alkylNR⁴C(=S)C₀₋₃alkyl-, —C₀₋₃alkylNR⁴C(=S)OC₀₋₃alkyl-, —C₀₋₃alkylNR⁴C(=S)NR⁴C₀₋₃alkyl-, —C₀₋₃alkylNR⁴S(=O)₂C₀₋₃alkyl-, —C₀₋₃alkylNR⁴S(=O)₂NR⁴C₀₋₃alkyl-, —C₀₋₃alkylOC₀₋₃alkyl-, —C₀₋₃alkylOC(=O)C₀₋₃alkyl-, —C₀₋₃alkylOC(=O)NR⁴C₀₋₃alkyl-, —C₀₋₃alkylOC(=O)OC₀₋₃alkyl-, —C₀₋₃alkylOC(=NR⁵)NR⁴C₀₋₃alkyl-, —C₀₋₃alkylOS(=O)C₀₋₃alkyl-, —C₀₋₃alkylOS(=O)₂C₀₋₃alkyl-, —C₀₋₃alkylOS(=O)₂OC₀₋₃alkyl-, —C₀₋₃alkylOS(=O)₂NR⁴C₀₋₃alkyl-, —C₀₋₃alkylS(=O)ₙC₀₋₃alkyl-, —C₀₋₃alkylS(=O)₂OC₀₋₃alkyl-, —C₀₋₃alkylSO₃C₀₋₃alkyl-, —C₀₋₃alkylS(=O)₂NR⁴C₀₋₃alkyl-, —C₀₋₃alkylS(=O)NR⁴C₀₋₃alkyl-, or absent;

A¹ is C₁₋₆alkylene optionally substituted by 1-12 Rᵃ, C₂₋₆alkenylene optionally substituted by 1-10 Rᵃ, C₂₋₆alkynylene optionally substituted by 1-8 Rᵃ, C₆₋₁₁arylene optionally substituted by 1-10 Rᵃ, C₇₋₁₆arylalkylene optionally substituted by 1-18 Rᵃ, C₃₋₁₁cycloalkylene optionally substituted by 1-20 Rᵃ, C₄₋₁₇cycloalkylalkylene optionally substituted by 1-31 Rᵃ, 3-15 membered heterocycloalkylene optionally substituted by 1-27 Rᵃ, 4-21 membered heterocycloalkylalkylene optionally substituted by 1-39 Rᵃ, 5-15 membered heteroarylene optionally substituted by 1-14 Rᵃ, or 6-21 membered heteroarylalkylene optionally substituted by 1-26 Rᵃ, wherein each Rᵃ is independently chosen from C₁₋₆alkyl optionally substituted by 1-13 R¹⁹, C₂₋₆alkenyl optionally substituted by 1-11 R¹⁹, C₂₋₆alkynyl optionally substituted by 1-9 R¹⁹, C₆₋₁₁aryl optionally substituted by 1-11 R¹⁹, C₇₋₁₆arylalkyl optionally substituted by 1-19 R¹⁹, C₃₋₁₁cycloalkyl optionally substituted by 1-21 R¹⁹, C₄₋₁₇cycloalkylalkyl optionally substituted by 1-32 R¹⁹, 3-15 membered heterocycloalkyl optionally substituted by 1-28 R¹⁹, 4-21 membered heterocycloalkylalkyl optionally substituted by 1-40 R¹⁹, 5-15 membered heteroaryl optionally substituted by 1-15 R¹⁹, 6-21 membered heteroarylalkyl optionally substituted by 1-27 R¹⁹, halogen, —CN, —C(=O)R¹⁰, —C(=O)OR¹⁰, —C(=O)NR¹²R¹³, —C(=O)R¹⁰, —C(=NR¹⁵)R¹⁰, —C(=NR¹⁵)NR¹²R¹³, —C(=NOH)NR¹²R¹³, —C(NOR¹⁶)R¹⁰, —C(=NNR¹²R¹³)R¹⁰, —C(=NNR¹⁴C(=O)R¹¹)R¹⁰, —C(=NNR¹⁴C(=O)OR¹¹)R¹⁰, —C(=S)NR¹²R¹³, —NC, —NO₂, —NR¹²R¹³, —NR¹⁴NR¹²R¹³, —N=NR¹⁴, =NR¹⁰, =NOR¹⁰, —NR¹⁴OR¹⁶, —NR¹⁴C(=O)R¹⁰, —NR¹⁴C(=O)C(=O)R¹⁰, —NR¹⁴C(=O)OR¹¹, —NR¹⁴C(=O)C(=O)OR¹¹, —NR¹⁴C(=O)NR¹²R¹³, —NR¹⁴C(=O)NR¹⁴C(=O)R¹⁰, —NR¹⁴C(=O)NR¹⁴C(=O)OR¹⁰, —NR¹⁴C(=NR¹⁵)NR¹²R¹³, —NR¹⁴C(=O)C(=O)NR¹²R¹³, —NR¹⁴C(=S)R¹⁰, —NR¹⁴C(=S)OR¹⁰, —NR¹⁴C(=S)NR¹²R¹³, —NR¹⁴S(=O)₂R¹¹, —NR¹⁴S(=O)₂NR¹²R¹³, —NR¹⁴P(=O)R¹⁸R¹⁸, —NR¹⁴P(=O)(NR¹²R¹³)(NR¹²R¹³), —NR¹⁴P(=O)(OR¹⁰)(OR¹⁰), —NR¹⁴P(=O)(SR¹⁰)(SR¹⁰), —OR¹⁰, =O, —OCN, —OC(=O)R¹⁰, —OC(=O)NR¹²R¹³, —OC(=O)OR¹⁰, —OC(=NR¹⁵)NR¹²R¹³, —OS(=O)R¹⁰, —OS(=O)₂R¹⁰, —OS(=O)₂OR¹⁰, —OS(=O)₂NR¹²R¹³, —OP(=O)R¹⁸R¹⁸, —OP(=O)(NR¹²R¹³)(NR¹²R¹³), —OP(=O)(OR¹⁰)(OR¹⁰), —OP(=O)(SR¹⁰)(SR¹⁰), —SCN, =S, —S(=O)ₙR¹⁰, —S(=O)₂OR¹⁰, —SO₃R¹⁷, —S(=O)₂NR¹²R¹³, —S(=O)NR¹²R¹³, —SP(=O)R¹⁸R¹⁸, —SP(=O)(NR¹²R¹³)(NR¹²R¹³), —SP(=O)(OR¹⁰)(OR¹⁰), —SP(=O)(SR¹⁰)(SR¹⁰), —P(=O)R¹⁸R¹⁸, —P(=O)(NR¹²R¹³)(NR¹²R¹³), —P(=O)(OR¹⁰)(OR¹⁰), and —P(=O)(SR¹⁰)(SR¹⁰);

G¹ is C₁₋₆alkylene optionally substituted by 1-12 R²⁹, C₂₋₆alkenylene optionally substituted by 1-10 R²⁹, C₂₋₆alkynylene optionally substituted by 1-8 R²⁹, C₆₋₁₁arylene optionally substituted by 1-10 R²⁹, C₇₋₁₆arylalkylene optionally substituted by 1-18 R²⁹, C₃₋₁₁cycloalkylene optionally substituted by 1-20 R²⁹, C₄₋₁₇cycloalkylalkylene optionally substituted by 1-31 R²⁹, 3-15 membered heterocycloalkylene optionally substituted by 1-27 R²⁹, 4-21 membered heterocycloalkylalkylene optionally substituted by 1-39 R²⁹, 5-15 membered heteroarylene optionally substituted by 1-14 R²⁹, 6-21 membered heteroarylalkylene optionally substituted by 1-26 R²⁹, —C₀₋₃alkylC(=O)C₀₋₃alkyl-, —C₀₋₃alkylC(=O)OC₀₋₃alkyl-, —C₀₋₃alkylC(=O)NR²⁴C₀₋₃alkyl-, —C₀₋₃alkylC(=O)C(=O)C₀₋₃alkyl-, —C₀₋₃alkylC(=NR²⁵)C₀₋₃alkyl-, —C₀₋₃alkylC(=NR²⁵)NR²⁴C₀₋₃alkyl-, —C₀₋₃alkylC(=NOH)NR²⁴C₀₋₃alkyl-, —C₀₋₃alkylC(=NOR²⁶)C₀₋₃alkyl-, —C₀₋₃alkylC(=NNR²²R²³)C₀₋₃alkyl-, —C₀₋₃alkylC(=NNR²⁴C(=O)R²¹)C₀₋₃alkyl-, —C₀₋₃alkylC(=NNR²⁴C(=O)OR²¹)C₀₋₃alkyl-, —C₀₋₃alkylC(=S)NR²⁴C₀₋₃alkyl-, —C₀₋₃alkylNR²⁴C₀₋₃alkyl-, —C₀₋₃alkylNR²⁴NR²⁴C₀₋₃alkyl-, —C₀₋₃alkylN=NC₀₋₃alkyl-, —C₀₋₃alkylNR²⁴C(=O)C₀₋₃alkyl-, —C₀₋₃alkylNR²⁴C(=O)C(=O)C₀₋₃alkyl-, —C₀₋₃alkylNR²⁴C(=O)OC₀₋₃alkyl-, —C₀₋₃alkylNR²⁴C(=O)C(=O)OC₀₋₃alkyl-, —C₀₋₃alkylNR²⁴C(=O)NR²⁴C₀₋₃alkyl-, —C₀₋₃alkylNR²⁴C(=O)NR²⁴C(=O)C₀₋₃alkyl-, —C₀₋₃alkylNR²⁴C(=O)NR²⁴C(=O)OC₀₋₃alkyl-, —C₀₋₃alkylNR²⁴C(=NR²⁵)NR²⁴C₀₋₃alkyl-, —C₀₋₃alkylNR²⁴C(=O)C(=O)NR²⁴C₀₋₃alkyl-, —C₀₋₃alkylNR²⁴C(=S)C₀₋₃alkyl-, —C₀₋₃alkylNR²⁴C(=S)OC₀₋₃alkyl-, —C₀₋₃alkylNR²⁴C(=S)NR²⁴C₀₋₃alkyl-, —C₀₋₃alkylNR²⁴S(=O)₂C₀₋₃alkyl-, —C₀₋₃alkylNR²⁴S(=O)₂NR²⁴C₀₋₃alkyl-, —C₀₋₃alkylOC₀₋₃alkyl-, —C₀₋₃alkylOC(=O)C₀₋₃alkyl-, —C₀₋₃alkylOC(=O)NR²⁴C₀₋₃alkyl-, —C₀₋₃alkylOC(=O)OC₀₋₃alkyl-, —C₀₋₃alkylOC(=NR²⁵)NR²⁴C₀₋₃alkyl-, —C₀₋₃alkylOS(=O)C₀₋₃alkyl-, —C₀₋₃alkylOS(=O)₂C₀₋₃alkyl-, —C₀₋₃alkylOS(=O)₂OC₀₋₃alkyl-, —C₀₋₃alkylOS(=O)₂NR²⁴C₀₋₃alkyl-, —C₀₋₃alkylS(=O)ₙC₀₋₃alkyl-, —C₀₋₃alkylS(=O)₂OC₀₋₃alkyl-, —C₀₋₃alkylSO₃C₀₋₃alkyl-, —C₀₋₃alkylS(=O)₂NR²⁴C₀₋₃alkyl-, —C₀₋₃alkylS(=O)NR²⁴C₀₋₃alkyl-, or absent;

X¹ is C₁₋₆alkylene optionally substituted by 1-12 R³⁹, C₂₋₆alkenylene optionally substituted by 1-10 R³⁹, C₂₋₆alkynylene optionally substituted by 1-8 R³⁹, C₆₋₁₁arylene optionally substituted by 1-10 R³⁹, C₇₋₁₆arylalkylene optionally substituted by 1-18 R³⁹, C₃₋₁₁cycloalkylene optionally substituted by 1-20 R³⁹, C₄₋₁₇cycloalkylalkylene optionally substituted by 1-31 R³⁹, 3-15 membered heterocycloalkylene optionally substituted by 1-27 R³⁹, 4-21 membered heterocycloalkylalkylene optionally substituted by 1-39 R³⁹, 5-15 membered heteroarylene optionally substituted by 1-14 $R^{39}$, 6-21 membered heteroarylalkylene optionally substituted by 1-26 $R^{39}$, $-C_{0-3}$alkylC(=O)$C_{0-3}$alkyl-, $-C_{0-3}$alkylC(=O)O$C_{0-3}$alkyl-, $-C_{0-3}$alkylC(=O)N$R^{34}C_{0-3}$alkyl-, $-C_{0-3}$alkylC(=O)C(=O)$C_{0-3}$alkyl-, $-C_{0-3}$alkylC(=N$R^{35}$)$C_{0-3}$alkyl-, $-C_{0-3}$alkylC(=N$R^{35}$)N$R^{34}C_{0-3}$ alkyl-, $-C_{0-3}$alkylC(=NOH)N$R^{34}C_{0-3}$ alkyl-, $-C_{0-3}$alkylC(=NO$R^{36}$)$C_{0-3}$alkyl-, $-C_{0-3}$alkylC(=NN$R^{32}R^{33}$)$C_{0-3}$alkyl-, $-C_{0-3}$alkylC(=NN$R^{34}$C(=O)$R^{31}$)$C_{0-3}$alkyl-, $-C_{0-3}$alkylC(=NN$R^{34}$C(=O)O$R^{31}$)$C_{0-3}$alkyl-, $-C_{0-3}$alkylC(=S)N$R^{34}C_{0-3}$ alkyl-, $-C_{0-3}$alkylN$R^{34}C_{0-3}$alkyl-, $-C_{0-3}$ alkylN$R^{34}$N$R^{34}C_{0-3}$alkyl-, $-C_{0-3}$alkylN=N$C_{0-3}$ alkyl-, $-C_{0-3}$alkylN$R^{34}$C(=O)$C_{0-3}$alkyl-, $-C_{0-3}$ alkylN$R^{34}$C(=O)C(=O)$C_{0-3}$alkyl-, $-C_{0-3}$alkylN$R^{34}$C(=O)O$C_{0-3}$alkyl-, $-C_{0-3}$alkylN$R^{34}$C(=O)C(=O)O$C_{0-3}$alkyl-, $-C_{0-3}$alkylN$R^{34}$C(=O)N$R^{34}C_{0-3}$alkyl-, $-C_{0-3}$alkylN$R^{34}$C(=O)N$R^{34}$C(=O)$C_{0-3}$alkyl-, $-C_{0-13}$alkylN$R^{34}$C(=O)N$R^{34}$C(=O)O$C_{0-3}$alkyl-, $-C_{0-3}$alkylN$R^{34}$C(=N$R^{35}$)N$R^{34}C_{0-3}$alkyl-, $-C_{0-3}$alkylN$R^{34}$C(=O)C(=O)N$R^{34}C_{0-3}$alkyl-, $-C_{0-3}$alkylN$R^{34}$C(=S)$C_{0-3}$alkyl-, $-C_{0-3}$alkylN$R^{34}$C(=S)O$C_{0-3}$alkyl-, $-C_{0-3}$ alkylN$R^{34}$C(=S)N$R^{34}C_{0-3}$ alkyl-, $-C_{0-3}$ alkylN$R^{34}$S(=O)$_2C_{0-3}$ alkyl-, $-C_{0-3}$ alkylN$R^{34}$S(=O)$_2$N$R^{34}C_{0-3}$alkyl-, $-C_{0-3}$ alkylO$C_{0-3}$alkyl-, $-C_{0-3}$alkylOC(=O)$C_{0-3}$alkyl-, $-C_{0-3}$alkylOC(=O)N$R^{34}C_{0-3}$alkyl-, $-C_{0-3}$alkylOC(=O)O$C_{0-3}$ alkyl-, $-C_{0-3}$alkylOC(=N$R^{35}$)N$R^{34}C_{0-3}$alkyl-, $-C_{0-3}$alkylOS(=O)$C_{0-3}$ alkyl-, $-C_{0-3}$alkylOS(=O)$_2C_{0-3}$alkyl-, $-C_{0-3}$ alkylOS(=O)$_2$O$C_{0-3}$alkyl-, $-C_{0-3}$alkylOS(=O)$_2$ N$R^{34}C_{0-3}$alkyl-, $-C_{0-3}$alkylS(=O)$_nC_{0-3}$alkyl-, $-C_{0-3}$alkylS(=O)$_2$O$C_{0-3}$alkyl-, $-C_{0-3}$alkylSO$_3C_{0-3}$ alkyl-, $-C_{0-3}$alkylS(=O)$_2$ N$R^{34}C_{0-3}$alkyl-, $-C_{0-3}$ alkylS(=O)N$R^{34}C_{0-3}$ alkyl-, or absent;

$Z^1$ is H, $C_{1-6}$alkyl optionally substituted by 1-13 $R^{49}$, $C_{2-6}$alkenyl optionally substituted by 1-11 $R^{49}$, $C_{2-6}$alkynyl optionally substituted by 1-9 $R^{49}$, $C_{6-11}$aryl optionally substituted by 1-11 $R^{49}$, $C_{7-16}$arylalkyl optionally substituted by 1-19 $R^{49}$, $C_{3-11}$cycloalkyl optionally substituted by 1-21 $R^{49}$, $C_{4-17}$cycloalkylalkyl optionally substituted by 1-32 $R^{49}$, 3-15 membered heterocycloalkyl optionally substituted by 1-28 $R^{49}$, 4-21 membered heterocycloalkylalkyl optionally substituted by 1-40 $R^{49}$, 5-15 membered heteroaryl optionally substituted by 1-15 $R^{49}$, 6-21 membered heteroarylalkyl optionally substituted by 1-27 $R^{49}$, halogen, $-CN$, $-C(=O)R^{100}$, $-C(=O)OR^{100}$, $-C(=O)NR^{102}R^{103}$, $-C(=O)C(=O)R^{100}$, $-C(=NR^{105})R^{100}$, $-C(=NR^{105})NR^{102}R^{103}$, $-C(=NOH)NR^{102}R^{103}$, $-C(=NOR^{106})R^{100}$, $-C(=NNR^{102}R^{103})R^{100}$, $-C(=NNR^{104}C(=O)R^{101})R^{100}$, $-C(=NNR^{104}C(=O)OR^{101})R^{100}$, $-C(=S)NR^{102}R^{103}$, $-NC$, $-NO_2$, $-NR^{102}R^{103}$, $-NR^{104}NR^{102}R^{103}$, $-N=NR^{104}$, $=NR^{100}$, $=NOR^{100}$, $-NR^{104}OR^{106}$, $-NR^{104}C(=O)R^{100}$, $-NR^{104}C(=O)C(=O)R^{100}$, $-NR^{104}C(=O)OR^{101}$, $-NR^{104}C(=O)C(=O)OR^{101}$, $-NR^{104}C(=O)NR^{102}R^{103}$, $-NR^{104}C(=O)NR^{104}C(=O)R^{100}$, $-NR^{104}C(=O)NR^{104}C(=O)OR^{100}$, $-NR^{104}C(NR^{105})NR^{102}R^{103}$, $-NR^{104}C(=O)NR^{102}R^{103}$, $-NR^{104}C(=S)R^{100}$, $-NR^{104}C(=S)OR^{100}$, $-NR^{104}C(=S)NR^{102}R^{103}$, $-NR^{104}S(=O)_2R^{101}$, $-NR^{104}S(=O)_2NR^{102}R^{103}$, $-NR^{104}P(=O)R^{108}R^{108}$, $-NR^{104}P(=O)(NR^{102}R^{103})(NR^{102}R^{103})$, $-NR^{104}P(=O)(OR^{100})(OR^{100})$, $-NR^{104}P(=O)(SR^{100})(SR^{100})$, $-OR^{100}$, $=O$, $-OCN$, $-OC(=O)R^{100}$, $-OC(=O)NR^{102}R^{103}$, $-OC(=O)OR^{100}$, $-OC(=NR^{105})NR^{102}R^{103}$, $-OS(=O)R^{100}$, $-OS(=O)_2R^{100}$, $-OS(=O)_2OR^{100}$, $-OS(=O)_2NR^{102}R^{103}$, $-OP(=O)R^{108}R^{108}$, $-OP(=O)(NR^{102}R^{103})(NR^{102}R^{103})$, $-OP(=O)(OR^{100})(OR^{100})$, $-OP(=O)(SR^{100})(SR^{100})$, $-SCN$, $=S$, $-S(=O)_nR^{100}$, $-S(=O)_2OR^{100}$, $-SO_3R^{107}$, $-S(=O)_2NR^{102}R^{103}$, $-S(=O)NR^{102}R^{103}$, $-SP(=O)R^{108}R^{108}$, $-SP(=O)(NR^{102}R^{103})(NR^{102}R^{103})$, $-SP(=O)(OR^{100})(OR^{100})$, $-SP(=O)(SR^{100})(SR^{100})$, $-P(=O)R^{108}R^{108}$, $-P(=O)(NR^{102}R^{103})(NR^{102}R^{103})$, $-P(=O)(OR^{100})(OR^{100})$, or $-P(=O)(SR^{100})(SR^{100})$;

$L^2$, $L^3$, and $L^4$ are independently present or absent, and if present each is independently chosen from $-C_{0-3}$alkylC(=O)$C_{0-3}$alkyl-, $-C_{0-3}$alkylC(=O)O$C_{0-3}$alkyl-, $-C_{0-3}$alkylC(=O)N$R^{44}C_{0-3}$alkyl-, $-C_{0-3}$alkylC(=O)C(=O)$C_{0-3}$alkyl-, $-C_{0-3}$alkylC(=N$R^{45}$)$C_{0-3}$alkyl-, $-C_{0-3}$alkylC(=N$R^{45}$)N$R^{44}C_{0-3}$ alkyl-, $-C_{0-3}$alkylC(=NOH)N$R^{44}C_{0-3}$ alkyl-, $-C_{0-3}$alkylC(=NO$R^{46}$)$C_{0-3}$alkyl-, $-C_{0-3}$alkylC(=NN$R^{42}R^{43}$)$C_{0-3}$alkyl-, $-C_{0-3}$alkylC(=NN$R^{44}$C(=O)$R^{41}$)$C_{0-3}$alkyl-, $-C_{0-3}$alkylC(=NN$R^{44}$C(=O)O$R^{41}$)$C_{0-3}$alkyl-, $-C_{0-3}$alkylC(=S)N$R^{44}C_{0-3}$ alkyl-, $-C_{0-3}$alkylN$R^{44}C_{0-3}$alkyl-, $-C_{0-3}$ alkylN$R^{44}$N$R^{44}C_{0-3}$alkyl-, $-C_{0-3}$alkylN=N$C_{0-3}$ alkyl-, $-C_{0-3}$alkylN$R^{44}$C(=O)$C_{0-3}$alkyl-, $-C_{0-3}$ alkylN$R^{44}$C(=O)C(=O)$C_{0-3}$alkyl-, $-C_{0-3}$ alkylN$R^{44}$C(=O)O$C_{0-3}$alkyl-, $-C_{0-3}$alkylN$R^{44}$C(=O)C(=O)O$C_{0-3}$alkyl-, $-C_{0-3}$alkylN$R^{44}$C(=O)N$R^{44}C_{0-3}$alkyl-, $-C_{0-3}$alkylN$R^{44}$C(=O)N$R^{44}$C(=O)$C_{0-3}$alkyl-, $-C_{0-3}$alkylN$R^{44}$C(=O)N$R^{44}$C(=O)O$C_{0-3}$alkyl-, $-C_{0-3}$alkylN$R^{44}$C(=N$R^{45}$)N$R^{44}C_{0-3}$alkyl-, $-C_{0-3}$alkylN$R^{44}$C(=O)C(=O)N$R^{44}C_{0-3}$alkyl-, $-C_{0-3}$alkylN$R^{44}$C(=S)$C_{0-3}$alkyl-, $-C_{0-3}$alkylN$R^{44}$C(=S)O$C_{0-3}$alkyl-, $-C_{0-3}$ alkylN$R^{44}$C(=S)N$R^{44}C_{0-3}$ alkyl-, $-C_{0-3}$ alkylN$R^{44}$S(=O)$_2C_{0-3}$ alkyl-, $-C_{0-3}$ alkylN$R^{44}$S(=O)$_2$N$R^{44}C_{0-3}$alkyl-, $-C_{0-3}$ alkylO$C_{0-3}$alkyl-, $-C_{0-3}$alkylOC(=O)$C_{0-3}$alkyl-, $-C_{0-3}$alkylOC(=O)N$R^{44}C_{0-3}$alkyl-, $-C_{0-3}$alkylOC(=O)O$C_{0-3}$ alkyl-, $-C_{0-3}$alkylOC(=N$R^{45}$)N$R^{44}C_{0-3}$alkyl-, $-C_{0-3}$alkylOS(=O)$C_{0-3}$ alkyl-, $-C_{0-3}$alkylOS(=O)$_2C_{0-3}$alkyl-, $-C_{0-3}$ alkylOS(=O)$_2$O$C_{0-3}$alkyl-, $-C_{0-3}$alkylOS(=O)$_2$ N$R^{44}C_{0-3}$alkyl-, $-C_{0-3}$alkylS(=O)$_nC_{0-3}$alkyl-, $-C_{0-3}$alkylS(=O)$_2$O$C_{0-3}$alkyl-, $-C_{0-3}$alkylSO$_3C_{0-3}$ alkyl-, $-C_{0-3}$alkylS(=O)$_2$ N$R^{44}C_{0-3}$alkyl-, and $-C_{0-3}$ alkylS(=O)N$R^{44}C_{0-3}$ alkyl-;

$A^2$, $A^3$, and $A^4$ are independently present or absent, and if present each is independently chosen from $C_{1-6}$alkylene optionally substituted by 1-12 $R^b$, $C_{2-6}$alkenylene optionally substituted by 1-10 $R^b$, $C_{2-6}$alkynylene optionally substituted by 1-8 $R^b$, $C_{6-11}$arylene optionally substituted by 1-10 $R^b$, $C_{7-16}$arylalkylene optionally substituted by 1-18 $R^b$, $C_{3-11}$cycloalkylene optionally substituted by 1-20 $R^b$, $C_{4-17}$cycloalkylalkylene optionally substituted by 1-31 $R^b$, 3-15 membered heterocycloalkylene optionally substituted by 1-27 $R^b$, 4-21 membered heterocycloalkylalkylene optionally substituted by 1-39 $R^b$, 5-15 membered heteroarylene optionally substituted by 1-14 $R^b$, or 6-21 membered heteroarylalkylene optionally substituted by 1-26 $R^b$;

wherein each $R^b$ is independently chosen from $C_{1-6}$alkyl optionally substituted by 1-13 $R^{59}$, $C_{2-6}$alkenyl optionally substituted by 1-11 $R^{59}$, $C_{2-6}$alkynyl optionally substituted by 1-9 $R^{59}$, $C_{6-11}$aryl optionally substituted by 1-11 $R^{59}$, $C_{7-16}$arylalkyl optionally substituted by 1-19 $R^{59}$, $C_{3-11}$cycloalkyl optionally substituted by 1-21 $R^{59}$, $C_{4-17}$cycloalkylalkyl optionally substituted by 1-32 $R^{59}$, 3-15 membered heterocycloalkyl optionally substituted by 1-28 $R^{59}$, 4-21 membered heterocycloalkylalkyl optionally substituted by 1-40 $R^{59}$, 5-15 membered heteroaryl optionally substituted by 1-15 $R^{59}$, 6-21 membered heteroarylalkyl optionally substituted by 1-27 $R^{59}$, halogen, —CN, —C(=O)$R^{50}$, —C(=O)O$R^{50}$, —C(=O)N$R^{52}R^{53}$, —C(=O)C(=O)$R^{50}$, —C(=N$R^{55}$)$R^{50}$, —C(=N$R^{55}$)N$R^{52}R^{53}$, —C(=NOH)N$R^{52}R^{53}$, —C(=NO$R^{56}$)$R^{50}$, —C(=NN$R^{52}R^{53}$)$R^{50}$, —C(=NN$R^{54}$C(=O)$R^{51}$)$R^{50}$, —C(=NN$R^{54}$C(=O)O$R^{51}$)$R^{50}$, —C(=S)N$R^{52}R^{53}$, —NC, —NO$_2$, —N$R^{52}R^{53}$, —N$R^{54}$N$R^{52}R^{53}$, —N=N$R^{54}$, =N$R^{50}$, =NO$R^{50}$, —N$R^{54}$O$R^{56}$, —N$R^{54}$C(=O)$R^{50}$, —N$R^{54}$C(=O)C(=O)$R^{50}$, —N$R^{54}$C(=O)O$R^{51}$, —N$R^{54}$C(=O)C(=O)O$R^{51}$, —N$R^{54}$C(=O)N$R^{52}R^{53}$, —N$R^{54}$C(=O)N$R^{54}$C(=O)$R^{50}$, —N$R^{54}$C(=O)N$R^{54}$C(=O)O$R^{50}$, —N$R^{54}$C(=N$R^{55}$)N$R^{52}R^{53}$, —N$R^{54}$C(=O)C(=O)N$R^{52}R^{53}$, —N$R^{54}$C(=S)$R^{50}$, —N$R^{54}$C(=S)O$R^{50}$, —N$R^{54}$C(=S)N$R^{52}R^{53}$, —N$R^{54}$S(=O)$_2$$R^{51}$, —N$R^{54}$S(=O)$_2$N$R^{52}R^{53}$, —N$R^{54}$P(=O)$R^{58}R^{58}$, —N$R^{54}$P(=O)(N$R^{52}R^{53}$)(N$R^{52}R^{53}$), —N$R^{54}$P(=O)(O$R^{50}$)(O$R^{50}$), —N$R^{54}$P(=O)(S$R^{50}$)(S$R^{50}$), —O$R^{50}$, =O, —OCN, —OC(=O)$R^{50}$, —OC(=O)N$R^{52}R^{53}$, —OC(=O)O$R^{50}$, —OC(=N$R^{55}$)N$R^{52}R^{53}$, —OS(=O)$R^{50}$, —OS(=O)$_2R^{50}$, —OS(=O)$_2$O$R^{50}$, —OS(=O)$_2$N$R^{52}R^{53}$, —OP(=O)$R^{58}R^{58}$, —OP(=O)(N$R^{52}R^{53}$)(N$R^{52}R^{53}$), —OP(=O)(O$R^{50}$)(O$R^{50}$), —OP(=O)(S$R^{50}$)(S$R^{50}$), —SCN, =S, —S(=O)$_n$ $R^{50}$, —S(=O)$_2$O$R^{50}$, —SO$_3R^{57}$, —S(=O)$_2$ N$R^{52}R^{53}$, —S(=O)N$R^{52}R^{53}$, —SP(=O)$R^{58}R^{58}$, —SP(=O)(N$R^{52}R^{53}$)(N$R^{52}R^{53}$), —SP(=O)(O$R^{50}$)(O$R^{50}$), —SP(=O)(S$R^{50}$)(S$R^{50}$), —P(=O)$R^{58}R^{58}$, —P(=O)(N$R^{52}R^{53}$)(N$R^{52}R^{53}$), —P(=O)(O$R^{50}$)(O$R^{50}$), and —P(=O)(S$R^{50}$)(S$R^{50}$);

$G^2$, $G^3$, and $G^4$ are independently present or absent, and if present each is independently chosen from $C_{1-6}$alkylene optionally substituted by 1-12 $R^{69}$, $C_{2-6}$alkenylene optionally substituted by 1-10 $R^{69}$, $C_{2-6}$alkynylene optionally substituted by 1-8 $R^{69}$, $C_{6-11}$arylene optionally substituted by 1-10 $R^{69}$, $C_{7-16}$arylalkylene optionally substituted by 1-18 $R^{69}$, $C_{3-11}$cycloalkylene optionally substituted by 1-20 $R^{69}$, $C_{4-17}$cycloalkylalkylene optionally substituted by 1-31 $R^{69}$, 3-15 membered heterocycloalkylene optionally substituted by 1-27 $R^{69}$, 4-21 membered heterocycloalkylalkylene optionally substituted by 1-39 $R^{69}$, 5-15 membered heteroarylene optionally substituted by 1-14 $R^{69}$, 6-21 membered heteroarylalkylene optionally substituted by 1-26 $R^{69}$, —$C_{0-3}$alkylC(=O)$C_{0-3}$alkyl-, —$C_{0-3}$alkylC(=O)O$C_{0-3}$alkyl-, —$C_{0-3}$alkylC(=O)N$R^{64}C_{0-3}$alkyl-, —$C_{0-3}$alkylC(=O)C(=O)$C_{0-3}$alkyl-, —$C_{0-3}$alkylC(=N$R^{65}$)$C_{0-3}$alkyl-, —$C_{0-3}$alkylC(=N$R^{65}$)N$R^{64}C_{0-3}$ alkyl-, —$C_{0-3}$alkylC(=NOH)N$R^{64}C_{0-3}$ alkyl-, —$C_{0-3}$alkylC(=NOR$^{66}$)$C_{0-3}$alkyl-, —$C_{0-3}$alkylC(=NN$R^{62}R^{63}$)$C_{0-3}$alkyl-, —$C_{0-3}$alkylC(=NN$R^{64}$C(=O)$R^{61}$)$C_{0-3}$alkyl-, —$C_{0-3}$alkylC(=NN$R^{64}$C(=O)O$R^{61}$)$C_{0-3}$alkyl-, —$C_{0-3}$alkylC(=S)N$R^{64}C_{0-3}$alkyl-, —$C_{0-3}$alkylN$R^{64}C_{0-3}$alkyl-, —$C_{0-3}$alkylN$R^{64}$N$R^{64}C_{0-3}$alkyl-, —$C_{0-3}$alkylN=N$C_{0-3}$alkyl-, —$C_{0-3}$alkylN$R^{64}$C(=O)$C_{0-3}$alkyl-, —$C_{0-3}$alkylN$R^{64}$C(=O)C(=O)$C_{0-3}$alkyl-, —$C_{0-3}$alkylN$R^{64}$C(=O)O$C_{0-3}$alkyl-, —$C_{0-3}$alkylN$R^{64}$C(=O)C(=O)O$C_{0-3}$alkyl-, —$C_{0-3}$alkylN$R^{64}$C(=O)N$R^{64}C_{0-3}$alkyl-, —$C_{0-3}$alkylN$R^{64}$C(=O)N$R^{64}$C(=O)$C_{0-3}$alkyl-, —$C_{0-3}$alkylN$R^{64}$C(=O)N$R^{64}$C(=O)O$C_{0-3}$alkyl-, —$C_{0-3}$alkylN$R^{64}$C(=N$R^{65}$)N$R^{64}C_{0-3}$alkyl-, —$C_{0-3}$alkylN$R^{64}$C(=O)C(=O)N$R^{64}C_{0-3}$alkyl-, —$C_{0-3}$alkylN$R^{64}$C(=S)$C_{0-3}$alkyl-, —$C_{0-3}$alkylN$R^{64}$C(=S)O$C_{0-3}$alkyl-, —$C_{0-3}$alkylN$R^{64}$C(=S)N$R^{64}C_{0-3}$alkyl-, —$C_{0-3}$alkylN$R^{64}$S(=O)$_2C_{0-3}$alkyl-, —$C_{0-3}$alkylN$R^{64}$S(=O)$_2$N$R^{64}C_{0-3}$alkyl-, —$C_{0-3}$alkylOC$_{0-3}$ alkyl-, —$C_{0-3}$alkylOC(=O)$C_{0-3}$alkyl-, —$C_{0-3}$ alkylOC(=O)N$R^{64}C_{0-3}$alkyl-, —$C_{0-3}$alkylOC(=O)O$C_{0-3}$alkyl-, —$C_{0-3}$alkylOC(=N$R^{65}$)N$R^{64}C_{0-3}$ alkyl-, —$C_{0-3}$alkylOS(=O)$C_{0-3}$alkyl-, —$C_{0-3}$ alkylOS(=O)$_2C_{0-3}$alkyl-, —$C_{0-3}$alkylOS(=O)$_2$ O$C_{0-3}$alkyl-, —$C_{0-3}$alkylOS(=O)$_2$N$R^{64}C_{0-3}$ alkyl-, —$C_{0-13}$alkylS(=O)$_nC_{0-3}$alkyl-, —$C_{0-3}$ alkylS(=O)$_2$ O$C_{0-3}$alkyl-, —$C_{0-3}$alkylSO$_3C_{0-3}$ alkyl-, —$C_{0-3}$ alkylS(=O)$_2$N$R^{64}C_{0-3}$alkyl-, and —$C_{0-3}$alkylS(=O)N$R^{64}C_{0-3}$alkyl-;

$X^2$, $X^3$, and $X^4$ are independently present or absent, and if present each is independently chosen from $C_{1-6}$alkylene optionally substituted by 1-12 $R^{79}$, $C_{2-6}$alkenylene optionally substituted by 1-10 $R^{79}$, $C_{2-6}$alkynylene optionally substituted by 1-8 $R^{79}$, $C_{6-11}$arylene optionally substituted by 1-10 $R^{79}$, $C_{2-6}$arylalkylene optionally substituted by 1-18 $R^{79}$, $C_{3-11}$cycloalkylene optionally substituted by 1-20 $R^{79}$, $C_{4-17}$cycloalkylalkylene optionally substituted by 1-31 $R^{79}$, 3-15 membered heterocycloalkylene optionally substituted by 1-27 $R^{79}$, 4-21 membered heterocycloalkylalkylene optionally substituted by 1-39 $R^{79}$, 5-15 membered heteroarylene optionally substituted by 1-14 $R^{79}$, 6-21 membered heteroarylalkylene optionally substituted by 1-26 $R^{79}$, —$C_{0-3}$alkylC(=O)$C_{0-3}$alkyl-, —$C_{0-3}$alkylC(=O)O$C_{0-3}$alkyl-, —$C_{0-3}$alkylC(=O)N$R^{74}C_{0-3}$alkyl-, —$C_{0-3}$alkylC(=O)C(=O)$C_{0-3}$alkyl-, —$C_{0-3}$alkylC(=N$R^{75}$)$C_{0-3}$alkyl-, —$C_{0-3}$alkylC(=N$R^{75}$)N$R^{74}C_{0-3}$ alkyl-, —$C_{0-3}$alkylC(=NOH)N$R^{74}C_{0-3}$ lkyl-, —$C_{0-3}$alkylC(=NOR$^{76}$)$C_{0-3}$alkyl-, —$C_{0-3}$alkylC(=NN$R^{22}R^{73}$)$C_{0-3}$alkyl-, —$C_{0-3}$alkylC(=NN$R^{74}$C(=O)$R^{71}$)$C_{0-3}$alkyl-, —$C_{0-3}$alkylC(=NN$R^{74}$C(=O)O$R^{71}$)$C_{0-3}$alkyl-, —$C_{0-3}$alkylC(=S)N$R^{74}C_{0-3}$ alkyl-, —$C_{0-3}$alkylN$R^{74}C_{0-3}$alkyl-, —$C_{0-3}$ alkylN$R^{74}$N$R^{74}C_{0-3}$alkyl-, —$C_{0-3}$alkylN=N$C_{0-3}$ alkyl-, —$C_{0-3}$alkylN$R^{74}$C(=O)$C_{0-3}$alkyl-, —$C_{0-3}$ alkylN$R^{74}$C(=O)C(=O)$C_{0-3}$alkyl-, —$C_{0-3}$ alkylN$R^{74}$C(=O)O$C_{0-3}$alkyl-, —$C_{0-3}$alkylN$R^{74}$C(=O)C(=O)O$C_{0-3}$alkyl-, —$C_{0-3}$alkylN$R^{74}$C(=O)N$R^{74}C_{0-3}$alkyl-, —$C_{0-3}$alkylN$R^{74}$C(=O)N$R^{74}$C(=O)$C_{0-3}$alkyl-, —$C_{0-3}$alkylN$R^{74}$C(=O)N$R^{74}$C(=O)O$C_{0-3}$alkyl-, —$C_{0-3}$alkylN$R^{74}$C(=N$R^{75}$)N$R^{74}C_{0-3}$alkyl-, —$C_{0-3}$ lkylN$R^{74}$C(=O)C(=O)N$R^{74}C_{0-3}$alkyl-, —$C_{0-3}$ alkylN$R^{74}$C(=S)$C_{0-3}$alkyl-, —$C_{0-3}$alkylN$R^{74}$C(=S)O$C_{0-3}$alkyl-, —$C_{0-3}$ alkylN$R^{74}$C(=S)N$R^{74}C_{0-3}$ alkyl-, —$C_{0-3}$ alkylN$R^{74}$S(=O)$_2C_{0-3}$ alkyl-, —$C_{0-3}$ alkylNR$^{74}$S(=O)$_2$NR$^{74}$$C_{0-3}$alkyl-, —$C_{0-3}$alkylOC$_{0-3}$alkyl-, —$C_{0-3}$alkylOC(=O)$C_{0-3}$ alkyl-, —$C_{0-3}$alkylOC(=O)NR$^{74}$$C_{0-3}$alkyl-, —$C_{0-3}$alkylOC(=O)O$C_{0-3}$alkyl-, —$C_{0-3}$alkylOC(=NR$^{75}$)NR$^{74}$$C_{0-3}$alkyl-, —$C_{0-3}$alkylOS(=O)$C_{0-3}$ alkyl-, —$C_{0-3}$alkylOS(=O)$_2$$C_{0-3}$alkyl-, —$C_{0-3}$ alkylOS(=O)$_2$O$C_{0-3}$alkyl-, —$C_{0-3}$alkylOS(=O)$_2$ NR$^{74}$$C_{0-3}$alkyl-, —$C_{0-3}$alkylS(=O)$_n$$C_{0-3}$alkyl-, —$C_{0-3}$alkylS(=O)$_2$O$C_{0-3}$alkyl-, —$C_{0-3}$alkylSO$_3$$C_{0-3}$ alkyl-, —$C_{0-3}$alkylS(=O)$_2$NR$^{74}$$C_{0-3}$alkyl-, and —$C_{0-3}$alkylS(=O)NR$^{74}$$C_{0-3}$alkyl-;

$Z^2$, $Z^3$, and $Z^4$ are independently chosen from H, $C_{1-6}$alkyl optionally substituted by 1-13 R$^{89}$, $C_{2-6}$alkenyl optionally substituted by 1-11 R$^{89}$, $C_{2-6}$alkynyl optionally substituted by 1-9 R$^{89}$, $C_{6-11}$aryl optionally substituted by 1-11 R$^{89}$, $C_{7-16}$arylalkyl optionally substituted by 1-19 R$^{89}$, $C_{3-11}$cycloalkyl optionally substituted by 1-21 R$^{89}$, $C_{4-17}$cycloalkylalkyl optionally substituted by 1-32 R$^{89}$, 3-15 membered heterocycloalkyl optionally substituted by 1-28 R$^{89}$, 4-21 membered heterocycloalkylalkyl optionally substituted by 1-40 R$^{89}$, 5-15 membered heteroaryl optionally substituted by 1-15 R$^{89}$, 6-21 membered heteroarylalkyl optionally substituted by 1-27 R$^{89}$, halogen, —CN, —C(=O)R$^{80}$, —C(=O)OR$^{80}$, —C(=O)NR$^{82}$R$^{83}$, —C(=O)C(=O)R$^{80}$, —C(=NR$^{85}$)R$^{80}$, —C(=NR$^{85}$)NR$^{82}$R$^{83}$, —C(=NOH)NR$^{82}$R$^{83}$, —C(=NOR$^{86}$)R$^{80}$, —C(=NNR$^{82}$R$^{83}$)R$^{80}$, —C(=NNR$^{84}$C(=O)R$^{81}$)R$^{80}$, —C(=NNR$^{84}$C(=O)OR$^{81}$)R$^{80}$, —C(=S)NR$^{82}$R$^{83}$, —NC, —NO$_2$, —NR$^{82}$R$^{83}$, —NR$^{84}$NR$^{82}$R$^{83}$, —N=NR$^{84}$, =NR$^{80}$, =NOR$^{80}$, —NR$^{84}$OR$^{86}$, —NR$^{84}$C(=O)R$^{80}$, —NR$^{84}$C(=O)C(=O)R$^{80}$, —NR$^{84}$C(=O)OR$^{81}$, —NR$^{84}$C(=O)C(=O)OR$^{81}$, —NR$^{84}$C(=O)NR$^{82}$R$^{83}$, —NR$^{84}$C(=O)NR$^{84}$C(=O)R$^{80}$, —NR$^{84}$C(=O)NR$^{84}$C(=O)OR$^{80}$, —NR$^{84}$C(=NR$^{85}$)NR$^{82}$R$^{83}$, —NR$^{84}$C(=O)C(=O)NR$^{82}$R$^{83}$, —NR$^{84}$C(=S)R$^{80}$, —NR$^{84}$C(=S)OR$^{80}$, —NR$^{84}$C(=S)NR$^{82}$R$^{83}$, —NR$^{84}$S(=O)$^2$ R$^{81}$, —NR$^{84}$S(=O)$_2$NR$^{82}$R$^{83}$, —NR$^{84}$P(=O)R$^{88}$R$^{88}$, —NR$^{84}$P(=O)(NR$^{82}$R$^{83}$)(NR$^{82}$R$^{83}$), —NR$^{84}$P(=O)(OR$^{80}$)(OR$^{80}$), —NR$^{84}$P(=O)(SR$^{80}$)(SR$^{80}$), —OR$^{80}$, =O, —OCN, —OC(=O)R$^{80}$, —OC(=O)NR$^{82}$R$^{83}$, —OC(=O)OR$^{80}$, —OC(=NR$^{85}$)NR$^{82}$R$^{83}$, —OS(=O)R$^{80}$, —OS(=O)$_2$R$^{80}$, —OS(=O)$_2$OR$^{80}$, —OS(=O)$_2$NR$^{82}$R$^{83}$, —OP(=O)R$^{88}$R$^{88}$, —OP(=O)(NR$^{82}$R$^{83}$)(NR$^{82}$R$^{83}$), —OP(=O)(OR$^{80}$)(OR$^{80}$), —OP(=O)(SR$^{80}$)(SR$^{80}$), —SCN, =S, —S(=O)$_n$R$^{80}$, —S(=O)$_2$OR$^{80}$, —SO$_3$R$^{87}$, —S(=O)$_2$NR$^{82}$R$^{83}$, —S(=O)NR$^{82}$R$^{83}$, —SP(=O)R$^{88}$R$^{88}$, —SP(=O)(NR$^{82}$R$^{83}$)(NR$^{82}$R$^{83}$), —SP(=O)(OR$^{80}$)(OR$^{80}$), —SP(=O)(SR$^{80}$)(SR$^{80}$), —P(=O)R$^{88}$R$^{88}$, —P(=O)(NR$^{82}$R$^{83}$)(NR$^{82}$R$^{83}$), —P(=O)(OR$^{80}$)(OR$^{80}$), and —P(=O)(SR$^{80}$)(SR$^{80}$);

alternatively,
when $L^2$, $A^2$, $G^2$, $X^2$, $L^3$, $A^3$, $G^3$ and $X^3$ are absent, $Z^2$ and $Z^3$ can together form a group of formula -A$^{21}$-A$^{22}$-A$^{23}$-, or when $L^3$, $A^3$, $G^3$, $X^3$, $L^4$, $A^4$, $G^4$ and $X^4$ are absent, $Z^3$ and $Z^4$ can together form a group of formula -A$^{21}$-A$^{22}$-A$^{23}$-;

wherein A$^{21}$, A$^{22}$, and A$^{23}$ are independently chosen from —CZ$^{21}$Z$^{22}$—, —CZ$^{23}$Z$^{24}$CZ$^{25}$Z$^{26}$-, —C(=O)—, —NZ$^{27}$—, —S—, —S(=O)—, —S(=O)$_2$—, or —O— wherein:

(a) when any two of Z$^{21}$, Z$^{22}$, Z$^{23}$, Z$^{24}$, Z$^{25}$, Z$^{26}$ and Z$^{27}$ are located on adjacent atoms, they may together form a bond between the atoms, and (b) any of Z$^{21}$, Z$^{22}$, Z$^{23}$, Z$^{24}$, Z$^{25}$, Z$^{26}$ and Z$^{27}$ may be independently chosen from H, $C_{1-6}$alkyl optionally substituted by 1-13 R$^{99}$, $C_{2-6}$alkenyl optionally substituted by 1-11 R$^{99}$, $C_{2-6}$alkynyl optionally substituted by 1-9 R$^{99}$, $C_{6-11}$aryl optionally substituted by 1-11 R$^{99}$, $C_{7-16}$arylalkyl optionally substituted by 1-19 R$^{99}$, $C_{3-11}$cycloalkyl optionally substituted by 1-21 R$^{99}$, $C_{4-17}$cycloalkylalkyl optionally substituted by 1-32 R$^{99}$, 3-15 membered heterocycloalkyl optionally substituted by 1-28 R$^{99}$, 4-21 membered heterocycloalkylalkyl optionally substituted by 1-40 R$^{99}$, 5-15 membered heteroaryl optionally substituted by 1-15 R$^{99}$, 6-21 membered heteroarylalkyl optionally substituted by 1-27 R$^{99}$, halogen, —CN, —C(=O)R$^{90}$, —C(=O)OR$^{90}$, —C(=O)NR$^{92}$R$^{93}$, —C(=O)C(=O)R$^{90}$, —C(=NR$^{95}$)R$^{90}$, —C(=NR$^{95}$)NR$^{92}$R$^{93}$, —C(=NOH)NR$^{92}$R$^{93}$, —C(=NOR$^{96}$)R$^{90}$, —C(=NNR$^{92}$R$^{93}$)R$^{90}$, —C(=NNR$^{94}$C(=O)R$^{91}$)R$^{90}$, —C(=NNR$^{94}$C(=O)OR$^{91}$)R$^{90}$, —C(=S)NR$^{92}$R$^{93}$, —NC, —NO$_2$, —NR$^{92}$R$^{93}$, —NR$^{94}$NR$^{92}$R$^{93}$, —N=NR$^{94}$, =NR$^{90}$, =NOR$^{90}$, —NR$^{94}$OR$^{96}$, —NR$^{94}$C(=O)R$^{90}$, —NR$^{94}$C(=O)C(=O)R$^{90}$, —NR$^{94}$C(=O)OR$^{91}$, —NR$^{94}$C(=O)C(=O)OR$^{91}$, —NR$^{94}$C(=O)NR$^{92}$R$^{93}$, —NR$^{94}$C(=O)NR$^{94}$C(=O)R$^{90}$, —NR$^{94}$C(=O)NR$^{94}$C(=O)OR$^{90}$, —NR$^{94}$C(=NR$^{95}$)NR$^{92}$R$^{93}$, —NR$^{94}$C(=O)C(=O)NR$^{92}$R$^{93}$, —NR$^{94}$C(=Os)R$^{90}$, —NR$^{94}$C(=S)OR$^{90}$, —NR$^{94}$C(=Os)NR$^{92}$R$^{93}$, —NR$^{94}$S(=O)$_2$R$^{91}$, —NR$^{94}$S(=O)$_2$NR$^{92}$R$^{93}$, —NR$^{94}$P(=O)R$^{98}$R$^{98}$, —NR$^{94}$P(=O)(NR$^{92}$R$^{93}$)(NR$^{92}$R$^{93}$), —NR$^{94}$O(=O)(OR$^{90}$)(OR$^{90}$), —NR$^{94}$P(=O)(SR$^{90}$)(SR$^{90}$), —OR$^{90}$, =O, —OCN, —OC(=O)R$^{90}$, —OC(=O)NR$^{92}$R$^{93}$, —OC(=O)OR$^{90}$, —OC(=NR$^{95}$)NR$^{92}$R$^{93}$, —OS(=O)R$^{90}$, —OS(=O)$_2$R$^{90}$, —OS(=O)$_2$OR$^{90}$, —OS(=O)$_2$NR$^{92}$R$^{93}$, —OP(=O)R$^{98}$R$^{98}$, —OP(=O)(NR$^{92}$R$^{93}$)(NR$^{92}$R$^{93}$), —OP(=O)(OR$^{90}$)(OR$^{90}$), —OP(=O)(SR$^{98}$)(SR$^{90}$), —SCN, =S, —S(=O)$_n$ R$^{90}$, —S(=O)$_2$OR$^{90}$, —SO$_3$R$^{97}$, —S(=O)$_2$ NR$^{92}$R$^{93}$, —S(=O)NR$^{92}$R$^{93}$, —SP(=O)R$^{98}$R$^{98}$, — SP(=O)(NR$^{92}$R$^{93}$)(NR$^{92}$R$^{93}$), —SP(=O)(OR$^{90}$)(OR$^{90}$), —SP(=O)(SR$^{90}$)(SR$^{90}$), —P(=O)R$^{98}$R$^{98}$, —P(=O)(NR$^{92}$R$^{93}$)(NR$^{92}$R$^{93}$), —P(=O)(OR$^{90}$)(OR$^{90}$), and —P(=O)(SR$^{90}$)(SR$^{90}$); and (c) any two of Z$^{21}$, Z$^{22}$, Z$^{23}$, Z$^{24}$, Z$^{25}$, Z$^{26}$ and Z$^{27}$ may together form a group of formula -A$^{31}$-A$^{32}$-A$^{33}$-, wherein A$^{31}$, A$^{32}$, and A$^{33}$ are independently chosen from —CZ$^{31}$Z$^{32}$—, —CZ$^{33}$Z$^{34}$CZ$^{35}$Z$^{36}$-, —C(=O)—, —NZ$^{37}$—, —S—, —S(=O)—, —S(=O)$_2$—, or —O— wherein:

(i) when any two of Z$^{31}$, Z$^{32}$, Z$^{33}$, Z$^{34}$, Z$^{35}$, Z$^{36}$ and Z$^{37}$ are located on adjacent atoms, they may together form a bond between the atoms, and (ii) any of any of Z$^{21}$, Z$^{22}$, Z$^{23}$, Z$^{24}$, Z$^{25}$, Z$^{26}$ and Z$^{27}$ may be independently chosen from H, $C_{1-6}$alkyl optionally substituted by 1-13 R$^{139}$, $C_{2-6}$alkenyl optionally substituted by 1-11 R$^{139}$, $C_{2-6}$alkynyl optionally substituted by 1-9 R$^{139}$, $C_{6-11}$aryl optionally substituted by 1-11 R$^{139}$, $C_{7-16}$arylalkyl optionally substituted by 1-19 R$^{139}$, $C_{3-11}$cycloalkyl optionally substituted by 1-21 $R^{139}$, $C_{4-17}$cycloalkylalkyl optionally substituted by 1-32 $R^{139}$, 3-15 membered heterocycloalkyl optionally substituted by 1-28 $R^{139}$, 4-21 membered heterocycloalkylalkyl optionally substituted by 1-40 $R^{139}$, 5-15 membered heteroaryl optionally substituted by 1-15 $R^{139}$, 6-21 membered heteroarylalkyl optionally substituted by 1-27 $R^{139}$, halogen, —CN, —C(=O)$R^{130}$, —C(=O)O$R^{130}$, —C(=O)N$R^{132}R^{133}$, —C(=O)C(=O)$R^{130}$, —C(=N$R^{135}$)$R^{130}$, —C(=N$R^{135}$)N$R^{132}R^{133}$, —C(=NOH)N$R^{132}R^{133}$, —C(=NO$R^{136}$)$R^{130}$, —C(=NN$R^{132}R^{133}$)$R^{130}$, —C(=NN$R^{134}$C(=O)$R^{131}$)$R^{130}$, —C(=NN$R^{134}$C(=O)O$R^{131}$)$R^{130}$, —C(=S)N$R^{132}R^{133}$, —NC, —NO$_2$, —N$R^{132}R^{133}$, —N$R^{134}$N$R^{132}R^{133}$, —N=N$R^{134}$, =N$R^{130}$, =NO$R^{130}$, —N$R^{134}$O$R^{136}$, —N$R^{134}$C(=O)$R^{130}$, —N$R^{134}$C(=O)C(=O)$R^{130}$, —N$R^{134}$C(=O)O$R^{131}$, —N$R^{134}$C(=O)C(=O)O$R^{131}$, —N$R^{134}$C(=O)N$R^{132}R^{133}$, —N$R^{134}$C(=O)N$R^{134}$C(=O)O$R^{130}$, —N$R^{134}$C(=O)N$R^{134}$C(=O)O$R^{130}$, —N$R^{134}$C(=N$R^{135}$)N$R^{132}R^{133}$, —N$R^{134}$C(=O)C(=O)N$R^{132}R^{133}$, —N$R^{134}$C(=S)$R^{130}$, —N$R^{134}$C(=S)O$R^{130}$, —N$R^{134}$C(=S)N$R^{132}R^{133}$, —N$R^{134}$S(=O)$_2$$R^{131}$, —N$R^{134}$S(=O)$_2$N$R^{132}R^{133}$, —N$R^{134}$P(=O)$R^{138}R^{138}$, —N$R^{134}$P(=O)(N$R^{132}R^{133}$)(N$R^{132}R^{133}$), —N$R^{134}$P(=O)(O$R^{130}$)(O$R^{130}$), —N$R^{134}$P(=O)(S$R^{130}$)(S$R^{130}$), —O$R^{130}$, =O, —OCN, —OC(=O)$R^{130}$, —OC(=O)N$R^{132}R^{133}$, —OC(=O)O$R^{130}$, —OC(=N$R^{135}$)N$R^{132}R^{133}$, —OS(=O)$R^{130}$, —OS(=O)$_2$$R^{130}$, —OS(=O)$_2$O$R^{130}$, —OS(=O)$_2$N$R^{132}R^{133}$, —OP(=O)$R^{138}R^{138}$, —OP(=O)(N$R^{132}R^{133}$)(N$R^{132}R^{133}$), —OP(=O)(O$R^{130}$)(O$R^{130}$), —OP(=O)(S$R^{130}$)(S$R^{130}$), —SCN, =S, —S(=O)$_n$$R^{130}$, —S(=O)$_2$O$R^{130}$, —SO$_3R^{137}$, —S(=O)$_2$N$R^{132}R^{133}$, —S(=O)N$R^{132}R^{133}$, —SP(=O)$R^{138}R^{138}$, —SP(=O)(N$R^{132}R^{133}$)(N$R^{132}R^{133}$), —SP(=O)(O$R^{130}$)(O$R^{130}$), —SP(=O)(S$R^{130}$)(S$R^{130}$), —P(=O)$R^{138}R^{138}$, —P(=O)(N$R^{132}R^{133}$)(N$R^{132}R^{133}$), —P(=O)(O$R^{130}$)(O$R^{130}$), and —P(=O)(S$R^{130}$)(S$R^{130}$);

$R^9$, $R^{19}$, $R^{29}$, $R^{39}$, $R^{49}$, $R^{59}$, $R^{69}$, $R^{79}$, $R^{89}$, $R^{99}$, and $R^{139}$ at each occurrence is independently chosen from $C_{1-6}$alkyl optionally substituted by 1-13 $R^{179}$, $C_{2-6}$alkenyl optionally substituted by 1-11 $R^{179}$, $C_{2-6}$alkynyl optionally substituted by 1-9 $R^{179}$, $C_{6-11}$aryl optionally substituted by 1-11 $R^{179}$, $C_{7-16}$arylalkyl optionally substituted by 1-19 $R^{179}$, $C_{3-11}$cycloalkyl optionally substituted by 1-21 $R^{179}$, $C_{4-17}$cycloalkylalkyl optionally substituted by 1-32 $R^{179}$, 3-15 membered heterocycloalkyl optionally substituted by 1-28 $R^{179}$, 4-21 membered heterocycloalkylalkyl optionally substituted by 1-40 $R^{179}$, 5-15 membered heteroaryl optionally substituted by 1-15 $R^{179}$, 6-21 membered heteroarylalkyl optionally substituted by 1-27 $R^{179}$, halogen, —CN, —C(=O)$R^{170}$, —C(=O)O$R^{170}$, —C(=O)N$R^{172}R^{173}$, —C(=O)C(=O)$R^{170}$, —C(=N$R^{175}$)$R^{170}$, —C(=N$R^{175}$)N$R^{172}R^{173}$, —C(=NOH)N$R^{172}R^{173}$, —C(=NO$R^{176}$)$R^{170}$, —C(=N$R^{172}$)$R^{173}$)$R^{170}$, —C(=NN$R^{174}$C(=O)$R^{171}$)$R^{170}$, —C(=NN$R^{174}$C(=O)O$R^{171}$)$R^{170}$, —C(=S)N$R^{172}R^{173}$, —NC, —NO$_2$, —N$R^{172}R^{173}$, —N$R^{174}$N$R^{172}R^{173}$, —N=N$R^{174}$, =N$R^{170}$, =NO$R^{170}$, —N$R^{174}$O$R^{176}$, —N$R^{174}$C(=O)$R^{170}$, —N$R^{174}$C(=O)C(=O)$R^{170}$, —N$R^{174}$C(=O)O$R^{171}$, —N$R^{174}$C(=O)C(=O)O$R^{171}$, —N$R^{174}$C(=O)N$R^{172}R^{173}$, —N$R^{174}$C(=O)N$R^{174}$C(=O)$R^{170}$, —N$R^{174}$C(=O)N$R^{174}$C(=O)O$R^{170}$, —N$R^{174}$C(=N$R^{175}$)N$R^{172}R^{173}$, —N$R^{174}$C(=O)C(=O)N$R^{172}R^{173}$, —N$R^{174}$C(=S)$R^{170}$, —N$R^{174}$C(=S)O$R^{170}$, —N$R^{174}$C(=S)N$R^{172}R^{173}$, —N$R^{174}$S(=O)$_2$$R^{171}$, —N$R^{174}$S(=O)$_2$N$R^{172}R^{173}$), —N$R^{174}$P(=O)$R^{178}R^{178}$, N$R^{174}$P(=O)(N$R^{172}R^{173}$)(N$R^{172}R^{173}$), —N$R^{174}$P(=O)(O$R^{170}$)(O$R^{170}$), —N$R^{174}$P(=O)(S$R^{170}$)(S$R^{170}$), —O$R^{170}$, =O, —OCN, —OC(=O)$R^{170}$, —OC(=O)N$R^{172}R^{173}$, —OC(=O)O$R^{170}$, —OC(=N$R^{175}$)N$R^{172}R^{173}$, —OS(=O)$R^{170}$, —OS(=O)$_2$$R^{170}$, —OS(=O)$_2$O$R^{170}$, —OS(=O)$_2$N$R^{172}R^{173}$, —OP(=O)$R^{178}R^{178}$, —OP(=O)(N$R^{172}R^{173}$)(N$R^{172}R^{173}$), —OP(=O)(O$R^{170}$)(O$R^{170}$), —OP(=O)(S$R^{170}$)(S$R^{170}$), —SCN, =S, —S(=O)$_n$$R^{170}$, —S(=O)$_2$O$R^{170}$, —SO$_3R^{177}$, —S(=O)$_2$N$R^{172}R^{173}$, —S(=O)N$R^{172}R^{173}$, —SP(=O)$R^{178}R^{178}$, —SP(=O)(N$R^{172}R^{173}$)(N$R^{172}R^{173}$), —SP(=O)(O$R^{170}$)(O$R^{170}$), —SP(=O)(S$R^{170}$)(S$R^{170}$), —P(=O)$R^{178}R^{178}$, —P(=O)(N$R^{172}R^{173}$)(N$R^{172}R^{173}$), —P(=O)(O$R^{170}$)(O$R^{170}$), and —P(=O)(S$R^{170}$)(S$R^{170}$);

$R^1$, $R^4$, $R^5$, $R^6$, $R^{10}$, $R^{11}$, $R^{14}$, $R^{15}$, $R^{16}$, $R^{17}$, $R^{21}$, $R^{24}$, $R^{25}$, $R^{26}$, $R^{31}$, $R^{34}$, $R^{35}$, $R^{36}$, $R^{41}$, $R^{44}$, $R^{45}$, $R^{46}$, $R^{50}$, $R^{51}$, $R^{54}$, $R^{55}$, $R^{56}$, $R^{57}$, $R^{61}$, $R^{64}$, $R^{65}$, $R^{66}$, $R^{71}$, $R^{74}$, $R^{75}$, $R^{76}$, $R^{80}$, $R^{81}$, $R^{84}$, $R^{85}$, $R^{86}$, $R^{87}$, $R^{90}$, $R^{91}$, $R^{94}$, $R^{95}$, $R^{96}$, $R^{97}$, $R^{100}$, $R^{101}$, $R^{104}$, $R^{105}$, $R^{106}$, $R^{107}$ $R^{130}$, $R^{131}$, $R^{134}$, $R^{135}$, $R^{136}$, $R^{137}$, $R^{170}$, $R^{171}$, $R^{174}$, $R^{175}$, $R^{176}$ and $R^{177}$ at each occurrence is independently chosen from H, $C_{1-6}$alkyl optionally substituted by 1-13 $R^{189}$, $C_{2-6}$alkenyl optionally substituted by 1-11 $R^{189}$, $C_{2-6}$alkynyl optionally substituted by 1-9 $R^{189}$, $C_{6-11}$aryl optionally substituted by 1-11 $R^{189}$, $C_{7-16}$arylalkyl optionally substituted by 1-19 $R^{189}$, $C_{3-11}$cycloalkyl optionally substituted by 1-21 $R^{189}$, $C_{4-17}$cycloalkylalkyl optionally substituted by 1-32 $R^{189}$, 3-15 membered heterocycloalkyl optionally substituted by 1-28 $R^{189}$, 4-21 membered heterocycloalkylalkyl optionally substituted by 1-40 $R^{189}$, 5-15 membered heteroaryl optionally substituted by 1-15 $R^{189}$, and 6-21 membered heteroarylalkyl optionally substituted by 1-27 $R^{189}$;

$R^{18}$, $R^{58}$, $R^{88}$, $R^{98}$, $R^{108}$, $R^{138}$, and $R^{178}$ at each occurrence is independently chosen from $C_{1-6}$alkyl optionally substituted by 1-13 $R^{189}$, $C_{2-6}$alkenyl optionally substituted by 1-11 $R^{189}$, $C_{2-6}$alkynyl optionally substituted by 1-9 $R^{189}$, $C_{6-11}$aryl optionally substituted by 1-11 $R^{189}$, $C_{7-16}$arylalkyl optionally substituted by 1-19 $R^{189}$, $C_{3-11}$cycloalkyl optionally substituted by 1-21 $R^{189}$, $C_{4-17}$cycloalkylalkyl optionally substituted by 1-32 $R^{189}$, 3-15 membered heterocycloalkyl optionally substituted by 1-28 $R^{189}$, 4-21 membered heterocycloalkylalkyl optionally substituted by 1-40 $R^{189}$, 5-15 membered heteroaryl optionally substituted by 1-15 $R^{189}$, and 6-21 membered heteroarylalkyl optionally substituted by 1-27 $R^{189}$;

$R^2$, $R^3$, $R^{12}$, $R^{13}$, $R^{22}$, $R^{23}$, $R^{32}$, $R^{33}$, $R^{42}$, $R^{43}$, $R^{52}$, $R^{53}$, $R^{62}$, $R^{63}$, $R^{72}$, $R^{73}$, $R^{82}$, $R^{83}$, $R^{92}$, $R^{93}$, $R^{102}$, $R^{103}$, $R^{132}$, $R^{133}$, $R^{172}$ and $R^{173}$ at each occurrence is independently chosen from H, $C_{1-6}$alkyl optionally substituted by 1-13 $R^{199}$, $C_{2-6}$alkenyl optionally substituted by 1-11 $R^{199}$, $C_{2-6}$alkynyl optionally substituted by 1-9 $R^{199}$, $C_{6-11}$aryl optionally substituted by 1-11 $R^{199}$, $C_{7-16}$arylalkyl optionally substituted by 1-19 $R^{199}$, $C_{3-11}$cycloalkyl optionally substituted by 1-21 $R^{199}$, $C_{4-17}$cycloalkylalkyl optionally substituted by 1-32 $R^{199}$, 3-15 membered heterocycloalkyl optionally substituted by 1-28 $R^{199}$, 4-21 membered heterocycloalkylalkyl optionally substituted by 1-40 $R^{199}$, 5-15 membered heteroaryl optionally substituted by 1-15 $R^{199}$, and 6-21 membered heteroarylalkyl optionally substituted by 1-27 $R^{199}$;

or any $R^2$ and $R^3$, $R^{12}$ and $R^{13}$, $R^{22}$ and $R^{23}$, $R^{32}$ and $R^{33}$, $R^{42}$ and $R^{43}$, $R^{52}$ and $R^{53}$, $R^{62}$ and $R^{63}$, $R^{72}$ and $R^{73}$, $R^{82}$ and $R^{83}$, $R^{92}$ and $R^{93}$, $R^{102}$ and $R^{103}$, $R^{132}$ and $R^{133}$, or $R^{172}$ and $R^{173}$ may form, together with the nitrogen atom to which they are attached, a 3-15 membered heterocycloalkyl optionally substituted by 1-28 $R^{209}$ or a 5-15 membered heteroaryl optionally substituted by 1-15 $R^{209}$;

$R^{179}$, $R^{189}$, $R^{199}$ and $R^{209}$ at each occurrence is independently chosen from $C_{1-6}$alkyl optionally substituted by 1-13 $R^{219}$, $C_{2-6}$alkenyl optionally substituted by 1-11 $R^{219}$, $C_{2-6}$alkynyl optionally substituted by 1-9 $R^{219}$, $C_{6-11}$aryl optionally substituted by 1-11 $R^{219}$, $C_{7-16}$arylalkyl optionally substituted by 1-19 $R^{219}$, $C_{3-11}$cycloalkyl optionally substituted by 1-21 $R^{219}$, $C_{4-17}$cycloalkylalkyl optionally substituted by 1-32 $R^{219}$, 3-15 membered heterocycloalkyl optionally substituted by 1-28 $R^{219}$, 4-21 membered heterocycloalkylalkyl optionally substituted by 1-40 $R^{219}$, 5-15 membered heteroaryl optionally substituted by 1-15 $R^{219}$, 6-21 membered heteroarylalkyl optionally substituted by 1-27 $R^{219}$, halogen, —CN, —C(=O)$R^{210}$, —C(=O)O$R^{210}$, —C(=O)N$R^{212}R^{213}$, —C(=O)C(=O)$R^{210}$, —C(=N$R^{215}$)$R^{210}$, —C(=N$R^{215}$)N$R^{212}R^{213}$, —C(=NOH)N$R^{212}R^{213}$, —C(=NO$R^{216}$)$R^{210}$, —C(=NN$R^{212}R^{213}$)$R^{210}$, —C(=NN$R^{214}$C(=O)$R^{211}$)$R^{210}$, —C(=NN$R^{214}$C(=O)O$R^{211}$)$R^{210}$, —C(=S)N$R^{212}R^{213}$, —NC, —NO$_2$, —N$R^{212}R^{213}$, —N$R^{214}$N$R^{212}R^{213}$, —N=N$R^{214}$, =N$R^{210}$, =NO$R^{210}$, —N$R^{214}$O$R^{216}$, —N$R^{214}$C(=O)$R^{210}$, —N$R^{214}$C(=O)C(=O)$R^{210}$, —N$R^{214}$C(=O)O$R^{211}$, —N$R^{214}$C(=O)C(=O)O$R^{211}$, —N$R^{214}$C(=O)N$R^{212}R^{213}$, —N$R^{214}$C(=O)N$R^{214}$C(=O)N$R^{214}$C(=O)$R^{210}$, —N$R^{214}$C(=O)N$R^{214}$C(=O)O$R^{210}$, —N$R^{214}$C(=N$R^{215}$)N$R^{212}$N$R^{213}R^{210}$, —N$R^{214}$C(=O)C(=O)N$R^{212}R^{213}$, —N$R^{214}$C(=S)$R^{210}$, —N$R^{214}$C(=S)O$R^{210}$, —N$R^{214}$C(=S)N$R^{212}R^{213}$, —N$R^{214}$S(=O)$_2R^{211}$, —N$R^{214}$S(=O)$_2$N$R^{212}R^{213}$, —N$R^{214}$P(=O)$R^{218}R^{218}$, —N$R^{214}$P(=O)(N$R^{212}R^{213}$)(N$R^{212}R^{213}$), —N$R^{214}$P(=O)(O$R^{210}$)(O$R^{210}$), —N$R^{214}$P(=O)(S$R^{210}$)(S$R^{210}$), —O$R^{210}$, =O, —OCN, —OC(=O)$R^{210}$, —OC(=O)N$R^{212}R^{213}$, —OC(=O)O$R^{210}$, —OC(=N$R^{215}$)N$R^{212}R^{213}$, —OS(=O)$R^{210}$, —OS(=O)$_2R^{210}$, —OS(=O)$_2$O$R^{210}$, —OS(=O)$_2$N$R^{212}R^{213}$, —OP(=O)$R^{218}R^{218}$, —OP(=O)(N$R^{212}R^{213}$)(N$R^{212}R^{213}$), —OP(=O)(O$R^{210}$)(O$R^{210}$), —OP(=O)(S$R^{210}$)(S$R^{210}$), —SCN, =S, —S(=O)$_nR^{210}$, —S(=O)$_2$O$R^{210}$, —SO$_3R^{217}$, —S(=O)$_2$N$R^{212}R^{213}$, —S(=O)N$R^{212}R^{213}$, —SP(=O)$R^{218}R^{218}$, —SP(=O)(N$R^{212}R^{213}$)(N$R^{212}R^{213}$), —SP(=O)(O$R^{210}$)(O$R^{210}$), —SP(=O)(S$R^{210}$)(S$R^{210}$), —P(=O)$R^{218}R^{218}$, —P(=O)(N$R^{212}R^{213}$)(N$R^{212}R^{213}$), —P(=O)(O$R^{210}$)(O$R^{210}$), and —P(=O)(S$R^{210}$)(S$R^{210}$);

$R^{210}$, $R^{211}$, $R^{214}$, $R^{215}$, $R^{216}$ and $R^{217}$ at each occurrence is independently chosen from H, $C_{1-6}$alkyl optionally substituted by 1-13 $R^{229}$, $C_{2-6}$alkenyl optionally substituted by 1-11 $R^{229}$, $C_{2-6}$alkynyl optionally substituted by 1-9 $R^{229}$, $C_{6-11}$aryl optionally substituted by 1-11 $R^{229}$, $C_{7-16}$arylalkyl optionally substituted by 1-19 $R^{229}$, $C_{3-11}$cycloalkyl optionally substituted by 1-21 $R^{229}$, $C_{4-17}$cycloalkylalkyl optionally substituted by 1-32 $R^{229}$, 3-15 membered heterocycloalkyl optionally substituted by 1-28 $R^{229}$, 4-21 membered heterocycloalkylalkyl optionally substituted by 1-40 $R^{229}$, 5-15 membered heteroaryl optionally substituted by 1-15 $R^{229}$, and 6-21 membered heteroarylalkyl optionally substituted by 1-27 $R^{229}$;

$R^{212}$ and $R^{213}$ at each occurrence is independently chosen from H, $C_{1-6}$alkyl optionally substituted by 1-13 $R^{239}$, $C_{2-6}$alkenyl optionally substituted by 1-11 $R^{239}$, $C_{2-6}$alkynyl optionally substituted by 1-9 $R^{239}$, $C_{6-11}$aryl optionally substituted by 1-11 $R^{239}$, $C_{7-16}$arylalkyl optionally substituted by 1-19 $R^{239}$, $C_{3-11}$cycloalkyl optionally substituted by 1-21 $R^{239}$, $C_{4-17}$cycloalkylalkyl optionally substituted by 1-32 $R^{239}$, 3-15 membered heterocycloalkyl optionally substituted by 1-28 $R^{239}$, 4-21 membered heterocycloalkylalkyl optionally substituted by 1-40 $R^{239}$, 5-15 membered heteroaryl optionally substituted by 1-15 $R^{239}$, and 6-21 membered heteroarylalkyl optionally substituted by 1-27 $R^{239}$;

or any $R^{212}$ and $R^{213}$ may form, together with the nitrogen atom to which they are attached, a 3-15 membered heterocycloalkyl optionally substituted by 1-28 $R^{249}$ or a 5-15 membered heteroaryl optionally substituted by 1-15 $R^{249}$;

$R^{218}$ at each occurrence is independently chosen from $C_{1-6}$alkyl optionally substituted by 1-13 $R^{229}$, $C_{2-6}$alkenyl optionally substituted by 1-11 $R^{229}$, $C_{2-6}$alkynyl optionally substituted by 1-9 $R^{229}$, $C_{6-11}$aryl optionally substituted by 1-11 $R^{229}$, $C_{7-16}$arylalkyl optionally substituted by 1-19 $R^{229}$, $C_{3-11}$cycloalkyl optionally substituted by 1-21 $R^{229}$, $C_{4-17}$cycloalkylalkyl optionally substituted by 1-32 $R^{229}$, 3-15 membered heterocycloalkyl optionally substituted by 1-28 $R^{229}$, 4-21 membered heterocycloalkylalkyl optionally substituted by 1-40 $R^{229}$, 5-15 membered heteroaryl optionally substituted by 1-15 $R^{229}$, and 6-21 membered heteroarylalkyl optionally substituted by 1-27 $R^{229}$;

$R^{219}$, $R^{229}$, $R^{239}$ and $R^{249}$ at each occurrence is independently chosen from $C_{1-6}$alkyl optionally substituted by 1-13 halogen, $C_{2-6}$alkenyl, $C_{2-6}$alkynyl, $C_{6-11}$aryl, $C_{7-16}$arylalkyl, $C_{3-11}$cycloalkyl, $C_{4-17}$cycloalkylalkyl, 3-15 membered heterocycloalkyl, 4-21 membered heterocycloalkylalkyl, 5-15 membered heteroaryl, 6-21 membered heteroarylalkyl, halogen, —CN, —C(=O)$R^{250}$, —C(=O)O$R^{250}$, —C(=O)N$R^{250}R^{250}$, —C(=O)C(=O)$R^{250}$, —C(=N$R^{250}$)$R^{250}$, —C(=N$R^{250}$)N$R^{250}R^{250}$, —C(=NOH)N$R^{250}R^{250}$, —C(=NO$R^{250}$)$R^{250}$, —C(=NN$R^{250}R^{250}$)$R^{250}$, —C(=N$R^{250}$C(=O)$R^{250}R^{250}$, —C(=NN$R^{250}$C(=O)O$R^{250}R^{250}$, —C(=S)N$R^{250}R^{250}$, —NC, —NO$_2$, —N$R^{250}R^{250}$, —N$R^{250}$N$R^{250}R^{250}$, —N=N$R^{250}$, =N$R^{250}$, =NO$R^{250}$, —N$R^{250}$O$R^{250}$, —N$R^{250}$C(=O)$R^{250}$, —N$R^{250}$C(=O)C(=O)$R^{250}$, —N$R^{250}$C(=O)O$R^{250}$, —N$R^{250}$C(=O)C(=O)O$R^{250}$, —N$R^{250}$C(=O)N$R^{250}R^{250}$, —N$R^{250}$C(=O)N$R^{250}$C(=O)$R^{250}$, —N$R^{250}$C(=O)N$R^{250}$C(=O)O$R^{250}$, —N$R^{250}$C(=N$R^{250}$)N$R^{250}R^{250}$, —N$R^{250}$C(=O)C(=O)N$R^{250}R^{250}$, —N$R^{250}$C(=S)$R^{250}$, —N$R^{250}$C (=S)OR$^{250}$, —NR$^{250}$C(=S)NR$^{250}$R$^{250}$, —NR$^{250}$S(=O)$_2$R$^{250}$, —NR$^{250}$S(=O)$_2$NR$^{250}$R$^{250}$, —NR$^{250}$P(=O)R$^{251}$R$^{251}$, —NR$^{250}$P(=O)(NR$^{250}$R$^{250}$)(NR$^{250}$R$^{250}$), —NR$^{250}$P(=O)(OR$^{250}$)(OR$^{250}$), —NR$^{250}$P(=O)(SR$^{250}$)(SR$^{250}$), —OR$^{250}$, =O, —OCN, —OC(=O)R$^{250}$, —OC(=O)NR$^{250}$R$^{250}$, —OC(=O)OR$^{250}$), —OC(=NR$^{250}$)NR$^{250}$R$^{250}$, —OS(=O)R$^{250}$, —OS(=O)$_2$R$^{250}$, —OS(=O)$_2$OR$^{250}$, —OS(=O)$_2$NR$^{250}$R$^{250}$, —OP(=O)R$^{251}$R$^{251}$, —OP(=O)(NR$^{250}$R$^{250}$)(NR$^{250}$R$^{250}$), —OP(=O)(OR$^{250}$)(OR$^{250}$), —OP(=O)(SR$^{250}$)(SR$^{250}$), —SCN, =S, —S(=O)$_n$R$^{250}$, —S(=O)$_2$OR$^{250}$O, —SO$_3$R$^{250}$, —S(=O)$_2$NR$^{250}$R$^{250}$, —S(=O)NR$^{250}$R$^{250}$, —SP(=O)R$^{251}$R$^{251}$, —SP(=O)(NR$^{250}$R$^{250}$)(NR$^{250}$R$^{250}$), —SP(=O)(OR$^{250}$)(OR$^{250}$), —SP(=O)(SR$^{250}$)(SR$^{250}$), —P(=O)R$^{251}$R$^{251}$, —P(=O)(NR$^{250}$R$^{250}$)(NR$^{250}$R$^{250}$), —P(=O)(OR$^{250}$)(OR$^{250}$), and —P(=O)(SR$^{250}$)(SR$^{250}$);

R$^{250}$ at each occurrence is independently chosen from H, C$_{1-6}$alkyl and C$_{1-6}$-haloalkyl;
R$^{251}$ at each occurrence is independently chosen from C$_{1-6}$alkyl and C$_{1-6}$-haloalkyl; and
n at each occurrence is independently chosen from 0, 1, and 2;

with the proviso that the compound is not:

(a)
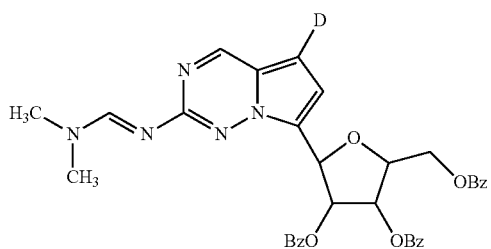

wherein
Bz is benzoyl, and
D is —C(=O)H or H, (b)
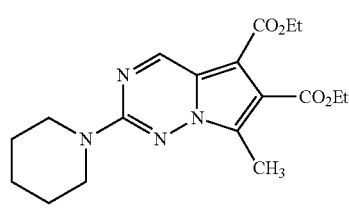

wherein Et is ethyl, or (c)
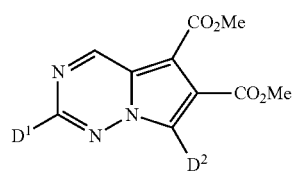

wherein
D$^1$ is methoxy, phenyl, or 4-methylphenyl,
D$^2$ is —CH$_2$C(=O)OMe or —C(=O)OMe, and
Me is methyl.

2. A compound as defined in claim 1, having an ALK kinase IC$_{50}$ of <0.1 μM.

3. A compound as defined in claim 1, having a JAK2 kinase IC$_{50}$ of <0.1 μM.

4. A pharmaceutical composition comprising a compound as defined in claim 1 and at least one pharmaceutically acceptable carrier, diluent, or excipient therefor.

5. A method of treating lung cancer in a subject with lung cancer, comprising administering to the subject a therapeutically effective amount of a compound as defined in claim 1.

6. A compound chosen from:
[7-(3-Chloro-phenyl)-pyrrolo[2,1-f][1,2,4]triazin-2-yl]-(4-morpholin-4-yl-phenyl)-amine;
(4-Morpholin-4-yl-phenyl)-(7-phenyl-pyrrolo[2,1-f][1,2,4]triazin-2-yl)amine;
[7-(5-Chloro-2-methoxy-phenyl)-pyrrolo[2,1-f][1,2,4]triazin-2-yl]-(4-morpholin-4-yl-phenyl)-amine;
(4-Morpholin-4-yl-phenyl)-(7-pyridin-4-yl-pyrrolo[2,1-f][1,2,4]triazin-2-yl)-amine;
[7-(2,3-Dihydro-benzo[1,4]dioxin-6-yl)-pyrrolo[2,1-f][1,2,4]triazin-2-yl]-(4-morpholin-4-yl-phenyl)-amine;
3-[2-(4-Morpholin-4-yl-phenylamino)-pyrrolo[2,1-f][1,2,4]triazin-7-yl]-benzoic acid methyl ester;
[4-(4-Methyl-piperazin-1-yl)-phenyl]-(7-phenyl-pyrrolo[2,1-f][1,2,4]triazin-2-yl)-amine;
[7-(2,3-Dihydro-benzo[1,4]dioxin-6-yl)-pyrrolo[2,1-f][1,2,4]triazin-2-yl]-[4-(4-methyl-piperazin-1-yl)-phenyl]-amine;
[3-(2-Methoxy-ethyl)-2,3,4,5-tetrahydro-1H-benzo[d]azepin-7-yl]-(7-phenyl-pyrrolo[2,1-f][1,2,4]triazin-2-yl)-amine;
[7-(1-Methyl-1H-pyrazol-4-yl)-pyrrolo[2,1-f][1,2,4]triazin-2-yl]-(4-morpholin-4-yl-phenyl)-amine;
(4-Morpholin-4-yl-phenyl)-(7-pyridin-3-yl-pyrrolo[2,1-f][1,2,4]triazin-2-yl)-amine;
(7-Phenyl-pyrrolo[2,1-f][1,2,4]triazin-2-yl)-pyridin-3-yl-methyl-amine;
(7-Phenyl-pyrrolo[2,1-f][1,2,4]triazin-2-yl)-(3,4,5-trimethoxy-phenyl)amine;
Morpholin-4-yl-{4-[2-(4-morpholin-4-yl-phenylamino)-pyrrolo[2,1-f][1,2,4]triazin-7-yl]-phenyl}-methanone;
{3-[2-(4-Morpholin-4-yl-phenylamino)-pyrrolo[2,1-f][1,2,4]triazin-7-yl]-phenyl}-pyrrolidin-1-yl-methanone;
[7-(2-Methoxy-pyridin-3-yl)-pyrrolo[2,1-f][1,2,4]triazin-2-yl]-(4-morpholin-4-yl-phenyl)-amine;
[7-(5-Chloro-2-methoxy-phenyl)-pyrrolo[2,1-f][1,2,4]triazin-2-yl]-[4-(4-methyl-piperazin-1-yl)-phenyl]-amine;
[4-(4-Methyl-piperazin-1-yl)-phenyl]-[7-(1-methyl-1H-pyrazol-4-yl)-pyrrolo[2,1-f][1,2,4]triazin-2-yl]-amine;
(4-{2-[4-(4-Methyl-piperazin-1-yl)-phenylamino]-pyrrolo[2,1-f][1,2,4]triazin-7-yl}-phenyl)-morpholin-4-yl-methanone;
[7-(2-Methoxy-phenyl)-pyrrolo[2,1-f][1,2,4]triazin-2-yl]-[4-(4-methyl-piperazin-1-1)-phenyl]-amine;
(3-{2-[4-(4-Methyl-piperazin-1-yl)-phenylamino]-pyrrolo[2,1-f][1,2,4]triazin-7-yl}-phenyl)-pyrrolidin-1-yl-methanone;
[7-(2-Methoxy-pyridin-3-yl)-pyrrolo[2,1-f][1,2,4]triazin-2-yl]-[4-(4-methyl-piperazin-1-yl)-phenyl]-amine;
N-tert-Butyl-3-{2-[4-(4-methyl-piperazin-1-yl)-phenylamino]-pyrrolo[2,1-f][1,2,4]triazin-7-yl}-benzenesulfonamide;

N(2)-[4-(4-Methyl-piperazin-1-yl)-phenyl]-N(7)-phenyl-pyrrolo[2,1-f][1,2,4]triazine-2,7-diamine;
[7-(2-Chloro-phenyl)-pyrrolo[2,1-f][1,2,4]triazin-2-yl]-[4-(4-methyl-piperazin-1-yl)-phenyl]-amine;
[7-(3-Chloro-phenyl)-pyrrolo[2,1-f][1,2,4]triazin-2-yl]-[4-(4-methyl-piperazin-1-yl)-phenyl]-amine;
[4-(4-Methyl-piperazin-1-yl)-phenyl]-(7-pyridin-3-yl-pyrrolo[2,1-f][1,2,4]triazin-2-yl)-amine;
(2-Morpholin-4-yl-ethyl)-(7-phenyl-pyrrolo[2,1-f][1,2,4]triazin-2-yl)-amine;
(3-Morpholin-4-yl-propyl)-(7-phenyl-pyrrolo[2,1-f][1,2,4]triazin-2-yl)-amine;
[3-(2-Methoxy-ethyl)-2,3,4,5-tetrahydro-1H-benzo[d]azepin-7-yl]-[7-(2-methoxy-phenyl)-pyrrolo[2,1-f][1,2,4]triazin-2-yl]-amine;
2-{2-[3-(2-Methoxy-ethyl)-2,3,4,5-tetrahydro-1H-benzo[d]azepin-7-ylamino]-pyrrolo[2,1-f][1,2,4]triazin-7-yl}-N,N-dimethyl-benzenesulfonamide;
[3-(2-Methoxy-ethyl)-2,3,4,5-tetrahydro-1H-benzo[d]azepin-7-yl]-{7-[2-(pyrrolidine-1-sulfonyl)-phenyl]-pyrrolo[2,1-f][1,2,4]triazin-2-yl}-amine;
[2-Methoxy-4-(4-methyl-piperazin-1-yl)-phenyl]-[7-(2-methoxy-phenyl)-pyrrolo[2,1-f][1,2,4]triazin-2-yl]-amine;
[2-Methoxy-4-(4-methyl-piperazin-1-yl)-phenyl]-[7-(2-methoxy-pyridin-3-yl)-pyrrolo[2,1-f][1,2,4]triazin-2-yl]-amine;
2-{2-[2-Methoxy-4-(4-methyl-piperazin-1-yl)-phenylamino]-pyrrolo[2,1-f][1,2,4]triazin-7-yl}-N,N-dimethyl-benzenesulfonamide;
2-[2-(4-Morpholin-4-yl-phenylamino)-pyrrolo[2,1-f][1,2,4]triazin-7-yl]-benzamide;
5-[2-(4-Morpholin-4-yl-phenylamino)-pyrrolo[2,1-f][1,2,4]triazin-7-yl]-pyridine-2-carbonitrile;
[7-(4-Methanesulfonyl-phenyl)-pyrrolo[2,1-f][1,2,4]triazin-2-yl]-(4-morpholin-4-yl-phenyl)-amine;
3-[2-(4-Morpholin-4-yl-phenylamino)-pyrrolo[2,1-f][1,2,4]triazin-7-yl]-benzonitrile;
[5-(2-Chloro-phenyl)-pyrrolo[2,1-f][1,2,4]triazin-2-yl]-[4-(4-methyl-piperazin-1-yl)-phenyl]-amine;
[4-(4-Methyl-piperazin-1-yl)-phenyl]-(5-phenyl-pyrrolo[2,1-f][1,2,4]triazin-2-yl)-amine;
[5-(2-Methoxy-phenyl)-pyrrolo[2,1-f][1,2,4]triazin-2-yl]-[4-(4-methyl-piperazin-1-yl)-phenyl]-amine;
[7-(3-Methanesulfonyl-phenyl)-pyrrolo[2,1-f][1,2,4]triazin-2-yl]-(4-morpholin-4-yl-phenyl)-amine;
4-[2-(4-Morpholin-4-yl-phenylamino)-pyrrolo[2,1-f][1,2,4]triazin-7-yl]-benzoic acid tert-butyl ester;
4-[2-(4-Morpholin-4-yl-phenylamino)-pyrrolo[2,1-f][1,2,4]triazin-7-yl]-benzoic acid;
(6-Morpholin-4-yl-pyridin-3-yl)-(7-phenyl-pyrrolo[2,1-f][1,2,4]triazin-2-yl)-amine;
[7-(2-Methoxy-phenyl)-pyrrolo[2,1-f][1,2,4]triazin-2-yl]-(6-morpholin-4-yl-pyridin-3-yl)-amine;
[8-Methoxy-3-(2-methoxy-ethyl)-2,3,4,5-tetrahydro-1H-benzo[d]azepin-7-yl]-[7-(2-methoxy-phenyl)-pyrrolo[2,1-f][1,2,4]triazin-2-yl]-amine;
[7-(3-Chloro-phenyl)-pyrrolo[2,1-f][1,2,4]triazin-2-yl]-(4-piperidin-1-yl-phenyl)-amine;
(4-Morpholin-4-yl-phenyl)-pyrrolo[2,1-f][1,2,4]triazin-2-yl-amine;
2-(4-Morpholin-4-yl-phenylamino)-pyrrolo[2,1-f][1,2,4]triazine-7-carbonitrile;
N-(2-Dimethylamino-ethyl)-4-[2-(4-morpholin-4-yl-phenylamino)-pyrrolo[2,1-f][1,2,4]triazin-7-yl]-benzamide;
2-Pyrrolidin-1-yl-ethylamine to give 4-[2-(4-Morpholin-4-yl-phenylamino)-pyrrolo[2,1-f][1,2,4]triazin-7-yl]-N-(2-pyrrolidin-1-yl-ethyl)-benzamide;
4-[2-(4-Morpholin-4-yl-phenylamino)-pyrrolo[2,1-f][1,2,4]triazin-7-yl]-N-(3-pyrrolidin-1-yl-propyl)-benzamide;
N-Methyl-4-[2-(4-morpholin-4-yl-phenylamino)-pyrrolo[2,1-f][1,2,4]triazin-7-yl]-benzamide;
N-(2-Morpholin-4-yl-ethyl)-4-[2-(4-morpholin-4-yl-phenylamino)-pyrrolo[2,1-f][1,2,4]triazin-7-yl]-benzamide;
4-[2-(4-Morpholin-4-yl-phenylamino)-pyrrolo[2,1-f][1,2,4]triazin-7-yl]-N-(3-morpholin-4-yl-propyl)-benzamide;
[7-(4-Chloro-3-trifluoromethyl-phenyl)-pyrrolo[2,1-f][1,2,4]triazin-2-yl]-(4-morpholin-4-yl-phenyl)-amine;
[7-(4-Methanesulfonyl-phenyl)-pyrrolo[2,1-f][1,2,4]triazin-2-yl]-[4-(4-methyl-piperazin-1-yl)-phenyl]-amine;
[7-(4-Methanesulfonyl-phenyl)-pyrrolo[2,1-f][1,2,4]triazin-2-yl]-(6-morpholin-4-yl-pyridin-3-yl)-amine;
[7-(4-Methanesulfonyl-phenyl)-pyrrolo[2,1-f][1,2,4]triazin-2-yl]-(4-piperidin-1-yl-phenyl)-amine;
[7-(4-Methanesulfonyl-phenyl)-pyrrolo[2,1-f][1,2,4]triazin-2-yl]-[2-methoxy-4-(4-methyl-piperazin-1-yl)-phenyl]-amine;
(4-Morpholin-4-yl-phenyl)-{7-[4-(pyrrolidine-1-sulfonyl)-phenyl]-pyrrolo[2,1-f][1,2,4]triazin-2-yl}-amine;
[7-(3-Chloro-phenyl)-pyrrolo[2,1-f][1,2,4]triazin-2-yl]-[3-methoxy-4-(4-methyl-piperazin-1-yl)-phenyl]-amine;
[7-(3-Chloro-phenyl)-pyrrolo[2,1-f][1,2,4]triazin-2-yl]-(3-methoxy-4-morpholin-4-yl-phenyl)-amine;
[7-(3-Chloro-phenyl)-pyrrolo[2,1-f][1,2,4]triazin-2-yl]-(3-methyl-4-morpholin-4-yl-phenyl)-amine;
[7-(4-Methanesulfonyl-phenyl)-pyrrolo[2,1-f][1,2,4]triazin-2-yl]-[2-methyl-4-(4-methyl-piperazin-1-yl)-phenyl]-amine;
[7-(3-Chloro-phenyl)-pyrrolo[2,1-f][1,2,4]triazin-2-yl]-[2-methyl-4-(4-methyl-piperazin-1-yl)-phenyl]-amine;
[7-(3-Chloro-phenyl)-pyrrolo[2,1-f][1,2,4]triazin-2-yl]-[3-methyl-4-(4-methyl-piperazin-1-yl)-phenyl]-amine;
[7-(2-Chloro-5-trifluoromethyl-phenyl)-pyrrolo[2,1-f][1,2,4]triazin-2-yl]-(4-morpholin-4-yl-phenyl)-amine;
N,N-Dimethylsulfonamide-4-benzeneboronic acid to give N,N-Dimethyl-4-[2-(4-morpholin-4-yl-phenylamino)-pyrrolo[2,1-f][1,2,4]triazin-7-yl]-benzenesulfonamide;
[2-(4-Morpholin-4-yl-phenylamino)-pyrrolo[2,1-f][1,2,4]triazin-7-yl]-phenyl-methanone;
[2-Methoxy-4-(4-methyl-piperazin-1-yl)-phenyl]-[7-(6-methoxy-pyridin-3-yl)-pyrrolo[2,1-f][1,2,4]triazin-2-yl]-amine;
4,N,N-Trimethyl-3-{2-[4-(4-methyl-piperazin-1-yl)-phenylamino]-pyrrolo[2,1-f][1,2,4]triazin-7-yl}-benzenesulfonamide;
3-{2-[2-Methoxy-4-(4-methyl-piperazin-1-yl)-phenylamino]-pyrrolo[2,1-f][1,2,4]triazin-7-yl}-4,N,N-trimethyl-benzenesulfonamide;
[7-(3-Methanesulfonyl-phenyl)-pyrrolo[2,1-f][1,2,4]triazin-2-yl]-[2-methoxy-4-(4-methyl-piperazin-1-yl)-phenyl]-amine;
5-{2-[2-Methoxy-4-(4-methyl-piperazin-1-yl)-phenylamino]-pyrrolo[2,1-f][1,2,4]triazin-7-yl}-pyridine-2-carbonitrile;
[4-(4-Methyl-piperazin-1-yl)-phenyl]-(7-phenylsulfanyl-pyrrolo[2,1-f][1,2,4]triazin-2-yl)-amine;

[7-(3-Chloro-phenyl)-pyrrolo[2,1-f][1,2,4]triazin-2-yl]-(6-morpholin-4-yl-pyridin-3-yl)-amine;
(2-Chloro-4-morpholin-4-yl-phenyl)-(5-chloro-7-phenyl-pyrrolo[2,1-f][1,2,4]triazin-2-yl)-amine;
[7-(6-Methoxy-pyridin-3-yl)-pyrrolo[2,1-f][1,2,4]triazin-2-yl]-[4-(4-methyl-piperazin-1-yl)-phenyl]-amine;
[7-(3-Methanesulfonyl-phenyl)-pyrrolo[2,1-f][1,2,4]triazin-2-yl]-[4-(4-methyl-piperazin-1-yl)-phenyl]-amine;
N,N-Dimethyl-4-{2-[4-(4-methyl-piperazin-1-yl)-phenylamino]-pyrrolo[2,1-f][1,2,4]triazin-7-yl}-benzenesulfonamide;
(5,7-Dibromo-pyrrolo[2,1-f][1,2,4]triazin-2-yl)-[4-(4-methyl-piperazin-1-yl)-phenyl]-amine;
[7-(4-Methanesulfonyl-phenyl)-pyrrolo[2,1-f][1,2,4]triazin-2-yl]-(4-piperidin-1-yl-phenyl)-amine;
N,N-Dimethyl-4-[2-(4-piperidin-1-yl-phenylamino)-pyrrolo[2,1-f][1,2,4]triazin-7-yl]-benzenesulfonamide;
(1-{4-[7-(4-Methanesulfonyl-phenyl)-pyrrolo[2,1-f][1,2,4]triazin-2-ylamino]-phenyl}-piperidin-4-yl)-methanol; compound with trifluoro-acetic acid;
2-(4-{4-[7-(4-Methanesulfonyl-phenyl)-pyrrolo[2,1-f][1,2,4]triazin-2-ylamino]-phenyl}-piperazin-1-yl)-ethanol;
[7-(4-Methanesulfonyl-phenyl)-pyrrolo[2,1-f][1,2,4]triazin-2-yl]-[3-(2-methoxy-ethyl)-2,3,4,5-tetrahydro-1H-benzo[d]azepin-7-yl]-amine;
[3-Fluoro-4-(4-methyl-piperazin-1-yl)-phenyl]-[7-(2-methoxy-phenyl)-pyrrolo[2,1-f][1,2,4]triazin-2-yl]-amine;
[5-Bromo-7-(4-methanesulfonyl-phenyl)-pyrrolo[2,1-f][1,2,4]triazin-2-yl]-[4-(4-methyl-piperazin-1-yl)-phenyl]-amine;
8-[7-(4-Methanesulfonyl-phenyl)-pyrrolo[2,1-f][1,2,4]triazin-2-ylamino]-5,5-dimethyl-1,3,4,5-tetrahydro-benzo[b]azepin-2-one;
[7-(3-Chloro-phenyl)-pyrrolo[2,1-f][1,2,4]triazin-2-yl]-{4-[2-(4-ethyl-piperazin-1-yl)-ethoxy]-phenyl}-amine;
[7-(2-Methoxy-phenyl)-pyrrolo[2,1-f][1,2,4]triazin-2-yl]-{4-[2-(4-methyl-piperazin-1-yl)-ethoxy]-phenyl}-amine;
2-[4-(4-Amino-phenyl)-piperazin-1-yl]-ethanol to give 2-(4-{4-[7-(3-Methanesulfonyl-phenyl)-pyrrolo[2,1-f][1,2,4]triazin-2-ylamino]-phenyl}-piperazin-1-yl)-ethanol;
(1-{4-[7-(3-Methanesulfonyl-phenyl)-pyrrolo[2,1-f][1,2,4]triazin-2-ylamino]-phenyl}-piperidin-4-yl)-methanol;
(4-Morpholin-4-yl-phenyl)-(7-phenylsulfanyl-pyrrolo[2,1-f][1,2,4]triazin-2-yl)-amine;
[7-(2-Methoxy-phenylsulfanyl)-pyrrolo[2,1-f][1,2,4]triazin-2-yl]-[4-(4-methyl-piperazin-1-yl)-phenyl]-amine;
[5-Bromo-7-(4-methanesulfonyl-phenyl)-pyrrolo[2,1-f][1,2,4]triazin-2-yl]-(4-morpholin-4-yl-phenyl)-amine;
(5-Bromo-7-phenyl-pyrrolo[2,1-f][1,2,4]triazin-2-yl)-[4-(4-methyl-piperazin-1-yl)-phenyl]-amine;
[5-Bromo-7-(2-methoxy-phenyl)-pyrrolo[2,1-f][1,2,4]triazin-2-yl]-[4-(4-methyl-piperazin-1-yl)-phenyl]-amine;
[7-Bromo-5-(2-methoxy-phenyl)-pyrrolo[2,1-f][1,2,4]triazin-2-yl]-[4-(4-methyl-piperazin-1-yl)-phenyl]-amine;
[7-(2-Methoxy-phenyl)-5-vinyl-pyrrolo[2,1-f][1,2,4]triazin-2-yl]-[4-(4-methyl-piperazin-1-yl)-phenyl]-amine;
[7-(4-Methanesulfonyl-phenyl)-5-vinyl-pyrrolo[2,1-f][1,2,4]triazin-2-yl]-[4-(4-methyl-piperazin-1-yl)-phenyl]-amine;
[7-(2-Methoxy-phenyl)-5-methyl-pyrrolo[2,1-f][1,2,4]triazin-2-yl]-[4-(4-methyl-piperazin-1-yl)-phenyl]-amine;
[5-Ethyl-7-(2-methoxy-phenyl)-pyrrolo[2,1-f][1,2,4]triazin-2-yl]-[4-(4-methyl-piperazin-1-yl)-phenyl]-amine;
[7-(4-Methanesulfonyl-phenyl)-5-methyl-pyrrolo[2,1-f][1,2,4]triazin-2-yl]-(4-morpholin-4-yl-phenyl)-amine;
[7-(4-Methanesulfonyl-phenyl)-5-methyl-pyrrolo[2,1-f][1,2,4]triazin-2-yl]-[4-(4-methyl-piperazin-1-yl)-phenyl]-amine;
[7-(2-Ethoxy-phenyl)-pyrrolo[2,1-f][1,2,4]triazin-2-yl]-[4-(4-methyl-piperazin-1-yl)-phenyl]-amine;
[5,6-Dibromo-7-(2-methoxy-phenyl)-pyrrolo[2,1-f][1,2,4]triazin-2-yl]-(4-morpholin-4-yl-phenyl)-amine;
(7-Benzenesulfonyl-pyrrolo[2,1-f][1,2,4]triazin-2-yl)-(4-morpholin-4-yl-phenyl)-amine;
[7-(2-Methoxy-phenyl)-5,6-dimethyl-pyrrolo[2,1-f][1,2,4]triazin-2-yl]-(4-morpholin-4-yl-phenyl)-amine;
7-(4-Methanesulfonyl-phenyl)-2-(2-methoxy-1-methyl-ethoxy)-pyrrolo[2,1-f][1,2,4]triazine;
7-(2-Methoxy-phenyl)-2-[4-(4-methyl-piperazin-1-yl)-phenylamino]-pyrrolo[2,1-f][1,2,4]triazine-5-carbonitrile;
2-{4-[4-(7-Pyridin-3-yl-pyrrolo[2,1-f][1,2,4]triazin-2-ylamino)-phenyl]-piperazin-1-yl}-ethanol;
{1-[4-(7-Pyridin-3-yl-pyrrolo[2,1-f][1,2,4]triazin-2-ylamino)-phenyl]-piperidin-4-yl}-methanol;
N-(2-Methanesulfonyl-ethyl)-4-[2-(4-morpholin-4-yl-phenylamino)-pyrrolo[2,1-f][1,2,4]triazin-7-yl]-benzamide;
N-tert-Butyl-3-{2-[4-(2-pyrrolidin-1-yl-ethoxy)-phenylamino]-pyrrolo[2,1-f][1,2,4]triazin-7-yl}-benzenesulfonamide;
{4-[2-(4-Methyl-piperazin-1-yl)-ethoxy]-phenyl}-(7-pyridin-3-yl-pyrrolo[2,1-f][1,2,4]triazin-2-yl)-amine;
{4-[3-(4-Methyl-piperazin-1-yl)-propoxy]-phenyl}-(7-pyridin-3-yl-pyrrolo[2,1-f][1,2,4]triazin-2-yl)-amine;
[7-(2-Methoxy-phenyl)-pyrrolo[2,1-f][1,2,4]triazin-2-yl]-[4-(2-pyrrolidin-1-yl-ethoxy)-phenyl]-amine;
[7-(2-Methoxy-phenyl)-pyrrolo[2,1-f][1,2,4]triazin-2-yl]-(1H-pyrazol-3-yl)-amine;
(7-Cyclohexyl-pyrrolo[2,1-f][1,2,4]triazin-2-yl)-[4-(4-methyl-piperazin-1-yl)-phenyl]-amine;
(1H-Pyrazol-3-yl)-(7-pyridin-3-yl-pyrrolo[2,1-f][1,2,4]triazin-2-yl)-amine;
[4-(2-Morpholin-4-yl-ethoxy)-phenyl]-(7-pyridin-3-yl-pyrrolo[2,1-f][1,2,4]triazin-2-yl)-amine;
(7-Pyridin-3-yl-pyrrolo[2,1-f][1,2,4]triazin-2-yl)-[4-(2-pyrrolidin-1-yl-ethoxy)-phenyl]-amine;
(7-Cyclohexyl-pyrrolo[2,1-f][1,2,4]triazin-2-yl)-(4-morpholin-4-yl-phenyl)-amine;
[7-(2-Methoxy-phenyl)-pyrrolo[2,1-f][1,2,4]triazin-2-yl]-[4-(2-morpholin-4-yl-ethoxy)-phenyl]-amine;
[7-(5-Chloro-2-methoxy-phenyl)-pyrrolo[2,1-f][1,2,4]triazin-2-yl]-(3,4,5-trimethoxy-phenyl)-amine;
[7-(2-Methoxy-phenyl)-pyrrolo[2,1-f][1,2,4]triazin-2-yl]-(3,4,5-trimethoxy-phenyl)-amine;
[7-(3-Chloro-phenyl)-pyrrolo[2,1-f][1,2,4]triazin-2-yl]-(3,4,5-trimethoxy-phenyl)-amine;
[7-(5-Chloro-2-methoxy-phenyl)-pyrrolo[2,1-f][1,2,4]triazin-2-yl]-(3-methoxy-phenyl)-amine;
(3-Methoxy-phenyl)-[7-(2-methoxy-phenyl)-pyrrolo[2,1-f][1,2,4]triazin-2-yl]-amine;

[7-(3-Chloro-phenyl)-pyrrolo[2,1-f][1,2,4]triazin-2-yl]-(3-methoxy-phenyl)-amine;
[7-(2-Methoxy-phenyl)-pyrrolo[2,1-f][1,2,4]triazin-2-yl]-(3-morpholin-4-yl-phenyl)-amine;
[7-(3-Chloro-phenyl)-pyrrolo[2,1-f][1,2,4]triazin-2-yl]-(3-morpholin-4-yl-phenyl)-amine;
1,3-Benzodioxol-5-yl-[7-(2-methoxy-phenyl)-pyrrolo[2,1-f][1,2,4]triazin-2-yl]-amine;
1,3-Benzodioxol-5-yl-[7-(3-chloro-phenyl)-pyrrolo[2,1-f][1,2,4]triazin-2-yl]-amine;
[7-(5-Chloro-2-methoxy-phenyl)-pyrrolo[2,1-f][1,2,4]triazin-2-yl]-(3,4-dimethoxy-phenyl)-amine;
[7-(3-Chloro-phenyl)-pyrrolo[2,1-f][1,2,4]triazin-2-yl]-(3,4-dimethoxy-phenyl)-amine;
[7-(5-Chloro-2-methoxy-phenyl)-pyrrolo[2,1-f][1,2,4]triazin-2-yl]-(4-methoxy-phenyl)-amine;
(4-Methoxy-phenyl)-[7-(2-methoxy-phenyl)-pyrrolo[2,1-f][1,2,4]triazin-2-yl]-amine;
[7-(3-Chloro-phenyl)-pyrrolo[2,1-f][1,2,4]triazin-2-yl]-(4-methoxy-phenyl)-amine;
[7-(3-Chloro-phenyl)-pyrrolo[2,1-f][1,2,4]triazin-2-yl]-(3,5-dimethoxy-phenyl)-amine;
[7-(5-Chloro-2-methoxy-phenyl)-pyrrolo[2,1-f][1,2,4]triazin-2-yl]-(3,5-dimethoxy-phenyl)-amine;
(3,5-Dimethoxy-phenyl)-[7-(2-methoxy-phenyl)-pyrrolo[2,1-f][1,2,4]triazin-2-yl]-amine;
N-[7-(3-Chloro-phenyl)-pyrrolo[2,1-f][1,2,4]triazin-2-yl]-N',N'-dimethyl-benzene-1,3-diamine;
[7-(2-Methoxy-phenyl)-pyrrolo[2,1-f][1,2,4]triazin-2-yl]-[3-(4-methyl-piperazin-1-yl)-phenyl]-amine;
[7-(3-Chloro-phenyl)-pyrrolo[2,1-f][1,2,4]triazin-2-yl]-[3-(4-methyl-piperazin-1-yl)-phenyl]-amine;
[7-(4-Methanesulfonyl-phenyl)-pyrrolo[2,1-f][1,2,4]triazin-2-yl]-(3,4,5-trimethoxy-phenyl)-amine;
[7-(4-Methanesulfonyl-phenyl)-pyrrolo[2,1-f][1,2,4]triazin-2-yl]-(3-morpholin-4-yl-phenyl)-amine;
3-[7-(2-Methoxy-phenyl)-pyrrolo[2,1-f][1,2,4]triazin-2-ylamino]-benzamide;
3-[7-(3-Chloro-phenyl)-pyrrolo[2,1-f][1,2,4]triazin-2-ylamino]-benzamide;
3-[7-(5-Chloro-2-methoxy-phenyl)-pyrrolo[2,1-f][1,2,4]triazin-2-ylamino]-benzamide;
[7-(3-Chloro-phenyl)-pyrrolo[2,1-f][1,2,4]triazin-2-yl]-(4-pyrrolidin-1-yl-phenyl)-amine;
[7-(5-Chloro-2-methoxy-phenyl)-pyrrolo[2,1-f][1,2,4]triazin-2-yl]-(4-pyrrolidin-1-yl-phenyl)-amine;
[7-(2-Methoxy-phenyl)-pyrrolo[2,1-f][1,2,4]triazin-2-yl]-(4-pyrrolidin-1-yl-phenyl)-amine;
(1H-Indol-5-yl)-[7-(2-methoxy-phenyl)-pyrrolo[2,1-f][1,2,4]triazin-2-yl]-amine;
[7-(5-Chloro-2-methoxy-phenyl)-pyrrolo[2,1-f][1,2,4]triazin-2-yl]-(1H-indol-5-yl)-amine;
[7-(2-Methoxy-phenyl)-pyrrolo[2,1-f][1,2,4]triazin-2-yl]-quinolin-6-yl-amine;
[7-(5-Chloro-2-methoxy-phenyl)-pyrrolo[2,1-f][1,2,4]triazin-2-yl]-quinolin-6-yl-amine;
(3-Morpholin-4-yl-phenyl)-pyrrolo[2,1-f][1,2,4]triazin-2-yl-amine;
[7-(3-Fluoro-phenyl)-pyrrolo[2,1-f][1,2,4]triazin-2-yl]-(3-morpholin-4-yl-phenyl)-amine;
[7-(3-Chloro-phenyl)-pyrrolo[2,1-f][1,2,4]triazin-2-yl]-(1H-indol-5-yl)-amine;
[7-(3-Chloro-phenyl)-pyrrolo[2,1-f][1,2,4]triazin-2-yl]-quinolin-6-yl-amine;
2-(4-{3-[7-(2-Methoxy-phenyl)-pyrrolo[2,1-f][1,2,4]triazin-2-ylamino]-phenyl}-piperazin-1-yl)-ethanol;
2-(4-{3-[7-(3-Chloro-phenyl)-pyrrolo[2,1-f][1,2,4]triazin-2-ylamino]-phenyl}-piperazin-1-yl)-ethanol;
2-(4-{3-[7-(5-Chloro-2-methoxy-phenyl)-pyrrolo[2,1-f][1,2,4]triazin-2-ylamino]-phenyl}-piperazin-1-yl)-ethanol;
2-(4-{3-[7-(4-Methanesulfonyl-phenyl)-pyrrolo[2,1-f][1,2,4]triazin-2-ylamino]-phenyl}-piperazin-1-yl)-ethanol;
N-{4-[2-(3-Morpholin-4-yl-phenylamino)-pyrrolo[2,1-f][1,2,4]triazin-7-yl]-phenyl}-methanesulfonamide;
N-{3-[2-(3-Morpholin-4-yl-phenylamino)-pyrrolo[2,1-f][1,2,4]triazin-7-yl]-phenyl}-methanesulfonamide;
[7-(3-Methanesulfonyl-phenyl)-pyrrolo[2,1-f][1,2,4]triazin-2-yl]-(3-morpholin-4-yl-phenyl)-amine;
[7-(3-Methanesulfonyl-phenyl)-pyrrolo[2,1-f][1,2,4]triazin-2-yl]-(3,4,5-trimethoxy-phenyl)-amine;
(3-Fluoro-4-morpholin-4-yl-phenyl)-[7-(2-methoxy-phenyl)-pyrrolo[2,1-f][1,2,4]triazin-2-yl]-amine;
[7-(3-Chloro-phenyl)-pyrrolo[2,1-f][1,2,4]triazin-2-yl]-(3-fluoro-4-morpholin-4-yl-phenyl)-amine;
[7-(5-Chloro-2-methoxy-phenyl)-pyrrolo[2,1-f][1,2,4]triazin-2-yl]-(3-fluoro-4-morpholin-4-yl-phenyl)-amine;
(3-Fluoro-4-morpholin-4-yl-phenyl)-[7-(4-methanesulfonyl-phenyl)-pyrrolo[2,1-f][1,2,4]triazin-2-yl]-amine;
7-(3-Chloro-phenyl)-2-(2-methoxy-ethoxy)-pyrrolo[2,1-f][1,2,4]triazine;
7-(5-Chloro-2-methoxy-phenyl)-2-(2-methoxy-ethoxy)-pyrrolo[2,1-f][1,2,4]triazine;
(3-Morpholin-4-yl-phenyl)-{7-[4-(propane-2-sulfonyl)-phenyl]-pyrrolo[2,1-f][1,2,4]triazin-2-yl}-amine;
[7-(3-Fluoro-4-methanesulfonyl-phenyl)-pyrrolo[2,1-f][1,2,4]triazin-2-yl]-(3-morpholin-4-yl-phenyl)-amine;
N-Methyl-4-[2-(3-morpholin-4-yl-phenylamino)-pyrrolo[2,1-f][1,2,4]triazin-7-yl]-benzamide;
[7-(2-Methoxy-phenyl)-pyrrolo[2,1-f][1,2,4]triazin-2-yl]-[3-(4-morpholin-4-yl-piperidin-1-yl)-phenyl]-amine;
[7-(5-Chloro-2-methoxy-phenyl)-pyrrolo[2,1-f][1,2,4]triazin-2-yl]-[3-(4-morpholin-4-yl-piperidin-1-yl)-phenyl]-amine;
7-(4-Methanesulfonyl-phenyl)-2-(2-methoxy-ethoxy)-pyrrolo[2,1-f][1,2,4]triazine;
[7-(1-Methyl-1H-pyrazol-4-yl)-pyrrolo[2,1-f][1,2,4]triazin-2-yl]-(3-morpholin-4-yl-phenyl)-amine;
(4-Morpholin-4-yl-phenyl)-{7-[4-(propane-2-sulfonyl)-phenyl]-pyrrolo[2,1-f][1,2,4]triazin-2-yl}-amine;
N-{4-[2-(4-Morpholin-4-yl-phenylamino)-pyrrolo[2,1-f][1,2,4]triazin-7-yl]-phenyl}-methanesulfonamide;
N-{3-[2-(4-Morpholin-4-yl-phenylamino)-pyrrolo[2,1-f][1,2,4]triazin-7-yl]-phenyl}-methanesulfonamide;
(S)-1-(4-{4-[7-(2-Methoxy-phenyl)-pyrrolo[2,1-f][1,2,4]triazin-2-ylamino]-phenyl}-piperazin-1-yl)-propan-2-ol;
(S)-1-(4-{4-[7-(5-Chloro-2-methoxy-phenyl)-pyrrolo[2,1-f][1,2,4]triazin-2-ylamino]-phenyl}-piperazin-1-yl)-propan-2-ol;
(S)-1-(4-{4-[7-(3-Chloro-phenyl)-pyrrolo[2,1-f][1,2,4]triazin-2-ylamino]-phenyl}-piperazin-1-yl)-propan-2-ol;
(S)-1-(4-{4-[7-(4-Methanesulfonyl-phenyl)-pyrrolo[2,1-f][1,2,4]triazin-2-ylamino]-phenyl}-piperazin-1-yl)-propan-2-ol;
(R)-1-(4-{4-[7-(2-Methoxy-phenyl)-pyrrolo[2,1-f][1,2,4]triazin-2-ylamino]-phenyl}-piperazin-1-yl)-propan-2-ol;
(R)-1-(4-{4-[7-(5-Chloro-2-methoxy-phenyl)-pyrrolo[2,1-f][1,2,4]triazin-2-ylamino]-phenyl}-piperazin-1-yl)-propan-2-ol;

(R)-1-(4-{4-[7-(3-Chloro-phenyl)-pyrrolo[2,1-f][1,2,4]triazin-2-ylamino]-phenyl}-piperazin-1-yl)-propan-2-ol;
(R)-1-(4-{4-[7-(4-Methanesulfonyl-phenyl)-pyrrolo[2,1-f][1,2,4]triazin-2-ylamino]-phenyl}-piperazin-1-yl)-propan-2-ol;
(S)-1-(4-{3-[7-(2-Methoxy-phenyl)-pyrrolo[2,1-f][1,2,4]triazin-2-ylamino]-phenyl}-piperazin-1-yl)-propan-2-ol;
(S)-1-(4-{3-[7-(5-Chloro-2-methoxy-phenyl)-pyrrolo[2,1-f][1,2,4]triazin-2-ylamino]-phenyl}-piperazin-1-yl)-propan-2-ol;
(S)-1-(4-{3-[7-(3-Chloro-phenyl)-pyrrolo[2,1-f][1,2,4]triazin-2-ylamino]-phenyl}-piperazin-1-yl)-propan-2-ol;
(R)-1-(4-{3-[7-(2-Methoxy-phenyl)-pyrrolo[2,1-f][1,2,4]triazin-2-ylamino]-phenyl}-piperazin-1-yl)-propan-2-ol;
(R)-1-(4-{3-[7-(5-Chloro-2-methoxy-phenyl)-pyrrolo[2,1-f][1,2,4]triazin-2-ylamino]-phenyl}-piperazin-1-yl)-propan-2-ol;
(R)-1-(4-{3-[7-(3-Chloro-phenyl)-pyrrolo[2,1-f][1,2,4]triazin-2-ylamino]-phenyl}-piperazin-1-yl)-propan-2-ol;
(S)-1-(4-{3-[7-(4-Methanesulfonyl-phenyl)-pyrrolo[2,1-f][1,2,4]triazin-2-ylamino]-phenyl}-piperazin-1-yl)-propan-2-ol;
(R)-1-(4-{3-[7-(4-Methanesulfonyl-phenyl)-pyrrolo[2,1-f][1,2,4]triazin-2-ylamino]-phenyl}-piperazin-1-yl)-propan-2-ol;
1-(4-{3-[7-(2-Methoxy-phenyl)-pyrrolo[2,1-f][1,2,4]triazin-2-ylamino]-phenyl}-piperazin-1-yl)-2-methyl-propan-2-ol;
1-(4-{3-[7-(5-Chloro-2-methoxy-phenyl)-pyrrolo[2,1-f][1,2,4]triazin-2-ylamino]-phenyl}-piperazin-1-yl)-2-methyl-propan-2-ol;
1-(4-{3-[7-(3-Chloro-phenyl)-pyrrolo[2,1-f][1,2,4]triazin-2-ylamino]-phenyl}-piperazin-1-yl)-2-methyl-propan-2-ol;
1-(4-{4-[7-(2-Methoxy-phenyl)-pyrrolo[2,1-f][1,2,4]triazin-2-ylamino]-phenyl}-piperazin-1-yl)-2-methyl-propan-2-ol;
1-(4-{4-[7-(5-Chloro-2-methoxy-phenyl)-pyrrolo[2,1-f][1,2,4]triazin-2-ylamino]-phenyl}-piperazin-1-yl)-2-methyl-propan-2-ol;
1-(4-{4-[7-(3-Chloro-phenyl)-pyrrolo[2,1-f][1,2,4]triazin-2-ylamino]-phenyl}-piperazin-1-yl)-2-methyl-propan-2-ol;
{2-Methoxy-4-[4-(1-methyl-piperidin-4-yl)-piperazin-1-yl]-phenyl}-[7-(2-methoxy-phenyl)-pyrrolo[2,1-f][1,2,4]triazin-2-yl]-amine;
1-[4-(1-{3-Methoxy-4-[7-(2-methoxy-phenyl)-pyrrolo[2,1-f][1,2,4]triazin-2-ylamino]-phenyl}-piperidin-3-yl)-piperazin-1-yl]-ethanone;
{4-[3-(4-Methanesulfonyl-piperazin-1-yl)-piperidin-1-yl]-2-methoxy-phenyl}-[7-(2-methoxy-phenyl)-pyrrolo[2,1-f][1,2,4]triazin-2-yl]-amine;
4-(1-{3-Methoxy-4-[7-(2-methoxy-phenyl)-pyrrolo[2,1-f][1,2,4]triazin-2-ylamino]-phenyl}-piperidin-3-yl)-piperazine-1-carboxylic acid benzyl ester;
{2-Methoxy-4-[3-(4-methyl-piperazin-1-yl)-piperidin-1-yl]-phenyl}-[7-(2-methoxy-phenyl)-pyrrolo[2,1-f][1,2,4]triazin-2-yl]-amine;
[2-Methoxy-4-(4-morpholin-4-yl-piperidin-1-yl)-phenyl]-[7-(2-methoxy-phenyl)-pyrrolo[2,1-f][1,2,4]triazin-2-yl]-amine;
2-Methoxy-4-[4-(4-methyl-piperazin-1-yl)-piperidin-1-yl]-phenyl}-(7-pyridin-3-yl-pyrrolo[2,1-f][1,2,4]triazin-2-yl)-amine;
4-(2-{2-Methoxy-4-[4-(4-methyl-piperazin-1-yl)-piperidin-1-yl]-phenylamino}-pyrrolo[2,1-f][1,2,4]triazin-7-yl)-N-methyl-benzamide;
{2-Methoxy-4-[4-(4-methyl-piperazin-1-yl)-piperidin-1-yl]-phenyl}-[7-(2-methoxy-phenyl)-pyrrolo[2,1-f][1,2,4]triazin-2-yl]-amine;
[4-(4-Ethyl-morpholin-2-yl)-phenyl]-[7-(2-methoxy-phenyl)-pyrrolo[2,1-f][1,2,4]triazin-2-yl]-amine;
[7-(5-Chloro-2-methoxy-phenyl)-pyrrolo[2,1-f][1,2,4]triazin-2-yl]-[4-(4-ethyl-morpholin-2-yl)-phenyl]-amine;
(4-Morpholin-4-yl-phenyl)-[1,2,4]triazino[1,6-a]indol-2-yl-amine;
{2-Methoxy-4-[4-(4-methyl-piperazin-1-yl)-piperidin-1-yl]-phenyl}-[1,2,4]triazino[1,6-a]indol-2-yl-amine;
[4-(4-Methyl-piperazin-1-yl)-phenyl]-[1,2,4]triazino[1,6-a]indol-2-yl-amine;
{4-[4-(4-Methyl-piperazin-1-yl)-piperidin-1-yl]-phenyl}-[1,2,4]triazino[1,6-a]indol-2-yl-amine;
5,5-Dimethyl-8-([1,2,4]triazino[1,6-a]indol-2-ylamino)-1,3,4,5-tetrahydro-benzo[b]azepin-2-one;
(2-Methoxy-4-morpholin-4-yl-phenyl)-[1,2,4]triazino[1,6-a]indol-2-yl-amine;
[2-Methoxy-4-(4-methyl-piperazin-1-yl)-phenyl]-[1,2,4]triazino[1,6-a]indol-2-yl-amine;
(7-Methoxy-[1,2,4]triazino[1,6-a]indol-2-yl)-(4-morpholin-4-yl-phenyl)-amine;
(2-Methoxy-4-morpholin-4-yl-phenyl)-(7-methoxy-[1,2,4]triazino[1,6-a]indol-2-yl)-amine;
Phenyl-[1,2,4]triazino[1,6-a]indol-2-yl-amine;
(3-Chloro-phenyl)-[1,2,4]triazino[1,6-a]indol-2-yl-amine;
(3-Methoxy-phenyl)-[1,2,4]triazino[1,6-a]indol-2-yl-amine;
N,N-Dimethyl-3-([1,2,4]triazino[1,6-a]indol-2-ylamino)-benzenesulfonamide;
N-{2-Isopropyl-5-[7-(2-methoxy-phenyl)-pyrrolo[2,1-f][1,2,4]triazin-2-ylamino]-phenyl}-acetamide;
N-{5-[7-(5-Chloro-2-methoxy-phenyl)-pyrrolo[2,1-f][1,2,4]triazin-2-ylamino]-2-isopropyl-phenyl}-acetamide;
N-{5-[7-(3-Chloro-phenyl)-pyrrolo[2,1-f][1,2,4]triazin-2-ylamino]-2-isopropyl-phenyl}-acetamide;
N-[2-Isopropyl-5-(7-pyridin-3-yl-pyrrolo[2,1-f][1,2,4]triazin-2-ylamino)-phenyl]-acetamide;
N-{2-tert-Butyl-5-[7-(5-chloro-2-methoxy-phenyl)-pyrrolo[2,1-f][1,2,4]triazin-2-ylamino]-phenyl}-acetamide;
N-{2-tert-Butyl-5-[7-(5-chloro-2-methoxy-phenyl)-pyrrolo[2,1-f][1,2,4]triazin-2-ylamino]-phenyl}-acetamide;
N-{2-tert-Butyl-5-[7-(3-chloro-phenyl)-pyrrolo[2,1-f][1,2,4]triazin-2-ylamino]-phenyl}-acetamide;
N-[2-tert-Butyl-5-(7-pyridin-3-yl-pyrrolo[2,1-f][1,2,4]triazin-2-ylamino)-phenyl]-acetamide;
(3-Morpholin-4-yl-phenyl)-(7-pyridin-3-yl-pyrrolo[2,1-f][1,2,4]triazin-2-yl)-amine;
[7-(2-Methoxy-phenyl)-pyrrolo[2,1-f][1,2,4]triazin-2-yl]-{4-[4-(4-methyl-piperazin-1-yl)-piperidin-1-yl]-phenyl}-amine;
[7-(5-Chloro-2-methoxy-phenyl)-pyrrolo[2,1-f][1,2,4]triazin-2-yl]-{4-[4-(4-methyl-piperazin-1-yl)-piperidin-1-yl]-phenyl}-amine;

[7-(3-Chloro-phenyl)-pyrrolo[2,1-f][1,2,4]triazin-2-yl]-{4-[4-(4-methyl-piperazin-1-yl)-piperidin-1-yl]-phenyl}-amine;
{4-[4-(4-Methyl-piperazin-1-yl)-piperidin-1-yl]-phenyl}-(7-pyridin-3-yl-pyrrolo[2,1-f][1,2,4]triazin-2-yl)-amine;
{4-[7-(2-Methoxy-phenyl)-pyrrolo[2,1-f][1,2,4]triazin-2-ylamino]-phenyl}-morpholin-4-yl-methanone;
{4-[7-(5-Chloro-2-methoxy-phenyl)-pyrrolo[2,1-f][1,2,4]triazin-2-ylamino]-phenyl}-morpholin-4-yl-methanone;
{4-[7-(3-Chloro-phenyl)-pyrrolo[2,1-f][1,2,4]triazin-2-ylamino]-phenyl}-morpholin-4-yl-methanone;
Morpholin-4-yl-[4-(7-pyridin-3-yl-pyrrolo[2,1-f][1,2,4]triazin-2-ylamino)-phenyl]-methanone;
{4-[7-(2-Methoxy-phenyl)-pyrrolo[2,1-f][1,2,4]triazin-2-ylamino]-phenyl}-(4-methyl-piperazin-1-yl)-methanone;
{4-[7-(5-Chloro-2-methoxy-phenyl)-pyrrolo[2,1-f][1,2,4]triazin-2-ylamino]-phenyl}-(4-methyl-piperazin-1-yl)-methanone;
{4-[7-(3-Chloro-phenyl)-pyrrolo[2,1-f][1,2,4]triazin-2-ylamino]-phenyl}-(4-methyl-piperazin-1-yl)-methanone;
(4-Methyl-piperazin-1-yl)-[4-(7-pyridin-3-yl-pyrrolo[2,1-f][1,2,4]triazin-2-ylamino)-phenyl]-methanone;
1-[7-(2-Methoxy-phenyl)-pyrrolo[2,1-f][1,2,4]triazin-2-yl]-1H-imidazo[4,5-c]pyridine;
1-[7-(5-Chloro-2-methoxy-phenyl)-pyrrolo[2,1-f][1,2,4]triazin-2-yl]-1H-imidazo[4,5-c]pyridine;
1-[7-(3-Chloro-phenyl)-pyrrolo[2,1-f][1,2,4]triazin-2-yl]-1H-imidazo[4,5-c]pyridine;
1-(7-Pyridin-3-yl-pyrrolo[2,1-f][1,2,4]triazin-2-yl)-1H-imidazo[4,5-c]pyridine;
N-{2-tert-Butyl-5-[7-(4-methanesulfonyl-phenyl)-pyrrolo[2,1-f][1,2,4]triazin-2-ylamino]-phenyl}-acetamide;
{3-[7-(2-Methoxy-phenyl)-pyrrolo[2,1-f][1,2,4]triazin-2-ylamino]-phenyl}-morpholin-4-yl-methanone;
{3-[7-(5-Chloro-2-methoxy-phenyl)-pyrrolo[2,1-f][1,2,4]triazin-2-ylamino]-phenyl}-morpholin-4-yl-methanone;
{3-[7-(3-Chloro-phenyl)-pyrrolo[2,1-f][1,2,4]triazin-2-ylamino]-phenyl}-morpholin-4-yl-methanone;
1-[7-(4-Methanesulfonyl-phenyl)-pyrrolo[2,1-f][1,2,4]triazin-2-yl]-1H-imidazo[4,5-c]pyridine;
5-[2-(4-Morpholin-4-yl-phenylamino)-pyrrolo[2,1-f][1,2,4]triazin-7-yl]-pyridin-2-ol;
5-[2-(3-Morpholin-4-yl-phenylamino)-pyrrolo[2,1-f][1,2,4]triazin-7-yl]-pyridin-2-ol;
[7-(2-Methoxy-phenyl)-pyrrolo[2,1-f][1,2,4]triazin-2-yl]-(4-morpholin-4-yl-phenyl)-amine;
[7-(2-Methoxy-phenyl)-pyrrolo[2,1-f][1,2,4]triazin-2-yl]-[4-(4-morpholin-4-yl-piperidin-1-yl)-phenyl]-amine;
[7-(5-Chloro-2-methoxy-phenyl)-pyrrolo[2,1-f][1,2,4]triazin-2-yl]-[4-(4-morpholin-4-yl-piperidin-1-yl)-phenyl]-amine;
[7-(3-Chloro-phenyl)-pyrrolo[2,1-f][1,2,4]triazin-2-yl]-[4-(4-morpholin-4-yl-piperidin-1-yl)-phenyl]-amine;
[4-(4-Morpholin-4-yl-piperidin-1-yl)-phenyl]-(7-pyridin-3-yl-pyrrolo[2,1-f][1,2,4]triazin-2-yl)-amine;
{3-[7-(2-Methoxy-phenyl)-pyrrolo[2,1-f][1,2,4]triazin-2-ylamino]-phenyl}-(4-methyl-piperazin-1-yl)-methanone;
{3-[7-(5-Chloro-2-methoxy-phenyl)-pyrrolo[2,1-f][1,2,4]triazin-2-ylamino]-phenyl}-(4-methyl-piperazin-1-yl)-methanone;
{3-[7-(3-Chloro-phenyl)-pyrrolo[2,1-f][1,2,4]triazin-2-ylamino]-phenyl}-(4-methyl-piperazin-1-yl)-methanone;
(4-Methyl-piperazin-1-yl)-[3-(7-pyridin-3-yl-pyrrolo[2,1-f][1,2,4]triazin-2-ylamino)-phenyl]-methanone;
{3-[7-(4-Methanesulfonyl-phenyl)-pyrrolo[2,1-f][1,2,4]triazin-2-ylamino]-phenyl}-(4-methyl-piperazin-1-yl)-methanone;
[7-(2-Methoxy-phenyl)-pyrrolo[2,1-f][1,2,4]triazin-2-yl]-[4-(3-morpholin-4-yl-piperidin-1-yl)-phenyl]-amine;
[7-(5-Chloro-2-methoxy-phenyl)-pyrrolo[2,1-f][1,2,4]triazin-2-yl]-[4-(3-morpholin-4-yl-piperidin-1-yl)-phenyl]-amine;
[7-(3-Chloro-phenyl)-pyrrolo[2,1-f][1,2,4]triazin-2-yl]-[4-(3-morpholin-4-yl-piperidin-1-yl)-phenyl]-amine;
[7-(4-Methanesulfonyl-phenyl)-pyrrolo[2,1-f][1,2,4]triazin-2-yl]-[4-(3-morpholin-4-yl-piperidin-1-yl)-phenyl]-amine;
[4-(3-Morpholin-4-yl-piperidin-1-yl)-phenyl]-(7-pyridin-3-yl-pyrrolo[2,1-f][1,2,4]triazin-2-yl)-amine;
[7-(2-Methoxy-phenyl)-pyrrolo[2,1-f][1,2,4]triazin-2-yl]-{4-[3-(4-methyl-piperazin-1-yl)-piperidin-1-yl]-phenyl}-amine;
[7-(5-Chloro-2-methoxy-phenyl)-pyrrolo[2,1-f][1,2,4]triazin-2-yl]-{4-[3-(4-methyl-piperazin-1-yl)-piperidin-1-yl]-phenyl}-amine;
[7-(3-Chloro-phenyl)-pyrrolo[2,1-f][1,2,4]triazin-2-yl]-{4-[3-(4-methyl-piperazin-1-yl)-piperidin-1-yl]-phenyl}-amine;
[7-(4-Methanesulfonyl-phenyl)-pyrrolo[2,1-f][1,2,4]triazin-2-yl]-{4-[3-(4-methyl-piperazin-1-yl)-piperidin-1-yl]-phenyl}-amine;
{4-[3-(4-Methyl-piperazin-1-yl)-piperidin-1-yl]-phenyl}-(7-pyridin-3-yl-pyrrolo[2,1-f][1,2,4]triazin-2-yl)-amine;
[7-(2-Methoxy-phenyl)-pyrrolo[2,1-f][1,2,4]triazin-2-yl]-[4-(4-methyl-piperazin-1-ylmethyl)-phenyl]-amine;
[7-(5-Chloro-2-methoxy-phenyl)-pyrrolo[2,1-f][1,2,4]triazin-2-yl]-[4-(4-methyl-piperazin-1-ylmethyl)-phenyl]-amine;
[7-(4-Methanesulfonyl-phenyl)-pyrrolo[2,1-f][1,2,4]triazin-2-yl]-[4-(4-methyl-piperazin-1-ylmethyl)-phenyl]-amine;
N-Cyclopropyl-3-[2-(4-morpholin-4-yl-phenylamino)-pyrrolo[2,1-f][1,2,4]triazin-7-yl]-benzenesulfonamide;
N-Methyl-3-[2-(4-morpholin-4-yl-phenylamino)-pyrrolo[2,1-f][1,2,4]triazin-7-yl]-benzenesulfonamide;
(4-Morpholin-4-yl-phenyl)-{7-[3-(pyrrolidine-1-sulfonyl)-phenyl]-pyrrolo[2,1-f][1,2,4]triazin-2-yl}-amine;
5-[7-(2-Methoxy-phenyl)-pyrrolo[2,1-f][1,2,4]triazin-2-ylamino]-1-methyl-1,3-dihydro-indol-2-one;
5-[7-(5-Chloro-2-methoxy-phenyl)-pyrrolo[2,1-f][1,2,4]triazin-2-ylamino]-1-methyl-1,3-dihydro-indol-2-one;
N-{3-[2-(1-Methyl-2-oxo-2,3-dihydro-1H-indol-5-ylamino)-pyrrolo[2,1-f][1,2,4]triazin-7-yl]-phenyl}-methanesulfonamide;
(4-Morpholin-4-yl-phenyl)-(7-phenylaminomethyl-pyrrolo[2,1-f][1,2,4]triazin-2-yl)-amine;
[4-(4-Methyl-piperazin-1-yl)-phenyl]-(7-phenylaminomethyl-pyrrolo[2,1-f][1,2,4]triazin-2-yl)-amine;
{7-[(2-Methoxy-phenylamino)-methyl]-pyrrolo[2,1-f][1,2,4]triazin-2-yl}-(4-morpholin-4-yl-phenyl)-amine;
{7-[(2-Methoxy-phenylamino)-methyl]-pyrrolo[2,1-f][1,2,4]triazin-2-yl}-[4-(4-methyl-piperazin-1-yl)-phenyl]-amine;

N-Methyl-3-{2-[4-(4-methyl-piperazin-1-yl)-phenylamino]-pyrrolo[2,1-f][1,2,4]triazin-7-yl}-benzenesulfonamide;
[4-(4-Methyl-piperazin-1-yl)-phenyl]-{7-[3-(pyrrolidine-1-sulfonyl)-phenyl]-pyrrolo[2,1-f][1,2,4]triazin-2-yl}-amine;
N-(2-Hydroxy-ethyl)-3-[2-(4-morpholin-4-yl-phenylamino)-pyrrolo[2,1-f][1,2,4]triazin-7-yl]-benzenesulfonamide;
N-(2-Hydroxy-ethyl)-3-{2-[4-(4-methyl-piperazin-1-yl)-phenylamino]-pyrrolo[2,1-f][1,2,4]triazin-7-yl}-benzenesulfonamide;
(2-Fluoro-4-morpholin-4-yl-phenyl)-[7-(2-methoxy-phenyl)-pyrrolo[2,1-f][1,2,4]triazin-2-yl]-amine;
N-{3-[2-(2-Fluoro-4-morpholin-4-yl-phenylamino)-pyrrolo[2,1-f][1,2,4]triazin-7-yl]-phenyl}-methanesulfonamide;
(2-Fluoro-4-morpholin-4-yl-phenyl)-(7-pyridin-3-yl-pyrrolo[2,1-f][1,2,4]triazin-2-yl)-amine;
5-[7-(4-Methanesulfonyl-phenyl)-pyrrolo[2,1-f][1,2,4]triazin-2-ylamino]-1-methyl-1,3-dihydro-indol-2-one;
1-Methyl-5-(7-pyridin-3-yl-pyrrolo[2,1-f][1,2,4]triazin-2-ylamino)-1,3-dihydro-indol-2-one;
N-Methyl-N-{2-[2-(1-methyl-2-oxo-2,3-dihydro-1H-indol-5-ylamino)-pyrrolo[2,1-f][1,2,4]triazin-7-yl]-phenyl}-methanesulfonamide;
7-(2-methoxy-phenyl)-pyrrolo(2,1-f)(1,2,4)triazin-2-yl-6-amino-1'-methyl-spiro(2H-1-benzopyran-2,4'-piperidin-4(3H)-one;
7-(2-methoxy-phenyl)-pyrrolo(2,1-f)(1,2,4)triazin-2-yl-6-amino-1'-methyl-spiro(2H-1-benzopyran-2,4'-piperidin-4(3H)-one;
N-(3-(2-(6-amino-1'-methyl-spiro(2H-1-benzopyran-2,4'-piperidine)-pyrrolo(2,1-f)(1,2,4)trazin-7-yl)phenyl)-methanesulfonamide;
N-(3-{2-[4-(4-Methyl-piperazin-1-yl)-phenylamino]-pyrrolo[2,1-f][1,2,4]triazin-7-yl}-phenyl)-methanesulfonamide;
N-[3-(2-{4-[4-(2-Hydroxy-ethyl)-piperazin-1-yl]-phenylamino}-pyrrolo[2,1-f][1,2,4]triazin-7-yl)-phenyl]-methanesulfonamide;
N-{3-[2-(5,5-Dimethyl-2-oxo-2,3,4,5-tetrahydro-1H-1-benzazepin-8-ylamino)-pyrrolo[2,1-f][1,2,4]triazin-7-yl]-phenyl}-methanesulfonamide;
N-{3-[2-(7-Morpholin-4-yl-6,7,8,9-tetrahydro-5H-benzocyclohepten-2-ylamino)-pyrrolo[2,1-f][1,2,4]triazin-7-yl]-phenyl}-methanesulfonamide;
[2-(4-Morpholin-4-yl-phenylamino)-pyrrolo[2,1-f][1,2,4]triazin-7-yl]-phenyl-methanol;
5-[7-(6-Methoxy-pyridin-3-yl)-pyrrolo[2,1-f][1,2,4]triazin-2-ylamino]-1-methyl-1,3-dihydro-indol-2-one;
N-Methyl-N-{3-[2-(4-morpholin-4-yl-phenylamino)-pyrrolo[2,1-f][1,2,4]triazin-7-ylamino]-pyridin-2-yl}-methanesulfonamide;
N-{2-[2-(2-Fluoro-4-morpholin-4-yl-phenylamino)-pyrrolo[2,1-f][1,2,4]triazin-7-yl]-phenyl}-N-methyl-methanesulfonamide;
N-Methyl-N-{3-[2-(1-methyl-2-oxo-2,3-dihydro-1H-indol-5-ylamino)-pyrrolo[2,1-f][1,2,4]triazin-7-ylamino]-pyridin-2-yl}-methanesulfonamide;
N-{2-[2-(4-Fluoro-3-morpholin-4-yl-phenylamino)-pyrrolo[2,1-f][1,2,4]triazin-7-yl]-phenyl}-N-methyl-methanesulfonamide;
(4-Fluoro-3-morpholin-4-yl-phenyl)-[7-(2-methoxy-phenyl)-pyrrolo[2,1-f][1,2,4]triazin-2-yl]-amine;
N-{3-[2-(4-Fluoro-3-morpholin-4-yl-phenylamino)-pyrrolo[2,1-f][1,2,4]triazin-7-yl]-phenyl}-methanesulfonamide;
(4-Fluoro-3-morpholin-4-yl-phenyl)-(7-pyridin-3-yl-pyrrolo[2,1-f][1,2,4]triazin-2-yl)-amine;
(4-Fluoro-3-morpholin-4-yl-phenyl)-[7-(6-methoxy-pyridin-3-yl)-pyrrolo[2,1-f][1,2,4]triazin-2-yl]-amine;
N-{2-[2-(4-Methoxy-3-morpholin-4-yl-phenylamino)-pyrrolo[2,1-f][1,2,4]triazin-7-yl]-phenyl}-N-methyl-methanesulfonamide;
(4-Methoxy-3-morpholin-4-yl-phenyl)-[7-(2-methoxy-phenyl)-pyrrolo[2,1-f][1,2,4]triazin-2-yl]-amine;
N-{3-[2-(4-Methoxy-3-morpholin-4-yl-phenylamino)-pyrrolo[2,1-f][1,2,4]triazin-7-yl]-phenyl}-methanesulfonamide;
(4-Methoxy-3-morpholin-4-yl-phenyl)-(7-pyridin-3-yl-pyrrolo[2,1-f][1,2,4]triazin-2-yl)-amine;
(4-Methoxy-3-morpholin-4-yl-phenyl)-[7-(6-methoxy-pyridin-3-yl)-pyrrolo[2,1-f][1,2,4]triazin-2-yl]-amine;
N-[2-(2-{4-[4-((S)-2-Hydroxy-propyl)-piperazin-1-yl]-phenylamino}-pyrrolo[2,1-f][1,2,4]triazin-7-yl)-phenyl]-N-methyl-methanesulfonamide;
N-[2-(2-{4-[4-((R)-2-Hydroxy-propyl)-piperazin-1-yl]-phenylamino}-pyrrolo[2,1-f][1,2,4]triazin-7-yl)-phenyl]-N-methyl-methanesulfonamide;
1-{2-[2-(4-Morpholin-4-yl-phenylamino)-pyrrolo[2,1-f][1,2,4]triazin-7-yl]-phenyl}-ethanone;
2,2-Dimethyl-N-{2-[2-(4-morpholin-4-yl-phenylamino)-pyrrolo[2,1-f][1,2,4]triazin-7-yl]-phenyl}-propionamide;
1-(2-{2-[4-(4-Methyl-piperazin-1-yl)-phenylamino]-pyrrolo[2,1-f][1,2,4]triazin-7-yl}-phenyl)-ethanone;
2,2-Dimethyl-N-(2-{2-[4-(4-methyl-piperazin-1-yl)-phenylamino]-pyrrolo[2,1-f][1,2,4]triazin-7-yl}-phenyl)-propionamide;
[7-(2-Methanesulfinyl-phenyl)-pyrrolo[2,1-f][1,2,4]triazin-2-yl]-[4-(4-methyl-piperazin-1-yl)-phenyl]-amine;
[7-(2-Methanesulfinyl-phenyl)-pyrrolo[2,1-f][1,2,4]triazin-2-yl]-(4-morpholin-4-yl-phenyl)-amine;
[7-(2-Methanesulfonyl-phenyl)-pyrrolo[2,1-f][1,2,4]triazin-2-yl]-[4-(4-methyl-piperazin-1-yl)-phenyl]-amine;
N,N-Diethyl-2-{2-[4-(4-methyl-piperazin-1-yl)-phenylamino]-pyrrolo[2,1-f][1,2,4]triazin-7-yl}-benzamide;
N,N-Diethyl-2-[2-(4-morpholin-4-yl-phenylamino)-pyrrolo[2,1-f][1,2,4]triazin-7-yl]-benzamide;
2-{2-[4-(4-Methyl-piperazin-1-yl)-phenylamino]-pyrrolo[2,1-f][1,2,4]triazin-7-yl}-benzamide;
N-Methyl-N-{2-[2-(3-morpholin-4-yl-phenylamino)-pyrrolo[2,1-f][1,2,4]triazin-7-yl]-phenyl}-methanesulfonamide;
2-Methyl-propane-2-sulfonic acid (2-{2-[4-(4-methyl-piperazin-1-yl)-phenylamino]-pyrrolo[2,1-f][1,2,4]triazin-7-yl}-phenyl)-amide;
2-Methyl-propane-2-sulfonic acid {2-[2-(4-morpholin-4-yl-phenylamino)-pyrrolo[2,1-f][1,2,4]triazin-7-yl]-phenyl}-amide;
Cyclopropanesulfonic acid (3-{2-[4-(4-methyl-piperazin-1-yl)-phenylamino]-pyrrolo[2,1-f][1,2,4]triazin-7-yl}-phenyl)-amide;
Cyclopropanesulfonic acid {3-[2-(4-morpholin-4-yl-phenylamino)-pyrrolo[2,1-f][1,2,4]triazin-7-yl]-phenyl}-amide;
Ethanesulfonic acid (3-{2-[4-(4-methyl-piperazin-1-yl)-phenylamino]-pyrrolo[2,1-f][1,2,4]triazin-7-yl}-phenyl)-amide;

Ethanesulfonic acid {3-[2-(4-morpholin-4-yl-phenylamino)-pyrrolo[2,1-f][1,2,4]triazin-7-yl]-phenyl}-amide;
Propane-1-sulfonic acid (3-{2-[4-(4-methyl-piperazin-1-yl)-phenylamino]-pyrrolo[2,1-f][1,2,4]triazin-7-yl}-phenyl)-amide;
Propane-1-sulfonic acid {3-[2-(4-morpholin-4-yl-phenylamino)-pyrrolo[2,1-f][1,2,4]triazin-7-yl]-phenyl}-amide;
N-Methyl-N-(3-{2-[4-(4-methyl-piperazin-1-yl)-phenylamino]-pyrrolo[2,1-f][1,2,4]triazin-7-yl}-phenyl)-methanesulfonamide;
N-Methyl-N-{3-[2-(4-morpholin-4-yl-phenylamino)-pyrrolo[2,1-f][1,2,4]triazin-7-yl]-phenyl}-methanesulfonamide;
[7-(4-Methoxy-phenyl)-pyrrolo[2,1-f][1,2,4]triazin-2-yl]-[4-(4-methyl-piperazin-1-yl)-phenyl]-amine;
[7-(3-Methoxy-phenyl)-pyrrolo[2,1-f][1,2,4]triazin-2-yl]-(4-morpholin-4-yl-phenyl)-amine;
[7-(3-Methoxy-phenyl)-pyrrolo[2,1-f][1,2,4]triazin-2-yl]-[4-(4-methyl-piperazin-1-yl)-phenyl]-amine;
[7-(2,5-Dimethoxy-phenyl)-pyrrolo[2,1-f][1,2,4]triazin-2-yl]-(4-morpholin-4-yl-phenyl)-amine;
[7-(2,5-Dimethoxy-phenyl)-pyrrolo[2,1-f][1,2,4]triazin-2-yl]-[4-(4-methyl-piperazin-1-yl)-phenyl]-amine;
N-tert-Butyl-3-(2-{4-[4-((R)-2-hydroxy-propyl)-piperazin-1-yl]-phenylamino}-pyrrolo[2,1-f][1,2,4]triazin-7-yl)-benzenesulfonamide;
N-tert-Butyl-3-(2-{4-[4-((S)-2-hydroxy-propyl)-piperazin-1-yl]-phenylamino}-pyrrolo[2,1-f][1,2,4]triazin-7-yl)-benzenesulfonamide;
N-{2-[2-(4-Morpholin-4-yl-phenylamino)-pyrrolo[2,1-f][1,2,4]triazin-7-yl]-phenyl}-methanesulfonamide;
N-(2-{2-[4-(4-Methyl-piperazin-1-yl)-phenylamino]-pyrrolo[2,1-f][1,2,4]triazin-7-yl}-phenyl)-methanesulfonamide;
N-[2-(2-{4-[4-((S)-2-Hydroxy-propyl)-piperazin-1-yl]-phenylamino}-pyrrolo[2,1-f][1,2,4]triazin-7-yl)-phenyl]-methanesulfonamide;
N-{2-[2-(3-Morpholin-4-yl-phenylamino)-pyrrolo[2,1-f][1,2,4]triazin-7-yl]-phenyl}-methanesulfonamide;
5-[7-(2-Methoxy-phenyl)-pyrrolo[2,1-f][1,2,4]triazin-2-ylamino]-1,3-dihydro-indol-2-one;
(3,4-Dimethoxy-benzyl)-[7-(2-methoxy-phenyl)-pyrrolo[2,1-f][1,2,4]triazin-2-yl]-amine;
(1-{4-[7-(2-Methoxy-phenyl)-pyrrolo[2,1-f][1,2,4]triazin-2-ylamino]-phenyl}-piperidin-3-yl)-(4-methyl-piperazin-1-yl)-methanone;
(1-{4-[7-(2-Methoxy-phenyl)-pyrrolo[2,1-f][1,2,4]triazin-2-ylamino]-phenyl}-piperidin-4-yl)-(4-methyl-piperazin-1-yl)-methanone;
(1-{4-[7-(4-Methanesulfonyl-phenyl)-pyrrolo[2,1-f][1,2,4]triazin-2-ylamino]-phenyl}-piperidin-4-yl)-(4-methyl-piperazin-1-yl)-methanone;
(1-{4-[7-(4-Methanesulfonyl-phenyl)-pyrrolo[2,1-f][1,2,4]triazin-2-ylamino]-phenyl}-piperidin-3-yl)-(4-methyl-piperazin-1-yl)-methanone;
N-Methyl-N-[2-(2-{4-[3-(4-methyl-piperazine-1-carbonyl)-piperidin-1-yl]-phenylamino}-pyrrolo[2,1-f][1,2,4]triazin-7-yl)-phenyl]-methanesulfonamide;
N-Methyl-N-[2-(2-{4-[4-(4-methyl-piperazine-1-carbonyl)-piperidin-1-yl]-phenylamino}-pyrrolo[2,1-f][1,2,4]triazin-7-yl)-phenyl]-methanesulfonamide;
1-[7-(2-Methoxy-phenyl)-pyrrolo[2,1-f][1,2,4]triazin-2-yl]-3-[4-(4-methyl-piperazin-1-yl)-phenyl]-urea;
N-Methyl-N-[2-(2-{4-[4-(4-methyl-piperazin-1-ylmethyl)-piperidin-1-yl]-phenylamino}-pyrrolo[2,1-f][1,2,4]triazin-7-yl)-phenyl]-methanesulfonamide;
[7-(2-Methoxy-phenyl)-pyrrolo[2,1-f][1,2,4]triazin-2-yl]-{4-[4-(4-methyl-piperazin-1-ylmethyl)-piperidin-1-yl]-phenyl}-amine;
[7-(4-Methanesulfonyl-phenyl)-pyrrolo[2,1-f][1,2,4]triazin-2-yl]-{4-[4-(4-methyl-piperazin-1-ylmethyl)-piperidin-1-yl]-phenyl}-amine;
N-(2-{2-[2-Methoxy-4-(4-morpholin-4-yl-piperidin-1-yl)-phenylamino]-pyrrolo[2,1-f][1,2,4]triazin-7-yl}-phenyl)-acetamide;
N-(2-{2-[4-(4-Morpholin-4-yl-piperidin-1-yl)-phenylamino]-pyrrolo[2,1-f][1,2,4]triazin-7-yl}-phenyl)-acetamide;
N-Methyl-N-[2-(2-{4-[3-(4-methyl-piperazin-1-ylmethyl)-piperidin-1-yl]-phenylamino}-pyrrolo[2,1-f][1,2,4]triazin-7-yl)-phenyl]-methanesulfonamide;
[7-(2-Methoxy-phenyl)-pyrrolo[2,1-f][1,2,4]triazin-2-yl]-{4-[3-(4-methyl-piperazin-1-ylmethyl)-piperidin-1-yl]-phenyl}-amine;
[7-(4-Methanesulfonyl-phenyl)-pyrrolo[2,1-f][1,2,4]triazin-2-yl]-{4-[3-(4-methyl-piperazin-1-ylmethyl)-piperidin-1-yl]-phenyl}-amine;
(1-{3-Methoxy-4-[7-(2-methoxy-phenyl)-pyrrolo[2,1-f][1,2,4]triazin-2-ylamino]-phenyl}-piperidin-4-yl)-(4-methyl-piperazin-1-yl)-methanone;
N-[2-(2-{2-Methoxy-4-[4-(4-methyl-piperazine-1-carbonyl)-piperidin1-yl]-phenylamino}-pyrrolo[2,1-f][1,2,4]triazin-7-yl)-phenyl]-N-methyl-methanesulfonamide;
N-[2-(2-{2-Methoxy-4-[(S)-3-(4-methyl-piperazine-1-carbonyl)-piperidin-1-yl]-phenylamino}-pyrrolo[2,1-f][1,2,4]triazin-7-yl)-phenyl]-N-methyl-methanesulfonamide;
((S)-1-{3-Methoxy-4-[7-(2-methoxy-phenyl)-pyrrolo[2,1-f][1,2,4]triazin-2-ylamino]-phenyl}-piperidin-3-yl)-(4-methyl-piperazin-1-yl)-methanone;
N-[2-(2-{2-Methoxy-4-[(R)-3-(4-methyl-piperazine-1-carbonyl)-piperidin-1-yl]-phenylamino}-pyrrolo[2,1-f][1,2,4]triazin-7-yl)-phenyl]-N-methyl-methanesulfonamide;
((R)-1-{3-Methoxy-4-[7-(2-methoxy-phenyl)-pyrrolo[2,1-f][1,2,4]triazin-2-ylamino]-phenyl}-piperidin-3-yl)-(4-methyl-piperazin-1-yl)-methanone;
((R)-1-{3-Methoxy-4-[7-(6-methoxy-pyridin-3-yl)-pyrrolo[2,1-f][1,2,4]triazin-2-ylamino]-phenyl}-piperidin-3-yl)-(4-methyl-piperazin-1-yl)-methanone;
N-[2-(2-{2-Methoxy-4-[(R)-3-(4-methyl-piperazin-1-ylmethyl)-piperidin-1-yl]-phenylamino}-pyrrolo[2,1-f][1,2,4]triazin-7-yl)-phenyl]-N-methyl-methanesulfonamide;
{2-Methoxy-4-[(R)-3-(4-methyl-piperazin-1-ylmethyl)-piperidin-1-yl]-phenyl}-[7-(2-methoxy-phenyl)-pyrrolo[2,1-f][1,2,4]triazin-2-yl]-amine;
N-[2-(2-{2-Methoxy-4-[4-(4-methyl-piperazin-1-ylmethyl)-piperidin-1-yl]-phenylamino}-pyrrolo[2,1-f][1,2,4]triazin-7-yl)-phenyl]-N-methyl-methanesulfonamide;
{2-Methoxy-4-[4-(4-methyl-piperazin-1-ylmethyl)-piperidin-1-yl]-phenyl}-[7-(2-methoxy-phenyl)-pyrrolo[2,1-f][1,2,4]triazin-2-yl]-amine;
N-[2-(2-{2-Methoxy-4-[(S)-3-(4-methyl-piperazin-1-ylmethyl)-piperidin-1-yl]-phenylamino}-pyrrolo[2,1-f][1,2,4]triazin-7-yl)-phenyl]-N-methyl-methanesulfonamide;

{2-Methoxy-4-[(S)-3-(4-methyl-piperazin-1-ylmethyl)-piperidin-1-yl]-phenyl}-[7-(2-methoxy-phenyl)-pyrrolo[2,1-f][1,2,4]triazin-2-yl]-amine;

N-(4-{7-[2-(Methanesulfonyl-methyl-amino)-phenyl]-pyrrolo[2,1-f][1,2,4]triazin-2-ylamino}-3-methoxy-phenyl)-N-methyl-2-(4-methyl-piperazin-1-yl)-acetamide;

N-{3-Methoxy-4-[7-(2-methoxy-phenyl)-pyrrolo[2,1-f][1,2,4]triazin-2-ylamino]-phenyl}-N-methyl-2-morpholin-4-yl-acetamide;

N-(4-{7-[2-(Methanesulfonyl-methyl-amino)-phenyl]-pyrrolo[2,1-f][1,2,4]triazin-2-ylamino}-3-methoxy-phenyl)-N-methyl-2-morpholin-4-yl-acetamide;

N-{3-Methoxy-4-[7-(2-methoxy-phenyl)-pyrrolo[2,1-f][1,2,4]triazin-2-ylamino]-phenyl}-N-methyl-2-(4-methyl-piperazin-1-yl)-acetamide;

N-(2-{2-[4-(4-Dimethylamino-piperidin-1-yl)-2-methoxy-phenylamino]-pyrrolo[2,1-f][1,2,4]triazin-7-yl}-phenyl)-N-methyl-methanesulfonamide;

[4-(4-Dimethylamino-piperidin-1-yl)-2-methoxy-phenyl]-[7-(2-methoxy-phenyl)-pyrrolo[2,1-f][1,2,4]triazin-2-yl]-amine;

[4-(4-Dimethylamino-piperidin-1-yl)-2-methoxy-phenyl]-[7-(4-methanesulfonyl-phenyl)-pyrrolo[2,1-f][1,2,4]triazin-2-yl]-amine;

N-[2-(2-{4-[4-((R)-3-Hydroxy-pyrrolidin-1-yl)-piperidin-1-yl]-2-methoxy-phenylamino}-pyrrolo[2,1-f][1,2,4]triazin-7-yl)-phenyl]-N-methyl-methanesulfonamide;

(R)-1-(1-{3-Methoxy-4-[7-(2-methoxy-phenyl)-pyrrolo[2,1-f][1,2,4]triazin-2-ylamino]-phenyl}-piperidin-4-yl)-pyrrolidin-3-ol;

N-(2-{2-[2-Methoxy-4-(4-pyrrolidin-1-yl-piperidin-1-yl)-phenylamino]-pyrrolo[2,1-f][1,2,4]triazin-7-yl}-phenyl)-N-methyl-methanesulfonamide;

[7-(2-Methoxy-phenyl)-pyrrolo[2,1-f][1,2,4]triazin-2-yl]-[2-methoxy-4-(4-pyrrolidin-1-yl-piperidin-1-yl)-phenyl]-amine;

[4-(1,4-Dioxa-8-aza-spiro[4.5]dec-8-yl)-2-methoxy-phenyl]-[7-(2-methoxy-phenyl)-pyrrolo[2,1-f][1,2,4]triazin-2-yl]-amine;

(S)-1-(1-{3-Methoxy-4-[7-(2-methoxy-phenyl)-pyrrolo[2,1-f][1,2,4]triazin-2-ylamino]-phenyl}-piperidin-4-yl)-pyrrolidin-3-ol;

(1-{4-[7-(4-Chloro-2-methoxy-phenyl)-pyrrolo[2,1-f][1,2,4]triazin-2-ylamino]-phenyl}-piperidin-4-yl)-(4-methyl-piperazin-1-yl)-methanone;

(1-{4-[7-(4-Chloro-2-hydroxy-phenyl)-pyrrolo[2,1-f][1,2,4]triazin-2-ylamino]-phenyl}-piperidin-4-yl)-(4-methyl-piperazin-1-yl)-methanone;

[7-(4-Chloro-2-methoxy-phenyl)-pyrrolo[2,1-f][1,2,4]triazin-2-yl]-[2-methoxy-4-(4-morpholin-4-yl-piperidin-1-yl)-phenyl]-amine;

(S)-1-(4-{4-[7-(4-Chloro-2-methoxy-phenyl)-pyrrolo[2,1-f][1,2,4]triazin-2-ylamino]-3-methoxy-phenyl}-piperazin-1-yl)-propan-2-ol;

{2-Methoxy-4-[2-(4-methyl-piperazin-1-yl)-ethyl]-phenyl}-[7-(2-methoxy-phenyl)-pyrrolo[2,1-f][1,2,4]triazin-2-yl]-amine;

{3-Methoxy-4-[7-(2-methoxy-phenyl)-pyrrolo[2,1-f][1,2,4]triazin-2-ylamino]-phenyl}-(4-methyl-piperazin-1-yl)-methanone;

N-(2-{2-[2-Methoxy-4-(4-methyl-piperazine-1-carbonyl)-phenylamino]-pyrrolo[2,1-f][1,2,4]triazin-7-yl}-phenyl)-N-methyl-methanesulfonamide;

N-[2-(2-{2-Methoxy-4-[2-(4-methyl-piperazin-1-yl)-ethyl]-phenylamino}-pyrrolo[2,1-f][1,2,4]triazin-7-yl)-phenyl]-N-methyl-methanesulfonamide;

[2-Methoxy-4-(2-morpholin-4-yl-ethyl)-phenyl]-[7-(2-methoxy-phenyl)-pyrrolo[2,1-f][1,2,4]triazin-2-yl]-amine;

N-(2-{2-[2-Methoxy-4-(2-morpholin-4-yl-ethyl)-phenylamino]-pyrrolo[2,1-f][1,2,4]triazin-7-yl}-phenyl)-N-methyl-methanesulfonamide;

{4-Methoxy-3-[7-(2-methoxy-phenyl)-pyrrolo[2,1-f][1,2,4]triazin-2-ylamino]-phenyl}-(4-methyl-piperazin-1-yl)-methanone;

[2-Methoxy-5-(4-methyl-piperazin-1-ylmethyl)-phenyl]-[7-(2-methoxy-phenyl)-pyrrolo[2,1-f][1,2,4]triazin-2-yl]-amine;

N-(2-{2-[2-Methoxy-5-(4-methyl-piperazine-1-carbonyl)-phenylamino]-pyrrolo[2,1-f][1,2,4]triazin-7-yl}-phenyl)-N-methyl-methanesulfonamide;

N-(2-{2-[2-Methoxy-5-(4-methyl-piperazin-1-ylmethyl)-phenylamino]-pyrrolo[2,1-f][1,2,4]triazin-7-yl}-phenyl)-N-methyl-methanesulfonamide;

N-{2-[2-(2-Methoxy-5-morpholin-4-ylmethyl-phenylamino)-pyrrolo[2,1-f][1,2,4]triazin-7-yl]-phenyl}-N-methyl-methanesulfonamide;

(2-Methoxy-5-morpholin-4-ylmethyl-phenyl)-[7-(2-methoxy-phenyl)-pyrrolo[2,1-f][1,2,4]triazin-2-yl]-amine;

(4-{4-[7-(2-Methoxy-phenyl)-pyrrolo[2,1-f][1,2,4]triazin-2-ylamino]-phenyl}-piperidin-1-yl)-(1-methyl-piperidin-4-yl)-methanone;

(4-{4-[7-(2-Methoxy-phenyl)-pyrrolo[2,1-f][1,2,4]triazin-2-ylamino]-phenyl}-piperidin-1-yl)-(4-methyl-piperazin-1-yl)-methanone;

N-Methyl-N-[2-(2-{4-[1-(1-methyl-piperidine-4-carbonyl)-piperidin-4-yl]-phenylamino}-pyrrolo[2,1-f][1,2,4]triazin-7-yl)-phenyl]-methanesulfonamide;

N-Methyl-N-[2-(2-{4-[1-(4-methyl-piperazine-1-carbonyl)-piperidin-4-yl]-phenylamino}-pyrrolo[2,1-f][1,2,4]triazin-7-yl)-phenyl]-methanesulfonamide;

N-(2-{2-[2-Methoxy-4-(2-methyl-imidazol-1-ylmethyl)-phenylamino]-pyrrolo[2,1-f][1,2,4]triazin-7-yl}-phenyl)-N-methyl-methanesulfonamide;

[2-Methoxy-4-(2-methyl-imidazol-1-ylmethyl)-phenyl]-[7-(2-methoxy-phenyl)-pyrrolo[2,1-f][1,2,4]triazin-2-yl]-amine;

N-(2-{2-[2-Chloro-4-(4-methyl-piperazin-1-yl)-phenylamino]-pyrrolo[2,1-f][1,2,4]triazin-7-yl}-phenyl)-N-methyl-methanesulfonamide;

[2-Chloro-4-(4-methyl-piperazin-1-yl)-phenyl]-[7-(2-methoxy-phenyl)-pyrrolo[2,1-f][1,2,4]triazin-2-yl]-amine;

[7-(2-Fluoro-6-methoxy-phenyl)-pyrrolo[2,1-f][1,2,4]triazin-2-yl]-[2-methoxy-4-(4-morpholin-4-yl-piperidin-1-yl)-phenyl]-amine;

[7-(4-Fluoro-2-methoxy-phenyl)-pyrrolo[2,1-f][1,2,4]triazin-2-yl]-[2-methoxy-4-(4-morpholin-4-yl-piperidin-1-yl)-phenyl]-amine;

2-{2-[2-Methoxy-4-(4-morpholin-4-yl-piperidin-1-yl)-phenylamino]-pyrrolo[2,1-f][1,2,4]triazin-7-yl}-benzonitrile;

[2-Methoxy-4-(4-morpholin-4-yl-piperidin-1-yl)-phenyl]-(7-quinolin-8-yl-pyrrolo[2,1-f][1,2,4]triazin-2-yl)-amine;

2-(4-{4-[7-(2-Cyano-phenyl)-pyrrolo[2,1-f][1,2,4]triazin-2-ylamino]-phenyl}-piperidin-1-yl)-acetamide;

2-{4-[4-(7-Quinolin-8-yl-pyrrolo[2,1-f][1,2,4]triazin-2-ylamino)-phenyl]-piperidin-1-yl}-acetamide;

2-[4-(4-{7-[2-(Methanesulfonyl-methyl-amino)-phenyl]-6-methyl-pyrrolo[2,1-f][1,2,4]triazin-2-ylamino}-3-methoxy-phenyl)-piperidin-1-yl]-acetamide;

2-[4-(4-{7-[2-(Methanesulfonyl-methyl-amino)-phenyl]-6-methyl-pyrrolo[2,1-f][1,2,4]triazin-2-ylamino}-phenyl)-piperidin-1-yl]-acetamide;

2-(4-{4-[7-(2-Cyano-phenyl)-pyrrolo[2,1-f][1,2,4]triazin-2-ylamino]-3-methoxy-phenyl}-piperidin-1-yl)-acetamide;

(R)-1-{7-[7-(2,3-Dihydro-benzofuran-7-yl)-pyrrolo[2,1-f]triazin-2-ylamino]-8-methoxy-1,2,4,5-tetrahydro-benzo[d]azepin-3-yl}-propan-2-ol;

N-Cyclopropyl-3-{2-[3-((R)-2-hydroxy-propyl)-8-methoxy-2,3,4,5-tetrahydro-1H-benzo[d]azepin-7-ylamino]-pyrrolo[2,1-f][1,2,4]triazin-7-yl}benzenesulfonamide;

2-{7-[7-(3-Cyclopropylsulfamoyl-phenyl)-pyrrolo[2,1-f][1,2,4]triazin-2-ylamino]-8-methoxy-1,2,4,5-tetrahydro-benzo[d]azepin-3-yl}-acetamide;

4-(1-{3-Methoxy-4-[7-(2-methoxy-phenyl)-pyrrolo[2,1-f][1,2,4]triazin-2-ylamino]-phenyl}-piperidin-4-yl)-piperazine-1-carboxylic acid benzyl ester;

2-(2-{2-Methoxy-4-[4-(4-methyl-piperazin-1-yl)-piperidin-1-yl]-phenylamino}-pyrrolo[2,1-f][1,2,4]triazin-7-yl)-N,N-dimethyl-benzenesulfonamide;

[7-(6-Chloro-pyridin-3-yl)-pyrrolo[2,1-f][1,2,4]triazin-2-yl]-{2-methoxy-4-[4-(4-methyl-piperazin-1-yl)-piperidin-1-yl]-phenyl}-amine trifluoroacetate;

N-tert-Butyl-3-(2-{2-methoxy-4-[4-(4-methyl-piperazin-1-yl)-piperidin-1-yl]-phenylamino}-pyrrolo[2,1-f][1,2,4]triazin-7-yl)-benzenesulfonamide;

{4-[4-(4-Methanesulfonyl-piperazin-1-yl)-piperidin-1-yl]-2-methoxy-phenyl}-[7-(2-methoxy-phenyl)-pyrrolo[2,1-f][1,2,4]triazin-2-yl]-amine trifluoroacetate;

1-[4-(1-{3-Methoxy-4-[7-(2-methoxy-phenyl)-pyrrolo[2,1-f][1,2,4]triazin-2-ylamino]-phenyl}-piperidin-4-yl)-piperazin-1-yl]-ethanone trifluoroacetate;

[7-(2-Methoxy-phenyl)-pyrrolo[2,1-f][1,2,4]triazin-2-yl]-[2-methoxy-4-(4-piperazin-1-yl-piperidin-1-yl)-phenyl]-amine;

[7-(2-Methoxymethyl-phenyl)-pyrrolo[2,1-f][1,2,4]triazin-2-yl]-{2-methoxy-4-[4-(4-methyl-piperazin-1-yl)-piperidin-1-yl]-phenyl}-amine;

[2-Methoxy-5-methyl-4-(morpholin-4-yl-piperidin-1-yl)-phenyl]-7(2-methoxy-phenyl)-pyrrolo[2,1-f][1,2,4]triazin-2-yl]-amine trifluoroacetate;

[7-(2-Methanesulfonyl-phenyl)-pyrrolo[2,1-f][1,2,4]triazin-2-yl]-[2-methoxy-4-(4-morpholin-4-yl-piperidin-1-yl)-phenyl]-amine;

(S)-1-(4-{4-[7-(2-Methanesulfonyl-phenyl)-pyrrolo[2,1-f][1,2,4]triazin-2-ylamino]-3-methoxy-phenyl}-piperazin-1-yl)-propan-2-ol;

[7-(2,6-Dimethoxy-phenyl)-pyrrolo[2,1-f][1,2,4]triazin-2-yl]-[2-methoxy-4-(4-morpholin-4-yl-piperidin-1-yl)-phenyl]-amine trifluoro acetate;

[(S)-1-(4-{4-[7-(2,6-Dimethoxy-phenyl)-pyrrolo[2,1-f][1,2,4]triazin-2-ylamino]-3-methoxy-phenyl}-piperazin-1-yl)-propan-2-ol trifluoroacetate;

[7-(2-Methanesulfinyl-phenyl)-pyrrolo[2,1-f][1,2,4]triazin-2-yl]-[2-methoxy-4-(4-morpholin-4-yl-piperidin-1-yl)-phenyl]-amine trifluoroacetate;

(S)-1-(4-{4-[7-(2-Methanesulfinyl-phenyl)-pyrrolo[2,1-f][1,2,4]triazin-2-ylamino]-3-methoxy-phenyl}-piperazin-1-yl)-propan-2-ol trifluoroacetate;

[7-(2,3-Dihydro-1,4-benzodioxin-5-yl)-pyrrolo[2,1-f][1,2,4]triazin-2-yl]-[2-methoxy-4-(4-morpholin-4-yl-piperidin-1-yl)-phenyl]-amine trifluoroacetate;

(S)-1-(4-{4-[7-(2,3-Dihydro-1,4-benzodioxin-5-yl)-pyrrolo[2,1-f][1,2,4]triazin-2-ylamino]-3-methoxy-phenyl}-piperazin-1-yl)-propan-2-ol trifluoroacetate;

[7-(2,3-Dihydro-1,4-benzodioxin-5-yl)-pyrrolo[2,1-f][1,2,4]triazin-2-yl]-[4-(4-methyl-piperazin-1-yl)-phenyl]-amine;

[7-(2-Methanesulfonylmethyl-phenyl)-pyrrolo[2,1-f][1,2,4]triazin-2-yl]-[2-methoxy-4-(4-morpholin-4-yl-piperidin-1-yl)-phenyl]-amine trifluoroacetate;

(R)-3-(4-{2-Fluoro-5-methoxy-4-[7-(2-methoxy-phenyl)-pyrrolo[2,1-f][1,2,4]triazin-2-ylamino]-phenyl}-piperidin-1-yl)-propane-1,2-diol trifluoroacetate;

N-[2-(2-{4-[1-((R)-2,3-Dihydroxy-propyl)-piperidin-4-yl]-5-fluoro-2-methoxy-phenylamino}-pyrrolo[2,1-f][1,2,4]triazin-7-yl)-phenyl]-N-methyl-methane-sulfonamide trifluoroacetate;

N-tert-Butyl-3-[2-(4-morpholin-4-yl-phenylamino)-pyrrolo[2,1-f][1,2,4]triazin-7-yl]-benzenesulfonamide;

N-tert-Butyl-3-(2-{4-[4-(3-oxo-piperazin-1-yl)-piperidin-1-yl]-phenylamino}-pyrrolo[2,1-f][1,2,4]triazin-7-yl)-benzenesulfonamide;

3-{1-[7-(3-Methanesulfonyl-phenyl)-pyrrolo[2,1-f][1,2,4]triazin-2-yl]-piperidin-4-yloxy}-phenylamine;

[7-(2-Methoxy-phenyl)-pyrrolo[2,1-f][1,2,4]triazin-2-yl]-(2-methyl-benzoxazol-5-yl)-amine;

N-tert-Butyl-3-{2-[4-(4-morpholin-4-yl-cyclohexyl)-phenylamino]-pyrrolo[2,1-f][1,2,4]triazin-7-yl}-benzenesulfonamide;

N-tert-Butyl-3-{2-[4-(4-pyrrolidin-1-yl-cyclohexyl)-phenylamino]-pyrrolo[2,1-f][1,2,4]triazin-7-yl}-benzenesulfonamide;

N-tert-Butyl-3-{2-[4-(4-dimethylamino-cyclohexyl)-phenylamino]-pyrrolo[2,1-f][1,2,4]triazin-7-yl}-benzenesulfonamide;

N-tert-Butyl-3-{2-[4-(4-hydroxy-cyclohexyl)-phenylamino]-pyrrolo[2,1-f][1,2,4]triazin-7-yl}-benzenesulfonamide;

N-tert-Butyl-3-{2-[3-(1-hydroxy-ethyl)-phenylamino]-pyrrolo[2,1-f][1,2,4]triazin-7-yl}-benzenesulfonamide;

2-[4-(4-{7-[3-(Propane-2-sulfonyl)-phenyl]-pyrrolo[2,1-f][1,2,4]triazin-2-ylamino}-phenyl)-piperidin-1-yl]-acetamide;

N-tert-Butyl-3-{2-[4-(4-methoxyimino-cyclohexyl)-phenylamino]-pyrrolo[2,1-f][1,2,4]triazin-7-yl}-benzenesulfonamide;

N-tert-Butyl-3-{2-(2-methyl-benzothiazol-6-ylamino)-pyrrolo[2,1-f][1,2,4]triazin-7-yl]-benzenesulfonamide;

3-[2-(Benzothiazol-6-ylamino)-pyrrolo[2,1-f][1,2,4]triazin-7-yl]-N-tert-butyl-benzenesulfonamide;

N-tert-Butyl-3-[2-(2-methyl-benzothiazol-5-ylamino)-pyrrolo[2,1-f][1,2,4]triazin-7-yl]-benzenesulfonamide;

3-[2-(Benzothiazol-5-ylamino)-pyrrolo[2,1-f][1,2,4]triazin-7-yl]-N-tert-butyl-benzenesulfonamide;

4-(4-{7-[3-(Propane-2-sulfonyl)-phenyl]-pyrrolo[2,1-f][1,2,4]triazin-2-ylamino}-phenyl)-cyclohexanone O-methyl-oxime;

2-(3-{4-[7-(3-tert-Butylsulfamoyl-phenyl)-pyrrolo[2,1-f][1,2,4]triazin-2-ylamino]-phenyl}-azetidin-1-yl)-acetamide;

2-(3-{4-[7-(3-Methanesulfonyl-phenyl)-pyrrolo[2,1-f][1,2,4]triazin-2-ylamino]-phenyl}-azetidin-1-yl)-acetamide;

2-(4-{4-[7-(2-Methanesulfonyl-2,3-dihydro-1H-isoindol-4-yl)-pyrrolo[2,1-f][1,2,4]triazin-2-ylamino]-phenyl}-piperidin-1-yl)-acetamide;

2-(4-{4-[7-(3,6-Dimethoxy-pyridazin-4-yl)-pyrrolo[2,1-f][1,2,4]triazin-2-ylamino]-phenyl}-piperidin-1-yl)-acetamide;
2-(3-{4-[7-(3,6-Dimethoxy-pyridazin-4-yl)-pyrrolo[2,1-f][1,2,4]triazin-2-ylamino]-phenyl}-azetidin-1-yl)-acetamide;
2-(3-{4-[7-(2-Methanesulfonyl-2,3-dihydro-1H-isoindol-4-yl)-pyrrolo[2,1-f][1,2,4]triazin-2-ylamino]-phenyl}-azetidin-1-yl)-acetamide;
2-(3-{4-[7-(2-Methoxy-phenyl)-pyrrolo[2,1-f][1,2,4]triazin-2-ylamino]-phenyl}-azetidin-1-yl)-acetamide;
2-(3-{4-[7-(6-Methoxy-pyridin-3-yl)-pyrrolo[2,1-f][1,2,4]triazin-2-ylamino]-phenyl}-azetidin-1-yl)-acetamide;
2-(3-{4-[7-(1-Methyl-1H-pyrazol-4-yl)-pyrrolo[2,1-f][1,2,4]triazin-2-ylamino]-phenyl}-azetidin-1-yl)-acetamide;
2-[3-(4-{7-[2-(Methanesulfonyl-methyl-amino)-phenyl]-pyrrolo[2,1-f][1,2,4]triazin-2-ylamino}-phenyl)-azetidin-1-yl]-acetamide;
2-(3-{4-[7-(2,3-Dihydro-benzofuran-7-yl)-pyrrolo[2,1-f][1,2,4]triazin-2-ylamino]-phenyl}-azetidin-1-yl)-acetamide;
2-(4-{4-[7-(3-Isopropoxy-phenyl)-pyrrolo[2,1-f][1,2,4]triazin-2-ylamino]-phenyl}-piperidin-1-yl)-acetamide;
N-tert-Butyl-3-(2-{4-[4-(4-methyl-piperazin-1-ylmethyl)-piperidin-1-yl]-phenylamino}-pyrrolo[2,1-f][1,2,4]triazin-7-yl)-benzenesulfonamide;
N-tert-Butyl-3-[2-(6-oxo-1,6-dihydro-pyridin-3-ylamino)-pyrrolo[2,1-f][1,2,4]triazin-7-yl]-benzenesulfonamide;
5-[7-(2-Methoxy-phenyl)-pyrrolo[2,1-f][1,2,4]triazin-2-ylamino]-1H-pyridin-2-one;
3-({7-[3-(tert-butylsulfamoyl)phenyl]pyrrolo[2,1-f][1,2,4]triazin-2-yl}amino)-N,N-dimethylbenzenesulfonamide;
4-({7-[3-(tert-butylsulfamoyl)phenyl]pyrrolo[2,1-f][1,2,4]triazin-2-yl}amino)-N,N-dimethylbenzenesulfonamide;
3-[7-(2-Methoxy-phenyl)-pyrrolo[2,1-f][1,2,4]triazin-2-ylamino]-N,N-dimethyl-benzenesulfonamide;
4-[7-(2-Methoxy-phenyl)-pyrrolo[2,1-f][1,2,4]triazin-2-ylamino]-N,N-dimethyl-benzenesulfonamide;
N-Methyl-N-{2-[2-(6-oxo-1,6-dihydro-pyridin-3-ylamino)-pyrrolo[2,1-f][1,2,4]triazin-7-yl]-phenyl}-methanesulfonamide;
(3-Chloro-4-fluoro-phenyl)-[7-(3-methanesulfonyl-phenyl)-pyrrolo[2,1-f][1,2,4]triazin-2-yl]-amine;
3-{1-[7-(1-Methyl-1H-pyrazol-4-yl)-pyrrolo[2,1-f][1,2,4]triazin-2-yl]-piperidin-4-yloxy}-phenylamine;
[7-(3-Methanesulfonyl-phenyl)-pyrrolo[2,1-f][1,2,4]triazin-2-yl]-(2-methyl-benzoxazol-5-yl)-amine;
N-tert-Butyl-3-[2-(2-methyl-benzoxazol-5-ylamino)-pyrrolo[2,1-f][1,2,4]triazin-7-yl]-benzenesulfonamide;
[7-(2-Methoxy-phenyl)-pyrrolo[2,1-f][1,2,4]triazin-2-yl]-H3-(piperidin-4-yloxy)-phenyl]-amine;
[7-(3-Methanesulfonyl-phenyl)-pyrrolo[2,1-f][1,2,4]triazin-2-yl]-(7-morpholin-4-yl-6,7,8,9-tetrahydro-5H-benzocyclohepten-2-yl)-amine;
[7-(4-Methanesulfonyl-phenyl)-pyrrolo[2,1-f][1,2,4]triazin-2-yl]-(7-morpholin-4-yl-6,7,8,9-tetrahydro-5H-benzocyclohepten-2-yl)-amine;
[7-(3,6-Dihydro-2H-thiopyran-4-yl)-pyrrolo[2,1-f][1,2,4]triazin-2-yl]-(4-morpholin-4-yl-phenyl)-amine;
[7-(2-methoxy-phenyl)-pyrrolo[2,1-f][1,2,4]triazin-2-yl]-(7-morpholin-4-yl-6,7,8,9-tetrahydro-5H-benzocyclohepten-2-yl)amine;
N-Methyl-N-{2-[2-(7-morpholin-4-yl-6,7,8,9-tetrahydro-5H-benzocyclohepten-2-ylamino)-pyrrolo[2,1-f][1,2,4]triazin-7-yl]-phenyl}-methanesulfonamide;
[7-(4-Methanesulfonyl-phenyl)-pyrrolo[2,1-f][1,2,4]triazin-2-yl]-(1-methyl-1,2,3,5-tetrahydro-benzo[e][1,4]oxazepin-7-yl)-amine;
[7-(2-Methoxy-phenyl)-pyrrolo[2,1-f][1,2,4]triazin-2-yl]-(1-methyl-1,2,3,5-tetrahydro-benzo[e][1,4oxazepin-7-yl)-amine;
N-{3-[2-(1-Methyl-1,2,3,5-tetrahydro-benzo[e][1,4]oxazepin-7-ylamino)-pyrrolo[2,1-f][1,2,4]triazin-7-yl]-phenyl}-methanesulfonamide;
[7-(4-Methanesulfonyl-cyclohex-1-enyl)-pyrrolo[2,1-f][1,2,4]triazin-2-yl]-[4-(4-methyl-piperazin-1-yl)-phenyl]-amine;
N-{2-[2-(4-Imidazol-1-ylmethylphenylamino)-pyrrolo[2,1-f][1,2,4]triazin-7-yl]phenyl}-N-methyl-methanesulfonamide;
N-[2-(2-Imidazol-1-yl-pyrrolo[2,1-f][1,2,4]triazin-7-yl)-phenyl]-N-methyl-methanesulfonamide;
N-Methyl-N-{2-[2-(2-oxo-2,3,4,5-tetrahydro-1H-benzo[b]azepin-7-ylamino)-pyrrolo[2,1-f][1,2,4]triazin-7-yl]-phenyl}-methanesulfonamide;
N-{2-[2-(5,5-Dimethyl-2-oxo-2,3,4,5-tetrahydro-1H-benzo[b]azepin-7-ylamino)pyrrolo[2,1-f][1,2,4]triazin-7-yl]-phenyl}methanesulfonamide;
N-{2-[2-(1-Methyl-2-oxo-2,3,4,5-tetrahydro-1H-benzo[b]azepin-7-ylamino)pyrrolo[2,1-f][1,2,4]triazin-7-yl]-phenyl}methanesulfonamide;
N-Methyl-N-{2-[2-(4-morpholin-4-yl-phenylamino)pyrrolo[2,1-f][1,2,4]triazin-7-yl]phenyl}methanesulfonamide;
N-Methyl-N-(2-{2-[4-(4-methyl-piperazin-1-yl)phenylamino]pyrrolo[2,1-f][1,2,4]triazin-7-yl}phenyl)methanesulfonamide;
N-Methyl-N-{2-[2-(4-methyl-2-oxo-2,3-dihydrobenzooxazol-6-ylamino)-pyrrolo[2,1-f][1,2,4]triazin-7-yl]phenyl}methanesulfonamide;
N-{2-[2-(2-oxo-2,3-dihydro-benzooxazol-6-ylamino)pyrrolo[2,1-f][1,2,4]triazin-7-yl]phenyl}methanesulfonamide;
N-{2-[2-(1-Acetyl-2,3,4,5-tetrahydro-1H-benzo[b]azepin-8-ylamino)-pyrrolo[2,1-f][1,2,4]triazin-7-yl]phenyl}-N-methylmethanesulfonamide;
1-{8-[7-(6-Methoxy-pyridin-3-yl)-pyrrolo[2,1-f][1,2,4]triazin-2-ylamino]-2,3,4,5-tetrahydro-benzo[b]azepin-1-yl}ethanone;
N-{2-[2-(3,3-Dimethyl-2-oxo-2,3-dihydro-1H-indol-5-ylamino)-pyrrolo[2,1-f][1,2,4]triazin-7-yl]phenyl}N-methyl-methanesulfonamide;
N-{3-[2-(1-Acetyl-2,3,4,5-tetrahydro-1H-benzo[b]azepin-8-ylamino)-pyrrolo[2,1-f][1,2,4]triazin-7-yl]phenyl}methanesulfonamide;
N-(2-{2-[1-(4-Amino-phenyl)-piperidin-4-yloxy]-pyrrolo[2,1-f][1,2,4]triazin-7-yl}-phenyl)-N-methyl-methanesulfonamide;
N-(2-{2-[4-(4-Hydroxy-piperidin-1-yl)-phenylamino]pyrrolo[2,1-f][1,2,4]triazin-7-yl}phenyl)-N-methyl-methanesulfonamide;
N-(3-{2-[4-(4-Morpholin-4-yl-piperidin-1-yl)-phenylamino]-pyrrolo[2,1-f][1,2,4]triazin-7-yl}-phenyl)-methanesulfonamide;
[7-(6-Methoxy-pyridin-3-yl)-pyrrolo[2,1-f][1,2,4]triazin-2-yl]-(1-methyl-1,2,3,5-tetrahydro-benzo[e][1,4oxazepin-7-yl)-amine;

N-{3-[2-(4-Methyl-3-oxo-3,4-dihydro-2H-benzo[1,4]ox-azin-7-ylamino)-pyrrolo[2,1-f][1,2,4]triazin-7-yl]-phenyl}methanesulfonamide;
1-{8-[7-(2-Methoxyphenyl)-pyrrolo[2,1-f][1,2,4]triazin-2-ylamino]-2,3,4,5-tetrahydrobenzo[b]azepin-1-yl}ethanone;
N-Methyl-N-{2-[2-(4-methyl-3-oxo-3,4-dihydro-2H-benzo[1,4oxazin-7-ylamino)-pyrrolo[2,1-f][1,2,4]triazin-7-yl]-phenyl}-methanesulfonamide;
N-Methyl-N-{2-[2-(4-methyl-3,4-dihydro-2H-benzo[1,4]oxazin-6-ylamino)-pyrrolo[2,1-f][1,2,4]triazin-7-yl]-phenyl}methanesulfonamide;
(4-Methyl-3,4-dihydro-2H-benzo[1,4]oxazin-6-yl)-(7-pyridin-3-yl-pyrrolo[2,1-f][1,2,4]triazin-2-yl)-amine;
N-{3-[2-(4-Methyl-3,4-dihydro-2H-benzo[1,4]oxazin-6-ylamino)-pyrrolo[2,1-f][1,2,4]triazin-7-yl]-phenyl}methanesulfonamide;
[7-(6-Methoxy-pyridin-3-yl)-pyrrolo[2,1-f][1,2,4]triazin-2-yl]-(4-methyl-3,4-dihydro-2H-benzo[1,4]oxazin-6-yl)-amine;
[7-(2-Methoxy-phenyl)-pyrrolo[2,1-f][1,2,4]triazin-2-yl]-(4-methyl-3,4-dihydro-2H-benzo[1,4]oxazin-6-yl)-amine;
6-[7-(1-Methyl-1H-pyrazol-4-yl)-pyrrolo[2,1-f][1,2,4]triazin-2-ylamino]-1,3-dihydro-indol-2-one;
7-[7-(2-Methoxy-phenyl)-pyrrolo[2,1-f][1,2,4]triazin-2-ylamino]-4-methyl-4H-benzo[1,4]oxazin-3-one;
N-tert-Butyl-3-[2-(4-methyl-3-oxo-3,4-dihydro-2H-benzo[1,4]oxazin-7-ylamino)-pyrrolo[2,1-f][1,2,4]triazin-7-yl]-benzenesulfonamide;
4-Methyl-7-(7-pyridin-3-yl-pyrrolo[2,1-f][1,2,4]triazin-2-ylamino)-4H-benzo[1,4]oxazin-3-one;
N-tert-Butyl-3-[2-(4-methyl-3,4-dihydro-2H-benzo[1,4]oxazin-6-ylamino)-pyrrolo[2,1-f][1,2,4]triazin-7-yl]-benzenesulfonamide;
N-(3-{2-[4-(4-Ethyl-morpholin-2-yl)-phenylamino]-pyrrolo[2,1-f][1,2,4]triazin-7-yl}phenyl)methanesulfonamide;
N-tert-Butyl-3-[2-(2-oxo-2,3-dihydro-1H-indol-6-ylamino)-pyrrolo[2,1-f][1,2,4]triazin-7-yl]-benzenesulfonamide;
N-tert-Butyl-3-{2-[4-(4-ethyl-morpholin-2-yl)-phenylamino]-pyrrolo[2,1-f][1,2,4]triazin-7-yl}benzenesulfonamide;
N-tert-Butyl-3-(2-{4-[1-((S)-2-hydroxy-propyl)-piperidin-4-yl]-phenylamino}-pyrrolo[2,1-f][1,2,4]triazin-7-yl)-benzenesulfonamide;
N-tert-Butyl-3-[2-(3,3-dimethyl-2-oxo-2,3-dihydro-1H-indol-6-ylamino)-pyrrolo[2,1-f][1,2,4]triazin-7-yl]-benzenesulfonamide;
6-[7-(2-Methoxy-phenyl)-pyrrolo[2,1-f][1,2,4]triazin-2-ylamino]-3,3-dimethyl-1,3-dihydro-indol-2-one;
(S)-1-(4-{4-[7-(6-Methoxy-pyridin-3-yl)-pyrrolo[2,1-f][1,2,4]triazin-2-ylamino]-phenyl}-piperidin-1-yl)-propan-2-ol;
6-[7-(6-Methoxy-pyridin-3-yl)-pyrrolo[2,1-f][1,2,4]triazin-2-ylamino]-3,3-dimethyl-1,3-dihydro-indol-2-one;
(2,2-Dioxo-2,3-dihydro-1H-2lambda*6*-benzo[c]thiophen-5-yl)-[7-(2-methoxy-phenyl)-pyrrolo[2,1-f][1,2,4]triazin-2-yl]-amine;
2-(4-{4-[7-(2-Methoxy-phenyl)-pyrrolo[2,1-f][1,2,4]triazin-2-ylamino]-phenyl}-piperidin-1-yl)-acetamide;
N-{2-[2-(3,3-Dimethyl-2-oxo-2,3-dihydro-1H-indol-6-ylmethyl)-pyrrolo[2,1-f][1,2,4]triazin-7-yl]-phenyl}-N-methyl-methanesulfonamide;
[7-(3-Dimethylamino-phenyl)-pyrrolo[2,1-f][1,2,4]triazin-2-yl]-[4-(1-methyl-piperidin-4-yl)-phenyl]-amine;
N-tert-Butyl-3-[2-(2,2-dioxo-2,3-dihydro-1H-2lambda*6*-benzo[c]thiophen-5-ylamino)-pyrrolo[2,1-f][1,2,4]triazin-7-yl]-benzenesulfonamide;
2-(4-{4-[7-(1,2,3,6-Tetrahydro-pyridin-4-yl)-pyrrolo[2,1-f][1,2,4]triazin-2-ylamino]-phenyl}-piperidin-1-yl)-acetamide;
5-[7-(3-tert-Butylsulfamoyl-phenyl)-pyrrolo[2,1-f][1,2,4]triazin-2-ylamino]-nicotinamide;
5-{7-[2-(Methanesulfonyl-methyl-amino)-phenyl]-pyrrolo[2,1-f][1,2,4]triazin-2-ylamino}-nicotinamide;
5-[7-(6-Methoxy-pyridin-3-yl)-pyrrolo[2,1-f][1,2,4]triazin-2-ylamino]-nicotinamide;
2-(4-{4-[7-(2-Methoxy-phenyl)-pyrrolo[2,1-f][1,2,4]triazin-2-ylamino]-phenyl}-piperidin-1-yl)-ethanol;
N-[2-(2-{4-[1-(2-Hydroxy-ethyl)-piperidin-4-yl]-phenylamino}-pyrrolo[2,1-f][1,2,5]triazin-7-yl)-phenyl]-N-methyl-methanesulfonamide;
2-(4-{4-[7-(6-Methoxy-pyridin-3-yl)-pyrrolo[2,1-f][1,2,4]triazin-2-ylamino]-phenyl}-piperidin-1-yl)-ethanol;
N-tert-Butyl-3-(2-{4-[1-(2-hydroxy-ethyl)-piperidin-4-yl]-phenylamino}-pyrrolo[2,1-f][1,2,4]triazin-7-yl)-benzenesulfonamide;
{6-[7-(3-tert-Butylsulfamoyl-phenyl)-pyrrolo[2,1-f][1,2,4]triazin-2-ylamino]-2-hydroxy-indan-1-yl}-carbamic acid tert-butyl ester;
{2-Hydroxy-6-[7-(2-methoxy-phenyl)-pyrrolo[2,1-f][1,2,4]triazin-2-ylamino]-indan-1-yl}-carbamic acid tert-butyl ester;
5-{2-[4-(1-Carbamoylmethyl-piperidin-4-yl)-phenylamino]-pyrrolo[2,1-f][1,2,4]triazin-7-yl}-3,4-dihydro-2H-pyridine-1-carboxylic acid tert-butyl ester;
[7-(2-Methoxy-pyridin-4-yl)-pyrrolo[2,1-f][1,2,4]triazin-2-yl]-[4-(1-methyl-piperidin-4-yl)-phenyl]-amine;
2-[4-(4-{7-[3-(Morpholine-4-sulfonyl)-phenyl]-pyrrolo[2,1-f][1,2,4]triazin-2-ylamino}-phenyl)-piperidin-1-yl]-ethanol;
2-[4-(4-{7-[3-(Pyrrolidine-1-sulfonyl)-phenyl]-pyrrolo[2,1-f][1,2,4]triazin-2-ylamino}-phenyl)-piperidin-1-yl]ethanol;
2-(4-{4-[7-(4-Methanesulfonyl-phenyl)-pyrrolo[2,1-f][1,2,4]triazin-2-ylamino]-phenyl}-piperidin-1-yl)-ethanol;
3-[2-(3-Amino-2-hydroxy-indan-5-ylamino)-pyrrolo[2,1-f][1,2,4]triazin-7-yl]-N-tert-butyl-benzenesulfonamide;
1-Amino-6-[7-(2-methoxy-phenyl)-pyrrolo[2,1-f][1,2,4]triazin-2-ylamino]-indan-2-ol
2-(4-{4-[7-(2,6-Dimethoxy-pyridin-3-yl)-pyrrolo[2,1-f][1,2,4]triazin-2-ylamino]-phenyl}-piperidin-1-yl)-acetamide;
N-tert-Butyl-3-[2-(2-methoxy-4-piperidin-4-yl-phenylamino)-pyrrolo[2,1-f][1,2,4]triazin-7-yl]-benzenesulfonamide;
N-tert-Butyl-3-{2-[2-methoxy-4-(1-methyl-piperidin-4-yl)-phenylamino]-pyrrolo[2,1-f][1,2,4]triazin-7-yl}-benzenesulfonamide;
2-(4-{4-[7-(3-tert-Butylsulfamoylphenyl)pyrrolo[2,1-f][1,2,4]triazin-2-ylamino]-3-methoxyphenyl)piperidin-1-yl)-acetamide;
N-tert-Butyl-3-(2-{4-[1-(2-hydroxy-ethyl)-piperidin-4-yl]-2-methoxy-phenylamino}-pyrrolo[2,1-f][1,2,4]triazin-7-yl)-benzenesulfonamide;

N-tert-Butyl-3-(2-{4-[1-((S)-2,3-dihydroxy-propyl)-piperidin-4-yl}-2-methoxy-phenylamino]-pyrrolo[2,1-f][1,2,4]triazin-7-yl)-benzenesulfonamide;
N-Cyclopropyl-3-{2-[2-methoxy-4-(1-methyl-piperidin-4-yl)phenylamino]pyrrolo[2,1-f][1,2,4]triazin-7-ylbenzenesulfonamide;
2-(4-{4-[7-(3-Cyclopropylsulfamoyl-phenyl)-pyrrolo[2,1-f][1,2,4]triazin-2-ylamino]-3-methoxy-phenyl}-piperidin-1-yl)-acetamide;
N-Cyclopropyl-3-(2-{4-[1-(2-hydroxy-ethyl)-piperidin-4-yl]-2-methoxyphenylaminopyrrolo[2,1-f][1,2,4]triazin-7-yl)benzenesulfonamide;
N-tert-Butyl-3{2-[3-(2-hydroxyethyl)-8-methoxy-2,3,4,5-tetrahydro-1H-3-benzazepin-7-ylamino]pyrrolo[2,1-f][1,2,4]triazin-7-ylbenzenesulfonamide;
N-tert-Butyl-3-{2-[3-((R)-2-hydroxypropyl)-8-methoxy-2,3,4,5-tetrahydro-1H-3-benzazepin-7-ylamino]pyrrolo[2,1-f][1,2,4]triazin-7-ylbenzenesulfonamide;
N-tert-Butyl-3{2-[3-((S)-2-hydroxypropyl)-8-methoxy-2,3,4,5-tetrahydro-1H-3-benzazepin-7-ylamino]-pyrrolo[2,1-f][1,2,4]triazin-7-ylbenzenesulfonamide;
2-(4-{4-[7-(2,3-Dihydro-benzofuran-7-yl)-pyrrolo[2,1-f][1,2,4]triazin-2-ylamino]-3-methoxy-phenyl}-piperidin-1-yl)-ethanol;
2-(4-{4-[7-(2,3-Dihydro-benzofuran-7-yl)-pyrrolo[2,1-f][1,2,4]triazin-2-ylamino]-3-methoxy-phenyl}-piperidin-1-yl)-acetamide;
2-{7-[7-(2,3-Dihydro-benzofuran-7-yl)-pyrrolo[2,1-f][1,2,4]triazin-2-ylamino]-8-methoxy-1,2,4,5-tetrahydro-3-benzazepin-3-yl}-ethanol;
[7-(2,3-Dihydro-benzofuran-7-yl)-pyrrolo[2,1-f][1,2,4]triazin-2-yl]-[2-methoxy-4-(1-methyl-piperidin-4-yl)-phenyl]-amine;
2-(4-{4-[7-(2,3-Dihydro-benzofuran-7-yl)-pyrrolo[2,1-f][1,2,4]triazin-2-ylamino]-phenyl}-piperidin-1-yl)-acetamide;
2-(4-{2-[7-(2,3-Dihydro-benzofuran-7-yl)-pyrrolo[2,1-f][1,2,4]triazin-2-ylamino]-3-methoxy-6,7,8,9-tetrahydro-5H-benzocyclohepten-6-yl}-piperazin-1-yl)-ethanol;
2-{7-[7-(2,3-Dihydro-benzofuran-7-yl)-pyrrolo[2,1-f][1,2,4]triazin-2-ylamino]-8-methoxy-1,2,4,5-tetrahydro-3-benzazepin-3-yl}-acetamide;
[7-(2,3-Dihydro-benzofuran-7-yl)-pyrrolo[2,1-f][1,2,4]triazin-2-yl]-(8-methoxy-2,3,4,5-tetrahydro-1H-3-benzazepin-7-yl)-amine;
[7-(2,3-Dihydro-benzofuran-7-yl)-pyrrolo[2,1-f][1,2,4]triazin-2-yl]-(8-piperazin-1-yl-quinolin-3-yl)-amine;
4-{4-[7-(2-Methoxy-phenyl)-pyrrolo[2,1-f][1,2,4]triazin-2-ylamino]-pyrazol-1-yl}-piperidine-1-carboxylic acid tert-butyl ester;
4-(4-{7-[2-Methanesulfonyl-methyl-amino)-phenyl]-pyrrolo[2,1-f][1,2,4]triazin-2-ylamino}-pyrazol-1-yl)-piperidine-1-carboxylic acid tert-butyl ester;
4-{4-[7-(2,3-Dihydro-benzofuran-7-yl)-pyrrolo[2,1-f][1,2,4]triazin-2-ylamino]-pyrazol-1-yl}-piperidine-1-carboxylic acid tert-butyl ester;
7-[2-(2-Methoxy-4-piperidin-4-ylphenylamino)pyrrolo[2,1-f][1,2,4]triazin-7-yl]-1,3-dihydro-indol-2-one;
[7-(2,3-Dihydrobenzofuran-7-yl)pyrrolo[2,1-f][1,2,4-triazin-2-yl]-(1-piperidin-4-yl-1H-pyrazol-4-yl]amine;
4-{4-[7-(2-Methoxy-phenyl)-pyrrolo[2,1-f][1,2,4]triazin-2-ylamino]-pyrazol-1-yl}-piperidine;
N-Methyl-N-{2-[2-(1-piperidin-4-yl-1H-pyrazol-4-ylamino)-pyrrolo[2,1-f][1,2,4]triazin-7-yl]-phenyl}-methanesulfonamide;
4-{4-[7-(2,3-Dihydro-benzofuran-7-yl)-pyrrolo[2,1-f][1,2,4]triazin-2-ylamino]-3-methoxy-phenyl}-piperidin-3-ol;
1-[2-(2-Methoxy-4-piperidin-4-yl-phenylamino)-pyrrolo[2,1-f][1,2,4]triazin-7-yl]-4-phenyl-pyrrolidin-2-one;
(3-Dimethylamino-benzyl)-[5-(2-methoxy-phenyl)-pyrrolo[2,1-f][1,2,4]triazin-2-yl]-amine;
[5-(2-Methoxy-phenyl)-pyrrolo[2,1-f][1,2,4]triazin-2-yl]-(2-methyl-1,2,3,4-tetrahydro-isoquinolin-7-yl)-amine;
(4-Ethyl-piperazin-1-yl)-{4-[5-(2-methoxy-phenyl)-pyrrolo[2,1-f][1,2,4]triazin-2-ylamino]-phenyl}-methanone;
[5-(4-Methoxy-phenyl)-pyrrolo[2,1-f][1,2,4]triazin-2-yl]-[4-(4-methyl-piperazin-1-yl)-phenyl]-amine;
[5-(3-Methoxy-phenyl)-pyrrolo[2,1-f][1,2,4]triazin-2-yl]-[4-(4-methyl-piperazin-1-yl)-phenyl]-amine;
[5-(4-Fluoro-phenyl)-pyrrolo[2,1-f][1,2,4]triazin-2-yl]-[4-(4-methyl-piperazin-1-yl)-phenyl]-amine;
(4-Ethyl-piperazin-1-yl)-{4-[5-(4-fluoro-phenyl)-pyrrolo[2,1-f][1,2,4]triazin-2-ylamino]-phenyl}-methanone;
[5-(4-Fluoro-phenyl)-pyrrolo[2,1-f][1,2,4]triazin-2-yl]-(2-methyl-1,2,3,4-tetrahydro-isoquinolin-7-yl)-amine;
(3-Dimethylamino-benzyl)-[5-(4-fluoro-phenyl)-pyrrolo[2,1-f][1,2,4]triazin-2-yl]-amine;
[5-(3-Fluoro-phenyl)-pyrrolo[2,1-f][1,2,4]triazin-2-yl]-[4-(4-methyl-piperazin-1-yl)-phenyl]-amine;
4-Hydroxy-4-(4-{7-[2-(methanesulfonyl-methyl-amino)-phenyl]-pyrrolo[2,1-f][1,2,4]triazin-2-ylamino}-3-methoxy-phenyl)-piperidine-1-carboxylic acid tert-butyl ester;
N-(2-{2-[2-Methoxy-4-(1,2,3,6-tetrahydro-pyridin-4-yl)-phenylamino]-pyrrolo[2,1-f][1,2,4]triazin-7-yl}-phenyl)-N-methyl-methanesulfonamide;
N-(2-{2-[4-(1-Ethyl-4-hydroxy-piperidin-4-yl)-2-methoxy-phenylamino]-pyrrolo[2,1-f][1,2,4]triazin-7-yl}-phenyl)-N-methyl-methanesulfonamide;
N-(2-{2-[4-(1-Ethyl-1,2,3,6-tetrahydro-pyridin-4-yl)-2-methoxy-phenylamino]-pyrrolo[2,1-f][1,2,4]triazin-7-yl}-phenyl)-N-methyl-methanesulfonamide;
2-(4-{4-[7-(2,4-Dimethoxy-phenyl)-pyrrolo[2,1-f][1,2,4]triazin-2-ylamino]-3-methoxy-phenyl}-piperidin-1-yl)-acetamide;
2-[4-(4-{7-[4,5-Difluoro-2-(methanesulfonyl-methyl-amino)-phenyl]-pyrrolo[2,1-f][1,2,4]triazin-2-ylamino}-3-methoxy-phenyl)-piperidin-1-yl]-acetamide;
(4-Bromo-phenyl)-[1,2,4]triazino[1,6-a]indol-2-yl-amine;
(4-Methoxy-phenyl)-[1,2,4]triazino[1,6-a]indol-2-yl-amine;
(S)-1-(4-{3-Methoxy-4-[7-(2-methoxy-phenyl)-pyrrolo[2,1-f][1,2,4]triazin-2-ylamino]-phenyl}-piperazin-1-yl)-propan-2-ol;
(R)-1-(4-{3-Methoxy-4-[7-(2-methoxy-phenyl)-pyrrolo[2,1-f][1,2,4]triazin-2-ylamino]-phenyl}-piperazin-1-yl)-propan-2-ol;
(S)-1-(4-{4-[7-(5-Chloro-2-methoxy-phenyl)-pyrrolo[2,1-f][1,2,4]triazin-2-ylamino]-3-methoxy-phenyl}-piperazin-1-yl)-propan-2-ol;
(R)-1-(4-{4-[7-(5-Chloro-2-methoxy-phenyl)-pyrrolo[2,1-f][1,2,4]triazin-2-ylamino]-3-methoxy-phenyl}-piperazin-1-yl)-propan-2-ol;
(R)-3-(4-{4-[7-(5-Chloro-2-methoxy-phenyl)-pyrrolo[2,1-f][1,2,4]triazin-2-ylamino]-3-methoxy-phenyl}-piperazin-1-yl)-propane-1,2-diol;

(R)-3-(4-{3-Methoxy-4-[7-(2-methoxy-phenyl)-pyrrolo[2,1-f][1,2,4]triazin-2-ylamino]-phenyl}-piperazin-1-yl)-propane-1,2-diol;

(S)-3-(4-{3-Methoxy-4-[7-(2-methoxy-phenyl)-pyrrolo[2,1-f][1,2,4]triazin-2-ylamino]-phenyl}-piperazin-1-yl)-propane-1,2-diol;

(S)-3-(4-{3-Methoxy-4-[7-(2-methoxy-phenyl)-pyrrolo[2,1-f][1,2,4]triazin-2-ylamino]-phenyl}-piperidin-1-yl)-propane-1,2-diol;

[2-Methoxy-4-(1-methyl-piperidin-4-yl)-phenyl]-[7-(2-methoxy-phenyl)-pyrrolo[2,1-f][1,2,4]triazin-2-yl]-amine;

[4-(3-Dimethylamino-pyrrolidin-1-yl)-2-methoxy-phenyl]-[7-(2-methoxy-phenyl)-pyrrolo[2,1-f][1,2,4]triazin-2-yl]-amine;

(3,4-Dihydro-2H-1,4-ethano-quinolin-7-yl)-[7-(2-methoxy-phenyl)-pyrrolo[2,1-f][1,2,4]triazin-2-yl]-amine;

[2-Methoxy-4-(4-methyl-[1,4]diazepan-1-yl)-phenyl]-[7-(2-methoxy-phenyl)-pyrrolo[2,1-f][1,2,4]triazin-2-yl]-amine;

(R)-1-(4-{3-Methoxy-4-[7-(2-methoxy-phenyl)-pyrrolo[2,1-f][1,2,4]triazin-2-ylamino]-phenyl}-[1,4]diazepan-1-yl)-propan-2-ol;

(S)-3-(4-{3-Methoxy-4-[7-(2-methoxy-phenyl)-pyrrolo[2,1-f][1,2,4]triazin-2-ylamino]-phenyl}-[1,4]diazepan-1-yl)-propane-1,2-diol;

(±)-1-Methoxy-8-morpholin-4-yl-6,7,8,9-tetrahydro-5H-enzocyclohepten-2-yl)-[7-(2-methoxy-phenyl)-pyrrolo[2,1-f][1,2,4]triazin-2-yl]-amine;

N-[2-(2-{4-[1-((S)-2,3-Dihydroxy-propyl)-piperidin-4-yl]-2-methoxy-phenylamino}-pyrrolo[2,1-f][1,2,4]triazin-7-yl)-phenyl]-N-methyl-methanesulfonamide;

[2-Methoxy-5-(1-methyl-piperidin-4-yl)-phenyl]-[7-(2-methoxy-phenyl)-pyrrolo[2,1-f][1,2,4]triazin-2-yl]-amine;

N-[2-{2-[2-Methoxy-4-(4-methyl-[1,4]diazepan-1-yl)-phenylamino]-pyrrolo[2,1-f][1,2,4]triazin-7-yl}-phenyl)-N-methyl-methanesulfonamide;

N-[2-(2-{4-[4-((R)-2-Hydroxy-propyl)-[1,4]diazepan-1-yl]-2-methoxy-phenylamino}-pyrrolo[2,1-f][1,2,4]triazin-7-yl)-phenyl]-N-methyl-methanesulfonamide;

N-[2-(2-{4-[4-((S)-2,3-Dihydroxy-propyl)-[1,4]diazepan-1-yl]-2-methoxy-phenylamino}-pyrrolo[2,1-f][1,2,4]triazin-7-yl)-phenyl]-N-methyl-methanesulfonamide;

N-(2-{2-[2-Methoxy-5-(1-methyl-piperidin-4-yl)-phenylamino]-pyrrolo-[2,1-f][1,2,4]triazin-7-yl}-phenyl)-N-methyl-methanesulfonamide;

[2-Methoxy-3-(1-methyl-piperidin-4-yl)-phenyl]-[7-(2-methoxy-phenyl)-pyrrolo[2,1-f][1,2,4]triazin-2-yl]-amine;

N-(2-{2-[2-Methoxy-3-(1-methyl-piperidin-4-yl)-phenylamino]-pyrrolo[2,1-f][1,2,4]triazin-7-yl}-phenyl)-N-methyl-methanesulfonamide;

(±)-[4(1,3-Diethyl-piperidin-3-yl)-phenyl]-[7-(2-methoxy-phenyl)pyrrolo-[2,1-f][1,2,4]triazin-2-yl]-amine;

(±)-N-(2-{2-[4-(1,3-Diethyl-piperidin-3-yl)-phenylamino]-pyrrolo[2,1-f][1,2,4]triazin-7-yl}-phenyl)-N-methyl-methanesulfonamide;

(±)-[2-Methoxy-4-(3-morpholin-4-yl-pyrrolidin-1-yl)-phenyl]-[7-(2-methoxyphenyl)-pyrrolo[2,1-f][1,2,4]triazin-2-yl]-amine;

[2-Methoxy-4-(4-[1,4]oxazepan-4-yl-piperidin-1-yl)-phenyl]-[7-(2-methoxy-phenyl)-pyrrolo[2,1-f][1,2,4]triazin-2-yl]-amine;

{2-Methoxy-4-[4-(4-methyl-[1,4]diazepan-1-yl)-piperidin-1-yl]-phenyl}-[7-(2-methoxy-phenyl)-pyrrolo[2,1-f][1,2,4]triazin-2-yl]-amine;

(±)-N-(2-{2-[2-Methoxy-4-(3-morpholin-4-yl-pyrrolidin-1-yl)-phenylamino]-pyrrolo[2,1-f][1,2,4]triazin-7-yl}-phenyl)-N-methyl-methanesulfonamide;

N-(2-{2-[2-Methoxy-4-(4-[1,4]oxazepan-4-yl-piperidin-1-yl)-henylamino]-pyrrolo[2,1-f][1,2,4]triazin-7-yl}-phenyl)-N-methyl-methanesulfonamide;

N-[2-(2-{2-Methoxy-4-[4-(4-methyl-[1,4]diazepan-1-yl)-piperidin-1-yl]-phenylamino}-pyrrolo[2,1-f][1,2,4]triazin-7-yl)-phenyl]-N-methyl-methanesulfonamide;

N-[2-(2-{(S)-1-[4-(4-Amino-3-methoxy-phenyl)-piperidin-1-ylmethyl]-2,2,2-trifluoro-ethoxy}-pyrrolo[2,1-f][1,2,4]triazin-7-yl)-phenyl]-N-methyl-methanesulfonamide;

2-Methoxy-4-(1-{(S)-3,3,3-trifluoro-2-[7-(2-methoxy-phenyl)-pyrrolo[2,1-f][1,2,4]triazin-2-yloxy]-propyl}-piperidin-4-yl)-phenylamine;

(R)-1-(4-{3-Methoxy-4-[7-(2-methoxy-phenyl)-pyrrolo[2,1-f][1,2,4]triazin-2-ylamino]-phenyl}-piperidin-1-yl)-propan-2-ol;

N-[2-(2-{4-[1-((R)-2-Hydroxy-propyl)-piperidin-4-yl]-2-methoxy-phenylamino}-pyrrolo[2,1-f][1,2,4]triazin-7-yl)-phenyl]-N-methyl-methanesulfonamide;

{2-Methoxy-4-[4-(1-methyl-piperidin-4-yl)-[1,4]diazepan-1-yl]-phenyl}-[7-(2-methoxy-phenyl)-pyrrolo[2,1-f][1,2,4]triazin-2-yl]-amine;

N-[2-(2-{2-Methoxy-4-[4-(1-methyl-piperidin-4-yl)-[1,4]diazepan-1-yl]-phenylamino}-pyrrolo[2,1-f][1,2,4]triazin-7-yl)-phenyl]-N-methyl-methanesulfonamide;

{4-[1-(2-Fluoro-ethyl)-piperidin-4-yl]-2-methoxy-phenyl}-[7-(2-methoxy-phenyl)-pyrrolo[2,1-f][1,2,4]triazin-2-yl]-amine;

N-[2-(2-{4-[1-(2-Fluoro-ethyl)-piperidin-4-yl]-2-methoxy-phenylamino}-pyrrolo[2,1-f][1,2,4]triazin-7-yl)-phenyl]-N-methyl-methanesulfonamide;

N-[2-(2-{4-[1-(2-Hydroxy-ethyl)-piperidin-4-yl]-2-methoxy-henylamino}-pyrrolo[2,1-f][1,2,4]triazin-7-yl)-phenyl]-N-methyl-methanesulfonamide;

(R)-1-(4-{4-[7-(5-Chloro-2-methoxy-phenyl)-pyrrolo[2,1-f][1,2,4]triazin-2-ylamino]-3-methoxy-phenyl}-piperidin-1-yl)-propan-2-ol;

N-{2-[2-(4-[4-[(2-Hydroxy-ethyl)-methyl-amino]-piperidin-1-yl]-2-ethoxy-phenylamino)-pyrrolo[2,1-f][1,2,4]triazin-7-yl]-phenyl}-N-methyl-methanesulfonamide;

2-[(1-{3-Methoxy-4-[7-(2-methoxy-phenyl)-pyrrolo[2,1-f][1,2,4]triazin-2-ylamino]-phenyl}-piperidin-4-yl)-methyl-amino]-ethanol;

2-(1-{3-Methoxy-4-[7-(2-methoxy-phenyl)-pyrrolo[2,1-f][1,2,4]triazin-2-ylamino]-phenyl}-piperidin-4-ylamino)-ethanol;

N-[2-(2-{4-[4-(2-Hydroxy-ethylamino)-piperidin-1-yl]-2-methoxy-phenylamino}-pyrrolo[2,1-f][1,2,4]triazin-7-yl)-phenyl]-N-methyl-methanesulfonamide;

(S)-1,1,1-Trifluoro-3-(4-{3-methoxy-4-[7-(2-methoxy-phenyl)-pyrrolo[2,1-f][1,2,4]triazin-2-ylamino]-phenyl}-piperidin-1-yl)-propan-2-ol;

2-[4-(4-{3-Methoxy-4-[7-(2-methoxy-phenyl)-pyrrolo[2,1-f][1,2,4]triazin-2-ylamino]-phenyl}[1,4]diazepan-1-yl)-piperidin-1-yl]-ethanol;

2-[4-(1-{3-Methoxy-4-[7-(2-methoxy-phenyl)-pyrrolo[2,1-f][1,2,4]triazin-2-ylamino]-phenyl}-piperidin-4-yl)-[1,4]diazepan-1-yl]-ethanol;

N-{2-[2-(4-[4-[1-(2-Hydroxy-ethyl)-piperidin-4-yl]-[1,4]
diazepan-1-yl]-2-methoxy-phenylamino)-pyrrolo[2,1-
f][1,2,4]triazin-7-yl]-phenyl}-N-methyl-methane-
sulfonamide;
N-{2-[2-(4-[4-[4-(2-Hydroxy-ethyl)-[1,4]diazepan-1-yl]-
piperidin-1-yl]-2-methoxy-phenylamino)-pyrrolo[2,1-
f][1,2,4]triazin-7-yl]-phenyl}-N-methyl-methane-
sulfonamide;
N-[2-(2-{2-Methoxy-4-[1-((S)-3,3,3-trifluoro-2-hy-
droxy-propyl)-piperidin-4-yl]-phenylamino}-pyrrolo
[2,1-f][1,2,4]triazin-7-yl)-phenyl]-N-methyl-methane-
sulfonamide;
[2-Methoxy-4-(1-methyl-piperidin-3-yl)-phenyl]-[7-(2-
methoxy-phenyl)-pyrrolo[2,1-f][1,2,4]triazin-2-yl]-
amine;
N-(2-{2-[2-Methoxy-4-(1-methyl-piperidin-3-yl)-pheny-
lamino]-pyrrolo[2,1-f][1,2,4]triazin-7-yl}-phenyl)-N-
methyl-methanesulfonamide;
[7-(2-Methoxy-phenyl)-pyrrolo[2,1-f][1,2,4]triazin-2-yl]-
(2-methoxy-4-pyridin-3-yl-phenyl)-amine;
N-{2-[2-(2-Methoxy-4-pyridin-3-yl-phenylamino)-pyr-
rolo[2,1-f][1,2,4]triazin-7-yl]-phenyl}-N-methyl-
methanesulfonamide;
N-{2-[2-(6-Methoxy-2-methyl-2,3-dihydro-1H-isoindol-
5-ylamino)-pyrrolo[2,1-f][1,2,4]triazin-7-yl]-phenyl}-
N-methyl-methanesulfonamide;
2-[4-(4-{7-[2-(Methanesulfonyl-methyl-amino)-phenyl]-
pyrrolo[2,1-f][1,2,4]triazin-2-ylamino}-3-methoxy-
phenyl)-piperidin-1-yl]-N,N-dimethyl-acetamide;
2-(4-{3-Methoxy-4-[7-(2-methoxy-phenyl)-pyrrolo[2,1-
f][1,2,4]triazin-2-ylamino]-phenyl}-piperidin-1-yl)-N,
N-dimethyl-acetamide;
2-[4-(4-{7-[2-(Methanesulfonyl-methyl-amino)-phenyl]-
pyrrolo[2,1-f][1,2,4]triazin-2-ylamino}-3-methoxy-
phenyl)-piperidin-1-yl]-acetamide;
N-[2-(2-{4-[1-(2-Dimethylamino-acetyl)-piperidin-4-yl]-
2-methoxy-phenylamino}-pyrrolo[2,1-f][1,2,4]triazin-
7-yl)-phenyl]-N-methyl-methanesulfonamide;
2-(4-{3-Methoxy-4-[7-(2-methoxy-phenyl)-pyrrolo[2,1-
f][1,2,4]triazin-2-ylamino]-phenyl}-piperidin-1-yl)-ac-
etamide;
2-Dimethylamino-1-(4-{3-methoxy-4-[7-(2-methoxy-
phenyl)-pyrrolo[2,1-f][1,2,4]triazin-2-ylamino]-phe-
nyl}-piperidin-1-yl)-ethanone;
(6-Methoxy-2-methyl-2,3-dihydro-1H-isoindol-5-yl)-[7-
(2-methoxy-phenyl)-pyrrolo[2,1-f][1,2,4]triazin-2-yl]-
amine;
4-{3-Methoxy-4-[7-(2-methoxy-phenyl)-pyrrolo[2,1-f]
[1,2,4]triazin-2-ylamino]-phenyl}-piperidine-1-car-
boxylic acid tert-butyl ester;
4-(4-{7-[2-(Methanesulfonyl-methyl-amino)-phenyl]-
pyrrolo[2,1-f][1,2,4]triazin-2-ylamino}-3-methoxy-
phenyl)-piperidine-1-carboxylic acid tert-butyl ester;
N-{2-[2-(2-Methoxy-4-piperidin-4-yl-phenylamino)-pyr-
rolo[2,1-f][1,2,4]triazin-7-yl]-phenyl}-N-methyl-
methanesulfonamide;
[7-(2-Methoxy-phenyl)-pyrrolo[2,1-f][1,2,4]triazin-2-yl]-
(2-methoxy-4-piperidin-4-yl-phenyl)-amine;
2-Amino-1-(4-{3-methoxy-4-[7-(2-methoxy-phenyl)-
pyrrolo[2,1-f][1,2,4]triazin-2-ylamino]-phenyl}-pip-
eridin-1-yl)-2-methyl-propan-1-one;
N-[2-(2-{4-[1-(2-Amino-2-methyl-propionyl)-piperidin-
4-yl]-2-methoxy-phenylamino}-pyrrolo[2,1-f][1,2,4]
triazin-7-yl)-phenyl]-N-methyl-methanesulfonamide;
2-Amino-1-(4-{3-methoxy-4-[7-(2-methoxy-phenyl)-
pyrrolo[2,1-f][1,2,4]triazin-2-ylamino]-phenyl}-pip-
eridin-1-yl)-ethanone;
N-[2-(2-{4-[1-(2-Amino-acetyl)-piperidin-4-yl]-2-meth-
oxy-phenylamino}-pyrrolo[2,1-f][1,2,4]triazin-7-yl)-
phenyl]-N-methyl-methanesulfonamide;
(±)-1-Fluoro-3-(4-{3-methoxy-4-[7-(2-methoxy-phenyl)-
pyrrolo[2,1-f][1,2,4]triazin-2-ylamino]-phenyl}-pip-
eridin-1-yl)-propan-2-ol;
(±)-N-[2-(2-{-4-[1-(3-Fluoro-2-hydroxy-propyl)-piperi-
din-4-yl]-2-methoxy-phenylamino}-pyrrolo[2,1-f][1,2,
4]triazin-7-yl)-phenyl]-N-methyl-methanesulfona-
mide;
[2-Methoxy-4-(1-oxetan-3-yl-piperidin-4-yl)-phenyl]-[7-
(2-methoxy-phenyl)-pyrrolo[2,1-f][1,2,4]triazin-2-yl]-
amine;
N-(2-{2-[2-Methoxy-4-(1-oxetan-3-yl-piperidin-4-yl)-
phenylamino]-pyrrolo[2,1-f][1,2,4]triazin-7-yl}-phe-
nyl)-N-methyl-methanesulfonamide;
(±)-(3S,4S)-4-{3-Methoxy-4-[7-(2-methoxy-phenyl)-pyr-
rolo[2,1-f][1,2,4]triazin-2-ylamino]-phenyl}-1-methyl-
piperidine-3,4-diol;
(±)-4-{3-Methoxy-4-[7-(2-methoxy-phenyl)-pyrrolo[2,1-
f][1,2,4]triazin-2-ylamino]-phenyl}-1-methyl-piperi-
din-3-ol;
(±)-(3S,4S)-3,4-Dihydroxy-4-{3-methoxy-4-[7-(2-meth-
oxy-phenyl)-pyrrolo[2,1-f][1,2,4]triazin-2-ylamino]-
phenyl}-piperidine-1-carboxylic acid tert-butyl ester;
(±)-(3S,4S)-4-{3-Methoxy-4-[7-(2-methoxy-phenyl)-pyr-
rolo[2,1-f][1,2,4]triazin-2-ylamino]-phenyl}-piperi-
dine-3,4-diol;
(±)-(3S,4S)-1-(2-Fluoro-ethyl)-4-{3-methoxy-4-[7-(2-
methoxy-phenyl)-pyrrolo[2,1-f][1,2,4]triazin-2-
ylamino]-phenyl}-piperidine-3,4-diol;
(±)-(3R,4S)-3-Hydroxy-4-{3-methoxy-4-[7-(2-methoxy-
phenyl)-pyrrolo[2,1-f][1,2,4]triazin-2-ylamino]-phe-
nyl}-piperidine-1-carboxylic acid tert-butyl ester;
(±)-(3R,4S)-4-{3-Methoxy-4-[7-(2-methoxy-phenyl)-
pyrrolo[2,1-f][1,2,4]triazin-2-ylamino]-phenyl}-pip-
eridin-3-ol;
(±)-2-(3-{3-Methoxy-4-[7-(2-methoxy-phenyl)-pyrrolo
[2,1-f][1,2,4]triazin-2-ylamino]-phenyl}-pyrrolidin-1-
yl)-acetamide;
(±)-2-[3-(4-{7-[2-(Methanesulfonyl-methyl-amino)-phe-
nyl]-pyrrolo[2,1-f][1,2,4]triazin-2-ylamino}-3-meth-
oxy-phenyl)-pyrrolidin-1-yl]-acetamide;
(±)-(3R,4S)-1-(2-Fluoro-ethyl)-4-{3-methoxy-4-[7-(2-
methoxy-phenyl)-pyrrolo[2,1-f][1,2,4]triazin-2-
ylamino]-phenyl}-piperidin-3-ol;
(±)-2-((3R,4S)-3-Hydroxy-4-{3-methoxy-4-[7-(2-meth-
oxy-phenyl)-pyrrolo[2,1-f][1,2,4]triazin-2-ylamino]-
phenyl}-piperidin-1-yl)-acetamide;
(±)-N-(2-{2-[4-((3S,4S)-3,4-Dihydroxy-piperidin-4-yl)-
2-methoxy-phenylamino]-pyrrolo[2,1-f][1,2,4]triazin-
7-yl}-phenyl)-N-methyl-methanesulfonamide;
(±)-N-(2-{2-[4-((3 R,4S)-3-Hydroxy-piperidin-4-yl)-2-
methoxy-phenylamino]-pyrrolo[2,1-f][1,2,4]triazin-7-
yl}-phenyl)-N-methyl-methanesulfonamide;
(±)-2-[(3R,4S)-3-Hydroxy-4-(4-{7-[2-(methanesulfonyl-
methyl-amino)-phenyl]-pyrrolo[2,1-f][1,2,4]triazin-2-
ylamino}-3-methoxy-phenyl)-piperidin-1-yl]-aceta-
mide;
(±)-N-[2-(2-{4-[(3R,4S)-1-(2-Fluoro-ethyl)-3-hydroxy-
piperidin-4-yl]-2-methoxy-phenylamino}-pyrrolo[2,1-
f][1,2,4]triazin-7-yl)-phenyl]-N-methyl-methane-
sulfonamide;
(±)-2-[(3S,4S)-3,4-Dihydroxy-4-(4-{7-[2-(methanesulfo-
nyl-methyl-amino)-phenyl]-pyrrolo[2,1-f][1,2,4]tri-
azin-2-ylamino}-3-methoxy-phenyl)-piperidin-1-yl]-
acetamide;

(±)-N-[2-(2-{4-[(3S,4S)-1-(2-Fluoro-ethyl)-3,4-dihydroxy-piperidin-4-yl]-2-methoxy-phenylamino}-pyrrolo[2,1-f][1,2,4]triazin-7-yl)-phenyl]-N-methyl-methanesulfonamide;

(±)-N-[2-(2-{4-[(3S,4S)-3,4-Dihydroxy-1-(2-methoxy-ethyl)-piperidin-4-yl]-2-methoxy-phenylamino}-pyrrolo[2,1-f][1,2,4]triazin-7-yl)-phenyl]-N-methyl-methanesulfonamide;

(±)-N-[2-(2-{4-[(3R,4S)-3-Hydroxy-1-(2-hydroxy-ethyl)-piperidin-4-yl]-2-methoxy-phenylamino}-pyrrolo[2,1-f][1,2,4]triazin-7-yl)-phenyl]-N-methyl-methanesulfonamide;

(±)-(3R,4S)-1-(2-Hydroxy-ethyl)-4-{3-methoxy-4-[7-(2-methoxy-phenyl)-pyrrolo[2,1-f][1,2,4]triazin-2-ylamino]-phenyl}-piperidin-3-ol;

(±)-2-((3S,4S)-3,4-Dihydroxy-4-{3-methoxy-4-[7-(2-methoxy-phenyl)-pyrrolo[2,1-f][1,2,4]triazin-2-ylamino]-phenyl}-piperidin-1-yl)-acetamide;

(6-Methoxy-2-oxetan-3-yl-2,3-dihydro-1H-isoindol-5-yl)-[7-(2-methoxy-phenyl)-pyrrolo[2,1-f][1,2,4]triazin-2-yl]-amine;

(4-Methoxy-2-oxetan-3-yl-2,3-dihydro-1H-isoindol-5-yl)-[7-(2-methoxy-phenyl)-pyrrolo[2,1-f][1,2,4]triazin-2-yl]-amine;

[6-Methoxy-2-(1-methyl-piperidin-4-yl)-2,3-dihydro-1H-isoindol-5-yl]-[7-(2-methoxy-phenyl)-pyrrolo[2,1-f][1,2,4]triazin-2-yl]-amine;

[4-Methoxy-2-(1-methyl-piperidin-4-yl)-2,3-dihydro-1H-isoindol-5-yl]-[7-(2-methoxy-phenyl)-pyrrolo[2,1-f][1,2,4]triazin-2-yl]-amine;

2-(4-{3-Methoxy-4-[7-(2-pyrazol-1-yl-phenyl)-pyrrolo[2,1-f][1,2,4]triazin-2-ylamino]-phenyl}-piperidin-1-yl)-acetamide;

(±)-(3S,4S)-4-{3-Methoxy-4-[7-(2-methoxy-phenyl)-pyrrolo[2,1-f][1,2,4]triazin-2-ylamino]-phenyl}-piperidin-3-ol;

(±)-(3S,4S)-1-(2-Hydroxy-ethyl)-4-{3-methoxy-4-[7-(2-methoxy-phenyl)-pyrrolo[2,1-f][1,2,4]triazin-2-ylamino]-phenyl}-piperidin-3-ol;

2-(4-{3-Methoxy-4-[7-(3-methoxy-pyridin-4-yl)-pyrrolo[2,1-f][1,2,4]triazin-2-ylamino]-phenyl}-piperidin-1-yl)-acetamide;

(±)-[4-(1,3-Dimethyl-piperidin-4-yl)-2-methoxy-phenyl]-[7-(2-methoxy-phenyl)-pyrrolo[2,1-f][1,2,4]triazin-2-yl]-amine;

(±)-[2-Methoxy-4-(3-methoxy-1-methyl-piperidin-4-yl)-phenyl]-[7-(2-methoxy-phenyl)-pyrrolo[2,1-f][1,2,4]triazin-2-yl]-amine;

(±)-2-(3-{3-Methoxy-4-[7-(2-methoxy-phenyl)-pyrrolo[2,1-f][1,2,4]triazin-2-ylamino]-phenyl}-piperidin-1-yl)-acetamide;

(±)-2-[3-(4-{7-[2-(Methanesulfonyl-methyl-amino)-phenyl]-pyrrolo[2,1-f][1,2,4]triazin-2-ylamino}-3-methoxy-phenyl)-piperidin-1-yl]-acetamide;

(±)-Azetidin-2-yl-(4-{3-methoxy-4-[7-(2-methoxy-phenyl)-pyrrolo[2,1-f][1,2,4]triazin-2-ylamino]-phenyl}-piperidin-1-yl)-methanone;

(±)-N-[2-(2-{4-[1-(Azetidine-2-carbonyl)-piperidin-4-yl]-2-methoxy-phenylamino}-pyrrolo[2,1-f][1,2,4]triazin-7-yl)-phenyl]-N-methyl-methanesulfonamide;

2-{5-Methoxy-6-[7-(2-methoxy-phenyl)-pyrrolo[2,1-f][1,2,4]triazin-2-ylamino]-1,3-dihydro-isoindol-2-yl}-acetamide;

1-(4-{3-Methoxy-4-[7-(2-methoxy-phenyl)-pyrrolo[2,1-f][1,2,4]triazin-2-ylamino]-phenyl}-piperidin-1-yl)-2-methyl-propan-2-ol;

N-[2-(2-{4-[1-(2-Hydroxy-2-methyl-propyl)-piperidin-4-yl]-2-methoxy-phenylamino}-pyrrolo[2,1-f][1,2,4]triazin-7-yl)-phenyl]-N-methyl-methanesulfonamide;

2-(4-{3-Methoxy-4-[7-(2-methoxy-phenyl)-pyrrolo[2,1-f][1,2,4]triazin-2-ylamino]-phenyl}-piperidin-1-yl)-N-methyl-acetamide;

{4-[1-(1H-Imidazol-2-ylmethyl)-piperidin-4-yl]-2-methoxy-phenyl}-[7-(2-methoxy-phenyl)-pyrrolo[2,1-f][1,2,4]triazin-2-yl]-amine;

2-(5-{7-[2-(Methanesulfonyl-methyl-amino)-phenyl]-pyrrolo[2,1-f][1,2,4]triazin-2-ylamino}-6-methoxy-1,3-dihydro-isoindol-2-yl)-acetamide;

2-[4-(4-{7-[2-(Methanesulfonyl-methyl-amino)-phenyl]-pyrrolo[2,1-f][1,2,4]triazin-2-ylamino}-3-methoxy-phenyl)-piperidin-1-yl]-N-methyl-acetamide;

(±)-N-[2-(2-{2-Methoxy-4-[1-(1-methyl-azetidin-2-ylmethyl)-piperidin-4-yl]-phenylamino}-pyrrolo[2,1-f][1,2,4]triazin-7-yl)-phenyl]-N-methyl-methanesulfonamide;

N-[2-(2-{4-[1-((S)-2,3-Dihydroxy-propyl)-piperidin-4-yl]-2-methoxy-phenylamino}-pyrrolo[2,1-f][1,2,4]triazin-7-yl)-phenyl]-N-ethyl-methanesulfonamide;

N-Ethyl-N-[2-(2-{4-[1-((R)-2-hydroxy-propyl)-piperidin-4-yl]-2-methoxy-phenylamino}-pyrrolo[2,1-f][1,2,4]triazin-7-yl)-phenyl]-methanesulfonamide;

5-Methoxy-6-[7-(2-methoxy-phenyl)-pyrrolo[2,1-f][1,2,4]triazin-2-ylamino]-1,3-dihydro-isoindole-2-carboxylic acid tert-butyl ester;

5-{7-[2-(Methanesulfonyl-methyl-amino)-phenyl]-pyrrolo[2,1-f][1,2,4]triazin-2-ylamino}-6-methoxy-1,3-dihydro-isoindole-2-carboxylic acid tert-butyl ester;

N-{2-[2-(2-Isopropyl-6-methoxy-2,3-dihydro-1H-isoindol-5-ylamino)-pyrrolo[2,1-f][1,2,4]triazin-7-yl]-phenyl}-N-methyl-methanesulfonamide;

(2-Isopropyl-6-methoxy-2,3-dihydro-1H-isoindol-5-yl)-[7-(2-methoxy-phenyl)-pyrrolo[2,1-f][1,2,4]triazin-2-yl]-amine;

2-Amino-1-{5-methoxy-6-[7-(2-methoxy-phenyl)-pyrrolo[2,1-f][1,2,4]triazin-2-ylamino]-1,3-dihydro-isoindol-2-yl}-ethanone;

N-(2-{2-[2-(2-Amino-acetyl)-6-methoxy-2,3-dihydro-1H-isoindol-5-ylamino)-pyrrolo[2,1-d][1,2,4]triazin-7-yl}-phenyl)-N-methyl-methanesulfonamide;

N-{3-[2-(3-Acetylamino-phenylamino)-pyrrolo[2,1-f][1,2,4]triazin-7-yl]-phenyl}-2,2-dimethyl-propionamide;

N-{3-[2-(1-Acetyl-2,3-dihydro-1H-indol-6-ylamino)-pyrrolo[2,1-f][1,2,4]triazin-7-yl]-phenyl}-2,2-dimethyl-propionamide;

N-tert-Butyl-3-{2-[3-(4-methyl-piperazin-1-yl)-phenylamino]-pyrrolo[2,1-f][1,2,4]triazin-7-yl}-benzenesulfonamide;

N-(3-{7-[3-((S)-3-Hydroxy-pyrrolidine-1-sulfonyl)-phenyl]-pyrrolo[2,1-f][1,2,4]triazin-2-ylamino}-phenyl)-acetamide;

1-(6-{7-[3-((S)-3-Hydroxy-pyrrolidine-1-sulfonyl)-phenyl]-pyrrolo[2,1-f][1,2,4]triazin-2-ylamino}-2,3-dihydro-indol-1-yl)-ethanone;

3-[2-(3-Acetylamino-phenylamino)-pyrrolo[2,1-f][1,2,4]triazin-7-yl]-N-tert-butyl-benzamide;

3-[2-(1-Acetyl-2,3-dihydro-1H-indol-6-ylamino)-pyrrolo[2,1-f][1,2,4]triazin-7-yl]-N-tert-butyl-benzamide;

N-{5-[7-(3-tert-Butylsulfamoyl-phenyl)-pyrrolo[2,1-f][1,2,4]triazin-2-ylamino]-2-chloro-phenyl}-acetamide;

N-tert-Butyl-3-[2-(3-methanesulfonylamino-phenylamino)-pyrrolo[2,1-f][1,2,4]triazin-7-yl]-benzenesulfonamide;

3-[7-(3-tert-Butylsulfamoyl-phenyl)-pyrrolo[2,1-f][1,2,4]triazin-2-ylamino]-benzoic acid ethyl ester;

N-tert-Butyl-3-{2-[3-(4-methyl-piperazine-1-carbonyl)-phenylamino]-pyrrolo[2,1-f][1,2,4]triazin-7-yl}-benzenesulfonamide;

N-tert-Butyl-3-{2-[3-(morpholine-4-carbonyl)-phenylamino]-pyrrolo[2,1-f][1,2,4]triazin-7-yl}-benzenesulfonamide;

N-(3-{7-[3-(2-Methanesulfonyl-ethylamino)-phenyl]-pyrrolo[2,1-f][1,2,4]triazin-2-ylamino}-phenyl)-acetamide;

{7-[3-(2-Methanesulfonyl-ethylamino)-phenyl]-pyrrolo[2,1-f][1,2,4]triazin-2-yl}-[3-(4-methyl-piperazin-1-yl)-phenyl]-amine;

3-[7-(3-tert-Butylsulfamoyl-phenyl)-pyrrolo[2,1-f][1,2,4]triazin-2-ylamino]-benzoic acid 3-[2-(3-Amino-phenylamino)-pyrrolo[2,1-f][1,2,4]triazin-7-yl]-N-tert-butyl-benzenesulfonamide;

N-{3-[7-(3-tert-Butylsulfamoyl-phenyl)-pyrrolo[2,1-f][1,2,4]triazin-2-ylamino]-phenyl}-2-dimethylamino-acetamide;

N-[7-(6-Methoxy-pyridin-3-yl)-pyrrolo[2,1-f][1,2,4]triazin-2-yl]-benzene-1,3-diamine 2-Dimethylamino-N-{3-[7-(6-methoxy-pyridin-3-yl)-pyrrolo[2,1-f][1,2,4]triazin-2-ylamino]-phenyl}-acetamide;

(R)-2-Methoxy-N-{3-[7-(6-methoxy-pyridin-3-yl)-pyrrolo[2,1-f][1,2,4]triazin-2-ylamino]-phenyl}-propionamide;

1-Ethyl-3-{3-[7-(6-methoxy-pyridin-3-yl)-pyrrolo[2,1-f][1,2,4]triazin-2-ylamino]-phenyl}-urea;

N,N-Dimethyl-3-{2-[4-(1-methyl-piperidin-4-yl)phenylamino]-pyrrolo[2,1-f][1,2,4]triazin-7-yl}-benzenesulfonamide;

[4-(1-Methyl-piperidin-4-yl)-phenyl]-{7-[3-(pyrrolidine-1-sulfonyl)-phenyl]-pyrrolo[2,1-f][1,2,4]triazin-2-yl}-amine;

N-Benzyl-3-{2-[4-(1-methyl-piperidin-4-yl)-phenylamino]-pyrrolo[2,1-f][1,2,4]triazin-7-yl}-benzenesulfonamide;

[4-(1-Methyl-piperidin-4-yl)-phenyl]-{7-[3-(piperidine-1-sulfonyl)-phenyl]-pyrrolo[2,1-f][1,2,4]triazin-2-yl}-amine;

N-Cyclopropyl-3-{2-[4-(1-methyl-piperidin-4-yl)-phenylamino]-pyrrolo[2,1-f][1,2,4]triazin-7-yl}-benzenesulfonamide;

N-Ethyl-3-{2-[4-(1-methyl-piperidin-4-yl)-phenylamino]-pyrrolo[2,1-f][1,2,4]triazin-7-yl}-benzenesulfonamide;

[3-Methoxy-4-(1-methyl-piperidin-4-yl)-phenyl]-[7-(2-methoxy-phenyl)-pyrrolo[2,1-f][1,2,4]triazin-2-yl]-amine;

[7-(6-Methoxy-pyridin-3-yl)-pyrrolo[2,1-f][1,2,4]triazin-2-yl]-(4-[1,2,3]thiadiazol-4-yl-phenyl)-amine;

[3-Methoxy-4-(1-methyl-piperidin-4-yl)-phenyl]-[7-(6-methoxy-pyridin-3-yl)-pyrrolo[2,1-f][1,2,4]triazin-2-yl]-amine;

2-(4-{2-Methoxy-4-[7-(6-methoxy-pyridin-3-yl)-pyrrolo[2,1-f][1,2,4]triazin-2-ylamino]-phenyl}-piperidin-1-yl)-acetamide;

2-(4-{2-Methoxy-4-[7-(2-methoxy-phenyl)-pyrrolo[2,1-f][1,2,4]triazin-2-ylamino]-phenyl}-piperidin-1-yl)-acetamide;

N-(2-{2-[3-Methoxy-4-(1-methyl-piperidin-4-yl)-phenylamino]-pyrrolo[2,1-f][1,2,4]triazin-7-yl}-phenyl)-N-methyl-methanesulfonamide;

2-[4-(4-{7-[2-(Methanesulfonyl-methyl-amino)-phenyl]-pyrrolo[2,1-f][1,2,4]triazin-2-ylamino}-2-methoxy-phenyl)-piperidin-1-yl]-acetamide;

[7-(2-Methoxy-phenyl)-pyrrolo[2,1-f][1,2,4]triazin-2-yl]-(2-methyl-1,2,3,4-tetrahydro-isoquinolin-6-yl)-amine;

2-{6-[7-(6-Methoxy-pyridin-3-yl)-pyrrolo[2,1-f][1,2,4]triazin-2-ylamino]-3,4-dihydro-1H-isoquinolin-2-yl}-acetamide;

2-{6-[7-(2-Methoxy-phenyl)-pyrrolo[2,1-f][1,2,4]triazin-2-ylamino]-3,4-dihydro-1H-isoquinolin-2-yl}-acetamide;

2-(6-{7-[2-(Methanesulfonyl-methyl-amino)-phenyl]-pyrrolo[2,1-f][1,2,4]triazin-2-ylamino}-3,4-dihydro-1H-isoquinolin-2-yl)-acetamide;

[7-(6-Methoxy-pyridin-3-yl)-pyrrolo[2,1-f][1,2,4]triazin-2-yl]-(2-methyl-1,2,3,4-tetrahydro-isoquinolin-6-yl)-amine;

2-{6-[7-(3-tert-Butylsulfamoyl-phenyl)-pyrrolo[2,1-f][1,2,4]triazin-2-ylamino]-3,4-dihydro-1H-isoquinolin-2-yl}-acetamide;

N-tert-Butyl-3-[2-(2-methyl-1,2,3,4-tetrahydro-isoquinolin-6-ylamino)-pyrrolo[2,1-f][1,2,4]triazin-7-yl]-benzenesulfonamide;

6-Fluoro-7-[7-(2-methoxy-phenyl)-pyrrolo[2,1-f][1,2,4]triazin-2-ylamino]-3,4-dihydro-1H-quinolin-2-one;

2-(4-{4-[7-(3-Methanesulfonyl-phenyl)-pyrrolo[2,1-f][1,2,4]triazin-2-ylamino]-2-methoxy-phenyl}-piperidin-1-yl)-acetamide;

2-(4-{4-[7-(3-tert-Butylsulfamoyl-phenyl)-pyrrolo[2,1-f][1,2,4]triazin-2-ylamino]-2-methoxy-phenyl}-piperidin-1-yl)-acetamide;

2-{5-[7-(2-Methoxy-phenyl)-pyrrolo[2,1-f][1,2,4]triazin-2-ylamino]-1,3-dihydro-isoindol-2-yl}-acetamide;

2-{5-[7-(6-Methoxy-pyridin-3-yl)-pyrrolo[2,1-f][1,2,4]triazin-2-ylamino]-1,3-dihydro-isoindol-2-yl}-acetamide;

2-{5-[7-(3-tert-Butylsulfamoyl-phenyl)-pyrrolo[2,1-f][1,2,4]triazin-2-ylamino]-1,3-dihydro-isoindol-2-yl}-acetamide;

2-[4-(4-{7-[3-(Pyrrolidine-1-sulfonyl)-phenyl]-pyrrolo[2,1-f][1,2,4]triazin-2-ylamino-}-phenyl)-piperidin-1-yl]-acetamide;

2-(4-{4-[7-(3-Ethylsulfamoyl-phenyl)-pyrrolo[2,1f][1,2,4]triazin-2-ylamino]-phenyl}-piperidin-1-yl)-acetamide;

2-(4-{4-[7-(3-Cyclopropylsulfamoyl-phenyl)-pyrrolo[2,1-f][1,2,4]triazin-2-ylamino]-phenyl}-piperidin-1-yl)-acetamide;

N-tert-Butyl-3-[2-(2-methyl-1,2,3,4-tetrahydro-isoquinolin-7-ylamino)-pyrrolo[2,1-f][1,2,4]triazin-7-yl]-benzenesulfonamide;

3-(4-{2-[4-(1-Methyl-piperidin-4-yl)-phenylamino]-pyrrolo[2,1-f][1,2,4]triazin-7-yl}-pyrazol-1-yl)-propionitrile;

2-[4-(4-{7-[1-(2-Cyano-ethyl)-1H-pyrazol-4-yl]-pyrrolo[2,1-f][1,2,4]triazin-2-ylamino}-phenyl)-piperidin-1-yl]-acetamide;

2-(4-{4-[7-(6-Methoxy-pyridin-3-yl)-pyrrolo[2,1-f][1,2,4]triazin-2-ylamino]-2-methyl-phenyl}-piperidin-1-yl)-acetamide;

2-(4-{4-[7-(2-Methoxy-phenyl)-pyrrolo[2,1-f][1,2,4]triazin-2-ylamino]-2-methyl-phenyl}-piperidin-1-yl)-acetamide;

N-tert-Butyl-3-[2-(2-methyl-2,3-dihydro-1H-isoindol-5-ylamino)-pyrrolo[2,1-f][1,2,4]triazin-7-yl]-benzenesulfonamide;

[7-(6-Methoxy-pyridin-3-yl)-pyrrolo[2,1-f][1,2,4]triazin-2-yl]-(2-methyl-2,3-dihydro-1H-isoindol-5-yl)-amine;

2-(4-{4-[7-(3-tert-Butylsulfamoyl-phenyl)-pyrrolo[2,1-f][1,2,4]triazin-2-ylamino]-2-methyl-phenyl}-piperidin-1-yl)-acetamide;

2-(4-{2-Acetylamino-4-[7-(6-methoxy-pyridin-3-yl)-pyrrolo[2,1-f][1,2,4]triazin-2-ylamino]-phenyl}-piperidin-1-yl)-acetamide;

N-tert-Butyl-3-{2-[3-methyl-4-(1-methyl-piperidin-4-yl)-phenylamino]-pyrrolo[2,1-f][1,2,4]triazin-7-yl}-benzenesulfonamide;

[7-(6-Methoxy-pyridin-3-yl)-pyrrolo[2,1-f][1,2,4]triazin-2-yl]-[3-methyl-4-(1-methyl-piperidin-4-yl)-phenyl]-amine;

[7-(2-Methoxy-phenyl)-pyrrolo[2,1-f][1,2,4]triazin-2-yl]-[3-methyl-4-(1-methyl-piperidin-4-yl)-phenyl]-amine;

N-tert-Butyl-3-{2-[4-(8-methyl-8-aza-bicyclo[3.2.1]oct-3-yl)-phenylamino]-pyrrolo[2,1-f][1,2,4]triazin-7-yl}-benzenesulfonamide;

[7-(6-Methoxy-pyridin-3-yl)-pyrrolo[2,1-f][1,2,4]triazin-2-yl]-[4-(8-methyl-8-aza-bicyclo[3.2.1]oct-3-yl)-phenyl]-amine;

[7-(2-Methoxy-phenyl)-pyrrolo[2,1-f][1,2,4]triazin-2-yl]-[4-(8-methyl-8-azabicyclo[3.2.1]oct-3-yl)-phenyl]-amine;

[7-(3-Methanesulfonyl-phenyl)-pyrrolo[2,1-f][1,2,4]triazin-2-yl]-[3-methyl-4-(1-methyl-piperidin-4-yl)-phenyl]-amine;

[7-(4-Methanesulfonyl-phenyl)-pyrrolo[2,1-f][1,2,4]triazin-2-yl]-[3-methyl-4-(1-methyl-piperidin-4-yl)-phenyl]-amine;

2-(4-{4-[7-(3-Methanesulfonyl-phenyl)-pyrrolo[2,1-f][1,2,4]triazin-2-ylamino]-2-methyl-phenyl}-piperidin-1-yl)-acetamide;

2-(4-{4-[7-(4-Methanesulfonyl-phenyl)-pyrrolo[2,1-f][1,2,4]triazin-2-ylamino]-2-methyl-phenyl}-piperidin-1-yl)-acetamide;

[7-(1-Methanesulfonyl-1H-pyrazol-4-yl)-pyrrolo[2,1-f][1,2,4]triazin-2-yl]-[3-(4-methyl-piperazin-1-yl)-phenyl]-amine;

2-(4-{4-[7-(3-Methanesulfonyl-phenyl)-pyrrolo[2,1-f][1,2,4]triazin-2-ylamino]-2-trifluoromethyl-phenyl}-3,6-dihydro-2H pyridin-1-yl)acetamide;

2-(4-{4-[7-(2-Methoxy-phenyl)-pyrrolo[2,1-f][1,2,4]triazin-2-ylamino]-2-trifluoromethyl-phenyl}-3,6-dihydro-2H-pyridin-1-yl)-acetamide;

2-(4-{4-[7-(6-Methoxy-pyridin-3-yl)-pyrrolo[2,1-f][1,2,4]triazin-2-ylamino]-2-trifluoromethyl-phenyl}-3,6-dihydro-2H-pyridin-1-yl)-acetamide;

[4-(1-Methyl-piperidin-4-yl)-phenyl]-[7-(1-methyl-1H-pyrazol-3-yl)-pyrrolo[2,1-f][1,2,4]triazin-2-yl]-amine;

2-(4-{4-[7-(1-Methyl-1H-pyrazol-3-yl)-pyrrolo[2,1-f][1,2,4]triazinylaminophenyl}-piperidin-1-yl)-acetamide;

2-(4-{4-[7-(3-Methanesulfonylamino-phenyl)-pyrrolo[2,1-f][1,2,4]triazin-2-ylamino]-phenyl}-piperidin-1-yl)-acetamide;

N-[3-(2-{4-[1((S)-2-Hydroxy-propyl)-piperidin-4-yl]-phenylamino}-pyrrolo[2,1-f][1,2,4]triazin-7-yl)-phenyl]-methanesulfonamide;

N-[3-(2-{4-[1-(2-Hydroxy-ethyl)-piperidin-4-yl]-phenylamino}-pyrrolo[2,1-f][1,2,4]triazin-7-yl)-phenyl]-methanesulfonamide;

2-[4-(4-{7-[3-(Methanesulfonyl-methyl-amino)-phenyl]-pyrrolo[2,1-f][1,2,4]triazin-2-ylamino}-phenyl)-piperidin-1-yl]-acetamide;

N-[3-(2-{4-[1-((S)-2-Hydroxy-propyl)-piperidin-4-yl]-phenylamino}-pyrrolo[2,1-f][1,2,4]triazin-7-yl)-phenyl]-N-methyl-methanesulfonamide;

N-[3-(2-{4-[1-(2-Hydroxy-ethyl)-piperidin-4-yl]-phenylamino}-pyrrolo[2,1-f][1,2,4]triazin-7-yl)-phenyl]-N-methyl-methanesulfonamide;

N-{2-Chloro-5-[7-(1-methyl-1H-pyrazol-4-yl)pyrrolo[2,1f][1,2,4]triazin-2-ylamino]-phenyl}-acetamide;

N-{3-[7-(1-Methyl-1H-pyrazol-4-yl)-pyrrolo[2,1-f][1,2,4]triazin-2-ylamino]-phenyl}-isobutyramide;

[7-(1-Methyl-1H-pyrazol-4-yl)pyrrolo[2,1f][1,2,4]triazin-2-yl]-(3-pyrazol-1-yl-phenyl)-amine;

N-Methyl-3-[7-(1-methyl-1H-pyrazol-4-yl)-pyrrolo[2,1-f][1,2,4]triazin-2-ylamino]-benzamide;

1-{6-[7-(1-Methyl-1H-pyrazol-4-yl)-pyrrolo[2,1-f][1,2,4]triazin-2-ylamino]-2,3-dihydro-indol-1-yl}-ethanone;

1-{3-[7-(1-Methyl-1H-pyrazol-4-yl)-\pyrrolo[2,1-f][1,2,4]triazin-2-ylamino]-phenyl}-pyrrolidin-2-one;

1-{3,3-Dimethyl-6-[7-(1-methyl-1H-pyrazol-4-yl)-pyrrolo[2,1-f][1,2,4]triazin-2-ylamino]-2,3-dihydro-indol-1-yl}-ethanone;

[3-(4-Methyl-piperazin-1-yl)-phenyl]-[7-(1-methyl-1H-pyrazol-4-yl)-pyrrolo[2,1-f][1,2,4]triazin-2-yl]-amine;

[3-(4-Methyl-piperazin-1-yl)-phenyl]-[7-(1H-pyrazol-4-yl)-pyrrolo[2,1-f][1,2,4]triazin-2-yl]-amine;

{7-[1-(3-Methyl-butyl)-1H-pyrazol-4-yl]-pyrrolo[2,1-f][1,2,4]triazin-2-yl}-[3-(4-methyl-piperazin-1-yl)-phenyl]-amine;

{7-[1-(2-Methoxy-ethyl)-1H-pyrazol-4-yl]-pyrrolo[2,1-f][1,2,4]triazin-2-yl}-[3-(4-methyl-piperazin-1-yl)-phenyl]-amine;

(4-Chloro-3-morpholin-4-ylmethyl-phenyl)-[7-(6-methoxy-pyridin-3-yl)-pyrrolo[2,1-f][1,2,4]triazin-2-yl]-amine;

3-[7-(6-Methoxy-pyridin-3-yl)pyrrolo[2,1f][1,2,4]triazin-2-ylamino]-benzonitrile;

2-{3-[7-(6-Methoxy-pyridin-3-yl)-pyrrolo[2,1-f][1,2,4]triazin-2-ylamino]-phenylamino}-acetamide;

3-(4-{2-[3-(4-Methyl-piperazin-1-yl)-phenylamino]-pyrrolo[2,1-f][1,2,4]triazin-7-yl}-pyrazol-1-yl)-propan-1-ol;

3-(4-{2-[3-(4-Methyl-piperazin-1-yl)-phenylamino]-pyrrolo[2,1-f][1,2,4]triazin-7-yl}-pyrazol-1-yl)-propionitrile;

2-(4-{2-[3-(4-Methyl-piperazin-1-yl)-phenylamino]-pyrrolo[2,1-f][1,2,4]triazin-7-yl}-pyrazol-1-yl)-acetamide;

7-[7-(6-Methoxy-pyridin-3-yl)-pyrrolo[2,1-f][1,2,4]triazin-2-ylamino]-3,4-dihydro-1H-quinolin-2-one;

[7-(6-Methoxy-pyridin-3-yl)-pyrrolo[2,1-f][1,2,4]triazin-2-yl]-(1-methyl-1,2,3,4-tetrahydro-quinolin-7-yl)-amine;

7-[7-(2-Methoxy-phenyl)-pyrrolo[2,1-f][1,2,4]triazin-2-ylamino]-3,4-dihydro-1H-quinolin-2-one;

[7-(2-Methoxy-phenyl)-pyrrolo[2,1-f][1,2,4]triazin-2-yl]-(1-methyl-1,2,3,4-tetrahydro-quinolin-7-yl)-amine;

6-Fluoro-7-[7-(6-methoxy-pyridin-3-yl)-pyrrolo[2,1-f][1,2,4]triazin-2-ylamino]-3,4-dihydro-1H-quinolin-2-one;

[7-(2-Methoxy-phenyl)-pyrrolo[2,1-f][1,2,4]triazin-2-yl]-(2-methyl-1,2,3,4-tetrahydro-isoquinolin-7-yl)-amine;

[7-(6-Methoxy-pyridin-3-yl)-pyrrolo[2,1-f][1,2,4]triazin-2-yl]-(2-methyl-1,2,3,4-tetrahydro-isoquinolin-7-yl)-amine;

2-{7-[7-(6-Methoxy-pyridin-3-yl)-pyrrolo[2,1-f][1,2,4]
triazin-2-ylamino]-3,4-dihydro-1H-isoquinolin-2-yl}-
acetamide;
2-{7-[7-(2-Methoxy-phenyl)-pyrrolo[2,1-f][1,2,4]triazin-
2-ylamino]-3,4-dihydro-1H-isoquinolin-2-yl}-aceta-
mide;
N-(3-{7-[3-(2-Methoxy-ethylamino)-phenyl]-pyrrolo[2,
1-f][1,2,4]triazin-2-ylamino}-phenyl)-acetamide;
(R)-1-{7-Methoxy-8-[7-(2-methoxy-phenyl)-pyrrolo[2,1-
f][1,2,4]triazin-2-ylamino]-1,2,4,5-tetrahydro-benzo
[d]azepin-3-yl}-propan-2-ol;
(3-Methoxy-6-morpholin-4-yl-6,7,8,9-tetrahydro-5H-
benzocyclohepten-2-yl)-[7-(2-methoxy-phenyl)-pyr-
rolo[2,1-f][1,2,4]triazin-2-yl]-amine;
N-{2-[2-(3-Methoxy-6-morpholin-4-yl-6,7,8,9-tetrahy-
dro-5H-benzocyclohepten-2-ylamino)-pyrrolo[2,1-f]
[1,2,4]triazin-7-yl]-phenyl}-N-methyl-methane-
sulfonamide;
[7-(2-Methoxy-phenyl)-pyrrolo[2,1-f][1,2,4]triazin-2-yl]-
[2-methoxy-4-(4-pyridin-2-yl-piperazin-1-yl)-phenyl]-
amine;
N-(2-{2-[4-(4-Ethyl-morpholin-2-yl)-phenylamino]-pyr-
rolo[2,1-f][1,2,4]triazin-7-yl}-phenyl)-N-methyl-
methanesulfonamide;
N-(2-{2-[(7-methoxy-1'-methyl-3,4-dihydrospiro
[chromene-2,4'-piperidin]-6-yl)amino]pyrrolo[2,1-f]
[1,2,4]triazin-7-yl}phenyl)-N-methylmethanesulfona-
mide;
7-methoxy-N-[7-(2-methoxyphenyl)pyrrolo[2,1-f][1,2,4]
triazin-2-yl]-1'-methyl-3,4-dihydrospiro[chromene-2,
4'-piperidin]-6-amine;
[2-Methoxy-4-(1-methyl-piperidin-4-yloxy)-phenyl]-[7-
(2-methoxy-phenyl)-pyrrolo[2,1-f][1,2,4]triazin-2-yl]-
amine;
N-(2-{2-[2-Methoxy-4-(1-methyl-piperidin-4-yloxy)-
phenylamino]-pyrrolo[2,1-f][1,2,4]triazin-7-yl}-phe-
nyl)-N-methyl-methanesulfonamide;
N-tert-Butyl-3-{2-[3-(2-morpholin-4-yl-ethoxy)-pheny-
lamino]-pyrrolo[2,1-f][1,2,4]triazin-7-yl}-benzene-
sulfonamide;
N-(2-{2-[3-(2-Morpholin-4-yl-ethoxy)-phenylamino]-
pyrrolo[2,1-f][1,2,4]triazin-7-yl}-phenyl)-methane-
sulfonamide;
[7-(2-Methoxy-phenyl)-pyrrolo[2,1-f][1,2,4]triazin-2-yl]-
[3-(2-morpholin-4-yl-ethoxy)-phenyl]-amine;
[7-(1-Methyl-1H-pyrazol-4-yl)-pyrrolo[2,1-f][1,2,4]tri-
azin-2-yl]-[3-(2-morpholin-4-yl-ethoxy)-phenyl]-
amine;
N-tert-Butyl-3-{2-[3-(1-methyl-pyrrolidin-2-ylmethoxy)-
phenylamino]-pyrrolo[2,1-f][1,2,4]triazin-7-yl}-ben-
zenesulfonamide;
[7-(2-Methoxy-phenyl)-pyrrolo[2,1-f][1,2,4]triazin-2-yl]-
[3-(1-methyl-pyrrolidin-2-ylmethoxy)-phenyl]-amine;
[7-(1-Methyl-1H-pyrazol-4-yl)-pyrrolo[2,1-f][1,2,4]tri-
azin-2-yl]-[3-(1-methyl-pyrrolidin-2-ylmethoxy)-phe-
nyl]-amine;
3-{4-[7-(2-Methoxy-phenyl)-pyrrolo[2,1-f][1,2,4]triazin-
2-ylamino]-phenyl}-pyrrolidine-1-carboxylic acid tert-
butyl ester;
N-tert-Butyl-3-{2-[4-chloro-3-(1-methyl-pyrrolidin-2-yl-
methoxy)-phenylamino]-pyrrolo[2,1-f][1,2,4]triazin-7-
yl}-benzenesulfonamide;
N-(2-{2-[4-Chloro-3-(1-methyl-pyrrolidin-2-yl-
methoxy)-phenylamino]-pyrrolo[2,1-f][1,2,4]triazin-7-
yl}-phenyl)-N-methyl-methanesulfonamide;
[4-Chloro-3-(1-methyl-pyrrolidin-2-ylmethoxy)-phenyl]-
[7-(2-methoxy-phenyl)-pyrrolo[2,1-f][1,2,4]triazin-2-
yl]-amine;
[7-(2-Methoxy-phenyl)-pyrrolo[2,1-f][1,2,4]triazin-2-yl]-
(4-pyrrolidin-3-yl-phenyl)-amine;
[4-Chloro-3-(1-methyl-pyrrolidin-2-ylmethoxy)-phenyl]-
[7-(3-methanesulfonyl-phenyl)-pyrrolo[2,1-f][1,2,4]
triazin-2-yl]-amine;
N-tert-Butyl-3-{2-[4-(3-hydroxy-piperidin-4-yl)-pheny-
lamino]-pyrrolo[2,1-f][1,2,4]triazin-7-yl}-benzene-
sulfonamide;
[4-Chloro-3-((S)-1-pyrrolidin-2-ylmethoxy)-phenyl]-{7-
[3-(propane-2-sulfonyl)-phenyl]-pyrrolo[2,1-f][1,2,4]
triazin-2-yl}-amine;
[4-Chloro-3-((R)-1-pyrrolidin-2-ylmethoxy)-phenyl]-{7-
[3-(propane-2-sulfonyl)-phenyl]-pyrrolo[2,1-f][1,2,4]
triazin-2-yl}-amine;
4-{4-[7-(3-tert-Butylsulfamoyl-phenyl)-pyrrolo[2,1-f][1,
2,4]triazin-2-ylamino]-phenyl}-3-hydroxy-piperidine-
1-carboxylic acid tert-butyl ester;
4-{4-[7-(3-methanesulfonyl-phenyl)-pyrrolo[2,1-f][1,2,
4]triazin-2-ylamino]-phenyl}-piperidine-3-ol;
3-Hydroxy-4-{4-[7-(3-methanesulfonyl-phenyl)-pyrrolo
[2,1-f]][1,2,4]triazin-2-ylamino]-phenyl}-piperidine-1-
carboxylic acid tert-butyl ester;
[4-Chloro-3-((S)-1-pyrrolidin-2-ylmethoxy)-phenyl]-[7-
(3-methanesulfonyl-phenyl)-pyrrolo[2,1-f][1,2,4]tri-
azin-2-yl]-amine;
[4-Chloro-3-((R)-1-pyrrolidin-2-ylmethoxy)-phenyl]-[7-
(3-methanesulfonyl-phenyl)-pyrrolo[2,1-f][1,2,4]tri-
azin-2-yl]-amine;
(S)-2-{2-Chloro-5-[7-(3-methanesulfonyl-phenyl)-pyr-
rolo[2,1-f][1,2,4]triazin-2-ylamino]-phenoxymethyl}-
pyrrolidine-1-carboxylic acid tert-butyl ester;
(R)-2-{2-Chloro-5-[7-(3-methanesulfonyl-phenyl)-pyr-
rolo[2,1-f][1,2,4]triazin-2-ylamino]-phenoxymethyl}-
pyrrolidine-1-carboxylic acid tert-butyl ester;
2-(4-{4-[7-(5-Chloro-2-methoxy-phenyl)-pyrrolo[2,1-f]
[1,2,4]triazin-2-ylamino]-phenyl}-piperidin-1-yl)-ac-
etamide;
(1',2',3',4',5',6'-Hexahydro-[2,4']bipyridinyl-5-yl)-[7-(3-
methanesulfonyl-phenyl)-pyrrolo[2,1-f][1,2,4]triazin-
2-yl]-amine;
(1',2',3',4',5',6'-Hexahydro-[2,4']bipyridinyl-5-yl)-[7-(2-
methoxy-phenyl)-pyrrolo[2,1-f][1,2,4]triazin-2-yl]-
amine;
{7-[4-(1,1-Dioxo-1$1(6)-thiomorpholin-4-ylmethyl)-
phenyl]-pyrrolo[2,1-f][1,2,4]triazin-2-yl}-[4-(4-me-
thyl-piperazin-1-yl)-phenyl]-amine;
{7-[4-(1,1-Dioxo-1$1(6)-thiomorpholin-4-ylmethyl)-
phenyl]-pyrrolo[2,1-f][1,2,4]triazin-2-yl}-(4-morpho-
lin-4-yl-phenyl)-amine;
(4-Morpholin-4-yl-phenyl)-(7-quinolin-3-yl-pyrrolo[2,1-
f][1,2,4]triazin-2-yl)-amine;
[7-(2-Chloro-pyridin-3-yl)-pyrrolo[2,1-f][1,2,4]triazin-2-
yl]-(4-morpholin-4-yl-phenyl)-amine;
[7-(2-Dimethylaminomethyl-phenyl)-pyrrolo[2,1-f][1,2,
4]triazin-2-yl]-(4-morpholin-4-yl-phenyl)-amine;
[7-(2-Chloro-pyridin-3-yl)-pyrrolo[2,1-f][1,2,4]triazin-2-
yl]-[4-(4-methyl-piperazin-1-yl)-phenyl]-amine;
[4-(4-Methyl-piperazin-1-yl)-phenyl]-(7-quinolin-3-yl-
pyrrolo[2,14-f][1,2,4]triazin-2-yl)-amine;
[7-(4-Methyl-pyridin-3-yl)-pyrrolo[2,1-f][1,2,4]triazin-2-
yl]-(4-morpholin-4-yl-phenyl)-amine;
[4-(4-Methyl-piperazin-1-yl)-phenyl]-[7-(4-methyl-pyri-
din-3-yl)-pyrrolo[2,1-f][1,2,4]triazin-2-yl]-amine;

[7-(2-Fluoro-pyridin-3-yl)-pyrrolo[2,1-f][1,2,4]triazin-2-yl]-(4-morpholin-4-yl-phenyl)-amine;
[7-(2-Fluoro-pyridin-3-yl)-pyrrolo[2,1-f][1,2,4]triazin-2-yl]-[4-(4-methyl-piperazin-1-yl)-phenyl]-amine;
[7-(1,2-Dimethyl-1H-imidazol-4-yl)-pyrrolo[2,1-f][1,2,4]triazin-2-yl]-[4-(4-methyl-piperazin-1-yl)-phenyl]-amine;
[7-(1-Methyl-1H-imidazol-4-yl)-pyrrolo[2,1-f][1,2,4]triazin-2-yl]-[4-(4-methyl-piperazin-1-yl)-phenyl]-amine;
[7-(1,2-Dimethyl-1H-imidazol-4-yl)-pyrrolo[2,1-f][1,2,4]triazin-2-yl]-(4-morpholin-4-yl-phenyl)-amine;
[7-(1-Methyl-1H-imidazol-4-yl)-pyrrolo[2,1-f][1,2,4]triazin-2-yl]-(4-morpholin-4-yl-phenyl)-amine;
[7-(6-Fluoro-5-methyl-pyridin-3-yl)-pyrrolo[2,1-f][1,2,4]triazin-2-yl]-[4-(4-methyl-piperazin-1-yl)-phenyl]-amine;
[7-(6-Fluoro-5-methyl-pyridin-3-yl)-pyrrolo[2,1-f][1,2,4]triazin-2-yl]-(4-morpholin-4-yl-phenyl)-amine;
N-Methyl-N-(3-{2-[4-(4-methyl-piperazin-1-yl)-phenylamino]-pyrrolo[2,1-f][1,2,4]triazin-7-yl}-benzyl)-methanesulfonamide;
[4-(1-Dioxo-1$1(6)-thiomorpholin-4-ylmethyl)-phenyl]-[7-(3-methanesulfonyl-phenyl)-pyrrolo[2,1-f][1,2,4]triazin-2-yl]-amine;
[4-(1,1-Dioxo-1 $1(6)-thiomorpholin-4-ylmethyl)-phenyl]-(7-pyridin-3-yl-pyrrolo[2,1-f][1,2,4]triazin-2-yl)-amine;
[4-(1,1-Dioxo-1$1(6)-thiomorpholin-4-ylmethyl)-phenyl]-[7-(6-methoxy-pyridin-3-yl)-pyrrolo[2,1-f][1,2,4]triazin-2-yl]-amine;
N-(3-{2-[(1,1-Dioxo-1$1(6)-thiomorpholin-4-ylmethyl)-phenylamino]-pyrrolo[2,1-f][1,2,4]triazin-7-yl}-phenyl)-methanesulfonamide;
N-[3-(7-{3-[(Methanesulfonyl-methyl-amino)-methyl]-phenyl}-pyrrolo[2,1-f][1,2,4]triazin-2-ylamino)-phenyl]-acetamide;
N-{3-[2-(3,3-Dimethyl-2-oxo-2,3-dihydro-1H-indol-6-ylamino)-pyrrolo[2,1-f][1,2,4]triazin-7-yl]-benzyl}-N-methyl-methanesulfonamide;
2-(4-{4-[7-(3-tert-Butylsulfamoyl-phenyl)-pyrrolo[2,1-f][1,2,4]triazin-2-ylamino}-phenyl]-piperidin-1-yl)-acetamide;
{7-[6-(1,1-Dioxo-1$1(6)-thiomorpholin-4-ylmethyl)-pyridin-3-yl]-pyrrolo[2,1-f][1,2,4]triazin-2-yl}-[4-(4-methyl-piperazin-1-yl)-phenyl]-amine;
N-tert-Butyl-3-{2-[4-(1,1-dioxo-1$1(6)-thiomorpholin-4-ylmethyl)-phenylamino]-pyrrolo[2,1-f][1,2,4]triazin-7-yl}-benzenesulfonamide;
4-{4-[7-(3-tert-Butylsulfamoyl-phenyl)-pyrrolo[2,1-f][1,2,4]triazin-2-ylamino]-phenyl}-piperidine-1-carboxylic acid tert-butyl ester;
N-tert-Butyl-3-[2-(4-piperidin-4-yl-phenylamino)-pyrrolo[2,1-f][1,2,4]triazin-7-yl]-benzenesulfonamide;
N-tert-Butyl-3-[2-(1-methanesulfonyl-1,2,3,4-tetrahydro-quinolin-7-ylamino)-pyrrolo[2,1-f][1,2,4]triazin-7-yl]-benzenesulfonamide;
(1-Methanesulfonyl-1,2,3,4-tetrahydro-quinolin-7-yl)-[7-(6-methoxy-pyridin-3-yl)-pyrrolo[2,1-f][1,2,4]triazin-2-yl]-amine;
N-{2-[2-(1-Methanesulfonyl-1,2,3,4-tetrahydro-quinolin-7-ylamino)-pyrrolo[2,1-f][1,2,4]triazin-7-yl]-phenyl}-N-methyl-methanesulfonamide;
2-[4-(4-{7-[3-(tert-Butyl-dimethyl-silanyloxymethyl)-phenyl]-pyrrolo[2,1-f][1,2,4]triazin-2-ylamino}-phenyl)-piperidin-1-yl]-acetamide;
(3H-Benzoimidazol-5-yl)-{7-[3-(tert-butyl-dimethyl-silanyloxymethyl)-phenyl]-pyrrolo[2,1-f][1,2,4]triazin-2-yl}-amine;
2-(4-{4-[7-(3-Hydroxymethyl-phenyl)-pyrrolo[2,1-f][1,2,4]triazin-2-ylamino]-phenyl}-piperidin-1-yl)-acetamide;
N-tert-Butyl-3-[2-(2-hydroxymethyl-3H-benzoimidazol-5-ylamino)-pyrrolo[2,1-f][1,2,4]triazin-7-yl]-benzenesulfonamide;
{6-[7-(2-Methoxy-phenyl)-pyrrolo[2,1-f][1,2,4]triazin-2-ylamino]-1H-benzoimidazol-2-yl}-methanol;
(6-{7-[3-(Morpholine-4-sulfonyl)-phenyl]-pyrrolo[2,1-f][1,2,4]triazin-2-ylamino}-1H-benzoimidazol-2-yl)-methanol;
{6-[7-(6-Methoxy-pyridin-3-yl)-pyrrolo[2,1-f][1,2,4]triazin-2-ylamino]-1H-benzoimidazol-2-yl}-methanol;
(6-{7-[3-(Pyrrolidine-1-sulfonyl)-phenyl]-pyrrolo[2,1-f][1,2,4]triazin-2-ylamino}-1H-benzoimidazol-2-yl)-methanol;
N-{2-[2-(2-Hydroxymethyl-3H-benzoimidazol-5-ylamino)-pyrrolo[2,1-f][1,2,4]triazin-7-yl]-phenyl}-N-methyl-methanesulfonamide;
3-{4-[7-(6-Methoxy-pyridin-3-yl)-pyrrolo[2,1-f][1,2,4]triazin-2-ylamino]-phenyl}-1,4-dimethyl-piperazin-2-one;
N-(2-{2-[4-(1,4-Dimethyl-3-oxo-piperazin-2-yl)-phenylamino}-pyrrolo[2,1-f][1,2,4]triazin-7-yl]-phenyl)-N-methyl-methanesulfonamide;
N-tert-Butyl-3-{2-[4-(1,4-dimethyl-3-oxo-piperazin-2-yl)-phenylamino]-pyrrolo[2,1-f][1,2,4]triazin-7-yl}-benzenesulfonamide;
1,4-Dimethyl-3-(4-{7-[3-(morpholine-4-sulfonyl)-phenyl]-pyrrolo[2,1-f][1,2,4]triazin-2-ylamino}-phenyl)-piperazin-2-one;
3-{4-[7-(2-Methoxy-phenyl)-pyrrolo[2,1-f][1,2,4]triazin-2-ylamino]-phenyl}-1,4-dimethyl-piperazin-2-one;
N-tert-Butyl-3-{2-[3-(1,4-dimethyl-3-oxo-piperazin-2-yl)-phenylamino]-pyrrolo[2,1-f][1,2,4]triazin-7-yl}-benzenesulfonamide;
1,4-Dimethyl-3-(3-{7-[3-(morpholine-4-sulfonyl)-phenyl]-pyrrolo[2,1-f][1,2,4]triazin-2-ylamino}-phenyl)-piperazin-2-one;
1,4-Dimethyl-3-(3-{7-[3-(pyrrolidine-1-sulfonyl)-phenyl]-pyrrolo[2,1-f][1,2,4]triazin-2-ylamino}-phenyl)-piperazin-2-one;
3-{3-[7-(3-Methanesulfonyl-phenyl)-pyrrolo[2,1-f][1,2,4]triazin-2-ylamino]-phenyl}-1,4-dimethyl-piperazin-2-one;
3-{3-[7-(6-Methoxy-pyridin-3-yl)-pyrrolo[2,1-f][1,2,4]triazin-2-ylamino]-phenyl}-1,4-dimethyl-piperazin-2-one;
3-{3-[7-(2-Methoxy-phenyl)-pyrrolo[2,1-f][1,2,4]triazin-2-ylamino]-phenyl}-1,4-dimethyl-piperazin-2-one;
N-(2-{2-[3-(1,4-Dimethyl-3-oxo-piperazin-2-yl)-phenylamino}-pyrrolo[2,1-f][1,2,4]triazin-7-yl]-phenyl)-N-methyl-methanesulfonamide;
3-{3-[7-(4-Methanesulfonyl-phenyl)-pyrrolo[2,1-f][1,2,4]triazin-2-ylamino]-phenyl}-1,4-dimethyl-piperazin-2-one;
N-tert-Butyl-3-[2-(4-pyridin-3-yl-phenylamino)-pyrrolo[2,1-f][1,2,4]triazin-7-yl]-benzenesulfonamide;
(4-Pyridin-3-yl-phenyl)-{7-[3-(pyrrolidine-1-sulfonyl)-phenyl]-pyrrolo[2,1-f][1,2,4]triazin-2-yl}-amine;
[7-(3-Methanesulfonyl-phenyl)-pyrrolo[2,1-f][1,2,4]triazin-2-yl]-(4-pyridin-3-yl-phenyl)-amine;
[7-(6-Methoxy-pyridin-3-yl)-pyrrolo[2,1-f][1,2,4]triazin-2-yl]-(4-pyridin-3-yl-phenyl)-amine;

[7-(4-Methanesulfonyl-phenyl)-pyrrolo[2,1-f][1,2,4]triazin-2-yl]-(4-pyridin-3-yl-phenyl)-amine;
{7-[3-(Morpholine-4-sulfonyl)-phenyl]-pyrrolo[2,1-f][1,2,4]triazin-2-yl}-(4-pyridin-3-yl-phenyl)-amine;
[7-(2-Methoxy-phenyl)-pyrrolo[2,1-f][1,2,4]triazin-2-yl]-(4-pyridin-3-yl-phenyl)-amine
N-Methyl-N-{2-[2-(4-pyridin-3-yl-phenylamino)-pyrrolo[2,1-f][1,2,4]triazin-7-yl]-phenyl}-methanesulfonamide;
[7-(2-Methoxy-phenyl)-pyrrolo[2,1-f][1,2,4]triazin-2-yl]-[4-(2-morpholin-4-yl-ethoxy)-phenyl]-amine;
(1-{4-[7-(6-Methoxy-pyridin-3-yl)-pyrrolo[2,1-f][1,2,4]triazin-2-ylamino]-phenyl}-piperidin-4-yl)-methanol
[7-(6-Methoxy-pyridin-3-yl)-pyrrolo[2,1-f][1,2,4]triazin-2-yl]-[4-(2-morpholin-4-yl-ethoxy)-phenyl]-amine;
2-(4-{4-[7-(6-Methoxy-pyridin-3-yl)-pyrrolo[2,1-f][1,2,4]triazin-2-ylamino]-phenyl}-piperazin-1-yl)-ethanol;
[7-(6-Methoxy-pyridin-3-yl)-pyrrolo[2,1-f][1,2,4]triazin-2-yl]-(4-morpholin-4-yl-phenyl)-amine;
7-(6-Methoxy-pyridin-3-yl)-pyrrolo[2,1-f][1,2,4]triazin-2-yl]-(6-morpholin-4-yl-pyridin-3-yl)-amine;
7-(2-Methoxy-phenyl)-5,6-dimethyl-pyrrolo[2,1-f][1,2,4]triazin-2-yl]-[4-(4-methyl-piperazin-1-yl)-phenyl]-amine;
[7-(2-Methoxy-phenyl)-pyrrolo[2,1-f][1,2,4]triazin-2-yl][6-(4-methyl-piperazin-1-yl)-pyridin-3-yl]-amine;
[7-(6-Methoxy-pyridin-3-yl)-pyrrolo[2,1-f][1,2,4]triazin-2-yl]-[6-(4-methyl-piperazin-1-yl)-pyridin-3-yl]-amine;
[7-(4-Methanesulfonyl-phenyl)-pyrrolo[2,1-f][1,2,4]triazin-2-yl]-[6-(4-methyl-piperazin-1-yl)-pyridin-3-yl]-amine;
2-{3-[7-(2-Methoxy-phenyl)-pyrrolo[2,1-f][1,2,4]triazin-2-ylamino]-pyrazol-1-yl}-1-morpholin-4-yl-ethanone;
2-{3-[7-(6-Methoxy-pyridin-3-yl)-pyrrolo[2,1-f][1,2,4]triazin-2-ylamino]-pyrazol-1-yl}-1-morpholin-4-yl-ethanone;
2-{4-[7-(2-Methoxy-phenyl)-pyrrolo[2,1-f][1,2,4]triazin-2-ylamino]-imidazol-1-yl}-1-morpholin-4-yl-ethanone;
2-{3 47-(2-Methoxy-phenyl)-pyrrolo[2,1-f][1,2,4]triazin-2-ylamino-1-pyrazol-1-yl}-1-(4-methyl-piperazin-1-yl)-ethanone;
2-{3-[7-(6-Methoxy-pyridin-3-yl)-pyrrolo[2,1-f][1,2,4]triazin-2-ylamino]-pyrazol-1-yl}-1-(4-methyl-piperazin-1-yl)-ethanone;
(4-Morpholin-4-yl-phenyl)-[7-(pyridin-4-ylsulfanyl)-pyrrolo[2,1-f][1,2,4]triazin-2-yl]-amine;
[4-(4-Methyl-piperazin-1-yl)-phenyl]-[7-(pyridin-4-ylsulfanyl)-pyrrolo[2,1-f][1,2,4]triazin-2-yl]-amine;
[7-(6-Amino-pyridin-3-yl)-pyrrolo[2,1-f][1,2,4]triazin-2-yl]-[4-(4-methyl-piperazin-1-yl)-phenyl]-amine;
[7-(4-Methanesulfonyl-phenyl)-pyrrolo[2,1-f][1,2,4]triazin-2-yl]-[4-(1-methyl-piperidin-4-yl)-phenyl]-amine;
[7-(3-Methanesulfonyl-phenyl)-pyrrolo[2,1-f][1,2,4]triazin-2-yl]-[4-(1-methyl-piperidin-4-yl)-phenyl]-amine;
[7-(5-Chloro-2-methoxy-phenyl)-pyrrolo[2,1-f][1,2,4]triazin-2-yl]-[4-(1-methyl-piperidin-4-yl)-phenyl]-amine;
N-(3-{2-[6-(4-Methyl-piperazin-1-yl)-pyridin-3-ylamino]-pyrrolo[2,1-f][1,2,4]triazin-7-yl}-phenyl)-methanesulfonamide;
[7-(3-Methanesulfonyl-phenyl)-pyrrolo[2,1-f][1,2,4]triazin-2-yl]-[6-(4-methyl-piperazin-1-yl)-pyridin-3-yl]-amine;
[7-(3-Methanesulfonyl-phenyl)-pyrrolo[2,1-f][1,2,4]triazin-2-yl]-[6-(4-methyl-piperazin-1-ylmethyl)-pyridin-2-yl]-amine;
(S)-3-(4-{4-[7-(2-Methoxy-phenyl)-pyrrolo[2,1-f][1,2,4]triazin-2-ylamino]-phenyl}-piperidin-1-yl)-propane-1,2-diol;
[7-(4-Methanesulfonyl-phenyl)-pyrrolo[2,1-f][1,2,4]triazin-2-yl]-[2-methoxy-4-(4-methyl-piperazin-1-yl)-phenyl]-amine;
N-tert-Butyl-3-{2-[6-(4-methyl-piperazin-1-yl)-pyridin-3-ylamino]-pyrrolo[2,1-f][1,2,4]triazin-7-yl}-benzenesulfonamide;
4-[2-(4-Morpholin-4-yl-phenylamino)-pyrrolo[2,1-f][1,2,4]triazin-7-yl]-piperidine-1-carboxylic acid tert-butyl ester;
[7-(1-Methanesulfonyl-1,2,3,6-tetrahydro-pyridin-4-yl)-pyrrolo[2,1-f][1,2,4]triazin-2-yl]-(4-morpholin-4-yl-phenyl)-amine;
(S)-3-(4-{4-[7-(3-Chloro-phenyl)-pyrrolo[2,1-f][1,2,4]triazin-2-ylamino]-phenyl}-piperidin-1-yl)-propane-1,2-diol;
[7-(3-Chloro-phenyl)-pyrrolo[2,1-f][1,2,4]triazin-2-yl]-[4-(1-methyl-piperidin-4-yl)-phenyl]-amine;
[7-(2-Methoxy-phenyl)-pyrrolo[2,1-f][1,2,4]triazin-2-yl]-[4-(1-methyl-piperidin-4-yl)-phenyl]-amine;
(1-{4-[7-(3-Chloro-phenyl)-pyrrolo[2,1-f][1,2,4]triazin-2-ylamino]-phenyl}-piperidin-4-yl)-methanol;
2-(4-{4-[7-(3-Chloro-phenyl)-pyrrolo[2,1-f][1,2,4]triazin-2-ylamino]-phenyl}-piperazin-1-yl)-ethanol;
4-{2-[4-(4-Methyl-piperazin-1-yl)-phenylamino]-pyrrolo[2,1-f][1,2,4]triazin-7-yl}-3,6-dihydro-2H-pyridine-1-carboxylic acid tert-butyl ester;
[4-(4-Diethylamino-piperidin-1-yl)-phenyl]-[7-(4-methanesulfonyl-phenyl)-pyrrolo[2,1-f][1,2,4]triazin-2-yl]-amine;
[4-(4-Diethylamino-piperidin-1-yl)-phenyl]-[7-(3-methanesulfonyl-phenyl)-pyrrolo[2,1-f][1,2,4]triazin-2-yl]-amine;
[4-(4-Diethylamino-piperidin-1-yl)-phenyl]-[7-(2-methoxy-phenyl)-pyrrolo[2,1-f][1,2,4]triazin-2-yl]-amine;
[7-(1-Methanesulfonyl-1,2,3,6-tetrahydro-pyridin-4-yl)-pyrrolo[2,1-f][1,2,4]triazin-2-yl]-[4-(4-methyl-piperazin-1-yl)-phenyl]-amine;
(7-Benzyl-pyrrolo[2,1-f][1,2,4]triazin-2-yl)-[4-(4-methyl-piperazin-1-yl)-phenyl]-amine
(2-{2-[4-(4-Methyl-piperazin-1-yl)-phenylamino]-pyrrolo[2,1-f][1,2,4]triazin-7-yl}-phenoxy)-acetonitrile;
3-(3-{2-[4-(4-Methyl-piperazin-1-yl)-phenylamino]-pyrrolo[2,1-f][1,2,4]triazin-7-yl}-phenyl)-propionitrile;
3-{2-[4-(4-Methyl-piperazin-1-yl)-phenylamino]-pyrrolo[2,1-f][1,2,4]triazin-7-yl}-benzoic acid tert-butyl ester;
{2-[2-(4-Morpholin-4-yl-phenylamino)-pyrrolo[2,1-f][1,2,4]triazin-7-yl]-phenoxy}-acetonitrile;
3-{3-[2-(4-Morpholin-4-yl-phenylamino)-pyrrolo[2,1-f][1,2,4]triazin-7-yl]-phenyl}-propionitrile;
2-{2-[4-(4-Methyl-piperazin-1-yl)-phenylamino]-pyrrolo[2,1-f][1,2,4]triazin-7-yl}-benzoic acid ethyl ester;
3-{2-[4-(4-Methyl-piperazin-1-yl)-phenylamino]-pyrrolo[2,1-f][1,2,4]triazin-7-yl}-N-prop-2-ynyl-benzamide;
3-{3-[2-(7-Morpholin-4-yl-6,7,8,9-tetrahydro-5H-benzocyclohepten-2-ylamino)-pyrrolo[2,1-f][1,2,4]triazin-7-yl]-phenyl}-propionitrile;
3-(3-{2-[4-(1-Methyl-piperidin-4-yl)-phenylamino]-pyrrolo[2,1-f][1,2,4]triazin-7-yl}-phenyl)-propionitrile;
3-(3-{2-[4-(4-Morpholin-4-yl-piperidin-1-yl)-phenylamino]-pyrrolo[2,1-f][1,2,4]triazin-7-yl}-phenyl)-propionitrile;

3-[3-(2-{4-[4-(2-Hydroxy-ethyl)-piperazin-1-yl]-phenylamino}-pyrrolo[2,1-f][1,2,4]triazin-7-yl)-phenyl]-propionitrile;

3-(3-{2-[3-(2-Methoxy-ethyl)-2,3,4,5-tetrahydro-1H-benzo[d]azepin-7-ylamino]-pyrrolo[2,1-f][1,2,4]triazin-7-yl}-phenyl)-propionitrile;

3-(3-{2-[3-(4-Methyl-piperazin-1-yl)-phenylamino]-pyrrolo[2,1-f][1,2,4]triazin-7-yl}-phenyl)-propionitrile;

2-{2-[4-(4-Methyl-piperazin-1-yl)-phenylamino]-pyrrolo[2,1-f][1,2,4]triazin-7-yl}-phenol;

(2-{2-[4-(4-Methyl-piperazin-1-yl)-phenylamino]-pyrrolo[2,1-f][1,2,4]triazin-6-yl}-phenoxy)-acetonitrile;

[6-(2-Methoxy-phenyl)-pyrrolo[2,1-f][1,2,4]triazin-2-yl]-[4-(4-methyl-piperazin-1-yl)-phenyl]-amine;

[4-(4-Methyl-piperazin-1-yl)-phenyl]-(6-pyridin-4-yl-pyrrolo[2,1-f][1,2,4]triazin-2-yl)-amine;

[4-(4-Methyl-piperazin-1-yl)-phenyl]-(6-pyridin-3-yl-pyrrolo[2,1-f][1,2,4]triazin-2-yl)-amine;

3-(3-{2-[2-Methoxy-4-(4-morpholin-4-yl-piperidin-1-yl)-phenylamino]-pyrrolo[2,1-f][1,2,4]triazin-7-yl}-phenyl)-propionitrile;

3-(3-{6-Methyl-2-[4-(4-methyl-piperazin-1-yl)-phenylamino]-pyrrolo[2,1-f][1,2,4]triazin-7-yl}-phenyl)-propionitrile;

3-(3-{2-[4-(4-Methyl-piperazin-1-yl)-phenylamino]-pyrrolo[2,1-f][1,2,4]triazin-6-yl}-phenyl)-propionitrile;

7-{3-[(2-Methanesulfonyl-ethylamino)-methyl]-phenyl}-pyrrolo[2,1-f][1,2,4]triazin-2-yl)-[4-(4-methyl-piperazin-1-yl)-phenyl]-amine;

N(2)-[4-(4-Methyl-piperazin-1-yl)-phenyl]-N(7)-(3-nitro-benzyl)-pyrrolo[2,1-f][1,2,4]triazine-2,7-diamine;

N(2)-[4-(4-Methyl-piperazin-1-yl)-phenyl]-N(7)-pyridin-3-ylmethyl-pyrrolo[2,1-f][1,2,4]triazine-2,7-diamine;

N(2)-[4-(4-Methyl-piperazin-1-yl)-phenyl]-N(7)-pyridin-4-ylmethyl-pyrrolo[2,1-f][1,2,4]triazine-2,7-diamine;

4-(3-{2-[4-(4-Methyl-piperazin-1-yl)-phenylamino]-pyrrolo[2,1-f][1,2,4]triazin-7-yl}-phenyl)-piperazine-1-carboxylic acid tert-butyl ester;

N(2)-[3-(4-Methyl-piperazin-1-yl)-phenyl]-N(7)-pyridin-4-ylmethyl-pyrrolo[2,1-f][1,2,4]triazine-2,7-diamine;

N-(2)-[3-(4-Methyl-piperazin-1-yl)-phenyl]-N(7)-pyridin-3-ylmethyl-pyrrolo[2,1-f][1,2,4]triazine-2,7-diamine;

[4-(4-Methyl-piperazin-1-yl)-phenyl]-[7-(3-piperazin-1-yl-phenyl)-pyrrolo[2,1-f][1,2,4]triazin-2-yl]-amine;

[2-Methoxy-4-(4-morpholin-4-yl-piperidin-1-yl)-phenyl]-(7-pyridin-3-yl-pyrrolo[2,1-f][1,2,4]triazin-2-yl)-amine;

N-[2-(2-{4-[4-(2-Hydroxy-ethyl)-piperazin-1-yl]-phenylamino}-pyrrolo[2,1-f][1,2,4]triazin-7-yl)-phenyl]-N-methyl-methanesulfonamide;

N-[2-(2-{2-[4-(4-Amino-phenyl)-piperazin-1-yl]-ethoxy}-pyrrolo[2,1-f][1,2,4]triazin-7-yl)-phenyl]-N-methyl-methanesulfonamide;

(2-{2-[4-(4-Methyl-piperazin-1-yl)-phenylamino]-pyrrolo[2,1-f][1,2,4]triazin-7-yl}-phenoxy)-acetic acid tert-butyl ester;

2,2,2-Trifluoro-N-{8-[7-(4-methanesulfonyl-phenyl)-pyrrolo[2,1-f][1,2,4]triazin-2-ylamino]-2-oxo-2,3,4,5-tetrahydro-1H-benzo[b]azepin-3-yl}-acetamide;

N-[2-(2-{4-[4-(2-Hydroxy-ethyl)-piperazin-1-yl]-phenylamino}-pyrrolo[2,1-f][1,2,4]triazin-7-yl)-phenyl]-N-methyl-methanesulfonamide;

N-Methyl-N-{2-[2-(5-morpholin-4-yl-pyridin-2-ylamino)-pyrrolo[2,1-f][1,2,4]triazin-7-yl]-phenyl}-methanesulfonamide;

[7-(2-Methoxy-phenyl)-pyrrolo[2,1-f][1,2,4]triazin-2-yl]-[5-(4-methyl-piperazin-1-yl)-pyridin-2-yl]-amine;

N-Methyl-N-(2-{2-[4-(1-methyl-piperidin-4-yl)-phenylamino]-pyrrolo[2,1-f][1,2,4]triazin-7-yl}-phenyl)-methanesulfonamide;

[4-(1-Methyl-piperidin-4-yl)-phenyl]-(7-pyridin-3-yl-pyrrolo[2,1-f][1,2,4]triazin-2-yl)-amine;

[7-(6-Methoxy-pyridin-3-yl)-pyrrolo[2,1-f][1,2,4]triazin-2-yl]-[4-(1-methyl-piperidin-4-yl)-phenyl]-amine;

2-(4-{4-[7-(1-Methyl-1H-pyrazol-4-yl)-pyrrolo[2,1-f][1,2,4]triazin-2-ylamino]-phenyl}-piperazin-1-yl)-ethanol;

(2-{2-[4-(4-Methyl-piperazin-1-yl)-phenylamino]-pyrrolo[2,1-f][1,2,4]triazin-7-yl}-phenoxy)-acetic acid;

[7-(2-Methoxy-phenyl)-pyrrolo[2,1-f][1,2,4]triazin-2-yl]-[1-(2-morpholin-4-yl-ethyl)-1H-pyrazol-3-yl]-amine;

[1-(2-Morpholin-4-yl-ethyl)-1H-pyrazol-3-yl]-(7-pyridin-3-yl-pyrrolo[2,1-f][1,2,4]triazin-2-yl)-amine;

N-(3-{2-[1-(2-Morpholin-4-yl-ethyl)-1H-pyrazol-3-ylamino]-pyrrolo[2,1-f][1,2,4]triazin-7-yl}-phenyl)-methanesulfonamide;

N-Methyl-N-(2-{2-[1-(2-morpholin-4-yl-ethyl)-1H-pyrazol-3-ylamino]-pyrrolo[2,1-f][1,2,4]triazin-7-yl}-phenyl)-methanesulfonamide;

[7-(1-Methyl-1H-pyrazol-4-yl)-pyrrolo[2,1-f][1,2,4]triazin-2-yl]-[4-(4-morpholin-4-yl-piperidin-1-yl)-phenyl]-amine;

(4-Methyl-piperazin-1-yl)-(1-{4-[7-(1-methyl-1H-pyrazol-4-yl)-pyrrolo[2,1-f][1,2,4]triazin-2-ylamino]-phenyl}-piperidin-4-yl)-methanone

[4-(4-Ethyl-morpholin-2-yl)-phenyl]-[7-(1-methyl-1H-pyrazol-4-yl)-pyrrolo[2,1-f][1,2,4]triazin-2-yl]-amine;

[7-(2-Methoxy-phenyl)-pyrrolo[2,1-f][1,2,4]triazin-2-yl]-[1-(2-morpholin-4-yl-ethyl)-1H-pyrazol-4-yl]-amine;

[1-(2-Morpholin-4-yl-ethyl)-1H-pyrazol-4-yl]-(7-pyridin-3-yl-pyrrolo[2,1-f][1,2,4]triazin-2-yl)-amine;

[7-(6-Methoxy-pyridin-3-yl)-pyrrolo[2,1-f][1,2,4]triazin-2-yl]-[1-(2-morpholin-4-yl-ethyl)-1H-pyrazol-4-yl]-amine;

N-Methyl-N-(2-{2-[1-(2-morpholin-4-yl-ethyl)-1H-pyrazol-4-ylamino]-pyrrolo[2,1-f][1,2,4]triazin-7-yl}-phenyl)-methanesulfonamide;

N-(3-{2-[5-(4-Methyl-piperazin-1-yl)-pyridin-2-ylamino]-pyrrolo[2,1-f][1,2,4]triazin-7-yl}-phenyl)-methanesulfonamide;

N-(3-{2-[1-(2-Morpholin-4-yl-ethyl)-1H-pyrazol-4-ylamino]-pyrrolo[2,1-f][1,2,4]triazin-7-yl}-phenyl)-methanesulfonamide;

5-{2-[4-(4-Methyl-piperazin-1-yl)-phenylamino]-pyrrolo[2,1-f][1,2,4]triazin-7-yl}-furan-2-carbaldehyde;

N-Methyl-N-(2-{2-[5-(4-methyl-piperazin-1-yl)-pyridin-2-ylamino]-pyrrolo[2,1-f][1,2,4]triazin-7-yl}-phenyl)-methanesulfonamide;

(7-{5-[(2-Methanesulfonyl-ethylamino)-methyl]-pyridin-3-yl}-pyrrolo[2,1-f][1,2,4]triazin-2-yl)-[4-(4-methyl-piperazin-1-yl)-phenyl]-amine;

(7-{2-[(2-Methanesulfonyl-ethylamino)-methyl]-phenyl}-pyrrolo[2,1-f][1,2,4]triazin-2-yl)-[4-(4-methyl-piperazin-1-yl)-phenyl]-amine;

(7-{5-[(2-Methanesulfonyl-ethylamino)-methyl]-furan-2-yl}-pyrrolo[2,1-f][1,2,4]triazin-2-yl)-[4-(4-methyl-piperazin-1-yl)-phenyl]-amine;

[7-(1-Methyl-1H-pyrazol-4-yl)-pyrrolo[2,1-f][1,2,4]triazin-2-yl]-(7-morpholin-4-yl-6,7,8,9-tetrahydro-5H-benzocyclohepten-2-yl)-amine;

[7-(2-Methoxy-phenyl)-pyrrolo[2,1-f][1,2,4]triazin-2-yl]-(5-morpholin-4-yl-pyridin-2-yl)-amine;

4-{2-[4-(4-Methyl-piperazin-1-yl)-phenylamino]-pyrrolo[2,1-f][1,2,4]triazin-7-yl}-benzaldehyde;
N-(2-{2-[4-(4-Diethylamino-piperidin-1-yl)-phenylamino]-pyrrolo[2,1-f][1,2,4]triazin-7-yl}-phenyl)-N-methyl-methanesulfonamide;
2-Methyl-propane-2-sulfonic acid (3-{2-[4-(4-diethylamino-piperidin-1-yl)-phenylamino]-pyrrolo[2,1-f][1,2,4]triazin-7-yl}-phenyl)-amide;
[4-(4-Diethylamino-piperidin-1-yl)-phenyl]-[7-(6-methoxy-pyridin-3-yl)-pyrrolo[2,1-f][1,2,4]triazin-2-yl]-amine;
[4-(4-Diethylamino-piperidin-1-yl)-phenyl]-[7-(1-methyl-1H-pyrazol-4-yl)-pyrrolo[2,1-f][1,2,4]triazin-2-yl]-amine;
(7-{4-[(2-Methanesulfonyl-ethylamino)-methyl]-phenyl}-pyrrolo[2,1-f][1,2,4]triazin-2-yl)-[4-(4-methyl-piperazin-1-yl)-phenyl]-amine;
(7-{3-[(2-Methanesulfonyl-ethylamino)-methyl]-phenyl}-pyrrolo[2,1-f][1,2,4]triazin-2-yl)-(4-morpholin-4-yl-phenyl)-amine;
[7-(4-Methoxy-pyridin-3-yl)-pyrrolo[2,1-f][1,2,4]triazin-2-yl]-[4-(4-methyl-piperazin-1-yl)-phenyl]-amine;
[7-(4-Methoxy-pyridin-3-yl)-pyrrolo[2,1-f][1,2,4]triazin-2-yl]-(4-morpholin-4-yl-phenyl)-amine;
N-Methyl-N-[2-(2-{1-[2-(4-methyl-piperazin-1-yl)-ethyl]-1H-pyrazol-4-ylamino}-pyrrolo[2,1-f][1,2,4]triazin-7-yl)-phenyl]-methanesulfonamide;
{1-[2-(4-Methyl-piperazin-1-yl)-ethyl]-1H-pyrazol-4-yl}-[7-(1-methyl-1H-pyrazol-4-yl)-pyrrolo[2,1-f][1,2,4]triazin-2-yl]-amine;
[7-(6-Methoxy-pyridin-3-yl)-pyrrolo[2,1-f][1,2,4]triazin-2-yl]-[4-(4-methyl-piperazin-1-ylmethyl)-phenyl]-amine;
[3-Fluoro-4-(4-methyl-piperazin-1-yl)-phenyl]-[7-(1-methyl-1H-pyrazol-4-yl)-pyrrolo[2,1-f][1,2,4]triazin-2-yl]-amine;
N-tert-Butyl-3-{2-[3-fluoro-4-(4-methyl-piperazin-1-yl)-phenylamino]-pyrrolo[2,1-f][1,2,4]triazin-7-yl}-benzenesulfonamide;
2-Methyl-propane-2-sulfonic acid (3-{2-[4-(4-diethylamino-piperidin-1-yl)-phenylamino]-pyrrolo[2,1-f][1,2,4]triazin-7-yl}-phenyl)-amide;
N-(3-{2-[4-(4-Methyl-piperazin-1-yl)-phenylamino]-pyrrolo[2,1-f][1,2,4]triazin-7-yl}-pyridin-4-yl)-methanesulfonamide;
N-{3-[2-(4-Morpholin-4-yl-phenylamino)-pyrrolo[2,1-f][1,2,4]triazin-7-yl]-pyridin-4-yl}-methanesulfonamide;
(2-Methoxy-4-morpholin-4-ylmethyl-phenyl)-[7-(2-methoxy-phenyl)-pyrrolo[2,1-f][1,2,4]triazin-2-yl]-amine;
N-{2-[2-(2-Methoxy-4-morpholin-4-ylmethyl-phenylamino)-pyrrolo[2,1-f][1,2,4]triazin-7-yl]-phenyl}-N-methyl-methanesulfonamide;
4-(4-{7-[2-(Methanesulfonyl-methyl-amino)-phenyl]-pyrrolo[2,1-f][1,2,4]triazin-2-ylamino}-3-methoxy-benzyl)-piperazine-1-carboxylic acid tert-butyl ester;
N-{2-[2-(2-Methoxy-4-piperazin-1-ylmethyl-phenylamino)-pyrrolo[2,1-f][1,2,4]triazin-7-yl]-phenyl}-N-methyl-methanesulfonamide;
N-[2-(2-{4-[4-((S)-2-Hydroxy-propyl)-piperazin-1-ylmethyl]-2-methoxy-phenylamino}-pyrrolo[2,1-f][1,2,4]triazin-7-yl)-phenyl]-N-methyl-methanesulfonamide;
N-[2-(2-{4-[4-((R)-2-Hydroxy-3-methoxy-propyl)-piperazin-1-ylmethyl]-2-methoxy-phenylamino}-pyrrolo[2,1-f][1,2,4]triazin-7-yl)-phenyl]-N-methyl-methanesulfonamide;
S)-1-(4-{3-Methoxy-4-[7-(2-methoxy-phenyl)-pyrrolo[2,1-f][1,2,4]triazin-2-ylamino]-benzyl}-piperazin-1-yl)-propan-2-ol;
R)-1-Methoxy-3-(4-{3-methoxy-4-[7-(2-methoxy-phenyl)-pyrrolo[2,1-f][1,2,4]triazin-2-ylamino]-benzyl}-piperazin-1-yl)-propan-2-ol;
N-[2-(2-{4-[4-((R)-2,3-Dihydroxy-propyl)-piperazin-1-ylmethyl]-2-methoxy-phenylamino}-pyrrolo[2,1-f][1,2,4]triazin-7-yl)-phenyl]-N-methyl-methanesulfonamide;
[7-(1,3-Dimethyl-1H-pyrazol-4-yl)-pyrrolo[2,1-f][1,2,4]triazin-2-yl]-[4-(4-methyl-piperazin-1-yl)-phenyl]-amine;
N-(2-{2-[2-Methoxy-3-(4-methyl-piperazine-1-carbonyl)-phenylamino]-pyrrolo[2,1-f][1,2,4]triazin-7-yl}-phenyl)-N-methyl-methanesulfonamide;
{2-Methoxy-3-[7-(2-methoxy-phenyl)-pyrrolo[2,1-f][1,2,4]triazin-2-ylamino]-phenyl}-(4-methyl-piperazin-1-yl)-methanone;
N-(2-(2-{3-[4-(2-Hydroxy-ethyl)-piperazine-1-carbonyl]-2-methoxy-phenylamino}-pyrrolo[2,1-f][1,2,4]triazin-7-yl)-phenyl]-N-methyl-methanesulfonamide;
[4-(2-Hydroxy-ethyl)-piperazin-1-yl]-{2-methoxy-3-[7-(2-methoxy-phenyl)-pyrrolo[2,1-f][1,2,4]triazin-2-ylamino]-phenyl}-methanone;
N-(2-{2-[4-(4-Hydroxy-piperidin-1-ylmethyl)-2-methoxy-phenylamino]-pyrrolo[2,1-f][1,2,4]triazin-7-yl}-phenyl)-N-methyl-methanesulfonamide;
1-{3-Methoxy-4-[7-(2-methoxy-phenyl)-pyrrolo[2,1-f][1,2,4]triazin-2-ylamino]-benzyl}-piperidin-4-ol;
N-(2-{2-[4-((3R,4R)-3,4-Dihydroxy-pyrrolidin-1-ylmethyl)-2-methoxy-phenylamino]-pyrrolo[2,1-f][1,2,4]triazin-7-yl}-phenyl)-N-methyl-methanesulfonamide;
(3R,4R)-1-{3-Methoxy-4-[7-(2-methoxy-phenyl)-pyrrolo[2,1-f][1,2,4]triazin-2-ylamino]-benzyl}-pyrrolidine-3,4-diol;
7-(2-Methoxy-phenyl)-2-(2-methoxy-4-piperazin-1-ylmethyl-phenoxy)-pyrrolo[2,1-f][1,2,4]triazine;
{2-[4-(4-{7-[2-(Methanesulfonyl-methyl-amino)-phenyl]-pyrrolo[2,1-f][1,2,4]triazin-2-ylamino}-3-methoxy-benzyl)-piperazin-1-yl]-2-oxo-ethyl}-carbamic acid tert-butyl ester;
N-(2-{2-[4-(4-Acetyl-piperazin-1-ylmethyl)-2-methoxy-phenylamino]-pyrrolo[2,1-f][1,2,4]triazin-7-yl}-phenyl)-N-methyl-methanesulfonamide;
N-[2-(2-{4-[4-(2-Amino-acetyl)-piperazin-1-ylmethyl]-2-methoxy-phenylamino}-pyrrolo[2,1-f][1,2,4]triazin-7-yl)-phenyl]-N-methyl-methanesulfonamide;
[2-(4-{3-Methoxy-4-[7-(2-methoxy-phenyl)-pyrrolo[2,1-f][1,2,4]triazin-2-ylamino]-benzyl}-piperazin-1-yl)-2-oxo-ethyl]-carbamic acid tert-butyl ester;
1-Fluoro-3-(4-{3-methoxy-4-[7-(2-methoxy-phenyl)-pyrrolo[2,1-f][1,2,4]triazin-2-ylamino]-benzyl}-piperazin-1-yl)-propan-2-ol;
2-Amino-1-(4-{3-methoxy-4-[7-(2-methoxy-phenyl)-pyrrolo[2,1-f][1,2,4]triazin-2-ylamino]-benzyl}-piperazin-1-yl)-ethanone;
N-{2-[2-({4-[trans-1-cyano-4-(morpholin-4-yl)cyclohexyl]-2-methoxyphenyl}amino)pyrrolo[2,1-f][1,2,4]triazin-7-yl]phenyl}-N-methylmethanesulfonamide;
trans-1-[3-methoxy-4-[[7-(2-methoxyphenyl)pyrrolo[2,1-f][1,2,4]triazin-2-yl]amino]phenyl]-4-morpholino-cyclohexanecarbonitrile;
N-{2-methoxy-4-[trans-4-(morpholin-4-yl)cyclohexyl]phenyl}-7-(2-methoxyphenyl)pyrrolo[2,1-f][1,2,4]triazin-2-amine;

N-{2-[2-({2-methoxy-4-[trans-4-(morpholin-4-yl)cyclohexyl]phenyl}amino)pyrrolo[2,1-f][1,2,4]triazin-7-yl]phenyl}-N-methylmethanesulfonamide;

N-{2-[2-({2-methoxy-4-[cis-4-(morpholin-4-yl)cyclohexyl]phenyl}amino)pyrrolo[2,1-f][1,2,4]triazin-7-yl]phenyl}-N-methylmethanesulfonamide;

N-Methyl-N-{2-[2-(4-methyl-piperazin-1-yl)-pyrrolo[2,1-f][1,2,4]triazin-7-yl]-phenyl}-methanesulfonamide;

N-(2-{2-[2-Methoxy-4-(4-methyl-piperazin-1-ylmethyl)-phenylamino]-pyrrolo[2,1-f][1,2,4]triazin-7-yl}-phenyl)-N-methyl-methanesulfonamide;

[2-Methoxy-4-(4-methyl-piperazin-1-ylmethyl)-phenyl]-[7-(2-methoxy-phenyl)-pyrrolo[2,1-f][1,2,4]triazin-2-yl]-amine;

1253   N-(2-{2-[4-(1-Cyano-4-hydroxy-cyclohexyl)-2-methoxy-phenylamino]-pyrrolo[2,1-f][1,2,4]triazin-7-yl}-phenyl)-N-methyl-methanesulfonamide;

2,2,2-Trifluoro-N-[1-(4-{7-[2-(methanesulfonyl-methyl-amino)-phenyl]-pyrrolo[2,1-f][1,2,4]triazin-2-ylamino}-3-methoxy-phenyl)-cyclobutyl]-acetamide;

2-[4-(4-{7-[2-(Methanesulfonyl-methyl-amino)-phenyl]-5-methyl-pyrrolo[2,1-f][1,2,4]triazin-2-ylamino}-3-methoxy-phenyl)-piperidin-1-yl]-acetamide;

2-[4-(4-{7-[2-(Methanesulfonyl-methyl-amino)-pyridin-3-yl]-pyrrolo[2,1-f][1,2,4]triazin-2-ylamino}-3-methoxy-phenyl)-piperidin-1-yl]-acetamide;

2-[4-(4-{7-[2-(Methanesulfonyl-methyl-amino)-pyridin-3-yl]-pyrrolo[2,1-f][1,2,4]triazin-2-ylamino}-3-methoxy-phenyl)-piperidin-1-yl]-acetamide;

2-[4-(4-{7-[2-(Methanesulfonyl-methyl-amino)-pyridin-3-yl]-pyrrolo[2,1-f][1,2,4]triazin-2-ylamino}-phenyl)-piperidin-1-yl]-acetamide;

2-[4-(4-{5-Hydroxy-7-[2-(methanesulfonyl-methyl-amino)-phenyl]-pyrrolo[2,1-f][1,2,4]triazin-2-ylamino}-3-methoxy-phenyl)-piperidin-1-yl]-acetamide;

2-(4-{4-[5-Hydroxy-7-(2-methoxy-phenyl)-pyrrolo[2,1-f][1,2,4]triazin-2-ylamino]-phenyl}-piperidin-1-yl)-acetamide;

2-[4-(4-{7-[2-(Methanesulfonyl-methyl-amino)-phenyl]-5-methyl-pyrrolo[2,1-f][1,2,4]triazin-2-ylamino}-phenyl)-piperidin-1-yl]-acetamide;

2-(4-{3-Methoxy-4-[7-(2-methoxy-phenyl)-5-methyl-pyrrolo[2,1-f][1,2,4]triazin-2-ylamino]-phenyl}-piperidin-1-yl)-acetamide;

N-{2-[2-(2-Methoxy-4-piperidin-4-yl-phenylamino)-5-methyl-pyrrolo[2,1-f][1,2,4]triazin-7-yl]-phenyl}-N-methyl-methanesulfonamide;

2-[4-(3-Methoxy-4-{7-[2-(2-methoxy-ethoxy)-phenyl]-pyrrolo[2,1-f][1,2,4]triazin-2-ylamino}-phenyl)-piperidin-1-yl]-acetamide;

[2-Methoxy-4-(4-morpholin-4-yl-piperidin-1-yl)-phenyl]-(7-pyrazol-1-yl-pyrrolo[2,1-f][1,2,4]triazin-2-yl)-amine;

2-[4-(4-{7-[2-(Methanesulfonyl-methyl-amino)-4-methoxy-phenyl]-pyrrolo[2,1-f][1,2,4]triazin-2-ylamino}-3-methoxy-phenyl)-piperidin-1-yl]-acetamide;

2-(4-{3-Methoxy-4-[7-(2-methoxy-phenyl)-pyrrolo[2,1-f][1,2,4]triazin-2-ylamino]-phenyl}-3,6-dihydro-2H-pyridin-1-yl)-acetamide;

2-(4-{3-Methoxy-4-[7-(2-methoxy-phenyl)-pyrrolo[2,1-f][1,2,4]triazin-2-ylamino]-phenyl}-piperidin-1-yl)-propionamide;

2-(4-{3-Methoxy-4-[7-(2-methoxy-phenyl)-pyrrolo[2,1-f][1,2,4]triazin-2-ylamino]-phenyl}-piperidin-1-yl)-1-piperazin-1-yl-ethanone;

(4-{3-Methoxy-4-[7-(2-methoxy-phenyl)-pyrrolo[2,1-f][1,2,4]triazin-2-ylamino]-phenyl}-piperidin-1-yl)-acetic acid tert-butyl ester;

(4-{3-Methoxy-4-[7-(2-methoxy-phenyl)-pyrrolo[2,1-f][1,2,4]triazin-2-ylamino]-phenyl}-piperidin-1-yl)-acetic acid;

N-(2-Hydroxy-1-hydroxymethyl-ethyl)-2-(4-{3-methoxy-4-[7-(2-methoxy-phenyl)-pyrrolo[2,1-f][1,2,4]triazin-2-ylamino]-phenyl}-piperidin-1-yl)-acetamide;

2-[4-(4-{7-[2-(Methanesulfonyl-methyl-amino)-4-methyl-phenyl]-pyrrolo[2,1-f][1,2,4]triazin-2-ylamino]-3-methoxy-phenyl)-piperidin-1-yl]-acetamide;

N-{2-[2-(2-Methoxy-4-piperidin-4-yl-phenylamino)-pyrrolo[2,1-f][1,2,4]triazin-7-yl]-5-methyl-phenyl}-N-methyl-methanesulfonamide;

2-[4-(4-{7-[5-Fluoro-2-(methanesulfonyl-methyl-amino)-phenyl]-pyrrolo[2,1-f][1,2,4]triazin-2-ylamino]-3-methoxy-phenyl)-piperidin-1-yl]-acetamide;

2-[4-(4-{7-[2-(Methanesulfonyl-methyl-amino)-5-methoxy-phenyl]-pyrrolo[2,1-f][1,2,4]triazin-2-ylamino}-3-methoxy-phenyl)-piperidin-1-yl]-acetamide;

(4-Morpholin-4-yl-phenyl)-[7-(1H-pyrrol-2-yl)-pyrrolo[2,1-f][1,2,4]triazin-2-yl]-amine;

(4-Morpholin-4-yl-phenyl)-(7-phenyl-pyrrolo[2,1-f][1,2,4]triazin-2-yl)-amine;

3-{2-[2-(4-Morpholin-4-yl-phenylamino)-pyrrolo[2,1-f][1,2,4]triazin-7-yl]-pyrrol-1-yl}-propionitrile;

N-(3-{7-[1-(2-Cyano-ethyl)-1H-pyrrol-2-yl]-pyrrolo[2,1-f][1,2,4]triazin-2-ylamino}-phenyl)-acetamide;

3-(2-{2-[3-(2-Methoxy-1-methyl-ethoxy)-phenylamino]-pyrrolo[2,1-f][1,2,4]triazin-7-yl}-pyrrol-1-yl)-propionitrile;

3-(2-{2-[3-(2-Oxo-pyrrolidin-1-yl)-phenylamino]-pyrrolo[2,1-f][1,2,4]triazin-7-yl}-pyrrol-1-yl)-propionitrile;

N-tert-Butyl-3-[2-(2-trifluoromethyl-3H-benzimidazol-5-ylamino)-pyrrolo[2,1-f][1,2,4]triazin-7-yl]-benzenesulfonamide;

N-tert-Butyl-3-[2-(2-oxo-2,3-dihydro-1H-benzimidazol-5-ylamino)-pyrrolo[2,1-f][1,2,4]triazin-7-yl]-benzenesulfonamide;

3-[2-(3H-Benzimidazol-5-ylamino)-pyrrolo[2,1-f][1,2,4]triazin-7-yl]-N-tert-butyl-Benzenesulfonamide;

N-tert-Butyl-3-[2-(3-methyl-3H-benzimidazol-5-ylamino)-pyrrolo[2,1-f][1,2,4]triazin-7-yl]-benzenesulfonamide;

[7-(4-Methanesulfonyl-phenyl)-pyrrolo[2,1-f][1,2,4]triazin-2-yl]-(3-methyl-3H-benzimidazol-5-yl)-amine;

[7-(4-Methanesulfonyl-phenyl)-pyrrolo[2,1-f][1,2,4]triazin-2-yl]-(2-trifluoromethyl-3H-benzimidazol-5-yl)-amine;

5-[7-(4-Methanesulfonyl-phenyl)-pyrrolo[2,1-f][1,2,4]triazin-2-ylamino]-1,3-dihydro-benzimidazol-2-one;

(3H-Benzimidazol-5-yl)-[7-(4-methanesulfonyl-phenyl)-pyrrolo[2,1-f][1,2,4]triazin-2-yl]-amine;

7-(2-Methoxy-phenyl)-pyrrolo[2,1-f][1,2,4]triazin-2-yl]-(2-trifluoromethyl-3H-benzimidazol-5-yl)-amine;

(3H-Benzimidazol-5-yl)-[7-(2-methoxy-phenyl)-pyrrolo[2,1-f][1,2,4]triazin-2-yl]-amine;

[7-(6-Methoxy-pyridin-3-yl)-pyrrolo[2,1-f][1,2,4]triazin-2-yl]-(3-methyl-3H-benzimidazol-5-yl)-amine;

[7-(6-Methoxy-pyridin-3-yl)-pyrrolo[2,1-f][1,2,4]triazin-2-yl]-(2-trifluoromethyl-3H-benzimidazol-5-yl)-amine;

5-[7-(6-Methoxy-pyridin-3-yl)-pyrrolo[2,1-f][1,2,4]triazin-2-ylamino]-1,3-dihydro-benzimidazol-2-one;

N-{2-[2-(3-Methyl-3H-benzoimidazol-5-ylamino)-pyrrolo[2,1-f][1,2,4]triazin-7-yl]-phenyl}-methanesulfonamide;
(3H-Benzimidazol-5-yl)-[7-(3-ethanesulfonyl-phenyl)-pyrrolo[2,1-f][1,2,4]triazin-2-yl]-amine;
[7-(3-Ethanesulfonyl-phenyl)-pyrrolo[2,1-f][1,2,4]triazin-2-yl]-(3-methyl-3H-benzimidazol-5-yl)-amine;
[7-(3-Ethanesulfonyl-phenyl)-pyrrolo[2,1-f][1,2,4]triazin-2-yl]-(2-trifluoromethyl-3H-benzimidazol-5-yl)-amine;
7-(3-Cyclopropylmethanesulfonyl-phenyl)-pyrrolo[2,1-f][1,2,4]triazin-2-yl]-(1H-indazol-5-yl)-amine;
N-tert-Butyl-3-[2-(1H-indazol-5-ylamino)-pyrrolo[2,1-f][1,2,4]triazin-7-yl]-benzenesulfonamide;
N-tert-Butyl-3-[2-(1-methyl-1H-indazol-5-ylamino)-pyrrolo[2,1-f][1,2,4]triazin-7-yl]-benzenesulfonamide;
N-tert-Butyl-3-[2-(1-methyl-1H-indazol-6-ylamino)-pyrrolo[2,1-f][1,2,4]triazin-7-yl]-benzenesulfonamide;
[7-(3-Cyclopropylmethanesulfonyl-phenyl)-pyrrolo[2,1-f][1,2,4]triazin-2-yl]-(2-trifluoromethyl-3H-benzimidazol-5-yl)-amine;
(3H-Benzimidazol-5-yl)-[7-(3-cyclopropylmethanesulfonyl-phenyl)-pyrrolo[2,1-f][1,2,4]triazin-2-yl]-amine;
[7-(3-Cyclopropylmethanesulfonyl-phenyl)-pyrrolo[2,1-f][1,2,4]triazin-2-yl]-(3-methyl-3H-benzimidazol-5-yl)-amine;
[7-(3-Cyclopropylmethanesulfonyl-phenyl)-pyrrolo[2,1-f][1,2,4]triazin-2-yl]-(1-methyl-1H-indazol-6-yl)-amine;
[7-(3-Cyclopropylmethanesulfonyl-phenyl)-pyrrolo[2,1-f][1,2,4]triazin-2-yl]-(1-methyl-1H-indazol-5-yl)-amine;
N-tert-Butyl-3-{2-[1-(2-morpholin-4-yl-ethyl)-1H-indazol-5-ylamino]-pyrrolo[2,1-f][1,2,4]triazin-7-yl}-benzenesulfonamide;
N-tert-Butyl-3-{2-[1-(2-morpholin-4-yl-ethyl)-1H-indazol-6-ylamino]-pyrrolo[2,1-f][1,2,4]triazin-7-yl}-benzenesulfonamide;
N-tert-Butyl-3-{2-[1-(2-morpholin-4-yl-ethyl)-1H-benzimidazol-5-ylamino]-pyrrolo[2,1-f][1,2,4]triazin-7-yl}-benzenesulfonamide;
N-tert-Butyl-3-{2-[3-(2-morpholin-4-yl-ethyl)-3H-benzimidazol-5-ylamino]-pyrrolo[2,1-f][1,2,4]triazin-7-yl}-benzenesulfonamide;
N-tert-Butyl-3-[2-(1H-indazol-6-ylamino)-pyrrolo[2,1-f][1,2,4]triazin-7-yl]-benzenesulfonamide;
N-tert-Butyl-3-[2-(2-ethyl-3H-benzimidazol-5-ylamino)-pyrrolo[2,1-f][1,2,4]triazin-7-yl]-benzenesulfonamide;
N-tert-Butyl-3-[2-(2-isopropyl-3H-benzimidazol-5-ylamino)-pyrrolo[2,1-f][1,2,4]triazin-7-yl]-benzenesulfonamide;
N-tert-Butyl-3-[2-(2-tert-butyl-3H-benzimidazol-5-ylamino)-pyrrolo[2,1-f][1,2,4]triazin-7-yl]-benzenesulfonamide;
N-tert-Butyl-3-[2-(2,3-dimethyl-3H-benzimidazol-5-ylamino)-pyrrolo[2,1-f][1,2,4]triazin-7-yl]-benzenesulfonamide;
N-tert-Butyl-3-[2-(1-methyl-1H-benzimidazol-5-ylamino)-pyrrolo[2,1-f][1,2,4]triazin-7-yl]-benzenesulfonamide;
N-Methyl-N-(2-{2-[1-(2-morpholin-4-yl-ethyl)-1H-indazol-5-ylamino]-pyrrolo[2,1-f][1,2,4]triazin-7-yl}-phenyl)-methanesulfonamide;
N-Methyl-N-(2-{2-[1-(2-morpholin-4-yl-ethyl)-1H-indazol-6-ylamino]-pyrrolo[2,1-f][1,2,4]triazin-7-yl}-phenyl)-methanesulfonamide;
N-Methyl-N-(2-{2-[1-(2-morpholin-4-yl-ethyl)-1H-benzimidazol-5-ylamino]-pyrrolo[2,1-f][1,2,4]triazin-7-yl}-phenyl)-methanesulfonamide;
N-Methyl-N-(2-{2-[3-(2-morpholin-4-yl-ethyl)-3H-benzimidazol-5-ylamino]-pyrrolo[2,1-f][1,2,4]triazin-7-yl}-phenyl)-methanesulfonamide;
N-{2-[2-(1H-Indazol-6-ylamino)-pyrrolo[2,1-f][1,2,4]triazin-7-yl]-phenyl}-N-methyl-methanesulfonamide;
N-{2-[2-(1H-Indazol-5-ylamino)-pyrrolo[2,1-f][1,2,4]triazin-7-yl]-phenyl}-N-methyl-methanesulfonamide;
N-Methyl-N-{2-[2-(1-methyl-1H-indazol-5-ylamino)-pyrrolo[2,1-f][1,2,4]triazin-7-yl]-phenyl}-methanesulfonamide;
N-Methyl-N-{2-[2-(1-methyl-1H-indazol-6-ylamino)-pyrrolo[2,1-f][1,2,4]triazin-7-yl]-phenyl}-methanesulfonamide;
N-{2-[2-(2-tert-Butyl-3H-benzimidazol-5-ylamino)-pyrrolo[2,1-f][1,2,4]triazin-7-yl]-phenyl}-N-methyl-methanesulfonamide;
N-Methyl-N-(2-{2-[2-(2-morpholin-4-yl-ethyl)-2H-indazol-6-ylamino]-pyrrolo[2,1-f][1,2,4]triazin-7-yl}-phenyl)-methanesulfonamide;
N-Methyl-N-(2-{2-[2-(2-morpholin-4-yl-ethyl)-2H-indazol-5-ylamino]-pyrrolo[2,1-f][1,2,4]triazin-7-yl}-phenyl)-methanesulfonamide;
N-tert-Butyl-3-{2-[2-(2-morpholin-4-yl-ethyl)-2H-indazol-6-ylamino]-pyrrolo[2,1-f][1,2,4]triazin-7-yl}-benzenesulfonamide;
N-tert-Butyl-3-{2-[2-(2-morpholin-4-yl-ethyl)-2H-indazol-5-ylamino]-pyrrolo[2,1-f][1,2,4]triazin-7-yl}-benzenesulfonamide;
[7-(2-Methoxy-phenyl)-pyrrolo[2,1-f][1,2,4]triazin-2-yl]-[1-(2-morpholin-4-yl-ethyl)-1H-indazol-5-yl]-amine;
[7-(2-Methoxy-phenyl)-pyrrolo[2,1-f][1,2,4]triazin-2-yl]-[1-(2-morpholin-4-yl-ethyl)-1H-indazol-6-yl]-amine;
[7-(2-Methoxy-phenyl)-pyrrolo[2,1-f][1,2,4]triazin-2-yl]-[1-(2-morpholin-4-yl-ethyl)-1H-benzimidazol-5-yl]-amine;
[7-(2-Methoxy-phenyl)-pyrrolo[2,1-f][1,2,4]triazin-2-yl]-[3-(2-morpholin-4-yl-ethyl)-3H-benzimidazol-5-yl]-amine;
[7-(2-Methoxy-phenyl)-pyrrolo[2,1-f][1,2,4]triazin-2-yl]-[2-(2-morpholin-4-yl-ethyl)-2H-indazol-6-yl]-amine;
[7-(2-Methoxy-phenyl)-pyrrolo[2,1-f][1,2,4]triazin-2-yl]-[2-(2-morpholin-4-yl-ethyl)-2H-indazol-5-yl]-amine;
(2-tert-Butyl-3H-benzimidazol-5-yl)-[7-(2-methoxy-phenyl)-pyrrolo[2,1-f][1,2,4]triazin-2-yl]-amine;
2-(4-{4-[7-(2-Fluoro-6-methoxy-phenyl)-pyrrolo[2,1-f][1,2,4]triazin-2-ylamino]-phenyl}-piperidin-1-yl)-acetamide;
N-Methyl-N-{2-[2-(pyridin-3-ylamino)-pyrrolo[2,1-f][1,2,4]triazin-7-yl]-phenyl}-methanesulfonamide;
N-Methyl-N-{2-[2-(thiazol-2-ylamino)-pyrrolo[2,1-f][1,2,4]triazin-7-yl]-phenyl}-methanesulfonamide;
N-{3-[7-(3-Methanesulfonylamino-phenyl)-pyrrolo[2,1-f][1,2,4]triazin-2-ylamino]-phenyl}-acetamide;
N-Methyl-N-{2-[2-(pyridin-4-ylamino)-pyrrolo[2,1-f][1,2,4]triazin-7-yl]-phenyl}-methanesulfonamide;
N-{3-[2-(1-Acetyl-5,5-dimethyl-2,3,4,5-tetrahydro-1H-benzo[b]azepin-8-ylamino)-pyrrolo[2,1-f][1,2,4]triazin-7-yl]-phenyl}-methanesulfonamide;
N-{2-[2-(1-Acetyl-5,5-dimethyl-2,3,4,5-tetrahydro-1H-benzo[b]azepin-8-ylamino)-pyrrolo[2,1-f][1,2,4]triazin-7-yl]-phenyl}-N-methyl-methanesulfonamide;
N-{3-[2-(1-Acetyl-2,3-dihydro-1H-indol-6-ylamino)-pyrrolo[2,1-f][1,2,4]triazin-7-yl]-phenyl}-methanesulfonamide;

N-{3-[7-(3-tert-Butylsulfamoyl-phenyl)-pyrrolo[2,1-f][1,2,4]triazin-2-ylamino]-phenyl}-acetamide;
3-[2-(1-Acetyl-5,5-dimethyl-2,3,4,5-tetrahydro-1H-benzo[b]azepin-8-ylamino)-pyrrolo[2,1-f][1,2,4]triazin-7-yl]-N-tert-butyl-benzenesulfonamide;
N-(2-{2-[4-Methoxy-3-(2-oxo-pyrrolidin-1-yl)-phenylamino]-pyrrolo[2,1-f][1,2,4]triazin-7-yl]-phenyl}-N-methyl-methanesulfonamide;
N-{2-[2-(2,2-Dimethyl-3-oxo-3,4-dihydro-2H-1,4-benzoxazin-6-ylamino)-pyrrolo[2,1-f][1,2,4]triazin-7-yl]-phenyl}-N-methyl-methanesulfonamide;
3-[2-(1-Acetyl-2,3-dihydro-1H-indol-6-ylamino)-pyrrolo[2,1-f][1,2,4]triazin-7-yl]-N-tert-butyl-benzenesulfonamide;
3-[2-(4-Acetyl-3,4-dihydro-2H-benzo[1,4]oxazin-6-ylamino)-pyrrolo[2,1-f][1,2,4]triazin-7-yl]-N-tert-butyl-benzenesulfonamide;
N-{2-[2-(4-Acetyl-3,4-dihydro-2H-1,4-benzoxazin-6-ylamino)-pyrrolo[2,1-f][1,2,4]triazin-7-yl]-phenyl}-N-methyl-methanesulfonamide;
N-(3-{7-[2-(Methanesulfonyl-methyl-amino)-phenyl]-pyrrolo[2,1-f][1,2,4]triazin-2-ylamino}-phenyl)-acetamide;
N-tert-Butyl-3-[2-(2,2-dimethyl-3-oxo-3,4-dihydro-2H-1,4-benzoxazin-6-ylamino)-pyrrolo[2,1-f][1,2,4]triazin-7-yl]-benzenesulfonamide;
N-tert-Butyl-3-{2-[4-methoxy-3-(2-oxo-pyrrolidin-1-yl)-phenylamino]-pyrrolo[2,1-f][1,2,4]triazin-7-yl}-benzenesulfonamide;
N-{3-[7-(1-Methyl-1H-pyrazol-4-yl)-pyrrolo[2,1-f][1,2,4]triazin-2-ylamino]-phenyl}-acetamide;
1-Ethyl-5,5-dimethyl-8-[7-(1-methyl-1H-pyrazol-4-yl)-pyrrolo[2,1-f][1,2,4]triazin-2-ylamino]-1,3,4,5-tetrahydro-benzo[b]azepin-2-one;
N-{2-tert-Butyl-5-[7-(1-methyl-1H-pyrazol-4-yl)-pyrrolo[2,1-f][1,2,4]triazin-2-ylamino]-phenyl}-acetamide;
1-{5,5-Dimethyl-8-[7-(1-methyl-1H-pyrazol-4-yl)-pyrrolo[2,1-f][1,2,4]triazin-2-ylamino]-2,3,4,5-tetrahydro-benzo[b]azepin-1-yl}ethanone;
N-{3-[7-(2-Methanesulfonylamino-phenyl)-pyrrolo[2,1-f][1,2,4]triazin-2-ylamino]-phenyl}-acetamide;
N-tert-Butyl-3-{2-[3-(2-oxo-pyrrolidin-1-yl)-phenylamino]-pyrrolo[2,1-f][1,2,4]triazin-7-yl}-benzenesulfonamide;
3-[7-(3-tert-Butylsulfamoyl-phenyl)-pyrrolo[2,1-f][1,2,4]triazin-2-ylamino]-N-methyl-benzamide;
N-{3-[7-(3-tert-Butylsulfamoyl-phenyl)-pyrrolo[2,1-f][1,2,4]triazin-2-ylamino]-phenyl}-isobutyramide;
N-tert-Butyl-3-[2-(3-pyrazol-1-yl-phenylamino)-pyrrolo[2,1-f][1,2,4]triazin-7-yl]-benzenesulfonamide;
N-{2-tert-Butyl-5-[7-(3-tert-butylsulfamoyl-phenyl)-pyrrolo[2,1-f][1,2,4]triazin-2-ylamino]-phenyl}-acetamide;
3-[2-(1-Acetyl-3,3-dimethyl-2,3-dihydro-1H-indol-6-ylamino)-pyrrolo[2,1-f][1,2,4]triazin-7-yl]-N-tert-butyl-benzenesulfonamide;
N-{3-[7-(1-Methyl-1H-pyrazol-4-yl)-pyrrolo[2,1-f][1,2,4]triazin-2-ylamino]-phenyl}-methanesulfonamide;
3-[7-(3-tert-Butylsulfamoyl-phenyl)-pyrrolo[2,1-f][1,2,4]triazin-2-ylamino]-benzamide;
N-tert-Butyl-3-[2-(3-[1,2,4]triazol-4-yl-phenylamino)-pyrrolo[2,1-f][1,2,4]triazin-7-yl]-benzenesulfonamide;
[3-(4-Methyl-piperazin-1-yl)-phenyl]-[7-(3-morpholin-4-yl-phenyl)-pyrrolo[2,1-f][1,2,4]triazin-2-yl]-amine;
N-tert-Butyl-3-[2-(3-morpholin-4-yl-phenylamino)-pyrrolo[2,1-f][1,2,4]triazin-7-yl]-benzenesulfonamide;
N-tert-Butyl-3-[2-(4-fluoro-3-morpholin-4-yl-phenylamino)-pyrrolo[2,1-f][1,2,4]triazin-7-yl]-benzenesulfonamide;
N-tert-Butyl-3-[2-(4-fluoro-4-morpholin-4-yl-phenylamino)-pyrrolo[2,1-f][1,2,4]triazin-7-yl]-benzenesulfonamide;
N-tert-Butyl-3-[2-(3-methoxy-phenylamino)-pyrrolo[2,1-f][1,2,4]triazin-7-yl]-benzenesulfonamide;
(2-{2-[3-Fluoro-4-(4-methyl-piperazin-1-yl)-phenylamino]-pyrrolo[2,1-f][1,2,4]triazin-7-yl}-phenoxy)-acetic acid 2-methoxy-1-methyl-ethyl ester;
N-{5-[7-(3-tert-Butylsulfamoyl-phenyl)-pyrrolo[2,1-f][1,2,4]triazin-2-ylamino]-2-methyl-phenyl}-acetamide;
4-[7-(3-tert-Butylsulfamoyl-phenyl)-pyrrolo[2,1-f][1,2,4]triazin-2-ylamino]-benzamide;
N-tert-Butyl-3-[2-(4-chloro-phenylamino)-pyrrolo[2,1-f][1,2,4]triazin-7-yl]-benzenesulfonamide;
(2-{2-[3-Fluoro-4-(4-methyl-piperazin-1-yl)-phenylamino]-pyrrolo[2,1-f][1,2,4]triazin-7-yl}-phenoxy)-acetic acid;
N-tert-Butyl-3-[2-(4-oxazol-5-yl-phenylamino)-pyrrolo[2,1-f][1,2,4]triazin-7-yl]-benzenesulfonamide;
N,N-Dimethyl-2-(2-{2-[4-(4-methyl-piperazin-1-yl)-phenylamino]-pyrrolo[2,1-f][1,2,4]triazin-7-yl}-phenoxy)-acetamide;
2-(2-{2-[3-Fluoro-4-(4-methyl-piperazin-1-yl)-phenylamino]-pyrrolo[2,1-f][1,2,4]triazin-7-yl}-phenoxy)-N,N-dimethyl-acetamide;
[7-(6-Methoxy-pyridin-3-yl)-pyrrolo[2,1-f][1,2,4]triazin-2-yl]-(4-pyrrolidin-1-ylmethyl-phenyl)-amine;
{4-[7-(6-Methoxy-pyridin-3-yl)-pyrrolo[2,1-f][1,2,4]triazin-2-ylamino]-phenyl}-morpholin-4-yl-methanone;
2-(4-{4-[7-(3-tert-Butylsulfamoyl-phenyl)-pyrrolo[2,1-f][1,2,4]triazin-2-ylamino]-2-fluoro-phenyl}-piperazin-1-yl)-acetamide;
2-[4-(4-{7-[2-(Methanesulfonyl-methyl-amino)-phenyl]-pyrrolo[2,1-f][1,2,4]triazin-2-ylamino}-phenyl)-piperidin-1-yl]-acetamide;
2-(2-{2-[4-(1-Methyl-piperidin-4-yl)-phenylamino]-pyrrolo[2,1-f][1,2,4]triazin-7-yl}-phenoxy)-acetamide;
N-tert-Butyl-3-{2-[4-(4-methyl-piperazine-1-carbonyl)-phenylamino]-pyrrolo[2,1-f][1,2,4]triazin-7-yl}-benzenesulfonamide;
N-tert-Butyl-3-{2-[3-chloro-4-(4-methyl-piperazin-1-yl)-phenylamino]-pyrrolo[2,1-f][1,2,4]triazin-7-yl}-benzenesulfonamide;
N-tert-Butyl-3-(2-{3-fluoro-4-[4-((S)-2-hydroxy-propyl)-piperazin-1-yl]-phenylamino}-pyrrolo[2,1-f][1,2,4]triazin-7-yl)-benzenesulfonamide;
2-(4-{4-[7-(6-Methoxy-pyridin-3-yl)-pyrrolo[2,1-f][1,2,4]triazin-2-ylamino]-phenyl}-piperidin-1-yl)-acetamide;
2-(4-{2-Fluoro-4-[7-(6-methoxy-pyridin-3-yl)-pyrrolo[2,1-f][1,2,4]triazin-2-ylamino]-phenyl}-piperazin-1-yl)-acetamide;
2-(4-{2-Fluoro-4-[7-(6-methoxy-pyridin-3-yl)-pyrrolo[2,1-f][1,2,4]triazin-2-ylamino]-phenyl}-piperazin-1-yl)-acetamide;
2-(4-{2-Fluoro-4-[7-(2-methoxy-phenyl)-pyrrolo[2,1-f][1,2,4]triazin-2-ylamino]-phenyl}-piperazin-1-yl)-acetamide;
(S)-1-(4-{2-Fluoro-4-[7-(2-methoxy-phenyl)-pyrrolo[2,1-f][1,2,4]triazin-2-ylamino]-phenyl}-piperazin-1-yl)-propan-2-ol;
[3-Chloro-4-(4-methyl-piperazin-1-yl)-phenyl]-[7-(2-methoxy-phenyl)-pyrrolo[2,1-f][1,2,4]triazin-2-yl]-amine;

[3-Chloro-4-(4-methyl-piperazin-1-yl)-phenyl]-[7-(6-methoxy-pyridin-3-yl)-pyrrolo[2,1-f][1,2,4]triazin-2-yl]-amine;

{4-[7-(6-Methoxy-pyridin-3-yl)-pyrrolo[2,1-f][1,2,4]triazin-2-ylamino]-phenyl}-(4-methyl-piperazin-1-yl)-methanone;

N-(2-{2-[3-Fluoro-4-(4-methyl-piperazin-1-yl)-phenylamino}-pyrrolo[2,1-f][1,2,4]triazin-7-yl]-phenyl)-N-methyl-methanesulfonamide;

2-[4-(2-Fluoro-4-{7-[2-(methanesulfonyl-methyl-amino)-phenyl]-pyrrolo[2,1-f][1,2,4]triazin-2-ylamino}-phenyl)-piperazin-1-yl]-acetamide;

N-[2-(2-{3-Fluoro-4-[4-((S)-2-hydroxy-propyl)-piperazin-1-yl]-phenylamino}-pyrrolo[2,1-f][1,2,4]triazin-7-yl)-phenyl]-N-methyl-methanesulfonamide;

N-(2-{2-[3-Chloro-4-(4-methyl-piperazin-1-yl)-phenylamino]-pyrrolo[2,1-f][1,2,4]triazin-7-yl}-phenyl)-N-methyl-methanesulfonamide;

N-Methyl-N-(2-{2-[4-(4-methyl-piper azine-1-carbonyl)-phenylamino]-pyrrolo[2,1-f][1,2,4]triazin-7-yl}-phenyl)-methanesulfonamide;

(S)-1-(4-{4-[7-(2-Methoxy-phenyl)-pyrrolo[2,1-f][1,2,4]triazin-2-ylamino}-phenyl]-piperidin-1-yl)-propan-2-ol;

2-(4-{4-[7-(2-Hydroxy-phenyl)-pyrrolo[2,1-f][1,2,4]triazin-2-ylamino]-phenyl}-piperidin-1-yl)-acetamide;

N-Methyl-N-{2-[2-(4-pyrrolidin-1-yl methyl-phenylamino)-pyrrolo[2,1-f][1,2,4]triazin-7-yl]-phenyl}-methane sulfonamide;

N-tert-Butyl-3-[2-(4-pyrrolidin-1-ylmethyl-phenylamino)-pyrrolo[2,1-f][1,2,4]triazin-7-yl]-benzenesulfonamide;

[7-(2-Methoxy-phenyl)-pyrrolo[2,1-f][1,2,4]triazin-2-yl]-(4-pyrrolidin-1-ylmethyl-phenyl)-amine;

(S)-1-(4-{4-[7-(3-Methanesulfonyl-phenyl)-pyrrolo[2,1-f][1,2,4]triazin-2-ylamino]-phenyl}-piperidin-1-yl)-propan-2-ol;

(S)-1-(4-{4-[7-(4-Methanesulfonyl-phenyl)-pyrrolo[2,1-f][1,2,4]triazin-2-ylamino]-phenyl}-piperidin-1-yl)-propan-2-ol;

2-(4-{4-[7-(4-Dimethylaminomethyl-phenyl)-pyrrolo[2,1-f][1,2,4]triazin-2-ylamino]-phenyl}-piperidin-1-yl)-acetamide;

2-(4-{4-[7-(3-Methanesulfonyl-phenyl)-pyrrolo[2,1-f][1,2,4]triazin-2-ylamino]-phenyl}-piperidin-1-yl)-acetamide;

2-(4-{4-[7-(4-Methanesulfonyl-phenyl)-pyrrolo[2,1-f][1,2,4]triazin-2-ylamino]-phenyl}-piperidin-1-yl)-acetamide;

N-[2-(2-{4-[1-((S)-2-Hydroxy-propyl)-piperidin-4-yl]-phenylamino}-pyrrolo[2,1-f][1,2,4]triazin-7-yl)-phenyl]-N-methyl-methanesulfonamide;

[3-Fluoro-4-(4-methyl-piperazin-1-yl)-phenyl]-[7-(4-methanesulfonyl-phenyl)-pyrrolo[2,1-f][1,2,4]triazin-2-yl]-amine;

(R)-{2-Methoxy-4-[3-(4-methyl-piperazin-1-yl)-piperidin-1-yl]-phenyl}-[7-(2-methoxy-phenyl)-pyrrolo[2,1-f][1,2,4]triazin-2-yl]-amine;

(S)-{2-Methoxy-4-[3-(4-methyl-piperazin-1-yl)-piperidin-1-yl]-phenyl}-[7-(2-methoxy-phenyl)-pyrrolo[2,1-f][1,2,4]triazin-2-yl]-amine;

2-[4-(1-{3-Methoxy-4-[7-(2-methoxy-phenyl)-pyrrolo[2,1-f][1,2,4]triazin-2-ylamino]-phenyl}-piperidin-3-yl)-piperazin-1-yl]-ethanol;

[2-Methoxy-4-(3-morpholin-4-yl-piperidin-1-yl)-phenyl]-[7-(2-methoxy-phenyl)-pyrrolo[2,1-f][1,2,4]triazin-2-yl]-amine;

{4-[3-(2,6-Dimethyl-morpholin-4-yl)-piperidin-1-yl]-2-methoxy-phenyl}-[7-(2-methoxy-phenyl)-pyrrolo[2,1-f][1,2,4]triazin-2-yl]-amine;

N-(3-{2-[2-Methoxy-4-(4-morpholin-4-yl-piperidin-1-yl)-phenylamino]-pyrrolo[2,1-f][1,2,4]triazin-7-yl}-phenyl)-methanesulfonamide;

[7-(2-Ethoxy-phenyl)-pyrrolo[2,1-f][1,2,4]triazin-2-yl]-[2-methoxy-4-(4-morpholin-4-yl-piperidin-1-yl)-phenyl]-amine;

[7-(2-Methoxy-phenyl)-pyrrolo[2,1-f][1,2,4]triazin-2-yl]-[2-methoxy-4-(3-piperazin-1-yl-piperidin-1-yl)-phenyl]-amine;

N-(3-{2-[2-Methoxy-4-(4-morpholin-4-yl-piperidin-1-yl)-phenylamino]-pyrrolo[2,1-f][1,2,4]triazin-7-yl}-phenyl)-N-methyl-methanesulfonamide;

N-(2-{2-[2-Methoxy-4-(4-morpholin-4-yl-piperidin-1-yl)-phenylamino]-pyrrolo[2,1-f][1,2,4]triazin-7-yl}-phenyl)-methanesulfonamide;

[7-(2-Isopropoxy-phenyl)-pyrrolo[2,1-f][1,2,4]triazin-2-yl]-[2-methoxy-4-(4-morpholin-4-yl-piperidin-1-yl)-phenyl]-amine;

(1-Methoxy-7-morpholin-4-yl-6,7,8,9-tetrahydro-5H-benzocyclohepten-2-yl)-[7-(2-methoxy-phenyl)-pyrrolo[2,1-f][1,2,4]triazin-2-yl]-amine;

N-(2-{2-[2-Methoxy-4-(4-morpholin-4-yl-piperidin-1-yl)-phenylamino]-pyrrolo[2,1-f][1,2,4]triazin-7-yl}-phenyl)-N-methyl-methanesulfonamide;

1-(2-{2-[2-Methoxy-4-(4-morpholin-4-yl-piperidin-1-yl)-phenylamino]-pyrrolo[2,1-f][1,2,4]triazin-7-yl}-phenyl)-ethanone;

[2-Methoxy-4-(4-morpholin-4-yl-piperidin-1-yl)-phenyl]-[7-(2-trifluoromethoxy-phenyl)-pyrrolo[2,1-f][1,2,4]triazin-2-yl]-amine;

N-Methyl-N-(2-{2-[4-(4-morpholin-4-yl-piperidin-1-yl)-phenylamino]-pyrrolo[2,1-f][1,2,4]triazin-7-yl}-phenyl)-methanesulfonamide;

N-(2-{2-[2-Methoxy-4-(4-methyl-piperazin-1-yl)-phenylamino]-pyrrolo[2,1-f][1,2,4]triazin-7-yl}-phenyl)-N-methyl-methanesulfonamide;

N-[2-(2-{4-[4-((S)-2-Hydroxy-propyl)-piperazin-1-yl]-2-methoxy-phenylamino}-pyrrolo[2,1-f][1,2,4]triazin-7-yl)-phenyl]-N-methyl-methanesulfonamide;

N-[2-(2-{4-[4-((R)-2-Hydroxy-propyl)-piperazin-1-yl]-2-methoxy-phenylamino}-pyrrolo[2,1-f][1,2,4]triazin-7-yl)-phenyl]-N-methyl-methanesulfonamide;

N-Ethyl-N-(2-{2-[2-methoxy-4-(4-morpholin-4-yl-piperidin-1-yl)-phenylamino]-pyrrolo[2,1-f][1,2,4]triazin-7-yl}-phenyl)-methanesulfonamide;

N-Cyclopropylmethyl-N-(2-{2-[2-methoxy-4-(4-morpholin-4-yl-piperidin-1-yl)-phenylamino]-pyrrolo[2,1-f][1,2,4]triazin-7-yl}-phenyl)-methanesulfonamide;

N-(2-Methoxy-ethyl)-N-(2-{2-[2-methoxy-4-(4-morpholin-4-yl-piperidin-1-yl)-phenylamino]-pyrrolo[2,1-f][1,2,4]triazin-7-yl}-phenyl)-methanesulfonamide;

N-(2-Fluoro-ethyl)-N-(2-{2-[2-methoxy-4-(4-morpholin-4-yl-piperidin-1-yl)-phenylamino]-pyrrolo[2,1-f][1,2,4]triazin-7-yl}-phenyl)-methanesulfonamide;

[2-Methoxy-4-(4-morpholin-4-yl-piperidin-1-yl)-phenyl]-[7-(2-trifluoromethyl-phenyl)-pyrrolo[2,1-f][1,2,4]triazin-2-yl]-amine;

[7-(2,3-Dimethoxy-phenyl)-pyrrolo[2,1-f][1,2,4]triazin-2-yl]-[2-methoxy-4-(4-morpholin-4-yl-piperidin-1-yl)-phenyl]-amine;

[7-(2-Chloro-phenyl)-pyrrolo[2,1-f][1,2,4]triazin-2-yl]-[2-methoxy-4-(4-morpholin-4-yl-piperidin-1-yl)-phenyl]-amine;

2-Methoxy-4-(4-methyl-4-morpholin-4-yl-piperidin-1-yl)-phenyl]-[7-(2-methoxy-phenyl)-pyrrolo[2,1-f][1,2,4]triazin-2-yl]-amine;
N-(2-{2-[2-Methoxy-4-(4-methyl-4-morpholin-4-yl-piperidin-1-yl)-phenylamino]-pyrrolo[2,1-f][1,2,4]triazin-7-yl}-phenyl)-N-methyl-methanesulfonamide;
N-(2-{2-[4-(4,4-Difluoro-piperidin-1-yl)-2-methoxy-phenylamino]-pyrrolo[2,1-f][1,2,4]triazin-7-yl}-phenyl)-N-methyl-methanesulfonamide;
[4-(4,4-Difluoro-piperidin-1-yl)-2-methoxy-phenyl]-[7-(2-methoxy-phenyl)-pyrrolo[2,1-f][1,2,4]triazin-2-yl]-amine;
N-[2-(2-{2-Methoxy-4-[4-(tetrahydro-pyran-4-yl)-piperazin-1-yl]-phenylamino}-pyrrolo[2,1-f][1,2,4]triazin-7-yl)-phenyl]-N-methyl-methanesulfonamide;
[7-(2-Methoxy-phenyl)-pyrrolo[2,1-f][1,2,4]triazin-2-yl]-{2-methoxy-4-[4-(tetrahydro-pyran-4-yl)-piperazin-1-yl]-phenyl}-amine;
[7-(2-Fluoro-phenyl)-pyrrolo[2,1-f][1,2,4]triazin-2-yl]-[2-methoxy-4-(4-morpholin-4-yl-piperidin-1-yl)-phenyl]-amine;
N-(2-{2-[4-(4,4-Difluoro-[1,4']bipiperidinyl-1'-yl)-2-methoxy-phenylamino]-pyrrolo[2,1-f][1,2,4]triazin-7-yl}-phenyl)-N-methyl-methanesulfonamide;
[4-(4,4-Difluoro-[1,4']bipiperidinyl-1'-yl)-2-methoxy-phenyl]-[7-(2-methoxy-phenyl)-pyrrolo[2,1-f][1,2,4]triazin-2-yl]-amine;
[7-(2,5-Dimethoxy-phenyl)-pyrrolo[2,1-f][1,2,4]triazin-2-yl]-[2-methoxy-4-(4-morpholin-4-yl-piperidin-1-yl)-phenyl]-amine;
(S)-1-(4-{4-[7-(2,5-Dimethoxy-phenyl)-pyrrolo[2,1-f][1,2,4]triazin-2-ylamino]-3-methoxy-phenyl}-piperazin-1-yl)-propan-2-ol;
N-[2-(2-{3-Fluoro-4-[4-((S)-2-hydroxy-propyl)-piperazin-1-yl]-2-methoxy-phenylamino}-pyrrolo[2,1-f][1,2,4]triazin-7-yl)-phenyl]-N-methyl-methanesulfonamide;
N-[2-(2-{5-Fluoro-4-[4-((S)-2-hydroxy-propyl)-piperazin-1-yl]-2-methoxy-phenylamino}-pyrrolo[2,1-f][1,2,4]triazin-7-yl)-phenyl]-N-methyl-methanesulfonamide;
(S)-1-(4-{2-Fluoro-5-methoxy-4-[7-(2-methoxy-phenyl)-pyrrolo[2,1-f][1,2,4]triazin-2-ylamino]-phenyl}-piperazin-1-yl)-propan-2-ol;
(S)-1-(4-{2,5-Difluoro-4-[7-(2-methoxy-phenyl)-pyrrolo[2,1-f][1,2,4]triazin-2-ylamino]-phenyl}-piperazin-1-yl)-propan-2-ol;
N-[2-(2-{2,5-Difluoro-4-[4-((S)-2-hydroxy-propyl)-piperazin-1-yl]-phenylamino}-pyrrolo[2,1-f][1,2,4]triazin-7-yl)-phenyl]-N-methyl-methanesulfonamide;
N-[2-(2-{5-Fluoro-4-[4-((S)-2-hydroxy-propyl)-piperazin-1-yl]-2-methylsulfanyl-phenylamino}-pyrrolo[2,1-f][1,2,4]triazin-7-yl)-phenyl]-N-methyl-methanesulfonamide;
(R)—N-[2-(2-{5-Fluoro-4-[4-((S)-2-hydroxy-propyl)-piperazin-1-yl]-2-methanesulfinyl-phenylamino}-pyrrolo[2,1-f][1,2,4]triazin-7-yl)-phenyl]-N-methyl-methanesulfonamide;
(S)—N-[2-(2-{5-Fluoro-4-[4-((S)-2-hydroxy-propyl)-piperazin-1-yl]-2-methanesulfinyl-phenylamino}-pyrrolo[2,1-f][1,2,4]triazin-7-yl)-phenyl]-N-methyl-methanesulfonamide;
7-methoxy-6-{[7-(2-methoxyphenyl)pyrrolo[2,1-f][1,2,4]triazin-2-yl]amino}-1'-methylspiro[chromene-2,4'-piperidin]-4(3H)-one;
N-Methyl-N-{2-[2-(5-methyl-2-oxo-2,3-dihydro-benzoxazol-6-ylamino)-pyrrolo[2,1-f][1,2,4]triazin-7-yl]-phenyl}-methanesulfonamide;
N-Methyl-N-{2-[2-(7-methyl-2-oxo-2,3-dihydro-benzoxazol-6-ylamino)-pyrrolo[2,1-f][1,2,4]triazin-7-yl]-phenyl}-methanesulfonamide;
7-(2-Methoxy-phenyl)-pyrrolo[2,1-f][1,2,4]triazine-2-carbonitrile;
7-(2-Methoxy-phenyl)-pyrrolo[2,1-f][1,2,4]triazine-2-carboxylic acid amide;
N-{2-[2-({1'-[(2S)-2-hydroxypropyl]-7-methoxy-3,4-dihydrospiro[chromene-2,4'-piperidin]-6-yl}amino)pyrrolo[2,1-f][1,2,4]triazin-7-yl]phenyl}-N-methyl-methanesulfonamide;
(4-{2-[4-(4-Methyl-piperazin-1-yl)-phenylamino]-pyrrolo[2,1-f][1,2,4]triazin-7-yl}-phenyl)-methanol;
(3-{2-[4-(4-Methyl-piperazin-1-yl)-phenylamino]-pyrrolo[2,1-f][1,2,4]triazin-7-yl}-phenyl)-methanol;
[7-(4-Methoxymethyl-phenyl)-pyrrolo[2,1-f][1,2,4]triazin-2-yl]-[4-(4-methyl-piperazin-1-yl)-phenyl]-amine;
7-[2-(methoxymethyl)phenyl]-N-[4-(4-methylpiperazin-1-yl)phenyl]pyrrolo[2,1-f][1,2,4]triazin-2-amine;
7-(2-Methoxy-phenyl)-2-(5-methyl-4H-[1,2,4]triazol-3-yl)-pyrrolo[2,1-f][1,2,4]triazine;
7-(2-Methoxy-phenyl)-2-(1H-tetrazol-5-yl)-pyrrolo[2,1-f][1,2,4]triazine;
[7-(3-Methoxymethyl-phenyl)-pyrrolo[2,1-f][1,2,4]triazin-2-yl]-[4-(4-methyl-piperazin-1-yl)-phenyl]-amine;
(2-{2-[4-(4-Methyl-piperazin-1-yl)-phenylamino]-pyrrolo[2,1-f][1,2,4]triazin-7-yl}-phenyl)-methanol;
7-(2-Methoxy-phenyl)-2-[5-(4-methyl-piperazin-1-yl)-1H-benzimidazol-2-yl]-pyrrolo[2,1-f][1,2,4]triazine;
7-[3-(1,1-Dioxido-1,2-thiazolidin-2-yl)phenyl]-N-[3-(1H-pyrazol-1-yl)phenyl]pyrrolo[2,1-f][1,2,4]triazin-2-amine;
7-[3-(1,1-Dioxido-1,2-thiazolidin-2-yl)phenyl]-N-[7-(morpholin-4-yl)-6,7,8,9-tetrahydro-5H-benzo[7]annulen-2-yl]pyrrolo[2,1-f][1,2,4]triazin-2-amine;
N-[3-({7-[3-(1,1-Dioxido-1,2-thiazolidin-2-yl)phenyl]pyrrolo[2,1-f][1,2,4]triazin-2-yl}amino)phenyl]acetamide;
7-[3-(1,1-Dioxido-1,2-thiazolidin-2-yl)phenyl]-N-[3-(4-methylpiperazin-1-yl)phenyl]pyrrolo[2,1-f][1,2,4]triazin-2-amine;
6-({7-[3-(1,1-Dioxido-1,2-thiazolidin-2-yl)phenyl]pyrrolo[2,1-f][1,2,4]triazin-2-yl}amino)-3,3-dimethyl-1,3-dihydro-2H-indol-2-one;
N-(1H-Benzimidazol-6-yl)-7-[3-(1,1-dioxido-1,2-thiazolidin-2-yl)phenyl]pyrrolo[2,1-f][1,2,4]triazin-2-amine;
2-{4-[4-({7-[3-(1,1-Dioxido-1,2-thiazolidin-2-yl)phenyl]pyrrolo[2,1-f][1,2,4]triazin-2-yl}amino)phenyl]piperidin-1-yl}acetamide;
[7-(6-Methoxy-pyridin-3-yl)-pyrrolo[2,1-f][1,2,4]triazin-2-yl]-(2-morpholin-4-ylmethyl-3H-benzimidazol-5-yl)-amine;
N-tert-Butyl-3-[2-(2-morpholin-4-ylmethyl-3H-benzimidazol-5-ylamino)-pyrrolo[2,1-f][1,2,4]triazin-7-yl]-benzenesulfonamide;
N-tert-Butyl-3-(2-{4-[1,1-difluoro-2-(4-methyl-piperazin-1-yl)-2-oxo-ethyl]-phenylamino}-pyrrolo[2,1-f][1,2,4]triazin-7-yl)-benzenesulfonamide;
2,2-Difluoro-2-{4-[7-(6-methoxy-pyridin-3-yl)-pyrrolo[2,1-f][1,2,4]triazin-2-ylamino]-phenyl}-1-(4-methyl-piperazin-1-yl)-ethanone;

N-Methyl-N-{2-[2-(2-morpholin-4-ylmethyl-3H-benzimidazol-5-ylamino)-pyrrolo[2,1-f][1,2,4]triazin-7-yl]-phenyl}-methanesulfonamide;
[7-(2-Methoxy-phenyl)-pyrrolo[2,1-f][1,2,4]triazin-2-yl]-(2-morpholin-4-ylmethyl-3H-benzimidazol-5-yl)-amine;
[3-(1,4-Dimethyl-piperazin-2-yl)-phenyl]-[7-(6-methoxy-pyridin-3-yl)-pyrrolo[2,1-f][1,2,4]triazin-2-yl]-amine;
N-tert-Butyl-3-(2-{2-[4-(2-hydroxy-ethyl)-piperazin-1-ylmethyl]-3H-benzimidazol-5-ylamino}-pyrrolo[2,1-f][1,2,4]triazin-7-yl)-benzenesulfonamide;
N-[2-(2-{2-[4-(2-Hydroxy-ethyl)-piperazin-1-ylmethyl]-3H-benzimidazol-5-ylamino}-pyrrolo[2,1-f][1,2,4]triazin-7-yl)-phenyl]-N-methyl-methanesulfonamide;
2-(4-{6-[7-(2-Methoxy-phenyl)-pyrrolo[2,1-f][1,2,4]triazin-2-ylamino]-1H-benzimidazol-2-ylmethyl}-piperazin-1-yl)-ethanol;
2-(4-{6-[7-(6-Methoxy-pyridin-3-yl)-pyrrolo[2,1-f][1,2,4]triazin-2-ylamino]-1H-benzimidazol-2-ylmethyl}-piperazin-1-yl)-ethanol;
N-tert-Butyl-3-{2-[2-(4-methyl-piperazin-1-ylmethyl)-3H-benzimidazol-5-ylamino]-pyrrolo[2,1-f][1,2,4]triazin-7-yl}-benzenesulfonamide;
N-Methyl-N-(2-{2-[2-(4-methyl-piperazin-1-ylmethyl)-3H-benzimidazol-5-ylamino]-pyrrolo[2,1-f][1,2,4]triazin-7-yl}-phenyl)-methanesulfonamide;
[7-(2-Methoxy-phenyl)-pyrrolo[2,1-f][1,2,4]triazin-2-yl]-[2-(4-methyl-piperazin-1-ylmethyl)-3H-benzimidazol-5-yl]-amine;
[7-(6-Methoxy-pyridin-3-yl)-pyrrolo[2,1-f][1,2,4]triazin-2-yl]-[2-(4-methyl-piperazin-1-ylmethyl)-3H-benzimidazol-5-yl]-amine;
N-tert-Butyl-3-[2-(4-piperazin-2-yl-phenylamino)-pyrrolo[2,1-f][1,2,4]triazin-7-yl]-benzenesulfonamide;
[7-(6-Methoxy-pyridin-3-yl)-pyrrolo[2,1-f][1,2,4]triazin-2-yl]-(4-piperazin-2-yl-phenyl)-amine;
[4-(1,4-Dimethyl-piperazin-2-yl)-phenyl]-[7-(6-methoxy-pyridin-3-yl)-pyrrolo[2,1-f][1,2,4]triazin-2-yl]-amine;
2-(4-{4-[7-(3-Methoxy-pyridin-2-yl)-pyrrolo[2,1-f][1,2,4]triazin-2-ylamino]-phenyl}-piperidin-1-yl)-acetamide;
2-(4-{3-Methoxy-4-[7-(3-methoxy-pyridin-2-yl)-pyrrolo[2,1-f][1,2,4]triazin-2-ylamino]-phenyl}-piperidin-1-yl)-acetamide;
2-(4-{4-[7-(2,2-Difluoro-benzo[1,3]dioxol-4-yl)-pyrrolo[2,1-f][1,2,4]triazin-2-ylamino]-3-methoxy-phenyl}-piperidin-1-yl)-acetamide;
[7-(2,2-Difluoro-benzo[1,3]dioxol-4-yl)-pyrrolo[2,1-f][1,2,4]triazin-2-yl]-[3-(4-methyl-piperazin-1-yl)-phenyl]-amine;
[7-(2,2-Difluoro-benzo[1,3]dioxol-4-yl)-pyrrolo[2,1-f][1,2,4]triazin-2-yl]-(7-morpholin-4-yl-6,7,8,9-tetrahydro-5H-benzocyclohepten-2-yl)-amine;
[7-(2,2-Difluoro-benzo[1,3]dioxol-4-yl)-pyrrolo[2,1-f][1,2,4]triazin-2-yl]-(2-morpholin-4-ylmethyl-1H-benzoimidazol-5-yl)-amine;
[7-(3-Methanesulfonyl-phenyl)-pyrrolo[2,1-f][1,2,4]triazin-2-yl]-(2-morpholin-4-ylmethyl-1H-benzimidazol-5-yl)-amine;
[7-(3-Methanesulfonyl-phenyl)-pyrrolo[2,1-f][1,2,4]triazin-2-yl]-[2-(4-methyl-piperazin-1-ylmethyl)-1H-benzimidazol-5-yl]-amine;
2-(4-{5-[7-(3-Methanesulfonyl-phenyl)-pyrrolo[2,1-f][1,2,4]triazin-2-ylamino]-1H-benzimidazol-2-ylmethyl}-piperazin-1-yl)-ethanol;
2-(4-{4-[7-(2,2-Difluoro-benzo[1,3]dioxol-4-yl)-pyrrolo[2,1-f][1,2,4]triazin-2-ylamino]-phenyl}-piperidin-1-yl)-acetamide;
[7-(4-Methanesulfonyl-phenyl)-pyrrolo[2,1-f][1,2,4]triazin-2-yl]-(2-morpholin-4-ylmethyl-1H-benzimidazol-5-yl)-amine;
[7-(4-Methanesulfonyl-phenyl)-pyrrolo[2,1-f][1,2,4]triazin-2-yl]-[2-(4-methyl-piperazin-1-ylmethyl)-1H-benzimidazol-5-yl]-amine;
2-(4-{5-[7-(4-Methanesulfonyl-phenyl)-pyrrolo[2,1-f][1,2,4]triazin-2-ylamino]-1H-benzimidazol-2-ylmethyl}-piperazin-1-yl)-ethanol;
2-(4-{4-[7-(3-tert-Butylsulfamoyl-phenyl)-pyrrolo[2,1-f][1,2,4]triazin-2-ylamino]-phenyl]-4-cyano-piperidin-1-yl)-acetamide;
2-(4-Cyano-4-{4-[7-(6-methoxy-pyridin-3-yl)-pyrrolo[2,1-f][1,2,4]triazin-2-ylamino]-phenyl}-piperidin-1-yl)-acetamide;
2-(4-Cyano-4-{4-[7-(3-methanesulfonyl-phenyl)-pyrrolo[2,1-f][1,2,4]triazin-2-ylamino]-phenyl}-piperidin-1-yl)-acetamide;
2-(4-Cyano-4-{4-[7-(4-methanesulfonyl-phenyl)-pyrrolo[2,1-f][1,2,4]triazin-2-ylamino]-phenyl}-piperidin-1-yl)-acetamide;
2-(4-Cyano-4-{4-[7-(2-methoxy-phenyl)-pyrrolo[2,1-f][1,2,4]triazin-2-ylamino]-phenyl}-piperidin-1-yl)-acetamide;
2-[4-Cyano-4-(4-{7-[2-(methanesulfonyl-methyl-amino)-phenyl]-pyrrolo[2,1-f][1,2,4]triazin-2-ylamino}-phenyl)-piperidin-1-yl]-acetamide;
N-tert-Butyl-3-{2-[3-(4-hydroxy-piperidin-4-yl)-phenylamino]-pyrrolo[2,1-f][1,2,4]triazin-7-yl}-benzenesulfonamide;
4-{3-[7-(6-Methoxy-pyridin-3-yl)-pyrrolo[2,1-f][1,2,4]triazin-2-ylamino]-phenyl}-piperidin-4-ol;
4-{3-[7-(3-Methanesulfonyl-phenyl)-pyrrolo[2,1-f][1,2,4]triazin-2-ylamino]-phenyl}-piperidin-4-ol;
2-[4-(4-{5-Chloro-7-[2-(methanesulfonyl-methyl-amino)-phenyl]-pyrrolo[2,1-f][1,2,4]triazin-2-ylamino}-phenyl)-piperidin-1-yl]-acetamide;
2-[4-(4-{5-Chloro-7-[2-(methanesulfonyl-methyl-amino)-phenyl]-pyrrolo[2,1-f][1,2,4]triazin-2-ylamino}-3-methoxy-phenyl)-piperidin-1-yl]-acetamide;
2-(4-{4-[5-Chloro-7-(6-methoxy-pyridin-3-yl)-pyrrolo[2,1-f][1,2,4]triazin-2-ylamino]-phenyl}-piperidin-1-yl)-acetamide;
5-({7-[2-(1,1-Dioxido-1,2-thiazolidin-2-yl)phenyl]pyrrolo[2,1-f][1,2,4]triazin-2-yl}amino)-3,3-dimethyl-1,3-dihydro-2H-indol-2-one;
(3-{2-[3-(4-Methyl-piperazin-1-yl)-phenylamino]-pyrrolo[2,1-f][1,2,4]triazin-7-yl}-phenyl)-methanol;
[7-(3-tert-Butoxymethyl-phenyl)-pyrrolo[2,1-f][1,2,4]triazin-2-yl]-[3-(4-methyl-piperazin-1-yl)-phenyl]-amine;
N-{3-[7-(3-tert-Butoxymethyl-phenyl)-pyrrolo[2,1-f][1,2,4]triazin-2-ylamino]-phenyl}-acetamide;
[7-(3-tert-Butoxymethyl-phenyl)-pyrrolo[2,1-f][1,2,4]triazin-2-yl]-(3-morpholin-4-yl-phenyl)-amine;
{3-[2-(3-Morpholin-4-yl-phenylamino)-pyrrolo[2,1-f][1,2,4]triazin-7-yl]-phenyl}-methanol;
(3H-Benzimidazol-5-yl)-(7-pyridin-2-yl-pyrrolo[2,1-f][1,2,4]triazin-2-yl)-amine;
3,3-Dimethyl-6-(7-pyridin-2-yl-pyrrolo[2,1-f][1,2,4]triazin-2-ylamino)-1,3-dihydro-indol-2-one;
2-{4-[4-(7-Pyrazin-2-yl-pyrrolo[2,1-f][1,2,4]triazin-2-ylamino)-phenyl]-piperidin-1-yl}-acetamide;

4-{3-[7-(2-Methoxy-phenyl)-pyrrolo[2,1-f][1,2,4]triazin-2-ylamino]-phenyl}-piperidin-4-ol;

[7-(6-Methoxy-pyridin-3-yl)-pyrrolo[2,1-f][1,2,4]triazin-2-yl]-(3-piperazin-2-yl-phenyl)-amine;

N-tert-Butyl-3-{2-[4-(1,4-dimethyl-piperazin-2-yl)-phenylamino]-pyrrolo[2,1-f][1,2,4]triazin-7-yl}-benzenesulfonamide;

2-{4-[4-(7-Pyrimidin-2-yl-pyrrolo[2,1-f][1,2,4]triazin-2-ylamino)-phenyl]-piperidin-1-yl}-acetamide;

[7-(4-Methanesulfonyl-phenyl)-pyrrolo[2,1-f][1,2,4]triazin-2-yl]-(4-piperidin-4-yl-phenyl)-amine;

2-{7-[7-(2-Methoxy-pyridin-3-yl)-pyrrolo[2,1-f][1,2,4]triazin-2-yl]-amino]-1,2,4,5-tetrahydro-benzo[d]azepin-3-yl)-N,N-dimethyl-acetamide;

2-{7-[7-(2-Methoxy-pyridin-3-yl)-pyrrolo[2,1-f][1,2,4]triazin-2-yl]-amino]-1,2,4,5-tetrahydro-benzo[d]azepin-3-yl)-N,N-dimethyl-acetamide;

2-[7-(7-Bromo-pyrrolo[2,1-f][1,2,4]triazin-2-yl]-amino)-1,2,4,5-tetrahydro-benzo[d]azepin-3-yl]-N,N-dimethyl-acetamide; and 2-{7-[7-(5-Methoxy-pyridin-3-yl)-pyrrolo[2,1-f][1,2,4]triazin-2-yl]-amino]-1,2,4,5-tetrahydro-benzo[d]azepin-3-yl)-N,N-dimethyl-acetamide;

and salt forms thereof.

7. A compound of formula (I)

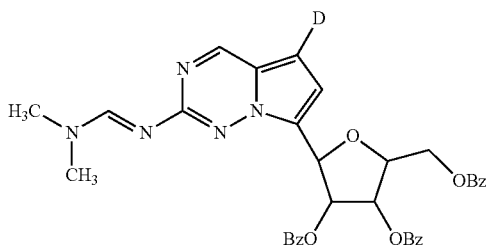

(a)

or a pharmaceutically acceptable salt form thereof, wherein $Q^1$ is $-L^1-A^1-G^1-X^1-Z^1$;

$Q^2$ is $-L^2-A^2-G^2-X^2-Z^2$, with the proviso that $Q^2$ is not

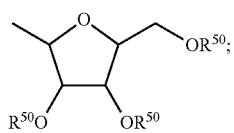

$Q^3$ is $-Z^3$;

$Q^4$ is $-Z^4$;

$L^1$ is $C_{1-6}$alkylene optionally substituted by 1-12 $R^9$, $C_{2-6}$alkenylene optionally substituted by 1-10 $R^9$, $C_{2-6}$alkynylene optionally substituted by 1-8 $R^9$, $C_{6-11}$arylene optionally substituted by 1-10 $R^9$, $C_{7-16}$arylalkylene optionally substituted by 1-18 $R^9$, $C_{3-11}$cycloalkylene optionally substituted by 1-20 $R^9$, $C_{4-17}$cycloalkylalkylene optionally substituted by 1-31 $R^9$, 3-15 membered heterocycloalkylene optionally substituted by 1-27 $R^9$, 4-21 membered heterocycloalkylalkylene optionally substituted by 1-39 $R^9$, 5-15 membered heteroarylene optionally substituted by 1-14 $R^9$, 6-21 membered heteroarylalkylene optionally substituted by 1-26 $R^9$, $-C_{0-3}$alkylC(=O)C$_{0-3}$alkyl-, $-C_{0-3}$alkylC(=O)OC$_{0-3}$alkyl-, $-C_{0-3}$alkylC(=O)NR$^4$C$_{0-3}$alkyl-, $-C_{0-3}$alkylC(=O)C(=O)C$_{0-3}$alkyl-, $-C_{0-3}$alkylC(=NR$^5$)C$_{0-3}$alkyl-, $-C_{0-3}$alkylC(=NR$^5$)NR$^4$C$_{0-3}$alkyl-, $-C_{0-3}$alkylC(=NOH)NR$^4$C$_{0-3}$alkyl-, $-C_{0-3}$alkylC(=NOR$^6$)C$_{0-3}$alkyl-, $-C_{0-3}$alkylC(=NNR$^2$R$^3$)C$_{0-3}$alkyl-, $-C_{0-3}$alkylC(=NNR$^4$C(=O)R$^1$)C$_{0-3}$ alkyl-, $-C_{0-3}$alkylC(=NNR$^4$C(=O)OR$^1$)C$_{0-3}$ alkyl-, $-C_{0-3}$alkylC(=S)NR$^4$C$_{0-3}$alkyl-, $-C_{0-3}$alkylNR$^4$C$_{0-3}$alkyl-, $-C_{0-3}$alkylNR$^4$NR$^4$C$_{0-3}$ alkyl-, $-C_{0-3}$alkylN=NC$_{0-3}$alkyl-, $-C_{0-3}$ alkylNR$^4$C(=O)C$_{0-3}$alkyl-, $-C_{0-3}$alkylNR$^4$C(=O)C(=O)C$_{0-3}$ alkyl-, $-C_{0-3}$alkylNR$^4$C(=O)OC$_{0-3}$alkyl-, $-C_{0-3}$ alkylNR$^4$C(=O)C(=O)OC$_{0-3}$ alkyl-, $-C_{0-3}$alkylNR$^4$C(=O)NR$^4$C$_{0-3}$alkyl-, $-C_{0-3}$alkylNR$^4$C(=O)NR$^4$C(=O)C$_{0-3}$alkyl-, $-C_{0-3}$alkylNR$^4$C(=O)NR$^4$C(=O)OC$_{0-3}$alkyl-, $-C_{0-3}$alkylNR$^4$C(=NR$^5$)NR$^4$C$_{0-3}$alkyl-, $-C_{0-3}$ alkylNR$^4$C(=O)C(=O)NR$^4$C$_{0-3}$alkyl-, $-C_{0-3}$ alkylNR$^4$C(=S)C$_{0-3}$alkyl-, $-C_{0-3}$alkylNR$^4$C(=S)OC$_{0-3}$alkyl-, $-C_{0-3}$ alkylNR$^4$C(=S)NR$^4$C$_{0-3}$alkyl-, $-C_{0-3}$alkylNR$^4$S(=O)$_2$OC$_{0-3}$alkyl-, $-C_{0-3}$ alkylNR$^4$S(=O)$_2$NR$^4$C$_{0-3}$ alkyl-, $-C_{0-3}$alkylOC$_{0-3}$ alkyl-, $-C_{0-3}$alkylOC(=O)C$_{0-3}$alkyl-, $-C_{0-3}$alkylOC(=O)NR$^4$C$_{0-3}$ alkyl-, $-C_{0-3}$alkylOC(=O)OC$_{0-3}$ alkyl-, $-C_{0-3}$ alkylOC(=NR$^5$)NR$^4$C$_{0-3}$alkyl-, $-C_{0-3}$alkylOS(=O)C$_{0-3}$alkyl-, $-C_{0-3}$alkylOS(=O)$_2$C$_{0-3}$ alkyl-, $-C_{0-3}$alkylOS(=O)$_2$OC$_{0-3}$alkyl-, $-C_{0-3}$ alkylOS(=O)$_2$NR$^4$C$_{0-3}$alkyl-, $-C_{0-3}$alkylS(=O)$_n$C$_{0-3}$ alkyl-, $-C_{0-3}$alkylS(=O)$_2$OC$_{0-3}$alkyl-, $-C_{0-3}$ alkylSO$_3$C$_{0-3}$alkyl-, $-C_{0-3}$alkylS(=O)$_2$ NR$^4$C$_{0-3}$ alkyl-, $-C_{0-3}$alkylS(=O)NR$^4$C$_{0-3}$alkyl-, or absent;

$A^1$ is $C_{1-6}$alkylene optionally substituted by 1-12 $R^a$, $C_{2-6}$alkenylene optionally substituted by 1-10 $R^a$, $C_{2-6}$alkynylene optionally substituted by 1-8 $R^a$, $C_{6-11}$arylene optionally substituted by 1-10 $R^a$, $C_{7-16}$arylalkylene optionally substituted by 1-18 $R^a$, $C_{3-11}$cycloalkylene optionally substituted by 1-20 $R^a$, $C_{4-17}$cycloalkylalkylene optionally substituted by 1-31 $R^a$, 3-15 membered heterocycloalkylene optionally substituted by 1-27 $R^a$, 4-21 membered heterocycloalkylalkylene optionally substituted by 1-39 $R^a$, 5-15 membered heteroarylene optionally substituted by 1-14 $R^a$, or 6-21 membered heteroarylalkylene optionally substituted by 1-26 $R^a$, wherein each $R^a$ is independently chosen from $C_{1-6}$alkyl optionally substituted by 1-13 $R^{19}$, $C_{2-6}$alkenyl optionally substituted by 1-11 $R^{19}$, $C_{2-6}$alkynyl optionally substituted by 1-9 $R^{19}$, $C_{6-11}$aryl optionally substituted by 1-11 $R^{19}$, $C_{7-16}$arylalkyl optionally substituted by 1-19 $R^{19}$, $C_{3-11}$cycloalkyl optionally substituted by 1-21 $R^{19}$, $C_{4-17}$cycloalkylalkyl optionally substituted by 1-32 $R^{19}$, 3-15 membered heterocycloalkyl optionally substituted by 1-28 $R^{19}$, 4-21 membered heterocycloalkylalkyl optionally substituted by 1-40 $R^{19}$, 5-15 membered heteroaryl optionally substituted by 1-15 $R^{19}$, 6-21 membered heteroarylalkyl optionally substituted by 1-27 $R^{19}$, halogen, $-CN$, $-C(=O)R^{10}$, $-C(=O)OR^{10}$, $-C(=O)NR^{12}R^{13}$, $-C(=O)C(=O)R^{10}$, $-C(=NR^{15})R^{10}$, $-C(=NR^{15})NR^{12}R^{13}$, $-C(=NOH)NR^{12}R^{13}$, $-C(=NOR^{16})R^{10}$, $-C(=NNR^{12}R^{13})R^{10}$, $-C(=NNR^{14}C(=O)R^{11})R^{10}$, $-C(=NNR^{14}C(=O)OR^{11})R^{10}$, $-C(=S)NR^{12}R^{13}$, $-NC$, $-NO_2$, $-NR^{12}R^{13}$, $-NR^{14}NR^{12}R^{13}$, $-N=NR^{14}$, $=NR^{10}$, =NOR$^{10}$, —NR$^{14}$OR$^{16}$, —NR$^{14}$C(=O)R$^{10}$, —NR$^{14}$C(=O)C(=O)R$^{10}$, —NR$^{14}$C(=O)OR$^{11}$, —NR$^{14}$C(=O)C(=O)OR$^{11}$, —NR$^{14}$C(=O)NR$^{12}$R$^{13}$, —NR$^{14}$C(=O)NR$^{14}$C(=O)R$^{10}$, —NR$^{14}$C(=O)NR$^{14}$C(=O)OR$^{10}$, —NR$^{14}$C(=NR$^{15}$)NR$^{12}$R$^{13}$, —NR$^{14}$C(=O)C(=O)NR$^{12}$R$^{13}$, —NR$^{14}$C(=S)R$^{10}$, —NR$^{14}$C(=S)OR$^{10}$, —NR$^{14}$C(=S)NR$^{12}$R$^{13}$, —NR$^{14}$S(=O)$_2$R$^{11}$, —NR$^{14}$S(=O)$_2$NR$^{12}$R$^{13}$, —NR$^{14}$P(=O)R$^{18}$R$^{18}$, —NR$^{14}$S(=O)(NR$^{12}$R$^{13}$)(NR$^{12}$R$^{13}$), —NR$^{14}$P(=O)(OR$^{10}$)(OR$^{10}$), —NR$^{14}$P(=O)(SR$^{10}$)(SR$^{10}$), —OR$^{10}$, =O, —OCN, —OC(=O)R$^{10}$, —OC(=O)NR$^{12}$R$^{13}$, —OC(=O)OR$^{10}$, —OC(=NR$^{15}$)NR$^{12}$R$^{13}$, —OS(=O)R$^{10}$, —OS(=O)$_2$R$^{10}$, —OS(=O)$_2$OR$^{10}$, —OS(=O)$_2$NR$^{12}$R$^{13}$, —OP(=O)R$^{18}$R$^{18}$, —OP(=O)(NR$^{12}$R$^{13}$)(NR$^{12}$,R$^{13}$), —OP(=O)(OR$^{10}$)(OR$^{10}$), —OP(=O)(SR$^{10}$)(SR$^{10}$), —SCN, =S, —S(=O)$_n$R$^{10}$, —S(=O)$_2$OR$^{10}$, —SO$_3$R$^{17}$, —S(=O)$_2$NR$^{12}$R$^{13}$, —S(=O)NR$^{12}$R$^{13}$, —SP(=O)R$^{18}$R$^{18}$, —SP(=O)(NR$^{12}$R$^{13}$)(NR$^{12}$R$^{13}$), —SP(=O)(OR$^{10}$)(OR$^{10}$), —SP(=O)(SR$^{10}$)(SR$^{10}$), —P(=O)R$^{18}$R$^{18}$, —P(=O)(NR$^{12}$R$^{13}$)(NR$^{12}$R$^{13}$), —P(=O)(OR$^{10}$)(OR$^{10}$), and —P(=O)(SR$^{10}$)(SR$^{10}$);

G$^1$ is C$_{1-6}$alkylene optionally substituted by 1-12 R$^{29}$, C$_{2-6}$alkenylene optionally substituted by 1-10 R$^{29}$, C$_{2-6}$alkynylene optionally substituted by 1-8 R$^{29}$, C$_{6-11}$arylene optionally substituted by 1-10 R$^{29}$, C$_{7-16}$arylalkylene optionally substituted by 1-18 R$^{29}$, C$_{3-11}$cycloalkylene optionally substituted by 1-20 R$^{29}$, C$_{4-17}$cycloalkylalkylene optionally substituted by 1-31 R$^{29}$, 3-15 membered heterocycloalkylene optionally substituted by 1-27 R$^{29}$, 4-21 membered heterocycloalkylalkylene optionally substituted by 1-39 R$^{29}$, 5-15 membered heteroarylene optionally substituted by 1-14 R$^{29}$, 6-21 membered heteroarylalkylene optionally substituted by 1-26 R$^{29}$, —C$_{0-3}$alkylC(=O)C$_{0-3}$alkyl-, —C$_{0-3}$alkylC(=O)OC$_{0-3}$alkyl-, —C$_{0-3}$alkylC(=O)NR$^{24}$C$_{0-3}$alkyl-, —C$_{0-3}$alkylC(=O)C(=O)C$_{0-3}$alkyl-, —C$_{0-3}$alkylC(=NR$^{25}$)C$_{0-3}$alkyl-, —C$_{0-3}$alkylC(=NR$^{25}$)NR$^{24}$C$_{0-3}$alkyl-, —C$_{0-3}$alkylC(=NOH)NR$^{24}$C$_{0-3}$alkyl-, —C$_{0-3}$alkylC(=NOR$^{26}$)C$_{0-3}$alkyl-, —C$_{0-3}$alkylC(=NNR$^{22}$R$^{23}$)C$_{0-3}$alkyl-, —C$_{0-3}$alkylC(=NNR$^{24}$C(=O)R$^{21}$)C$_{0-3}$alkyl-, —C$_{0-3}$alkylC(=NNR$^{24}$C(=O)OR$^{21}$)C$_{0-3}$alkyl-, —C$_{0-3}$alkylC(=S)NR$^{24}$C$_{0-3}$alkyl-, —C$_{0-3}$alkylNR$^{24}$C$_{0-3}$alkyl-, —C$_{0-3}$alkylNR$^{24}$NR$^{24}$C$_{0-3}$alkyl-, —C$_{0-3}$alkylN=NC$_{0-3}$alkyl-, —C$_{0-3}$alkylNR$^{24}$C(=O)C$_{0-3}$alkyl-, —C$_{0-3}$alkylNR$^{24}$C(=O)C(=O)C$_{0-3}$alkyl-, —C$_{0-3}$alkylNR$^{24}$C(=O)OC$_{0-3}$alkyl-, —C$_{0-3}$alkylNR$^{24}$C(=O)C(=O)OC$_{0-3}$alkyl-, —C$_{0-3}$alkylNR$^{24}$C(=O)NR$^{24}$C$_{0-3}$alkyl-, —C$_{0-3}$alkylNR$^{24}$C(=O)NR$^{24}$C(=O)C$_{0-3}$alkyl-, —C$_{0-3}$alkylNR$^{24}$C(=O)NR$^{24}$C(=O)OC$_{0-3}$alkyl-, —C$_{0-3}$alkylNR$^{24}$C(=NR$^{25}$)NR$^{24}$C$_{0-3}$alkyl-, —C$_{0-3}$alkylNR$^{24}$C(=O)C(=O)NR$^{24}$C$_{0-3}$alkyl-, —C$_{0-3}$alkylNR$^{24}$C(=S)C$_{0-3}$alkyl-, —C$_{0-3}$alkylNR$^{24}$C(=S)OC$_{0-3}$alkyl-, —C$_{0-3}$alkylNR$^{24}$C(=S)NR$^{24}$C$_{0-3}$alkyl-, —C$_{0-3}$alkylNR$^{24}$S(=O)$_2$C$_{0-3}$alkyl-, —C$_{0-3}$alkylNR$^{24}$S(=O)$_2$NR$^{24}$C$_{0-3}$alkyl-, —C$_{0-3}$alkylOC$_{0-3}$alkyl-, —C$_{0-3}$alkylOC(=O)C$_{0-3}$alkyl-, —C$_{0-3}$alkylOC(=O)NR$^{24}$C$_{0-3}$alkyl-, —C$_{0-3}$alkylOC(=O)OC$_{0-3}$alkyl-, —C$_{0-3}$alkylOC(=NR$^{25}$)NR$^{24}$C$_{0-3}$alkyl-, —C$_{0-3}$alkylOS(=O)C$_{0-3}$alkyl-, —C$_{0-3}$alkylOS(=O)$_2$C$_{0-3}$alkyl-, —C$_{0-3}$alkylOS(=O)$_2$OC$_{0-3}$alkyl-, —C$_{0-3}$alkylOS(=O)$_2$NR$^{24}$C$_{0-3}$alkyl-, —C$_{0-3}$alkylS(=O)$_n$C$_{0-3}$alkyl-, —C$_{0-3}$alkylS(=O)$_2$OC$_{0-3}$alkyl-, —C$_{0-3}$alkylSO$_3$C$_{0-3}$alkyl-, —C$_{0-3}$alkylS(=O)$_2$NR$^{24}$C$_{0-3}$alkyl-, —C$_{0-3}$alkylS(=O)NR$^{24}$C$_{0-3}$alkyl-, —C$_{0-3}$alkylS(=O)NR$^{24}$C$_{0-3}$alkyl-, or absent;

X$^1$ is C$_{1-6}$alkylene optionally substituted by 1-12 R$^{39}$, C$_{2-6}$alkenylene optionally substituted by 1-10 R$^{39}$, C$_{2-6}$alkynylene optionally substituted by 1-8 R$^{39}$, C$_{6-11}$arylene optionally substituted by 1-10 R$^{39}$, C$_{7-16}$arylalkylene optionally substituted by 1-18 R$^{39}$, C$_{3-11}$cycloalkylene optionally substituted by 1-20 R$^{39}$, C$_{4-17}$cycloalkylalkylene optionally substituted by 1-31 R$^{39}$, 3-15 membered heterocycloalkylene optionally substituted by 1-27 R$^{39}$, 4-21 membered heterocycloalkylalkylene optionally substituted by 1-39 R$^{39}$, 5-15 membered heteroarylene optionally substituted by 1-14 R$^{39}$, 6-21 membered heteroarylalkylene optionally substituted by 1-26 R$^{39}$, —C$_{0-3}$alkylC(=O)C$_{0-3}$alkyl-, —C$_{0-3}$alkylC(=O)OC$_{0-3}$alkyl-, —C$_{0-3}$alkylC(=O)NR$^{34}$C$_{0-3}$alkyl-, —C$_{0-3}$alkylC(=O)C(=O)C$_{0-3}$alkyl-, —C$_{0-3}$alkylC(=NR$^{35}$)C$_{0-3}$alkyl-, —C$_{0-3}$alkylC(=NR$^{35}$)NR$^{34}$C$_{0-3}$alkyl-, —C$_{0-3}$alkylC(=NOH)NR$^{34}$C$_{0-3}$alkyl-, alkylC(=NOR$^{36}$)C$_{0-3}$alkyl-, —C$_{0-3}$alkylC(=NNR$^{32}$R$^{33}$)C$_{0-3}$alkyl-, —C$_{0-3}$alkylC(=NNR$^{34}$C(=O)R$^{31}$)C$_{0-3}$alkyl-, —C$_{0-3}$alkylC(=NNR$^{34}$C(=O)OR$^{31}$)C$_{0-3}$alkyl-, —C$_{0-3}$alkylC(=S)NR$^{34}$C$_{0-3}$alkyl-, —C$_{0-3}$alkylNR$^{34}$C$_{0-3}$alkyl-, —C$_{0-3}$alkylNR$^{34}$NR$^{34}$C$_{0-3}$alkyl-, —C$_{0-3}$alkylN=NC$_{0-3}$alkyl-, —C$_{0-3}$alkylNR$^{34}$C(=O)C$_{0-3}$alkyl-, —C$_{0-3}$alkylNR$^{34}$C(=O)C(=O)C$_{0-3}$alkyl-, —C$_{0-3}$alkylNR$^{34}$C(=O)OC$_{0-3}$alkyl-, —C$_{0-3}$alkylNR$^{34}$C(=O)C(=O)OC$_{0-3}$alkyl-, —C$_{0-3}$alkylNR$^{34}$C(=O)NR$^{34}$C$_{0-3}$alkyl-, —C$_{0-3}$alkylNR$^{34}$C(=O)NR$^{34}$C(=O)C$_{0-3}$alkyl-, —C$_{0-3}$alkylNR$^{34}$C(=O)NR$^{34}$C(=O)OC$_{0-3}$alkyl-, —C$_{0-3}$alkylNR$^{34}$C(=NR$^{35}$)NR$^{34}$C$_{0-3}$alkyl-, —C$_{0-3}$alkylNR$^{34}$C(=O)C(=O)NR$^{34}$C$_{0-3}$alkyl-, —C$_{0-3}$alkylNR$^{34}$C(=S)C$_{0-3}$alkyl-, —C$_{0-3}$alkylNR$^{34}$C(=S)OC$_{0-3}$alkyl-, —C$_{0-3}$alkylNR$^{34}$C(=S)NR$^{34}$C$_{0-3}$alkyl-, —C$_{0-3}$alkylNR$^{34}$S(=O)$_2$C$_{0-3}$alkyl-, —C$_{0-3}$alkylNR$^{34}$S(=O)$_2$NR$^{34}$C$_{0-3}$alkyl-, —C$_{0-3}$alkylOC$_{0-3}$alkyl-, —C$_{0-3}$alkylOC(=O)C$_{0-3}$alkyl-, —C$_{0-3}$alkylOC(=O)NR$^{34}$C$_{0-3}$alkyl-, —C$_{0-3}$alkylOC(=O)OC$_{0-3}$alkyl-, —C$_{0-3}$alkylOC(=NR$^{35}$)NR$^{34}$C$_{0-3}$alkyl-, —C$_{0-3}$alkylOS(=O)C$_{0-3}$alkyl-, —C$_{0-3}$alkylOS(=O)$_2$C$_{0-3}$alkyl-, —C$_{0-3}$alkylOS(=O)$_2$OC$_{0-3}$alkyl-, —C$_{0-3}$alkylOS(=O)$_2$NR$^{34}$C$_{0-3}$alkyl-, —C$_{0-3}$alkylS(=O)$_n$C$_{0-3}$alkyl-, —C$_{0-3}$alkylS(=O)$_2$OC$_{0-3}$alkyl-, —C$_{0-3}$alkylSO$_3$C$_{0-3}$alkyl-, —C$_{0-3}$alkylS(=O)$_2$NR$^{34}$C$_{0-3}$alkyl-, —C$_{0-3}$alkylS(=O)NR$^{34}$C$_{0-3}$alkyl-, or absent;

Z$^1$ is H, C$_{1-6}$alkyl optionally substituted by 1-13 R$^{49}$, C$_{2-6}$alkenyl optionally substituted by 1-11 R$^{49}$, C$_{2-6}$alkynyl optionally substituted by 1-9 R$^{49}$, C$_{6-11}$aryl optionally substituted by 1-11 R$^{49}$, C$_{7-16}$arylalkyl optionally substituted by 1-19 R$^{49}$, C$_{3-11}$cycloalkyl optionally substituted by 1-21 R$^{49}$, C$_{4-17}$cycloalkylalkyl optionally substituted by 1-32 R$^{49}$, 3-15 membered heterocycloalkyl optionally substituted by 1-28 R$^{49}$, 4-21 membered heterocycloalkylalkyl optionally substituted by 1-40 R$^{49}$, 5-15 membered heteroaryl optionally substituted by 1-15 R$^{49}$, 6-21 membered heteroarylalkyl optionally substituted by 1-27 R$^{49}$, halogen, —CN, —C(=O)R$^{100}$, —C(=O)OR$^{100}$, —C(=O)NR$^{102}$R$^{103}$, —C(=O)C(=O)R$^{100}$, —C(=NR$^{105}$)R$^{100}$, —C(NR$^{105}$)

$NR^{102}R^{103}$, —C(=NOH)$NR^{102}R^{103}$, —C(=NOR$^{106}$)R$^{100}$, —C(=NN$R^{102}R^{103}$)R$^{100}$, —C(NNR$^{104}$C(=O)R$^{101}$)R$^{100}$, —C(=NNR$^{104}$C(=O)OR$^{101}$)R$^{100}$, —C(=S)NR$^{102}R^{103}$, —NC, —NO$_2$, —NR$^{102}R^{103}$, —NR$^{104}$NR$^{102}R^{103}$, —N=NR$^{104}$, =NR$^{100}$, =NOR$^{100}$, —NR$^{104}$OR$^{106}$, —NR$^{104}$C(=O)R$^{100}$, —NR$^{104}$C(=O)C(=O)R$^{100}$, —NR$^{104}$C(=O)OR$^{101}$, —NR$^{104}$C(=O)C(=O)OR$^{101}$, —NR$^{104}$C(=O)NR$^{102}R^{103}$, —NR$^{104}$C(=O)NR$^{104}$C(=O)R$^{100}$, —NR$^{104}$C(=O)NR$^{104}$C(=O)OR$^{100}$, —NR$^{104}$C(=NR$^{105}$)NR$^{102}R^{103}$, —NR$^{104}$C(=O)C(=O)NR$^{102}R^{103}$, —NR$^{104}$C(=S)R$^{100}$, —NR$^{104}$C(=S)OR$^{100}$, —NR$^{104}$C(=S)NR$^{102}R^{103}$, —NR$^{104}$S(=O)$_2$R$^{101}$, —NR$^{104}$S(=O)$_2$NR$^{102}R^{103}$, —NR$^{104}$P(=O)R$^{108}R^{108}$, NR$^{104}$P(=O)(NR$^{102}R^{103}$)(NR$^{102}R^{103}$), NR$^{104}$P(=O)(OR$^{100}$)(OR$^{100}$), —NR$^{104}$P(=O)(SR$^{100}$)(SR$^{100}$), —OR$^{100}$, =O, —OCN, —OC(=O)R$^{100}$, —OC(=O)NR$^{102}R^{103}$—OC(=O)OR$^{100}$, —OC(=NR$^{105}$)NR$^{102}R^{103}$, OS(=O)R$^{100}$, —OS(=O)$_2$R$^{100}$, —OS(=O)$_n$OR$^{100}$, —OS(=O)$_2$NR$^{102}R^{103}$, —OP(=O)R$^{108}R^{108}$, OP(=OP(=O)(NR$^{102}R^{103}$)(NR$^{102}R^{103}$), —OP(=O)(OR$^{100}$)(OR$^{100}$), —OP(=O)(SR$^{100}$)(SR$^{100}$), —SCN, =S, —S(=O)$_n$R$^{100}$, —S(=O)$_2$OR$^{100}$, —SO$_3$R$^{107}$, —S(=O)$_2$NR$^{102}R^{103}$, —S(=O)NR$^{102}R^{103}$, —SP(=O)R$^{108}R^{108}$, —SP(=O)(NR$^{102}R^{103}$)(NR$^{102}R^{103}$), —SP(=O)(OR$^{100}$)(OR$^{100}$), —SP(=O)(SR$^{100}$)(SR$^{100}$), —P(=O)R$^{108}R^{108}$, —P(=O)(NR$^{102}R^{103}$)(NR$^{102}R^{103}$), —P(=O)(OR$^{100}$)(OR$^{100}$), or —P(=O)(SR$^{100}$)(SR$^{100}$);

$L^2$ is present or absent, and if present is chosen from —C$_{0-3}$alkylC(=O)C$_{0-3}$alkyl-, —C$_{0-3}$alkylC(=O)OC$_{0-3}$alkyl-, —C$_{0-3}$alkylC(=O)NR$^{44}$C$_{0-3}$alkyl-, —C$_{0-3}$alkylC(=O)C(=O)C$_{0-3}$alkyl-, —C$_{0-3}$alkylC(=NR$^{45}$)C$_{0-3}$alkyl-, —C$_{0-3}$alkylC(=NR$^{45}$)NR$^{44}$C$_{0-3}$ alkyl-, —C$_{0-3}$alkylC(=NOH)NR$^{44}$C$_{0-3}$ alkyl-, —C$_{0-3}$alkylC(=NOR$^{46}$)C$_{0-3}$alkyl-, —C$_{0-3}$alkylC(=NNR$^{42}R^{43}$)C$_{0-3}$alkyl-, —C$_{0-3}$alkylC(=NNR$^{44}$C(=O)R$^{41}$)C$_{0-3}$alkyl-, —C$_{0-3}$alkylC(=NNR$^{44}$C(=O)OR$^{41}$)C$_{0-3}$alkyl-, —C$_{0-3}$alkylC(=S)NR$^{44}$C$_{0-3}$ alkyl-, —C$_{0-3}$ alkylNR$^{44}$C$_{0-3}$alkyl-, —C$_{0-3}$ alkylNR$^{44}$NR$^{44}$C$_{0-3}$ alkyl-, —C$_{0-3}$ alkylN=NC$_{0-3}$ alkyl-, —C$_{0-3}$ alkylNR$^{44}$C(=O)C$_{0-3}$ alkyl-, —C$_{0-3}$ alkylNR$^{44}$C(=O)C(=O)C$_{0-3}$ alkyl-, —C$_{0-3}$ alkylNR$^{44}$C(=O)OC$_{0-3}$ alkyl-, —C$_{0-3}$ alkylNR$^{44}$C(=O)C(=O)OC$_{0-3}$alkyl-, —C$_{0-3}$ alkylNR$^{44}$C(=O)NR$^{44}$C$_{0-3}$alkyl-, —C$_{0-3}$ alkylNR$^{44}$C(=O)NR$^{44}$C(=O)C$_{0-3}$alkyl-, —C$_{0-3}$ alkylNR$^{44}$C(=O)NR$^{44}$C(=O)OC$_{0-3}$alkyl-, —C$_{0-3}$ alkylNR$^{44}$C(=NR$^{45}$)NR$^{44}$C$_{0-3}$alkyl-, —C$_{0-3}$ alkylNR$^{44}$C(=O)C(=O)NR$^{44}$C$_{0-3}$alkyl-, —C$_{0-3}$ lkylNR$^{44}$C(=S)C$_{0-3}$alkyl-, —C$_{0-3}$alkylNR$^{44}$C(=S)OC$_{0-3}$alkyl-, —C$_{0-3}$ alkylNR$^{44}$C(=S)NR$^{44}$C$_{0-3}$ alkyl-, —C$_{0-3}$ alkylNR$^{44}$S(=O)$_2$C$_{0-3}$alkyl-, —C$_{0-3}$ alkylNR$^{44}$S(=O)$_2$NR$^{44}$C$_{0-3}$alkyl-, —C$_{0-3}$ alkylOC$_{0-3}$ alkyl-, —C$_{0-3}$alkylOC(=O)C$_{0-3}$alkyl-, —C$_{0-3}$ alkylOC(=O)NR$^{44}$C$_{0-3}$ alkyl-, —C$_{0-3}$alkylOC(=O)OC$_{0-3}$ alkyl-, —C$_{0-3}$alkylOC(=NR$^{45}$)NR$^{44}$C$_{0-3}$ alkyl-, —C$_{0-3}$alkylOS(=O)C$_{0-3}$alkyl-, —C$_{0-3}$ alkylOS(=O)$_2$C$_{0-3}$alkyl-, —C$_{0-3}$alkylOS(=O)$_2$OC$_{0-3}$ alkyl-, —C$_{0-3}$alkylOS(=O)$_2$NR$^{44}$C$_{0-3}$ alkyl-, —C$_{0-3}$ alkylS(=O)$_n$C$_{0-3}$alkyl-, —C$_{0-3}$alkylS(=O)$_2$OC$_{0-3}$ alkyl-, —C$_{0-3}$alkylSO$_3$C$_{0-3}$alkyl-, —C$_{0-3}$ alkylS(=O)$_2$ NR$^{44}$C$_{0-3}$alkyl-, and —C$_{0-3}$ alkylS(=O)NR$^{44}$C$_{0-3}$ alkyl-;

$A^2$ is present or absent, and if present is chosen from C$_{1-6}$alkylene optionally substituted by 1-12 R$^b$, C$_{2-6}$alkenylene optionally substituted by 1-10 R$^b$, C$_{2-6}$alkynylene optionally substituted by 1-8 R$^b$, C$_{6-11}$ arylene optionally substituted by 1-10 R$^b$, C$_{7-16}$arylalkylene optionally substituted by 1-18 R$^b$, C$_{3-11}$cycloalkylene optionally substituted by 1-20 R$^b$, C$_{4-17}$cycloalkylalkylene optionally substituted by 1-31 R$^b$, 3-15 membered heterocycloalkylene optionally substituted by 1-27 R$^b$, 4-21 membered heterocycloalkylalkylene optionally substituted by 1-39 R$^b$, 5-15 membered heteroarylene optionally substituted by 1-14 R$^b$, or 6-21 membered heteroarylalkylene optionally substituted by 1-26 R$^b$;

wherein each R$^b$ is independently chosen from C$_{1-6}$alkyl optionally substituted by 1-13 R$^{59}$, C$_{2-6}$alkenyl optionally substituted by 1-11 R$^{59}$, C$_{2-6}$alkynyl optionally substituted by 1-9 R$^{59}$, C$_{6-11}$aryl optionally substituted by 1-11 R$^{59}$, C$_{7-16}$arylalkyl optionally substituted by 1-19 R$^{59}$, C$_{3-11}$cycloalkyl optionally substituted by 1-21 R$^{59}$, C$_{4-17}$cycloalkylalkyl optionally substituted by 1-32 R$^{59}$, 3-15 membered heterocycloalkyl optionally substituted by 1-28 R$^{59}$, 4-21 membered heterocycloalkylalkyl optionally substituted by 1-40 R$^{59}$, 5-15 membered heteroaryl optionally substituted by 1-15 R$^{59}$, 6-21 membered heteroarylalkyl optionally substituted by 1-27 R$^{59}$, halogen, —CN, —C(=O)R$^{50}$, —C(=O)OR$^{50}$, —C(=O)NR$^{52}R^{53}$, —C(=O)C(=O)R$^{50}$, —C(=NR$^{55}$)R$^{50}$, —C(=NR$^{55}$)NR$^{52}R^{53}$, —C(=NOH)NR$^{52}R^{53}$, —C(=NOR$^{56}$)R$^{50}$, —C(=NNR$^{52}R^{53}$)R$^{50}$, —C(=NNR$^{54}$C(=O)R$^{51}$)R$^{50}$, —C(=NNR$^{54}$C(=O)OR$^{51}$)R$^{50}$, —C(=S)NR$^{52}R^{53}$, —NC, —NO$_2$, —NR$^{52}R^{53}$, —NR$^{54}$NR$^{52}R^{53}$, —N=NR$^{54}$, =NR$^{50}$, =NOR$^{50}$, —NR$^{54}$OR$^{56}$, —NR$^{54}$C(=O)R$^{50}$, —NR$^{54}$C(=O)C(=O)R$^{50}$, —NR$^{54}$C(=O)OR$^{51}$, —NR$^{54}$C(=O)C(=O)OR$^{51}$, —NR$^{54}$C(=O)NR$^{52}R^{53}$, —NR$^{54}$C(=O)NR$^{54}$C(=O)R$^{50}$, —NR$^{54}$C(=O)NR$^{54}$C(=O)OR$^{50}$, —NR$^{54}$C(=NR$^{55}$)NR$^{52}R^{53}$, —NR$^{54}$C(=O)C(=O)NR$^{52}R^{53}$, —NR$^{54}$C(=S)R$^{50}$, —NR$^{54}$C(=S)OR$^{50}$, —NR$^{54}$C(=S)NR$^{52}R^{53}$, —NR$^{54}$S(=O)$_2$R$^{51}$, —NR$^{54}$S(=O)$_2$NR$^{52}R^{53}$, —NR$^{54}$P(=O)R$^{58}R^{58}$, —NR$^{54}$P(=O)(NR$^{52}R^{53}$)(NR$^{52}R^{53}$), —NR$^{54}$P(=O)(OR$^{50}$)(OR$^{50}$), —NR$^{54}$P(=O)(SR$^{50}$)(SR$^{50}$), —OR$^{50}$, =O, —OCN, —OC(=O)R$^{50}$, —OC(=O)NR$^{52}R^{53}$, —OC(=O)OR$^{50}$, —OC(=NR$^{55}$)NR$^{52}R^{53}$, —OS(=O)R$^{50}$, —OS(=O)$_2$R$^{50}$, —OS(=O)$_2$OR$^{50}$, —OS(=O)$_2$NR$^{52}R^{53}$, —OP(=O)R$^{58}R^{58}$, —OP(=O)(NR$^{52}R^{53}$)(NR$^{52}R^{53}$), —OP(=O)(OR$^{50}$)(OR$^{50}$), —OP(=O)(SR$^{50}$)(SR$^{50}$), —SCN, =S, —S(=O)$_n$ R$^{50}$, —S(=O)$_2$OR$^{50}$, —SO$_3$R$^{57}$, —S(=O)$_2$ NR$^{52}R^{53}$, —S(=O)NR$^{52}R^{53}$, —SP(=O)R$^{58}R^{58}$, —SP(=O)(NR$^{52}R^{53}$)(NR$^{52}R^{53}$), —SP(=O)(OR$^{50}$)(OR$^{50}$), —SP(=O)(SR$^{50}$)(SR$^{50}$), —P(=O)R$^{58}R^{58}$, —P(=O)(NR$^{52}R^{53}$)(NR$^{52}R^{53}$), —P(=O)(OR$^{50}$)(OR$^{50}$), and —P(=O)(SR$^{50}$)(SR$^{50}$);

$G^2$ is present or absent, and if present is chosen from C$_{1-6}$alkylene optionally substituted by 1-12 R$^{69}$, C$_{2-6}$alkenylene optionally substituted by 1-10 R$^{69}$, C$_{2-6}$alkynylene optionally substituted by 1-8 R$^{69}$, C$_{6-11}$arylene optionally substituted by 1-10 R$^{69}$, C$_{7-16}$arylalkylene optionally substituted by 1-18 R$^{69}$, $C_{3-11}$cycloalkylene optionally substituted by 1-20 $R^{69}$, $C_{4-17}$cycloalkylalkylene optionally substituted by 1-31 $R^{69}$, 3-15 membered heterocycloalkylene optionally substituted by 1-27 $R^{69}$, 4-21 membered heterocycloalkylalkylene optionally substituted by 1-39 $R^{69}$, 5-15 membered heteroarylene optionally substituted by 1-14 $R^{69}$, 6-21 membered heteroarylalkylene optionally substituted by 1-26 $R^{69}$, —$C_{0-3}$alkylC(=O)$C_{0-3}$alkyl-, —$C_{0-3}$alkylC(=O)O$C_{0-3}$alkyl-, —$C_{0-3}$alkylC(=O)NR$^{64}$$C_{0-3}$alkyl-, —$C_{0-3}$alkylC(=O)C(=O)$C_{0-3}$alkyl-, —$C_{0-3}$alkylC(=NR$^{65}$)$C_{0-3}$alkyl-, —$C_{0-3}$alkylC(=NR$^{65}$)NR$^{64}$$C_{0-3}$ alkyl-, —$C_{0-3}$alkylC(=NOH)NR$^{64}$$C_{0-3}$alkyl-, —$C_{0-3}$alkylC(=NOR$^{66}$)$C_{0-3}$alkyl-, —$C_{0-3}$alkylC(=NNR$^{62}$R$^{63}$)$C_{0-3}$alkyl-, —$C_{0-3}$alkylC(=NNR$^{64}$C(=O)R$^{61}$)$C_{0-3}$alkyl-, —$C_{0-3}$alkylC(=NNR$^{64}$C(=O)OR$^{61}$)$C_{0-3}$alkyl-, —$C_{0-3}$alkylC(=S)NR$^{64}$$C_{0-3}$ alkyl-, —$C_{0-3}$alkylNR$^{64}$$C_{0-3}$alkyl-, —$C_{0-3}$ alkylNR$^{64}$NR$^{64}$$C_{0-3}$alkyl-, —$C_{0-3}$alkylN=N$C_{0-3}$ alkyl-, —$C_{0-3}$alkylNR$^{64}$C(=O)$C_{0-3}$ alkyl-, —$C_{0-3}$ alkylNR$^{64}$C(=O)C(=O)$C_{0-3}$alkyl-, —$C_{0-3}$ alkylNR$^{64}$C(=O)O$C_{0-3}$alkyl-, —$C_{0-3}$ alkylNR$^{64}$C(=O)C(=O)O$C_{0-3}$alkyl-, —$C_{0-3}$ alkylNR$^{64}$C(=O)NR$^{64}$$C_{0-3}$alkyl-, —$C_{0-3}$ alkylNR$^{64}$C(=O)NR$^{64}$C(=O)$C_{0-3}$alkyl-, —$C_{0-3}$ alkylNR$^{64}$C(=O)NR$^{64}$C(=O)O$C_{0-3}$alkyl-, —$C_{0-3}$ alkylNR$^{64}$C(=NR$^{65}$)NR$^{64}$$C_{0-3}$alkyl-, —$C_{0-3}$ alkylNR$^{64}$C(=O)C(=O)NR$^{64}$$C_{0-3}$alkyl-, —$C_{0-3}$ alkylNR$^{64}$C(=S)$C_{0-3}$alkyl-, —$C_{0-3}$alkylNR$^{64}$C(=S)O$C_{0-3}$alkyl-, —$C_{0-3}$ alkylNR$^{64}$C(=S)NR$^{64}$$C_{0-3}$ alkyl-, —$C_{0-3}$ alkylNR$^{64}$S(=O)$_2$$C_{0-3}$ alkyl-, —$C_{0-3}$ alkylNR$^{64}$S(=O)$_2$NR$^{64}$$C_{0-3}$alkyl-, —$C_{0-3}$ alkylO$C_{0-3}$alkyl-, —$C_{0-3}$alkylOC(=O)$C_{0-3}$ alkyl-, —$C_{0-3}$alkylOC(=O)NR$^{64}$$C_{0-3}$alkyl-, —$C_{0-3}$ alkylOC(=O)O$C_{0-3}$ alkyl-, —$C_{0-3}$alkylOC(=NR$^{65}$)NR$^{64}$$C_{0-3}$alkyl-, —$C_{0-3}$alkylOS(=O)$C_{0-3}$ alkyl-, —$C_{0-3}$alkylOS(=O)$_2$$C_{0-3}$alkyl-, —$C_{0-3}$ alkylOS(=O)$_2$O$C_{0-3}$alkyl-, —$C_{0-3}$alkylOS(=O)$_2$ NR$^{64}$$C_{0-3}$alkyl-, —$C_{0-3}$alkylS(=O)$_n$$C_{0-3}$alkyl-, —$C_{0-3}$alkylS(=O)$_2$O$C_{0-3}$alkyl-, —$C_{0-3}$alkylSO$_3$$C_{0-3}$ alkyl-, —$C_{0-3}$alkylS(=O)$_2$ NR$^{64}$$C_{0-3}$alkyl-, and —$C_{0-3}$alkylS(=O)NR$^{64}$$C_{0-3}$alkyl-;

$X^2$ is present or absent, and if present is chosen from $C_{1-6}$alkylene optionally substituted by 1-12 $R^{79}$, $C_{2-6}$alkenylene optionally substituted by 1-10 $R^{79}$, $C_{2-6}$alkynylene optionally substituted by 1-8 $R^{79}$, $C_{6-11}$arylene optionally substituted by 1-10 $R^{79}$, $C_{7-16}$arylalkylene optionally substituted by 1-18 $R^{79}$, $C_{3-11}$cycloalkylene optionally substituted by 1-20 $R^{79}$, $C_{4-17}$cycloalkylalkylene optionally substituted by 1-31 $R^{79}$, 3-15 membered heterocycloalkylene optionally substituted by 1-27 $R^{79}$, 4-21 membered heterocycloalkylalkylene optionally substituted by 1-39 $R^{79}$, 5-15 membered heteroarylene optionally substituted by 1-14 $R^{79}$, 6-21 membered heteroarylalkylene optionally substituted by 1-26 $R^{79}$, —$C_{0-3}$lkylC(=O)$C_{0-3}$alkyl-, —$C_{0-3}$alkylC(=O)O$C_{0-3}$alkyl-, —$C_{0-3}$alkylC(=O)NR$^{74}$$C_{0-3}$alkyl-, —$C_{0-3}$alkylC(=O)C(=O)$C_{0-3}$alkyl-, —$C_{0-3}$alkylC(=NR$^{75}$)$C_{0-3}$ alkyl-, —$C_{0-3}$alkylC(=NR$^{75}$)NR$^{74}$$C_{0-3}$alkyl-, —$C_{0-3}$alkylC(=NOH)NR$^{74}$$C_{0-3}$alkyl-, —$C_{0-3}$alkylC(=NOR$^{76}$)$C_{0-3}$alkyl-, —$C_{0-3}$alkylC(=NNR$^{72}$R$^{73}$)$C_{0-3}$alkyl-, —$C_{0-3}$alkylC(=NNR$^{74}$C(=O)R$^{71}$)$C_{0-3}$alkyl-, —$C_{0-3}$alkylC(=NNR$^{74}$C(=O)OR$^{71}$)$C_{0-3}$alkyl-, —$C_{0-3}$alkylC(=S)NR$^{74}$$C_{0-3}$alkyl-, —$C_{0-3}$alkylNR$^{74}$$C_{0-3}$alkyl-, —$C_{0-3}$alkylNR$^{74}$NR$^{74}$$C_{0-3}$alkyl-, —$C_{0-3}$alkylN=N$C_{0-3}$alkyl-, —$C_{0-3}$alkylNR$^{74}$C(=O)$C_{0-3}$alkyl-, —$C_{0-3}$alkylNR$^{74}$C(=O)C(=O)$C_{0-3}$alkyl-, —$C_{0-3}$alkylNR$^{74}$C(=O)O$C_{0-3}$alkyl-, —$C_{0-3}$alkylNR$^{74}$C(=O)C(=O)O$C_{0-3}$alkyl-, —$C_{0-3}$alkylNR$^{74}$C(=O)NR$^{74}$$C_{0-3}$alkyl-, —$C_{0-3}$alkylNR$^{74}$C(=O)NR$^{74}$C(=O)$C_{0-3}$alkyl-, —$C_{0-3}$alkylNR$^{74}$C(=O)NR$^{74}$C(=O)O$C_{0-3}$alkyl-, —$C_{0-3}$alkylNR$^{74}$C(=NR$^{75}$)NR$^{74}$$C_{0-3}$alkyl-, —$C_{0-3}$alkylNR$^{74}$C(=O)C(=O)NR$^{74}$$C_{0-3}$alkyl-, —$C_{0-3}$alkylNR$^{74}$C(=S)$C_{0-3}$alkyl-, —$C_{0-3}$alkylNR$^{74}$C(=S)O$C_{0-3}$alkyl-, —$C_{0-3}$alkylNR$^{74}$C(=S)NR$^{74}$$C_{0-3}$alkyl-, —$C_{0-3}$alkylNR$^{74}$S(=O)$_2$$C_{0-3}$alkyl-, —$C_{0-3}$alkylNR$^{74}$S(=O)$_2$NR$^{74}$$C_{0-3}$alkyl-, —$C_{0-3}$ alkylO$C_{0-3}$ alkyl-, —$C_{0-3}$alkylOC(=O)$C_{0-3}$alkyl-, —$C_{0-3}$ alkylOC(=O)NR$^{74}$$C_{0-3}$alkyl-, —$C_{0-3}$alkylOC(=O)O$C_{0-3}$alkyl-, —$C_{0-3}$alkylOC(=NR$^{75}$)NR$^{74}$$C_{0-3}$ alkyl-, —$C_{0-3}$alkylOS(=O)$C_{0-3}$alkyl-, —$C_{0-3}$ alkylOS(=O)$_2$$C_{0-3}$alkyl-, —$C_{0-3}$alkylOS(=O)$_2$ O$C_{0-3}$alkyl-, —$C_{0-3}$alkylOS(=O)$_2$NR$^{74}$$C_{0-3}$ alkyl-, —$C_{0-3}$alkylS(=O)$_n$$C_{0-3}$alkyl-, —$C_{0-3}$alkylS(=O)$_2$ O$C_{0-3}$alkyl-, —$C_{0-3}$alkylSO$_3$$C_{0-3}$alkyl-, —$C_{0-3}$ alkylS(=O)$_2$NR$^{74}$$C_{0-3}$alkyl-, and —$C_{0-3}$alkylS(=O)NR$^{74}$$C_{0-3}$alkyl-;

$Z^2$ is chosen from H, $C_{1-6}$alkyl optionally substituted by 1-13 $R^{89}$, $C_{2-6}$alkenyl optionally substituted by 1-11 $R^{89}$, $C_{2-6}$alkynyl optionally substituted by 1-9 $R^{89}$, $C_{6-11}$aryl optionally substituted by 1-11 $R^{89}$, $C_{7-16}$arylalkyl optionally substituted by 1-19 $R^{89}$, $C_{3-11}$cycloalkyl optionally substituted by 1-21 $R^{89}$, $C_{4-17}$cycloalkylalkyl optionally substituted by 1-32 $R^{89}$, 3-15 membered heterocycloalkyl optionally substituted by 1-28 $R^{89}$, 4-21 membered heterocycloalkylalkyl optionally substituted by 1-40 $R^{89}$, 5-15 membered heteroaryl optionally substituted by 1-15 $R^{89}$, 6-21 membered heteroarylalkyl optionally substituted by 1-27 $R^{89}$, halogen, —CN, —C(=O)R$^{80}$, —C(=O)OR$^{80}$, —C(=O)NR$^{82}$R$^{83}$, —C(=O)C(=O)R$^{80}$, —C(=NR$^{85}$)R$^{80}$, —C(=NR$^{85}$)NR$^{82}$R$^{83}$, —C(=NOH)NR$^{82}$R$^{83}$, —C(=NOR$^{86}$)R$^{80}$, —C(=NNR$^{82}$R$^{83}$)R$^{80}$, —C(=NNR$^{84}$C(=O)R$^{81}$)R$^{80}$, —C(=NNR$^{84}$C(=O)OR$^{81}$)R$^{80}$, —C(=S)NR$^{82}$R$^{83}$, —NC, —NO$_2$, —NR$^{82}$R$^{83}$, —NR$^{84}$NR$^{82}$R$^{83}$, —N=NR$^{84}$, =NR$^{80}$, =NOR$^{80}$, —NR$^{84}$OR$^{86}$, —NR$^{84}$C(=O)R$^{80}$, —NR$^{84}$C(=O)C(=O)R$^{80}$, —NR$^{84}$C(=O)OR$^{81}$, —NR$^{84}$C(=O)C(=O)OR$^{81}$, —NR$^{84}$C(=O)NR$^{82}$R$^{83}$, —NR$^{84}$C(=O)NR$^{84}$C(=O)R$^{80}$, —NR$^{84}$C(=O)NR$^{84}$C(=O)OR$^{80}$, —NR$^{84}$C(=NR$^{85}$)NR$^{82}$R$^{83}$, —NR$^{84}$C(=O)C(=O)NR$^{82}$R$^{83}$, —NR$^{84}$C(=S)R$^{80}$, —NR$^{84}$C(=S)OR$^{80}$, —NR$^{84}$C(=S)NR$^{82}$R$^{83}$, —NR$^{84}$S(=O)$_2$R$^{81}$, —NR$^{84}$S(=O)$_2$NR$^{82}$R$^{83}$, —NR$^{84}$P(=O)R$^{88}$R$^{88}$, —NR$^{84}$P(=O)(NR$^{82}$R$^{83}$)(NR$^{82}$R$^{83}$), —NR$^{84}$P(=O)(OR$^{80}$)(OR$^{80}$), —NR$^{84}$P(=O)(SR$^{80}$)(SR$^{80}$), —OR$^{80}$, =O, —OCN, —OC(=O)R$^{80}$, —OC(=O)NR$^{82}$R$^{83}$, —OC(=O)OR$^{80}$, —OC(=NR$^{85}$)NR$^{82}$R$^{83}$, —OS(=O)R$^{80}$, —OS(=O)$_2$R$^{80}$, —OS(=O)$_2$OR$^{80}$, —OS(=O)$_2$NR$^{82}$R$^{83}$, —OP(=O)R$^{88}$R$^{88}$, —OP(=O)(NR$^{82}$R$^{83}$)(NR$^{82}$R$^{83}$), —OP(=O)(OR$^{80}$)(OR$^{80}$), —OP(=O)(SR$^{80}$)(SR$^{80}$), —SCN, =S, —S(=O)$_6$R$^{80}$, —S(=O)$_2$OR$^{80}$, —SO$_3$R$^{87}$, —S(=O)$_2$NR$^{82}$R$^{83}$, —S(=O)NR$^{82}$R$^{83}$, —SP(=O)R$^{88}$R$^{88}$, —SP(=O)(NR$^{82}$R$^{83}$)(NR$^{82}$R$^{83}$), —SP(=O)(OR$^{80}$)(OR$^{80}$), —SP(=O)(SR$^{80}$)(SR$^{80}$), —P(=O)R$^{88}$R$^{88}$, —P(=O)(NR$^{82}$R$^{83}$)(NR$^{82}$R$^{83}$), —P(=O)(OR$^{80}$)(OR$^{80}$), and —P(=O)(SR$^{80}$)(SR$^{80}$);

$Z^3$ is H, $C_{1-6}$alkyl optionally substituted by 1-13 $R^{89}$, or halogen;

$Z^4$ is H, $C_{1-6}$alkyl optionally substituted by 1-13 $R^{89}$, $C_{2-6}$alkenyl optionally substituted by 1-11 $R^{89}$, halogen, —$OR^{80}$, or —CN;

alternatively, when $L^2$, $A^2$, $G^2$, and $X^2$ are absent, $Z^2$ and $Z^3$ can together form a group of formula -$A^{21}$-$A^{22}$-$A^{23}$-, wherein $A^{21}$, $A^{22}$, and $A^{23}$ are independently chosen from —$CZ^{21}Z^{22}$—, —$CZ^{23}Z^{24}CZ^{25}Z^{26}$—, wherein when any two of $Z^{21}$, $Z^{22}$, $Z^{23}$, $Z^{24}$, $Z^{25}$, $Z^{26}$ and $Z^{27}$ are located on adjacent atoms, they may together form a bond between the atoms, and wherein any of $Z^{21}$, $Z^{22}$, $Z^{23}$, $Z^{24}$, $Z^{25}$, $Z^{26}$ and $Z^{27}$ may be independently chosen from H and —$OR^{90}$;

$R^9$, $R^{19}$, $R^{29}$, $R^{39}$, $R^{49}$, $R^{59}$, $R^{69}$, $R^{79}$, and $R^{89}$ at each occurrence is independently chosen from $C_{1-6}$alkyl optionally substituted by 1-13 $R^{179}$, $C_{2-6}$alkenyl optionally substituted by 1-11 $R^{179}$, $C_{2-6}$alkynyl optionally substituted by 1-9 $R^{179}$, $C_{6-11}$aryl optionally substituted by 1-11 $R^{179}$, $C_{7-16}$arylalkyl optionally substituted by 1-19 $R^{179}$, $C_{3-11}$cycloalkyl optionally substituted by 1-21 $R^{179}$, $C_{4-17}$cycloalkylalkyl optionally substituted by 1-32 $R^{179}$, 3-15 membered heterocycloalkyl optionally substituted by 1-28 $R^{179}$, 4-21 membered heterocycloalkylalkyl optionally substituted by 1-40 $R^{179}$, 5-15 membered heteroaryl optionally substituted by 1-15 $R^{179}$, 6-21 membered heteroarylalkyl optionally substituted by 1-27 $R^{179}$, halogen, —CN, —C(=O)$R^{170}$, —C(=O)O$R^{170}$, —C(=O)N$R^{172}R^{173}$, —C(=O)C(=O)$R^{170}$, —C(=N$R^{175}$)$R^{170}$, —C(=N$R^{175}$)N$R^{172}R^{173}$, —C(=NOH)N$R^{172}R^{173}$, —C(=NO$R^{176}$)$R^{170}$, —C(=NN$R^{172}R^{173}$)$R^{170}$, —C(NN$R^{174}$C(=O)$R^{171}$)$R^{170}$, —C(=NN$R^{174}$C(=O)O$R^{171}$)$R^{170}$, —C(=S)N$R^{172}R^{173}$, —NC, —NO$_2$, —N$R^{172}R^{173}$, —N$R^{174}$N$R^{172}R^{173}$, —N=N$R^{174}$, —N$R^{170}$, =NO$R^{170}$, —N$R^{174}$O$R^{176}$, —N$R^{174}$C(=O)$R^{170}$, —N$R^{174}$C(=O)C(=O)$R^{170}$, —N$R^{174}$C(=O)O$R^{171}$, —N$R^{174}$C(=O)C(=O)O$R^{171}$, —N$R^{174}$C(=O)N$R^{172}R^{173}$, —N$R^{174}$C(=O)N$R^{174}$C(=O)$R^{170}$, —N$R^{174}$C(=O)N$R^{174}$C(=O)O$R^{170}$, —N$R^{174}$C(=N$R^{175}$)N$R^{172}R^{173}$, —N$R^{174}$C(=O)C(=O)N$R^{172}R^{173}$, —N$R^{174}$C(=S)$R^{170}$, —N$R^{174}$C(=S)O$R^{170}$, —N$R^{174}$C(=S)N$R^{172}R^{173}$, —N$R^{174}$S(=O)$_2R^{171}$, —N$R^{174}$S(=O)$_2$N$R^{172}R^{173}$, —N$R^{174}$P(=O)$R^{178}R^{178}$, —N$R^{174}$P(=O)(N$R^{172}R^{173}$)(N$R^{172}R^{173}$), —N$R^{174}$P(=O)(O$R^{170}$)(O$R^{170}$), —N$R^{174}$P(=O)(S$R^{170}$)(S$R^{170}$), —O$R^{170}$, =O, —OCN, —OC(=O)$R^{170}$, —OC(=O)N$R^{172}R^{173}$, —OC(=O)O$R^{170}$, —OC(=N$R^{175}$)N$R^{172}R^{173}$, —OS(=O)$R^{170}$, —OS(=O)$_2R^{170}$, —OS(=O)$_2$O$R^{170}$, —OS(=O)$_2$N$R^{172}R^{173}$, —OP(=O)$R^{178}R^{178}$, —OP(=O)(N$R^{172}R^{173}$)(N$R^{172}R^{173}$), —OP(=O)(O$R^{170}$)(O$R^{170}$), —OP(=O)(S$R^{170}$)(S$R^{170}$), —SCN, =S, —S(=O)$_nR^{170}$, —S(=O)$_2$O$R^{170}$, —SO$_3R^{177}$, —S(=O)$_2$N$R^{172}R^{173}$, —S(=O)N$R^{172}R^{173}$, —SP(=O)$R^{178}R^{178}$, —SP(=O)(N$R^{172}R^{173}$)(N$R^{172}R^{173}$), —SP(=O)(O$R^{170}$)(O$R^{170}$), —SP(=O)(S$R^{170}$)(S$R^{170}$), —P(=O)$R^{178}R^{178}$, —P(=O)(N$R^{172}R^{173}$)(N$R^{172}R^{173}$), —P(=O)(O$R^{170}$)(O$R^{170}$), and —P(=O)(S$R^{170}$)(S$R^{170}$);

$R^1$, $R^4$, $R^5$, $R^6$, $R^{10}$, $R^{11}$, $R^{14}$, $R^{15}$, $R^{16}$, $R^{17}$, $R^{21}$, $R^{24}$, $R^{25}$, $R^{26}$, $R^{31}$, $R^{34}$, $R^{35}$, $R^{36}$, $R^{41}$, $R^{44}$, $R^{45}$, $R^{46}$, $R^{50}$, $R^{51}$, $R^{54}$, $R^{55}$, $R^{56}$, $R^{57}$, $R^{61}$, $R^{64}$, $R^{65}$, $R^{66}$, $R^{71}$, $R^{74}$, $R^{75}$, $R^{76}$, $R^{80}$, $R^{81}$, $R^{84}$, $R^{85}$, $R^{86}$, $R^{87}$, $R^{90}$, $R^{100}$, $R^{101}$, $R^{104}$, $R^{105}$, $R^{106}$, $R^{107}$, $R^{170}$, $R^{171}$, $R^{174}$, $R^{175}$, $R^{176}$ and $R^{177}$ at each occurrence is independently chosen from H, $C_{1-6}$alkyl optionally substituted by 1-13 $R^{189}$, $C_{2-6}$alkenyl optionally substituted by 1-11 $R^{189}$, $C_{2-6}$alkynyl optionally substituted by 1-9 $R^{189}$, $C_{6-11}$aryl optionally substituted by 1-11 $R^{189}$, $C_{7-16}$arylalkyl optionally substituted by 1-19 $R^{189}$, $C_{3-11}$cycloalkyl optionally substituted by 1-21 $R^{189}$, $C_{4-17}$cycloalkylalkyl optionally substituted by 1-32 $R^{189}$, 3-15 membered heterocycloalkyl optionally substituted by 1-28 $R^{189}$, 4-21 membered heterocycloalkylalkyl optionally substituted by 1-40 $R^{189}$, 5-15 membered heteroaryl optionally substituted by 1-15 $R^{189}$, and 6-21 membered heteroarylalkyl optionally substituted by 1-27 $R^{189}$;

$R^{18}$, $R^{58}$, $R^{88}$, $R^{108}$, and $R^{178}$ at each occurrence is independently chosen from $C_{1-6}$alkyl optionally substituted by 1-13 $R^{189}$, $C_{2-6}$alkenyl optionally substituted by 1-11 $R^{189}$, $C_{2-6}$alkynyl optionally substituted by 1-9 $R^{189}$, $C_{6-11}$aryl optionally substituted by 1-11 $R^{189}$, $C_{7-16}$arylalkyl optionally substituted by 1-19 $R^{189}$, $C_{3-11}$cycloalkyl optionally substituted by 1-21 $R^{189}$, $C_{4-17}$cycloalkylalkyl optionally substituted by 1-32 $R^{189}$, 3-15 membered heterocycloalkyl optionally substituted by 1-28 $R^{189}$, 4-21 membered heterocycloalkylalkyl optionally substituted by 1-40 $R^{189}$, 5-15 membered heteroaryl optionally substituted by 1-15 $R^{189}$, and 6-21 membered heteroarylalkyl optionally substituted by 1-27 $R^{189}$;

$R^2$, $R^3$, $R^{12}$, $R^{13}$, $R^{22}$, $R^{23}$, $R^{32}$, $R^{33}$, $R^{42}$, $R^{43}$, $R^{52}$, $R^{53}$, $R^{62}$, $R^{63}$, $R^{72}$, $R^{73}$, $R^{82}$, $R^{83}$, $R^{102}$, $R^{103}$, $R^{172}$ and $R^{173}$ at each occurrence is independently chosen from H, $C_{1-6}$alkyl optionally substituted by 1-13 $R^{199}$, $C_{2-6}$alkenyl optionally substituted by 1-11 $R^{199}$, $C_{2-6}$alkynyl optionally substituted by 1-9 $R^{199}$, $C_{6-11}$aryl optionally substituted by 1-11 $R^{199}$, $C_{7-16}$arylalkyl optionally substituted by 1-19 $R^{199}$, $C_{3-11}$cycloalkyl optionally substituted by 1-21 $R^{199}$, $C_{4-17}$cycloalkylalkyl optionally substituted by 1-32 $R^{199}$, 3-15 membered heterocycloalkyl optionally substituted by 1-28 $R^{199}$, 4-21 membered heterocycloalkylalkyl optionally substituted by 1-40 $R^{199}$, 5-15 membered heteroaryl optionally substituted by 1-15 $R^{199}$, and 6-21 membered heteroarylalkyl optionally substituted by 1-27 $R^{199}$;

or any $R^2$ and $R^3$, $R^{12}$ and $R^{13}$, $R^{22}$ and $R^{23}$, $R^{32}$ and $R^{33}$, $R^{42}$ and $R^{43}$, $R^{52}$ and $R^{53}$, $R^{62}$ and $R^{63}$, $R^{72}$ and $R^{73}$, $R^{82}$ and $R^{83}$, $R^{102}$ and $R^{103}$, or $R^{172}$ and $R^{173}$ may form, together with the nitrogen atom to which they are attached, a 3-15 membered heterocycloalkyl optionally substituted by 1-28 $R^{209}$ or a 5-15 membered heteroaryl optionally substituted by 1-15 $R^{209}$;

$R^{179}$, $R^{189}$, $R^{199}$ and $R^{209}$ at each occurrence is independently chosen from $C_{1-6}$alkyl optionally substituted by 1-13 $R^{219}$, $C_{2-6}$alkenyl optionally substituted by 1-11 $R^{219}$, $C_{2-6}$alkynyl optionally substituted by 1-9 $R^{219}$, $C_{6-11}$aryl optionally substituted by 1-11 $R^{219}$, $C_{7-16}$arylalkyl optionally substituted by 1-19 $R^{219}$, $C_{3-11}$cycloalkyl optionally substituted by 1-21 $R^{219}$, $C_{4-17}$cycloalkylalkyl optionally substituted by 1-32 $R^{219}$, 3-15 membered heterocycloalkyl optionally substituted by 1-28 $R^{219}$, 4-21 membered heterocycloalkylalkyl optionally substituted by 1-40 $R^{219}$, 5-15 membered heteroaryl optionally substituted by 1-15 $R^{219}$, 6-21 membered heteroarylalkyl optionally substituted by 1-27 $R^{219}$, halogen, —CN, —C(=O)$R^{210}$, —C(=O)O$R^{210}$, —C(=O)N$R^{212}R^{213}$, —C(=O)C(=O)$R^{210}$, —C(=N$R^{215}$)$R^{210}$, —C(=N$R^{215}$)N$R^{212}R^{213}$, —C(=NOH)N$R^{212}R^{213}$, —C(=NO$R^{216}$)$R^{210}$, —C(=NN$R^{212}R^{213}$)$R^{210}$, —C(NN$R^{214}$C(=O)$R^{211}$)$R^{210}$, —C(=NN$R^{214}$C(=O)O$R^{211}$)$R^{210}$, —C(=S)N$R^{212}R^{213}$, —NC, —NO$_2$, —N$R^{212}R^{213}$, —N$R^{214}$N$R^{212}R^{213}$, —N=N$R^{214}$, =N$R^{210}$, =NO$R^{210}$, —N$R^{214}$O$R^{216}$, —N$R^{214}$C(=O)$R^{210}$, —N$R^{214}$C(=O)C(=O)$R^{210}$, —N$R^{214}$C(=O)O$R^{211}$, —N$R^{214}$C(=O)C(=O)O$R^{211}$, —N$R^{214}$C(=O)N$R^{212}R^{213}$, —N$R^{214}$C(=O)N$R^{214}$C(=O)$R^{210}$, —N$R^{214}$C(=O)N$R^{214}$C(=O)O$R^{210}$, —N$R^{214}$C(=N$R^{215}$)N$R^{212}R^{213}$, —N$R^{214}$C(=O)C(=O)N$R^{212}R^{213}$, —N$R^{214}$C(=S)$R^{210}$, —N$R^{214}$C(=S)O$R^{210}$, —N$R^{214}$C(=S)N$R^{212}R^{213}$, —N$R^{214}$S(=O)$_2R^{211}$, —N$R^{214}$S(=O)$_2$N$R^{212}R^{213}$, —N$R^{214}$P(=O)$R^{218}R^{218}$, —N$R^{214}$P(=O)(N$R^{212}R^{213}$)(N$R^{212}R^{213}$), —N$R^{214}$P(=O)(O$R^{210}$)(O$R^{210}$), —N$R^{214}$P(=O)(S$R^{210}$)(S$R^{210}$), —O$R^{210}$, =O, —OCN, —OC(=O)$R^{210}$, —OC(=O)N$R^{212}R^{213}$, —OC(=O)O$R^{210}$, —OC(=N$R^{215}$)N$R^{212}R^{213}$, —OS(=O)$R^{210}$, —OS(=O)$_2R^{210}$, —OS(=O)$_2$O$R^{210}$, —OS(=O)$_2$N$R^{212}R^{213}$, —OP(=O)$R^{218}R^{218}$, —OP(=O)(N$R^{212}R^{213}$)(N$R^{212}R^{213}$), —OP(=O)(O$R^{210}$)(O$R^{210}$), —OP(=O)(S$R^{210}$)(S$R^{210}$), —SCN, =S, —S(=O)$_nR^{210}$, —S(=O)$_2$O$R^{210}$, —SO$_3R^{217}$, —S(=O)$_2$N$R^{212}R^{213}$, —S(=O)N$R^{212}R^{213}$, —SP(=O)$R^{218}R^{218}$, —SP(=O)(N$R^{212}R^{213}$)(N$R^{212}R^{213}$), —SP(=O)(O$R^{210}$)(O$R^{210}$), —SP(=O)(S$R^{210}$)(S$R^{210}$), —P(=O)$R^{218}R^{218}$, —P(=O)(N$R^{212}R^{213}$)(N$R^{212}R^{213}$), —P(=O)(O$R^{210}$)(O$R^{210}$), and —P(=O)(S$R^{210}$)(S$R^{210}$);

$R^{210}$, $R^{211}$, $R^{214}$, $R^{215}$, $R^{216}$ and $R^{217}$ at each occurrence is independently chosen from H, $C_{1-6}$alkyl optionally substituted by 1-13 $R^{229}$, $C_{2-6}$alkenyl optionally substituted by 1-11 $R^{229}$, $C_{2-6}$alkynyl optionally substituted by 1-9 $R^{229}$, $C_{6-11}$aryl optionally substituted by 1-11 $R^{229}$, $C_{7-16}$arylalkyl optionally substituted by 1-19 $R^{229}$, $C_{3-11}$cycloalkyl optionally substituted by 1-21 $R^{229}$, $C_{4-17}$cycloalkylalkyl optionally substituted by 1-32 $R^{229}$, 3-15 membered heterocycloalkyl optionally substituted by 1-28 $R^{229}$, 4-21 membered heterocycloalkylalkyl optionally substituted by 1-40 $R^{229}$, 5-15 membered heteroaryl optionally substituted by 1-15 $R^{229}$, and 6-21 membered heteroarylalkyl optionally substituted by 1-27 $R^{229}$;

$R^{212}$ and $R^{213}$ at each occurrence is independently chosen from H, $C_{1-6}$alkyl optionally substituted by 1-13 $R^{239}$, $C_{2-6}$alkenyl optionally substituted by 1-11 $R^{239}$, $C_{2-6}$alkynyl optionally substituted by 1-9 $R^{239}$, $C_{6-11}$aryl optionally substituted by 1-11 $R^{239}$, $C_{7-16}$arylalkyl optionally substituted by 1-19 $R^{239}$, $C_{3-11}$cycloalkyl optionally substituted by 1-21 $R^{239}$, $C_{4-17}$cycloalkylalkyl optionally substituted by 1-32 $R^{239}$, 3-15 membered heterocycloalkyl optionally substituted by 1-28 $R^{239}$, 4-21 membered heterocycloalkylalkyl optionally substituted by 1-40 $R^{239}$, 5-15 membered heteroaryl optionally substituted by 1-15 $R^{239}$, and 6-21 membered heteroarylalkyl optionally substituted by 1-27 $R^{239}$;

or any $R^{212}$ and $R^{213}$ may form, together with the nitrogen atom to which they are attached, a 3-15 membered heterocycloalkyl optionally substituted by 1-28 $R^{249}$ or a 5-15 membered heteroaryl optionally substituted by 1-15 $R^{249}$;

$R^{218}$ at each occurrence is independently chosen from $C_{1-6}$alkyl optionally substituted by 1-13 $R^{229}$, $C_{2-6}$alkenyl optionally substituted by 1-11 $R^{229}$, $C_{2-6}$alkynyl optionally substituted by 1-9 $R^{229}$, $C_{6-11}$aryl optionally substituted by 1-11 $R^{229}$, $C_{7-16}$arylalkyl optionally substituted by 1-19 $R^{229}$, $C_{3-11}$cycloalkyl optionally substituted by 1-21 $R^{229}$, $C_{4-17}$cycloalkylalkyl optionally substituted by 1-32 $R^{229}$, 3-15 membered heterocycloalkyl optionally substituted by 1-28 $R^{229}$, 4-21 membered heterocycloalkylalkyl optionally substituted by 1-40 $R^{229}$, 5-15 membered heteroaryl optionally substituted by 1-15 $R^{229}$, and 6-21 membered heteroarylalkyl optionally substituted by 1-27 $R^{229}$;

$R^{219}$, $R^{229}$, $R^{239}$ and $R^{249}$ at each occurrence is independently chosen from $C_{1-6}$alkyl optionally substituted by 1-13 halogen, $C_{2-6}$alkenyl, $C_{2-6}$alkynyl, $C_{6-11}$aryl, $C_{7-16}$arylalkyl, $C_{3-11}$cycloalkyl, $C_{4-17}$cycloalkylalkyl, 3-15 membered heterocycloalkyl, 4-21 membered heterocycloalkylalkyl, 5-15 membered heteroaryl, 6-21 membered heteroarylalkyl, halogen, —CN, —C(=O)$R^{250}$, —C(=O)O$R^{250}$, —C(=O)N$R^{250}R^{250}$, —C(=O)C(=O)$R^{250}$, —C(=N$R^{250}$)$R^{250}$, —C(=N$R^{250}$)N$R^{250}R^{250}$, —C(=NOH)N$R^{250}R^{250}$, —C(=NO$R^{250}$)$R^{250}$, —C(=NN$R^{250}R^{250}$)$R^{250}$, —C(=NN$R^{250}$C(=O)$R^{250}$)$R^{250}$, —C(=NN$R^{250}$C(=O)O$R^{250}$)$R^{250}$, —C(=S)N$R^{250}R^{250}$, —NC, —NO$_2$, —N$R^{250}R^{250}$, —N$R^{250}$N$R^{250}R^{250}$, —N=N$R^{250}$, =N$R^{250}$, =NO$R^{250}$, —N$R^{250}$O$R^{250}$, —N$R^{250}$C(=O)$R^{250}$, —N$R^{250}$C(=O)C(=O)$R^{250}$, —N$R^{250}$C(=O)O$R^{250}$, —N$R^{250}$C(=O)C(=O)O$R^{250}$, —N$R^{250}$C(=O)N$R^{250}R^{250}$, —N$R^{250}$C(=O)N$R^{250}$C(=O)$R^{250}$, —N$R^{250}$C(=O)N$R^{250}$C(=O)O$R^{250}$, —N$R^{250}$C(=N$R^{250}$)N$R^{250}R^{250}$, —N$R^{250}$C(=O)C(=O)N$R^{250}R^{250}$, —N$R^{250}$C(S)$R^{250}$, —N$R^{250}$C(S)O$R^{250}$, —N$R^{250}$C(=S)N$R^{250}R^{250}$, —N$R^{250}$S(=O)$_2R^{250}$, —N$R^{250}$S(=O)$_2$N$R^{250}R^{250}$, —N$R^{250}$P(=O)$R^{251}R^{251}$, —N$R^{250}$P(=O)(N$R^{250}R^{250}$)(N$R^{250}R^{250}$), —N$R^{250}$P(=O)(O$R^{250}$)(O$R^{250}$), —N$R^{250}$P(=O)(S$R^{250}$)(S$R^{250}$), —O$R^{250}$, =O, —OCN, —OC(=O)$R^{250}$, —OC(=O)N$R^{250}R^{250}$, —OC(=O)O$R^{250}$, —OC(=N$R^{250}$)N$R^{250}R^{250}$, —OS(=O)$R^{250}$, —OS(=O)$_2R^{250}$, —OS(=O)$_2$O$R^{250}$, —OS(=O)$_2$N$R^{250}R^{250}$, —OP(=O)$R^{251}R^{251}$, —OP(=O)(N$R^{250}R^{250}$)(N$R^{250}R^{250}$), —OP(=O)(O$R^{250}$)(O$R^{250}$), —OP(=O)(S$R^{250}$)(S$R^{250}$), —SCN, =S, —S(=O)$_nR^{250}$, —S(=O)$_2$O$R^{250}$, —SO$_3R^{250}$, —S(=O)$_2$N$R^{250}R^{250}$, —S(=O)N$R^{250}R^{250}$, —SP(=O)$R^{251}R^{251}$, —SP(=O)(N$R^{250}R^{250}$)(N$R^{250}R^{250}$), —SP(=O)(O$R^{250}$)(O$R^{250}$), —SP(=O)(S$R^{250}$)(S$R^{250}$), —P(=O)$R^{251}R^{251}$, —P(=O)(N$R^{250}R^{250}$)(N$R^{250}R^{250}$), —P(=O)(O$R^{250}$)(O$R^{250}$), and —P(=O)(S$R^{250}$)(S$R^{250}$);

$R^{250}$ at each occurrence is independently chosen from H, $C_{1-6}$alkyl and $C_{1-6}$-haloalkyl;

$R^{251}$ at each occurrence is independently chosen from $C_{1-6}$alkyl and $C_{1-6}$-haloalkyl; and n at each occurrence is independently chosen from 0, 1, and 2.

8. A compound as defined in claim 7, wherein $Q^2$ is —$X^2$—$Z^2$.

9. A compound as defined in claim 7, wherein $L^1$ is —$C_{0-3}$alkylN$R^4C_{0-3}$alkyl-, —N$R^4$N$R^4$—, —N$R^4$C(=O)—, —N$R^4$C(=O)O—, —N$R^4$C(=O)N$R^4$—, —N$R^4$C(=O)

$NR^4C(=O)-$, $-NR^4C(=S)-$, $-NR^4C(=S)NR^4-$, $-NR^4S(=O)_2-$, $-C_{0-3}alkylOC_{0-3}alkyl-$, $-S(=O)_n-$, or absent.

10. A compound as defined in claim 8, wherein $L^1$ is $-C_{0-3}alkylNR^4C_{0-3}alkyl-$, $-NR^4NR^4-$, $-NR^4C(=O)-$, $-NR^4C(=O)O-$, $-NR^4C(=O)NR^4-$, $-NR^4C(=O)NR^4C(=O)-$, $-NR^4C(=S)-$, $-NR^4C(=S)NR^4-$, $-NR^4S(=O)_2-$, $-C_{0-3}alkylOC_{0-3}alkyl-$, $-S(=O)_n-$, or absent.

\* \* \* \* \*